United States Patent
Arnold et al.

(10) Patent No.: US 12,145,911 B2
(45) Date of Patent: Nov. 19, 2024

(54) INHIBITORS OF CYSTEINE PROTEASES AND METHODS OF USE THEREOF

(71) Applicant: Pardes Biosciences, Inc., Carlsbad, CA (US)

(72) Inventors: Lee D. Arnold, Rancho Santa Fe, CA (US); Andy Jennings, San Diego, CA (US); Walter Keung, Encinitas, CA (US)

(73) Assignee: Pardes Biosciences, Inc., Carlsbad, CA (US)

( * ) Notice: Subject to any disclaimer, the term of this patent is extended or adjusted under 35 U.S.C. 154(b) by 0 days.

(21) Appl. No.: 17/828,881

(22) Filed: May 31, 2022

(65) Prior Publication Data

US 2024/0270693 A1     Aug. 15, 2024

Related U.S. Application Data

(63) Continuation of application No. 17/525,514, filed on Nov. 12, 2021, now Pat. No. 11,524,940, which is a continuation of application No. 17/322,221, filed on May 17, 2021, now Pat. No. 11,174,231.

(60) Provisional application No. 63/179,128, filed on Apr. 23, 2021, provisional application No. 63/173,146, filed on Apr. 9, 2021, provisional application No. 63/172,478, filed on Apr. 8, 2021, provisional application No. 63/171,675, filed on Apr. 7, 2021, provisional application No. 63/129,018, filed on Dec. 22, 2020, provisional application No. 63/091,630, filed on Oct. 14, 2020, provisional application No. 63/067,669, filed on Aug. 19, 2020, provisional application No. 63/039,297, filed on Jun. 15, 2020, provisional application No. 63/036,866, filed on Jun. 9, 2020.

(51) Int. Cl.
    *C07D 213/90*     (2006.01)
    *A61K 31/445*     (2006.01)
    *A61K 45/06*     (2006.01)

(52) U.S. Cl.
    CPC ............ *C07D 213/90* (2013.01); *A61K 45/06* (2013.01)

(58) Field of Classification Search
    CPC .................................................... A61K 31/445
    USPC ........................................................ 514/315
    See application file for complete search history.

(56) References Cited

U.S. PATENT DOCUMENTS

| | | | |
|---|---|---|---|
| 6,514,997 B2 | 2/2003 | Dragovich et al. |
| 7,504,382 B2 | 3/2009 | Cai et al. |
| 7,504,392 B2 | 3/2009 | Forbes et al. |
| 9,309,284 B2 | 4/2016 | Chang et al. |
| 9,474,759 B2 | 10/2016 | Chang et al. |
| 9,975,885 B2 | 5/2018 | St. John et al. |
| 2004/0235952 A1 | 11/2004 | Fuhrman et al. |
| 2005/0143319 A1 | 6/2005 | Yang et al. |
| 2005/0143320 A1 | 6/2005 | Yang et al. |
| 2006/0014821 A1 | 1/2006 | He et al. |
| 2014/0243341 A1 | 8/2014 | Chang et al. |
| 2019/0151400 A1 | 5/2019 | Chang et al. |
| 2021/0008150 A1 | 1/2021 | Schinazi et al. |

FOREIGN PATENT DOCUMENTS

| | | |
|---|---|---|
| CN | 102838523 A | 12/2012 |
| CN | 103130710 A | 6/2013 |
| CN | 103145608 B | 9/2015 |
| CN | 110105348 A | 8/2019 |
| CN | 110818691 A | 2/2020 |
| CN | 107459511 B | 5/2020 |
| CN | 111135167 A | 5/2020 |
| CN | 113444144 A | 9/2021 |
| CN | 114057702 A | 2/2022 |
| JP | 2006169176 A | 6/2006 |
| WO | WO-97/31939 A1 | 9/1997 |
| WO | WO-99/24460 A2 | 5/1999 |
| WO | WO-2001/010894 A2 | 2/2001 |
| WO | WO-01/19816 A1 | 3/2001 |
| WO | WO-2001/40189 A1 | 6/2001 |
| WO | WO-01/49288 A1 | 7/2001 |
| WO | WO-2004/020441 A1 | 3/2004 |
| WO | WO-2004092360 A2 | 10/2004 |
| WO | WO-2004/093860 A1 | 11/2004 |
| WO | WO-2005058821 A1 | 6/2005 |
| WO | WO-2005/113580 A1 | 12/2005 |
| WO | WO-2006/061714 A2 | 6/2006 |
| WO | WO-2007/120160 A2 | 10/2007 |
| WO | WO-2013/049382 A2 | 4/2013 |
| WO | WO-2017/114509 A1 | 7/2017 |
| WO | WO-2017/197377 A1 | 11/2017 |
| WO | WO-2017/222935 A1 | 12/2017 |
| WO | WO-2018/042343 A2 | 3/2018 |
| WO | WO-2020/030143 A1 | 2/2020 |
| WO | WO-2020/247665 A1 | 12/2020 |
| WO | WO-2021/191827 A1 | 9/2021 |

(Continued)

OTHER PUBLICATIONS

Abranyi-Balogh, et al. "A road map for prioritizing warheads for cysteine targeting covalent inhibitors," European Journal of Medicinal Chemistry, vol. 160, 2018, pp. 94-107.

(Continued)

*Primary Examiner* — Raymond J Henley, III

(74) *Attorney, Agent, or Firm* — Goodwin Procter LLP

(57) ABSTRACT

The disclosure provides compounds with warheads and their use in treating medical diseases or disorders, such as viral infections. Pharmaceutical compositions and methods of making various compounds with warheads are provided. The compounds are contemplated to inhibit proteases, such as the 3C, CL- or 3CL-like protease.

4 Claims, No Drawings

(56) References Cited

FOREIGN PATENT DOCUMENTS

| WO | WO-2021/206876 A1 | 10/2021 |
|---|---|---|
| WO | WO-2021/216195 A1 | 10/2021 |
| WO | WO-2021205298 A1 | 10/2021 |
| WO | WO-2021226546 A1 | 11/2021 |
| WO | WO-2021250648 A1 | 12/2021 |
| WO | WO-202202042 A1 | 1/2022 |
| WO | WO-2022020242 A1 | 1/2022 |
| WO | WO-2022036018 A1 | 2/2022 |

OTHER PUBLICATIONS

Adedeji, et al. "Antiviral drugs specific for coronaviruses in preclinical development," Curr Opin Virol. Oct. 2014;8:45-53.

Albuquerque, et al. "MurineHepatitis Virus Strain 1 Produces a Clinically Relevant Model of Severe Acute Respiratory Syndrome in A/J Mice," Journal of Virology Oct. 2006, 80 (21) 10382-10394.

Altmann, et al "Dipeptide nitrile inhibitors of cathepsin K." Bioorg Med Chem Lett. May 1, 2006;16(9):2549-54. doi: 10.1016/j.bmcl. 2006.01.104. Epub Feb. 9, 2006.

Amblard, et al., "Synthesis and antiviral evaluation of novel peptidomimetics as norovirus protease inhibitors," Bioorganic & Medicinal Chemistry Letters, vol. 28, Issue 12, 2018, pp. 2165-2170.

Amin, Sk Abdul et al. "Protease targeted COVID-19 drug discovery and its challenges: Insight into viral main protease (Mpro) and papain-like protease (PLpro) inhibitors." *Bioorganic & medicinal chemistry* vol. 29 (2021): 115860. doi:10.1016/j.bmc.2020.115860.

Bai et al: "Peptidomimetic nitrile warheads as SARS-CoV-2 3CL protease inhibitors," RSC Med. Chem., 2021,12, 1722-1730 DOI:10. 1039/D1MD00247C.

Bandyopadhyay, et al. "Targeting biomolecules with reversible covalent chemistry," Current Opinion in Chemical Biology, vol. 34, 2016, pp. 110-116.

Bernassola, et al. "HECT-Type E3 Ubiquitin Ligases in Cancer," Trends Biochem Sci. Dec. 2019;44(12):1057-1075.

Berteottti, et al. "Predicting the Reactivity of Nitrile-Carrying Compounds with Cysteine: A Combined Computational and Experimental Study," ACS Med. Chem. Lett. 2014, 5, 5, 501-505.

Boras, et al "Discovery of a Novel Inhibitor of Coronavirus 3CL Protease as a Clinical Candidate for the Potential Treatment of COVID-19" bioRxiv 2020.09.12.293498; doi: https://doi.org/10. 1101/2020.09.12.293498.

Cai, et al. "4-(3-Trifluoromethylphenyl)-pyrimidine-2-carbonitrile as cathepsin S inhibitors: N3, not N1 is critically important," Bioorg Med Chem Lett . Aug. 1, 2010;20(15):4507-10.

Casimiro-Garcia, et al. "Identification of Cyanamide-Based Janus Kinase 3 (JAK3) Covalent Inhibitors," J. Med. Chem. 2018, 61, 23, 10665-10699.

Chang, Kyeong-Ok et al. "Antiviral Drug Discovery: Norovirus Proteases and Development of Inhibitors." *Viruses* vol. 11,2 197. Feb. 25, 2019, doi:10.3390/v11020197.

Chatterjee, et al. "Can Relative Binding Free Energy Predict Selectivity of Reversible Covalent Inhibitors?," J. Am. Chem. Soc. 2017, 139, 49, 17945-17952.

Chuck, et al., "Design, synthesis and crystallographic analysis of nitrile-based broad-spectrum peptidomimetic inhibitors for coronavirus 3C-like proteases," Eur J Med Chem. Jan. 2013;59:1-6.

Chuck, et al., "Supplementary Material: Design, synthesis and crystallographic analysis of nitrile-based broad-spectrum peptidomimetic inhibitors for coronavirus 3C-like proteases," Eur J Med Chem. Jan. 2013;59:1-6.

Cianni, et al. "Optimization strategy of single-digit nanomolar cross-class inhibitors of mammalian and protozoa cysteine proteases," Bioorganic Chemistry 101 (2020) June; pp. 1-20.

Coteron, et al. "Falcipain Inhibitors: Optimization Studies of the 2-Pyrimidinecarbonitrile Lead Series," J. Med. Chem. 2010, 53, 16, 6129-6152.

Dai, et al. "Design, Synthesis, and Biological Evaluation of Peptidomimetic Aldehydes as Broad-Spectrum Inhibitors against Enterovirus and SARS-CoV-2," Journal of Medicinal Chemistry, (Ahead of Print), 2021 (available online on Apr. 19, 2021), pp. A-O, ISSN: 0022-2623.

Dai, et al., "Structure-based design of antiviral drug candidates targeting the SARS-CoV-2 main protease," Science Jun. 19, 2020: vol. 368, Issue 6497, pp. 1331-1335.

Dai, Rongchen et al. "Cathepsin K: The Action in and Beyond Bone." *Frontiers in cell and developmental biology* vol. 8 433. Jun. 4, 2020, doi:10.3389/fcell.2020.00433.

Dai, Wenhao et al. "Supplementary Materials for: Structure-based design of antiviral drug candidates targeting the SARS-CoV-2 main protease." *Science* (New York, N. Y.) vol. 368,6497 (2020): 1331-1335. doi:10.1126/science.abb4489.

Damalanka, et al., "Structure-guided design, synthesis and evaluation of oxazolidinone-based inhibitors of norovirus 3CL protease," European Journal of Medicinal Chemistry, vol. 143, 2018, pp. 881-890.

De Cesco, et al. "Covalent inhibitors design and discovery," Eur J Med Chem . Sep. 29, 2017;138:96-114.

De Vries, et al: "Comparative study of a 3CLpro inhibitor and remdesivir against both major SARS-CoV-2 clades in human airway models" bioRxiv 2020.08.28.272880.

Doheny, et al. "Are Human Challenge Trials for COVID-19 Vaccine Worth the Risk?" Medscape, Medscape, Oct. 7, 2020, www.medscape.com/viewarticle/935377#:~:text=The%20trials%20could%20effectively%20deliver,or%20potentially%20the%20life%2C%20of.

Dong, et al. "Discovering drugs to treat coronavirus disease 2019 (COVID-19)," Drug Discov Ther. 2020;14(1):58-60.

Douangamath, Alice et al. "Crystallographic and electrophilic fragment screening of the SARS-CoV-2 main protease." *Nature communications* vol. 11,1 5047. Oct. 7, 2020, doi:10.1038/s41467-020-18709-w.

Dragovich et al "Structure-based design, synthesis, and biological evaluation of irreversible human rhinovirus 3C protease inhibitors. 2. Peptide structure-activity studies." J Med Chem. Jul. 16, 1998;41(15):2819-34. doi: 10.1021/jm9800696. PMID: 9667971.

Dragovich, et al. "Structure-Based Design, Synthesis, and Biological Evaluation of Irreversible Human Rhinovirus 3C Protease Inhibitors. 4. Incorporation of P1 Lactam Moieties as I-Glutamine Replacements," J. Med. Chem. 1999, 42, 7, 1213-1224.

Dragovich, P S et al. "Structure-based design, synthesis, and biological evaluation of irreversible human rhinovirus 3C protease inhibitors. 3. Structure-activity studies of ketomethylene-containing peptidomimetics." *Journal of medicinal chemistry* vol. 42,7 (1999): 1203-12. doi:10.1021/jm980537b.

Dragovich, Peter S et al. "Structure-based design, synthesis, and biological evaluation of irreversible human rhinovirus 3C protease inhibitors. 6. Structure-activity studies of orally bioavailable, 2-pyridone-containing peptidomimetics." Journal of medicinal chemistry vol. 45,8 (2002): 1607-23. doi:10.1021/jm010469k.

Dragovich, Peter S et al. "Structure-based design, synthesis, and biological evaluation of irreversible human rhinovirus 3C protease inhibitors. Part 7: structure-activity studies of bicyclic 2-pyridone-containing peptidomimetics." Bioorganic & medicinal chemistry letters vol. 12,5 (2002): 733-8. doi:10.1016/s0960-894x(02)00008-2.

Dragovich, Peter S. et al. "Structure-based design, synthesis, and biological evaluation of irreversible human rhinovirus 3C protease inhibitors. 1. Michael acceptor structure-activity studies." Journal of medicinal chemistry 41 15 (1998): 2806-18.

Dragovich, Peter S. et al. "Structure-Based Design, Synthesis, and Biological Evaluation of Irreversible Human Rhinovirus 3C Protease Inhibitors. 8. Pharmacological Optimization ofOrally Bioavailable 2-Pyridone-Containing Peptidomimetics." Journal of medicinal chemistry 46 21 (2003): 4572-85.

Eaton, et al. "Selective covalent targeting of GPX4 using masked nitrile-oxide electrophiles," Nature Chemical Biology vol. 16, pp. 497-506(2020).

(56) References Cited

OTHER PUBLICATIONS

Ehmke, et al., "Tuning and predicting biological affinity: arylnitriles as cysteine protease inhibitors," Org. Biomol. Chem., 2012, 10, 5764-5768.

Fischer, et al. "Inhibitors for Novel Coronavirus Protease Identified by Virtual Screening of 687 Million Compounds," Mar. 2020; Preprint. https://doi.org/10.26434/chemrxiv.11923239.v1.

Flanagan, et al., "Chemical and Computational Methods for the Characterization of Covalent Reactive Groups for the Prospective Design of Irreversible Inhibitors," Journal of Medicinal Chemistry, 2014, 57, 23, 10072-10079.

Fleming, et al. "Nitrile-Containing Pharmaceuticals: Efficacious Roles of the Nitrile Pharmacophore," J. Med. Chem. 2010, 53, 22, 7902-7917.

Frizler, et al "Development of nitrile-based peptidic inhibitors of cysteine cathepsins." Curr Top Med Chem. 2010;10(3):294-322. doi: 10.2174/156802610790725452.

Gehringer, et al., "Emerging and Re-Emerging Warheads for Targeted Covalent Inhibitors: Applications in Medicinal Chemistry and Chemical Biology," J. Med. Chem. Jun. 27, 2019;62(12):5673-5724.

Ghosh, Arun K., and Sandra Gemma. "Design of Cysteine Protease Inhibitors." Structure-Based Design of Drugs and Other Bioactive Molecules, May 29, 2015, pp. 131-142, 10.1002/9783527665211. ch5. Accessed Feb. 14, 2022.

Good, et al: "AT-527, a double prodrug of a guanosine nucleotide analog, is a potent inhibitor of SARS-CoV-2 in vitro and a promising oral antiviral for treatment of COVID-19," Antimicrob Agents Chemother 65:e02479-20.

Gurard-Levin, Zachary A et al. "Evaluation of SARS-CoV-2 3C-like protease inhibitors using self-assembled monolayer desorption ionization mass spectrometry." Antiviral research vol. 182 (2020): 104924. doi: 10.1016/j.antiviral.2020.104924.

Günther, Sebastian et al. "X-ray screening identifies active site and allosteric inhibitors of SARS-CoV-2 main protease." Science (New York, N.Y.) vol. 372,6542 (2021): 642-646. doi:10.1126/science.abf7945.

He, Jun et al. "Potential of coronavirus 3C-like protease inhibitors for the development of new anti-SARS-CoV-2 drugs: Insights from structures of protease and inhibitors." International journal of antimicrobial agents vol. 56,2 (2020): 106055. doi:10.1016/j.ijantimicag.2020.106055.

Hoffman, et al. "Discovery of Ketone-Based Covalent Inhibitors of Coronavirus 3CL Proteases for the Ptential Therapeutic Treatment of COVID-19," Journal of Medicinal Chemistry, vol. 63(21), 2020 (published on Oct. 15, 2020), pp. 12725-12747.

Hoffman, Robert L et al. "Discovery of Ketone-Based Covalent Inhibitors of Coronavirus 3CL Proteases for the Potential Therapeutic Treatment of COVID-19." Journal of medicinal chemistry vol. 63,21 (2020): 12725-12747. doi:10.1021/acs.jmedchem.0c01063.

Hou, et al. "SARS-COV-2 Reverse Genetics Reveals a Variable Infection Gradient in the Respiratory Tract," Cell . Jul. 23, 2020;182(2):429-446.e14.

Iketani, et al: "Lead compounds for the development of SARS-CoV-2 3CL protease inhibitors." Nat Commun. Apr. 1, 2021;12(1):2016. doi: 10.1038/s41467-021-22362-2. Erratum in: Nat Commun. May 5, 2021;12(1):2708.

Jacobs, et al. "Discovery, synthesis, and structure-based optimization of a Series of N-(tert-butyl)-2-(N-arylamido)-2-(pyridine-3-yl) acetamides (ML188) as potent noncovalent small molecule inhibitors of the severe acute respiratory syndrome coronavirus (SARS-CoV) 3CL protease," Journal of Medicinal Chemistry, 2013, vol. 56, No. 2, 534-546.

Jeon, et al. "Identification of Antiviral Drug Candidates against SARS-CoV-2 from FDA-Approved Drugs," Antimicrobial Agents and Chemotherapy Jun. 2020, 64 (7) e00819-20.

Jeong, Gi Uk et al. "Therapeutic Strategies Against COVID-19 and Structural Characterization of SARS-CoV-2: A Review." Frontiers in microbiology vol. 11 1723. Jul. 14, 2020, doi:10.3389/fmicb.2020.01723.

Johnson, et al. "Structure-based design of a parallel synthetic array directed toward the discovery of irreversible inhibitors of human rhinovirus 3C protease," J Med Chem. May 9, 2002;45(10):2016-23.

Keyser, et al. "Computation-Guided Rational Design of a Peptide Motif That Reacts with Cyanobenzothiazoles via Internal Cysteine-Lysine Relay," J. Org. Chem. 2018, 83, 14, 7467-7479.

Kim, et al., "Broad-spectrum antivirals against 3C or 3C-like proteases of picornaviruses, noroviruses, and coronaviruses," J Virol . Nov. 2012;86(21):11754-62.

Kim, et al., "Broad-spectrum inhibitors against 3CL-like proteases of feline coronaviruses and feline caliciviruses," J Virol . May 2015;89(9):4942-50.

Kim, et al., "Reversal of the Progression of Fatal Coronavirus Infection in Cats by a Broad-Spectrum Coronavirus Protease Inhibitor," PLoS Pathog . Mar. 30, 2016;12(3):e1005531.

Kitamura, et al., "Expedited Approach toward the Rational Design of Noncovalent SARS-CoV-2 Main Protease Inhibitors," J. Med. Chem., 2021, Publication Date:Apr. 23, 2021; https://doi.org/10.1021/acs.jmedchem.1c00509.

Kneller, et al "Direct Observation of Protonation State Modulation in SARS-CoV-2 Main Protease upon Inhibitor Binding with Neutron Crystallography." J Med Chem. Apr. 22, 2021;64(8):4991-5000. doi: 10.1021/acs.jmedchem.1c00058.

Konno, et al., "Design and synthesis of new tripeptide-type SARS-CoV 3CL protease inhibitors containing an electrophilic arylketone moiety," Bioorg Med Chem, Jan. 15, 2013;21(2):412-24.

Korkmaz, et al: "Lung Protection by Cathepsin C Inhibition: A New Hope for COVID-19 and ARDS?" J Med Chem. Nov. 25, 2020;63(22):13258-13265. doi: 10.1021/acs.jmedchem.0c00776. Epub Aug. 7, 2020.

Kruse, et al., "Therapeutic strategies in an outbreak scenario to treat the novel coronavirus originating in Wuhan, China," F1000Res. Jan. 31, 2020;9:72.

Kuhn, et al. "Prospective Evaluation of Free Energy Calculations for the Prioritization of Cathepsin L Inhibitors," J. Med. Chem. 2017, 60, 6, 2485-2497.

Lagoutte, et al. "Covalent inhibitors: an opportunity for rational target selectivity," Curr Opin Chem Biol . Aug. 2017;39:54-63.

Laine, et al. "Discovery of Novel Cyanamide-Based Inhibitors of Cathepsin C," ACS Med. Chem. Lett. 2011, 2, 2, 142-147.

Liu, et al. "Research and Development on Therapeutic Agents and Vaccines for COVID-19 and Related Human Coronavirus Diseases," ACS Cent. Sci. 2020, 6, 3, 315-331.

Liu, et al: "The development of Coronavirus 3C-Like protease (3CLpro) inhibitors from 2010 to 2020." Eur J Med Chem. Nov. 15, 2020;206:112711. doi: 10.1016/j.ejmech.2020.112711. Epub Aug. 6, 2020.

Lockbaum, et al "Pan-3C Protease Inhibitor Rupintrivir Binds SARS-CoV-2 Main Protease in a Unique Binding Mode. Biochemistry." Oct. 5, 2021;60(39):2925-2931. doi: 10.1021/acs.biochem.1c00414. Epub Sep. 10, 2021.

Lonsdale, et al. "Structure-based design of targeted covalent inhibitors," Chem. Soc. Rev., 2018, 47, 3816-3830.

Ma, et al., "Boceprevir, GC-376, and calpain inhibitors II, XII inhibit SARS-CoV-2 viral replication by targeting the viral main protease," Cell Res. Aug. 2020; 30(8): 678-692.

MacFaul, et al. "A simple in vitro assay for assessing the reactivity of nitrile containing compounds," Bioorganic & Medicinal Chemistry Letters, vol. 19, Issue 4, 2009, pp. 1136-1138.

Martin, et al., "Characterising covalent warhead reactivity," Bioorganic & Medicinal Chemistry, May 15, 2019;27(10):2066-2074.

Masand, et al. "Structure features of peptide-type SARS-CoV main protease inhibitors: Quantitative structure activity relationship study," Chemometrics and Intelligent Laboratory Systems, vol. 206, 104172, 2020 (available online on Oct. 3, 2020).

Montagutelli, et al. "The B1.351 and P.1 variants extend SARS-CoV-2 host range to mice," bioRxiv 2021.03.18.436013.

(56) References Cited

OTHER PUBLICATIONS

Mott, et al., "Identification and optimization of inhibitors of Trypanosomal cysteine proteases: cruzain, rhodesain, and TbCatB," Journal of Medicinal Chemistry, Jan. 14, 2010;53(1):52-60.

Namoto, et al. "Structure-based design and synthesis of macrocyclic human rhinovirus 3C protease inhibitors," Bioorg Med Chem Lett. Mar. 1, 2018;28(5):906-909.

Oballa, et al., "A generally applicable method for assessing the electrophilicity and reactivity of diverse nitrile-containing compounds," Bioorganic & Medicinal Chemistry Letters, vol. 17, Issue 4, 2007, pp. 998-1002.

Ono, Yasuko et al. "Calpain research for drug discovery: challenges and potential." *Nature reviews. Drug discovery* vol. 15,12 (2016): 854-876. doi:10.1038/nrd.2016.212.

Owen et al: "An Oral SARS-CoV-2 Mpro Inhibitor Clinical Candidate for the Treatment of COVID-19," medRxiv 2021.07.28. 21261232; DOI: https://doi.org/10.1101/2021.07.28.21261232.

Paasche, et al. "Mechanistic Insights into SARS Coronavirus Main Protease by Computational Chemistry Methods," 2012: n. pag. Print. Doctoral Thesis, University of Würzburg. https://d-nb.info/1037687825/34.

Patick, et al. "Protease Inhibitors as Antiviral Agents," Clin Microbiol Rev. Oct. 1998; 11(4): 614-627.

Pillaiyar, et al., "An Overview of Severe Acute Respiratory Syndrome-Coronavirus (SARS-CoV) 3CL Protease Inhibitors: Peptidomimetics and Small Molecule Chemotherapy," J. Med. Chem. 2016, 59, 14, 6595-6628.

Prior, et al., "Design, synthesis, and bioevaluation of viral 3C and 3C-like protease inhibitors," Bioorganic & Medicinal Chemistry Letters, vol. 23, Issue 23, 2013, pp. 6317-6320.

Qiao et al: "SARS-CoV-2 M pro inhibitors with antiviral activity in a transgenic mouse model," Science. Mar. 26, 2021;371(6536):1374-1378. DOI: 10.1126/science.abf1611. Epub Feb. 18, 2021.

Qin, et al "Acrylamide Fragment Inhibitors that Induce Unprecedented Conformational Distortions in Enterovirus 71 3C and SARS-CoV-2 Main Protease" bioRxiv 2020.11.06.370916; doi: <https://doi.org/10.1101/2020.11.06.370916>.

Rathnayake, et al "Structure-Guided Optimization of Dipeptidyl Inhibitors of Norovirus 3CL Protease." J Med Chem. Oct. 22, 2020;63(20):11945-11963. doi: 10.1021/acs.jmedchem.0c01252.

Rathnayake, et al., "3C-like protease inhibitors block coronavirus replication in vitro and improve survival in MERS-CoV-infected mice," Science Translational Medicine, Aug. 19, 2020: vol. 12, Issue 557, eabc5332.

Ray, et al. "New Electrophiles and Strategies for Mechanism-Based and Targeted Covalent Inhibitor Design," Biochemistry 2019, 58, 52, 5234-5244.

Rut Wioletta et al "Substrate specificity profiling of SARS-CoV-2 Mpro protease provides basis for anti-COVID-19 drug design" Marcin Drag bioRxiv 2020.03.07.981928; doi: https://doi.org/10.1101/2020.03.07.981928.

Sacco, Michael Dominic et al. "Structure and inhibition of the SARS-CoV-2 main protease reveals strategy for developing dual inhibitors against Mpro and cathepsin L." *bioRxiv : the preprint server for biology* 2020.07.27.223727. Jul. 27, 2020, doi:10.1101/2020.07.27.223727.

Santos, et al., "Experimental study and computational modelling of cruzain cysteine protease inhibition by dipeptidyl nitriles," Phys. Chem. Chem. Phys., 2018, 20, 24317-24328.

Santos, et al., "Michael acceptors as cysteine protease inhibitors," Mini Rev Med Chem . Oct. 2007;7(10):1040-50.

Schade, et al. "Highly Selective Sub-Nanomolar Cathepsin S Inhibitors by Merging Fragment Binders with Nitrile Inhibitors," J. Med. Chem. 2020, 63, 20, 11801-11808.

Schnute, et al. "Aminopyrazole Carboxamide Bruton's Tyrosine Kinase Inhibitors. Irreversible to Reversible Covalent Reactive Group Tuning," ACS Med. Chem. Lett. 2019, 10, 1, 80-85.

Schuller, Marion et al. "Fragment binding to the Nsp3 macrodomain of SARS-CoV-2 identified through crystallographic screening and computational docking." *Science advances* vol. 7,16 eabf8711. Apr. 14, 2021, doi:10.1126/sciadv.abf8711.

Serafimova, et al. (2013). Reversible targeting of noncatalytic cysteines with chemically tuned electrophiles. UCSF. ProQuest ID: Serafimova_ucsf_0034D_10695.REDACTED. Merritt ID: ark:/13030/m5x36bhx. Retrieved from https://escholarship.org/uc/item/0cj6m628.

Silva, et al. "A comparative study of warheads for design of cysteine protease inhibitors," Bioorg Med Chem Lett. Nov. 15, 2017;27(22):5031-5035.

Simplicio, et al., "Prodrugs for Amines," Molecules (Basel, Switzerland), 13(3), 519-547.

Sinha, et al. "Electrophilicity of pyridazine-3-carbonitrile, pyrimidine-2-carbonitrile, and pyridine-carbonitrile derivatives: a chemical model to describe the formation of thiazoline derivatives in human liver microsomes," Chem Res Toxicol. Dec. 15, 2014;27(12):2052-61.

St. John, et al. "Targeting zoonotic viruses: Structure-based inhibition of the 3C-like protease from bat coronavirus HKU4—The likely reservoir host to the human coronavirus that causes Middle East Respiratory Syndrome (MERS)," Bioorganic & Medicinal Chemistry, vol. 23, No. 17, 6036-6048.

Steinhauer, et al., "Rapid evolution of RNA viruses," Annu Rev Microbiol. 1987;41:409-33.

Steuten, et al. "Challenges for Targeting SARS-CoV-2 Proteases as a Therapeutic Strategy for COVID-19," ACS Infect. Dis. 2021, Publication date: Feb. 11, 2021; https://doi.org/10.1021/acsinfecdis.0c00815.

STN Registry Database Entry for 1831065-26-9 entered STN Dec. 16, 2015.

STN Registry Database Entry for 2248095-92-1 entered STN Nov. 13, 2018.

STN Registry Database Entry for 2628280-40-8 entered STN Apr. 7, 2021.

Thanigaimalai Pillaiyar et al: "Design, synthesis, and biological evaluation of novel dipeptide-type SARS-CoV 3CL protease inhibitors: Structure-activity relationships," European Journal of Medicinal Chemistry, Elsevier, Amsterdam, NL, vol. 65, May 20, 2013 (May 20, 2013), pp. 436-447, DOI: 10.1016/J.EJMECH.2013.05.005.

Thanigaimalai, et al. "Development of potent dipeptide-type SARS-CoV 3CL protease inhibitors with novel P3 scaffolds: Design, synthesis, biological evaluation, and docking studies," European Journal of Medicinal Chemistry, vol. 68, 2013, pp. 372-384, ISSN: 0223-5234.

Tomar, et al. "Understanding the determinants for substrate recognition, regulation of enzymatic activity and the development of broad-spectrum inhibitors of coronavirus 3- chymotrypsin-like proteases," (2015). Open Access Dissertations. 1322. https://docs.lib.purdue.edu/open_access_dissertations/1322.

Totura, et al. "Broad-spectrum coronavirus antiviral drug discovery," Expert Opin Drug Discov. Apr. 2019;14(4):397-412.

Vandyck, et al: "ALG-097111, a potent and selective SARS-CoV-2 3-chymotrypsin-like cysteine protease inhibitor exhibits in vivo efficacy in a Syrian Hamster model." Biochem Biophys Res Commun. May 28, 2021;555:134-139. doi: 10.1016/j.bbrc.2021.03.096. Epub Mar. 26, 2021.

Verma, Sonia et al. "Cysteine Proteases: Modes of Activation and Future Prospects as Pharmacological Targets." *Frontiers in pharmacology* vol. 7 107. Apr. 25, 2016, doi:10.3389/fphar.2016.00107.

Vuong et al: "Improved Synthesis of a Cyclic Glutamine Analogue Used in Antiviral Agents Targeting 3C and 3CL Proteases Including SARS-CoV-2 MPRO," The Journal of Organic Chemistry 2021 86 (18), 13104-13110 DOI: 10.1021/acs.joc.1c01299.

Vuong, et al., "Feline coronavirus drug inhibits the main protease of SARS-CoV-2 and blocks virus replication," Nat Commun . Aug. 27, 2020;11(1):4282.

Wang, et al "Comprehensive Insights into the Catalytic Mechanism of Middle East Respiratory Syndrome 3C-Like Protease and Severe Acute Respiratory Syndrome 3C-Like Protease." ACS Catal. 2020; 10:5871-5890. doi: 10.1021/acscatal.0c00110. Epub Apr. 28, 2020.

(56) References Cited

OTHER PUBLICATIONS

Wang, et al., "Covalent binding design strategy: A prospective method for discovery of potent targeted anticancer agents," European Journal of Medicinal Chemistry, vol. 142, 2017, pp. 493-505.
Wang, et al., "Inhibition of enterovirus 71 replication by an ?-hydroxynitrile derivative NK-1.9k," Antiviral Res . May 2017;141:91-100.
Wang, et al., "Recent progress in the discovery of inhibitors targeting coronavirus proteases," Virologica Sinica, Springer, DE, vol. 31, No. 1, 24-30.
Westberg et al: "Rational design of a new class of protease inhibitors for the potential treatment of coronavirus diseases," bioRxiv 2020. 09.15.275891; DOI: https://doi.org/10.1101/2020.09.15.275891.
White, et al., "Plitidepsin has potent preclinical efficacy against SARS-CoV-2 by targeting the host protein eEF1A," Science Feb. 26, 2021: vol. 371, Issue 6532, pp. 926-931.
Yang, Syaulan et al. "Synthesis, crystal structure, structure-activity relationships, and antiviral activity of a potent SARS coronavirus 3CL protease inhibitor." *Journal of medicinal chemistry* vol. 49,16 (2006): 4971-80. doi:10.1021/jm0603926.
Ye, et al., "Structural Basis for Inhibiting Porcine Epidemic Diarrhea Virus Replication with the 3C-Like Protease Inhibitor GC376," Viruses. Feb. 21, 2020;12(2):240.
Yuto Unoh et al "Discovery of S-217622, a Non-Covalent Oral SARS-CoV-2 3CL Protease Inhibitor Clinical Candidate for Treating COVID-19", bioRxiv 2022.01.26.477782; doi: https://doi.org/10.1101/2022.01.26.477782.
Zaidman, et al. "An automatic pipeline for the design of irreversible derivatives identifies a potent SARS-CoV-2 Mpro inhibitor," bioRxiv 2020.09.21.299776.
Zhai, et al., "Cyanohydrin as an Anchoring Group for Potent and Selective Inhibitors of Enterovirus 71 3C Protease," J. Med. Chem. 2015, 58, 23, 9414-9420.
Zhang, Chun-Hui et al. "Potent Noncovalent Inhibitors of the Main Protease of SARS-CoV-2 from Molecular Sculpting of the Drug Perampanel Guided by Free Energy Perturbation Calculations." ACS central science vol. 7,3 (2021): 467-475. doi:10.1021/acscentsci.1c00039.
Zhang, et al Supplementary Materials for: Crystal structure of SARS-CoV-2 main protease provides a basis for design of improved ?-ketoamide inhibitors. Science. 2020;368(6489):409-412. doi:10.1126/science.abb3405.
Zhang, Linlin et al. "Crystal structure of SARS-CoV-2 main protease provides a basis for design of improved ?-ketoamide inhibitors." Science (New York, N.Y.) vol. 368,6489 (2020): 409-412. doi:10.1126/science.abb3405.
Zhao, et al. "Progress with covalent small-molecule kinase inhibitors," vol. 23, Issue 3, 2018, pp. 727-735, ISSN 1359-6446.

INHIBITORS OF CYSTEINE PROTEASES AND METHODS OF USE THEREOF

CROSS REFERENCE TO RELATED APPLICATIONS

This application is a continuation of U.S. Ser. No. 17/525,514, filed Nov. 12, 2021, which is a continuation of U.S. Ser. No. 17/322,221, filed May 17, 2021, which claims the benefit of, and priority to, U.S. Ser. No. 63/036,866 filed Jun. 9, 2020; U.S. Ser. No. 63/039,297 filed Jun. 15, 2020; U.S. Ser. No. 63/067,669 filed Aug. 19, 2020; U.S. Ser. No. 63/091,630 filed Oct. 14, 2020; U.S. Ser. No. 63/129,018 filed Dec. 22, 2020; U.S. Ser. No. 63/171,675 filed Apr. 7, 2021; U.S. Ser. No. 63/172,478 filed Apr. 8, 2021; U.S. Ser. No. 63/173,146 filed Apr. 9, 2021; and U.S. Ser. No. 63/179,128, filed Apr. 23, 2021; the contents of each of which is incorporated herein by reference in its entirety.

BACKGROUND

The Coronaviridae family of viruses are enveloped, single-stranded, positive-sense RNA viruses and include 141 species that are classified into four genera according to their phylogenetic relationships: α-, β-, γ-, and δ-coronavirus. Coronaviruses (CoVs) are zoonotic viruses that infect a variety of animals from whales to birds, bats, cats, and humans. Typically, CoV infection results in mild to moderate respiratory tract infections; however, some CoV species are extremely virulent and can result in widespread fatality. Severe acute respiratory syndrome coronavirus (SARS-CoV) is a human CoV that was responsible for the first pandemic of the $21^{st}$ century, infecting over 8,000 people with a 10% mortality rate. Middle East respiratory syndrome coronavirus (MERS-CoV) was identified in November 2012 and had since infected over 1,600 people in 26 countries with 36% mortality rate. More recently, COVID-19 (SARS CoV2) coronaviruses have raised a global pandemic since they had been first identified in China in late 2019. Therefore, it is important to identify coronavirus drug targets that can be utilized for the development of broad-spectrum anti-coronaviral therapeutics to combat infections of existing and emerging coronaviruses.

All CoVs express a >800 kDa replicase polyprotein that contains either two or three cysteine proteases, the papain-like protease(s) (PLPpro, or PLP1 and PLP2) and the 3C-like protease (3CLpro, nsp5, or Mpro). These proteases process the CoV replicase polyprotein by cleaving it into 16 non-structural proteins, which are responsible for a variety of aspects of CoV replication. The CoV 3CLpro is responsible for processing 11 cleavage sites of within the replicase polyprotein and is essential for CoV replication, making it a highly valuable target for therapeutic development. The overall active site architecture and substrate recognition pockets are structurally conserved across CoV 3CLpros, increasing its attractiveness as a target for the development of broad-spectrum anti-CoV therapeutics. Moreover, high sequence conservation in the vicinity of active site among CoV 3CLpros from different coronavirus subclasses make them an excellent target for the development of broad-spectrum therapeutics for coronavirus infections. Accordingly, the development of CoV 3CLpro inhibitors is a promising path for the treatment of respiratory tract infections and related diseases.

Numerous studies on targeting the immediate zoonotic reservoirs of coronaviruses with small molecule inhibitors have helped inform structure-based design strategies aimed at creating molecular scaffolds that may aid in the development of therapeutic against coronaviral infection; however, small molecule antiviral agents nor effective commercially available broad-spectrum therapeutics have not yet been identified. There is a critical need for the development of broad-spectrum CoV therapeutics to overcome the challenges of traditional anti-CoV therapeutic development, as broad-spectrum therapeutics can be rapidly implemented upon zoonotic disease outbreak.

SUMMARY

The disclosure is directed to, in part, viral protease inhibitors. Also provided are pharmaceutical compositions comprising at least one disclosed compound and a pharmaceutically acceptable carrier.

In an embodiment, provided herein is a viral protease inhibitor, comprising a warhead covalently bound to a 3C or 3CL protease inhibitor, wherein the antiviral compound covalently binds to Cys on the protease, and wherein the antiviral compound is active against one or more viruses.

Also provided herein are compounds represented by Formula II:

Formula II $$\underset{R^{1b}}{\overset{R^2}{\diagdown}}\underset{R^{1a}}{\overset{O}{\underset{\|}{C}}}\underset{R^{3b}}{\overset{R^{3a}}{\diagup}}N$$

$R^{3a}$ is selected from and 4-10 membered heterocycle, wherein the heterocycle may optionally be substituted by one, two or three substituents each selected from the group consisting of hydroxyl, $C_1$-$C_8$alkoxy, oxo and a warhead A; $R^{3b}$ is selected from hydrogen and $C_1$-$C_8$alkyl; wherein $R^{3a}$ and $R^{3b}$ may be joined together to form, together with the carbon to which they are attached, a 4-10 membered heterocycle, wherein the heterocycle may optionally be substituted by one, two or three substituents each selected from $C_6$-$C_{14}$aryl and a warhead A; $R^{1a}$ is selected from the group consisting of hydrogen, $C_1$-$C_8$alkyl, $C_1$-$C_8$heteroalkyl, —($C_1$-$C_8$alkyl)-$R^1$, —($C_1$-$C_8$alkyl)-CN, $C_3$-$C_{10}$cycloalkyl, $C_6$-$C_{14}$aryl, 4-10 membered heterocycle and 5-10 membered heteroaryl; $R^{1b}$ is selected from hydrogen and $C_1$-$C_8$alkyl; or $R^{1a}$ and $R^{1b}$ may be joined together to form, together with the carbon to which they are attached, a 4-10 membered heterocycle having a ring nitrogen, $NR^G$, or a $C_3$-$C_{10}$cycloalkyl; $R^1$ is selected from the group consisting of $C_1$-$C_8$alkyl, $C_2$-$C_{10}$alkenyl, $C_2$-$C_{10}$alkynyl, $C_3$-$C_{10}$cycloalkyl, $C_6$-$C_{14}$aryl, 5-10 membered heteroaryl and 4-10 membered heterocycle, wherein $R^1$ may optionally be substituted by one, two, or three substituents each selected from $R^A$; $R^A$ is independently selected for each occurrence from the group consisting of halogen, cyano, hydroxyl, oxo, $SF_5$, —$CH_2CF_3$, —$CF_3$, —O—$CF_3$, —O—$CHF_2$, —S—$CH_3$, —S(O)$_2$—CH$_3$, —NH$_2$, —O-phenyl, —O—(C$_1$-C$_8$alkyl)-phenyl, —NHC(O)R$^B$, —NHC(O)OR$^B$, —NHC(O)O—(C$_1$-C$_8$alkyl)-R$^B$, —N(R$^y$)$_2$, —N(R$^y$)(C$_1$-C$_8$alkyl)C(O)O—phenyl, —N(R$^y$)(C$_1$-C$_8$alkyl)C(O)N(R$^y$)$_2$, —C(O)—OC(CH$_3$)$_3$, C$_1$-C$_8$alkyl, C$_2$-C$_{10}$alkenyl, C$_2$-C$_{10}$alkynyl, C$_1$-C$_8$heteroalkyl, C$_1$-C$_8$alkoxy, C$_3$-C$_{10}$cycloalkyl, —(C$_1$-C$_8$alkyl)-(C$_3$-C$_{10}$cycloalkyl), (C$_1$-C$_8$alkyl)-(C$_6$-C$_{14}$aryl), —(C$_1$-C$_8$alkyl)-(5-10 membered heteroaryl), C$_6$-C$_{14}$aryl, 5-10 membered heteroaryl and 4-10 membered heterocyclyl, wherein the R$^B$, alkyl, heterocyclyl, heteroaryl, or aryl may optionally be substituted by one, two or three substituents of halogen, C$_1$-C$_8$alkyl, C$_1$-C$_8$alkoxy, SF$_5$, —NH$_2$, hydroxyl or oxo; R$^2$ is selected from the group consisting of —NHC(O)R$^B$, —NHC(O)N(R$^B$)$_2$, —NHC(O)C(R$^C$)$_2$R$^B$, —NHS(O)$_2$R$^B$, —O—(C$_1$-C$_5$alkyl)-(C$_3$-C$_{10}$cycloalkyl), 4-10 membered heterocycle, C$_6$-C$_{14}$aryl and 5-10 membered heteroaryl bound through the carbon or nitrogen atom, wherein R$^B$ or R$^2$ may optionally be substituted by one, two, or three substituents each selected from R$^x$; or R$^{1a}$ and R$^2$ may be joined together to form, together with the carbon to which they are attached, a 4-10 membered mono or bicyclic heterocycle having a ring nitrogen NR$^G$, or a C$_3$-C$_{10}$cycloalkyl, wherein the cycloalkyl or heterocycle may optionally be substituted by one, two or three substituents on a free carbon each selected from R$^A$; R$^3$ is selected from 5-10 membered heteroaryl and 4-10 membered heterocycle, wherein R$^3$ may optionally be substituted by one, two, or three substituents each selected from R$^A$; R$^B$ is independently selected, for each occurrence, from the group consisting of C$_1$-C$_8$alkyl, C$_2$-C$_{10}$alkenyl, C$_2$-C$_{10}$alkynyl, C$_3$-C$_{16}$cycloalkyl, fluorenylmethyloxy, C$_6$-C$_{14}$aryl, 5-10 membered heteroaryl and 4-10 membered heterocycle; R$^C$ is independently selected, for each occurrence, from hydrogen, halogen and C$_1$-C$_8$alkyl; R$^x$ is independently selected, for each occurrence, from the group consisting of halogen, hydroxyl, oxo, CF$_3$, SF$_5$, cyano, —O—(R$^{xx}$)—OCH$_3$, —OCHF$_2$, —OCF$_3$, —O—(C$_1$-C$_8$alkyl), —C(O)O(CH$_3$), —N(R$^y$)$_2$, —N(R$^y$)C(O)R$^y$, —N(R$^y$)(C$_1$-C$_8$alkyl)C(O)N(R$^y$)$_2$, —N(R$^y$)(C$_1$-C$_8$alkyl)C(O)OH, —(C$_1$-C$_8$alkyl)-(C$_3$-C$_{10}$cycloalkyl), C$_1$-C$_8$alkyl, C$_1$-C$_8$alkoxy, C$_3$-C$_{10}$cycloalkyl, C$_6$-C$_{14}$aryl, —O—C$_6$-C$_{14}$aryl, 5-10 membered heteroaryl and 4-10 membered heterocycle; wherein two geminal C$_1$-C$_8$alkyl groups, together with the carbon to which they are attached, may be joined together to form a C$_3$-C$_6$cycloalkyl optionally substituted by one, two or three substituents each selected from halogen, hydroxyl or oxo; and wherein the alkyl, aryl, heterocycle or heteroaryl may optionally be substituted by one or more substituents each selected from oxo, halogen and C$_1$-C$_8$alkyl; R$^G$ is selected from the group consisting of hydrogen, C$_{1-6}$alkyl optionally substituted by one, two or three R$^{gg}$, —C(=O)—C$_{1-6}$alkyl optionally substituted by one, two or three R$^{hh}$, —C(=O)—C$_{3-6}$cycloalkyl, —C(O)—(C$_2$-C$_{10}$alkenyl)-(C$_6$-C$_{14}$aryl), —C(O)-(5-10 membered heteroaryl), —C(O)-(4-10 membered heterocyclyl), and —C(O)-(4-10 membered heterocyclyloxy); wherein the aryl, heterocyclyl, or heteroaryl may optionally be substituted by one, two or three R$^{jj}$; R$^{gg}$ is independently selected for each occurrence from the group consisting of —C(=O), halo, cyano, —NR$^m$R$^m$, and —NH(C=O)R$^m$; R$^{hh}$ is independently selected for each occurrence from the group consisting of halo, cyano, —NR$^m$R$^m$, —NR$^m$(C=O)R$^m$, phenyl, cycloalkyl, heterocyclyl and C$_1$-C$_6$alkoxy; R$^{jj}$ is independently selected for each occurrence from the group consisting of halo, oxo, hydroxyl, cyano, C$_1$-C$_6$alkyl, C$_1$-C$_6$haloalkyl, C$_1$-C$_6$alkoxy, C$_{3-6}$cycloalkyl, SF$_5$, and NH$_2$; R$^m$ is independently selected for each occurrence from the group consisting of hydrogen, C$_{1-3}$alkyl, phenyl, —S(O)$_2$—CH$_3$, C$_{3-6}$cycloalkyl, and 5-6 membered heteroaryl; wherein C$_{1-3}$alkyl, phenyl, and C$_{3-6}$cycloalkyl may optionally be substituted by one, two or three halo; R$^{xx}$ is —(OCH$_2$CH$_2$)$_{nn}$—, wherein nn is selected from 1, 2, 3, 4, 5 and 6; R$^y$ is independently selected, for each occurrence, from the group consisting of hydrogen, C$_1$-C$_8$alkyl, C$_1$-C$_8$heteroalkyl, —CF$_3$, —CH$_2$CF$_3$, C$_1$-C$_8$alkoxy, —(C$_1$-C$_8$alkoxy)-(5-10 membered aryl), C$_3$-C$_6$cycloalkyl and —(C$_1$-C$_8$alkyl)COOH; A is a warhead; X is selected from the group consisting of C(R$^{xy}$) and N, wherein R$^{xy}$ is selected from the group consisting of H, D, —OH, —NH$_2$, halogen, C$_1$-C$_8$alkyl, C$_1$-C$_8$ haloalkyl, and C$_1$-C$_8$alkoxy; and pharmaceutically acceptable salts, stereoisomers, esters, and prodrugs thereof.

In some embodiments, provided herein are compounds represented by Formula II-A:

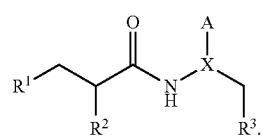

Formula II-A

In some embodiments, provided herein are compounds represented by Formula II-B:

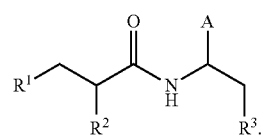

Formula II-B

In some embodiments, provided herein are compounds represented by Formula II-C:

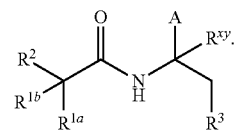

Formula II-C

In some embodiments, provided herein are compounds represented by Formula II-D-A or Formula II-D-B:

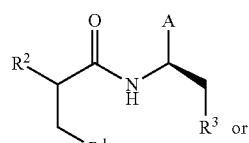

(Formula II-D-A)

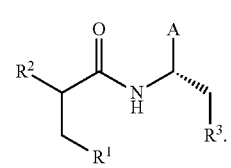

(Formula II-D-B)

In some embodiments, provided herein are compounds represented by Formula II-E-A or Formula II-E-B:

(Formula II-E-A)

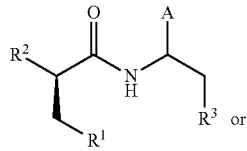

or (Formula II-E-B)

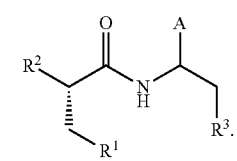

In some embodiments, provided herein are compounds represented by Formula II-F:

Formula II-F

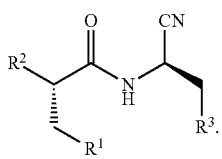

In some embodiments, provided herein are compounds represented by Formula II-G:

Formula II-G

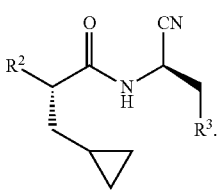

In some embodiments, provided herein are compounds represented by Formula II-H-A or Formula II-H-B:

(Formula II-D-I)

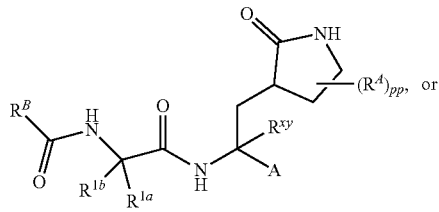

or (Formula II-D-II)

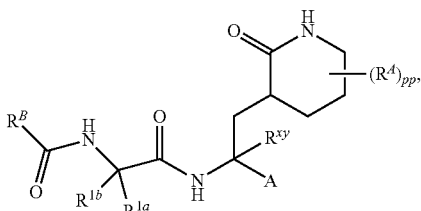

wherein pp is selected from 0, 1, 2, and 3.

In some embodiments, provided herein are compounds represented by Formula II-E:

(Formula II-E)

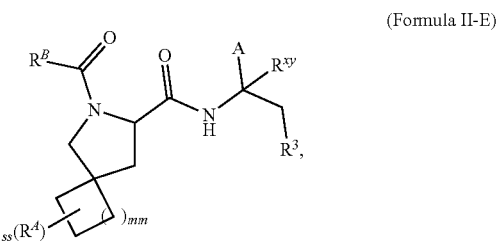

wherein ss is selected from 0, 1, 2, and 3, and mm is selected from 1, 2, and 3.

In some embodiments, provided herein are compounds represented by Formula II-I:

Formula II-I

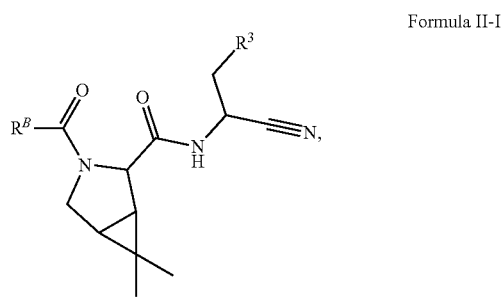

wherein: $R^3$ is

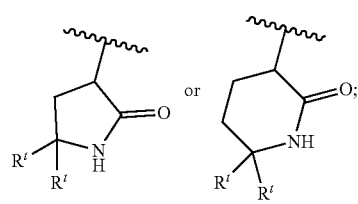

$R^t$ is independently, for each occurrence, H or methyl; or each $R^t$ may be taken, together with the carbon to which they are attached, to form a cyclopropyl; $R^B$ is selected from the group consisting of: a 9-10 membered bicyclic heteroaryl having one ring nitrogen, $C_1$-$C_6$alkyl, and $C_2$-$C_3$alkenyl; wherein $R^B$ is optionally substituted by one, two or three substituents each independently selected from the group consisting of halogen, $C_1$-$C_3$alkoxy, $NHR^m$, and phenyl (optionally substituted by one or two halogens); $R^m$ is $C_1$-$C_3$alkyl or —C(O)—$C_{1-3}$alkyl, wherein each $C_1$-$C_3$alkyl is independently optionally substituted by one, two or three halogens; or a pharmaceutically acceptable salt thereof.

In certain embodiments, provided herein are conjugates represented by Formula III:

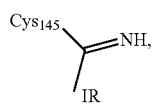

Formula III wherein $Cys_{145}$ is cysteine at position 145 or equivalent active site cysteine on a CL or 3CL protease; IR is a viral protease inhibitor; and wherein the compound that forms the conjugate comprises a —CN warhead.

DETAILED DESCRIPTION

The features and other details of the disclosure will now be more particularly described. Before further description of the present disclosure, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

The term "treating" includes any effect, e.g., lessening, reducing, modulating, or eliminating, that results in the improvement of the condition, disease, disorder and the like, including a reduction of viral shedding in asymptomatic individuals and prophylaxis of exposed individuals, independent of symptoms.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_1$-$C_3$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_1$-$C_5$alkenyl, $C_2$-$C_6$alkenyl, and $C_3$-$C_4$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_1$-$C_5$alkoxy, $C_1$-$C_6$alkoxy, and $C_2$-$C_6$alkoxy, respectively. Exemplary alkoxy groups include, but are not limited to methoxy, ethoxy, isopropoxy, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_1$-$C_5$alkoxy, $C_1$-$C_6$alkoxy, and $C_2$-$C_6$alkoxy, respectively. Exemplary alkoxy groups include, but are not limited to methoxy, ethoxy, isopropoxy, etc.

The term "alkoxyalkyl" as used herein refers to a straight or branched alkyl group attached to oxygen, attached to a second straight or branched alkyl group (alkyl-O-alkyl-). Exemplary alkoxyalkyl groups include, but are not limited to, alkoxyalkyl groups in which each of the alkyl groups independently contains 1-6 carbon atoms, referred to herein as $C_{1-6}$alkoxy-$C_{1-6}$alkyl. Exemplary alkoxyalkyl groups include, but are not limited to methoxymethyl, 2-methoxyethyl, 1-methoxyethyl, 2-methoxypropyl, ethoxymethyl, 2-isopropoxyethyl etc.

The term "alkyoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$ alkoxycarbonyl. Exemplary alkoxycarbonyl groups include, but are not limited to, methoxycarbonyl, ethoxycarbonyl, t-butoxycarbonyl, etc.

The term "alkenyloxy" used herein refers to a straight or branched alkenyl group attached to oxygen (alkenyl-O—). Exemplary alkenyloxy groups include, but are not limited to, groups with an alkenyl group of 3-6 carbon atoms, referred to herein as $C_{3-6}$alkenyloxy. Exemplary "alkenyloxy" groups include, but are not limited to allyloxy, butenyloxy, etc.

The term "alkynyloxy" used herein refers to a straight or branched alkynyl group attached to oxygen (alkynyl-O). Exemplary alkynyloxy groups include, but are not limited to, groups with an alkynyl group of 3-6 carbon atoms, referred to herein as $C_{3-6}$alkynyloxy. Exemplary alkynyloxy groups include, but are not limited to, propynyloxy, butynyloxy, etc.

The term "aryl" refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl.

Examples of representative substituted aryls include the following:

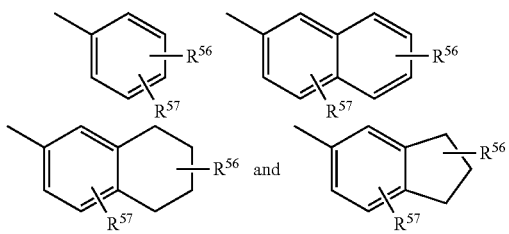

wherein one of $R^{56}$ and $R^{57}$ may be hydrogen and at least one of $R^{56}$ and $R^{57}$ is each independently selected from halogen, $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group consisting of N, O, and S. $R^{60}$ and $R^{61}$ are independently hydrogen, $C_1$-$C_8$ alkyl, $C_1$-$C_4$haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

The term "carbonyl" as used herein refers to the radical —C(O)—.

The term "cyano" as used herein refers to the radical —CN.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc.

The terms "cycloalkyl" or a "carbocyclic group" as used herein refers to a saturated or partially unsaturated hydrocarbon group of, for example, 3-6, or 4-6 carbons, referred to herein as $C_3$-$C_{10}$cycloalkyl, $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The term "hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

The terms "heteroaryl" or "heteroaromatic group" as used herein refers to an aromatic 5-10 membered ring system containing one or more heteroatoms, for example one to three heteroatoms, such as nitrogen, oxygen, and sulfur. The term may also be used to refer to a 5-7 membered monocyclic heteroaryl or an 8-10 membered bicyclic heteroaryl. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

Examples of representative heteroaryls include the following:

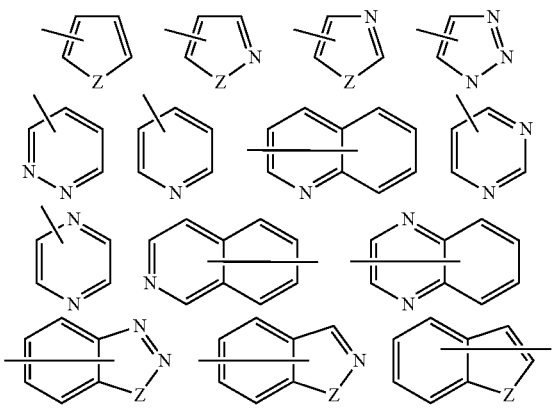

wherein each Z is selected from carbonyl, N, $NR^{65}$, O, and S; and $R^{65}$ is each independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

The terms "heterocyclyl," "heterocycle," or "heterocyclic group" are art-recognized and refer to saturated or partially unsaturated 4-10 membered ring structures, whose ring structures include one to three heteroatoms, such as nitrogen, oxygen, and sulfur. Where possible, heterocyclyl rings may be linked to the adjacent radical through carbon or nitrogen. The term may also be used to refer to 4-10 membered saturated or partially unsaturated ring structures that are bridged, fused or spirocyclic ring structures, whose ring structures include one to three heteroatoms, such as nitrogen, oxygen, and sulfur. Examples of heterocyclyl groups include, but are not limited to, pyrrolidine, piperidine, morpholine, thiomorpholine, piperazine, oxetane, azetidine, tetrahydrofuran or dihydrofuran etc. In some embodiments, the heterocycle is a spiro heterocycle (e.g. 2,8-diazaspiro[4.5]decane). In some embodiments, the heterocycle is a bridged heterocycle (e.g. octahydro-1H-4,7-methanoisoindole). "Spiro heterocyclyl," or "spiro heterocycle" refers to a polycyclic heterocyclyl with rings connected through one common atom (called a spiro atom), wherein the rings have one or more heteroatoms selected from the group consisting of N, O, and $S(O)_m$ (wherein m is an integer of 0 to 2) as ring atoms. Representative examples of heterocyclyl include, for example:

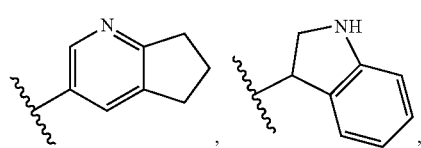

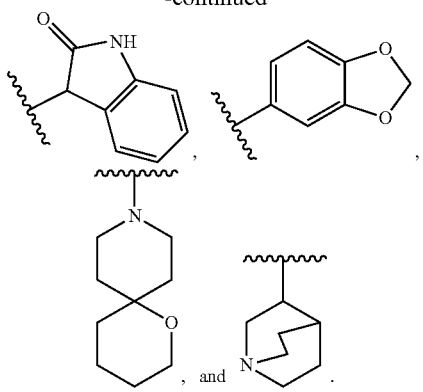
, and

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well-known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the disclosure can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds of the disclosure are administered in therapeutically effective amounts to treat a disease. Alternatively, a therapeutically effective amount of a compound is the quantity required to achieve a desired therapeutic and/or prophylactic effect.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of compounds of the present disclosure can be prepared synthetically from commercially available starting materials that contain asymmetric or stereogenic centers, or by preparation of racemic mixtures followed by resolution methods well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well-known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the disclosure embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The disclosure also embraces isotopically labeled compounds of the disclosure which are identical to those recited herein, except that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the disclosure may have one or more H atom replaced with deuterium.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the disclosure can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well-known in the art (for example, see Rautio, Kumpulainen, et al, Nature Reviews Drug Discovery 2008, 7, 255). For example, if a compound of the disclosure or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_{1-2})$alkylamino$(C_{2-3})$alkyl (such as p-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino$(C_{2-3})$alkyl.

Similarly, if a compound of the disclosure contains an alcohol functional group, a prodrug can be formed by the replacement of the hydrogen atom of the alcohol group with a group such as $(C_{1-6})$alkylcarbonyloxymethyl, 1-(($C_{1-6}$)alkylcarbonyloxy)ethyl, 1-methyl-1-(($C_{1-6}$)alkylcarbonyloxy)ethyl $(C_{1-6})$alkoxycarbonyloxymethyl, N—$(C_{1-6})$alkoxycarbonylaminomethyl, succinoyl, $(C_{1-6})$alkylcarbonyl, α-amino$(C_{1-4})$alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

If a compound of the disclosure incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

The term "warhead" or "warhead group" as used herein refers to a functional group present on a compound wherein that functional group is capable of reversibly or irreversibly participating in a reaction with a protein, e.g., 3C or 3CL protease (e.g., with a cysteine on the protease such as Cys 145). Warheads may, for example, form covalent bonds with the protein, or may create stable transition states, or be a reversible or an irreversible alkylating agent. For example, the warhead moiety can be a functional group on an inhibitor that can participate in a bond-forming reaction, wherein a new covalent bond is formed between a portion of the warhead and a donor, for example an amino acid residue of a protein. In embodiments, the warhead is an electrophile and the "donor" is a nucleophile such as the side chain of a cysteine residue. As provided herein, a warhead may include a nitrile or halo group. As also provided herein, a warhead may include an aldehyde, ketoamides, hydroxybisulfite salts, heterocyclic moieties, aziridine, oxirane, epoxy ketones, halomethyl ketones, hydroxymethyl ketones, electrophilic ketones (e.g. trifluoromethyl ketones), acyloxymethyl ketones, benzothiazolyl ketones and a Michael acceptor. For example, nitriles may be reversible covalent warheads for cysteine protease inhibition, for example, where the mechanism of action may involve aformation of reversible covalent bond between the nitrile and the active cysteine to form a thioimidate adduct. Reaction of cysteine of glutathione or other proteins is generally reversible, while the reaction with cysteine or aminoethylthiols generally irreversibly forms a thiazolidine adduct. It can be appreciated that contemplated compounds herein may be a reversible or an irreversible inhibitor.

Examples of exemplary warheads include, but not limited to, a moiety with a cyano, halomethyl, an aldehyde, ketoamide, hydroxybisulfite salt, heterocycle, epoxy ketone, halomethyl ketone, hydroxymethyl ketone, electrophilic ketone, acyloxymethyl ketone, benzothiazolyl ketone or a Michael acceptor, for example:

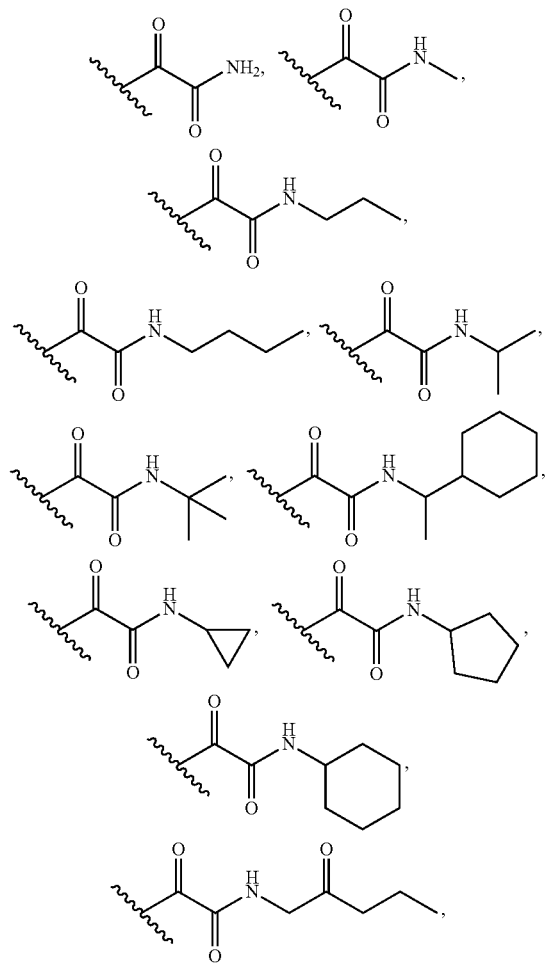

-continued

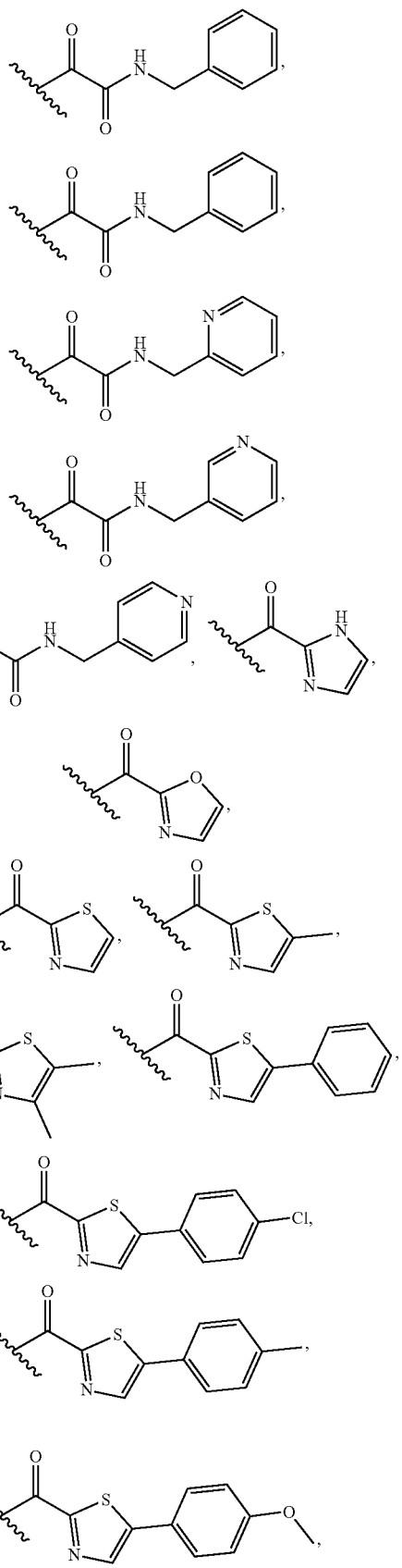

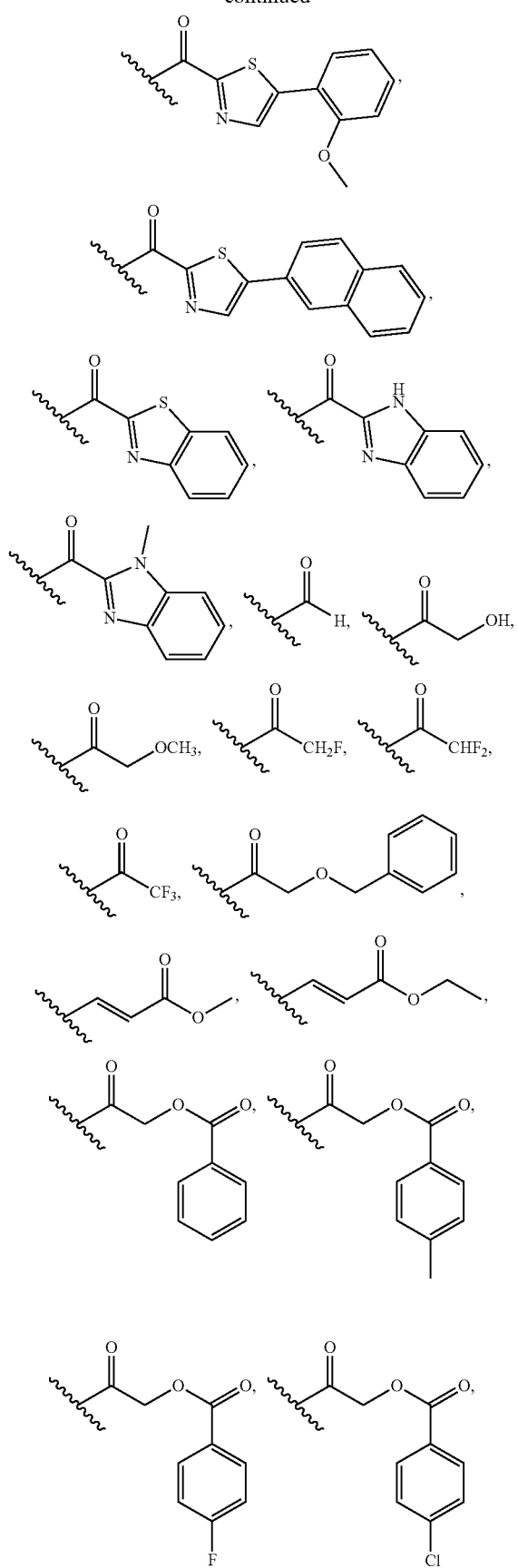
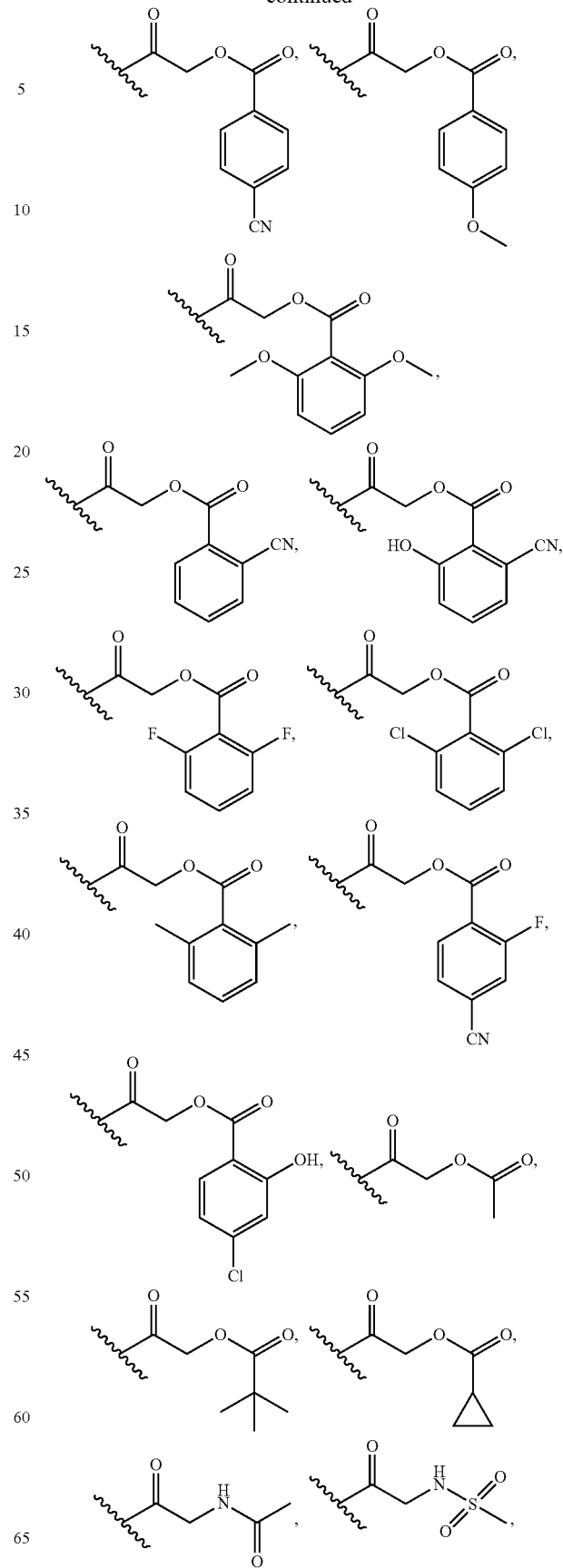

-continued

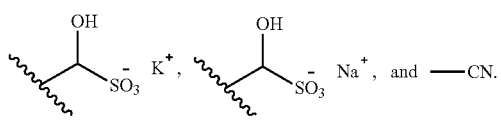

In some embodiments, the warhead is a moiety with a cyanohydrin or cyanoacrylate moiety. Examples of exemplary cyanohydrin and cyanoacrylate warheads include, but not limited to:

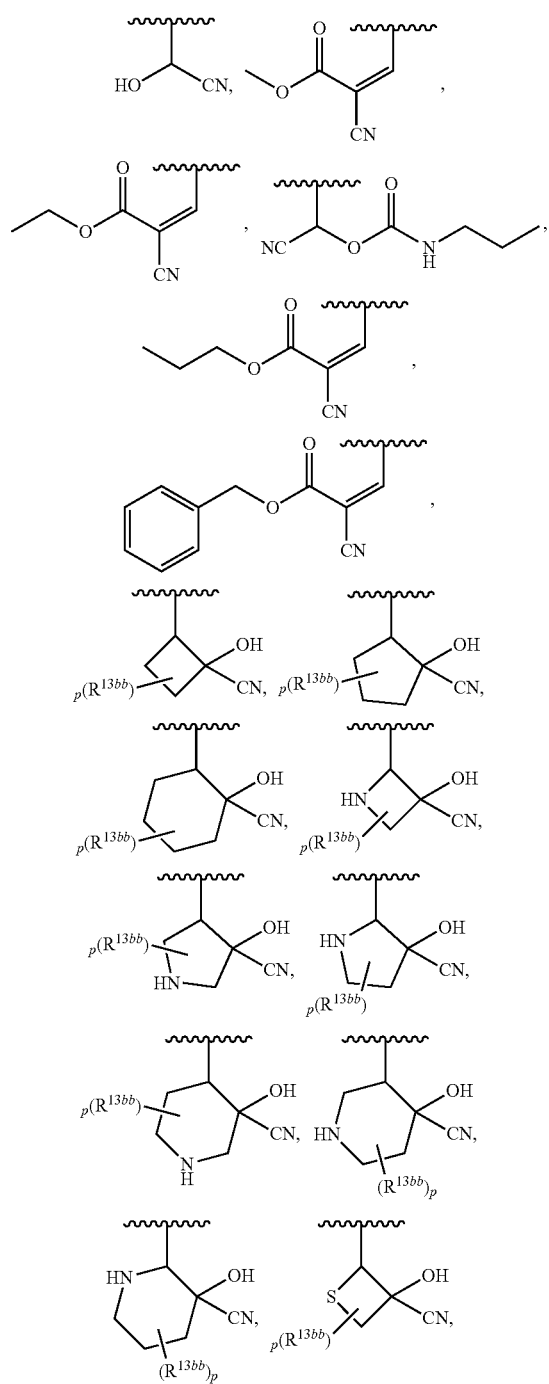

-continued

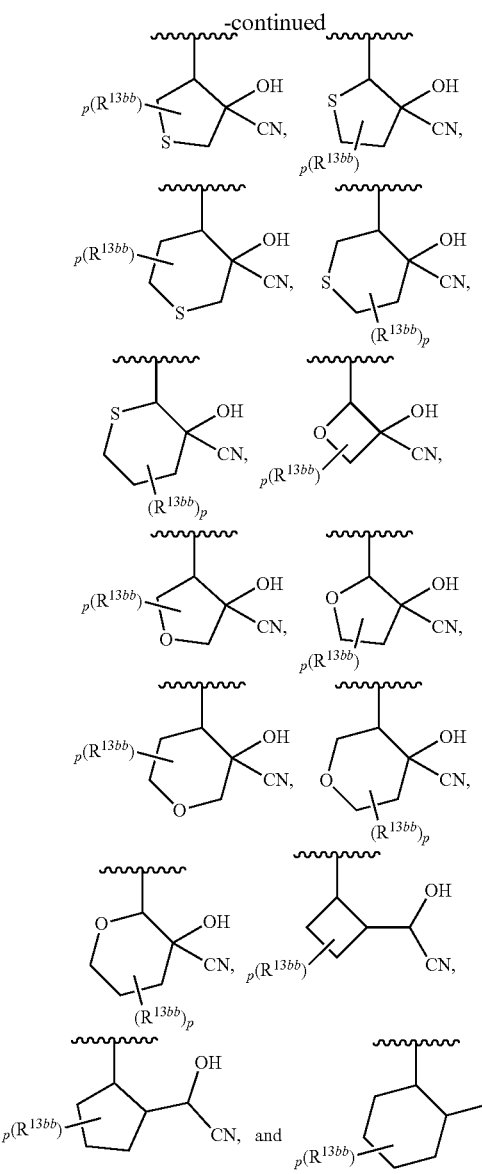

wherein $R^{13bb}$ is selected from the group consisting of halogen, $C_1$-$C_6$alkyl, $C_1$-$C_6$haloalkyl, $C_1$-$C_6$alkoxy, $C_3$-$C_{10}$cycloalkyl, —N($R^e R^f$), and —C(O)—N($R^e R^f$); $R^e$ and $R^f$ are each selected from the group consisting of hydrogen and $C_1$-$C_6$alkyl; or $R^e$ and $R^f$ may form, together with the nitrogen to which they are attached, a 4-6 membered heterocycle; and p is 0, 1, 2, 3, or 4, as valency permits.

In some embodiments, the warhead is a moiety with a cyano amine or cyano amide moiety. Examples of exemplary cyanoamine warheads include, but not limited to:

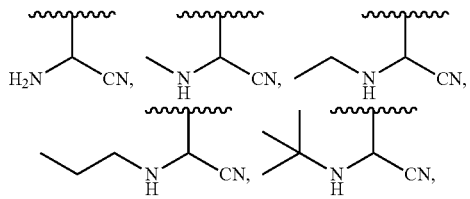

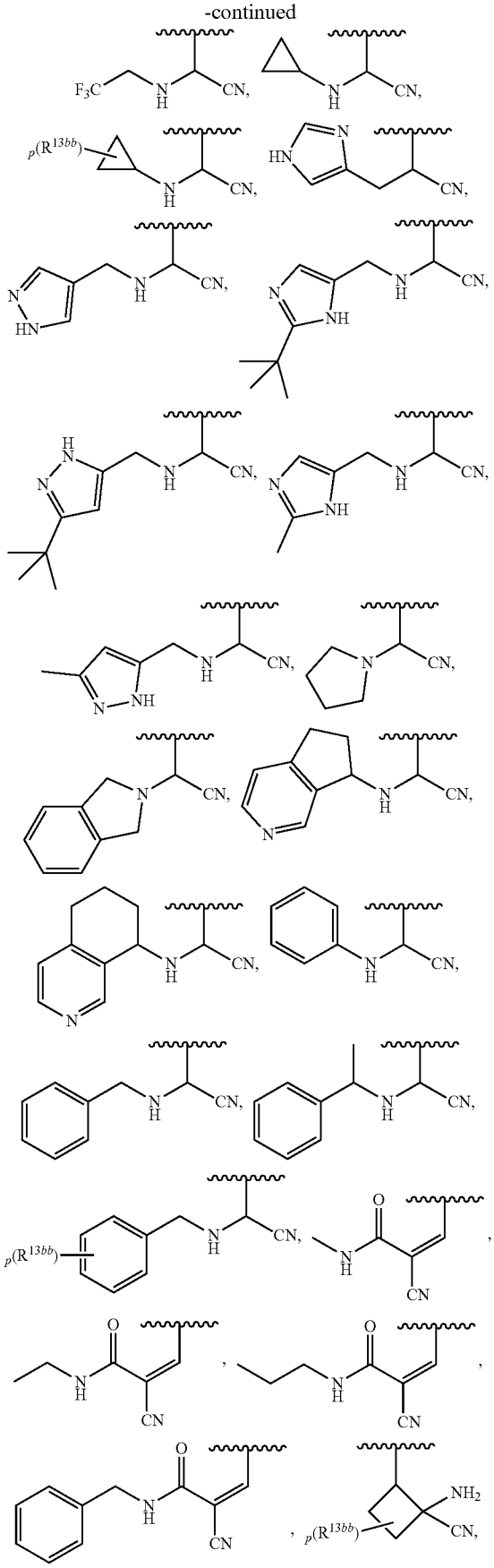

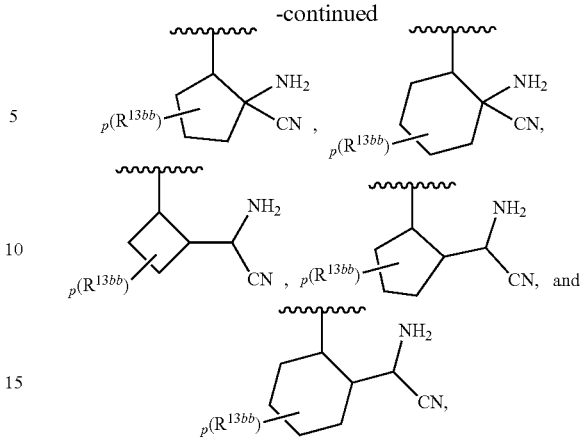

wherein $R^{13bb}$ is selected from the group consisting of halogen, $C_1$-$C_6$alkyl, $C_1$-$C_6$haloalkyl, $C_1$-$C_6$alkoxy, $C_3$-$C_{10}$cycloalkyl, —N($R^eR^f$), and —C(O)—N($R^eR^f$); $R^e$ and $R^f$ are each selected from the group consisting of hydrogen and $C_1$-$C_6$alkyl; or $R^e$ and $R^f$ may form, together with the nitrogen to which they are attached, a 4-6 membered heterocycle; and p is 0, 1, 2, 3, or 4, as valency permits.

In some embodiments, the warhead is a moiety with an imino-oxazolidinone moiety. Examples of exemplary imino-oxazolidinone warheads include, but not limited to:

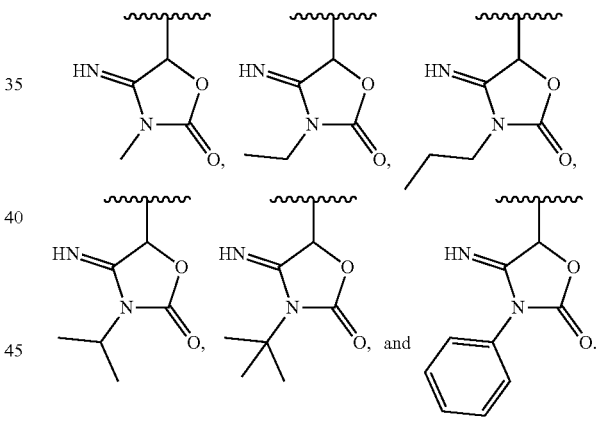

In some embodiments, the warhead is a moiety with an iminoimidazolidinone. Examples of exemplary iminoimidazolidinone warheads include, but not limited to:

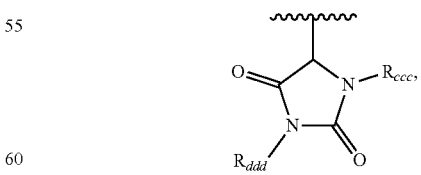

wherein each $R^{ccc}$ and $R^{ccc}$ is selected from the group consisting of hydrogen, $C_1$-$C_8$alkyl, $C_3$-$C_6$cycloalkyl, —($C_1$-$C_8$alkyl)-($C_6$-$C_{14}$aryl), and $C_6$-$C_{14}$aryl. In some embodiments, the warhead is selected from the group consisting of Other examples of exemplary warheads include, but not limited to:

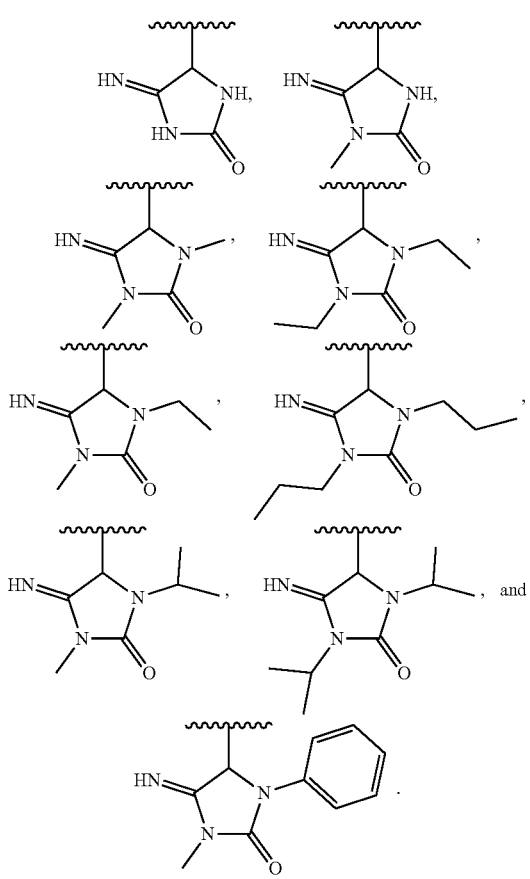

Other examples of exemplary warheads include, but not limited to:

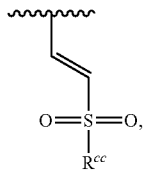

wherein $R^{cc}$ is selected from the group consisting of hydrogen, $C_1$-$C_8$alkyl, $C_3$-$C_6$cycloalkyl, —($C_1$-$C_8$alkyl)-($C_6$-$C_{14}$aryl), $C_6$-$C_{14}$aryl, 5-10 membered heteroaryl, —($C_1$-$C_8$alkyl)-(5-10 membered heteroaryl), 5-10 membered heterocycle and —N($R^b R^c$), wherein $R^b$ and $R^c$ are each selected from the group consisting of hydrogen, C1-$C_8$alkyl, and $C_3$-$C_6$cycloalkyl, or $R^b$ and $R^c$ may be joined together to form, together with the nitrogen to which they are attached, a 5-10 membered heterocycle.

Some other examples of exemplary warheads include, but not limited to:

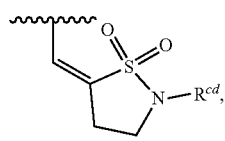

wherein $R^c$ is selected from the group consisting of hydrogen, $C_1$-$C_8$alkyl, and $C_3$-$C_6$cycloalkyl.

Other examples of exemplary warheads include, but not limited to:

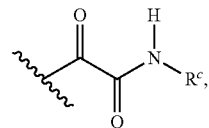

wherein $R^c$ is selected from the group consisting of hydrogen, —$CH_2C(O)O(C_1$-$C_8$alkyl), $C_1$-$C_8$alkyl, and $C_3$-$C_6$cycloalkyl, wherein the $C_1$-$C_8$alkyl may optionally be substituted by one or more substituents each selected from the group consisting of halogen, $C_3$-$C_6$cycloalkyl, 5-10 membered aryl and 5-10 membered heteroaryl;

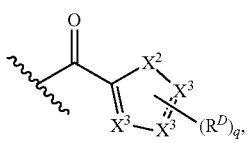

wherein $X^2$ is selected from the group consisting of NH, O and S; $X^3$ is independently selected, for each occurrence, from N and CH; $R^D$ is independently selected, for each occurrence, from the group consisting of $C_1$-$C_8$alkyl,

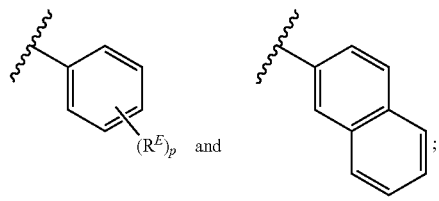

$R^E$ is independently selected, for each occurrence, from the group consisting of halogen, hydroxyl, $C_1$-$C_8$alkyl and $C_1$-$C_8$alkoxy; p is selected from 0, 1 and 2; and q is selected from 0, 1 and 2;

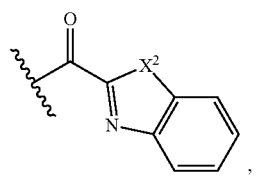

wherein $X^2$ is selected from the group consisting of NH, $NR^P$, O and S, wherein $R^P$ is $C_1$-$C_8$alkyl; and

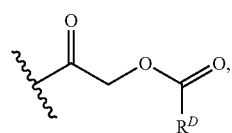

wherein $R^D$ is selected from the group consisting of $C_3$-$C_6$cycloalkyl, $C_1$-$C_8$alkyl, and

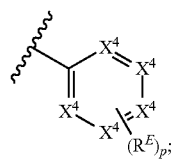

$X^4$ is independently selected, for each occurrence, from CH and N; $R^E$ is independently selected, for each occurrence, from the group consisting of halogen, —CH$_3$, —OCH$_3$, —OCH$_2$CH$_3$, —OCH(CH$_3$)$_2$, —CN, —CF$_3$, —OCF$_3$ and —SCF$_3$; and p is selected from 0, 1 and 2; —C(O)R$^D$, wherein R$^D$ is selected from the group consisting of hydrogen, —CH$_2$OH, —CH$_2$OR' and —CH$_x$F$_y$, wherein x is 0, 1 or 2; y is 1, 2 or 3; and the sum of x and y is 3, wherein R' is selected from the group consisting of C$_1$-C$_8$alkyl, —(C$_1$-C$_8$alkyl)-(5-10 membered aryl), C$_1$-C$_8$heteroalkyl, C$_3$-C$_6$cycloalkyl and 5-10 membered aryl; and —(CH=CH)C(O)OR$^D$, wherein R$^D$ is C$_1$-C$_8$alkyl.

It will be appreciated to one of skilled in the art that the compounds disclosed herein that include the warheads above also contemplate the precursors to those compounds, for example, where a cyano moiety involved in a warheads may be replaced with e.g., a halo moiety.

It will be appreciated to one of skilled in the art that the compounds disclosed herein can also irreversibly bind, or may otherwise inhibit e.g., a virus protein via any other mechanism of action.

The term "inhibitor" as used herein refers to a compound that binds to and/or inhibits a target protease with measurable affinity.

The term "reversible" or "reversible inhibitor" as used herein refers to a protease inhibitor that associates with a protease in such a way as to inhibit the activity of the protease while the protease and inhibitor are bound, but does not associate with a protease in such a way as to inhibit the activity of the protease when the protease and inhibitor are no longer bound. Reversible inhibitors can effect inhibition by competing with substrate for binding to the active site of the protease (competitive reversible inhibitor), or by associating with the protease bound to its substrate in a way to make the complex inactive (uncompetitive reversible inhibitor), or by associating with the protease and/or protease-substrate complex in a way that inhibits the activity of either and/or both.

As used herein, the term "irreversible" or "irreversible inhibitor" refers to an inhibitor (i.e. a compound) that is able to be covalently bonded to a target protease in a substantially non-reversible manner. An irreversible inhibitor will remain substantially bound to the target protease once covalent bond formation has occurred. Irreversible inhibitors usually display time dependency, whereby the degree of inhibition increases with the time with which the inhibitor is in contact with the enzyme. In certain embodiments, an irreversible inhibitor will remain substantially bound to target protease once covalent bond formation has occurred and will remain bound for a time period that is longer than the life of the protein.

I. Reversible or Irreversible Viral Protease Inhibitor Compounds

The disclosure is directed to, in part, compounds that inhibit a viral protease. Examples of viral proteases include, but not limited to, Cathepsin K, coronavirus main protease (Mpro), Caspase 3, Calpain 1, and Cathepsin S. Accordingly, in various embodiments, a compound of the present disclosure (e.g. a compound of Formula II, II-A, II-B, II-C, II-D-A, II-D-B, II-E-A, II-E-B, II-F, II-G, II-H-A, II-H-B, II-E, and II-I) is a viral protease inhibitor, wherein the viral protease is selected from the group consisting of Cathepsin K, coronavirus main protease (Mpro), Caspase 3, Calpain 1, and Cathepsin S. In certain embodiments, the viral protease is a coronavirus main protease (Mpro). In some embodiments, the viral protease is Cathepsin K. In some embodiments, the viral protease is Caspase 3. In some embodiments, the viral protease is Calpain 1. In some embodiments, the viral protease is Cathepsin S.

Also provided herein are compounds represented by

Formula II

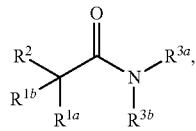

$R^{3a}$ is selected from

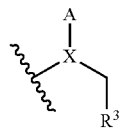

and 4-10 membered heterocycle, wherein the heterocycle may optionally be substituted by one, two or three substituents each selected from the group consisting of hydroxyl, C$_1$-C$_8$alkoxy, oxo and a warhead A; R$^{3b}$ is selected from hydrogen and C$_1$-C$_8$alkyl; wherein R$^{3a}$ and R$^{3b}$ may be joined together to form, together with the carbon to which they are attached, a 4-10 membered heterocycle, wherein the heterocycle may optionally be substituted by one, two or three substituents each selected from C$_6$-C$_{14}$aryl and a warhead A; R$^{1a}$ is selected from the group consisting of hydrogen, C$_1$-C$_8$alkyl, C$_1$-C$_8$heteroalkyl, —(C$_1$-C$_8$alkyl)-R$^1$, —(C$_1$-C$_8$alkyl)-CN, C$_3$-C$_{10}$cycloalkyl, C$_6$-C$_{14}$aryl, 4-10 membered heterocycle and 5-10 membered heteroaryl; R$^{1b}$ is selected from hydrogen and C$_1$-C$_8$alkyl; or R$^{1a}$ and R$^{1b}$ may be joined together to form, together with the carbon to which they are attached, a 4-10 membered heterocycle having a ring nitrogen, NR$^G$, or a C$_3$-C$_{10}$cycloalkyl; R$^1$ is selected from the group consisting of C$_1$-C$_8$alkyl, C$_2$-C$_{10}$alkenyl, C$_2$-C$_{10}$alkynyl, C$_3$-C$_{10}$cycloalkyl, C$_6$-C$_{14}$aryl, 5-10 membered heteroaryl and 4-10 membered heterocycle, wherein R$^1$ may optionally be substituted by one, two, or three substituents each selected from R$^A$; R$^A$ is independently selected for each occurrence from the group consisting of halogen, cyano, hydroxyl, oxo, SF$_5$, —CH$_2$CF$_3$, —CF$_3$, —O—CF$_3$, —O—CHF$_2$, —S—CH$_3$, —S(O)$_2$—CH$_3$, —NH$_2$, —O-phenyl, —O—(C$_1$-C$_8$alkyl)-phenyl, —NHC(O)R$^B$, —NHC(O)OR$^B$, —NHC(O)O—(C$_1$-C$_8$alkyl)-R$^B$, —N(R$^y$)$_2$, —N(R$^y$)(C$_1$-C$_8$alkyl)C(O)O—phenyl, —N(R$^y$)(C$_1$-C$_8$alkyl)C(O)N(R$^y$)$_2$, —C(O)—OC(CH$_3$)$_3$, C$_1$-C$_8$alkyl, C$_2$-C$_{10}$alkenyl, C$_2$-C$_{10}$alkynyl, C$_1$-C$_8$heteroalkyl, C$_1$-C$_8$alkoxy, C$_3$-C$_{10}$cycloalkyl, —(C$_1$-C$_8$alkyl)-(C$_3$-C$_{10}$cycloalkyl), —(C$_1$-C$_8$alkyl)-(C$_6$-C$_{14}$aryl), —(C$_1$-C$_8$alkyl)-(5-10 membered heteroaryl), C$_6$-C$_{14}$aryl, 5-10 membered heteroaryl and 4-10 membered heterocyclyl, wherein the $R^B$, alkyl, heterocyclyl, heteroaryl, or aryl may optionally be substituted by one, two or three substituents of halogen, $C_1$-$C_8$alkyl, $C_1$-$C_8$alkoxy, $SF_5$, —$NH_2$, hydroxyl or oxo; $R^2$ is selected from the group consisting of —NHC(O)$R^B$, —NHC(O)N($R^B$)$_2$, —NHC(O)C($R^C$)$_2R^B$, —NHS(O)$_2R^B$, —O—($C_1$-$C_8$alkyl)-($C_3$-$C_{10}$cycloalkyl), 4-10 membered heterocycle, $C_6$-$C_{14}$aryl and 5-10 membered heteroaryl bound through the carbon or nitrogen atom, wherein $R^B$ or $R^2$ may optionally be substituted by one, two, or three substituents each selected from $R^x$; or $R^{1a}$ and $R^2$ may be joined together to form, together with the carbon to which they are attached, a 4-10 membered mono or bicyclic heterocycle having a ring nitrogen $NR^G$, or a $C_3$-$C_{10}$cycloalkyl, wherein the cycloalkyl or heterocycle may optionally be substituted by one, two or three substituents on a free carbon each selected from $R^A$; $R^3$ is selected from 5-10 membered heteroaryl and 4-10 membered heterocycle, wherein $R^3$ may optionally be substituted by one, two, or three substituents each selected from $R^A$; $R^B$ is independently selected, for each occurrence, from the group consisting of $C_1$-$C_8$alkyl, $C_2$-$C_{10}$alkenyl, $C_2$-$C_{10}$alkynyl, $C_3$-$C_6$cycloalkyl, fluorenylmethyloxy, $C_6$-$C_{14}$aryl, 5-10 membered heteroaryl and 4-10 membered heterocycle; $R^C$ is independently selected, for each occurrence, from hydrogen, halogen and $C_1$-$C_8$alkyl; $R^x$ is independently selected, for each occurrence, from the group consisting of halogen, hydroxyl, oxo, $CF_3$, $SF_5$, cyano, —O—($R^{xx}$)—$OCH_3$, —$OCHF_2$, —$OCF_3$, —O—($C_1$-$C_8$alkyl), —C(O)O($CH_3$), —N($R^y$)$_2$, —N($R^y$)C(O)$R^y$, —N($R^y$)($C_1$-$C_8$alkyl)C(O)N($R^y$)$_2$, —N($R^y$)($C_1$-$C_8$alkyl)C(O)OH, —($C_1$-$C_8$alkyl)-($C_3$-$C_{10}$cycloalkyl), $C_1$-$C_8$alkyl, $C_1$-$C_8$alkoxy, $C_3$-$C_{10}$cycloalkyl, $C_6$-$C_{14}$aryl, —O—$C_6$-$C_{14}$aryl, 5-10 membered heteroaryl and 4-10 membered heterocycle; wherein two geminal $C_1$-$C_8$alkyl groups, together with the carbon to which they are attached, may be joined together to form a $C_3$-$C_6$cycloalkyl optionally substituted by one, two or three substituents each selected from halogen, hydroxyl or oxo; and wherein the alkyl, aryl, heterocycle or heteroaryl may optionally be substituted by one or more substituents each selected from oxo, halogen and $C_1$-$C_8$alkyl; $R^G$ is selected from the group consisting of hydrogen, $C_{1-6}$alkyl optionally substituted by one, two or three $R^{gg}$, —C(=O)—$C_{1-6}$alkyl optionally substituted by one, two or three $R^{hh}$, —C(=O)—$C_{3-6}$cycloalkyl, —C(O)—($C_2$-$C_{10}$alkenyl)-($C_6$-$C_{14}$aryl), —C(O)-(5-10 membered heteroaryl), —C(O)-(4-10 membered heterocyclyl), and —C(O)-(4-10 membered heterocyclyloxy); wherein the aryl, heterocyclyl, or heteroaryl may optionally be substituted by one, two or three $R^{jj}$; $R^{gg}$ is independently selected for each occurrence from the group consisting of —C(=O), halo, cyano, —$NR^m R^m$, and —NH(C=O)$R^m$; $R^{hh}$ is independently selected for each occurrence from the group consisting of halo, cyano, —$NR^m R^m$, —$NR^m$(C=O)$R^m$, phenyl, cycloalkyl, heterocyclyl and $C_1$-$C_6$alkoxy; $R^{jj}$ is independently selected for each occurrence from the group consisting of halo, oxo, hydroxyl, cyano, $C_1$-$C_6$alkyl, $C_{1-6}$haloalkyl, $C_1$-$C_6$alkoxy, $C_{3-6}$cycloalkyl, $SF_5$, and $NH_2$; $R^m$ is independently selected for each occurrence from the group consisting of hydrogen, $C_{1-3}$alkyl, phenyl, —S(O)$_2$—$CH_3$, $C_{3-6}$cycloalkyl, and 5-6 membered heteroaryl; wherein $C_{1-3}$alkyl, phenyl, and $C_{3-6}$cycloalkyl may optionally be substituted by one, two or three halo; $R^{xx}$ is —(OCH$_2$CH$_2$)$_{nn}$—, wherein nn is selected from 1, 2, 3, 4, 5 and 6; $R^y$ is independently selected, for each occurrence, from the group consisting of hydrogen, $C_1$-$C_8$alkyl, $C_1$-$C_8$heteroalkyl, —$CF_3$, —$CH_2CF_3$, $C_1$-$C_8$alkoxy, —($C_1$-$C_8$alkoxy)-(5-10 membered aryl), $C_3$-$C_6$cycloalkyl and —($C_1$-$C_8$alkyl)COOH; A is a warhead; X is selected from the group consisting of C($R^{xy}$) and N, wherein $R^{xy}$ is selected from the group consisting of H, D, —OH, —$NH_2$, halogen, $C_1$-$C_8$alkyl, $C_1$-$C_8$ haloalkyl, and $C_1$-$C_8$alkoxy; and pharmaceutically acceptable salts, stereoisomers, esters, and prodrugs thereof.

In some embodiments, $R^{3b}$ is hydrogen.

In certain embodiments, the present disclosure provides compounds of Formula II-A:

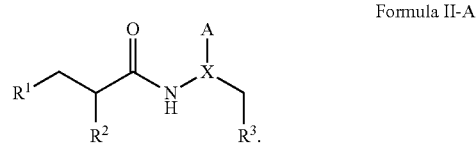

Formula II-A

In certain embodiments, the present disclosure provides compounds of Formula II-B:

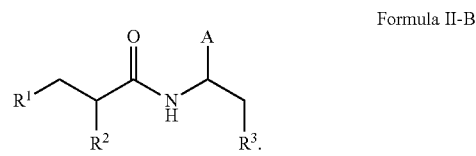

Formula II-B

In various embodiments, the present disclosure provides compounds of Formula II-C:

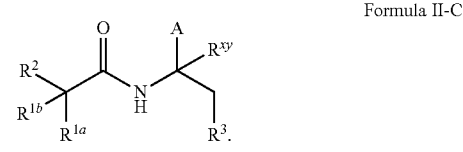

Formula II-C

In some embodiments, provided herein are compounds represented by Formula II-D-A or Formula II-D-B:

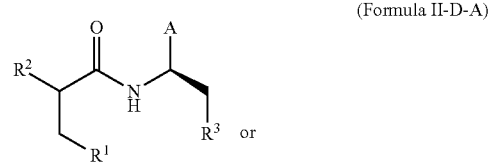

(Formula II-D-A)

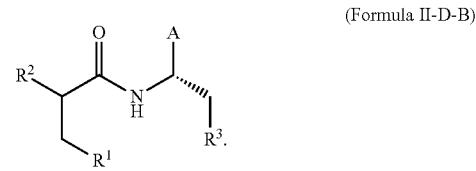

(Formula II-D-B)

In some embodiments, provided herein are compounds represented by Formula II-E-A or Formula II-E-B:

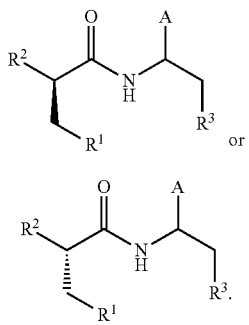
(Formula II-E-A)

or

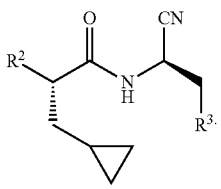
(Formula II-E-B)

In some embodiments, provided herein are compounds represented by Formula II-F:

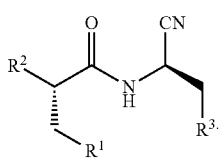
Formula II-F

In some embodiments, provided herein are compounds represented by Formula II-G:

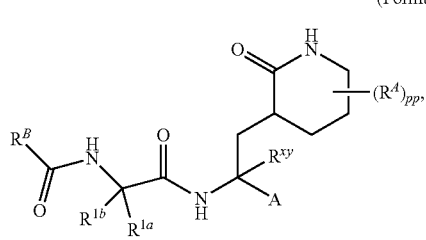
Formula II-G

In some embodiments, provided herein are compounds represented by Formula II-H-A or Formula II-H-B:

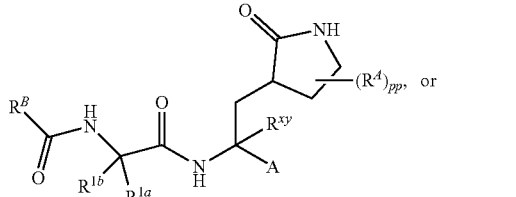
(Formula II-H-A)

(Formula II-H-B)

wherein pp is selected from 0, 1, 2, and 3.

In some embodiments, provided herein are compounds represented by Formula II-E:

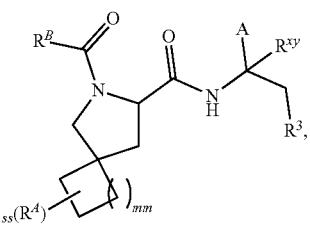
(Formula II-E)

wherein ss is selected from 0, 1, 2, and 3, and mm is selected from 1, 2, and 3.

In some embodiments, provided herein are compounds represented by Formula II-I:

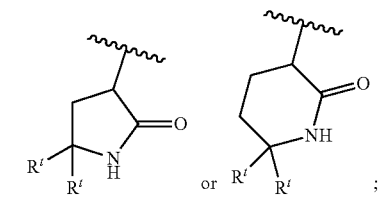
Formula II-I wherein: $R^3$ is

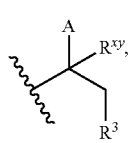

$R^t$ is independently, for each occurrence, H or methyl; or each $R^t$ may be taken, together with the carbon to which they are attached, to form a cyclopropyl; $R^B$ is selected from the group consisting of: a 9-10 membered bicyclic heteroaryl having one ring nitrogen, $C_1$-$C_6$alkyl, and $C_2$-$C_3$alkenyl; wherein $R^B$ is optionally substituted by one, two or three substituents each independently selected from the group consisting of halogen, $C_1$-$C_3$alkoxy, NHR$^m$, and phenyl (optionally substituted by one or two halogens); R$^m$ is $C_{1-3}$alkyl or —C(O)—$C_{1-3}$alkyl, wherein each $C_{1-3}$alkyl is independently optionally substituted by one, two or three halogens; or a pharmaceutically acceptable salt thereof.

In certain embodiments, $R^{3a}$ is wherein $R^{xy}$ is selected from the group consisting of H, D, OH, NH$_2$, halogen, $C_1$-$C_8$alkyl, $C_1$-$C_8$ haloalkyl, and $C_1$-$C_8$alkoxy. In embodiments, $R^{xy}$ is selected from the group consisting of H, D, $CH_3$, $CH_2CH_3$, F, and $CF_3$. In some embodiments, $R^{xy}$ is F. In some embodiments, $R^{xy}$ is $CF_3$. In some embodiments, $CH_3$. In some embodiments, $R^{xy}$ is H.

In various embodiments, X is selected from the group consisting of CH, CD, C($CH_3$), C($CH_2CH_3$), N, CF, CCl, CBr, C($CHF_2$), C($CH_2F$), and C($CF_3$). In some embodiments, X is CH. In some embodiments, X is CD. In some embodiments, X is C($CH_3$). In some embodiments, X is C($CF_3$). In some embodiments, X is CF. In some embodiments, X is N.

In some embodiments, A is selected from the group consisting of cyano, —C(O)$R^D$, —C(O)$CH_2$N($R^bR^c$), —C(O)$CH_2$OC(O)$R^D$, —C(O)C(O)$R^D$, —(CH═CH)C(O)O$R^D$, —(CH═CCN)C(O)O$R^D$, —(CH═CCN)C(O)(NH)$R^D$, —CH(CN)(OH), —CH(CN)(N$R^bR^c$),

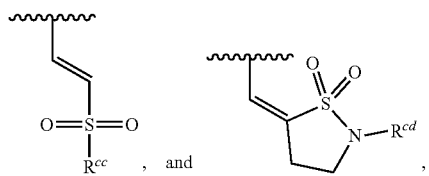

and wherein $R^D$ is selected from the group consisting of hydrogen, hydroxyl, —O$R^{bb}$—N($R^bR^c$), $C_1$-$C_8$alkyl, $C_1$-$C_8$alkoxy, $C_3$-$C_6$cycloalkyl, $C_6$-$C_{14}$aryl, 5-10 membered heteroaryl, and 4-10 membered heterocycle; wherein $R^D$ may optionally be substituted by one, two, or three substituents each selected from the group consisting of halogen, hydroxyl, and $R^E$; $R^E$ is selected from the group consisting of $C_1$-$C_8$alkyl, $C_1$-$C_8$alkoxy, $C_6$-$C_{14}$aryl, 4-10 membered heterocycle, and 5-10 membered heteroaryl, wherein $R^E$ may optionally be substituted by one, two, or three substituents each selected from halogen, cyano, $C_1$-$C_5$alkyl and $C_1$-$C_8$alkoxy; $R^{bb}$ is selected from the group consisting of $C_3$-$C_6$cycloalkyl, $C_6$-$C_{14}$aryl, —($C_1$-$C_8$alkyl)-$C_6$-$C_{14}$aryl, 5-10 membered heteroaryl, and 4-10 membered heterocycle; $R^{cc}$ is selected from the group consisting of hydrogen, $C_1$-$C_8$alkyl, $C_3$-$C_6$cycloalkyl, —($C_1$-$C_8$alkyl)-($C_6$-$C_{14}$aryl), $C_6$-$C_{14}$aryl, 5-10 membered heteroaryl, —($C_1$-$C_8$alkyl)-(5-10 membered heteroaryl), 5-10 membered heterocycle and —N($R^bR^c$), wherein $R^b$ and $R^c$ are each selected from the group consisting of hydrogen, $C_1$-$C_8$alkyl, and $C_3$-$C_6$cycloalkyl, or $R^b$ and $R^c$ may be joined together to form, together with the nitrogen to which they are attached, a 5-10 membered heterocycle; $R^{cd}$ is selected from the group consisting of hydrogen, $C_1$-$C_8$alkyl, and $C_3$-$C_6$cycloalkyl; and $R^b$ and $R^c$ are each selected from the group consisting of hydrogen, —$CH_2$C(O)O($C_1$-$C_8$alkyl), —C(O)—($C_1$-$C_8$alkyl), —S(O)$_2$—($C_1$-$C_8$alkyl), $C_1$-$C_8$alkyl, $C_3$-$C_6$cycloalkyl and —($C_1$-$C_8$alkyl)-$C_6$-$C_{14}$aryl, wherein the $C_1$-$C_8$alkyl may optionally be substituted by one or more substituents each selected from the group consisting of halogen, $C_3$-$C_6$cycloalkyl, $C_6$-$C_{14}$aryl, 4-10 membered heterocycle, and 5-10 membered heteroaryl.

In embodiments, A is selected from the group consisting of —CN,

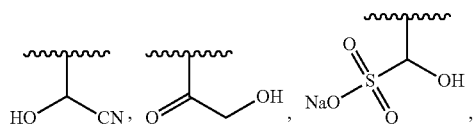

-continued

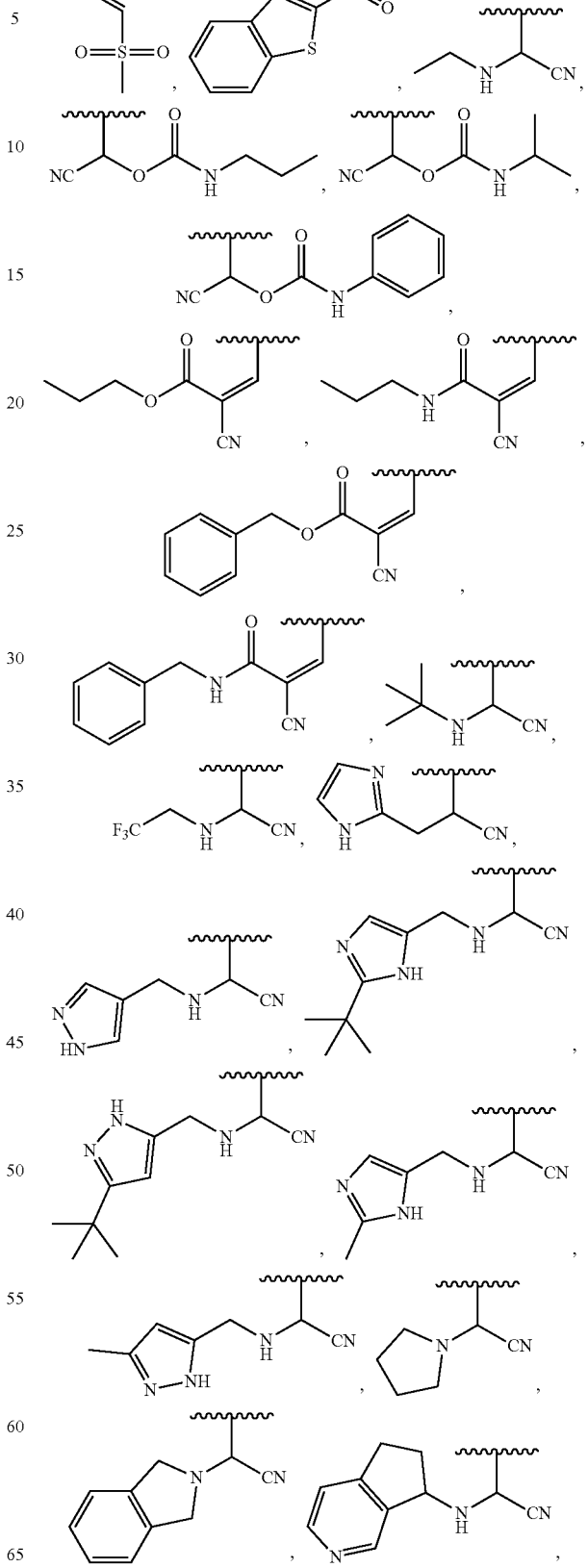

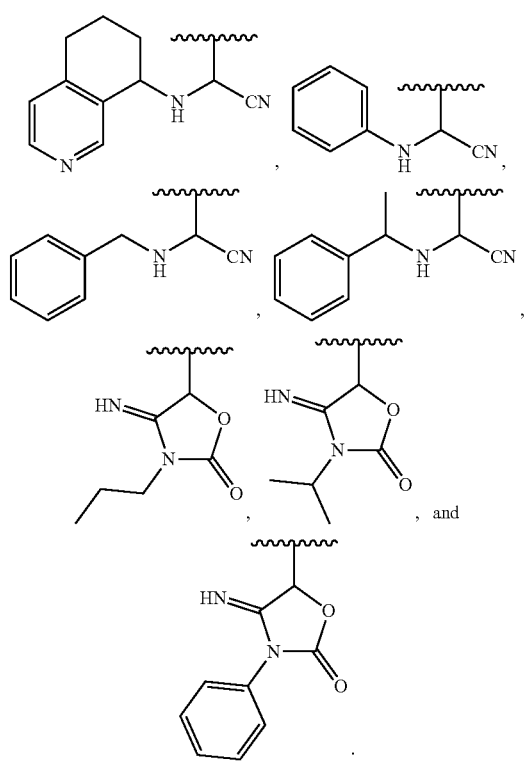
In embodiments, $R^{1a}$ is selected from the group consisting of
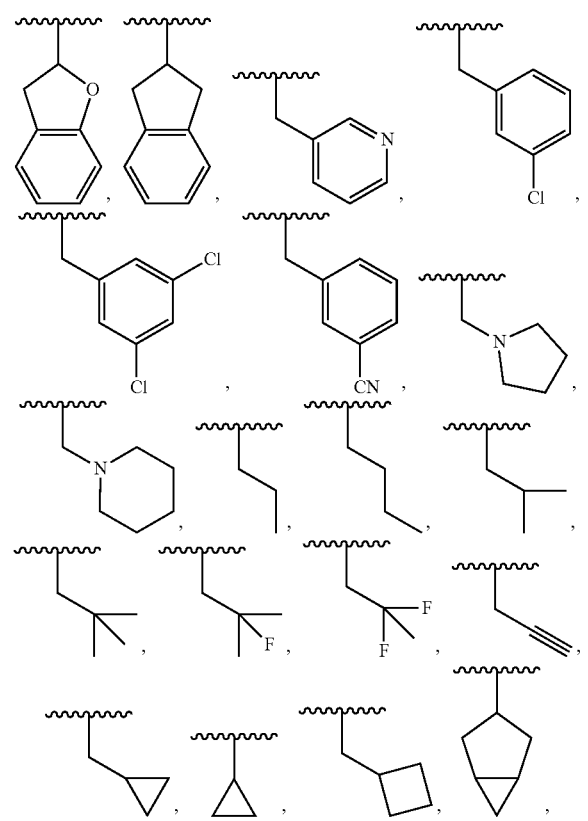
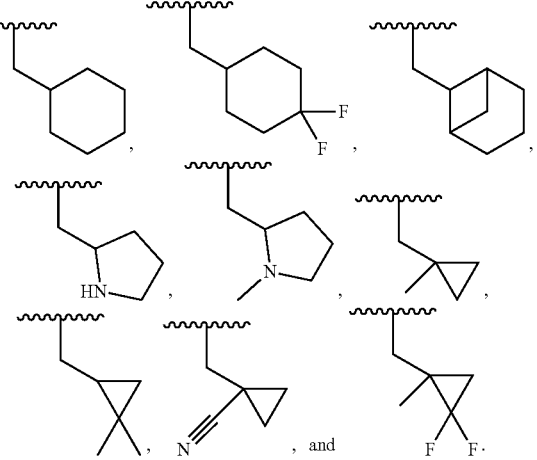
In embodiments, $R^{1a}$ is —($C_1$-$C_8$alkyl)-$R^1$.
In embodiments, $R^{1b}$ is hydrogen.
In certain embodiments, $R^{1a}$ and $R^{1b}$ are joined to together to form
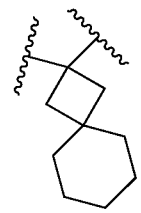
In certain embodiments, $R^{3a}$ is a 4-10 membered heterocycle.
In some embodiments, $R^{3a}$ is selected from the group consisting of
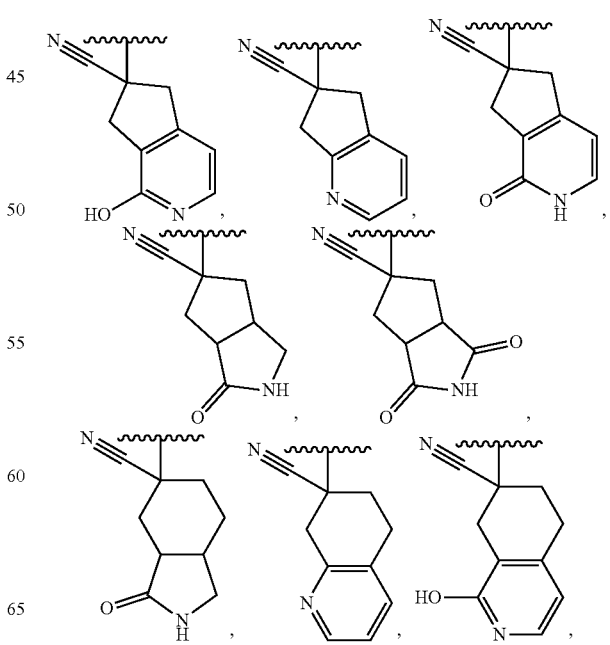

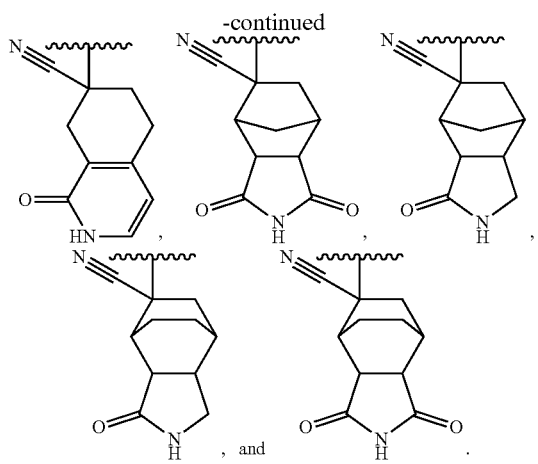, and

In some embodiments, $R^3$ is a 4-10 membered heterocycle.

In some embodiments, $R^3$ is selected from

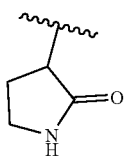

and

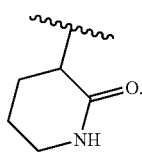 [SMILES: *C1CCCNC1=O]

In some embodiments, $R^3$ is

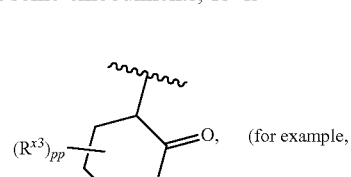 (for example, 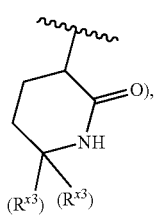), wherein $R^{x3}$ are independently for each occurrence selected from the group consisting of hydrogen, halogen, $C_1$-$C_8$alkyl, $C_1$-$C_8$ haloalkyl, $C_3$-$C_6$cycloalkyl, and $C_1$-$C_8$alkoxy; and pp is selected from 0, 1, 2, and 3. In some embodiments, $R^3$ is

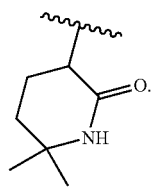 [SMILES: *C1CCC(C)(C)NC1=O]

In some embodiments, $R^3$ is

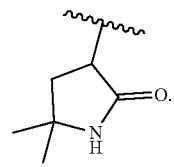 [SMILES: *C1CC(C)(C)NC1=O]

In some embodiments, $R^3$ is

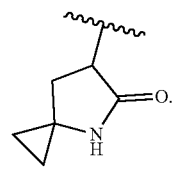 [SMILES: *C1CC2(CC2)NC1=O]

In some embodiments, $R^3$ is

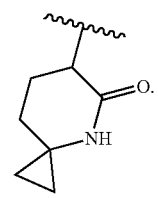 [SMILES: *C1CCC2(CC2)NC1=O]

In some embodiments, $R^3$ is

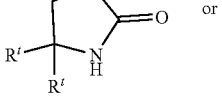 or 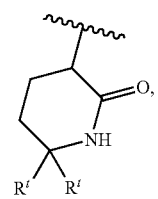

and $R^t$ is independently, for each occurrence, H or methyl; or each $R^t$ may be taken, together with the carbon to which they are attached, to form a cyclopropyl.

In some embodiments, $R^3$ is selected from the group consisting of

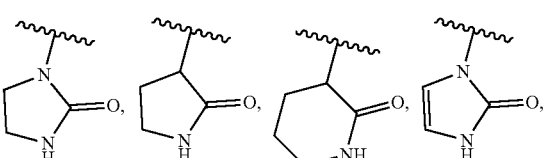

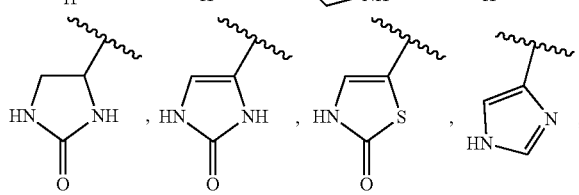

-continued
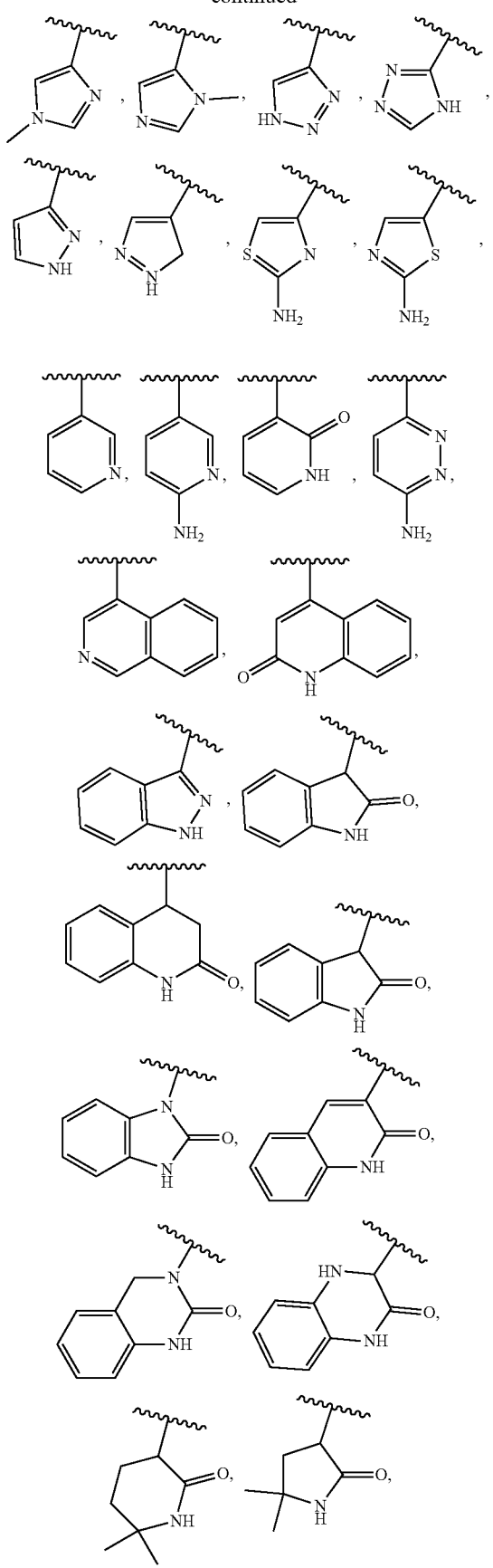
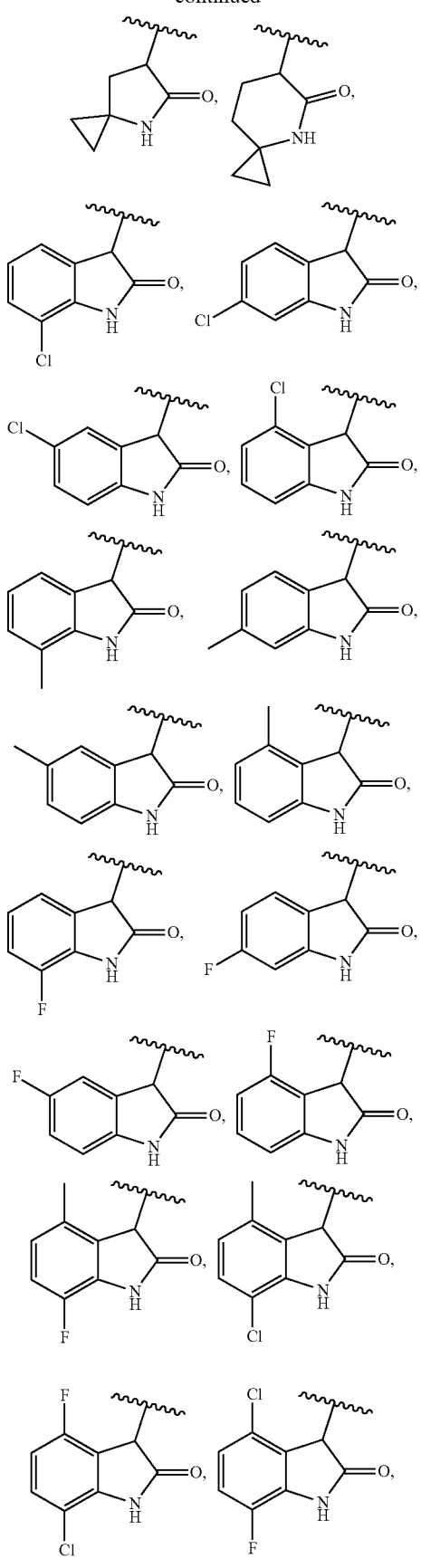

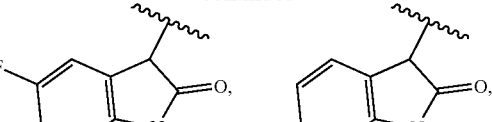
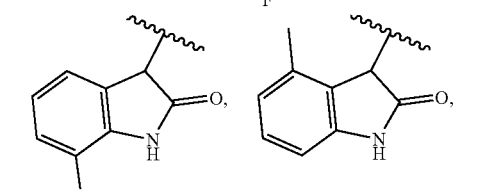
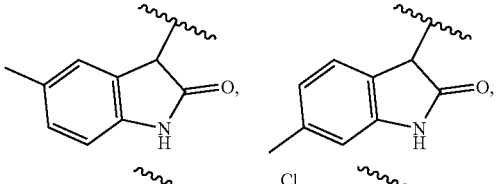
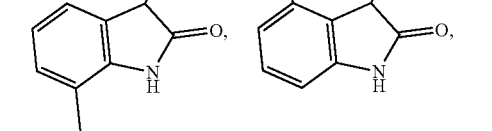
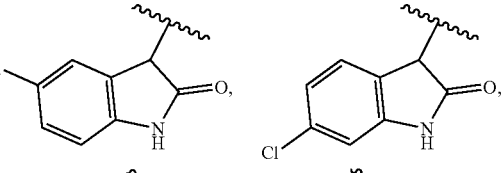
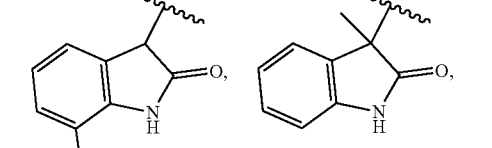
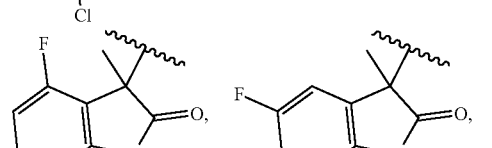
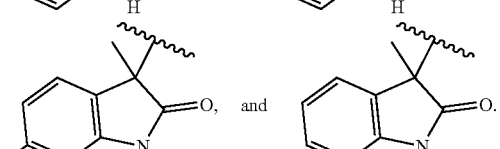
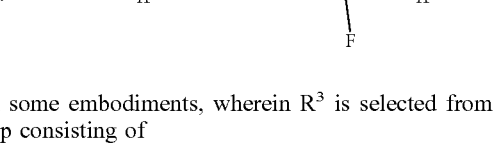
In some embodiments, wherein R³ is selected from the group consisting of
-continued
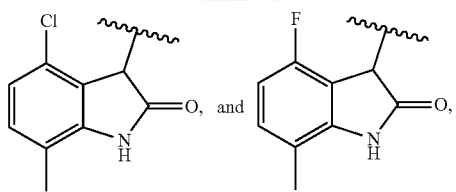
In some embodiments, wherein R³ is selected from the group consisting of
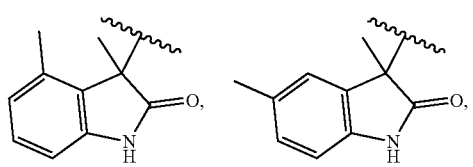
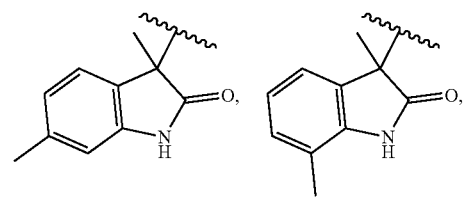
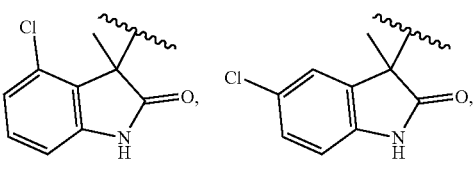
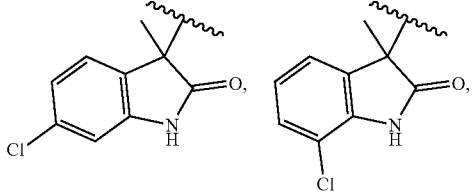
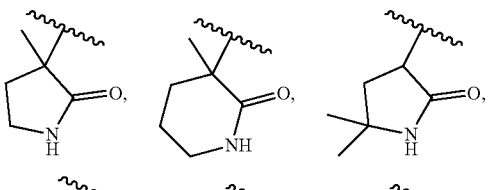
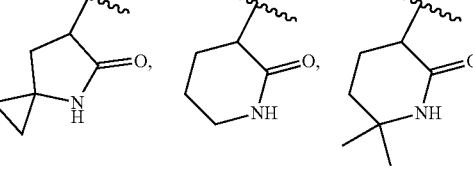
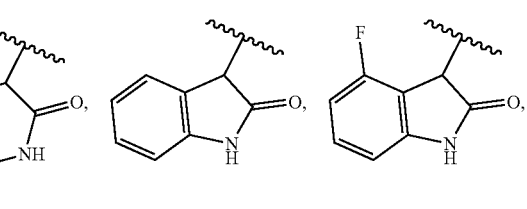
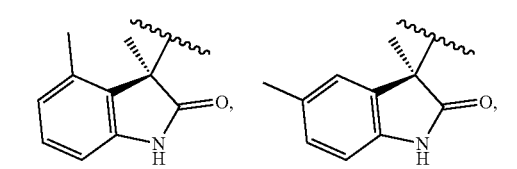

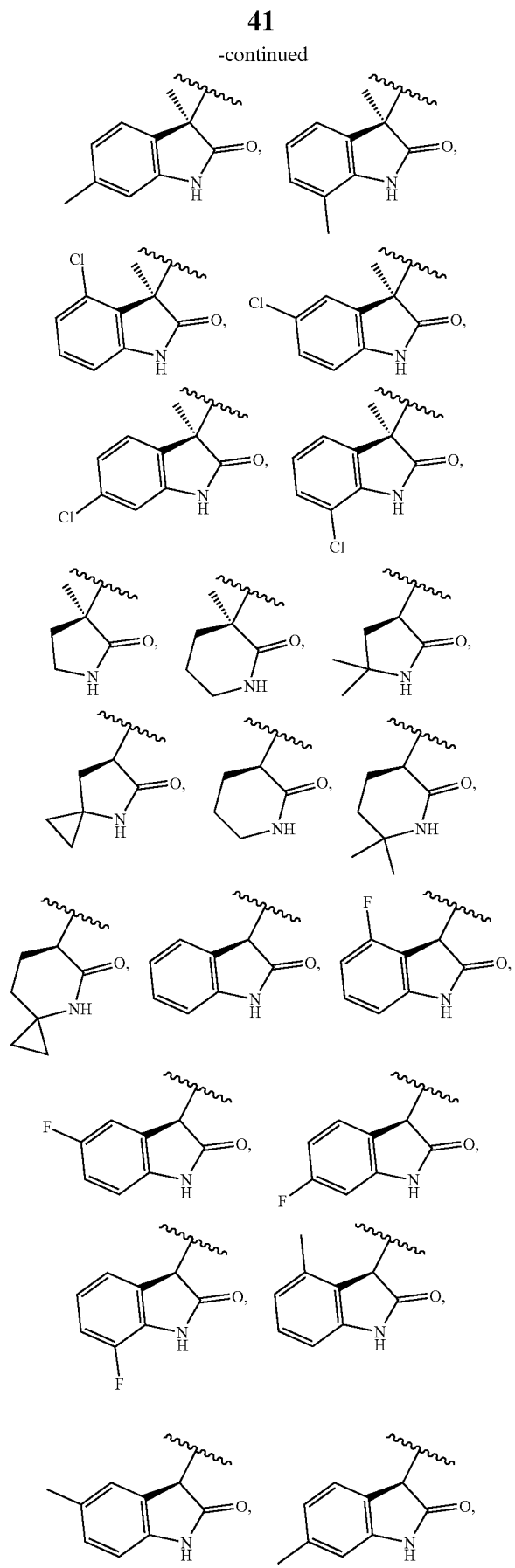
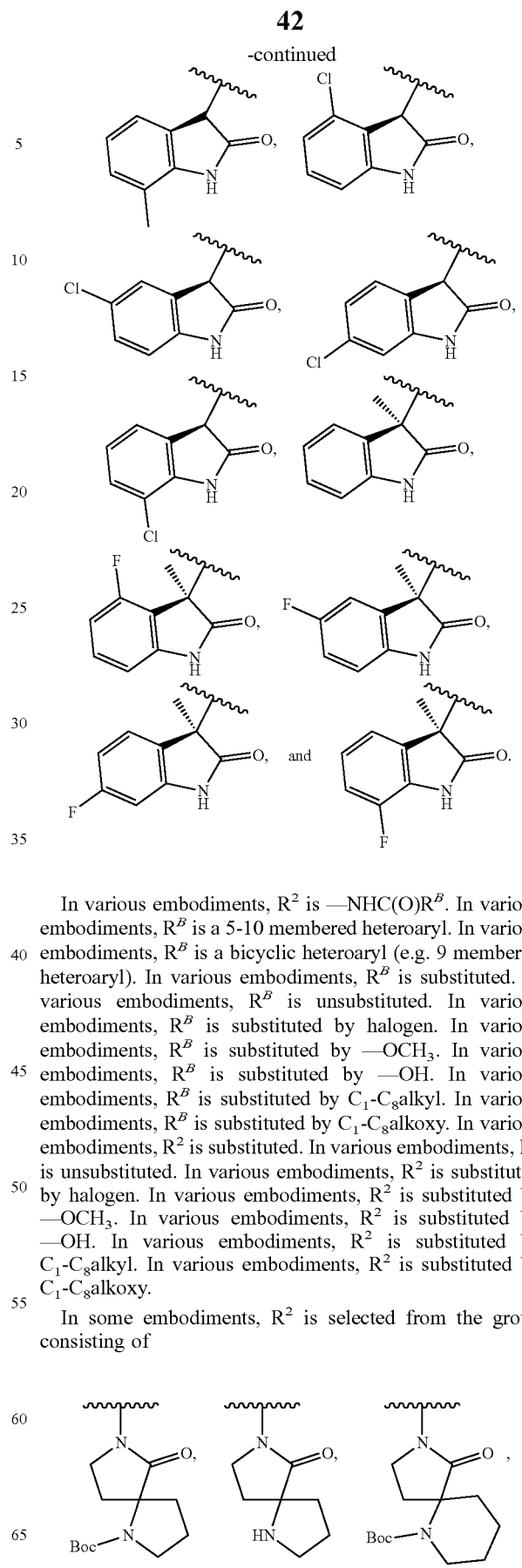

In various embodiments, $R^2$ is —NHC(O)$R^B$. In various embodiments, $R^B$ is a 5-10 membered heteroaryl. In various embodiments, $R^B$ is a bicyclic heteroaryl (e.g. 9 membered heteroaryl). In various embodiments, $R^B$ is substituted. In various embodiments, $R^B$ is unsubstituted. In various embodiments, $R^B$ is substituted by halogen. In various embodiments, $R^B$ is substituted by —OCH$_3$. In various embodiments, $R^B$ is substituted by —OH. In various embodiments, $R^B$ is substituted by $C_1$-$C_8$alkyl. In various embodiments, $R^B$ is substituted by $C_1$-$C_8$alkoxy. In various embodiments, $R^2$ is substituted. In various embodiments, $R^2$ is unsubstituted. In various embodiments, $R^2$ is substituted by halogen. In various embodiments, $R^2$ is substituted by —OCH$_3$. In various embodiments, $R^2$ is substituted by —OH. In various embodiments, $R^2$ is substituted by $C_1$-$C_8$alkyl. In various embodiments, $R^2$ is substituted by $C_1$-$C_8$alkoxy.

In some embodiments, $R^2$ is selected from the group consisting of

-continued
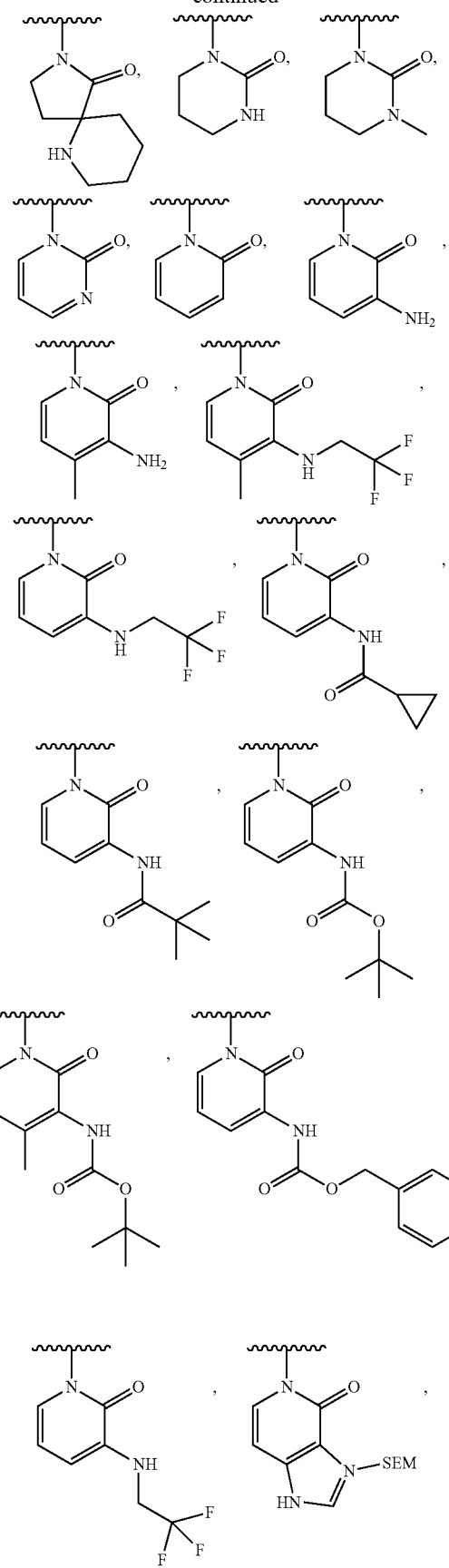
-continued
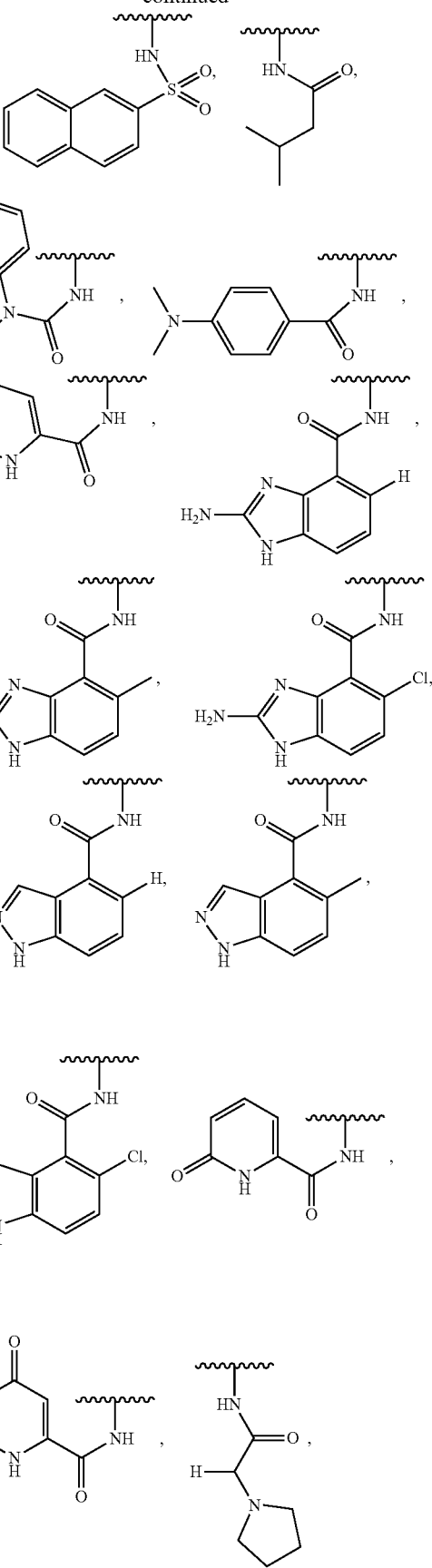

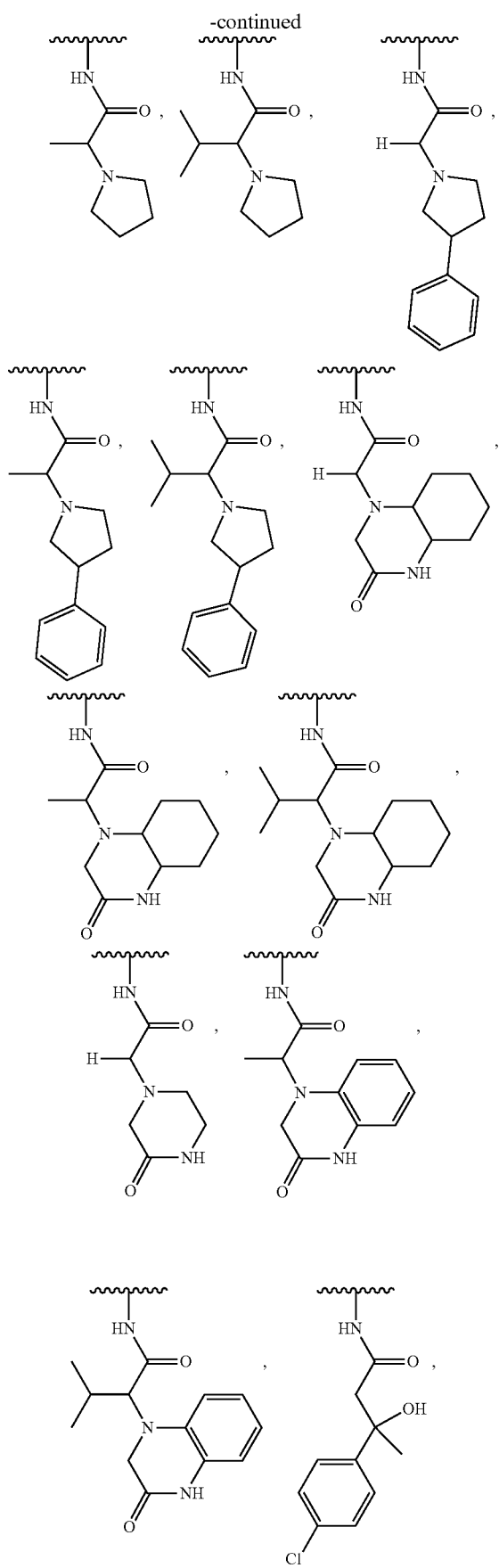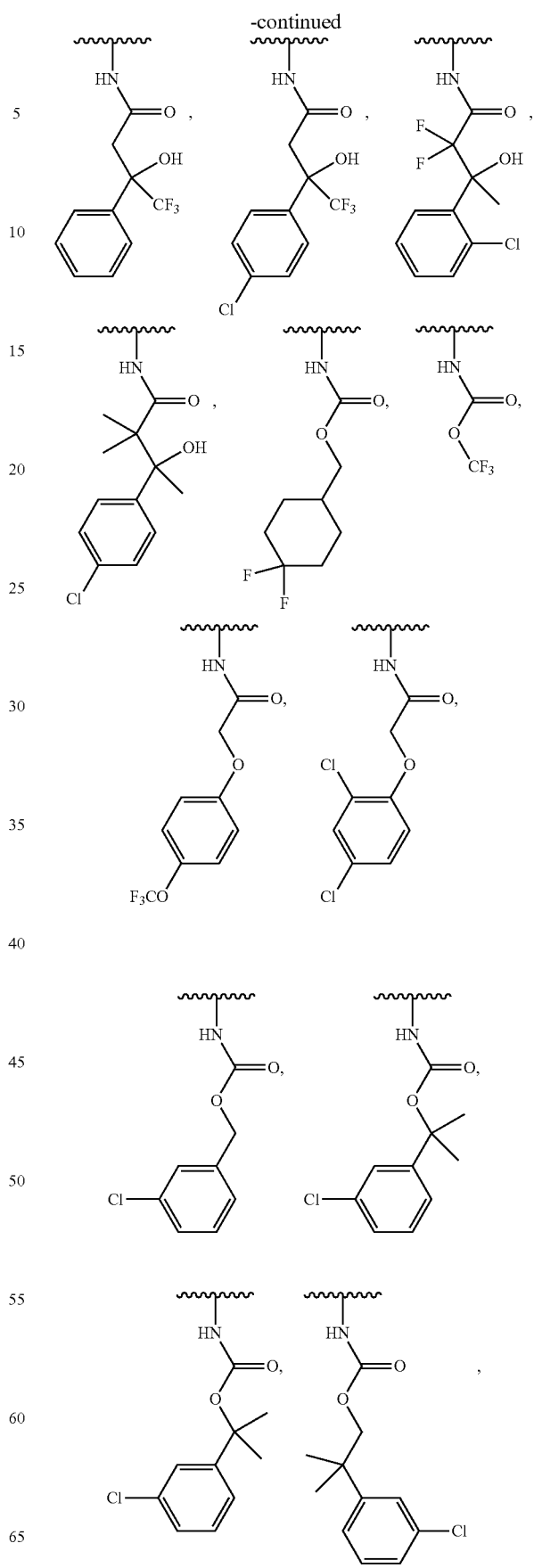

-continued
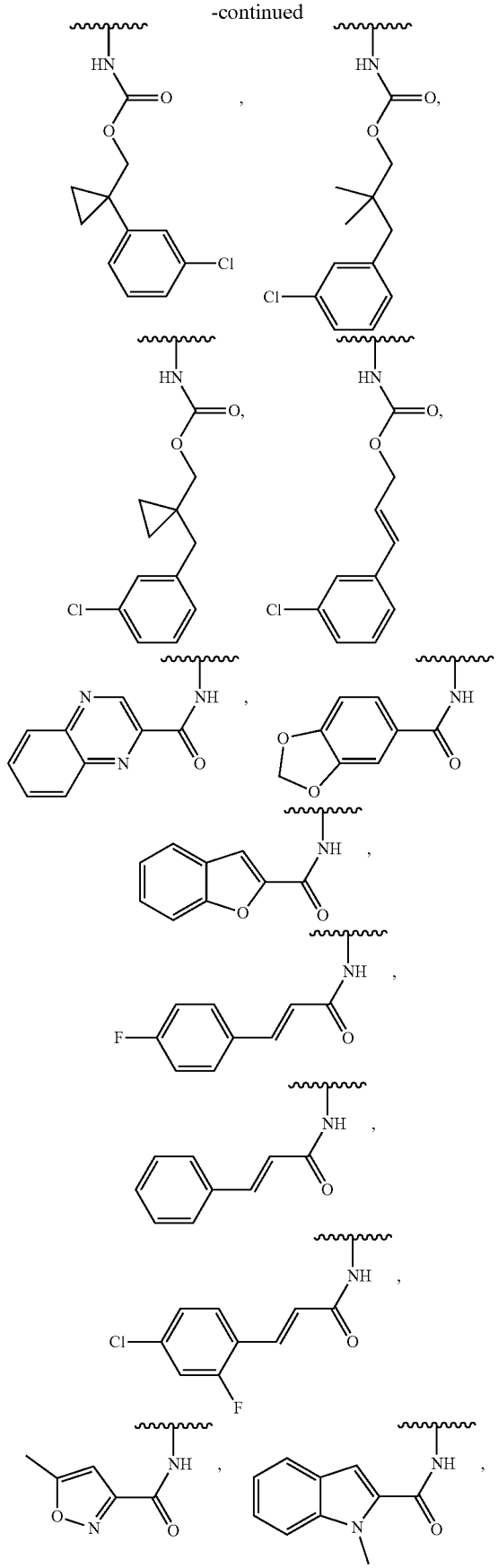
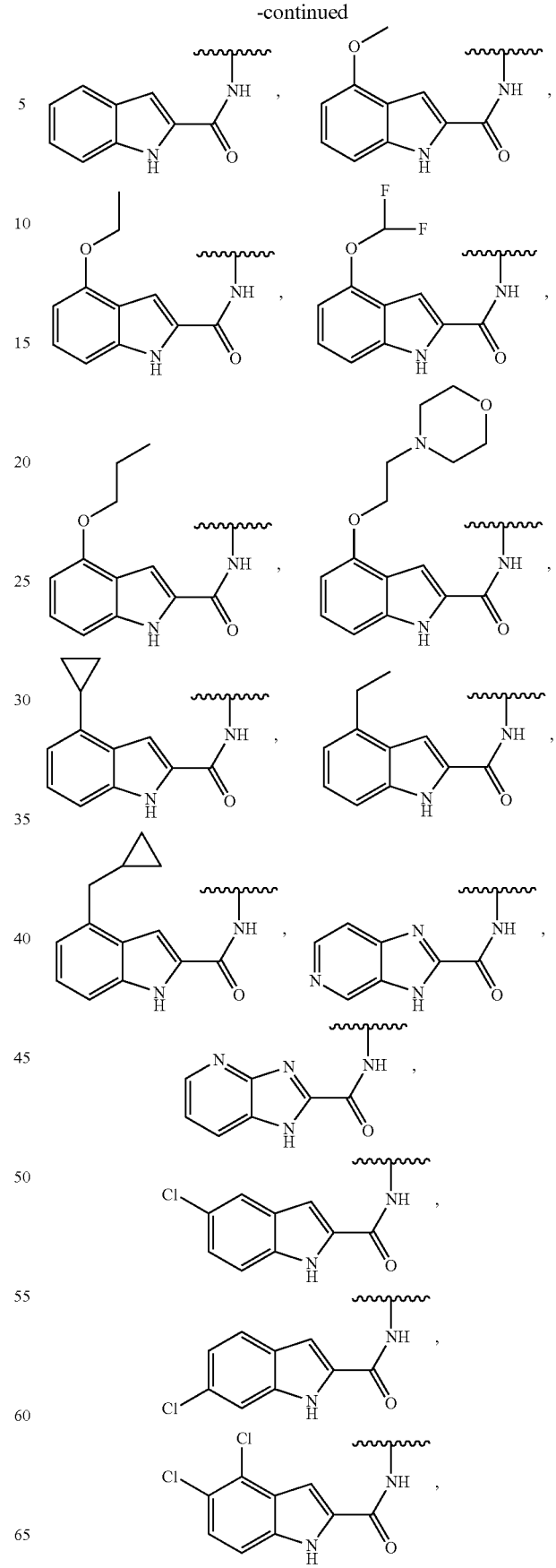

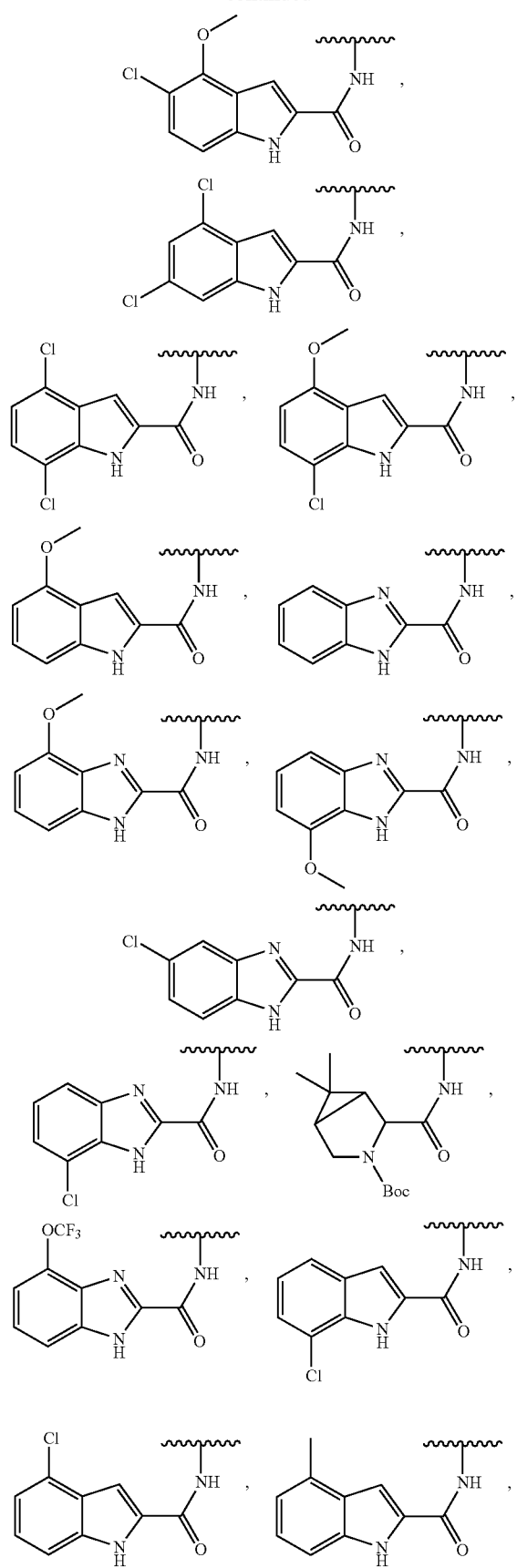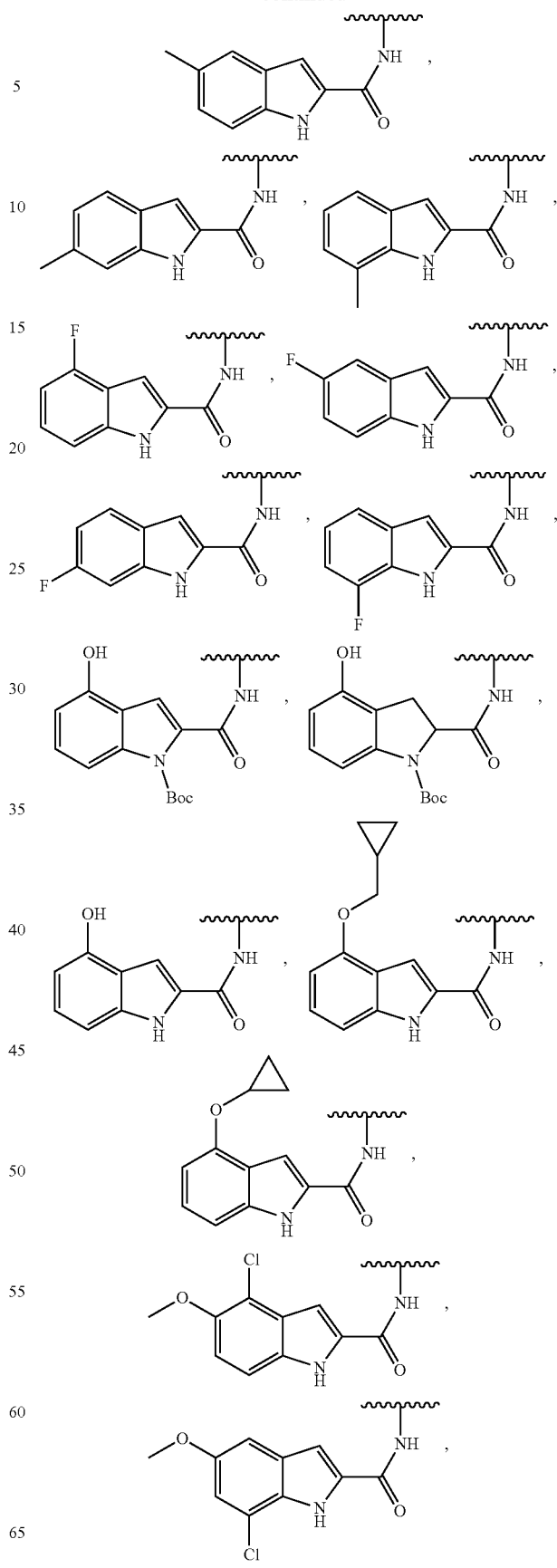

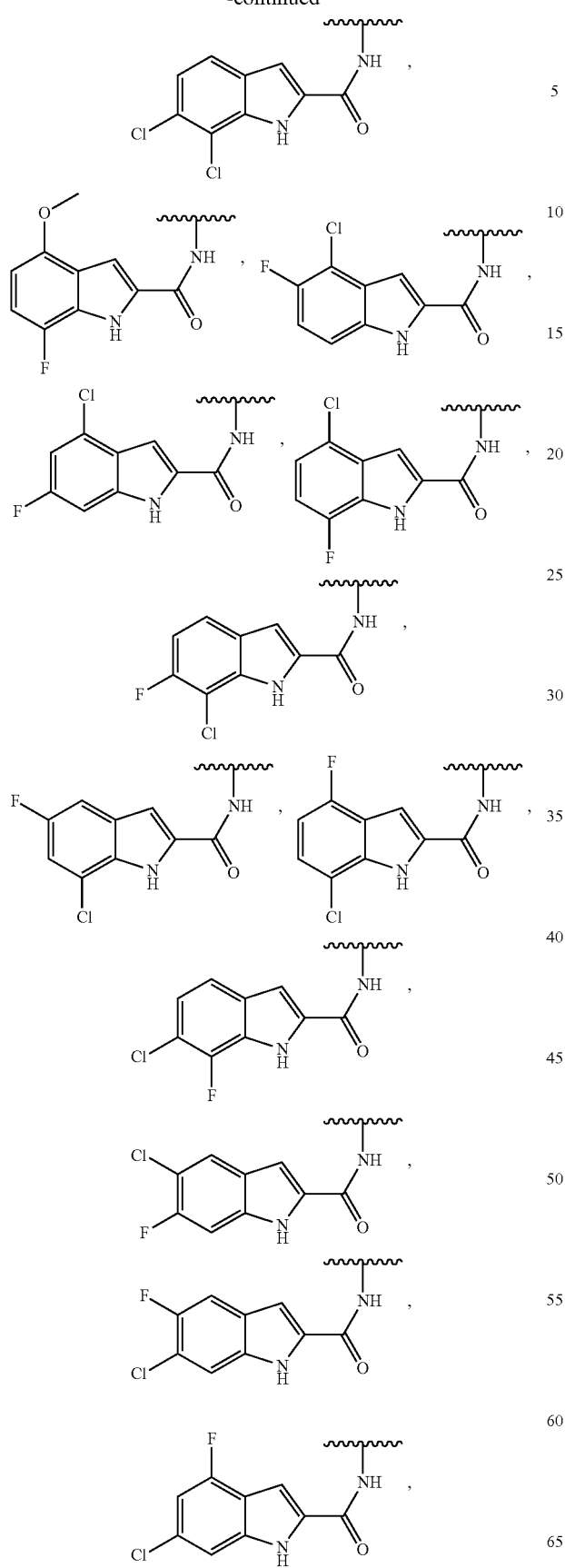
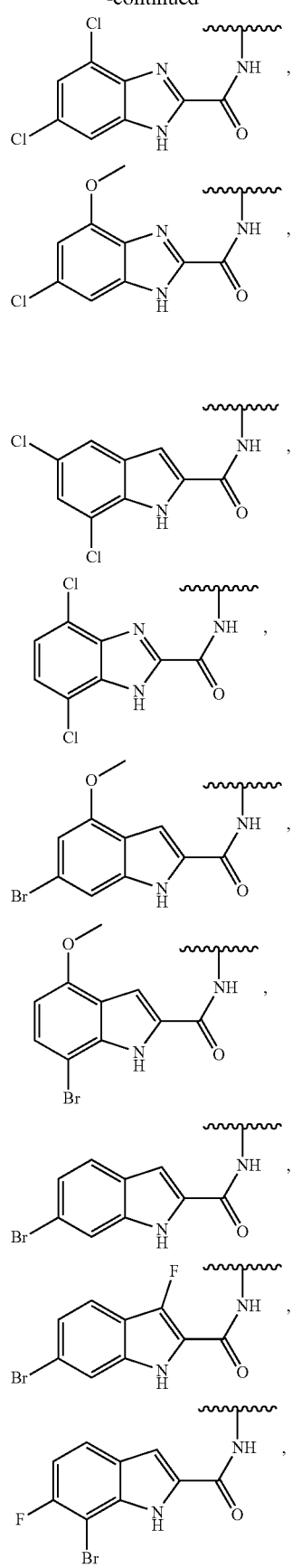

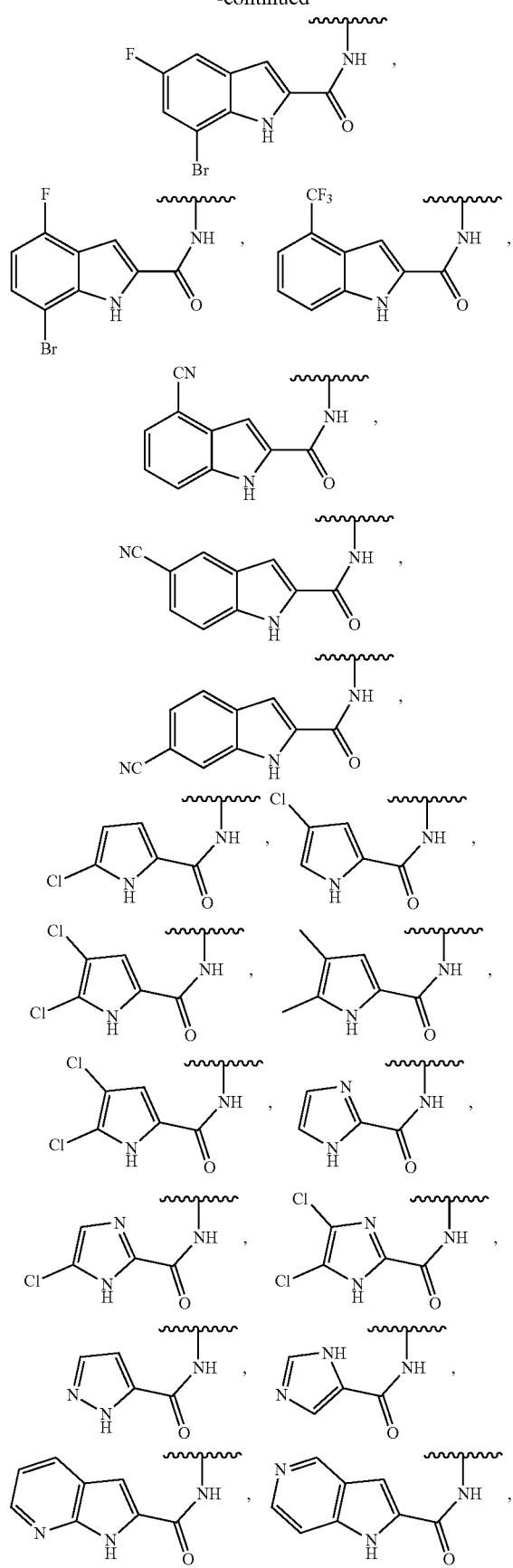
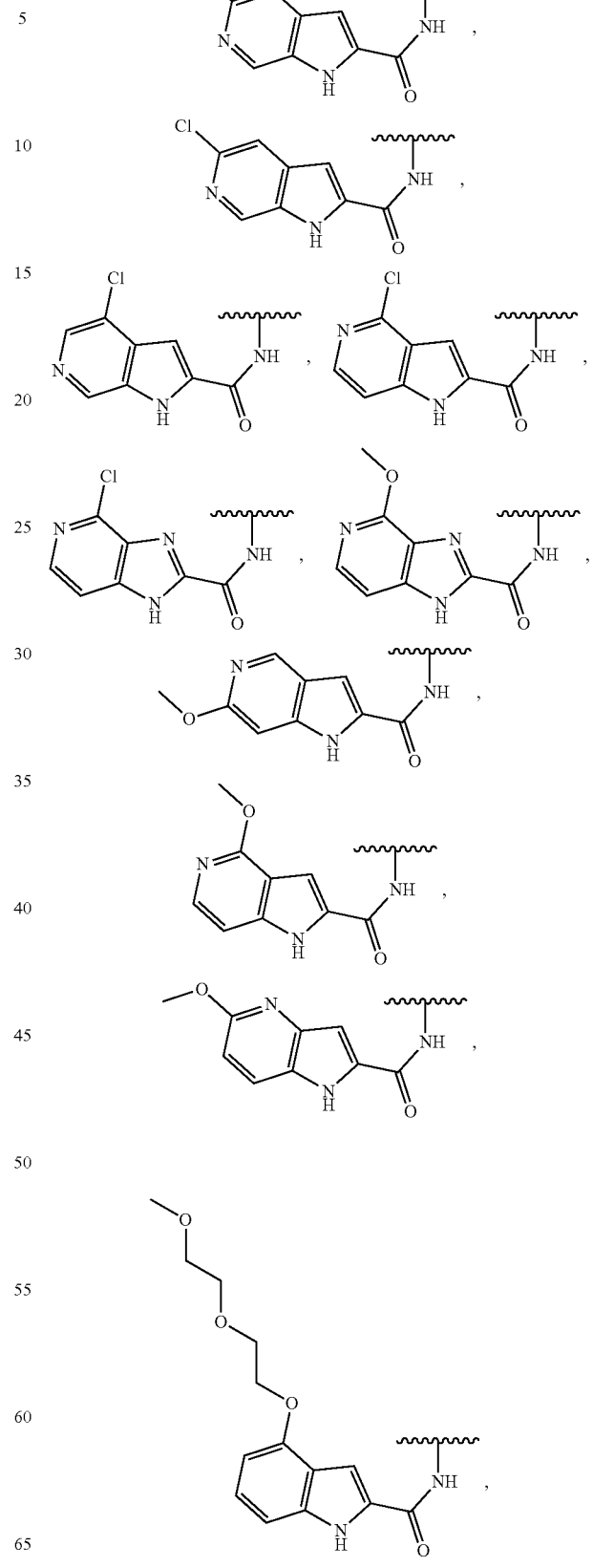

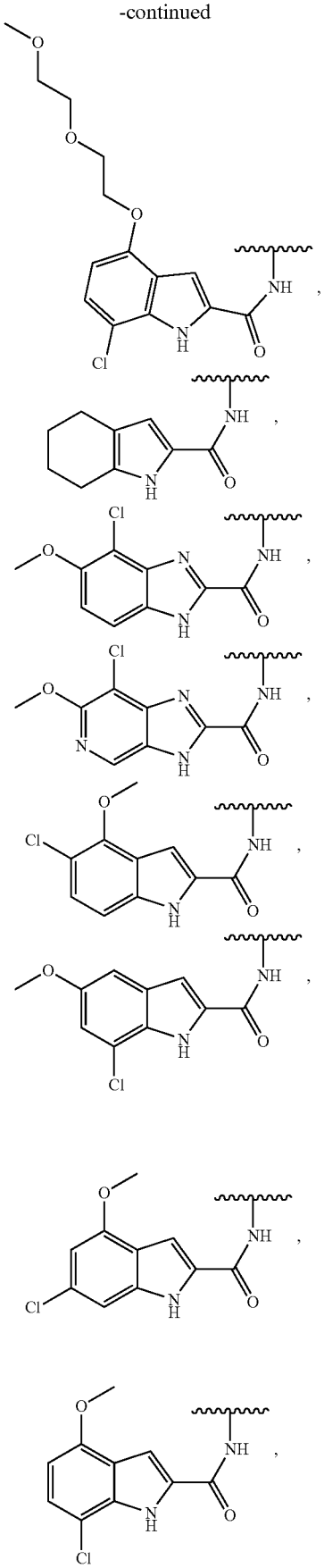
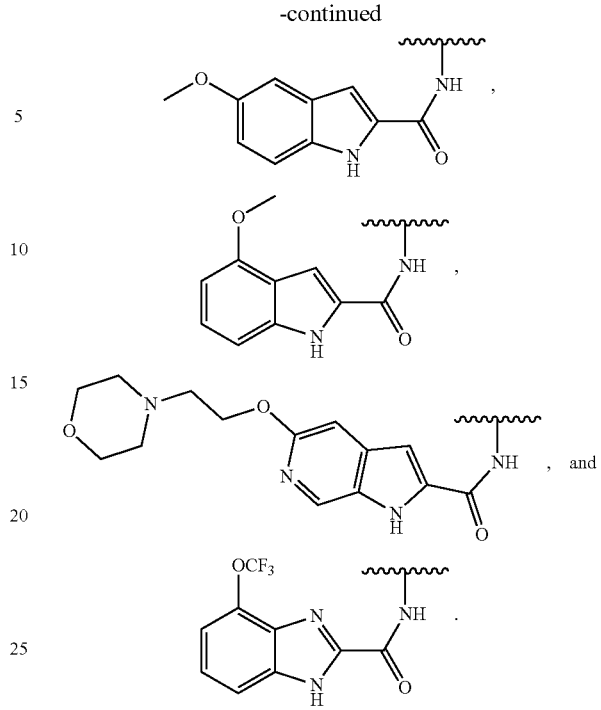
In some embodiments, $R^{1a}$ and $R^2$ are joined to together to form the heterocycle selected from the group consisting of:
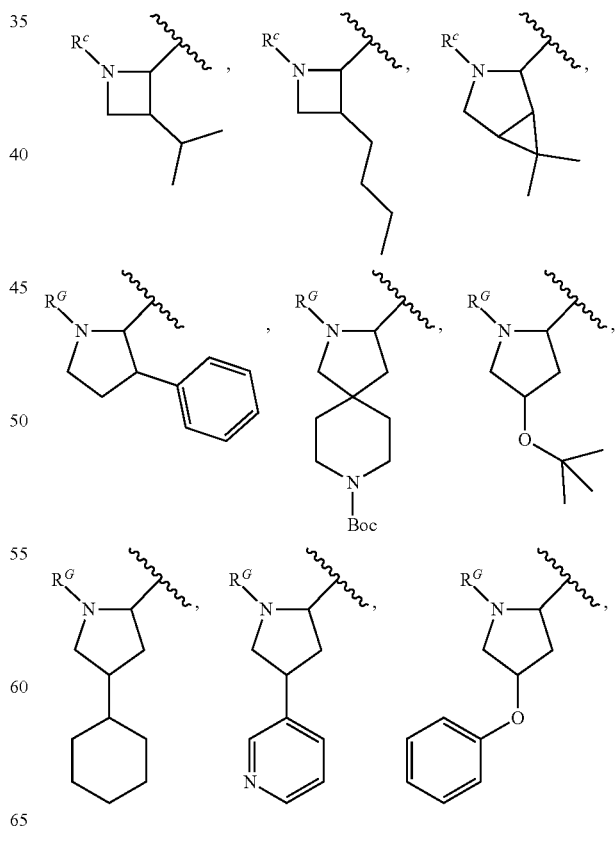

-continued
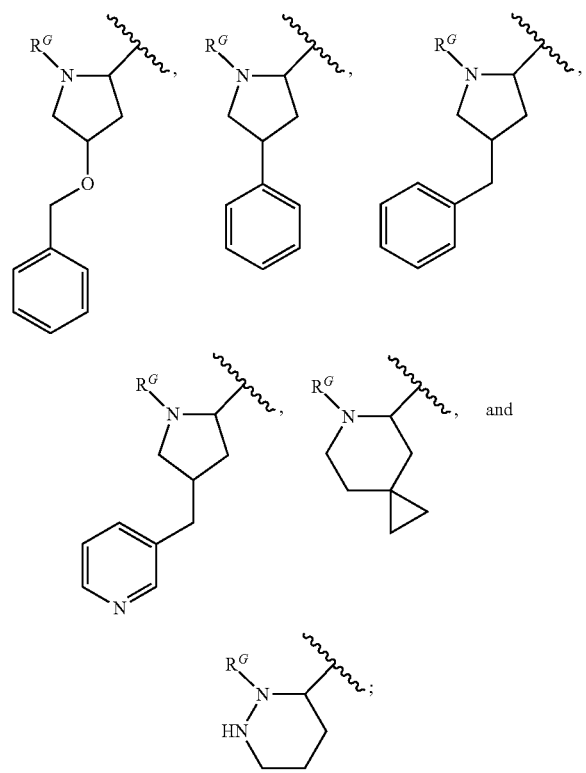
and R[1b] H.
In some embodiments, R[1a] and R[2] are joined to together to form the heterocycle selected from the group consisting of:
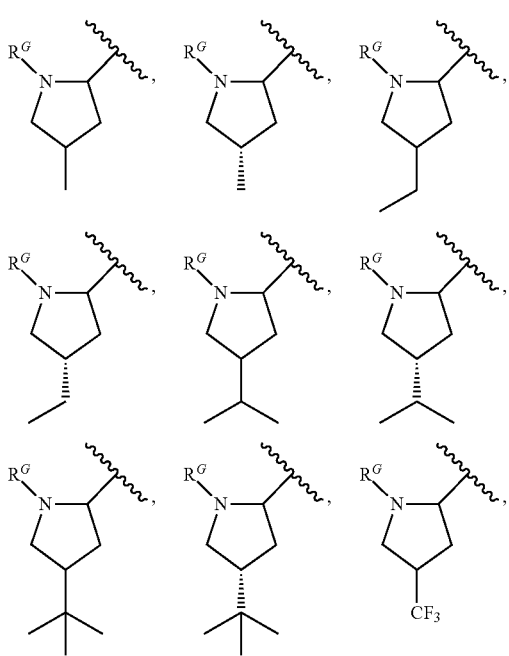
-continued
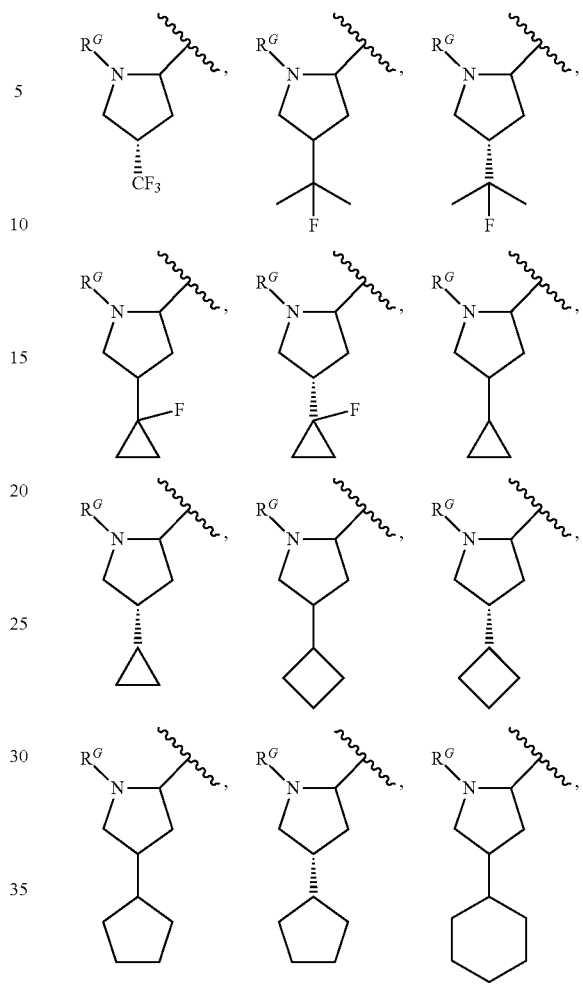

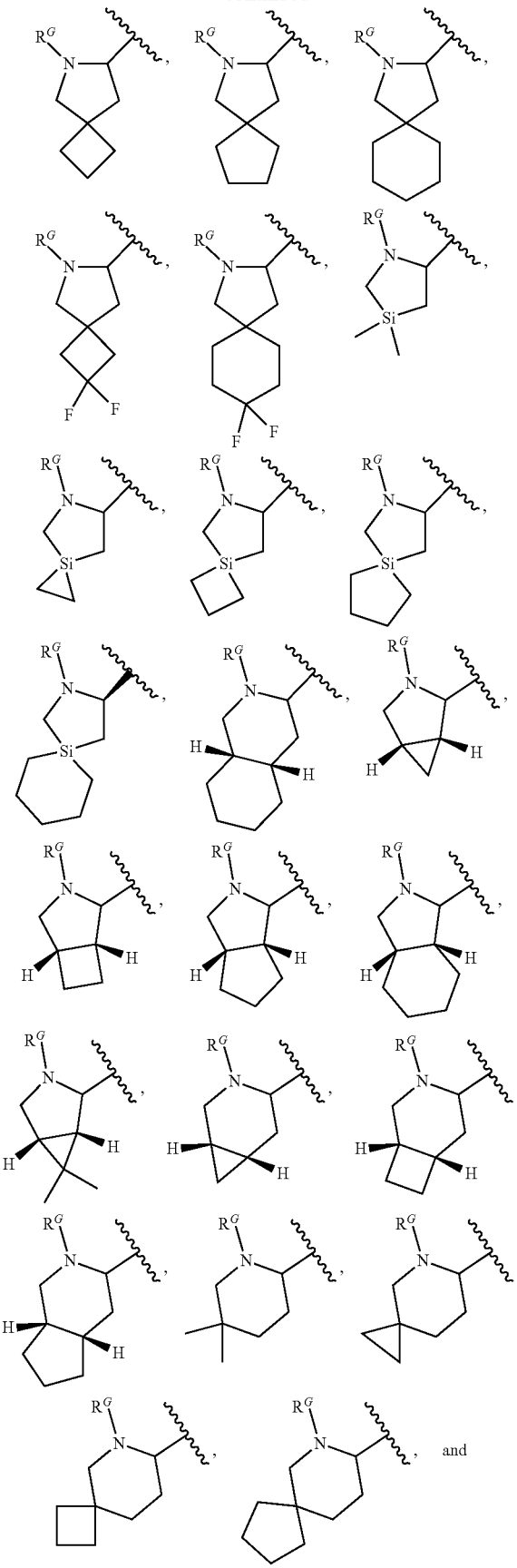
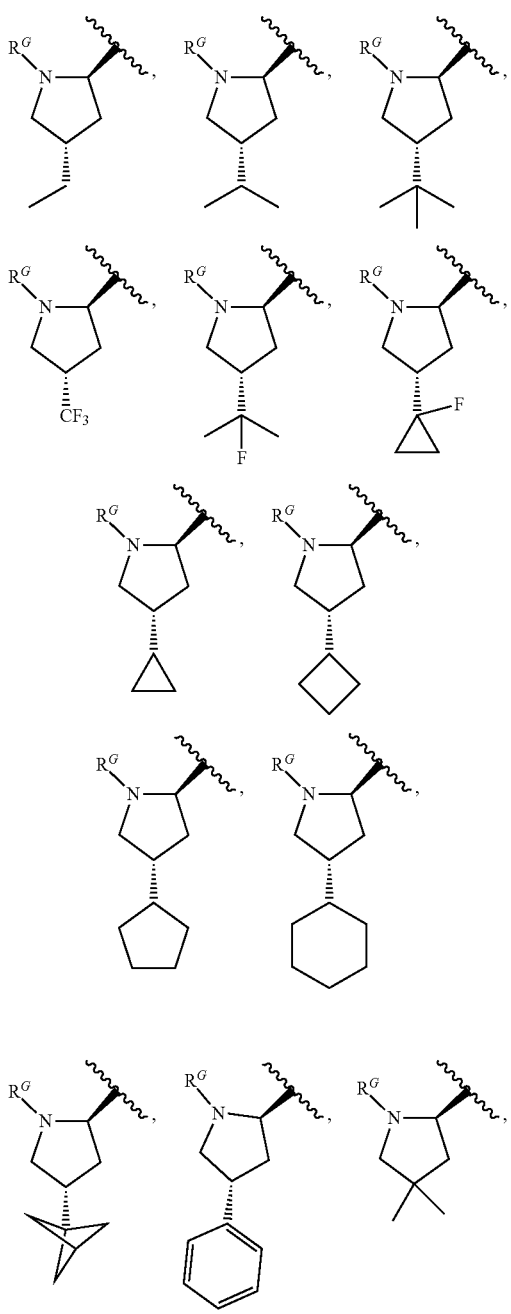
and $R^{1b}$ is H.
In some embodiments, $R^{1a}$ and $R^Z$ are joined to together to form the heterocycle selected from the group consisting of:

-continued

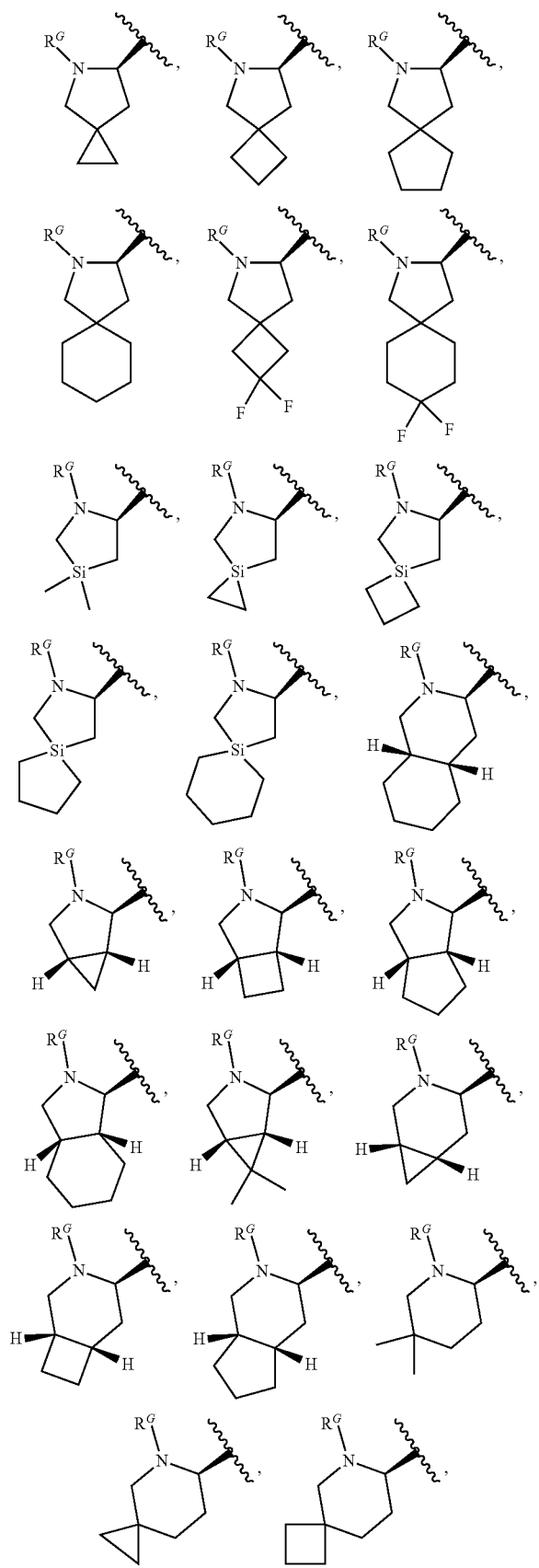

-continued

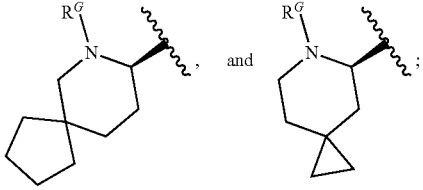

and $R^{1b}$ is H.

In some embodiments, $R^G$ is selected from the group consisting of hydrogen, $C_{1-6}$alkyl optionally substituted by one, two or three $R^{gg}$, —C(=O)—$C_{1-6}$alkyl optionally substituted by one, two or three $R^{hh}$, —C(=O)—$C_{3-6}$cycloalkyl, —C(O)—($C_2$-$C_{10}$alkenyl)-($C_6$-$C_{14}$aryl), —C(O)-(5-10 membered heteroaryl), —C(O)-(4-10 membered heterocyclyl), and —C(O)-(4-10 membered heterocyclyloxy); wherein the aryl, heterocyclyl, or heteroaryl may optionally be substituted by one, two or three $R^{jj}$.

In some embodiments, $R^{gg}$ is independently selected for each occurrence from the group consisting of —C(=O), halo, cyano, —NR$^m$R$^m$, and —NH(C=O)R$^m$. In other embodiments, $R^{hh}$ is independently selected for each occurrence from the group consisting of halo, cyano, —NR$^m$R$^m$, —NR$^m$(C=O)R$^m$, phenyl, cycloalkyl, heterocyclyl and $C_1$-$C_6$alkoxy. In further embodiments, $R^{jj}$ is independently selected for each occurrence from the group consisting of halo, oxo, hydroxyl, cyano, $C_1$-$C_6$alkyl, $C_{1-6}$haloalkyl, $C_1$-$C_6$alkoxy, $C_{3-6}$cycloalkyl, SF$_5$, and NH$_2$.

In certain embodiments, R$^m$ is independently selected for each occurrence from the group consisting of hydrogen, $C_{1-3}$alkyl (optionally substituted by one, two or three F), phenyl (optionally substituted by halo), —S(O)$_2$—CH$_3$, $C_{3-6}$cycloalkyl (optionally substituted by one, two, or three F), and 5-6 membered heteroaryl.

In some embodiments, $R^G$ is selected from the group consisting of H, $C_{1-6}$alkyl (optionally substituted by one, two or three substituents each independently selected from the group consisting of —C(=O), halo, cyano, —NR$^m$R$^m$, and —NH(C=O)R$^m$) and C(=O)—$C_{1-6}$alkyl (optionally substituted by one, two or three substituents each independently selected from the group consisting of halo, cyano, —NR$^m$R$^m$, —NR$^m$(C=O)R$^m$, phenyl, cycloalkyl and heterocycle, wherein R$^m$ is selected for each occurrence by H or $C_{1-3}$alkyl (optionally substituted by one, two or three halogens, e.g., F), or $C_3$-$C_6$cycloalkyl (optionally substituted by one, two, or three F).

In some embodiments, $R^G$ is selected from the group consisting of a —C(O)-monocyclic 5-6 membered or —C(O)-bicyclic heteroaryl each having at least one ring nitrogen and optionally substituted by one, two, or three substituents each selected from halo, methoxy, cyano, and hydroxyl; and —C(O)—C(R$^{55}$R$^{56}$)—NH—C(O)—R$^{57}$, wherein R$^{55}$ is H and R$^{56}$ is a straight or branched $C_{1-5}$alkyl (optionally substituted by halo), or R$^{55}$ and R$^{56}$ taken together with the carbon to which they are attached form a $C_{3-5}$cycloalkyl (optionally substituted by halo) and wherein R$^{57}$ is $C_{1-3}$alkyl (optionally substituted by one, two or three halo).

In some embodiments, $R^G$ is selected from the group consisting of
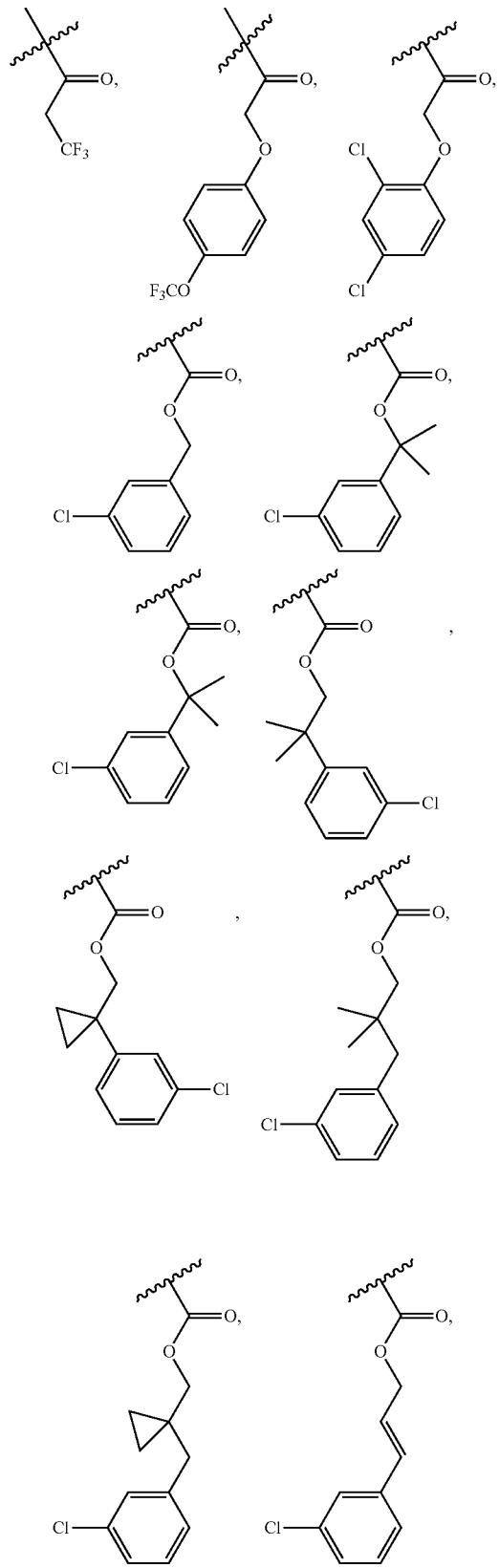
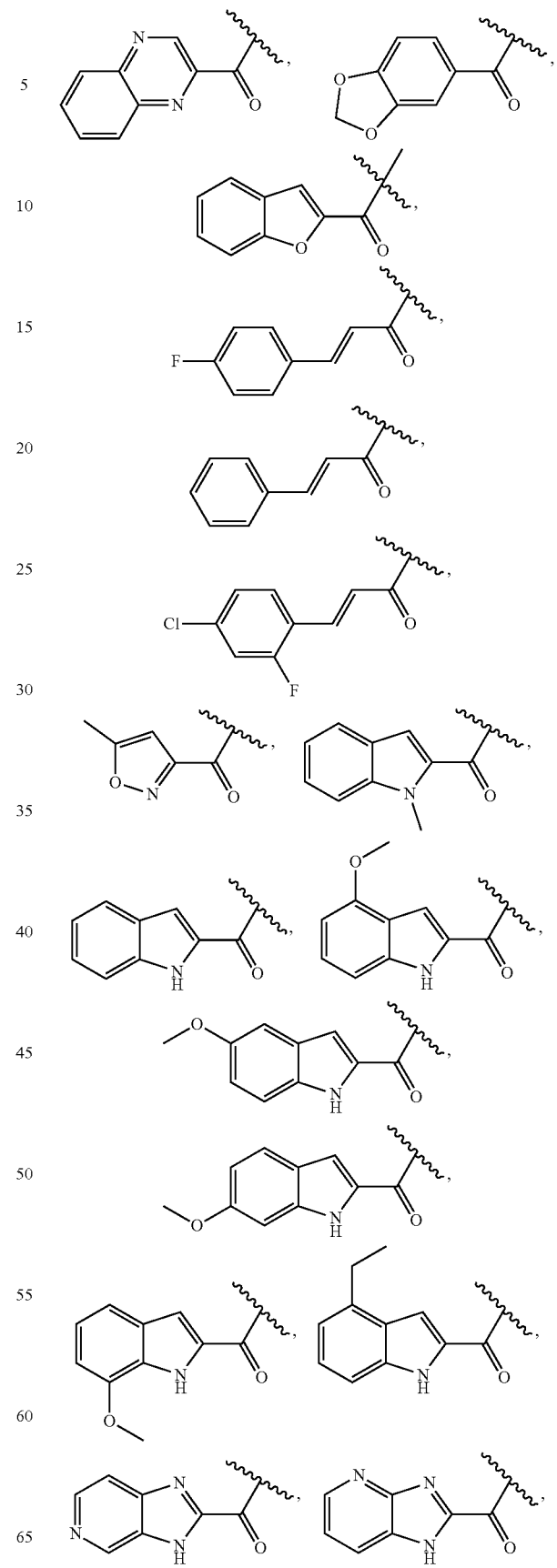

-continued

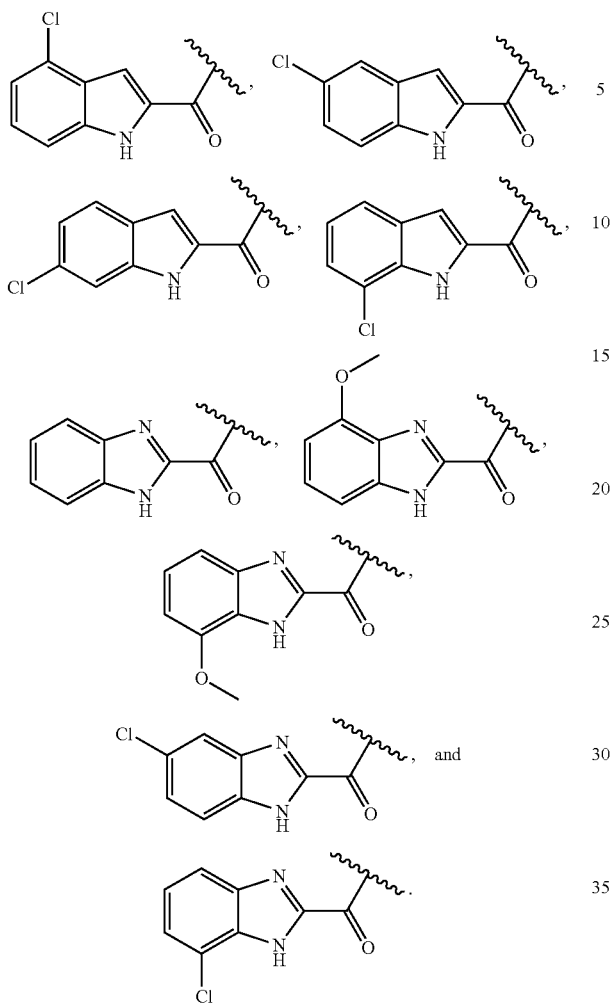

In some embodiments, $R^G$ is

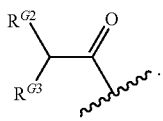

In some embodiments, the compound is represented by

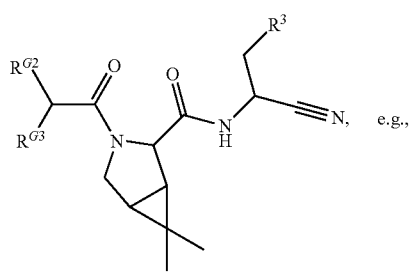, e.g.,

-continued

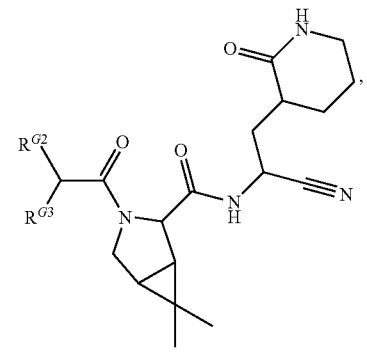

wherein $R^{G3}$ is selected from the group consisting of H, $C_{1-6}$alkyl, $C_{3-6}$cycloalkyl (e.g., t-butyl, propyl, cyclopropyl), phenyl and heterocycle; and $R^{G2}$ is —NH(C=O)R$^m$, wherein R$^m$ is selected for each occurrence by H, methyl or CF$_3$.

In some embodiments, the compound is represented by

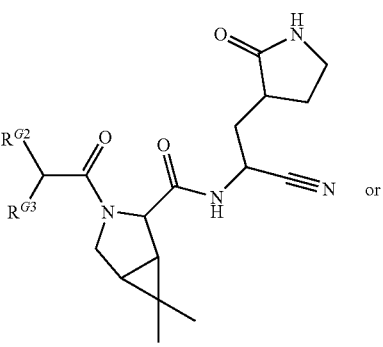 or

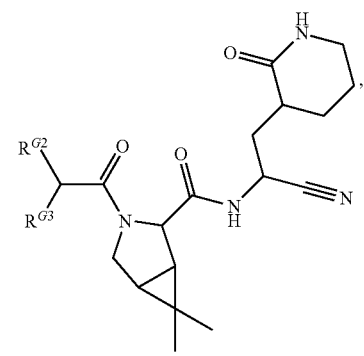

wherein $R^{G3}$ is selected from the group consisting of H, $C_{1-6}$alkyl, $C_{3-6}$cycloalkyl, phenyl and heterocycle; and $R^{G2}$ is —NH(C=O)R$^m$, wherein R$^m$ is selected for each occurrence by H, methyl or CF$_3$.

In some embodiments, the compound is represented by

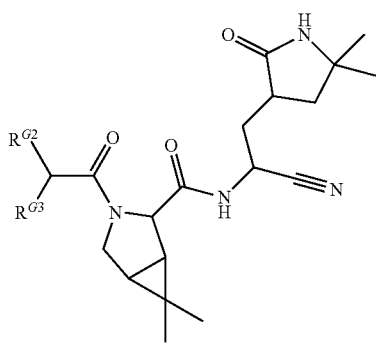

or

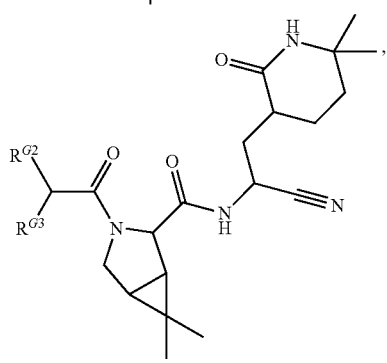

wherein $R^{G3}$ is selected from the group consisting of H, $C_{1-6}$alkyl, $C_{3-6}$cycloalkyl, phenyl and heterocycle; and $R^{G2}$ is —NH(C=O)$R^m$, wherein $R^m$ is selected for each occurrence by H, methyl or $CF_3$.

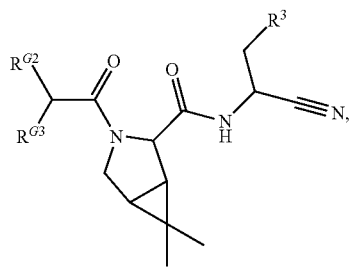

In some embodiments, the compound is represented by wherein $R^{G3}$ is selected from the group consisting of H, $C_{1-6}$alkyl (optionally substituted by one, two or three $C_1$-$C_6$alkoxy), $C_{3-6}$cycloalkyl, phenyl and heterocycle; and $R^{G2}$ is selected from the group consisting of —NH($C_{1-3}$alkyl) (optionally substituted by one, two or three substituents each independently selected from the group consisting of halo, optionally substituted phenyl, —S(O)$_2$—CH$_3$, $C_{3-6}$cycloalkyl, and 5-6 membered heteroaryl) and —NH(C=O)$R^m$, wherein $R^m$ is selected for each occurrence by H, $C_{1-6}$alkyl (optionally substituted by one, two or three substituents each independently selected from the group consisting of halo, cyano and $C_1$-$C_6$alkoxy), CHF$_2$, CF$_3$, or 5-6 membered heteroaryl (optionally substituted by halo, cyano, hydroxyl, NH$_2$, $C_{1-6}$alkyl, $C_{3-6}$cycloalkyl, $C_1$-$C_6$alkoxy, CHF$_2$, and CF$_3$).

In some embodiments, the compound is represented by

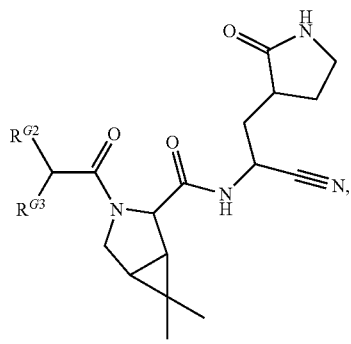

wherein $R^{G3}$ is selected from the group consisting of H, $C_{1-6}$ alkyl (optionally substituted by one, two or three $C_1$-$C_6$alkoxy), $C_{3-6}$cycloalkyl, phenyl and heterocycle; and $R^{G2}$ is selected from the group consisting of —NH($C_{1-3}$alkyl) (optionally substituted by one, two or three substituents each independently selected from the group consisting of halo, optionally substituted phenyl, —S(O)$_2$—CH$_3$, $C_{3-6}$cycloalkyl, and 5-6 membered heteroaryl) and —NH(C=O)$R^m$, wherein $R^m$ is selected for each occurrence by H, $C_{1-6}$alkyl (optionally substituted by one, two or three substituents each independently selected from the group consisting of halo, cyano and $C_1$-$C_6$alkoxy), CHF$_2$, CF$_3$, or 5-6 membered heteroaryl (optionally substituted by halo, cyano, hydroxyl, NH$_2$, $C_{1-6}$alkyl, $C_{3-6}$cycloalkyl, $C_1$-$C_6$alkoxy, CHF$_2$, and CF$_3$).

In some embodiments, $R^{G3}$ is selected from the group consisting of

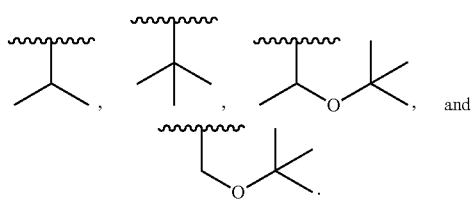

In some embodiments, $R^{G2}$ is selected from the group consisting of

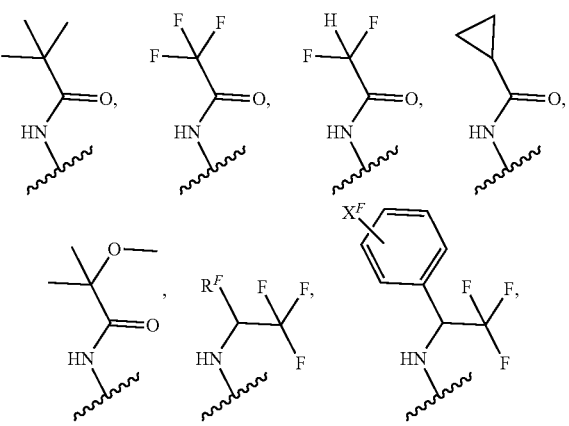

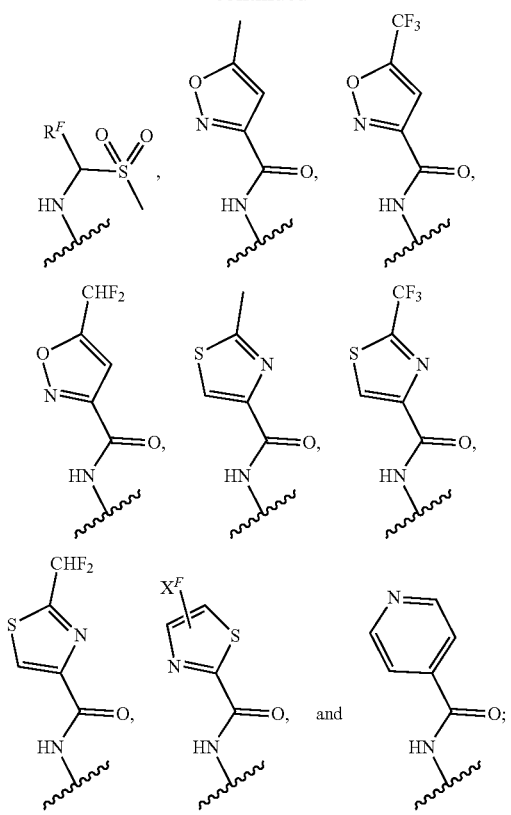

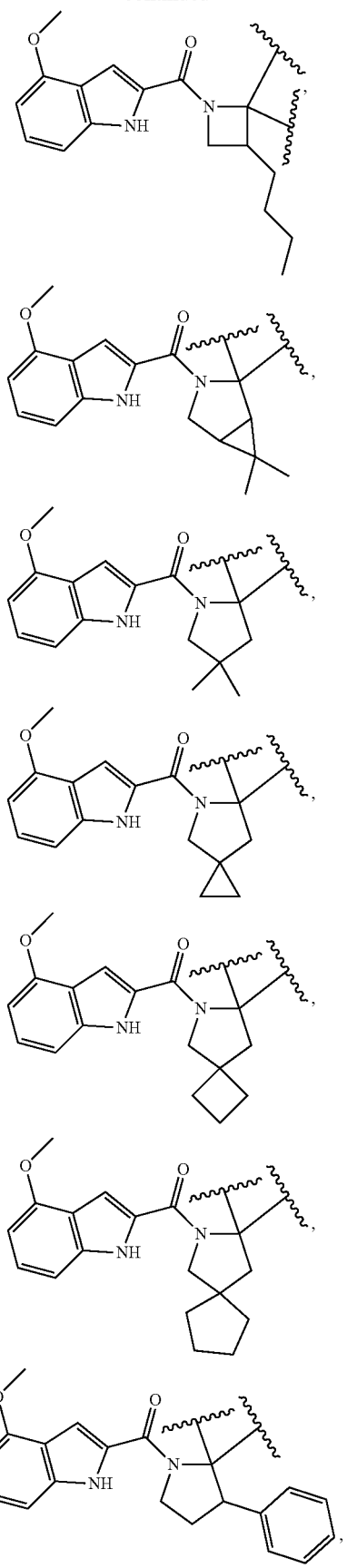

wherein $R^F$ is selected from the group consisting of $C_{1-6}$alkyl, $C_{3-6}$cycloalkyl, phenyl and 5-6 membered heteroaryl, wherein $R^F$ may optionally be substituted by one, two or three substituents selected from the group consisting of halo, cyano, hydroxyl and $C_1$-$C_6$alkoxy; and $X^F$ is selected from the group consisting of H, halo, cyano, hydroxyl, $NH_2$, $C_{1-6}$alkyl, $C_{3-6}$cycloalkyl, $C_1$-$C_6$alkoxy, and $C_{1-6}$haloalkyl.

In some embodiments, $R^{1a}$ and $R^2$ are joined to together to form the heterocycle selected from the group consisting of:

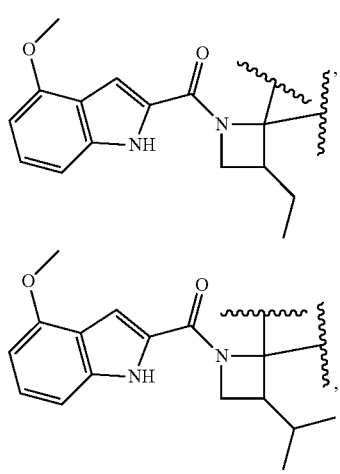

-continued
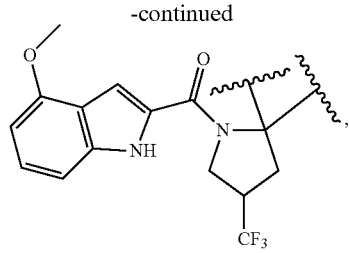
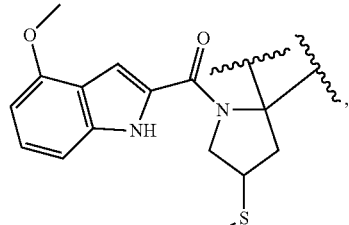
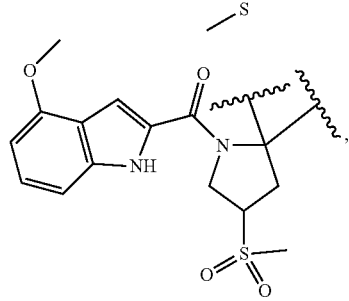
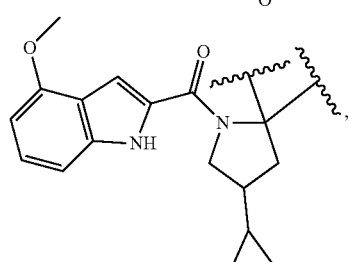
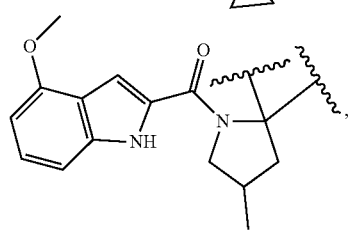
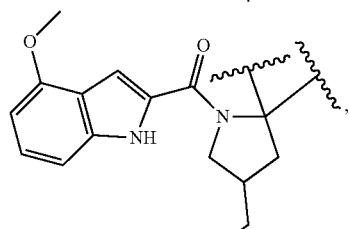
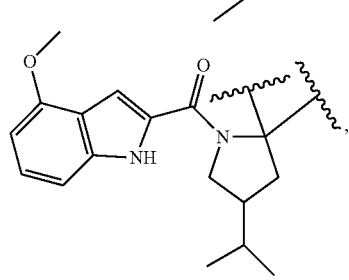
-continued
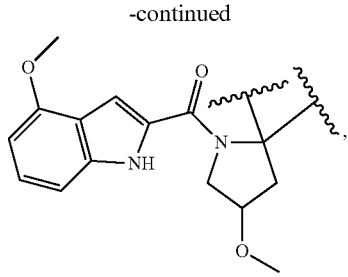
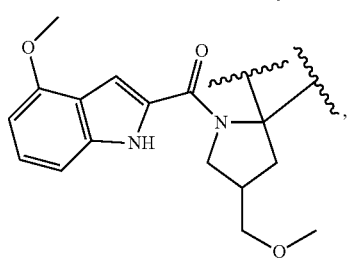
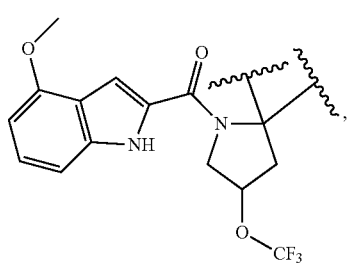
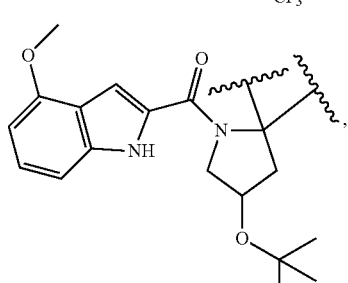
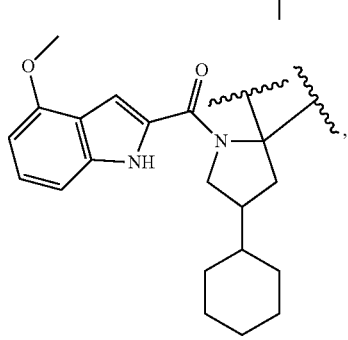
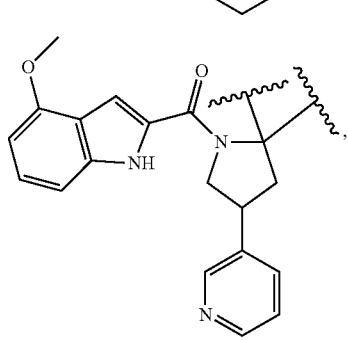

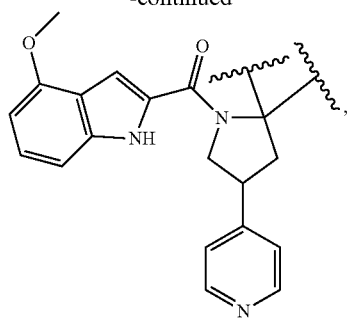
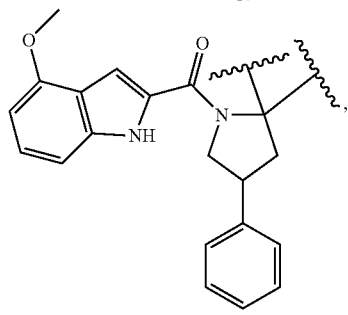
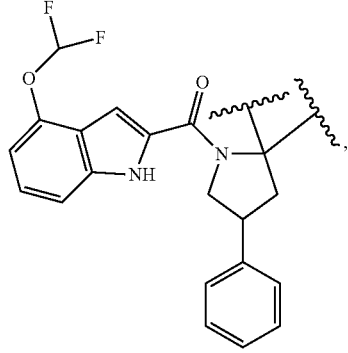
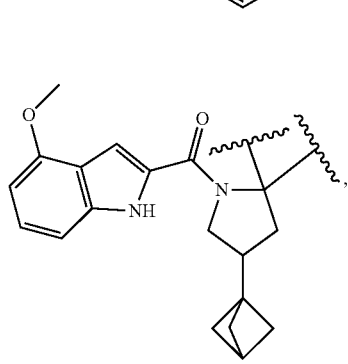
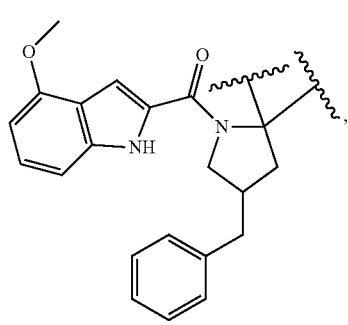
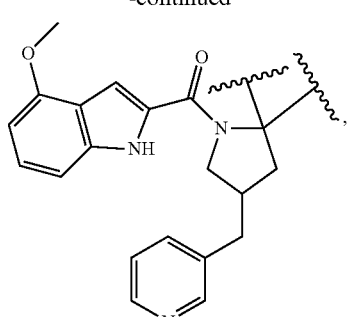
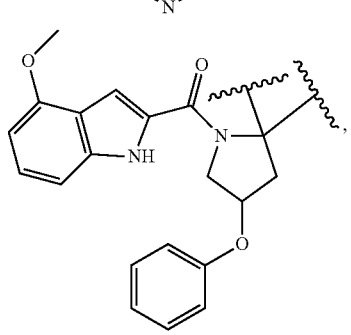
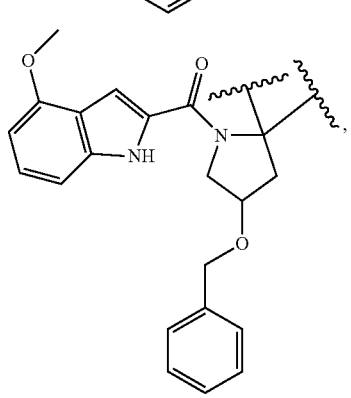
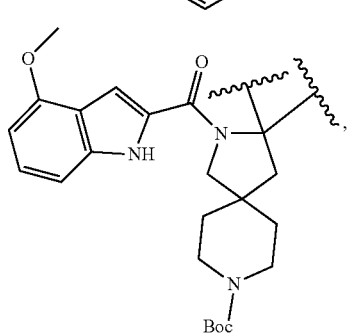
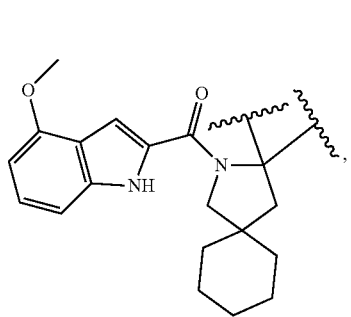

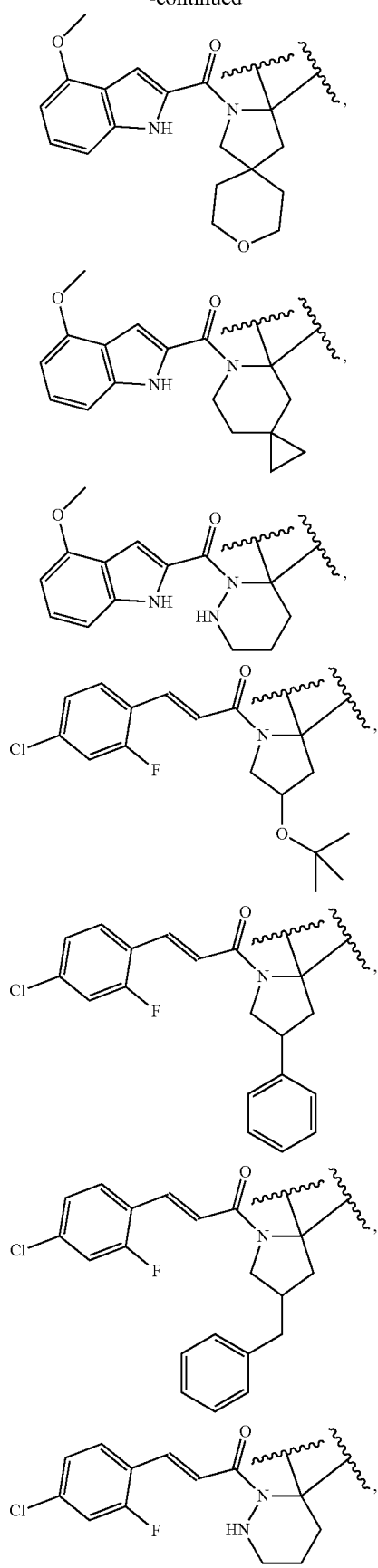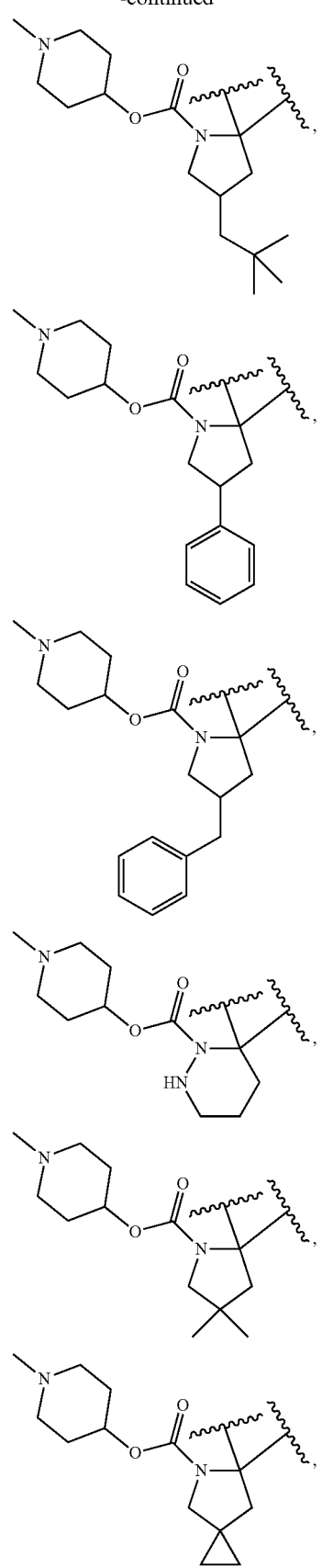

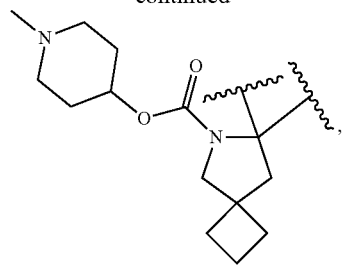
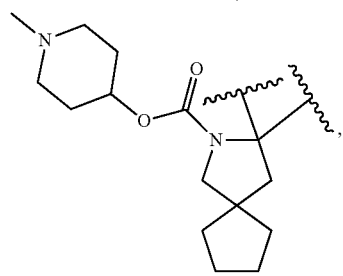
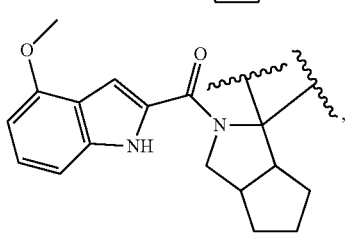
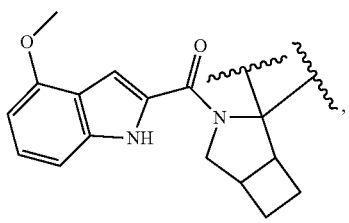
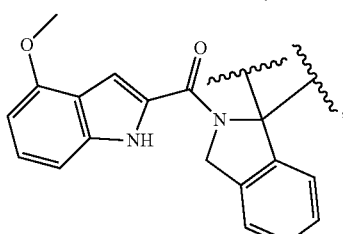
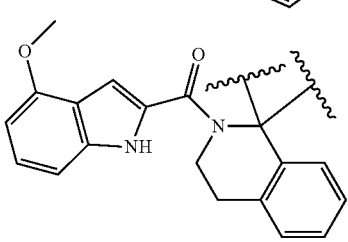
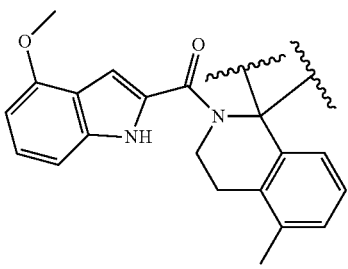
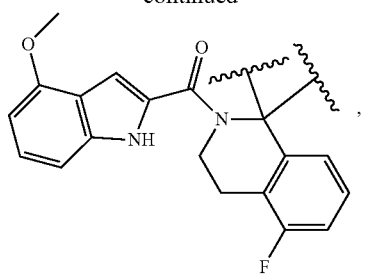
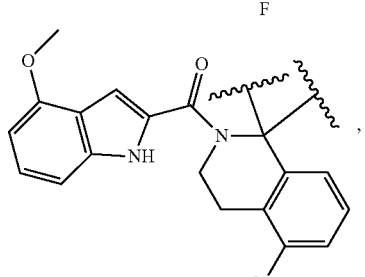
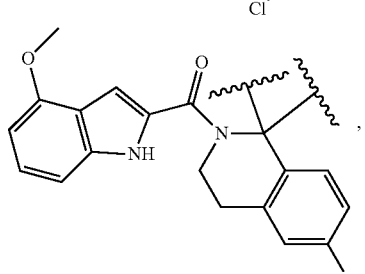
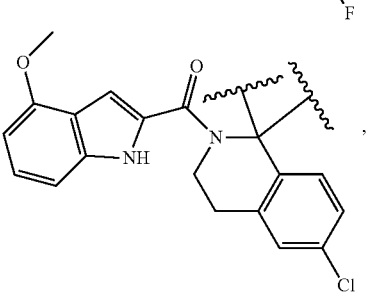
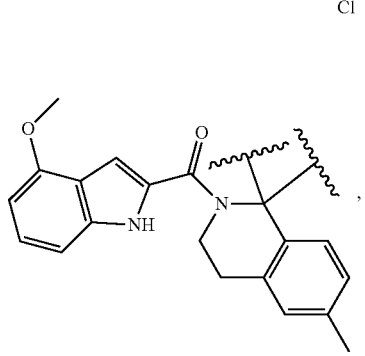
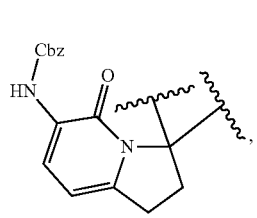
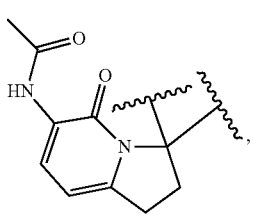

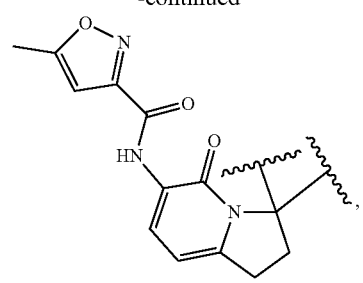
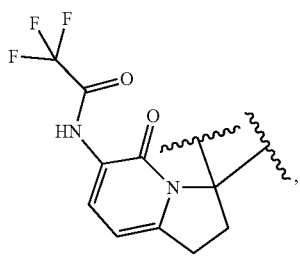
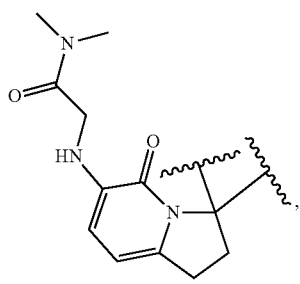
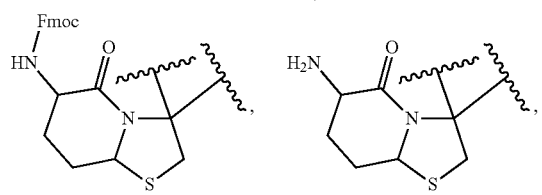
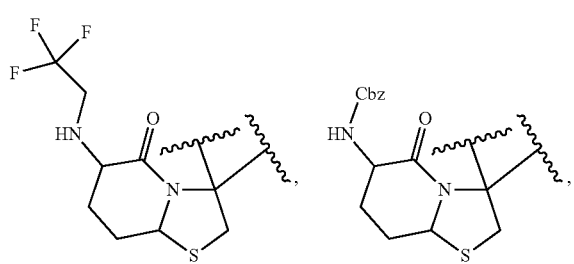
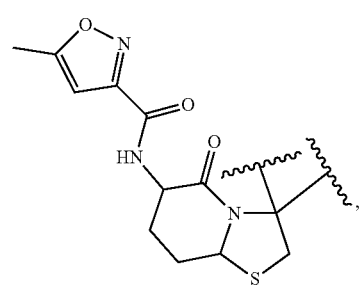
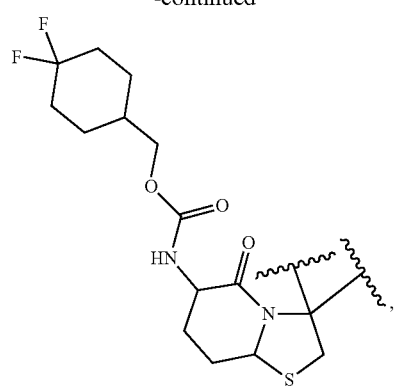
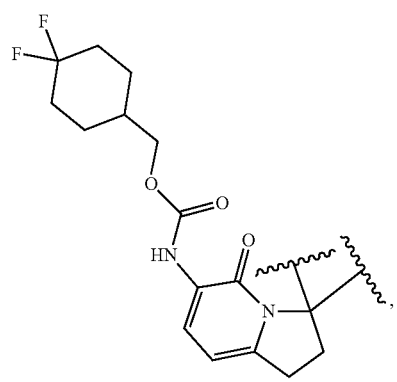
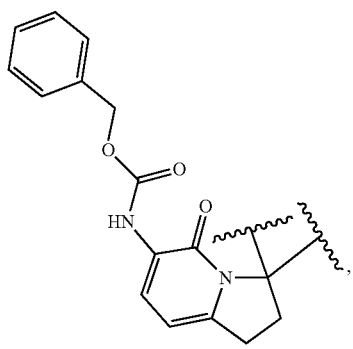
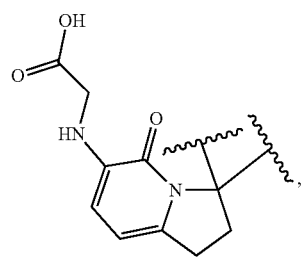
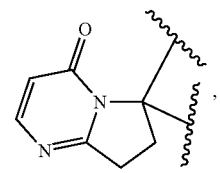
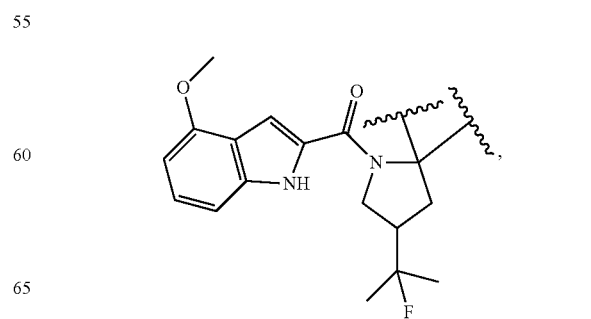

-continued
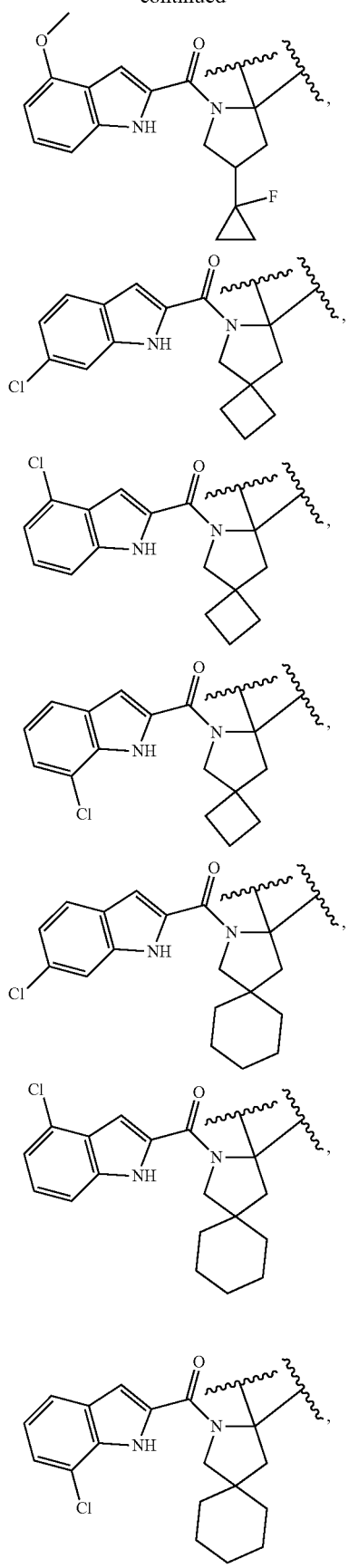
-continued
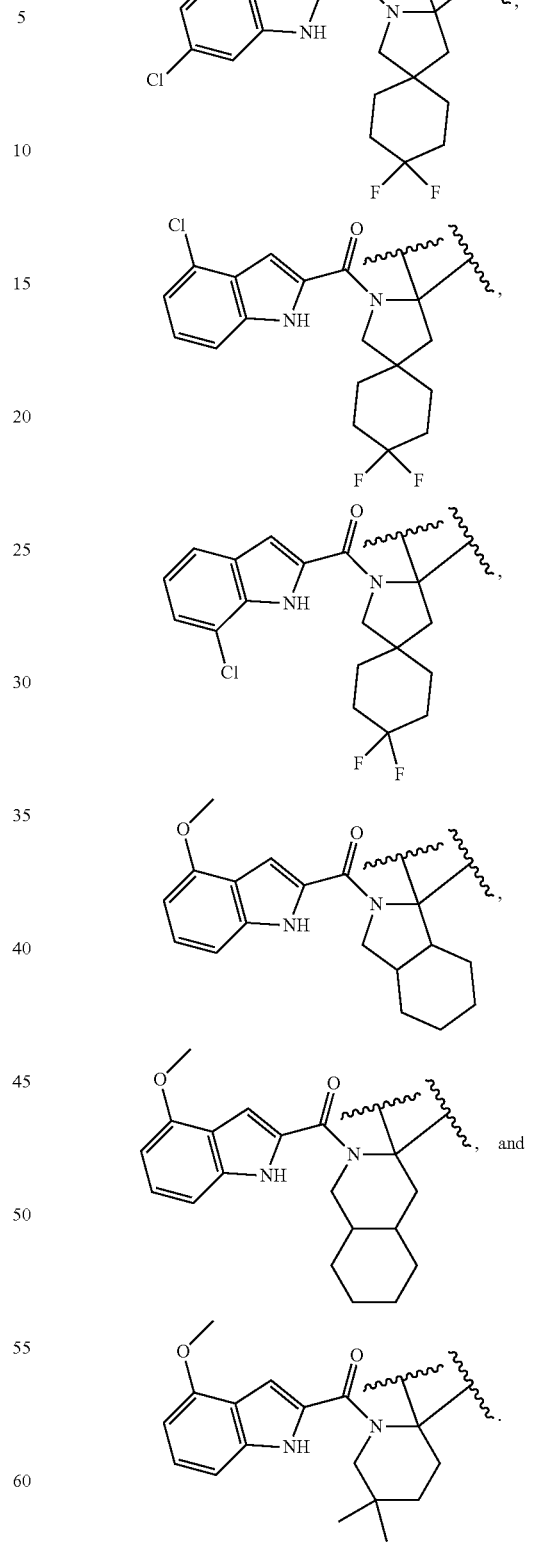
and
In some embodiments, the compound is selected from the group consisting of the compounds identified in Table 1 and Table 2 below:

TABLE 1

Exemplary compounds.

| Cmpd No. | Structure |
| --- | --- |
| 100 | 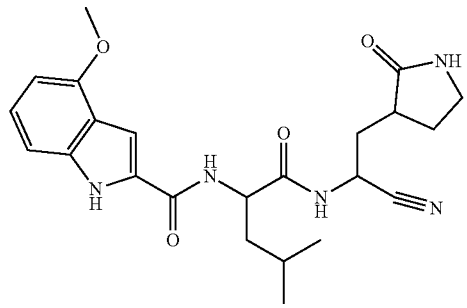 [SMILES: COc1cccc2[nH]c(C(=O)NC(CC(C)C)C(=O)NC(C#N)CC3CCNC3=O)cc12] |
| 101 | 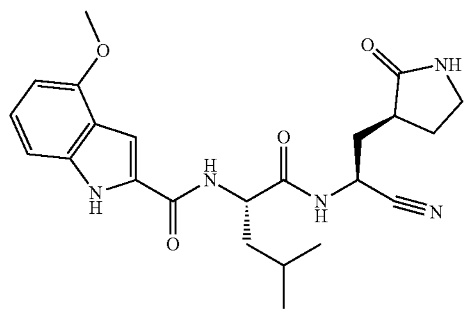 [SMILES: COc1cccc2[nH]c(C(=O)N[C@@H](CC(C)C)C(=O)N[C@H](C#N)C[C@@H]3CCNC3=O)cc12] |
| 102 | 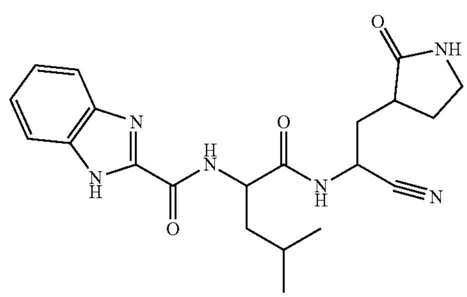 [SMILES: CC(C)CC(NC(=O)c1nc2ccccc2[nH]1)C(=O)NC(C#N)CC1CCNC1=O] |
| 103 | 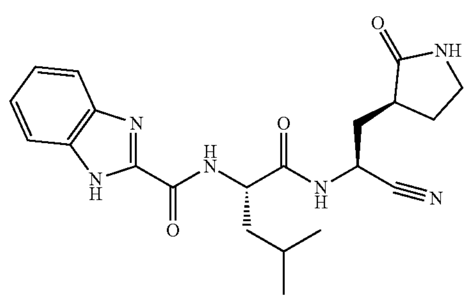 [SMILES: CC(C)C[C@H](NC(=O)c1nc2ccccc2[nH]1)C(=O)N[C@H](C#N)C[C@@H]1CCNC1=O] |
| 104 | 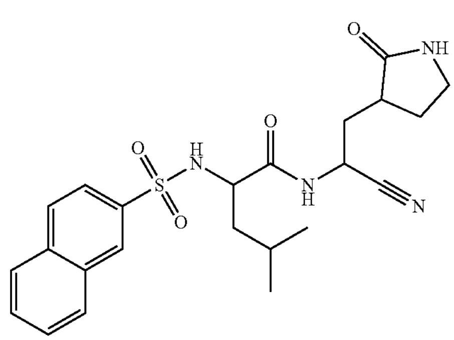 [SMILES: CC(C)CC(NS(=O)(=O)c1ccc2ccccc2c1)C(=O)NC(C#N)CC1CCNC1=O] |

TABLE 1-continued

Exemplary compounds.

| Cmpd No. | Structure |
| --- | --- |
| 105 | 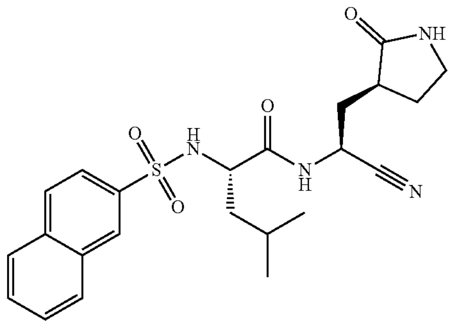 [SMILES: CC(C)C[C@H](NS(=O)(=O)c1ccc2ccccc2c1)C(=O)N[C@H](C#N)C[C@@H]1CCNC1=O] |
| 120 | 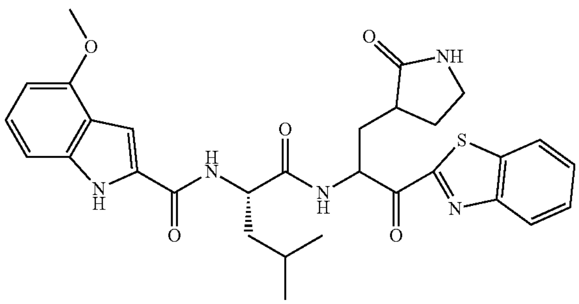 [SMILES: COc1cccc2[nH]c(C(=O)N[C@@H](CC(C)C)C(=O)NC(CC3CCNC3=O)C(=O)c3nc4ccccc4s3)cc12] |
| 121 | 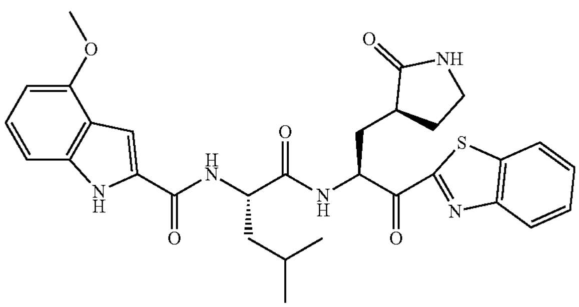 [SMILES: COc1cccc2[nH]c(C(=O)N[C@@H](CC(C)C)C(=O)N[C@@H](C[C@@H]3CCNC3=O)C(=O)c3nc4ccccc4s3)cc12] |
| 122 | 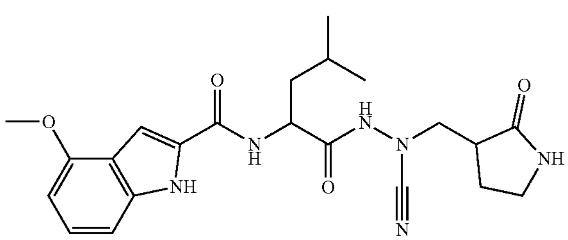 [SMILES: COc1cccc2[nH]c(C(=O)NC(CC(C)C)C(=O)NN(C#N)CC3CCNC3=O)cc12] |
| 123 | 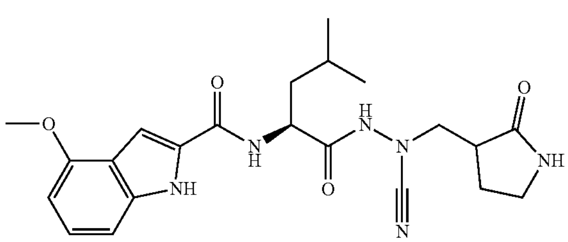 [SMILES: COc1cccc2[nH]c(C(=O)N[C@@H](CC(C)C)C(=O)NN(C#N)CC3CCNC3=O)cc12] |

TABLE 1-continued
Exemplary compounds.
| Cmpd No. | Structure |
|---|---|
| 124 | 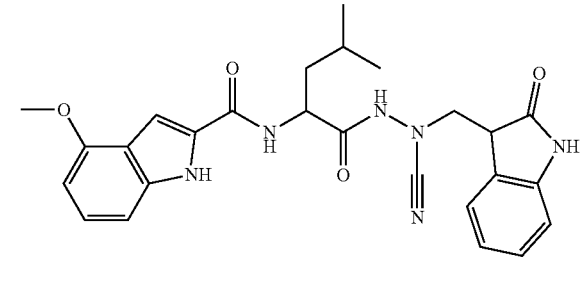 [SMILES: COc1cccc2[nH]c(C(=O)NC(CC(C)C)C(=O)NN(C#N)CC3C(=O)Nc4ccccc43)cc12] |
| 125 | 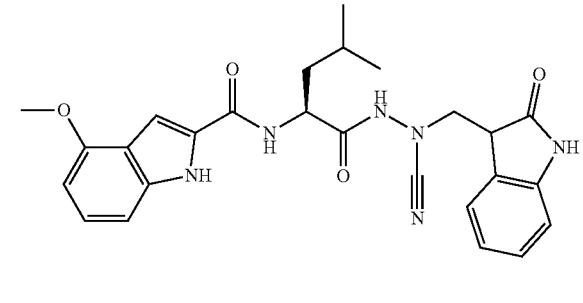 [SMILES: COc1cccc2[nH]c(C(=O)N[C@@H](CC(C)C)C(=O)NN(C#N)CC3C(=O)Nc4ccccc43)cc12] |
| 128 | 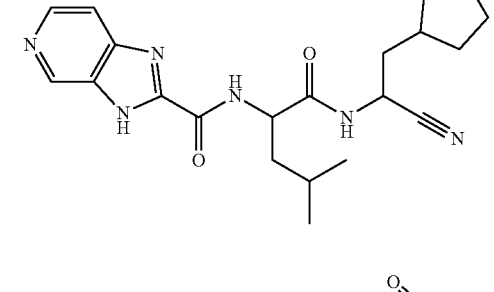 |
| 129 | 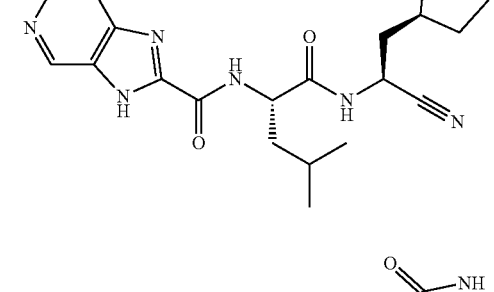 |
| 130 | 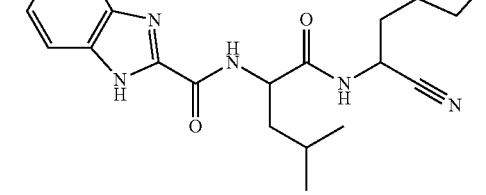 |

TABLE 1-continued

Exemplary compounds.

| Cmpd No. | Structure |
|---|---|
| 131 | 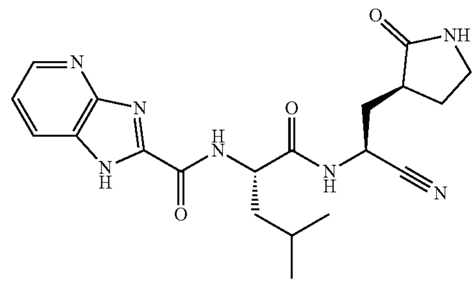 [SMILES: CC(C)C[C@H](NC(=O)c1nc2ncccc2[nH]1)C(=O)N[C@H](C#N)C[C@@H]1CCNC1=O] |
| 132 | 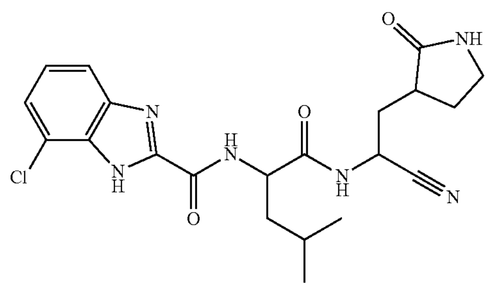 [SMILES: CC(C)CC(NC(=O)c1nc2cccc(Cl)c2[nH]1)C(=O)NC(C#N)CC1CCNC1=O] |
| 133 | 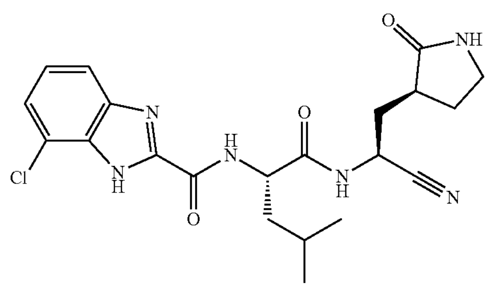 [SMILES: CC(C)C[C@H](NC(=O)c1nc2cccc(Cl)c2[nH]1)C(=O)N[C@H](C#N)C[C@@H]1CCNC1=O] |
| 134 | 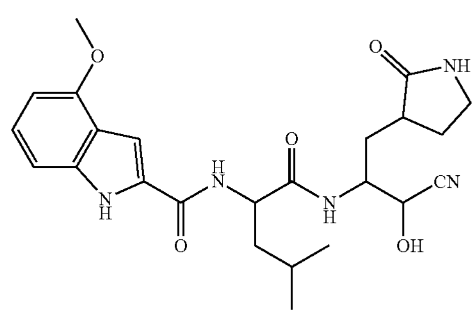 [SMILES: COc1cccc2[nH]c(C(=O)NC(CC(C)C)C(=O)NC(CC3CCNC3=O)C(O)C#N)cc12] |
| 135 | 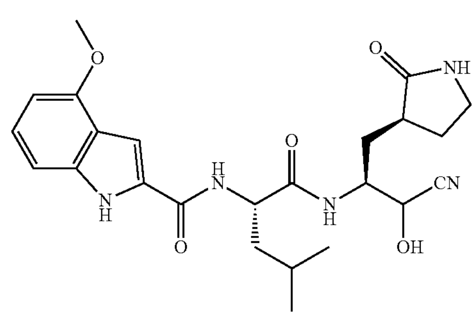 [SMILES: COc1cccc2[nH]c(C(=O)N[C@@H](CC(C)C)C(=O)N[C@@H](C[C@@H]3CCNC3=O)C(O)C#N)cc12] |

TABLE 1-continued

Exemplary compounds.

| Cmpd No. | Structure |
|---|---|
| 136 | 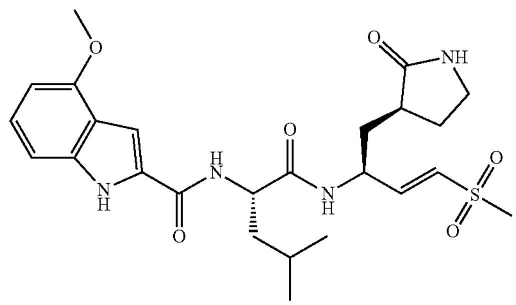 [SMILES: COc1cccc2[nH]c(C(=O)N[C@@H](CC(C)C)C(=O)N[C@H](/C=C/S(C)(=O)=O)C[C@@H]3CCNC3=O)cc12] |
| 137 | 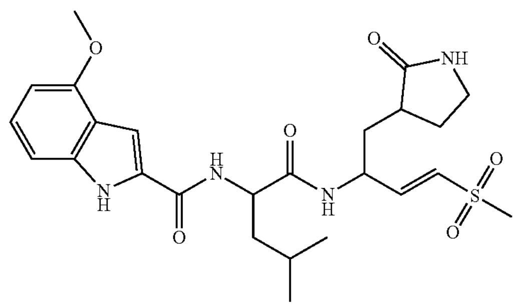 [SMILES: COc1cccc2[nH]c(C(=O)NC(CC(C)C)C(=O)NC(/C=C/S(C)(=O)=O)CC3CCNC3=O)cc12] |
| 138 | 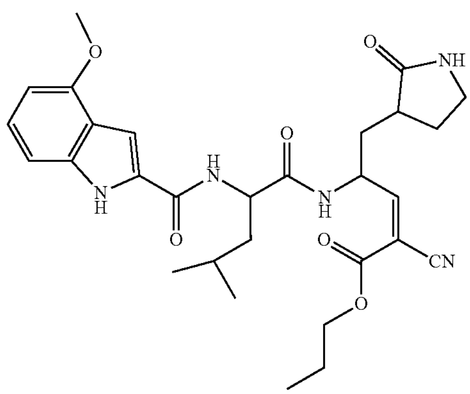 [SMILES: CCCOC(=O)/C(C#N)=C\C(CC1CCNC1=O)NC(=O)C(CC(C)C)NC(=O)c1cc2c(OC)cccc2[nH]1] |
| 139 | 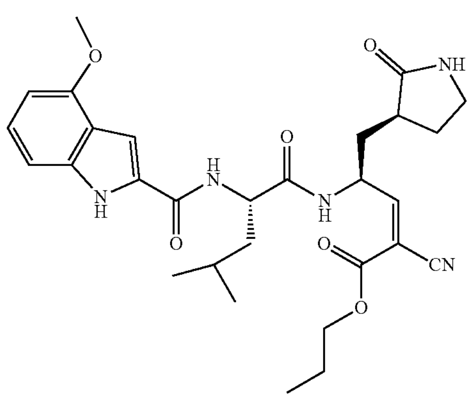 [SMILES: CCCOC(=O)/C(C#N)=C\[C@H](C[C@@H]1CCNC1=O)NC(=O)[C@H](CC(C)C)NC(=O)c1cc2c(OC)cccc2[nH]1] |

TABLE 1-continued

Exemplary compounds.

| Cmpd No. | Structure |
| --- | --- |
| 140 | 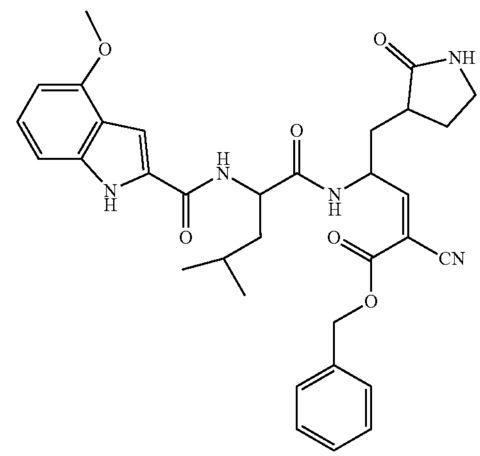 [SMILES: COc1cccc2[nH]c(C(=O)NC(CC(C)C)C(=O)NC(/C=C(/C#N)C(=O)OCc3ccccc3)CC3CCNC3=O)cc12] |
| 141 | 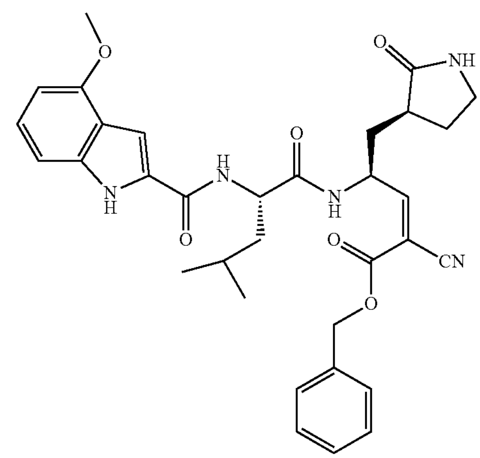 [SMILES: COc1cccc2[nH]c(C(=O)N[C@@H](CC(C)C)C(=O)N[C@H](/C=C(/C#N)C(=O)OCc3ccccc3)C[C@@H]3CCNC3=O)cc12] |
| 142 | 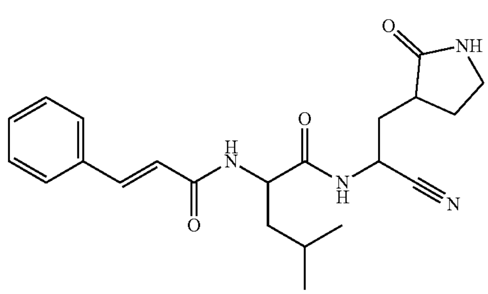 [SMILES: CC(C)CC(NC(=O)/C=C/c1ccccc1)C(=O)NC(C#N)CC1CCNC1=O] |
| 143 | 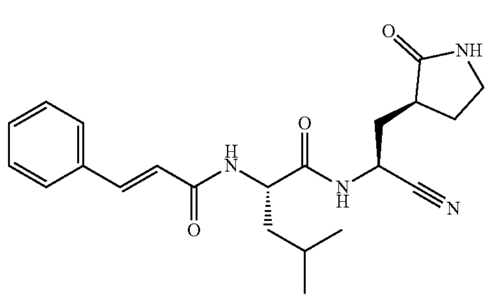 [SMILES: CC(C)C[C@H](NC(=O)/C=C/c1ccccc1)C(=O)N[C@H](C#N)C[C@@H]1CCNC1=O] |

TABLE 1-continued
Exemplary compounds.
| Cmpd No. | Structure |
|---|---|
| 144 | 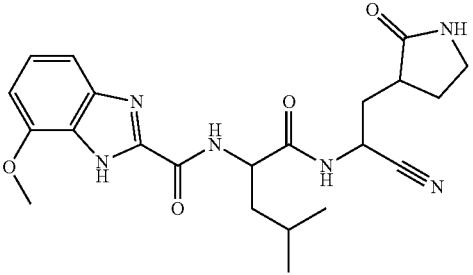 [SMILES: COc1cccc2nc(C(=O)NC(CC(C)C)C(=O)NC(C#N)CC3CCNC3=O)[nH]c12] |
| 145 | 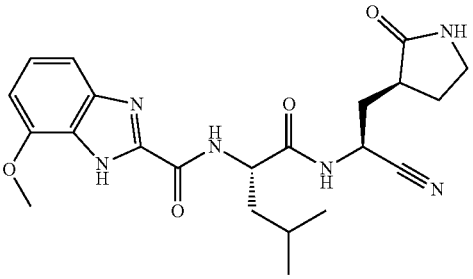 [SMILES: COc1cccc2nc(C(=O)N[C@@H](CC(C)C)C(=O)N[C@H](C#N)C[C@@H]3CCNC3=O)[nH]c12] |
| 146 | 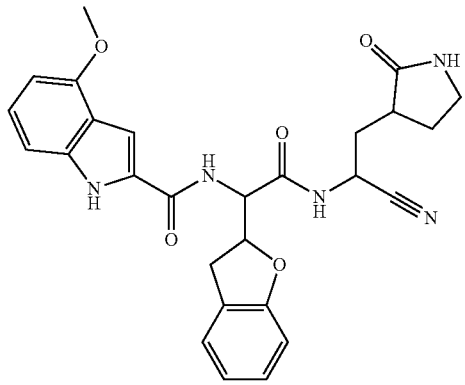 [SMILES: COc1cccc2[nH]c(C(=O)NC(C(=O)NC(C#N)CC3CCNC3=O)C3Cc4ccccc4O3)cc12] |
| 147 | 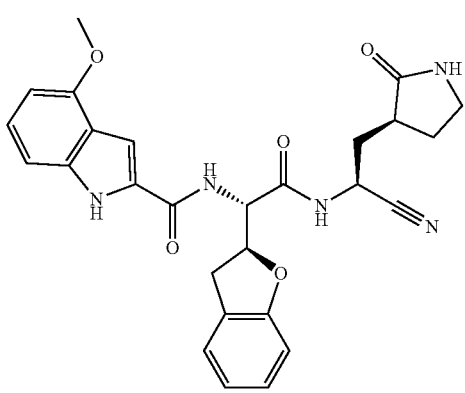 [SMILES: COc1cccc2[nH]c(C(=O)N[C@H](C(=O)N[C@H](C#N)C[C@@H]3CCNC3=O)[C@@H]3Cc4ccccc4O3)cc12] |

TABLE 1-continued

Exemplary compounds.

| Cmpd No. | Structure |
|---|---|
| 148 | 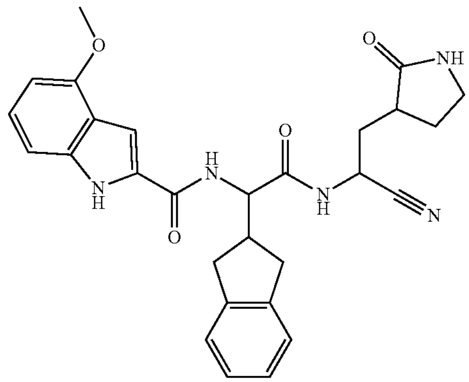 [SMILES: COc1cccc2[nH]c(C(=O)NC(C(=O)NC(C#N)CC3CCNC3=O)C3Cc4ccccc4C3)cc12] |
| 149 | 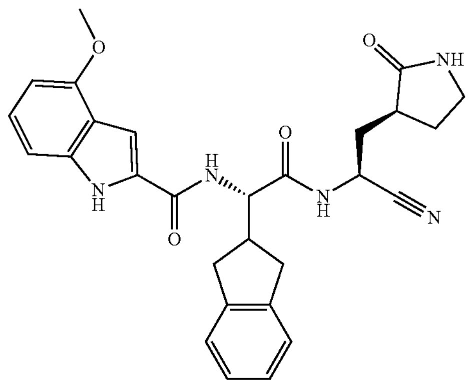 [SMILES: COc1cccc2[nH]c(C(=O)N[C@H](C(=O)N[C@H](C#N)C[C@@H]3CCNC3=O)C3Cc4ccccc4C3)cc12] |
| 150 | 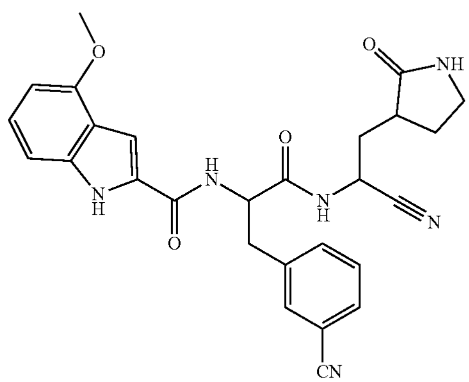 [SMILES: COc1cccc2[nH]c(C(=O)NC(Cc3cccc(C#N)c3)C(=O)NC(C#N)CC3CCNC3=O)cc12] |
| 151 | 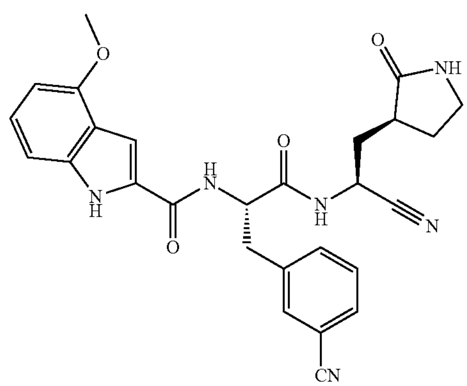 |

TABLE 1-continued
Exemplary compounds.
| Cmpd No. | Structure |
|---|---|
| 152 | 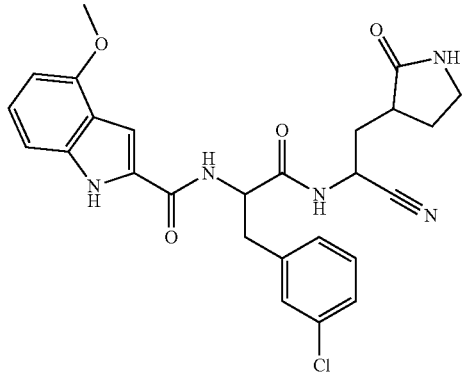 [SMILES: COc1cccc2[nH]c(C(=O)NC(Cc3cccc(Cl)c3)C(=O)NC(C#N)CC3CCNC3=O)cc12] |
| 153 | 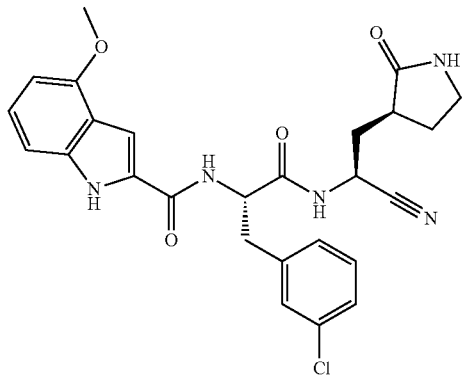 [SMILES: COc1cccc2[nH]c(C(=O)N[C@@H](Cc3cccc(Cl)c3)C(=O)N[C@H](C#N)C[C@@H]3CCNC3=O)cc12] |
| 154 | 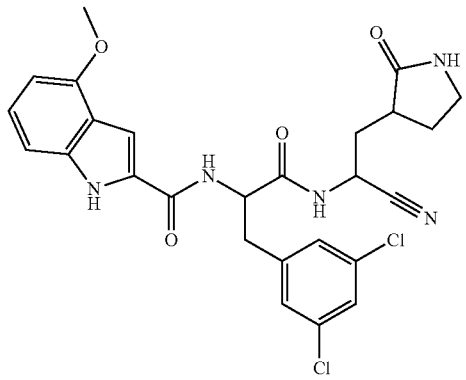 [SMILES: COc1cccc2[nH]c(C(=O)NC(Cc3cc(Cl)cc(Cl)c3)C(=O)NC(C#N)CC3CCNC3=O)cc12] |
| 155 | 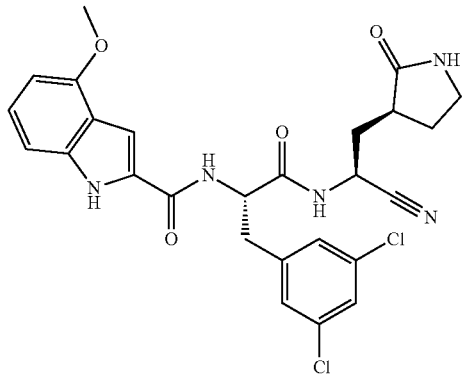 [SMILES: COc1cccc2[nH]c(C(=O)N[C@@H](Cc3cc(Cl)cc(Cl)c3)C(=O)N[C@H](C#N)C[C@@H]3CCNC3=O)cc12] |

TABLE 1-continued
Exemplary compounds.
| Cmpd No. | Structure |
|---|---|
| 156 | 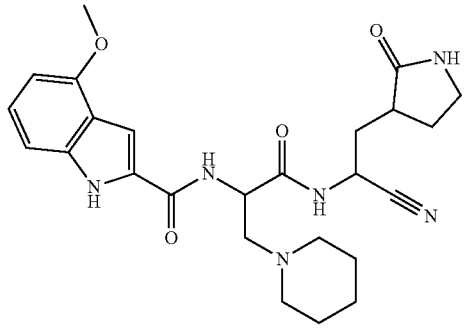 [SMILES: COc1cccc2[nH]c(C(=O)NC(CN3CCCCC3)C(=O)NC(C#N)CC3CCNC3=O)cc12] |
| 157 | 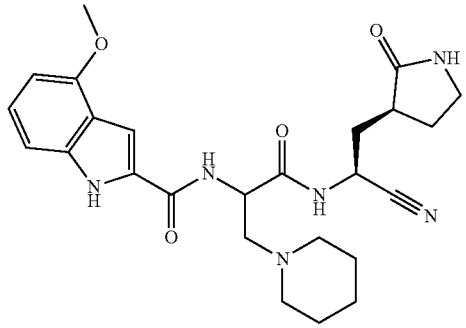 [SMILES: COc1cccc2[nH]c(C(=O)NC(CN3CCCCC3)C(=O)N[C@H](C#N)C[C@@H]3CCNC3=O)cc12] |
| 158 | 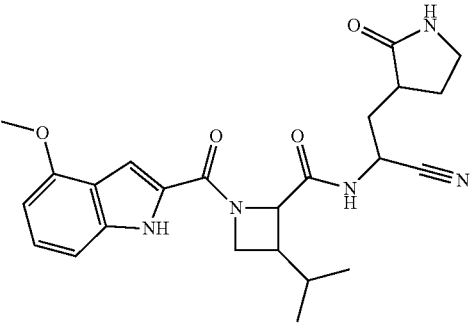 [SMILES: COc1cccc2[nH]c(C(=O)N3CC(C(C)C)C3C(=O)NC(C#N)CC3CCNC3=O)cc12] |
| 159 | 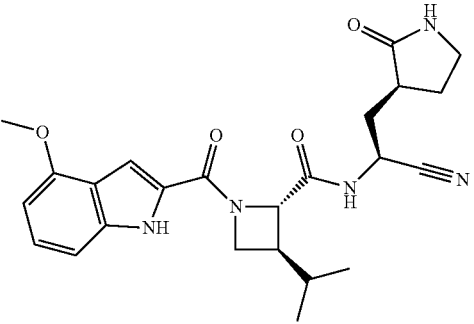 [SMILES: COc1cccc2[nH]c(C(=O)N3C[C@H](C(C)C)[C@H]3C(=O)N[C@H](C#N)C[C@@H]3CCNC3=O)cc12] |

TABLE 1-continued
Exemplary compounds.
| Cmpd No. | Structure |
|---|---|
| 160 | 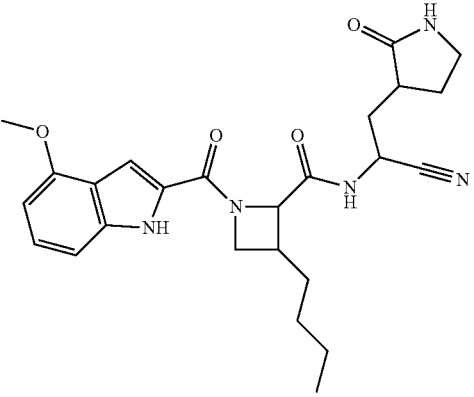 [SMILES: CCCCC1CN(C(=O)c2cc3c(OC)cccc3[nH]2)C1C(=O)NC(C#N)CC1CCNC1=O] |
| 161 | 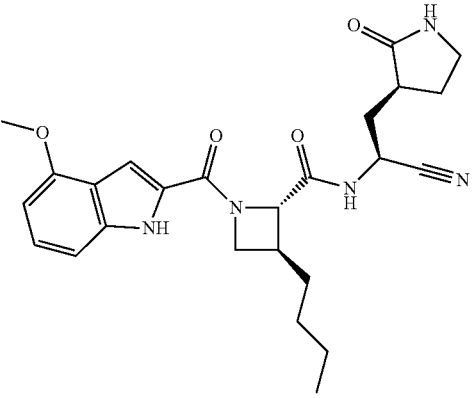 [SMILES: CCCC[C@H]1CN(C(=O)c2cc3c(OC)cccc3[nH]2)[C@@H]1C(=O)N[C@H](C#N)C[C@@H]1CCNC1=O] |
| 162 | 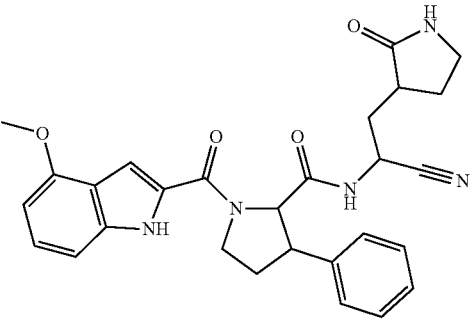 [SMILES: COc1cccc2[nH]c(C(=O)N3CCC(c4ccccc4)C3C(=O)NC(C#N)CC3CCNC3=O)cc12] |
| 163 | 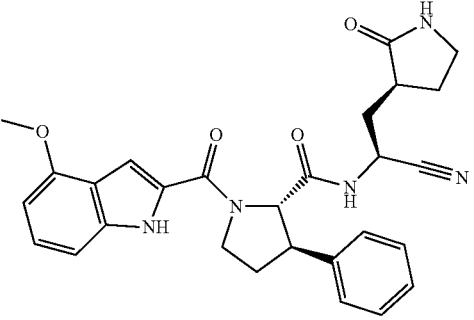 [SMILES: COc1cccc2[nH]c(C(=O)N3CC[C@H](c4ccccc4)[C@H]3C(=O)N[C@H](C#N)C[C@@H]3CCNC3=O)cc12] |

TABLE 1-continued

Exemplary compounds.

| Cmpd No. | Structure |
|---|---|
| 164 | 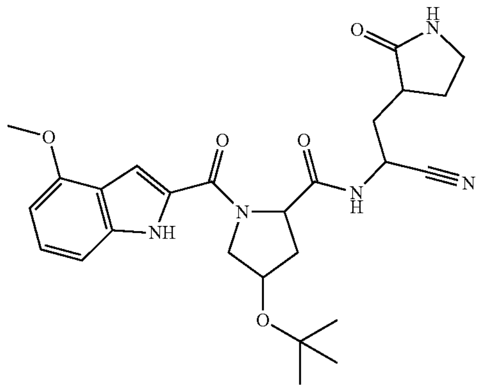 [SMILES: COc1cccc2[nH]c(C(=O)N3CC(OC(C)(C)C)CC3C(=O)NC(C#N)CC3CCNC3=O)cc12] |
| 165 | 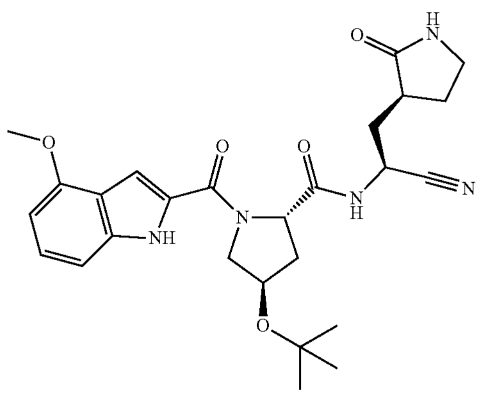 [SMILES: COc1cccc2[nH]c(C(=O)N3C[C@H](OC(C)(C)C)C[C@H]3C(=O)N[C@H](C#N)C[C@@H]3CCNC3=O)cc12] |
| 166 | 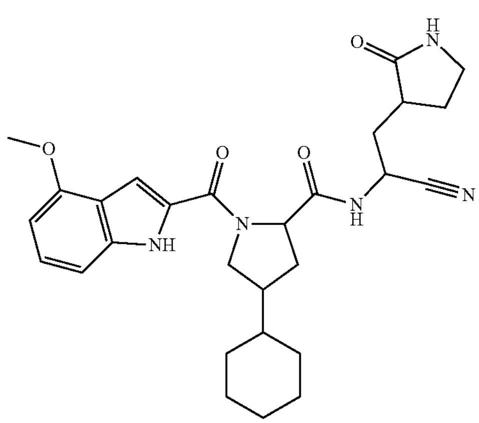 [SMILES: COc1cccc2[nH]c(C(=O)N3CC(C4CCCCC4)CC3C(=O)NC(C#N)CC3CCNC3=O)cc12] |

TABLE 1-continued
Exemplary compounds.
| Cmpd No. | Structure |
|---|---|
| 167 | 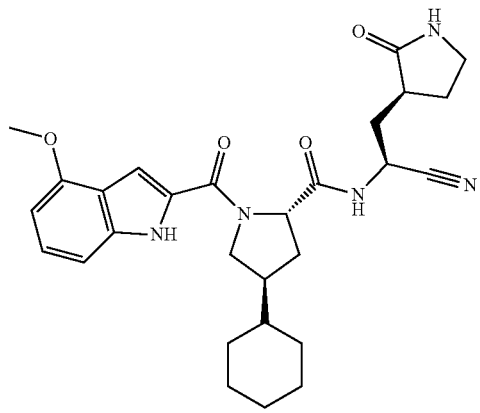 [SMILES: COc1cccc2[nH]c(C(=O)N3C[C@H](C4CCCCC4)C[C@H]3C(=O)N[C@H](C#N)C[C@@H]3CCNC3=O)cc12] |
| 168 | 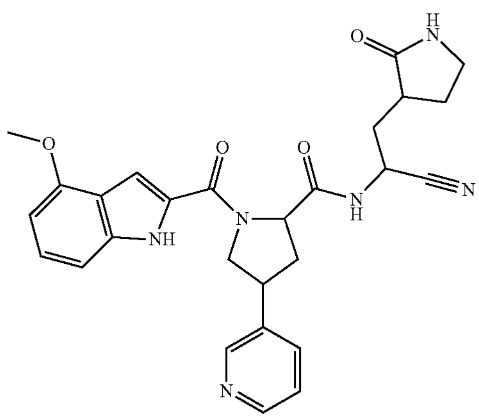 [SMILES: COc1cccc2[nH]c(C(=O)N3CC(c4cccnc4)CC3C(=O)NC(C#N)CC3CCNC3=O)cc12] |
| 169 | 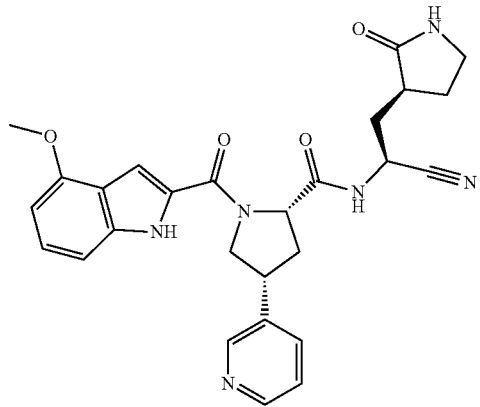 [SMILES: COc1cccc2[nH]c(C(=O)N3C[C@@H](c4cccnc4)C[C@H]3C(=O)N[C@H](C#N)C[C@@H]3CCNC3=O)cc12] |

TABLE 1-continued
Exemplary compounds.
| Cmpd No. | Structure |
|---|---|
| 170 | 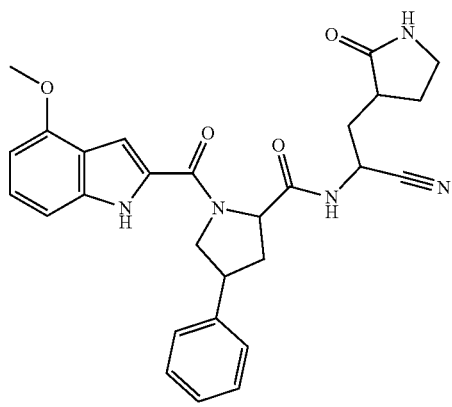 [SMILES: COc1cccc2[nH]c(C(=O)N3CC(c4ccccc4)CC3C(=O)NC(C#N)CC3CCNC3=O)cc12] |
| 171 | 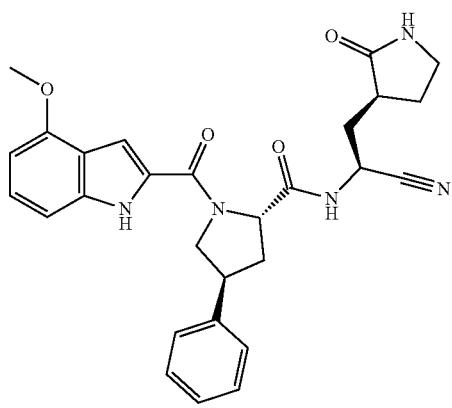 [SMILES: COc1cccc2[nH]c(C(=O)N3C[C@H](c4ccccc4)C[C@H]3C(=O)N[C@H](C#N)C[C@@H]3CCNC3=O)cc12] |
| 172 | 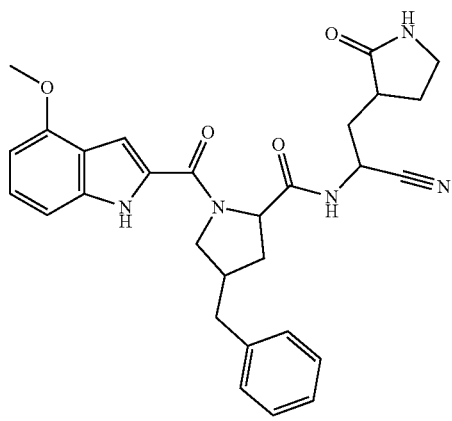 [SMILES: COc1cccc2[nH]c(C(=O)N3CC(Cc4ccccc4)CC3C(=O)NC(C#N)CC3CCNC3=O)cc12] |

TABLE 1-continued
Exemplary compounds.
| Cmpd No. | Structure |
|---|---|
| 173 | 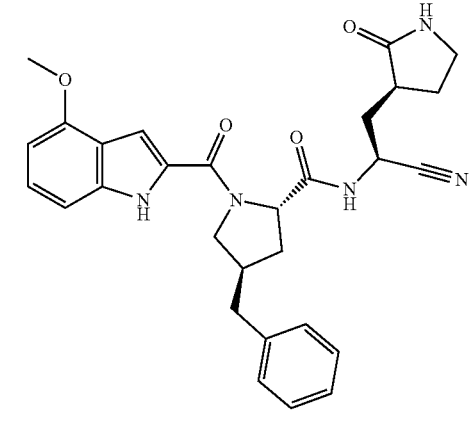 [SMILES: COc1cccc2[nH]c(C(=O)N3C[C@H](Cc4ccccc4)C[C@H]3C(=O)N[C@H](C#N)C[C@@H]3CCNC3=O)cc12] |
| 174 | 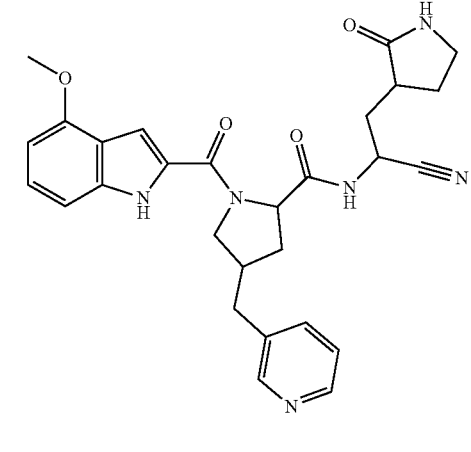 [SMILES: COc1cccc2[nH]c(C(=O)N3CC(Cc4cccnc4)CC3C(=O)NC(C#N)CC3CCNC3=O)cc12] |
| 175 | 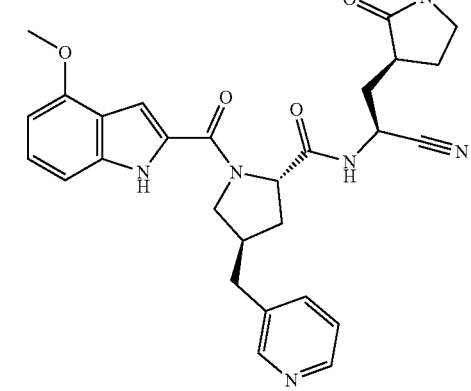 |

TABLE 1-continued

Exemplary compounds.

| Cmpd No. | Structure |
|---|---|
| 176 | 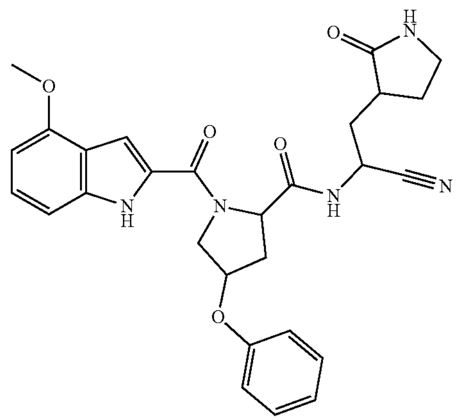 [SMILES: COc1cccc2[nH]c(C(=O)N3CC(Oc4ccccc4)CC3C(=O)NC(C#N)CC3CCNC3=O)cc12] |
| 177 | 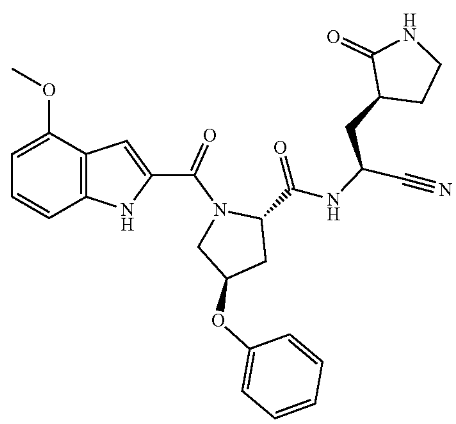 [SMILES: COc1cccc2[nH]c(C(=O)N3C[C@H](Oc4ccccc4)C[C@H]3C(=O)N[C@H](C#N)C[C@@H]3CCNC3=O)cc12] |
| 178 | 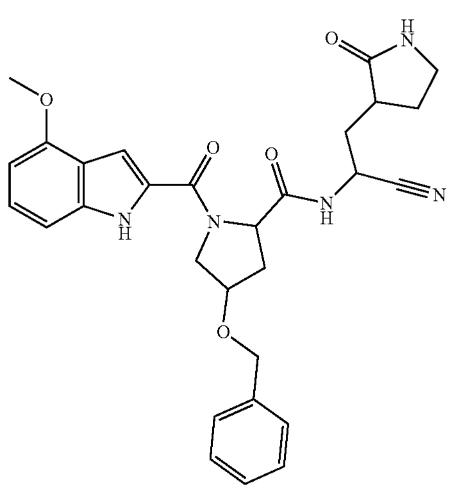 [SMILES: COc1cccc2[nH]c(C(=O)N3CC(OCc4ccccc4)CC3C(=O)NC(C#N)CC3CCNC3=O)cc12] |

TABLE 1-continued
Exemplary compounds.
| Cmpd No. | Structure |
|---|---|
| 179 | 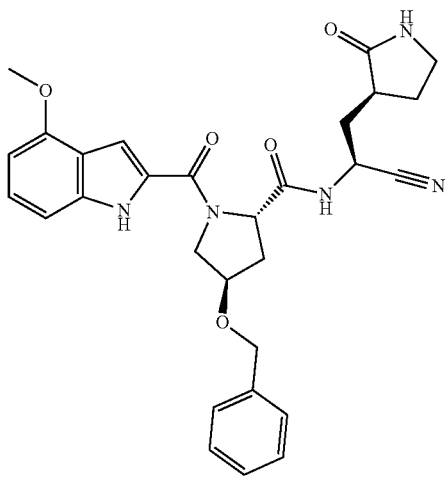 [SMILES: COc1cccc2[nH]c(C(=O)N3C[C@H](OCc4ccccc4)C[C@H]3C(=O)N[C@H](C#N)C[C@@H]3CCNC3=O)cc12] |
| 180 | 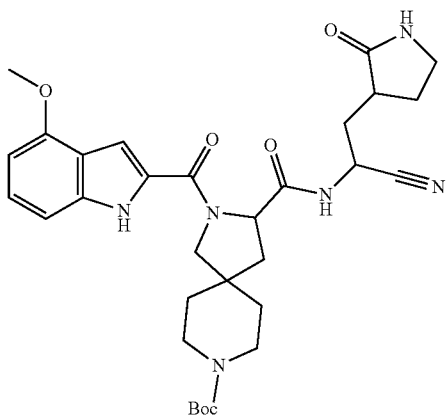 [SMILES: COc1cccc2[nH]c(C(=O)N3CC4(CCN(C(=O)OC(C)(C)C)CC4)CC3C(=O)NC(C#N)CC3CCNC3=O)cc12] |
| 181 | 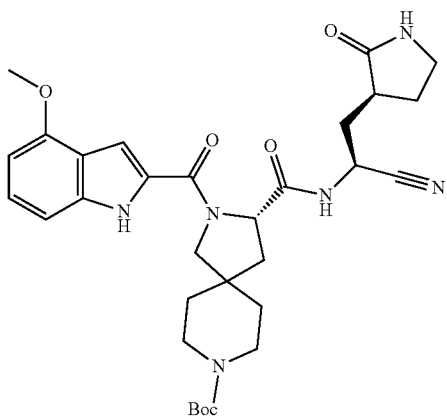 [SMILES: COc1cccc2[nH]c(C(=O)N3CC4(CCN(C(=O)OC(C)(C)C)CC4)C[C@H]3C(=O)N[C@H](C#N)C[C@@H]3CCNC3=O)cc12] |

TABLE 1-continued

Exemplary compounds.

| Cmpd No. | Structure |
| --- | --- |
| 182 | 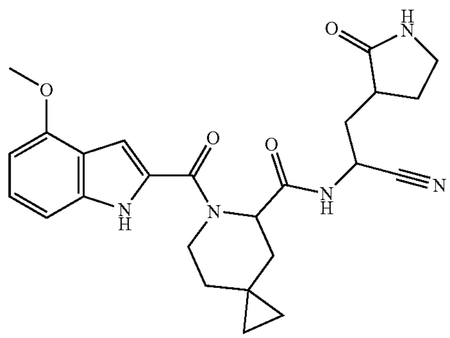 [SMILES: COc1cccc2[nH]c(C(=O)N3CCC4(CC4)CC3C(=O)NC(C#N)CC3CCNC3=O)cc12] |
| 183 | 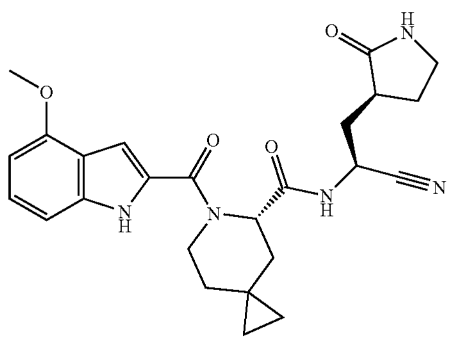 [SMILES: COc1cccc2[nH]c(C(=O)N3CCC4(CC4)C[C@H]3C(=O)N[C@H](C#N)C[C@@H]3CCNC3=O)cc12] |
| 184 | 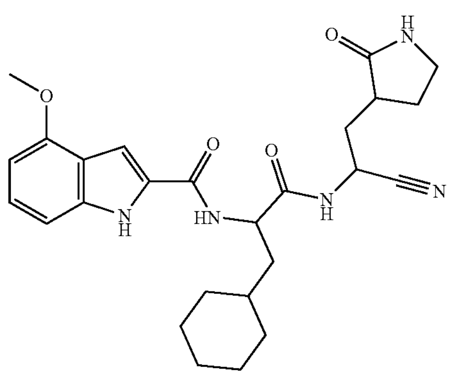 [SMILES: COc1cccc2[nH]c(C(=O)NC(CC3CCCCC3)C(=O)NC(C#N)CC3CCNC3=O)cc12] |
| 185 | 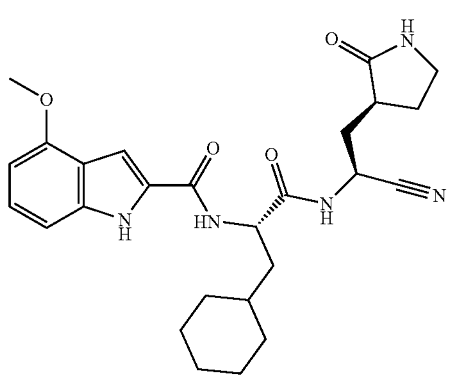 [SMILES: COc1cccc2[nH]c(C(=O)N[C@@H](CC3CCCCC3)C(=O)N[C@H](C#N)C[C@@H]3CCNC3=O)cc12] |

TABLE 1-continued
Exemplary compounds.
| Cmpd No. | Structure |
|---|---|
| 186 | 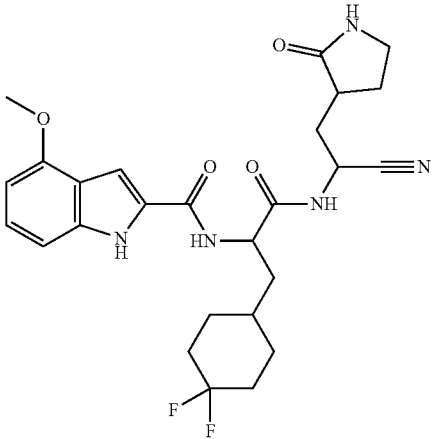 [SMILES: COc1cccc2[nH]c(C(=O)NC(CC3CCC(F)(F)CC3)C(=O)NC(C#N)CC3CCNC3=O)cc12] |
| 187 | 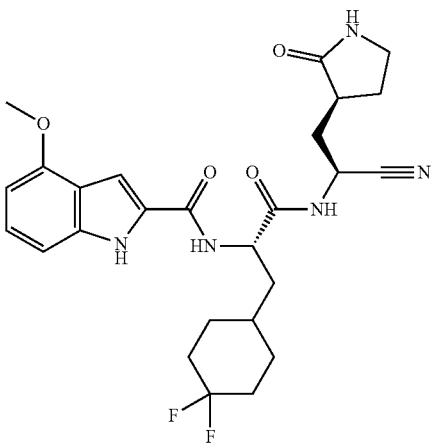 [SMILES: COc1cccc2[nH]c(C(=O)N[C@@H](CC3CCC(F)(F)CC3)C(=O)N[C@H](C#N)C[C@@H]3CCNC3=O)cc12] |
| 188 | 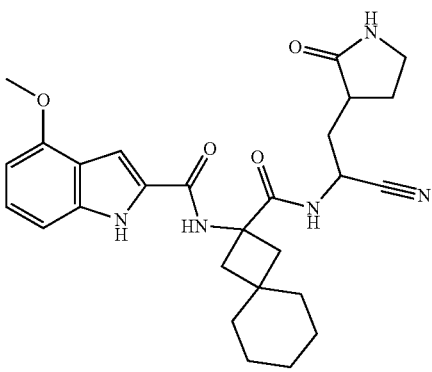 [SMILES: COc1cccc2[nH]c(C(=O)NC3(C(=O)NC(C#N)CC4CCNC4=O)CC4(CCCCC4)C3)cc12] |

TABLE 1-continued

| Exemplary compounds. | |
|---|---|
| Cmpd No. | Structure |
| 189 | |
| 190 | |
| 191 | |
| 196 | |

TABLE 1-continued

Exemplary compounds.

| Cmpd No. | Structure |
|---|---|
| 197 | 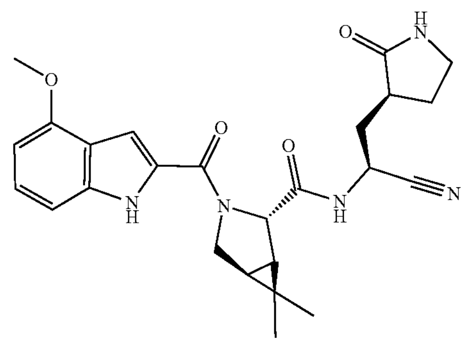 |
| 198 | 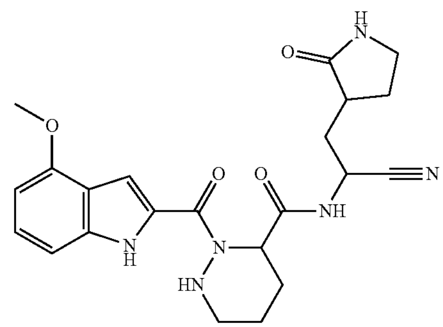 [SMILES: COc1cccc2[nH]c(C(=O)N3NCCCC3C(=O)NC(C#N)CC3CCNC3=O)cc12] |
| 199 | 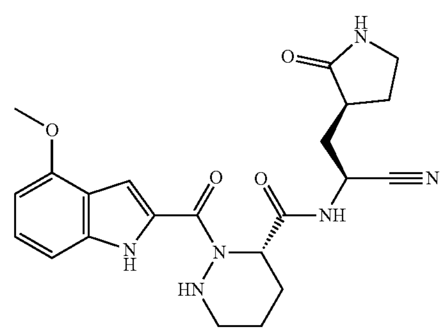 [SMILES: COc1cccc2[nH]c(C(=O)N3NCCC[C@H]3C(=O)N[C@H](C#N)C[C@@H]3CCNC3=O)cc12] |
| 200 | 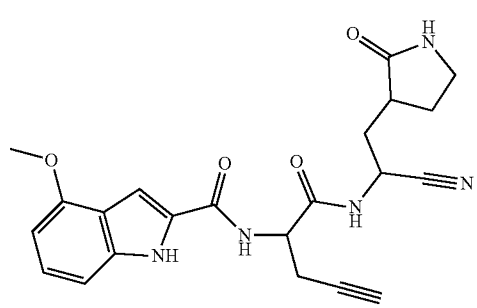 [SMILES: C#CCC(NC(=O)c1cc2c(OC)cccc2[nH]1)C(=O)NC(C#N)CC1CCNC1=O] |

TABLE 1-continued
Exemplary compounds.
| Cmpd No. | Structure |
|---|---|
| 201 | 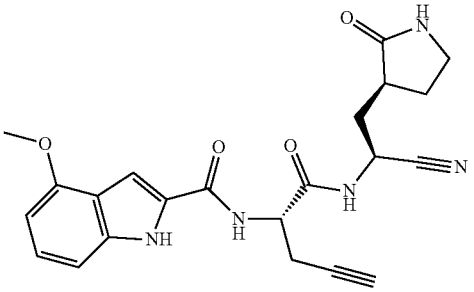 [SMILES: C#CC[C@H](NC(=O)c1cc2c(OC)cccc2[nH]1)C(=O)N[C@H](C#N)C[C@@H]1CCNC1=O] |
| 202 | 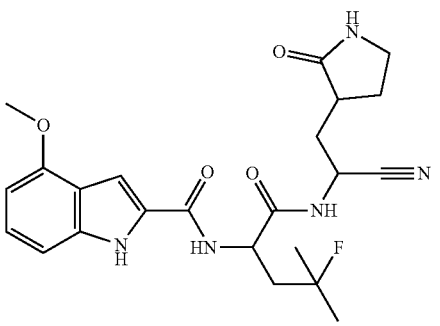 [SMILES: COc1cccc2[nH]c(C(=O)NC(CC(C)(C)F)C(=O)NC(C#N)CC3CCNC3=O)cc12] |
| 203 | 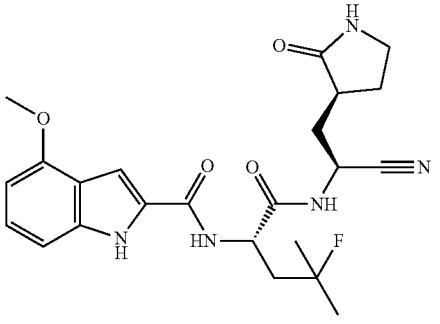 [SMILES: COc1cccc2[nH]c(C(=O)N[C@@H](CC(C)(C)F)C(=O)N[C@H](C#N)C[C@@H]3CCNC3=O)cc12] |
| 204 | 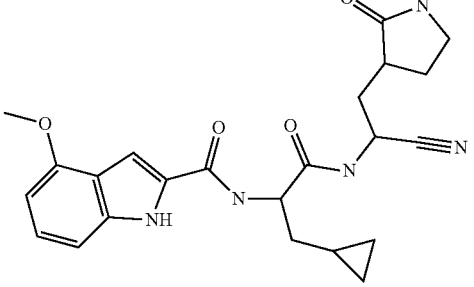 |

TABLE 1-continued

Exemplary compounds.

| Cmpd No. | Structure |
|---|---|
| 205 | 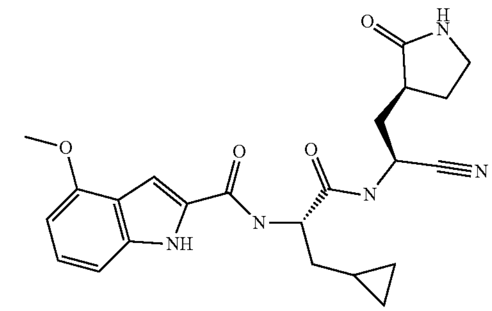 [SMILES: COc1cccc2[nH]c(C(=O)N[C@@H](CC3CC3)C(=O)N[C@H](C#N)C[C@@H]3CCNC3=O)cc12] |
| 206 | 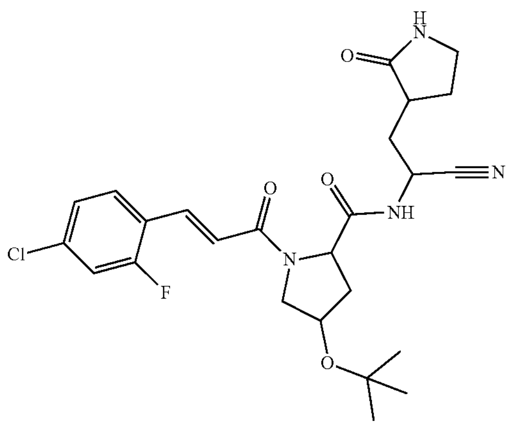 [SMILES: CC(C)(C)OC1CC(C(=O)NC(C#N)CC2CCNC2=O)N(C(=O)/C=C/c2ccc(Cl)cc2F)C1] |
| 207 | 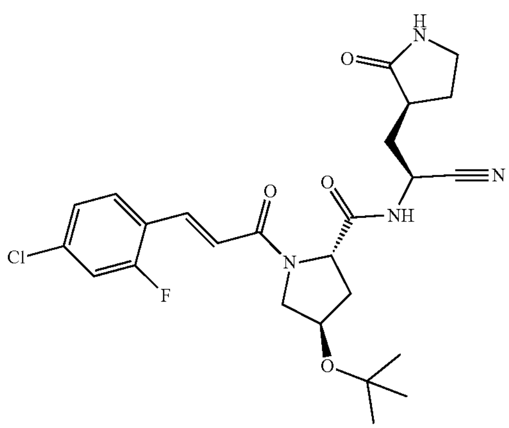 [SMILES: CC(C)(C)O[C@@H]1C[C@@H](C(=O)N[C@H](C#N)C[C@@H]2CCNC2=O)N(C(=O)/C=C/c2ccc(Cl)cc2F)C1] |
| 208 | 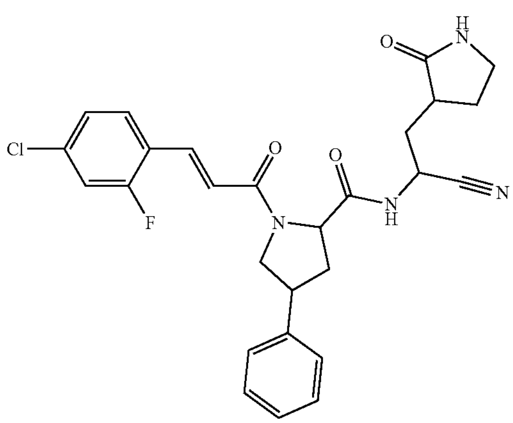 [SMILES: N#CC(CC1CCNC1=O)NC(=O)C1CC(c2ccccc2)CN1C(=O)/C=C/c1ccc(Cl)cc1F] |

TABLE 1-continued
Exemplary compounds.
| Cmpd No. | Structure |
|---|---|
| 209 | 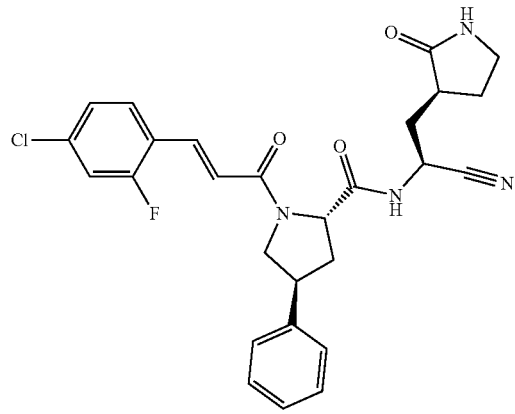 [SMILES: N#C[C@H](C[C@@H]1CCNC1=O)NC(=O)[C@@H]1C[C@@H](c2ccccc2)CN1C(=O)/C=C/c1ccc(Cl)cc1F] |
| 210 | 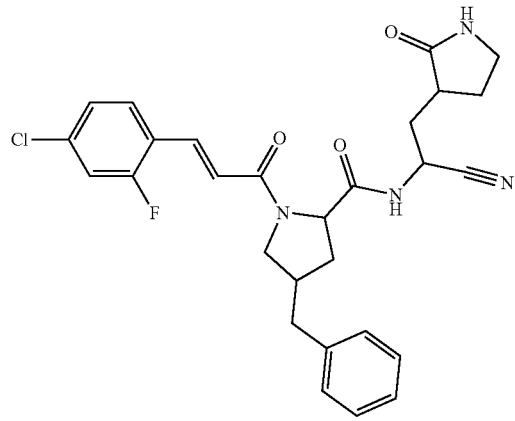 [SMILES: N#CC(CC1CCNC1=O)NC(=O)C1CC(Cc2ccccc2)CN1C(=O)/C=C/c1ccc(Cl)cc1F] |
| 211 | 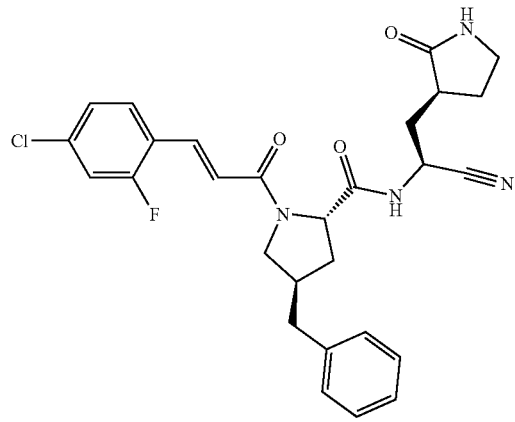 [SMILES: N#C[C@H](C[C@@H]1CCNC1=O)NC(=O)[C@@H]1C[C@@H](Cc2ccccc2)CN1C(=O)/C=C/c1ccc(Cl)cc1F] |

TABLE 1-continued
Exemplary compounds.
| Cmpd No. | Structure |
|---|---|
| 212 | 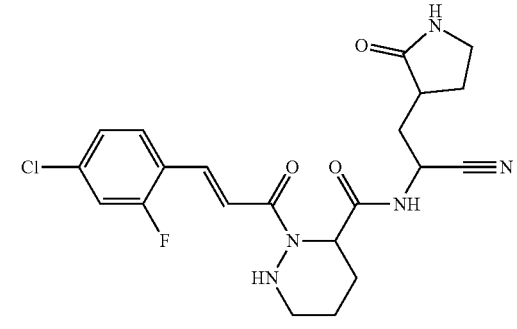 [SMILES: N#CC(CC1CCNC1=O)NC(=O)C1CCCNN1C(=O)/C=C/c1ccc(Cl)cc1F] |
| 213 | 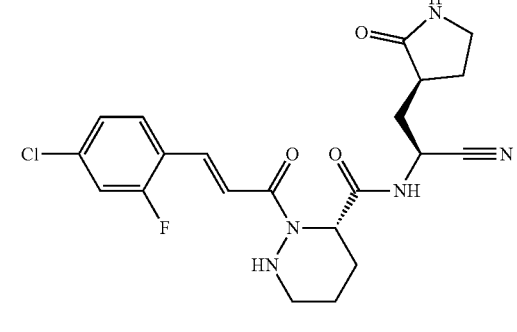 |
| 214 | 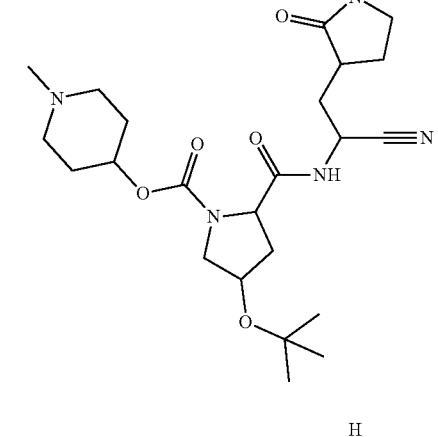 |
| 215 | 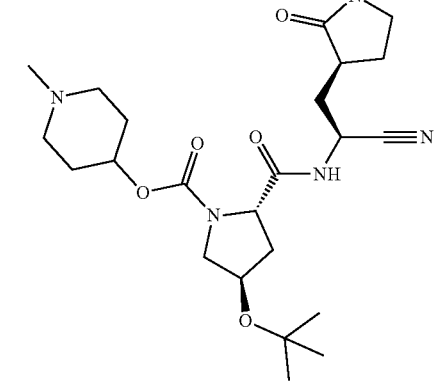 |

TABLE 1-continued
Exemplary compounds.
| Cmpd No. | Structure |
|---|---|
| 216 | 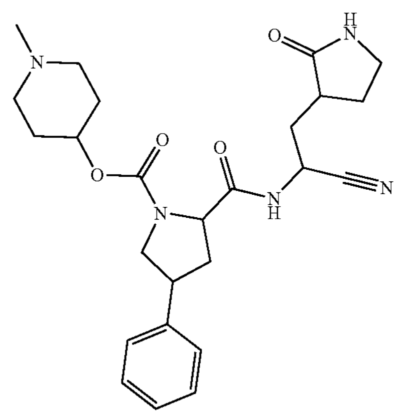 [SMILES: CN1CCC(OC(=O)N2CC(c3ccccc3)CC2C(=O)NC(C#N)CC2CCNC2=O)CC1] |
| 217 | 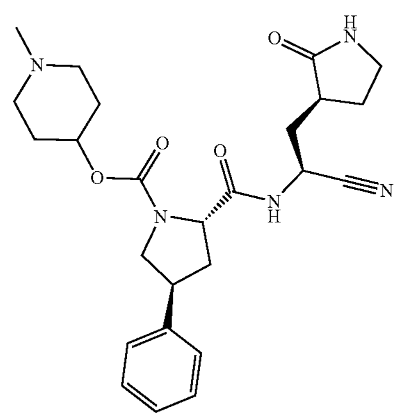 [SMILES: CN1CCC(OC(=O)N2C[C@H](c3ccccc3)C[C@H]2C(=O)N[C@H](C#N)C[C@@H]2CCNC2=O)CC1] |
| 218 | 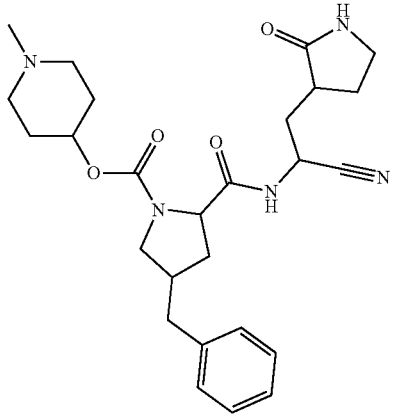 [SMILES: CN1CCC(OC(=O)N2CC(Cc3ccccc3)CC2C(=O)NC(C#N)CC2CCNC2=O)CC1] |

TABLE 1-continued

Exemplary compounds.

| Cmpd No. | Structure |
| --- | --- |
| 219 | 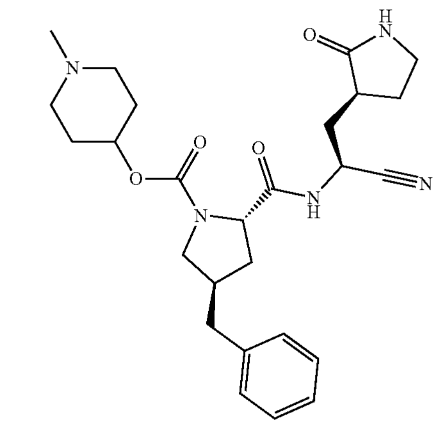 [SMILES: CN1CCC(OC(=O)N2C[C@H](Cc3ccccc3)C[C@H]2C(=O)N[C@H](C#N)C[C@@H]2CCNC2=O)CC1] |
| 220 | 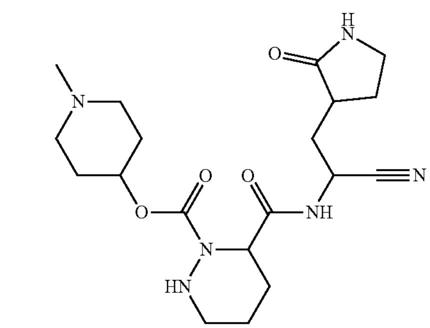 [SMILES: CN1CCC(OC(=O)N2NCCCC2C(=O)NC(C#N)CC2CCNC2=O)CC1] |
| 221 | 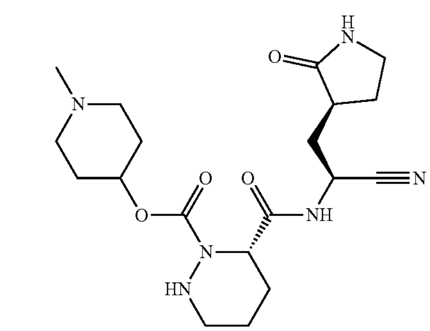 [SMILES: CN1CCC(OC(=O)N2NCCC[C@H]2C(=O)N[C@H](C#N)C[C@@H]2CCNC2=O)CC1] |
| 222 | 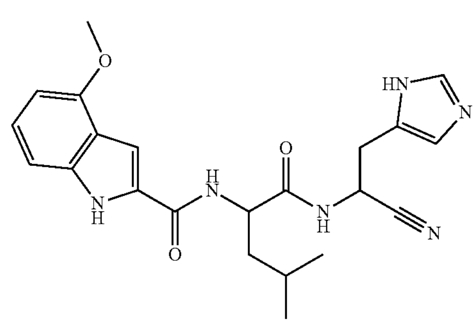 [SMILES: COc1cccc2[nH]c(C(=O)NC(CC(C)C)C(=O)NC(C#N)Cc3cnc[nH]3)cc12] |

TABLE 1-continued
Exemplary compounds.
| Cmpd No. | Structure |
|---|---|
| 223 | 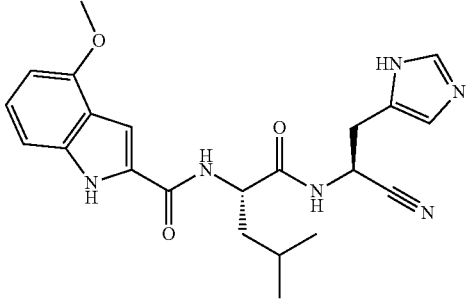 [SMILES: COc1cccc2[nH]c(C(=O)N[C@@H](CC(C)C)C(=O)N[C@H](C#N)Cc3cnc[nH]3)cc12] |
| 224 | 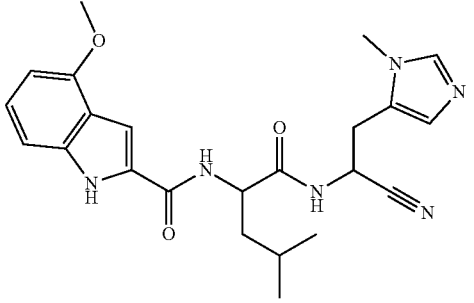 [SMILES: COc1cccc2[nH]c(C(=O)NC(CC(C)C)C(=O)NC(C#N)Cc3cncn3C)cc12] |
| 225 | 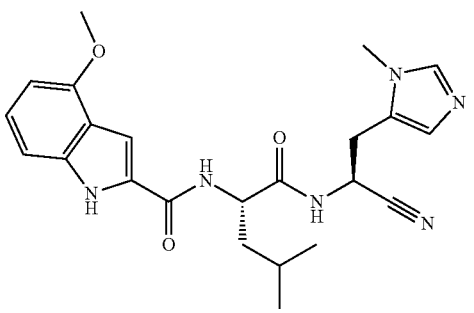 [SMILES: COc1cccc2[nH]c(C(=O)N[C@@H](CC(C)C)C(=O)N[C@H](C#N)Cc3cncn3C)cc12] |
| 226 | 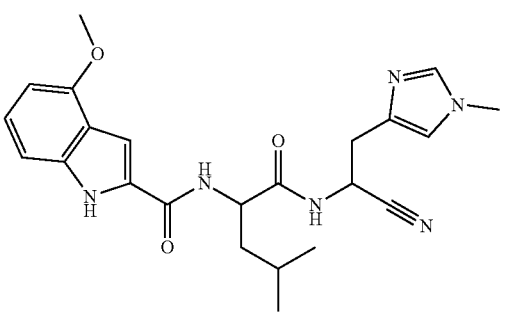 [SMILES: COc1cccc2[nH]c(C(=O)NC(CC(C)C)C(=O)NC(C#N)Cc3cn(C)cn3)cc12] |
| 227 | 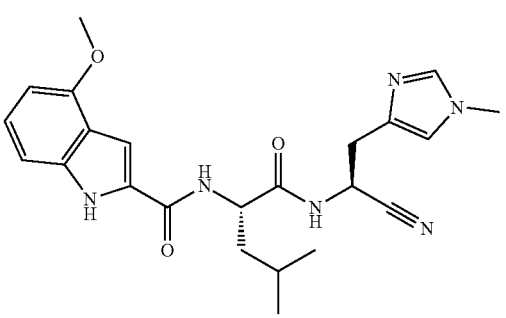 [SMILES: COc1cccc2[nH]c(C(=O)N[C@@H](CC(C)C)C(=O)N[C@H](C#N)Cc3cn(C)cn3)cc12] |

TABLE 1-continued
Exemplary compounds.
| Cmpd No. | Structure |
|---|---|
| 230 | 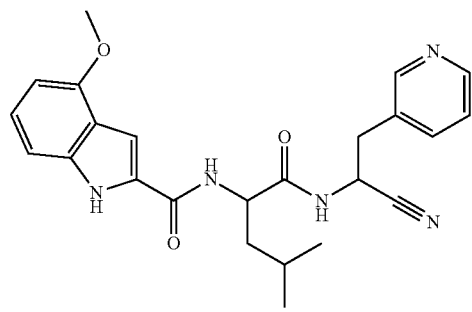 [SMILES: COc1cccc2[nH]c(C(=O)NC(CC(C)C)C(=O)NC(C#N)Cc3cccnc3)cc12] |
| 231 | 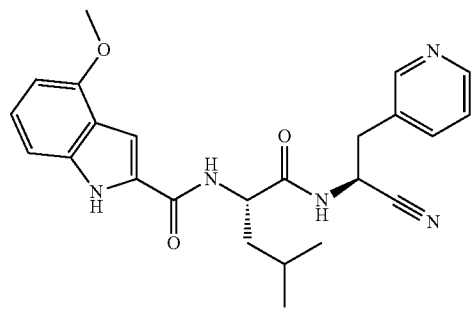 [SMILES: COc1cccc2[nH]c(C(=O)N[C@@H](CC(C)C)C(=O)N[C@H](C#N)Cc3cccnc3)cc12] |
| 234 | 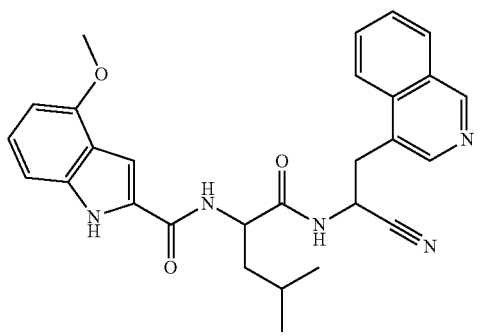 [SMILES: COc1cccc2[nH]c(C(=O)NC(CC(C)C)C(=O)NC(C#N)Cc3cncc4ccccc34)cc12] |
| 235 | 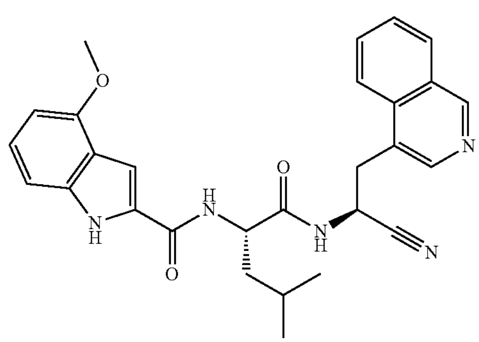 [SMILES: COc1cccc2[nH]c(C(=O)N[C@@H](CC(C)C)C(=O)N[C@H](C#N)Cc3cncc4ccccc34)cc12] |

141
142
TABLE 1-continued
Exemplary compounds.
| Cmpd No. | Structure |
|---|---|
| 236 | 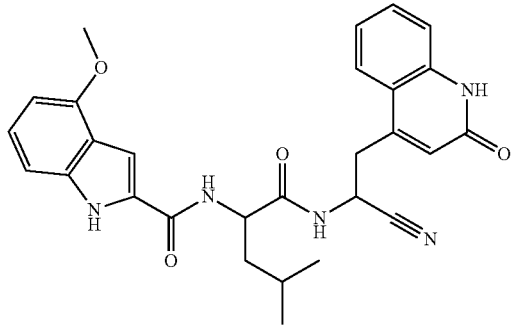 [SMILES: COc1cccc2[nH]c(C(=O)NC(CC(C)C)C(=O)NC(C#N)Cc3cc(=O)[nH]c4ccccc34)cc12] |
| 237 | 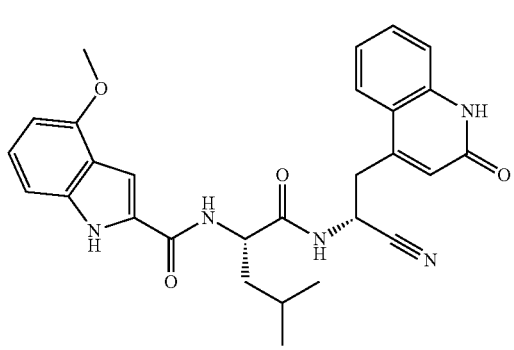 [SMILES: COc1cccc2[nH]c(C(=O)N[C@@H](CC(C)C)C(=O)N[C@@H](C#N)Cc3cc(=O)[nH]c4ccccc34)cc12] |
| 238 | 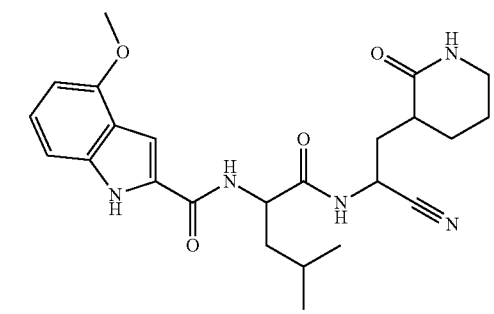 [SMILES: COc1cccc2[nH]c(C(=O)NC(CC(C)C)C(=O)NC(C#N)CC3CCCNC3=O)cc12] |
| 239 | 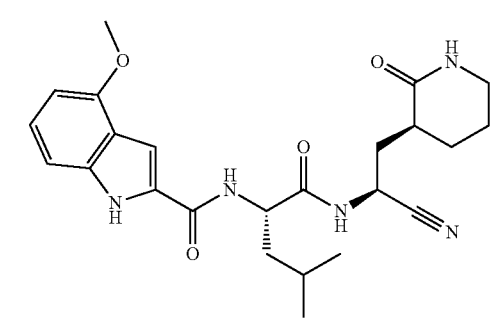 [SMILES: COc1cccc2[nH]c(C(=O)N[C@@H](CC(C)C)C(=O)N[C@H](C#N)C[C@@H]3CCCNC3=O)cc12] |

TABLE 1-continued
Exemplary compounds.
| Cmpd No. | Structure |
|---|---|
| 240 | 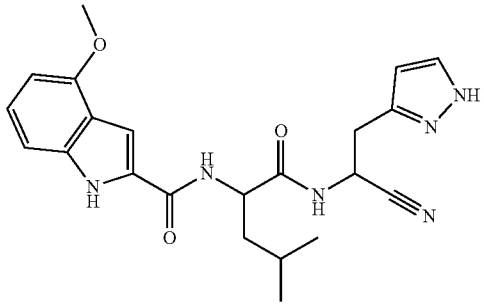 [SMILES: COc1cccc2[nH]c(C(=O)NC(CC(C)C)C(=O)NC(C#N)Cc3cc[nH]n3)cc12] |
| 241 | 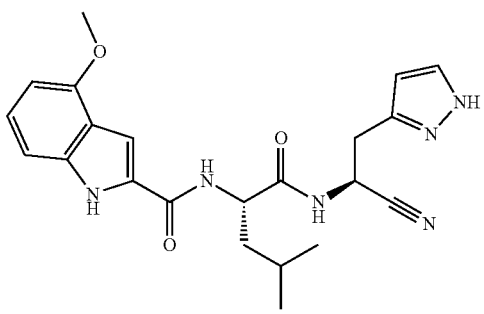 [SMILES: COc1cccc2[nH]c(C(=O)N[C@@H](CC(C)C)C(=O)N[C@H](C#N)Cc3cc[nH]n3)cc12] |
| 244 | 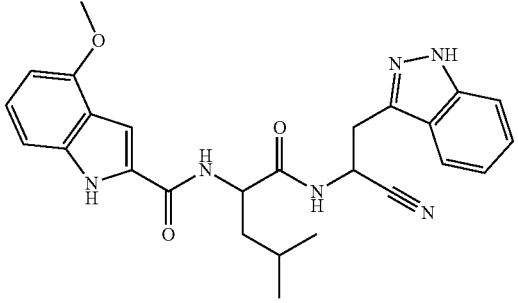 [SMILES: COc1cccc2[nH]c(C(=O)NC(CC(C)C)C(=O)NC(C#N)Cc3n[nH]c4ccccc34)cc12] |
| 245 | 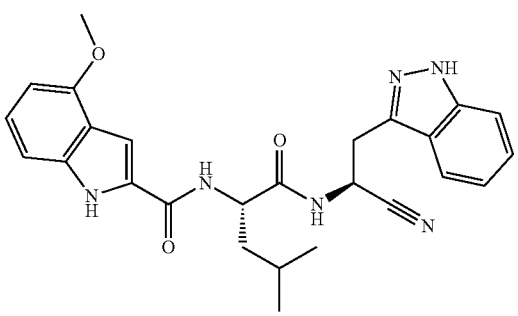 [SMILES: COc1cccc2[nH]c(C(=O)N[C@@H](CC(C)C)C(=O)N[C@H](C#N)Cc3n[nH]c4ccccc34)cc12] |
| 246 | 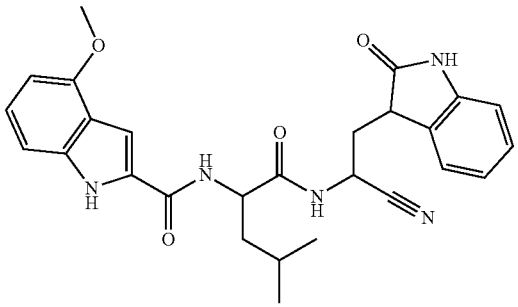 [SMILES: COc1cccc2[nH]c(C(=O)NC(CC(C)C)C(=O)NC(C#N)CC3C(=O)Nc4ccccc43)cc12] |

TABLE 1-continued

Exemplary compounds.

| Cmpd No. | Structure |
|---|---|
| 247 | 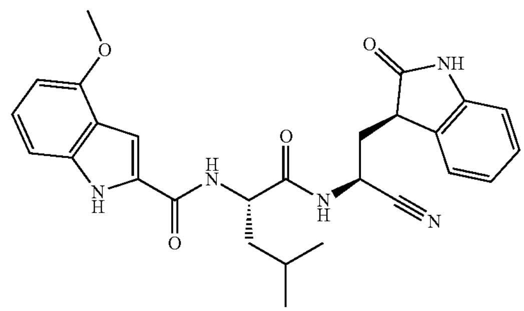 [SMILES: COc1cccc2[nH]c(C(=O)N[C@@H](CC(C)C)C(=O)N[C@H](C#N)C[C@H]3C(=O)Nc4ccccc43)cc12] |
| 248 | 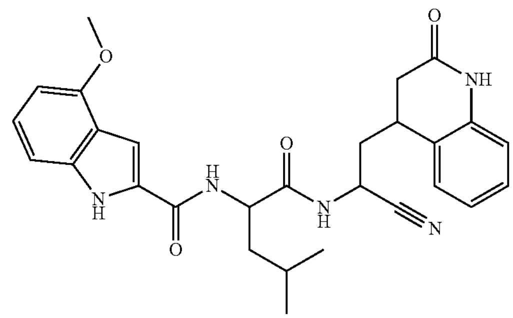 [SMILES: COc1cccc2[nH]c(C(=O)NC(CC(C)C)C(=O)NC(C#N)CC3CC(=O)Nc4ccccc43)cc12] |
| 249 | 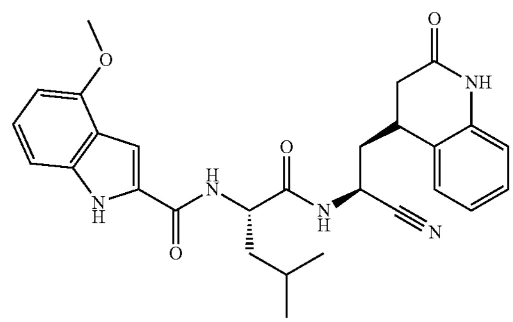 |
| 250 | 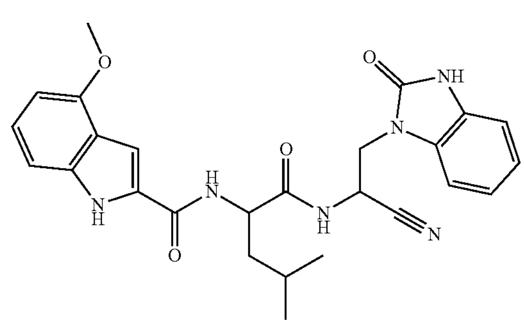 |

147 148
TABLE 1-continued
Exemplary compounds.
| Cmpd No. | Structure |
|---|---|
| 251 | 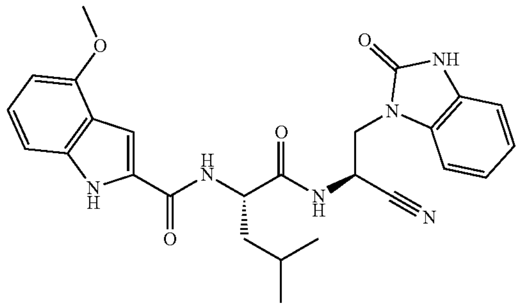 [SMILES: COc1cccc2[nH]c(C(=O)N[C@@H](CC(C)C)C(=O)N[C@H](C#N)Cn3c(=O)[nH]c4ccccc43)cc12] |
| 252 | 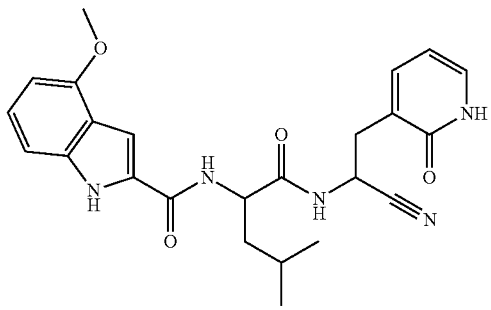 [SMILES: COc1cccc2[nH]c(C(=O)NC(CC(C)C)C(=O)NC(C#N)Cc3ccc[nH]c3=O)cc12] |
| 253 | 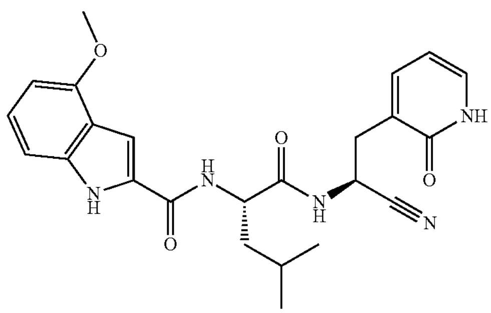 [SMILES: COc1cccc2[nH]c(C(=O)N[C@@H](CC(C)C)C(=O)N[C@H](C#N)Cc3ccc[nH]c3=O)cc12] |
| 254 | 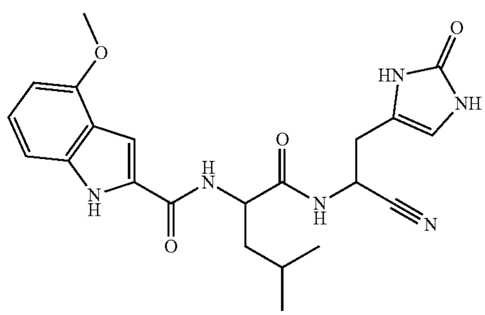 [SMILES: COc1cccc2[nH]c(C(=O)NC(CC(C)C)C(=O)NC(C#N)Cc3c[nH]c(=O)[nH]3)cc12] |
| 255 | 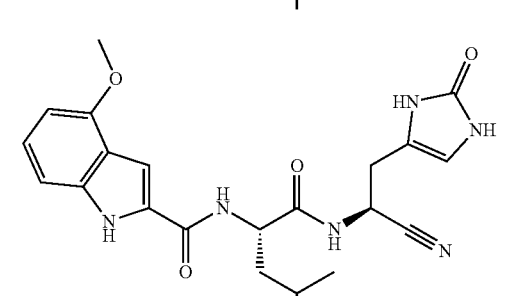 |

TABLE 1-continued
Exemplary compounds.
| Cmpd No. | Structure |
|---|---|
| 256 | 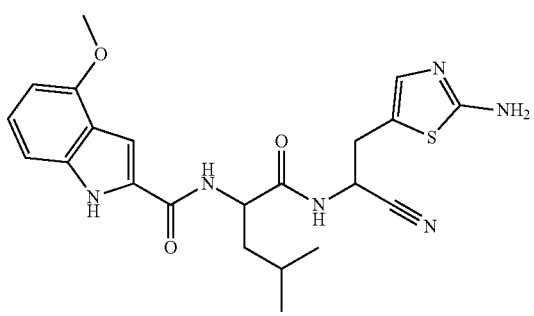 [SMILES: COc1cccc2[nH]c(C(=O)NC(CC(C)C)C(=O)NC(C#N)Cc3cnc(N)s3)cc12] |
| 257 | 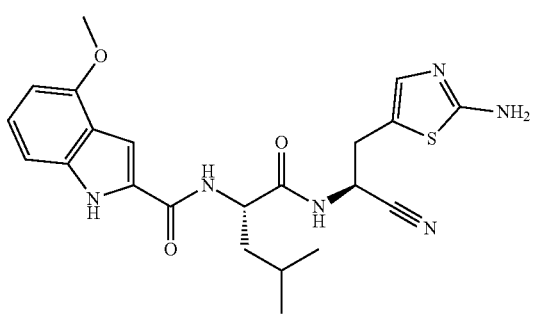 [SMILES: COc1cccc2[nH]c(C(=O)N[C@@H](CC(C)C)C(=O)N[C@H](C#N)Cc3cnc(N)s3)cc12] |
| 258 | 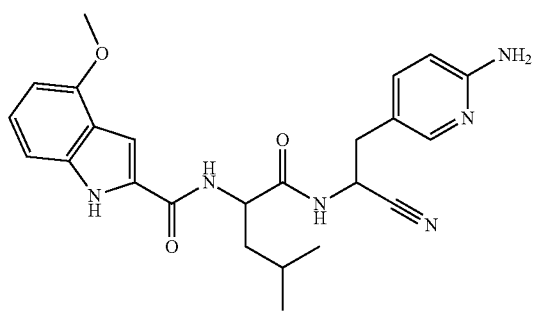 [SMILES: COc1cccc2[nH]c(C(=O)NC(CC(C)C)C(=O)NC(C#N)Cc3ccc(N)nc3)cc12] |
| 259 | 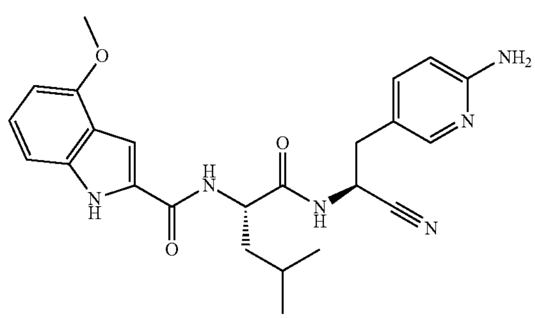 [SMILES: COc1cccc2[nH]c(C(=O)N[C@@H](CC(C)C)C(=O)N[C@H](C#N)Cc3ccc(N)nc3)cc12] |

151
TABLE 1-continued
Exemplary compounds.
| Cmpd No. | Structure |
|---|---|
| 260 | 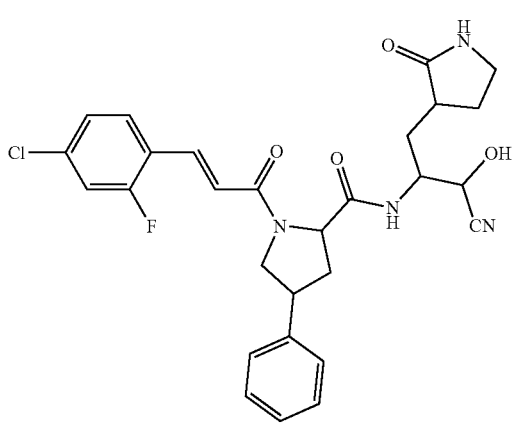 [SMILES: N#CC(O)C(CC1CCNC1=O)NC(=O)C1CC(c2ccccc2)CN1C(=O)/C=C/c1ccc(Cl)cc1F] |
| 261 | 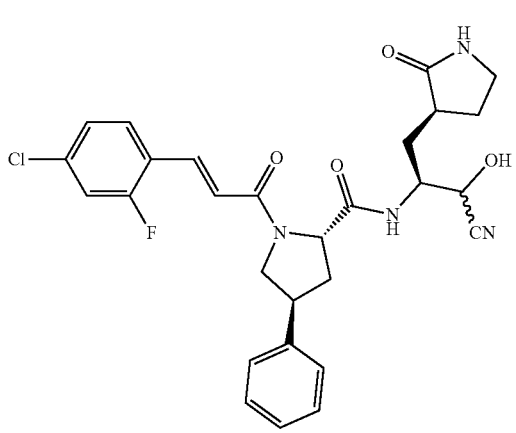 [SMILES: N#CC(O)[C@H](C[C@@H]1CCNC1=O)NC(=O)[C@@H]1C[C@@H](c2ccccc2)CN1C(=O)/C=C/c1ccc(Cl)cc1F] |
| 262 | 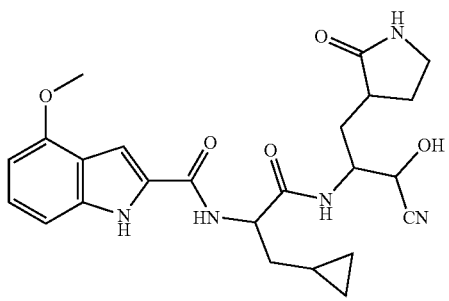 [SMILES: COc1cccc2[nH]c(C(=O)NC(CC3CC3)C(=O)NC(CC3CCNC3=O)C(O)C#N)cc12] |
| 263 | 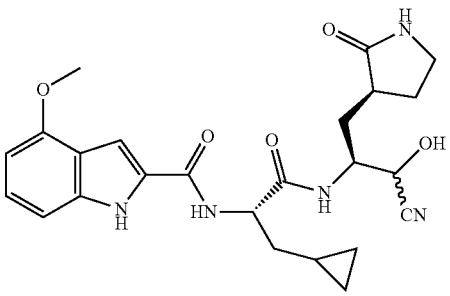 [SMILES: COc1cccc2[nH]c(C(=O)N[C@@H](CC3CC3)C(=O)N[C@@H](C[C@@H]3CCNC3=O)C(O)C#N)cc12] |

TABLE 1-continued
Exemplary compounds.
| Cmpd No. | Structure |
|---|---|
| 264 | 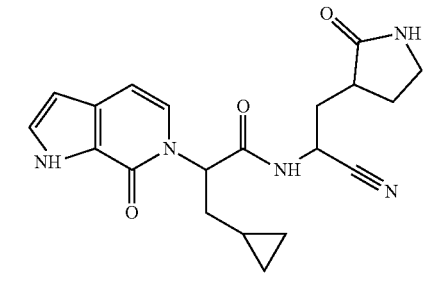 [SMILES: N#CC(CC1CCNC1=O)NC(=O)C(CC1CC1)n1ccc2cc[nH]c2c1=O] |
| 265 | 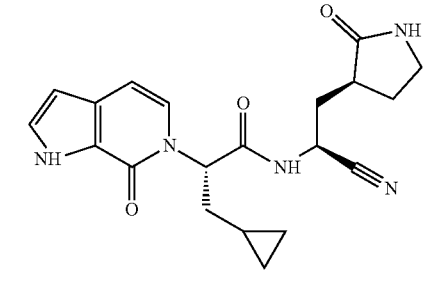 [SMILES: N#C[C@H](C[C@@H]1CCNC1=O)NC(=O)[C@H](CC1CC1)n1ccc2cc[nH]c2c1=O] |
| 266 | 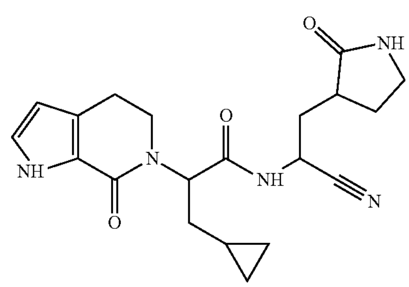 [SMILES: N#CC(CC1CCNC1=O)NC(=O)C(CC1CC1)N1CCc2cc[nH]c2C1=O] |
| 267 | 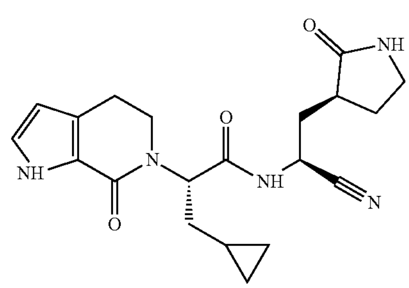 [SMILES: N#C[C@H](C[C@@H]1CCNC1=O)NC(=O)[C@H](CC1CC1)N1CCc2cc[nH]c2C1=O] |
| 268 | 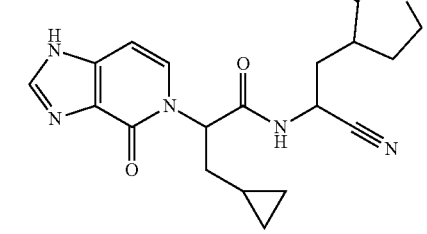 |

TABLE 1-continued

| Cmpd No. | Structure |
|---|---|
| 269 | 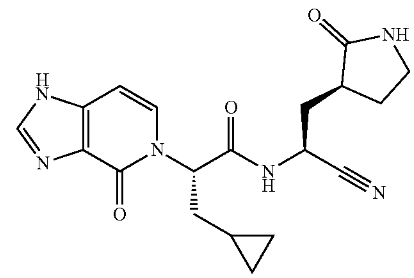 [SMILES: N#C[C@H](C[C@@H]1CCNC1=O)NC(=O)[C@H](CC1CC1)n1ccc2[nH]cnc2c1=O] |
| 270 | 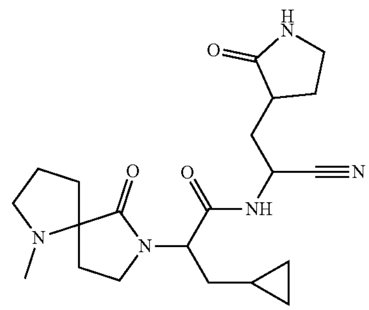 [SMILES: CN1CCCC12CCN(C(CC1CC1)C(=O)NC(C#N)CC1CCNC1=O)C2=O] |
| 271 | 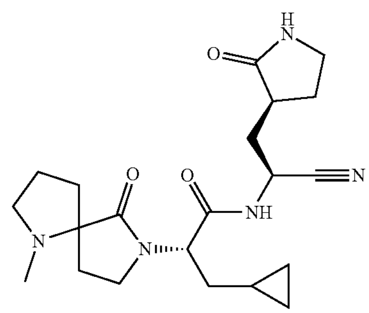 [SMILES: CN1CCCC12CCN([C@@H](CC1CC1)C(=O)N[C@H](C#N)C[C@@H]1CCNC1=O)C2=O] |
| 272 | 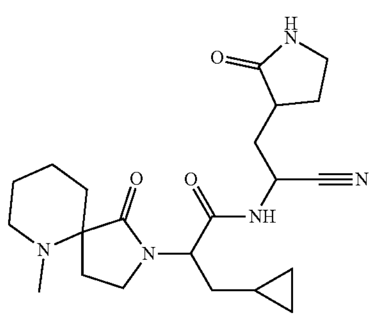 [SMILES: CN1CCCCC12CCN(C(CC1CC1)C(=O)NC(C#N)CC1CCNC1=O)C2=O] |
| 273 | 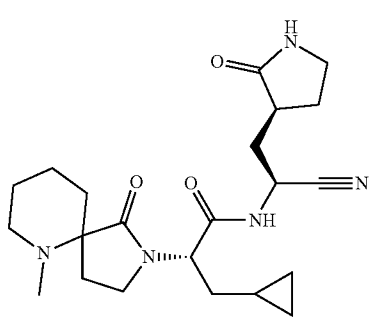 [SMILES: CN1CCCCC12CCN([C@@H](CC1CC1)C(=O)N[C@H](C#N)C[C@@H]1CCNC1=O)C2=O] |

157
158
TABLE 1-continued
Exemplary compounds.
| Cmpd No. | Structure |
|---|---|
| 274 | 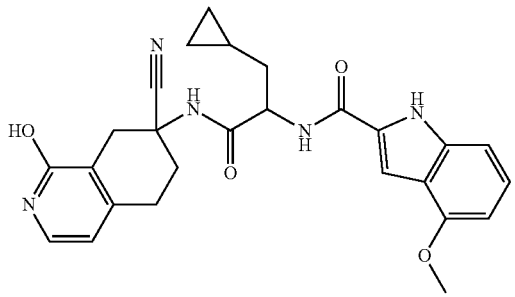 [SMILES: COc1cccc2[nH]c(C(=O)NC(CC3CC3)C(=O)NC3(C#N)CCc4ccnc(O)c4C3)cc12] |
| 275 | 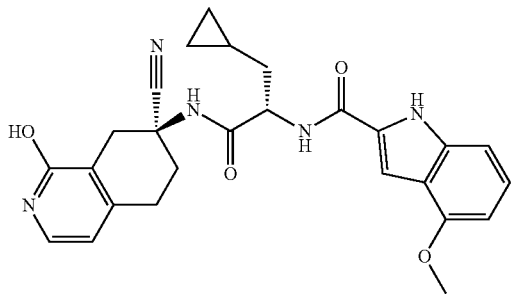 [SMILES: COc1cccc2[nH]c(C(=O)N[C@@H](CC3CC3)C(=O)N[C@@]3(C#N)CCc4ccnc(O)c4C3)cc12] |
| 276 | 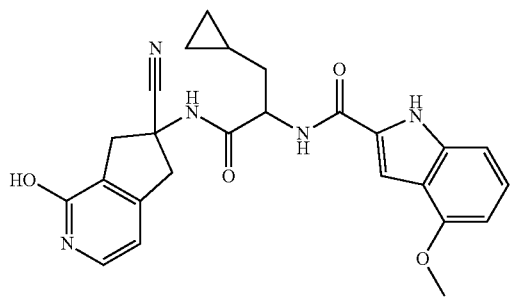 [SMILES: COc1cccc2[nH]c(C(=O)NC(CC3CC3)C(=O)NC3(C#N)Cc4ccnc(O)c4C3)cc12] |
| 277 | 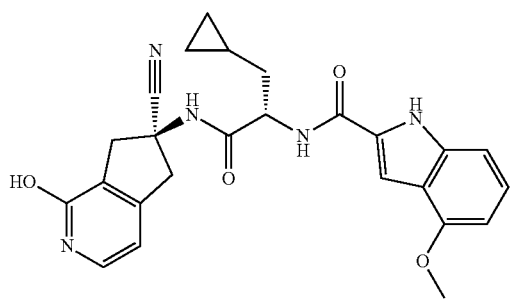 [SMILES: COc1cccc2[nH]c(C(=O)N[C@@H](CC3CC3)C(=O)N[C@@]3(C#N)Cc4ccnc(O)c4C3)cc12] |
| 278 | 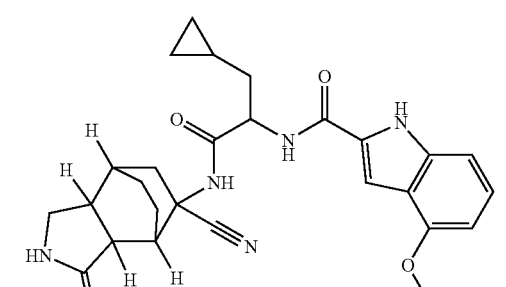 |

TABLE 1-continued

Exemplary compounds.

| Cmpd No. | Structure |
|---|---|
| 279 | 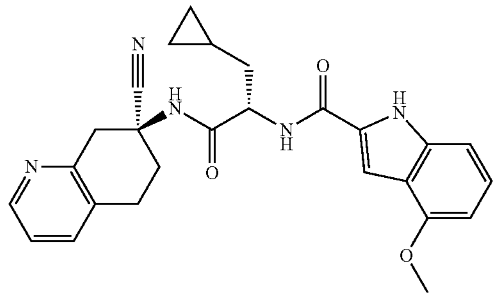 [SMILES: COc1cccc2[nH]c(C(=O)N[C@@H](CC3CC3)C(=O)N[C@@]3(C#N)CCc4cccnc4C3)cc12] |
| 280 | 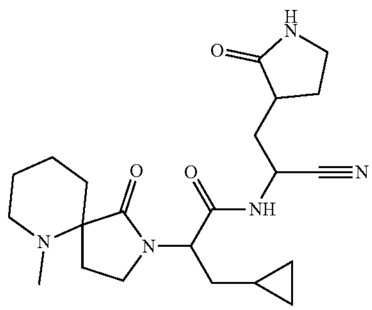 [SMILES: CN1CCCCC12CCN(C(CC1CC1)C(=O)NC(C#N)CC1CCNC1=O)C2=O] |
| 281 | 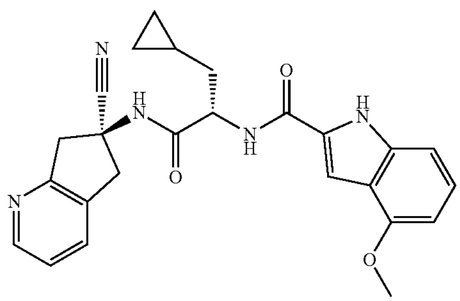 [SMILES: COc1cccc2[nH]c(C(=O)N[C@@H](CC3CC3)C(=O)N[C@@]3(C#N)Cc4cccnc4C3)cc12] |
| 282 | 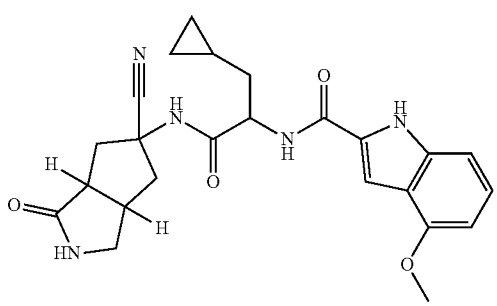 [SMILES: COc1cccc2[nH]c(C(=O)NC(CC3CC3)C(=O)NC3(C#N)CC4CNC(=O)C4C3)cc12] |
| 283 | 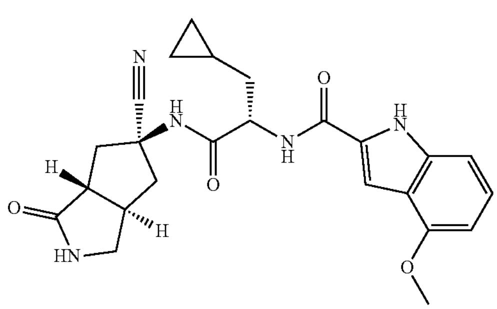 [SMILES: COc1cccc2[nH]c(C(=O)N[C@@H](CC3CC3)C(=O)N[C@@]3(C#N)C[C@H]4CNC(=O)[C@@H]4C3)cc12] |

TABLE 1-continued

Exemplary compounds.

| Cmpd No. | Structure |
|---|---|
| 284 | 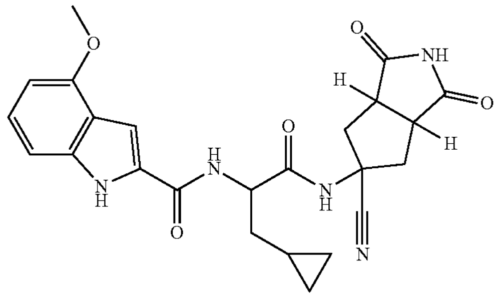 [SMILES: COc1cccc2[nH]c(C(=O)NC(CC3CC3)C(=O)NC3(C#N)CC4C(=O)NC(=O)C4C3)cc12] |
| 285 | 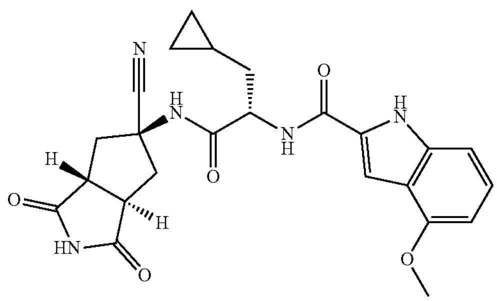 |
| 286 | 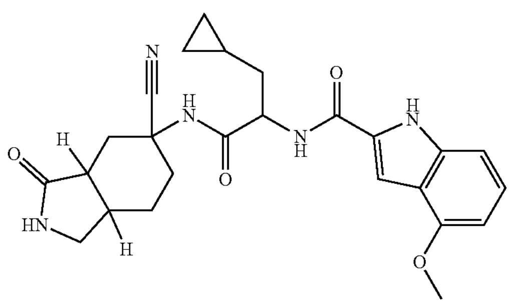 [SMILES: COc1cccc2[nH]c(C(=O)NC(CC3CC3)C(=O)NC3(C#N)CCC4CNC(=O)C4C3)cc12] |
| 287 | 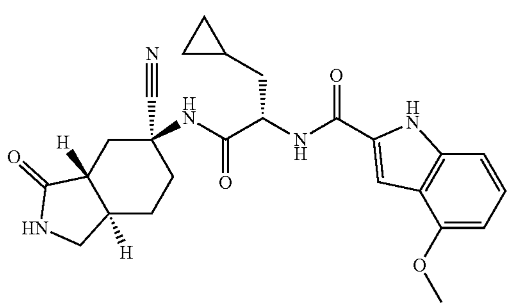 [SMILES: COc1cccc2[nH]c(C(=O)N[C@@H](CC3CC3)C(=O)N[C@@]3(C#N)CC[C@H]4CNC(=O)[C@@H]4C3)cc12] |
| 288 | 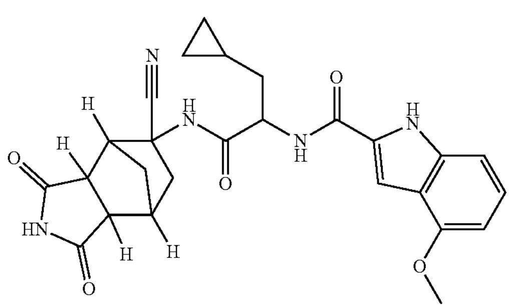 [SMILES: COc1cccc2[nH]c(C(=O)NC(CC3CC3)C(=O)NC3(C#N)CC4CC3C3C(=O)NC(=O)C43)cc12] |

TABLE 1-continued

Exemplary compounds.

| Cmpd No. | Structure |
|---|---|
| 289 | 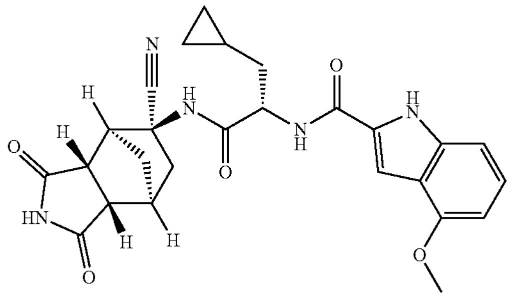 |
| 290 | 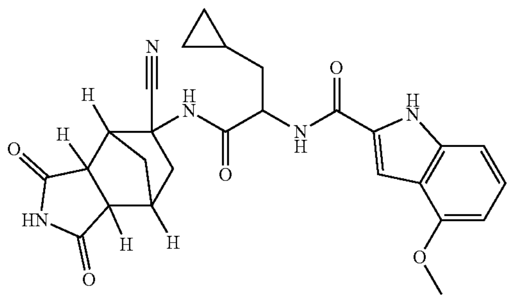 [SMILES: COc1cccc2[nH]c(C(=O)NC(CC3CC3)C(=O)NC3(C#N)CC4CC3C3C(=O)NC(=O)C43)cc12] |
| 291 | 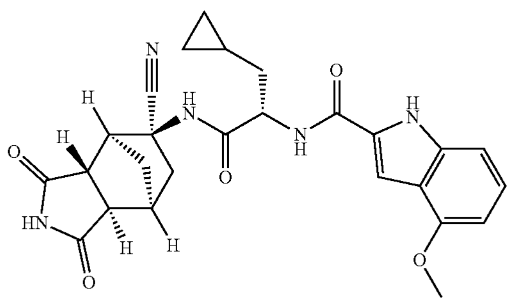 [SMILES: COc1cccc2[nH]c(C(=O)N[C@@H](CC3CC3)C(=O)N[C@@]3(C#N)C[C@@H]4C[C@H]3[C@H]3C(=O)NC(=O)[C@H]43)cc12] |
| 292 | 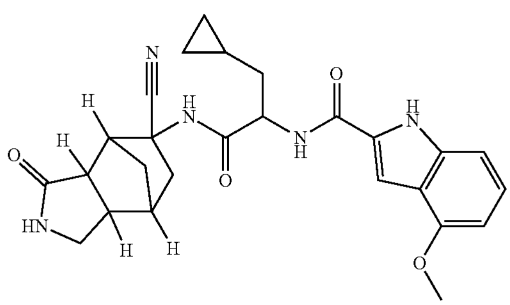 [SMILES: COc1cccc2[nH]c(C(=O)NC(CC3CC3)C(=O)NC3(C#N)CC4CC3C3C(=O)NCC43)cc12] |
| 293 | 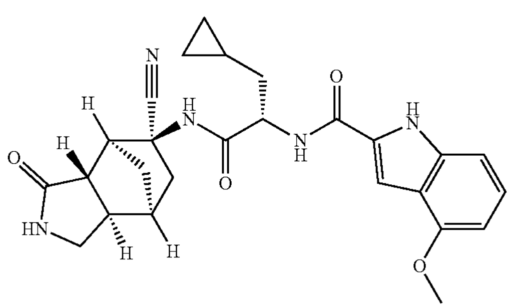 [SMILES: COc1cccc2[nH]c(C(=O)N[C@@H](CC3CC3)C(=O)N[C@@]3(C#N)C[C@@H]4C[C@H]3[C@H]3C(=O)NC[C@H]43)cc12] |

TABLE 1-continued
Exemplary compounds.
| Cmpd No. | Structure |
|---|---|
| 294 | 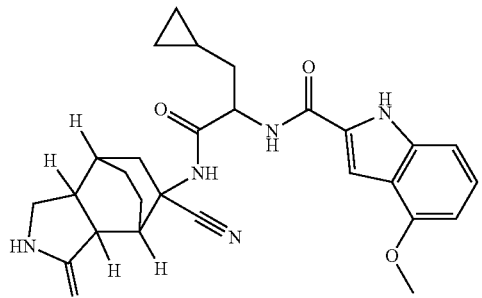 |
| 295 | 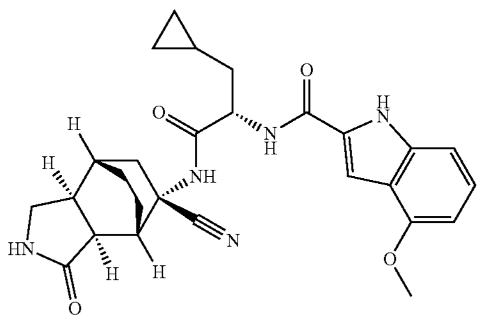 [SMILES: COc1cccc2[nH]c(C(=O)N[C@@H](CC3CC3)C(=O)N[C@@]3(C#N)C[C@@H]4CC[C@H]3[C@H]3C(=O)NC[C@@H]43)cc12] |
| 296 | 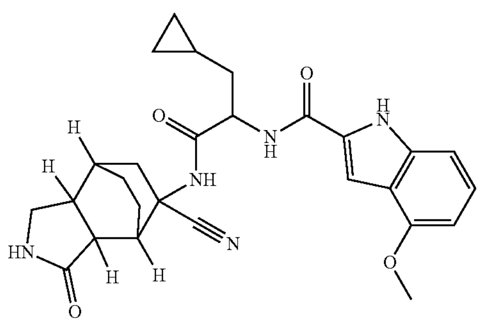 [SMILES: COc1cccc2[nH]c(C(=O)NC(CC3CC3)C(=O)NC3(C#N)CC4CCC3C3C(=O)NCC43)cc12] |
| 297 | 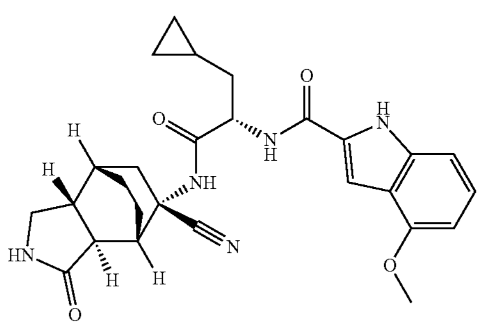 [SMILES: COc1cccc2[nH]c(C(=O)N[C@@H](CC3CC3)C(=O)N[C@@]3(C#N)C[C@@H]4CC[C@H]3[C@H]3C(=O)NC[C@H]43)cc12] |

TABLE 1-continued
Exemplary compounds.
| Cmpd No. | Structure |
|---|---|
| 298 | 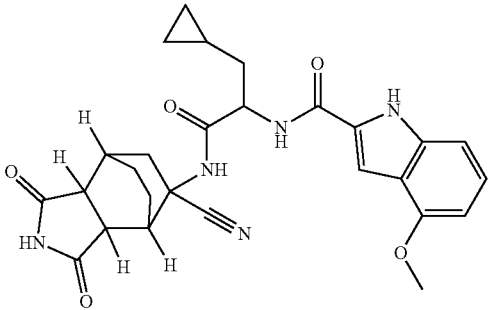 [SMILES: COc1cccc2[nH]c(C(=O)NC(CC3CC3)C(=O)NC3(C#N)CC4CCC3C3C(=O)NC(=O)C43)cc12] |
| 299 | 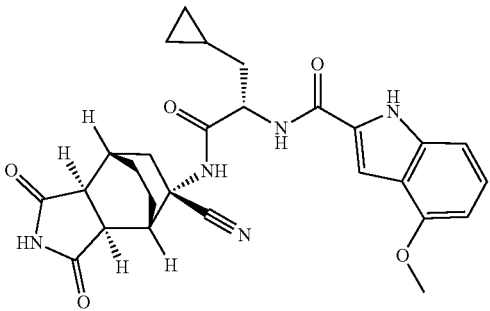 [SMILES: COc1cccc2[nH]c(C(=O)N[C@@H](CC3CC3)C(=O)N[C@@]3(C#N)C[C@@H]4CC[C@H]3[C@H]3C(=O)NC(=O)[C@@H]43)cc12] |
| 300 | 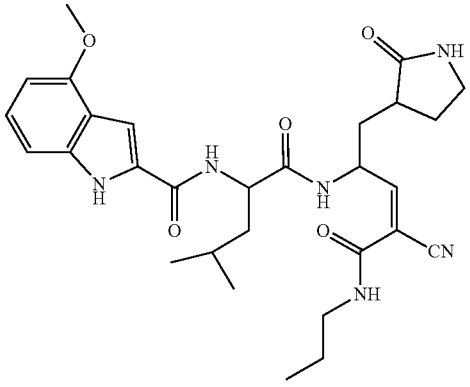 [SMILES: CCCNC(=O)/C(C#N)=C\C(CC1CCNC1=O)NC(=O)C(CC(C)C)NC(=O)c1cc2c(OC)cccc2[nH]1] |
| 301 | 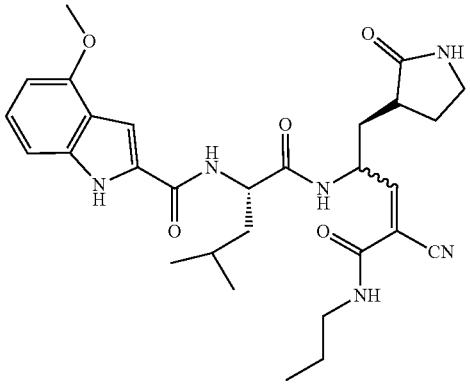 |

TABLE 1-continued

Exemplary compounds.

| Cmpd No. | Structure |
|---|---|
| 302 | 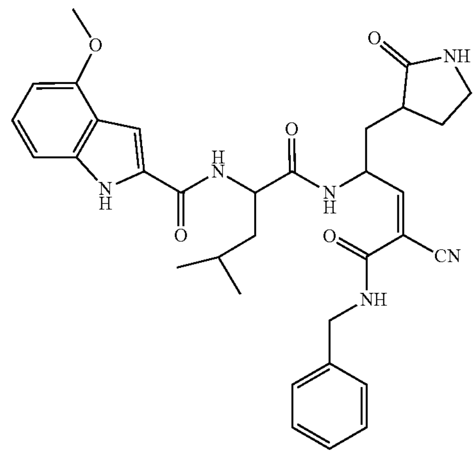 [SMILES: COc1cccc2[nH]c(C(=O)NC(CC(C)C)C(=O)NC(/C=C(/C#N)C(=O)NCc3ccccc3)CC3CCNC3=O)cc12] |
| 303 | 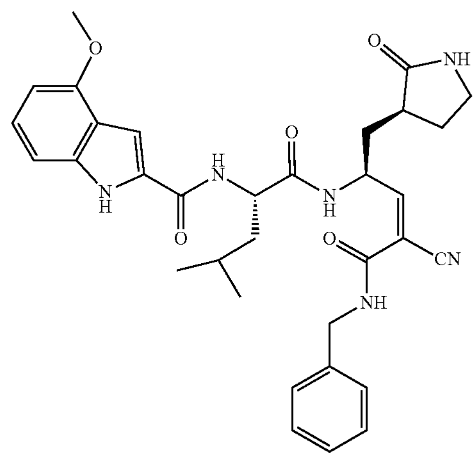 [SMILES: COc1cccc2[nH]c(C(=O)N[C@@H](CC(C)C)C(=O)N[C@H](/C=C(/C#N)C(=O)NCc3ccccc3)C[C@@H]3CCNC3=O)cc12] |
| 304 | 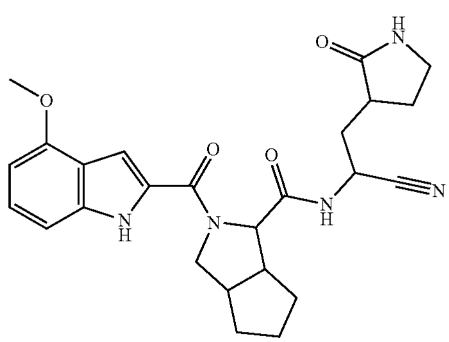 [SMILES: COc1cccc2[nH]c(C(=O)N3CC4CCCC4C3C(=O)NC(C#N)CC3CCNC3=O)cc12] |
| 305 | 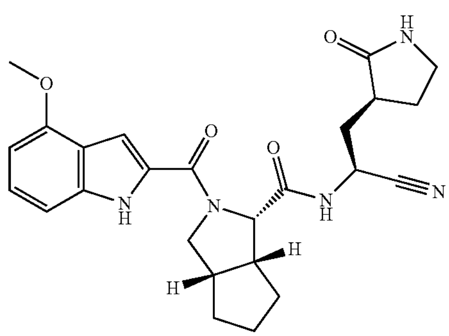 [SMILES: COc1cccc2[nH]c(C(=O)N3C[C@H]4CCC[C@H]4[C@H]3C(=O)N[C@H](C#N)C[C@@H]3CCNC3=O)cc12] |

TABLE 1-continued
Exemplary compounds.
| Cmpd No. | Structure |
|---|---|
| 306 | 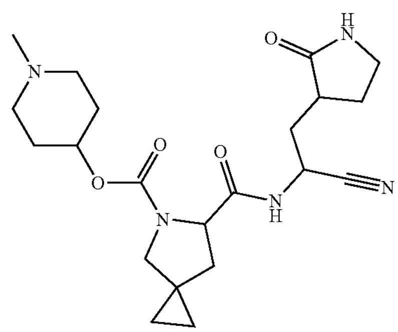 [SMILES: CN1CCC(OC(=O)N2CC3(CC3)CC2C(=O)NC(C#N)CC2CCNC2=O)CC1] |
| 307 | 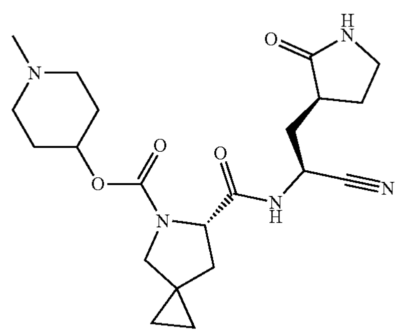 [SMILES: CN1CCC(OC(=O)N2CC3(CC3)C[C@H]2C(=O)N[C@H](C#N)C[C@@H]2CCNC2=O)CC1] |
| 308 | 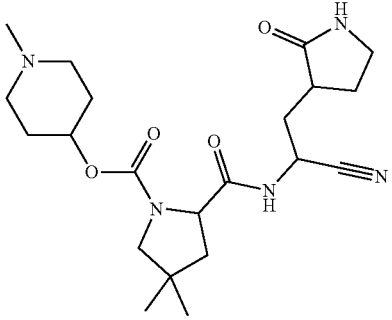 [SMILES: CN1CCC(OC(=O)N2CC(C)(C)CC2C(=O)NC(C#N)CC2CCNC2=O)CC1] |
| 309 | 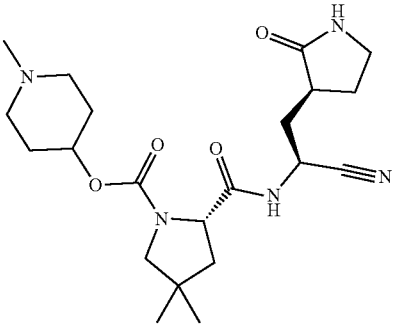 [SMILES: CN1CCC(OC(=O)N2CC(C)(C)C[C@H]2C(=O)N[C@H](C#N)C[C@@H]2CCNC2=O)CC1] |

TABLE 1-continued

Exemplary compounds.

| Cmpd No. | Structure |
|---|---|
| 310 | 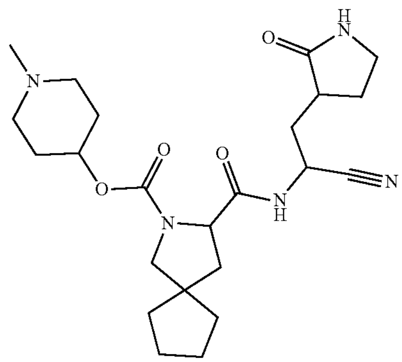 [SMILES: CN1CCC(OC(=O)N2CC3(CCCC3)CC2C(=O)NC(C#N)CC2CCNC2=O)CC1] |
| 311 | 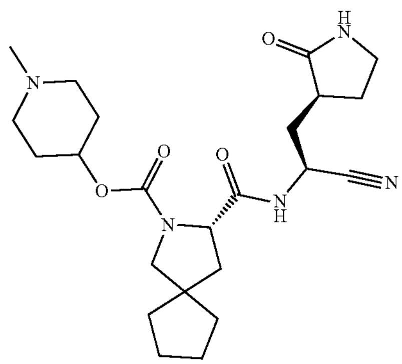 [SMILES: CN1CCC(OC(=O)N2CC3(CCCC3)C[C@H]2C(=O)N[C@H](C#N)C[C@@H]2CCNC2=O)CC1] |
| 312 | 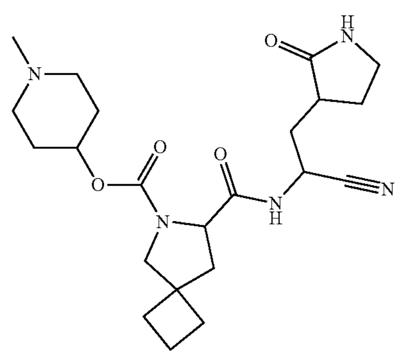 [SMILES: CN1CCC(OC(=O)N2CC3(CCC3)CC2C(=O)NC(C#N)CC2CCNC2=O)CC1] |
| 313 | 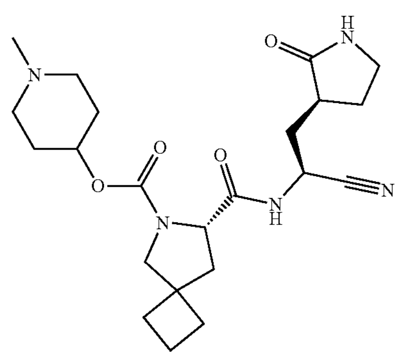 [SMILES: CN1CCC(OC(=O)N2CC3(CCC3)C[C@H]2C(=O)N[C@H](C#N)C[C@@H]2CCNC2=O)CC1] |

TABLE 1-continued

| Exemplary compounds. | |
|---|---|
| Cmpd No. | Structure |
| 314 | |
| 315 | |
| 316 | |
| 317 | |

177
178
TABLE 1-continued
Exemplary compounds.
| Cmpd No. | Structure |
|---|---|
| 318 | 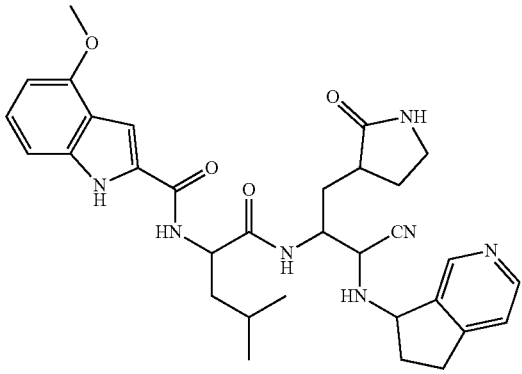 [SMILES: COc1cccc2[nH]c(C(=O)NC(CC(C)C)C(=O)NC(CC3CCNC3=O)C(C#N)NC3CCc4ccncc43)cc12] |
| 319 | 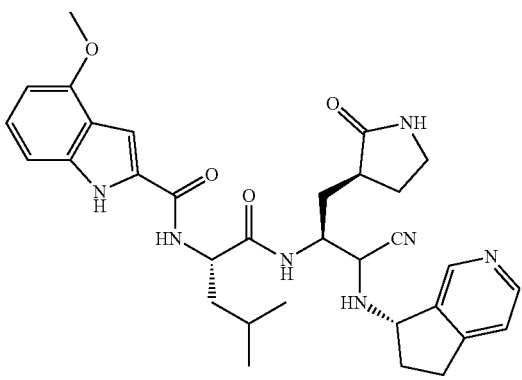 [SMILES: COc1cccc2[nH]c(C(=O)N[C@@H](CC(C)C)C(=O)N[C@@H](C[C@@H]3CCNC3=O)C(C#N)N[C@H]3CCc4ccncc43)cc12] |
| 320 | 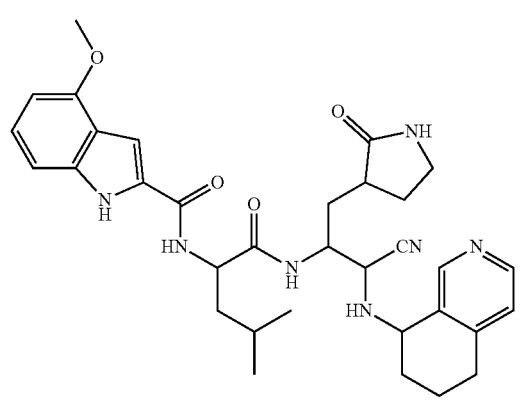 [SMILES: COc1cccc2[nH]c(C(=O)NC(CC(C)C)C(=O)NC(CC3CCNC3=O)C(C#N)NC3CCCc4ccncc43)cc12] |
| 321 | 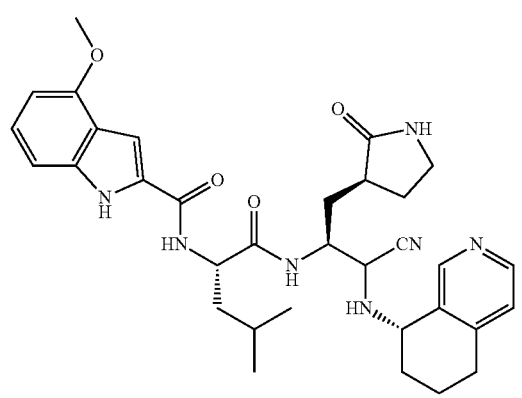 [SMILES: COc1cccc2[nH]c(C(=O)N[C@@H](CC(C)C)C(=O)N[C@@H](C[C@@H]3CCNC3=O)C(C#N)N[C@H]3CCCc4ccncc43)cc12] |

TABLE 1-continued

Exemplary compounds.

| Cmpd No. | Structure |
|---|---|
| 322 | 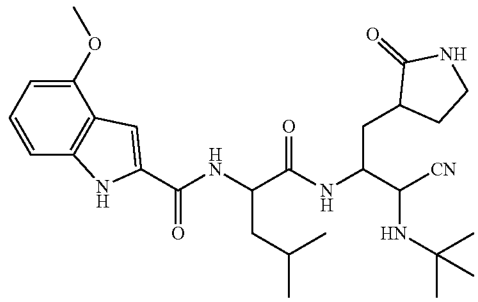 [SMILES: COc1cccc2[nH]c(C(=O)NC(CC(C)C)C(=O)NC(CC3CCNC3=O)C(C#N)NC(C)(C)C)cc12] |
| 323 | 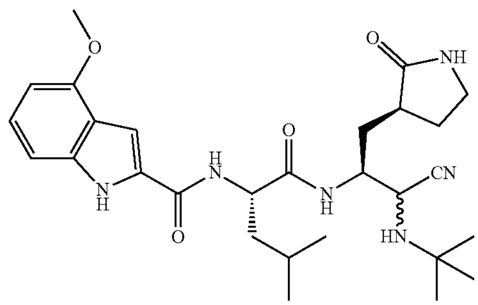 [SMILES: COc1cccc2[nH]c(C(=O)N[C@@H](CC(C)C)C(=O)N[C@@H](C[C@@H]3CCNC3=O)C(C#N)NC(C)(C)C)cc12] |
| 324 | 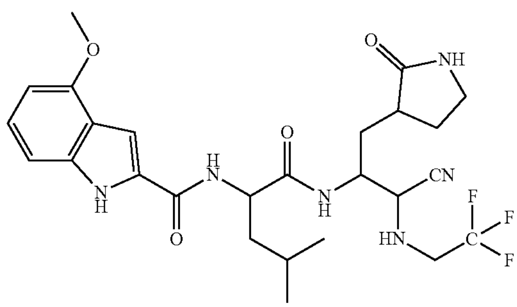 [SMILES: COc1cccc2[nH]c(C(=O)NC(CC(C)C)C(=O)NC(CC3CCNC3=O)C(C#N)NCC(F)(F)F)cc12] |
| 325 | 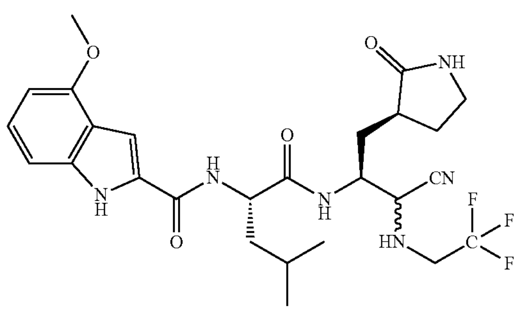 [SMILES: COc1cccc2[nH]c(C(=O)N[C@@H](CC(C)C)C(=O)N[C@@H](C[C@@H]3CCNC3=O)C(C#N)NCC(F)(F)F)cc12] |
| 326 | 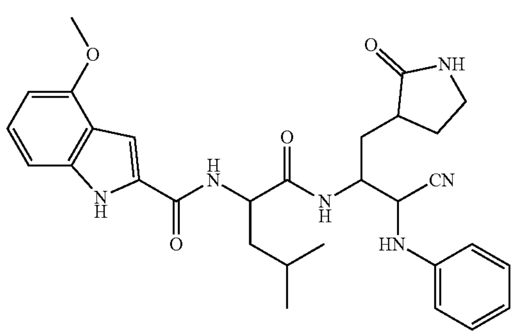 [SMILES: COc1cccc2[nH]c(C(=O)NC(CC(C)C)C(=O)NC(CC3CCNC3=O)C(C#N)Nc3ccccc3)cc12] |

TABLE 1-continued
Exemplary compounds.
| Cmpd No. | Structure |
|---|---|
| 327 | 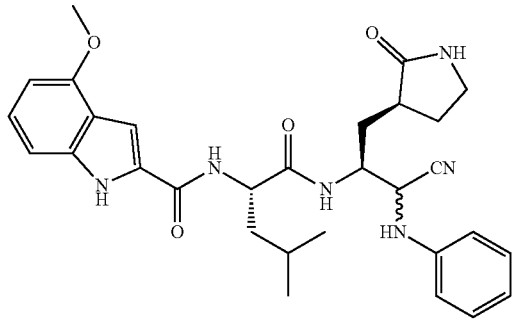 [SMILES: COc1cccc2[nH]c(C(=O)N[C@@H](CC(C)C)C(=O)N[C@@H](C[C@@H]3CCNC3=O)C(C#N)Nc3ccccc3)cc12] |
| 328 | 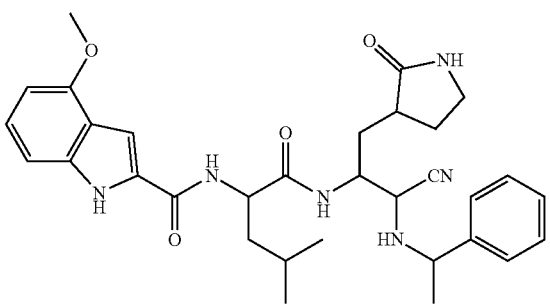 [SMILES: COc1cccc2[nH]c(C(=O)NC(CC(C)C)C(=O)NC(CC3CCNC3=O)C(C#N)NC(C)c3ccccc3)cc12] |
| 329 | 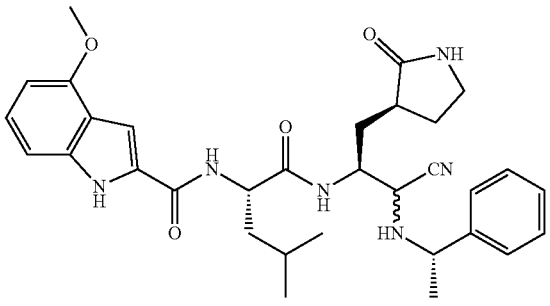 [SMILES: COc1cccc2[nH]c(C(=O)N[C@@H](CC(C)C)C(=O)N[C@@H](C[C@@H]3CCNC3=O)C(C#N)N[C@@H](C)c3ccccc3)cc12] |
| 330 | 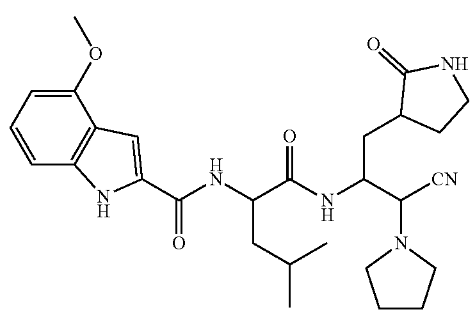 [SMILES: COc1cccc2[nH]c(C(=O)NC(CC(C)C)C(=O)NC(CC3CCNC3=O)C(C#N)N3CCCC3)cc12] |
| 331 | 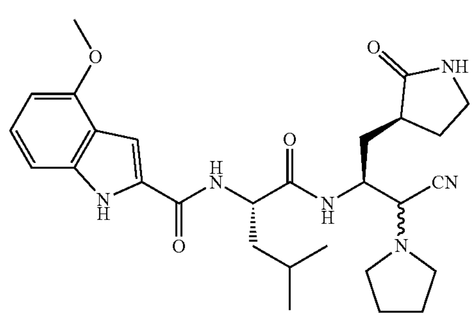 [SMILES: COc1cccc2[nH]c(C(=O)N[C@@H](CC(C)C)C(=O)N[C@@H](C[C@@H]3CCNC3=O)C(C#N)N3CCCC3)cc12] |

TABLE 1-continued
Exemplary compounds.
| Cmpd No. | Structure |
|---|---|
| 332 | 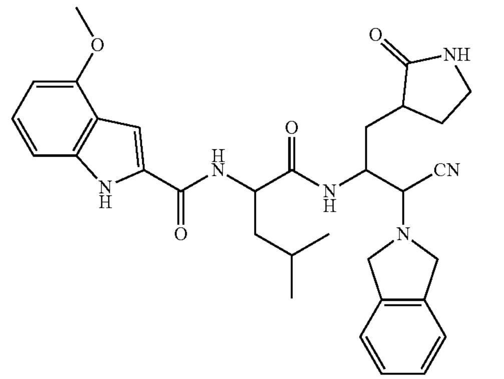 [SMILES: COc1cccc2[nH]c(C(=O)NC(CC(C)C)C(=O)NC(CC3CCNC3=O)C(C#N)N3Cc4ccccc4C3)cc12] |
| 333 | 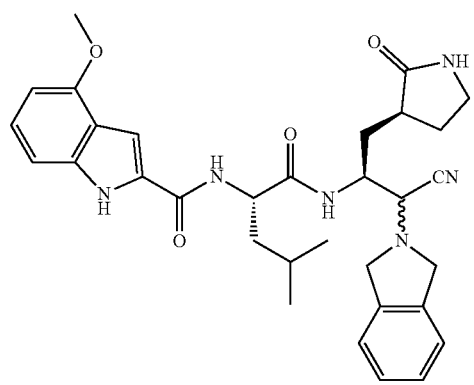 [SMILES: COc1cccc2[nH]c(C(=O)N[C@@H](CC(C)C)C(=O)N[C@@H](C[C@@H]3CCNC3=O)C(C#N)N3Cc4ccccc4C3)cc12] |
| 334 | 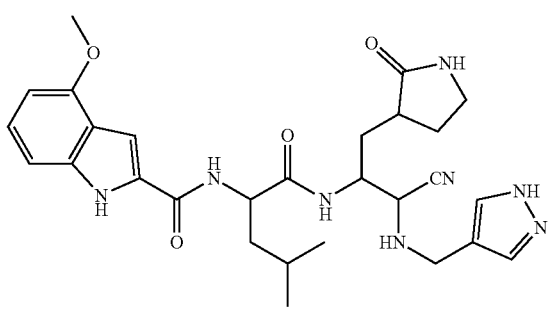 [SMILES: COc1cccc2[nH]c(C(=O)NC(CC(C)C)C(=O)NC(CC3CCNC3=O)C(C#N)NCc3cn[nH]c3)cc12] |
| 335 | 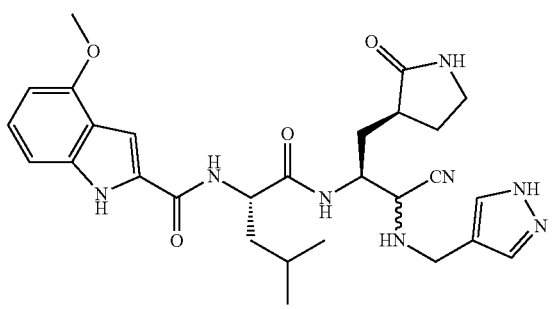 [SMILES: COc1cccc2[nH]c(C(=O)N[C@@H](CC(C)C)C(=O)N[C@@H](C[C@@H]3CCNC3=O)C(C#N)NCc3cn[nH]c3)cc12] |

TABLE 1-continued

Exemplary compounds.

| Cmpd No. | Structure |
|---|---|
| 336 | 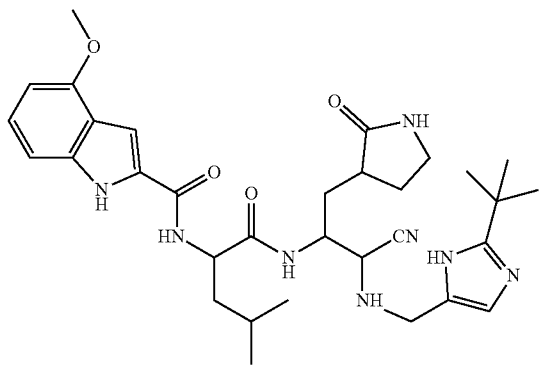 [SMILES: COc1cccc2[nH]c(C(=O)NC(CC(C)C)C(=O)NC(CC3CCNC3=O)C(C#N)NCc3cnc(C(C)(C)C)[nH]3)cc12] |
| 337 | 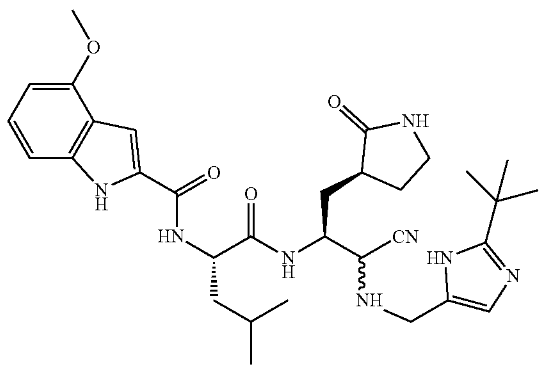 [SMILES: COc1cccc2[nH]c(C(=O)N[C@@H](CC(C)C)C(=O)N[C@@H](C[C@@H]3CCNC3=O)C(C#N)NCc3cnc(C(C)(C)C)[nH]3)cc12] |
| 338 | 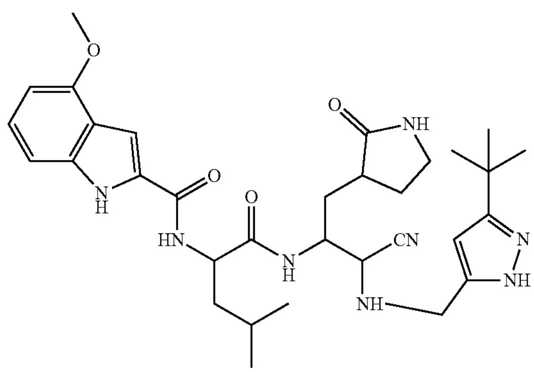 [SMILES: COc1cccc2[nH]c(C(=O)NC(CC(C)C)C(=O)NC(CC3CCNC3=O)C(C#N)NCc3cc(C(C)(C)C)n[nH]3)cc12] |
| 339 | 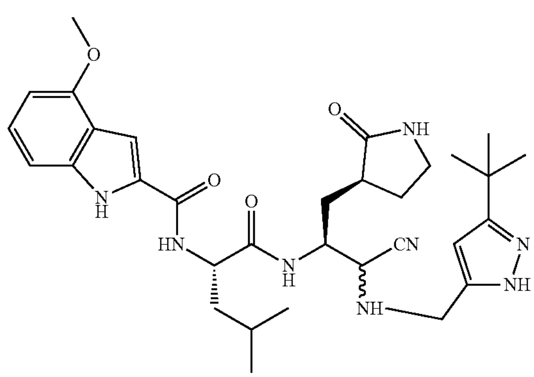 [SMILES: COc1cccc2[nH]c(C(=O)N[C@@H](CC(C)C)C(=O)N[C@@H](C[C@@H]3CCNC3=O)C(C#N)NCc3cc(C(C)(C)C)n[nH]3)cc12] |

TABLE 1-continued

Exemplary compounds.

| Cmpd No. | Structure |
|---|---|
| 340 | 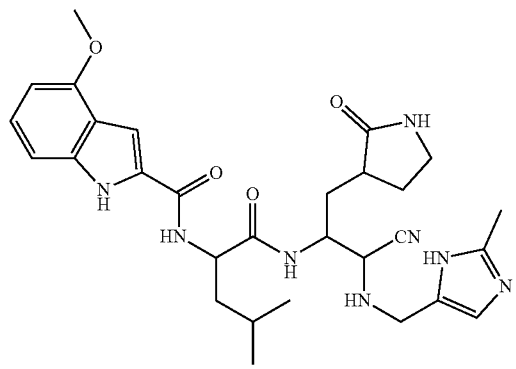 [SMILES: COc1cccc2[nH]c(C(=O)NC(CC(C)C)C(=O)NC(CC3CCNC3=O)C(C#N)NCc3cnc(C)[nH]3)cc12] |
| 341 | 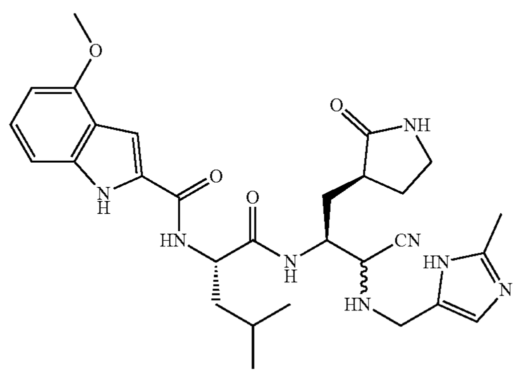 [SMILES: COc1cccc2[nH]c(C(=O)N[C@@H](CC(C)C)C(=O)N[C@@H](C[C@@H]3CCNC3=O)C(C#N)NCc3cnc(C)[nH]3)cc12] |
| 342 | 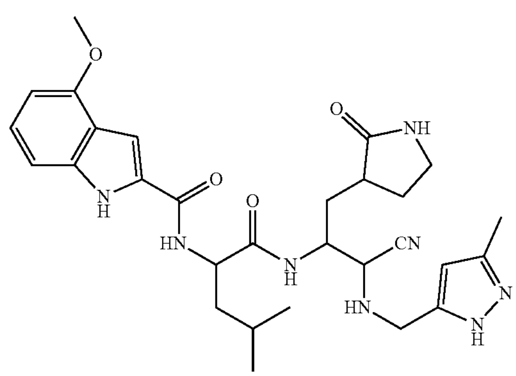 [SMILES: COc1cccc2[nH]c(C(=O)NC(CC(C)C)C(=O)NC(CC3CCNC3=O)C(C#N)NCc3cc(C)n[nH]3)cc12] |
| 343 | 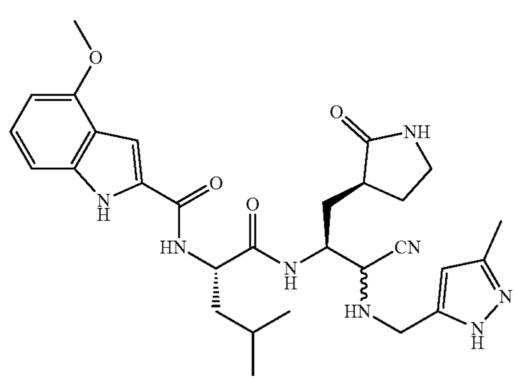 [SMILES: COc1cccc2[nH]c(C(=O)N[C@@H](CC(C)C)C(=O)N[C@@H](C[C@@H]3CCNC3=O)C(C#N)NCc3cc(C)n[nH]3)cc12] |

TABLE 1-continued
Exemplary compounds.
| Cmpd No. | Structure |
|---|---|
| 344 | 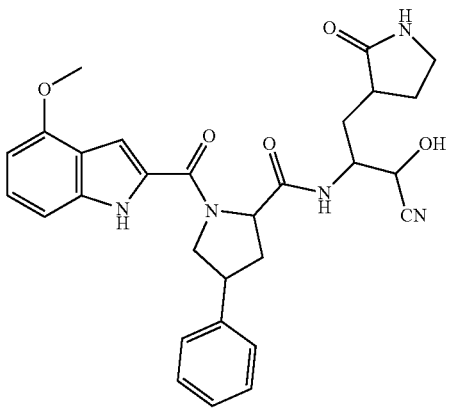 [SMILES: COc1cccc2[nH]c(C(=O)N3CC(c4ccccc4)CC3C(=O)NC(CC3CCNC3=O)C(O)C#N)cc12] |
| 345 | 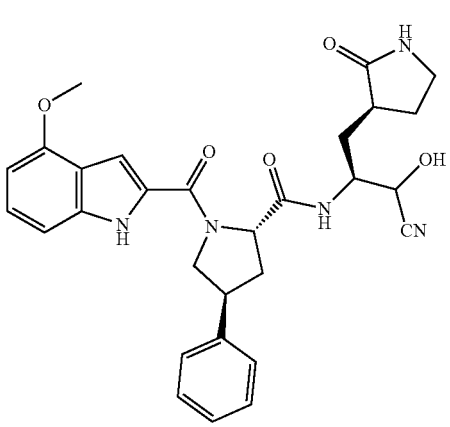 [SMILES: COc1cccc2[nH]c(C(=O)N3C[C@H](c4ccccc4)C[C@H]3C(=O)N[C@@H](C[C@@H]3CCNC3=O)C(O)C#N)cc12] |
| 346 | 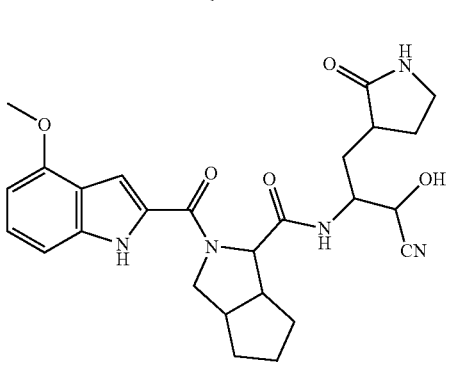 |
| 347 | 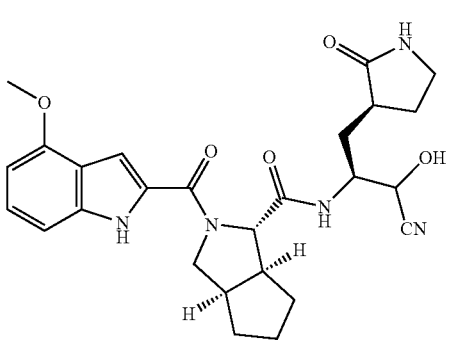 [SMILES: COc1cccc2[nH]c(C(=O)N3C[C@@H]4CCC[C@@H]4[C@H]3C(=O)N[C@@H](C[C@@H]3CCNC3=O)C(O)C#N)cc12] |

TABLE 1-continued
Exemplary compounds.
| Cmpd No. | Structure |
|---|---|
| 348 | 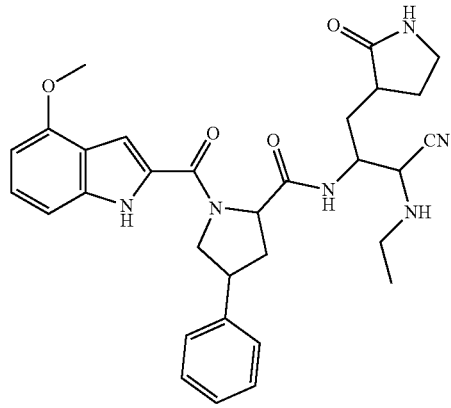 [SMILES: CCNC(C#N)C(CC1CCNC1=O)NC(=O)C1CC(c2ccccc2)CN1C(=O)c1cc2c(OC)cccc2[nH]1] |
| 349 | 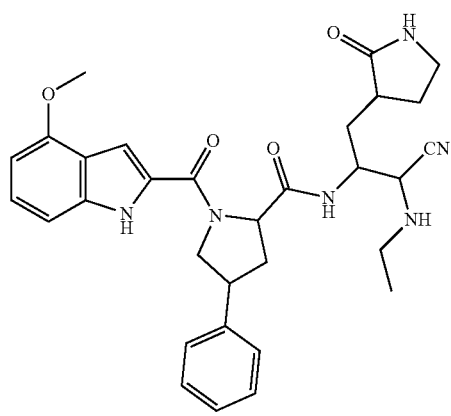 [SMILES: CCNC(C#N)C(CC1CCNC1=O)NC(=O)C1CC(c2ccccc2)CN1C(=O)c1cc2c(OC)cccc2[nH]1] |
| 350 | 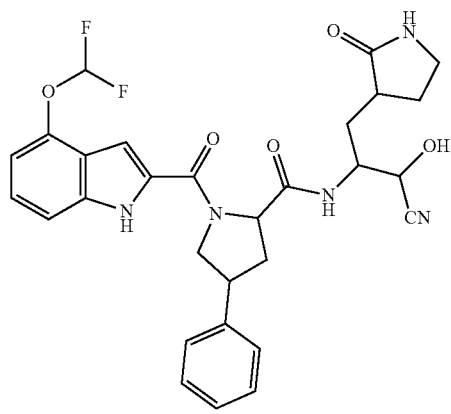 [SMILES: N#CC(O)C(CC1CCNC1=O)NC(=O)C1CC(c2ccccc2)CN1C(=O)c1cc2c(OC(F)F)cccc2[nH]1] |

TABLE 1-continued

| Exemplary compounds. | |
|---|---|
| Cmpd No. | Structure |
| 351 | |
| 352 | |
| 353 | |

TABLE 1-continued

Exemplary compounds.

| Cmpd No. | Structure |
| --- | --- |
| 354 | 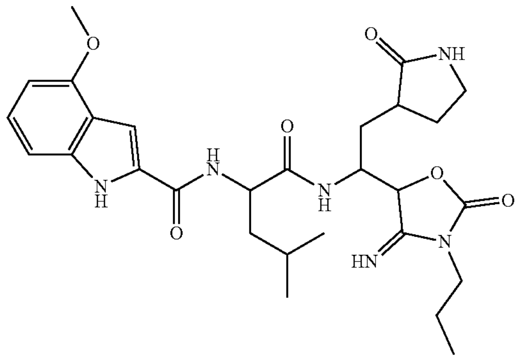 [SMILES: CCCN1C(=N)C(C(CC2CCNC2=O)NC(=O)C(CC(C)C)NC(=O)c2cc3c(OC)cccc3[nH]2)OC1=O] |
| 355 | 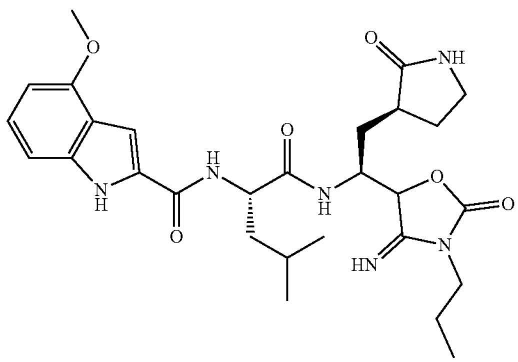 [SMILES: CCCN1C(=N)C([C@H](C[C@@H]2CCNC2=O)NC(=O)[C@H](CC(C)C)NC(=O)c2cc3c(OC)cccc3[nH]2)OC1=O] |
| 356 | 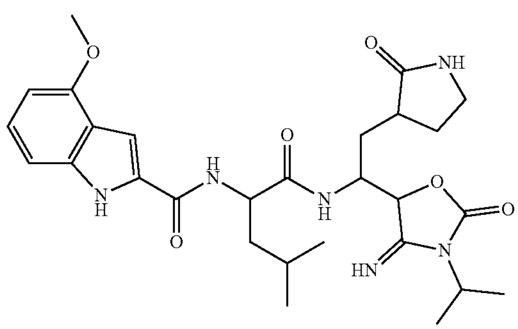 [SMILES: COc1cccc2[nH]c(C(=O)NC(CC(C)C)C(=O)NC(CC3CCNC3=O)C3OC(=O)N(C(C)C)C3=N)cc12] |
| 357 | 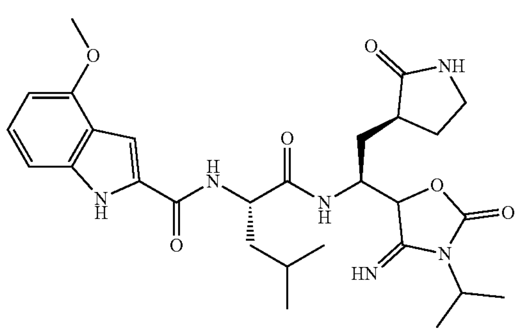 [SMILES: COc1cccc2[nH]c(C(=O)N[C@@H](CC(C)C)C(=O)N[C@@H](C[C@@H]3CCNC3=O)C3OC(=O)N(C(C)C)C3=N)cc12] |

TABLE 1-continued

Exemplary compounds.

| Cmpd No. | Structure |
|---|---|
| 358 | 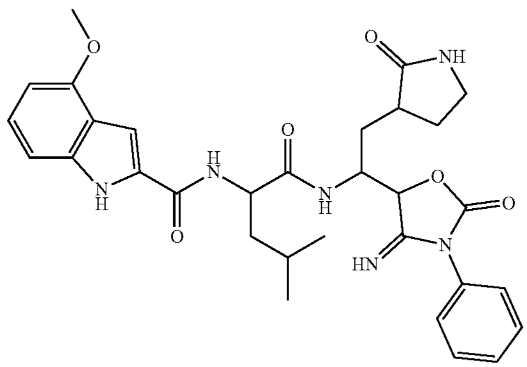 [SMILES: COc1cccc2[nH]c(C(=O)NC(CC(C)C)C(=O)NC(CC3CCNC3=O)C3OC(=O)N(c4ccccc4)C3=N)cc12] |
| 359 | 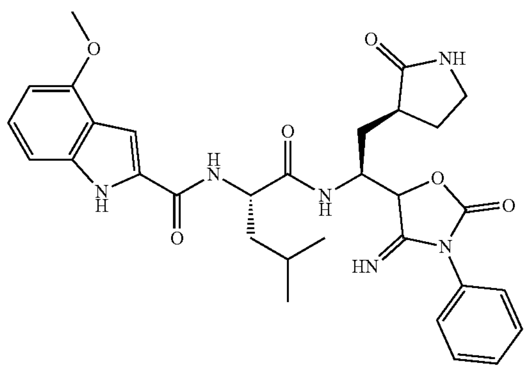 [SMILES: COc1cccc2[nH]c(C(=O)N[C@@H](CC(C)C)C(=O)N[C@@H](C[C@@H]3CCNC3=O)C3OC(=O)N(c4ccccc4)C3=N)cc12] |
| 360 | 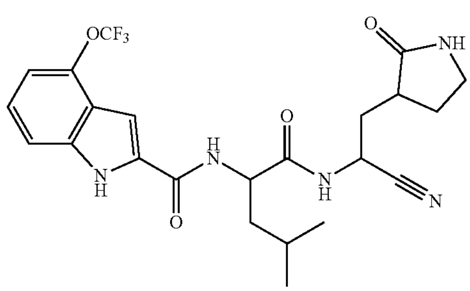 [SMILES: CC(C)CC(NC(=O)c1cc2c(OC(F)(F)F)cccc2[nH]1)C(=O)NC(C#N)CC1CCNC1=O] |
| 361 | 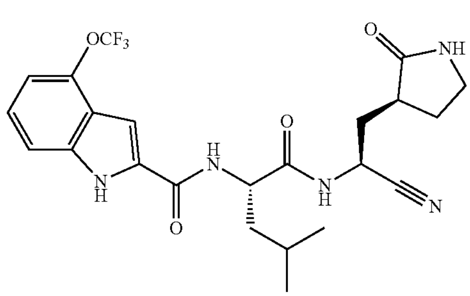 [SMILES: CC(C)C[C@H](NC(=O)c1cc2c(OC(F)(F)F)cccc2[nH]1)C(=O)N[C@H](C#N)C[C@@H]1CCNC1=O] |

TABLE 1-continued

Exemplary compounds.

| Cmpd No. | Structure |
|---|---|
| 362 | *(structure image)* |
| 363 | *(structure image)* |
| 364 | *(structure image)* |
| 365 | *(structure image)* |
| 356a | *(structure image)* |

TABLE 1-continued

Exemplary compounds.

| Cmpd No. | Structure |
|---|---|
| 356b | 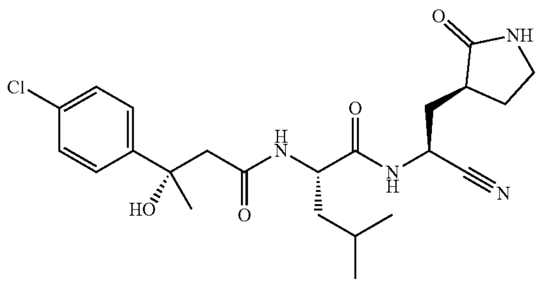 [SMILES: CC(C)C[C@H](NC(=O)C[C@](C)(O)c1ccc(Cl)cc1)C(=O)N[C@H](C#N)C[C@@H]1CCNC1=O] |
| 366 | 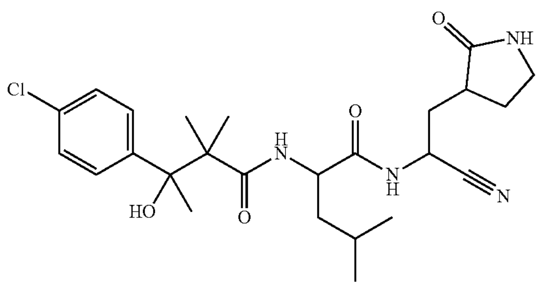 [SMILES: CC(C)CC(NC(=O)C(C)(C)C(C)(O)c1ccc(Cl)cc1)C(=O)NC(C#N)CC1CCNC1=O] |
| 367 | 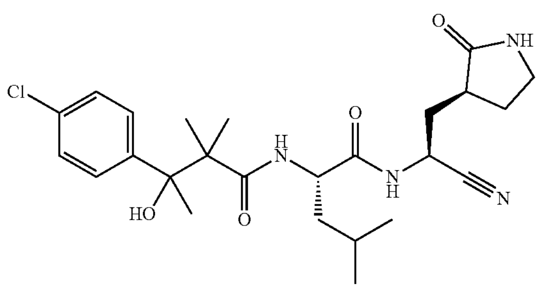 [SMILES: CC(C)C[C@H](NC(=O)C(C)(C)C(C)(O)c1ccc(Cl)cc1)C(=O)N[C@H](C#N)C[C@@H]1CCNC1=O] |
| 367a | 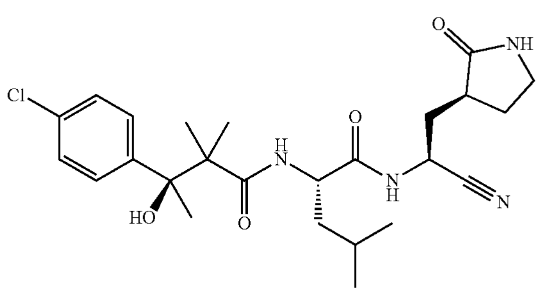 [SMILES: CC(C)C[C@H](NC(=O)C(C)(C)[C@@](C)(O)c1ccc(Cl)cc1)C(=O)N[C@H](C#N)C[C@@H]1CCNC1=O] |
| 367b | 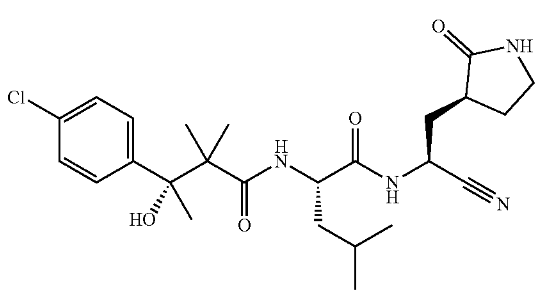 [SMILES: CC(C)C[C@H](NC(=O)C(C)(C)[C@](C)(O)c1ccc(Cl)cc1)C(=O)N[C@H](C#N)C[C@@H]1CCNC1=O] |

TABLE 1-continued

Exemplary compounds.

| Cmpd No. | Structure |
|---|---|
| 368 | 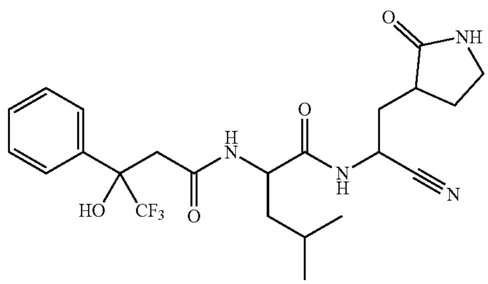 [SMILES: CC(C)CC(NC(=O)CC(O)(c1ccccc1)C(F)(F)F)C(=O)NC(C#N)CC1CCNC1=O] |
| 369 | 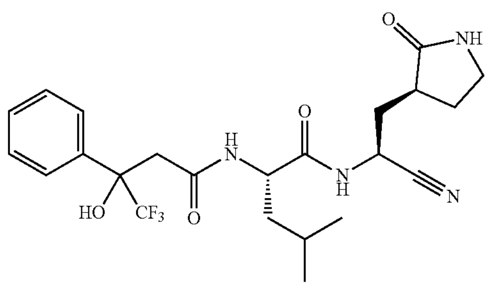 [SMILES: CC(C)C[C@H](NC(=O)CC(O)(c1ccccc1)C(F)(F)F)C(=O)N[C@H](C#N)C[C@@H]1CCNC1=O] |
| 369a | 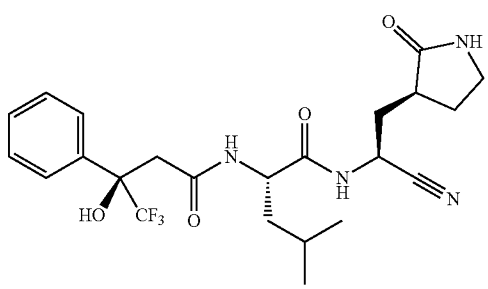 [SMILES: CC(C)C[C@H](NC(=O)C[C@@](O)(c1ccccc1)C(F)(F)F)C(=O)N[C@H](C#N)C[C@@H]1CCNC1=O] |
| 369b | 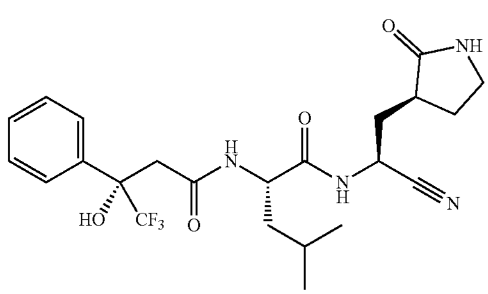 [SMILES: CC(C)C[C@H](NC(=O)C[C@](O)(c1ccccc1)C(F)(F)F)C(=O)N[C@H](C#N)C[C@@H]1CCNC1=O] |
| 370 | 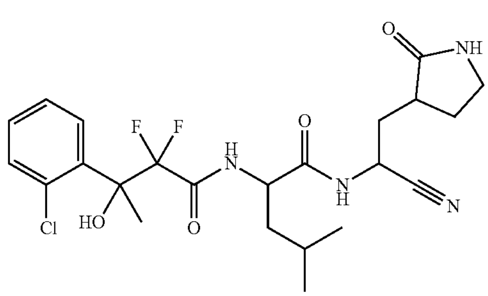 [SMILES: CC(C)CC(NC(=O)C(F)(F)C(C)(O)c1ccccc1Cl)C(=O)NC(C#N)CC1CCNC1=O] |

TABLE 1-continued
Exemplary compounds.
| Cmpd No. | Structure |
|---|---|
| 371 | 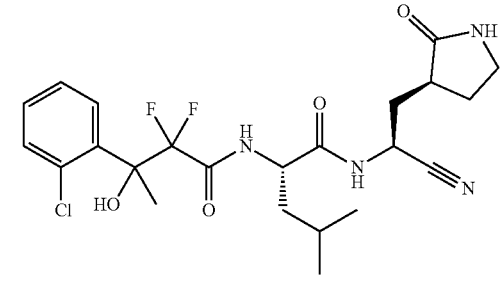 [SMILES: CC(C)C[C@H](NC(=O)C(F)(F)C(C)(O)c1ccccc1Cl)C(=O)N[C@H](C#N)C[C@@H]1CCNC1=O] |
| 371a | 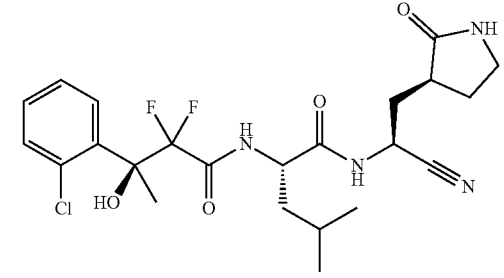 [SMILES: CC(C)C[C@H](NC(=O)C(F)(F)[C@@](C)(O)c1ccccc1Cl)C(=O)N[C@H](C#N)C[C@@H]1CCNC1=O] |
| 371b | 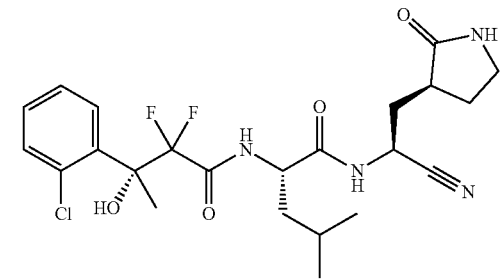 [SMILES: CC(C)C[C@H](NC(=O)C(F)(F)[C@](C)(O)c1ccccc1Cl)C(=O)N[C@H](C#N)C[C@@H]1CCNC1=O] |
| 372 | 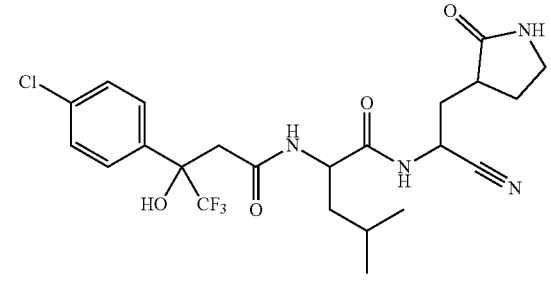 [SMILES: CC(C)CC(NC(=O)CC(O)(c1ccc(Cl)cc1)C(F)(F)F)C(=O)NC(C#N)CC1CCNC1=O] |
| 373 | 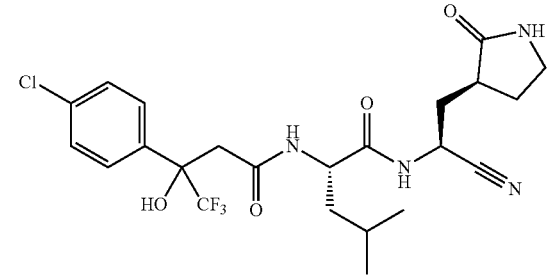 [SMILES: CC(C)C[C@H](NC(=O)CC(O)(c1ccc(Cl)cc1)C(F)(F)F)C(=O)N[C@H](C#N)C[C@@H]1CCNC1=O] |

TABLE 1-continued

Exemplary compounds.

| Cmpd No. | Structure |
|---|---|
| 373a | 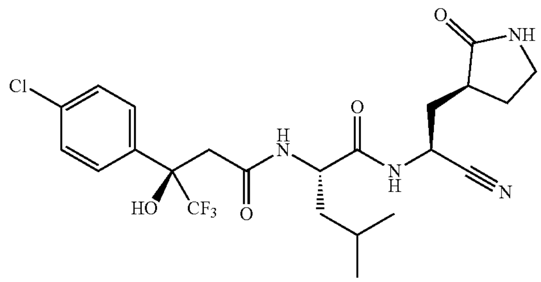 [SMILES: CC(C)C[C@H](NC(=O)C[C@@](O)(c1ccc(Cl)cc1)C(F)(F)F)C(=O)N[C@H](C#N)C[C@@H]1CCNC1=O] |
| 373b | 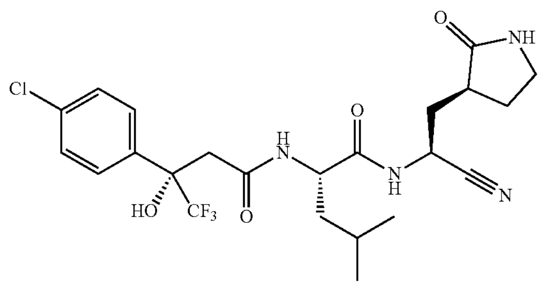 [SMILES: CC(C)C[C@H](NC(=O)C[C@](O)(c1ccc(Cl)cc1)C(F)(F)F)C(=O)N[C@H](C#N)C[C@@H]1CCNC1=O] |
| 374 | 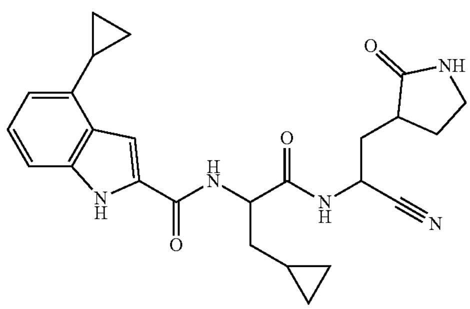 [SMILES: N#CC(CC1CCNC1=O)NC(=O)C(CC1CC1)NC(=O)c1cc2c(C3CC3)cccc2[nH]1] |
| 375 | 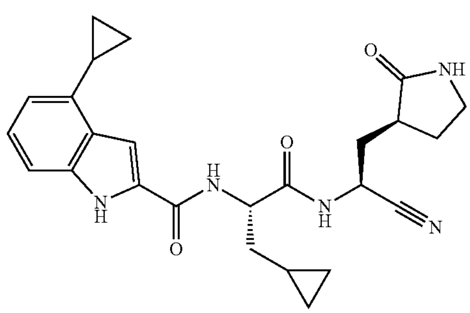 [SMILES: N#C[C@H](C[C@@H]1CCNC1=O)NC(=O)[C@H](CC1CC1)NC(=O)c1cc2c(C3CC3)cccc2[nH]1] |
| 376 | 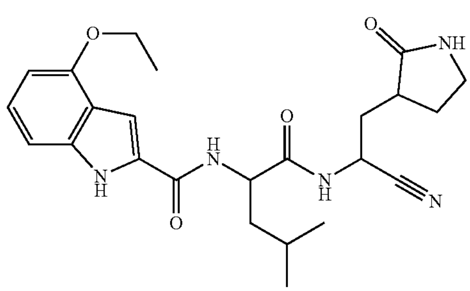 [SMILES: CCOc1cccc2[nH]c(C(=O)NC(CC(C)C)C(=O)NC(C#N)CC3CCNC3=O)cc12] |

TABLE 1-continued

Exemplary compounds.

| Cmpd No. | Structure |
|---|---|
| 377 | 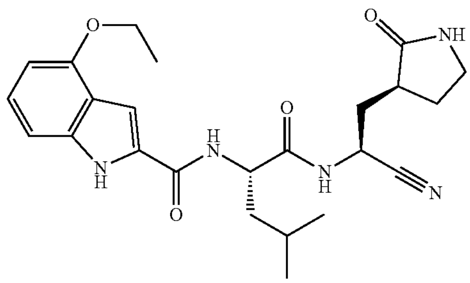 [SMILES: CCOc1cccc2[nH]c(C(=O)N[C@@H](CC(C)C)C(=O)N[C@H](C#N)C[C@@H]3CCNC3=O)cc12] |
| 378 | 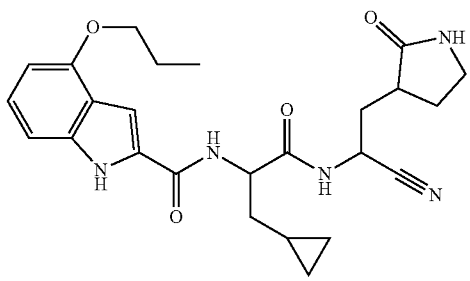 [SMILES: CCCOc1cccc2[nH]c(C(=O)NC(CC3CC3)C(=O)NC(C#N)CC3CCNC3=O)cc12] |
| 379 | 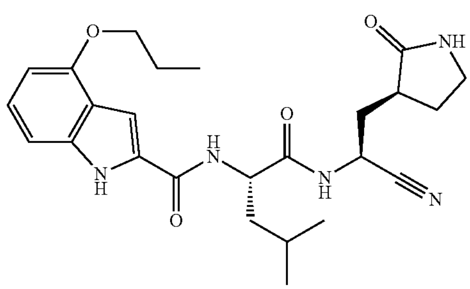 [SMILES: CCCOc1cccc2[nH]c(C(=O)N[C@@H](CC(C)C)C(=O)N[C@H](C#N)C[C@@H]3CCNC3=O)cc12] |
| 380 | 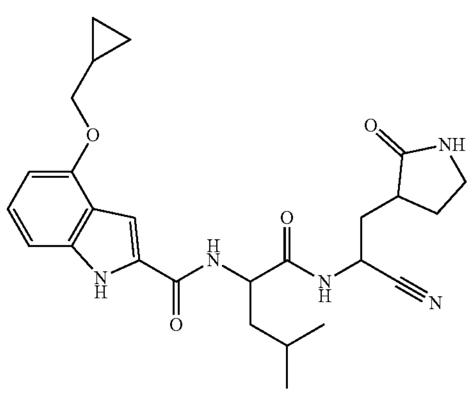 [SMILES: CC(C)CC(NC(=O)c1cc2c(OCC3CC3)cccc2[nH]1)C(=O)NC(C#N)CC1CCNC1=O] |

TABLE 1-continued

Exemplary compounds.

| Cmpd No. | Structure |
|---|---|
| 381 | 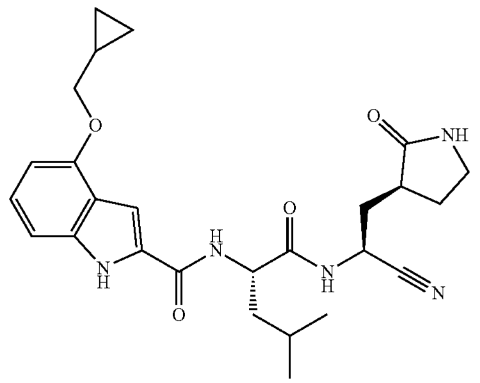 [SMILES: CC(C)C[C@H](NC(=O)c1cc2c(OCC3CC3)cccc2[nH]1)C(=O)N[C@H](C#N)C[C@@H]1CCNC1=O] |
| 382 | 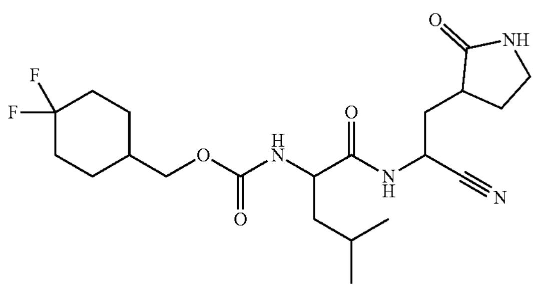 [SMILES: CC(C)CC(NC(=O)OCC1CCC(F)(F)CC1)C(=O)NC(C#N)CC1CCNC1=O] |
| 383 | 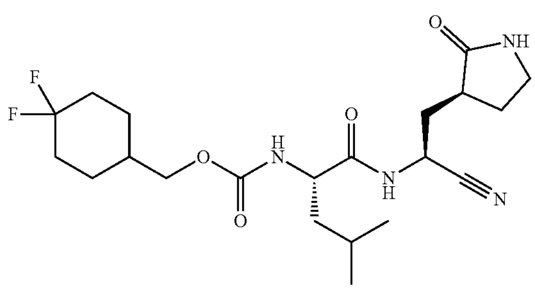 [SMILES: CC(C)C[C@H](NC(=O)OCC1CCC(F)(F)CC1)C(=O)N[C@H](C#N)C[C@@H]1CCNC1=O] |
| 384 | 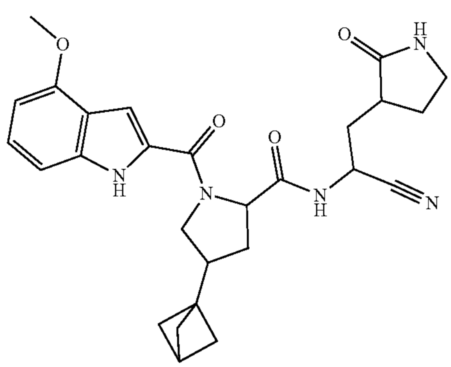 [SMILES: COc1cccc2[nH]c(C(=O)N3CC(C45CC(C4)C5)CC3C(=O)NC(C#N)CC3CCNC3=O)cc12] |

213
214
TABLE 1-continued
Exemplary compounds.
| Cmpd No. | Structure |
|---|---|
| 385 | 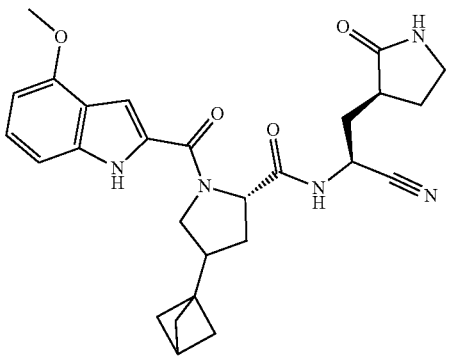 [SMILES: COc1cccc2[nH]c(C(=O)N3CC(C45CC(C4)C5)C[C@H]3C(=O)N[C@H](C#N)C[C@@H]3CCNC3=O)cc12] |
| 386 | 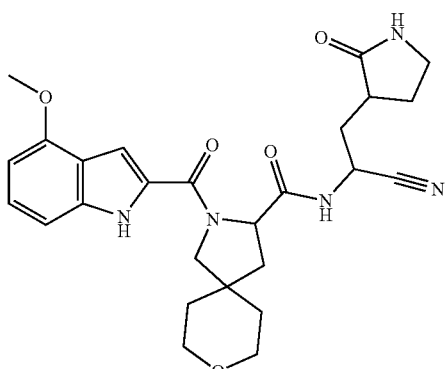 |
| 387 | 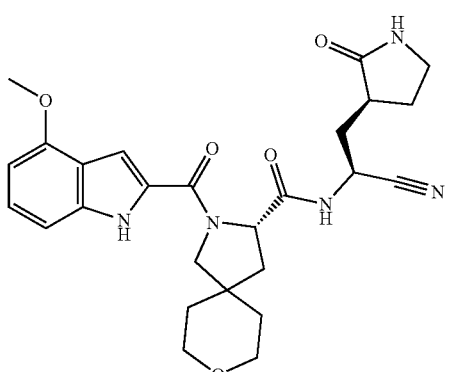 |
| 388 | 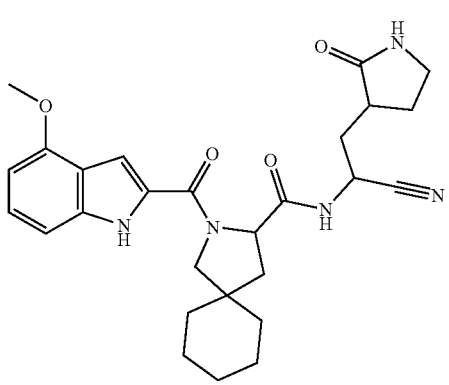 [SMILES: COc1cccc2[nH]c(C(=O)N3CC4(CCCCC4)CC3C(=O)NC(C#N)CC3CCNC3=O)cc12] |

TABLE 1-continued

Exemplary compounds.

| Cmpd No. | Structure |
|---|---|
| 389 | 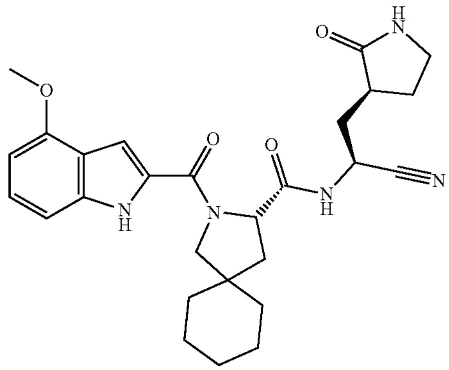 |
| 390 | 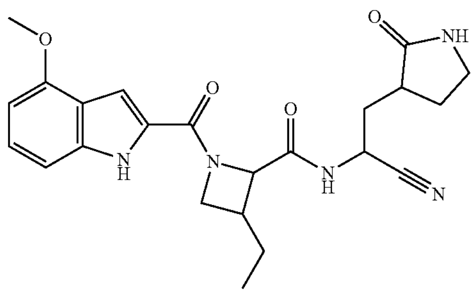 [SMILES: CCC1CN(C(=O)c2cc3c(OC)cccc3[nH]2)C1C(=O)NC(C#N)CC1CCNC1=O] |
| 391 | 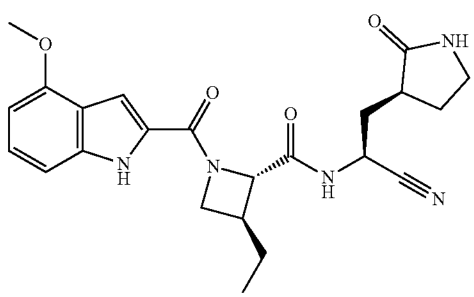 [SMILES: CC[C@H]1CN(C(=O)c2cc3c(OC)cccc3[nH]2)[C@@H]1C(=O)N[C@H](C#N)C[C@@H]1CCNC1=O] |
| 392 | 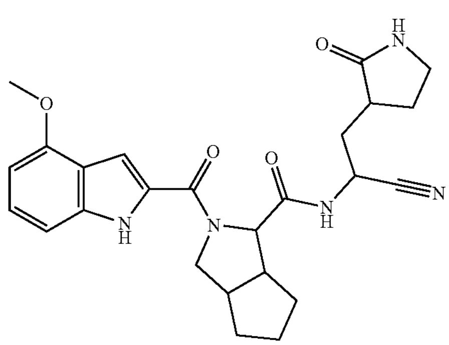 [SMILES: COc1cccc2[nH]c(C(=O)N3CC4CCCC4C3C(=O)NC(C#N)CC3CCNC3=O)cc12] |

TABLE 1-continued

Exemplary compounds.

| Cmpd No. | Structure |
|---|---|
| 393 | 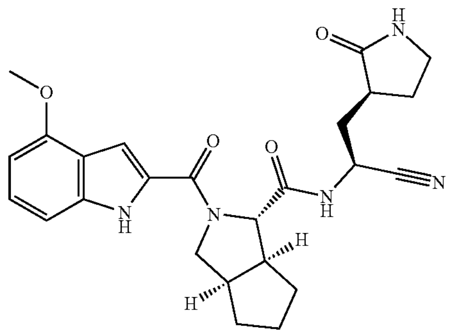 [SMILES: COc1cccc2[nH]c(C(=O)N3C[C@@H]4CCC[C@@H]4[C@H]3C(=O)N[C@H](C#N)C[C@@H]3CCNC3=O)cc12] |
| 394 | 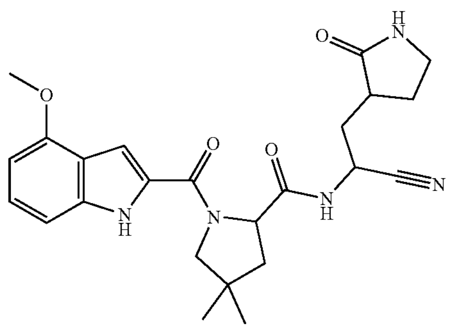 [SMILES: COc1cccc2[nH]c(C(=O)N3CC(C)(C)CC3C(=O)NC(C#N)CC3CCNC3=O)cc12] |
| 395 | 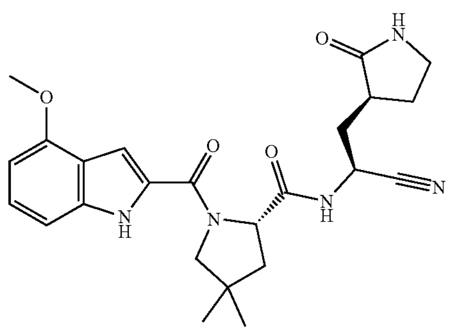 [SMILES: COc1cccc2[nH]c(C(=O)N3CC(C)(C)C[C@H]3C(=O)N[C@H](C#N)C[C@@H]3CCNC3=O)cc12] |
| 396 | 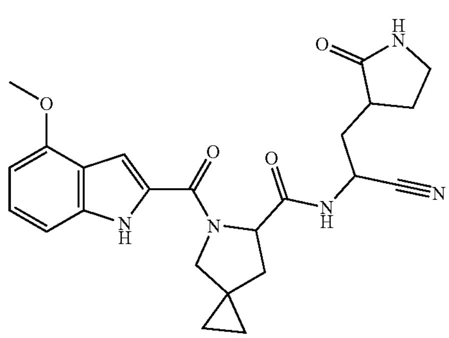 [SMILES: COc1cccc2[nH]c(C(=O)N3CC4(CC4)CC3C(=O)NC(C#N)CC3CCNC3=O)cc12] |

TABLE 1-continued

Exemplary compounds.

| Cmpd No. | Structure |
| --- | --- |
| 397 | 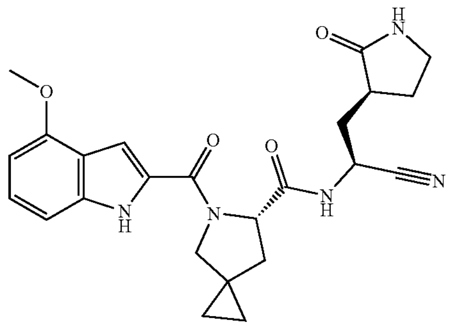 [SMILES: COc1cccc2[nH]c(C(=O)N3CC4(CC4)C[C@H]3C(=O)N[C@H](C#N)C[C@@H]3CCNC3=O)cc12] |
| 398 | 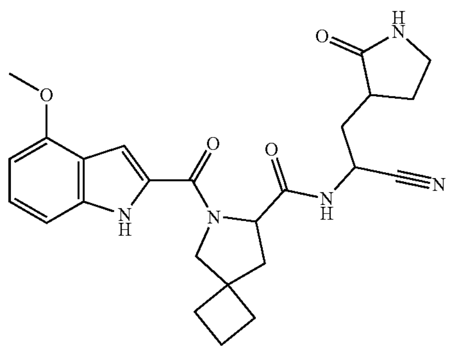 [SMILES: COc1cccc2[nH]c(C(=O)N3CC4(CCC4)CC3C(=O)NC(C#N)CC3CCNC3=O)cc12] |
| 399 | 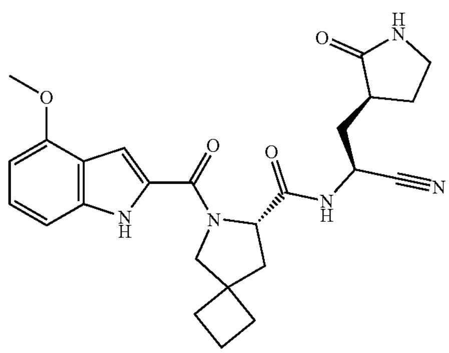 [SMILES: COc1cccc2[nH]c(C(=O)N3CC4(CCC4)C[C@H]3C(=O)N[C@H](C#N)C[C@@H]3CCNC3=O)cc12] |
| 399A | 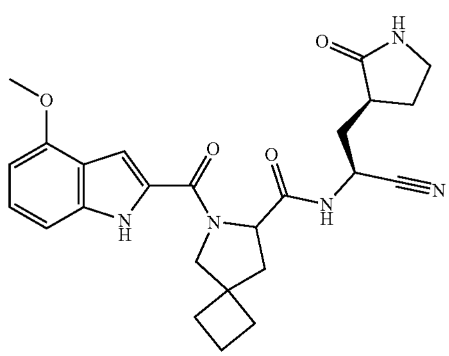 [SMILES: COc1cccc2[nH]c(C(=O)N3CC4(CCC4)CC3C(=O)N[C@H](C#N)C[C@@H]3CCNC3=O)cc12] |

TABLE 1-continued
Exemplary compounds.
| Cmpd No. | Structure |
|---|---|
| 400 | 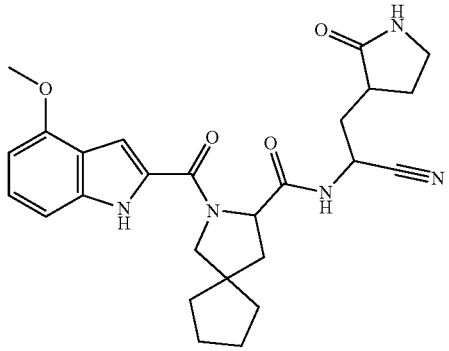 [SMILES: COc1cccc2[nH]c(C(=O)N3CC4(CCCC4)CC3C(=O)NC(C#N)CC3CCNC3=O)cc12] |
| 401 | 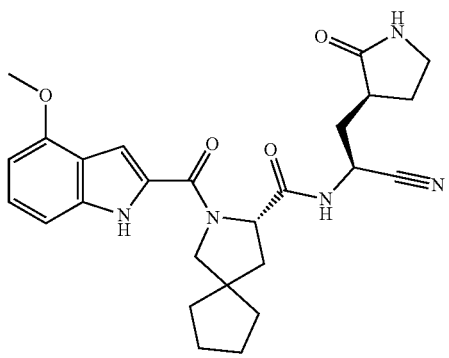 [SMILES: COc1cccc2[nH]c(C(=O)N3CC4(CCCC4)C[C@H]3C(=O)N[C@H](C#N)C[C@@H]3CCNC3=O)cc12] |
| 402 | 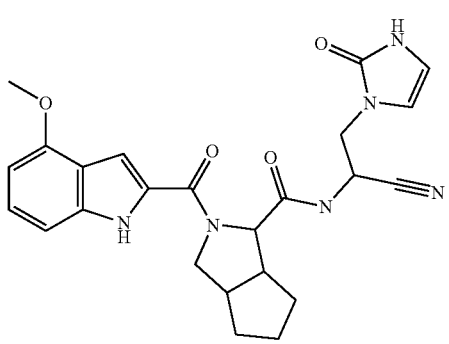 [SMILES: COc1cccc2[nH]c(C(=O)N3CC4CCCC4C3C(=O)NC(C#N)Cn3cc[nH]c3=O)cc12] |
| 403 | 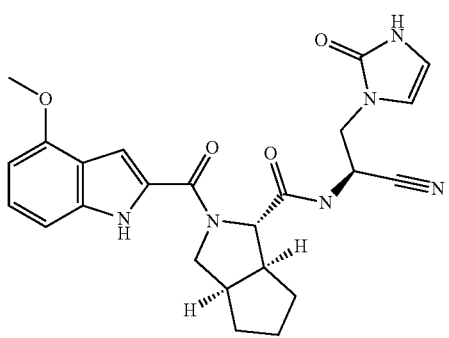 [SMILES: COc1cccc2[nH]c(C(=O)N3C[C@@H]4CCC[C@@H]4[C@H]3C(=O)N[C@H](C#N)Cn3cc[nH]c3=O)cc12] |

TABLE 1-continued
Exemplary compounds.
| Cmpd No. | Structure |
|---|---|
| 404 | 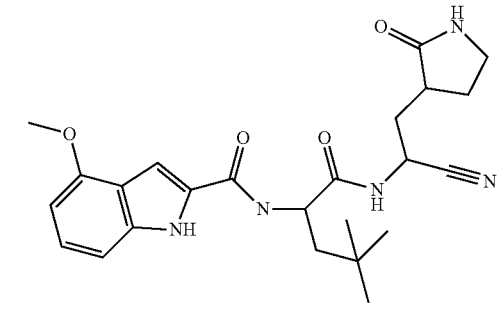 [SMILES: COc1cccc2[nH]c(C(=O)NC(CC(C)(C)C)C(=O)NC(C#N)CC3CCNC3=O)cc12] |
| 405 | 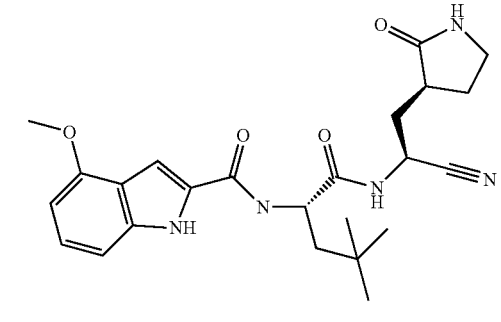 [SMILES: COc1cccc2[nH]c(C(=O)N[C@@H](CC(C)(C)C)C(=O)N[C@H](C#N)C[C@@H]3CCNC3=O)cc12] |
| 406 | 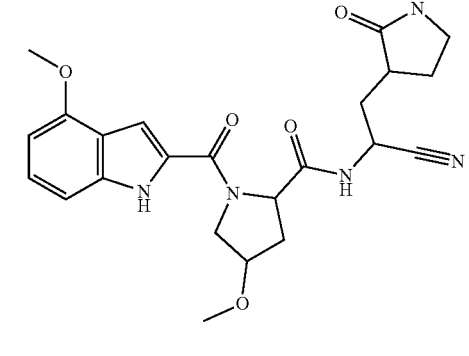 |
| 407 | 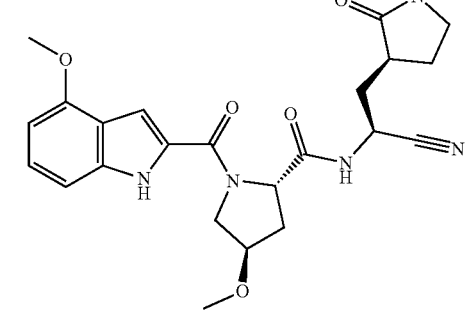 |

TABLE 1-continued

Exemplary compounds.

| Cmpd No. | Structure |
| --- | --- |
| 408 | 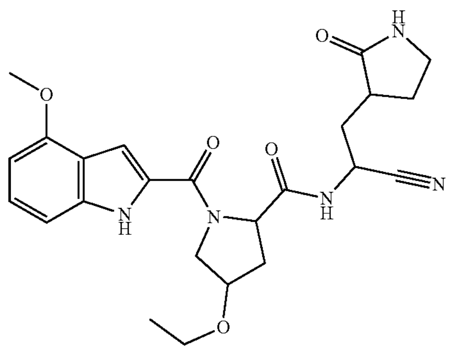 [SMILES: CCOC1CC(C(=O)NC(C#N)CC2CCNC2=O)N(C(=O)c2cc3c(OC)cccc3[nH]2)C1] |
| 409 | 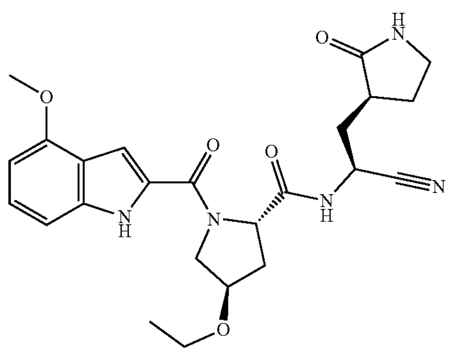 [SMILES: CCO[C@@H]1C[C@@H](C(=O)N[C@H](C#N)C[C@@H]2CCNC2=O)N(C(=O)c2cc3c(OC)cccc3[nH]2)C1] |
| 410 | 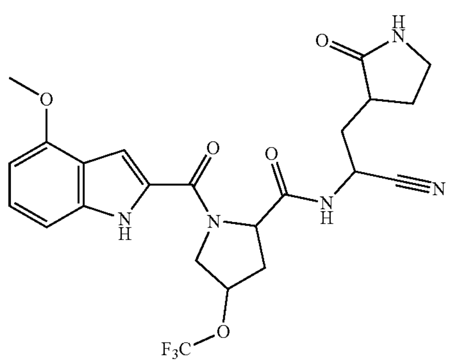 [SMILES: COc1cccc2[nH]c(C(=O)N3CC(OC(F)(F)F)CC3C(=O)NC(C#N)CC3CCNC3=O)cc12] |
| 411 | 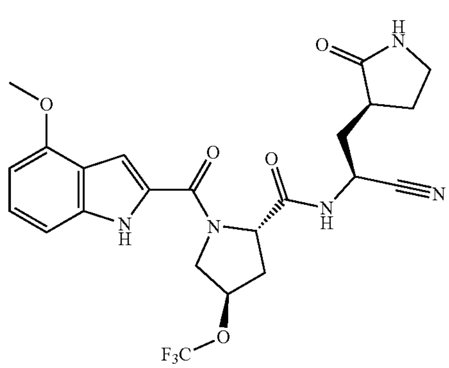 [SMILES: COc1cccc2[nH]c(C(=O)N3C[C@H](OC(F)(F)F)C[C@H]3C(=O)N[C@H](C#N)C[C@@H]3CCNC3=O)cc12] |

TABLE 1-continued
Exemplary compounds.
| Cmpd No. | Structure |
|---|---|
| 412 | 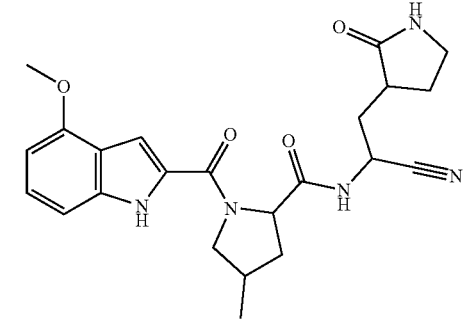 [SMILES: COc1cccc2[nH]c(C(=O)N3CC(C)CC3C(=O)NC(C#N)CC3CCNC3=O)cc12] |
| 413 | 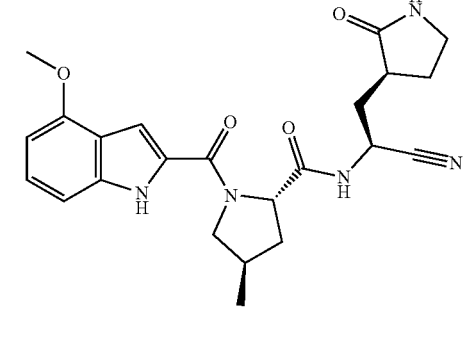 |
| 414 | 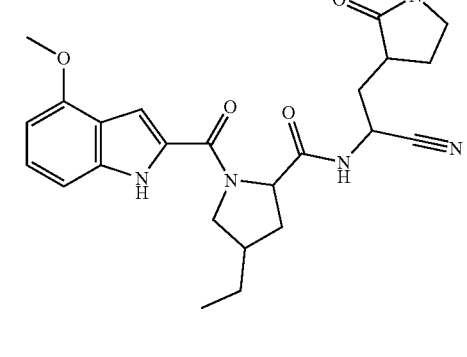 |
| 415 | 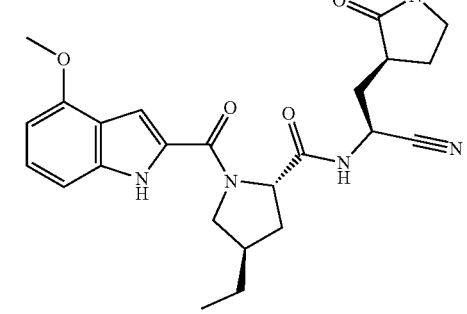 |

TABLE 1-continued

Exemplary compounds.

| Cmpd No. | Structure |
|---|---|
| 416 | 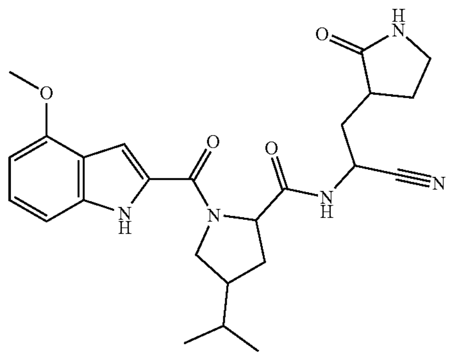 [SMILES: COc1cccc2[nH]c(C(=O)N3CC(C(C)C)CC3C(=O)NC(C#N)CC3CCNC3=O)cc12] |
| 417 | 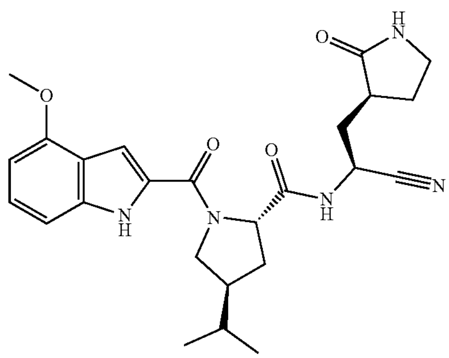 [SMILES: COc1cccc2[nH]c(C(=O)N3C[C@H](C(C)C)C[C@H]3C(=O)N[C@H](C#N)C[C@@H]3CCNC3=O)cc12] |
| 418 | 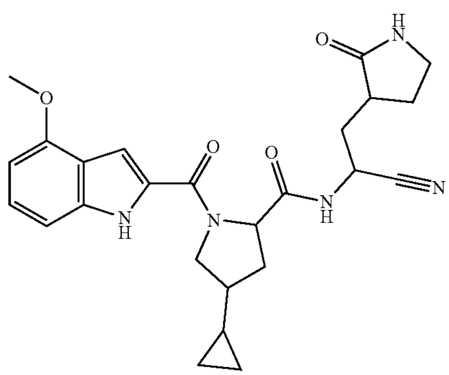 [SMILES: COc1cccc2[nH]c(C(=O)N3CC(C4CC4)CC3C(=O)NC(C#N)CC3CCNC3=O)cc12] |
| 419 | 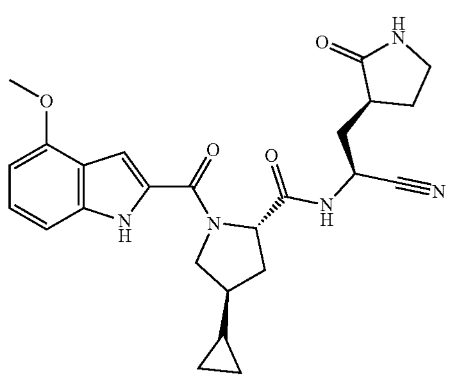 [SMILES: COc1cccc2[nH]c(C(=O)N3C[C@H](C4CC4)C[C@H]3C(=O)N[C@H](C#N)C[C@@H]3CCNC3=O)cc12] |

TABLE 1-continued

Exemplary compounds.

| Cmpd No. | Structure |
|---|---|
| 420 | 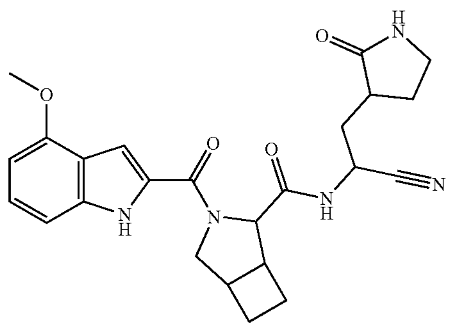 [SMILES: COc1cccc2[nH]c(C(=O)N3CC4CCC4C3C(=O)NC(C#N)CC3CCNC3=O)cc12] |
| 421 | 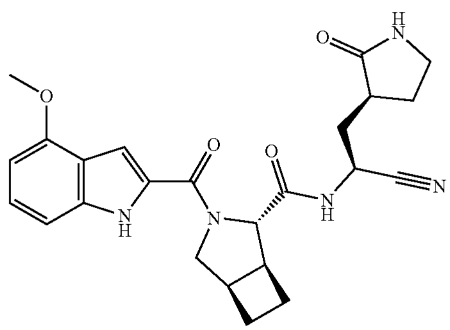 [SMILES: COc1cccc2[nH]c(C(=O)N3C[C@@H]4CC[C@@H]4[C@H]3C(=O)N[C@H](C#N)C[C@@H]3CCNC3=O)cc12] |
| 422 | 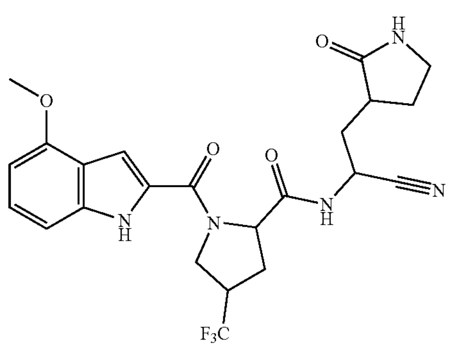 [SMILES: COc1cccc2[nH]c(C(=O)N3CC(C(F)(F)F)CC3C(=O)NC(C#N)CC3CCNC3=O)cc12] |
| 423 | 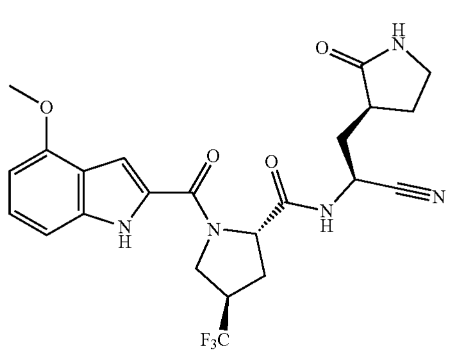 [SMILES: COc1cccc2[nH]c(C(=O)N3C[C@H](C(F)(F)F)C[C@H]3C(=O)N[C@H](C#N)C[C@@H]3CCNC3=O)cc12] |

TABLE 1-continued
Exemplary compounds.
| Cmpd No. | Structure |
|---|---|
| 424 | 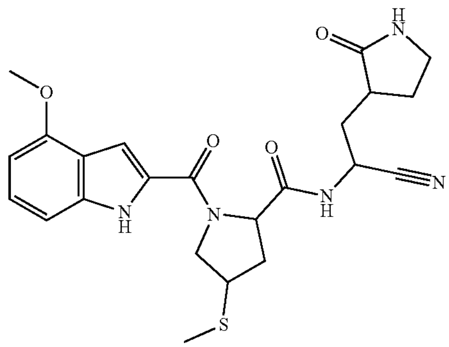 |
| 425 | 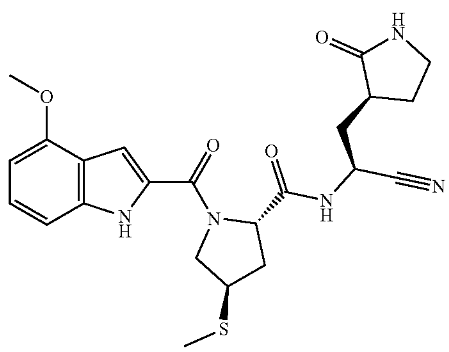 |
| 426 | 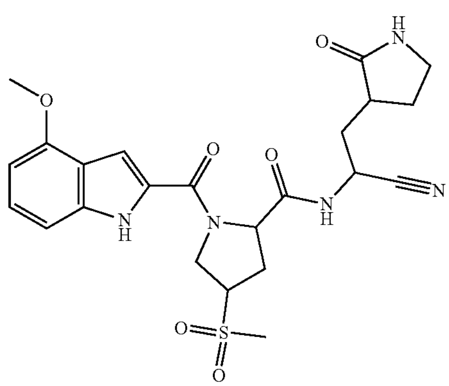 [SMILES: COc1cccc2[nH]c(C(=O)N3CC(S(C)(=O)=O)CC3C(=O)NC(C#N)CC3CCNC3=O)cc12] |
| 427 | 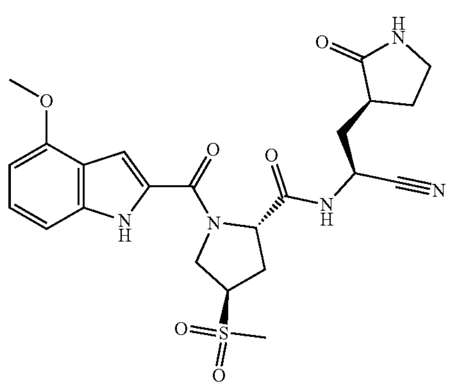 [SMILES: COc1cccc2[nH]c(C(=O)N3C[C@H](S(C)(=O)=O)C[C@H]3C(=O)N[C@H](C#N)C[C@@H]3CCNC3=O)cc12] |

TABLE 1-continued
Exemplary compounds.
| Cmpd No. | Structure |
|---|---|
| 428 | 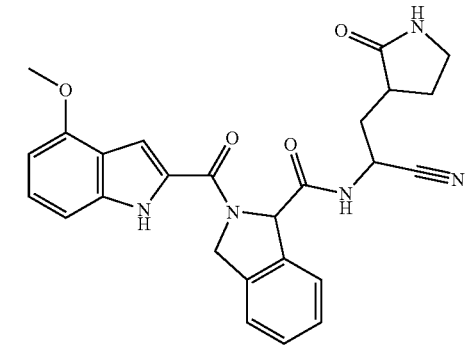 [SMILES: COc1cccc2[nH]c(C(=O)N3Cc4ccccc4C3C(=O)NC(C#N)CC3CCNC3=O)cc12] |
| 429 | 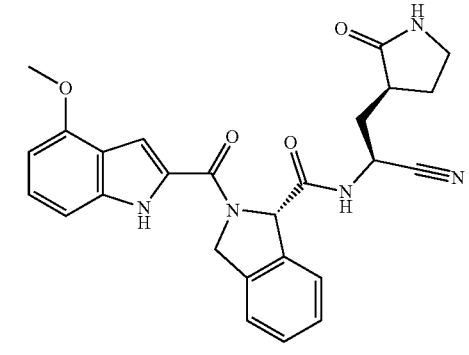 [SMILES: COc1cccc2[nH]c(C(=O)N3Cc4ccccc4[C@H]3C(=O)N[C@H](C#N)C[C@@H]3CCNC3=O)cc12] |
| 429A | 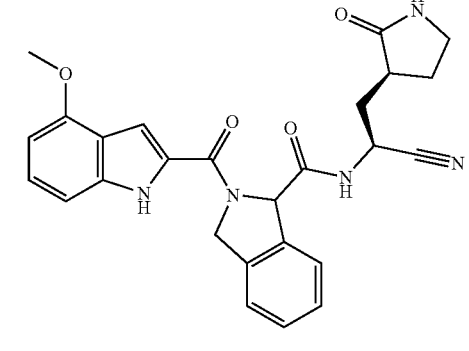 |
| 430 | 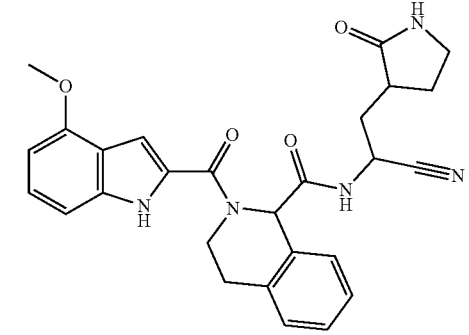 [SMILES: COc1cccc2[nH]c(C(=O)N3CCc4ccccc4C3C(=O)NC(C#N)CC3CCNC3=O)cc12] |

TABLE 1-continued

Exemplary compounds.

| Cmpd No. | Structure |
|---|---|
| 431 | 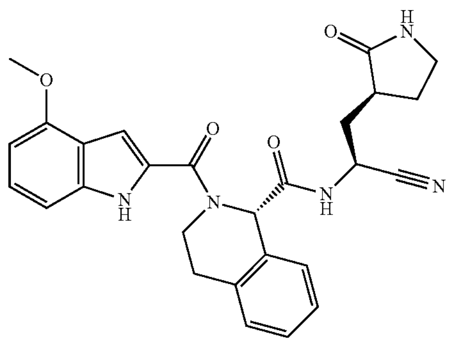 [SMILES: COc1cccc2[nH]c(C(=O)N3CCc4ccccc4[C@H]3C(=O)N[C@H](C#N)C[C@@H]3CCNC3=O)cc12] |
| 432 | 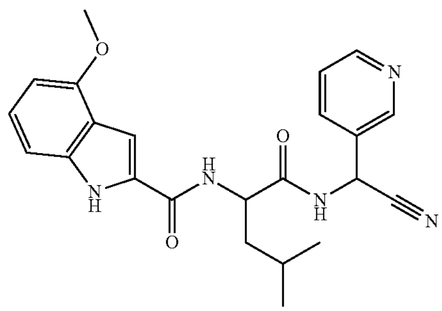 [SMILES: COc1cccc2[nH]c(C(=O)NC(CC(C)C)C(=O)NC(C#N)c3cccnc3)cc12] |
| 433 | 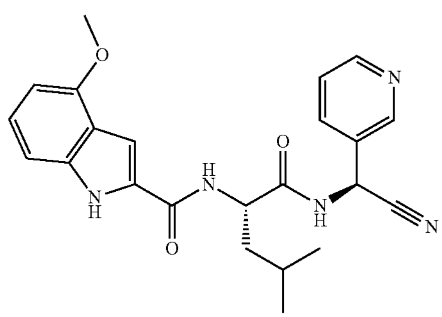 [SMILES: COc1cccc2[nH]c(C(=O)N[C@@H](CC(C)C)C(=O)N[C@H](C#N)c3cccnc3)cc12] |
| 434 | 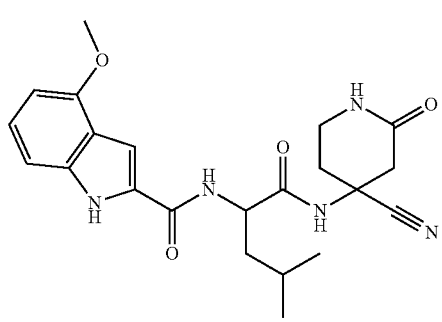 [SMILES: COc1cccc2[nH]c(C(=O)NC(CC(C)C)C(=O)NC3(C#N)CCNC(=O)C3)cc12] |

TABLE 1-continued

Exemplary compounds.

| Cmpd No. | Structure |
|---|---|
| 435 | 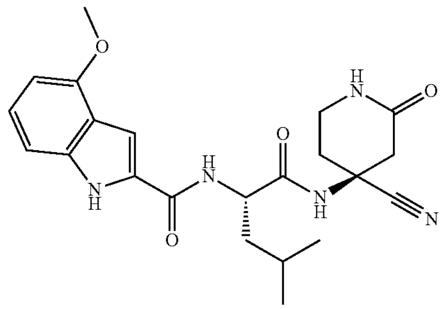 [SMILES: COc1cccc2[nH]c(C(=O)N[C@@H](CC(C)C)C(=O)N[C@@]3(C#N)CCNC(=O)C3)cc12] |
| 436 | 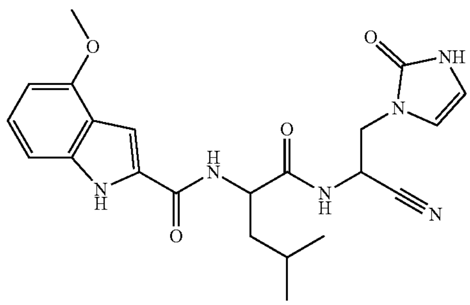 [SMILES: COc1cccc2[nH]c(C(=O)NC(CC(C)C)C(=O)NC(C#N)Cn3cc[nH]c3=O)cc12] |
| 437 | 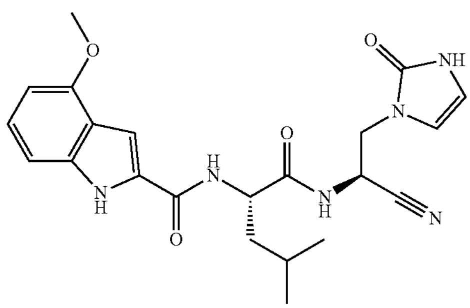 [SMILES: COc1cccc2[nH]c(C(=O)N[C@@H](CC(C)C)C(=O)N[C@H](C#N)Cn3cc[nH]c3=O)cc12] |
| 438 | 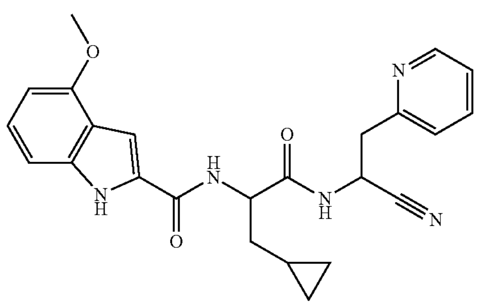 [SMILES: COc1cccc2[nH]c(C(=O)NC(CC3CC3)C(=O)NC(C#N)Cc3ccccn3)cc12] |
| 439 | 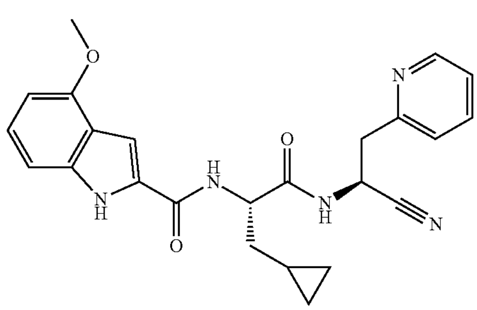 [SMILES: COc1cccc2[nH]c(C(=O)N[C@@H](CC3CC3)C(=O)N[C@H](C#N)Cc3ccccn3)cc12] |

TABLE 1-continued
Exemplary compounds.
| Cmpd No. | Structure |
|---|---|
| 440 | 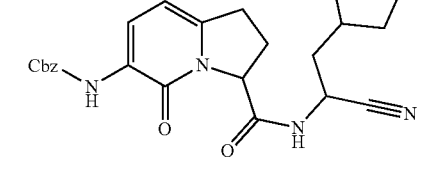 |
| 441 | 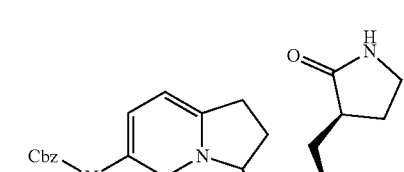 |
| 442 | 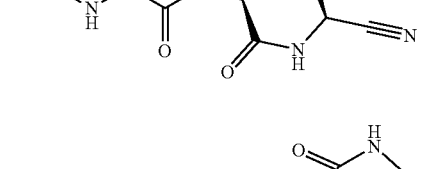 |
| 443 | 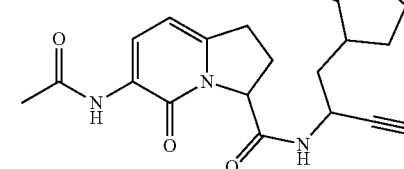 |
| 444 | 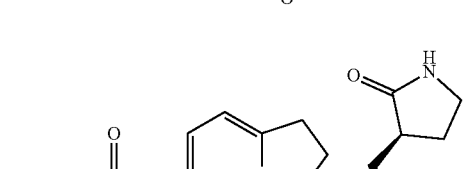 |
| 445 | 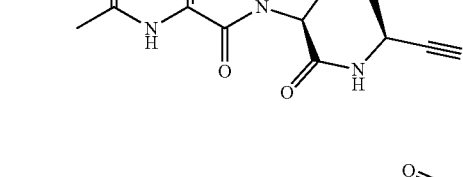 |

TABLE 1-continued

Exemplary compounds.

| Cmpd No. | Structure |
|---|---|
| 446 | 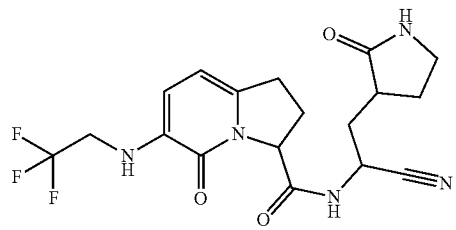 [SMILES: N#CC(CC1CCNC1=O)NC(=O)C1CCc2ccc(NCC(F)(F)F)c(=O)n21] |
| 447 | 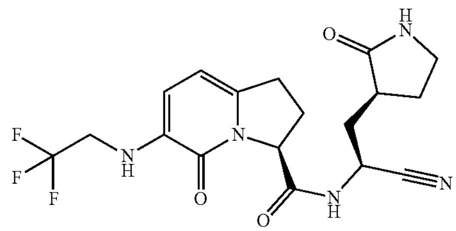 [SMILES: N#C[C@H](C[C@@H]1CCNC1=O)NC(=O)[C@@H]1CCc2ccc(NCC(F)(F)F)c(=O)n21] |
| 448 | 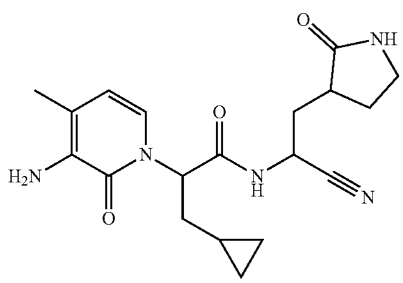 [SMILES: Cc1ccn(C(CC2CC2)C(=O)NC(C#N)CC2CCNC2=O)c(=O)c1N] |
| 449 | 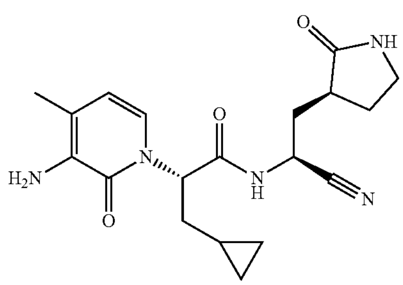 [SMILES: Cc1ccn([C@@H](CC2CC2)C(=O)N[C@H](C#N)C[C@@H]2CCNC2=O)c(=O)c1N] |
| 450 | 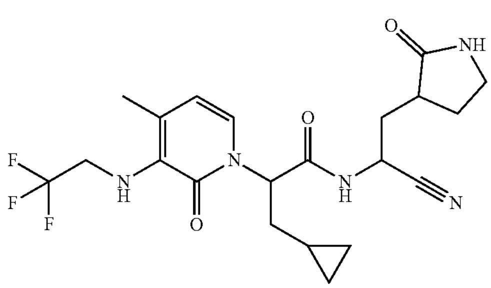 [SMILES: Cc1ccn(C(CC2CC2)C(=O)NC(C#N)CC2CCNC2=O)c(=O)c1NCC(F)(F)F] |

TABLE 1-continued

Exemplary compounds.

| Cmpd No. | Structure |
|---|---|
| 451 | 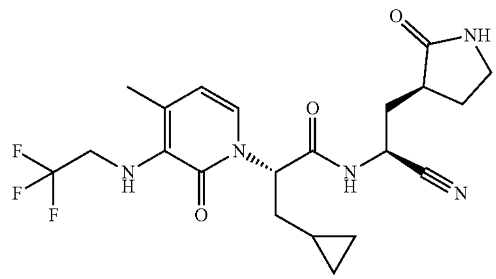 [SMILES: Cc1ccn([C@@H](CC2CC2)C(=O)N[C@H](C#N)C[C@@H]2CCNC2=O)c(=O)c1NCC(F)(F)F] |
| 452 | 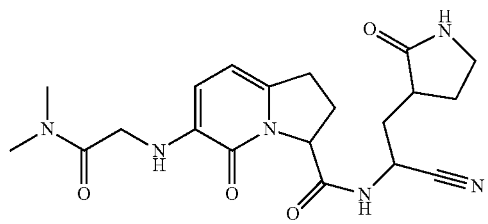 [SMILES: CN(C)C(=O)CNc1ccc2n(c1=O)C(C(=O)NC(C#N)CC1CCNC1=O)CC2] |
| 453 | 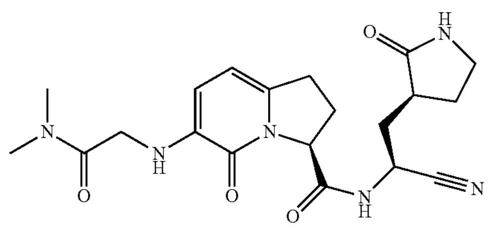 [SMILES: CN(C)C(=O)CNc1ccc2n(c1=O)[C@H](C(=O)N[C@H](C#N)C[C@@H]1CCNC1=O)CC2] |
| 454 | 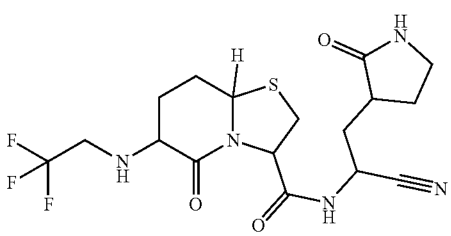 [SMILES: N#CC(CC1CCNC1=O)NC(=O)C1CSC2CCC(NCC(F)(F)F)C(=O)N21] |
| 455 | 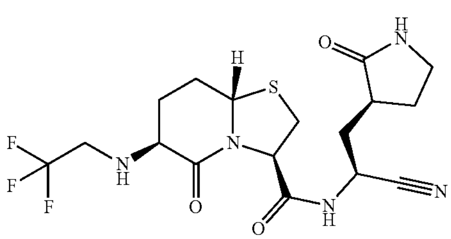 [SMILES: N#C[C@H](C[C@@H]1CCNC1=O)NC(=O)[C@@H]1CS[C@H]2CC[C@H](NCC(F)(F)F)C(=O)N21] |
| 456 | 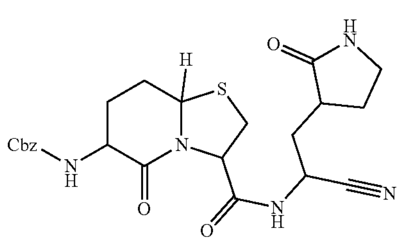 [SMILES: N#CC(CC1CCNC1=O)NC(=O)C1CSC2CCC(NC(=O)OCc3ccccc3)C(=O)N21] |

TABLE 1-continued

Exemplary compounds.

| Cmpd No. | Structure |
|---|---|
| 457 | 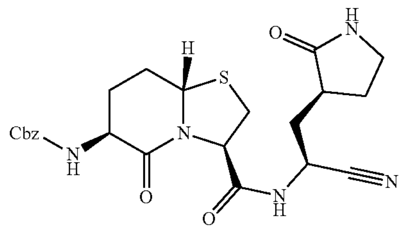 [SMILES: N#C[C@H](C[C@@H]1CCNC1=O)NC(=O)[C@@H]1CS[C@H]2CC[C@H](NC(=O)OCc3ccccc3)C(=O)N21] |
| 458 | 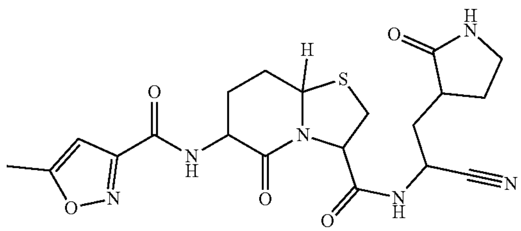 [SMILES: Cc1cc(C(=O)NC2CCC3SCC(C(=O)NC(C#N)CC4CCNC4=O)N3C2=O)no1] |
| 459 | 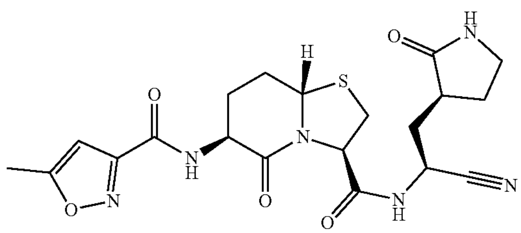 [SMILES: Cc1cc(C(=O)N[C@H]2CC[C@@H]3SC[C@@H](C(=O)N[C@H](C#N)C[C@@H]4CCNC4=O)N3C2=O)no1] |
| 460 | 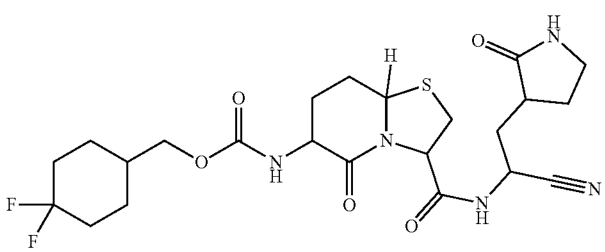 [SMILES: N#CC(CC1CCNC1=O)NC(=O)C1CSC2CCC(NC(=O)OCC3CCC(F)(F)CC3)C(=O)N21] |
| 461 | 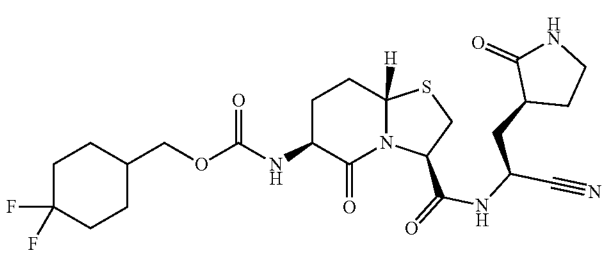 [SMILES: N#C[C@H](C[C@@H]1CCNC1=O)NC(=O)[C@@H]1CS[C@H]2CC[C@H](NC(=O)OCC3CCC(F)(F)CC3)C(=O)N21] |
| 462 | 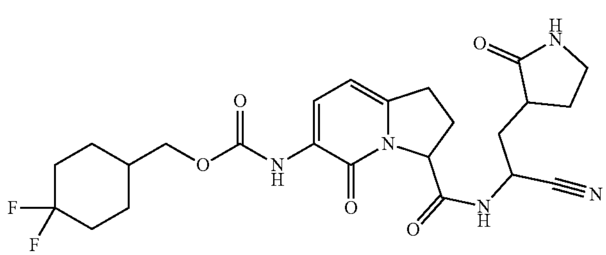 [SMILES: N#CC(CC1CCNC1=O)NC(=O)C1CCc2ccc(NC(=O)OCC3CCC(F)(F)CC3)c(=O)n21] |

TABLE 1-continued
Exemplary compounds.
| Cmpd No. | Structure |
|---|---|
| 463 | 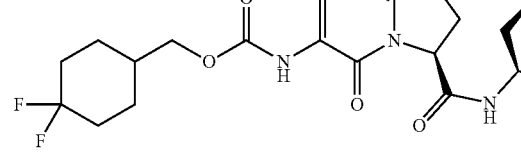 |
| 464 | 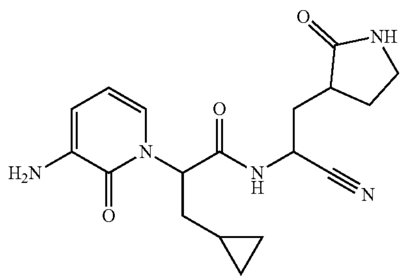 [SMILES: N#CC(CC1CCNC1=O)NC(=O)C(CC1CC1)n1cccc(N)c1=O] |
| 465 | 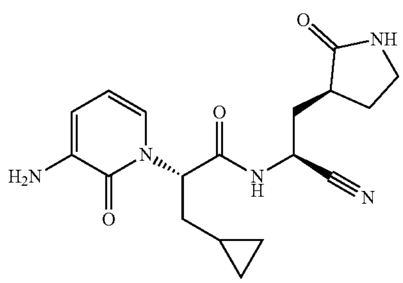 [SMILES: N#C[C@H](C[C@@H]1CCNC1=O)NC(=O)[C@H](CC1CC1)n1cccc(N)c1=O] |
| 466 | 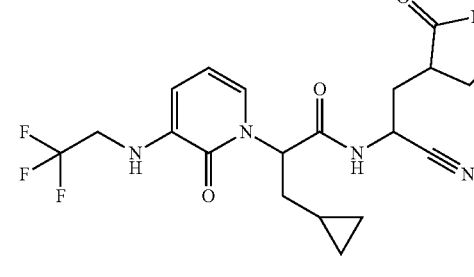 |
| 467 | 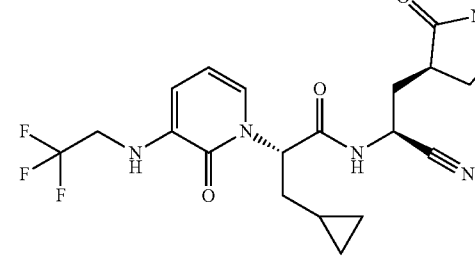 |

TABLE 1-continued
Exemplary compounds.
| Cmpd No. | Structure |
|---|---|
| 468 | 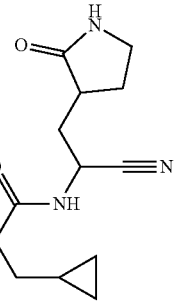 |
| 469 | 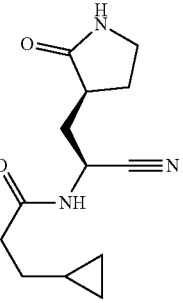 |
| 470 | 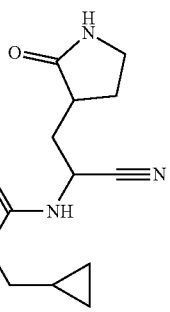 |
| 471 | 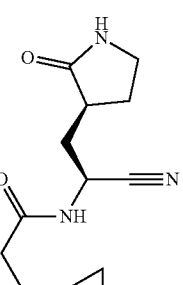 |
| 472 | 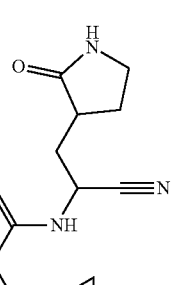 |

TABLE 1-continued

Exemplary compounds.

| Cmpd No. | Structure |
|---|---|
| 473 | 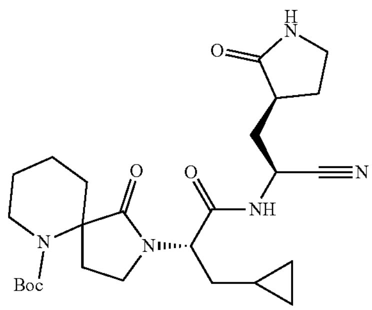 [SMILES: CC(C)(C)OC(=O)N1CCCCC12CCN([C@@H](CC1CC1)C(=O)N[C@H](C#N)C[C@@H]1CCNC1=O)C2=O] |
| 474 | 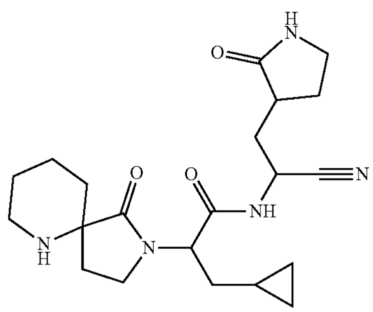 |
| 475 | 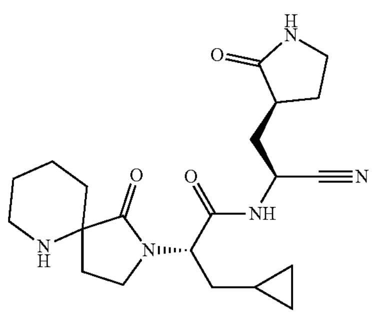 [SMILES: N#C[C@H](C[C@@H]1CCNC1=O)NC(=O)[C@H](CC1CC1)N1CCC2(CCCCN2)C1=O] |
| 476 | 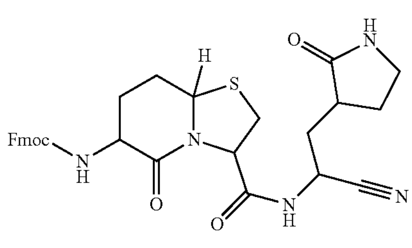 |
| 477 | 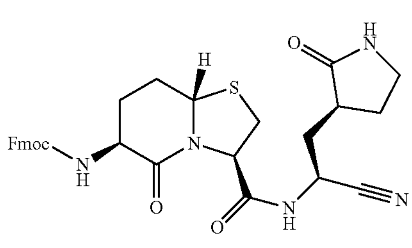 |

255 256
TABLE 1-continued
Exemplary compounds.
| Cmpd No. | Structure |
|---|---|
| 478 | 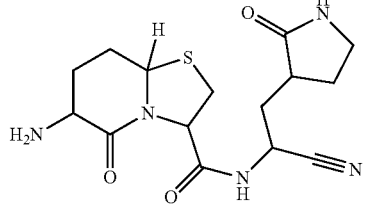 |
| 479 | 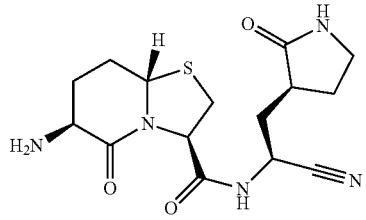 [SMILES: N#C[C@H](C[C@@H]1CCNC1=O)NC(=O)[C@@H]1CS[C@H]2CC[C@H](N)C(=O)N21] |
| 480 | 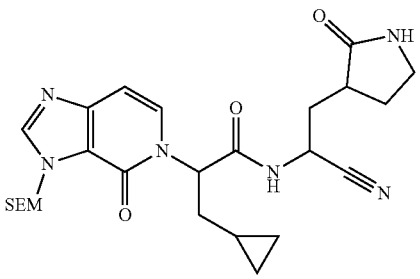 [SMILES: C[Si](C)(C)CCOCn1cnc2ccn(C(CC3CC3)C(=O)NC(C#N)CC3CCNC3=O)c(=O)c21] |
| 481 | 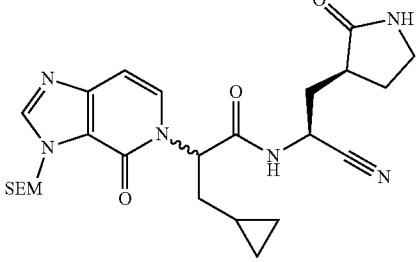 |
| 482 | 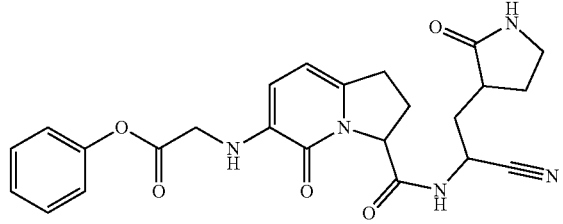 [SMILES: N#CC(CC1CCNC1=O)NC(=O)C1CCc2ccc(NCC(=O)Oc3ccccc3)c(=O)n21] |
| 483 | 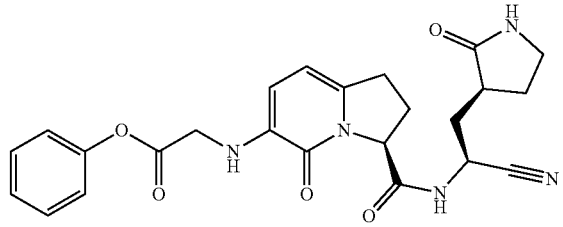 [SMILES: N#C[C@H](C[C@@H]1CCNC1=O)NC(=O)[C@@H]1CCc2ccc(NCC(=O)Oc3ccccc3)c(=O)n21] |

TABLE 1-continued

Exemplary compounds.

| Cmpd No. | Structure |
|---|---|
| 484 | 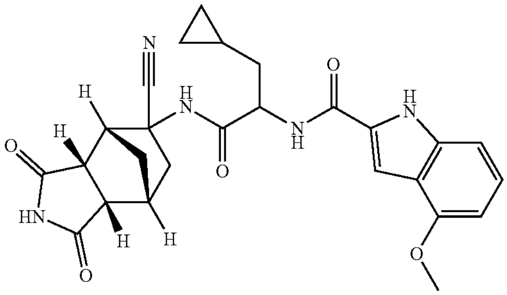 [SMILES: COc1cccc2[nH]c(C(=O)NC(CC3CC3)C(=O)NC3(C#N)C[C@H]4C[C@@H]3[C@H]3C(=O)NC(=O)[C@@H]43)cc12] |
| 485 | 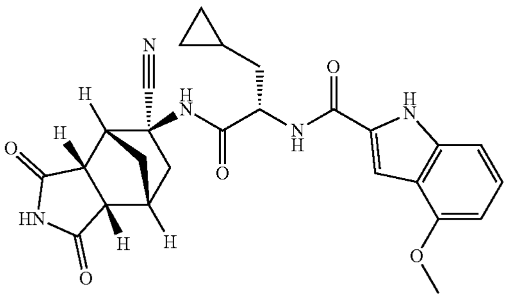 [SMILES: COc1cccc2[nH]c(C(=O)N[C@@H](CC3CC3)C(=O)N[C@@]3(C#N)C[C@H]4C[C@@H]3[C@H]3C(=O)NC(=O)[C@@H]43)cc12] |
| 486 | 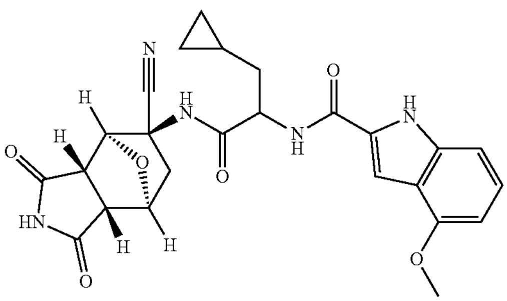 [SMILES: COc1cccc2[nH]c(C(=O)NC(CC3CC3)C(=O)N[C@@]3(C#N)C[C@@H]4O[C@H]3[C@H]3C(=O)NC(=O)[C@H]34)cc12] |
| 487 | 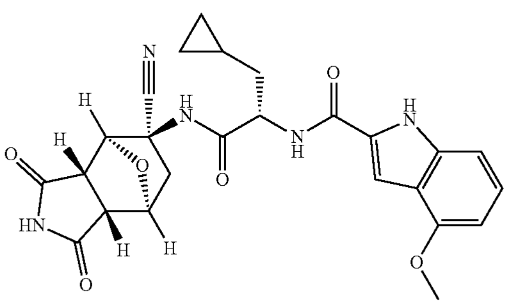 [SMILES: COc1cccc2[nH]c(C(=O)N[C@@H](CC3CC3)C(=O)N[C@@]3(C#N)C[C@@H]4O[C@H]3[C@H]3C(=O)NC(=O)[C@H]34)cc12] |
| 488 | 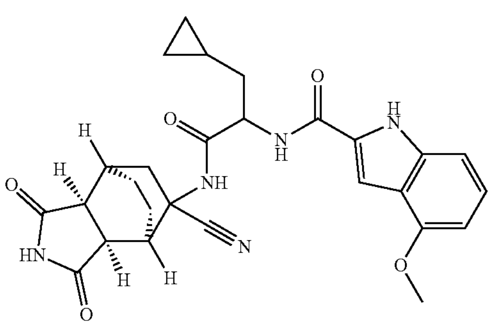 |

TABLE 1-continued

Exemplary compounds.

| Cmpd No. | Structure |
|---|---|
| 489 | 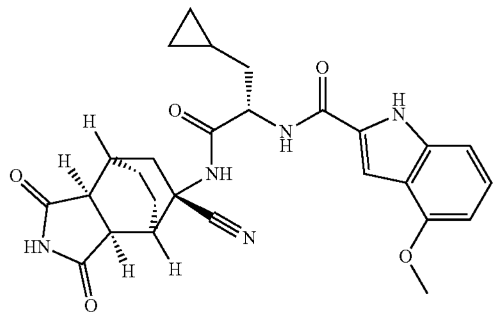 |
| 490 | 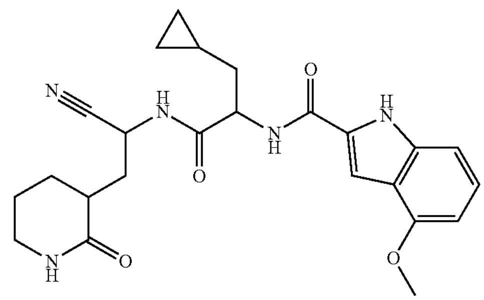 [SMILES: COc1cccc2[nH]c(C(=O)NC(CC3CC3)C(=O)NC(C#N)CC3CCCNC3=O)cc12] |
| 491 | 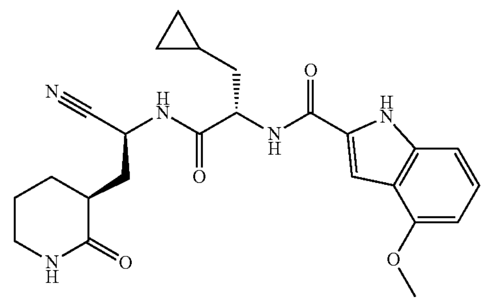 [SMILES: COc1cccc2[nH]c(C(=O)N[C@@H](CC3CC3)C(=O)N[C@H](C#N)C[C@@H]3CCCNC3=O)cc12] |
| 491B | 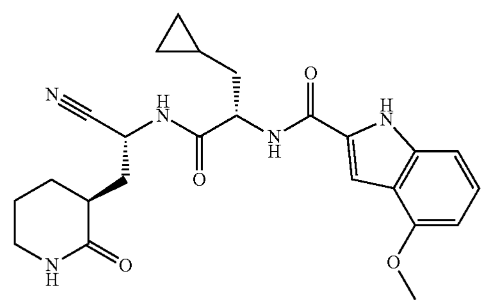 [SMILES: COc1cccc2[nH]c(C(=O)N[C@@H](CC3CC3)C(=O)N[C@@H](C#N)C[C@@H]3CCCNC3=O)cc12] |
| 492 | 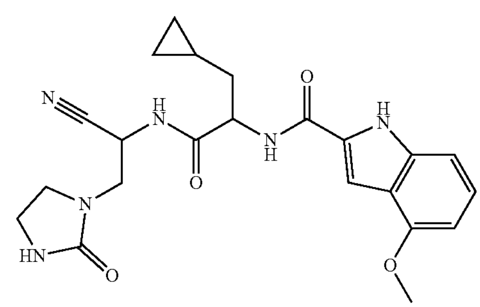 [SMILES: COc1cccc2[nH]c(C(=O)NC(CC3CC3)C(=O)NC(C#N)CN3CCNC3=O)cc12] |

TABLE 1-continued
Exemplary compounds.
| Cmpd No. | Structure |
|---|---|
| 493 | 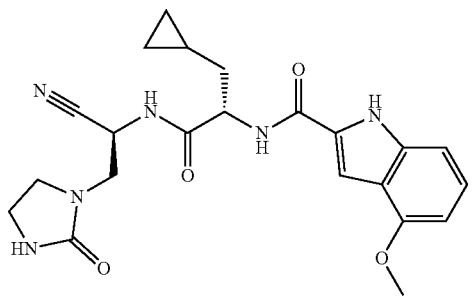 [SMILES: COc1cccc2[nH]c(C(=O)N[C@@H](CC3CC3)C(=O)N[C@H](C#N)CN3CCNC3=O)cc12] |
| 494 | 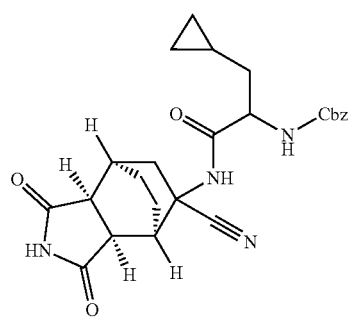 [SMILES: N#CC1(NC(=O)C(CC2CC2)NC(=O)OCc2ccccc2)C[C@H]2CC[C@@H]1[C@H]1C(=O)NC(=O)[C@@H]21] |
| 495 | 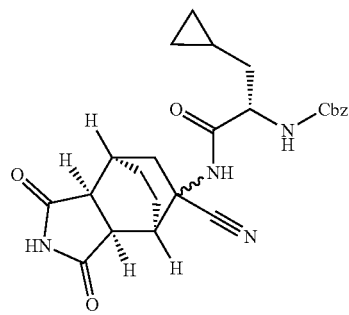 [SMILES: N#CC1(NC(=O)[C@H](CC2CC2)NC(=O)OCc2ccccc2)C[C@H]2CC[C@@H]1[C@H]1C(=O)NC(=O)[C@@H]21] |
| 496 | 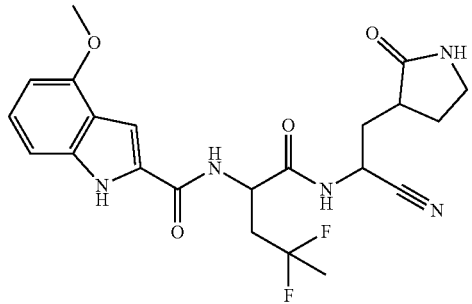 [SMILES: COc1cccc2[nH]c(C(=O)NC(CC(C)(F)F)C(=O)NC(C#N)CC3CCNC3=O)cc12] |
| 497 | 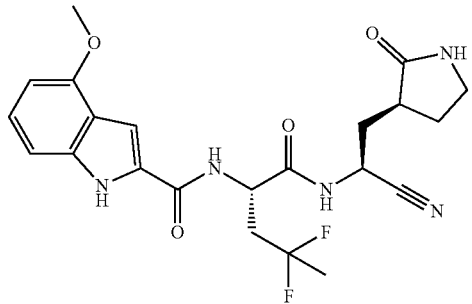 [SMILES: COc1cccc2[nH]c(C(=O)N[C@@H](CC(C)(F)F)C(=O)N[C@H](C#N)C[C@@H]3CCNC3=O)cc12] |

TABLE 1-continued
Exemplary compounds.
| Cmpd No. | Structure |
|---|---|
| 498 | 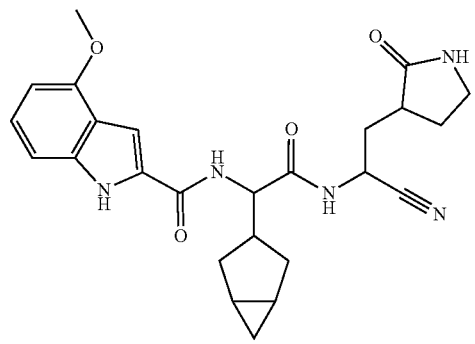 [SMILES: COc1cccc2[nH]c(C(=O)NC(C(=O)NC(C#N)CC3CCNC3=O)C3CC4CC4C3)cc12] |
| 499 | 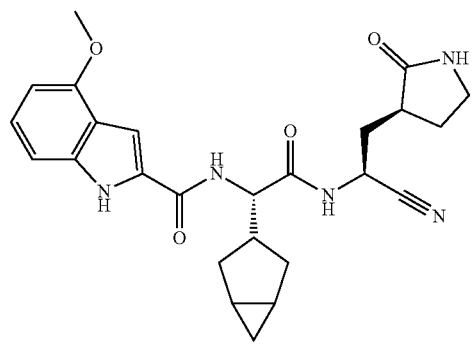 [SMILES: COc1cccc2[nH]c(C(=O)N[C@H](C(=O)N[C@H](C#N)C[C@@H]3CCNC3=O)C3CC4CC4C3)cc12] |
| 500 | 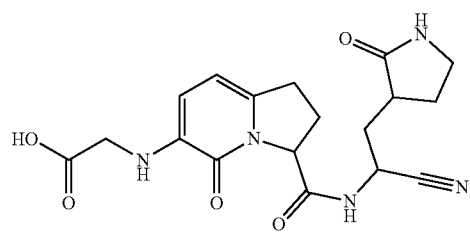 [SMILES: N#CC(CC1CCNC1=O)NC(=O)C1CCc2ccc(NCC(=O)O)c(=O)n21] |
| 501 | 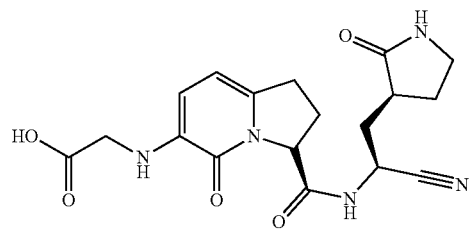 |
| 502 | 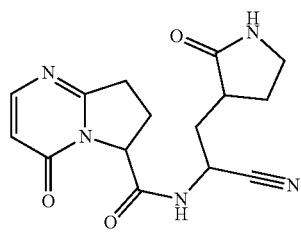 [SMILES: N#CC(CC1CCNC1=O)NC(=O)C1CCc2nccc(=O)n21] |

TABLE 1-continued
| Cmpd No. | Structure |
|---|---|
| 503 | 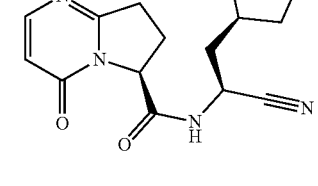 |
| 504 | 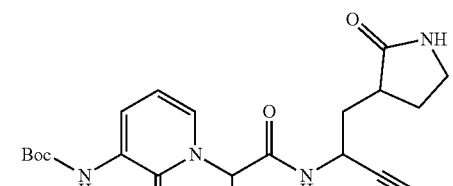 |
| 505 | 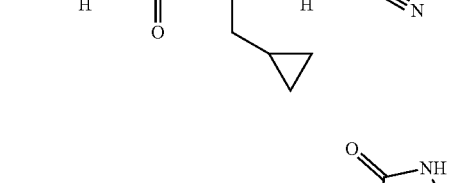 |
| 506 | 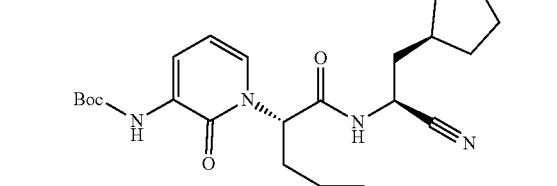 |
| 507 | 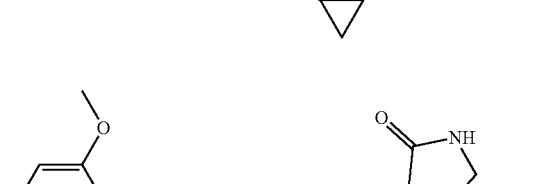 |

TABLE 1-continued
Exemplary compounds.
| Cmpd No. | Structure |
|---|---|
| 508 | 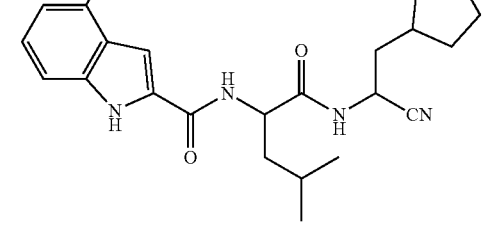 |
| 509 | 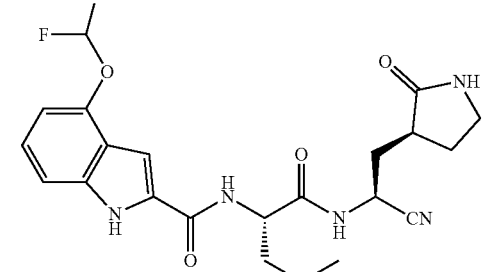 |
| 510 | 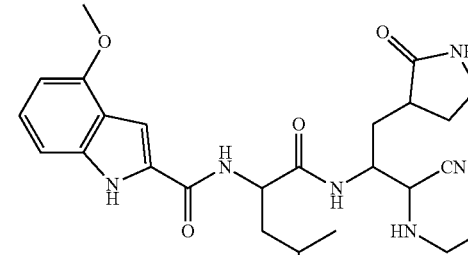 |
| 511 | 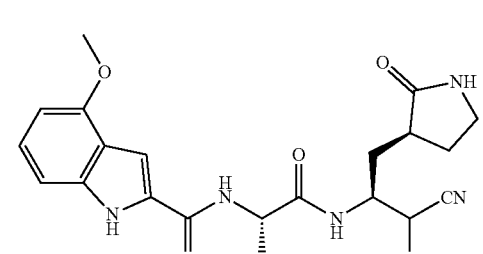 |

TABLE 1-continued
Exemplary compounds.
| Cmpd No. | Structure |
|---|---|
| 512 | 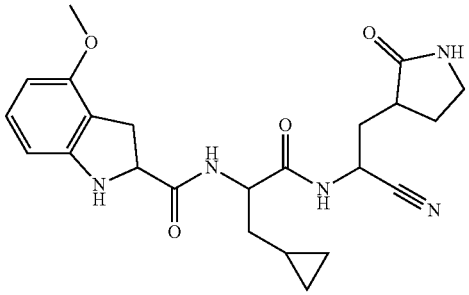 [SMILES: COc1cccc2c1CC(C(=O)NC(CC1CC1)C(=O)NC(C#N)CC1CCNC1=O)N2] |
| 513 | 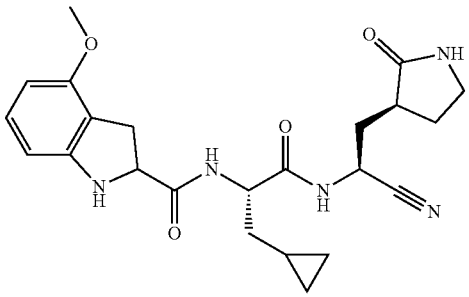 [SMILES: COc1cccc2c1CC(C(=O)N[C@@H](CC1CC1)C(=O)N[C@H](C#N)C[C@@H]1CCNC1=O)N2] |
| 513a | 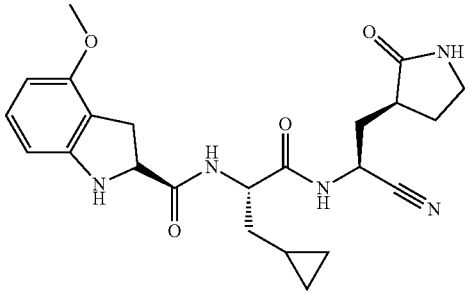 |
| 513b | 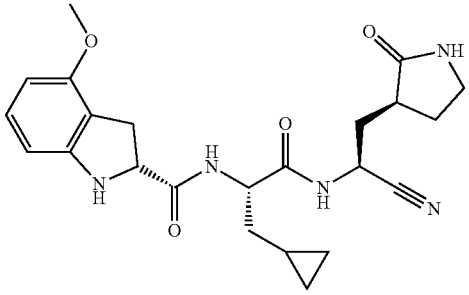 |

TABLE 1-continued

Exemplary compounds.

| Cmpd No. | Structure |
|---|---|
| 514 | 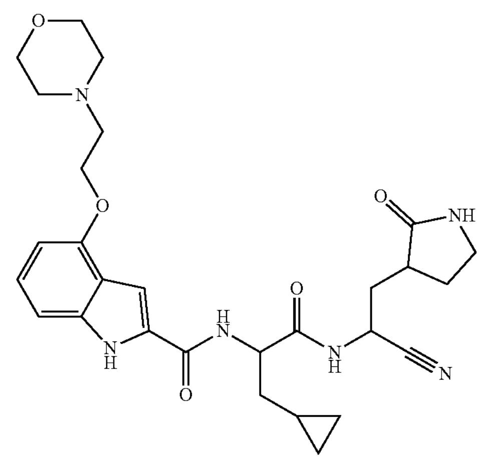 [SMILES: N#CC(CC1CCNC1=O)NC(=O)C(CC1CC1)NC(=O)c1cc2c(OCCN3CCOCC3)cccc2[nH]1] |
| 515 | 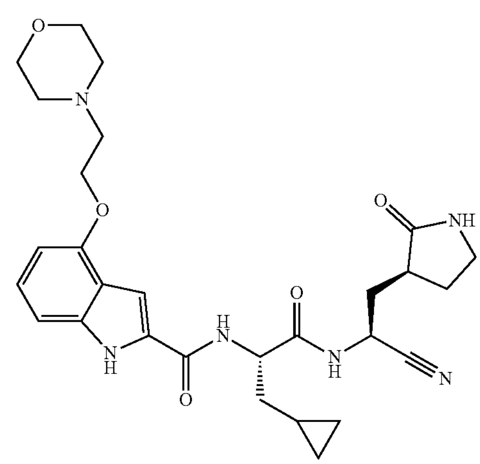 [SMILES: N#C[C@H](C[C@@H]1CCNC1=O)NC(=O)[C@H](CC1CC1)NC(=O)c1cc2c(OCCN3CCOCC3)cccc2[nH]1] |
| 516 | 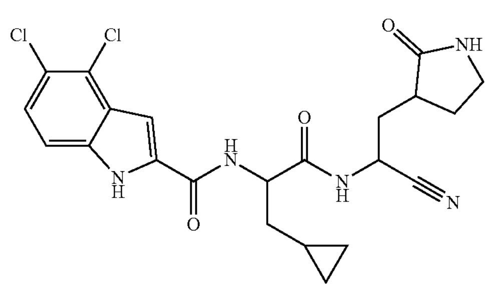 [SMILES: N#CC(CC1CCNC1=O)NC(=O)C(CC1CC1)NC(=O)c1cc2c(Cl)c(Cl)ccc2[nH]1] |
| 517 | 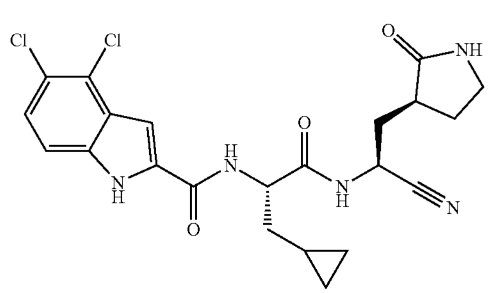 [SMILES: N#C[C@H](C[C@@H]1CCNC1=O)NC(=O)[C@H](CC1CC1)NC(=O)c1cc2c(Cl)c(Cl)ccc2[nH]1] |

TABLE 1-continued

Exemplary compounds.

| Cmpd No. | Structure |
|---|---|
| 518 | 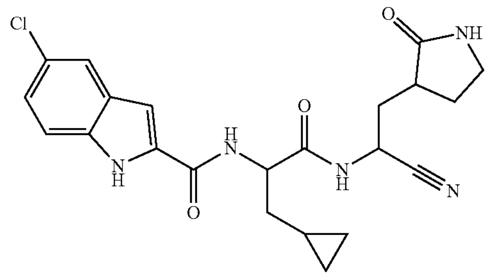 [SMILES: N#CC(CC1CCNC1=O)NC(=O)C(CC1CC1)NC(=O)c1cc2cc(Cl)ccc2[nH]1] |
| 519 | 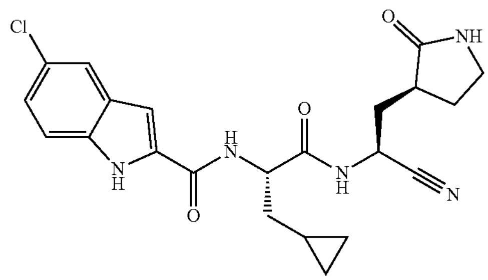 [SMILES: N#C[C@H](C[C@@H]1CCNC1=O)NC(=O)[C@H](CC1CC1)NC(=O)c1cc2cc(Cl)ccc2[nH]1] |
| 520 | 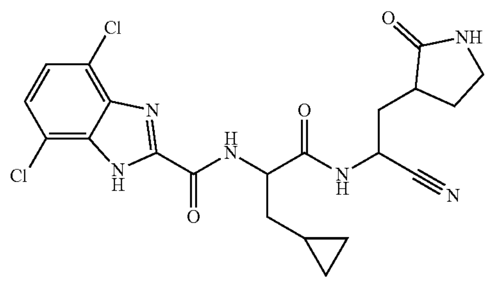 [SMILES: N#CC(CC1CCNC1=O)NC(=O)C(CC1CC1)NC(=O)c1nc2c(Cl)ccc(Cl)c2[nH]1] |
| 521 | 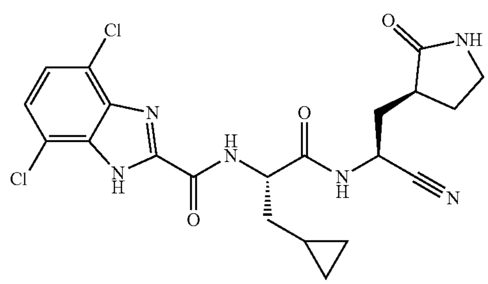 [SMILES: N#C[C@H](C[C@@H]1CCNC1=O)NC(=O)[C@H](CC1CC1)NC(=O)c1nc2c(Cl)ccc(Cl)c2[nH]1] |
| 522 | 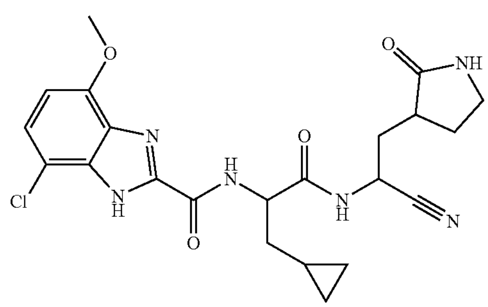 [SMILES: COc1ccc(Cl)c2[nH]c(C(=O)NC(CC3CC3)C(=O)NC(C#N)CC3CCNC3=O)nc12] |

TABLE 1-continued

Exemplary compounds.

| Cmpd No. | Structure |
|---|---|
| 523 | 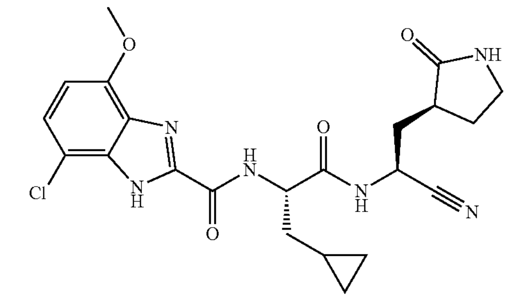 [SMILES: COc1ccc(Cl)c2[nH]c(C(=O)N[C@@H](CC3CC3)C(=O)N[C@H](C#N)C[C@@H]3CCNC3=O)nc12] |
| 524 | 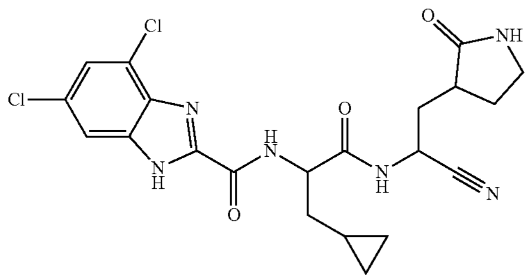 [SMILES: N#CC(CC1CCNC1=O)NC(=O)C(CC1CC1)NC(=O)c1nc2c(Cl)cc(Cl)cc2[nH]1] |
| 525 | 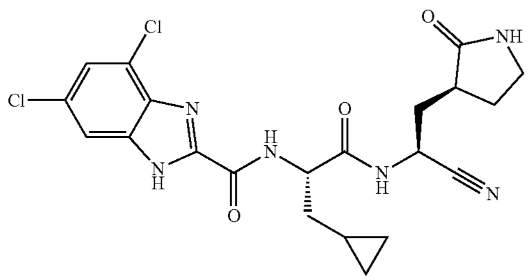 [SMILES: N#C[C@H](C[C@@H]1CCNC1=O)NC(=O)[C@H](CC1CC1)NC(=O)c1nc2c(Cl)cc(Cl)cc2[nH]1] |
| 526 | 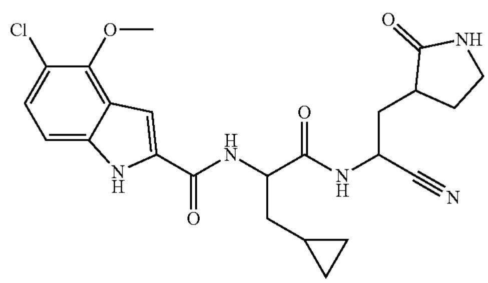 [SMILES: COc1c(Cl)ccc2[nH]c(C(=O)NC(CC3CC3)C(=O)NC(C#N)CC3CCNC3=O)cc12] |
| 527 | 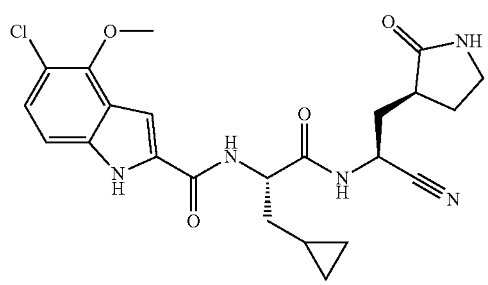 [SMILES: COc1c(Cl)ccc2[nH]c(C(=O)N[C@@H](CC3CC3)C(=O)N[C@H](C#N)C[C@@H]3CCNC3=O)cc12] |

TABLE 1-continued

Exemplary compounds.

| Cmpd No. | Structure |
|---|---|
| 528 | 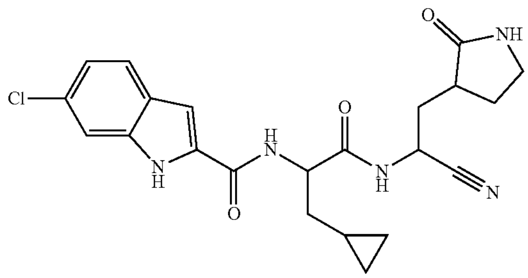 [SMILES: N#CC(CC1CCNC1=O)NC(=O)C(CC1CC1)NC(=O)c1cc2ccc(Cl)cc2[nH]1] |
| 529 | 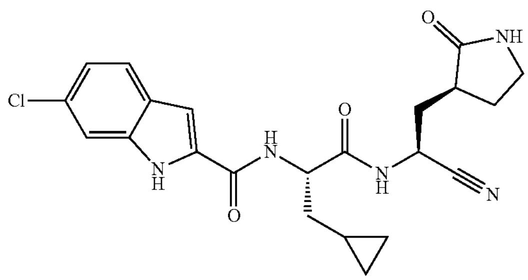 [SMILES: N#C[C@H](C[C@@H]1CCNC1=O)NC(=O)[C@H](CC1CC1)NC(=O)c1cc2ccc(Cl)cc2[nH]1] |
| 530 | 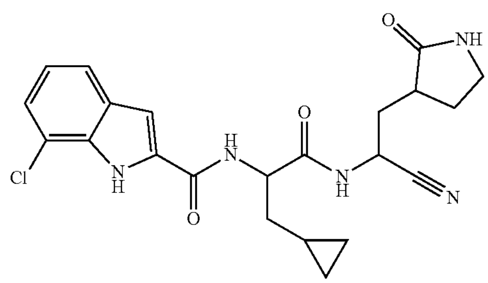 [SMILES: N#CC(CC1CCNC1=O)NC(=O)C(CC1CC1)NC(=O)c1cc2cccc(Cl)c2[nH]1] |
| 531 | 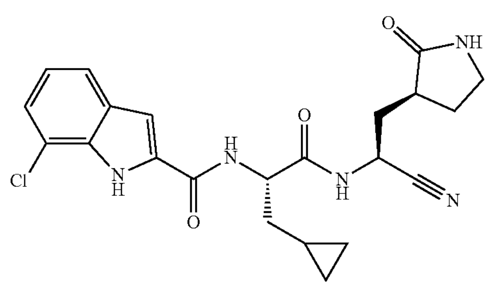 [SMILES: N#C[C@H](C[C@@H]1CCNC1=O)NC(=O)[C@H](CC1CC1)NC(=O)c1cc2cccc(Cl)c2[nH]1] |
| 532 | 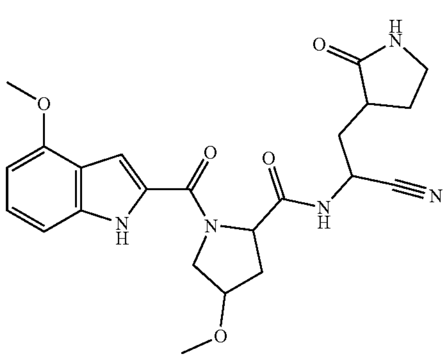 [SMILES: COc1cccc2[nH]c(C(=O)N3CC(OC)CC3C(=O)NC(C#N)CC3CCNC3=O)cc12] |

TABLE 1-continued

Exemplary compounds.

| Cmpd No. | Structure |
|---|---|
| 533 | 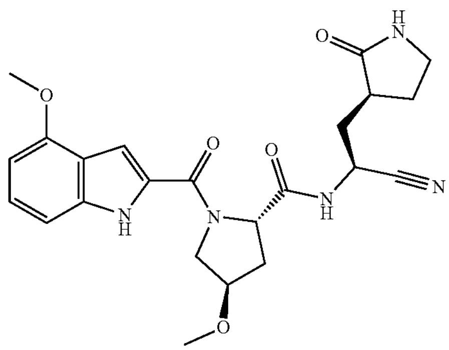 [SMILES: COc1cccc2[nH]c(C(=O)N3C[C@H](OC)C[C@H]3C(=O)N[C@H](C#N)C[C@@H]3CCNC3=O)cc12] |
| 534 | 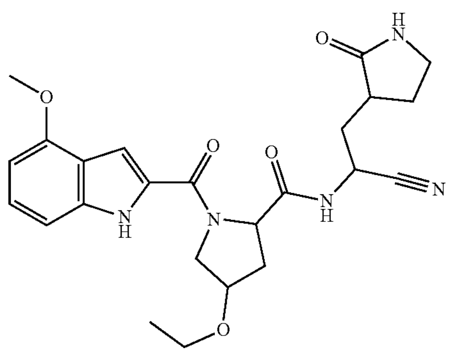 [SMILES: CCOC1CC(C(=O)NC(C#N)CC2CCNC2=O)N(C(=O)c2cc3c(OC)cccc3[nH]2)C1] |
| 535 | 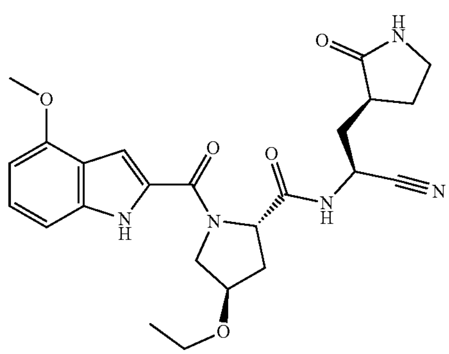 [SMILES: CCO[C@@H]1C[C@@H](C(=O)N[C@H](C#N)C[C@@H]2CCNC2=O)N(C(=O)c2cc3c(OC)cccc3[nH]2)C1] |
| 536 | 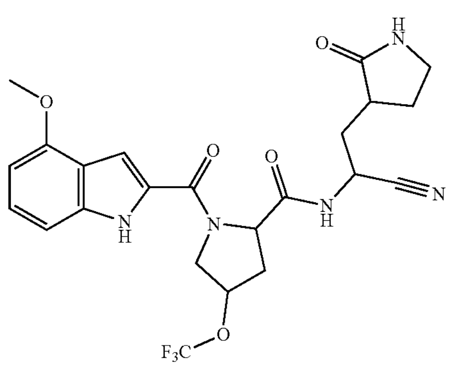 [SMILES: COc1cccc2[nH]c(C(=O)N3CC(OC(F)(F)F)CC3C(=O)NC(C#N)CC3CCNC3=O)cc12] |

TABLE 1-continued

Exemplary compounds.

| Cmpd No. | Structure |
|---|---|
| 537 | 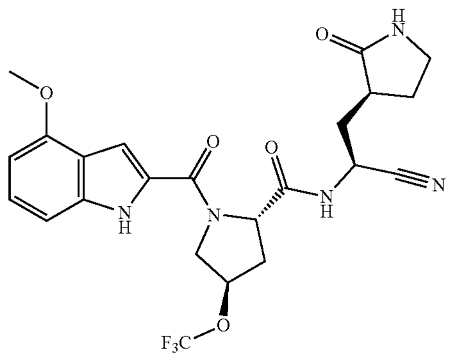 [SMILES: COc1cccc2[nH]c(C(=O)N3C[C@H](OC(F)(F)F)C[C@H]3C(=O)N[C@H](C#N)C[C@@H]3CCNC3=O)cc12] |
| 538 | 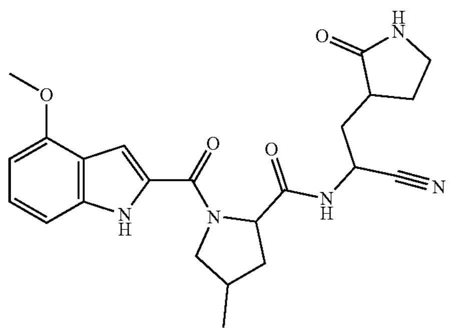 [SMILES: COc1cccc2[nH]c(C(=O)N3CC(C)CC3C(=O)NC(C#N)CC3CCNC3=O)cc12] |
| 539 | 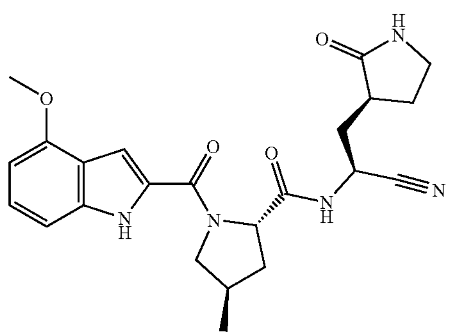 [SMILES: COc1cccc2[nH]c(C(=O)N3C[C@H](C)C[C@H]3C(=O)N[C@H](C#N)C[C@@H]3CCNC3=O)cc12] |
| 540 | 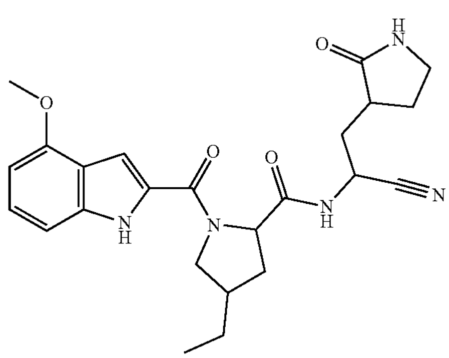 |

TABLE 1-continued

Exemplary compounds.

| Cmpd No. | Structure |
| --- | --- |
| 541 | 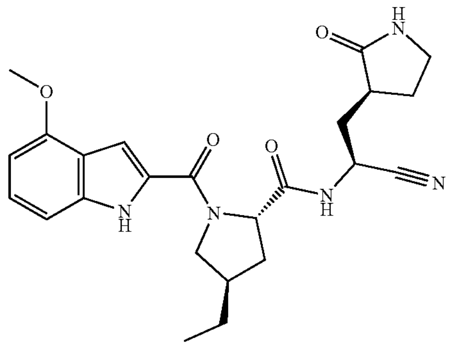 [SMILES: CC[C@@H]1C[C@@H](C(=O)N[C@H](C#N)C[C@@H]2CCNC2=O)N(C(=O)c2cc3c(OC)cccc3[nH]2)C1] |
| 542 | 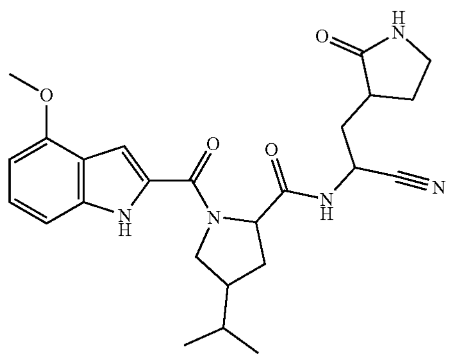 [SMILES: COc1cccc2[nH]c(C(=O)N3CC(C(C)C)CC3C(=O)NC(C#N)CC3CCNC3=O)cc12] |
| 543 | 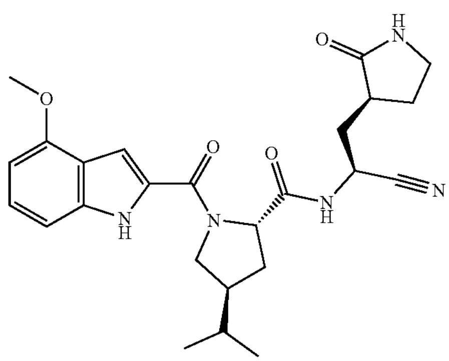 [SMILES: COc1cccc2[nH]c(C(=O)N3C[C@H](C(C)C)C[C@H]3C(=O)N[C@H](C#N)C[C@@H]3CCNC3=O)cc12] |
| 544 | 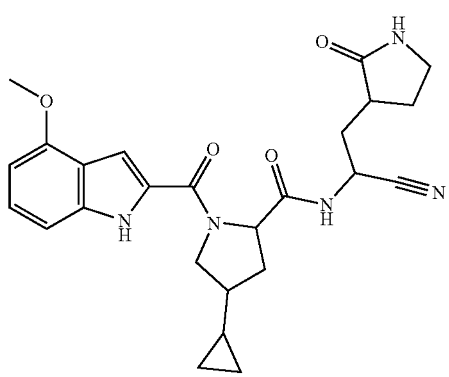 [SMILES: COc1cccc2[nH]c(C(=O)N3CC(C4CC4)CC3C(=O)NC(C#N)CC3CCNC3=O)cc12] |

TABLE 1-continued

Exemplary compounds.

| Cmpd No. | Structure |
|---|---|
| 545 | 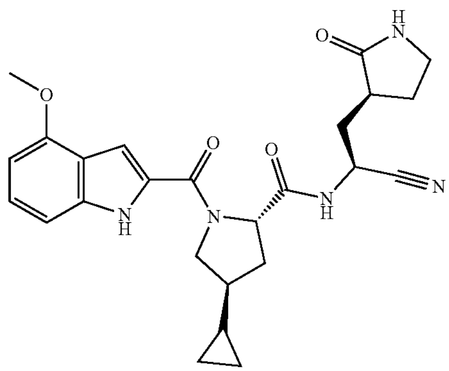 [SMILES: COc1cccc2[nH]c(C(=O)N3C[C@H](C4CC4)C[C@H]3C(=O)N[C@H](C#N)C[C@@H]3CCNC3=O)cc12] |
| 546 | 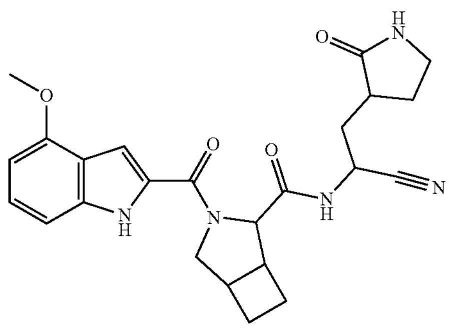 [SMILES: COc1cccc2[nH]c(C(=O)N3CC4CCC4C3C(=O)NC(C#N)CC3CCNC3=O)cc12] |
| 547 | 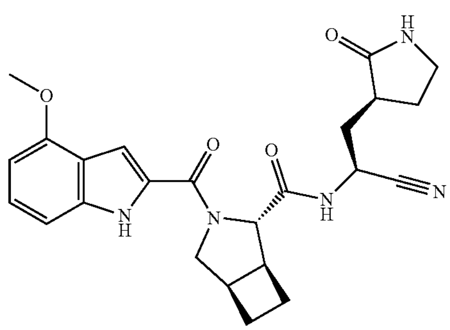 [SMILES: COc1cccc2[nH]c(C(=O)N3C[C@@H]4CC[C@@H]4[C@H]3C(=O)N[C@H](C#N)C[C@@H]3CCNC3=O)cc12] |
| 548 | 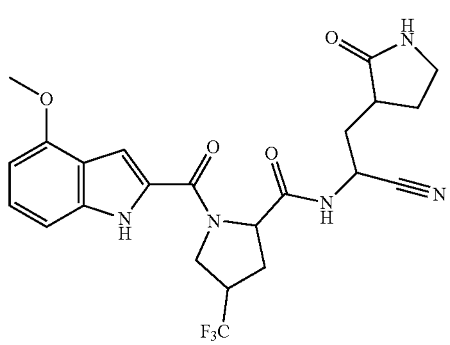 [SMILES: COc1cccc2[nH]c(C(=O)N3CC(C(F)(F)F)CC3C(=O)NC(C#N)CC3CCNC3=O)cc12] |

TABLE 1-continued
Exemplary compounds.
| Cmpd No. | Structure |
|---|---|
| 549 | 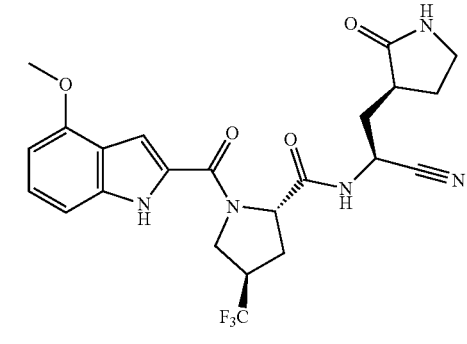 [SMILES: COc1cccc2[nH]c(C(=O)N3C[C@H](C(F)(F)F)C[C@H]3C(=O)N[C@H](C#N)C[C@@H]3CCNC3=O)cc12] |
| 550 | 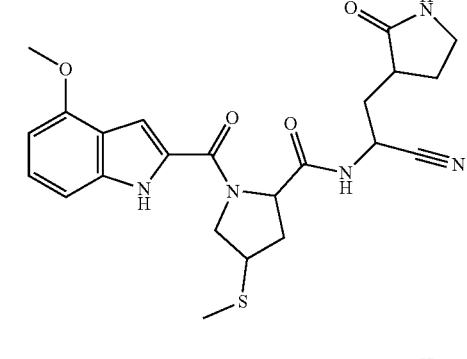 |
| 551 | 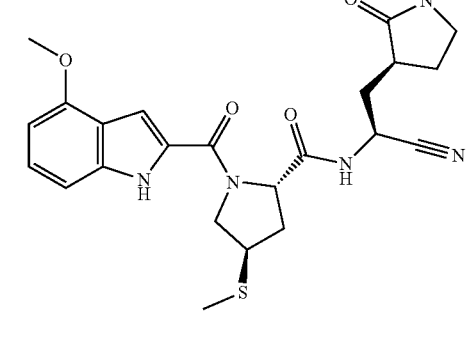 |
| 552 | 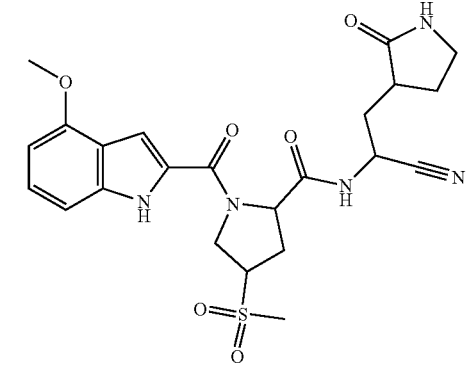 [SMILES: COc1cccc2[nH]c(C(=O)N3CC(S(C)(=O)=O)CC3C(=O)NC(C#N)CC3CCNC3=O)cc12] |

TABLE 1-continued
Exemplary compounds.
| Cmpd No. | Structure |
|---|---|
| 553 | 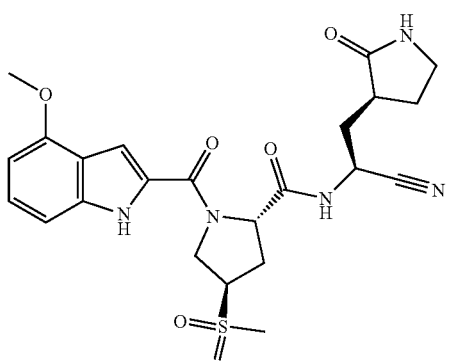 |
| 554 | 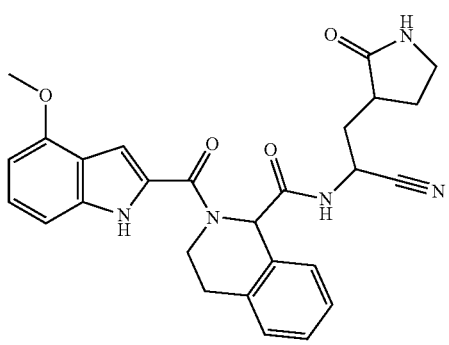 [SMILES: COc1cccc2[nH]c(C(=O)N3CCc4ccccc4C3C(=O)NC(C#N)CC3CCNC3=O)cc12] |
| 555 | 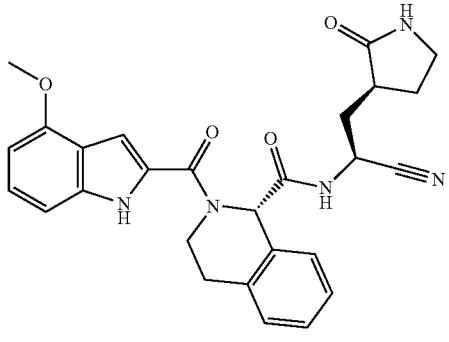 [SMILES: COc1cccc2[nH]c(C(=O)N3CCc4ccccc4[C@H]3C(=O)N[C@H](C#N)C[C@@H]3CCNC3=O)cc12] |
| 556 | 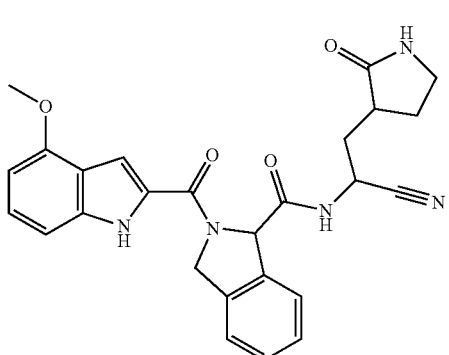 |

TABLE 1-continued
Exemplary compounds.
| Cmpd No. | Structure |
|---|---|
| 557 | 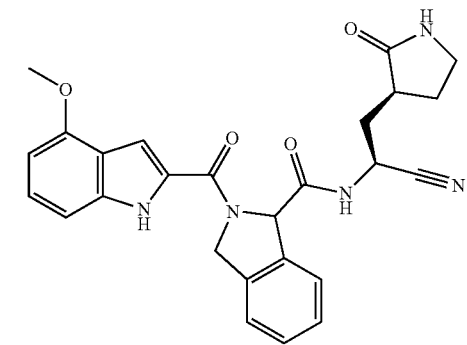 [SMILES: COc1cccc2[nH]c(C(=O)N3Cc4ccccc4C3C(=O)N[C@H](C#N)C[C@@H]3CCNC3=O)cc12] |
| 557a | 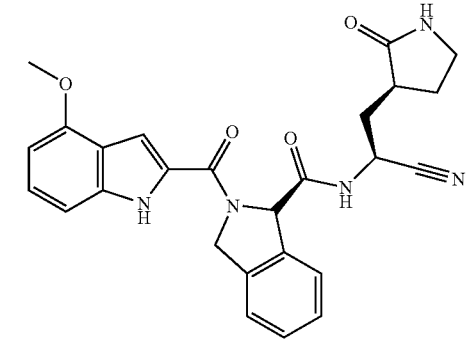 |
| 557b | 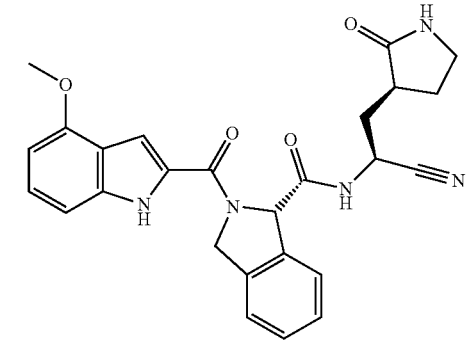 |
| 558 | 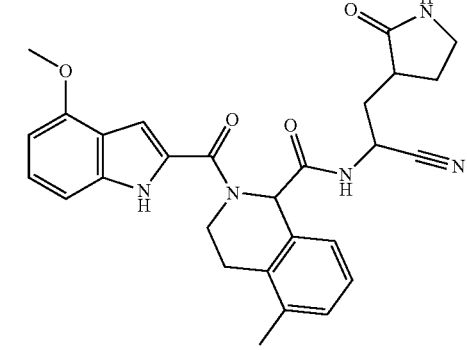 |

TABLE 1-continued
Exemplary compounds.
| Cmpd No. | Structure |
|---|---|
| 559 | 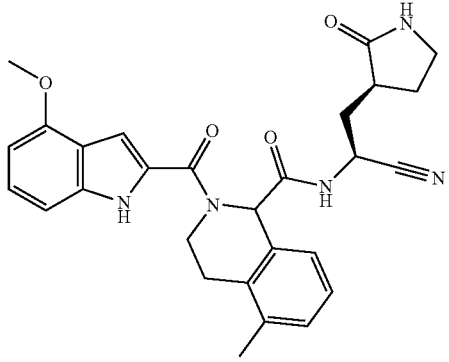 [SMILES: COc1cccc2[nH]c(C(=O)N3CCc4c(C)cccc4C3C(=O)N[C@H](C#N)C[C@@H]3CCNC3=O)cc12] |
| 559a | 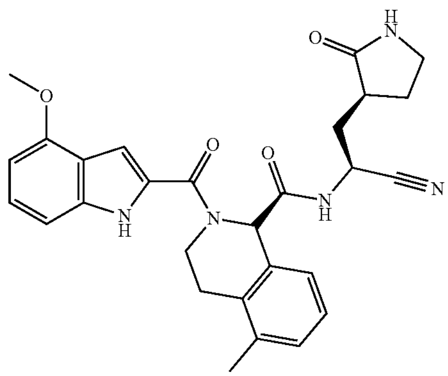 |
| 559b | 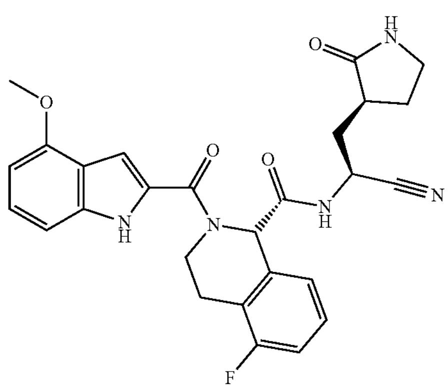 |
| 560 | 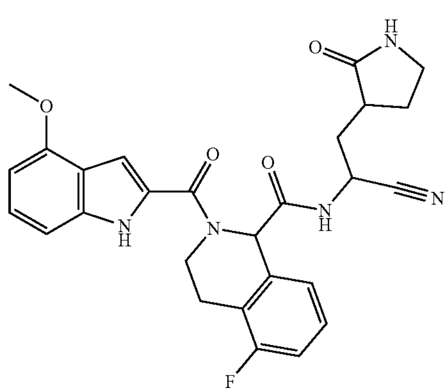 [SMILES: COc1cccc2[nH]c(C(=O)N3CCc4c(F)cccc4C3C(=O)NC(C#N)CC3CCNC3=O)cc12] |

TABLE 1-continued

Exemplary compounds.

| Cmpd No. | Structure |
|---|---|
| 561 | 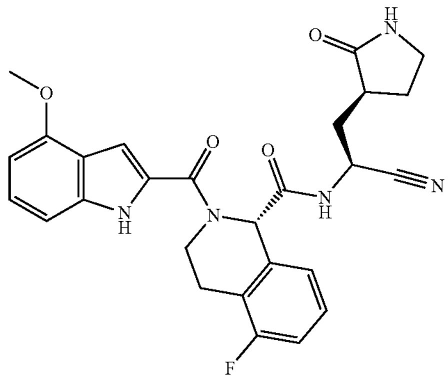 [SMILES: COc1cccc2[nH]c(C(=O)N3CCc4c(F)cccc4[C@H]3C(=O)N[C@H](C#N)C[C@@H]3CCNC3=O)cc12] |
| 562 | 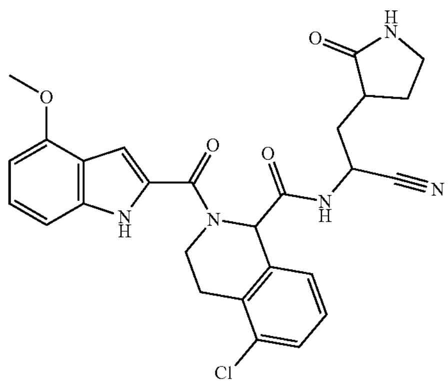 [SMILES: COc1cccc2[nH]c(C(=O)N3CCc4c(Cl)cccc4C3C(=O)NC(C#N)CC3CCNC3=O)cc12] |
| 563 | 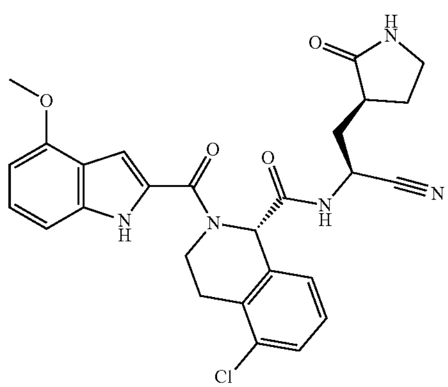 [SMILES: COc1cccc2[nH]c(C(=O)N3CCc4c(Cl)cccc4[C@H]3C(=O)N[C@H](C#N)C[C@@H]3CCNC3=O)cc12] |
| 564 | 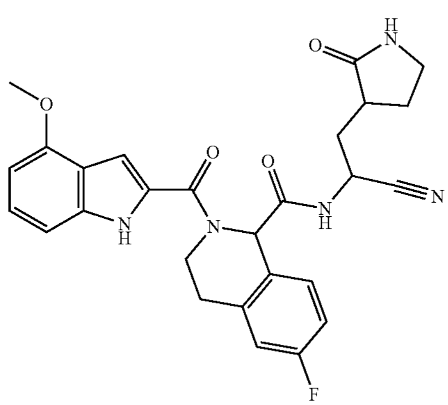 [SMILES: COc1cccc2[nH]c(C(=O)N3CCc4cc(F)ccc4C3C(=O)NC(C#N)CC3CCNC3=O)cc12] |

297 298
TABLE 1-continued
Exemplary compounds.
| Cmpd No. | Structure |
|---|---|
| 565 | 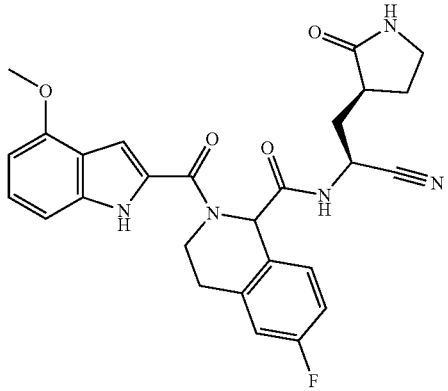 [SMILES: COc1cccc2[nH]c(C(=O)N3CCc4cc(F)ccc4C3C(=O)N[C@H](C#N)C[C@@H]3CCNC3=O)cc12] |
| 565a | 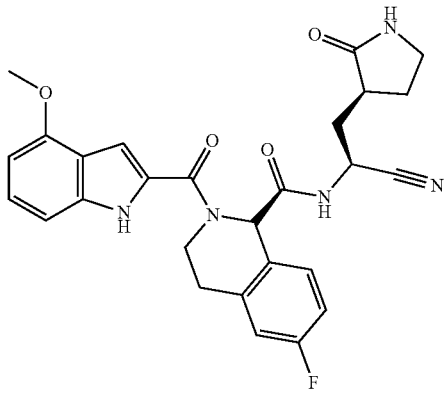 |
| 565b | 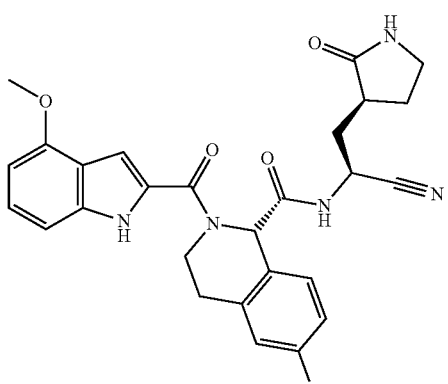 |
| 566 | 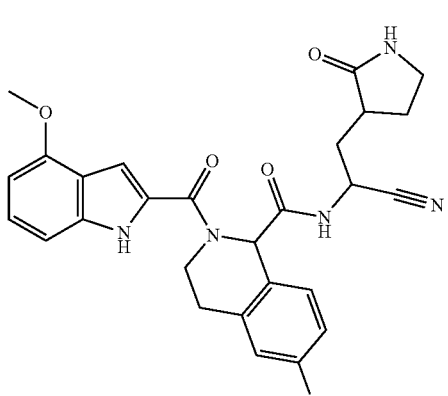 |

TABLE 1-continued
Exemplary compounds.
| Cmpd No. | Structure |
|---|---|
| 567 | 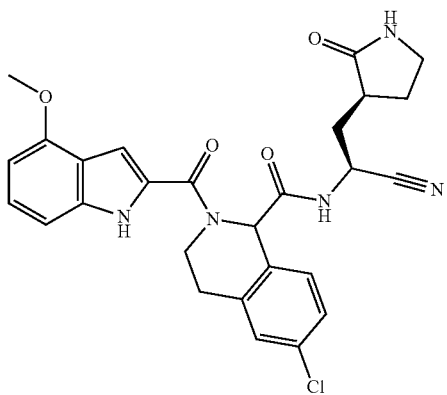 [SMILES: COc1cccc2[nH]c(C(=O)N3CCc4cc(Cl)ccc4C3C(=O)N[C@H](C#N)C[C@@H]3CCNC3=O)cc12] |
| 567a | 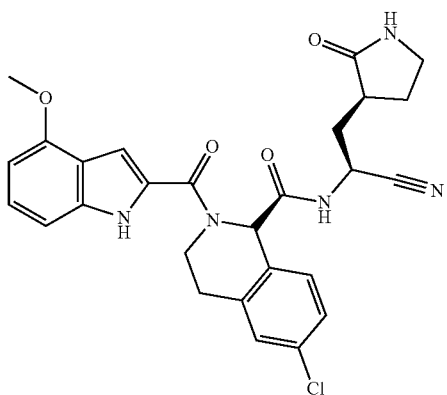 |
| 567b | 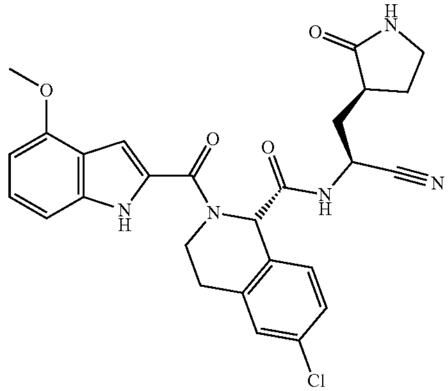 |

TABLE 1-continued

Exemplary compounds.

| Cmpd No. | Structure |
|---|---|
| 568 | 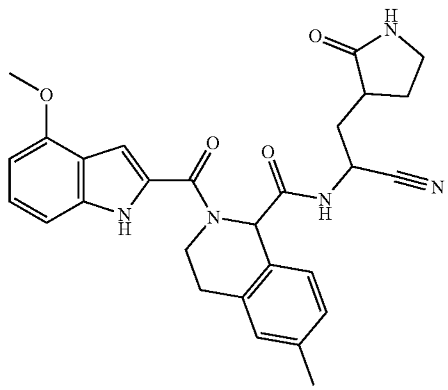 [SMILES: COc1cccc2[nH]c(C(=O)N3CCc4cc(C)ccc4C3C(=O)NC(C#N)CC3CCNC3=O)cc12] |
| 569 | 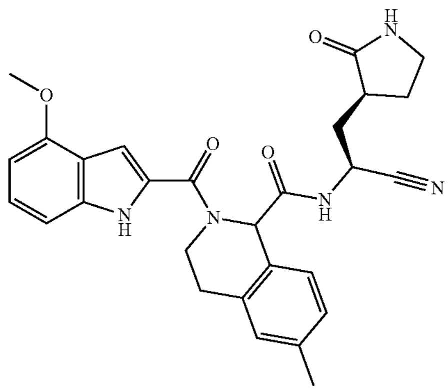 [SMILES: COc1cccc2[nH]c(C(=O)N3CCc4cc(C)ccc4C3C(=O)N[C@H](C#N)C[C@@H]3CCNC3=O)cc12] |
| 569a | 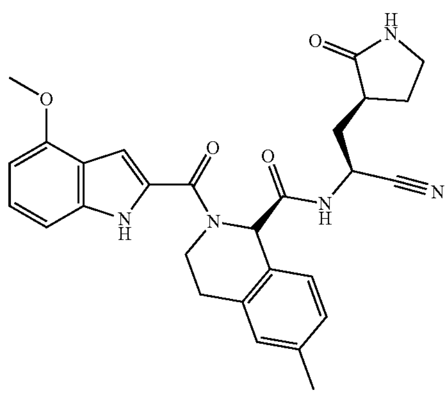 |
| 569b | 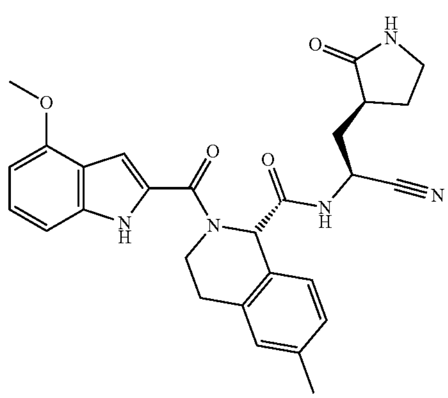 |

TABLE 1-continued

Exemplary compounds.

| Cmpd No. | Structure |
|---|---|
| 570 | 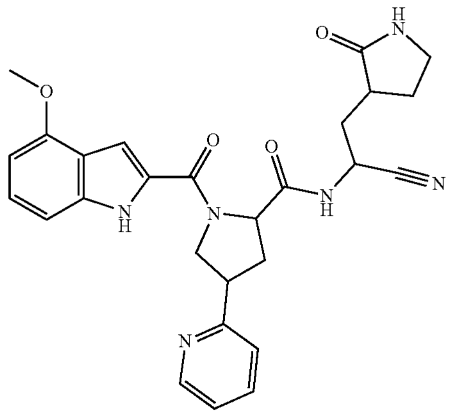 [SMILES: COc1cccc2[nH]c(C(=O)N3CC(c4ccccn4)CC3C(=O)NC(C#N)CC3CCNC3=O)cc12] |
| 571 | 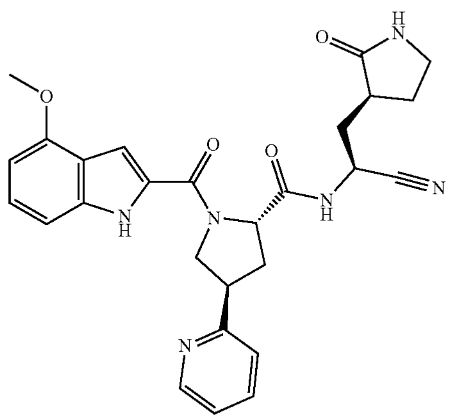 [SMILES: COc1cccc2[nH]c(C(=O)N3C[C@H](c4ccccn4)C[C@H]3C(=O)N[C@H](C#N)C[C@@H]3CCNC3=O)cc12] |
| 572 | 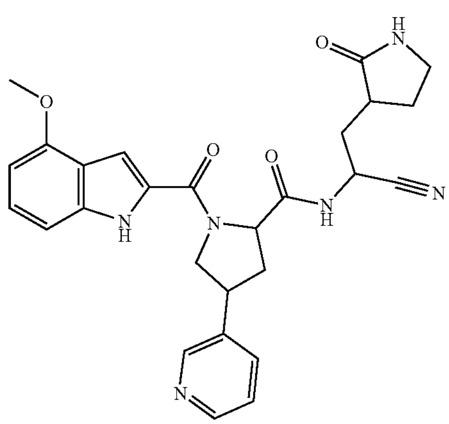 [SMILES: COc1cccc2[nH]c(C(=O)N3CC(c4cccnc4)CC3C(=O)NC(C#N)CC3CCNC3=O)cc12] |

TABLE 1-continued
Exemplary compounds.
| Cmpd No. | Structure |
|---|---|
| 573 | 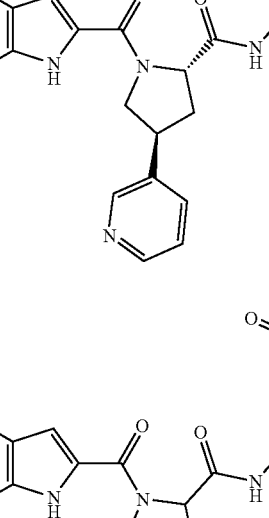 |
| 574 | 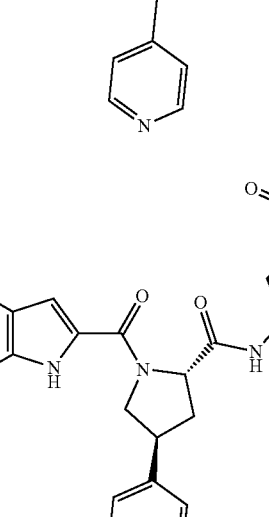 |
| 575 | 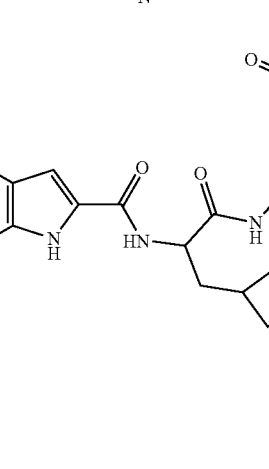 |
| 576 | 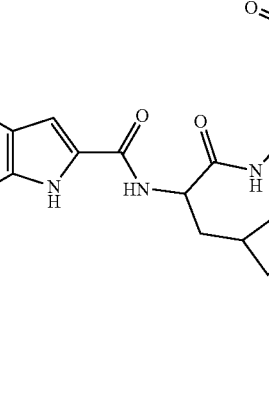 |

TABLE 1-continued
Exemplary compounds.
| Cmpd No. | Structure |
|---|---|
| 577 | 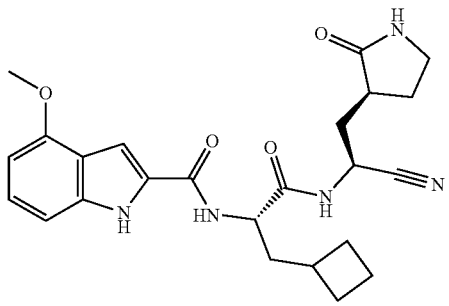 [SMILES: COc1cccc2[nH]c(C(=O)N[C@@H](CC3CCC3)C(=O)N[C@H](C#N)C[C@@H]3CCNC3=O)cc12] |
| 578 | 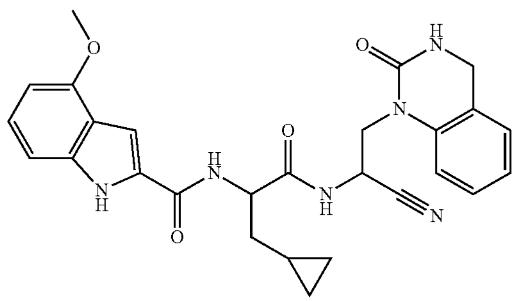 [SMILES: COc1cccc2[nH]c(C(=O)NC(CC3CC3)C(=O)NC(C#N)CN3C(=O)NCc4ccccc43)cc12] |
| 579 | 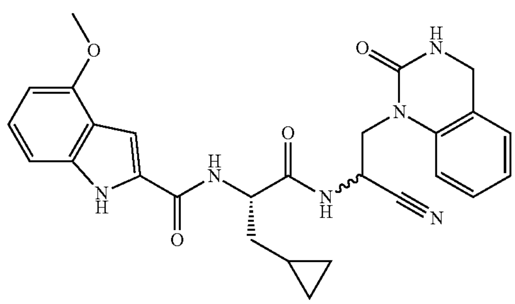 [SMILES: COc1cccc2[nH]c(C(=O)N[C@@H](CC3CC3)C(=O)NC(C#N)CN3C(=O)NCc4ccccc43)cc12] |
| 579a | 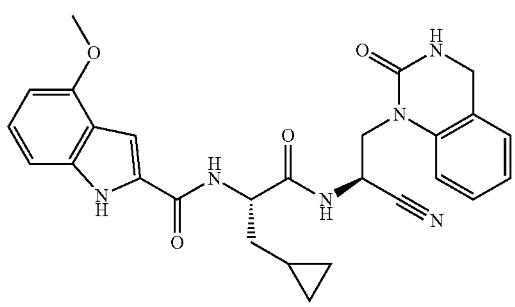 [SMILES: COc1cccc2[nH]c(C(=O)N[C@@H](CC3CC3)C(=O)N[C@H](C#N)CN3C(=O)NCc4ccccc43)cc12] |
| 579b | 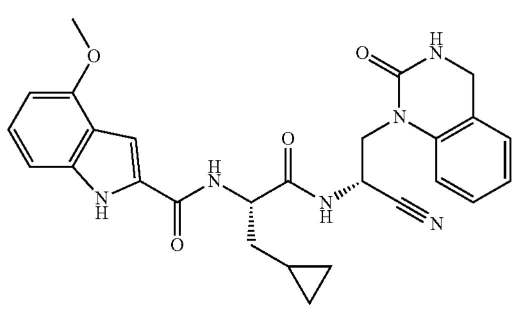 [SMILES: COc1cccc2[nH]c(C(=O)N[C@@H](CC3CC3)C(=O)N[C@@H](C#N)CN3C(=O)NCc4ccccc43)cc12] |

TABLE 1-continued
Exemplary compounds.
| Cmpd No. | Structure |
|---|---|
| 580 | 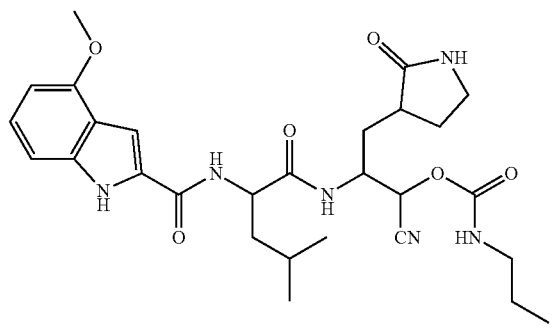 [SMILES: CCCNC(=O)OC(C#N)C(CC1CCNC1=O)NC(=O)C(CC(C)C)NC(=O)c1cc2c(OC)cccc2[nH]1] |
| 581 | 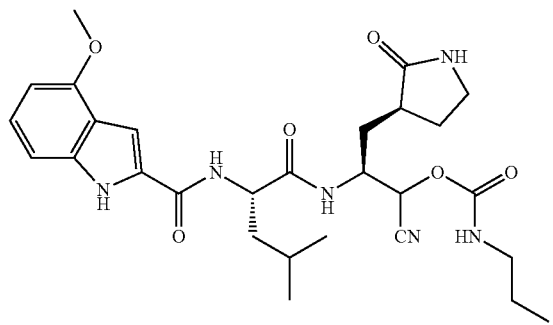 [SMILES: CCCNC(=O)OC(C#N)[C@H](C[C@@H]1CCNC1=O)NC(=O)[C@H](CC(C)C)NC(=O)c1cc2c(OC)cccc2[nH]1] |
| 582 | 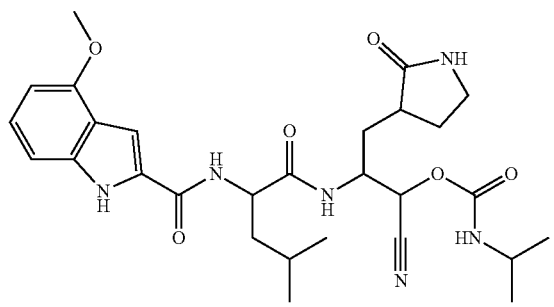 [SMILES: COc1cccc2[nH]c(C(=O)NC(CC(C)C)C(=O)NC(CC3CCNC3=O)C(C#N)OC(=O)NC(C)C)cc12] |
| 583 | 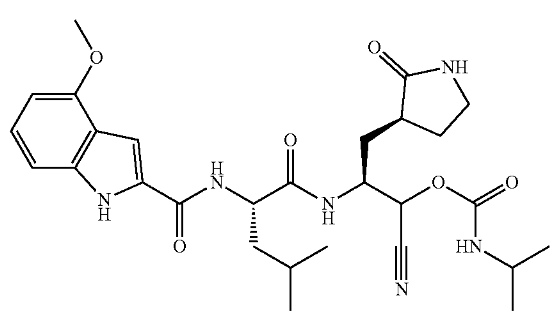 [SMILES: COc1cccc2[nH]c(C(=O)N[C@@H](CC(C)C)C(=O)N[C@@H](C[C@@H]3CCNC3=O)C(C#N)OC(=O)NC(C)C)cc12] |

311
312
TABLE 1-continued
Exemplary compounds.
| Cmpd No. | Structure |
|---|---|
| 584 | 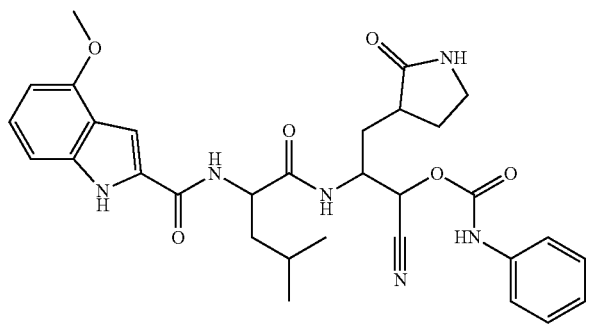 [SMILES: COc1cccc2[nH]c(C(=O)NC(CC(C)C)C(=O)NC(CC3CCNC3=O)C(C#N)OC(=O)Nc3ccccc3)cc12] |
| 585 | 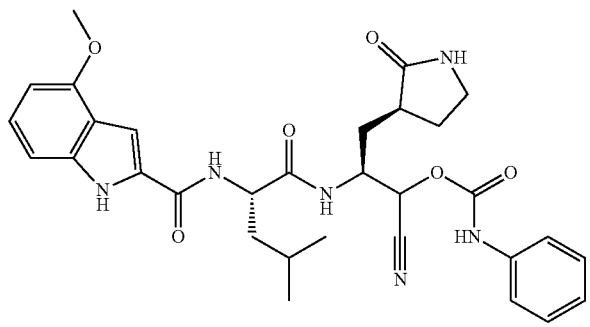 [SMILES: COc1cccc2[nH]c(C(=O)N[C@@H](CC(C)C)C(=O)N[C@@H](C[C@@H]3CCNC3=O)C(C#N)OC(=O)Nc3ccccc3)cc12] |
| 586 | 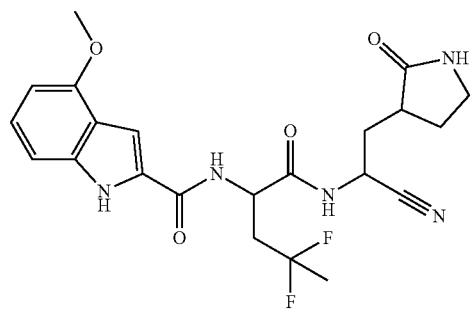 [SMILES: COc1cccc2[nH]c(C(=O)NC(CC(C)(F)F)C(=O)NC(C#N)CC3CCNC3=O)cc12] |
| 587 | 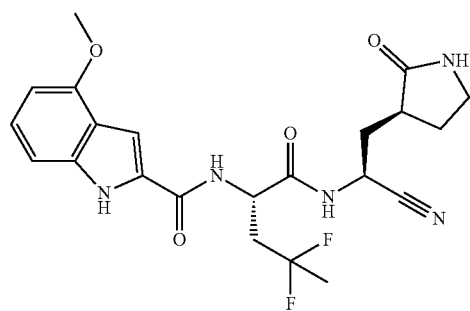 [SMILES: COc1cccc2[nH]c(C(=O)N[C@@H](CC(C)(F)F)C(=O)N[C@H](C#N)C[C@@H]3CCNC3=O)cc12] |

TABLE 1-continued

Exemplary compounds.

| Cmpd No. | Structure |
|---|---|
| 588 | 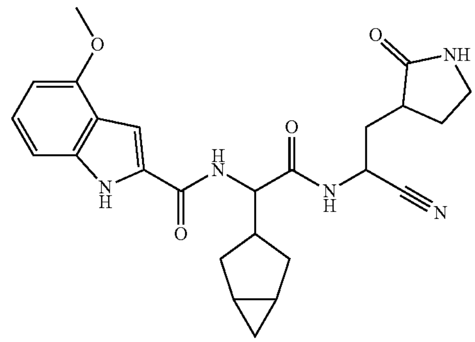 [SMILES: COc1cccc2[nH]c(C(=O)NC(C(=O)NC(C#N)CC3CCNC3=O)C3CC4CC4C3)cc12] |
| 589 | 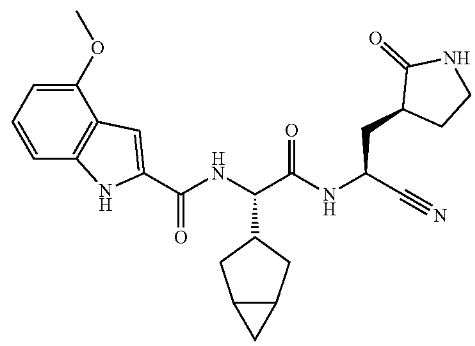 [SMILES: COc1cccc2[nH]c(C(=O)N[C@H](C(=O)N[C@H](C#N)C[C@@H]3CCNC3=O)C3CC4CC4C3)cc12] |
| 590 | 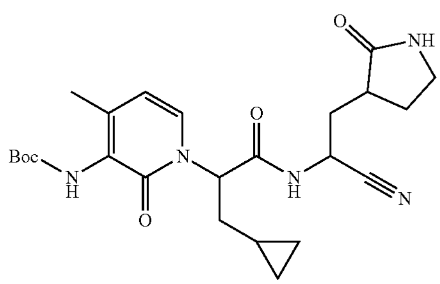 [SMILES: Cc1ccn(C(CC2CC2)C(=O)NC(C#N)CC2CCNC2=O)c(=O)c1NC(=O)OC(C)(C)C] |
| 591 | 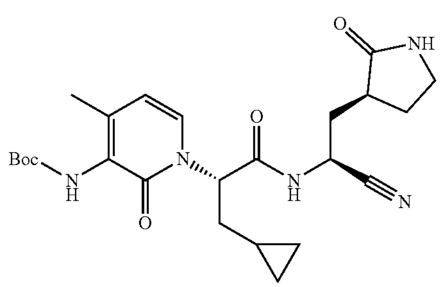 [SMILES: Cc1ccn([C@@H](CC2CC2)C(=O)N[C@H](C#N)C[C@@H]2CCNC2=O)c(=O)c1NC(=O)OC(C)(C)C] |
| 592 | 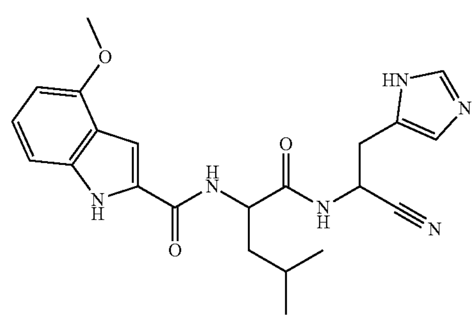 [SMILES: COc1cccc2[nH]c(C(=O)NC(CC(C)C)C(=O)NC(C#N)Cc3cnc[nH]3)cc12] |

TABLE 1-continued

Exemplary compounds.

| Cmpd No. | Structure |
|---|---|
| 593 | 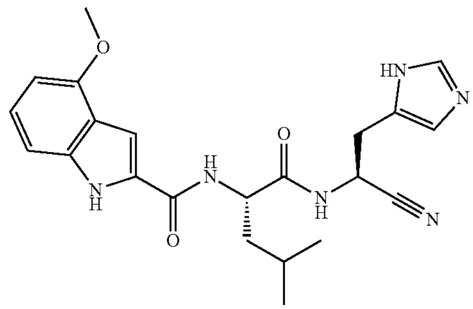 [SMILES: COc1cccc2[nH]c(C(=O)N[C@@H](CC(C)C)C(=O)N[C@H](C#N)Cc3cnc[nH]3)cc12] |
| 594 | 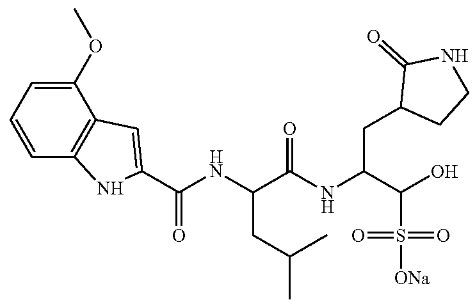 |
| 595 | 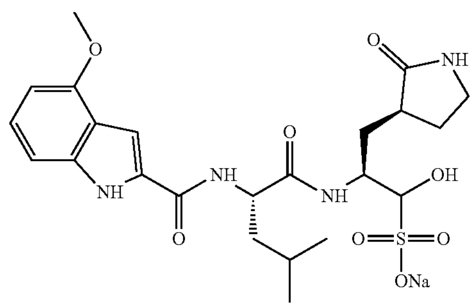 |
| 596 | 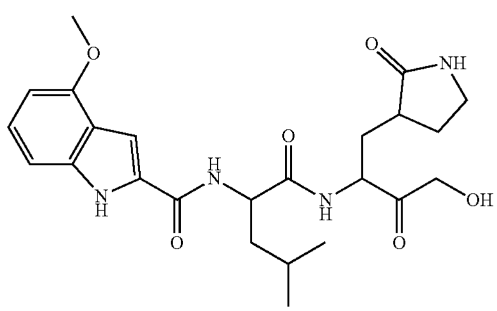 [SMILES: COc1cccc2[nH]c(C(=O)NC(CC(C)C)C(=O)NC(CC3CCNC3=O)C(=O)CO)cc12] |
| 597 | 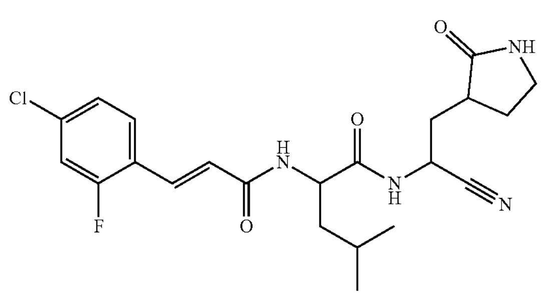 [SMILES: CC(C)CC(NC(=O)/C=C/c1ccc(Cl)cc1F)C(=O)NC(C#N)CC1CCNC1=O] |

TABLE 1-continued

Exemplary compounds.

| Cmpd No. | Structure |
|---|---|
| 598 | 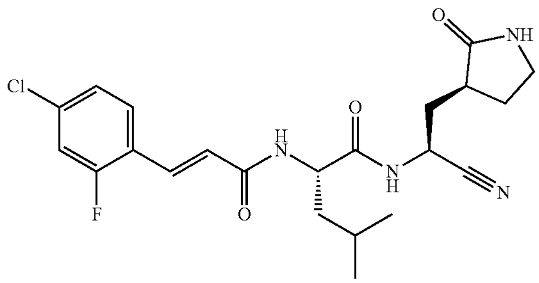 [SMILES: CC(C)C[C@H](NC(=O)/C=C/c1ccc(Cl)cc1F)C(=O)N[C@H](C#N)C[C@@H]1CCNC1=O] |
| 599A | 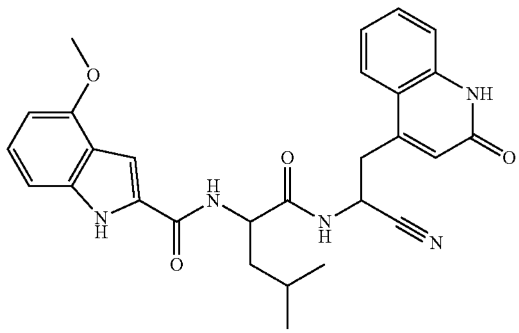 [SMILES: COc1cccc2[nH]c(C(=O)NC(CC(C)C)C(=O)NC(C#N)Cc3cc(=O)[nH]c4ccccc34)cc12] |
| 599 | 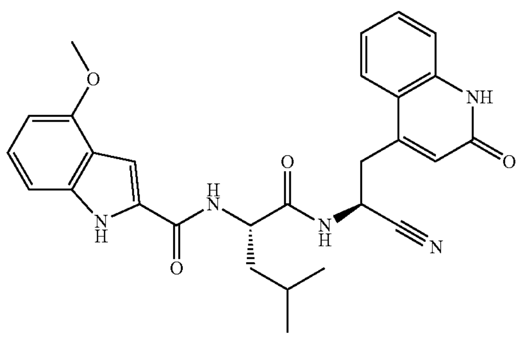 [SMILES: COc1cccc2[nH]c(C(=O)N[C@@H](CC(C)C)C(=O)N[C@H](C#N)Cc3cc(=O)[nH]c4ccccc34)cc12] |
| 600A | 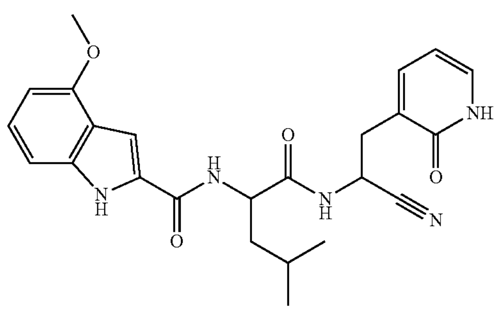 [SMILES: COc1cccc2[nH]c(C(=O)NC(CC(C)C)C(=O)NC(C#N)Cc3ccc[nH]c3=O)cc12] |
| 600 | 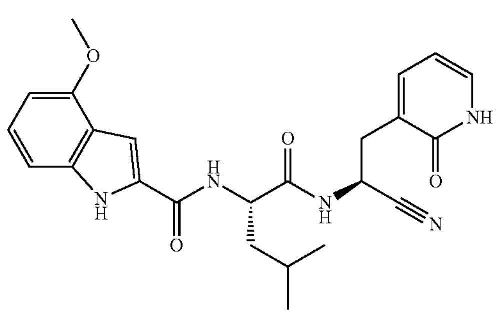 [SMILES: COc1cccc2[nH]c(C(=O)N[C@@H](CC(C)C)C(=O)N[C@H](C#N)Cc3ccc[nH]c3=O)cc12] |

TABLE 1-continued

Exemplary compounds.

| Cmpd No. | Structure |
|---|---|
| 344A | 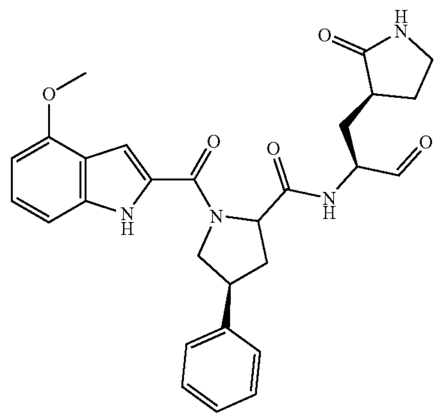 [SMILES: COc1cccc2[nH]c(C(=O)N3C[C@H](c4ccccc4)CC3C(=O)N[C@H](C=O)C[C@@H]3CCNC3=O)cc12] |
| 344B | 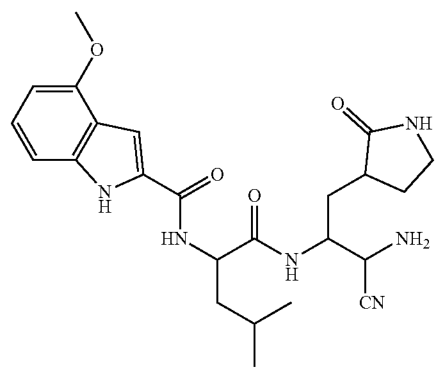 [SMILES: COc1cccc2[nH]c(C(=O)NC(CC(C)C)C(=O)NC(CC3CCNC3=O)C(N)C#N)cc12] |
| 344C | 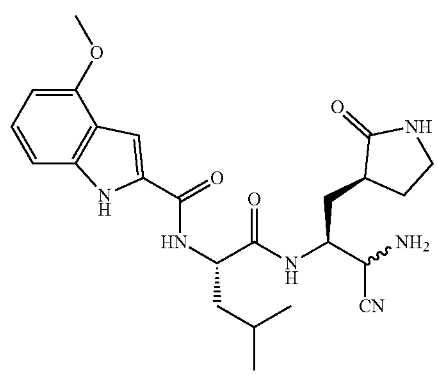 [SMILES: COc1cccc2[nH]c(C(=O)N[C@@H](CC(C)C)C(=O)N[C@@H](C[C@@H]3CCNC3=O)C(N)C#N)cc12] |
| 344D | 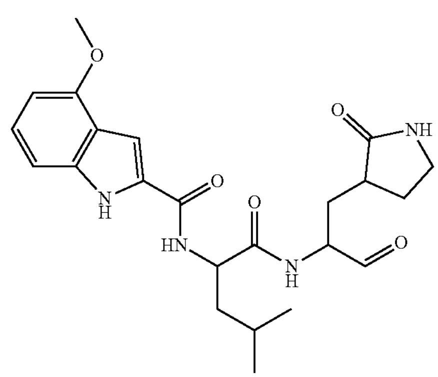 [SMILES: COc1cccc2[nH]c(C(=O)NC(CC(C)C)C(=O)NC(C=O)CC3CCNC3=O)cc12] |

TABLE 1-continued
Exemplary compounds.
| Cmpd No. | Structure |
|---|---|
| 602A | 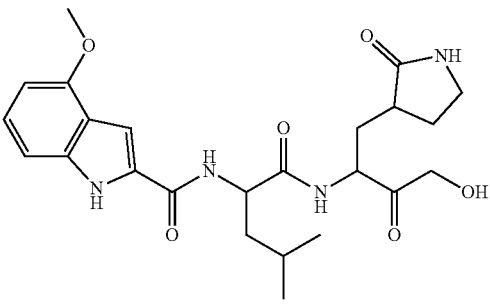 [SMILES: COc1cccc2[nH]c(C(=O)NC(CC(C)C)C(=O)NC(CC3CCNC3=O)C(=O)CO)cc12] |
| 602 | 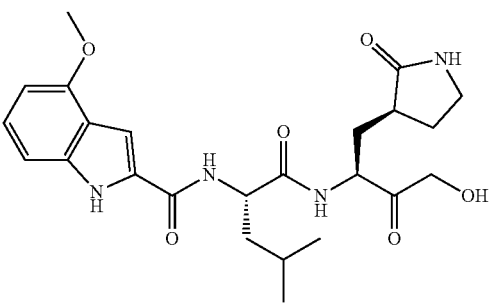 [SMILES: COc1cccc2[nH]c(C(=O)N[C@@H](CC(C)C)C(=O)N[C@@H](C[C@@H]3CCNC3=O)C(=O)CO)cc12] |
| 603 | 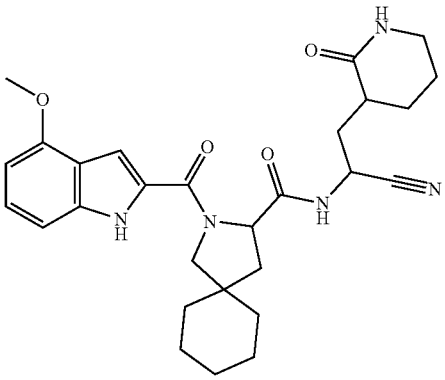 [SMILES: COc1cccc2[nH]c(C(=O)N3CC4(CCCCC4)CC3C(=O)NC(C#N)CC3CCCNC3=O)cc12] |
| 603a | 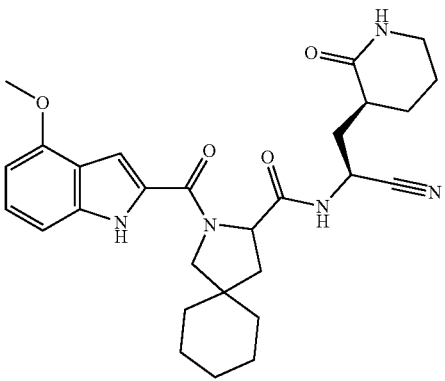 |

TABLE 1-continued

Exemplary compounds.

| Cmpd No. | Structure |
|---|---|
| 604 | 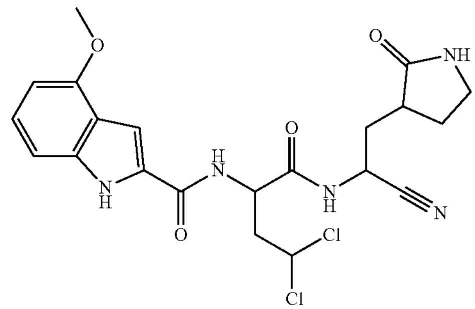 [SMILES: COc1cccc2[nH]c(C(=O)NC(CC(Cl)Cl)C(=O)NC(C#N)CC3CCNC3=O)cc12] |
| 605 | 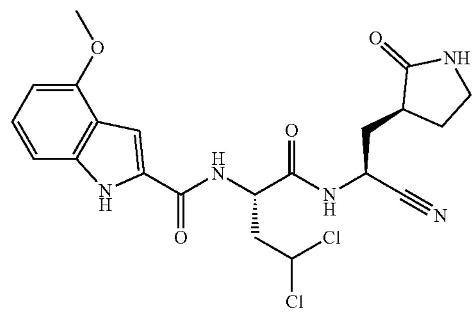 [SMILES: COc1cccc2[nH]c(C(=O)N[C@@H](CC(Cl)Cl)C(=O)N[C@H](C#N)C[C@@H]3CCNC3=O)cc12] |
| 606 | 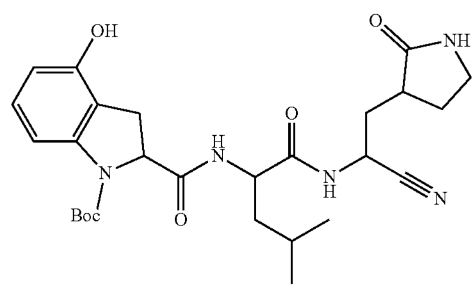 [SMILES: CC(C)CC(NC(=O)C1Cc2c(O)cccc2N1C(=O)OC(C)(C)C)C(=O)NC(C#N)CC1CCNC1=O] |
| 607 | 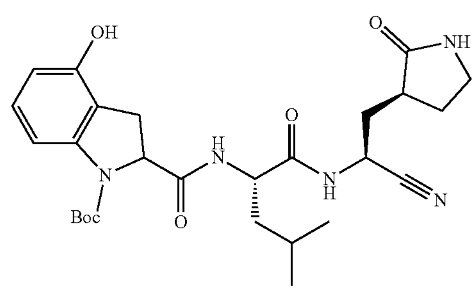 [SMILES: CC(C)C[C@H](NC(=O)C1Cc2c(O)cccc2N1C(=O)OC(C)(C)C)C(=O)N[C@H](C#N)C[C@@H]1CCNC1=O] |
| 608 | 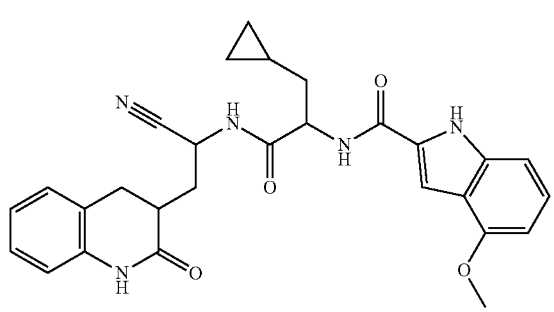 [SMILES: COc1cccc2[nH]c(C(=O)NC(CC3CC3)C(=O)NC(C#N)CC3Cc4ccccc4NC3=O)cc12] |

TABLE 1-continued

Exemplary compounds.

| Cmpd No. | Structure |
|---|---|
| 609 | 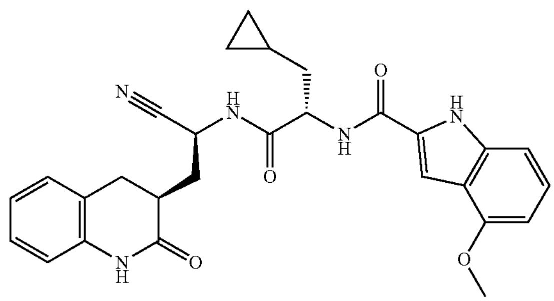 [SMILES: COc1cccc2[nH]c(C(=O)N[C@@H](CC3CC3)C(=O)N[C@H](C#N)C[C@@H]3Cc4ccccc4NC3=O)cc12] |
| 610 | 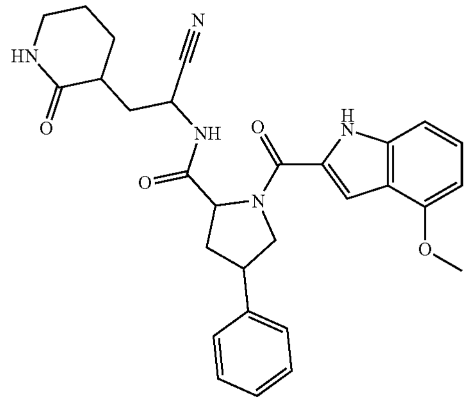 [SMILES: COc1cccc2[nH]c(C(=O)N3CC(c4ccccc4)CC3C(=O)NC(C#N)CC3CCCNC3=O)cc12] |
| 611 | 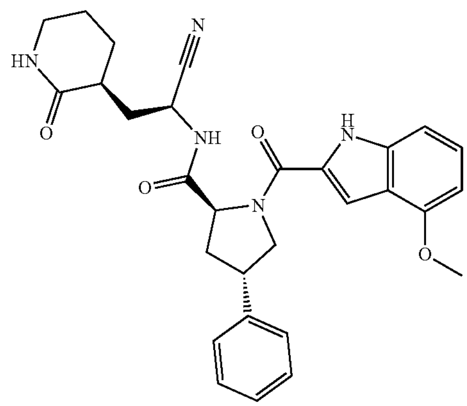 [SMILES: COc1cccc2[nH]c(C(=O)N3C[C@H](c4ccccc4)C[C@H]3C(=O)N[C@H](C#N)C[C@@H]3CCCNC3=O)cc12] |
| 612 | 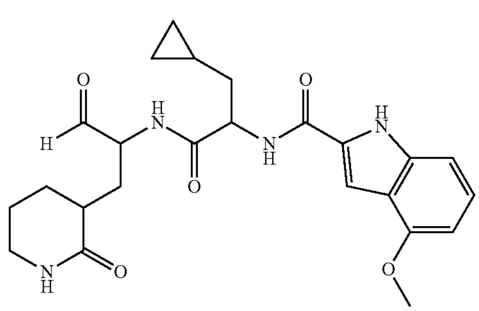 [SMILES: COc1cccc2[nH]c(C(=O)NC(CC3CC3)C(=O)NC(C=O)CC3CCCNC3=O)cc12] |

TABLE 1-continued

Exemplary compounds.

| Cmpd No. | Structure |
|---|---|
| 613 | 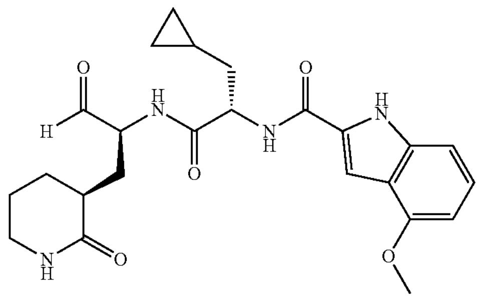 [SMILES: COc1cccc2[nH]c(C(=O)N[C@@H](CC3CC3)C(=O)N[C@H](C=O)C[C@@H]3CCCNC3=O)cc12] |
| 614 | 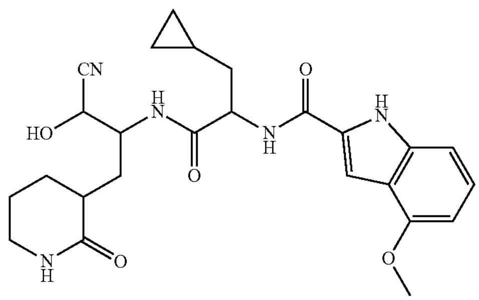 [SMILES: COc1cccc2[nH]c(C(=O)NC(CC3CC3)C(=O)NC(CC3CCCNC3=O)C(O)C#N)cc12] |
| 615 | 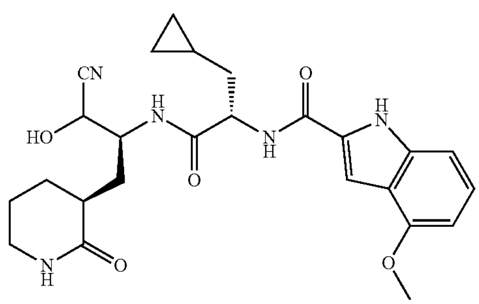 [SMILES: COc1cccc2[nH]c(C(=O)N[C@@H](CC3CC3)C(=O)N[C@@H](C[C@@H]3CCCNC3=O)C(O)C#N)cc12] |
| 616 | 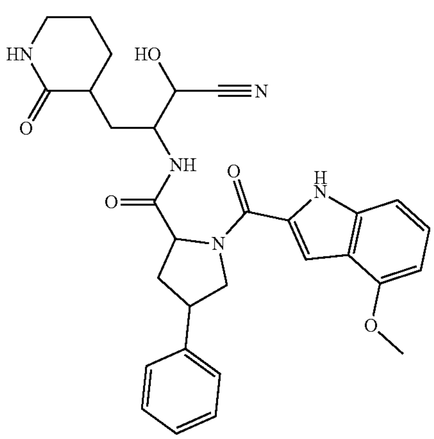 [SMILES: COc1cccc2[nH]c(C(=O)N3CC(c4ccccc4)CC3C(=O)NC(CC3CCCNC3=O)C(O)C#N)cc12] |

TABLE 1-continued

Exemplary compounds.

| Cmpd No. | Structure |
| --- | --- |
| 617 | 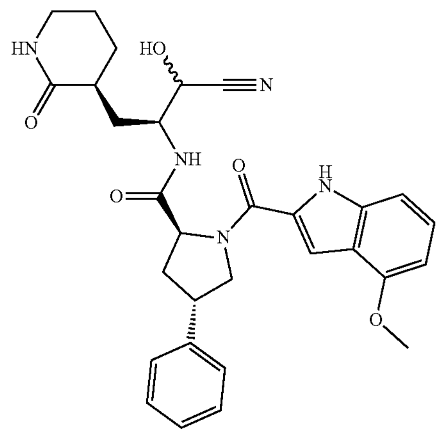 [SMILES: COc1cccc2[nH]c(C(=O)N3C[C@H](c4ccccc4)C[C@H]3C(=O)N[C@@H](C[C@@H]3CCCNC3=O)C(O)C#N)cc12] |
| 618 | 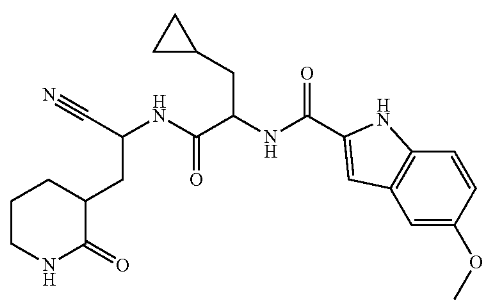 [SMILES: COc1ccc2[nH]c(C(=O)NC(CC3CC3)C(=O)NC(C#N)CC3CCCNC3=O)cc2c1] |
| 619 | 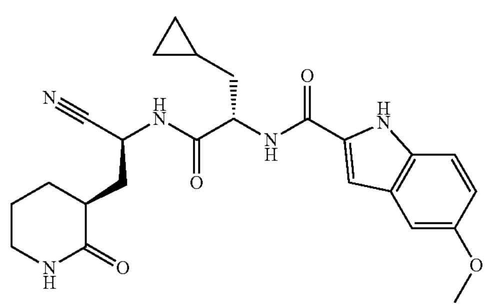 [SMILES: COc1ccc2[nH]c(C(=O)N[C@@H](CC3CC3)C(=O)N[C@H](C#N)C[C@@H]3CCCNC3=O)cc2c1] |
| 620 | 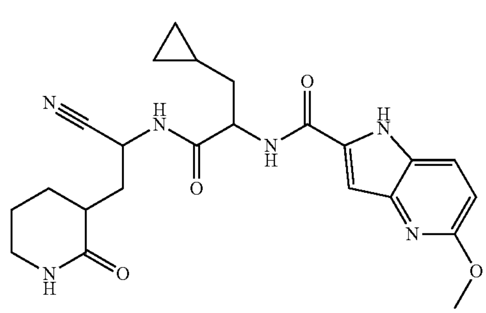 [SMILES: COc1ccc2[nH]c(C(=O)NC(CC3CC3)C(=O)NC(C#N)CC3CCCNC3=O)cc2n1] |

TABLE 1-continued
Exemplary compounds.
| Cmpd No. | Structure |
|---|---|
| 621 | 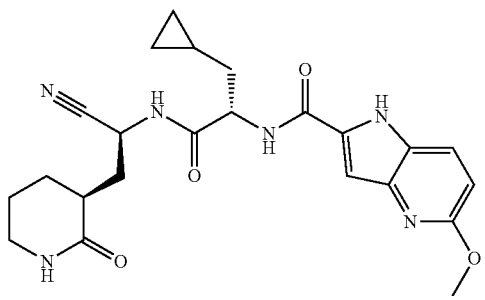 [SMILES: COc1ccc2[nH]c(C(=O)N[C@@H](CC3CC3)C(=O)N[C@H](C#N)C[C@@H]3CCCNC3=O)cc2n1] |
| 622 | 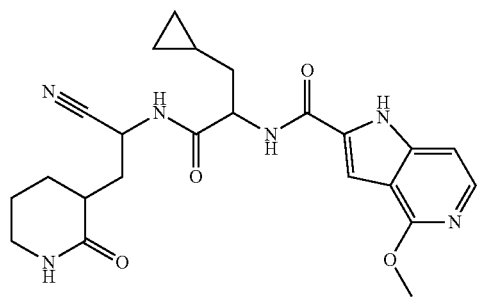 [SMILES: COc1nccc2[nH]c(C(=O)NC(CC3CC3)C(=O)NC(C#N)CC3CCCNC3=O)cc12] |
| 623 | 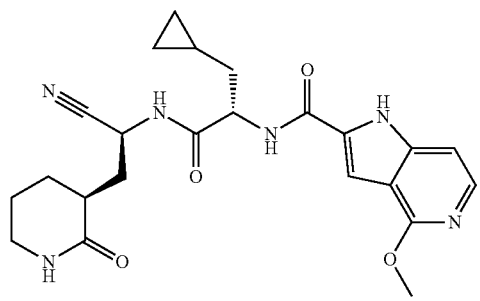 [SMILES: COc1nccc2[nH]c(C(=O)N[C@@H](CC3CC3)C(=O)N[C@H](C#N)C[C@@H]3CCCNC3=O)cc12] |
| 624 | 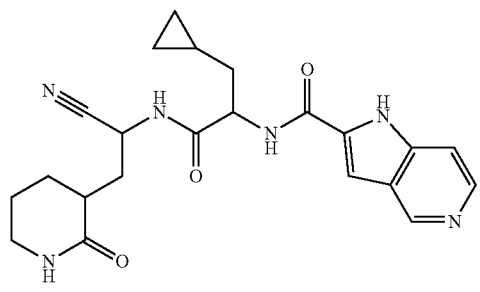 [SMILES: N#CC(CC1CCCNC1=O)NC(=O)C(CC1CC1)NC(=O)c1cc2cnccc2[nH]1] |
| 625 | 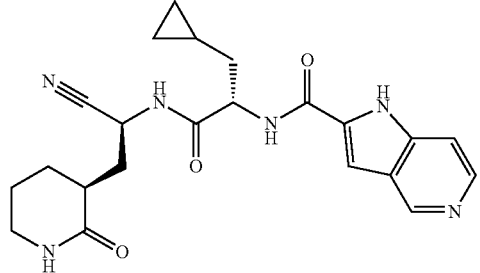 [SMILES: N#C[C@H](C[C@@H]1CCCNC1=O)NC(=O)[C@H](CC1CC1)NC(=O)c1cc2cnccc2[nH]1] |

TABLE 1-continued
Exemplary compounds.
| Cmpd No. | Structure |
|---|---|
| 626 | 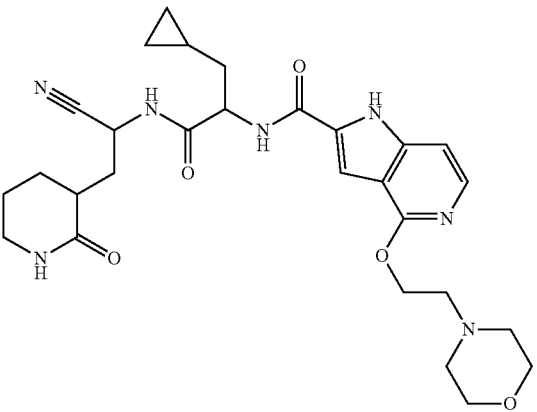 [SMILES: N#CC(CC1CCCNC1=O)NC(=O)C(CC1CC1)NC(=O)c1cc2c(OCCN3CCOCC3)nccc2[nH]1] |
| 627 | 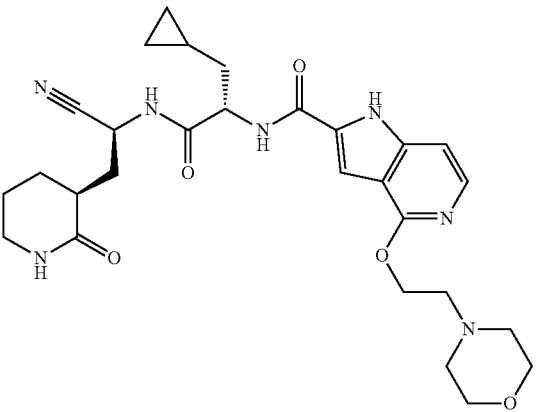 [SMILES: N#C[C@H](C[C@@H]1CCCNC1=O)NC(=O)[C@H](CC1CC1)NC(=O)c1cc2c(OCCN3CCOCC3)nccc2[nH]1] |
| 628 | 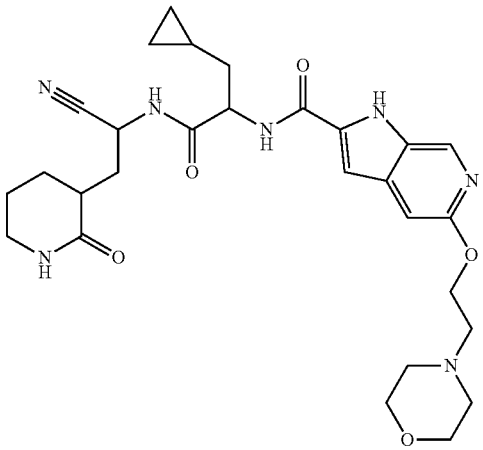 [SMILES: N#CC(CC1CCCNC1=O)NC(=O)C(CC1CC1)NC(=O)c1cc2cc(OCCN3CCOCC3)ncc2[nH]1] |

TABLE 1-continued
Exemplary compounds.
| Cmpd No. | Structure |
|---|---|
| 629 | 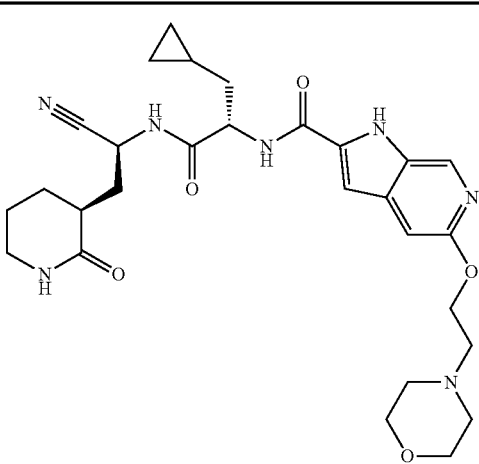 |
| 630 | 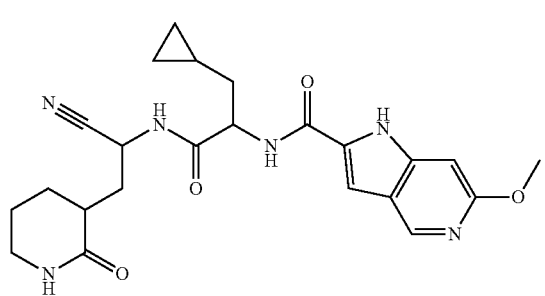 [SMILES: COc1cc2[nH]c(C(=O)NC(CC3CC3)C(=O)NC(C#N)CC3CCCNC3=O)cc2cn1] |
| 631 | 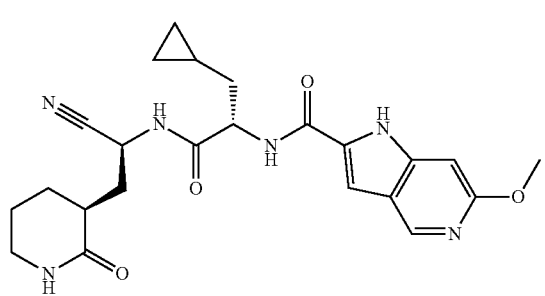 [SMILES: COc1cc2[nH]c(C(=O)N[C@@H](CC3CC3)C(=O)N[C@H](C#N)C[C@@H]3CCCNC3=O)cc2cn1] |
| 632 | 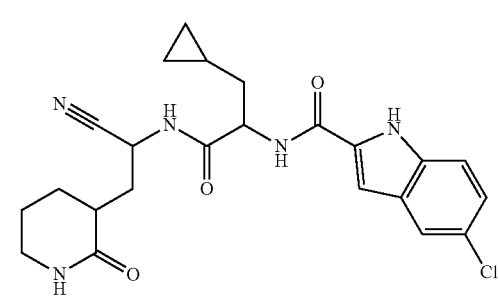 [SMILES: N#CC(CC1CCCNC1=O)NC(=O)C(CC1CC1)NC(=O)c1cc2cc(Cl)ccc2[nH]1] |

TABLE 1-continued
Exemplary compounds.
| Cmpd No. | Structure |
|---|---|
| 633 | 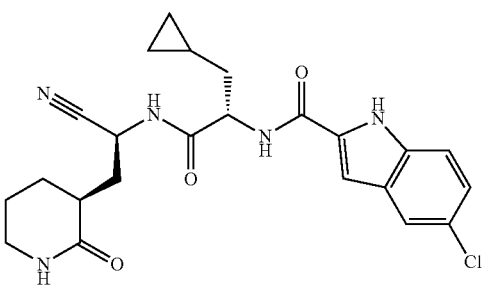 [SMILES: N#C[C@H](C[C@@H]1CCCNC1=O)NC(=O)[C@H](CC1CC1)NC(=O)c1cc2cc(Cl)ccc2[nH]1] |
| 634 | 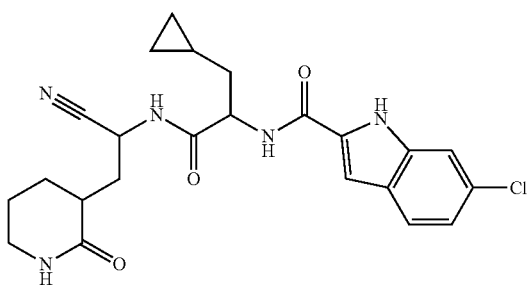 [SMILES: N#CC(CC1CCCNC1=O)NC(=O)C(CC1CC1)NC(=O)c1cc2ccc(Cl)cc2[nH]1] |
| 635 | 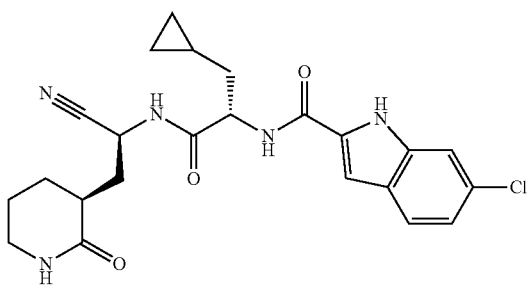 [SMILES: N#C[C@H](C[C@@H]1CCCNC1=O)NC(=O)[C@H](CC1CC1)NC(=O)c1cc2ccc(Cl)cc2[nH]1] |
| 636 | 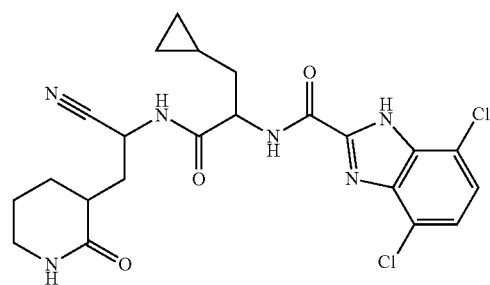 [SMILES: N#CC(CC1CCCNC1=O)NC(=O)C(CC1CC1)NC(=O)c1nc2c(Cl)ccc(Cl)c2[nH]1] |
| 637 | 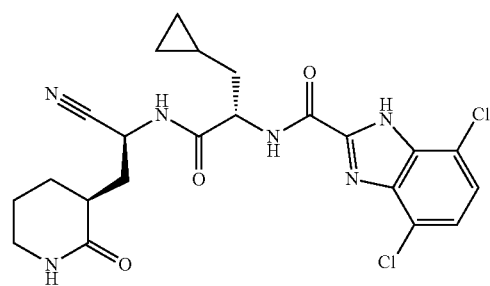 [SMILES: N#C[C@H](C[C@@H]1CCCNC1=O)NC(=O)[C@H](CC1CC1)NC(=O)c1nc2c(Cl)ccc(Cl)c2[nH]1] |

TABLE 1-continued
Exemplary compounds.
| Cmpd No. | Structure |
|---|---|
| 638 | 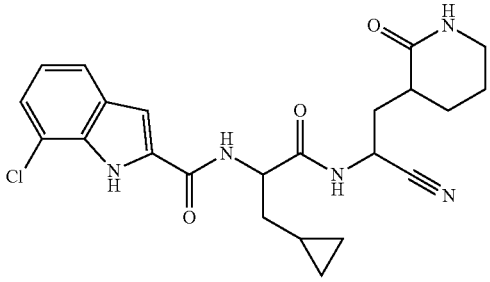 [SMILES: N#CC(CC1CCCNC1=O)NC(=O)C(CC1CC1)NC(=O)c1cc2cccc(Cl)c2[nH]1] |
| 639 | 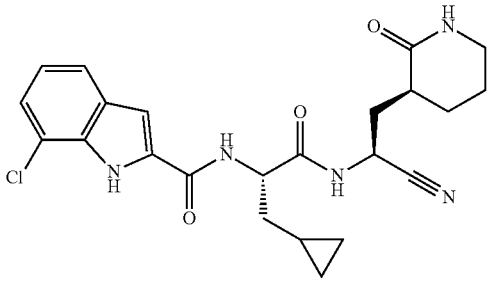 [SMILES: N#C[C@H](C[C@@H]1CCCNC1=O)NC(=O)[C@H](CC1CC1)NC(=O)c1cc2cccc(Cl)c2[nH]1] |
| 640 | 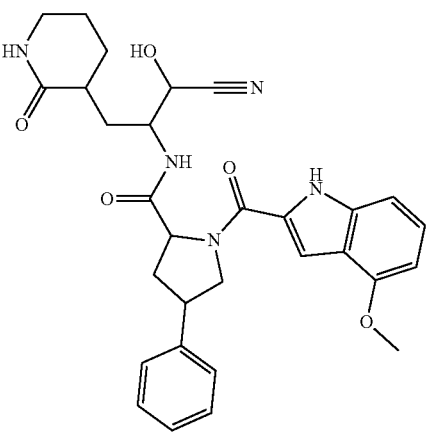 [SMILES: COc1cccc2[nH]c(C(=O)N3CC(c4ccccc4)CC3C(=O)NC(CC3CCCNC3=O)C(O)C#N)cc12] |
| 641 | 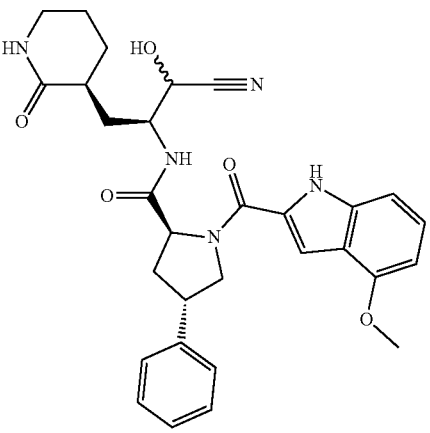 [SMILES: COc1cccc2[nH]c(C(=O)N3C[C@H](c4ccccc4)C[C@H]3C(=O)N[C@@H](C[C@@H]3CCCNC3=O)C(O)C#N)cc12] |

TABLE 1-continued

Exemplary compounds.

| Cmpd No. | Structure |
|---|---|
| 642 | 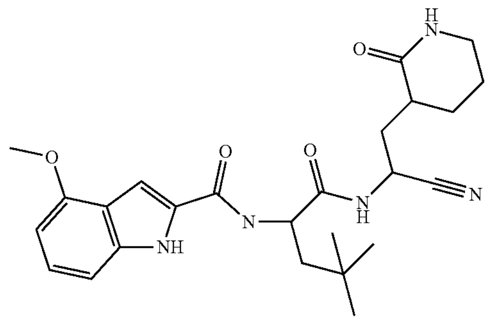 [SMILES: COc1cccc2[nH]c(C(=O)NC(CC(C)(C)C)C(=O)NC(C#N)CC3CCCNC3=O)cc12] |
| 643 | 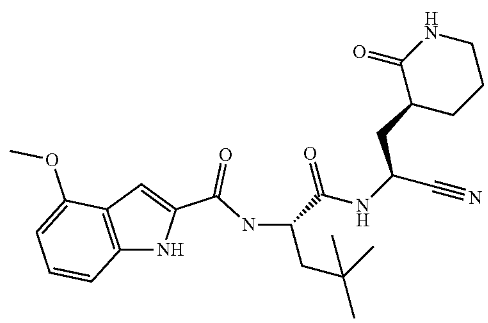 [SMILES: COc1cccc2[nH]c(C(=O)N[C@@H](CC(C)(C)C)C(=O)N[C@H](C#N)C[C@@H]3CCCNC3=O)cc12] |
| 644 | 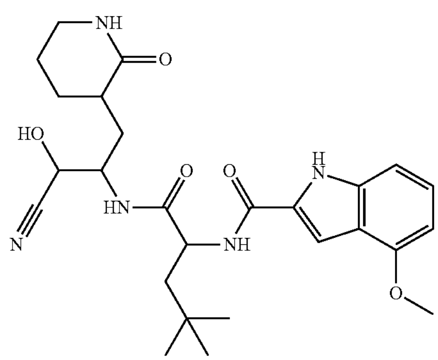 [SMILES: COc1cccc2[nH]c(C(=O)NC(CC(C)(C)C)C(=O)NC(CC3CCCNC3=O)C(O)C#N)cc12] |
| 645 | 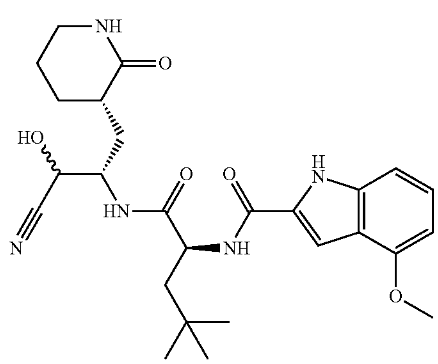 [SMILES: COc1cccc2[nH]c(C(=O)N[C@@H](CC(C)(C)C)C(=O)N[C@@H](C[C@@H]3CCCNC3=O)C(O)C#N)cc12] |

TABLE 1-continued

Exemplary compounds.

| Cmpd No. | Structure |
|---|---|
| 646 | 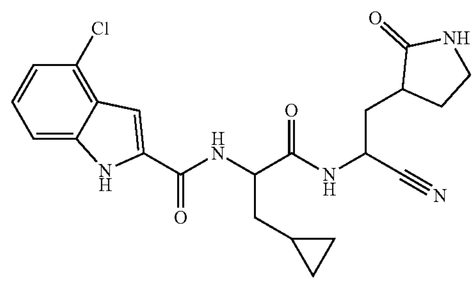 [SMILES: N#CC(CC1CCNC1=O)NC(=O)C(CC1CC1)NC(=O)c1cc2c(Cl)cccc2[nH]1] |
| 647 | 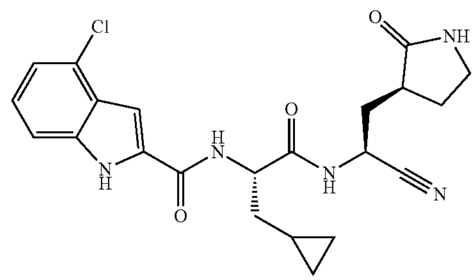 [SMILES: N#C[C@H](C[C@@H]1CCNC1=O)NC(=O)[C@H](CC1CC1)NC(=O)c1cc2c(Cl)cccc2[nH]1] |
| 648 | 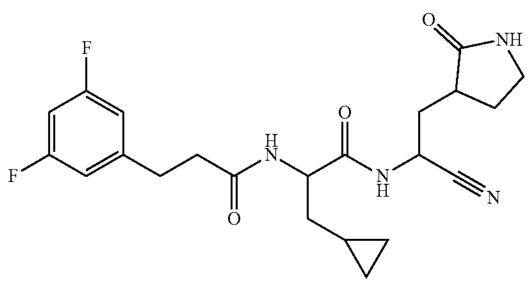 [SMILES: N#CC(CC1CCNC1=O)NC(=O)C(CC1CC1)NC(=O)CCc1cc(F)cc(F)c1] |
| 649 | 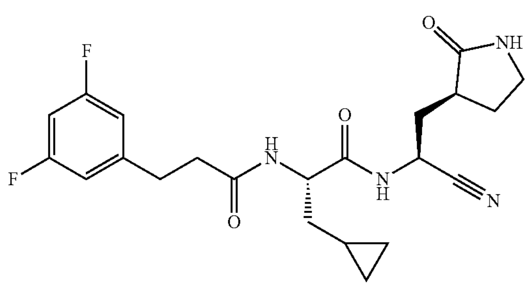 [SMILES: N#C[C@H](C[C@@H]1CCNC1=O)NC(=O)[C@H](CC1CC1)NC(=O)CCc1cc(F)cc(F)c1] |
| 650 | 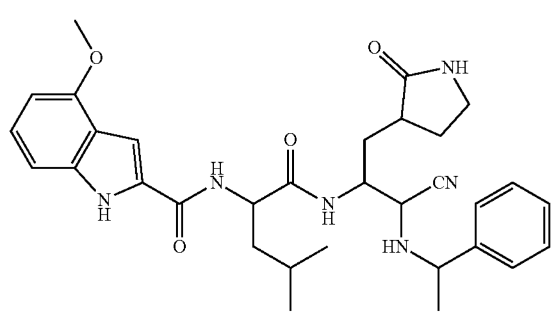 [SMILES: COc1cccc2[nH]c(C(=O)NC(CC(C)C)C(=O)NC(CC3CCNC3=O)C(C#N)NC(C)c3ccccc3)cc12] |

TABLE 1-continued
Exemplary compounds.
| Cmpd No. | Structure |
|---|---|
| 651 | 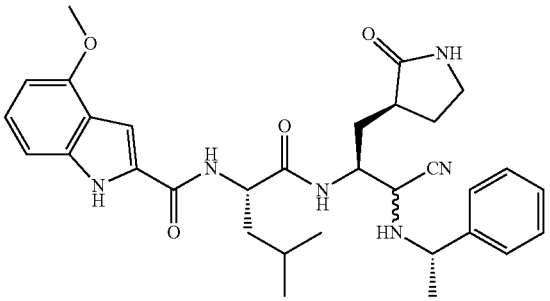 [SMILES: COc1cccc2[nH]c(C(=O)N[C@@H](CC(C)C)C(=O)N[C@@H](C[C@@H]3CCNC3=O)C(C#N)N[C@@H](C)c3ccccc3)cc12] |
| 652 | 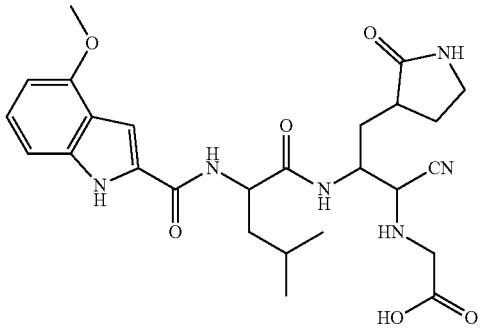 [SMILES: COc1cccc2[nH]c(C(=O)NC(CC(C)C)C(=O)NC(CC3CCNC3=O)C(C#N)NCC(=O)O)cc12] |
| 653 | 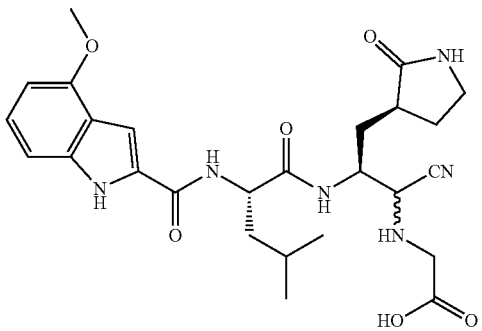 [SMILES: COc1cccc2[nH]c(C(=O)N[C@@H](CC(C)C)C(=O)N[C@@H](C[C@@H]3CCNC3=O)C(C#N)NCC(=O)O)cc12] |
| 654 | 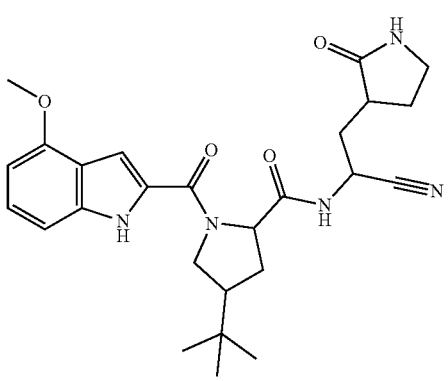 [SMILES: COc1cccc2[nH]c(C(=O)N3CC(C(C)(C)C)CC3C(=O)NC(C#N)CC3CCNC3=O)cc12] |

TABLE 1-continued

Exemplary compounds.

| Cmpd No. | Structure |
|---|---|
| 655 | 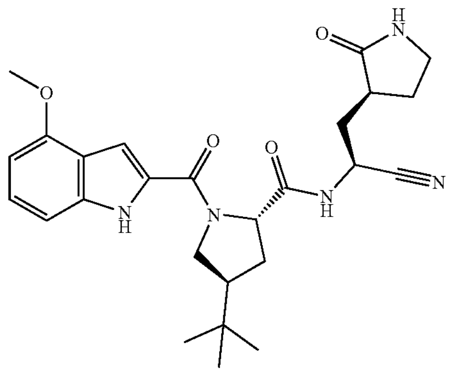 [SMILES: COc1cccc2[nH]c(C(=O)N3C[C@H](C(C)(C)C)C[C@H]3C(=O)N[C@H](C#N)C[C@@H]3CCNC3=O)cc12] |
| 656 | 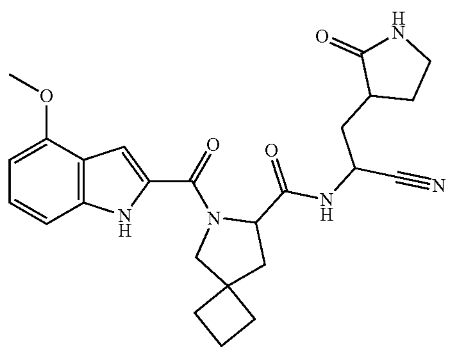 [SMILES: COc1cccc2[nH]c(C(=O)N3CC4(CCC4)CC3C(=O)NC(C#N)CC3CCNC3=O)cc12] |
| 657 | 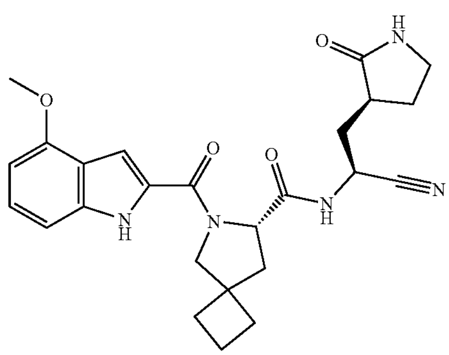 [SMILES: COc1cccc2[nH]c(C(=O)N3CC4(CCC4)C[C@H]3C(=O)N[C@H](C#N)C[C@@H]3CCNC3=O)cc12] |
| 658 | 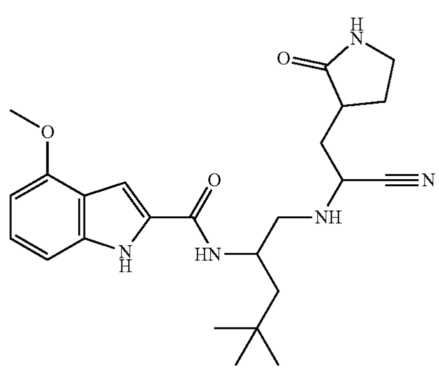 [SMILES: COc1cccc2[nH]c(C(=O)NC(CNC(C#N)CC3CCNC3=O)CC(C)(C)C)cc12] |

TABLE 1-continued

Exemplary compounds.

| Cmpd No. | Structure |
|---|---|
| 659 | 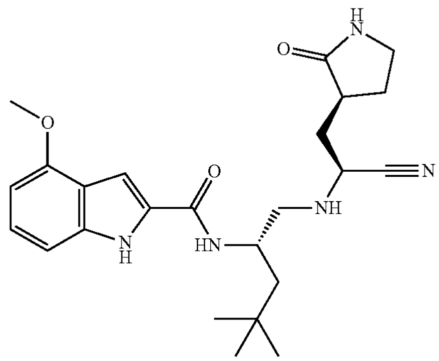 [SMILES: COc1cccc2[nH]c(C(=O)N[C@H](CN[C@H](C#N)C[C@@H]3CCNC3=O)CC(C)(C)C)cc12] |
| 660 | 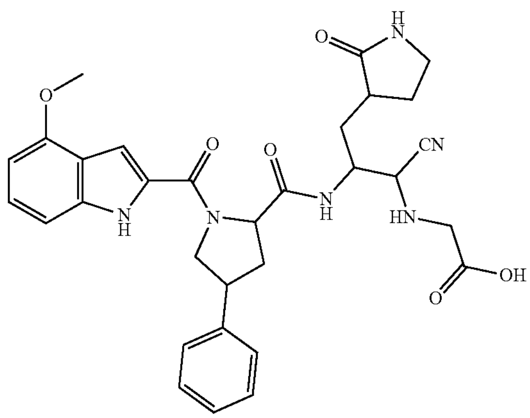 [SMILES: COc1cccc2[nH]c(C(=O)N3CC(c4ccccc4)CC3C(=O)NC(CC3CCNC3=O)C(C#N)NCC(=O)O)cc12] |
| 661 | 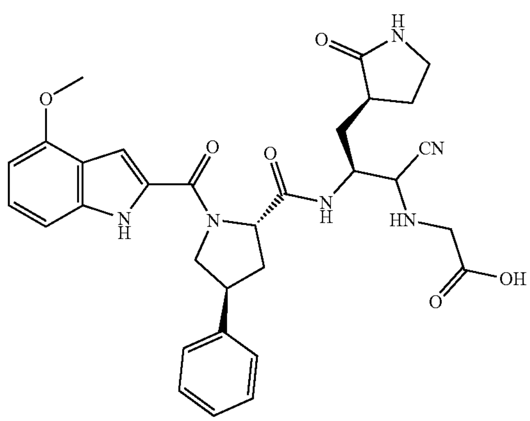 [SMILES: COc1cccc2[nH]c(C(=O)N3C[C@H](c4ccccc4)C[C@H]3C(=O)N[C@@H](C[C@@H]3CCNC3=O)C(C#N)NCC(=O)O)cc12] |
| 666 | 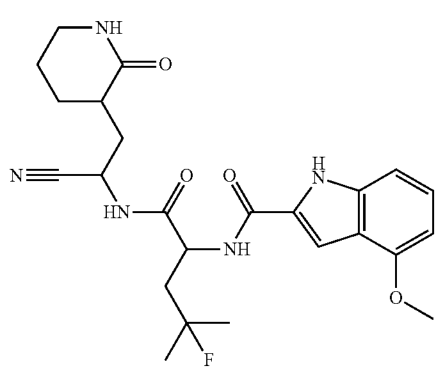 [SMILES: COc1cccc2[nH]c(C(=O)NC(CC(C)(C)F)C(=O)NC(C#N)CC3CCCNC3=O)cc12] |

351
TABLE 1-continued
Exemplary compounds.
| Cmpd No. | Structure |
|---|---|
| 667 | 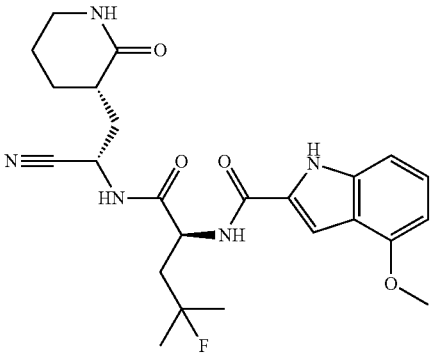 [SMILES: COc1cccc2[nH]c(C(=O)N[C@@H](CC(C)(C)F)C(=O)N[C@H](C#N)C[C@@H]3CCCNC3=O)cc12] |
| 668 | 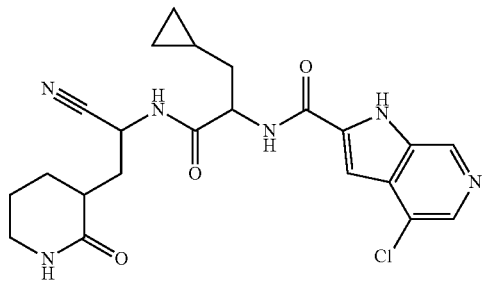 [SMILES: N#CC(CC1CCCNC1=O)NC(=O)C(CC1CC1)NC(=O)c1cc2c(Cl)cncc2[nH]1] |
| 669 | 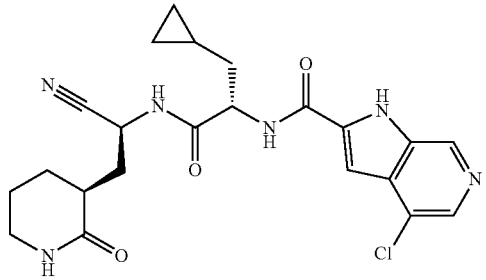 [SMILES: N#C[C@H](C[C@@H]1CCCNC1=O)NC(=O)[C@H](CC1CC1)NC(=O)c1cc2c(Cl)cncc2[nH]1] |
| 670 | 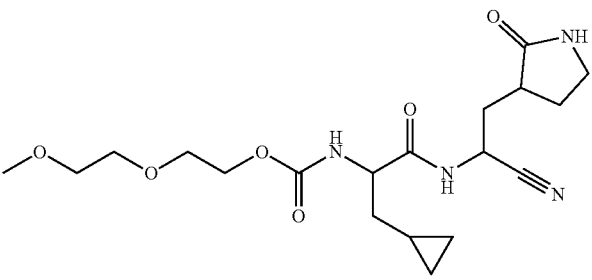 [SMILES: COCCOCCOC(=O)NC(CC1CC1)C(=O)NC(C#N)CC1CCNC1=O] |
| 671 | 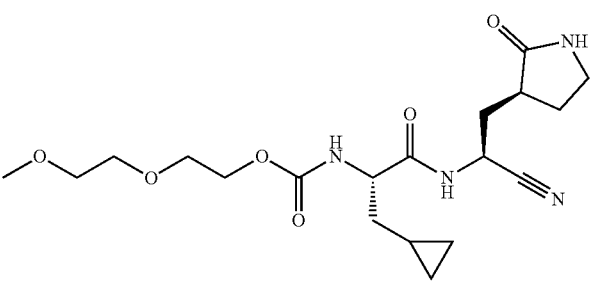 [SMILES: COCCOCCOC(=O)N[C@@H](CC1CC1)C(=O)N[C@H](C#N)C[C@@H]1CCNC1=O] |

TABLE 1-continued

Exemplary compounds.

| Cmpd No. | Structure |
|---|---|
| 672 | 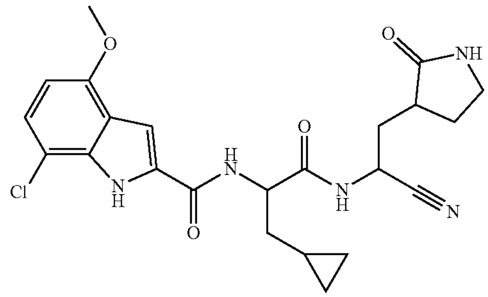 [SMILES: COc1ccc(Cl)c2[nH]c(C(=O)NC(CC3CC3)C(=O)NC(C#N)CC3CCNC3=O)cc12] |
| 673 | 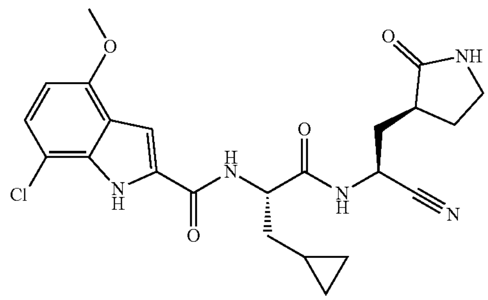 [SMILES: COc1ccc(Cl)c2[nH]c(C(=O)N[C@@H](CC3CC3)C(=O)N[C@H](C#N)C[C@@H]3CCNC3=O)cc12] |
| 674 | 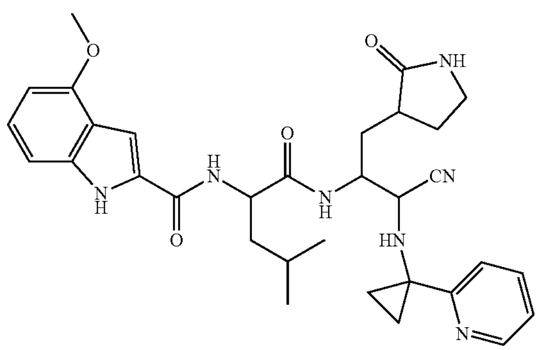 [SMILES: COc1cccc2[nH]c(C(=O)NC(CC(C)C)C(=O)NC(CC3CCNC3=O)C(C#N)NC3(c4ccccn4)CC3)cc12] |
| 675 | 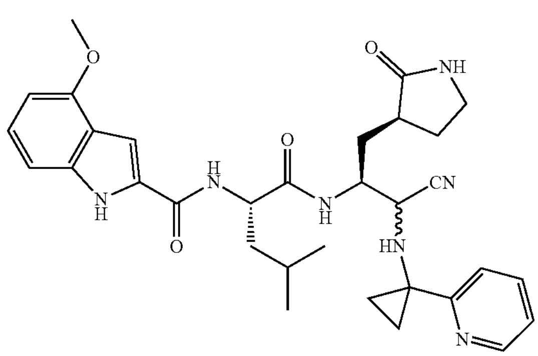 [SMILES: COc1cccc2[nH]c(C(=O)N[C@@H](CC(C)C)C(=O)N[C@@H](C[C@@H]3CCNC3=O)C(C#N)NC3(c4ccccn4)CC3)cc12] |

TABLE 1-continued

Exemplary compounds.

| Cmpd No. | Structure |
| --- | --- |
| 676 | 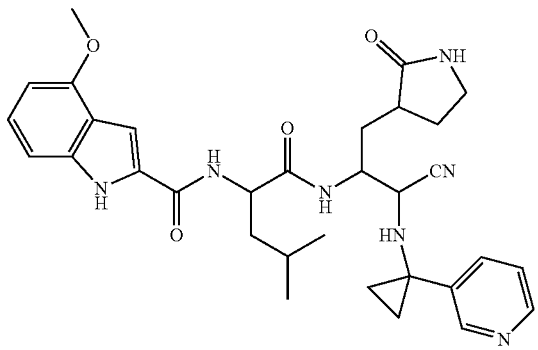 [SMILES: COc1cccc2[nH]c(C(=O)NC(CC(C)C)C(=O)NC(CC3CCNC3=O)C(C#N)NC3(c4cccnc4)CC3)cc12] |
| 677 | 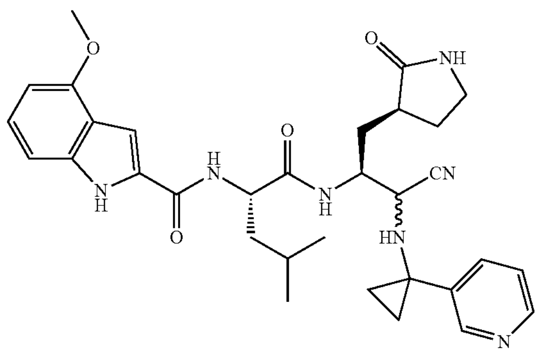 [SMILES: COc1cccc2[nH]c(C(=O)N[C@@H](CC(C)C)C(=O)N[C@@H](C[C@@H]3CCNC3=O)C(C#N)NC3(c4cccnc4)CC3)cc12] |
| 678 | 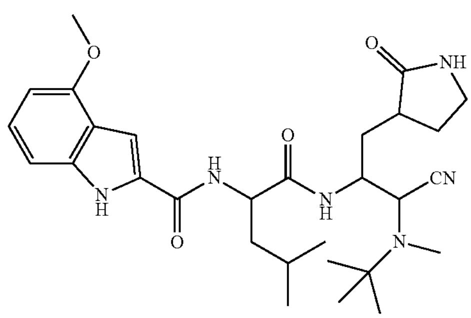 [SMILES: COc1cccc2[nH]c(C(=O)NC(CC(C)C)C(=O)NC(CC3CCNC3=O)C(C#N)N(C)C(C)(C)C)cc12] |
| 679 | 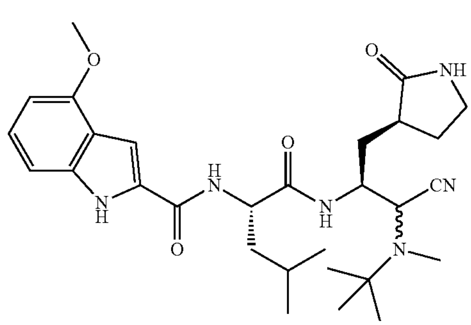 [SMILES: COc1cccc2[nH]c(C(=O)N[C@@H](CC(C)C)C(=O)N[C@@H](C[C@@H]3CCNC3=O)C(C#N)N(C)C(C)(C)C)cc12] |

TABLE 1-continued

Exemplary compounds.

| Cmpd No. | Structure |
|---|---|
| 680 | 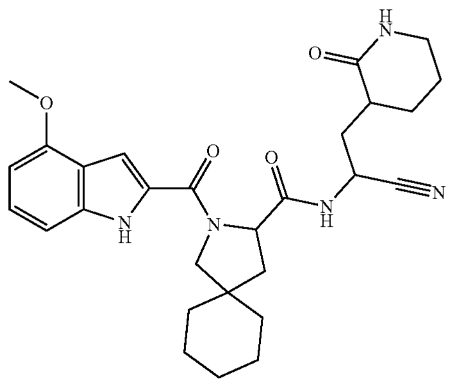 [SMILES: COc1cccc2[nH]c(C(=O)N3CC4(CCCCC4)CC3C(=O)NC(C#N)CC3CCCNC3=O)cc12] |
| 681 | 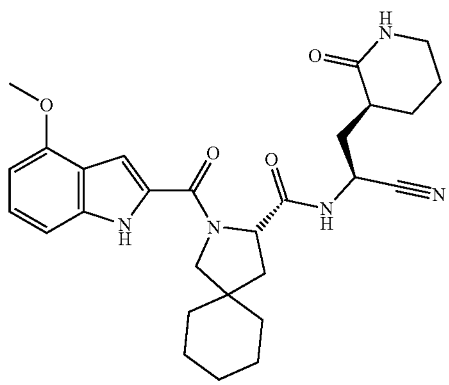 |
| 682 | 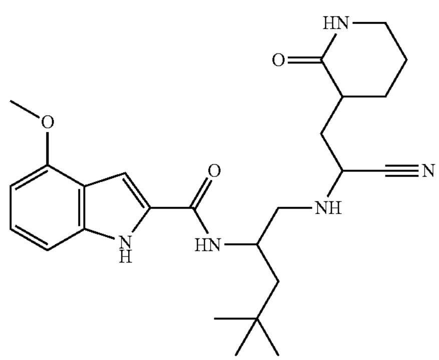 [SMILES: COc1cccc2[nH]c(C(=O)NC(CNC(C#N)CC3CCCNC3=O)CC(C)(C)C)cc12] |
| 683 | 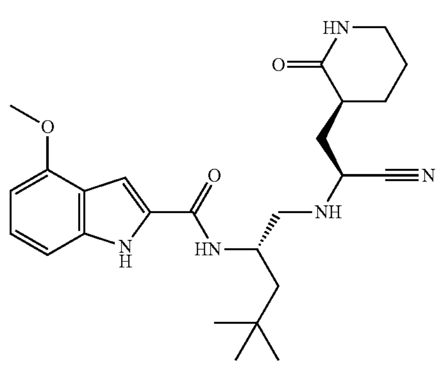 [SMILES: COc1cccc2[nH]c(C(=O)N[C@H](CN[C@H](C#N)C[C@@H]3CCCNC3=O)CC(C)(C)C)cc12] |

TABLE 1-continued
Exemplary compounds.
| Cmpd No. | Structure |
|---|---|
| 686 | 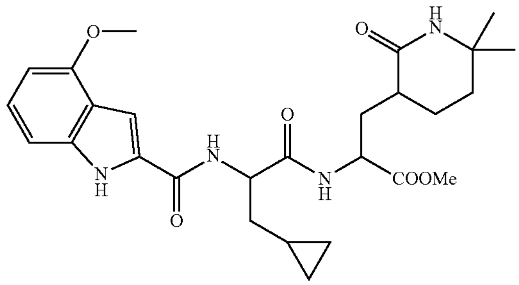 [SMILES: COC(=O)C(CC1CCC(C)(C)NC1=O)NC(=O)C(CC1CC1)NC(=O)c1cc2c(OC)cccc2[nH]1] |
| 687 | 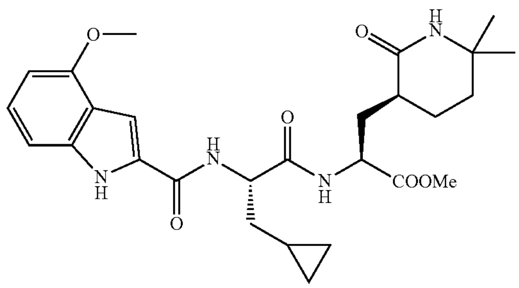 [SMILES: COC(=O)[C@H](C[C@@H]1CCC(C)(C)NC1=O)NC(=O)[C@H](CC1CC1)NC(=O)c1cc2c(OC)cccc2[nH]1] |
| 688 | 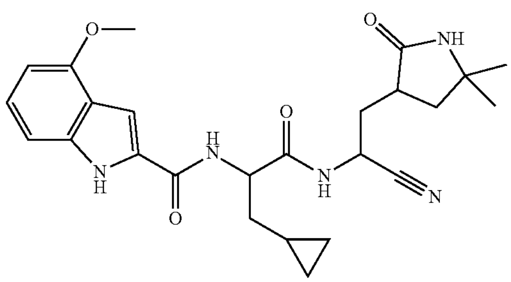 [SMILES: COc1cccc2[nH]c(C(=O)NC(CC3CC3)C(=O)NC(C#N)CC3CC(C)(C)NC3=O)cc12] |
| 689 | 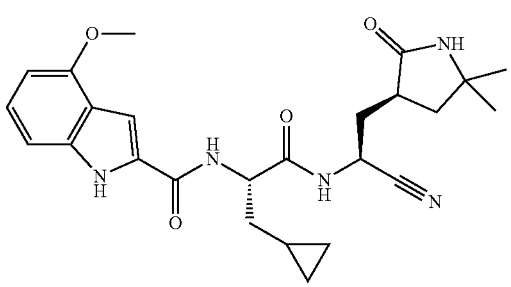 [SMILES: COc1cccc2[nH]c(C(=O)N[C@@H](CC3CC3)C(=O)N[C@H](C#N)C[C@@H]3CC(C)(C)NC3=O)cc12] |
| 690 | 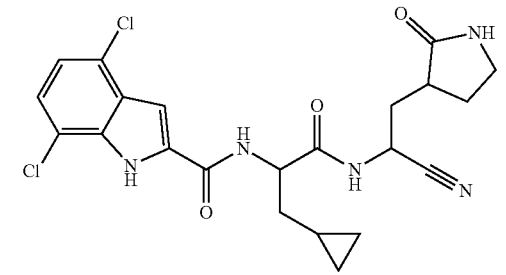 [SMILES: N#CC(CC1CCNC1=O)NC(=O)C(CC1CC1)NC(=O)c1cc2c(Cl)ccc(Cl)c2[nH]1] |

TABLE 1-continued

| Cmpd No. | Structure |
|---|---|
| 691 | 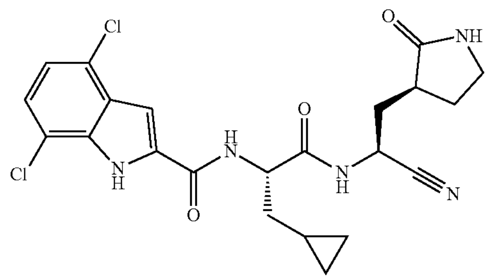 [SMILES: N#C[C@H](C[C@@H]1CCNC1=O)NC(=O)[C@H](CC1CC1)NC(=O)c1cc2c(Cl)ccc(Cl)c2[nH]1] |
| 692 | 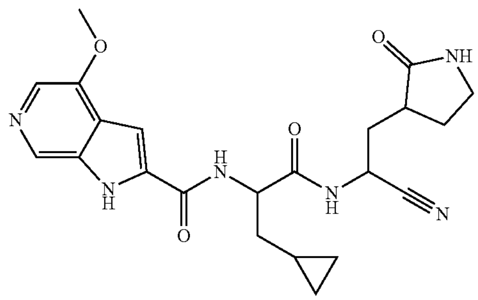 |
| 693 | 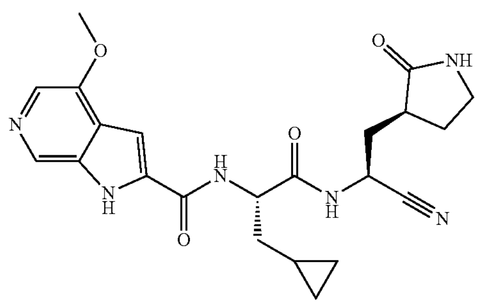 |
| 694 | 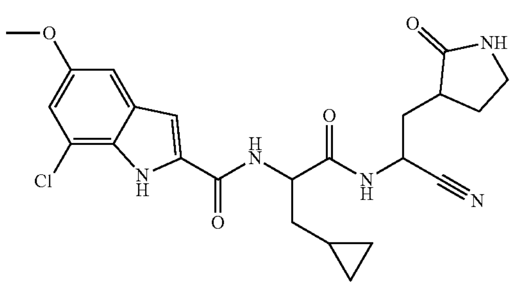 [SMILES: COc1cc(Cl)c2[nH]c(C(=O)NC(CC3CC3)C(=O)NC(C#N)CC3CCNC3=O)cc2c1] |
| 695 | 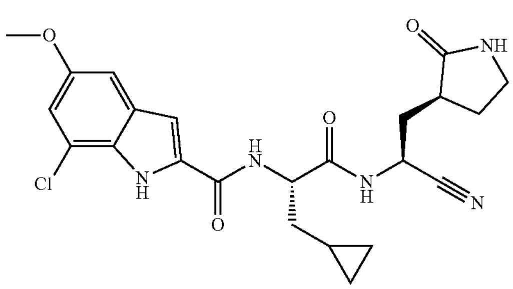 [SMILES: COc1cc(Cl)c2[nH]c(C(=O)N[C@@H](CC3CC3)C(=O)N[C@H](C#N)C[C@@H]3CCNC3=O)cc2c1] |

TABLE 1-continued

Exemplary compounds.

| Cmpd No. | Structure |
|---|---|
| 696 | 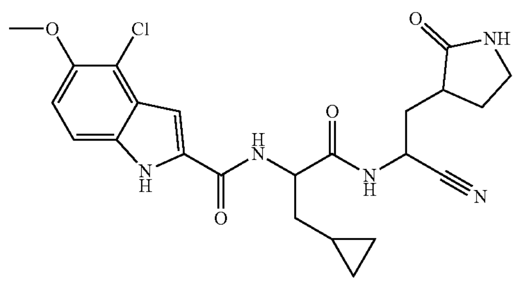 |
| 697 | 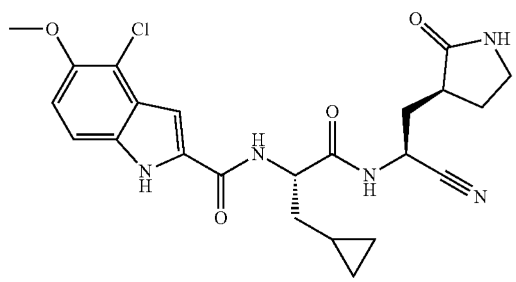 [SMILES: COc1ccc2[nH]c(C(=O)N[C@@H](CC3CC3)C(=O)N[C@H](C#N)C[C@@H]3CCNC3=O)cc2c1Cl] |
| 698 | 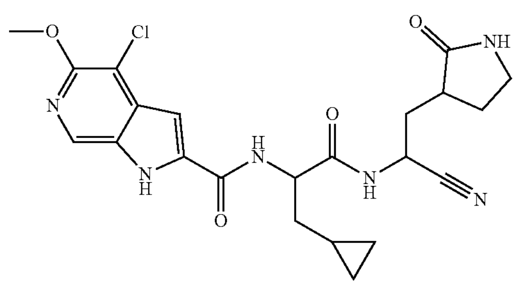 [SMILES: COc1ncc2[nH]c(C(=O)NC(CC3CC3)C(=O)NC(C#N)CC3CCNC3=O)cc2c1Cl] |
| 699 | 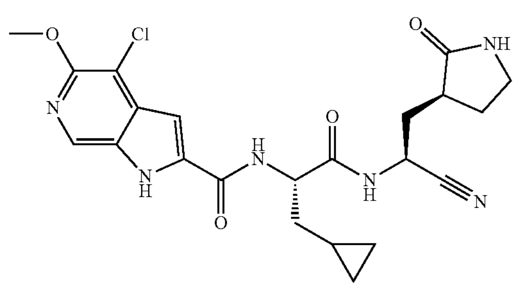 [SMILES: COc1ncc2[nH]c(C(=O)N[C@@H](CC3CC3)C(=O)N[C@H](C#N)C[C@@H]3CCNC3=O)cc2c1Cl] |
| 700 | 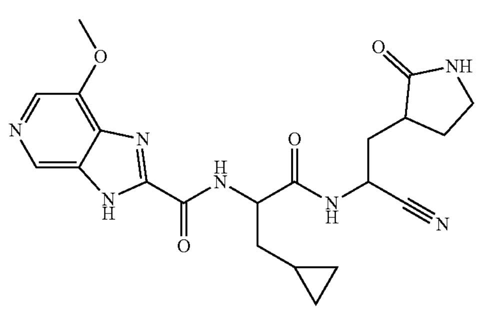 [SMILES: COc1cncc2[nH]c(C(=O)NC(CC3CC3)C(=O)NC(C#N)CC3CCNC3=O)nc12] |

TABLE 1-continued
Exemplary compounds.
| Cmpd No. | Structure |
|---|---|
| 701 | 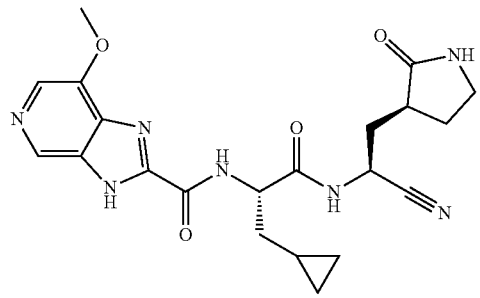 [SMILES: COc1cncc2[nH]c(C(=O)N[C@@H](CC3CC3)C(=O)N[C@H](C#N)C[C@@H]3CCNC3=O)nc12] |
| 702 | 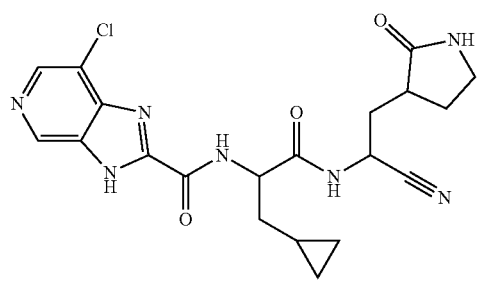 [SMILES: N#CC(CC1CCNC1=O)NC(=O)C(CC1CC1)NC(=O)c1nc2c(Cl)cncc2[nH]1] |
| 703 | 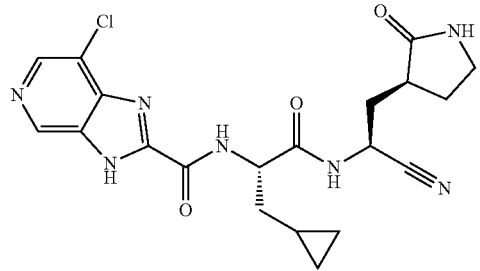 [SMILES: N#C[C@H](C[C@@H]1CCNC1=O)NC(=O)[C@H](CC1CC1)NC(=O)c1nc2c(Cl)cncc2[nH]1] |
| 704 | 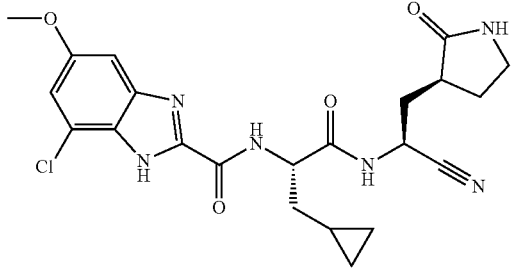 [SMILES: COc1cc(Cl)c2[nH]c(C(=O)N[C@@H](CC3CC3)C(=O)N[C@H](C#N)C[C@@H]3CCNC3=O)nc2c1] |
| 705 | 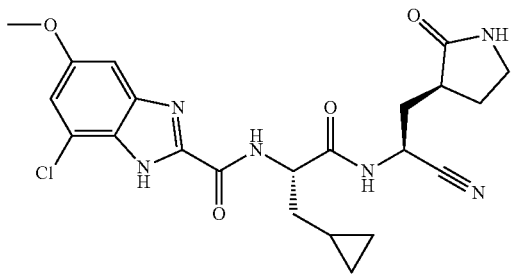 [SMILES: COc1cc(Cl)c2[nH]c(C(=O)N[C@@H](CC3CC3)C(=O)N[C@H](C#N)C[C@@H]3CCNC3=O)nc2c1] |

TABLE 1-continued

Exemplary compounds.

| Cmpd No. | Structure |
|---|---|
| 706 | 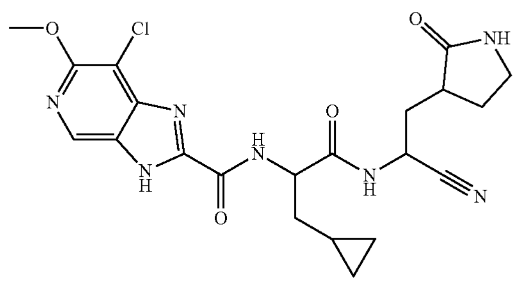 [SMILES: COc1ncc2[nH]c(C(=O)NC(CC3CC3)C(=O)NC(C#N)CC3CCNC3=O)nc2c1Cl] |
| 707 | 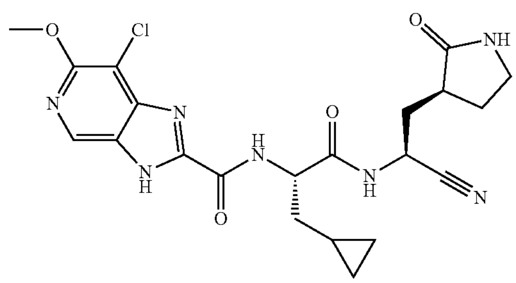 |
| 708 | 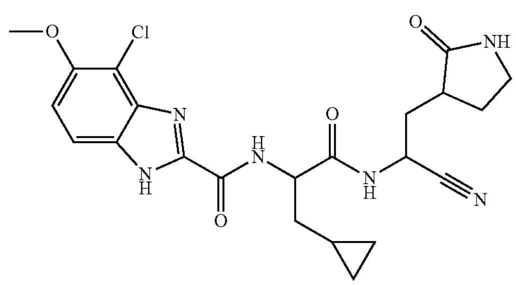 [SMILES: COc1ccc2[nH]c(C(=O)NC(CC3CC3)C(=O)NC(C#N)CC3CCNC3=O)nc2c1Cl] |
| 709 | 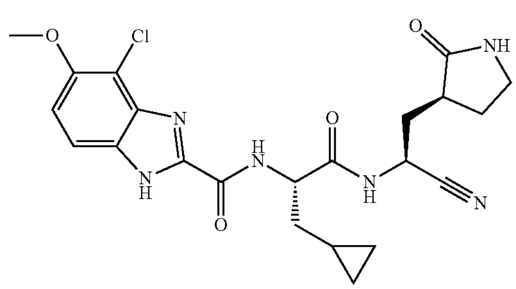 |
| 710 | 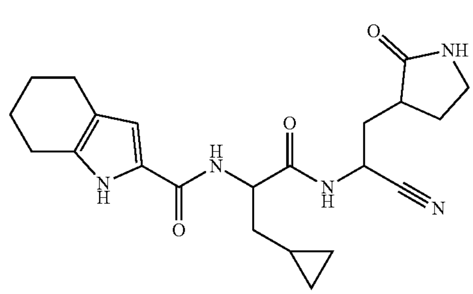 [SMILES: N#CC(CC1CCNC1=O)NC(=O)C(CC1CC1)NC(=O)c1cc2c([nH]1)CCCC2] |

TABLE 1-continued
Exemplary compounds.
| Cmpd No. | Structure |
|---|---|
| 711 | 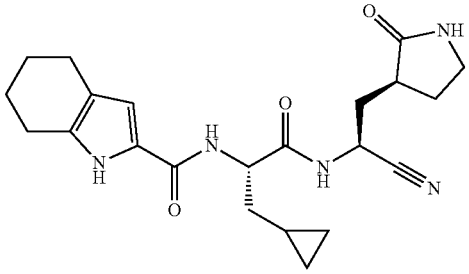 [SMILES: N#C[C@H](C[C@@H]1CCNC1=O)NC(=O)[C@H](CC1CC1)NC(=O)c1cc2c([nH]1)CCCC2] |
| 712 | 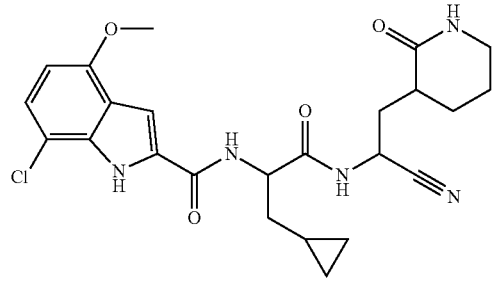 [SMILES: COc1ccc(Cl)c2[nH]c(C(=O)NC(CC3CC3)C(=O)NC(C#N)CC3CCCNC3=O)cc12] |
| 713 | 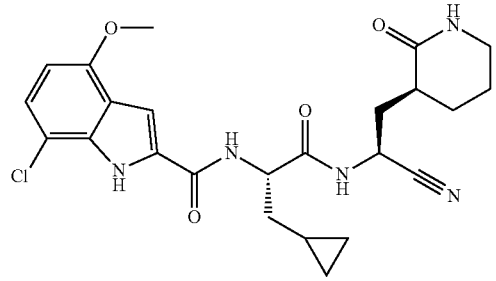 [SMILES: COc1ccc(Cl)c2[nH]c(C(=O)N[C@@H](CC3CC3)C(=O)N[C@H](C#N)C[C@@H]3CCCNC3=O)cc12] |
| 714 | 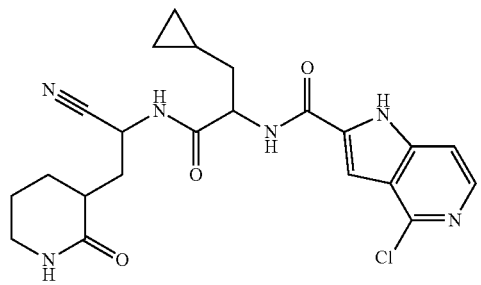 [SMILES: N#CC(CC1CCCNC1=O)NC(=O)C(CC1CC1)NC(=O)c1cc2c(Cl)nccc2[nH]1] |
| 715 | 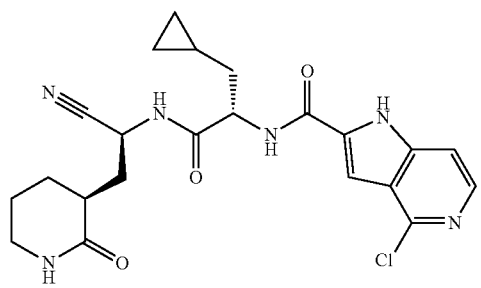 [SMILES: N#C[C@H](C[C@@H]1CCCNC1=O)NC(=O)[C@H](CC1CC1)NC(=O)c1cc2c(Cl)nccc2[nH]1] |

TABLE 1-continued
Exemplary compounds.
| Cmpd No. | Structure |
|---|---|
| 716 | 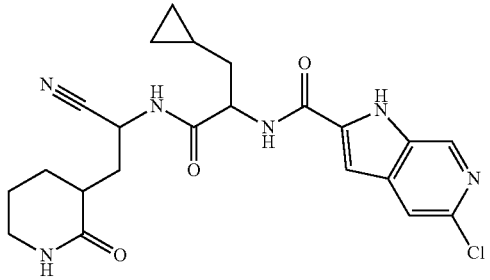 [SMILES: N#CC(CC1CCCNC1=O)NC(=O)C(CC1CC1)NC(=O)c1cc2cc(Cl)ncc2[nH]1] |
| 717 | 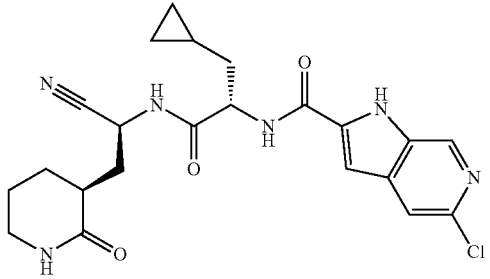 [SMILES: N#C[C@H](C[C@@H]1CCCNC1=O)NC(=O)[C@H](CC1CC1)NC(=O)c1cc2cc(Cl)ncc2[nH]1] |
| 718 | 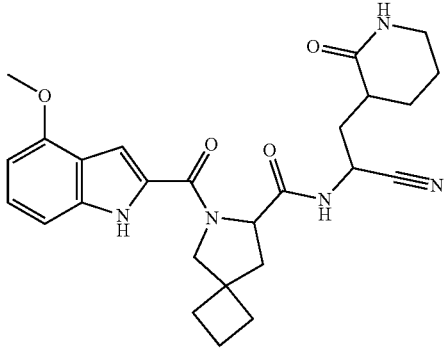 [SMILES: COc1cccc2[nH]c(C(=O)N3CC4(CCC4)CC3C(=O)NC(C#N)CC3CCCNC3=O)cc12] |
| 719 | 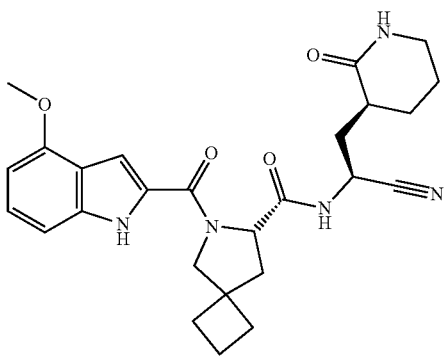 |

TABLE 1-continued
Exemplary compounds.
| Cmpd No. | Structure |
|---|---|
| 719A | 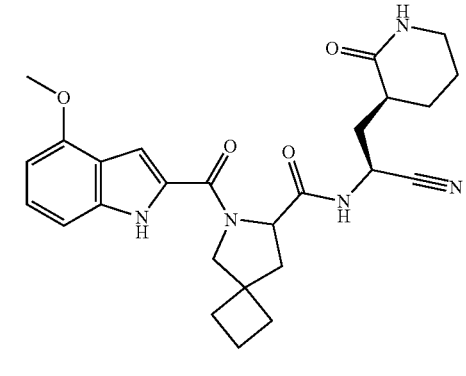 |
| 720 | 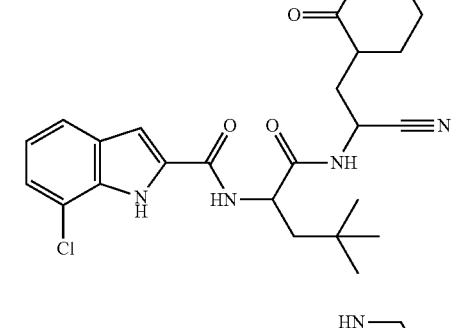 |
| 721 | 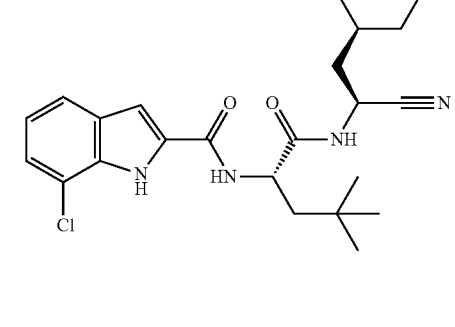 |
| 722 | 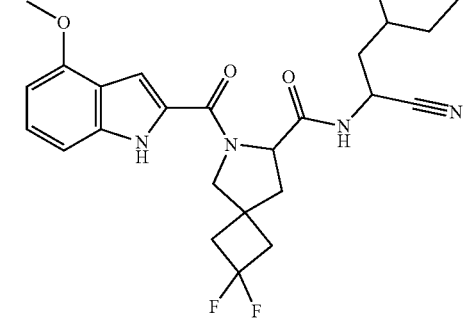 |

TABLE 1-continued
Exemplary compounds.
| Cmpd No. | Structure |
|---|---|
| 723 | 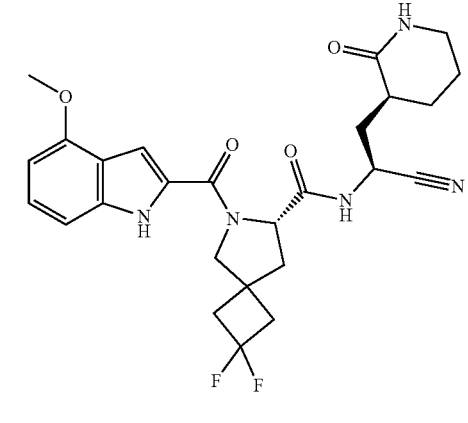 [SMILES: COc1cccc2[nH]c(C(=O)N3CC4(C[C@H]3C(=O)N[C@H](C#N)C[C@@H]3CCCNC3=O)CC(F)(F)C4)cc12] |
| 724 | 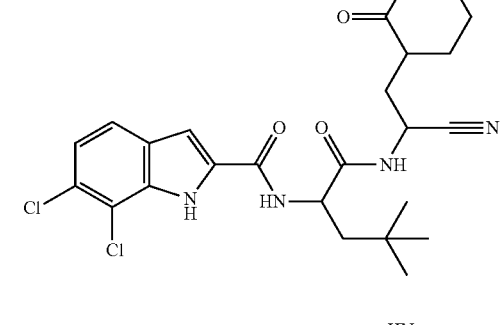 |
| 725 | 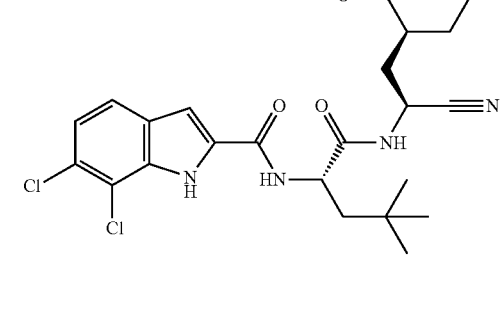 |
| 726 | 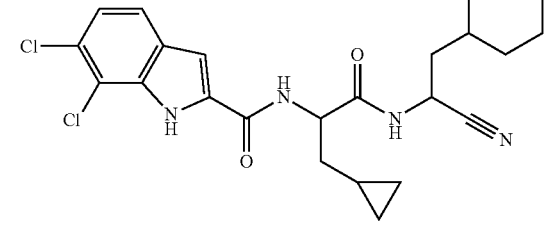 |

377

TABLE 1-continued

Exemplary compounds.

| Cmpd No. | Structure |
|---|---|
| 727 | 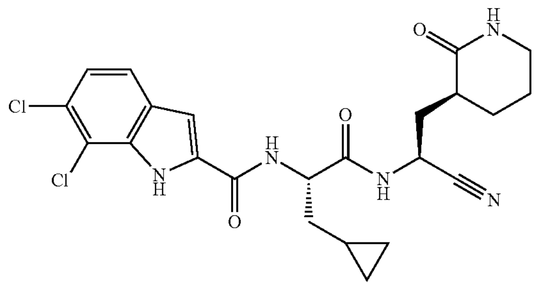 [SMILES: N#C[C@H](C[C@@H]1CCCNC1=O)NC(=O)[C@H](CC1CC1)NC(=O)c1cc2ccc(Cl)c(Cl)c2[nH]1] |
| 728 | 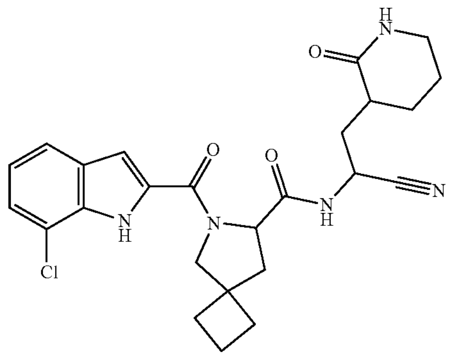 [SMILES: N#CC(CC1CCCNC1=O)NC(=O)C1CC2(CCC2)CN1C(=O)c1cc2cccc(Cl)c2[nH]1] |
| 729 | 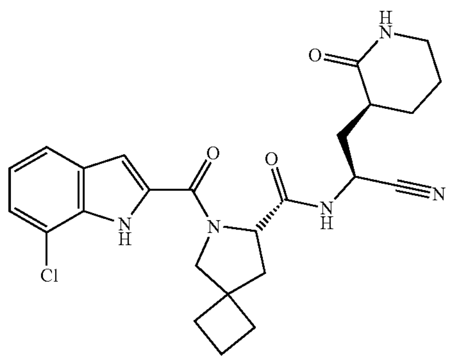 |
| 730 | 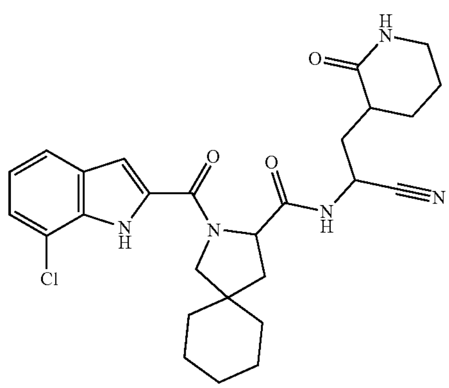 [SMILES: N#CC(CC1CCCNC1=O)NC(=O)C1CC2(CCCCC2)CN1C(=O)c1cc2cccc(Cl)c2[nH]1] |

TABLE 1-continued

Exemplary compounds.

| Cmpd No. | Structure |
|---|---|
| 731 | 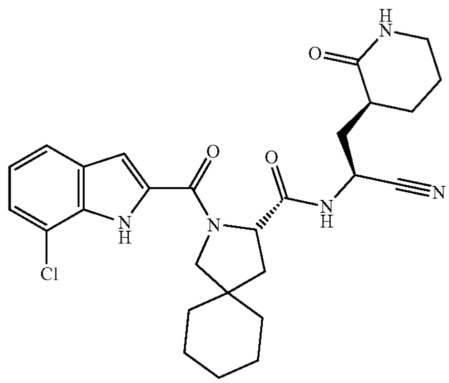 |
| 732 | 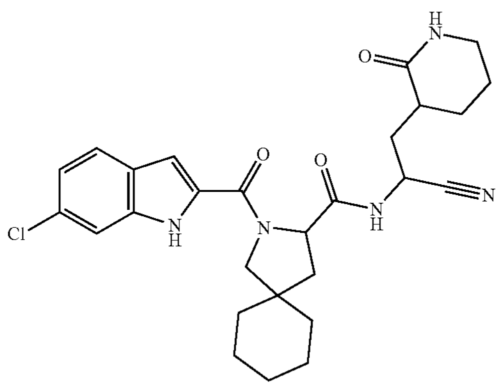 [SMILES: N#CC(CC1CCCNC1=O)NC(=O)C1CC2(CCCCC2)CN1C(=O)c1cc2ccc(Cl)cc2[nH]1] |
| 733 | 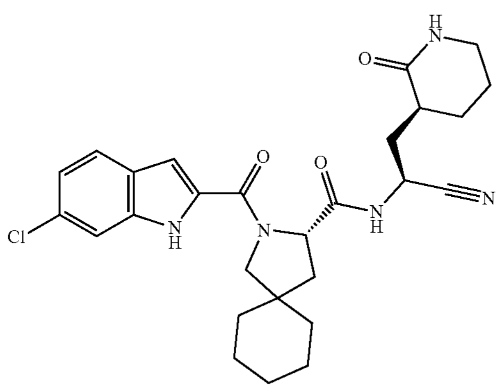 [SMILES: N#C[C@H](C[C@@H]1CCCNC1=O)NC(=O)[C@@H]1CC2(CCCCC2)CN1C(=O)c1cc2ccc(Cl)cc2[nH]1] |
| 734 | 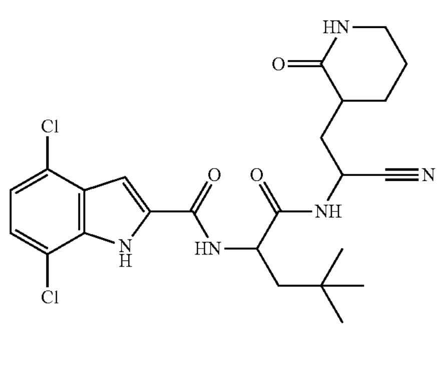 [SMILES: CC(C)(C)CC(NC(=O)c1cc2c(Cl)ccc(Cl)c2[nH]1)C(=O)NC(C#N)CC1CCCNC1=O] |

TABLE 1-continued

Exemplary compounds.

| Cmpd No. | Structure |
|---|---|
| 735 | 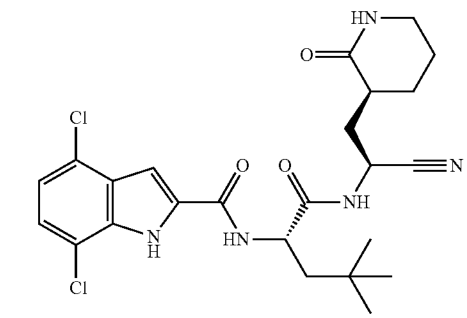 [SMILES: CC(C)(C)C[C@H](NC(=O)c1cc2c(Cl)ccc(Cl)c2[nH]1)C(=O)N[C@H](C#N)C[C@@H]1CCCNC1=O] |
| 736 | 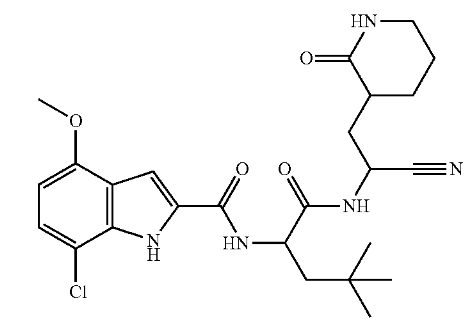 [SMILES: COc1ccc(Cl)c2[nH]c(C(=O)NC(CC(C)(C)C)C(=O)NC(C#N)CC3CCCNC3=O)cc12] |
| 737 | 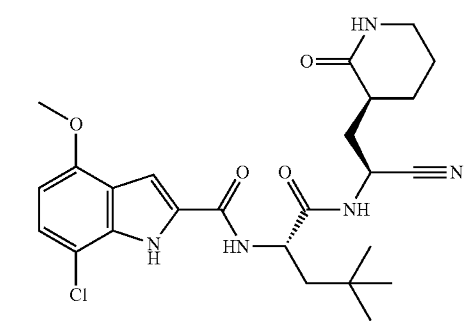 [SMILES: COc1ccc(Cl)c2[nH]c(C(=O)N[C@@H](CC(C)(C)C)C(=O)N[C@H](C#N)C[C@@H]3CCCNC3=O)cc12] |
| 738 | 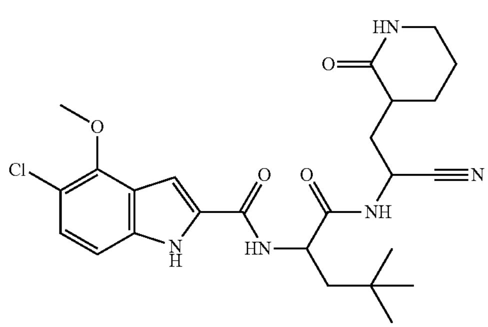 [SMILES: COc1c(Cl)ccc2[nH]c(C(=O)NC(CC(C)(C)C)C(=O)NC(C#N)CC3CCCNC3=O)cc12] |

TABLE 1-continued

Exemplary compounds.

| Cmpd No. | Structure |
|---|---|
| 739 | 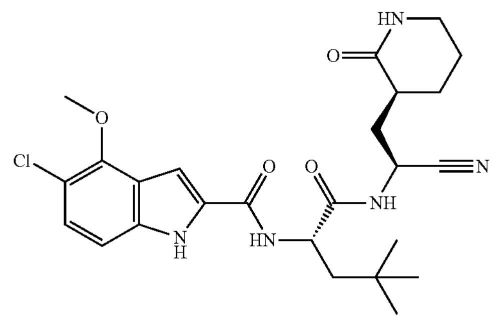 [SMILES: COc1c(Cl)ccc2[nH]c(C(=O)N[C@@H](CC(C)(C)C)C(=O)N[C@H](C#N)C[C@@H]3CCCNC3=O)cc12] |
| 740 | 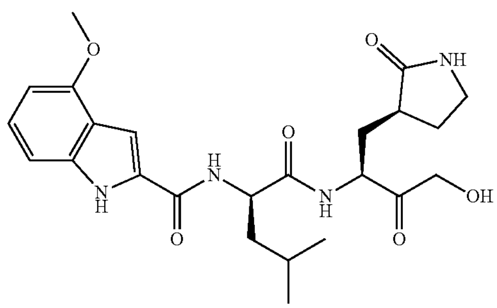 [SMILES: COc1cccc2[nH]c(C(=O)N[C@H](CC(C)C)C(=O)N[C@@H](C[C@@H]3CCNC3=O)C(=O)CO)cc12] |
| 741 | 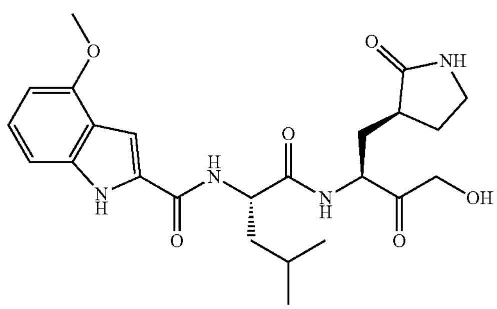 [SMILES: COc1cccc2[nH]c(C(=O)N[C@@H](CC(C)C)C(=O)N[C@@H](C[C@@H]3CCNC3=O)C(=O)CO)cc12] |
| 742 | 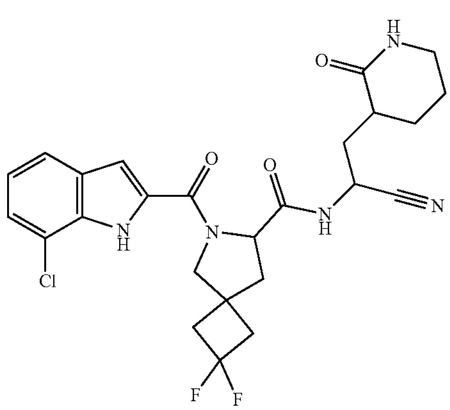 [SMILES: N#CC(CC1CCCNC1=O)NC(=O)C1CC2(CN1C(=O)c1cc3cccc(Cl)c3[nH]1)CC(F)(F)C2] |

TABLE 1-continued

Exemplary compounds.

| Cmpd No. | Structure |
|---|---|
| 743 | 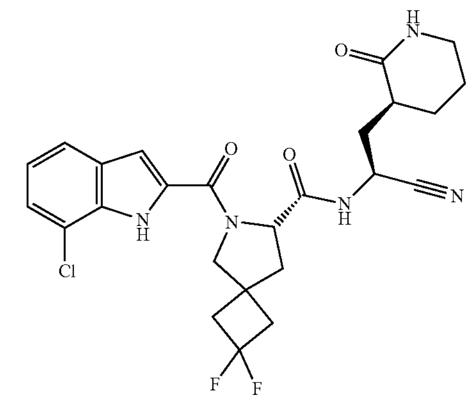 |
| 744 | 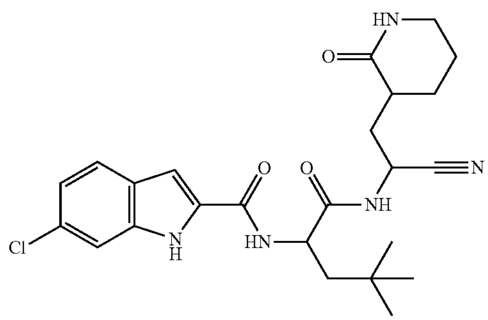 [SMILES: CC(C)(C)CC(NC(=O)c1cc2ccc(Cl)cc2[nH]1)C(=O)NC(C#N)CC1CCCNC1=O] |
| 745 | 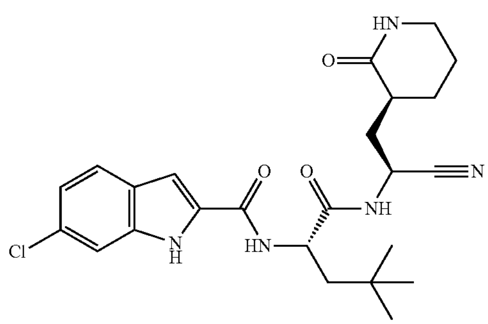 [SMILES: CC(C)(C)C[C@H](NC(=O)c1cc2ccc(Cl)cc2[nH]1)C(=O)N[C@H](C#N)C[C@@H]1CCCNC1=O] |
| 267A | 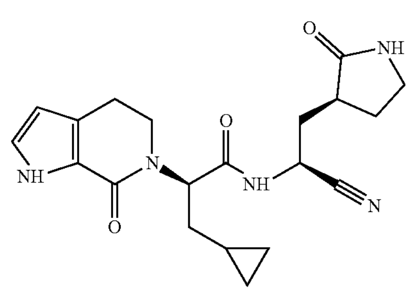 [SMILES: N#C[C@H](C[C@@H]1CCNC1=O)NC(=O)[C@@H](CC1CC1)N1CCc2cc[nH]c2C1=O] |

TABLE 1-continued

Exemplary compounds.

| Cmpd No. | Structure |
|---|---|
| 269A | 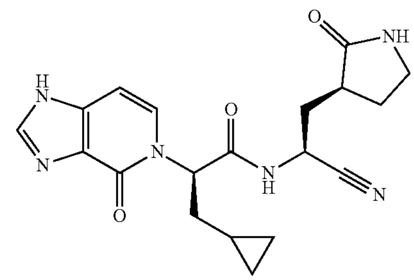 [SMILES: N#C[C@H](C[C@@H]1CCNC1=O)NC(=O)[C@@H](CC1CC1)n1ccc2[nH]cnc2c1=O] |
| 271A | 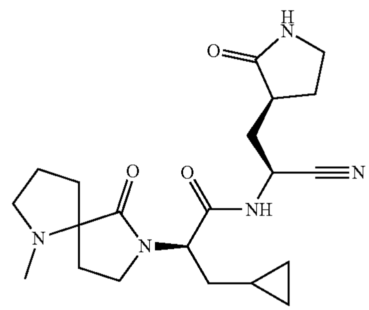 [SMILES: CN1CCCC12CCN([C@H](CC1CC1)C(=O)N[C@H](C#N)C[C@@H]1CCNC1=O)C2=O] |
| 273A | 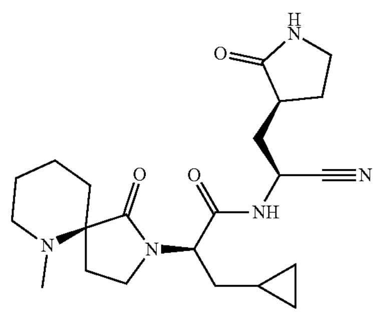 [SMILES: CN1CCCC[C@]12CCN([C@H](CC1CC1)C(=O)N[C@H](C#N)C[C@@H]1CCNC1=O)C2=O] |
| 273B | 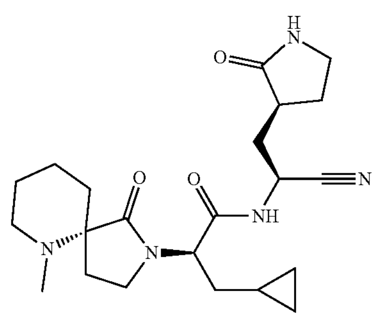 [SMILES: CN1CCCC[C@@]12CCN([C@H](CC1CC1)C(=O)N[C@H](C#N)C[C@@H]1CCNC1=O)C2=O] |
| 273C | 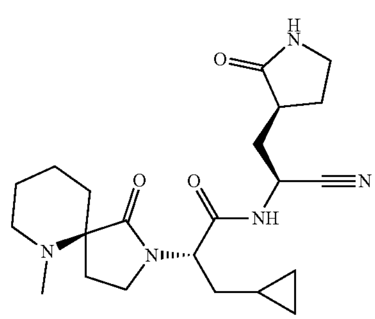 [SMILES: CN1CCCC[C@]12CCN([C@@H](CC1CC1)C(=O)N[C@H](C#N)C[C@@H]1CCNC1=O)C2=O] |

389

TABLE 1-continued

Exemplary compounds.

| Cmpd No. | Structure |
|---|---|
| 491A | 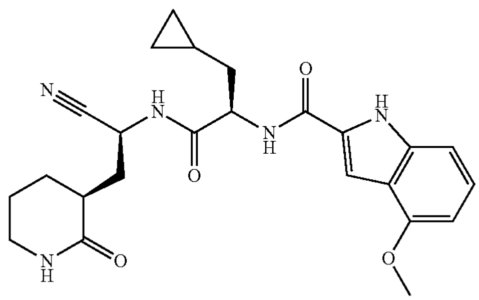 [SMILES: COc1cccc2[nH]c(C(=O)N[C@H](CC3CC3)C(=O)N[C@H](C#N)C[C@@H]3CCCNC3=O)cc12] |
| 491C | 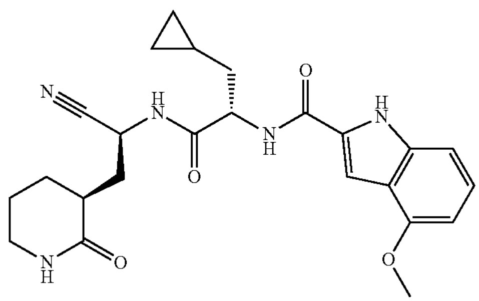 [SMILES: COc1cccc2[nH]c(C(=O)N[C@@H](CC3CC3)C(=O)N[C@H](C#N)C[C@@H]3CCCNC3=O)cc12] |
| 375A | 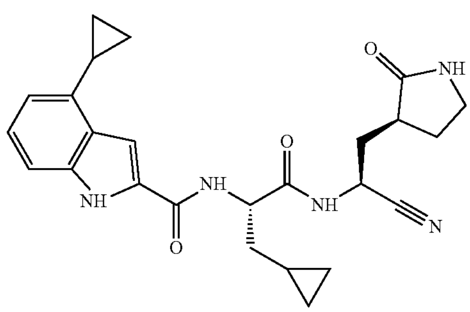 [SMILES: N#C[C@H](C[C@@H]1CCNC1=O)NC(=O)[C@H](CC1CC1)NC(=O)c1cc2c(C3CC3)cccc2[nH]1] |
| 389A | 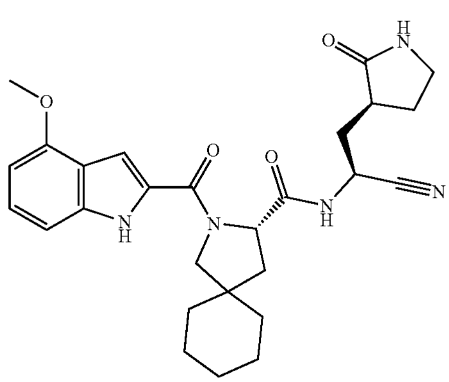 [SMILES: COc1cccc2[nH]c(C(=O)N3CC4(CCCCC4)C[C@H]3C(=O)N[C@H](C#N)C[C@@H]3CCNC3=O)cc12] |

TABLE 1-continued

Exemplary compounds.

| Cmpd No. | Structure |
|---|---|
| 389B | 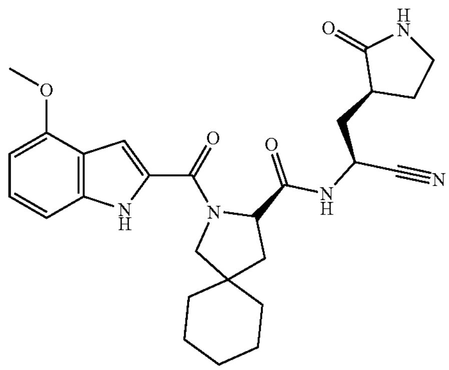 |
| 746 | 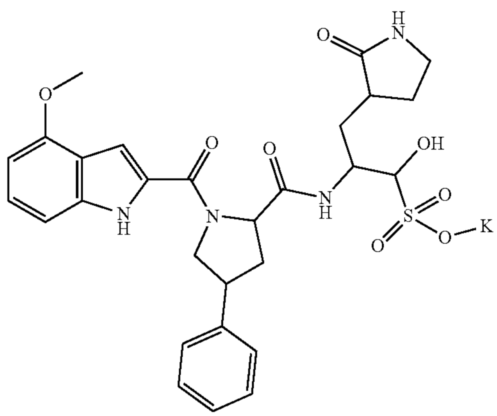 |
| 747 | 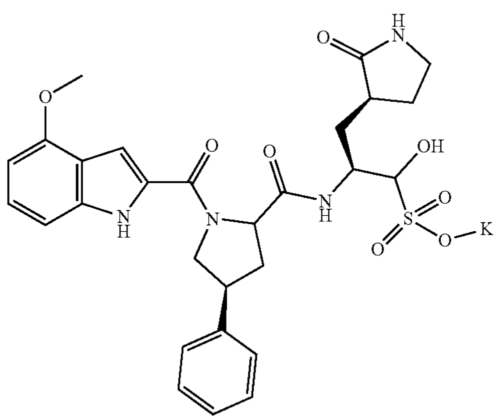 |
| 748 | 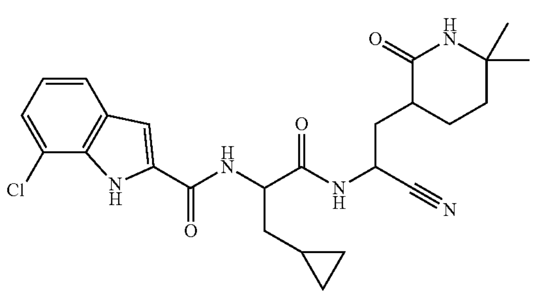 [SMILES: CC1(C)CCC(CC(C#N)NC(=O)C(CC2CC2)NC(=O)c2cc3cccc(Cl)c3[nH]2)C(=O)N1] |

TABLE 1-continued
Exemplary compounds.
| Cmpd No. | Structure |
|---|---|
| 749 | 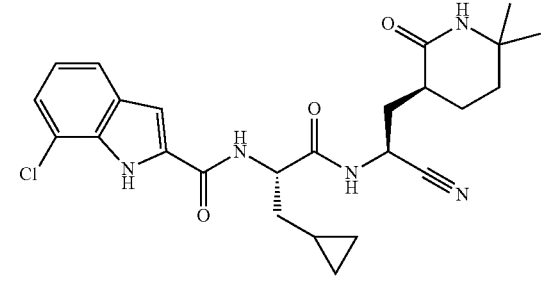 [SMILES: CC1(C)CC[C@@H](C[C@@H](C#N)NC(=O)[C@H](CC2CC2)NC(=O)c2cc3cccc(Cl)c3[nH]2)C(=O)N1] |
| 749A | 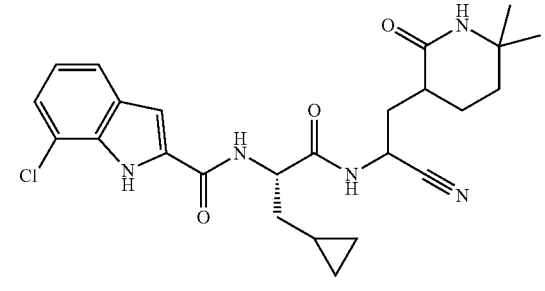 [SMILES: CC1(C)CCC(CC(C#N)NC(=O)[C@H](CC2CC2)NC(=O)c2cc3cccc(Cl)c3[nH]2)C(=O)N1] |
| 750 | 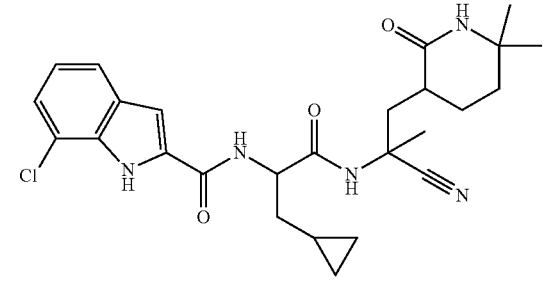 [SMILES: CC1(C)CCC(CC(C)(C#N)NC(=O)C(CC2CC2)NC(=O)c2cc3cccc(Cl)c3[nH]2)C(=O)N1] |
| 751 | 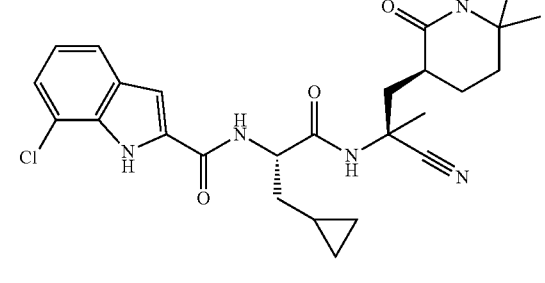 |
| 752 | 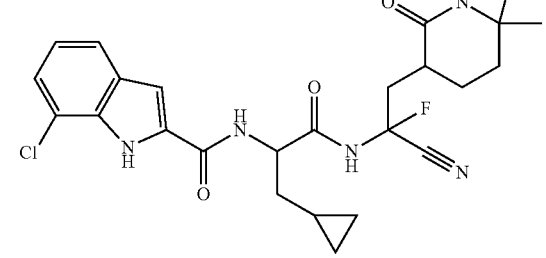 |

TABLE 1-continued

Exemplary compounds.

| Cmpd No. | Structure |
|---|---|
| 753 | 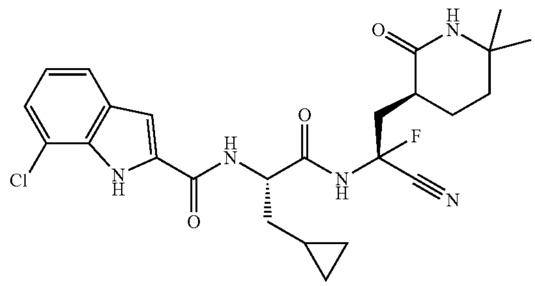 [SMILES: CC1(C)CC[C@@H](C[C@@](F)(C#N)NC(=O)[C@H](CC2CC2)NC(=O)c2cc3cccc(Cl)c3[nH]2)C(=O)N1] |
| 754 | 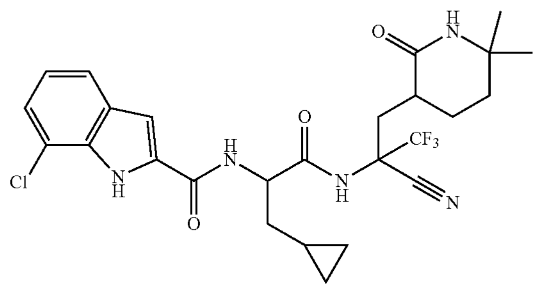 [SMILES: CC1(C)CCC(CC(C#N)(NC(=O)C(CC2CC2)NC(=O)c2cc3cccc(Cl)c3[nH]2)C(F)(F)F)C(=O)N1] |
| 755 | 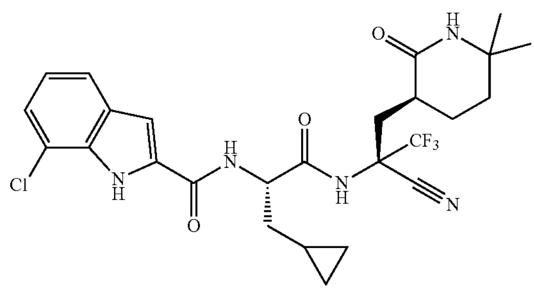 [SMILES: CC1(C)CC[C@@H](C[C@@](C#N)(NC(=O)[C@H](CC2CC2)NC(=O)c2cc3cccc(Cl)c3[nH]2)C(F)(F)F)C(=O)N1] |
| 756 | 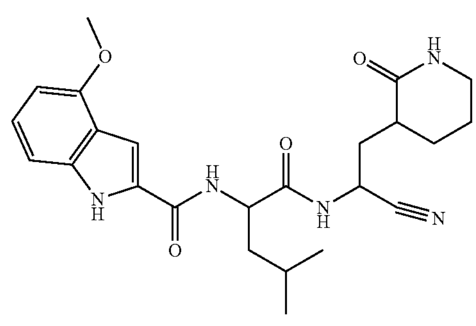 [SMILES: COc1cccc2[nH]c(C(=O)NC(CC(C)C)C(=O)NC(C#N)CC3CCCNC3=O)cc12] |
| 757 | 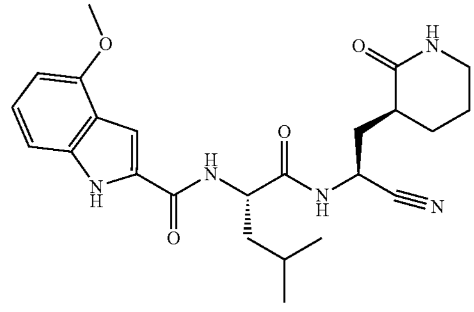 [SMILES: COc1cccc2[nH]c(C(=O)N[C@@H](CC(C)C)C(=O)N[C@H](C#N)C[C@@H]3CCCNC3=O)cc12] |

TABLE 1-continued

Exemplary compounds.

| Cmpd No. | Structure |
|---|---|
| 758 | 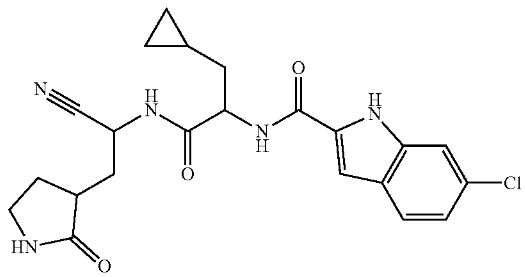 [SMILES: N#CC(CC1CCNC1=O)NC(=O)C(CC1CC1)NC(=O)c1cc2ccc(Cl)cc2[nH]1] |
| 759 | 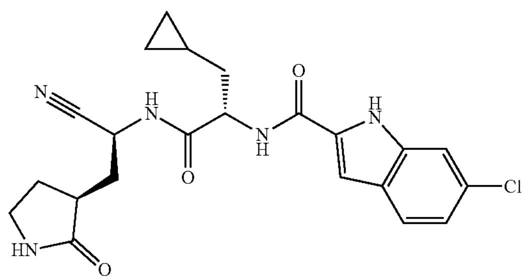 [SMILES: N#C[C@H](C[C@@H]1CCNC1=O)NC(=O)[C@H](CC1CC1)NC(=O)c1cc2ccc(Cl)cc2[nH]1] |
| 760 | 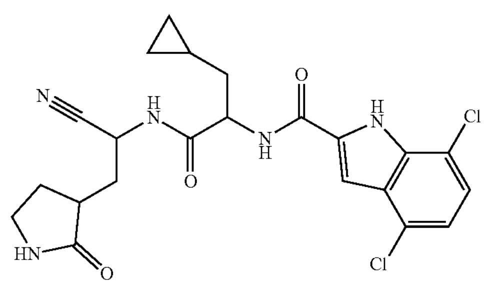 [SMILES: N#CC(CC1CCNC1=O)NC(=O)C(CC1CC1)NC(=O)c1cc2c(Cl)ccc(Cl)c2[nH]1] |
| 761 | 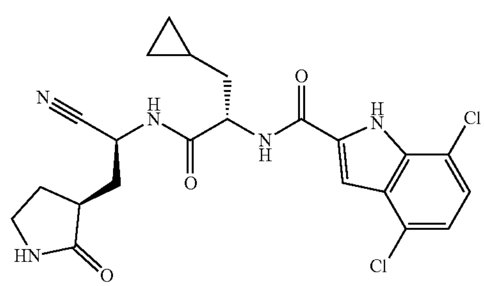 [SMILES: N#C[C@H](C[C@@H]1CCNC1=O)NC(=O)[C@H](CC1CC1)NC(=O)c1cc2c(Cl)ccc(Cl)c2[nH]1] |
| 762 | 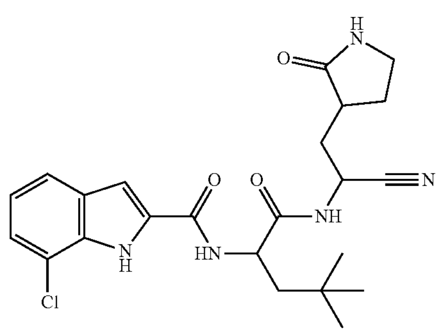 [SMILES: CC(C)(C)CC(NC(=O)c1cc2cccc(Cl)c2[nH]1)C(=O)NC(C#N)CC1CCNC1=O] |

TABLE 1-continued
Exemplary compounds.
| Cmpd No. | Structure |
|---|---|
| 763 | 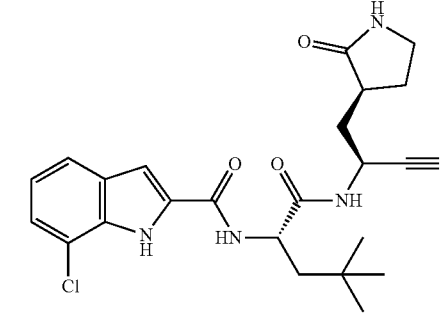 |
| 764 | 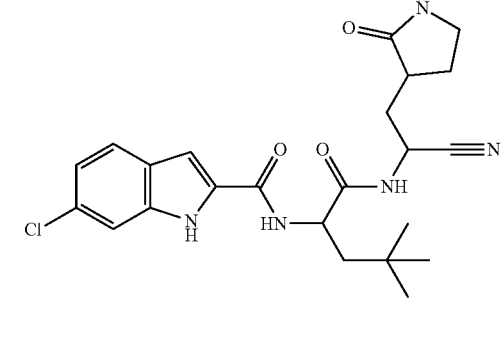 |
| 765 | 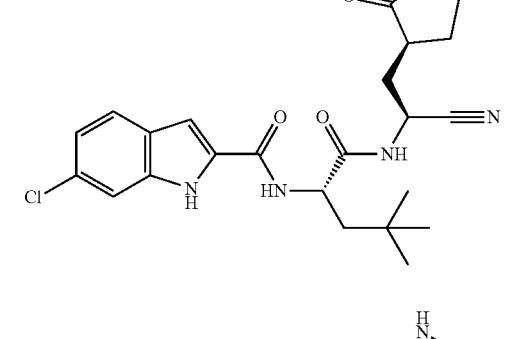 |
| 766 | 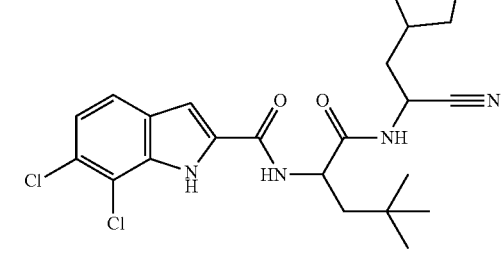 |

TABLE 1-continued
Exemplary compounds.
| Cmpd No. | Structure |
|---|---|
| 767 | 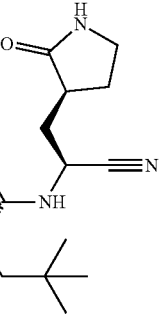 |
| 768 | 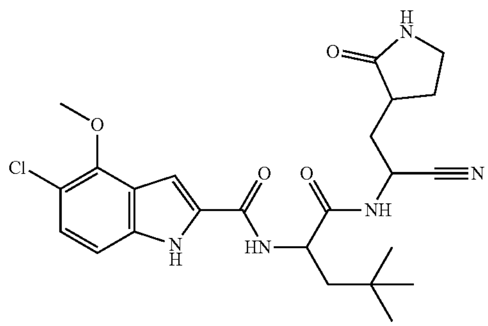 [SMILES: COc1c(Cl)ccc2[nH]c(C(=O)NC(CC(C)(C)C)C(=O)NC(C#N)CC3CCNC3=O)cc12] |
| 769 | 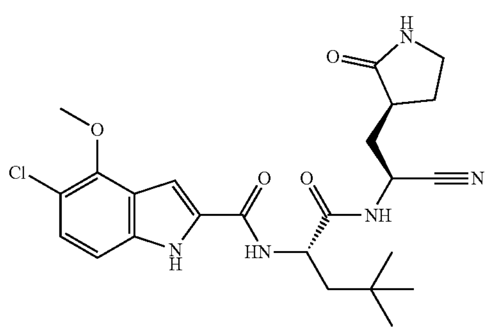 [SMILES: COc1c(Cl)ccc2[nH]c(C(=O)N[C@@H](CC(C)(C)C)C(=O)N[C@H](C#N)C[C@@H]3CCNC3=O)cc12] |
| 770 | 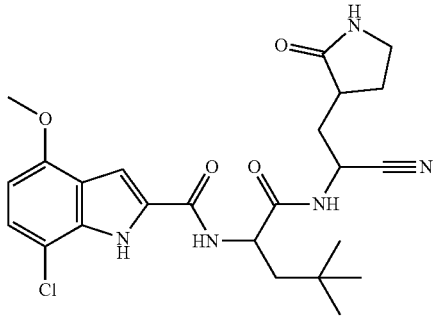 [SMILES: COc1ccc(Cl)c2[nH]c(C(=O)NC(CC(C)(C)C)C(=O)NC(C#N)CC3CCNC3=O)cc12] |

TABLE 1-continued
Exemplary compounds.
| Cmpd No. | Structure |
|---|---|
| 771 | 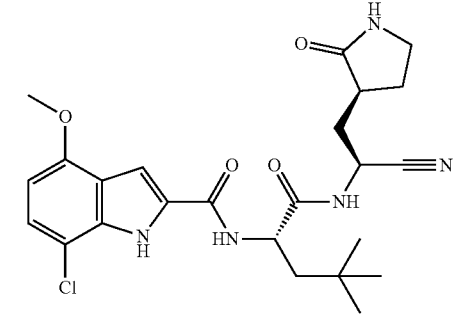 [SMILES: COc1ccc(Cl)c2[nH]c(C(=O)N[C@@H](CC(C)(C)C)C(=O)N[C@H](C#N)C[C@@H]3CCNC3=O)cc12] |
| 772 | 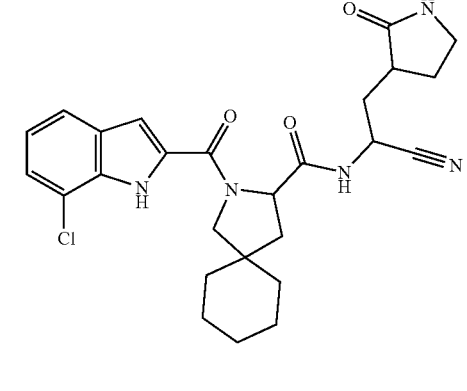 |
| 773 | 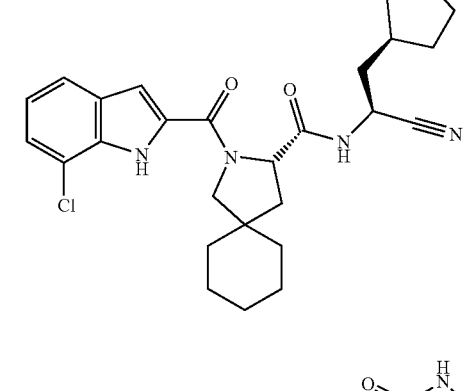 |
| 774 | 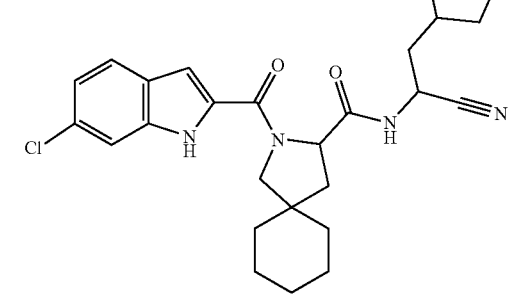 |

TABLE 1-continued

Exemplary compounds.

| Cmpd No. | Structure |
|---|---|
| 775 | 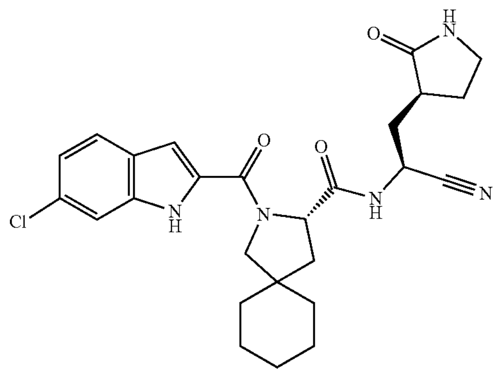 [SMILES: N#C[C@H](C[C@@H]1CCNC1=O)NC(=O)[C@@H]1CC2(CCCCC2)CN1C(=O)c1cc2ccc(Cl)cc2[nH]1] |
| 776 | 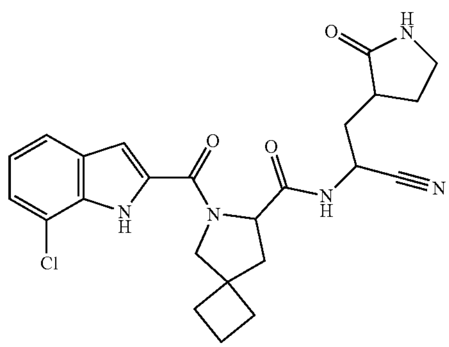 [SMILES: N#CC(CC1CCNC1=O)NC(=O)C1CC2(CCC2)CN1C(=O)c1cc2cccc(Cl)c2[nH]1] |
| 777 | 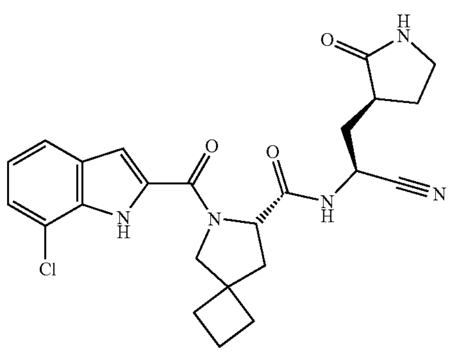 |
| 778 | 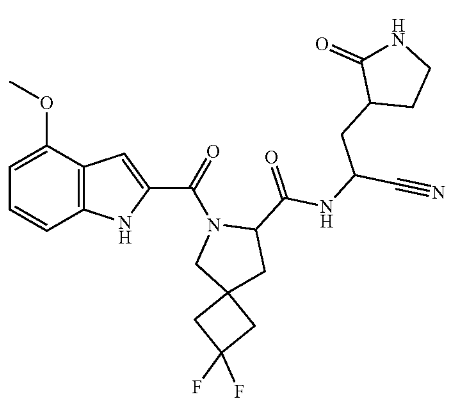 [SMILES: COc1cccc2[nH]c(C(=O)N3CC4(CC3C(=O)NC(C#N)CC3CCNC3=O)CC(F)(F)C4)cc12] |

TABLE 1-continued

Exemplary compounds.

| Cmpd No. | Structure |
|---|---|
| 779 | 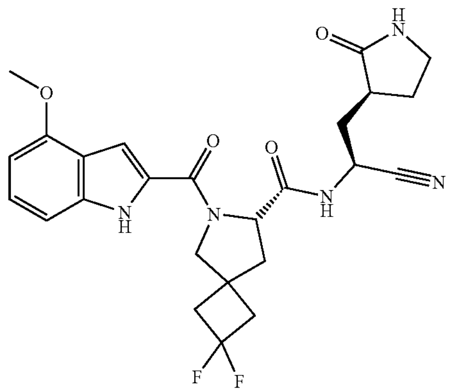 |
| 780 | 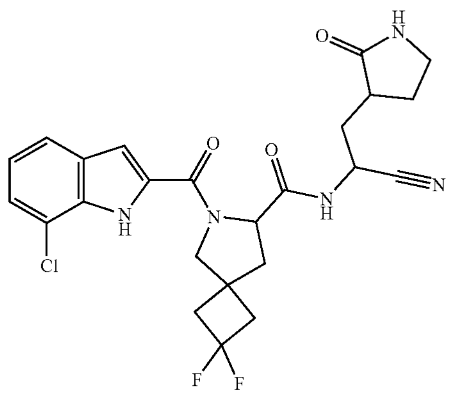 [SMILES: N#CC(CC1CCNC1=O)NC(=O)C1CC2(CN1C(=O)c1cc3cccc(Cl)c3[nH]1)CC(F)(F)C2] |
| 781 | 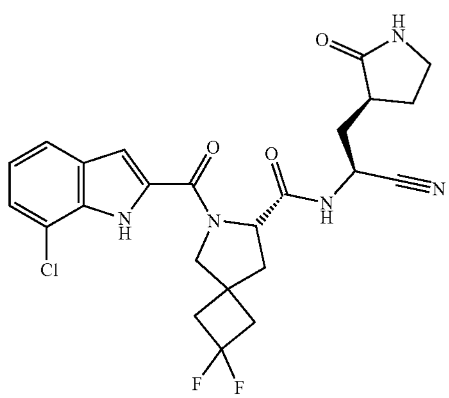 |
| 639A | 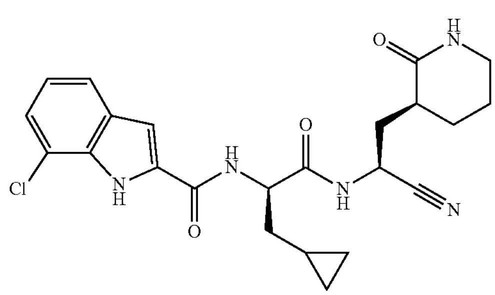 [SMILES: N#C[C@H](C[C@@H]1CCCNC1=O)NC(=O)[C@@H](CC1CC1)NC(=O)c1cc2cccc(Cl)c2[nH]1] |

TABLE 1-continued
Exemplary compounds.
| Cmpd No. | Structure |
|---|---|
| 782 | 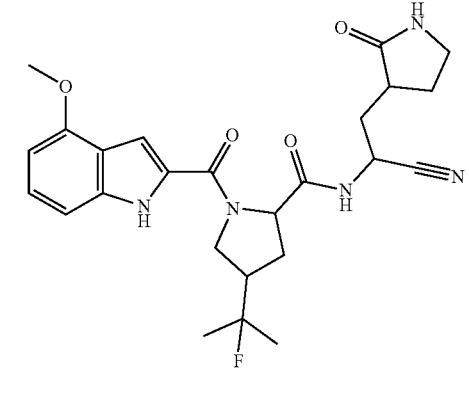 [SMILES: COc1cccc2[nH]c(C(=O)N3CC(C(C)(C)F)CC3C(=O)NC(C#N)CC3CCNC3=O)cc12] |
| 783 | 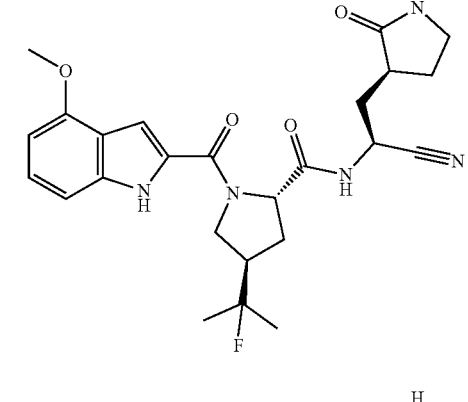 |
| 784 | 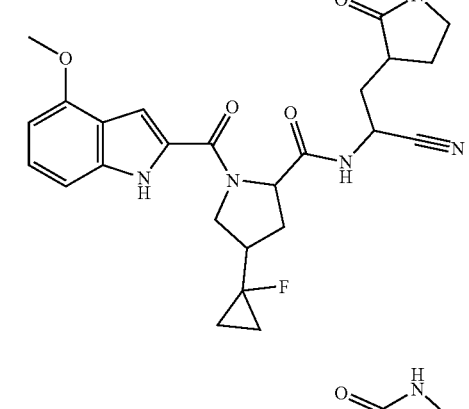 |
| 785 | 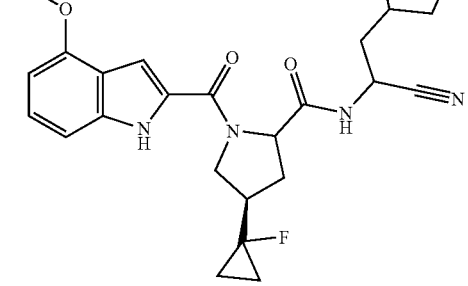 |

TABLE 1-continued

Exemplary compounds.

| Cmpd No. | Structure |
| --- | --- |
| 786 | 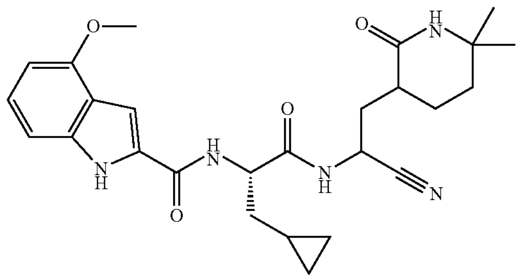 [SMILES: COc1cccc2[nH]c(C(=O)N[C@@H](CC3CC3)C(=O)NC(C#N)CC3CCC(C)(C)NC3=O)cc12] |
| 787 | 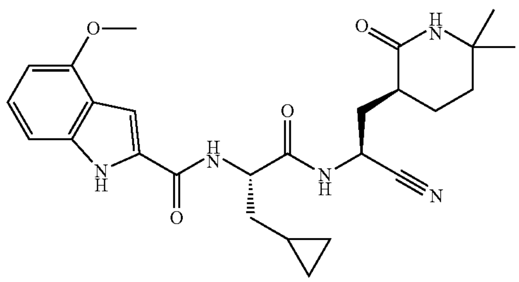 [SMILES: COc1cccc2[nH]c(C(=O)N[C@@H](CC3CC3)C(=O)N[C@H](C#N)C[C@@H]3CCC(C)(C)NC3=O)cc12] |
| 787A | 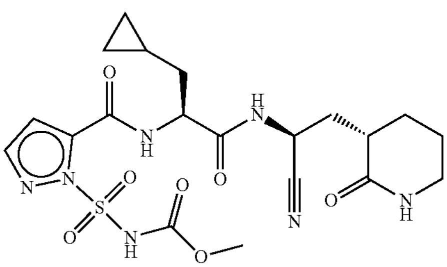 |
| 788 | 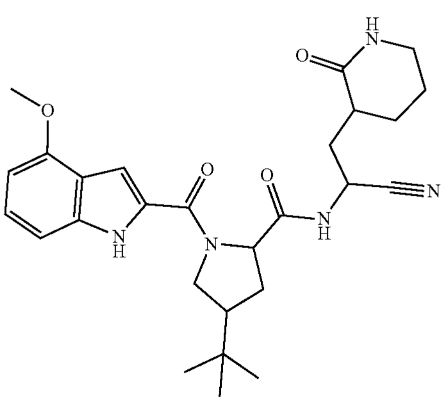 [SMILES: COc1cccc2[nH]c(C(=O)N3CC(C(C)(C)C)CC3C(=O)NC(C#N)CC3CCCNC3=O)cc12] |

TABLE 1-continued

Exemplary compounds.

| Cmpd No. | Structure |
|---|---|
| 789 | 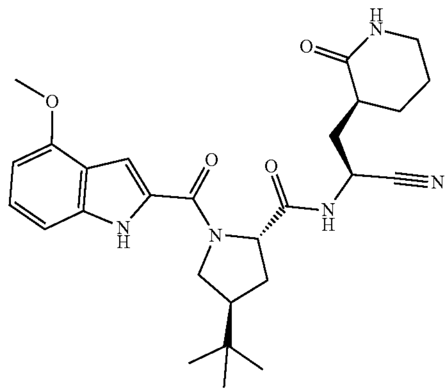 [SMILES: COc1cccc2[nH]c(C(=O)N3C[C@H](C(C)(C)C)C[C@H]3C(=O)N[C@H](C#N)C[C@@H]3CCCNC3=O)cc12] |
| 790 | 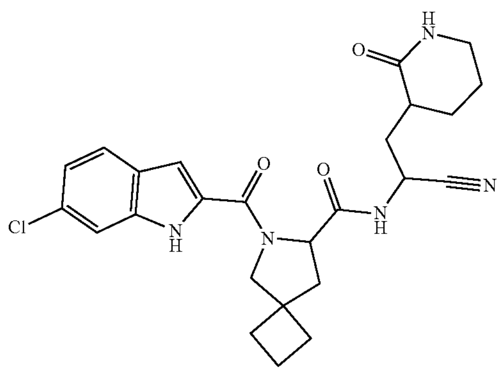 [SMILES: N#CC(CC1CCCNC1=O)NC(=O)C1CC2(CCC2)CN1C(=O)c1cc2ccc(Cl)cc2[nH]1] |
| 791 | 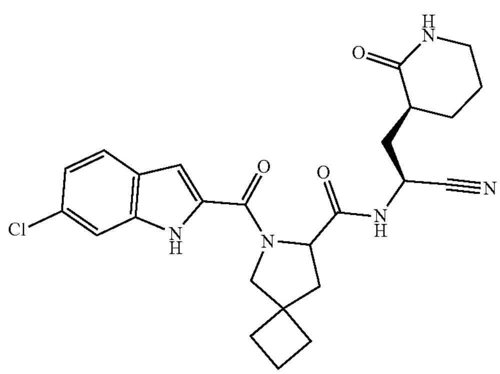 [SMILES: N#C[C@H](C[C@@H]1CCCNC1=O)NC(=O)C1CC2(CCC2)CN1C(=O)c1cc2ccc(Cl)cc2[nH]1] |
| 792 | 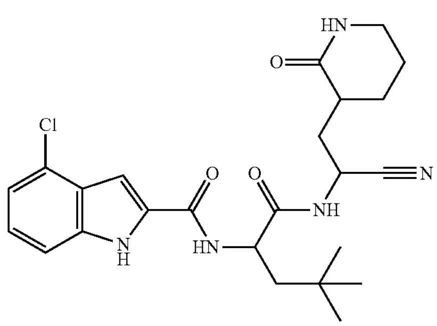 [SMILES: CC(C)(C)CC(NC(=O)c1cc2c(Cl)cccc2[nH]1)C(=O)NC(C#N)CC1CCCNC1=O] |

TABLE 1-continued

Exemplary compounds.

| Cmpd No. | Structure |
|---|---|
| 793 | 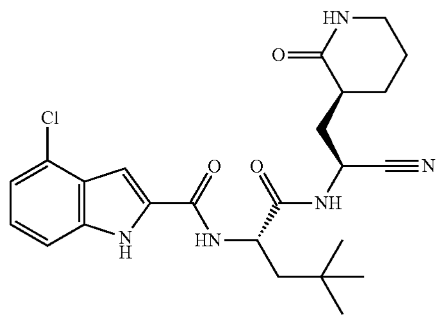 [SMILES: CC(C)(C)C[C@H](NC(=O)c1cc2c(Cl)cccc2[nH]1)C(=O)N[C@H](C#N)C[C@@H]1CCCNC1=O] |
| 794 | 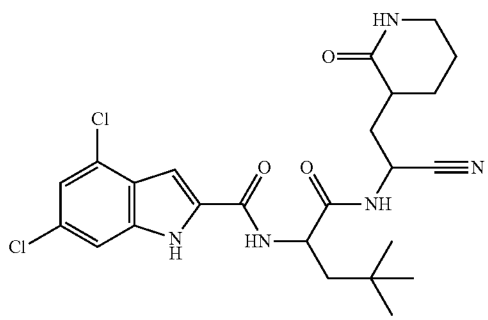 [SMILES: CC(C)(C)CC(NC(=O)c1cc2c(Cl)cc(Cl)cc2[nH]1)C(=O)NC(C#N)CC1CCCNC1=O] |
| 795 | 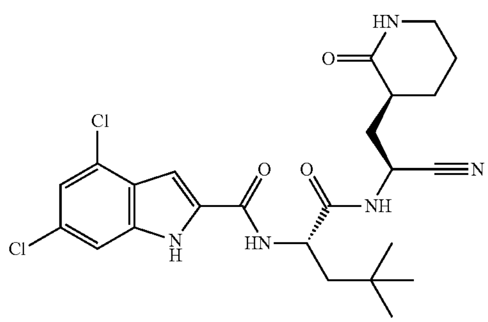 [SMILES: CC(C)(C)C[C@H](NC(=O)c1cc2c(Cl)cc(Cl)cc2[nH]1)C(=O)N[C@H](C#N)C[C@@H]1CCCNC1=O] |
| 796 | 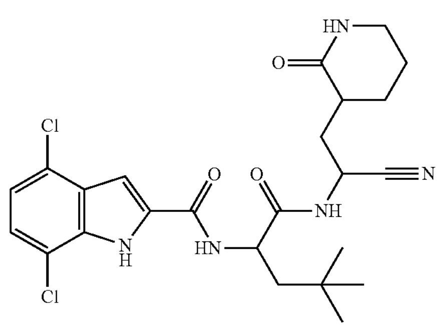 [SMILES: CC(C)(C)CC(NC(=O)c1cc2c(Cl)ccc(Cl)c2[nH]1)C(=O)NC(C#N)CC1CCCNC1=O] |

TABLE 1-continued

Exemplary compounds.

| Cmpd No. | Structure |
|---|---|
| 797 | 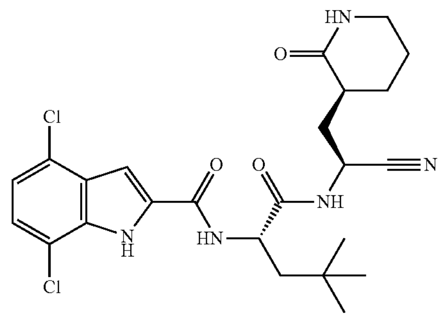 |
| 798 | 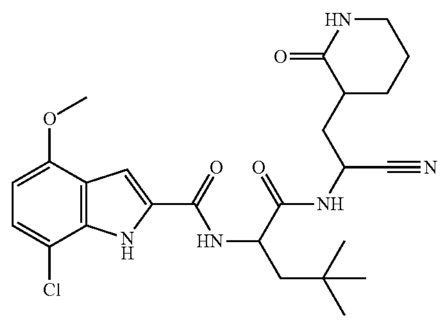 [SMILES: COc1ccc(Cl)c2[nH]c(C(=O)NC(CC(C)(C)C)C(=O)NC(C#N)CC3CCCNC3=O)cc12] |
| 799 | 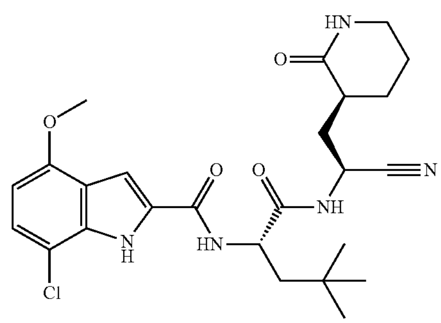 [SMILES: COc1ccc(Cl)c2[nH]c(C(=O)N[C@@H](CC(C)(C)C)C(=O)N[C@H](C#N)C[C@@H]3CCCNC3=O)cc12] |
| 800 | 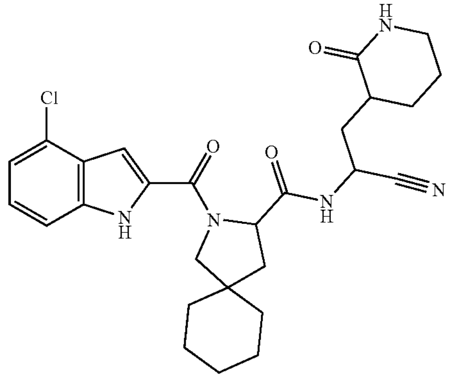 [SMILES: N#CC(CC1CCCNC1=O)NC(=O)C1CC2(CCCCC2)CN1C(=O)c1cc2c(Cl)cccc2[nH]1] |

TABLE 1-continued
Exemplary compounds.
| Cmpd No. | Structure |
|---|---|
| 801 | 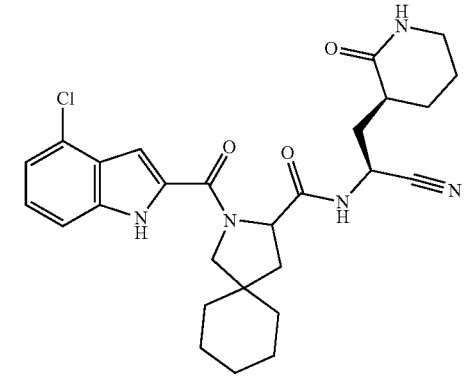 [SMILES: N#C[C@H](C[C@@H]1CCCNC1=O)NC(=O)C1CC2(CCCCC2)CN1C(=O)c1cc2c(Cl)cccc2[nH]1] |
| 802 | 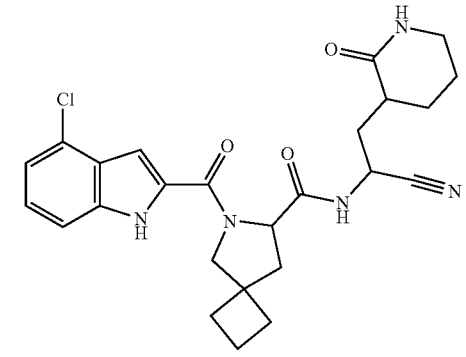 [SMILES: N#CC(CC1CCCNC1=O)NC(=O)C1CC2(CCC2)CN1C(=O)c1cc2c(Cl)cccc2[nH]1] |
| 803 | 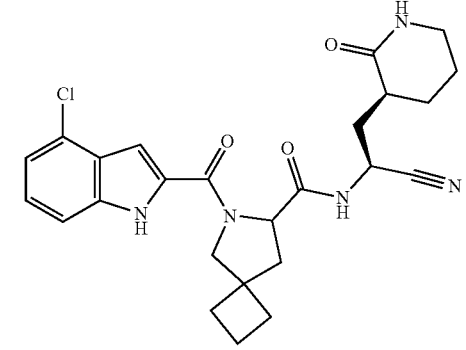 [SMILES: N#C[C@H](C[C@@H]1CCCNC1=O)NC(=O)C1CC2(CCC2)CN1C(=O)c1cc2c(Cl)cccc2[nH]1] |
| 804 | 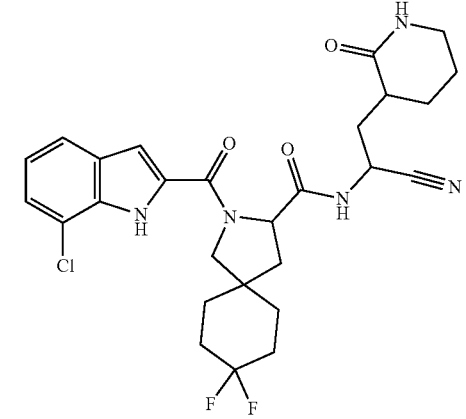 [SMILES: N#CC(CC1CCCNC1=O)NC(=O)C1CC2(CCC(F)(F)CC2)CN1C(=O)c1cc2cccc(Cl)c2[nH]1] |

TABLE 1-continued

Exemplary compounds.

| Cmpd No. | Structure |
|---|---|
| 805 | 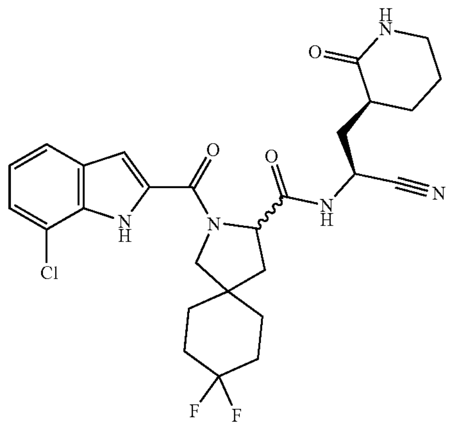 [SMILES: N#C[C@H](C[C@@H]1CCCNC1=O)NC(=O)C1CC2(CCC(F)(F)CC2)CN1C(=O)c1cc2cccc(Cl)c2[nH]1] |
| 805a | 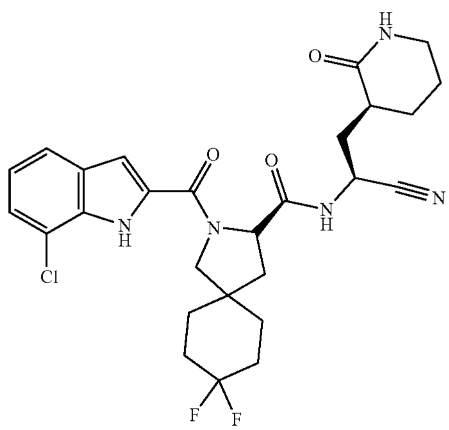 |
| 805b | 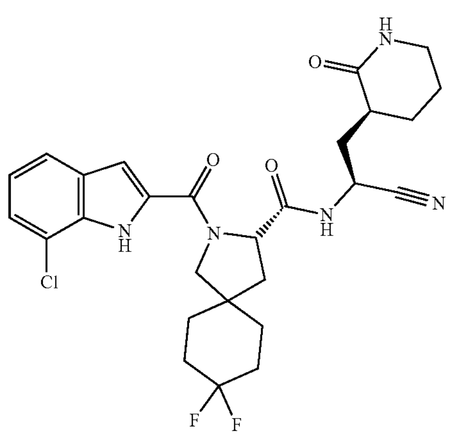 |

TABLE 1-continued
Exemplary compounds.
| Cmpd No. | Structure |
|---|---|
| 806 | 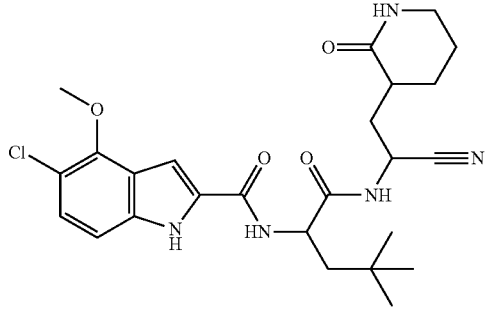 [SMILES: COc1c(Cl)ccc2[nH]c(C(=O)NC(CC(C)(C)C)C(=O)NC(C#N)CC3CCCNC3=O)cc12] |
| 806a | 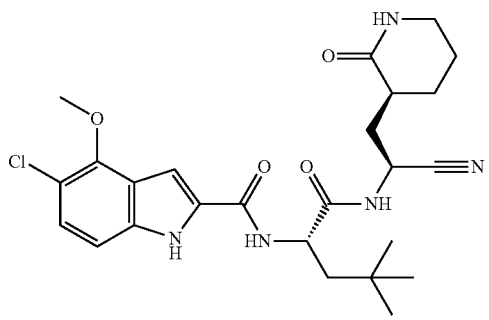 [SMILES: COc1c(Cl)ccc2[nH]c(C(=O)N[C@@H](CC(C)(C)C)C(=O)N[C@H](C#N)C[C@@H]3CCCNC3=O)cc12] |
| 807 | 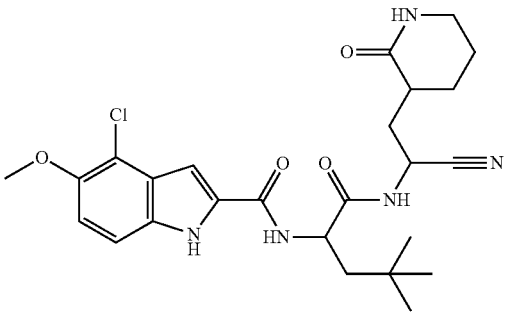 [SMILES: COc1ccc2[nH]c(C(=O)NC(CC(C)(C)C)C(=O)NC(C#N)CC3CCCNC3=O)cc2c1Cl] |
| 808 | 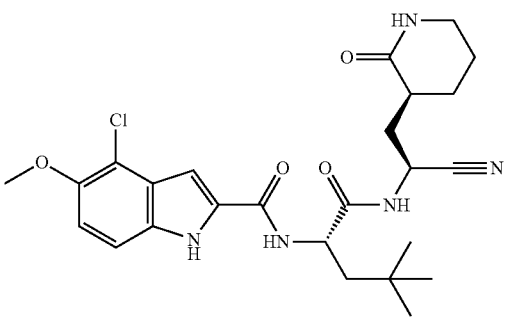 [SMILES: COc1ccc2[nH]c(C(=O)N[C@@H](CC(C)(C)C)C(=O)N[C@H](C#N)C[C@@H]3CCCNC3=O)cc2c1Cl] |

TABLE 1-continued

Exemplary compounds.

| Cmpd No. | Structure |
|---|---|
| 809 | 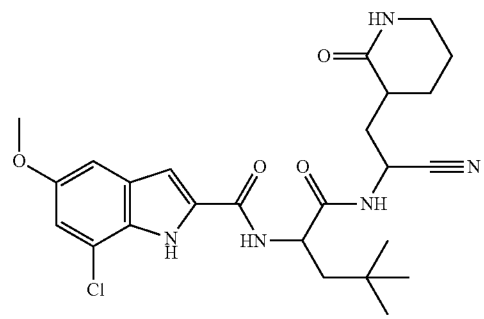 [SMILES: COc1cc(Cl)c2[nH]c(C(=O)NC(CC(C)(C)C)C(=O)NC(C#N)CC3CCCNC3=O)cc2c1] |
| 810 | 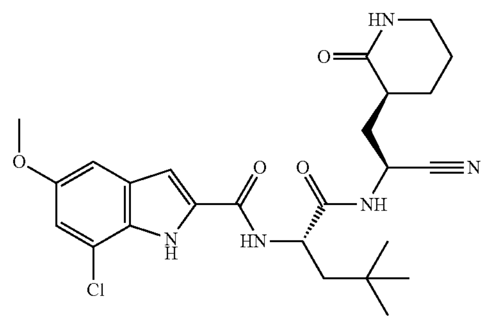 [SMILES: COc1cc(Cl)c2[nH]c(C(=O)N[C@@H](CC(C)(C)C)C(=O)N[C@H](C#N)C[C@@H]3CCCNC3=O)cc2c1] |
| 811 | 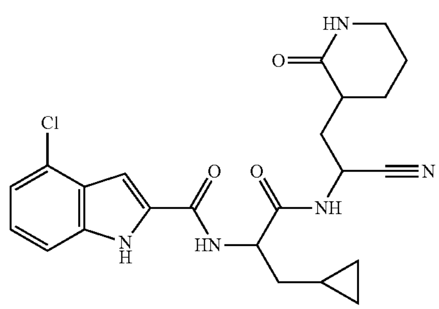 [SMILES: N#CC(CC1CCCNC1=O)NC(=O)C(CC1CC1)NC(=O)c1cc2c(Cl)cccc2[nH]1] |
| 812 | 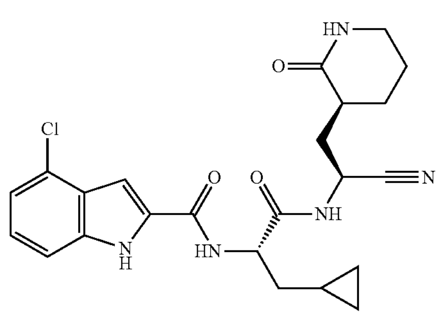 [SMILES: N#C[C@H](C[C@@H]1CCCNC1=O)NC(=O)[C@H](CC1CC1)NC(=O)c1cc2c(Cl)cccc2[nH]1] |

TABLE 1-continued

Exemplary compounds.

| Cmpd No. | Structure |
|---|---|
| 813 | 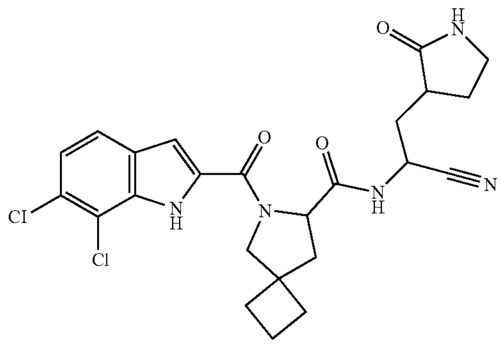 |
| 814 | 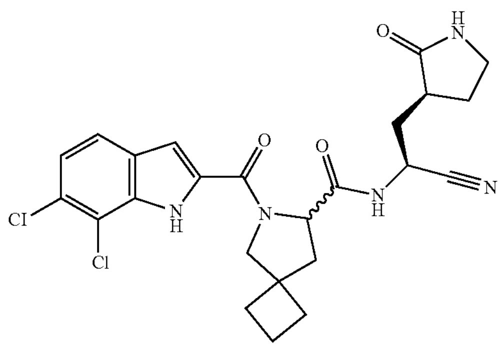 |
| 814a | 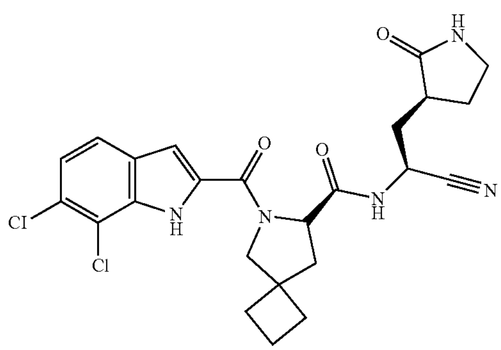 |
| 814b | 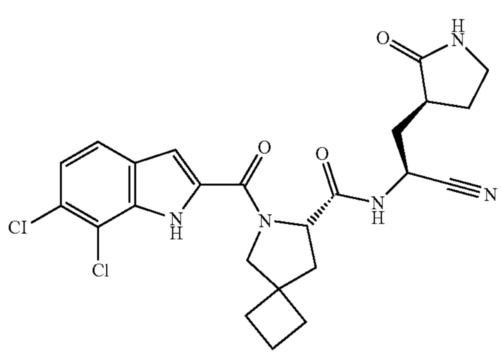 |

TABLE 1-continued
Exemplary compounds.
| Cmpd No. | Structure |
|---|---|
| 815 | 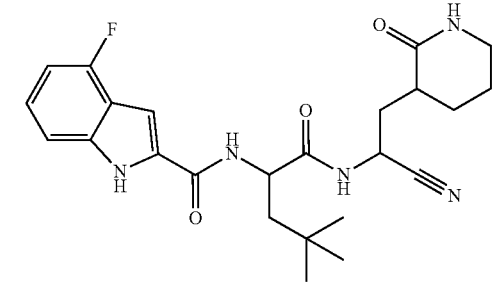 [SMILES: CC(C)(C)CC(NC(=O)c1cc2c(F)cccc2[nH]1)C(=O)NC(C#N)CC1CCCNC1=O] |
| 816 | 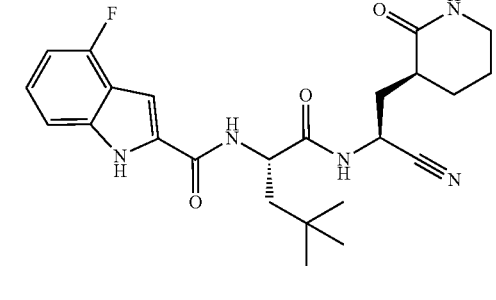 |
| 817 | 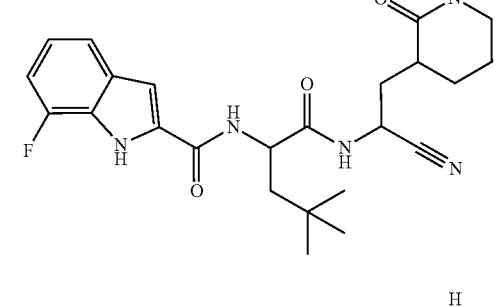 |
| 818 | 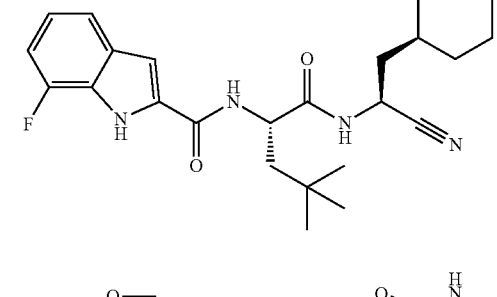 |
| 819 | 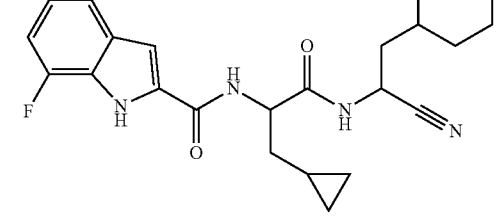 |

TABLE 1-continued

Exemplary compounds.

| Cmpd No. | Structure |
|---|---|
| 820 | 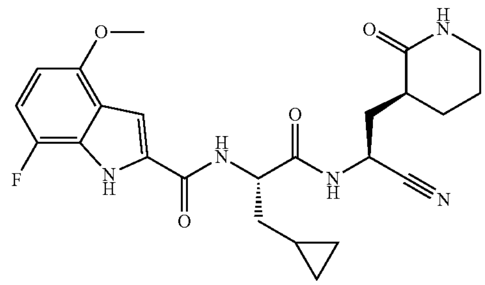 [SMILES: COc1ccc(F)c2[nH]c(C(=O)N[C@@H](CC3CC3)C(=O)N[C@H](C#N)C[C@@H]3CCCNC3=O)cc12] |
| 821 | 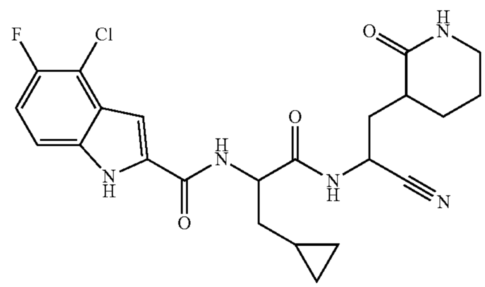 [SMILES: N#CC(CC1CCCNC1=O)NC(=O)C(CC1CC1)NC(=O)c1cc2c(Cl)c(F)ccc2[nH]1] |
| 822 | 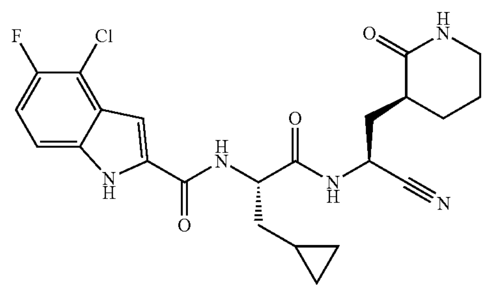 [SMILES: N#C[C@H](C[C@@H]1CCCNC1=O)NC(=O)[C@H](CC1CC1)NC(=O)c1cc2c(Cl)c(F)ccc2[nH]1] |
| 823 | 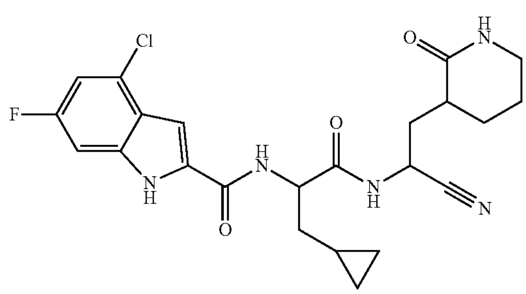 [SMILES: N#CC(CC1CCCNC1=O)NC(=O)C(CC1CC1)NC(=O)c1cc2c(Cl)cc(F)cc2[nH]1] |
| 824 | 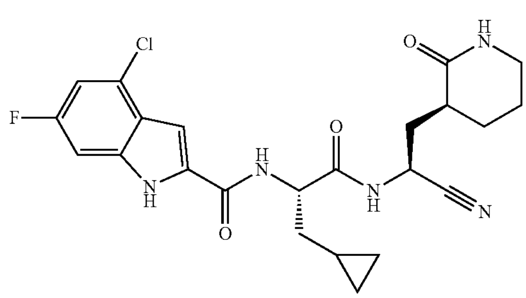 [SMILES: N#C[C@H](C[C@@H]1CCCNC1=O)NC(=O)[C@H](CC1CC1)NC(=O)c1cc2c(Cl)cc(F)cc2[nH]1] |

TABLE 1-continued
Exemplary compounds.
| Cmpd No. | Structure |
|---|---|
| 825 | 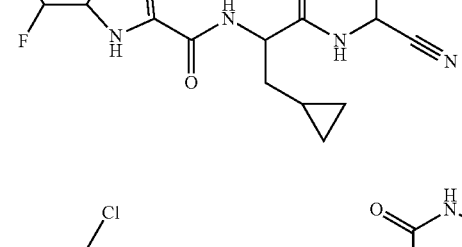 |
| 826 | 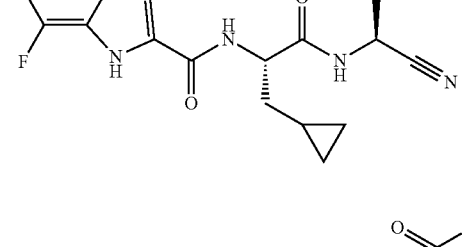 |
| 827 | 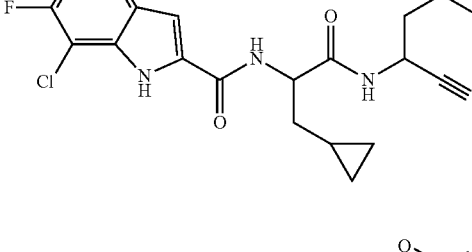 |
| 828 | 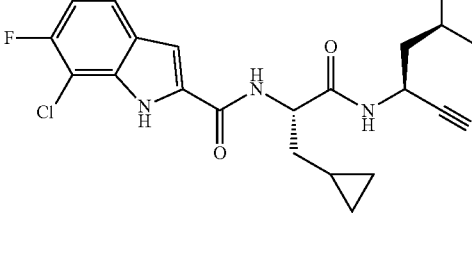 |
| 829 | 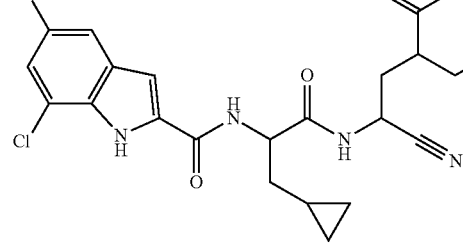 |

435

TABLE 1-continued

Exemplary compounds.

| Cmpd No. | Structure |
|---|---|
| 830 | 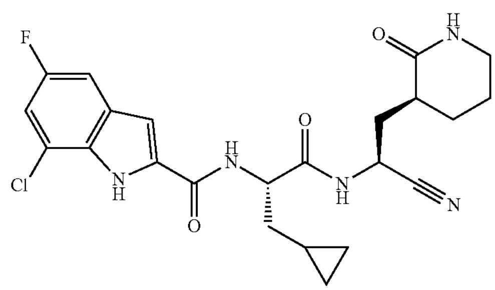 [SMILES: N#C[C@H](C[C@@H]1CCCNC1=O)NC(=O)[C@H](CC1CC1)NC(=O)c1cc2cc(F)cc(Cl)c2[nH]1] |
| 831 | 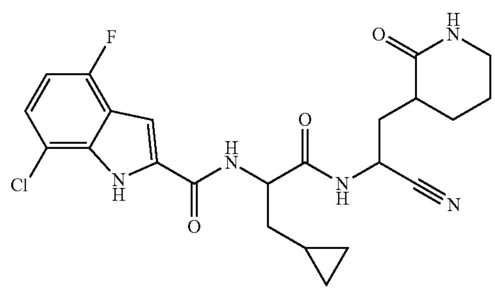 [SMILES: N#CC(CC1CCCNC1=O)NC(=O)C(CC1CC1)NC(=O)c1cc2c(F)ccc(Cl)c2[nH]1] |
| 832 | 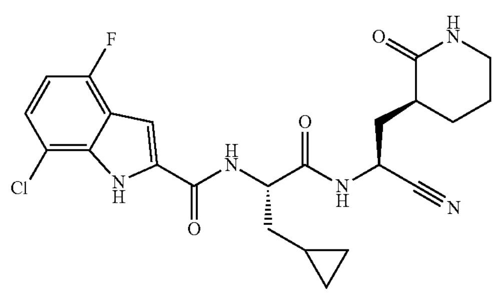 [SMILES: N#C[C@H](C[C@@H]1CCCNC1=O)NC(=O)[C@H](CC1CC1)NC(=O)c1cc2c(F)ccc(Cl)c2[nH]1] |
| 833 | 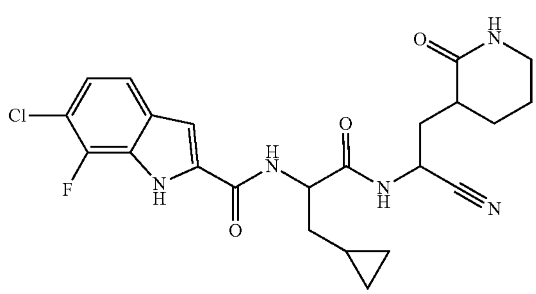 [SMILES: N#CC(CC1CCCNC1=O)NC(=O)C(CC1CC1)NC(=O)c1cc2ccc(Cl)c(F)c2[nH]1] |
| 834 | 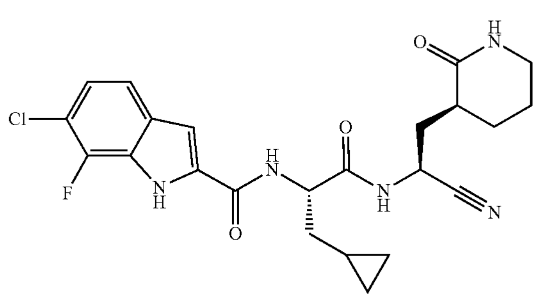 [SMILES: N#C[C@H](C[C@@H]1CCCNC1=O)NC(=O)[C@H](CC1CC1)NC(=O)c1cc2ccc(Cl)c(F)c2[nH]1] |

436

TABLE 1-continued

Exemplary compounds.

| Cmpd No. | Structure |
|---|---|
| 835 | 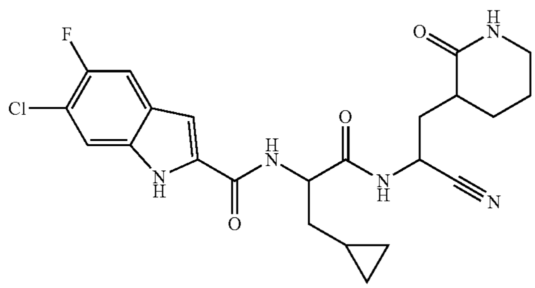 [SMILES: N#CC(CC1CCCNC1=O)NC(=O)C(CC1CC1)NC(=O)c1cc2cc(F)c(Cl)cc2[nH]1] |
| 836 | 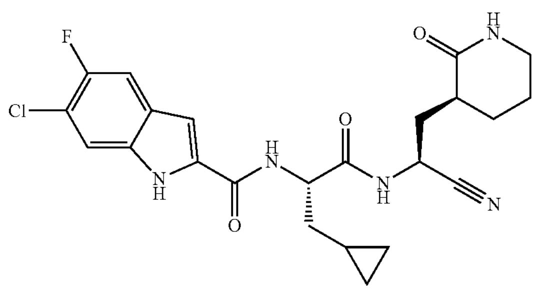 [SMILES: N#C[C@H](C[C@@H]1CCCNC1=O)NC(=O)[C@H](CC1CC1)NC(=O)c1cc2cc(F)c(Cl)cc2[nH]1] |
| 837 | 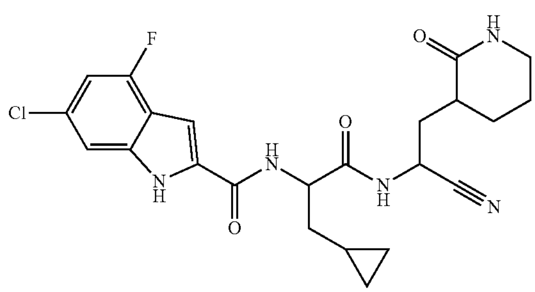 [SMILES: N#CC(CC1CCCNC1=O)NC(=O)C(CC1CC1)NC(=O)c1cc2c(F)cc(Cl)cc2[nH]1] |
| 838 | 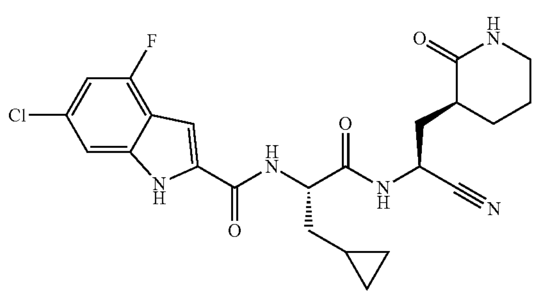 [SMILES: N#C[C@H](C[C@@H]1CCCNC1=O)NC(=O)[C@H](CC1CC1)NC(=O)c1cc2c(F)cc(Cl)cc2[nH]1] |
| 839 | 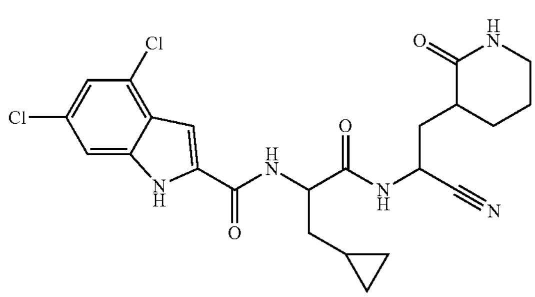 [SMILES: N#CC(CC1CCCNC1=O)NC(=O)C(CC1CC1)NC(=O)c1cc2c(Cl)cc(Cl)cc2[nH]1] |

TABLE 1-continued

| Cmpd No. | Structure |
|---|---|
| 840 | 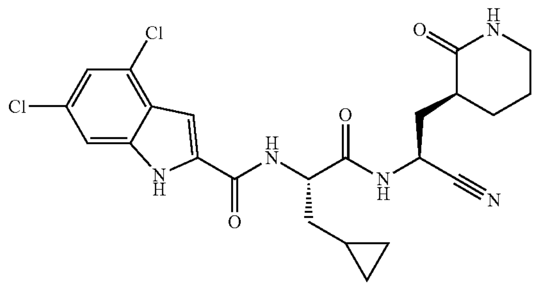 [SMILES: N#C[C@H](C[C@@H]1CCCNC1=O)NC(=O)[C@H](CC1CC1)NC(=O)c1cc2c(Cl)cc(Cl)cc2[nH]1] |
| 841 | 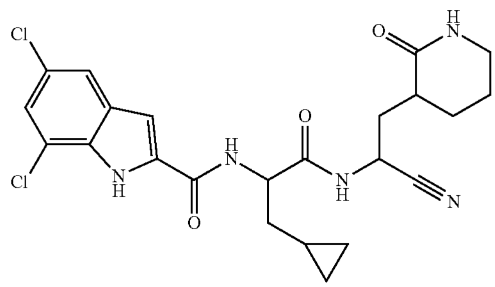 [SMILES: N#CC(CC1CCCNC1=O)NC(=O)C(CC1CC1)NC(=O)c1cc2cc(Cl)cc(Cl)c2[nH]1] |
| 842 | 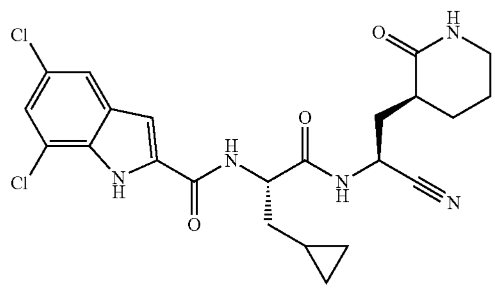 [SMILES: N#C[C@H](C[C@@H]1CCCNC1=O)NC(=O)[C@H](CC1CC1)NC(=O)c1cc2cc(Cl)cc(Cl)c2[nH]1] |
| 843 | 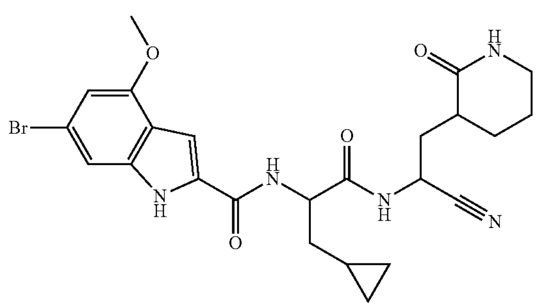 [SMILES: COc1cc(Br)cc2[nH]c(C(=O)NC(CC3CC3)C(=O)NC(C#N)CC3CCCNC3=O)cc12] |
| 844 | 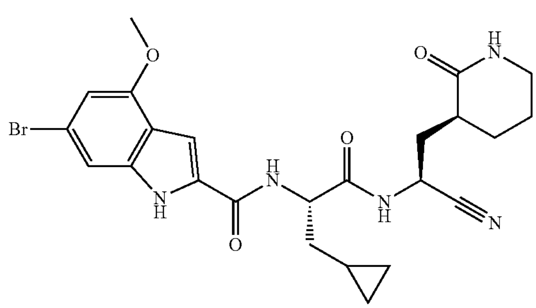 [SMILES: COc1cc(Br)cc2[nH]c(C(=O)N[C@@H](CC3CC3)C(=O)N[C@H](C#N)C[C@@H]3CCCNC3=O)cc12] |

TABLE 1-continued

Exemplary compounds.

| Cmpd No. | Structure |
|---|---|
| 845 | 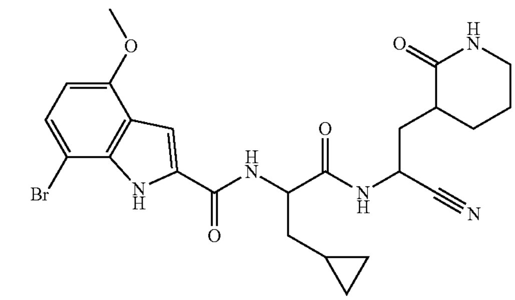 |
| 846 | 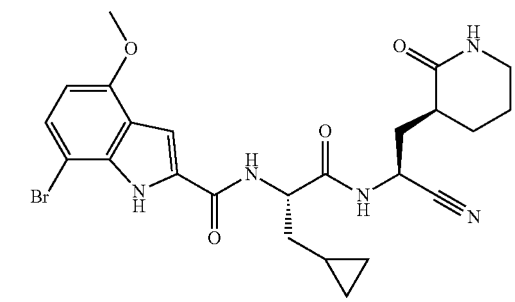 [SMILES: COc1ccc(Br)c2[nH]c(C(=O)N[C@@H](CC3CC3)C(=O)N[C@H](C#N)C[C@@H]3CCCNC3=O)cc12] |
| 847 | 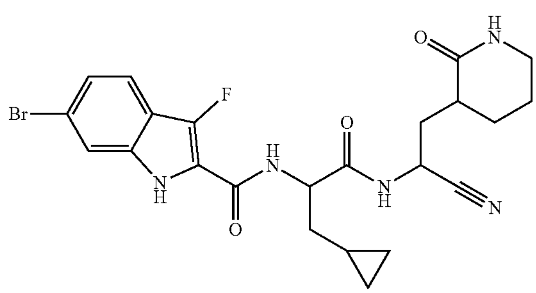 [SMILES: N#CC(CC1CCCNC1=O)NC(=O)C(CC1CC1)NC(=O)c1[nH]c2cc(Br)ccc2c1F] |
| 848 | 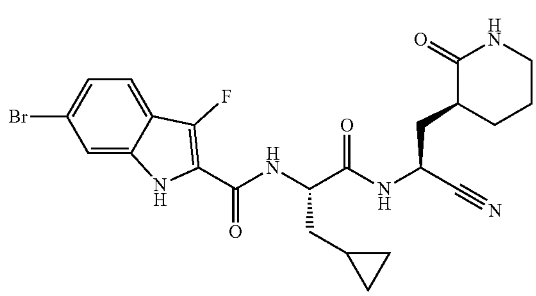 [SMILES: N#C[C@H](C[C@@H]1CCCNC1=O)NC(=O)[C@H](CC1CC1)NC(=O)c1[nH]c2cc(Br)ccc2c1F] |
| 849 | 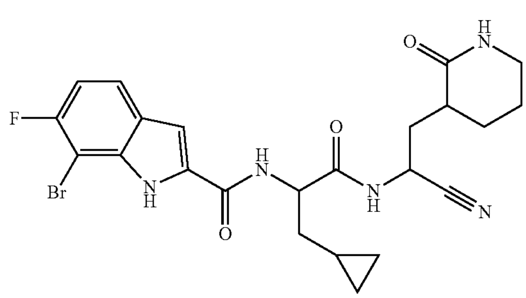 [SMILES: N#CC(CC1CCCNC1=O)NC(=O)C(CC1CC1)NC(=O)c1cc2ccc(F)c(Br)c2[nH]1] |

TABLE 1-continued

Exemplary compounds.

| Cmpd No. | Structure |
|---|---|
| 850 | 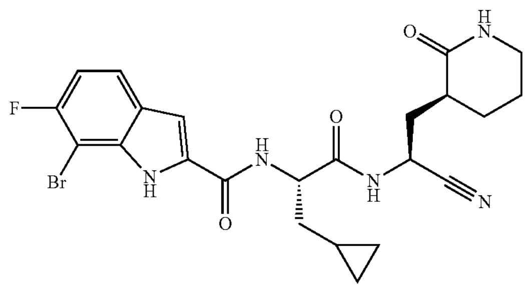 [SMILES: N#C[C@H](C[C@@H]1CCCNC1=O)NC(=O)[C@H](CC1CC1)NC(=O)c1cc2ccc(F)c(Br)c2[nH]1] |
| 851 | 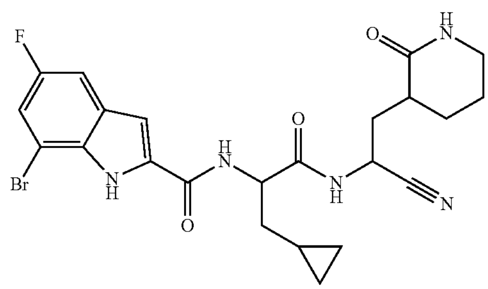 [SMILES: N#CC(CC1CCCNC1=O)NC(=O)C(CC1CC1)NC(=O)c1cc2cc(F)cc(Br)c2[nH]1] |
| 852 | 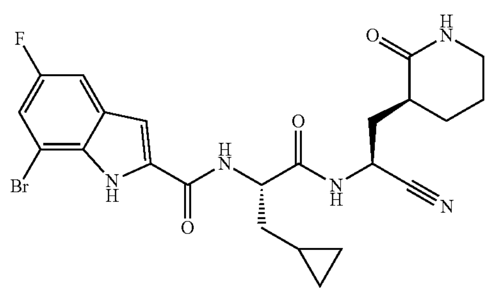 [SMILES: N#C[C@H](C[C@@H]1CCCNC1=O)NC(=O)[C@H](CC1CC1)NC(=O)c1cc2cc(F)cc(Br)c2[nH]1] |
| 853 | 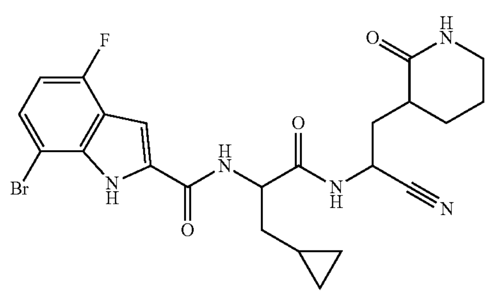 [SMILES: N#CC(CC1CCCNC1=O)NC(=O)C(CC1CC1)NC(=O)c1cc2c(F)ccc(Br)c2[nH]1] |
| 854 | 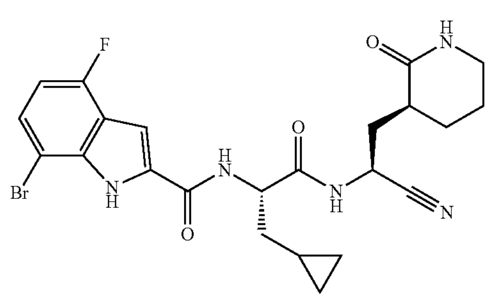 [SMILES: N#C[C@H](C[C@@H]1CCCNC1=O)NC(=O)[C@H](CC1CC1)NC(=O)c1cc2c(F)ccc(Br)c2[nH]1] |

TABLE 1-continued

Exemplary compounds.

| Cmpd No. | Structure |
|---|---|
| 855 | 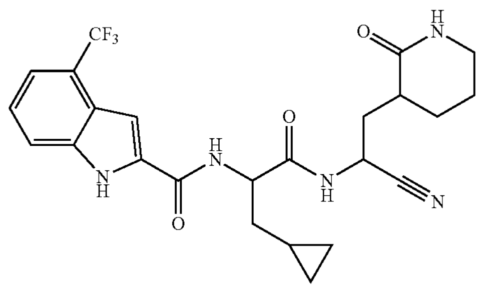 |
| 856 | 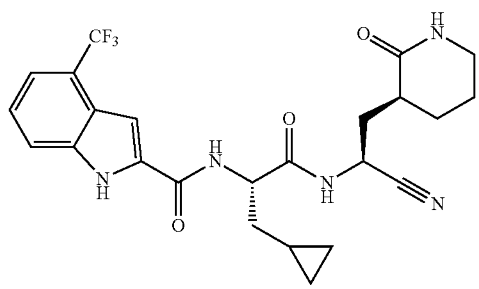 [SMILES: N#C[C@H](C[C@@H]1CCCNC1=O)NC(=O)[C@H](CC1CC1)NC(=O)c1cc2c(C(F)(F)F)cccc2[nH]1] |
| 857 | 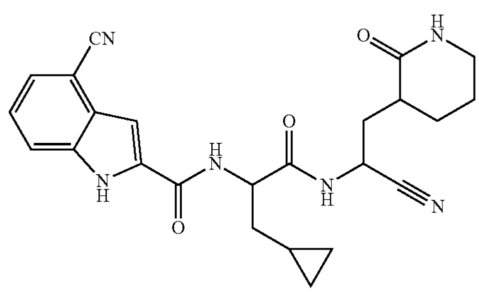 [SMILES: N#Cc1cccc2[nH]c(C(=O)NC(CC3CC3)C(=O)NC(C#N)CC3CCCNC3=O)cc12] |
| 858 | 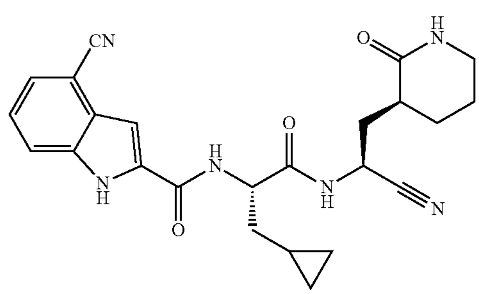 [SMILES: N#Cc1cccc2[nH]c(C(=O)N[C@@H](CC3CC3)C(=O)N[C@H](C#N)C[C@@H]3CCCNC3=O)cc12] |
| 859 | 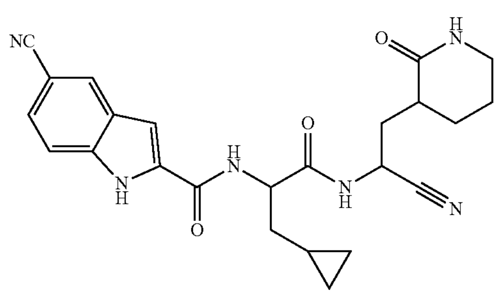 [SMILES: N#Cc1ccc2[nH]c(C(=O)NC(CC3CC3)C(=O)NC(C#N)CC3CCCNC3=O)cc2c1] |

TABLE 1-continued

Exemplary compounds.

| Cmpd No. | Structure |
|---|---|
| 860 | 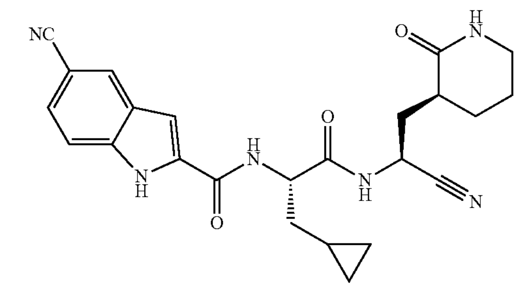 [SMILES: N#Cc1ccc2[nH]c(C(=O)N[C@@H](CC3CC3)C(=O)N[C@H](C#N)C[C@@H]3CCCNC3=O)cc2c1] |
| 861 | 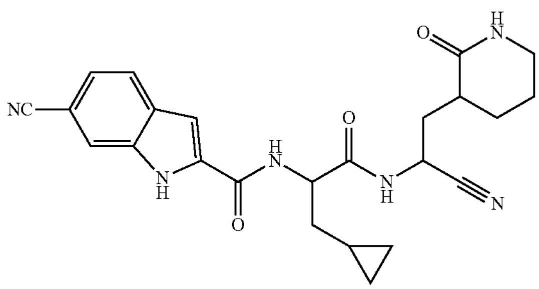 [SMILES: N#Cc1ccc2cc(C(=O)NC(CC3CC3)C(=O)NC(C#N)CC3CCCNC3=O)[nH]c2c1] |
| 862 | 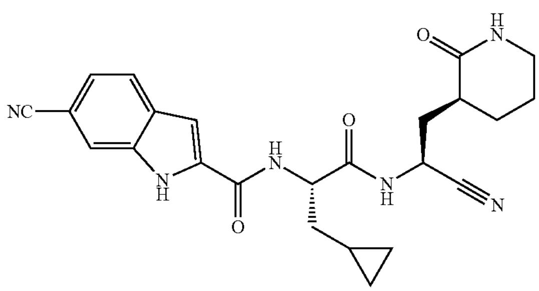 [SMILES: N#Cc1ccc2cc(C(=O)N[C@@H](CC3CC3)C(=O)N[C@H](C#N)C[C@@H]3CCCNC3=O)[nH]c2c1] |
| 863 | 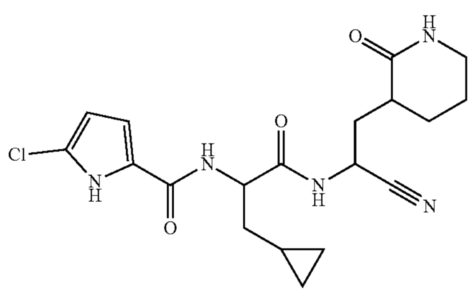 [SMILES: N#CC(CC1CCCNC1=O)NC(=O)C(CC1CC1)NC(=O)c1ccc(Cl)[nH]1] |
| 864 | 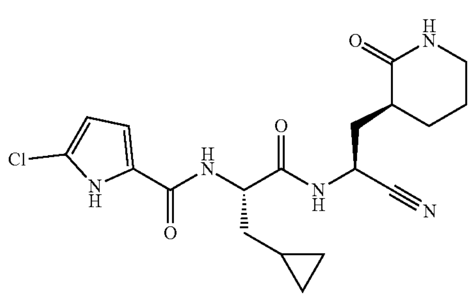 [SMILES: N#C[C@H](C[C@@H]1CCCNC1=O)NC(=O)[C@H](CC1CC1)NC(=O)c1ccc(Cl)[nH]1] |

TABLE 1-continued
Exemplary compounds.
| Cmpd No. | Structure |
|---|---|
| 865 | 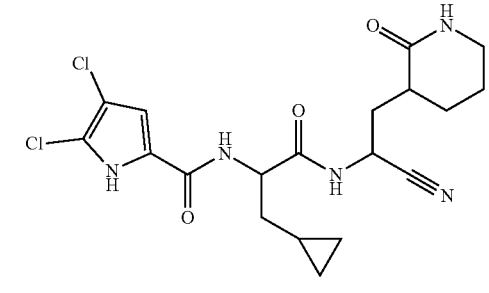 [SMILES: N#CC(CC1CCCNC1=O)NC(=O)C(CC1CC1)NC(=O)c1cc(Cl)c(Cl)[nH]1] |
| 866 | 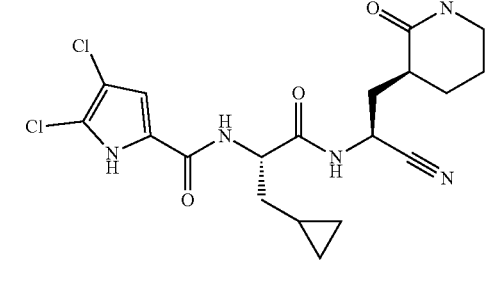 |
| 867 | 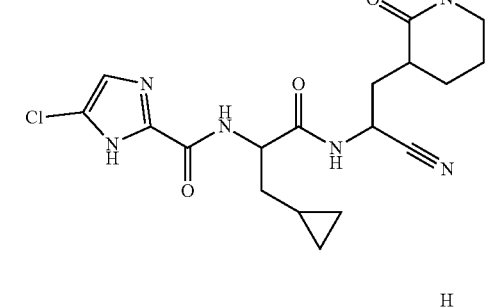 |
| 868 | 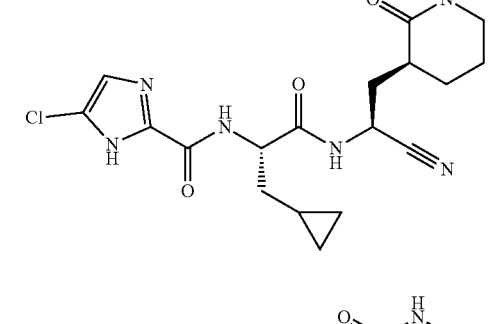 |
| 869 | 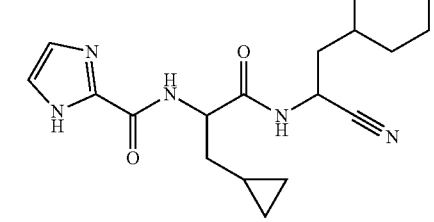 |

TABLE 1-continued

Exemplary compounds.

| Cmpd No. | Structure |
|---|---|
| 870 | 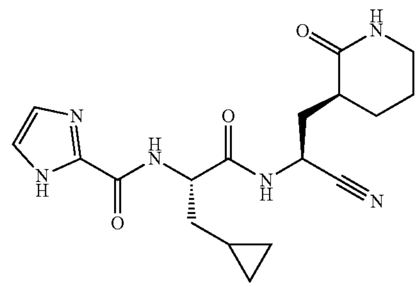 [SMILES: N#C[C@H](C[C@@H]1CCCNC1=O)NC(=O)[C@H](CC1CC1)NC(=O)c1ncc[nH]1] |
| 871 | 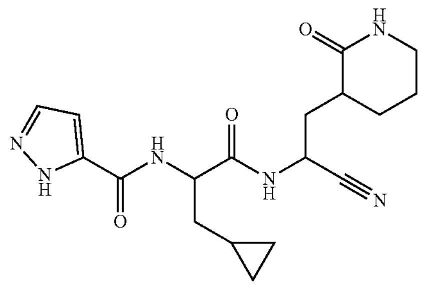 [SMILES: N#CC(CC1CCCNC1=O)NC(=O)C(CC1CC1)NC(=O)c1ccn[nH]1] |
| 872 | 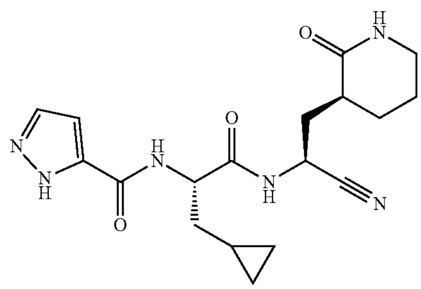 [SMILES: N#C[C@H](C[C@@H]1CCCNC1=O)NC(=O)[C@H](CC1CC1)NC(=O)c1ccn[nH]1] |
| 873 | 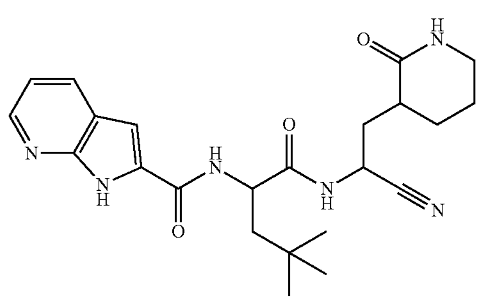 [SMILES: CC(C)(C)CC(NC(=O)c1cc2cccnc2[nH]1)C(=O)NC(C#N)CC1CCCNC1=O] |
| 874 | 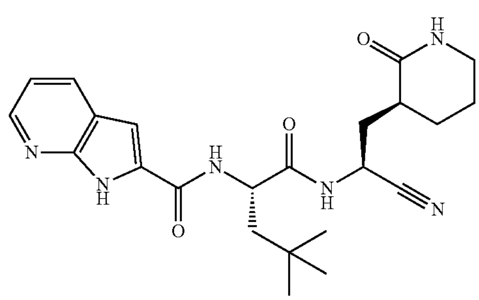 [SMILES: CC(C)(C)C[C@H](NC(=O)c1cc2cccnc2[nH]1)C(=O)N[C@H](C#N)C[C@@H]1CCCNC1=O] |

TABLE 1-continued
| Cmpd No. | Structure |
|---|---|
| 875 | 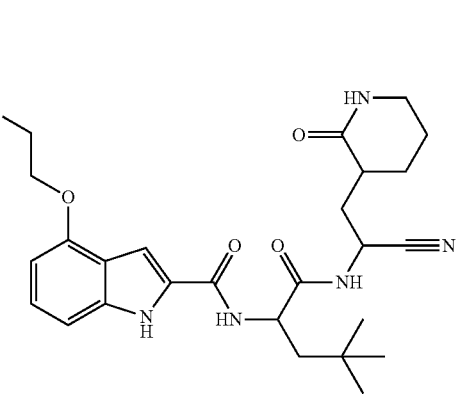 |
| 876 | 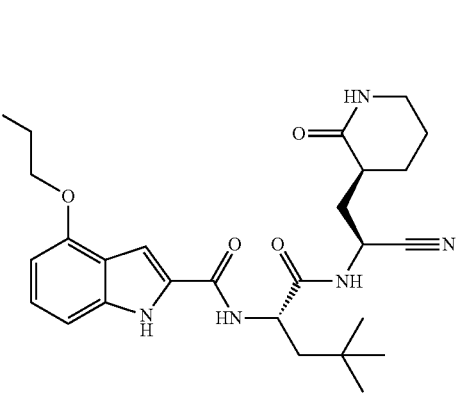 |
| 877 | 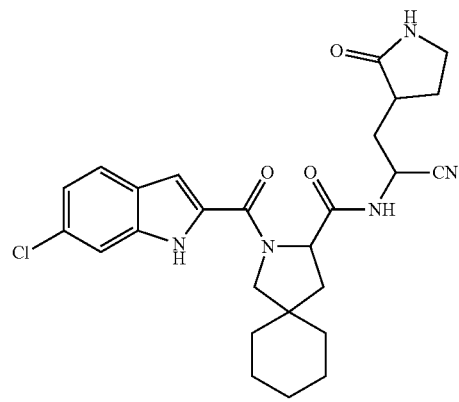 [SMILES: N#CC(CC1CCNC1=O)NC(=O)C1CC2(CCCCC2)CN1C(=O)c1cc2ccc(Cl)cc2[nH]1] |

TABLE 1-continued
Exemplary compounds.
| Cmpd No. | Structure |
|---|---|
| 878 | 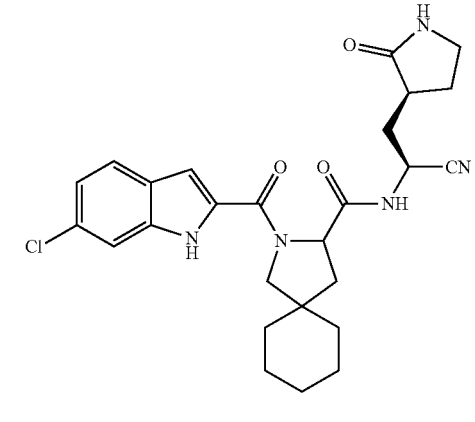 [SMILES: N#C[C@H](C[C@@H]1CCNC1=O)NC(=O)C1CC2(CCCCC2)CN1C(=O)c1cc2ccc(Cl)cc2[nH]1] |
| 879 | 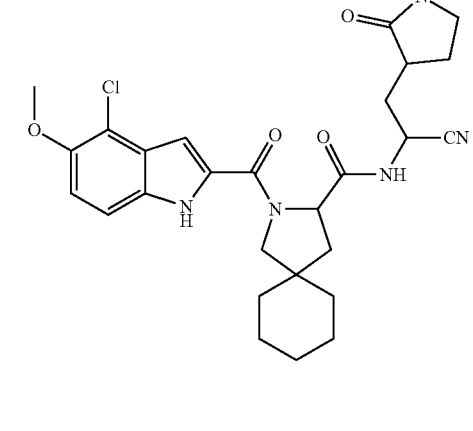 |
| 880 | 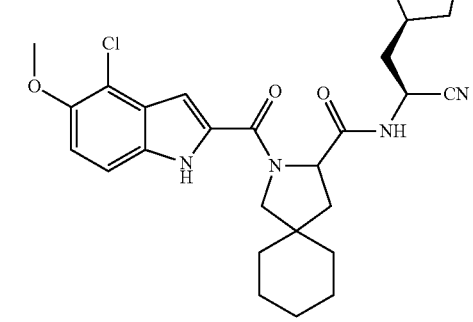 |

TABLE 1-continued

Exemplary compounds.

| Cmpd No. | Structure |
|---|---|
| 881 | 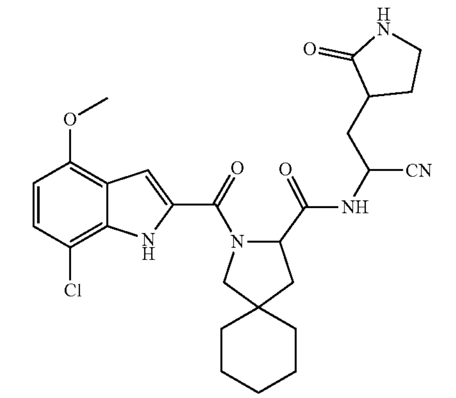 [SMILES: COc1ccc(Cl)c2[nH]c(C(=O)N3CC4(CCCCC4)CC3C(=O)NC(C#N)CC3CCNC3=O)cc12] |
| 882 | 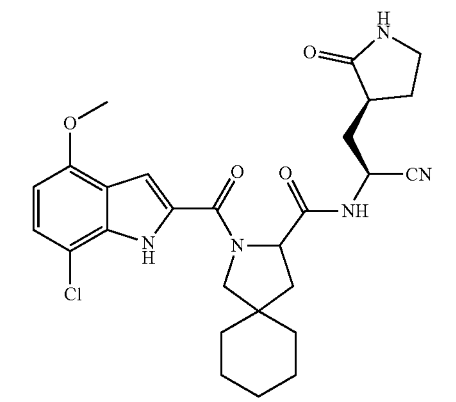 [SMILES: COc1ccc(Cl)c2[nH]c(C(=O)N3CC4(CCCCC4)CC3C(=O)N[C@H](C#N)C[C@@H]3CCNC3=O)cc12] |
| 883 | 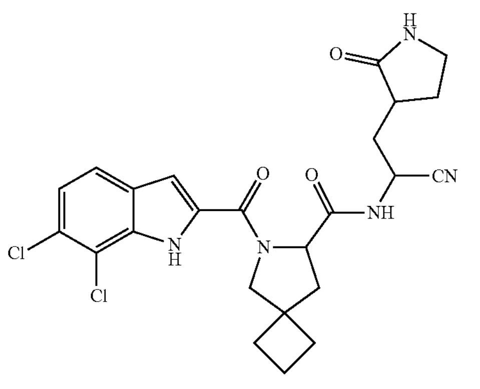 [SMILES: N#CC(CC1CCNC1=O)NC(=O)C1CC2(CCC2)CN1C(=O)c1cc2ccc(Cl)c(Cl)c2[nH]1] |
| 884 | 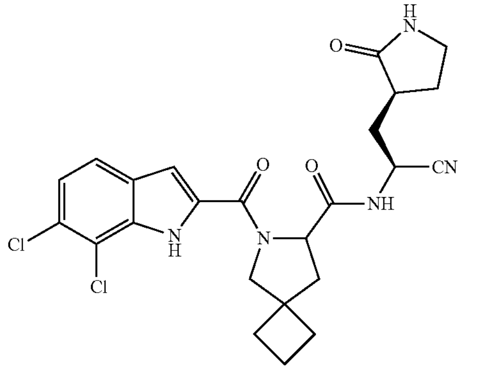 [SMILES: N#C[C@H](C[C@@H]1CCNC1=O)NC(=O)C1CC2(CCC2)CN1C(=O)c1cc2ccc(Cl)c(Cl)c2[nH]1] |

TABLE 1-continued

Exemplary compounds.

| Cmpd No. | Structure |
|---|---|
| 885 | 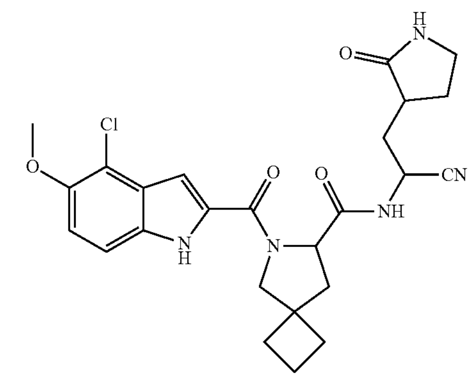 [SMILES: COc1ccc2[nH]c(C(=O)N3CC4(CCC4)CC3C(=O)NC(C#N)CC3CCNC3=O)cc2c1Cl] |
| 886 | 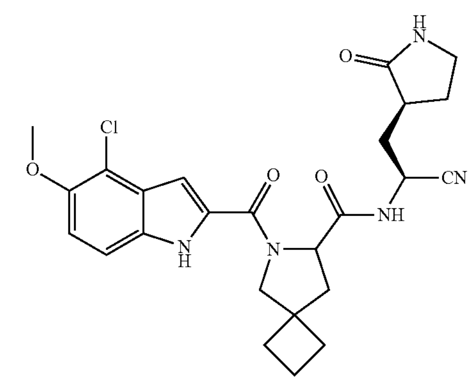 [SMILES: COc1ccc2[nH]c(C(=O)N3CC4(CCC4)CC3C(=O)N[C@H](C#N)C[C@@H]3CCNC3=O)cc2c1Cl] |
| 887 | 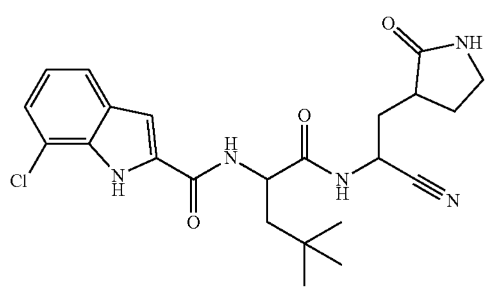 [SMILES: CC(C)(C)CC(NC(=O)c1cc2cccc(Cl)c2[nH]1)C(=O)NC(C#N)CC1CCNC1=O] |
| 888 | 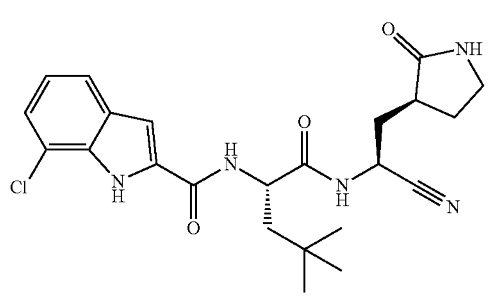 [SMILES: CC(C)(C)C[C@H](NC(=O)c1cc2cccc(Cl)c2[nH]1)C(=O)N[C@H](C#N)C[C@@H]1CCNC1=O] |

TABLE 1-continued
Exemplary compounds.
| Cmpd No. | Structure |
|---|---|
| 889 | 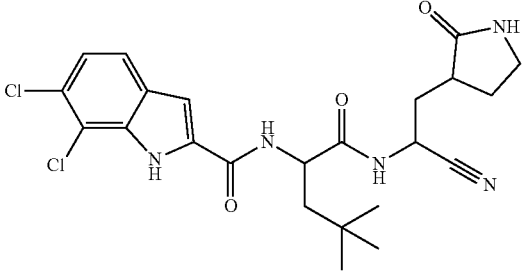 [SMILES: CC(C)(C)CC(NC(=O)c1cc2ccc(Cl)c(Cl)c2[nH]1)C(=O)NC(C#N)CC1CCNC1=O] |
| 890 | 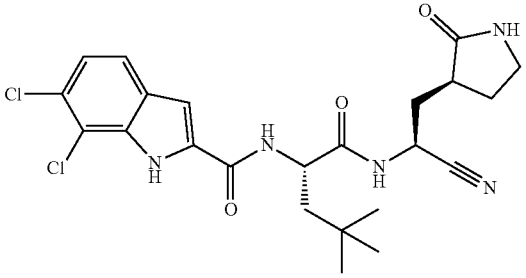 [SMILES: CC(C)(C)C[C@H](NC(=O)c1cc2ccc(Cl)c(Cl)c2[nH]1)C(=O)N[C@H](C#N)C[C@@H]1CCNC1=O] |
| 891 | 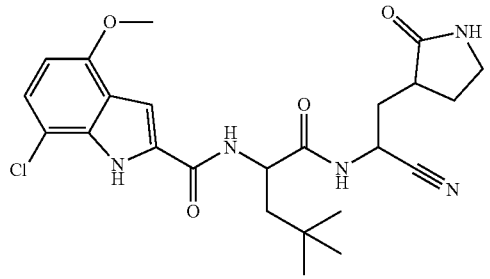 [SMILES: COc1ccc(Cl)c2[nH]c(C(=O)NC(CC(C)(C)C)C(=O)NC(C#N)CC3CCNC3=O)cc12] |
| 892 | 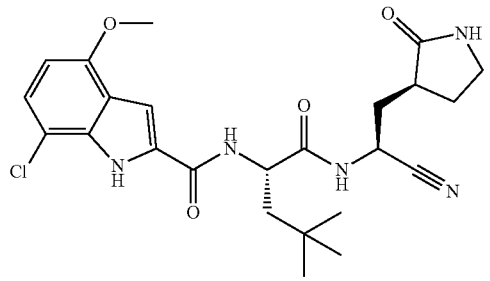 [SMILES: COc1ccc(Cl)c2[nH]c(C(=O)N[C@@H](CC(C)(C)C)C(=O)N[C@H](C#N)C[C@@H]3CCNC3=O)cc12] |
| 893 | 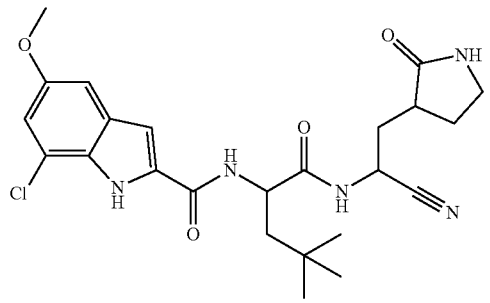 [SMILES: COc1cc(Cl)c2[nH]c(C(=O)NC(CC(C)(C)C)C(=O)NC(C#N)CC3CCNC3=O)cc2c1] |

463 464
TABLE 1-continued
Exemplary compounds.
| Cmpd No. | Structure |
|---|---|
| 894 | 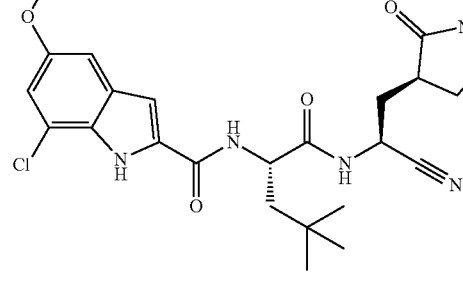 |
| 895 | 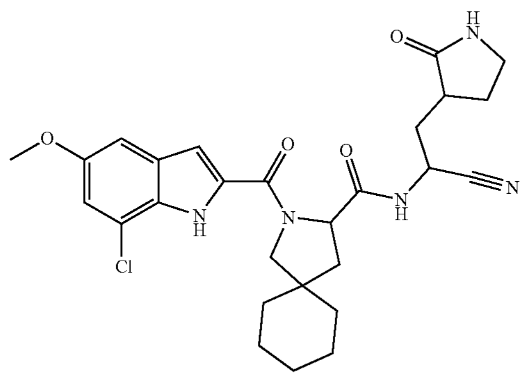 [SMILES: COc1cc(Cl)c2[nH]c(C(=O)N3CC4(CCCCC4)CC3C(=O)NC(C#N)CC3CCNC3=O)cc2c1] |
| 896 | 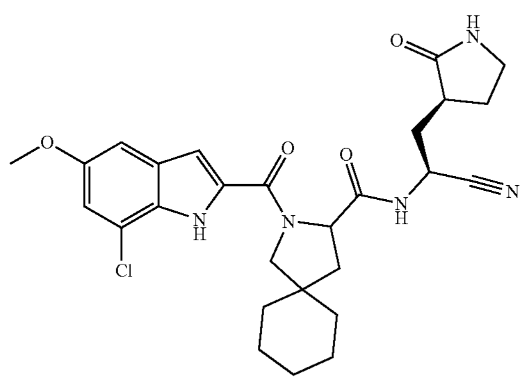 [SMILES: COc1cc(Cl)c2[nH]c(C(=O)N3CC4(CCCCC4)CC3C(=O)N[C@H](C#N)C[C@@H]3CCNC3=O)cc2c1] |
| 897 | 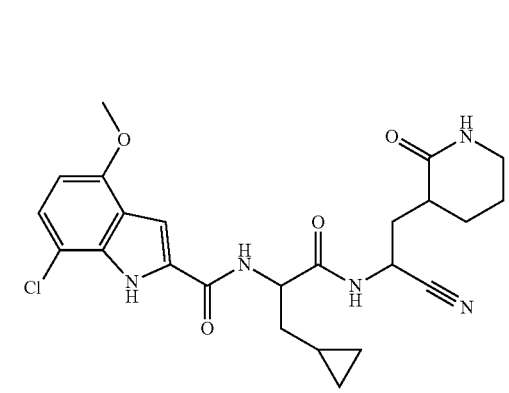 [SMILES: COc1ccc(Cl)c2[nH]c(C(=O)NC(CC3CC3)C(=O)NC(C#N)CC3CCCNC3=O)cc12] |

TABLE 1-continued

Exemplary compounds.

| Cmpd No. | Structure |
|---|---|
| 898 | 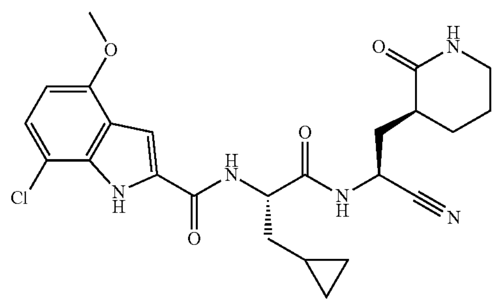 [SMILES: COc1ccc(Cl)c2[nH]c(C(=O)N[C@@H](CC3CC3)C(=O)N[C@H](C#N)C[C@@H]3CCCNC3=O)cc12] |
| 899 | 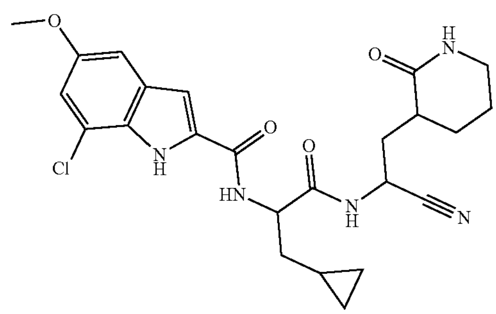 [SMILES: COc1cc(Cl)c2[nH]c(C(=O)NC(CC3CC3)C(=O)NC(C#N)CC3CCCNC3=O)cc2c1] |
| 900 | 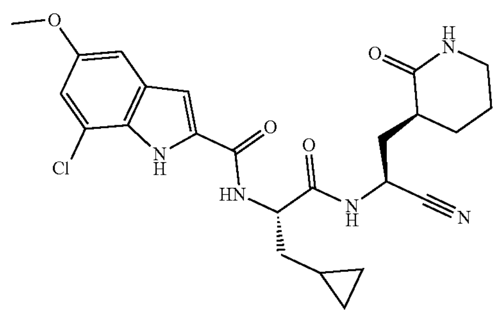 [SMILES: COc1cc(Cl)c2[nH]c(C(=O)N[C@@H](CC3CC3)C(=O)N[C@H](C#N)C[C@@H]3CCCNC3=O)cc2c1] |
| 901 | 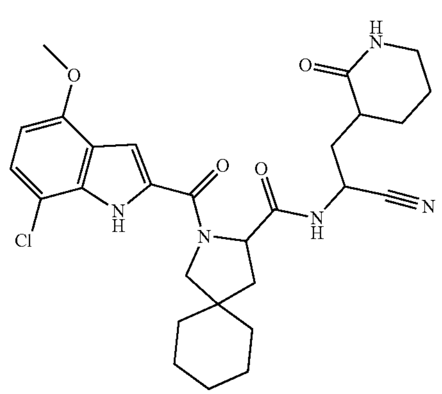 [SMILES: COc1ccc(Cl)c2[nH]c(C(=O)N3CC4(CCCCC4)CC3C(=O)NC(C#N)CC3CCCNC3=O)cc12] |

TABLE 1-continued

Exemplary compounds.

| Cmpd No. | Structure |
|---|---|
| 902 | 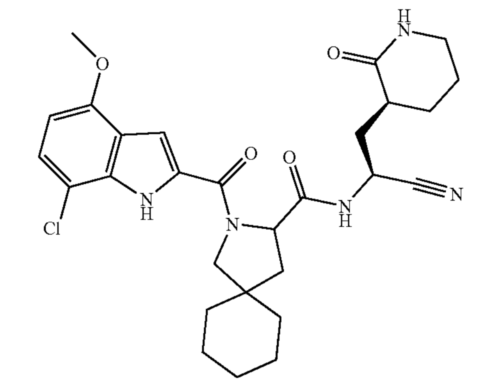 [SMILES: COc1ccc(Cl)c2[nH]c(C(=O)N3CC4(CCCCC4)CC3C(=O)N[C@H](C#N)C[C@@H]3CCCNC3=O)cc12] |
| 903 | 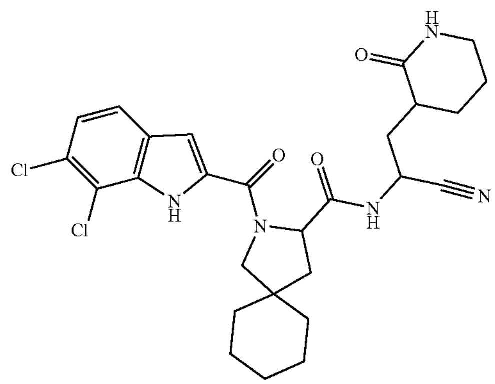 [SMILES: N#CC(CC1CCCNC1=O)NC(=O)C1CC2(CCCCC2)CN1C(=O)c1cc2ccc(Cl)c(Cl)c2[nH]1] |
| 904 | 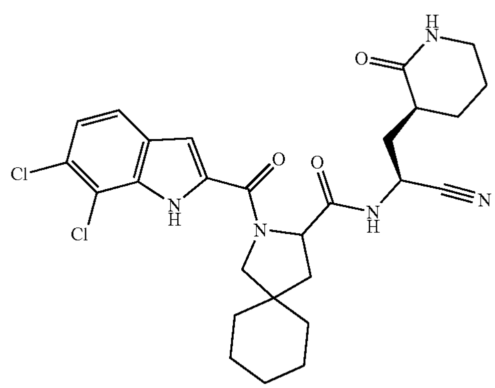 [SMILES: N#C[C@H](C[C@@H]1CCCNC1=O)NC(=O)C1CC2(CCCCC2)CN1C(=O)c1cc2ccc(Cl)c(Cl)c2[nH]1] |
| 905 | 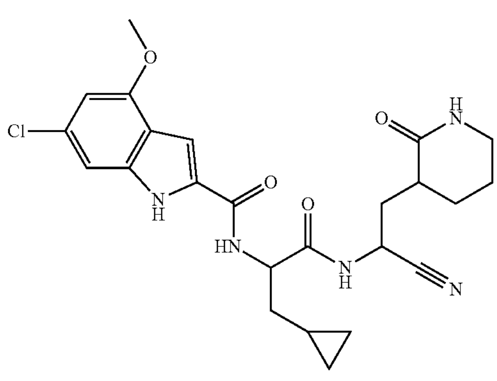 [SMILES: COc1cc(Cl)cc2[nH]c(C(=O)NC(CC3CC3)C(=O)NC(C#N)CC3CCCNC3=O)cc12] |

TABLE 1-continued
Exemplary compounds.
| Cmpd No. | Structure |
|---|---|
| 906 | 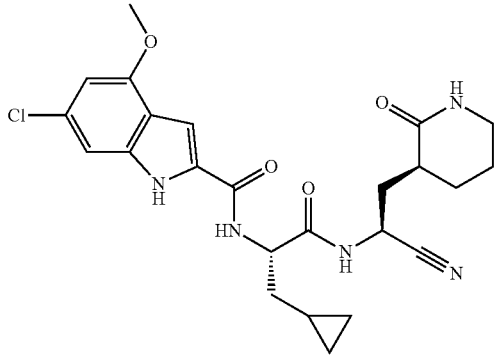 [SMILES: COc1cc(Cl)cc2[nH]c(C(=O)N[C@@H](CC3CC3)C(=O)N[C@H](C#N)C[C@@H]3CCCNC3=O)cc12] |
| 907 | 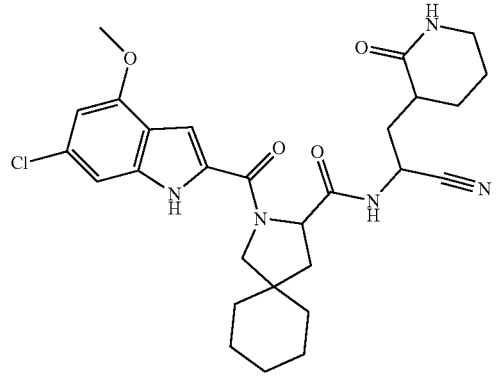 [SMILES: COc1cc(Cl)cc2[nH]c(C(=O)N3CC4(CCCCC4)CC3C(=O)NC(C#N)CC3CCCNC3=O)cc12] |
| 908 | 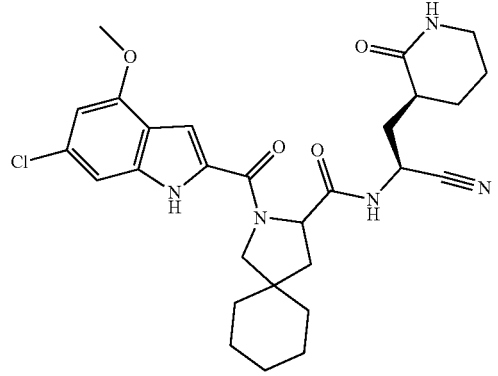 [SMILES: COc1cc(Cl)cc2[nH]c(C(=O)N3CC4(CCCCC4)CC3C(=O)N[C@H](C#N)C[C@@H]3CCCNC3=O)cc12] |
| 909 | 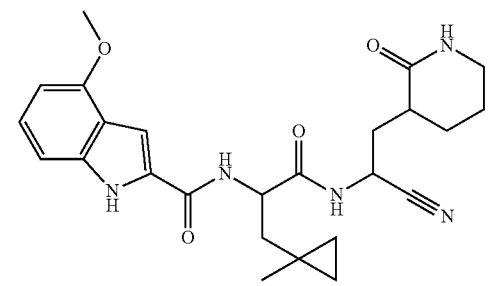 [SMILES: COc1cccc2[nH]c(C(=O)NC(CC3(C)CC3)C(=O)NC(C#N)CC3CCCNC3=O)cc12] |

471 472
TABLE 1-continued
Exemplary compounds.
| Cmpd No. | Structure |
|---|---|
| 910 | 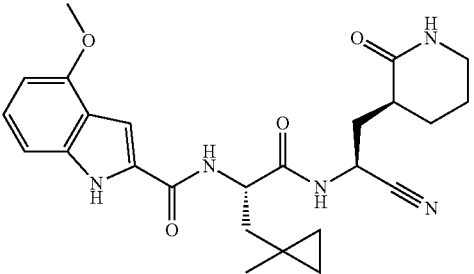 [SMILES: COc1cccc2[nH]c(C(=O)N[C@@H](CC3(C)CC3)C(=O)N[C@H](C#N)C[C@@H]3CCCNC3=O)cc12] |
| 911 | 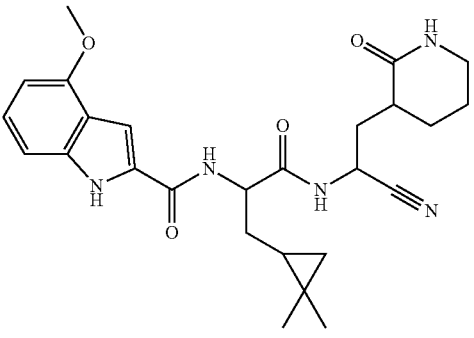 [SMILES: COc1cccc2[nH]c(C(=O)NC(CC3CC3(C)C)C(=O)NC(C#N)CC3CCCNC3=O)cc12] |
| 912 | 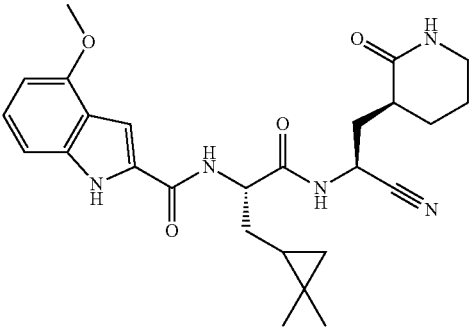 [SMILES: COc1cccc2[nH]c(C(=O)N[C@@H](CC3CC3(C)C)C(=O)N[C@H](C#N)C[C@@H]3CCCNC3=O)cc12] |
| 913 | 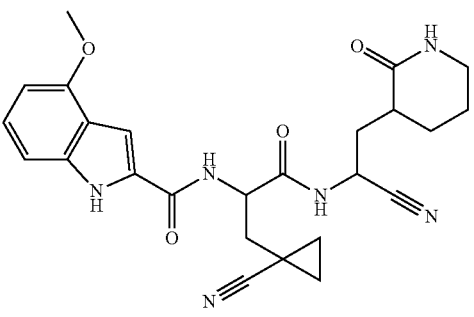 [SMILES: COc1cccc2[nH]c(C(=O)NC(CC3(C#N)CC3)C(=O)NC(C#N)CC3CCCNC3=O)cc12] |

TABLE 1-continued
Exemplary compounds.
| Cmpd No. | Structure |
|---|---|
| 914 | 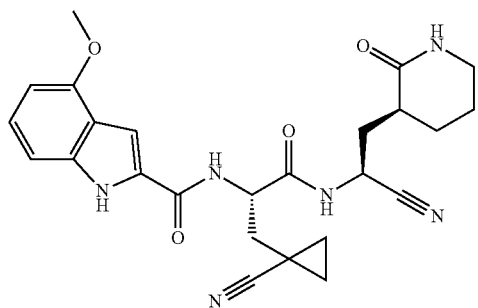 [SMILES: COc1cccc2[nH]c(C(=O)N[C@@H](CC3(C#N)CC3)C(=O)N[C@H](C#N)C[C@@H]3CCCNC3=O)cc12] |
| 915 | 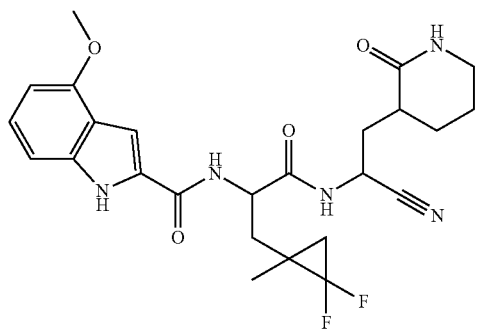 [SMILES: COc1cccc2[nH]c(C(=O)NC(CC3(C)CC3(F)F)C(=O)NC(C#N)CC3CCCNC3=O)cc12] |
| 916 | 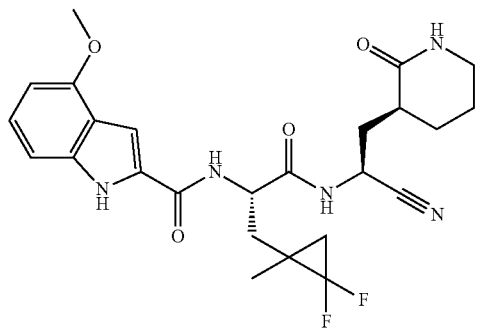 [SMILES: COc1cccc2[nH]c(C(=O)N[C@@H](CC3(C)CC3(F)F)C(=O)N[C@H](C#N)C[C@@H]3CCCNC3=O)cc12] |
| 917 | 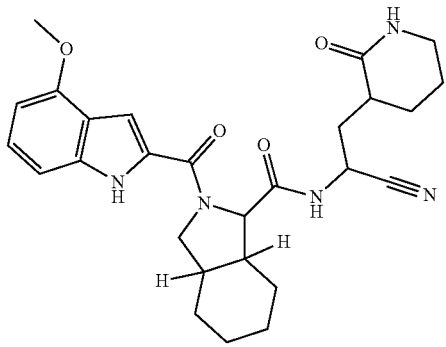 [SMILES: COc1cccc2[nH]c(C(=O)N3CC4CCCCC4C3C(=O)NC(C#N)CC3CCCNC3=O)cc12] |

TABLE 1-continued

Exemplary compounds.

| Cmpd No. | Structure |
|---|---|
| 918 | 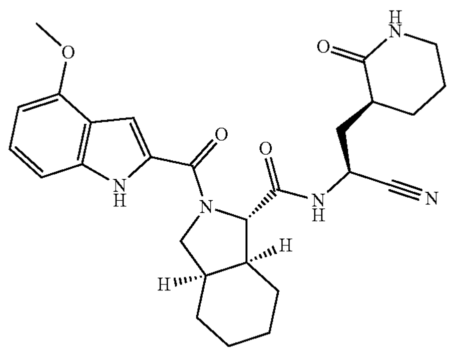 [SMILES: COc1cccc2[nH]c(C(=O)N3C[C@@H]4CCCC[C@@H]4[C@H]3C(=O)N[C@H](C#N)C[C@@H]3CCCNC3=O)cc12] |
| 919 | 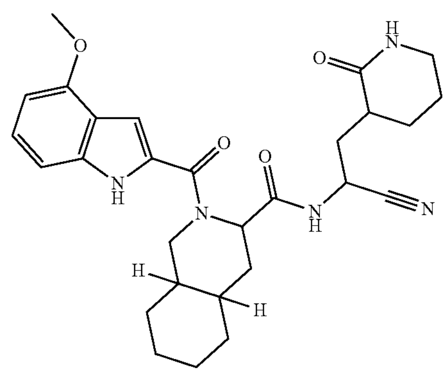 [SMILES: COc1cccc2[nH]c(C(=O)N3CC4CCCCC4CC3C(=O)NC(C#N)CC3CCCNC3=O)cc12] |
| 920 | 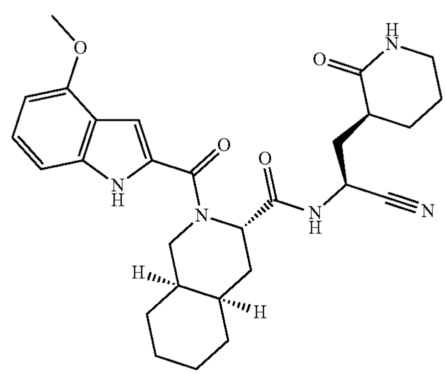 [SMILES: COc1cccc2[nH]c(C(=O)N3C[C@@H]4CCCC[C@@H]4C[C@H]3C(=O)N[C@H](C#N)C[C@@H]3CCCNC3=O)cc12] |
| 921 | 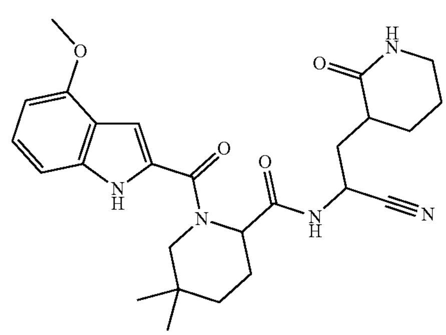 [SMILES: COc1cccc2[nH]c(C(=O)N3CC(C)(C)CCC3C(=O)NC(C#N)CC3CCCNC3=O)cc12] |

TABLE 1-continued

Exemplary compounds.

| Cmpd No. | Structure |
|---|---|
| 922 | 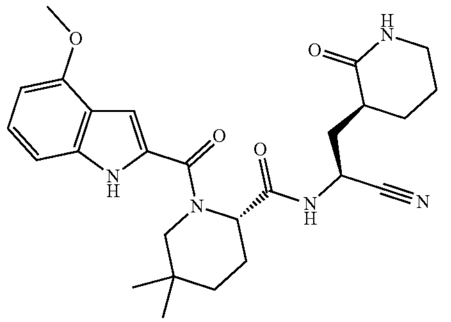 [SMILES: COc1cccc2[nH]c(C(=O)N3CC(C)(C)CC[C@H]3C(=O)N[C@H](C#N)C[C@@H]3CCCNC3=O)cc12] |
| 927 | 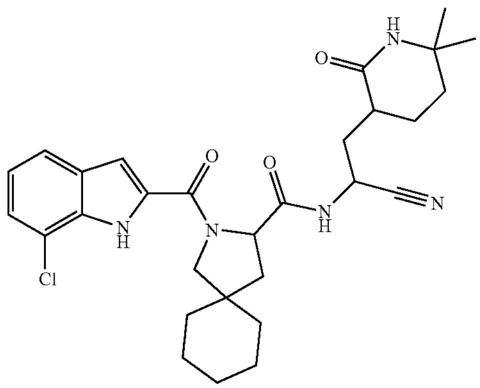 [SMILES: CC1(C)CCC(CC(C#N)NC(=O)C2CC3(CCCCC3)CN2C(=O)c2cc3cccc(Cl)c3[nH]2)C(=O)N1] |
| 928 | 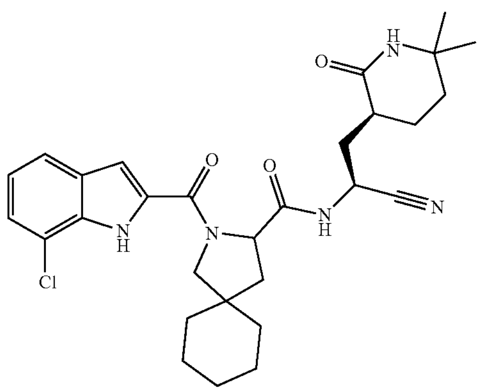 [SMILES: CC1(C)CC[C@@H](C[C@@H](C#N)NC(=O)C2CC3(CCCCC3)CN2C(=O)c2cc3cccc(Cl)c3[nH]2)C(=O)N1] |
| 929 | 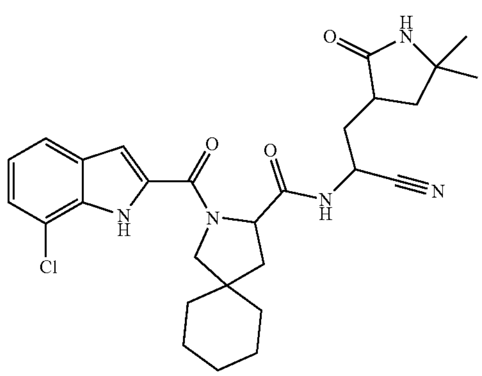 [SMILES: CC1(C)CC(CC(C#N)NC(=O)C2CC3(CCCCC3)CN2C(=O)c2cc3cccc(Cl)c3[nH]2)C(=O)N1] |

TABLE 1-continued

Exemplary compounds.

| Cmpd No. | Structure |
|---|---|
| 930 | 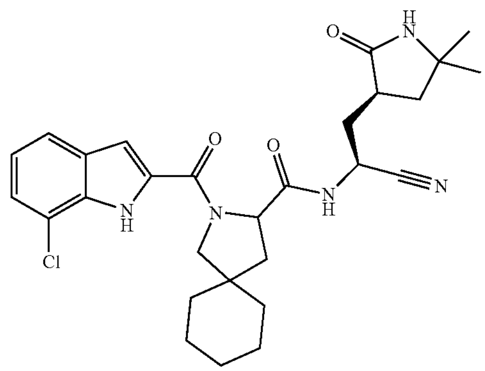 [SMILES: CC1(C)C[C@@H](C[C@@H](C#N)NC(=O)C2CC3(CCCCC3)CN2C(=O)c2cc3cccc(Cl)c3[nH]2)C(=O)N1] |
| 931 | 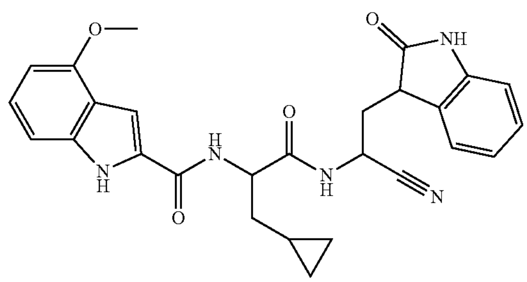 [SMILES: COc1cccc2[nH]c(C(=O)NC(CC3CC3)C(=O)NC(C#N)CC3C(=O)Nc4ccccc43)cc12] |
| 932 | 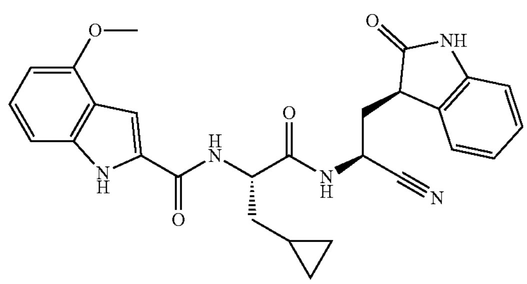 [SMILES: COc1cccc2[nH]c(C(=O)N[C@@H](CC3CC3)C(=O)N[C@H](C#N)C[C@H]3C(=O)Nc4ccccc43)cc12] |
| 933 | 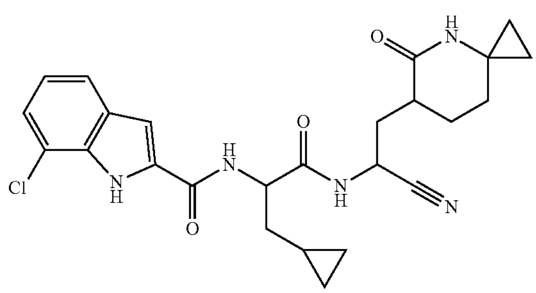 [SMILES: N#CC(CC1CCC2(CC2)NC1=O)NC(=O)C(CC1CC1)NC(=O)c1cc2cccc(Cl)c2[nH]1] |
| 934 | 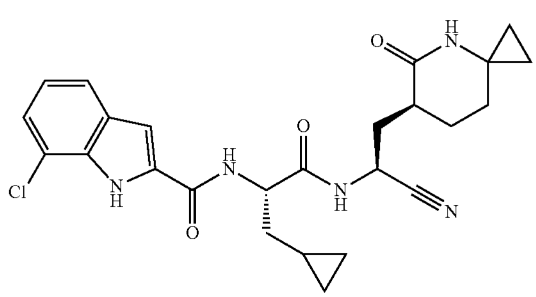 [SMILES: N#C[C@H](C[C@@H]1CCC2(CC2)NC1=O)NC(=O)[C@H](CC1CC1)NC(=O)c1cc2cccc(Cl)c2[nH]1] |

TABLE 1-continued

Exemplary compounds.

| Cmpd No. | Structure |
|---|---|
| 935 | 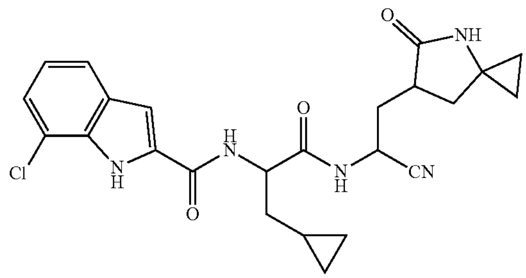 [SMILES: N#CC(CC1CC2(CC2)NC1=O)NC(=O)C(CC1CC1)NC(=O)c1cc2cccc(Cl)c2[nH]1] |
| 936 | 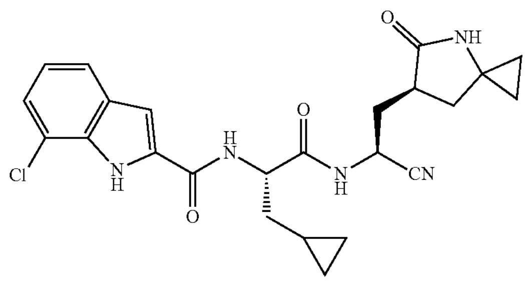 [SMILES: N#C[C@H](C[C@@H]1CC2(CC2)NC1=O)NC(=O)[C@H](CC1CC1)NC(=O)c1cc2cccc(Cl)c2[nH]1] |
| 973 | 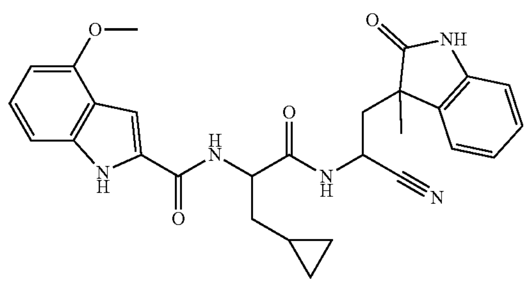 [SMILES: COc1cccc2[nH]c(C(=O)NC(CC3CC3)C(=O)NC(C#N)CC3(C)C(=O)Nc4ccccc43)cc12] |
| 974 | 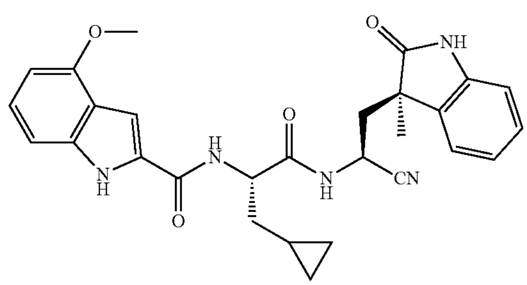 [SMILES: COc1cccc2[nH]c(C(=O)N[C@@H](CC3CC3)C(=O)N[C@H](C#N)C[C@@]3(C)C(=O)Nc4ccccc43)cc12] |
| 975 | 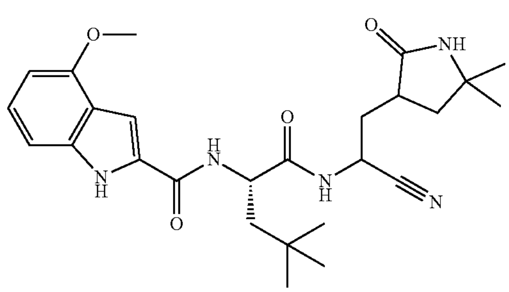 |

483                                                                        484

TABLE 1-continued

Exemplary compounds.

| Cmpd No. | Structure |
|---|---|
| 976 | 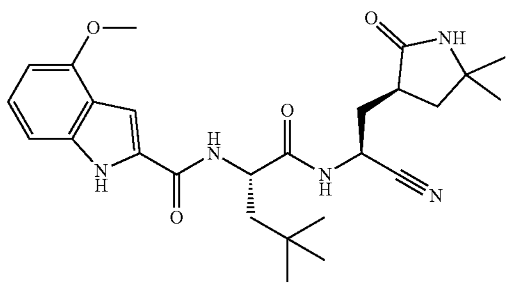 [SMILES: COc1cccc2[nH]c(C(=O)N[C@@H](CC(C)(C)C)C(=O)N[C@H](C#N)C[C@@H]3CC(C)(C)NC3=O)cc12] |
| 977 | 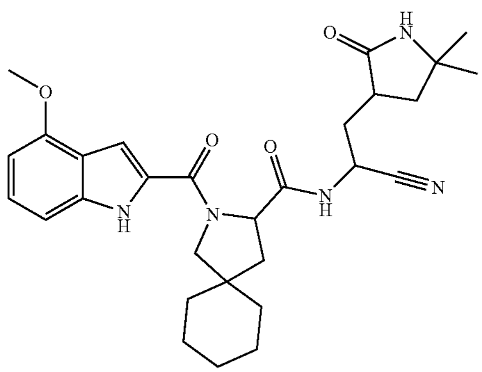 [SMILES: COc1cccc2[nH]c(C(=O)N3CC4(CCCCC4)CC3C(=O)NC(C#N)CC3CC(C)(C)NC3=O)cc12] |
| 978 | 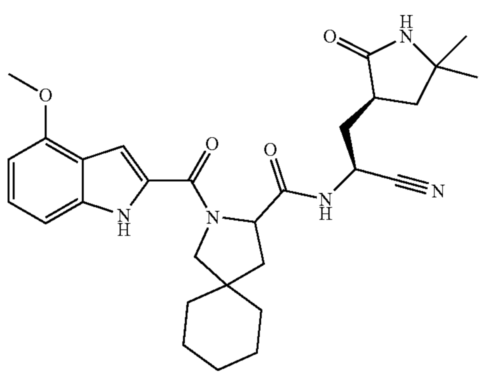 [SMILES: COc1cccc2[nH]c(C(=O)N3CC4(CCCCC4)CC3C(=O)N[C@H](C#N)C[C@@H]3CC(C)(C)NC3=O)cc12] |
| 979 | 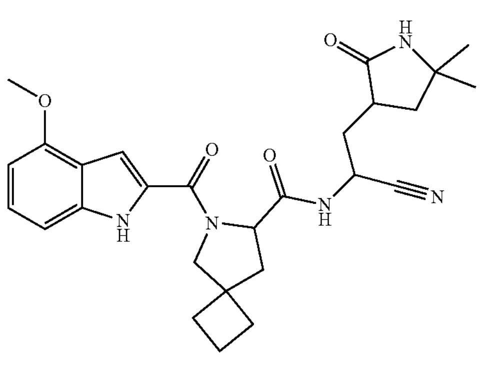 |

TABLE 1-continued

Exemplary compounds.

| Cmpd No. | Structure |
|---|---|
| 980 | 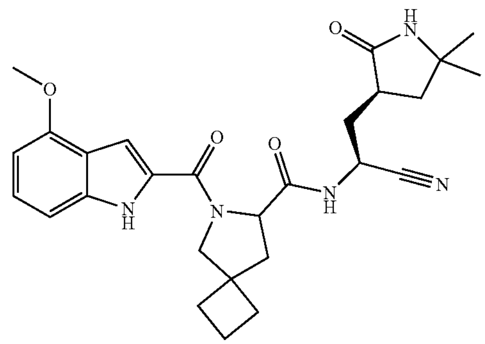 |
| 981 | 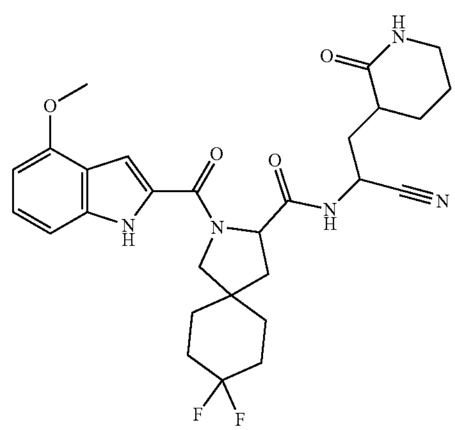 [SMILES: COc1cccc2[nH]c(C(=O)N3CC4(CCC(F)(F)CC4)CC3C(=O)NC(C#N)CC3CCCNC3=O)cc12] |
| 982 | 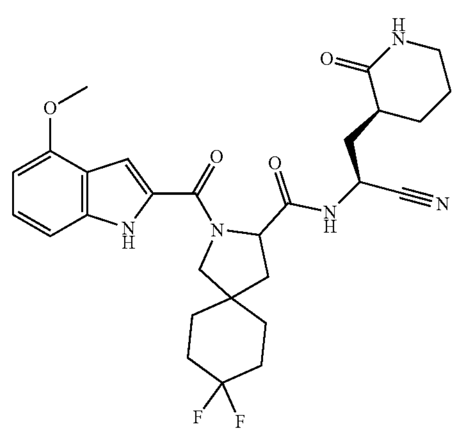 [SMILES: COc1cccc2[nH]c(C(=O)N3CC4(CCC(F)(F)CC4)CC3C(=O)N[C@H](C#N)C[C@@H]3CCCNC3=O)cc12] |

TABLE 1-continued

Exemplary compounds.

| Cmpd No. | Structure |
|---|---|
| 983 | 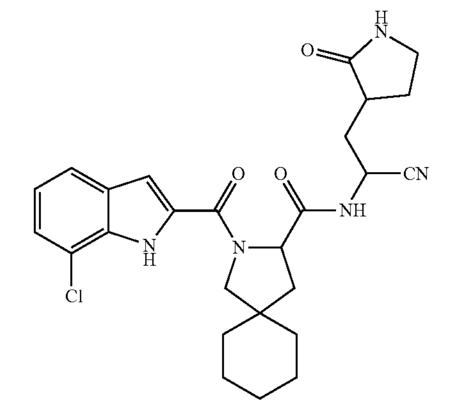 [SMILES: N#CC(CC1CCNC1=O)NC(=O)C1CC2(CCCCC2)CN1C(=O)c1cc2cccc(Cl)c2[nH]1] |
| 984 | 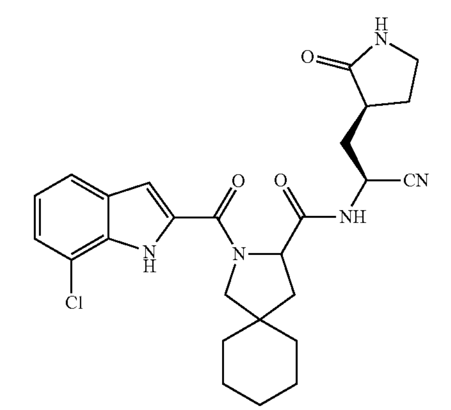 [SMILES: N#C[C@H](C[C@@H]1CCNC1=O)NC(=O)C1CC2(CCCCC2)CN1C(=O)c1cc2cccc(Cl)c2[nH]1] |
| 985 | 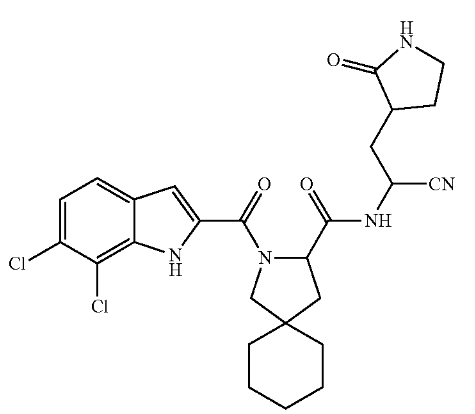 [SMILES: N#CC(CC1CCNC1=O)NC(=O)C1CC2(CCCCC2)CN1C(=O)c1cc2ccc(Cl)c(Cl)c2[nH]1] |

TABLE 1-continued
Exemplary compounds.
| Cmpd No. | Structure |
|---|---|
| 986 | 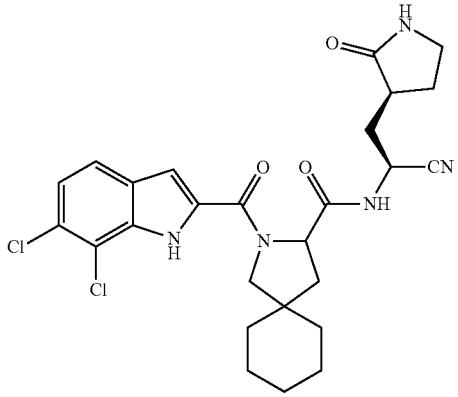 [SMILES: N#C[C@H](C[C@@H]1CCNC1=O)NC(=O)C1CC2(CCCCC2)CN1C(=O)c1cc2ccc(Cl)c(Cl)c2[nH]1] |
| 987 | 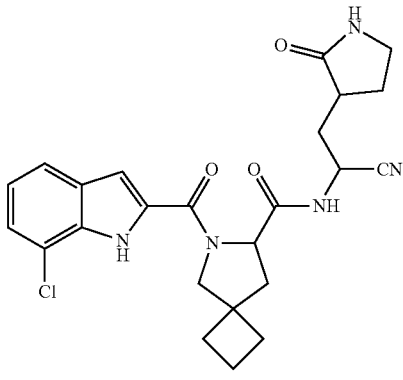 [SMILES: N#CC(CC1CCNC1=O)NC(=O)C1CC2(CCC2)CN1C(=O)c1cc2cccc(Cl)c2[nH]1] |
| 988 | 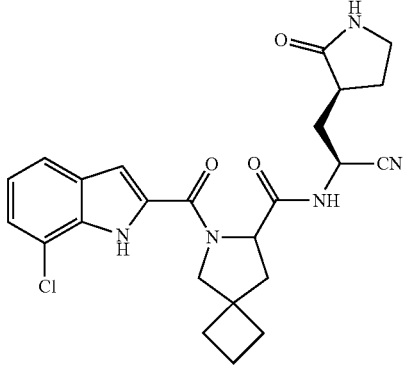 [SMILES: N#C[C@H](C[C@@H]1CCNC1=O)NC(=O)C1CC2(CCC2)CN1C(=O)c1cc2cccc(Cl)c2[nH]1] |
| 989 | 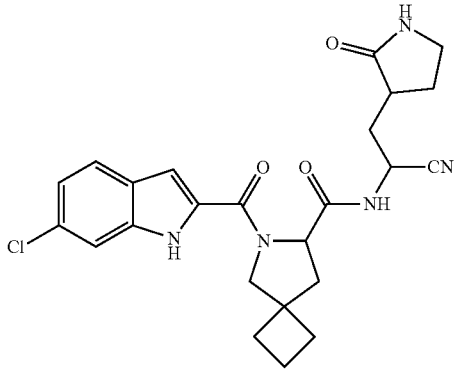 [SMILES: N#CC(CC1CCNC1=O)NC(=O)C1CC2(CCC2)CN1C(=O)c1cc2ccc(Cl)cc2[nH]1] |

TABLE 1-continued

Exemplary compounds.

| Cmpd No. | Structure |
|---|---|
| 990 | 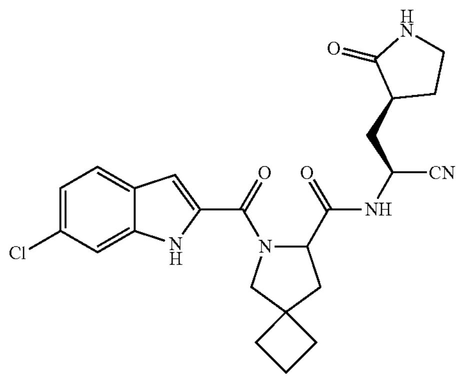 [SMILES: N#C[C@H](C[C@@H]1CCNC1=O)NC(=O)C1CC2(CCC2)CN1C(=O)c1cc2ccc(Cl)cc2[nH]1] |
| 991 | 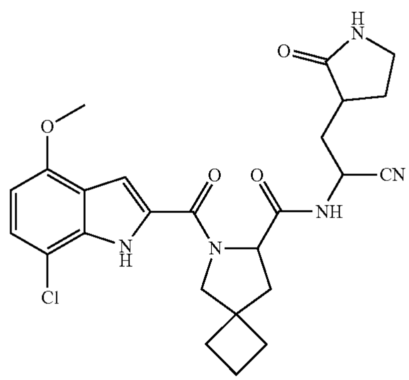 [SMILES: COc1ccc(Cl)c2[nH]c(C(=O)N3CC4(CCC4)CC3C(=O)NC(C#N)CC3CCNC3=O)cc12] |
| 992 | 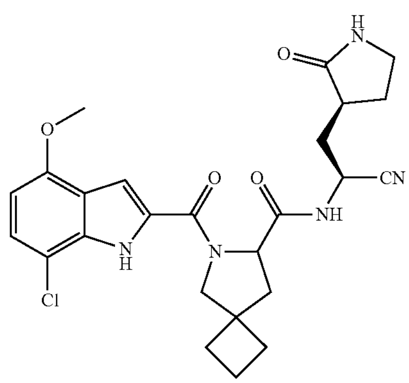 [SMILES: COc1ccc(Cl)c2[nH]c(C(=O)N3CC4(CCC4)CC3C(=O)N[C@H](C#N)C[C@@H]3CCNC3=O)cc12] |
| 993 | 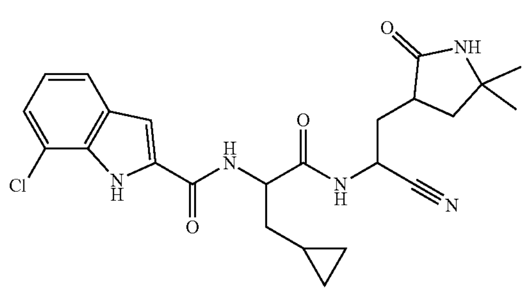 [SMILES: CC1(C)CC(CC(C#N)NC(=O)C(CC2CC2)NC(=O)c2cc3cccc(Cl)c3[nH]2)C(=O)N1] |

TABLE 1-continued
Exemplary compounds.
| Cmpd No. | Structure |
|---|---|
| 994 | 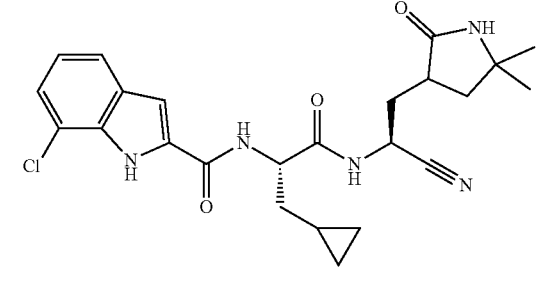 [SMILES: CC1(C)CC(C[C@@H](C#N)NC(=O)[C@H](CC2CC2)NC(=O)c2cc3cccc(Cl)c3[nH]2)C(=O)N1] |
| 995 | 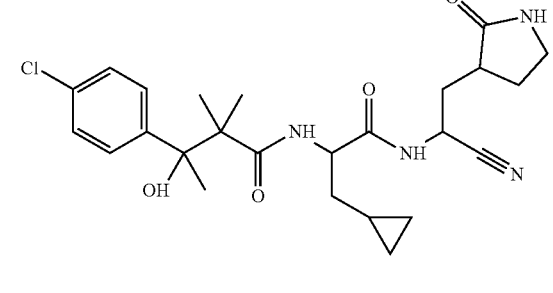 |
| 996 | 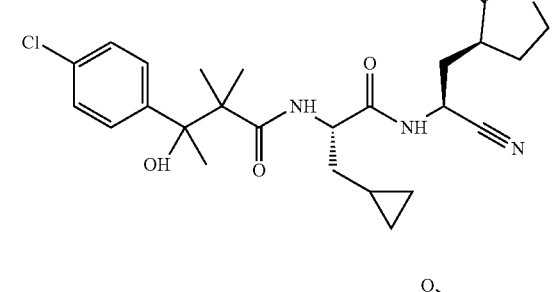 |
| 997 | 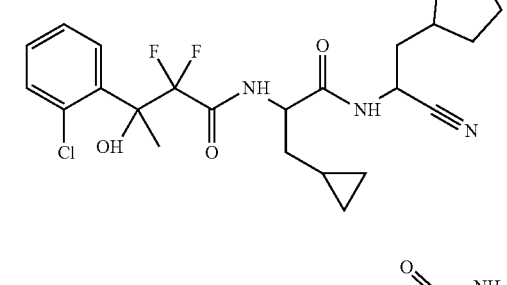 |
| 998 | 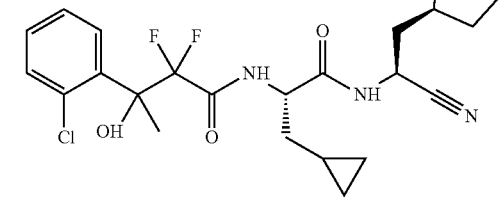 |

TABLE 1-continued

Exemplary compounds.

| Cmpd No. | Structure |
|---|---|
| 999 | 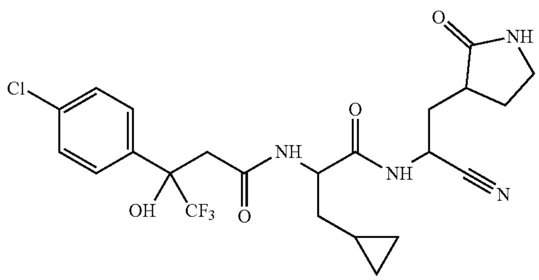 [SMILES: N#CC(CC1CCNC1=O)NC(=O)C(CC1CC1)NC(=O)CC(O)(c1ccc(Cl)cc1)C(F)(F)F] |
| 1000 | 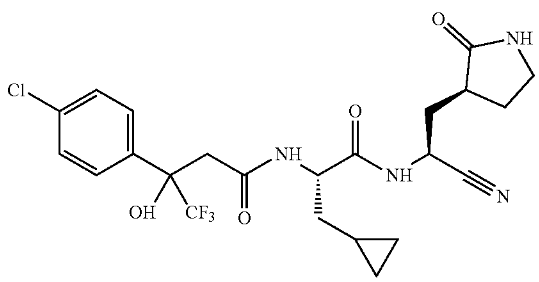 [SMILES: N#C[C@H](C[C@@H]1CCNC1=O)NC(=O)[C@H](CC1CC1)NC(=O)CC(O)(c1ccc(Cl)cc1)C(F)(F)F] |
| 1001 | 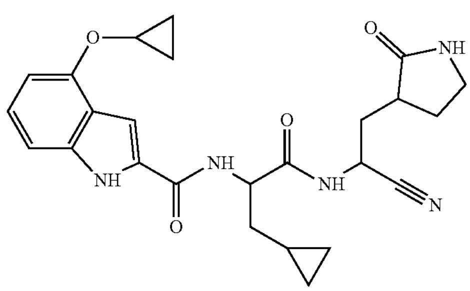 [SMILES: N#CC(CC1CCNC1=O)NC(=O)C(CC1CC1)NC(=O)c1cc2c(OC3CC3)cccc2[nH]1] |
| 1002 | 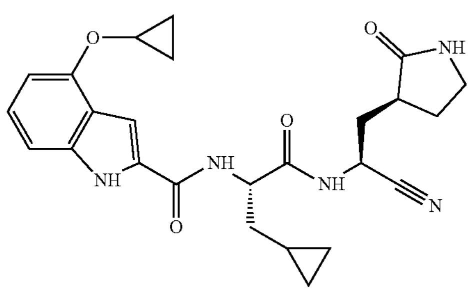 [SMILES: N#C[C@H](C[C@@H]1CCNC1=O)NC(=O)[C@H](CC1CC1)NC(=O)c1cc2c(OC3CC3)cccc2[nH]1] |
| 1003 | 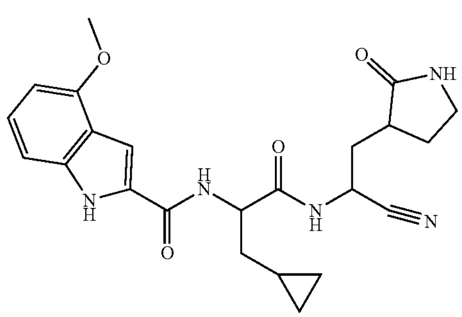 [SMILES: COc1cccc2[nH]c(C(=O)NC(CC3CC3)C(=O)NC(C#N)CC3CCNC3=O)cc12] |

TABLE 1-continued
Exemplary compounds.
| Cmpd No. | Structure |
|---|---|
| 1004 | 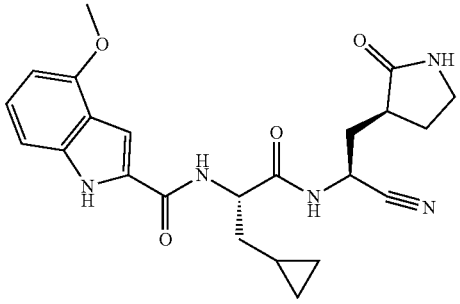 [SMILES: COc1cccc2[nH]c(C(=O)N[C@@H](CC3CC3)C(=O)N[C@H](C#N)C[C@@H]3CCNC3=O)cc12] |
| 1005 | 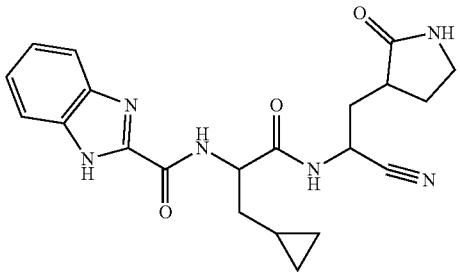 [SMILES: N#CC(CC1CCNC1=O)NC(=O)C(CC1CC1)NC(=O)c1nc2ccccc2[nH]1] |
| 1006 | 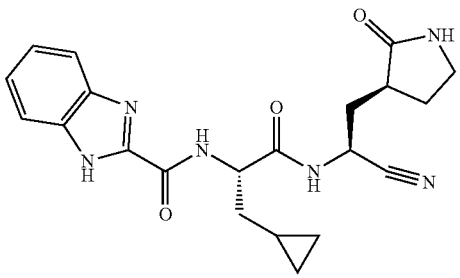 [SMILES: N#C[C@H](C[C@@H]1CCNC1=O)NC(=O)[C@H](CC1CC1)NC(=O)c1nc2ccccc2[nH]1] |
| 1007 | 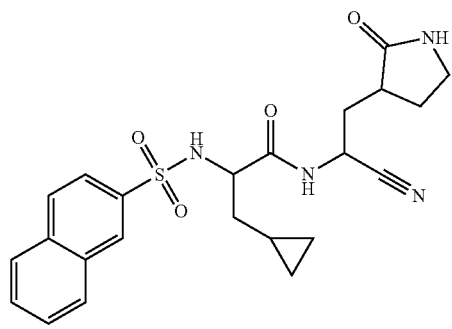 [SMILES: N#CC(CC1CCNC1=O)NC(=O)C(CC1CC1)NS(=O)(=O)c1ccc2ccccc2c1] |
| 1008 | 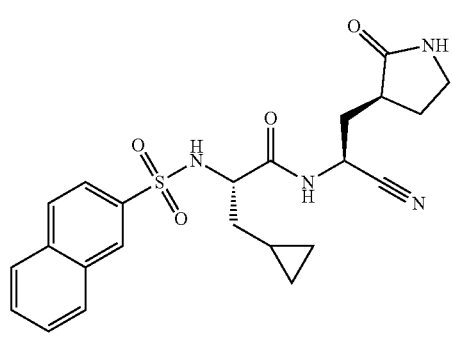 [SMILES: N#C[C@H](C[C@@H]1CCNC1=O)NC(=O)[C@H](CC1CC1)NS(=O)(=O)c1ccc2ccccc2c1] |

TABLE 1-continued

Exemplary compounds.

| Cmpd No. | Structure |
|---|---|
| 1009 | 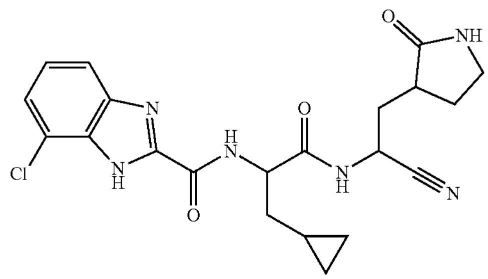 [SMILES: N#CC(CC1CCNC1=O)NC(=O)C(CC1CC1)NC(=O)c1nc2cccc(Cl)c2[nH]1] |
| 1010 | 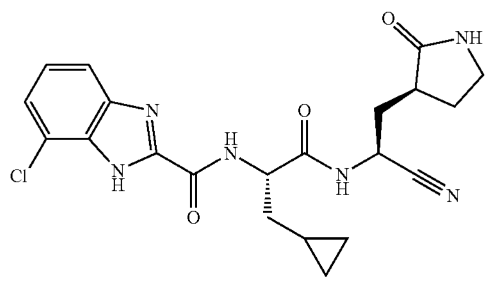 [SMILES: N#C[C@H](C[C@@H]1CCNC1=O)NC(=O)[C@H](CC1CC1)NC(=O)c1nc2cccc(Cl)c2[nH]1] |
| 1011 | 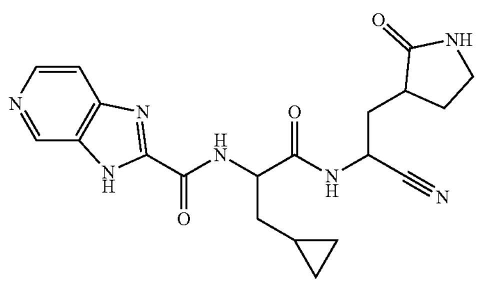 [SMILES: N#CC(CC1CCNC1=O)NC(=O)C(CC1CC1)NC(=O)c1nc2ccncc2[nH]1] |
| 1012 | 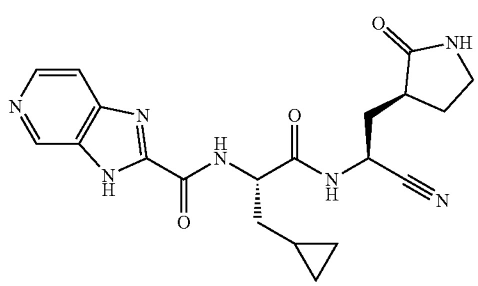 [SMILES: N#C[C@H](C[C@@H]1CCNC1=O)NC(=O)[C@H](CC1CC1)NC(=O)c1nc2ccncc2[nH]1] |
| 1013 | 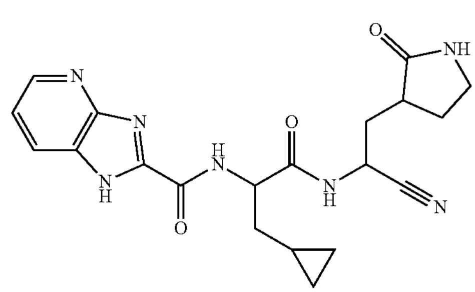 [SMILES: N#CC(CC1CCNC1=O)NC(=O)C(CC1CC1)NC(=O)c1nc2ncccc2[nH]1] |

TABLE 1-continued
Exemplary compounds.
| Cmpd No. | Structure |
|---|---|
| 1014 | 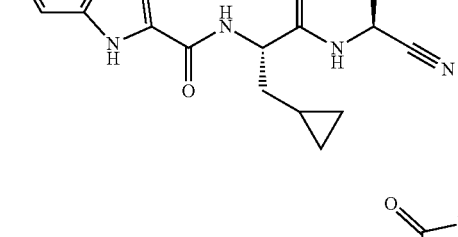 |
| 1015 | 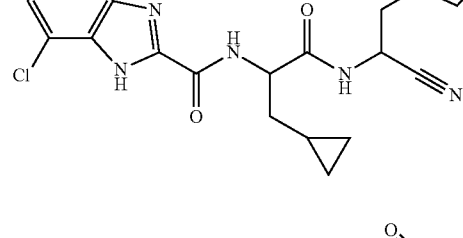 |
| 1016 | 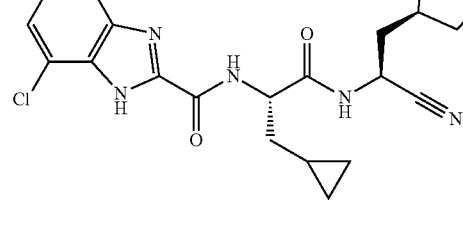 |
| 1017 | 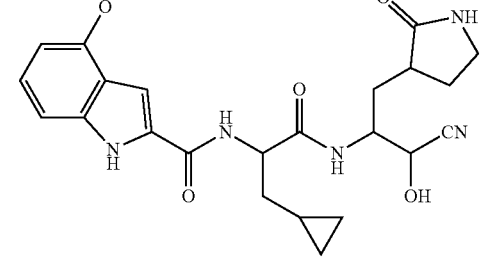 |
| 1018 | 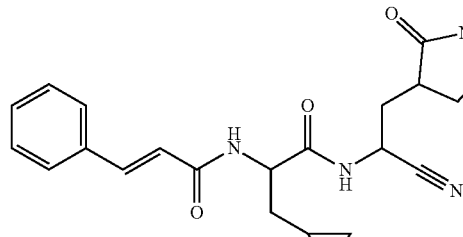 |

503 504

TABLE 1-continued

Exemplary compounds.

| Cmpd No. | Structure |
|---|---|
| 1019 | 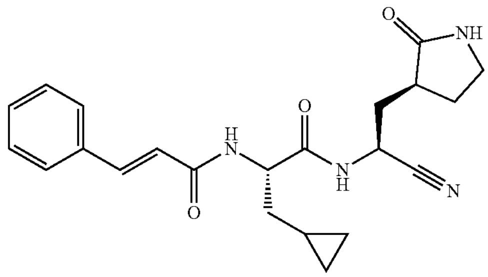 [SMILES: N#C[C@H](C[C@@H]1CCNC1=O)NC(=O)[C@H](CC1CC1)NC(=O)/C=C/c1ccccc1] |
| 1020 | 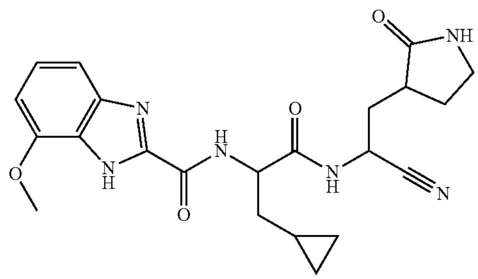 [SMILES: COc1cccc2nc(C(=O)NC(CC3CC3)C(=O)NC(C#N)CC3CCNC3=O)[nH]c12] |
| 1021 | 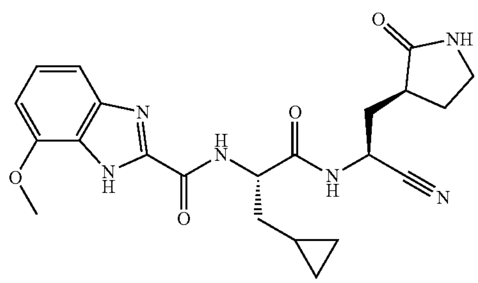 [SMILES: COc1cccc2nc(C(=O)N[C@@H](CC3CC3)C(=O)N[C@H](C#N)C[C@@H]3CCNC3=O)[nH]c12] |
| 1022 | 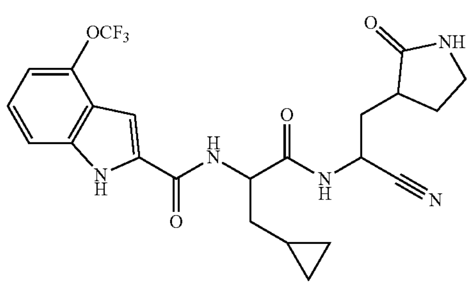 [SMILES: N#CC(CC1CCNC1=O)NC(=O)C(CC1CC1)NC(=O)c1cc2c(OC(F)(F)F)cccc2[nH]1] |
| 1023 | 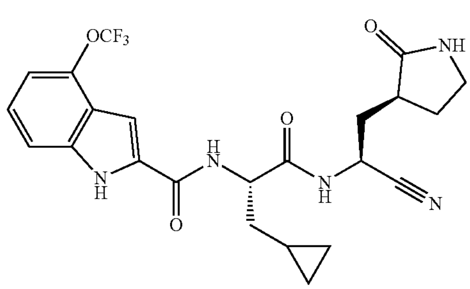 [SMILES: N#C[C@H](C[C@@H]1CCNC1=O)NC(=O)[C@H](CC1CC1)NC(=O)c1cc2c(OC(F)(F)F)cccc2[nH]1] |

TABLE 1-continued

Exemplary compounds.

| Cmpd No. | Structure |
|---|---|
| 1024 | *(4-(difluoromethoxy)-1H-indole-2-carboxamide linked to cyclopropylmethyl-substituted amino acid amide bearing cyano and 2-oxopyrrolidin-3-ylmethyl substituents)* |
| 1025 | *(same indole-2-carboxamide scaffold as 1024, with defined stereochemistry at the α-carbon)* |
| 1026 | *(4-(trifluoromethoxy)-1H-benzimidazole-2-carboxamide linked to cyclopropylmethyl amino acid amide bearing cyano and 2-oxopyrrolidin-3-ylmethyl substituents)* |
| 1027 | *(same benzimidazole-2-carboxamide scaffold as 1026, with defined stereochemistry)* |
| 1028 | *((E)-3-(4-chloro-2-fluorophenyl)acrylamide linked to cyclopropylmethyl amino acid amide bearing cyano and 2-oxopyrrolidin-3-ylmethyl substituents)* |

TABLE 1-continued
Exemplary compounds.
| Cmpd No. | Structure |
|---|---|
| 1029 | 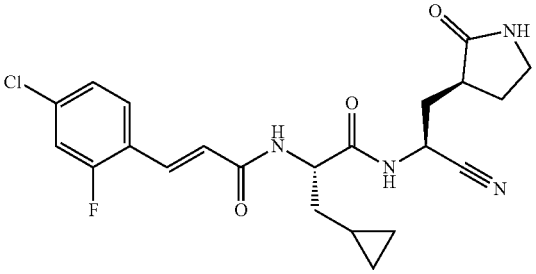 [SMILES: N#C[C@H](C[C@@H]1CCNC1=O)NC(=O)[C@H](CC1CC1)NC(=O)/C=C/c1ccc(Cl)cc1F] |
| 1030 | 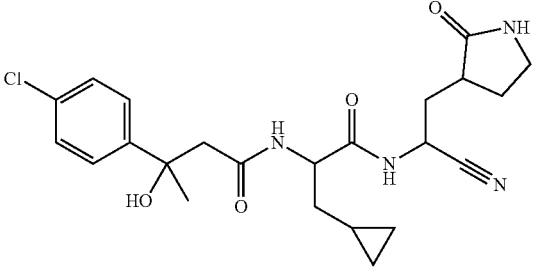 [SMILES: CC(O)(CC(=O)NC(CC1CC1)C(=O)NC(C#N)CC1CCNC1=O)c1ccc(Cl)cc1] |
| 1031 | 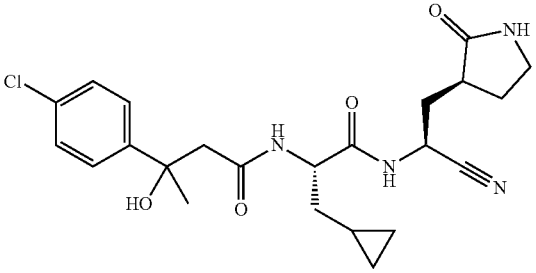 [SMILES: CC(O)(CC(=O)N[C@@H](CC1CC1)C(=O)N[C@H](C#N)C[C@@H]1CCNC1=O)c1ccc(Cl)cc1] |
| 1032 | 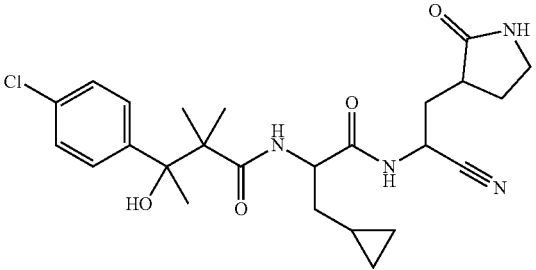 [SMILES: CC(C)(C(=O)NC(CC1CC1)C(=O)NC(C#N)CC1CCNC1=O)C(C)(O)c1ccc(Cl)cc1] |
| 1033 | 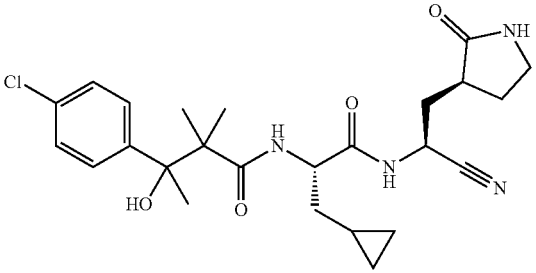 [SMILES: CC(C)(C(=O)N[C@@H](CC1CC1)C(=O)N[C@H](C#N)C[C@@H]1CCNC1=O)C(C)(O)c1ccc(Cl)cc1] |

TABLE 1-continued

Exemplary compounds.

| Cmpd No. | Structure |
|---|---|
| 1034 | 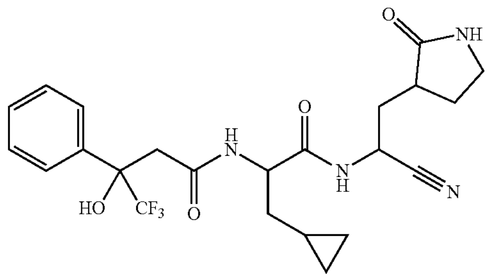 [SMILES: N#CC(CC1CCNC1=O)NC(=O)C(CC1CC1)NC(=O)CC(O)(c1ccccc1)C(F)(F)F] |
| 1035 | 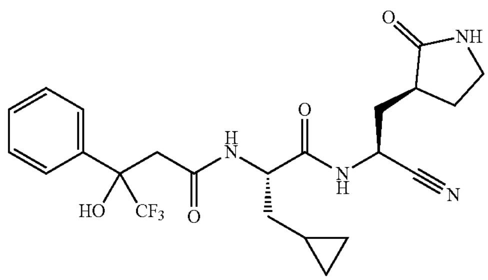 [SMILES: N#C[C@H](C[C@@H]1CCNC1=O)NC(=O)[C@H](CC1CC1)NC(=O)CC(O)(c1ccccc1)C(F)(F)F] |
| 1036 | 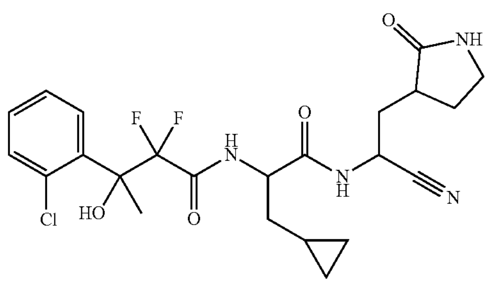 [SMILES: CC(O)(c1ccccc1Cl)C(F)(F)C(=O)NC(CC1CC1)C(=O)NC(C#N)CC1CCNC1=O] |
| 1037 | 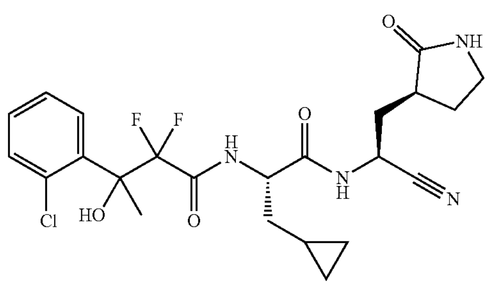 [SMILES: CC(O)(c1ccccc1Cl)C(F)(F)C(=O)N[C@@H](CC1CC1)C(=O)N[C@H](C#N)C[C@@H]1CCNC1=O] |
| 1038 | 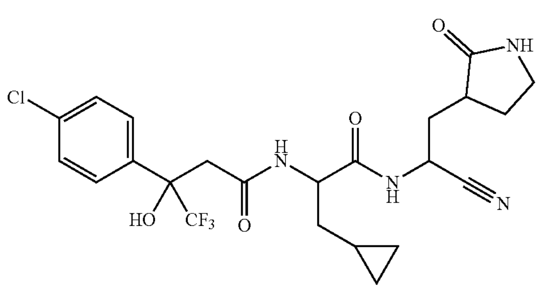 [SMILES: N#CC(CC1CCNC1=O)NC(=O)C(CC1CC1)NC(=O)CC(O)(c1ccc(Cl)cc1)C(F)(F)F] |

TABLE 1-continued
Exemplary compounds.
| Cmpd No. | Structure |
|---|---|
| 1039 | 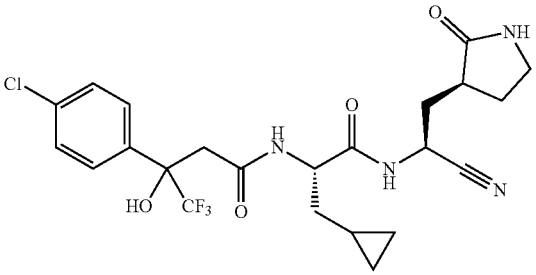 |
| 1040 | 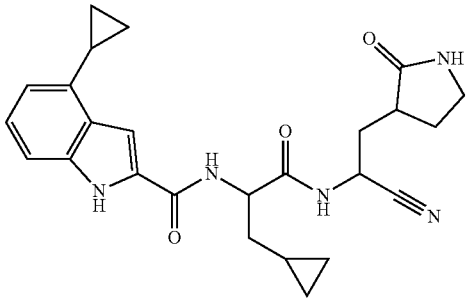 [SMILES: N#CC(CC1CCNC1=O)NC(=O)C(CC1CC1)NC(=O)c1cc2c(C3CC3)cccc2[nH]1] |
| 1041 | 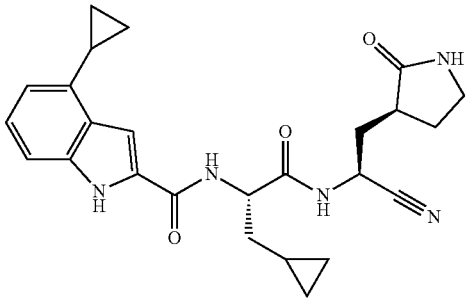 [SMILES: N#C[C@H](C[C@@H]1CCNC1=O)NC(=O)[C@H](CC1CC1)NC(=O)c1cc2c(C3CC3)cccc2[nH]1] |
| 1042 | 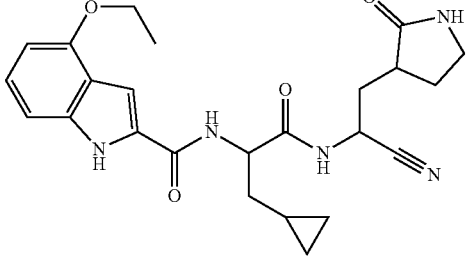 |
| 1043 | 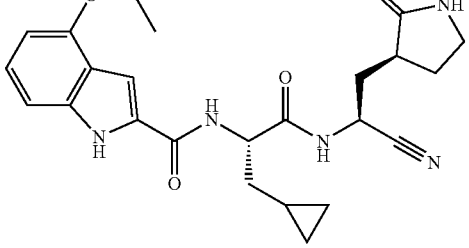 |

TABLE 1-continued

Exemplary compounds.

| Cmpd No. | Structure |
|---|---|
| 1046 | 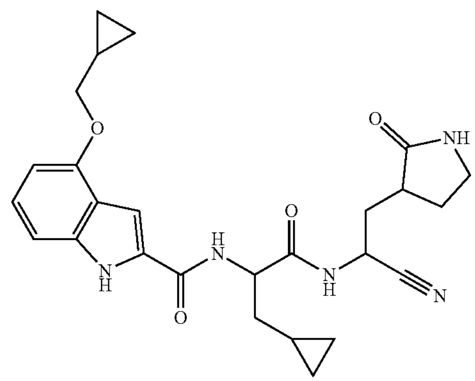 [SMILES: N#CC(CC1CCNC1=O)NC(=O)C(CC1CC1)NC(=O)c1cc2c(OCC3CC3)cccc2[nH]1] |
| 1047 | 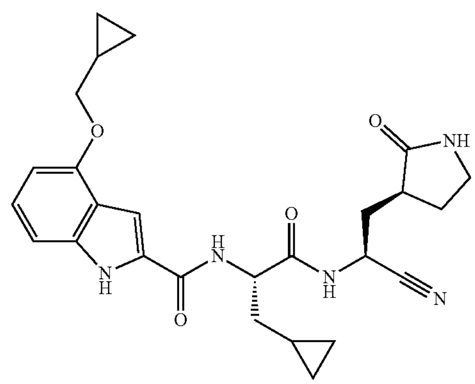 [SMILES: N#C[C@H](C[C@@H]1CCNC1=O)NC(=O)[C@H](CC1CC1)NC(=O)c1cc2c(OCC3CC3)cccc2[nH]1] |
| 1048 | 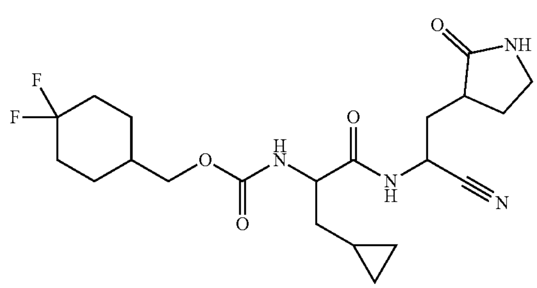 [SMILES: N#CC(CC1CCNC1=O)NC(=O)C(CC1CC1)NC(=O)OCC1CCC(F)(F)CC1] |
| 1049 | 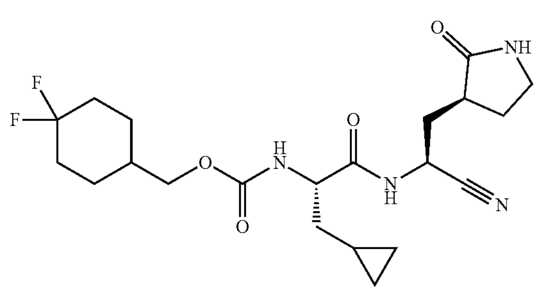 [SMILES: N#C[C@H](C[C@@H]1CCNC1=O)NC(=O)[C@H](CC1CC1)NC(=O)OCC1CCC(F)(F)CC1] |

TABLE 1-continued
Exemplary compounds.
| Cmpd No. | Structure |
|---|---|
| 1050 | 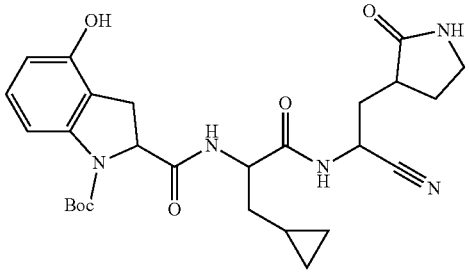 [SMILES: CC(C)(C)OC(=O)N1c2cccc(O)c2CC1C(=O)NC(CC1CC1)C(=O)NC(C#N)CC1CCNC1=O] |
| 1051 | 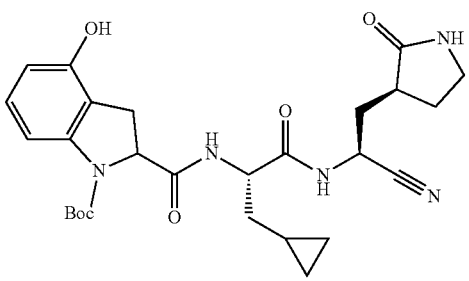 [SMILES: CC(C)(C)OC(=O)N1c2cccc(O)c2CC1C(=O)N[C@@H](CC1CC1)C(=O)N[C@H](C#N)C[C@@H]1CCNC1=O] |
| 1052 | 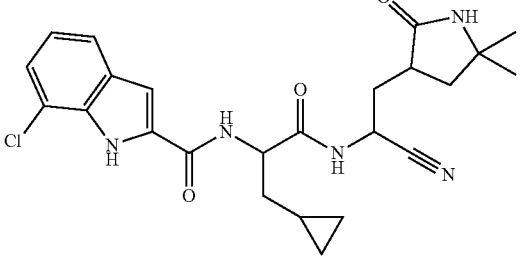 |
| 1053 | 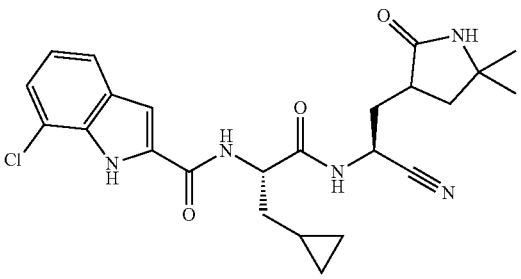 [SMILES: CC1(C)CC(C[C@@H](C#N)NC(=O)[C@H](CC2CC2)NC(=O)c2cc3cccc(Cl)c3[nH]2)C(=O)N1] |
| 1054 | 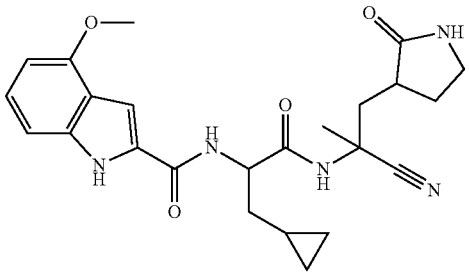 [SMILES: COc1cccc2[nH]c(C(=O)NC(CC3CC3)C(=O)NC(C)(C#N)CC3CCNC3=O)cc12] |

TABLE 1-continued

Exemplary compounds.

| Cmpd No. | Structure |
|---|---|
| 1055 | 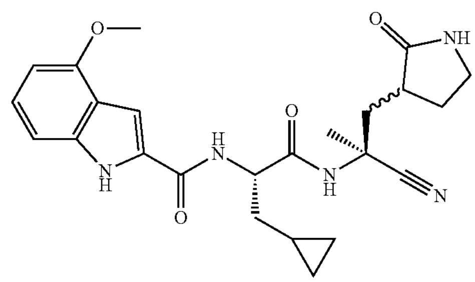 [SMILES: COc1cccc2[nH]c(C(=O)N[C@@H](CC3CC3)C(=O)N[C@](C)(C#N)CC3CCNC3=O)cc12] |
| 1056 | 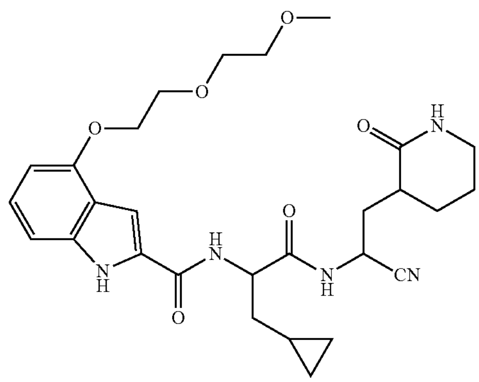 [SMILES: COCCOCCOc1cccc2[nH]c(C(=O)NC(CC3CC3)C(=O)NC(C#N)CC3CCCNC3=O)cc12] |
| 1057 | 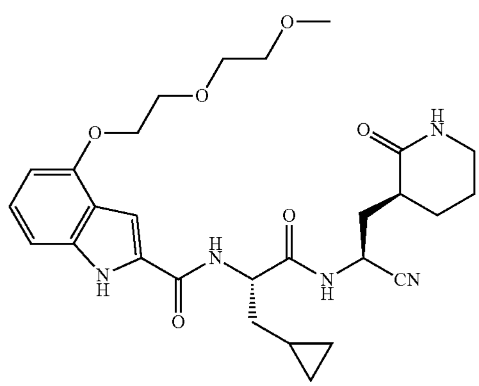 [SMILES: COCCOCCOc1cccc2[nH]c(C(=O)N[C@@H](CC3CC3)C(=O)N[C@H](C#N)C[C@@H]3CCCNC3=O)cc12] |
| 1058 | 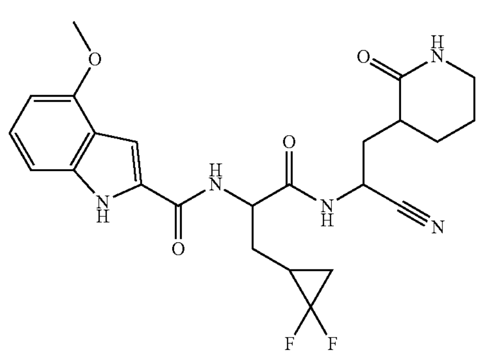 [SMILES: COc1cccc2[nH]c(C(=O)NC(CC3CC3(F)F)C(=O)NC(C#N)CC3CCCNC3=O)cc12] |

519 520

TABLE 1-continued

Exemplary compounds.

| Cmpd No. | Structure |
|---|---|
| 1059 | 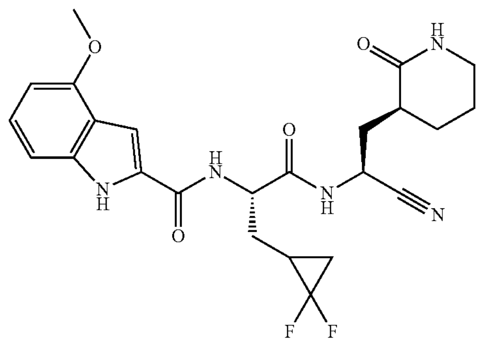 [SMILES: COc1cccc2[nH]c(C(=O)N[C@@H](CC3CC3(F)F)C(=O)N[C@H](C#N)C[C@@H]3CCCNC3=O)cc12] |
| 1060 | 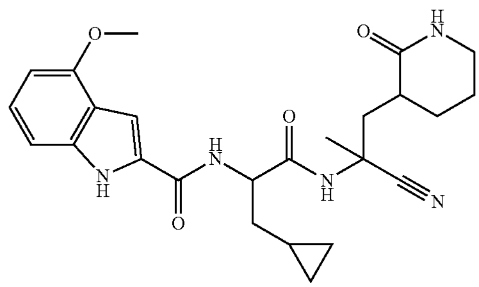 [SMILES: COc1cccc2[nH]c(C(=O)NC(CC3CC3)C(=O)NC(C)(C#N)CC3CCCNC3=O)cc12] |
| 1061 | 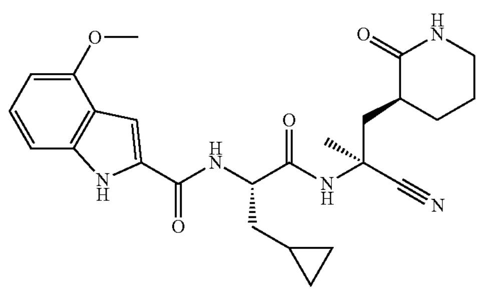 [SMILES: COc1cccc2[nH]c(C(=O)N[C@@H](CC3CC3)C(=O)N[C@](C)(C#N)C[C@@H]3CCCNC3=O)cc12] |
| 1062 | 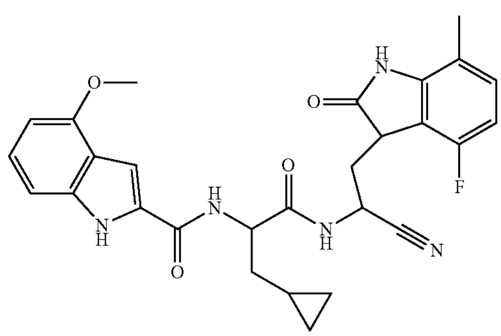 |
| 1063 | 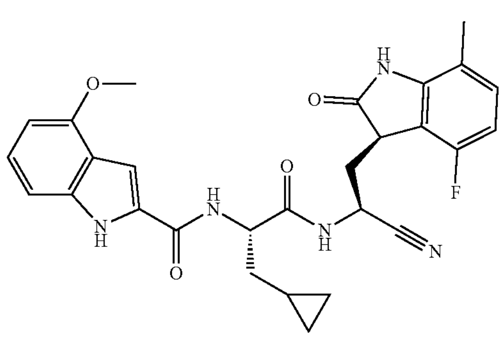 [SMILES: COc1cccc2[nH]c(C(=O)N[C@@H](CC3CC3)C(=O)N[C@H](C#N)C[C@H]3C(=O)Nc4c(C)ccc(F)c43)cc12] |

TABLE 1-continued
Exemplary compounds.
| Cmpd No. | Structure |
|---|---|
| 1064 | 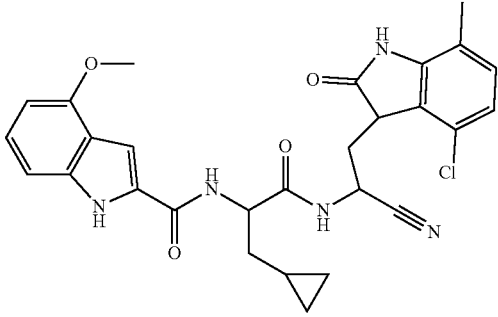 [SMILES: COc1cccc2[nH]c(C(=O)NC(CC3CC3)C(=O)NC(C#N)CC3C(=O)Nc4c(C)ccc(Cl)c43)cc12] |
| 1065 | 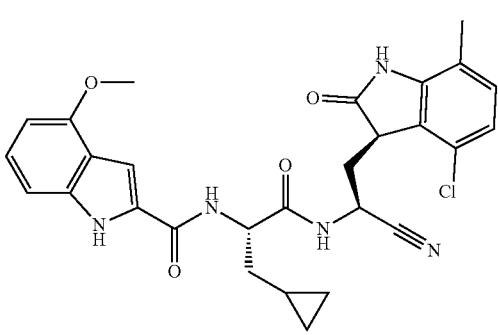 [SMILES: COc1cccc2[nH]c(C(=O)N[C@@H](CC3CC3)C(=O)N[C@H](C#N)C[C@H]3C(=O)Nc4c(C)ccc(Cl)c43)cc12] |
| 1066 | 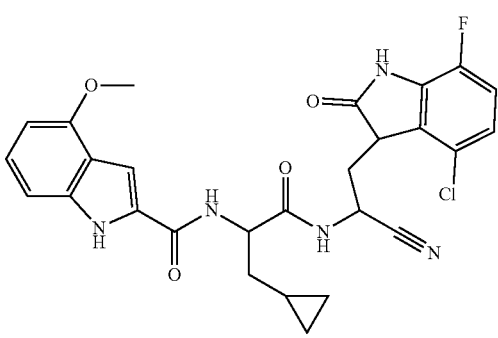 [SMILES: COc1cccc2[nH]c(C(=O)NC(CC3CC3)C(=O)NC(C#N)CC3C(=O)Nc4c(F)ccc(Cl)c43)cc12] |
| 1067 | 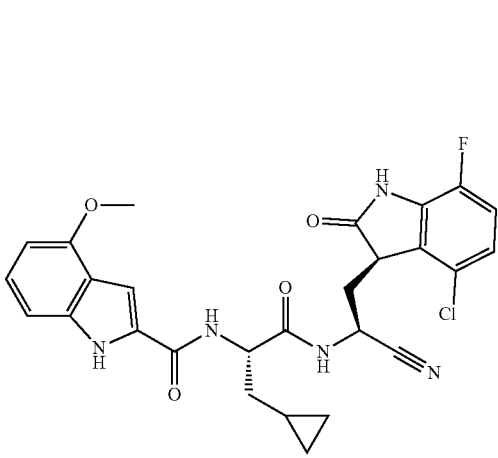 [SMILES: COc1cccc2[nH]c(C(=O)N[C@@H](CC3CC3)C(=O)N[C@H](C#N)C[C@H]3C(=O)Nc4c(F)ccc(Cl)c43)cc12] |

TABLE 1-continued
Exemplary compounds.
| Cmpd No. | Structure |
|---|---|
| 1068 | 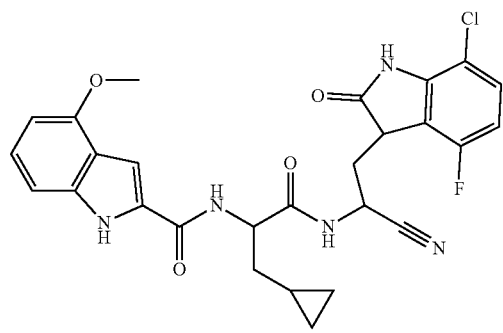 |
| 1069 | 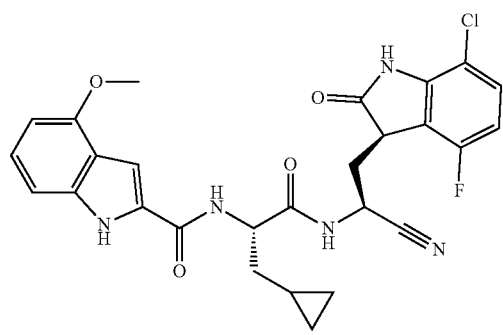 |
| 1070 | 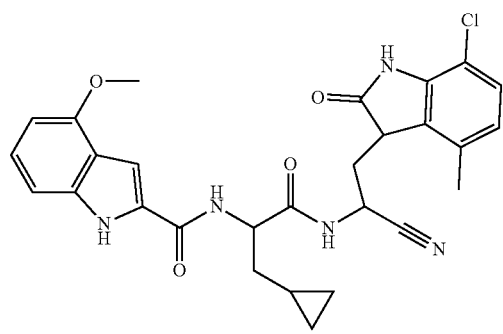 [SMILES: COc1cccc2[nH]c(C(=O)NC(CC3CC3)C(=O)NC(C#N)CC3C(=O)Nc4c(F)ccc(C)c43)cc12] |
| 1071 | 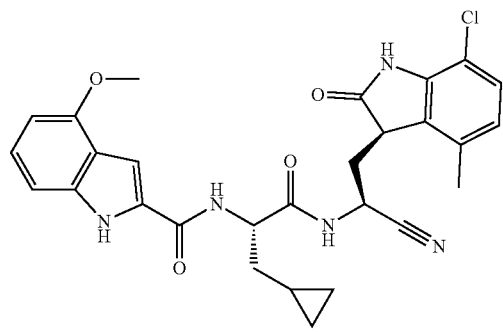 [SMILES: COc1cccc2[nH]c(C(=O)N[C@@H](CC3CC3)C(=O)N[C@H](C#N)C[C@H]3C(=O)Nc4c(F)ccc(C)c43)cc12] |

TABLE 1-continued

Exemplary compounds.

| Cmpd No. | Structure |
|---|---|
| 1072 | 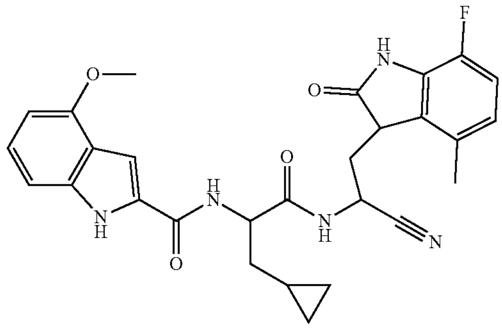 |
| 1073 | 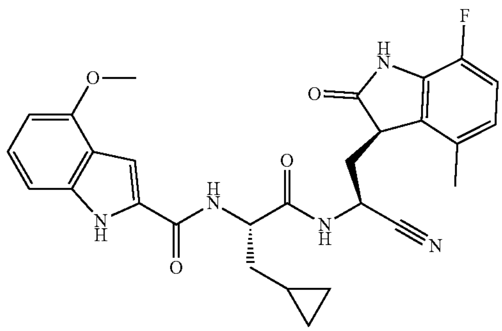 |
| 1074 | 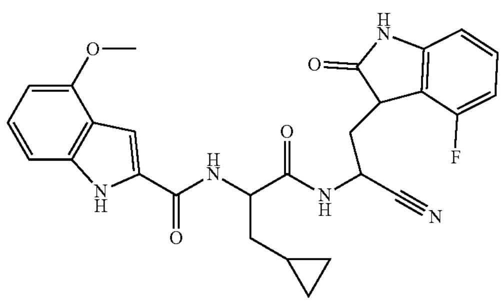 [SMILES: COc1cccc2[nH]c(C(=O)NC(CC3CC3)C(=O)NC(C#N)CC3C(=O)Nc4cccc(F)c43)cc12] |
| 1075 | 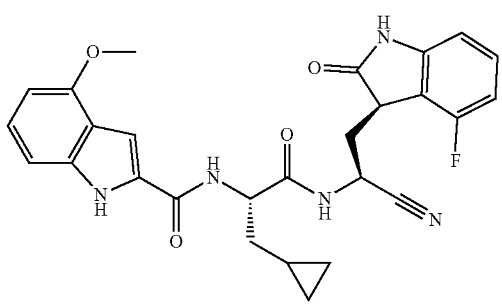 [SMILES: COc1cccc2[nH]c(C(=O)N[C@@H](CC3CC3)C(=O)N[C@H](C#N)C[C@H]3C(=O)Nc4cccc(F)c43)cc12] |
| 1076 | 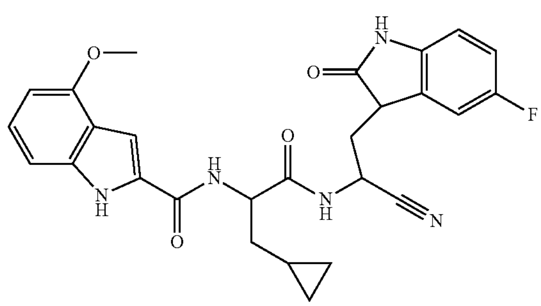 [SMILES: COc1cccc2[nH]c(C(=O)NC(CC3CC3)C(=O)NC(C#N)CC3C(=O)Nc4ccc(F)cc43)cc12] |

TABLE 1-continued

Exemplary compounds.

| Cmpd No. | Structure |
| --- | --- |
| 1077 | 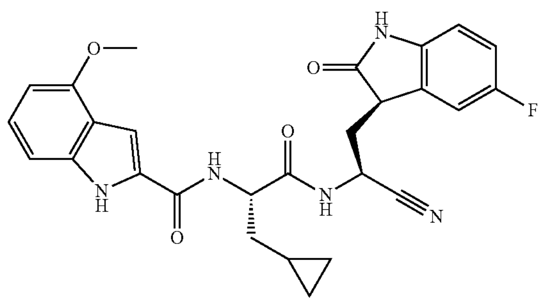 [SMILES: COc1cccc2[nH]c(C(=O)N[C@@H](CC3CC3)C(=O)N[C@H](C#N)C[C@H]3C(=O)Nc4ccc(F)cc43)cc12] |
| 1078 | 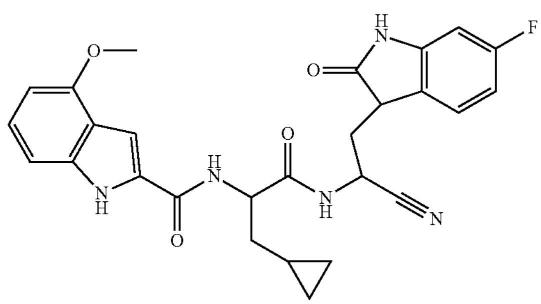 [SMILES: COc1cccc2[nH]c(C(=O)NC(CC3CC3)C(=O)NC(C#N)CC3C(=O)Nc4cc(F)ccc43)cc12] |
| 1079 | 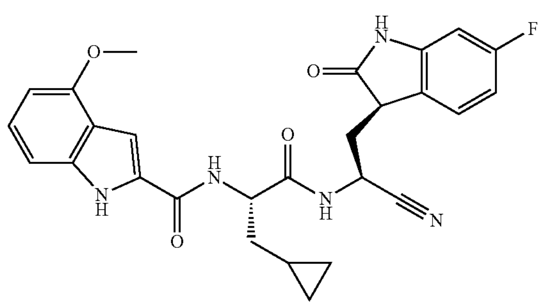 [SMILES: COc1cccc2[nH]c(C(=O)N[C@@H](CC3CC3)C(=O)N[C@H](C#N)C[C@H]3C(=O)Nc4cc(F)ccc43)cc12] |
| 1080 | 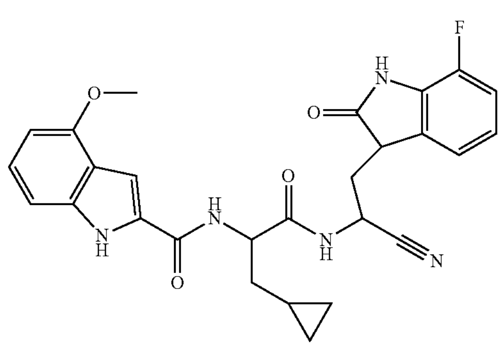 [SMILES: COc1cccc2[nH]c(C(=O)NC(CC3CC3)C(=O)NC(C#N)CC3C(=O)Nc4c(F)cccc43)cc12] |

TABLE 1-continued

Exemplary compounds.

| Cmpd No. | Structure |
|---|---|
| 1081 | 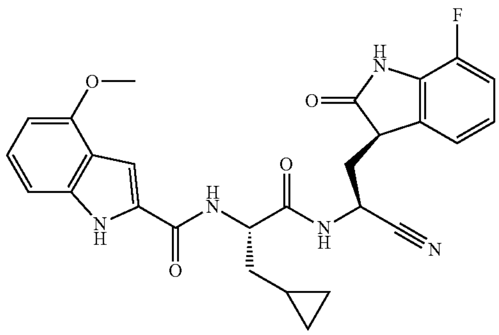 [SMILES: COc1cccc2[nH]c(C(=O)N[C@@H](CC3CC3)C(=O)N[C@H](C#N)C[C@H]3C(=O)Nc4c(F)cccc43)cc12] |
| 1082 | 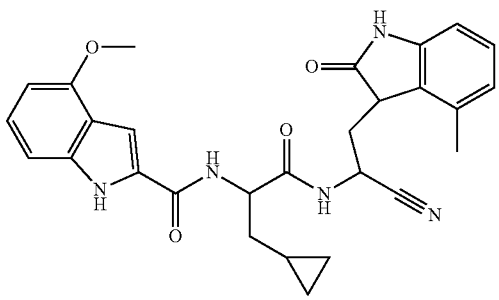 [SMILES: COc1cccc2[nH]c(C(=O)NC(CC3CC3)C(=O)NC(C#N)CC3C(=O)Nc4cccc(C)c43)cc12] |
| 1083 | 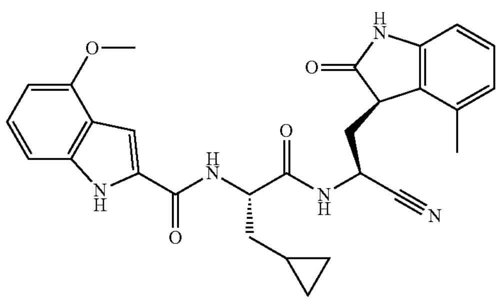 [SMILES: COc1cccc2[nH]c(C(=O)N[C@@H](CC3CC3)C(=O)N[C@H](C#N)C[C@H]3C(=O)Nc4cccc(C)c43)cc12] |
| 1084 | 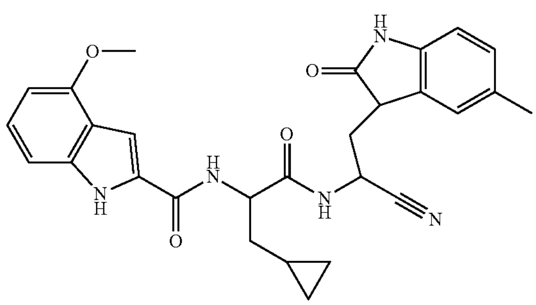 [SMILES: COc1cccc2[nH]c(C(=O)NC(CC3CC3)C(=O)NC(C#N)CC3C(=O)Nc4ccc(C)cc43)cc12] |
| 1085 | 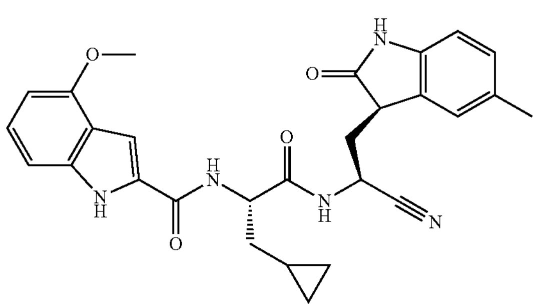 [SMILES: COc1cccc2[nH]c(C(=O)N[C@@H](CC3CC3)C(=O)N[C@H](C#N)C[C@H]3C(=O)Nc4ccc(C)cc43)cc12] |

TABLE 1-continued

Exemplary compounds.

| Cmpd No. | Structure |
|---|---|
| 1086 | 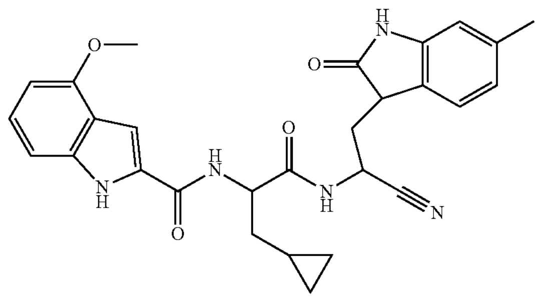 [SMILES: COc1cccc2[nH]c(C(=O)NC(CC3CC3)C(=O)NC(C#N)CC3C(=O)Nc4cc(C)ccc43)cc12] |
| 1087 | 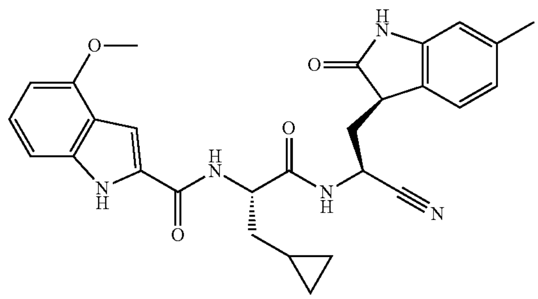 [SMILES: COc1cccc2[nH]c(C(=O)N[C@@H](CC3CC3)C(=O)N[C@H](C#N)C[C@H]3C(=O)Nc4cc(C)ccc43)cc12] |
| 1088 | 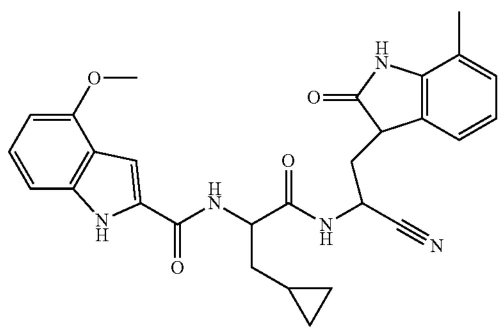 [SMILES: COc1cccc2[nH]c(C(=O)NC(CC3CC3)C(=O)NC(C#N)CC3C(=O)Nc4c(C)cccc43)cc12] |
| 1089 | 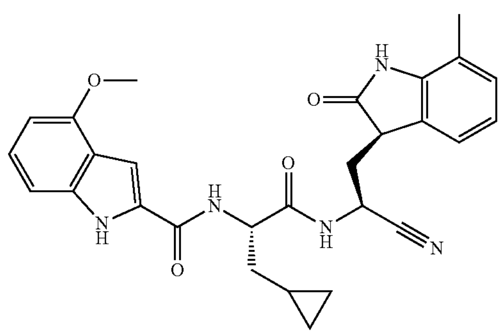 [SMILES: COc1cccc2[nH]c(C(=O)N[C@@H](CC3CC3)C(=O)N[C@H](C#N)C[C@H]3C(=O)Nc4c(C)cccc43)cc12] |
| 1090 | 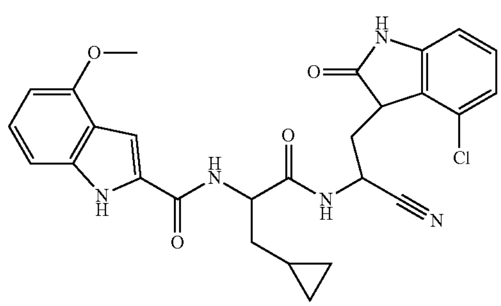 [SMILES: COc1cccc2[nH]c(C(=O)NC(CC3CC3)C(=O)NC(C#N)CC3C(=O)Nc4cccc(Cl)c43)cc12] |

TABLE 1-continued
Exemplary compounds.
| Cmpd No. | Structure |
|---|---|
| 1091 | 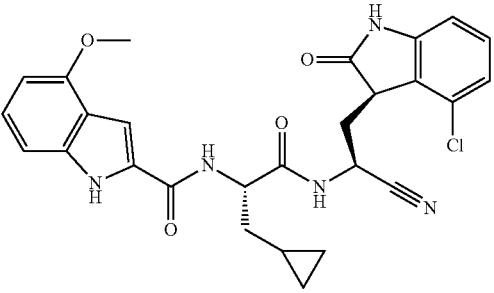 [SMILES: COc1cccc2[nH]c(C(=O)N[C@@H](CC3CC3)C(=O)N[C@H](C#N)C[C@H]3C(=O)Nc4cccc(Cl)c43)cc12] |
| 1092 | 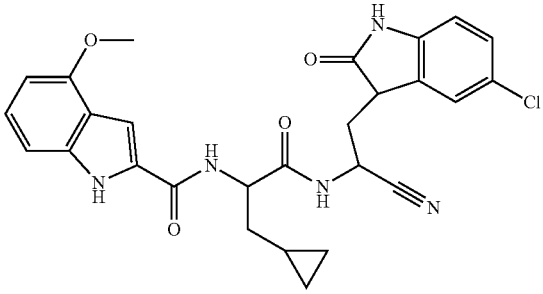 [SMILES: COc1cccc2[nH]c(C(=O)NC(CC3CC3)C(=O)NC(C#N)CC3C(=O)Nc4ccc(Cl)cc43)cc12] |
| 1093 | 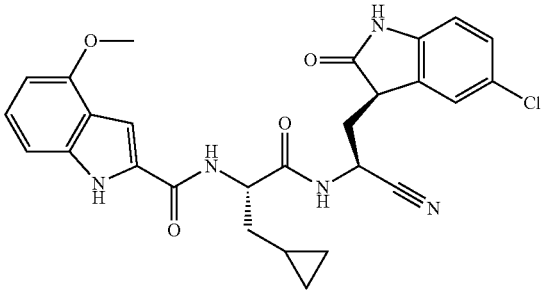 [SMILES: COc1cccc2[nH]c(C(=O)N[C@@H](CC3CC3)C(=O)N[C@H](C#N)C[C@H]3C(=O)Nc4ccc(Cl)cc43)cc12] |
| 1094 | 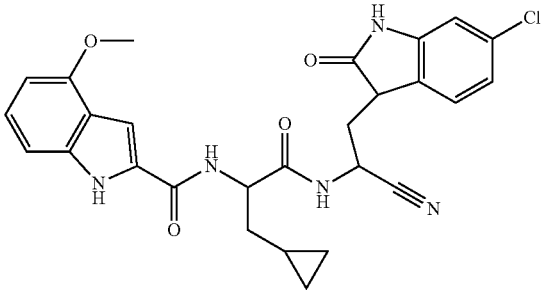 [SMILES: COc1cccc2[nH]c(C(=O)NC(CC3CC3)C(=O)NC(C#N)CC3C(=O)Nc4cc(Cl)ccc43)cc12] |
| 1095 | 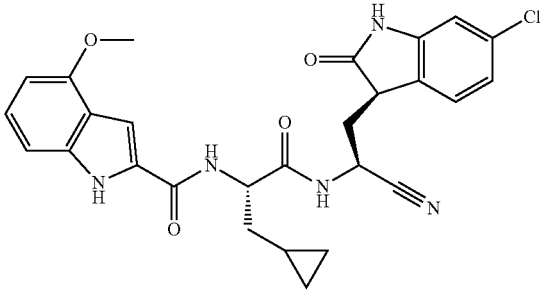 [SMILES: COc1cccc2[nH]c(C(=O)N[C@@H](CC3CC3)C(=O)N[C@H](C#N)C[C@H]3C(=O)Nc4cc(Cl)ccc43)cc12] |

TABLE 1-continued

Exemplary compounds.

| Cmpd No. | Structure |
|---|---|
| 1096 | 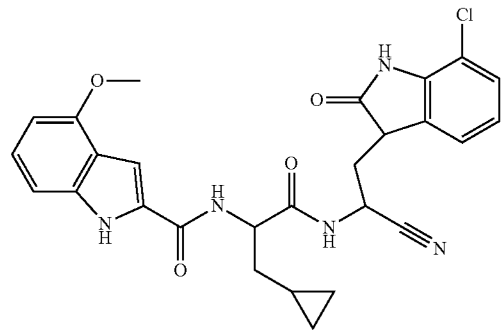 |
| 1097 | 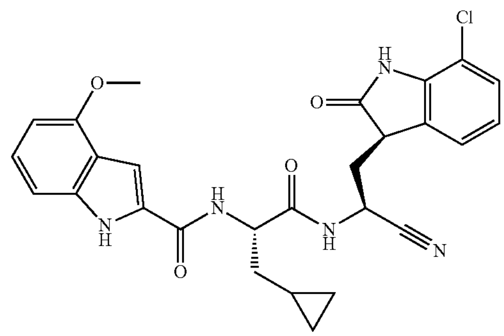 [SMILES: COc1cccc2[nH]c(C(=O)N[C@@H](CC3CC3)C(=O)N[C@H](C#N)C[C@H]3C(=O)Nc4c(Cl)cccc43)cc12] |
| 1098 | 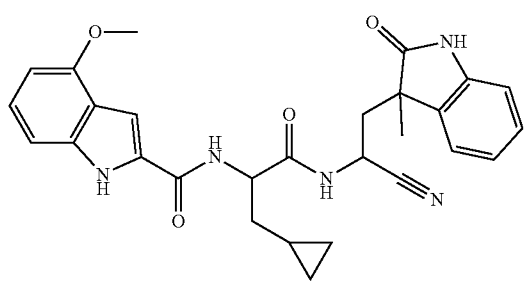 [SMILES: COc1cccc2[nH]c(C(=O)NC(CC3CC3)C(=O)NC(C#N)CC3(C)C(=O)Nc4ccccc43)cc12] |
| 1099 | 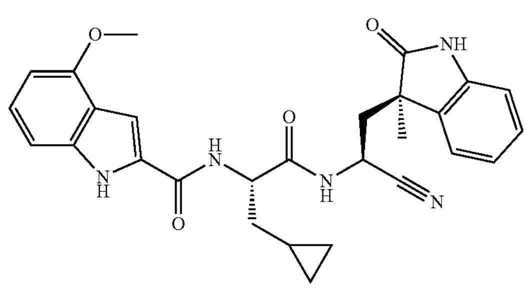 [SMILES: COc1cccc2[nH]c(C(=O)N[C@@H](CC3CC3)C(=O)N[C@H](C#N)C[C@@]3(C)C(=O)Nc4ccccc43)cc12] |
| 1100 | 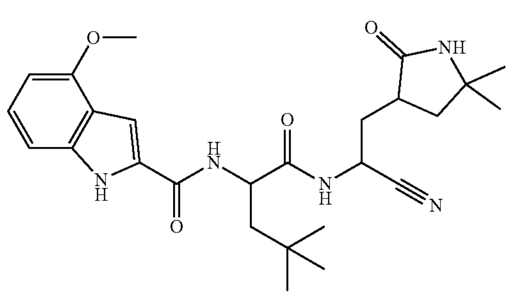 [SMILES: COc1cccc2[nH]c(C(=O)NC(CC(C)(C)C)C(=O)NC(C#N)CC3CC(C)(C)NC3=O)cc12] |

TABLE 1-continued

Exemplary compounds.

| Cmpd No. | Structure |
|---|---|
| 1101 | 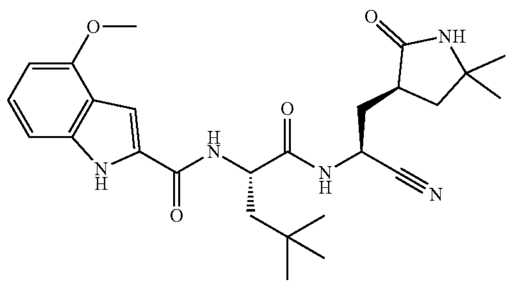 [SMILES: COc1cccc2[nH]c(C(=O)N[C@@H](CC(C)(C)C)C(=O)N[C@H](C#N)C[C@@H]3CC(C)(C)NC3=O)cc12] |
| 1102 | 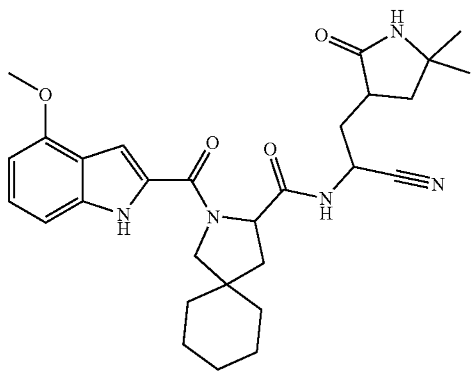 [SMILES: COc1cccc2[nH]c(C(=O)N3CC4(CCCCC4)CC3C(=O)NC(C#N)CC3CC(C)(C)NC3=O)cc12] |
| 1103 | 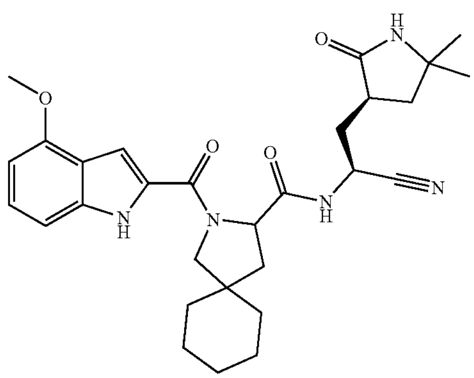 [SMILES: COc1cccc2[nH]c(C(=O)N3CC4(CCCCC4)CC3C(=O)N[C@H](C#N)C[C@@H]3CC(C)(C)NC3=O)cc12] |
| 1104 | 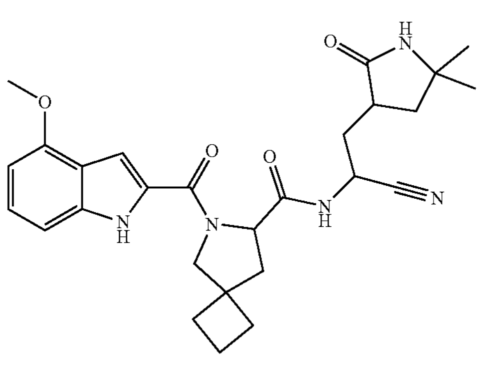 |

TABLE 1-continued

Exemplary compounds.

| Cmpd No. | Structure |
|---|---|
| 1105 | 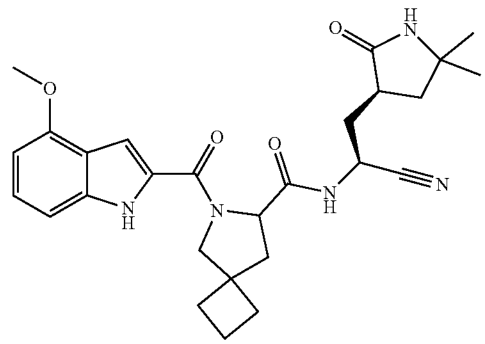 |
| 1106 | 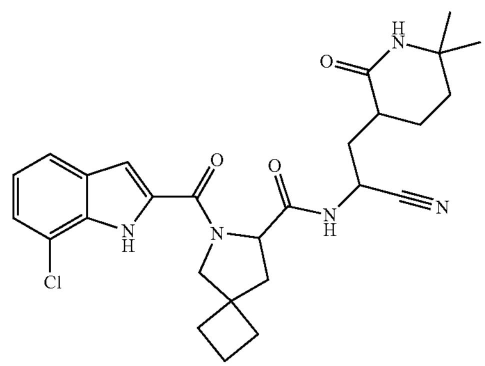 [SMILES: CC1(C)CCC(CC(C#N)NC(=O)C2CC3(CCC3)CN2C(=O)c2cc3cccc(Cl)c3[nH]2)C(=O)N1] |
| 1107 | 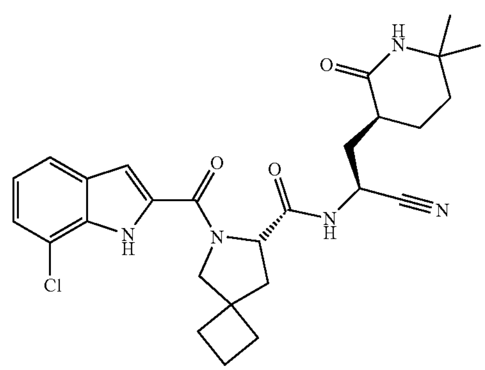 |
| 1108 | 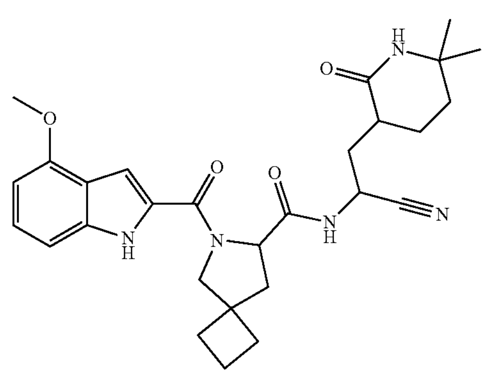 [SMILES: COc1cccc2[nH]c(C(=O)N3CC4(CCC4)CC3C(=O)NC(C#N)CC3CCC(C)(C)NC3=O)cc12] |

TABLE 1-continued
Exemplary compounds.
| Cmpd No. | Structure |
|---|---|
| 1109 | 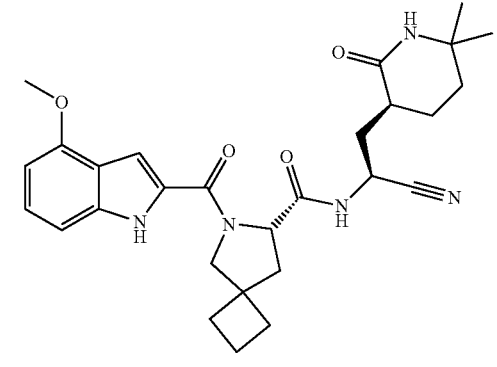 |
| 1110 | 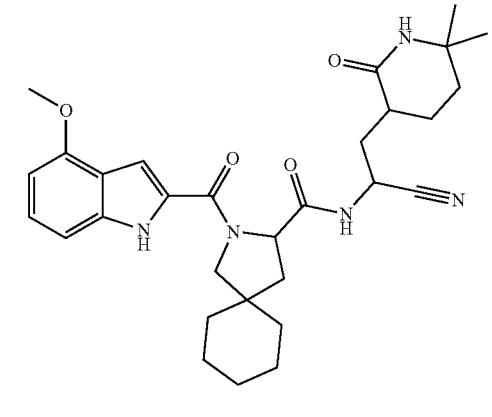 [SMILES: COc1cccc2[nH]c(C(=O)N3CC4(CCCCC4)CC3C(=O)NC(C#N)CC3CCC(C)(C)NC3=O)cc12] |
| 1111 | 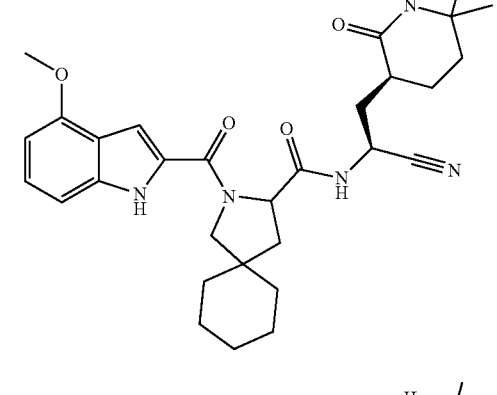 |
| 1112 | 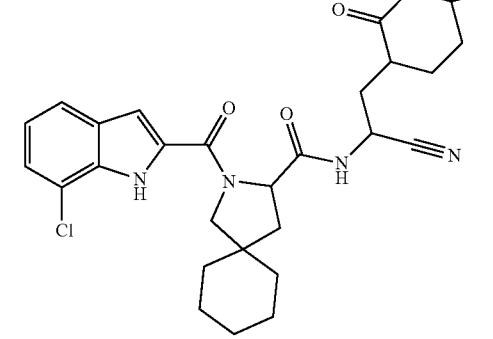 |

TABLE 1-continued

Exemplary compounds.

| Cmpd No. | Structure |
|---|---|
| 1113 | 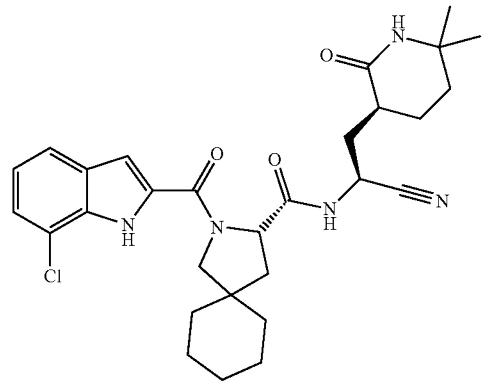 |
| 1114 | 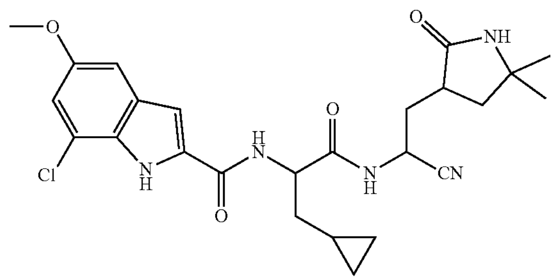 |
| 1115 | 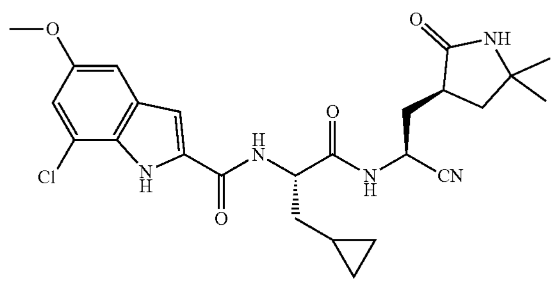 |
| 1116 | 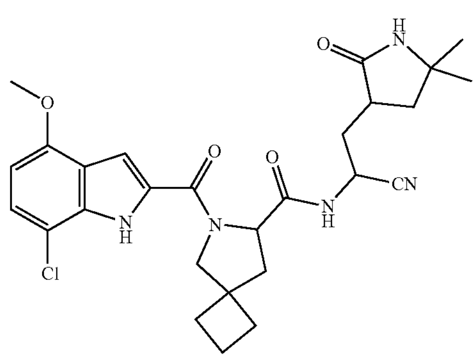 [SMILES: COc1ccc(Cl)c2[nH]c(C(=O)N3CC4(CCC4)CC3C(=O)NC(C#N)CC3CC(C)(C)NC3=O)cc12] |

TABLE 1-continued
Exemplary compounds.
| Cmpd No. | Structure |
|---|---|
| 1117 | 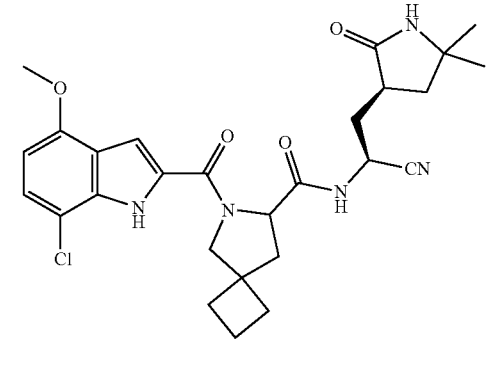 [SMILES: COc1ccc(Cl)c2[nH]c(C(=O)N3CC4(CCC4)CC3C(=O)N[C@H](C#N)C[C@@H]3CC(C)(C)NC3=O)cc12] |
| 1118 | 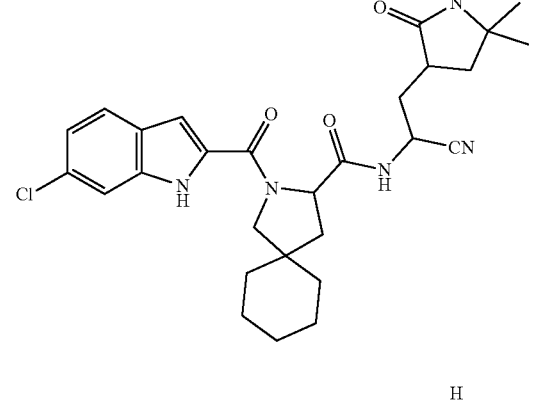 |
| 1119 | 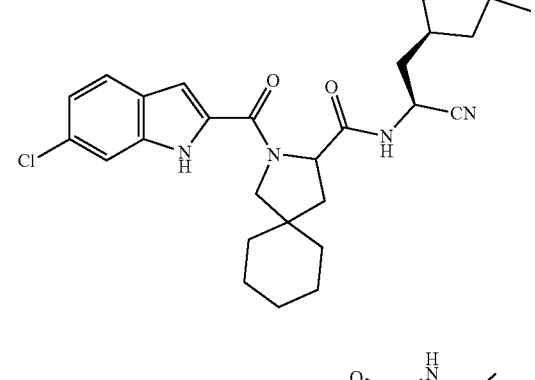 |
| 1120 | 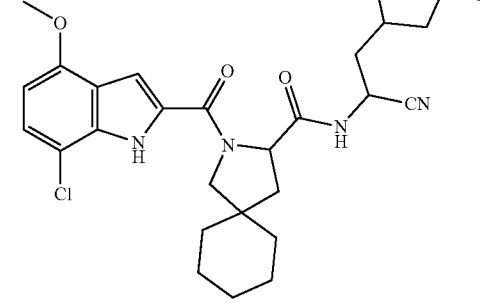 |

TABLE 1-continued
Exemplary compounds.
| Cmpd No. | Structure |
|---|---|
| 1121 | 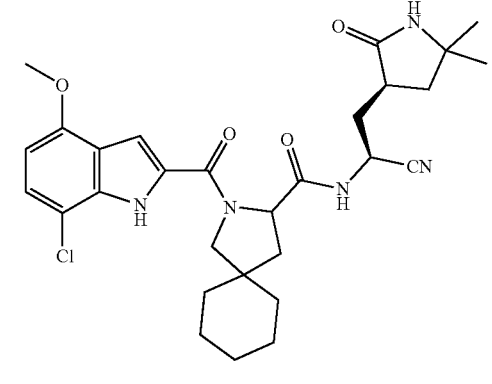 [SMILES: COc1ccc(Cl)c2[nH]c(C(=O)N3CC4(CCCCC4)CC3C(=O)N[C@H](C#N)C[C@@H]3CC(C)(C)NC3=O)cc12] |
| 1122 | 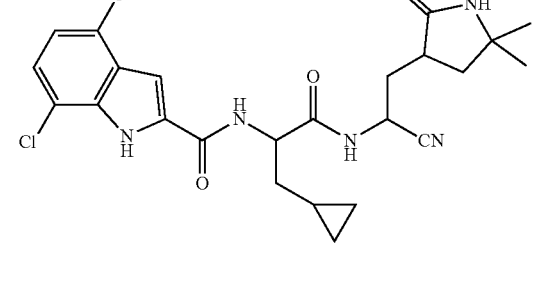 |
| 1123 | 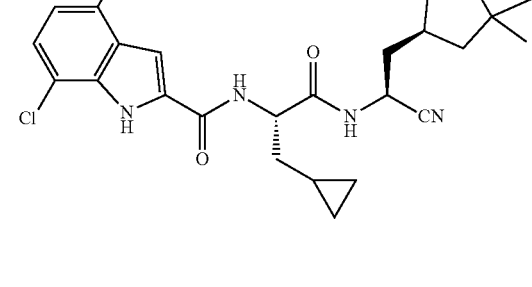 |
| 1124 | 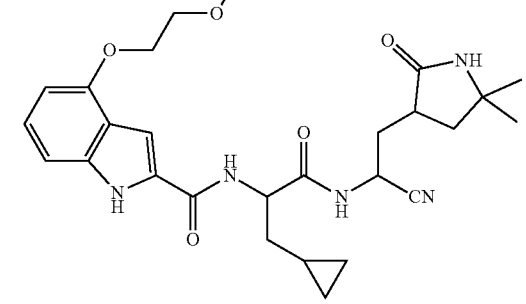 |

TABLE 1-continued

Exemplary compounds.

| Cmpd No. | Structure |
|---|---|
| 1125 | (structure) |
| 1128 | (structure) |
| 1129 | (structure) |
| 1130 | (structure) |

TABLE 1-continued

Exemplary compounds.

| Cmpd No. | Structure |
|---|---|
| 1131 | 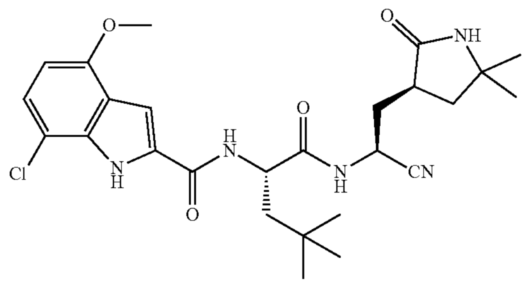 [SMILES: COc1ccc(Cl)c2[nH]c(C(=O)N[C@@H](CC(C)(C)C)C(=O)N[C@H](C#N)C[C@@H]3CC(C)(C)NC3=O)cc12] |
| 1132 | 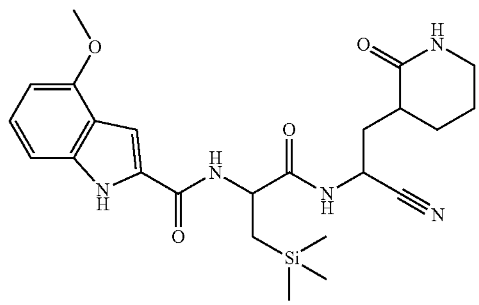 [SMILES: COc1cccc2[nH]c(C(=O)NC(C[Si](C)(C)C)C(=O)NC(C#N)CC3CCCNC3=O)cc12] |
| 1133 | 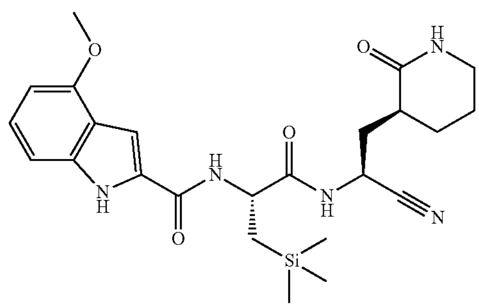 [SMILES: COc1cccc2[nH]c(C(=O)N[C@@H](C[Si](C)(C)C)C(=O)N[C@H](C#N)C[C@@H]3CCCNC3=O)cc12] |
| 1134 | 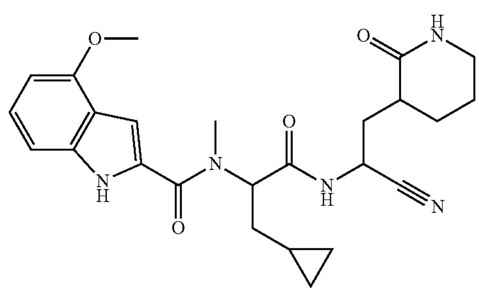 [SMILES: COc1cccc2[nH]c(C(=O)N(C)C(CC3CC3)C(=O)NC(C#N)CC3CCCNC3=O)cc12] |
| 1135 | 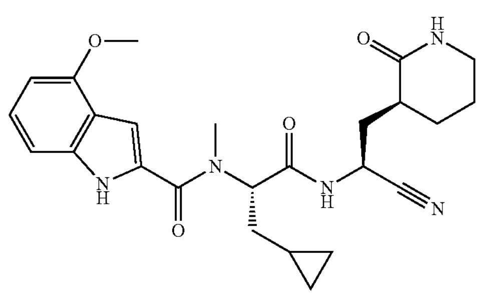 [SMILES: COc1cccc2[nH]c(C(=O)N(C)[C@@H](CC3CC3)C(=O)N[C@H](C#N)C[C@@H]3CCCNC3=O)cc12] |

TABLE 1-continued
Exemplary compounds.
| Cmpd No. | Structure |
|---|---|
| 1136 | 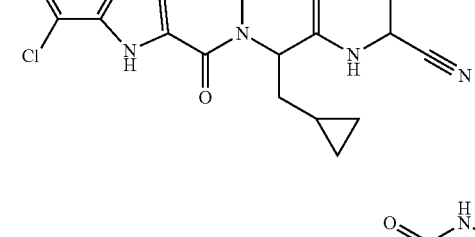 |
| 1137 | 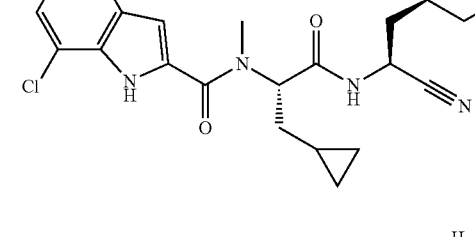 |
| 1138 | 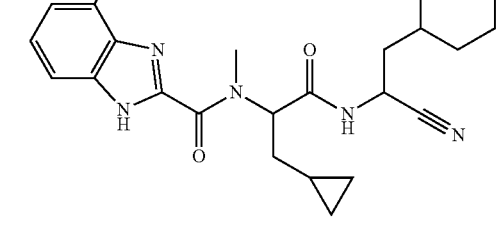 |
| 1139 | 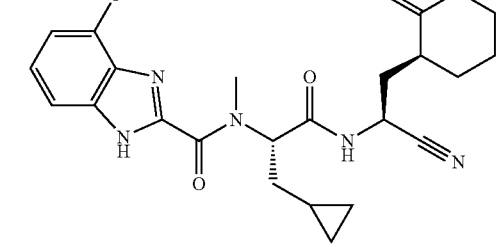 |
| 1140 | 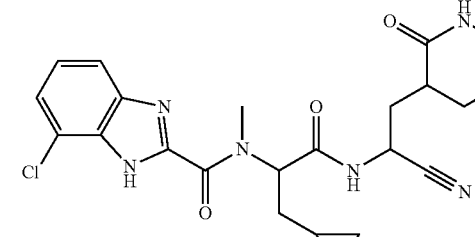 |

TABLE 1-continued
Exemplary compounds.
| Cmpd No. | Structure |
|---|---|
| 1141 | 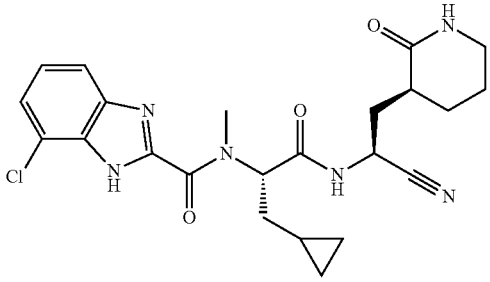 [SMILES: CN(C(=O)c1nc2cccc(Cl)c2[nH]1)[C@@H](CC1CC1)C(=O)N[C@H](C#N)C[C@@H]1CCCNC1=O] |
| 1142 | 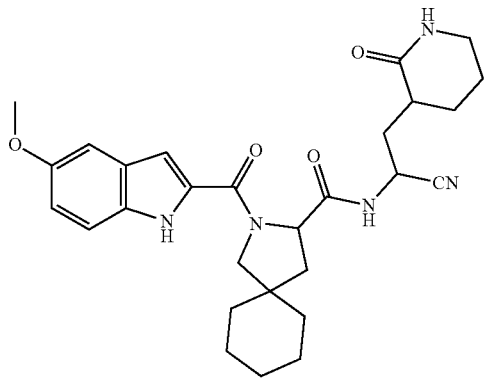 [SMILES: COc1ccc2[nH]c(C(=O)N3CC4(CCCCC4)CC3C(=O)NC(C#N)CC3CCCNC3=O)cc2c1] |
| 1143 | 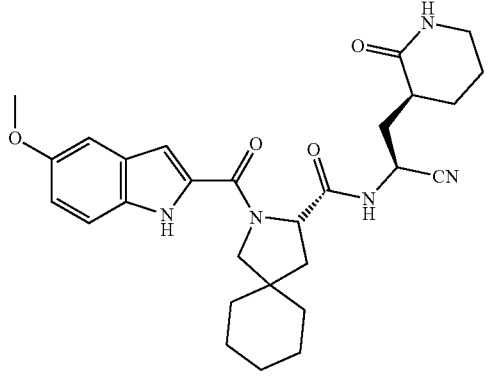 |
| 1144 | 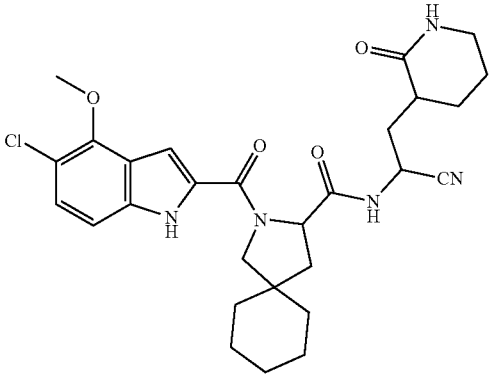 [SMILES: COc1c(Cl)ccc2[nH]c(C(=O)N3CC4(CCCCC4)CC3C(=O)NC(C#N)CC3CCCNC3=O)cc12] |

TABLE 1-continued

Exemplary compounds.

| Cmpd No. | Structure |
|---|---|
| 1145 | 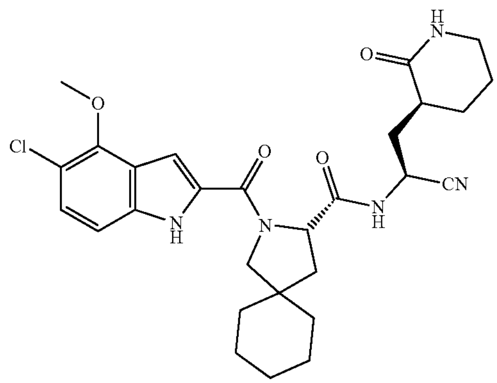 |
| 1146 | 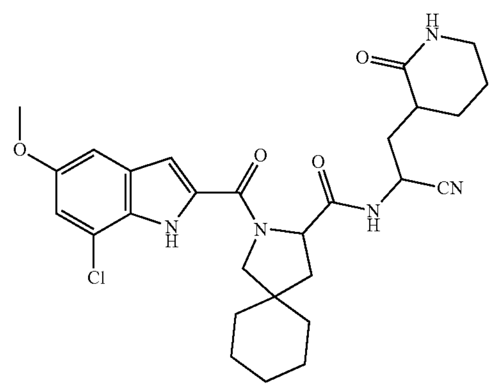 [SMILES: COc1cc(Cl)c2[nH]c(C(=O)N3CC4(CCCCC4)CC3C(=O)NC(C#N)CC3CCCNC3=O)cc2c1] |
| 1147 | 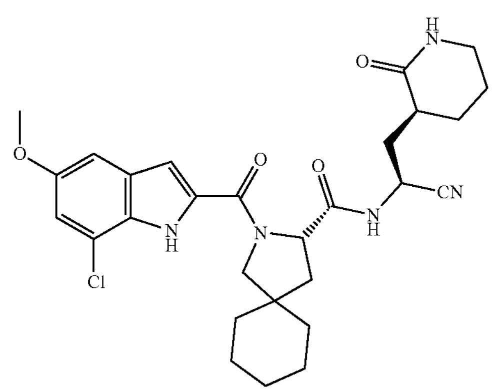 [SMILES: COc1cc(Cl)c2[nH]c(C(=O)N3CC4(CCCCC4)CC3C(=O)N[C@H](C#N)C[C@@H]3CCCNC3=O)cc2c1] |
| 1147A | 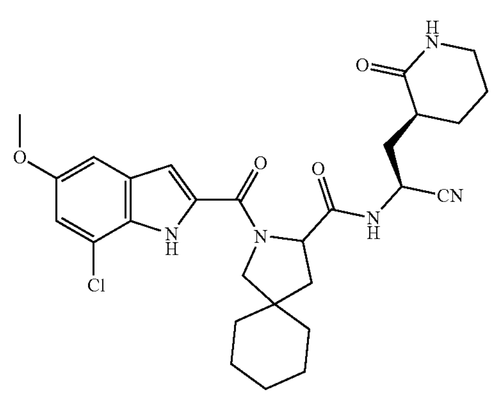 |

TABLE 1-continued
Exemplary compounds.
| Cmpd No. | Structure |
|---|---|
| 1148 | 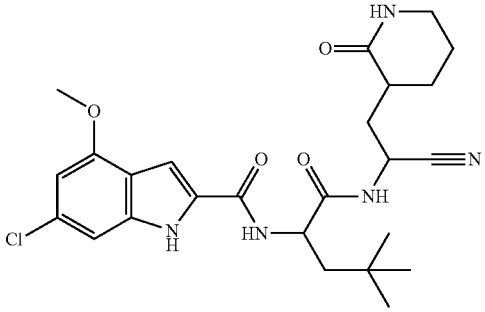 [SMILES: COc1cc(Cl)cc2[nH]c(C(=O)NC(CC(C)(C)C)C(=O)NC(C#N)CC3CCCNC3=O)cc12] |
| 1149 | 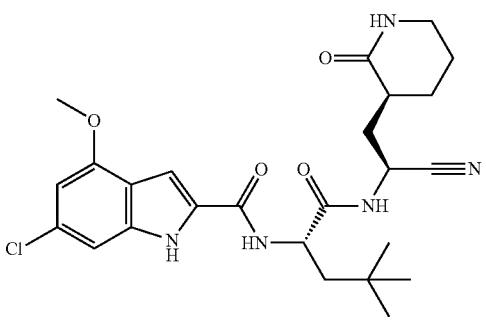 [SMILES: COc1cc(Cl)cc2[nH]c(C(=O)N[C@@H](CC(C)(C)C)C(=O)N[C@H](C#N)C[C@@H]3CCCNC3=O)cc12] |
| 1150 | 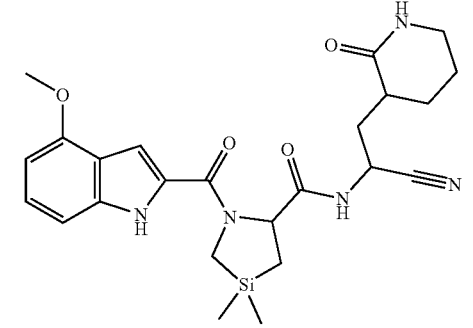 [SMILES: COc1cccc2[nH]c(C(=O)N3C[Si](C)(C)CC3C(=O)NC(C#N)CC3CCCNC3=O)cc12] |
| 1151 | 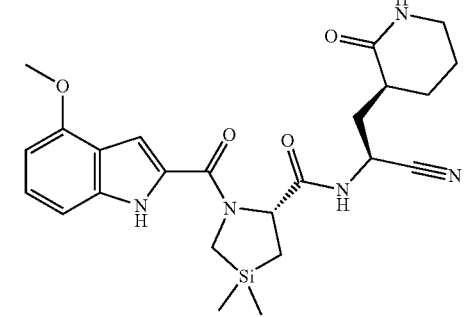 |

TABLE 1-continued
Exemplary compounds.
| Cmpd No. | Structure |
|---|---|
| 1152 | 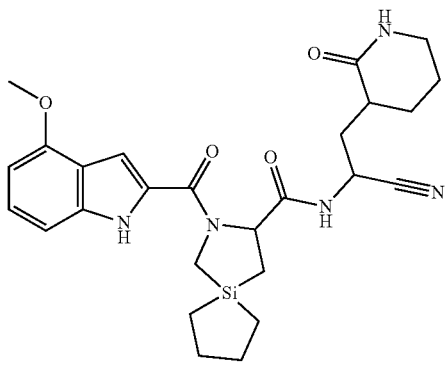 [SMILES: COc1cccc2[nH]c(C(=O)N3C[Si]4(CCCC4)CC3C(=O)NC(C#N)CC3CCCNC3=O)cc12] |
| 1153 | 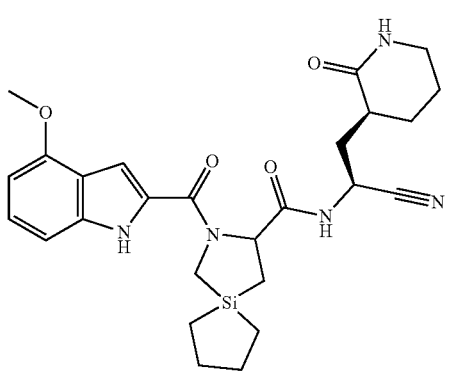 [SMILES: COc1cccc2[nH]c(C(=O)N3C[Si]4(CCCC4)CC3C(=O)N[C@H](C#N)C[C@@H]3CCCNC3=O)cc12] |
| 1154 | 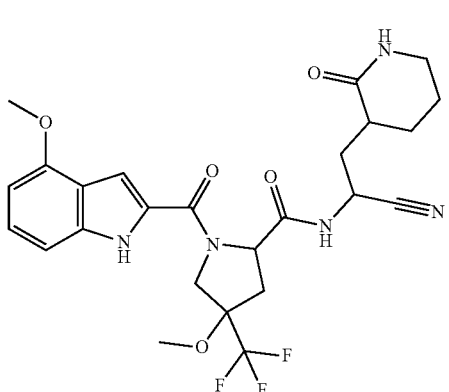 |
| 1155 | 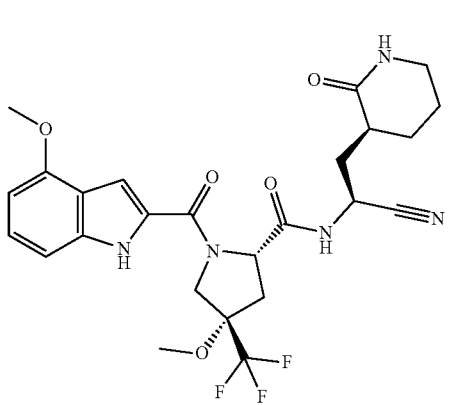 [SMILES: COc1cccc2[nH]c(C(=O)N3C[C@](OC)(C(F)(F)F)C[C@H]3C(=O)N[C@H](C#N)C[C@@H]3CCCNC3=O)cc12] |

TABLE 1-continued
Exemplary compounds.
| Cmpd No. | Structure |
|---|---|
| 1156 | 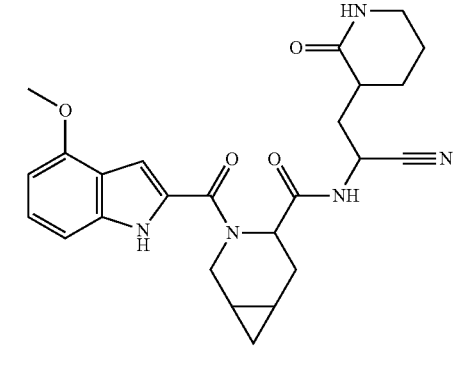 [SMILES: COc1cccc2[nH]c(C(=O)N3CC4CC4CC3C(=O)NC(C#N)CC3CCCNC3=O)cc12] |
| 1157 | 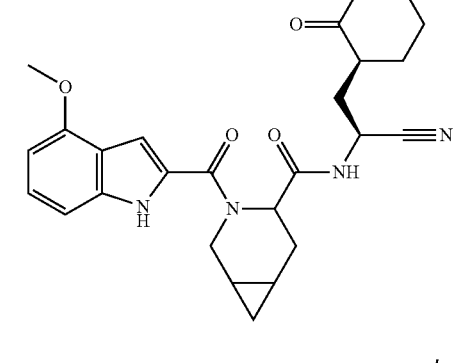 |
| 1158 | 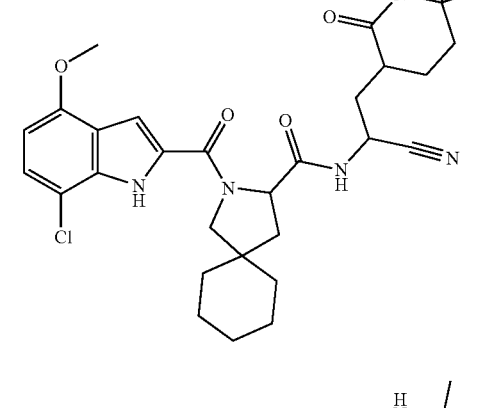 |
| 1159 | 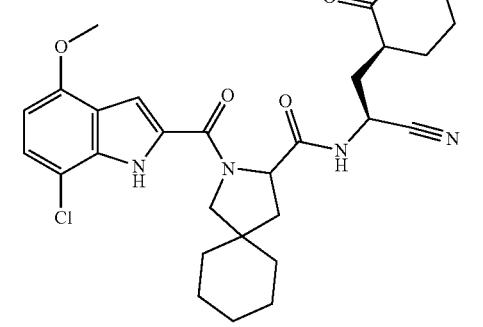 |

TABLE 1-continued

Exemplary compounds.

| Cmpd No. | Structure |
|---|---|
| 1160 | 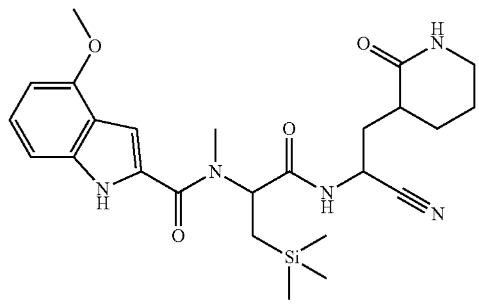 [SMILES: COc1cccc2[nH]c(C(=O)N(C)C(C[Si](C)(C)C)C(=O)NC(C#N)CC3CCCNC3=O)cc12] |
| 1161 | 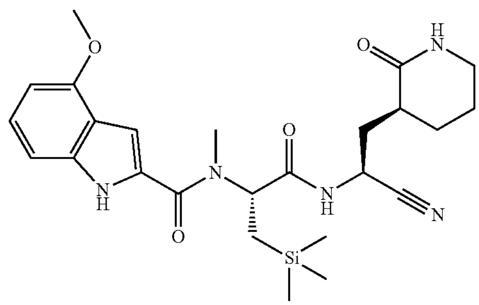 [SMILES: COc1cccc2[nH]c(C(=O)N(C)[C@@H](C[Si](C)(C)C)C(=O)N[C@H](C#N)C[C@@H]3CCCNC3=O)cc12] |
| 1162 | 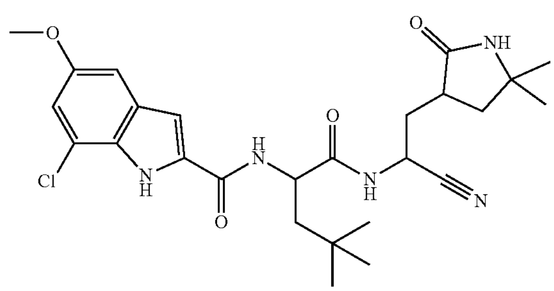 |
| 1163 | 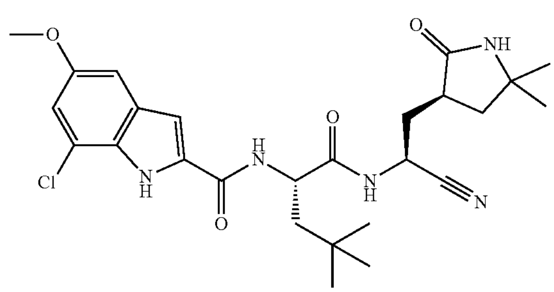 |
| 1164 | 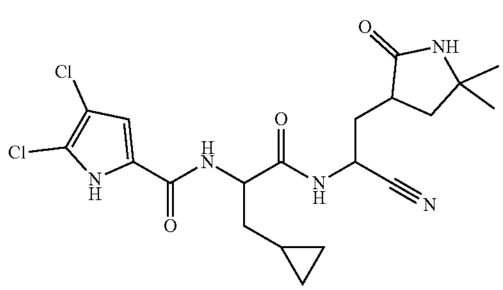 [SMILES: CC1(C)CC(CC(C#N)NC(=O)C(CC2CC2)NC(=O)c2cc(Cl)c(Cl)[nH]2)C(=O)N1] |

TABLE 1-continued

Exemplary compounds.

| Cmpd No. | Structure |
|---|---|
| 1165 | 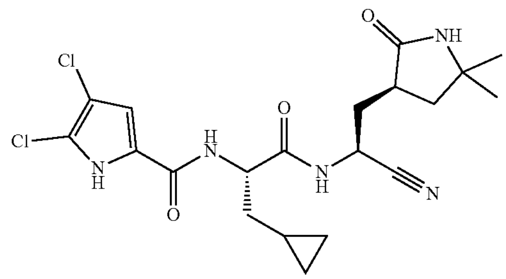 [SMILES: CC1(C)C[C@@H](C[C@@H](C#N)NC(=O)[C@H](CC2CC2)NC(=O)c2cc(Cl)c(Cl)[nH]2)C(=O)N1] |
| 1166 | 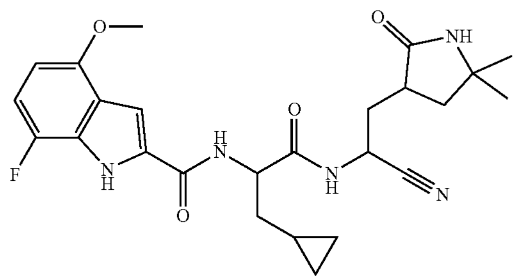 [SMILES: COc1ccc(F)c2[nH]c(C(=O)NC(CC3CC3)C(=O)NC(C#N)CC3CC(C)(C)NC3=O)cc12] |
| 1167 | 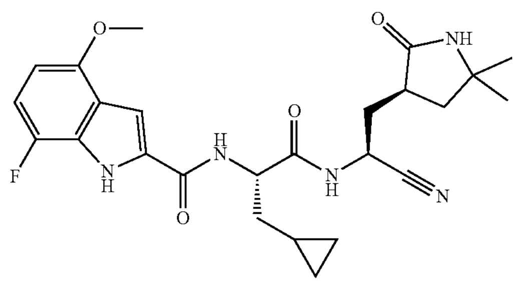 [SMILES: COc1ccc(F)c2[nH]c(C(=O)N[C@@H](CC3CC3)C(=O)N[C@H](C#N)C[C@@H]3CC(C)(C)NC3=O)cc12] |
| 1168 | 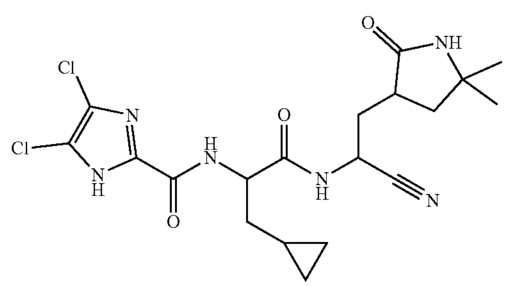 [SMILES: CC1(C)CC(CC(C#N)NC(=O)C(CC2CC2)NC(=O)c2nc(Cl)c(Cl)[nH]2)C(=O)N1] |
| 1169 | 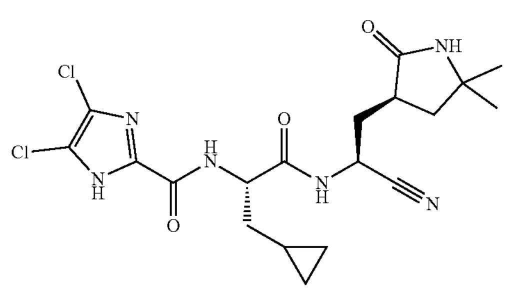 [SMILES: CC1(C)C[C@@H](C[C@@H](C#N)NC(=O)[C@H](CC2CC2)NC(=O)c2nc(Cl)c(Cl)[nH]2)C(=O)N1] |

TABLE 1-continued

Exemplary compounds.

| Cmpd No. | Structure |
|---|---|
| 1170 | 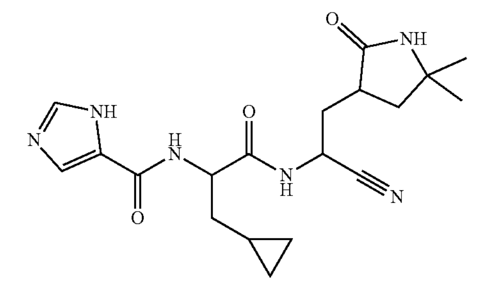 [SMILES: CC1(C)CC(CC(C#N)NC(=O)C(CC2CC2)NC(=O)c2cnc[nH]2)C(=O)N1] |
| 1171 | 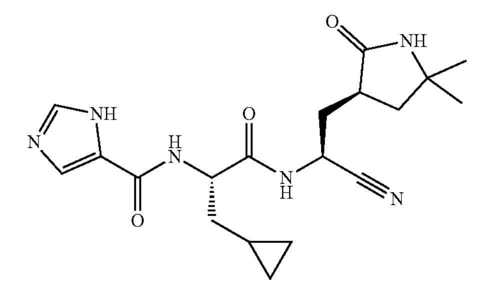 [SMILES: CC1(C)C[C@@H](C[C@@H](C#N)NC(=O)[C@H](CC2CC2)NC(=O)c2cnc[nH]2)C(=O)N1] |
| 1172 | 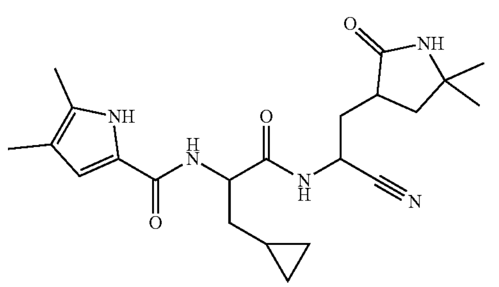 |
| 1173 | 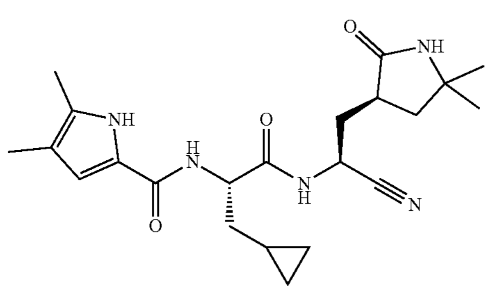 |
| 1174 | 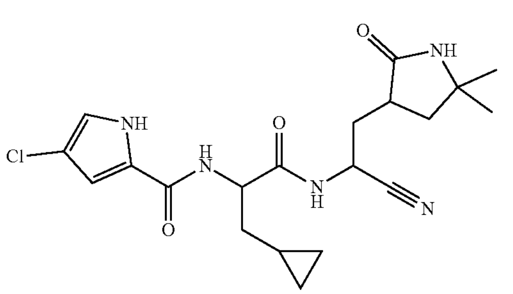 [SMILES: CC1(C)CC(CC(C#N)NC(=O)C(CC2CC2)NC(=O)c2cc(Cl)c[nH]2)C(=O)N1] |

TABLE 1-continued

Exemplary compounds.

| Cmpd No. | Structure |
|---|---|
| 1175 | 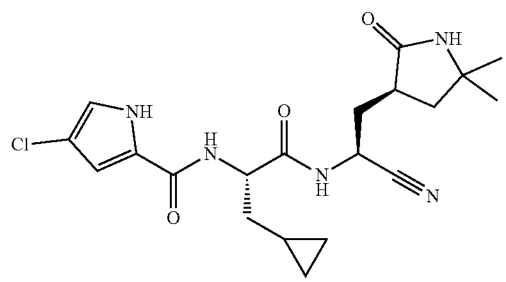 [SMILES: CC1(C)C[C@@H](C[C@@H](C#N)NC(=O)[C@H](CC2CC2)NC(=O)c2cc(Cl)c[nH]2)C(=O)N1] |
| 1176 | 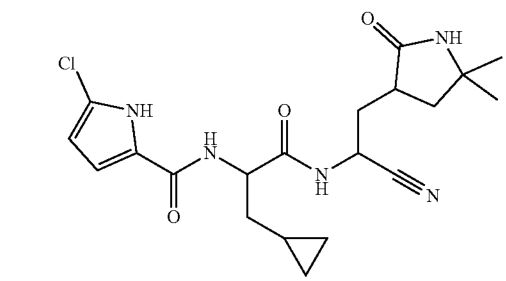 [SMILES: CC1(C)CC(CC(C#N)NC(=O)C(CC2CC2)NC(=O)c2ccc(Cl)[nH]2)C(=O)N1] |
| 1177 | 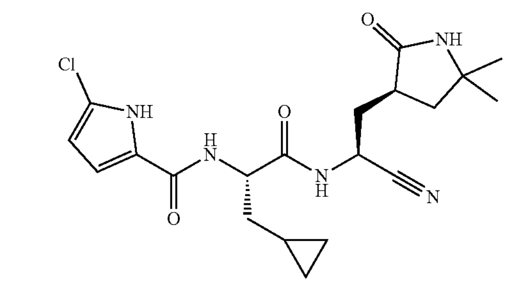 [SMILES: CC1(C)C[C@@H](C[C@@H](C#N)NC(=O)[C@H](CC2CC2)NC(=O)c2ccc(Cl)[nH]2)C(=O)N1] |
| 1178 | 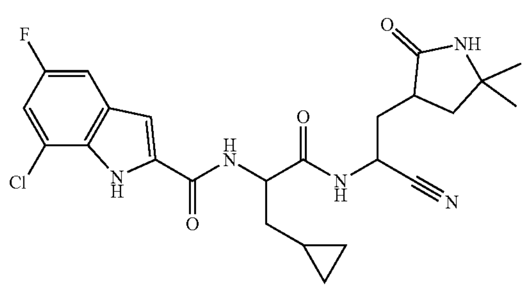 [SMILES: CC1(C)CC(CC(C#N)NC(=O)C(CC2CC2)NC(=O)c2cc3cc(F)cc(Cl)c3[nH]2)C(=O)N1] |
| 1179 | 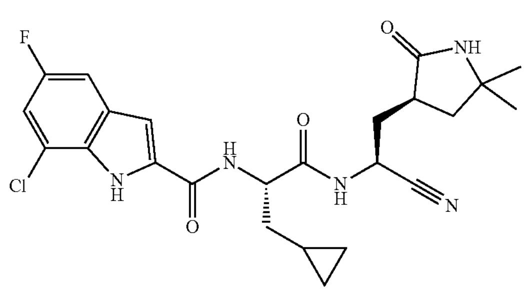 [SMILES: CC1(C)C[C@@H](C[C@@H](C#N)NC(=O)[C@H](CC2CC2)NC(=O)c2cc3cc(F)cc(Cl)c3[nH]2)C(=O)N1] |

TABLE 1-continued

Exemplary compounds.

| Cmpd No. | Structure |
|---|---|
| 1180 | 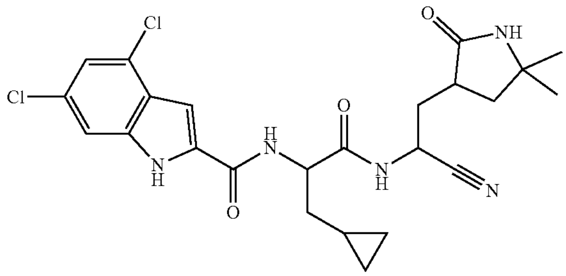 [SMILES: CC1(C)CC(CC(C#N)NC(=O)C(CC2CC2)NC(=O)c2cc3c(Cl)cc(Cl)cc3[nH]2)C(=O)N1] |
| 1181 | 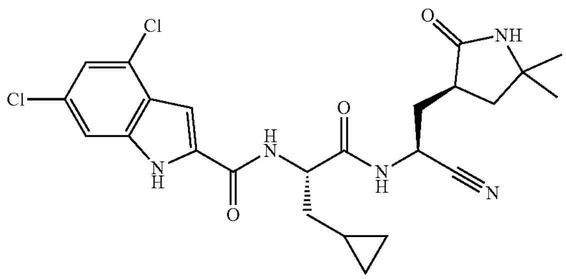 [SMILES: CC1(C)C[C@@H](C[C@@H](C#N)NC(=O)[C@H](CC2CC2)NC(=O)c2cc3c(Cl)cc(Cl)cc3[nH]2)C(=O)N1] |
| 1182 | 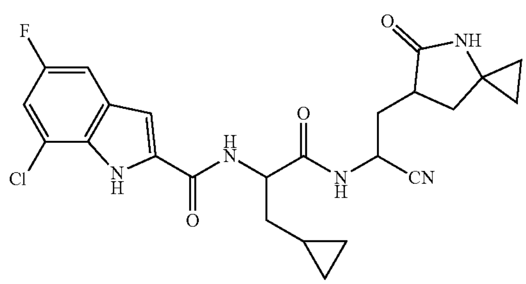 [SMILES: N#CC(CC1CC2(CC2)NC1=O)NC(=O)C(CC1CC1)NC(=O)c1cc2cc(F)cc(Cl)c2[nH]1] |
| 1183 | 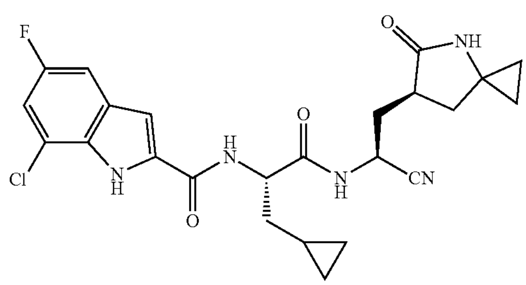 |
| 1184 | 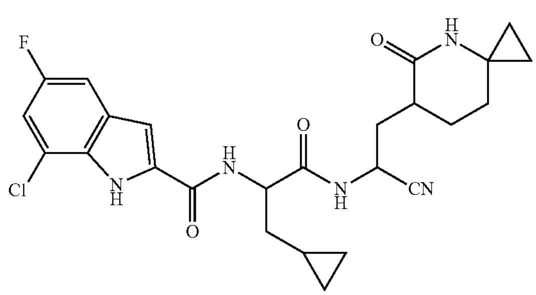 [SMILES: N#CC(CC1CCC2(CC2)NC1=O)NC(=O)C(CC1CC1)NC(=O)c1cc2cc(F)cc(Cl)c2[nH]1] |

TABLE 1-continued

Exemplary compounds.

| Cmpd No. | Structure |
|---|---|
| 1185 | 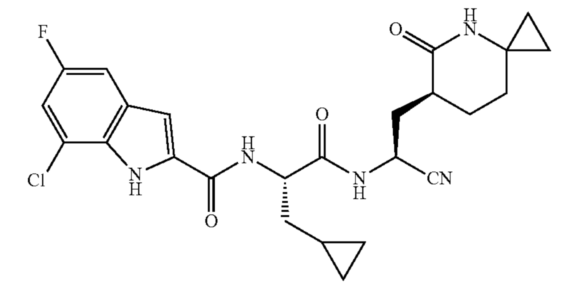 [SMILES: N#C[C@H](C[C@@H]1CCC2(CC2)NC1=O)NC(=O)[C@H](CC1CC1)NC(=O)c1cc2cc(F)cc(Cl)c2[nH]1] |
| 1186 | 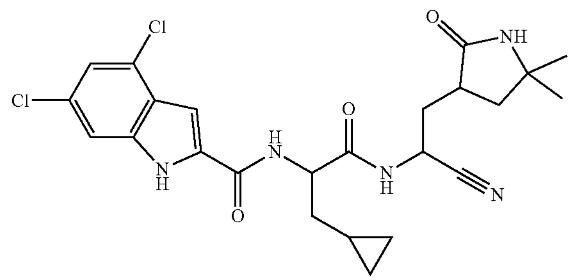 [SMILES: CC1(C)CC(CC(C#N)NC(=O)C(CC2CC2)NC(=O)c2cc3c(Cl)cc(Cl)cc3[nH]2)C(=O)N1] |
| 1187 | 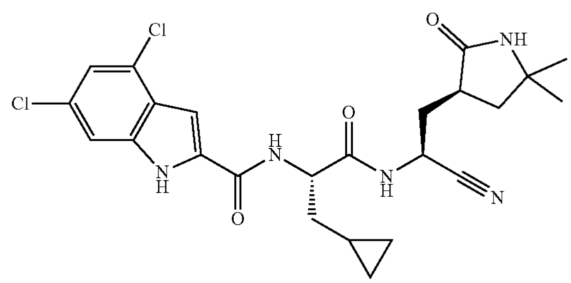 [SMILES: CC1(C)C[C@@H](C[C@@H](C#N)NC(=O)[C@H](CC2CC2)NC(=O)c2cc3c(Cl)cc(Cl)cc3[nH]2)C(=O)N1] |
| 1188 | 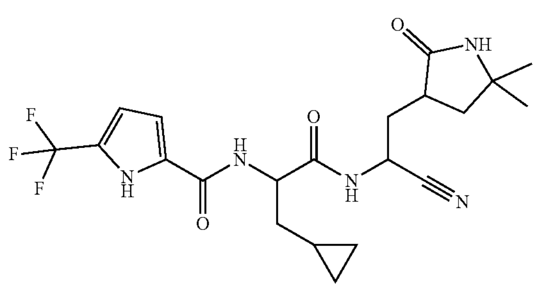 [SMILES: CC1(C)CC(CC(C#N)NC(=O)C(CC2CC2)NC(=O)c2ccc(C(F)(F)F)[nH]2)C(=O)N1] |
| 1189 | 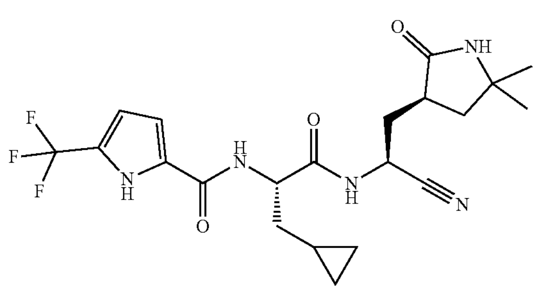 [SMILES: CC1(C)C[C@@H](C[C@@H](C#N)NC(=O)[C@H](CC2CC2)NC(=O)c2ccc(C(F)(F)F)[nH]2)C(=O)N1] |

TABLE 1-continued

| Cmpd No. | Structure |
|---|---|
| 1190 | 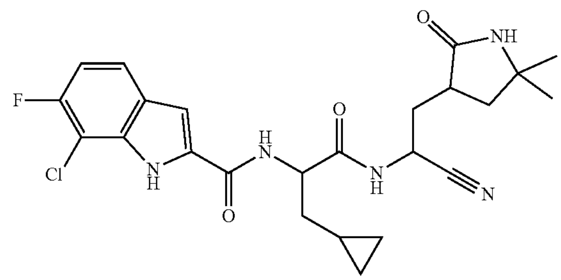 [SMILES: CC1(C)CC(CC(C#N)NC(=O)C(CC2CC2)NC(=O)c2cc3ccc(F)c(Cl)c3[nH]2)C(=O)N1] |
| 1191 | 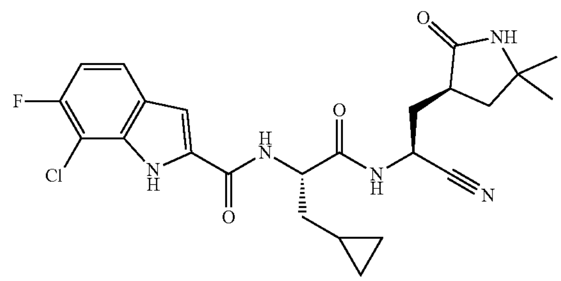 [SMILES: CC1(C)C[C@@H](C[C@@H](C#N)NC(=O)[C@H](CC2CC2)NC(=O)c2cc3ccc(F)c(Cl)c3[nH]2)C(=O)N1] |
| 1192 | 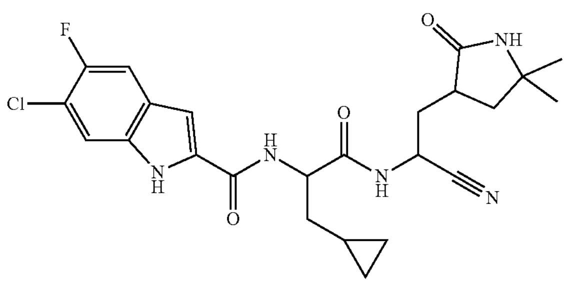 [SMILES: CC1(C)CC(CC(C#N)NC(=O)C(CC2CC2)NC(=O)c2cc3cc(F)c(Cl)cc3[nH]2)C(=O)N1] |
| 1193 | 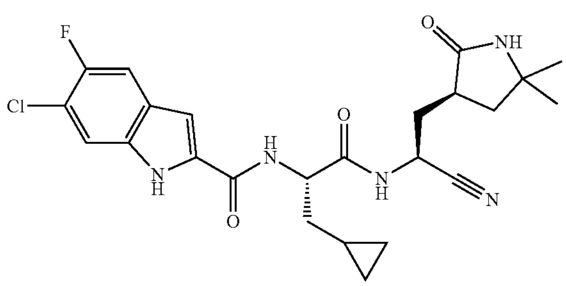 [SMILES: CC1(C)C[C@@H](C[C@@H](C#N)NC(=O)[C@H](CC2CC2)NC(=O)c2cc3cc(F)c(Cl)cc3[nH]2)C(=O)N1] |
| 1194 | 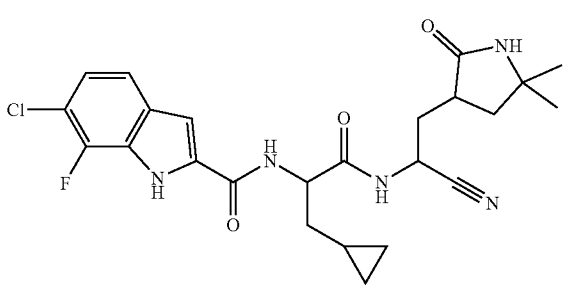 [SMILES: CC1(C)CC(CC(C#N)NC(=O)C(CC2CC2)NC(=O)c2cc3ccc(Cl)c(F)c3[nH]2)C(=O)N1] |

TABLE 1-continued
Exemplary compounds.
| Cmpd No. | Structure |
|---|---|
| 1195 | 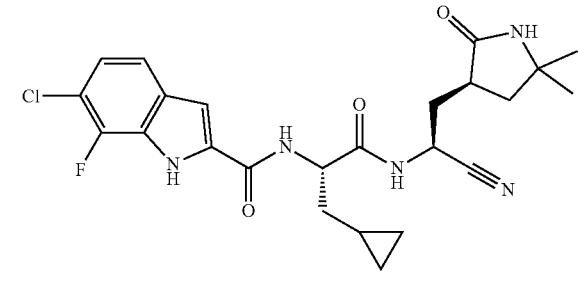 [SMILES: CC1(C)C[C@@H](C[C@@H](C#N)NC(=O)[C@H](CC2CC2)NC(=O)c2cc3ccc(Cl)c(F)c3[nH]2)C(=O)N1] |
| 1196 | 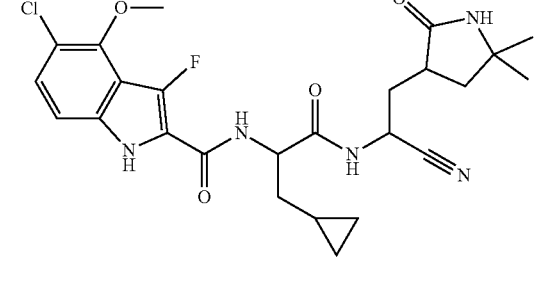 |
| 1197 | 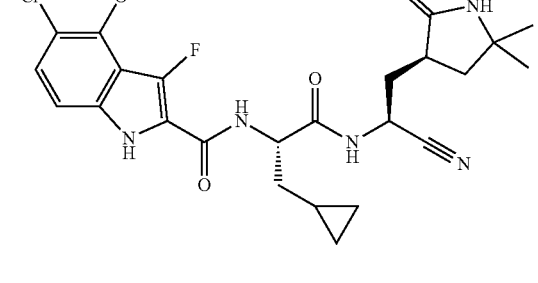 |
| 1198 | 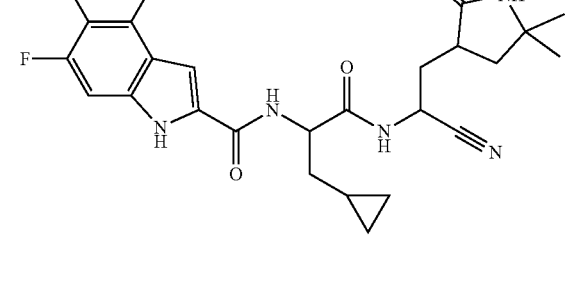 |
| 1199 | 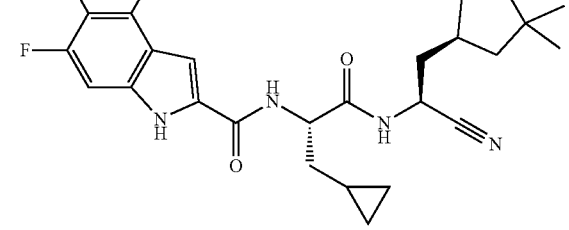 |

TABLE 1-continued
Exemplary compounds.
| Cmpd No. | Structure |
|---|---|
| 1200 | 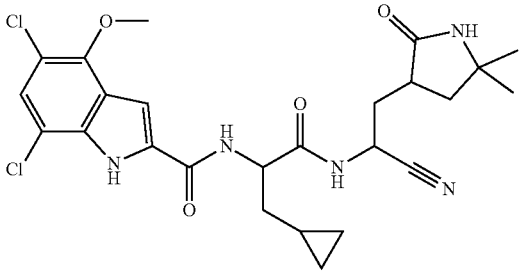 [SMILES: COc1c(Cl)cc(Cl)c2[nH]c(C(=O)NC(CC3CC3)C(=O)NC(C#N)CC3CC(C)(C)NC3=O)cc12] |
| 1201 | 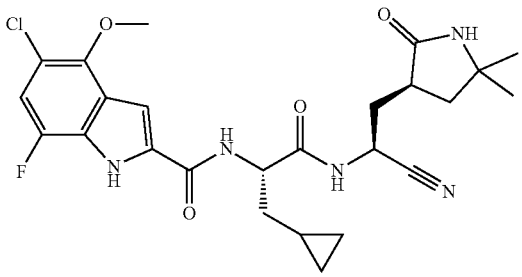 |
| 1202 | 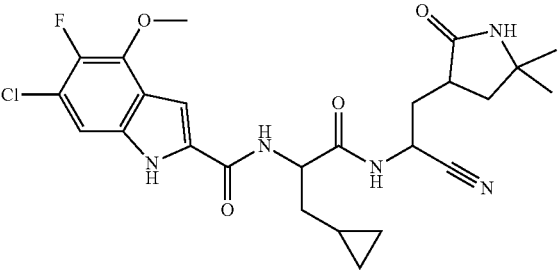 [SMILES: COc1c(F)c(Cl)cc2[nH]c(C(=O)NC(CC3CC3)C(=O)NC(C#N)CC3CC(C)(C)NC3=O)cc12] |
| 1203 | 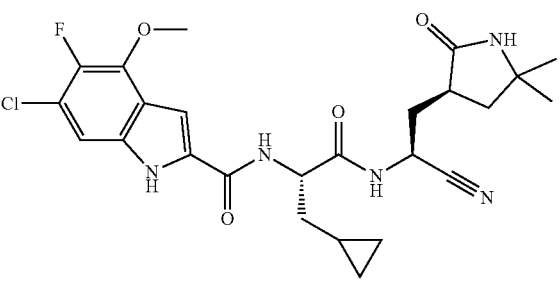 [SMILES: COc1c(F)c(Cl)cc2[nH]c(C(=O)N[C@@H](CC3CC3)C(=O)N[C@H](C#N)C[C@@H]3CC(C)(C)NC3=O)cc12] |
| 1204 | 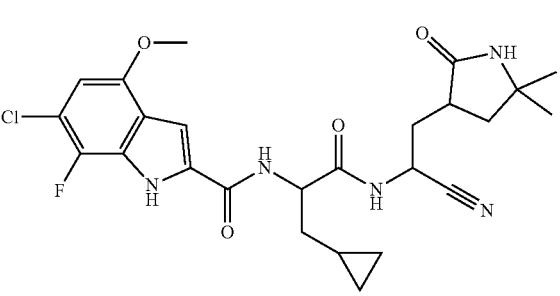 [SMILES: COc1cc(Cl)c(F)c2[nH]c(C(=O)NC(CC3CC3)C(=O)NC(C#N)CC3CC(C)(C)NC3=O)cc12] |

TABLE 1-continued

Exemplary compounds.

| Cmpd No. | Structure |
|---|---|
| 1205 | 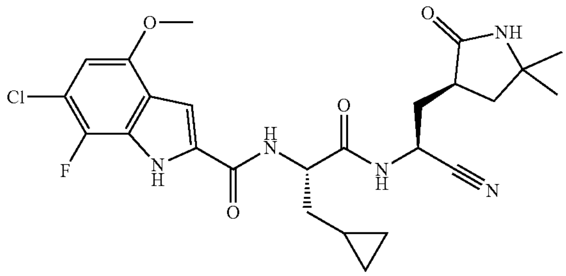 [SMILES: COc1cc(Cl)c(F)c2[nH]c(C(=O)N[C@@H](CC3CC3)C(=O)N[C@H](C#N)C[C@@H]3CC(C)(C)NC3=O)cc12] |
| 1206 | 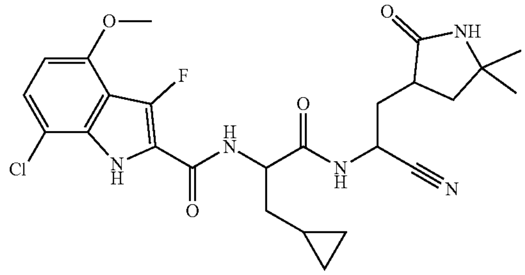 [SMILES: COc1ccc(Cl)c2[nH]c(C(=O)NC(CC3CC3)C(=O)NC(C#N)CC3CC(C)(C)NC3=O)c(F)c12] |
| 1207 | 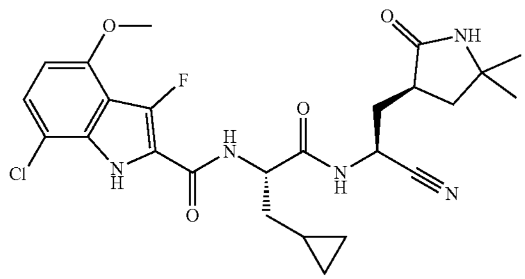 [SMILES: COc1ccc(Cl)c2[nH]c(C(=O)N[C@@H](CC3CC3)C(=O)N[C@H](C#N)C[C@@H]3CC(C)(C)NC3=O)c(F)c12] |
| 1208 | 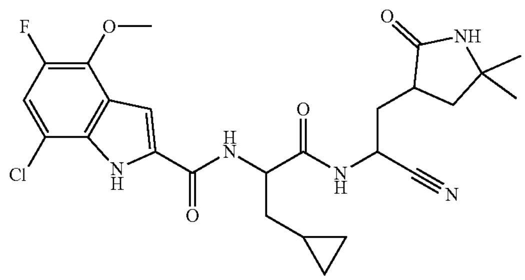 |
| 1209 | 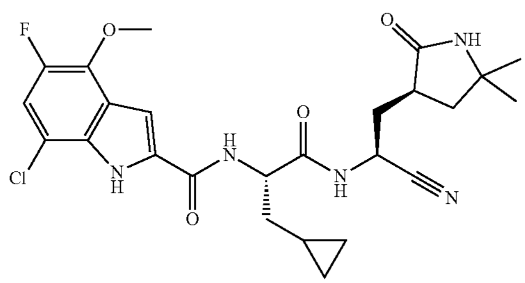 [SMILES: COc1c(F)cc(Cl)c2[nH]c(C(=O)N[C@@H](CC3CC3)C(=O)N[C@H](C#N)C[C@@H]3CC(C)(C)NC3=O)cc12] |

TABLE 1-continued
Exemplary compounds.
| Cmpd No. | Structure |
|---|---|
| 1210 | 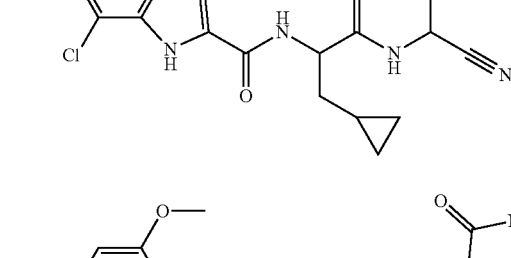 |
| 1211 | 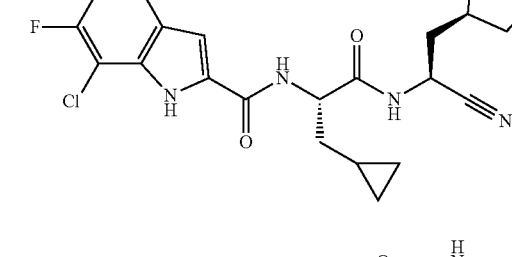 |
| 1212 | 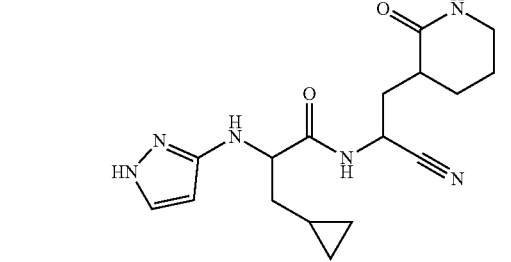 |
| 1213 | 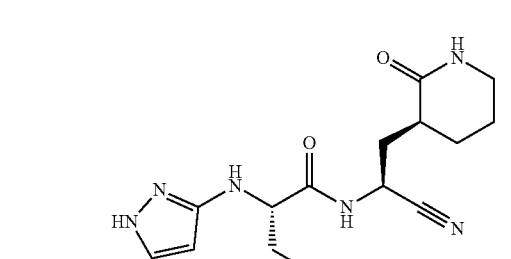 |
| 1214 | 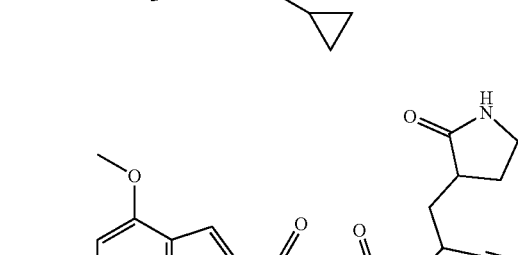 |

TABLE 1-continued

Exemplary compounds.

| Cmpd No. | Structure |
|---|---|
| 1215 | 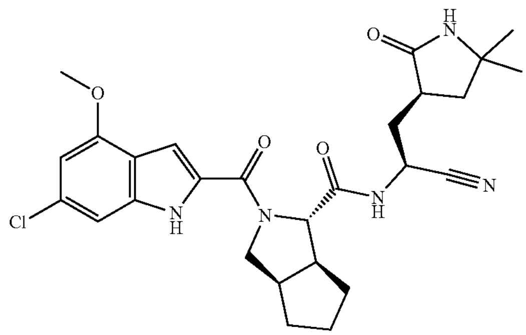 [SMILES: COc1cc(Cl)cc2[nH]c(C(=O)N3C[C@@H]4CCC[C@@H]4[C@H]3C(=O)N[C@H](C#N)C[C@@H]3CC(C)(C)NC3=O)cc12] |
| 1216 | 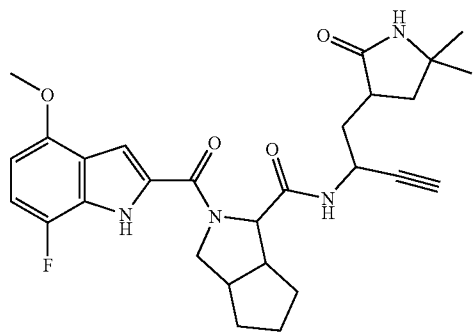 [SMILES: C#CC(CC1CC(C)(C)NC1=O)NC(=O)C1C2CCCC2CN1C(=O)c1cc2c(OC)ccc(F)c2[nH]1] |
| 1217 | 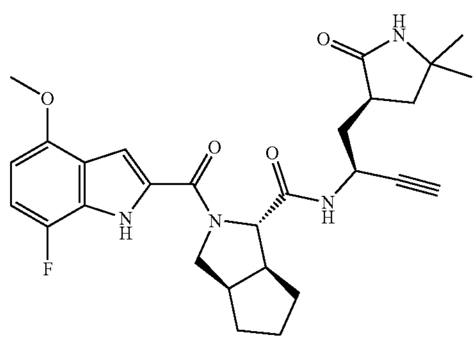 [SMILES: C#C[C@H](C[C@@H]1CC(C)(C)NC1=O)NC(=O)[C@@H]1[C@H]2CCC[C@H]2CN1C(=O)c1cc2c(OC)ccc(F)c2[nH]1] |
| 1218 | 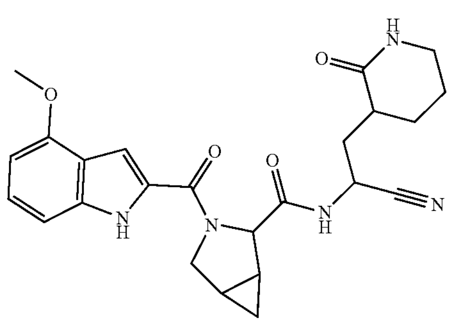 [SMILES: COc1cccc2[nH]c(C(=O)N3CC4CC4C3C(=O)NC(C#N)CC3CCCNC3=O)cc12] |

TABLE 1-continued

Exemplary compounds.

| Cmpd No. | Structure |
|---|---|
| 1219 | 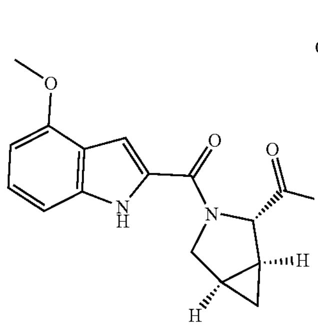 |
| 1220 | 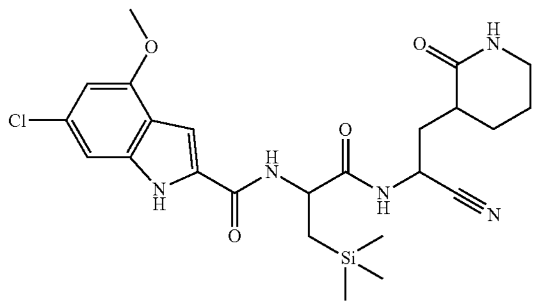 [SMILES: COc1cc(Cl)cc2[nH]c(C(=O)NC(C[Si](C)(C)C)C(=O)NC(C#N)CC3CCCNC3=O)cc12] |
| 1221 | 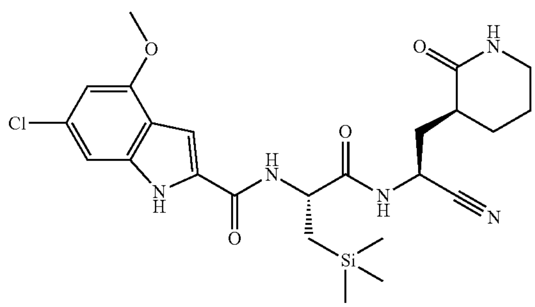 [SMILES: COc1cc(Cl)cc2[nH]c(C(=O)N[C@@H](C[Si](C)(C)C)C(=O)N[C@H](C#N)C[C@@H]3CCCNC3=O)cc12] |
| 1222 | 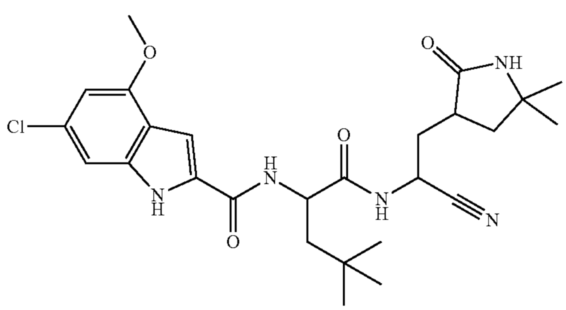 [SMILES: COc1cc(Cl)cc2[nH]c(C(=O)NC(C[Si](C)(C)C)C(=O)NC(C#N)CC3CC(C)(C)NC3=O)cc12] |
| 1223 | 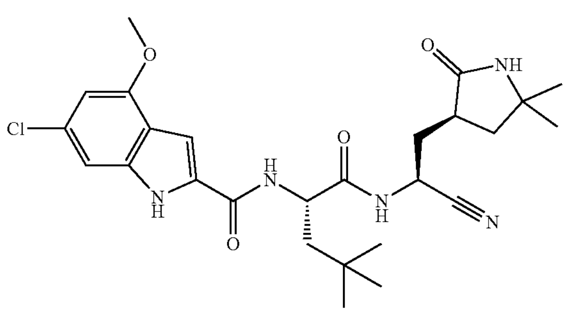 [SMILES: COc1cc(Cl)cc2[nH]c(C(=O)N[C@@H](C[Si](C)(C)C)C(=O)N[C@H](C#N)C[C@@H]3CC(C)(C)NC3=O)cc12] |

TABLE 1-continued
Exemplary compounds.
| Cmpd No. | Structure |
|---|---|
| 1224 | 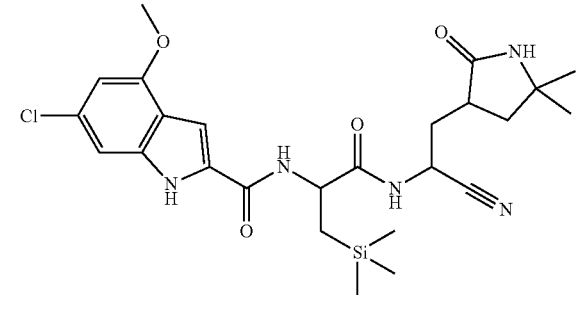 |
| 1225 | 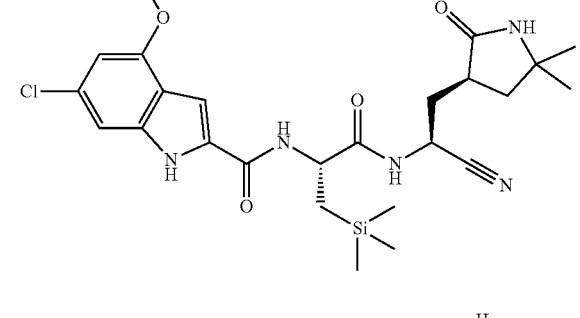 |
| 1226 | 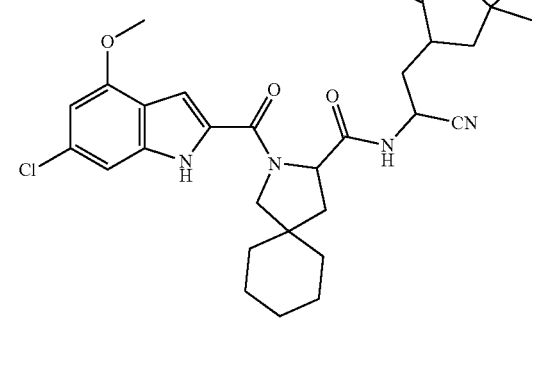 |
| 1227 | 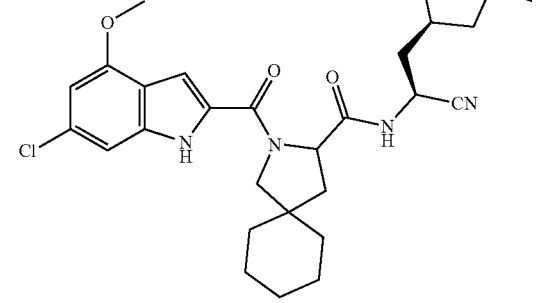 |

TABLE 1-continued

Exemplary compounds.

| Cmpd No. | Structure |
|---|---|
| 1228 | 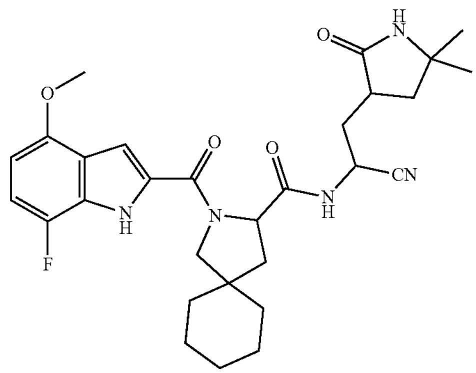 [SMILES: COc1ccc(F)c2[nH]c(C(=O)N3CC4(CCCCC4)CC3C(=O)NC(C#N)CC3CC(C)(C)NC3=O)cc12] |
| 1229 | 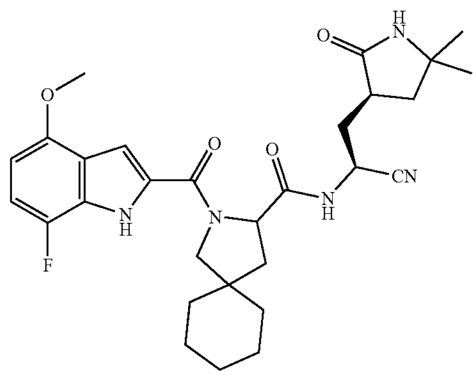 [SMILES: COc1ccc(F)c2[nH]c(C(=O)N3CC4(CCCCC4)CC3C(=O)N[C@H](C#N)C[C@@H]3CC(C)(C)NC3=O)cc12] |
| 1230 | 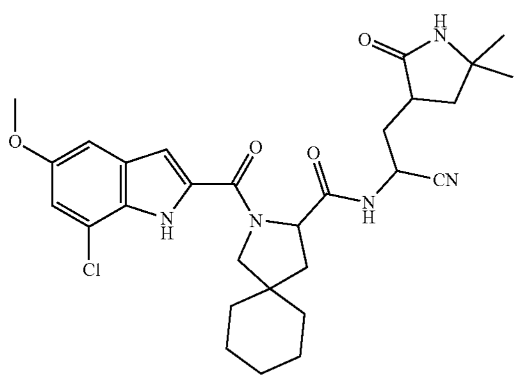 [SMILES: COc1cc(Cl)c2[nH]c(C(=O)N3CC4(CCCCC4)CC3C(=O)NC(C#N)CC3CC(C)(C)NC3=O)cc2c1] |
| 1231 | 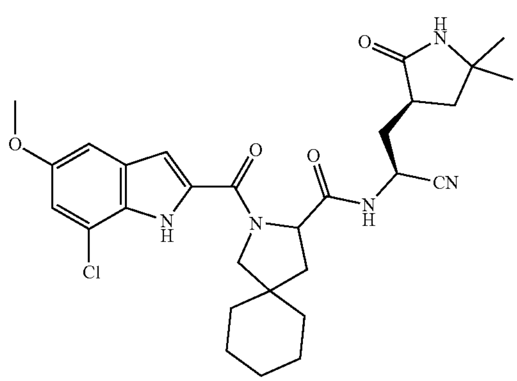 [SMILES: COc1cc(Cl)c2[nH]c(C(=O)N3CC4(CCCCC4)CC3C(=O)N[C@H](C#N)C[C@@H]3CC(C)(C)NC3=O)cc2c1] |

TABLE 1-continued
Exemplary compounds.
| Cmpd No. | Structure |
|---|---|
| 1232 | 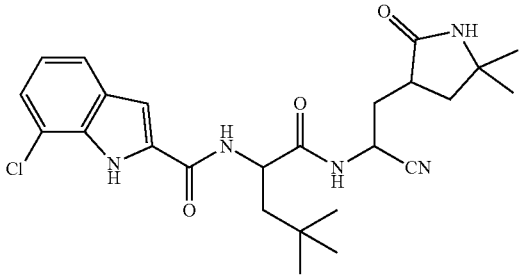 [SMILES: CC(C)(C)CC(NC(=O)c1cc2cccc(Cl)c2[nH]1)C(=O)NC(C#N)CC1CC(C)(C)NC1=O] |
| 1233 | 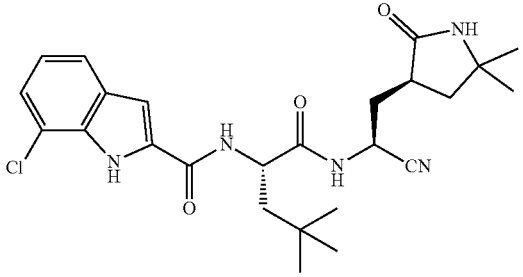 [SMILES: CC(C)(C)C[C@H](NC(=O)c1cc2cccc(Cl)c2[nH]1)C(=O)N[C@H](C#N)C[C@@H]1CC(C)(C)NC1=O] |
| 1234 | 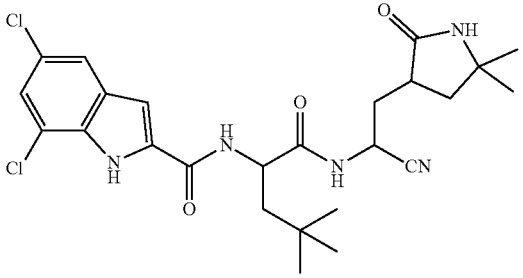 [SMILES: CC(C)(C)CC(NC(=O)c1cc2cc(Cl)cc(Cl)c2[nH]1)C(=O)NC(C#N)CC1CC(C)(C)NC1=O] |
| 1235 | 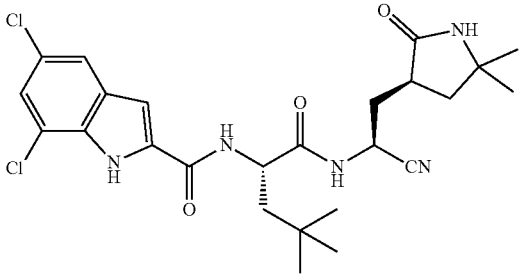 [SMILES: CC(C)(C)C[C@H](NC(=O)c1cc2cc(Cl)cc(Cl)c2[nH]1)C(=O)N[C@H](C#N)C[C@@H]1CC(C)(C)NC1=O] |
| 1236 | 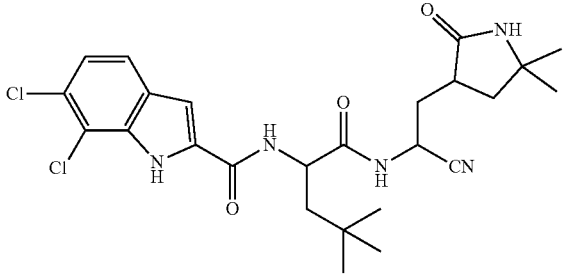 [SMILES: CC(C)(C)CC(NC(=O)c1cc2ccc(Cl)c(Cl)c2[nH]1)C(=O)NC(C#N)CC1CC(C)(C)NC1=O] |

TABLE 1-continued
Exemplary compounds.
| Cmpd No. | Structure |
|---|---|
| 1237 | 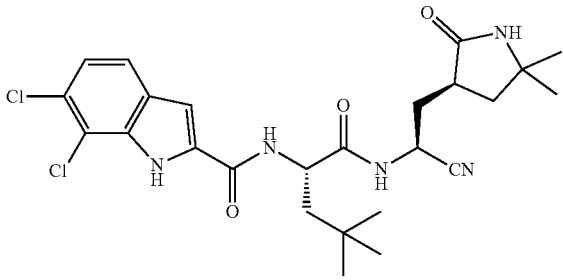 [SMILES: CC(C)(C)C[C@H](NC(=O)c1cc2ccc(Cl)c(Cl)c2[nH]1)C(=O)N[C@H](C#N)C[C@@H]1CC(C)(C)NC1=O] |
| 1238 | 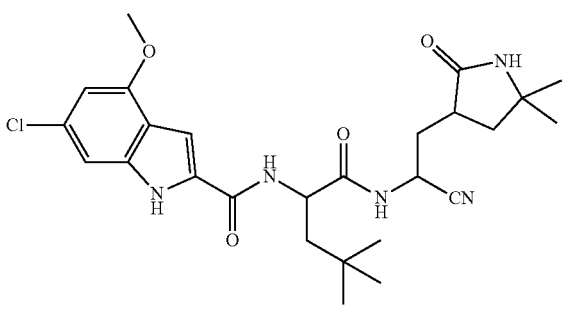 [SMILES: COc1cc(Cl)cc2[nH]c(C(=O)NC(CC(C)(C)C)C(=O)NC(C#N)CC3CC(C)(C)NC3=O)cc12] |
| 1239 | 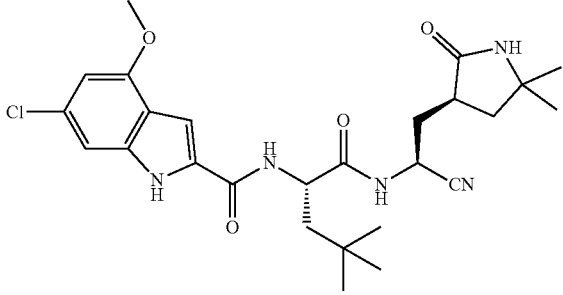 [SMILES: COc1cc(Cl)cc2[nH]c(C(=O)N[C@@H](CC(C)(C)C)C(=O)N[C@H](C#N)C[C@@H]3CC(C)(C)NC3=O)cc12] |
| 1240 | 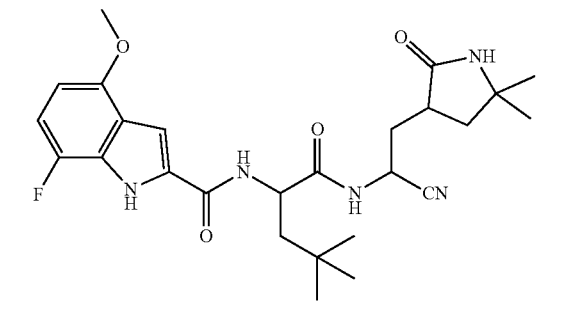 [SMILES: COc1ccc(F)c2[nH]c(C(=O)NC(CC(C)(C)C)C(=O)NC(C#N)CC3CC(C)(C)NC3=O)cc12] |
| 1241 | 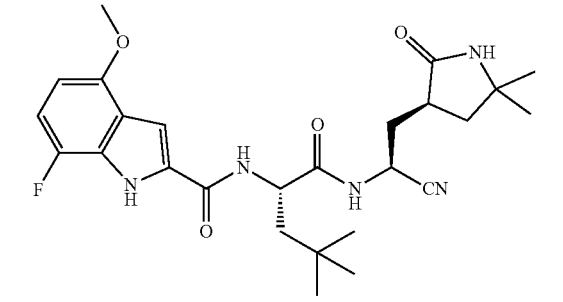 [SMILES: COc1ccc(F)c2[nH]c(C(=O)N[C@@H](CC(C)(C)C)C(=O)N[C@H](C#N)C[C@@H]3CC(C)(C)NC3=O)cc12] |

TABLE 1-continued
Exemplary compounds.
| Cmpd No. | Structure |
|---|---|
| 1242 | 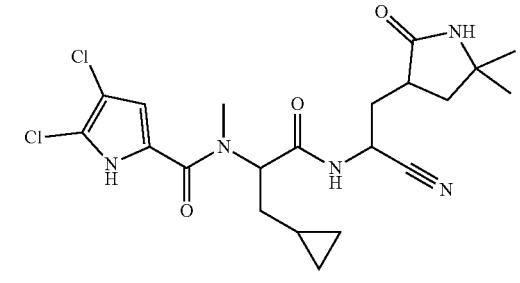 [SMILES: CN(C(=O)c1cc(Cl)c(Cl)[nH]1)C(CC1CC1)C(=O)NC(C#N)CC1CC(C)(C)NC1=O] |
| 1243 | 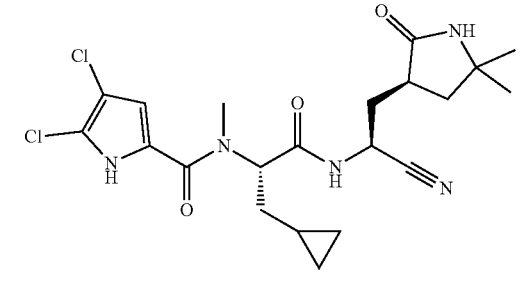 [SMILES: CN(C(=O)c1cc(Cl)c(Cl)[nH]1)[C@@H](CC1CC1)C(=O)N[C@H](C#N)C[C@@H]1CC(C)(C)NC1=O] |
| 1244 | 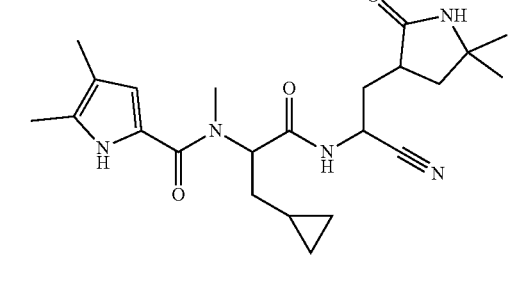 |
| 1245 | 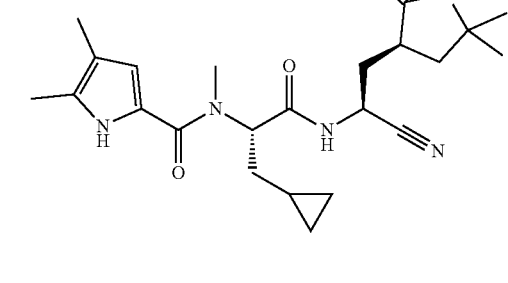 |
| 1246 | 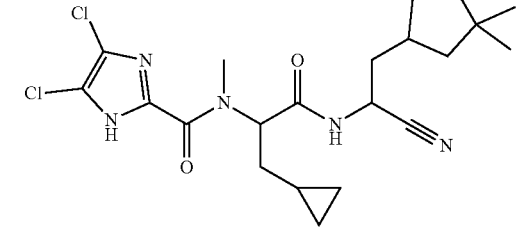 |

TABLE 1-continued
Exemplary compounds.
| Cmpd No. | Structure |
|---|---|
| 1247 | 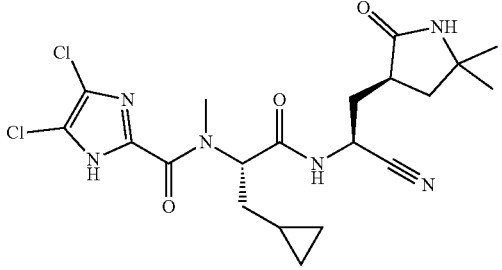 [SMILES: CN(C(=O)c1nc(Cl)c(Cl)[nH]1)[C@@H](CC1CC1)C(=O)N[C@H](C#N)C[C@@H]1CC(C)(C)NC1=O] |
| 1248 | 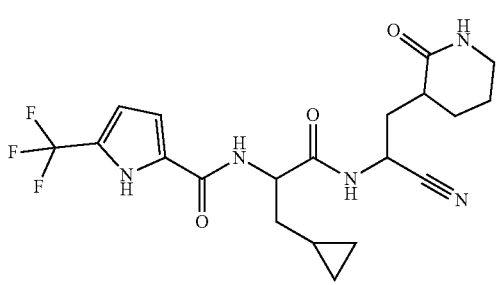 [SMILES: N#CC(CC1CCCNC1=O)NC(=O)C(CC1CC1)NC(=O)c1ccc(C(F)(F)F)[nH]1] |
| 1249 | 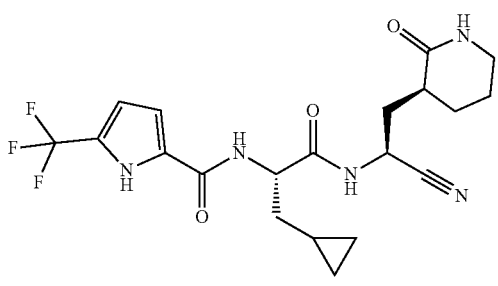 [SMILES: N#C[C@H](C[C@@H]1CCCNC1=O)NC(=O)[C@H](CC1CC1)NC(=O)c1ccc(C(F)(F)F)[nH]1] |
| 1250 | 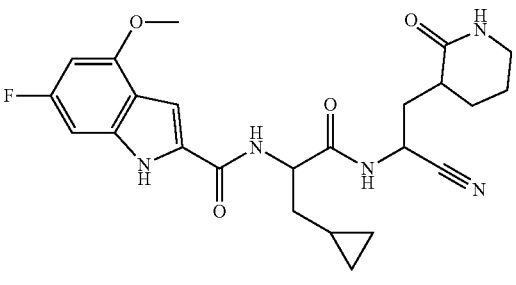 [SMILES: COc1cc(F)cc2[nH]c(C(=O)NC(CC3CC3)C(=O)NC(C#N)CC3CCCNC3=O)cc12] |
| 1251 | 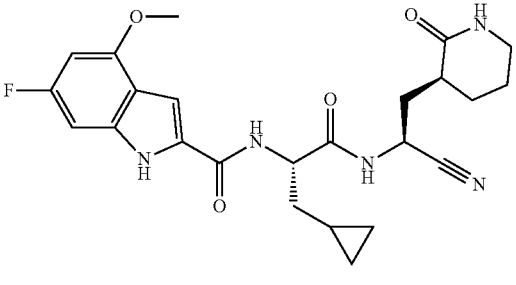 [SMILES: COc1cc(F)cc2[nH]c(C(=O)N[C@@H](CC3CC3)C(=O)N[C@H](C#N)C[C@@H]3CCCNC3=O)cc12] |

TABLE 1-continued

Exemplary compounds.

| Cmpd No. | Structure |
|---|---|
| 1252 | 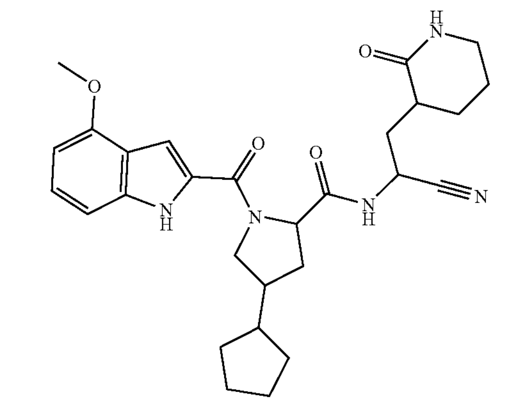 [SMILES: COc1cccc2[nH]c(C(=O)N3CC(C4CCCC4)CC3C(=O)NC(C#N)CC3CCCNC3=O)cc12] |
| 1253 | 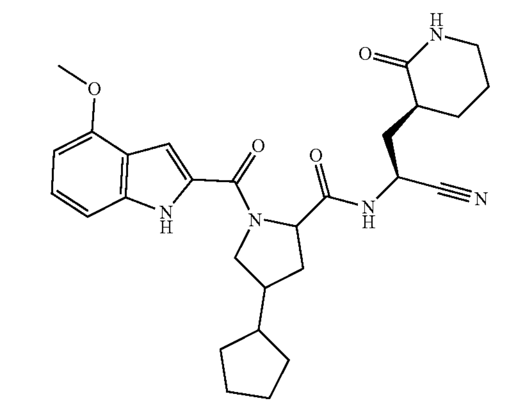 [SMILES: COc1cccc2[nH]c(C(=O)N3CC(C4CCCC4)CC3C(=O)N[C@H](C#N)C[C@@H]3CCCNC3=O)cc12] |
| 1254 | 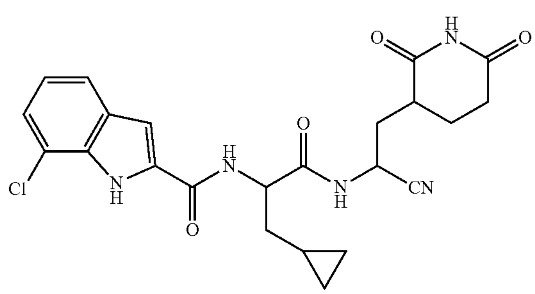 [SMILES: N#CC(CC1CCC(=O)NC1=O)NC(=O)C(CC1CC1)NC(=O)c1cc2cccc(Cl)c2[nH]1] |
| 1255 | 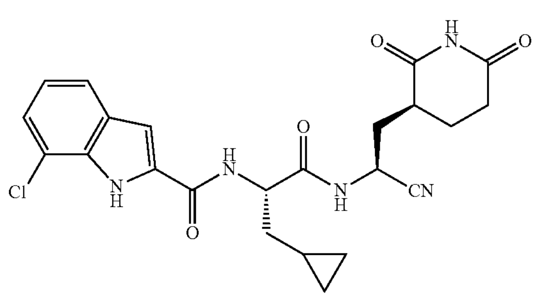 [SMILES: N#C[C@H](C[C@@H]1CCC(=O)NC1=O)NC(=O)[C@H](CC1CC1)NC(=O)c1cc2cccc(Cl)c2[nH]1] |

TABLE 1-continued
Exemplary compounds.
| Cmpd No. | Structure |
|---|---|
| 1256 | 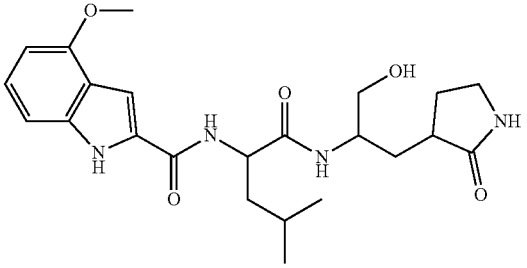 [SMILES: COc1cccc2[nH]c(C(=O)NC(CC(C)C)C(=O)NC(CO)CC3CCNC3=O)cc12] |
| 1257 | 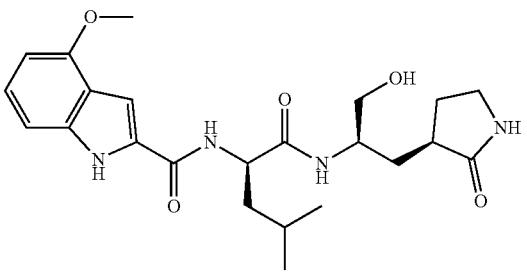 [SMILES: COc1cccc2[nH]c(C(=O)N[C@H](CC(C)C)C(=O)N[C@@H](CO)C[C@H]3CCNC3=O)cc12] |
| 1258 | 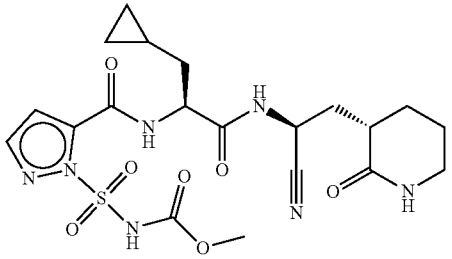 |
| 1259 | 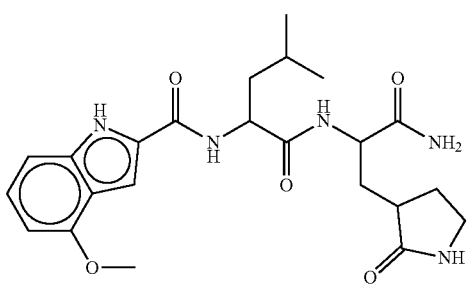 |
| 1260 | 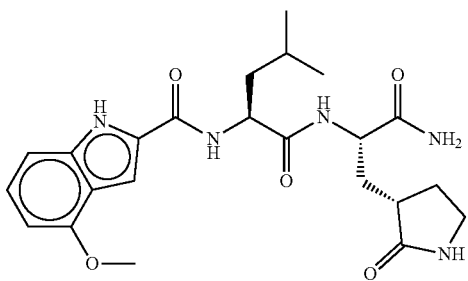 |

TABLE 1-continued

Exemplary compounds.

| Cmpd No. | Structure |
|---|---|
| 1261 | 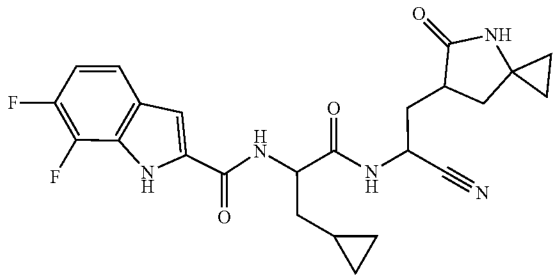 [SMILES: N#CC(CC1CC2(CC2)NC1=O)NC(=O)C(CC1CC1)NC(=O)c1cc2ccc(F)c(F)c2[nH]1] |
| 1262 | 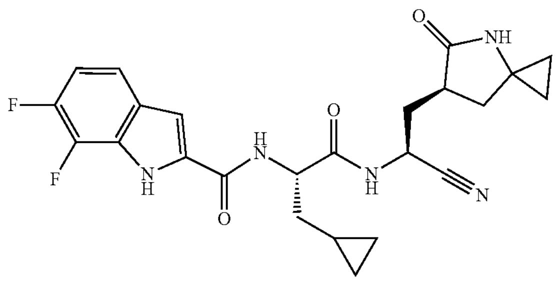 [SMILES: N#C[C@H](C[C@@H]1CC2(CC2)NC1=O)NC(=O)[C@H](CC1CC1)NC(=O)c1cc2ccc(F)c(F)c2[nH]1] |
| 1263 | 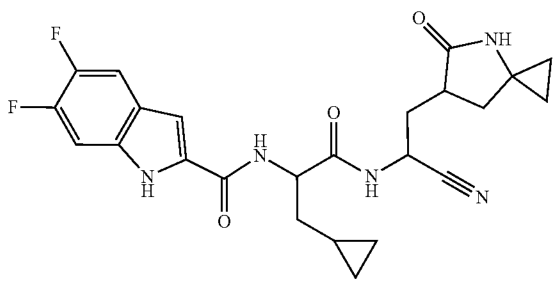 [SMILES: N#CC(CC1CC2(CC2)NC1=O)NC(=O)C(CC1CC1)NC(=O)c1cc2cc(F)c(F)cc2[nH]1] |
| 1264 | 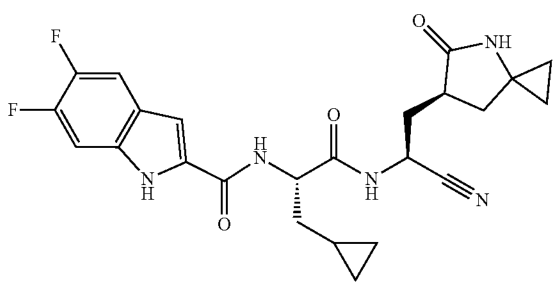 [SMILES: N#C[C@H](C[C@@H]1CC2(CC2)NC1=O)NC(=O)[C@H](CC1CC1)NC(=O)c1cc2cc(F)c(F)cc2[nH]1] |
| 1265 | 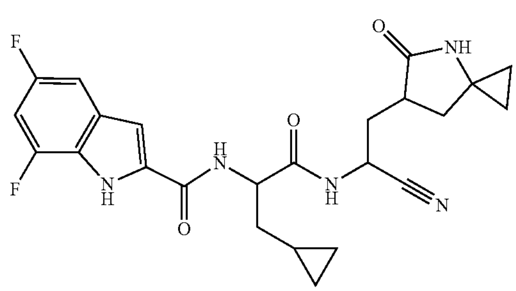 [SMILES: N#CC(CC1CC2(CC2)NC1=O)NC(=O)C(CC1CC1)NC(=O)c1cc2cc(F)cc(F)c2[nH]1] |

TABLE 1-continued

Exemplary compounds.

| Cmpd No. | Structure |
|---|---|
| 1266 | 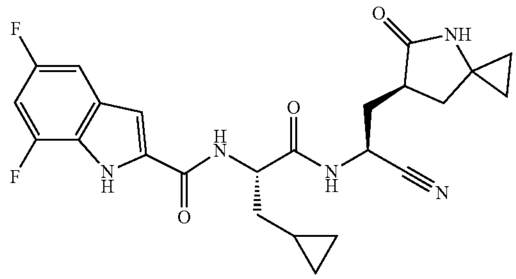 [SMILES: N#C[C@H](C[C@@H]1CC2(CC2)NC1=O)NC(=O)[C@H](CC1CC1)NC(=O)c1cc2cc(F)cc(F)c2[nH]1] |
| 1267 | 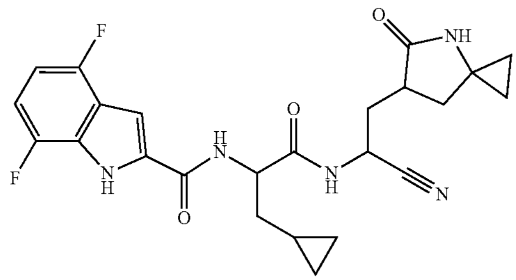 [SMILES: N#CC(CC1CC2(CC2)NC1=O)NC(=O)C(CC1CC1)NC(=O)c1cc2c(F)ccc(F)c2[nH]1] |
| 1268 | 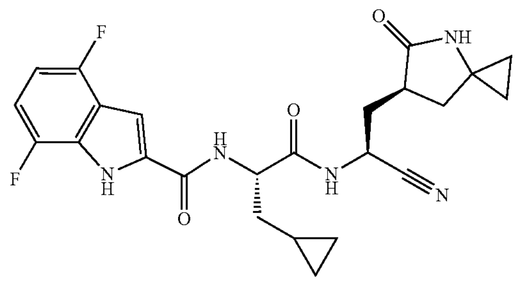 [SMILES: N#C[C@H](C[C@@H]1CC2(CC2)NC1=O)NC(=O)[C@H](CC1CC1)NC(=O)c1cc2c(F)ccc(F)c2[nH]1] |
| 1269 | 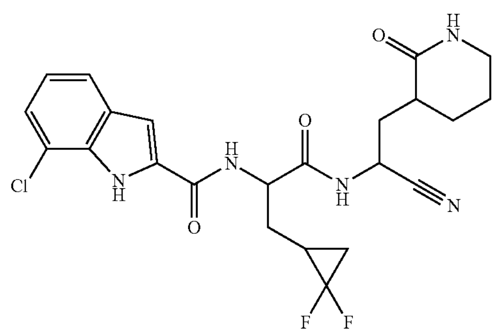 [SMILES: N#CC(CC1CCCNC1=O)NC(=O)C(CC1CC1(F)F)NC(=O)c1cc2cccc(Cl)c2[nH]1] |
| 1270 | 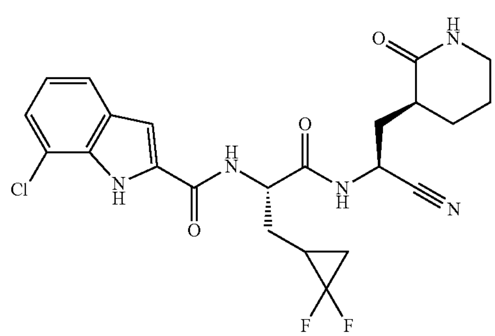 [SMILES: N#C[C@H](C[C@@H]1CCCNC1=O)NC(=O)[C@H](CC1CC1(F)F)NC(=O)c1cc2cccc(Cl)c2[nH]1] |

TABLE 1-continued

Exemplary compounds.

| Cmpd No. | Structure |
|---|---|
| 1271 | 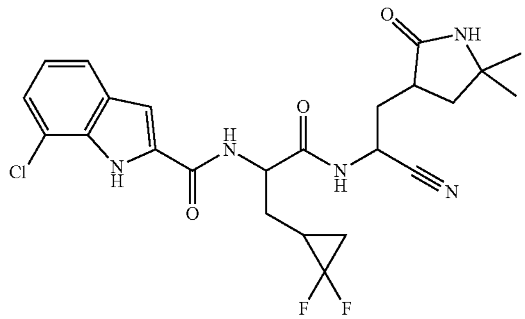 [SMILES: CC1(C)CC(CC(C#N)NC(=O)C(CC2CC2(F)F)NC(=O)c2cc3cccc(Cl)c3[nH]2)C(=O)N1] |
| 1272 | 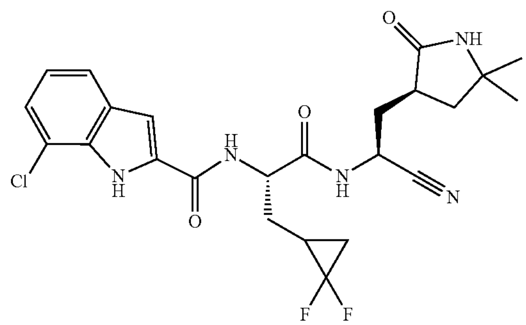 [SMILES: CC1(C)C[C@@H](C[C@@H](C#N)NC(=O)[C@H](CC2CC2(F)F)NC(=O)c2cc3cccc(Cl)c3[nH]2)C(=O)N1] |
| 1273 | 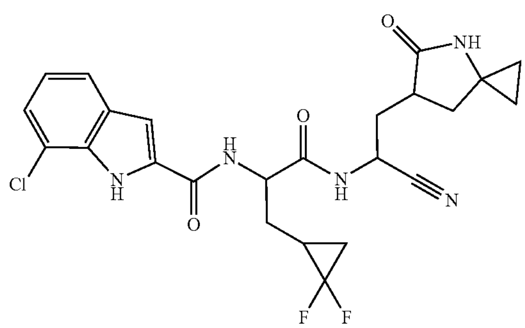 [SMILES: N#CC(CC1CC2(CC2)NC1=O)NC(=O)C(CC1CC1(F)F)NC(=O)c1cc2cccc(Cl)c2[nH]1] |
| 1274 | 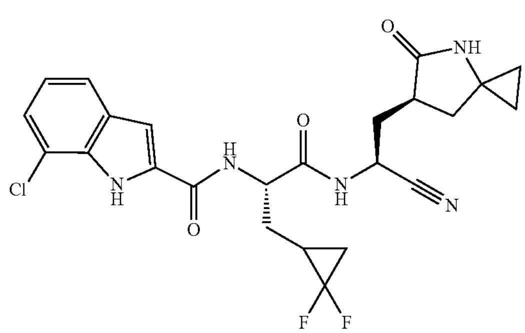 [SMILES: N#C[C@H](C[C@@H]1CC2(CC2)NC1=O)NC(=O)[C@H](CC1CC1(F)F)NC(=O)c1cc2cccc(Cl)c2[nH]1] |

TABLE 1-continued

Exemplary compounds.

| Cmpd No. | Structure |
|---|---|
| 1275 | 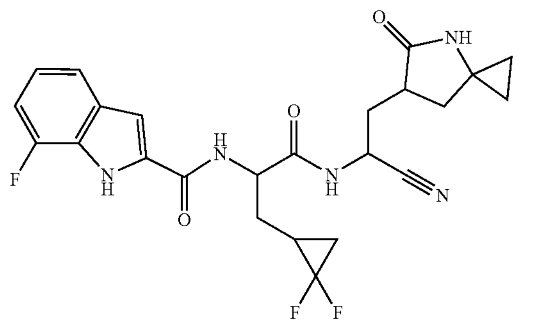 [SMILES: N#CC(CC1CC2(CC2)NC1=O)NC(=O)C(CC1CC1(F)F)NC(=O)c1cc2cccc(F)c2[nH]1] |
| 1276 | 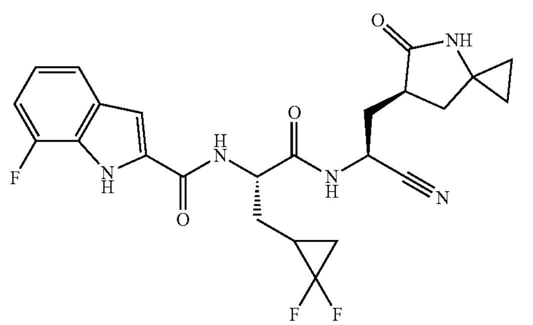 [SMILES: N#C[C@H](C[C@@H]1CC2(CC2)NC1=O)NC(=O)[C@H](CC1CC1(F)F)NC(=O)c1cc2cccc(F)c2[nH]1] |
| 1277 | 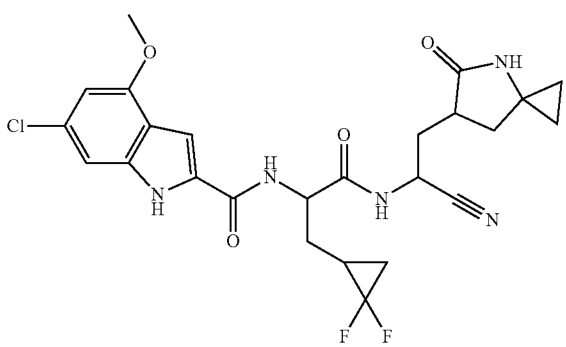 [SMILES: COc1cc(Cl)cc2[nH]c(C(=O)NC(CC3CC3(F)F)C(=O)NC(C#N)CC3CC4(CC4)NC3=O)cc12] |
| 1278 | 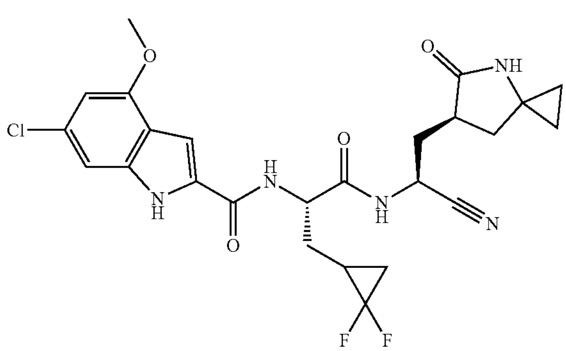 [SMILES: COc1cc(Cl)cc2[nH]c(C(=O)N[C@@H](CC3CC3(F)F)C(=O)N[C@H](C#N)C[C@@H]3CC4(CC4)NC3=O)cc12] |

TABLE 1-continued
Exemplary compounds.
| Cmpd No. | Structure |
|---|---|
| 1279 | 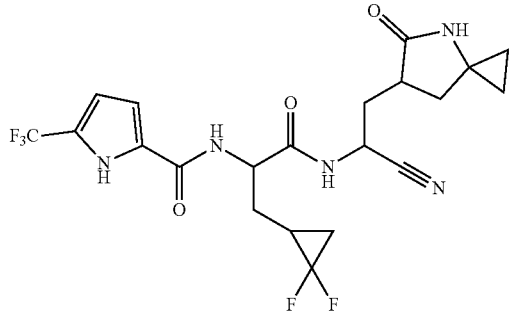 [SMILES: N#CC(CC1CC2(CC2)NC1=O)NC(=O)C(CC1CC1(F)F)NC(=O)c1ccc(C(F)(F)F)[nH]1] |
| 1280 | 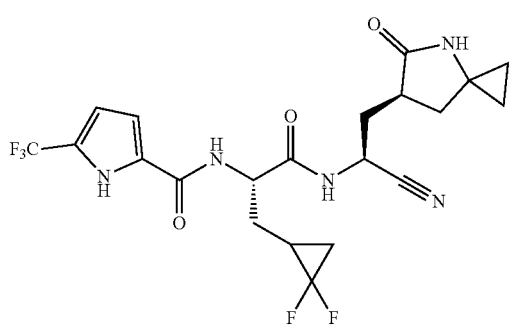 [SMILES: N#C[C@H](C[C@@H]1CC2(CC2)NC1=O)NC(=O)[C@H](CC1CC1(F)F)NC(=O)c1ccc(C(F)(F)F)[nH]1] |
| 1281 | 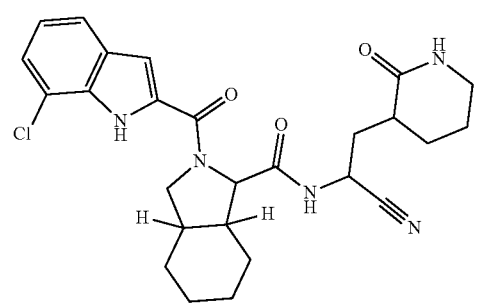 [SMILES: N#CC(CC1CCCNC1=O)NC(=O)C1C2CCCCC2CN1C(=O)c1cc2cccc(Cl)c2[nH]1] |
| 1282 | 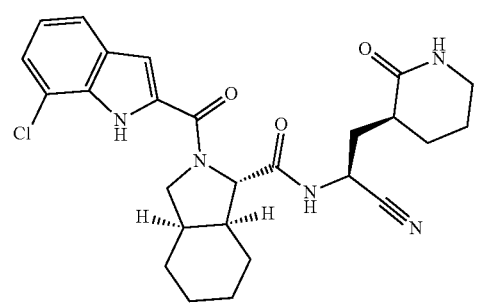 [SMILES: N#C[C@H](C[C@@H]1CCCNC1=O)NC(=O)[C@@H]1[C@H]2CCCC[C@H]2CN1C(=O)c1cc2cccc(Cl)c2[nH]1] |
| 1283 | 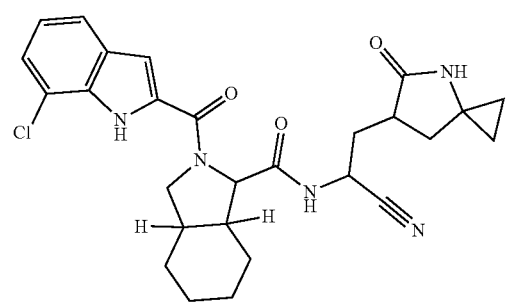 [SMILES: N#CC(CC1CC2(CC2)NC1=O)NC(=O)C1C2CCCCC2CN1C(=O)c1cc2cccc(Cl)c2[nH]1] |

TABLE 1-continued

Exemplary compounds.

| Cmpd No. | Structure |
|---|---|
| 1284 | 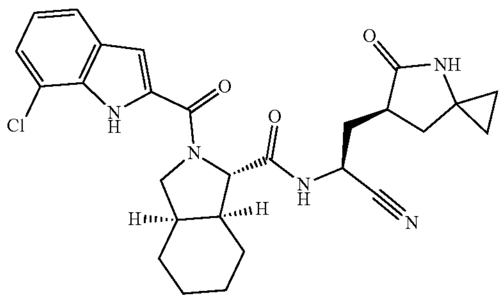 [SMILES: N#C[C@H](C[C@@H]1CC2(CC2)NC1=O)NC(=O)[C@@H]1[C@H]2CCCC[C@H]2CN1C(=O)c1cc2cccc(Cl)c2[nH]1] |
| 1285 | 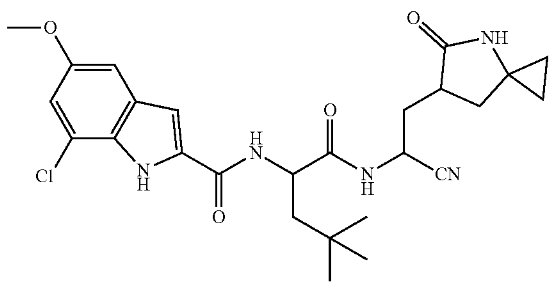 [SMILES: COc1cc(Cl)c2[nH]c(C(=O)NC(CC(C)(C)C)C(=O)NC(C#N)CC3CC4(CC4)NC3=O)cc2c1] |
| 1286 | 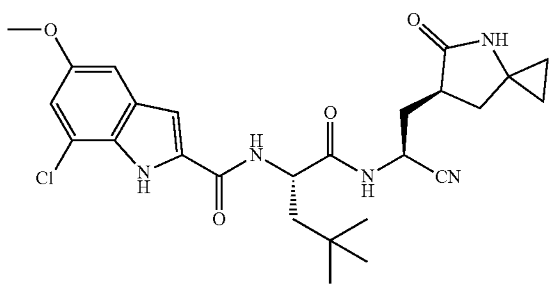 [SMILES: COc1cc(Cl)c2[nH]c(C(=O)N[C@@H](CC(C)(C)C)C(=O)N[C@H](C#N)C[C@@H]3CC4(CC4)NC3=O)cc2c1] |
| 1287 | 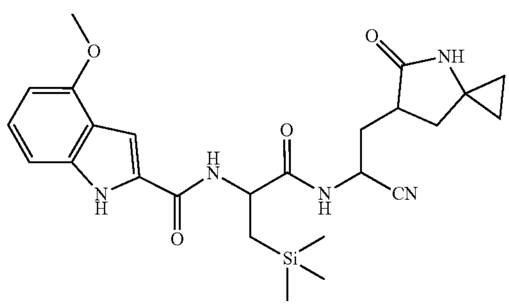 [SMILES: COc1cccc2[nH]c(C(=O)NC(C[Si](C)(C)C)C(=O)NC(C#N)CC3CC4(CC4)NC3=O)cc12] |
| 1288 | 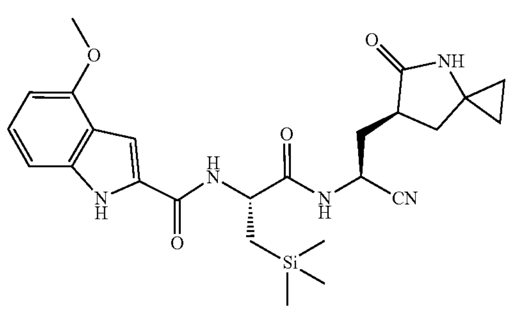 [SMILES: COc1cccc2[nH]c(C(=O)N[C@@H](C[Si](C)(C)C)C(=O)N[C@H](C#N)C[C@@H]3CC4(CC4)NC3=O)cc12] |

TABLE 1-continued

Exemplary compounds.

| Cmpd No. | Structure |
|---|---|
| 1289 | 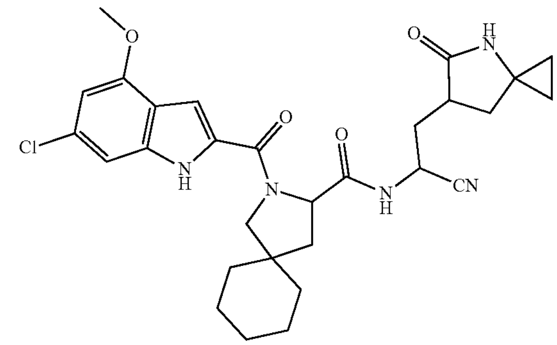 [SMILES: COc1cc(Cl)cc2[nH]c(C(=O)N3CC4(CCCCC4)CC3C(=O)NC(C#N)CC3CC4(CC4)NC3=O)cc12] |
| 1290 | 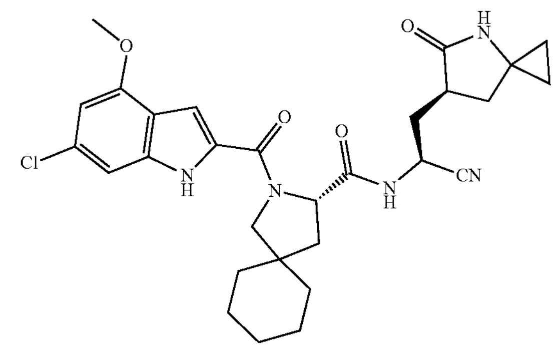 [SMILES: COc1cc(Cl)cc2[nH]c(C(=O)N3CC4(CCCCC4)C[C@H]3C(=O)N[C@H](C#N)C[C@@H]3CC4(CC4)NC3=O)cc12] |
| 1291 | 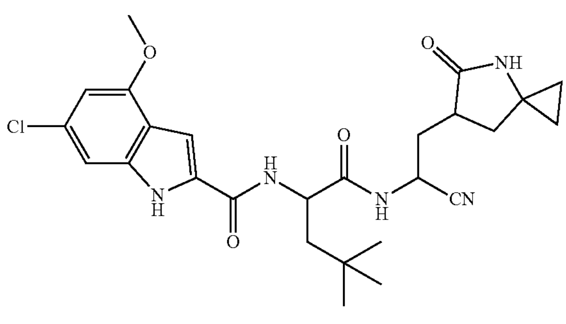 [SMILES: COc1cc(Cl)cc2[nH]c(C(=O)NC(CC(C)(C)C)C(=O)NC(C#N)CC3CC4(CC4)NC3=O)cc12] |
| 1292 | 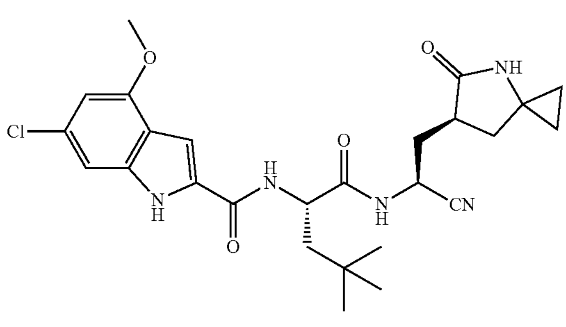 [SMILES: COc1cc(Cl)cc2[nH]c(C(=O)N[C@@H](CC(C)(C)C)C(=O)N[C@H](C#N)C[C@@H]3CC4(CC4)NC3=O)cc12] |

TABLE 1-continued

Exemplary compounds.

| Cmpd No. | Structure |
| --- | --- |
| 1293 | 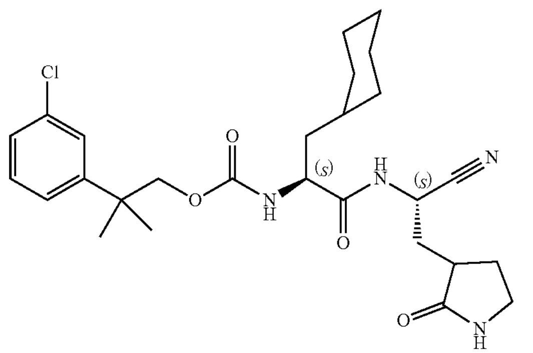 |
| 1294 | 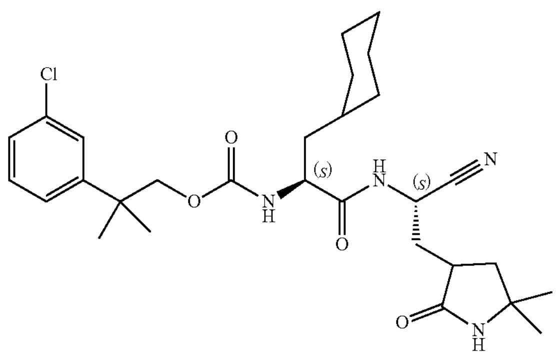 |
| 1295 | 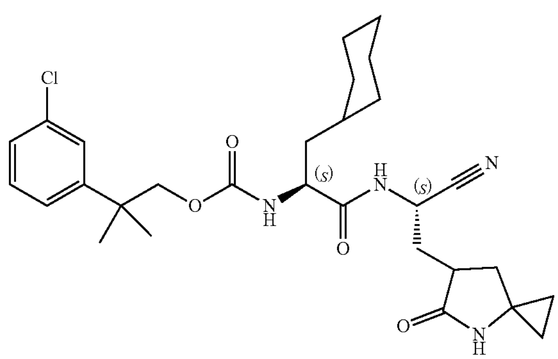 |
| 1296 | 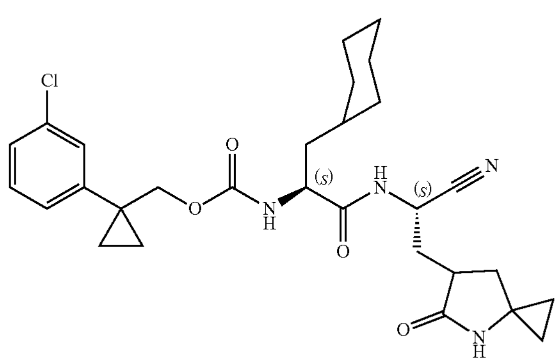 |

TABLE 1-continued

Exemplary compounds.

| Cmpd No. | Structure |
|---|---|
| 1297 | 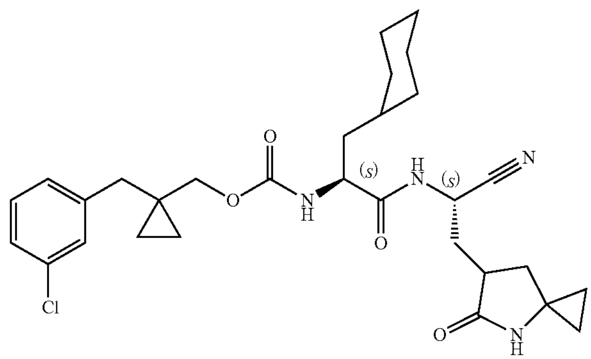 |
| 1298 | 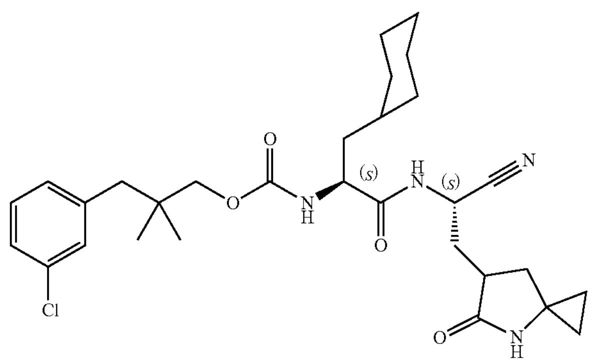 |
| 1299 | 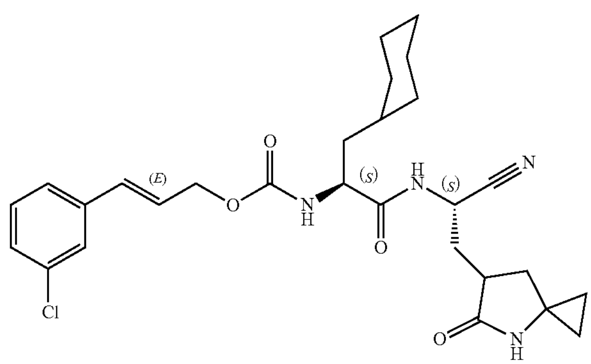 |
| 1300 | 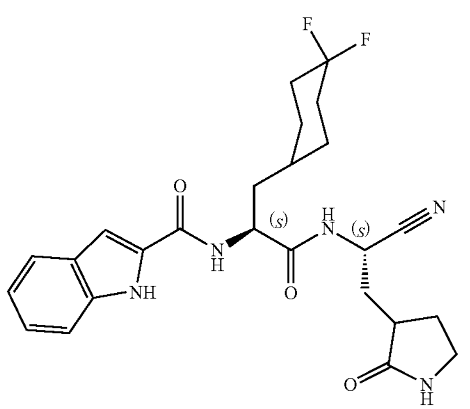 |

TABLE 1-continued
Exemplary compounds.
| Cmpd No. | Structure |
|---|---|
| 1301 | 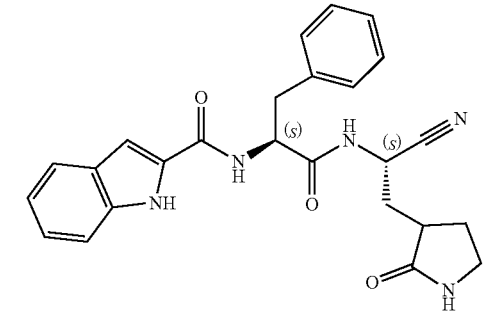 |
| 1302 | 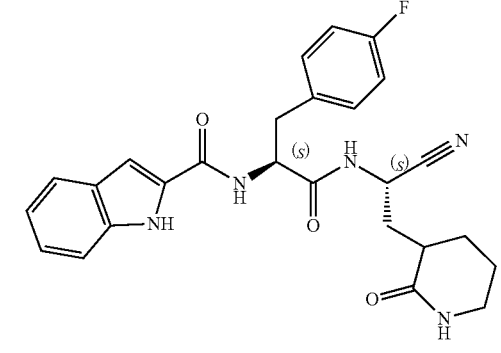 |
| 1303 | 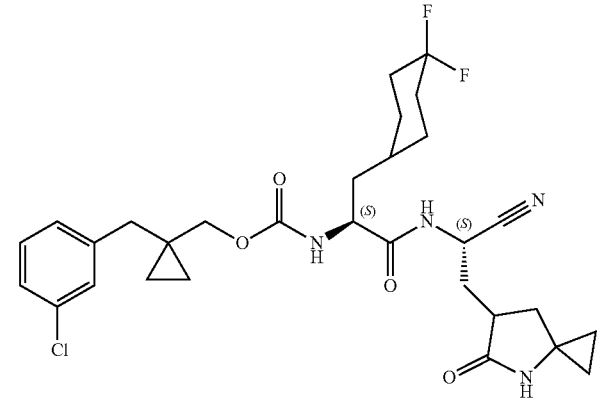 |
| 1304 | 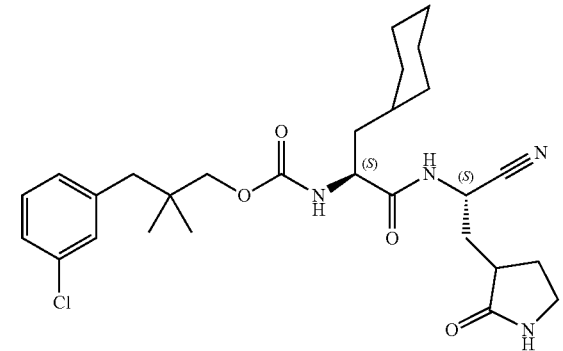 |

TABLE 1-continued

Exemplary compounds.

| Cmpd No. | Structure |
|---|---|
| 1305 | 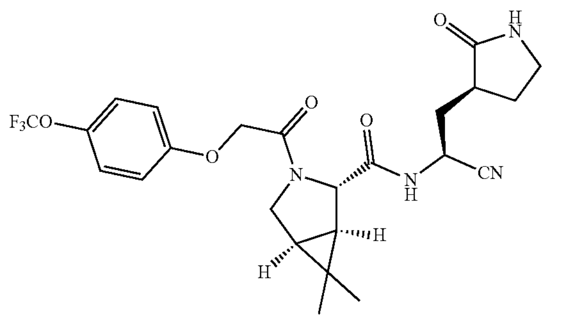 [SMILES: CC1(C)[C@@H]2[C@@H](C(=O)N[C@H](C#N)C[C@@H]3CCNC3=O)N(C(=O)COc3ccc(OC(F)(F)F)cc3)C[C@@H]21] |
| 1306 | 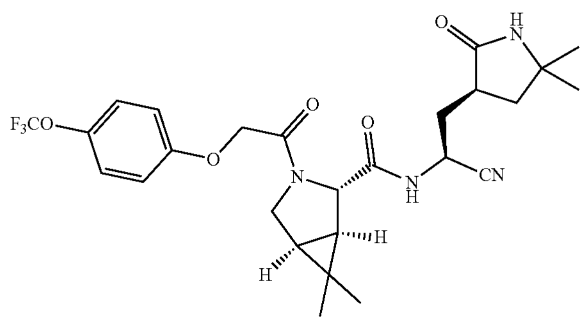 [SMILES: CC1(C)C[C@@H](C[C@@H](C#N)NC(=O)[C@@H]2[C@@H]3[C@H](CN2C(=O)COc2ccc(OC(F)(F)F)cc2)C3(C)C)C(=O)N1] |
| 1307 | 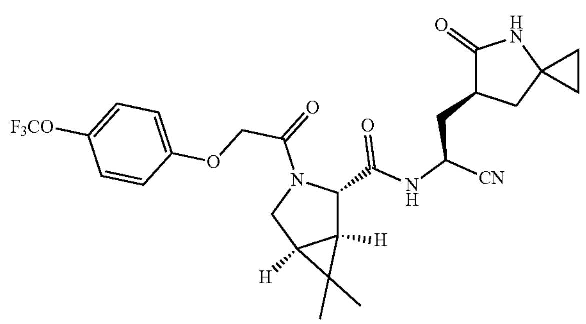 [SMILES: CC1(C)[C@@H]2[C@@H](C(=O)N[C@H](C#N)C[C@@H]3CC4(CC4)NC3=O)N(C(=O)COc3ccc(OC(F)(F)F)cc3)C[C@@H]21] |
| 1308 | 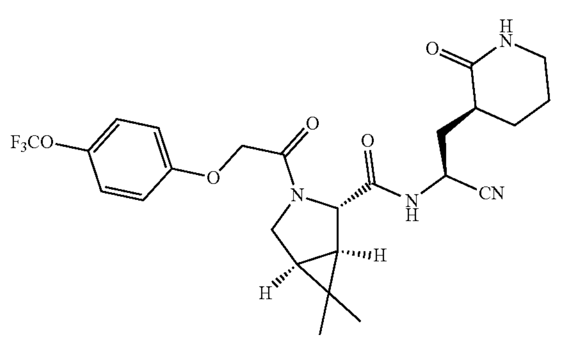 [SMILES: CC1(C)[C@@H]2[C@@H](C(=O)N[C@H](C#N)C[C@@H]3CCCNC3=O)N(C(=O)COc3ccc(OC(F)(F)F)cc3)C[C@@H]21] |

TABLE 1-continued

Exemplary compounds.

| Cmpd No. | Structure |
|---|---|
| 1309 | 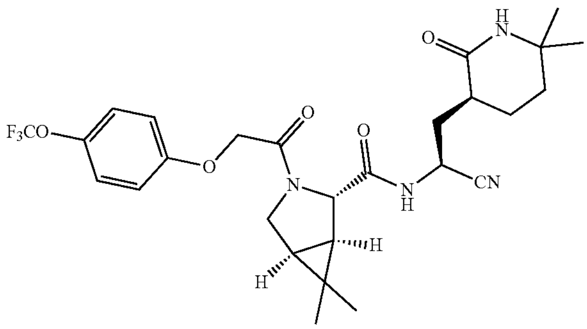 [SMILES: CC1(C)CC[C@@H](C[C@@H](C#N)NC(=O)[C@@H]2[C@@H]3[C@H](CN2C(=O)COc2ccc(OC(F)(F)F)cc2)C3(C)C)C(=O)N1] |
| 1310 | 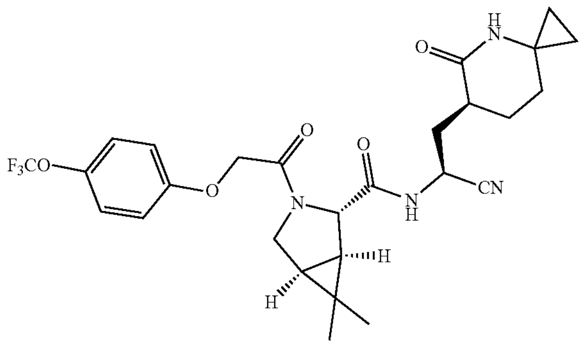 [SMILES: CC1(C)[C@@H]2[C@@H](C(=O)N[C@H](C#N)C[C@@H]3CCC4(CC4)NC3=O)N(C(=O)COc3ccc(OC(F)(F)F)cc3)C[C@@H]21] |
| 1311 | 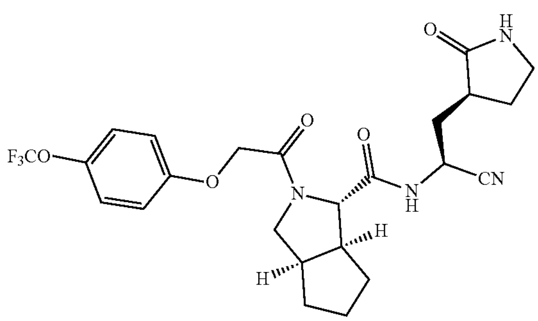 [SMILES: N#C[C@H](C[C@@H]1CCNC1=O)NC(=O)[C@@H]1[C@H]2CCC[C@H]2CN1C(=O)COc1ccc(OC(F)(F)F)cc1] |
| 1312 | 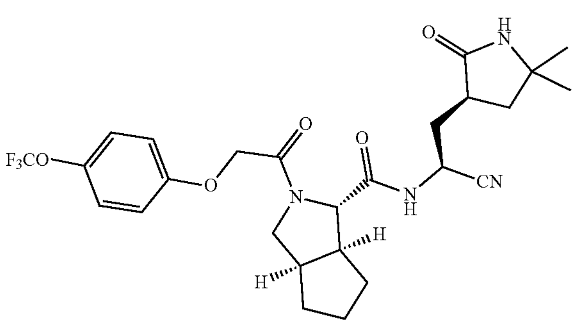 |

TABLE 1-continued

Exemplary compounds.

| Cmpd No. | Structure |
|---|---|
| 1313 | 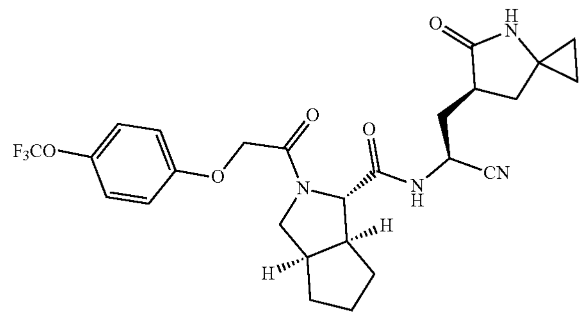 [SMILES: N#C[C@H](C[C@@H]1CC2(CC2)NC1=O)NC(=O)[C@@H]1[C@H]2CCC[C@H]2CN1C(=O)COc1ccc(OC(F)(F)F)cc1] |
| 1314 | 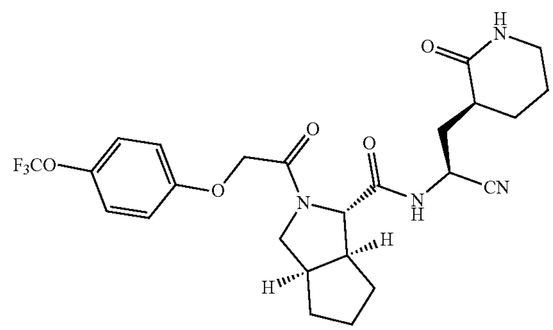 [SMILES: N#C[C@H](C[C@@H]1CCCNC1=O)NC(=O)[C@@H]1[C@H]2CCC[C@H]2CN1C(=O)COc1ccc(OC(F)(F)F)cc1] |
| 1315 | 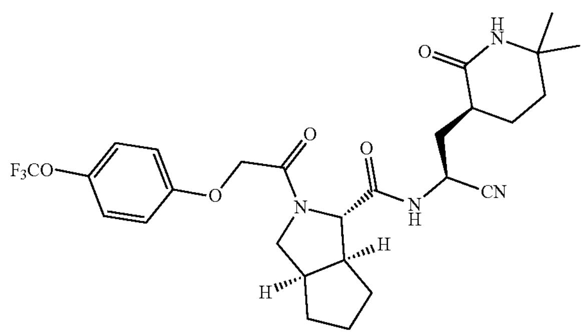 [SMILES: CC1(C)CC[C@@H](C[C@@H](C#N)NC(=O)[C@@H]2[C@H]3CCC[C@H]3CN2C(=O)COc2ccc(OC(F)(F)F)cc2)C(=O)N1] |
| 1316 | 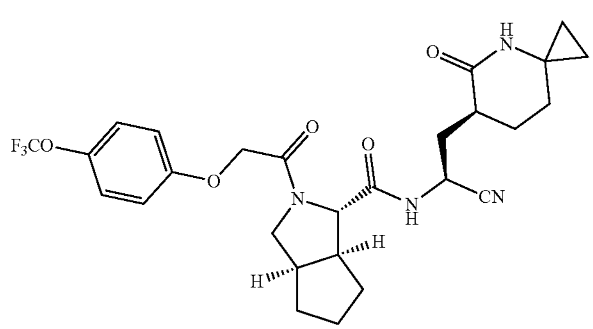 [SMILES: N#C[C@H](C[C@@H]1CCC2(CC2)NC1=O)NC(=O)[C@@H]1[C@H]2CCC[C@H]2CN1C(=O)COc1ccc(OC(F)(F)F)cc1] |

TABLE 1-continued
Exemplary compounds.
| Cmpd No. | Structure |
|---|---|
| 1317 | 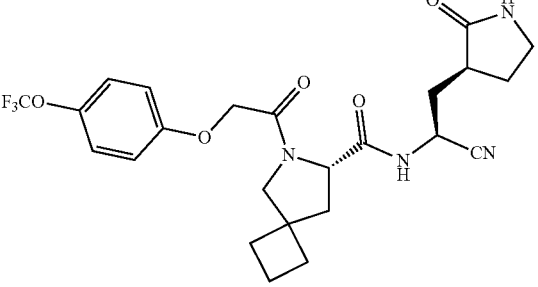 |
| 1318 | 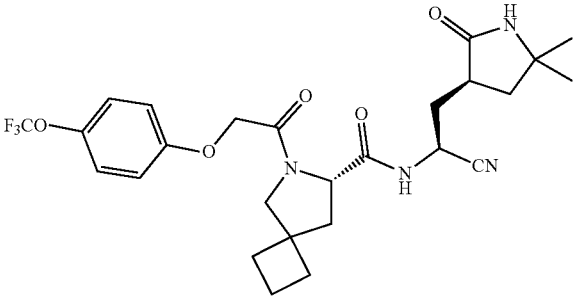 [SMILES: CC1(C)C[C@@H](C[C@@H](C#N)NC(=O)[C@@H]2CC3(CCC3)CN2C(=O)COc2ccc(OC(F)(F)F)cc2)C(=O)N1] |
| 1319 | 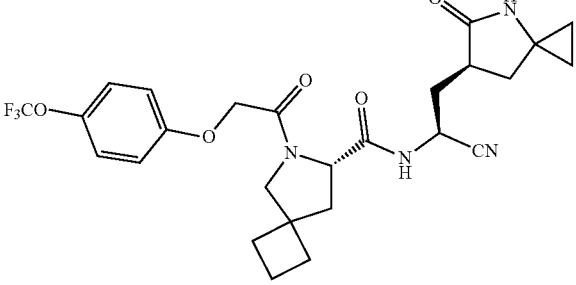 |
| 1320 | 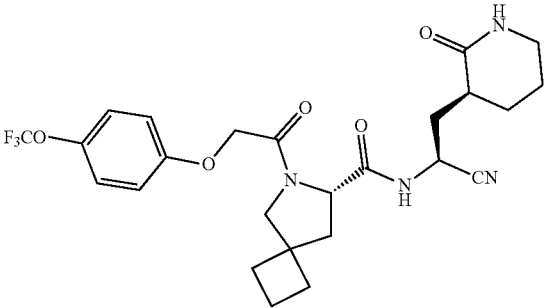 [SMILES: N#C[C@H](C[C@@H]1CCCNC1=O)NC(=O)[C@@H]1CC2(CCC2)CN1C(=O)COc1ccc(OC(F)(F)F)cc1] |
| 1321 | 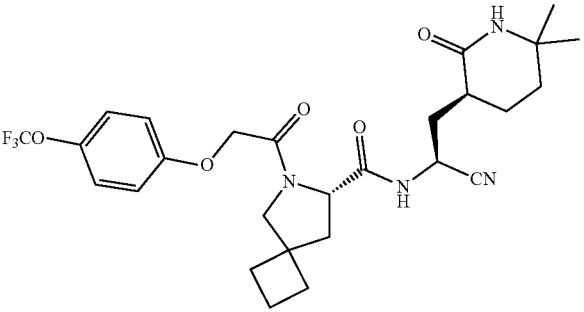 [SMILES: CC1(C)CC[C@@H](C[C@@H](C#N)NC(=O)[C@@H]2CC3(CCC3)CN2C(=O)COc2ccc(OC(F)(F)F)cc2)C(=O)N1] |

TABLE 1-continued

Exemplary compounds.

| Cmpd No. | Structure |
|---|---|
| 1322 | 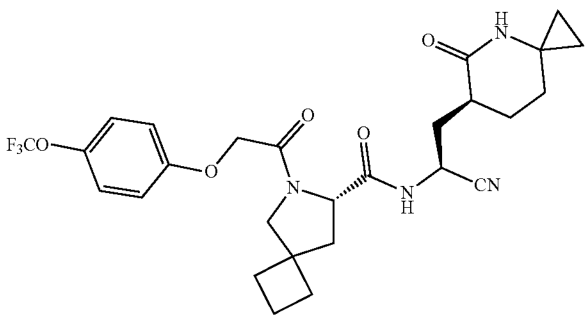 [SMILES: N#C[C@H](C[C@@H]1CCC2(CC2)NC1=O)NC(=O)[C@@H]1CC2(CCC2)CN1C(=O)COc1ccc(OC(F)(F)F)cc1] |
| 1323 | 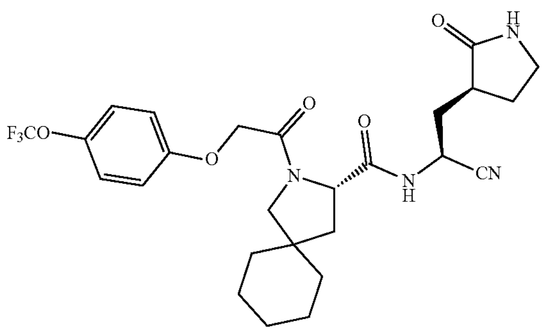 [SMILES: N#C[C@H](C[C@@H]1CCNC1=O)NC(=O)[C@@H]1CC2(CCCCC2)CN1C(=O)COc1ccc(OC(F)(F)F)cc1] |
| 1324 | 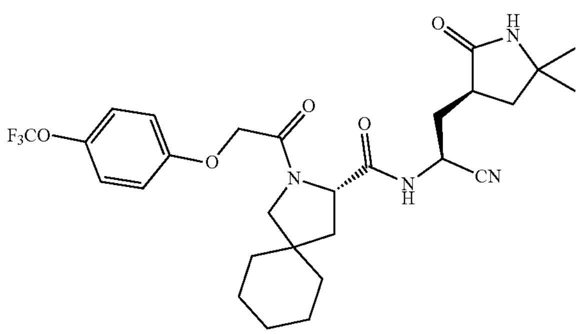 [SMILES: CC1(C)C[C@@H](C[C@@H](C#N)NC(=O)[C@@H]2CC3(CCCCC3)CN2C(=O)COc2ccc(OC(F)(F)F)cc2)C(=O)N1] |
| 1325 | 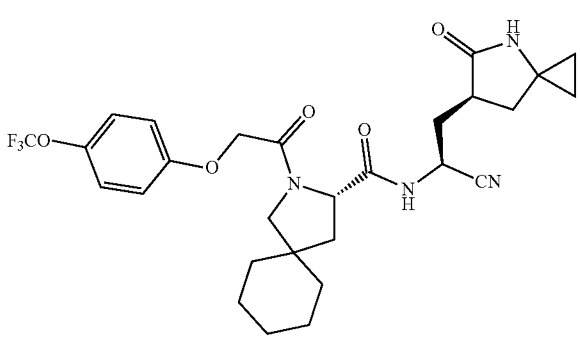 [SMILES: N#C[C@H](C[C@@H]1CC2(CC2)NC1=O)NC(=O)[C@@H]1CC2(CCCCC2)CN1C(=O)COc1ccc(OC(F)(F)F)cc1] |

TABLE 1-continued

Exemplary compounds.

| Cmpd No. | Structure |
|---|---|
| 1326 | 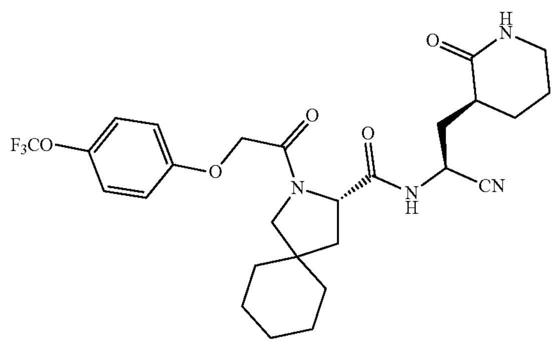 [SMILES: N#C[C@H](C[C@@H]1CCCNC1=O)NC(=O)[C@@H]1CC2(CCCCC2)CN1C(=O)COc1ccc(OC(F)(F)F)cc1] |
| 1327 | 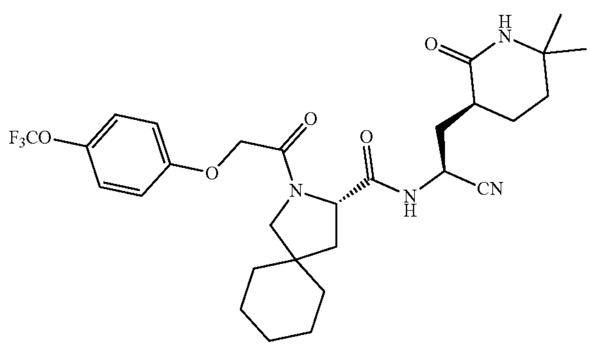 [SMILES: CC1(C)CC[C@@H](C[C@@H](C#N)NC(=O)[C@@H]2CC3(CCCCC3)CN2C(=O)COc2ccc(OC(F)(F)F)cc2)C(=O)N1] |
| 1328 | 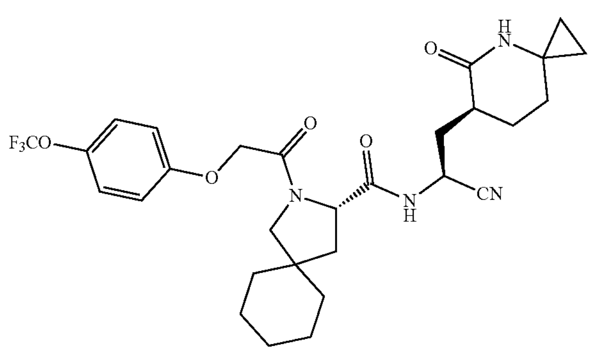 [SMILES: N#C[C@H](C[C@@H]1CCC2(CC2)NC1=O)NC(=O)[C@@H]1CC2(CCCCC2)CN1C(=O)COc1ccc(OC(F)(F)F)cc1] |
| 1329 | 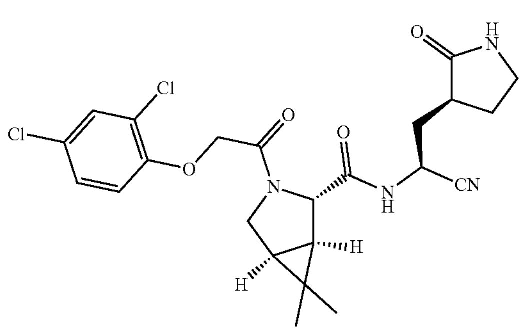 [SMILES: CC1(C)[C@@H]2[C@@H](C(=O)N[C@H](C#N)C[C@@H]3CCNC3=O)N(C(=O)COc3ccc(Cl)cc3Cl)C[C@@H]21] |

TABLE 1-continued

Exemplary compounds.

| Cmpd No. | Structure |
| --- | --- |
| 1330 | 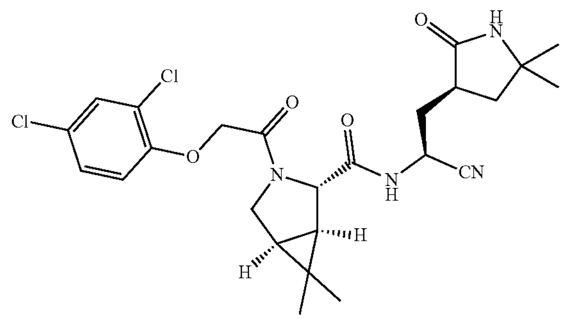 |
| 1331 | 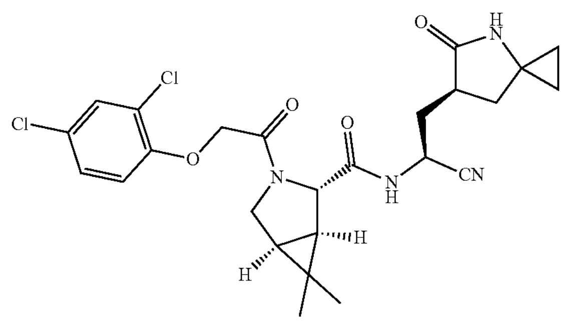 [SMILES: CC1(C)[C@@H]2[C@@H](C(=O)N[C@H](C#N)C[C@@H]3CC4(CC4)NC3=O)N(C(=O)COc3ccc(Cl)cc3Cl)C[C@@H]21] |
| 1332 | 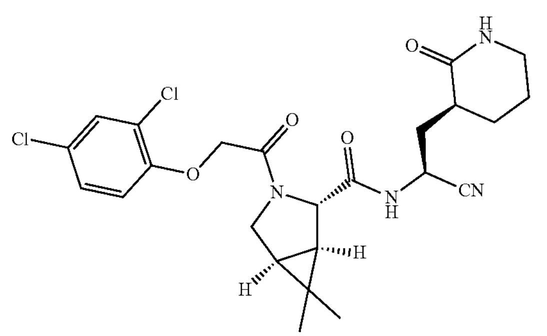 [SMILES: CC1(C)[C@@H]2[C@@H](C(=O)N[C@H](C#N)C[C@@H]3CCCNC3=O)N(C(=O)COc3ccc(Cl)cc3Cl)C[C@@H]21] |
| 1333 | 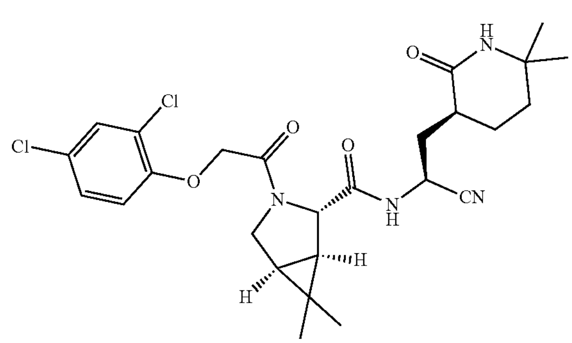 [SMILES: CC1(C)CC[C@@H](C[C@@H](C#N)NC(=O)[C@@H]2[C@@H]3[C@H](CN2C(=O)COc2ccc(Cl)cc2Cl)C3(C)C)C(=O)N1] |

TABLE 1-continued

Exemplary compounds.

| Cmpd No. | Structure |
|---|---|
| 1334 | 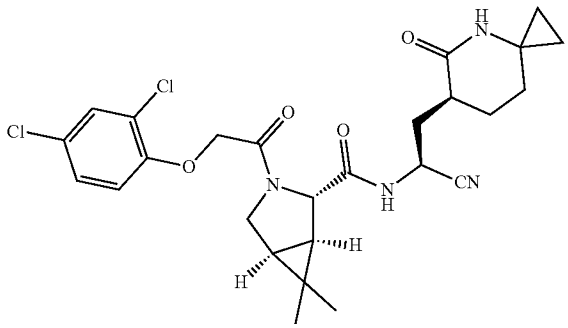 [SMILES: CC1(C)[C@@H]2[C@@H](C(=O)N[C@H](C#N)C[C@@H]3CCC4(CC4)NC3=O)N(C(=O)COc3ccc(Cl)cc3Cl)C[C@@H]21] |
| 1335 | 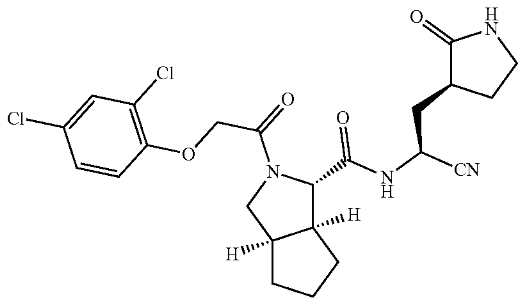 [SMILES: N#C[C@H](C[C@@H]1CCNC1=O)NC(=O)[C@@H]1[C@H]2CCC[C@H]2CN1C(=O)COc1ccc(Cl)cc1Cl] |
| 1336 | 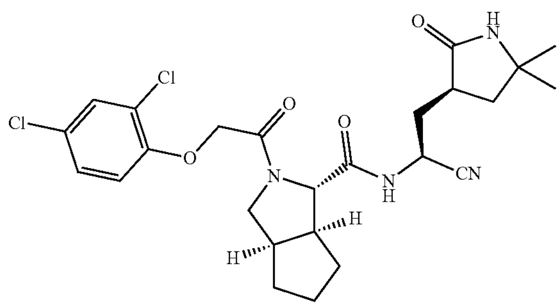 [SMILES: CC1(C)C[C@@H](C[C@@H](C#N)NC(=O)[C@@H]2[C@H]3CCC[C@H]3CN2C(=O)COc2ccc(Cl)cc2Cl)C(=O)N1] |
| 1337 | 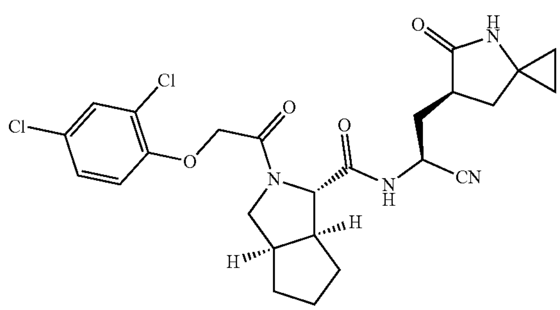 [SMILES: N#C[C@H](C[C@@H]1CC2(CC2)NC1=O)NC(=O)[C@@H]1[C@H]2CCC[C@H]2CN1C(=O)COc1ccc(Cl)cc1Cl] |
| 1338 | 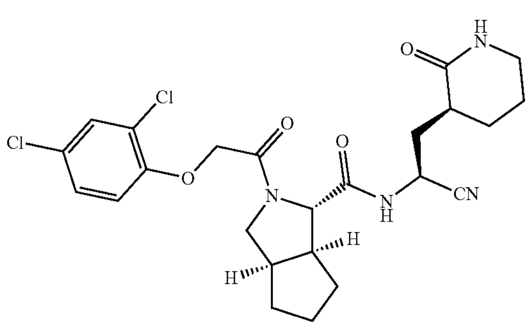 [SMILES: N#C[C@H](C[C@@H]1CCCNC1=O)NC(=O)[C@@H]1[C@H]2CCC[C@H]2CN1C(=O)COc1ccc(Cl)cc1Cl] |

TABLE 1-continued

Exemplary compounds.

| Cmpd No. | Structure |
|---|---|
| 1339 | 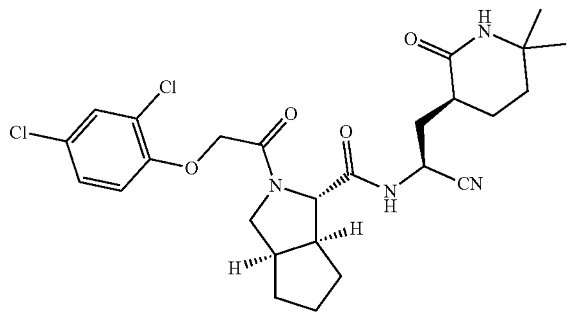 [SMILES: CC1(C)CC[C@@H](C[C@@H](C#N)NC(=O)[C@@H]2[C@H]3CCC[C@H]3CN2C(=O)COc2ccc(Cl)cc2Cl)C(=O)N1] |
| 1340 | 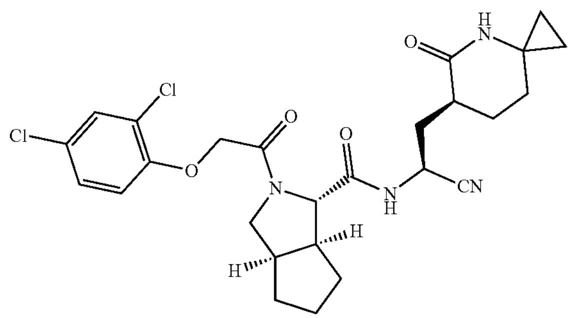 [SMILES: N#C[C@H](C[C@@H]1CCC2(CC2)NC1=O)NC(=O)[C@@H]1[C@H]2CCC[C@H]2CN1C(=O)COc1ccc(Cl)cc1Cl] |
| 1341 | 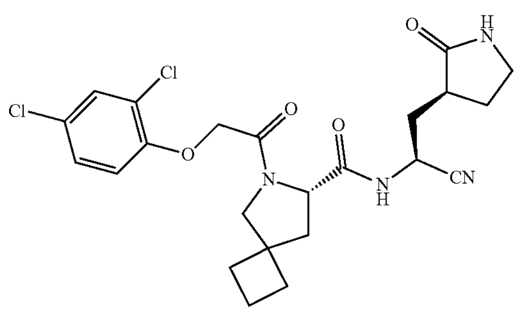 [SMILES: N#C[C@H](C[C@@H]1CCNC1=O)NC(=O)[C@@H]1CC2(CCC2)CN1C(=O)COc1ccc(Cl)cc1Cl] |
| 1342 | 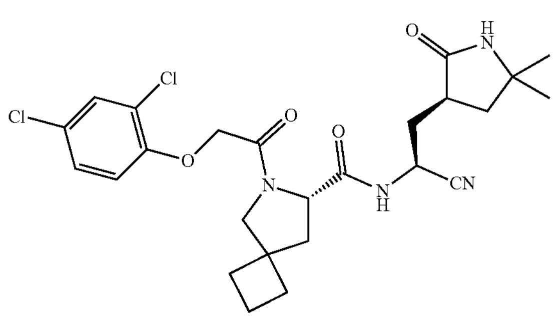 [SMILES: CC1(C)C[C@@H](C[C@@H](C#N)NC(=O)[C@@H]2CC3(CCC3)CN2C(=O)COc2ccc(Cl)cc2Cl)C(=O)N1] |

TABLE 1-continued

Exemplary compounds.

| Cmpd No. | Structure |
|---|---|
| 1343 | 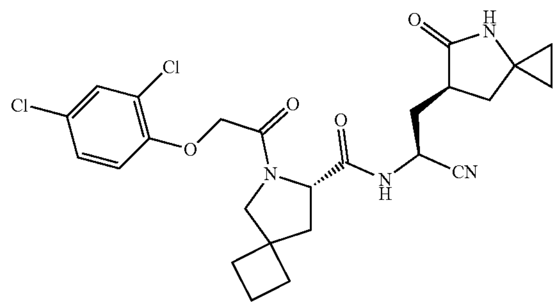 [SMILES: N#C[C@H](C[C@@H]1CC2(CC2)NC1=O)NC(=O)[C@@H]1CC2(CCC2)CN1C(=O)COc1ccc(Cl)cc1Cl] |
| 1344 | 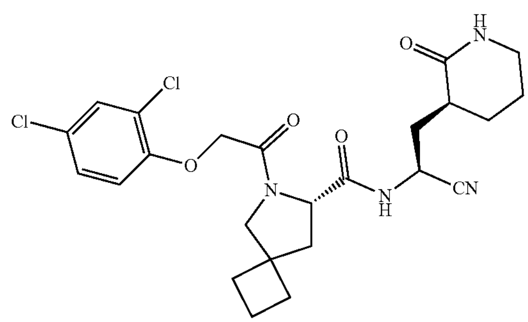 [SMILES: N#C[C@H](C[C@@H]1CCCNC1=O)NC(=O)[C@@H]1CC2(CCC2)CN1C(=O)COc1ccc(Cl)cc1Cl] |
| 1345 | 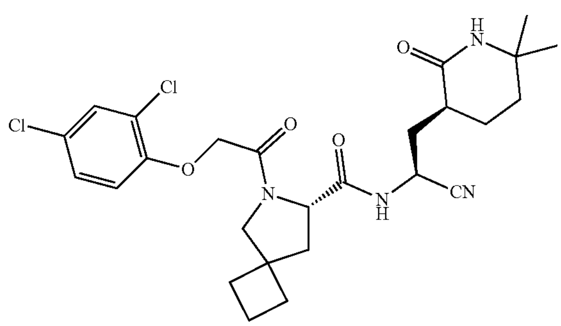 [SMILES: CC1(C)CC[C@@H](C[C@@H](C#N)NC(=O)[C@@H]2CC3(CCC3)CN2C(=O)COc2ccc(Cl)cc2Cl)C(=O)N1] |
| 1346 | 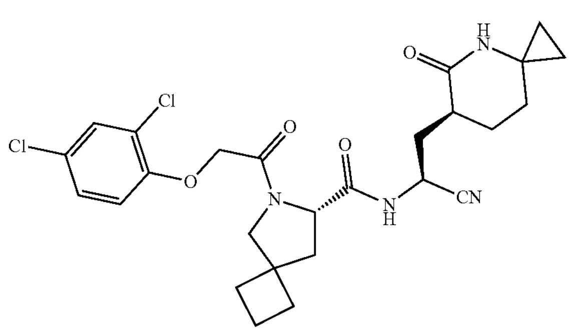 [SMILES: N#C[C@H](C[C@@H]1CCC2(CC2)NC1=O)NC(=O)[C@@H]1CC2(CCC2)CN1C(=O)COc1ccc(Cl)cc1Cl] |

TABLE 1-continued

Exemplary compounds.

| Cmpd No. | Structure |
|---|---|
| 1347 | 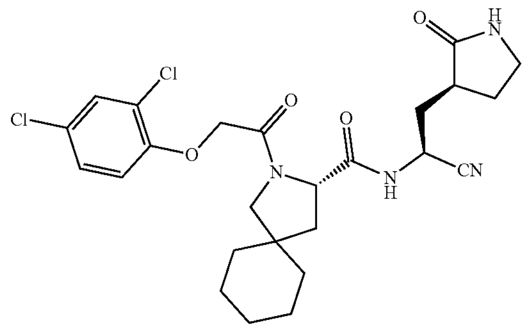 [SMILES: N#C[C@H](C[C@@H]1CCNC1=O)NC(=O)[C@@H]1CC2(CCCCC2)CN1C(=O)COc1ccc(Cl)cc1Cl] |
| 1348 | 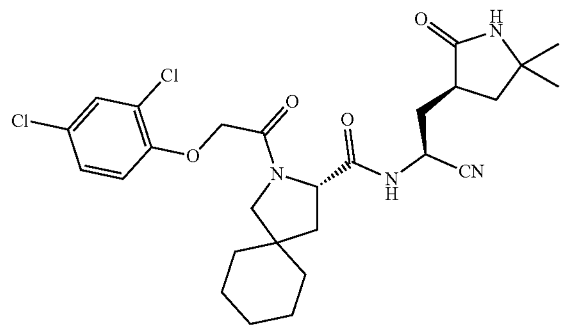 |
| 1349 | 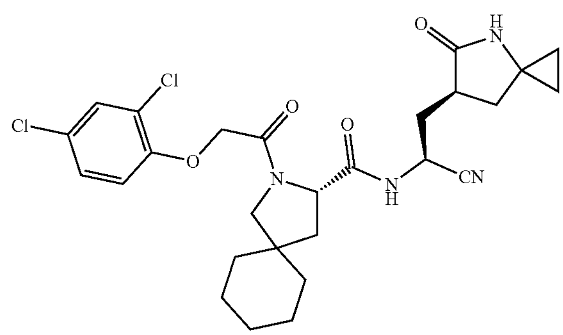 [SMILES: N#C[C@H](C[C@@H]1CC2(CC2)NC1=O)NC(=O)[C@@H]1CC2(CCCCC2)CN1C(=O)COc1ccc(Cl)cc1Cl] |
| 1350 | 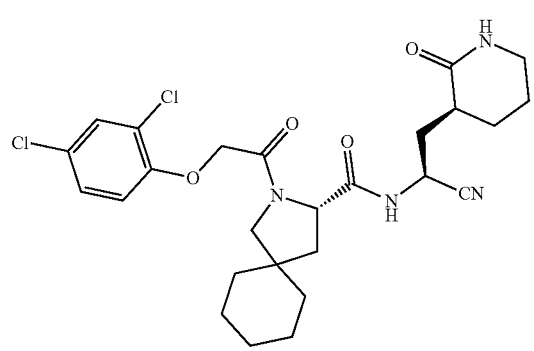 [SMILES: N#C[C@H](C[C@@H]1CCCNC1=O)NC(=O)[C@@H]1CC2(CCCCC2)CN1C(=O)COc1ccc(Cl)cc1Cl] |

TABLE 1-continued

Exemplary compounds.

| Cmpd No. | Structure |
|---|---|
| 1351 | (structure) |
| 1352 | (structure) |

TABLE 2

Exemplary compounds.

| Cmpd No. | Structure |
|---|---|
| 3000 | (structure) |
| 3001 | (structure) |

TABLE 2-continued

Exemplary compounds.

| Cmpd No. | Structure |
|---|---|
| 3002 | 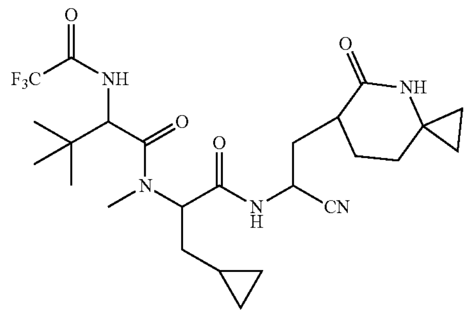 [SMILES: CN(C(=O)C(NC(=O)C(F)(F)F)C(C)(C)C)C(CC1CC1)C(=O)NC(C#N)CC1CCC2(CC2)NC1=O] |
| 3003 | 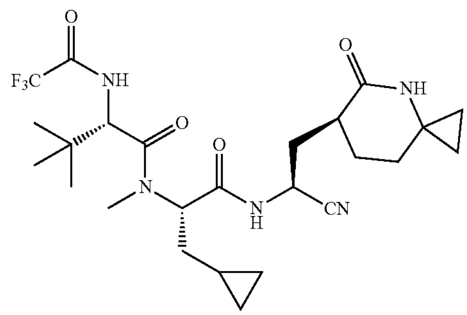 [SMILES: CN(C(=O)[C@@H](NC(=O)C(F)(F)F)C(C)(C)C)[C@@H](CC1CC1)C(=O)N[C@H](C#N)C[C@@H]1CCC2(CC2)NC1=O] |
| 3004 | 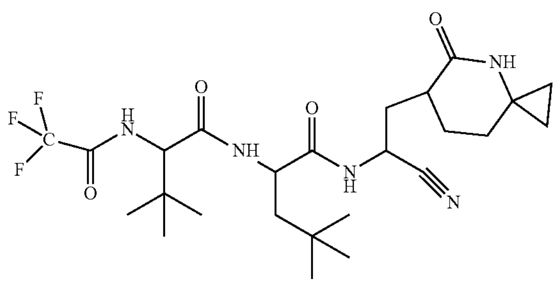 [SMILES: CC(C)(C)CC(NC(=O)C(NC(=O)C(F)(F)F)C(C)(C)C)C(=O)NC(C#N)CC1CCC2(CC2)NC1=O] |
| 3005 | 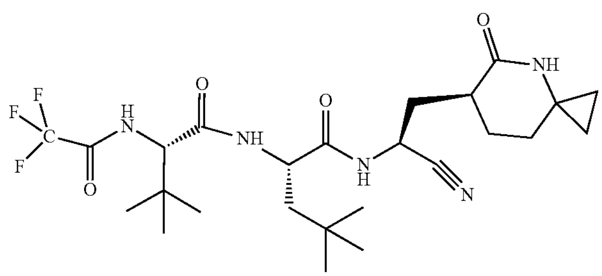 [SMILES: CC(C)(C)C[C@H](NC(=O)[C@@H](NC(=O)C(F)(F)F)C(C)(C)C)C(=O)N[C@H](C#N)C[C@@H]1CCC2(CC2)NC1=O] |
| 3006 | 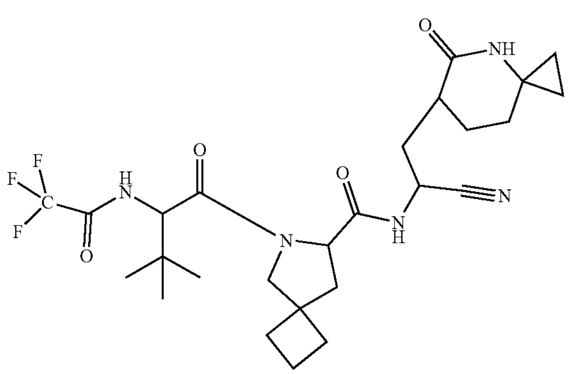 [SMILES: CC(C)(C)C(NC(=O)C(F)(F)F)C(=O)N1CC2(CCC2)CC1C(=O)NC(C#N)CC1CCC2(CC2)NC1=O] |

TABLE 2-continued
Exemplary compounds.
| Cmpd No. | Structure |
|---|---|
| 3007 | 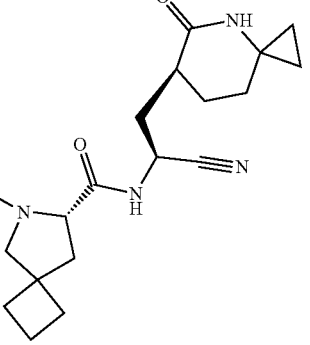 |
| 3008 | 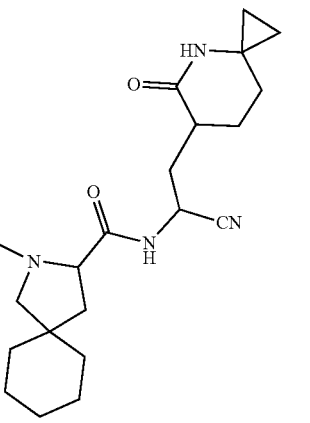 |
| 3009 | 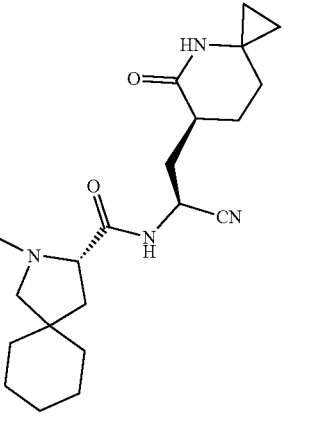 |
| 3010 | 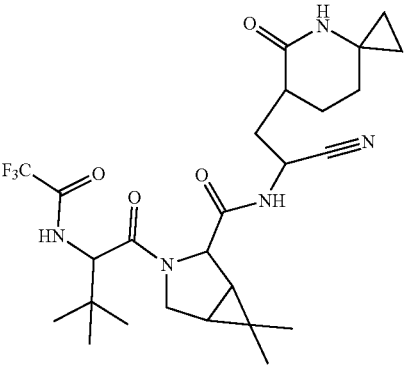 [SMILES: CC(C)(C)C(NC(=O)C(F)(F)F)C(=O)N1CC2C(C1C(=O)NC(C#N)CC1CCC3(CC3)NC1=O)C2(C)C] |

TABLE 2-continued

Exemplary compounds.

| Cmpd No. | Structure |
|---|---|
| 3011 | 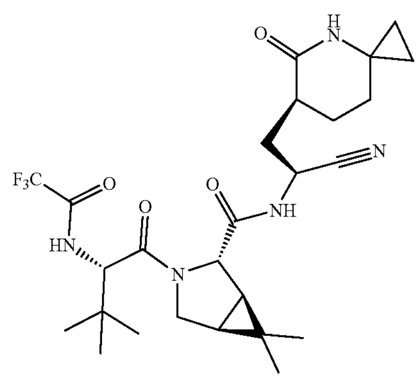 [SMILES: CC(C)(C)[C@H](NC(=O)C(F)(F)F)C(=O)N1C[C@H]2[C@@H]([C@H]1C(=O)N[C@H](C#N)C[C@@H]1CCC3(CC3)NC1=O)C2(C)C] |
| 3012 | 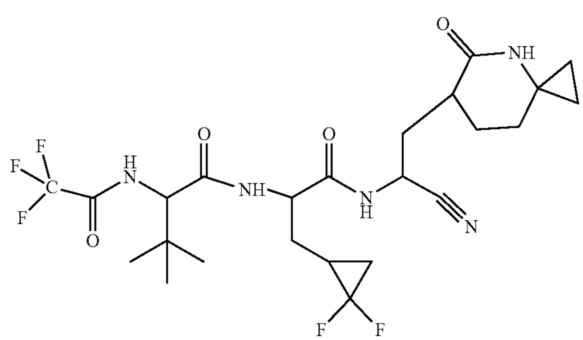 [SMILES: CC(C)(C)C(NC(=O)C(F)(F)F)C(=O)NC(CC1CC1(F)F)C(=O)NC(C#N)CC1CCC2(CC2)NC1=O] |
| 3013 | 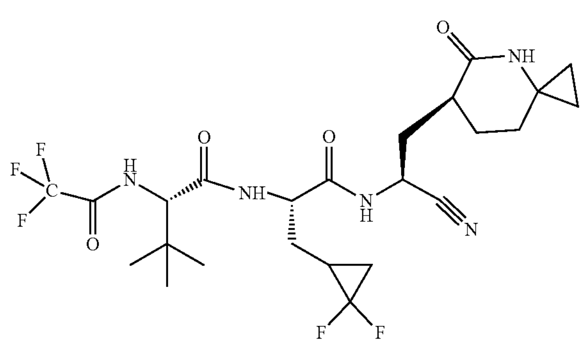 [SMILES: CC(C)(C)[C@H](NC(=O)C(F)(F)F)C(=O)N[C@@H](CC1CC1(F)F)C(=O)N[C@H](C#N)C[C@@H]1CCC2(CC2)NC1=O] |
| 3014 | 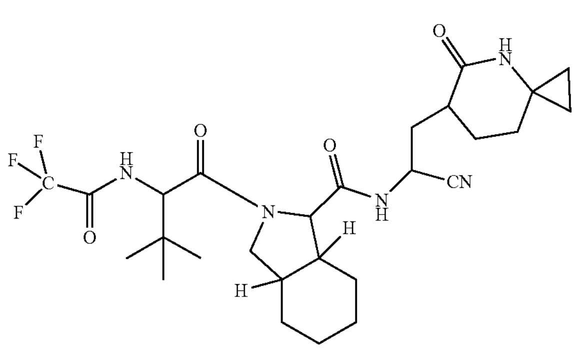 [SMILES: CC(C)(C)C(NC(=O)C(F)(F)F)C(=O)N1CC2CCCCC2C1C(=O)NC(C#N)CC1CCC2(CC2)NC1=O] |

TABLE 2-continued

Exemplary compounds.

| Cmpd No. | Structure |
|---|---|
| 3015 | 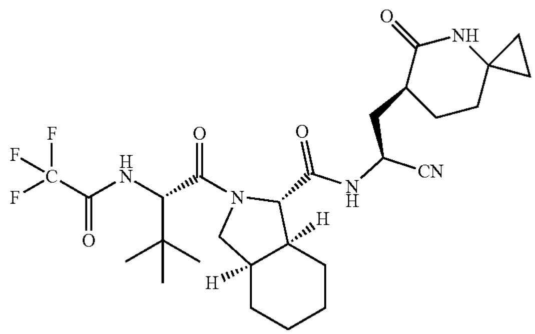 [SMILES: CC(C)(C)[C@H](NC(=O)C(F)(F)F)C(=O)N1C[C@@H]2CCCC[C@@H]2[C@H]1C(=O)N[C@H](C#N)C[C@@H]1CCC2(CC2)NC1=O] |
| 3016 | 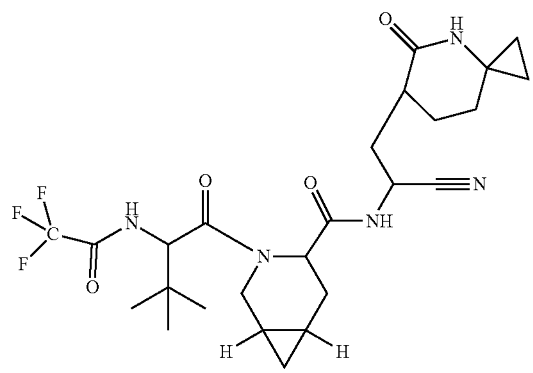 |
| 3017 | 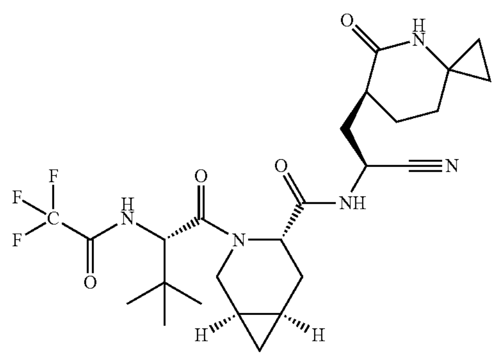 [SMILES: CC(C)(C)[C@H](NC(=O)C(F)(F)F)C(=O)N1C[C@@H]2C[C@@H]2C[C@H]1C(=O)N[C@H](C#N)C[C@@H]1CCC2(CC2)NC1=O] |
| 3018 | 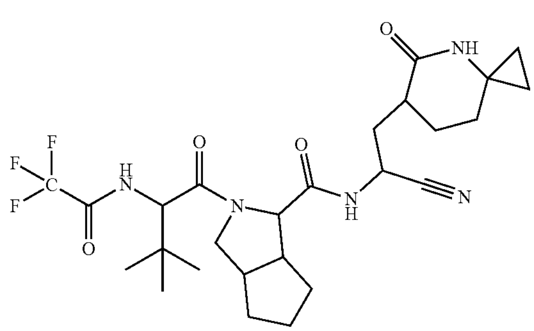 [SMILES: CC(C)(C)C(NC(=O)C(F)(F)F)C(=O)N1CC2CCCC2C1C(=O)NC(C#N)CC1CCC2(CC2)NC1=O] |

TABLE 2-continued

Exemplary compounds.

| Cmpd No. | Structure |
|---|---|
| 3019 | 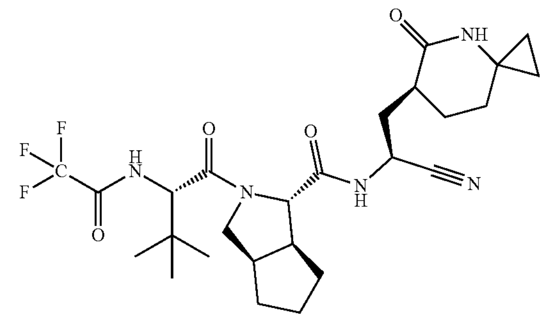 [SMILES: CC(C)(C)[C@H](NC(=O)C(F)(F)F)C(=O)N1C[C@@H]2CCC[C@@H]2[C@H]1C(=O)N[C@H](C#N)C[C@@H]1CCC2(CC2)NC1=O] |
| 3020 | 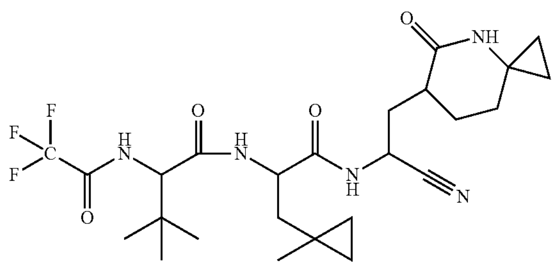 [SMILES: CC1(CC(NC(=O)C(NC(=O)C(F)(F)F)C(C)(C)C)C(=O)NC(C#N)CC2CCC3(CC3)NC2=O)CC1] |
| 3021 | 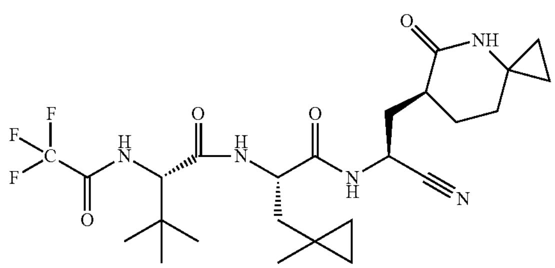 [SMILES: CC1(C[C@H](NC(=O)[C@@H](NC(=O)C(F)(F)F)C(C)(C)C)C(=O)N[C@H](C#N)C[C@@H]2CCC3(CC3)NC2=O)CC1] |
| 3022 | 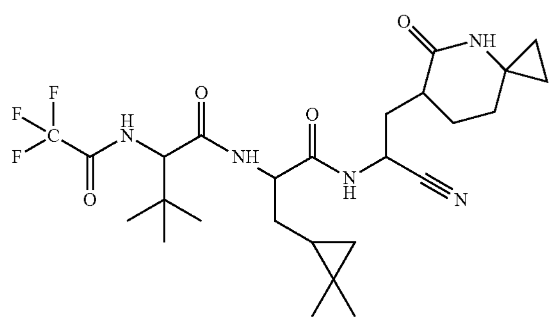 [SMILES: CC(C)(C)C(NC(=O)C(F)(F)F)C(=O)NC(CC1CC1(C)C)C(=O)NC(C#N)CC1CCC2(CC2)NC1=O] |
| 3023 | 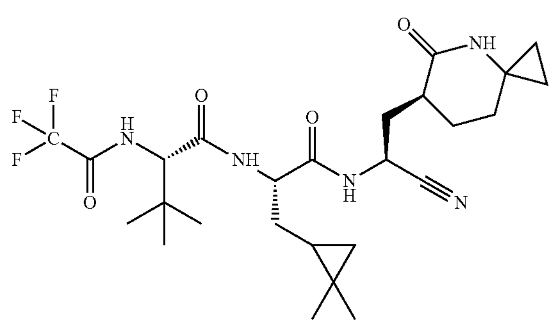 [SMILES: CC1(C)CC1C[C@H](NC(=O)[C@@H](NC(=O)C(F)(F)F)C(C)(C)C)C(=O)N[C@H](C#N)C[C@@H]1CCC2(CC2)NC1=O] |

TABLE 2-continued

Exemplary compounds.

| Cmpd No. | Structure |
|---|---|
| 3024 | 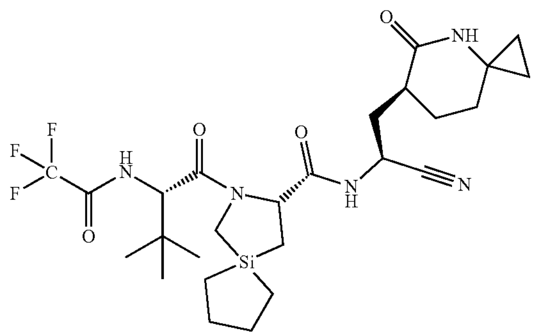 |
| 3025 | 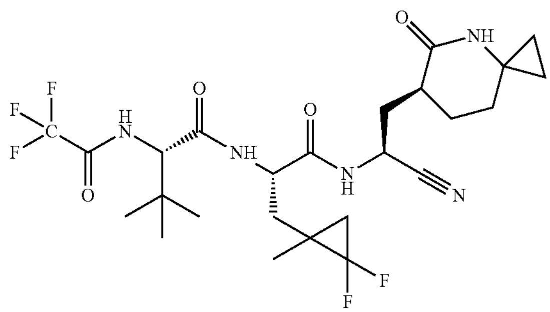 [SMILES: CC(C)(C)[C@H](NC(=O)C(F)(F)F)C(=O)N[C@@H](CC1(C)CC1(F)F)C(=O)N[C@H](C#N)C[C@@H]1CCC2(CC2)NC1=O] |
| 3026 | 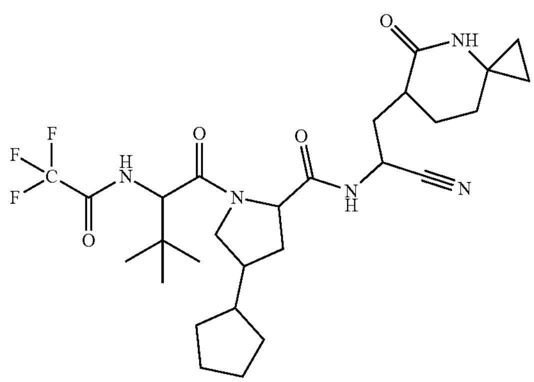 [SMILES: CC(C)(C)C(NC(=O)C(F)(F)F)C(=O)N1CC(C2CCCC2)CC1C(=O)NC(C#N)CC1CCC2(CC2)NC1=O] |
| 3027 | 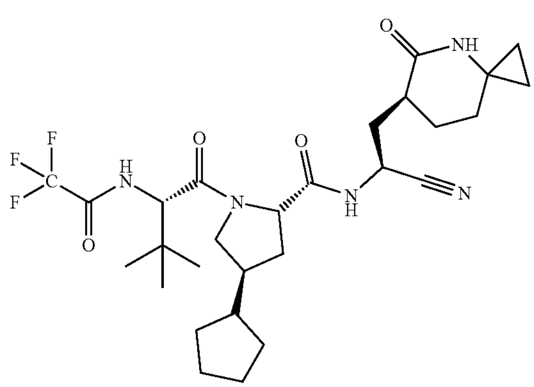 |

TABLE 2-continued
Exemplary compounds.
| Cmpd No. | Structure |
|---|---|
| 3028 | 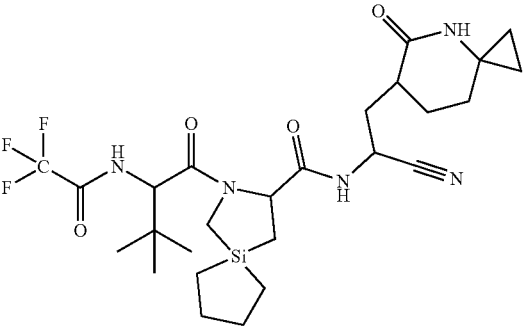 [SMILES: CC(C)(C)C(NC(=O)C(F)(F)F)C(=O)N1C[Si]2(CCCC2)CC1C(=O)NC(C#N)CC1CCC2(CC2)NC1=O] |
| 3029 | 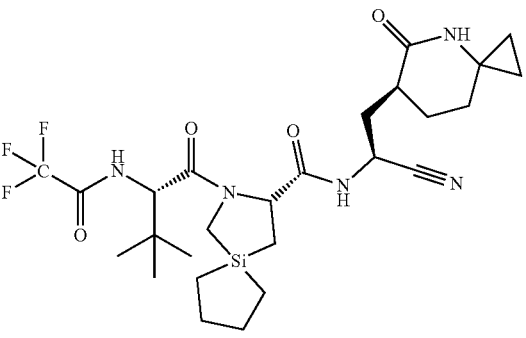 |
| 3030 | 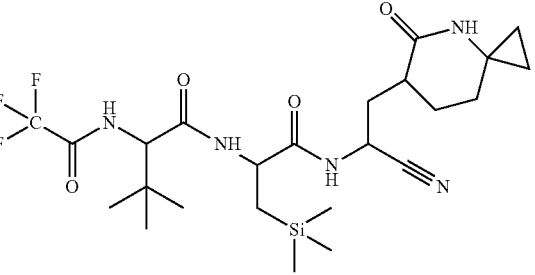 |
| 3031 | 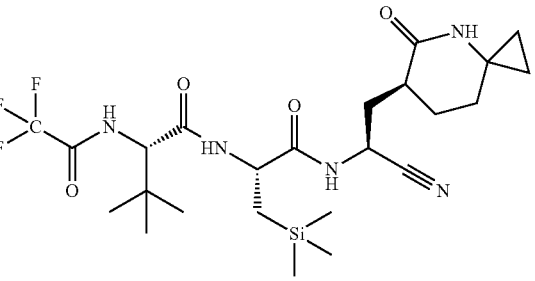 |
| 3032 | 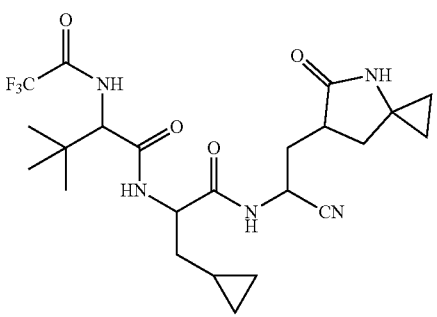 [SMILES: CC(C)(C)C(NC(=O)C(F)(F)F)C(=O)NC(CC1CC1)C(=O)NC(C#N)CC1CC2(CC2)NC1=O] |

TABLE 2-continued
Exemplary compounds.
| Cmpd No. | Structure |
|---|---|
| 3033 | 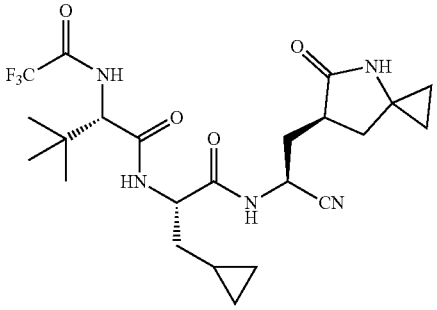 [SMILES: CC(C)(C)[C@H](NC(=O)C(F)(F)F)C(=O)N[C@@H](CC1CC1)C(=O)N[C@H](C#N)C[C@@H]1CC2(CC2)NC1=O] |
| 3034 | 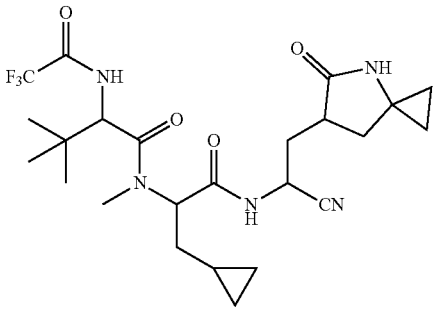 [SMILES: CN(C(=O)C(NC(=O)C(F)(F)F)C(C)(C)C)C(CC1CC1)C(=O)NC(C#N)CC1CC2(CC2)NC1=O] |
| 3035 | 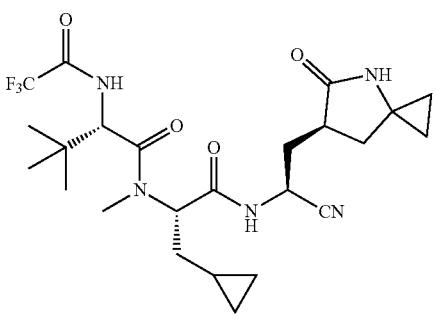 [SMILES: CN(C(=O)[C@@H](NC(=O)C(F)(F)F)C(C)(C)C)[C@@H](CC1CC1)C(=O)N[C@H](C#N)C[C@@H]1CC2(CC2)NC1=O] |
| 3036 | 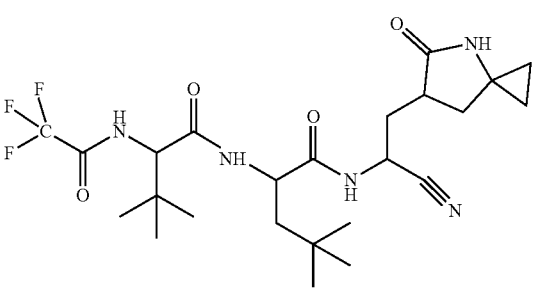 [SMILES: CC(C)(C)CC(NC(=O)C(NC(=O)C(F)(F)F)C(C)(C)C)C(=O)NC(C#N)CC1CC2(CC2)NC1=O] |
| 3037 | 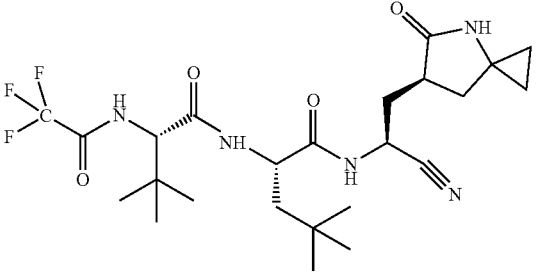 [SMILES: CC(C)(C)C[C@H](NC(=O)[C@@H](NC(=O)C(F)(F)F)C(C)(C)C)C(=O)N[C@H](C#N)C[C@@H]1CC2(CC2)NC1=O] |

TABLE 2-continued
Exemplary compounds.
| Cmpd No. | Structure |
|---|---|
| 3038 | 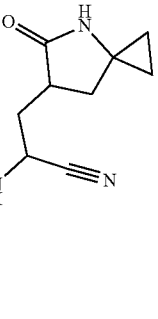 |
| 3039 | 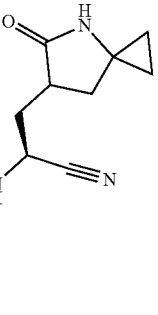 |
| 3040 | 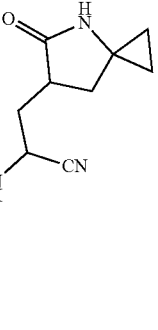 |
| 3041 | 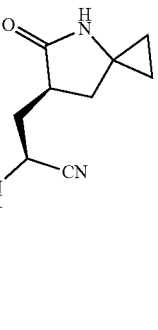 |

TABLE 2-continued

Exemplary compounds.

| Cmpd No. | Structure |
|---|---|
| 3042 | 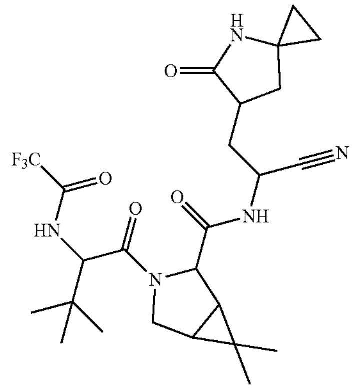 [SMILES: CC(C)(C)C(NC(=O)C(F)(F)F)C(=O)N1CC2C(C1C(=O)NC(C#N)CC1CC3(CC3)NC1=O)C2(C)C] |
| 3043 | 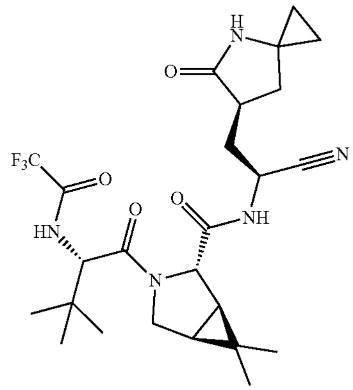 [SMILES: CC(C)(C)[C@H](NC(=O)C(F)(F)F)C(=O)N1C[C@H]2[C@@H]([C@H]1C(=O)N[C@H](C#N)C[C@@H]1CC3(CC3)NC1=O)C2(C)C] |
| 3044 | 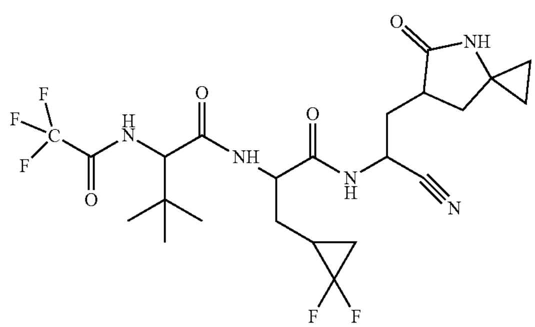 [SMILES: CC(C)(C)C(NC(=O)C(F)(F)F)C(=O)NC(CC1CC1(F)F)C(=O)NC(C#N)CC1CC2(CC2)NC1=O] |
| 3045 | 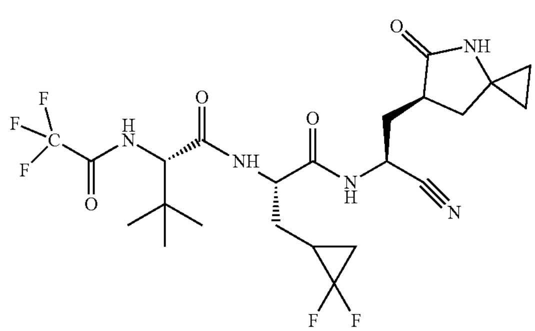 [SMILES: CC(C)(C)[C@H](NC(=O)C(F)(F)F)C(=O)N[C@@H](CC1CC1(F)F)C(=O)N[C@H](C#N)C[C@@H]1CC2(CC2)NC1=O] |

TABLE 2-continued

Exemplary compounds.

| Cmpd No. | Structure |
|---|---|
| 3046 | 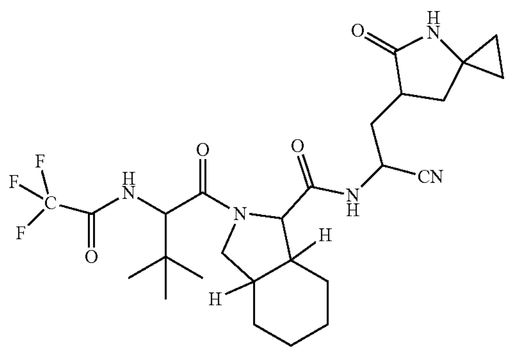 [SMILES: CC(C)(C)C(NC(=O)C(F)(F)F)C(=O)N1CC2CCCCC2C1C(=O)NC(C#N)CC1CC2(CC2)NC1=O] |
| 3047 | 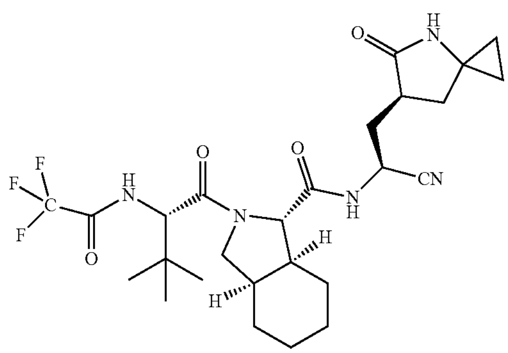 [SMILES: CC(C)(C)[C@H](NC(=O)C(F)(F)F)C(=O)N1C[C@@H]2CCCC[C@@H]2[C@H]1C(=O)N[C@H](C#N)C[C@@H]1CC2(CC2)NC1=O] |
| 3048 | 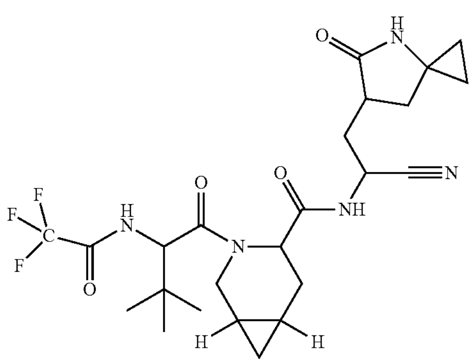 [SMILES: CC(C)(C)C(NC(=O)C(F)(F)F)C(=O)N1CC2CC2CC1C(=O)NC(C#N)CC1CC2(CC2)NC1=O] |
| 3049 | 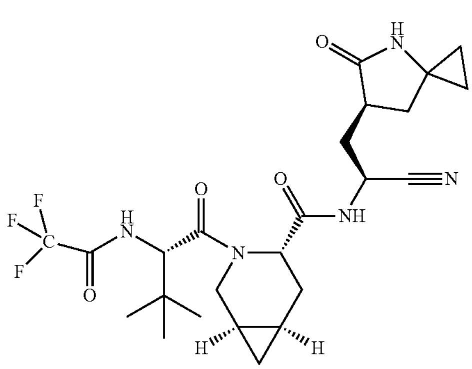 [SMILES: CC(C)(C)[C@H](NC(=O)C(F)(F)F)C(=O)N1C[C@@H]2C[C@@H]2C[C@H]1C(=O)N[C@H](C#N)C[C@@H]1CC2(CC2)NC1=O] |

TABLE 2-continued

Exemplary compounds.

| Cmpd No. | Structure |
|---|---|
| 3050 | 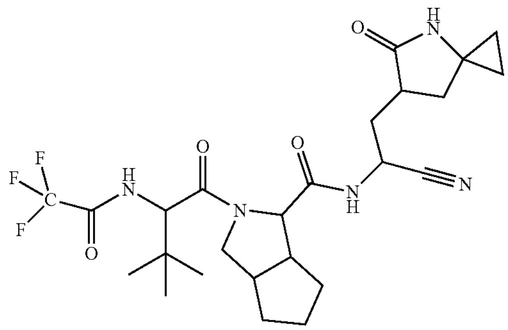 [SMILES: CC(C)(C)C(NC(=O)C(F)(F)F)C(=O)N1CC2CCCC2C1C(=O)NC(C#N)CC1CC2(CC2)NC1=O] |
| 3051 | 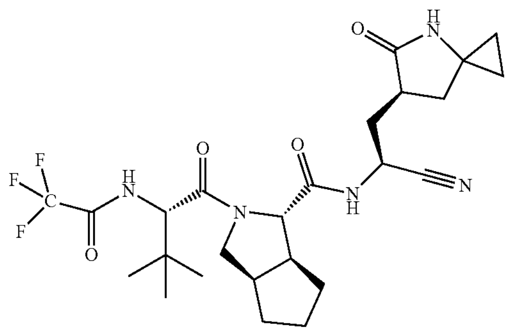 [SMILES: CC(C)(C)[C@H](NC(=O)C(F)(F)F)C(=O)N1C[C@@H]2CCC[C@@H]2[C@H]1C(=O)N[C@H](C#N)C[C@@H]1CC2(CC2)NC1=O] |
| 3052 | 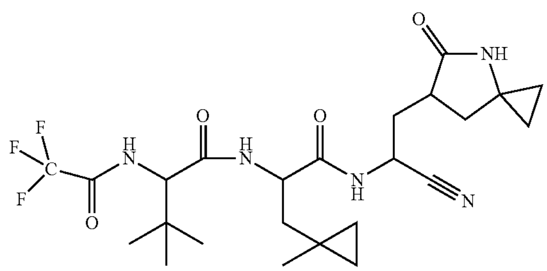 [SMILES: CC1(CC(NC(=O)C(NC(=O)C(F)(F)F)C(C)(C)C)C(=O)NC(C#N)CC2CC3(CC3)NC2=O)CC1] |
| 3053 | 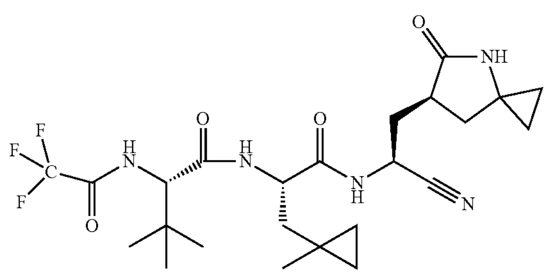 [SMILES: CC1(C[C@H](NC(=O)[C@@H](NC(=O)C(F)(F)F)C(C)(C)C)C(=O)N[C@H](C#N)C[C@@H]2CC3(CC3)NC2=O)CC1] |
| 3054 | 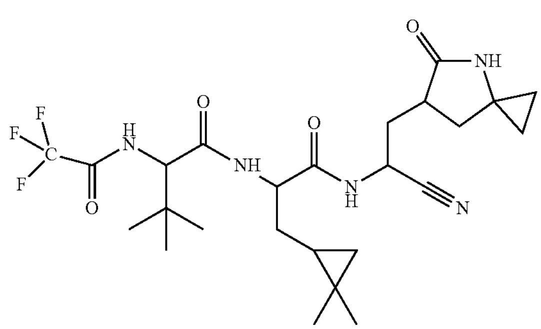 [SMILES: CC(C)(C)C(NC(=O)C(F)(F)F)C(=O)NC(CC1CC1(C)C)C(=O)NC(C#N)CC1CC2(CC2)NC1=O] |

TABLE 2-continued

Exemplary compounds.

| Cmpd No. | Structure |
| --- | --- |
| 3055 | 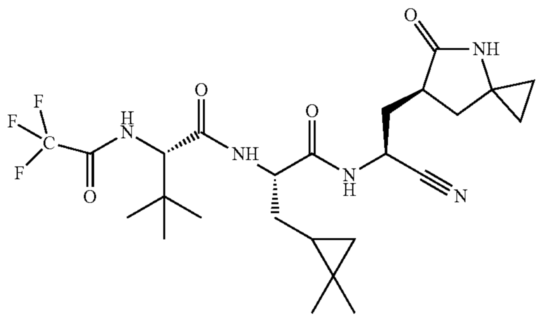 [SMILES: CC1(C)CC1C[C@H](NC(=O)[C@@H](NC(=O)C(F)(F)F)C(C)(C)C)C(=O)N[C@H](C#N)C[C@@H]1CC2(CC2)NC1=O] |
| 3056 | 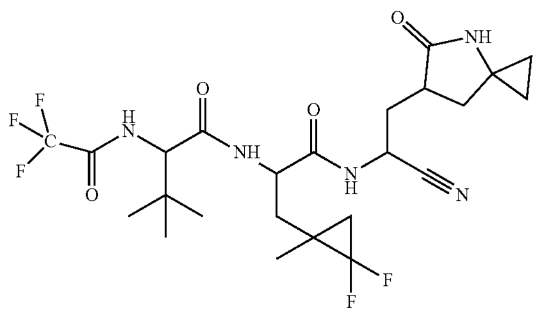 [SMILES: CC(C)(C)C(NC(=O)C(F)(F)F)C(=O)NC(CC1(C)CC1(F)F)C(=O)NC(C#N)CC1CC2(CC2)NC1=O] |
| 3057 | 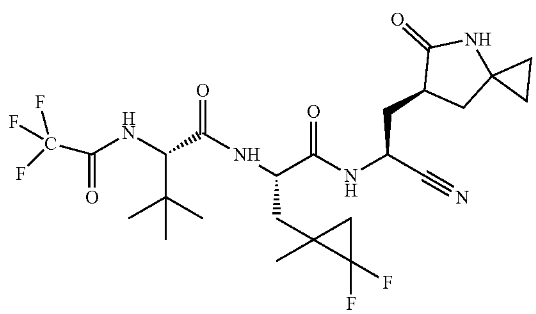 [SMILES: CC(C)(C)[C@H](NC(=O)C(F)(F)F)C(=O)N[C@@H](CC1(C)CC1(F)F)C(=O)N[C@H](C#N)C[C@@H]1CC2(CC2)NC1=O] |
| 3058 | 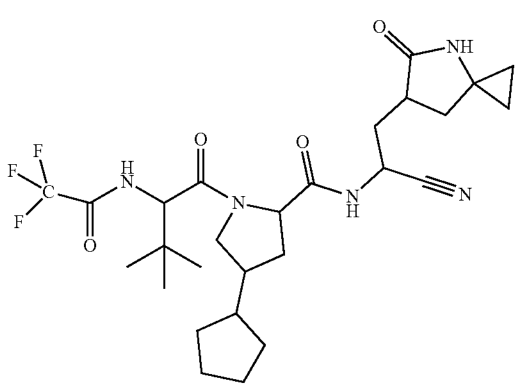 [SMILES: CC(C)(C)C(NC(=O)C(F)(F)F)C(=O)N1CC(C2CCCC2)CC1C(=O)NC(C#N)CC1CC2(CC2)NC1=O] |

TABLE 2-continued

Exemplary compounds.

| Cmpd No. | Structure |
|---|---|
| 3059 | 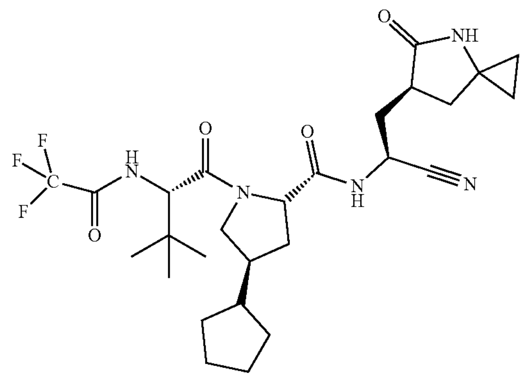 |
| 3060 | 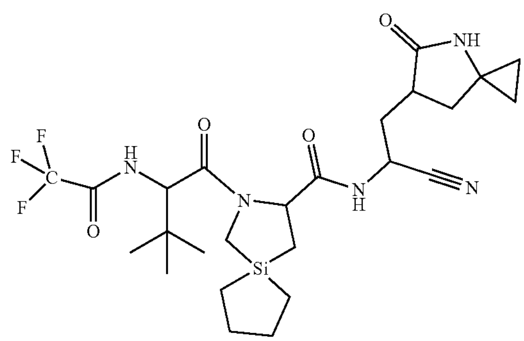 [SMILES: CC(C)(C)C(NC(=O)C(F)(F)F)C(=O)N1C[Si]2(CCCC2)CC1C(=O)NC(C#N)CC1CC2(CC2)NC1=O] |
| 3061 | 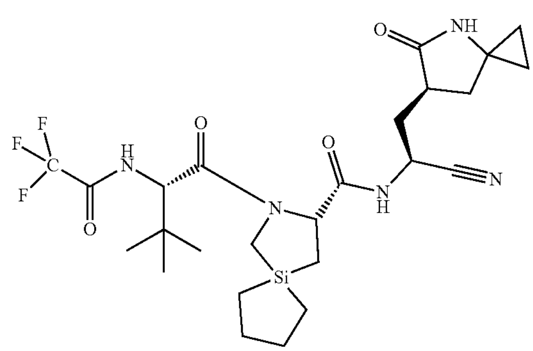 |
| 3062 | 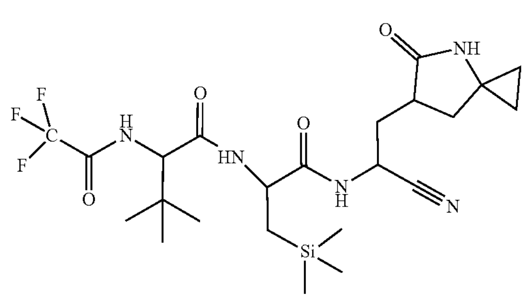 [SMILES: CC(C)(C)C(NC(=O)C(F)(F)F)C(=O)NC(C[Si](C)(C)C)C(=O)NC(C#N)CC1CC2(CC2)NC1=O] |

TABLE 2-continued

Exemplary compounds.

| Cmpd No. | Structure |
|---|---|
| 3063 | 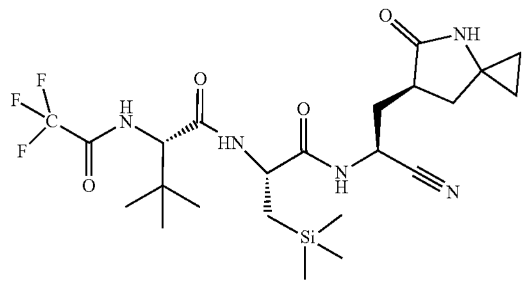 [SMILES: CC(C)(C)[C@H](NC(=O)C(F)(F)F)C(=O)N[C@@H](C[Si](C)(C)C)C(=O)N[C@H](C#N)C[C@@H]1CC2(CC2)NC1=O] |
| 3064 | 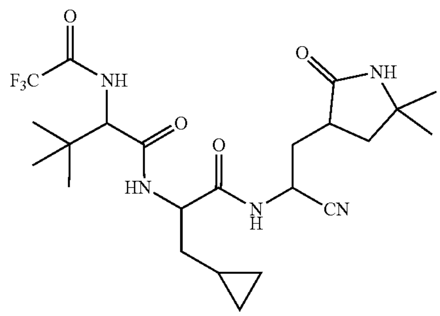 [SMILES: CC1(C)CC(CC(C#N)NC(=O)C(CC2CC2)NC(=O)C(NC(=O)C(F)(F)F)C(C)(C)C)C(=O)N1] |
| 3065 | 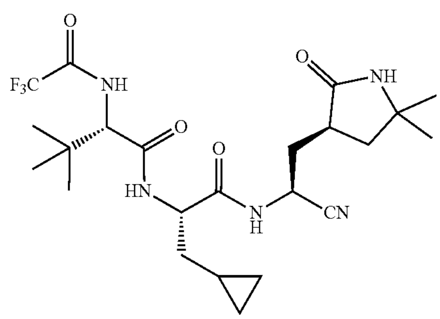 [SMILES: CC1(C)C[C@@H](C[C@@H](C#N)NC(=O)[C@H](CC2CC2)NC(=O)[C@@H](NC(=O)C(F)(F)F)C(C)(C)C)C(=O)N1] |
| 3066 | 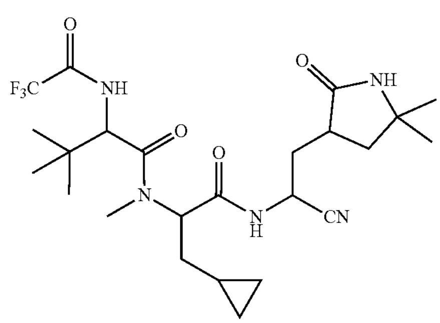 [SMILES: CN(C(=O)C(NC(=O)C(F)(F)F)C(C)(C)C)C(CC1CC1)C(=O)NC(C#N)CC1CC(C)(C)NC1=O] |
| 3067 | 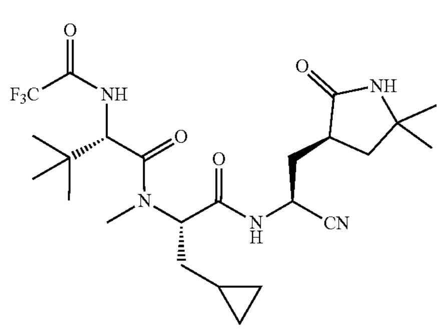 [SMILES: CN(C(=O)[C@@H](NC(=O)C(F)(F)F)C(C)(C)C)[C@@H](CC1CC1)C(=O)N[C@H](C#N)C[C@@H]1CC(C)(C)NC1=O] |

TABLE 2-continued

Exemplary compounds.

| Cmpd No. | Structure |
|---|---|
| 3068 | 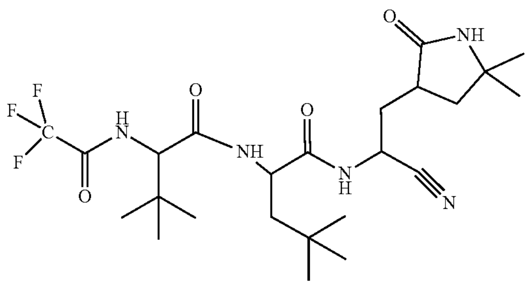 [SMILES: CC(C)(C)CC(NC(=O)C(NC(=O)C(F)(F)F)C(C)(C)C)C(=O)NC(C#N)CC1CC(C)(C)NC1=O] |
| 3069 | 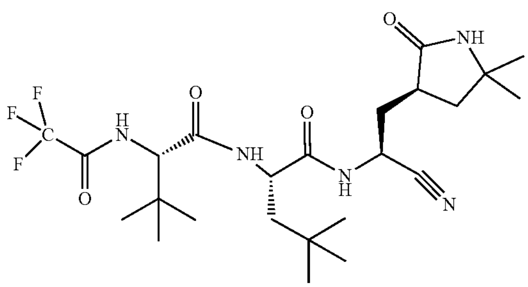 [SMILES: CC(C)(C)C[C@H](NC(=O)[C@@H](NC(=O)C(F)(F)F)C(C)(C)C)C(=O)N[C@H](C#N)C[C@@H]1CC(C)(C)NC1=O] |
| 3070 | 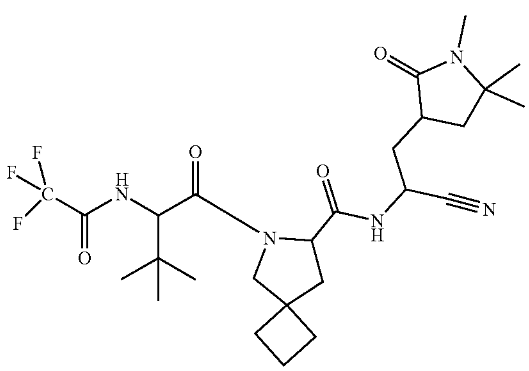 [SMILES: CN1C(=O)C(CC(C#N)NC(=O)C2CC3(CCC3)CN2C(=O)C(NC(=O)C(F)(F)F)C(C)(C)C)CC1(C)C] |
| 3071 | 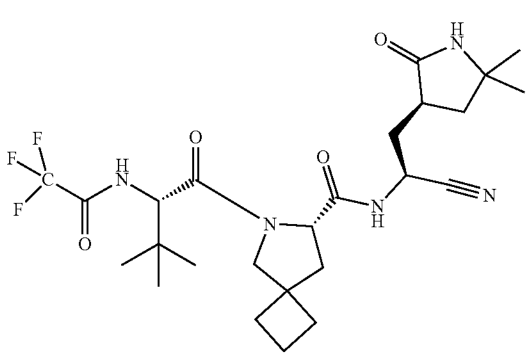 [SMILES: CC1(C)C[C@@H](C[C@@H](C#N)NC(=O)[C@@H]2CC3(CCC3)CN2C(=O)[C@@H](NC(=O)C(F)(F)F)C(C)(C)C)C(=O)N1] |

TABLE 2-continued

Exemplary compounds.

| Cmpd No. | Structure |
|---|---|
| 3072 | 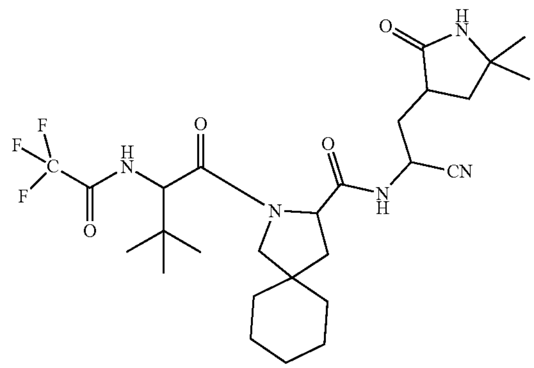 [SMILES: CC1(C)CC(CC(C#N)NC(=O)C2CC3(CCCCC3)CN2C(=O)C(NC(=O)C(F)(F)F)C(C)(C)C)C(=O)N1] |
| 3073 | 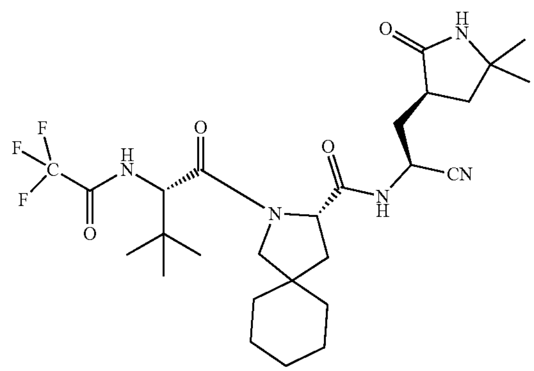 [SMILES: CC1(C)C[C@@H](C[C@@H](C#N)NC(=O)[C@@H]2CC3(CCCCC3)CN2C(=O)[C@@H](NC(=O)C(F)(F)F)C(C)(C)C)C(=O)N1] |
| 3074 | 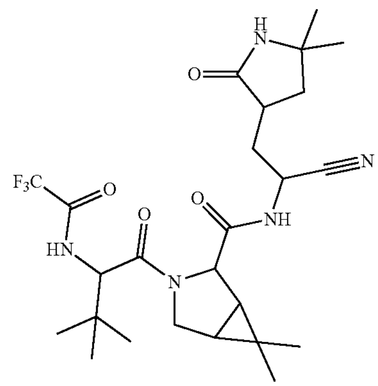 [SMILES: CC1(C)CC(CC(C#N)NC(=O)C2C3C(CN2C(=O)C(NC(=O)C(F)(F)F)C(C)(C)C)C3(C)C)C(=O)N1] |
| 3075 | 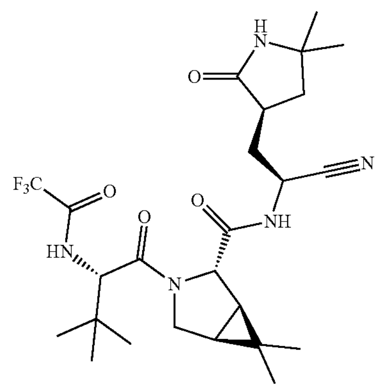 [SMILES: CC1(C)C[C@@H](C[C@@H](C#N)NC(=O)[C@@H]2[C@@H]3[C@H](CN2C(=O)[C@@H](NC(=O)C(F)(F)F)C(C)(C)C)C3(C)C)C(=O)N1] |

TABLE 2-continued

Exemplary compounds.

| Cmpd No. | Structure |
|---|---|
| 3076 | 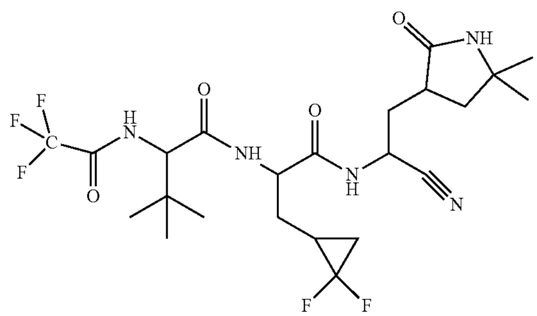 [SMILES: CC1(C)CC(CC(C#N)NC(=O)C(CC2CC2(F)F)NC(=O)C(NC(=O)C(F)(F)F)C(C)(C)C)C(=O)N1] |
| 3077 | 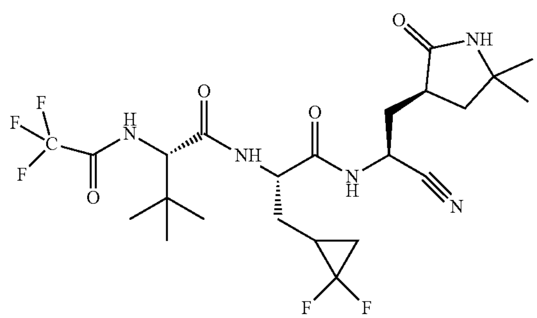 [SMILES: CC1(C)C[C@@H](C[C@@H](C#N)NC(=O)[C@H](CC2CC2(F)F)NC(=O)[C@@H](NC(=O)C(F)(F)F)C(C)(C)C)C(=O)N1] |
| 3078 | 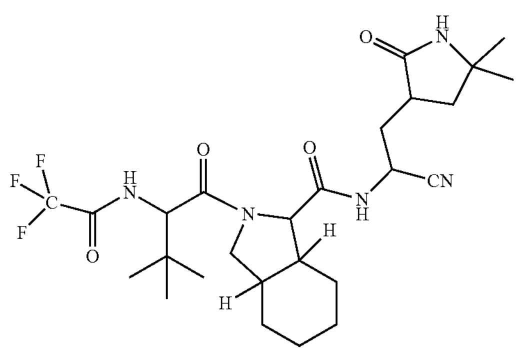 [SMILES: CC1(C)CC(CC(C#N)NC(=O)C2C3CCCCC3CN2C(=O)C(NC(=O)C(F)(F)F)C(C)(C)C)C(=O)N1] |
| 3079 | 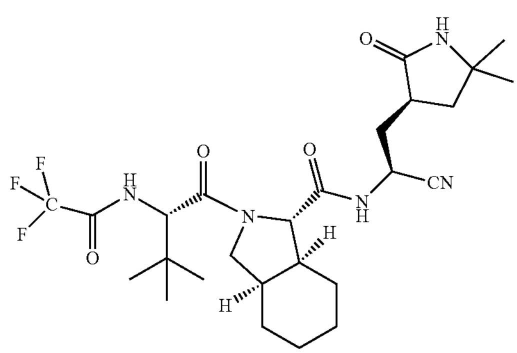 [SMILES: CC1(C)C[C@@H](C[C@@H](C#N)NC(=O)[C@@H]2[C@H]3CCCC[C@H]3CN2C(=O)[C@@H](NC(=O)C(F)(F)F)C(C)(C)C)C(=O)N1] |

TABLE 2-continued

Exemplary compounds.

| Cmpd No. | Structure |
|---|---|
| 3080 | 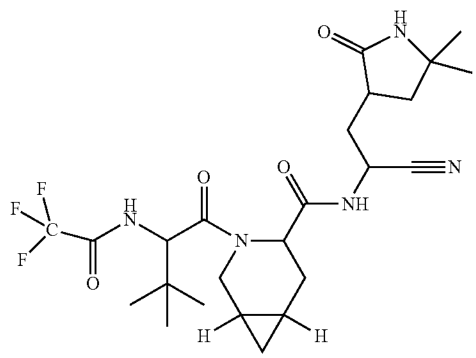 [SMILES: CC1(C)CC(CC(C#N)NC(=O)C2CC3CC3CN2C(=O)C(NC(=O)C(F)(F)F)C(C)(C)C)C(=O)N1] |
| 3081 | 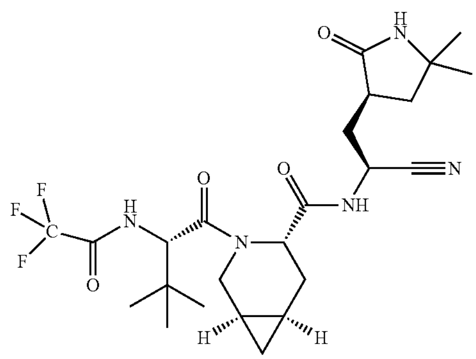 [SMILES: CC1(C)C[C@@H](C[C@@H](C#N)NC(=O)[C@@H]2C[C@H]3C[C@H]3CN2C(=O)[C@@H](NC(=O)C(F)(F)F)C(C)(C)C)C(=O)N1] |
| 3082 | 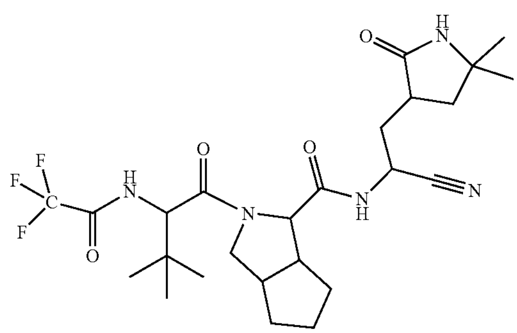 [SMILES: CC1(C)CC(CC(C#N)NC(=O)C2C3CCCC3CN2C(=O)C(NC(=O)C(F)(F)F)C(C)(C)C)C(=O)N1] |
| 3083 | 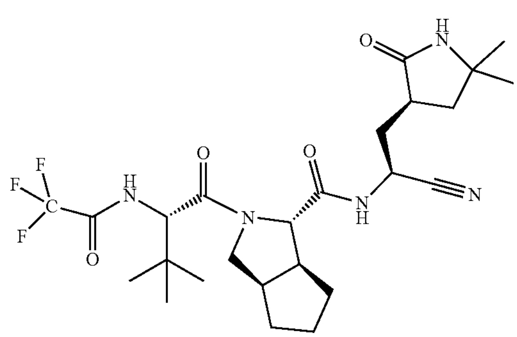 [SMILES: CC1(C)C[C@@H](C[C@@H](C#N)NC(=O)[C@@H]2[C@H]3CCC[C@H]3CN2C(=O)[C@@H](NC(=O)C(F)(F)F)C(C)(C)C)C(=O)N1] |

TABLE 2-continued

Exemplary compounds.

| Cmpd No. | Structure |
|---|---|
| 3084 | 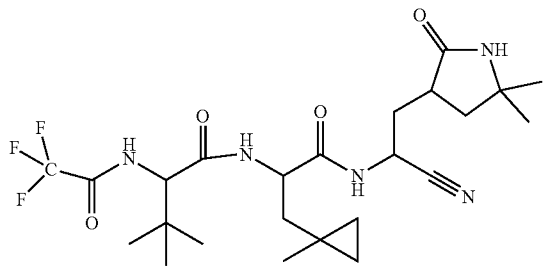 [SMILES: CC1(CC(NC(=O)C(NC(=O)C(F)(F)F)C(C)(C)C)C(=O)NC(C#N)CC2CC(C)(C)NC2=O)CC1] |
| 3085 | 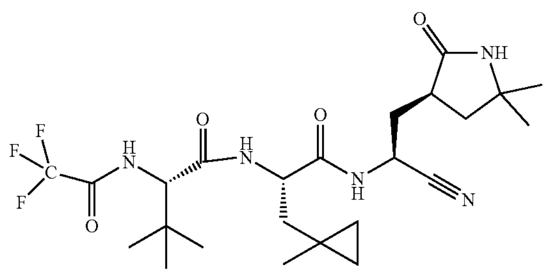 [SMILES: CC1(C[C@H](NC(=O)[C@@H](NC(=O)C(F)(F)F)C(C)(C)C)C(=O)N[C@H](C#N)C[C@@H]2CC(C)(C)NC2=O)CC1] |
| 3086 | 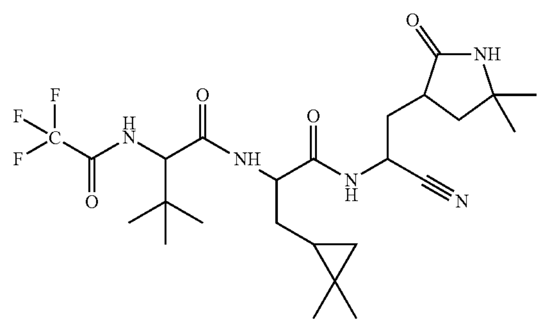 [SMILES: CC1(C)CC(CC(C#N)NC(=O)C(CC2CC2(C)C)NC(=O)C(NC(=O)C(F)(F)F)C(C)(C)C)C(=O)N1] |
| 3087 | 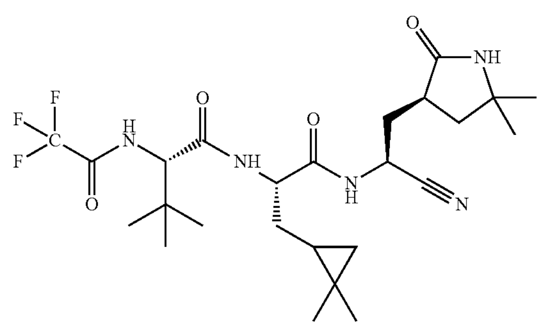 [SMILES: CC1(C)C[C@@H](C[C@@H](C#N)NC(=O)[C@H](CC2CC2(C)C)NC(=O)[C@@H](NC(=O)C(F)(F)F)C(C)(C)C)C(=O)N1] |
| 3088 | 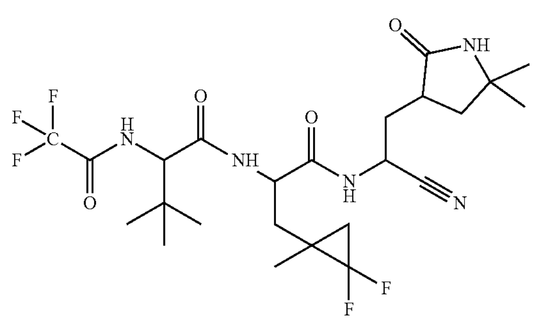 [SMILES: CC1(C)CC(CC(C#N)NC(=O)C(CC2(C)CC2(F)F)NC(=O)C(NC(=O)C(F)(F)F)C(C)(C)C)C(=O)N1] |

TABLE 2-continued

Exemplary compounds.

| Cmpd No. | Structure |
|---|---|
| 3089 | 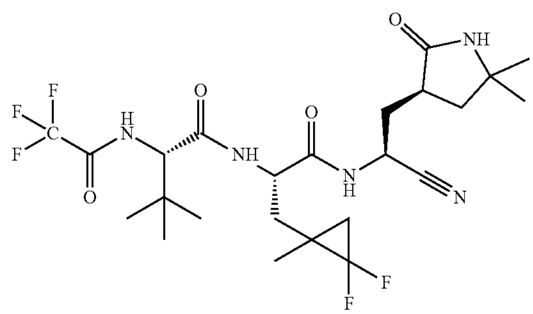 [SMILES: CC1(C)C[C@@H](C[C@@H](C#N)NC(=O)[C@H](CC2(C)CC2(F)F)NC(=O)[C@@H](NC(=O)C(F)(F)F)C(C)(C)C)C(=O)N1] |
| 3090 | 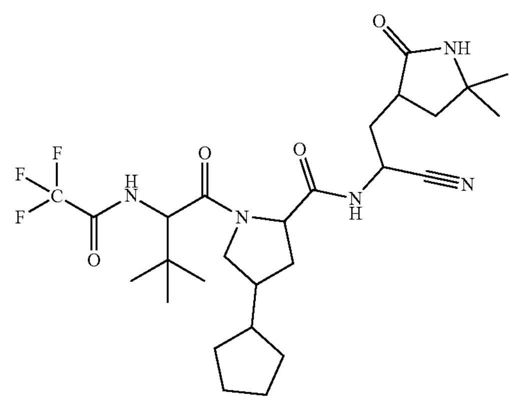 [SMILES: CC1(C)CC(CC(C#N)NC(=O)C2CC(C3CCCC3)CN2C(=O)C(NC(=O)C(F)(F)F)C(C)(C)C)C(=O)N1] |
| 3091 | 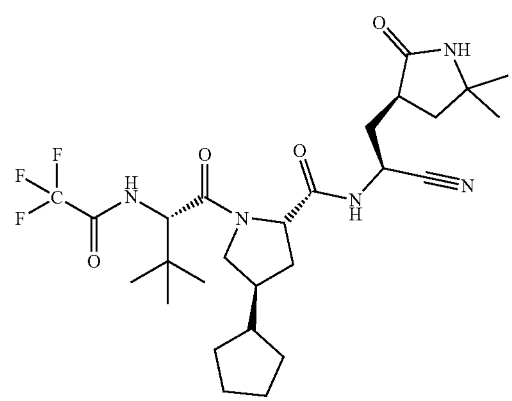 |
| 3092 | 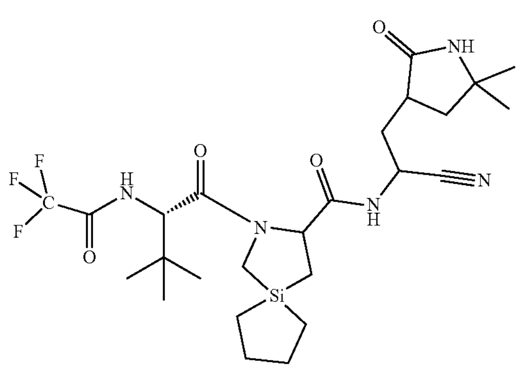 [SMILES: CC1(C)CC(CC(C#N)NC(=O)C2C[Si]3(CCCC3)CN2C(=O)[C@@H](NC(=O)C(F)(F)F)C(C)(C)C)C(=O)N1] |

TABLE 2-continued
Exemplary compounds.
| Cmpd No. | Structure |
|---|---|
| 3093 | 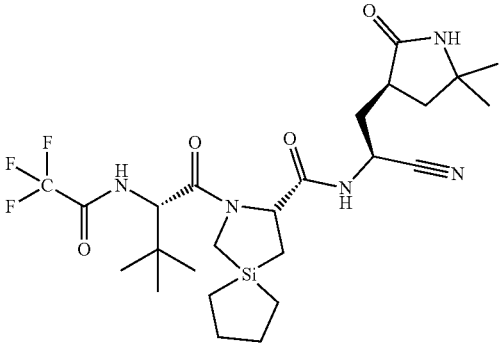 |
| 3094 | 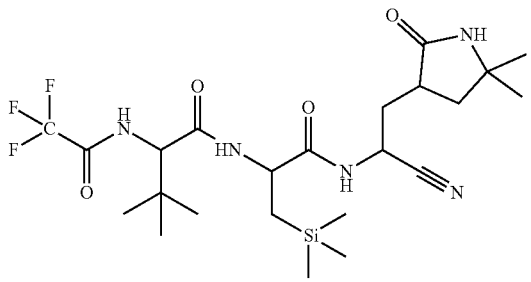 [SMILES: CC1(C)CC(CC(C#N)NC(=O)C(C[Si](C)(C)C)NC(=O)C(NC(=O)C(F)(F)F)C(C)(C)C)C(=O)N1] |
| 3095 | 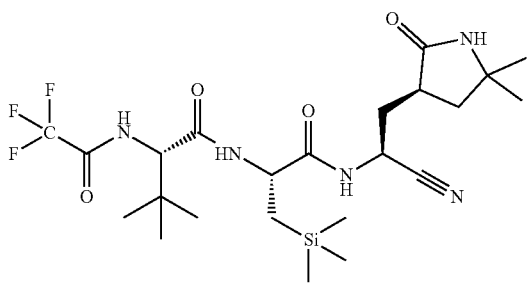 [SMILES: CC1(C)C[C@@H](C[C@@H](C#N)NC(=O)[C@H](C[Si](C)(C)C)NC(=O)[C@@H](NC(=O)C(F)(F)F)C(C)(C)C)C(=O)N1] |
| 3096 | 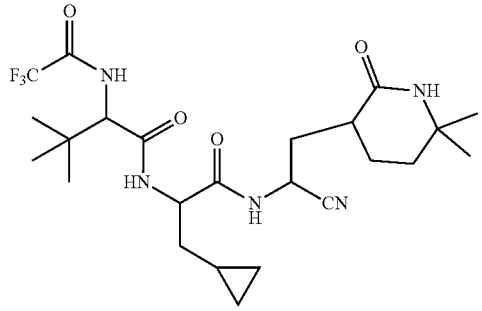 [SMILES: CC1(C)CCC(CC(C#N)NC(=O)C(CC2CC2)NC(=O)C(NC(=O)C(F)(F)F)C(C)(C)C)C(=O)N1] |
| 3097 | 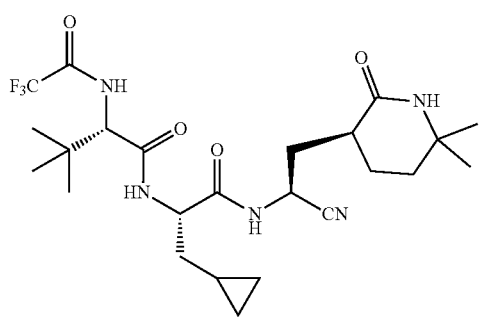 [SMILES: CC1(C)CC[C@@H](C[C@@H](C#N)NC(=O)[C@H](CC2CC2)NC(=O)[C@@H](NC(=O)C(F)(F)F)C(C)(C)C)C(=O)N1] |

TABLE 2-continued
Exemplary compounds.
| Cmpd No. | Structure |
|---|---|
| 3098 | 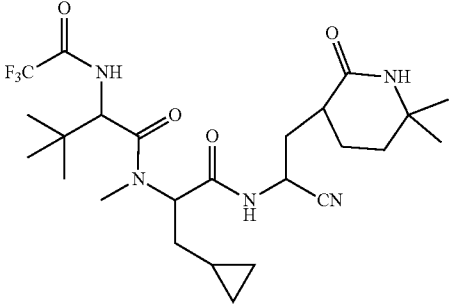 [SMILES: CN(C(=O)C(NC(=O)C(F)(F)F)C(C)(C)C)C(CC1CC1)C(=O)NC(C#N)CC1CCC(C)(C)NC1=O] |
| 3099 | 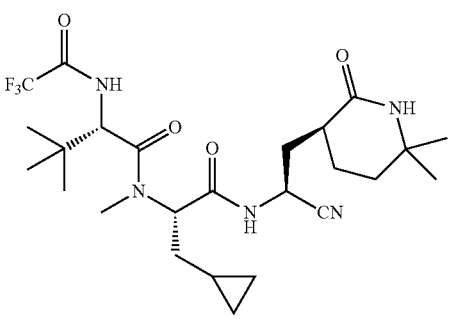 [SMILES: CN(C(=O)[C@@H](NC(=O)C(F)(F)F)C(C)(C)C)[C@@H](CC1CC1)C(=O)N[C@H](C#N)C[C@@H]1CCC(C)(C)NC1=O] |
| 3100 | 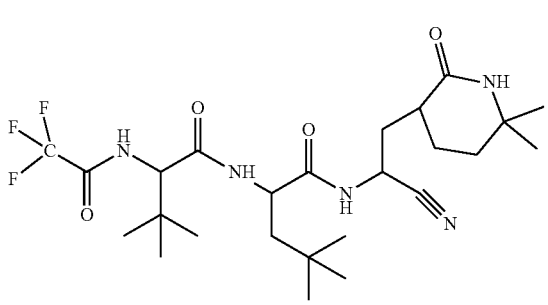 [SMILES: CC(C)(C)CC(NC(=O)C(NC(=O)C(F)(F)F)C(C)(C)C)C(=O)NC(C#N)CC1CCC(C)(C)NC1=O] |
| 3101 | 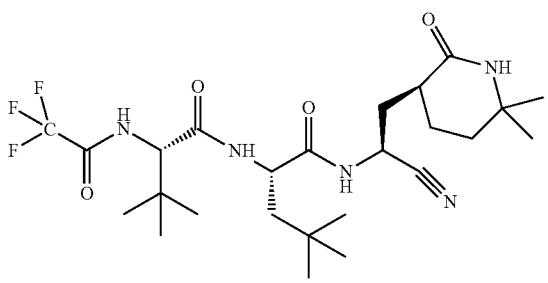 [SMILES: CC(C)(C)C[C@H](NC(=O)[C@@H](NC(=O)C(F)(F)F)C(C)(C)C)C(=O)N[C@H](C#N)C[C@@H]1CCC(C)(C)NC1=O] |
| 3102 | 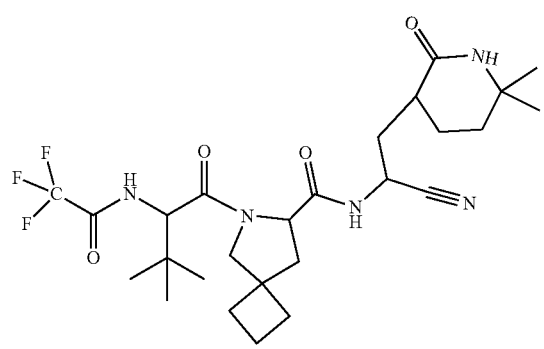 [SMILES: CC1(C)CCC(CC(C#N)NC(=O)C2CC3(CCC3)CN2C(=O)C(NC(=O)C(F)(F)F)C(C)(C)C)C(=O)N1] |

TABLE 2-continued

Exemplary compounds.

| Cmpd No. | Structure |
|---|---|
| 3103 | 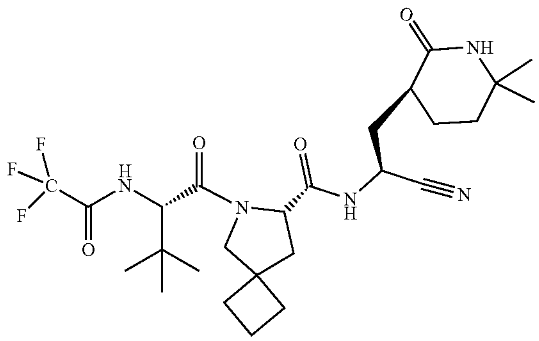 |
| 3104 | 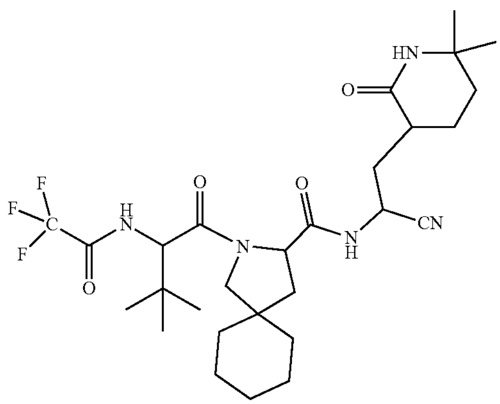 [SMILES: CC1(C)CCC(CC(C#N)NC(=O)C2CC3(CCCCC3)CN2C(=O)C(NC(=O)C(F)(F)F)C(C)(C)C)C(=O)N1] |
| 3105 | 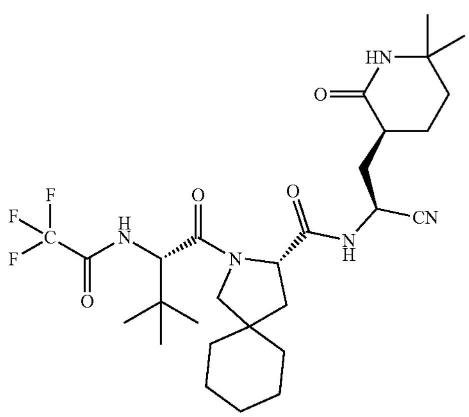 [SMILES: CC1(C)CC[C@@H](C[C@@H](C#N)NC(=O)[C@@H]2CC3(CCCCC3)CN2C(=O)[C@@H](NC(=O)C(F)(F)F)C(C)(C)C)C(=O)N1] |
| 3106 | 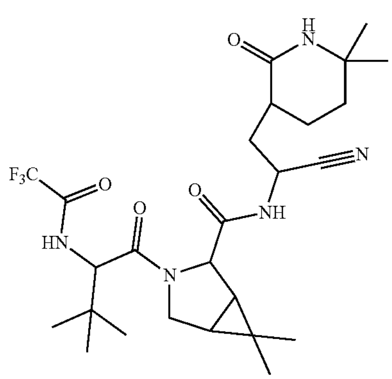 [SMILES: CC1(C)CCC(CC(C#N)NC(=O)C2C3C(CN2C(=O)C(NC(=O)C(F)(F)F)C(C)(C)C)C3(C)C)C(=O)N1] |

TABLE 2-continued

Exemplary compounds.

| Cmpd No. | Structure |
| --- | --- |
| 3107 | 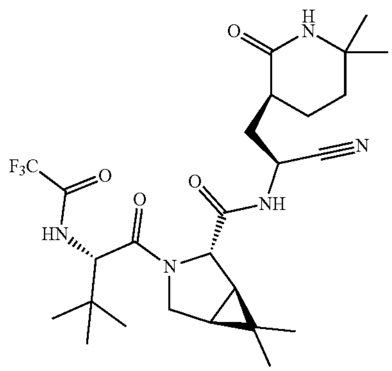 [SMILES: CC1(C)CC[C@@H](C[C@@H](C#N)NC(=O)[C@@H]2[C@@H]3[C@H](CN2C(=O)[C@@H](NC(=O)C(F)(F)F)C(C)(C)C)C3(C)C)C(=O)N1] |
| 3108 | 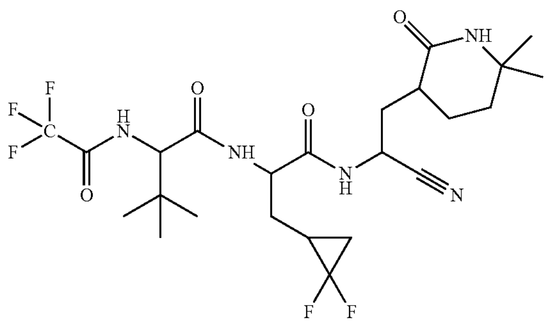 [SMILES: CC1(C)CCC(CC(C#N)NC(=O)C(CC2CC2(F)F)NC(=O)C(NC(=O)C(F)(F)F)C(C)(C)C)C(=O)N1] |
| 3109 | 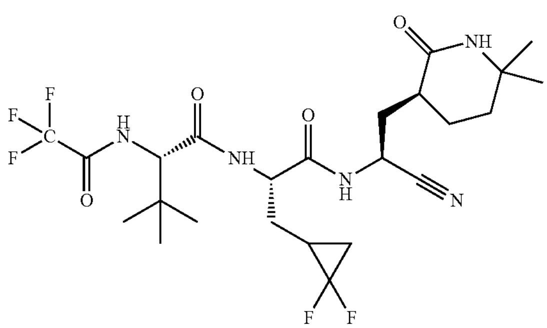 [SMILES: CC1(C)CC[C@@H](C[C@@H](C#N)NC(=O)[C@H](CC2CC2(F)F)NC(=O)[C@@H](NC(=O)C(F)(F)F)C(C)(C)C)C(=O)N1] |
| 3110 | 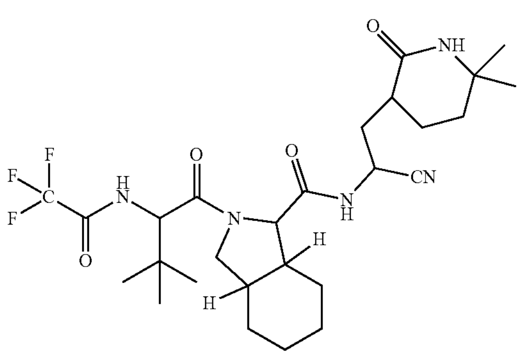 [SMILES: CC1(C)CCC(CC(C#N)NC(=O)C2C3CCCCC3CN2C(=O)C(NC(=O)C(F)(F)F)C(C)(C)C)C(=O)N1] |

TABLE 2-continued

Exemplary compounds.

| Cmpd No. | Structure |
|---|---|
| 3111 | 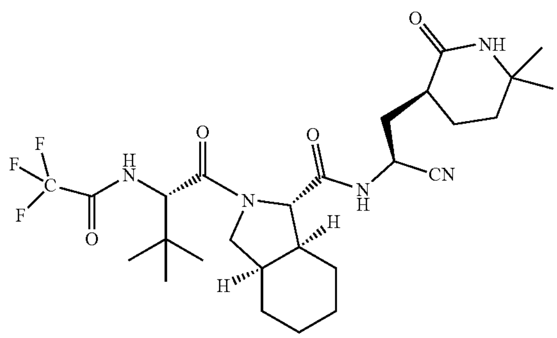 [SMILES: CC1(C)CC[C@@H](C[C@@H](C#N)NC(=O)[C@@H]2[C@H]3CCCC[C@H]3CN2C(=O)[C@@H](NC(=O)C(F)(F)F)C(C)(C)C)C(=O)N1] |
| 3112 | 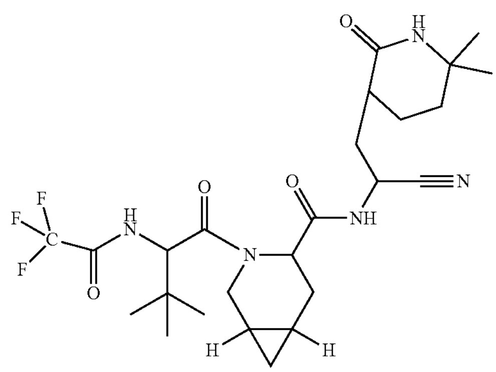 [SMILES: CC1(C)CCC(CC(C#N)NC(=O)C2CC3CC3CN2C(=O)C(NC(=O)C(F)(F)F)C(C)(C)C)C(=O)N1] |
| 3113 | 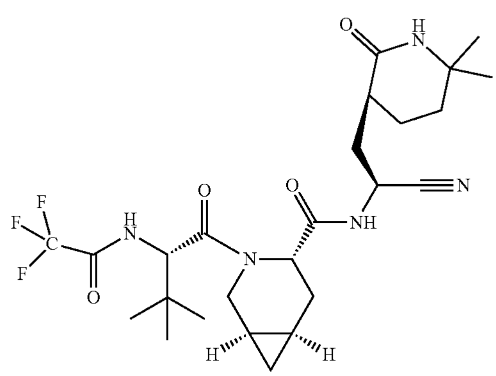 [SMILES: CC1(C)CC[C@@H](C[C@@H](C#N)NC(=O)[C@@H]2C[C@H]3C[C@H]3CN2C(=O)[C@@H](NC(=O)C(F)(F)F)C(C)(C)C)C(=O)N1] |
| 3114 | 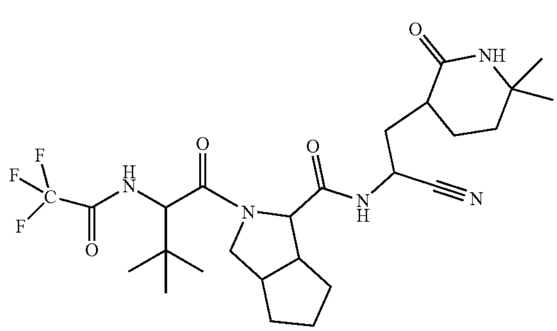 [SMILES: CC1(C)CCC(CC(C#N)NC(=O)C2C3CCCC3CN2C(=O)C(NC(=O)C(F)(F)F)C(C)(C)C)C(=O)N1] |

TABLE 2-continued

Exemplary compounds.

| Cmpd No. | Structure |
|---|---|
| 3115 | 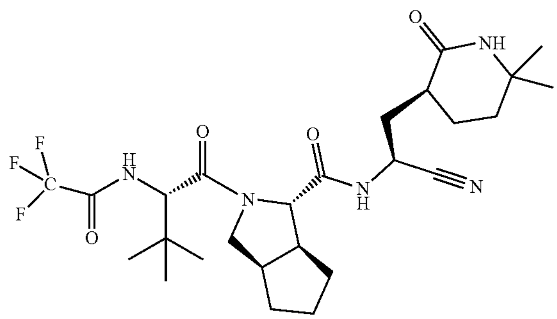 [SMILES: CC1(C)CC[C@@H](C[C@@H](C#N)NC(=O)[C@@H]2[C@H]3CCC[C@H]3CN2C(=O)[C@@H](NC(=O)C(F)(F)F)C(C)(C)C)C(=O)N1] |
| 3116 | 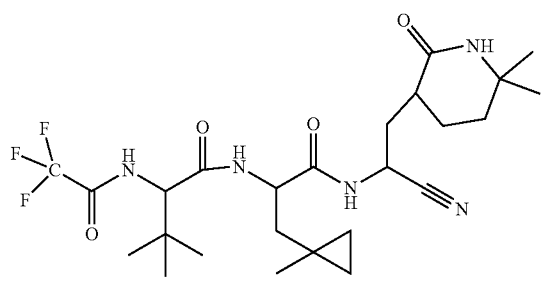 [SMILES: CC1(CC(NC(=O)C(NC(=O)C(F)(F)F)C(C)(C)C)C(=O)NC(C#N)CC2CCC(C)(C)NC2=O)CC1] |
| 3117 | 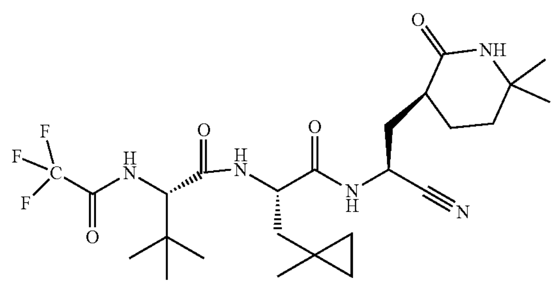 [SMILES: CC1(C[C@H](NC(=O)[C@@H](NC(=O)C(F)(F)F)C(C)(C)C)C(=O)N[C@H](C#N)C[C@@H]2CCC(C)(C)NC2=O)CC1] |
| 3118 | 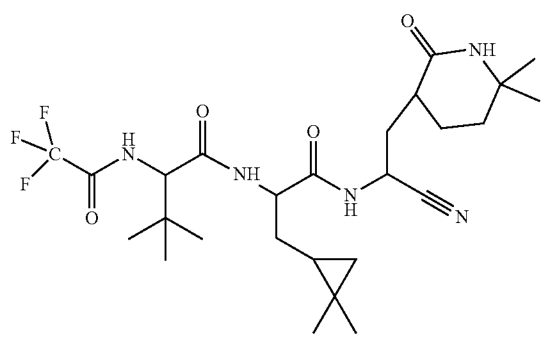 [SMILES: CC1(C)CCC(CC(C#N)NC(=O)C(CC2CC2(C)C)NC(=O)C(NC(=O)C(F)(F)F)C(C)(C)C)C(=O)N1] |
| 3119 | 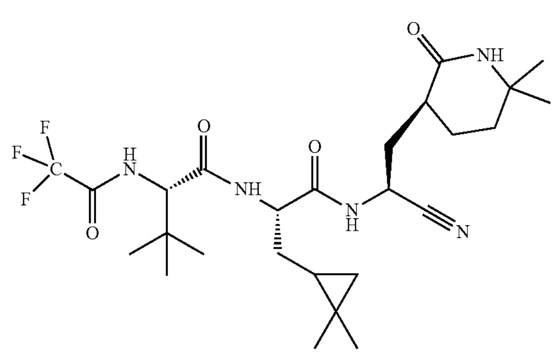 [SMILES: CC1(C)CC[C@@H](C[C@@H](C#N)NC(=O)[C@H](CC2CC2(C)C)NC(=O)[C@@H](NC(=O)C(F)(F)F)C(C)(C)C)C(=O)N1] |

TABLE 2-continued

Exemplary compounds.

| Cmpd No. | Structure |
|---|---|
| 3120 | 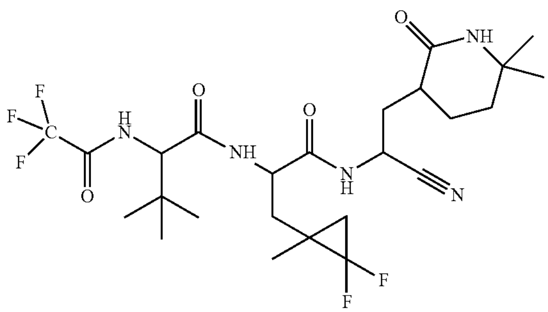 [SMILES: CC1(C)CCC(CC(C#N)NC(=O)C(CC2(C)CC2(F)F)NC(=O)C(NC(=O)C(F)(F)F)C(C)(C)C)C(=O)N1] |
| 3121 | 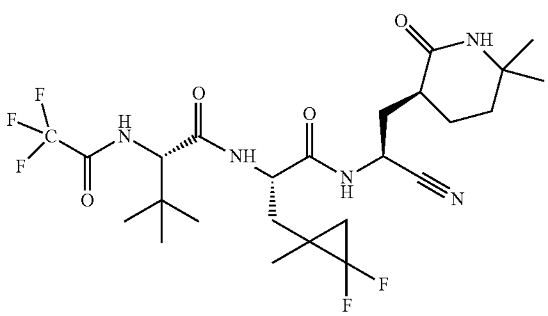 [SMILES: CC1(C)CC[C@@H](C[C@@H](C#N)NC(=O)[C@H](CC2(C)CC2(F)F)NC(=O)[C@@H](NC(=O)C(F)(F)F)C(C)(C)C)C(=O)N1] |
| 3122 | 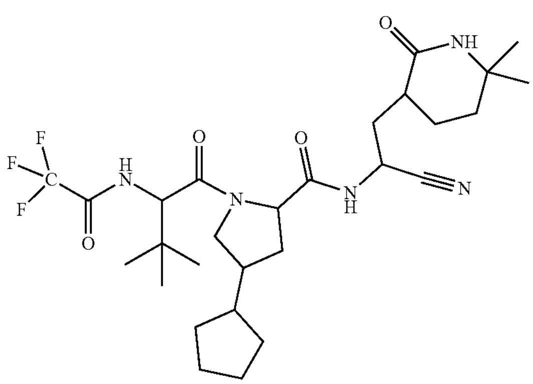 [SMILES: CC1(C)CCC(CC(C#N)NC(=O)C2CC(C3CCCC3)CN2C(=O)C(NC(=O)C(F)(F)F)C(C)(C)C)C(=O)N1] |
| 3123 | 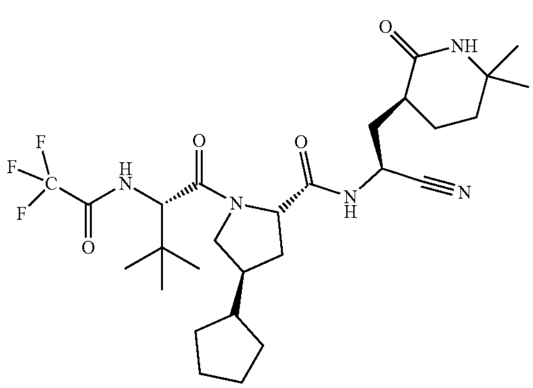 |

TABLE 2-continued

Exemplary compounds.

| Cmpd No. | Structure |
|---|---|
| 3124 | 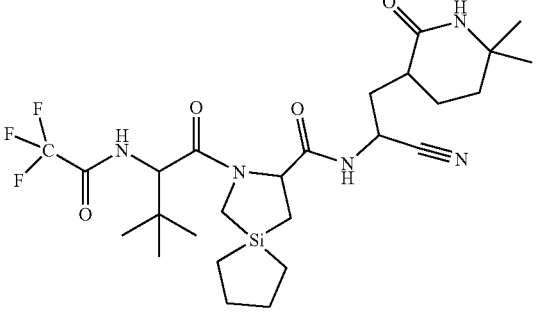 [SMILES: CC1(C)CCC(CC(C#N)NC(=O)C2C[Si]3(CCCC3)CN2C(=O)C(NC(=O)C(F)(F)F)C(C)(C)C)C(=O)N1] |
| 3125 | 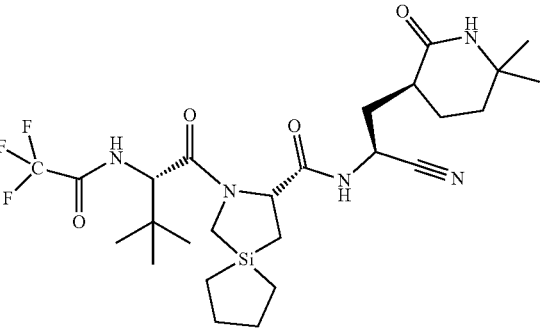 |
| 3126 | 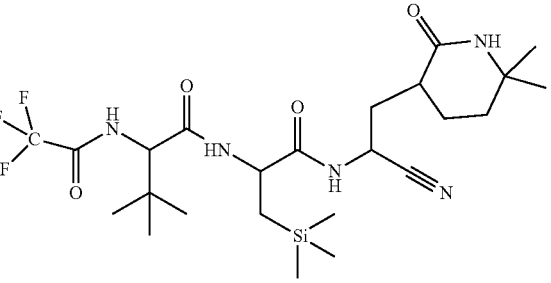 |
| 3127 | 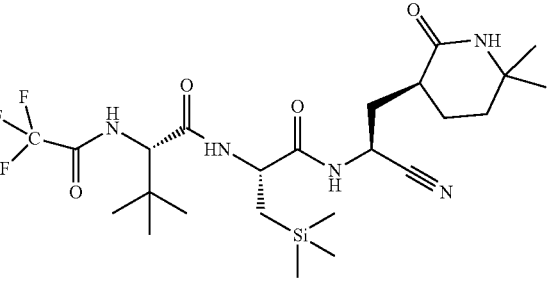 |

II. Methods

Another aspect of the disclosure provides methods of treating patients suffering from a viral infection, e.g., a coronaviral infection. In particular, in certain embodiments, the disclosure provides a method of treating the below medical indications comprising administering to a subject in need thereof a therapeutically effective amount of a compound described herein, such as a compound of Formula II, II-A, II-B, II-C, II-D-A, II-D-B, II-E-A, II-E-B, II-F, II-G, II-H-A, II-H-B, II-E, and II-I.

In certain embodiments, the disclosure provides a method of ameliorating or treating a viral infection in a patient in need thereof, comprising administering to the patient a therapeutically effective amount of any of the compounds described herein. In some embodiments, the viral infection is from a virus selected from the group consisting of an RNA virus, a DNA virus, a coronavirus, a papillomavirus, a pneumovirus, a picornavirus, an influenza virus, an adenovirus, a cytomegalovirus, a polyomavirus, a poxvirus, a flavivirus, an alphavirus, an ebola virus, a morbillivirus, an enterovirus (e.g., enterovirus 71 (EV71), an orthopneumovirus, a lentivirus, arenavirus, a herpes virus, and a hepatovirus. In certain embodiments, the viral infection is a coronavirus infection. In some embodiments, the viral infection is a coronavirus selected from the group consisting of: 229E alpha coronavirus, NL63 alpha coronavirus, OC43 beta coronavirus, HKU1 beta coronavirus, Middle East Respiratory Syndrome (MERS) coronavirus (MERS-CoV), severe acute respiratory syndrome (SARS) coronavirus (SARS-CoV), and SARS-CoV-2 (COVID-19). In embodiments, the viral infection is SARS-CoV-2.

In some embodiments, the viral infection is from a virus selected from the group consisting of calicivimses, MD145, murine norovirus, vesicular exanthema of swine virus, abbit hemorrhagic disease virus, porcine teschovirus, bovine coronavirus, feline infectious peritonitis virus, EV-68 virus, EV-71 virus, poliovirus, norovirus, human rhinovirus (HRV), hepatitis A virus (HAV) and foot-and-mouth disease virus (FMDV).

In embodiments, the viral infection is an arenavirus infection. In some embodiments, the arenavirus is selected from the group consisting of: Junin virus, Lassa virus, Lujo virus, Machupo virus, and Sabia virus. In some embodiments, the viral infection is an influenza infection. In some embodiments, the influenza is influenza H1N1, H3N2 or H5N1.

Another aspect of the disclosure provides methods of treating patients suffering from a viral infection, e.g., a noroviral infection. In some embodiments, the disclosure provides a method of treating a viral infection from a norovirus in a patient in need thereof, comprising administering to the patient a therapeutically effective amount of any of the compounds described herein.

Also provided herein, in certain embodiments, is a method of inhibiting transmission of a virus, a method of inhibiting viral replication, a method of minimizing expression of viral proteins, or a method of inhibiting virus release, comprising administering a therapeutically effective amount of a compound described herein to a patient suffering from the virus, and/or contacting an effective amount of a compound described herein with a virally infected cell. In some embodiments, the method further comprises administering another therapeutic. In some embodiments, the method further comprises administering an additional anti-viral therapeutic. In embodiments, the anti-viral therapeutic is selected from the group consisting of ribavirin, favipiravir, ST-193, oseltamivir, zanamivir, peramivir, danoprevir, ritonavir, remdesivir, cobicistat, elvitegravir, emtricitabine, tenofovir, tenofovir disoproxil, tenofovir alafenamide hemifumarate, abacavir, dolutegravir, efavirenz, elbasvir, ledipasvir, glecaprevir, sofosbuvir, bictegravir, dasabuvir, lamivudine, atazanavir, ombitasvir, lamivudine, stavudine, nevirapine, rilpivirine, paritaprevir, simeprevir, daclatasvir, grazoprevir, pibrentasvir, adefovir, amprenavir, ampligen, aplaviroc, anti-caprine antibody, balavir, cabotegravir, cytarabine, ecoliever, epigallocatechin gallate, etravirine, fostemsavir, gemcitabine, griffithsin, imunovir, indinavir, maraviroc, methisazone, MK-2048, nelfmavir, nevirapine, nitazoxanide, norvir, plerixafor, PRO 140, raltegravir, pyramidine, saquinavir, telbivudine, TNX-355, valacyclovir, VIR-576, and zalcitabine. In some embodiments, the another therapeutic is selected from the group consisting of protease inhibitors, fusion inhibitors, M2 proton channel blockers, polymerase inhibitors, 6-endonuclease inhibitors, neuraminidase inhibitors, reverse transcriptase inhibitor, aciclovir, acyclovir, protease inhibitors, arbidol, atazanavir, atripla, boceprevir, cidofovir, combivir, darunavir, docosanol, edoxudine, entry inhibitors, entecavir, famciclovir, fomivirsen, fosamprenavir, foscarnet, fosfonet, ganciclovir, ibacitabine, immunovir, idoxuridine, imiquimod, inosine, integrase inhibitor, interferons, lopinavir, loviride, moroxydine, nexavir, nucleoside analogues, penciclovir, pleconaril, podophyllotoxin, ribavirin, tipranavir, trifluridine, trizivir, tromantadine, truvada, valaciclovir, valganciclovir, vicriviroc, vidarabine, viramidine, and zodovudine. In embodiments, the additional anti-viral therapeutic is selected from the group consisting of lamivudine, an interferon alpha, a VAP anti-idiotypic antibody, enfuvirtide, amantadine, rimantadine, pleconaril, aciclovir, zidovudine, fomivirsen, a morpholino, a protease inhibitor, double-stranded RNA activated caspase oligomerizer (DRACO), rifampicin, zanamivir, oseltamivir, danoprevir, ritonavir, remdesivir, cobicistat, elvitegravir, emtricitabine, tenofovir, tenofovir disoproxil, tenofovir alafenamide hemifumarate, abacavir, dolutegravir, efavirenz, elbasvir, ledipasvir, glecaprevir, sofosbuvir, bictegravir, dasabuvir, lamivudine, atazanavir, ombitasvir, lamivudine, stavudine, nevirapine, rilpivirine, paritaprevir, simeprevir, daclatasvir, grazoprevir, pibrentasvir, adefovir, amprenavir, ampligen, aplaviroc, anti-caprine antibody, balavir, cabotegravir, cytarabine, ecoliever, epigallocatechin gallate, etravirine, fostemsavir, gemcitabine, griffithsin, imunovir, indinavir, maraviroc, methisazone, MK-2048, nelfmavir, nevirapine, nitazoxanide, norvir, plerixafor, PRO 140, raltegravir, pyramidine, saquinavir, telbivudine, TNX-355, valacyclovir, VIR-576, and zalcitabine.

Contemplated patients include not only humans, but other animals such as companion animals (e.g. dogs, cats), domestic animals (e.g. cow, swine), and wild animals (e.g. monkeys, bats, snakes).

Accordingly, in one embodiment, described herein is a method of ameliorating or treating a viral infection in a patient in need thereof, comprising administering to the patient a therapeutically effective amount of a compound described herein (e.g., a compound of Formulas II, II-A, II-B, II-C, II-D-A, II-D-B, II-E-A, II-E-B, II-F, II-G, II-H-A, II-H-B, II-E, and II-I, as described herein) or a pharmaceutically acceptable salt thereof.

Other contemplated methods of treatment include method of treating or ameliorating a virus infection condition or co-morbidity, by administering a compound disclosed herein to a subject.

Exemplary co-morbidities include lung diseases, cardiac disorders, endocrine disorders, respiratory disorders, hepatic disorders, skeletal disorders, psychiatric disorders, metabolic disorders, and reproductive disorders.

In some embodiments, the viral infection is from a virus selected from the group consisting of an RNA virus, a DNA virus, a coronavirus, a papillomavirus, a pneumovirus, a picornavirus, an influenza virus, an adenovirus, a cytomegalovirus, a polyomavirus, a poxvirus, a flavivirus, an alphavirus, an ebola virus, a morbillivirus, an enterovirus, an orthopneumovirus, a lentivirus, arenavirus, a herpes virus, and a hepatovirus. In some embodiments, the viral infection is a coronavirus infection. In some embodiments, the viral infection is a coronavirus selected from the group consisting of: 229E alpha coronavirus, NL63 alpha coronavirus, OC43 beta coronavirus, HKU1 beta coronavirus, Middle East Respiratory Syndrome (MERS) coronavirus (MERS-CoV), severe acute respiratory syndrome (SARS) coronavirus (SARS-CoV), and SARS-CoV-2 (COVID-19). In some embodiments, the viral infection is SARS-CoV-2. In some embodiments, the viral infection is an arenavirus infection. In some embodiments, the arenavirus is selected from the group consisting of: Junin virus, Lassa virus, Lujo virus, Machupo virus, and Sabia virus. In some embodiments, the viral infection is an influenza infection. In some embodiments, the influenza is influenza H1N1, H3N2 or H5N1. In some embodiments, the viral infection is a respiratory viral infection. In some embodiments, the viral infection is an upper respiratory viral infection or a lower respiratory viral infection. In some embodiments, the method further comprises administering another therapeutic.

In certain embodiments, the virus is selected from the group consisting of a retrovirus (e.g., human immunodeficiency virus (HIV), simian immunodeficiency virus (SIV), human T-cell lymphotropic virus (HTLV)-1, HTLV-2, HTLV-3, HTLV-4), Ebola virus, hepatitis A virus, hepatitis B virus, hepatitis C virus, a herpes simplex virus (HSV) (e.g., HSV-1, HSV-2, varicella zoster virus, cytomegalovirus), an adenovirus, an orthomyxovirus (e.g., influenza virus A, influenza virus B, influenza virus C, influenza virus D, togavirus), a flavivirus (e.g., dengue virus, Zika virus), West Nile virus, Rift Valley fever virus, an arenavirus, Crimean-Congo hemorrhagic fever virus, an echovirus, a rhinovirus, coxsackie virus, a coronavirus (e.g., Severe acute respiratory syndrome coronavirus 2 (SARS-CoV-2), coronavirus disease 2019 (COVID-19), a respiratory syncytial virus, a mumps virus, a rotavirus, measles virus, rubella virus, a parvovirus (e.g., an adeno-associated virus), a vaccinia virus, a variola virus, a molluscum virus, bovine leukemia virus, bovine diarrhea virus, a poliovirus, St. Louis encephalitis virus, Japanese encephalitis virus, a tick-borne encephalitis virus, Murray Valley virus, Powassan virus, Rocio virus, louping-ill virus, Banzi virus, Ilheus virus, Kokobera virus, Kunjin virus, Alfuy virus, a rabies virus, a polyomavirus (e.g., JC virus, BK virus), an alphavirus, and a rubivirus (e.g., rubella virus).

In certain embodiments, the disease or disorder is a viral infection, e.g., a disease or disorder selected from the group consisting of acquired immune deficiency syndrome (AIDS), HTLV-1 associated myelopathy/tropical spastic paraparesis, Ebola virus disease, hepatitis A, hepatitis B, hepatitis C, herpes, herpes zoster, acute varicella, mononucleosis, respiratory infections, pneumonia, influenza, dengue fever, encephalitis (e.g., Japanese encephalitis, St. Louis encephalitis, or tick-borne encephalitis such as Powassan encephalitis), West Nile fever, Rift Valley fever, Crimean-Congo hemorrhagic fever, Kyasanur Forest disease, Yellow fever, Zika fever, aseptic meningitis, myocarditis, common cold, lung infections, molloscum contagiosum, enzootic bovine leucosis, coronavirus disease 2019 (COVID-19), mumps, gastroenteritis, measles, rubella, slapped-cheek disease, smallpox, warts (e.g., genital warts), molluscum contagiosum, polio, rabies, and *Pityriasis rosea*.

In some embodiments, the virus is an RNA virus (having a genome that is composed of RNA). RNA viruses may be single-stranded RNA (ssRNA) or double-stranded RNA (dsRNA). RNA viruses have high mutation rates compared to DNA viruses, as RNA polymerase lacks proofreading capability (see Steinhauer D A, Holland J J (1987). *"Rapid evolution of RNA viruses". Annu. Rev. Microbiol.* 41: 409-33). In some embodiments, the RNA virus is a positive-strand RNA virus (e.g., a SARS-CoV virus, polio virus, Coxsackie virus, Enterovirus, Human rhinovirus, Foot/Mouth disease virus, encephalomyocarditis virus, Dengue virus, Zika virus, Hepatitis C virus, or New Castle Disease virus).

RNA viruses are classified by the type of genome (double-stranded, negative (−), or positive (+) single-stranded). Double-stranded RNA viruses contain a number of different RNA molecules, each coding for one or more viral proteins. Positive-sense ssRNA viruses utilize their genome directly as mRNA; ribosomes within the host cell translate mRNA into a single protein that is then modified to form the various proteins needed for viral replication. One such protein is RNA-dependent RNA polymerase (RNA replicase), which copies the viral RNA in order to form a double-stranded, replicative form. Negative-sense ssRNA viruses have their genome copied by an RNA replicase enzyme to produce positive-sense RNA for replication. Therefore, the virus comprises an RNA replicase enzyme. The resultant positive-sense RNA then acts as viral mRNA and is translated by the host ribosomes. In some embodiments, the virus is a dsRNA virus. In some embodiments, the virus is a negative ssRNA virus. In some embodiments, the virus is a positive ssRNA virus. In some embodiments, the positive ssRNA virus is a coronavirus.

SARS-CoV2, also sometimes referred to as the novel coronavirus of 2019 or 2019-nCoV, is a positive-sense single-stranded RNA virus. SARS-CoV-2 has four structural proteins, known as the S (spike), E (envelope), M (membrane), and N (nucleocapsid) proteins. The N protein holds the RNA genome together; the S, E, and M proteins form the viral envelope. Spike allows the virus to attach to the membrane of a host cell, such as the ACE2 receptor in human cells (Kruse R. L. (2020), Therapeutic strategies in an outbreak scenario to treat the novel coronavirus originating in Wuhan, China (version 2). *F*1000*Research,* 9:72). SARS-CoV2 is the highly contagious, causative viral agent of coronavirus disease 2019 (COVID19), a global pandemic.

In some embodiments, the virus is a DNA virus (having a genome that is composed of DNA). Exemplary DNA viruses include, without limitation, parvoviruses (e.g., adeno-associated viruses), adenoviruses, asfarviruses, herpesviruses (e.g., herpes simplex virus 1 and 2 (HSV-1 and HSV-2), Epstein-Barr virus (EBV), cytomegalovirus (CMV)), papillomaviruses (e.g., HPV), polyomaviruses (e.g., simian vacuolating virus 40 (SV40)), and poxviruses (e.g., vaccinia virus, cowpox virus, smallpox virus, fowlpox virus, sheeppox virus, myxoma virus). Exemplary RNA viruses include, without limitation, bunyaviruses (e.g., hantavirus), coronaviruses, flaviviruses (e.g., yellow fever virus, west Nile virus, dengue virus), hepatitis viruses (e.g., hepatitis A virus, hepatitis C virus, hepatitis E virus), influenza viruses (e.g., influenza virus type A, influenza virus type B, influenza virus type C), measles virus, mumps virus, calicivirus, noroviruses (e.g., Norwalk virus), poliovirus, respiratory syncytial virus (RSV), retroviruses (e.g., human immunodeficiency virus-1 (HIV-1)) and toroviruses.

The methods described herein may inhibit viral replication transmission, replication, assembly, or release, or minimize expression of viral proteins. In one embodiment, described herein is a method of inhibiting transmission of a virus, a method of inhibiting viral replication, a method of minimizing expression of viral proteins, or a method of inhibiting virus release, comprising administering a therapeutically effective amount of a compound described herein, or a pharmaceutically acceptable salt thereof, to a patient suffering from the virus, and/or contacting an effective amount of a compound described herein or a pharmaceutically acceptable salt thereof, with a virally infected cell.

Also described herein is a method of treating a respiratory disorder in a subject in need thereof, comprising administering to the patient a therapeutically effective amount of a compound described herein (e.g., a compound of Formulas II, II-A, II-B, II-C, II-D-A, II-D-B, II-E-A, II-E-B, II-F, II-G, II-H-A, II-H-B, II-E, and II-I, etc. described herein) or a pharmaceutically acceptable salt thereof. In embodiments, the respiratory disorder is selected from the group consisting of chronic obstructive pulmonary disease (COPD), asthma, fibrosis, chronic asthma, acute asthma, lung disease secondary to environmental exposures, acute lung infection, chronic lung infection, al antitrypsin disease, cystic fibrosis and an autoimmune disease. In some embodiments, the respiratory disorder is associated with a heart attack.

Also described herein is a method of treating a disorder associated with cathepsin (e.g. Cathepsin K) in a subject in need thereof, comprising administering to the patient a therapeutically effective amount of a compound described herein (e.g., a compound of Formulas II, II-A, II-B, II-C, II-D-A, II-D-B, II-E-A, II-E-B, II-F, II-G, II-H-A, II-H-B, II-E, and II-I, etc. described herein) or a pharmaceutically acceptable salt thereof. In some embodiments, the disorder is a cathepsin dependent condition or disease. In embodiments, the disorder is selected from the group consisting of breast cancer, pycnodysostosis, glioblastoma, osteoschlerosis, osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, atherosclerosis, obesity, glaucoma, chronic obstructive pulmonary disease, metastatic bone disease, hypercalcemia of malignancy, and multiple myeloma.

Compounds described herein, e.g., a compound of Formula II, II-A, II-B, II-C, II-D-A, II-D-B, II-E-A, II-E-B, II-F, II-G, II-H-A, II-H-B, II-E, II-I, etc. as defined herein, can be administered in combination with one or more additional therapeutic agents to treat a disorder described herein, such as an infection by a pathogen described herein, e.g., a virus, fungus, or protozoan. For clarity, contemplated herein are both a fixed composition comprising a disclosed compound and another therapeutic agent such as disclosed herein, and methods of administering, separately a disclosed compound and a disclosed therapeutic. For example, provided in the present disclosure is a pharmaceutical composition comprising a compound described herein, e.g., a compound of Formula I as defined herein, one or more additional therapeutic agents, and a pharmaceutically acceptable excipient. In some embodiments, a compound of Formula I as defined herein and one additional therapeutic agent is administered. In some embodiments, a disclosed compound as defined herein and two additional therapeutic agents are administered. In some embodiments, a disclosed compound as defined herein and three additional therapeutic agents are administered. Combination therapy can be achieved by administering two or more therapeutic agents, each of which is formulated and administered separately. For example, a compound of Formula II, II-A, II-B, II-C, II-D-A, II-D-B, II-E-A, II-E-B, II-F, II-G, II-H-A, II-H-B, II-E, II-I, etc. as defined herein and an additional therapeutic agent can be formulated and administered separately. Combination therapy can also be achieved by administering two or more therapeutic agents in a single formulation, for example a pharmaceutical composition comprising a compound of Formula I as one therapeutic agent and one or more additional therapeutic agents such as an antibiotic, a viral protease inhibitor, or an anti-viral nucleoside anti-metabolite. For example, a compound of Formula I as defined herein and an additional therapeutic agent can be administered in a single formulation. Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination using different sequencing of the component agents. For example, if agent X and agent Y are used in a combination, one could administer them sequentially in any combination one or more times, e.g., in the order X-Y-X, X-X-Y, Y-X-Y, Y-Y-X, X-X-Y-Y, etc.

In some embodiments, the one or more additional therapeutic agents that may be administered in combination with a compound provided herein can be an antibiotic, a viral protease inhibitor, an anti-viral anti-metabolite, a lysosomotropic agent, a M2 proton channel blocker, a polymerase inhibitor (e.g., EIDD-2801, which is also known as MOLNUPIRAVIR), aneuraminidase inhibitor, a reverse transcriptase inhibitor, a viral entry inhibitor, an integrase inhibitor, interferons (e.g., types I, II, and III), or a nucleoside analogue. In some embodiments, the one or more additional therapeutic agents that may be administered in combination with a compounds provided herein can be a steroid (e.g., corticosteroids, such as bethamethasone, prednisone, prednisolone, triamcinolone, methylprednisolone, dexamethasone; mineralocorticoid such as fludrocortisone; glucocorticoids, such as hydrocortisone, cortisone, bethamethasone, prednisone, prednisolone, triamcinolone, dexamethasone; vitamin D such as dihydrotachysterol; androgens such as apoptone, oxandrolone, oxabolone, testosterone, nandrolone (also known as anabolic steroids), oestrogens such as diethylstilbestrol, progestins such as danazol, norethindrone, medroxyprogesterone acetate, 17-Hydroxyprogesterone caproate; and progestins such as mifepristone and gestrinone) or an immunomodulator (e.g., 6Mercaptopurine, 6MP, Alferon N, anakinra, Arcalyst, Avonex, AVOSTARTGRIP, Bafiertam, Berinert, Betaseron, BG-12, C1 esterase inhibitor recombinant, C1 inhibitor human, Cinryze, Copaxone, dimethyl fumarate, diroximel fumarate, ecallantide, emapalumab, emapalumab-lzsg, Extavia, fingolimod, Firazyr, Gamifant, Gilenya, glatiramer, Glatopa, Haegarda, icatibant, Infergen, interferon alfa n3, interferon alfacon 1, interferon beta 1a, interferon beta 1b, Kalbitor, Kineret, mercaptopurine, monomethyl fumarate, peginterferon beta-1a, Plegridy, Purinethol, Purixan, Rebif, Rebif Rebidose, remestemcel-L, rilonacept, ropeginterferon alfa 2b, Ruconest, Ryoncil, siltuximab, sutimlimab, Sylvant, Tecfidera, and Vumerity). In some embodiments, the one or more additional therapeutic agent is Cathepsin L. In some embodiments, the one or more additional therapeutic agent is dehydrodidemnin B (also known as Plitidepsin or APLIDIN) or Zotatifin (eFT226).

In some embodiments, methods described herein further comprise administering an additional anti-viral therapeutic. In some embodiments, the anti-viral therapeutic is selected from the group consisting of ribavirin, favipiravir, ST-193, oseltamivir, zanamivir, peramivir, danoprevir, ritonavir, remdesivir, cobicistat, elvitegravir, emtricitabine, tenofovir, tenofovir disoproxil, tenofovir alafenamide hemifumarate, abacavir, dolutegravir, efavirenz, elbasvir, ledipasvir, glecaprevir, sofosbuvir, bictegravir, dasabuvir, lamivudine, atazanavir, ombitasvir, lamivudine, stavudine, nevirapine, rilpivirine, paritaprevir, simeprevir, daclatasvir, grazoprevir, pibrentasvir, adefovir, amprenavir, ampligen, aplaviroc, anti-caprine antibody, balavir, cabotegravir, cytarabine, ecoliever, epigallocatechin gallate, etravirine, fostemsavir, gemcitabine, griffithsin, imunovir, indinavir, maraviroc, methisazone, MK-2048, nelfmavir, nevirapine, nitazoxanide, norvir, plerixafor, PRO 140, raltegravir, pyramidine, saquinavir, telbivudine, TNX-355, valacyclovir, VIR-576, and zalcitabine. In some embodiments, the another therapeutic is selected from the group consisting of protease inhibitors (e.g., nafamostat, camostat, gabexate, epsilon-aminocapronic acid and aprotinin), fusion inhibitors (e.g., BMY-27709, CL 61917, and CL 62554), M2 proton channel blockers (e.g., amantadine and rimantadine), polymerase inhibitors (e.g., 2-deoxy-2'fluoroguanosides (2'-fluoroGuo), 6-endonuclease inhibitors (e.g., L-735,822 and flutamide) neuraminidase inhibitors (e.g., zanamivir (Relenza), oseltamivir, peramivir and ABT-675 (A-315675), reverse transcriptase inhibitor (e.g., abacavir, adefovir, delavirdine, didanosine, efavirenz, emtricitabine, lamivudine, nevirapine, stavudine, tenofovir, tenofovir disoproxil, and zalcitabine), acyclovir, acyclovir, protease inhibitors (e.g., amprenavir, indinavir, nelfinavir, ritonavir, and saquinavir), arbidol, atazanavir, atripla, boceprevir, cidofovir, combivir, darunavir, docosanol, edoxudine, entry inhibitors (e.g., enfuvirtide and maraviroc), entecavir, famciclovir, fomivirsen, fosamprenavir, foscarnet, fosfonet, ganciclovir, ibacitabine, immunovir, idoxuridine, imiquimod, inosine, integrase inhibitor (e.g., raltegravir), interferons (e.g., types I, II, and III), lopinavir, loviride, moroxydine, nexavir, nucleoside analogues (e.g., aciclovir), penciclovir, pleconaril, podophyllotoxin, ribavirin, tipranavir, trifluridine, trizivir, tromantadine, truvada, valaciclovir, valganciclovir, vicriviroc, vidarabine, viramidine, and zodovudine. In some embodiments, the additional anti-viral therapeutic is selected from the group consisting of lamivudine, an interferon alpha, a VAP anti-idiotypic antibody, enfuvirtide, amantadine, rimantadine, pleconaril, aciclovir, zidovudine, fomivirsen, a morpholino, a protease inhibitor, double-stranded RNA activated caspase oligomerizer (DRACO), rifampicin, zanamivir, oseltamivir, danoprevir, ritonavir, remdesivir, cobicistat, elvitegravir, emtricitabine, tenofovir, tenofovir disoproxil, tenofovir alafenamide hemifumarate, abacavir, dolutegravir, efavirenz, elbasvir, ledipasvir, glecaprevir, sofosbuvir, bictegravir, dasabuvir, lamivudine, atazanavir, ombitasvir, lamivudine, stavudine, nevirapine, rilpivirine, paritaprevir, simeprevir, daclatasvir, grazoprevir, pibrentasvir, adefovir, amprenavir, ampligen, aplaviroc, anti-caprine antibody, balavir, cabotegravir, cytarabine, ecoliever, epigallocatechin gallate, etravirine, fostemsavir, gemcitabine, griffithsin, imunovir, indinavir, maraviroc, methisazone, MK-2048, nelfmavir, nevirapine, nitazoxanide, norvir, plerixafor, PRO 140, raltegravir, pyramidine, saquinavir, telbivudine, TNX-355, valacyclovir, VIR-576, and zalcitabine. In some embodiments, the another therapeutic is selected from the group consisting of quinine (optionally in combination with clindamycin), chloroquine, amodiaquine, artemisinin and its derivatives (e.g., artemether, artesunate, dihydroartemisinin, arteether), doxycycline, pyrimethamine, mefloquine, halofantrine, hydroxychloroquine, eflornithine, nitazoxanide, ornidazole, paromomycin, pentamidine, primaquine, pyrimethamine, proguanil (optionally in combination with atovaquone), a sulfonamide (e.g., sulfadoxine, sulfamethoxypyridazine), tafenoquine, tinidazole and a PPT1 inhibitor (including Lys05 and DC661). In some embodiments, the another therapeutic is an antibiotic. In some embodiments, the antibiotic is a penicillin antibiotic, a quinolone antibiotic, a tetracycline antibiotic, a macrolide antibiotic, a lincosamide antibiotic, a cephalosporin antibiotic, or an RNA synthetase inhibitor. In some embodiments, the antibiotic is selected from the group consisting of azithromycin, vancomycin, metronidazole, gentamicin, colistin, fidaxomicin, telavancin, oritavancin, dalbavancin, daptomycin, cephalexin, cefuroxime, cefadroxil, cefazolin, cephalothin, cefaclor, cefamandole, cefoxitin, cefprozil, ceftobiprole, cipro, Levaquin, floxin, tequin, avelox, norflox, tetracycline, minocycline, oxytetracycline, doxycycline, amoxicillin, ampicillin, penicillin V, dicloxacillin, carbenicillin, methicillin, ertapenem, doripenem, imipenem/cilastatin, meropenem, amikacin, kanamycin, neomycin, netilmicin, tobramycin, paromomycin, cefixime, cefdinir, cefditoren, cefoperazone, cefotaxime, ceftazidime, ceftibuten, ceftizoxime, ceftriaxone, cefoxotin, and streptomycin. In some embodiments, the antibiotic is azithromycin.

In some embodiments, the one or more additional therapeutic agents that may be administered in combination with a compound provided herein can be selected from the group consisting of ribavirin, favipiravir, ST-193, oseltamivir, zanamivir, peramivir, danoprevir, ritonavir, remdesivir, cobicistat, elvitegravir, emtricitabine, tenofovir, tenofovir disoproxil, tenofovir alafenamide hemifumarate, abacavir, dolutegravir, efavirenz, elbasvir, ledipasvir, glecaprevir, sofosbuvir, bictegravir, dasabuvir, lamivudine, atazanavir, ombitasvir, lamivudine, stavudine, nevirapine, rilpivirine, paritaprevir, simeprevir, daclatasvir, grazoprevir, pibrentasvir, adefovir, amprenavir, ampligen, aplaviroc, anti-caprine antibody, balavir, cabotegravir, cytarabine, ecoliever, epigallocatechin gallate, etravirine, fostemsavir, gemcitabine, griffithsin, imunovir, indinavir, maraviroc, methisazone, MK-2048, nelfmavir, nevirapine, nitazoxanide, norvir, plerixafor, PRO 140, raltegravir, pyramidine, saquinavir, telbivudine, TNX-355, valacyclovir, VIR-576, and zalcitabine.

In some embodiments, the compounds described herein (e.g. of Formula II, II-A, II-B, II-C, II-D-A, II-D-B, II-E-A, II-E-B, II-F, II-G, II-H-A, II-H-B, II-E, II-I, etc.) and pharmaceutically acceptable salts thereof may be used in combination with one or more other agents which may be useful in the prevention or treatment of respiratory disease, inflammatory disease, autoimmune disease, for example; antihistamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast.pranlukast), tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-ethylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents), suitable anti-infective agents including antibiotic agents, antifungal agents, anthelmintic agents, antimalarial agents, antiprotozoal agents and antituberculosis agents.

In some embodiments, the additional therapeutic agents can be kinase inhibitors including but not limited to erlotinib, gefitinib, neratinib, afatinib, osimertinib, lapatanib, crizotinib, brigatinib, ceritinib, alectinib, lorlatinib, everolimus, temsirolimus, abemaciclib, LEE011, palbociclib, cabozantinib, sunitinib, pazopanib, sorafenib, regorafenib, sunitinib, axitinib, dasatinib, imatinib, nilotinib, ponatinib, idelalisib, ibrutinib, Loxo 292, larotrectinib, and quizartinib.

In some embodiments, the additional therapeutic agents can be therapeutic anti-viral vaccines.

In some embodiments, the additional therapeutic agents can be immunomodulatory agents including but not limited to anti-PD-1 or anti-PDL-1 therapeutics including pembrolizumab, nivolumab, atezolizumab, durvalumab, BMS-936559, or avelumab, anti-TIM3 (anti-HAVcr2) therapeutics including but not limited to TSR-022 or MBG453, anti-LAG3 therapeutics including but not limited to relatlimab, LAG525, or TSR-033, anti-4-1BB (anti-CD37, anti-TNFRSF9), CD40 agonist therapeutics including but not limited to SGN-40, CP-870,893 or RO7009789, anti-CD47 therapeutics including but not limited to Hu5F9-G4, anti-CD20 therapeutics, anti-CD38 therapeutics, STING agonists including but not limited to ADU-S100, MK-1454, ASA404, or amidobenzimidazoles, anthracyclines including but not limited to doxorubicin or mitoxanthrone, hypomethylating agents including but not limited to azacytidine or decitabine, other immunomodulatory therapeutics including but not limited to epidermal growth factor inhibitors, statins, metformin, angiotensin receptor blockers, thalidomide, lenalidomide, pomalidomide, prednisone, or dexamethasone. In some embodiments, the additional therapeutic agent is a p2-adrenoreceptor agonist including, but not limited to, vilanterol, salmeterol, salbutamol.formoterol, salmefamol, fenoterol carmoterol, etanterol, naminterol, clenbuterol, pirbuterol.flerbuterol, reproterol, bambuterol, indacaterol, terbutaline and salts thereof, for example the xinafoate (1-hydroxy-2-naphthalenecarboxylate) salt of salmeterol, the sulphate salt of salbutamol or the fumarate salt of formoterol. In some embodiments, the additional therapeutic agent is an anticholinergic agent, including, but not limited to, umeclidinium (for example, as the bromide), ipratropium (for example, as the bromide), oxitropium (for example, as the bromide) and tiotropium (for example, as the bromide).

In particular, in certain embodiments, the disclosure provides a method of treating the above medical indications comprising administering a subject in need thereof a therapeutically effective amount of a compound described herein, such as a disclosed compound.

The term "boosting amount" or "boosting dose" is the amount of a compound needed to improve the pharmacokinetics of a second compound (or increase availability or exposure). The boosting amount or boosting dose may improve the pharmacokinetics (or increase availability or exposure) of the second compound to a level to therapeutic levels in a subject.

In one embodiment, the disclosure provides for a disclosed compound to be administered together with an antiviral therapeutic such as disclosed herein, and e.g., thereby boosting the dose of the anti-viral therapeutic or therapeutics. Such a boost combination may be used, e.g., as prophylactic or therapeutic treatment of a viral infection in a subject in need thereof. In one embodiment, the protease inhibitor is a compound described herein (e.g. of Formula II, II-A, II-B, II-C, II-D-A, II-D-B, II-E-A, II-E-B, II-F, II-G, IL-H-A, II-H-B, II-E, II-I, etc.).

III. Reversible or Irreversible Conjugates

In certain embodiments, provided herein are conjugates represented by Formula III:

Formula III wherein $Cys_{145}$ is cysteine at position 145 or equivalent active site cysteine on a CL or 3CL protease; IR is a viral protease inhibitor; and wherein the compound that forms the conjugate comprises a —CN warhead.

IV. Pharmaceutical Compositions and Kits

Another aspect of the disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this disclosure may be used in the form of a pharmaceutical preparation, for example, in solid, semisolid or liquid form, which contains one or more of the compound of the disclosure, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well-known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the disclosure provides enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methylacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present disclosure.

Advantageously, the disclosure also provides kits for use by a e.g. a consumer in need of 3CL inhibitor. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well-known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Also contemplated herein are methods and compositions that include a second active agent or administering a second active agent. For example, in addition to having a viral infection, a subject or patient can further have viral infection- or virus-related co-morbidities, i.e., diseases and other adverse health conditions associated with, exacerbated by, or precipitated by being infected by a virus. Contemplated herein are disclosed compounds in combination with at least one other agent that has previously been shown to treat these virus-related conditions.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as compounds of the disclosure.

$^1$H NMR spectra are recorded at ambient temperature using e.g., a Varian Unity Inova (400 MHz) spectrometer with a triple resonance 5 mm probe for Example compounds, and either a Bruker Avance DRX (400 MHz) spectrometer or a Bruker Avance DPX (300 MHz) spectrometer for Intermediate compounds. Chemical shifts are expressed in ppm relative to tetramethylsilane. The following abbreviations have been used: br=broad signal, s=singlet, d=doublet, dd=double doublet, dt=double triplet, ddd=double doublet, t=triplet, td=triple doublet, tdd=triple double doublet, q=quartet, m=multiplet.

Abbreviations

AcOH acetic acid
Boc tert-butoxycarbonyl protecting group
CbzCl benzyl chloroformate
DCE dichloroethane
DCM dichloromethane
DDQ 2,3-dichloro-5,6-dicyano-1,4-benzoquinone
DIEA N,N-diisopropylethylamine
DIPEA N,N-diisopropylethylamine
DMA dimethylacetamide
DMAP 4-dimethylaminopyridine
DMF dimethylformamide
EA ethyl acetate
EtOAc ethyl acetate
EDCI 1-ethyl-3-(3-dimethylaminopropyl)carbodiimide
EDTA ethylenediaminetetraacetic acid
EtOH ethanol
FA formic acid HATU (1-[bis(dimethylamino)methylene]-1H-1,2,3-tri-azolo[4,5-b]pyridinium 3-oxide hexafluorophosphate
HOBt hydroxybenzotirazole
LiHMDS lithium bis(trimethylsilyl)amide
MTBA 1-4-(3-Methyltriazeno)benzoic acid
MTBE methyl tert-butyl ether
MeOH methanol
MeCN acetonitrile
MS mass spectrometry
NMR nuclear magnetic resonance
PE petroleum ether
PMA phosphomolybdic acid
PMBCl p-methoxybenzyl chloride
Pht phthaloyl
PyBOP (benzotriazol-1-yloxytripyrrolidinophosphonium hexafluorophosphate)
t-BuLi tert-butyllithium
$T_3P$ propanephosphonic acid anhydride
TEA triethylamine
TFA trifluoroacetic acid
TFAA trifluoroacetic anhydride
THF tetrahydrofuran
TMSCN trimethylsilyl cyanide General Chemistry Exemplary compounds described herein are available by the general synthetic method illustrated in the Scheme below, including preparations of Intermediates and preparation of accompanying Examples.

Synthetic Scheme(s)

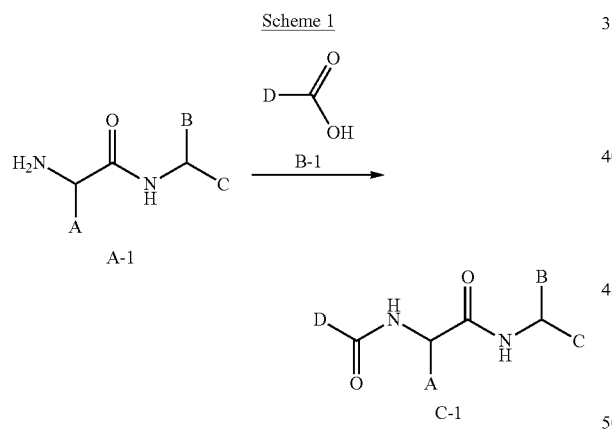

Scheme 1

Scheme 1 illustrates an exemplary preparation of C-1. Reacting a solution of amine A-1, and acid B-1 with a coupling agent such as $T_3P$, EDCI/HOBt, in the presence of a base such as TEA, DMAP and DIEA, and solvent such as DMF and DCM, affords C-1.

In Scheme 1, examples of A include a substituted or unsubstituted alkyl and a substituted or unsubstituted cycloalkyl, examples of B include a warhead moiety, such as cyano, aldehyde, hydroxymethylketone, ketoamide, heteroaryl-ketone, enone, and Michael acceptor warhead, examples of C include an alkyl substituted with a 4-, 5-, or 6-membered lactam, and examples of D include a substituted or unsubstituted bicyclic heteroaryl moiety. In Scheme 1, exemplary preparation of a cyano moiety at B include a dehydration of an amide to nitrile with a dehydration agent such as Burgess reagent.

Compounds of Table 1 have been prepared following general Scheme 1, which follows the examples described below, such as examples 19, 25, 27, 32, 39, and 41.

Example 1. Synthesis of Viral Protease Inhibitor Compound 103

Step 1: (2S)-2-[[(2S)-2-(1H-benzimidazole-2-carbonylamino)-4-methyl-pentanoyl]amino]-3-[(3S)-2-oxopyrrolidin-3-yl]propanoate

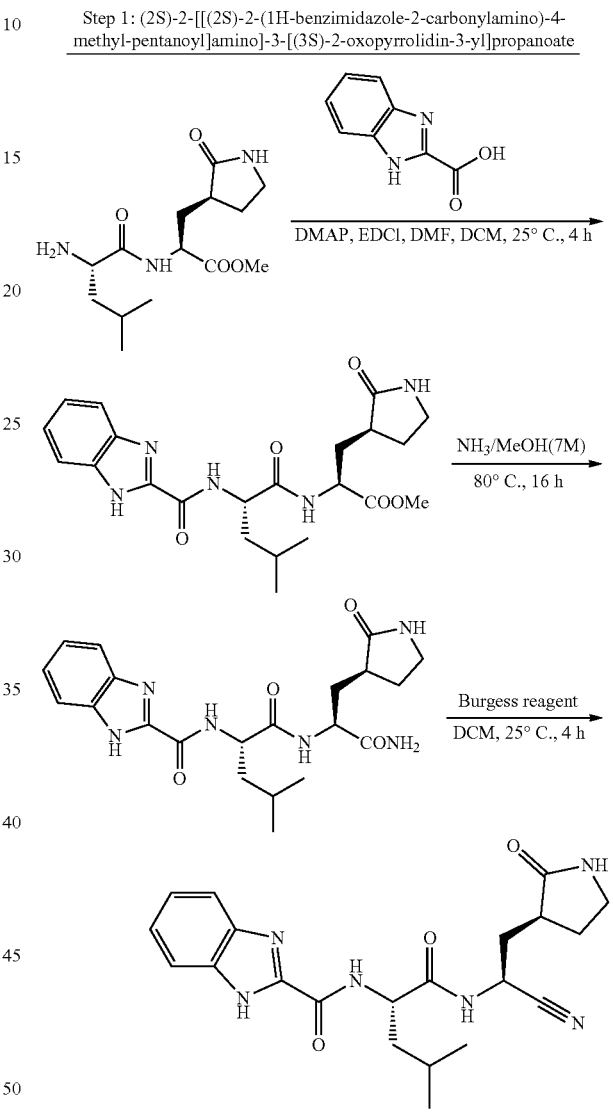

To a mixture of methyl (2S)-2-[[(2S)-2-amino-4-methyl-pentanoyl]amino]-3-[(3S)-2-oxopyrrolidin-3-yl]propanoate (200 mg, 483.81 umol, 1 eq, TFA) and 1H-benzimidazole-2-carboxylic acid (94.14 mg, 580.57 umol, 1.2 eq) in DCM (2 mL) was added EDCI (185.49 mg, 967.61 umol, 2 eq) and DMAP (118.21 mg, 967.61 umol, 2 eq). The mixture was added DMF (1 mL) and stirred at 25° C. for 4 h. The resulting mixture was diluted with $H_2O$ (20 mL) and extracted with DCM (10 mL*3). The combined organic layers were dried over $Na_2SO_4$, filtered and concentrated under reduced pressure to give a residue. The residue was purified by prep-TLC ($SiO_2$, DCM/MeOH=5/1), to give methyl (2S)-2-[[(2S)-2-(1H-benzimidazole-2-carbonylamino)-4-methyl-pentanoyl]amino]-3-[(3S)-2-oxopyrrolidin-3-yl]propanoate (150 mg, 338.22 umol) as a solid.

Step 2: N-[(1S)-3-methyl-1-[[(1S)-1-(nitrosomethyl)-2-[(3S)-2-oxopyrrolidin-3-yl]ethyl]carbamoyl]butyl]-1H-benzimidazole-2-carboxamide Methyl(2S)-2-[[(2S)-2-(1H-benzimidazole-2-carbonylamino)-4-methyl-pentanoyl]amino]-3-[(3S)-2-oxopyrrolidin-3-yl]propanoate (150 mg, 338.22 umol, 1 eq) was added NH₃/MeOH (7 M, 5 mL, 103.48 eq). The mixture was stirred at 80° C. for 16 h in a sealed tube. The reaction was concentrated in vacuo to dryness, give compound N-[(1S)-3-methyl-1-[[(1S)-1-(nitrosomethyl)-2-[(3S)-2-oxopyrrolidin-3-yl]ethyl]carbamoyl]butyl]-1H-benzimidazole-2-carboxamide (140 mg, crude) as a solid. The crude product was used directly in next step.

Step 3: N-[(1S)-1-[[(1S)-1-cyano-2-[(3S)-2-oxopyrrolidin-3-yl]ethyl]carbamoyl]-3-methyl-butyl]-1H-benzimidazole-2-carboxamide N-[(1S)-3-methyl-1-[[(1S)-1-(nitrosomethyl)-2-[(3S)-2-oxopyrrolidin-3-yl]ethyl]carbamoyl]butyl]-1H-benzimidazole-2-carboxamide (120.00 mg, 280.06 umol, 1 eq) in DCM (5 mL) was added Burgess reagent (150 mg, 629.45 umol, 2.25 eq). The mixture was stirred at 25° C. for 4 h. The reaction was blow-dried under N₂. The residue was purified by prep-HPLC (column: Waters Xbridge Prep OBD C18 150*40 mm*10 um; mobile phase: [water (10 mM NH4HCO3)-ACN]; B %: 20%-40%, 8 min), give N-[(1S)-1-[[(1S)-1-cyano-2-[(3S)-2-oxopyrrolidin-3-yl]ethyl]carbamoyl]-3-methyl-butyl]-1H-benzimidazole-2-carboxamide (40 mg, 97.45 umol) was obtained as a solid. MS (ESI) m/z 411.1 [M+H]⁺, ¹H NMR (400 MHz, DMSO-d₆) δ ppm 13.11 (br s, 1H), 8.97-8.81 (m, 2H), 7.90-7.64 (m, 2H), 7.54 (br s, 1H), 7.31 (br s, 2H), 5.08-4.93 (m, 1H), 4.62-4.43 (m, 1H), 3.19-3.05 (m, 2H), 2.44-2.29 (m, 1H), 2.23-2.05 (m, 2H), 1.91-1.50 (m, 5H), 0.91 (dd, J=6.3, 8.9 Hz, 6H).

Example 2. Synthesis of Viral Protease Inhibitor Compound 105

Step 1: (2s)-2-[[(2S)-4-methyl-2-(2-naphthylsulfonylamino)pentanoyl]amino]-3-[(3S)-2-oxopyrrolidin-3-yl]propanoate

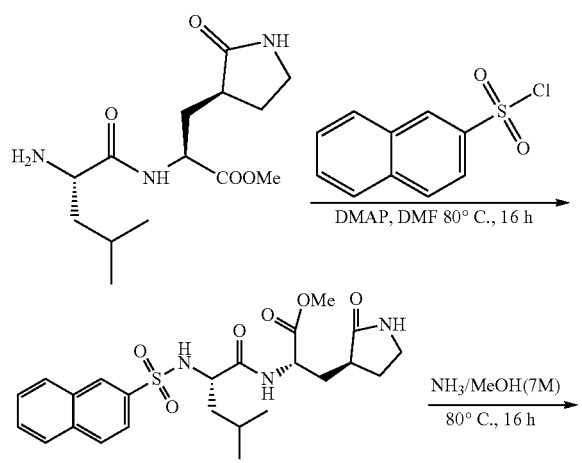

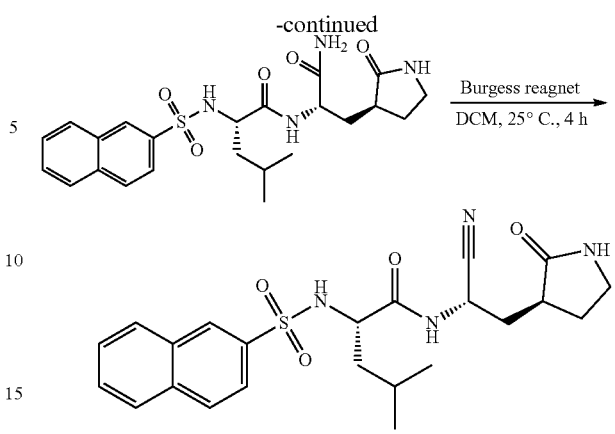

To a mixture of methyl (2S)-2-[[(2S)-2-amino-4-methyl-pentanoyl]amino]-3-[(3S)-2-oxopyrrolidin-3-yl]propanoate (150 mg, 501.06 umol, 1 eq) in DMF (5 mL) was added naphthalene-2-sulfonyl chloride (227.16 mg, 1.00 mmol, 2 eq) and DMAP (155.35 mg, 1.27 mmol, 2.54 eq) and stirred at 25° C. Then the reaction was stirred at 80° C. for 16 h. The reaction mixture was diluted with H₂O (20 mL) and extracted with EtOAc (10 mL*3). The combined organic layers were dried over Na₂SO₄, filtered and concentrated under reduced pressure to give a residue. The residue was purified by prep-TLC (SiO₂, DCM/MeOH=10/1). Give methyl (2S)-2-[[(2S)-4-methyl-2-(2-naphthylsulfonylamino)pentanoyl]amino]-3-[(3S)-2-oxopyrrolidin-3-yl]propanoate (70 mg, 142.98 umol) as an oil.

Step 2: (2S)-N-[(1S)-2-amino-2-oxo-1-[[(3S)-2-oxopyrrolidin-3-yl]methyl]ethyl]-4-methyl-2-(2-naphthylsulfonylamino)pentanamide To a mixture of methyl (2S)-2-[[(2S)-4-methyl-2-(2-naphthylsulfonylamino)pentanoyl]amino]-3-[(3S)-2-oxopyrrolidin-3-yl]propanoate (50 mg, 102.13 umol, 1 eq) was added NH₃/MeOH (7 M, 10 mL, 685.42 eq) and stirred at 80° C. for 16 h. The reaction was concentrated in vacuo to dryness to give the crude of (2S)-N-[(1S)-2-amino-2-oxo-1-[[(3S)-2-oxopyrrolidin-3-yl]methyl]ethyl]-4-methyl-2-(2-naphthylsulfonylamino)pentanamide (50 mg, crude) as an oil.

Step 3: (2S)-N-[(1S)-1-cyano-2-[(3S)-2-oxopyrrolidin-3-yl]ethyl]-4-methyl-2-(2-naphthylsulfonylamino)pentanamide (2S)-N-[(1S)-2-amino-2-oxo-1-[[(3S)-2-oxopyrrolidin-3-yl]methyl]ethyl]-4-methyl-2-(2-naphthylsulfonylamino)pentanamide (70 mg, 147.50 umol, 1 eq) in DCM (0.5 mL) was added Burgess reagent (79.00 mg, 331.52 umol, 2.25 eq). The mixture was stirred at 25° C. for 4 h. The reaction was blow-dried under N₂. The residue was purified by prep-HPLC: column: Waters Xbridge Prep OBD C18 150*40 mm*10 um; mobile phase: [water (10 mM NH₄HCO₃)-ACN]; B %: 25%-55%, 8 min, give compound (2S)-N-[(1S)-1-cyano-2-[(3S)-2-oxopyrrolidin-3-yl]ethyl]-4-methyl-2-(2-naphthylsulfonylamino)pentanamide (30 mg, 65.71 umol) as a solid. MS (ESI) m/z 457.1 [M+H]⁺. ¹H NMR (400 MHz, DMSO-d₆) δ ppm 8.81 (br d, J=7.5 Hz, 1H), 8.38 (s, 1H), 8.21 (br s, 1H), 8.12-8.03 (m, 2H), 8.00 (d, J=7.7 Hz, 1H), 7.82-7.72 (m, 1H), 7.71-7.56 (m, 3H), 4.64 (q, J=7.6 Hz, 1H), 3.78-3.67 (m, 1H), 3.09-3.01 (m, 1H), 3.00-2.89 (m, 1H), 2.08-1.96 (m, 1H), 1.90-1.78 (m, 1H), 1.71-1.60 (m, 1H), 1.58-1.33 (m, 4H), 1.31-1.19 (m, 1H), 0.78 (d, J=6.6 Hz, 3H), 0.63 (d, J=6.6 Hz, 3H).

Example 3. Synthesis of benzyl N-[(1S)-1-[[(1S)-1-cyano-2-[(3S)-2-oxopyrrolidin-3-yl]ethyl]carbamoyl]-3-methyl-butyl] carbamate Step 1: methyl (2S)-2-amino-3-[(3S)-2-oxopyrrolidin-3-yl]propanoate

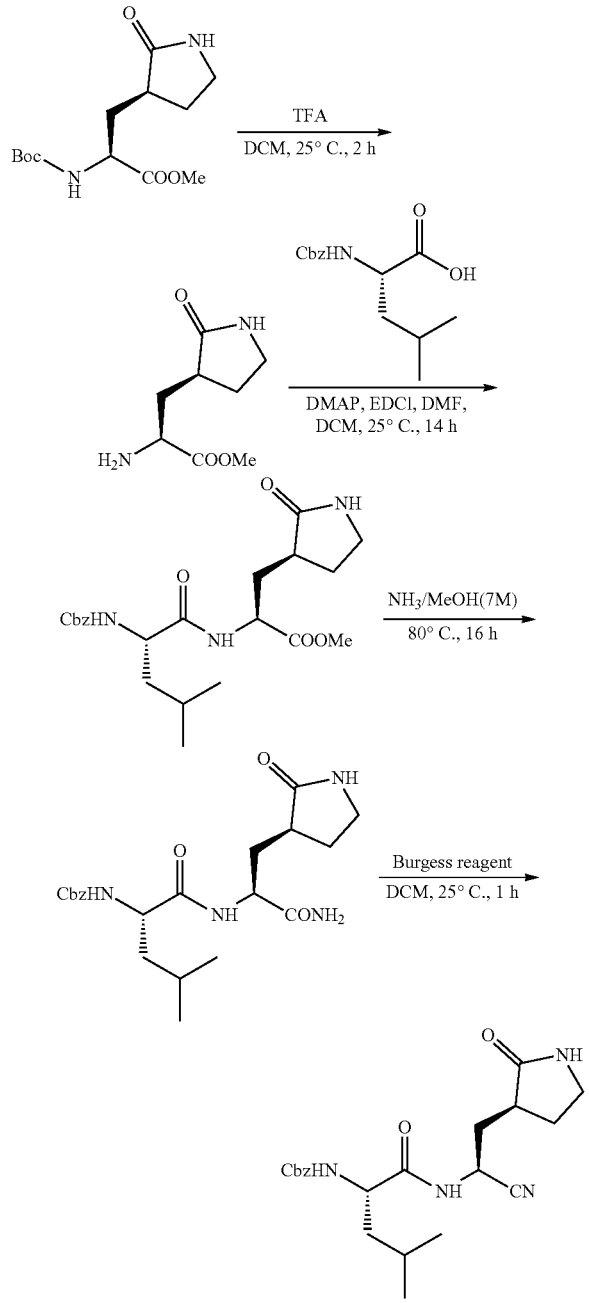

To a mixture of methyl (2S)-2-(tert-butoxycarbonylamino)-3-[(3S)-2-oxopyrrolidin-3-yl]propanoate (300 mg, 1.05 mmol, 1 eq) in DCM (5 mL) was added TFA (4.62 g, 40.52 mmol, 3 mL, 38.67 eq), then the mixture was stirred at 25° C. for 2 h. Once the reaction was completed, the reaction mixture was concentrated under reduced pressure to give a residue and used next step. Compound methyl (2S)-2-amino-3-[(3S)-2-oxopyrrolidin-3-yl]propanoate (180 mg, 918.33 umol) was obtained as a colorless oil. MS (ESI) m/z 187.1 [M+H]$^+$ Step 2: methyl (2S)-2-[[(2S)-2-(tert-butoxycarbonylamino)-4-methyl-pentanoyl]amino]-3-[(3S)-2-oxopyrrolidin-3-yl]propanoate To a mixture of methyl (2S)-2-amino-3-[(3S)-2-oxopyrrolidin-3-yl]propanoate (189.47 mg, 966.66 umol) and (2S)-2-(benzyloxycarbonylamino)-4-methyl-pentanoic acid (256.46 mg, 966.66 umol, 1 eq) in DCM (2 mL) was added DMAP (236.19 mg, 1.93 mmol, 2 eq) and EDCI (370.62 mg, 1.93 mmol, 2 eq). The mixture was added with DMF (1 mL) and stirred at 25° C. for 14 h. Once the reaction was completed, the reaction mixture was diluted with H$_2$O (50 mL) and extracted with DCM (30 mL*3). The combined organic layers were washed with brine (50 mL), dried over Na$_2$SO$_4$, filtered and concentrated under reduced pressure to give a residue. The residue was purified by column chromatography (SiO$_2$, petroleum ether/EtOAc=3/1 to 0/1) to get the compound methyl (2S)-2-[[(2S)-2-(benzyloxycarbonylamino)-4-methyl-pentanoyl]amino]-3-[(3S)-2-oxopyrrolidin-3-yl]propanoate (250 mg, 461.36 umol) as a solid. MS (ESI) m/z 434.3 [M+H]$^+$ Step 3: benzyl N-[(1S)-1-[[(1S)-2-amino-2-oxo-1-[[(3S)-2-oxopyrrolidin-3-yl]methyl]ethyl]carbamoyl]-3-methyl-butyl]carbamate Methyl (2S)-2-[[(2S)-2-(benzyloxycarbonylamino)-4-methyl-pentanoyl]amino]-3-[(3S)-2-oxopyrrolidin-3-yl]propanoate (200 mg, 369.09 umol, 1 eq) was added NH$_3$/MeOH (7 M, 58.14 mL, 1102.58 eq). The mixture was stirred at 80° C. for 16 h. Once the reaction was completed, the reaction mixture was concentrated under reduced pressure to give a residue and used directly next step. Compound benzyl N-[(1S)-1-[[(1S)-2-amino-2-oxo-1-[[(3S)-2-oxopyrrolidin-3-yl] methyl]ethyl]carbamoyl]-3-methyl-butyl]carbamate (150 mg, 322.59 umol) was obtained as a colorless oil.

Step 4: benzyl N-[(1S)-1-[[(1S)-1-cyano-2-[(3S)-2-oxopyrrolidin-3-yl]ethyl]carbamoyl]-3-methyl-butyl] carbamate To a mixture of benzyl N-[(1S)-1-[[(1S)-2-amino-2-oxo-1-[[(3S)-2-oxopyrrolidin-3-yl]methyl]ethyl] carbamoyl]-3-methyl-butyl]carbamate (150 mg, 179.22 umol, 1 eq) in DCM (5 mL) was added Burgess reagent (42.71 mg, 179.22 umol, 1 eq). The mixture was stirred at 25° C. for 1 h. Once the reaction was completed, the reaction mixture was concentrated under reduced pressure to give a residue. The residue was purified by neutral prep-HPLC (column: Waters Xbridge BEH C18 100*30 mm*10 um; mobile phase: [water (10 mM NH$_4$HCO$_3$)-ACN]; B %: 20%-50%, 8 min) to get the compound benzyl N-[(1S)-1-[[(1S)-1-cyano-2-[(3S)-2-oxopyrrolidin-3-yl]ethyl]carbamoyl]-3-methyl-butyl]carbamate (28 mg, 69.92 umol) as a solid. MS (ESI) m/z 401.1 [M+H]$^+$. $^1$H NMR (400 MHz, DMSO-d$_6$) δ ppm 8.84 (br d, J=7.9 Hz, 1H), 7.70 (s, 1H), 7.54 (br d, J=7.8 Hz, 1H), 7.41-7.24 (m, 5H), 5.02 (s, 2H), 4.97-4.88 (m, 1H), 4.07-3.91 (m, 1H), 3.20-2.94 (m, 2H), 2.38-2.22 (m, 1H), 2.22-1.98 (m, 2H), 1.85-1.26 (m, 5H), 0.87 (br dd, J=6.5, 11.2 Hz, 6H)

Example 4. Synthesis of Viral Protease Inhibitor Compound 131

Step 1: (2S)-2-[[(2S)-2-(1H-imidazo[4,5-b]pyridine-2-carbonylamino)-4-methyl-pentanoyl]amino]-3-[(3S)-2-oxopyrrolidin-3-yl]propanoate

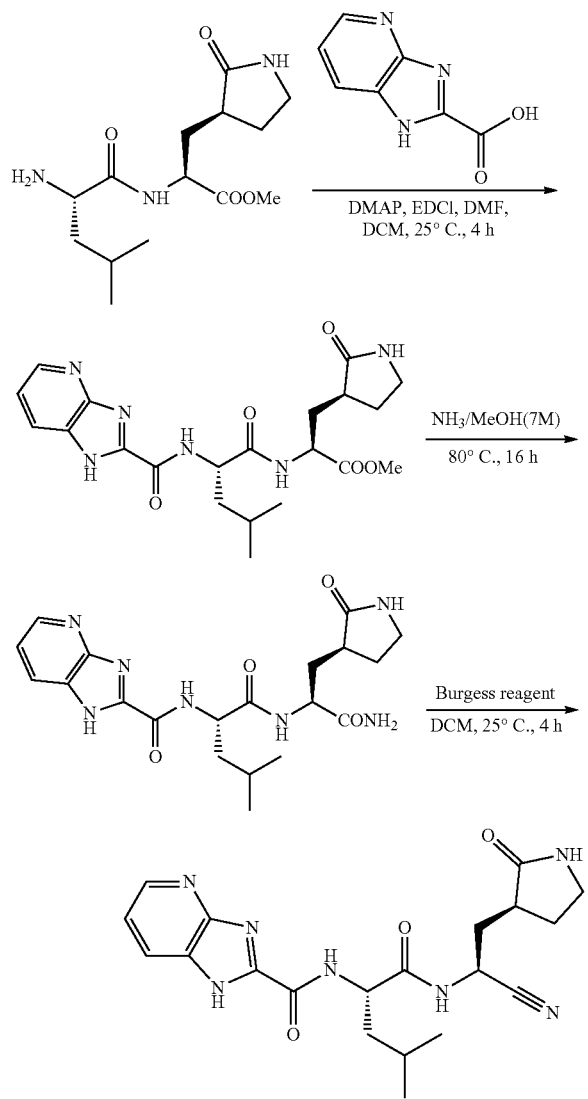

To a mixture of methyl (2S)-2-[[(2S)-2-amino-4-methyl-pentanoyl]amino]-3-[(3S)-2-oxopyrrolidin-3-yl]propanoate (250 mg, 604.76 umol, 1 eq, TFA) and 1H-imidazo[4,5-b]pyridine-2-carboxylic acid (118.39 mg, 725.71 umol, 1.2 eq) in DCM (4 mL) was added EDCI (231.86 mg, 1.21 mmol, 2 eq) and DMAP (147.77 mg, 1.21 mmol, 2 eq). The mixture was added with DMF (2 mL) and stirred at 25° C. for 4 h. The reaction mixture was diluted with H$_2$O (20 mL) and extracted with DCM (30 mL). The combined organic layers were dried over Na$_2$SO$_4$, filtered and concentrated under reduced pressure to give a residue. The residue was purified by prep-TLC (SiO$_2$, DCM/MeOH=5/1) to give compound methyl (2S)-2-[[(2S)-2-(1H-imidazo[4,5-b]pyridine-2-carbonylamino)-4-methyl-pentanoyl]amino]-3-[(3S)-2-oxopyrrolidin-3-yl]propanoate (100 mg, 224.98 umol) as a solid.

Step 2: N-[(1S)-1-[[(1S)-2-amino-2-oxo-1-[[(3S)-2-oxopyrrolidin-3-yl]methyl]ethyl]carbamoyl]-3-methyl-butyl]-1H-imidazo[4,5-b]pyridine-2-carboxamide To a mixture of methyl (2S)-2-[[(2S)-2-(1H-imidazo[4,5-b]pyridine-2-carbonylamino)-4-methyl-pentanoyl]amino]-3-[(3S)-2-oxopyrrolidin-3-yl]propanoate (100 mg, 224.98 umol, 1 eq) was added NH$_3$/MeOH (7 M, 27.54 mL, 856.77 eq) and stirred at 80° C. for 16 h. The reaction was concentrated in vacuo to dryness to give the crude of N-[(1S)-1-[[(1S)-2-amino-2-oxo-1-[[(3S)-2-oxopyrrolidin-3-yl]methyl]ethyl]carbamoyl]-3-methyl-butyl]-1H-imidazo[4,5-b]pyridine-2-carboxamide (90 mg, crude) as an oil.

Step 3: N-[(1S)-1-[[(1S)-1-cyano-2-[(3 S)-2-oxopyrrolidin-3-yl]ethyl]carbamoyl]-3-methyl-butyl]-1H-imidazo[4,5-b]pyridine-2-carboxamide N-[(1S)-1-[[(1S)-2-amino-2-oxo-1-[[(3S)-2-oxopyrrolidin-3-yl]methyl]ethyl]carbamoyl]-3-methyl-butyl]-1H-imidazo[4,5-b]pyridine-2-carboxamide (80 mg, 186.28 umol, 1 eq) in DCM (3 mL) was added Burgess reagent (100.00 mg, 419.62 umol, 2.25 eq). The mixture was stirred at 25° C. for 4 h. The reaction was blow-dried under N$_2$. The residue was purified by prep-HPLC (column: Waters Xbridge Prep OBD C18 150*40 mm*10 um; mobile phase: [water (10 mM NH4HCO3)-ACN]; B %: 10%-35%, 8 min) to give N-[(1S)-1-[[(1S)-1-cyano-2-[(3S)-2-oxopyrrolidin-3-yl]ethyl]carbamoyl]-3-methyl-butyl]-1H-imidazo[4,5-b]pyridine-2-carboxamide (25 mg, 60.76 umol) as a solid. MS (ESI) m/z 412.1 [M+H]$^+$. $^1$H NMR (400 MHz, DMSO-d$_6$) δ ppm 13.58 (br s, 1H), 9.29-8.96 (m, 1H), 8.89 (d, J=7.9 Hz, 1H), 8.49 (br s, 1H), 8.28-7.84 (m, 1H), 7.71 (s, 1H), 7.36 (dd, J=4.6, 8.2 Hz, 1H), 5.06-4.93 (m, 1H), 4.61-4.44 (m, 1H), 3.20-3.06 (m, 2H), 2.43-2.31 (m, 1H), 2.20-2.07 (m, 2H), 1.90-1.53 (m, 5H), 0.92 (dd, J=6.4, 9.5 Hz, 6H).

Example 5. Synthesis of Viral Protease Inhibitor Compound 121

Step 1: (2S)-2-(tert-butoxycarbonylamino)-3-[(3S)-2-oxopyrrolidin-3-yl]propanoic acid

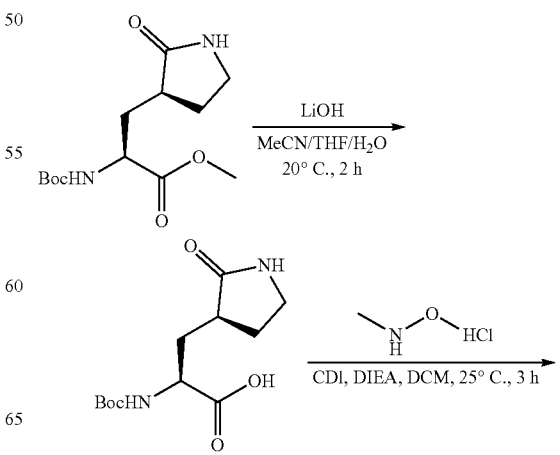

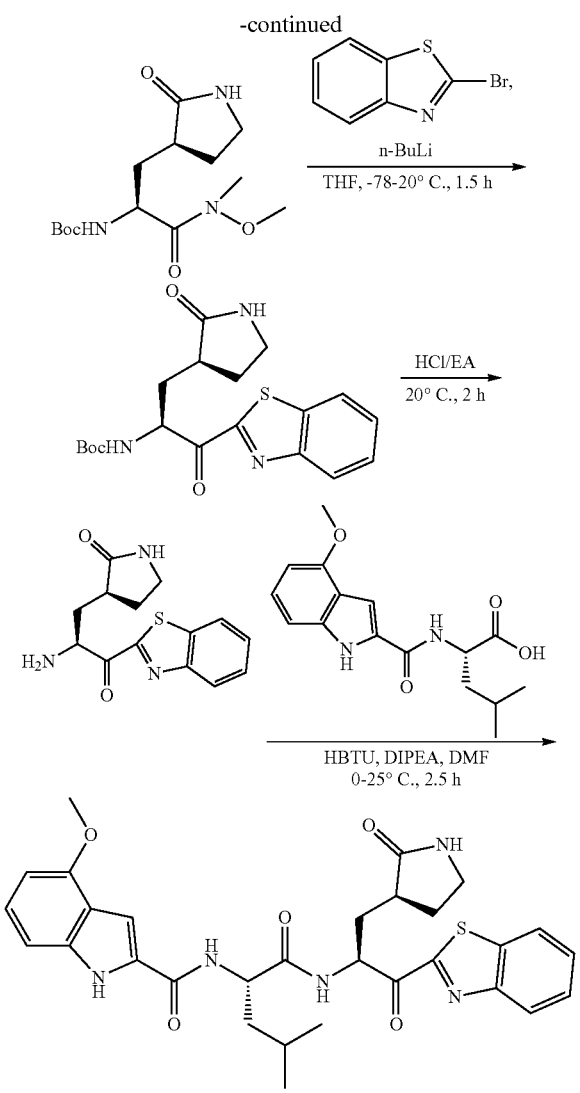

To a mixture of methyl (2S)-2-(tert-butoxycarbonylamino)-3-[(3S)-2-oxopyrrolidin-3-yl] propanoate (1.2 g, 3.77 mmol) in THF (3 mL), ACN (3 mL) and H₂O (3 mL) was added LiOH·H₂O (158.29 mg, 3.77 mmol, 1 eq). The mixture was stirred at 25° C. for 2 h. Once the reaction was completed, the solution was concentrated to give a residue, and then the residue was adjusted to pH-4 with HCl. The resulting residue was extracted with EtOAc (20 mL*3) and brine (20 mL), and then concentrated to give a residue compound (2S)-2-(tert-butoxycarbonylamino)-3-[(3S)-2-oxopyrrolidin-3-yl]propanoic acid (1 g, 3.31 mmol) was obtained as an oil. MS (ESI) m/z 217.1 [M+H−56]⁺.

Step 2: tert-butyl N-[(1S)-2-[methoxy(methyl) amino]-2-oxo-1-[[(3S)-2-oxopyrrolidin-3-yl]methyl] ethyl]carbamate To a mixture of (2S)-2-(tert-butoxycarbonylamino)-3-[(3S)-2-oxopyrrolidin-3-yl]propanoic acid (1.0 g, 3.31 mmol) in DCM (20 mL) was added CDI (535.94 mg, 3.31 mmol, 1 eq). The mixture was stirred at 0° C. for 30 min, then added with DIEA (512.61 mg, 3.97 mmol, 690.85 uL, 1.2 eq) and N,O-DIMETHYLHYDROXYLAMINE HYDROCHLORIDE (322.40 mg, 3.31 mmol, 1 eq). The resulting mixture was stirred at 25° C. for 3 h. Once the reaction was complete, the reaction mixture was diluted with H₂O (30 mL) and extracted with ethyl acetate (30 mL*3). The combined organic layers were washed with brine (30 mL), dried over Na₂SO₄, filtered and concentrated under reduced pressure to give a residue. The residue was purified by column chromatography (SiO₂, petroleum ether/EtOAc=5/1 to 0/1) to get the compound tert-butyl N-[(1S)-2-[methoxy(methyl)amino]-2-oxo-1-[[(3S)-2-oxopyrrolidin-3-yl]methyl]ethyl]carbamate (0.9 g, 2.57 mmol) which was obtained as an oil. MS (ESI) m/z 316.2 [M+H]⁺

Step 3: tert-butyl N-[(1S)-2-(1,3-benzothiazol-2-yl)-2-oxo-1-[[(3S)-2-oxopyrrolidin-3-yl]methyl]ethyl] carbamate To a mixture of 2-bromo-1,3-benzothiazole (458.22 mg, 2.14 mmol, 1.5 eq) in THF (20 mL) was added n-BuLi (2.5 M, 684.92 uL, 1.2 eq) in one portion at −78° C. under N₂. The mixture was stirred at −78° C. for 30 min, and then added with tert-butyl N-[(1S)-2-[methoxy(methyl)amino]-2-oxo-1-[[(3S)-2-oxopyrrolidin-3-yl]methyl]ethyl]carbamate (500 mg, 1.43 mmol) at −78° C. The resulting mixture was stirred for 1 hour, and then the reaction mixture was quenched by the addition of NH₄Cl (10 mL) at 0° C., and then stirred for 10 min at 0° C. The resulting mixture was diluted with water (100 mL) and extracted with EtOAc (50 mL*3). The combined organic layers were washed with brine (50 mL), dried over Na₂SO₄, filtered and concentrated under reduced pressure to give a residue. The residue was purified by MPLC (SiO₂, petroleum ether/EtOAc~MeOH=10/1 to 0/1) to get the compound tert-butyl N-[(1S)-2-(1,3-benzothiazol-2-yl)-2-oxo-1-[[(3S)-2-oxopyrrolidin-3-yl]methyl]ethyl]carbamate (150 mg, 346.63 umol) as a colorless oil. MS (ESI) m/z 390.1 [M+H]⁺

Step 4: (3S)-3-[(2S)-2-amino-3-(1,3-benzothiazol-2-yl)-3-oxo-propyl]pyrrolidin-2-one To a mixture of tert-butyl N-[(1S)-2-(1,3-benzothiazol-2-yl)-2-oxo-1-[[(3S)-2-oxopyrrolidin-3-yl] methyl]ethyl]carbamate (150 mg, 346.63 umol) was added HCl/EtOAc (4 M, 86.66 uL, 1 eq). The resulting mixture was stirred at 20° C. for 2 h, and then concentrated under reduced pressure to give a residue (3S)-3-[(2S)-2-amino-3-(1,3-benzothiazol-2-yl)-3-oxo-propyl]pyrrolidin-2-one (100 mg, crude) as an oil which was directly used in the next step. MS (ESI) m/z 290.1 [M+H]⁺

Step 5: N-[(1S)-1-[[(1S)-2-(1,3-benzothiazol-2-yl)-2-oxo-1-[[(3S)-2-oxopyrrolidin-3-yl]methyl]ethyl] carbamoyl]-3-methyl-butyl]-4-methoxy-1H-indole-2-carboxamide To a mixture of (2S)-2-[(4-methoxy-1H-indole-2-carbonyl)amino]-4-methyl-pentanoic acid (18.93 mg, 62.21 umol, 1 eq) in DMF (1 mL) was added 1-methylimidazole (25.54 mg, 311.04 umol, 24.79 uL, 5 eq) and [chloro(dimethylamino)methylene]-dimethyl-ammonium hexafluorophosphate (20.95 mg, 74.65 umol, 1.2 eq) at 0° C. The resulting mixture was stirred at 0° C. for 30 min, and then added with (3S)-3-[(2S)-2-amino-3-(1,3-benzothiazol-2-yl)-3-oxo-propyl]pyrrolidin-2-one (18 mg, 62.21 umol, 1 eq). The resulting mixture was stirred at 25° C. for 2 h. Once the reaction was completed, the reaction mixture was filtered and concentrated under reduced pressure to give a residue. The crude was purified by neutral prep-HPLC (column: Waters Xbridge BEH C18 100*30 mm*10 um; mobile phase: [water (10 mM NH4HCO3)-ACN]; B %: 35%-65%, 10 min) and SFC (column: DAICEL CHIRALCEL OX (250 mm*30 mm, 10 um); mobile phase: [0.1% NH3H2O MEOH]; B %: 50%-50%, 12 min) separation to get the compound N-[(1S)-1-[[(1S)-2-(1,3-benzothiazol-2-yl)-2-oxo-1-[[(3S)-2-oxopyrrolidin-3-yl]methyl]ethyl]carbamoyl]-3-methyl-butyl]-4-methoxy-1H-indole-2-carboxamide (8 mg, 13.48 umol) as a solid. MS (ESI) m/z 576.3 [M+H]$^+$.
$^1$H NMR (400 MHz, DMSO-d$_6$) δ=11.69 (s, 1H), 8.75-8.51 (m, 2H), 8.08 (d, J=7.9 Hz, 1H), 7.95 (d, J=8.2 Hz, 1H), 7.68 (s, 1H), 7.50 (t, J=7.4 Hz, 1H), 7.44-7.37 (m, 1H), 7.19-7.07 (m, 4H), 6.93 (d, J=8.2 Hz, 1H), 6.49 (d, J=7.7 Hz, 1H), 3.89 (s, 3H), 3.15-2.99 (m, 2H), 2.46-2.30 (m, 1H), 2.21-1.94 (m, 4H), 1.93-1.74 (m, 1H), 1.57-1.40 (m, 2H), 0.83-0.71 (m, 6H).

Example 6. Synthesis of Viral Protease Inhibitor Compound 185

Step 1: (S)-methyl 2-((S)-2-((tert-butoxycarbonyl)amino)-3-cyclohexylpropanamido)-3-((S)-2-oxopyrrolidin-3-yl)propanoate

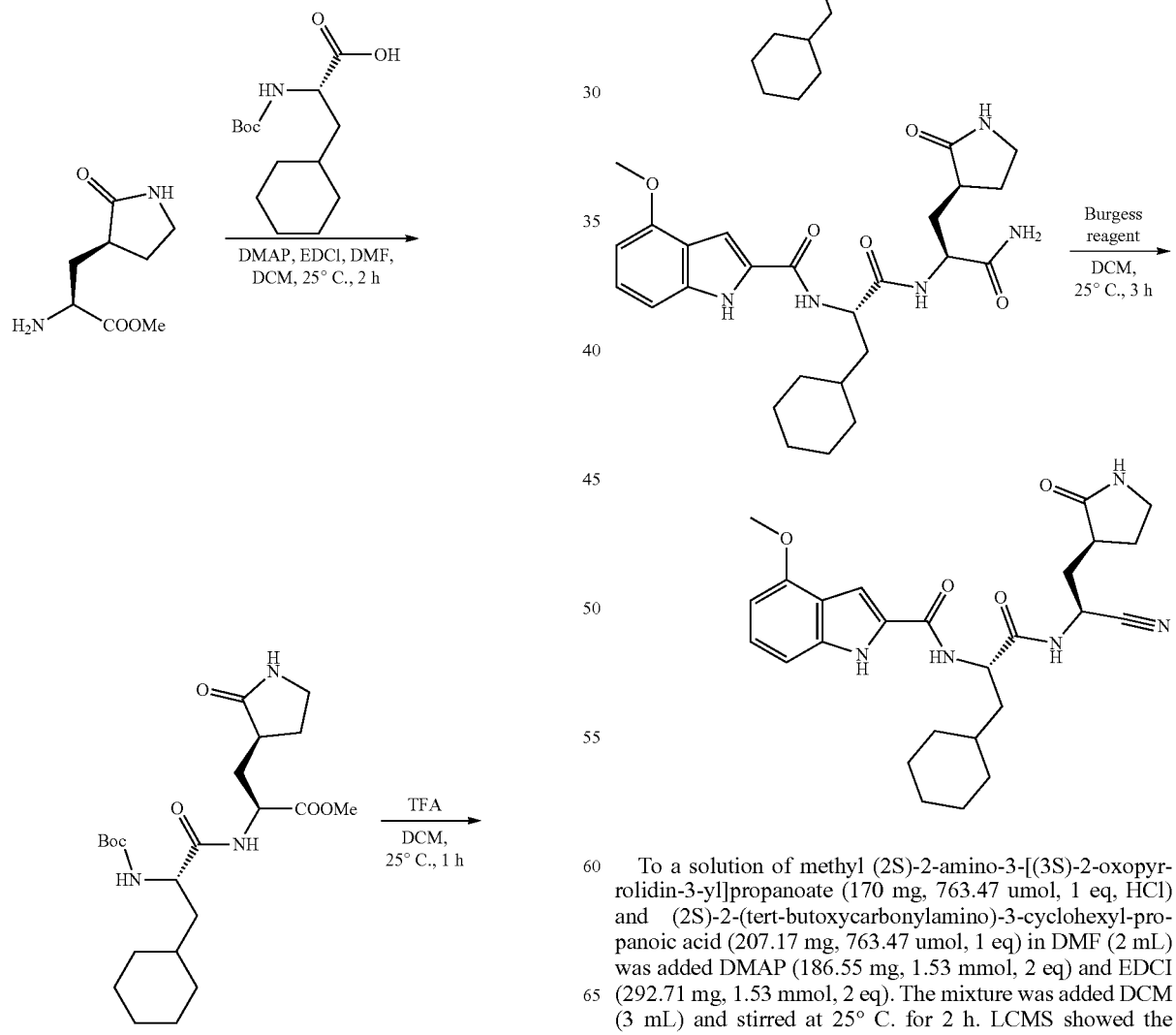

To a solution of methyl (2S)-2-amino-3-[(3S)-2-oxopyrrolidin-3-yl]propanoate (170 mg, 763.47 umol, 1 eq, HCl) and (2S)-2-(tert-butoxycarbonylamino)-3-cyclohexyl-propanoic acid (207.17 mg, 763.47 umol, 1 eq) in DMF (2 mL) was added DMAP (186.55 mg, 1.53 mmol, 2 eq) and EDCI (292.71 mg, 1.53 mmol, 2 eq). The mixture was added DCM (3 mL) and stirred at 25° C. for 2 h. LCMS showed the reaction was completed, and desired MS was observed. The reaction mixture was quenched by addition H₂O (30 mL) at 0° C., and then extracted with DCM (20 mL*3). The combined organic layers were washed with brine (10 mL), dried over Na₂SO₄, filtered and concentrated under reduced pressure to give a residue. The residue was purified by prep-TLC (SiO₂, petroleum ether/EtOAc=0/1) to get the product methyl (2S)-2-[[(2S)-2-(tert-butoxycarbonylamino)-3-cyclohexyl-propanoyl]amino]-3-[(3S)-2-oxopyrrolidin-3-yl]propanoate (250 mg, 568.77 umol, 74.50% yield) was obtained as a solid. MS (ESI) m/z 440.3 [M+H]⁺

Step 2: (S)-methyl 2-((S)-2-amino-3-cyclohexylpropanamido)-3-((S)-2-oxopyrrolidin-3-yl)propanoate A solution of methyl (2S)-2-[[(2S)-2-(tert-butoxycarbonylamino)-3-cyclohexyl-propanoyl]amino]-3-[(3S)-2-oxopyrrolidin-3-yl]propanoate (200 mg, 455.02 umol, 1 eq) in EtOAc (0.5 mL) was added drop-wise HCl/EtOAc (4 M, 2.00 mL, 17.58 eq) at 25° C. The mixture was stirred at 25° C. for 1 h. The reaction mixture was concentrated under reduced pressure to give a product methyl (2S)-2-[[(2S)-2-amino-3-cyclohexyl-propanoyl]amino]-3-[(3S)-2-oxopyrrolidin-3-yl]propanoate (150 mg, crude, HCl) was obtained as a solid and used directly next step. MS (ESI) m/z 340.1 [M+H]⁺

Step 3: ((S)-methyl 2-((S)-3-cyclohexyl-2-(4-methoxy-1H-indole-2-carboxamido)propanamido)-3-((S)-2-oxopyrrolidin-3-yl)propanoate A solution of 4-methoxy-1H-indole-2-carboxylic acid (99.18 mg, 518.77 umol, 1.3 eq) and methyl (2S)-2-[[(2S)-2-amino-3-cyclohexyl-propanoyl]amino]-3-[(3S)-2-oxopyrrolidin-3-yl]propanoate (150 mg, 399.05 umol, 1 eq, HCl) in DMF (2 mL) was added DMAP (97.50 mg, 798.11 umol, 2.0 eq) and EDCI (153.00 mg, 798.11 umol, 2 eq). The mixture was added DCM (4 mL) and stirred at 25° C. for 2 h. The reaction mixture was quenched by addition H₂O (20 mL) at 0° C., and then extracted with DCM (20 mL*3). The combined organic layers were washed with brine (20 mL), dried over Na₂SO₄, filtered and concentrated under reduced pressure to give a residue. The residue was purified by column chromatography (SiO₂, DCM:MeOH=1:0 to 10:1) to get a product methyl (2S)-2-[[(2S)-3-cyclohexyl-2-[(4-methoxy-1H-indole-2-carbonyl)amino]propanoyl]amino]-3-[(3S)-2-oxopyrrolidin-3-yl]propanoate (150 mg, 292.63 umol, 73.33% yield) was obtained as a solid. ¹H NMR (METHANOL-d₄, 400 MHz): δ ppm 7.26 (s, 1H), 7.09-7.20 (m, 1H), 7.02 (d, J=8.3 Hz, 1H), 6.51 (d, J=7.6 Hz, 1H), 4.66 (br dd, J=9.0, 6.3 Hz, 1H), 4.52-4.58 (m, 1H), 3.93 (s, 3H), 3.72 (s, 3H), 3.22-3.29 (m, 2H), 2.54-2.62 (m, 1H), 2.26-2.33 (m, 1H), 2.15-2.23 (m, 1H), 1.66-1.87 (m, 9H), 1.47-1.54 (m, 1H), 1.25-1.40 (m, 3H), 0.96-1.06 (m, 2H)

Step 4: N-((S)-1-(((S)-1-amino-1-oxo-3-((S)-2-oxopyrrolidin-3-yl)propan-2-yl)amino)-3-cyclohexyl-1-oxopropan-2-yl)-4-methoxy-1H-indole-2-carboxamide A solution of methyl (2S)-2-[[(2S)-3-cyclohexyl-2-[(4-methoxy-1H-indole-2-carbonyl)amino]propanoyl]amino]-3-[(3S)-2-oxopyrrolidin-3-yl]propanoate (150 mg, 292.63 umol, 1 eq) in ammonia (15.30 g, 898.39 mmol, 15.00 mL, 3070.07 eq) was heated at 80° C. for 12 hours in a sealed tube. The reaction mixture was concentrated under reduced pressure to get a product N-[(1S)-2-[[(1S)-2-amino-2-oxo-1-[[(3S)-2-oxopyrrolidin-3-yl]methyl]ethyl]amino]-1-(cyclohexylmethyl)-2-oxo-ethyl]-4-methoxy-1H-indole-2-carboxamide (140 mg, crude) was obtained as a solid. MS (ESI) m/z 498.2 [M+H]⁺ ¹H NMR (METHANOL-d₄, 400 MHz): δ ppm 7.27-7.34 (m, 1H), 7.13-7.20 (m, 1H), 7.05 (d, J=8.3 Hz, 1H), 6.53 (d, J=7.7 Hz, 1H), 4.62 (t, J=7.6 Hz, 1H), 4.42-4.51 (m, 1H), 3.95 (s, 3H), 3.22-3.30 (m, 2H), 2.53 (td, J=9.2, 4.5 Hz, 1H), 2.33 (ddd, J=9.2, 6.4, 3.4 Hz, 1H), 2.17 (ddd, J=14.1, 11.4, 4.6 Hz, 1H), 1.71-1.88 (m, 9H), 1.46-1.53 (m, 1H), 1.21-1.32 (m, 3H), 0.97-1.09 (m, 2H)

Step 5: N-((S)-1-(((S)-1-amino-1-oxo-3-((S)-2-oxopyrrolidin-3-yl)propan-2-yl)amino)-3-cyclohexyl-1-oxopropan-2-yl)-4-methoxy-1H-indole-2-carboxamide To a solution of N-[(1S)-2-[[(1S)-2-amino-2-oxo-1-[[(3S)-2-oxopyrrolidin-3-yl]methyl]ethyl]amino]-1-(cyclohexylmethyl)-2-oxo-ethyl]-4-methoxy-1H-indole-2-carboxamide (80 mg, 160.78 umol, 1 eq) in DCM (3 mL) was added Burgess reagent (114.94 mg, 482.33 umol, 3 eq), and then the resulting mixture was stirred at 25° C. for 3 h. The reaction mixture was concentrated under reduced pressure to give a residue. The residue was purified by neutral prep-HPLC to give a product N-[(1S)-2-[[(1S)-1-cyano-2-[(3S)-2-oxopyrrolidin-3-yl]ethyl]amino]-1-(cyclohexylmethyl)-2-oxo-ethyl]-4-methoxy-1H-indole-2-carboxamide (20.02 mg, 41.75 umol) was obtained as a solid. MS (ESI) m/z 480.1 [M+H]⁺.

Prep-HPLC condition: column: Waters Xbridge BEH C18 100*25 mm*5 um; mobile phase: [water (10 mM NH₄HCO₃)-ACN]; B %: 30%-60%, 10 min ¹H NMR (METHANOL-d₄, 400 MHz): δ ppm 7.28 (s, 1H), 7.11-7.18 (m, 1H), 7.02 (d, J=8.3 Hz, 1H), 6.51 (d, J=7.6 Hz, 1H), 5.05 (dd, J=10.1, 5.9 Hz, 1H), 4.56-4.61 (m, 1H), 3.93 (s, 3H), 3.22-3.30 (m, 2H), 2.55-2.66 (m, 1H), 2.23-2.40 (m, 2H), 1.65-1.94 (m, 9H), 1.41-1.52 (m, 1H), 1.17-1.36 (m, 3H), 0.94-1.10 (m, 2H).

Example 7. Synthesis of Viral Protease Inhibitor Compound 101

Step 1: Methyl (2S)-2-amino-3-[(3S)-2-oxopyrrolidin-3-yl]propanoate; hydrochloride

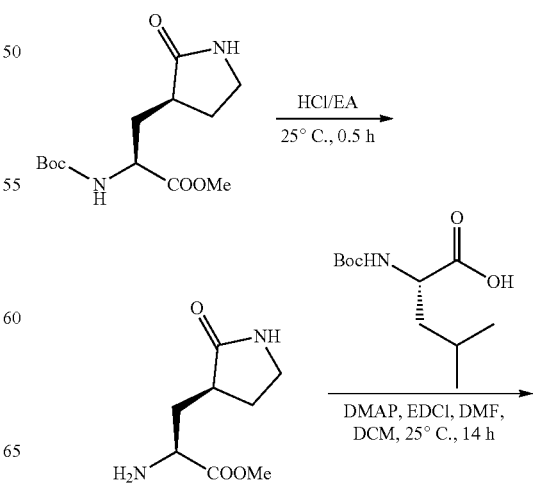

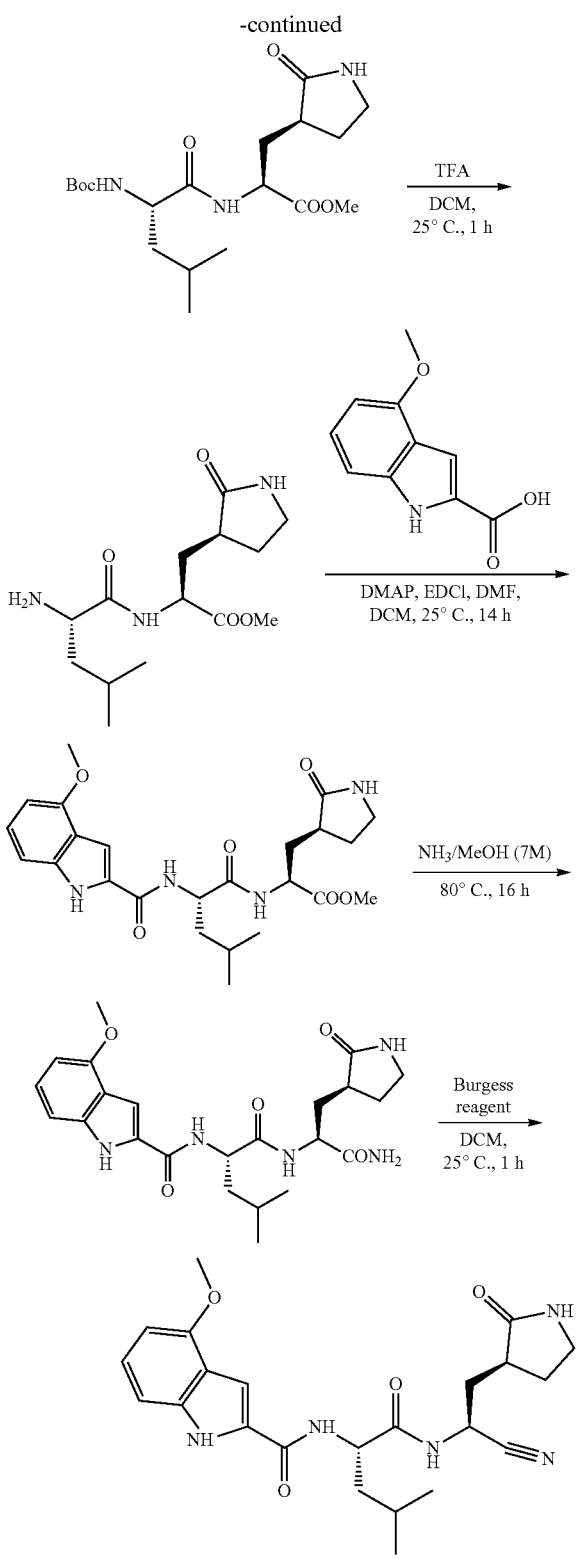

Methyl (2S)-2-(tert-butoxycarbonylamino)-3-[(3S)-2-oxopyrrolidin-3-yl]propanoate (500 mg, 1.75 mmol, 1 eq) was added HCl/EtOAc (4 M, 10 mL, 22.91 eq) at 25° C. The mixture was stirred at 25° C. for 0.5 h. The resulting mixture was concentrated under reduced pressure to give a product methyl (2S)-2-amino-3-[(3S)-2-oxopyrrolidin-3-yl]pro-panoate; hydrochloride (300 mg, 1.28 mmol, 73.29% yield, 95% purity) as a solid and used directly next step. MS (ESI) m/z 187.1 [M+H]+

Step 2: methyl (2S)-2-[[(2S)-2-(tert-butoxycarbonylamino)-4-methyl-pentanoyl]amino]-3-[(3S)-2-oxopyrrolidin-3-yl]propanoate To a mixture of methyl (2S)-2-amino-3-[(3S)-2-oxopyrrolidin-3-yl]propanoate; hydrochloride (157.89 mg, 673.65 umol, 95% purity, 1 eq) and (2S)-2-(tert-butoxycarbonylamino)-4-methyl-pentanoic acid (155.81 mg, 673.65 umol, 1 eq) in DMF (2 mL) was added EDCI (258.28 mg, 1.35 mmol, 2 eq) and DMAP (164.60 mg, 1.35 mmol, 2 eq). The mixture was added DCM (3 mL) and stirred at 25° C. for 14 h. The resulting mixture was diluted with H2O (50 mL) and extracted with DCM (30 mL*3). The combined organic layers were washed with brine, dried over Na2SO4, filtered and concentrated under reduced pressure to give a residue. The residue was purified by column chromatography (SiO2, petroleum ether/EtOAc=3/1 to 1/1) to get the product methyl (2S)-2-[[(2S)-2-(tert-butoxycarbonylamino)-4-methyl-pentanoyl]amino]-3-[(3S)-2-oxopyrrolidin-3-yl]propanoate (250 mg, 500.65 umol, 74.32% yield, 80% purity) was obtained as a solid. MS (ESI) m/z 400.3 [M+H]+

Step 3: (2S)-2-amino-N-[(1S)-1-cyano-2-[(3S)-2-oxopyrrolidin-3-yl]ethyl]-4-methyl-pentanamide tert-butylN-[(1S)-1-[[(1S)-1-cyano-2-[(3S)-2-oxopyrrolidin-3-yl]ethyl]carbamoyl]-3-methyl-butyl] carbamate (200 mg, 491.19 umol, 90% purity, 1 eq) in DCM (5 mL) was added TFA (770.00 mg, 6.75 mmol, 0.5 mL, 13.75 eq) at 25° C. The mixture was stirred at 25° C. for 1 h. The resulting mixture was concentrated under reduced pressure to give a product (2S)-2-amino-N-[(1S)-1-cyano-2-[(3S)-2-oxopyrrolidin-3-yl]ethyl]-4-methyl-pentanamide (120 mg, 405.50 umol, 82.55% yield, 90% purity) as an oil and used directly next step. MS (ESI) m/z 300.2 [M+H]+

Step 4: methyl(2S)-2-[[(2S)-2-[(4-methoxy-1H-indole-2-carbonyl)amino]-4-methyl-pentanoyl]amino]-3-[(3S)-2-oxopyrrolidin-3-yl]propanoate To a mixture of 4-methoxy-1H-indole-2-carboxylic acid (120 mg, 627.67 umol, 1 eq) and methyl (2S)-2-[[(2S)-2-amino-4-methyl-pentanoyl]amino]-3-[(3S)-2-oxopyrrolidin-3-yl]propanoate (208.78 mg, 627.67 umol, 90% purity, 1 eq) in DCM (1 mL) was added EDCI (240.65 mg, 1.26 mmol, 2 eq) and DMAP (153.36 mg, 1.26 mmol, 2 eq). The mixture was added DMF (0.5 mL) and stirred at 25° C. for 14 h. The resulting mixture was diluted with H2O (50 mL) and extracted with DCM (30 mL*3). The combined organic layers were washed with brine (50 mL), dried over Na2SO4, filtered and concentrated under reduced pressure to give a residue. The residue was purified by column chromatography (SiO2, petroleum ether/EtOAc=3/1 to 0/1) to get the compound methyl(2S)-2-[[(2S)-2-[(4-methoxy-1H-indole-2-carbonyl)amino]-4-methyl-pentanoyl] amino]-3-[(3S)-2-oxopyrrolidin-3-yl]propanoate (160 mg, 304.74 umol, 48.55% yield, 90% purity) as a solid. MS (ESI) m/z 473.3 [M+H]+

Step 5: N-[(1S)-1-[[(1S)-2-amino-2-oxo-1-[[(3S)-2-oxopyrrolidin-3-yl]methyl]ethyl]carbamoyl]-3-methyl-butyl]-4-methoxy-1H-indole-2-carboxamide methyl (2S)-2-[[(2S)-2-[(4-methoxy-1H-indole-2-carbonyl)amino]-4-methyl-pentanoyl]amino]3-[(3S)-2-oxopyrrolidin-3-yl]propanoate (180 mg, 342.83 umol, 90% purity, 1 eq) was added NH₃/MeOH (7 M, 54.00 mL, 1102.58 eq), The mixture was stirred at 80° C. for 16 h. The resulting mixture was concentrated under reduced pressure to give a residue N-[(1S)-1-[[(1S)-2-amino-2-oxo-1-[[(3S)-2-oxopyr-rolidin-3-yl]methyl]ethyl]carbamoyl]-3-methyl-butyl]-4-methoxy-1H-indole-2-carboxamide (130 mg, 255.73 umol, 74.59% yield, 90% purity) as an oil. MS (ESI) m/z 458.3 [M+H]⁺

1H NMR (400 MHz, METHANOL-d4) δ ppm 0.97-1.02 (dd, J=14.55, 6.11 Hz, 6H) 1.74-1.82 (m, 5H) 2.15 (ddd, J=14.03, 11.34, 4.58 Hz, 1H) 2.25-2.37 (m, 1H) 2.52 (ddt, J=13.82, 9.41, 4.71, 4.71 Hz, 1H) 3.17-3.29 (m, 2H) 3.90 (s, 3H) 4.46 (dd, J=11.25, 4.16 Hz, 1H) 4.60 (dd, J=9.66, 5.01 Hz, 1H) 6.50-6.52 (d, J=7.70 Hz, 1H) 7.02-7.04 (d, J=8.31 Hz, 1H) 7.15-7.17 (m, 1H) 7.28-7.29 (d, J=0.73 Hz, 1H)

Step 6: N-[(1S)-1-[[(1S)-1-cyano-2-[(3S)-2-oxopyr-rolidin-3-yl]ethyl]carbamoyl]-3-methyl-butyl]-4-methoxy-1H-indole-2-carboxamide To a mixture of N-[(1S)-1-[[(1S)-2-amino-2-oxo-1-[[(3S)-2-oxopyrrolidin-3-yl]methyl]ethyl] carbamoyl]-3-methyl-butyl]-4-methoxy-1H-indole-2-carboxamide (100 mg, 196.71 umol, 90% purity, 1 eq) in DCM (4 mL) was added Burgess reagent (93.75 mg, 393.42 umol, 2 eq). The mixture was stirred at 25° C. for 1 h. The resulting mixture was concentrated under reduced pressure to give a residue. The residue was purified by neutral prep-HPLC to get the product N-[(1S)-1-[[(1S)-1-cyano-2-[(3S)-2-oxopyrrolidin-3-yl]ethyl]carbamoyl]-3-methyl-butyl]-4-methoxy-1H-indole-2-carboxamide (23 mg, 49.50 umol, 25.16% yield, 94.59% purity) as a solid. MS (ESI) m/z 440.1 [M+H]⁺.
Prep-HPLC Condition:
column: Waters Xbridge BEH C18 100*30 mm*10 um; mobile phase: [water (10 mM NH4HCO3)-ACN]; B %: 27%-57%, 10 min 1H NMR (400 MHz, DMSO-d6) δ ppm 0.88-0.94 (m, 6H) 1.67-1.74 (m, 5H) 2.11-2.13 (m, 2H) 2.14-2.34 (m, 1H) 3.09-3.14 (m, 2H) 3.88 (s, 3H) 4.36-4.57 (m, 1H) 4.90-5.00 (m, 1H) 6.49-6.51 (d, J=7.58 Hz, 1H) 6.99-7.01 (m, 2H) 7.38 (s, 1H) 7.70 (s, 1H) 8.45-8.47 (br d, J=7.70 Hz, 1H) 8.89-8.91 (br d, J=7.95 Hz, 1H) 11.57 (br s, 1H)

Example 8. Synthesis of Viral Protease Inhibitor Compound 593

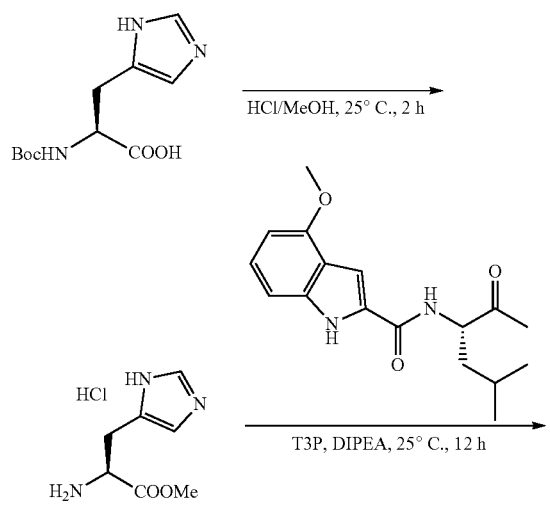

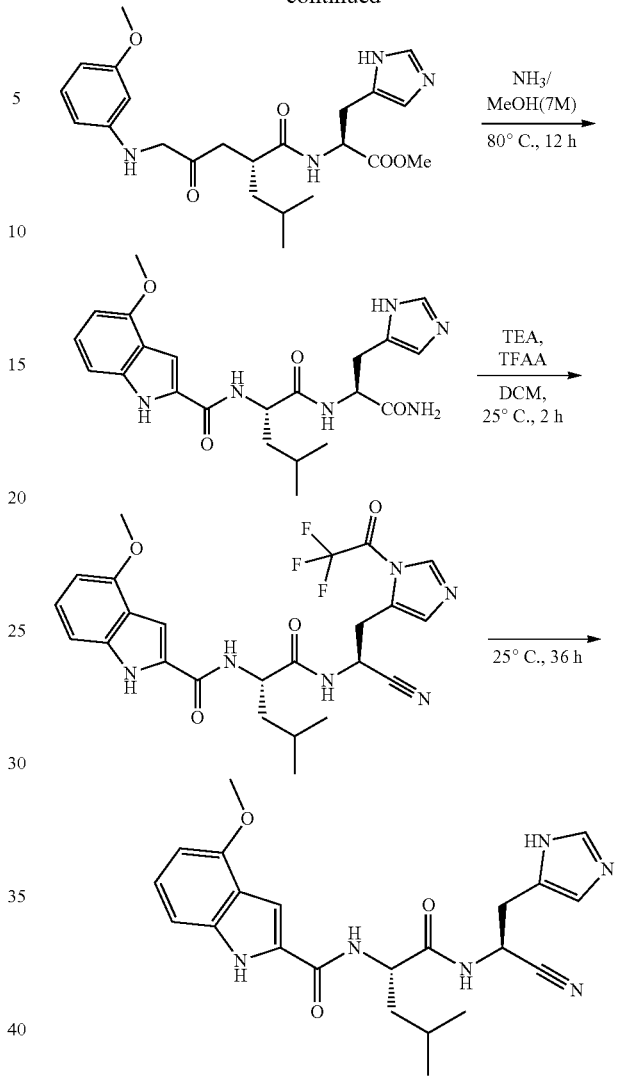

To the solution of (2S)-2-(tert-butoxycarbonylamino)-3-(1H-imidazol-5-yl)propanoic acid (0.5 g, 1.96 mmol, 1 eq) in MeOH (0.6 mL) was added HCl/MeOH (4 M, 4.90 mL, 10 eq) at 25° C. The reaction mixture was stirred at 25° C. for 12 h. The reaction mixture was concentrated to get the product. Methyl (2S)-2-amino-3-(1H-imidazol-5-yl) propanoate (400 mg, crude, HCl) was obtained as a solid and used directly next step. MS (ESI) m/z 170.1 [M+H]⁺

Step 2: methyl (2S)-3-(1H-imidazol-5-yl)-2-[[(2S)-2-[(4-methoxy-1H-indole-2-carbonyl)amino]-4-methyl-pentanoyl]amino]propanoate To a mixture of (2S)-2-[(4-methoxy-1H-indole-2-carbonyl)amino]-4-methyl-pentanoic acid (741.86 mg, 1.77 mmol, 1 eq, TFA) and methyl (2S)-2-amino-3-(1H-imidazol-5-yl)propanoate (0.3 g, 1.77 mmol, 1 eq, HCl), DIPEA (1.15 g, 8.87 mmol, 1.54 mL, 5 eq) in THF (0.3 mL) and DCM (0.3 mL) was added T3P (1.69 g, 2.66 mmol, 1.58 mL, 50% purity, 1.5 eq) at 0° C. under N₂. The mixture was stirred at 25° C. for 12 h. The reaction mixture was added saturated sodium bicarbonate solution (10 mL) and extracted with DCM (10 mL*2) to get the organic phase. The organic phase was washed with brine (3 mL*3) and dried over anhydrous sodium sulfate and concentrated to get the crude product. Methyl (2S)-3-(1H-imidazol-5-yl)-2-[[(2S)-2-[(4-methoxy-1H-indole-2-carbonyl)amino]-4-methyl-pentanoyl]amino]propanoate (300 mg, crude) was obtained as a solid and used directly next step. MS (ESI) m/z 456.2 [M+H]$^+$ 1H NMR (400 MHz, METHANOL-d$_4$) δ ppm 7.48 (s, 1H), 7.27 (s, 1H), 7.11-7.18 (m, 1H), 7.02 (d, J=8.16 Hz, 1H), 6.85 (s, 1H), 6.51 (d, J=7.72 Hz, 1H), 4.60-4.71 (m, 2H), 3.93 (s, 3H), 3.68 (s, 3H), 3.00-3.17 (m, 3H), 1.62-1.78 (m, 3H), 0.97 (dd, J=13.78, 6.06 Hz, 6H)

Step 3: N-[(1S)-1-[[(1S)-2-amino-1-(1H-imidazol-5-ylmethyl)-2-oxo-ethyl]carbamoyl]-3-methyl-butyl]-4-methoxy-1H-indole-2-carboxamide To methyl (2S)-3-(1H-imidazol-5-yl)-2-[[(2S)-2-[(4-methoxy-1H-indole-2-carbonyl)amino]-4-methyl-pentanoyl]amino]propanoate (200 mg, 439.07 umol, 1 eq) was added NH$_3$/MeOH (7 M, 11.76 mL, 187.56 eq) in one portion at 25° C. under N$_2$. The mixture was stirred at 80° C. and stirred for 12 h. The reaction mixture was cooled to 25° C. and concentrated to get the crude product. N-[(1S)-1-[[(1S)-2-amino-1-(1H-imidazol-5-ylmethyl)-2-oxo-ethyl]carbamoyl]-3-methyl-butyl]-4-methoxy-1H-indole-2-carboxamide (170 mg, 378.83 umol, 86.28% yield, 98.16% purity) was obtained as a solid and used directly next step. MS (ESI) m/z 441.2 [M+H]$^+$ Step 4: N-[(1S)-1-[[(1S)-1-cyano-2-(1H-imidazol-5-yl)ethyl]carbamoyl]-3-methyl-butyl]-4-methoxy-1H-indole-2-carboxamide To a mixture of N-[(1S)-1-[[(1S)-2-amino-1-(1H-imidazol-5-ylmethyl)-2-oxo-ethyl]carbamoyl]-3-methyl-butyl]-4-methoxy-1H-indole-2-carboxamide (140 mg, 317.82 umol, 1 eq) in DCM (2 mL) was added TFAA (133.51 mg, 635.65 umol, 88.41 uL, 2 eq) at 25° C. under N$_2$. The mixture was stirred at 25° C. for 2 h. The reaction mixture was concentrated to get the crude product. Crude product turned into compound 593 after 36 h in storage. The residue was purified by prep-HPLC. N-[(1S)-1-[[(1S)-1-cyano-2-(1H-imidazol-5-yl)ethyl]carbamoyl]-3-methyl-butyl]-4-methoxy-1H-indole-2-carboxamide (23.89 mg, 56.31 umol, 17.72% yield, 99.581% purity) was obtained as a solid. MS (ESI) m/z 423.2 [M+H]$^+$ Prep-HPLC Condition:
column: Waters Xbridge BEH C18 100*25 mm*5 um; mobile phase: [water (10 mM NH$_4$HCO$_3$)-ACN]; B %: 25%-55%, 10 min $^1$H NMR (400 MHz, METHANOL-d$_4$) δ ppm 7.58 (s, 1H), 7.30 (s, 1H), 7.12-7.21 (m, 1H), 6.99-7.09 (m, 2H), 6.52 (d, J=7.72 Hz, 1H), 5.05 (t, J=7.06 Hz, 1H), 4.61 (br dd, J=9.70, 4.85 Hz, 1H), 3.94 (s, 3H), 3.06-3.21 (m, 2H), 1.60-1.83 (m, 3H), 0.99 (dd, J=13.89, 6.17 Hz, 6H)

Step 5: tert-butyl (2S)-2-[(4-methoxy-1H-indole-2-carbonyl)amino]-4-methyl-pentanoate To a mixture of 4-methoxy-1H-indole-2-carboxylic acid (5 g, 26.15 mmol, 1 eq) and tert-butyl (2S)-2-amino-4-methyl-pentanoate (5.88 g, 31.38 mmol, 1.2 eq, HCl), EDCI (6.52 g, 34.00 mmol, 1.3 eq), HOBt (4.59 g, 34.00 mmol, 1.3 eq) in DMF (30 mL) was added TEA (7.94 g, 78.46 mmol, 10.92 mL, 3 eq) in one portion at 25° C. under N$_2$. The mixture was stirred at 25° C. and stirred for 2 h. The reaction mixture was added water (90 mL) and extracted with EtOAc (25 mL*3) to get the organic phase. The organic phase was washed with 5% citric acid (25 mL) and 5% aqueous solution of sodium bicarbonate (25 mL) and dried over anhydrous sodium sulfate, filtered and concentrated to get the product. The residue was purified by column chromatography (SiO$_2$, petroleum ether:EtOAc=30:1 to 10:1). Tert-butyl (2S)-2-[(4-methoxy-1H-indole-2-carbonyl)amino]-4-methyl-pentanoate (5.93 g, 16.45 mmol, 62.91% yield) was obtained as a solid. MS (ESI) m/z 361.2 [M+H]$^+$ $^1$H NMR (400 MHz, CHLOROFORM-d) δ ppm 9.25 (br s, 1H), 7.10-7.16 (m, 1H), 6.93-7.00 (m, 2H), 6.56 (br d, J=8.31 Hz, 1H), 6.44 (d, J=7.70 Hz, 1H), 4.66 (td, J=8.50, 5.14 Hz, 1H), 3.88 (s, 3H), 1.62-1.75 (m, 2H), 1.57-1.62 (m, 1H), 1.42 (s, 9H), 0.92 (dd, J=6.17, 3.85 Hz, 6H).

Step 6: (2S)-2-[(4-methoxy-1H-indole-2-carbonyl)amino]-4-methyl-pentanoic acid

To a mixture of tert-butyl (2S)-2-[(4-methoxy-1H-indole-2-carbonyl)amino]-4-methyl-pentanoate (2.00 g, 5.55 mmol, 1 eq) in DCM (8 mL) was added TFA (10.27 g, 90.04 mmol, 6.67 mL, 16.23 eq) and H$_2$O (666.67 mg, 37.01 mmol, 666.67 uL, 6.67 eq) in one portion at 0° C. under N$_2$. The mixture was stirred at 25° C. and stirred for 4 h. The reaction mixture was concentrated to get the crude product. (2S)-2-[(4-methoxy-1H-indole-2-carbonyl)amino]-4-methyl-pentanoic acid (2.24 g, 5.35 mmol, 96.50% yield, TFA) was obtained as a solid and used directly next step. MS (ESI) m/z 305.1 [M+H]$^+$ Example 9. Synthesis of Viral Protease Inhibitor Compounds 135, 595 and 136

Step 1: N-[(1S)-1-[[(1S)-1-(hydroxymethyl)-2-[(3S)-2-oxopyrrolodin-3-yl]ethyl]carbamoyl]-3-methyl-butyl]-4-methoxy-1H-indole-2-carboxamide

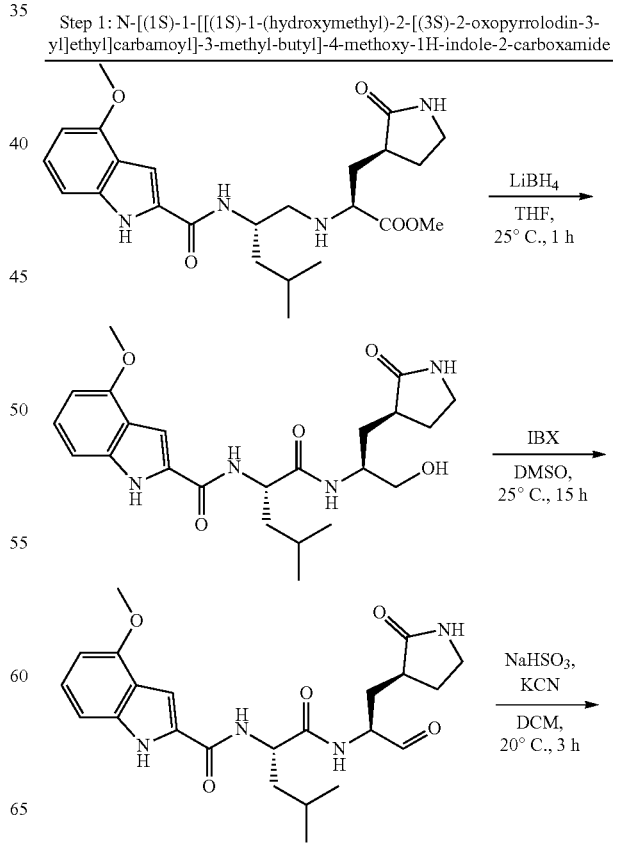

743
-continued

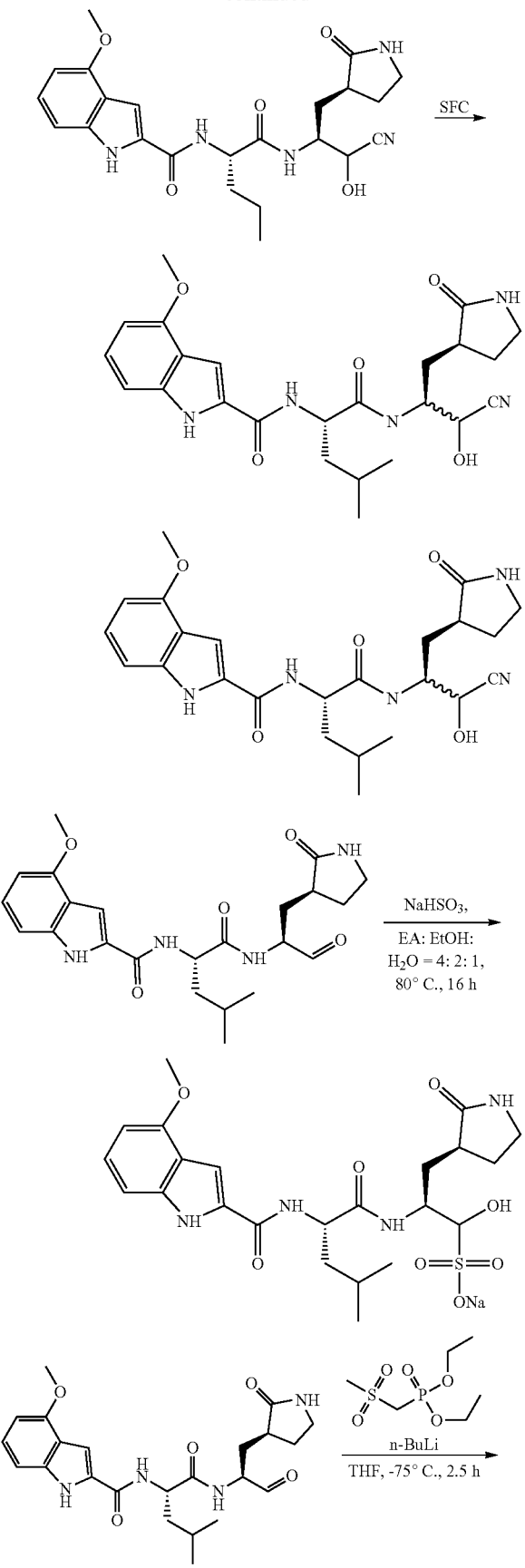

744
-continued

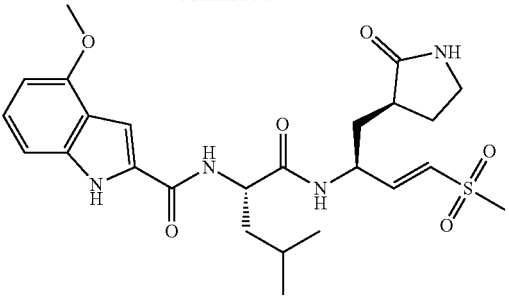

To a mixture of methyl (2S)-2-[[(2S)-2-[(4-methoxy-1H-indole-2-carbonyl)amino]-4-methyl-pentanoyl]amino]-3-[(3S)-2-oxopyrrolidin-3-yl]propanoate (1.5 g, 2.86 mmol, 90% purity, 1 eq) in THF (20 mL) was added LiBH$_4$ (124.45 mg, 5.71 mmol, 2 eq). The mixture was stirred at 25° C. for 2 h. Once the reaction was completed, the reaction mixture was quenched by addition H$_2$O (10 mL) at 0° C., and extracted with EtOAc (30 mL*3). The combined organic layers were washed with brine (30 mL), dried over Na$_2$SO$_4$, filtered and concentrated under reduced pressure to give a residue compound N-[(1S)-1-[[(1S)-1-(hydroxymethyl)-2-[(3S)-2-oxopyrrolidin-3-yl]ethyl]carbamoyl]-3-methyl-butyl]-4-methoxy-1H-indole-2-carboxamide (1.0 g, 2.25 mmol, 78.74% yield) was obtained as a solid. MS (ESI) m/z 445.1 [M+H]$^+$. $^1$H NMR (400 MHz, METHANOL-d$_4$) δ=7.27 (s, 1H), 7.19-7.10 (m, 1H), 7.02 (d, J=8.3 Hz, 1H), 6.51 (d, J=7.7 Hz, 1H), 4.65-4.53 (m, 1H), 4.05-3.97 (m, 1H), 3.93 (s, 3H), 3.60-3.43 (m, 2H), 3.27-3.10 (m, 2H), 2.59-2.43 (m, 1H), 2.39-2.19 (m, 1H), 2.08-1.89 (m, 1H), 1.85-1.63 (m, 4H), 1.60-1.46 (m, 1H), 1.00 (dd, J=6.1, 12.5 Hz, 6H).

Step 2: N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide To a mixture of N-[(1S)-1-[[(1S)-1-(hydroxymethyl)-2-[(3S)-2-oxopyrrolidin-3-yl]ethyl]carbamoyl]-3-methyl-butyl]-4-methoxy-1H-indole-2-carboxamide (674 mg, 1.52 mmol, 1 eq) in DMSO (25 mL) was added IBX (849.14 mg, 3.03 mmol, 2 eq). The mixture was stirred at 25° C. for 15 h. Once the reaction was completed, the reaction mixture was diluted with H$_2$O (30 mL) and extracted with EtOAc (30 mL*2). The combined organic layers were washed with brine (30 mL), dried over Na$_2$SO$_4$, filtered and concentrated under reduced pressure to give a residue. The residue was added ethyl acetate (10 mL) and filtered to give the product N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (420 mg, 759.31 umol, 50.08% yield, 80% purity) as a solid. MS (ESI) m/z 443.1 [M+H]$^+$. $^1$H NMR (400 MHz, METHANOL-d$_4$) δ=7.27 (s, 1H), 7.20-7.09 (m, 1H), 7.02 (d, J=8.3 Hz, 1H), 6.51 (d, J=7.7 Hz, 1H), 4.60 (dt, J=5.5, 9.9 Hz, 1.5H), 4.47 (dd, J=1.4, 4.1 Hz, 0.5H), 4.02-3.94 (m, 1H), 3.93 (s, 3H), 3.28-3.15 (m, 2H), 2.54-2.39 (m, 1H), 2.37-2.21 (m, 1H), 2.10-1.93 (m, 1H), 1.89-1.49 (m, 5H), 1.17-0.91 (m, 6H).

Step 3: N-[(1S)-1-[[(1S)-2-cyano-2-hydroxy-1-[[(3S)-2-oxopyrrolidin-3-yl]methyl]ethyl]carbamoyl]-3-methyl-butyl]-4-methoxy-1H-indole-2-carboxamide To a mixture of N-[(1S)-1-[[(1S)-1-formyl-2-[(3S)-2-oxopyrrolidin-3-yl]ethyl]carbamoyl]-3-methyl-butyl]-4- methoxy-1H-indole-2-carboxamide (400 mg, 723.15 umol, 80% purity, 1 eq) in DCM (10 mL) was added saturated NaHSO$_3$ (301.01 mg, 2.89 mmol, 203.38 uL, 4 eq). The mixture was stirred at 25° C. for 30 min, and then an aq solution of KCN (42 mg, 644.96 umol, 27.63 uL, 8.92 e−1 eq) in H$_2$O (0.8 mL) was added. The mixture was stirred at 25° C. for 3 h. Once the reaction was completed, the organic phase was collected and the aqueous layer was extracted with DCM (30 mL*3). The combined organic phase was washed with brine (30 mL*2), dried over Na$_2$SO$_4$, and concentrated to get the crude. The liquid was added NaOH to pH=9, then quenched by adding aq NaCl, then added NaOH to pH>14. The crude was purified by HCl prep-HPLC to get the mixture 120 mg, and SFC separation to get compound N-[(1S)-1-[[(1S)-2-cyano-2-hydroxy-1-[[(3S)-2-oxopyrrolidin-3-yl]methyl]ethyl]carbamoyl]-3-methyl-butyl]-4-methoxy-1H-indole-2-carboxamide (34 mg, 70.96 umol, 9.81% yield, 97.99% purity) and compound N-[(1S)-1-[[(1S)-2-cyano-2-hydroxy-1-[[(3S)-2-oxopyrrolidin-3-yl]methyl]ethyl]carbamoyl]-3-methyl-butyl]-4-methoxy-1H-indole-2-carboxamide (64 mg, 131.75 umol, 18.22% yield, 96.66% purity) as a solid. MS (ESI) m/z 470.2 [M+H]$^+$.

prep-HPLC condition: column: Phenomenex luna C18 80*40 mm*3 um; mobile phase: [water (0.04% HCl)-ACN]; B %: 26%-50%, 7 min SFC condition: column: REGIS (R,R)WHELK-O1 (250 mm*25 mm, 10 um); mobile phase: [Neu-IPA]; B %: 35%-35%, 11 min Compound 134 Isomer 1: $^1$H NMR (400 MHz, DMSO-d$_6$) δ=11.57 (d, J=1.8 Hz, 1H), 8.40 (d, J=7.9 Hz, 1H), 8.13 (d, J=9.3 Hz, 1H), 7.57 (s, 1H), 7.36 (d, J=1.5 Hz, 1H), 7.13-7.06 (m, 1H), 7.03-6.97 (m, 1H), 6.69 (d, J=7.3 Hz, 1H), 6.50 (d, J=7.7 Hz, 1H), 4.50-4.40 (m, 1H), 4.33 (t, J=7.8 Hz, 1H), 4.10-3.97 (m, 1H), 3.88 (s, 3H), 3.16-2.98 (m, 2H), 2.39-2.26 (m, 1H), 2.15-2.01 (m, 1H), 1.92-1.80 (m, 1H), 1.80-1.63 (m, 2H), 1.62-1.40 (m, 3H), 0.90 (dd, J=6.3, 15.5 Hz, 6H).

Compound 134 Isomer 2: $^1$H NMR (400 MHz, DMSO-d$_6$) δ=11.55 (br d, J=1.5 Hz, 1H), 8.35 (d, J=7.9 Hz, 1H), 8.21 (d, J=8.6 Hz, 1H), 7.60 (s, 1H), 7.34 (d, J=1.8 Hz, 1H), 7.12-7.06 (m, 1H), 7.03-6.97 (m, 1H), 6.64 (d, J=6.0 Hz, 1H), 6.50 (d, J=7.5 Hz, 1H), 4.60-4.49 (m, 2H), 4.12-3.96 (m, 1H), 3.88 (s, 3H), 3.19-2.98 (m, 2H), 2.41-2.26 (m, 1H), 2.16-1.95 (m, 2H), 1.92-1.35 (m, 5H), 0.98-0.82 (m, 6H).

Step 4: [(2S)-1-hydroxy-2-[[(2S)-2-[(4-methoxy-1H-indole-2-carbonyl)amino]-4-methyl-pentanoyl]amino]-3-[(3S)-2-oxopyrrolidin-3-yl]propyl]sulfonyloxysodium To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (50 mg, 112.99 umol, 1 eq) in EtOH (0.4 mL), EtOAc (0.2 mL) and H$_2$O (0.1 mL) was added NaHSO$_3$ (11.76 mg, 112.99 umol, 7.94 uL, 1 eq). The mixture was stirred at 80° C. for 16 h. Once the reaction was completed, the reaction mixture was concentrated under reduced pressure to give a residue. The residue was added DCM (3 mL) and ACN (3 mL), filtered to get the compound [(2S)-1-hydroxy-2-[[(2S)-2-[(4-methoxy-1H-indole-2-carbonyl)amino]-4-methyl-pentanoyl] amino]-3-[(3S)-2-oxopyrrolidin-3-yl]propyl]sulfonyloxysodium (5 mg, 5.26 umol, 4.66% yield, 57.5% purity) as a solid. (ESI) m/z 525.1 [M+H]$^+$ $^1$H NMR (400 MHz, DMSO-d6) δ=11.67-11.44 (m, 1H), 9.42 (s, 0.02H), 8.52-8.27 (m, 1H), 7.74-7.59 (m, 1H), 7.43 (s, 1H), 7.32 (dd, J=1.8, 4.9 Hz, 1H), 7.15-6.93 (m, 2H), 6.50 (d, J=7.7 Hz, 1H), 5.40-5.24 (m, 1H), 4.61-4.33 (m, 1H), 4.31-4.15 (m, 0.5H), 4.11-3.96 (m, 0.5H), 3.94 (dd, J=2.4, 5.7 Hz, 0.5H), 3.88 (s, 3H), 3.85-3.81 (m, 0.511H), 3.19-2.94 (m, 2H), 2.27-1.87 (m, 3H), 1.85-1.42 (m, 5H), 0.99-0.79 (m, 6H)

Step 5: 4-methoxy-N-[(1S)-3-methyl-1-[[(E, 1S)-3-methylsulfonyl-1-[[(3S)-2-oxopyrrolidin-3-yl] methyl] allyl]carbamoyl]butyl]-1H-indole-2-carboxamide To a mixture of 1-[ethoxy(methylsulfonylmethyl)phosphoryl]oxyethane (130.06 mg, 564.96 umol, 5 eq) in THF (2 mL) was added n-BuLi (2.5 M, 180.79 uL, 4 eq) at 0° C. under N$_2$. The mixture was stirred at −75° C. for 30 min, then added N-[(1S)-1-[[(1S)-1-formyl-2-[(3S)-2-oxopyrrolidin-3-yl]ethyl] carbamoyl]-3-methyl-butyl]-4-methoxy-1H-indole-2-carboxamide (50 mg, 112.99 umol, 1 eq). The mixture was stirred at −75° C. for 2 h. Once the reaction was completed, the reaction mixture was quenched by addition H$_2$O (10 mL) at 0° C., and then concentrated under reduced pressure to give a residue. The residue was purified by prep-HPLC to get the compound 4-methoxy-N-[(1S)-3-methyl-1-[[(E, 1S)-3-methylsulfonyl-1-[[(3S)-2-oxopyrrolidin-3-yl]methyl]allyl]carbamoyl]butyl]-1H-indole-2-carboxamide (15 mg, 28.82 umol, 25.50% yield, 99.638% purity) as a solid. (ESI) m/z 519.1 [M+H]$^+$ column: Phenomenex luna C18 80*40 mm*3 um; mobile phase: [water (0.04% HCl)-ACN]; B %: 26%-52%, 7 min $^1$H NMR (400 MHz, METHANOL-d$_4$) δ=7.33-7.26 (m, 1H), 7.20-7.10 (m, 1H), 7.03 (d, J=8.3 Hz, 1H), 6.85 (dd, J=4.8, 15.3 Hz, 1H), 6.68 (dd, J=1.6, 15.3 Hz, 1H), 6.52 (d, J=7.7 Hz, 1H), 4.77-4.67 (m, 1H), 4.61-4.50 (m, 1H), 3.99-3.83 (m, 3H), 3.28-3.18 (m, 2H), 3.01-2.88 (m, 3H), 2.65-2.50 (m, 1H), 2.39-2.22 (m, 1H), 2.15-1.97 (m, 1H), 1.91-1.62 (m, 5H), 1.09-0.92 (m, 6H)

Example 10. Synthesis of Viral Protease Inhibitor Compound 740 and 741

Step 1: tert-butyl ((S)-4-chloro-3-oxo-1-((S)-2-oxopyrrolidin-3-yl)butan-2-yl)carbamate

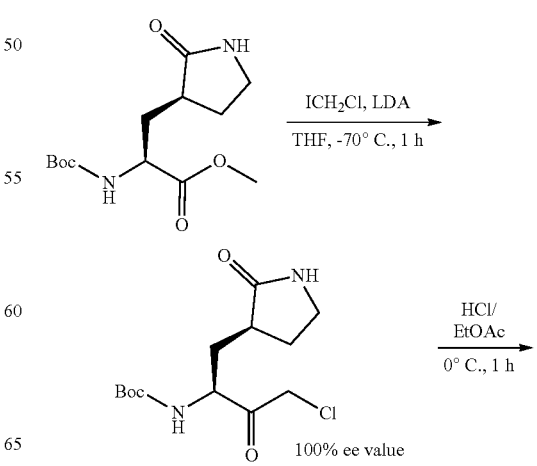

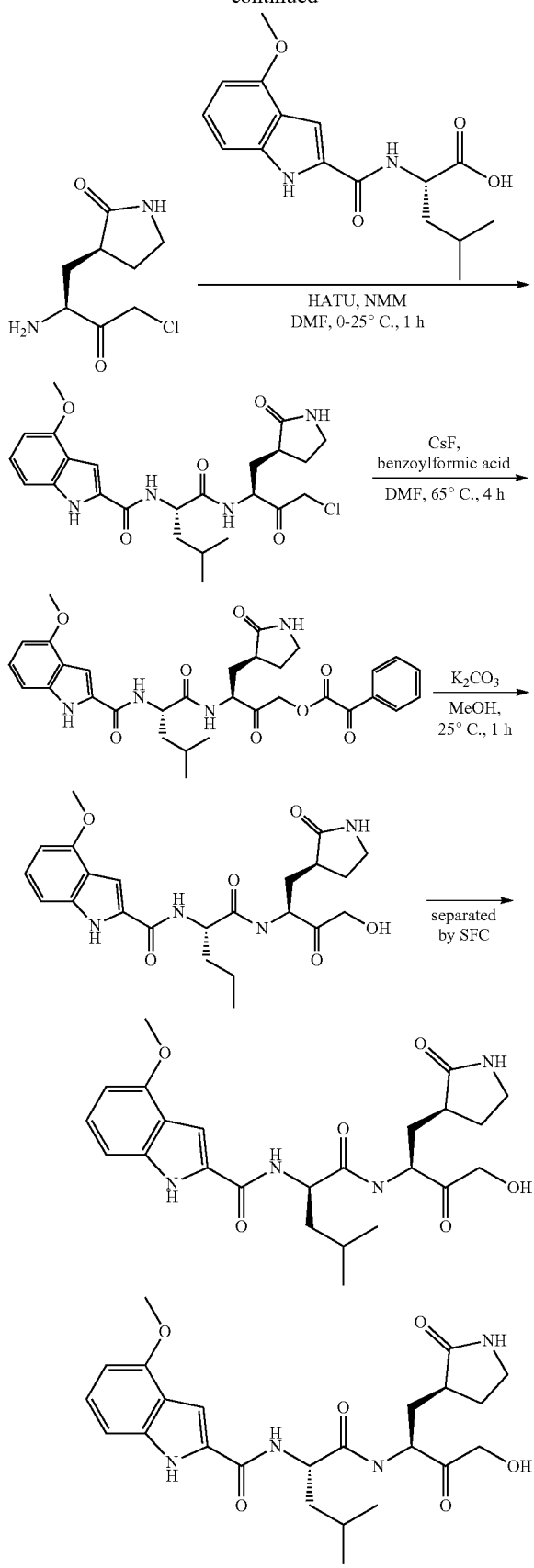

To a solution of methyl (2S)-2-(tert-butoxycarbonylamino)-3-[(3S)-2-oxopyrrolidin-3-yl]propanoate (0.6 g, 2.10 mmol, 1 eq) in THF (24 mL) was added chloro(iodo)methane (1.48 g, 8.38 mmol, 608.42 uL, 4 eq), then the solution was cooled to −70° C. and LDA (2 M, 6.29 mL, 6 eq) was added drop-wise. The reaction was stirred at −70° C. for 1 h. Upon completion, the reaction mixture was quenched by addition a mixture of AcOH (4.5 mL) and THF (22 mL) at −70° C., and then diluted with ethyl acetate (50 mL) and extracted with water (30 mL*2), sat. $NaHCO_3$ (30 mL). The organic layers were washed dried over $Na_2SO_4$, filtered and concentrated under reduced pressure to give a residue. The residue was purified by column chromatography ($SiO_2$, petroleum ether:EtOAc=2:1 to 0:1) and then triturated with methyl tertiary butyl ether:petroleum ether=4:1 (3 mL) to give tert-butyl N-[(1S)-3-chloro-2-oxo-1-[[(3S)-2-oxopyrrolidin-3-yl]methyl]propyl]carbamate (0.35 g, 1.03 mmol, 49.32% yield, 90% purity) as a solid. MS (ESI) m/z 308.0 $[M+H]^+$.

$^1$H NMR (400 MHz, DMSO-$d_6$) δ=7.66 (br s, 1H), 7.53 (br d, J=7.7 Hz, 1H), 4.61 (d, J=2.2 Hz, 2H), 4.22-4.10 (m, 1H), 3.21-3.11 (m, 2H), 2.34-2.06 (m, 2H), 1.93-1.80 (m, 1H), 1.73-1.54 (m, 2H), 1.39 (s, 9H).

Step 2: (S)-3-((S)-2-amino-4-chloro-3-oxobutyl)pyrrolidin-2-one

A solution of tert-butyl N-[(1S)-3-chloro-2-oxo-1-[[(3S)-2-oxopyrrolidin-3-yl]methyl]propyl]carbamate (0.33 g, 1.08 mmol, 1 eq) in HCl/EtOAc (4 M, 5 mL, 18.47 eq) was stirred at 0° C. for 1 h. Upon completion, the reaction mixture was concentrated under reduced pressure to give (3S)-3-[(2S)-2-amino-4-chloro-3-oxo-butyl]pyrrolidin-2-one (0.3 g, crude, HCl) as an oil. MS (ESI) m/z 205.0 $[M+H]^+$.

$^1$H NMR (400 MHz, DMSO-$d_6$) δ=8.75 (br s, 3H), 7.97 (br s, 1H), 4.96-4.91 (m, 1H), 4.77 (s, 1H), 4.37-4.23 (m, 1H), 3.26-3.07 (m, 2H), 2.60 (br d, J=8.6 Hz, 1H), 2.37-2.27 (m, 1H), 1.96-1.90 (m, 1H), 1.79-1.66 (m, 1H).

Step 3: N-((S)-1-(((S)-4-chloro-3-oxo-1-((S)-2-oxopyrrolidin-3-yl)butan-2-yl)amino)-4-methyl-1-oxopentan-2-yl)-4-methoxy-1H-indole-2-carboxamide A solution of (2S)-2-[(4-methoxy-1H-indole-2-carbonyl)amino]-4-methyl-pentanoic acid (416.53 mg, 1.37 mmol, 1.1 eq) in DMF (5 mL) was added HATU (946.18 mg, 2.49 mmol, 2 eq) and NMM (251.71 mg, 2.49 mmol, 273.59 uL, 2 eq), the solution was stirred at 0° C. for 0.5 h. Then a solution of (3S)-3-[(2S)-2-amino-4-chloro-3-oxo-butyl]pyrrolidin-2-one (0.3 g, 1.24 mmol, 1 eq, HCl) in DMF (5 mL) was added drop-wise at 0° C. The reaction was stirred at 25° C. for 0.5 h. Upon completion, the reaction mixture was diluted with water (50 mL) at 0° C. drop-wise and extracted with EtOAc (20 mL*3). The combined organic layers were dried over $Na_2SO_4$, filtered and concentrated under reduced pressure to give a residue. The residue was purified by column chromatography ($SiO_2$, petroleum ether:EtOAc=2:1 to 0:1). To give N-[(1S)-1-[[(1S)-3-chloro-2-oxo-1-[[(3S)-2-oxopyrrolidin-3-yl]methyl]propyl]carbamoyl]-3-methyl-butyl]-4-methoxy-1H-indole-2-carboxamide (0.3 g, 549.92 umol, 44.20% yield, 90% purity) as a solid. MS (ESI) m/z 491.1 $[M+H]^+$.

$^1$H NMR (400 MHz, DMSO-$d_6$) δ=11.58 (br s, 1H), 8.74-8.57 (m, 1H), 8.44 (br d, J=5.0 Hz, 1H), 7.65 (br d, J=4.5 Hz, 1H), 7.37 (br s, 1H), 7.15-7.06 (m, 1H), 7.01 (br d, J=8.1 Hz, 1H), 6.50 (br d, J=7.6 Hz, 1H), 4.75-4.60 (m,

1H), 4.59-4.55 (m, 1H), 4.44 (br d, J=9.2 Hz, 2H), 3.88 (s, 3H), 3.13-3.01 (m, 2H), 2.34-2.18 (m, 1H), 2.09 (br dd, J=2.5, 3.9 Hz, 1H), 1.99-1.90 (m, 1H), 1.78-1.49 (m, 5H), 0.97-0.81 (m, 6H).

Step 4: (S)-3-((S)-2-(4-methoxy-1H-indole-2-carboxamido)-4-methylpentanamido)-2-oxo-4-((S)-2-oxopyrrolidin-3-yl)butyl 2-oxo-2-phenylacetate To a solution of N-[(1S)-1-[[(1S)-3-chloro-2-oxo-1-[[(3S)-2-oxopyrrolidin-3-yl]methyl]propyl]carbamoyl]-3-methyl-butyl]-4-methoxy-1H-indole-2-carboxamide (0.25 g, 509.19 umol, 1 eq) in DMF (6 mL) was added benzoylformic acid (99.38 mg, 661.94 umol, 1.3 eq) and CsF (177.89 mg, 1.17 mmol, 43.18 uL, 2.3 eq). The reaction was stirred at 65° C. for 4 h under N₂ atmosphere. Upon completion, the reaction mixture was diluted with water (20 mL) and extracted with EtOAc (10 mL*3). The combined organic layers were dried over Na₂SO₄, filtered and concentrated under reduced pressure to give [(3S)-3-[[(2S)-2-[(4-methoxy-1H-indole-2-carbonyl)amino]-4-methyl-pentanoyl]amino]-2-oxo-4-[(3S)-2-oxopyrrolidin-3-yl]butyl] 2-oxo-2-phenyl-acetate (0.3 g, crude) as an oil. MS (ESI) m/z 605.2 [M+H]⁺.

Step 5&6: N-[(1R)-1-[[(1S)-3-hydroxy-2-oxo-1-[[(3S)-2-oxopyrrolidin-3-yl]methyl]propyl]carbamoyl]-3-methyl-butyl]-4-methoxy-1H-indole-2-carboxamide N-[(1S)-1-[[(1S)-3-hydroxy-2-oxo-1-[[(3S)-2-oxopyrrolidin-3-yl]methyl]propyl]carbamoyl]-3-methyl-butyl]-4-methoxy-1H-indole-2-carboxamide To a solution of [(3S)-3-[[(2S)-2-[(4-methoxy-1H-indole-2-carbonyl)amino]-4-methyl-pentanoyl]amino]-2-oxo-4-[(3S)-2-oxopyrrolidin-3-yl]butyl] 2-oxo-2-phenyl-acetate (0.3 g, 496.16 umol, 1 eq) in MeOH (10 mL) was added K₂CO₃ (3.43 mg, 24.81 umol, 0.05 eq). The reaction was stirred at 25° C. for 1 h. Upon completion, the reaction mixture was concentrated under reduced pressure to give a residue. The residue was purified by prep-TLC (SiO₂, DCM:MeOH=10:1) to give the product.

¹H NMR (400 MHz, DMSO-d₆) δ=11.58 (s, 1H), 8.50 (d, J=7.8 Hz, 1H), 8.41 (d, J=7.9 Hz, 1H), 7.63 (s, 1H), 7.35 (d, J=1.5 Hz, 1H), 7.14-7.05 (m, 1H), 7.04-6.94 (m, 1H), 6.50 (d, J=7.7 Hz, 1H), 5.05-4.98 (m, 1H), 4.57-4.46 (m, 1H), 4.41 (ddd, J=4.0, 7.7, 11.2 Hz, 1H), 4.34-4.25 (m, 1H), 4.22-4.13 (m, 1H), 3.88 (s, 3H), 3.18-3.01 (m, 2H), 2.25-2.14 (m, 1H), 2.13-2.04 (m, 1H), 1.99-1.84 (m, 1H), 1.77-1.48 (m, 5H), 0.93 (br d, J=6.2 Hz, 3H), 0.89 (br d, J=6.4 Hz, 3H).

To give N-[(1S)-1-[[(1S)-3-hydroxy-2-oxo-1-[[(3S)-2-oxopyrrolidin-3-yl]methyl]propyl]carbamoyl]-3-methyl-butyl]-4-methoxy-1H-indole-2-carboxamide (23.86 mg, 49.08 umol, 9.89% yield, 97.2% purity) as a solid. MS (ESI) m/z 473.2 [M+H]⁺. The product was separated by chiral-SFC (column: DAICEL CHIRALCEL OJ (250 mm*30 mm, 10 um); mobile phase: [Neu-MeOH]; B %: 20%-20%, 15 min) to give N-[(1R)-1-[[(1S)-3-hydroxy-2-oxo-1-[[(3S)-2-oxopyrrolidin-3-yl]methyl]propyl]carbamoyl]-3-methyl-butyl]-4-methoxy-1H-indole-2-carboxamide (15.43 mg, 31.22 umol, 6.29% yield, 95.6% purity) as a solid. MS (ESI) m/z 473.2 [M+H]⁺.

¹H NMR (400 MHz, DMSO-d₆) δ=11.57 (s, 1H), 8.45 (br d, J=8.1 Hz, 1H), 8.41 (br d, J=7.8 Hz, 1H), 7.62 (s, 1H), 7.36 (d, J=1.3 Hz, 1H), 7.14-7.05 (m, 1H), 7.04-6.97 (m, 1H), 6.50 (d, J=7.6 Hz, 1H), 5.06 (br s, 1H), 4.62-4.38 (m, 2H), 4.30-4.19 (m, 1H), 4.19-4.09 (m, 1H), 3.88 (s, 3H), 3.19-3.01 (m, 2H), 2.37-2.22 (m, 1H), 2.09 (br dd, J=3.2, 6.2 Hz, 1H), 1.99-1.86 (m, 1H), 1.80-1.43 (m, 5H), 0.94 (d, J=6.2 Hz, 3H), 0.89 (d, J=6.2 Hz, 3H).

Example 11. Synthesis of Viral Protease Inhibitor Compound 143

Step 1: methyl (2S)-2-[[(2S)-2-amino-4-methyl-pentanoyl]amino]-3-[(3S)-2-oxopyrrolidin-3-yl]propanoate

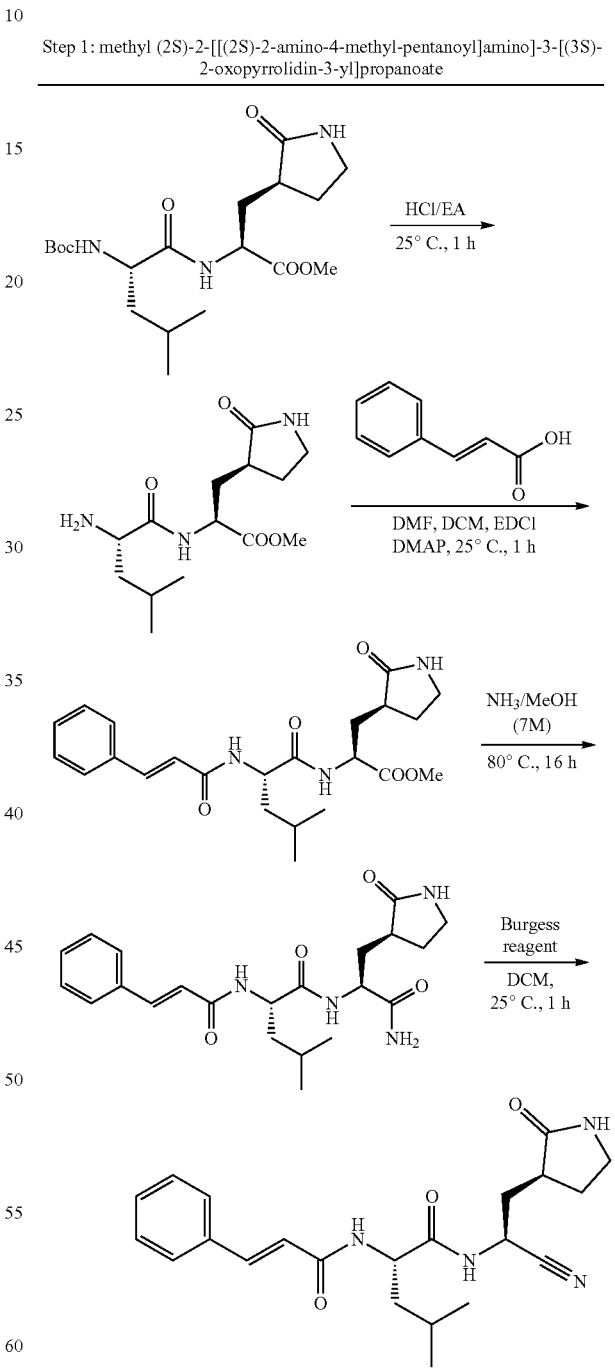

A mixture of methyl (2S)-2-[[(2S)-2-(tert-butoxycarbonylamino)-4-methyl-pentanoyl]amino]-3-[(3S)-2-oxopyrrolidin-3-yl]propanoate (250 mg, 625.81 umol, 1 eq) was added HCl/EtOAc (8 mL) at 25° C. for 1 h. Upon completion, the reaction mixture was concentrated under reduced pressure to give a residue get a product methyl (2S)-2-[[(2S)-2-amino-4-methyl-pentanoyl]amino]-3-[(3S)-2-oxopyrrolidin-3-yl]propanoate (230 mg, crude) as an oil. MS (ESI) m/z 300.0 [M+H]⁺.

Step 2: methyl (2S)-2-[[(2S)-4-methyl-2-[[(E)-3-phenylprop-2-enoyl]amino]pentanoyl]amino]-3-[(3S)-2-oxopyrrolidin-3-yl]propanoate A mixture of methyl (2S)-2-[[(2S)-2-amino-4-methyl-pentanoyl]amino]-3-[(3S)-2-oxopyrrolidin-3-yl]propanoate (230 mg, 684.88 umol, 1 eq, HCl) and (E)-3-phenylprop-2-enoic acid (202.94 mg, 1.37 mmol, 162.35 uL, 2 eq) in DMF (2 mL) and DCM (4 mL), and added EDCI (262.59 mg, 1.37 mmol, 2 eq) and DMAP (167.34 mg, 1.37 mmol, 2 eq). The mixture was stirred at 25° C. for 1 h. Upon completion, the reaction mixture was diluted with H₂O (10 mL) and extracted with DCM (10 mL*3). The combined organic layers were washed with brine (50 mL), dried over Na₂SO₄, filtered and concentrated under reduced pressure to give a residue. The residue was purified by silica gel chromatography (SiO₂, petroleum ether:EtOAc=1:1) to get a product methyl (2S)-2-[[(2S)-4-methyl-2-[[(E)-3-phenylprop-2-enoyl]amino]pentanoyl]amino]-3-[(3S)-2-oxopyrrolidin-3-yl]propanoate (200 mg, 465.65 umol, 67.99% yield) as an oil. MS (ESI) m/z 430.1 [M+H]⁺.

Step 3: (2S)-N-[(1S)-2-amino-2-oxo-1-[[(3S)-2-oxopyrrolidin-3-yl]methyl]ethyl]-4-methyl-2-[[(E)-3-phenylprop-2-enoyl]amino]pentanamide A mixture of methyl (2S)-2-[[(2S)-4-methyl-2-[[(E)-3-phenylprop-2-enoyl]amino]pentanoyl]amino]-3-[(3S)-2-oxopyrrolidin-3-yl]propanoate (200 mg, 465.65 umol, 1 eq) in NH₃/MeOH (7 M, 7 mL, 97% purity, 105.23 eq) heated to 80° C. for 16 h in the sealed tube. Upon completion, the reaction mixture was concentrated under reduced pressure to give a residue to get the product (2S)-N-[(1S)-2-amino-2-oxo-1-[[(3S)-2-oxopyrrolidin-3-yl]methyl]ethyl]-4-methyl-2-[[(E)-3-phenylprop-2-enoyl]amino]pentanamide (200 mg, crude) as an oil. MS (ESI) m/z 415.1 [M+H]⁺.

Step 4: (2S)-N-[(1S)-1-cyano-2-[(3S)-2-oxopyrrolidin-3-yl]ethyl]-4-methyl-2-[[(E)-3-phenylprop-2-enoyl]amino]pentanamide A mixture of (2S)-N-[(1S)-2-amino-2-oxo-1-[[(3S)-2-oxopyrrolidin-3-yl]methyl]ethyl]-4-methyl-2-[[(E)-3-phenylprop-2-enoyl]amino]pentanamide (200 mg, 482.51 umol, 1 eq) in DCM (2 mL) was added methoxycarbonyl-(triethylammonio)sulfonyl-azanide (574.93 mg, 2.41 mmol, 5 eq), the mixture was stirred at 25° C. for 1 h. Upon completion, the reaction mixture was concentrated under reduced pressure to give a residue. The residue was purified by prep-HPLC (column: Waters Xbridge Prep OBD C18 150*40 mm*10 um; mobile phase: [water (10 mM NH₄HCO₃)-ACN]; B %: 25%-55%, 8 min) to give a product (2S)-N-[(1S)-1-cyano-2-[(3S)-2-oxopyrrolidin-3-yl]ethyl]-4-methyl-2-[[(E)-3-phenylprop-2-enoyl]amino]pentanamide (23.1 mg, 58.26 umol, 12.07% yield, 100% purity) as a solid. MS (ESI) m/z 397.2 [M+H]⁺.

¹H NMR (400 MHz, CDCl₃)=8.70 (br d, J=6.6 Hz, 1H), 7.66-7.55 (m, 1H), 7.54-7.44 (m, 2H), 7.35 (br s, 3H), 6.72-6.52 (m, 2H), 6.47 (d, J=15.7 Hz, 1H), 5.02-4.67 (m, 2H), 3.49-3.22 (m, 2H), 2.56-2.27 (m, 3H), 2.02-1.88 (m, 1H), 1.88-1.80 (m, 1H), 1.75-1.61 (m, 3H), 1.07-0.87 (m, 6H)

Example 12. Synthesis of Viral Protease Inhibitor Compound 598

Step 1: methyl (2S)-2-[[(2S)-2-amino-4-methyl-pentanoyl]amino]-3-[(3S)-2-oxopyrrolidin-3-yl]propanoate

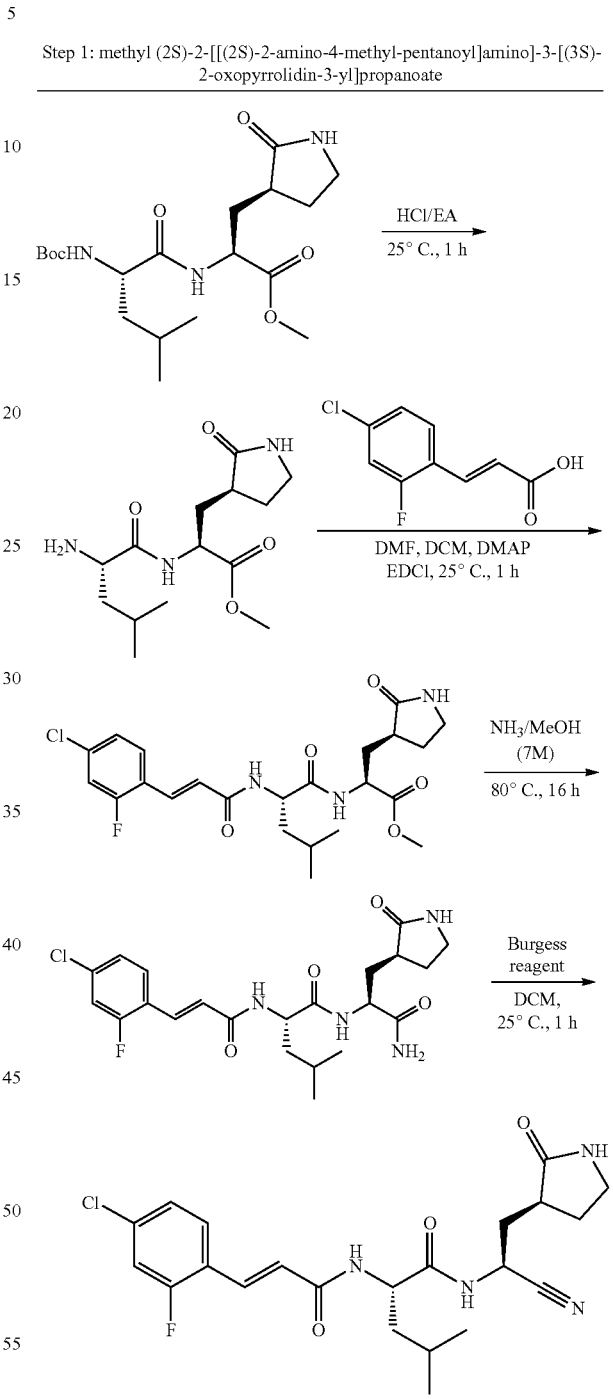

A mixture of methyl (2S)-2-[[(2S)-2-(tert-butoxycarbonylamino)-4-methyl-pentanoyl]amino]-3-[(3S)-2-oxopyrrolidin-3-yl]propanoate (300 mg, 750.98 umol, 1 eq) was added HCl/EtOAc (4 M, 6 mL, 31.96 eq) at 25° C. for 1 h. Upon completion, the product blow-dried directly with N₂ to get the product methyl (2S)-2-[[(2S)-2-amino-4-methyl-pentanoyl]amino]-3-[(3S)-2-oxopyrrolidin-3-yl]propanoate (260 mg, crude) as an oil. MS (ESI) m/z 300.1 [M+H]⁺.

Step 2: methyl (2S)-2-[[(2S)-2-[[(E)-3-(4-chloro-2-fluoro-phenyl)prop-2-enoyl]amino]-4-methyl-pentanoyl]amino]-3-[(3S)-2-oxopyrrolidin-3-yl]propanoate A mixture of methyl (2S)-2-[[(2S)-2-amino-4-methyl-pentanoyl]amino]-3-[(3S)-2-oxopyrrolidin-3-yl]propanoate (250 mg, 744.43 umol, 1 eq, HCl) and (E)-3-(4-chloro-2-fluoro-phenyl)prop-2-enoic acid (298.66 mg, 1.49 mmol, 81.96 uL, 2 eq) in DMF (2 mL) and DCM (4 mL) was added EDCI (285.42 mg, 1.49 mmol, 2 eq) and DMAP (181.89 mg, 1.49 mmol, 2 eq). The mixture was stirred at 25° C. for 1 h. Upon completion, the reaction mixture was diluted with H₂O (10 mL) and extracted with DCM (10 mL*3). The combined organic layers were washed with brine (50 mL), dried over Na₂SO₄, filtered and concentrated under reduced pressure to give a residue. The residue was purified by silica gel chromatography (SiO₂, petroleum ether:EtOAc=0:1) to get a product methyl (2S)-2-[[(2S)-2-[[(E)-3-(4-chloro-2-fluoro-phenyl)prop-2-enoyl]amino]-4-methyl-pentanoyl]amino]-3-[(3S)-2-oxopyrrolidin-3-yl]propanoate (80 mg, 165.99 umol, 22.30% yield) as an oil. MS (ESI) m/z 482.1 [M+H]⁺.

Step 3: (2S)-N-[(1S)-2-amino-2-oxo-1-[[(3S)-2-oxopyrrolidin-3-yl]methyl]ethyl]-2-[[(E)-3-(4-chloro-2-fluoro-phenyl)prop-2-enoyl]amino]-4-methyl-pentanamide A mixture of methyl (2S)-2-[[(2S)-2-[[(E)-3-(4-chloro-2-fluoro-phenyl)prop-2-enoyl]amino]-4-methyl-pentanoyl]amino]-3-[(3S)-2-oxopyrrolidin-3-yl]propanoate (70 mg, 145.25 umol, 1 eq) in NH₃/MeOH (7 M, 6 mL, 97% purity, 289.17 eq) was stirred at 80° C. for 16 h. Upon completion, the reaction mixture was concentrated under reduced pressure to give the product (2S)-N-[(1S)-2-amino-2-oxo-1-[[(3S)-2-oxopyrrolidin-3-yl]methyl]ethyl]-2-[[(E)-3-(4-chloro-2-fluoro-phenyl)prop-2-enoyl]amino]-4-methyl-pentanamide (70 mg, crude) as an oil. MS (ESI) m/z 467.1 [M+H]⁺.

Step 4: (2S)-2-[[(E)-3-(4-chloro-2-fluoro-phenyl)prop-2-enoyl]amino]-N-[(1S)-1-cyano-2-[(3S)-2-oxopyrrolidin-3-yl]ethyl]-4-methyl-pentanamide A mixture of (2S)-N-[(1S)-2-amino-2-oxo-1-[[(3S)-2-oxopyrrolidin-3-yl]methyl]ethyl]-2-[[(E)-3-(4-chloro-2-fluoro-phenyl)prop-2-enoyl]amino]-4-methyl-pentanamide (70 mg, 149.91 umol, 1 eq) in DCM (1.5 mL) was added methoxycarbonyl-(triethylammonio)sulfonyl-azanide (160.77 mg, 674.62 umol, 4.5 eq), the mixture was stirred at 25° C. for 1 h. Upon completion, the reaction mixture was concentrated under reduced pressure to give a residue. The residue was purified by prep-HPLC (column: Waters Xbridge Prep OBD C18 150*40 mm*10 um; mobile phase: [water (10 mM NH₄HCO₃)-ACN]; B %: 30%-60%, 8 min) to get product (2S)-N-[(1S)-1-cyano-2-[(3S)-2-oxopyrrolidin-3-yl]ethyl]-4-methyl-2-[[(E)-3-phenylprop-2-enoyl]amino]pentanamide (13.4 mg, 58.26 umol, 12.07% yield, 100% purity) as a solid. MS (ESI) m/z 449.1 [M+H]⁺.

¹H NMR (400 MHz, CDCl₃) δ=8.67 (br d, J=5.7 Hz, 1H), 7.63 (d, J=15.7 Hz, 1H), 7.42 (t, J=8.3 Hz, 1H), 7.19-7.06 (m, 2H), 6.55 (d, J=15.7 Hz, 1H), 6.34 (br s, 1H), 6.19 (br s, 1H), 4.83-4.67 (m, 2H), 3.47-3.33 (m, 2H), 2.58-2.28 (m, 3H), 2.04 (br s, 1H), 1.95-1.82 (m, 1H), 1.81-1.62 (m, 3H), 0.99 (d, J=6.0 Hz, 6H)

Example 13. Synthesis of Viral Protease Inhibitor Compound 149

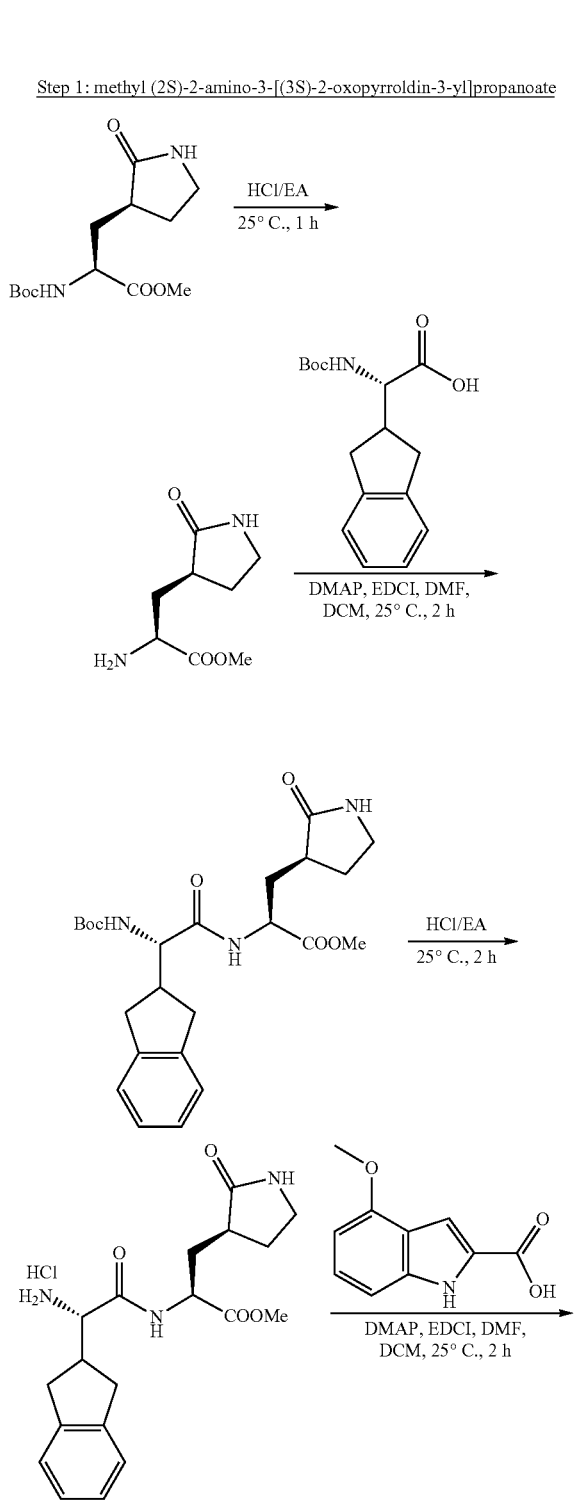

Step 1: methyl (2S)-2-amino-3-[(3S)-2-oxopyrroldin-3-yl]propanoate

-continued

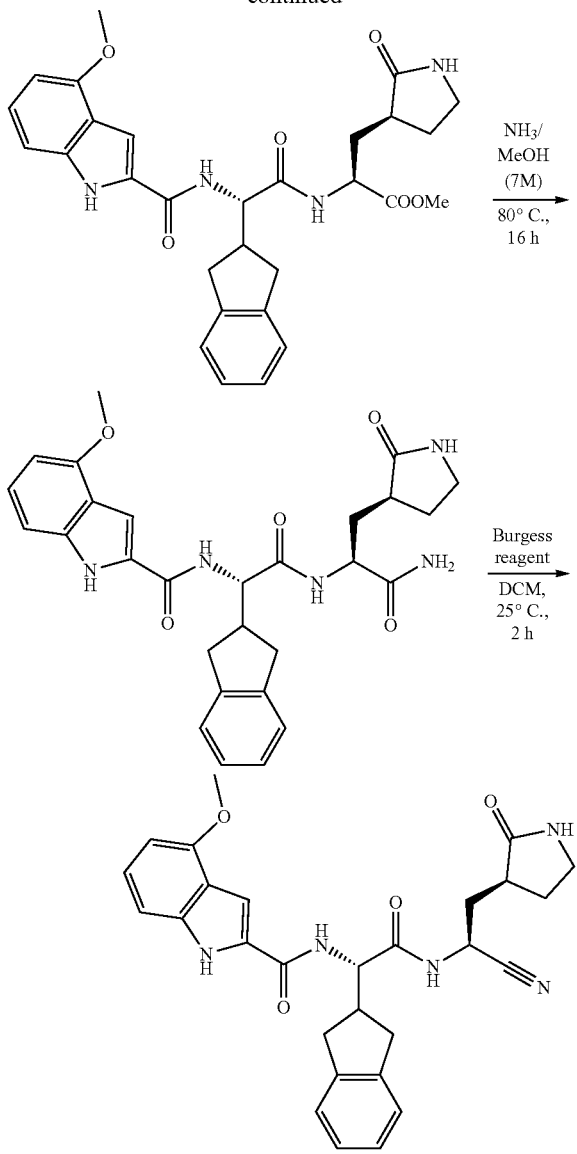

To a mixture of methyl (2S)-2-(tert-butoxycarbonylamino)-3-[(3S)-2-oxopyrrolidin-3-yl]propanoate (500 mg, 1.75 mmol, 1 eq) in HCl/EtOAc (4 M, 20 mL). The mixture was stirred at 25° C. and stirred for 1 h. Once the reaction was completed, the reaction was concentrated to give the crude methyl (2S)-2-amino-3-[(3S)-2-oxopyrrolidin-3-yl]propanoate (400 mg, crude) (oil). The crude product was used directly without further purification. MS (ESI) m/z 187.1 [M+H]$^+$ Step 2: methyl (2S)-2-[[(2S)-2-(tert-butoxycarbonylamino)-2-indan-2-yl-acetyl]amino]-3-[(3S)-2-oxopyrrolidin-3-yl]propanoate To a mixture of methyl (2S)-2-amino-3-[(3S)-2-oxopyrrolidin-3-yl]propanoate (190 mg, 1.02 mmol, 1 eq) and (2S)-2-(tert-butoxycarbonylamino)-2-indan-2-yl-acetic acid (297.27 mg, 1.02 mmol, 1 eq) in DCM (9 mL) and DMF (3 mL) was added DMAP (249.31 mg, 2.04 mmol, 2 eq) and EDCI (391.21 mg, 2.04 mmol, 2 eq). The mixture was stirred at 25° C. for 2 h. Once the reaction was completed, the reaction was poured into ice-water (30 mL) and extracted with EtOAc (20 mL*3). The combined organic phase was dried with anhydrous Na$_2$SO$_4$, filtered and concentrated in vacuum. The residue was purified by silica gel chromatography (column height: 250 mm, diameter: 100 mm, 100-200 mesh silica gel, petroleum ether/EtOAc=1/1, 0/1) to give methyl (2S)-2-[[(2S)-2-(tert-butoxycarbonylamino)-2-indan-2-yl-acetyl]amino]-3-[(3S)-2-oxopyrrolidin-3-yl]propanoate (300 mg, 522.27 umol, 51.18% yield, 80% purity) (solid). MS (ESI) m/z 460.3 [M+H]$^+$ Step 3: methyl (2S)-2-[[(2S)-2-(tert-butoxycarbonylamino)-2-indan-2-yl-acetyl]amino]-3-[(3S)-2-oxopyrrolidin-3-yl]propanoate To a mixture of (S)-methyl 2-((tert-butoxycarbonyl)amino)-3-((S)-2-oxopyrrolidin-3-yl)propanoate (400 mg, 870.4 umol, 1 eq) in HCl/EtOAc (4 M, 20 mL). The mixture was stirred at 25° C. for 2 h. Once the reaction was completed, the reaction mixture was concentrated to get the product methyl (2S)-2-[[(2S)-2-(tert-butoxycarbonylamino)-2-indan-2-yl-acetyl]amino]-3-[(3S)-2-oxopyrrolidin-3-yl]propanoate (330 mg, crude) was obtained as an oil and used directly next step. MS (ESI) m/z 360.2 [M+H]$^+$ Step 4: methyl (2S)-2-[[(2S)-2-amino-2-indan-2-yl-acetyl]amino]-3-[(3S)-2-oxopyrrolidin-3-yl]propanoate To a mixture of methyl (2S)-2-[[(2S)-2-(tert-butoxycarbonylamino)-2-indan-2-yl-acetyl]amino]-3-[(3S)-2-oxopyrrolidin-3-yl]propanoate (300 mg, 652.84 umol, 1 eq) and 4-methoxy-1H-indole-2-carboxylic acid (149.77 mg, 783.40 umol, 1.2 eq) in DCM (6 mL) and DMF (2 mL) was added DMAP (159.51 mg, 1.31 mmol, 2 eq) and EDCI (250.30 mg, 1.31 mmol, 2 eq). The mixture was stirred at 25° C. and stirred for 2 h. Once the reaction was completed, the reaction was poured into ice-water (30 mL) and extracted with ethyl acetate (20 mL*3). The combined organic phase was dried with anhydrous Na$_2$SO$_4$, filtered and concentrated in vacuum. The residue was purified by silica gel chromatography (column height: 250 mm, diameter: 100 mm, 100-200 mesh silica gel, petroleum ether/ethyl acetate=1/1, 0/1) to give methyl (2S)-2-[[(2S)-2-amino-2-indan-2-yl-acetyl]amino]-3-[(3S)-2-oxopyrrolidin-3-yl]propanoate (300 mg, 506.96 umol, 77.66% yield, 90% purity) (solid). MS (ESI) m/z 533.2 [M+H]$^+$ Step 5: N-[(1S)-1-[[(1S)-2-amino-1-[(3-methylimidazol-4-yl)methyl]-2-oxo-ethyl]carbamoyl]-3-methyl-butyl]-4-methoxy-1H-indole-2-carboxamide To a mixture of (S)-methyl 2-((S)-2-(2,3-dihydro-1H-inden-2-yl)-2-(4-methoxy-1H-indole-2-carboxamido)acetamido)-3-((S)-2-oxopyrrolidin-3-yl)propanoate (100 mg, 187.76 umol, 1 eq) was added ammonia (3.20 mg, 187.76 umol, 3.13 uL, 1 eq). The mixture was stirred at 80° C. and stirred for 16 h. Once the reaction was completed, the reaction was concentrated to give the crude N-((S)-2-(((S)-1-amino-1-oxo-3-((S)-2-oxopyrrolidin-3-yl)propan-2-yl)amino)-1-(2,3-dihydro-1H-inden-2-yl)-2-oxoethyl)-4-methoxy-1H-indole-2-carboxamide (70 mg, 108.20 umol, 57.62% yield, 80% purity) as a solid. Crude product was used directly without further purification. MS (ESI) m/z 518.2 [M+H]$^+$

Step 6: N-[(1S)-2-[[(1S)-1-cyano-2-[(3S)-2-oxopyr-rolidin-3-yl]ethyl]amino]-1-indan-2-yl-2-oxo-ethyl]-4-methoxy-1H-indole-2-carboxamide To a mixture of N-[(1S)-2-[[(1S)-2-amino-2-oxo-1-[[(3S)-2-oxopyrrolidin-3-yl]methyl]ethyl]amino]-1-indan-2-yl-2-oxo-ethyl]-4-methoxy-1H-indole-2-carboxamide (60 mg, 115.93 umol, 1 eq) and methoxycarbonyl-(triethylammonio)sulfonyl-azanide (55.25 mg, 231.85 umol, 2 eq) in DCM (0.5 mL). The mixture was stirred at 25° C. and stirred for 2 h. Once the reaction was completed, the reaction was poured into ice-water (30 mL) and extracted with DCM (20 mL*3). The combined organic phase was dried with anhydrous $Na_2SO_4$, filtered and concentrated in vacuum. The residue was purified by prep-HPLC (column: Phenomenex Gemini-NX 80*40 mm*3 um; mobile phase: [water (10 Mm $NH_4HCO_3$)-ACN]; B %: 20%-50%, 8 min) to give N-[(1S)-2-[[(1S)-1-cyano-2-[(3S)-2-oxopyrrolidin-3-yl]ethyl]amino]-1-indan-2-yl-2-oxo-ethyl]-4-methoxy-1H-indole-2-carboxamide (23.83 mg, 47.70 umol, 41.15% yield, 100% purity) (solid). MS (ESI) m/z 500.3 $[M+H]^+$.

$^1$H NMR (400 MHz, METHANOL-$d_4$) δ ppm 7.26 (s, 1H), 7.13-7.17 (m, 2H), 7.11-7.12 (m, 3H), 7.03 (s, 1H), 6.55-6.52 (d, J=12.4 Hz, 1H), 5.05-5.01 (m, 1H), 4.85-5.00 (m, 1H), 3.92 (s, 3H), 3.25-3.26 (m, 3H), 3.21-3.24 (m, 2H), 2.90-3.01 (m, 2H), 2.88-2.89 (m, 1H), 2.31-3.33 (m, 2H), 1.81-1.92 (m, 2H)

Example 14. Synthesis of Viral Protease Inhibitor Compound 165

Step 1: methyl (2S)-2-amino-3-[(3S)-2-oxopyrroldin-3-yl]propanoate; hydrochloride

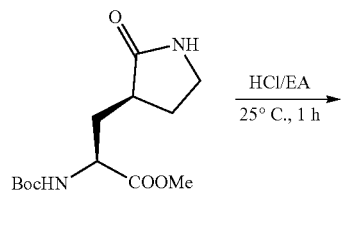

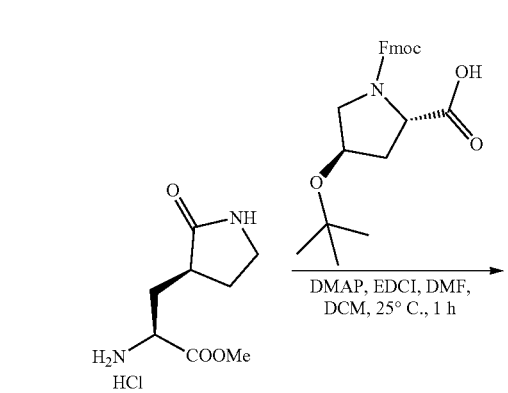

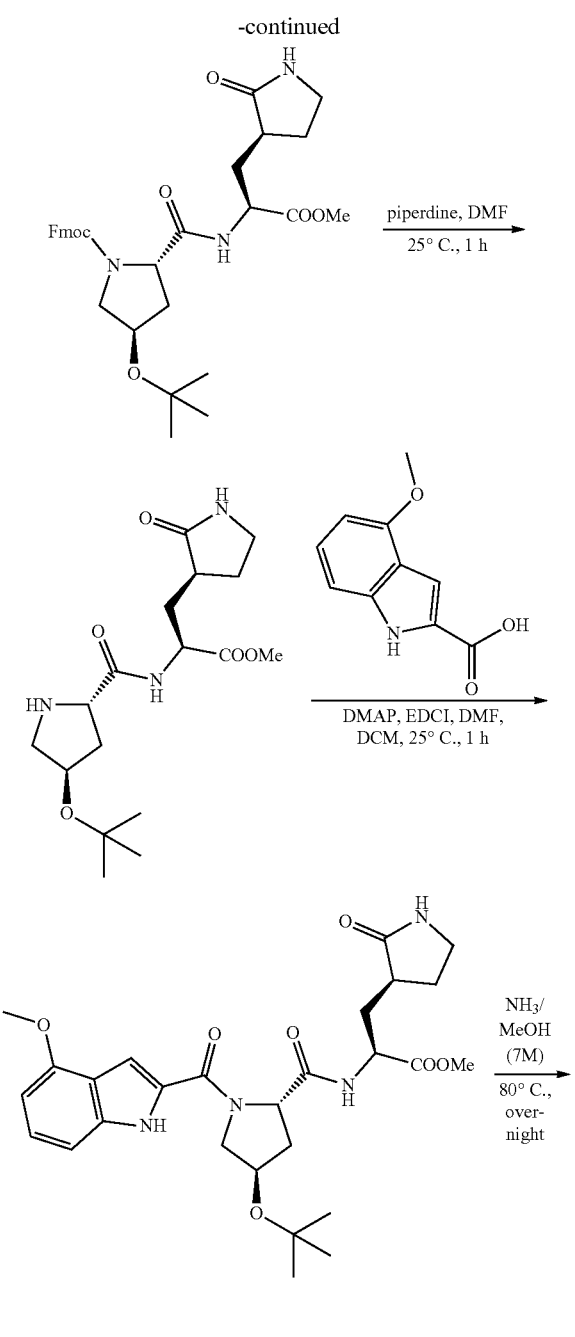

-continued

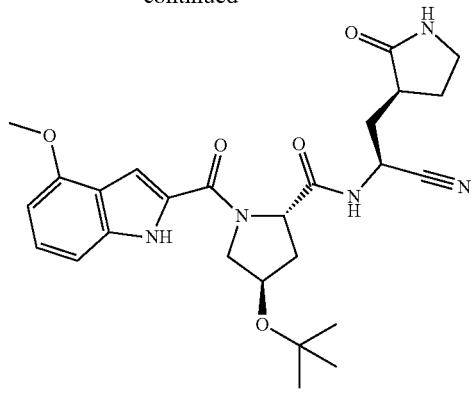

Methyl (2S)-2-(tert-butoxycarbonylamino)-3-[(3S)-2-oxopyrrolidin-3-yl]propanoate (250 mg, 873.14 umol, 1 eq) was added HCl/EtOAc (4 M, 30 mL) at 25° C. The mixture was stirred at 25° C. for 1 h. The reaction mixture was concentrated under reduced pressure to give a product methyl (2S)-2-amino-3-[(3S)-2-oxopyrrolidin-3-yl]propanoate; hydrochloride (200 mg, crude) as a solid and used directly for next step.

Step 2: (2S,4R)-(9H-fluoren-9-yl)methyl-4-(tert-butoxy)-2-(((S)-1-methoxy-1-oxo-3-((S)-2-oxopyrrolidin-3-yl)propan-2-yl)carbamoyl)pyrrolidine-1-carboxylate A mixture of methyl (2S)-2-amino-3-[(3S)-2-oxopyrrolidin-3-yl]propanoate (190 mg, 853.29 umol, 1 eq, HCl), (2S,4R)-4-tert-butoxy-1-(9H-fluoren-9-ylmethoxycarbonyl)pyrrolidine-2-carboxylic acid (349.40 mg, 853.29 umol, 1 eq), EDCI (327.15 mg, 1.71 mmol, 2 eq), DMAP (208.49 mg, 1.71 mmol, 2 eq), DMF (3 mL) and DCM (6 mL) was stirred at 25° C. for 1 h. The reaction mixture was diluted with H$_2$O (30 mL) and extracted with DCM (30 mL*3). The combined organic layers were washed with brine (50 mL), dried over Na$_2$SO$_4$, filtered and concentrated under reduced pressure to give a residue. The residue was purified by column chromatography (SiO$_2$, petroleum ether/EtOAc=0/1) to get the product (2S,4R)-(9H-fluoren-9-yl)methyl-4-(tert-butoxy)-2-(((S)-1-methoxy-1-oxo-3-((S)-2-oxopyrrolidin-3-yl)propan-2-yl)carbamoyl)pyrrolidine-1-carboxylate (230 mg, 319.96 umol, 37.50% yield, 80.36% purity), as an oil. MS (ESI) m/z 578.2 [M+H]$^+$ Step 3: (S)-methyl-2-((2S,4R)-4-(tert-butoxy)pyrrolidine-2-carboxamido)-3-((S)-2-oxopyrrolidin-3-yl)propanoate A mixture of (2S,4R)-(9H-fluoren-9-yl)methyl-4-(tert-butoxy)-2-(((S)-1-methoxy-1-oxo-3-((S)-2-oxopyrrolidin-3-yl)propan-2-yl)carbamoyl)pyrrolidine-1-carboxylate (170 mg, 294.29 umol, 1 eq), piperidine (3.76 g, 8.83 mmol, 4.36 mL, 20% purity, 30 eq), DMF (1 mL) was stirred at 25° C. for 1 h. The reaction mixture was concentrated under reduced pressure to give a residue. The residue was purified by prep-TLC (DCM/MeOH=10/1) to get the product (S)-methyl-2-((2S,4R)-4-(tert-butoxy)pyrrolidine-2-carbox-amido)-3-((S)-2-oxopyrrolidin-3-yl)propanoate (40 mg, 112.54 umol, 38.24% yield) as an oil.

Step 4: (S)-methyl-2-((2S,4R)-4-(tert-butoxy)-1-(4-methoxy-1H-indole-2-carbonyl)pyrrolidine-2-carboxamido)-3-((S)-2-oxopyrrolidin-3-yl)propanoate A mixture of (S)-methyl-2-((2S,4R)-4-(tert-butoxy)pyrrolidine-2-carboxamido)-3-((S)-2-oxopyrrolidin-3-yl)propanoate (40 mg, 112.54 umol, 1 eq), 4-methoxy-1H-indole-2-carboxylic acid (21.52 mg, 112.54 umol, 1 eq), EDCI (43.15 mg, 225.08 umol, 2 eq), DMAP (27.50 mg, 225.08 umol, 2 eq), DMF (0.5 mL) and DCM (1 mL) was stirred at 25° C. for 1 h. The reaction mixture was diluted with H$_2$O (30 mL) and extracted with DCM (30 mL*3). The combined organic layers were washed with brine (50 mL), dried over Na$_2$SO$_4$, filtered and concentrated under reduced pressure to give a residue. The residue was purified by column chromatography (SiO$_2$, petroleum ether/EtOAc=0/1) to get the compound (S)-methyl-2-((2S,4R)-4-(tert-butoxy)-1-(4-methoxy-1H-indole-2-carbonyl)pyrrolidine-2-carboxamido)-3-((S)-2-oxopyrrolidin-3-yl)propanoate (30 mg, 22.33 umol, 19.84% yield), as an oil.

Step 5: (2S,4R)-N-((S)-1-amino-1-oxo-3-((S)-2-oxopyrrolidin-3-yl)propan-2-yl)-4-(tert-butoxy)-1-(4-methoxy-1H-indole-2-carbonyl)pyrrolidine-2-carboxamide A mixture of (S)-methyl-2-((2S,4R)-4-(tert-butoxy)-1-(4-methoxy-1H-indole-2-carbonyl)pyrrolidine-2-carboxamido)-3-((S)-2-oxopyrrolidin-3-yl)propanoate (27 mg, 20.10 umol, 39.35% purity, 1 eq) and NH$_3$/MeOH (7 M, 3 mL) was stirred at 80° C. for 16 h. The reaction mixture was concentrated under reduced pressure to give a product (2S,4R)-N-((S)-1-amino-1-oxo-3-((S)-2-oxopyrrolidin-3-yl)propan-2-yl)-4-(tert-butoxy)-1-(4-methoxy-1H-indole-2-carbonyl)pyrrolidine-2-carboxamide (22 mg, crude) as a solid. MS (ESI) m/z 514.2 [M+H]$^+$ Step 6: (2S,4R)-4-(tert-butoxy)-N-((S)-1-cyano-2-((S)-2-oxopyrrolidin-3-yl)ethyl)-1-(4-methoxy-1H-indole-2-carbonyl)pyrrolidine-2-carboxamide A mixture of (2S,4R)-N-((S)-1-amino-1-oxo-3-((S)-2-oxopyrrolidin-3-yl)propan-2-yl)-4-(tert-butoxy)-1-(4-methoxy-1H-indole-2-carbonyl)pyrrolidine-2-carboxamide (20 mg, 38.94 umol, 1 eq), Burgess reagent (27.84 mg, 116.83 umol, 3 eq) and DCM (1 mL) was stirred at 25° C. for 4 h. The reaction mixture was concentrated under reduced pressure to give a residue. The residue was purified by prep-HPLC (column: Phenomenex Gemini-NX C18 75*30 mm*3 um; mobile phase: [water(0.05% NH$_3$H$_2$O+10 mM NH$_4$HCO$_3$)-ACN]; B %: 20%-40%, 8 min) to get the product (2S,4R)-4-(tert-butoxy)-N-((S)-1-cyano-2-((S)-2-oxopyrrolidin-3-yl)ethyl)-1-(4-methoxy-1H-indole-2-carbonyl)pyrrolidine-2-carboxamide (5 mg, 10.09 umol, 25.91% yield, 100% purity), as a solid. MS (ESI) m/z 496.3 [M+H]$^+$.

$^1$H NMR (400 MHz, DMSO-d$_6$) δ=11.73-11.43 (m, 1H), 9.26-8.84 (m, 1H), 7.84-7.49 (m, 1H), 7.19-7.07 (m, 1H), 7.05-6.96 (m, 1H), 6.94-6.65 (m, 1H), 6.57-6.41 (m, 1H), 5.08-4.92 (m, 1H), 4.85-4.40 (m, 2H), 4.34-4.08 (m, 1H), 3.98-3.75 (m, 3H), 3.74-3.50 (m, 1H), 3.22-2.80 (m, 2H), 2.47-2.37 (m, 1H), 2.27-2.04 (m, 3H), 2.03-1.87 (m, 1H), 1.86-1.36 (m, 2H), 1.15 (s, 9H)

Example 15. Synthesis of Viral Protease Inhibitor Compound 167

Step 1: (S)-methyl 2-amino-3-((S)-2-oxopyrrolidin-3-yl)propanoate

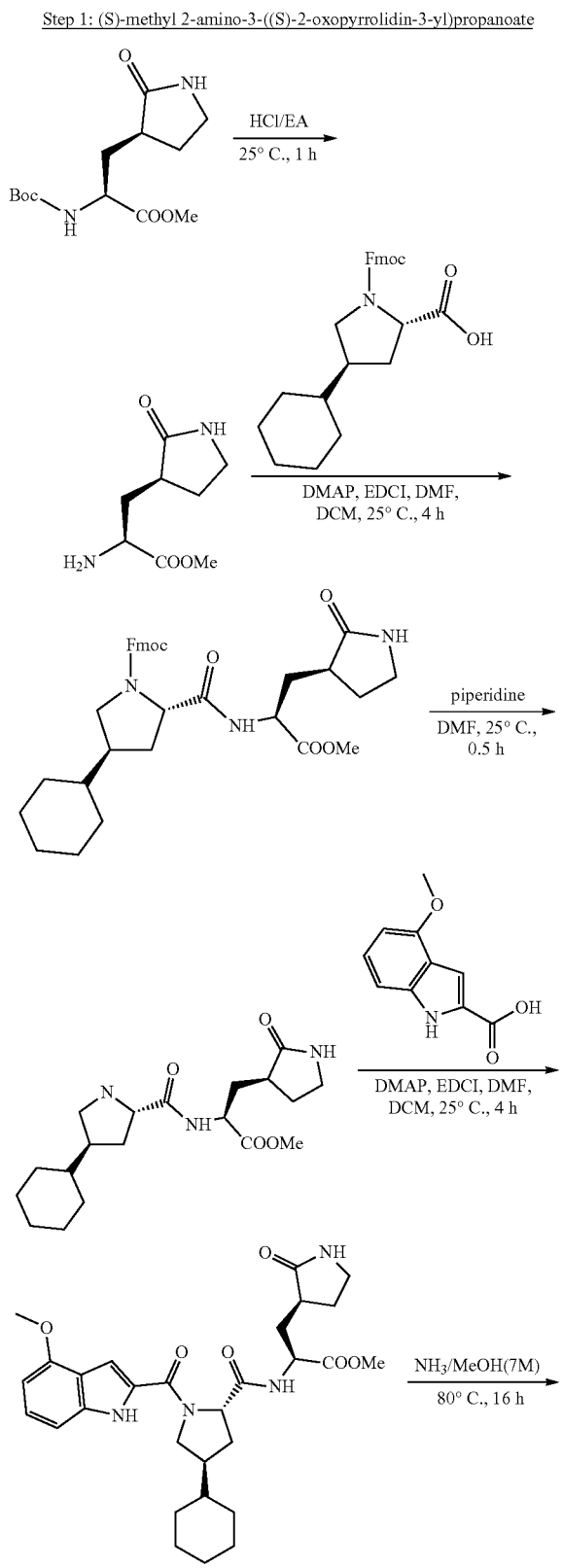

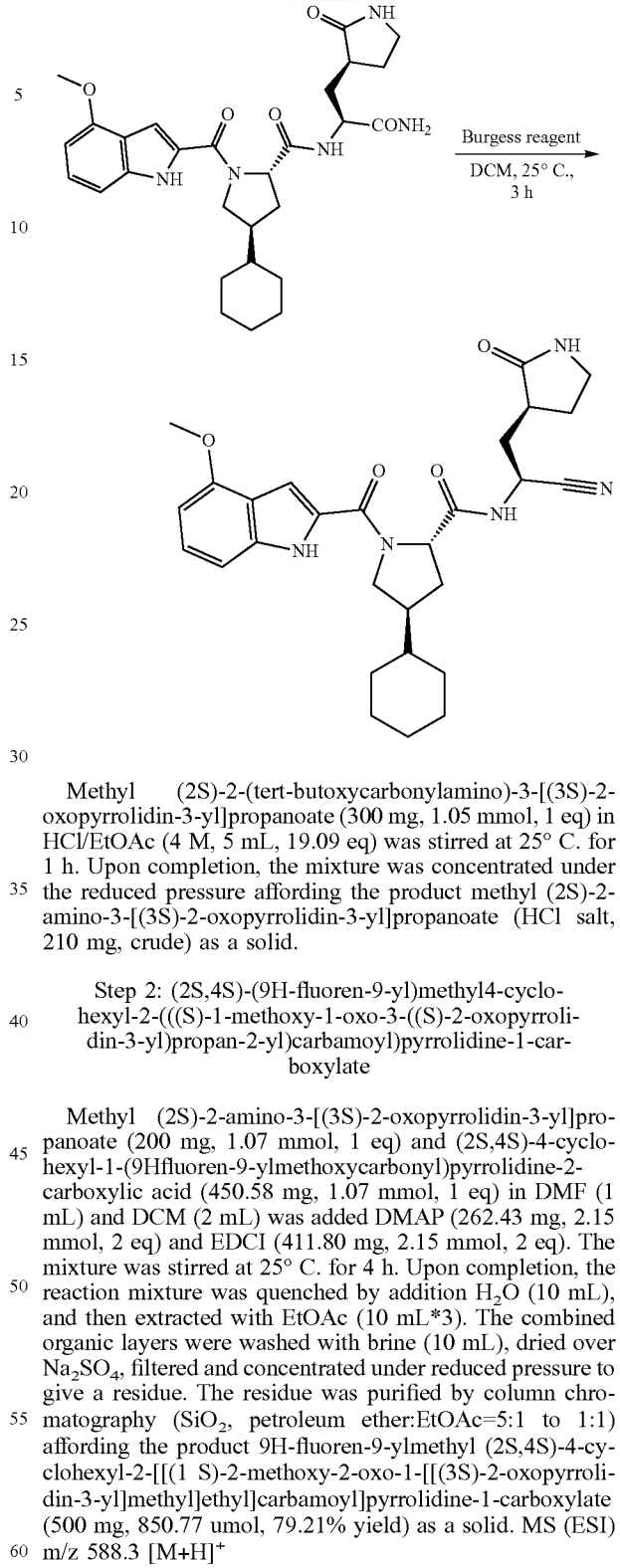

Methyl (2S)-2-(tert-butoxycarbonylamino)-3-[(3S)-2-oxopyrrolidin-3-yl]propanoate (300 mg, 1.05 mmol, 1 eq) in HCl/EtOAc (4 M, 5 mL, 19.09 eq) was stirred at 25° C. for 1 h. Upon completion, the mixture was concentrated under the reduced pressure affording the product methyl (2S)-2-amino-3-[(3S)-2-oxopyrrolidin-3-yl]propanoate (HCl salt, 210 mg, crude) as a solid.

Step 2: (2S,4S)-(9H-fluoren-9-yl)methyl4-cyclohexyl-2-(((S)-1-methoxy-1-oxo-3-((S)-2-oxopyrrolidin-3-yl)propan-2-yl)carbamoyl)pyrrolidine-1-carboxylate Methyl (2S)-2-amino-3-[(3S)-2-oxopyrrolidin-3-yl]propanoate (200 mg, 1.07 mmol, 1 eq) and (2S,4S)-4-cyclohexyl-1-(9Hfluoren-9-ylmethoxycarbonyl)pyrrolidine-2-carboxylic acid (450.58 mg, 1.07 mmol, 1 eq) in DMF (1 mL) and DCM (2 mL) was added DMAP (262.43 mg, 2.15 mmol, 2 eq) and EDCI (411.80 mg, 2.15 mmol, 2 eq). The mixture was stirred at 25° C. for 4 h. Upon completion, the reaction mixture was quenched by addition $H_2O$ (10 mL), and then extracted with EtOAc (10 mL*3). The combined organic layers were washed with brine (10 mL), dried over $Na_2SO_4$, filtered and concentrated under reduced pressure to give a residue. The residue was purified by column chromatography ($SiO_2$, petroleum ether:EtOAc=5:1 to 1:1) affording the product 9H-fluoren-9-ylmethyl (2S,4S)-4-cyclohexyl-2-[[(1 S)-2-methoxy-2-oxo-1-[[(3S)-2-oxopyrrolidin-3-yl]methyl]ethyl]carbamoyl]pyrrolidine-1-carboxylate (500 mg, 850.77 umol, 79.21% yield) as a solid. MS (ESI) m/z 588.3 [M+H]$^+$ Step 3: (S)-methyl2-((2S,4S)-4-cyclohexylpyrrolidine-2-carboxamido)-3-((S)-2-oxopyrrolidin-3-yl)propanoate 9H-fluoren-9-ylmethyl (2S,4S)-4-cyclohexyl-2-[[(1S)-2-methoxy-2-oxo-1-[[(3S)-2-oxopyrrolidin-3-yl]methyl]

ethyl]carbamoyl]pyrrolidine-1-carboxylate (480 mg, 816.74 umol, 1 eq) in DMF (4 mL) and PIPERIDINE (862.20 mg, 10.13 mmol, 1 mL, 12.40 eq) was stirred at 25° C. for 0.5 h. Upon completion, the mixture was drying with $N_2$ and then diluted with DCM (10 mL), concentrated under the reduced pressure to give a residue. The residue was purified by prep-TLC ($SiO_2$, DCM:MeOH=10:1) affording the product methyl (2S)-2-[[(2S,4S)-4-cyclohexylpyrrolidine-2-carbonyl]amino]-3-[(3S)-2-oxopyrrolidin-3-yl]propanoate (210 mg, 574.61 umol, 70.35% yield) as a solid.

Step 4: (S)-methyl2-((2S,4S)-4-cyclohexyl-1-(4-methoxy-1H-indole-2-carbonyl)pyrrolidine-2-carboxamido)-3-((S)-2-oxopyrrolidin-3-yl)propanoate Methyl(2S)-2-[[(2S,4S)-4-cyclohexylpyrrolidine-2-carbonyl]amino]-3-[(3S)-2-oxopyrrolidin-3-yl]propanoate (200 mg, 547.25 umol, 1 eq) and 4-methoxy-1H-indole-2-carboxylic acid (104.62 mg, 547.25 umol, 1 eq) in DMF (2 mL) and DCM (3 mL) was added DMAP (133.71 mg, 1.09 mmol, 2 eq) and EDCI (209.82 mg, 1.09 mmol, 2 eq). The mixture was stirred at 25° C. for 4 h. Upon completion, the reaction mixture was quenched by addition $H_2O$ (10 mL), and then extracted with DCM (10 mL*3). The combined organic layers were washed with brine (10 mL), dried over $Na_2SO_4$, filtered and concentrated under reduced pressure to give a residue. The residue was purified by prep-TLC ($SiO_2$, petroleum ether:EtOAc=0:1) affording the product methyl (2S)-2-[[(2S,4S)-4-cyclohexyl-1-(4-methoxy-1H-indole-2-carbonyl)pyrrolidine-2-carbonyl]amino]-3-[(3S)-2-oxopyrrolidin-3-yl]propanoate (210 mg, 389.88 umol, 71.24% yield) as a solid. MS (ESI) m/z 539.2 [M+H]$^+$ Step 5: (2S,4S)-N-((S)-1-amino-1-oxo-3-((S)-2-oxopyrrolidin-3-yl)propan-2-yl)-4-cyclohexyl-1-(4-methoxy-1H-indole-2-carbonyl)pyrrolidine-2-carboxamide Methyl(2S)-2-[[(2S,4S)-4-cyclohexyl-1-(4-methoxy-1H-indole-2-carbonyl)pyrrolidine-2-carbonyl]amino]-3-[(3S)-2-oxopyrrolidin-3-yl]propanoate (200 mg, 371.31 umol, 1 eq) was in $NH_3$/MeOH (7 M, 10 mL, 188.52 eq). The mixture was stirred at 80° C. for 16 h. Upon completion, the mixture was concentrated under the reduced pressure affording the product (2S,4S)-N-[(1S)-2-amino-2-oxo-1-[[(3S)-2-oxopyrrolidin-3-yl]methyl]ethyl]-4-cyclohexyl-1-(4-methoxy-1Hindole-2-carbonyl)pyrrolidine-2-carboxamide (110 mg, crude) as a solid. MS (ESI) m/z 524.2 [M+H]$^+$ Step 6: (2S,4S)-N-((S)-1-cyano-2-((S)-2-oxopyrrolidin-3-yl)ethyl)-4-cyclohexyl-1-(4-methoxy-1H-indole-2-carbonyl)pyrrolidine-2-carboxamide (2S,4S)-N-[(1S)-2-amino-2-oxo-1-[[(3S)-2-oxopyrrolidin-3-yl]methyl]ethyl]-4-cyclohexyl-1-(4-methoxy-1H-indole-2-carbonyl)pyrrolidine-2-carboxamide (100 mg, 190.98 umol, 1 eq) in DCM (1 mL) was added methoxycarbonyl-(triethylammonio)sulfonyl-azanide (227.55 mg, 954.89 umol, 5 eq). The mixture was stirred at 25° C. for 3 h. Upon completion, the mixture was concentrated under the reduced pressure to give a residue. The residue was purified by prep-HPLC (column: Waters Xbridge BEH C18 100*25 mm*5 um; mobile phase: [water (10 mM $NH_4HCO_3$)-ACN]; B %: 30%-60%, 10 min) affording the product (2S,4S)-N-[(1S)-1-cyano-2-[(3S)-2-oxopyrrolidin-3-yl]ethyl]-4-cyclohexyl-1-(4-methoxy-1H-indole-2-carbonyl)pyrrolidine-2-carboxamide (30.7 mg, 60.17 umol, 31.51% yield, 99.1% purity) as a solid. MS (ESI) m/z 506.3 [M+H]$^+$ $^1$H NMR (400 MHz, MeOD-$d_4$) δ=7.23-6.82 (m, 3H), 6.60-6.36 (m, 1H), 5.21-4.96 (m, 1H), 4.72-4.56 (m, 1H), 4.34-4.07 (m, 1H), 4.00-3.80 (m, 3H), 3.57 (br t, J=9.4 Hz, 1H), 3.02-2.54 (m, 1H), 2.46-0.92 (m, 20H)

Example 16. Synthesis of Viral Protease Inhibitor Compound 209

Step 1: (S)-methyl 2-amino-3-((S)-2-oxopyrrolidin-3-yl)propanoate

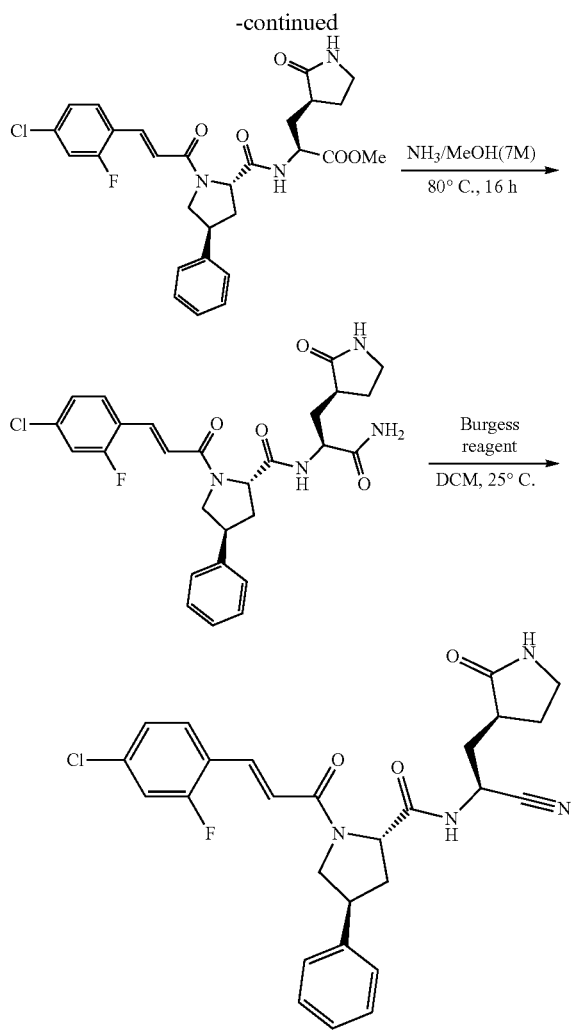

A mixture of methyl (2S)-2-(tert-butoxycarbonylamino)-3-[(3S)-2-oxopyrrolidin-3-yl]propanoate (0.55 g, 1.92 mmol, 1 eq) and HCl/EtOAc (4 M, 10 mL, 20.82 eq) was stirred at 25° C. for 0.5 h. Upon completion, the reaction mixture was concentrated under reduced pressure to give (S)-methyl 2-amino-3-((S)-2-oxopyrrolidin-3-yl)propanoate (0.35 g, crude) as an oil.

Step 2: (2S,4S)-tert-butyl 2-(((S)-1-methoxy-1-oxo-3-((S)-2-oxopyrrolidin-3-yl)propan-2-yl)carbamoyl)-4-phenylpyrrolidine-1-carboxylate A mixture of (S)-methyl 2-amino-3-((S)-2-oxopyrrolidin-3-yl)propanoate (0.15 g, 805.55 umol, 1 eq), (2S,4S)-1-tert-butoxycarbonyl-4-phenyl-pyrrolidine-2-carboxylic acid (234.69 mg, 805.55 umol, 1 eq), DMAP (196.83 mg, 1.61 mmol, 2 eq), EDCI (308.85 mg, 1.61 mmol, 2 eq) in DMF (1 mL) and DCM (2 mL) was stirred at 25° C. for 0.5 h. Upon completion, the reaction mixture was diluted with water (10 mL) and extracted with ethyl acetate (5 mL*3). The combined organic layers were dried over Na$_2$SO$_4$, filtered and concentrated under reduced pressure to give a residue. The residue was purified by column chromatography (SiO$_2$, petroleum ether:EtOAc=2:1 to 0:1) to give (2S,4S)-tert-butyl 2-[[(1S)-2-methoxy-2-oxo-1-[[(3S)-2-oxopyrrolidin-3-yl]methyl]ethyl]carbamoyl]-4-phenyl-pyrrolidine-1-carboxylate (0.25 g, 500.51 umol, 62.13% yield, 92% purity) as a colorless oil. MS (ESI) m/z 460.1 [M+H]$^+$.

Step 3: (S)-methyl 3-((S)-2-oxopyrrolidin-3-yl)-2-((2S,4S)-4-phenylpyrrolidine-2-carboxamido)propanoate A mixture of tert-butyl (2S,4S)-2-[[(1S)-2-methoxy-2-oxo-1-[[(3S)-2-oxopyrrolidin-3-yl]methyl]ethyl]carbamoyl]-4-phenyl-pyrrolidine-1-carboxylate (0.25 g, 544.03 umol, 1 eq) and HCl/EtOAc (4 M, 10 mL, 73.53 eq) was stirred at 25° C. for 0.5 h. Upon completion, the reaction mixture was concentrated under reduced pressure to give methyl (2S)-3-[(3S)-2-oxopyrrolidin-3-yl]-2-[[(2S,4S)-4-phenylpyrrolidine-2-carbonyl]amino]propanoate (0.2 g, crude) as an oil. MS (ESI) m/z 360.1 [M+H]$^+$.

Step 4: (S)-methyl 2-((2S,4S)-1-((E)-3-(4-chloro-2-fluorophenyl)acryloyl)-4-phenylpyrrolidine-2-carboxamido)-3-((S)-2-oxopyrrolidin-3-yl)propanoate A mixture of methyl (2S)-3-[(3S)-2-oxopyrrolidin-3-yl]-2-[[(2S,4S)-4-phenylpyrrolidine-2-carbonyl]amino]propanoate (0.17 g, 472.99 umol, 1 eq), (E)-3-(4-chloro-2-fluoro-phenyl)prop-2-enoic acid (94.88 mg, 472.99 umol, 1 eq), T3P (451.48 mg, 709.48 umol, 421.95 uL, 50% purity, 1.5 eq), TEA (143.58 mg, 1.42 mmol, 197.50 uL, 3 eq) in DMF (4 mL) was degassed stirred at 25° C. for 0.5 h. Upon completion, the reaction mixture was diluted with water (20 mL) and extracted with ethyl acetate (10 mL*3). The combined organic layers were dried over Na$_2$SO$_4$, filtered and concentrated under reduced pressure to give a residue. The residue was purified by column chromatography (SiO$_2$, petroleum ether:EtOAc=2:1 to 0:1) to give methyl (2S)-2-[[(2S,4S)-1-[(E)-3-(4-chloro-2-fluoro-phenyl)prop-2-enoyl]-4-phenyl-pyrrolidine-2-carbonyl]amino]-3-[(3S)-2-oxopyrrolidin-3-yl]propanoate (0.11 g, 162.36 umol, 34.33% yield, 80% purity) as a solid. MS (ESI) m/z 542.1 [M+H]$^+$.

Step 5: (2S,4S)-N-((S)-1-amino-1-oxo-3-((S)-2-oxopyrrolidin-3-yl)propan-2-yl)-1-((E)-3-(4-chloro-2-fluorophenyl)acryloyl)-4-phenylpyrrolidine-2-carboxamide A mixture of methyl (2S)-2-[[(2S,4S)-1-[(E)-3-(4-chloro-2-fluoro-phenyl)prop-2-enoyl]-4-phenyl-pyrrolidine-2-carbonyl]amino]-3-[(3S)-2-oxopyrrolidin-3-yl]propanoate (0.1 g, 184.50 umol, 1 eq) in NH$_3$/MeOH (7M, 3 mL) was stirred at 80° C. for 16 h in the sealed tube. Upon completion, the reaction mixture was concentrated under reduced pressure to give (2S,4S)-N-[(1S)-2-amino-2-oxo-1-[[(3S)-2-oxopyrrolidin-3-yl]methyl]ethyl]-1-[(E)-3-(4-chloro-2-fluoro-phenyl)prop-2-enoyl]-4-phenyl-pyrrolidine-2-carboxamide (0.09 g, crude) as a yellow oil. MS (ESI) m/z 527.0 [M+H]$^+$.

Step 6: (2S,4S)-1-((E)-3-(4-chloro-2-fluorophenyl)acryloyl)-N-((S)-1-cyano-2-((S)-2-oxopyrrolidin-3-yl)ethyl)-4-phenylpyrrolidine-2-carboxamide To a solution of (2S,4S)-N-[(1S)-2-amino-2-oxo-1-[[(3S)-2-oxopyrrolidin-3-yl]methyl]ethyl]-1-[(E)-3-(4-chloro-2-fluoro-phenyl)prop-2-enoyl]-4-phenyl-pyrrolidine-2-carboxamide (0.09 g, 170.78 umol, 1 eq) in DCM (1 mL) was added Burgess reagent (203.50 mg, 853.91 umol, 5 eq), the solution was stirred at 25° C. for 1 h. Upon completion, the reaction mixture was concentrated under reduced pressure to give a residue. The residue was purified by prep-HPLC (column: Waters Xbridge BEH C18 100*25 mm*5 um; mobile phase: [water (10 mM NH$_4$HCO$_3$)-ACN]; B %: 30%-60%, 10 min) to give (2S,4S)-1-[(E)-3-(4-chloro-2-fluoro-phenyl)prop-2-enoyl]-N-[(1S)-1-cyano-2-[(3S)-2-oxopyrrolidin-3-yl]ethyl]-4-phenyl-pyrrolidine-2-carboxamide (29.73 mg, 56.89 umol, 33.31% yield, 97.4% purity) as a solid. MS (ESI) m/z 509.1 [M+H]$^+$.

1H NMR (400 MHz, DMSO-d$_6$) δ=9.17-8.86 (m, 1H), 8.07-7.75 (m, 1H), 7.75-7.65 (m, 1H), 7.62-7.49 (m, 2H), 7.48-7.30 (m, 5H), 7.26 (tt, J=3.0, 5.6 Hz, 1H), 7.22-6.73 (m, 1H), 5.09-4.83 (m, 1H), 4.69-4.47 (m, 1H), 4.40-4.01 (m, 1H), 3.77-3.50 (m, 3H), 3.19-3.04 (m, 2H), 2.44-2.31 (m, 2H), 2.22-2.09 (m, 2H), 1.88-1.59 (m, 2H).

Example 17. Synthesis of Viral Protease Inhibitor Compound 183

Step 1: methyl (2S)-2-amino-3-[(3S)-2-oxopyrrolidin-3-yl]propanoate; hydrochloride

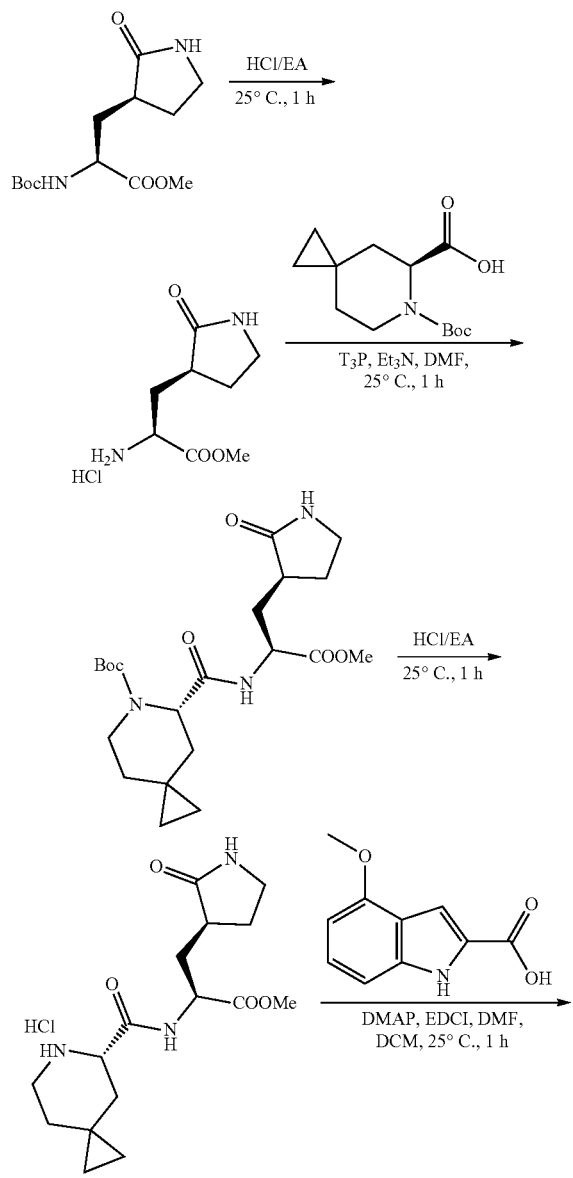

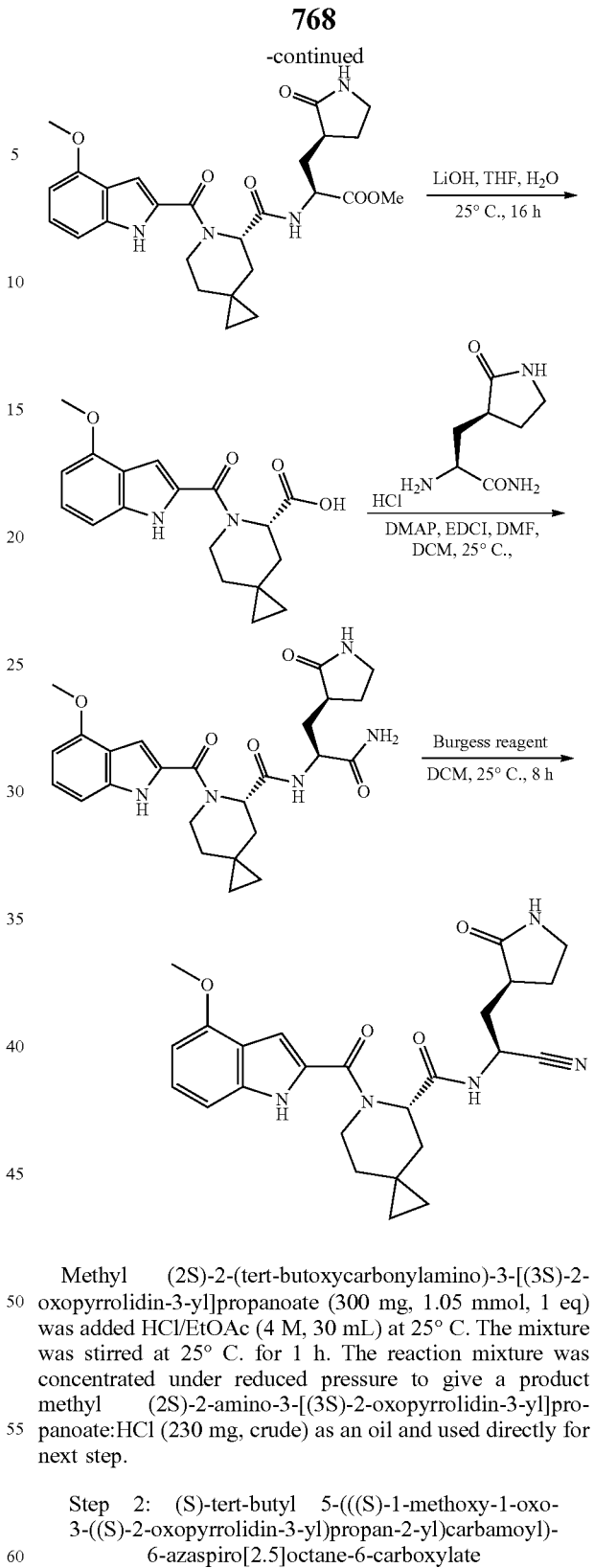

Methyl (2S)-2-(tert-butoxycarbonylamino)-3-[(3S)-2-oxopyrrolidin-3-yl]propanoate (300 mg, 1.05 mmol, 1 eq) was added HCl/EtOAc (4 M, 30 mL) at 25° C. The mixture was stirred at 25° C. for 1 h. The reaction mixture was concentrated under reduced pressure to give a product methyl (2S)-2-amino-3-[(3S)-2-oxopyrrolidin-3-yl]propanoate:HCl (230 mg, crude) as an oil and used directly for next step.

Step 2: (S)-tert-butyl 5-(((S)-1-methoxy-1-oxo-3-((S)-2-oxopyrrolidin-3-yl)propan-2-yl)carbamoyl)-6-azaspiro[2.5]octane-6-carboxylate A mixture of methyl (2S)-2-amino-3-[(3S)-2-oxopyrrolidin-3-yl]propanoate (230 mg, 1.03 mmol, 1 eq, HCl), (7S)-6-tert-butoxycarbonyl-6-azaspiro[2.5]octane-7-carboxylic acid (263.72 mg, 1.03 mmol, 1 eq), T$_3$P (657.31 mg, 2.07 mmol, 614.31 uL, 2 eq), Et$_3$N (522.60 mg, 5.16 mmol, 718.85 uL, 5 eq) and DMF (5 mL) was stirred at 25° C. for 1 h. The reaction mixture was diluted with H₂O (30 mL) and extracted with DCM (30 mL*3). The combined organic layers were washed with brine (50 mL), dried over Na₂SO₄, filtered and concentrated under reduced pressure to give a residue. The residue was purified by column chromatography (SiO₂, petroleum ether/EtOAc=0/1) to get the product (S)-tert-butyl 5-(((S)-1-methoxy-1-oxo-3-((S)-2-oxopyrrolidin-3-yl)propan-2-yl)carbamoyl)-6-azaspiro[2.5]octane-6-carboxylate (300 mg, 708.38 umol, 68.58% yield), as yellow oil. MS (ESI) m/z 424.1 [M+H]⁺

Step 3: (S)-methyl 3-((S)-2-oxopyrrolidin-3-yl)-2-((S)-6-azaspiro[2.5]octane-5-carboxamido)propanoate A mixture of (S)-tert-butyl 5-(((S)-1-methoxy-1-oxo-3-((S)-2-oxopyrrolidin-3-yl)propan-2-yl)carbamoyl)-6-azaspiro[2.5]octane-6-carboxylate (290 mg, 684.77 umol, 1 eq) and HCl/EtOAc (4 M, 30 mL) was stirred at 25° C. for 1 h. The reaction mixture was concentrated under reduced pressure to give a product (S)-methyl 3-((S)-2-oxopyrrolidin-3-yl)-2-((S)-6-azaspiro[2.5]octane-5-carboxamido)propanoate (240 mg, crude, HCl) as a an oil and used directly for next step.

Step 4: (S)-methyl 2-((S)-6-(4-methoxy-1H-indole-2-carbonyl)-6-azaspiro[2.5]octane-5-carboxamido)-3-((S)-2-oxopyrrolidin-3-yl)propanoate A mixture of (S)-methyl 3-((S)-2-oxopyrrolidin-3-yl)-2-((S)-6-azaspiro[2.5]octane-5-carboxamido)propanoate (240 mg, 666.95 umol, 1 eq, HCl), 4-methoxy-1H-indole-2-carboxylic acid (127.51 mg, 666.95 umol, 1 eq), DMAP (162.96 mg, 1.33 mmol, 2 eq), EDCI (255.71 mg, 1.33 mmol, 2 eq), DMF (2 mL) and DCM (4 mL) was stirred at 25° C. for 1 h. The reaction mixture was diluted with H₂O (30 mL) and extracted with DCM (30 mL*3). The combined organic layers were washed with brine (50 mL), dried over Na₂SO₄, filtered and concentrated under reduced pressure to give a residue. The residue was purified by column chromatography (SiO₂, petroleum ether/EtOAc=0/1) to get the compound (S)-methyl 2-((S)-6-(4-methoxy-1H-indole-2-carbonyl)-6-azaspiro[2.5]octane-5-carboxamido)-3-((S)-2-oxopyrrolidin-3-yl)propanoate (150 mg, 275.74 umol, 41.34% yield, 91.28% purity) as an oil. MS (ESI) m/z 495.2 [M−H]⁻

Step 5: (S)-6-(4-methoxy-1H-indole-2-carbonyl)-6-azaspiro[2.5]octane-5-carboxylic acid A mixture of (S)-methyl 2-((S)-6-(4-methoxy-1H-indole-2-carbonyl)-6-azaspiro[2.5]octane-5-carboxamido)-3-((S)-2-oxopyrrolidin-3-yl)propanoate, LiOH (24.12 mg, 1.01 mmol, 5 eq), H₂O (1 mL) and THF (4 mL) was stirred at 25° C. for 16 h. The reaction mixture was concentrated under reduced pressure to give a product (S)-6-(4-methoxy-1H-indole-2-carbonyl)-6-azaspiro[2.5]octane-5-carboxylic acid (65 mg, crude) as a solid. MS (ESI) m/z 327.1 [M−H]⁻

Step 6: tert-butyl ((S)-1-amino-1-oxo-3-((S)-2-oxopyrrolidin-3-yl)propan-2-yl)carbamate A mixture of methyl (2S)-2-(tert-butoxycarbonylamino)-3-[(3S)-2-oxopyrrolidin-3-yl]propanoate (400 mg, 1.40 mmol, 1 eq) and NH₃/MeOH (7 M, 10 mL) was stirred at 80° C. for 16 h. The reaction mixture was concentrated under reduced pressure to give a product tert-butyl ((S)-1-amino-1-oxo-3-((S)-2-oxopyrrolidin-3-yl)propan-2-yl)carbamate (380 mg, crude) as a solid.

Step 7: (S)-2-amino-3-((S)-2-oxopyrrolidin-3-yl)propanamide

A mixture of tert-butyl ((S)-1-amino-1-oxo-3-((S)-2-oxopyrrolidin-3-yl)propan-2-yl)carbamate (300 mg, 1.11 mmol, 1 eq) and HCl/EtOAc (4 M, 15 mL, 54.26 eq) was stirred at 25° C. for 0.5 h. The reaction mixture was concentrated under reduced pressure to give a product (S)-2-amino-3-((S)-2-oxopyrrolidin-3-yl)propanamide (190 mg, crude) as a solid and used directly for next step.

Step 8: (S)-N-((S)-1-amino-1-oxo-3-((S)-2-oxopyrrolidin-3-yl)propan-2-yl)-6-(4-methoxy-1H-indole-2-carbonyl)-6-azaspiro[2.5]octane-5-carboxamide A solution of (S)-6-(4-methoxy-1H-indole-2-carbonyl)-6-azaspiro[2.5]octane-5-carboxylic acid (65 mg, 197.95 umol, 1 eq), (S)-2-amino-3-((S)-2-oxopyrrolidin-3-yl)propanamide (33.89 mg, 197.95 umol, 1 eq), DMAP (48.37 mg, 395.91 umol, 2 eq), EDCI (75.90 mg, 395.91 umol, 2 eq), DMF (1 mL) and DCM (3 mL) was stirred at 25° C. for 16 h. The reaction mixture was diluted with H₂O (30 mL) and extracted with DCM (30 mL*3). The combined organic layers were washed with brine (50 mL), dried over Na₂SO₄, filtered and concentrated under reduced pressure to give a residue. The residue was purified by prep-HPLC (column: Phenomenex Gemini-NX C18 75*30 mm*3 um; mobile phase: [water(0.05% NH₃H₂O+10 mM NH₄HCO₃)-ACN]; B %: 10%-40%, 8 min) to get the compound (S)-N-((S)-1-amino-1-oxo-3-((S)-2-oxopyrrolidin-3-yl)propan-2-yl)-6-(4-methoxy-1H-indole-2-carbonyl)-6-azaspiro[2.5]octane-5-carboxamide (45 mg, 79.43 umol, 40.13% yield, 85% purity) as a solid. MS (ESI) m/z 480.2 [M−H]⁻

Step 9: (S)-N-((S)-1-cyano-2-((S)-2-oxopyrrolidin-3-yl)ethyl)-6-(4-methoxy-1H-indole-2-carbonyl)-6-azaspiro[2.5]octane-5-carboxamide A mixture of (S)-N-((S)-1-amino-1-oxo-3-((S)-2-oxopyrrolidin-3-yl)propan-2-yl)-6-(4-methoxy-1H-indole-2-carbonyl)-6-azaspiro[2.5]octane-5-carboxamide (40 mg, 83.07 umol, 1 eq), Burgess reagent (237.55 mg, 996.80 umol, 12 eq) and DCM (20 mL) was stirred at 25° C. for 8 h. The reaction mixture was concentrated under reduced pressure to give a residue. The residue was purified by prep-HPLC (column: Phenomenex Gemini-NX C18 75*30 mm*3 um; mobile phase: [water(0.05% NH₃H₂O+10 mM NH4HCO₃)-ACN]; B %: 20%-40%, 8 min) to get the product (S)-N-((S)-1-cyano-2-((S)-2-oxopyrrolidin-3-yl)ethyl)-6-(4-methoxy-1H-indole-2-carbonyl)-6-azaspiro[2.5]octane-5-carboxamide (17 mg, 34.79 umol, 41.89% yield, 94.87% purity), as a solid. MS (ESI) m/z 462.2 [M−H]⁻.

¹H NMR (400 MHz, DMSO-d₆) δ=11.64 (s, 1H), 9.26-8.52 (m, 1H), 7.87-7.61 (m, 1H), 7.18-7.07 (m, 1H), 7.06-6.96 (m, 1H), 6.85-6.60 (m, 1H), 6.51 (d, 1H), 5.30-4.93 (m, 2H), 4.61-4.41 (m, 1H), 3.85 (s, 3H), 3.21-2.96 (m, 2H), 2.39-2.03 (m, 5H), 1.96-1.56 (m, 4H), 0.99 (d, 1H), 0.45-0.15 (m, 4H)

Example 18. Synthesis of Viral Protease Inhibitor Compound 185

Step 1: (S)-methyl 2-((S)-2-((tert-butoxycarbonyl)amino)-3-cyclohexyl propanamido)-3-((S)-2-oxopyrrolidin-3-yl)propanoate

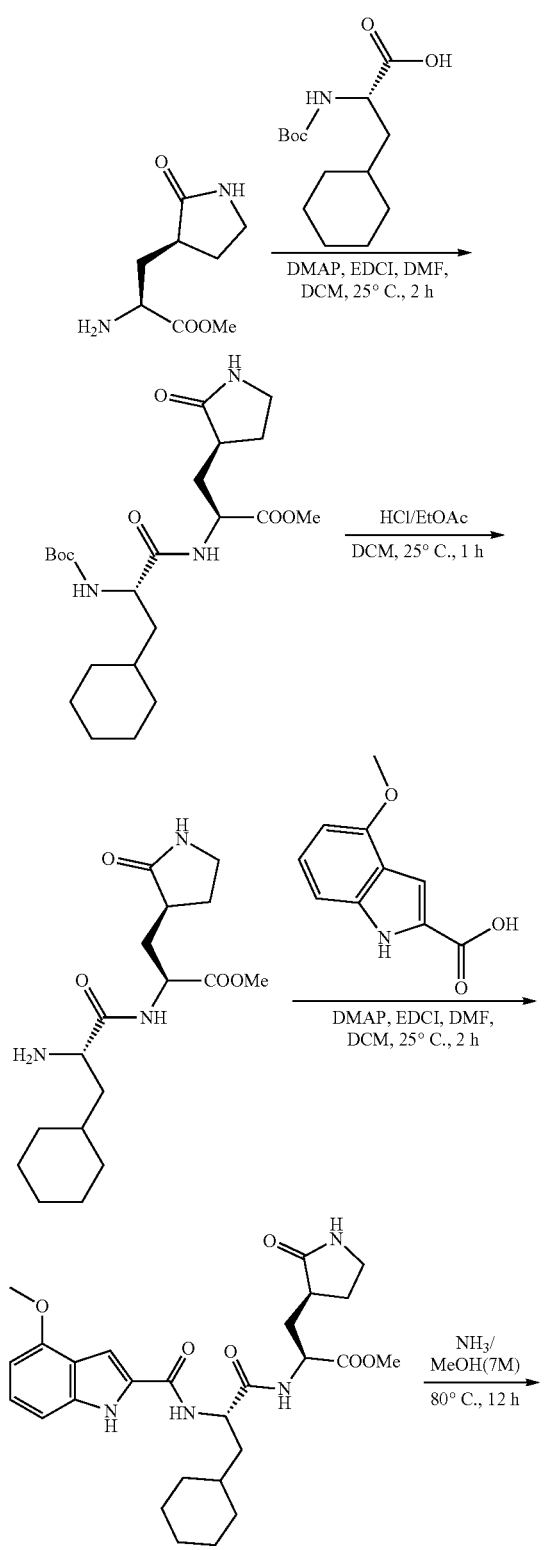

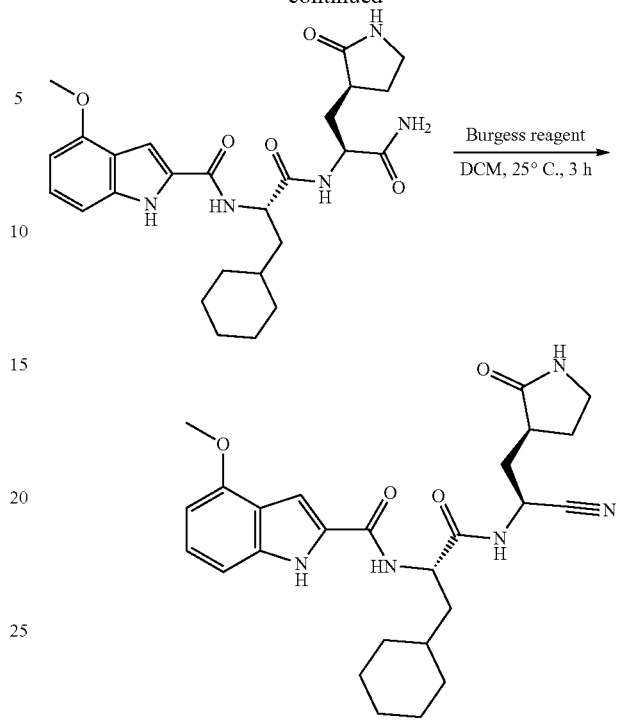

To a solution of methyl (2S)-2-amino-3-[(3S)-2-oxopyrrolidin-3-yl]propanoate (170 mg, 763.47 umol, 1 eq, HCl) and (2S)-2-(tert-butoxycarbonylamino)-3-cyclohexyl-propanoic acid (207.17 mg, 763.47 umol, 1 eq) in DMF (2 mL) was added DMAP (186.55 mg, 1.53 mmol, 2 eq) and EDCI (292.71 mg, 1.53 mmol, 2 eq). The mixture was added DCM (3 mL) and stirred at 25° C. for 2 h. The reaction mixture was quenched by addition H$_2$O (30 mL) at 0° C., and then extracted with DCM (20 mL*3). The combined organic layers were washed with brine, dried over Na$_2$SO$_4$, filtered and concentrated under reduced pressure to give a residue. The residue was purified by prep-TLC (SiO$_2$, petroleum ether/EtOAc=0/1) to get the product methyl (2S)-2-[[(2S)-2-(tert-butoxycarbonylamino)-3-cyclohexyl-propanoyl]amino]-3-[(3S)-2-oxopyrrolidin-3-yl]propanoate (250 mg, 568.77 umol, 74.50% yield) was obtained as a solid. MS (ESI) m/z 440.3 [M+H]$^+$ Step 2. (S)-methyl 2-((S)-2-amino-3-cyclohexylpropanamido)-3-((S)-2-oxopyrrolidin-3-yl)propanoate A solution of methyl (2S)-2-[[(2S)-2-(tert-butoxycarbonylamino)-3-cyclohexyl-propanoyl]amino]-3-[(3S)-2-oxopyrrolidin-3-yl]propanoate (200 mg, 455.02 umol, 1 eq) in EtOAc (0.5 mL) was added drop-wise HCl/EtOAc (4 M, 2.00 mL, 17.58 eq) at 25° C. The mixture was stirred at 25° C. for 1 h. The reaction mixture was concentrated under reduced pressure to give a product methyl (2S)-2-[[(2S)-2-amino-3-cyclohexyl-propanoyl]amino]-3-[(3S)-2-oxopyrrolidin-3-yl]propanoate (150 mg, crude, HCl) was obtained as a solid and used directly next step. MS (ESI) m/z 340.1 [M+H]$^+$ Step 3: ((S)-methyl 2-((S)-3-cyclohexyl-2-(4-methoxy-1H-indole-2-carboxamido)propanamido)-3-((S)-2-oxopyrrolidin-3-yl)propanoate A solution of 4-methoxy-1H-indole-2-carboxylic acid (99.18 mg, 518.77 umol, 1.3 eq) and methyl (2S)-2-[[(2S)-

2-amino-3-cyclohexyl-propanoyl]amino]-3-[(3S)-2-oxopyrrolidin-3-yl]propanoate (150 mg, 399.05 umol, 1 eq, HCl) in DMF (2 mL) was added DMAP (97.50 mg, 798.11 umol, 2.0 eq) and EDCI (153.00 mg, 798.11 umol, 2 eq). The mixture was added DCM (4 mL) and stirred at 25° C. for 2 h. The reaction mixture was quenched by addition H₂O (20 mL) at 0° C., and then extracted with DCM (20 mL*3). The combined organic layers were washed with brine (20 mL), dried over Na₂SO₄, filtered and concentrated under reduced pressure to give a residue. The residue was purified by column chromatography (SiO₂, DCM:MeOH=1:0 to 10:1) to get a product methyl (2S)-2-[[(2S)-3-cyclohexyl-2-[(4-methoxy-1H-indole-2-carbonyl)amino]propanoyl]amino]-3-[(3S)-2-oxopyrrolidin-3-yl]propanoate (150 mg, 292.63 umol, 73.33% yield) was obtained as a solid.

¹H NMR (METHANOL-d₄, 400 MHz): δ ppm 7.26 (s, 1H), 7.09-7.20 (m, 1H), 7.02 (d, J=8.3 Hz, 1H), 6.51 (d, J=7.6 Hz, 1H), 4.66 (br dd, J=9.0, 6.3 Hz, 1H), 4.52-4.58 (m, 1H), 3.93 (s, 3H), 3.72 (s, 3H), 3.22-3.29 (m, 2H), 2.54-2.62 (m, 1H), 2.26-2.33 (m, 1H), 2.15-2.23 (m, 1H), 1.66-1.87 (m, 9H), 1.47-1.54 (m, 1H), 1.25-1.40 (m, 3H), 0.96-1.06 (m, 2H)

Step 4: N-((S)-1-(((S)-1-amino-1-oxo-3-((S)-2-oxopyrrolidin-3-yl)propan-2-yl)amino)-3-cyclohexyl-1-oxopropan-2-yl)-4-methoxy-1H-indole-2-carboxamide To a solution of methyl (2S)-2-[[(2S)-3-cyclohexyl-2-[(4-methoxy-1H-indole-2-carbonyl)amino]propanoyl]amino]-3-[(3S)-2-oxopyrrolidin-3-yl]propanoate (150 mg, 292.63 umol, 1 eq) in ammonia (15.30 g, 898.39 mmol, 15.00 mL, 3070.07 eq) was heated to 80° C. for 12 h in a sealed tube. The reaction mixture was concentrated under reduced pressure to get a product N-[(1S)-2-[[(1S)-2-amino-2-oxo-1-[[(3S)-2-oxopyrrolidin-3-yl]methyl]ethyl]amino]-1-(cyclohexylmethyl)-2-oxo-ethyl]-4-methoxy-1H-indole-2-carboxamide (140 mg, crude) was obtained as a solid. MS (ESI) m/z 498.2 [M+H]⁺

¹H NMR (METHANOL-d4, 400 MHz): δ ppm 7.27-7.34 (m, 1H), 7.13-7.20 (m, 1H), 7.05 (d, J=8.3 Hz, 1H), 6.53 (d, J=7.7 Hz, 1H), 4.62 (t, J=7.6 Hz, 1H), 4.42-4.51 (m, 1H), 3.95 (s, 3H), 3.22-3.30 (m, 2H), 2.53 (td, J=9.2, 4.5 Hz, 1H), 2.33 (ddd, J=9.2, 6.4, 3.4 Hz, 1H), 2.17 (ddd, J=14.1, 11.4, 4.6 Hz, 1H), 1.71-1.88 (m, 9H), 1.46-1.53 (m, 1H), 1.21-1.32 (m, 3H), 0.97-1.09 (m, 2H)

Step 5: N-((S)-1-(((S)-1-amino-1-oxo-3-((S)-2-oxopyrrolidin-3-yl)propan-2-yl)amino)-3-cyclohexyl-1-oxopropan-2-yl)-4-methoxy-1H-indole-2-carboxamide To a solution of N-[(1S)-2-[[(1S)-2-amino-2-oxo-1-[[(3S)-2-oxopyrrolidin-3-yl]methyl]ethyl]amino]-1-(cyclohexylmethyl)-2-oxo-ethyl]-4-methoxy-1H-indole-2-carboxamide (80 mg, 160.78 umol, 1 eq) in DCM (3 mL) was added Burgess reagent (114.94 mg, 482.33 umol, 3 eq), then the mixture was stirred at 25° C. for 3 h. The reaction mixture was concentrated under reduced pressure to give a residue. The residue was purified by neutral prep-HPLC to get a product N-[(1S)-2-[[(1S)-1-cyano-2-[(3S)-2-oxopyrrolidin-3-yl]ethyl]amino]-1-(cyclohexylmethyl)-2-oxo-ethyl]-4-methoxy-1H-indole-2-carboxamide (20.02 mg, 41.75 umol, 25.97% yield, 100% purity) was obtained as a solid. MS (ESI) m/z 480.1 [M+H]⁺.

Prep-HPLC condition: column: Waters Xbridge BEH C18 100*25 mm*5 um; mobile phase: [water (10 mM NH₄HCO₃)-ACN]; B %: 30%-60%, 10 min ¹H NMR (METHANOL-d₄, 400 MHz): δ ppm 7.28 (s, 1H), 7.11-7.18 (m, 1H), 7.02 (d, J=8.3 Hz, 1H), 6.51 (d, J=7.6 Hz, 1H), 5.05 (dd, J=10.1, 5.9 Hz, 1H), 4.56-4.61 (m, 1H), 3.93 (s, 3H), 3.22-3.30 (m, 2H), 2.55-2.66 (m, 1H), 2.23-2.40 (m, 2H), 1.65-1.94 (m, 9H), 1.41-1.52 (m, 1H), 1.17-1.36 (m, 3H), 0.94-1.10 (m, 2H).

Example 19. Synthesis of Viral Protease Inhibitor Compound 197

Step 1: methyl (2S)-2-amino-3-[(3S)-2-oxopyrrolidin-3-yl]propanoate

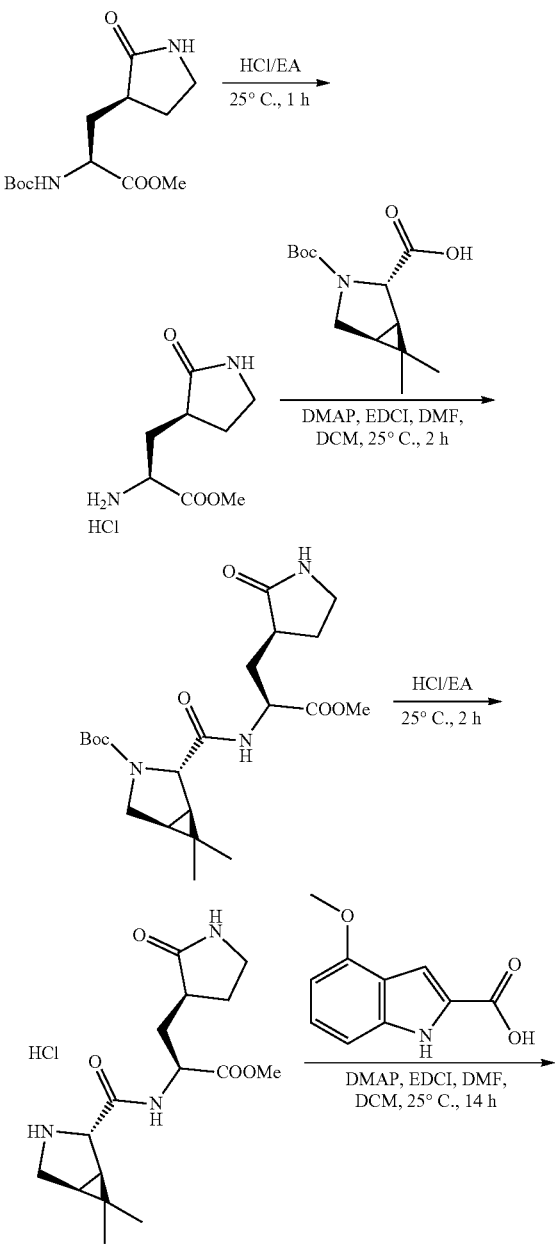

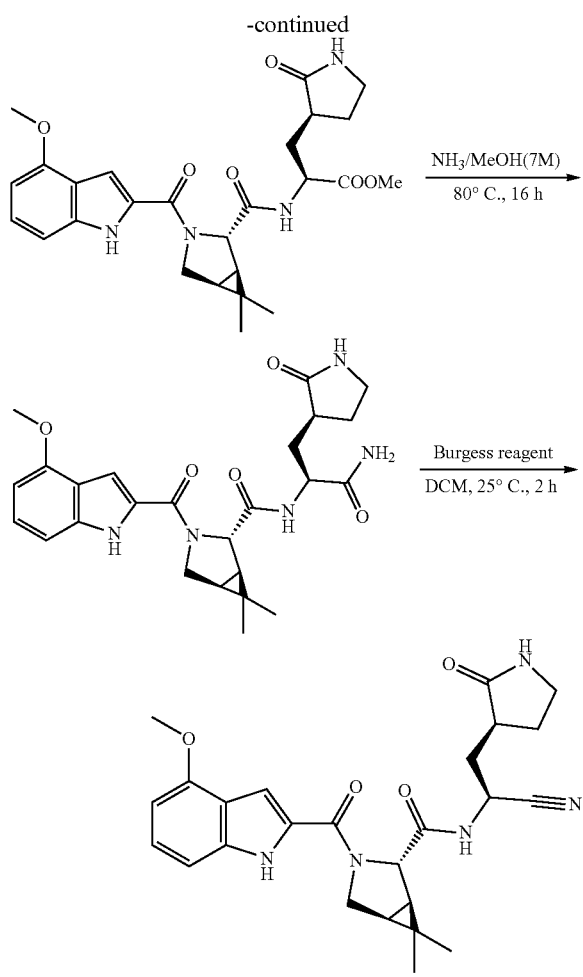

To a mixture of methyl (2S)-2-(tert-butoxycarbonylamino)-3-[(3S)-2-oxopyrrolidin-3-yl]propanoate (500 mg, 1.75 mmol, 1 eq) in HCl/EtOAc (4M, 20 mL). The mixture was stirred at 25° C. and stirred for 1 h. Once the reaction was completed, the reaction was concentrated to give the crude methyl (2S)-2-amino-3-[(3S)-2-oxopyrrolidin-3-yl]propanoate (400 mg, crude, an oil). The crude product was used directly without further purification. MS (ESI) m/z 187.1 [M+H]+

Step 2: tert-butyl (2S,5S)-2-[[(1S)-2-methoxy-2-oxo-1-[[(3S)-2-oxopyrrolidin-3-yl]methyl]ethyl]carbamoyl]-6,6-dimethyl-3-azabicyclo[3.1.0]hexane-3-carboxylate To a mixture of methyl (2S)-2-amino-3-[(3S)-2-oxopyrrolidin-3-yl]propanoate (230 mg, 1.24 mmol, 1 eq) and (2S,5S)-3-tert-butoxycarbonyl-6,6-dimethyl-3-azabicyclo[3.1.0]hexane-2-carboxylic acid (315.35 mg, 1.24 mmol, 1 eq) in DCM (4.5 mL) and DMF (1.5 mL) was added EDCI (473.57 mg, 2.47 mmol, 2 eq) and DMAP (301.80 mg, 2.47 mmol, 2 eq). The mixture was stirred at 25° C. for 2 h. Once the reaction was completed, the reaction was concentrated and purified by prep-HPLC (column: Waters Xbridge BEH C18 100*30 mm*10 um; mobile phase: [water (10 mM NH4HCO3)-ACN]; B %: 25%-55%, 10 min) to give tert-butyl (2S,5S)-2-[[(1S)-2-methoxy-2-oxo-1-[[(3S)-2-oxopyrrolidin-3-yl]methyl]ethyl]carbamoyl]-6,6-dimethyl-3-azabicyclo[3.1.0]hexane-3-carboxylate (200 mg, 425.03 umol, 34.41% yield, 90% purity) (solid). MS (ESI) m/z 424.1 [M+H]+

Step 3: (S)-methyl 2-((1S,2S,5S)-6,6-dimethyl-3-azabicyclo[3.1.0]hexane-2-carboxamido)-3-((S)-2-oxopyrrolidin-3-yl)propanoate To a mixture of (1S,2S,5S)-tert-butyl 2-(((S)-1-methoxy-1-oxo-3-((S)-2-oxopyrrolidin-3-yl)propan-2-yl)carbamoyl)-6,6-dimethyl-3-azabicyclo[3.1.0]hexane-3-carboxylate (200 mg, 236.13 umol, 50% purity, 1 eq) in HCl/EtOAc (4M, 20 mL). The mixture was stirred at 25° C. and stirred for 2 h. Once the reaction was completed, the reaction was concentrated to give the crude (S)-methyl 2-((1S,2S,5S)-6,6-dimethyl-3-azabicyclo[3.1.0]hexane-2-carboxamido)-3-((S)-2-oxopyrrolidin-3-yl)propanoate (150 mg, crude, an oil). Crude product was used directly without further purification. MS (ESI) m/z 324.1 [M+H]+

Step 4: methyl (2S)-2-[[(2S,5S)-3-(4-methoxy-1H-indole-2-carbonyl)-6,6-dimethyl-3-azabicyclo[3.1.0]hexane-2-carbonyl]amino]-3-[(3S)-2-oxopyrrolidin-3-yl]propanoate To a mixture of (S)-methyl 2-((1S,2S,5S)-6,6-dimethyl-3-azabicyclo[3.1.0]hexane-2-carboxamido)-3-((S)-2-oxopyrrolidin-3-yl)propanoate (150 mg, 463.84 umol, 1 eq) and 4-methoxy-1H-indole-2-carboxylic acid (88.68 mg, 463.84 umol, 1 eq) in DCM (3 mL) and DMF (1 mL) was added EDCI (177.84 mg, 927.68 umol, 2 eq) and DMAP (113.33 mg, 927.68 umol, 2 eq). The mixture was stirred at 25° C. and stirred for 14 h. Once the reaction was completed, the mixture was poured into water (50 mL) and extracted with DCM (20 mL*3). The combined organic phase was washed with brine (60 mL*3), dried with anhydrous Na2SO4, filtered and concentrated in vacuum. The residue was purified by silica gel chromatography (column height: 250 mm, diameter: 100 mm, 100-200 mesh silica gel, petroleum ether/ethyl acetate=1/1, 0/1) to afford methyl (2S)-2-[[(2S,5S)-3-(4-methoxy-1H-indole-2-carbonyl)-6,6-dimethyl-3-azabicyclo[3.1.0]hexane-2-carbonyl]amino]-3-[(3S)-2-oxopyrrolidin-3-yl]propanoate (50 mg, 80.56 umol, 17.37% yield, 80% purity) as solid. MS (ESI) m/z 497.2 [M+H]+

Step 5: (2S,5S)-N-[(1S)-2-amino-2-oxo-1-[[(3S)-2-oxopyrrolidin-3-yl]methyl]ethyl]-3-(4-methoxy-1H-indole-2-carbonyl)-6,6-dimethyl-3-azabicyclo[3.1.0]hexane-2-carboxamide To a mixture of methyl (2S)-2-[[(2S,5S)-3-(4-methoxy-1H-indole-2-carbonyl)-6,6-dimethyl-3-azabicyclo[3.1.0]hexane-2-carbonyl]amino]-3-[(3S)-2-oxopyrrolidin-3-yl]propanoate (100 mg, 201.39 umol, 1 eq) in ammonia (5.10 g, 299.46 mmol, 5 mL, 1486.99 eq). The mixture was stirred at 80° C. and stirred for 16 h. Once the reaction was completed, the reaction was concentrated to give the crude (2S,5S)-N-[(1S)-2-amino-2-oxo-1-[[(3S)-2-oxopyrrolidin-3-yl]methyl]ethyl]-3-(4-methoxy-1H-indole-2-carbonyl)-6,6-dimethyl-3-azabicyclo[3.1.0]hexane-2-carboxamide (100 mg, crude) (solid). Crude product was used directly without further purification. MS (ESI) m/z 482.3[M+H]+

Step 6: (2S,5S)-N-[(1S)-1-cyano-2-[(3S)-2-oxopyrrolidin-3-yl]ethyl]-3-(4-methoxy-1H-indole-2-carbonyl)-6,6-dimethyl-3-azabicyclo[3.1.0]hexane-2-carboxamide To a mixture of (2S,5S)-N-[(1S)-2-amino-2-oxo-1-[[(3S)-2-oxopyrrolidin-3-yl]methyl]ethyl]-3-(4-methoxy-1H-indole-2-carbonyl)-6,6-dimethyl-3-azabicyclo[3.1.0]hexane-2-carboxamide (50 mg, 103.83 umol, 1 eq) in DCM (3 mL) was added methoxycarbonyl-(triethylammonio)sulfonyl-azanide (49.49 mg, 207.67 umol, 2 eq). The mixture was stirred at 25° C. for 2 h. Once the reaction was completed, the reaction was concentrated and purified by prep-HPLC (column: Phenomenex Gemini-NX 80*40 mm*3 um; mobile phase: [water (10 mM NH4HCO3)-ACN]; B %: 20%-40%, 8 min) to give (2S,5S)-N-[(1S)-1-cyano-2-[(3S)-2-oxopyrrolidin-3-yl]ethyl]-3-(4-methoxy-1H-indole-2-carbonyl)-6,6-dimethyl-3-azabicyclo[3.1.0]hexane-2-carboxamide (14.44 mg, 31.15 umol, 30.00% yield, 100% purity) as a solid. MS (ESI) m/z 464.2 [M+H]+.

1H NMR (400 MHz, METHANOL-d4): δ ppm 7.16-7.18 (m, 1H), 7.11-7.14 (m, 2H), 6.4-6.88 (m, 1H), 5.05-5.08 (m, 0.5H), 4.06 (s, 2H), 3.94-3.98 (m, 0.5H), 3.77-3.86 (m, 4H), 3.28 (s, 2H), 2.61-3.69 (m, 1H), 2.27-2.32 (m, 1H), 2.25-2.26 (m, 1H), 1.78-2.00 (m, 1H), 1.74-1.75 (m, 1H) 1.35-1.64 (m, 2H), 0.97-1.15 (m, 6H)

Example 20. Synthesis of Viral Protease Inhibitor Compound 213

Step 1: (S)-Methyl 2-amino-3-((S)-2-oxopyrrolidin-3-yl)propanoate

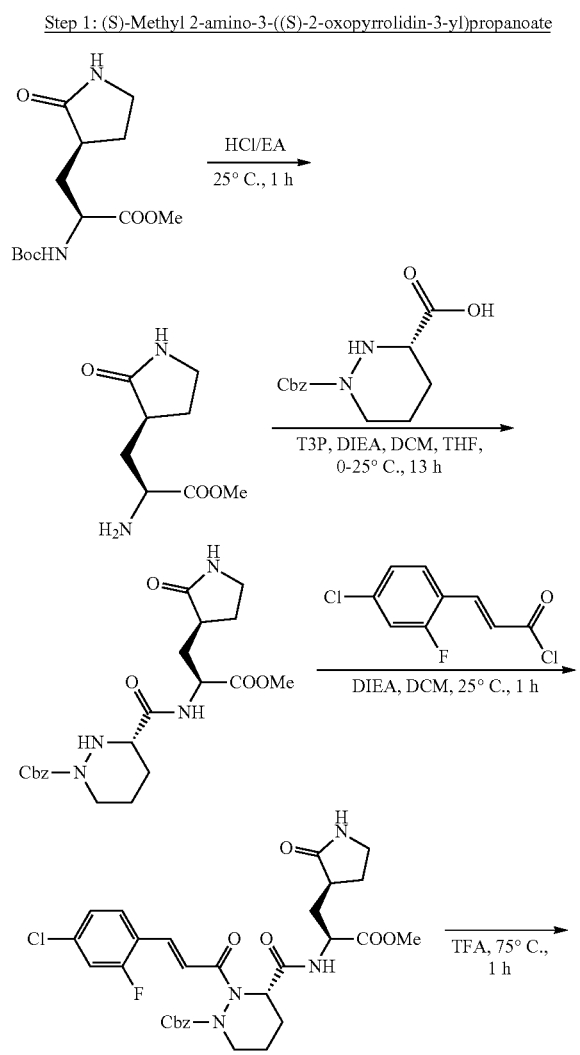

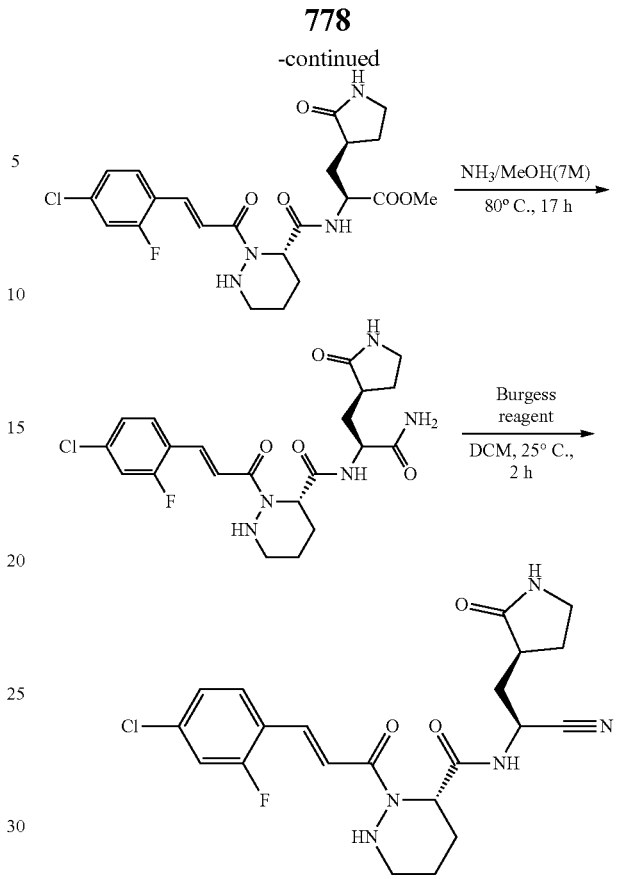

Methyl (2S)-2-(tert-butoxycarbonylamino)-3-[(3S)-2-oxopyrrolidin-3-yl]propanoate (501 mg, 1.75 mmol, 1 eq) in HCl/EtOAc (4 M, 10.02 mL, 22.91 eq) was stirred at 25° C. for 1 h. Upon completion, the solution was concentrated. The crude was used to next step directly and without further purification. Methyl (2S)-2-amino-3-[(3S)-2-oxopyrrolidin-3-yl]propanoate (300 mg, crude) was obtained as yellow oil.

Step 2: (S)-benzyl 3-(((S)-1-methoxy-1-oxo-3-((S)-2-oxopyrrolidin-3-yl)propan-2-yl)carbamoyl)tetrahydropyridazine-1(2H)-carboxylate Methyl (2S)-2-amino-3-[(3S)-2-oxopyrrolidin-3-yl]propanoate (295.93 mg, 1.59 mmol, 1.4 eq) and (3S)-1-benzyloxycarbonylhexahydropyridazine-3-carboxylic acid (300 mg, 1.14 mmol, 1 eq) in DCM (2 mL)/THF (2 mL) was cooled to 0° C., then the T3P (1.08 g, 1.70 mmol, 1.01 mL, 50% purity, 1.5 eq) and DIEA (440.14 mg, 3.41 mmol, 593.18 uL, 3 eq) was added and the solution was stirred at 25° C. for 13 h. Upon completion, the solution was diluted with H2O (20 mL), extracted with Ethyl acetate (30 mL*3), the combined organic phase was dried over Na2SO4, filtrated and concentrated to give the crude. The crude was used to next step directly and without further purification. Benzyl (3S)-3-[[(1S)-2-methoxy-2-oxo-1-[[(3S)-2-oxopyrrolidin-3-yl] methyl] ethyl] carbamoyl]hexahydropyridazine-1-carboxylate (455 mg, crude) was obtained as yellow oil. MS (ESI) m/z 433.1 [M+H]+.

Step 3: (S)-benzyl 2-((E)-3-(4-chloro-2-fluorophenyl)acryloyl)-3-(((S)-1-methoxy-1-oxo-3-((S)-2-oxopyrrolidin-3-yl)propan-2-yl)carbamoyl)tetrahydropyridazine-1(2H)-carboxylate Benzyl (3S)-3-[[(1S)-2-methoxy-2-oxo-1-[[(3S)-2-oxopyrrolidin-3-yl]methyl]ethyl]carbamoyl]hexahydropyridazine-1-carboxylate (200 mg, 462.46 umol, 1 eq) in DCM (2 mL) was added the DIEA (119.54 mg, 924.92 umol, 161.10 uL, 2 eq), (E)-3-(4-chloro-2-fluoro-phenyl)prop-2-enoyl chloride (121.56 mg, 554.95 umol, 1.2 eq) was added and the solution was stirred at 25° C. for 1 h. Upon completion, the solution was diluted with H₂O (10 mL), extracted with DCM (20 mL*3), the combined organic phase was dried over Na₂SO₄, filtrated and concentrated to give the crude. The residue was purified by prep-TLC (SiO₂, DCM:MeOH=10:1). Benzyl (3S)-2-[(E)-3-(4-chloro-2-fluoro-phenyl) prop-2-enoyl]-3-[[(1S)-2-methoxy-2-oxo-1-[[(3S)-2-oxopyrrolidin-3-yl] methyl] ethyl] carbamoyl] hexahydropyridazine-1-carboxylate (160 mg, 248.88 umol, 53.82% yield, 95.67% purity) was obtained as yellow oil. MS (ESI) m/z 433.1 [M+H]⁺.

Step 4: (S)-methyl 2-((S)-2-((E)-3-(4-chloro-2-fluorophenyl)acryloyl)hexahydropyridazine-3-carboxamido)-3-((S)-2-oxopyrrolidin-3-yl)propanoate Benzyl (3S)-2-[(E)-3-(4-chloro-2-fluoro-phenyl)prop-2-enoyl]-3-[[(1S)-2-methoxy-2-oxo-1-[[(3S)-2-oxopyrrolidin-3-yl]methyl]ethyl]carbamoyl]hexahydropyridazine-1-carboxylate (160 mg, 260.14 umol, 1 eq) in TFA (5 mL) was stirred at 75° C. for 1 h. Upon completion, the solution was concentrated to remove the TFA, diluted with the solution of NaHCO₃, extracted with EtOAc (20 mL*3), the combined organic phase was dried over Na₂SO₄, filtrated and concentrated to give the crude. The crude was used to next step directly and without further purification. Methyl (2S)-2-[[(3S)-2-[(E)-3-(4-chloro-2-fluoro-phenyl) prop-2-enoyl] hexahydropyridazine-3-carbonyl] amino]-3-[(3S)-2-oxopyrrolidin-3-yl]propanoate (80 mg, crude) was obtained as solid. MS (ESI) m/z 481.0 [M+H]⁺.

Step 5: (S)-N-((S)-1-amino-1-oxo-3-((S)-2-oxopyrrolidin-3-yl)propan-2-yl)-2-((E)-3-(4-chloro-2-fluorophenyl)acryloyl)hexahydropyridazine-3-carboxamide Methyl (2S)-2-[[(3S)-2-[(E)-3-(4-chloro-2-fluoro-phenyl)prop-2-enoyl]hexahydropyridazine-3-carbonyl]amino]-3-[(3S)-2-oxopyrrolidin-3-yl]propanoate (80 mg, 166.35 umol, 1 eq) in NH₃/MeOH (7 M, 4.00 mL, 168.32 eq) was stirred at 80° C. for 17 h. Upon completion, the solution was concentrated to remove the MeOH. The crude was used to next step directly and without further purification. (3S)-N-[(1S)-2-amino-2-oxo-1-[[(3S)-2-oxopyrrolidin-3-yl] methyl] ethyl]-2-[(E)-3-(4-chloro-2-fluoro-phenyl) prop-2-enoyl] hexahydropyridazine-3-carboxamide (75 mg, crude) was obtained as yellow oil. MS (ESI) m/z 481.0 [M+H]⁺.

Step 6: (S)-2-((E)-3-(4-chloro-2-fluorophenyl)acryloyl)-N-((S)-1-cyano-2-((S)-2-oxopyrrolidin-3-yl)ethyl)hexahydropyridazine-3-carboxamide (3S)-N-[(1S)-2-amino-2-oxo-1-[[(3S)-2-oxopyrrolidin-3-yl]methyl]ethyl]-2-[(E)-3-(4-chloro-2-fluoro-phenyl)prop-2-enoyl]hexahydropyridazine-3-carboxamide (75 mg, 160.98 umol, 1 eq) in DCM (0.5 mL) was added the Burgess reagent (76.72 mg, 321.95 umol, 2 eq) and the solution was stirred at 25° C. for 2 h. Upon completion, the solution was concentrated to remove the DCM. The residue was purified by prep-HPLC (neutral condition). Column: Phenomenex Gemini-NX 80*40 mm*3 um; mobile phase: [water (10 mM NH4HCO3)-ACN]; B %: 25%-45%, 8 min. (3S)-2-[(E)-3-(4-chloro-2-fluoro-phenyl)prop-2-enoyl]-N-[(1S)-1-cyano-2-[(3S)-2-oxopyrrolidin-3-yl]ethyl]hexahydropyridazine-3-carboxamide (20 mg, 44.65 umol, 27.74% yield, 100% purity) was obtained as a solid. ¹H NMR (400 MHz, METHANOL-d₄) δ=7.79-7.60 (m, 3H), 7.32-7.22 (m, 2H), 5.17 (dd, J=2.2, 6.0 Hz, 1H), 5.07 (dd, J=6.4, 9.7 Hz, 1H), 3.38-3.32 (m, 2H), 3.12 (br d, J=13.7 Hz, 1H), 2.90-2.74 (m, 1H), 2.56 (dq, J=5.8, 9.0 Hz, 1H), 2.44-2.14 (m, 3H), 2.08-1.79 (m, 3H), 1.75-1.53 (m, 2H). MS (ESI) m/z 448.2 [M+H]⁺.

Step 7: (E)-3-(4-chloro-2-fluorophenyl)acryloyl chloride (E)-3-(4-chloro-2-fluoro-phenyl)prop-2-enoic acid (120 mg, 598.22 umol, 1 eq) in DCM (0.5 mL) was added the DMF (437.26 ug, 5.98 umol, 0.46 uL, 0.01 eq) and cooled to 0° C., then the (COCl)₂ (151.86 mg, 1.20 mmol, 104.73 uL, 2 eq) was added and the solution was stirred at 25° C. for 1 h. Upon completion, the solution was concentrated to remove the DCM and give the crude. The crude was used to next step directly and without further purification. (E)-3-(4-chloro-2-fluoro-phenyl)prop-2-enoyl chloride (125 mg, crude) was obtained as a solid.

Example 21. Synthesis of Viral Protease Inhibitor Compound 201

Step 1: methyl (2S)-2-amino-3-[(3S)-2-oxopyrrolidin-3-yl]propanoate; hydrochloride

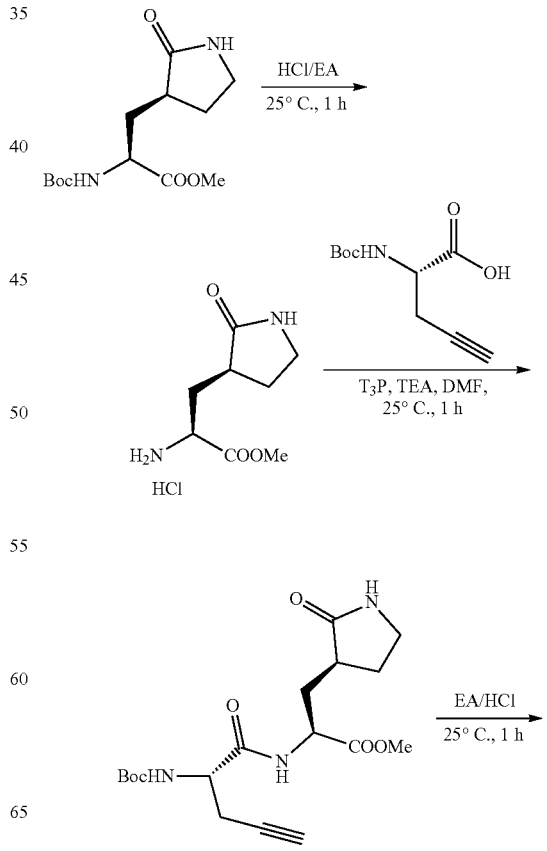

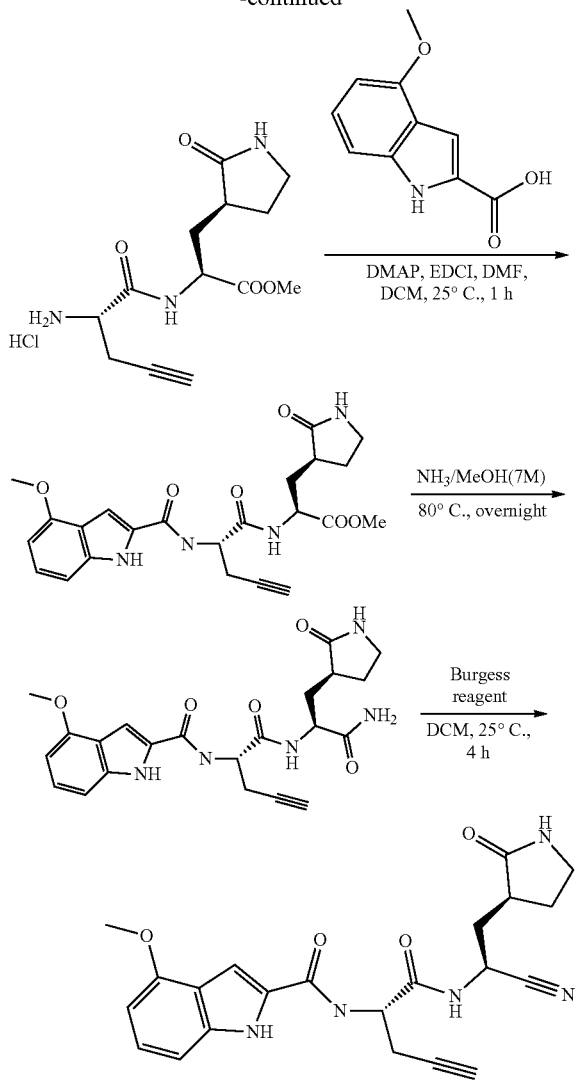

Methyl (2S)-2-(tert-butoxycarbonylamino)-3-[(3S)-2-oxopyrrolidin-3-yl]propanoate (250 mg, 873.14 umol, 1 eq) was added HCl/EtOAc (4 M, 30 mL) at 25° C. The mixture was stirred at 25° C. for 1 h. The reaction mixture was concentrated under reduced pressure to give a product methyl (2S)-2-amino-3-[(3S)-2-oxopyrrolidin-3-yl]propanoate; hydrochloride (200 mg, crude) as a solid and used directly for next step.

Step 2: (S)-methyl-2-((S)-2-((tert-butoxycarbonyl) amino)pent-4-ynamido)-3-((S)-2-oxopyrrolidin-3-yl) propanoate A mixture of methyl (2S)-2-amino-3-[(3S)-2-oxopyrrolidin-3-yl]propanoate; hydrochloride (180 mg, 808.38 umol, 1 eq), (2S)-2-(tert-butoxycarbonylamino)pent-4-ynoic acid (172.37 mg, 808.38 umol, 1 eq), TEA (572.59 mg, 5.66 mmol, 787.61 uL, 7 eq), $T_3P$ (1.03 g, 1.62 mmol, 961.53 uL, 50% purity, 2 eq) and DMF (3 mL) was stirred at 25° C. for 1 h. The reaction mixture was diluted with $H_2O$ (30 mL) and extracted with DCM (30 mL*3). The combined organic layers were washed with brine (50 mL), dried over $Na_2SO_4$, filtered and concentrated under reduced pressure to give a residue. The residue was purified by column chromatography ($SiO_2$, petroleum ether/EtOAc=0/1) to afford the product (S)-methyl-2-((S)-2-((tert-butoxycarbonyl)amino)pent-4-ynamido)-3-((S)-2-oxopyrrolidin-3-yl)propanoate (150 mg, 393.26 umol, 48.65% yield), as an oil. MS (ESI) m/z 382.1 $[M+H]^+$ Step 3: (S)-methyl 2-((S)-2-aminopent-4-ynamido)-3-((S)-2-oxopyrrolidin-3-yl)propanoate A mixture of (S)-methyl-2-((S)-2-((tert-butoxycarbonyl) amino)pent-4-ynamido)-3-((S)-2-oxopyrrolidin-3-yl)propanoate (140 mg, 367.05 umol, 1 eq) and HCl/EtOAc (4 M, 30 mL) was stirred at 25° C. for 1 h. The reaction mixture was concentrated under reduced pressure to give a product (S)-methyl 2-((S)-2-aminopent-4-ynamido)-3-((S)-2-oxopyrrolidin-3-yl)propanoate (120 mg, crude, HCl) as an oil and used directly for next step.

Step 4: (S)-methyl-2-((S)-2-(4-methoxy-1H-indole-2-carboxamido)pent-4-ynamido)-3-((S)-2-oxopyrrolidin-3-yl)propanoate A mixture of (S)-methyl 2-((S)-2-aminopent-4-ynamido)-3-((S)-2-oxopyrrolidin-3-yl)propanoate (120 mg, 377.63 umol, 1 eq, HCl), 4-methoxy-1H-indole-2-carboxylic acid (72.20 mg, 377.63 umol, 1 eq), EDCI (144.78 mg, 755.27 umol, 2 eq), DMAP (92.27 mg, 755.27 umol, 2 eq), DMF (2 mL) and DCM (4 mL) was stirred at 25° C. for 1 h. The reaction mixture was diluted with $H_2O$ (30 mL) and extracted with DCM (30 mL*3). The combined organic layers were washed with brine (50 mL), dried over $Na_2SO_4$, filtered and concentrated under reduced pressure to give a residue. The residue was purified by column chromatography ($SiO_2$, petroleum ether/EtOAc=0/1) to get the compound (S)-methyl-2-((S)-2-(4-methoxy-1H-indole-2-carboxamido)pent-4-ynamido)-3-((S)-2-oxopyrrolidin-3-yl) propanoate (90 mg, 160.56 umol, 42.52% yield, 81.08% purity), as an oil. MS (ESI) m/z 455.1 $[M+H]^+$ Step 5: N-((S)-1-(((S)-1-amino-1-oxo-3-((S)-2-oxopyrrolidin-3-yl)propan-2-yl)amino)-1-oxopent-4-yn-2-yl)-4-methoxy-1H-indole-2-carboxamide A mixture of (S)-methyl-2-((S)-2-(4-methoxy-1H-indole-2-carboxamido)pent-4-ynamido)-3-((S)-2-oxopyrrolidin-3-yl)propanoate (85 mg, 187.03 umol, 1 eq) and $NH_3$/MeOH (7 M, 10 mL) was stirred at 80° C. for 16 h. The reaction mixture was concentrated under reduced pressure to give a product N-((S)-1-(((S)-1-amino-1-oxo-3-((S)-2-oxopyrrolidin-3-yl)propan-2-yl)amino)-1-oxopent-4-yn-2-yl)-4-methoxy-1H-indole-2-carboxamide (85 mg, crude) as a solid. MS (ESI) m/z 440.2 $[M+H]^+$ Step 6. N-((S)-1-(((S)-1-cyano-2-((S)-2-oxopyrrolidin-3-yl)ethyl)amino)-1-oxopent-4-yn-2-yl)-4-methoxy-1H-indole-2-carboxamide A mixture of N-((S)-1-(((S)-1-amino-1-oxo-3-((S)-2-oxopyrrolidin-3-yl)propan-2-yl)amino)-1-oxopent-4-yn-2-yl)-4-methoxy-1H-indole-2-carboxamide (80 mg, 182.04 umol, 1 eq), Burgess reagent (216.91 mg, 910.20 umol, 5 eq) and DCM (5 mL) was stirred at 25° C. for 4 h. The reaction mixture was concentrated under reduced pressure to give a residue. The residue was purified by prep-HPLC (column: Waters Xbridge BEH C18 100*30 mm*10 um; mobile phase: [water(0.04% $NH_3H_2O$+10 mM $NH4HCO_3$)-ACN]; B %: 20%-50%, 10 min) to get the product N-((S)-1-(((S)-

1-cyano-2-((S)-2-oxopyrrolidin-3-yl)ethyl)amino)-1-oxopent-4-yn-2-yl)-4-methoxy-1H-indole-2-carboxamide (20 mg, 47.46 umol, 26.07% yield, 100% purity), as solid. MS (ESI) m/z 422.2 [M+H]+.

$^1$H NMR (400 MHz, DMSO-$d_6$) δ=11.61 (d, J=1.8 Hz, 1H), 9.18-8.93 (m, 1H), 8.74-8.58 (m, 1H), 7.78-7.62 (m, 1H), 7.37-7.29 (m, 1H), 7.15-7.07 (m, 1H), 7.05-6.97 (m, 1H), 6.51 (d, J=7.5 Hz, 1H), 5.03-4.91 (m, 1H), 4.65-4.50 (m, 1H), 3.89 (s, 3H), 3.20-3.05 (m, 2H), 2.91-2.85 (m, 1H), 2.78-2.59 (m, 2H), 2.43-2.29 (m, 1H), 2.21-2.06 (m, 2H), 1.88-1.59 (m, 2H)

Example 22. Synthesis of Viral Protease Inhibitor Compound 205

Step 1: (S)-2-((tert-butoxycarbonyl)amino)-3-cyclopropylpropanoic acid

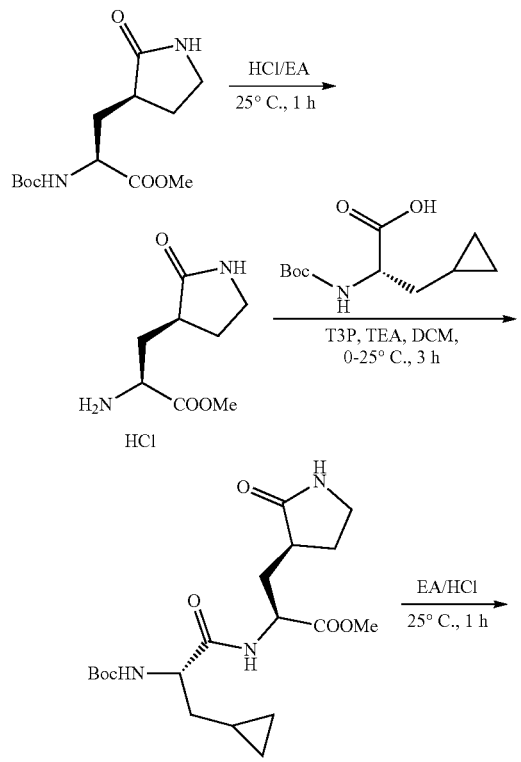

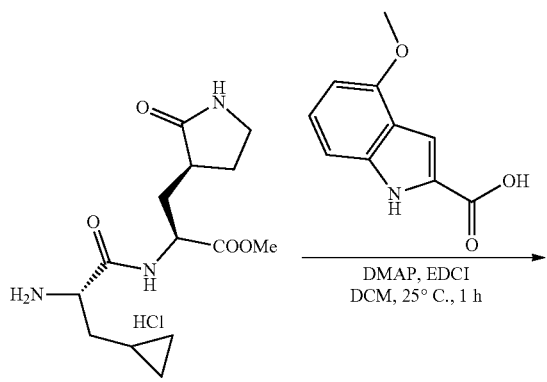

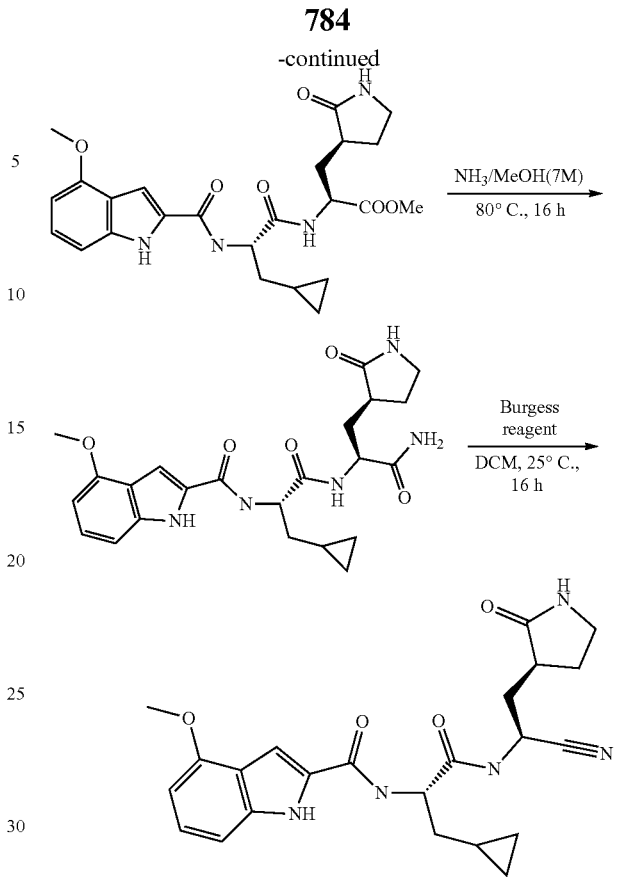

To a solution of (2S)-2-amino-3-cyclopropyl-propanoic acid (1 g, 7.74 mmol, 1 eq) in THF (5 mL) and H$_2$O (5 mL), was added K$_2$CO$_3$ (3.75 g, 27.10 mmol, 3.5 eq) and (Boc)$_2$O (2.20 g, 10.07 mmol, 2.31 mL, 1.3 eq). Additional water was added to the mixture, and then the mixture was stirred at 25° C. for 16 h. The organic solvent was then evaporated and the aqueous solution was washed with petroleum ether (10 mL) and acidified to pH ~3 with 1N aqueous citric acid (30 mL). The solution was extracted with DCM (30 mL*3) and was concentrated in vacuum to afford (S)-2-((tert-butoxycarbonyl) amino)-3-cyclopropyl propanoic acid (1.8 g, crude) as an oil.

Step 2: (S)-methyl 2-amino-3-((S)-2-oxopyrrolidin-3-yl)propanoate (S)-methyl 2-((tert-butoxycarbonyl) amino)-3-((S)-2-oxopyrrolidin-3-yl) propanoate (500 mg, 1.75 mmol, 1 eq) was added HCl/EtOAc (4 M, 5 mL) at 25° C. The mixture was stirred at 25° C. for 1 h. The reaction mixture was concentrated under reduced pressure to give a product (S)-methyl 2-amino-3-((S)-2-oxopyrrolidin-3-yl) propanoate (350 mg, HCl, crude) as a yellow gum and used to next step directly.

Step 3: (S)-methyl2-((S)-2-((tert-butoxycarbonyl) amino)-3-cyclopropylpropanamido)-3-((S)-2-oxopyrrolidin-3-yl)propanoate To a mixture of (S)-methyl 2-amino-3-((S)-2-oxopyrrolidin-3-yl) propanoate (250 mg, 1.12 mmol, 1 eq, HCl) and (S)-2-((tert-butoxycarbonyl) amino)-3-cyclopropyl propanoic acid (386.12 mg, 1.68 mmol, 1.5 eq) in DCM (5 mL) was added TEA (568.05 mg, 5.61 mmol, 781.36 uL, 5 eq) at 0° C., the mixture was added T3P (2.14 g, 3.37 mmol, 2.00 mL, 50% purity, 3 eq) at 0° C., then the mixture was stirred at 25° C. for 2 h. The reaction mixture was quenched by water (10 mL) and was extracted with DCM (5 mL*3). The resulting solution was dried with Na₂SO₄, filtered and concentration in vacuum to give a residue. The residue was purified by column chromatography (SiO₂, petroleum ether:EtOAc=1:0 to 0:1) to afford the product (S)-methyl 2-((S)-2-((tert-butoxycarbonyl)amino)-3-cyclopropylpropanamido)-3-((S)-2-oxopyrrolidin-3-yl)propanoate (400 mg, 905.74 umol, 80.67% yield, 90% purity) was obtained as a gum.

¹H NMR (400 MHz, CDCl₃) δ ppm 7.60 (d, J=5.6 Hz, 1H), 5.96 (s, 1H), 5.24 (d, J=7.5 Hz, 1H), 4.65-4.47 (m, 1H), 4.24 (d, J=6.6 Hz, 1H), 3.73 (s, 3H), 3.44-3.27 (m, 2H), 2.51-2.36 (m, 2H), 2.25-2.13 (m, 1H), 1.98-1.82 (m, 1H), 1.66-1.58 (m, 1H), 1.44 (s, 9H), 1.30-1.21 (m, 1H), 0.86-0.71 (m, 1H), 0.49 (d, J=7.9 Hz, 2H), 0.13 (d, J=4.4 Hz, 2H).

Step 4: (S)-methyl 2-((S)-2-amino-3-cyclopropylpropanamido)-3-((S)-2-oxopyrrolidin-3-yl)propanoate A solution of (S)-methyl2-((S)-2-((tert-butoxycarbonyl)amino)-3-cyclopropylpropanamido)-3-((S)-2-oxopyrrolidin-3-yl)propanoate in HCl/EtOAc (4 M, 4 mL), the mixture was stirred at 25° C. for 1 h. The reaction mixture was concentrated under reduced pressure to give a product (S)-methyl 2-((S)-2-amino-3-cyclopropylpropanamido)-3-((S)-2-oxopyrrolidin-3-yl) propanoate (330 mg, crude, HCl) as a yellow gum and used directly next step.

1H NMR (400 MHz, MeOD-d₄) δ ppm 4.57 (dd, J=4.1, 11.0 Hz, 1H), 3.94 (t, J=6.7 Hz, 1H), 3.73 (s, 3H), 3.40-3.33 (m, 2H), 2.55-2.33 (m, 2H), 2.19-2.07 (m, 1H), 2.03-2.00 (m, 1H), 1.93-1.84 (m, 2H), 1.24 (t, J=7.1 Hz, 1H), 0.89-0.79 (m, 1H), 0.59 (dd, J=4.5, 7.9 Hz, 2H), 0.26-0.17 (m, 2H).

Step 5: (S)-methyl2-((S)-3-cyclopropyl-2-(4-methoxy-5H-indole-2-carboxamido)propanamido)-3-((S)-2-oxopyrrolidin-3-yl)propanoate To a mixture of 4-methoxy-1H-indole-2-carboxylic acid (257.73 mg, 1.35 mmol, 1.5 eq) and (S)-methyl 2-((S)-2-amino-3-cyclopropylpropanamido)-3-((S)-2-oxopyrrolidin-3-yl) propanoate (300 mg, 898.71 umol, 1 eq, HCl) in DCM (8 mL) was added EDCI (861.43 mg, 4.49 mmol, 5 eq) and DMAP (329.38 mg, 2.70 mmol, 3 eq), then the mixture was stirred at 25° C. for 2 h. The combined organic layers were quenched with water (10 mL) and were extracted with DCM (4 mL*3). The resulting solution was dried over Na₂SO₄, filtered and concentrated under reduced pressure to give a residue. The residue was purified by column chromatography (SiO₂, EtOAc) to get the compound (S)-methyl2-((S)-3-cyclopropyl-2-(4-methoxy-1H-indole-2-carboxamido)propanamido)-3-((S)-2-oxopyrrolidin-3-yl)propanoate (250 mg, 425.06 umol, 47.30% yield, 80% purity) as yellow oil. MS (ESI) m/z 471.1 [M+H]⁺

Step 6: N-((S)-1-(((S)-1-amino-1-oxo-3-((S)-2-oxopyrrolidin-3-yl)propan-2-yl)amino)-3-cyclopropyl-1-oxopropan-2-yl)-4-methoxy-1H-indole-2-carboxamide (S)-Methyl2-((S)-3-cyclopropyl-2-(4-methoxy-1H-indole-2-carboxamido)propanamido)-3-((S)-2-oxopyrrolidin-3-yl)propanoate (250 mg, 531.33 umol, 1 eq) was added with NH₃/MeOH (7 M, 6.00 mL). The mixture was stirred at 80° C. for 16 h. The resulting mixture was concentrated under reduced pressure to give a residue N-((S)-1-(((S)-1-amino-1-oxo-3-((S)-2-oxopyrrolidin-3-yl)propan-2-yl)amino)-3-cyclopropyl-1-oxopropan-2-yl)-4-methoxy-1H-indole-2-carboxamide (200 mg, crude) as a solid. MS (ESI) m/z 456.1 [M+H]⁺

Step 7: N-((S)-1-(((S)-1-cyano-2-((S)-2-oxopyrrolidin-3-yl)ethyl)amino)-3-cyclopropyl-1-oxopropan-2-yl)-4-methoxy-1H-indole-2-carboxamide To a mixture of N-((S)-1-(((S)-1-amino-1-oxo-3-((S)-2-oxopyrrolidin-3-yl)propan-2-yl) amino)-3-cyclopropyl-1-oxopropan-2-yl)-4-methoxy-1H-indole-2-carboxamide (100 mg, crude) in DCM (4 mL) was added Burgess reagent (104.63 mg, 439.07 umol, 2 eq). The mixture was stirred at 25° C. for 16 h. The reaction mixture was quenched by water (0.5 mL) and was dried by blowing N₂. The residue was purified by neutral prep-HPLC to get the product N-((S)-1-(((S)-1-cyano-2-((S)-2-oxopyrrolidin-3-yl)ethyl)amino)-3-cyclopropyl-1-oxopropan-2-yl)-4-methoxy-1H-indole-2-carboxamide (15 mg, 34.29 umol, 15.62% yield, 100% purity) as a solid. MS (ESI) m/z 438.2 [M+H]⁺.

Prep-HPLC Condition:

column: Waters Xbridge BEH C18 100*25 mm*5 um; mobile phase: [water (10 mM NH₄HCO₃)-ACN]; B %: 20%-50%, 10 min.

¹H NMR (400 MHz, DMSO-d₆) δ ppm 11.57 (d, J=1.8 Hz, 1H), 8.90 (d, J=8.2 Hz, 1H), 8.50 (d, J=7.5 Hz, 1H), 7.78-7.65 (m, 1H), 7.36 (d, J=1.5 Hz, 1H), 7.13-7.04 (m, 1H), 7.03-6.96 (m, 1H), 6.50 (d, J=7.8 Hz, 1H), 5.04-4.94 (m, 1H), 4.54-4.38 (m, 1H), 3.89 (s, 3H), 3.19-3.06 (m, 2H), 2.44-2.33 (m, 1H), 2.22-2.07 (m, 2H), 1.90-1.75 (m, 2H), 1.74-1.63 (m, 1H), 1.54-1.41 (m, 1H), 0.87-0.73 (m, 1H), 0.47-0.34 (m, 2H), 0.25-0.15 (m, 1H), 0.14-0.04 (m, 1H).

Example 23. Synthesis of Viral Protease Inhibitor Compound 401

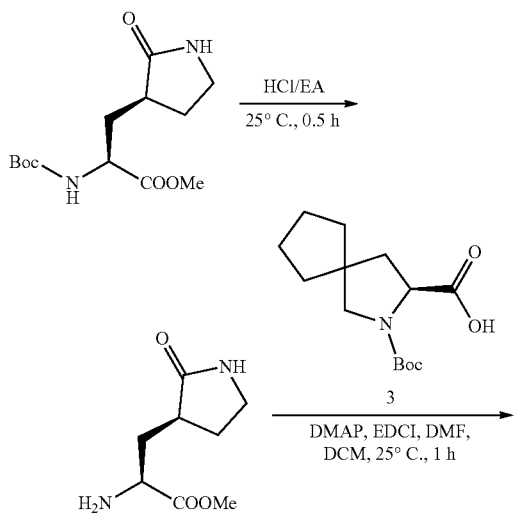

787

-continued

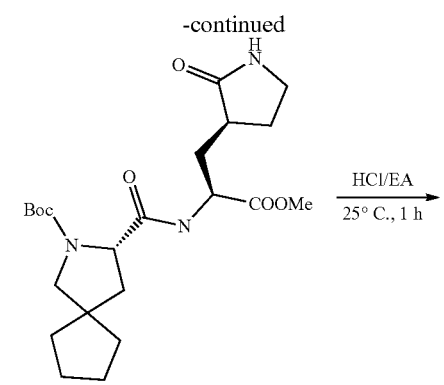

HCl/EA
25° C., 1 h

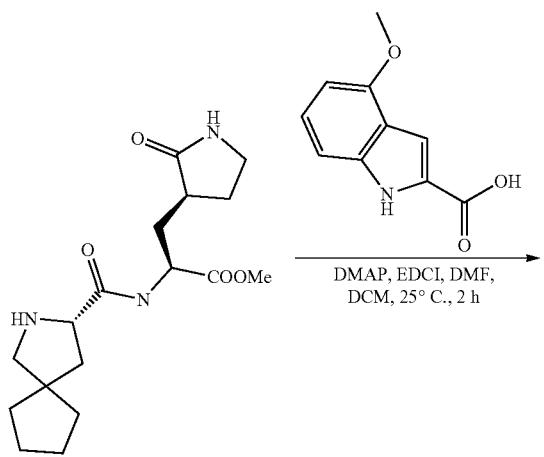

DMAP, EDCI, DMF,
DCM, 25° C., 2 h

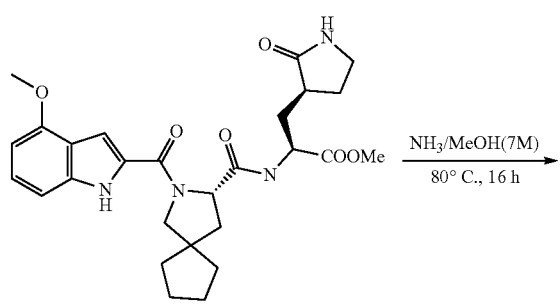

NH₃/MeOH(7M)
80° C., 16 h

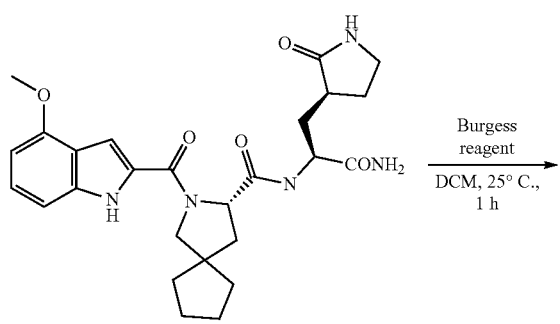

Burgess reagent
DCM, 25° C., 1 h

788

-continued

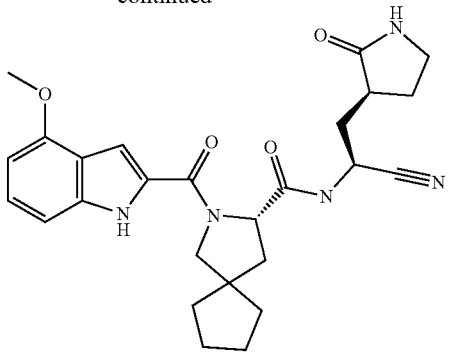

Methyl (2S)-2-(tert-butoxycarbonylamino)-3-[(3S)-2-oxopyrrolidin-3-yl]propanoate (400 mg, 1.40 mmol, 1 eq) in HCl/EtOAc (4 M, 10 mL, 28.63 eq) was stirred at 25° C. for 0.5 h. Upon completion, the mixture was concentrated under the reduced pressure affording the product methyl (2S)-2-amino-3-[(3S)-2-oxopyrrolidin-3-yl]propanoate (300 mg, crude, HCl) as a solid.

Step 2: (S)-tert-butyl3-(((S)-1-methoxy-1-oxo-3-((S)-2-oxopyrrolidin-3-yl)propan-2-yl)carbamoyl)-2-azaspiro[4.4]nonane-2-carboxylate Methyl (2S)-2-amino-3-[(3S)-2-oxopyrrolidin-3-yl]propanoate (300 mg, 1.35 mmol, 1 eq, HCl) and (3S)-2-tertbutoxycarbonyl-2-azaspiro[4.4]nonane-3-carboxylic acid (362.87 mg, 1.35 mmol, 1 eq) in DMF (2 mL) and DCM (5 mL) was added DMAP (329.19 mg, 2.69 mmol, 2 eq) and EDCI (516.56 mg, 2.69 mmol, 2 eq). The mixture was stirred at 25° C. for 1 h. Upon completion, the reaction mixture was quenched by addition H₂O (10 mL), and then extracted with DCM (10 mL*3). The combined organic layers were washed with brine (10 mL), dried over Na₂SO₄, filtered and concentrated under reduced pressure to give a residue. The residue was purified by column chromatography (SiO₂, petroleum ether:EtOAc=5:1 to 0:1) affording the product tert-butyl(3S)-3-[[(1S)-2-methoxy-2-oxo-1-[[(3S)-2-oxopyrrolidin-3-yl]methyl]ethyl]carbamoyl]-2-azaspiro[4.4]nonane-2-carboxylate (340 mg, 777.09 umol, 57.68% yield) as an oil.

Step 3: (S)-methyl3-((S)-2-oxopyrrolidin-3-yl)-2-((S)-2-azaspiro[4.4]nonane-3-carboxamido)propanoate tert-Butyl(3S)-3-[[(1S)-2-methoxy-2-oxo-1-[[(3S)-2-oxopyrrolidin-3-yl]methyl]ethyl]carbamoyl]-2-azaspiro[4.4]nonane-2-carboxylate (340 mg, 777.09 umol, 1 eq) in HCl/EtOAc (4 M, 10 mL, 51.47 eq) was stirred at 25° C. for 1 h. Upon completion, the mixture was concentrated under the reduced pressured affording the product methyl(2S)-2-[[(3S)-2-azaspiro[4.4]nonane-3-carbonyl]amino]-3-[(3S)-2-oxopyrrolidin-3-yl]propanoate (250 mg, crude, HCl) as an oil.

Step 4: (S)-methyl2-((S)-2-(4-methoxy-1H-indole-2-carbonyl)-2-azaspiro[4.4]nonane-3-carboxamido)-3-((S)-2-oxopyrrolidin-3-yl)propanoate Methyl(2S)-2-[[(3S)-2-azaspiro[4.4]nonane-3-carbonyl]amino]-3-[(3S)-2-oxopyrrolidin-3-yl]propanoate (250 mg, 668.67 umol, 1 eq, HCl) and 4-methoxy-1H-indole-2-carboxylic acid (127.84 mg, 668.67 umol, 1 eq) in DMF (2 mL) and DCM (6 mL) was added DMAP (163.38 mg, 1.34 mmol, 2 eq) and EDCI (256.37 mg, 1.34 mmol, 2 eq). The mixture was stirred at 25° C. for 2 h. Upon completion, the reaction mixture was quenched by addition H₂O (10 mL), and then extracted with DCM (10 mL*3). The combined organic layers were washed with brine (10 mL), dried over Na₂SO₄, filtered and concentrated under reduced pressure to give a residue. The residue was purified by prep-TLC (SiO₂, petroleum ether:EtOAc=0:1) affording the product methyl (2S)-2-[[(3S)-2-(4-methoxy-1H-indole-2-carbonyl)-2-azaspiro[4.4]nonane-3-carbonyl]amino]-3-[(3S)-2-oxopyrrolidin-3-yl]propanoate (180 mg, 352.54 umol, 52.72% yield) as an oil. MS (ESI) m/z 511.2 [M+H]⁺

Step 5: (S)-N-((S)-1-amino-1-oxo-3-((S)-2-oxopyrrolidin-3-yl)propan-2-yl)-2-(4-methoxy-1H-indole-2-carbonyl)-2-azaspiro[4.4]nonane-3-carboxamide Methyl(2S)-2-[[(3S)-2-(4-methoxy-1H-indole-2-carbonyl)-2-azaspiro[4.4]nonane-3-carbonyl]amino]-3-[(3S)-2-oxopyrrolidin-3-yl]propanoate (180 mg, 352.54 umol, 1 eq) in ammonia (7 M, 20 mL, 397.12 eq) was stirred at 80° C. for 16 h. Upon completion, the mixture was concentrated under the reduced pressure affording the product (3S)-N-[(1S)-2-amino-2-oxo-1-[[(3S)-2-oxopyrrolidin-3-yl]methyl]ethyl]-2-(4-methoxy-1H-indole-2-carbonyl)-2-azaspiro[4.4]nonane-3-carboxamide (170 mg, crude) as an oil.

Step 6: (S)-N-((S)-1-cyano-2-((S)-2-oxopyrrolidin-3-yl)ethyl)-2-(4-methoxy-1H-indole-2-carbonyl)-2-azaspiro[4.4]nonane-3-carboxamide (3S)-N-[(1S)-2-amino-2-oxo-1-[[(3S)-2-oxopyrrolidin-3-yl]methyl]ethyl]-2-(4-methoxy-1H-indole-2-carbonyl)-2-azaspiro[4.4]nonane-3-carboxamide (170 mg, 343.04 umol, 1 eq) in DCM (3 mL) was added methoxycarbonyl-(triethylammonio)sulfonyl-azanide (408.74 mg, 1.72 mmol, 5 eq). The mixture was stirred at 25° C. for 1 h. Upon completion, the mixture was concentrated under the reduced pressure to give a residue. The residue was purified by prep-HPLC (column: Waters Xbridge BEH C18 100*25 mm*5 um; mobile phase: [water (10 mM NH₄HCO₃)-ACN]; B %: 30%-60%, 10 min) affording the product (3S)-N-[(1S)-1-cyano-2-[(3S)-2-oxopyrrolidin-3-yl]ethyl]-2-(4-methoxy-1H-indole-2-carbonyl)-2-azaspiro[4.4]nonane-3-carboxamide (25 mg, 51.09 umol, 14.89% yield, 97.6% purity) as a solid. MS (ESI) m/z 478.2 [M+H]⁺

¹H NMR (400 MHz, MMeOD-d₄) δ=7.22-7.12 (m, 1H), 7.11-6.98 (m, 2H), 6.58-6.45 (m, 1H), 5.11-4.95 (m, 1H), 4.65-4.52 (m, 1H), 3.94 (s, 3H), 3.93-3.80 (m, 2H), 3.28-3.18 (m, 1H), 2.54-2.02 (m, 4H), 2.01-1.48 (m, 12H).

Example 24. Synthesis of Viral Protease Inhibitor Compound 225

Step 1: methyl (2S)-2-amino-3-(3-methylimidazol-4-yl)propanoate

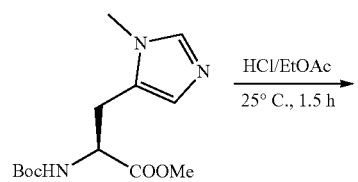

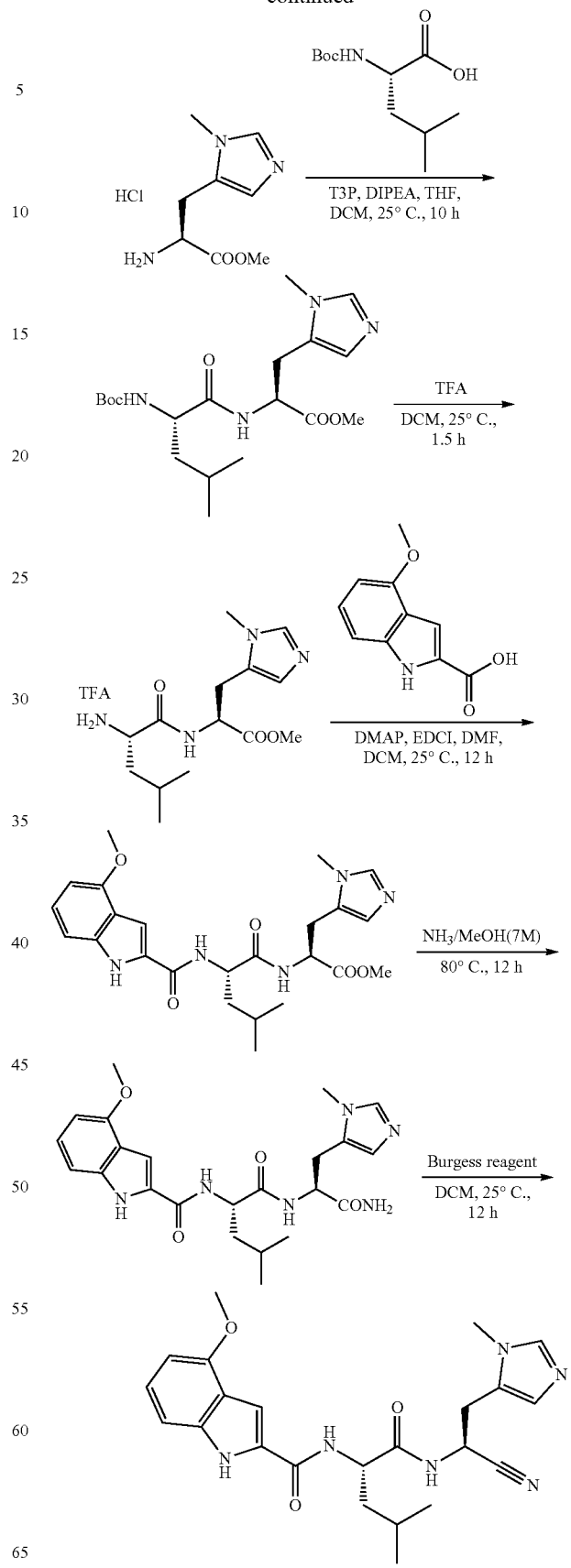

To the solution of (2S)-2-(tert-butoxycarbonylamino)-3-(3-methylimidazol-4-yl)propanoic acid (300 mg, 1.11 mmol, 1 eq) in EtOAc (1.2 mL) was added HCl/EtOAc (4 M, 2.79 mL, 10 eq) at 25° C. The reaction mixture was stirred at 25° C. for 1.5 h. The resulting mixture was concentrated to get the product. Methyl (2S)-2-amino-3-(3-methylimidazol-4-yl)propanoate (250 mg, crude, HCl) was obtained as a solid and used directly next step. MS (ESI) m/z 183.2 [M+H]$^+$ $^1$H NMR (400 MHz, METHANOL-d$_4$) δ ppm 8.94 (s, 1H), 7.56 (s, 1H), 4.51 (t, J=7.17 Hz, 1H), 3.93 (s, 3H), 3.87 (s, 3H), 3.46-3.55 (m, 1H), 3.32-3.42 (m, 1H).

Step 2: methyl (2S)-2-[[(2S)-2-(tert-butoxycarbonylamino)-4-methyl-pentanoyl]amino]-3-(3-methylimidazol-4-yl)propanoate To a mixture of methyl (2S)-2-amino-3-(3-methylimidazol-4-yl)propanoate (250 mg, 1.14 mmol, 1 eq, HCl) and (2S)-2-(tert-butoxycarbonylamino)-4-methyl-pentanoic acid (263.22 mg, 1.14 mmol, 1 eq) in THF (1 mL) and DCM (1 mL) and DIPEA (441.26 mg, 3.41 mmol, 594.69 uL, 3 eq) was added T3P (1.09 g, 1.71 mmol, 1.02 mL, 50% purity, 1.5 eq) at 0° C. under N$_2$. The mixture was stirred at 25° C. for 10 h. LCMS showed the reaction mixture was completed. The reaction mixture was added saturated sodium bicarbonate solution (10 mL) and extracted with DCM (10 mL×2) to get the organic phase. The organic phase was washed with brine (3 mL×3), dried over anhydrous sodium sulfate and concentrated to get the crude product. Methyl (2S)-2-[[(2S)-2-(tert-butoxy carbonyl amino)-4-methyl-pentanoyl]amino]-3-(3-methylimidazol-4-yl)propanoate (360 mg, crude) was obtained as an oil and used directly next step. MS (ESI) m/z 397.3 [M+H]$^+$ Step 3: methyl(2S)-2-[[(2S)-2-amino-4-methyl-pentanoyl]amino]-3-(3-methylimidazol-4-yl)propanoate To a mixture of methyl (2S)-2-[[(2S)-2-(tert-butoxycarbonylamino)-4-methyl-pentanoyl]amino]-3-(3-methylimidazol-4-yl)propanoate (360 mg, 907.99 umol, 1 eq) in DCM (3.3 mL) was added TFA (1.04 g, 9.08 mmol, 672.27 uL, 10 eq) at 25° C. under N$_2$. The mixture was stirred at 25° C. for 1.5 h. LCMS showed the reaction mixture was completed. The reaction mixture was concentrated to get the product. Methyl (2S)-2-[[(2S)-2-amino-4-methyl-pentanoyl]amino]-3-(3-methylimidazol-4-yl) propanoate (370 mg, crude, TFA) was obtained as an oil and used directly next step. MS (ESI) m/z 297.2 [M+H]$^+$ Step 4: methyl (2S)-2-[[(2S)-2-[(4-methoxy-1H-indole-2-carbonyl)amino]-4-methyl-pentanoyl]amino]-3-(3-methylimidazol-4-yl)propanoate To a mixture of methyl (2S)-2-[[(2S)-2-amino-4-methyl-pentanoyl]amino]-3-(3-methylimidazol-4-yl)propanoate (370 mg, 1.25 mmol, 1 eq, TFA) and 4-methoxy-1H-indole-2-carboxylic acid (238.69 mg, 1.25 mmol, 1 eq) in DMF (1.5 mL) and DCM (1.5 mL) was added EDCI (478.66 mg, 2.50 mmol, 2 eq) and DMAP (305.05 mg, 2.50 mmol, 2 eq) in one portion at 25° C. under N$_2$. The mixture was stirred at 25° C. for 12 h. The resulting mixture was added with water (10 mL) and extracted with DCM (10 mL*2) to get the organic phase. The organic phase was washed with brine (3 mL*3) and dried over anhydrous sodium sulfate and concentrated to get the crude product. The residue was purified by column chromatography (SiO2, petroleum ether/EtOAc=2/1 to EtOAc/Methanol=10/1). Methyl (2S)-2-[[(2S)-2-[(4-methoxy-1H-indole-2-carbonyl)amino]-4-methyl-pentanoyl]amino]-3-(3-methylimidazol-4-yl)propanoate (270 mg, crude) was obtained as an oil. MS (ESI) m/z 469.5 [M+H]$^+$ Step 5: N-[(1S)-1-[[(1S)-2-amino-1-[(3-methylimidazol-4-yl)methyl]-2-oxo-ethyl]carbamoyl]-3-methyl-butyl]-4-methoxy-1H-indole-2-carboxamide To methyl (2S)-2-[[(2S)-2-[(4-methoxy-1H-indole-2-carbonyl)amino]-4-methyl-pentanoyl]amino]-3-(3-methylimidazol-4-yl)propanoate (235.00 mg, 500.50 umol, 1 eq) was added NH$_3$/MeOH (7 M, 1.94 mL, 27.14 eq) in one portion at 25° C. under N$_2$. The mixture was stirred at 80° C. and stirred for 12 h. LCMS showed the reaction mixture was completed. The reaction mixture was cooled to 25° C. and concentrated to get the crude product. The residue was purified by prep-TLC. N-[(1S)-1-[[(1S)-2-amino-1-[(3-methylimidazol-4-yl)methyl]-2-oxo-ethyl]carbamoyl]-3-methyl-butyl]-4-methoxy-1H-indole-2-carboxamide (170 mg, crude) was obtained as a solid. MS (ESI) m/z 455.3 [M+H]$^+$ Step 6: N-[(1S)-1-[[(1S)-1-cyano-2-(3-methylimidazol-4-yl)ethyl]carbamoyl]-3-methyl-butyl]-4-methoxy-1H-indole-2-carboxamide To a mixture of N-[(1S)-1-[[(1S)-2-amino-1-[(3-methylimidazol-4-yl)methyl]-2-oxo-ethyl]carbamoyl]-3-methyl-butyl]-4-methoxy-1H-indole-2-carboxamide (140 mg, 308.02 umol, 1 eq) in DCM (2 mL) was added Burgess reagent (293.61 mg, 1.23 mmol, 4 eq) at 25° C. under N$_2$. The mixture was stirred at 25° C. for 12 h, and then concentrated to get the crude product. The crude product was purified by pre-HPLC. N-[(1S)-1-[[(1S)-1-cyano-2-(3-methylimidazol-4-yl)ethyl]carbamoyl]-3-methyl-butyl]-4-methoxy-1H-indole-2-carboxamide (10.59 mg, 23.82 umol, 7.73% yield, 98.2% purity) was obtained as a solid. MS (ESI) m/z 437.2 [M+H]$^+$.

Prep-HPLC Condition:
column: Phenomenex Gemini-NX C18 75*30 mm*3 um; mobile phase: [water (10 mM NH$_4$HCO$_3$)-ACN]; B %: 25%-50%, 6 min
column: Waters Xbridge BEH C18 100*30 mm*10 um; mobile phase: [water (10 mM NH$_4$HCO$_3$)-ACN]; B %: 20%-45%, 8 min $^1$H NMR (400 MHz, METHANOL-d$_4$) δ ppm 7.52-7.57 (m, 1H), 7.28 (s, 1H), 7.12-7.18 (m, 1H), 7.03 (d, J=8.38 Hz, 1H), 6.85-6.96 (m, 1H), 6.52 (d, J=7.72 Hz, 1H), 5.05-5.13 (m, 1H), 4.55-4.62 (m, 1H), 3.86-3.99 (m, 3H), 3.68 (s, 3H), 3.21 (tt, J=15.24, 7.80 Hz, 2H), 1.55-1.81 (m, 3H), 0.86-1.07 (m, 6H)

Example 25. Synthesis of Viral Protease Inhibitor Compound 227

Step 1: methyl (2S)-2-amino-3- (1-methylimidazol-4-yl)propanoate

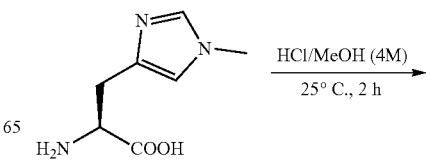

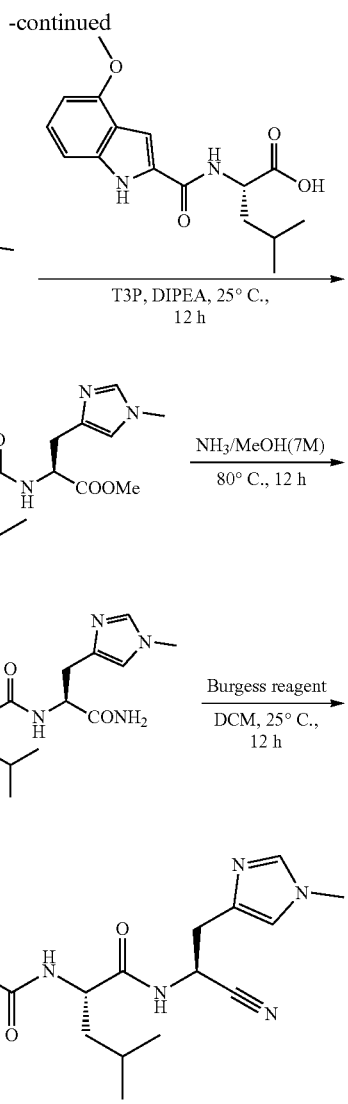

To a mixture of (2S)-2-amino-3-(1-methylimidazol-4-yl) propanoic acid (0.5 g, 2.96 mmol, 1 eq) was added HCl/MeOH (4 M, 7.39 mL, 10 eq) in one portion at 25° C. under $N_2$. The mixture was stirred at 25° C. for 2 h. The reaction mixture was concentrated to get the product. Methyl (2S)-2-amino-3-(1-methylimidazol-4-yl)propanoate (0.6 g, crude, HCl) was obtained as a solid and used directly next step. MS (ESI) m/z 184.1 [M+H]$^+$ Step 2: methyl (2S)-2-[[(2S)-2-[(4-methoxy-1H-indole-2-carbonyl)amino]-4-methyl-pentanoyl] amino]-3-(1-methylimidazol-4-yl)propanoate To a mixture of (2S)-2-[(4-methoxy-1H-indole-2-carbonyl)amino]-4-methyl-pentanoic acid (498.76 mg, 1.64 mmol, 1.2 eq) and methyl (2S)-2-amino-3-(1-methylimidazol-4-yl)propanoate (0.3 g, 1.37 mmol, 1 eq, HCl), DIPEA (882.53 mg, 6.83 mmol, 1.19 mL, 5 eq) in THF (0.9 mL) and DCM (0.9 mL) was added T3P (1.30 g, 2.05 mmol, 1.22 mL, 50% purity, 1.5 eq) at 0° C. under $N_2$. The mixture was stirred at 25° C. for 12 h. The reaction mixture was added to saturated sodium bicarbonate solution (10 mL) and extracted with DCM (10 mL*2) to get the organic phase. The organic phase was washed with brine (3 mL*3) and dried over anhydrous sodium sulfate and concentrated to get the crude product. The residue was purified by prep-HPLC. Methyl (2S)-2-[[(2S)-2-[(4-methoxy-1H-indole-2-carbonyl)amino]-4-methyl-pentanoyl]amino]-3-(1-methylimidazol-4-yl)propanoate (100 mg, 202.97 umol, 14.86% yield, 95.3% purity) was obtained as a solid. MS (ESI) m/z 470.2 [M+H]$^+$ Prep-HPLC Condition:
column: Kromasil C18 (250*50 mm*10 um); mobile phase: [water (10 mM $NH_4HCO_3$)-ACN]; B %: 25%-50%, 10 min Step 3: N-[(1S)-1-[[(1S)-2-amino-1-[(1-methylimidazol-4-yl)methyl]-2-oxo-ethyl]carbamoyl]-3-methyl-butyl]-4-methoxy-1H-indole-2-carboxamide To methyl (2S)-2-[[(2S)-2-[(4-methoxy-1H-indole-2-carbonyl)amino]-4-methyl-pentanoyl]amino]-3-(1-methylimidazol-4-yl)propanoate (100 mg, 212.98 umol, 1 eq) was added $NH_3$/MeOH (7 M, 10.00 mL, 328.67 eq) in one portion at 25° C. under $N_2$. The mixture was stirred at 80° C. for 12 h. The reaction mixture was cooled to 25° C. and concentrated to get the product. N-[(1S)-1-[[(1S)-2-amino-1-[(1-methylimidazol-4-yl)methyl]-2-oxo-ethyl]carbamoyl]-3-methyl-butyl]-4-methoxy-1H-indole-2-carboxamide (95.5 mg, 190.57 umol, 89.48% yield, 90.7% purity) was obtained as a solid and used directly next step. MS (ESI) m/z 455.2 [M+H]$^+$ Step 4: N-[(1S)-1-[[(1S)-1-cyano-2-(1-methylimidazol-4-yl)ethyl]carbamoyl]-3-methyl-butyl]-4-methoxy-1H-indole-2-carboxamide To a mixture of N-[(1S)-1-[[(1S)-2-amino-1-[(1-methylimidazol-4-yl)methyl]-2-oxo-ethyl]carbamoyl]-3-methyl-butyl]-4-methoxy-1H-indole-2-carboxamide (80.00 mg, 176.01 umol, 1 eq) in DCM (1 mL) was added Burgess reagent (83.89 mg, 352.02 umol, 2 eq) in one portion at 25° C. under $N_2$. The mixture was stirred at 25° C. for 12 h. The reaction mixture was added the water (0.3 mL) and stirred for 10 min. Then the reaction mixture was concentrated to get the crude product. The crude product was purified by prep-HPLC. N-[(1S)-1-[[(1S)-1-cyano-2-(1-methylimidazol-4-yl)ethyl] carbamoyl]-3-methyl-butyl]-4-methoxy-1H-indole-2-carboxamide (26.39 mg, 60.27 umol, 34.24% yield, 99.684% purity) was obtained as a solid. MS (ESI) m/z 437.2 [M+H]$^+$ Prep-HPLC Condition:
column: Waters Xbridge BEH C18 100*25 mm*5 um; mobile phase: [water (10 mM $NH_4HCO_3$)-ACN]; B %: 25%-55%, 10 min $^1$H NMR (400 MHz, METHANOL-$d_4$) δ ppm 7.35 (s, 1H), 7.28 (s, 1H), 7.12-7.20 (m, 1H), 7.05 (d, J=8.38 Hz, 1H), 6.91-6.98 (m, 1H), 6.53 (d, J=7.72 Hz, 1H), 5.01 (t, J=7.06 Hz, 1H), 4.63 (br dd, J=9.59, 4.96 Hz, 1H), 3.94 (s, 3H), 3.46-3.59 (m, 3H), 3.00-3.13 (m, 2H), 1.61-1.81 (m, 3H), 0.89-1.07 (m, 6H)

Step 5: tert-butyl (2S)-2-[(4-methoxy-1H-indole-2-carbonyl)amino]-4-methyl-pentanoate To a mixture of 4-methoxy-1H-indole-2-carboxylic acid (5 g, 26.15 mmol, 1 eq) and tert-butyl (2S)-2-amino-4-methyl-pentanoate (5.88 g, 31.38 mmol, 1.2 eq, HCl), EDCI (6.52 g, 34.00 mmol, 1.3 eq), HOBt (4.59 g, 34.00 mmol, 1.3 eq) in DMF (30 mL) was added TEA (7.94 g, 78.46 mmol, 10.92 mL, 3 eq) in one portion at 25° C. under $N_2$. The mixture was stirred at 25° C. and stirred for 2 h. The reaction mixture was added water (90 mL) and extracted with EtOAc (25 mL*3) to get the organic phase. The organic phase was washed with 5% citric acid (25 mL) and 5% aqueous solution of sodium bicarbonate (25 mL) and dried over anhydrous sodium sulfate, filtered and concentrated to get the product. The residue was purified by column chromatography (SiO$_2$, petroleum ether:EtOAc=30:1 to 10:1). Tert-butyl (2S)-2-[(4-methoxy-1H-indole-2-carbonyl)amino]-4-methyl-pentanoate (5.93 g, 16.45 mmol, 62.91% yield) was obtained as solid. MS (ESI) m/z 361.2 [M+H]$^+$ $^1$H NMR (400 MHz, CHLOROFORM-d) δ ppm 9.25 (br s, 1H), 7.10-7.16 (m, 1H), 6.93-7.00 (m, 2H), 6.56 (br d, J=8.31 Hz, 1H), 6.44 (d, J=7.70 Hz, 1H), 4.66 (td, J=8.50, 5.14 Hz, 1H), 3.88 (s, 3H), 1.62-1.75 (m, 2H), 1.57-1.62 (m, 1H), 1.42 (s, 9H), 0.92 (dd, J=6.17, 3.85 Hz, 6H).

Step 6: (2S)-2-[(4-methoxy-1H-indole-2-carbonyl)amino]-4-methyl-pentanoic acid

To a mixture of tert-butyl (2S)-2-[(4-methoxy-1H-indole-2-carbonyl)amino]-4-methyl-pentanoate (2.00 g, 5.55 mmol, 1 eq) in DCM (8 mL) was added TFA (10.27 g, 90.04 mmol, 6.67 mL, 16.23 eq) and H$_2$O (666.67 mg, 37.01 mmol, 666.67 uL, 6.67 eq) in one portion at 0° C. under N$_2$. The mixture was stirred at 25° C. and stirred for 4 h. The reaction mixture was concentrated to get the crude product. (2S)-2-[(4-methoxy-1H-indole-2-carbonyl)amino]-4-methyl-pentanoic acid (2.24 g, 5.35 mmol, 96.50% yield, TFA) was obtained as a solid and used directly next step. MS (ESI) m/z 305.1 [M+H]$^+$ Example 26. Synthesis of Viral Protease Inhibitor Compound 231

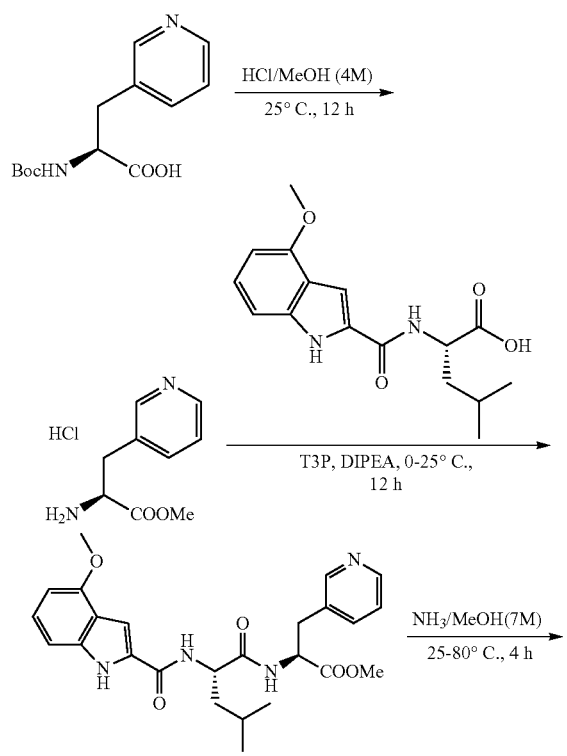

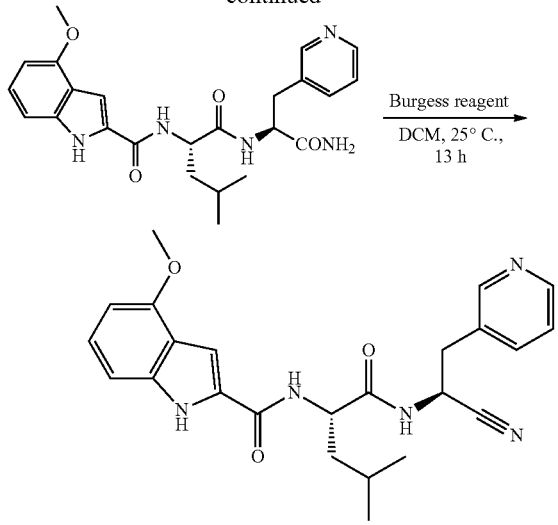

To a mixture of (2S)-2-(tert-butoxycarbonylamino)-3-(3-pyridyl)propanoic acid (500 mg, 1.88 mmol, 1 eq) was added HCl/MeOH (4 M, 20.80 mL, 44.31 eq) in one portion at 25° C. under N$_2$. The mixture was stirred at 25° C. and stirred for 12 h. Upon completion, the reaction mixture was concentrated to get methyl (2S)-2-amino-3-(3-pyridyl)propanoate (400 mg, crude, HCl) as an oil and used directly for the next step. MS (ESI) m/z 181.1 [M+H]$^+$ Step 2: (S)-methyl 2-((S)-2-(4-methoxy-1H-indole-2-carboxamido)-4-methylpentanamido)-3-(pyridine-3-yl)propanoate To a mixture of methyl (2S)-2-amino-3-(3-pyridyl)propanoate (0.3 g, 1.66 mmol, 1 eq, HCl) and (2S)-2-[(4-methoxy-1H-indole-2-carbonyl)amino]-4-methyl-pentanoic acid (506.66 mg, 1.66 mmol, 1 eq), DIPEA (1.08 g, 8.32 mmol, 1.45 mL, 5 eq) in THF (0.6 mL) and DCM (0.6 mL) was added T$_3$P (1.59 g, 2.50 mmol, 1.49 mL, 50% purity, 1.5 eq) at 0° C. under N$_2$. The mixture was stirred at 25° C. for 12 h. Upon completion, the reaction mixture was added saturated sodium bicarbonate solution (10 mL) and extracted with DCM (10 mL*2) to get the organic phase. The organic phase was concentrated to get the crude product. The residue was purified by pulping with petroleum ether (20 mL) and filtered to get the filter cake as the product. Methyl (2S)-2-[[(2S)-2-[(4-methoxy-1H-indole-2-carbonyl)amino]-4-methyl-pentanoyl]amino]-3-(3-pyridyl)propanoate (0.4 g, crude) was obtained as a solid and used directly next step. MS (ESI) m/z 467.1 [M+H]$^+$ Step 3: N-((S)-1-(((S)-1-amino-1-oxo-3-(pyridin-3-yl)propan-2-yl)amino)-4-methyl-1-oxopentan-2-yl)-4-methoxy-1H-indole-2-carboxamide To a mixture of methyl (2S)-2-[[(2S)-2-[(4-methoxy-1H-indole-2-carbonyl)amino]-4-methyl-pentanoyl]amino]-3-(3-pyridyl)propanoate (200.00 mg, 428.70 umol, 1 eq) was added NH$_3$/MeOH (7 M, 5 mL, 81.64 eq) in one portion at 25° C. under N$_2$. The mixture was stirred at 80° C. for 4 h. Upon completion, the reaction mixture was cooled to 25° C. and concentrated to get N-[(1S)-1-[[(1S)-2-amino-2-oxo-1-(3-pyridylmethyl)ethyl]carbamoyl]-3-methyl-butyl]-4-methoxy-1H-indole-2-carboxamide (0.18 g, 339.65 umol, 79.23% yield, 85.2% purity) as a solid and used directly next step. MS (ESI) m/z 452.2 [M+H]+

Step 3: N-((S)-1-(((S)-1-cyano-2-(pyridin-3-yl) ethyl)amino)-4-methyl-1-oxopentan-2-yl)-4-methoxy-1H-indole-2-carboxamide To a mixture of N-[(1S)-1-[[(1S)-2-amino-2-oxo-1-(3-pyridylmethyl)ethyl]carbamoyl]-3-methyl-butyl]-4-methoxy-1H-indole-2-carboxamide (0.1 g, 221.48 umol, 1 eq) in DCM (1 mL) was added Burgess reagent (105.56 mg, 442.95 umol, 2 eq) in one portion at 25° C. under $N_2$. The mixture was stirred at 25° C. for 12 h. The Burgess reagent (105.56 mg, 442.95 umol, 2 eq) was re-added into the above solution at 25° C. and the reaction mixture was stirred at 25° C. for 1 h. Upon completion, the reaction mixture was added the water (0.5 mL) and stirred for 10 min. Then the mixture was concentrated to get the crude product. The crude product was purified by pre-HPLC to give N-[(1S)-1-[[(1S)-1-cyano-2-(3-pyridyl)ethyl]carbamoyl]-3-methyl-butyl]-4-methoxy-1H-indole-2-carboxamide (23.18 mg, 52.94 umol, 23.90% yield, 99.009% purity) as a solid. MS (ESI) m/z 434.2 [M+H]+
Prep-HPLC Condition:
column: Waters Xbridge BEH C18 100*25 mm*5 um; mobile phase: [water (10 mM $NH_4HCO_3$)-ACN]; B %: 30%-60%, 10 min
$^1$H NMR (400 MHz, METHANOL-$d_4$) δ ppm 8.47-8.52 (m, 1H), 8.34-8.45 (m, 1H), 7.77-7.84 (m, 1H), 7.28-7.38 (m, 1H), 7.23-7.28 (m, 1H), 7.12-7.19 (m, 1H), 6.99-7.07 (m, 1H), 6.52 (d, J=7.63 Hz, 1H), 5.08-5.18 (m, 1H), 4.48-4.61 (m, 1H), 3.94 (s, 3H), 3.12-3.29 (m, 2H), 1.41-1.76 (m, 3H), 0.87-1.03 (m, 6H).

Step 5: (S)-tert-butyl 2-(4-methoxy-1H-indole-2-carboxamido)-4-methylpentanoate

To a mixture of 4-methoxy-1H-indole-2-carboxylic acid (5 g, 26.15 mmol, 1 eq) and tert-butyl (2S)-2-amino-4-methyl-pentanoate (5.88 g, 31.38 mmol, 1.2 eq, HCl), EDCI (6.52 g, 34.00 mmol, 1.3 eq), HOBt (4.59 g, 34.00 mmol, 1.3 eq) in DMF (30 mL) was added TEA (7.94 g, 78.46 mmol, 10.92 mL, 3 eq) in one portion at 25° C. under $N_2$. The mixture was stirred at 25° C. and stirred for 2 h. Upon completion, the reaction mixture was added water (90 mL) and extracted with ethyl acetate (25 mL*3) to get the organic phase. The organic phase was washed with 5% citric acid (25 mL) and 5% aqueous solution of sodium bicarbonate (25 mL) and dried over anhydrous sodium sulfate, filtered and concentrated to get the crude product. The residue was purified by column chromatography ($SiO_2$, petroleum ether: EtOAc=30:1 to 10:1) to give tert-butyl (2S)-2-[(4-methoxy-1H-indole-2-carbonyl)amino]-4-methyl-pentanoate (5.93 g, 16.45 mmol, 62.91% yield) as a solid. MS (ESI) m/z 361.2 [M+H]+
$^1$H NMR (400 MHz, CHLOROFORM-d) δ ppm 9.25 (br s, 1H), 7.10-7.16 (m, 1H), 6.93-7.00 (m, 2H), 6.56 (br d, J=8.31 Hz, 1H), 6.44 (d, J=7.70 Hz, 1H), 4.66 (td, J=8.50, 5.14 Hz, 1H), 3.88 (s, 3H), 1.62-1.75 (m, 2H), 1.57-1.62 (m, 1H), 1.42 (s, 9H), 0.92 (dd, J=6.17, 3.85 Hz, 6H).

Step 6: (S)-2-(4-methoxy-1H-indole-2-carboxamido)-4-methylpentanoic acid

To a mixture of tert-butyl (2S)-2-[(4-methoxy-1H-indole-2-carbonyl)amino]-4-methyl-pentanoate (0.5 g, 1.39 mmol, 1 eq) in DCM (0.33 mL) was added TFA (2.57 g, 22.51 mmol, 1.67 mL, 16.23 eq) and $H_2O$ (166.71 mg, 9.25 mmol, 166.71 uL, 6.67 eq) in one portion at 0° C. under $N_2$. The mixture was stirred at 25° C. and stirred for 2 h. Upon completion, the reaction mixture was concentrated to give (S)-2-(4-methoxy-1H-indole-2-carboxamido)-4-methylpentanoic acid (400 mg, crude, TFA) as a solid and used directly next step. MS (ESI) m/z 305.1 [M+H]+

Example 27. Synthesis of Viral Protease Inhibitor Compound 599

Step 1: tert-butyl (2S)-2-[(4-methoxy-1H-indole-2-carbonyl)amino]-4-methyl- pentanoate

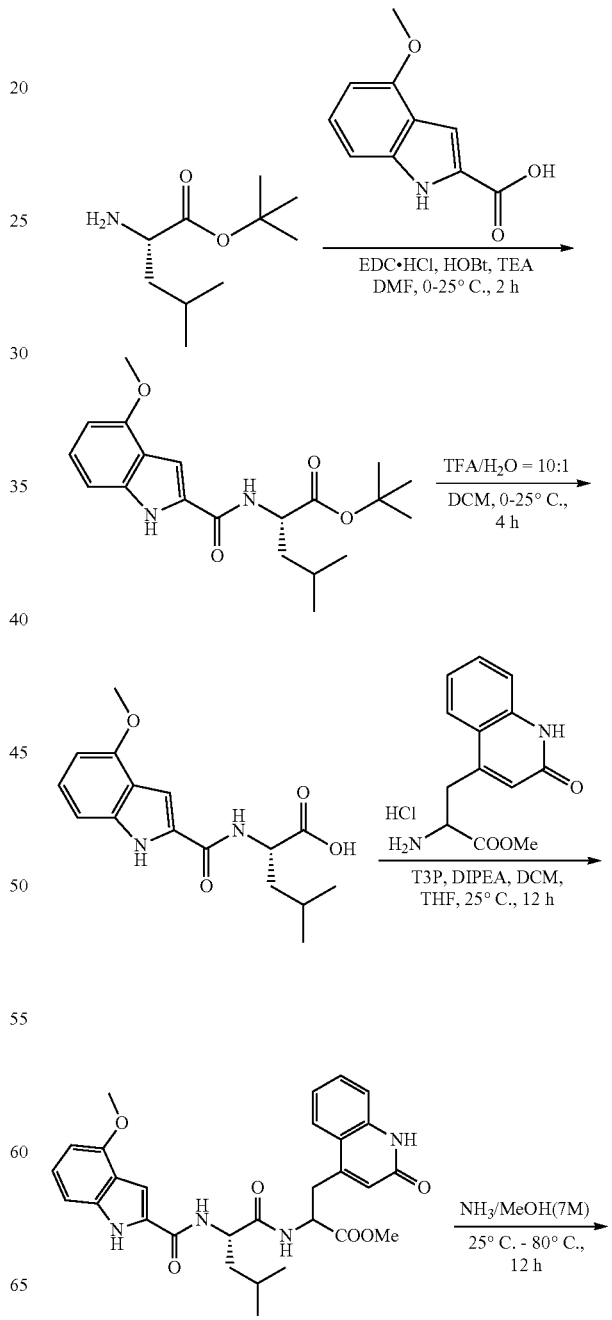

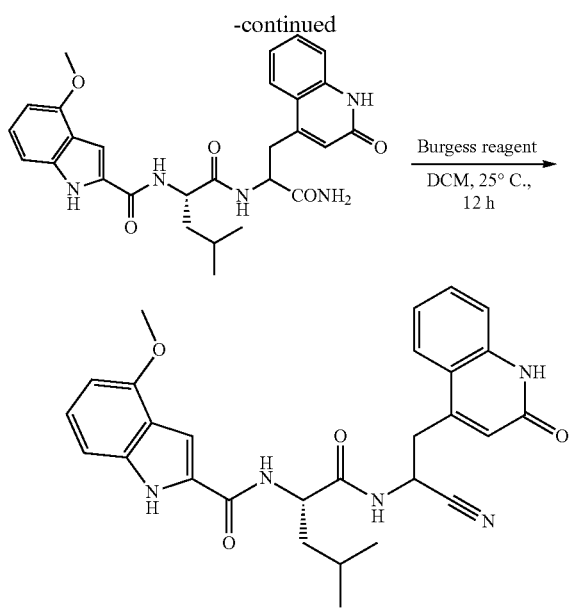

To a mixture of 4-methoxy-1H-indole-2-carboxylic acid (5 g, 26.15 mmol, 1 eq) and tert-butyl (2S)-2-amino-4-methyl-pentanoate (5.88 g, 31.38 mmol, 1.2 eq, HCl), EDCI (6.52 g, 34.00 mmol, 1.3 eq), HOBt (4.59 g, 34.00 mmol, 1.3 eq) in DMF (30 mL) was added TEA (7.94 g, 78.46 mmol, 10.92 mL, 3 eq) in one portion at 25° C. under N$_2$. The mixture was stirred at 25° C. and stirred for 2 h. The reaction mixture was added with water (90 mL) and extracted with EtOAc (25 mL*3) to get the organic phase. The organic phase was washed with 5% citric acid (25 mL) and 5% aqueous solution of sodium bicarbonate (25 mL) and dried over anhydrous sodium sulfate, filtered and concentrated to get the product. The residue was purified by column chromatography (SiO$_2$, petroleum ether:EtOAc=30:1 to 10:1). Tert-butyl (2S)-2-[(4-methoxy-1H-indole-2-carbonyl) amino]-4-methyl-pentanoate (5.93 g, 16.45 mmol, 62.91% yield) was obtained as a solid. MS (ESI) m/z 361.2 [M+H]$^+$ $^1$H NMR (400 MHz, CHLOROFORM-d) δ ppm 9.25 (br s, 1H), 7.10-7.16 (m, 1H), 6.93-7.00 (m, 2H), 6.56 (br d, J=8.31 Hz, 1H), 6.44 (d, J=7.70 Hz, 1H), 4.66 (td, J=8.50, 5.14 Hz, 1H), 3.88 (s, 3H), 1.62-1.75 (m, 2H), 1.57-1.62 (m, 1H), 1.42 (s, 9H), 0.92 (dd, J=6.17, 3.85 Hz, 6H).

Step 2: (2S)-2-[(4-methoxy-1H-indole-2-carbonyl) amino]-4-methyl-pentanoic acid

To a mixture of tert-butyl (2S)-2-[(4-methoxy-1H-indole-2-carbonyl)amino]-4-methyl-pentanoate (2.00 g, 5.55 mmol, 1 eq) in DCM (8 mL) was added TFA (10.27 g, 90.04 mmol, 6.67 mL, 16.23 eq) and H$_2$O (666.67 mg, 37.01 mmol, 666.67 uL, 6.67 eq) in one portion at 0° C. under N$_2$. The mixture was stirred at 25° C. and stirred for 4 h. The reaction mixture was concentrated to get the crude product. (2S)-2-[(4-methoxy-1H-indole-2-carbonyl)amino]-4-methyl-pentanoic acid (2.24 g, 5.35 mmol, 96.50% yield, TFA) was obtained as a solid and used directly next step. MS (ESI) m/z 305.1 [M+H]$^+$ Step 3: methyl 2-[[(2S)-2-[(4-methoxy-1H-indole-2-carbonyl)amino]-4-methyl-pentanoyl]amino]-3-(2-oxo-1H-quinolin-4-yl)propanoate To a mixture of (2S)-2-[(4-methoxy-1H-indole-2-carbonyl)amino]-4-methyl-pentanoic acid (568.23 mg, 1.36 mmol, 1.2 eq, TFA) and methyl 2-amino-3-(2-oxo-1H-quinolin-4-yl)propanoate (320 mg, 1.13 mmol, 1 eq, HCl), DIPEA (731.40 mg, 5.66 mmol, 985.72 uL, 5 eq) in THF (1 mL) and DCM (1 mL) was added T3P (1.08 g, 1.70 mmol, 1.01 mL, 50% purity, 1.5 eq) at 0° C. under N$_2$. The mixture was stirred at 25° C. for 12 h. The reaction mixture was added with saturated sodium bicarbonate solution (10 mL) and extracted with DCM (10 mL*2) to get the organic phase. The organic phase was concentrated to get the crude product. The residue was purified by prep-HPLC. Methyl 2-[[(2S)-2-[(4-methoxy-1H-indole-2-carbonyl)amino]-4-methyl-pentanoyl]amino]-3-(2-oxo-1H-quinolin-4-yl)propanoate (0.2 g, 375.53 umol, 33.18% yield) was obtained as a solid. MS (ESI) m/z 533.2 [M+H]$^+$ Prep-HPLC condition: column: Kromasil C18 (250*50 mm*10 um); mobile phase: [water (10 mM NH$_4$HCO$_3$)-ACN]; B %: 30%-60%, 10 min Step 4: N-[(1S)-1-[[2-amino-2-oxo-1-[(2-oxo-1H-quinolin-4-yl)methyl]ethyl]carbamoyl]-3-methyl-butyl]-4-methoxy-1H-indole-2-carboxamide To a mixture of methyl2-[[(2S)-2-[(4-methoxy-1H-indole-2-carbonyl)amino]-4-methyl-pentanoyl] amino]-3-(2-oxo-1H-quinolin-4-yl)propanoate (200.00 mg, 375.53 umol, 1 eq) was added NH$_3$/MeOH (7 M, 10.00 mL, 186.41 eq) in one portion at 25° C. under N$_2$. The mixture was stirred at 80° C. for 12 h. The reaction mixture was cooled to 25° C. and concentrated to get the product. N-[(1S)-1-[[2-amino-2-oxo-1-[(2-oxo-1H-quinolin-4-yl)methyl]ethyl]carbamoyl]-3-methyl-butyl]-4-methoxy-1H-indole-2-carboxamide (180 mg, 326.21 umol, 86.87% yield, 93.8% purity) was obtained as a solid and used directly next step. MS (ESI) m/z 518.2 [M+H]$^+$ Step 5: N-[(1S)-1-[[1-cyano-2-(2-oxo-1H-quinolin-4-yl)ethyl]carbamoyl]-3-methyl-butyl]-4-methoxy-1H-indole-2-carboxamide To a mixture of N-[(1S)-1-[[2-amino-2-oxo-1-[(2-oxo-1H-quinolin-4-yl)methyl]ethyl]carbamoyl]-3-methyl-butyl]-4-methoxy-1H-indole-2-carboxamide (90 mg, 173.89 umol, 1 eq) in DCM (5 mL) was added Burgess reagent (207.19 mg, 869.44 umol, 5 eq) in one portion at 25° C. under N$_2$. The mixture was stirred at 25° C. for 12 h, and then concentrated to get the crude product.

The residue was purified by prep-HPLC. N-[(1S)-1-[[1-cyano-2-(2-oxo-1H-quinolin-4-yl)ethyl] carbamoyl]-3-methyl-butyl]-4-methoxy-1H-indole-2-carboxamide (20.74 mg, 41.13 umol, 23.66% yield, 99.079% purity) was obtained as a solid. MS (ESI) m/z 500.2 [M+H]$^+$ Prep-HPLC condition: column: Waters Xbridge BEH C18 100*25 mm*5 um; mobile phase: [water (10 mM NH$_4$HCO$_3$)-ACN]; B %: 30%-65%, 10 min $^1$H NMR (400 MHz, METHANOL-d$_4$) δ ppm 7.93 (br d, J=8.16 Hz, 1H), 7.50-7.58 (m, 1H), 7.28-7.40 (m, 2H), 7.26 (dd, J=11.47, 0.66 Hz, 1H), 7.11-7.19 (m, 1H), 7.04 (dd, J=8.27, 4.08 Hz, 1H), 6.59-6.70 (m, 1H), 6.46-6.56 (m, 1H), 5.24-5.34 (m, 1H), 4.53 (td, J=10.31, 5.18 Hz, 1H), 3.93 (d, J=4.41 Hz, 3H), 3.40-3.59 (m, 3H), 1.72 (ddd, J=15.16, 9.87, 5.18 Hz, 1H), 1.53-1.66 (m, 2H), 1.40-1.50 (m, 1H), 0.87-1.01 (m, 5H)

Step 6: methyl 2-amino-3-(2-oxo-1H-quinolin-4-yl)propanoate

To 2-amino-3-(2-oxo-1H-quinolin-4-yl)propanoic acid (400 mg, 1.72 mmol, 1 eq) was added HCl/MeOH (4 M, 4.31 mL, 10 eq) in one portion at 25° C. under N$_2$. The mixture was stirred at 25° C. and stirred for 1 h. The reaction mixture was concentrated to get the product. Methyl 2-amino-3-(2-oxo-1H-quinolin-4-yl)propanoate (370 mg, crude, HCl) was obtained as a solid and used directly next step.

Example 28. Synthesis of Viral Protease Inhibitor Compound 249

Step 1: 2-amino-3-(2-oxo-3,4-dihydro-1H-quinolin-4-yl)propanoic acid

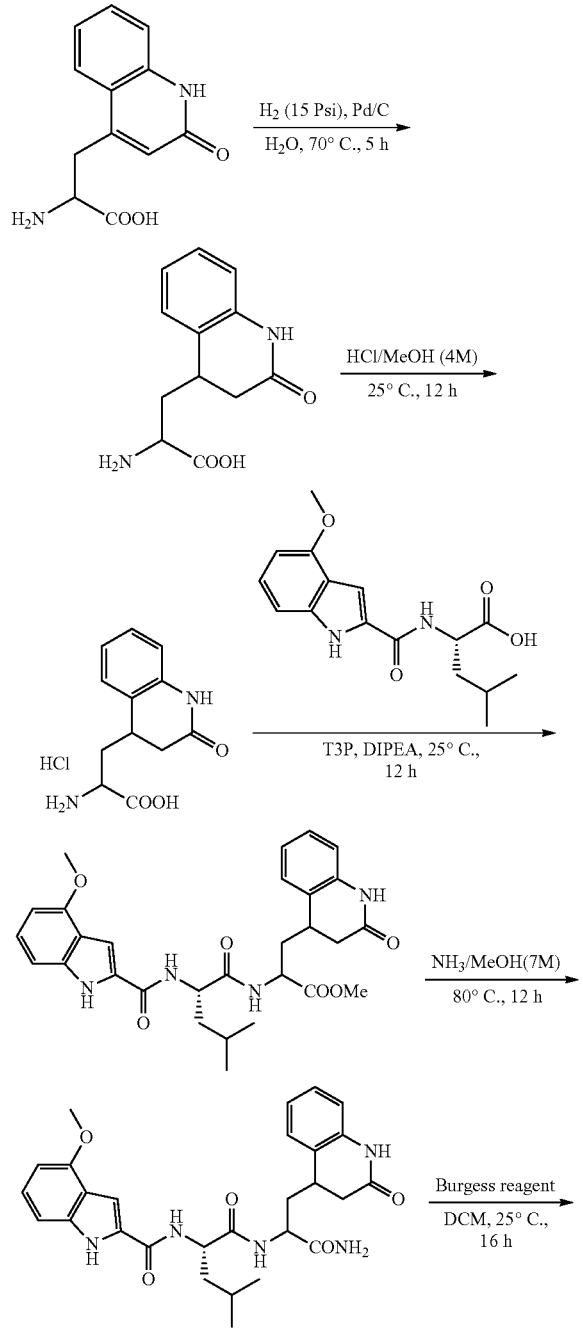

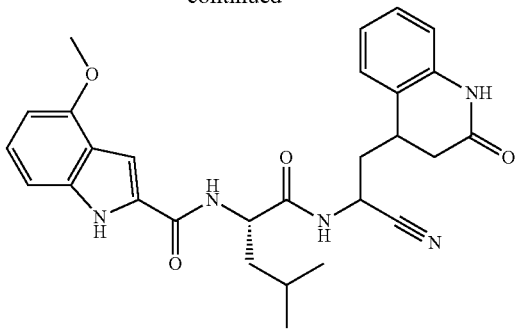

To a solution of 2-amino-3-(2-oxo-1H-quinolin-4-yl)propanoic acid (200 mg, 861.20 umol, 1 eq) in H$_2$O (1 mL) was added Pd/C (20 mg, 861.20 umol, 10% purity) at 25° C. under N$_2$. The suspension was degassed under vacuum and purged with H$_2$ several times. The mixture was stirred under H$_2$ (861.20 umol) (15 psi) at 70° C. for 5 h. The reaction mixture was cooled to 25° C. and filtered to get the filtrate. The filtrate was concentrated to get the product. 2-amino-3-(2-oxo-3,4-dihydro-1H-quinolin-4-yl)propanoic acid (200 mg, crude) was obtained as a solid and used directly next step. MS (ESI) m/z 235.0 [M+H]$^+$ $^1$H NMR (400 MHz, METHANOL-d$_4$) δ ppm 1.92-2.03 (m, 1H) 2.06-2.21 (m, 1H) 2.45-2.62 (m, 1H) 2.86 (dd, J=16.43, 6.06 Hz, 1H) 3.32-3.40 (m, 1H) 3.83 (br dd, J=8.49, 5.84 Hz, 1H) 3.93 (br t, J=6.95 Hz, 1H) 6.93 (d, J=7.72 Hz, 1H) 7.01-7.10 (m, 1H) 7.24 (br t, J=7.72 Hz, 1H) 7.36 (d, J=7.06 Hz, 1H)

Step 2: methyl 2-amino-3-(2-oxo-3,4-dihydro-1H-quinolin-4-yl)propanoate

To 2-amino-3-(2-oxo-3,4-dihydro-1H-quinolin-4-yl)propanoic acid (200 mg, 853.79 umol, 1 eq) was added HCl/MeOH (4 M, 9.91 mL, 46.45 eq) in one portion at 25° C. under N$_2$. The mixture was stirred at 25° C. for 12 h. The reaction mixture was concentrated to get the crude product. Methyl 2-amino-3-(2-oxo-3,4-dihydro-1H-quinolin-4-yl)propanoate (260 mg, crude, HCl) was obtained as the yellow oil and used directly next step. MS (ESI) m/z 249.1 [M+H]$^+$ Step 3: methyl2-[[(2S)-2-[(4-methoxy-1H-indole-2-carbonyl)amino]-4-methyl-pentanoyl]amino]-3-(2-oxo-3,4-dihydro-1H-quinolin-4-yl)propanoate To a mixture of methyl2-amino-3-(2-oxo-3,4-dihydro-1H-quinolin-4-yl)propanoate (260 mg, 913.12 umol, 1 eq, HCl) and (2S)-2-[(4-methoxy-1H-indole-2-carbonyl)amino]-4-methyl-pentanoic acid (277.90 mg, 913.12 umol, 1 eq), DIPEA (590.07 mg, 4.57 mmol, 795.24 uL, 5 eq) in THF (0.6 mL) and DCM (0.6 mL) was added T$_3$P (871.61 mg, 1.37 mmol, 814.59 uL, 50% purity, 1.5 eq) at 0° C. under N$_2$. The mixture was stirred at 25° C. for 12 h. The reaction mixture was added saturated sodium bicarbonate solution (10 mL) and extracted with DCM (10 mL*2) to get the organic phase. The organic phase was concentrated to get the crude product. The residue was purified by pre-HPLC. Methyl 2-[[(2S)-2-[(4-methoxy-1H-indole-2-carbonyl)amino]-4-methyl-pentanoyl]amino]-3-(2-oxo-3,4-dihydro-1H-quinolin-4-yl)propanoate (85 mg, 151.05 umol, 16.54% yield, 95% purity) was obtained as a solid. MS (ESI) m/z 535.2 [M+H]$^+$ Prep-HPLC condition: column: Phenomenex Gemini-NX 80*40 mm*3 um; mobile phase: [water (10 mM NH4HCO3)-ACN]; B %: 27%-47%, 8 min

Step 4: N-[(1S)-1-[[2-amino-2-oxo-1-[(2-oxo-3,4-dihydro-1H-quinolin-4-yl)methyl]ethyl]carbamoyl]-3-methyl-butyl]-4-methoxy-1H-indole-2-carboxamide To a mixture of methyl 2-[[(2S)-2-[(4-methoxy-1H-indole-2-carbonyl)amino]-4-methyl-pentanoyl] amino]-3-(2-oxo-3,4-dihydro-1H-quinolin-4-yl)propanoate (55 mg, 102.88 umol, 1 eq) was added $NH_3$/MeOH (7 M, 1.83 mL, 124.74 eq) in one portion at 25° C. under $N_2$. The mixture was stirred at 80° C. for 12 h. The reaction mixture was cooled to the 25° C. and concentrated to get the product. N-[(1S)-1-[[2-amino-2-oxo-1-[(2-oxo-3,4-dihydro-1H-quinolin-4-yl)methyl]ethyl]carbamoyl]-3-methyl-butyl]-4-methoxy-1H-indole-2-carboxamide (55 mg, crude) was obtained as a solid and used directly next step. MS (ESI) m/z 518.2 $[M+H]^+$

Step 5: N-[(1S)-1-[[1-cyano-2-(2-oxo-1H-quinolin-4-yl)ethyl]carbamoyl]-3-methyl-butyl]-4-methoxy-1H-indole-2-carboxamide To a mixture of N-[(1S)-1-[[2-amino-2-oxo-1-[(2-oxo-3,4-dihydro-1H-quinolin-4-yl)methyl]ethyl] carbamoyl]-3-methyl-butyl]-4-methoxy-1H-indole-2-carboxamide (75 mg, 144.34 umol, 1 eq) in DCM (0.1 mL) was added Burgess reagent (103.19 mg, 433.03 umol, 3 eq) in one portion at 25° C. under $N_2$. The mixture was stirred at 25° C. and stirred for 16 h. The reaction mixture was added with water (0.5 mL) and stirred for 10 min. Then the mixture was concentrated to get the crude product. The crude product was purified by pre-HPLC. N-[(1S)-1-[[1-cyano-2-(2-oxo-3,4-dihydro-1H-quinolin-4-yl) ethyl]carbamoyl]-3-methyl-butyl]-4-methoxy-1H-indole-2-carboxamide (26.51 mg, 52.85 umol, 36.62% yield, 100% purity) was obtained as a solid. MS (ESI) m/z 502.2 $[M+H]^+$ Prep-HPLC condition: column: Waters Xbridge BEH C18 100*25 mm*5 um; mobile phase: [water (10 mM $NH_4HCO_3$)-ACN]; B %: 30%-60%, 10 min $^1$H NMR (400 MHz, DMSO-$d_6$) δ ppm 11.51-11.61 (m, 1H), 10.14-10.20 (m, 1H), 8.84-9.01 (m, 1H), 8.42-8.59 (m, 1H), 7.32-7.42 (m, 1H), 7.05-7.22 (m, 3H), 6.81-7.04 (m, 3H), 6.50 (dd, J=7.64, 3.85 Hz, 1H), 4.37-4.66 (m, 2H), 3.83-3.95 (m, 3H), 2.95-3.12 (m, 1H), 2.63-2.82 (m, 1H), 2.26-2.42 (m, 1H), 1.88-2.08 (m, 2H), 1.45-1.82 (m, 3H), 0.81-1.02 (m, 6H)

Step 6: (S)-tert-butyl 2-(4-methoxy-1H-indole-2-carboxamido)-4-methylpentanoate To a mixture of 4-methoxy-1H-indole-2-carboxylic acid (15 g, 78.46 mmol, 1 eq) and tert-butyl (2S)-2-amino-4-methyl-pentanoate (21.07 g, 94.15 mmol, 1.2 eq, HCl) in DMF (150 mL) was added EDCI (19.55 g, 102.00 mmol, 1.3 eq), HOBt (13.78 g, 102.00 mmol, 1.3 eq), TEA (23.82 g, 235.38 mmol, 32.76 mL, 3 eq) at 25° C. under $N_2$. The mixture was stirred at 25° C. and stirred for 2 h. The reaction mixture was added water (450 mL) and extracted with EtOAc (250 mL*3) to get the organic phase. The organic phase was washed with 5% citric acid (300 mL) and 5% aqueous solution of sodium bicarbonate (300 mL) and dried over anhydrous sodium sulfate, filtered and concentrated to get the product. The residue was purified by column chromatography ($SiO_2$, petroleum ether:EtOAc=30:1 to 10:1). tert-butyl (2S)-2-[(4-methoxy-1H-indole-2-carbonyl)amino]-4-methyl-pentanoate (24 g, 66.58 mmol, 84.87% yield) was obtained as a solid. MS (ESI) m/z 361.2 $[M+H]^+$

Step 7: (S)-2-(4-methoxy-1H-indole-2-carboxamido)-4-methylpentanoic acid

To a mixture of tert-butyl (2S)-2-[(4-methoxy-1H-indole-2-carbonyl)amino]-4-methyl-pentanoate (10 g, 27.74 mmol, 1 eq) in DCM (30 mL) was added TFA (61.60 g, 540.26 mmol, 40 mL, 19.47 eq) and $H_2O$ (4.00 g, 221.98 mmol, 4.00 mL, 8.00 eq) in one portion at 0° C. under $N_2$. The mixture was stirred at 25° C. for 2 h. The reaction mixture was concentrated to get the crude product. The crude product was purified with petroleum ether:ethyl acetate=10:1 (20 mL) and filtered to get the product. (2S)-2-[(4-methoxy-1H-indole-2-carbonyl)amino]-4-methyl-pentanoic acid (6 g, 19.22 mmol, 69.27% yield, 97.48% purity) was obtained as a solid. MS (ESI) m/z 305.1 $[M+H]^+$

Example 29. Synthesis of Viral Protease Inhibitor Compound 600

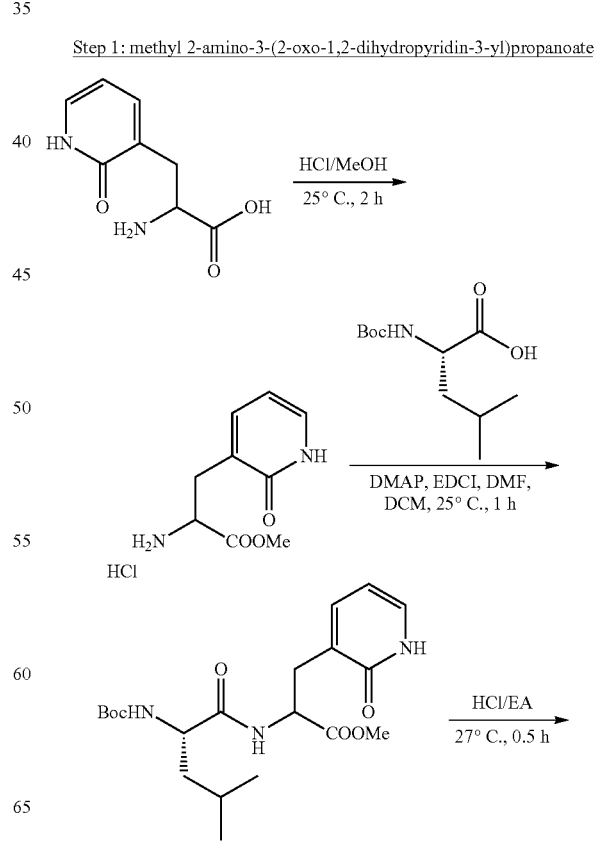

Step 1: methyl 2-amino-3-(2-oxo-1,2-dihydropyridin-3-yl)propanoate

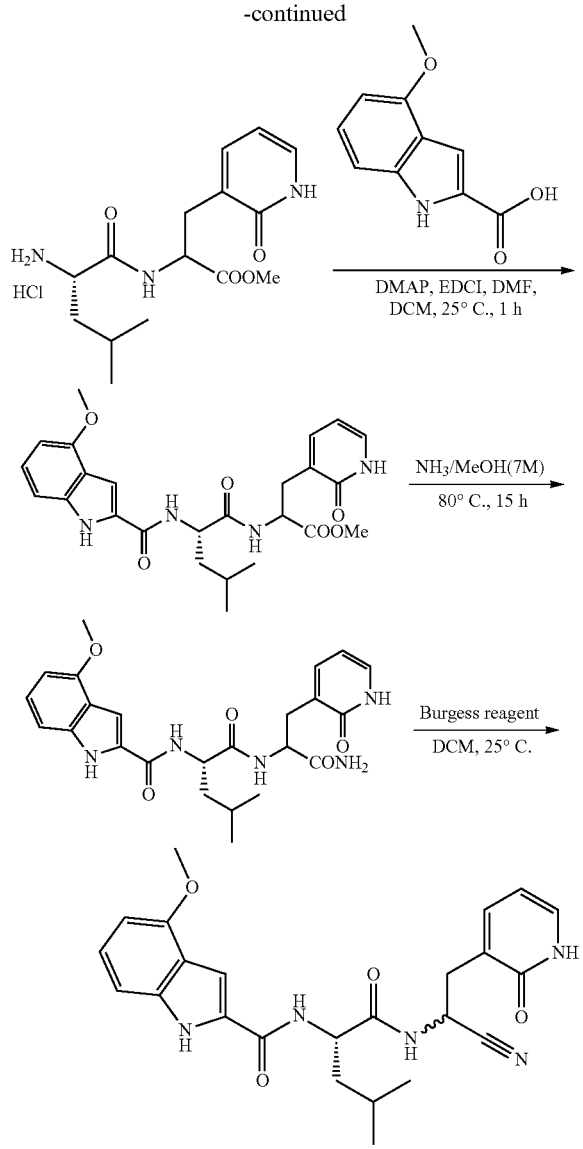

A mixture of 2-amino-3-(2-oxo-1H-pyridin-3-yl)propanoic acid (500 mg, 2.74 mmol, 1 eq) and HCl/MeOH (4 M, 30 mL, 43.72 eq) was stirred at 25° C. for 2 h. The reaction mixture was concentrated under reduced pressure to give a product methyl 2-amino-3-(2-oxo-1,2-dihydropyridin-3-yl)propanoate (650 mg, crude, HCl) as a yellow oil and used directly for next step. MS (ESI) m/z 197.0 [M+H]$^+$ Step 2: methyl-2-((S)-2-((tert-butoxycarbonyl)amino)-4-methylpentanamido)-3-(2-oxo-1,2-dihydropyridin-3-yl)propanoate A mixture of methyl 2-amino-3-(2-oxo-1H-pyridin-3-yl)propanoate (650 mg, 2.79 mmol, 1 eq, HCl), (2S)-2-(tert-butoxycarbonylamino)-4-methyl-pentanoic acid (646.16 mg, 2.79 mmol, 1 eq), EDCI (1.07 g, 5.59 mmol, 2 eq), DMAP (682.62 mg, 5.59 mmol, 2 eq), DMF (2 mL) and DCM (4 mL) was stirred at 25° C. for 1 h. The reaction mixture was diluted with H$_2$O (30 mL) and extracted with DCM (30 mL*3). The combined organic layers were washed with brine (50 mL), dried over Na$_2$SO$_4$, filtered and concentrated under reduced pressure to give a residue. The residue was purified by column chromatography (SiO$_2$, petroleum ether/EtOAc=0/1) to get the product methyl-2-((S)-2-((tert-butoxycarbonyl)amino)-4-methylpentanamido)-3-(2-oxo-1,2-dihydropyridin-3-yl)propanoate (900 mg, 1.89 mmol, 67.68% yield, 86.02% purity), as a solid. MS (ESI) m/z 410.1 [M+H]$^+$ Step 3: methyl 2-((S)-2-amino-4-methylpentanamido)-3-(2-oxo-1,2-dihydropyridin-3-yl)propanoate A mixture of methyl-2-((S)-2-((tert-butoxycarbonyl)amino)-4-methylpentanamido)-3-(2-oxo-1,2-dihydropyridin-3-yl)propanoate (200 mg, 488.43 umol, 1 eq) and HCl/EtOAc (4 M, 30 mL) was stirred at 27° C. for 0.5 h. The reaction mixture was concentrated under reduced pressure to give a product methyl 2-((S)-2-amino-4-methylpentanamido)-3-(2-oxo-1,2-dihydropyridin-3-yl)propanoate (170 mg, crude, HCl) as a solid and used directly for next step.

Step 4: methyl 2-((S)-2-(4-methoxy-1H-indole-2-carboxamido)-4-methylpentanamido)-3-(2-oxo-1,2-dihydropyridin-3-yl)propanoate A mixture of methyl 2-((S)-2-amino-4-methylpentanamido)-3-(2-oxo-1,2-dihydropyridin-3-yl)propanoate (170 mg, 491.58 umol, 1 eq, HCl), 4-methoxy-1H-indole-2-carboxylic acid (93.98 mg, 491.58 umol, 1 eq), EDCI (188.47 mg, 983.17 umol, 2 eq), DMAP (120.11 mg, 983.17 umol, 2 eq), DMF (2 mL) and DCM (4 mL) was stirred at 25° C. for 1 h. The reaction mixture was diluted with H$_2$O (30 mL) and then extracted with DCM (30 mL*3). The combined organic layers were washed with brine (50 mL), dried over Na$_2$SO$_4$, filtered and concentrated under reduced pressure to give a residue. The residue was purified by column chromatography (SiO$_2$, petroleum ether/EtOAc=0/1) to get the compound methyl 2-((S)-2-(4-methoxy-1H-indole-2-carboxamido)-4-methylpentanamido)-3-(2-oxo-1,2-dihydropyridin-3-yl)propanoate (130 mg, 269.41 umol, 54.81% yield), as a solid. MS (ESI) m/z 483.1 [M+H]$^+$ Step 5: N-((2S)-1-((1-amino-1-oxo-3-(2-oxo-1,2-dihydropyridin-3-yl)propan-2-yl)amino)-4-methyl-1-oxopentan-2-yl)-4-methoxy-1H-indole-2-carboxamide A mixture of methyl 2-((S)-2-(4-methoxy-1H-indole-2-carboxamido)-4-methylpentanamido)-3-(2-oxo-1,2-dihydropyridin-3-yl)propanoate (190 mg, 393.76 umol, 1 eq), NH$_3$/MeOH (7 M, 10 mL) was stirred at 80° C. for 15 h. The reaction mixture was concentrated under reduced pressure to give N-((2S)-1-((1-amino-1-oxo-3-(2-oxo-1,2-dihydropyridin-3-yl)propan-2-yl)amino)-4-methyl-1-oxopentan-2-yl)-4-methoxy-1H-indole-2-carboxamide (190 mg, crude) as a solid. MS (ESI) m/z 468.2 [M+H]$^+$ Step 6: N-((2S)-1-((1-cyano-2-(2-oxo-1,2-dihydropyridin-3-yl)ethyl)amino)-4-methyl-1-oxopentan-2-yl)-4-methoxy-1H-indole-2-carboxamide A mixture of N-((2S)-1-((1-amino-1-oxo-3-(2-oxo-1,2-dihydropyridin-3-yl)propan-2-yl)amino)-4-methyl-1-oxopentan-2-yl)-4-methoxy-1H-indole-2-carboxamide (180 mg, 385.01 umol, 1 eq), Burgess reagent (917.53 mg, 3.85 mmol, 10 eq) and DCM (30 mL) was stirred at 25° C. for 8 h. The reaction mixture was concentrated under reduced pressure to give a residue. The residue was purified by prep-HPLC (column: Phenomenex Gemini-NX C18 75*30 mm*3 um; mobile phase: [water(0.05% NH₃H₂O+10 mM NH₄HCO₃)-ACN]; B %: 25%-45%, 8 min) to get the product N-((2S)-1-((1-cyano-2-(2-oxo-1,2-dihydropyridin-3-yl)ethyl)amino)-4-methyl-1-oxopentan-2-yl)-4-methoxy-1H-indole-2-carboxamide (24 mg, 52.18 umol, 13.55% yield, 97.73% purity), as a solid. MS (ESI) m/z 450.2 [M+H]⁺.

¹H NMR (400 MHz, DMSO-d₆) δ=11.90-11.40 (m, 2H), 9.08-8.85 (m, 1H), 8.55-8.35 (m, 1H), 7.51-7.26 (m, 3H), 7.16-7.05 (m, 1H), 7.04-6.94 (m, 1H), 6.51 (d, J=7.5 Hz, 1H), 6.15 (t, J=6.6 Hz, 1H), 5.19-5.01 (m, 1H), 4.55-4.33 (m, 1H), 3.89 (s, 3H), 3.02-2.78 (m, 2H), 1.75-1.33 (m, 3H), 0.98-0.72 (m, 6H)

Example 30. Synthesis of Viral Protease Inhibitor Compounds 344C, 344D, 507 and 511

Step for compound 344C: N-[(1S)-1-[[(1S)-2-amino-2-cyano-1-[[(3S)-2-oxopyrrolidin-3-yl]methyl]ethyl] carbamoyl]-3-methyl-butyl]-4-methoxy-1H-indole-2-carboxamide

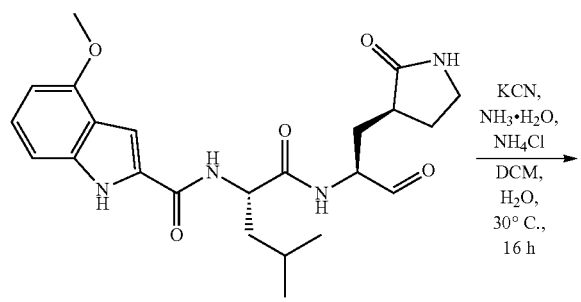

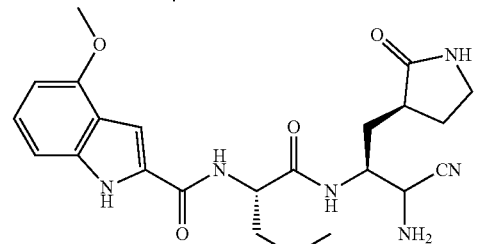

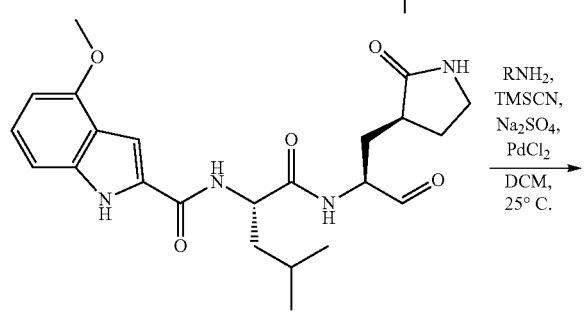

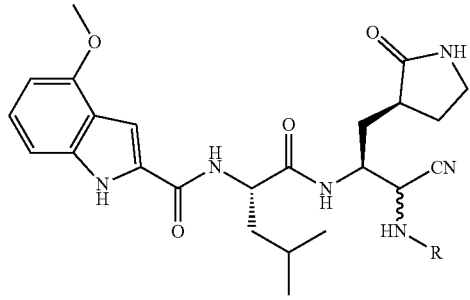

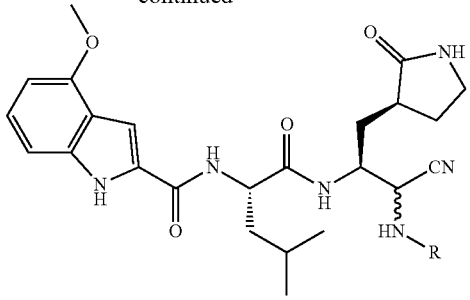

Compound 511: R = Et;
Compound 507: R = Bn

To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (100 mg, 180.79 umol, 80% purity, 1 eq) in DCM (10 mL) was added NH₃·H₂O (46.93 mg, 361.58 umol, 51.57 uL, 27% purity, 2 eq) and NH₄Cl (19.34 mg, 361.58 umol, 2 eq). The mixture was stirred at 25° C. for 30 min, then added KCN (94.18 mg, 1.45 mmol, 61.96 uL) in H₂O (0.2 mL), the mixture was stirred at 30° C. for 16 h. Once the reaction was completed, the reaction mixture was then quenched by addition H₂O (10 mL) at 0° C., and then diluted with H₂O (10 mL) and extracted with EtOAc (30 mL*2). The combined organic layers were washed with brine (30 mL), dried over Na₂SO₄, filtered and concentrated under reduced pressure to give a residue. The liquid water was added with NaOH to adjust pH=9, quenched with aq NaCl, and then added with NaOH to adjust pH>14. The residue was purified by HCl prep-HPLC to get the compound N-[(1S)-1-[[(1S)-2-amino-2-cyano-1-[[(3S)-2-oxopyrrolidin-3-yl]methyl]ethyl]carbamoyl]-3-methyl-butyl]-4-methoxy-1H-indole-2-carboxamide (50 mg, 103.83 umol, 57.43% yield, 97.3% purity) as a solid. MS (ESI) m/z 469.2 [M+H]⁺

Prep-HPLC Condition:
column: Phenomenex luna C18 80*40 mm*3 um; mobile phase: [water(0.04% HCl)-ACN]; B %: 15%-40%, 7 min ¹H NMR (400 MHz, DMSO-d6) δ=11.59 (dd, J=1.9, 5.0 Hz, 1H), 9.16-8.58 (m, 2H), 8.54-8.26 (m, 2H), 7.66 (d, J=9.0 Hz, 1H), 7.37 (dd, J=2.0, 4.2 Hz, 1H), 7.14-7.06 (m, 1H), 7.04-6.97 (m, 1H), 6.51 (d, J=7.5 Hz, 1H), 4.61-4.42 (m, 2H), 4.39-4.21 (m, 1H), 3.88 (s, 3H), 3.20-2.98 (m, 2H), 2.48-2.34 (m, 1H), 2.14-1.88 (m, 2H), 1.82-1.47 (m, 5H), 0.92 (dd, J=6.0, 14.8 Hz, 6H)

Step for compound 511: N-[(1S)-1-[[(1S)-2-cyano-2-(ethylamino)-1-[[(3S)-2-oxopyrrolidin-3-yl]methyl]ethyl]carbamoyl]-3-methyl-butyl]-4-methoxy-1H-indole-2-carboxamide To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (80 mg, 108.47 umol, 60% purity, 1 eq) in DCM (5 mL) was added PdCl₂ (3.85 mg, 21.69 umol, 0.2 eq), Na₂SO₄ (53.93 mg, 379.66 umol, 38.52 uL, 3.5 eq), and ethanamine (9.78 mg, 216.95 umol, 14.19 uL, 2 eq). The resulting mixture was stirred at 25° C. for 30 min, and then added with TMSCN (21.52 mg, 216.95 umol, 27.14 uL, 2 eq). The resulting mixture was stirred at 25° C. for 1 h. Once the reaction was completed, the reaction mixture was filtered and concentrated under reduced pressure to give a residue. The residue was purified by HCl prep-HPLC to yield 70 mg of the mixture. The mixture was purified by SFC to get the N-[(1S)-1-[[(1S)-2-cyano-2-(ethylamino)-1-[[(3S)-2-oxo pyrrolidin-3-yl]methyl]ethyl]carbamoyl]-3-methyl-butyl]-4-methoxy-1H-indole-2-carboxamide (16 mg, 28.20 umol, 26.00% yield, 87.525% purity) as an oil and N-[(1S)-1-[[(1S)-2-cyano-2-(ethylamino)-1-[[(3S)-2-oxopyrrolidin-3-yl]methyl]ethyl]carbamoyl]-3-methyl-butyl]-4-methoxy-1H-indole-2-carboxamide (16 mg, 31.44 umol, 28.98% yield, 97.569% purity) as a solid. MS (ESI) m/z 497.3 [M+H]$^+$
Prep-HPLC Condition:
column: Phenomenex luna C18 80*40 mm*3 um; mobile phase: [water(0.04% HCl)-ACN]; B %: 25%-40%, 7 min
SFC condition:
column: DAICEL CHIRALCEL OX (250 mm*30 mm, 10 um); mobile phase: [Neu-ETOH]; B %: 38%-38%, 9 min Compound 511 Isomer 1: $^1$H NMR (400 MHz, DMSO-d6) δ=11.56 (br s, 1H), 8.37 (br d, J=7.7 Hz, 1H), 8.29-8.20 (m, 1H), 7.80-7.48 (m, 3H), 7.35 (br d, J=2.0 Hz, 1H), 7.17-6.96 (m, 2H), 6.50 (d, J=7.7 Hz, 1H), 4.53-4.40 (m, 1H), 4.05 (td, J=3.9, 7.7 Hz, 1H), 3.88 (s, 3H), 3.77 (br dd, J=4.9, 10.1 Hz, 1H), 3.18-2.97 (m, 2H), 2.88-2.63 (m, 2H), 2.40-2.24 (m, 1H), 2.14-2.06 (m, 2H), 1.82-1.31 (m, 5H), 1.09-0.98 (m, 3H), 0.91 (br dd, J=6.2, 16.1 Hz, 6H)

Compound 511 Isomer 2: $^1$H NMR (400 MHz, DMSO-d6) δ=11.58 (d, J=7.9 Hz, 1H), 8.41 (br d, J=7.9 Hz, 1H), 8.17 (br s, 1H), 7.63-7.50 (m, 1H), 7.37 (d, J=1.8 Hz, 1H), 7.14-7.05 (m, 1H), 7.00 (d, J=8.2 Hz, 1H), 6.50 (d, J=7.5 Hz, 1H), 4.58-4.37 (m, 1H), 4.25-3.99 (m, 1H), 3.88 (s, 3H), 3.81-3.51 (m, 1H), 3.16-2.96 (m, 2H), 2.89-2.54 (m, 2H), 2.43-2.23 (m, 1H), 2.20-1.99 (m, 1H), 1.95-1.43 (m, 6H), 1.10-0.98 (m, 3H), 0.91 (dd, J=6.4, 15.2 Hz, 6H)

Step for compound 507: N-[(1S)-1-[[(1S)-2-(benzylamino)-2-cyano-1-[[(3S)-2-oxopyrrolidin-3-yl]methyl]ethyl]carbamoyl]-3-methyl-butyl]-4-methoxy-1H-indole-2-carboxamide To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (150 mg, 271.18 umol, 80% purity, 1 eq) in DCM (15 mL) was added PdCl$_2$ (9.62 mg, 54.24 umol, 0.2 eq), Na$_2$SO$_4$ (134.82 mg, 949.14 umol, 96.30 uL, 3.5 eq) and BnNH$_2$ (58.11 mg, 542.36 umol, 59.12 uL, 2 eq). The mixture was stirred at 25° C. for 30 min, then added with TMSCN (53.81 mg, 542.36 umol, 67.85 uL, 2 eq). The mixture was stirred at 25° C. for 2 hours. Once the reaction was completed, the reaction mixture was filtered and concentrated under reduced pressure to give a residue. The residue was purified by HCl prep-HPLC to get the compound N-[(1S)-1-[[(1S)-2-(benzylamino)-2-cyano-1-[[(3S)-2-oxopyrrolidin-3-yl]methyl]ethyl]carbamoyl]-3-methyl-butyl]-4-methoxy-1H-indole-2-carboxamide (30 mg, 51.71 umol, 19.07% yield, 96.291% purity) and N-[(1S)-1-[[(1S)-2-(benzylamino)-2-cyano-1-[[(3S)-2-oxopyrrolidin-3-yl]methyl]ethyl] carbamoyl]-3-methyl-butyl]-4-methoxy-1H-indole-2-carboxamide (18 mg, 31.04 umol, 11.44% yield, 96.329% purity) as a solid. MS (ESI) m/z 559.3 [M+H]$^+$
Prep-HPLC Condition:
column: Phenomenex luna C18 80*40 mm*3 um; mobile phase: [water(0.04% HCl)-ACN]; B %: 38%-62%, 7 min Compound 507 Isomer 1: $^1$H NMR: (400 MHz, DMSO-d6) δ=11.58 (d, J=1.8 Hz, 1H), 8.48-8.34 (m, 1H), 8.23 (br d, J=9.5 Hz, 1H), 7.69-7.53 (m, 1H), 7.51-7.23 (m, 1H), 7.14-7.05 (m, 1H), 7.02-6.97 (m, 1H), 6.50 (d, J=7.7 Hz, 1H), 4.56-4.37 (m, 1H), 4.23 (br d, J=9.3 Hz, 1H), 4.13-3.91 (m, 2H), 3.88 (s, 3H), 3.84 (br d, J=13.2 Hz, 1H), 3.17-2.95 (m, 2H), 2.42-2.24 (m, 1H), 2.16-1.98 (m, 1H), 1.93-1.44 (m, 6H), 0.90 (dd, J=6.3, 16.2 Hz, 6H)

Compound 507 Isomer 2: $^1$H NMR (400 MHz, DMSO-d6) δ=11.56 (br d, J=1.5 Hz, 1H), 8.52-8.14 (m, 2H), 7.69-7.55 (m, 1H), 7.49-7.22 (m, 6H), 7.13-7.05 (m, 1H), 7.00 (d, J=8.4 Hz, 1H), 6.50 (d, J=7.5 Hz, 1H), 4.56-4.41 (m, 1H), 4.21 (br s, 1H), 4.06-3.94 (m, 2H), 3.88 (s, 3H), 3.83 (br d, J=12.8 Hz, 1H), 3.17-2.97 (m, 2H), 2.42-2.29 (m, 1H), 2.17-2.00 (m, 2H), 1.83-1.44 (m, 5H), 0.90 (dd, J=6.3, 17.8 Hz, 6H)

Example 31. Synthesis of Viral Protease Inhibitor Compound 129

Step 1. 2-(trichloromethyl)-3H-imidazo[4,5-c]pyridine

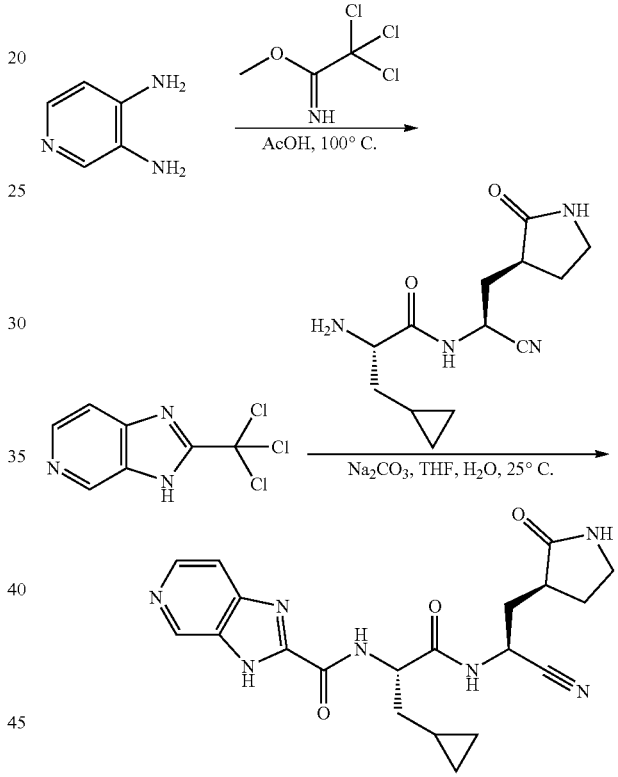

To a solution of pyridine-3,4-diamine (2 g, 18.33 mmol, 1 eq) in AcOH (25 mL) was added methyl 2,2,2-trichloroethanimidoate (3.88 g, 21.99 mmol, 2.71 mL, 1.2 eq). The solution was stirred for 5 h at 100° C. The reaction was added with H$_2$O (90 mL) and extracted with ethyl acetate (70 mL*3) and washed with NaHCO$_3$ (90 mL*2). The organic layer was cautiously concentrated to give crude 2-(trichloromethyl)-3H-imidazo[4,5-c]pyridine (800 mg, crude) was obtained as a yellow solid. The crude was used directly for the next step. MS (ESI) m/z 235.9 [M+H]$^+$ Step 2: N-[(1S)-2-[[(1S)-1-cyano-2-[(3S)-2-oxopyrrolidin-3-yl]ethyl]amino]-1-(cyclopropylmethyl)-2-oxo-ethyl]-3H-imidazo[4,5-c]pyridine-2-carboxamide To a solution of 2-(trichloromethyl)-3H-imidazo[4,5-c]pyridine (150 mg, 634.29 umol, 1 eq) and (2S)-2-amino-N-[(1S)-1-cyano-2-[(3S)-2-oxopyrrolidin-3-yl]ethyl]-3-cyclopropyl-propanamide (167.66 mg, 634.29 umol, 1 eq) in THF (5 mL) and H₂O (2.5 mL) was added Na₂CO₃ (201.68 mg, 1.90 mmol, 3 eq). The solution was stirred for 1 h at 20° C. The solution was added with H₂O (20 mL), extracted with ethyl acetate (40 mL*3) and concentrated to give crude. The crude was purified by pre-HPLC (Column: Waters Xbridge BEH C18 100*30 mm*10 um; mobile phase: [water (10 mM NH₄HCO₃)-ACN]; B %: 1%-23%, 8 min) to give 70% purity product and then continue purified by pre-HPLC (Column: Phenomenex Luna C18 75*30 mm*3 um; mobile phase: [water (0.2% FA)-ACN]; B %: 1%-30%, 8 min) to give product N-[(1S)-2-[[(1S)-1-cyano-2-[(3S)-2-oxopyrrolidin-3-yl]ethyl]amino]-1-(cyclopropylmethyl)-2-oxoethyl]-3H-imidazo[4,5-c]pyridine-2-carboxamide (3 mg, 6.96 umol, 1.10% yield, 95% purity) was obtained as a solid. MS (ESI) m/z 410.1 [M+H]⁺. ¹H NMR (400 MHz, DMSO-d₆) δ=8.89-8.81 (m, 2H), 8.77 (d, J=7.9 Hz, 1H), 8.21 (d, J=5.4 Hz, 2H), 7.54 (s, 1H), 7.43 (br d, J=5.4 Hz, 1H), 4.91-4.76 (m, 1H), 4.44-4.32 (m, 1H), 3.02-2.92 (m, 2H), 2.25-2.16 (m, 1H), 2.03-1.91 (m, 2H), 1.78-1.38 (m, 4H), 0.59 (br s, 1H), 0.25 (br d, J=7.9 Hz, 2H), 0.05-0.11 (m, 2H).

Example 32. Synthesis of Viral Protease Inhibitor Compound 389A and 389B

Step 1: (S)-2-amino-3-((S)-2-oxopyrrolidin-3-yl)propanamide

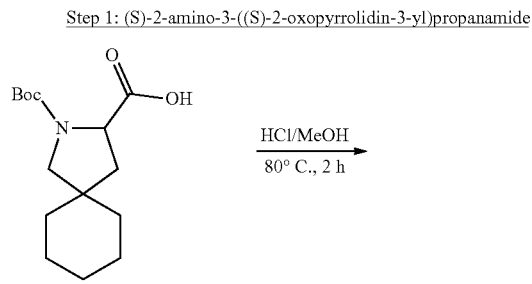

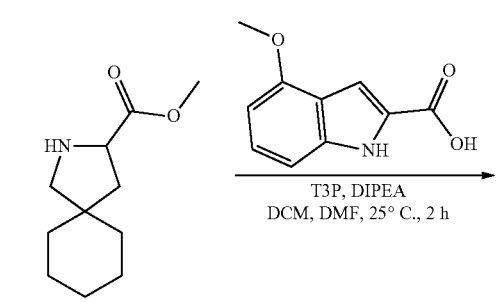

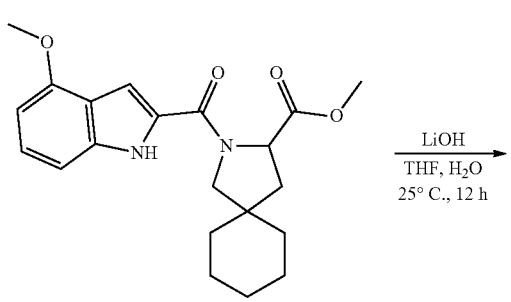

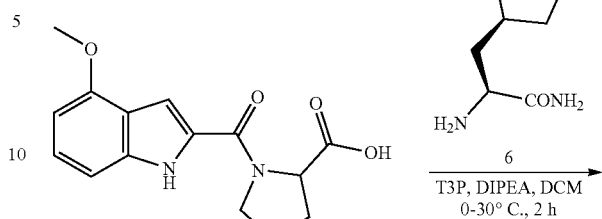

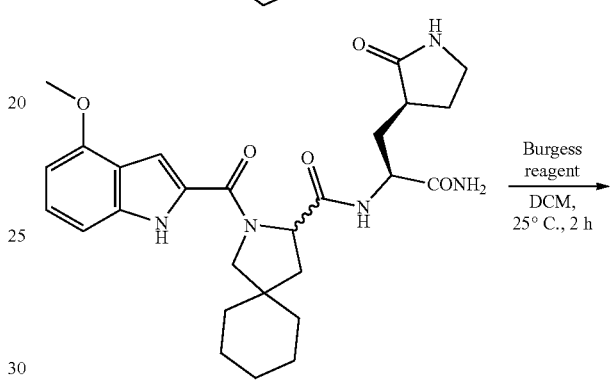

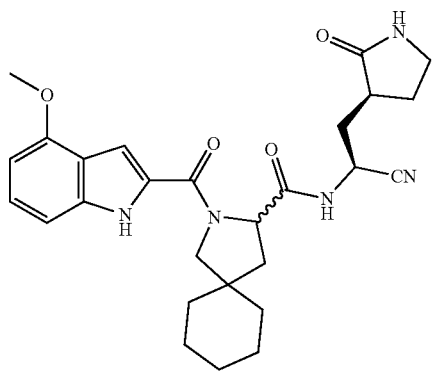

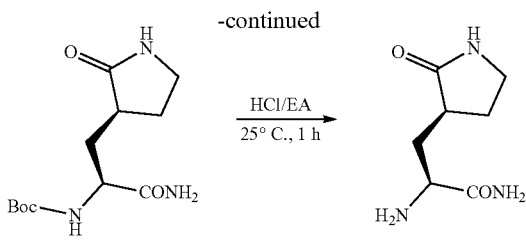

tert-Butyl N-[(1S)-2-amino-2-oxo-1-[[(3S)-2-oxopyrrolidin-3-yl]methyl]ethyl]carbamate (2 g, 7.37 mmol, 1 eq) in HCl/EtOAc (4 M, 50 mL, 27.13 eq) was stirred at 25° C. for 1 h. Upon completion, the mixture was concentrated under the reduced pressure affording the product (2S)-2-amino-3-[(3S)-2-oxopyrrolidin-3-yl]propanamide (1.2 g, crude) as a solid.

Step 2: Methyl 2-azaspiro[4.5]decane-3-carboxylate

A solution of 2-tert-butoxycarbonyl-2-azaspiro[4.5]decane-3-carboxylic acid (3 g, 10.59 mmol, 1 eq) in HCl/MeOH (4 M, 50 mL, 18.89 eq) was stirred at 80° C. for 2 h. The mixture was concentrated under the reduced pressure to afford the product methyl 2-azaspiro[4.5]decane-3-carboxylate (2 g, crude) as a yellow oil.

Step 3: Methyl 2-(4-methoxy-1H-indole-2-carbonyl)-2-azaspiro[4.5]decane-3-carboxylate To a solution of methyl 2-azaspiro[4.5]decane-3-carboxylate (2 g, 10.14 mmol, 1 eq) and 4-methoxy-1H-indole-2-carboxylic acid (2.33 g, 12.17 mmol, 1.2 eq) in DCM (30 mL) and DMF (5 mL) was added T3P (12.90 g, 20.28 mmol, 12.06 mL, 50% purity, 2 eq) and DIEA (3.93 g, 30.41 mmol, 5.30 mL, 3 eq). The mixture was stirred at 25° C. for 2 h. Upon completion, the reaction mixture was quenched by addition $H_2O$ (100 mL), and extracted with DCM (50 mL*3). The combined organic layers were washed with brine (50 mL), dried over $Na_2SO_4$, filtered and concentrated under reduced pressure to give a residue. The residue was purified by column chromatography ($SiO_2$, Petroleum ether: Ethyl acetate=10:1 to 0:1) to afford the product methyl 2-(4-methoxy-1H-indole-2-carbonyl)-2-azaspiro[4.5]decane-3-carboxylate (3 g, 8.10 mmol, 79.88% yield) as a solid. MS (ESI) m/z 371.1 $[M+H]^+$ Step 4: 2-(4-methoxy-1H-indole-2-carbonyl)-2-azaspiro[4.5]decane-3-carboxylic acid To a solution of methyl 2-(4-methoxy-1H-indole-2-carbonyl)-2-azaspiro[4.5]decane-3-carboxylate (3 g, 8.10 mmol, 1 eq) in THF (45 mL) and $H_2O$ (15 mL) was added LiOH·$H_2O$ (1.70 g, 40.49 mmol, 5 eq). The mixture was stirred at 25° C. for 12 h. Upon completion, the mixture was quenched by addition $H_2O$ (50 mL), and then added aq. HCl (1 M) to adjust the pH=3-4, and then extracted with ethyl acetate (50 mL*3). The combined organic layers were washed with brine (30 mL), dried over $Na_2SO_4$, filtered and concentrated under reduced pressure affording the product 2-(4-methoxy-1H-indole-2-carbonyl)-2-azaspiro[4.5]decane-3-carboxylic acid (2.6 g, crude) as a white solid. MS (ESI) m/z 357.1 $[M+H]^+$ Step 5: N-((S)-1-amino-1-oxo-3-((S)-2-oxopyrrolidin-3-yl)propan-2-yl)-2-(4-methoxy-1H-indole-2-carbonyl)-2-azaspiro[4.5]decane-3-carboxamide To a solution of 2-(4-methoxy-1H-indole-2-carbonyl)-2-azaspiro[4.5]decane-3-carboxylic acid (1 g, 2.81 mmol, 1 eq) and (2S)-2-amino-3-[(3S)-2-oxopyrrolidin-3-yl]propanamide (720.49 mg, 4.21 mmol, 1.5 eq) in DCM (30 mL) was added T3P (3.57 g, 5.61 mmol, 3.34 mL, 50% purity, 2 eq) and DIEA (1.09 g, 8.42 mmol, 1.47 mL, 3 eq) at 0° C. The mixture was stirred at 30° C. for 1 h. Upon completion, the mixture was quenched by addition $H_2O$ (100 mL), and then extracted with DCM (50 mL*3). The combined organic layers were washed with brine (50 mL), dried over $Na_2SO_4$, filtered and concentrated under reduced pressure to give a residue. The residue was purified by column chromatography ($SiO_2$, DCM:MeOH=1:0 to 10:1) affording the product N-[(1S)-2-amino-2-oxo-1-[[(3S)-2-oxopyrrolidin-3-yl]methyl]ethyl]-2-(4-methoxy-1H-indole-2-carbonyl)-2-azaspiro[4.5]decane-3-carboxamide (700 mg, 1.37 mmol, 48.96% yield) as a white solid. MS (ESI) m/z 510.3 $[M+H]^+$ Step 6: N-((S)-1-cyano-2-((S)-2-oxopyrrolidin-3-yl)ethyl)-2-(4-methoxy-1H-indole-2-carbonyl)-2-azaspiro[4.5]decane-3-carboxamide To a solution of N-[(1S)-2-amino-2-oxo-1-[[(3S)-2-oxopyrrolidin-3-yl]methyl]ethyl]-2-(4-methoxy-1H-indole-2-carbonyl)-2-azaspiro[4.5]decane-3-carboxamide (700 mg, 1.37 mmol, 1 eq) in DCM (10 mL) was added Burgess reagent (982.03 mg, 4.12 mmol, 3 eq). The mixture was stirred at 25° C. for 2 h. Upon completion, the mixture was concentrated under the reduced pressure to give a residue. The residue was purified by prep-HPLC (column: Kromasil C18 (250*50 mm*10 um); mobile phase: [water (10 mM $NH_4HCO_3$)-ACN]; B %: 30%-60%, 10 min) affording the product N-[(1S)-1-cyano-2-[(3S)-2-oxopyrrolidin-3-yl]ethyl]-2-(4-methoxy-1H-indole-2-carbonyl)-2-azaspiro[4.5]decane-3-carboxamide (500 mg, 1.02 mmol, 74.05% yield) as a white solid. MS (ESI) m/z 492.3 $[M+H]^+$ Step 7: N-((S)-1-cyano-2-((S)-2-oxopyrrolidin-3-yl)ethyl)-2-(4-methoxy-1H-indole-2-carbonyl)-2-azaspiro[4.5]decane-3-carboxamide N-[(1S)-1-cyano-2-[(3S)-2-oxopyrrolidin-3-yl]ethyl]-2-(4-methoxy-1H-indole-2-carbonyl)-2-azaspiro[4.5]decane-3-carboxamide (500 mg, 1.02 mmol) was separated by SFC (column: DAICEL CHIRALPAK AD (250 mm*30 mm, 10 um); mobile phase: [0.1% $NH_3H_2O$ IPA]; B %: 55%-55%, 9 min) to afford the product N-[(1S)-1-cyano-2-[(3S)-2-oxopyrrolidin-3-yl]ethyl]-2-(4-methoxy-1H-indole-2-carbonyl)-2-azaspiro[4.5]decane-3-carboxamide, Isomer 1 (264 mg, 537.04 umol, 52.80% yield) as a solid. MS (ESI) m/z 492.3 $[M+H]^+$; 1H NMR (400 MHz, METHANOL-$d_4$) δ=7.28-6.76 (m, 3H), 6.60-6.38 (m, 1H), 5.05 (br dd, J=5.2, 10.2 Hz, 1H), 4.63-4.60 (m, 1H), 4.03-3.85 (m, 5H), 3.74-3.28 (m, 1H), 2.73 (br dd, J=5.0, 8.6 Hz, 1H), 2.51-2.28 (m, 2H), 2.27-2.08 (m, 1H), 1.96-1.72 (m, 2H), 1.69-1.38 (m, 1H), 1.37-1.09 (m, 1H); and N-[(1S)-1-cyano-2-[(3S)-2-oxopyrrolidin-3-yl]ethyl]-2-(4-methoxy-1H-indole-2-carbonyl)-2-azaspiro[4.5]decane-3-carboxamide, Isomer 2 (140 mg, 284.51 umol, 27.97% yield) as a solid. MS (ESI) m/z 492.3 $[M+H]^+$; $^1$H NMR (400 MHz, METHANOL-$d_4$) δ=7.30-6.81 (m, 3H), 6.53 (br d, J=2.0 Hz, 1H), 5.12-4.95 (m, 2H), 4.70-4.55 (m, 2H), 4.08-3.86 (m, 4H), 3.84-3.72 (m, 1H), 2.62-2.40 (m, 1H), 2.36-2.18 (m, 2H), 1.94-1.69 (m, 3H), 1.68-1.34 (m, 11H).

Example 33. Synthesis of Viral Protease Inhibitor Compound 399

Step 1: (S)-methyl 2-amino-3-((S)-2-oxopyrrolidin-3-yl)propanoate hydrochloride

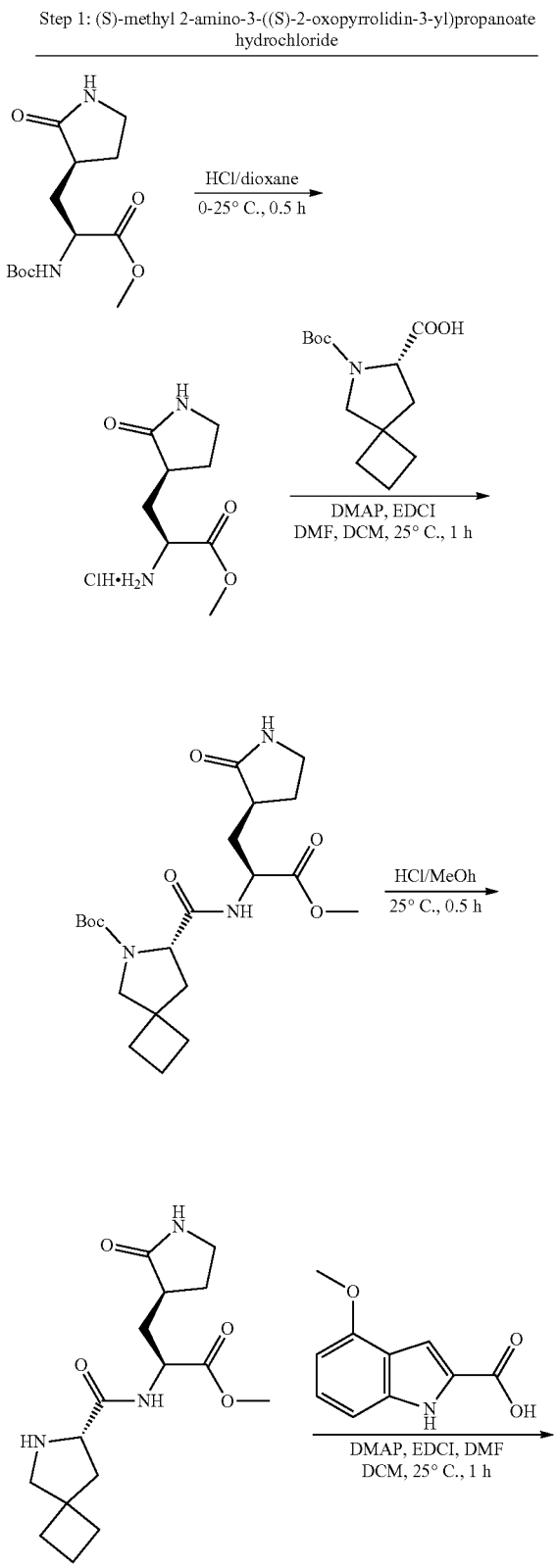

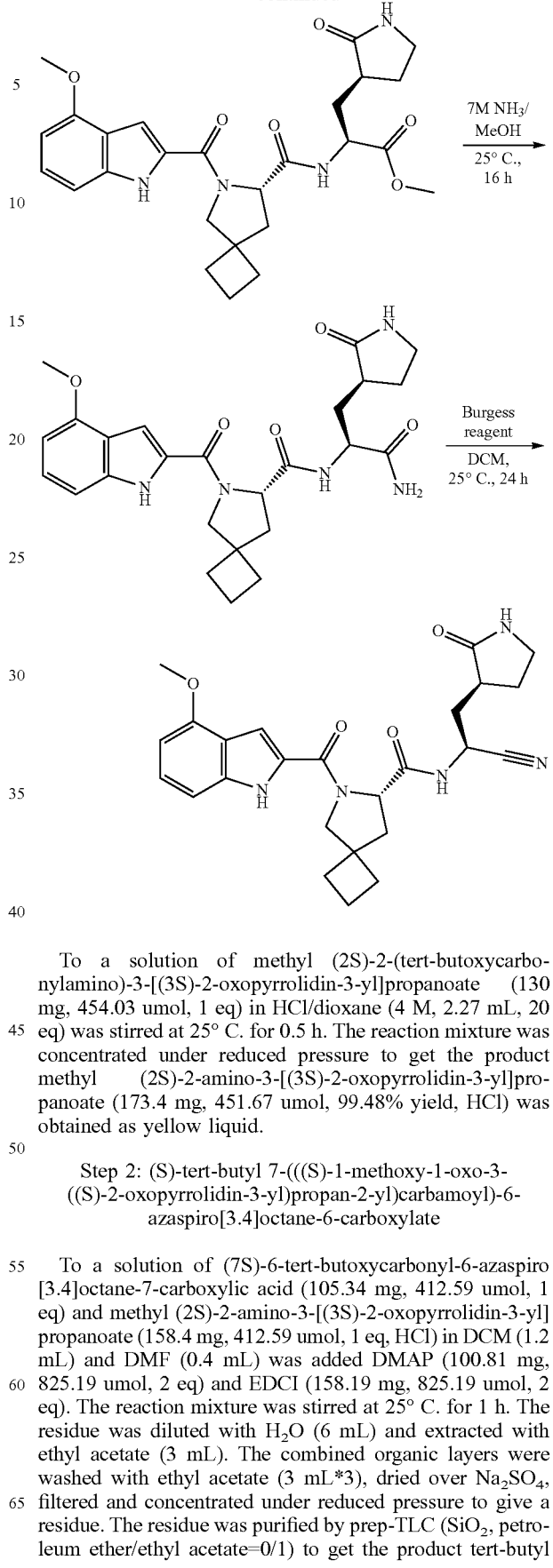

To a solution of methyl (2S)-2-(tert-butoxycarbonylamino)-3-[(3S)-2-oxopyrrolidin-3-yl]propanoate (130 mg, 454.03 umol, 1 eq) in HCl/dioxane (4 M, 2.27 mL, 20 eq) was stirred at 25° C. for 0.5 h. The reaction mixture was concentrated under reduced pressure to get the product methyl (2S)-2-amino-3-[(3S)-2-oxopyrrolidin-3-yl]propanoate (173.4 mg, 451.67 umol, 99.48% yield, HCl) was obtained as yellow liquid.

Step 2: (S)-tert-butyl 7-(((S)-1-methoxy-1-oxo-3-((S)-2-oxopyrrolidin-3-yl)propan-2-yl)carbamoyl)-6-azaspiro[3.4]octane-6-carboxylate To a solution of (7S)-6-tert-butoxycarbonyl-6-azaspiro[3.4]octane-7-carboxylic acid (105.34 mg, 412.59 umol, 1 eq) and methyl (2S)-2-amino-3-[(3S)-2-oxopyrrolidin-3-yl]propanoate (158.4 mg, 412.59 umol, 1 eq, HCl) in DCM (1.2 mL) and DMF (0.4 mL) was added DMAP (100.81 mg, 825.19 umol, 2 eq) and EDCI (158.19 mg, 825.19 umol, 2 eq). The reaction mixture was stirred at 25° C. for 1 h. The residue was diluted with H₂O (6 mL) and extracted with ethyl acetate (3 mL). The combined organic layers were washed with ethyl acetate (3 mL*3), dried over Na₂SO₄, filtered and concentrated under reduced pressure to give a residue. The residue was purified by prep-TLC (SiO₂, petroleum ether/ethyl acetate=0/1) to get the product tert-butyl (7S)-7-[[(1S)-2-methoxy-2-oxo-1-[[(3S)-2-oxopyrrolidin-3-yl]methyl]ethyl]carbamoyl]-6-azaspiro[3.4]octane-6-carboxylate (66.3 mg, 156.55 umol, 37.94% yield) was obtained as a liquid. MS (ESI) m/z 424.0 [M+H]⁺

Step 3: (S)-methyl 3-((S)-2-oxopyrrolidin-3-yl)-2-((S)-6-azaspiro[3.4]octane-7-carboxamido)propanoate A solution of tert-butyl (7S)-7-[[(1S)-2-methoxy-2-oxo-1-[[(3S)-2-oxopyrrolidin-3-yl]methyl]ethyl]carbamoyl]-6-azaspiro[3.4]octane-6-carboxylate (66.3 mg, 156.55 umol, 1 eq) in HCl/MeOH (4 M, 782.76 uL, 20 eq) was stirred at 25° C. for 0.5 h. The reaction mixture was concentrated under reduced pressure to get the product methyl (2S)-2-[[(7S)-6-azaspiro[3.4]octane-7-carbonyl]amino]-3-[(3S)-2-oxopyrrolidin-3-yl]propanoate (71.1 mg, 156.09 umol, 99.71% yield, 79% purity, HCl) was obtained as a yellow liquid.

Step 4: (S)-methyl 2-((S)-6-(4-methoxy-1H-indole-2-carbonyl)-6-azaspiro[3.4]octane-7-carboxamido)-3-((S)-2-oxopyrrolidin-3-yl)propanoate To a solution of methyl (2S)-2-[[(7S)-6-azaspiro[3.4]octane-7-carbonyl]amino]-3-[(3S)-2-oxopyrrolidin-3-yl]propanoate (62.8 mg, 137.87 umol, 1 eq, HCl) and 4-methoxy-1H-indole-2-carboxylic acid (26.36 mg, 137.87 umol, 1 eq) in DCM (1.2 mL) and DMF (0.4 mL) was added DMAP (33.69 mg, 275.74 umol, 2 eq) and EDCI (52.86 mg, 275.74 umol, 2 eq) at 25° C. for 1 h. The residue was diluted with brine (6 mL) and extracted with ethyl acetate (3 mL*3). The combined organic layers were dried over Na₂SO₄, filtered and concentrated under reduced pressure to give a residue. The residue was purified by prep-TLC (SiO₂, petroleum ether/ethyl acetate=0/1) to get the product methyl (2S)-2-[[(7S)-6-(4-methoxy-1H-indole-2-carbonyl)-6-azaspiro[3.4]octane-7-carbonyl]amino]-3-[(3S)-2-oxopyrrolidin-3-yl]propanoate (33.2 mg, 66.86 umol, 48.50% yield) was obtained as a white solid. MS (ESI) m/z 497.1 [M+H]⁺

Step 5: (S)-N-((S)-1-amino-1-oxo-3-((S)-2-oxopyrrolidin-3-yl)propan-2-yl)-6-(4-methoxy-1H-indole-2-carbonyl)-6-azaspiro[3.4]octane-7-carboxamide A mixture of methyl (2S)-2-[[(7S)-6-(4-methoxy-1H-indole-2-carbonyl)-6-azaspiro[3.4]octane-7-carbonyl]amino]-3-[(3S)-2-oxopyrrolidin-3-yl]propanoate (23.0 mg, 46.32 umol, 1 eq) and ammonia (7 M, 4 mL, 604.50 eq) was stirred at 25° C. for 16 h. The reaction mixture was concentrated under reduced pressure to get the product (7S)-N-[(1S)-2-amino-2-oxo-1-[[(3S)-2-oxopyrrolidin-3-yl]methyl]ethyl]-6-(4-methoxy-1H-indole-2-carbonyl)-6-azaspiro[3.4]octane-7-carboxamide (15 mg, crude) was obtained as a yellow solid. MS (ESI) m/z 482.2 [M+H]⁺

Step 6: (S)-N-((S)-1-cyano-2-((S)-2-oxopyrrolidin-3-yl)ethyl)-6-(4-methoxy-1H-indole-2-carbonyl)-6-azaspiro[3.4]octane-7-carboxamide A solution of (7S)-N-[(1S)-2-amino-2-oxo-1-[[(3S)-2-oxopyrrolidin-3-yl]methyl]ethyl]-6-(4-methoxy-1H-indole-2-carbonyl)-6-azaspiro[3.4]octane-7-carboxamide (15 mg, 28.66 umol, 1 eq) and Burgess reagent (13.66 mg, 57.32 umol, 2 eq) was stirred at 25° C. for 24 h. The reaction mixture was concentrated under reduced pressure to give a residue. The residue was purified by prep-HPLC (column: Waters Xbridge BEH C18 100*30 mm*10 um; mobile phase: [water (10 mM NH₄HCO₃)-ACN]; B %: 20%-45%, 8 min) to get the product (7S)-N-[(1S)-1-cyano-2-[(3S)-2-oxopyrrolidin-3-yl]ethyl]-6-(4-methoxy-1H-indole-2-carbonyl)-6-azaspiro[3.4]octane-7-carboxamide (3.01 mg, 6.49 umol, 22.66% yield) was obtained as a solid. MS (ESI) m/z 464.3 [M+H]⁺ ¹H NMR (400 MHz, METHANOL-d₄) δ ppm 6.95-7.24 (m, 3H) 6.47-6.58 (m, 1H) 5.01 (br dd, J=10.67, 5.19 Hz, 1H) 4.58 (t, J=7.09 Hz, 1H) 3.82-4.19 (m, 5H) 3.19 (br t, J=8.52 Hz, 1H) 2.93-3.07 (m, 1H) 2.28-2.56 (m, 3H) 2.16-2.27 (m, 2H) 1.94-2.14 (m, 6H) 1.47-1.86 (m, 2H).

Example 34. Synthesis of Viral Protease Inhibitor Compound 405

Step 1: methyl (2S)-2-[[(2S)-2-(tert-butoxycarbonylamino)-4,4-dimethylpentanoyl]amino]-3-[(3S)-2-oxopyrrolidin-3-yl]propanoate

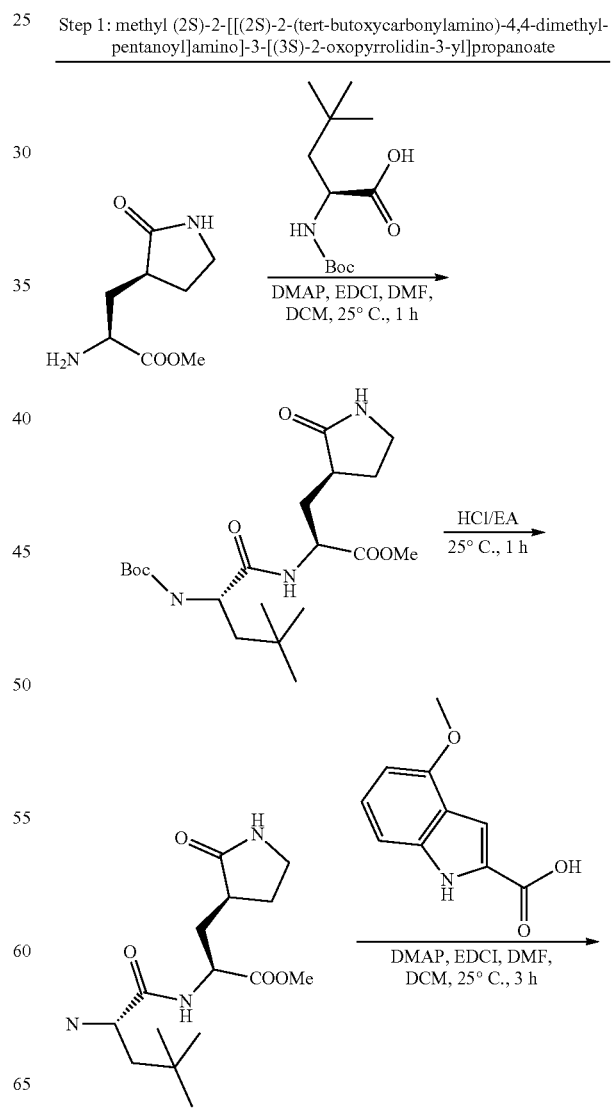

-continued

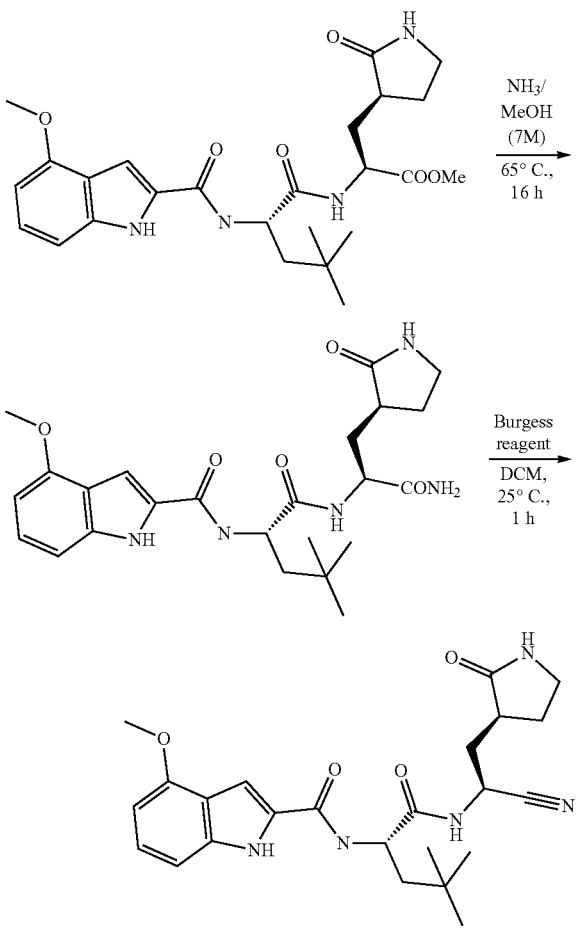

To a solution of methyl (2S)-2-amino-3-[(3S)-2-oxopyrrolidin-3-yl]propanoate (225 mg, 1.21 mmol, 1 eq) in DMF (2 mL) and DCM (4 mL) was added TEA (733.62 mg, 7.25 mmol, 1.01 mL, 6 eq) and T₃P (1.15 g, 3.62 mmol, 1.08 mL, 3 eq) and (2S)-2-(tert-butoxycarbonylamino)-4,4-dimethyl-pentanoic acid (296.42 mg, 1.21 mmol, 1 eq). The solution was stirred for 1 h at 25° C. The reaction was added with H₂O (40 mL) and extracted with ethyl acetate (50 mL*3) and the organic layer was cautiously concentrated to give crude compound methyl (2S)-2-[[(2S)-2-(tert-butoxycarbonylamino)-4,4-dimethyl-pentanoyl]amino]-3-[(3S)-2-oxopyrrolidin-3-yl]propanoate (440 mg, crude) as a solid used directly for the next step. MS (ESI) m/z 414.1 [M+H]⁺

Step 2: methyl (2S)-2-[[(2S)-2-amino-4,4-dimethyl-pentanoyl]amino]-3-[(3S)-2-oxopyrrolidin-3-yl]propanoate A solution of methyl (2S)-2-[[(2S)-2-(tert-butoxycarbonylamino)-4,4-dimethyl-pentanoyl]amino]-3-[(3S)-2-oxopyrrolidin-3-yl]propanoate (440 mg, 1.06 mmol, 1 eq) in HCl/MeOH (10 mL) was stirred for 1 h at 25° C. TLC (DCM:MeOH=10:1). The reaction was cautiously concentrated to give crude. Compound methyl (2S)-2-[[(2S)-2-amino-4,4-dimethyl-pentanoyl]amino]-3-[(3S)-2-oxopyrrolidin-3-yl]propanoate (310 mg, crude) as a solid used directly for the next step. MS (ESI) m/z 314.3 [M+H]⁺

Step 3: methyl (2S)-2-[[(2S)-2-[(4-methoxy-1H-indole-2-carbonyl)amino]-4,4-dimethyl-pentanoyl]amino]-3-[(3S)-2-oxopyrrolidin-3-yl]propanoate To a solution of methyl (2S)-2-[[(2S)-2-amino-4,4-dimethyl-pentanoyl]amino]-3-[(3S)-2-oxopyrrolidin-3-yl]propanoate (310 mg, 989.18 umol, 1 eq) in DMF (4 mL) and DCM (4 mL) was added EDCI (379.25 mg, 1.98 mmol, 2 eq) and DMAP (241.70 mg, 1.98 mmol, 2 eq) and 4-methoxy-1H-indole-2-carboxylic acid (189.11 mg, 989.18 umol, 1 eq) was added. The solution was stirred for 3 h at 25° C. The reaction was added with H₂O (40 mL) and extracted with ethyl acetate (80 mL*3) and the organic layer was cautiously concentrated to give crude. The crude was purified by pre-TLC(SiO₂, ethyl acetate:MeOH=10:1) to afford methyl (2S)-2-[[(2S)-2-[(4-methoxy-1H-indole-2-carbonyl)amino]-4,4-dimethyl-pentanoyl]amino]-3-[(3S)-2-oxopyrrolidin-3-yl]propanoate (200 mg, 411.05 umol, 41.55% yield). MS (ESI) m/z 487.2 [M−H]⁺

Step 4: N-[(1S)-1-[[(1S)-2-amino-2-oxo-1-[[(3S)-2-oxopyrrolidin-3-yl]methyl]ethyl]carbamoyl]-3,3-dimethyl-butyl]-4-methoxy-1H-indole-2-carboxamide A solution of methyl (2S)-2-[[(2S)-2-[(4-methoxy-1H-indole-2-carbonyl)amino]-4,4-dimethyl-pentanoyl]amino]-3-[(3S)-2-oxopyrrolidin-3-yl]propanoate (135 mg, 277.46 umol, 1 eq) in NH₃/MeOH (7 M, 8 mL, 201.83 eq) was stirred for 16 h at 65° C. The reaction was cautiously concentrated to give crude. Compound N-[(1S)-1-[[(1S)-2-amino-2-oxo-1-[[(3S)-2-oxopyrrolidin-3-yl]methyl]ethyl]carbamoyl]-3,3-dimethyl-butyl]-4-methoxy-1H-indole-2-carboxamide (130 mg, crude) as a solid used directly for the next step. MS (ESI) m/z 472.3 [M+H]⁺; Prep-HPLC condition: column: Phenomenex Gemini-NX C18 75*30 mm*3 um; mobile phase: [water(0.05% NH₃H₂O+10 mM NH₄HCO₃)-ACN]; B %: 35%-55%, 8 min Step 5: N-[(1S)-1-[[(1S)-1-cyano-2-[(3S)-2-oxopyrrolidin-3-yl]ethyl]carbamoyl]-3,3-dimethyl-butyl]-4-methoxy-1H-indole-2-carboxamide To a solution of N-[(1S)-1-[[(1S)-2-amino-2-oxo-1-[[(3S)-2-oxopyrrolidin-3-yl]methyl]ethyl]carbamoyl]-3,3-dimethyl-butyl]-4-methoxy-1H-indole-2-carboxamide (130 mg, 275.69 umol, 1 eq) in DCM (7 mL) was added Burgess reagent (197.09 mg, 827.06 umol, 3 eq). The solution was stirred for 1 h at 25° C. The reaction was cautiously concentrated to give crude. The crude was purified by pre-HPLC (TFA) to afford N-[(1S)-1-[[(1S)-1-cyano-2-[(3S)-2-oxopyrrolidin-3-yl]ethyl]carbamoyl]-3,3-dimethyl-butyl]-4-methoxy-1H-indole-2-carboxamide (36 mg, 75.41 umol, 27.35% yield, 95% purity) as a solid. MS (ESI) m/z 454.1 [M+H]⁺. Prep-HPLC condition: column: Phenomenex luna C18 80*40 mm*3 um; mobile phase: [water(0.04% HCl)-ACN]; B %: 30%-55%, 7 min; ¹H NMR (400 MHz, METHANOL-d₄) δ ppm 1.02 (s, 9H) 1.74-1.94 (m, 4H) 2.21-2.37 (m, 2H) 2.52-2.63 (m, 1H) 3.16-3.26 (m, 2H) 3.92 (s, 3H) 4.63 (dd, J=8.49, 4.30 Hz, 1H) 4.98-5.06 (m, 1H) 6.50 (d, J=7.72 Hz, 1H) 7.02 (d, J=8.38 Hz, 1H) 7.10-7.16 (m, 1H) 7.23 (d, J=0.88 Hz, 1H).

Example 35. Synthesis of Viral Protease Inhibitor Compound 491 and 491A

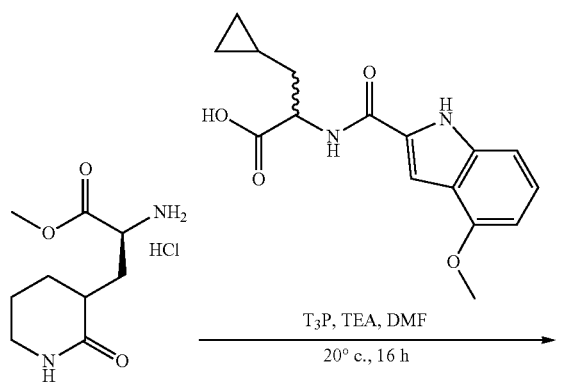

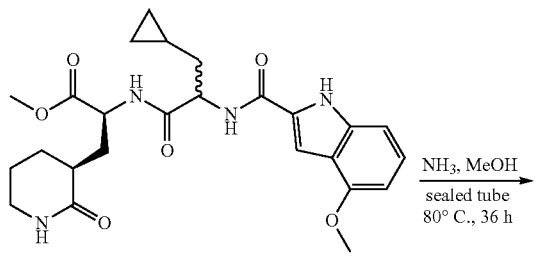

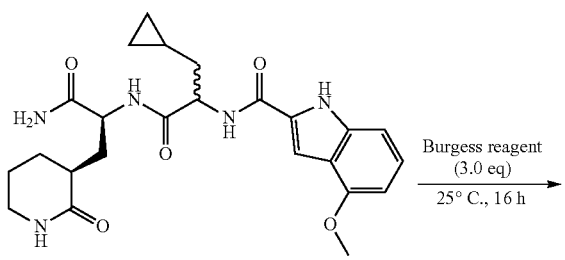

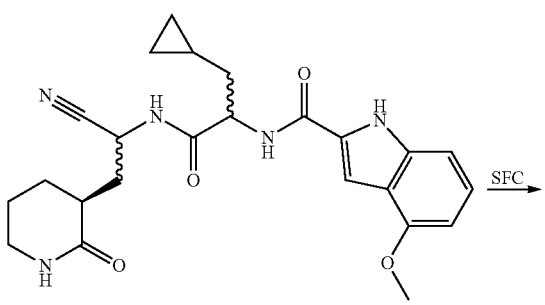

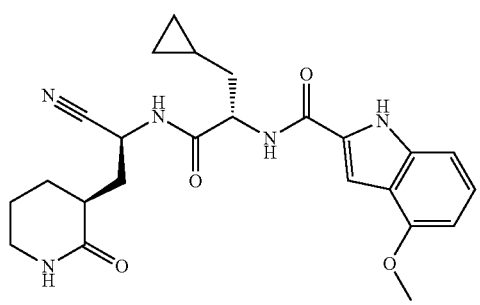

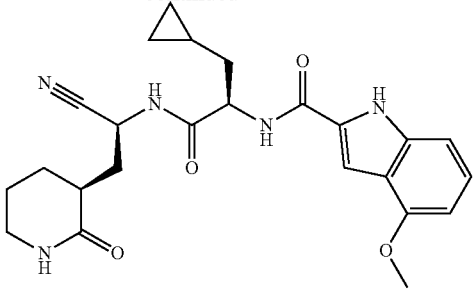

Step 1: Methyl (2S)-2-[[3-cyclopropyl-2-[(4-methoxy-1H-indole-2-carbonyl)amino]propanoyl]amino]-3-[(3S)-2-oxo-3-piperidyl]propanoate To the mixture of methyl (2S)-2-amino-3-[(3S)-2-oxo-3-piperidyl]propanoate (1 g, 4.22 mmol, 1 eq, HCl), 3-cyclopropyl-2-[(4-methoxy-1H-indole-2-carbonyl)amino]propanoic acid (1.5 g, 5.06 mmol, 1.2 eq, HCl) and TEA (1.7 g, 16.88 mmol, 2.35 mL, 4 eq) in DMF (5 mL) was added $T_3P$ (5.3 g, 8.44 mmol, 5.02 mL, 50% purity, 2 eq) at 25° C. The mixture was stirred at 25° C. for 16 h. TLC (DCM:MeOH=10:1/UV254 nm) showed new spot was detected. The reaction mixture was diluted with $H_2O$ (10 mL) and the mixture was extracted with ethyl acetate (10 mL*3). The combined organic phase was washed with brine (10 mL*2), dried with anhydrous $Na_2SO_4$, filtered and concentrated in vacuum. The residue was purified by flash silica gel chromatography (ISCO®; 12 g SepaFlash® Silica Flash Column, Eluent of 100~25% Ethyl acetate/MeOH@ 30 mL/min). Compound methyl (2S)-2-[[3-cyclopropyl-2-[(4-methoxy-1H-indole-2-carbonyl)amino]propanoyl]amino]-3-[(3S)-2-oxo-3-piperidyl]propanoate (1.9 g, 3.84 mmol, 91.0% yield) was obtained as a solid. Methyl (2S)-2-[[(2S)-3-cyclopropyl-2-[(4-methoxy-1H-indole-2-carbonyl)amino]propanoyl]amino]-3-[(3S)-2-oxo-3-piperidyl]propanoate (50 mg, 0.10 mmol, 1 eq) was purified by prep-HPLC (column: Phenomenex Gemini-NX 80*30 mm*3 um; mobile phase: [water(0.05% $NH_3H_2O$+10 mM $NH_4HCO_3$)-ACN]; B %: 20%-50%, 9.5 min). Compound methyl (2S)-2-[[(2S)-3-cyclopropyl-2-[(4-methoxy-1H-indole-2-carbonyl)amino]propanoyl]amino]-3-[(3S)-2-oxo-3-piperidyl]propanoate (50 mg, 0.10 mmol, 1 eq) was obtained as a solid.

Step 2: N-[2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-indole-2-carboxamide The mixture of methyl (2S)-2-[[3-cyclopropyl-2-[(4-methoxy-1H-indole-2-carbonyl)amino]propanoyl]amino]-3-[(3S)-2-oxo-3-piperidyl]propanoate (1.00 g, 1.73 mmol, 84% purity, 1 eq) in $NH_3$ (7 M, 24.77 mL, 100 eq) (7M in MeOH) was stirred at 80° C. for 36 h. Then, the reaction mixture was concentrated in vacuum. Compound N-[2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-indole-2-carboxamide (813 mg, crude) was obtained as yellow solid.

N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-indole-2-carboxamide (50 mg, 0.10 mmol, 1 eq) was purified by prep-HPLC (column: Phenomenex Gemini-NX 80*40 mm*3 um; mobile phase: [water (0.05% NH₃H₂O+10 mM NH₄HCO₃)-ACN]; B %: 23%-53%, 7.8 min). Compound N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-indole-2-carboxamide (20.3 mg, 42.5 umol, 39.9% yield, 98.4% purity) was obtained as white solid.

Step 3: N-[2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide A mixture of N-[2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-indole-2-carboxamide (663.0 mg, 1.41 mmol, 1 eq) and methoxycarbonyl-(triethylammonio)sulfonyl-azanide (673.0 mg, 2.82 mmol, 2 eq) in DCM (8 mL) was stirred at 25° C. for 16 h. Then, methoxycarbonyl-(triethylammonio)sulfonyl-azanide (336.5 mg, 1.41 mmol, 1 eq) was added at the mixture and the mixture was stirred at 25° C. for 16 hr. LC-MS showed that the desired compound was detected. TLC (petroleum ether:ethyl acetate=0:1/I₂) showed new spots were detected. The reaction mixture was diluted with H₂O (10 mL) and the mixture was extracted with ethyl acetate (10 mL*3). The combined organic phase was washed with brine (10 mL*2), dried with anhydrous Na₂SO₄, filtered and concentrated in vacuum. The residue was purified by prep-HPLC (column: Phenomenex Gemini-NX 80*30 mm*3 um; mobile phase: [water (0.05% NH₃H₂O+10 mM NH₄HCO₃)-ACN]; B %: 23%-53%, 9.5 min). Compound N-[2-[[(1 S)-1-cyano-2-[(3S)-2-oxo-3-piperidyl]ethyl]amino]-1-(cyclopropylmethyl)-2-oxo-ethyl]-4-methoxy-1H-indole-2-carboxamide (450 mg, 0.98 mmol, 69.9% yield) was obtained as yellow solid.

Step 4: N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide N-[2-[[1-cyano-2-[(3S)-2-oxo-3-piperidyl]ethyl]amino]-1-(cyclopropylmethyl)-2-oxo-ethyl]-4-methoxy-1H-indole-2-carboxamide (550.0 mg, 1.22 mmol, 1 eq) was purified by SFC (column: DAICEL CHIRALPAK AD (250 mm*30 mm, 10 um); mobile phase: [0.1% NH₃H₂O ETOH]; B %: 55%-55%, min). Compound N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide, Isomer 1 (147.1 mg, 0.25 mmol, 22.1% yield) was obtained as a solid. LCMS: Rt=0.756 min; for C₂₄H₂₉N₅O₄ MS Calcd: 451.22, MS Found: 452.1 [M+H⁺]. ¹H NMR (400 MHz, DMSO-d₆) δ 11.56 (br s, 1H), 8.90 (br d, J=8.0 Hz, 1H), 8.49 (br d, J=7.4 Hz, 1H), 7.52 (br s, 1H), 7.36 (s, 1H), 7.12-7.06 (m, 1H), 7.03-6.98 (m, 1H), 6.50 (d, J=7.6 Hz, 1H), 5.17-4.96 (m, 1H), 4.56-4.33 (m, 1H), 3.88 (s, 3H), 3.09 (br s, 2H), 2.33-2.19 (m, 2H), 1.88-1.76 (m, 3H), 1.70 (br dd, J=3.8, 8.3 Hz, 1H), 1.57 (br s, 1H), 1.50-1.35 (m, 2H), 0.80 (br s, 1H), 0.41 (br d, J=6.6 Hz, 2H), 0.25-0.03 (m, 2H); and N-[(1R)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide, Isomer 2 (113.1 mg, 0.32 mmol, 28.8% yield, 100% purity) was obtained as a solid. LCMS: Rt=0.761 min; for C₂₄H₂₉N₅O₄ MS Calcd: 451.22, MS Found: 452.0 [M+H⁺]. ¹H NMR (400 MHz, DMSO-d₆) δ 11.57 (s, 1H), 8.89 (br d, J=8.0 Hz, 1H), 8.49 (br d, J=7.6 Hz, 1H), 7.51 (br s, 1H), 7.36 (d, J=1.6 Hz, 1H), 7.13-7.06 (m, 1H), 7.03-6.97 (m, 1H), 6.50 (d, J=7.5 Hz, 1H), 5.08-4.99 (m, 1H), 4.52-4.42 (m, 1H), 3.88 (s, 3H), 3.08 (br s, 2H), 2.23-2.13 (m, 2H), 1.90-1.68 (m, 4H), 1.64-1.36 (m, 3H), 0.85-0.70 (m, 1H), 0.45-0.33 (m, 2H), 0.24-0.11 (m, 1H), 0.13-0.03 (m, 1H).

Example 36. Synthesis of Viral Protease Inhibitor Compound 531

Step 1: methyl (2S)-2-[[(2S)-2-[(7-chloro-1H-indole-2-carbonyl)amino]-3-cyclopropyl-propanoyl]amino]-3-[(3S)-2-oxopyrrolidin-3-yl]propanoate

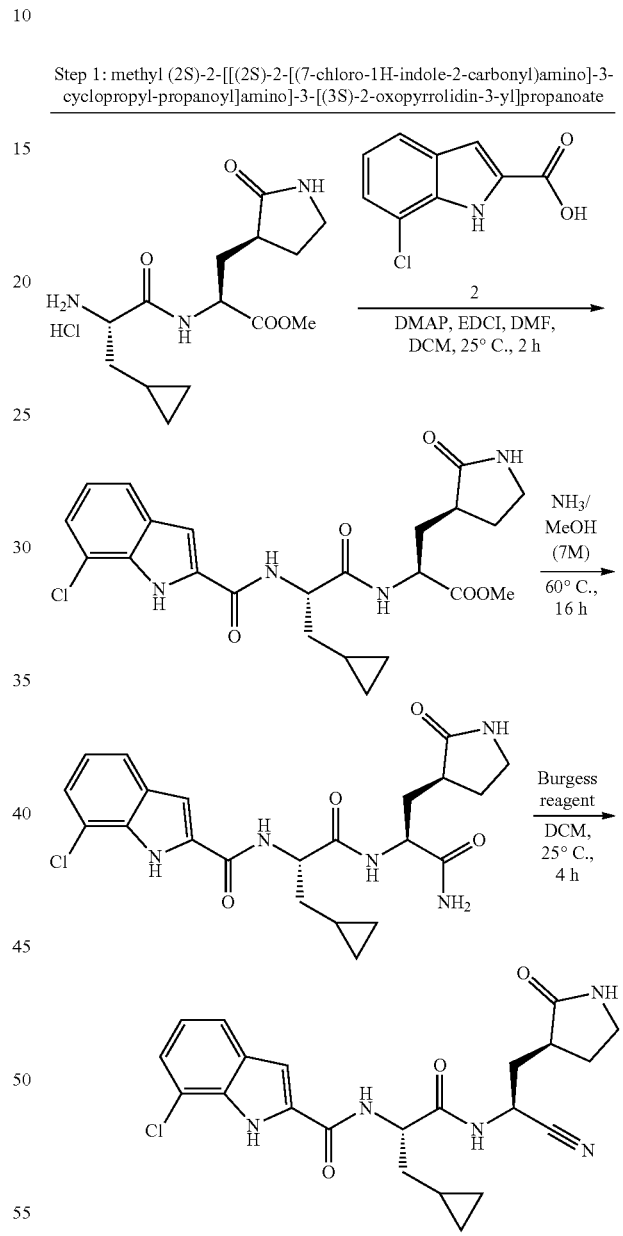

To a mixture of methyl (2S)-2-[[(2S)-2-amino-3-cyclopropyl-propanoyl]amino]-3-[(3S)-2-oxopyrrolidin-3-yl]propanoate (500 mg, 1.68 mmol, 1 eq) in DCM (10 mL) and DMF (2.5 mL), was added DMAP (616.30 mg, 5.04 mmol, 3 eq) in one portion at 25° C. The mixture was added 7-chloro-1H-indole-2-carboxylic acid (394.69 mg, 2.02 mmol, 1.2 eq) and EDCI (967.04 mg, 5.04 mmol, 3 eq). The resulting mixture was stirred at 25° C. for 2 h. Then, the mixture was concentrated under reduced pressure to give the crude product. The crude was purified by column chromatography (SiO$_2$, Petroleum ether/Ethyl acetate=5/1 to 0/1) to give methyl (2S)-2-[[(2S)-2-[(7-chloro-1H-indole-2-carbonyl)amino]-3-cyclopropyl-propanoyl]amino]-3-[(3S)-2-oxopyrrolidin-3-yl]propanoate (550 mg, 1.16 mmol, 68.87% yield) as a white solid. MS (ESI) m/z 475.1 [M+H]$^+$ Step 2: N-[(1S)-2-[[(1 S)-2-amino-2-oxo-1-[[(3S)-2-oxopyrrolidin-3-yl]methyl]ethyl]amino]-1-(cyclopropylmethyl)-2-oxo-ethyl]-7-chloro-1H-indole-2-carboxamide A mixture of methyl (2S)-2-[[(2S)-2-[(7-chloro-1H-indole-2-carbonyl)amino]-3-cyclopropyl-propanoyl]amino]-3-[(3S)-2-oxopyrrolidin-3-yl]propanoate (500 mg, 1.05 mmol, 1 eq) in NH$_3$/MeOH (7 M, 10 mL, 66.49 eq) was stirred at 60° C. for 16 h. The reaction mixture was concentrated under reduced pressure to give N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-7-chloro-1H-indole-2-carboxamide (440 mg, 956.68 umol, 90.87% yield) as a solid. MS (ESI) m/z 460.3 [M+H]$^+$ Step 3: 7-chloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-indole-2-carboxamide To a mixture of N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-7-chloro-1H-indole-2-carboxamide (430 mg, 934.94 umol, 1 eq) in DCM (6 mL) was added Burgess reagent (445.61 mg, 1.87 mmol, 2 eq) in one portion at 25° C. The mixture was stirred at 25° C. for 4 h. The reaction mixture was concentrated under reduced pressure to give the crude product. The crude was purified by prep-HPLC (column: Phenomenex Gemini-NX C18 75*30 mm*3 um; mobile phase: [water(0.05% NH$_3$H$_2$O+10 mM NH$_4$HCO$_3$)-ACN]; B %: 30%-60%, 8 min) to give 7-chloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-indole-2-carboxamide (180 mg, 407.32 umol, 43.57% yield) as a solid. MS (ESI) m/z 442.2 [M+H]$^+$; $^1$H NMR (400 MHz, DMSO-d$_6$) δ=11.71 (br s, 1H), 9.01 (d, J=7.9 Hz, 1H), 8.72 (d, J=7.5 Hz, 1H), 7.71 (s, 1H), 7.63 (dd, J=0.7, 7.9 Hz, 1H), 7.34-7.25 (m, 2H), 7.07 (t, J=7.8 Hz, 1H), 5.00 (q, J=7.9 Hz, 1H), 4.58-4.49 (m, 1H), 3.13 (quin, J=9.2 Hz, 2H), 2.42-2.31 (m, 1H), 2.22-2.05 (m, 2H), 1.89-1.64 (m, 3H), 1.57-1.46 (m, 1H), 0.89-0.75 (m, 1H), 0.50-0.37 (m, 2H), 0.25-0.07 (m, 2H).

Example 37. Synthesis of Viral Protease Inhibitor Compound 635

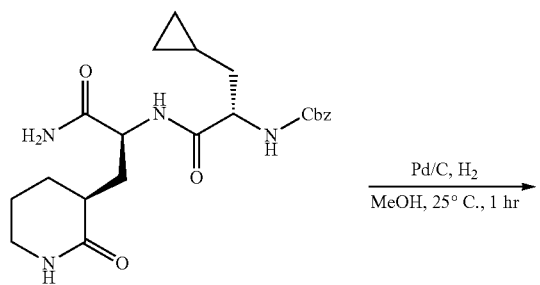

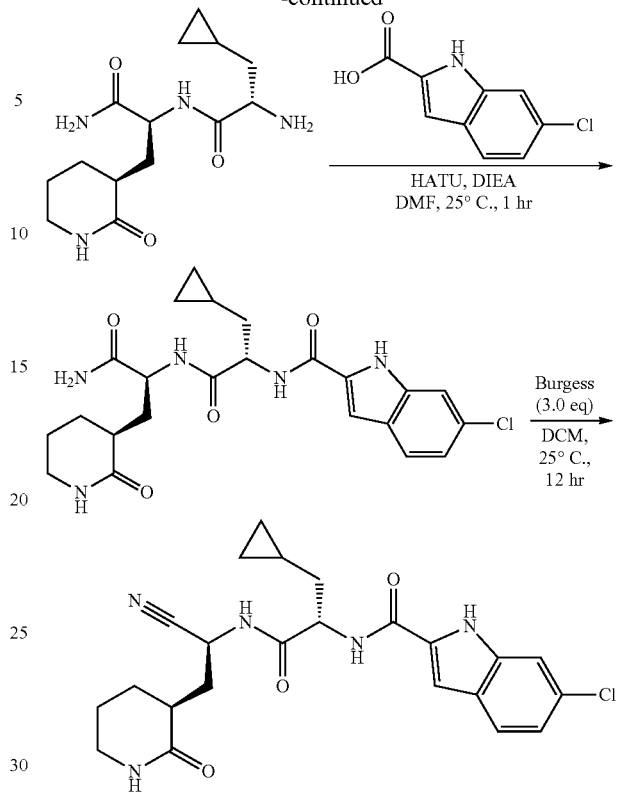

Step 1: (2S)-2-amino-N-[(1S)-2-amino-2-oxo-1-[[(3S)-2-oxo-3-piperidyl]methyl]ethyl]-3-cyclopropyl-propanamide To a solution of benzyl N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]carbamate (400 mg, 0.92 mmol, 1 eq) in MeOH (5 mL) was added Pd (200 mg, 10% purity) and H$_2$ (0.92 mmol). The mixture was stirred at 25° C. under 15 psi for 1 hr. The mixture was filtered to give the filter liquor. The mixture was concentrated under reduce pressure to give compound (2S)-2-amino-N-[(1S)-2-amino-2-oxo-1-[[(3S)-2-oxo-3-piperidyl]methyl]ethyl]-3-cyclopropyl-propanamide (274 mg, 0.92 mmol, 99.5% yield) as a solid.

Step 2: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-chloro-1H-indole-2-carboxamide To a solution of (2S)-2-amino-N-[(1S)-2-amino-2-oxo-1-[[(3S)-2-oxo-3-piperidyl]methyl]ethyl]-3-cyclopropyl-propanamide (137 mg, 0.46 mmol, 1 eq) and 6-chloro-1H-indole-2-carboxylic acid (90.4 mg, 0.46 mmol, 1 eq) in DMF (2 mL) was added DIPEA (119.4 mg, 0.92 mmol, 0.16 mL, 2 eq) and HATU (210.9 mg, 0.55 mmol, 1.2 eq). The mixture was stirred at 25° C. for 1 hr. LCMS showed one peak with desired MS was detected. The mixture was concentrated under reduce pressure. The residue was purified by flash silica gel chromatography (ISCO®; 12 g SepaFlash® Silica Flash Column, Eluent of 0~10% DCM/MeOH @ 30 mL/min) to give Compound N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-chloro-1H- indole-2-carboxamide (200 mg, 89.0% yield) as a solid. LCMS: Rt=0.780 min; for $C_{23}H_{28}ClN_5O_4$ MS Calcd.: 473.18; MS Found: 474.1 [M+H$^+$].

Step 3: 6-Chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-chloro-1H-indole-2-carboxamide (47.5 mg, 0.1 mmol, 1 eq) in DCM (1 mL) was added Burgess reagent (71.6 mg, 0.3 mmol, 3 eq) at 0° C. The mixture was stirred at 25° C. for 12 hr. The mixture was concentrated under reduce pressure. The residue was purified by prep-HPLC (column: Phenomenex Gemini-NX 80*40 mm*3 um; mobile phase: [water(0.05% NH$_3$H$_2$O+10 mM NH$_4$HCO$_3$)-ACN]; B %: 31%-61%, 7.8 min) to give compound 6-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide (64.33 mg, 34.7% yield) as a solid. LCMS: Rt=0.832 min; for $C_{23}H_{26}ClN_5O_3$; MS Calcd.: 455.17; MS Found: 456.1 [M+H$^+$]. $^1$H NMR (400 MHz, DMSO-d$_6$) δ 11.73 (br s, 1H), 8.95 (br d, J=8.0 Hz, 1H), 8.66 (br d, J=7.5 Hz, 1H), 7.66 (d, J=8.5 Hz, 1H), 7.53 (br s, 1H), 7.44 (s, 1H), 7.31 (s, 1H), 7.05 (dd, J=1.8, 8.5 Hz, 1H), 5.11-4.96 (m, 1H), 4.52-4.42 (m, 1H), 3.09 (br s, 2H), 2.34-2.21 (m, 2H), 1.89-1.75 (m, 3H), 1.74-1.65 (m, 1H), 1.56 (br s, 1H), 1.51-1.29 (m, 2H), 0.79 (br s, 1H), 0.42 (br d, J=7.0 Hz, 2H), 0.23-0.01 (m, 2H)

Example 38. Synthesis of Viral Protease Inhibitor Compound 637

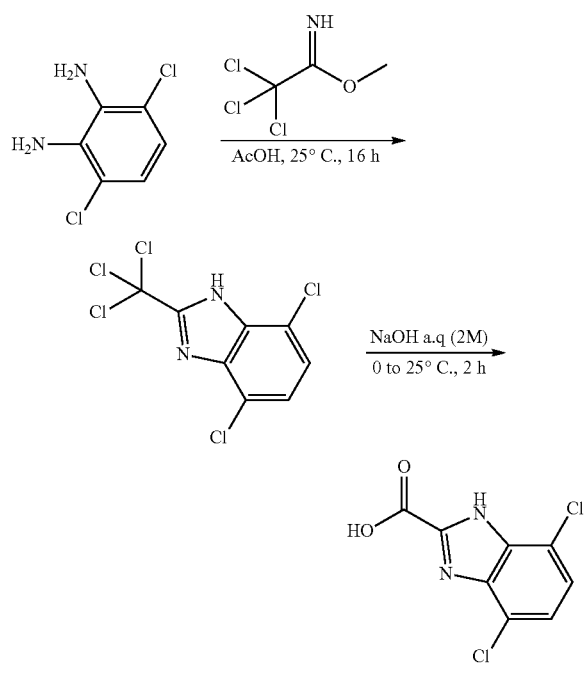

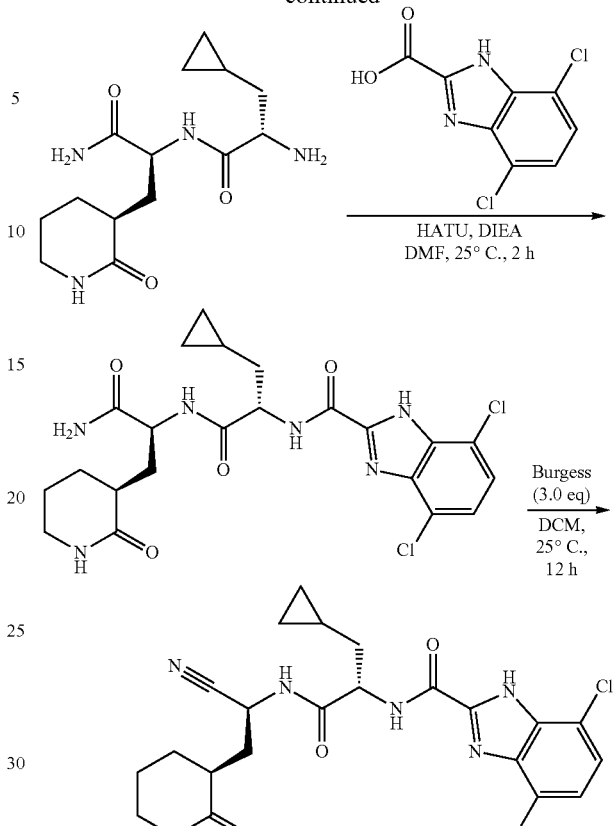

Step 1: 4,7-Dichloro-2-(trichloromethyl)-1H-benzimidazole

To a solution of 3,6-dichlorobenzene-1,2-diamine (0.3 g, 1.69 mmol, 1 eq) in AcOH (12.57 g, 209.2 mmol, 11.97 mL, 123.8 eq) was added methyl 2,2,2-trichloroacetimidate (313.0 mg, 1.77 mmol, 0.21 mL, 1.05 eq) at 0° C. The mixture was stirred at 25° C. for 16 hr. The resulting mixture was diluted with H$_2$O (40 mL) and filtered to give 4,7-dichloro-2-(trichloromethyl)-1H-benzo[d]imidazole (300 mg, crude) as a solid.

Step 2: 4,7-Dichloro-1H-benzimidazole-2-carboxylic acid

To a solution of NaOH (0.8 g, 20.0 mmol, 20.2 eq) in H$_2$O (10 mL) was added 4,7-dichloro-2-(trichloromethyl)-1H-benzo[d]imidazole (0.3 g, 985.58 umol, 1 eq) at 0° C. The mixture was stirred at 25° C. for 1 hr. The pH of the mixture was adjusted with HCl (2 M) to pH=2-3 and then the mixture was filtered to give 4,7-dichloro-1H-benzo[d]imidazole-2-carboxylic acid (0.2 g, crude) as a solid.

Step 3: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4,6-dichloro-1H-benzimidazole-2-carboxamide To a solution of (S)-2-amino-N-((S)-1-amino-1-oxo-3-((S)-2-oxopiperidin-3-yl)propan-2-yl)-3-cyclopropylpropanamide (130 mg, 0.43 mmol, 1 eq) and 4,7-dichloro-1H- benzo[d]imidazole-2-carboxylic acid (101.3 mg, 0.43 mmol, 1.0 eq) in DMF (3 mL) was added HATU (250.1 mg, 0.65 mmol, 1.5 eq) and DIPEA (113.3 mg, 0.87 mmol, 0.15 mL, 2.0 eq). The mixture was stirred at 25° C. for 1 hr. TLC (Dichloromethane:Methanol=10/1) indicated 4,7-dichloro-1H-benzo[d]imidazole-2-carboxylic acid was consumed completely and one new spot formed. The reaction mixture was concentrated under reduced pressure to give a residue. The residue was purified by column chromatography (SiO$_2$, Petroleum ether/Ethyl acetate=100/1 to 10/1) to give N-((S)-1-(((S)-1-amino-1-oxo-3-((S)-2-oxopiperidin-3-yl)propan-2-yl)amino)-3-cyclopropyl-1-oxopropan-2-yl)-4,7-dichloro-1H-benzo[d]imidazole-2-carboxamide (0.2 g, 0.39 mmol, 89% yield) as a solid.

Step 4: 4,7-dichloro-N-[(1S)-2-[[(1S)-1-cyano-2-[(3S)-2-oxo-3-piperidyl]ethyl]amino]-1-(cyclopropylmethyl)-2-oxo-ethyl]-1H-benzimidazole-2-carboxamide To a solution of N-((S)-1-(((S)-1-amino-1-oxo-3-((S)-2-oxopiperidin-3-yl)propan-2-yl)amino)-3-cyclopropyl-1-oxopropan-2-yl)-4,7-dichloro-1H-benzo[d]imidazole-2-carboxamide (100.00 mg, 0.19 mmol, 1 eq) in DCM (3.0 mL) was added Burgess Reagent (140.3 mg, 0.58 mmol, 3.0 eq). The mixture was stirred at 25° C. for 1 hr. The reaction mixture was concentrated under reduced pressure to give a residue. The residue was purified by prep-HPLC (column: Phenomenex Gemini-NX 80*40 mm*3 um; mobile phase: [water (0.05% NH3H2O+10 mM NH4HCO3)-ACN]; B %: 20%-50%, 7.8 min) to give the product (22.11 mg, 22% yield) as a solid. LCMS: Rt=0.824 min; for C$_{22}$H$_{24}$Cl$_2$N$_6$O$_3$ MS Calcd.: 490.13; MS Found: 491.1 [M+H$^+$]. $^1$H NMR (400 MHz, CD$_3$OD) δ 7.30 (s, 2H), 5.22-5.09 (m, 1H), 4.60 (t, J=7.1 Hz, 1H), 3.27-3.19 (m, 2H), 2.56-2.37 (m, 2H), 2.06-1.88 (m, 3H), 1.87-1.79 (m, 1H), 1.73 (td, J=7.2, 14.0 Hz, 2H), 1.60-1.44 (m, 1H), 0.96-0.75 (m, 1H), 0.54 (d, J=6.9 Hz, 2H), 0.21 (dd, J=4.8, 10.4 Hz, 2H).

Example 39. Synthesis of Viral Protease Inhibitor Compound 639 and 639A

Step 1: Methyl (2S)-2-[[2S)-2-(tert-butoxycarbonylamino)-3-cyclopropyl-propanoyl]amino]-3-[(3S)-2-oxo-3-piperidyl]propanoate

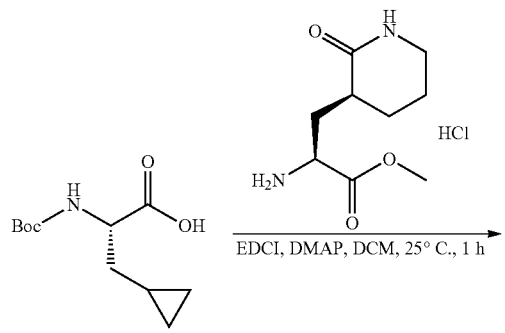

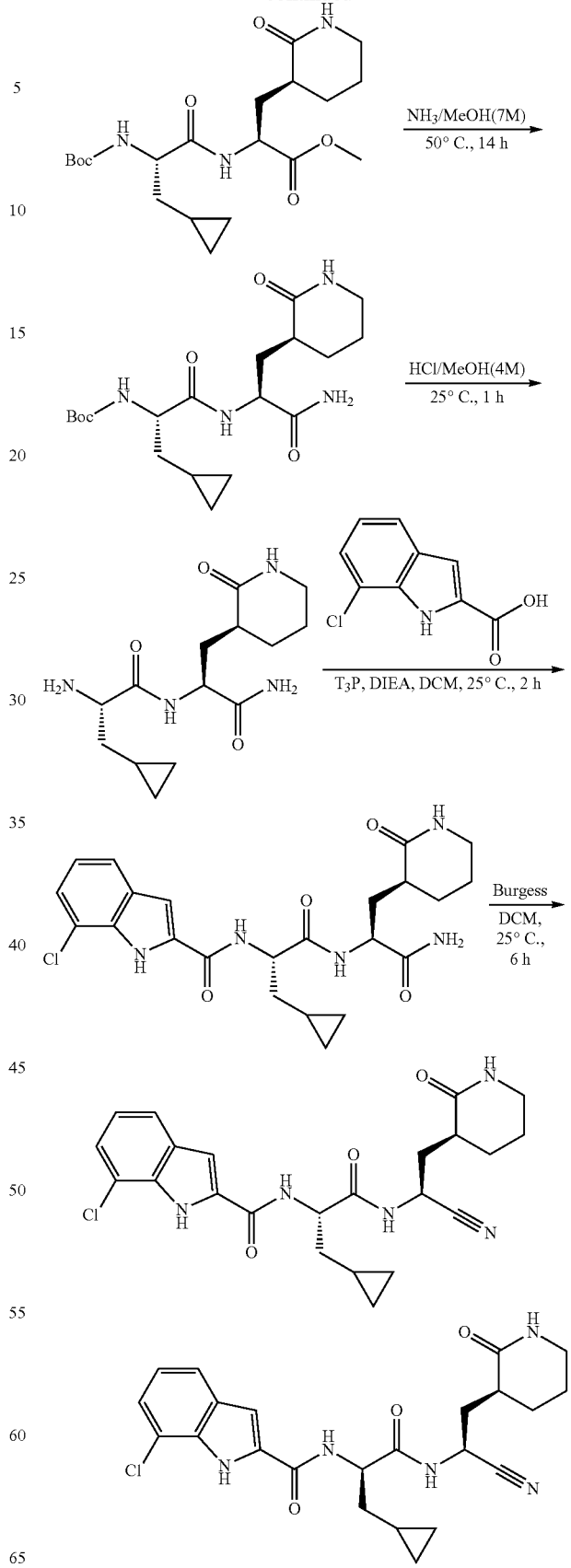

To a solution of (2S)-2-(tert-butoxycarbonylamino)-3-cyclopropyl-propanoic acid (1.07 g, 4.65 mmol, 1.1 eq) and methyl (2S)-2-amino-3-[(3S)-2-oxo-3-piperidyl]propanoate (1 g, 4.22 mmol, 1 eq, HCl) in DCM (10 mL) was added DMAP (1.55 g, 12.67 mmol, 3 eq) and EDCI (1.62 g, 8.45 mmol, 2 eq). The resulting mixture was stirred at 25° C. for 1 h. Upon completion, the solution was added with H₂O (30 mL), and then extracted with ethyl acetate (30 mL*3). The combined organic phase was dried over Na₂SO₄, filtrated and concentrated. The residue was purified by column chromatography (SiO₂, DCM/MeOH=30/1 to 10/1) to give methyl (2S)-2-[[(2S)-2-(tert-butoxycarbonylamino)-3-cyclopropyl-propanoyl]amino]-3-[(3S)-2-oxo-3-piperidyl]propanoate (1.2 g, 2.92 mmol, 68.97% yield, 100% purity) was obtained as yellow oil. MS (ESI) m/z 412.3 [M+H]⁺.

Step 2: (2R)-N-(4-(tert-butyl)phenyl)-N-(2-oxo-1-(pyridin-3-yl)-2-((pyridin-4-ylmethyl)amino)ethyl) pyrrolidine-2-carboxamide Methyl (2S)-2-[[(2S)-2-(tert-butoxycarbonylamino)-3-cyclopropyl-propanoyl]amino]-3-[(3S)-2-oxo-3-piperidyl]propanoate (600 mg, 1.46 mmol, 1 eq) in ammonia (7 M, 7.2 mL, 8.30 eq) was stirred at 50° C. for 14 h. Upon completion, the solution was concentrated to give tert-butyl N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]carbamate (580 mg, crude) as yellow oil. MS (ESI) m/z 397.3 [M+H]⁺.

Step 3: (2S)-2-amino-N-[(1S)-2-amino-2-oxo-1-[[(3S)-2-oxo-3-piperidyl]methyl]ethyl]-3-cyclopropyl-propanamide Tert-butyl N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]carbamate (580 mg, 1.46 mmol, 1 eq) in HCl/MeOH (4 M, 10.00 mL, 7.93 eq) was stirred at 25° C. for 1 h. Upon completion, the solution was concentrated to give (2S)-2-amino-N-[(1S)-2-amino-2-oxo-1-[[(3S)-2-oxo-3-piperidyl]methyl]ethyl]-3-cyclopropyl-propanamide (380 mg, crude) was obtained as yellow oil. MS (ESI) m/z 297.2 [M+H]⁺.

Step 4: (2S)-2-amino-N-[(1S)-2-amino-2-oxo-1-[[(3S)-2-oxo-3-piperidyl]methyl]ethyl]-3-cyclopropyl-propanamide To a solution of (2S)-2-amino-N-[(1S)-2-amino-2-oxo-1-[[(3S)-2-oxo-3-piperidyl]methyl]ethyl]-3-cyclopropyl-propanamide (380 mg, 1.28 mmol, 1 eq) in DCM (3 mL) was added 7-chloro-1H-indole-2-carboxylic acid (275.88 mg, 1.41 mmol, 1.1 eq), T₃P (1.22 g, 1.93 mmol, 1.14 mL, 50% purity, 1.5 eq), and DIEA (331.44 mg, 2.56 mmol, 446.68 uL, 2 eq). The mixture was stirred at 25° C. for 2 h. Upon completion, the solution was diluted with H₂O (20 mL), extracted with DCM (30 mL*3), the combined organic phase was dried over Na₂SO₄, filtrated and concentrated. The residue was purified by prep-TLC (SiO₂, DCM:MeOH=10:1) to give N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-1H-indole-2-carboxamide (350 mg, 738.47 umol, 57.59% yield, 100% purity) as yellow oil. MS (ESI) m/z 474.3 [M+H]⁺.

Step 5: 7-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-1H-indole-2-carboxamide (350 mg, 738.47 umol, 1 eq) in DCM (4 mL) was added Burgess reagent (527.94 mg, 2.22 mmol, 3 eq), and the solution was stirred at 25° C. for 6 h. Upon completion, DCM was removed using blow dry. The residue was purified by prep-HPLC (column: Waters Xbridge Prep OBD C18 150*40 mm*10 um; mobile phase: [water(0.05% NH₃H₂O+10mM NH4HCO₃)-ACN]; B %: 25%-55%, 8 min) to afford the product as a solid, which was further separated by SFC (column: DAICEL CHIRALPAK AS (250 mm*30 mm, 10 um); mobile phase: [0.1% NH₃H₂O ETOH]; B %: 33%-33%, 8 min) to give:

7-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide (250 mg, 530.89 umol, 74.25% yield, 96.82% purity) as a solid. MS (ESI) m/z 456.2 [M+H]⁺. ¹H NMR (400 MHz, METHANOL-d₄) δ=7.58 (d, J=7.9 Hz, 1H), 7.35-7.20 (m, 2H), 7.06 (t, J=7.8 Hz, 1H), 5.22-5.05 (m, 1H), 4.57 (t, J=7.5 Hz, 1H), 3.27-3.14 (m, 2H), 2.61-2.34 (m, 2H), 2.09-1.61 (m, 6H), 1.59-1.43 (m, 1H), 0.98-0.76 (m, 1H), 0.55 (dd, J=1.3, 8.2 Hz, 2H), 0.31-0.09 (m, 2H); and 7-chloro-N-[(1R)-2-[[(1S)-1-cyano-2-[(3S)-2-oxo-3-piperidyl]ethyl]amino]-1-(cyclopropylmethyl)-2-oxo-ethyl]-1H-indole-2-carboxamide (45 mg, 98.70 umol, 13.37% yield, 100% purity) as a solid. MS (ESI) m/z 456.2 [M+H]⁺. ¹H NMR (400 MHz, METHANOL-d₄) δ=7.59 (dd, J=0.9, 7.9 Hz, 1H), 7.32-7.21 (m, 2H), 7.07 (t, J=7.8 Hz, 1H), 5.12-5.02 (m, 1H), 4.59 (dd, J=6.4, 7.9 Hz, 1H), 3.21 (dd, J=4.6, 7.7 Hz, 2H), 2.44-2.23 (m, 2H), 2.09-1.62 (m, 6H), 1.60-1.47 (m, 1H), 0.94-0.78 (m, 1H), 0.62-0.43 (m, 2H), 0.27-0.11 (m, 2H).

Example 40. Synthesis of Viral Protease Inhibitor Compound 643

Step 1: Methyl (2S)-2-[[(2S)-2-(tert-butoxycarbonylamino)-4,4-dimethyl-pentanoyl]amino]-3-[(3S)-2-oxo-3-piperidyl]propanoate

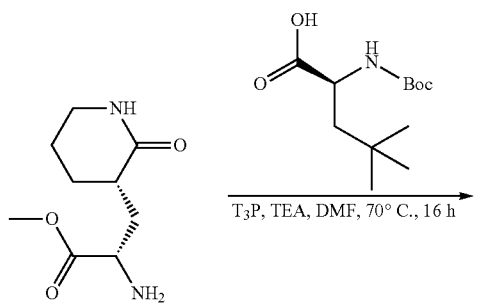

833

-continued

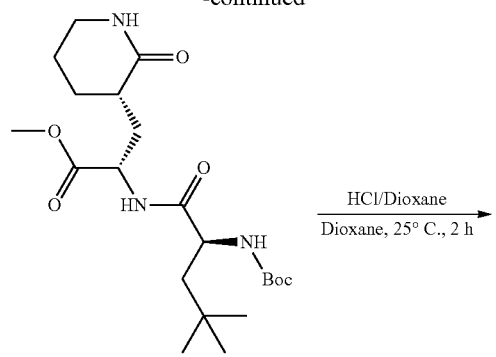

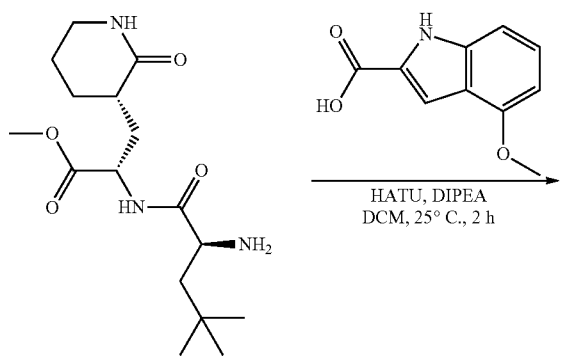

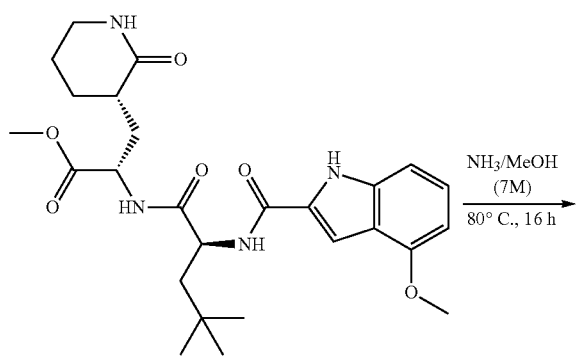

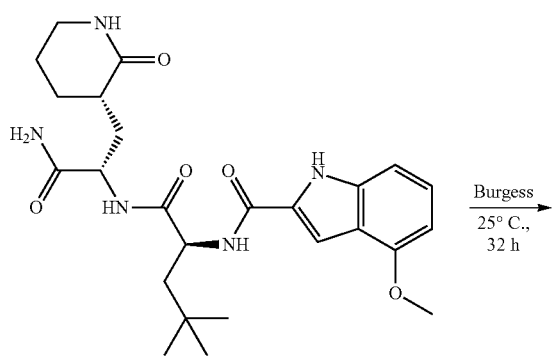

834

-continued

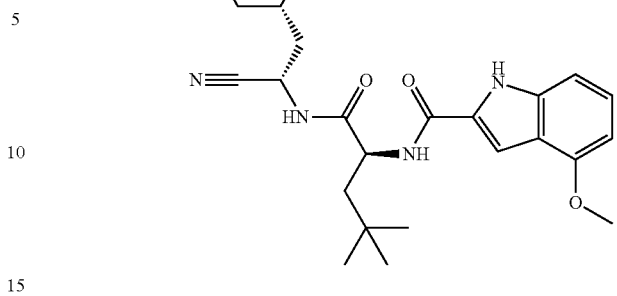

T₃P (2.69 g, 4.22 mmol, 2.51 mL, 50% purity, 2 eq) was added to a mixture of methyl (2S)-2-amino-3-[(3S)-2-oxo-3-piperidyl]propanoate (500 mg, 2.11 mmol, 1 eq, HCl), (2S)-2-(tert-butoxycarbonylamino)-4,4-dimethyl-pentanoic acid (570.0 mg, 2.32 mmol, 1.1 eq) and TEA (855.0 mg, 8.45 mmol, 1.18 mL, 4 eq) in DMF (5 mL). The resulting mixture was stirred at 70° C. for 16 hr. TLC (petroleum ether:ethyl acetate=0:1/PMA) showed new spots were detected. The reaction mixture was diluted with H₂O (10 mL) and the mixture was extracted with ethyl acetate (10 mL*3). The combined organic phase was washed with brine (10 mL*2), dried with anhydrous Na₂SO₄, filtered and concentrated in vacuum. The residue was purified by flash silica gel chromatography (ISCO®; 20 g SepaFlash® Silica Flash Column, Eluent of 0~100% Ethyl acetate/Petroleum ethergradient @30 mL/min). Compound methyl (2S)-2-[[(2S)-2-(tert-butoxycarbonylamino)-4,4-dimethyl-pentanoyl]amino]-3-[(3S)-2-oxo-3-piperidyl]propanoate (436 mg, 0.99 mmol, 47.2% yield, 97.9% purity) was obtained as a solid.

Step 2: Methyl (2S)-2-[[(2S)-2-amino-4,4-dimethyl-pentanoyl]amino]-3-[(3S)-2-oxo-3-piperidyl]propanoate Methyl (2S)-2-[[(2S)-2-(tert-butoxycarbonylamino)-4,4-dimethyl-pentanoyl]amino]-3-[(3S)-2-oxo-3-piperidyl]propanoate (300 mg, 0.70 mmol, 1 eq) in HCl/dioxane (4 M, 175.42 uL, 1 eq) was stirred at 25° C. for 2 hr. Compound methyl (2S)-2-[[(2S)-2-amino-4,4-dimethyl-pentanoyl]amino]-3-[(3S)-2-oxo-3-piperidyl]propanoate (250 mg, crude, HCl) was obtained as a solid and was used into next step without further purification.

Step 3: Methyl (2S)-2-[[(2S)-2-[(4-methoxy-1H-indole-2-carbonyl)amino]-4,4-dimethyl-pentanoyl]amino]-3-[(3S)-2-oxo-3-piperidyl]propanoate A mixture of methyl (2S)-2-[[(2S)-2-amino-4,4-dimethyl-pentanoyl]amino]-3-[(3S)-2-oxo-3-piperidyl]propanoate (310 mg, 0.85 mmol, 1 eq, HCl), 4-methoxy-1H-indole-2-carboxylic acid (179.1 mg, 0.93 mmol, 1.1 eq), HATU (647.8 mg, 1.70 mmol, 2 eq) and DIPEA (440.4 mg, 3.41 mmol, 0.60 mL, 4 eq) in DCM (4 mL) was stirred at 25° C. for 2 hr. TLC (petroleum ether/ethyl acetate=0:1/UV 254 nm) showed new spots were detected. The reaction mixture was diluted with H₂O (10 mL) and the mixture was extracted with ethyl acetate (10 mL*3). The combined organic phase was washed with brine (10 mL*2), dried with anhydrous Na₂SO₄, filtered and concentrated in vacuum. The residue was purified by flash silica gel chromatography (ISCO®; 12 g SepaFlash® Silica Flash Column, Eluent of 0~100% Ethyl acetate/Petroleum ethergradient @ 30 mL/min). Compound methyl (2S)-2-[[(2S)-2-[(4-methoxy-1H-indole-2-carbonyl)amino]-4,4-dimethyl-pentanoyl]amino]-3-[(3S)-2-oxo-3-piperidyl]propanoate (451 mg, 0.68 mmol, 80.1% yield) was obtained as an oil and confirmed by LC-MS.

Step 4: N-[(1S)-1-[[(1S)-2-amino-2-oxo-1-[[(3S)-2-oxo-3-piperidyl]methyl]ethyl]carbamoyl]-3,3-dimethyl-butyl]-4-methoxy-1H-indole-2-carboxamide $NH_3$ (7 M, 11.42 mL, 100 eq) was added to a mixture of methyl (2S)-2-[[(2S)-2-[(4-methoxy-1H-indole-2-carbonyl)amino]-4,4-dimethyl-pentanoyl]amino]-3-[(3S)-2-oxo-3-piperidyl]propanoate (400 mg, 0.79 mmol, 1 eq) in MeOH. Then, the mixture was stirred at 80° C. for 16 hr. TLC (DCM:MeOH=10:1/UV 254 nm) showed new spot was detected. The reaction mixture was concentrated in vacuum. The residue was purified by flash silica gel chromatography (ISCO®; 12 g SepaFlash® Silica Flash Column, Eluent of 0~50% Ethyl acetate/MeOH @30 mL/min). Compound N-[(1S)-1-[[(1S)-2-amino-2-oxo-1-[[(3S)-2-oxo-3-piperidyl]methyl]ethyl]carbamoyl]-3,3-dimethyl-butyl]-4-methoxy-1H-indole-2-carboxamide (295 mg, 0.60 mmol, 75.1% yield, 98.9% purity) was obtained as a solid.

Step 5: N-[(1S)-1-[[(1S)-1-cyano-2-[(3S)-2-oxo-3-piperidyl]ethyl]carbamoyl]-3,3-dimethyl-butyl]-4-methoxy-1H-indole-2-carboxamide Methoxycarbonyl-(triethylammonio)sulfonyl-azanide (284.6 mg, 1.19 mmol, 2 eq) was added at the mixture of N-[(1S)-1-[[(1S)-2-amino-2-oxo-1-[[(3S)-2-oxo-3-piperidyl]methyl]ethyl]carbamoyl]-3,3-dimethyl-butyl]-4-methoxy-1H-indole-2-carboxamide (290 mg, 0.59 mmol, 1 eq) in DCM (3 mL) at 25° C. Then the mixture was stirred at 25° C. for 16 hr. Then methoxycarbonyl-(triethylammonio)sulfonyl-azanide (142.3 mg, 0.59 mmol, 1 eq) was added to the mixture and the mixture was stirred at 25° C. for anther 16 hr. The reaction mixture was diluted with $H_2O$ (10 mL) and the mixture was extracted with ethyl acetate (10 mL*3). The combined organic phase was washed with brine (10 mL*2), dried with anhydrous $Na_2SO_4$, filtered and concentrated in vacuum. The residue was purified by prep-HPLC (column: Welch Xtimate C18 150*25 mm*5 um; mobile phase: [water (0.05% ammonia hydroxide v/v)-MeOH]; B %: 55%-85%, 9.5 min). Compound N-[(1S)-1-[[(1S)-1-cyano-2-[(3S)-2-oxo-3-piperidyl]ethyl]carbamoyl]-3,3-dimethyl-butyl]-4-methoxy-1H-indole-2-carboxamide (28.1 mg, 59.3 umol, 9.9% yield, 98.7% purity) was obtained as a solid. Rt=0.832 min; for $C_{25}H_{33}N_5O_4$ MS Calcd.: 467.25, MS Found: 468.2 [M+H$^+$]. $^1$H NMR (400 MHz, CD$_3$OD) δ 7.26-7.22 (m, 1H), 7.18-7.12 (m, 1H), 7.05-7.00 (m, 1H), 6.51 (d, J=7.5 Hz, 1H), 5.08 (dd, J=6.3, 9.8 Hz, 1H), 4.67-4.63 (m, 1H), 3.93 (s, 3H), 3.21-3.15 (m, 2H), 2.47-2.38 (m, 21H), 1.98-1.72 (m, 6H), 1.70-1.58 (m, 1H), 1.54-1.43 (m, 1H), 1.02 (s, 8H), 1.04-1.01 (m, 21H).

Example 41. Synthesis of Viral Protease Inhibitor Compound 681

Step 1: (2S)-methyl 2-(2-(4-methoxy-1H-indole-2-carbonyl)-2-azaspiro[4.5]decane-3-carboxamido)-3-((S)-2-oxopiperidin-3-yl)propanoate

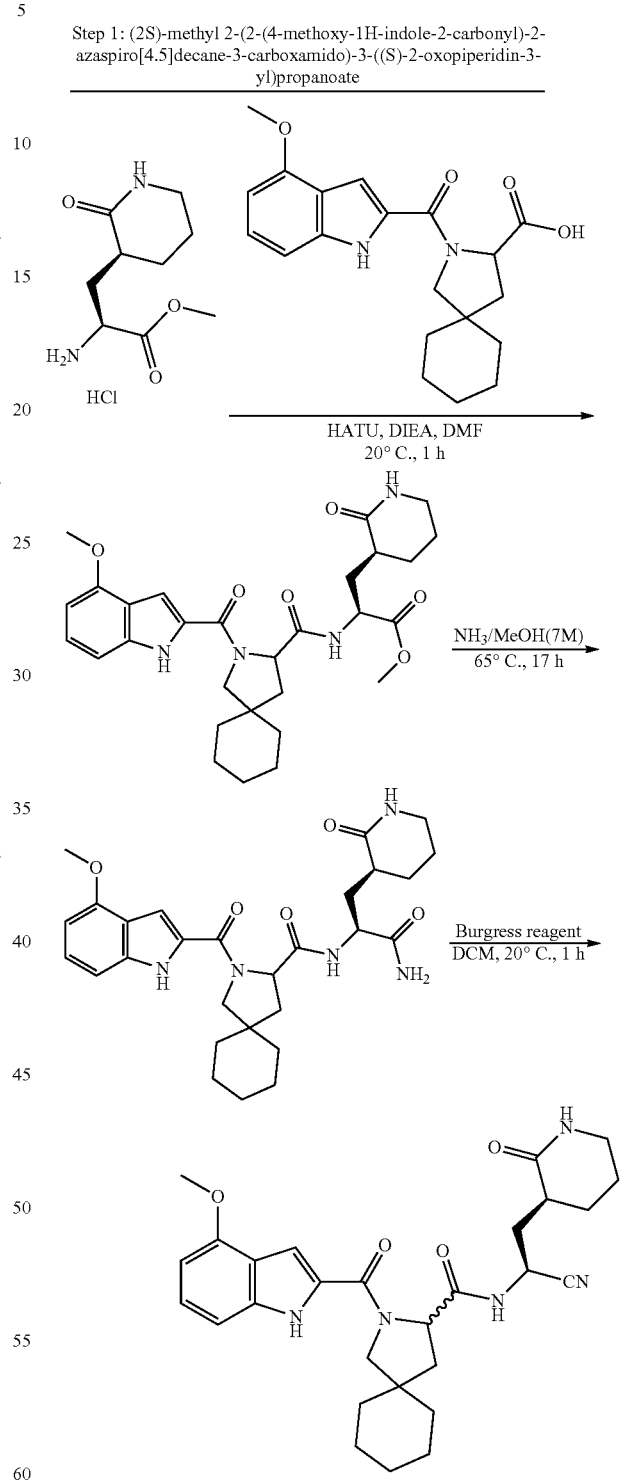

To a solution of methyl (2S)-2-amino-3-[(3S)-2-oxo-3-piperidyl]propanoate (500 mg, 2.11 mmol, 1.1 eq, HCl) and 2-(4-methoxy-1H-indole-2-carbonyl)-2-azaspiro[4.5]decane-3-carboxylic acid (684.45 mg, 1.92 mmol, 1 eq) in DMF (15 mL) was added N,N-diisopropylethylamine (DIEA) (744.57 mg, 5.76 mmol, 1.00 mL, 3 eq) and (1-[bis (dimethylamino)methylene]-1H-1,2,3-triazolo[4,5-b]pyridinium 3-oxide hexafluorophosphate (HATU) (730.19 mg, 1.92 mmol, 1 eq). The mixture was stirred at 20° C. for 1 h. Upon completion, the two batch reaction mixture was quenched by addition H₂O (80 mL), and extracted with ethyl acetate (40 mL*3). The combined organic layers were washed with brine 40 mL, dried over Na₂SO₄, filtered and concentrated under reduced pressure to get the product methyl (2S)-2-[[2-(4-methoxy-1H-indole-2-carbonyl)-2-azaspiro[4.5]decane-3-carbonyl]amino]-3-[(3S)-2-oxo-3-piperidyl]propanoate (1.35 g, crude) was obtained as white solid. MS (ESI) m/z 539.3 [M+H]⁺.

Step 2: N-((S)-1-amino-1-oxo-3-((S)-2-oxopiperidin-3-yl)propan-2-yl)-2-(4-methoxy-1H-indole-2-carbonyl)-2-azaspiro[4.5]decane-3-carboxamide A solution of methyl (2S)-2-[[2-(4-methoxy-1H-indole-2-carbonyl)-2-azaspiro[4.5]decane-3-carbonyl]amino]-3-[(3S)-2-oxo-3-piperidyl]propanoate (650 mg, 1.21 mmol, 1 eq) in NH₃/MeOH (7 M, 3.45 mL, 20 eq) was stirred at 65° C. for 17 h. Upon completion, the two batch reaction mixture was concentrated under reduced pressure to get the product N-[(1S)-2-amino-2-oxo-1-[[(3S)-2-oxo-3-piperidyl]methyl]ethyl]-2-(4-methoxy-1H-indole-2-carbonyl)-2-azaspiro[4.5]decane-3-carboxamide (1.22 g, crude) as colorless oil. MS (ESI) m/z 524.3 [M+H]⁺.

Step 3: N-((S)-1-cyano-2-((S)-2-oxopiperidin-3-yl)ethyl)-2-(4-methoxy-1H-indole-2-carbonyl)-2-azaspiro[4.5]decane-3-carboxamide To a solution of N-[(1S)-2-amino-2-oxo-1-[[(3S)-2-oxo-3-piperidyl]methyl]ethyl]-2-(4-methoxy-1H-indole-2-carbonyl)-2-azaspiro[4.5]decane-3-carboxamide (1.22 g, 2.33 mmol, 1 eq) in DCM (20 mL) was added Burgess reagent (1.39 g, 5.82 mmol, 2.5 eq). The mixture was stirred at 20° C. for 1 h. Upon completion, the reaction mixture was quenched by the addition of H₂O (3 mL) and then concentrated under reduced pressure to give a residue. The residue was purified by prep-HPLC (column: Agela DuraShell C18 250*70 mm*10 um; mobile phase: [water (10 mM NH₄HCO₃)-ACN]; B %: 43%-63%, 20 min) to give desired compound (490 mg) as a solid, which was further separated by SFC (column: DAICEL CHIRALPAK AD (250 mm*30 mm, 10 um); mobile phase: [0.1% NH₃H₂O IPA]; B %: 58%-58%, 10 min) to afford the product N-[(1S)-1-cyano-2-[(3S)-2-oxo-3-piperidyl]ethyl]-2-(4-methoxy-1H-indole-2-carbonyl)-2-azaspiro[4.5]decane-3-carboxamide, Isomer 1 (201.77 mg, 394.36 umol, 16.93% yield) was obtained as white solid. MS (ESI) m/z 506.3[M+H]⁺. ¹H NMR (400 MHz, DMSO-d₆) δ ppm 11.26 (br s, 1H) 8.50-8.85 (m, 1H) 7.23 (br s, 1H) 7.00-7.16 (m, 2H) 6.89 (br s, 1H) 6.52 (br d, J=7.46 Hz, 1H) 4.86-5.06 (m, 1H) 4.48-4.79 (m, 1H) 3.80-3.98 (m, 4H) 3.59 (br d, J=4.65 Hz, 1H) 3.09 (br s, 2H) 2.15-2.31 (m, 3H) 1.73-2.01 (m, 2H) 1.67 (br dd, J=12.17, 8.62 Hz, 2H) 1.33-1.61 (m, 12H); and
N-[(1S)-1-cyano-2-[(3S)-2-oxo-3-piperidyl]ethyl]-2-(4-methoxy-1H-indole-2-carbonyl)-2-azaspiro[4.5]decane-3-carboxamide, Isomer 2 (200.95 mg, 394.35 umol, 16.93% yield) was obtained as white solid. MS (ESI) m/z 506.3[M+H]⁺. ¹H NMR (400 MHz, DMSO-d₆) δ ppm 11.27 (br s, 1H) 8.61 (br d, J=1.22 Hz, 1H) 7.02-7.26 (m, 3H) 6.91 (br s, 1H) 6.53 (d, J=7.46 Hz, 1H) 4.91-5.06 (m, 1H) 4.62 (br s, 1H) 3.82-3.98 (m, 4H) 3.52-3.75 (m, 1H) 3.09 (br s, 2H) 2.09-2.28 (m, 3H) 1.63-1.92 (m, 4H) 1.33-1.62 (m, 12H).

Example 42. Synthesis of Viral Protease Inhibitor Compound 721

Step 1: (S)-methyl 2-((S)-2-((tert-butoxycarbonyl)amino)-4,4-dimethylpentanamido)-3-((S)-2-oxopiperidin-3-yl)propanoate

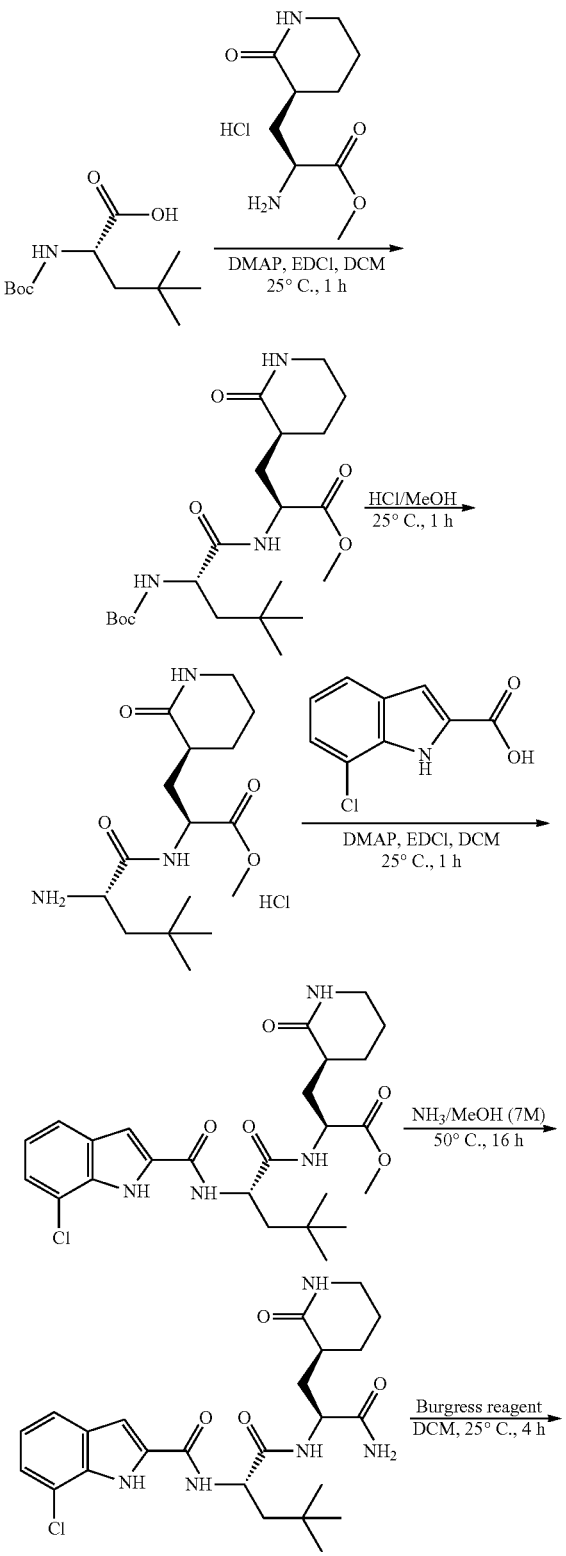

-continued

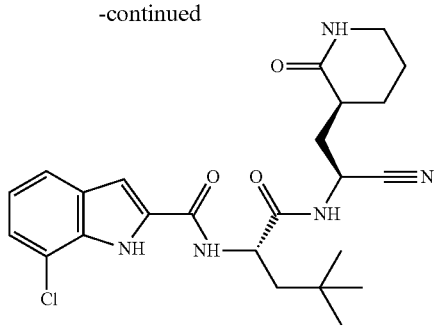

To a solution of (2S)-2-(tert-butoxycarbonylamino)-4,4-dimethyl-pentanoic acid (2.49 g, 10.14 mmol, 1.2 eq) and methyl (2S)-2-amino-3-[(3S)-2-oxo-3-piperidyl] propanoate (2 g, 8.45 mmol, 1 eq, HCl) in DCM (60 mL) was added DMAP (3.10 g, 25.35 mmol, 3 eq). Then, EDCI (3.24 g, 16.90 mmol, 2 eq) was added, and the resulting mixture was stirred at 25° C. for 1 h. Upon the reaction completement, the mixture was quenched by water (400 mL), extracted with DCM (150 mL*3), and then was dried by sat. NaCl (50 mL). The resulting solution was concentrated in vacuum and was purified by column (SiO$_2$, petroleum ether:ethyl acetate=2:1 to 0:1). The resulting residue was washed with HCl (1 M, 150 mL), extracted with DCM (50 mL*3), and then the pH of the solution was adjust pH=~8 with sat. NaHCO$_3$ (30 mL). The resulting mixture was extracted with DCM (100 mL), and then concentrated under vacuum to afford (S)-methyl 2-((S)-2-((tert-butoxycarbonyl)amino)-4,4-dimethylpentanamido)-3-((S)-2-oxopiperidin-3-yl) propanoate (3 g, 6.32 mmol, 74.74% yield) as a solid. $^1$H NMR (400 MHz, CDCl$_3$-d) S ppm 7.61 (d, J=7.0 Hz, 1H), 6.85-6.51 (m, 1H), 6.22 (s, 1H), 5.06-4.85 (m, 1H), 4.63-4.47 (m, 1H), 4.30-4.02 (m, 1H), 3.79-3.66 (m, 3H), 3.35-3.25 (m, 2H), 2.42-2.24 (m, 1H), 2.14-2.05 (m, 1H), 1.96-1.66 (m, 4H), 1.63-1.52 (m, 1H), 1.43 (s, 9H), 1.03-0.90 (m, 9H).

Step 2: (S)-methyl 2-((S)-2-amino-4,4-dimethylpentanamido)-3-((S)-2-oxopiperidin-3-yl)propanoate A solution of (S)-methyl 2-((S)-2-((tert-butoxycarbonyl)amino)-4,4-dimethylpentanamido)-3-((S)-2-oxopiperidin-3-yl) propanoate (1.5 g, 3.51 mmol, 1 eq) in HCl/MeOH (4 M, 20 mL) was stirred at 25° C. for 1 h. Upon the reaction completement, the mixture was concentrated under vacuum to obtain (S)-methyl 2-((S)-2-amino-4,4-dimethylpentanamido)-3-((S)-2-oxopiperidin-3-yl)propanoate (1.1 g, crude, HCl) as a solid. $^1$H NMR (400 MHz, D$_2$O) δ ppm 4.57 (dd, J=4.8, 10.3 Hz, 1H), 3.98 (dd, J=5.2, 7.8 Hz, 1H), 3.78-3.65 (m, 3H), 3.29-3.14 (m, 2H), 2.75-2.33 (m, 1H), 2.24-1.47 (m, 8H), 1.04-0.86 (m, 9H).

Step 3: (S)-methyl2-((S)-2-(7-chloro-1H-indole-2-carboxamido)-4,4-dimethylpentanamido)-3-((S)-2-oxopiperidin-3-yl)propanoate To a solution of (S)-methyl 2-((S)-2-amino-4,4-dimethylpentanamido)-3-((S)-2-oxopiperidin-3-yl)propanoate (550 mg*2, HCl salt, 1.68 mmol, 1 eq) and 7-chloro-1H-indole-2-carboxylic acid (394.29 mg, 2.02 mmol, 1.2 eq) in DCM (6 mL) was added DMAP (615.66 mg, 5.04 mmol, 3 eq). EDCI (644.05 mg, 3.36 mmol, 2 eq) was added to the mixture at 25° C., and the mixture was stirred at 25° C. for 1 h. Upon the reaction completement, the mixture was quenched by water (200 mL), extracted with DCM (70 mL*3), and then concentrated under vacuum. The resulting residue was purified by column (SiO$_2$, petroleum ether:ethyl acetate=1:1 to 0:1), concentrated in vacuum, and then was washed with 1M HCl (100 mL) and extracted with DCM (30 mL*3). The organic phase was adjusted to pH=~7 with sat. NaHCO$_3$ (30 mL), and then concentrated in vacuum to obtain (S)-methyl 2-((S)-2-(7-chloro-1H-indole-2-carboxamido)-4,4-dimethylpentanamido)-3-((S)-2-oxopiperidin-3-yl)propanoate (650 mg, 1.16 mmol, 40% yield) as a solid. MS (ESI) m/z 505.2 [M+H]$^+$; $^1$H NMR (400 MHz, MeOD-d$_4$) δ ppm 7.58 (d, J=7.8 Hz, 1H), 7.32-7.17 (m, 2H), 7.06 (t, J=7.8 Hz, 1H), 4.73 (dd, J=3.8, 8.6 Hz, 1H), 4.55 (dd, J=4.0, 11.7 Hz, 1H), 3.71 (s, 3H), 3.35 (s, 1H), 3.24-3.01 (m, 2H), 2.49-2.22 (m, 2H), 2.02-1.40 (m, 8H), 1.08-0.96 (m, 9H).

Step 4: N-((S)-1-(((S)-1-amino-1-oxo-3-((S)-2-oxopiperidin-3-yl)propan-2-yl)amino)-4,4-dimethyl-1-oxopentan-2-yl)-7-chloro-1H-indole-2-carboxamide A solution of (S)-methyl 2-((S)-2-(7-chloro-1H-indole-2-carboxamido)-4,4-dimethylpentanamido)-3-((S)-2-oxopiperidin-3-yl)propanoate (650 mg, 1.29 mmol, 1 eq) in NH$_3$/MeOH (7M, 10 mL) was stirred at 50° C. for 16 h. Upon the reaction completement, the mixture was concentrated in vacuum to obtain N-((S)-1-(((S)-1-amino-1-oxo-3-((S)-2-oxopiperidin-3-yl) propan-2-yl) amino)-4,4-dimethyl-1-oxopentan-2-yl)-7-chloro-1H-indole-2-carboxamide (450 mg, crude) as a light yellow solid. MS (ESI) m/z 490.3 [M+H]$^+$ Step 5: 7-chloro-N-((S)-1-(((S)-1-cyano-2-((S)-2-oxopiperidin-3-yl)ethyl)amino)-4,4-dimethyl-1-oxopentan-2-yl)-1H-indole-2-carboxamide To a solution of N-((S)-1-(((S)-1-amino-1-oxo-3-((S)-2-oxopiperidin-3-yl) propan-2-yl) amino)-4,4-dimethyl-1-oxopentan-2-yl)-7-chloro-1H-indole-2-carboxamide (430 mg, 877.56 umol, 1 eq) in DCM (10 mL) was added Burgess reagent (627.38 mg, 2.63 mmol, 3 eq). The reaction mixture was stirred at 25° C. for 4 h. Upon the reaction completement, the mixture was quenched by water (10 mL), dried with a stream of N$_2$ and purified by prep-HPLC (column: Kromasil C18 (250*50 mm*10 um); mobile phase: [water (10 mM NH$_4$HCO$_3$)-ACN]; B %: 35%-65%, 10 min) to obtain 7-chloro-N-((S)-1-(((S)-1-cyano-2-((S)-2-oxopiperidin-3-yl)ethyl)amino)-4,4-dimethyl-1-oxopentan-2-yl)-1H-indole-2-carboxamide (205 mg, 424.79 umol, 48.41% yield) as a white solid. MS (ESI) m/z 472.2 [M+H]$^+$; 1H NMR (400 MHz, DMSO-d$_6$) δ ppm 11.70 (s, 1H), 9.02 (d, J=8.0 Hz, 1H), 8.71 (d, J=8.0 Hz, 1H), 7.63 (d, J=8.0 Hz, 1H), 7.52 (s, 1H), 7.34-7.23 (m, 2H), 7.07 (t, J=7.8 Hz, 1H), 5.05 (q, J=8.2 Hz, 1H), 4.63-4.54 (m, 1H), 3.07 (s, 2H), 2.30-2.18 (m, 2H), 1.88-1.32 (m, 7H), 0.95 (s, 9H).

Example 43. Synthesis of Viral Protease Inhibitor Compound 133

Step 1: 7-chloro-1H-benzo[d]imidazole-2-carboxylic acid

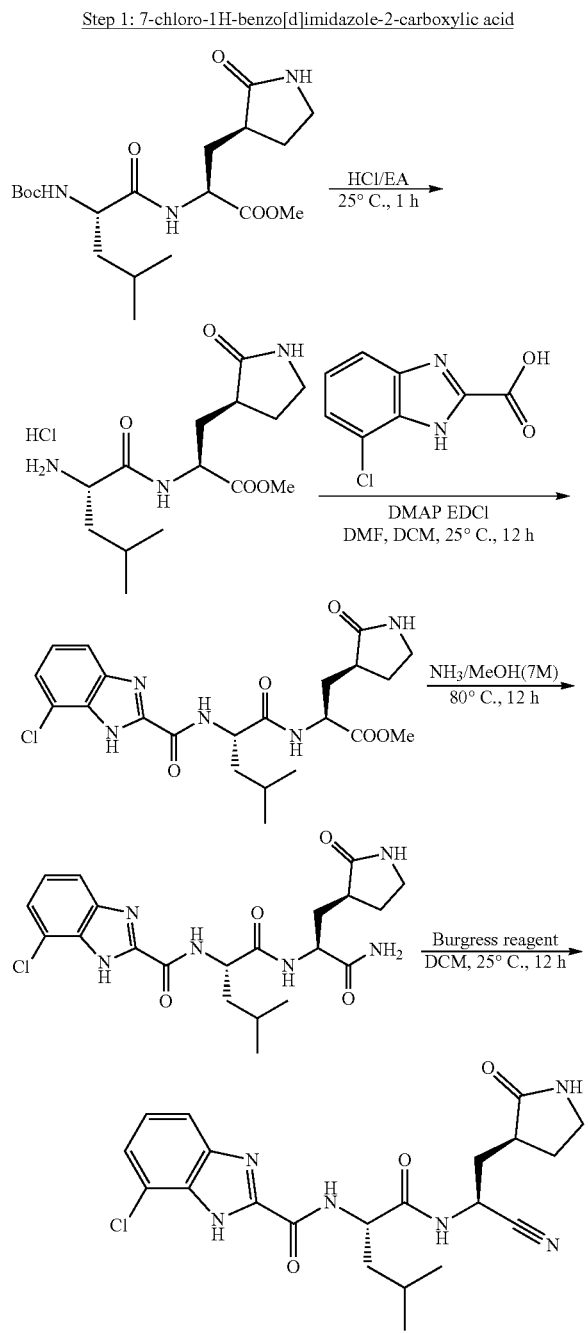

A solution of 3-chlorobenzene-1,2-diamine (500 mg, 3.51 mmol, 1 eq) in AcOH (9 mL) was added drop-wise methyl 2,2,2-trichloroethanimidoate (619.29 mg, 3.51 mmol, 433.07 uL, 1 eq), and the mixture was stirred at 25° C. for 2 h. The reaction mixture was quenched with H₂O 10 mL at 0° C., and the resultant precipitate was collected. The solid was washed with H₂O (2*10 mL) and dried under vacuum to get the product 7-chloro-1H-benzimidazole-2-carboxylic acid (500 mg, crude) was obtained as a solid. MS (ESI) m/z 195.1 [M−H]⁺

Step 2: (S)-methyl 2-((S)-2-amino-4-methylpentanamido)-3-((S)-2-oxopyrrolidin-3-yl)propanoate hydrochloride To a solution of methyl (2S)-2-[[(2S)-2-(tert-butoxycarbonylamino)-4-methyl-pentanoyl]amino]-3-[(3S)-2-oxopyrrolidin-3-yl]propanoate (300 mg, 750.98 umol, 1 eq) in EtOAc (2 mL) was added drop-wise HCl/EtOAc (4 M, 20 mL, 106.53 eq), and the mixture was stirred at 25° C. for 1 h. The reaction mixture was concentrated under reduced pressure to get a product methyl (2S)-2-[[(2S)-2-amino-4-methyl-pentanoyl]amino]-3-[(3S)-2-oxopyrrolidin-3-yl] propanoate (250 mg, crude, HCl) was obtained as a solid.

Step 3: (S)-methyl 2-((S)-2-(7-chloro-1H-benzo[d]imidazole-2-carboxamido)-4-methylpentanamido)-3-((S)-2-oxopyrrolidin-3-yl)propanoate To a solution of methyl (2S)-2-[[(2S)-2-amino-4-methylpentanoyl]amino]-3-[(3S)-2-oxopyrrolidin-3-yl]propanoate (250 mg, 744.43 umol, 1.0 eq, HCl) and 7-chloro-1H-benzimidazole-2-carboxylic acid (243.91 mg, 744.43 umol, 60% purity, 1 eq) in DMF (3 mL) was added EDCI (285.42 mg, 1.49 mmol, 2.0 eq), DMAP (181.89 mg, 1.49 mmol, 2.0 eq). After the addition of DCM (9 mL), the reaction was stirred at 25° C. for 12 h. The reaction mixture was quenched by addition H₂O (40 mL) at 0° C., and then extracted with DCM (20 mL*3). The combined organic layers were washed with brine (20 mL), dried over Na₂SO₄, filtered and concentrated under reduced pressure to give a residue. The residue was purified by column chromatography (SiO₂, Petroleum ether/Ethyl acetate=1/0 to 0/1) to get a product methyl (2S)-2-[[(2S)-2-[(7-chloro-1H-benzimidazole-2-carbonyl)amino]-4-methyl-pentanoyl]amino]-3-[(3S)-2-oxopyrrolidin-3-yl]propanoate (220 mg, 327.28 umol, 43.96% yield, 71.1% purity) was obtained as a yellow solid. MS (ESI) m/z 478.0 [M+H]⁺

Step 4: N-((S)-1-(((S)-1-amino-1-oxo-3-((S)-2-oxopyrrolidin-3-yl)propan-2-yl)amino)-4-methyl-1-oxopentan-2-yl)-7-chloro-1H-benzo[d]imidazole-2-carboxamide A solution of methyl (2S)-2-[[(2S)-2-[(7-chloro-1H-benzimidazole-2-carbonyl)amino]-4-methyl-pentanoyl]amino]-3-[(3S)-2-oxopyrrolidin-3-yl]propanoate (200 mg, 418.46 umol, 1 eq) in ammonia (7 M, 20 mL, 334.56 eq) was stirred at 80° C. for 12 h. The reaction mixture was concentrated under reduced pressure to get a product N-[(1S)-1-[[(1S)-2-amino-2-oxo-1-[[(3S)-2-oxopyrrolidin-3-yl]methyl]ethyl]carbamoyl]-3-methyl-butyl]-7-chloro-1H-benzimidazole-2-carboxamide (160 mg, crude) was obtained as a yellow solid. MS (ESI) m/z 463.2 [M+H]⁺

Step 5: 7-chloro-N-((S)-1-(((S)-1-cyano-2-((S)-2-oxopyrrolidin-3-yl)ethyl)amino)-4-methyl-1-oxopentan-2-yl)-1H-benzo[d]imidazole-2-carboxamide To a solution of N-[(1S)-1-[[(1S)-2-amino-2-oxo-1-[[(3S)-2-oxopyrrolidin-3-yl]methyl]ethyl]carbamoyl]-3-methyl-butyl]-7-chloro-1H-benzimidazole-2-carboxamide (80 mg, 108.87 umol, 63% purity, 1 eq) in DCM (4 mL) was added methoxycarbonyl-(triethylammonio)sulfonyl-azanide (129.73 mg, 544.36 umol, 5.0 eq), and then the mixture was stirred at 25° C. for 12 h. The reaction mixture was concentrated under reduced pressure to give a residue. The residue was purified by prep-HPLC (column: Waters Xbridge BEH C18 100*25 mm*5 um; mobile phase: [water (10 mM NH₄HCO₃)-ACN]; B %: 20%-50%, 10 min) and by prep-HPLC (column: Phenomenex Luna C18 75*30 mm*3 um; mobile phase: [water(0.2% FA)-ACN]; B %: 10%-60%, 8 min) to afford 7-chloro-N-[(1S)-1-[[(1S)-1-cyano-2-[(3S)-2-oxopyrrolidin-3-yl]ethyl]carbamoyl]-3-methyl-butyl]-1H-benzimidazole-2-carboxamide (13.28 mg, 29.85 umol, 27.42% yield, 100% purity) as a white solid. MS (ESI) m/z 445.1 [M+H]⁺. ¹H NMR (400 MHz, DMSO-d₆) δ ppm 13.64 (br s, 1H), 8.76-9.00 (m, 2H), 7.70 (s, 1H), 7.51 (br d, J=6.2 Hz, 1H), 7.25-7.42 (m, 2H), 4.90-5.06 (m, 1H), 4.55 (br t, J=7.4 Hz, 1H), 3.05-3.18 (m, 2H), 2.33-2.42 (m, 1H), 2.05-2.23 (m, 2H), 1.54-1.90 (m, 5H), 0.92 (br dd, J=8.5, 6.3 Hz, 6H).

Example 44. Synthesis of Viral Protease Inhibitor Compound 145

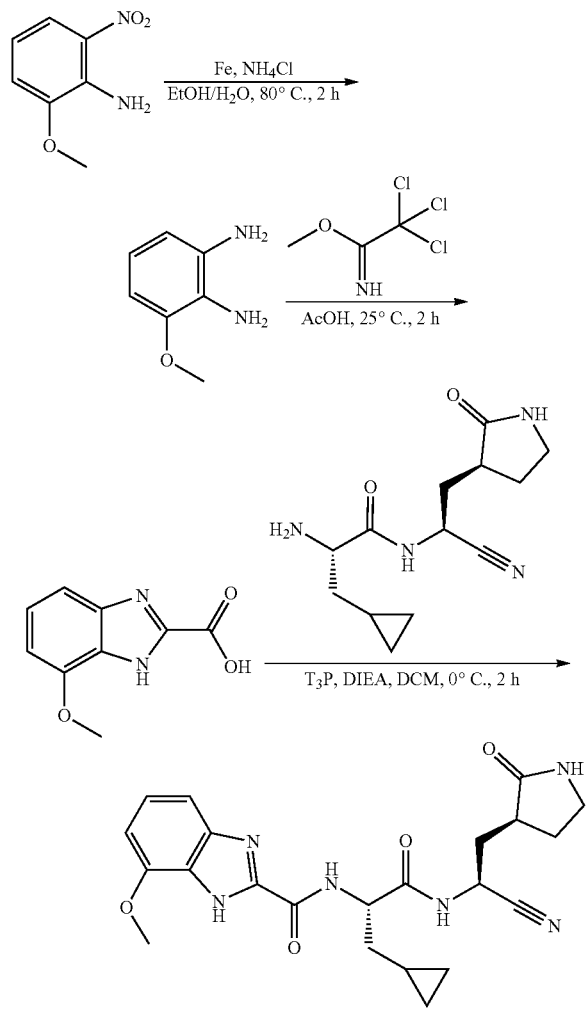

To a mixture of 2-methoxy-6-nitro-aniline (1 g, 5.95 mmol, 1.00 mL, 1 eq) in EtOH (12 mL) and H₂O (4 mL) was added NH₄Cl (1.59 g, 29.74 mmol, 5 eq) in one portion at 25° C., and then the reaction was heated to 80° C. Fe (1.66 g, 29.74 mmol, 5 eq) was added and stirred for 2 hours at 80° C. The reaction mixture was filtered and concentrated under reduced pressure to give a residue, and then diluted with H₂O (10 mL) and extracted with ethyl acetate 30 mL (10 mL*3). The combined organic layers were washed with brine 20 mL (20 mL*1), dried over Na₂SO₄, and filtered and concentrated under reduced pressure to give 3-methoxybenzene-1,2-diamine (770 mg, 5.02 mmol, 84.34% yield, 90% purity) as a black oil. MS (ESI) m/z 139.1 [M+H]⁺

Step 2: 7-methoxy-1H-benzimidazole-2-carboxylic acid

A mixture of 3-methoxybenzene-1,2-diamine (750 mg, 5.43 mmol, 1 eq) and methyl 2,2,2-trichloroethanimidoate (1.15 g, 6.51 mmol, 803.66 uL, 1.2 eq) in AcOH (8 mL) was added in one portion at 25° C. The mixture was stirred at 25° C. for 2 h. The reaction mixture was adjusted to neutral by Na₂CO₃ solution, and then diluted with H₂O (5 mL) and extracted with ethyl acetate (5 mL*3). The combined organic layers were washed with brine (10 mL*1) and concentrated under reduced pressure to give the crude product. The crude was purified by prep-HPLC (TFA condition) to give 7-methoxy-1H-benzimidazole-2-carboxylic acid (300 mg, 1.56 mmol, 28.76% yield) as a yellow solid. MS (ESI) m/z 193.1 [M+H]⁺ column: Phenomenex luna C18 100*40 mm*5 um; mobile phase: [water(0.1% TFA)-ACN]; B %: 20%-55%, 8 min Step 3: N-[(1S)-2-[[(1S)-1-cyano-2-[(3S)-2-oxopyrrolidin-3-yl]ethyl]amino]-1-(cyclopropylmethyl)-2-oxo-ethyl]-7-methoxy-1H-benzimidazole-2-carboxamide To a mixture of 7-methoxy-1H-benzimidazole-2-carboxylic acid (150 mg, 780.55 umol, 1 eq) and (2S)-2-amino-N-[(1S)-1-cyano-2-[(3S)-2-oxopyrrolidin-3-yl]ethyl]-3-cyclopropyl-propanamide (711.44 mg, 780.55 umol, 29% purity, 1 eq) in DCM (3 mL) was added DIEA (302.64 mg, 2.34 mmol, 407.88 uL, 3 eq) and T₃P (745.07 mg, 1.17 mmol, 696.33 uL, 50% purity, 1.5 eq) in one portion at 0° C. The mixture was stirred at 0° C. for 2 h. The reaction mixture was diluted with H₂O (5 mL) and then extracted with DCM (5 mL*3). The combined organic layers were washed with brine (8 mL*1), dried over Na₂SO₄, filtered and concentrated under reduced pressure to give the crude product. The crude was purified by prep-HPLC (neutral condition) to give N-[(1S)-2-[[(1S)-1-cyano-2-[(3S)-2-oxopyrrolidin-3-yl]ethyl]amino]-1-(cyclopropylmethyl)-2-oxo-ethyl]-7-methoxy-1H-benzimidazole-2-carboxamide (48 mg, 109.47 umol, 14.02% yield) as a white solid. MS (ESI) m/z 439.2 [M+H]⁺. column: Waters Xbridge Prep OBD C18 150*40 mm*10 um; mobile phase: [water (10 mM NH₄HCO₃)-ACN]; B %: 20%-40%, 8 min.

¹H NMR (400 MHz, DMSO-d₆) δ=13.29 (br s, 1H), 9.09-8.90 (m, 1H), 8.80-8.66 (m, 1H), 7.79-7.67 (m, 1H), 7.27-7.17 (m, 1H), 7.09 (d, J=8.2 Hz, 1H), 6.76 (d, J=7.9 Hz, 1H), 5.06-4.83 (m, 1H), 4.61-4.48 (m, 1H), 3.98-3.88 (m, 3H), 3.20-3.05 (m, 2H), 2.44-2.30 (m, 1H), 2.27-2.06 (m, 2H), 1.96-1.84 (m, 1H), 1.83-1.66 (m, 2H), 1.65-1.55 (m, 1H), 0.74 (br s, 1H), 0.40 (br d, J=8.2 Hz, 2H), 0.23-0.01 (m, 2H)

Example 45. Synthesis of Viral Protease Inhibitor Compound 163

Step 1: (S)-methyl 2-amino-3-((S)-2-oxopyrrolidin-3-yl)propanoate

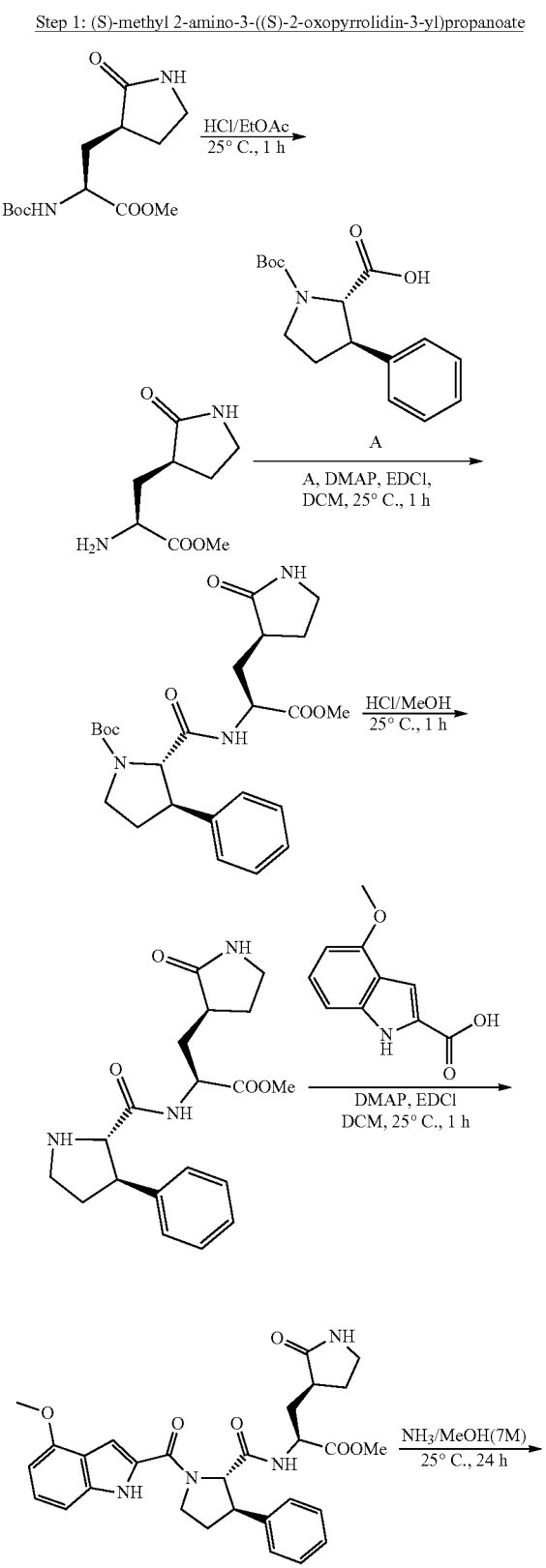

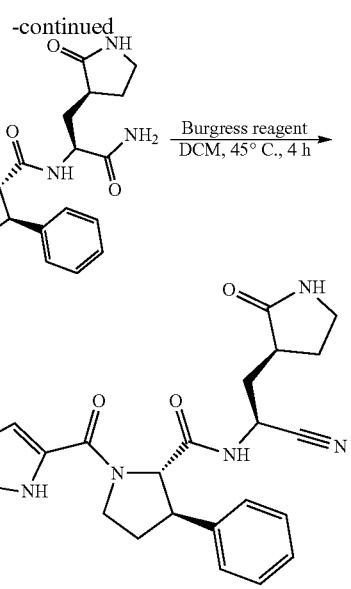

A solution of methyl (2S)-2-(tert-butoxycarbonylamino)-3-[(3S)-2-oxopyrrolidin-3-yl] propanoate (500 mg, 1.75 mmol, 1 eq) in HCl/EtOAc (3 mL) was stirred at 25° C. for 1 h. Upon completion, the mixture was concentrated in vacuum to afford (S)-methyl 2-amino-3-((S)-2-oxopyrrolidin-3-yl) propanoate (350 mg, crude, HCl) as a yellow gum.

Step 2: (2S,3R)-tert-butyl2-(((S)-1-methoxy-1-oxo-3-((S)-2-oxopyrrolidin-3-yl)propan-2-yl)carbamoyl)-3-phenylpyrrolidine-1-carboxylate To a solution of methyl (S)-methyl 2-amino-3-((S)-2-oxopyrrolidin-3-yl) propanoate (320 mg, 1.44 mmol, 1 eq, HCl) and (2S,3R)-1-tert-butoxycarbonyl-3-phenyl-pyrrolidine-2-carboxylic acid (502.43 mg, 1.72 mmol, 1.2 eq) in DCM (15 mL) was added DMAP (526.70 mg, 4.31 mmol, 3 eq) and EDCI (1.38 g, 7.19 mmol, 5 eq), and then the mixture was stirred at 25° C. for 1 h. Upon completion, the mixture was poured into water (45 mL) and was extracted with DCM (20 mL*3), then was concentrated in vacuum and was purified by column (SiO$_2$, PE:EA=1:1 to 0:1 and then DCM:MeOH=10:1 to 5:1) to afford (2S,3R)-tert-butyl2-(((S)-1-methoxy-1-oxo-3-((S)-2-oxopyrrolidin-3-yl) propan-2-yl)carbamoyl)-3-phenylpyrrolidine-1-carboxylate (500 mg, 544.03 umol, 37.86% yield, 50% purity) as a white solid. MS (ESI) m/z 460.3 [M+H]$^+$ Step 3: (S)-methyl 3-((S)-2-oxopyrrolidin-3-yl)-2-((2S,3R)-3-phenylpyrrolidine-2-carboxamido)propanoate A solution of (2S,3R)-tert-butyl2-(((S)-1-methoxy-1-oxo-3-((S)-2-oxopyrrolidin-3-yl)propan-2-yl) carbamoyl)-3-phenylpyrrolidine-1-carboxylate (500 mg, 1.09 mmol, 1 eq) in HCl/MeOH (4 M, 5 mL) was stirred at 25° C. for 1 h. Upon reaction completion, the mixture was concentrated in vacuum to afford (S)-methyl 3-((S)-2-oxopyrrolidin-3-yl)-2-((2S,3R)-3-phenylpyrrolidine-2-carboxamido) propanoate (340 mg, crude, HCl) as a light yellow solid.

Step 4: (S)-methyl2-((2S,3R)-1-(4-methoxy-1H-indole-2-carbonyl)-3-phenylpyrrolidine-2-carboxamido)-3-((S)-2-oxopyrrolidin-3-yl)propanoate To a solution of (S)-methyl 3-((S)-2-oxopyrrolidin-3-yl)-2-((2S,3R)-3-phenylpyrrolidine-2-carboxamido) propanoate (200 mg, 278.23 umol, 50% purity, 1 eq) and 4-methoxy-1H-indole-2-carboxylic acid (63.83 mg, 333.87 umol, 1.2 eq) in DCM (5 mL) was added DMAP (101.97 mg, 834.68 umol, 3 eq) and EDCI (106.67 mg, 556.45 umol, 2 eq), and then the mixture was stirred at 25° C. for 1 h. Upon the reaction completion, the mixture was quenched by water (30 mL) and was extracted with DCM (10 mL*3). The resultant was concentrated in vacuum and was purified by prep-TLC (SiO$_2$, ethyl acetate=1) to afford (S)-methyl 2-((2S,3R)-1-(4-methoxy-1H-indole-2-carbonyl)-3-phenylpyrrolidine-2-carboxamido)-3-((S)-2-oxopyrrolidin-3-yl)propanoate (130 mg, 216.51 umol, 77.82% yield, 88.7% purity) as a white solid. MS (ESI) m/z 533.3 [M+H]$^+$ Step 5: (2S,3R)-N-((S)-1-amino-1-oxo-3-((S)-2-oxopyrrolidin-3-yl)propan-2-yl)-1-(4-methoxy-1H-indole-2-carbonyl)-3-phenylpyrrolidine-2-carboxamide A solution of (S)-methyl 2-((2S,3R)-1-(4-methoxy-1H-indole-2-carbonyl)-3-phenylpyrrolidine-2-carboxamido)-3-((S)-2-oxopyrrolidin-3-yl)propanoate (180 mg, 337.97 umol, 1 eq) in NH$_3$/MeOH (7M, 7.00 mL) was stirred at 25° C. for 24 h. Upon the reaction completion, the mixture was concentrated in vacuum to afford (2S,3R)-N-((S)-1-amino-1-oxo-3-((S)-2-oxopyrrolidin-3-yl) propan-2-yl)-1-(4-methoxy-1H-indole-2-carbonyl)-3-phenylpyrrolidine-2-carboxamide (160 mg, crude) as a white solid. MS (ESI) m/z 518.3 [M+H]$^+$ Step 6: (2S,3R)-N-((S)-1-cyano-2-((S)-2-oxopyrrolidin-3-yl)ethyl)-1-(4-methoxy-1H-indole-2-carbonyl)-3-phenylpyrrolidine-2-carboxamide To a solution of (2S,3R)-N-((S)-1-amino-1-oxo-3-((S)-2-oxopyrrolidin-3-yl)propan-2-yl)-1-(4-methoxy-1H-indole-2-carbonyl)-3-phenylpyrrolidine-2-carboxamide (160 mg, 309.13 umol, 1 eq) in DCM (5 mL) was added Burgess reagent (294.67 mg, 1.24 mmol, 4 eq), and then the mixture was stirred at 45° C. for 4 h. Upon the reaction completion, the mixture was quenched by water (3 mL) and was dried by blowing N$_2$ and was purified by prep-HPLC (column: Waters Xbridge BEH C18 100*25 mm*5 um; mobile phase: [water (10 mM NH$_4$HCO$_3$)-ACN]; B %: 25%-55%, 10 min) to afford (2S,3R)-N-((S)-1-cyano-2-((S)-2-oxopyrrolidin-3-yl)ethyl)-1-(4-methoxy-1H-indole-2-carbonyl)-3-phenylpyrrolidine-2-carboxamide (45 mg, 89.18 umol, 28.85% yield, 99% purity) as a white solid. MS (ESI) m/z 500.2 [M+H]$^+$.

$^1$H NMR (400 MHz, DMSO-d$_6$) δ ppm 11.69-11.50 (m, 1H), 9.21-8.79 (m, 1H), 7.76-7.49 (m, 1H), 7.42-7.20 (m, 5H), 7.17-6.72 (m, 3H), 6.57-6.39 (m, 1H), 5.00-4.76 (m, 1H), 4.47 (d, J=6.8 Hz, 1H), 4.17-3.72 (m, 5H), 3.55-3.38 (m, 1H), 3.17-2.77 (m, 2H), 2.46-2.34 (m, 2H), 2.30-2.01 (m, 3H), 1.79-1.31 (m, 2H).

$^1$H NMR (400 MHz, DMSO-d$_6$, 273+80K) δ ppm 11.33 (s, 1H), 8.75 (br s, 1H), 7.43-7.22 (m, 6H), 7.17-7.03 (m, 2H), 6.96 (s, 1H), 6.52 (d, J=7.3 Hz, 1H), 4.99-4.87 (m, 1H), 4.63 (s, 1H), 4.08 (s, 2H), 3.90 (s, 3H), 3.50 (q, J=6.8 Hz, 1H), 3.17-3.06 (m, 2H), 2.42 (s, 2H), 2.25-2.03 (m, 3H), 1.84-1.57 (m, 2H).

Example 46. Synthesis of Viral Protease Inhibitor Compound 191

Step 1: methyl (2S)-2-amino-3-[(3S)-2-oxopyrrolidin-3-yl]propanoate

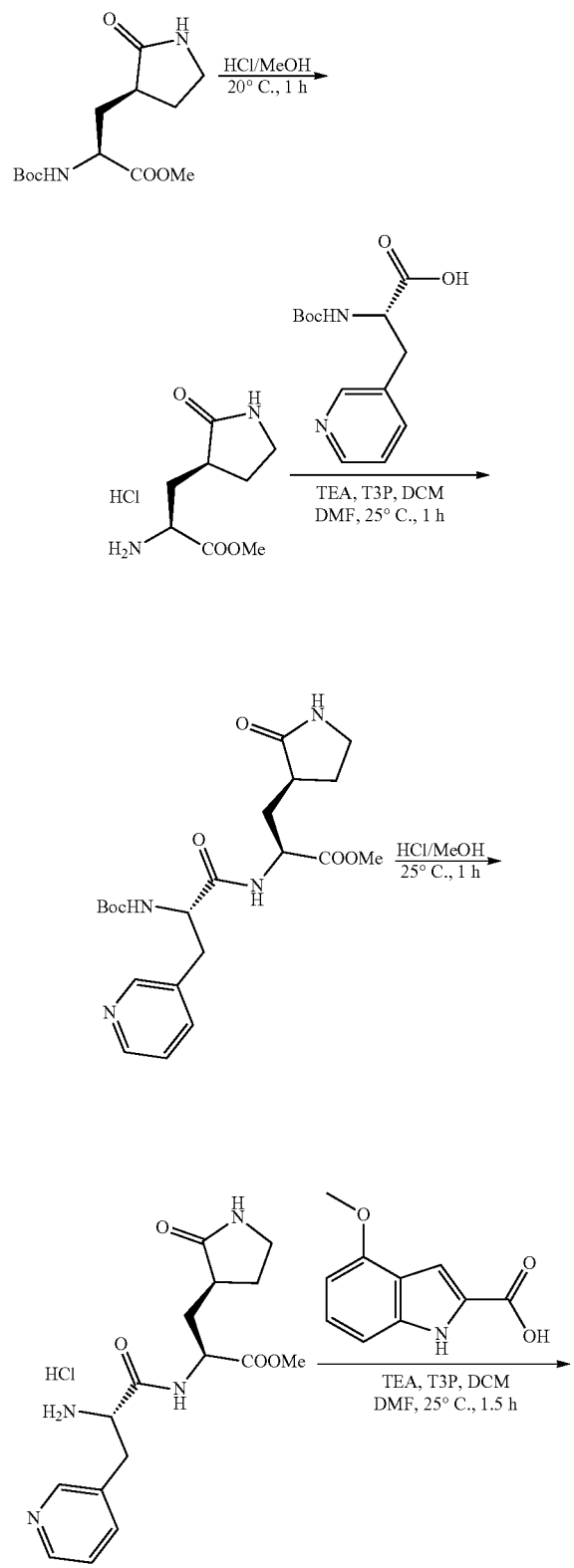

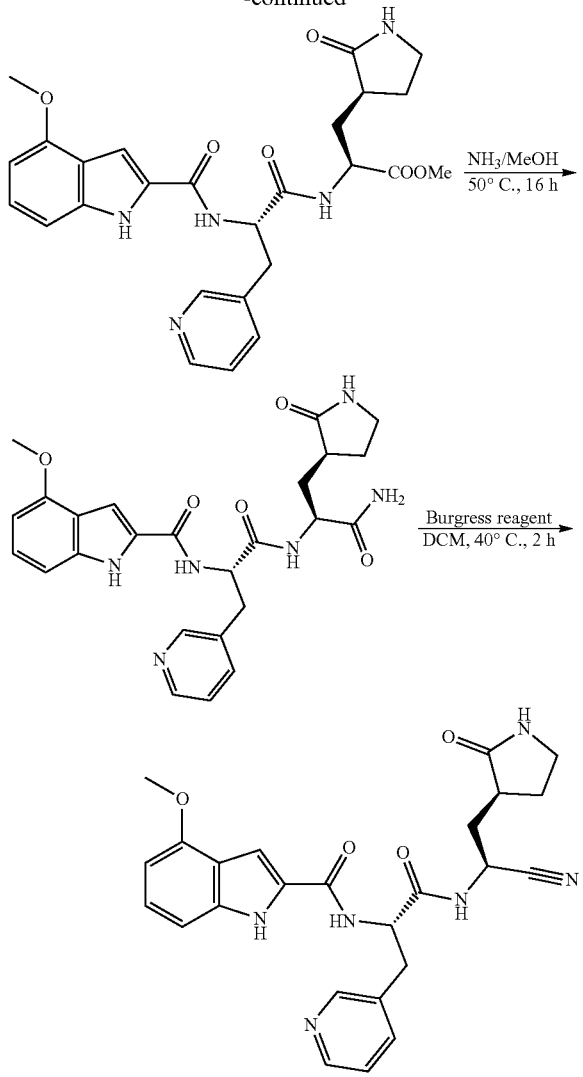

A mixture of methyl (2S)-2-(tert-butoxycarbonylamino)-3-[(3S)-2-oxopyrrolidin-3-yl]propanoate (500 mg, 1.75 mmol, 1 eq) in HCl/MeOH (4 M, 7 mL, 16.03 eq) was stirred at 25° C. for 1 h. Upon completion, the mixture was concentrated under reduced pressure to give a residue, and then the residue was dissolved with DCM (10 mL*3). The resultant was concentrated under reduced pressure to get afford methyl (2S)-2-amino-3-[(3S)-2-oxopyrrolidin-3-yl]propanoate (320 mg, crude) as a white oil. MS (ESI) m/z 187.2 [M+H]$^+$.

Step 2: methyl (2S)-2-[[(2S)-2-(tert-butoxycarbonylamino)-3-(3-pyridyl)propanoyl]amino]-3-[(3S)-2-oxopyrrolidin-3-yl]propanoate A mixture of methyl (2S)-2-amino-3-[(3S)-2-oxopyrrolidin-3-yl]propanoate (320 mg, 1.44 mmol, 1.2 eq, HCl) in DCM (4 mL) and DMF (1 mL) added (2S)-2-(tert-butoxycarbonylamino)-3-(3-pyridyl)propanoic acid (318.91 mg, 1.20 mmol, 1 eq), TEA (727.10 mg, 7.19 mmol, 1.00 mL, 6 eq) and T3P (1.14 g, 1.80 mmol, 1.07 mL, 50% purity, 1.5 eq) was stirred at 25° C. for 1 h. Upon completion, the reaction mixture was diluted with water (10 mL) and extracted with DCM (3 mL*3). The combined organic layers were dried over Na$_2$SO$_4$, filtered and concentrated under reduced pressure to give a residue. The residue was purified by silica gel chromatography (SiO$_2$, DCM:MeOH=9:1) and TLC (SiO$_2$, DCM:MeOH=10:1) to get the product methyl (2S)-2-[[(2S)-2-(tert-butoxycarbonylamino)-3-(3-pyridyl)propanoyl]amino]-3-[(3S)-2-oxopyrrolidin-3-yl]propanoate (490 mg, 1.13 mmol, 94.17% yield) as a yellow oil. MS (ESI) m/z 435.3 [M+H]$^+$.

Step 3: methyl (2S)-2-[[(2S)-2-amino-3-(3-pyridyl)propanoyl]amino]-3-[(3S)-2-oxopyrrolidin-3-yl]propanoate A mixture of methyl (2S)-2-[[(2S)-2-(tert-butoxycarbonylamino)-3-(3-pyridyl)propanoyl]amino]-3-[(3S)-2-oxopyrrolidin-3-yl]propanoate (450 mg, 1.04 mmol, 1 eq) in HCl/MeOH (4 M, 6 mL, 23.17 eq) was stirred at 25° C. for 1 h. Upon completion, the mixture was concentrated under reduced pressure to give a residue, was dissolved with DCM (10 mL*3) and concentrated under reduced pressure to get the product methyl (2S)-2-[[(2S)-2-amino-3-(3-pyridyl)propanoyl]amino]-3-[(3S)-2-oxopyrrolidin-3-yl]propanoate (340 mg, crude) as white oil. MS (ESI) m/z 335.1 [M+H]$^+$.

Step 4: methyl (2S)-2-[[(2S)-2-[(4-methoxy-1H-indole-2-carbonyl)amino]-3-(3-pyridyl)propanoyl]amino]-3-[(3S)-2-oxopyrrolidin-3-yl]propanoate A mixture of methyl (2S)-2-[[(2S)-2-amino-3-(3-pyridyl)propanoyl]amino]-3-[(3S)-2-oxopyrrolidin-3-yl]propanoate (340 mg, 916.86 umol, 1 eq, HCl) in DCM (2 mL) and DMF (2 mL) then added 4-methoxy-1H-indole-2-carboxylic acid (210.35 mg, 1.10 mmol, 1.2 eq), TEA (556.66 mg, 5.50 mmol, 765.70 uL, 6 eq) and T3P (875.18 mg, 1.38 mmol, 817.93 uL, 50% purity, 1.5 eq) was stirred at 25° C. for 1.5 h. Upon completion, the reaction mixture was diluted with water (10 mL) and extracted with DCM (3 mL*3). The combined organic layers were dried over Na$_2$SO$_4$, filtered and concentrated under reduced pressure to give a residue. The residue was purified by prep-TLC (SiO$_2$, DCM:MeOH=10:1) and TLC (SiO$_2$, DCM:MeOH=10:1) to get the product methyl (2S)-2-[[(2S)-2-[(4-methoxy-1H-indole-2-carbonyl)amino]-3-(3-pyridyl)propanoyl]amino]-3-[(3S)-2-oxopyrrolidin-3-yl]propanoate (180 mg, 354.65 umol, 38.68% yield) as yellow solid. MS (ESI) m/z 508.2 [M+H]$^+$.

Step 5: N-[(1S)-2-[[(1S)-2-amino-2-oxo-1-[[(3S)-2-oxopyrrolidin-3-yl]methyl]ethyl]amino]-2-oxo-1-(3-pyridylmethyl)ethyl]-4-methoxy-1H-indole-2-carboxamide A mixture of methyl (2S)-2-[[(2S)-2-[(4-methoxy-1H-indole-2-carbonyl)amino]-3-(3-pyridyl)propanoyl]amino]-3-[(3S)-2-oxopyrrolidin-3-yl]propanoate (165 mg, 325.10 umol, 1 eq) in NH$_3$/MeOH (7 M, 5 mL, 107.66 eq) was stirred at 50° C. for 16 h. Upon completion, the reaction mixture was concentrated under reduced pressure to get the product N-[(1S)-2-[[(1S)-2-amino-2-oxo-1-[[(3S)-2-oxopyrrolidin-3-yl]methyl]ethyl]amino]-2-oxo-1-(3-pyridylmethyl)ethyl]-4-methoxy-1H-indole-2-carboxamide (150 mg, crude) as yellow solid. MS (ESI) m/z 493.2 [M+H]$^+$.

Step 6: N-[(1S)-2-[[(1S)-1-cyano-2-[(3S)-2-oxopyrrolidin-3-yl]ethyl]amino]-2-oxo-1-(3-pyridylmethyl)ethyl]-4-methoxy-1H-indole-2-carboxamide To a mixture of N-[(1S)-2-[[(1S)-2-amino-2-oxo-1-[[(3S)-2-oxopyrrolidin-3-yl]methyl]ethyl]amino]-2-oxo-1-

(3-pyridylmethyl)ethyl]-4-methoxy-1H-indole-2-carboxamide (126 mg, 255.82 umol, 1 eq) in DCM (3 mL) was added methoxycarbonyl-(triethylammonio)sulfonyl-azanide (243.86 mg, 1.02 mmol, 4 eq), and the reaction was stirred at 40° C. for 2 h. Upon completion, the mixture were quenched with water (1 mL) and blow-dried with N₂. The residue was purified by prep-HPLC (column: Waters X bridge BEH C18 100*25 mm*5 um; mobile phase: [water (10 mM NH₄HCO₃)-ACN]; B %: 15%-45%, 10 min) to afford N-[(1S)-2-[[(1S)-1-cyano-2-[(3S)-2-oxopyrrolidin-3-yl]ethyl]amino]-2-oxo-1-(3-pyridylmethyl)ethyl]-4-methoxy-1H-indole-2-carboxamide (30.52 mg, 64.32 umol, 25.14% yield, 100% purity) as a white solid. MS (ESI) m/z 475.2 [M+H]$^+$. $^1$H NMR (400 MHz, METHANOL-d₄) δ=8.50 (d, J=1.5 Hz, 1H), 8.41-8.34 (m, 1H), 7.80 (br d, J=7.9 Hz, 1H), 7.37 (dd, J=4.9, 7.8 Hz, 1H), 7.21 (s, 1H), 7.13 (d, J=7.7 Hz, 1H), 7.00 (d, J=8.2 Hz, 1H), 6.50 (d, J=7.7 Hz, 1H), 5.03 (dd, J=6.0, 10.0 Hz, 1H), 4.76 (s, 1H), 3.92 (s, 3H), 3.30-3.21 (m, 3H), 3.17 (dd, J=8.8, 13.9 Hz, 1H), 2.56 (dq, J=5.5, 9.3 Hz, 1H), 2.36-2.21 (m, 2H), 1.96-1.73 (m, 2H).

Example 47. Synthesis of Viral Protease Inhibitor Compound 213

Step 1: (S)-methyl 2-amino-3-((S)-2-oxopyrrolidin-3-yl)propanoate

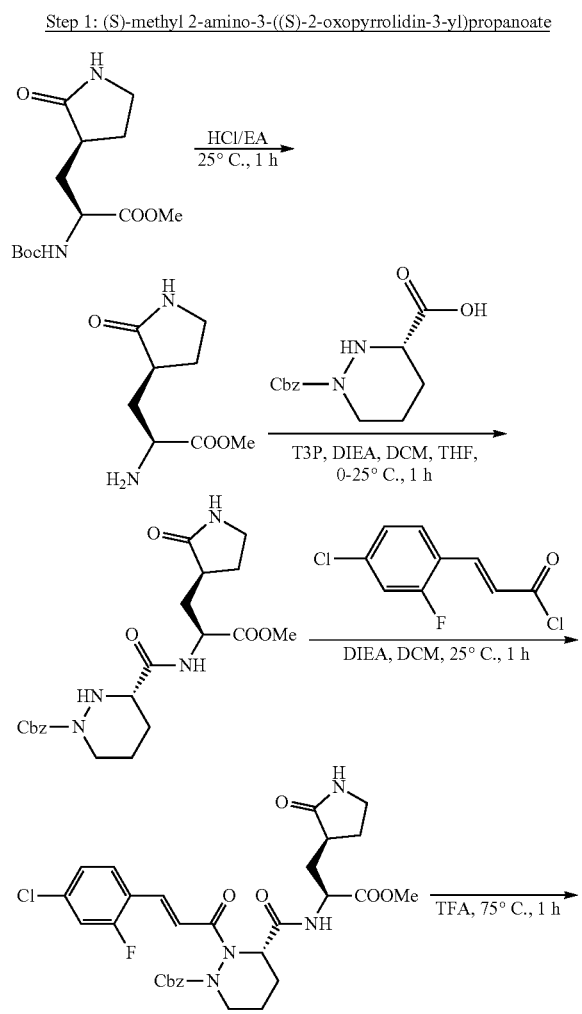

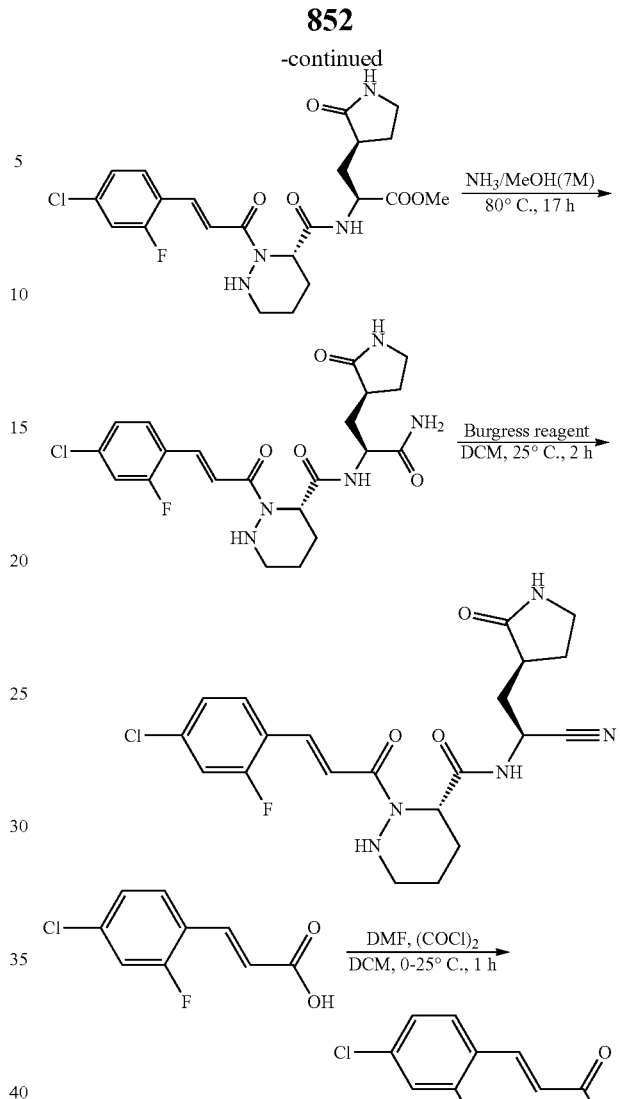

Methyl (2S)-2-(tert-butoxycarbonylamino)-3-[(3S)-2-oxopyrrolidin-3-yl]propanoate (501 mg, 1.75 mmol, 1 eq) in HCl/EtOAc (4 M, 10.02 mL, 22.91 eq) was stirred at 25° C. for 1 h. Upon completion, the solution was concentrated to remove the HCl/EA. The crude was used to next step directly and without further purification. Methyl (2S)-2-amino-3-[(3S)-2-oxopyrrolidin-3-yl] propanoate (300 mg, crude) was obtained as yellow oil.

Step 2: (S)-benzyl 3-(((S)-1-methoxy-1-oxo-3-((S)-2-oxopyrrolidin-3-yl)propan-2-yl)carbamoyl)tetrahydropyridazine-1(2H)-carboxylate A solution of methyl (2S)-2-amino-3-[(3S)-2-oxopyrrolidin-3-yl]propanoate (295.93 mg, 1.59 mmol, 1.4 eq) and (3S)-1-benzyloxycarbonylhexahydropyridazine-3-carboxylic acid (300 mg, 1.14 mmol, 1 eq) in DCM (2 mL)/THF (2 mL) was cooled to 0° C., and then the T3P (1.08 g, 1.70 mmol, 1.01 mL, 50% purity, 1.5 eq) and DIEA (440.14 mg, 3.41 mmol, 593.18 uL, 3 eq) were added. After stirring at 25° C. for 13 h, the solution was diluted with H₂O (20 mL) and extracted with ethyl acetate (30 mL*3). The combined organic phase was dried over Na₂SO₄, filtrated and concentrated to give the crude. The crude was used to next step directly and without further purification. Benzyl (3S)-3-[[(1S)-2-methoxy-2-oxo-1-[[(3S)-2-oxopyrrolidin-3-yl]methyl] ethyl] carbamoyl] hexahydropyridazine-1-carboxylate (455 mg, crude) was obtained as yellow oil. MS (ESI) m/z 433.1 [M+H]$^+$.

Step 3: (S)-benzyl 2-((E)-3-(4-chloro-2-fluorophenyl)acryloyl)-3-(((S)-1-methoxy-1-oxo-3-((S)-2-oxopyrrolidin-3-yl)propan-2-yl)carbamoyl)tetrahydropyridazine-1(2H)-carboxylate To a solution of benzyl (3S)-3-[[(1S)-2-methoxy-2-oxo-1-[[(3S)-2-oxopyrrolidin-3-yl]methyl]ethyl]carbamoyl] hexahydropyridazine-1-carboxylate (200 mg, 462.46 umol, 1 eq) in DCM (2 mL) was added the DIEA (119.54 mg, 924.92 umol, 161.10 uL, 2 eq), (E)-3-(4-chloro-2-fluorophenyl)prop-2-enoyl chloride (121.56 mg, 554.95 umol, 1.2 eq), and then the solution was stirred at 25° C. for 1 h. Upon completion, the solution was diluted with H$_2$O (10 mL), extracted with DCM (20 mL*3), the combined organic phase was dried over Na$_2$SO$_4$, filtrated and concentrated to give the crude. The residue was purified by prep-TLC (SiO$_2$, DCM:MeOH=10:1). Benzyl (3S)-2-[(E)-3-(4-chloro-2-fluoro-phenyl) prop-2-enoyl]-3-[[(1S)-2-methoxy-2-oxo-1-[[(3S)-2-oxopyrrolidin-3-yl] methyl] ethyl] carbamoyl] hexahydropyridazine-1-carboxylate (160 mg, 248.88 umol, 53.82% yield, 95.67% purity) was obtained as yellow oil. MS (ESI) m/z 433.1 [M+H]$^+$.

Step 4: (S)-methyl 2-((S)-2-((E)-3-(4-chloro-2-fluorophenyl)acryloyl)hexahydropyridazine-3-carboxamido)-3-((S)-2-oxopyrrolidin-3-yl)propanoate Benzyl (3S)-2-[(E)-3-(4-chloro-2-fluoro-phenyl)prop-2-enoyl]-3-[[(1S)-2-methoxy-2-oxo-1-[[(3S)-2-oxopyrrolidin-3-yl]methyl]ethyl]carbamoyl]hexahydropyridazine-1-carboxylate (160 mg, 260.14 umol, 1 eq) in TFA (5 mL) was stirred at 75° C. for 1 h. Upon completion, the solution was concentrated to remove the TFA, diluted with the solution of NaHCO$_3$, and extracted with ethyl acetate (20 mL*3). The combined organic phase was dried over Na$_2$SO$_4$, filtered and concentrated to give the crude. The crude was used to next step directly and without further purification. Methyl (2S)-2-[[(3S)-2-[(E)-3-(4-chloro-2-fluoro-phenyl) prop-2-enoyl] hexahydropyridazine-3-carbonyl] amino]-3-[(3S)-2-oxopyrrolidin-3-yl] propanoate (80 mg, crude) was obtained as yellow solid. MS (ESI) m/z 481.0 [M+H]$^+$.

Step 5: (S)-N-((S)-1-amino-1-oxo-3-((S)-2-oxopyrrolidin-3-yl)propan-2-yl)-2-((E)-3-(4-chloro-2-fluorophenyl)acryloyl)hexahydropyridazine-3-carboxamide Methyl (2S)-2-[[(3S)-2-[(E)-3-(4-chloro-2-fluoro-phenyl)prop-2-enoyl]hexahydropyridazine-3-carbonyl]amino]-3-[(3S)-2-oxopyrrolidin-3-yl]propanoate (80 mg, 166.35 umol, 1 eq) in ammonia (7 M, 4.00 mL, 168.32 eq) was stirred at 80° C. for 17 h. Upon completion, the solution was concentrated to remove the MeOH. The crude was used for the next step directly and without further purification. (3S)-N-[(1S)-2-amino-2-oxo-1-[[(3S)-2-oxopyrrolidin-3-yl] methyl] ethyl]-2-[(E)-3-(4-chloro-2-fluoro-phenyl) prop-2-enoyl] hexahydropyridazine-3-carboxamide (75 mg, crude) was obtained as yellow oil. MS (ESI) m/z 481.0 [M+H]$^+$.

Step 6: (S)-2-((E)-3-(4-chloro-2-fluorophenyl)acryloyl)-N-((S)-1-cyano-2-((S)-2-oxopyrrolidin-3-yl)ethyl)hexahydropyridazine-3-carboxamide To a solution of (3S)-N-[(1S)-2-amino-2-oxo-1-[[(3S)-2-oxopyrrolidin-3-yl]methyl]ethyl]-2-[(E)-3-(4-chloro-2-fluoro-phenyl)prop-2-enoyl]hexahydropyridazine-3-carboxamide (75 mg, 160.98 umol, 1 eq) in DCM (0.5 mL) was added the Burgess reagent (76.72 mg, 321.95 umol, 2 eq) and the solution was stirred at 25° C. for 2 h. Upon completion, the solution was concentrated to remove the DCM. The residue was purified by prep-HPLC (neutral condition). Column: Phenomenex Gemini-NX 80*40 mm*3 um; mobile phase: [water (10 mM NH4HCO3)-ACN]; B %: 25%-45%, 8 min. (3S)-2-[(E)-3-(4-chloro-2-fluoro-phenyl)prop-2-enoyl]-N-[(1S)-1-cyano-2-[(3S)-2-oxopyrrolidin-3-yl]ethyl]hexahydropyridazine-3-carboxamide (20 mg, 44.65 umol, 27.74% yield, 100% purity) was obtained as a white solid. $^1$H NMR (400 MHz, METHANOL-d$_4$) δ=7.79-7.60 (m, 3H), 7.32-7.22 (m, 2H), 5.17 (dd, J=2.2, 6.0 Hz, 1H), 5.07 (dd, J=6.4, 9.7 Hz, 1H), 3.38-3.32 (m, 2H), 3.12 (br d, J=13.7 Hz, 1H), 2.90-2.74 (m, 1H), 2.56 (dq, J=5.8, 9.0 Hz, 1H), 2.44-2.14 (m, 3H), 2.08-1.79 (m, 3H), 1.75-1.53 (m, 2H). MS (ESI) m/z 448.2 [M+H]$^+$.

Step 7: (E)-3-(4-chloro-2-fluorophenyl)acryloyl chloride

To a solution of (E)-3-(4-chloro-2-fluoro-phenyl)prop-2-enoic acid (120 mg, 598.22 umol, 1 eq) in DCM (0.5 mL) was added the DMF (437.26 ug, 5.98 umol, 0.46 uL, 0.01 eq), and the reaction was cooled to 0° C. (COCl)$_2$ (151.86 mg, 1.20 mmol, 104.73 uL, 2 eq) was added and the solution was stirred at 25° C. for 1 h. Upon completion, the solution was concentrated to remove the DCM and give the crude. The crude was used to next step directly and without further purification. (E)-3-(4-chloro-2-fluoro-phenyl)prop-2-enoyl chloride (125 mg, crude) was obtained as white solid.

Example 48. Synthesis of Viral Protease Inhibitor Compound 203

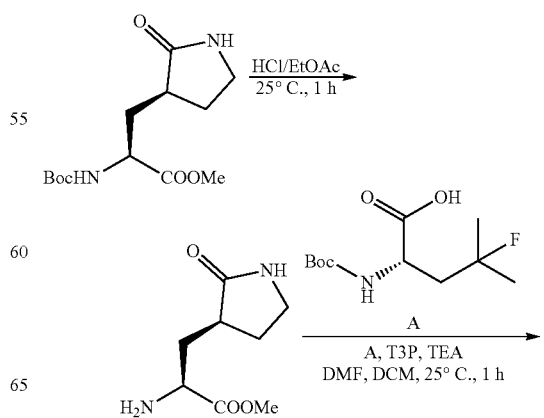

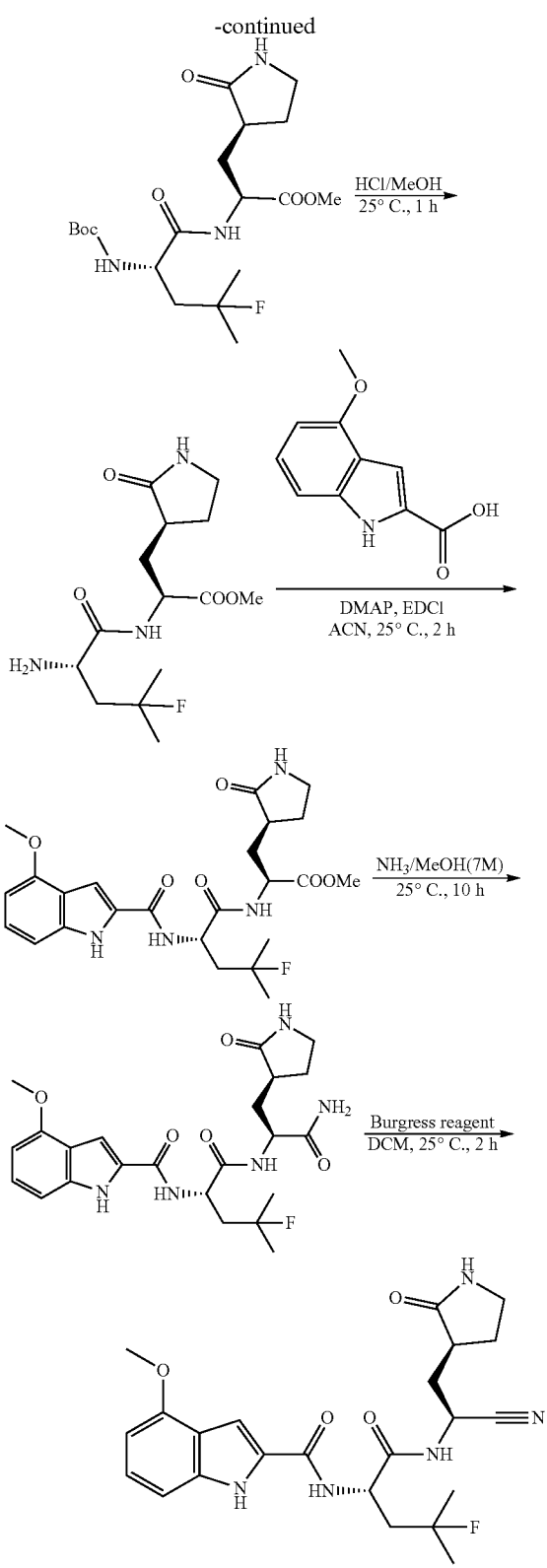

Step 1: (S)-methyl 2-amino-3-((S)-2-oxopyrrolidin-3-yl)propanoate

A solution of (S)-methyl 2-((tert-butoxycarbonyl)amino)-3-((S)-2-oxopyrrolidin-3-yl)propanoate (600 mg, 2.10 mmol, 1 eq) in HCl/EtOAc (20 mL) was stirred at 25° C. for 1 h. Upon completion, the mixture was concentrated in the vacuum to give a crude product (S)-methyl 2-amino-3-((S)-2-oxopyrrolidin-3-yl)propanoate (530 mg, crude) as yellow solid. MS (ESI) m/z 187.1 [M+H]$^+$ Step 2: (S)-methyl2-((S)-2-((tert-butoxycarbonyl)amino)-4-fluoro-4-methylpentanamido)-3-((S)-2-oxopyrrolidin-3-yl)propanoate To a solution of methyl (S)-methyl 2-amino-3-((S)-2-oxopyrrolidin-3-yl)propanoate (530 mg, 2.85 mmol, 1 eq) in DMF (1 mL) and DCM (10 mL) was added (S)-2-((tert-butoxycarbonyl)amino)-4-fluoro-4-methylpentanoic acid (710.44 mg, 2.85 mmol, 1 eq), T3P (2.36 g, 3.71 mmol, 2.20 mL, 50% purity, 1.3 eq) and TEA (865.17 mg, 8.55 mmol, 1.19 mL, 3 eq), and the mixture was stirred at 25° C. for 1 h. Upon completion, the mixture was quenched by addition H$_2$O (50 mL) and then extracted with EtOAc (20 mL*3). The combined organic layers were washed with brine (20 mL), dried over Na$_2$SO$_4$, filtered and concentrated under reduced pressure to give a residue and was purified by column chromatography (SiO$_2$, petroleum ether:ethyl acetate=0:1) to give the crude product (S)-methyl 2-((S)-2-((tert-butoxycarbonyl)amino)-4-fluoro-4-methylpentanamido)-3-((S)-2-oxopyrrolidin-3-yl)propanoate (730 mg, 1.57 mmol, 55.19% yield, 89.95% purity) was yellow oil. MS (ESI) m/z 418.2 [M+H]$^+$ Step 3: (S)-methyl2-((S)-2-amino-4-fluoro-4-methylpentanamido)-3-((S)-2-oxopyrrolidin-3-yl)propanoate A solution of (S)-methyl 2-((S)-2-((tert-butoxycarbonyl)amino)-4-fluoro-4-methylpentanamido)-3-((S)-2-oxopyrrolidin-3-yl)propanoate (530.00 mg, 1.27 mmol, 1 eq) in HCl/MeOH (20 mL) was stirred at 25° C. for 1 h. Upon completion, the reaction was concentrated in the vacuum to give the crude product (S)-methyl 2-((S)-2-amino-4-fluoro-4-methylpentanamido)-3-((S)-2-oxopyrrolidin-3-yl)propanoate (500 mg, crude) was yellow solid. MS (ESI) m/z 318.2 [M+H]$^+$ Step 4: (S)-methyl2-((S)-4-fluoro-2-(4-methoxy-1H-indole-2-carboxamido)-4-methylpentanamido)-3-((S)-2-oxopyrrolidin-3-yl)propanoate To a solution of (S)-methyl 2-((S)-2-amino-4-fluoro-4-methylpentanamido)-3-((S)-2-oxopyrrolidin-3-yl)propanoate (500.00 mg, 1.58 mmol, 1 eq) in ACN (20 mL) was added 4-methoxy-1H-indole-2-carboxylic acid (301.21 mg, 1.58 mmol, 1 eq), DMAP (384.96 mg, 3.15 mmol, 2 eq), EDCI (604.06 mg, 3.15 mmol, 2 eq) and the mixture was stirred at 25° C. for 1 h. Upon completion, the residue was poured into H$_2$O (50 mL) and was extracted with EtOAc (20 mL*3). The combined organic phase was washed with brine (10 mL*2), dried with Na$_2$SO$_4$, filtered and concentrated in vacuum and was purified by column chromatography (SiO$_2$, petroleum ether:ethyl acetate=0:1) to give product (S)-methyl 2-((S)-4-fluoro-2-(4-methoxy-1H-indole-2-carboxamido)-4-methylpentanamido)-3-((S)-2-oxopyrrolidin-3-yl)propanoate (340 mg, 652.80 umol, 41.43% yield, 94.18% purity). MS (ESI) m/z 491.2 [M+H]$^+$ Step5: N-((S)-1-(((S)-1-amino-1-oxo-3-((S)-2-oxopyrrolidin-3-yl)propan-2-yl)amino)-4-fluoro-4-methyl-1-oxopentan-2-yl)-4-methoxy-1H-indole-2-carboxamide A solution of (S)-methyl 2-((S)-4-fluoro-2-(4-methoxy-1H-indole-2-carboxamido)-4-methylpentanamido)-3-((S)-

2-oxopyrrolidin-3-yl)propanoate (330 mg, 672.75 umol, 1 eq) in NH₃/MeOH (7 M, 10 mL, 104.05 eq) was stirred at 25° C. for 10 h. Upon, completion, the mixture was concentrated in the vacuum, to give crude product N-((S)-1-(((S)-1-amino-1-oxo-3-((S)-2-oxopyrrolidin-3-yl)propan-2-yl)amino)-4-fluoro-4-methyl-1-oxopentan-2-yl)-4-methoxy-1H-indole-2-carboxamide (280 mg, crude) as a yellow solid. MS (ESI) m/z 476.2 [M+H]⁺

Step6: N-((S)-1-(((S)-1-cyano-2-((S)-2-oxopyrrolidin-3-yl)ethyl)amino)-4-fluoro-4-methyl-1-oxopentan-2-yl)-4-methoxy-1H-indole-2-carboxamide To a solution of N-((S)-1-(((S)-1-amino-1-oxo-3-((S)-2-oxopyrrolidin-3-yl)propan-2-yl)amino)-4-fluoro-4-methyl-1-oxopentan-2-yl)-4-methoxy-1H-indole-2-carboxamide (220 mg, 462.66 umol, 1 eq) in DCM (10 mL) was added Burgess reagent (1.10 g, 4.63 mmol, 10 eq) and the mixture was stirred at 25° C. for 1 h. Upon completion, the mixture was concentrated in the vacuum and was purified by prep-HPLC (column: Phenomenex Gemini-NX C18 75*30 mm*3 um; mobile phase: [water(0.05% NH₃H₂O+10 mM NH₄HCO₃)-ACN]; B %: 20%-50%, 8 min) to give product N-((S)-1-(((S)-1-cyano-2-((S)-2-oxopyrrolidin-3-yl)ethyl)amino)-4-fluoro-4-methyl-1-oxopentan-2-yl)-4-methoxy-1H-indole-2-carboxamide (10 mg, 21.86 umol, 4.72% yield, 100% purity). MS (ESI) m/z 458.2 [M+H]⁺¹H NMR (400 MHz, MeOD-d₄) δ=7.22 (s, 1H), 7.18-7.12 (m, 1H), 7.03-7.02 (m, 1H), 6.52-6.50 (m, 1H), 5.06-5.03 (m, 1H), 4.74-4.72 (m, 1H), 3.93 (s, 3H), 3.29-3.19 (m, 2H), 2.32-2.31 (m, 1H), 2.36-2.25 (m, 3H), 2.24-2.14 (m, 1H), 1.93-1.76 (m, 2H), 1.48-1.46 (m, 3H), 1.43-1.41 (m, 3H)

Example 49. Synthesis of Viral Protease Inhibitor Compound 223

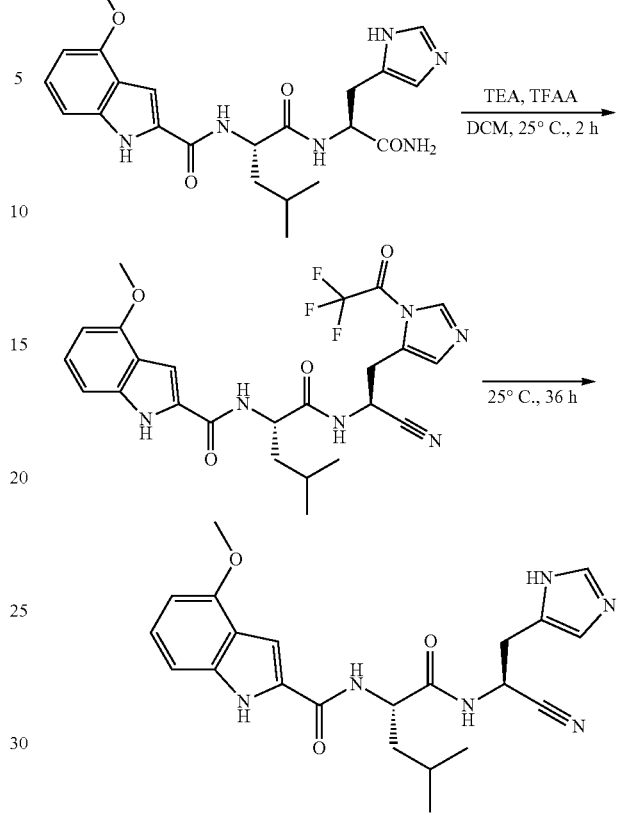

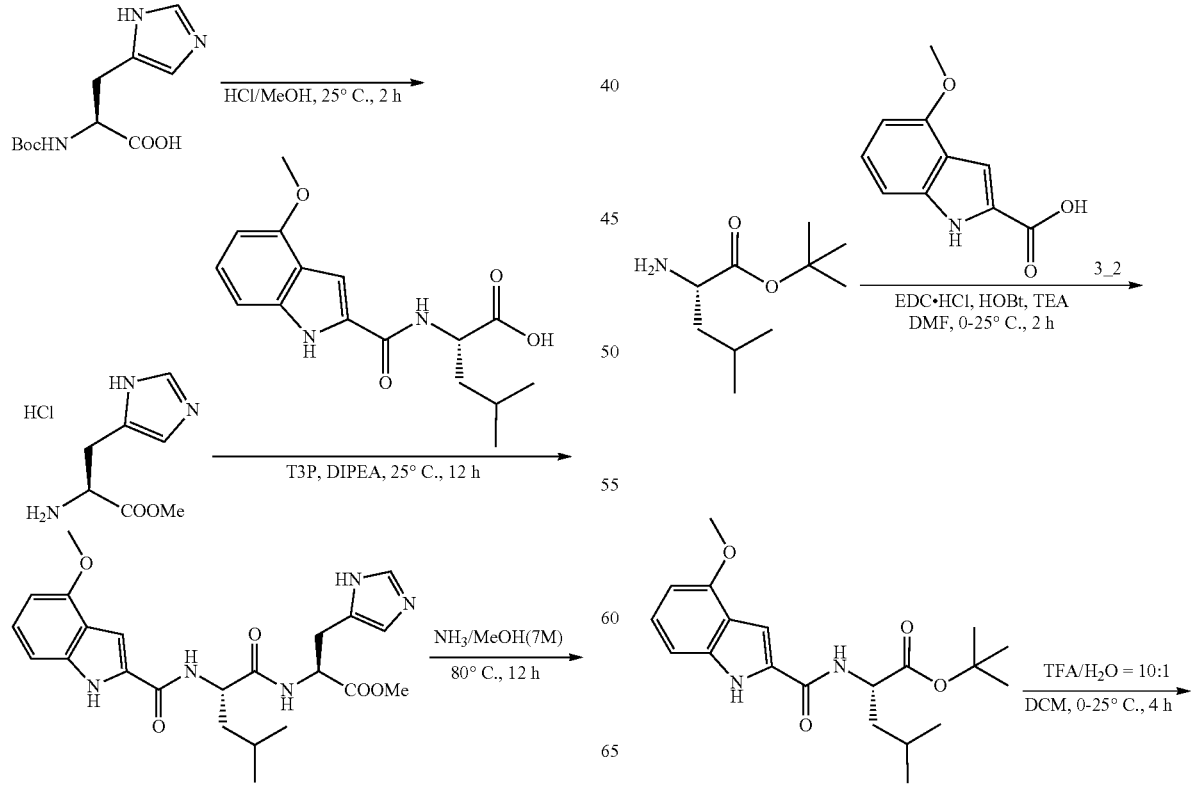

-continued

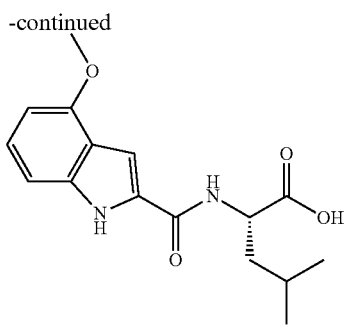

Step 1: methyl (2S)-2-amino-3-(1H-imidazol-5-yl) propanoate

To the solution of (2S)-2-(tert-butoxycarbonylamino)-3-(1H-imidazol-5-yl)propanoic acid (0.5 g, 1.96 mmol, 1 eq) in MeOH (0.6 mL) was added HCl/MeOH (4 M, 4.90 mL, 10 eq) at 25° C. The reaction mixture was stirred at 25° C. for 12 h. The reaction mixture was concentrated to afford methyl (2S)-2-amino-3-(1H-imidazol-5-yl) propanoate (400 mg, crude, HCl) as white solid, which was used directly next step. MS (ESI) m/z 170.1 [M+H]$^+$

Step 2: methyl (2S)-3-(1H-imidazol-5-yl)-2-[[(2S)-2-[(4-methoxy-1H-indole-2-carbonyl)amino]-4-methyl-pentanoyl]amino]propanoate To a mixture of (2S)-2-[(4-methoxy-1H-indole-2-carbonyl)amino]-4-methyl-pentanoic acid (741.86 mg, 1.77 mmol, 1 eq, TFA) and methyl (2S)-2-amino-3-(1H-imidazol-5-yl)propanoate (0.3 g, 1.77 mmol, 1 eq, HCl), DIPEA (1.15 g, 8.87 mmol, 1.54 mL, 5 eq) in THF (0.3 mL) and DCM (0.3 mL) was added T3P (1.69 g, 2.66 mmol, 1.58 mL, 50% purity, 1.5 eq) at 0° C. under N$_2$. The mixture was stirred at 25° C. for 12 h. The reaction mixture was added saturated sodium bicarbonate solution (10 mL) and extracted with DCM (10 mL*2) to get the organic phase. The organic phase was washed with brine (3 mL*3) and dried over anhydrous sodium sulfate and concentrated to get the crude product. Methyl (2S)-3-(1H-imidazol-5-yl)-2-[[(2S)-2-[(4-methoxy-1H-indole-2-carbonyl)amino]-4-methyl-pentanoyl]amino]propanoate (300 mg, crude) was obtained as the white solid and used directly next step. MS (ESI) m/z 456.2 [M+H]$^+$. 1H NMR (400 MHz, METHANOL-d$_4$) δ ppm 7.48 (s, 1H), 7.27 (s, 1H), 7.11-7.18 (m, 1H), 7.02 (d, J=8.16 Hz, 1H), 6.85 (s, 1H), 6.51 (d, J=7.72 Hz, 1H), 4.60-4.71 (m, 2H), 3.93 (s, 3H), 3.68 (s, 3H), 3.00-3.17 (m, 3H), 1.62-1.78 (m, 3H), 0.97 (dd, J=13.78, 6.06 Hz, 6H)

Step 3: N-[(1S)-1-[[(1S)-2-amino-1-(1H-imidazol-5-ylmethyl)-2-oxo-ethyl]carbamoyl]-3-methyl-butyl]-4-methoxy-1H-indole-2-carboxamide To methyl (2S)-3-(1H-imidazol-5-yl)-2-[[(2S)-2-[(4-methoxy-1H-indole-2-carbonyl)amino]-4-methyl-pentanoyl]amino]propanoate (200 mg, 439.07 umol, 1 eq) was added NH$_3$/MeOH (7 M, 11.76 mL, 187.56 eq) in one portion at 25° C. under N$_2$. The mixture was stirred at 80° C. and stirred for 12 h. The reaction mixture was cooled to 25° C. and concentrated to get the crude product. N-[(1S)-1-[[(1S)-2-amino-1-(1H-imidazol-5-ylmethyl)-2-oxo-ethyl]carbamoyl]-3-methyl-butyl]-4-methoxy-1H-indole-2-carboxamide (170 mg, 378.83 umol, 86.28% yield, 98.16% purity) was obtained as the light yellow solid and used directly next step. MS (ESI) m/z 441.2 [M+H]$^+$

Step 4: N-[(1S)-1-[[(1S)-1-cyano-2-(1H-imidazol-5-yl)ethyl]carbamoyl]-3-methyl-butyl]-4-methoxy-1H-indole-2-carboxamide To a mixture of N-[(1S)-1-[[(1S)-2-amino-1-(1H-imidazol-5-ylmethyl)-2-oxo-ethyl]carbamoyl]-3-methyl-butyl]-4-methoxy-1H-indole-2-carboxamide (140 mg, 317.82 umol, 1 eq) in DCM (2 mL) was added TFAA (133.51 mg, 635.65 umol, 88.41 uL, 2 eq) at 25° C. under N$_2$. The mixture was stirred at 25° C. for 2 h. The reaction mixture was concentrated to get the crude product, which turned into N-[(1S)-1-[[(1S)-1-cyano-2-(1H-imidazol-5-yl)ethyl]carbamoyl]-3-methyl-butyl]-4-methoxy-1H-indole-2-carboxamide after 36 h in storage. The residue was purified by prep-HPLC to afford N-[(1S)-1-[[(1S)-1-cyano-2-(1H-imidazol-5-yl)ethyl]carbamoyl]-3-methyl-butyl]-4-methoxy-1H-indole-2-carboxamide (23.89 mg, 56.31 umol, 17.72% yield, 99.581% purity) as a white solid. MS (ESI) m/z 423.2 [M+H]$^+$ Prep-HPLC condition: column: Waters Xbridge BEH C18 100*25 mm*5 um; mobile phase: [water (10 mM NH$_4$HCO$_3$)-ACN]; B %: 25%-55%, 10 min; $^1$H NMR (400 MHz, METHANOL-d$_4$) δ ppm 7.58 (s, 1H), 7.30 (s, 1H), 7.12-7.21 (m, 1H), 6.99-7.09 (m, 2H), 6.52 (d, J=7.72 Hz, 1H), 5.05 (t, J=7.06 Hz, 1H), 4.61 (br dd, J=9.70, 4.85 Hz, 1H), 3.94 (s, 3H), 3.06-3.21 (m, 2H), 1.60-1.83 (m, 3H), 0.99 (dd, J=13.89, 6.17 Hz, 6H)

Step 5: tert-butyl (2S)-2-[(4-methoxy-1H-indole-2-carbonyl)amino]-4-methyl-pentanoate To a mixture of 4-methoxy-1H-indole-2-carboxylic acid (5 g, 26.15 mmol, 1 eq) and tert-butyl (2S)-2-amino-4-methyl-pentanoate (5.88 g, 31.38 mmol, 1.2 eq, HCl), EDCI (6.52 g, 34.00 mmol, 1.3 eq), HOBt (4.59 g, 34.00 mmol, 1.3 eq) in DMF (30 mL) was added TEA (7.94 g, 78.46 mmol, 10.92 mL, 3 eq) in one portion at 25° C. under N$_2$. The mixture was stirred at 25° C. and stirred for 2 h. The reaction mixture was added water (90 mL) and extracted with ethyl acetate (25 mL*3) to get the organic phase. The organic phase was washed with 5% citric acid (25 mL) and 5% aqueous solution of sodium bicarbonate (25 mL) and dried over anhydrous sodium sulfate, filtered and concentrated to get the product. The residue was purified by column chromatography (SiO$_2$, petroleum ether:ethyl acetate=30:1 to 10:1). Tert-butyl (2S)-2-[(4-methoxy-1H-indole-2-carbonyl)amino]-4-methyl-pentanoate (5.93 g, 16.45 mmol, 62.91% yield) was obtained as light yellow solid. MS (ESI) m/z 361.2 [M+H]$^+$ $^1$H NMR (400 MHz, CHLOROFORM-d) δ ppm 9.25 (br s, 1H), 7.10-7.16 (m, 1H), 6.93-7.00 (m, 2H), 6.56 (br d, J=8.31 Hz, 1H), 6.44 (d, J=7.70 Hz, 1H), 4.66 (td, J=8.50, 5.14 Hz, 1H), 3.88 (s, 3H), 1.62-1.75 (m, 2H), 1.57-1.62 (m, 1H), 1.42 (s, 9H), 0.92 (dd, J=6.17, 3.85 Hz, 6H).

Step 6: (2S)-2-[(4-methoxy-1H-indole-2-carbonyl)amino]-4-methyl-pentanoic acid To a mixture of tert-butyl (2S)-2-[(4-methoxy-1H-indole-2-carbonyl)amino]-4-methyl-pentanoate (2.00 g, 5.55 mmol, 1 eq) in DCM (8 mL) was added TFA (10.27 g, 90.04 mmol, 6.67 mL, 16.23 eq) and H$_2$O (666.67 mg, 37.01 mmol, 666.67 uL, 6.67 eq) in one portion at 0° C. under N$_2$. The mixture was stirred at 25° C. and stirred for 4 h. The reaction mixture was concentrated to get the crude product.

(2S)-2-[(4-methoxy-1H-indole-2-carbonyl)amino]-4-methyl-pentanoic acid (2.24 g, 5.35 mmol, 96.50% yield, TFA) was obtained as the yellow solid and used directly next step. MS (ESI) m/z 305.1 [M+H]+

Example 50. Synthesis of Viral Protease Inhibitor Compound 237

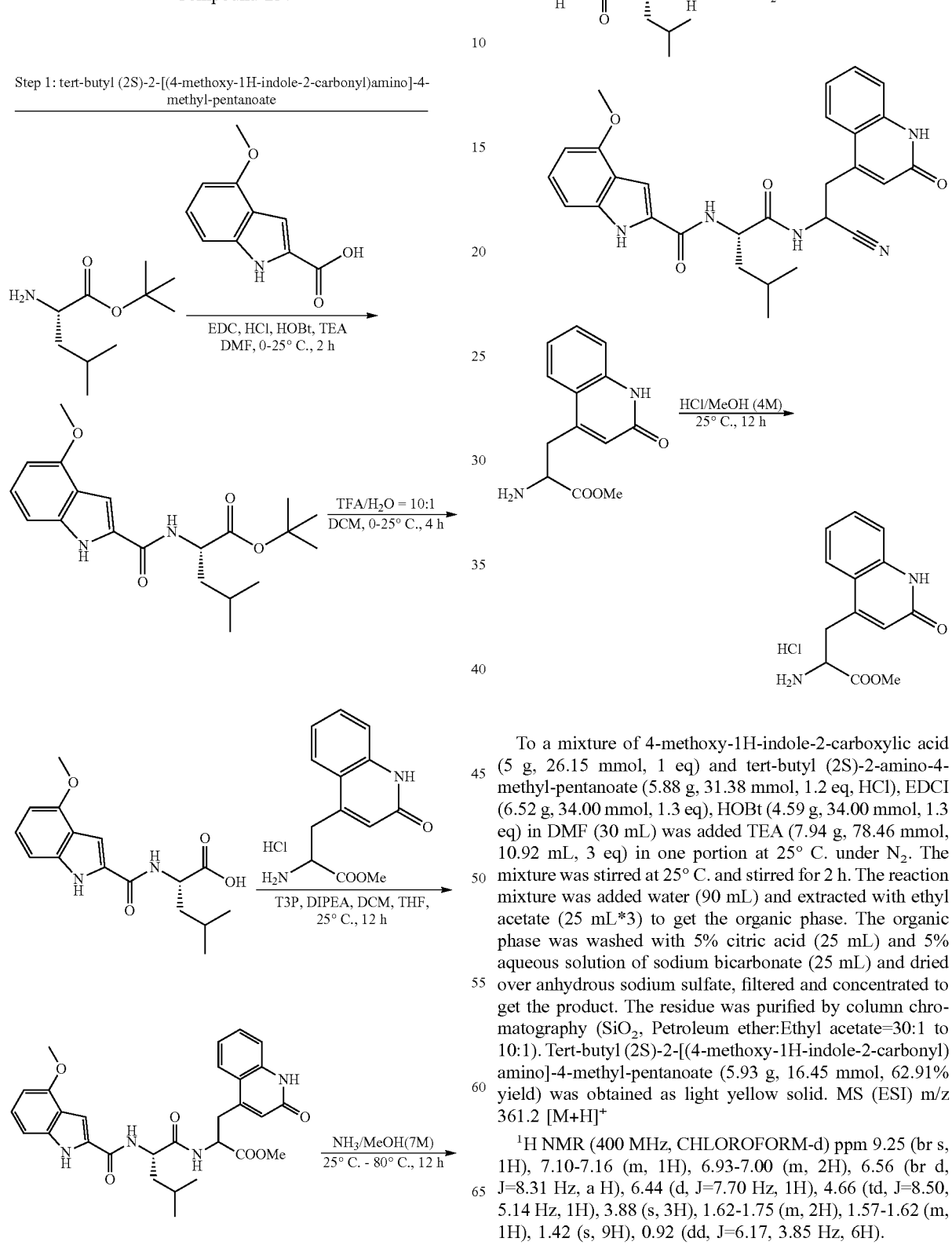

To a mixture of 4-methoxy-1H-indole-2-carboxylic acid (5 g, 26.15 mmol, 1 eq) and tert-butyl (2S)-2-amino-4-methyl-pentanoate (5.88 g, 31.38 mmol, 1.2 eq, HCl), EDCI (6.52 g, 34.00 mmol, 1.3 eq), HOBt (4.59 g, 34.00 mmol, 1.3 eq) in DMF (30 mL) was added TEA (7.94 g, 78.46 mmol, 10.92 mL, 3 eq) in one portion at 25° C. under $N_2$. The mixture was stirred at 25° C. and stirred for 2 h. The reaction mixture was added water (90 mL) and extracted with ethyl acetate (25 mL*3) to get the organic phase. The organic phase was washed with 5% citric acid (25 mL) and 5% aqueous solution of sodium bicarbonate (25 mL) and dried over anhydrous sodium sulfate, filtered and concentrated to get the product. The residue was purified by column chromatography (SiO$_2$, Petroleum ether:Ethyl acetate=30:1 to 10:1). Tert-butyl (2S)-2-[(4-methoxy-1H-indole-2-carbonyl)amino]-4-methyl-pentanoate (5.93 g, 16.45 mmol, 62.91% yield) was obtained as light yellow solid. MS (ESI) m/z 361.2 [M+H]+

$^1$H NMR (400 MHz, CHLOROFORM-d) ppm 9.25 (br s, 1H), 7.10-7.16 (m, 1H), 6.93-7.00 (m, 2H), 6.56 (br d, J=8.31 Hz, a H), 6.44 (d, J=7.70 Hz, 1H), 4.66 (td, J=8.50, 5.14 Hz, 1H), 3.88 (s, 3H), 1.62-1.75 (m, 2H), 1.57-1.62 (m, 1H), 1.42 (s, 9H), 0.92 (dd, J=6.17, 3.85 Hz, 6H).

Step 2: (2S)-2-[(4-methoxy-1H-indole-2-carbonyl)amino]-4-methyl-pentanoic acid To a mixture of tert-butyl (2S)-2-[(4-methoxy-1H-indole-2-carbonyl)amino]-4-methyl-pentanoate (2.00 g, 5.55 mmol, 1 eq) in DCM (8 mL) was added TFA (10.27 g, 90.04 mmol, 6.67 mL, 16.23 eq) and $H_2O$ (666.67 mg, 37.01 mmol, 666.67 uL, 6.67 eq) in one portion at 0° C. under $N_2$. The mixture was stirred at 25° C. and stirred for 4 h. The reaction mixture was concentrated to afford (2S)-2-[(4-methoxy-1H-indole-2-carbonyl)amino]-4-methyl-pentanoic acid (2.24 g, 5.35 mmol, 96.50% yield, TFA) as the yellow solid, which was used directly next step. MS (ESI) m/z 305.1 $[M+H]^+$

Step 3: methyl 2-[[(2S)-2-[(4-methoxy-1H-indole-2-carbonyl)amino]-4-methyl-pentanoyl]amino]-3-(2-oxo-1H-quinolin-4-yl)propanoate To a mixture of (2S)-2-[(4-methoxy-1H-indole-2-carbonyl)amino]-4-methyl-pentanoic acid (568.23 mg, 1.36 mmol, 1.2 eq, TFA) and methyl 2-amino-3-(2-oxo-1H-quinolin-4-yl)propanoate (320 mg, 1.13 mmol, 1 eq, HCl), DIPEA (731.40 mg, 5.66 mmol, 985.72 uL, 5 eq) in THF (1 mL) and DCM (1 mL) was added T3P (1.08 g, 1.70 mmol, 1.01 mL, 50% purity, 1.5 eq) at 0° C. under $N_2$. The mixture was stirred at 25° C. for 12 h. The reaction mixture was added with saturated sodium bicarbonate solution (10 mL) and extracted with DCM (10 mL*2) to get the organic phase. The organic phase was concentrated to get the crude product. The residue was purified by prep-HPLC. Methyl 2-[[(2S)-2-[(4-methoxy-1H-indole-2-carbonyl)amino]-4-methyl-pentanoyl]amino]-3-(2-oxo-1H-quinolin-4-yl)propanoate (0.2 g, 375.53 umol, 33.18% yield) was obtained as the white solid. MS (ESI) m/z 533.2 $[M+H]^+$ Prep-HPLC condition: column: Kromasil C18 (250*50 mm*10 um); mobile phase: [water (10 mM $NH_4HCO_3$)-ACN]; B %: 30%-60%, 10 min

Step 4: N-[(1S)-1-[[2-amino-2-oxo-1-[(2-oxo-1H-quinolin-4-yl)methyl]ethyl]carbamoyl]-3-methyl-butyl]-4-methoxy-1H-indole-2-carboxamide To a mixture of methyl 2-[[(2S)-2-[(4-methoxy-1H-indole-2-carbonyl)amino]-4-methyl-pentanoyl] amino]-3-(2-oxo-1H-quinolin-4-yl)propanoate (200.00 mg, 375.53 umol, 1 eq) was added $NH_3$/MeOH (7 M, 10.00 mL, 186.41 eq) in one portion at 25° C. under $N_2$. The mixture was stirred at 80° C. for 12 h. The reaction mixture was cooled to 25° C. and concentrated to afford N-[(1S)-1-[[2-amino-2-oxo-1-[(2-oxo-1H-quinolin-4-yl)methyl]ethyl]carbamoyl]-3-methyl-butyl]-4-methoxy-1H-indole-2-carboxamide (180 mg, 326.21 umol, 86.87% yield, 93.8% purity) as the light yellow solid and used directly next step. MS (ESI) m/z 518.2 $[M+H]^+$

Step 5: N-[(1S)-1-[[1-cyano-2-(2-oxo-1H-quinolin-4-yl)ethyl]carbamoyl]-3-methyl-butyl]-4-methoxy-1H-indole-2-carboxamide To a mixture of N-[(1S)-1-[[2-amino-2-oxo-1-[(2-oxo-1H-quinolin-4-yl)methyl]ethyl]carbamoyl]-3-methyl-butyl]-4-methoxy-1H-indole-2-carboxamide (90 mg, 173.89 umol, 1 eq) in DCM (5 mL) was added Burgess reagent (207.19 mg, 869.44 umol, 5 eq) in one portion at 25° C. under $N_2$. The mixture was stirred at 25° C. for 12 h. The reaction mixture was concentrated and purified by prep-HPLC. N-[(1S)-1-[[1-cyano-2-(2-oxo-1H-quinolin-4-yl)ethyl] carbamoyl]-3-methyl-butyl]-4-methoxy-1H-indole-2-carboxamide (20.74 mg, 41.13 umol, 23.66% yield, 99.079% purity) was obtained as the white solid. MS (ESI) m/z 500.2 $[M+H]^+$ Prep-HPLC condition: column: Waters Xbridge BEH C18 100*25 mm*5 um; mobile phase: [water (10 mM $NH_4HCO_3$)-ACN]; B %: 30%-65%, 10 min $^1$H NMR (400 MHz, METHANOL-$d_4$) δ ppm 7.93 (br d, J=8.16 Hz, 1H), 7.50-7.58 (m, 1H), 7.28-7.40 (m, 2H), 7.26 (dd, J=11.47, 0.66 Hz, 1H), 7.11-7.19 (m, 1H), 7.04 (dd, J=8.27, 4.08 Hz, 1H), 6.59-6.70 (m, 1H), 6.46-6.56 (m, 1H), 5.24-5.34 (m, 1H), 4.53 (td, J=10.31, 5.18 Hz, 1H), 3.93 (d, J=4.41 Hz, 3H), 3.40-3.59 (m, 3H), 1.72 (ddd, J=15.16, 9.87, 5.18 Hz, 1H), 1.53-1.66 (m, 2H), 1.40-1.50 (m, 1H), 0.87-1.01 (m, 5H)

Step 6: methyl2-amino-3-(2-oxo-1H-quinolin-4-yl)propanoate

To 2-amino-3-(2-oxo-1H-quinolin-4-yl)propanoic acid (400 mg, 1.72 mmol, 1 eq) was added HCl/MeOH (4 M, 4.31 mL, 10 eq) in one portion at 25° C. under $N_2$. The mixture was stirred at 25° C. and stirred for 1 h. The reaction mixture was concentrated to get the product. Methyl 2-amino-3-(2-oxo-1H-quinolin-4-yl)propanoate (370 mg, crude, HCl) was obtained as the white solid and used directly next step.

Example 51. Synthesis of Viral Protease Inhibitor Compound 241

Step 1: methyl 2-amino-3-(1H-pyrazol-3-yl)propanoate

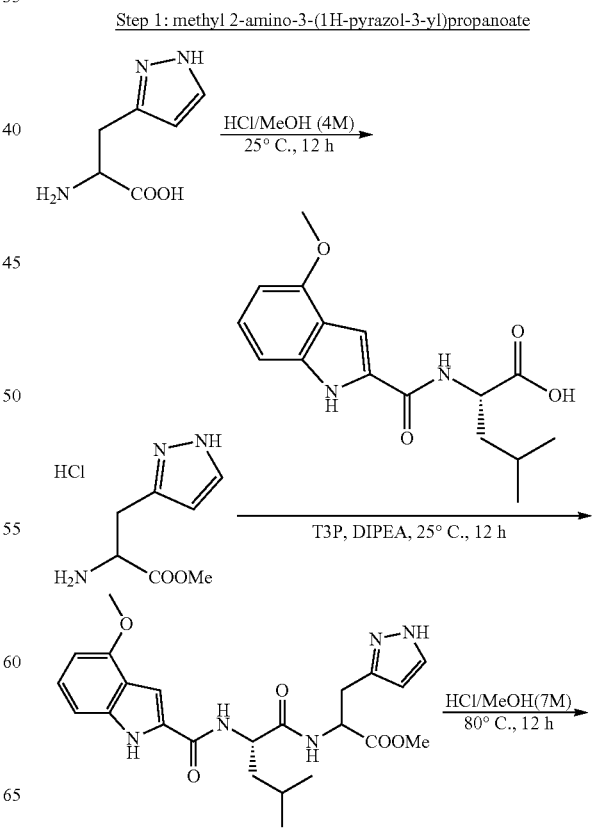

-continued

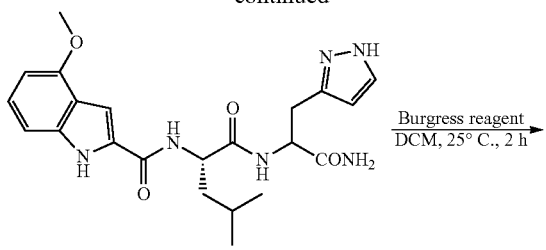

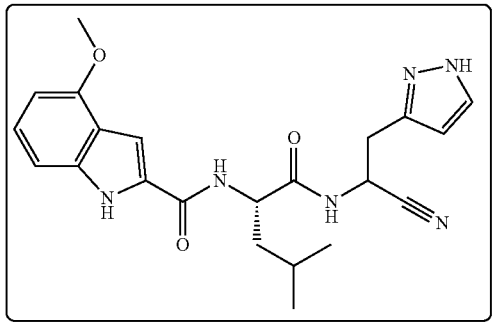

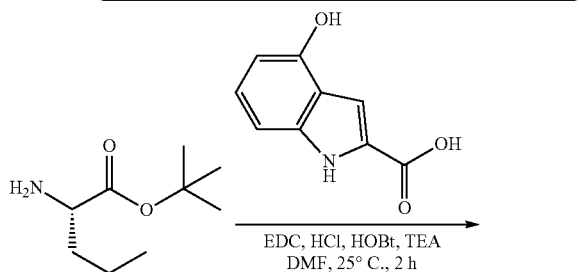

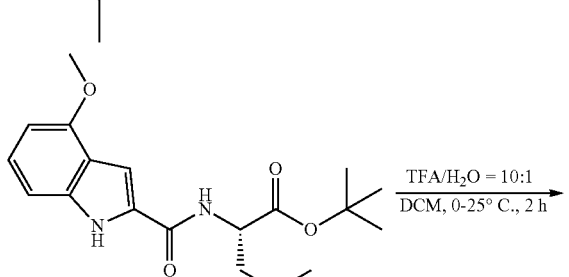

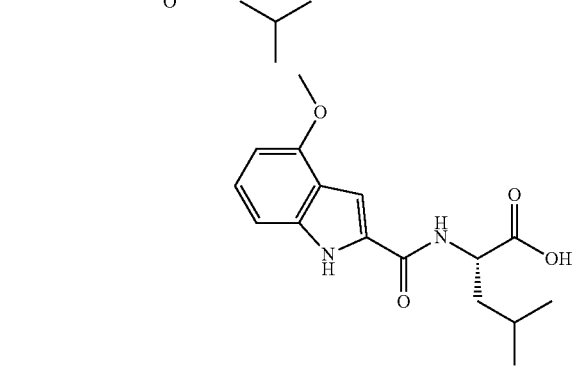

To 2-amino-3-(1H-pyrazol-3-yl)propanoic acid (0.5 g, 2.19 mmol, 1 eq, 2HCl) was added HCl/MeOH (4 M, 17.01 mL, 31.03 eq) in one portion at 25° C. under $N_2$. The mixture was stirred at 25° C. for 12 h. The reaction mixture was concentrated to get the crude product. Methyl 2-amino-3-(1H-pyrazol-3-yl)propanoate (530 mg, crude, 2HCl) was obtained as the yellow solid and used directly next step. MS (ESI) m/z 170.1 [M+H]$^+$ Step 2: methyl 2-[[(2S)-2-[(4-methoxy-1H-indole-2-carbonyl)amino]-4-methyl-pentanoyl]amino]-3-(1H-pyrazol-3-yl)propanoate To a mixture of (2S)-2-[(4-methoxy-1H-indole-2-carbonyl)amino]-4-methyl-pentanoic acid (377.12 mg, 1.24 mmol, 1 eq) and methyl 2-amino-3-(1H-pyrazol-3-yl)propanoate (300 mg, 1.24 mmol, 1 eq, 2HCl), DIPEA (800.75 mg, 6.20 mmol, 1.08 mL, 5 eq) in THF (0.9 mL) and DCM (0.9 mL) was added T3P (1.18 g, 1.86 mmol, 1.11 mL, 50% purity, 1.5 eq) at 0° C. under $N_2$. The mixture was stirred at 25° C. and stirred for 12 h. The reaction mixture was added saturated sodium bicarbonate solution (10 mL) and extracted with DCM (10 mL*2) to get the organic phase. The organic phase was concentrated to get the crude product. The residue was purified by pre-HPLC. Methyl 2-[[(2S)-2-[(4-methoxy-1H-indole-2-carbonyl)amino]-4-methyl-pentanoyl]amino]-3-(1H-pyrazol-3-yl)propanoate (130 mg, 285.40 umol, 23.03% yield) was obtained as the white solid. MS (ESI) m/z 456.2 [M+H]$^+$ Prep-HPLC condition: column: Phenomenex Gemini-NX 80*40 mm*3 um; mobile phase: [water (10 mM $NH_4HCO_3$)-ACN]; B %: 25%-45%, 8 min Step 3: N-[(1S)-1-[[2-amino-2-oxo-1-(1H-pyrazol-3-ylmethyl)ethyl]carbamoyl]-3-methyl-butyl]-4-methoxy-1H-indole-2-carboxamide To a mixture of methyl 2-[[(2S)-2-[(4-methoxy-1H-indole-2-carbonyl)amino]-4-methyl-pentanoyl] amino]-3-(1H-pyrazol-3-yl)propanoate (100 mg, 219.54 umol, 1 eq) was added $NH_3$/MeOH (7 M, 3.33 mL, 106.28 eq) in one portion at 25° C. under $N_2$. The mixture was stirred at 80° C. for 12 h. The reaction mixture was cooled to 25° C. and concentrated to get the product. N-[(1S)-1-[[2-amino-2-oxo-1-(1H-pyrazol-3-ylmethyl)ethyl]carbamoyl]-3-methyl-butyl]-4-methoxy-1H-indole-2-carboxamide (95 mg, crude) was obtained as the light yellow solid and used directly next step. MS (ESI) m/z 441.2 [M+H]$^+$ Step 4: N-[(1S)-1-[[1-cyano-2-(1H-pyrazol-3-yl)ethyl]carbamoyl]-3-methyl-butyl]-4-methoxy-1H-indole-2-carboxamide To a mixture of N-[(1S)-1-[[2-amino-2-oxo-1-(1H-pyrazol-3-ylmethyl)ethyl]carbamoyl]-3-methyl-butyl]-4-methoxy-1H-indole-2-carboxamide (95 mg, 215.67 umol, 1 eq) TEA (43.65 mg, 431.33 umol, 60.04 uL, 2 eq) in DCM (0.1 mL) was added TFAA (90.59 mg, 431.33 umol, 60.00 uL, 2 eq) at 25° C. under $N_2$. The mixture was stirred at 25° C. for 2 h. The reaction mixture was concentrated to get the crude product. The crude product was purified by pre-HPLC. N-[(1S)-1-[[1-cyano-2-(1H-pyrazol-3-yl)ethyl]carbamoyl]-3-methyl-butyl]-4-methoxy-1H-indole-2-carboxamide (23.35 mg, 54.93 umol, 25.47% yield, 99.384% purity) was obtained as the white solid MS (ESI) m/z 423.2 [M+H]$^+$ Prep-HPLC condition: column: Waters Xbridge Prep OBD C18 150*40 mm*10 um; mobile phase: [water (10 mM NH4HCO3)-ACN]; B %: 25%-55%, 8 min $^1$H NMR (400 MHz, METHANOL-$d_4$) δ ppm 7.55 (br d, J=11.25 Hz, 1H), 7.30 (s, 1H), 7.13-7.22 (m, 1H), 7.05 (d, J=7.95 Hz, 1H), 6.54 (d, J=7.70 Hz, 1H), 6.31 (dd, J=10.58, 2.14 Hz, 1H), 5.04-5.17 (m, 1H), 4.56-4.64 (m, 1H), 3.95 (s, 3H), 3.13-3.30 (m, 2H), 1.52-1.83 (m, 3H), 0.90-1.08 (m, 6H)

Step 6: (S)-tert-butyl 2-(4-methoxy-1H-indole-2-carboxamido)-4-methylpentanoate To a mixture of 4-methoxy-1H-indole-2-carboxylic acid (15 g, 78.46 mmol, 1 eq) and tert-butyl (2S)-2-amino-4-methyl-pentanoate (21.07 g, 94.15 mmol, 1.2 eq, HCl) in DMF (150 mL) was added EDCI (19.55 g, 102.00 mmol, 1.3 eq), HOBt (13.78 g, 102.00 mmol, 1.3 eq), TEA (23.82 g, 235.38 mmol, 32.76 mL, 3 eq) at 25° C. under N₂. The mixture was stirred at 25° C. and stirred for 2 h. The reaction mixture was added water (450 mL) and extracted with ethyl acetate (250 mL*3) to get the organic phase. The organic phase was washed with 5% citric acid (300 mL) and 5% aqueous solution of sodium bicarbonate (300 mL) and dried over anhydrous sodium sulfate, filtered and concentrated to get the product. The residue was purified by column chromatography (SiO₂, Petroleum ether:Ethyl acetate=30:1 to 10:1). tert-butyl (2S)-2-[(4-methoxy-1H-indole-2-carbonyl)amino]-4-methyl-pentanoate (24 g, 66.58 mmol, 84.87% yield) was obtained as light yellow solid. MS (ESI) m/z 361.2 [M+H]⁺

Step 7: (S)-2-(4-methoxy-1H-indole-2-carboxamido)-4-methylpentanoic acid

To a mixture of tert-butyl (2S)-2-[(4-methoxy-1H-indole-2-carbonyl)amino]-4-methyl-pentanoate (10 g, 27.74 mmol, 1 eq) in DCM (30 mL) was added TFA (61.60 g, 540.26 mmol, 40 mL, 19.47 eq) and H₂O (4.00 g, 221.98 mmol, 4.00 mL, 8.00 eq) in one portion at 0° C. under N₂. The mixture was stirred at 25° C. and stirred for 2 h. The reaction mixture was concentrated to get the crude product. The crude product was purified by petroleum ether:Ethyl acetate=10:1 (20 mL) and filtered to get the product. (2S)-2-[(4-methoxy-1H-indole-2-carbonyl)amino]-4-methyl-pentanoic acid (6 g, 19.22 mmol, 69.27% yield, 97.48% purity) was obtained as the light yellow solid. MS (ESI) m/z 305.1 [M+H]⁺

Example 52. Synthesis of Viral Protease Inhibitor Compound 245

Step 1: methyl 2-amino-3-(1H-indazol-3-yl)propanoate

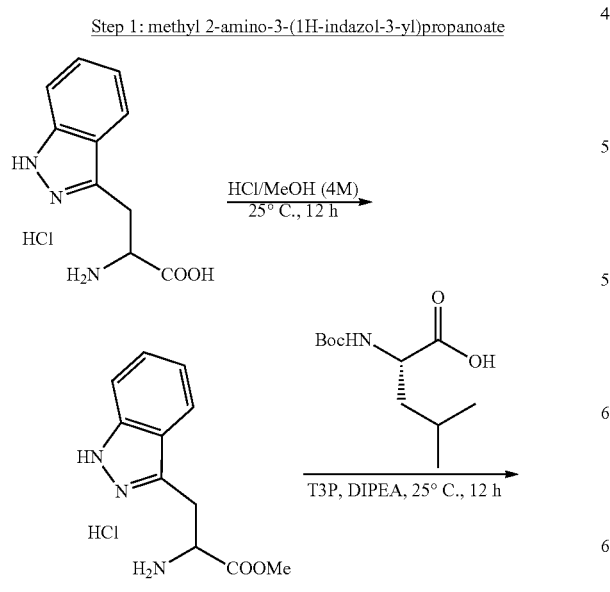

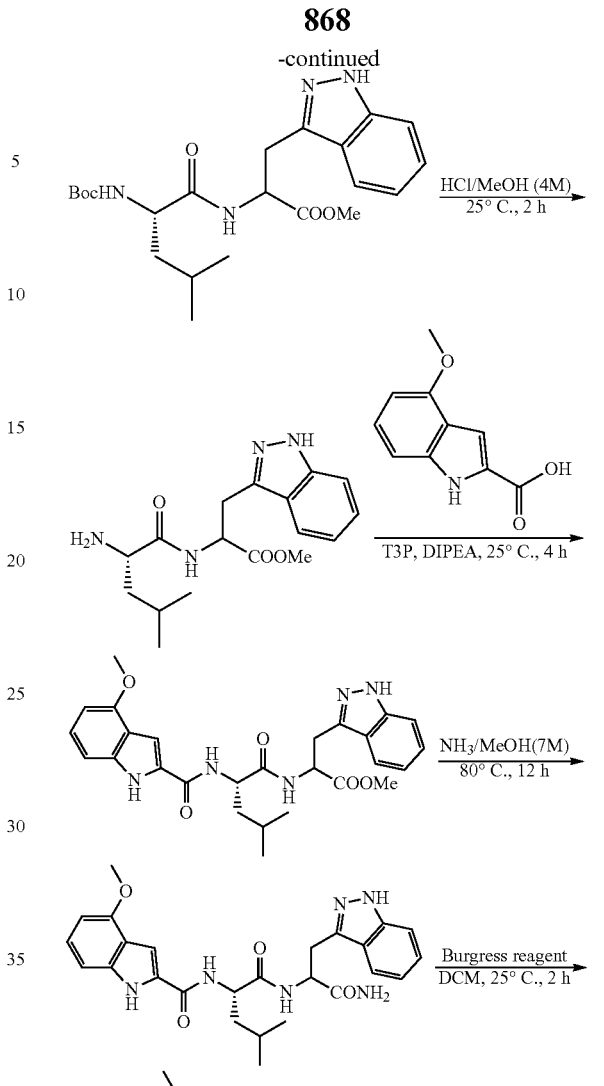

To a mixture of 2-amino-3-(1H-indazol-3-yl) propanoic acid (200 mg, 827.56 umol, 1 eq, HCl) was added HCl/MeOH (4 M, 2 mL, 9.67 eq) at 25° C. under N₂. The mixture was stirred at 25° C. for 12 h. The reaction mixture was concentrated to get the crude product. Methyl 2-amino-3-(1H-indazol-3-yl) propanoate (200 mg, crude, HCl) was obtained as the light yellow solid and used directly next step. MS (ESI) m/z 220.1 [M+H]⁺

Step 2: methyl 2-[[(2S)-2-(tert-butoxycarbonylamino)-4-methyl-pentanoyl]amino]-3-(1H-indazol-3-yl) propanoate To a mixture of methyl 2-amino-3-(1H-indazol-3-yl)propanoate (150 mg, 586.62 umol, 1 eq, HCl) and (2S)-2-(tert-butoxycarbonylamino)-4-methyl-pentanoic acid (203.52 mg, 879.94 umol, 1.5 eq), DIPEA (379.09 mg, 2.93 mmol, 510.90 uL, 5 eq) in DCM (1.5 mL) and THF (1.5 mL) was added T3P (559.96 mg, 879.94 umol, 523.33 uL, 50% purity, 1.5 eq) at 0° C. under $N_2$. The mixture was stirred at 25° C. for 12 h. The reaction mixture was added with saturated sodium bicarbonate solution (10 mL) and extracted with DCM (10 mL*2). The organic phase was concentrated to afford methyl 2-[[(2S)-2-(tert-butoxycarbonylamino)-4-methyl-pentanoyl]amino]-3-(1H-indazol-3-yl)propanoate (180 mg, crude) as a light yellow solid. MS (ESI) m/z 433.2 $[M+H]^+$ Step 3: methyl 2-[[(2S)-2-amino-4-methyl-pentanoyl]amino]-3-(1H-indazol-3-yl)propanoate To a mixture of methyl 2-[[(2S)-2-(tert-butoxycarbonylamino)-4-methyl-pentanoyl]amino]-3-(1H-indazol-3-yl)propanoate (180 mg, 416.17 umol, 1 eq) was added HCl/MeOH (4 M, 5.14 mL, 49.43 eq) in one portion at 25° C. under $N_2$. The mixture was stirred at 25° C. for 2 h. The reaction mixture was concentrated to afford methyl 2-[[(2S)-2-amino-4-methyl-pentanoyl] amino]-3-(1H-indazol-3-yl) propanoate (160 mg, crude, HCl) as light yellow oil and used directly next step. MS (ESI) m/z 333.2 $[M+H]^+$ Step 4: methyl 3-(1H-indazol-3-yl)-2-[[(2S)-2-[(4-methoxy-1H-indole-2-carbonyl)amino]-4-methyl-pentanoyl]amino]propanoate To a mixture of methyl 2-[[(2S)-2-amino-4-methyl-pentanoyl]amino]-3-(1H-indazol-3-yl) propanoate (160 mg, 433.77 umol, 1 eq, HCl) and 4-methoxy-1H-indole-2-carboxylic acid (99.52 mg, 520.53 umol, 1.2 eq), DIPEA (280.31 mg, 2.17 mmol, 377.78 uL, 5 eq) in DCM (1 mL) and THF (1 mL) was added T3P (414.05 mg, 650.66 umol, 386.97 uL, 50% purity, 1.5 eq) in one portion at 0° C. under $N_2$. The mixture was stirred at 25° C. for 4 h. The reaction mixture was added with saturated sodium bicarbonate solution (10 mL) and extracted with DCM (10 mL*2). The organic phase was concentrated to get the crude product. The residue was purified by pre-HPLC. Methyl 3-(1H-indazol-3-yl)-2-[[(2S)-2-[(4-methoxy-1H-indole-2-carbonyl) amino]-4-methyl-pentanoyl] amino]propanoate (80 mg, crude) was obtained as the light yellow solid. MS (ESI) m/z 506.2 $[M+H]^+$ Prep-HPLC condition: column: Phenomenex Gemini-NX 80*40 mm*3 um; mobile phase: [water (10 mM $NH_4HCO_3$)-ACN]; B %: 35%-65%, 8 min Step 5: N-[(1S)-1-[[1-(1H-indazol-3-ylmethyl)-2-nitroso-ethyl]carbamoyl]-3-methyl-butyl]-4-methoxy-1H-indole-2-carboxamide To a mixture of methyl 3-(1H-indazol-3-yl)-2-[[(2S)-2-[(4-methoxy-1H-indole-2-carbonyl)amino]-4-methyl-pentanoyl]amino]propanoate (80 mg, 158.24 umol, 1 eq) was added $NH_3$/MeOH (7 M, 1 mL, 44.24 eq) in one portion at 25° C. under $N_2$. The mixture was stirred at 80° C. for 12 h. The reaction mixture was cooled to 25° C. and concentrated. N-[(1S)-1-[[1-(1H-indazol-3-ylmethyl)-2-nitroso-ethyl]carbamoyl]-3-methyl-butyl]-4-methoxy-1H-indole-2-carboxamide (75 mg, crude) was obtained as light yellow solid and used directly next step. MS (ESI) m/z 491.2 $[M+H]^+$ Step 6: N-[(1S)-1-[[1-cyano-2-(1H-indazol-3-yl) ethyl]carbamoyl]-3-methyl-butyl]-4-methoxy-1H-indole-2-carboxamide To a mixture of N-[(1S)-1-[[1-(1H-indazol-3-ylmethyl)-2-nitroso-ethyl]carbamoyl]-3-methyl-butyl]-4-methoxy-1H-indole-2-carboxamide (75 mg, 152.89 umol, 1 eq) in DCM (0.5 mL) was added methoxycarbonyl-(triethylammonio)sulfonyl-azanide (75.00 mg, 314.72 umol, 2.06 eq) at 25° C. under $N_2$. The mixture was stirred at 25° C. for 12 h. The reaction mixture was concentrated and purified by pre-HPLC. N-[(1S)-1-[[1-cyano-2-(1H-indazol-3-yl)ethyl]carbamoyl]-3-methyl-butyl]-4-methoxy-1H-indole-2-carboxamide (12.0 mg, 25.39 umol, 16.61% yield) was obtained as a white solid. MS (ESI) m/z 473.2 $[M+H]^+$ Prep-HPLC condition: column: Waters Xbridge BEH C18 100*30 mm*10 um; mobile phase: [water (10 Mm $NH_4HCO_3$)-ACN]; B %: 28%-58%, 10 min $^1$H NMR (400 MHz, DMSO-$d_6$) δ ppm 12.95 (br d, J=8.82 Hz, 1H), 11.59 (br dd, J=6.50, 1.87 Hz, 1H), 9.02 (br dd, J=14.11, 7.94 Hz, 1H), 8.39-8.51 (m, 1H), 7.82 (dd, J=11.14, 8.27 Hz, 1H), 7.48-7.55 (m, 1H), 7.31-7.41 (m, 1H), 7.07-7.16 (m, 2H), 6.99-7.05 (m, 1H), 6.49-6.56 (m, 1H), 5.24 (quin, J=7.77 Hz, 1H), 4.39-4.57 (m, 1H), 3.90 (d, J=3.97 Hz, 3H), 3.37-3.62 (m, 2H), 1.60-1.73 (m, 1H), 1.43-1.53 (m, 1H), 1.15-1.28 (m, 1H), 0.84-0.98 (m, 3H), 0.80 (d, J=6.39 Hz, 2H)

Example 53. Synthesis of Viral Protease Inhibitor Compound 1045

Step 1: methyl (2S)-2-[[(2S)-2-amino-3-cyclopropyl-propanoyl]amino-3-[(3S)-2-oxopyrrolidin-3-yl]propanoate

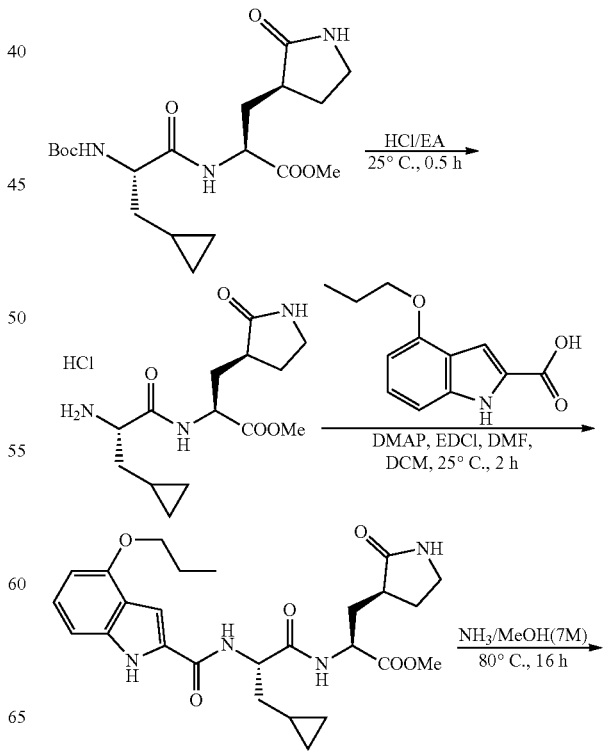

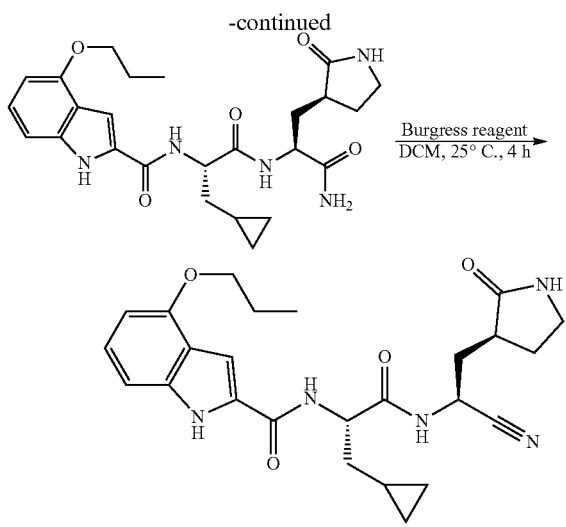

A mixture of methyl (2S)-2-[[(2S)-2-(tert-butoxycarbonylamino)-3-cyclopropyl-propanoyl]amino]-3-[(3S)-2-oxopyrrolidin-3-yl]propanoate (1.3 g, 3.27 mmol, 1 eq) in HCl/MeOH (10 mL) was stirred at 25° C. for 30 min. The reaction mixture was concentrated under reduced pressure to give crude methyl (2S)-2-[[(2S)-2-amino-3-cyclopropyl-propanoyl]amino]-3-[(3S)-2-oxopyrrolidin-3-yl]propanoate (900 mg, 3.03 mmol, 92.54% yield) as a yellow oil.

Step 2: methyl (2S)-2-[[(2S)-3-cyclopropyl-2-[(4-propoxy-1H-indole-2-carbonyl)amino]propanoyl]amino]-3-[(3S)-2-oxopyrrolidin-3-yl]propanoate To a mixture of methyl (2S)-2-[[(2S)-2-amino-3-cyclopropyl-propanoyl]amino]-3-[(3S)-2-oxopyrrolidin-3-yl]propanoate (448 mg, 1.51 mmol, 1 eq) and 4-propoxy-1H-indole-2-carboxylic acid (396.37 mg, 1.81 mmol, 1.2 eq) in DMF (2 mL) was added DCM (8 mL) and EDCI (866.48 mg, 4.52 mmol, 3 eq) in one portion at 25° C. The mixture was added DMAP (552.19 mg, 4.52 mmol, 3 eq) and stirred at 25° C. for 2 h. The reaction mixture was diluted with H$_2$O (10 mL) and extracted with ethyl acetate (10 mL*3). The combined organic layers were washed with brine (10 mL*1), dried over Na$_2$SO$_4$, filtered and concentrated under reduced pressure to give a residue. The crude product was purified by column chromatography (SiO$_2$, petroleum ether/ethyl acetate=5/1 to 0/1) to afford methyl (2S)-2-[[(2S)-3-cyclopropyl-2-[(4-propoxy-1H-indole-2-carbonyl)amino]propanoyl]amino]-3-[(3S)-2-oxopyrrolidin-3-yl]propanoate (480 mg, 962.75 umol, 63.90% yield) as a white solid. MS (ESI) m/z 499.2 [M+H]$^+$ Step 3: N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4-propoxy-1H-indole-2-carboxamide A mixture of methyl (2S)-2-[[(2S)-3-cyclopropyl-2-[(4-propoxy-1H-indole-2-carbonyl)amino]propanoyl]amino]-3-[(3S)-2-oxopyrrolidin-3-yl]propanoate (480 mg, 962.75 umol, 1 eq) in NH$_3$/MeOH (7M) (3 mL) was stirred at 80° C. for 16 h. The reaction mixture was concentrated under reduced pressure to give the crude N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4-propoxy-1H-indole-2-carboxamide (380 mg, 785.84 umol, 81.62% yield) as a white solid. MS (ESI) m/z 484.3 [M+H]$^+$ Step 4: N-[(1S)-2-[[(1S)-1-cyano-2-[(3S)-2-oxopyrrolidin-3-yl]ethyl]amino]-1-(cyclopropylmethyl)-2-oxo-ethyl]-4-propoxy-1H-indole-2-carboxamide To a mixture of N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4-propoxy-1H-indole-2-carboxamide (380 mg, 785.84 umol, 1 eq) in DCM (7 mL) was added Burgess reagent (1.12 g, 4.72 mmol, 6 eq) in one portion at 25° C. The mixture was stirred at 25° C. for 4 h. The reaction mixture was concentrated under reduced pressure to give a residue. The crude product was purified by prep-HPLC (neutral condition) to give N-[(1S)-2-[[(1S)-1-cyano-2-[(3S)-2-oxopyrrolidin-3-yl]ethyl]amino]-A-(cyclopropylmethyl)-2-oxo-ethyl]-4-propoxy-1H-indole-2-carboxamide (120 mg, 257.76 umol, 32.80% yield) was obtained as a white solid. MS (ESI) m/z 466.3 [M+H]$^+$ column: Waters Xbridge Prep OBD C18 150*40 mm*10 um; mobile phase: [water (10 mM NH$_4$HCO$_3$)-ACN]; B %: 30%-60%, 8 min $^1$H NMR (400 MHz, DMSO-d$_6$) δ=11.55 (br d, J=1.7 Hz, 1H), 9.07-8.85 (m, 1H), 8.57 (d, J=7.6 Hz, 1H), 7.83-7.61 (m, 1H), 7.39 (d, J=1.6 Hz, 1H), 7.14-6.90 (m, 2H), 6.48 (d, J=7.6 Hz, 1H), 5.09-4.86 (m, 1H), 4.60-4.28 (m, 1H), 4.04 (t, J=6.4 Hz, 2H), 3.22-3.01 (m, 2H), 2.45-2.03 (m, 3H), 1.94-1.59 (m, 5H), 1.58-1.34 (m, 1H), 1.06 (t, J=7.4 Hz, 3H), 0.95-0.69 (m, 1H), 0.55-0.30 (m, 2H), 0.28-0.02 (m, 2H)

Example 54. Synthesis of Viral Protease Inhibitor Compound 147

Step 1: (S)-methyl 2-amino-3-((S)-2-oxopyrrolidin-3-yl)propanoate

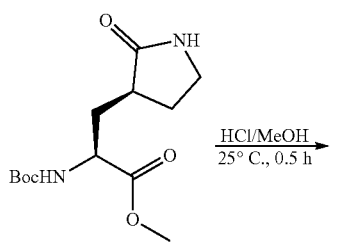

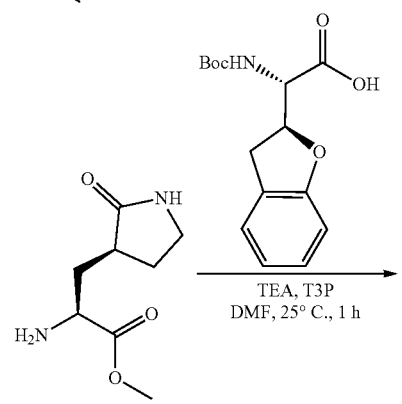

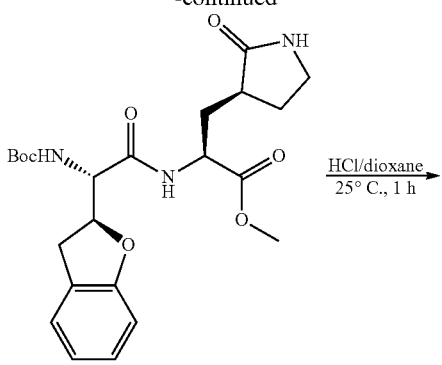

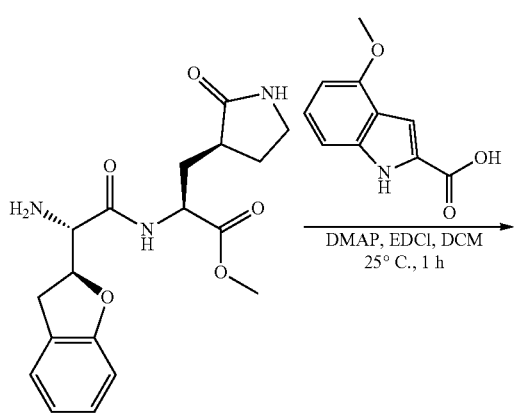

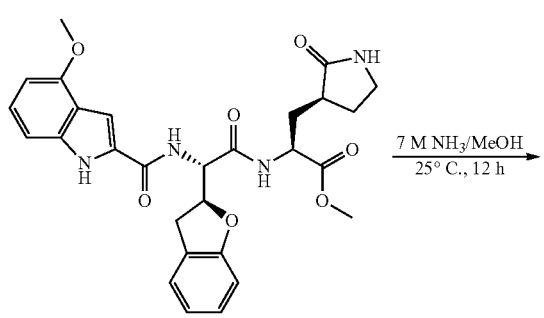

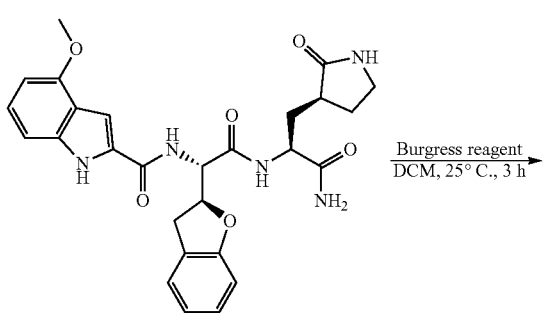

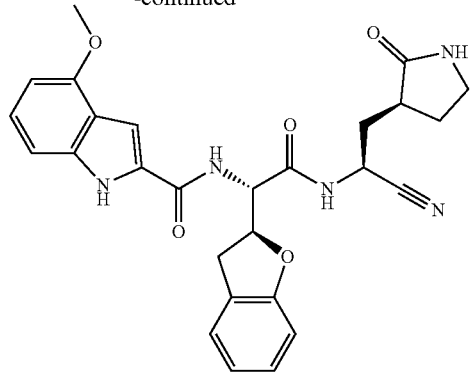

A solution of (S)-methyl 2-((tert-butoxycarbonyl)amino)-3-((S)-2-oxopyrrolidin-3-yl)propanoate (100 mg, 349.26 umol, 1 eq) in HCl/MeOH (4 M, 2 mL, 22.91 eq) was stirred at 25° C. for 0.5 h. The reaction mixture was concentrated to give the crude product (S)-methyl 2-amino-3-((S)-2-oxopyrrolidin-3-yl)propanoate (65 mg, crude) as white solid. MS (ESI) m/z 187.1 [M+H]$^+$ Step 2: (S)-methyl 2-((S)-2-((tert-butoxycarbonyl)amino)-2-((S)-2,3-dihydrobenzofuran-2-yl)acetamido)-3-((S)-2-oxopyrrolidin-3-yl)propanoate To a mixture of (S)-2-((tert-butoxycarbonyl)amino)-2-((S)-2,3-dihydrobenzofuran-2-yl)acetic acid (100 mg, 340.93 umol, 1 eq) and (S)-methyl 2-amino-3-((S)-2-oxopyrrolidin-3-yl)propanoate (65 mg, 349.07 umol, 1.02 eq) in DMF (3 mL) was added TEA (206.99 mg, 2.05 mmol, 284.72 uL, 6 eq) and T$_3$P (325.43 mg, 511.40 umol, 304.14 uL, 50% purity, 1.5 eq). The reaction was stirred at 25° C. for 1 h, and then diluted with H$_2$O (20 mL) and extracted with ethyl acetate (30 mL*3). The combined organic layers were washed with brine (10 mL), dried over Na$_2$SO$_4$, filtered and concentrated under reduced pressure to give (S)-methyl 2-((S)-2-((tert-butoxycarbonyl)amino)-2-((S)-2,3-dihydrobenzofuran-2-yl)acetamido)-3-((S)-2-oxopyrrolidin-3-yl)propanoate (110 mg, crude) as white solid. MS (ESI) m/z 462.2 [M+H]$^+$ Step 3: (S)-methyl 2-((S)-2-amino-2-((S)-2,3-dihydrobenzofuran-2-yl)acetamido)-3-((S)-2-oxopyrrolidin-3-yl)propanoate A solution of (S)-methyl 2-((S)-2-((tert-butoxycarbonyl)amino)-2-((S)-2,3-dihydrobenzofuran-2-yl)acetamido)-3-((S)-2-oxopyrrolidin-3-yl)propanoate (110 mg, 238.35 umol, 1 eq) in HCL/dioxane (2 mL) was stirred at 25° C. for 1 h. The residue was concentrated in vacuum to afford (S)-methyl 2-((S)-2-amino-2-((S)-2,3-dihydrobenzofuran-2-yl)acetamido)-3-((S)-2-oxopyrrolidin-3-yl)propanoate (95 mg, crude, HCl) as white solid. MS (ESI) m/z 362.2 [M+H]$^+$ Step 4: (S)-methyl 2-((S)-2-((S)-2,3-dihydrobenzofuran-2-yl)-2-(4-methoxy-1H-indole-2-carboxamido)acetamido)-3-((S)-2-oxopyrrolidin-3-yl)propanoate To a solution of (S)-methyl 2-((S)-2-amino-2-((S)-2,3-dihydrobenzofuran-2-yl)acetamido)-3-((S)-2-oxopyrrolidin-3-yl)propanoate (95 mg, 238.78 umol, 1 eq, HCl) and 4-methoxy-1H-indole-2-carboxylic acid (45.65 mg, 238.78 umol, 1 eq) in DMF (3 mL) was added EDCI (91.55 mg, 477.56 umol, 2 eq) and DMAP (58.34 mg, 477.56 umol, 2 eq) then was stirred at 25° C. for 1 h. The residue was poured into water (20 mL). The aqueous phase was extracted with ethyl acetate (10 mL*3). The combined organic phase was washed with brine (10 mL*3), dried with anhydrous $Na_2SO_4$, filtered and concentrated in vacuum. The residue was purified by prep-HPLC column: Waters Xbridge BEH C18 100*25 mm*5 um; mobile phase: [water (10 mM $NH_4HCO_3$)-ACN]; B %: 20%-50%, 10 min to give (S)-methyl 2-((S)-2-((S)-2,3-dihydrobenzofuran-2-yl)-2-(4-methoxy-1H-indole-2-carboxamido)acetamido)-3-((S)-2-oxopyrrolidin-3-yl)propanoate (21 mg, 39.28 umol, 16.45% yield) as light yellow solid. MS (ESI) m/z 535.2 [M+H]$^+$ Step 5: —((S)-2-(((S)-1-amino-1-oxo-3-((S)-2-oxopyrrolidin-3-yl)propan-2-yl)amino)-1-((S)-2,3-dihydrobenzofuran-2-yl)-2-oxoethyl)-4-methoxy-1H-indole-2-carboxamide A solution of (S)-methyl 2-((S)-2-((S)-2,3-dihydrobenzofuran-2-yl)-2-(4-methoxy-1H-indole-2-carboxamido)acetamido)-3-((S)-2-oxopyrrolidin-3-yl)propanoate (19 mg, 35.54 umol, 1 eq) in $NH_3$·MeOH (7 M, 5 mL, 984.71 eq) was stirred at 25° C. for 12 h. The reaction was concentrated to afford N-((S)-2-(((S)-1-amino-1-oxo-3-((S)-2-oxopyrrolidin-3-yl)propan-2-yl)amino)-1-((S)-2,3-dihydrobenzofuran-2-yl)-2-oxoethyl)-4-methoxy-1H-indole-2-carboxamide (19 mg, crude) as white solid. MS (ESI) m/z 520.1 [M+H]$^+$ Step 6: N-((S)-2-(((S)-1-cyano-2-((S)-2-oxopyrrolidin-3-yl)ethyl)amino)-1-((S)-2,3-dihydrobenzofuran-2-yl)-2-oxoethyl)-4-methoxy-1H-indole-2-carboxamide A mixture of N-((S)-2-(((S)-1-amino-1-oxo-3-((S)-2-oxopyrrolidin-3-yl)propan-2-yl)amino)-1-((S)-2,3-dihydrobenzofuran-2-yl)-2-oxoethyl)-4-methoxy-1H-indole-2-carboxamide (19 mg, 36.57 umol, 1 eq), methoxycarbonyl-(triethylammonio)sulfonyl-azanide (26.14 mg, 109.71 umol, 3 eq) in DCM (2 mL) was stirred at 25° C. for 3 h. The reaction mixture was concentrated and purified by prep-HPLC column: Waters Xbridge Prep OBD C18 150*40 mm*10 um; mobile phase: [water (10 mM $NH_4HCO_3$)-ACN]; B %: 20%-50%, 8 min to give N-((S)-2-(((S)-1-cyano-2-((S)-2-oxopyrrolidin-3-yl)ethyl)amino)-1-((S)-2,3-dihydrobenzofuran-2-yl)-2-oxoethyl)-4-methoxy-1H-indole-2-carboxamide (2.13 mg, 3.74 umol, 10.22% yield, 88% purity) as white solid. MS (ESI) m/z 502.2 [M+H]$^+$.

$^1$H NMR (400 MHz, METHANOL-$d_4$) δ ppm 7.29-7.32 (m, 1H) 7.19-7.25 (m, 1H) 7.17 (d, J=8.07 Hz, 1H) 7.08-7.14 (m, 1H) 7.05 (d, J=8.31 Hz, 1H) 6.87 (t, J=7.40 Hz, 1H) 6.74 (d, J=7.95 Hz, 1H) 6.54 (d, J=7.70 Hz, 1H) 5.04-5.24 (m, 2H) 4.71-4.78 (m, 1H) 4.63 (s, 1H) 3.96 (s, 3H) 3.35-3.51 (m, 2H) 3.06-3.30 (m, 2H) 2.68 (ddt, J=14.09, 9.63, 4.83, 4.83 Hz, 0.4H) 2.24-2.45 (m, 2H) 2.13-2.22 (m, 0.6H) 1.70-1.94 (m, 2H)

Example 55. Synthesis of Viral Protease Inhibitor Compound 491

Step 1: methyl (2S)-2-[[3-cyclopropyl-2-[(4-methoxy-1H-indole-2-carbonyl)amino]propanoyl]amino]-3-[(3S)-2-oxo-3-piperidyl]propanoate

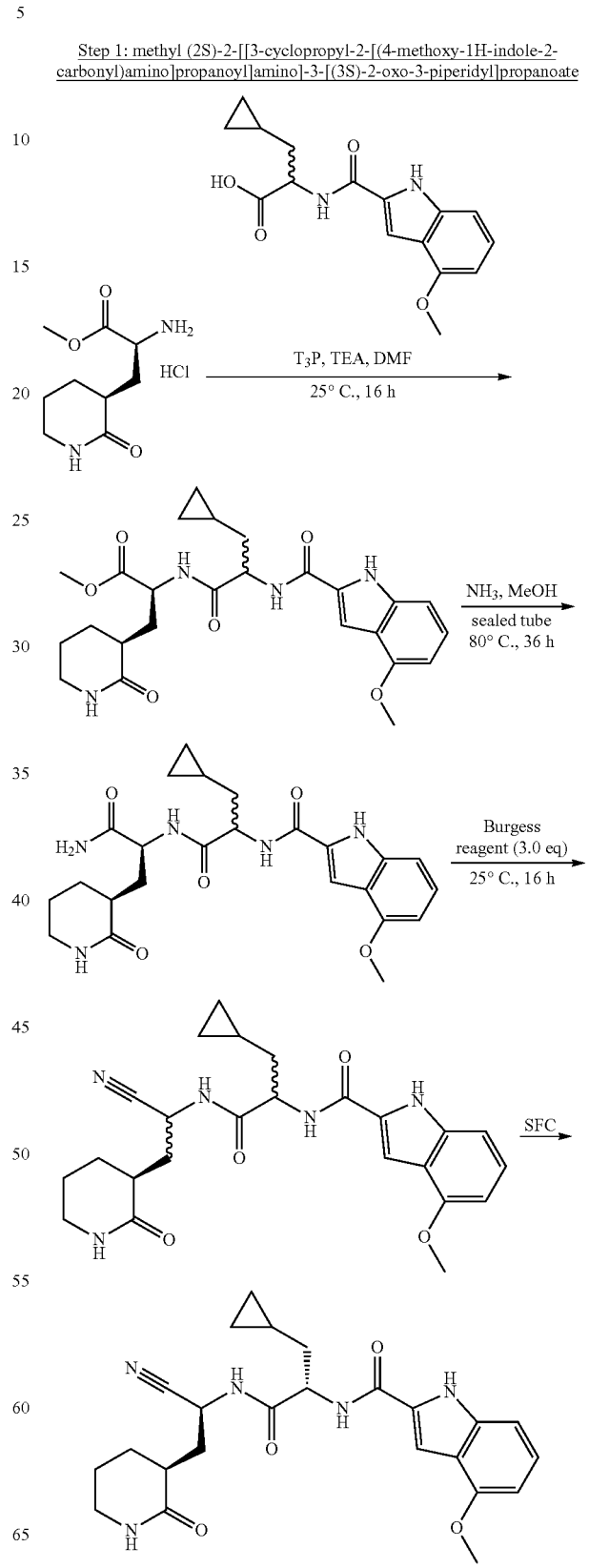

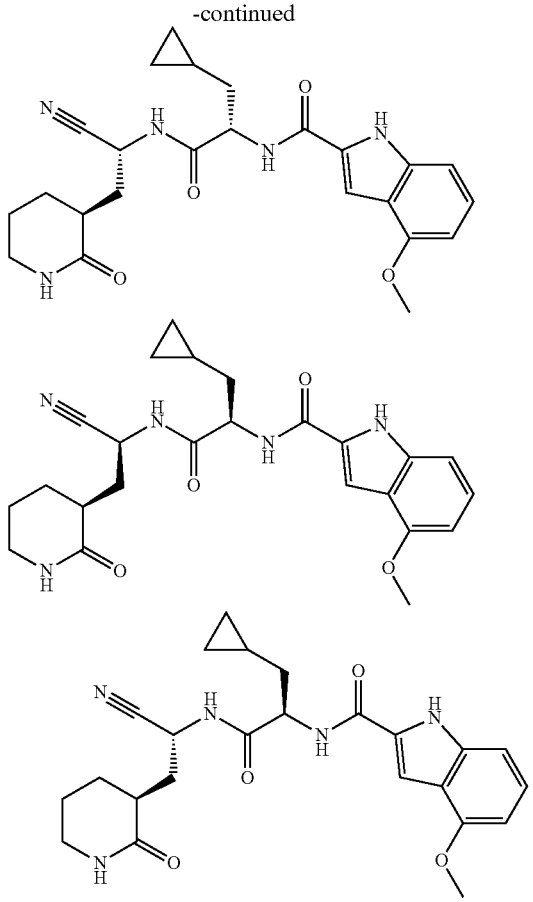

To the mixture of methyl (2S)-2-amino-3-[(3S)-2-oxo-3-piperidyl]propanoate (240 mg, 1.01 mmol, 1 eq, HCL), (2S)-3-cyclopropyl-2-[(4-methoxy-1H-indole-2-carbonyl)amino]propanoic acid (412.2 mg, 1.22 mmol, 1.2 eq, HC) and TEA (410.4 mg, 4.06 mmol, 0.56 mL, 4 eq) in DMF (3 mL) was added T$_3$P (1.2 g, 2.03 mmol, 1.21 mL, 50% purity, 2 eq) at 25° C. The mixture was stirred at 25° C. for 16 h. TLC (DCM:MeOH=10:1/UV254 nm) showed new spot was detected. The reaction mixture was diluted with H$_2$O (10 mL) and the mixture was extracted with ethyl acetate (10 mL*3). The combined organic phase was washed with brine (10 mL*2), dried with anhydrous Na$_2$SO$_4$, filtered and concentrated in vacuum. The residue was purified by flash silica gel chromatography (ISCO®; 12 g SepaFlash® Silica Flash Column, Eluent of 100~25% Ethyl acetate/MeOH@30 mL/min). Compound methyl (2S)-2-[[(2S)-3-cyclopropyl-2-[(4-methoxy-1H-indole-2-carbonyl)amino]propanoyl]amino]-3-[(3S)-2-oxo-3-piperidyl]propanoate (256 mg, 0.48 mmol, 48.2% yield, 92.5% purity) was obtained as yellow solid.

Step 2: N-[2-[[(1S)-2-amino-2-oxo-1-[[(3S)-2-oxo-3piperidyl]ethyl]ethyl]amino]-1-(cyclopropylmethyl)-2-oxo-ethyl]-4-methoxy-1H-indole-2-carboxamide A mixture of methyl (2S)-2-[[(2S)-3-cyclopropyl-2-[(4-methoxy-1H-indole-2-carbonyl)amino]propanoyl]amino]-3-[(3S)-2-oxo-3-piperidyl]propanoate (246.3 mg, 0.47 mmol, 92.5% purity, 1 eq) in NH$_3$ (7 M, 6.72 mL, 100 eq) (7M in MeOH) was stirred at 80° C. for 36 h in a sealed tube. LC-MS showed the desired compound was detected. The reaction mixture was concentrated in vacuum. Compound N-[(1 S)-2-[[(1 S)-2-amino-2-oxo-1-[[(3 S)-2-oxo-3-piperidyl]methyl]ethyl]amino]-1-(cyclopropylmethyl)-2-oxo-ethyl]-4-methoxy-1H-indole-2-carboxamide (220 mg, crude) was obtained as yellow solid, which was used into the next step without further purification.

Step 3: N-[2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide A mixture of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-indole-2-carboxamide (250 mg, 0.53 mmol, 1 eq) and methoxycarbonyl-(triethylammonio)sulfonyl-azanide (444.0 mg, 1.86 mmol, 3.5 eq) in DCM (3 mL) was stirred at 25° C. for 16 h. The reaction mixture was diluted with H$_2$O (10 mL) and the mixture was extracted with ethyl acetate (10 mL*3). The combined organic phase was washed with brine (10 mL*2), dried with anhydrous Na$_2$SO$_4$, filtered and concentrated in vacuum. The residue was purified by prep-HPLC (column: Phenomenex Gemini-NX 80*30 mm*3 um; mobile phase: [water (0.05% NH$_3$H$_2$O+10 mM NH$_4$HCO$_3$)-ACN]; B %: 23%-53%, 9.5 min). Compound N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide (83 mg, 0.18 mmol, 34.2% yield, 99.0% purity) was obtained as white solid.

Isomer 1: N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide Isomer 2: N-[(1S)-2-[[(1R)-1-cyano-2-[(3S)-2-oxo-3-piperidyl]ethyl]amino]-1-(cyclopropylmethyl)-2-oxo-ethyl]-4-methoxy-1H-indole-2-carboxamide Isomer 3: N-[(1R)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide Isomer 4: N-[(1R)-2-[[(1R)-1-cyano-2-[(3S)-2-oxo-3-piperidyl]ethyl]amino]-1-(cyclopropylmethyl)-2-oxo-ethyl]-4-methoxy-1H-indole-2-carboxamide N-[2-[[1-cyano-2-[(3S)-2-oxo-3-piperidyl]ethyl]amino]-1-(cyclopropylmethyl)-2-oxo-ethyl]-4-methoxy-1H-indole-2-carboxamide (50 mg, 0.11 mmol, 1 eq) was purified by SFC (column: DAICEL CHIRALPAK AD (250 mm*30 mm, 10 um); mobile phase: [0.1% NH$_3$H$_2$O ETOH]; B %: 55%-55%, min) to get three fragments.

Isomer 1: N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide. Compound N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide (28.1 mg, 62.2 umol, 56.2% yield, 100% purity) was obtained as white solid. LCMS: Rt=0.755 min; for C$_{24}$H$_{29}$N$_5$O$_4$ MS Calcd.: 451.22, MS Found: 452.2 [M+H$^+$].

$^1$H NMR (400 MHz, DMSO-d$_6$) δ 11.57 (s, 1H), 8.91 (br d, J=8.0 Hz, 1H), 8.50 (br d, J=7.5 Hz, 1H), 7.53 (br s, 1H), 7.37 (d, J=1.4 Hz, 1H), 7.15-7.06 (m, 1H), 7.04-6.97 (m, 1H), 6.51 (d, J=7.6 Hz, 1H), 5.07 (q, J=8.2 Hz, 1H), 4.49-4.40 (m, 1H), 3.89 (s, 3H), 3.15-3.01 (m, 2H), 2.34-2.20 (m, 2H), 1.91-1.76 (m, 3H), 1.70 (br dd, J=4.4, 8.7 Hz, 1H), 1.64-1.53 (m, 1H), 1.35 (br s, 1H), 0.86-0.76 (m, 1H), 0.48-0.35 (m, 2H), 0.25-0.04 (m, 1H).

Isomer 4: N-[(1R)-2-[[(1R)-1-cyano-2-[(3S)-2-oxo-3-piperidyl]ethyl]amino]-1-(cyclopropylmethyl)-2-oxo-ethyl]-

4-methoxy-1H-indole-2-carboxamide. Compound N-[(1R)-2-[[(1R)-1-cyano-2-[(3S)-2-oxo-3-piperidyl]ethyl]amino]-1-(cyclopropylmethyl)-2-oxo-ethyl]-4-methoxy-1H-indole-2-carboxamide (6.1 mg, 13.5 umol, 12.2% yield, 100% purity) was obtained as white solid. LCMS: Rt=0.752 min; for C$_{24}$H$_{29}$N$_5$O$_4$ MS Calcd.: 451.22, MS Found: 452.2 [M+H$^+$].

$^1$H NMR (400 MHz, CD$_3$OD) δ 7.27 (s, 1H), 7.18-7.12 (m, 1H), 7.03 (d, J=8.4 Hz, 1H), 6.51 (d, J=7.6 Hz, 1H), 5.12 (dd, J=6.4, 7.7 Hz, 1H), 4.85 (br s, 1H), 3.93 (s, 3H), 3.24-3.16 (m, 2H), 2.50-2.32 (m, 2H), 2.06-1.92 (m, 2H), 1.92-1.82 (m, 2H), 1.70 (dt, J=7.0, 14.2 Hz, 2H), 1.63-1.54 (m, 1H), 1.31-1.31 (m, 1H), 1.41-1.27 (m, 1H), 0.91-0.80 (m, 1H), 0.53 (br d, J=8.0 Hz, 2H), 0.25-0.14 (m, 2H).

The mixture of Isomer 2 & Isomer 3 (20.0 mg, 44.3 umol, 1 eq) was purified by SFC (column: DAICEL CHIRALCEL OD-H (250 mm*30 mm, 5 um); mobile phase: [0.1% NH$_3$H$_2$O ETOH]; B %: 45%-45%, min) to get two fragments.

Isomer 3: N-[(1R)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide. Compound N-[(1R)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide (5.1 mg, 11.3 umol, 25.6% yield, 100% purity) was obtained as white solid. LCMS: Rt=0.754 min; for C$_{24}$H$_{29}$N$_5$O$_4$ MS Calcd: 451.22, MS Found: 452.1 [M+H$^+$].

$^1$H NMR (400 MHz, CD$_3$OD) δ 7.28 (s, 1H), 7.18-7.12 (m, 1H), 7.03 (d, J=8.3 Hz, 1H), 6.52 (d, J=7.5 Hz, 1H), 5.06 (dd, J=6.5, 9.8 Hz, 1H), 4.81 (br s, 1H), 3.93 (s, 3H), 3.18 (br s, 2H), 2.43-2.35 (m, 1H), 2.45-2.27 (m, 1H), 2.31 (br s, 1H), 2.06-1.95 (m, 1H), 1.94-1.78 (m, 3H), 1.76-1.59 (m, 2H), 1.58-1.45 (m, 1H), 1.40 (s, 1H), 1.29 (s, 1H), 0.92-0.79 (m, 1H), 0.58-0.44 (m, 2H), 0.26-0.12 (m, 2H).

Isomer 2: N-[(1S)-2-[[(1R)-1-cyano-2-[(3S)-2-oxo-3-piperidyl]ethyl]amino]-1-(cyclopropylmethyl)-2-oxo-ethyl]-4-methoxy-1H-indole-2-carboxamide. Compound N-[(1S)-2-[[(1R)-1-cyano-2-[(3S)-2-oxo-3-piperidyl]ethyl]amino]-1-(cyclopropylmethyl)-2-oxo-ethyl]-4-methoxy-1H-indole-2-carboxamide (6.3 mg, 14.0 umol, 31.6% yield, 100% purity) was obtained white solid. LCMS: Rt=0.754 min; for C$_{24}$H$_{29}$N$_5$O$_4$ MS Calcd: 451.22, MS Found: 452.1 [M+H$^+$].

$^1$H NMR (400 MHz, CD$_3$OD) δ 7.12 (s, 1H), 7.01-6.96 (m, 1H), 6.87 (d, J=8.3 Hz, 1H), 6.35 (d, J=7.8 Hz, 1H), 4.89 (t, J=7.2 Hz, 1H), 4.43 (dd, J=6.3, 8.3 Hz, 2H), 3.77 (s, 3H), 3.08-3.00 (m, 2H), 2.32-2.22 (m, 1H), 2.20-2.10 (m, 1H), 2.27-2.07 (m, 1H), 1.84-1.73 (m, 2H), 1.72-1.62 (m, 2H), 1.60-1.50 (m, 2H), 1.43-1.34 (m, 1H), 0.75-0.62 (m, 1H), 0.40-0.27 (m, 2H), 0.08-0.04 (m, 2H).

Example 56. Synthesis of Viral Protease Inhibitor Compound 247

Step 1: (2S)-2-(benzyloxycarbonylamino)-3-(1H-indol-3-yl)propanoic acid

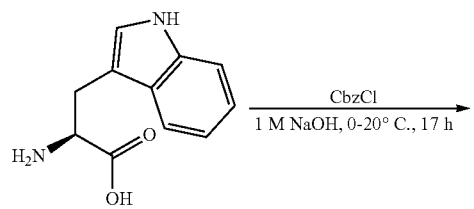

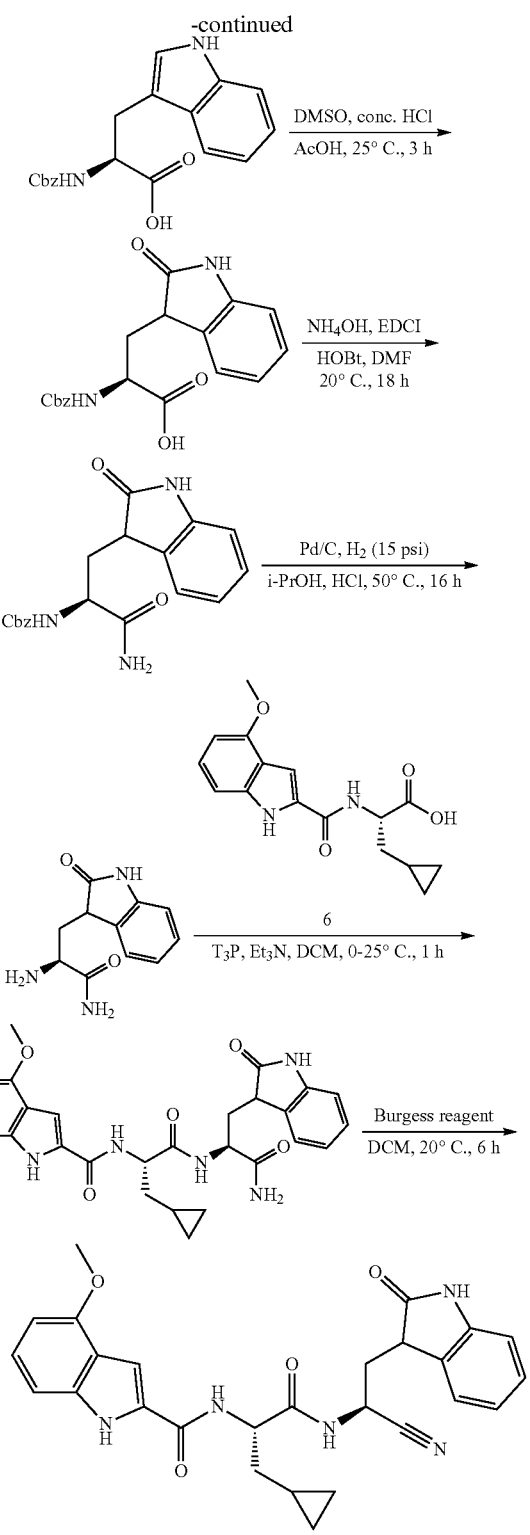

(2S)-2-amino-3-(1H-indol-3-yl)propanoic acid (3 g, 14.69 mmol, 1 eq) was dissolved in NaOH (1 M, 14.65 mL) and stirred at 0° C. CbzCl (2.51 g, 14.73 mmol, 2.09 mL, 1 eq) and NaOH (1 M, 14.65 mL) were then simultaneously added drop-wise. The mixture was stirred for 17 h at 20° C. Upon completion, the solution was acidified with 6 M HCl to pH=1 after which the product was extracted with EtOAc (80 mL*3). The organic layers were combined, dried by Na₂SO₄ and evaporated. The crude product was purified by silica gel chromatography (SiO₂, DCM:MeOH=7:1) and re-purified by prep-HPLC (HPLC:ET40319-84-P1D; column: Xtimate C18 10 u 250 mm*80 mm; mobile phase: [water (10 mM NH₄HCO₃)-ACN]; B %: 5%-35%, 25 min) to give (2S)-2-(benzyloxycarbonylamino)-3-(1H-indol-3-yl) propanoic acid (1.6 g, 4.63 mmol, 31.55% yield, 98% purity) as light yellow solid. MS (ESI) m/z 339.1 [M+H]⁺

¹H NMR (400 MHz, DMSO-d₆) δ=10.79 (br s, 1H), 7.57-7.44 (m, 1H), 7.35-7.23 (m, 5H), 7.21-7.13 (m, 1H), 7.10 (d, J=2.1 Hz, 1H), 7.07-7.01 (m, 1H), 6.98-6.88 (m, 2H), 6.98-6.88 (m, 1H), 4.97 (s, 2H), 4.09 (dt, J=4.6, 7.7 Hz, 1H), 3.22 (dd, J=4.3, 14.4 Hz, 1H), 3.00 (dd, J=8.0, 14.5 Hz, 1H).

Step 2: (2S)-2-(benzyloxycarbonylamino)-3-(2-oxoindolin-3-yl)propanoic acid

A mixture of (2S)-2-(benzyloxycarbonylamino)-3-(1H-indol-3-yl)propanoic acid (1.5 g, 4.00 mmol, 1 eq, HCl) in AcOH (60 mL) was added DMSO (469.01 mg, 6.00 mmol, 469.01 uL, 1.5 eq) and HCl (12 M, 1.33 mL, 4 eq) at 25° C., and the mixture was stirred at 25° C. for 3 h under N₂. Upon completion, the mixture was quenched with water (100 mL), extracted with ethyl acetate (60 mL*3), the combined organic layer washed with brine (200 mL), dried with Na₂SO₄, filtered and concentrated in reduced pressure at 40° C. The mixture was purified by prep-HPLC (column: Welch Xtimate C18 250*70 mm #10 um; mobile phase: [water (10 mM NH₄HCO₃)-ACN]; B %: 7%-37%, 20 min) to give (2S)-2-(benzyloxycarbonylamino)-3-(2-oxoindolin-3-yl) propanoic acid (800 mg, 2.03 mmol, 50.77% yield, 90% purity) as white solid. MS (ESI) m/z 337.0 [M+H]⁺

Step 3: benzyl N-[(1S)-2-amino-2-oxo-1-[(2-oxoindolin-3-yl)methyl]ethyl]carbamate A mixture of (2S)-2-(benzyloxycarbonylamino)-3-(2-oxoindolin-3-yl)propanoic acid (600 mg, 1.54 mmol, 1 eq, HCl) in DMF (20 mL) was added 1-hydroxybenzotriazole (207.45 mg, 1.54 mmol, 1 eq) and EDCI (323.74 mg, 1.69 mmol, 1.1 eq) at 20° C. After the mixture was stirred at 20° C. for 2 h under N₂, NH₃·H₂O (1.01 g, 7.22 mmol, 1.11 mL, 25% purity, 4.7 eq) was added drop-wise. The mixture was stirred at 20° C. for 16 h. Upon completion, the mixture quenched with water (30 mL) and extracted with ethyl acetate (30 mL*3). The combined organic layers washed with brine (100 mL), dried with Na₂SO₄, filtered and concentrated in reduced pressure at 40° C. to give benzyl N-[(1S)-2-amino-2-oxo-1-[(2-oxoindolin-3-yl)methyl] ethyl]carbamate (500 mg, crude) as white solid which was used for next step without further purification. MS (ESI) m/z 354.1 [M+H]⁺

Step 4: (2S)-2-amino-3-(2-oxoindolin-3-yl)propanamide

To a solution of benzyl N-[(1S)-2-amino-2-oxo-1-[(2-oxoindolin-3-yl)methyl]ethyl]carbamate (500 mg, 1.41 mmol, 1 eq) in i-PrOH (100 mL) was added Pd/C (339.59 mg, 282.99 umol, 10% purity, 0.2 eq) and HCl (12 M, 1.30 mL, 11 eq) under N₂. The suspension was degassed under vacuum and purged with H₂ several times. The mixture was stirred under H₂ (15 psi) at 50° C. for 16 h. Upon completion, the reaction mixture was filtered and the filter was concentrated. The crude product was purified by prep-HPLC (HPLC:ET40319-96-P1C; column: Waters Xbridge Prep OBD C18 150*40 mm*10 um; mobile phase: [water (10 mM NH₄HCO₃)-ACN]; B %: 1%-20%, 8 min) to give (2S)-2-amino-3-(2-oxoindolin-3-yl)propanamide (130 mg, 549.67 umol, 38.85% yield, 92.7% purity) as white solid. MS (ESI) m/z 220.1 [M+H]⁺

Step 5: N-[(1S)-2-[[(1S)-2-amino-2-oxo-1-[(2-oxoindolin-3-yl)methyl]ethyl]amino]-1-(cyclopropylmethyl)-2-oxo-ethyl]-4-methoxy-1H-indole-2-carboxamide To a mixture of (2S)-2-amino-3-(2-oxoindolin-3-yl)propanamide (60 mg, 273.67 umol, 1 eq), (2S)-3-cyclopropyl-2-[(4-methoxy-1H-indole-2-carbonyl)amino]propanoic acid (99.29 mg, 328.41 umol, 1.2 eq) and Et₃N (166.16 mg, 1.64 mmol, 228.55 uL, 6 eq) in DCM (10 mL) was added T3P (522.46 mg, 821.02 umol, 488.28 uL, 50% purity, 3 eq) drop-wise at 0° C. The solution was stirred at 25° C. for 1 h under N₂. Upon completion, the mixture was quenched with water (20 mL) and extracted with DCM:MeOH=7:1 (15 mL*2). The combined organic layers washed with brine (30 mL), dried with Na₂SO₄, filtered and concentrated in reduced pressure at 40° C. The residue was purified by prep-TLC (SiO₂, DCM:MeOH=10:1) to give N-[(1S)-2-[[(1S)-2-amino-2-oxo-1-[(2-oxoindolin-3-yl)methyl]ethyl] amino]-1-(cyclopropylmethyl)-2-oxo-ethyl]-4-methoxy-1H-indole-2-carboxamide (40 mg, 55.61 umol, 20.32% yield, 70% purity) as colorless oil. MS (ESI) m/z 504.3 [M+H]⁺

Step 6: N-[(1S)-2-[[(1S)-1-cyano-2-(2-oxoindolin-3-yl)ethyl]amino]-1-(cyclopropylmethyl)-2-oxo-ethyl]-4-methoxy-1H-indole-2-carboxamide To a mixture of N-[(1S)-2-[[(1S)-2-amino-2-oxo-1-[(2-oxoindolin-3-yl)methyl]ethyl]amino]-1-(cyclopropylmethyl)-2-oxo-ethyl]-4-methoxy-1H-indole-2-carboxamide (35 mg, 69.51 umol, 1 eq) in DCM (6 mL) was added methoxycarbonyl-(triethylammonio)sulfonyl-azanide (49.69 mg, 208.52 umol, 3 eq) in one portion at 20° C. and stirred at 20° C. for 2 h. Methoxycarbonyl-(triethylammonio)sulfonyl-azanide (82.82 mg, 347.53 umol, 5 eq) was added at 20° C. and stirred at 20° C. for 4 h. Upon completion, the crude was dried by N₂ and purified by prep-HPLC (column: Waters Xbridge Prep OBD C18 150*40 mm*10 um; mobile phase: [water (10 mM NH₄HCO₃)-ACN]; B %: 30%-60%, 8 min) and re-purified by prep-HPLC (column: Phenomenex Luna C18 75*30 mm*3 um; mobile phase: [water(0.2% FA)-ACN]; B %: 30%-70%, 8 min) to afford N-[(1S)-2-[[(1S)-1-cyano-2-(2-oxoindolin-3-yl)ethyl]amino]-1-(cyclopropylmethyl)-2-oxo-ethyl]-4-methoxy-1H-indole-2-carboxamide (5 mg, 10.23 umol, 14.72% yield, 99.36% purity, 99.36% purity) as white solid. MS (ESI) m/z 486.2 [M+H]⁺

¹H NMR (400 MHz, METHANOL-d₄) δ=7.39-7.09 (m, 4H), 7.07-6.95 (m, 2H), 6.92-6.80 (m, 1H), 6.51 (dd, J=3.1, 7.5 Hz, 1H), 5.37-5.14 (m, 1H), 4.65-4.47 (m, 1H), 3.93 (dd, J=1.4, 3.4 Hz, 3H), 3.70-3.52 (m, 1H), 2.63-2.27 (m, 2H), 1.92-1.60 (m, 2H), 0.84 (br s, 1H), 0.59-0.43 (m, 2H), 0.27-0.10 (m, 2H)

Example 57. Synthesis of Viral Protease Inhibitor Compound 331

Steps for Isomer 1 and 2: N-[(1S)-1-[[(1S)-2-cyano-1-[[(3S)-2-oxopyrrolidin-3-yl]methyl]-2-pyrrolidin-1-yl-ethyl]carbamoyl]-3-methyl-butyl]-4-methoxy-1H-indole-2-carboxamide

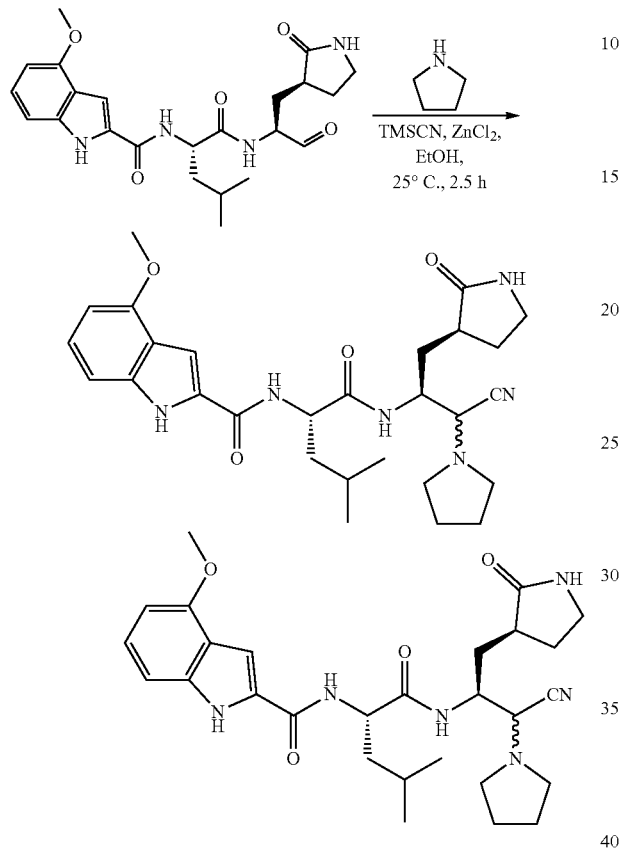

To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (700 mg, 1.27 mmol, 80% purity, 1 eq) in EtOH (10 mL) was added pyrrolidine (180.01 mg, 2.53 mmol, 211.28 uL, 2 eq) and ZnCl2 (1 M, 12.66 uL, 0.01 eq). The mixture was stirred at 25° C. for 30 min, and then added TMSCN (251.10 mg, 2.53 mmol, 316.65 uL, 2 eq). The mixture was stirred at 25° C. for 2 h. The reaction mixture was filtered and concentrated under reduced pressure to give a residue. The residue was purified by neutral prep-HPLC to get the compound N-[(1S)-1-[[(1S)-2-cyano-1-[[(3S)-2-oxopyrrolidin-3-yl]methyl]-2-pyrrolidin-1-yl-ethyl]carbamoyl]-3-methyl-butyl]-4-methoxy-1H-indole-2-carboxamide (110 mg, 199.95 umol, 15.80% yield, 95% purity) and N-[(1S)-1-[[(1S)-2-cyano-1-[[(3S)-2-oxopyrrolidin-3-yl]methyl]-2-pyrrolidin-1-yl-ethyl]carbamoyl]-3-methyl-butyl]-4-methoxy-1H-indole-2-carboxamide (110 mg, 199.95 umol, 15.80% yield, 95% purity) as white solid. MS (ESI) m/z 523.4 [M+H]+ column: Phenomenex luna CN 5 u 100*30 mm; mobile phase: [Hexane-IPA]; B %: 5%-40%, 20 min Isomer 1: $^1$H NMR (400 MHz, DMSO-d6) δ=11.58 (s, 1H), 8.43 (d, J=7.7 Hz, 1H), 8.20 (d, J=9.4 Hz, 1H), 7.68-7.49 (m, 1H), 7.38 (d, J=1.2 Hz, 1H), 7.18-6.93 (m, 2H), 6.50 (d, J=7.6 Hz, 1H), 4.57-3.99 (m, 3H), 3.88 (s, 3H), 3.19-2.95 (m, 2H), 2.64-2.53 (m, 4H), 2.38-2.27 (m, 1H), 2.15-2.01 (m, 1H), 1.85-1.44 (m, 10H), 0.91 (dd, J=6.4, 16.3 Hz, 6H)

Isomer 2: $^1$H NMR (400 MHz, DMSO-d6) δ=11.59 (br s, 1H), 8.39 (br d, J=7.6 Hz, 1H), 8.01 (br d, J=9.1 Hz, 1H), 7.69-7.49 (m, 1H), 7.43-7.28 (m, 1H), 7.16-6.86 (m, 2H), 6.50 (d, J=7.6 Hz, 1H), 4.59-4.24 (m, 3H), 3.88 (s, 3H), 3.19-2.94 (m, 2H), 2.71-2.57 (m, 2H), 2.49-2.32 (m, 3H), 2.18-2.08 (m, 1H), 2.06-1.93 (m, 1H), 1.83-1.37 (m, 9H), 0.90 (dd, J=6.5, 15.2 Hz, 6H)

Example 58. Synthesis of Viral Protease Inhibitor Compound 389

Step 1: (S)-2-amino-3-((S)-2-oxopyrrolidin-3-yl)propanamide

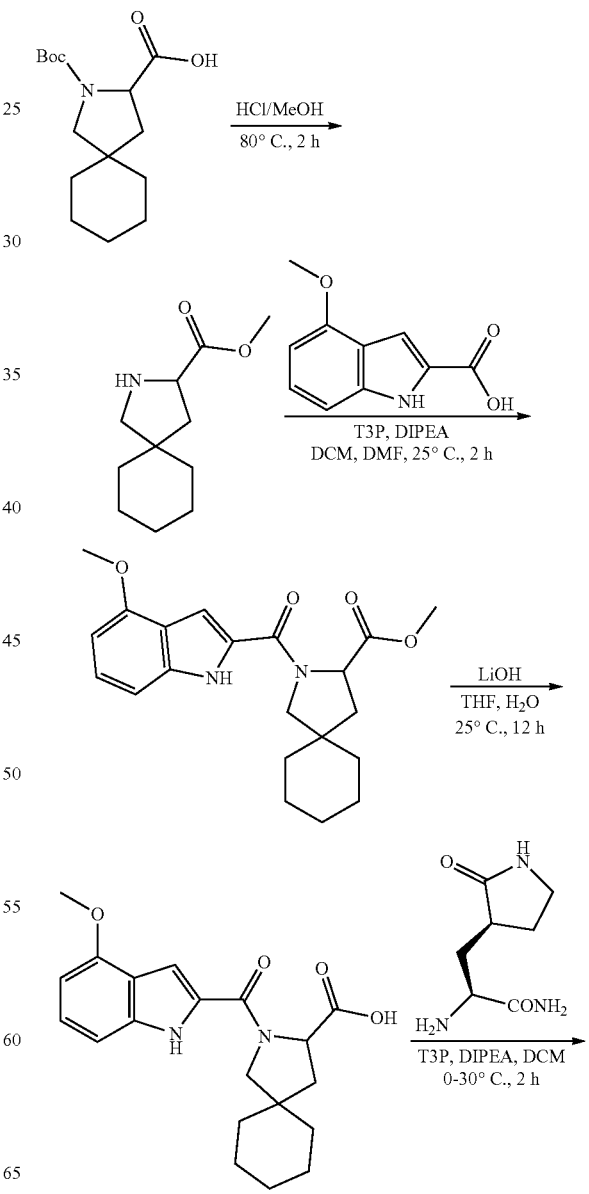

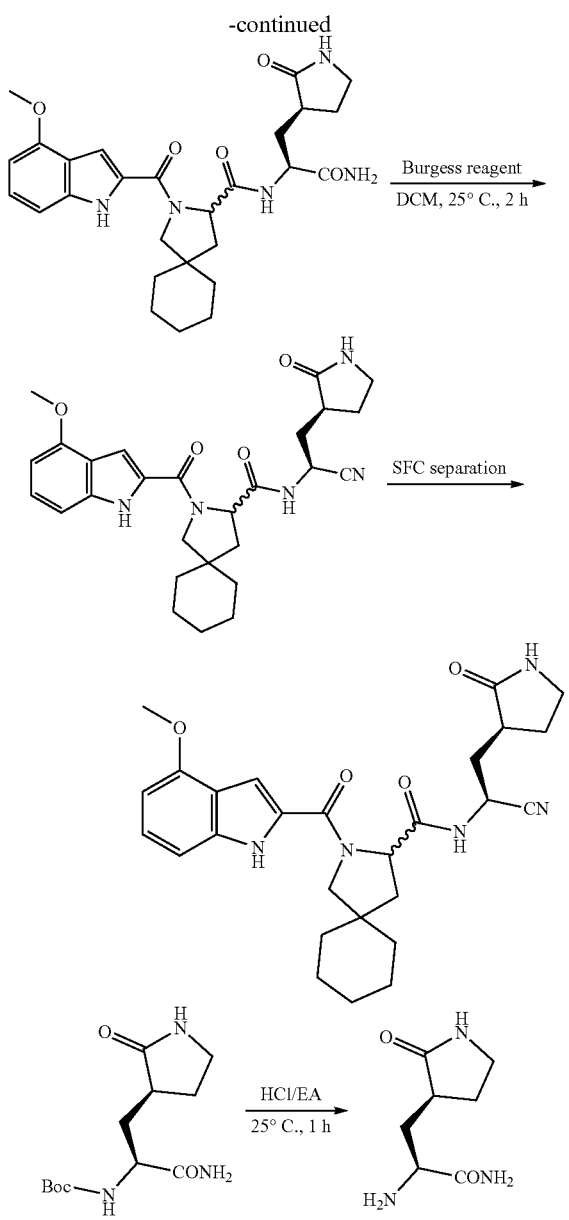

tert-butyl N-[(1S)-2-amino-2-oxo-1-[[(3S)-2-oxopyrrolidin-3-yl]methyl]ethyl]carbamate (2 g, 7.37 mmol, 1 eq) in HCl/EtOAc (4 M, 50 mL, 27.13 eq) was stirred at 25° C. for 1 h. Upon completion, the mixture was concentrated under the reduced pressure to afford (2S)-2-amino-3-[(3S)-2-oxopyrrolidin-3-yl]propanamide (1.2 g, crude) as a white solid.

Step 2: methyl 2-azaspiro[4.5]decane-3-carboxylate 2-tert-butoxycarbonyl-2-azaspiro[4.5]decane-3-carboxylic acid (3 g, 10.59 mmol, 1 eq) was added in HCl/MeOH (4 M, 50 mL, 18.89 eq). The mixture was stirred at 80° C. for 2 h. The mixture was concentrated under the reduced pressure affording the product methyl 2-azaspiro[4.5]decane-3-carboxylate (2 g, crude) as a yellow oil.

Step 3: methyl 2-(4-methoxy-1H-indole-2-carbonyl)-2-azaspiro[4.5]decane-3-carboxylate To a solution of methyl 2-azaspiro[4.5]decane-3-carboxylate (2 g, 10.14 mmol, 1 eq) and 4-methoxy-1H-indole-2-carboxylic acid (2.33 g, 12.17 mmol, 1.2 eq) in DCM (30 mL) and DMF (5 mL) was added T3P (12.90 g, 20.28 mmol, 12.06 mL, 50% purity, 2 eq) and DIEA (3.93 g, 30.41 mmol, 5.30 mL, 3 eq). The mixture was stirred at 25° C. for 2 h. Upon completion, the reaction mixture was quenched by addition H$_2$O (100 mL) and extracted with DCM (50 mL*3). The combined organic layers were washed with brine (50 mL), dried over Na$_2$SO$_4$, filtered and concentrated under reduced pressure to give a residue. The residue was purified by column chromatography (SiO$_2$, Petroleum ether:Ethyl acetate=10:1 to 0:1) affording the product methyl 2-(4-methoxy-1H-indole-2-carbonyl)-2-azaspiro[4.5]decane-3-carboxylate (3 g, 8.10 mmol, 79.88% yield) as a white solid. MS (ESI) m/z 371.1 [M+H]$^+$ Step 4: 2-(4-methoxy-1H-indole-2-carbonyl)-2-azaspiro[4.5]decane-3-carboxylic acid To a solution of methyl 2-(4-methoxy-1H-indole-2-carbonyl)-2-azaspiro[4.5]decane-3-carboxylate (3 g, 8.10 mmol, 1 eq) in THF (45 mL) and H$_2$O (15 mL) was added LiOH·H$_2$O (1.70 g, 40.49 mmol, 5 eq). The mixture was stirred at 25° C. for 12 h. Upon completion, the mixture was quenched by addition H$_2$O (50 mL), and then added aq. HCl (1 M) to adjust the pH=3-4, and extracted with ethyl acetate (50 mL*3). The combined organic layers were washed with brine (30 mL), dried over Na$_2$SO$_4$, filtered and concentrated under reduced pressure affording the product 2-(4-methoxy-1H-indole-2-carbonyl)-2-azaspiro[4.5]decane-3-carboxylic acid (2.6 g, crude) as a white solid. MS (ESI) m/z 357.1 [M+H]$^+$ Step 5: N-((S)-1-amino-1-oxo-3-((S)-2-oxopyrrolidin-3-yl)propan-2-yl)-2-(4-methoxy-1H-indole-2-carbonyl)-2-azaspiro[4.5]decane-3-carboxamide To a solution of 2-(4-methoxy-1H-indole-2-carbonyl)-2-azaspiro[4.5]decane-3-carboxylic acid (1 g, 2.81 mmol, 1 eq) and (2S)-2-amino-3-[(3S)-2-oxopyrrolidin-3-yl]propanamide (720.49 mg, 4.21 mmol, 1.5 eq) in DCM (30 mL) was added T3P (3.57 g, 5.61 mmol, 3.34 mL, 50% purity, 2 eq) and DIEA (1.09 g, 8.42 mmol, 1.47 mL, 3 eq) at 0° C. The mixture was stirred at 30° C. for 1 h. Upon completion, the mixture was quenched by the addition of H$_2$O (100 mL), and then extracted with DCM (50 mL*3). The combined organic layers were washed with brine (50 mL), dried over Na$_2$SO$_4$, filtered and concentrated under reduced pressure to give a residue. The residue was purified by column chromatography (SiO$_2$, DCM:MeOH=1:0 to 10:1) affording the product N-[(1S)-2-amino-2-oxo-1-[[(3S)-2-oxopyrrolidin-3-yl]methyl]ethyl]-2-(4-methoxy-1H-indole-2-carbonyl)-2-azaspiro[4.5]decane-3-carboxamide (700 mg, 1.37 mmol, 48.96% yield) as a white solid. MS (ESI) m/z 510.3 [M+H]$^+$ Step 6: N-((S)-1-cyano-2-((S)-2-oxopyrrolidin-3-yl)ethyl)-2-(4-methoxy-1H-indole-2-carbonyl)-2-azaspiro[4.5]decane-3-carboxamide To a solution of N-[(1S)-2-amino-2-oxo-1-[[(3S)-2-oxopyrrolidin-3-yl]methyl]ethyl]-2-(4-methoxy-1H-indole-2-carbonyl)-2-azaspiro[4.5]decane-3-carboxamide (700 mg, 1.37 mmol, 1 eq) in DCM (10 mL) was added Burgess reagent (982.03 mg, 4.12 mmol, 3 eq). The mixture was stirred at 25° C. for 2 h. Upon completion, the mixture was concentrated under the reduced pressure to give a residue. The residue was purified by prep-HPLC (column: Kromasil C18 (250*50 mm*10 um); mobile phase: [water (10 mM NH₄HCO₃)-ACN]; B %: 30%-60%, 10 min) affording the product N-[(1S)-1-cyano-2-[(3S)-2-oxopyrrolidin-3-yl]ethyl]-2-(4-methoxy-1H-indole-2-carbonyl)-2-azaspiro[4.5]decane-3-carboxamide (500 mg, 1.02 mmol, 74.05% yield) as a white solid. MS (ESI) m/z 492.3 [M+H]⁺

Step 7: N-((S)-1-cyano-2-((S)-2-oxopyrrolidin-3-yl)ethyl)-2-(4-methoxy-1H-indole-2-carbonyl)-2-azaspiro[4.5]decane-3-carboxamide N-[(1S)-1-cyano-2-[(3S)-2-oxopyrrolidin-3-yl]ethyl]-2-(4-methoxy-H-indole-2-carbonyl)-2-azaspiro[4.5]decane-3-carboxamide (500 mg, 1.02 mmol) was separated by SFC (column: DAICEL CHIRALPAK AD (250 mm*30 mm, 10 um); mobile phase: [0.1% NH₃H₂O IPA]; B %: 55%-55%, 9 min) affording the product N-[(1S)-1-cyano-2-[(3S)-2-oxopyrrolidin-3-yl]ethyl]-2-(4-methoxy-1H-indole-2-carbonyl)-2-azaspiro[4.5]decane-3-carboxamide Isomer 1 (264 mg, 537.04 umol, 52.80% yield, 100% purity) as a white solid. MS (ESI) m/z 492.3 [M+H]⁺

¹H NMR (400 MHz, METHANOL-d₄) δ=7.28-6.76 (m, 3H), 6.60-6.38 (m, 1H), 5.05 (br dd, J=5.2, 10.2 Hz, 1H), 4.63-4.60 (m, 1H), 4.03-3.85 (m, 5H), 3.74-3.28 (m, 1H), 2.73 (br dd, J=5.0, 8.6 Hz, 1H), 2.51-2.28 (m, 2H), 2.27-2.08 (m, 1H), 1.96-1.72 (m, 2H), 1.69-1.38 (m, 11H), 1.37-1.09 (m, 1H).

N-[(1S)-1-cyano-2-[(3S)-2-oxopyrrolidin-3-yl]ethyl]-2-(4-methoxy-1H-indole-2-carbonyl)-2-azaspiro[4.5]decane-3-carboxamide Isomer 2 (140 mg, 284.51 umol, 27.97% yield, 99.9% purity) as a white solid. MS (ESI) m/z 492.3 [M+H]⁺

¹H NMR (400 MHz, METHANOL-d₄) δ=7.30-6.81 (m, 3H), 6.53 (br d, J=2.0 Hz, 1H), 5.12-4.95 (m, 2H), 4.70-4.55 (m, 2H), 4.08-3.86 (m, 4H), 3.84-3.72 (m, 1H), 2.62-2.40 (m, 1H), 2.36-2.18 (m, 2H), 1.94-1.69 (m, 3H), 1.68-1.34 (m, 11H).

Example 59. Synthesis of Viral Protease Inhibitor Compound 513

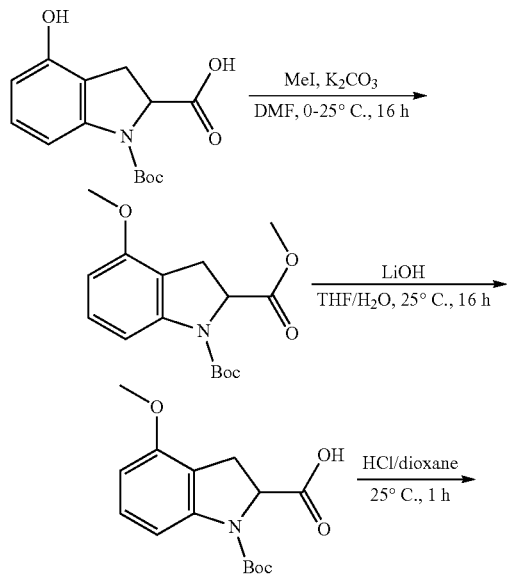

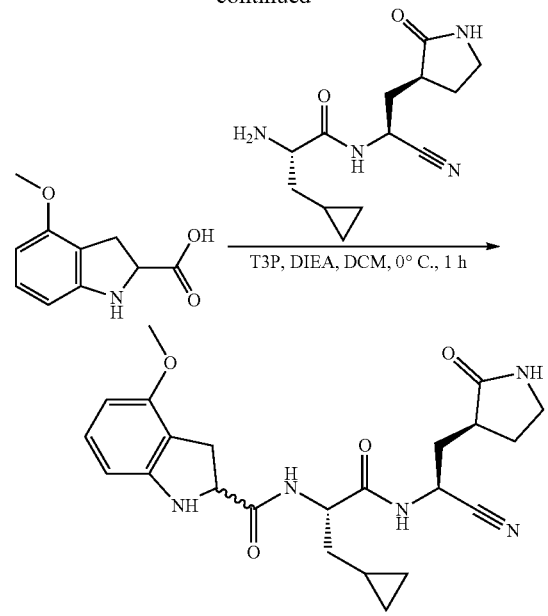

Step 1: O1-tert-butyl O2-methyl 4-methoxyinoline-1,2-dicarboxylate

A mixture of 1-tert-butoxycarbonyl-4-hydroxy-indoline-2-carboxylic acid (300 mg, 1.07 mmol, 1 eq) in DMF (4 mL) was added K₂CO₃ (445.37 mg, 3.22 mmol, 3 eq), and the mixture was added with MeI (381.16 mg, 2.69 mmol, 167.18 uL, 2.5 eq) at 0° C. After stirring at 25° C. for 16 h, the reaction mixture was diluted with H₂O (10 mL) and extracted with ethyl acetate (10 mL*3). The combined organic layers were washed with brine (10 mL*1), dried over Na₂SO₄, filtered and concentrated under reduced pressure to give the crude product. The crude was purified by column chromatography (SiO₂, Petroleum ether/Ethyl acetate=10/1 to 5/1) to give O1-tert-butyl O2-methyl 4-methoxyinoline-1,2-dicarboxylate (220 mg, 715.82 umol, 66.64% yield) as a yellow solid. MS (ESI) m/z 208.0 [M+H−Boc]⁺

Step 2: 1-tert-butoxycarbonyl-4-methoxy-indoline-2-carboxylic acid

A mixture of O1-tert-butyl O2-methyl 4-methoxyinoline-1,2-dicarboxylate (200 mg, 650.74 umol, 1 eq) in THF (1 mL) and H₂O (1 mL) was added LiOH (46.75 mg, 1.95 mmol, 3 eq) in one portion at 25° C. The mixture was stirred at 25° C. for 16 h. The reaction mixture was adjusted to acidity by HCl solution and extracted with ethyl acetate (2 mL*3). The combined organic layers were washed with brine (5 mL*1), dried over Na₂SO₄, filtered and concentrated under reduced pressure to give 1-tert-butoxycarbonyl-4-methoxy-indoline-2-carboxylic acid (175 mg, 596.63 umol, 45.84% yield) as a yellow oil. MS (ESI) m/z 237.9 [M+H−56]⁺

Step 3: 4-methoxyinoline-2-carboxylic acid

To a mixture of 1-tert-butoxycarbonyl-4-methoxy-indoline-2-carboxylic acid (150 mg, 511.40 umol, 1 eq) was added HCl/dioxane (4 M, 7.50 mL, 58.66 eq). The reaction was stirred at 25° C. for 1 h. The reaction mixture was concentrated under reduced pressure to give a residue and used next step directly to get the compound 4-methoxyinoline-2-carboxylic acid (110 mg, 431.07 umol, 84.29% yield, 90% purity, HCl) as yellow oil. MS (ESI) m/z 194.1 [M+H]+

Step 4: N-[(1S)-2-[[(1S)-1-cyano-2-[(3S)-2-oxopyrrolidin-3-yl]ethyl]amino]-1-(cyclopropylmethyl)-2-oxo-ethyl]-4-methoxy-indoline-2-carboxamide To a mixture of 4-methoxyinoline-2-carboxylic acid (110 mg, 478.97 umol, 1 eq, HCl) and (2S)-2-amino-N-[(1S)-1-cyano-2-[(3S)-2-oxopyrrolidin-3-yl]ethyl]-3-cyclopropyl-propanamide (316.51 mg, 478.97 umol, 40% purity, 1 eq) in DCM (8 mL) was added DIEA (123.81 mg, 957.94 umol, 166.86 uL, 2 eq) and T₃P (457.20 mg, 718.45 umol, 427.29 uL, 50% purity, 1.5 eq) at 0° C. The mixture was stirred at 0° C. for 1 h. The mixture was stirred with EDTA (10 mL) at 25° C., The reaction mixture was diluted with H₂O (30 mL) and extracted with DCM (30 mL*2). The combined organic layer was concentrated under reduced pressure to give a residue. The residue was purified with neutral prep-HPLC to get the compound N-[(1S)-2-[[(1S)-1-cyano-2-[(3S)-2-oxopyrrolidin-3-yl]ethyl]amino]-1-(cyclopropylmethyl)-2-oxo-ethyl]-4-methoxy-indoline-2-carboxamide (29 mg, 63.81 umol, 13.32% yield, 96.7% purity) and N-[(1S)-2-[[(1S)-1-cyano-2-[(3S)-2-oxopyrrolidin-3-yl]ethyl]amino]-1-(cyclopropylmethyl)-2-oxo-ethyl]-4-methoxy-indoline-2-carboxamide (26 mg, 55.61 umol, 11.61% yield, 94% purity) as a white solid. MS (ESI) m/z 440.2 [M+H]+
column: Waters Xbridge BEH C18 100*30 mm*10 um; mobile phase: [water (10 mM NH4HCO3)-ACN]; B %: 20%-50%, 10 min ¹H NMR (400 MHz, DMSO-d6) δ=8.99-8.83 (m, 1H), 8.08-7.89 (m, 1H), 7.71 (s, 1H), 6.92 (t, J=8.0 Hz, 1H), 6.25 (dd, J=4.4, 7.9 Hz, 2H), 5.91 (d, J=3.5 Hz, 1H), 5.05-4.85 (m, 1H), 4.42-4.14 (m, 2H), 3.70 (s, 3H), 3.28-2.97 (m, 3H), 2.90-2.76 (m, 1H), 2.43-2.26 (m, 1H), 2.19-1.98 (m, 2H), 1.87-1.54 (m, 3H), 1.50-1.31 (m, 1H), 0.79-0.54 (m, 1H), 0.47-0.26 (m, 2H), 0.20-0.10 (m, 2H)

¹H NMR (400 MHz, DMSO-d6) δ=8.88 (d, J=7.9 Hz, 1H), 7.95 (d, J=8.0 Hz, 1H), 7.70 (s, 1H), 6.93 (t, J=8.0 Hz, 1H), 6.26 (dd, J=4.5, 7.9 Hz, 2H), 5.92 (d, J=3.6 Hz, 1H), 5.08-4.84 (m, 1H), 4.50-4.17 (m, 2H), 3.70 (s, 3H), 3.27-2.99 (m, 3H), 2.88-2.72 (m, 1H), 2.40-2.25 (m, 1H), 2.17-2.02 (m, 2H), 1.87-1.57 (m, 3H), 1.51-1.39 (m, 1H), 0.70 (br s, 1H), 0.49-0.26 (m, 2H), 0.21-0.14 (m, 2H)

Example 60. Synthesis of Viral Protease Inhibitor Compound 515

Step 1: 4-hydroxy-1H-indole-2-carboxylic acid

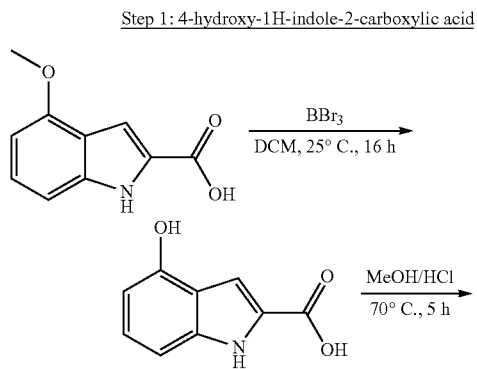

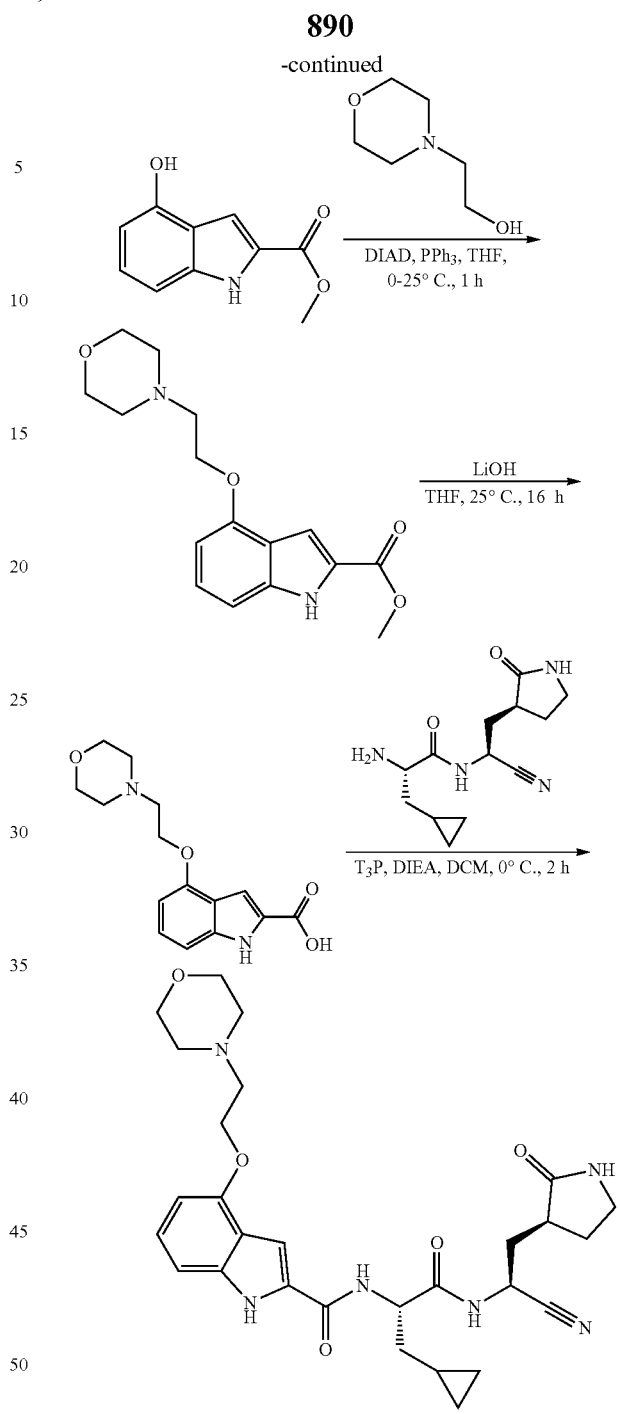

To a mixture of 4-methoxy-1H-indole-2-carboxylic acid (500 mg, 2.62 mmol, 1 eq) in DCM (10 mL) was added BBr₃ (1.31 g, 5.23 mmol, 2 eq) at 0° C. The mixture was stirred at 25° C. for 16 h. The mixture was diluted with H₂O (30 mL) and extracted with DCM (30 mL*2). The combined organic layers were washed with brine 20 mL, dried over Na₂SO₄, filtered and concentrated under reduced pressure to give 4-hydroxy-1H-indole-2-carboxylic acid (200 mg, crude) as a red solid. MS (ESI) m/z 176.1 [M–H]+

Step 2: methyl 4-hydroxy-1H-indole-2-carboxylate 4-hydroxy-1H-indole-2-carboxylic acid (200 mg, 1.13 mmol, 1 eq) was added with HCl/MeOH (4 M, 10 mL, 35.43 eq), and the mixture was stirred at 70° C. for 5 h. The reaction mixture was concentrated under reduced pressure to give the crude product. The crude was purified by column chromatography (SiO$_2$, Petroleum ether/Ethyl acetate=9/1 to 8/1) to give methyl 4-hydroxy-1H-indole-2-carboxylate (170 mg, 800.28 umol, 70.89% yield, 90% purity) as a yellow solid. MS (ESI) m/z 190.1 [M–H]$^+$ Step 3: methyl 4-(2-morpholinoethoxy)-1H-indole-2-carboxylate To a mixture of methyl 4-hydroxy-1H-indole-2-carboxylate (300 mg, 1.57 mmol, 1 eq) and 2-morpholinoethanol (205.83 mg, 1.57 mmol, 192.37 uL, 1 eq) in THF (4 mL) was added PPh$_3$ (452.73 mg, 1.73 mmol, 1.1 eq), DIAD (317.30 mg, 1.57 mmol, 305.10 uL, 1 eq) was added at 0° C. under N$_2$. The mixture was stirred at 25° C. for 60 min. The reaction mixture was diluted with H$_2$O (10 mL) and extracted with ethyl acetate (10 mL*2). The combined organic layers were washed with brine (20 mL), filtered and concentrated under reduced pressure to give a residue. The residue was purified by prep-TLC (PE:EA=0:1) to give methyl 4-(2-morpholinoethoxy)-1H-indole-2-carboxylate (200 mg, 591.44 umol, 37.69% yield, 90% purity) as a yellow solid. MS (ESI) m/z 304.9 [M+H]$^+$ Step 4: 4-(2-morpholinoethoxy)-1H-indole-2-carboxylic acid To a mixture of methyl 4-(2-morpholinoethoxy)-1H-indole-2-carboxylate (200 mg, 657.16 umol, 1 eq) in THF (2 mL) and H$_2$O (1 mL) was added LiOH·H$_2$O (41.37 mg, 985.74 umol, 1.5 eq) at 25° C. The mixture was stirred at 25° C. for 16 h. The reaction mixture was concentrated under reduced pressure to give a residue. The crude was purified by HCl prep-HPLC to give 4-(2-morpholinoethoxy)-1H-indole-2-carboxylic acid (80 mg, 261.79 umol, 39.84% yield, 95% purity) as a white solid. MS (ESI) m/z 289.2 [M–H]$^+$
column: Phenomenex luna C18 80*40 mm*3 um; mobile phase: [water(0.04% HCl)-ACN]; B %: 1%-32%, 6.5 min Step 5: N-[(1S)-2-[[(1S)-1-cyano-2-[(3S)-2-oxopyrrolidin-3-yl]ethyl]amino]-1-(cyclopropylmethyl)-2-oxo-ethyl]-4-(2-morpholinoethoxy)-1H-indole-2-carboxamide To a mixture of 4-(2-morpholinoethoxy)-1H-indole-2-carboxylic acid (70 mg, 241.12 umol, 1 eq) and (2S)-2-amino-N-[(1S)-1-cyano-2-[(3S)-2-oxopyrrolidin-3-yl]ethyl]-3-cyclopropyl-propanamide (159.33 mg, 241.12 umol, 40% purity, 1 eq) in DCM (2 mL) was added DIEA (93.49 mg, 723.36 umol, 125.99 uL, 3 eq) and T$_3$P (230.16 mg, 361.68 umol, 215.10 uL, 50% purity, 1.5 eq) in one portion at 0° C., and the mixture was stirred at 0° C. for 2 h. The reaction mixture was added with EDTA solution (2 mL) and stirred at 25° C. for 10 min, and then extracted with DCM (2 mL*3). The combined organic layers were washed with brine (5 mL*1), and concentrated under reduced pressure to give a residue. The residue was purified by prep-HPLC (neutral condition) to give N-[(1S)-2-[[(1S)-1-cyano-2-[(3S)-2-oxopyrrolidin-3-yl]ethyl]amino]-1-(cyclopropylmethyl)-2-oxo-ethyl]-4-(2-morpholinoethoxy)-1H-indole-2-carboxamide (13 mg, 24.23 umol, 10.05% yield) as a white solid. MS (ESI) m/z 537.3 [M+H]$^+$ column: Waters Xbridge Prep OBD C18 150*40 mm*10 um; mobile phase: [water (10 mM NH$_4$HCO$_3$)-ACN]; B %: 20%-50%, 8 min $^1$H NMR (400 MHz, DMSO-d$_6$) δ=11.57 (s, 1H), 8.92 (d, J=7.9 Hz, 1H), 8.60 (br d, J=7.5 Hz, 1H), 7.79-7.68 (m, 1H), 7.35 (d, J=1.5 Hz, 1H), 7.14-6.93 (m, 2H), 6.51 (d, J=7.5 Hz, 1H), 4.98 (q, J=7.9 Hz, 1H), 4.54-4.38 (m, 1H), 4.21 (br d, J=3.5 Hz, 2H), 3.59 (t, J=4.5 Hz, 4H), 3.20-3.05 (m, 2H), 2.78 (t, J=5.6 Hz, 2H), 2.60-2.52 (m, 4H), 2.43-2.28 (m, 1H), 2.23-2.04 (m, 2H), 1.92-1.60 (m, 3H), 1.56-1.38 (m, 1H), 0.80 (br d, J=5.3 Hz, 1H), 0.51-0.30 (m, 2H), 0.25-0.05 (m, 2H)

$^1$H NMR (400 MHz, METHANOL-d$_4$) δ=7.34-7.28 (m, 1H), 7.18-7.11 (m, 1H), 7.04 (d, J=8.4 Hz, 1H), 6.53 (d, J=7.5 Hz, 1H), 5.08 (dd, J=5.8, 10.3 Hz, 1H), 4.54 (t, J=7.4 Hz, 1H), 4.30 (t, J=5.3 Hz, 2H), 3.77-3.72 (m, 4H), 3.30-3.27 (m, 2H), 2.92 (t, J=5.3 Hz, 2H), 2.75-2.59 (m, 5H), 2.40-2.26 (m, 2H), 1.99-1.79 (m, 3H), 1.78-1.60 (m, 1H), 0.93-0.76 (m, 1H), 0.58-0.52 (m, 2H), 0.20 (br dd, J=5.0, 11.6 Hz, 2H)

Example 61. Synthesis of Viral Protease Inhibitor Compound 525

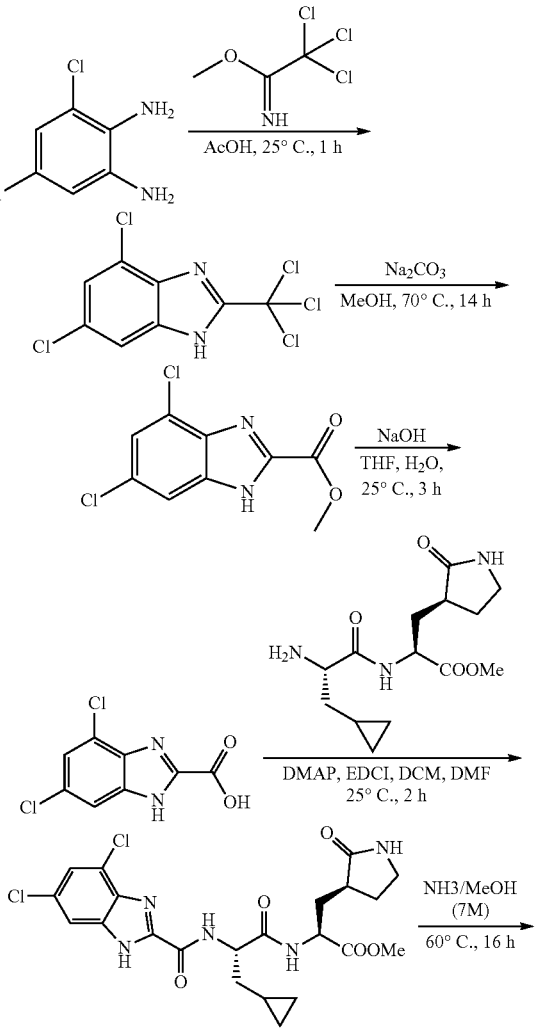

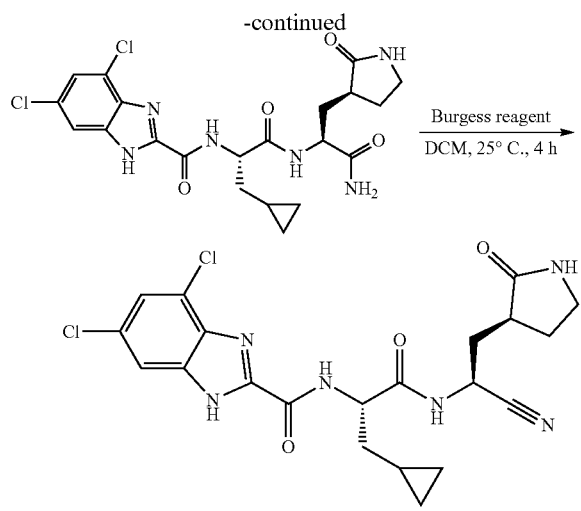

Step 1:
4,6-dichloro-2-(trichloromethyl)-1H-benzimidazole

A mixture of 3,5-dichlorobenzene-1,2-diamine (640.64 mg, 3.62 mmol, 1 eq) and methyl 2,2,2-trichloroethanimidoate (766.16 mg, 4.34 mmol, 535.78 uL, 1.2 eq) in AcOH (5 mL) was stirred at 25° C. for 1 h. Upon completion, the reaction mixture was diluted with H$_2$O (10 mL) and filtered to afford 4,6-dichloro-2-(trichloromethyl)-1H-benzimidazole (860 mg, 2.83 mmol, 78.07% yield) as a brown solid. MS (ESI) m/z 304.5 [M+2H]$^+$ Step 2: methyl 4,6-dichloro-1H-benzimidazole-2-carboxylate A mixture of 4,6-dichloro-2-(trichloromethyl)-1H-benzimidazole (420 mg, 1.38 mmol, 1 eq) in MeOH (5 mL) was added Na$_2$CO$_3$ (146.25 mg, 1.38 mmol, 1 eq) in one portion at 25° C. The mixture was heated to 70° C. and stirred for 14 hours. Upon completion, the reaction mixture was diluted with HCl (10 mL) and stirred at 25° C. for 1 h and extracted with ethyl acetate (8 mL*3). The combined organic layers were washed with brine (10 mL*1), dried over Na$_2$SO$_4$, filtered and concentrated under reduced pressure to give methyl 4,6-dichloro-1H-benzimidazole-2-carboxylate (330 mg, 1.35 mmol, 97.59% yield) as a brown solid. MS (ESI) m/z 245.0 [M+H]$^+$ Step 3: 4,6-dichloro-1H-benzimidazole-2-carboxylic acid To a mixture of methyl 4,6-dichloro-1H-benzimidazole-2-carboxylate (330 mg, 1.35 mmol, 1 eq) in THF (2 mL) and H$_2$O (2 mL) was added NaOH (161.58 mg, 4.04 mmol, 3 eq) in one portion at 25° C. The mixture was stirred at 25° C. for 3 h. Upon completion, the reaction mixture was adjusted to acidity with 1M HCl solution (5 mL), and then extracted with ethyl acetate (5 mL*3). The combined organic layers were washed with brine (10 mL*1), dried over Na$_2$SO$_4$, filtered and concentrated under reduced pressure to give 4,6-dichloro-1H-benzimidazole-2-carboxylic acid (200 mg, 865.67 umol, 64.29% yield) as a brown solid. MS (ESI) m/z 229.0 [M−H]$^+$ Step 4: methyl (2S)-2-[[(2S)-3-cyclopropyl-2-[(4,6-dichloro-1H-benzimidazole-2-carbonyl)amino]propanoyl]amino]-3-[(3S)-2-oxopyrrolidin-3-yl]propanoate To a mixture of methyl (2S)-2-[[(2S)-2-amino-3-cyclopropyl-propanoyl]amino]-3-[(3S)-2-oxopyrrolidin-3-yl]propanoate (140 mg, 470.83 umol, 1 eq) and 4,6-dichloro-1H-benzimidazole-2-carboxylic acid (197.78 mg, 470.83 umol, 55% purity, 1 eq) in DCM (3 mL) and DMF (1 mL) was added DMAP (172.56 mg, 1.41 mmol, 3 eq) in one portion at 25° C. The mixture was added EDCI (270.78 mg, 1.41 mmol, 3 eq) and stirred at 25° C. for 2 h. Upon completion, the reaction mixture was diluted with H$_2$O (4 mL) and extracted with ethyl acetate (5 mL*3). The combined organic layers were washed with brine (8 mL*1), dried over Na$_2$SO$_4$, filtered and concentrated under reduced pressure to give the crude product. The crude was purified by prep-HPLC (basic condition, column: Phenomenex Gemini-NX C18 75*30 mm*3 um; mobile phase: [water(0.05% NH$_3$H$_2$O+10 mM NH$_4$HCO$_3$)-ACN]; B %: 30%-60%, 8 min) to give methyl (2S)-2-[[(2S)-3-cyclopropyl-2-[(4,6-dichloro-1H-benzimidazole-2-carbonyl)amino]propanoyl]amino]-3-[(3S)-2-oxopyrrolidin-3-yl]propanoate (70 mg, 137.16 umol, 29.13% yield) as a white solid. MS (ESI) m/z 510.2 [M+H]$^+$ Step 5: N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4,6-dichloro-1H-benzimidazole-2-carboxamide A mixture of methyl (2S)-2-[[(2S)-3-cyclopropyl-2-[(4,6-dichloro-1H-benzimidazole-2-carbonyl)amino]propanoyl]amino]-3-[(3S)-2-oxopyrrolidin-3-yl]propanoate (60 mg, 117.56 umol, 1 eq) in NH$_3$/MeOH (7 M, 8 mL, 476.34 eq) was stirred at 60° C. for 16 h. Upon completion, the reaction mixture was concentrated under reduced pressure to give N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4,6-dichloro-1H-benzimidazole-2-carboxamide (58 mg, 117.09 umol, 99.60% yield) as a white solid. MS (ESI) m/z 495.2 [M+H]$^+$ Step 6: 4,6-dichloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-benzimidazole-2-carboxamide To a mixture of N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4,6-dichloro-1H-benzimidazole-2-carboxamide (50 mg, 100.94 umol, 1 eq) in DCM (1 mL) was added Burgess reagent (48.11 mg, 201.87 umol, 2 eq) in one portion at 25° C. The mixture was stirred at 25° C. for 4 h. Upon completion, the reaction mixture was concentrated under reduced pressure to give the crude product. The crude was purified by prep-HPLC (basic condition, column: Phenomenex Gemini-NX C18 75*30 mm*3 um; mobile phase: [water(0.05% NH$_3$H$_2$O+10 mM NH$_4$HCO$_3$)-ACN]; B %: 15%-45%, 8 min) to give 4,6-dichloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-benzimidazole-2-carboxamide (13 mg, 27.23 umol, 26.98% yield) as a white solid. MS (ESI) m/z 477.1 [M+H]$^+$
$^1$H NMR (400 MHz, DMSO-d$_6$) δ=13.77 (br s, 1H), 8.97-8.81 (m, 2H), 7.71 (s, 1H), 7.66-7.40 (m, 2H), 5.05-

4.91 (m, 1H), 4.60-4.48 (m, 1H), 3.21-3.03 (m, 2H), 2.43-2.28 (m, 1H), 2.22-2.06 (m, 2H), 2.02-1.85 (m, 1H), 1.84-1.54 (m, 3H), 0.81-0.69 (m, 1H), 0.48-0.34 (m, 211), 0.20-0.04 (m, 2H)

Example 62. Synthesis of Viral Protease Inhibitor Compound 529

Step 1: methyl (2S)-2-[[(2S)-2-[(6-chloro-1H-indole-2-carbonyl)amino]-3-cyclopropyl-propanoyl]amino]-3-[(3S)-2-oxopyrrolidin-3-yl]propanoate

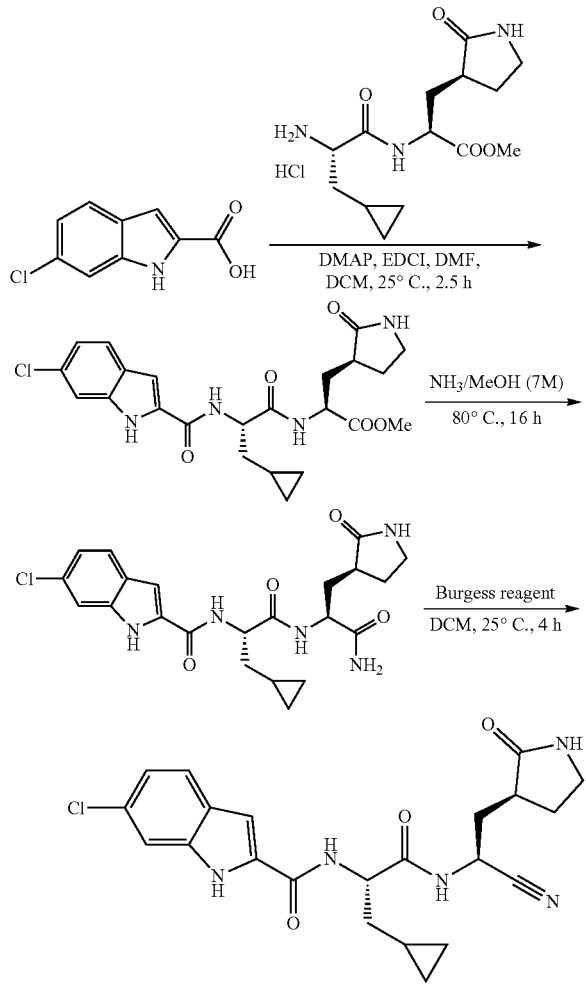

A mixture of 6-chloro-1H-indole-2-carboxylic acid (800 mg, 4.08 mmol, 1 eq) in DCM (6 mL) and DMF (3 mL) was added DMAP (1.50 g, 12.24 mmol, 3 eq) in one portion at 25° C. The mixture added methyl(2S)-2-[[(2S)-2-amino-3-cyclopropyl-propanoyl]amino]-3-[(3S)-2-oxopyrrolidin-3-yl]propanoate (1.36 g, 4.08 mmol, 1 eq, HCl) and EDCI (2.34 g, 12.24 mmol, 3 eq) in one portion at 25° C. and stirred for 2.5 h. Upon completion, the reaction mixture was concentrated under reduced pressure to give a residue. The residue was purified by prep-TLC (SiO$_2$, DCM:MeOH=10:1). Compound methyl (2S)-2-[[(2S)-2-[(6-chloro-1H-indole-2-carbonyl)amino]-3-cyclopropyl-propanoyl]amino]-3-[(3S)-2-oxopyrrolidin-3-yl]propanoate (900 mg, 1.89 mmol, 46.45% yield, 90% purity) was obtained as a white solid. MS (ESI) m/z 475.1 [M+H]$^+$.

Step 2: N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-6-chloro-1H-indole-2-carboxamide To a mixture of methyl(2S)-2-[[(2S)-2-[(6-chloro-1H-indole-2-carbonyl)amino]-3-cyclopropyl-propanoyl]amino]-3-[(3S)-2-oxopyrrolidin-3-yl]propanoate (900 mg, 1.89 mmol, 1 eq) in NH$_3$/MeOH (7 M, 10 mL, 94.99 eq) in one portion at 25° C. The mixture was stirred at 80° C. for 16 h. Upon completion, the reaction mixture was concentrated under reduced pressure to give a residue. Compound N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-6-chloro-1H-indole-2-carboxamide (750 mg, crude) was obtained as a white solid and was used fort the next step directly. MS (ESI) m/z 460.1 [M+H]$^+$.

Step 3: 6-chloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-indole-2-carboxamide A mixture of N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-6-chloro-1H-indole-2-carboxamide (700 mg, 1.52 mmol, 1 eq) in DCM (7 mL) was added Burgess reagent (725.41 mg, 3.04 mmol, 2.5 eq) in one portion at 25° C. The mixture was stirred at 25° C. for 4 h. Upon completion, the reaction mixture was concentrated under reduced pressure to give a residue. The residue was purified by prep-HPLC (column: Waters Xbridge Prep OBD C18 150*40 mm*10 um; mobile phase: [water (10 mM NH$_4$HCO$_3$)-ACN]; B %: 30%-60%, 8 min). Compound 6-chloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-indole-2-carboxamide (60 mg, 133.90 umol, 30.79% yield, 98.622% purity) was obtained as a white solid. MS (ESI) m/z 442.1 [M+H]$^+$.

$^1$H NMR (400 MHz, DMSO-d$_6$) δ ppm 11.74 (br s, 1H), 8.95 (br d, J=7.72 Hz, 1H), 8.66 (br d, J=7.28 Hz, 1H), 7.65-7.74 (m, 2H), 7.43 (s, 1H), 7.32 (s, 1H), 7.05 (dd, J=8.49, 1.87 Hz, 1H), 4.95-5.03 (m, 1H), 4.47 (br dd, J=13.67, 7.94 Hz, 1H), 3.07-3.18 (m, 2H), 2.31-2.41 (m, 1H), 2.07-2.18 (m, 2H), 1.65-1.89 (m, 3H), 1.42-1.54 (m, 1H), 0.80 (br s, 1H), 0.36-0.49 (m, 2H), 0.07-0.24 (m, 2H), −0.69--0.69 (m, 1H)

Example 63. Synthesis of Viral Protease Inhibitor Compound 539

Step 1: (S)-methyl 2-amino-3-((S)-2-oxopyrrolidin-3-yl)propanoate hydrochloride

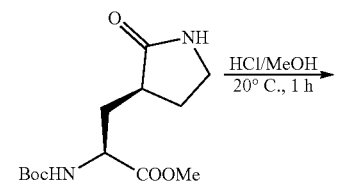

897
-continued

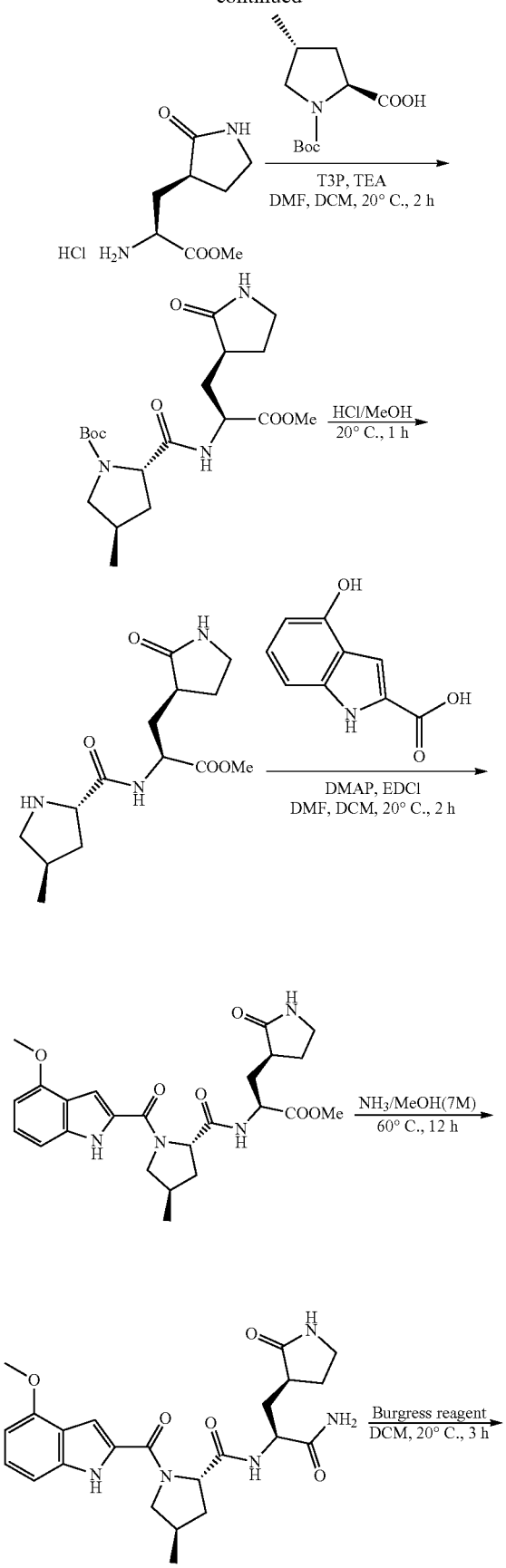

898
-continued

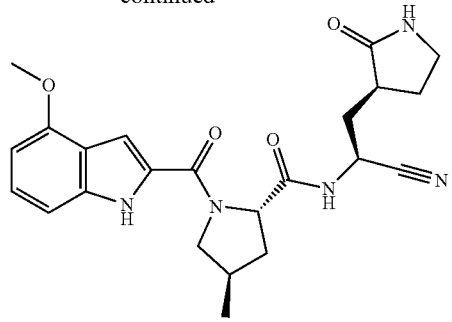

A solution of methyl (2S)-2-(tert-butoxycarbonylamino)-3-[(3S)-2-oxopyrrolidin-3-yl]propanoate (500 mg, 1.75 mmol, 1 eq) in HCl/MeOH (4 M, 20 mL, 45.81 eq) was stirred at 20° C. for 1 h, and the reaction mixture was concentrated under reduced pressure to afford methyl (2S)-2-amino-3-[(3S)-2-oxopyrrolidin-3-yl]propanoate (350 mg, crude, HCl) as a yellow solid.

Step 2: (2S,4R)-tert-butyl 2-(((S)-1-methoxy-1-oxo-3-((S)-2-oxopyrrolidin-3-yl)propan-2-yl)carbamoyl)-4-methylpyrrolidine-1-carboxylate To a solution of (2S,4R)-1-tert-butoxycarbonyl-4-methyl-pyrrolidine-2-carboxylic acid (250 mg, 1.09 mmol, 1 eq) and methyl (2S)-2-amino-3-[(3S)-2-oxopyrrolidin-3-yl]propanoate (304.45 mg, 1.64 mmol, 1.5 eq) in DCM (10 mL) was added drop-wise T3P (1.04 g, 1.64 mmol, 972.75 uL, 50% purity, 1.5 eq) and Et₃N (662.02 mg, 6.54 mmol, 910.62 uL, 6 eq), and the mixture was stirred at 20° C. for 2 h. The reaction mixture was quenched by addition H₂O (40 mL) at 0° C., and then extracted with DCM (30 mL*3). The combined organic layers were washed with brine (40 mL), dried over Na₂SO₄, filtered and concentrated under reduced pressure to give a residue. The residue was purified by column chromatography (SiO₂, Petroleum ether:Ethyl acetate=10:1 to 0:1) to afford tert-butyl (2S,4R)-2-[[(1S)-2-methoxy-2-oxo-1-[[(3S)-2-oxopyrrolidin-3-yl]methyl]ethyl]carbamoyl]-4-methyl-pyrrolidine-1-carboxylate (320 mg, 805.10 umol, 73.86% yield) as a colorless oil. MS (ESI) m/z 398.2 [M+H]⁺.

Step 3: (S)-methyl 2-((2S,4R)-4-methylpyrrolidine-2-carboxamido)-3-((S)-2-oxopyrrolidin-3-yl)propanoate A solution of tert-butyl (2S,4R)-2-[[(1S)-2-methoxy-2-oxo-1-[[(3S)-2-oxopyrrolidin-3-yl]methyl]ethyl]carbamoyl]-4-methyl-pyrrolidine-1-carboxylate (260 mg, 654.15 umol, 1 eq) in HCl/MeOH (4 M, 8 mL, 48.92 eq) was stirred at 20° C. for 1 h. The reaction mixture was concentrated under reduced pressure to afford methyl (2S)-2-[[(2S,4R)-4-methylpyrrolidine-2-carbonyl]amino]-3-[(3S)-2-oxopyrrolidin-3-yl]propanoate (200 mg, crude, HCl) as a colorless oil. MS (ESI) m/z 298.2 [M+H]⁺.

Step 4: (S)-methyl 2-((2S,4R)-1-(4-methoxy-1H-indole-2-carbonyl)-4-methylpyrrolidine-2-carboxamido)-3-((S)-2-oxopyrrolidin-3-yl)propanoate To a solution of methyl (2S)-2-[[(2S,4R)-4-methylpyrrolidine-2-carbonyl]amino]-3-[(3S)-2-oxopyrrolidin-3-yl]propanoate (200 mg, 599.14 umol, 1 eq, HCl) and 4-methoxy- 1H-indole-2-carboxylic acid (229.09 mg, 1.20 mmol, 2.0 eq) in DMF (2.0 mL) was added DMAP (219.59 mg, 1.80 mmol, 3.0 eq) and EDCI (229.71 mg, 1.20 mmol, 2 eq) and DCM (8.0 mL), the mixture was stirred at 20° C. for 2 h. The reaction mixture was quenched by addition H$_2$O (50 mL) at 0° C., and then extracted with DCM (40 mL*3). The combined organic layers were washed with brine (60 mL), dried over Na$_2$SO$_4$, filtered and concentrated under reduced pressure to give a residue. The residue was purified by column chromatography (SiO$_2$, Petroleum ether:Ethyl acetate=1:1 to 0:1) to afford methyl (2S)-2-[[(2S,4R)-1-(4-methoxy-1H-indole-2-carbonyl)-4-methyl-pyrrolidine-2-carbonyl]amino]-3-[(3S)-2-oxopyrrolidin-3-yl]propanoate (250 mg, 494.14 umol, 82.47% yield, 93% purity) as a yellow solid. MS (ESI) m/z 471.3 [M+H]$^+$.

Step 5: (2S,4R)-N-[(1S)-2-amino-2-oxo-1-[[(3S)-2-oxopyrrolidin-3-yl]methyl]ethyl]-1-(4-methoxy-1H-indole-2-carbonyl)-4-methyl-pyrrolidine-2-carboxamide A solution of methyl (2S)-2-[[(2S,4R)-1-(4-methoxy-1H-indole-2-carbonyl)-4-methyl-pyrrolidine-2-carbonyl]amino]-3-[(3S)-2-oxopyrrolidin-3-yl]propanoate (220 mg, 434.84 umol, 93% purity, 1 eq) in NH$_3$/MeOH (7 M, 20 mL, 321.96 eq) was stirred at 60° C. for 12 h. The reaction mixture was concentrated under reduced pressure to afford (2S,4R)-N-[(1S)-2-amino-2-oxo-1-[[(3S)-2-oxopyrrolidin-3-yl]methyl]ethyl]-1-(4-methoxy-1H-indole-2-carbonyl)-4-methyl-pyrrolidine-2-carboxamide (200 mg, crude) as a yellow solid. MS (ESI) m/z 456.2 [M+H]$^+$.

Step 6: (2S,4R)-N-[(1S)-1-cyano-2-[(3S)-2-oxopyrrolidin-3-yl]ethyl]-1-(4-methoxy-1H-indole-2-carbonyl)-4-methyl-pyrrolidine-2-carboxamide A solution of (2S,4R)-N-[(1S)-2-amino-2-oxo-1-[[(3S)-2-oxopyrrolidin-3-yl]methyl]ethyl]-1-(4-methoxy-1H-indole-2-carbonyl)-4-methyl-pyrrolidine-2-carboxamide (100 mg, 219.54 umol, 1 eq) in DCM (5 mL) was added methoxycarbonyl-(triethylammonio)sulfonyl-azanide (313.90 mg, 1.32 mmol, 6 eq) was stirred at 20° C. for 3 h. The reaction mixture was concentrated under reduced pressure to give a residue. The residue was purified by prep-HPLC (column: Phenomenex Luna C18 75*30 mm*3 um; mobile phase: [water (0.2% FA)-ACN]; B %: 25%-60%, 8 min) to afford (2S,4R)-N-[(1S)-1-cyano-2-[(3S)-2-oxopyrrolidin-3-yl]ethyl]-1-(4-methoxy-1H-indole-2-carbonyl)-4-methyl-pyrrolidine-2-carboxamide (33 mg, 75.43 umol, 34.36% yield, 100% purity) as a white solid. MS (ESI) m/z 438.2 [M+H]$^+$.

$^1$H NMR (400 MHz, DMSO-d$_6$) δ=11.73-11.47 (m, 1H), 8.85 (br d, J=8.3 Hz, 1H), 7.84-7.54 (m, 1H), 7.24-6.84 (m, 3H), 6.74-6.48 (m, 1H), 5.10-4.47 (m, 2H), 4.20-3.75 (m, 4H), 3.47 (t, J=9.0 Hz, 1H), 3.16 (d, J=7.9 Hz, 1H), 2.61 (s, 1H), 2.43-2.36 (m, 1H), 2.27-1.43 (m, 7H), 1.07 (d, J=6.4 Hz, 3H).

$^1$H NMR (400 MHz, METHANOL-d$_4$) δ=7.25-6.75 (m, 3H), 6.59-6.40 (m, 1H), 5.15-5.00 (m, 1H), 4.84-4.61 (m, 1H), 4.30-4.06 (m, 1H), 3.98-3.84 (m, 3H), 3.55 (t, J=8.9 Hz, 1H), 3.30-3.24 (m, 1H), 3.01-2.54 (m, 2H), 2.46-2.09 (m, 4H), 2.01-1.38 (m, 3H), 1.15 (br d, J=6.6 Hz, 3H).

Example 64. Synthesis of Viral Protease Inhibitor Compound 547

Step 1: 9H-fluoren-9-ylmethyl (1S,2S,5R)-2-[[(1S)-1-cyano-2-[(3S)-2-oxopyrrolidin-3-yl]ethyl]carbamoyl]-3-axabicyclo[3.2.0]heptane-3-carboxylate

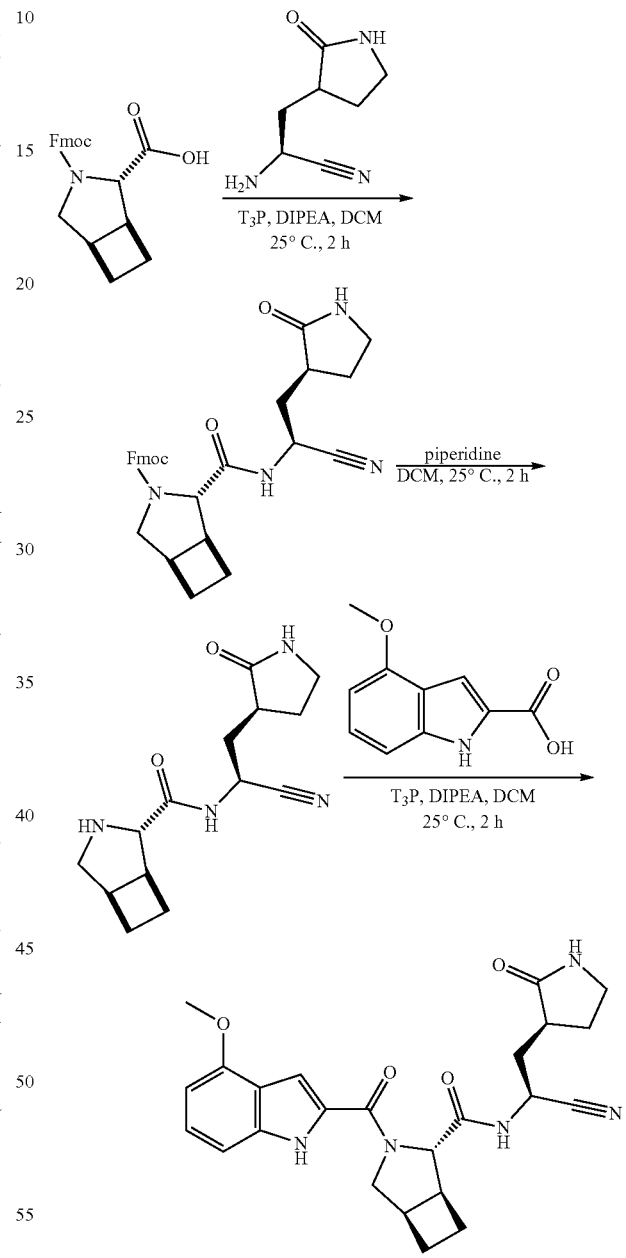

(1S,2S,5R)-3-(9H-fluoren-9-ylmethoxycarbonyl)-3-azabicyclo[3.2.0]heptane-2-carboxylic acid (150 mg, 412.76 umol, 1 eq), (2S)-2-amino-3-[(3S)-2-oxopyrrolidin-3-yl]propanenitrile (75.87 mg, 495.31 umol, 1.2 eq) in DCM (2 mL) was added T3P (394.00 mg, 619.14 umol, 368.22 uL, 50% purity, 1.5 eq) and DIEA (160.04 mg, 1.24 mmol, 215.69 uL, 3 eq), and the resulting mixture was stirred at 25° C. for 2 h. Upon completion, the solution was diluted with H$_2$O (20 mL), extracted with ethyl acetate (20 mL*3), the combined organic phase was dried over Na₂SO₄, filtrated and concentrated to give the crude. The residue was purified by prep-TLC (SiO₂, DCM:MeOH=10:1) to afford 9H-fluoren-9-ylmethyl (1S,2S,5R)-2-[[(1S)-1-cyano-2-[(3S)-2-oxopyrrolidin-3-yl]ethyl]carbamoyl]-3-azabicyclo[3.2.0]heptane-3-carboxylate (130 mg, 260.74 umol, 63.17% yield, 100% purity) as white solid. MS (ESI) m/z 499.3 [M+H]⁺.

Step 2: (1S,2S,5R)-N-[(1S)-1-cyano-2-[(3S)-2-oxopyrrolidin-3-yl]ethyl]-3-azabicyclo[3.2.0]heptane-2-carboxamide To a solution of 9H-fluoren-9-ylmethyl (1S,2S,5R)-2-[[(1S)-1-cyano-2-[(3S)-2-oxopyrrolidin-3-yl]ethyl]carbamoyl]-3-azabicyclo[3.2.0]heptane-3-carboxylate (250 mg, 401.15 umol, 80% purity, 1 eq) in DCM (2.5 mL) was added piperidine (68.31 mg, 802.29 umol, 79.23 uL, 2 eq), and the solution was stirred at 25° C. for 2 h. Upon completion, DCM was removed with blow-dry to afford a residue. The residue was purified by prep-TLC (SiO₂, DCM:MeOH=10:1) to give (1S,2S,5R)-N-[(1S)-1-cyano-2-[(3S)-2-oxopyrrolidin-3-yl]ethyl]-3-azabicyclo[3.2.0]heptane-2-carboxamide (80 mg, 289.51 umol, 72.17% yield, 100% purity) as yellow solid. MS (ESI) m/z 277.2 [M+H]⁺.

Step 3: (1S,2S,5R)-N-[(1S)-1-cyano-2-[(3S)-2-oxopyrrolidin-3-yl]ethyl]-3-(4-methoxy-1H-indole-2-carbonyl)-3-azabicyclo[3.2.0]heptane-2-carboxamide To a solution of (1S,2S,5R)-N-[(1S)-1-cyano-2-[(3S)-2-oxopyrrolidin-3-yl]ethyl]-3-azabicyclo[3.2.0]heptane-2-carboxamide (80 mg, 289.51 umol, 1 eq), 4-methoxy-1H-indole-2-carboxylic acid (83.02 mg, 434.26 umol, 1.5 eq) in DCM (1.5 mL) was added the T3P (276.35 mg, 434.26 umol, 258.27 uL, 50% purity, 1.5 eq) and DIEA (112.25 mg, 868.52 umol, 151.28 uL, 3 eq). The resulting solution was stirred at 25° C. for 1 h. Upon completion, the solution was diluted with H₂O (20 mL), extracted with ethyl acetate (20 mL*3), and the combined organic phase was dried over Na₂SO₄, filtrated and concentrated to give the crude. The residue was purified by prep-HPLC (column: Waters Xbridge BEH C18 100*30 mm*10 um; mobile phase: [water (10 mM NH₄HCO₃)-ACN]; B %: 20%-50%, 8 min) to afford (1S,2S,5R)-N-[(1S)-1-cyano-2-[(3S)-2-oxopyrrolidin-3-yl]ethyl]-3-(4-methoxy-1H-indole-2-carbonyl)-3-azabicyclo[3.2.0]heptane-2-carboxamide (50 mg, 111.23 umol, 38.42% yield, 100% purity) as white solid. MS (ESI) m/z 449.9 [M+H]⁺.

¹H NMR (400 MHz, DMSO-d₆) δ=11.57 (br s, 1H), 9.23-8.65 (m, 1H), 7.69 (br s, 1H), 7.23-6.82 (m, 3H), 6.52 (br d, J=7.4 Hz, 1H), 5.08-4.84 (m, 1H), 4.63 (br d, J=8.2 Hz, 1H), 4.25 (br s, 1H), 4.06 (br s, 1H), 3.89 (br s, 3H), 3.27-2.79 (m, 4H), 2.28-1.53 (m, 9H).

Example 65. Synthesis of Viral Protease Inhibitor Compound 549

Step 1: tert-butyl (2S,4R)-2-[[(1S)-2-methoxy-2-oxo-1-[[(3S)-2-oxopyrrolidin-3-yl]methyl]ethyl]carbamoyl]-4-(trifluoromethyl)pyrrolidine-1-carboxylate

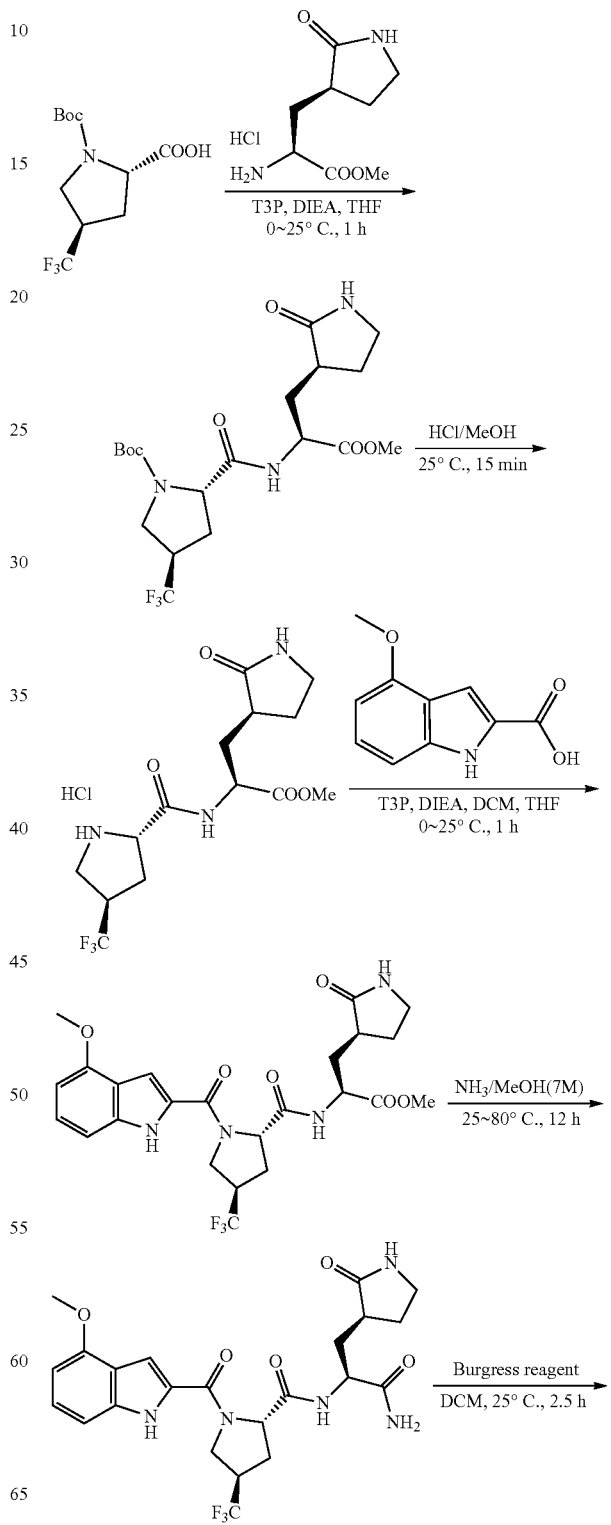

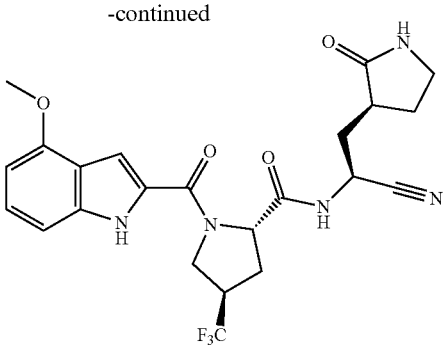

To a mixture of methyl (2S)-2-amino-3-[(3S)-2-oxopyrrolidin-3-yl]propanoate (283.01 mg, 1.27 mmol, 1.2 eq, HCl) and (2S,4R)-1-tert-butoxycarbonyl-4-(trifluoromethyl)pyrrolidine-2-carboxylic acid (300 mg, 1.06 mmol, 1 eq), DIEA (684.44 mg, 5.30 mmol, 922.43 uL, 5 eq) in THF (3 mL) was added T3P (1.01 g, 1.59 mmol, 944.87 uL, 50% purity, 1.5 eq) at 0° C. under $N_2$. The mixture was stirred at 25° C. for 1 h. Upon completion, the residue was poured into saturated sodium bicarbonate solution (10 mL) and stirred for 1 min. The aqueous phase was extracted with ethyl acetate (10 mL*2). The combined organic phase was washed with brine (10 mL), dried with anhydrous $Na_2SO_4$, filtered and concentrated in vacuum to give tert-butyl(2S,4R)-2-[[(1S)-2-methoxy-2-oxo-1-[[(3S)-2-oxopyrrolidin-3-yl]methyl]ethyl]carbamoyl]-4-(trifluoromethyl)pyrrolidine-1-carboxylate (0.5 g, crude) as light yellow oil and used directly next step. MS (ESI) m/z 452.1 $[M+H]^+$.

Step 2: methyl (2S)-3-[(3S)-2-oxopyrrolidin-3-yl]-2-[[(2S,4R)-4-(trifluoromethyl)pyrrolidine-2-carbonyl]amino]propanoate To tert-butyl (2S,4R)-2-[[(1S)-2-methoxy-2-oxo-1-[[(3S)-2-oxopyrrolidin-3-yl]methyl]ethyl]carbamoyl]-4-(trifluoromethyl)pyrrolidine-1-carboxylate (0.5 g, 1.11 mmol, 1 eq) was added HCl/MeOH (4 M, 3 mL, 10.83 eq) at 25° C. under $N_2$. The mixture was stirred at 25° C. for 15 min. Upon completion, the reaction mixture was concentrated to get the crude product methyl (2S)-3-[(3S)-2-oxopyrrolidin-3-yl]-2-[[(2S,4R)-4-(trifluoromethyl)pyrrolidine-2-carbonyl]amino]propanoate (450 mg, crude, HCl) as the light yellow oil. MS (ESI) m/z 352.1 $[M+H]^+$.

Step 3: methyl (2S)-2-[[(2S,4R)-1-(4-methoxy-1H-indole-2-carbonyl)-4-(trifluoromethyl)pyrrolidine-2-carbonyl]amino]-3-[(3S)-2-oxopyrrolidin-3-yl]propanoate To a mixture of methyl (2S)-3-[(3S)-2-oxopyrrolidin-3-yl]-2-[[(2S,4R)-4-(trifluoromethyl) pyrrolidine-2-carbonyl]amino]propanoate (395.52 mg, 1.02 mmol, 1.3 eq, HCl) and 4-methoxy-1H-indole-2-carboxylic acid (150 mg, 784.59 umol, 1 eq) and DIPEA (507.01 mg, 3.92 mmol, 683.31 uL, 5 eq) in THF (3 mL) and DCM (3 mL) was added T3P (748.92 mg, 1.18 mmol, 699.93 uL, 50% purity, 1.5 eq) at 0° C. under $N_2$. The mixture was stirred at 25° C. for 1 h. Upon completion, the reaction mixture was poured into saturated sodium bicarbonate solution (5 mL) and stirred for 2 min. The aqueous phase was extracted with ethyl acetate (5 mL*2). The combined organic phase was washed with brine (5 mL), dried with anhydrous $Na_2SO_4$, filtered and concentrated in vacuum. The crude product was purified by prep-TLC (dichloromethane:methanol=10:1, $R_f$=0.43) to give Methyl (2S)-2-[[(2S,4R)-1-(4-methoxy-1H-indole-2-carbonyl)-4-(trifluoromethyl)pyrrolidine-2-carbonyl]amino]-3-[(3S)-2-oxopyrrolidin-3-yl]propanoate (250 mg, crude) was obtained as the light yellow solid. MS (ESI) m/z 525.2 $[M+H]^+$.

Step 4: (2S,4R)-1-(4-methoxy-1H-indole-2-carbonyl)-N-[(1S)-1-(nitrosomethyl)-2-[(3S)-2-oxopyrrolidin-3-yl]ethyl]-4-(trifluoromethyl)pyrrolidine-2-carboxamide To a mixture of methyl (2S)-2-[[(2S,4R)-1-(4-methoxy-1H-indole-2-carbonyl)-4-(trifluoromethyl)pyrrolidine-2-carbonyl]amino]-3-[(3S)-2-oxopyrrolidin-3-yl]propanoate (250 mg, 476.65 umol, 1 eq) was added $NH_3$/MeOH (7 M, 3 mL, 44.06 eq) in one portion at 25° C. under $N_2$. The mixture was stirred at 80° C. for 12 h. Upon completion, the reaction mixture was cooled to 25° C. and concentrated to get the crude product. The crude product was purified by prep-TLC (dichloromethane:methanol=10:1, Rf=0.3) to afford (2S,4R)-1-(4-methoxy-1H-indole-2-carbonyl)-N-[(1S)-1-(nitrosomethyl)-2-[(3S)-2-oxopyrrolidin-3-yl]ethyl]-4-(trifluoromethyl)pyrrolidine-2-carboxamide (130 mg, 247.51 umol, 51.93% yield, 97% purity) as a light yellow solid. MS (ESI) m/z 510.2 $[M+H]^+$.

Step 5: (2S,4R)-N-[(1S)-1-cyano-2-[(3S)-2-oxopyrrolidin-3-yl]ethyl]-1-(4-methoxy-1H-indole-2-carbonyl)-4-(trifluoromethyl)pyrrolidine-2-carboxamide To a mixture of (2S,4R)-1-(4-methoxy-1H-indole-2-carbonyl)-N-[(1S)-1-(nitrosomethyl)-2-[(3S)-2-oxopyrrolidin-3-yl]ethyl]-4-(trifluoromethyl)pyrrolidine-2-carboxamide (120 mg, 235.54 umol, 1 eq) in DCM (6 mL) was added Burgess reagent (112.26 mg, 471.07 umol, 2 eq) in one portion at 25° C. under $N_2$. The mixture was stirred at 25° C. for 4.5 h. Upon completion, the residue was poured into water (0.5 mL) and stirred for 10 min. Then the reaction mixture was concentrated to get the crude product. The crude product was purified by prep-HPLC (column: Phenomenex Gemini-NX 80*40 mm*3 um; mobile phase: [water (10 mM $NH_4HCO_3$)-ACN]; B %: 25%-45%, 8 min) to give (2S,4R)-N-[(1S)-1-cyano-2-[(3S)-2-oxopyrrolidin-3-yl]ethyl]-1-(4-methoxy-1H-indole-2-carbonyl)-4-(trifluoromethyl)pyrrolidine-2-carboxamide (22.56 mg, 45.90 umol, 19.49% yield, 100% purity) as a white solid. MS (ESI) m/z 492.2 $[M+H]^+$.

$^1$H NMR (400 MHz, METHANOL-$d_4$) δ ppm 7.12-7.21 (m, 1H), 6.84-7.10 (m, 2H), 6.50 (br s, 1H), 4.94-5.26 (m, 1H), 4.75 (br s, 1H), 4.07-4.47 (m, 2H), 3.79-4.01 (m, 3H), 3.45 (br s, 1H), 2.16-2.98 (m, 6H), 1.62-2.02 (m, 2H), 1.39 (br s, 1H).

Example 66. Synthesis of Viral Protease Inhibitor Compound 557

Step 1: (S)-methyl 2-amino-3-((S)-2-oxopyrrolidin-3-yl) propanoate hydrochloride

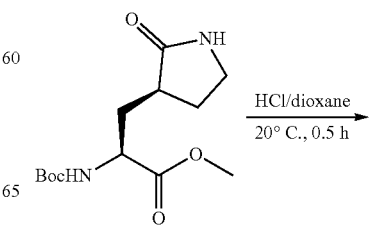

905
-continued

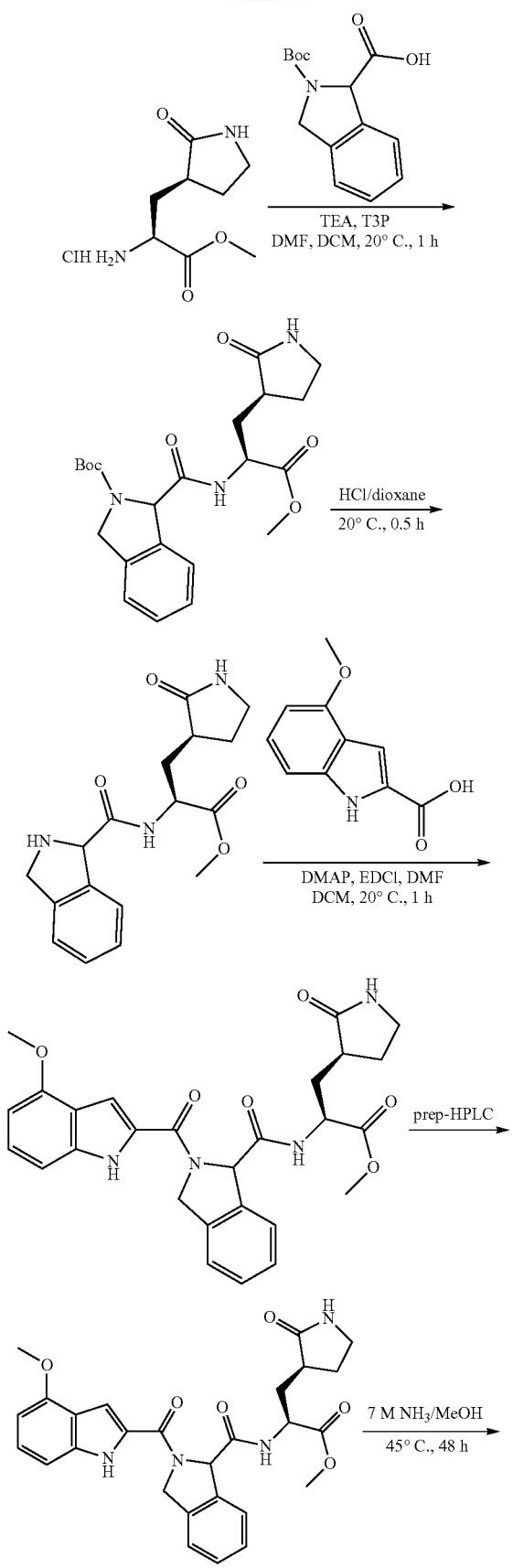

906
-continued

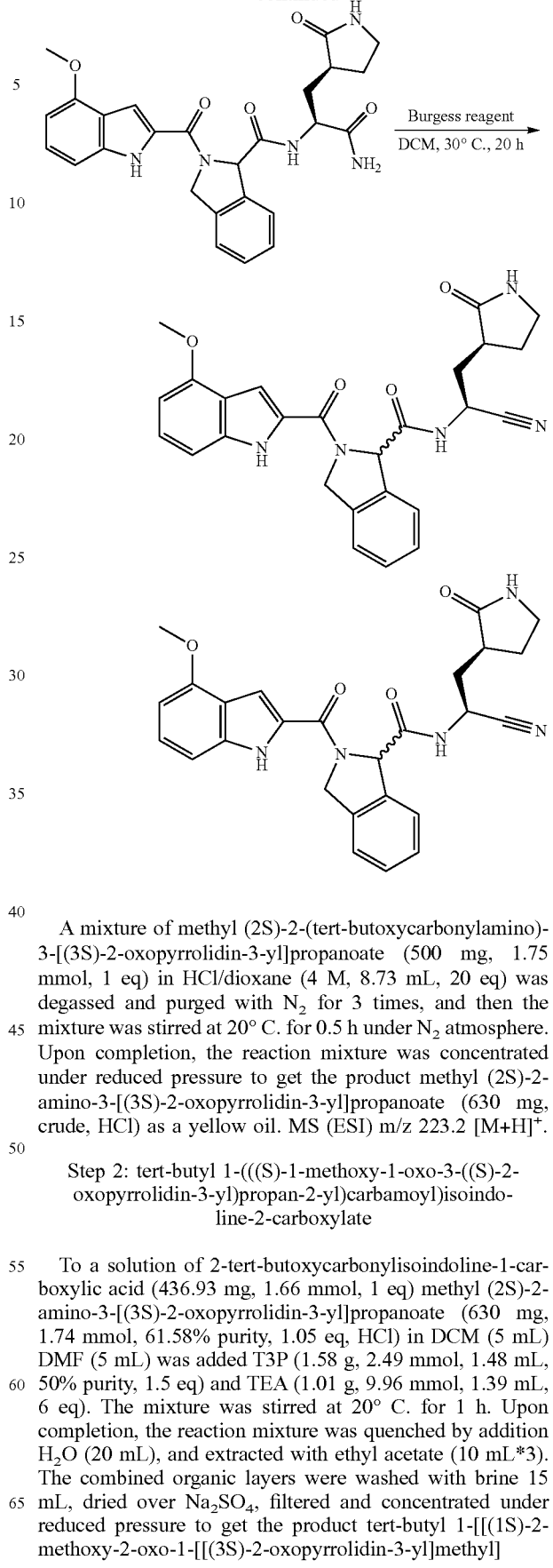

A mixture of methyl (2S)-2-(tert-butoxycarbonylamino)-3-[(3S)-2-oxopyrrolidin-3-yl]propanoate (500 mg, 1.75 mmol, 1 eq) in HCl/dioxane (4 M, 8.73 mL, 20 eq) was degassed and purged with $N_2$ for 3 times, and then the mixture was stirred at 20° C. for 0.5 h under $N_2$ atmosphere. Upon completion, the reaction mixture was concentrated under reduced pressure to get the product methyl (2S)-2-amino-3-[(3S)-2-oxopyrrolidin-3-yl]propanoate (630 mg, crude, HCl) as a yellow oil. MS (ESI) m/z 223.2 [M+H]$^+$.

Step 2: tert-butyl 1-(((S)-1-methoxy-1-oxo-3-((S)-2-oxopyrrolidin-3-yl)propan-2-yl)carbamoyl)isoindo-line-2-carboxylate To a solution of 2-tert-butoxycarbonylisoindoline-1-carboxylic acid (436.93 mg, 1.66 mmol, 1 eq) methyl (2S)-2-amino-3-[(3S)-2-oxopyrrolidin-3-yl]propanoate (630 mg, 1.74 mmol, 61.58% purity, 1.05 eq, HCl) in DCM (5 mL) DMF (5 mL) was added T3P (1.58 g, 2.49 mmol, 1.48 mL, 50% purity, 1.5 eq) and TEA (1.01 g, 9.96 mmol, 1.39 mL, 6 eq). The mixture was stirred at 20° C. for 1 h. Upon completion, the reaction mixture was quenched by addition $H_2O$ (20 mL), and extracted with ethyl acetate (10 mL*3). The combined organic layers were washed with brine 15 mL, dried over $Na_2SO_4$, filtered and concentrated under reduced pressure to get the product tert-butyl 1-[[(1S)-2-methoxy-2-oxo-1-[[(3S)-2-oxopyrrolidin-3-yl]methyl]

ethyl]carbamoyl]isoindoline-2-carboxylate (720 mg, crude) as a white solid. MS (ESI) m/z 432.2 [M+H]+.

Step 3: (2S)-methyl 2-(isoindoline-1-carboxamido)-3-((S)-2-oxopyrrolidin-3-yl)propanoate A mixture of tert-butyl 1-[[(1S)-2-methoxy-2-oxo-1-[[(3S)-2-oxopyrrolidin-3-yl]methyl]ethyl]carbamoyl]isoindoline-2-carboxylate (720 mg, 1.67 mmol, 1 eq) in HCl/dioxane (4 M, 8.34 mL, 20 eq) was degassed and purged with N₂ for 3 times, and then the mixture was stirred at 20° C. for 0.5 h under N₂ atmosphere. Upon completion, the reaction mixture was concentrated under reduced pressure to get the product methyl (2S)-2-(isoindoline-1-carbonylamino)-3-[(3S)-2-oxopyrrolidin-3-yl]propanoate (770 mg, crude, HCl) as a brown oil. MS (ESI) m/z 332.3[M+H]+.

Step 4: (2S)-methyl 2-(2-(4-methoxy-1H-indole-2-carbonyl)isoindoline-1-carboxamido)-3-((S)-2-oxopyrrolidin-3-yl)propanoate A mixture of 4-methoxy-1H-indole-2-carboxylic acid (287.43 mg, 1.50 mmol, 1 eq), methyl (2S)-2-(isoindoline-1-carbonylamino)-3-[(3S)-2-oxopyrrolidin-3-yl]propanoate (770 mg, 1.65 mmol, 79% purity, 1.1 eq, HCl), DMAP (367.34 mg, 3.01 mmol, 2 eq), EDCI (576.42 mg, 3.01 mmol, 2 eq) in DCM (8 mL) and DMF (2.7 mL) was degassed and purged with N₂ for 3 times, and then the mixture was stirred at 20° C. for 1 h under N₂ atmosphere. Upon completion, the reaction mixture was quenched by addition H₂O (25 mL), and then extracted with DCM (10 mL*3). The combined organic layers were washed with brine (15 mL), dried over Na₂SO₄, filtered and concentrated under reduced pressure to give a residue. The residue was purified by neutral prep-HPLC (column: Kromasil C18 (250*50 mm*10 um); mobile phase: [water (10 mM NH₄HCO₃)-ACN]; B %: 25%-45%, 10 min) to afford methyl (2S)-2-[[2-(4-methoxy-1H-indole-2-carbonyl)isoindoline-1-carbonyl]amino]-3-[(3S)-2-oxopyrrolidin-3-yl]propanoate (Isomer 1: 150 mg, 297.30 umol, 19.78% yield) as white solid. MS (ESI) m/z 505.3[M+H]+; and to afford methyl (2S)-2-[[2-(4-methoxy-1H-indole-2-carbonyl)isoindoline-1-carbonyl]amino]-3-[(3S)-2-oxopyrrolidin-3-yl]propanoate (Isomer 2: 140 mg, 277.48 umol, 18.46% yield) as white solid. MS (ESI) m/z 505.3[M+H]+.

Step 5 N-((S)-1-amino-1-oxo-3-((S)-2-oxopyrrolidin-3-yl)propan-2-yl)-2-(4-methoxy-1H-indole-2-carbonyl)isoindoline-1-carboxamide A solution of methyl (2S)-2-[[2-(4-methoxy-1H-indole-2-carbonyl)isoindoline-1-carbonyl]amino]-3-[(3S)-2-oxopyrrolidin-3-yl]propanoate (150 mg, 297.30 umol, 1 eq) in MeOH/NH₃ (7 M, 849.44 uL, 20 eq) was stirred at 45° C. for 48 h. Upon completion, the reaction mixture was concentrated under reduced pressure to get the product N-[(1S)-2-amino-2-oxo-1-[[(3S)-2-oxopyrrolidin-3-yl]methyl]ethyl]-2-(4-methoxy-1H-indole-2-carbonyl)isoindoline-1-carboxamide (130 mg, crude) as colorless oil. MS (ESI) m/z 490.3[M+H]+.

Step 5 N-((S)-1-amino-1-oxo-3-((S)-2-oxopyrrolidin-3-yl)propan-2-yl)-2-(4-methoxy-1H-indole-2-carbonyl)isoindoline-1-carboxamide A solution of methyl (2S)-2-[[2-(4-methoxy-1H-indole-2-carbonyl)isoindoline-1-carbonyl] amino]-3-[(3S)-2-oxopyrrolidin-3-yl]propanoate (140 mg, 277.48 umol, 1 eq) in MeOH/NH₃ (7 M, 792.81 uL, 20 eq) was stirred at 45° C. for 24 h. Upon completion, the reaction mixture was concentrated under reduced pressure to get the product N-[(1S)-2-amino-2-oxo-1-[[(3S)-2-oxopyrrolidin-3-yl]methyl]ethyl]-2-(4-methoxy-1H-indole-2-carbonyl)isoindoline-1-carboxamide (110 mg, crude) as colorless oil. MS (ESI) m/z 490.3[M+H]+.

Step 6 N-((S)-1-cyano-2-((S)-2-oxopyrrolidin-3-yl)ethyl)-2-(4-methoxy-1H-indole-2-carbonyl)isoindoline-1-carboxamide To a solution of N-[(1S)-2-amino-2-oxo-1-[[(3S)-2-oxopyrrolidin-3-yl]methyl]ethyl]-2-(4-methoxy-1H-indole-2-carbonyl)isoindoline-1-carboxamide (125 mg, 255.35 umol, 1 eq) in DCM (8 mL) was added Burgess reagent (273.84 mg, 1.15 mmol, 4.5 eq), and the resulting mixture was stirred at 30° C. for 20 h. Upon completion, the reaction mixture was quenched by addition H₂O (0.5 mL), and then concentrated under reduced pressure to give a residue. The residue was purified by neutral prep-HPLC (column: Waters Xbridge BEH C18 100*25 mm*5 um; mobile phase: [water (10 mM NH₄HCO₃)-ACN]; B %: 20%-50%, 10 min) to afford product N-[(1S)-1-cyano-2-[(3S)-2-oxopyrrolidin-3-yl]ethyl]-2-(4-methoxy-1H-indole-2-carbonyl)isoindoline-1-carboxamide (31.50 mg, 66.81 umol, 26.16% yield, 100% purity) as a white solid. MS (ESI) m/z 472.3[M+H]+.

¹H NMR (400 MHz, DMSO-d₆) δ ppm 11.53-11.83 (m, 1H) 9.11-9.78 (m, 1H) 7.31-7.78 (m, 5H) 6.95-7.29 (m, 3H) 6.42-6.63 (m, 1H) 5.73 (s, 1H) 5.27-5.41 (m, 1H) 4.91-5.05 (m, 1H) 3.76-3.99 (m, 3H) 2.71-3.19 (m, 2H) 2.00-2.30 (m, 3H) 1.20-1.87 (m, 2H).

Step 6 N-((S)-1-cyano-2-((S)-2-oxopyrrolidin-3-yl)ethyl)-2-(4-methoxy-1H-indole-2-carbonyl)isoindoline-1-carboxamide To a solution of N-[(1S)-2-amino-2-oxo-1-[[(3S)-2-oxopyrrolidin-3-yl]methyl]ethyl]-2-(4-methoxy-1H-indole-2-carbonyl)isoindoline-1-carboxamide (105 mg, 214.49 umol, 1 eq) in DCM (6 mL) was added Burgess reagent (204.47 mg, 857.98 umol, 4 eq). The mixture was stirred at 30° C. for 7 h. Upon completion, the reaction mixture was quenched by addition H₂O (0.5 mL), and then concentrated under reduced pressure to give a residue. The residue was purified by neutral prep-HPLC (column: Waters Xbridge Prep OBD C18 150*40 mm*10 um; mobile phase: [water (10 mM NH4HCO3)-ACN]; B %: 25%-55%, 8 min) to afford N-[(1S)-1-cyano-2-[(3S)-2-oxopyrrolidin-3-yl]ethyl]-2-(4-methoxy-1H-indole-2-carbonyl)isoindoline-1-carboxamide (34.83 mg, 73.72 umol, 34.37% yield, 99.791% purity) as a white solid. MS (ESI) m/z 472.3[M+H]+.

¹H NMR (400 MHz, DMSO-d₆) δ ppm 11.72 (s, 1H) 9.19 (d, J=8.11 Hz, 1H) 7.31-7.76 (m, 5H) 6.92-7.29 (m, 3H) 6.56 (d, J=7.75 Hz, 1H) 5.74 (s, 1H) 5.34 (br d, J=10.13 Hz, 1H) 4.96 (q, J=8.23 Hz, 1H) 3.86-3.89 (m, 1H) 3.86-4.55 (m, 1H) 3.84-4.01 (m, 3H) 2.96-3.22 (m, 2H) 2.25-2.41 (m, 1H) 2.02-2.20 (m, 2H) 1.47-1.87 (m, 2H).

Example 67. Synthesis of Viral Protease Inhibitor Compound 647

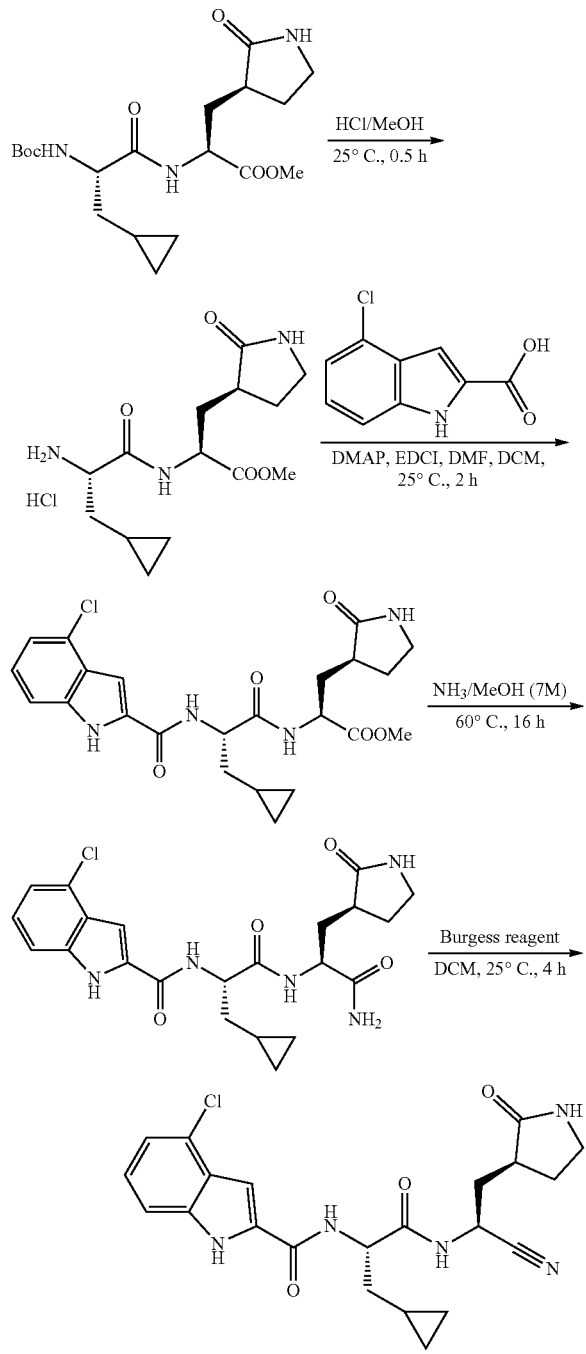

A mixture of methyl 2S)-2-[[(2S)-2-(tert-butoxycarbonylamino)-3-cyclopropyl-propanoyl]amino]-3-[(3S)-2-oxopyrrolidin-3-yl]propanoate (1.3 g, 3.27 mmol, 1 eq) in HCl/MeOH (15 mL) was stirred at 25° C. for 30 min. Upon completion, the reaction mixture was concentrated under reduced pressure to give methyl (2S)-2-[[(2S)-2-amino-3-cyclopropyl-propanoyl]amino]-3-[(3S)-2-oxopyrrolidin-3-yl]propanoate (1.3 g, crude) as a white solid.

Step 2: methyl (2S)-2-[[(2S)-2-[(4-chloro-1H-indole-2-carbonyl)amino]-3-cyclopropyl-propanoyl]amino]-3-[(3S)-2-oxopyrrolidin-3-yl]propanoate To a mixture of methyl (2S)-2-[[(2S)-2-amino-3-cyclopropyl-propanoyl]amino]-3-[(3S)-2-oxopyrrolidin-3-yl]propanoate (500 mg, 1.68 mmol, 1 eq) in DCM (6 mL) and DMF (2 mL), the mixture was added DMAP (616.30 mg, 5.04 mmol, 3 eq) in one portion at 25° C. The mixture was added 4-chloro-1H-indole-2-carboxylic acid (394.69 mg, 2.02 mmol, 1.2 eq) and EDCI (967.04 mg, 5.04 mmol, 3 eq) and stirred at 25° C. for 2 h. Upon completion, the reaction mixture was concentrated under reduced pressure to give the crude product. The crude was purified by column chromatography (SiO$_2$, petroleum ether/ethyl acetate=5/1 to ethyl acetate/methanol=10/1) to give methyl (2S)-2-[[(2S)-2-[(4-chloro-1H-indole-2-carbonyl)amino]-3-cyclopropyl-propanoyl]amino]-3-[(3S)-2-oxopyrrolidin-3-yl]propanoate (760 mg, 1.60 mmol, 95.16% yield) as a white solid. MS (ESI) m/z 475.2 [M+H]$^+$.

Step 3: N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4-chloro-1H-indole-2-carboxamide A mixture of methyl (2S)-2-[[(2S)-2-[(4-chloro-1H-indole-2-carbonyl)amino]-3-cyclopropyl-propanoyl]amino]-3-[(3S)-2-oxopyrrolidin-3-yl]propanoate (700 mg, 1.47 mmol, 1 eq) in NH$_3$/MeOH (7 M, 15 mL, 71.24 eq) was stirred at 60° C. for 16 h. Upon completion, the reaction mixture was concentrated under reduced pressure to give N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4-chloro-1H-indole-2-carboxamide (660 mg, 1.44 mmol, 97.36% yield) as a white solid. MS (ESI) m/z 460.2 [M+H]$^+$.

Step 4: 4-chloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-indole-2-carboxamide To a mixture of N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4-chloro-1H-indole-2-carboxamide (630 mg, 1.37 mmol, 1 eq) in DCM (10 mL) was added Burgess reagent (652.87 mg, 2.74 mmol, 2 eq) in one portion at 25° C. The mixture was stirred at 25° C. for 4 h. Upon completion, the reaction mixture was concentrated under reduced pressure to give the crude product. The crude was purified by prep-HPLC (neutral condition, column: Phenomenex Gemini-NX C18 75*30 mm*3 um; mobile phase: [water (10 mM NH$_4$HCO$_3$)-ACN]; B %: 30%-50%, 8 min) to give 4-chloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-indole-2-carboxamide (110 mg, 248.92 umol, 18.17% yield) as a white solid. MS (ESI) m/z 442.2 [M+H]$^+$.

$^1$H NMR (400 MHz, DMSO-d$_6$) δ=11.96 (br s, 1H), 8.93 (d, J=8.2 Hz, 1H), 8.76 (d, J=7.7 Hz, 1H), 7.78-7.67 (m, 1H), 7.46-7.36 (m, 2H), 7.21-7.09 (m, 2H), 5.04-4.89 (m, 1H), 4.55-4.43 (m, 1H), 3.12 (quin, J=9.3 Hz, 2H), 2.43-2.29 (m, 1H), 2.19-2.07 (m, 2H), 1.91-1.63 (m, 3H), 1.54-1.41 (m, 1H), 0.82 (br dd, J=5.6, 7.4 Hz, 1H), 0.50-0.34 (m, 2H), 0.26-0.04 (m, 2H).

Example 68. Synthesis of Viral Protease Inhibitor Compound 649

Step 1: methyl (2S)-2-[[(2S)-2-amino-3-cyclopropyl-propanoyl]amino]-3-[(3S)-2-oxopyrrolidin-3-yl]propanoate

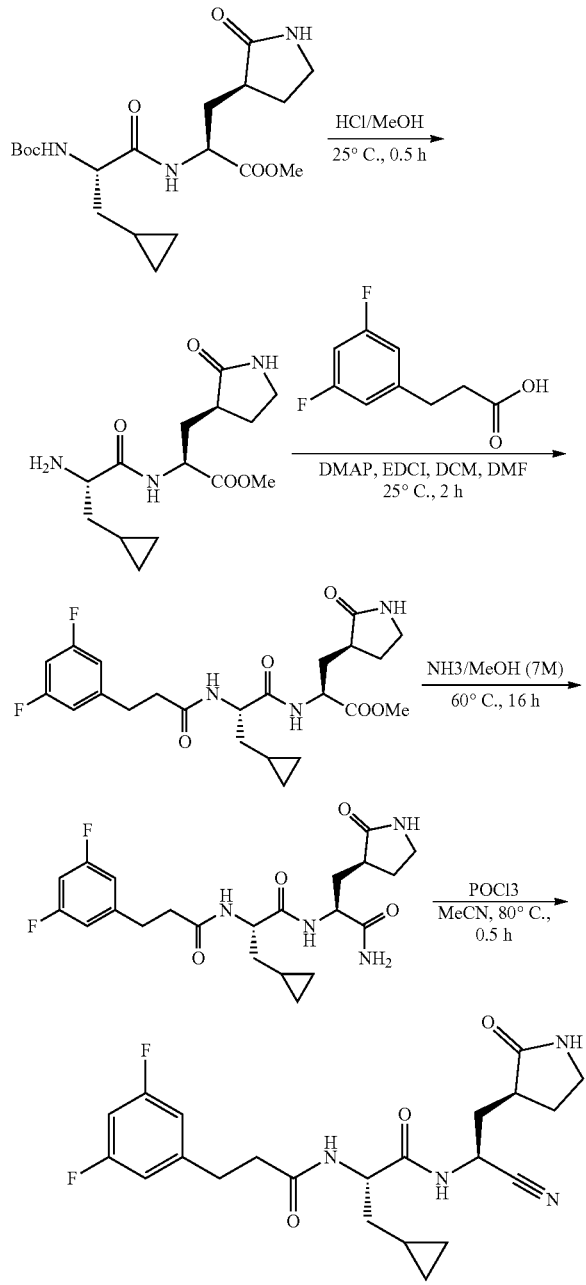

A mixture of methyl (2S)-2-[[(2S)-2-(tert-butoxycarbonylamino)-3-cyclopropyl-propanoyl]amino]-3-[(3S)-2-oxopyrrolidin-3-yl]propanoate (500 mg, 968.64 umol, 77% purity, 1 eq) in HCl/MeOH (10 mL) was stirred at 25° C. for 30 min. Upon completion, the reaction mixture was concentrated under reduced pressure to give methyl (2S)-2-[[(2S)-2-amino-3-cyclopropyl-propanoyl]amino]-3-[(3S)-2-oxopyrrolidin-3-yl]propanoate (300 mg, crude) as a white solid.

Step 2: methyl (2S)-2-[[(2S)-3-cyclopropyl-2-[3-(3,5-difluorophenyl)propanoylamino]propanoyl]amino]-3-[(3S)-2-oxopyrrolidin-3-yl]propanoate A mixture of methyl (2S)-2-[[(2S)-2-amino-3-cyclopropyl-propanoyl]amino]-3-[(3S)-2-oxopyrrolidin-3-yl]propanoate (288 mg, 968.56 umol, 1 eq) in DCM (5 mL) and DMF (2.5 mL) was added DMAP (354.98 mg, 2.91 mmol, 3 eq) and the mixture was added with 3-(3,5-difluorophenyl) propanoic acid (180.30 mg, 968.56 umol, 1 eq) and EDCI (928.37 mg, 4.84 mmol, 5 eq) in one portion at 25° C. The mixture was stirred at 25° C. for 2 h. Upon completion, the reaction mixture was diluted with H$_2$O (5 mL) and extracted with ethyl acetate (8 mL*3). The combined organic layers were washed with brine (15 mL*1), dried over with Na$_2$SO$_4$, filtered and concentrated under reduced pressure to give the crude product The crude was purified by column chromatography (SiO$_2$, petroleum ether/ethyl acetate=5/1 to ethyl acetate/methanol=5:1) to give methyl (2S)-2-[[(2S)-3-cyclopropyl-2-[3-(3,5-difluorophenyl)propanoylamino]propanoyl]amino]-3-[(3S)-2-oxopyrrolidin-3-yl]propanoate (300 mg, 547.81 umol, 56.56% yield, 85% purity) as a white solid. MS (ESI) m/z 466.2 [M+H]$^+$.

Step 3: (2S)-N-[(1S)-2-amino-2-oxo-1-[[(3S)-2-oxopyrrolidin-3-yl]methyl]ethyl]-3-cyclopropyl-2-[3-(3,5-difluorophenyl)propanoylamino]propanamide A mixture of methyl (2S)-2-[[(2S)-3-cyclopropyl-2-[3-(3,5-difluorophenyl)propanoylamino]propanoyl]amino]-3-[(3S)-2-oxopyrrolidin-3-yl]propanoate (300 mg, 644.48 umol, 1 eq) in NH$_3$/methanol (7 M, 5.45 mL, 59.24 eq) was stirred at 60° C. for 16 h. Upon completion, the reaction mixture was concentrated under reduced pressure to give (2S)-N-[(1S)-2-amino-2-oxo-1-[[(3S)-2-oxopyrrolidin-3-yl]methyl]ethyl]-3-cyclopropyl-2-[3-(3,5-difluorophenyl)propanoylamino]propanamide (260 mg, 577.16 umol, 89.55% yield) as a white solid. MS (ESI) m/z 451.2 [M+H]$^+$.

Step 4: (2S)-N-[(1S)-1-cyano-2-[(3S)-2-oxopyrrolidin-3-yl]ethyl]-3-cyclopropyl-2-[3-(3,5-difluorophenyl)propanoylamino]propanamide To a mixture of (2S)-N-[(1S)-2-amino-2-oxo-1-[[(3S)-2-oxopyrrolidin-3-yl]methyl]ethyl]-3-cyclopropyl-2-[3-(3,5-difluorophenyl)propanoylamino]propanamide (70 mg, 155.39 umol, 1 eq) in ACN (1 mL) was added POCl$_3$ (47.65 mg, 310.78 umol, 28.88 uL, 2 eq) in one portion at 25° C. The mixture was stirred at 80° C. for 0.5 h. Upon completion, the reaction mixture was quenched by addition NaHCO$_3$ (1 mL) at 25° C., and then extracted with ethyl acetate (1 mL*3). The combined organic layers were concentrated under reduced pressure to give crude product. The crude was purified by prep-HPLC (neutral condition, column: Waters Xbridge Prep OBD C18 150*40 mm*10 um; mobile phase: [water (10 mM NH$_4$HCO$_3$)-ACN]; B %: 20%-50%, 8 min) to give (2S)-N-[(1S)-1-cyano-2-[(3S)-2-oxopyrrolidin-3-yl]ethyl]-3-cyclopropyl-2-[3-(3,5-difluorophenyl)propanoylamino]propanamide (7 mg, 16.19 umol, 10.42% yield) as a white solid. MS (ESI) m/z 433.2 [M+H]$^+$.

$^1$H NMR (400 MHz, DMSO-d$_6$) δ=9.09-8.81 (m, 1H), 8.15 (br d, J=7.5 Hz, 1H), 7.83-7.70 (m, 1H), 7.10-6.89 (m, 3H), 4.99-4.83 (m, 1H), 4.33-4.19 (m, 1H), 3.19-3.04 (m, 2H), 2.89-2.78 (m, 2H), 2.46 (br s, 2H), 2.39-2.03 (m, 3H), 1.84-1.46 (m, 3H), 1.40-1.19 (m, 1H), 0.59 (br s, 1H), 0.34 (br s, 2H), 0.14-0.05 (m, 2H).

¹H NMR (400 MHz, METHANOL-d₄) δ=6.84 (br t, J=5.7 Hz, 2H), 6.74 (tt, J=2.2, 9.3 Hz, 1H), 5.06-4.92 (m, 1H), 4.37-4.22 (m, 1H), 3.38-3.32 (m, 2H), 2.97-2.88 (m, 2H), 2.71-2.57 (m, 2H), 2.54-2.10 (m, 3H), 2.01-1.77 (m, 2H), 1.76-1.58 (m, 1H), 1.55-1.36 (m, 1H), 0.72-0.59 (m, 1H), 0.53-0.36 (m, 2H), 0.18-0.02 (m, 2H).

Example 69. Synthesis of Viral Protease Inhibitor Compound 653

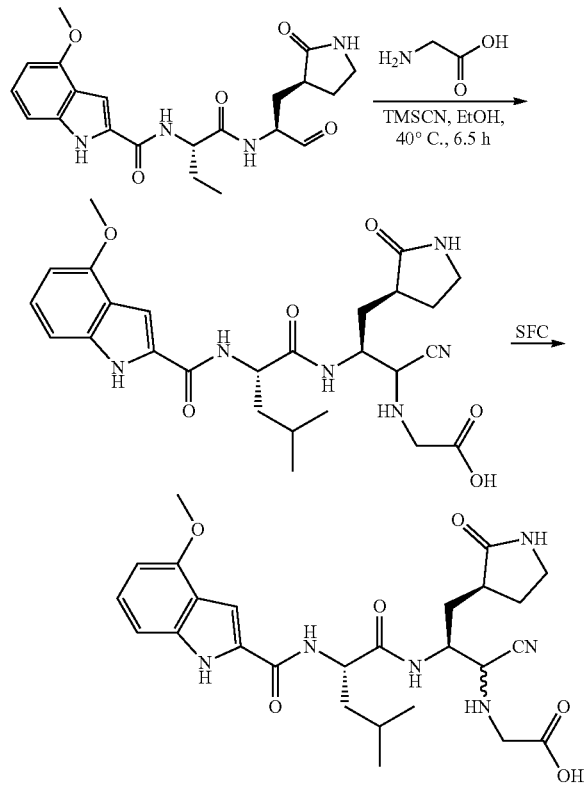

To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (1 g, 1.81 mmol, 80% purity, 1 eq) in EtOH (20 mL) was added 2-aminoacetic acid (271.74 mg, 3.62 mmol, 20.52 uL, 2 eq), ZnCl₂ (1 M, 18.10 uL, 0.01 eq). The mixture was stirred at 25° C. for 30 min, and then TMSCN (359.14 ng, 3.62 mmol, 452.89 uL, 2 eq) was added and the resulting mixture was stirred at 40° C. for 6 h. Upon the reaction was completed, the reaction mixture was filtered and concentrated under reduced pressure to give a residue. The residue was purified by HCl prep-HPLC (column: Phenomenex luna C18 80*40 mm*3 urn; mobile phase: [water (0.04% HCl)-ACN]; B %: 25%-45%, 7 min) to get the mixture product 400 mg. The mixture was separated by SFC (column: DAICEL CHIRALPAK AD (250 mm*30 mm, 10 um); mobile phase: [Neu-ETOH]; B %: 50%-50%, 10 min) to get the compound 2-[[(2S)-1-cyano-2-[[(2S)-2-[(4-methoxy-1H-indole-2-carbonyl)amino]-4-methyl-pentanoyl]amino]-3-[(3S)-2-oxopyrrolidin-3-yl]propyl]amino]acetic acid (125 mg, 235.87 umol, 13.03% yield, 99.363% purity) and 2-[[(2S)-1-cyano-2-[[(2S)-2-[(4-methoxy-1H-indole-2-carbonyl)amino]-4-methyl-pentanoyl]amino]-3-[(3S)S)-oxopyrrolidin-3-yl] propyl]amino]acetic acid (205 mg, 373.82 umol, 20.65% yield, 96.023% purity) as a white solid. MS (ESI) m/z 527.3 [M+H]⁺.

Isomer 1: ¹H NMR (400 MHz, DMSO-d6) δ=11.56 (d, J=2.0 Hz, 1H), 8.52-8.21 (m, 2H), 7.58 (s, 1H), 7.35 (d, J=1.7 Hz, 1H), 7.14-7.05 (m, 1H), 7.03-6.97 (m, 1H), 6.50 (d, J=7.7 Hz, 1H), 4.57-4.41 (m, 1H), 4.14 (tdd, J=4.2, 8.2, 12.2 Hz, 1H), 3.97-3.82 (m, 4H), 3.52-3.36 (m, 2H), 3.18-2.98 (m, 2H), 2.41-2.27 (m, 1H), 2.12-2.04 (m, 2H), 1.82-1.36 (m, 5H), 0.91 (dd, J=6.4, 15.8 Hz, 6H)

Isomer 2: ¹H NMR (400 MHz, DMSO-d6) δ=11.57 (d, J=2.0 Hz, 1H), 8.39 (d, J=7.8 Hz, 1H), 8.20 (d, J=9.5 Hz, 1H), 7.54 (s, 1H), 7.37 (d, J=1.6 Hz, 1H), 7.16-6.94 (m, 1H), 6.50 (d, J=7.6 Hz, 1H), 4.53-4.36 (m, 1H), 4.18-4.01 (m, 1H), 3.88 (s, 3H), 3.77 (d, J=8.8 Hz, 1H), 3.43-3.33 (m, 2H), 3.15-2.96 (m, 2H), 2.38-2.25 (m, 1H), 2.08-2.01 (m, 1H), 1.91-1.47 (m, 6H), 0.91 (dd, J=6.4, 14.8 Hz, 6H)

To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (700 mg, 1.27 mmol, 80% purity, 1 eq) in EtOH (10 mL) was added pyrrolidine (180.01 mg, 2.53 mmol, 211.28 uL, 2 eq), ZnCl2 (1 M, 12.66 uL, 0.01 eq), and the resulting mixture was stirred at 25° C. for 30 min. After the addition of TMSCN (251.10 mg, 2.53 mmol, 316.65 uL, 2 eq), the mixture was stirred at 25° C. for 2 h. Upon completion, the reaction mixture was filtered and concentrated under reduced pressure to give a residue. The residue was purified by neutral prep-HPLC to afford N-[(1S)-1-[[(1S)-2-cyano-1-[[(3S)-2-oxopyrrolidin-3-yl]methyl]-2-pyrrolidin-1-yl-ethyl]carbamoyl]-3-methyl-butyl]-4-methoxy-1H-indole-2-carboxamide (110 mg, 199.95 umol, 15.80% yield, 95% purity) and N-[(1S)-1-[[(1S)-2-cyano-1-[[(3S)-2-oxopyrrolidin-3-yl]methyl]-2-pyrrolidin-1-yl-ethyl] carbamoyl]-3-methyl-butyl]-4-methoxy-1H-indole-2-carboxamide (110 mg, 199.95 umol, 15.80% yield, 95% purity) as a white solid. MS (ESI) m/z 523.4 [M+H]⁺ column: Phenomenex luna CN 5 u 100*30 mm; mobile phase: [Hexane-IPA]; B %: 5%-40%, 20 min Isomer 1: ¹H NMR (400 MHz, DMSO-d6) δ=11.58 (s, 1H), 8.43 (d, J=7.7 Hz, 1H), 8.20 (d, J=9.4 Hz, 1H), 7.68-7.49 (m, 1H), 7.38 (d, J=1.2 Hz, 1H), 7.18-6.93 (m, 2H), 6.50 (d, J=7.6 Hz, 1H), 4.57-3.99 (m, 3H), 3.88 (s, 3H), 3.19-2.95 (m, 2H), 2.64-2.53 (m, 4H), 2.38-2.27 (m, 1H), 2.15-2.01 (m, 1H), 1.85-1.44 (m, 101H), 0.91 (dd, J=6.4, 16.3 Hz, 6H)

Isomer 2: ¹H NMR (400 MHz, DMSO-d6) δ=11.59 (br s, 1H), 8.39 (br d, J=7.6 Hz, 1H), 8.01 (br d, J=9.1 Hz, 1H), 7.69-7.49 (m, 1H), 7.43-7.28 (m, 1H), 7.16-6.86 (m, 2H), 6.50 (d, J=7.6 Hz, 1H), 4.59-4.24 (m, 3H), 3.88 (s, 3H), 3.19-2.94 (m, 2H), 2.71-2.57 (m, 2H), 2.49-2.32 (m, 3H), 2.18-2.08 (m, 1H), 2.06-1.93 (m, 1H), 1.83-1.37 (m, 9H), 0.90 (dd, J=6.5, 15.2 Hz, 6H)

Example 70. Synthesis of Viral Protease Inhibitor Compound 655

Step 1: (2S,4R)-di-tert-butyl 4-hydroxypyrrolidine-1,2-dicarboxylate

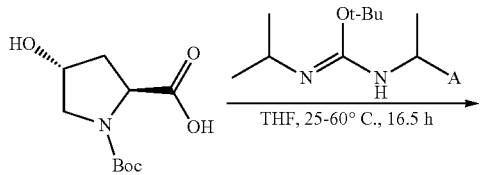

915
-continued

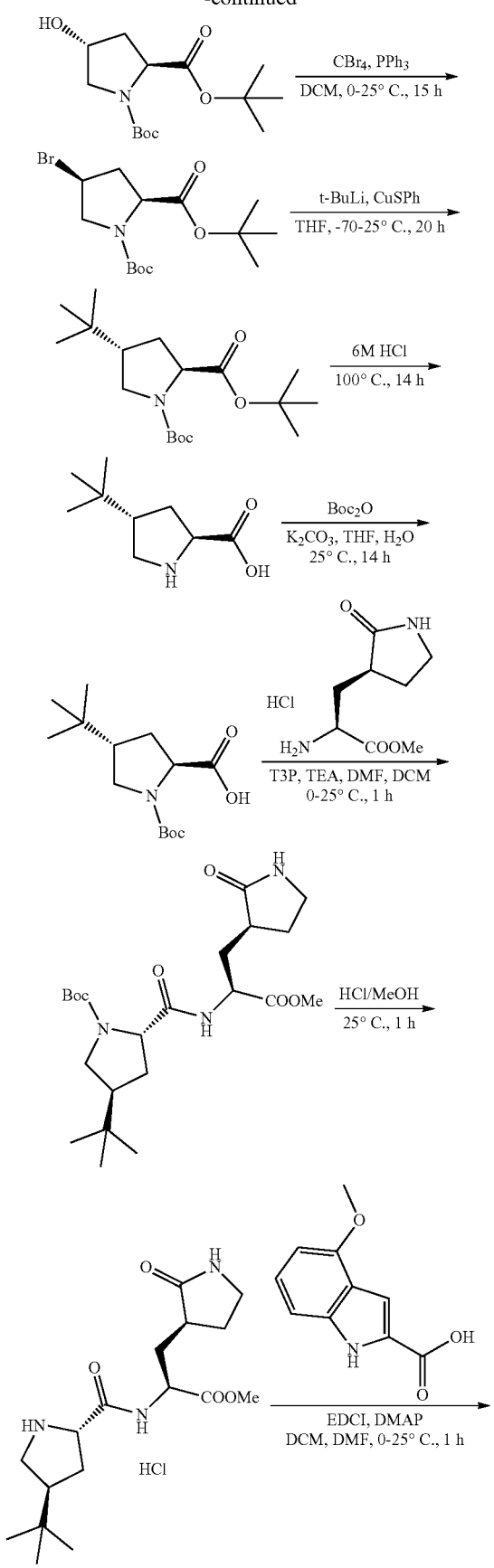

916
-continued

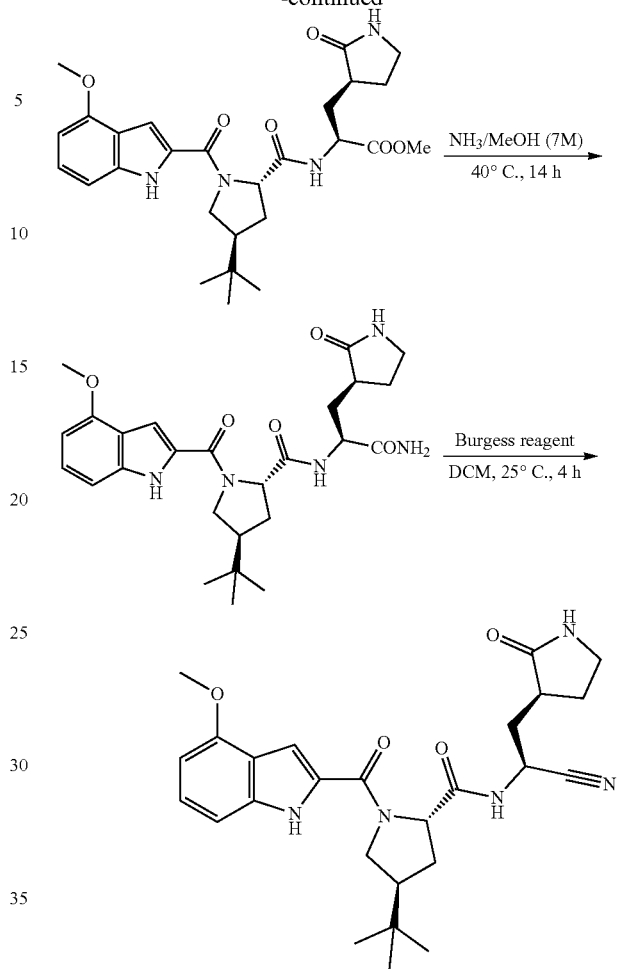

To a solution of (2S,4R)-1-tert-butoxycarbonyl-4-hydroxy-pyrrolidine-2-carboxylic acid (5 g, 21.62 mmol, 1 eq) in THF (75 mL) was added 2-tert-butyl-1,3-diisopropyl-isourea (6.50 g, 32.43 mmol, 1.5 eq) at 25° C., and then the resulting solution was stirred at 60° C. for 2.5 h. 2-tert-butyl-1,3-diisopropyl-isourea (6.50 g, 32.43 mmol, 1.5 eq) was added to the mixture and then stirred at 60° C. for 14 h. Upon completion, the reaction mixture was filtered through celite and the filtrate was concentrated under reduced pressure to give (2S,4R)-di-tert-butyl 4-hydroxypyrrolidine-1,2-dicarboxylate (4.3 g, 14.22 mmol, 65.75% yield, 95% purity) as a colorless oil. MS (ESI) m/z 288.2 [M+H]$^+$ Step 2: (2S,4S)-di-tert-butyl 4-bromopyrrolidine-1,2-dicarboxylate To a solution of (2S,4R)-di-tert-butyl 4-hydroxypyrrolidine-1,2-dicarboxylate (4 g, 13.92 mmol, 1 eq) in DCM (40 mL) was added CBr$_4$ (14.08 g, 42.46 mmol, 3.05 eq) at 25° C. The mixture was cooled to 0° C., and PPh$_3$ (11.32 g, 43.15 mmol, 3.1 eq) was added carefully. The reaction was stirred at 25° C. for 15 h. Upon completion, ethanol (4 mL) was added, and the solution was stirred for 2 h. MTBE (40 mL) was added dropwise to precipitate the phosphine oxide, which was filtered off, the filter cake was washed with DCM (30 mL*2), and the filtrate was concentrated under reduced pressure to give a brown oil. The residue was purified by column chromatography (SiO$_2$, petroleum ether:ethyl acetate=100:0 to 10:1) to give (2S,4S)-di-tert-butyl 4-bromopyrrolidine-1,2-dicarboxylate (1.5 g, 4.07 mmol, 29.23% yield, 95% purity) as light yellow oil.

Step 3: (2S,4S)-di-tert-butyl 4-(tert-butyl)pyrrolidine-1,2-dicarboxylate

A mixture of phenylsulfanylcopper (1.58 g, 9.14 mmol, 6.4 eq) in dry THF (30 mL) was cooled to −70° C., and then treated with careful addition of t-BuLi (1.3 M, 7.03 mL, 6.4 eq). The resulting mixture was stirred for 30 min, and a precooled (−20° C.) solution of (2S,4S)-di-tert-butyl 4-bromopyrrolidine-1,2-dicarboxylate (500 mg, 1.43 mmol, 1 eq) in dry THF (5 mL) was added. The reaction was stirred at −70° C. for 5 h, and then warmed to 25° C. for 15 h under $N_2$. Upon completion, the reaction was quenched by pouring into a solution of saturated aqueous $NH_4Cl$ (30 mL). The aqueous mixture was stirred vigorously for 30 min. Solids were filtered off, and the phases were separated. The aqueous phase was extracted with MTBE (10 mL*3), and the combined organic phases were washed with saturated aqueous $NaHCO_3$ (10 mL) and brine (10 mL), dried over $Na_2SO_4$, concentrated under reduced pressure to give a crude. The residue was purified by column chromatography ($SiO_2$, petroleum ether:ethyl acetate=100:0 to 10:1) to give (2S,4S)-di-tert-butyl 4-(tert-butyl)pyrrolidine-1,2-dicarboxylate (290 mg, 797.05 umol, 55.83% yield, 90% purity) as an off-white solid.

Step 4: (2S,4S)-4-(tert-butyl)pyrrolidine-2-carboxylic acid

A mixture of (2S,4S)-di-tert-butyl 4-(tert-butyl)pyrrolidine-1,2-dicarboxylate (250 mg, 763.46 umol, 1 eq) in HCl (6 M, 2.5 mL, 19.65 eq) was stirred at 100° C. for 14 h. Upon completion, the reaction mixture was concentrated under reduced pressure to give (2S,4S)-4-tert-butylpyrrolidine-2-carboxylic acid (158 mg, crude, HCl) as a yellow solid.

Step 5: (2S,4S)-1-(tert-butoxycarbonyl)-4-(tert-butyl)pyrrolidine-2-carboxylic acid To a mixture of (2S,4S)-4-tert-butylpyrrolidine-2-carboxylic acid (158 mg, 760.72 umol, 1 eq, HCl) in THF (1 mL) and $H_2O$ (1 mL) was added $K_2CO_3$ (315.41 mg, 2.28 mmol, 3 eq) and $Boc_2O$ (199.23 mg, 912.87 umol, 209.72 uL, 1.2 eq). The reaction was stirred at 25° C. for 14 h under $N_2$. Upon completion, the reaction mixture was concentrated under reduced pressure to afford (2S,4S)-1-(tert-butoxycarbonyl)-4-(tert-butyl)pyrrolidine-2-carboxylic acid (650 mg, crude) as a yellow solid.

Step 6: (2S,4S)-tert-butyl 4-(tert-butyl)-2-(((S)-1-methoxy-1-oxo-3-((S)-2-oxopyrrolidin-3-yl)propan-2-yl)carbamoyl)pyrrolidine-1-carboxylate To a solution of (2S,4S)-1-(tert-butoxycarbonyl)-4-(tert-butyl)pyrrolidine-2-carboxylic acid (630 mg, 696.51 umol, 30% purity, 1 eq) in DCM (6 mL) and DMF (3 mL) was added TEA (422.88 mg, 4.18 mmol, 581.68 uL, 6 eq), methyl (2S)-2-amino-3-[(3S)-2-oxopyrrolidin-3-yl]propanoate (186.11 mg, 835.82 umol, 1.2 eq, HCl). After adding T3P (1.33 g, 2.09 mmol, 1.24 mL, 50% purity, 3 eq) at 0° C., the mixture was stirred at 25° C. for 1 h. Upon completion, the mixture was quenched with water (10.0 mL) and extracted with DCM (10.0 mL*3). The organic layers were washed with brine (10.0 mL), dried over $Na_2SO_4$, filtered and concentrated under reduced pressure to give a residue. The residue was purified by column chromatography ($SiO_2$, petroleum ether:ethyl acetate=10:1 to 0:1) to afford tert-butyl (2S,4S)-tert-butyl 4-(tert-butyl)-2-(((S)-1-methoxy-1-oxo-3-((S)-2-oxopyrrolidin-3-yl)propan-2-yl)carbamoyl)pyrrolidine-1-carboxylate (240 mg, 546.02 umol, 78.39% yield) as yellow solid. MS (ESI) m/z 440.3 $[M+H]^+$.

Step 7: (S)-methyl 2-((2S,4S)-4-(tert-butyl)pyrrolidine-2-carboxamido)-3-((S)-2-oxopyrrolidin-3-yl)propanoate A solution of tert-butyl (2S,4S)-tert-butyl 4-(tert-butyl)-2-(((S)-1-methoxy-1-oxo-3-((S)-2-oxopyrrolidin-3-yl)propan-2-yl)carbamoyl)pyrrolidine-1-carboxylate (230 mg, 523.27 umol, 1 eq) in HCl/MeOH (4 M, 2.3 mL, 17.58 eq) was stirred at 25° C. for 1 h. Upon completion, the reaction mixture was concentrated under reduced pressure to give (S)-methyl 2-((2S,4S)-4-(tert-butyl)pyrrolidine-2-carboxamido)-3-((S)-2-oxopyrrolidin-3-yl)propanoate (196 mg, crude, HCl) as a light yellow solid. MS (ESI) m/z 340.2 $[M+H]^+$.

Step 8: (S)-methyl 2-((2S,4S)-4-(tert-butyl)-1-(4-methoxy-1H-indole-2-carbonyl)pyrrolidine-2-carboxamido)-3-((S)-2-oxopyrrolidin-3-yl)propanoate To a solution of (S)-methyl 2-((2S,4S)-4-(tert-butyl)pyrrolidine-2-carboxamido)-3-((S)-2-oxopyrrolidin-3-yl)propanoate (196 mg, 521.43 umol, 1 eq, HCl) in DCM (2 mL) and DMF (1 mL) was added 4-methoxy-1H-indole-2-carboxylic acid (99.69 mg, 521.43 umol, 1 eq), DMAP (127.41 mg, 1.04 mmol, 2 eq), and then EDCI (199.92 mg, 1.04 mmol, 2 eq) at 0° C. The mixture was then stirred at 25° C. for 1 h. Upon completion, the mixture was quenched with water (10.0 mL) and extracted with DCM (10 mL*3). The organic layers were washed with brine (10 mL), dried over $Na_2SO_4$, filtered and concentrated under reduced pressure to give a residue. The residue was purified by column chromatography ($SiO_2$, dichloromethane:methanol=10:1 to 4:1) to give (S)-methyl 2-((2S,4S)-4-(tert-butyl)-1-(4-methoxy-1H-indole-2-carbonyl)pyrrolidine-2-carboxamido)-3-((S)-2-oxopyrrolidin-3-yl)propanoate (250 mg, 414.56 umol, 79.50% yield, 85% purity) as a yellow solid. MS (ESI) m/z 513.3 $[M+H]^+$.

Step 9: (2S,4S)-N-((S)-1-amino-1-oxo-3-((S)-2-oxopyrrolidin-3-yl)propan-2-yl)-4-(tert-butyl)-1-(4-methoxy-1H-indole-2-carbonyl)pyrrolidine-2-carboxamide A solution of (S)-methyl 2-((2S,4S)-4-(tert-butyl)-1-(4-methoxy-1H-indole-2-carbonyl)pyrrolidine-2-carboxamido)-3-((S)-2-oxopyrrolidin-3-yl)propanoate (235 mg, 389.68 umol, 85% purity, 1 eq) in $NH_3$/methanol (7 M, 5 mL) was stirred at 40° C. for 14 h. Upon completion, the reaction mixture was concentrated under reduced pressure to give (2S,4S)-N-((S)-1-amino-1-oxo-3-((S)-2-oxopyrrolidin-3-yl)propan-2-yl)-4-(tert-butyl)-1-(4-methoxy-1H-indole-2-carbonyl)pyrrolidine-2-carboxamide (193 mg, crude) as a yellow solid. MS (ESI) m/z 498.3 $[M+H]^+$.

Step 10: (2S,4S)-4-(tert-butyl)-N-((S)-1-cyano-2-((S)-2-oxopyrrolidin-3-yl)ethyl)-1-(4-methoxy-1H-indole-2-carbonyl)pyrrolidine-2-carboxamide To a solution of (2S,4S)-N-((S)-1-amino-1-oxo-3-((S)-2-oxopyrrolidin-3-yl)propan-2-yl)-4-(tert-butyl)-1-(4- methoxy-1H-indole-2-carbonyl)pyrrolidine-2-carboxamide (193 mg, 329.69 umol, 85% purity, 1 eq) in DCM (3 mL) was added Burgess reagent (235.71 mg, 989.08 umol, 3 eq), and then was stirred at 25° C. for 4 h. Upon completion, the reaction mixture was concentrated under reduced pressure to give a residue. The residue was purified by prep-HPLC (column: Waters Xbridge BEH C18 100*25 mm*5 um; mobile phase: [water (10 mM NH$_4$HCO$_3$)-ACN]; B %: 30%-55%, 10 min) to give (2S,4S)-4-(tert-butyl)-N-((S)-1-cyano-2-((S)-2-oxopyrrolidin-3-yl)ethyl)-1-(4-methoxy-1H-indole-2-carbonyl)pyrrolidine-2-carboxamide (59.58 mg, 124.24 umol, 37.68% yield, 100% purity) as a white solid. MS (ESI) m/z 480.2 [M+H]$^+$.

$^1$H NMR (400 MHz, DMSO-d$_6$) δ=11.69-11.55 (m, 1H), 9.17-8.75 (m, 1H), 7.81-7.44 (m, 1H), 7.16-7.07 (m, 1H), 7.06-6.98 (m, 2H), 6.55-6.46 (m, 1H), 5.03-4.53 (m, 2H), 4.04-3.74 (m, 4H), 3.69-3.36 (m, 1H), 3.22-2.55 (m, 2H), 2.35-1.95 (m, 5H), 1.83-1.51 (m, 3H), 1.00-0.82 (m, 9H).

$^1$H NMR (400 MHz, DMSO-d$_6$, 273+80K) δ=11.31 (s, 1H), 8.68 (s, 1H), 7.38 (s, 1H), 7.18-7.02 (m, 2H), 6.90 (s, 1H), 6.60-6.47 (m, 1H), 4.96 (q, J=7.6 Hz, 1H), 4.72 (s, 1H), 4.07-3.80 (m, 4H), 3.66-3.50 (m, 1H), 3.28-3.05 (m, 2H), 2.32-1.97 (m, 5H), 1.95-1.64 (m, 3H), 0.95 (s, 9H).

Example 71. Synthesis of Viral Protease Inhibitor Compound 659

Step 1: (S)-tert-butyl (1-hydroxy-4,4-dimethylpentan-2-yl)carbamate

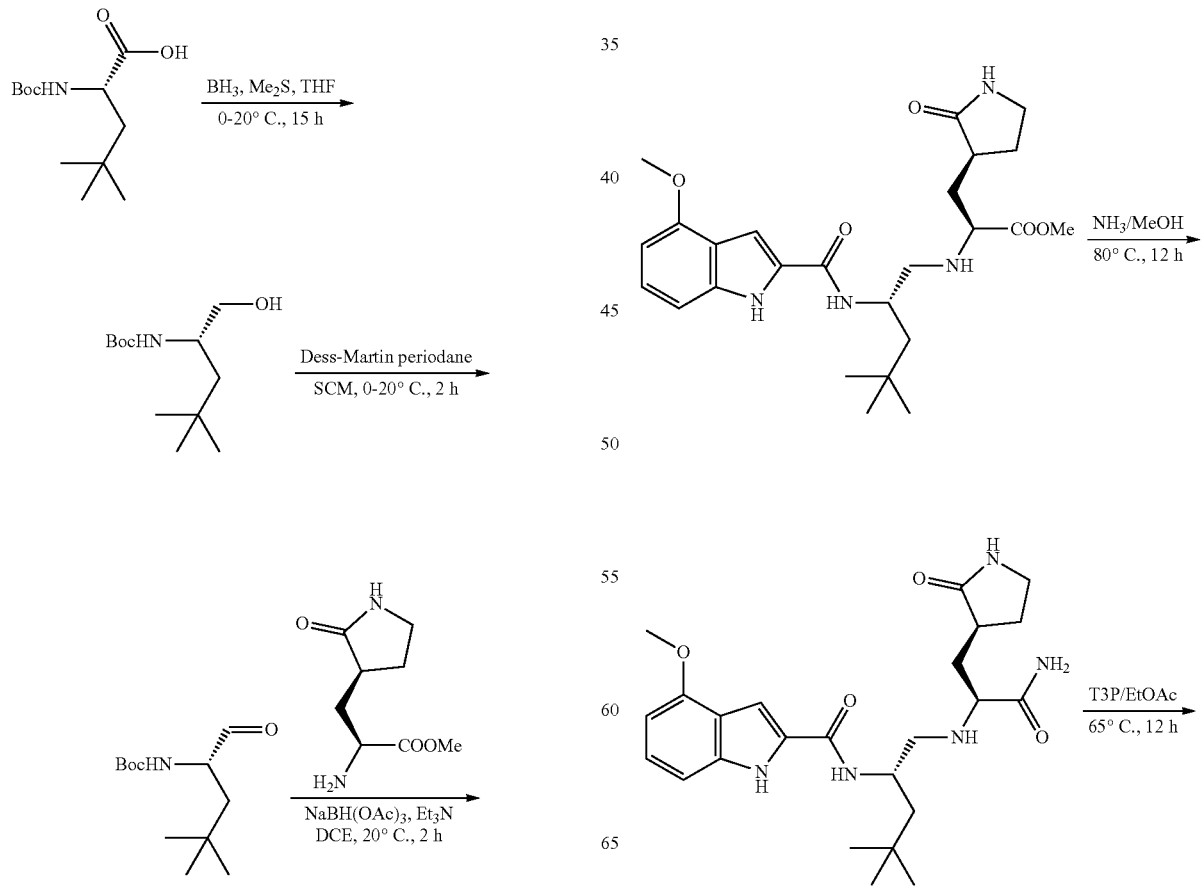

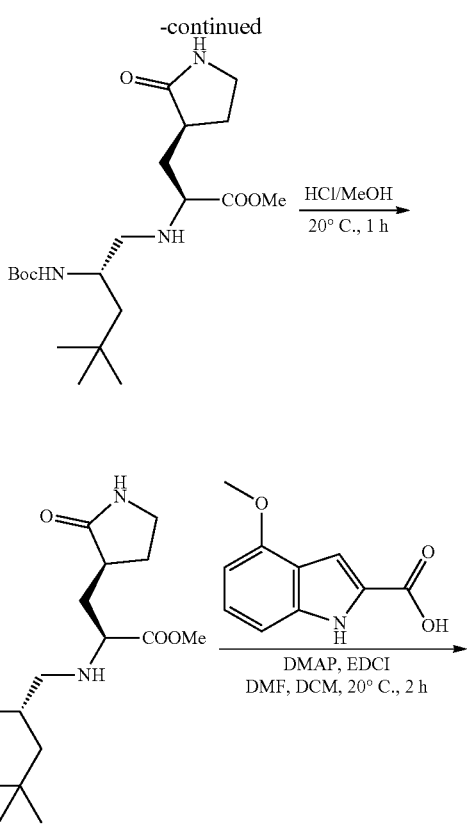

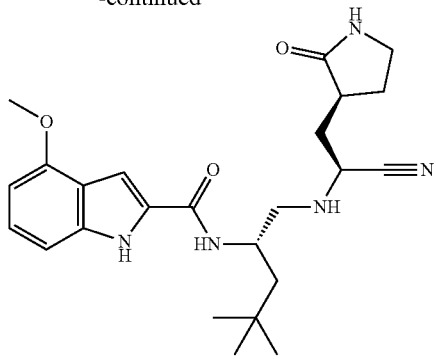

To a solution of (2S)-2-(tert-butoxycarbonylamino)-4,4-dimethyl-pentanoic acid (5 g, 20.38 mmol, 1 eq) in THF (100 mL) at 0° C., BH₃-Me₂S (10 M, 4.08 mL, 2.0 eq) was added drop-wise slowly, then the mixture was stirred at 20° C. for 15 h. The reaction mixture was added into MeOH (40 mL) and stirred for 20 min, then the mixture was concentrated. The residue was diluted with aq. NaHCO₃ (150 mL) and extracted with DCM (100 mL*3). The combined organic layers were washed with brine (100 mL), dried over Na₂SO₄, filtered and concentrated under reduced pressure to give a residue. The residue was purified by column chromatography (SiO₂, petroleum ether:ethyl acetate=1:0 to 1:1) to afford tert-butyl N-[(1S)-1-(hydroxymethyl)-3,3-dimethyl-butyl]carbamate (2.5 g, 10.81 mmol, 53.02% yield) as a colorless oil.

Step 2: (S)-tert-butyl (4,4-dimethyl-1-oxopentan-2-yl)carbamate

To a solution of tert-butyl N-[(1S)-1-(hydroxymethyl)-3,3-dimethyl-butyl]carbamate (2.4 g, 10.37 mmol, 1 eq) in DCM (40 mL) was added periodinane (5.72 g, 13.49 mmol, 4.18 mL, 1.3 eq) via Dess-martin at 0° C., and the reaction was stirred for 1 h. The mixture was warm to 20° C. and stirred for 1 h. The reaction mixture was quenched by addition H₂O (60 mL) at 0° C., and then added drop-wise aq. NaHCO₃ to pH=8 at 0° C., and extracted with EtOAc (40 mL*3). The combined organic layers were washed with brine (50 mL), dried over Na₂SO₄, filtered and concentrated under reduced pressure to give a residue. The residue was purified by column chromatography (SiO₂, petroleum ether:ethyl acetate=0:1 to 1:1) to afford tert-butyl N-[(1S)-1-formyl-3,3-dimethyl-butyl]carbamate (1.6 g, 6.98 mmol, 67.25% yield) as a colorless oil.

¹H NMR (400 MHz, DMSO-d₆) δ ppm 9.40 (s, 1H) 7.30 (br d, J=8.00 Hz, 1H) 3.91-3.82 (m, 1H) 1.66 (dd, J=14.38, 2.75 Hz, 1H) 1.39 (s, 9H) 1.32 (br d, J=9.26 Hz, 1H) 0.90 (s, 9H).

Step 3: (S)-methyl2-(((S)-2-((tert-butoxycarbonyl)amino)-4,4-dimethylpentyl)amino)-3-((S)-2-oxopyrrolidin-3-yl)propanoate To a solution of tert-butyl N-[(1S)-1-formyl-3,3-dimethyl-butyl]carbamate (0.8 g, 3.49 mmol, 1 eq) and methyl (2S)-2-amino-3-[(3S)-2-oxopyrrolidin-3-yl]propanoate (1.17 g, 5.23 mmol, 1.5 eq, HCl) in DCE (20 mL) was added Et₃N (529.52 mg, 5.23 mmol, 728.36 uL, 1.5 eq) and NaBH(OAc)₃ (2.22 g, 10.47 mmol, 3 eq), and the reaction was stirred at 20° C. for 2 h.

The reaction mixture was quenched by addition aq. NaHCO₃ (100 mL) at 0° C. and stirred for 0.5 h, then extracted with DCM (60 mL*3). The combined organic layers were washed with brine (50 mL), dried over Na₂SO₄, filtered and concentrated under reduced pressure to give a residue. The residue was purified by column chromatography (SiO₂, petroleum ether:ethyl acetate=0:1 to 1:3) to get the product methyl (2S)-2-[[(2S)-2-(tert-butoxycarbonylamino)-4,4-dimethyl-pentyl]amino]-3-[(3S)-2-oxopyrrolidin-3-yl]propanoate (450 mg, 1.13 mmol, 32.29% yield) as a white solid. MS (ESI) m/z 400.3 [M+H]⁺.

Step 4: (S)-methyl 2-(((S)-2-amino-4,4-dimethyl-pentyl)amino)-3-((S)-2-oxopyrrolidin-3-yl)propanoate A solution of methyl (2S)-2-[[(2S)-2-(tert-butoxycarbonylamino)-4,4-dimethyl-pentyl]amino]-3-[(3S)-2-oxopyrrolidin-3-yl]propanoate (200 mg, 500.60 umol, 1 eq) in HCl/MeOH (4 M, 4.00 mL, 31.96 eq) was stirred at 20° C. for 1 h. The reaction mixture was concentrated under reduced pressure to afford methyl (2S)-2-[[(2S)-2-amino-4,4-dimethyl-pentyl]amino]-3-[(3S)-2-oxopyrrolidin-3-yl]propanoate (168 mg, crude, HCl) as a white solid.

Step 5: (S)-methyl 2-(((S)-2-(4-methoxy-1H-indole-2-carboxamido)-4,4-dimethylpentyl)amino)-3-((S)-2-oxopyrrolidin-3-yl)propanoate To a solution of methyl (2S)-2-[[(2S)-2-amino-4,4-dimethyl-pentyl]amino]-3-[(3S)-2-oxopyrrolidin-3-yl]propanoate (168 mg, 500.20 umol, 1 eq, HCl) and 4-methoxy-1H-indole-2-carboxylic acid (95.63 mg, 500.20 umol, 1 eq) in DMF (1 mL) was added DMAP (183.32 mg, 1.50 mmol, 3.0 eq) and EDCI (191.78 mg, 1.00 mmol, 2 eq) and DCM (3 mL), the mixture was stirred at 20° C. for 2 h. The reaction mixture was quenched by addition H₂O 40 mL at 0° C., and then extracted with DCM (20 mL*3). The combined organic layers were washed with brine (40 mL), dried over Na₂SO₄, filtered and concentrated under reduced pressure to give a residue. The residue was purified by column chromatography (SiO₂, petroleum ether:ethyl acetate=1:0 to 0:1) to afford methyl (2S)-2-[[(2S)-2-[(4-methoxy-1H-indole-2-carbonyl)amino]-4,4-dimethyl-pentyl]amino]-3-[(3S)-2-oxopyrrolidin-3-yl]propanoate (150 mg, 301.54 umol, 60.28% yield, 95% purity) as a yellow oil. MS (ESI) m/z 473.2 [M+H]⁺.

Step 6: N-((S)-1-(((S)-1-amino-1-oxo-3-((S)-2-oxopyrrolidin-3-yl)propan-2-yl)amino)-4,4-dimethylpentan-2-yl)-4-methoxy-H-indole-2-carboxamide A solution of methyl (2S)-2-[[(2S)-2-[(4-methoxy-1H-indole-2-carbonyl)amino]-4,4-dimethyl-pentyl]amino]-3-[(3S)-2-oxopyrrolidin-3-yl]propanoate (130 mg, 275.09 umol, 1 eq) in NH₃/MeOH (7 M, 15 mL, 381.70 eq) was stirred at 80° C. for 12 h. Upon completion, the reaction mixture was concentrated under reduced pressure to give a residue. The residue was purified by prep-TLC (SiO₂, ethyl acetate:methanol=50:3) to get the product N-[(1S)-1-[[[(1S)-2-amino-2-oxo-1-[[(3S)-2-oxopyrrolidin-3-yl]methyl]ethyl]amino]methyl]-3,3-dimethyl-butyl]-4-methoxy-1H-indole-2-carboxamide (60 mg, 131.13 umol, 47.67% yield) as a yellow solid. MS (ESI) m/z 458.3 [M+H]⁺.

Step 7: N-((S)-1-(((S)-1-cyano-2-((S)-2-oxopyrrolidin-3-yl)ethyl)amino)-4,4-dimethylpentan-2-yl)-4-methoxy-1H-indole-2-carboxamide To a solution of N-[(1S)-1-[[[(1S)-2-amino-2-oxo-1-[[(3S)-2-oxopyrrolidin-3-yl]methyl]ethyl]amino]methyl]-3,3-dimethyl-butyl]-4-methoxy-1H-indole-2-carboxamide (50 mg, 109.27 umol, 1 eq) in EtOAc (2 mL) was added $T_3P$ (2.14 g, 3.36 mmol, 2 mL, 50% purity, 30.77 eq) drop-wise, and then the mixture was stirred at 65° C. for 12 h. The reaction mixture was concentrated under reduced pressure to give a residue. The residue was purified by prep-HPLC (column: Phenomenex Luna C18 75*30 mm*3 um; mobile phase: [water (0.2% FA)-ACN]; B %: 15%-45%, 8 min) and was separated by SFC (column: DAICEL CHIRALPAK AD (250 mm*30 mm, 10 um); mobile phase: [0.1% $NH_3H_2O$ ETOH]; B %: 25%-25%, 20 min) to afford N-[(1S)-1-[[[(1S)-1-cyano-2-[(3S)-2-oxopyrrolidin-3-yl]ethyl]amino]methyl]-3,3-dimethyl-butyl]-4-methoxy-1H-indole-2-carboxamide (4.4 mg, 9.92 umol, 29.07% yield, 99.1% purity) as a white solid. MS (ESI) m/z 440.2 $[M+H]^+$.

$^1$H NMR (400 MHz, METHANOL-$d_4$) δ=7.22-6.99 (m, 3H) 6.52 (br d, J=7.72 Hz, 1H) 4.74-4.65 (m, 1H) 4.61-4.48 (m, 1H) 4.03-3.91 (m, 4H) 3.62-3.51 (m, 1H) 3.47-3.36 (m, 1H) 3.27-3.19 (m, 1H) 2.50-2.41 (m, 1H) 2.29-2.18 (m, 1H) 1.81 (br s, 1H) 1.74-1.64 (m, 2H) 1.60 (br d, J=10.14 Hz, 1H) 1.34-1.28 (m, 1H) 0.98 (s, 9H).

Example 72. Synthesis of Viral Protease Inhibitor Compound 671

Step 1: 2-(2-methoxyethoxy)ethyl carbonochloridate

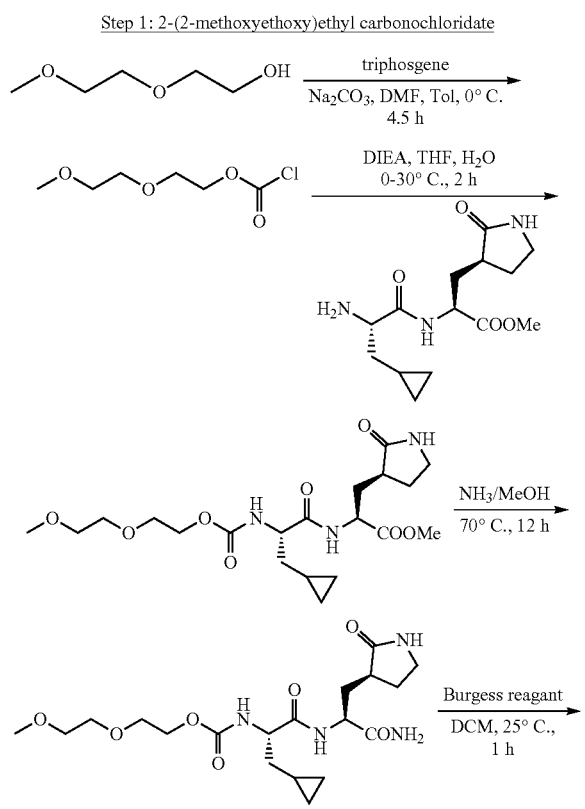

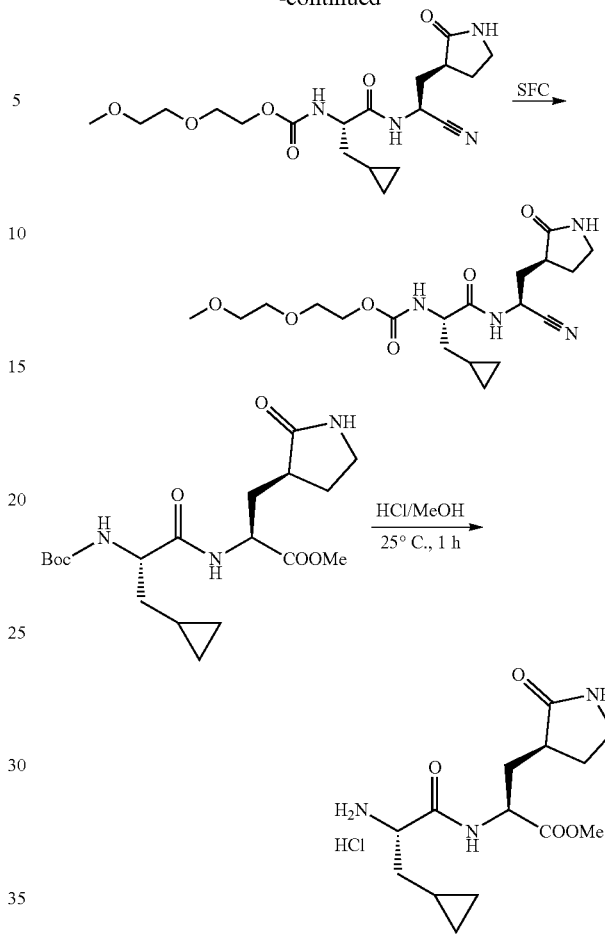

A mixture of triphosgene (4.93 g, 16.61 mmol, 4.99 e−1 eq), $Na_2CO_3$ (3.53 g, 33.29 mmol, 1 eq) and DMF (95.00 mg, 1.30 mmol, 0.1 mL, 3.90 e−2 eq) in toluene (50 mL) was cooled to 0° C. and stirred for 0.5 h under $N_2$ atmosphere. Then a solution of 2-(2-methoxyethoxy)ethanol (4 g, 33.29 mmol, 3.92 mL, 1 eq) was added dropwise. The mixture was stirred at 0° C. for 4 h. Upon completion, the mixture was filtered, and the filtrate was concentrated under the reduced pressure affording 2-(2-methoxyethoxy)ethyl carbonochloridate (6 g) as a yellow oil.

Step 2: (S)-methyl 2-((S)-2-amino-3-cyclopropyl-propanamido)-3-((S)-2-oxopyrrolidin-3-yl)propanoate A mixture of methyl(2S)-2-[[(2S)-2-(tert-butoxycarbonylamino)-3-cyclopropyl-propanoyl]amino]-3-[(3S)-2-oxopyrrolidin-3-yl]propanoate (600 mg, 1.51 mmol, 1 eq) was in HCl/MeOH (4 M, 12.00 mL, 31.80 eq) was stirred at 25° C. for 1 h. Upon completion, the mixture was concentrated under the reduced pressure affording methyl (2S)-2-[[(2S)-2-amino-3-cyclopropyl-propanoyl]amino]-3-[(3S)-2-oxopyrrolidin-3-yl]propanoate (450 mg) as a white solid.

Step 3: (11S,14S)-methyl11-(cyclopropylmethyl)-9,12-dioxo-14-(((S)-2-oxopyrrolidin-3-yl)methyl)-2,5,8-trioxa-10,13-diazapentadecan-15-oate To a solution of methyl (2S)-2-[[(2S)-2-amino-3-cyclopropyl-propanoyl]amino]-3-[(3S)-2-oxopyrrolidin-3-yl]propanoate (450 mg, 1.51 mmol, 1 eq) in THF (10 mL) and H$_2$O (1 mL) was added DIEA (391.19 mg, 3.03 mmol, 527.20 uL, 2 eq), and then 2-(2-methoxyethoxy)ethyl carbonochloridate (414.52 mg, 2.27 mmol, 1.5 eq) was added at 0° C. The mixture was stirred at 30° C. for 2 h. Upon completion, the reaction mixture was quenched by addition H$_2$O (100 mL), and then extracted with ethyl acetate (30 mL*3). The combined organic layers were washed with brine (100 mL), dried over Na$_2$SO$_4$, filtered and concentrated under reduced pressure to give a residue. The residue was purified by prep-HPLC (column: Kromasil C18 (250*50 mm*10 um); mobile phase: [water (10 mM NH$_4$HCO$_3$)-ACN]; B %: 1%-25%, 10 min) affording methyl(2S)-2-[[(2S)-3-cyclopropyl-2-[2-(2-methoxyethoxy)ethoxycarbonylamino]propanoyl]amino]-3-[(3S)-2-oxopyrrolidin-3-yl]propanoate (400 mg, 901.94 umol, 59.60% yield) as a yellow oil. MS (ESI) m/z 444.2 [M+H]$^+$.

Step 4: 2-(2-methoxyethoxy)ethyl((S)-1-(((S)-1-amino-1-oxo-3-((S)-2-oxopyrrolidin-3-yl)propan-2-yl)amino)-3-cyclopropyl-1-oxopropan-2-yl)carbamate A mixture of methyl(2S)-2-[[(2S)-3-cyclopropyl-2-[2-(2-methoxyethoxy)ethoxycarbonylamino]propanoyl]amino]-3-[(3S)-2-oxopyrrolidin-3-yl]propanoate (400 mg, 901.94 umol, 1 eq) in NH$_3$/MeOH (7 M, 10 mL, 77.61 eq) was stirred at 70° C. for 12 h. Upon completion, the mixture was concentrated under the reduced pressure to afford 2-(2-methoxyethoxy)ethylN-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]carbamate (400 mg, crude) as a yellow oil. MS (ESI) m/z 429.2 [M+H]$^+$ Step 5: 2-(2-methoxyethoxy)ethyl((S)-1-(((S)-1-cyano-2-((S)-2-oxopyrrolidin-3-yl)ethyl)amino)-3-cyclopropyl-1-oxopropan-2-yl)carbamate To a solution of 2-(2-methoxyethoxy)ethyl N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]carbamate (380 mg, 886.86 umol, 1 eq) in DCM (5 mL) was added Burgess reagent (422.69 mg, 1.77 mmol, 2 eq). The mixture was stirred at 25° C. for 1 h. Upon completion, the reaction mixture was quenched by addition H$_2$O (50 mL), and extracted with ethyl acetate (30 mL*3). The combined organic layers were washed with brine (30 mL), dried over Na$_2$SO$_4$, filtered and concentrated under reduced pressure to give a residue. The residue was purified with prep-HPLC (column: Waters Xbridge Prep OBD C18 150*40 mm*10 um; mobile phase: [water (10 mM NH$_4$HCO$_3$)-ACN]; B %: 10%-40%, 8 min) affording 2-(2-methoxyethoxy)ethyl N-[(1S)-2-[[(1S)-1-cyano-2-[(3S)-2-oxopyrrolidin-3-yl] ethyl]amino]-1-(cyclopropylmethyl)-2-oxo-ethyl]carbamate (150 mg, crude) as a white solid. MS (ESI) m/z 411.2 [M+H]$^+$ Step 6: 2-(2-methoxyethoxy)ethyl((S)-1-(((S)-1-cyano-2-((S)-2-oxopyrrolidin-3-yl)ethyl)amino)-3-cyclopropyl-1-oxopropan-2-yl)carbamate 2-(2-methoxyethoxy)ethylN-[(1S)-2-[[(1S)-1-cyano-2-[(3S)-2-oxopyrrolidin-3-yl]ethyl]amino]-1-(cyclopropylmethyl)-2-oxo-ethyl]carbamate (150 mg, crude) was separated by SFC (column: DAICEL CHIRALPAK AD (250 mm*30 mm, 10 um); mobile phase: [Neu-EtOH]; B %: 44%-44%, 8 min) affording 2-(2-methoxyethoxy)ethyl N-[(1S)-2-[[(1S)-1-cyano-2-[(3S)-2-oxopyrrolidin-3-yl] ethyl]amino]-1-(cyclopropylmethyl)-2-oxo-ethyl]carbamate (110 mg, 262.36 umol, 71.79% yield, 97.9% purity) as a colorless gum. MS (ESI) m/z 411.2 [M+H]$^+$.

$^1$H NMR (400 MHz, DMSO-d$_6$) δ=8.81 (br d, J=7.8 Hz, 1H), 7.72 (s, 1H), 7.54 (br d, J=7.4 Hz, 1H), 4.95 (q, J=8.2 Hz, 1H), 4.08-3.86 (m, 3H), 3.53 (td, J=4.6, 15.2 Hz, 4H), 3.47-3.39 (m, 2H), 3.33 (s, 3H), 3.19-3.05 (m, 2H), 2.41-2.28 (m, 1H), 2.19-2.03 (m, 2H), 1.81-1.59 (m, 3H), 1.28 (td, J=6.8, 13.6 Hz, 1H), 0.74 (br d, J=5.6 Hz, 1H), 0.46-0.33 (m, 2H), 0.18-0.01 (m, 2H).

Example 73. Synthesis of Viral Protease Inhibitor Compound 691

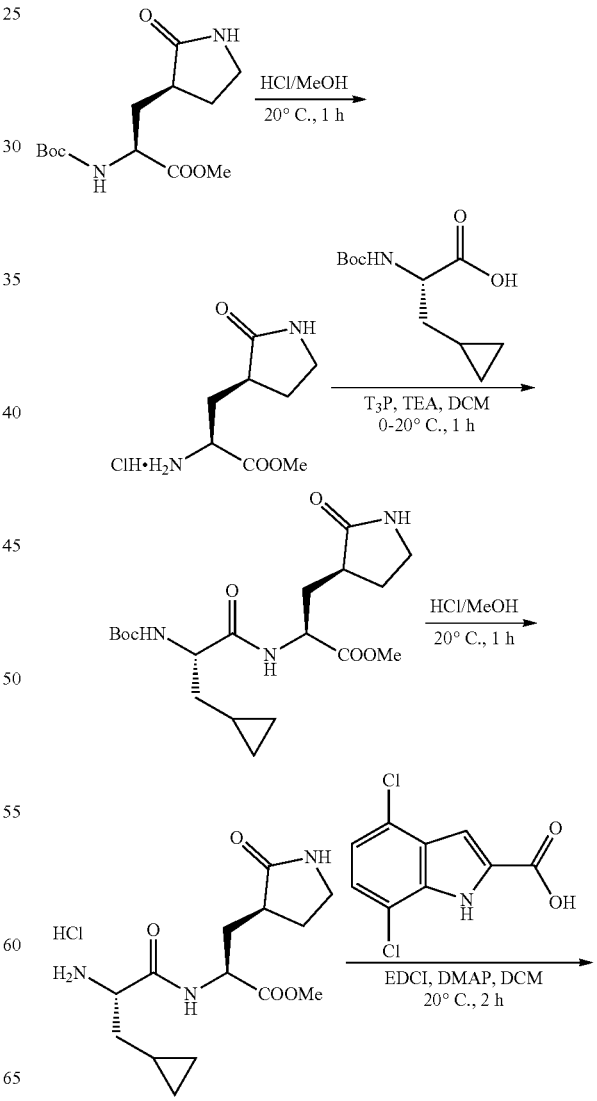

Step 1: methyl (2S)-2-amino-3-[(3S)-2-oxopyrrolidin-3-yl]propanoate

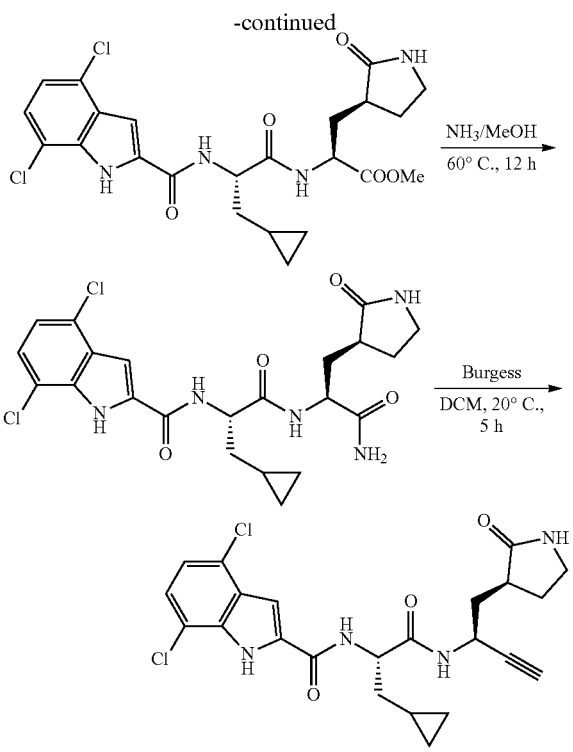

A mixture of methyl (2S)-2-(tert-butoxycarbonylamino)-3-[(3S)-2-oxopyrrolidin-3-yl]propanoate (13.00 g, 45.40 mmol, 1 eq) and HCl/MeOH (4 M, 35 mL, 3.08 eq) was stirred at 20° C. for 1 h. Upon completion, the reaction mixture was concentrated under reduced pressure to afford methyl (2S)-2-amino-3-[(3S)-2-oxopyrrolidin-3-yl]propanoate (10 g, crude, HCl) was obtained as white solid. MS (ESI) m/z 223.1 [M+H]+.

Step 2: methyl (2S)-2-[[(2S)-2-(tert-butoxycarbonylamino)-3-cyclopropyl-propanoyl]amino]-3-[(3S)-2-oxopyrrolidin-3-yl]propanoate A solution of methyl (2S)-2-amino-3-[(3S)-2-oxopyrrolidin-3-yl]propanoate (9.71 g, 43.62 mmol, 1 eq, HCl), (2S)-2-(tert-butoxycarbonylamino)-3-cyclopropyl-propanoic acid (10 g, 43.62 mmol, 1 eq) and TEA (22.07 g, 218.08 mmol, 30.35 mL, 5 eq) in DCM (100 mL) was cooled to 0° C., and then T3P (83.27 g, 130.85 mmol, 77.82 mL, 50% purity, 3 eq) was added into the solution. The mixture was stirred for 1 h and warmed to 20° C. gradually. Upon completion, the mixture was added H2O (100 mL) and then extracted with ethyl acetate (100 mL*3). The combined organic layers were washed with brine (50 mL), dried over Na2SO4, filtered and concentrated under reduced pressure to give a residue. Then the residue was purified by column chromatography (SiO2, petroleum ether:ethyl acetate=0:1) to afford methyl(2S)-2-[[(2S)-2-(tert-butoxycarbonylamino)-3-cyclopropyl-propanoyl]amino]-3-[(3S)-2-oxopyrrolidin-3-yl]propanoate (12 g, 23.41 mmol, 53.67% yield, 77.53% purity) as a white solid. MS (ESI) m/z 398.2 [M+H]+.

Step 3: methyl (2S)-2-[[(2S)-2-amino-3-cyclopropyl-propanoyl]amino]-3-[(3S)-2-oxopyrrolidin-3-yl]propanoate A mixture of methyl (2S)-2-[[(2S)-2-(tert-butoxycarbonylamino)-3-cyclopropyl-propanoyl]amino]-3-[(3S)-2-oxopyrrolidin-3-yl]propanoate (1.5 g, 3.77 mmol, 1 eq) in HCl/methanol (4 M, 100 mL, 105.99 eq) was stirred at 20° C. for 1 h. Upon completion, the mixture was concentrated under reduced pressure to give methyl (2S)-2-[[(2S)-2-amino-3-cyclopropyl-propanoyl]amino]-3-[(3S)-2-oxopyrrolidin-3-yl]propanoate (1.1 g, crude, HCl) as a white solid. MS (ESI) m/z 298.2 [M+H]+.

Step 4: methyl (2S)-2-[[(2S)-3-cyclopropyl-2-[(4,7-dichloro-1H-indole-2-carbonyl)amino]propanoyl]amino]-3-[(3S)-2-oxopyrrolidin-3-yl]propanoate A mixture of 4,7-dichloro-1H-indole-2-carboxylic acid (650 mg, 2.83 mmol, 1 eq), methyl (2S)-2-[[(2S)-2-amino-3-cyclopropyl-propanoyl]amino]-3-[(3S)-2-oxopyrrolidin-3-yl]propanoate (943.18 mg, 2.83 mmol, 1 eq, HCl), EDCI (1.08 g, 5.65 mmol, 2 eq) and DMAP (1.04 g, 8.48 mmol, 3 eq) in DCM (10 mL) was stirred at 20° C. for 1 h. Upon completion, the mixture was added H2O (50 mL) and then extracted with ethyl acetate (30 mL*3). The combined organic layers were washed with brine (50 mL), dried over Na2SO4, filtered and concentrated under reduced pressure to give a residue. The residue was purified by column chromatography (SiO2, petroleum ether:ethyl acetate=0:1) to afford methyl (2S)-2-[[(2S)-3-cyclopropyl-2-[(4,7-dichloro-1H-indole-2-carbonyl)amino]propanoyl]amino]-3-[(3S)-2-oxopyrrolidin-3-yl]propanoate (550 mg, 1.01 mmol, 35.92% yield, 93.99% purity) as a white solid. MS (ESI) m/z 509.1 [M+H]+.

Step5: N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4,7-dichloro-1H-indole-2-carboxamide A mixture of methyl (2S)-2-[[(2S)-3-cyclopropyl-2-[(4,7-dichloro-1H-indole-2-carbonyl)amino]propanoyl]amino]-3-[(3S)-2-oxopyrrolidin-3-yl]propanoate (550 mg, 1.08 mmol, 1 eq) in NH3/methanol (7 M, 154.25 uL, 1 eq) was stirred at 60° C. for 12 h. Upon completion, the mixture was concentrated under reduced pressure to give N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4,7-dichloro-1H-indole-2-carboxamide (500 mg, crude) as white solid. MS (ESI) m/z 494.1 [M+H]+.

Step6: 4,7-dichloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-indole-2-carboxamide A mixture of N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4,7-dichloro-1H-indole-2-carboxamide (450 mg, 910.25 umol, 1 eq) and Burgess reagent (1.30 g, 5.46 mmol, 6 eq) in DCM (10 mL) was stirred at 20° C. for 9 h. Upon completion, the mixture was concentrated under reduced pressure to give the residue. Then the residue was purified by prep-HPLC (column: Phenomenex Gemini-NX 80*40 mm*3 um; mobile phase: [water (10 mM NH4HCO3)-ACN]; B %: 25%-55%, 8 min) to give the product 4,7-dichloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-indole-2-carboxamide (300 mg, 629.78 umol, 69.19% yield, 100% purity) as white solid. MS (ESI) m/z 476.1 [M+H]+.

¹H NMR (400 MHz, METHANOL-d₄) δ=7.66-7.56 (m, 1H), 7.52-7.45 (m, 1H), 7.22-7.14 (m, 1H), 5.16-5.05 (m, 1H), 4.68-4.61 (m, 1H), 3.36-3.32 (m, 2H), 2.70-2.57 (m, 1H), 2.40-2.27 (m, 2H), 1.99-1.69 (m, 4H), 0.91-0.79 (m, 1H), 0.62-0.52 (m, 2H), 0.27-0.15 (m, 2H).

Example 74. Synthesis of Viral Protease Inhibitor Compound 695

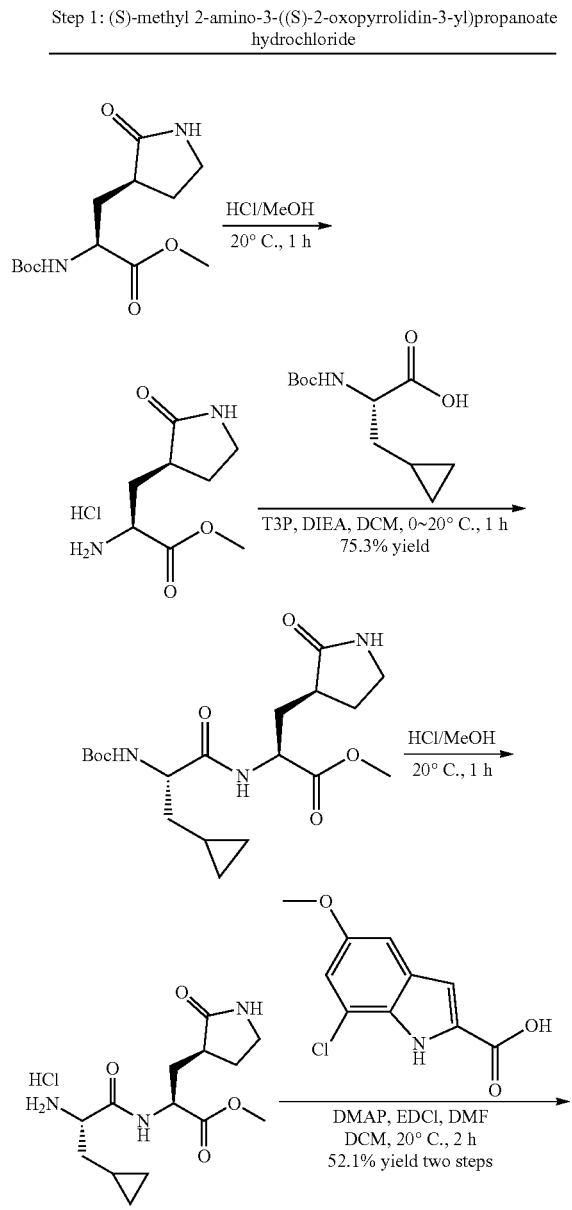

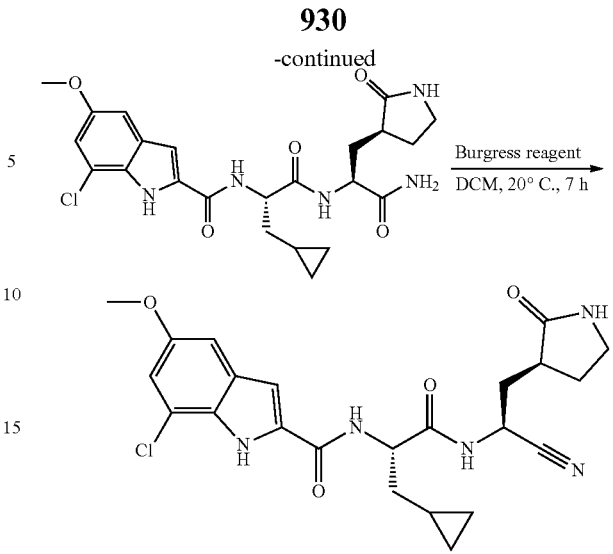

A solution of methyl (2S)-2-(tert-butoxycarbonylamino)-3-[(3S)-2-oxopyrrolidin-3-yl]propanoate (2 g, 6.99 mmol, 1 eq) in HCl/EtOAc (4 M, 40.00 mL, 22.91 eq), the mixture was stirred at 20° C. for 1 h. Upon completion, the reaction mixture was concentrated under reduced pressure to give the product methyl (2S)-2-amino-3-[(3S)-2-oxopyrrolidin-3-yl]propanoate (1.5 g, crude, HCl) as a white solid.

Step 2. (S)-methyl 2-((S)-2-((tert-butoxycarbonyl)amino)-3-cyclopropylpropanamido)-3-((S)-2-oxopyrrolidin-3-yl)propanoate To a solution of methyl (2S)-2-amino-3-[(3S)-2-oxopyrrolidin-3-yl]propanoate (1.4 g, 6.29 mmol, 1 eq, HCl) and (2S)-2-(tert-butoxycarbonylamino)-3-cyclopropyl-propanoic acid (1.44 g, 6.29 mmol, 1.00 eq) in DCM (30 mL) at 0° C. was added DIEA (3.25 g, 25.15 mmol, 4.38 mL, 4 eq) and T₃P (12.00 g, 18.86 mmol, 11.22 mL, 50% purity, 3 eq) was added dropwise, and then the mixture was stirred at 20° C. for 1 h. Upon completion, the reaction mixture was quenched by addition H₂O (60 mL) at 0° C., and then extracted with DCM (30 mL*3). The combined organic layers were washed with brine (30 mL), dried over Na₂SO₄, filtered and concentrated under reduced pressure to give a residue. The residue was purified by column chromatography (SiO₂, petroleum ether:ethyl acetate=5:1 to 0:1) to give the product methyl (2S)-2-[[(2S)-2-(tert-butoxycarbonylamino)-3-cyclopropyl-propanoyl]amino]-3-[(3S)-2-oxopyrrolidin-3-yl]propanoate (1.9 g, 4.73 mmol, 75.27% yield, 99% purity) as a yellow solid. MS (ESI) m/z 398.4 [M+H]⁺.

Step 3: (S)-methyl 2-((S)-2-amino-3-cyclopropyl-propanamido)-3-((S)-2-oxopyrrolidin-3-yl)propanoate hydrochloride A solution of methyl (2S)-2-[[(2S)-2-(tert-butoxycarbonylamino)-3-cyclopropyl-propanoyl]amino]-3-[(3S)-2-oxopyrrolidin-3-yl]propanoate (0.8 g, 2.01 mmol, 1 eq) in HCl/MeOH (4 M, 15 mL, 29.81 eq) was stirred at 20° C. for 1 h. Upon completion, the reaction mixture was concentrated under reduced pressure to give the product methyl (2S)-2-[[(2S)-2-amino-3-cyclopropyl-propanoyl]amino]-3-[(3S)-2-oxopyrrolidin-3-yl]propanoate (670 mg, crude, HCl) as a white solid.

Step 4: (S)-methyl 2-((S)-2-(7-chloro-5-methoxy-1H-indole-2-carboxamido)-3-cyclopropylpropanamido)-3-((S)-2-oxopyrrolidin-3-yl)propanoate To a solution of methyl (2S)-2-[[(2S)-2-amino-3-cyclopropyl-propanoyl]amino]-3-[(3S)-2-oxopyrrolidin-3-yl]propanoate (670 mg, 2.01 mmol, 1.51 eq, HCl) and 7-chloro-5-methoxy-1H-indole-2-carboxylic acid (300 mg, 1.33 mmol, 1 eq) in DMF (5 mL) was added DMAP (487.32 mg, 3.99 mmol, 3 eq), EDCI (509.78 mg, 2.66 mmol, 2 eq) and DCM (15 mL), and the mixture was stirred at 20° C. for 2 h. Upon completion, the reaction mixture was quenched by addition H$_2$O (40 mL) at 0° C., and then extracted with DCM (20 mL*3). The combined organic layers were washed with brine (30 mL), dried over Na$_2$SO$_4$, filtered and concentrated under reduced pressure to give a residue. The residue was purified by column chromatography (SiO$_2$, petroleum ether:ethyl acetate=5:1 to 0:1) to afford methyl (2S)-2-[[(2S)-2-[(7-chloro-5-methoxy-1H-indole-2-carbonyl)amino]-3-cyclopropyl-propanoyl]amino]-3-[(3S)-2-oxopyrrolidin-3-yl]propanoate (350 mg, 658.47 umol, 49.52% yield, 95% purity) as a yellow solid. MS (ESI) m/z 505.2 [M+H]$^+$.

Step 5: N-((S)-1-(((S)-1-amino-1-oxo-3-((S)-2-oxopyrrolidin-3-yl)propan-2-yl)amino)-3-cyclopropyl-1-oxopropan-2-yl)-7-chloro-5-methoxy-1H-indole-2-carboxamide A solution of methyl(2S)-2-[[(2S)-2-[(7-chloro-5-methoxy-1H-indole-2-carbonyl)amino]-3-cyclopropyl-propanoyl]amino]-3-[(3S)-2-oxopyrrolidin-3-yl]propanoate (320 mg, 633.71 umol, 1 eq) in NH$_3$/MeOH (7 M, 40 mL, 441.84 eq) was stirred at 50° C. for 12 h. Upon completion, the reaction mixture was concentrated under reduced pressure to give the product N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-7-chloro-5-methoxy-1H-indole-2-carboxamide (290 mg, crude) as a yellow solid. MS (ESI) m/z 490.2 [M+H]$^+$.

Step 6: 7-chloro-N-((S)-1-(((S)-1-cyano-2-((S)-2-oxopyrrolidin-3-yl)ethyl)amino)-3-cyclopropyl-1-oxopropan-2-yl)-5-methoxy-1H-indole-2-carboxamide To a solution of N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-7-chloro-5-methoxy-1H-indole-2-carboxamide (270 mg, 551.08 umol, 1 eq) in DCM (10 mL) was added Burgess reagent (393.97 mg, 1.65 mmol, 3 eq). After stirring at 20° C. for 7 h, the reaction mixture was concentrated under reduced pressure to give a residue. The residue was purified by prep-HPLC (column: Waters Xbridge Prep OBD C18 150*40 mm*10 um; mobile phase: [water (10 mM NH$_4$HCO$_3$)-ACN]; B %: 20%-50%, 8 min) to give the product 7-chloro-N-[(1S)-2-[[(1S)-1-cyano-2-[(3S)-2-oxopyrrolidin-3-yl]ethyl]amino]-1-(cyclopropylmethyl)-2-oxo-ethyl]-5-methoxy-1H-indole-2-carboxamide (139.27 mg, 295.10 umol, 53.55% yield, 100% purity) as a white solid. MS (ESI) m/z 472.2 [M+H]$^+$.

$^1$H NMR (400 MHz, MeOD-d$_4$) δ=7.17 (s, 1H), 7.07 (d, J=2.0 Hz, 1H), 6.96 (d, J=2.1 Hz, 1H), 5.08 (dd, J=6.0, 10.3 Hz, 1H), 4.55 (t, J=7.4 Hz, 1H), 3.82 (s, 3H), 3.30-3.27 (m, 2H), 2.70-2.60 (m, 1H), 2.40-2.28 (m, 2H), 1.97-1.77 (m, 3H), 1.72-1.60 (m, 1H), 0.86 (br s, 1H), 0.55 (d, J=8.0 Hz, 2H), 0.20 (dd, J=4.8, 9.4 Hz, 2H)

$^1$H NMR (400 MHz, DMSO-d$_6$) δ=11.59 (br s, 1H), 9.00 (d, J=7.9 Hz, 1H), 8.66 (d, J=7.6 Hz, 1H), 7.72 (s, 1H), 7.17 (s, 1H), 7.13 (d, J=2.2 Hz, 1H), 7.00 (d, J=2.2 Hz, 1H), 5.00 (q, J=7.9 Hz, 1H), 4.60-4.45 (m, 1H), 3.78 (s, 3H), 3.18-3.05 (m, 2H), 2.40-2.34 (m, 1H), 2.21-2.06 (m, 2H), 1.86-1.64 (m, 3H), 1.50 (ddd, J=6.1, 7.6, 13.9 Hz, 1H), 0.90-0.75 (m, 1H), 0.50-0.37 (m, 2H), 0.25-0.15 (m, 1H), 0.13-0.04 (m, 1H)

Example 75. Synthesis of Viral Protease Inhibitor Compound 711

Step 1: methyl (2S)-2-[[(2S)-2-amino-3-cyclopropyl-propanoyl]amino]-3-[(3S)-2-oxopyrrolidin-3-yl]propanoate

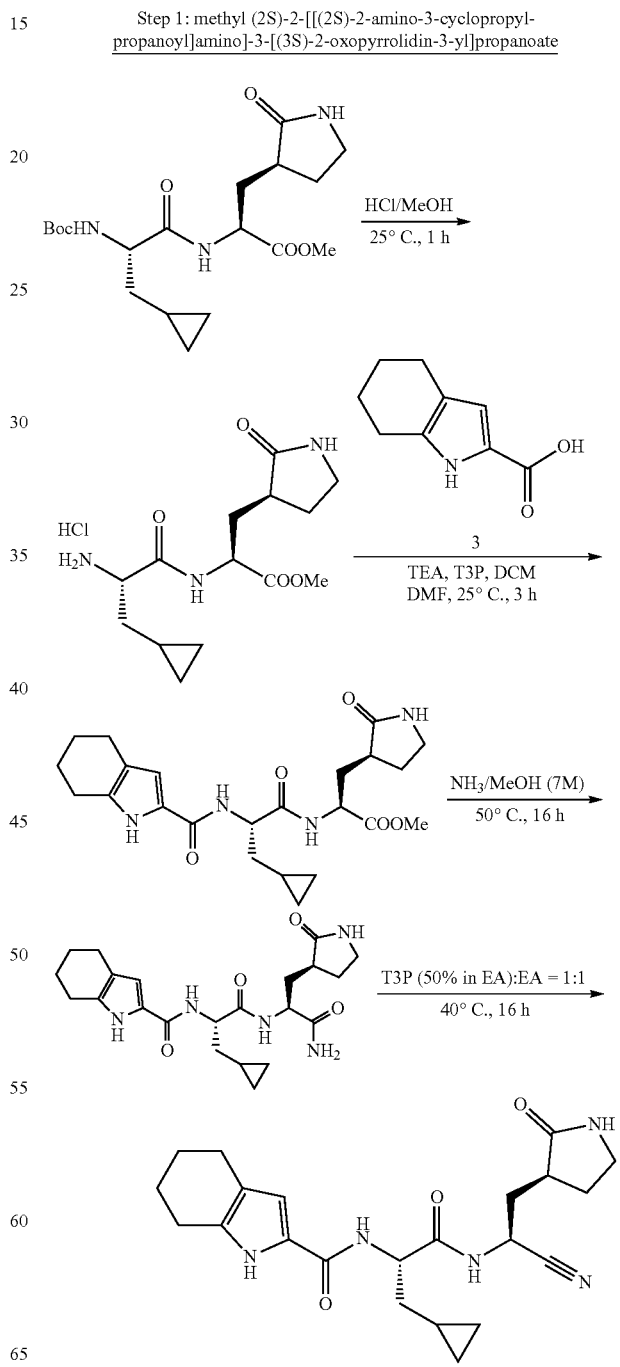

A mixture of methyl (2S)-2-[[(2S)-2-(tert-butoxycarbonylamino)-3-cyclopropyl-propanoyl]amino]-3-[(3S)-2-oxopyrrolidin-3-yl]propanoate (900 mg, 1.81 mmol, 80% purity, 1 eq) in HCl/MeOH (4 M, 12.00 mL, 26.50 eq) was stirred at 25° C. for 1 h. Upon completion, the mixture was concentrated under reduced pressure to give a residue, then was dissolved with DCM (10 mL*3) and concentrated under reduced pressure to afford methyl (2S)-2-[[(2S)-2-amino-3-cyclopropyl-propanoyl]amino]-3-[(3S)-2-oxopyrrolidin-3-yl]propanoate (600 mg, crude, HCl) as white oil. MS (ESI) m/z 298.1 [M+H]$^+$.

Step 2: methyl (2S)-2-[[(2S)-3-cyclopropyl-2-(4,5,6,7-tetrahydro-1H-indole-2-carbonylamino)propanoyl]amino]-3-[(3S)-2-oxopyrrolidin-3-yl]propanoate To a mixture of methyl (2S)-2-[[(2S)-2-amino-3-cyclopropyl-propanoyl]amino]-3-[(3S)-2-oxopyrrolidin-3-yl]propanoate (600 mg, 1.80 mmol, 1 eq, HCl) in DCM (7 mL) and DMF (0.5 mL) was added 4,5,6,7-tetrahydro-1H-indole-2-carboxylic acid (415.68 mg, 2.52 mmol, 1.4 eq), TEA (1.09 g, 10.78 mmol, 1.50 mL, 6 eq) and T3P (1.72 g, 2.70 mmol, 1.60 mL, 50% purity, 1.5 eq). After stirring at 25° C. for 3 h, the reaction mixture was diluted with water (10 mL) and extracted with DCM (3 mL*3). The combined organic layers were dried over Na$_2$SO$_4$, filtered and concentrated under reduced pressure to give a residue. The residue was purified by prep-TLC (SiO$_2$, DCM:MeOH=10:1) and TLC (SiO$_2$, DCM:MeOH=10:1) to get the product methyl (2S)-2-[[(2S)-3-cyclopropyl-2-(4,5,6,7-tetrahydro-1H-indole-2-carbonylamino)propanoyl]amino]-3-[(3S)-2-oxopyrrolidin-3-yl]propanoate (350 mg, 787.36 umol, 43.80% yield) as yellow oil. MS (ESI) m/z 445.3 [M+H]$^+$.

Step 3: N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4,5,6,7-tetrahydro-1H-indole-2-carboxamide A mixture of methyl (2S)-2-[[(2S)-3-cyclopropyl-2-(4,5,6,7-tetrahydro-1H-indole-2-carbonylamino)propanoyl]amino]-3-[(3S)-2-oxopyrrolidin-3-yl]propanoate (350 mg, 787.36 umol, 1 eq) in NH$_3$/MeOH (7 M, 10 mL, 88.90 eq) was stirred at 50° C. for 16 h. Upon completion, the reaction mixture was concentrated under reduced pressure to afford N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4,5,6,7-tetrahydro-1H-indole-2-carboxamide (300 mg, crude) as yellow solid. MS (ESI) m/z 430.2 [M+H]$^+$.

Step 4: N-[(1S)-2-[[(1S)-1-cyano-2-[(3S)-2-oxopyrrolidin-3-yl]ethyl]amino]-1-(cyclopropylmethyl)-2-oxo-ethyl]-4,5,6,7-tetrahydro-1H-indole-2-carboxamide A mixture of N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4,5,6,7-tetrahydro-1H-indole-2-carboxamide (290 mg, 675.19 umol, 1 eq) in T3P (3 mL, 50% purity) and ethyl acetate (3 mL) was stirred at 40° C. for 16 h. Upon completion, the reaction mixture was diluted with water (10 mL) and extracted with ethyl acetate (3 mL*3). The combined organic layers were dried over Na$_2$SO$_4$, filtered and concentrated under reduced pressure to give a residue. The residue was purified by prep-HPLC (column: Waters X bridge BEH C18 100*25 mm*5 um; mobile phase: [water (10 mM NH$_4$HCO$_3$)-ACN]; B %: 25%-55%, 10 min) to afford N-[(1S)-2-[[(1S)-1-cyano-2-[(3S)-2-oxopyrrolidin-3-yl]ethyl]amino]-1-(cyclopropylmethyl)-2-oxo-ethyl]-4,5,6,7-tetrahydro-1H-indole-2-carboxamide (61.92 mg, 150.48 umol, 22.29% yield, 100% purity) as white solid. MS (ESI) m/z 412.3 [M+H]$^+$.

$^1$H NMR (400 MHz, DMSO-d$_6$) δ=10.96 (br s, 1H), 9.00-8.77 (m, 1H), 7.89-7.66 (m, 2H), 6.60 (br s, 1H), 5.04-4.81 (m, 1H), 4.48-4.28 (m, 1H), 3.24-3.04 (m, 2H), 2.47-1.96 (m, 7H), 1.81-1.61 (m, 7H), 1.40 (br dd, J=6.6, 13.1 Hz, 1H), 0.74 (br s, 1H), 0.38 (br s, 2H), 0.22-0.03 (m, 2H).

$^1$H NMR (400 MHz, DMSO-d$_6$) δ=10.67 (br s, 1H), 8.74-8.49 (m, 1H), 7.53-7.28 (m, 2H), 6.54 (d, J=2.2 Hz, 1H), 5.05-4.84 (m, 1H), 4.54-4.38 (m, 1H), 3.17 (br d, J=7.2 Hz, 2H), 2.54 (br t, J=6.1 Hz, 2H), 2.43 (br t, J=5.6 Hz, 3H), 2.28-2.08 (m, 2H), 1.90-1.79 (m, 1H), 1.77-1.65 (m, 6H), 1.56 (qd, J=6.7, 13.7 Hz, 1H), 0.83-0.70 (m, 1H), 0.42 (br d, J=7.8 Hz, 2H), 0.20-0.04 (m, 2H).

Example 76. Synthesis of Viral Protease Inhibitor Compound 719

Step 1: tert-butyl 7-(((S)-1-methoxy-1-oxo-3-((S)-2-oxopiperidin-3-yl)propan-2-yl)carbamoyl)-6-azaspiro[3.4]octane-6-carboxylate

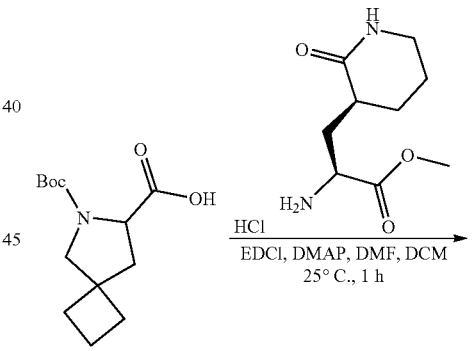

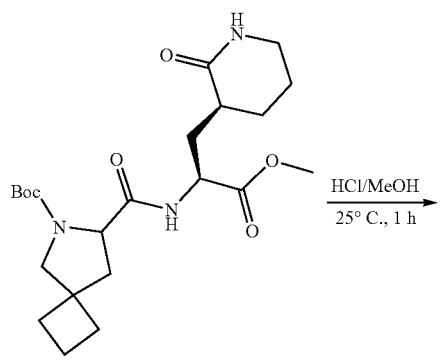

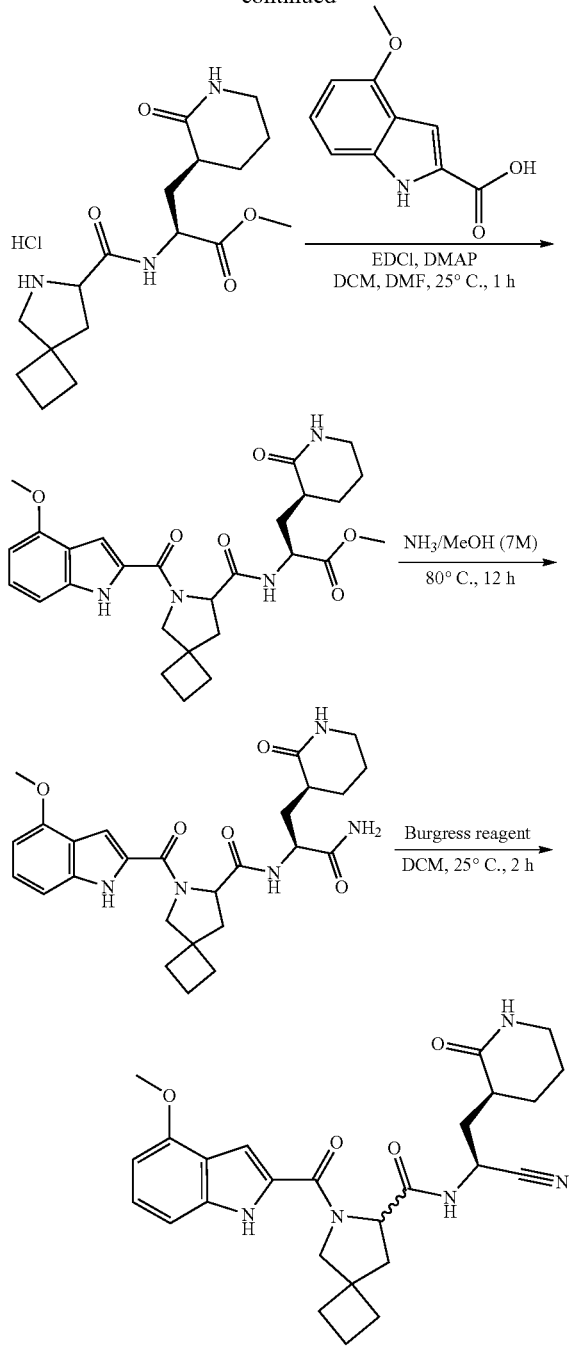

To a solution of methyl (2S)-2-amino-3-[(3S)-2-oxo-3-piperidyl]propanoate (1.08 g, 4.57 mmol, 1 eq, HCl) and 6-tert-butoxycarbonyl-6-azaspiro[3.4]octane-7-carboxylic acid (1.4 g, 5.48 mmol, 1.2 eq) in DCM (15 mL) and DMF (1 mL) was added EDCI (1.75 g, 9.14 mmol, 2 eq) and DMAP (1.67 g, 13.71 mmol, 3 eq), and the mixture was stirred at 25° C. for 1 h. Upon completion, the reaction mixture was diluted with water (50 mL) and extracted with DCM (30 mL*3). The combined organic layers were dried over Na$_2$SO$_4$, filtered and concentrated under reduced pressure to give a residue. The residue was purified by column chromatography (SiO$_2$, petroleum ether/ethyl acetate=2/1 to 0:1) to give tert-butyl 7-[[(1S)-2-methoxy-2-oxo-1-[[(3S)-2-oxo-3-piperidyl]methyl]ethyl]carbamoyl]-6-azaspiro[3.4]octane-6-carboxylate (1.4 g, 2.56 mmol, 56.02% yield, 80% purity) as a yellow oil. MS (ESI) m/z 438.3 [M+H]$^+$.

Step 2: tert-butyl 7-(((S)-1-amino-1-oxo-3-((S)-2-oxopiperidin-3-yl)propan-2-yl)carbamoyl)-6-azaspiro[3.4]octane-6-carboxylate A mixture of tert-butyl 7-[[(1S)-2-methoxy-2-oxo-1-[[(3S)-2-oxo-3-piperidyl]methyl]ethyl]carbamoyl]-6-azaspiro[3.4]octane-6-carboxylate (0.7 g, 1.60 mmol, 1 eq) in HCl/MeOH (4 M, 20 mL, 50.00 eq) was stirred at 25° C. for 2 h. Upon completion, the reaction mixture was concentrated under reduced pressure to give methyl (2S)-2-(6-azaspiro[3.4]octane-7-carbonylamino)-3-[(3S)-2-oxo-3-piperidyl]propanoate (0.6 g, crude, HCl) as a white solid. MS (ESI) m/z 338.1 [M+H]$^+$.

Step 3: methyl (2S)-2-[[6-(4-methoxy-1H-indole-2-carbonyl)-6-azaspiro[3.4]octane-7-carbonyl]amino]-3-[(3S)-2-oxo-3-piperidyl]propanoate To a mixture of methyl (2S)-2-(6-azaspiro[3.4]octane-7-carbonylamino)-3-[(3S)-2-oxo-3-piperidyl]propanoate (0.6 g, 1.60 mmol, 1 eq, HCl) and 4-methoxy-1H-indole-2-carboxylic acid (368.18 mg, 1.93 mmol, 1.2 eq) in DCM (10 mL) and DMF (2 mL) was added EDCI (461.47 mg, 2.41 mmol, 1.5 eq) and DMAP (588.18 mg, 4.81 mmol, 3 eq). After stirring at 25° C. for 1 h, the reaction mixture was diluted with water (50 mL) and extracted with DCM (20 mL*2). The combined organic layers were dried over Na$_2$SO$_4$, filtered and concentrated under reduced pressure to give a residue. The residue was purified by column chromatography (SiO$_2$, petroleum ether/ethyl acetate=2:1 to 0/1) to give methyl (2S)-2-[[6-(4-methoxy-1H-indole-2-carbonyl)-6-azaspiro[3.4]octane-7-carbonyl]amino]-3-[(3S)-2-oxo-3-piperidyl]propanoate (0.65 g, 1.15 mmol, 71.39% yield, 90% purity) as a yellow solid. MS (ESI) m/z 511.3 [M+H]$^+$.

Step 4: N-[(1S)-2-amino-2-oxo-1-[[(3S)-2-oxo-3-piperidyl]methyl]ethyl]-6-(4-methoxy-1H-indole-2-carbonyl)-6-azaspiro[3.4]octane-7-carboxamide A mixture of methyl (2S)-2-[[6-(4-methoxy-1H-indole-2-carbonyl)-6-azaspiro[3.4]octane-7-carbonyl]amino]-3-[(3S)-2-oxo-3-piperidyl]propanoate (0.65 g, 1.15 mmol, 90% purity, 1 eq) in NH$_3$/MeOH (7 M, 10 mL, 61.10 eq) was stirred at 80° C. for 12 h. Upon completion, the reaction mixture was concentrated under reduced pressure to give N-[(1S)-2-amino-2-oxo-1-[[(3S)-2-oxo-3-piperidyl]methyl]ethyl]-6-(4-methoxy-1H-indole-2-carbonyl)-6-azaspiro[3.4]octane-7-carboxamide (0.6 g, crude) as a yellow solid. MS (ESI) m/z 496.3 [M+H]$^+$.

Step 5: N-[(1S)-2-amino-2-oxo-1-[[(3S)-2-oxo-3-piperidyl]methyl]ethyl]-6-(4-methoxy-1H-indole-2-carbonyl)-6-azaspiro[3.4]octane-7-carboxamide To a solution of N-[(1S)-2-amino-2-oxo-1-[[(3S)-2-oxo-3-piperidyl]methyl]ethyl]-6-(4-methoxy-1H-indole-2-carbonyl)-6-azaspiro[3.4]octane-7-carboxamide (0.58 g, 1.17 mmol, 1 eq) in DCM (7 mL) was added Burgess reagent (1.39 g, 5.85 mmol, 5 eq), and the solution was stirred at 25° C. for 2 h. Upon completion, the reaction mixture was diluted with water (30 mL) and extracted with DCM (20 mL*3). The combined organic layers were dried over Na$_2$SO$_4$, filtered and concentrated under reduced pressure to give a residue. The residue was separated by prep-TLC (SiO₂, ethyl acetate:MeOH=20:1) to get N-[(1S)-1-cyano-2-[(3S)-2-oxo-3-piperidyl]ethyl]-6-(4-methoxy-1H-indole-2-carbonyl)-6-azaspiro[3.4]octane-7-carboxamide Isomer 1 and N-[(1S)-1-cyano-2-[(3S)-2-oxo-3-piperidyl]ethyl]-6-(4-methoxy-1H-indole-2-carbonyl)-6-azaspiro[3.4]octane-7-carboxamide Isomer 2.

N-[(1S)-1-cyano-2-[(3S)-2-oxo-3-piperidyl]ethyl]-6-(4-methoxy-1H-indole-2-carbonyl)-6-azaspiro[3.4]octane-7-carboxamide Isomer 1 was purified by prep-HPLC (column: Waters Xbridge Prep OBD C18 150*40 mm*10 um; mobile phase: [water (10 mM NH₄HCO₃)-ACN]; B %: 25%-55%, 8 min) to give N-[(1S)-1-cyano-2-[(3S)-2-oxo-3-piperidyl]ethyl]-6-(4-methoxy-1H-indole-2-carbonyl)-6-azaspiro[3.4]octane-7-carboxamide Isomer 1 (92.10 mg, 192.86 umol, 16.48% yield, 100% purity) as a white solid. MS (ESI) m/z 478.3 [M+H]⁺.

¹H NMR (400 MHz, DMSO-d₆) δ=7.17-7.07 (m, 1H), 7.03 (d, J=8.2 Hz, 1H), 7.01-6.96 (m, 1H), 6.55-6.44 (m, 1H), 5.05-4.89 (m, 1H), 4.43 (t, J=7.2 Hz, 1H), 4.01-3.79 (m, 5H), 3.13-2.76 (m, 2H), 2.31-2.05 (m, 4H), 2.03-1.73 (m, 8H), 1.60-0.97 (m, 3H);

¹H NMR (400 MHz, DMSO-d₆) δ=11.49-11.19 (m, 1H), 8.81-8.41 (m, 1H), 7.31-7.20 (m, 1H), 7.11 (br d, J=7.7 Hz, 1H), 7.09-7.02 (m, 1H), 7.02-6.81 (m, 1H), 6.53 (br d, J=7.7 Hz, 1H), 5.06-4.89 (m, 1H), 4.53 (br s, 1H), 4.07-3.79 (m, 5H), 3.10-3.02 (m, 2H), 2.19 (br s, 4H), 2.06-1.31 (m, 1H).

N-[(1S)-1-cyano-2-[(3S)-2-oxo-3-piperidyl]ethyl]-6-(4-methoxy-1H-indole-2-carbonyl)-6-azaspiro[3.4]octane-7-carboxamide Isomer 2 was purified by prep-HPLC (column: Waters Xbridge Prep OBD C18 150*40 mm*10 um; mobile phase: [water (10 mM NH₄HCO₃)-ACN]; B %: 25%-55%, 8 min) to give N-[(1S)-1-cyano-2-[(3S)-2-oxo-3-piperidyl]ethyl]-6-(4-methoxy-1H-indole-2-carbonyl)-6-azaspiro[3.4]octane-7-carboxamide Isomer 2 (30.29 mg, 63.43 umol, 5.42% yield, 100% purity) as a white solid. MS (ESI) m/z 478.3 [M+H]⁺.

¹H NMR (400 MHz, CHLOROFORM-d) δ=10.26-9.64 (m, 1H), 8.99-8.34 (m, 1H), 7.26-7.16 (m, 1H), 7.15-6.74 (m, 2H), 6.62-6.32 (m, 1H), 6.27-5.80 (m, 1H), 5.06-4.83 (m, 1H), 4.81-4.54 (m, 1H), 4.14-3.82 (m, 5H), 3.31-3.03 (m, 2H), 2.56-2.35 (m, 2H), 2.35-2.16 (m, 2H), 2.11-1.73 (m, 9H), 1.52-1.23 (m, 2H).

Example 77. Synthesis of Viral Protease Inhibitor Compound 721

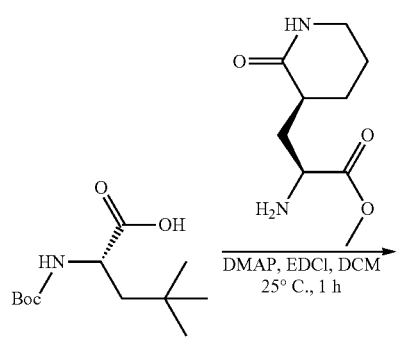

Step 1: (S)-methyl 2-((S)-2-((tert-butoxycarbonyl)amino)-4,4-dimethylpentanamido)-3-((S)-2-oxopiperidin-3-yl)propanoate To a solution of (2S)-2-(tert-butoxycarbonylamino)-4,4-dimethyl-pentanoic acid (2.49 g, 10.14 mmol, 1.2 eq) and methyl (2S)-2-amino-3-[(3S)-2-oxo-3-piperidyl] propanoate (2 g, 8.45 mmol, 1 eq, HCl) in DCM (60 mL) was added DMAP (3.10 g, 25.35 mmol, 3 eq). After EDCI (3.24 g, 16.90 mmol, 2 eq) was added, the mixture was stirred at 25° C. for 1 h. Upon the reaction completement, the mixture was quenched by water (400 mL) and was extracted with DCM (150 mL*3). The organic layer was dried by sat. NaCl (50 mL), concentrated in vacuum and was purified by column (SiO$_2$, petroleum ether:ethyl acetate=2:1 to 0:1), washed with HCl (1 M, 150 mL), extracted with DCM (50 mL*3), and then the pH was adjusted to ~8 with sat. NaHCO$_3$ (30 mL). After extracting with DCM (100 mL), the residue was concentrated in vacuum to obtain (S)-methyl 2-((S)-2-((tert-butoxycarbonyl)amino)-4,4-dimethylpentanamido)-3-((S)-2-oxopiperidin-3-yl) propanoate (3 g, 6.32 mmol, 74.74% yield, 90% purity) as a white solid.

$^1$H NMR (400 MHz, CDCl$_3$-d) δ ppm 7.61 (d, J=7.0 Hz, 1H), 6.85-6.51 (m, 1H), 6.22 (s, 1H), 5.06-4.85 (m, 1H), 4.63-4.47 (m, 1H), 4.30-4.02 (m, 1H), 3.79-3.66 (m, 3H), 3.35-3.25 (m, 2H), 2.42-2.24 (m, 1H), 2.14-2.05 (m, 1H), 1.96-1.66 (m, 4H), 1.63-1.52 (m, 1H), 1.43 (s, 9H), 1.03-0.90 (m, 9H).

Step 2: (S)-methyl 2-((S)-2-amino-4,4-dimethylpentanamido)-3-((S)-2-oxopiperidin-3-yl)propanoate A solution of (S)-methyl 2-((S)-2-((tert-butoxycarbonyl)amino)-4,4-dimethylpentanamido)-3-((S)-2-oxopiperidin-3-yl) propanoate (1.5 g, 3.51 mmol, 1 eq) in HCl/MeOH (4 M, 20 mL)n was stirred at 25° C. for 1 h. Upon the reaction completed, the mixture was concentrated in vacuum to obtain (S)-methyl 2-((S)-2-amino-4,4-dimethylpentanamido)-3-((S)-2-oxopiperidin-3-yl)propanoate (1.1 g, crude, HCl) as a white solid.

$^1$H NMR (400 MHz, D$_2$O) δ ppm 4.57 (dd, J=4.8, 10.3 Hz, 1H), 3.98 (dd, J=5.2, 7.8 Hz, 1H), 3.78-3.65 (m, 3H), 3.29-3.14 (m, 2H), 2.75-2.33 (m, 1H), 2.24-1.47 (m, 8H), 1.04-0.86 (m, 9H).

Step 3: (S)-methyl2-((S)-2-(7-chloro-1H-indole-2-carboxamido)-4,4-dimethylpentanamido)-3-((S)-2-oxopiperidin-3-yl)propanoate To a solution of (S)-methyl 2-((S)-2-amino-4,4-dimethylpentanamido)-3-((S)-2-oxopiperidin-3-yl)propanoate (550 mg*2, HCl salt, 1.68 mmol, 1 eq) and 7-chloro-1H-indole-2-carboxylic acid (394.29 mg, 2.02 mmol, 1.2 eq) in DCM (6 mL) was added DMAP (615.66 mg, 5.04 mmol, 3 eq), and then was added EDCI (644.05 mg, 3.36 mmol, 2 eq) to the mixture at 25° C. After stirring at 25° C. for 1 h, the mixture was quenched by water (200 mL) and was extracted with DCM (70 mL*3), then was concentrated in vacuum and was purified by column (SiO$_2$, petroleum ether:ethyl acetate=1:1 to 0:1) and was concentrated in vacuum, then was washed with 1M HCl (100 mL) and was extracted with DCM (30 mL*3) and the pH of the organic phase was adjusted to pH~7 with sat. NaHCO$_3$ (30 mL). The residue was concentrated in vacuum to obtain (S)-methyl 2-((S)-2-(7-chloro-1H-indole-2-carboxamido)-4,4-dimethylpentanamido)-3-((S)-2-oxopiperidin-3-yl)propanoate (650 mg, 1.16 mmol, 40% yield, 90% purity) as a light yellow solid. MS (ESI) m/z 505.2 [M+H]$^+$ $^1$H NMR (400 MHz, MeOD-d$_4$) δ ppm 7.58 (d, J=7.8 Hz, 1H), 7.32-7.17 (m, 2H), 7.06 (t, J=7.8 Hz, 1H), 4.73 (dd, J=3.8, 8.6 Hz, 1H), 4.55 (dd, J=4.0, 11.7 Hz, 1H), 3.71 (s, 3H), 3.35 (s, 1H), 3.24-3.01 (m, 211), 2.49-2.22 (m, 2H), 2.02-1.40 (m, 8H), 1.08-0.96 (m, 9H).

Step 4: N-((S)-1-(((S)-1-amino-1-oxo-3-((S)-2-oxopiperidin-3-yl)propan-2-yl)amino)-4,4-dimethyl-1-oxopentan-2-yl)-7-chloro-1H-indole-2-carboxamide A solution of (S)-methyl 2-((S)-2-(7-chloro-1H-indole-2-carboxamido)-4,4-dimethylpentanamido)-3-((S)-2-oxopiperidin-3-yl)propanoate (650 mg, 1.29 mmol, 1 eq) in NH$_3$/MeOH (7M, 10 mL) was stirred at 50° C. for 16 h. Upon the reaction completement, the mixture was concentrated in vacuum to obtained N-((S)-1-(((S)-1-amino-1-oxo-3-((S)-2-oxopiperidin-3-yl) propan-2-yl) amino)-4,4-dimethyl-1-oxopentan-2-yl)-7-chloro-1H-indole-2-carboxamide (450 mg, crude) as a light yellow solid. MS (ESI) m/z 490.3 [M+H]$^+$.

Step 5: 7-chloro-N-((S)-1-(((S)-1-cyano-2-((S)-2-oxopiperidin-3-yl)ethyl)amino)-4,4-dimethyl-1-oxopentan-2-yl)-1H-indole-2-carboxamide To a solution of N-((S)-1-(((S)-1-amino-1-oxo-3-((S)-2-oxopiperidin-3-yl) propan-2-yl) amino)-4,4-dimethyl-1-oxopentan-2-yl)-7-chloro-1H-indole-2-carboxamide (430 mg, 877.56 umol, 1 eq) in DCM (10 mL) was added Burgess reagent (627.38 mg, 2.63 mmol, 3 eq), and the reaction was stirred at 25° C. for 4 h. Upon the reaction completement, the mixture was quenched by water (10 mL) and was dried by blowing N$_2$ and was purified by prep-HPLC (column: Kromasil C18 (250*50 mm*10 um); mobile phase: [water (10 mM NH$_4$HCO$_3$)-ACN]; B %: 35%-65%, 10 min) to obtain 7-chloro-N-((S)-1-(((S)-1-cyano-2-((S)-2-oxopiperidin-3-yl)ethyl)amino)-4,4-dimethyl-1-oxopentan-2-yl)-1H-indole-2-carboxamide (205 mg, 424.79 umol, 48.41% yield, 97.8% purity) as a white solid. MS (ESI) m/z 472.2 [M+H]$^+$.

$^1$H NMR (400 MHz, DMSO-d$_6$) δ ppm 11.70 (s, 1H), 9.02 (d, J=8.0 Hz, 1H), 8.71 (d, J=8.0 Hz, 1H), 7.63 (d, J=8.0 Hz, 1H), 7.52 (s, 1H), 7.34-7.23 (m, 2H), 7.07 (t, J=7.8 Hz, 1H), 5.05 (q, J=8.2 Hz, 1H), 4.63-4.54 (m, 1H), 3.07 (s, 2H), 2.30-2.18 (m, 2H), 1.88-1.32 (m, 7H), 0.95 (s, 9H).

Example 78. Synthesis of Viral Protease Inhibitor Compound 723

Step 1: tert-butyl 2,2-difluoro-7-(((S)-1-methoxy-1-oxo-3-((S)-2-oxopiperidin-3-yl)propan-2-yl)carbamoyl)-6-azaspiro[3.4]octane-6-carboxylate

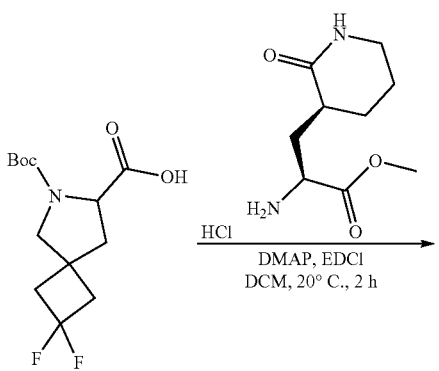

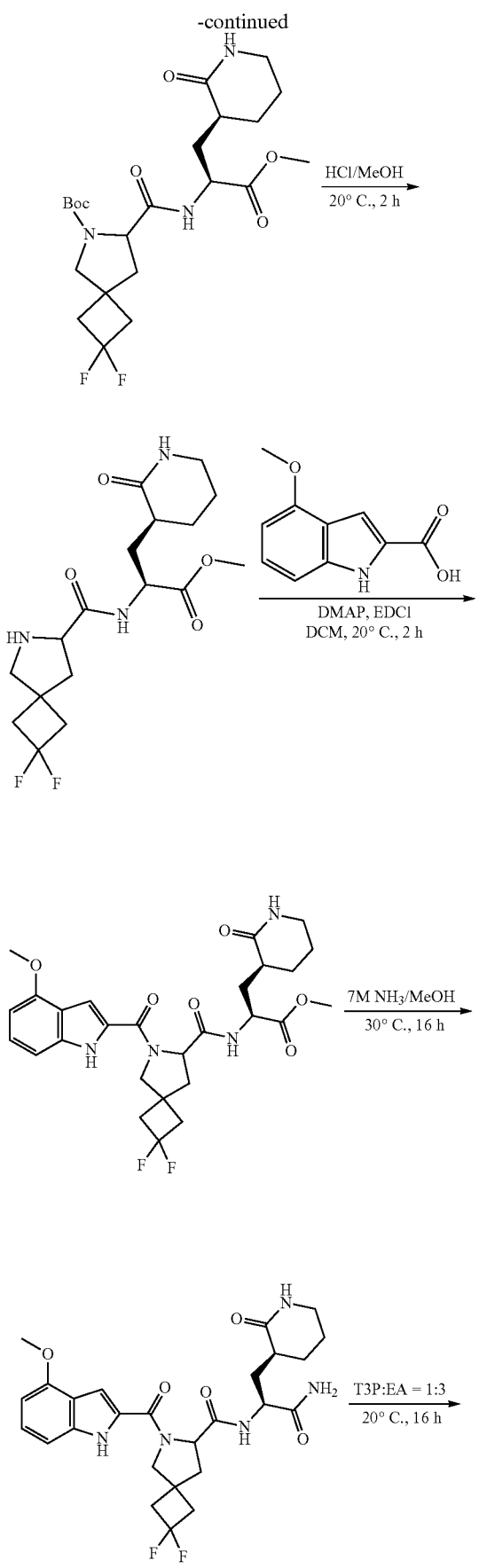

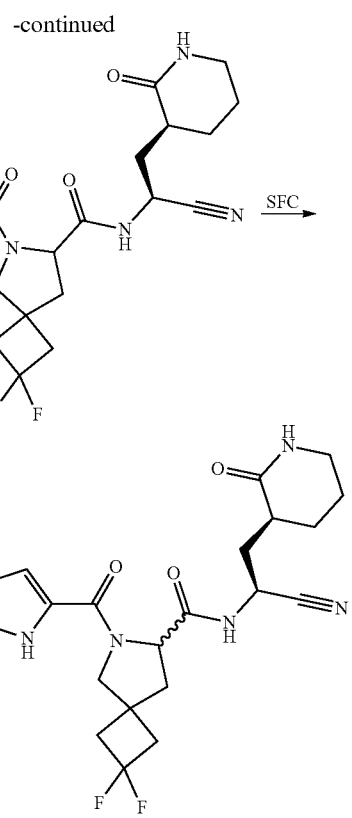

A mixture of (7S)-6-tert-butoxycarbonyl-2,2-difluoro-6-azaspiro[3.4]octane-7-carboxylic acid (500 mg, 1.72 mmol, 1 eq), methyl (2S)-2-amino-3-[(3S)-2-oxo-3-piperidyl]propanoate (406.29 mg, 1.72 mmol, 1 eq, HCl), EDCI (987.17 mg, 5.15 mmol, 3 eq), DMAP (629.10 mg, 5.15 mmol, 3 eq) in DCM (5 mL) was degassed and purged with $N_2$ for 3 times, and then the mixture was stirred at 20° C. for 2 h under $N_2$ atmosphere. Upon completion, the reaction mixture was poured into $H_2O$ (25 mL) at 20° C., and then extracted with DCM (25 mL*3). The combined organic layers were washed with brine (25 mL*2), dried over $Na_2SO_4$, filtered and concentrated under reduced pressure to give a residue. The residue was purified by column chromatography ($SiO_2$, petroleum ether/ethyl acetate=1/0 to 1/1) to afford tert-butyl (7S)-2,2-difluoro-7-[[(1S)-2-methoxy-2-oxo-1-[[(3S)-2-oxo-3-piperidyl]methyl]ethyl]carbamoyl]-6-azaspiro[3.4]octane-6-carboxylate (800 mg, crude) as a white solid. MS (ESI) m/z 474.1 $[M+H]^+$.

Step 2: (2S)-methyl 2-(2,2-difluoro-6-azaspiro[3.4] octane-7-carboxamido)-3-((S)-2-oxopiperidin-3-yl) propanoate A solution of tert-butyl (7S)-2,2-difluoro-7-[[(1S)-2-methoxy-2-oxo-1-[[(3S)-2-oxo-3-piperidyl]methyl]ethyl] carbamoyl]-6-azaspiro[3.4]octane-6-carboxylate (710 mg, 1.50 mmol, 1 eq) in HCl/MeOH (4 M, 8 mL, 21.34 eq) was stirred at 20° C. for 2 h. Upon completion, the reaction mixture was concentrated under reduced pressure to remove solvent to give methyl (2S)-2-[[(7S)-2,2-difluoro-6-azaspiro [3.4]octane-7-carbonyl]amino]-3-[(3S)-2-oxo-3-piperidyl] propanoate (614 mg, crude, HCl) as a yellow oil. MS (ESI) m/z 374.1 $[M+H]^+$.

Step 3: (2S)-methyl 2-(2,2-difluoro-6-(4-methoxy-1H-indole-2-carbonyl)-6-azaspiro[3.4]octane-7-carboxamido)-3-((S)-2-oxopiperidin-3-yl)propanoate To a solution of methyl (2S)-2-[[(7S)-2,2-difluoro-6-azaspiro[3.4]octane-7-carbonyl]amino]-3-[(3S)-2-oxo-3-piperidyl]propanoate (614 mg, 1.50 mmol, 1 eq, HCl), 4-methoxy-1H-indole-2-carboxylic acid (286.41 mg, 1.50 mmol, 1 eq), DMAP (549.06 mg, 4.49 mmol, 3 eq) in DCM (7 mL) was added EDCI (861.56 mg, 4.49 mmol, 3 eq). The mixture was stirred at 20° C. for 2 h. Upon completion, the reaction mixture was poured into H₂O (25 mL) at 20° C., and then extracted with DCM (25 mL*3). The combined organic layers were washed with brine (20 mL*2), dried over Na₂SO₄, filtered and concentrated under reduced pressure to give a residue. The residue was purified by column chromatography (SiO₂, petroleum ether/ethyl acetate=80/1 to 1/1) to give methyl (2S)-2-[[(7S)-2,2-difluoro-6-(4-methoxy-1H-indole-2-carbonyl)-6-azaspiro[3.4]octane-7-carbonyl]amino]-3-[(3S)-2-oxo-3-piperidyl]propanoate (550 mg, 1.01 mmol, 67.17% yield) as a yellow solid. MS (ESI) m/z 547.2 [M+H]⁺.

Step 4: N-((S)-1-amino-1-oxo-3-((S)-2-oxopiperidin-3-yl)propan-2-yl)-2,2-difluoro-6-(4-methoxy-1H-indole-2-carbonyl)-6-azaspiro[3.4]octane-7-carboxamide A solution of methyl (2S)-2-[[(7S)-2,2-difluoro-6-(4-methoxy-1H-indole-2-carbonyl)-6-azaspiro[3.4]octane-7-carbonyl]amino]-3-[(3S)-2-oxo-3-piperidyl]propanoate (535 mg, 978.85 umol, 1 eq) in NH₃/MeOH (7 M, 10.70 mL, 76.52 eq) was stirred at 30° C. for 16 h. Upon completion, the reaction mixture was concentrated under reduced pressure to remove solvent to afford (7S)-N-[(1S)-2-amino-2-oxo-1-[[(3S)-2-oxo-3-piperidyl]methyl]ethyl]-2,2-difluoro-6-(4-methoxy-1H-indole-2-carbonyl)-6-azaspiro[3.4]octane-7-carboxamide (520 mg, crude) as a yellow solid. MS (ESI) m/z 532.2 [M+H]⁺.

Step 5: N-((S)-1-cyano-2-((S)-2-oxopiperidin-3-yl)ethyl)-2,2-difluoro-6-(4-methoxy-1H-indole-2-carbonyl)-6-azaspiro[3.4]octane-7-carboxamide A solution of (7S)-N-[(1S)-2-amino-2-oxo-1-[[(3S)-2-oxo-3-piperidyl]methyl]ethyl]-2,2-difluoro-6-(4-methoxy-1H-indole-2-carbonyl)-6-azaspiro[3.4]octane-7-carboxamide (515 mg, 968.86 umol, 1 eq) in EtOAc (2.5 mL) was added T3P (2.68 g, 4.20 mmol, 2.5 mL, 50% purity, 4.34 eq) was stirred at 20° C. for 16 h. Upon completion, the reaction mixture was poured into H₂O (25 mL) at 20° C., and then extracted with EtOAc (25 mL*3). The combined organic layers were washed with brine (25 mL*2), dried over Na₂SO₄, filtered and concentrated under reduced pressure to give a residue. The residue was purified by prep-HPLC (column: Kromasil C18 (250*50 mm*10 um); mobile phase: [water (10 mM NH₄HCO₃)-ACN]; B %: 45%-75%, 10 min) to give (7S)-N-[(1S)-1-cyano-2-[(3S)-2-oxo-3-piperidyl]ethyl]-2,2-difluoro-6-(4-methoxy-1H-indole-2-carbonyl)-6-azaspiro[3.4]octane-7-carboxamide (188 mg, 364.99 umol, 37.67% yield, 99.7% purity) as a white solid. MS (ESI) m/z 514.3 [M+H]⁺.

Step 6: N-((S)-1-cyano-2-((S)-2-oxopiperidin-3-yl)ethyl)-2,2-difluoro-6-(4-methoxy-1H-indole-2-carbonyl)-6-azaspiro[3.4]octane-7-carboxamide Isomer 1: (7S)-N-[(1S)-1-cyano-2-[(3S)-2-oxo-3-piperidyl]ethyl]-2,2-difluoro-6-(4-methoxy-1H-indole-2-carbonyl)-6-azaspiro[3.4]octane-7-carboxamide (170 mg) was separated by SFC (column: REGIS(S,S)WHELK-O1 (250 mm*25 mm, 10 um); mobile phase: [0.1% NH₃H₂O ETOH]; B %: 60%-60%, 10 min) to give (7S)-N-[(1S)-1-cyano-2-[(3S)-2-oxo-3-piperidyl]ethyl]-2,2-difluoro-6-(4-methoxy-1H-indole-2-carbonyl)-6-azaspiro[3.4]octane-7-carboxamide (42.5 mg, 82.76 umol, 25.00% yield, 100% purity) as a white solid. MS (ESI) m/z 514.3 [M+H]⁺.

Isomer 1: ¹H NMR (400 MHz, MeOD-d₄) δ=7.26-6.72 (m, 3H), 6.53 (d, J=7.6 Hz, 1H), 5.03 (d, J=5.7, 10.5 Hz, 1H), 4.64 (d, J=1.7 Hz, 1H), 4.25 (d, J=10.1 Hz, 1H), 4.15-4.01 (m, 1H), 3.98-3.87 (m, 2H), 4.16-3.86 (m, 1H), 3.13 (s, 2H), 2.87-2.15 (m, 8H), 1.99-1.28 (m, 5H); and to give (7S)-N-[(1S)-1-cyano-2-[(3S)-2-oxo-3-piperidyl]ethyl]-2,2-difluoro-6-(4-methoxy-1H-indole-2-carbonyl)-6-azaspiro[3.4]octane-7-carboxamide (89.8 mg, 173.47 umol, 52.40% yield, 99.2% purity) as a white solid. MS (ESI) m/z 514.3 [M+H]⁺.

Isomer 2: ¹H NMR (400 MHz, MeOD-d₄) δ=7.17-6.82 (m, 3H), 6.56-6.44 (m, 1H), 5.17-5.03 (m, 4H), 4.61 (t, J=7.5 Hz, 1H), 4.15 (s, 1H), 4.01-3.78 (m, 4H), 3.26-2.86 (m, 2H), 2.75-2.14 (m, 8H), 2.06-1.30 (m, 5H).

Example 79. Synthesis of Viral Protease Inhibitor Compound 725

Step 1: (S)-methyl2-((S)-2-((tert-butoxycarbonyl)amino)-4,4-dimethylpentanamido)-3-((S)-2-oxopiperidin-3-yl)propanoate

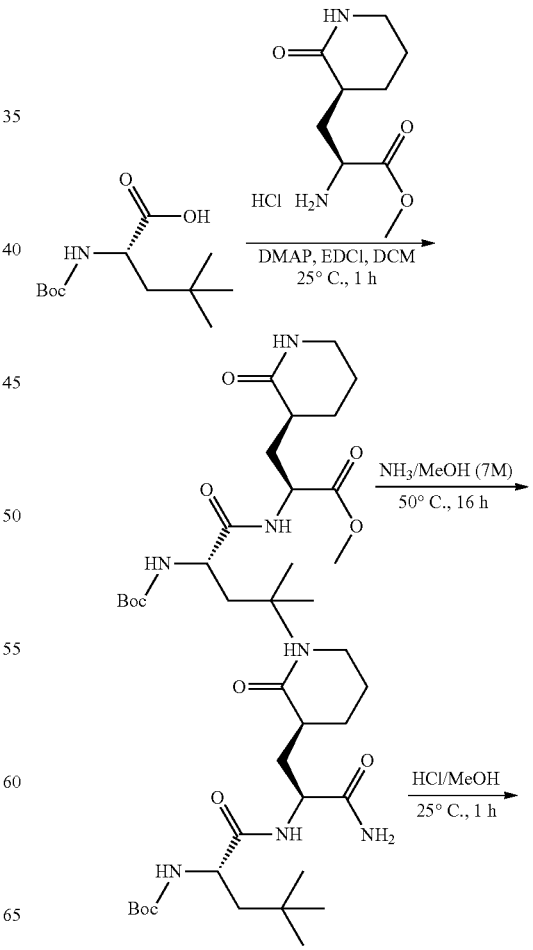

-continued

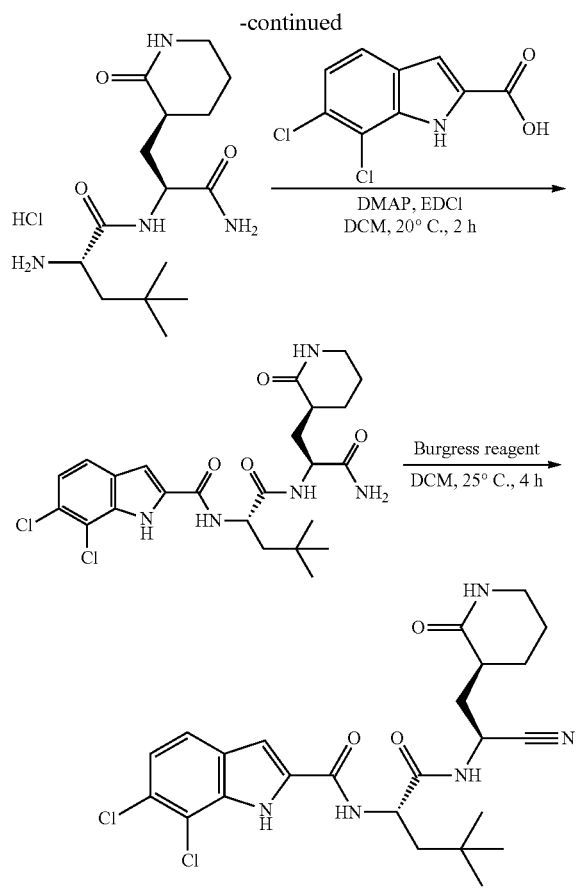

To a solution of (2S)-2-(tert-butoxycarbonylamino)-4,4-dimethylpentanoic acid (1.24 g, 5.07 mmol, 1.2 eq) and methyl (2S)-2-amino-3-[(3S)-2-oxo-3-piperidyl] propanoate (1 g, 4.22 mmol, 1 eq, HCl) in DCM (30 mL) was added DMAP (1.55 g, 12.67 mmol, 3 eq), and then was added EDCI (1.62 g, 8.45 mmol, 2 eq). The mixture was stirred at 25° C. for 1 h. Upon completion, the reaction was quenched by water (400 mL) and was extracted with DCM (150 mL*3). After drying with sat. NaCl (50 mL), the reaction was concentrated in vacuum. The crude product was purified by column (SiO$_2$, petroleum ether:ethyl acetate=2:1 to 0:1) and was washed with 1M HCl (100 mL), extracted with DCM (50 mL*3), the pH was adjusted to pH-8 with sat. NaHCO$_3$ (50 mL), extracted with DCM (50 mL) and concentrated to afford (S)-methyl2-((S)-2-((tert-butoxycarbonyl)amino)-4,4-dimethylpentanamido)-3-((S)-2-oxopiperidin-3-yl)propanoate (1.4 g, 2.95 mmol, 69.76% yield, 90% purity) as a white solid.

Step 2: tert-butyl((S)-1-(((S)-1-amino-1-oxo-3-((S)-2-oxopiperidin-3-yl)propan-2-yl)amino)-4,4-dimethyl-1-oxopentan-2-yl)carbamate A solution of (S)-methyl 2-((S)-2-((tert-butoxycarbonyl) amino)-4, 4-dimethylpentanamido)-3-((S)-2-oxopiperidin-3-yl) propanoate (1.4 g, 3.27 mmol, 1 eq) in NH$_3$/MeOH (18 mL, 7M) was stirred at 50° C. for 16 h. Upon completion, the mixture was concentrated in vacuum to give tert-butyl((S)-1-(((S)-1-amino-1-oxo-3-((S)-2-oxopiperidin-3-yl)propan-2-yl)amino)-4,4-dimethyl-1-oxopentan-2-yl) carbamate (1.1 g, crude) as a white solid.

Step 3: (S)-2-amino-N-((S)-1-amino-1-oxo-3-((S)-2-oxopiperidin-3-yl)propan-2-yl)-4,4-dimethylpentanamide A solution of tert-butyl ((S)-1-(((S)-1-amino-1-oxo-3-((S)-2-oxopiperidin-3-yl) propan-2-yl) amino)-4,4-dimethyl-1-oxopentan-2-yl) carbamate (1.5 g, 3.64 mmol, 1 eq) in HCl/MeOH (4 M, 20 mL) was stirred at 25° C. for 1 h. Upon the reaction completion, the mixture was concentrated in vacuum to give (S)-2-amino-N-((S)-1-amino-1-oxo-3-((S)-2-oxopiperidin-3-yl)propan-2-yl)-4,4-dimethylpentanamide (1.2 g, crude) as a white solid.

Step 4: N-[(1S)-1-[[(1S)-2-amino-2-oxo-1-[[(3S)-2-oxo-3-piperidyl]methyl]ethyl]carbamoyl]-3,3-dimethyl-butyl]-6,7-dichloro-1H-indole-2-carboxamide A mixture of (2S)-2-amino-N-[(1S)-2-amino-2-oxo-1-[[(3S)-2-oxo-3-piperidyl]methyl]ethyl]-4,4-dimethyl-pentanamide (900 mg, 2.58 mmol, 1 eq, HCl) in DCM (8 mL) and DMF (3 mL) was added DMAP (945.50 mg, 7.74 mmol, 3 eq) in one portion at 25° C. The mixture was added 6,7-dichloro-1H-indole-2-carboxylic acid (593.47 mg, 2.58 mmol, 1 eq) and EDCI (1.48 g, 7.74 mmol, 3 eq), and the reaction was stirred at 25° C. for 2 h. Upon completion, the reaction mixture was diluted with H$_2$O (10 mL) and extracted with ethyl acetate (10 mL*3). The combined organic layers were washed with brine (20 mL), dried over Na$_2$SO$_4$, filtered and concentrated under reduced pressure to give the crude product. The crude was purified by column chromatography (SiO$_2$, petroleum ether/ethyl acetate=5/1 to 0/1) to give N-[(1S)-1-[[(1S)-2-amino-2-oxo-1-[[(3S)-2-oxo-3-piperidyl]methyl]ethyl]carbamoyl]-3,3-dimethyl-butyl]-6,7-dichloro-1H-indole-2-carboxamide (450 mg, 858.06 umol, 33.26% yield) as a yellow solid. MS (ESI) m/z 524.2 [M+H]$^+$.

Step 5: 6,7-dichloro-N-[(1S)-1-[[(1S)-1-cyano-2-[(3S)-2-oxo-3-piperidyl]ethyl]carbamoyl]-3,3-dimethyl-butyl]-1H-indole-2-carboxamide To a mixture of N-[(1S)-1-[[(1S)-2-amino-2-oxo-1-[[(3S)-2-oxo-3-piperidyl]methyl]ethyl]carbamoyl]-3,3-dimethyl-butyl]-6,7-dichloro-1H-indole-2-carboxamide (400 mg, 762.72 umol, 1 eq) in DCM (5 mL) was added Burgess reagent (363.53 mg, 1.53 mmol, 2 eq) in one portion at 25° C. The mixture was stirred at 25° C. for 4 h. Upon completion, the reaction mixture was quenched by addition H$_2$O (3 mL), and then combined organic layer was concentrated under reduced pressure to give the crude product. The crude was purified by prep-HPLC (column: Phenomenex Gemini-NX C18 75*30 mm*3 um; mobile phase: [water(0.05% NH3H2O+10 mM NH4HCO3)-ACN]; B %: 35%-65%, 8 min) to give 6,7-dichloro-N-[(1S)-1-[[(1S)-1-cyano-2-[(3S)-2-oxo-3-piperidyl]ethyl]carbamoyl]-3,3-dimethyl-butyl]-1H-indole-2-carboxamide (165 mg, 325.81 umol, 42.72% yield) as a white solid. MS (ESI) m/z 506.1 [M+H]$^+$.

$^1$H NMR (400 MHz, METHANOL-d$_4$) δ=7.54 (d, J=8.4 Hz, 1H), 7.25-7.16 (m, 2H), 5.13-5.05 (m, 1H), 4.66 (dd, J=4.3, 8.3 Hz, 1H), 3.25-3.13 (m, 2H), 2.50-2.35 (m, 2H), 1.99-1.88 (m, 2H), 1.87 (d, J=4.4 Hz, 1H), 1.79 (br dd, J=8.4, 14.6 Hz, 2H), 1.71-1.56 (m, 1H), 1.55-1.43 (m, 1H), 1.03 (s, 9H).

Example 80. Synthesis of Viral Protease Inhibitor Compound 727

Step 1: methyl (2S)-2-[[(2S)-2-(tert-butoxycarbonylamino)-3-cyclopropyl-propanoyl]amino]-3-[(3S)-2-oxo-3-piperidyl]propanoate

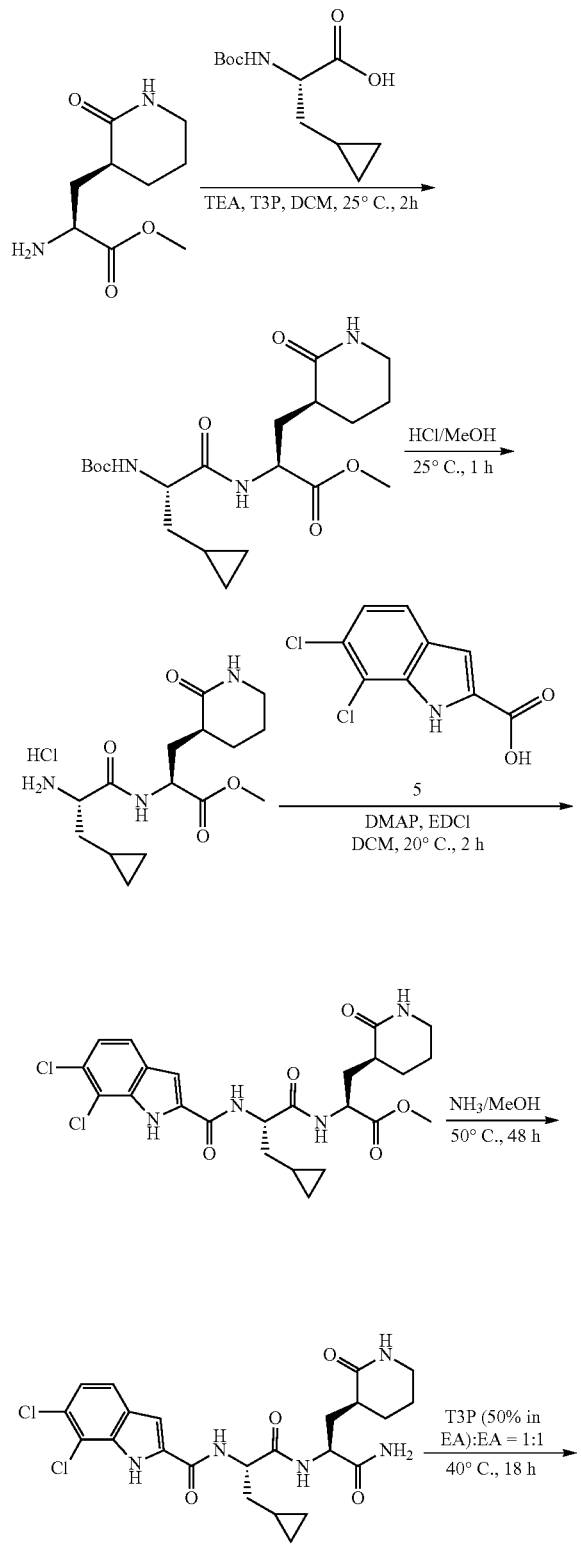

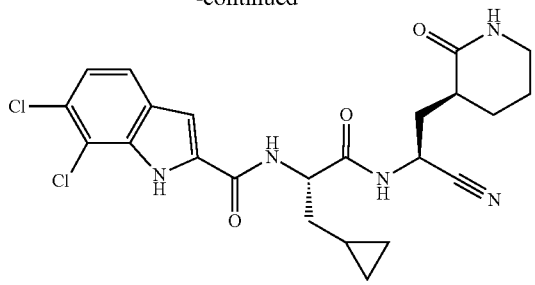

A mixture of methyl (2S)-2-amino-3-[(3S)-2-oxo-3-piperidyl]propanoate (1.3 g, 5.49 mmol, 1 eq, HCl) in DCM (12 mL) was added (2S)-2-(tert-butoxycarbonylamino)-3-cyclopropyl-propanoic acid (1.51 g, 6.59 mmol, 1.2 eq), TEA (3.33 g, 32.95 mmol, 4.59 mL, 6 eq) and T3P (5.24 g, 8.24 mmol, 4.90 mL, 50% purity, 1.5 eq). The reaction was stirred at 25° C. for 2 h. Upon completion, the reaction mixture was diluted with water (10 mL) and extracted with DCM (3 mL*3). The combined organic layers were dried over $Na_2SO_4$, filtered and concentrated under reduced pressure to give a residue. The residue was purified by column ($SiO_2$, DCM:MeOH=10:1) and TLC ($SiO_2$, DCM:MeOH=10:1) to afford methyl (2S)-2-[[(2S)-2-(tert-butoxycarbonylamino)-3-cyclopropyl-propanoyl]amino]-3-[(3S)-2-oxo-3-piperidyl]propanoate (1.99 g, 4.11 mmol, 74.84% yield, 85% purity) as a yellow oil. MS (ESI) m/z 412.2 $[M+H]^+$.

Step 2: methyl (2S)-2-[[(2S)-2-amino-3-cyclopropyl-propanoyl]amino]-3-[(3S)-2-oxo-3-piperidyl]propanoate A mixture of methyl (2S)-2-[[(2S)-2-(tert-butoxycarbonylamino)-3-cyclopropyl-propanoyl]amino]-3-[(3S)-2-oxo-3-piperidyl]propanoate (1.20 g, 2.48 mmol, 85% purity, 1 eq) in HCl/MeOH (4 M, 15 mL, 24.21 eq) was stirred at 25° C. for 1 h. Upon completion, the mixture was concentrated under reduced pressure to give a residue, then was dissolved with DCM (10 mL*3) and concentrated under reduced pressure to afford methyl (2S)-2-[[(2S)-2-amino-3-cyclopropyl-propanoyl]amino]-3-[(3S)-2-oxo-3-piperidyl]propanoate (850 mg, crude, HCl) as a yellow oil. MS (ESI) m/z 312.1 $[M+H]^+$.

Step 3: methyl (2S)-2-[[(2S)-3-cyclopropyl-2-[(6,7-dichloro-1H-indole-2-carbonyl)amino]propanoyl]amino]-3-[(3S)-2-oxo-3-piperidyl]propanoate A mixture of methyl (2S)-2-[[(2S)-2-amino-3-cyclopropyl-propanoyl]amino]-3-[(3S)-2-oxo-3-piperidyl]propanoate (850 mg, 2.44 mmol, 1 eq, HCl) in DCM (10 mL) and DMF (0.5 mL) was added with 6,7-dichloro-1H-indole-2-carboxylic acid (674.59 mg, 2.93 mmol, 1.2 eq, 1.2), DMAP (746.35 mg, 6.11 mmol, 2.5 eq) and EDCI (936.91 mg, 4.89 mmol, 2 eq), and then the resulting mixture was stirred at 25° C. for 2 h. Upon completion, the reaction mixture was diluted with water (10 mL) and extracted with DCM (3 mL*3). The combined organic layers were dried over $Na_2SO_4$, filtered and concentrated under reduced pressure to give a residue. The residue was purified by column ($SiO_2$, DCM:MeOH=10:1) and TLC ($SiO_2$, DCM:MeOH=10:1) to afford methyl (2S)-2-[[(2S)-3-cyclopropyl-2-[(6,7-dichloro-1H-indole-2-carbonyl)amino]propanoyl]amino]-3-[(3S)-2- oxo-3-piperidyl]propanoate (1.24 g, 1.50 mmol, 61.27% yield, 63% purity) as a yellow solid. MS (ESI) m/z 523.2 [M+H]⁺.

Step 4: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6,7-dichloro-1H-indole-2-carboxamide A mixture of methyl (2S)-2-[[(2S)-3-cyclopropyl-2-[(6,7-dichloro-1H-indole-2-carbonyl)amino]propanoyl]amino]-3-[(3S)-2-oxo-3-piperidyl]propanoate (0.38 g, 3 batches in parallel, 726.01 umol, 1 eq) in NH₃/MEOH (7 M, 12.06 mL, 116.31 eq) was stirred at 50° C. for 48 h. Upon completion, The mixture was concentrated under reduced pressure to give a residue, and then was dissolved with DCM (10 mL*3) and concentrated under reduced pressure to afford N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6,7-dichloro-1H-indole-2-carboxamide (1 g, crude) as a yellow oil. MS (ESI) m/z 508.2 [M+H]⁺.

Step 5: 6,7-dichloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide A mixture of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6,7-dichloro-1H-indole-2-carboxamide (1 g, 1.97 mmol, 1 eq) in T3P (5 mL, 50% purity) and ethyl acetate (5 mL) was stirred at 40° C. for 18 h. Upon completion, the reaction mixture was diluted with water (50 mL) and extracted with DCM (20 mL*3). The combined organic layers were dried over Na₂SO₄, filtered and concentrated under reduced pressure to give a residue. The residue was purified by prep-HPLC (column: Waters X bridge Prep OBD C18 150*40 mm*10 um; mobile phase: [water (10 mM NH₄HCO₃)-ACN]; B %: 30%-60%, 8 min) to get the product 6,7-dichloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide (288.22 mg, 587.75 umol, 29.88% yield, 100% purity) as a white solid. MS (ESI) m/z 490.1 [M+H]⁺.

¹H NMR (400 MHz, DMSO-d₆) δ=11.94 (br s, 1H), 9.01 (d, J=7.9 Hz, 1H), 8.76 (br d, J=7.5 Hz, 1H), 7.66 (d, J=8.4 Hz, 1H), 7.55 (br s, 1H), 7.33-7.21 (m, 2H), 5.21-4.90 (m, 1H), 4.60-4.38 (m, 1H), 3.16-3.01 (m, 2H), 2.35-2.18 (m, 2H), 1.90-1.65 (m, 4H), 1.63-1.33 (m, 3H), 0.80 (br d, J=5.5 Hz, 1H), 0.49-0.35 (m, 2H), 0.26-0.05 (m, 2H).

Example 81. Synthesis of Viral Protease Inhibitor Compound 729

Step 1: (2S)-methyl 3-((S)-2-oxopiperidin-3-yl)-2-(6-azaspiro[3.4]octane-7-carboxamido)propanoate

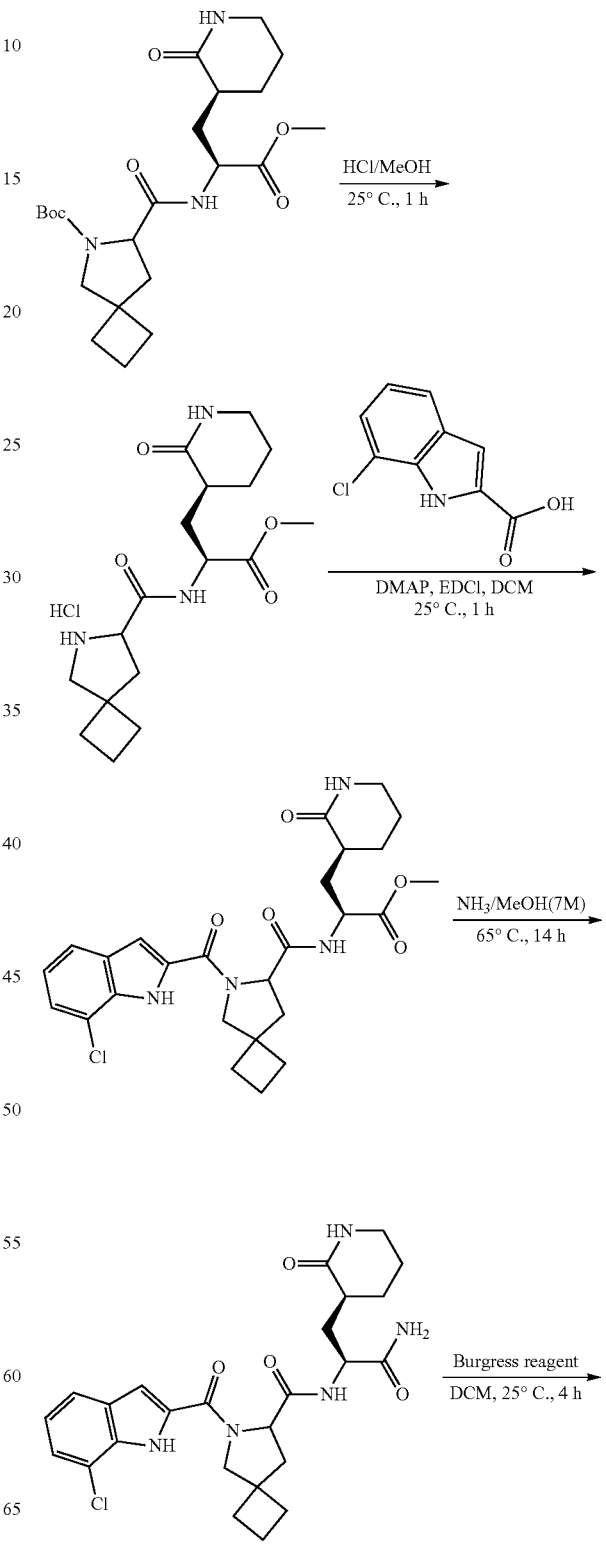

-continued

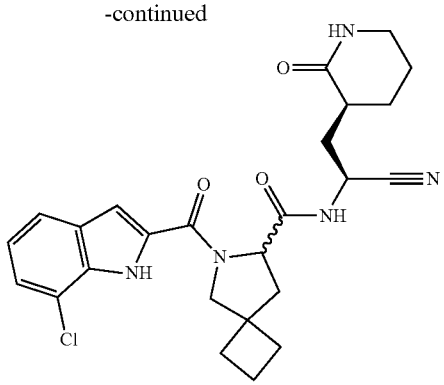

A solution of tert-butyl 7-(((S)-1-methoxy-1-oxo-3-((S)-2-oxopiperidin-3-yl)propan-2-yl)carbamoyl)-6-azaspiro[3.4]octane-6-carboxylate (1 g, 2.29 mmol, 1 eq) in HCl/MeOH (40 mL) was stirred at 25° C. for 1 h. Upon completion, the reaction mixture was concentrated under reduced pressure to remove HCl/MeOH, and then DCM (50 mL) (three times) was added. The reaction was concentrated under reduced pressure to give a crude product (2S)-methyl 3-((S)-2-oxopiperidin-3-yl)-2-(6-azaspiro[3.4]octane-7-carboxamido)propanoate (800 mg, crude, HCl) was obtained as a yellow solid. MS (ESI) m/z 338.2 [M+H]⁺.

Step 2: (2S)-methyl 2-(6-(7-chloro-1H-indole-2-carbonyl)-6-azaspiro[3.4]octane-7-carboxamido)-3-((S)-2-oxopiperidin-3-yl)propanoate To a solution of (2S)-methyl 3-((S)-2-oxopiperidin-3-yl)-2-(6-azaspiro[3.4]octane-7-carboxamido)propanoate (580 mg, 1.72 mmol, 1 eq) and 7-chloro-1H-indole-2-carboxylic acid (504.35 mg, 2.58 mmol, 1.5 eq) in DCM (10 mL) was added DMAP (420.00 mg, 3.44 mmol, 2 eq) and EDCI (494.29 mg, 2.58 mmol, 1.5 eq). The mixture was stirred at 25° C. for 1 h. Upon completion, the reaction was quenched by H₂O (100 mL) and then extracted with DCM (50 mL*3). The combined organic phase was washed with brine (50 mL*2), dried over anhydrous Na₂SO₄, filtered and concentrated in vacuo. The residue was purified by column chromatography (SiO₂, petroleum ether/ethyl acetate=3/1 to 0/1) to afford (2S)-methyl 2-(6-(7-chloro-1H-indole-2-carbonyl)-6-azaspiro[3.4]octane-7-carboxamido)-3-((S)-2-oxopiperidin-3-yl)propanoate (680 mg, 1.19 mmol, 69.13% yield, 90% purity) as a yellow solid. MS (ESI) m/z 515.2 [M+H]⁺.

Step 3: N-[(1S)-2-amino-2-oxo-1-[[(3S)-2-oxo-3-piperidyl]methyl]ethyl]-6-(7-chloro-1H-indole-2-carbonyl)-6-azaspiro[3.4]octane-7-carboxamide To a solution of methyl (2S)-2-[[6-(7-chloro-1H-indole-2-carbonyl)-6-azaspiro[3.4]octane-7-carbonyl]amino]-3-[(3S)-2-oxo-3-piperidyl]propanoate (675 mg, 1.31 mmol, 1 eq) in NH₃ (7 M, in MeOH, 29.53 mL, 157.72 eq). The mixture was stirred at 65° C. for 16 h. Upon completion, the reaction mixture was concentrated under reduced pressure to give a residue. The mixture was added with DCM (50 mL) (three times), and then the reaction was concentrated under reduced pressure to give a residue. The crude product N-[(1S)-2-amino-2-oxo-1-[[(3S)-2-oxo-3-piperidyl]methyl]ethyl]-6-(7-chloro-1H-indole-2-carbonyl)-6-azaspiro[3.4]octane-7-carboxamide (700 mg, crude) was used into the next step and obtained as a yellow solid. MS (ESI) m/z 500.2 [M+H]⁺.

Step 4: 6-(7-chloro-1H-indole-2-carbonyl)-N-[(1S)-1-cyano-2-[(3S)-2-oxo-3-piperidyl]ethyl]-6-azaspiro[3.4]octane-7-carboxamide To a solution of N-[(1S)-2-amino-2-oxo-1-[[(3S)-2-oxo-3-piperidyl]methyl]ethyl]-6-(7-chloro-1H-indole-2-carbonyl)-6-azaspiro[3.4]octane-7-carboxamide (695 mg, 1.39 mmol, 1 eq) in DCM (15 mL) was added Burgess reagent (1.66 g, 6.95 mmol, 5 eq) under N₂. The mixture was stirred at 25° C. for 2 h. Upon completion, the reaction mixture was concentrated under reduced pressure to give a residue at 30° C. The residue was purified by prep-TLC (SiO₂, ethyl acetate:MeOH=20:1) to give desired compound (450 mg, purity 96%) as a yellow solid, which was further separated by SFC (condition: column: DAICEL CHIRALPAK AS (250 mm*30 mm, 10 um); mobile phase: [Neu-ETOH]; B %: 50%-50%, min) to give 6-(7-chloro-1H-indole-2-carbonyl)-N-[(1S)-1-cyano-2-[(3S)-2-oxo-3-piperidyl]ethyl]-6-azaspiro[3.4]octane-7-carboxamide (145 mg, 300.85 umol, 21.64% yield, 100% purity) as a white solid. MS (ESI) m/z 482.3 [M+H]⁺.

¹H NMR (400 MHz, MeOD-d₄) δ=7.67-7.49 (m, 1H), 7.31-7.23 (m, 1H), 7.19-6.99 (m, 2H), 5.14-4.95 (m, 1H), 4.60-4.52 (m, 1H), 4.07-3.77 (m, 2H), 3.27-3.16 (m, 2H), 2.56-1.50 (m, 15H).

¹H NMR (400 MHz, DMSO-d₆) δ=11.27-11.09 (m, 1H), 8.82-8.62 (m, 1H), 7.72-7.53 (m, 1H), 7.36-7.24 (m, 2H), 7.19-7.02 (m, 2H), 5.11-4.85 (m, 1H), 4.67-4.42 (m, 1H), 4.05-3.73 (m, 2H), 3.10-3.06 (m, 2H), 2.30-1.38 (m, 15H).

6-(7-chloro-1H-indole-2-carbonyl)-N-[(1S)-1-cyano-2-[(3S)-2-oxo-3-piperidyl]ethyl]-6-azaspiro[3.4]octane-7-carboxamide (170 mg, 348.13 umol, 25.04% yield, 98.7% purity) as a white solid. MS (ESI) m/z 482.3 [M+H]⁺.

¹H NMR (400 MHz, MeOD-d₄) δ=7.67-7.55 (m, 1H), 7.31-7.25 (m, 1H), 7.18-7.11 (m, 1H), 7.10-7.04 (m, 1H), 4.93 (br s, 1H), 4.60-4.54 (m, 1H), 4.13-3.79 (m, 2H), 2.98 (br s, 2H), 2.42-1.54 (m, 15H).

¹H NMR (400 MHz, DMSO-d₆) δ=11.27-10.98 (m, 1H), 8.88-8.54 (m, 1H), 7.82-7.49 (m, 1H), 7.34-6.98 (m, 4H), 5.10-4.95 (m, 1H), 4.69-4.39 (m, 1H), 4.03-3.72 (m, 2H), 3.10-3.05 (m, 2H), 2.32-1.39 (m, 15H).

Example 82. Synthesis of Viral Protease Inhibitor Compound 731

Step 1: tert-butyl 3-[[[(1S)-2-methoxy-2-oxo-1-[[(3S)-2-oxo-3-piperidyl]methyl]ethyl]carbamoyl]-2-azaspiro[4.5]decane-2-carboxylate

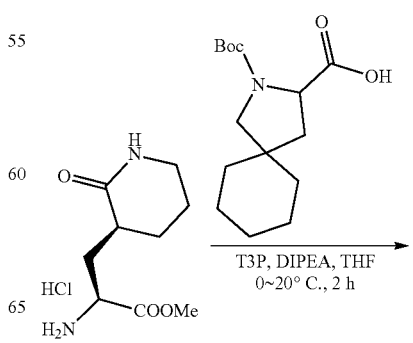

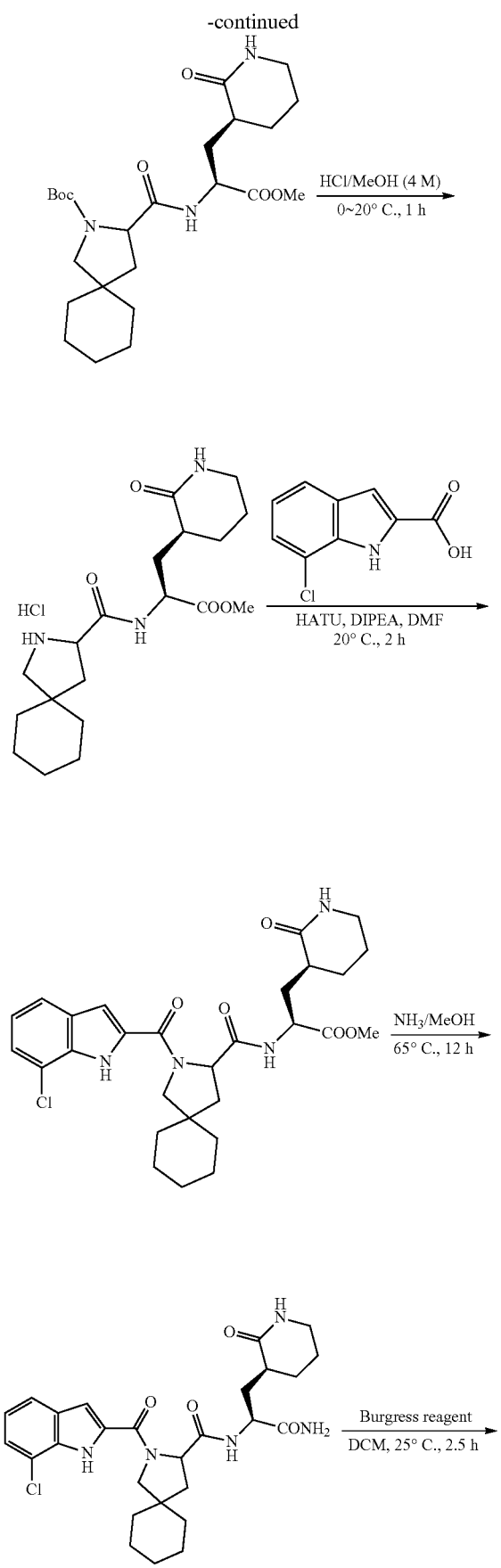

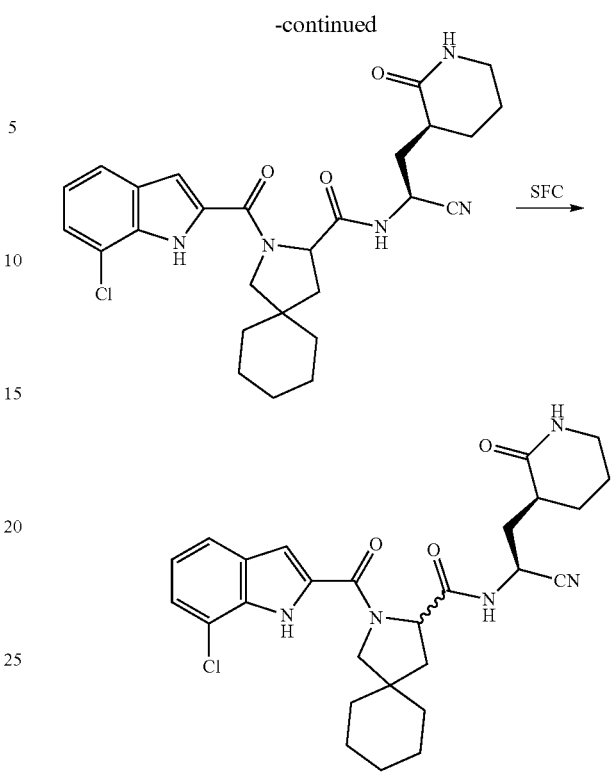

To a mixture of methyl (2S)-2-amino-3-[(3S)-2-oxo-3-piperidyl]propanoate (1 g, 4.22 mmol, 1 eq, HCl) and 2-tert-butoxycarbonyl-2-azaspiro[4.5]decane-3-carboxylic acid (1.26 g, 4.44 mmol, 1.05 eq), DIPEA (2.73 g, 21.12 mmol, 3.68 mL, 5 eq) in THF (10 mL) was added T3P (4.03 g, 6.34 mmol, 3.77 mL, 50% purity, 1.5 eq) at 0° C. under $N_2$. The mixture was stirred at 20° C. for 2 h. Upon completion, the residue was poured into saturated sodium bicarbonate solution (30 mL) and stirred for 2 min. The aqueous phase was extracted with ethyl acetate (20 mL*2). The combined organic phase was washed with brine (20 mL), dried with anhydrous $Na_2SO_4$, filtered and concentrated in vacuum. The residue was purified by column chromatography ($SiO_2$, petroleum ether/ethyl acetate=5/1 to 0/1) to afford tert-butyl 3-[[(1S)-2-methoxy-2-oxo-1-[[(3S)-2-oxo-3-piperidyl]methyl]ethyl]carbamoyl]-2-azaspiro[4.5]decane-2-carboxylate (1.6 g, crude) as a light yellow oil. MS (ESI) m/z 466.3 [M+H]$^+$.

Step 2: methyl (2S)-2-(2-azaspiro[4.5]decane-3-carbonylamino)-3-[(3S)-2-oxo-3-piperidyl]propanoate To a mixture of tert-butyl 3-[[(1S)-2-methoxy-2-oxo-1-[[(3S)-2-oxo-3-piperidyl]methyl] ethyl]carbamoyl]-2-azaspiro[4.5]decane-2-carboxylate (1.6 g, 3.44 mmol, 1 eq) was added HCl/MeOH (4 M, 16.00 mL, 18.62 eq) at 0° C. under $N_2$. The mixture was stirred at 20° C. for 1 h. Upon completion, the reaction mixture was concentrated to get methyl (2S)-2-(2-azaspiro[4.5]decane-3-carbonylamino)-3-[(3S)-2-oxo-3-piperidyl]propanoate (1.5 g, crude, HCl) as a light yellow oil. MS (ESI) m/z 366.2 [M+H]$^+$.

Step 3: methyl (2S)-2-[[2-(7-chloro-1H-indole-2-carbonyl)-2-azaspiro[4.5]decane-3-carbonyl]amino]-3-[(3S)-2-oxo-3-piperidyl]propanoate To a mixture of methyl(2S)-2-(2-azaspiro[4.5]decane-3-carbonylamino)-3-[(3S)-2-oxo-3-piperidyl]propanoate (1.5 g, 3.73 mmol, 1 eq, HCl) and 7-chloro-1H-indole-2-carboxylic acid (729.99 mg, 3.73 mmol, 1 eq), DIPEA (1.45 g, 11.20 mmol, 1.95 mL, 3 eq) in DMF (10 mL) was added HATU (1.70 g, 4.48 mmol, 1.2 eq) at 20° C. under $N_2$. The mixture was stirred at 20° C. for 2 h. Upon completion, the residue was poured into ice-water (10 mL) and stirred for 2 min. The aqueous phase was extracted with ethyl acetate (10 mL*3). The combined organic phase was washed with brine (5 mL*3), dried with anhydrous $Na_2SO_4$, filtered and concentrated in vacuum. The residue was purified by column chromatography ($SiO_2$, petroleum ether/ethyl acetate=2/1 to 0/1) to afford methyl (2S)-2-[[2-(7-chloro-1H-indole-2-carbonyl)-2-azaspiro[4.5]decane-3-carbonyl]amino]-3-[(3S)-2-oxo-3-piperidyl]propanoate (1.60 g, crude) as a light yellow oil. MS (ESI) m/z 543.2 $[M+H]^+$.

Step 4: N-[(1S)-2-amino-2-oxo-1-[[(3S)-2-oxo-3-piperidyl]methyl]ethyl]-2-(7-chloro-1H-indole-2-carbonyl)-2-azaspiro[4.5]decane-3-carboxamide To a mixture of methyl (2S)-2-[[2-(7-chloro-1H-indole-2-carbonyl)-2-azaspiro[4.5]decane-3-carbonyl]amino]-3-[(3S)-2-oxo-3-piperidyl]propanoate (1.6 g, 2.95 mmol, 1 eq) was added $NH_3$/MeOH (7 M, 22.86 mL, 54.31 eq) at 20° C. under $N_2$. The mixture was stirred at 65° C. for 12 h. Upon completion, the mixture was cooled to 25° C. and concentrated in reduced pressure. The residue was purified by column chromatography ($SiO_2$, petroleum ether/ethyl acetate=5/1 to 0/1) to give N-[(1S)-2-amino-2-oxo-1-[[(3S)-2-oxo-3-piperidyl]methyl]ethyl]-2-(7-chloro-1H-indole-2-carbonyl)-2-azaspiro[4.5]decane-3-carboxamide (1.2 g, crude) as a light yellow solid. MS (ESI) m/z 528.2 $[M+H]^+$.

Step 5: 2-(7-chloro-1H-indole-2-carbonyl)-N-[(1S)-1-cyano-2-[(3S)-2-oxo-3-piperidyl]ethyl]-2-azaspiro[4.5]decane-3-carboxamide To a mixture of N-[(1S)-2-amino-2-oxo-1-[[(3S)-2-oxo-3-piperidyl]methyl]ethyl]-2-(7-chloro-1H-indole-2-carbonyl)-2-azaspiro[4.5]decane-3-carboxamide (1.2 g, 2.27 mmol, 1 eq) in DCM (5 mL) was added Burgess reagent (1.2 g, 5.04 mmol, 2.22 eq) in one portion at 20° C. under $N_2$. The mixture was stirred at 20° C. for 2.5 h. Upon completion, the mixture was added water (3 mL) and stirred for 20 min, then concentrated to get the crude. The residue was purified by prep-TLC ($SiO_2$, EtOAc:MeOH=25:1) to afford 2-(7-chloro-1H-indole-2-carbonyl)-N-[(1S)-1-cyano-2-[(3S)-2-oxo-3-piperidyl]ethyl]-2-azaspiro[4.5]decane-3-carboxamide (0.75 g, 1.45 mmol, 64.00% yield, 98.9% purity) as a light yellow solid. MS (ESI) m/z 528.2 $[M+H]^+$.

Step 6: 2-(7-chloro-1H-indole-2-carbonyl)-N-[(1S)-1-cyano-2-[(3S)-2-oxo-3-piperidyl]ethyl]-2-azaspiro[4.5]decane-3-carboxamide 2-(7-chloro-1H-indole-2-carbonyl)-N-[(1S)-1-cyano-2-[(3S)-2-oxo-3-piperidyl]ethyl]-2-azaspiro[4.5]decane-3-carboxamide (0.9 g, 1.76 mmol, 1 eq) was separated by chiral separation (column: REGIS(S,S)WHELK-O1 (250 mm*25 mm, 10 um); mobile phase: [0.1% $NH_3H_2O$ ETOH]; B %: 60%-60%, 6.7 min) to afford 2-(7-chloro-1H-indole-2-carbonyl)-N-[(1 S)-1-cyano-2-[(3S)-2-oxo-3-piperidyl]ethyl]-2-azaspiro[4.5]decane-3-carboxamide Isomer 1 (298.31 mg, 578.46 umol, 32.78% yield, 98.9% purity) as a white solid. MS (ESI) m/z 510.3 $[M+H]^+$.

$^1$H NMR (400 MHz, METHANOL-$d_4$) δ ppm 7.62 (br d, J=7.94 Hz, 1H), 7.56-7.56 (m, 1H), 7.22-7.30 (m, 1H), 7.01-7.13 (m, 2H), 5.11 (br dd, J=10.58, 5.73 Hz, 1 H), 4.62 (br dd, J=9.81, 7.83 Hz, 1H), 3.83-3.96 (m, 1H), 3.71 (br d, J=10.36 Hz, 1H), 3.16-3.27 (m, 2H), 2.40-2.62 (m, 2H), 1.70-2.08 (m, 4H), 1.29-1.65 (m, 12H).

$^1$H NMR (400 MHz, DMSO-$d_6$) δ ppm 11.15 (br s, 1H), 8.71 (br s, 1H), 7.62 (br s, 1H), 7.18-7.35 (m, 2H), 6.94-7.13 (m, 2H), 4.96 (br s, 1H), 4.62 (br s, 1H), 3.51-3.87 (m, 2H), 3.09-3.20 (m, 2H), 2.09-2.36 (m, 3H), 1.60-1.89 (m, 4H), 1.19-1.55 (m, 12H).

To give 2-(7-chloro-1H-indole-2-carbonyl)-N-[(1S)-1-cyano-2-[(3S)-2-oxo-3-piperidyl]ethyl]-2-azaspiro[4.5]decane-3-carboxamide Isomer 2 (252.99 mg, 487.10 umol, 27.60% yield, 98.20% purity) as the white solid. MS (ESI) m/z 510.3 $[M+H]^+$;

$^1$H NMR (400 MHz, METHANOL-$d_4$) δ ppm 7.64 (d, J=7.72 Hz, 1H), 7.21-7.33 (m, 1H), 7.12 (s, 1H), 7.04-7.10 (m, 1H), 7.07 (t, J=7.83 Hz, 1H), 5.02 (dd, J=10.25, 6.06 Hz, 1H), 4.62 (dd, J=9.70, 7.72 Hz, 1H), 3.95 (br d, J=10.14 Hz, 1H), 3.77 (br d, J=10.58 Hz, 1H), 3.01-3.22 (m, 2H), 2.22-2.40 (m, 3H), 1.86-2.04 (m, 2H), 1.77-1.86 (m, 1H), 1.72 (br dd, J=12.46, 10.03 Hz, 1H), 1.39-1.68 (m, 12H).

$^1$H NMR (400 MHz, DMSO-$d_6$) δ ppm 11.10 (br s, 1H), 8.65 (br d, J=6.24 Hz, 1H), 7.63 (br d, J=6.85 Hz, 1H), 7.17-7.34 (m, 2H), 7.08 (br t, J=7.70 Hz, 2H), 4.99 (br d, J=7.46 Hz, 1H), 4.61 (br s, 1H), 3.56-3.89 (m, 2H), 3.10 (br s, 2H), 2.09-2.31 (m, 3H), 1.64-1.95 (m, 4H), 1.38-1.62 (m, 12H).

Example 83. Synthesis of Viral Protease Inhibitor Compound 733

Step 1: tert-butyl 3-(((S)-1-methoxy-1-oxo-3-((S)-2-oxopiperidin-3-yl)propan-2-yl)carbamoyl)-2-azaspiro[4.5]decane-2-carboxylate

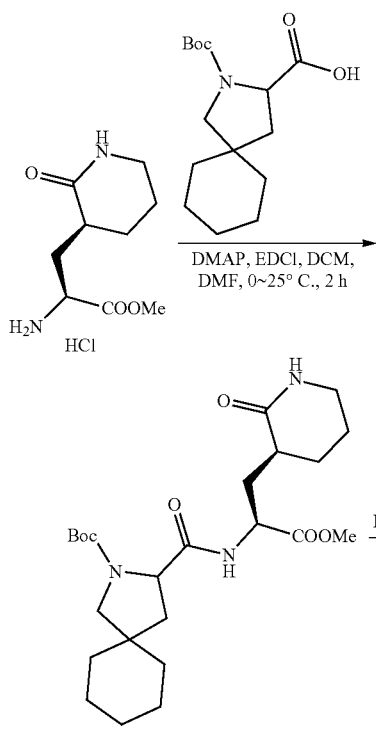

-continued

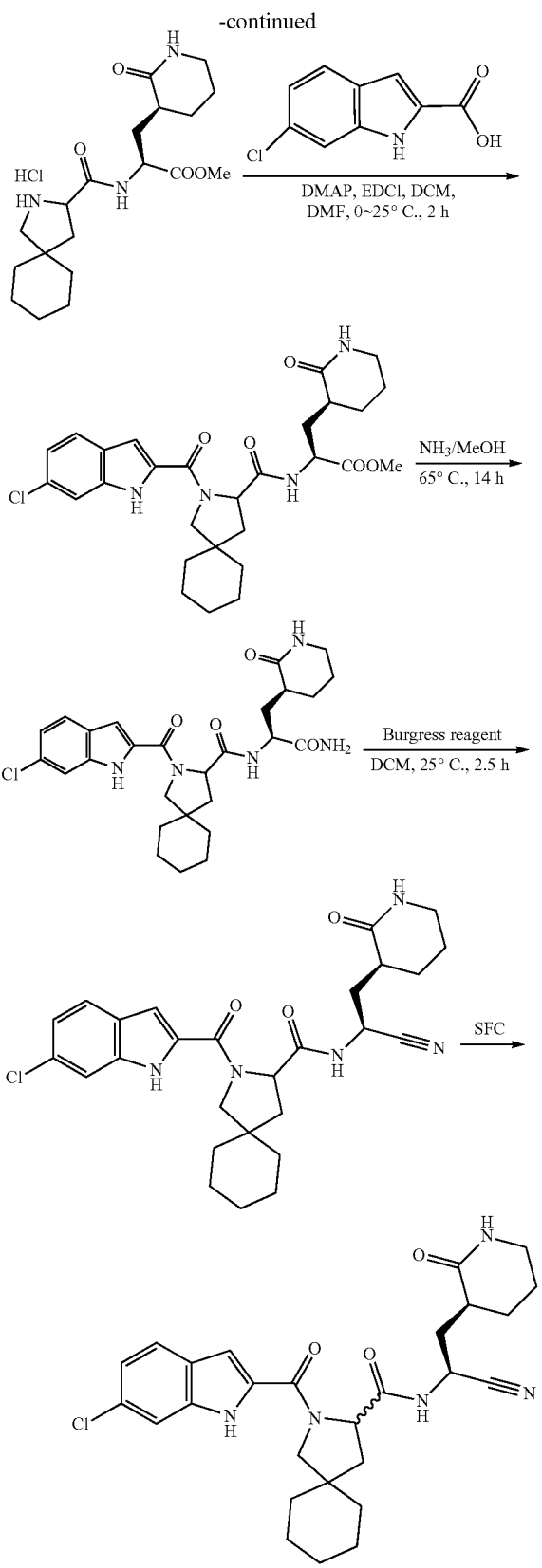

To a solution of methyl (S)-methyl 2-amino-3-((S)-2-oxopiperidin-3-yl)propanoate (500 mg, 2.11 mmol, 1 eq, HCl) in DCM (4 mL) and DMF (2 mL) was added 2-tert-butoxycarbonyl-2-azaspiro[4.5]decane-3-carboxylic acid (718.30 mg, 2.53 mmol, 1.2 eq), DMAP (774.22 mg, 6.34 mmol, 3 eq), and then EDCI (809.90 mg, 4.22 mmol, 2 eq) at 0° C. The mixture was then stirred at 25° C. for 2 h. Upon completion, the reaction mixture was diluted with water (10 mL) and extracted with DCM (10 mL*3). The combined organic layers were washed with brine (10 mL), dried over Na₂SO₄, filtered and concentrated under reduced pressure to give a residue. The residue was purified by column chromatography (SiO₂, DCM:MeOH=1:0 to 10:1) to give tert-butyl 3-(((S)-1-methoxy-1-oxo-3-((S)-2-oxopiperidin-3-yl)propan-2-yl)carbamoyl)-2-azaspiro[4.5]decane-2-carboxylate (775 mg, 1.50 mmol, 70.92% yield, 90% purity) as a yellow solid. MS (ESI) m/z 466.3 [M+H]⁺.

Step 2: (2S)-methyl 3-((S)-2-oxopiperidin-3-yl)-2-(2-azaspiro[4.5]decane-3-carboxamido)propanoate A mixture of tert-butyl 3-(((S)-1-methoxy-1-oxo-3-((S)-2-oxopiperidin-3-yl)propan-2-yl)carbamoyl)-2-azaspiro[4.5]decane-2-carboxylate (775 mg, 1.50 mmol, 90% purity, 1 eq) in HCl/MeOH (4 M, 8 mL, 21.36 eq) was stirred at 25° C. for 1 h. Upon completion, the reaction mixture was concentrated under reduced pressure to give (2S)-methyl 3-((S)-2-oxopiperidin-3-yl)-2-(2-azaspiro[4.5]decane-3-carboxamido)propanoate (800 mg, crude, HCl) as a yellow solid.

Step 3: (2S)-methyl 2-(2-(6-chloro-1H-indole-2-carbonyl)-2-azaspiro[4.5]decane-3-carboxamido)-3-((S)-2-oxopiperidin-3-yl)propanoate To a solution of (2S)-methyl 3-((S)-2-oxopiperidin-3-yl)-2-(2-azaspiro[4.5]decane-3-carboxamido)propanoate (740 mg, 1.38 mmol, 75% purity, 1 eq, HCl) in DCM (6 mL) and DMF (3 mL) was added 6-chloro-1H-indole-2-carboxylic acid (297.11 mg, 1.52 mmol, 1.1 eq), DMAP (506.09 mg, 4.14 mmol, 3 eq), then EDCI (529.42 mg, 2.76 mmol, 2 eq) at 0° C., and then the mixture was then stirred at 25° C. for 2 h. Upon completion, the reaction mixture was diluted with water (10 mL) and extracted with DCM (10 mL*3). The combined organic layers were washed with brine (10 mL), dried over Na₂SO₄, filtered and concentrated under reduced pressure to give a residue. The residue was purified by column chromatography (SiO₂, DCM:MeOH=1:0 to 10:1) to give (2S)-methyl 2-(2-(6-chloro-1H-indole-2-carbonyl)-2-azaspiro[4.5]decane-3-carboxamido)-3-((S)-2-oxopiperidin-3-yl)propanoate (980 mg, 1.35 mmol, 98.02% yield, 75% purity) as a yellow solid. MS (ESI) m/z 543.3 [M+H]⁺.

Step 4: N-((S)-1-amino-1-oxo-3-((S)-2-oxopiperidin-3-yl)propan-2-yl)-2-(6-chloro-1H-indole-2-carbonyl)-2-azaspiro[4.5]decane-3-carboxamide A mixture of (2S)-methyl 2-(2-(6-chloro-1H-indole-2-carbonyl)-2-azaspiro[4.5]decane-3-carboxamido)-3-((S)-2-oxopiperidin-3-yl)propanoate (980 mg, 1.35 mmol, 75% purity, 1 eq) in NH₃·MeOH (7 M, 15 mL, 77.58 eq) was stirred at 65° C. for 14 h. Upon completion, the reaction mixture was concentrated under reduced pressure to give N-((S)-1-amino-1-oxo-3-((S)-2-oxopiperidin-3-yl)propan-2-yl)-2-(6-chloro-1H-indole-2-carbonyl)-2-azaspiro[4.5]decane-3-carboxamide (960 mg, crude) as a yellow solid. MS (ESI) m/z 528.2 [M+H]⁺.

Step 5: 2-(6-chloro-1H-indole-2-carbonyl)-N-((S)-1-cyano-2-((S)-2-oxopiperidin-3-yl)ethyl)-2-azaspiro[4.5]decane-3-carboxamide To a solution of N-((S)-1-amino-1-oxo-3-((S)-2-oxopiperidin-3-yl)propan-2-yl)-2-(6-chloro-1H-indole-2-carbonyl)-2-azaspiro[4.5]decane-3-carboxamide (960 mg, 1.36 mmol, 75% purity, 1 eq) in DCM (10 mL) was added Burgess reagent (1.95 g, 8.18 mmol, 6 eq) and then stirred at 25° C. for 4 h. Upon completion, the reaction mixture was diluted with water (10 mL) and extracted with DCM (10 mL*3). The combined organic layers were washed with brine (10 mL), dried over Na$_2$SO$_4$, filtered and concentrated under reduced pressure to give a residue. The residue was purified by prep-HPLC (column: Kromasil C18 (250*50 mm*10 um); mobile phase: [water (10 mM NH$_4$HCO$_3$)-ACN]; B %: 35%-65%, 10 min) to give 2-(6-chloro-1H-indole-2-carbonyl)-N-((S)-1-cyano-2-((S)-2-oxopiperidin-3-yl)ethyl)-2-azaspiro[4.5]decane-3-carboxamide (280 mg, 39.66% yield, 98.5% purity) as a white solid. MS (ESI) m/z 510.2 [M+H]$^+$.

Step 6: 2-(6-chloro-1H-indole-2-carbonyl)-N-((S)-1-cyano-2-((S)-2-oxopiperidin-3-yl)ethyl)-2-azaspiro[4.5]decane-3-carboxamide 2-(6-chloro-1H-indole-2-carbonyl)-N-((S)-1-cyano-2-((S)-2-oxopiperidin-3-yl)ethyl)-2-azaspiro[4.5]decane-3-carboxamide (280 mg, 98.5% purity) was purified by SFC (column: REGIS(S, S)WHELK-O1 (250 mm*25 mm, 10 um); mobile phase: [0.1% NH$_3$H$_2$O IPA]; B %: 60%-60%, 8 min) to give 2-(6-chloro-1H-indole-2-carbonyl)-N-((S)-1-cyano-2-((S)-2-oxopiperidin-3-yl)ethyl)-2-azaspiro[4.5]decane-3-carboxamide Isomer 1 (90.34 mg, 175.89 umol, 12.90% yield, 99.3% purity) as a white solid. MS (ESI) m/z 510.2 [M+H]$^+$.

$^1$H NMR (400 MHz, DMSO-d$_6$) δ=11.68 (s, 1H), 9.10-8.79 (m, 1H), 7.69 (d, J=8.4 Hz, 1H), 7.58-7.47 (m, 1H), 7.46-7.36 (m, 1H), 7.14-6.62 (m, 2H), 5.10-4.73 (m, 1H), 4.51 (t, J=8.4 Hz, 1H), 3.95-3.73 (m, 1H), 3.65 (d, J=10.4 Hz, 1H), 3.17-2.83 (m, 2H), 2.35-2.07 (m, 3H), 1.93-1.19 (m, 16H).

$^1$H NMR (400 MHz, DMSO-d$_6$) (T=273+80K) δ=11.48 (br s, 1H), 8.74 (br s, 1H), 7.65 (br s, 1H), 7.47 (br s, 1H), 7.31 (br s, 1H), 7.06 (br d, J=9.0 Hz, 2H), 4.98 (br s, 1H), 4.57 (br s, 1H), 3.87 (br d, J=10.1 Hz, 1H), 3.64 (br s, 1H), 3.10-3.04 (m, 2H), 2.39-2.11 (m, 3H), 1.90-1.36 (m, 16H).

To give 2-(6-chloro-1H-indole-2-carbonyl)-N-((S)-1-cyano-2-((S)-2-oxopiperidin-3-yl)ethyl)-2-azaspiro[4.5]decane-3-carboxamide Isomer 2 (143.12 mg, 280.61 umol, 20.58% yield, 100% purity) as a white solid. MS (ESI) m/z 510.2 [M+H]$^+$.

$^1$H NMR (400 MHz, DMSO-d$_6$) δ=11.69 (s, 1H), 9.12-8.72 (m, 1H), 7.69 (d, J=8.6 Hz, 1H), 7.57-7.40 (m, 2H), 7.14-6.60 (m, 2H), 5.08-4.78 (m, 1H), 4.51 (t, J=8.4 Hz, 1H), 3.92-3.78 (m, 1H), 3.69 (d, J=10.4 Hz, 1H), 3.13-2.92 (m, 2H), 2.28-2.06 (m, 3H), 1.87-1.29 (m, 16H).

$^1$H NMR (400 MHz, DMSO-d$_6$) (T=273+80K) δ=11.49 (br s, 1H), 8.69 (br s, 1H), 7.79-7.57 (m, 1H), 7.48 (s, 1H), 7.27 (br s, 1H), 7.06 (br d, J=8.4 Hz, 2H), 4.97 (br s, 1H), 4.57 (br s, 1H), 3.88 (d, J=10.4 Hz, 1H), 3.68 (br s, 1H), 3.10-3.04 (m, 2H), 2.20 (br s, 3H), 1.91-1.31 (m, 16H).

Example 83. Synthesis of Viral Protease Inhibitor Compound 743

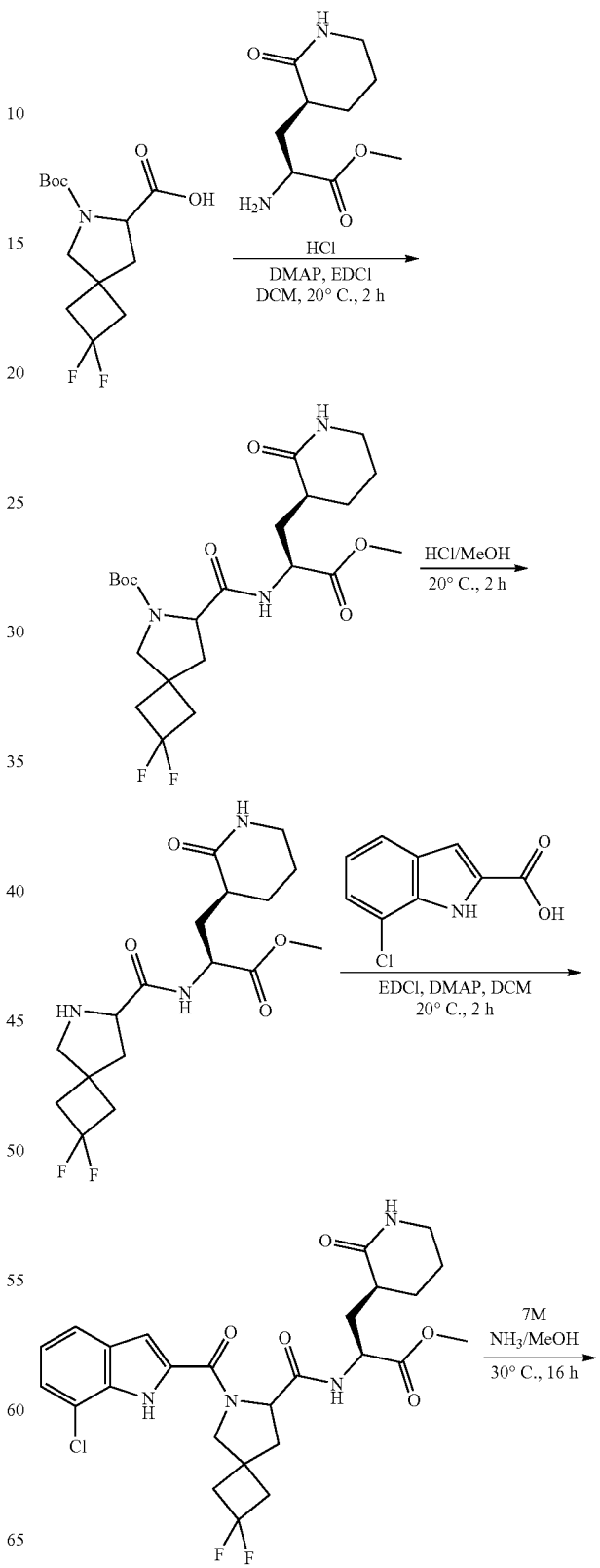

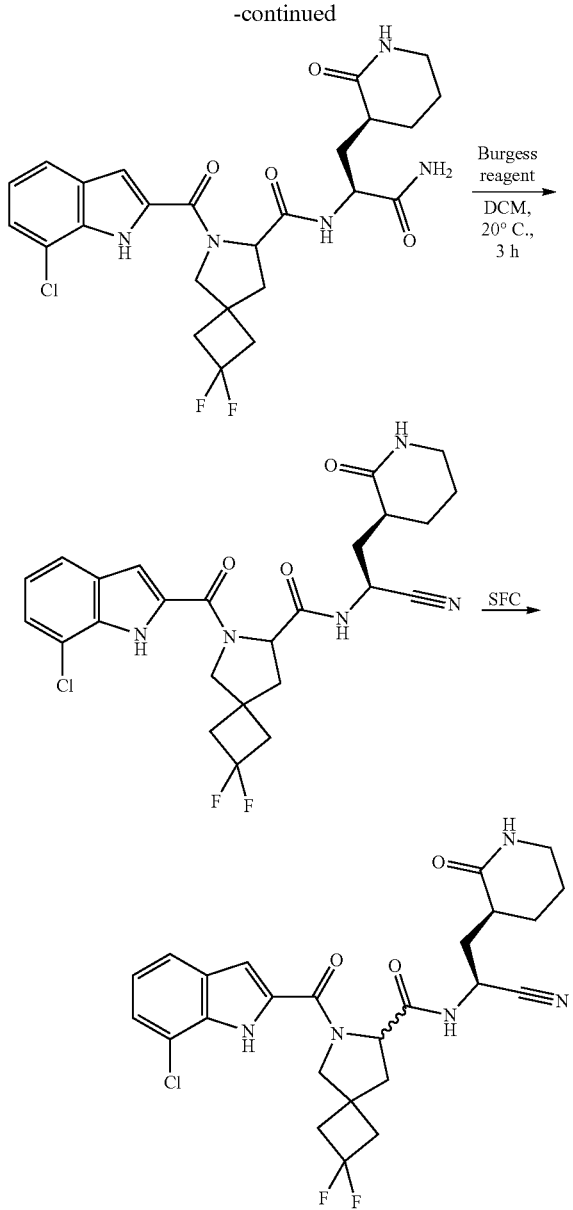

Step 1: tert-butyl 2,2-difluoro-7-(((S)-1-methoxy-1-oxo-3-((S)-2-oxopiperidin-3-yl)propan-2-yl)carbamoyl)-6-azaspiro[3.4]octane-6-carboxylate A mixture of (7S)-6-tert-butoxycarbonyl-2,2-difluoro-6-azaspiro[3.4]octane-7-carboxylic acid (500 mg, 1.72 mmol, 1 eq), methyl (2S)-2-amino-3-[(3S)-2-oxo-3-piperidyl]propanoate (406.29 mg, 1.72 mmol, 1 eq, HCl), EDCI (987.17 mg, 5.15 mmol, 3 eq), DMAP (629.10 mg, 5.15 mmol, 3 eq) in DCM (5 mL) was degassed and purged with N₂ for 3 times, and then the mixture was stirred at 20° C. for 2 h under N₂ atmosphere. Upon completion, the reaction mixture was poured into H₂O (50 mL) at 20° C., and then extracted with DCM (50 mL*3). The combined organic layers were washed with brine (50 mL*2), dried over Na₂SO₄, filtered and concentrated under reduced pressure to give a residue. The residue was purified by column chromatography (SiO₂, petroleum ether/ethyl acetate=1/0 to 1/1) to give tert-butyl (7S)-2,2-difluoro-7-[[(1S)-2-methoxy-2-oxo-1-[[(3S)-2-oxo-3-piperidyl]methyl]ethyl]carbamoyl]-6-azaspiro[3.4]octane-6-carboxylate (800 mg, crude) was obtained as a white solid. MS (ESI) m/z 474.1 [M+H]⁺.

Step 2: (2S)-methyl 2-(2,2-difluoro-6-azaspiro[3.4]octane-7-carboxamido)-3-((S)-2-oxopiperidin-3-yl)propanoate A solution of tert-butyl (7S)-2,2-difluoro-7-[[(1S)-2-methoxy-2-oxo-1-[[(3S)-2-oxo-3-piperidyl]methyl]ethyl]carbamoyl]-6-azaspiro[3.4]octane-6-carboxylate (800 mg, 1.69 mmol, 1 eq) in HCl/MeOH (4 M, 8 mL, 18.94 eq) was stirred at 20° C. for 2 h. Upon completion, the reaction mixture was concentrated under reduced pressure to remove solvent to give methyl (2S)-2-[[(7S)-2,2-difluoro-6-azaspiro[3.4]octane-7-carbonyl]amino]-3-[(3S)-2-oxo-3-piperidyl]propanoate (690 mg, crude, HCl) as a yellow oil. MS (ESI) m/z 374.1 [M+H]⁺.

Step 3: (2S)-methyl 2-(6-(7-chloro-1H-indole-2-carbonyl)-2,2-difluoro-6-azaspiro[3.4]octane-7-carboxamido)-3-((S)-2-oxopiperidin-3-yl)propanoate To a solution of methyl (2S)-2-[[(7S)-2,2-difluoro-6-azaspiro[3.4]octane-7-carbonyl]amino]-3-[(3S)-2-oxo-3-piperidyl]propanoate (690 mg, 1.68 mmol, 1 eq, HCl), 7-chloro-1H-indole-2-carboxylic acid (329.30 mg, 1.68 mmol, 1 eq), DMAP (617.03 mg, 5.05 mmol, 3 eq) in DCM (10 mL), was added EDCI (968.19 mg, 5.05 mmol, 3 eq). The mixture was stirred at 20° C. for 2 h. Upon completion, the reaction mixture was poured into H₂O (35 mL) at 20° C., and then extracted with (35 mL*3). The combined organic layers were washed with brine (35 mL*2), dried over Na₂SO₄, filtered and concentrated under reduced pressure to give a residue. The residue was purified by column chromatography (SiO₂, petroleum ether/ethyl acetate=80/1 to 1/1) to give methyl (2S)-2-[[(7S)-6-(7-chloro-1H-indole-2-carbonyl)-2,2-difluoro-6-azaspiro[3.4]octane-7-carbonyl]amino]-3-[(3S)-2-oxo-3-piperidyl]propanoate (640 mg, 1.16 mmol, 69.00% yield) as a yellow solid. MS (ESI) m/z 551.2 [M+H]⁺.

Step 4: N-((S)-1-amino-1-oxo-3-((S)-2-oxopiperidin-3-yl)propan-2-yl)-6-(7-chloro-1H-indole-2-carbonyl)-2,2-difluoro-6-azaspiro[3.4]octane-7-carboxamide To a solution of methyl (2S)-2-[[(7S)-6-(7-chloro-1H-indole-2-carbonyl)-2,2-difluoro-6-azaspiro[3.4]octane-7-carbonyl]amino]-3-[(3S)-2-oxo-3-piperidyl]propanoate (625 mg, 1.13 mmol, 1 eq) in NH₃/MeOH (7 M, 12 mL, 74.05 eq). The mixture was stirred at 30° C. for 16 h. Upon completion, the reaction mixture was concentrated under reduced pressure to remove solvent to give (7S)-N-[(1S)-2-amino-2-oxo-1-[[(3S)-2-oxo-3-piperidyl]methyl]ethyl]-6-(7-chloro-1H-indole-2-carbonyl)-2,2-difluoro-6-azaspiro[3.4]octane-7-carboxamide (605 mg, crude) as a yellow solid. MS (ESI) m/z 536.2 [M+H]⁺.

Step 5: 6-(7-chloro-1H-indole-2-carbonyl)-N-((S)-1-cyano-2-((S)-2-oxopiperidin-3-yl)ethyl)-2,2-difluoro-6-azaspiro[3.4]octane-7-carboxamide To a solution of (7S)-N-[(1S)-2-amino-2-oxo-1-[[(3S)-2-oxo-3-piperidyl]methyl]ethyl]-6-(7-chloro-11H-indole-2-carbonyl)-2,2-difluoro-6-azaspiro[3.4]octane-7-carboxamide (585 mg, 1.09 mmol, 1 eq) in DCM (10 mL) was added Burgess reagent (1.17 g, 4.91 mmol, 4.5 eq). The mixture was stirred at 20° C. for 3 h. Upon completion, the reaction mixture was poured into H₂O (30 mL) at 20° C., and then extracted with DCM (35 mL*3). The combined organic layers were washed with brine (30 mL*2), dried over Na₂SO₄, filtered and concentrated under reduced pressure to give a residue. The residue was purified by prep-HPLC (column: Kromasil C18 (250*50 mm*10 um); mobile phase: [water (10 mM NH₄HCO₃)-ACN]; B %: 30%-60%, 10 min) to give (7S)-6-(7-chloro-1H-indole-2-carbonyl)-N-[(1S)-1-cyano-2-[(3S)-2-oxo-3-piperidyl]ethyl]-2,2-difluoro-6-azaspiro[3.4]octane-7-carboxamide (135 mg, 260.64 umol, 23.88% yield) as a white solid. MS (ESI) m/z 518.2 [M+H]⁺.

Step 6: 6-(7-chloro-1H-indole-2-carbonyl)-N-((S)-1-cyano-2-((S)-2-oxopiperidin-3-yl)ethyl)-2,2-difluoro-6-azaspiro[3.4]octane-7-carboxamide Isomer 1: 6-(7-chloro-1H-indole-2-carbonyl)-N-((S)-1-cyano-2-((S)-2-oxopiperidin-3-yl)ethyl)-2,2-difluoro-6-azaspiro[3.4]octane-7-carboxamide (133 mg) was separated by SFC (column: REGIS(S,S)WHELK-O1 (250 mm*25 mm, 10 um); mobile phase: [0.1% NH₃H₂O ETOH]; B %: 60%-60%, 15 min) to give (7S)-6-(7-chloro-1H-indole-2-carbonyl)-N-[(1S)-1-cyano-2-[(3S)-2-oxo-3-piperidyl]ethyl]-2,2-difluoro-6-azaspiro[3.4]octane-7-carboxamide (48.2 mg, 93.06 umol, 36.24% yield) as a white solid. MS (ESI) m/z 518.2 [M+H]⁺.

Isomer 1: ¹H NMR (400 MHz, DMSO-d₆) δ=11.34-11.12 (m, 1H), 8.83-8.63 (m, 1H), 7.71-7.55 (m, 1H), 7.30 (d, J=7.1 Hz, 2H), 7.13-7.04 (m, 1H), 5.09-4.92 (m, 1H), 4.71-4.52 (m, 1H), 4.20-3.87 (m, 2H), 3.09-3.05 (m, 1H), 3.10-3.03 (m, 2H), 2.91-2.52 (m, 4H), 2.48-2.35 (m, 2H), 2.29-2.08 (m, 2H), 1.96-1.31 (m, 5H).

Isomer 2: To give (7S)-6-(7-chloro-1H-indole-2-carbonyl)-N-[(1S)-1-cyano-2-[(3S)-2-oxo-3-piperidyl]ethyl]-2,2-difluoro-6-azaspiro[3.4]octane-7-carboxamide (83.2 mg, 160.63 umol, 62.56% yield) as a white solid. MS (ESI) m/z 518.2 [M+H]⁺.

Isomer 2: ¹H NMR (400 MHz, DMSO-d₆) δ=11.32-11.13 (m, 1H), 8.90-8.67 (m, 1H), 7.69-7.48 (m, 1H), 7.33-7.26 (m, 1H), 7.19-6.89 (m, 2H), 5.07-4.88 (m, 1H), 4.74-4.51 (m, 1H), 4.15-3.84 (m, 2H), 3.11-3.06 (m, 2H), 3.10-3.06 (m, 1H), 2.82-2.55 (m, 4H), 2.43 (d, J=3.2, 5.2 Hz, 2H), 2.32-2.07 (m, 2H), 2.02-1.01 (m, 5H).

Example 84. Synthesis of Viral Protease Inhibitor Compound 745

Step 1: methyl(2S)-2-[[(2S)-2-amino-4,4-dimethyl-pentanoyl]amino]-3-[(3S)-2-oxo-3-piperidyl]propanoate

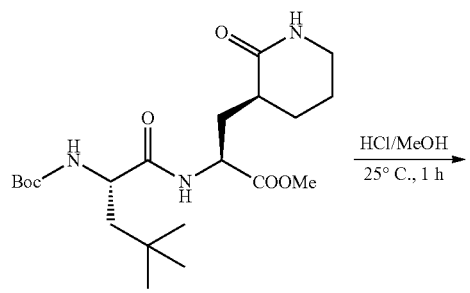

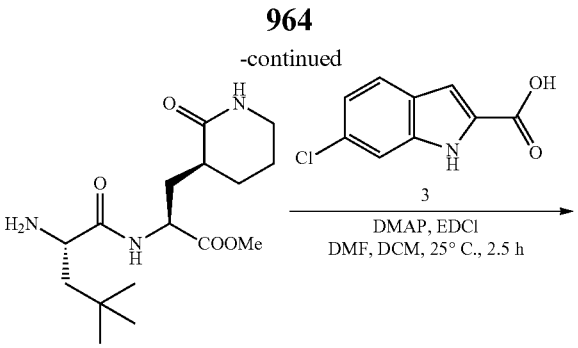

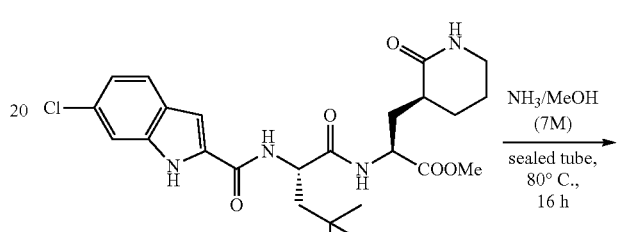

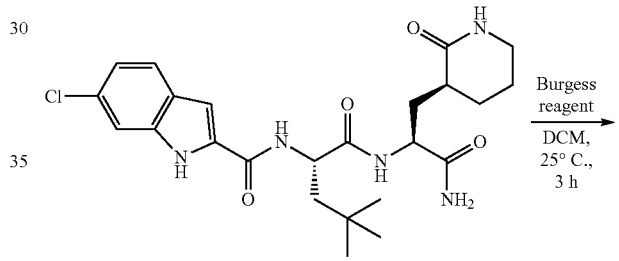

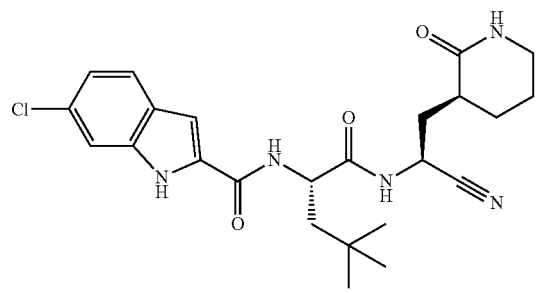

A mixture of methyl (2S)-2-[[(2S)-2-(tert-butoxycarbonylamino)-4,4-dimethyl-pentanoyl]amino]-3-[(3S)-2-oxo-3-piperidyl]propanoate (1 g, 2.34 mmol, 1 eq) in HCl/MeOH (4 M) (10 mL) was stirred at 25° C. for 1 h. Upon completion, the reaction mixture was concentrated under reduced pressure to give a residue. Compound methyl (2S)-2-[[(2S)-2-amino-4,4-dimethyl-pentanoyl]amino]-3-[(3S)-2-oxo-3-piperidyl]propanoate (900 mg, crude) was obtained as a white solid and used to the next step directly. MS (ESI) m/z 328.3 [M+H]⁺.

Step 2: methyl (2S)-2-[[(2S)-2-[(6-chloro-1H-indole-2-carbonyl)amino]-4,4-dimethyl-pentanoyl]amino]-3-[(3S)-2-oxo-3-piperidyl]propanoate To a mixture of 6-chloro-1H-indole-2-carboxylic acid (400 mg, 2.04 mmol, 1 eq) in DCM (10 mL) and DMF (5 mL) was added DMAP (749.49 mg, 6.13 mmol, 3 eq) in one portion at 25° C. The mixture was added with methyl (2S)-2-[[(2S)-2-amino-4,4-dimethyl-pentanoyl]amino]-3-[(3S)-2-oxo-3-piperidyl]propanoate (892.94 mg, 2.45 mmol, 1.20 eq, HCl) and EDCI (784.05 mg, 4.09 mmol, 2 eq) in one portion at 25° C. and the reaction was stirred for 2.5 h. Upon completion, the reaction mixture was concentrated under reduced pressure to give a residue. The residue was purified by prep-TLC (SiO$_2$, DCM:MeOH=10:1). Compound methyl (2S)-2-[[(2S)-2-[(6-chloro-1H-indole-2-carbonyl)amino]-4,4-dimethyl-pentanoyl]amino]-3-[(3S)-2-oxo-3-piperidyl]propanoate (800 mg, 1.58 mmol, 77.47% yield) was obtained as a yellow solid. MS (ESI) m/z 505.2 [M+H]$^+$.

Step 3: N-[(1S)-1-[[(1S)-2-amino-2-oxo-1-[[(3S)-2-oxo-3-piperidyl]methyl]ethyl]carbamoyl]-3,3-dimethyl-butyl]-6-chloro-1H-indole-2-carboxamide To a mixture of methyl (2S)-2-[[(2S)-2-[(6-chloro-1H-indole-2-carbonyl)amino]-4,4-dimethyl-pentanoyl]amino]-3-[(3S)-2-oxo-3-piperidyl]propanoate (605 mg, 1.20 mmol, 1 eq) in NH$_3$/MeOH (7 M) (30.60 mg, 1.80 mmol, 30.00 uL, 1.5 eq) in one portion at 25° C. The mixture was stirred at 80° C. for 16 h. Upon completion, the reaction mixture was concentrated under reduced pressure to give a residue. Compound N-[(1S)-1-[[(1S)-2-amino-2-oxo-1-[[(3S)-2-oxo-3-piperidyl]methyl]ethyl]carbamoyl]-3,3-dimethyl-butyl]-6-chloro-1H-indole-2-carboxamide (600 mg, crude) was obtained as a white solid and used to the next step directly. MS (ESI) m/z 490.1 [M+H]$^+$.

Step 4: 6-chloro-N-[(1S)-1-[[(1S)-1-cyano-2-[(3S)-2-oxo-3-piperidyl]ethyl]carbamoyl]-3,3-dimethyl-butyl]-1H-indole-2-carboxamide A mixture of N-[(1S)-1-[[(1S)-2-amino-2-oxo-1-[[(3S)-2-oxo-3-piperidyl]methyl]ethyl]carbamoyl]-3,3-dimethyl-butyl]-6-chloro-1H-indole-2-carboxamide (500 mg, 1.02 mmol, 1 eq) in DCM (6 mL) was added Burgess reagent (607.94 mg, 2.55 mmol, 2.5 eq), and the mixture was stirred at 25° C. for 3 h. Upon completion, the reaction mixture was concentrated under reduced pressure to give a residue. The residue was purified by prep-HPLC {column: Waters Xbridge Prep OBD C18 150*40 mm*10 um; mobile phase: [water (10 mM NH$_4$HCO$_3$)-ACN]; B %: 40%-60%, 8 min}. Compound 6-chloro-N-[(1S)-1-[[(1S)-1-cyano-2-[(3S)-2-oxo-3-piperidyl]ethyl]carbamoyl]-3,3-dimethyl-butyl]-1H-indole-2-carboxamide (202 mg, 405.64 umol, 39.75% yield, 94.78% purity) was obtained as a white solid. MS (ESI) m/z 472.3 [M+H]$^+$.

$^1$H NMR (400 MHz, METHANOL-d$_4$) δ ppm 7.41-7.65 (m, 2H), 7.01-7.22 (m, 2H), 5.08 (br s, 1H), 4.65 (br s, 1H), 3.15-3.25 (m, 2H), 2.43 (br s, 1H), 1.46-2.05 (m, 8H), 1.02 (br s, 9H)

Example 85. Synthesis of Viral Protease Inhibitor Compound 791

Step 1: tert-butyl 7-[[(1S)-2-methoxy-2-oxo-1-[[(3S)-2-oxo-3-piperidyl]methyl]ethyl]carbamoyl]-6-azaspiro[3.4]octane-6-carboxylate

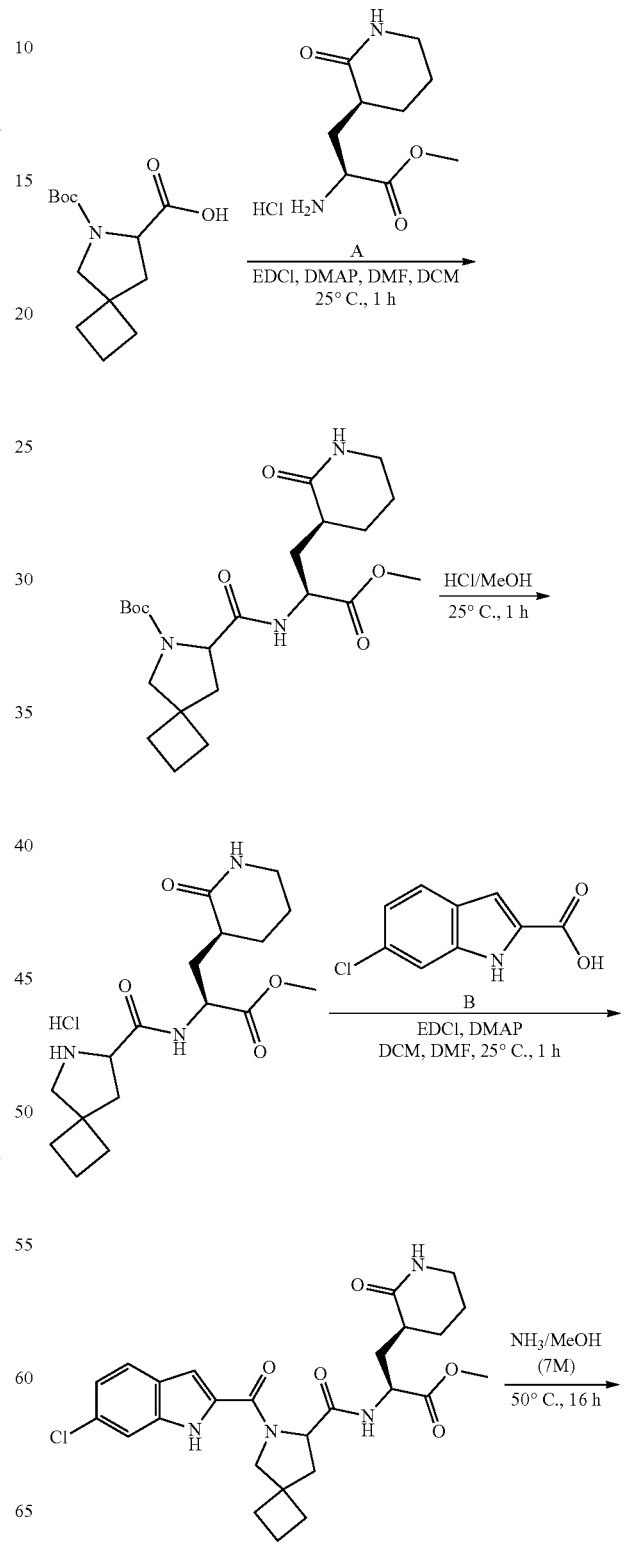

-continued

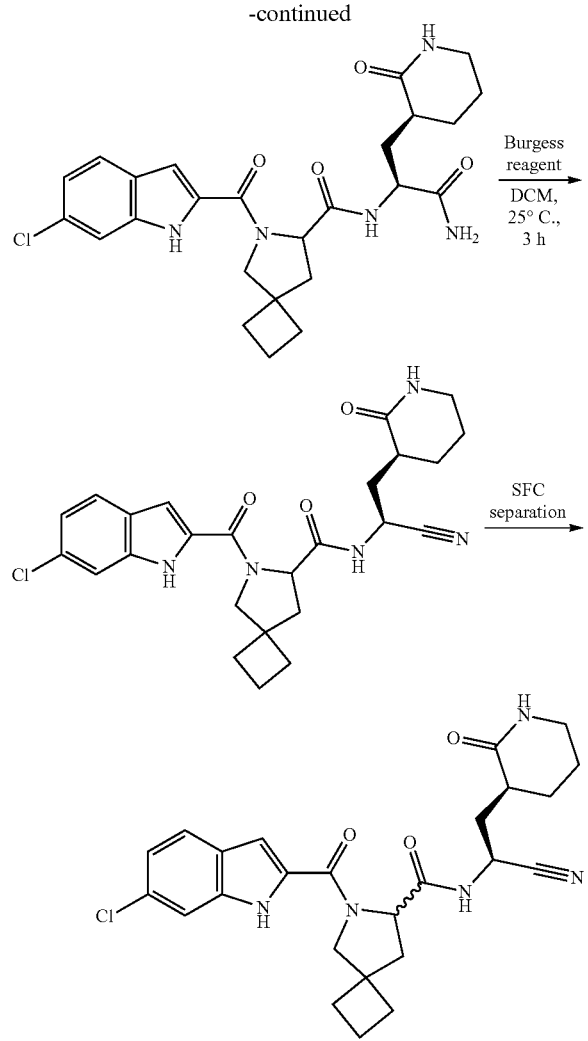

To a mixture of methyl (2S)-2-amino-3-[(3S)-2-oxo-3-piperidyl]propanoate (2.32 g, 9.79 mmol, 1 eq, HCl) in DCM (30 mL) and DMF (10 mL) was added DMAP (3.59 g, 29.38 mmol, 3 eq) in one portion at 25° C. The mixture was added 6-tert-butoxycarbonyl-6-azaspiro[3.4]octane-7-carboxylic acid (3 g, 11.75 mmol, 1.2 eq) and EDCI (3.75 g, 19.58 mmol, 2 eq) stirred at 25° C. for 1 h. Upon completion, the reaction mixture was diluted with H₂O (40 mL) and extracted with ethyl acetate (50 mL*3). The combined organic layers were washed with brine (80 mL*1), dried over Na₂SO₄, filtered and concentrated under reduced pressure to give the crude product. The crude was purified by column chromatography (SiO₂, petroleum ether/ethyl acetate=5/1 to 0/1) to give tert-butyl 7-[[(1S)-2-methoxy-2-oxo-1-[[(3S)-2-oxo-3-piperidyl]methyl]ethyl]carbamoyl]-6-azaspiro[3.4]octane-6-carboxylate (5 g, crude) as a yellow oil. MS (ESI) m/z 438.2 [M+H]⁺.

Step 2: methyl (2S)-2-(6-azaspiro[3.4]octane-7-carbonylamino)-3-[(3S)-2-oxo-3-piperidyl]propanoate A mixture of tert-butyl 7-[[(1S)-2-methoxy-2-oxo-1-[[(3S)-2-oxo-3-piperidyl]methyl]ethyl]carbamoyl]-6-azaspiro[3.4]octane-6-carboxylate (1.6 g, 3.66 mmol, 1 eq) in HCl/MeOH (20 mL) was stirred at 25° C. for 1 h. Upon completion, the reaction mixture was concentrated under reduced pressure to give methyl (2S)-2-(6-azaspiro[3.4]octane-7-carbonylamino)-3-[(3S)-2-oxo-3-piperidyl]propanoate (1.3 g, crude) as a yellow solid.

Step 3: methyl (2S)-2-[[6-(6-chloro-1H-indole-2-carbonyl)-6-azaspiro[3.4]octane-7-carbonyl]amino]-3-[(3S)-2-oxo-3-piperidyl]propanoate To a mixture of methyl (2S)-2-(6-azaspiro[3.4]octane-7-carbonylamino)-3-[(3S)-2-oxo-3-piperidyl]propanoate (1.3 g, 3.85 mmol, 1 eq) and 6-chloro-1H-indole-2-carboxylic acid (904.35 mg, 4.62 mmol, 1.2 eq) in DCM (9 mL) and DMF (3 mL) was added DMAP (1.41 g, 11.56 mmol, 3 eq) and EDCI (1.48 g, 7.71 mmol, 2 eq) in one portion at 25° C. The mixture was stirred at 25° C. for 1 h. Upon completion, the reaction mixture was diluted with H₂O (10 mL) and extracted with ethyl acetate (25 mL*3). The combined organic layers were washed with brine (20 mL*1), dried over with Na₂SO₄, filtered and concentrated under reduced pressure to give the crude product. The crude was purified by column chromatography (SiO₂, petroleum ether/ethyl acetate=3/1 to 0/1) to give methyl (2S)-2-[[6-(6-chloro-1H-indole-2-carbonyl)-6-azaspiro[3.4]octane-7-carbonyl]amino]-3-[(3S)-2-oxo-3-piperidyl]propanoate (1.2 g, 2.21 mmol, 57.45% yield, 95% purity) as a yellow oil. MS (ESI) m/z 515.3 [M+H]⁺

Step 4: N-[(1S)-2-amino-2-oxo-1-[[(3S)-2-oxo-3-piperidyl]methyl]ethyl]-6-(6-chloro-1H-indole-2-carbonyl)-6-azaspiro[3.4]octane-7-carboxamide A mixture of methyl (2S)-2-[[6-(6-chloro-1H-indole-2-carbonyl)-6-azaspiro[3.4]octane-7-carbonyl]amino]-3-[(3S)-2-oxo-3-piperidyl]propanoate (1.2 g, 2.33 mmol, 1 eq) in NH₃/MeOH (7 M, 15 mL, 45.06 eq) was stirred at 50° C. for 16 h. Upon completion, the reaction mixture was concentrated under reduced pressure to give N-[(1S)-2-amino-2-oxo-1-[[(3S)-2-oxo-3-piperidyl]methyl]ethyl]-6-(6-chloro-1H-indole-2-carbonyl)-6-azaspiro[3.4]octane-7-carboxamide (980 mg, 1.96 mmol, 84.12% yield) as a yellow solid. MS (ESI) m/z 500.2 [M+H]⁺.

Step 5: 6-(6-chloro-1H-indole-2-carbonyl)-N-[(1S)-1-cyano-2-[(3S)-2-oxo-3-piperidyl]ethyl]-6-azaspiro[3.4]octane-7-carboxamide To a mixture of N-[(1S)-2-amino-2-oxo-1-[[(3S)-2-oxo-3-piperidyl]methyl]ethyl]-6-(6-chloro-1H-indole-2-carbonyl)-6-azaspiro[3.4]octane-7-carboxamide (980 mg, 1.96 mmol, 1 eq) in DCM (10 mL) was added Burgess reagent (1.87 g, 7.84 mmol, 4 eq) in one portion at 25° C. The mixture was stirred at 25° C. for 3 h. Upon completion, the reaction mixture was concentrated under reduced pressure to give the crude product. The crude was purified by prep-HPLC (neutral condition; column: Kromasil C18 (250*50 mm*10 um); mobile phase: [water (10 mM NH₄HCO₃)-ACN]; B %: 30%-50%, 10 min) to afford 6-(6-chloro-1H-indole-2-carbonyl)-N-[(1S)-1-cyano-2-[(3S)-2-oxo-3-piperidyl]ethyl]-6-azaspiro[3.4]octane-7-carboxamide (600 mg, 1.24 mmol, 63.51% yield) as a white solid. MS (ESI) m/z 482.2 [M+H]⁺

Step 6: 6-(6-chloro-1H-indole-2-carbonyl)-N-[(1S)-1-cyano-2-[(3S)-2-oxo-3-piperidyl]ethyl]-6-azaspiro[3.4]octane-7-carboxamide The white solid was separated by SFC (column: REGIS (S,S)WHELK-O1 (250 mm*25 mm, 10 um); mobile phase:

[0.1% NH₃H₂O ETOH]; B %: 60%-60%, min) to give 6-(6-chloro-1H-indole-2-carbonyl)-N-[(1S)-1-cyano-2-[(3S)-2-oxo-3-piperidyl]ethyl]-6-azaspiro[3.4]octane-7-carboxamide (140 mg, 290.47 umol, 23.33% yield) and 6-(6-chloro-1H-indole-2-carbonyl)-N-[(1S)-1-cyano-2-[(3S)-2-oxo-3-piperidyl]ethyl]-6-azaspiro[3.4]octane-7-carboxamide (110 mg, 228.23 umol, 18.33% yield) as a white solid. MS (ESI) m/z 482.2 [M+H]⁺.

¹H NMR (400 MHz, DMSO-d₆) δ=11.41 (br s, 1H), 8.60 (br s, 1H), 7.65 (br d, J=8.3 Hz, 1H), 7.49 (s, 1H), 7.24-6.88 (m, 3H), 5.10-4.82 (m, 1H), 4.56 (br s, 1H), 4.02-3.86 (m, 2H), 3.09 (br s, 2H), 2.36-2.26 (m, 1H), 2.25-2.07 (m, 3H), 2.07-1.77 (m, 8H), 1.73-1.32 (m, 3H).

¹H NMR (400 MHz, METHANOL-d₄) δ=7.70-7.53 (m, 1H), 7.46 (s, 1H), 7.15-6.63 (m, 2H), 5.02 (dd, J=6.0, 10.6 Hz, 1H), 4.65-4.52 (m, 1H), 4.17-3.74 (m, 2H), 3.25-2.90 (m, 2H), 2.56-2.13 (m, 4H), 2.11-1.74 (m, 8H), 1.72-0.99 (m, 3H).

¹H NMR (400 MHz, DMSO-d₆) δ=11.42 (br s, 1H), 8.66 (br s, 1H), 7.64 (br s, 1H), 7.49 (br s, 1H), 7.32-6.79 (m, 3H), 4.97 (br s, 1H), 4.57 (br s, 1H), 3.93 (br s, 2H), 3.11 (br s, 2H), 2.38-2.11 (m, 4H), 2.05-1.77 (m, 8H), 1.73-1.34 (m, 3H).

¹H NMR (400 MHz, METHANOL-d₄) δ=7.64 (d, J=8.6 Hz, 1H), 7.55-7.42 (m, 1H), 7.13-6.99 (m, 2H), 5.09 (dd, J=6.3, 10.7 Hz, 1H), 4.55 (t, J=7.5 Hz, 1H), 4.12-3.95 (m, 2H), 3.27-3.17 (m, 2H), 2.63-2.36 (m, 3H), 2.13-1.90 (m, 9H), 1.80 (br s, 2H), 1.51 (br d, J=9.3 Hz, 1H).

Example 86. Synthesis of Viral Protease Inhibitor Compound 793

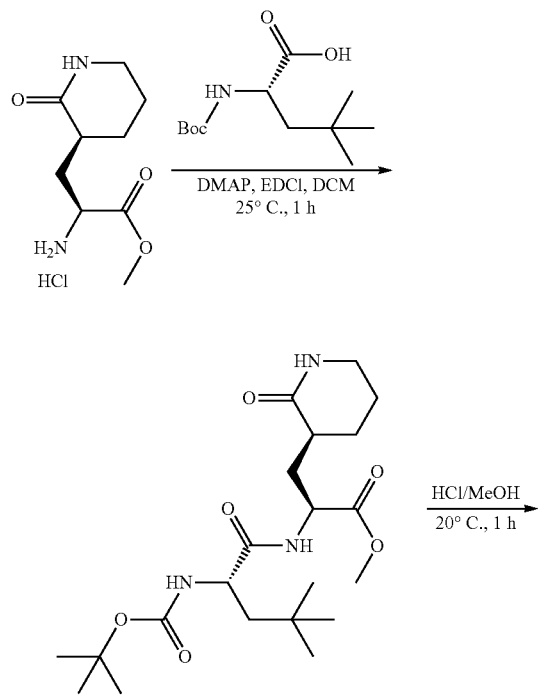

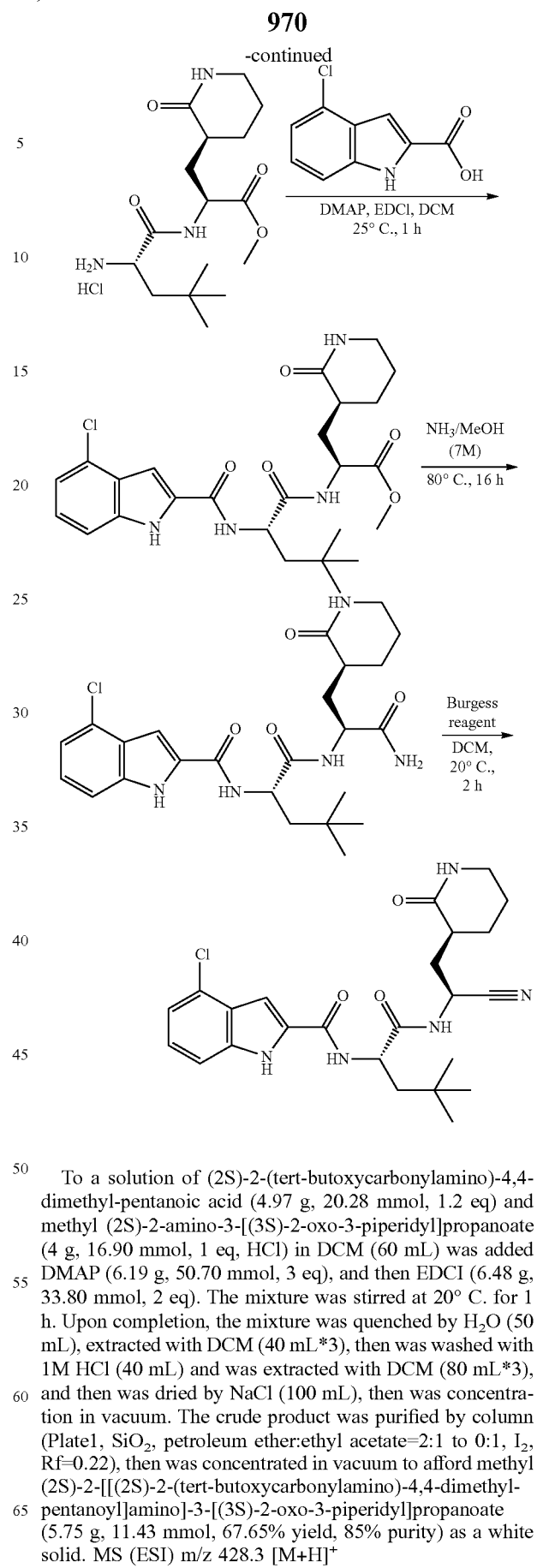

To a solution of (2S)-2-(tert-butoxycarbonylamino)-4,4-dimethyl-pentanoic acid (4.97 g, 20.28 mmol, 1.2 eq) and methyl (2S)-2-amino-3-[(3S)-2-oxo-3-piperidyl]propanoate (4 g, 16.90 mmol, 1 eq, HCl) in DCM (60 mL) was added DMAP (6.19 g, 50.70 mmol, 3 eq), and then EDCI (6.48 g, 33.80 mmol, 2 eq). The mixture was stirred at 20° C. for 1 h. Upon completion, the mixture was quenched by H₂O (50 mL), extracted with DCM (40 mL*3), then was washed with 1M HCl (40 mL) and was extracted with DCM (80 mL*3), and then was dried by NaCl (100 mL), then was concentration in vacuum. The crude product was purified by column (Plate1, SiO₂, petroleum ether:ethyl acetate=2:1 to 0:1, I₂, Rf=0.22), then was concentrated in vacuum to afford methyl (2S)-2-[[(2S)-2-(tert-butoxycarbonylamino)-4,4-dimethyl-pentanoyl]amino]-3-[(3S)-2-oxo-3-piperidyl]propanoate (5.75 g, 11.43 mmol, 67.65% yield, 85% purity) as a white solid. MS (ESI) m/z 428.3 [M+H]⁺

Step 2: methyl (2S)-2-[[(2S)-2-amino-4,4-dimethyl-pentanoyl]amino]-3-[(3S)-2-oxo-3-piperidyl]propanoate A solution of methyl (2S)-2-[[(2S)-2-(tert-butoxycarbonylamino)-4,4-dimethyl-pentanoyl]amino]-3-[(3S)-2-oxo-3-piperidyl]propanoate (500 mg, 1.17 mmol, 1 eq) in HCl/MeOH (10 mL) was stirred at 20° C. for 1 h. Upon completion, the reaction mixture was concentrated under reduced pressure to remove solvent to give methyl (2S)-2-[[(2S)-2-amino-4,4-dimethyl-pentanoyl]amino]-3-[(3S)-2-oxo-3-piperidyl]propanoate (425 mg, crude, HCl) as a white solid. MS (ESI) m/z 328.2 [M+H]$^+$

Step 3: methyl (2S)-2-[[(2S)-2-[(4-chloro-1H-indole-2-carbonyl)amino]-4,4-dimethyl-pentanoyl]amino]-3-[(3S)-2-oxo-3-piperidyl]propanoate To a solution of methyl (2S)-2-[[(2S)-2-amino-4,4-dimethyl-pentanoyl]amino]-3-[(3S)-2-oxo-3-piperidyl]propanoate (409.27 mg, 1.12 mmol, 1 eq, HCl) and 4-chloro-1H-indole-2-carboxylic acid (220 mg, 1.12 mmol, 1 eq) in DCM (15 mL) was added EDCI (646.84 mg, 3.37 mmol, 3 eq), and then was added DMAP (412.22 mg, 3.37 mmol, 3 eq). The mixture was stirred at 20° C. for 1 h. Upon completion, the reaction mixture was poured into H$_2$O (50 mL) at 20° C., and extracted with DCM (20 mL*3). The combined organic layers were washed with 1M HCl (20 mL*2), and then was dried by NaCl (10 mL*2), dried over Na$_2$SO$_4$, filtered and concentrated under reduced pressure to give methyl (2S)-2-[[(2S)-2-[(4-chloro-1H-indole-2-carbonyl)amino]-4,4-dimethyl-pentanoyl]amino]-3-[(3S)-2-oxo-3-piperidyl]propanoate (321 mg, 572.07 umol, 50.86% yield, 90% purity) as a white solid. MS (ESI) m/z 505.2 [M+H]$^+$.

Step 4: N-[(1S)-1-[[(1S)-2-amino-2-oxo-1-[[(3S)-2-oxo-3-piperidyl]methyl]ethyl]carbamoyl]-3,3-dimethyl-butyl]-4-chloro-1H-indole-2-carboxamide A solution of methyl (2S)-2-[[(2S)-2-[(4-chloro-1H-indole-2-carbonyl)amino]-4,4-dimethyl-pentanoyl]amino]-3-[(3S)-2-oxo-3-piperidyl]propanoate (306 mg, 605.93 umol, 1 eq) in NH$_3$/MeOH (7 M, 3 mL, 34.66 eq) was stirred at 80° C. for 16 h. Upon completion, the reaction mixture was concentrated under reduced pressure to give N-[(1S)-1-[[(1S)-2-amino-2-oxo-1-[[(3S)-2-oxo-3-piperidyl]methyl]ethyl]carbamoyl]-3,3-dimethyl-butyl]-4-chloro-1H-indole-2-carboxamide (250 mg, crude) as a yellow solid. MS (ESI) m/z 490.2 [M+H]$^+$.

Step 5: 4-chloro-N-[(1S)-1-[[(1S)-1-cyano-2-[(3S)-2-oxo-3-piperidyl]ethyl]carbamoyl]-3,3-dimethyl-butyl]-1H-indole-2-carboxamide To a solution of N-[(1S)-1-[[(1S)-2-amino-2-oxo-1-[[(3S)-2-oxo-3-piperidyl]methyl]ethyl]carbamoyl]-3,3-dimethyl-butyl]-4-chloro-1H-indole-2-carboxamide (230 mg, 469.39 umol, 1 eq) in DCM (3 mL) was added Burgess reagent (335.58 mg, 1.41 mmol, 3 eq). The mixture was stirred at 20° C. for 2 h. Upon completion, the reaction mixture was concentrated under reduced pressure to give 4-chloro-N-[(1S)-1-[[(1S)-1-cyano-2-[(3S)-2-oxo-3-piperidyl]ethyl]carbamoyl]-3,3-dimethyl-butyl]-1H-indole-2-carboxamide (114 mg, 241.54 umol, 51.46% yield, 100% purity) as a white solid. MS (ESI) m/z 472.2 [M+H]$^+$.

1H NMR (400 MHz, MeOD-d$_4$) δ=7.39 (d, J=8.4 Hz, 1H), 7.28 (s, 1H), 7.18 (t, J=7.8 Hz, 1H), 7.12-7.04 (m, 1H), 7.09 (d, J=7.4 Hz, 1H), 5.16-5.02 (m, 1H), 4.65 (d, J=4.4, 8.4 Hz, 1H), 3.24-3.16 (m, 2H), 2.49-2.38 (m, 2H), 2.00-1.73 (m, 5H), 1.66 (d, J=8.4 Hz, 1H), 1.55-1.45 (m, 1H), 1.03 (s, 8H)

Example 87. Synthesis of Viral Protease Inhibitor Compound 795

Step 1: (S)-methyl2-((S)-2-((tert-butoxycarbonyl)amino)-4,4-dimethylpentanamido)-3-((S)-2-oxopiperidin-3-yl)propanoate

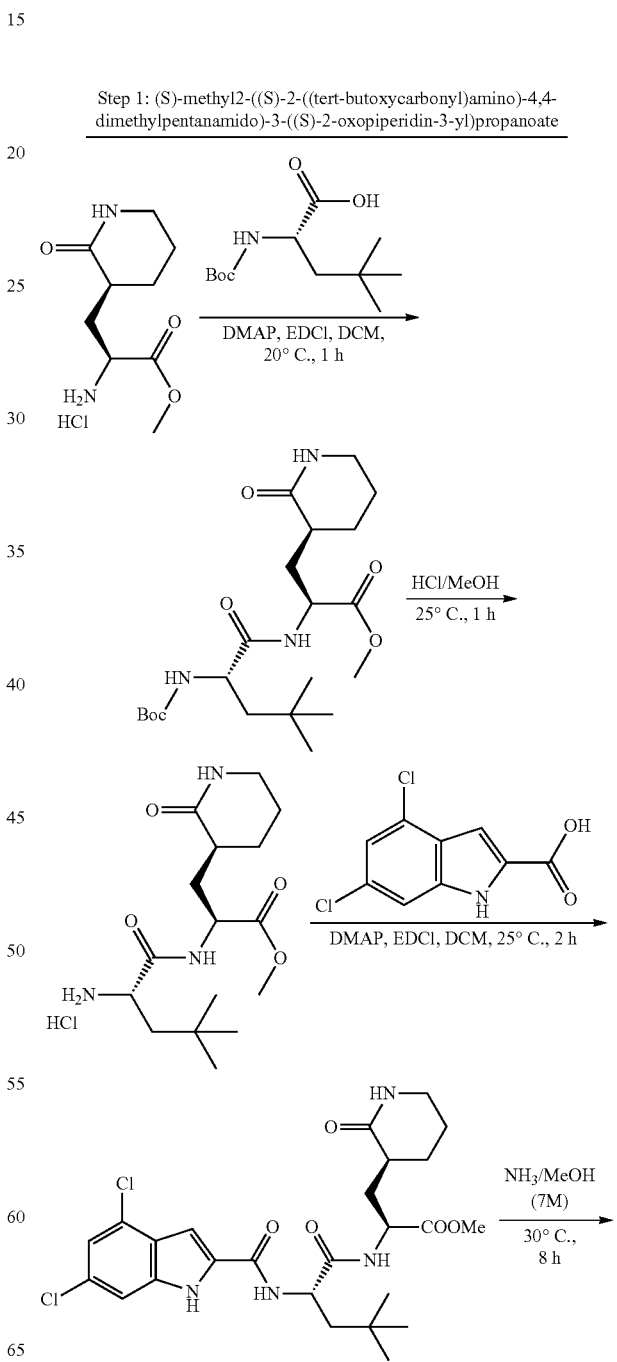

-continued

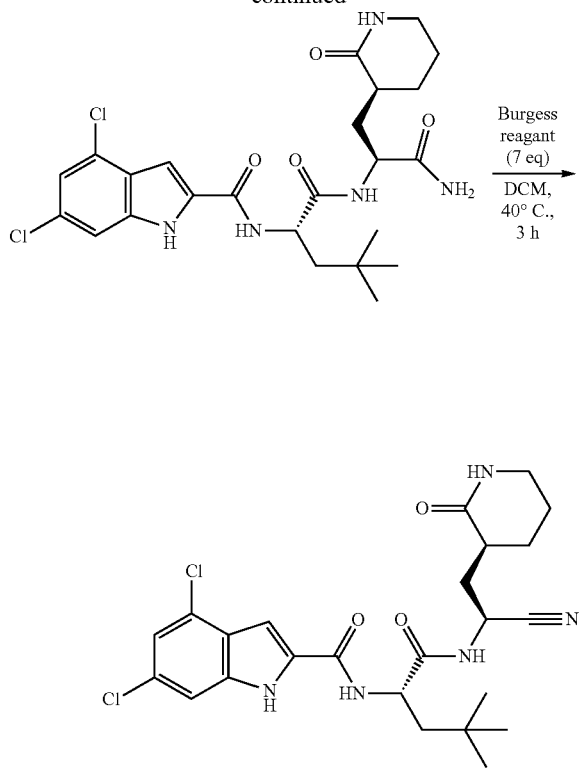

To a solution of (2S)-2-(tert-butoxycarbonylamino)-4,4-dimethyl-pentanoic acid (4.97 g, 20.28 mmol, 1.2 eq) and methyl (2S)-2-amino-3-[(3S)-2-oxo-3-piperidyl]propanoate (4 g, 16.90 mmol, 1 eq, HCl) in DCM (120 mL) was added DMAP (6.19 g, 50.70 mmol, 3 eq), and then was added EDCI (6.48 g, 33.80 mmol, 2 eq). The resulting mixture was stirred at 20° C. for 1 h. Upon completion, The mixture was quenched by H$_2$O (500 mL) and was extracted with DCM (200 mL*3), then was washed with 1M HCl (200 mL) and was extracted with DCM (80 mL*3), and then was dried by NaCl (100 mL), then was concentrated in vacuum. The crude product was purified by column (Plate1, SiO$_2$, petroleum ether:ethyl acetate=2:1 to 0:1, I$_2$, Rf=0.22), then was concentrated in vacuum to give (S)-methyl 2-((S)-2-((tert-butoxycarbonyl)amino)-4,4-dimethylpentanamido)-3-((S)-2-oxopiperidin-3-yl)propanoate (5.75 g, 11.43 mmol, 67.65% yield, 85% purity) as a white solid. MS (ESI) m/z 428.3 [M+H]$^+$.

Step 2: (S)-methyl2-((S)-2-amino-4,4-dimethylpentanamido)-3-((S)-2-oxopiperidin-3-yl)propanoate A solution of (S)-methyl 2-((S)-2-((tert-butoxycarbonyl)amino)-4,4-dimethylpentanamido)-3-((S)-2-oxopiperidin-3-yl)propanoate (700 mg, 1.64 mmol, 1 eq) in HCl/MeOH (10 mL) was stirred at 25° C. for 1 h. Upon completion, the reaction was concentrated in the vacuum to give (S)-methyl 2-((S)-2-amino-4,4-dimethylpentanamido)-3-((S)-2-oxopiperidin-3-yl)propanoate (630 mg, crude, HCl) as yellow solid. MS (ESI) m/z 328.2 [M+H]$^+$.

Step 3: (S)-methyl 2-((S)-2-(4,6-dichloro-1H-indole-2-carboxamido)-4,4-dimethylpentanamido)-3-((S)-2-oxopiperidin-3-yl)propanoate To a solution of (S)-methyl 2-((S)-2-amino-4,4-dimethylpentanamido)-3-((S)-2-oxopiperidin-3-yl)propanoate (630 mg, 1.73 mmol, 1 eq, HCl) in DCM (20 mL) was added 4,6-dichloro-1H-indole-2-carboxylic acid (438.12 mg, 1.90 mmol, 1.1 eq), DMAP (634.54 mg, 5.19 mmol, 3 eq), and EDCI (431.47 mg, 2.25 mmol, 1.3 eq). The mixture was stirred at 25° C. for 2 h. Upon completion, the reaction was quenched by addition H$_2$O (100 mL) and then extracted with EtOAc (100 mL*3). The combined organic layers were washed with brine (100 mL), dried over Na$_2$SO$_4$, filtered and concentrated under reduced pressure and purified by column chromatography (SiO$_2$, petroleum ether/ethyl acetate=7/3 to 0/1) to give product (S)-methyl 2-((S)-2-(4,6-dichloro-1H-indole-2-carboxamido)-4,4-dimethylpentanamido)-3-((S)-2-oxopiperidin-3-yl)propanoate (400 mg, 595.42 umol, 34.39% yield, 80.3% purity) as yellow solid. MS (ESI) m/z 539.2 [M+H]$^+$.

Step 4: N-((S)-1-(((S)-1-amino-1-oxo-3-((S)-2-oxopiperidin-3-yl)propan-2-yl)amino)-4,4-dimethyl-1-oxopentan-2-yl)-4,6-dichloro-1H-indole-2-carboxamide A solution of (S)-methyl 2-((S)-2-(4,6-dichloro-1H-indole-2-carboxamido)-4,4-dimethylpentanamido)-3-((S)-2-oxopiperidin-3-yl)propanoate (370 mg, 685.88 umol, 1 eq) in NH$_3$ (7 M, 20 mL, 204.12 eq) was stirred at 30° C. for 8 h. Upon completion, the reaction was concentrated in the vacuum to afford product N-((S)-1-(((S)-1-amino-1-oxo-3-((S)-2-oxopiperidin-3-yl)propan-2-yl)amino)-4,4-dimethyl-1-oxopentan-2-yl)-4,6-dichloro-1H-indole-2-carboxamide (340 mg, crude) was yellow solid. MS (ESI) m/z 524.2 [M+H]$^+$.

Step5: 4,6-dichloro-N-((S)-1-(((S)-1-cyano-2-((S)-2-oxopiperidin-3-yl)ethyl)amino)-4,4-dimethyl-1-oxopentan-2-yl)-1H-indole-2-carboxamide To a solution of N-((S)-1-(((S)-1-amino-1-oxo-3-((S)-2-oxopiperidin-3-yl)propan-2-yl)amino)-4,4-dimethyl-1-oxopentan-2-yl)-4,6-dichloro-1H-indole-2-carboxamide (320 mg, 610.18 umol, 1 eq) in DCM (15 mL) was added Burgess reagent (1.02 g, 4.27 mmol, 7 eq), and the mixture was stirred at 40° C. for 3 h. Upon completion, the reaction was concentrated in the vacuum and purified by prep-HPLC (column: Waters Xbridge Prep OBD C18 150*40 mm*10 um; mobile phase: [water(0.05% NH$_3$H$_2$O+10 mM NH$_4$HCO$_3$)-ACN]; B %: 40%-60%, 8 min) to afford 4,6-dichloro-N-((S)-1-(((S)-1-cyano-2-((S)-2-oxopiperidin-3-yl)ethyl)amino)-4,4-dimethyl-1-oxopentan-2-yl)-1H-indole-2-carboxamide (110 mg, 217.21 umol, 35.60% yield, 100% purity) as a white solid. MS (ESI) m/z 506.2 [M+H]$^+$ $^1$H NMR (400 MHz, DMSO-d$_6$) δ=12.00 (br s, 1H), 8.94-8.92 (m, 1H), 8.81-8.80 (m, 1H), 7.52 (br s, 1H), 7.42 (s, 2H), 7.24 (s, 1H), 5.11-4.98 (m, 1H), 4.54-4.49 (m, 1H), 3.12-3.01 (m, 2H), 2.34-2.19 (m, 2H), 1.85-1.63 (m, 5H), 1.58-1.45 (m, 1H), 1.43-1.32 (m, 1H), 0.94 (s, 9H)

Example 88. Synthesis of Viral Protease Inhibitor Compound 797

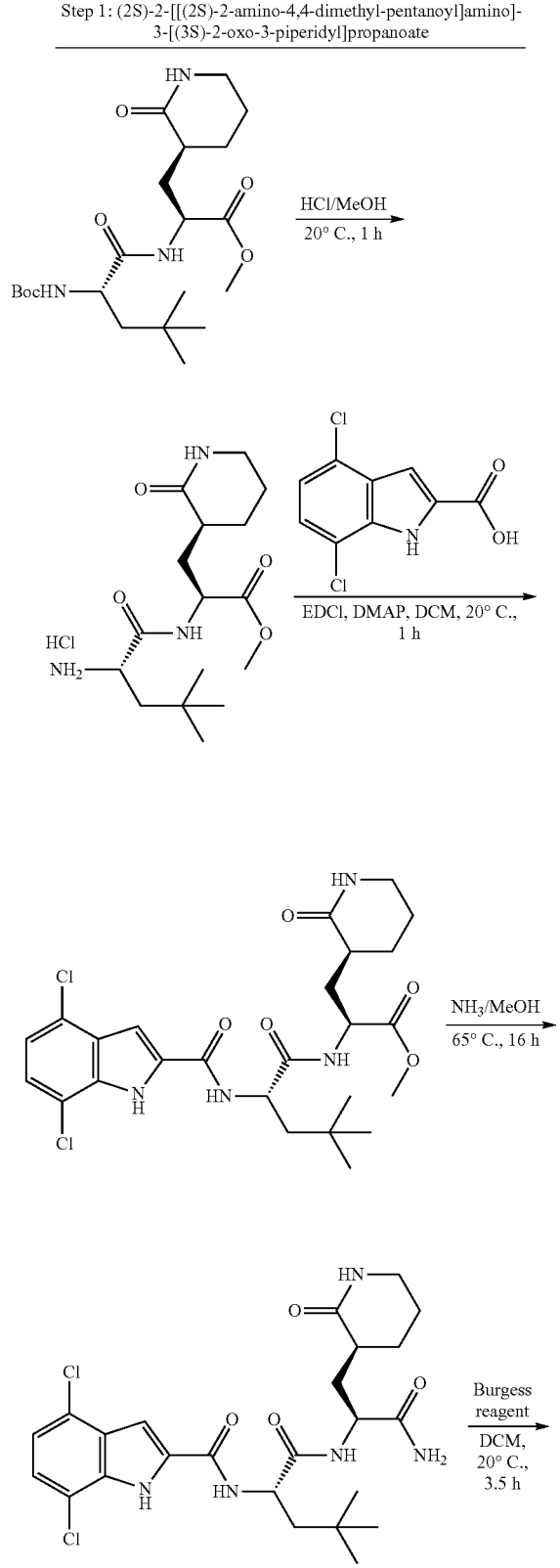

Step 1: (2S)-2-[[(2S)-2-amino-4,4-dimethyl-pentanoyl]amino]-3-[(3S)-2-oxo-3-piperidyl]propanoate

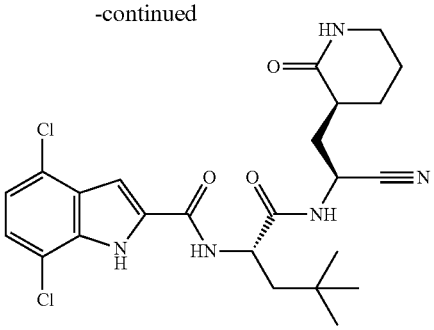

A mixture of methyl (2S)-2-[[(2S)-2-(tert-butoxycarbonylamino)-4,4-dimethyl-pentanoyl]amino]-3-[(3S)-2-oxo-3-piperidyl]propanoate (800 mg, 1.87 mmol, 1 eq) and HCl/MeOH (4 M, 25 mL, 53.44 eq) was stirred at 20° C. for 1 h. Upon completion, the reaction mixture was concentrated under reduced pressure to give the product methyl (2S)-2-[[(2S)-2-amino-4,4-dimethyl-pentanoyl]amino]-3-[(3S)-2-oxo-3-piperidyl]propanoate (650 mg, crude, HCl) as a white solid. MS (ESI) m/z 328.2 [M+H]$^+$.

Step 2: methyl (2S)-2-[[(2S)-2-[(4,7-dichloro-1H-indole-2-carbonyl)amino]-4,4-dimethyl-pentanoyl]amino]-3-[(3S)-2-oxo-3-piperidyl]propanoate A mixture of methyl (2S)-2-[[(2S)-2-amino-4,4-dimethyl-pentanoyl]amino]-3-[(3S)-2-oxo-3-piperidyl]propanoate (650 mg, 1.79 mmol, 1.2 eq, HCl), 4,7-dichloro-1H-indole-2-carboxylic acid (342.45 mg, 1.49 mmol, 1 eq), EDCI (856.10 mg, 4.47 mmol, 3 eq) and DMAP (545.57 mg, 4.47 mmol, 3 eq) in DCM (10 mL) was stirred at 20° C. for 1 h. Upon completion, the mixture was added H$_2$O (50 mL) and then extracted with ethyl acetate (50 mL*3). The combined organic layers were washed with brine (50 mL), dried over Na$_2$SO$_4$, filtered and concentrated under reduced pressure to give a residue. The residue was purified by column chromatography (SiO$_2$, petroleum ether:ethyl acetate=10:1) to afford methyl (2S)-2-[[(2S)-2-[(4,7-dichloro-1H-indole-2-carbonyl)amino]-4,4-dimethyl-pentanoyl]amino]-3-[(3S)-2-oxo-3-piperidyl]propanoate (650 mg, 1.17 mmol, 78.79% yield, 97.34% purity) as a white solid. MS (ESI) m/z 539.2 [M+H]$^+$.

Step 3: N-[(1S)-1-[[(1S)-2-amino-2-oxo-1-[[(3S)-2-oxo-3-piperidyl]methyl]ethyl]carbamoyl]-3,3-dimethyl-butyl]-4,7-dichloro-1H-indole-2-carboxamide A mixture of methyl (2S)-2-[[(2S)-2-[(4,7-dichloro-1H-indole-2-carbonyl)amino]-4,4-dimethyl-pentanoyl]amino]-3-[(3S)-2-oxo-3-piperidyl]propanoate (620 mg, 1.15 mmol, 1 eq) and NH$_3$/MeOH (7 M, 20 mL, 121.81 eq) was stirred at 65° C. for 16 h. Upon completion, the mixture was concentrated under reduced pressure to give the product N-[(1S)-1-[[(1S)-2-amino-2-oxo-1-[[(3S)-2-oxo-3-piperidyl]methyl]ethyl]carbamoyl]-3,3-dimethyl-butyl]-4,7-dichloro-1H-indole-2-carboxamide (550 mg, crude) as a white solid. MS (ESI) m/z 524.2 [M+H]$^+$.

Step 4: 4,7-dichloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-indole-2-carboxamide A mixture of N-[(1S)-1-[[(1S)-2-amino-2-oxo-1-[[(3S)-2-oxo-3-piperidyl]methyl]ethyl]carbamoyl]-3,3-dimethylbutyl]-4,7-dichloro-1H-indole-2-carboxamide (530 mg, 1.01 mmol, 1 eq) and Burgess reagent (722.50 mg, 3.03 mmol, 3 eq) in DCM (10 mL) was stirred at 20° C. for 3.5 h. Upon completion, the mixture was concentrated under reduced pressure to give the residue. Then the residue was purified by prep-HPLC (column: Kromasil C18 (250*50 mm*10 um); mobile phase: [water (10 mM $NH_4HCO_3$)-ACN]; B %: 45%-75%, 10 min) to afford 4,7-dichloro-N-[(1S)-1-[[(1S)-1-cyano-2-[(3S)-2-oxo-3-piperidyl]ethyl]carbamoyl]-3,3-dimethyl-butyl]-1H-indole-2-carboxamide (170 mg, 334.61 umol, 33.11% yield, 99.68% purity) as a white solid. MS (ESI) m/z 506.2 $[M+H]^+$.

$^1$H NMR (400 MHz, METHANOL-$d_4$) δ=7.62-7.56 (m, 1H), 7.52-7.46 (m, 1H), 7.21-7.14 (m, 1H), 5.14-5.07 (m, 1H), 4.70-4.64 (m, 1H), 3.25-3.17 (m, 2H), 2.51-2.38 (m, 2H), 2.02-1.85 (m, 3H), 1.85-1.61 (m, 3H), 1.58-1.44 (m, 1H), 1.08-1.02 (m, 9H)

Example 89. Synthesis of Viral Protease Inhibitor Compound 799

Step 1: 7-chloro-4-methoxy-1H-indole-2-carboxylic acid

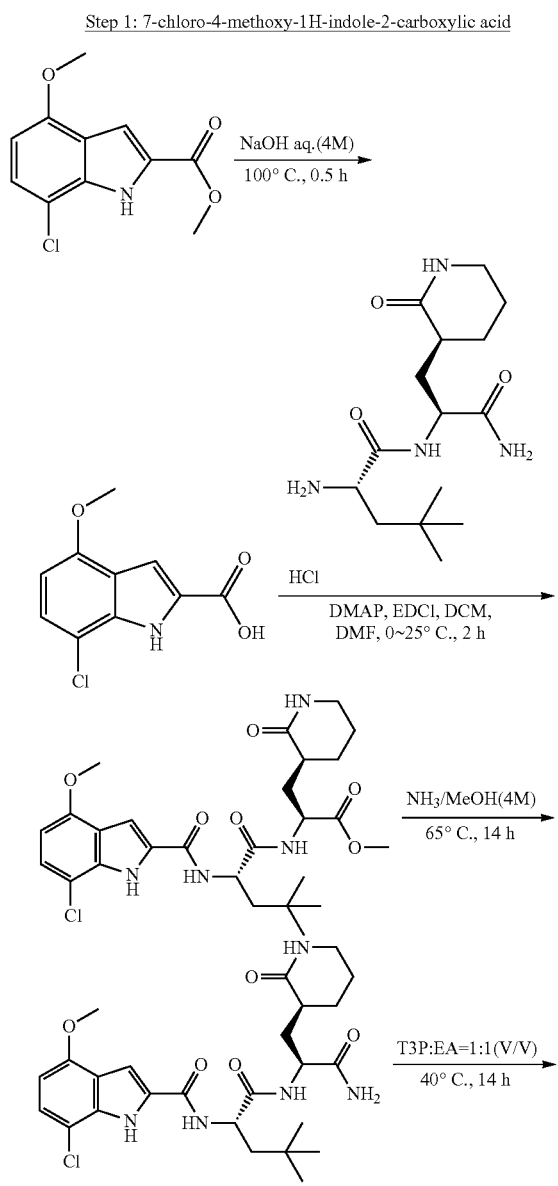

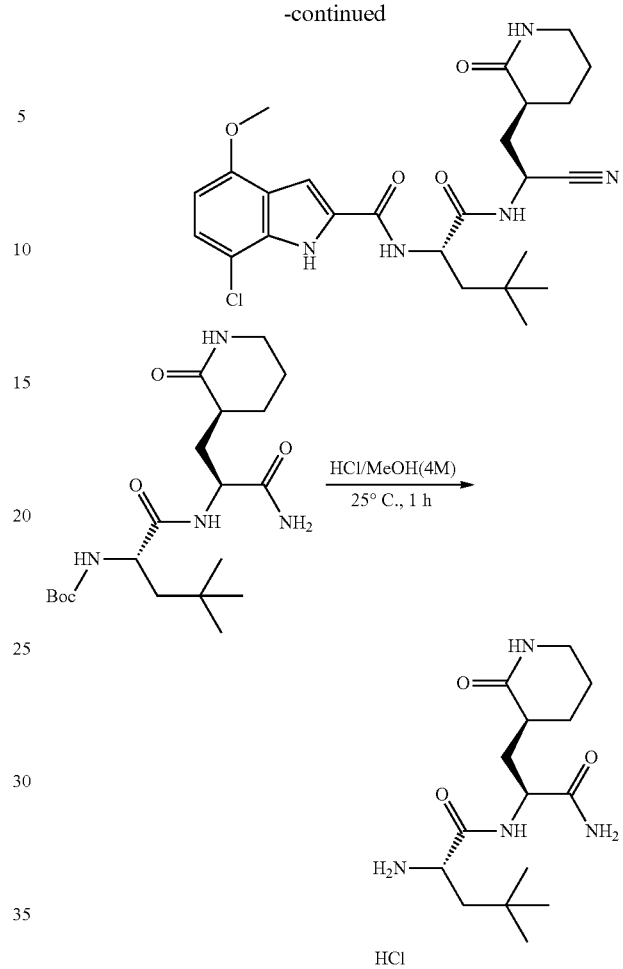

A mixture of methyl 7-chloro-4-methoxy-1H-indole-2-carboxylate (500 mg, 2.09 mmol, 1 eq) in NaOH (2 M, 10.43 mL, 10 eq) was then stirred at 100° C. for 0.5 h. Upon completion, the mixture was acidified by HC (3M) to adjust the pH to about 3, and then the reaction was extracted with EtOAc (10 mL*3). The organic layers were washed with water (10 mL), dried over $Na_2SO_4$, filtered, concentrated under reduced pressure to give 7-chloro-4-methoxy-1H-indole-2-carboxylic acid (400 mg, crude) as a yellow solid.

Step 2: (S)-2-amino-N-((S)-1-amino-1-oxo-3-((S)-2-oxopiperidin-3-yl)propan-2-yl)-4,4-dimethylpentanamide A solution of methyl (2S)-2-[[(2S)-2-(tert-butoxycarbonylamino)-4,4-dimethyl-pentanoyl]amino]-3-[(3S)-2-oxo-3-piperidyl]propanoate (800 mg, 1.87 mmol, 1 eq) in HCl/MeOH (4 M, 8 mL, 17.10 eq) was stirred at 25° C. for 1 h. Upon completion, the mixture was concentrated under reduced pressure to give (S)-2-amino-N-((S)-1-amino-1-oxo-3-((S)-2-oxopiperidin-3-yl)propan-2-yl)-4,4-dimethylpentanamide (810 mg, crude, HCl) as a white solid.

Step 3: (S)-methyl 2-((S)-2-(7-chloro-4-methoxy-1H-indole-2-carboxamido)-4,4-dimethylpentanamido)-3-((S)-2-oxopiperidin-3-yl)propanoate To a solution of 7-chloro-4-methoxy-1H-indole-2-carboxylic acid (440 mg, 1.95 mmol, 1 eq) in DCM (8 mL) and DMF (4 mL) was added (S)-2-amino-N-((S)-1-amino-1-oxo-3-((S)-2-oxopiperidin-3-yl)propan-2-yl)-4,4-dimethylpentanamide (851.53 mg, 2.34 mmol, 1.2 eq, HCl), DMAP (714.74 mg, 5.85 mmol, 3 eq), and then was added EDCI (747.67 mg, 3.90 mmol, 2 eq) at 0° C. The mixture was then stirred at 25° C. for 2 h. Upon completion, the mixture was quenched with water (20 mL) and extracted with DCM (10 mL*3). The organic layers were washed with brine (10 mL), dried over $Na_2SO_4$, filtered, concentrated under reduced pressure to give a residue. The residue was purified by column chromatography ($SiO_2$, DCM:MeOH=100:1 to 10:1) to give (S)-methyl 2-((S)-2-(7-chloro-4-methoxy-1H-indole-2-carboxamido)-4,4-dimethylpentanamido)-3-((S)-2-oxopiperidin-3-yl)propanoate (1.3 g, 1.82 mmol, 93.45% yield, 75% purity) as yellow solid. MS (ESI) m/z 535.1 $[M+H]^+$.

Step 4: N-((S)-1-(((S)-1-amino-1-oxo-3-((S)-2-oxopiperidin-3-yl)propan-2-yl)amino)-4,4-dimethyl-1-oxopentan-2-yl)-7-chloro-4-methoxy-1H-indole-2-carboxamide A solution of (S)-methyl 2-((S)-2-(7-chloro-4-methoxy-1H-indole-2-carboxamido)-4,4-dimethylpentanamido)-3-((S)-2-oxopiperidin-3-yl)propanoate (1.3 g, 1.82 mmol, 75% purity, 1 eq) in $NH_3$/MeOH (7 M, 15 mL, 57.62 eq) was stirred at 65° C. for 14 h. Upon completion, the reaction mixture was concentrated under reduced pressure to give N-((S)-1-(((S)-1-amino-1-oxo-3-((S)-2-oxopiperidin-3-yl)propan-2-yl)amino)-4,4-dimethyl-1-oxopentan-2-yl)-7-chloro-4-methoxy-1H-indole-2-carboxamide (1.25 g, crude) as a yellow solid. MS (ESI) m/z 520.3 $[M+H]^+$.

Step 5: 7-chloro-N-((S)-1-(((S)-1-cyano-2-((S)-2-oxopiperidin-3-yl)ethyl)amino)-4,4-dimethyl-1-oxopentan-2-yl)-4-methoxy-1H-indole-2-carboxamide To a mixture of N-((S)-1-(((S)-1-amino-1-oxo-3-((S)-2-oxopiperidin-3-yl)propan-2-yl)amino)-4,4-dimethyl-1-oxopentan-2-yl)-7-chloro-4-methoxy-1H-indole-2-carboxamide (1.21 g, 1.75 mmol, 75% purity, 1 eq) in EtOAc (6 mL) was added T3P (6.42 g, 10.09 mmol, 6 mL, 50% purity, 5.78 eq), and then the reaction was stirred at 40° C. for 14 h. Upon completion, the mixture was quenched with water (20 mL) and extracted with EtOAc (10 mL*3). The organic layers were washed with brine (10 mL), dried over $Na_2SO_4$, filtered and concentrated under reduced pressure to give a residue. The residue was purified by prep-HPLC (column: Kromasil C18 (250*50 mm*10 um); mobile phase: [water (10 mM $NH_4HCO_3$)-ACN]; B %: 30%-60%, 10 min) to give 7-chloro-N-((S)-1-(((S)-1-cyano-2-((S)-2-oxopiperidin-3-yl)ethyl)amino)-4,4-dimethyl-1-oxopentan-2-yl)-4-methoxy-1H-indole-2-carboxamide (496.09 mg, 988.22 umol, 56.63% yield, 100% purity) as a white solid. MS (ESI) m/z 502.2 $[M+H]^+$.

$^1$H NMR (400 MHz, DMSO-$d_6$) δ=11.64 (br s, 1H), 9.12-8.90 (m, 1H), 8.72-8.54 (m, 1H), 7.52 (br s, 1H), 7.28 (s, 1H), 7.20 (d, J=8.3 Hz, 1H), 6.56 (d, J=8.3 Hz, 1H), 5.05 (q, J=8.0 Hz, 1H), 4.62-4.50 (m, 1H), 3.89 (s, 3H), 3.07 (br s, 2H), 2.31-2.15 (m, 2H), 1.88-1.63 (m, 5H), 1.60-1.33 (m, 2H), 1.06-0.85 (m, 9H).

Example 90. Synthesis of Viral Protease Inhibitor Compound 801

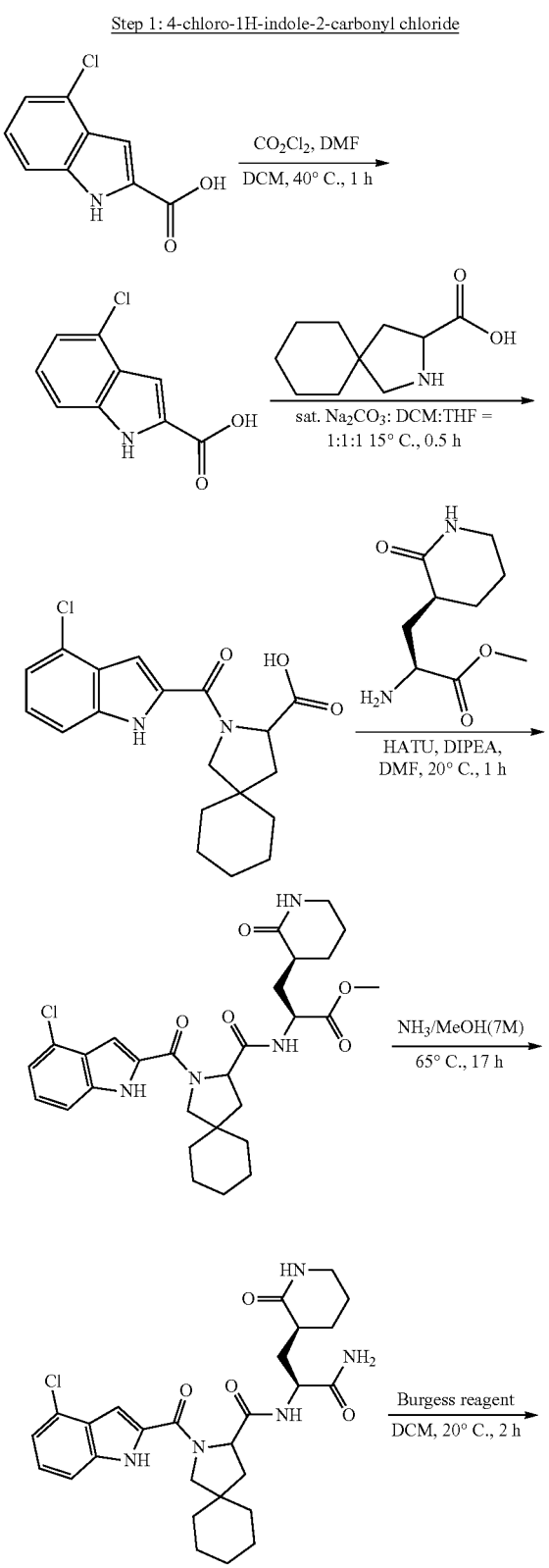

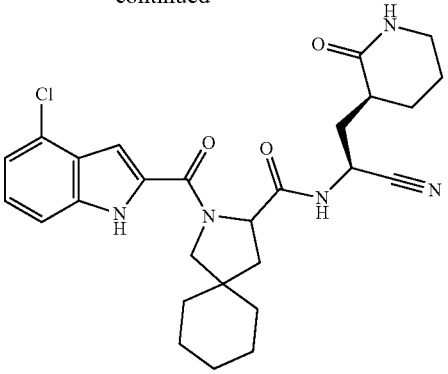

A solution of 4-chloro-1H-indole-2-carboxylic acid (600 mg, 3.07 mmol, 1 eq) in DCM (9 mL) was added DMF (6.73 mg, 92.02 umol, 7.08 uL, 0.03 eq) and (COCl)₂ (778.70 mg, 6.13 mmol, 537.04 uL, 2 eq) was stirred at 40° C. for 1 h. Upon completion, the reaction mixture was concentrated under reduced pressure to give 4-chloro-1H-indole-2-carbonyl chloride (655 mg, crude) was obtained as a yellow oil.

Step 2: 2-(4-chloro-1H-indole-2-carbonyl)-2-azaspiro[4.5]decane-3-carboxylic acid A mixture of 4-chloro-1H-indole-2-carbonyl chloride (655 mg, 3.06 mmol, 1.1 eq) in THF (6 mL) DCM (6 mL) was poured into a mixture of 2-azaspiro[4.5]decane-3-carboxylic acid (611.20 mg, 2.78 mmol, 1 eq, HCl), Na₂CO₃ (884.85 mg, 2.78 mmol, 3 eq) in DCM (6 mL) and H₂O (6 mL). The mixture was stirred at 15° C. for 0.5 h under N₂ atmosphere. Upon completion, the reaction mixture was quenched by addition HCl (1M) (15 mL) and extracted with DCM (10 mL*4). The combined organic layers were concentrated under reduced pressure to give a residue. The crude product was triturated with EtOAc (3 mL) at 20° C. for 15 min. to give 2-(4-chloro-1H-indole-2-carbonyl)-2-azaspiro[4.5]decane-3-carboxylic acid (710 mg, 1.97 mmol, 70.73% yield) was obtained as white solid. MS (ESI) m/z 361.2 [M+H]⁺.

Step 3: (2S)-methyl 2-(2-(4-chloro-1H-indole-2-carbonyl)-2-azaspiro[4.5]decane-3-carboxamido)-3-((S)-2-oxopiperidin-3-yl)propanoate To a solution of methyl (2S)-2-amino-3-[(3S)-2-oxo-3-piperidyl]propanoate (512.31 mg, 2.16 mmol, 1.1 eq, HCl) 2-(4-chloro-1H-indole-2-carbonyl)-2-azaspiro[4.5]decane-3-carboxylic acid (710 mg, 1.97 mmol, 1 eq) in DMF (15 mL) was added DIPEA (762.90 mg, 5.90 mmol, 1.03 mL, 3 eq) and HATU (748.17 mg, 1.97 mmol, 1 eq). The mixture was stirred at 20° C. for 1 h. Upon completion, the reaction mixture was quenched by addition H₂O (40 mL), and then extracted with ethyl acetate (20 mL*4). The combined organic layers were washed with brine (20 mL*1), dried over Na₂SO₄, filtered and concentrated under reduced pressure to give methyl (2S)-2-[[2-(4-chloro-1H-indole-2-carbonyl)-2-azaspiro[4.5]decane-3-carbonyl]amino]-3-[(3S)-2-oxo-3-piperidyl]propanoate (850 mg, 1.57 mmol, 79.55% yield) as a yellow oil.

Step 4: N-((S)-1-amino-1-oxo-3-((S)-2-oxopiperidin-3-yl)propan-2-yl)-2-(4-chloro-1H-indole-2-carbonyl)-2-azaspiro[4.5]decane-3-carboxamide A solution of methyl (2S)-2-[[2-(4-chloro-1H-indole-2-carbonyl)-2-azaspiro[4.5]decane-3-carbonyl]amino]-3-[(3S)-2-oxo-3-piperidyl]propanoate (850 mg, 1.57 mmol, 1 eq) in MeOH/NH₃ (7 M, 11.05 mL, 49.42 eq) was stirred at 65° C. for 17 h. Upon completion, The reaction mixture was concentrated under reduced pressure to give N-[(1S)-2-amino-2-oxo-1-[[(3S)-2-oxo-3-piperidyl]methyl]ethyl]-2-(4-chloro-1H-indole-2-carbonyl)-2-azaspiro[4.5]decane-3-carboxamide (820 mg, crude) was obtained as colorless oil. MS (ESI) m/z 528.3 [M+H]⁺.

Step 5: 2-(4-chloro-1H-indole-2-carbonyl)-N-((S)-1-cyano-2-((S)-2-oxopiperidin-3-yl)ethyl)-2-azaspiro[4.5]decane-3-carboxamide To a solution of N-[(1S)-2-amino-2-oxo-1-[[(3S)-2-oxo-3-piperidyl]methyl]ethyl]-2-(4-chloro-1H-indole-2-carbonyl)-2-azaspiro[4.5]decane-3-carboxamide (820 mg, 1.55 mmol, 1 eq) in DCM (15 mL) was added Burgess reagent (999.20 mg, 4.19 mmol, 2.7 eq). The mixture was stirred at 20° C. for 2 h. Upon completion, the reaction mixture was quenched by addition H₂O (3 mL) and concentrated under reduced pressure to give a residue. The residue was purified by prep-HPLC (column: Kromasil C18 (250*50 mm*10 um); mobile phase: [water (10 mM NH₄HCO₃)-ACN]; B %: 45%-75%, 10 min) to give desired compound (450 mg) as a white solid, which was further separated by SFC (column: REGIS(S,S)WHELK-O1 (250 mm*25 mm, 10 um); mobile phase: [0.1% NH₃H₂O ETOH]; B %: 60%-60%, min) to afford 2-(4-chloro-1H-indole-2-carbonyl)-N-[(1S)-1-cyano-2-[(3S)-2-oxo-3-piperidyl]ethyl]-2-azaspiro[4.5]decane-3-carboxamide (168.83 mg, 331.02 umol, 21.32% yield, 100% purity) as white solid. MS (ESI) m/z 510.3 [M+H]⁺.

¹H NMR (400 MHz, DMSO-d₆) δ ppm 11.72 (br s, 1H) 8.52-9.07 (m, 1H) 6.72-7.49 (m, 5H) 4.81-5.16 (m, 1H) 4.43-4.78 (m, 1H) 3.51-3.92 (m, 2H) 2.10-2.39 (m, 3H) 1.25-1.98 (m, 16H).

To give 2-(4-chloro-1H-indole-2-carbonyl)-N-[(1S)-1-cyano-2-[(3S)-2-oxo-3-piperidyl]ethyl]-2-azaspiro[4.5]decane-3-carboxamide (180.55 mg, 354.00 umol, 22.80% yield, 100% purity) was obtained as white solid. MS (ESI) m/z 510.3 [M+H]⁺.

¹H NMR (400 MHz, DMSO-d₆) δ ppm 11.56-11.85 (m, 1H) 8.45-8.94 (m, 1H) 7.43 (br d, J=8.16 Hz, 1H) 7.04-7.35 (m, 3H) 6.75-7.03 (m, 1H) 4.42-5.12 (m, 2H) 3.58-3.91 (m, 2H) 2.06-2.30 (m, 3H) 1.21-1.94 (m, 16H).

Example 91. Synthesis of Viral Protease Inhibitor Compound 803

Step 1: (2S)-methyl 3-((S)-2-oxopiperidin-3-yl)-2-(6-azaspiro[3.4]octane-7-carboxamido)propanoate

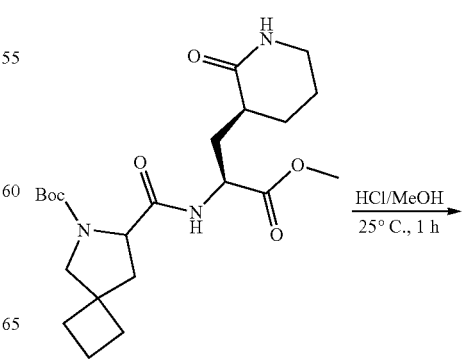

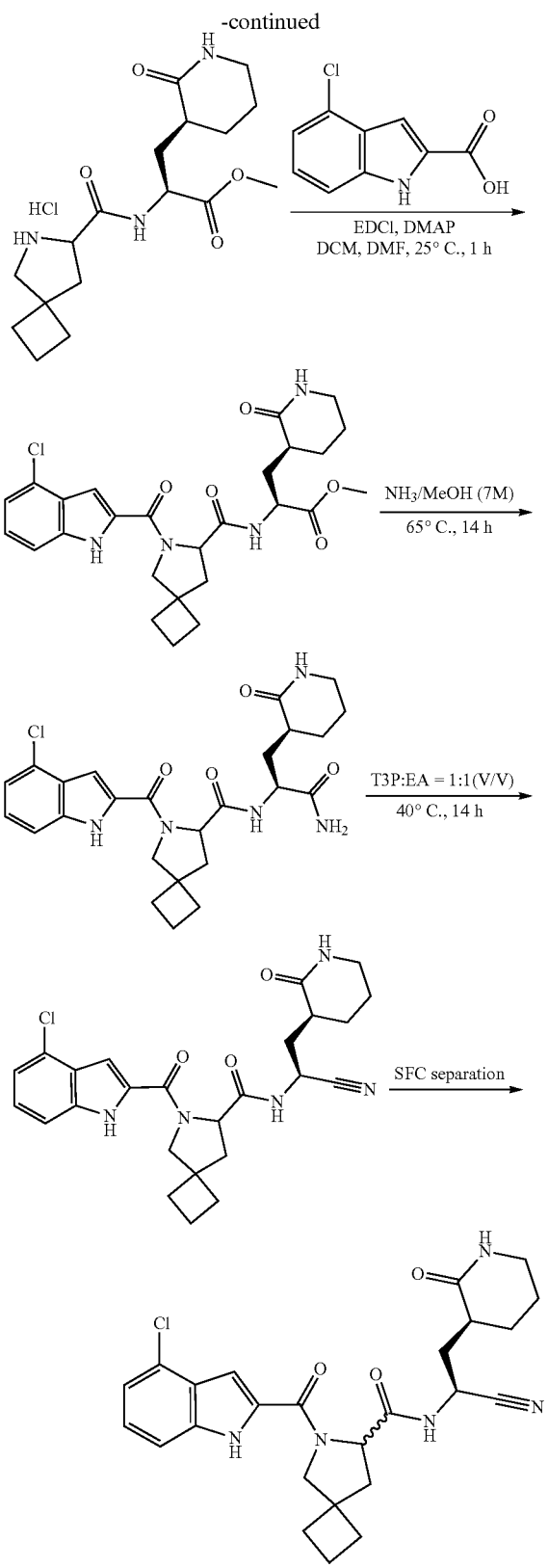

A solution of tert-butyl 7-(((S)-1-methoxy-1-oxo-3-((S)-2-oxopiperidin-3-yl)propan-2-yl)carbamoyl)-6-azaspiro[3.4]octane-6-carboxylate (1.2 g, 2.47 mmol, 90% purity, 1 eq) in HCl/MeOH (4 M, 12 mL, 19.45 eq) was stirred at 25° C. for 1 h. Upon completion, the reaction mixture was concentrated under reduced pressure to give (2S)-methyl 3-((S)-2-oxopiperidin-3-yl)-2-(6-azaspiro[3.4]octane-7-carboxamido)propanoate (1.3 g, crude, HCl) as a yellow solid. MS (ESI) m/z 338.2 [M+H]$^+$.

Step 2: (2S)-methyl 2-(6-(4-chloro-1H-indole-2-carbonyl)-6-azaspiro[3.4]octane-7-carboxamido)-3-((S)-2-oxopiperidin-3-yl)propanoate To a solution of (2S)-methyl 3-((S)-2-oxopiperidin-3-yl)-2-(6-azaspiro[3.4]octane-7-carboxamido)propanoate (1.25 g, 2.34 mmol, 70% purity, 1 eq, HCl) in DCM (8 mL) and DMF (4 mL) was added 4-chloro-1H-indole-2-carboxylic acid (457.78 mg, 2.34 mmol, 1 eq), DMAP (857.77 mg, 7.02 mmol, 3 eq), and then was added EDCI (897.29 mg, 4.68 mmol, 2 eq). The mixture was then stirred at 25° C. for 1 h. Upon completion, the reaction mixture was diluted with water (20 mL) and extracted with DCM (10 mL*3). The organic layers were washed with brine (10 mL), dried over Na$_2$SO$_4$, filtered and concentrated under reduced pressure to give a residue. The residue was purified by column chromatography (SiO$_2$, dichloromethane:methanol=100:1 to 10:1) to give (2S)-methyl 2-(6-(4-chloro-1H-indole-2-carbonyl)-6-azaspiro[3.4]octane-7-carboxamido)-3-((S)-2-oxopiperidin-3-yl)propanoate (1.51 g, 2.20 mmol, 93.96% yield, 75% purity) as a yellow solid. MS (ESI) m/z 515.2 [M+H]$^+$.

Step 3: N-((S)-1-amino-1-oxo-3-((S)-2-oxopiperidin-3-yl)propan-2-yl)-6-(4-chloro-1H-indole-2-carbonyl)-6-azaspiro[3.4]octane-7-carboxamide A solution of (2S)-methyl 2-(6-(4-chloro-1H-indole-2-carbonyl)-6-azaspiro[3.4]octane-7-carboxamido)-3-((S)-2-oxopiperidin-3-yl)propanoate (1.51 g, 2.20 mmol, 75% purity, 1 eq) in NH$_3$/MeOH (7 M, 15 mL, 47.75 eq) was stirred at 65° C. for 14 h. Upon completion, the reaction mixture was concentrated under reduced pressure to give N-((S)-1-amino-1-oxo-3-((S)-2-oxopiperidin-3-yl)propan-2-yl)-6-(4-chloro-1H-indole-2-carbonyl)-6-azaspiro[3.4]octane-7-carboxamide (1.5 g, crude) as a yellow solid. MS (ESI) m/z 500.3 [M+H]$^+$.

Step 4: 6-(4-chloro-1H-indole-2-carbonyl)-N-((S)-1-cyano-2-((S)-2-oxopiperidin-3-yl)ethyl)-6-azaspiro[3.4]octane-7-carboxamide To a solution of N-((S)-1-amino-1-oxo-3-((S)-2-oxopiperidin-3-yl)propan-2-yl)-6-(4-chloro-1H-indole-2-carbonyl)-6-azaspiro[3.4]octane-7-carboxamide (1.5 g, 2.10 mmol, 70% purity, 1 eq) in EtOAc (8 mL) was added T3P (8.56 g, 13.45 mmol, 8 mL, 50% purity, 6.41 eq), and then the reaction was stirred at 40° C. for 14 h. Upon completion, the mixture was quenched with water (25 mL) and extracted with EtOAc (15 mL*3). The organic layers were washed with brine (15 mL), dried over Na$_2$SO$_4$, filtered, and concentrated under reduced pressure to give a residue. The residue was purified by prep-HPLC (column: Kromasil C18 (250*50 mm*10 um); mobile phase: [water (10 mM NH$_4$HCO$_3$)-ACN]; B %: 30%-50%, 10 min) to give 6-(4-chloro-1H-indole-2-carbonyl)-N-((S)-1-cyano-2-((S)-2-oxopiperidin-3-yl)ethyl)-6-azaspiro[3.4]octane-7-carboxamide (420 mg, 865.32 umol, 41.20% yield, 99.3% purity) as a white solid. MS (ESI) m/z 482.2 [M+H]$^+$.

Step 5: 6-(4-chloro-1H-indole-2-carbonyl)-N-((S)-1-cyano-2-((S)-2-oxopiperidin-3-yl)ethyl)-6-azaspiro[3.4]octane-7-carboxamide 6-(4-chloro-1H-indole-2-carbonyl)-N-((S)-1-cyano-2-((S)-2-oxopiperidin-3-yl)ethyl)-6-azaspiro[3.4]octane-7-carboxamide (420 mg, 99.3% purity) was separation by SFC (column: REGIS(S,S)WHELK-O1 (250 mm*25 mm, 10 um); mobile phase: [0.1% $NH_3H_2O$ EtOH]; B %: 60%-60%, min) to give 6-(4-chloro-1H-indole-2-carbonyl)-N-((S)-1-cyano-2-((S)-2-oxopiperidin-3-yl)ethyl)-6-azaspiro[3.4]octane-7-carboxamide Isomer 1 (8.72 mg, 18.09 umol, 2.09% yield, 100% purity) as a white solid. MS (ESI) m/z 482.2 $[M+H]^+$.

$^1$H NMR (400 MHz, METHANOL-$d_4$) δ=7.49-7.34 (m, 1H), 7.20 (br t, J=7.5 Hz, 1H), 7.15-6.67 (m, 2H), 5.15-5.00 (m, 1H), 4.65-4.54 (m, 1H), 4.15-3.78 (m, 2H), 3.25-2.99 (m, 2H), 2.58-1.25 (m, 15H).

$^1$H NMR (400 MHz, DMSO-$d_6$) δ=11.96 (br s, 1H), 9.06-8.67 (m, 1H), 7.53 (br d, J=11.2 Hz, 1H), 7.43 (br d, J=7.7 Hz, 1H), 7.27-7.05 (m, 2H), 7.04-6.54 (m, 1H), 5.06-4.86 (m, 1H), 4.57-4.36 (m, 1H), 4.18-3.66 (m, 2H), 3.08 (br s, 2H), 2.37-2.11 (m, 4H), 2.07-1.17 (m, 1H).

To give 6-(4-chloro-1H-indole-2-carbonyl)-N-((S)-1-cyano-2-((S)-2-oxopiperidin-3-yl)ethyl)-6-azaspiro[3.4]octane-7-carboxamide Isomer 2 (197.12 mg, 408.99 umol, 47.26% yield, 100% purity) as a white solid. MS (ESI) m/z 482.2 $[M+H]^+$.

$^1$H NMR (400 MHz, METHANOL-$d_4$) δ=7.46-7.34 (m, 1H), 7.25-7.18 (m, 1H), 7.17-6.65 (m, 2H), 5.08-4.97 (m, 1H), 4.58 (t, J=7.5 Hz, 1H), 4.22-3.72 (m, 2H), 3.24-2.87 (m, 2H), 2.53-2.18 (m, 4H), 2.13-1.75 (m, 8H), 1.70-1.22 (m, 3H).

$^1$H NMR (400 MHz, DMSO-$d_6$) δ=11.95 (s, 1H), 9.30-8.55 (m, 1H), 7.58-7.32 (m, 2H), 7.31-7.07 (m, 2H), 7.05-6.55 (m, 1H), 5.16-4.85 (m, 1H), 4.47 (t, J=7.2 Hz, 1H), 4.13-3.68 (m, 2H), 3.17-2.82 (m, 2H), 2.34-2.10 (m, 4H), 2.10-1.67 (m, 9H), 1.63-1.01 (m, 2H).

To give 6-(4-chloro-1H-indole-2-carbonyl)-N-((S)-1-cyano-2-((S)-2-oxopiperidin-3-yl)ethyl)-6-azaspiro[3.4]octane-7-carboxamide Isomer 3 (111.90 mg, 232.17 umol, 26.83% yield, 100% purity) as a white solid. MS (ESI) m/z 482.2 $[M+H]^+$.

$^1$H NMR (400 MHz, METHANOL-$d_4$) δ=7.43-7.34 (m, 1H), 7.22-7.16 (m, 1H), 7.13-6.73 (m, 2H), 5.10 (dd, J=5.7, 10.3 Hz, 1H), 4.57 (t, J=7.9 Hz, 1H), 4.16-3.97 (m, 2H), 3.27-3.19 (m, 2H), 2.63-2.33 (m, 3H), 2.30-2.19 (m, 1H), 2.11-1.92 (m, 8H), 1.85-1.68 (m, 2H), 1.55-1.47 (m, 1H).

$^1$H NMR (400 MHz, DMSO-$d_6$) δ=11.95 (br s, 1H), 9.43-8.64 (m, 1H), 7.63-7.33 (m, 2H), 7.27-7.05 (m, 2H), 7.04-6.56 (m, 1H), 5.10-4.86 (m, 1H), 4.46 (br t, J=7.4 Hz, 1H), 4.08-3.60 (m, 2H), 3.18-2.88 (m, 2H), 2.36-2.09 (m, 4H), 2.04-1.17 (m, 11H).

To give 6-(4-chloro-1H-indole-2-carbonyl)-N-((S)-1-cyano-2-((S)-2-oxopiperidin-3-yl)ethyl)-6-azaspiro[3.4]octane-7-carboxamide Isomer 4 (2.11 mg, 4.24 umol, 0.49% yield, 96.8% purity) as a white solid. MS (ESI) m/z 482.2 $[M+H]^+$.

$^1$H NMR (400 MHz, METHANOL-$d_4$) δ=7.44-7.36 (m, 1H), 7.24-7.17 (m, 1H), 7.16-6.69 (mz, 2H), 5.21-5.01 (m, 1H), 4.68-4.51 (m, 1H), 4.12-3.81 (m, 2H), 3.25-3.19 (m, 2H), 2.56-2.15 (m, 3H), 2.12-1.69 (m, 8H), 1.64-1.26 (m, 4H).

$^1$H NMR (400 MHz, DMSO-d6) δ=11.96 (br s, 1H), 9.02-8.65 (m, 1H), 7.62-7.46 (m, 1H), 7.45-7.34 (m, 1H), 7.27-7.06 (m, 2H), 7.04-6.57 (m, 1H), 5.04-4.86 (m, 1H), 4.57-4.37 (m, 1H), 4.10-3.63 (m, 2H), 3.17-2.83 (m, 2H), 2.34-2.26 (m, 2H), 2.23-2.10 (m, 2H), 2.04-1.82 (m, 7H), 1.80-1.37 (m, 2H), 1.37-1.13 (m, 2H).

Example 92. Synthesis of Viral Protease Inhibitor Compound 805

Step 1: ethyl 2-(7-chloro-1H-indole-2-carbonyl)-8,8-difluoro-2-azaspiro[4.5]decane-3-carboxylate

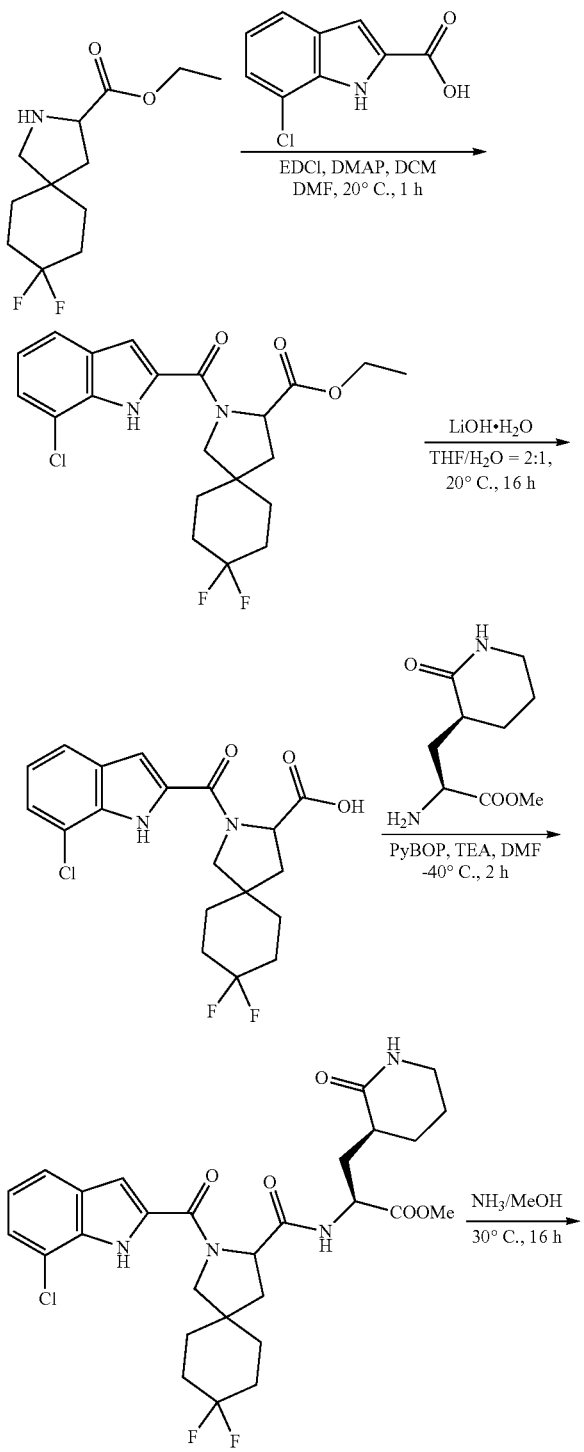

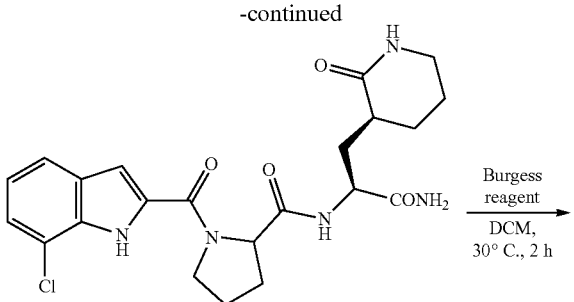

To a solution of ethyl 8,8-difluoro-2-azaspiro[4.5]decane-3-carboxylate (1.5 g, 6.07 mmol, 1 eq) and 7-chloro-1H-indole-2-carboxylic acid (1.42 g, 7.28 mmol, 1.2 eq) in DCM (25 mL) was added DMAP (1.48 g, 12.13 mmol, 2 eq) and EDCI (2.33 g, 12.13 mmol, 2 eq), then the mixture was stirred at 20° C. for 2 h. Upon the reaction completement, the mixture was quenched by water (20 mL) and was extracted with DCM (10 mL*3), then was concentrated in vacuum and was purified by column (SiO₂, petroleum ether:ethyl acetate=20:1 to 2.5:1) to obtained ethyl 2-(7-chloro-1H-indole-2-carbonyl)-8, 8-difluoro-2-azaspiro[4.5] decane-3-carboxylate (1.6 g, 3.58 mmol, 58.98% yield, 95% purity) as a pink oil. MS (ESI) m/z 425.2 [M+H]⁺.

Step 2: 2-(7-chloro-1H-indole-2-carbonyl)-8,8-difluoro-2-azaspiro[4.5]decane-3-carboxylic acid To a solution of ethyl 2-(7-chloro-1H-indole-2-carbonyl)-8, 8-difluoro-2-azaspiro [4.5] decane-3-carboxylate (1.6 g, 3.77 mmol, 1 eq) in THF (12 mL) and H₂O (6 mL) was added LiOH·H₂O (474.09 mg, 11.30 mmol, 3 eq), and then the mixture was stirred at 20° C. for 16 h. Upon completion, the mixture was concentrated in vacuum and the pH was adjusted to pH=~1 with 1M HCl (30 mL). The reaction was triturated by DCM (30 mL), and then was filtered and the filtered cake was dried in vacuum to obtain 2-(7-chloro-1H-indole-2-carbonyl)-8,8-difluoro-2-azaspiro[4.5]decane-3-carboxylic acid (1.4 g, 3.53 mmol, 93.69% yield) as a white solid.

Step 3: (2S)-methyl2-(2-(7-chloro-1H-indole-2-carbonyl)-8,8-difluoro-2-azaspiro[4.5]decane-3-carboxamido)-3-((S)-2-oxopiperidin-3-yl)propanoate To a solution of 2-(7-chloro-1H-indole-2-carbonyl)-8,8-difluoro-2-azaspiro[4.5]decane-3-carboxylic acid (1.7 g, 4.28 mmol, 1 eq) and methyl (2S)-2-amino-3-[(3S)-2-oxo-3-piperidyl] propanoate (1.01 g, 4.28 mmol, 1 eq, HCl) in DMF (30 mL) was added PyBOP (2.23 g, 4.28 mmol, 1 eq), and then was added TEA (1.30 g, 12.85 mmol, 1.79 mL, 3 eq) in DMF (5 mL) at −40° C. The mixture was stirred at −40° C. for 2 h. Upon the reaction completion, the mixture was poured into water (100 mL) and was extracted with DCM (40 mL*3), then was dried by Na₂SO₄ and was concentrated in vacuum and was purified by column (SiO₂, petroleum ether:ethyl acetate=1:1 to DCM:MeOH=10:1) to obtained (2S)-methyl 2-(2-(7-chloro-1H-indole-2-carbonyl)-8, 8-difluoro-2-azaspiro [4.5]decane-3-carboxamido)-3-((S)-2-oxopiperidin-3-yl) propanoate (2.2 g, 3.04 mmol, 70.95% yield, 80% purity) as a colorless solid. MS (ESI) m/z 579.3 [M+H]⁺.

Step 4: N-((S)-1-amino-1-oxo-3-((S)-2-oxopiperidin-3-yl)propan-2-yl)-2-(7-chloro-1H-indole-2-carbonyl)-8,8-difluoro-2-azaspiro[4.5]decane-3-carboxamide A solution of (2S)-methyl 2-(2-(7-chloro-1H-indole-2-carbonyl)-8,8-difluoro-2-azaspiro [4.5] decane-3-carboxamido)-3-((S)-2-oxopiperidin-3-yl) propanoate (400 mg, 518.10 umol, 75% purity, 1 eq) in NH₃/MeOH (6 mL, 7M) was stirred at 30° C. for 16 h. Upon the reaction completion, the mixture was concentrated in vacuum to obtain N-((S)-1-amino-1-oxo-3-((S)-2-oxopiperidin-3-yl) propan-2-yl)-2-(7-chloro-1H-indole-2-carbonyl)-8, 8-difluoro-2-azaspiro [4.5]decane-3-carboxamide (1.4 g, batch 5, crude) as a white solid. MS (ESI) m/z 564.2 [M+H]⁺

Step 5: 2-(7-chloro-1H-indole-2-carbonyl)-N-((S)-1-cyano-2-((S)-2-oxopiperidin-3-yl)ethyl)-8,8-difluoro-2-azaspiro[4.5]decane-3-carboxamide To a solution of N-((S)-1-amino-1-oxo-3-((S)-2-oxopiperidin-3-yl) propan-2-yl)-2-(7-chloro-1H-indole-2-carbonyl)-8,8-difluoro-2-azaspiro[4.5] decane-3-carboxamide (1.4 g, 2.48 mmol, 1 eq) in DCM (30 mL) was added Burgess reagent (1.77 g, 7.45 mmol, 3 eq). The mixture was stirred at 30° C. for 2 h. Upon the reaction completion, the reaction mixture was quenched with water (2 mL) and was dried by blowing N₂. The concentrate was purified by prep-HPLC (column: Welch Xtimate C18 250*70 mm #10 um; mobile phase: [water (10 mM NH₄HCO₃)-ACN]; B %: 30%-60%, 20 min) to obtain 2-(7-chloro-1H-indole-2-carbonyl)-N-((S)-1-cyano-2-((S)-2-oxopiperidin-3-yl)ethyl)-8, 8-difluoro-2-azaspiro[4.5]decane-3-carboxamide (740 mg, 1.33 mmol, 53.51% yield, 98% purity) as a white solid. MS (ESI) m/z 546.2 [M+H]+

Step 6: 2-(7-chloro-1H-indole-2-carbonyl)-N-((S)-1-cyano-2-((S)-2-oxopiperidin-3-yl)ethyl)-8,8-difluoro-2-azaspiro[4.5]decane-3-carboxamide)

The 2-(7-chloro-1H-indole-2-carbonyl)-N-((S)-1-cyano-2-((S)-2-oxopiperidin-3-yl)ethyl)-8,8-difluoro-2-azaspiro[4.5]decane-3-carboxamide (740 mg, 1.33 mmol, 53.51% yield, 98% purity) was separated by SFC (column: REGIS (S,S)WHELK-O1 (250 mm*25 mm, 10 um); mobile phase: [Neu-ETOH]; B %: 60%-60%, 7 min) to obtained 2-(7-chloro-1H-indole-2-carbonyl)-N-((S)-1-cyano-2-((S)-2-oxopiperidin-3-yl)ethyl)-8,8-difluoro-2-azaspiro[4.5]decane-3-carboxamide (Isomer 1: 340 mg, 622.70 umol, 45.95% yield, 100% purity) as a white solid. MS (ESI) m/z 546.1 [M+H]+

$^1$H NMR (400 MHz, MeOD-$d_4$) δ ppm 7.67-7.47 (m, 1H), 7.28 (d, J=7.6 Hz, 1H), 7.18-6.82 (m, 2H), 5.15-4.97 (m, 1H), 4.82-4.58 (m, 1H), 4.05-3.73 (m, 2H), 3.27-2.92 (m, 2H), 2.63-2.44 (m, 2H), 2.39 (dd, J=7.7, 12.5 Hz, 1H), 2.07-1.72 (m, 11H), 1.68-1.40 (m, 3H).

2-(7-chloro-1H-indole-2-carbonyl)-N-((S)-1-cyano-2-((S)-2-oxopiperidin-3-yl)ethyl)-8,8-difluoro-2-azaspiro[4.5]decane-3-carboxamide (Isomer 2: 325 mg, 595.23 umol, 43.92% yield, 100% purity) as a white solid. MS (ESI) m/z 546.2 [M+H]+.

$^1$H NMR (400 MHz, MeOD-$d_4$) S ppm 7.64 (d, J=8.0 Hz, 1H), 7.28 (d, J=7.4 Hz, 1H), 7.20-6.81 (m, 2H), 5.02 (dd, J=6.2, 10.1 Hz, 1H), 4.66 (dd, J=7.9, 9.4 Hz, 1H), 4.08-3.81 (m, 2H), 3.23-3.00 (m, 2H), 2.55-2.23 (m, 3H), 2.02-1.72 (m, 10H), 1.71-1.59 (m, 3H), 1.58-1.44 (m, 1H).

Example 93. Synthesis of Viral Protease Inhibitor Compound 806a

Step 1: methyl (Z)-2-azido-3-(3-chloro-2-methoxy-phenyl)prop-2-enoate

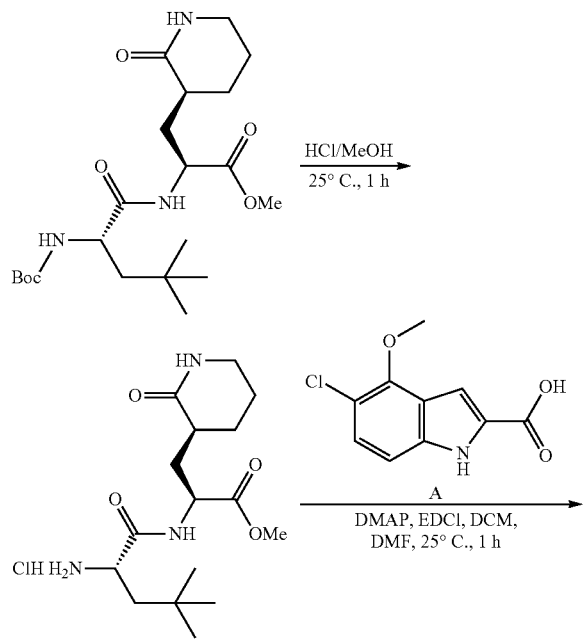

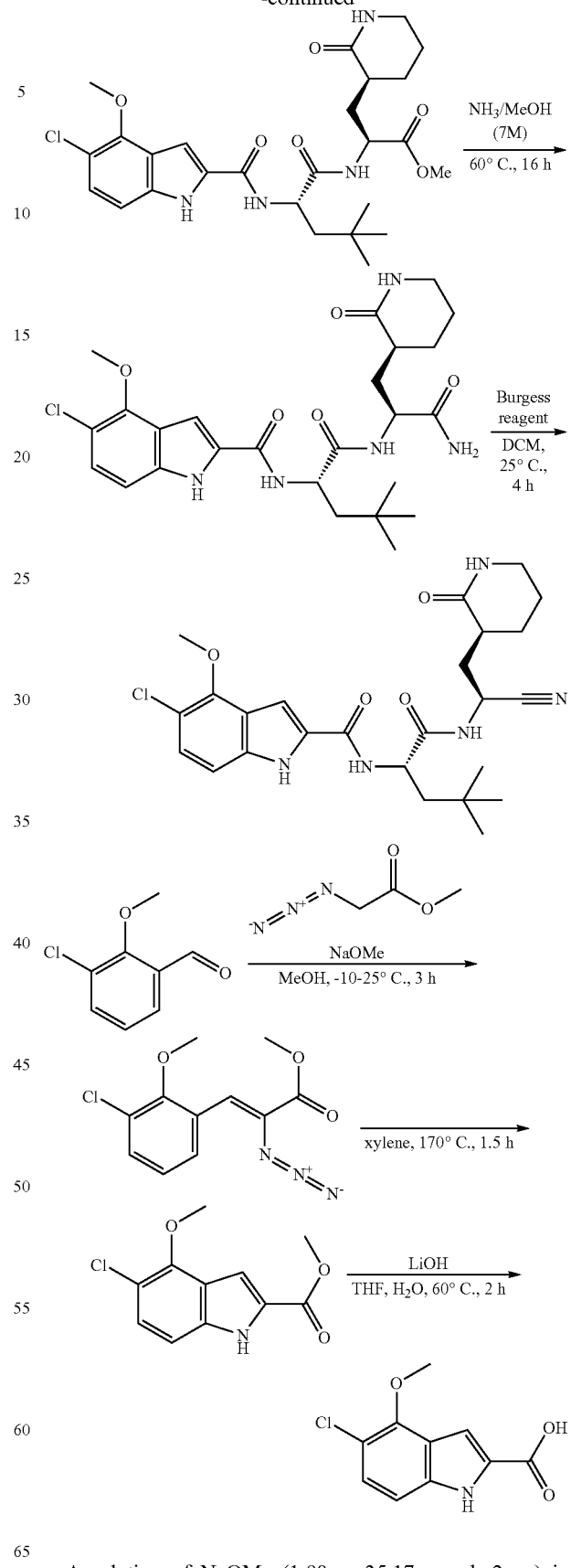

A solution of NaOMe (1.90 g, 35.17 mmol, 2 eq) in MeOH (20 mL) was cooled to −10° C., and a mixture 3-chloro-2-methoxy-benzaldehyde (3 g, 17.59 mmol, 1 eq) and methyl azide acetate (4.12 g, 35.17 mmol, 2 eq) in MeOH (10 mL) was added drop-wise. The mixture was stirred at 25° C. for 3 h. Upon completion, the reaction mixture was quenched by addition H₂O 5 (0 mL) at 0° C., and then diluted with H₂O (30 mL) and extracted with ethyl acetate (100 mL, which extracted as 50 mL*2). The combined organic layers were washed with brine (50 mL), dried over Na₂SO₄, filtered and concentrated under reduced pressure to give a residue. The residue was purified by column chromatography (SiO₂, petroleum ether/ethyl acetate=20/1 to 10/1) to afford (Z)-2-azido-3-(3-chloro-2-methoxy-phenyl)prop-2-enoate (2.1 g, 7.45 mmol, 42.38% yield, 95% purity) as a yellow solid.

Step 2: methyl 5-chloro-4-methoxy-1H-indole-2-carboxylate

Methyl (Z)-2-azido-3-(3-chloro-2-methoxy-phenyl)prop-2-enoate (2.1 g, 7.85 mmol, 1 eq) in xylene (20 mL), the mixture was stirred at 170° C. for 1.5 h. Upon completion, the reaction mixture was concentrated under reduced pressure to give a residue. The residue was purified by column chromatography (SiO₂, petroleum ether/ethyl acetate=10/1 to 5/1) to get the compound methyl 5-chloro-4-methoxy-1H-indole-2-carboxylate (1.7 g, 6.38 mmol, 81.37% yield, 90% purity) as a white solid.

Step 3: 5-chloro-4-methoxy-1H-indole-2-carboxylic acid

To a mixture of methyl 5-chloro-4-methoxy-1H-indole-2-carboxylate (1.2 g, 5.01 mmol, 1 eq) in THF (20 mL) and H₂O (10 mL) was added LiOH·H₂O (420.24 mg, 10.01 mmol, 2 eq). The mixture was stirred at 60° C. for 2 h. Upon completion, the pH of the reaction mixture was adjusted to pH=3 by addition HCl, and then diluted with H₂O (30 mL). The reaction was extracted with ethyl acetate (50 mL*2). The combined organic layers were washed with brine (50 mL), dried over Na₂SO₄, filtered and concentrated under reduced pressure to give a residue 5-chloro-4-methoxy-1H-indole-2-carboxylic acid (0.95 g, 4.00 mmol, 79.88% yield, 95% purity) as a white solid.

Step 4: methyl (2S)-2-[[(2S)-2-[(5-chloro-4-methoxy-1H-indole-2-carbonyl)amino]-4,4-dimethyl-pentanoyl]amino]-3-[(3S)-2-oxo-3-piperidyl]propanoate To a mixture of methyl (2S)-2-[[(2S)-2-amino-4,4-dimethyl-pentanoyl]amino]-3-[(3S)-2-oxo-3-piperidyl]propanoate (468 mg, 1.29 mmol, 1 eq, HCl) and 5-chloro-4-methoxy-1H-indole-2-carboxylic acid (290.19 mg, 1.29 mmol, 1 eq) in DMF (10 mL) and DCM (20 mL) was added EDCI (493.11 mg, 2.57 mmol, 2 eq) and DMAP (314.25 mg, 2.57 mmol, 2 eq). The mixture was stirred at 25° C. for 1 h. Upon completion, the reaction mixture was diluted with H₂O (100 mL) and extracted with ethyl acetate (200 mL, which was extracted as 100 mL*2). The combined organic layers were washed with HCl (1 M, 100 mL) and brine (100 mL), dried over Na₂SO₄, filtered and concentrated under reduced pressure to give a residue. The residue was purified by column chromatography (SiO2, petroleum ether/ethyl acetate=5/1 to 0/1) to get the compound methyl (2S)-2-[[(2S)-2-[(5-chloro-4-methoxy-1H-indole-2-carbonyl)amino]-4,4-dimethyl-pentanoyl]amino]-3-[(3S)-2-oxo-3-piperidyl]propanoate (600 mg, 1.02 mmol, 79.35% yield, 91% purity) as a white solid. MS (ESI) m/z 535.2/537.2 [M+H]⁺

Step 5: N-[(1S)-2-[[(1S)-1-cyano-2-[(3S)-2-oxopyrrolidin-3-yl]ethyl]amino]-1-(cyclopropylmethyl)-2-oxo-ethyl]-7-methoxy-1H-benzimidazole-2-carboxamide A mixture of methyl (2S)-2-[[(2S)-2-[(5-chloro-4-methoxy-1H-indole-2-carbonyl)amino]-4,4-dimethyl-pentanoyl]amino]-3-[(3S)-2-oxo-3-piperidyl]propanoate (450 mg, 841.07 umol, 1 eq) and NH₃/MeOH (7 M, 15 mL, 124.84 eq) was stirred at 60° C. for 16 h. Upon completion, the reaction mixture was concentrated under reduced pressure to afford N-[(1S)-1-[[(1S)-2-amino-2-oxo-1-[[(3S)-2-oxo-3-piperidyl]methyl]ethyl]carbamoyl]-3,3-dimethyl-butyl]-5-chloro-4-methoxy-1H-indole-2-carboxamide (440 mg, 719.20 umol, 85.51% yield, 85% purity) as a white solid. MS (ESI) m/z 520.3 [M+H]⁺

Step 6: 5-chloro-N-[(1S)-1-[[(1S)-1-cyano-2-[(3S)-2-oxo-3-piperidyl]ethyl]carbamoyl]-3,3-dimethyl-butyl]-4-methoxy-1H-indole-2-carboxamide To a mixture of N-[(1S)-1-[[(1S)-2-amino-2-oxo-1-[[(3S)-2-oxo-3-piperidyl]methyl]ethyl]carbamoyl]-3,3-dimethyl-butyl]-5-chloro-4-methoxy-1H-indole-2-carboxamide (440 mg, 846.12 umol, 1 eq) in DCM (6 mL) was added Burgess reagent (604.92 mg, 2.54 mmol, 3 eq). The mixture was stirred at 25° C. for 4 h. Upon completion, the reaction mixture was diluted with H₂O (20 mL) and then extracted with DCM (20 mL*2). The combined organic layers were concentrated and blow-drying by N₂ to give a residue. The residue was purified by neutral prep-HPLC (column: Kromasil C18 (250*50 mm*10 um); mobile phase: [water (10 mM NH₄HCO₃)-ACN]; B %: 30%-60%, 10 min) to afford 5-chloro-N-[(1S)-1-[[(1 S)-1-cyano-2-[(3S)-2-oxo-3-piperidyl]ethyl]carbamoyl]-3,3-dimethyl-butyl]-4-methoxy-1H-indole-2-carboxamide (220 mg, 430.07 umol, 50.83% yield, 98.134% purity) as a white solid. MS (ESI) m/z 502.2 [M+H]⁺.

¹H NMR (400 MHz, DMSO-d₆) δ=11.85 (br s, 1H), 8.96 (d, J=7.9 Hz, 1H), 8.63 (d, J=8.1 Hz, 1H), 7.67-7.38 (m, 2H), 7.24-7.05 (m, 2H), 5.16-4.92 (m, 1H), 4.63-4.42 (m, 1H), 4.11-4.02 (m, 3H), 3.14-3.00 (m, 2H), 2.36-2.17 (m, 2H), 1.88-1.62 (m, 5H), 1.59-1.29 (m, 2H), 0.94 (s, 9H),

Example 94. Synthesis of Viral Protease Inhibitor Compound 808

Step 1: methyl (Z)-2-azido-3-(2-chloro-3-methoxy-phenyl)prop-2-enoate

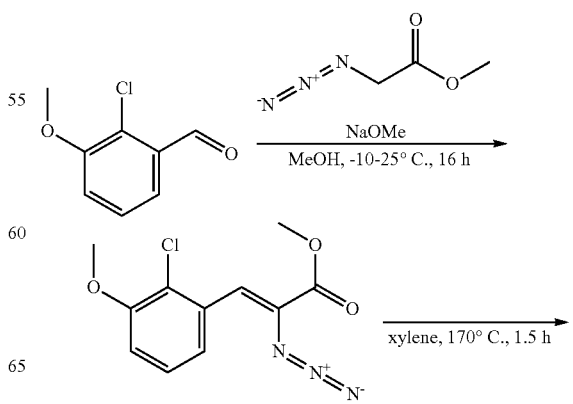

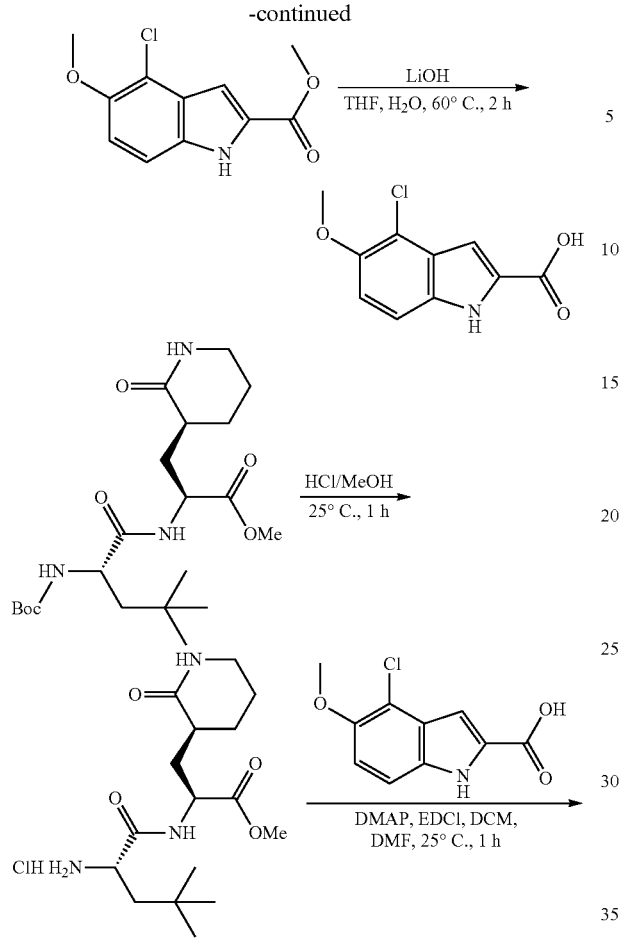

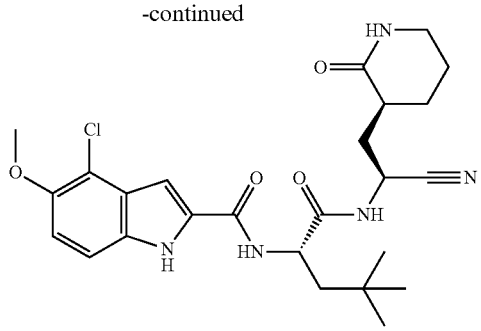

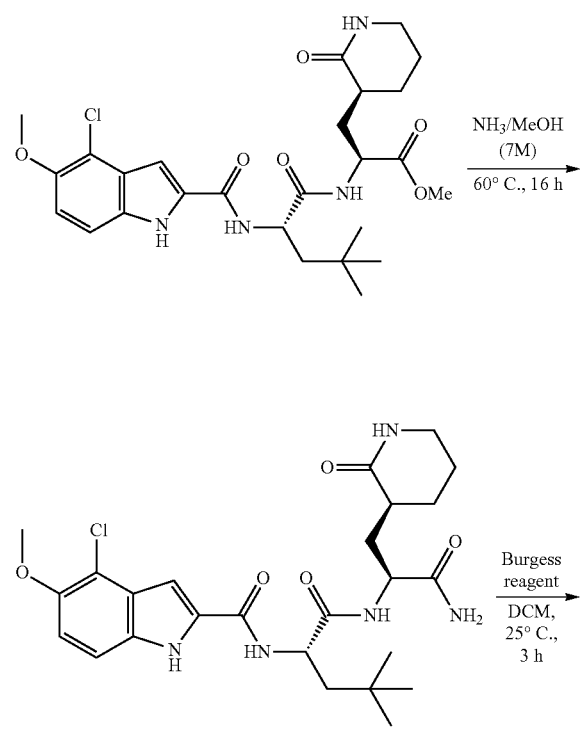

A mixture of 2-chloro-3-methoxy-benzaldehyde (4 g, 23.45 mmol, 1 eq) and NaOMe (2.53 g, 46.90 mmol, 2 eq) with MeOH (20 mL) was cooled to −10° C., and then a mixture of methyl azide acetate (5.49 g, 46.90 mmol, 2 eq) in MeOH (50 mL) was added dropwise to the solution. The mixture was stirred at 25° C. for 16 h, and a white solid was observed. Upon completion, the reaction mixture was filtered to give a residue compound methyl (Z)-2-azido-3-(2-chloro-3-methoxy-phenyl)prop-2-enoate (3 g, 10.09 mmol, 43.02% yield, 90% purity) as a white solid.

Step 2: methyl 4-chloro-5-methoxy-1H-indole-2-carboxylate

A solution of methyl (Z)-2-azido-3-(2-chloro-3-methoxy-phenyl)prop-2-enoate (1 g, 3.74 mmol, 1 eq) in xylene (20 mL) was warmed to 170° C., and stirred at 170° C. for 1.5 hours. Upon completion, the reaction mixture was concentrated under reduced pressure to give a residue. The residue was triturated with petroleum ether:ethyl acetate=5:1 at 25° C. to afford methyl 4-chloro-5-methoxy-1H-indole-2-carboxylate (450 mg, 1.13 mmol, 30.16% yield, 60% purity) as a yellow solid.

Step 3: 4-chloro-5-methoxy-1H-indole-2-carboxylic acid

To a mixture of methyl 4-chloro-5-methoxy-1H-indole-2-carboxylate (450.00 mg, 1.88 mmol, 1 eq) in THF (10 mL) and H$_2$O (5 mL) was added LiOH·H$_2$O (157.59 mg, 3.76 mmol, 2 eq). The mixture was stirred at 60° C. for 2 h. Upon completion, the pH of the reaction mixture was adjusted pH=3 by addition HCl, and then diluted with H$_2$O (30 mL) and extracted with ethyl acetate (50 mL*2). The combined organic layers were washed with brine (50 mL), dried over Na$_2$SO$_4$, filtered and concentrated under reduced pressure to give a residue compound 4-chloro-5-methoxy-1H-indole-2-carboxylic acid (320 mg, 992.78 umol, 52.87% yield, 70% purity) as a yellow solid.

Step 4: methyl (2S)-2-[[(2S)-2-amino-4,4-dimethyl-pentanoyl]amino]-3-[(3S)-2-oxo-3-piperidyl]propanoate A solution of methyl (2S)-2-[[(2S)-2-(tert-butoxycarbonylamino)-4,4-dimethyl-pentanoyl]amino]-3-[(3S)-2-oxo-3-piperidyl]propanoate (500 mg, 1.17 mmol, 1 eq) in HCl/MeOH (4 M, 50.00 mL, 171.01 eq) was stirred at 25° C. for 1 hr. Upon completion, the reaction mixture was concentrated under reduced pressure to give a residue compound methyl(2S)-2-[[(2S)-2-amino-4,4-dimethyl-pentanoyl]

amino]-3-[(3S)-2-oxo-3-piperidyl]propanoate (420 mg, 1.15 mmol, 98.69% yield, HCl) as a white solid.

Step 5: methyl (2S)-2-[[(2S)-2-[(4-chloro-5-methoxy-1H-indole-2-carbonyl)amino]-4,4-dimethyl-pentanoyl]amino]-3-[(3S)-2-oxo-3-piperidyl]propanoate To a mixture of methyl (2S)-2-[[(2S)-2-amino-4,4-dimethyl-pentanoyl]amino]-3-[(3S)-2-oxo-3-piperidyl]propanoate (420 mg, 1.15 mmol, 1 eq, HCl) and 4-chloro-5-methoxy-1H-indole-2-carboxylic acid (260.43 mg, 1.15 mmol, 1 eq) in DMF (10 mL) and DCM (20 mL) was added EDCI (442.53 mg, 2.31 mmol, 2 eq) and DMAP (282.02 mg, 2.31 mmol, 2 eq). The mixture was stirred at 25° C. for 1 h. Upon completion, the reaction mixture was filtered and then diluted with H₂O (100 mL) and extracted with ethyl acetate 300 mL (150 mL*2). The combined organic layers were washed with brine (100 mL), dried over Na₂SO₄, filtered and concentrated under reduced pressure to give a residue. The residue was purified by column chromatography (SiO₂, petroleum ether/ethyl acetate=3/1 to 0/1) to afford methyl (2S)-2-[[(2S)-2-[(4-chloro-5-methoxy-1H-indole-2-carbonyl)amino]-4,4-dimethyl-pentano yl]amino]-3-[(3S)-2-oxo-3-piperidyl]propanoate (350 mg, 588.75 umol, 51.01% yield, 90% purity) as a yellow solid. MS (ESI) m/z 535.3 [M+H]⁺

Step 6: N-[(1S)-1-[[(1S)-2-amino-2-oxo-1-[[(3S)-2-oxo-3-piperidyl]methyl]ethyl]carbamoyl]-3,3-dimethyl-butyl]-4-chloro-5-methoxy-1H-indole-2-carboxamide A mixture of methyl (2S)-2-[[(2S)-2-[(4-chloro-5-methoxy-1H-indole-2-carbonyl)amino]-4,4-dimethyl-pentano yl]amino]-3-[(3S)-2-oxo-3-piperidyl]propanoate (300.00 mg, 560.72 umol, 1 eq) and NH₃/MeOH (7 M, 10 mL, 124 eq) was stirred at 60° C. for 16 h in seal tube. The reaction mixture was concentrated under reduced pressure to give a residue compound N-[(1S)-1-[[(1S)-2-amino-2-oxo-1-[[(3S)-2-oxo-3-piperidyl]methyl]ethyl]carbamoyl]-3,3-dimethyl-butyl]-4-chloro-5-methoxy-1H-indole-2-carboxamide (290 mg, 501.90 umol, 89.51% yield, 90% purity) as a white solid. MS (ESI) m/z 520.3 [M+H]⁺

Step7: 4-chloro-N-[(1S)-1-[[(1S)-1-cyano-2-[(3S)-2-oxo-3-piperidyl]ethyl]carbamoyl]-3,3-dimethyl-butyl]-5-methoxy-1H-indole-2-carboxamide To a mixture of N-[(1S)-1-[[(1S)-2-amino-2-oxo-1-[[(3S)-2-oxo-3-piperidyl]methyl]ethyl] carbamoyl]-3,3-dimethyl-butyl]-4-chloro-5-methoxy-1H-indole-2-carboxamide (330 mg, 634.59 umol, 1 eq) in DCM (10 mL) was added Burgess reagent (453.69 mg, 1.90 mmol, 3 eq). The mixture was stirred at 25° C. for 3 h. Upon completion, the reaction mixture was diluted with H₂O (20 mL) and extracted with DCM (40 mL, which was extracted as 20 mL*2). The combined organic layers were concentrated by blow-drying by N₂ to give a residue. The residue was purified by neutral prep-HPLC (column: Waters Xbridge BEH C18 100*30 mm*10 um; mobile phase: [water (10 mM NH4HCO3)-ACN]; B %: 30%-60%, 10 min) to get the compound 4-chloro-N-[(1S)-1-[[(1S)-1-cyano-2-[(3S)-2-oxo-3-piperidyl] ethyl]carbamoyl]-3,3-dimethyl-butyl]-5-methoxy-1H-indole-2-carboxamide (140 mg, 276.09 umol, 43.51% yield, 99% purity) as a white solid. MS (ESI) m/z 502.2 [M+H]⁺.

¹H NMR (400 MHz, DMSO-d6) δ=11.74 (s, 1H), 8.89 (d, J=8.1 Hz, 1H), 8.68 (d, J=8.1 Hz, 1H), 7.51 (br s, 1H), 7.41-7.25 (m, 2H), 7.13 (d, J=8.9 Hz, 1H), 5.12-4.96 (m, 1H), 4.52 (dt, J=3.8, 8.4 Hz, 1H), 3.91-3.76 (m, 3H), 3.14-2.95 (m, 2H), 2.37-2.13 (m, 2H), 1.90-1.29 (m, 7H), 1.01-0.81 (m, 9H)

Example 95. Synthesis of Viral Protease Inhibitor Compound 810

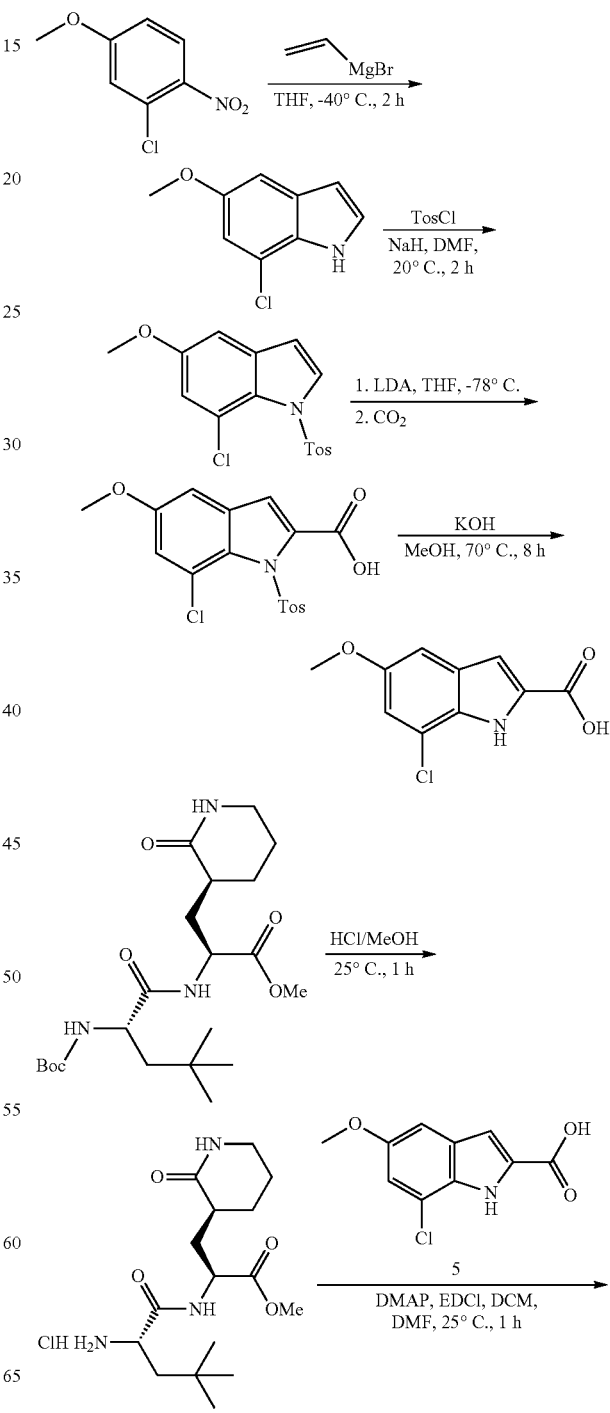

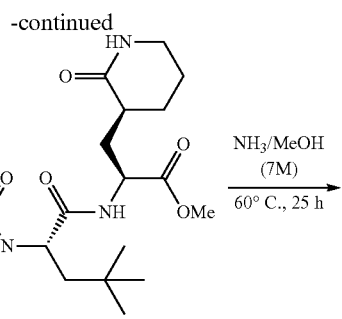

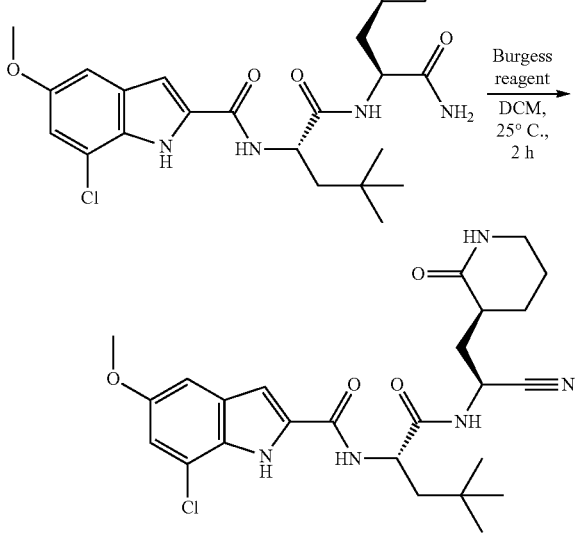

tolylsulfonyl)indole (2800 mg, 8.34 mmol, 72.11% yield) as a brown solid. MS (ESI) m/z 336.3 [M+H]+

Step 3: 7-chloro-5-methoxy-1-(p-tolylsulfonyl)indole-2-carboxylic acid

To a solution of 7-chloro-5-methoxy-1-(p-tolylsulfonyl)indole (2800 mg, 8.34 mmol, 1 eq) in THF (40 mL) was added LDA (1 M, 16.68 mL, 2 eq) at −70° C. and the solution was stirred for 2.5 h at −70° C. Upon completion, the solution was poured into dry ice quickly and diluted with $H_2O$ (80 mL) and the solution was concentrated and extracted with ethyl acetate (80 mL) to recycle reactant 3. The water layer was acidified to pH=5-6 with HCl (con) and extracted with ethyl acetate (90 mL*2) and dried over $Na_2SO_4$ and concentrated to give crude 7-chloro-5-methoxy-1-(p-tolylsulfonyl)indole-2-carboxylic acid (2300 mg, crude) as a brown solid. The crude was used directly for the next step. MS (ESI) n/z 380.2 [M+H]+

Step 4: 7-chloro-5-methoxy-1H-indole-2-carboxylic acid

A solution of 7-chloro-5-methoxy-1-(p-tolylsulfonyl)indole-2-carboxylic acid (2100 mg, 5.53 mmol, 1 eq) and KOH (682.51 mg, 12.16 mmol, 14.41 uL, 2.2 eq) in MeOH (30 mL) was stirred for 8 h at 70° C. Upon completion, the solution was concentrated and diluted with $H_2O$ (40 mL) and acidified to pH=5-6 with HCl (1M) and filtered and the cake was collected to give 7-chloro-5-methoxy-1H-indole-2-carboxylic acid (570 mg, crude) as a brown solid. The crude was used directly for the next step. MS (ESI) m/z 226.3 [M+H]+

Step 5: methyl (2S)-2-[[(2S)-2-amino-4,4-dimethyl-pentanoyl]amino]-3-[(3S)-2-oxo-3-piperidyl]propanoate; hydrochloride A solution of methyl (2S)-2-[[(2S)-2-(tert-butoxycarbonylamino)-4,4-dimethyl-pentanoyl]amino]-3-[(3S)-2-oxo-3-piperidyl]propanoate (500 mg, 1.17 mmol, 1 eq) in HCl/MeOH (20 mL) was stirred for 1 h at 25° C. Upon completion, the solution was concentrated to give crude product methyl (2S)-2-[[(2S)-2-amino-4,4-dimethyl-pentanoyl]amino]-3-[(3S)-2-oxo-3-piperidyl]propanoate; hydrochloride (420 mg, crude) as an off-white solid. The crude was used directly for the next step. MS (ESI) m/z 364.3 [M+H]+

Step 1: 7-chloro-5-methoxy-1H-indole

To a solution of 2-chloro-4-methoxy-1-nitro-benzene (4300 mg, 22.92 mmol, 1 eq) in THF (70 mL) was added bromo(vinyl)magnesium (1 M, 80.23 mL, 3.5 eq) at −40° C. The solution was stirred for 2 h at −40° C. Upon completion, the solution was poured into $NH_4Cl$ (200 mL) and concentrated and extracted with ethyl acetate (80 mL*3) and concentrated to give a crude. The crude was purified by column ($SiO_2$, petroleum ether:ethyl acetate=30:1 to 10:1) to give product 7-chloro-5-methoxy-1H-indole (2100 mg, 11.56 mmol, 50.44% yield) as a brown oil. MS (ESI) m/z 182.1 [M+H]+.

Step 2: 7-chloro-5-methoxy-1-(p-tolylsulfonyl)indole

To a solution of 7-chloro-5-methoxy-1H-indole (2100 mg, 11.56 mmol, 1 eq) in DMF (25 mL) was added NaH (739.94 mg, 18.50 mmol, 60% purity, 1.6 eq) at 0° C. The solution was stirred for 0.5 h at 20° C. 4-Methylbenzenesulfonyl chloride (2.09 g, 10.98 mmol, 0.95 eq) was added and the solution was stirred for 1.5 h at 20° C. Upon completion, the solution was diluted with $H_2O$ (60 mL) and extracted with ethyl acetate (60 mL*3) and then washed with brine (60 mL*2) and concentrated to give crude. The crude was purified by column ($SiO_2$, petroleum ether:ethyl acetate=30:1 to 2:1) to give 7-chloro-5-methoxy-1-(p-

Step 6: methyl (2S)-2-[[(2S)-2-[(7-chloro-5-methoxy-1H-indole-2-carbonyl)amino]-4,4-dimethyl-pentanoyl]amino]-3-[(3S)-2-oxo-3-piperidyl]propanoate A solution of methyl (2S)-2-[[(2S)-2-amino-4,4-dimethyl-pentanoyl]amino]-3-[(3S)-2-oxo-3-piperidyl]propanoate; hydrochloride (420 mg, 1.15 mmol, 1 eq) and DMAP (282.02 mg, 2.31 mmol, 2 eq) in DCM (20 mL) and DMF (10 mL) was added 7-chloro-5-methoxy-1H-indole-2-carboxylic acid (299.49 mg, 1.33 mmol, 1.15 eq) and EDCI (442.54 mg, 2.31 mmol, 2 eq). The reaction was stirred for 1 h at 25° C. Upon completion, the solution was diluted with $H_2O$ (40 mL), extracted with ethyl acetate (50 mL*3), and washed with brine (80 mL*2) and concentrated to give crude product. The crude was purified by column ($SiO_2$, ethyl acetate:MeOH=1:0 to 10:1) to give product methyl(2S)-2-[[(2S)-2-[(7-chloro-5-methoxy-1H-indole-2- carbonyl)amino]-4,4-dimethyl-pentanoyl]amino]-3-[(3S)-2-oxo-3-piperidyl]propanoate (370 mg, 691.55 umol, 59.91% yield) as a yellow solid. MS (ESI) m/z 535.3 [M+H]$^+$ Step 7: N-[(1S)-1-[[(1S)-2-amino-2-oxo-1-[[(3S)-2-oxo-3-piperidyl]methyl]ethyl]carbamoyl]-3,3-dimethyl-butyl]-7-chloro-5-methoxy-1H-indole-2-carboxamide A solution of methyl (2S)-2-[[(2S)-2-[(7-chloro-5-methoxy-1H-indole-2-carbonyl)amino]-4,4-dimethyl-pentanoyl]amino]-3-[(3S)-2-oxo-3-piperidyl]propanoate (370 mg, 691.55 umol, 1 eq) in NH$_3$/MeOH (7 M, 16.44 mL, 166.45 eq) was stirred for 25 h at 60° C. Upon completion, the solution was concentrated to give N-[(1S)-1-[[(1S)-2-amino-2-oxo-1-[[(3S)-2-oxo-3-piperidyl]methyl]ethyl]carbamoyl]-3,3-dimethyl-butyl]-7-chloro-5-methoxy-1H-indole-2-carboxamide (350 mg, crude) as an off-white solid. The crude was used directly for the next step. MS (ESI) m/z 520.3 [M+H]$^+$ Step 8: 7-chloro-N-[(1S)-1-[[(1S)-1-cyano-2-[(3S)-2-oxo-3-piperidyl]ethyl]carbamoyl]-3,3-dimethyl-butyl]-S-methoxy-1H-indole-2-carboxamide A solution of N-[(1S)-1-[[(1S)-2-amino-2-oxo-1-[[(3S)-2-oxo-3-piperidyl]methyl]ethyl]carbamoyl]-3,3-dimethyl-butyl]-7-chloro-5-methoxy-1H-indole-2-carboxamide (350 mg, 673.05 umol, 1 eq) and Burgess reagent (641.57 mg, 2.69 mmol, 4 eq) in DCM (20 mL) was stirred for 2 h at 25° C. Upon completion, the solution was washed with brine (30 mL*2) and blow dried with N$_2$ to give crude product. The crude was purified by prep-HPLC (Column: Waters Xbridge Prep OBD C18 150*40 mm*10 um; mobile phase: [water (0.05% NH$_3$H$_2$O+10 mM NH$_4$HCO$_3$)-ACN]; B %: 30%-60%, 8 min) to afford 7-chloro-N-[(1S)-1-[[(1S)-1-cyano-2-[(3S)-2-oxo-3-piperidyl]ethyl]carbamoyl]-3,3-dimethyl-butyl]-5-methoxy-1H-indole-2-carboxamide (100 mg, 199.20 umol, 29.60% yield) as a white solid. MS (ESI) m/z 502.1 [M+H]$^+$.

$^1$H NMR (400 MHz, DMSO-d$_6$) δ=11.55 (br s, 1H), 9.11-8.94 (m, 1H), 8.64 (br d, J=8.4 Hz, 1H), 7.52 (br s, 1H), 7.17-7.08 (m, 2H), 6.98 (d, J=2.0 Hz, 1H), 5.27-4.92 (m, 1H), 4.69-4.37 (m, 1H), 3.76 (s, 3H), 3.05 (br s, 2H), 2.30-2.16 (m, 2H), 2.06 (s, 1H), 1.83-1.66 (m, 4H), 1.57-1.32 (m, 2H),

Example 96. Synthesis of Viral Protease Inhibitor Compound 812

Step 1: methyl (2S)-2-[[(2S)-2-(tert-butoxycarbonylamino)-3-cyclopropyl-propanoyl]amino]-3-[(3S)-2-oxo-3-piperidyl]propanoate

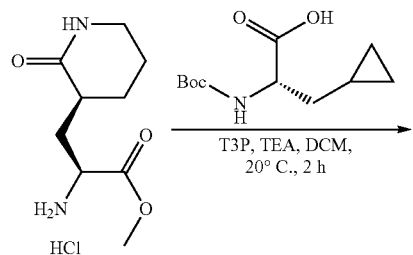

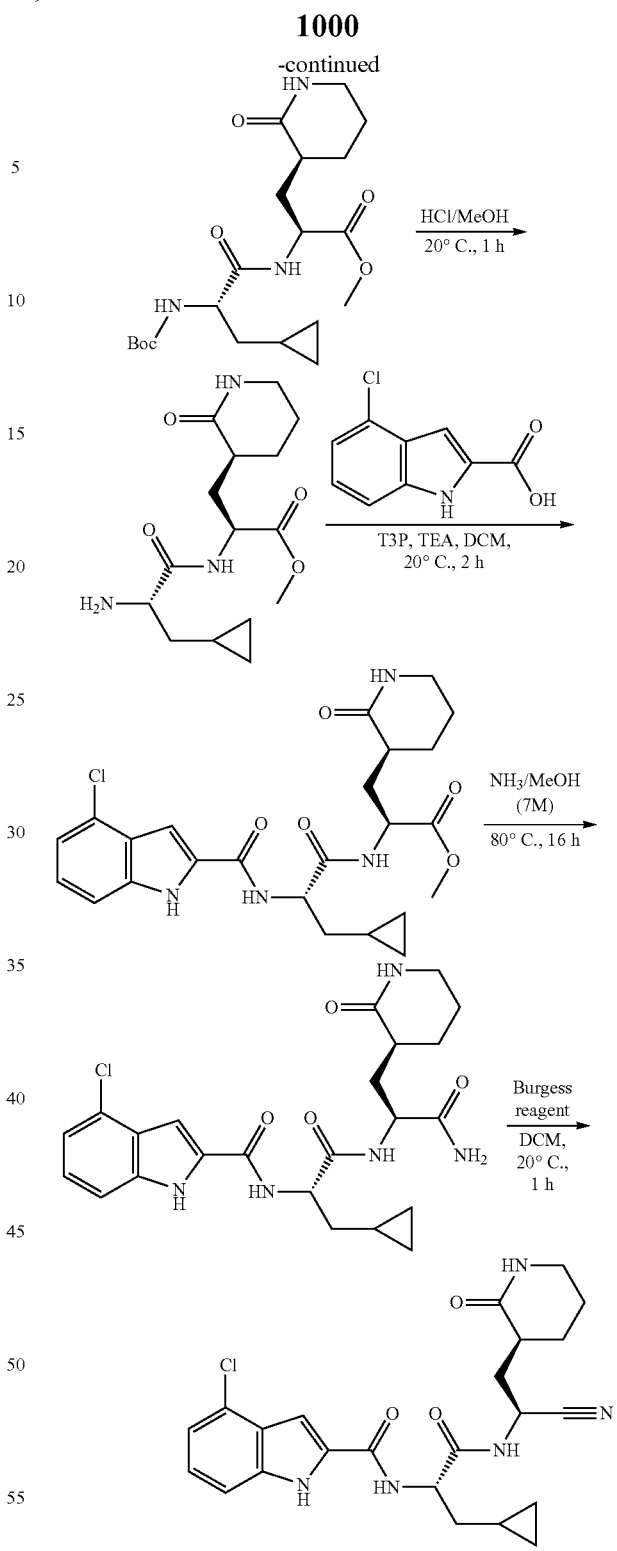

To a solution of methyl (2S)-2-amino-3-[(3S)-2-oxo-3-piperidyl]propanoate (1 g, 4.22 mmol, 1 eq, HCl) and (2S)-2-(tert-butoxycarbonylamino)-3-cyclopropyl-propanoic acid (968.64 mg, 4.22 mmol, 1 eq), TEA (1.28 g, 12.67 mmol, 1.76 mL, 3 eq) in DCM (15 mL) was added T3P (8.07 g, 12.67 mmol, 7.54 mL, 50% purity, 3 eq). The mixture was stirred at 20° C. for 2 h. Upon completion, the reaction mixture was quenched by addition H$_2$O (20 mL) at 0° C., the combined organic layers were washed with DCM (10 mL*3), dried over Na$_2$SO$_4$, filtered and concentrated under reduced pressure to give a residue. The residue was purified by column chromatography (SiO$_2$, petroleum ether/ethyl acetate=2/1 to 0/1) to give methyl (2S)-2-[[(2S)-2-(tert-butoxycarbonylamino)-3-cyclopropyl-propanoyl]amino]-3-[(3S)-2-oxo-3-piperidyl]propanoate (1.08 g, 2.05 mmol, 48.46% yield, 78% purity) as a yellow oil. MS (ESI) m/z 413.2 [M+H]$^+$.

Step 2: methyl (2S)-2-[[(2S)-2-amino-3-cyclopropyl-propanoyl]amino]-3-[(3S)-2-oxo-3-piperidyl]propanoate A solution of methyl (2S)-2-[[(2S)-2-(tert-butoxycarbonylamino)-3-cyclopropyl-propanoyl]amino]-3-[(3S)-2-oxo-3-piperidyl]propanoate (1.04 g, 2.53 mmol, 1 eq) in HCl/MeOH (15 mL) was stirred at 20° C. for 1 h. Upon completion, the reaction mixture was concentrated under reduced pressure to remove solvent to give methyl (2S)-2-[[(2S)-2-amino-3-cyclopropyl-propanoyl]amino]-3-[(3S)-2-oxo-3-piperidyl]propanoate (879 mg, crude, HCl) as a yellow oil. MS (ESI) m/z 313.2 [M+H]$^+$ Step 3: methyl (2S)-2-[[(2S)-2-[(4-chloro-1H-indole-2-carbonyl)amino]-3-cyclopropyl-propanoyl]amino]-3-[(3S)-2-oxo-3-piperidyl]propanoate To a solution of methyl (2S)-2-[[(2S)-2-amino-3-cyclopropyl-propanoyl]amino]-3-[(3S)-2-oxo-3-piperidyl]propanoate (879 mg, 2.82 mmol, 1 eq) and 4-chloro-1H-indole-2-carboxylic acid (552.18 mg, 2.82 mmol, 1 eq) TEA (856.96 mg, 8.47 mmol, 1.18 mL, 3 eq) in DCM (10 mL) was added T3P (5.39 g, 8.47 mmol, 5.04 mL, 50% purity, 3 eq). The mixture was stirred at 20° C. for 2 h. Upon completion, the reaction mixture was quenched by addition H$_2$O (20 mL) at 0° C., the combined organic layers were washed with DCM (10 mL*3), dried over Na$_2$SO$_4$, filtered and concentrated under reduced pressure to give a residue. The residue was purified by column chromatography (SiO$_2$, petroleum ether/ethyl acetate=2/1 to 0/1) to afford methyl (2S)-2-[[(2S)-2-[(4-chloro-1H-indole-2-carbonyl)amino]-3-cyclopropyl-propanoyl]amino]-3-[(3S)-2-oxo-3-piperidyl]propanoate (636 mg, 1.04 mmol, 36.86% yield, 80% purity) as a yellow solid. MS (ESI) m/z 489.2 [M+H]$^+$ Step 4: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-chloro-1H-indole-2-carboxamide A solution of methyl (2S)-2-[[(2S)-2-[(4-chloro-1H-indole-2-carbonyl)amino]-3-cyclopropyl-propanoyl]amino]-3-[(3S)-2-oxo-3-piperidyl]propanoate (621 mg, 1.27 mmol, 1 eq) in NH$_3$/MeOH (7 M, 5 mL, 27.56 eq) was stirred at 80° C. for 16 h. Upon completion, the reaction mixture was concentrated under reduced pressure to give N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-chloro-1H-indole-2-carboxamide (460 mg, crude) as a yellow solid. MS (ESI) m/z 474.2 [M+H]$^+$.

Step 5: 4-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-chloro-1H-indole-2-carboxamide (440 mg, 928.37 umol, 1 eq) in DCM (8 mL) was added Burgess reagent (663.70 mg, 2.79 mmol, 3 eq). The mixture was stirred at 20° C. for 1 h. Upon completion, the reaction mixture was concentrated under reduced pressure to give 4-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide (105.2 mg, 229.35 umol, 24.70% yield, 99.4% purity) as a white solid. MS (ESI) m/z 456.2 [M+H]$^+$.

$^1$H NMR (400 MHz, DMSO-d$_6$) δ=11.95 (s, 1H), 8.92 (d, J=8.4 Hz, 1H), 8.81-8.70 (m, 1H), 7.55-7.49 (m, 1H), 7.44-7.37 (m, 2H), 7.24-7.07 (m, 2H), 5.14-5.00 (m, 1H), 4.54-4.40 (m, 1H), 3.18-2.99 (m, 2H), 2.31-2.21 (m, 2H), 1.93-1.66 (m, 4H), 1.61-1.34 (m, 3H), 0.89-0.76 (m, 1H), 0.52-0.33 (m, 2H), 0.24-0.04 (m, 2H)

Example 97. Synthesis of Viral Protease Inhibitor Compound 814

Step 1: (2S)-methyl 3-((S)-2-oxopyrrolidin-3-yl)-2-(6-azaspiro[3.4]octane-7-carboxamido)propanoate

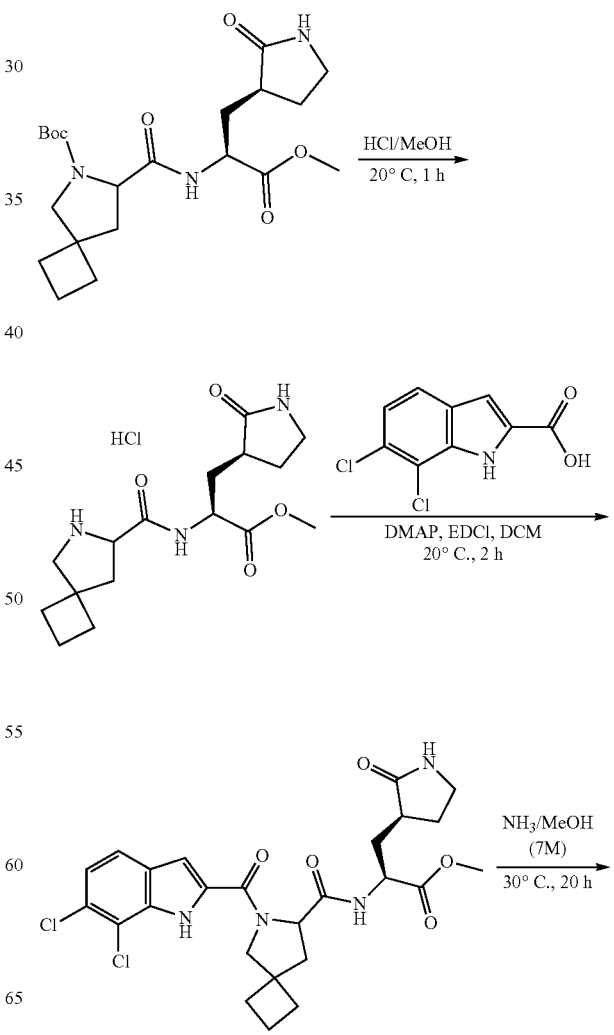

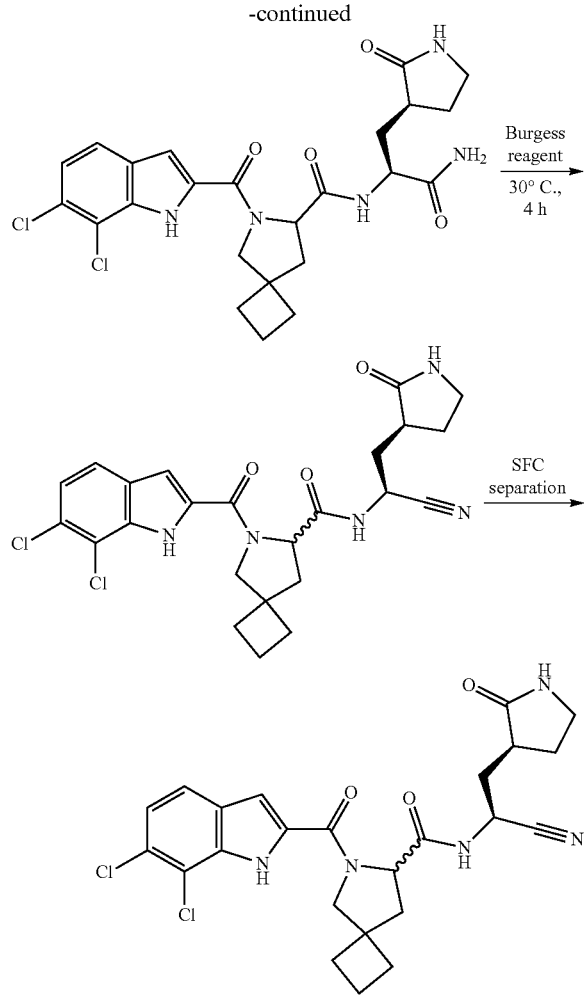

A solution of tert-butyl 7-(((S)-1-methoxy-1-oxo-3-((S)-2-oxopyrrolidin-3-yl)propan-2-yl) carbamoyl)-6-azaspiro[3.4]octane-6-carboxylate (1.4 g, 3.31 mmol, 1 eq) in HCl/MeOH (4 M, 14 mL) was stirred at 20° C. for 1 h. Upon the reaction completion, the mixture was concentrated in vacuum to obtain (2S)-methyl 3-((S)-2-oxopyrrolidin-3-yl)-2-(6-azaspiro[3.4] octane-7-carboxamido) propanoate (1.29 g, crude) as a light yellow solid.

Step 2: (2S)-methyl2-(6-(6,7-dichloro-1H-indole-2-carbonyl)-6-azaspiro[3.4]octane-7-carboxamido)-3-((S)-2-oxopyrrolidin-3-yl)propanoate To a solution of (2S)-methyl 3-((S)-2-oxopyrrolidin-3-yl)-2-(6-azaspiro[3.4]octane-7-carboxamido) propanoate (1.14 g, 2.22 mmol, 70% purity, 1 eq, HCl) in DCM (25 mL) was added 6,7-dichloro-1H-indole-2-carboxylic acid (612.19 mg, 2.66 mmol, 1.2 eq) and DMAP (541.85 mg, 4.44 mmol, 2 eq) and EDCI (850.23 mg, 4.44 mmol, 2 eq). The mixture was stirred at 20° C. for 2 h. Upon the reaction completion, the residue was poured into water (60 mL) and was extracted with DCM (20 mL*3). The combined organic phase was washed with brine (10 mL), dried with anhydrous Na$_2$SO$_4$, filtered and concentrated in vacuum and was purified by prep-TLC (SiO$_2$, DCM:MeOH=10:1, Rf=0.35) to obtained (2S)-methyl 2-(6-(6,7-dichloro-1H-indole-2-carbonyl)-6-azaspiro[3.4]octane-7-carboxamido)-3-((S)-2-oxopyrrolidin-3-yl) propanoate (800 mg, 1.48 mmol, 66.70% yield, 99% purity) as a light yellow solid. MS (ESI) m/z 535.2 [M+H]$^+$ Step 3: N-((S)-1-amino-1-oxo-3-((S)-2-oxopyrrolidin-3-yl)propan-2-yl)-6-(6,7-dichloro-1H-indole-2-carbonyl)-6-azaspiro[3.4]octane-7-carboxamide A solution of (2S)-methyl 2-(6-(6,7-dichloro-1H-indole-2-carbonyl)-6-azaspiro[3.4]octane-7-carboxamido)-3-((S)-2-oxopyrrolidin-3-yl) propanoate (270 mg, 504.28 umol, 1 eq) in NH$_3$/MeOH (6 mL, 7 M) was stirred at 30° C. for 20 h. Upon the reaction completement, the mixture was concentrated in vacuum to obtained N-((S)-1-amino-1-oxo-3-((S)-2-oxopyrrolidin-3-yl) propan-2-yl)-6-(6,7-dichloro-1H-indole-2-carbonyl)-6-azaspiro[3.4]octane-7-carboxamide (800 mg, crude) as a light yellow solid. MS (ESI) m/z 520.2 [M+H]$^+$ Step 4: N-((S)-1-cyano-2-((S)-2-oxopyrrolidin-3-yl)ethyl)-6-(6,7-dichloro-1H-indole-2-carbonyl)-6-azaspiro[3.4]octane-7-carboxamide To a solution of N-((S)-1-amino-1-oxo-3-((S)-2-oxopyrrolidin-3-yl) propan-2-yl)-6-(6,7-dichloro-1H-indole-2-carbonyl)-6-azaspiro[3.4]octane-7-carboxamide (800 mg, 1.54 mmol, 1 eq) in DCM (15 mL) was added Burgess reagent (1.10 g, 4.61 mmol, 3 eq), and the mixture was stirred at 30° C. for 4 h. Upon the reaction completion, the mixture was quenched by H$_2$O (2 mL) and dried by blowing N$_2$ and was purified by prep-HPLC (column: Waters Xbridge C18 150*50 mm*10 um; mobile phase: [water (10 mM NH$_4$HCO$_3$)-ACN]; B %: 35%-65%, 10 min) to obtained N-((S)-1-cyano-2-((S)-2-oxopyrrolidin-3-yl)ethyl)-6-(6,7-dichloro-1H-indole-2-carbonyl)-6-azaspiro[3.4]octane-7-carboxamide (380 mg, 756.38 umol, 49.20% yield) as a white solid. MS (ESI) m/z 502.2 [M+H]$^+$.

Step 5: N-((S)-1-cyano-2-((S)-2-oxopyrrolidin-3-yl)ethyl)-6-(6,7-dichloro-1H-indole-2-carbonyl)-6-azaspiro[3.4]octane-7-carboxamide The N-((S)-1-cyano-2-((S)-2-oxopyrrolidin-3-yl) ethyl)-6-(6,7-dichloro-1H-indole-2-carbonyl)-6-azaspiro[3.4]octane-7-carboxamide was separated by SFC (column: DAICEL CHIRALPAK AS (250 mm*30 mm, 10 um); mobile phase: [0.1% NH$_3$H$_2$O MEOH]; B %: 45%-45%, 15 min) to obtained N-((S)-1-cyano-2-((S)-2-oxopyrrolidin-3-yl) ethyl)-6-(6,7-dichloro-1H-indole-2-carbonyl)-6-azaspiro [3.4]octane-7-carboxamide (Isomer 1: 110 mg, 218.95 umol, 28.95% yield, 100% purity) as a white solid. MS (ESI) m/z 502.1 [M+H]$^+$ $^1$H NMR (400 MHz, MeOD-d$_4$) δ ppm 7.62 (d, J=8.6 Hz, 1H), 7.23 (d, J=8.6 Hz, 1H), 7.17 (s, 1H), 5.01 (dd, J=5.8, 10.3 Hz, 1H), 4.58 (t, J=7.6 Hz, 1H), 4.08-3.80 (m, 2H), 3.15-2.58 (m, 1H), 2.55-2.15 (m, 5H), 2.11-1.74 (m, 9H).

To obtain N-((S)-1-cyano-2-((S)-2-oxopyrrolidin-3-yl) ethyl)-6-(6,7-dichloro-1H-indole-2-carbonyl)-6-azaspiro [3.4]octane-7-carboxamide (Isomer 2: 85 mg, 169.19 umol, 22.37% yield, 100% purity) after repurification by prep-HPLC (column: Waters Xbridge BEH C18 100*25 mm*5 um; mobile phase: [water (10 mM NH$_4$HCO$_3$)-ACN]; B %: 30%-65%, 10 min) as a white solid. MS (ESI) m/z 502.1 [M+H]$^+$ $^1$H NMR (400 MHz, MeOD-d$_4$) δ ppm 7.61 (d, J=8.6 Hz, 1H), 7.24-7.15 (m, 1H), 7.13 (s, 1H), 5.09-4.90 (m, 1H), 4.78-4.51 (m, 1H), 4.06-3.72 (m, 2H), 2.83-2.63 (m, 1H), 2.61-2.28 (m, 3H), 2.22-1.76 (m, 10H), 1.72-1.40 (m, 1H).

Example 98. Synthesis of Viral Protease Inhibitor Compound 171

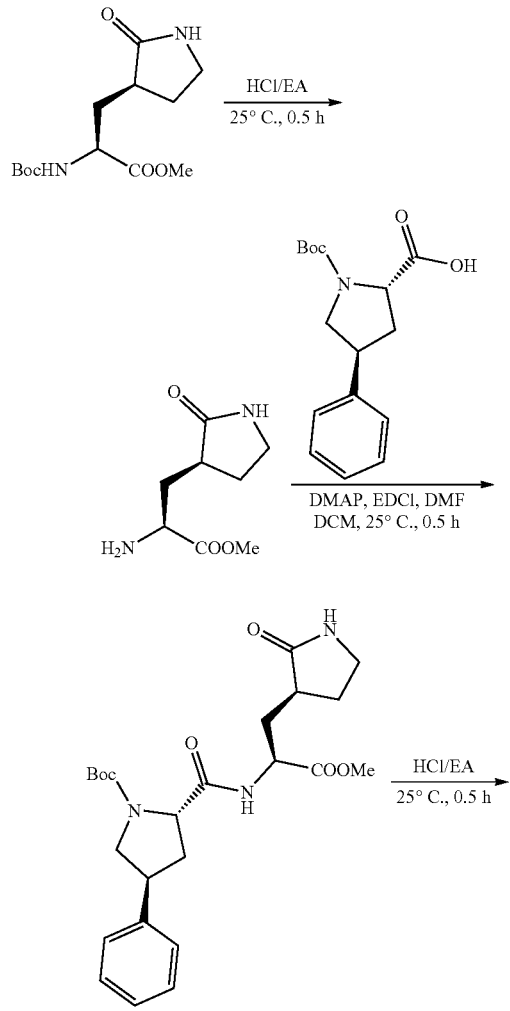

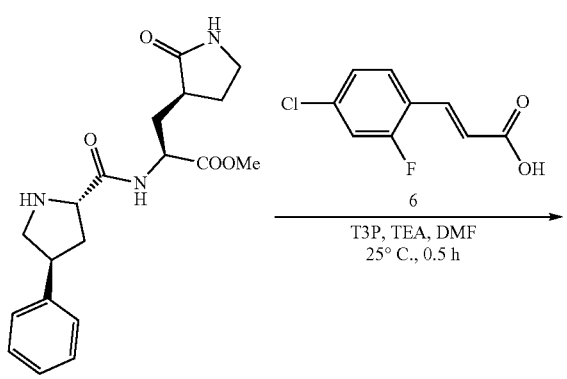

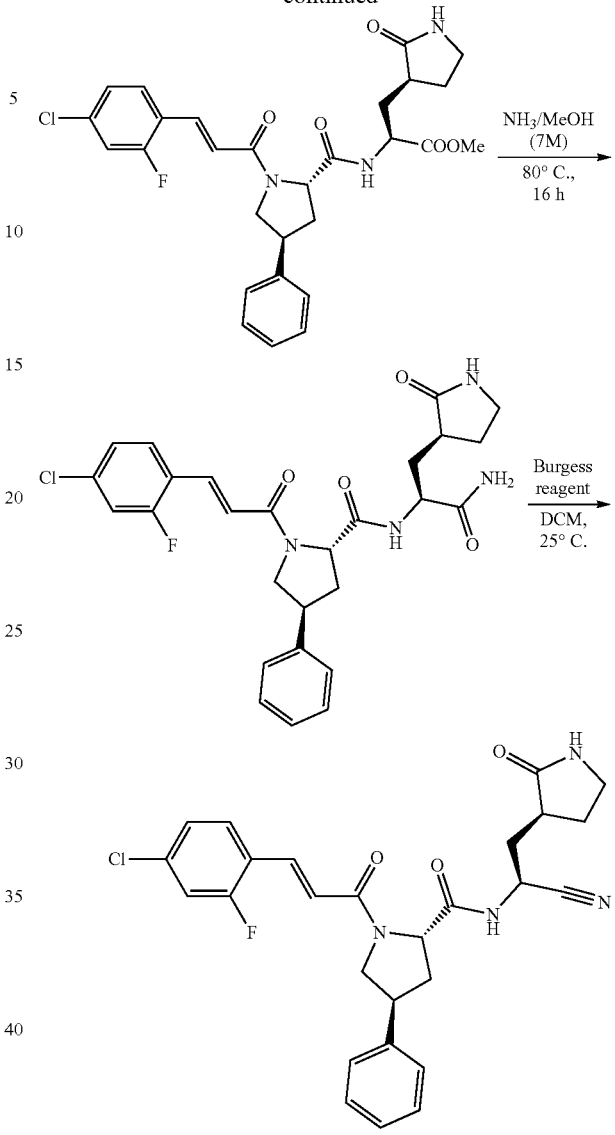

A mixture of methyl (2S)-2-(tert-butoxycarbonylamino)-3-[(3S)-2-oxopyrrolidin-3-yl]propanoate (0.55 g, 1.92 mmol, 1 eq) and HCl/EtOAc (4 M, 10 mL, 20.82 eq) was stirred at 25° C. for 0.5 h. Upon completion, the reaction mixture was concentrated under reduced pressure to give (S)-methyl 2-amino-3-((S)-2-oxopyrrolidin-3-yl)propanoate (0.35 g, crude) as a yellow oil.

Step 2: (2S,4S)-tert-butyl 2-(((S)-1-methoxy-1-oxo-3-((S)-2-oxopyrrolidin-3-yl)propan-2-yl)carbamoyl)-4-phenylpyrrolidine-1-carboxylate A mixture of (S)-methyl 2-amino-3-((S)-2-oxopyrrolidin-3-yl)propanoate (0.15 g, 805.55 umol, 1 eq), (2S,4S)-1-tert-butoxycarbonyl-4-phenyl-pyrrolidine-2-carboxylic acid (234.69 mg, 805.55 umol, 1 eq), DMAP (196.83 mg, 1.61 mmol, 2 eq), EDCI (308.85 mg, 1.61 mmol, 2 eq) in DMF (1 mL) and DCM (2 mL) was stirred at 25° C. for 0.5 h. Upon completion, the reaction mixture was diluted with water (10 mL) and extracted with ethyl acetate (5 mL*3). The combined organic layers were dried over Na₂SO₄, filtered and concentrated under reduced pressure to give a residue. The residue was purified by column chromatography (SiO$_2$, petroleum ether:ethyl acetate=2:1 to 0:1) to give (2S,4S)-tert-butyl 2-[[(1S)-2-methoxy-2-oxo-1-[[(3S)-2-oxopyrrolidin-3-yl]methyl]ethyl]carbamoyl]-4-phenyl-pyrrolidine-1-carboxylate (0.25 g, 500.51 umol, 62.13% yield, 92% purity) as a colorless oil. MS (ESI) m/z 460.1 [M+H]$^+$.

Step 3: (S)-methyl 3-((S)-2-oxopyrrolidin-3-yl)-2-((2S,4S)-4-phenylpyrrolidine-2-carboxamido)propanoate A mixture of tert-butyl (2S,4S)-2-[[(1S)-2-methoxy-2-oxo-1-[[(3S)-2-oxopyrrolidin-3-yl]methyl]ethyl]carbamoyl]-4-phenyl-pyrrolidine-1-carboxylate (0.25 g, 544.03 umol, 1 eq) and HCl/EtOAc (4 M, 10 mL, 73.53 eq) was stirred at 25° C. for 0.5 h. Upon completion, the reaction mixture was concentrated under reduced pressure to give methyl (2S)-3-[(3S)-2-oxopyrrolidin-3-yl]-2-[[(2S,4S)-4-phenylpyrrolidine-2-carbonyl]amino]propanoate (0.2 g, crude) as a yellow oil. MS (ESI) m/z 360.1 [M+H]$^+$.

Step 4: (S)-methyl 2-((2S,4S)-1-((E)-3-(4-chloro-2-fluorophenyl)acryloyl)-4-phenylpyrrolidine-2-carboxamido)-3-((S)-2-oxopyrrolidin-3-yl)propanoate A mixture of methyl (2S)-3-[(3S)-2-oxopyrrolidin-3-yl]-2-[[(2S,4S)-4-phenylpyrrolidine-2-carbonyl]amino]propanoate (0.17 g, 472.99 umol, 1 eq), (E)-3-(4-chloro-2-fluoro-phenyl)prop-2-enoic acid (94.88 mg, 472.99 umol, 1 eq), T3P (451.48 mg, 709.48 umol, 421.95 uL, 50% purity, 1.5 eq), TEA (143.58 mg, 1.42 mmol, 197.50 uL, 3 eq) in DMF (4 mL) was degassed and stirred at 25° C. for 0.5 h. Upon completion, the reaction mixture was diluted with water (20 mL) and extracted with ethyl acetate (10 mL*3). The combined organic layers were dried over Na$_2$SO$_4$, filtered and concentrated under reduced pressure to give a residue. The residue was purified by column chromatography (SiO$_2$, petroleum ether:ethyl acetate=2:1 to 0:1) to give methyl (2S)-2-[[(2S,4S)-1-[(E)-3-(4-chloro-2-fluoro-phenyl)prop-2-enoyl]-4-phenyl-pyrrolidine-2-carbonyl]amino]-3-[(3S)-2-oxopyrrolidin-3-yl]propanoate (0.11 g, 162.36 umol, 34.33% yield, 80% purity) as a white solid. MS (ESI) m/z 542.1 [M+H]$^+$.

Step 5: (2S,4S)-N-((S)-1-amino-1-oxo-3-((S)-2-oxopyrrolidin-3-yl)propan-2-yl)-1-((E)-3-(4-chloro-2-fluorophenyl)acryloyl)-4-phenylpyrrolidine-2-carboxamide A mixture of methyl (2S)-2-[[(2S,4S)-1-[(E)-3-(4-chloro-2-fluoro-phenyl)prop-2-enoyl]-4-phenyl-pyrrolidine-2-carbonyl]amino]-3-[(3S)-2-oxopyrrolidin-3-yl]propanoate (0.1 g, 184.50 umol, 1 eq) in NH$_3$/MeOH (3 mL, 7 M) was stirred at 80° C. for 16 h in the sealed tube. Upon completion, the reaction mixture was concentrated under reduced pressure to give (2S,4S)-N-[(1S)-2-amino-2-oxo-1-[[(3S)-2-oxopyrrolidin-3-yl]methyl]ethyl]-1-[(E)-3-(4-chloro-2-fluoro-phenyl)prop-2-enoyl]-4-phenyl-pyrrolidine-2-carboxamide (0.09 g, crude) as a yellow oil. MS (ESI) m/z 527.0 [M+H]$^+$.

Step 6: (2S,4S)-1-((E)-3-(4-chloro-2-fluorophenyl)acryloyl)-N-((S)-1-cyano-2-((S)-2-oxopyrrolidin-3-yl)ethyl)-4-phenylpyrrolidine-2-carboxamide To a solution of (2S,4S)-N-[(1S)-2-amino-2-oxo-1-[[(3S)-2-oxopyrrolidin-3-yl]methyl]ethyl]-1-[(E)-3-(4-chloro-2-fluoro-phenyl)prop-2-enoyl]-4-phenyl-pyrrolidine-2-carboxamide (0.09 g, 170.78 umol, 1 eq) in DCM (1 mL) was added Burgess reagent (203.50 mg, 853.91 umol, 5 eq), and then the solution was stirred at 25° C. for 1 h. Upon completion, the reaction mixture was concentrated under reduced pressure to give a residue. The residue was purified by prep-HPLC (column: Waters Xbridge BEH C18 100*25 mm*5 um; mobile phase: [water (10 mM NH$_4$HCO$_3$)-ACN]; B %: 30%-60%, 10 min) to give (2S, 4S)-1-[(E)-3-(4-chloro-2-fluoro-phenyl)prop-2-enoyl]-N-[(1S)-1-cyano-2-[(3S)-2-oxopyrrolidin-3-yl]ethyl]-4-phenyl-pyrrolidine-2-carboxamide (29.73 mg, 56.89 umol, 33.31% yield, 97.4% purity) as a white solid. MS (ESI) m/z 509.1 [M+H]$^+$.

$^1$H NMR (400 MHz, DMSO-d$_6$) δ=9.17-8.86 (m, 1H), 8.07-7.75 (m, 1H), 7.75-7.65 (m, 1H), 7.62-7.49 (m, 2H), 7.48-7.30 (m, 5H), 7.26 (tt, J=3.0, 5.6 Hz, 1H), 7.22-6.73 (m, 1H), 5.09-4.83 (m, 1H), 4.69-4.47 (m, 1H), 4.40-4.01 (m, 1H), 3.77-3.50 (m, 3H), 3.19-3.04 (m, 2H), 2.44-2.31 (m, 2H), 2.22-2.09 (m, 2H), 1.88-1.59 (m, 2H).

Example 99. Synthesis of Viral Protease Inhibitor Compound 253

Step 1: methyl 2-amino-3-(2-oxo-1,2-dihydropyridin-3-yl)propanoate

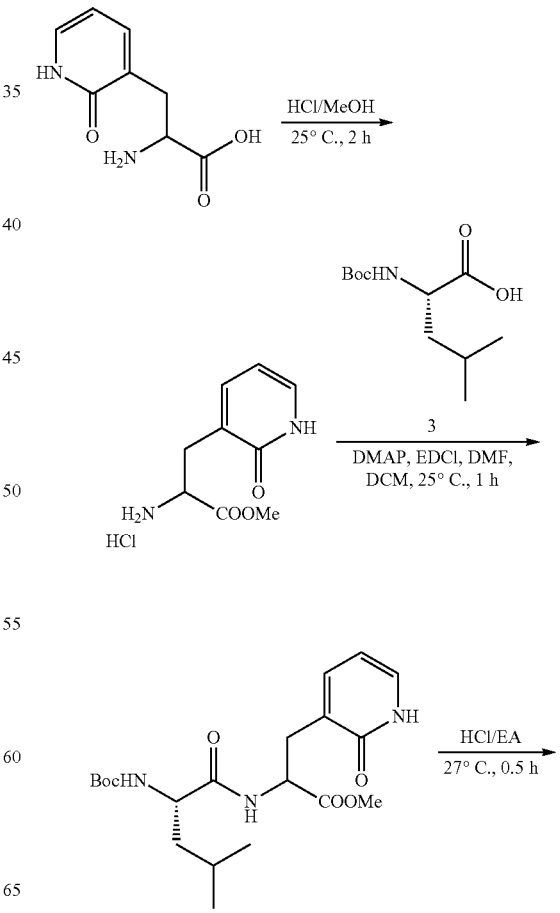

-continued

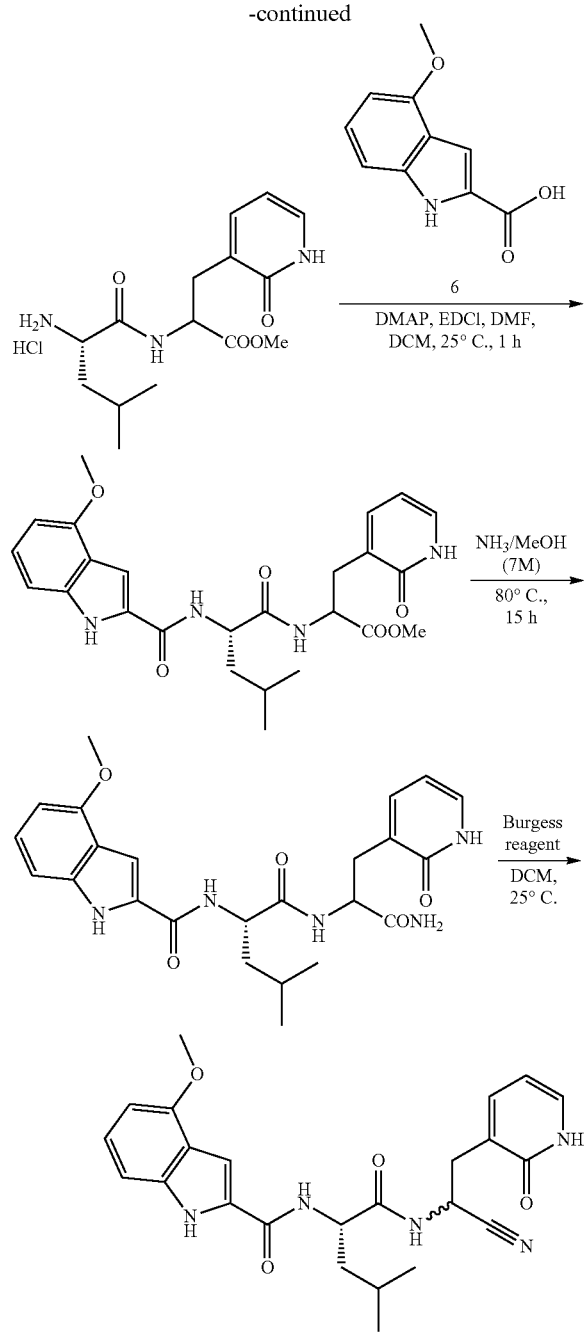

A mixture of 2-amino-3-(2-oxo-1H-pyridin-3-yl)propanoic acid (500 mg, 2.74 mmol, 1 eq) and HCl/MeOH (4 M, 30 mL, 43.72 eq) was stirred at 25° C. for 2 h. The reaction mixture was concentrated under reduced pressure to give a product methyl 2-amino-3-(2-oxo-1,2-dihydropyridin-3-yl)propanoate (650 mg, crude, HCl) as a yellow oil and used directly for next step. MS (ESI) m/z 197.0 [M+H]$^+$ Step 2: methyl-2-((S)-2-((tert-butoxycarbonyl)amino)-4-methylpentanamido)-3-(2-oxo-1,2-dihydropyridin-3-yl)propanoate A mixture of methyl 2-amino-3-(2-oxo-1H-pyridin-3-yl) propanoate (650 mg, 2.79 mmol, 1 eq, HCl), (2S)-2-(tert-butoxycarbonylamino)-4-methyl-pentanoic acid (646.16 mg, 2.79 mmol, 1 eq), EDCI (1.07 g, 5.59 mmol, 2 eq), DMAP (682.62 mg, 5.59 mmol, 2 eq), DMF (2 mL) and DCM (4 mL) was stirred at 25° C. for 1 h. The reaction mixture was diluted with H$_2$O (30 mL) and extracted with DCM (30 mL*3). The combined organic layers were washed with brine (50 mL), dried over Na$_2$SO$_4$, filtered and concentrated under reduced pressure to give a residue. The residue was purified by column chromatography (SiO$_2$, petroleum ether/ethyl acetate=0/1) to get the product methyl-2-((S)-2-((tert-butoxycarbonyl)amino)-4-methylpentanamido)-3-(2-oxo-1,2-dihydropyridin-3-yl)propanoate (900 mg, 1.89 mmol, 67.68% yield, 86.02% purity), as white solid. MS (ESI) m/z 410.1 [M+H]$^+$ Step 3: methyl 2-((S)-2-amino-4-methylpentanamido)-3-(2-oxo-1,2-dihydropyridin-3-yl)propanoate A mixture of methyl-2-((S)-2-((tert-butoxycarbonyl)amino)-4-methylpentanamido)-3-(2-oxo-1,2-dihydropyridin-3-yl)propanoate (200 mg, 488.43 umol, 1 eq) and HCl/EtOAc (4 M, 30 mL) was stirred at 27° C. for 0.5 h. The reaction mixture was concentrated under reduced pressure to give methyl 2-((S)-2-amino-4-methylpentanamido)-3-(2-oxo-1,2-dihydropyridin-3-yl)propanoate (170 mg, crude, HCl) as a white solid and used directly for next step.

Step 4: methyl 2-((S)-2-(4-methoxy-1H-indole-2-carboxamido)-4-methylpentanamido)-3-(2-oxo-1,2-dihydropyridin-3-yl)propanoate A mixture of methyl 2-((S)-2-amino-4-methylpentanamido)-3-(2-oxo-1,2-dihydropyridin-3-yl)propanoate (170 mg, 491.58 umol, 1 eq, HCl), 4-methoxy-1H-indole-2-carboxylic acid (93.98 mg, 491.58 umol, 1 eq), EDCI (188.47 mg, 983.17 umol, 2 eq), DMAP (120.11 mg, 983.17 umol, 2 eq), DMF (2 mL) and DCM (4 mL) was stirred at 25° C. for 1 h. The reaction mixture was diluted with H$_2$O (30 mL) and extracted with DCM (30 mL*3). The combined organic layers were washed with brine (50 mL), dried over Na$_2$SO$_4$, filtered and concentrated under reduced pressure to give a residue. The residue was purified by column chromatography (SiO$_2$, petroleum ether/ethyl acetate=0/1) to afford methyl 2-((S)-2-(4-methoxy-1H-indole-2-carboxamido)-4-methylpentanamido)-3-(2-oxo-1,2-dihydropyridin-3-yl)propanoate (130 mg, 269.41 umol, 54.81% yield) as white solid. MS (ESI) m/z 483.1 [M+H]$^+$ Step 5: N-((2S)-1-((1-amino-1-oxo-3-(2-oxo-1,2-dihydropyridin-3-yl)propan-2-yl)amino)-4-methyl-1-oxopentan-2-yl)-4-methoxy-1H-indole-2-carboxamide A mixture of methyl 2-((S)-2-(4-methoxy-1H-indole-2-carboxamido)-4-methylpentanamido)-3-(2-oxo-1,2-dihydropyridin-3-yl)propanoate (190 mg, 393.76 umol, 1 eq), NH$_3$/MeOH (7 M, 10 mL) was stirred at 80° C. for 15 h. The reaction mixture was concentrated under reduced pressure to give a residue N-((2S)-1-((1-amino-1-oxo-3-(2-oxo-1,2-dihydropyridin-3-yl)propan-2-yl)amino)-4-methyl-1-oxopentan-2-yl)-4-methoxy-1H-indole-2-carboxamide (190 mg, crude) as a yellow solid. MS (ESI) m/z 468.2 [M+H]$^+$ Step 6: N-((2S)-1-((1-cyano-2-(2-oxo-1,2-dihydropyridin-3-yl)ethyl)amino)-4-methyl-1-oxopentan-2-yl)-4-methoxy-1H-indole-2-carboxamide A mixture of N-((2S)-1-((1-amino-1-oxo-3-(2-oxo-1,2-dihydropyridin-3-yl)propan-2-yl)amino)-4-methyl-1-oxopentan-2-yl)-4-methoxy-1H-indole-2-carboxamide (180 mg, 385.01 umol, 1 eq), Burgess reagent (917.53 mg, 3.85 mmol, 10 eq) and DCM (30 mL) was stirred at 25° C. for 8 h. The reaction mixture was concentrated under reduced pressure to give a residue. The residue was purified by prep-HPLC (column: Phenomenex Gemini-NX C18 75*30 mm*3 um; mobile phase: [water(0.05% NH$_3$H$_2$O+10 mM NH$_4$HCO$_3$)-ACN]; B %: 25%-45%, 8 min) to get the product N-((2S)-1-((1-cyano-2-(2-oxo-1,2-dihydropyridin-3-yl)ethyl)amino)-4-methyl-1-oxopentan-2-yl)-4-methoxy-1H-indole-2-carboxamide (24 mg, 52.18 umol, 13.55% yield, 97.73% purity), as yellow solid. MS (ESI) m/z 450.2 [M+H]$^+$.

$^1$H NMR (400 MHz, DMSO-d$_6$) δ=11.90-11.40 (m, 2H), 9.08-8.85 (m, 1H), 8.55-8.35 (m, 1H), 7.51-7.26 (m, 3H), 7.16-7.05 (m, 1H), 7.04-6.94 (m, 1H), 6.51 (d, J=7.5 Hz, 1H), 6.15 (t, J=6.6 Hz, 1H), 5.19-5.01 (m, 1H), 4.55-4.33 (m, 1H), 3.89 (s, 3H), 3.02-2.78 (m, 2H), 1.75-1.33 (m, 3H), 0.98-0.72 (m, 6H).

Example 100. Synthesis of Viral Protease Inhibitor Compound 267 & 267A

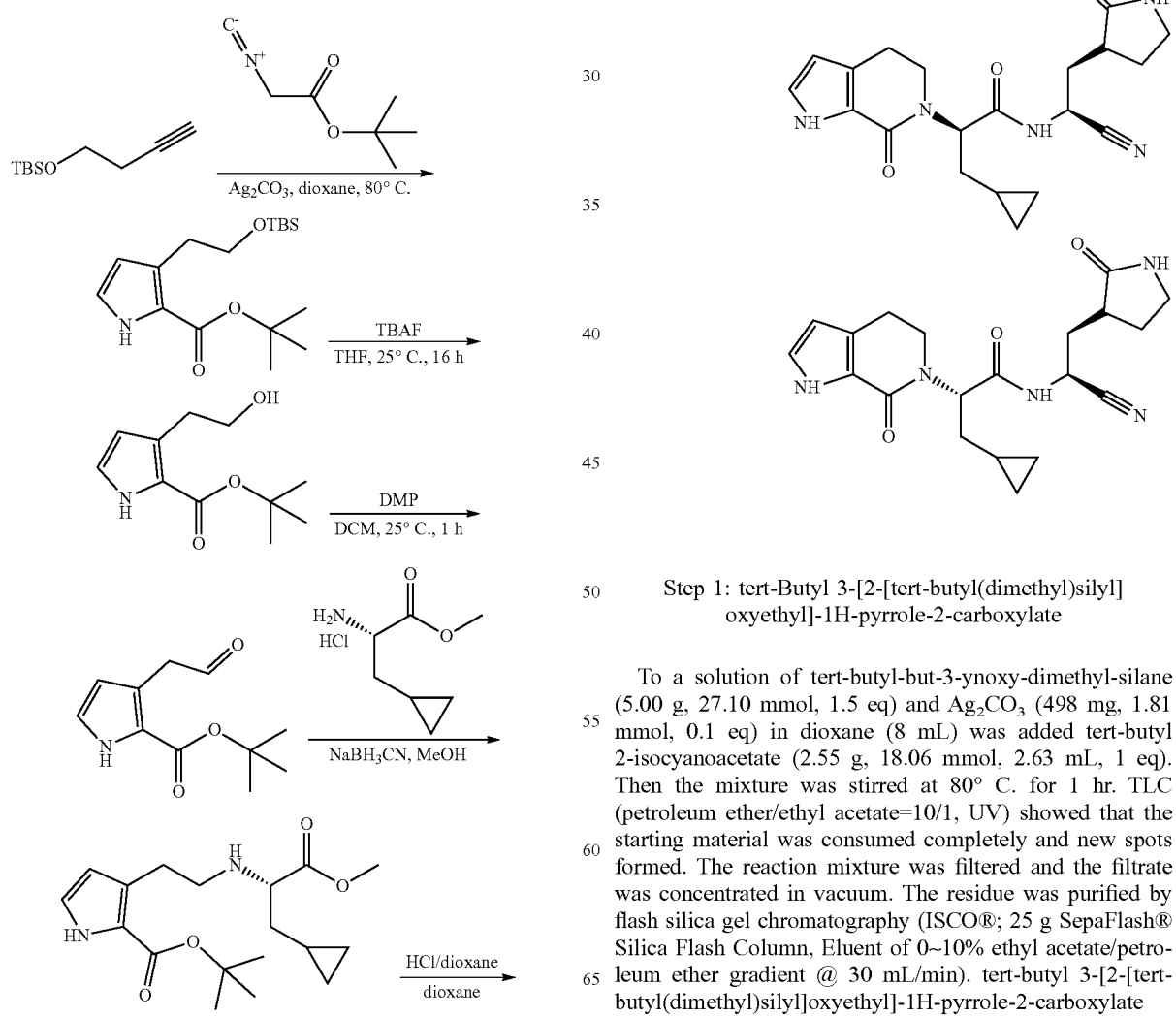

Step 1: tert-Butyl 3-[2-[tert-butyl(dimethyl)silyl]oxyethyl]-1H-pyrrole-2-carboxylate To a solution of tert-butyl-but-3-ynoxy-dimethyl-silane (5.00 g, 27.10 mmol, 1.5 eq) and Ag$_2$CO$_3$ (498 mg, 1.81 mmol, 0.1 eq) in dioxane (8 mL) was added tert-butyl 2-isocyanoacetate (2.55 g, 18.06 mmol, 2.63 mL, 1 eq). Then the mixture was stirred at 80° C. for 1 hr. TLC (petroleum ether/ethyl acetate=10/1, UV) showed that the starting material was consumed completely and new spots formed. The reaction mixture was filtered and the filtrate was concentrated in vacuum. The residue was purified by flash silica gel chromatography (ISCO®; 25 g SepaFlash® Silica Flash Column, Eluent of 0~10% ethyl acetate/petroleum ether gradient @ 30 mL/min). tert-butyl 3-[2-[tert-butyl(dimethyl)silyl]oxyethyl]-1H-pyrrole-2-carboxylate (2.5 g, 42.5% yield) was obtained as a white solid.

Step 2: tert-Butyl 3-(2-hydroxyethyl)-1H-pyrrole-2-carboxylate

To a solution of tert-butyl 3-[2-[tert-butyl(dimethyl)silyl]oxyethyl]-1H-pyrrole-2-carboxylate (2.5 g, 7.68 mmol, 1 eq) in THF (20 mL) was added TBAF (1 M, 15.3 mL, 2 eq) at 0° C., and then the mixture was stirred at 25° C. for 16 hr. TLC (petroleum ether/ethyl acetate=5/1, UV) showed that the starting material was consumed completely and new spot formed. The reaction mixture was concentrated in vacuum. The residue was purified by flash silica gel chromatography (ISCO®; 40 g SepaFlash® Silica Flash Column, Eluent of 0~10% DCM/MeOH @ 30 mL/min). tert-butyl 3-(2-hydroxyethyl)-1H-pyrrole-2-carboxylate (1.3 g, 80.1% yield) was obtained as colorless oil.

Step 3: tert-Butyl 3-(2-oxoethyl)-1H-pyrrole-2-carboxylate

To a solution of tert-butyl 3-(2-hydroxyethyl)-1H-pyrrole-2-carboxylate (1.15 g, 5.44 mmol, 1 eq) in DCM (20 mL) was added DMP (3.23 g, 7.62 mmol, 1.4 eq) and the mixture was stirred at 25° C. for 1 hr. LCMS showed that the starting material was remained and ~60% of the desired product was detected. TLC (petroleum ether/ethyl acetate=5/1, UV) showed that the starting material was consumed completely and new spot formed. The reaction mixture was filtered and the filtrated was concentrated in vacuum. The residue was diluted with ethyl acetate (50 mL), washed with $H_2O$ (10 mL), brine (10 mL) and dried over $Na_2SO_4$, filtered and concentrated in vacuum. The residue was purified by flash silica gel chromatography (ISCO®; 25 g SepaFlash® Silica Flash Column, Eluent of 0~20% ethyl acetate/petroleum ether gradient @ 30 mL/min). tert-butyl 3-(2-oxoethyl)-1H-pyrrole-2-carboxylate (1.5 g, 65.8% yield) was obtained as colorless oil.

$^1$H NMR (400 MHz, $CDCl_3$) δ 9.80-9.60 (m, 1H), 9.48 (br s, 1H), 6.91 (t, J=2.76 Hz, 1H), 6.16 (t, J=2.51 Hz, 1H), 3.82 (d, J=1.76 Hz, 2H), 1.56 (s, 9H).

Step 4: tert-Butyl 3-[2-[[(1S)-1-(cyclopropylmethyl)-2-methoxy-2-oxo-ethyl]amino]ethyl]-1H-pyrrole-2-carboxylate A solution of tert-butyl 3-(2-oxoethyl)-1H-pyrrole-2-carboxylate (1.5 g, 7.17 mmol, 1 eq) and methyl (2S)-2-amino-3-cyclopropyl-propanoate (1.29 g, 7.17 mmol, 1 eq, HCl) in MeOH (20 mL) was stirred at 25° C. for 0.5 hr. Then $NaBH_3CN$ (900.9 mg, 14.34 mmol, 2 eq) was added to the mixture and the result solution was stirred at 25° C. for 16 hr. LCMS showed that the starting material was consumed completely and 40% of the desired product was detected. TLC (petroleum ether/ethyl acetate=5/1, UV) showed that the starting material was consumed completely and new spots formed. The reaction mixture was quenched with $H_2O$ (10 mL), extracted with ethyl acetate (15 mL×3). The combined organic phase was washed with $H_2O$ (10 ml) and brine (10 mL×2), dried over $Na_2SO_4$, filtered and concentrated in vacuum. The residue was purified by flash silica gel chromatography (ISCO®; 25 g SepaFlash® Silica Flash Column, Eluent of 0~20% ethyl acetate/petroleum ether gradient @ 30 mL/min). tert-butyl 3-[2-[[(1S)-1-(cyclopropylmethyl)-2-methoxy-2-oxo-ethyl]amino]ethyl]-1H-pyrrole-2-carboxylate (0.6 g, 24.8% yield) was obtained as colorless oil.

$^1$H NMR (400 MHz, $CDCl_3$) δ 8.98 (br s, 1H), 6.91-6.65 (m, 1H), 6.15 (t, J=2.56 Hz, 1H), 3.71 (s, 3H), 3.40 (t, J=6.69 Hz, 1H), 2.99-2.92 (m, 2H), 2.82-2.90 (m, 1H), 2.78-2.69 (m, 1H), 1.68-1.63 (m, 1H), 1.57 (s, 9H), 1.50-1.42 (m, 1H), 0.76-0.66 (m, 1H), 0.48-0.36 (m, 2H), 0.11-0.01 (m, 2H).

Step 5: 3-[2-[[(1S)-1-(Cyclopropylmethyl)-2-methoxy-2-oxo-ethyl]amino]ethyl]-1H-pyrrole-2-carboxylic acid To a solution of tert-butyl 3-[2-[[(1S)-1-(cyclopropylmethyl)-2-methoxy-2-oxo-ethyl]amino]ethyl]-1H-pyrrole-2-carboxylate (0.2 g, 0.59 mmol, 1 eq) in dioxane (1 mL) was added HCl/dioxane (4 M, 1.49 mL, 10 eq) and the mixture was stirred at 25° C. for 16 hr. LCMS showed that the starting material was consumed completely and 88% of the desired product was detected. The reaction mixture was concentrated in vacuum. The crude product was used for the next step directly. 3-[2-[[(1S)-1-(cyclopropylmethyl)-2-methoxy-2-oxo-ethyl]amino]ethyl]-1H-pyrrole-2-carboxylic acid (0.15 g, 90% yield) was obtained as black brown oil.

Step 6: Methyl (2S)-3-cyclopropyl-2-(7-oxo-4,5-dihydro-1H-pyrrolo[2,3-c]pyridin-6-yl)propanoate To a solution of 3-[2-[[(1S)-1-(cyclopropylmethyl)-2-methoxy-2-oxo-ethyl]amino]ethyl]-1H-pyrrole-2-carboxylic acid (150 mg, 0.53 mmol, 1 eq) in DMF (1 mL) were added HOBt (108.4 mg, 0.802 mmol, 1.5 eq), DIEA (207.4 mg, 1.61 mmol, 0.28 mL, 3 eq) and EDCI (153.8 mg, 0.80 mmol, 1.5 eq). The mixture was stirred at 25° C. for 16 hr. LCMS showed that the starting material was consumed completely and 45% of the desired product was detected. TLC (petroleum ether/ethyl acetate=2/1, UV) showed that the starting material was consumed completely and new spots formed. The reaction mixture was quenched with $H_2O$ (20 mL), extracted with ethyl acetate (20 mL*3). The combined organic phase was washed with $H_2O$ (10 mL), brine (10 mL) and dried over $Na_2SO_4$, filtered and concentrated in vacuum. The residue was purified by flash silica gel chromatography (ISCO®; 24 g SepaFlash® Silica Flash Column, Eluent of 0~50% Ethyl acetate/Petroleum ether gradient @ 30 mL/min). methyl (2S)-3-cyclopropyl-2-(7-oxo-4,5-dihydro-1H-pyrrolo[2,3-c]pyridin-6-yl)propanoate (85 mg, 58.1% yield) was obtained as colorless oil.

LCMS: Rt=0.773 min; for $C_{14}H_{18}N_2O_3$ MS Calcd. 262.13; MS Found 263.0 [M+H$^+$].

$^1$H NMR (400 MHz, $CD_3OD$) δ 6.97-6.85 (m, 1H), 6.04 (d, J=2.26 Hz, 1H), 5.09 (dd, J=10.26, 5.27 Hz, 1H), 3.71 (s, 3H), 3.67-3.58 (m, 2H), 2.93-2.74 (m, 2H), 2.02-1.87 (m, 1H), 1.81-1.70 (m, 1H), 0.83-0.68 (m, 1H), 0.56-0.39 (m, 2H), 0.22-0.07 (m, 2H).

Step 7: (2S)-3-cyclopropyl-2-(7-oxo-4,5-dihydro-1H-pyrrolo[2,3-c]pyridin-6-yl)propanoic acid To a solution of methyl (2S)-3-cyclopropyl-2-(7-oxo-4,5-dihydro-1H-pyrrolo[2,3-c]pyridin-6-yl)propanoate (60 mg, 0.228 mmol, 1 eq) in MeOH (2 mL) was added $K_2CO_3$ (94.8 mg, 0.686 mmol, 3 eq) in $H_2O$ (1 mL) and the mixture was stirred at 25° C. for 16 hr. LCMS showed that the starting material was consumed completely and 100% of the desired product was detected. The reaction mixture was diluted with $H_2O$ (5 mL), adjusted pH=3 with 0.5 M aq.HCl and extracted with ethyl acetate (15 mL*3). The combined organic phase was washed with $H_2O$ (5 mL), brine (5 mL) and dried over $Na_2SO_4$, filtered and concentrated in vacuum. The crude product was used for the next step directly.

(2S)-3-cyclopropyl-2-(7-oxo-4,5-dihydro-1H-pyrrolo[2,3-c]pyridin-6-yl)propanoic acid was obtained as a white solid.
LCMS: Rt=0.706 min; for $C_{13}H_{16}N_2O_3$ MS Calcd. 248.12; MS Found 248.9 [M+H$^+$].

267A: (2R)-N-[(1S)-1-cyano-2-[(3S)-2-oxopyrrolidin-3-yl]ethyl]-3-cyclopropyl-2-(7-oxo-4,5-dihydro-1H-pyrrolo[2,3-c]pyridin-6-yl)propanamide 267: (2S)-N-[(1S)-1-cyano-2-[(3S)-2-oxopyrrolidin-3-yl]ethyl]-3-cyclopropyl-2-(7-oxo-4,5-dihydro-1H-pyrrolo[2,3-c]pyridin-6-yl)propanamide To a solution of (2S)-3-cyclopropyl-2-(7-oxo-4,5-dihydro-1H-pyrrolo[2,3-c]pyridin-6-yl)propanoic acid (40 mg, 0.16 mmol, 1 eq) and (2S)-2-amino-3-[(3S)-2-oxopyrrolidin-3-yl]propanenitrile (30.5 mg, 0.16 mmol, 1 eq, HCl) in DMF (1 mL) were added TEA (32.6 mg, 0.32 mmol, 44 uL, 2 eq) and T$_3$P (153.7 mg, 0.241 mmol, 0.14 mL, 50% purity, 1.5 eq) at 25° C., and the mixture was stirred at 25° C. for 1 hr. LCMS showed that the starting material was consumed completely and 86% of the desired product was detected. The reaction mixture was concentrated in vacuum. The residue was checked by HPLC and purified by prep-HPLC (column: Phenomenex Gemini-NX 80*40 mm*3 um; mobile phase: [water (0.05% NH$_3$H$_2$O+10 mM NH$_4$HCO$_3$)-ACN]; B %: 20%-50%, 7.8 min). (2S)-N-[(1S)-1-cyano-2-[(3S)-2-oxopyrrolidin-3-yl]ethyl]-3-cyclopropyl-2-(7-oxo-4,5-dihydro-1H-pyrrolo[2,3-c]pyridin-6-yl)propanamide (22 mg, 35.6% yield) was obtained as a white solid.

The crude product was purified by chiral SFC (column: DAICEL CHIRALPAK AS (250 mm*30 mm, 10 um); mobile phase: [0.1% NH$_3$H$_2$O ETOH]; B %: 30%-30%, min). (2R)-N-[(1S)-1-cyano-2-[(3S)-2-oxopyrrolidin-3-yl]ethyl]-3-cyclopropyl-2-(7-oxo-4,5-dihydro-1H-pyrrolo[2,3-c]pyridin-6-yl)propanamide (2.0 mg, 8.7% yield) was obtained as a white solid and (2S)-N-[(1S)-1-cyano-2-[(3S)-2-oxopyrrolidin-3-yl]ethyl]-3-cyclopropyl-2-(7-oxo-4,5-dihydro-1H-pyrrolo[2,3-c]pyridin-6-yl)propanamide (15.1 mg, 68.2% yield) was obtained as a white solid. 267A:
LCMS: Rt=0.746 min; for $C_{20}H_{25}N_5O_3$ MS Calcd. 383.20; MS Found 384.1 [M+H$^+$].
$^1$H NMR (400 MHz, CD$_3$OD) δ 6.91 (d, J=2.50 Hz, 1H). 6.04 (d, J=2.38 Hz, 1H), 5.15 (dd, J=8.44, 6.94 Hz, 1H), 5.04 (br d, J=6.75 Hz, 1H), 3.66-3.55 (m, 2H), 3.33 (br s, 2H), 2.88-2.76 (m, 2H), 2.55-2.42 (m, 1H), 2.39-2.23 (m, 2H), 1.96-1.83 (m, 2H), 1.82-1.74 (m, 2H), 0.70 (br s, 1H), 0.46 (t, J=7.88 Hz, 2H), 0.15 (d, J=4.38 Hz, 2H). 267:
LCMS: Rt=0.751 min; for $C_{20}H_{25}N_5O_3$ MS Calcd. 383.20; MS Found 384.1 [M+H$^+$].
$^1$H NMR (400 MHz, CD$_3$OD) δ 6.90 (d, J=2.38 Hz, 1H), 6.03 (d, J=2.25 Hz, 1H), 5.02 (dd, J=10.13, 6.63 Hz, 2H), 3.66 (tq, J=13.12, 6.34 Hz, 2H), 3.30-3.18 (m, 2H), 2.80 (br t, J=6.19 Hz, 2H), 2.59-2.44 (m, 1H), 2.37-2.21 (m, 2H), 1.97-1.69 (m, 4H), 0.78-0.67 (m, 1H), 0.60-0.42 (m, 2H), 0.17 (d, J=4.50 Hz, 2H).

Example 101. Synthesis of Viral Protease Inhibitor Compound 481 & 269A

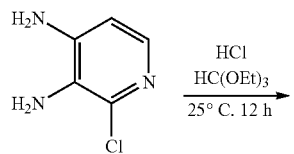

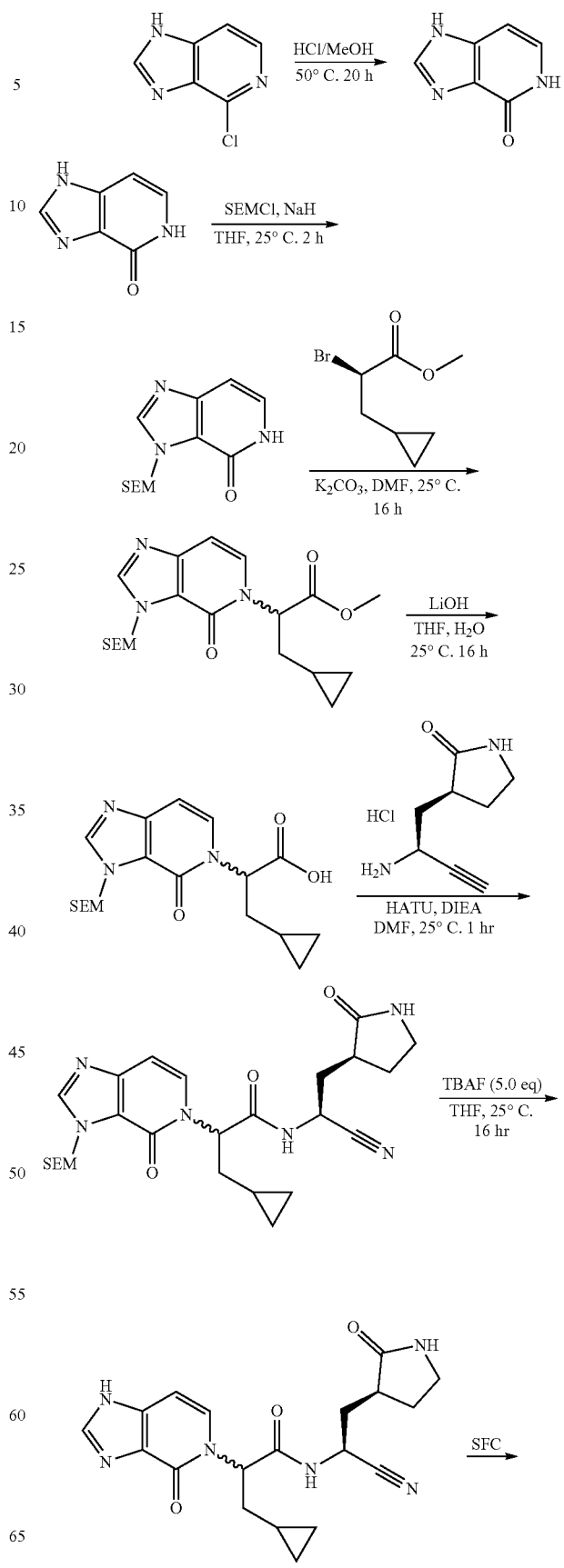

-continued

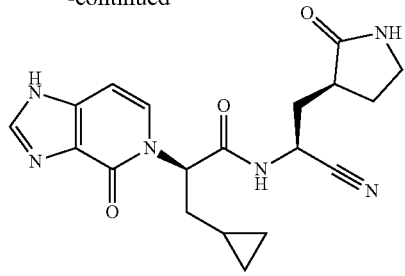

A mixture of 2-chloropyridine-3,4-diamine (3 g, 20.90 mmol, 1 eq) and HCl (2.06 g, 20.90 mmol, 2.0 mL, 37% purity, 1 eq) in diethoxymethoxyethane (30.9 g, 208.95 mmol, 34.7 mL, 10 eq) was degassed and purged with $N_2$ for 3 times, and then the mixture was stirred at 25° C. for 12 hr under $N_2$ atmosphere. The precipitate formed was filtered, washed with PE. No purification. Compound 4-chloro-1H-imidazo[4,5-c]pyridine (3 g, 93.4% yield) was obtained as a white solid.

Step 2: 1,5-dihydroimidazo[4,5-c]pyridin-4-one

To a solution of 4-chloro-1H-imidazo[4,5-c]pyridine (3 g, 19.54 mmol, 1 eq) and HCl (1.9 g, 19.54 mmol, 1.8 mL, 37% purity, 1 eq) in MeOH (10 mL). The mixture was stirred at 50° C. for 30 hr. The reaction mixture was concentrated under reduced pressure to remove HCl/MeOH. The crude product was triturated with PE at 25° C. for 150 min. Compound 1,5-dihydroimidazo[4,5-c]pyridin-4-one (2.5 g, crude) was obtained as yellow solid.

Step 3: 3-(2-trimethylsilylethoxymethyl)-5H-imidazo[4,5-c]pyridin-4-one

To a solution of 1,5-dihydroimidazo[4,5-c]pyridin-4-one (2.5 g, 18.50 mmol, 1 eq) and SEM-Cl (3.0 g, 18.50 mmol, 3.2 mL, 1 eq) in THF (1 mL) was added NaH (2.2 g, 55.50 mmol, 60% purity, 3 eq). The mixture was stirred at 25° C. for 2 hr. TLC (petroleum ether/ethyl acetate=0:1, UV 254) indicated starting material was remained and new spots formed. The reaction mixture was diluted with $H_2O$ (30 mL) and extracted with ethyl acetate (30 mL*3). The combined organic layers were washed with brine (30 mL*2), dried with anhydrous $Na_2SO_4$, filtered and concentrated under reduced pressure to give a residue. The residue was purified by flash silica gel chromatography (ISCO®; 25 g SepaFlash® Silica Flash Column, Eluent of 0~100% petroleum ether/ethyl acetate @ 35 mL/min). Compound 3-(2-trimethylsilylethoxymethyl)-5H-imidazo[4,5-c]pyridin-4-one (1.8 g, 32.2% yield, 88% purity) was obtained as yellow solid.

Step 4: Methyl 3-cyclopropyl-2-[4-oxo-3-(2-trimethylsilylethoxymethyl)imidazo[4,5-c]pyridin-5-yl]propanoate To a solution of 3-(2-trimethylsilylethoxymethyl)-5H-imidazo[4,5-c]pyridin-4-one (1.5 g, 5.65 mmol, 1 eq) and methyl (2R)-2-bromo-3-cyclopropyl-propanoate (1.1 g, 5.65 mmol, 1 eq) in DMF (4 mL) was added $K_2CO_3$ (1.5 g, 11.30 mmol, 2 eq). The mixture was stirred at 25° C. for 16 hr. TLC (petroleum ether/ethyl acetate=3:1, UV 254) indicated starting material was remained and new spots formed. The reaction mixture was diluted with $H_2O$ (30 mL) and extracted with ethyl acetate (30 mL*3). The combined organic layers were washed with brine (30 mL*2), dried with anhydrous $Na_2SO_4$, filtered and concentrated under reduced pressure to give a residue. The residue was purified by flash silica gel chromatography (ISCO®; 12 g SepaFlash® Silica Flash Column, Eluent of 0~40% petroleum ether/ethyl acetate @ 35 mL/min). Compound methyl 3-cyclopropyl-2-[4-oxo-3-(2-trimethylsilylethoxymethyl)imidazo[4,5-c]pyridin-5-yl]propanoate (865 mg, 36.7% yield, 94% purity) was obtained as a white solid.

Step 5: 3-cyclopropyl-2-[4-oxo-3-(2-trimethylsilylethoxymethyl)imidazo[4,5-c]pyridin-5-yl]propanoic acid To a solution of methyl 3-cyclopropyl-2-[4-oxo-3-(2-trimethylsilylethoxymethyl)imidazo[4,5-c]pyridin-5-yl]propanoate (865 mg, 2.21 mmol, 1 eq) in $H_2O$ (1 mL) and THF (1 mL) was added LiOH·$H_2O$ (185.4 mg, 4.42 mmol, 2 eq). The mixture was stirred at 25° C. for 16 hr. The reaction mixture was concentrated under reduced pressure to remove THF. The residue was diluted with $H_2O$ (2 mL) and added HCl (2 mL, 2 N). The reaction mixture was diluted with $H_2O$ (30 mL) and extracted with ethyl acetate (30 mL*3). The combined organic layers were washed with brine (30 mL*2), dried with anhydrous $Na_2SO_4$, filtered and concentrated under reduced pressure to give a residue. The crude product was triturated with PE at 25° C. for 60 min. Compound 3-cyclopropyl-2-[4-oxo-3-(2-trimethylsilylethoxymethyl) imidazo[4,5-c]pyridin-5-yl]propanoic acid (746 mg, 86.7% yield, 97% purity) was obtained as a white solid.

481 (N-[(1S)-1-cyano-2-[(3S)-2-oxopyrrolidin-3-yl]ethyl]-3-cyclopropyl-2-[4-oxo-3-(2-trimethylsilylethoxymethyl)imidazo[4,5-c]pyridin-5-yl]propenamide): A mixture of (2S)-3-cyclopropyl-2-[4-oxo-3-(2-trimethylsilylethoxymethyl)imidazo[4,5-c]pyridin-5-yl]propanoic acid (600 mg, 1.59 mmol, 1 eq), (2S)-2-amino-3-[(3S)-2-oxopyrrolidin-3-yl]propanenitrile (301.4 mg, 1.59 mmol, 1 eq, HCl), HATU (604.3 mg, 1.59 mmol, 1 eq), DIPEA (410.8 mg, 3.18 mmol, 0.55 mL, 2 eq) in DCM (1 mL) was degassed and purged with $N_2$ for 3 times, and then the mixture was stirred at 25° C. for 1 hr under $N_2$ atmosphere. TLC (petroleum ether/ethyl acetate=3:1, UV 254) indicated starting material was remained and new spots formed. The reaction mixture was diluted with $H_2O$ (30 mL) and extracted with ethyl acetate (30 mL*3). The combined organic layers were washed with brine (30 mL*2), dried with anhydrous $Na_2SO_4$, filtered and concentrated under reduced pressure to give a residue. The residue was purified by flash silica gel chromatography (ISCO®; 12 g SepaFlash® Silica Flash Column, Eluent of 0~45% petroleum ether/ethyl acetate @ 35 mL/min). Compound N-[(1S)-1-cyano-2-[(3S)-2-oxopyrrolidin-3-yl]ethyl]-3-cyclopropyl-2-[4-oxo-3-(2-trimethylsilylethoxymethyl)imidazo[4,5-c]pyridin-5-yl]propanamide (645 mg, 66.4% yield, 84% purity) was obtained as a white solid.

269A: To a solution of N-[(1S)-1-cyano-2-[(3S)-2-oxopyrrolidin-3-yl]ethyl]-3-cyclopropyl-2-[4-oxo-3-(2-trimethylsilylethoxymethyl)imidazo[4,5-c]pyridin-5-yl]propanamide (600 mg, 1.17 mmol, 1 eq) in THF (1 mL) was added TBAF (1 M, 2.3 mL, 2 eq). The mixture was stirred at 60° C. for 2 hr. The reaction mixture was concentrated under reduced pressure to remove THF. The residue was purified by prep-HPLC (column: Phenomenex Gemini-NX 80*40 mm*3 um; mobile phase: [water(0.05% $NH_3H_2O$+10 mM $NH_4HCO_3$)-ACN]; B %: 5%-35%, 9.5 min). Compound $C_{19}H_{22}N_6O_3$ (34 mg, 7.6% yield, 100% purity) was obtained as white solid.

(2R)-N-[(1S)-1-cyano-2-[(3S)-2-oxopyrrolidin-3-yl]ethyl]-3-cyclopropyl-2-(4-oxo-3H-imidazo[4,5-c]pyridin-5-yl)propanamide (34 mg, 88.9 umol, 1 eq) was purity by SFC. The residue was purified by prep-HPLC (column: (s,s) WHELK-O1 (250 mm*30 mm, 5 um); mobile phase: [0.1% NH$_3$H$_2$O EtOH]; B %: 40%-40%, min). Compound (2R)-N-[(1S)-1-cyano-2-[(3S)-2-oxopyrrolidin-3-yl]ethyl]-3-cyclopropyl-2-(4-oxo-3H-imidazo[4,5-c]pyridin-5-yl)propanamide (18.56 mg, 54.5% yield, 100% purity) was obtained as white solid.

LCMS: Rt=0.627 min; for C$_{19}$H$_{22}$N$_6$O$_3$ MS Calcd.: 382.42; MS Found: 383.1 [M+H$^+$].

$^1$H NMR (400 MHz, CD$_3$OD) δ 9.28 (br s, 1H), 7.94-7.79 (m, 1H), 6.86 (br d, J=7.3 Hz, 1H), 5.74-5.50 (m, 2H), 4.62-4.18 (m, 2H), 3.50-3.32 (m, 1H), 3.14 (br s, 1H), 2.66-2.37 (m, 1H), 2.28 (br s, 1H), 2.16-1.95 (m, 3H), 1.92-1.72 (m, 2H), 0.62 (br s, 1H), 0.41 (br d, J=3.8 Hz, 2H), 0.18 (br s, 1H), 0.03 (br d, J=4.5 Hz, 1H).

Example 102. Synthesis of Viral Protease Inhibitor Compound 269

(2S)-N-[(1S)-1-cyano-2-[(3S)-2-oxopyrrolidin-3-yl]ethyl]-3-cyclopropyl-2-(4-oxo-3H-imidazo[4,5-c]pyridin-5-yl)propanamide (28 mg, 73.2 umol, 1 eq) was purity by SFC. The residue was purified by prep-HPLC (column: (s,s) WHELK-O1 (250 mm*30 mm, 5 um); mobile phase: [0.1% NH$_3$H$_2$O ETOH]; B %: 40%-40%, min). Compound (2S)-N-[(1S)-1-cyano-2-[(3S)-2-oxopyrrolidin-3-yl]ethyl]-3-cyclopropyl-2-(4-oxo-3H-imidazo[4,5-c]pyridin-5-yl)propanamide (15.52 mg, 55.4% yield, 100% purity) was obtained as a white solid.

LCMS: Rt=0.647 min; for C$_{19}$H$_{22}$N$_6$O$_3$ MS Calcd.: 382.42; MS Found: 383.1 [M+H$^+$].

$^1$H NMR (400 MHz, CD$_3$OD) δ 9.29 (br s, 1H), 7.88 (br d, J=6.3 Hz, 1H), 6.87 (br d, J=6.5 Hz, 1H), 5.89-5.41 (m, 1H), 4.74-4.29 (m, 1H), 3.48 (br s, 1H), 3.30-3.09 (m, 1H), 2.67-2.42 (m, 1H), 2.39-2.21 (m, 1H), 2.21-1.99 (m, 3H), 1.94-1.55 (m, 1H), 0.63 (br s, 1H), 0.42 (br s, 2H), 0.27-0.08 (m, 2H).

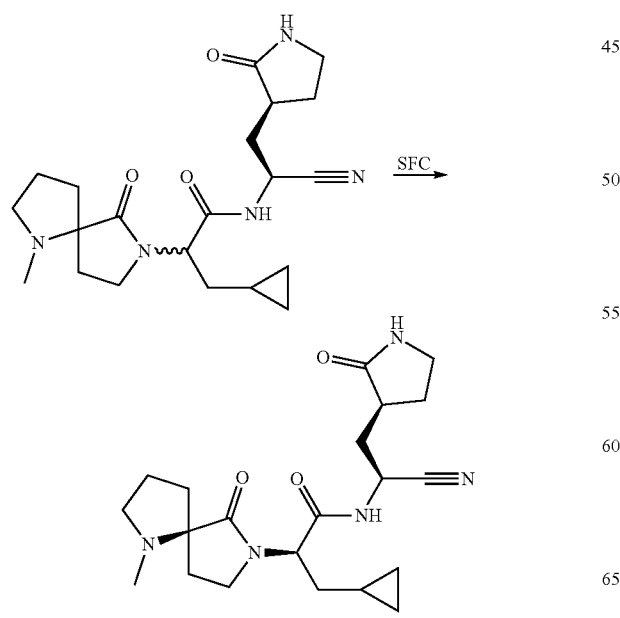

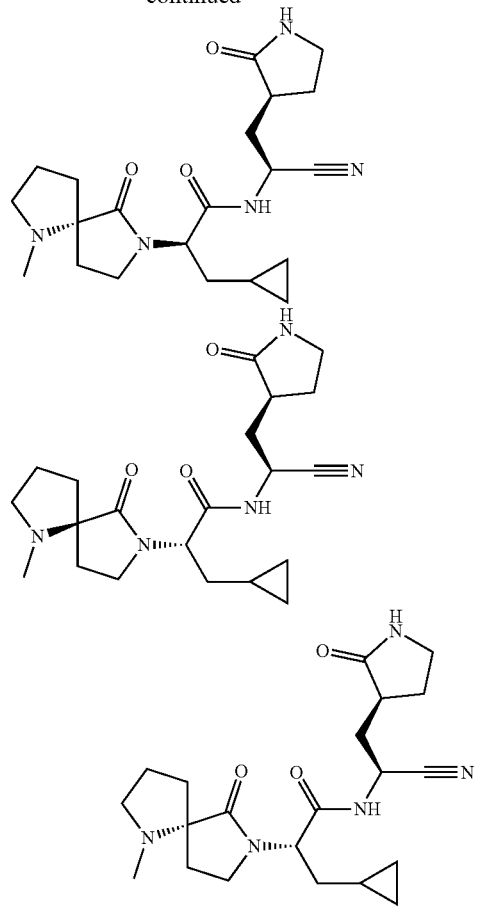

271A Isomer 1: (2R)-N-[(1S)-1-cyano-2-[(3S)-2-oxopyrrolidin-3-yl]ethyl]-3-cyclopropyl-2-[(5R)-1-methyl-6-oxo-1,7-diazaspiro[4.4]nonan-7-yl]propanamide 271A Isomer 2: (2R)-N-[(1S)-1-cyano-2-[(3S)-2-oxopyrrolidin-3-yl]ethyl]-3-cyclopropyl-2-[(5S)-1-methyl-6-oxo-1,7-diazaspiro[4.4]nonan-7-yl]propanamide 271 Isomer 3: (2S)-N-[(1S)-1-cyano-2-[(3S)-2-oxopyrrolidin-3-yl]ethyl]-3-cyclopropyl-2-[(5R)-1-methyl-6-oxo-1,7-diazaspiro[4.4]nonan-7-yl]propanamide 271 Isomer 4: (2S)-N-[(1S)-1-cyano-2-[(3S)-2-oxopyrrolidin-3-yl]ethyl]-3-cyclopropyl-2-[(5S)-1-methyl-6-oxo-1,7-diazaspiro[4.4]nonan-7-yl]propanamide 270 was purified by prep-SFC (column: DAICEL CHIRALPAK AS (250 mm*30 mm, 10 um); mobile phase: [0.1% NH3H2O ETOH]; B %: 20%-20%, min) to give 271A (30 mg) and 271 (20 mg). 271A Isomer 1 & 2 was purified by prep-SFC (column: DAICEL CHIRALPAK AD (250 mm*30 mm, 10 um); mobile phase: [0.1% NH$_3$H$_2$O IPA]; B %: 25%-25%, min) to give 271A Isomer 1 (2.65 mg, 2% yield) and 271A Isomer 2 (2.76 mg, 2% yield) as two white solid. 271 Isomer 1 & 271 Isomer 2 was purified by prep-SFC (column: DAICEL CHIRALPAK IG (250 mm*30 mm, 10 um); mobile phase: [0.1% NH$_3$H$_2$O MEOH]; B %: 40%-40%, min) to give 271 Isomer 1 (15.96 mg, 15% yield) and 271 Isomer 2 (13.71 mg, 13% yield) as two white solid.

271A Isomer 1: LCMS: Rt=1.208 min; for C$_{21}$H$_{31}$N$_5$O$_3$ MS Calcd.: 401.24; MS Found: 402.2 [M+H$^+$]; $^1$H NMR (400 MHz, CD$_3$OD) δ 4.96 (dd, J=6.8, 9.3 Hz, 1H), 4.66-4.61 (m, 1H), 3.50 (dd, J=5.6, 8.1 Hz, 2H), 3.37-3.31 (m, 2H), 3.11-3.02 (m, 1H), 2.91-2.81 (m, 1H), 2.53-2.42 (m, 1H), 2.40-2.31 (m, 4H), 2.30-2.09 (m, 3H), 2.02-1.81 (m, 7H), 1.61 (td, J=7.2, 14.1 Hz, 1H), 0.69-0.60 (m, 1H), 0.55-0.40 (m, 2H), 0.20-0.13 (m, 2H).

271A Isomer 2: LCMS: Rt=1.180 min; for C$_{21}$H$_{31}$N$_5$O$_3$ MS Calcd.: 401.24; MS Found: 402.2 [M+H$^+$]; $^1$H NMR (400 MHz, CD$_3$OD) δ 5.01 (dd, J=6.3, 9.9 Hz, 1H), 4.57 (t, J=7.8 Hz, 1H), 3.55-3.47 (m, 2H), 3.37-3.31 (m, 2H), 3.11-2.99 (m, 1H), 2.90-2.80 (m, 1H), 2.60-2.46 (m, 1H), 2.37-2.14 (m, 6H), 2.09-1.72 (m, 8H), 1.63-1.50 (m, 1H), 0.74-0.63 (m, 1H), 0.58-0.44 (m, 2H), 0.24-0.15 (m, 2H).

271 Isomer 1: LCMS: Rt=1.217 min; for C$_{21}$H$_{31}$N$_5$O$_3$ MS Calcd.: 401.24; MS Found: 402.2 [M+H$^+$]; $^1$H NMR (400 MHz, CD$_3$OD) δ 5.04-4.92 (m, 1H), 4.67-4.60 (m, 1H), 3.73-3.39 (m, 2H), 3.37-3.32 (m, 2H), 3.15-3.00 (m, 1H), 2.88 (d, J=6.5 Hz, 1H), 2.62-2.42 (m, 1H), 2.40-2.15 (m, 6H), 2.11-1.76 (m, 8H), 1.68-1.51 (m, 1H), 0.75-0.57 (m, 1H), 0.57-0.39 (m, 2H), 0.23-0.11 (m, 2H).

271 Isomer 2: LCMS: Rt=1.222 min; for C$_{21}$H$_{31}$N$_5$O$_3$ MS Calcd.: 401.24; MS Found: 402.2 [M+H$^+$]; $^1$H NMR (400 MHz, CD$_3$OD) δ 5.01 (dd, J=6.1, 9.9 Hz, 1H), 4.56 (t, J=7.8 Hz, 1H), 3.70-3.61 (m, 1H), 3.49-3.40 (m, 1H), 3.37-3.32 (m, 1H), 3.30-3.23 (m, 1H), 3.06-2.98 (m, 1H), 2.87-2.77 (m, 1H), 2.53 (dq, J=5.5, 9.3 Hz, 1H), 2.37-2.16 (m, 6H), 2.10-1.75 (m, 8H), 1.65-1.54 (m, 1H), 0.72-0.61 (m, 1H), 0.57-0.46 (m, 2H), 0.21-0.11 (m, 2H).

Example 104. Synthesis of Viral Protease Inhibitor Compound 273A, 273B & 273C

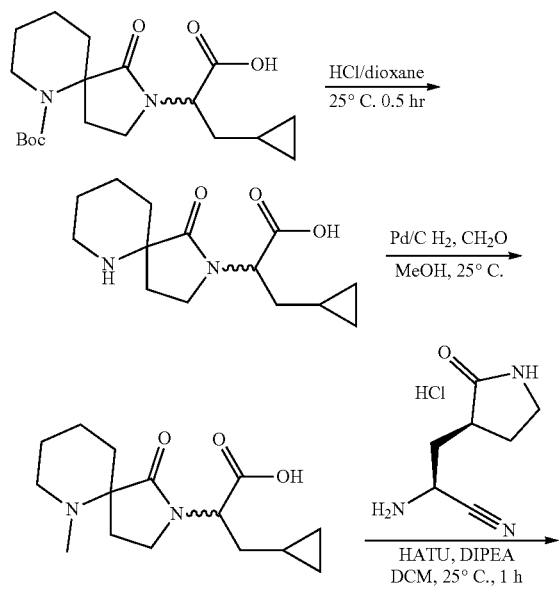

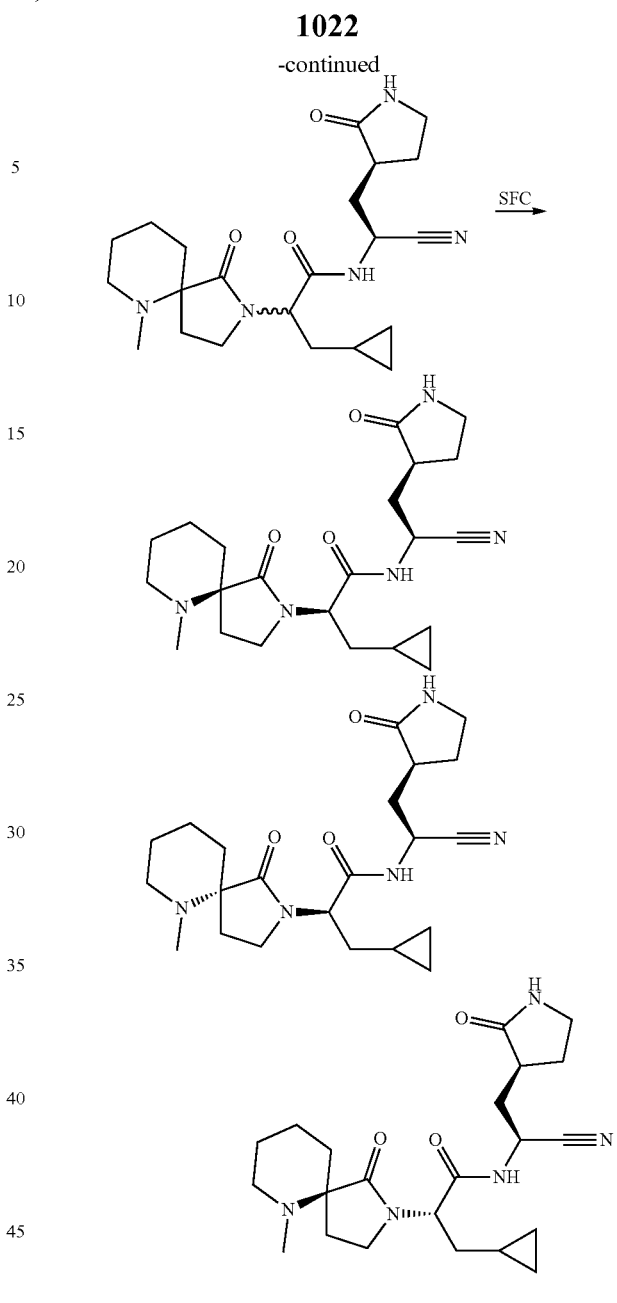

A solution of 1 (0.7 g, 1.91 mmol, 1 eq) in HCl/dioxane (4 M, 10 mL, 20.9 eq) was stirred at 25° C. for 0.5 hr. LC-MS showed 1 was consumed completely and 45% of desired compound was detected. The reaction mixture was concentrated under reduced pressure to give a residue. The crude product was used into the next step without further purification. 3-cyclopropyl-2-(1-oxo-2,6-diazaspiro[4.5]decan-2-yl)propanoic acid (500 mg, crude) was obtained as a colorless oil.

Step 2: (2S)-3-cyclopropyl-2-(6-methyl-1-oxo-2,6-diazaspiro[4.5]decan-2-yl)propanoic acid A solution of 3-cyclopropyl-2-(1-oxo-2,6-diazaspiro[4.5]decan-2-yl)propanoic acid (0.5 g, 1.88 mmol, 1 eq) in MeOH (4 mL) was added Pd/C (50 mg, 0.37 mmol, 10% purity) and formaldehyde (1.52 g, 18.7 mmol, 1.4 mL, 37% purity, 10 eq) was degassed under vacuum and purged with H$_2$ several times. The mixture was stirred under H$_2$ (15 psi)

at 25° C. for 0.5 hour. One spot was detected on TLC (Dichloromethane:Methanol=5/1, KMnO₄). LC-MS showed 2 was consumed completely and 71% of desired compound was detected. The reaction mixture was filtered and concentrated under reduced pressure to give a residue. The residue was purified by column chromatography (SiO₂, dichloromethane:methanol=100/1 to 5/1) to give (2S)-3-cyclopropyl-2-(6-methyl-1-oxo-2,6-diazaspiro[4.5]decan-2-yl)propanoic acid (0.4 g, 76% yield) as a white solid.

Step 3: (2S)-N-[(1S)-1-cyano-2-[(3S)-2-oxopyrrolidin-3-yl]ethyl]-3-cyclopropyl-2-(6-methyl-1-oxo-2,6-diazaspiro[4.5]decan-2-yl)propanamide To a solution of (2S)-3-cyclopropyl-2-(6-methyl-1-oxo-2,6-diazaspiro[4.5]decan-2-yl)propanoic acid (0.3 g, 1.0 mmol, 1 eq) in DCM (6 mL) was added HATU (610.3 mg, 1.61 mmol, 1.5 eq), DIPEA (276.5 mg, 2.14 mmol, 0.37 mL, 2.0 eq), and 3a (243.51 mg, 1.28 mmol, 1.2 eq, HCl). The mixture was stirred at 25° C. for 1 hr. LC-MS showed 3 was consumed completely and 15% of desired compound was detected. The reaction mixture was filtered and concentrated under reduced pressure to give a residue. The residue was purified by prep-HPLC (column: Phenomenex Gemini-NX 80*40 mm*3 um; mobile phase: [water (0.05% NH₃H₂O+ 10 mM NH₄HCO₃)-ACN]; B %: 17%-47%, 9.5 min) to give (2S)-N-[(1S)-1-cyano-2-[(3S)-2-oxopyrrolidin-3-yl]ethyl]-3-cyclopropyl-2-(6-methyl-1-oxo-2,6-diazaspiro[4.5]decan-2-yl)propanamide (60 mg, 13% yield) as a white solid.

273A: (2R)-N-[(1S)-1-cyano-2-[(3S)-2-oxopyrrolidin-3-yl]ethyl]-3-cyclopropyl-2-[(5R)-6-methyl-1-oxo-2,6-diazaspiro[4.5]decan-2-yl]propanamide 273B: (2R)-N-[(1S)-1-cyano-2-[(3S)-2-oxopyrrolidin-3-yl]ethyl]-3-cyclopropyl-2-[(5S)-6-methyl-1-oxo-2,6-diazaspiro[4.5]decan-2-yl]propanamide 273C: (2S)-N-[(1S)-1-cyano-2-[(3S)-2-oxopyrrolidin-3-yl]ethyl]-3-cyclopropyl-2-[(5R)-6-methyl-1-oxo-2,6-diazaspiro[4.5]decan-2-yl]propanamide 4 was purified by prep-SFC (column: DAICEL CHIRALPAK AS (250 mm*30 mm, 10 um); mobile phase: [0.1% NH₃H₂O ETOH]; B %: 20%-20%, min) to give 273A & 273B (20 mg) and 273C (2.79 mg, 6.5 umol, 4% yield, 97% purity). 273A & 273B (20 mg) was purified by prep-SFC (column: DAICEL CHIRALPAK AD (250 mm*30 mm, 10 um); mobile phase: [0.1% NH₃H₂O ETOH]; B %: 40%-40%, min) to give 273A (2.50 mg, 4.1% yield) and 273B (2.59 mg, 4% yield).

273A: LCMS: Rt=1.362 min; for C₂₂H₃₃N₅O₃ MS Calcd.: 415.26; MS Found: 416.2 [M+H⁺]. ¹H NMR (400 MHz, CD₃OD) δ 4.79 (s, 1H), 4.52-4.47 (m, 1H), 3.34-3.24 (m, 2H), 3.20-3.15 (m, 2H), 2.60-2.44 (m, 1H), 2.35-2.24 (m, 1H), 2.22-2.00 (m, 4H), 1.94 (s, 3H), 1.83-1.64 (m, 4H), 1.60-1.31 (m, 7H), 0.55-0.38 (m, 1H), 0.37-0.20 (m, 2H), 0.06-0.12 (m, 2H).

273B: LCMS: Rt=1.353 min; for C₂₂H₃₃N₅O₃ MS Calcd.: 415.26; MS Found: 416.2 [M+H⁺]. ¹H NMR (400 MHz, CD₃OD) δ 4.83 (dd, J=6.8, 9.3 Hz, 1H), 4.52-4.49 (m, 1H), 3.47-3.38 (m, 1H), 3.34-3.25 (m, 1H), 3.23-3.17 (m, 2H), 2.60-2.50 (m, 1H), 2.41-2.27 (m, 1H), 2.25-2.03 (m, 4H), 1.97 (s, 3H), 1.82-1.31 (m, 1H), 0.50-0.40 (m, 1H), 0.37-0.23 (m, 2H), 0.05-0.06 (m, 2H).

273C: LCMS: Rt=1.363 min; for C₂₂H₃₃N₅O₃ MS Calcd.: 415.26; MS Found: 416.2 [M+H⁺]. ¹H NMR (400 MHz, CD₃OD) δ 4.82 (dd, J=6.0, 10.0 Hz, 1H), 4.42-4.38 (m, 1H), 3.41-3.23 (m, 2H), 3.18-3.14 (m, 1H), 3.12-3.06 (m, 1H), 2.57-2.46 (m, 1H), 2.45-2.29 (m, 1H), 2.17-1.95 (m, 4H), 1.93 (s, 3H), 1.80-1.58 (m, 4H), 1.57-1.26 (m, 7H), 0.57-0.41 (m, 1H), 0.40-0.23 (m, 2H), 0.06-0.07 (m, 2H).

Example 105. Synthesis of Viral Protease Inhibitor Compound 278

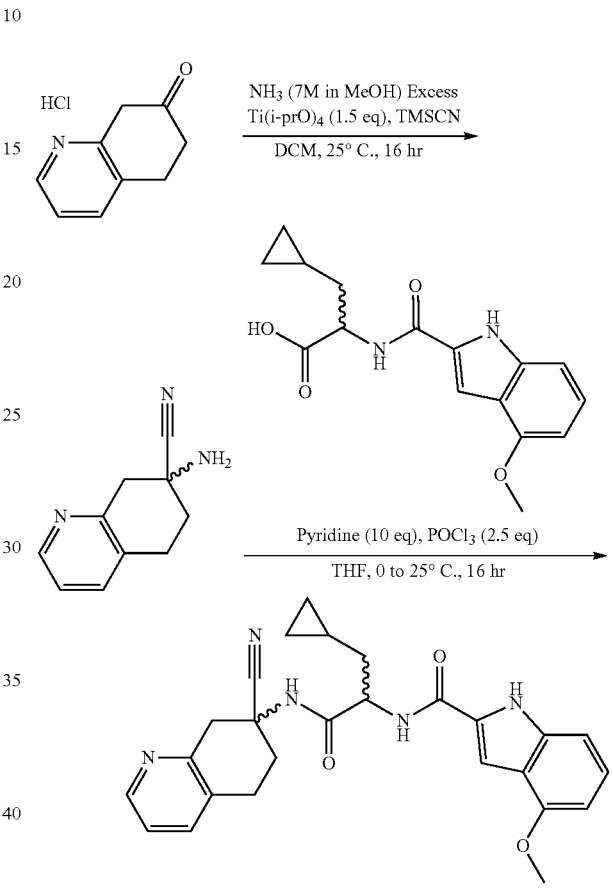

A solution of 6,8-dihydro-5H-quinolin-7-one (350 mg, 1.91 mmol, 1 eq, HCl) in DCM (7 mL) were added NH₃ (7 M, 2.72 mL, 10 eq) and Ti(i-PrO)₄ (650.0 mg, 2.29 mmol, 0.67 mL, 1.2 eq) was stirred at 25° C. for 2 hr. TMSCN (283.6 mg, 2.86 mmol, 0.35 mL, 1.5 eq) was added and the solution was stirred at 25° C. for 16 hr. LC-MS showed starting material was consumed completely and one main peak with desired MS was detected. Ethyl acetate (50 mL) and H₂O (2.0 mL) were added, the reaction mixture was filtered, the filtrate was concentrated to reduce pressure. Compound 7-amino-6,8-dihydro-5H-quinoline-7-carbonitrile (260 mg, crude) was obtained as a yellow solid.

278: N-(1-((7-Cyano-5,6,7,8-tetrahydroquinolin-7-yl)amino)-3-cyclopropyl-1-oxopropan-2-yl)-4-methoxy-1H-indole-2-carboxamide A solution of 7-amino-6,8-dihydro-5H-quinoline-7-carbonitrile (80 mg, 0.46 mmol, 1 eq), (2S)-3-cyclopropyl-2-[(4-methoxy-1H-indole-2-carbonyl)amino]propanoic acid (153.5 mg, 0.50 mmol, 1.1 eq) and pyridine (365.3 mg, 4.62 mmol, 0.37 mL, 10 eq) in THF (2 mL) was stirred at 25° C. for 15 min. After POCl₃ (177.0 mg, 1.15 mmol, 0.10 mL, 2.5 eq) was added dropwise at 0° C., the reaction mixture was stirred at 25° C. for 16 hours. LC-MS showed starting material was remained and one peak with desired MS was detected. The reaction mixture was basified with Sat.NaHCO₃ to pH=8 and extracted with ethyl acetate (30 mL*3). The combined organic layers were dried over Na₂SO₄, filtered and concentrated under reduce pressure. The residue was purified by prep-HPLC (column: Phenomenex Gemini-NX 80*30 mm*3 um; mobile phase: [water (0.05% NH₃H₂O+10 mM NH₄HCO₃)-ACN]; B %: 23%-53%, 9.5 min) to give the title compound as a light yellow solid. Compound N-[2-[(7-cyano-6,8-dihydro-5H-quinolin-7-yl)amino]-1-(cyclopropylmethyl)-2-oxo-ethyl]-4-methoxy-1H-indole-2-carboxamide (2.32 mg, 1.08% yield, 98.6% purity) was obtained as a light yellow solid.

LCMS: Rt=0.754 min; for C₂₆H₂₇N₅O₃ MS Calcd.: 457.21; MS Found: 458.1 [M+H⁺].

¹H NMR (400 MHz, CD₃OD) δ 8.37-8.24 (m, 1H), 7.65-7.56 (m, 1H), 7.29-7.12 (m, 3H), 7.03 (d, J=8.3 Hz, 1H), 6.52 (d, J=7.8 Hz, 1H), 4.64-4.60 (m, 1H), 3.93 (s, 3H), 3.76-3.57 (m, 1H), 3.45-3.33 (m, 1H), 3.17-2.94 (m, 2H), 2.60-2.36 (m, 2H), 1.88-1.78 (m, 1H), 1.75-1.60 (m, 1H), 0.89-0.72 (m, 1H), 0.56-0.41 (m, 2H), 0.24-0.12 (m, 2H).

¹H NMR (400 MHz, DMSO-d₆) δ 11.56 (s, 1H), 8.79 (d, J=15.8 Hz, 1H), 8.53-8.43 (m, 1H), 8.36 (dd, J=4.6, 11.4 Hz, 1H), 7.56 (d, J=7.5 Hz, 1H), 7.35 (d, J=14.3 Hz, 1H), 7.25-7.15 (m, 1H), 7.14-7.06 (m, 1H), 7.05-6.98 (m, 1H), 6.51 (d, J=7.5 Hz, 1H), 4.61-4.45 (m, 1H), 3.89 (s, 3H), 3.59 (d, J=16.8 Hz, 1H), 3.23 (d, J=16.8 Hz, 1H), 2.98-2.83 (m, 2H), 2.42 (dd, J=6.1, 12.9 Hz, 1H), 2.36-2.18 (m, 1H), 1.87-1.68 (m, 1H), 1.57-1.34 (m, 1H), 0.88-0.64 (m, 1H), 0.46-0.25 (m, 2H), 0.23-0.01 (m, 2H)

Example 106. Synthesis of Viral Protease Inhibitor Compound 323

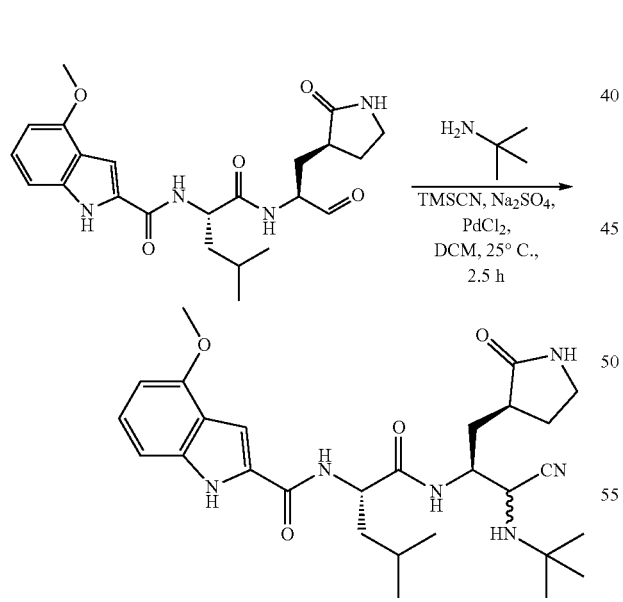

To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (100 mg, 180.79 umol, 80% purity, 1 eq) in DCM (5 mL) was added PdCl₂ (6.41 mg, 36.16 umol, 0.2 eq), Na₂SO₄ (89.88 mg, 632.76 umol, 64.20 uL, 3.5 eq) and 2-methylpropan-2-amine (26.44 mg, 361.58 umol, 37.99 uL, 2 eq). The mixture was stirred at 25° C. for 30 min, then added TMSCN (35.87 mg, 361.58 umol, 45.23 uL, 2 eq), the mixture was stirred at 25° C. for 2 h. Upon the reaction was completed. The reaction mixture was filtered and concentrated under reduced pressure to give a residue. The residue was purified by Hexane-IPA prep-HPLC to get the compound N-[(1S)-1-[[(1S)-2-(tert-butylamino)-2-cyano-1-[[(3S)-2-oxo pyrrolidin-3-yl]methyl]ethyl]carbamoyl]-3-methyl-butyl]-4-methoxy-1H-indole-2-carboxamide (16.10 mg, 25.59 umol, 14.16% yield, 83.4% purity) and N-[(1S)-1-[[(1S)-2-(tert-butylamino)-2-cyano-1-[[(3S)-2-oxopyrrolidin-3-yl]methyl]ethyl]carbamoyl]-3-methyl-butyl]-4-methoxy-1H-indole-2-carboxamide (7.92 mg, 12.27 umol, 6.79% yield, 81.3% purity) as white solid. MS (ESI) m/z 524.8 [M+H]⁺ column: Phenomenex luna CN 5 u 100*30 mm; mobile phase: [Hexane-IPA]; B %: 5%-60%, 10 min 1H NMR (400 MHz, DMSO-d6) δ=11.57 (s, 1H), 8.45-8.35 (m, 1H), 7.98 (d, J=9.3 Hz, 1H), 7.56 (s, 1H), 7.42-7.30 (m, 1H), 7.15-7.05 (m, 1H), 7.03-6.96 (m, 1H), 6.50 (d, J=7.6 Hz, 1H), 4.51-4.41 (m, 1H), 3.99-3.91 (m, 1H), 3.88 (s, 3H), 3.63 (dd, J=7.7, 10.2 Hz, 1H), 3.16-2.99 (m, 2H), 2.37-2.21 (m, 1H), 2.16-2.03 (m, 1H), 1.90-1.45 (m, 6H), 1.05-1.00 (m, 9H), 0.97-0.84 (m, 6H)

1H NMR (400 MHz, DMSO-d6) δ=11.81-11.42 (m, 1H), 8.62-7.84 (m, 2H), 7.69-7.47 (m, 1H), 7.42-7.28 (m, 1H), 7.20-6.94 (m, 2H), 6.50 (d, J=7.6 Hz, 1H), 4.61-4.40 (m, 1H), 4.13-3.58 (m, 5H), 3.23-2.91 (m, 2H), 2.38-1.98 (m, 3H), 1.91-1.37 (m, 5H), 1.12-1.00 (m, 9H), 0.97-0.79 (m, 6H)

Example 107. Synthesis of Viral Protease Inhibitor Compound 325

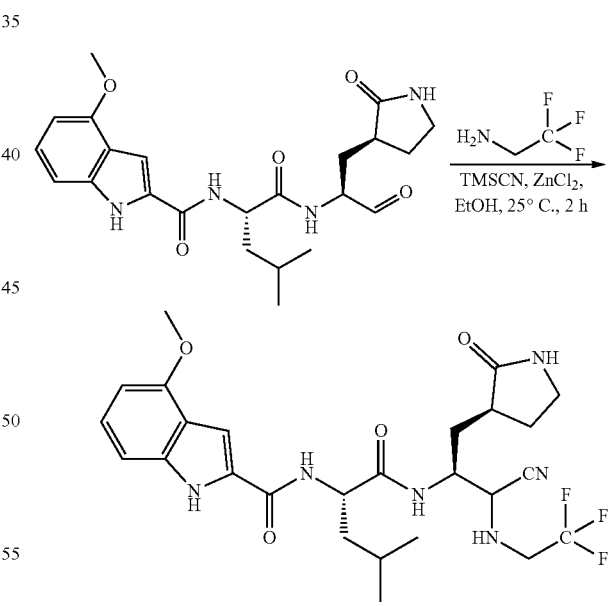

To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (180 mg, 325.42 umol, 80% purity, 1 eq) in EtOH (2 mL) was added 2,2,2-trifluoroethanamine (64.47 mg, 650.84 umol, 51.17 uL, 2 eq) and ZnCl₂ (8.87 mg, 65.08 umol, 3.05 uL, 0.2 eq). The mixture was stirred at 25° C. for 30 min, and then TMSCN (64.57 mg, 650.84 umol, 81.42 uL, 2 eq) was added. The mixture was stirred at 25° C. for 2 h. The residue was purified by HCl prep-HPLC to get the compound N-[(1S)-1-[[(1S)-2-cyano-1-[[(3S)-2-oxopyrrolidin-3-yl]methyl]-2-(2,2,2-trifluoroethylamino)ethyl]carbamoyl]-3-methyl-butyl]-4-methoxy-1H-indole-2-carboxamide (120 mg, 215.78 umol, 66.31% yield, 99% purity) as a white solid. MS (ESI) m/z 551.2 [M+H]+

Column: Phenomenex luna C18 80*40 mm*3 um; mobile phase: [water(0.04% HCl)-ACN]; B %: 38%-62%, 7 min ¹H NMR (400 MHz, DMSO-d6) δ=11.56 (dd, J=2.0, 5.5 Hz, 1H), 8.39 (br t, J=8.6 Hz, 1H), 8.32-8.16 (m, 1H), 7.59 (br d, J=17.6 Hz, 1H), 7.37 (dd, J=1.5, 5.7 Hz, 1H), 7.15-6.92 (m, 2H), 6.50 (d, J=7.7 Hz, 1H), 4.57-4.36 (m, 1H), 4.25-4.02 (m, 1H), 4.00-3.81 (m, 4H), 3.78-3.40 (m, 2H), 3.19-2.94 (m, 2H), 2.42-1.94 (m, 3H), 1.88-1.36 (m, 5H), 0.91 (dd, J=6.3, 15.1 Hz, 6H).

Example 108. Synthesis of Viral Protease Inhibitor Compound 327

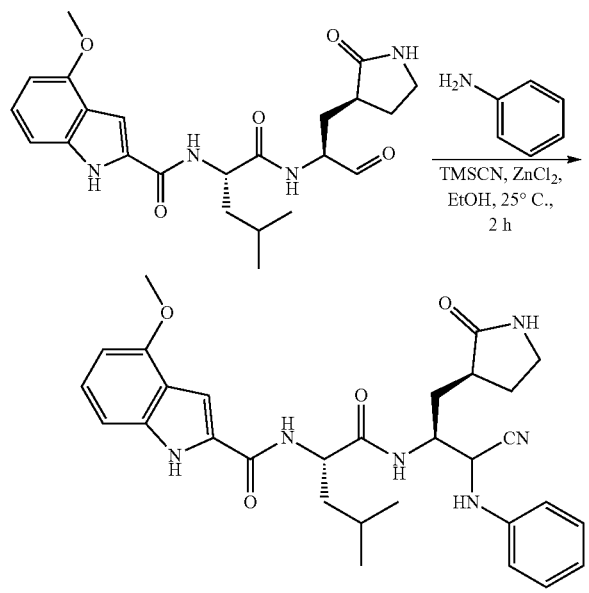

To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (180 mg, 325.42 umol, 80% purity, 1 eq) in EtOH (4 mL) was added ZnCl₂ (8.87 mg, 65.08 umol, 3.05 uL, 0.2 eq) and aniline (60.61 mg, 650.84 umol, 59.42 uL, 2 eq), and the mixture was stirred at 25° C. for 30 min. After the addition of TMSCN (64.57 mg, 650.84 umol, 81.42 uL, 2 eq), the mixture was stirred at 25° C. for 2 h. Upon the reaction was completed. The reaction mixture was filtered to get the product. The reaction mixture was purified by prep-HPLC to get the product N-[(1S)-1-[[(1S)-2-anilino-2-cyano-1-[[(3S)-2-oxopyrrolidin-3-yl]methyl]ethyl]carbamoyl]-3-methyl-butyl]-4-methoxy-1H-indole-2-carboxamide (70 mg, 122.10 umol, 37.52% yield, 95% purity) as a white solid. MS (ESI) m/z 545.3 [M+H]+

1H NMR (400 MHz, DMSO-d6) δ=11.59 (br d, J=2.0 Hz, 1H), 8.44 (br d, J=7.7 Hz, 1H), 8.26 (d, J=9.5 Hz, 1H), 7.63-7.51 (m, 1H), 7.38 (d, J=1.8 Hz, 1H), 7.26-6.94 (m, 4H), 6.80-6.65 (m, 3H), 6.51 (d, J=7.5 Hz, 1H), 6.34 (d, J=9.9 Hz, 1H), 4.59-4.20 (m, 3H), 3.89 (s, 3H), 3.18-2.95 (m, 2H), 2.44-2.30 (m, 1H), 2.24-2.00 (m, 1H), 1.97-1.43 (m, 6H), 0.99-0.82 (m, 6H)

Example 109. Synthesis of Viral Protease Inhibitor Compound 329

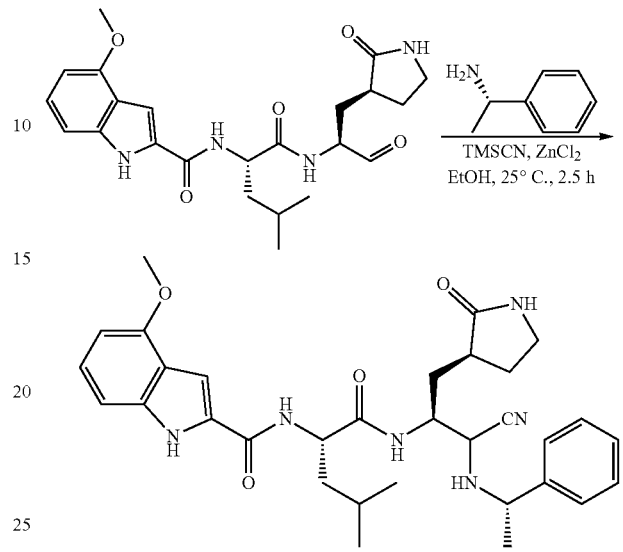

To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (100 mg, 180.79 umol, 80% purity, 1 eq) in EtOH (4 mL) was added (1S)-1-phenylethanamine (43.82 mg, 361.58 umol, 46.02 uL, 2 eq), ZnCl₂ (4.93 mg, 36.16 umol, 1.69 uL, 0.2 eq). The mixture was stirred at 25° C. for 30 min, and then TMSCN (35.87 mg, 361.58 umol, 45.24 uL, 2 eq) was added. After stirring the mixture at 25° C. for 2 h, the reaction mixture was filtered and concentrated under reduced pressure to give a residue. The residue was purified by HCl prep-HPLC to provide compound N-[(1 S)-1-[[(1S)-2-cyano-1-[[(3S)-2-oxopyrrolidin-3-yl]methyl]-2-[[(1S)-1-phenylethyl]amino]ethyl]carbamoyl]-3-methyl-butyl]-4-methoxy-1H-indole-2-carboxamide (90 mg, 154.01 umol, 85.19% yield, 98% purity) as a white solid. MS (ESI) m/z 573.2 [M+H]+ column: Phenomenex luna C18 80*40 mm*3 um; mobile phase: [water(0.04% HCl)-ACN]; B %: 40%-70%, 7 min 1H NMR (400 MHz, DMSO-d6) δ=11.39 (br s, 1H), 8.46-7.80 (m, 2H), 7.52-6.89 (m, 9H), 6.51 (br d, J=7.5 Hz, 1H), 4.64-4.35 (m, 1H), 4.26-4.03 (m, 1H), 3.96-3.83 (m, 4H), 3.36-3.03 (m, 3H), 2.37-1.51 (m, 8H), 1.39-1.21 (m, 3H), 0.90 (br dd, J=5.7, 14.6 Hz, 6H)

Example 110. Synthesis of Viral Protease Inhibitor Compound 331

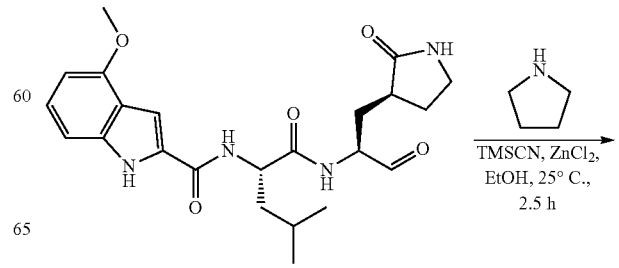

-continued

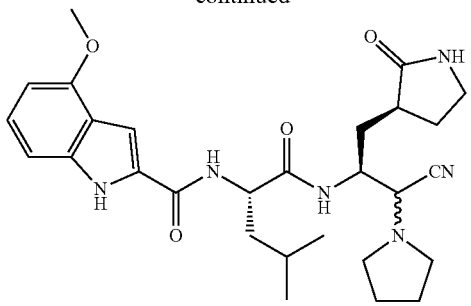

1H), 3.88 (s, 3H), 3.14-2.94 (m, 2H), 2.64-2.53 (m, 4H), 2.39-2.27 (m, 1H), 2.17-2.02 (m, 1H), 1.88-1.66 (m, 7H), 1.63-1.44 (m, 3H), 0.91 (dd, J=6.3, 16.2 Hz, 6H)

1H NMR (400 MHz, DMSO-d6) δ=11.56 (br d, J=1.8 Hz, 1H), 8.43-8.30 (m, 1H), 8.00 (d, J=9.2 Hz, 1H), 7.60 (s, 1H), 7.35 (d, J=1.8 Hz, 1H), 7.16-6.94 (m, 2H), 6.50 (d, J=7.6 Hz, 1H), 4.55-4.35 (m, 1H), 4.13-4.03 (m, 1H), 4.02-3.94 (m, 1H), 3.88 (s, 3H), 3.13-3.01 (m, 2H), 2.70-2.57 (m, 2H), 2.43-2.29 (m, 1H), 2.17-1.94 (m, 2H), 1.88-1.34 (m, 9H), 0.90 (dd, J=6.5, 15.2 Hz, 6H)

Example 111. Synthesis of Viral Protease Inhibitor Compound 345

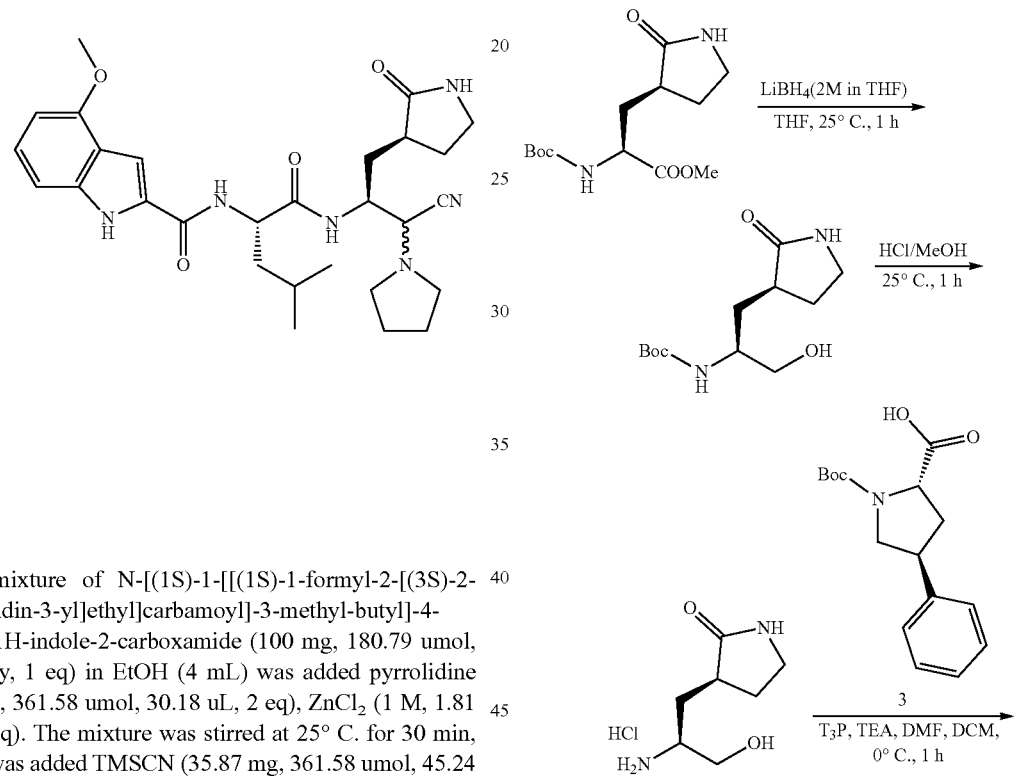

To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (100 mg, 180.79 umol, 80% purity, 1 eq) in EtOH (4 mL) was added pyrrolidine (25.72 mg, 361.58 umol, 30.18 uL, 2 eq), ZnCl₂ (1 M, 1.81 uL, 0.01 eq). The mixture was stirred at 25° C. for 30 min, and then was added TMSCN (35.87 mg, 361.58 umol, 45.24 uL, 2 eq). The mixture was stirred at 25° C. for 2 h, and then the reaction mixture was filtered and concentrated under reduced pressure to give a residue. The residue was purified by Hexane-IPA prep-HPLC to get the compound N-[(1S)-1-[[(1S)-2-cyano-1-[[(3S)-2-oxopyrrolidin-3-yl]methyl]-2-pyrrolidin-1-yl-ethyl]carbamoyl]-3-methyl-butyl]-4-methoxy-1H-indole-2-carboxamide (19.34 mg, 33.19 umol, 18.36% yield, 89.7% purity) and N-[(1S)-1-[[(1S)-2-cyano-1-[[(3S)-2-oxopyrrolidin-3-yl]methyl]-2-pyrrolidin-1-yl-ethyl]carbamoyl]-3-methyl-butyl]-4-methoxy-1H-indole-2-carboxamide (10.41 mg, 13.70 umol, 7.58% yield, 68.8% purity) as white solid. MS (ESI) m/z 523.4 [M+H]⁺ column: Phenomenex luna CN 5 u 100*30 mm; mobile phase: [Hexane-IPA]; B %: 5%-60%, 10 min 1H NMR (400 MHz, DMSO-d6) δ=11.58 (s, 1H), 8.43 (d, J=7.7 Hz, 1H), 8.19 (d, J=9.4 Hz, 1H), 7.61-7.50 (m, 1H), 7.38 (d, J=1.8 Hz, 1H), 7.14-6.95 (m, 2H), 6.50 (d, J=7.6 Hz, 1H), 4.54-4.35 (m, 1H), 4.17-4.00 (m, 1H), 3.99-3.92 (m,

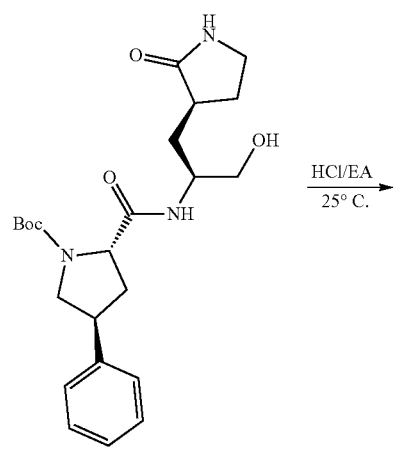

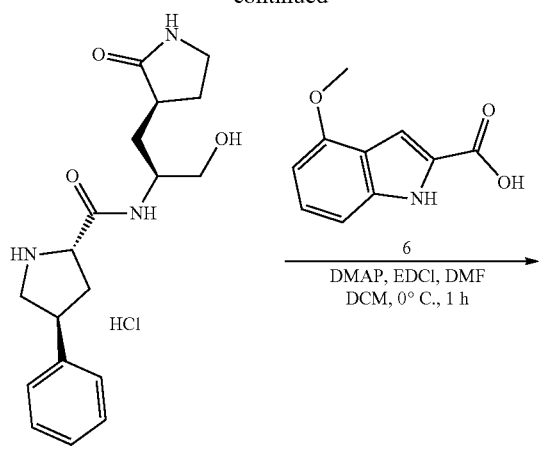

To a solution of methyl (2S)-2-(tert-butoxycarbonylamino)-3-[(3S)-2-oxopyrrolidin-3-yl]propanoate (2.00 g, 6.99 mmol, 1 eq) in THF (20 mL) was added LiBH4 (2 M, 6.99 mL, 2 eq) at 25° C. under N₂. The mixture was then stirred at 25° C. for 1 h. The mixture was quenched with NH₄Cl aq. (20.0 mL), and extracted with EtOAc (20.0 mL*5). The organic layers were washed with brine (20.0 mL), dried over Na₂SO₄, filtered, and concentrated under reduced pressure to give a residue. The residue was triturated with ethyl acetate:petroleum ether=1:2 at 25° C. for 1 h to give tert-butyl ((S)-1-hydroxy-3-((S)-2-oxopyrrolidin-3-yl)propan-2-yl)carbamate (1.57 g, crude) as white solid. MS (ESI) m/z 259.2 [M+H]⁺.

Step 2: (S)-3-((S)-2-amino-3-hydroxypropyl)pyrrolidin-2-one

A solution of tert-butyl ((S)-1-hydroxy-3-((S)-2-oxopyrrolidin-3-yl)propan-2-yl)carbamate (2.39 g, 9.25 mmol, 1 eq) in HCl/MeOH (4 M, 23.9 mL, 10.33 eq) was stirred at 25° C. for 1 h. The mixture was concentrated under reduced pressure to give (S)-3-((S)-2-amino-3-hydroxypropyl)pyrrolidin-2-one (1.8 g, crude, HCl) as a yellow oil.

Step 3: (2S,4S)-tert-butyl 2-(((S)-1-hydroxy-3-((S)-2-oxopyrrolidin-3-yl)propan-2-yl)carbamoyl)-4-phenylpyrrolidine-1-carboxylate To a solution of (S)-3-((S)-2-amino-3-hydroxypropyl)pyrrolidin-2-one (1.8 g, 9.25 mmol, 1 eq, HCl) in DMF (12 mL) and DCM (6 mL) was added TEA (5.61 g, 55.48 mmol, 7.72 mL, 6 eq), (2S,4S)-1-tert-butoxycarbonyl-4-phenylpyrrolidine-2-carboxylic acid (2.69 g, 9.25 mmol, 1 eq), then T3P (17.65 g, 27.74 mmol, 16.5 mL, 50% purity, 3 eq) at 0° C. After the mixture was stirred at 0° C. for 1 h, the mixture was quenched with water (40 mL) and extracted with EtOAc (20 mL*5). The organic layers were washed with brine (20.0 mL), dried over Na₂SO₄, filtered, concentrated under reduced pressure, and purified by column chromatography (SiO₂, DCM:MeOH=10:1 to 1:1) to give (2S,4S)-tert-butyl 2-(((S)-1-hydroxy-3-((S)-2-oxopyrrolidin-3-yl)propan-2-yl)carbamoyl)-4-phenylpyrrolidine-1-carboxylate (3.04 g, 6.69 mmol, 72.38% yield, 95% purity) as yellow solid. MS (ESI) m/z 432.2 [M+H]⁺.

Step 4: (2S,4S)-N-((S)-1-hydroxy-3-((S)-2-oxopyrrolidin-3-yl)propan-2-yl)-4-phenylpyrrolidine-2-carboxamide A mixture of (2S,4S)-tert-butyl 2-(((S)-1-hydroxy-3-((S)-2-oxopyrrolidin-3-yl)propan-2-yl)carbamoyl)-4-phenylpyrrolidine-1-carboxylate (3.04 g, 7.04 mmol, 1 eq) in HCl/EtOAc (4 M, 30 mL, 17.03 eq) was stirred at 25° C. for 1 h. The mixture was concentrated under reduced pressure to give (2S,4S)-N-((S)-1-hydroxy-3-((S)-2-oxopyrrolidin-3-yl)propan-2-yl)-4-phenylpyrrolidine-2-carboxamide (2.59 g, crude, HCl) as white solid. MS (ESI) m/z 332.2 [M+H]$^+$.

Step 5: (2S,4S)-N-((S)-1-hydroxy-3-((S)-2-oxopyrrolidin-3-yl)propan-2-yl)-1-(4-methoxy-1H-indole-2-carbonyl)-4-phenylpyrrolidine-2-carboxamide To a solution of (2S,4S)-N-((S)-1-hydroxy-3-((S)-2-oxopyrrolidin-3-yl)propan-2-yl)-4-phenylpyrrolidine-2-carboxamide (2.58 g, 7.01 mmol, 1 eq, HCl) in DMF (16 mL) and DCM (8 mL) was added 4-methoxy-1H-indole-2-carboxylic acid (1.34 g, 7.01 mmol, 1 eq), DMAP (1.71 g, 14.03 mmol, 2 eq), and EDCI (2.69 g, 14.03 mmol, 2 eq). The mixture was stirred at 0° C. for 1 h. The mixture was quenched with water (50.0 mL) and extracted with EtOAc (20.0 mL*4). The organic layers were washed with brine (20.0 mL), dried over Na$_2$SO$_4$, filtered, concentrated under reduced pressure, and purified by column chromatography (SiO$_2$, DCM:MeOH=10:1 to 3:1) to give (2S,4S)-N-((S)-1-hydroxy-3-((S)-2-oxopyrrolidin-3-yl)propan-2-yl)-1-(4-methoxy-1H-indole-2-carbonyl)-4-phenylpyrrolidine-2-carboxamide (2.1 g, 3.79 mmol, 54.00% yield, 91% purity) as light yellow solid. MS (ESI) m/z 505.1 [M+H]$^+$.

Step 6: (2S,4S)-1-(4-methoxy-1H-indole-2-carbonyl)-N-((S)-1-oxo-3-((S)-2-oxopyrrolidin-3-yl)propan-2-yl)-4-phenylpyrrolidine-2-carboxamide To a mixture of (2S,4S)-N-((S)-1-hydroxy-3-((S)-2-oxopyrrolidin-3-yl)propan-2-yl)-1-(4-methoxy-1H-indole-2-carbonyl)-4-phenylpyrrolidine-2-carboxamide (200 mg, 376.55 umol, 95% purity, 1 eq) in DMSO (2 mL) was added TFA (64.40 mg, 564.83 umol, 41.82 uL, 1.5 eq) and IBX (332.97 mg, 1.13 mmol, 95% purity, 3 eq), the mixture was stirred at 25° C. for 14 h. The mixture was quenched with NaHCO$_3$ aq. (15.0 mL) and extracted with EtOAc (10.0 mL*3). The organic layers were washed with brine (10.0 mL), dried over Na$_2$SO$_4$, filtered, concentrated under reduced pressure, and purified by prep-HPLC to give (2S,4S)-1-(4-methoxy-1H-indole-2-carbonyl)-N-((S)-1-oxo-3-((S)-2-oxopyrrolidin-3-yl)propan-2-yl)-4-phenylpyrrolidine-2-carboxamide (58 mg, 111.95 umol, 29.73% yield, 97.0% purity) as white solid. MS (ESI) m/z 503.2 [M+H]$^+$.

prep-HPLC condition: column: Waters Xbridge BEH C18 100*30 mm*10 um; mobile phase: [water (10 mM NH4HCO3)-ACN]; B %: 20%-50%, 10 min.

$^1$H NMR (400 MHz, DMSO-d$_6$) δ ppm 11.66-11.41 (m, 1H), 9.51-7.92 (m, 1H), 7.82-7.47 (m, 1H), 7.43-7.20 (m, 5H), 7.17-6.98 (m, 2H), 6.98-6.78 (m, 1H), 6.55-6.39 (m, 1H), 5.83-5.67 (m, 1H), 4.84-4.59 (m, 1H), 4.48-4.35 (m, 1H), 4.32-4.12 (m, 1H), 3.94-3.66 (m, 4H), 3.64-3.39 (m, 1H), 3.20-3.03 (m, 1H), 2.98-2.54 (m, 1H), 2.47-2.12 (m, 3H), 2.03-1.78 (m, 1H), 1.72-1.22 (m, 2H)

Step 7: (2S,4S)-N-((2S)-1-cyano-1-hydroxy-3-((S)-2-oxopyrrolidin-3-yl)propan-2-yl)-1-(4-methoxy-1H-indole-2-carbonyl)-4-phenylpyrrolidine-2-carboxamide To a mixture of (2S,4S)-1-(4-methoxy-1H-indole-2-carbonyl)-N-((S)-1-oxo-3-((S)-2-oxopyrrolidin-3-yl)propan-2-yl)-4-phenylpyrrolidine-2-carboxamide (90 mg, 179.08 umol, 1 eq) in DCM (1 mL) was added a solution of NaHSO$_3$ (74.54 mg, 716.33 umol, 50.37 uL, 4 eq) in H$_2$O (0.5 mL), and then KCN (46.64 mg, 716.33 umol, 30.69 uL, 4 eq) at 0° C. The mixture was stirred at 25° C. for 14 h. The mixture was quenched with water (15.0 mL) and extracted with EtOAc (10.0 mL*3). The organic layers were washed with brine (10.0 mL), dried over Na$_2$SO$_4$, filtered, concentrated under reduced pressure, and purified by prep-HPLC to give (2S,4S)-N-((2S)-1-cyano-1-hydroxy-3-((S)-2-oxopyrrolidin-3-yl)propan-2-yl)-1-(4-methoxy-1H-indole-2-carbonyl)-4-phenylpyrrolidine-2-carboxamide (29 mg, 54.76 umol, 30.58% yield, 100% purity) as white solid. MS (ESI) m/z 530.2 [M+H]$^+$.

prep-HPLC condition: column: Phenomenex luna C18 80*40 mm*3 um; mobile phase: [water(0.04% HCl)-ACN]; B %: 32%-48%, 7 min.

$^1$H NMR (400 MHz, DMSO-d$_6$) δ ppm 11.66-11.42 (m, 1H), 8.63-8.22 (m, 1H), 7.62 (d, J=5.6 Hz, 0.5H), 7.44 (s, 0.5H), 7.41-7.29 (m, 4H), 7.29-7.21 (m, 1H), 7.15-7.07 (m, 1H), 7.06-6.99 (m, 1H), 6.98-6.92 (m, 0.5H), 6.86-6.78 (m, 0.5H), 6.70 (s, 1H), 6.53-6.41 (m, 1H), 5.32-5.18 (m, 0.5H), 4.86-4.66 (m, 0.5H), 4.66-4.54 (m, 0.5H), 4.45-4.34 (m, 1H), 4.24-4.15 (m, 0.5H), 4.12-3.96 (m, 1H), 3.95-3.87 (m, 0.5H), 3.87-3.76 (m, 3H), 3.76-3.66 (m, 0.5H), 3.64-3.56 (m, 0.5H), 3.52-3.42 (m, 1H), 3.20-3.09 (m, 1H), 2.85-2.74 (0.5, 1H), 2.62-2.54 (m, 0.5H), 2.46-2.35 (m, 1.511), 2.30-1.98 (m, 2H), 1.92-1.80 (m, 0.5H), 1.68-1.19 (m, 2.5H).

Step 8: (2S,4S)-N-((2S)-1-cyano-1-hydroxy-3-((S)-2-oxopyrrolidin-3-yl)propan-2-yl)-1-(4-methoxy-1H-indole-2-carbonyl)-4-phenylpyrrolidine-2-carboxamide (2S,4S)-N-((2S)-1-cyano-1-hydroxy-3-((S)-2-oxopyrrolidin-3-yl)propan-2-yl)-1-(4-methoxy-1H-indole-2-carbonyl)-4-phenylpyrrolidine-2-carboxamide (27 mg, 50.98 umol, 1 eq) was purified by SFC separation to give (2S,4S)-N-((2S)-1-cyano-1-hydroxy-3-((S)-2-oxopyrrolidin-3-yl)propan-2-yl)-1-(4-methoxy-1H-indole-2-carbonyl)-4-phenylpyrrolidine-2-carboxamide (13.03 mg, 22.71 umol, 44.54% yield, 92.3% purity) as a white solid. MS (ESI) m/z 530.2 [M+H]$^+$, (2S,4S)-N-((2S)-1-cyano-1-hydroxy-3-((S)-2-oxopyrrolidin-3-yl)propan-2-yl)-1-(4-methoxy-1H-indole-2-carbonyl)-4-phenylpyrrolidine-2-carboxamide (12.12 mg, 19.86 umol, 38.96% yield, 86.8% purity) as white solid. MS (ESI) m/z 530.2 [M+H]$^+$.

Isomer 1: $^1$H NMR (400 MHz, DMSO-d$_6$) δ ppm 11.64-11.47 (m, 1H), 8.62-8.30 (m, 1H), 7.64 (s, 0.5H), 7.45 (s, 0.511), 7.42-7.30 (m, 4H), 7.30-7.21 (m, 1H), 7.16-7.06 (m, 1H), 7.05-6.99 (m, 1H), 6.97-6.92 (m, 0.511), 6.86-6.80 (m, 0.5H), 6.75-6.65 (m, 1H), 6.53-6.41 (m, 1H), 5.32-5.23 (m, 0.511), 4.85-4.78 (m, 0.5H), 4.66-4.54 (m, 1H), 4.45-4.35 (m, 0.5H), 4.24-4.14 (m, 0.5H), 4.13-3.98 (m, 1H), 3.95-3.87 (m, 0.5H), 3.87-3.75 (m, 3H), 3.75-3.66 (m, 0.5H), 3.64-3.56 (m, 0.5H), 3.53-3.41 (m, 0.5H), 3.22-3.11 (m, 1H), 2.80 (t, J=8.8 Hz, 0.5H), 2.62-2.53 (m, 0.5H), 2.46-2.36 (m, 2H), 2.29-2.15 (m, 1.5H), 2.14-1.97 (m, 1H), 1.69-1.54 (m, 0.511), 1.51-1.12 (m, 2.5H)

Isomer 2: $^1$H NMR (400 MHz, DMSO-d$_6$) δ ppm 11.64-11.506 (m, 1H), 8.48 (d, J=9.6 Hz, 0.511), 8.29 (d, J=9.6 Hz, 0.511), 7.62 (s, 0.511), 7.44 (s, 0.5H), 7.40-7.31 (m, 4H), 7.29-7.23 (m, 1H), 7.11 (q, J=8.4 Hz, 1H), 7.05-6.99 (m, 1H), 6.98-6.94 (s, 0.5H), 6.84-6.78 (m, 0.5H), 6.77-6.69 (m, 1H), 6.52-6.42 (m, 1H), 5.23 (d, J=7.2 Hz, 0.511), 4.70 (d, J=6.8 Hz, 0.5H), 4.48-4.32 (m, 1H), 4.26-4.15 (m, 0.5H), 4.13-3.95 (m, 1H), 3.94-3.88 (m, 0.5H), 3.86-3.76 (m, 3H), 3.76-3.69 (m, 0.511), 3.66-3.53 (m, 0.5H), 3.51-3.40 (m, 0.511), 3.20-3.09 (m, 1H), 2.84-2.74 (m, 1H), 2.45-2.35 (m, 2H), 2.31-2.11 (m, 2H), 1.92-1.80 (m, 1H), 1.60-1.21 (m, 3H)

Example 112. Synthesis of Viral Protease Inhibitor Compound 355

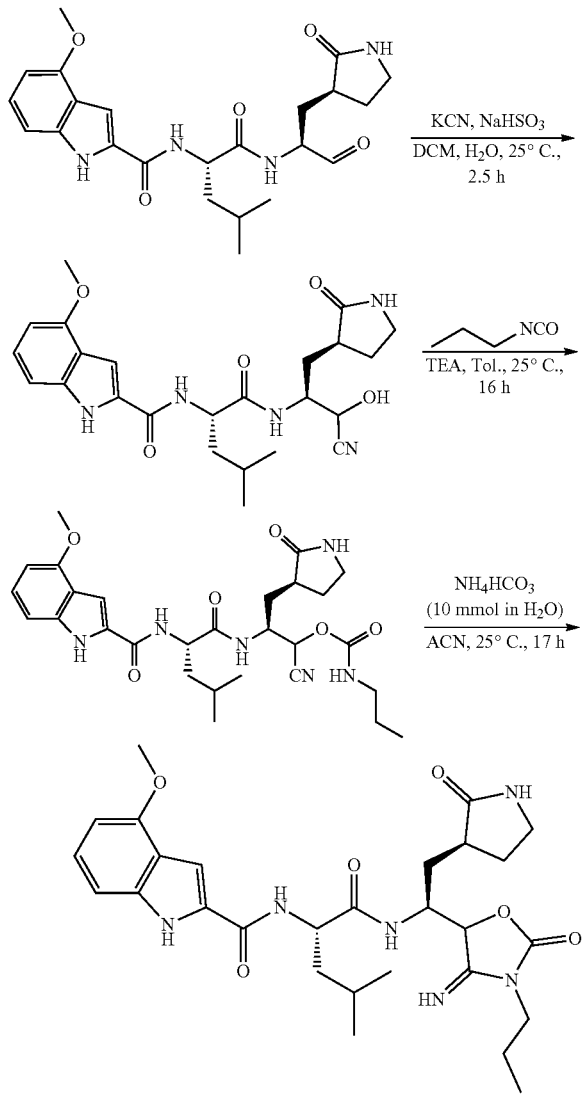

Step 1: N-((2S)-1-(((2S)-1-cyano-1-hydroxy-3-((S)-2-oxopyrrolidin-3-yl)propan-2-yl)amino)-4-methyl-1-oxopentan-2-yl)-4-methoxy-1H-indole-2-carboxamide To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (150 mg, 338.98 umol, 1 eq) in DCM (2 mL) was added saturated NaHSO₃ (35.27 mg, 338.98 umol, 23.83 uL, 1 eq), and the mixture was stirred at 25° C. for 30 min. A solution of KCN (100 mg, 1.54 mmol, 65.79 uL, 4.53 eq) in H₂O (0.5 mL) was added, and the mixture was stirred at 25° C. for 2 h. Upon completion, the organic phase was collected and the aqueous layer was extracted with DCM (30 mL*3). The combined organic phase was washed with brine (30 mL*2), dried over Na₂SO₄, and concentrated to get the crude. The liquid water was added NaOH to pH=9, then quenched by aq NaClO, then added NaOH to pH>14. The crude was used to next step directly and without further purification. N-[(1S)-1-[[(1S)-2-cyano-2-hydroxy-1-[[(3S)-2-oxopyrrolidin-3-yl]methyl]ethyl]carbamoyl]-3-methyl-butyl]-4-methoxy-1H-indole-2-carboxamide (140 mg, crude) was obtained as yellow solid. MS (ESI) m/z 470.1 [M+H]⁺.

Step 2: (2S)-1-cyano-2-((S)-2-(4-methoxy-1H-indole-2-carboxamido)-4-methylpentanamido)-3-((S)-2-oxopyrrolidin-3-yl)propyl propylcarbamate A solution of 1-isocyanatopropane (27.19 mg, 319.47 umol, 30.21 uL, 5 eq) in dry toluene (0.1 mL) was added dropwise to a solution of the N-[(1S)-1-[[(1S)-2-cyano-2-hydroxy-1-[[(3S)-2-oxopyrrolidin-3-yl]methyl]ethyl]carbamoyl]-3-methyl-butyl]-4-methoxy-1H-indole-2-carboxamide (30 mg, 63.89 umol, 1 eq) in dry toluene (0.5 mL) at 0° C., then the TEA (64.65 ug, 6.39 e−1 umol, 8.89 e−2 uL, 0.01 eq) was added and the solution was stirred at 25° C. for 17 h under N₂. Upon completion, the solution was concentrated to give the crude. The residue was purified by prep-HPLC (FA condition), column: Phenomenex Luna C18 200*40 mm*10 um; mobile phase: [water (0.2% FA)-ACN]; B %: 30%-80%, 8 min. [(2S)-1-cyano-2-[[(2S)-2-[(4-methoxy-1H-indole-2-carbonyl) amino]-4-methyl-pentanoyl] amino]-3-[(3S)-2-oxopyrrolidin-3-yl] propyl] N-propylcarbamate (8 mg, 14.15 umol, 22.15% yield, 98.124% purity) was obtained as white solid.
¹H NMR (400 MHz, METHANOL-d₄) δ=7.27 (s, 1H), 7.19-7.10 (m, 1H), 7.02 (d, J=8.3 Hz, 1H), 6.51 (d, J=7.7 Hz, 1H), 5.48-5.40 (m, 1H), 4.64-4.53 (m, 1H), 4.46-4.34 (m, 1H), 3.93 (s, 3H), 3.29-3.19 (m, 2H), 3.15-3.03 (m, 2H), 2.72-2.57 (m, 1H), 2.34-2.11 (m, 2H), 1.89-1.44 (m, 7H), 1.07-0.88 (m, 9H). MS (ESI) m/z 555.3 [M+H]⁺.

Step 3: N-((2S)-1-(((1S)-1-(4-imino-2-oxo-3-propyloxazolidin-5-yl)-2-((S)-2-oxopyrrolidin-3-yl)ethyl)amino)-4-methyl-1-oxopentan-2-yl)-4-methoxy-1H-indole-2-carboxamide A mixture of [(2S)-1-cyano-2-[[(2S)-2-[(4-methoxy-1H-indole-2-carbonyl) amino]-4-methyl-pentanoyl] amino]-3-[(3S)-2-oxopyrrolidin-3-yl] propyl] N-propylcarbamate (50 mg, 90.15 umol, 1 eq) in NH₄HCO₃ (0.01 M, 45.07 mL, 5 eq) and ACN (5 mL) was stirred at 25° C. for 17 h. Upon completion, the solution was extracted with EA (40 mL*3), the combined organic phase was dried over Na₂SO₄, filtrated and concentrated to give the crude. The residue was purified by prep-HPLC, column: Waters Xbridge Prep OBD C18 150*40 mm*10 um; mobile phase: [water (10 mM NH₄HCO₃)-ACN]; B %: 25%-55%, 8 mm. N-[(1S)-1-[[(1S)-1-(4-imino-2-oxo-3-propyl-oxazolidin-5-yl)-2-[(3S)-2-oxopyrrolidin-3-yl]ethyl]carbamoyl]-3-methyl-butyl]-4-methoxy-1H-indole-2-carboxamide (20 mg, 34.21 umol, 16.06% yield, 94.871% purity) was obtained as white solid.
¹H NMR (400 MHz, METHANOL-d₄) δ=7.31-7.21 (m, 1H), 7.19-7.10 (m, 1H), 7.06-6.98 (m, 1H), 6.56-6.46 (m, 1H), 5.16-5.03 (m, 1H), 4.79-4.37 (m, 2H), 3.96-3.88 (m, 3H), 3.58-3.40 (m, 2H), 3.28-3.13 (m, 2H), 2.65-2.51 (m, 1H), 2.41-2.05 (m, 2H), 1.90-1.40 (m, 7H), 1.07-0.87 (m, 9H).

Example 113. Synthesis of Viral Protease Inhibitor Compound 357

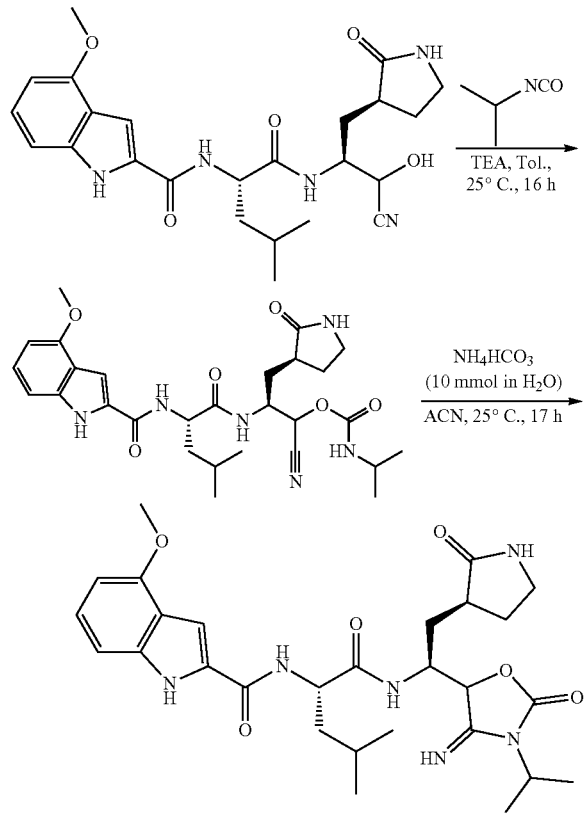

A solution of 2-isocyanatopropane (10.88 mg, 127.79 umol, 12.53 uL, 3 eq) in dry toluene (0.1 mL) was added dropwise to a solution of the N-[(1S)-1-[[(1S)-2-cyano-2-hydroxy-1-[[(3S)-2-oxopyrrolidin-3-yl]methyl]ethyl]carbamoyl]-3-methyl-butyl]-4-methoxy-1H-indole-2-carboxamide (20 mg, 42.60 umol, 1 eq) in dry toluene (0.5 mL) at 0° C. After the addition of TEA (4.31 mg, 42.60 umol, 5.93 uL, 1 eq), the solution was stirred at 25° C. for 16 h under dry argon atmosphere. Upon completion, the solution was concentrated to remove the toluene. The residue was purified by prep-HPLC (FA condition), column: Phenomenex Luna C18 75*30 mm*3 um; mobile phase: [water (0.2% FA)-ACN]; B %: 30%-70%, 8 min. [(2S)-1-cyano-2-[[(2S)-2-[(4-methoxy-1H-indole-2-carbonyl) amino]-4-methyl-pentanoyl] amino]-3-[(3S)-2-oxopyrrolidin-3-yl] propyl] N-isopropylcarbamate (8 mg, 14.30 umol, 33.57% yield, 99.129% purity) was obtained as white solid.

$^1$H NMR (400 MHz, METHANOL-$d_4$) δ=7.27 (s, 1H), 7.19-7.10 (m, 1H), 7.02 (d, J=8.4 Hz, 1H), 6.51 (d, J=7.7 Hz, 1H), 5.48-5.39 (m, 1H), 4.64-4.53 (m, 1H), 4.44-4.33 (m, 1H), 3.93 (s, 3H), 3.80-3.64 (m, 1H), 3.28-3.17 (m, 2H), 2.72-2.58 (m, 1H), 2.34-2.10 (m, 2H), 1.88-1.58 (m, 5H), 1.23-1.09 (m, 6H), 1.01 (td, J=5.7, 11.5 Hz, 6H). MS (ESI) m/z 555.3 [M+H]$^+$.

Step 2: N-((2S)-1-(((1S)-1-(4-imino-3-isopropyl-2-oxooxazolidin-5-yl)-2-((S)-2-oxopyrrolidin-3-yl) ethyl)amino)-4-methyl-1-oxopentan-2-yl)-4-methoxy-1H-indole-2-carboxamide

[(2S)-1-cyano-2-[[(2S)-2-[(4-methoxy-1H-indole-2-carbonyl) amino]-4-methyl-pentanoyl] amino]-3-[(3S)-2-oxopyrrolidin-3-yl] propyl] N-isopropylcarbamate (110 mg, 198.33 umol, 1 eq) in NH$_4$HCO$_3$ (0.01 M, 30 mL, 1.51 eq)/ACN (5 mL) was stirred at 25° C. for 17 h. Upon completion, the solution was extracted with ethyl acetate (30 mL*3); the combined organic phase was dried over Na$_2$SO$_4$, filtrated and concentrated to give the crude. The residue was purified by prep-HPLC (neutral condition), column: Waters Xbridge Prep OBD C18 150*40 mm*10 um; mobile phase: [water (10 mM NH4HCO3)-ACN]; B %: 20%-50%, 8 min. N-[(1 S)-1-[[(1 S)-1-(4-imino-3-isopropyl-2-oxo-oxazolidin-5-yl)-2-[(3S)-2-oxopyrrolidin-3-yl]ethyl]carbamoyl]-3-methyl-butyl]-4-methoxy-1H-indole-2-carboxamide (27 mg, 48.55 umol, 24.48% yield, 99.738% purity) was obtained as white solid. $^1$H NMR (400 MHz, METHANOL-$d_4$) δ=7.33-7.21 (m, 1H), 7.19-7.10 (m, 1H), 7.07-6.97 (m, 1H), 6.57-6.46 (m, 1H), 5.06-4.96 (m, 1H), 4.73 (br d, J=11.2 Hz, 1H), 4.64-4.53 (m, 1H), 4.44-4.28 (m, 1H), 3.96-3.89 (m, 3H), 3.27-3.15 (m, 2H), 2.66-2.49 (m, 1H), 2.43-2.15 (m, 2H), 1.85-1.24 (m, 4H), 1.07-0.91 (m, 6H)

Example 114. Synthesis of Viral Protease Inhibitor Compound 359

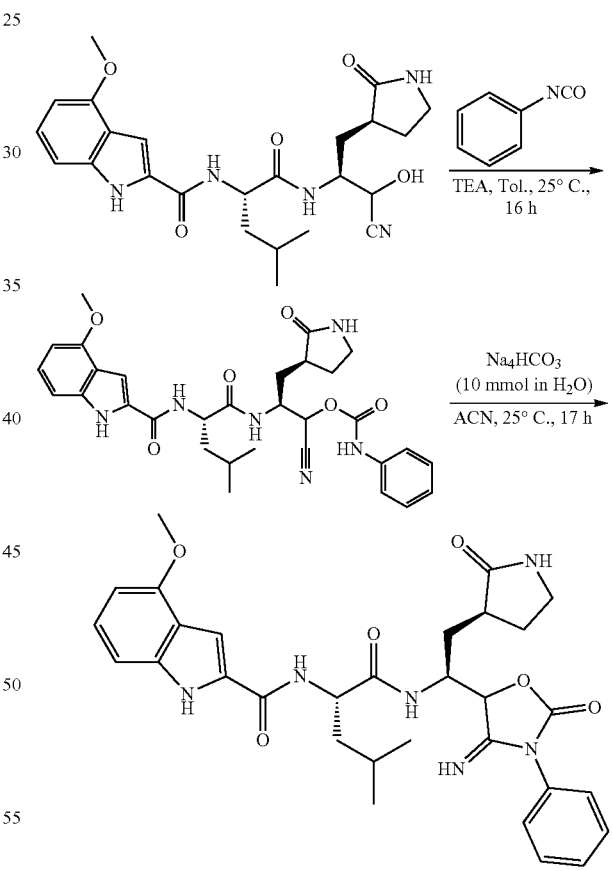

A solution of isocyanatobenzene (127 mg, 1.07 mmol, 115.32 uL, 5 eq) in dry toluene (0.2 mL) was added dropwise to a solution of the N-[(1S)-1-[[(1S)-2-cyano-2-hydroxy-1-[[(3S)-2-oxopyrrolidin-3-yl]methyl]ethyl]carbamoyl]-3-methyl-butyl]-4-methoxy-1H-indole-2-carboxamide (100 mg, 212.98 umol, 1 eq) in dry toluene (1 mL) at 0° C., and then the TEA (215.51 ug, 2.13 umol, 2.96 e−1 uL, 0.01 eq) was added. After the solution was stirred at 25° C. for 16 h under dry argon atmosphere, the solution was quenched with H₂O (10 mL), extracted with ethyl acetate (20 mL*3), the combined organic phase was dried over Na₂SO₄, filtrated and concentrated to give the crude. The crude was used to next step directly and without further purification. (2S)-1-cyano-2-((S)-2-(4-methoxy-1H-indole-2-carboxamido)-4-methylpentanamido)-3-((S)-2-oxopyrrolidin-3-yl) propyl phenylcarbamate (50 mg, 84.94 umol, 1 eq) was obtained as white solid. MS (ESI) m/z 589.2 [M+H]⁺.

Step 2: N-[(1S)-1-[[(1S)-1-(4-imino-2-oxo-3-phenyl-oxazolidin-5-yl)-2-[(3S)-2-oxopyrrolidin-3-yl]ethyl]carbamoyl]-3-methyl-butyl]-4-methoxy-1H-indole-2-carboxamide

[(2S)-1-cyano-2-[[(2S)-2-[(4-methoxy-1H-indole-2-carbonyl) amino]-4-methyl-pentanoyl] amino]-3-[(3S)-2-oxopyrrolidin-3-yl] propyl] N-phenylcarbamate (50 mg, 84.94 umol, 1 eq) in the solution of NH₄HCO₃ (0.01 M, 42.47 mL, 5 eq) and ACN (3 mL) was stirred at 25° C. for 17 h. Upon completion, the solution was extracted with ethyl acetate (40 mL*3), and the combined organic phase was dried over Na₂SO₄, filtrated and concentrated to give the crude, the residue was purified by prep-HPLC (neutral condition), column: Waters Xbridge BEH C18 100*30 mm*10 um; mobile phase: [water (10 mM NH₄HCO₃)-ACN]; B %: 25%-50%, 8 min. N-[(1S)-1-[[(1S)-1-(4-imino-2-oxo-3-phenyl-oxazolidin-5-yl)-2-[(3S)-2-oxopyrrolidin-3-yl]ethyl]carbamoyl]-3-methyl-butyl]-4-methoxy-1H-indole-2-carboxamide (6 mg, 9.70 umol, 11.42% yield, 95.16% purity) was obtained as white solid. ¹H NMR (400 MHz, METHANOL-d₄) δ=7.60-7.38 (m, 4H), 7.38-7.20 (m, 2H), 7.18-7.10 (m, 1H), 7.07-6.98 (m, 1H), 6.55-6.46 (m, 1H), 5.29-5.15 (m, 1H), 4.85-4.74 (m, 1H), 4.61-4.47 (m, 1H), 3.98-3.87 (m, 3H), 3.29-3.18 (m, 2H), 2.72-2.56 (m, 1H), 2.48-2.20 (m, 2H), 1.91-1.42 (m, 5H), 1.08-0.85 (m, 6H) MS (ESI) m/z 589.3 [M+H]⁺.

Example 115. Synthesis of Viral Protease Inhibitor Compound 361

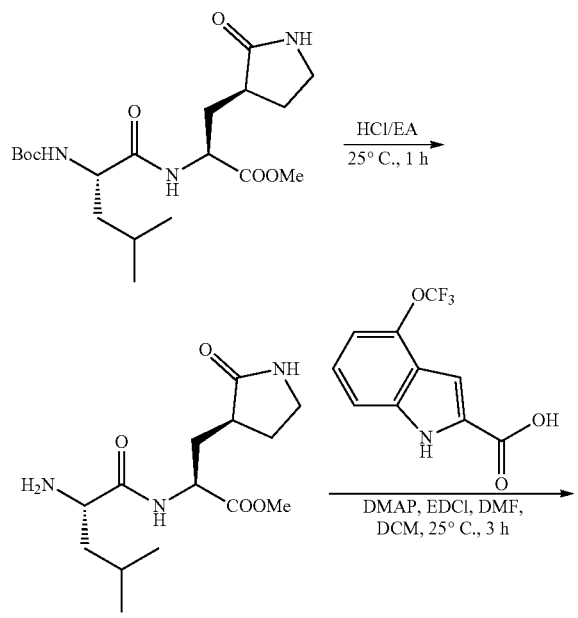

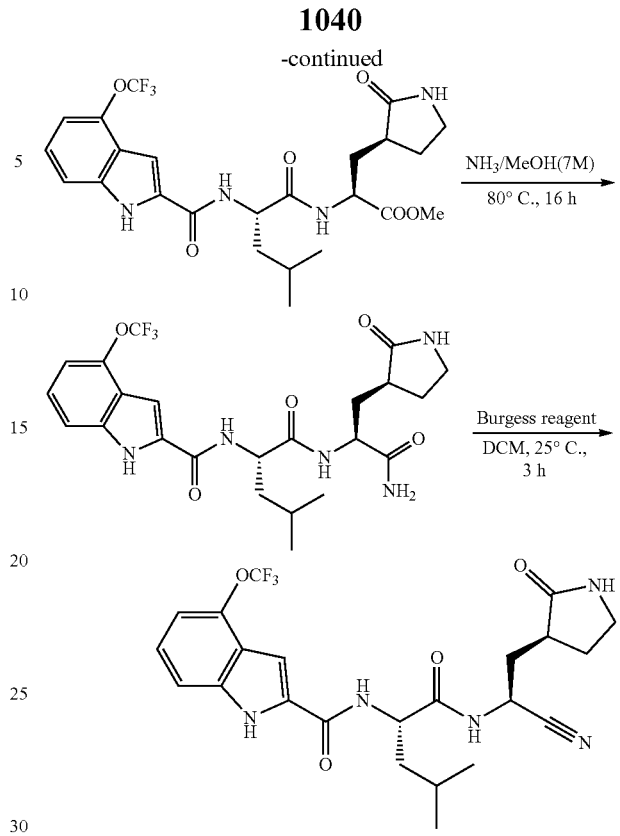

A mixture of methyl (2S)-2-[[(2S)-2-(tert-butoxycarbonylamino)-4-methyl-pentanoyl]amino]-3-[(3S)-2-oxopyrrolidin-3-yl]propanoate (500 mg, 1.25 mmol, 1 eq) in HCl/EtOAc (20 mL) was stirred at 25° C. for 1 h. TLC showed the reaction was finished. The reaction was concentrated to give the crude methyl (2S)-2-[[(2S)-2-amino-4-methyl-pentanoyl]amino]-3-[(3S)-2-oxopyrrolidin-3-yl]propanoate (360 mg, crude) as colorless oil. Crude product was used directly without further purification. MS (ESI) m/z 299.2 [M+H]⁺

Step 2: methyl (2S)-2-[[(2S)-4-methyl-2-[[4-(trifluoromethoxy)-1H-indole-2-carbonyl]amino]pentanoyl]amino]-3-[(3S)-2-oxopyrrolidin-3-yl]propanoate To a mixture of methyl (2S)-2-[[(2S)-2-amino-4-methyl-pentanoyl]amino]-3-[(3S)-2-oxopyrrolidin-3-yl]propanoate (300 mg, 901.91 umol, 90% purity, 1 eq) and 4-(trifluoromethoxy)-1H-indole-2-carboxylic acid (221.11 mg, 901.91 umol, 1 eq) in DCM (12 mL) and DMF (4 mL) was added EDCI (691.58 mg, 3.61 mmol, 4 eq) and DMAP (440.74 mg, 3.61 mmol, 4 eq). The mixture was stirred at 25° C. and stirred for 3 hours.

LCMS showed the reaction was finished. The residue was concentrated in vacuum. The residue was purified by prep-HPLC (column: Kromasil C18 (250*50 mm*10 um); mobile phase: [water (10 mM NH₄HCO₃)-ACN]; B %: 30%-70%, 10 min) to give methyl (2S)-2-[[(2S)-4-methyl-2-[[4-(trifluoromethoxy)-1H-indole-2-carbonyl]amino]pentanoyl]amino]-3-[(3S)-2-oxopyrrolidin-3-yl]propanoate (250 mg, 427.35 umol, 47.38% yield, 90% purity) as white solid. MS (ESI) m/z 526.2 [M+H]⁺

Step 3: N-[(1S)-1-[[(1S)-2-amino-2-oxo-1-[[(3S)-2-oxopyrrolidin-3-yl]methyl]ethyl]carbamoyl]-3-methyl-butyl]-4-(trifluoromethoxy)-1H-indole-2-carboxamide A mixture of methyl (2S)-2-[[(2S)-4-methyl-2-[[4-(trifluoromethoxy)-1H-indole-2-carbonyl]amino]pentanoyl]amino]-3-[(3S)-2-oxopyrrolidin-3-yl]propanoate (250 mg, 474.83 umol, 1 eq) in ammonia (29.14 g, 1.71 mol, 28.57 mL, 3603.85 eq) was stirred at 80° C. and stirred for 16 hours. LCMS showed the reaction was finished. The reaction was concentrated to give the crude N-[(1S)-1-[[(1S)-2-amino-2-oxo-1-[[(3S)-2-oxopyrrolidin-3-yl]methyl]ethyl]carbamoyl]-3-methyl-butyl]-4-(trifluoromethoxy)-1H-indole-2-carboxamide (200 mg, crude) (white solid). Crude product was used directly without further purification. MS (ESI) m/z 511.2 [M+H]$^+$

Step 4: N-[(1S)-1-[[(1S)-1-cyano-2-[(3S)-2-oxopyrrolidin-3-yl]ethyl]carbamoyl]-3-methyl-butyl]-4-(triuoromethoxy)-1H-indole-2-carboxamide To a mixture of N-[(1S)-1-[[(1S)-2-amino-2-oxo-1-[[(3S)-2-oxopyrrolidin-3-yl]methyl]ethyl]carbamoyl]-3-methyl-butyl]-4-(trifluoromethoxy)-1H-indole-2-carboxamide (35 mg, 68.43 umol, 1 eq) in DCM (2 mL) was added Burgess reagent (65.23 mg, 273.71 umol, 4 eq). The mixture was stirred at 25° C. and stirred for 3 hours. LCMS and HPLC showed the reaction was finished. The reaction was concentrated and purified by prep-HPLC (column: Phenomenex Gemini-NX C18 75*30 mm*3 um; mobile phase: [water (10 mm NH$_4$HCO$_3$)-ACN]; B %: 35%-55%, 8 min) to give N-[(1S)-1-[[(1S)-1-cyano-2-[(3S)-2-oxopyrrolidin-3-yl]ethyl]carbamoyl]-3-methyl-butyl]-4-(trifluoromethoxy)-1H-indole-2-carboxamide (10.02 mg, 20.30 umol, 29.67% yield, 100% purity) (white solid). MS (ESI) m/z 493.2 [M+H]$^+$ $^1$H NMR (400 MHz, METHANOL-d$_4$) δ ppm 12.04 (s, 1H), 8.94-9.08 (m, 1H), 8.72-8.74 (d, J=7.60 Hz, 1H), 7.71-7.76 (m, 1H), 7.44-7.46 (d, J=7.60 Hz, 2H), 7.21-7.23 (m, 1H), 7.02-7.05 (d, J=7.60 Hz, 1H), 4.97-5.01 (m, 1H), 4.47-4.50 (m, 1H), 3.10-3.14 (m, 2H), 2.14-2.15 (m, 1H), 2.01-2.10 (m, 2H), 1.67-1.70 (m, 1H) 1.67-1.70 (m, 1H), 1.69-1.72 (m, 4H), 0.92-0.95 (m, 3H), 1.69-1.72 (m, 3H),

Example 116. Synthesis of Viral Protease Inhibitor Compound 363

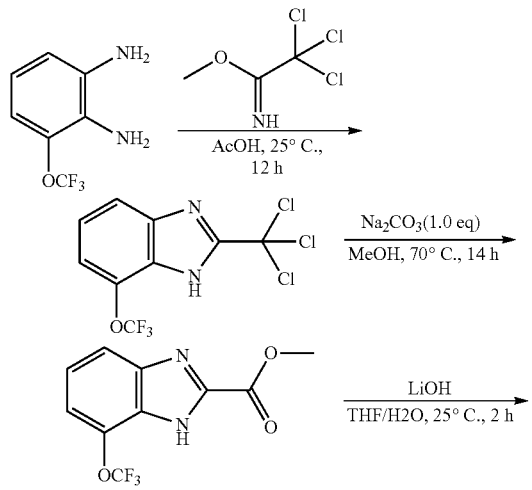

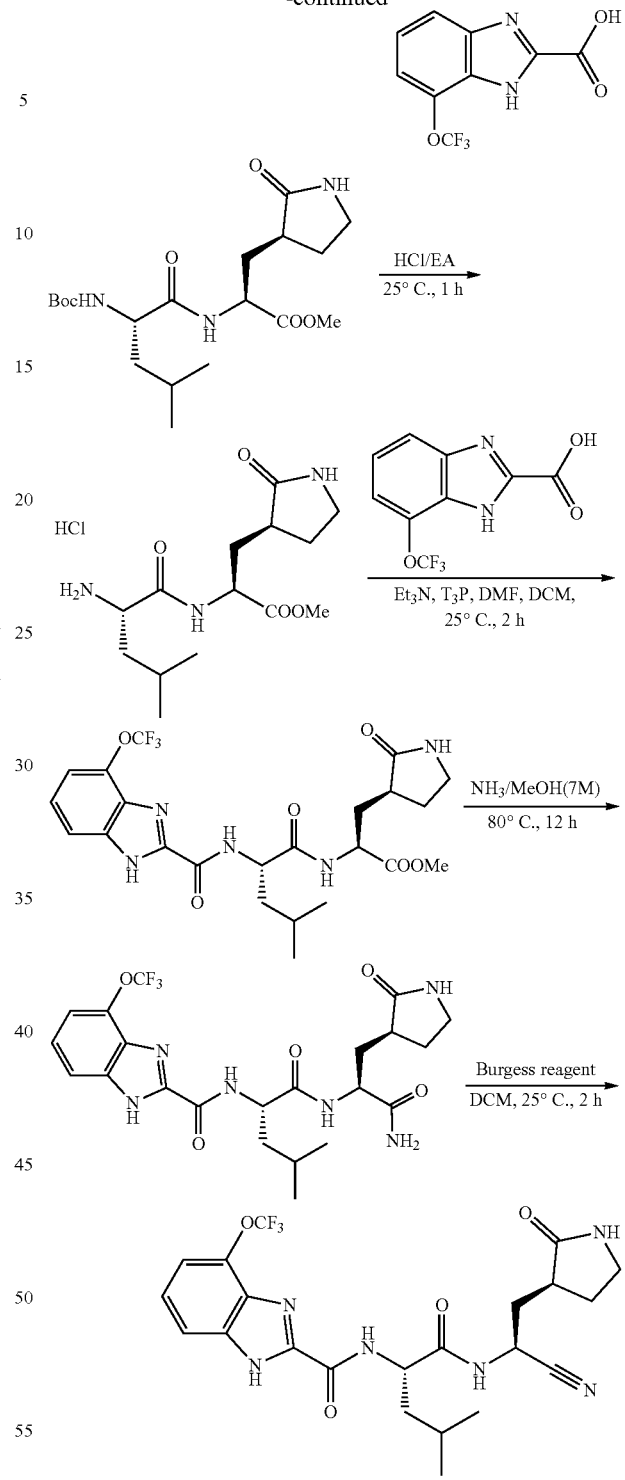

To a solution of 3-(trifluoromethoxy)benzene-1,2-diamine (500 mg, 2.60 mmol, 1 eq) in AcOH (15 mL) was added drop-wise methyl 2,2,2-trichloroethanimidoate (459.12 mg, 2.60 mmol, 321.06 uL, 1.00 eq), and then the reaction was stirred at 25° C. for 12 h. The reaction mixture was quenched by addition H$_2$O (50 mL) at 0° C., and then extracted with EtOAc (25 mL*3). The combined organic layers were washed with brine (30 mL), filtered and concentrated under reduced pressure to get the product 2-(trichloromethyl)-7-(trifluoromethoxy)-1H-benzimidazole (720 mg, crude) was obtained as a yellow solid. MS (ESI) m/z 320.8 [M+H]+

Step 2: methyl 7-(trifluoromethoxy)-1H-benzo[d]imidazole-2-carboxylate

To a solution of 2-(trichloromethyl)-7-(trifluoromethoxy)-1H-benzimidazole (720 mg, 2.25 mmol, 1 eq) in MeOH (10 mL) was added $Na_2CO_3$ (238.85 mg, 2.25 mmol, 1 eq), and the mixture was stirred at 70° C. for 14 h. 1N HCl was added to the solution and the reaction was stirred for 0.5 h. The mixture was extracted with EtOAc (30 mL*3), and the combined organic layers were washed with brine (30 mL), dried over $Na_2SO_4$, filtered and the filtrate was concentrated under reduced pressure to get the product methyl 7-(trifluoromethoxy)-1H-benzimidazole-2-carboxylate (520 mg, crude) was obtained as a yellow solid. MS (ESI) m/z 260.8 [M+H]+

Step 3: 7-(trifluoromethoxy)-1H-benzo[d]imidazole-2-carboxylic acid

To a solution of methyl 7-(trifluoromethoxy)-1H-benzimidazole-2-carboxylate (300 mg, 1.15 mmol, 1 eq) in THF (6 mL) and $H_2O$ (2 mL) was added LiOH (165.69 mg, 6.92 mmol, 6 eq), and the mixture was stirred at 25° C. for 2 h. The reaction mixture was concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 2%-40%, 9 min) to get the product 7-(trifluoromethoxy)-1H-benzimidazole-2-carboxylic acid (150 mg, 591.12 umol, 51.26% yield, 97% purity) as a white solid. MS (ESI) m/z 245.1 [M−H]+

$^1$H NMR (DMSO-$d_6$, 400 MHz): δ ppm 7.46 (d, J=8.2 Hz, 1H), 7.22 (t, J=7.9 Hz, 1H), 7.10-7.14 (m, 1H)

Step 4: (S)-methyl 2-((S)-2-amino-4-methylpentanamido)-3-((S)-2-oxopyrrolidin-3-yl)propanoate hydrochloride To a solution of methyl (2S)-2-[[(2S)-2-(tert-butoxycarbonylamino)-4-methyl-pentanoyl]amino]-3-[(3S)-2-oxopyrrolidin-3-yl]propanoate (250 mg, 625.81 umol, 1 eq) in EtOAc (0.5 mL) was added drop-wise HCl/EtOAc (4 M, 10 mL, 63.92 eq), and the mixture was stirred at 25° C. for 1 h. The reaction mixture was concentrated under reduced pressure to get the product methyl (2S)-2-[[(2S)-2-amino-4-methyl-pentanoyl]amino]-3-[(3S)-2-oxopyrrolidin-3-yl]propanoate (200 mg, crude, HCl) as a white solid.

Step 5: (S)-methyl 2-((S)-4-methyl-2-(4-(trifluoromethoxy)-1H-benzo[d]imidazole-2-carboxamido)pentanamido)-3-((S)-2-oxopyrrolidin-3-yl)propanoate To a solution of methyl (2S)-2-[[(2S)-2-amino-4-methylpentanoyl]amino]-3-[(3S)-2-oxopyrrolidin-3-yl]propanoate (200 mg, 595.55 umol, 1.22 eq, HCl) and 7-(trifluoromethoxy)-1H-benzimidazole-2-carboxylic acid (120 mg, 487.52 umol, 1 eq) in DMF (1 mL) and DCM (6 mL) was added drop-wise $Et_3N$ (295.99 mg, 2.93 mmol, 407.14 uL, 6.0 eq) and $T_3P$ (930.72 mg, 1.46 mmol, 869.83 uL, 50% purity, 3.0 eq). The mixture was stirred at 25° C. for 2 h. The reaction mixture was quenched by addition $H_2O$ (40 mL) at 0° C., and then extracted with DCM (20 mL*3). The combined organic layers were washed with brine (30 mL), dried over $Na_2SO_4$, filtered and concentrated under reduced pressure to give a residue. The residue was purified by column chromatography ($SiO_2$, petroleum ether/ethyl acetate=10/1 to 0/1) to get the product methyl (2S)-2-[[(2S)-4-methyl-2-[[7-(trifluoromethoxy)-1H-benzimidazole-2-carbonyl]amino]pentanoyl]amino]-3-[(3S)-2-oxopyrrolidin-3-yl]propanoate (180 mg, 307.11 umol, 62.99% yield, 90% purity) was obtained as a colorless oil. MS (ESI) m/z 528.2 [M+H]+.

$^1$H NMR (400 MHz, METHANOL-$d_4$): δ ppm 7.58 (br d, J=7.9 Hz, 1H), 7.40 (br t, J=8.0 Hz, 1H), 7.21-7.33 (m, 1H), 4.64 (br t, J=6.9 Hz, 1H), 4.55-4.59 (m, 1H), 3.72 (s, 3H), 3.22-3.30 (m, 2H), 2.60 (br d, J=9.0 Hz, 1H), 2.27-2.37 (m, 1H), 2.15-2.24 (m, 1H), 1.72-1.92 (m, 5H), 1.02 (br dd, J=12.8, 6.1 Hz, 6H)

Step 6: N-((S)-1-(((S)-1-amino-1-oxo-3-((S)-2-oxopyrrolidin-3-yl)propan-2-yl)amino)-4-methyl-1-oxopentan-2-yl)-4-(trifluoromethoxy)-1H-benzo[d]imidazole-2-carboxamide A solution of methyl (2S)-2-[[(2S)-4-methyl-2-[[7-(trifluoromethoxy)-1H-benzimidazole-2-carbonyl]amino]pentanoyl]amino]-3-[(3S)-2-oxopyrrolidin-3-yl]propanoate (170 mg, 322.28 umol, 1 eq) in ammonia (7 M, 17 mL, 369.24 eq) was stirred at 80° C. for 12 h.

The reaction mixture was concentrated under reduced pressure to get the product N-[(1S)-1-[[(1S)-2-amino-2-oxo-1-[[(3S)-2-oxopyrrolidin-3-yl]methyl]ethyl]carbamoyl]-3-methyl-butyl]-7-(trifluoromethoxy)-1H-benzimidazole-2-carboxamide (150 mg, crude) was obtained as a white solid. MS (ESI) m/z 513.2 [M+H]+.

Step 7: N-((S)-1-(((S)-1-cyano-2-((S)-2-oxopyrrolidin-3-yl)ethyl)amino)-4-methyl-1-oxopentan-2-yl)-4-(trifluoromethoxy)-1H-benzo[d]imidazole-2-carboxamide To a solution of N-[(1S)-1-[[(1S)-2-amino-2-oxo-1-[[(3S)-2-oxopyrrolidin-3-yl]methyl]ethyl]carbamoyl]-3-methyl-butyl]-7-(trifluoromethoxy)-1H-benzimidazole-2-carboxamide (100 mg, 195.13 umol, 1 eq) in DCM (6 mL) was added methoxycarbonyl-(triethylammonio)sulfonylazanide (232.51 mg, 975.65 umol, 5.0 eq). The mixture was stirred at 25° C. for 2 h. The reaction mixture was concentrated under reduced pressure to give a residue. The residue was purified by prep-HPLC (column: Phenomenex Luna C18 75*30 mm*3 um; mobile phase: [water (0.2% FA)-ACN]; B %: 30%-70%, 8 min) to get the product N-[(1S)-1-[[(1S)-1-cyano-2-[(3S)-2-oxopyrrolidin-3-yl]ethyl]carbamoyl]-3-methyl-butyl]-7-(trifluoromethoxy)-1H-benzimidazole-2-carboxamide (35.5 mg, 70.86 umol, 36.32% yield, 98.7% purity) was obtained as a white solid. MS (ESI) m/z 495.1 [M+H]+.

$^1$H NMR (400 MHz, DMSO-$d_6$) δ ppm 13.73 (s, 1H), 8.86-9.04 (m, 2H), 7.71 (s, 1H), 7.56 (d, J=7.6 Hz, 1H), 7.37-7.44 (m, 1H), 7.26-7.37 (m, 1H), 4.98 (dd, J=6.9, 1.2 Hz, 1H), 4.54 (br s, 1H), 3.07-3.19 (m, 2H), 2.33-2.43 (m, 1H), 2.14 (br dd, J=8.8, 4.9 Hz, 2H), 1.55-1.90 (m, 5H), 0.92 (dd, J=8.8, 6.2 Hz, 6H)

Example 117. Synthesis of Viral Protease Inhibitor Compound 365

Step 1: methyl (2S)-2-[[(2S)-2-[[3-(4-chlorophenyl)-3-hydroxy-butanoyl]amino]-4-methyl-penta noyl]amino-3-[(3S)-2-oxopyrrolidin-3-yl]propanoate

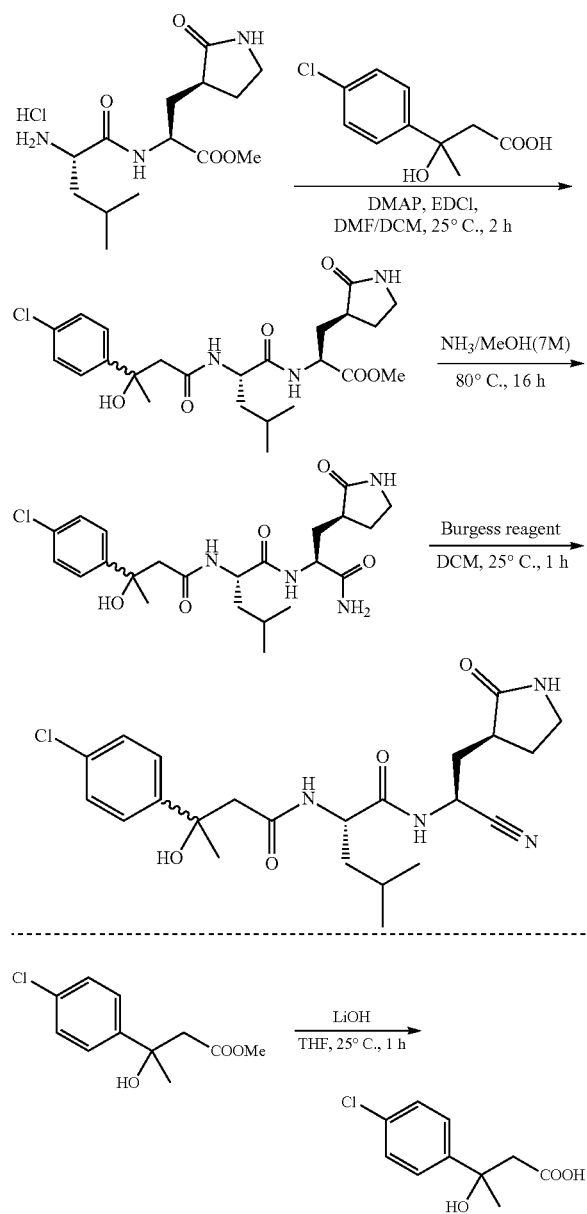

To a mixture of methyl (2S)-2-[[(2S)-2-amino-4-methyl-pentanoyl]amino]-3-[(3S)-2-oxopyrrolidin-3-yl]propanoate; hydro chloride (315.00 mg, 937.99 umol, 1 eq) and 3-(4-chlorophenyl)-3-hydroxy-butanoic acid (201.33 mg, 937.99 umol, 1 eq) in DCM (3 mL) and DMF (6 mL) was added EDCI (359.62 mg, 1.88 mmol, 2 eq) and DMAP (229.19 mg, 1.88 mmol, 2 eq). The mixture was stirred at 25° C. for 2 h. Upon the reaction was completed. The reaction mixture was filtered and concentrated under reduced pressure to give a residue. The residue was purified by neutral prep-HPLC to get the compound methyl (2S)-2-[[(2S)-2-[[3-(4-chlorophenyl)-3-hydroxy-butanoyl]amino]-4-methyl-pentanoyl]amino]-3-[(3S)-2-oxopyrrolidin-3-yl]propanoate (90 mg, 172.38 umol, 18.38% yield, 95% purity) and methyl (2S)-2-[[(2S)-2-[[3-(4-chlorophenyl)-3-hydroxy-butanoyl]amino]-4-methyl-pentaenyl]amino]-3-[(3S)-2-oxopyrrolidin-3-yl]propanoate (120 mg, 229.84 umol, 24.50% yield, 95% purity) as white solid. MS (ESI) m/z 496.3 [M+H]⁺ column: Kromasil C18 (250*50 mm*10 um); mobile phase: [water (10 mM NH4HCO3)-ACN]; B %: 25%-55%, 10 min.

Step 2: 3-(4-chlorophenyl)-3-hydroxy-butanoic acid

To a mixture of ethyl 3-(4-chlorophenyl)-3-hydroxy-butanoate (500 mg, 2.06 mmol, 1 eq) in H₂O (3 mL) and THF (6 mL) was added LiOH·H₂O (172.90 mg, 4.12 mmol, 2 eq). The mixture was stirred at 25° C. for 1 h. Upon the reaction was completed. The reaction mixture was diluted with H₂O (20 mL) and extracted with ethyl acetate 60 mL (30 mL*2). The combined organic layers were washed with brine 930 mL), dried over Na₂SO₄, filtered and concentrated under reduced pressure to give a residue compound 3-(4-chlorophenyl)-3-hydroxy-butanoic acid (400 mg, 1.68 mmol, 81.41% yield, 90% purity) as a white solid.

Step 3: (2S)-N-[(1S)-2-amino-2-oxo-1-[[(3S)-2-oxopyrrolidin-3-yl]methyl]ethyl]-2-[[3-(4-chloro phenyl)-3-hydroxy-butanoyl]amino]-4-methyl-pentanamide To a mixture of methyl (2S)-2-[[(2S)-2-[[3-(4-chlorophenyl)-3-hydroxy-butanoyl]amino]-4-methyl-pentanoyl]amino]-3-[(3S)-2-oxopyrrolidin-3-yl]propanoate (80 mg, 153.23 umol, 95% purity, 1 eq) was added NH₃/MeOH (7M) (7 M, 9.50 mL, 434.00 eq). The mixture was stirred at 80° C. for 16 h, and then the reaction mixture was concentrated under reduced pressure to give a residue compound (2S)-N-[(1S)-2-amino-2-oxo-1-[[(3S)-2-oxopyrrolidin-3-yl]methyl]ethyl]-2-[[3-(4-chlorophenyl)-3-hydroxy-butanoyl]amino]-4-methyl-pentanamide (70 mg, 130.98 umol, 85.48% yield, 90% purity) as a yellow oil. MS (ESI) m/z 481.2 [M+H]⁺.

Step 3: (2S)-2-[[3-(4-chlorophenyl)-3-hydroxy-butanoyl]amino]-N-[(1S)-1-cyano-2-[(3S)-2-oxopyrrolidin-3-yl]ethyl]-4-methyl-pentanamide To a mixture of (2S)-N-[(1S)-2-amino-2-oxo-1-[[(3S)-2-oxopyrrolidin-3-yl]methyl]ethyl]-2-[[3-(4-chlorophenyl)-3-hydroxy-butanoyl]amino]-4-methyl-pentanamide (70 mg, 145.54 umol, 1 eq) in DCM (4 mL) was added Burgess reagent (69.36 mg, 291.07 umol, 2 eq). After stirring the mixture at 25° C. for 60 min, the reaction mixture was diluted with H₂O (10 mL) and extracted with ethyl acetate (10 mL*2). The combined organic layers were concentrated under reduced pressure to give a residue. The residue was purified by neutral prep-HPLC to get the compound (2S)-2-[[3-(4-chlorophenyl)-3-hydroxy-butanoyl]amino]-N-[(1S)-1-cyano-2-[(3S)-2-oxopyrrolidin-3-yl]ethyl]-4-methyl-pentanamide (11 mg, 23.76 umol, 16.33% yield, 100% purity) as a white solid. MS (ESI) m/z 463.2 [M+H]⁺

Isomer 1: 1H NMR (400 MHz, METHANOL-d4) δ=7.51-7.42 (m, 2H), 7.36-7.26 (m, 2H), 4.96 (dd, J=6.0, 10.1 Hz, 1H), 4.27-4.17 (m, 1H), 3.30-3.23 (m, 2H), 2.83-2.63 (m, 2H), 2.51 (dq, J=5.3, 9.3 Hz, 1H), 2.34-2.17 (m, 2H), 1.94-1.72 (m, 2H), 1.57 (s, 3H), 1.54-1.26 (m, 3H), 0.93-0.77 (m, 6H)

Isomer 2: 1H NMR (400 MHz, METHANOL-d4) δ=7.44 (d, J=8.6 Hz, 2H), 7.34-7.24 (m, 2H), 5.06-4.93 (m, 1H), 4.26-4.13 (m, 1H), 3.38-3.32 (m, 1H), 3.29-3.24 (m, 1H), 2.85-2.62 (m, 2H), 2.53 (dq, J=5.5, 9.3 Hz, 1H), 2.42-2.17 (m, 2H), 1.98-1.74 (m, 2H), 1.52 (s, 3H), 1.49-1.36 (m, 2H), 1.31-1.18 (m, 1H), 0.90-0.79 (m, 3H), 0.72 (d, J=6.5 Hz, 3H)

Example 118. Synthesis of Viral Protease Inhibitor Compound 6

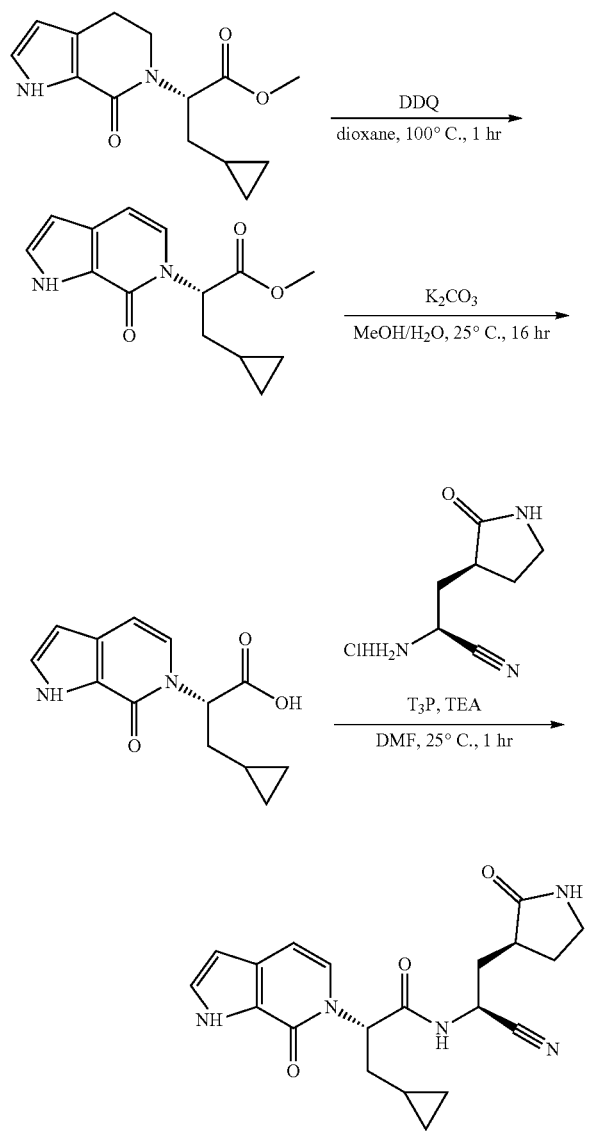

Step 1: Methyl (2S)-3-cyclopropyl-2-(7-oxo-1H-pyrrolo[2,3-c]pyridin-6-yl)propanoate To a solution of methyl (2S)-3-cyclopropyl-2-(7-oxo-4,5-dihydro-1H-pyrrolo[2,3-c]pyridin-6-yl)propanoate (20 mg, 76.2 umol, 1 eq) in dioxane (2 mL) was added DDQ (51.9 mg, 0.22 mmol, 3 eq) and the mixture was stirred at 100° C. for 1 hr under microwave. The reaction mixture was concentrated in vacuum. The residue was diluted with ethyl acetate (30 mL), washed with 10% aq. NaOH (10 mL), brine (10 mL) and dried over Na$_2$SO$_4$, filtered and concentrated in vacuum. The crude product was purified by prep-TLC (petroleum ether/ethyl acetate=1/1). methyl (2S)-3-cyclopropyl-2-(7-oxo-1H-pyrrolo[2,3-c]pyridin-6-yl)propanoate (10 mg, 38 umol, 50% yield, 100% purity) was obtained as a yellow oil.

LCMS: Rt=0.746 min; for C$_{14}$H$_{16}$N$_2$O$_3$ MS Calcd.: 260.12; MS Found: 260.9 [M+H$^+$].

$^1$H NMR (400 MHz, CDCl$_3$) δ 11.17 (br s, 1H), 7.29 (t, J=2.76 Hz, 1H), 6.98 (d, J=7.03 Hz, 1H), 6.64 (d, J=7.03 Hz, 1H), 6.39 (t, J=2.38 Hz, 1H), 5.61 (dd, J=9.79, 5.52 Hz, 1H), 3.74 (s, 3H), 2.17-2.07 (m, 1H), 2.06-1.99 (m, 1H), 0.71-0.55 (m, 1H), 0.49-0.32 (m, 2H), 0.18-0.10 (m, 1H), 0.05-0.00 (m, 1H).

Step 2: (2S)-3-cyclopropyl-2-(7-oxo-1H-pyrrolo[2,3-c]pyridin-6-yl)propanoic acid To a solution of methyl (2S)-3-cyclopropyl-2-(7-oxo-1H-pyrrolo[2,3-c]pyridin-6-yl)propanoate (10 mg, 38.4 umol, 1 eq) in MeOH (0.5 mL) was added K$_2$CO$_3$ (15.9 mg, 0.115 mmol, 3 eq) in H$_2$O (0.2 mL) and the mixture was stirred at 25° C. for 16 hr. After the reaction mixture was concentrated in vacuum, the residue was diluted with H$_2$O (5 mL), adjusted pH to about 4 with 1M aq. HCl and extracted with ethyl acetate (5 mL*3). The combined organic phase was washed with brine (5 mL) and dried over Na$_2$SO$_4$, filtered and concentrated in vacuum. The crude product was used for the next step directly. (2S)-3-cyclopropyl-2-(7-oxo-1H-pyrrolo[2,3-c]pyridin-6-yl)propanoic acid (8 mg, 32.1 umol, 83.7% yield, 99% purity) was obtained as a white solid.

LCMS: Rt=0.701 min; for C$_{13}$H$_{14}$N$_2$O$_3$ MS Calcd.: 246.10; MS Found: 246.9 [M+H$^+$].

265: N-[(1S)-1-cyano-2-[(3S)-2-oxopyrrolidin-3-yl]ethyl]-3-cyclopropyl-2-(7-oxo-1H-pyrrolo[2,3-c]pyridin-6-yl)propanamide To a solution of (2S)-3-cyclopropyl-2-(7-oxo-1H-pyrrolo[2,3-c]pyridin-6-yl)propanoic acid (8 mg, 32.4 umol, 1 eq) and (2S)-2-amino-3-[(3S)-2-oxopyrrolidin-3-yl]propanenitrile (4.9 mg, 26.2 umol, HCl) in DMF (1 mL) was added TEA (3.2 mg, 32.4 umol, 4 uL, 1 eq) and T$_3$P (31.0 mg, 48.7 umol, 28 uL, 50% purity, 1.5 eq). The mixture was stirred at 25° C. for 1 hr. The reaction mixture was concentrated in vacuum. The crude product was checked by HPLC and purified by prep-HPLC (column: Phenomenex Gemini-NX 80*40 mm*3 um; mobile phase: [water(0.05% NH$_3$H$_2$O+10 mM NH$_4$HCO$_3$)-ACN]; B %: 14%-44%, 9.5 min). N-[(1S)-1-cyano-2-[(3S)-2-oxopyrrolidin-3-yl]ethyl]-3-cyclopropyl-2-(7-oxo-1H-pyrrolo[2,3-c]pyridin-6-yl)propanamide (2.9 mg, 23.5% yield) was obtained as a white solid.

LCMS: Rt=0.702 min; for C$_{20}$H$_{23}$N$_5$O$_3$ MS Calcd.: 381.18; MS Found: 382.0 [M+H$^+$].

$^1$H NMR (400 MHz, CD$_3$OD) δ 7.21-7.15 (m, 1H), 7.11-7.02 (m, 1H), 6.60-6.49 (m, 1H), 6.28-6.19 (m, 1H), 5.55-5.35 (m, 1H), 4.95-4.78 (m, 1H), 3.12-2.94 (m, 2H), 2.39-2.27 (m, 1H), 2.16-1.99 (m, 2H), 1.90-1.82 (m, 2H), 1.76-1.61 (m, 2H), 0.56-0.43 (m, 1H), 0.31-0.17 (m, 2H), 0.04-0.02 (m, 1H), 0.02-0.00 (m, 1H).

Example 118a. Synthesis of Viral Protease Inhibitor Compound 369

Step 1: (2S)-methyl 2-((2S)-4-methyl-2-(4,4,4-trifluoro-3-hydroxy-3-phenylbutanamido)pentanamido)-3-((S)-2-oxopyrrolidin-3-yl)propanoate

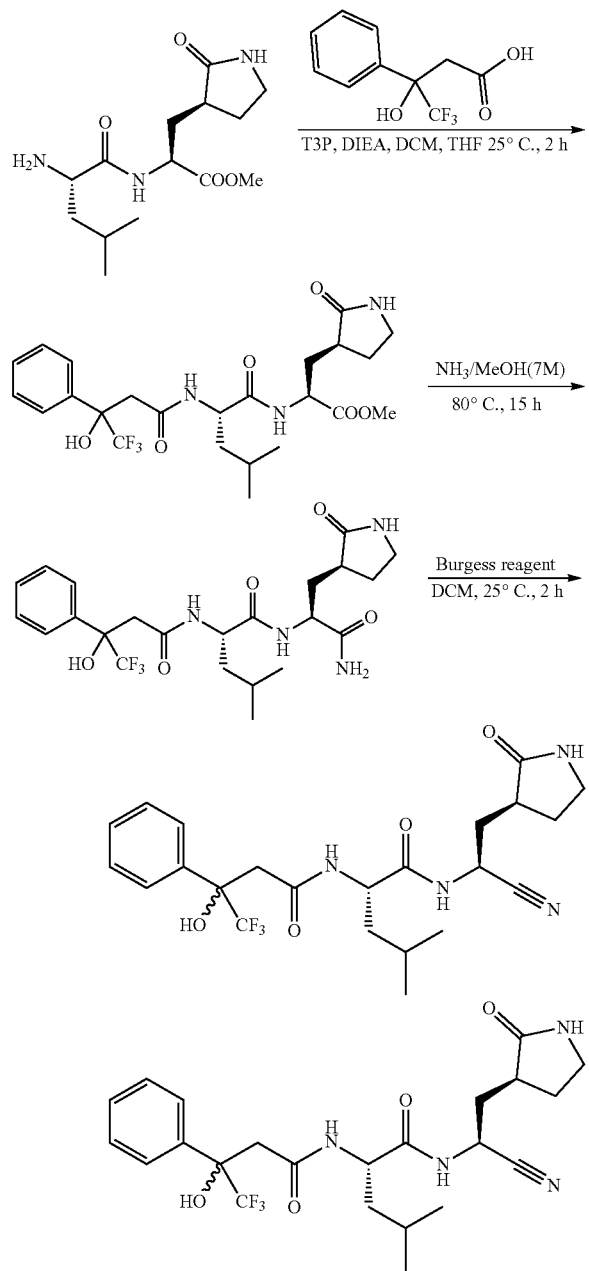

To a solution of methyl (2S)-2-[[(2S)-2-amino-4-methyl-pentanoyl]amino]-3-[(3S)-2-oxopyrrolidin-3-yl]propanoate (140 mg, 467.66 umol, 1 eq) 4,4,4-trifluoro-3-hydroxy-3-phenyl-butanoic acid (164.27 mg, 701.48 umol, 1.5 eq) in DCM (1.5 mL) THF (1.5 mL) was added T$_3$P (446.40 mg, 701.48 umol, 417.19 uL, 50% purity, 1.5 eq) and DIEA (181.32 mg, 1.40 mmol, 244.37 uL, 3 eq). The mixture was stirred at 25° C. for 2 h. LCMS showed the reaction was completed, and desired MS was observed. The reaction mixture was concentrated under reduced pressure to remove solvent. The residue was purified by neutral prep-HPLC to get the product methyl (2S)-2-[[(2S)-4-methyl-2-[(4,4,4-trifluoro-3-hydroxy-3-phenyl-butanoyl)amino]pentanoyl]amino]-3-[(3S)-2-oxopyrrolidin-3-yl]propanoate (120 mg, 232.77 umol, 49.77% yield) was obtained as white solid. MS (ESI) m/z 516.2 [M+H]$^+$.

Step 2: (2S)-N-((S)-1-amino-1-oxo-3-((S)-2-oxopyrrolidin-3-yl)propan-2-yl)-4-methyl-2-(4,4,4-trifluoro-3-hydroxy-3-phenylbutanamido)pentanamide To a solution of methyl (2S)-2-[[(2S)-4-methyl-2-[(4,4,4-trifluoro-3-hydroxy-3-phenyl-butanoyl)amino]pentanoyl]amino]-3-[(3S)-2-oxopyrrolidin-3-yl]propanoate (120 mg, 232.77 umol, 1 eq) in MeOH/NH$_3$ (7 M, 5 mL, 150.36 eq) The mixture was stirred at 80° C. for 15 h. LCMS showed the reaction was completed, and desired MS was observed. The reaction mixture was filtered and concentrated under reduced pressure to give a residue to get the product (2S)-N-[(1S)-2-amino-2-oxo-1-[[(3R)-2-oxopyrrolidin-3-yl]methyl]ethyl]-4-methyl-2-[(4,4,4-trifluoro-3-hydroxy-3-phenyl-butanoyl)amino]pentanamide (120 mg, crude) was obtained as colorless oil. MS (ESI) m/z 501.2 [M+H]$^+$.

Step 3: (2S)-N-((S)-1-cyano-2-((S)-2-oxopyrrolidin-3-yl)ethyl)-4-methyl-2-(4,4,4-trifluoro-3-hydroxy-3-phenylbutanamido)pentanamide To a solution of (2S)-N-[(1S)-2-amino-2-oxo-1-[[(3S)-2-oxopyrrolidin-3-yl]methyl]ethyl]-4-methyl-2-[(4,4,4-trifluoro-3-hydroxy-3-phenyl-butanoyl)amino]pentanamide (120 mg, 239.76 umol, 1 eq) in DCM (3 mL) was added Burgess reagent (114.27 mg, 479.51 umol, 2 eq). The mixture was stirred at 25° C. for 1 h. LCMS showed the reaction was completed, and desired MS was observed. The reaction mixture was quenched by addition H$_2$O 5 mL, and then extracted with DCM (2.5 mL*3). The combined organic layers were washed with brine (3 mL), dried over Na$_2$SO$_4$, filtered and concentrated under reduced pressure to give a residue. The residue was purified by neutral prep-HPLC to get the product (2S)-N-[(1S)-1-cyano-2-[(3S)-2-oxopyrrolidin-3-yl]ethyl]-4-methyl-2-[(4,4,4-trifluoro-3-hydroxy-3-phenyl-butanoyl)amino]pentanamide (20.18 mg, 38.77 umol, 16.17% yield, 92.698% purity) was obtained as white solid. MS (ESI) m/z 483.3[M+H]$^+$.

Prep-HPLC Condition:
column: Waters Xbridge Prep OBD C18 150*40 mm*10 um; mobile phase: [water (10 mM NH$_4$HCO$_3$)-ACN]; B %: 25%-55%, 8 min column: Phenomenex Luna C18 75*30 mm*3 um; mobile phase: [water(0.2% FA)-ACN]; B %: 40%-65%, 8 min $^1$H NMR (400 MHz, DMSO-d6) δ ppm 8.83 (d, J=7.72 Hz, 1H) 8.37 (d, J=8.16 Hz, 1H) 7.72 (s, 1H) 7.53 (br d, J=7.06 Hz, 2H) 7.29-7.42 (m, 3H) 7.16 (s, 1H) 4.77-4.99 (m, 1H) 4.15-4.28 (m, 1H) 3.03-3.20 (m, 4H) 2.16-2.27 (m, 1H) 1.95-2.09 (m, 2H) 1.57-1.78 (m, 2H) 1.29-1.44 (m, 3H) 0.69-0.88 (m, 6H).

(2S)-N-[(1S)-1-cyano-2-[(3S)-2-oxopyrrolidin-3-yl]ethyl]-4-methyl-2-[(4,4,4-trifluoro-3-hydroxy-3-phenyl-butanoyl)amino]pentanamide (13.28 mg, 27.20 umol, 11.34% yield, 98.809% purity) was obtained as white solid MS (ESI) m/z 483.3[M+H]+.

$^1$H NMR (400 MHz, DMSO-d6) δ ppm 8.86 (d, J=7.94 Hz, 1H) 8.58 (d, J=8.16 Hz, 1H) 7.73 (s, 1H) 7.51-7.62 (m, 2H) 7.31-7.42 (m, 3H) 6.92 (s, 1H) 4.86-4.96 (m, 1H) 4.11 (ddd, J=9.65, 8.32, 5.18 Hz, 1H) 3.29 (br d, J=14.55 Hz, 1H) 3.06-3.20 (m, 2H) 2.89 (d, J=14.55 Hz, 1H) 2.21-2.36 (m, 1H) 2.02-2.17 (m, 2H) 1.62-1.82 (m, 2H) 1.20-1.38 (m, 2H) 1.02-1.14 (m, 1H) 0.73 (d, J=6.62 Hz, 3H) 0.49 (d, J=6.39 Hz, 3H).

Example 119. Synthesis of Viral Protease Inhibitor Compound 375

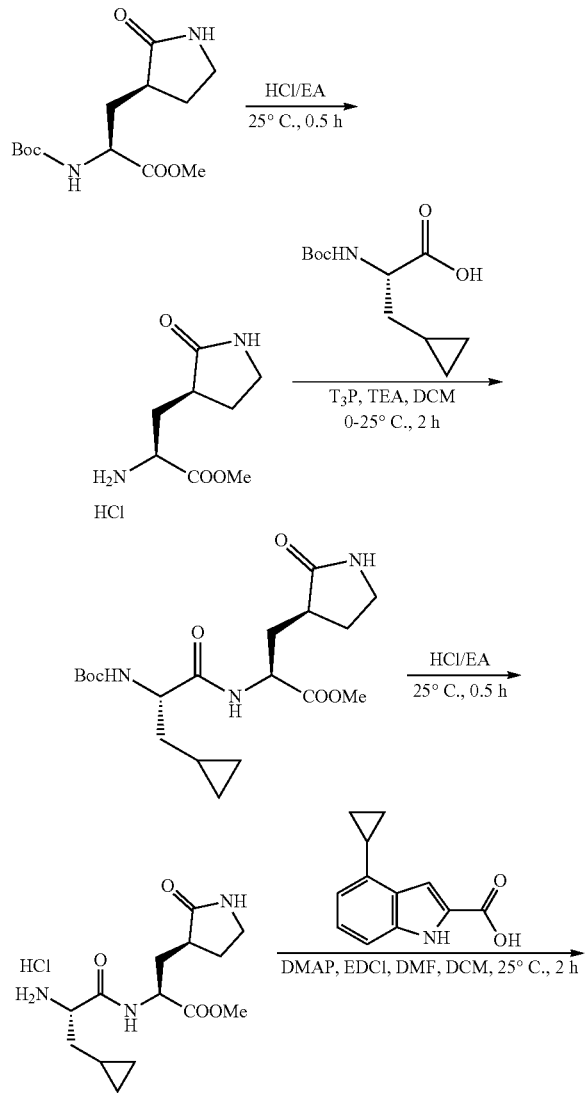

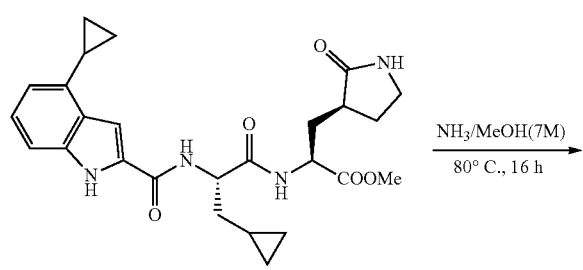

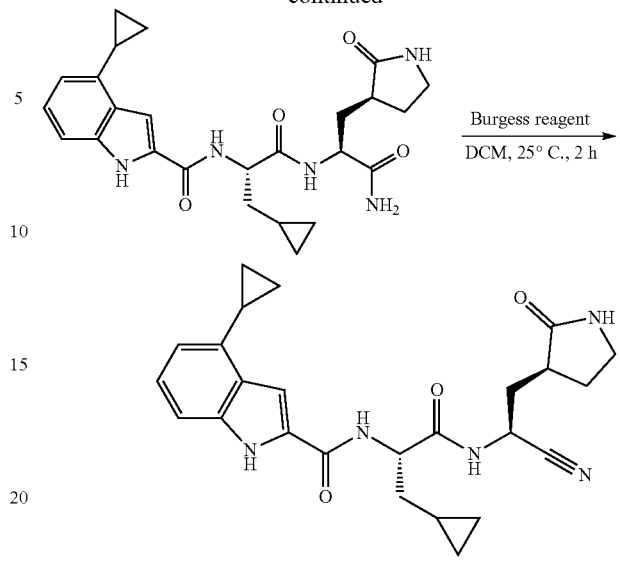

A mixture of methyl (2S)-2-(tert-butoxycarbonylamino)-3-[(3S)-2-oxopyrrolidin-3-yl]propanoate (1.2 g, 4.19 mmol, 1 eq) in HCl/MeOH (10 mL) was stirred at 25° C. for 30 min. The reaction mixture was concentrated under reduced pressure to crude methyl (2S)-2-amino-3-[(3S)-2-oxopyrrolidin-3-yl]propanoate (770 mg, 4.14 mmol, 98.67% yield) as a yellow oil.

Step 2: methyl(2S)-2-[[(2S)-2-(tert-butoxycarbonylamino)-3-cyclopropyl-propanoyl]amino]-3-[(3S)-2-oxopyrrolidin-3-yl]propanoate To a mixture of methyl (2S)-2-amino-3-[(3S)-2-oxopyrrolidin-3-yl]propanoate (750 mg, 4.03 mmol, 1 eq) and (2S)-2-(tert-butoxycarbonylamino)-3-cyclopropyl-propanoic acid (923.45 mg, 4.03 mmol, 1 eq) in DCM (3 mL) was added TEA (2.04 g, 20.14 mmol, 2.80 mL, 5 eq) in one portion at 0° C. The mixture was added with T₃P (3.84 g, 12.08 mmol, 3.59 mL, 3 eq) at 0° C. and stirred at 25° C. for 2 h. The reaction mixture was diluted with H₂O (10 mL) and extracted with DCM (10 mL*3). The combined organic layers were washed with brine 10 mL (10 mL*1), dried over Na₂SO₄, filtered and concentrated under reduced pressure to give crude methyl (2S)-2-[[(2S)-2-(tert-butoxycarbonylamino)-3-cyclopropyl-propanoyl]amino]-3-[(3S)-2-oxopyrrolidin-3-yl]propanoate (1.5 g, 3.77 mmol, 93.70% yield) as a yellow oil. MS (ESI) m/z 398.3 [M+H]⁺

Step 3: methyl (2S)-2-[[(2S)-2-amino-3-cyclopropyl-propanoyl]amino]-3-[(3S)-2-oxopyrrolidin-3-yl]propanoate A mixture of methyl (2S)-2-[[(2S)-2-(tert-butoxycarbonylamino)-3-cyclopropyl-propanoyl]amino]-3-[(3S)-2-oxopyrrolidin-3-yl]propanoate (1.3 g, 3.27 mmol, 1 eq) in HCl/MeOH (10 mL) was stirred at 25° C. for 30 min. The reaction mixture was concentrated under reduced pressure to give crude methyl (2S)-2-[[(2S)-2-amino-3-cyclopropyl-propanoyl]amino]-3-[(3S)-2-oxopyrrolidin-3-yl]propanoate (900 mg, 3.03 mmol, 92.54% yield) as a yellow oil.

Step 4: methyl(2S)-2-[[(2S)-3-cyclopropyl-2-[(4-cyclopropyl-1H-indole-2-carbonyl)amino]propanoyl] amino]-3-[(3S)-2-oxopyrrolidin-3-yl]propanoate To a mixture of methyl (2S)-2-[[(2S)-2-amino-3-cyclopropyl-propanoyl]amino]-3-[(3S)-2-oxopyrrolidin-3-yl]propanoate (448 mg, 1.51 mmol, 1 eq) and 4-cyclopropyl-1H-indole-2-carboxylic acid (364.61 mg, 1.81 mmol, 1.2 eq) in DCM (8 mL) was added DMF (2 mL) and EDCI (868.40 mg, 4.53 mmol, 3 eq) in one portion at 25° C. The mixture was added with DMAP (553.43 mg, 4.53 mmol, 3 eq) and the reaction was stirred at 25° C. for 2 h. The reaction mixture was concentrated under reduced pressure to give a residue. The crude product was purified by column chromatography (SiO₂, petroleum ether/ethyl acetate=5/1 to 0/1) to afford methyl (2S)-2-[[(2S)-3-cyclopropyl-2-[(4-cyclopropyl-1H-indole-2-carbonyl)amino]propanoyl]amino]-3-[(3S)-2-oxopyrrolidin-3-yl]propanoate (500 mg, 1.04 mmol, 68.90% yield) as a white solid. MS (ESI) m/z 481.2 [M+H]⁺

Step 5: N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4-cyclopropyl-1H-indole-2-carboxamide A mixture of methyl (2S)-2-[[(2S)-3-cyclopropyl-2-[(4-cyclopropyl-1H-indole-2-carbonyl)amino]propanoyl]amino]-3-[(3S)-2-oxopyrrolidin-3-yl]propanoate (500 mg, 1.04 mmol, 1 eq) in NH₃/MeOH (7M) (7 mL) was stirred at 80° C. for 16 h. The reaction mixture was concentrated under reduced pressure to give N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4-cyclopropyl-1H-indole-2-carboxamide (390 mg, 837.73 umol, 80.52% yield) as a white solid. MS (ESI) m/z 466.3 [M+H]⁺

Step 6: N-[(1S)-2-[[(1S)-1-cyano-2-[(3S)-2-oxopyrrolidin-3-yl]ethyl]amino]-1-(cyclopropylmethyl)-2-oxo-ethyl]-4-cyclopropyl-1H-indole-2-carboxamide To a mixture of N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4-cyclopropyl-1H-indole-2-carboxamide (390 mg, 837.73 umol, 1 eq) in DCM (7 mL) was added Burgess reagent (1.20 g, 5.03 mmol, 6 eq) in one portion at 25° C. The mixture was stirred at 25° C. for 2 h. The reaction mixture was concentrated under reduced pressure to give a residue. The residue was purified by prep-HPLC (neutral condition) to give N-[(1S)-2-[[(1S)-1-cyano-2-[(3S)-2-oxopyrrolidin-3-yl]ethyl]amino]-1-(cyclopropylmethyl)-2-oxo-ethyl]-4-cyclopropyl-1H-indole-2-carboxamide (68 mg, 151.95 umol, 18.14% yield) as a white solid. MS (ESI) m/z 448.3 [M+H]⁺

Column: Waters Xbridge Prep OBD C18 150*40 mm*10 um; mobile phase: [water (10 mM NH₄HCO₃)-ACN]; B %: 30%-55%, 8 min ¹H NMR (400 MHz, DMSO-d₆) δ=11.55 (s, 1H), 9.12-8.84 (m, 1H), 8.59 (d, J=7.6 Hz, 1H), 7.84-7.65 (m, 1H), 7.48 (d, J=1.3 Hz, 1H), 7.21 (d, J=8.2 Hz, 1H), 7.06 (t, J=7.7 Hz, 1H), 6.64 (d, J=7.2 Hz, 1H), 5.09-4.87 (m, 1H), 4.69-4.36 (m, 1H), 3.20-3.06 (m, 2H), 2.46-2.07 (m, 4H), 1.95- 1.39 (m, 4H), 1.01 (br dd, J=2.2, 8.3 Hz, 2H), 0.92-0.74 (m, 3H), 0.55-0.34 (m, 2H), 0.28-0.00 (m, 2H)

Example 120. Synthesis of Viral Protease Inhibitor Compound 377

Step 1: methyl (2S)-2-[[(2S)-2-[(4-ethoxy -1H-indole-2-carbonyl)amino] -4-methyl-pentanoyl]amino] -3-[(3S)-2-oxopyrrolidin-3-yl]propanoate

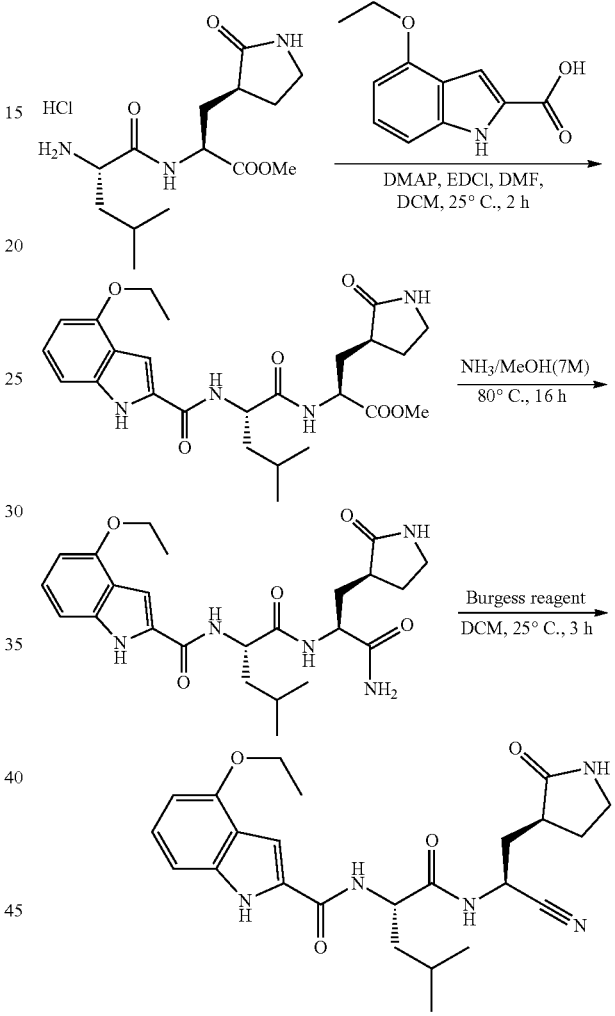

To a mixture of methyl (2S)-2-[[(2S)-2-amino-4-methyl-pentanoyl]amino]-3-[(3S)-2-oxopyrrolidin-3-yl]propanoate; hydrochloride (250.00 mg, 671.53 umol, 1 eq, HCl) and 4-ethoxy-1H-indole-2-carboxylicacid (165.36 mg, 805.83 umol, 1.2 eq) in DCM (10 mL) and DMF (5 mL) was added EDCI (257.46 mg, 1.34 mmol, 2 eq) and DMAP (164.08 mg, 1.34 mmol, 2 eq). After stirring the mixture at 25° C. for 2 h, the reaction mixture was diluted with H₂O (20 mL) and extracted with ethyl acetate (60 mL, which was extracted as 30 mL*2). The combined organic layers were washed with brine (30 mL), dried over Na₂SO₄, filtered and concentrated under reduced pressure to give a residue. The residue was purified by prep-TLC (SiO₂, petroleum ether:ethyl acetate=0:1) to afford methyl(2S)-2-[[(2S)-2-[(4-ethoxy-1H-indole-2-carbonyl)amino]-4-methyl-pentanoyl]amino]-3-[(3S)-2-oxopyrrolidin-3-yl]propanoate (200 mg, 369.94 umol, 55.09% yield, 90% purity) as a yellow oil.

Step 2: N-[(1S)-1-[[(1S)-2-amino-2-oxo-1-[[(3S)-2-oxopyrrolidin-3-yl]methyl]ethyl]carbamoyl]-3-methyl-butyl]-4-ethoxy-1H-indole-2-carboxamide A mixture of methyl (2S)-2-[[(2S)-2-[(4-ethoxy-1H-indole-2-carbonyl)amino]-4-methyl-pentanoyl]amino]-3-[(3S)-2-oxopyrrolidin-3-yl]propanoate (120 mg, 246.63 umol, 1 eq) was added NH₃/MeOH (7M) (4.20 mg, 246.63 umol, 20 mL, 1 eq) was stirred at 80° C. for 16 h. Upon completion, the mixture was concentrated under reduced pressure to give a residue and used next directly. Compound N-[(1S)-1-[[(1S)-2-amino-2-oxo-1-[[(3S)-2-oxopyrrolidin-3-yl]methyl] ethyl]carbamoyl]-3-methyl-butyl]-4-ethoxy-1H-indole-2-carboxamide (112 mg, 213.76 umol, 86.67% yield, 90% purity) was obtained as a yellow oil.

Step 3: N-[(1S)-1-[[(1S)-1-cyano-2-[(3S)-2-oxopyrrolidin-3-yl]ethyl]carbamoyl]-3-methyl-butyl]-4-ethoxy-1H-indole-2-carboxamide To a mixture of N-[(1S)-1-[[(1S)-2-amino-2-oxo-1-[[(3S)-2-oxopyrrolidin-3-yl]methyl]ethyl] carbamoyl]-3-methyl-butyl]-4-ethoxy-1H-indole-2-carboxamide (111.11 mg, 212.07 umol, 90% purity, 1 eq) in DCM (2 mL) was added Burgess reagent (151.61 mg, 636.20 umol, 3 eq). After the mixture was stirred at 25° C. for 3 h, the reaction mixture was filtered and concentrated under reduced pressure to give a residue. The residue was purified by HCl prep-HPLC to get the compound N-[(1S)-1-[[(1S)-1-cyano-2-[(3S)-2-oxopyrrolidin-3-yl]ethyl] carbamoyl]-3-methyl-butyl]-4-ethoxy-1H-indole-2-carboxamide (38 mg, 81.87 umol, 38.61% yield, 97.716% purity) as a white solid. MS (ESI) m/z 454.2 [M+H]⁺

Column: Waters Xbridge BEH C18 100*30 mm*10 um; mobile phase: [water (10 mM NH4HCO3)-ACN]; B %: 30%-60%, 10 min H NMR (400 MHz, DMSO-d6) δ=11.56 (br s, 1H), 8.90 (d, J=8.1 Hz, 1H), 8.52 (br d, J=7.6 Hz, 1H), 7.72 (s, 1H), 7.39 (s, 1H), 7.11-7.03 (m, 1H), 7.01-6.96 (m, 1H), 6.48 (d, J=7.6 Hz, 1H), 5.04-4.92 (m, 1H), 4.57-4.37 (m, 1H), 4.14 (q, J=7.0 Hz, 2H), 3.21-3.03 (m, 2H), 2.43-2.28 (m, 1H), 2.21-2.04 (m, 2H), 1.82-1.46 (m, 5H), 1.41 (t, J=7.0 Hz, 3H), 0.91 (dd, J=6.4, 19.5 Hz, 6H)

Example 121. Synthesis of Viral Protease Inhibitor Compound 379

Step 1: methyl (2S)-2-[[(2S)-2-amino-3-cyclopropyl-propanoyl]amino-3-[(3S)-2-oxopyrrolidin-3-yl]propanoate

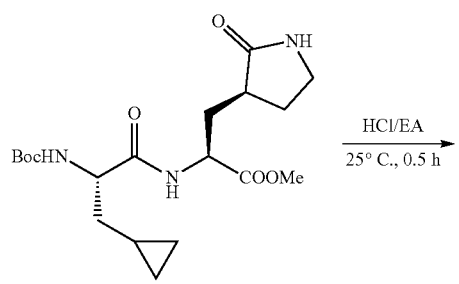

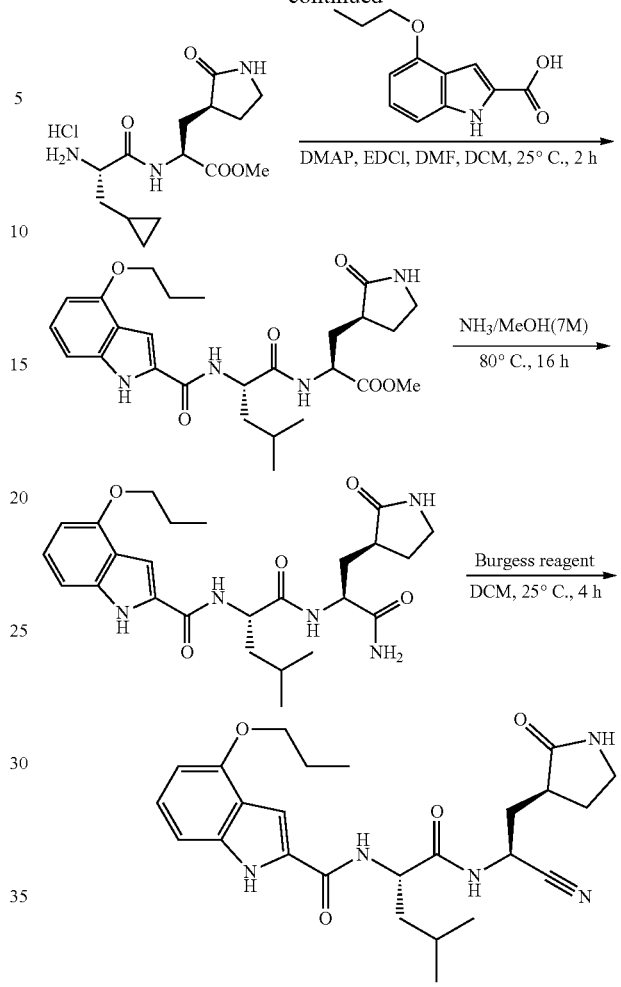

A mixture of methyl (2S)-2-[[(2S)-2-(tert-butoxycarbonylamino)-3-cyclopropyl-propanoyl]amino]-3-[(3S)-2-oxopyrrolidin-3-yl]propanoate (1.3 g, 3.27 mmol, 1 eq) in HCl/MeOH (10 mL) was stirred at 25° C. for 30 min. The reaction mixture was concentrated under reduced pressure to give methyl (2S)-2-[[(2S)-2-amino-3-cyclopropyl-propanoyl]amino]-3-[(3S)-2-oxopyrrolidin-3-yl]propanoate (900 mg, 3.03 mmol, 92.54% yield) as a yellow oil.

Step 2: methyl (2S)-2-[[(2S)-3-cyclopropyl-2-[(4-propoxy-1H-indole-2-carbonyl)amino]propanoyl]amino]-3-[(3S)-2-oxopyrrolidin-3-yl]propanoate To a mixture of methyl (2S)-2-[[(2S)-2-amino-3-cyclopropyl-propanoyl]amino]-3-[(3S)-2-oxopyrrolidin-3-yl]propanoate (448 mg, 1.51 mmol, 1 eq) and 4-propoxy-1H-indole-2-carboxylic acid (396.37 mg, 1.81 mmol, 1.2 eq) in DMF (2 mL) was added DCM (8 mL) and EDCI (866.48 mg, 4.52 mmol, 3 eq) in one portion at 25° C. The mixture was added with DMAP (552.19 mg, 4.52 mmol, 3 eq), and the reaction was stirred at 25° C. for 2 h. The reaction mixture was diluted with H₂O (10 mL) and extracted with ethyl acetate (30 mL, which extracted added as 10 mL*3). The combined organic layers were washed with brine (10 mL*1), dried over Na₂SO₄, filtered and concentrated under reduced pressure to give a residue. The crude product was purified by column chromatography (SiO2, petroleum ether/ ethyl acetate=5/1 to 0/1) to afford methyl (2S)-2-[[(2S)-3-cyclopropyl-2-[(4-propoxy-1H-indole-2-carbonyl)amino]propanoyl]amino]-3-[(3S)-2-oxopyrrolidin-3-yl]propanoate (480 mg, 962.75 umol, 63.90% yield) as a white solid. MS (ESI) m/z 499.2 [M+H]⁺

Step 3: N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4-propoxy-1H-indole-2-carboxamide A mixture of methyl (2S)-2-[[(2S)-3-cyclopropyl-2-[(4-propoxy-1H-indole-2-carbonyl)amino]propanoyl]amino]-3-[(3S)-2-oxopyrrolidin-3-yl]propanoate (480 mg, 962.75 umol, 1 eq) in NH₃/MeOH (7M) (3 mL) was stirred at 80° C. for 16 h. The reaction mixture was concentrated under reduced pressure to give the crude N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4-propoxy-1H-indole-2-carboxamide (380 mg, 785.84 umol, 81.62% yield) as a white solid. MS (ESI) m/z 484.3 [M+H]⁺

Step 4: N-[(1S)-2-[[(1S)-1-cyano-2-[(3S)-2-oxopyrrolidin-3-yl]ethyl]amino]-1-(cyclopropylmethyl)-2-oxo-ethyl]-4-propoxy-H-indole-2-carboxamide To a mixture of N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4-propoxy-1H-indole-2-carboxamide (380 mg, 785.84 umol, 1 eq) in DCM (7 mL) was added Burgess reagent (1.12 g, 4.72 mmol, 6 eq) in one portion at 25° C. The mixture was stirred at 25° C. for 4 h. The reaction mixture was concentrated under reduced pressure to give a residue. The crude product was purified by prep-HPLC (neutral condition) to give N-[(1S)-2-[[(1S)-1-cyano-2-[(3S)-2-oxopyrrolidin-3-yl]ethyl]amino]-1-(cyclopropylmethyl)-2-oxo-ethyl]-4-propoxy-1H-indole-2-carboxamide (120 mg, 257.76 umol, 32.80% yield) was obtained as a white solid. MS (ESI) m/z 466.3 [M+H]⁺

Column: Waters Xbridge Prep OBD C18 150*40 mm*10 um; mobile phase: [water (10 mM NH₄HCO₃)-ACN]; B %: 30%-60%, 8 min ¹H NMR (400 MHz, DMSO-d₆) δ=11.55 (br d, J=1.7 Hz, 1H), 9.07-8.85 (m, 1H), 8.57 (d, J=7.6 Hz, 1H), 7.83-7.61 (m, 1H), 7.39 (d, J=1.6 Hz, 1H), 7.14-6.90 (m, 2H), 6.48 (d, J=7.6 Hz, 1H), 5.09-4.86 (m, 1H), 4.60-4.28 (m, 1H), 4.04 (t, J=6.4 Hz, 2H), 3.22-3.01 (m, 2H), 2.45-2.03 (m, 3H), 1.94-1.59 (m, 5H), 1.58-1.34 (m, 1H), 1.06 (t, J=7.4 Hz, 3H), 0.95-0.69 (m, 1H), 0.55-0.30 (m, 2H), 0.28-0.02 (m, 2H)

Example 122. Synthesis of Viral Protease Inhibitor Compound 383

Step 1: methyl (2S)-2-[[(2S)-2-[(4,4-difluorocyclohexyl)methoxycarbonylamino]-4-methyl-pentanoyl]amino]-3-[(3S)-2-oxopyrrolidin-3-yl]propanoate

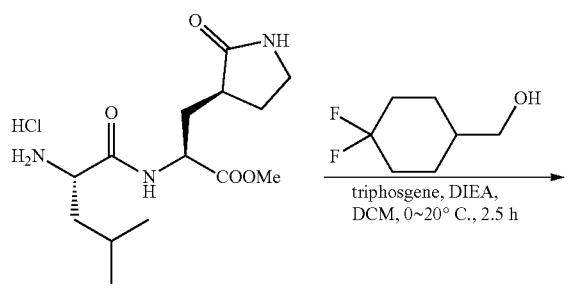

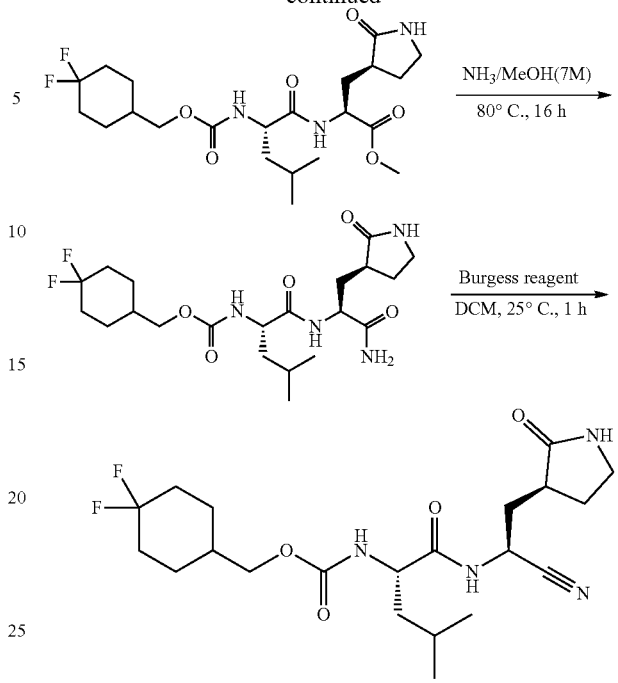

To a mixture of bis(trichloromethyl) carbonate (940 mg, 3.17 mmol, 1.36 eq) in THF (2 mL) was added DIEA (602.47 mg, 4.66 mmol, 811.95 uL, 2 eq) at 25° C., and then (4,4-difluorocyclohexyl)methanol (350 mg, 2.33 mmol, 1 eq) in THF (2 mL) was added at 0° C. After stirring the mixture at 0° C. for 15 min, the reaction was heated to 25° C. and stirred for 1 h. Upon completion, the reaction mixture was concentrated under reduced pressure to give a residue (4,4-difluorocyclohexyl)methyl carbonochloridate (400 mg, 1.51 mmol, 64.57% yield, 80% purity) as a yellow oil.

To a mixture of methyl (2S)-2-[[(2S)-2-amino-4-methylpentanoyl]amino]-3-[(3S)-2-oxopyrrolidin-3-yl]propanoate; hydrochloride (300 mg, 893.32 umol, 1 eq) in THF (3 mL) was added DIEA (346.37 mg, 2.68 mmol, 466.80 uL, 3 eq) and (4,4-difluorocyclohexyl)methyl carbonochloridate (356.14 mg, 1.34 mmol, 80% purity, 1.5 eq) in THF (2 mL) at 0° C. The mixture was stirred at 0° C. for 10 min and stirred at 25° C. for 1 h. Upon completion, the reaction mixture was concentrated under reduced pressure to give a residue. The residue was purified by column chromatography (SiO₂, petroleum ether/ethyl acetate=8/1 to 0/1) to afford methyl (2S)-2-[[(2S)-2-[(4,4-difluorocyclohexyl)methoxycarbonylamino]-4-methyl-pentanoyl]amino]-3-[(3S)-2-oxopyrrolidin-3-yl]propanoate (320 mg, 605.65 umol, 67.80% yield, 90% purity) as a yellow oil. MS (ESI) m/z 476 [M+H]⁺

Step 2: 4,4-difluorocyclohexyl)methyl N-[(1S)-1-[[(1S)-2-amino-2-oxo-1-[[(3S)-2-oxopyrrolidin-3-yl]methyl]ethyl]carbamoyl]-3-methyl-butyl]carbamate To a mixture of methyl (2S)-2-[[(2S)-2-[(4,4-difluorocyclohexyl)methoxycarbonylamino]-4-methyl-pentanoyl]amino]-3-[(3S)-2-oxopyrrolidin-3-yl]propanoate (300 mg, 630.88 umol, 1 eq) was added NH₃/MeOH (7M) (10.74 mg, 630.89 umol, 1 eq). After stirring the mixture at 80° C. for 16 h, the reaction mixture was concentrated under reduced pressure to give a residue and used next step directly. Compound (4,4-difluorocyclohexyl)methyl N-[(1S)-1-

[[(1S)-2-amino-2-oxo-1-[[(3S)-2-oxopyrrolidin-3-yl] methyl]ethyl]carbamoyl]-3-methyl-butyl]carbamate (280 mg, 364.81 umol, 57.83% yield, 60% purity) was obtained as a yellow oil. MS (ESI) m/z 461.3 [M+H]+

Step 3: (4,4-difluorocyclohexyl)methyl N-[(1S)-1-[[(1S)-1-cyano-2-[(3S)-2-oxopyrrolidin-3-yl]ethyl] carbamoyl]-3-methyl-butyl]carbamate To a mixture of (4,4-difluorocyclohexyl)methyl N-[(1S)-1-[[(1S)-2-amino-2-oxo-1-[[(3S)-2-oxopyrrolidin-3-yl] methyl]ethyl]carbamoyl]-3-methyl-butyl]carbamate (230 mg, 299.67 umol, 60% purity, 1 eq) in DCM (6 mL) was added Burgess reagent (142.83 mg, 599.33 umol, 2 eq). The mixture was stirred at 25° C. for 60 min. Upon completion, the reaction mixture was diluted with H2O (10 mL) and extracted with DCM (20 mL). The combined organic layers concentrated under reduced pressure to give a residue. The residue was purified by neutral prep-HPLC to get the compound (4,4-difluorocyclohexyl)methyl N-[(1S)-1-[[(1S)-1-cyano-2-[(3S)-2-oxopyrrolidin-3-yl] ethyl]carbamoyl]-3-methyl-butyl]carbamate (48 mg, 100.77 umol, 33.63% yield, 92.9% purity) as a white solid. MS (ESI) m/z 443.3 [M+H]+

Column: Waters Xbridge BEH C18 100*30 mm*10 um; mobile phase: [water (10 mM NH4HCO3)-ACN]; B %: 25%-45%, 8 min H NMR (400 MHz, DMSO-d6) δ=8.81 (d, J=8.0 Hz, 1H), 7.81-7.66 (m, 1H), 7.40 (br d, J=7.8 Hz, 1H), 5.01-4.81 (m, 1H), 4.03-3.88 (m, 1H), 3.83 (br d, J=6.1 Hz, 2H), 3.21-3.03 (m, 2H), 2.40-2.22 (m, 1H), 2.18-1.94 (m, 4H), 1.90-1.54 (m, 8H), 1.53-1.30 (m, 2H), 1.29-1.10 (m, 2H), 0.87 (dd, J=6.5, 12.8 Hz, 6H)

Example 123. Synthesis of Viral Protease Inhibitor Compound 385

Step 1: (S)-methyl 2-amino-3-((S)-2-oxopyrrolidin-3-yl)propanoate

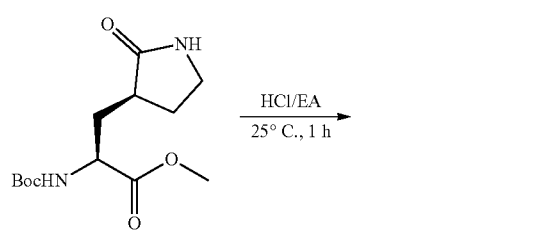

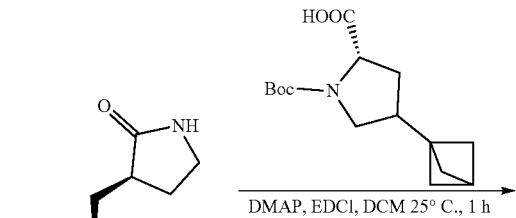

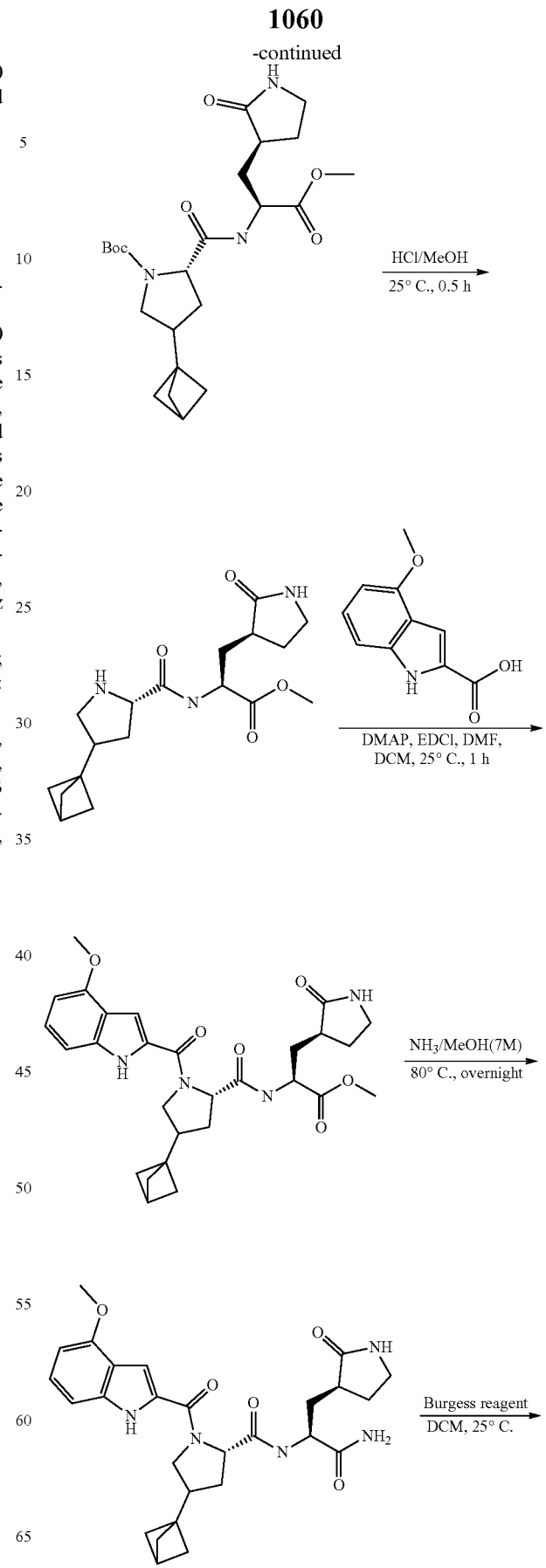

-continued

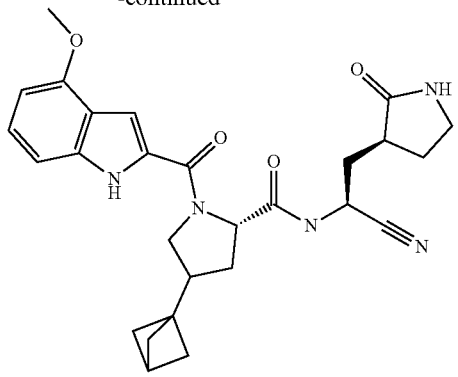

A solution of methyl (2S)-2-(tert-butoxycarbonylamino)-3-[(3S)-2-oxopyrrolidin-3-yl]propanoate (350 mg, 1.22 mmol, 1 eq) in HCl/EtOAc (4 M, 5 mL, 16.36 eq) was stirred at 25° C. for 1 h. Upon completion, the reaction mixture was concentrated to give methyl (2S)-2-amino-3-[(3S)-2-oxopyrrolidin-3-yl]propanoate (272 mg, crude, HCl) as a yellow oil.

Step 2: (2S)-tert-butyl 4-(bicyclo[1.1.1]pentan-1-yl)-2-(((S)-1-methoxy-1-oxo-3-((S)-2-oxopyrrolidin-3-yl)propan-2-yl)carbamoyl)pyrrolidine-1-carboxylate To a solution of methyl (2S)-2-amino-3-[(3S)-2-oxopyrrolidin-3-yl]propanoate (272 mg, 1.22 mmol, 1 eq, HCl) in DCM (6 mL) was added DMAP (298.47 mg, 2.44 mmol, 2 eq) and EDCI (468.34 mg, 2.44 mmol, 2 eq), and then (2S)-4-(1-bicyclo[1.1.1]pentanyl)-1-tert-butoxycarbonyl-pyrrolidine-2-carboxylic acid (343.68 mg, 1.22 mmol, 1 eq) was added. The mixture was stirred at 25° C. for 2 h. Upon completion, the reaction mixture was poured into H$_2$O (20 mL) at 25° C., and then extracted with DCM (25 mL*3). The combined organic layers were washed with brine (25 mL*2), dried over Na$_2$SO$_4$, filtered and concentrated under reduced pressure to give a residue. The residue was purified by column chromatography (SiO$_2$, petroleum ether/ethyl acetate=1/0 to 0/1) to give tert-butyl (2S)-4-(1-bicyclo[1.1.1]pentanyl)-2-[[(1S)-2-methoxy-2-oxo-1-[[(3S)-2-oxopyrrolidin-3-yl]methyl]ethyl]carbamoyl]pyrrolidine-1-carboxylate (450 mg, 1.00 mmol, 81.95% yield) as a yellow solid. MS (ESI) m/z 450.1 [M+H]$^+$ Step 3: (2S)-methyl 2-((2S)-4-(bicyclo[1.1.1]pentan-1-yl)pyrrolidine-2-carboxamido)-3-((S)-2-oxopyrrolidin-3-yl)propanoate A solution of tert-butyl (2S)-4-(1-bicyclo[1.1.1]pentanyl)-2-[[(1S)-2-methoxy-2-oxo-1-[[(3S)-2-oxopyrrolidin-3-yl]methyl]ethyl]carbamoyl]pyrrolidine-1-carboxylate (350 mg, 778.58 umol, 1 eq) in HCl/MeOH (5 mL) was stirred at 25° C. for 0.5 h. Upon completion, the reaction mixture was concentrated to give methyl (2S)-2-[[(2S)-4-(1-bicyclo[1.1.1]pentanyl)pyrrolidine-2-carbonyl]amino]-3-[(3S)-2-oxopyrrolidin-3-yl]propanoate (300 mg, crude, HCl) as a yellow solid.

Step 4: (2S)-methyl 2-((2S)-4-(bicyclo[1.1.1]pentan-1-yl)-1-(4-methoxy-1H-indole-2-carbonyl)pyrrolidine-2-carboxamido)-3-((S)-2-oxopyrrolidin-3-yl)propanoate To a solution of 4-methoxy-1H-indole-2-carboxylic acid (222.95 mg, 1.17 mmol, 1.5 eq), methyl (2S)-2-[[(2S)-4-(1-bicyclo[1.1.1]pentanyl)pyrrolidine-2-carbonyl]amino]-3-[(3S)-2-oxopyrrolidin-3-yl]propanoate (300 mg, 777.43 umol, 1 eq, HCl) in DCM (6 mL) was added DMAP (284.94 mg, 2.33 mmol, 3 eq) and CDI (378.18 mg, 2.33 mmol, 3 eq). The mixture was stirred at 25° C. for 4 h. Upon completion, the reaction mixture was poured into H$_2$O (20 mL) at 25° C., and then extracted with DCM (30 mL*3). The combined organic layers were washed with brine (25 mL*2), dried over Na$_2$SO$_4$, filtered and concentrated under reduced pressure to give a residue. The residue was purified by prep-HPLC (Column: Kromasil C18 (250*50 mm*10 um); mobile phase: [water (10 mM HCOONH$_4$)-ACN]; B %: 35%-55%, 10 min) to give methyl (2S)-2-[[(2S)-4-(1-bicyclo[1.1.1]pentanyl)-1-(4-methoxy-1H-indole-2-carbonyl)pyrrolidine-2-carbonyl]amino]-3-[(3S)-2-oxopyrrolidin-3-yl]propanoate (200 mg, 373.91 umol, 48.09% yield, 97.70% purity) and methyl (2S)-2-[[(2S)-4-(1-bicyclo[1.1.1]pentanyl)-1-(4-methoxy-1H-indole-2-carbonyl)pyrrolidine-2-carbonyl]amino]-3-[(3S)-2-oxopyrrolidin-3-yl]propanoate (70 mg, 127.20 umol, 16.36% yield, 94.96% purity) as a yellow solid. MS (ESI) m/z 523.2 [M+H]$^+$ Step 5: (2S)-N-((S)-1-amino-1-oxo-3-((S)-2-oxopyrrolidin-3-yl)propan-2-yl)-4-(bicyclo[1.1.1]pentan-1-yl)-1-(4-methoxy-1H-indole-2-carbonyl)pyrrolidine-2-carboxamide Isomer 1: A solution of methyl (2S)-2-[[(2S)-4-(1-bicyclo[1.1.1]pentanyl)-1-(4-methoxy-1H-indole-2-carbonyl)pyrrolidine-2-carbonyl]amino]-3-[(3S)-2-oxopyrrolidin-3-yl]propanoate (200 mg, 382.71 umol, 1 eq) in NH$_3$/MeOH (7 M, 8 mL, 146.33 eq) was stirred at 80° C. for 24 h. Upon completion, the reaction mixture was concentrated to give (2S)-N-[(1S)-2-amino-2-oxo-1-[[(3S)-2-oxopyrrolidin-3-yl]methyl]ethyl]-4-(1-bicyclo[1.1.1]pentanyl)-1-(4-methoxy-1H-indole-2-carbonyl)pyrrolidine-2-carboxamide (150 mg, crude) as a yellow solid. MS (ESI) m/z 508.2 [M+H]$^+$ Isomer 2: A solution of methyl (2S)-2-[[(2S)-4-(1-bicyclo[1.1.1]pentanyl)-1-(4-methoxy-1H-indole-2-carbonyl)pyrrolidine-2-carbonyl]amino]-3-[(3S)-2-oxopyrrolidin-3-yl]propanoate (70 mg, 133.95 umol, 1 eq) in NH$_3$/MeOH (7 M, 4 mL, 209.04 eq) was stirred at 80° C. for 24 hr. Upon completion, the reaction mixture was concentrated to give (2S)-N-[(1S)-2-amino-2-oxo-1-[[(3S)-2-oxopyrrolidin-3-yl]methyl]ethyl]-4-(1-bicyclo[1.1.1]pentanyl)-1-(4-methoxy-1H-indole-2-carbonyl)pyrrolidine-2-carboxamide (50 mg, crude) as a yellow solid. MS (ESI) m/z 508.2 [M+H]$^+$ Step 6: (2S)-4-(bicyclo[1.1.1]pentan-1-yl)-N-((S)-1-cyano-2-((S)-2-oxopyrrolidin-3-yl)ethyl)-1-(4-methoxy-1H-indole-2-carbonyl)pyrrolidine-2-carboxamide Isomer 1: To a solution of (2S)-N-[(1S)-2-amino-2-oxo-1-[[(3S)-2-oxopyrrolidin-3-yl]methyl]ethyl]-4-(1-bicyclo[1.1.1]pentanyl)-1-(4-methoxy-1H-indole-2-carbonyl)pyrrolidine-2-carboxamide (145 mg, 285.67 umol, 1 eq) in DCM (4 mL) was added Burgess reagent (680.76 mg, 2.86 mmol, 10 eq). The mixture was stirred at 25° C. for 2 h. Upon completion, the reaction mixture was poured into H$_2$O (20 mL) at 25° C., and then extracted with DCM (30 mL*3). The combined organic layers were washed with brine (30 mL*2), dried over Na$_2$SO$_4$, filtered and concentrated under reduced pressure to give a residue. The residue was purified by prep-HPLC (column: Phenomenex Gemini-NX C18 75*30 mm*3 um; mobile phase: [water (10 mM NH4HCO3)-ACN]; B %: 30%-50%, 8 min) to give (2S)-4-

(1-bicyclo[1.1.1]pentanyl)-N-[(1S)-1-cyano-2-[(3S)-2-oxopyrrolidin-3-yl]ethyl]-1-(4-methoxy-1H-indole-2-carbonyl)pyrrolidine-2-carboxamide (46 mg, 93.11 umol, 32.59% yield, 99.09% purity) as a white solid. MS (ESI) m/z 490.2 [M+H]+; $^1$H NMR (400 MHz, MeOD-d$_4$) δ=7.24-6.79 (m, 3H), 6.56-6.41 (m, 1H), 5.05 (s, 1H), 4.63 (d, J=4.4 Hz, 1H), 4.34-3.36 (m, 6H), 3.03-1.50 (m, 15H), 1.37 (d, J=8.4 Hz, 1H).

Isomer 2: To a solution of (2S)-N-[(1S)-2-amino-2-oxo-1-[[(3S)-2-oxopyrrolidin-3-yl]methyl]ethyl]-4-(1-bicyclo[1.1.1]pentanyl)-1-(4-methoxy-1H-indole-2-carbonyl)pyrrolidine-2-carboxamide (50 mg, 98.51 umol, 1 eq) in DCM (2 mL) was added Burgess reagent (70.42 mg, 295.52 umol, 3 eq). The mixture was stirred at 25° C. for 2 h. Upon completion, the reaction mixture was poured into H$_2$O (20 mL) at 25° C., and then extracted with DCM (20 mL*3). The combined organic layers were washed with brine (20 mL*2), dried over Na$_2$SO$_4$, filtered and concentrated under reduced pressure to give a residue. The residue was purified by prep-HPLC (column: Phenomenex Gemini-NX C18 75*30 mm*3 um; mobile phase: [water (10 mM NH4HCO3)-ACN]; B %: 30%-50%, 8 min) to give (2S)-4-(1-bicyclo[1.1.1]pentanyl)-N-[(1S)-1-cyano-2-[(3S)-2-oxopyrrolidin-3-yl]ethyl]-1-(4-methoxy-1H-indole-2-carbonyl)pyrrolidine-2-carboxamide (10 mg, 20.14 umol, 20.45% yield, 98.61% purity) as a white solid. MS (ESI) m/z 490.2 [M+H]+; $^1$H NMR (400 MHz, MeOD-d$_4$) δ=7.16 (d, J=7.9 Hz, 1H), 7.10-7.00 (m, 2H), 6.53 (d, J=7.7 Hz, 1H), 5.01 (s, 1H), 4.66 (d, J=5.4, 8.3 Hz, 1H), 4.18-4.05 (m, 1H), 3.95 (s, 3H), 3.89 (s, 1H), 3.79 (d, J=6.4, 9.9 Hz, 1H), 2.70-2.60 (m, 1H), 2.51 (d, J=17.0 Hz, 2H), 2.43 (d, J=4.3, 8.5, 12.5 Hz, 1H), 2.30 (d, J=6.6, 13.7 Hz, 1H), 2.20-2.11 (m, 1H), 2.04-1.83 (m, 3H), 1.81-1.69 (m, 7H).

Example 124. Synthesis of Viral Protease Inhibitor Compound 387

Step 1: (S)-methyl 2-amino-3-((S)-2-oxopyrrolidin-3-yl)propanoate

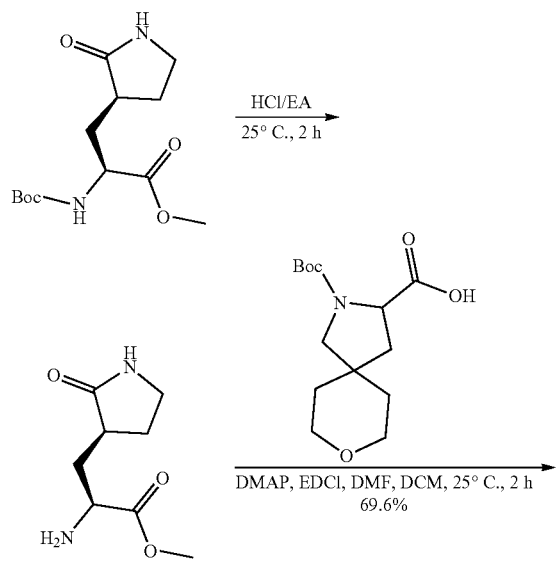

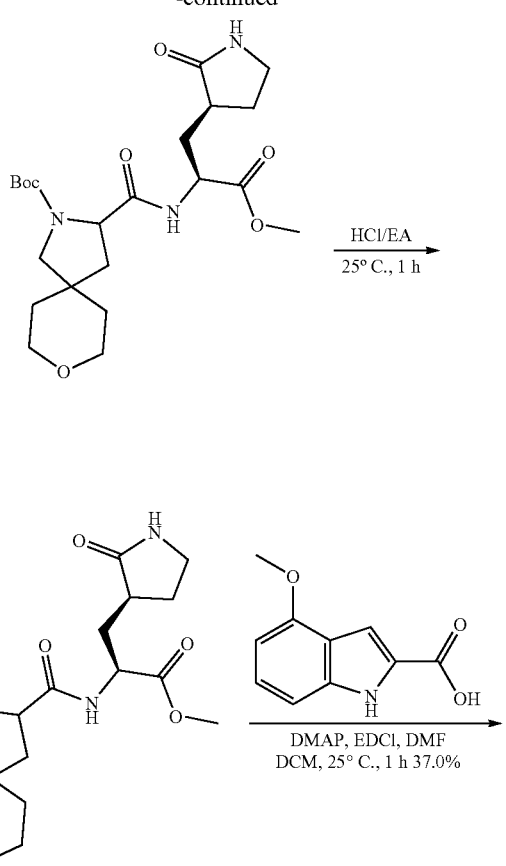

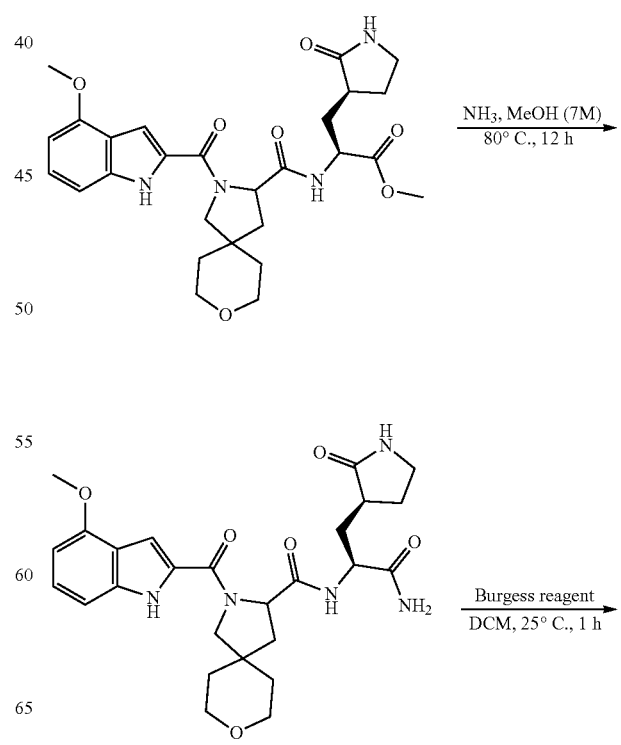

-continued

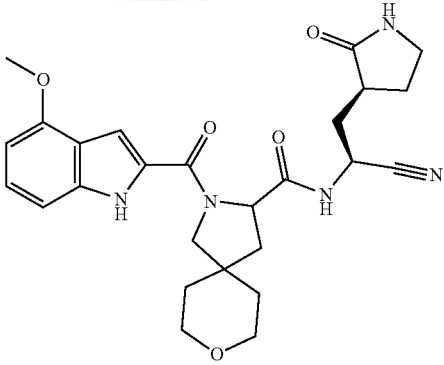

A mixture of methyl (2S)-2-(tert-butoxycarbonylamino)-3-[(3S)-2-oxopyrrolidin-3-yl]propanoate (0.3 g, 1.05 mmol, 1 eq) in HCl/EtOAc (4 M, 5 mL, 19.09 eq) was stirred at 25° C. for 2 h. Upon completion, the reaction mixture was concentrated under reduced pressure to give methyl (2S)-2-amino-3-[(3S)-2-oxopyrrolidin-3-yl]propanoate (0.2 g, crude) as a yellow gum.

Step 2: tert-butyl 3-(((S)-1-methoxy-1-oxo-3-((S)-2-oxopyrrolidin-3-yl)propan-2-yl)carbamoyl)-8-oxa-2-azaspiro[4.5]decane-2-carboxylate To a solution of methyl (2S)-2-amino-3-[(3S)-2-oxopyrrolidin-3-yl]propanoate (0.18 g, 808.38 umol, 1 eq, HCl) in DMF (1 mL) and DCM (2 mL) was added DMAP (197.52 mg, 1.62 mmol, 2 eq), 2-tert-butoxycarbonyl-8-oxa-2-azaspiro[4.5]decane-3-carboxylic acid (230.66 mg, 808.38 umol, 1 eq) and EDCI (309.93 mg, 1.62 mmol, 2 eq), and then the resulting solution was stirred at 25° C. for 2 h. Upon completion, the reaction mixture was diluted with water (20 mL) and extracted with DCM (10 mL*3). The combined organic layers were dried over Na$_2$SO$_4$, filtered and concentrated under reduced pressure to give a residue. The residue was purified by column chromatography (SiO$_2$, petroleum ether:ethyl acetate=1:1 to 0:1) to give tert-butyl 3-[[(1S)-2-methoxy-2-oxo-1-[[(3S)-2-oxopyrrolidin-3-yl]methyl]ethyl]carbamoyl]-8-oxa-2-azaspiro[4.5]decane-2-carboxylate (0.3 g, 562.26 umol, 69.55% yield, 85% purity) as a colorless oil. MS (ESI) m/z 454.2 [M+H]$^+$.

Step 3: (2S)-methyl 3-((S)-2-oxopyrrolidin-3-yl)-2-(8-oxa-2-azaspiro[4.5]decane-3-carboxamido)propanoate A mixture of tert-butyl 3-[[(1S)-2-methoxy-2-oxo-1-[[(3S)-2-oxopyrrolidin-3-yl]methyl]ethyl]carbamoyl]-8-oxa-2-azaspiro[4.5]decane-2-carboxylate (0.25 g, 551.23 umol, 1 eq) in HCl/EtOAc (5 mL) was stirred at 25° C. for 1 h. Upon completion, the reaction mixture was concentrated under reduced pressure to give methyl (2S)-2-(8-oxa-2-azaspiro[4.5]decane-3-carbonylamino)-3-[(3S)-2-oxopyrrolidin-3-yl]propanoate (0.2 g, crude, HCl) as a yellow oil.

Step 4: (2S)-methyl 2-(2-(4-methoxy-1H-indole-2-carbonyl)-8-oxa-2-azaspiro[4.5]decane-3-carboxamido)-3-((S)-2-oxopyrrolidin-3-yl)propanoate To a solution of methyl (2S)-2-(8-oxa-2-azaspiro[4.5]decane-3-carbonylamino)-3-[(3S)-2-oxopyrrolidin-3-yl]propanoate (0.2 g, 512.99 umol, 1 eq, HCl) in DMF (1 mL) and DCM (2 mL) was added DMAP (125.34 mg, 1.03 mmol, 2 eq), and then 4-methoxy-1H-indole-2-carboxylic acid (107.88 mg, 564.29 umol, 1.1 eq) and EDCI (196.68 mg, 1.03 mmol, 2 eq) was added. The solution was stirred at 25° C. for 1 h. Upon completion, the reaction mixture was diluted with water (10 mL) and extracted with DCM (5 mL*3). The combined organic layers were dried over Na$_2$SO$_4$, filtered and concentrated under reduced pressure to give a residue. The residue was purified by column chromatography (SiO$_2$, petroleum ether:ethyl acetate=0:1 to DCM:MeOH=10:1) to give methyl (2S)-2-[[2-(4-methoxy-1H-indole-2-carbonyl)-8-oxa-2-azaspiro[4.5]decane-3-carbonyl]amino]-3-[(3S)-2-oxopyrrolidin-3-yl]propanoate (0.13 g, 232.06 umol, 45.24% yield, 94% purity) as a yellow solid. MS (ESI) m/z 527.2 [M+H]$^+$.

Step 5: N-((S)-1-amino-1-oxo-3-((S)-2-oxopyrrolidin-3-yl)propan-2-yl)-2-(4-methoxy-1H-indole-2-carbonyl)-8-oxa-2-azaspiro[4.5]decane-3-carboxamide A mixture of methyl (2S)-2-[[2-(4-methoxy-1H-indole-2-carbonyl)-8-oxa-2-azaspiro[4.5]decane-3-carbonyl]amino]-3-[(3S)-2-oxopyrrolidin-3-yl]propanoate (0.13 g, 246.88 umol, 1 eq) in NH$_3$·MeOH (7 M, 3 mL, 85.06 eq) was stirred at 80° C. for 12 h. Upon completion, the reaction mixture was concentrated under reduced pressure to give N-[(1S)-2-amino-2-oxo-1-[[(3S)-2-oxopyrrolidin-3-yl]methyl]ethyl]-2-(4-methoxy-1H-indole-2-carbonyl)-8-oxa-2-azaspiro[4.5]decane-3-carboxamide (0.12 g, crude) as a yellow oil. MS (ESI) m/z 512.2 [M+H]$^+$.

Step 6: N-((S)-1-cyano-2-((S)-2-oxopyrrolidin-3-yl)ethyl)-2-(4-methoxy-1H-indole-2-carbonyl)-8-oxa-2-azaspiro[4.5]decane-3-carboxamide To a solution of N-[(1S)-2-amino-2-oxo-1-[[(3S)-2-oxopyrrolidin-3-yl]methyl]ethyl]-2-(4-methoxy-1H-indole-2-carbonyl)-8-oxa-2-azaspiro[4.5]decane-3-carboxamide (0.12 g, 234.57 umol, 1 eq) in DCM (2 mL) was added Burgess reagent (167.70 mg, 703.72 umol, 3 eq), and then the solution was stirred at 25° C. for 1 h. Upon completion, the reaction mixture was diluted with water (10 mL) and extracted with ethyl acetate (5 mL*3). The combined organic layers were dried over Na$_2$SO$_4$, filtered and concentrated under reduced pressure to give a residue. The residue was purified by prep-HPLC (column: Waters Xbridge BEH C18 100*25 mm*5 um; mobile phase: [water (10 mM NH$_4$HCO$_3$)-ACN]; B %: 15%-45%, 10 min) to give N-[(1S)-1-cyano-2-[(3S)-2-oxopyrrolidin-3-yl]ethyl]-2-(4-methoxy-1H-indole-2-carbonyl)-8-oxa-2-azaspiro[4.5]decane-3-carboxamide (44.25 mg, 88.76 umol, 37.84% yield, 99% purity) as a white solid. MS (ESI) m/z 494.2 [M+H]$^+$.

$^1$H NMR (400 MHz, METHANOL-d$_4$) δ=7.23-7.08 (m, 2H), 7.08-6.98 (m, 1H), 6.53 (br d, J=7.6 Hz, 1H), 5.02 (br dd, J=5.7, 10.1 Hz, 1H), 4.72-4.62 (m, 2H), 4.19-4.03 (m, 1H), 3.98-3.81 (m, 4H), 3.77-3.62 (m, 4H), 3.29-3.17 (m, 1H), 2.52-2.20 (m, 3H), 2.02-1.42 (m, 8H).

Example 125. Synthesis of Viral Protease Inhibitor Compound 389

Step 1: (S)-2-amino-3-((S)-2-oxopyrrolidin-3-yl)propanamide

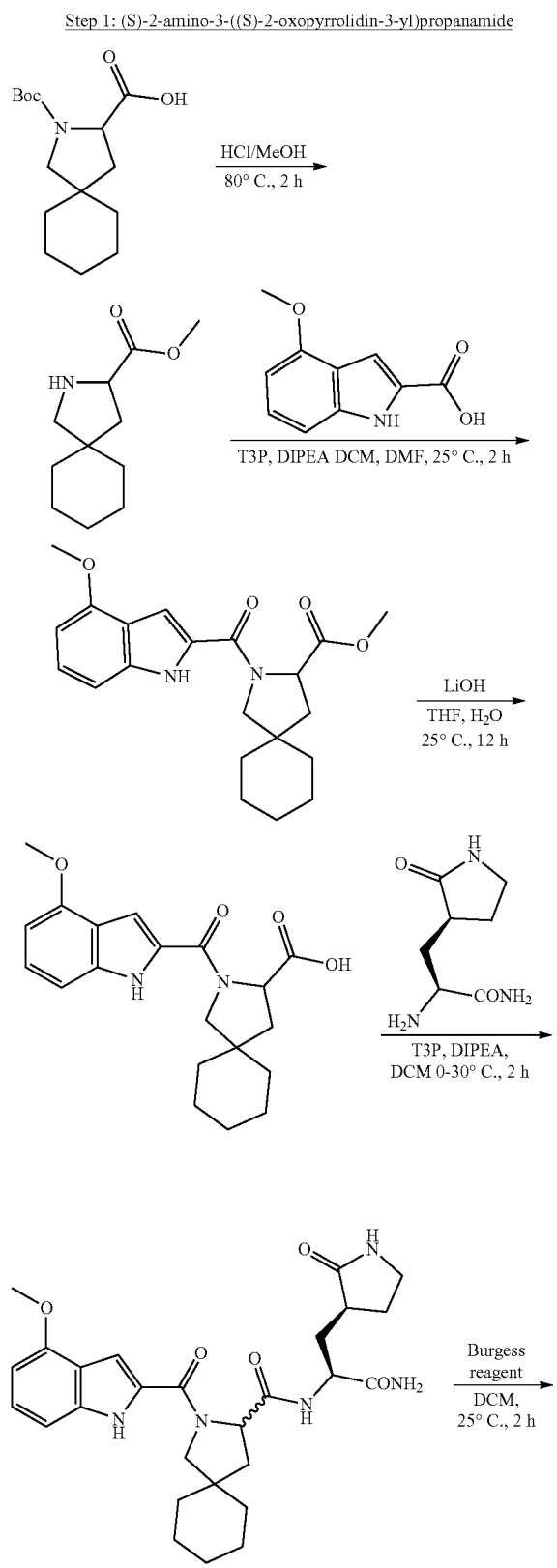

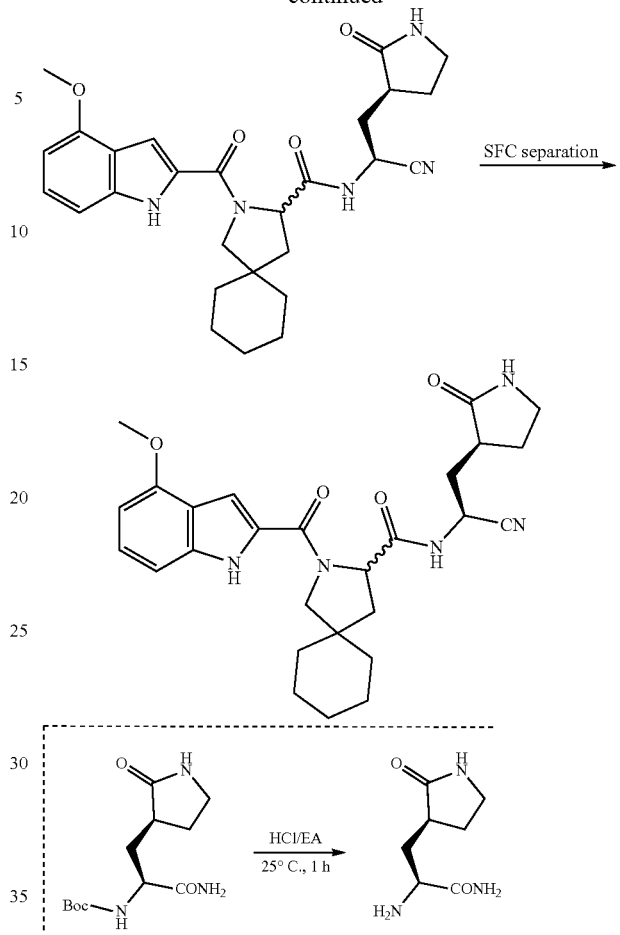

A solution of tert-butyl N-[(1S)-2-amino-2-oxo-1-[[(3S)-2-oxopyrrolidin-3-yl]methyl]ethyl]carbamate (2 g, 7.37 mmol, 1 eq) in HCl/EtOAc (4 M, 50 mL, 27.13 eq) was stirred at 25° C. for 1 h. Upon completion, the mixture was concentrated under the reduced pressure affording the product (2S)-2-amino-3-[(3S)-2-oxopyrrolidin-3-yl]propanamide (1.2 g, crude) as a white solid.

Step 2: methyl 2-azaspiro[4.5]decane-3-carboxylate

A solution of 2-tert-butoxycarbonyl-2-azaspiro[4.5]decane-3-carboxylic acid (3 g, 10.59 mmol, 1 eq) was added in HCl/MeOH (4 M, 50 mL, 18.89 eq) was stirred at 80° C. for 2 h. The mixture was concentrated under the reduced pressure affording the product methyl 2-azaspiro[4.5]decane-3-carboxylate (2 g, crude) as a yellow oil.

Step 3: methyl 2-(4-methoxy-1H-indole-2-carbonyl)-2-azaspiro[4.5]decane-3-carboxylate To a solution of methyl 2-azaspiro[4.5]decane-3-carboxylate (2 g, 10.14 mmol, 1 eq) and 4-methoxy-1H-indole-2-carboxylic acid (2.33 g, 12.17 mmol, 1.2 eq) in DCM (30 mL) and DMF (5 mL) was added T3P (12.90 g, 20.28 mmol, 12.06 mL, 50% purity, 2 eq) and DIEA (3.93 g, 30.41 mmol, 5.30 mL, 3 eq). The mixture was stirred at 25° C. for 2 h. Upon completion, the reaction mixture was quenched by addition H₂O (100 mL), and extracted with DCM (50 mL*3). The combined organic layers were washed with brine (50 mL), dried over Na₂SO₄, filtered and concentrated under reduced pressure to give a residue. The residue was purified by column chromatography (SiO₂, petroleum ether: ethyl acetate=10:1 to 0:1) affording the product methyl 2-(4-methoxy-1H-indole-2-carbonyl)-2-azaspiro[4.5]decane-3-carboxylate (3 g, 8.10 mmol, 79.88% yield) as a white solid. MS (ESI) m/z 371.1 [M+H]⁺

Step 4: 2-(4-methoxy-1H-indole-2-carbonyl)-2-azaspiro[4.5]decane-3-carboxylic acid To a solution of methyl 2-(4-methoxy-1H-indole-2-carbonyl)-2-azaspiro[4.5]decane-3-carboxylate (3 g, 8.10 mmol, 1 eq) in THF (45 mL) and H₂O (15 mL) was added LiOH·H₂O (1.70 g, 40.49 mmol, 5 eq). The mixture was stirred at 25° C. for 12 h. Upon completion, the mixture was quenched by addition H₂O (50 mL), and then added aq. HCl (1 M) to adjust the pH to about 3-4, and then extracted with ethyl acetate (50 mL*3). The combined organic layers were washed with brine (30 mL), dried over Na₂SO₄, filtered and concentrated under reduced pressure affording the product 2-(4-methoxy-1H-indole-2-carbonyl)-2-azaspiro[4.5]decane-3-carboxylic acid (2.6 g, crude) as a white solid. MS (ESI) m/z 357.1 [M+H]⁺

Step 5: N-((S)-1-amino-1-oxo-3-((S)-2-oxopyrrolidin-3-yl)propan-2-yl)-2-(4-methoxy-1H-indole-2-carbonyl)-2-azaspiro[4.5]decane-3-carboxamide To a solution of 2-(4-methoxy-1H-indole-2-carbonyl)-2-azaspiro[4.5]decane-3-carboxylic acid (1 g, 2.81 mmol, 1 eq) and (2S)-2-amino-3-[(3S)-2-oxopyrrolidin-3-yl]propanamide (720.49 mg, 4.21 mmol, 1.5 eq) in DCM (30 mL) was added T₃P (3.57 g, 5.61 mmol, 3.34 mL, 50% purity, 2 eq) and DIEA (1.09 g, 8.42 mmol, 1.47 mL, 3 eq) at 0° C. The mixture was stirred at 30° C. for 1 h. Upon completion, the mixture was quenched by addition H₂O (100 mL), and then extracted with DCM (50 mL*3). The combined organic layers were washed with brine (50 mL), dried over Na₂SO₄, filtered and concentrated under reduced pressure to give a residue. The residue was purified by column chromatography (SiO₂, DCM:MeOH=1:0 to 10:1) affording the product N-[(1S)-2-amino-2-oxo-1-[[(3S)-2-oxopyrrolidin-3-yl]methyl]ethyl]-2-(4-methoxy-1H-indole-2-carbonyl)-2-azaspiro[4.5]decane-3-carboxamide (700 mg, 1.37 mmol, 48.96% yield) as a white solid. MS (ESI) m/z 510.3 [M+H]⁺

Step 6: N-((S)-1-cyano-2-((S)-2-oxopyrrolidin-3-yl)ethyl)-2-(4-methoxy-1H-indole-2-carbonyl)-2-azaspiro[4.5]decane-3-carboxamide To a solution of N-[(1S)-2-amino-2-oxo-1-[[(3S)-2-oxopyrrolidin-3-yl]methyl]ethyl]-2-(4-methoxy-1H-indole-2-carbonyl)-2-azaspiro[4.5]decane-3-carboxamide (700 mg, 1.37 mmol, 1 eq) in DCM (10 mL) was added Burgess reagent (982.03 mg, 4.12 mmol, 3 eq). The mixture was stirred at 25° C. for 2 h. Upon completion, the mixture was concentrated under the reduced pressure to give a residue. The residue was purified by prep-HPLC (column: Kromasil C18 (250*50 mm*10 um); mobile phase: [water (10 mM NH₄HCO₃)-ACN]; B %: 30%-60%, 10 min) affording the product N-[(1S)-1-cyano-2-[(3S)-2-oxopyrrolidin-3-yl]ethyl]-2-(4-methoxy-1H-indole-2-carbonyl)-2-azaspiro[4.5]decane-3-carboxamide (500 mg, 1.02 mmol, 74.05% yield) as a white solid. MS (ESI) m/z 492.3 [M+H]⁺

Step 7: N-((S)-1-cyano-2-((S)-2-oxopyrrolidin-3-yl)ethyl)-2-(4-methoxy-1H-indole-2-carbonyl)-2-azaspiro[4.5]decane-3-carboxamide N-[(1S)-1-cyano-2-[(3S)-2-oxopyrrolidin-3-yl]ethyl]-2-(4-methoxy-1H-indole-2-carbonyl)-2-azaspiro[4.5]decane-3-carboxamide (500 mg, 1.02 mmol) was separated by SFC (column: DAICEL CHIRALPAK AD (250 mm*30 mm, 10 um); mobile phase: [0.1% NH₃H₂O IPA]; B %: 55%-55%, 9 min) affording the product N-[(1S)-1-cyano-2-[(3S)-2-oxopyrrolidin-3-yl]ethyl]-2-(4-methoxy-1H-indole-2-carbonyl)-2-azaspiro[4.5]decane-3-carboxamide Isomer 1 (264 mg, 537.04 umol, 52.80% yield, 100% purity) as a white solid. MS (ESI) m/z 492.3 [M+H]⁺

¹H NMR (400 MHz, METHANOL-d₄) δ=7.28-6.76 (m, 3H), 6.60-6.38 (m, 1H), 5.05 (br dd, J=5.2, 10.2 Hz, 1H), 4.63-4.60 (m, 1H), 4.03-3.85 (m, 5H), 3.74-3.28 (m, 1H), 2.73 (br dd, J=5.0, 8.6 Hz, 1H), 2.51-2.28 (m, 2H), 2.27-2.08 (m, 1H), 1.96-1.72 (m, 2H), 1.69-1.38 (m, 1H), 1.37-1.09 (m, 1H).

N-[(1S)-1-cyano-2-[(3S)-2-oxopyrrolidin-3-yl]ethyl]-2-(4-methoxy-1H-indole-2-carbonyl)-2-azaspiro[4.5]decane-3-carboxamide Isomer 2 (140 mg, 284.51 umol, 27.97% yield, 99.9% purity) as a white solid. MS (ESI) m/z 492.3 [M+H]⁺

¹H NMR (400 MHz, METHANOL-d₄) δ=7.30-6.81 (m, 3H), 6.53 (br d, J=2.0 Hz, 1H), 5.12-4.95 (m, 2H), 4.70-4.55 (m, 2H), 4.08-3.86 (m, 4H), 3.84-3.72 (m, 1H), 2.62-2.40 (m, 1H), 2.36-2.18 (m, 2H), 1.94-1.69 (m, 3H), 1.68-1.34 (m, 11H).

Example 126. Synthesis of Viral Protease Inhibitor Compound 391

Step 1: (S)-methyl 2-amino-3-((S)-2-oxopyrrolidin-3-yl)propanoate

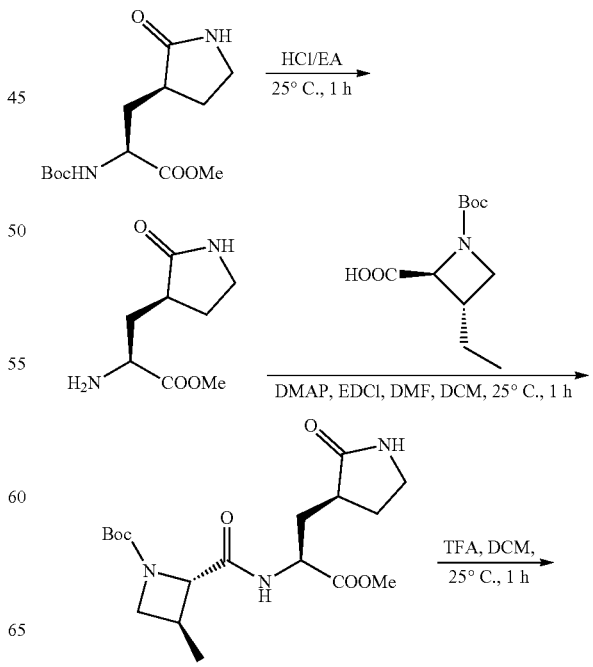

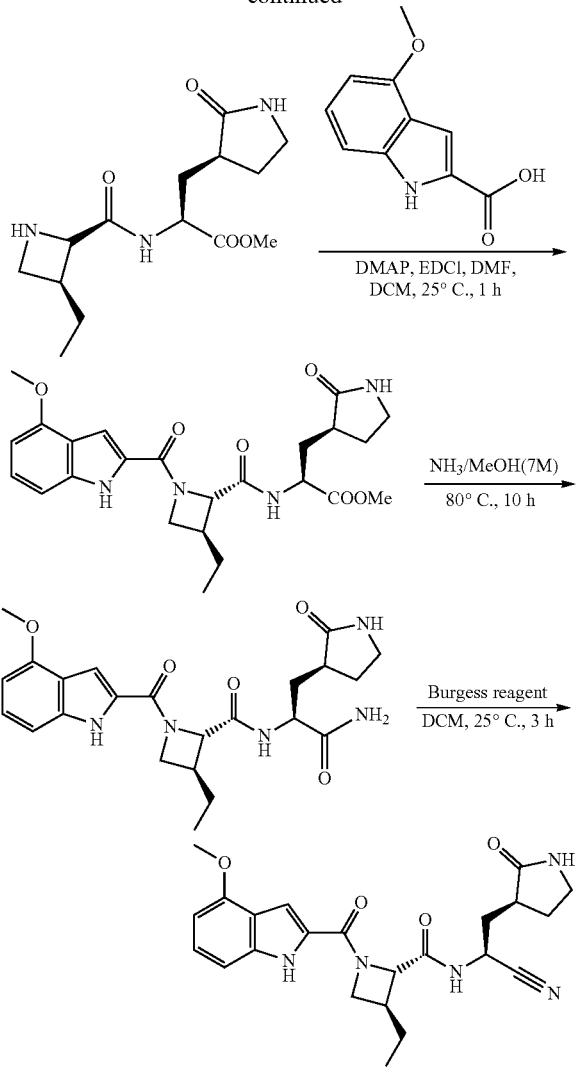

To a solution of methyl (S)-methyl 2-((tert-butoxycarbonyl)amino)-3-((S)-2-oxopyrrolidin-3-yl)propanoate (350 mg, 1.22 mmol, 1 eq) was added HCl/EtOAc (12 mL) and the mixture was stirred at 25° C. for 1 h. Upon completion, the mixture was concentrated in the vacuum to give a crude product (S)-methyl 2-amino-3-((S)-2-oxopyrrolidin-3-yl)propanoate (330 mg, crude) as yellow oil. MS (ESI) m/z 187.1 [M+H]$^+$ Step 2: (2S,3S)-tert-butyl3-ethyl-2-(((S)-1-methoxy-1-oxo-3-((S)-2-oxopyrrolidin-3-yl)propan-2-yl)carbamoyl)azetidine-1-carboxylate To a solution of (S)-methyl 2-amino-3-((S)-2-oxopyrrolidin-3-yl)propanoate (330 mg, 1.77 mmol, 1 eq), (2S,3S)-1-(tert-butoxycarbonyl)-3-ethylazetidine-2-carboxylic acid (406.32 mg, 1.77 mmol, 1 eq) in DMF (2 mL) and DCM (10 mL) was added EDCI (679.47 mg, 3.54 mmol, 2 eq) and DMAP (433.02 mg, 3.54 mmol, 2 eq). After stirring the mixture at 25° C. for 1 h, the mixture was quenched by addition H$_2$O (50 mL) and then extracted with EtOAc (30 mL*3). The combined organic layers were washed with brine (30 mL), dried over Na$_2$SO$_4$, filtered and concentrated under reduced pressure to give a residue and was purified by prep-TLC (SiO$_2$, petroleum ether:ethyl acetate=0:1) to give the crude product (2S,3S)-tert-butyl 3-ethyl-2-(((S)-1-methoxy-1-oxo-3-((S)-2-oxopyrrolidin-3-yl)propan-2-yl)carbamoyl)azetidine-1-carboxylate (270 mg, 679.31 umol, 38.33% yield) was obtained as yellow oil. MS (ESI) m/z 398.2 [M+H]$^+$ Step 3: (S)-methyl 2-((2S,3S)-3-ethylazetidine-2-carboxamido)-3-((S)-2-oxopyrrolidin-3-yl)propanoate To a solution of (2S,3S)-tert-butyl 3-ethyl-2-(((S)-1-methoxy-1-oxo-3-((S)-2-oxopyrrolidin-3-yl)propan-2-yl)carbamoyl)azetidine-1-carboxylate (240 mg, 603.83 umol, 1 eq) in DCM (1 mL) was added TFA (4.13 g, 36.23 mmol, 2.68 mL, 60 eq), and the resulting mixture was stirred at 25° C. for 1 h. Upon completion, the residue was poured into NaHCO$_3$ (10 mL) and was extracted with EtOAc (10 mL*3). The combined organic phase was washed with brine (10 mL*2), dried with anhydrous Na$_2$SO$_4$, filtered and concentrated in vacuum to give the crude product (S)-methyl 2-((2S,3S)-3-ethylazetidine-2-carboxamido)-3-((S)-2-oxopyrrolidin-3-yl)propanoate (200 mg, crude) as white solid. MS (ESI) m/z 298.2 [M+H]$^+$ Step 4: (S)-methyl2-((2S,3S)-3-ethyl-1-(4-methoxy-1H-indole-2-carbonyl)azetidine-2-carboxamido)-3-((S)-2-oxopyrrolidin-3-yl)propanoate To a solution of (S)-methyl 2-((2S,3S)-3-ethylazetidine-2-carboxamido)-3-((S)-2-oxopyrrolidin-3-yl)propanoate (200 mg, 672.61 umol, 1 eq), 4-methoxy-1H-indole-2-carboxylic acid (128.59 mg, 672.61 umol, 1 eq) in DCM (1 mL) was added EDCI (257.88 mg, 1.35 mmol, 2 eq), and DMAP (164.34 mg, 1.35 mmol, 2 eq), and the mixture was stirred at 25° C. for 1 h. Upon completion, the residue was poured into H$_2$O (10 mL) and was extracted with EtOAc (10 mL*3). The combined organic phase was washed with brine (10 mL*2), dried with anhydrous Na$_2$SO$_4$, filtered and concentrated in vacuum and was purified by prep-TLC (SiO$_2$, [petroleum ether:ethyl acetate=0:1) to give product (S)-methyl 2-((2S,3S)-3-ethyl-1-(4-methoxy-1H-indole-2-carbonyl)azetidine-2-carboxamido)-3-((S)-2-oxopyrrolidin-3-yl)propanoate (90 mg, 191.28 umol, 28.44% yield) as white solid. MS (ESI) m/z 471.2 [M+H]$^+$ Step5:(2S,3S)-N-((S)-1-amino-1-oxo-3-((S)-2-oxopyrrolidin-3-yl)propan-2-yl)-3-ethyl-1-(4-methoxy-1H-indole-2-carbonyl)azetidine-2-carboxamide A solution of (S)-methyl 2-((2S,3S)-3-ethyl-1-(4-methoxy-1H-indole-2-carbonyl)azetidine-2-carboxamido)-3-((S)-2-oxopyrrolidin-3-yl)propanoate (80 mg, 170.03 umol, 1 eq) in NH$_3$/MeOH (7 M, 16.00 mL, 658.72 eq) was stirred at 80° C. for 16 h. Upon completion, the mixture was concentrated in the vacuum to give product (2S,3S)-N-((S)-1-amino-1-oxo-3-((S)-2-oxopyrrolidin-3-yl)propan-2-yl)-3-ethyl-1-(4-methoxy-1H-indole-2-carbonyl)azetidine-2-carboxamide (66 mg, crude) as a white solid. MS (ESI) m/z 456.2 [M+H]$^+$ Step6:(2S,3S)-N-((S)-1-cyano-2-((S)-2-oxopyrrolidin-3-yl)ethyl)-3-ethyl-1-(4-methoxy-1H-indole-2-carbonyl)azetidine-2-carboxamide To a solution of (2S,3S)-N-((S)-1-amino-1-oxo-3-((S)-2-oxopyrrolidin-3-yl)propan-2-yl)-3-ethyl-1-(4-methoxy-1H- indole-2-carbonyl)azetidine-2-carboxamide (66 mg, 144.89 umol, 1 eq) in DCM (3 mL) was added Burgess reagent (414.35 mg, 1.74 mmol, 12 eq), and then the mixture was stirred at 25° C. for 3 h. Upon completion, the mixture was concentrated in the vacuum and was purified by prep-HPLC (column: Phenomenex Gemini-NX C18 75*30 mm*3 um; mobile phase: [water(0.05% NH$_3$H$_2$O+10 mM NH$_4$HCO$_3$)-ACN]; B %: 15%-45%, 8 min) to give (2S,3S)-N-((S)-1-cyano-2-((S)-2-oxopyrrolidin-3-yl)ethyl)-3-ethyl-1-(4-methoxy-1H-indole-2-carbonyl)azetidine-2-carboxamide (5 mg, 11.43 umol, 7.89% yield). MS (ESI) m/z 438.2 [M+H]$^+$ $^1$H NMR (400 MHz, MeOD-d$_4$) δ=7.24-7.11 (m, 1H), 7.09-6.61 (m, 2H), 6.52-6.51 (m, 1H), 5.08-4.87 (m, 0.5H), 4.75-4.73 (m, 1.5H), 4.56-4.43 (m, 1H), 4.42-4.00 (m, 1H), 3.93 (s, 3H), 3.22-2.90 (m, 1H), 2.65-2.63 (m, 2H), 2.42-2.07 (m, 2H), 2.04-1.49 (m, 5H), 1.01-0.99 (m, 3H)

Example 127. Synthesis of Viral Protease Inhibitor Compound 395

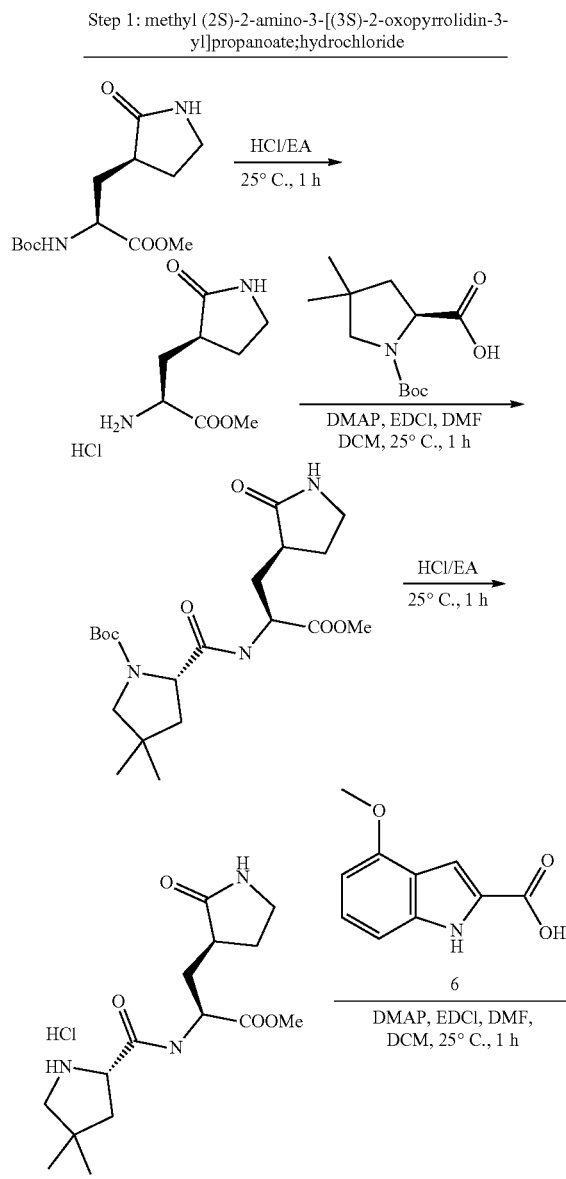

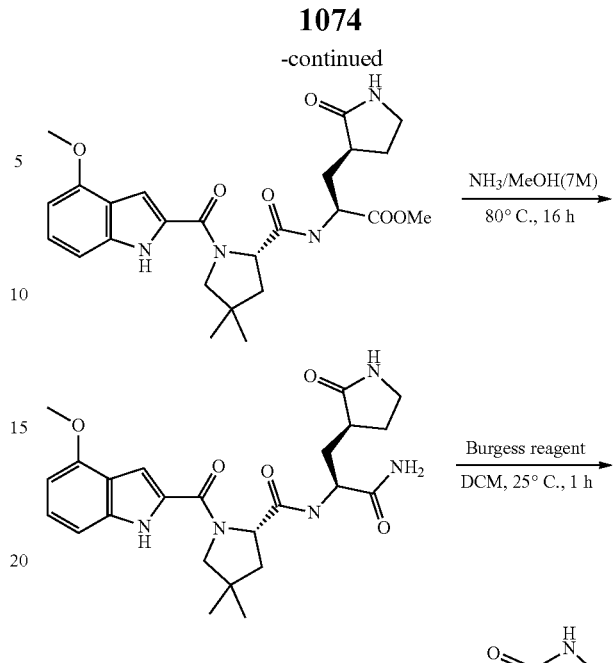

To methyl (2S)-2-(tert-butoxycarbonylamino)-3-[(3S)-2-oxopyrrolidin-3-yl]propanoate (300 mg, 1.05 mmol, 1 eq) was added HCl/EtOAc (4 M, 30 mL) at 25° C., and the mixture was stirred at 25° C. for 1 h. The reaction mixture was concentrated under reduced pressure to give methyl (2S)-2-amino-3-[(3S)-2-oxopyrrolidin-3-yl]propanoate; hydrochloride (230 mg, crude) as a yellow oil and used directly for next step.

Step 2: (S)-tert-butyl 2-(((S)-1-methoxy-1-oxo-3-((S)-2-oxopyrrolidin-3-yl)propan-2-yl)carbamoyl)-4,4-dimethylpyrrolidine-1-carboxylate A mixture of methyl (2S)-2-amino-3-[(3S)-2-oxopyrrolidin-3-yl]propanoate (230 mg, 1.03 mmol, 1 eq, HCl), (2S)-1-tert-butoxycarbonyl-4,4-dimethyl-pyrrolidine-2-carboxylic acid (251.31 mg, 1.03 mmol, 1 eq), DMAP (252.38 mg, 2.07 mmol, 2 eq), EDCI (396.02 mg, 2.07 mmol, 2 eq), DMF (2 mL) and DCM (4 mL) was stirred at 25° C. for 1 h. The reaction mixture was diluted with H$_2$O (30 mL) and extracted with DCM (30 mL*3). The combined organic layers were washed with brine (50 mL), dried over Na$_2$SO$_4$, filtered and concentrated under reduced pressure to give a residue. The residue was purified by column chromatography (SiO$_2$, petroleum ether/ethyl acetate=0/1) to afford (S)-tert-butyl 2-(((S)-1-methoxy-1-oxo-3-((S)-2-oxopyrrolidin-3-yl)propan-2-yl)carbamoyl)-4,4-dimethylpyrrolidine-1-carboxylate (200 mg, 486.04 umol, 47.05% yield), as a yellow oil. MS (ESI) m/z 412.2 [M+H]$^+$.

Step 3: (S)-methyl-2-((S)-4,4-dimethylpyrrolidine-2-carboxamido)-3-((S)-2-oxopyrrolidin-3-yl)propanoate A mixture of (S)-tert-butyl 2-(((S)-1-methoxy-1-oxo-3-((S)-2-oxopyrrolidin-3-yl)propan-2-yl)carbamoyl)-4,4-dimethylpyrrolidine-1-carboxylate (200 mg, 486.04 umol, 1 eq) and HCl/EtOAc (4 M, 20 mL) was stirred at 25° C. for 1 h. The reaction mixture was concentrated under reduced pressure to give a product (S)-methyl-2-((S)-4,4-dimethylpyrrolidine-2-carboxamido)-3-((S)-2-oxopyrrolidin-3-yl)propanoate (170 mg, crude, HCl) as a yellow oil and used directly for next step.

Step 4: (S)-methyl 2-((S)-1-(4-methoxy-1H-indole-2-carbonyl)-4,4-dimethylpyrrolidine-2-carboxamido)-3-((S)-2-oxopyrrolidin-3-yl)propanoate A mixture of (S)-methyl-2-((S)-4,4-dimethylpyrrolidine-2-carboxamido)-3-((S)-2-oxopyrrolidin-3-yl)propanoate (170 mg, 488.74 umol, 1 eq, HCl), 4-methoxy-1H-indole-2-carboxylic acid (93.44 mg, 488.74 umol, 1 eq), DMAP (119.42 mg, 977.47 umol, 2 eq), EDCI (187.38 mg, 977.47 umol, 2 eq), DMF (2 mL) and DCM (4 mL) was stirred at 25° C. for 1 h. The reaction mixture was diluted with $H_2O$ (30 mL) and extracted with DCM (30 mL*3). The combined organic layers were washed with brine (50 mL), dried over $Na_2SO_4$, filtered and concentrated under reduced pressure to give a residue. The residue was purified by column chromatography ($SiO_2$, petroleum ether/ethyl acetate=0/1) to get the compound (S)-methyl-2-((S)-1-(4-methoxy-1H-indole-2-carbonyl)-4,4-dimethylpyrrolidine-2-carboxamido)-3-((S)-2-oxopyrrolidin-3-yl)propanoate (180 mg, 371.48 umol, 76.01% yield) as yellow solid. MS (ESI) m/z 485.2 $[M+H]^+$.

Step 5: (S)-N-((S)-1-amino-1-oxo-3-((S)-2-oxopyrrolidin-3-yl)propan-2-yl)-1-(4-methoxy-1H-indole-2-carbonyl)-4,4-dimethylpyrrolidine-2-carboxamide A mixture of (S)-methyl-2-((S)-1-(4-methoxy-1H-indole-2-carbonyl)-4,4-dimethylpyrrolidine-2-carboxamido)-3-((S)-2-oxopyrrolidin-3-yl)propanoate (180 mg, 371.48 umol, 1 eq), and $NH_3$/MeOH (7 M, 7 mL) was stirred at 80° C. for 16 h. The reaction mixture was concentrated under reduced pressure to give a product (S)-N-((S)-1-amino-1-oxo-3-((S)-2-oxopyrrolidin-3-yl)propan-2-yl)-1-(4-methoxy-1H-indole-2-carbonyl)-4,4-dimethylpyrrolidine-2-carboxamide (170 mg, crude) as a yellow solid. MS (ESI) m/z 470.2 $[M+H]^+$.

Step 6: (S)-N-((S)-1-cyano-2-((S)-2-oxopyrrolidin-3-yl)ethyl)-1-(4-methoxy-1H-indole-2-carbonyl)-4,4-dimethylpyrrolidine-2-carboxamide A mixture of (S)-N-((S)-1-amino-1-oxo-3-((S)-2-oxopyrrolidin-3-yl)propan-2-yl)-1-(4-methoxy-1H-indole-2-carbonyl)-4,4-dimethylpyrrolidine-2-carboxamide (160 mg, 340.76 umol, 1 eq), Burgess reagent (649.66 mg, 2.73 mmol, 8 eq) and DCM (25 mL) was stirred at 25° C. for 1 h. The reaction mixture was concentrated under reduced pressure to give a residue. The residue was purified by prep-HPLC (column: Phenomenex Gemini-NX C18 75*30 mm*3 um; mobile phase: [water(0.05% $NH_3H_2O$+10 mM $NH_4HCO_3$)-ACN]; B %: 15%-40%, 8 min) to get the product (S)-N-((S)-1-cyano-2-((S)-2-oxopyrrolidin-3-yl)ethyl)-1-(4-methoxy-1H-indole-2-carbonyl)-4,4-dimethylpyrrolidine-2-carboxamide Isomer 1 (27 mg, 58.95 umol, 17.30% yield, 98.58% purity), as white solid. MS (ESI) m/z 452.3 $[M+H]^+$.

$^1$H NMR (400 MHz, DMSO-$d_6$) δ=11.76-11.39 (m, 1H), 9.18-8.79 (m, 1H), 7.85-7.46 (m, 1H), 7.21-6.67 (m, 3H), 6.58-6.35 (m, 1H), 5.13-4.81 (m, 1H), 4.74-4.31 (m, 1H), 3.97-3.55 (m, 5H), 3.31-3.05 (m, 2H), 2.47-1.96 (m, 4H), 1.85-1.27 (m, 3H), 1.25-0.80 (m, 6H).

(S)-N-((S)-1-cyano-2-((S)-2-oxopyrrolidin-3-yl)ethyl)-1-(4-methoxy-1H-indole-2-carbonyl)-4,4-dimethylpyrrolidine-2-carboxamide Isomer 2 (3 mg, 6.41 umol, 1.88% yield, 96.44% purity), as white solid. MS (ESI) m/z 452.3 $[M+H]^+$.

$^1$H NMR (400 MHz, DMSO-$d_6$) δ=11.78-11.34 (m, 1H), 9.33-8.76 (m, 1H), 7.91-7.53 (m, 1H), 7.23-6.67 (m, 3H), 6.61-6.31 (m, 1H), 5.09-4.80 (m, 1H), 4.61-4.43 (m, 1H), 4.01-3.67 (m, 5H), 3.20-2.99 (m, 2H), 2.43-1.91 (m, 4H), 1.86-1.55 (m, 3H), 1.33-0.83 (m, 6H).

Example 128. Synthesis of Viral Protease Inhibitor Compound 397

Step 1: tert-butyl N-[(1S)-2-amino-2-oxo-1-[[(3S)-2-oxopyrrolidin-3-yl]methyl]ethyl]carbamate

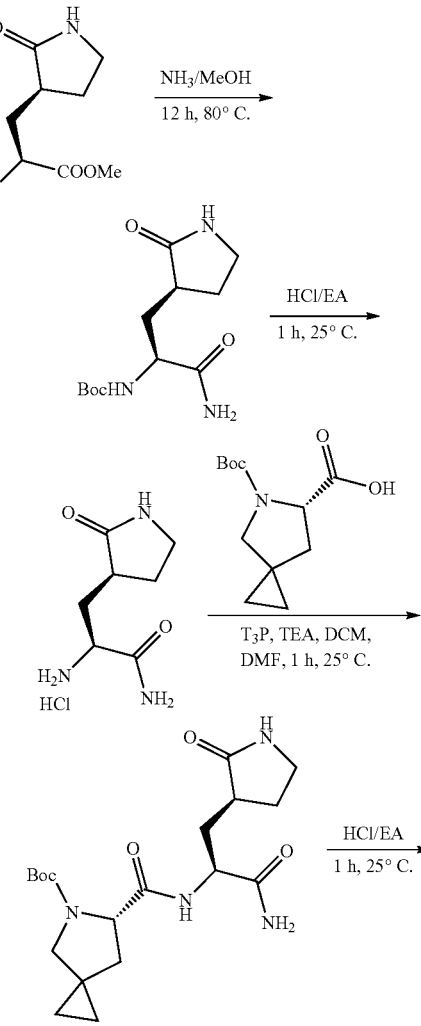

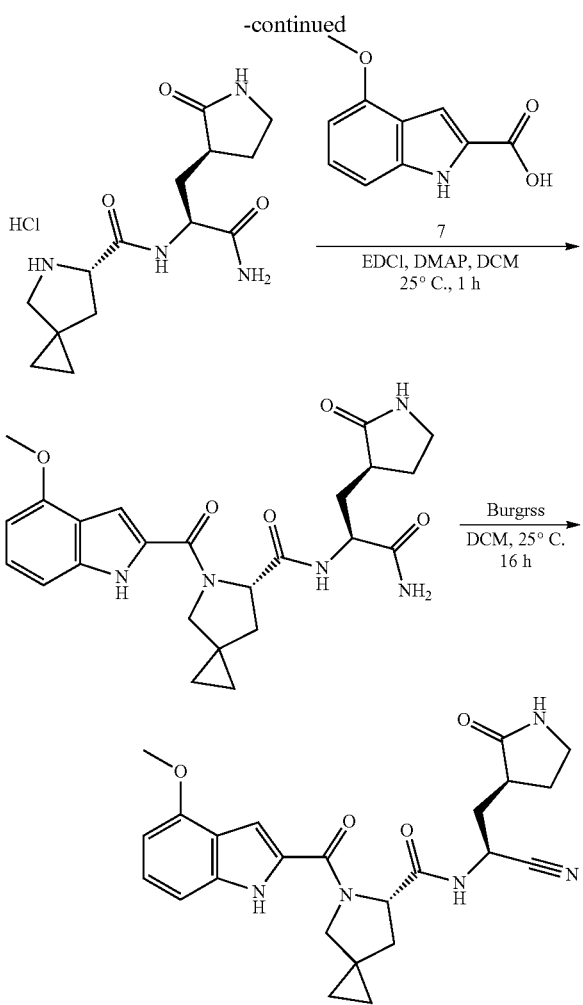

To a solution of methyl (2S)-2-(tert-butoxycarbonylamino)-3-[(3S)-2-oxopyrrolidin-3-yl]propanoate (1 g, 3.49 mmol, 1 eq) in NH₃/MeOH (7 M, 15 mL) was stirred at 80° C. for 12 h. Upon completion, the reaction mixture was concentrated under reduced pressure. The tert-butyl N-[(1S)-2-amino-2-oxo-1-[[(3S)-2-oxopyrrolidin-3-yl]methyl]ethyl]carbamate (900 mg, crude) was obtained as white solid. MS (ESI) m/z 272.2 [M+H]⁺.

Step 2: (2S)-2-amino-3-[(3S)-2-oxopyrrolidin-3-yl]propanamide

A solution of tert-butyl N-[(1S)-2-amino-2-oxo-1-[[(3S)-2-oxopyrrolidin-3-yl]methyl]ethyl]carbamate (900 mg, 3.32 mmol, 1 eq) in HCl/EA (4 M, 15 mL) was stirred at 25° C. for 1 h. Upon completion, the reaction mixture was concentrated under reduced pressure to get the product (2S)-2-amino-3-[(3S)-2-oxopyrrolidin-3-yl]propanamide (650 mg, crude, HCl) as white solid. MS (ESI) m/z 172.1 [M+H]⁺.

Step 3: tert-butyl (6S)-6-[[(1S)-2-amino-2-oxo-1-[[(3S)-2-oxopyrrolidin-3-yl]methyl]ethyl]carbamoyl]-5-azaspiro[2.4]heptane-5-carboxylate A solution of (2S)-2-amino-3-[(3S)-2-oxopyrrolidin-3-yl]propanamide (400 mg, 1.93 mmol, 1 eq, HCl), (6S)-5-tert-butoxycarbonyl-5-azaspiro[2.4]heptane-6-carboxylic acid (464.77 mg, 1.93 mmol, 1 eq) and TEA (974.58 mg, 9.63 mmol, 1.34 mL, 5 eq) was dissolved in DCM (8 mL) and DMF (3 mL), and then the solution cooled to 0° C. After adding T₃P (3.68 g, 5.78 mmol, 3.44 mL, 50% purity, 3 eq) to the solution, the mixture was stirred for 1 h and warmed to 25° C. gradually. Upon completion, the mixture was added H₂O (50 mL) and then extracted with ethyl acetate (50 mL*3). The combined organic layers were washed with brine (50 mL), dried over Na₂SO₄, filtered and concentrated under reduced pressure to get the product tert-butyl (6S)-6-[[(1S)-2-amino-2-oxo-1-[[(3S)-2-oxopyrrolidin-3-yl]methyl]ethyl]carbamoyl]-5-azaspiro[2.4]heptane-5-carboxylate (200 mg, crude) was obtained as yellow solid. MS (ESI) m/z 395.2 [M+H]⁺.

Step 4: (6S)-N-[(1S)-2-amino-2-oxo-1-[[(3S)-2-oxopyrrolidin-3-yl]methyl]ethyl]-5-azaspiro[2.4]heptane-6-carboxamide A solution of tert-butyl (6S)-6-[[(1S)-2-amino-2-oxo-1-[[(3S)-2-oxopyrrolidin-3-yl]methyl]ethyl]carbamoyl]-5-azaspiro[2.4]heptane-5-carboxylate (200 mg, 464.12 umol, 1 eq, HCl) in HCl/EtOAc (4 M, 15 mL) was stirred at 25° C. for 1 h. Upon completion, the reaction mixture was concentrated under reduced pressure to afford (6S)-N-[(1S)-2-amino-2-oxo-1-[[(3S)-2-oxopyrrolidin-3-yl]methyl]ethyl]-5-azaspiro[2.4]heptane-6-carboxamide (140 mg, crude, HCl) as a white solid. MS (ESI) m/z 295.2 [M+H]⁺.

Step 5: (6S)-N-[(1S)-2-amino-2-oxo-1-[[(3S)-2-oxopyrrolidin-3-yl]methyl]ethyl]-5-(4-methoxy-1H-indole-2-carbonyl)-5-azaspiro[2.4]heptane-6-carboxamide To a solution of (6S)-N-[(1S)-2-amino-2-oxo-1-[[(3S)-2-oxopyrrolidin-3-yl]methyl]ethyl]-5-azaspiro[2.4]heptane-6-carboxamide (140 mg, 423.20 umol, 1 eq, HCl), 4-methoxy-1H-indole-2-carboxylic acid (80.91 mg, 423.20 umol, 1 eq), EDCI (202.82 mg, 1.06 mmol, 2.5 eq) was added DMAP (155.11 mg, 1.27 mmol, 3 eq) in DCM (3 mL), and then the reaction was stirred at 25° C. for 1 h. Upon completion, the mixture was added H₂O (30 mL) and then extracted with ethyl acetate (30 mL*3). The combined organic layers were washed with brine (30 mL), dried over Na₂SO₄, filtered and concentrated under reduced pressure to afford (6S)-N-[(1S)-2-amino-2-oxo-1-[[(3S)-2-oxopyrrolidin-3-yl]methyl]ethyl]-5-(4-methoxy-1H-indole-2-carbonyl)-5-azaspiro[2.4]heptane-6-carboxamide (80 mg, 117.37 umol, 27.73% yield, 68.59% purity) as yellow solid. MS (ESI) m/z 468.2 [M+H]⁺.

Step 6: (6S)-N-[(1S)-1-cyano-2-[(3S)-2-oxopyrrolidin-3-yl]ethyl]-5-(4-methoxy-1H-indole-2-carbonyl)-5-azaspiro[2.4]heptane-6-carboxamide A solution of (6S)-N-[(1S)-2-amino-2-oxo-1-[[(3S)-2-oxopyrrolidin-3-yl]methyl]ethyl]-5-(4-methoxy-1H-indole-2-carbonyl)-5-azaspiro[2.4]heptane-6-carboxamide (80 mg, 171.12 umol, 1 eq) and methoxycarbonyl-(triethylammonio)sulfonyl-azanide (163.11 mg, 684.47 umol, 4 eq) in DCM (5 mL) was stirred at 25° C. for 16 h. Upon completion, the reaction mixture was concentrated and concentrated under reduced pressure to afford (6S)-N-[(1S)-1-cyano-2-[(3S)-2-oxopyrrolidin-3-yl]ethyl]-5-(4-methoxy-1H-indole-2-carbonyl)-5-azaspiro[2.4]heptane-6-carboxamide (15.5 mg, 34.44 umol, 20.13% yield, 99.88% purity) as a white solid. MS (ESI) m/z 450.2 [M+H]⁺.

$^1$H NMR (400 MHz, METHANOL-d$_4$) δ=7.23-7.12 (m, 1H), 6.87-7.10 (m, 2H), 6.59-6.39 (m, 1H), 5.35-5.07 (m, 2H), 4.85-4.69 (m, 1H), 4.10-3.61 (m, 5H), 3.03-2.17 (m, 4H), 2.13-1.62 (m, 3H), 1.62-1.22 (m, 1H), 0.87-0.57 (m, 4H).

Example 129. Synthesis of Viral Protease Inhibitor Compound 399

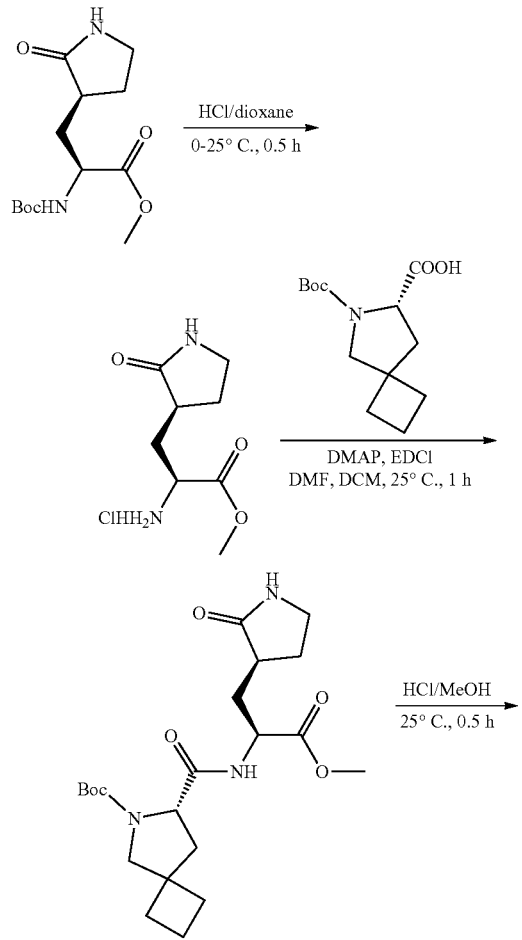

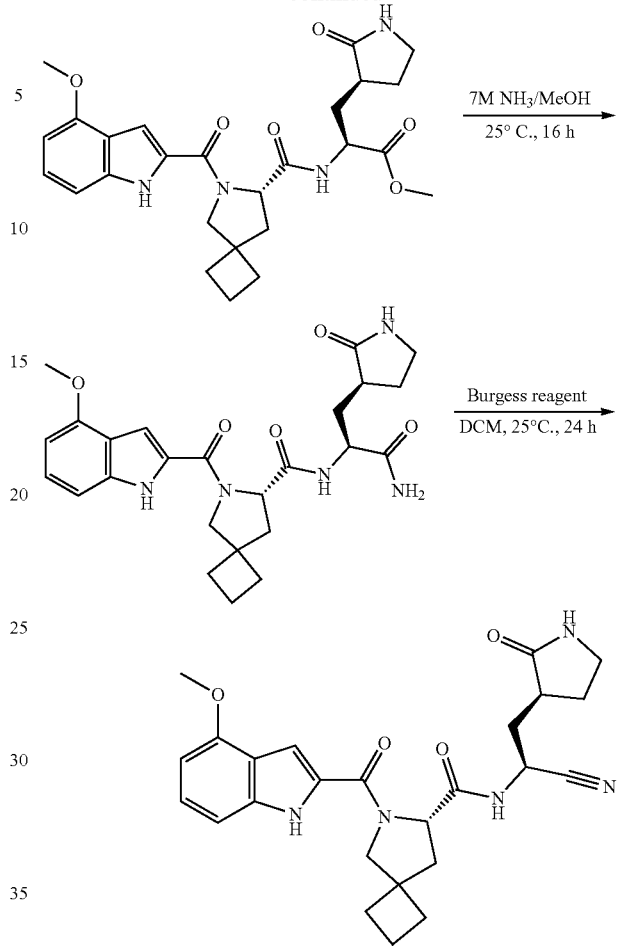

A solution of methyl (2S)-2-(tert-butoxycarbonylamino)-3-[(3S)-2-oxopyrrolidin-3-yl]propanoate (130 mg, 454.03 umol, 1 eq) in HCl/dioxane (4 M, 2.27 mL, 20 eq) was stirred at 25° C. for 0.5 h. The reaction mixture was concentrated under reduced pressure to afford methyl (2S)-2-amino-3-[(3S)-2-oxopyrrolidin-3-yl]propanoate (173.4 mg, 451.67 umol, 99.48% yield, 58% purity, HCl) as a yellow liquid.

Step 2: (S)-tert-butyl 7-(((S)-1-methoxy-1-oxo-3-((S)-2-oxopyrrolidin-3-yl)propan-2-yl)carbamoyl)-6-azaspiro[3.4]octane-6-carboxylate To a solution of (7S)-6-tert-butoxycarbonyl-6-azaspiro [3.4]octane-7-carboxylic acid (105.34 mg, 412.59 umol, 1 eq) and methyl (2S)-2-amino-3-[(3S)-2-oxopyrrolidin-3-yl] propanoate (158.4 mg, 412.59 umol, 58% purity, 1 eq, HCl) in DCM (1.2 mL) and DMF (0.4 mL) was added DMAP (100.81 mg, 825.19 umol, 2 eq) and EDCI (158.19 mg, 825.19 umol, 2 eq). After stirring the mixture at 25° C. for 1 h, the residue was diluted with H$_2$O (6 mL) and extracted with ethyl acetate (3 mL). The combined organic layers were washed with ethyl acetate (3 mL*3), dried over Na$_2$SO$_4$, filtered and concentrated under reduced pressure to give a residue. The residue was purified by prep-TLC (SiO$_2$, petroleum ether/ethyl acetate=0/1) afford tert-butyl (7S)-7-[[(1S)-2-methoxy-2-oxo-1-[[(3S)-2-oxopyrrolidin-3-yl]methyl]

ethyl]carbamoyl]-6-azaspiro[3.4]octane-6-carboxylate (66.3 mg, 156.55 umol, 37.94% yield) as a yellow liquid. MS (ESI) m/z 424.0 [M+H]+

Step 3: (S)-methyl 3-((S)-2-oxopyrrolidin-3-yl)-2-((S)-6-azaspiro[3.4]octane-7-carboxamido)propanoate A solution of tert-butyl (7S)-7-[[(1S)-2-methoxy-2-oxo-1-[[(3S)-2-oxopyrrolidin-3-yl]methyl]ethyl]carbamoyl]-6-azaspiro[3.4]octane-6-carboxylate (66.3 mg, 156.55 umol, 1 eq) in HCl/MeOH (4 M, 782.76 uL, 20 eq) was stirred at 25° C. for 0.5 h. The reaction mixture was concentrated under reduced pressure to afford methyl (2S)-2-[[(7S)-6-azaspiro[3.4]octane-7-carbonyl]amino]-3-[(3S)-2-oxopyrrolidin-3-yl]propanoate (71.1 mg, 156.09 umol, 99.71% yield, 79% purity, HCl) as a yellow liquid.

Step 4: (S)-methyl 2-((S)-6-(4-methoxy-1H-indole-2-carbonyl)-6-azaspiro[3.4]octane-7-carboxamido)-3-((S)-2-oxopyrrolidin-3-yl)propanoate To a solution of methyl (2S)-2-[[(7S)-6-azaspiro[3.4]octane-7-carbonyl]amino]-3-[(3S)-2-oxopyrrolidin-3-yl]propanoate (62.8 mg, 137.87 umol, 79% purity, 1 eq, HCl) and 4-methoxy-1H-indole-2-carboxylic acid (26.36 mg, 137.87 umol, 1 eq) in DCM (1.2 mL) and DMF (0.4 mL) was added DMAP (33.69 mg, 275.74 umol, 2 eq) and EDCI (52.86 mg, 275.74 umol, 2 eq) at 25° C. for 1 h. The residue was diluted with brine (6 mL) and extracted with EtOAc (3 mL*3). The combined organic layers were dried over Na$_2$SO$_4$, filtered and concentrated under reduced pressure to give a residue. The residue was purified by prep-TLC (SiO$_2$, petroleum ether/ethyl acetate=0/1) to get the product methyl (2S)-2-[[(7S)-6-(4-methoxy-1H-indole-2-carbonyl)-6-azaspiro[3.4]octane-7-carbonyl]amino]-3-[(3S)-2-oxopyrrolidin-3-yl]propanoate (33.2 mg, 66.86 umol, 48.50% yield) was obtained as a white solid. MS (ESI) m/z 497.1 [M+H]+

Step 5: (S)-N-((S)-1-amino-1-oxo-3-((S)-2-oxopyrrolidin-3-yl)propan-2-yl)-6-(4-methoxy-1H-indole-2-carbonyl)-6-azaspiro[3.4]octane-7-carboxamide A mixture of methyl (2S)-2-[[(7S)-6-(4-methoxy-1H-indole-2-carbonyl)-6-azaspiro[3.4]octane-7-carbonyl]amino]-3-[(3S)-2-oxopyrrolidin-3-yl]propanoate (23.0 mg, 46.32 umol, 1 eq) and ammonia (7 M, 4 mL, 604.50 eq) was stirred at 25° C. for 16 h. The reaction mixture was concentrated under reduced pressure to afford (7S)-N-[(1S)-2-amino-2-oxo-1-[[(3S)-2-oxopyrrolidin-3-yl]methyl]ethyl]-6-(4-methoxy-1H-indole-2-carbonyl)-6-azaspiro[3.4]octane-7-carboxamide (15 mg, crude) as a yellow solid. MS (ESI) m/z 482.2 [M+H]+

Step 6: (S)-N-((S)-1-cyano-2-((S)-2-oxopyrrolidin-3-yl)ethyl)-6-(4-methoxy-1H-indole-2-carbonyl)-6-azaspiro[3.4]octane-7-carboxamide A solution of (7S)-N-[(1S)-2-amino-2-oxo-1-[[(3S)-2-oxopyrrolidin-3-yl]methyl]ethyl]-6-(4-methoxy-1H-indole-2-carbonyl)-6-azaspiro[3.4]octane-7-carboxamide (15 mg, 28.66 umol, 92% purity, 1 eq) and Burgess reagent (13.66 mg, 57.32 umol, 2 eq) was stirred at 25° C. for 24 h. The reaction mixture was concentrated under reduced pressure to give a residue. The residue was purified by prep-HPLC (column: Waters Xbridge BEH C18 100*30 mm*10 um; mobile phase: [water (10 mM NH$_4$HCO$_3$)-ACN]; B %: 20%-45%, 8 min) to afford (7S)-N-[(1S)-1-cyano-2-[(3S)-2-oxopyrrolidin-3-yl]ethyl]-6-(4-methoxy-1H-indole-2-carbonyl)-6-azaspiro[3.4]octane-7-carboxamide (3.01 mg, 6.49 umol, 22.66% yield, 100% purity) as a white solid. MS (ESI) m/z 464.3 [M+H]+

$^1$H NMR (400 MHz, METHANOL-d$_4$) δ ppm 6.95-7.24 (m, 3H) 6.47-6.58 (m, 1H) 5.01 (br dd, J=10.67, 5.19 Hz, 1H) 4.58 (t, J=7.09 Hz, 1H) 3.82-4.19 (m, 5H) 3.19 (br t, J=8.52 Hz, 1H) 2.93-3.07 (m, 1H) 2.28-2.56 (m, 3H) 2.16-2.27 (m, 2H) 1.94-2.14 (m, 6H) 1.47-1.86 (m, 2H).

Example 130. Synthesis of Viral Protease Inhibitor Compound 401

Step 1: (S)-methyl 2-amino-3-((S)-2-oxopyrrolidin-3-yl)propanoate

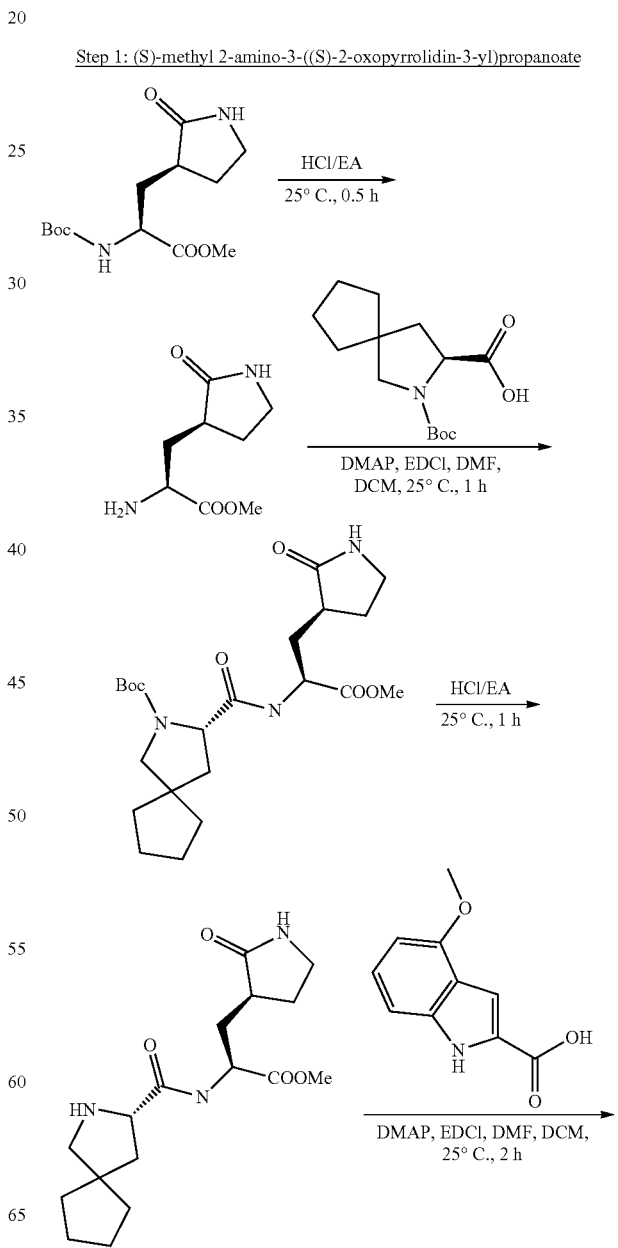

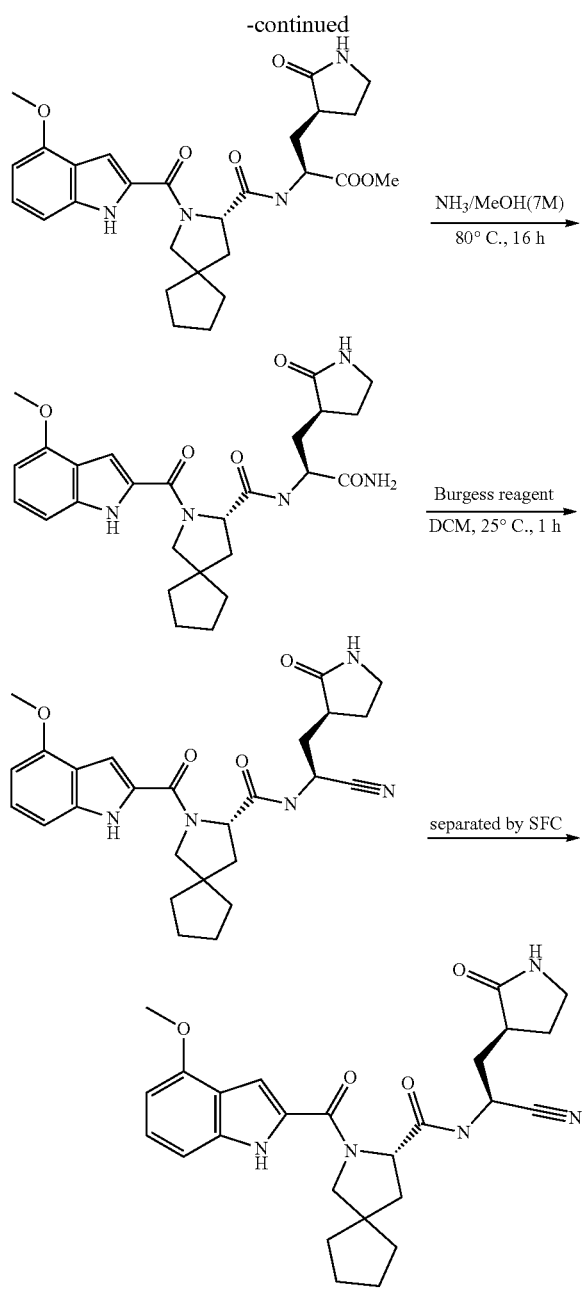

methyl (2S)-2-(tert-butoxycarbonylamnino)-3-[(3S)-2-oxopyrrolidin-3-yl]propanoate (400 mg, 1.40 mmol, 1 eq) in HCl/EtOAc (4 M, 10 mL, 28.63 eq) was stirred at 25° C. for 0.5 h. Upon completion, the mixture was concentrated under the reduced pressure affording the product methyl (2S)-2-amino-3-[(3S)-2-oxopyrrolidin-3-yl]propanoate (300 mg, crude, HCl) as a yellow solid.

Step 2: (S)-tert-butyl3-(((S)-1-methoxy-1-oxo-3-((S)-2-oxopyrrolidin-3-yl)propan-2-yl)carbamoyl)-2-azaspiro[4.4]nonane-2-carboxylate methyl (2S)-2-amino-3-[(3S)-2-oxopyrrolidin-3-yl]propanoate (300 mg, 1.35 mmol, 1 eq, HCl) and (3S)-2-tertbutoxycarbonyl-2-azaspiro[4.4]nonane-3-carboxylic acid (362.87 mg, 1.35 mmol, 1 eq) in DMF (2 mL) and DCM (5 mL) was added DMAP (329.19 mg, 2.69 mmol, 2 eq) and EDCI (516.56 mg, 2.69 mmol, 2 eq). The mixture was stirred at 25° C. for 1 h. Upon completion, the reaction mixture was quenched by addition H₂O (10 mL), and then extracted with DCM (10 mL*3). The combined organic layers were washed with brine (10 mL), dried over Na₂SO₄, filtered and concentrated under reduced pressure to give a residue. The residue was purified by column chromatography (SiO₂, Petroleum ether:Ethyl acetate=5:1 to 0:1) affording the product tert-butyl(3S)-3-[[(1S)-2-methoxy-2-oxo-1-[[(3S)-2-oxopyrrolidin-3-yl]methyl]ethyl]carbamoyl]-2-azaspiro[4.4]nonane-2-carboxylate (340 mg, 777.09 umol, 57.68% yield) as a yellow oil.

Step 3: (S)-methyl3-((S)-2-oxopyrrolidin-3-yl)-2-((S)-2-azaspiro[4.4]nonane-3-carboxamido)propanoate tert-butyl(3S)-3-[[(1S)-2-methoxy-2-oxo-1-[[(3S)-2-oxopyrrolidin-3-yl]methyl]ethyl]carbamoyl]-2-azaspiro[4.4]nonane-2-carboxylate (340 mg, 777.09 umol, 1 eq) in HCl/EtOAc (4 M, 10 mL, 51.47 eq) was stirred at 25° C. for 1 h. Upon completion, the mixture was concentrated under the reduced pressured affording the product methyl(2S)-2-[[(3S)-2-azaspiro[4.4]nonane-3-carbonyl]amino]-3-[(3S)-2-oxopyrrolidin-3-yl]propanoate (250 mg, crude, HCl) as a yellow oil.

Step 4: (S)-methyl2-((S)-2-(4-methoxy-1H-indole-2-carbonyl)-2-azaspiro[4.4]nonane-3-carboxamido)-3-((S)-2-oxopyrrolidin-3-yl)propanoate methyl(2S)-2-[[(3S)-2-azaspiro[4.4]nonane-3-carbonyl]amino]-3-[(3S)-2-oxopyrrolidin-3-yl]propanoate (250 mg, 668.67 umol, 1 eq, HCl) and 4-methoxy-1H-indole-2-carboxylic acid (127.84 mg, 668.67 umol, 1 eq) in DMF (2 mL) and DCM (6 mL) was added DMAP (163.38 mg, 1.34 mmol, 2 eq) and EDCI (256.37 mg, 1.34 mmol, 2 eq). The mixture was stirred at 25° C. for 2 h. Upon completion, the reaction mixture was quenched by addition H₂O (10 mL), and then extracted with DCM (10 mL*3). The combined organic layers were washed with brine (10 mL), dried over Na₂SO₄, filtered and concentrated under reduced pressure to give a residue. The residue was purified by prep-TLC (SiO₂, PE:EA=0:1) affording the product methyl(2S)-2-[[(3S)-2-(4-methoxy-1H-indole-2-carbonyl)-2-azaspiro[4.4]nonane-3-carbonyl]amino]-3-[(3S)-2-oxopyrrolidin-3-yl]propanoate (180 mg, 352.54 umol, 52.72% yield) as a yellow oil. MS (ESI) m/z 511.2 [M+H]⁺

Step 5: (S)-N-((S)-1-amino-1-oxo-3-((S)-2-oxopyrrolidin-3-yl)propan-2-yl)-2-(4-methoxy-1H-indole-2-carbonyl)-2-azaspiro[4.4]nonane-3-carboxamide methyl(2S)-2-[[(3S)-2-(4-methoxy-1H-indole-2-carbonyl)-2-azaspiro[4.4]nonane-3-carbonyl]amino]-3-[(3S)-2-oxopyrrolidin-3-yl]propanoate (180 mg, 352.54 umol, 1 eq) in ammonia (7 M, 20 mL, 397.12 eq) was stirred as 80° C. for 16 h. Upon completion, the mixture was concentrated under the reduced pressure affording the product (3S)-N-[(1S)-1-amino-2-oxo-1-[[(3S)-2-oxopyrrolidin-3-yl]

methyl]ethyl]-2-(4-methoxy-1H-indole-2-carbonyl)-2-azaspiro[4.4]nonane-3-carboxamide (170 mg, crude) as a yellow oil.

Step 6: (S)-N-((S)-1-cyano-2-((S)-2-oxopyrrolidin-3-yl)ethyl)-2-(4-methoxy-1H-indole-2-carbonyl)-2-azaspiro[4.4]nonane-3-carboxamide (3S)-N-[(1S)-2-amino-2-oxo-1-[[(3S)-2-oxopyrrolidin-3-yl]methyl]ethyl]-2-(4-methoxy-1H-indole-2-carbonyl)-2-azaspiro[4.4]nonane-3-carboxamide (170 mg, 343.04 umol, 1 eq) in DCM (3 mL) was added methoxycarbonyl-(triethylammonio)sulfonyl-azanide (408.74 mg, 1.72 mmol, 5 eq). The mixture was stirred at 25° C. for 1 h. Upon completion, the mixture was concentrated under the reduced pressure to give a residue. The residue was purified by prep-HPLC (column: Waters Xbridge BEH C18 100*25 mm*5 um; mobile phase: [water (10 mM NH$_4$HCO$_3$)-ACN]; B %: 30%-60%, 10 min) affording the product (3S)-N-[(1S)-1-cyano-2-[(3S)-2-oxopyrrolidin-3-yl]ethyl]-2-(4-methoxy-1H-indole-2-carbonyl)-2-azaspiro[4.4]nonane-3-carboxamide (25 mg, 51.09 umol, 14.89% yield, 97.6% purity) as a white solid. MS (ESI) m/z 478.2 [M+H]$^+$ $^1$H NMR (400 MHz, MeOD-d$_4$) δ=7.22-7.12 (m, 1H), 7.11-6.98 (m, 2H), 6.58-6.45 (m, 1H), 5.11-4.95 (m, 1H), 4.65-4.52 (m, 1H), 3.94 (s, 3H), 3.93-3.80 (m, 2H), 3.28-3.18 (m, 1H), 2.54-2.02 (m, 4H), 2.01-1.48 (m, 12H).

Step 7: (S)-N-((S)-1-cyano-2-((S)-2-oxopyrrolidin-3-yl)ethyl)-2-(4-methoxy-1H-indole-2-carbonyl)-2-azaspiro[4.4]nonane-3-carboxamide Isomer 1: (S)-N-((S)-1-cyano-2-((S)-2-oxopyrrolidin-3-yl)ethyl)-2-(4-methoxy-11H-indole-2-carbonyl)-2-azaspiro[4.4]nonane-3-carboxamide (30 mg, 62.82 umol) was separated by prep-SFC (column: DAICEL CHIRALPAK IC (250 mm*30 mm, 5 um); mobile phase: [Neu-ETOH]; B %: 40%-40%, 15 min) affording the product (3S)-N-[(1S)-1-cyano-2-[(3S)-2-oxopyrrolidin-3-yl]ethyl]-2-(4-methoxy-1H-indole-2-carbonyl)-2-azaspiro[4.4]nonane-3-carboxamide (12.11 mg, 24.62 umol, 39.20% yield, 97.1% purity) as a white solid. MS (ESI) m/z 478.2 [M+H]$^+$ $^1$H NMR (400 MHz, MeOD-d$_4$) δ=7.20-7.11 (m, 1H), 7.08-6.85 (m, 2H), 6.59-6.42 (m, 1H), 5.05 (br dd, J=5.6, 10.4 Hz, 1H), 4.58 (br dd, J=7.4, 9.6 Hz, 1H), 3.97-3.92 (m, 3H), 3.88-3.52 (m, 2H), 3.28 (br s, 1H), 2.87-2.65 (m, 1H), 2.47-2.29 (m, 2H), 2.25-2.16 (m, 1H), 2.03-1.53 (m, 1H), 1.34-1.20 (m, 1H).

Isomer 2: (S)-N-((S)-1-cyano-2-((S)-2-oxopyrrolidin-3-yl)ethyl)-2-(4-methoxy-1H-indole-2-carbonyl)-2-azaspiro[4.4]nonane-3-carboxamide (30 mg, 62.82 umol) was separated by prep-SFC (column: DAICEL CHIRALPAK IC (250 mm*30 mm, 5 um); mobile phase: [Neu-ETOH]; B %: 40%-40%, 15 min) affording the product (3S)-N-[(1S)-1-cyano-2-[(3S)-2-oxopyrrolidin-3-yl]ethyl]-2-(4-methoxy-1H-indole-2-carbonyl)-2-azaspiro[4.4]nonane-3-carboxamide (16.81 mg, 34.46 umol, 54.86% yield, 97.9% purity) as a white solid. MS (ESI) m/z 478.2 [M+H]$^+$ $^1$H NMR (400 MHz, MeOD-d$_4$) δ=7.23-7.13 (m, 1H), 7.10-6.84 (m, 2H), 6.52 (d, J=7.7 Hz, 1H), 5.03 (br dd, J=5.7, 10.4 Hz, 1H), 4.67-4.54 (m, 1H), 4.00-3.57 (m, 5H), 3.27-3.16 (m, 1H), 2.55-2.39 (m, 1H), 2.37-2.04 (m, 3H), 2.02-1.44 (m, 1H), 1.43-1.16 (m, 1H).

Example 131. Synthesis of Viral Protease Inhibitor Compound 405

Step 1: methyl (2S)-2-[[(2S)-2-(tert-butoxycarbonylamino)-4,4-dimethyl-pentanoyl]amino]-3-[(3S)-2-oxopyrrolidin-3-yl]propanoate

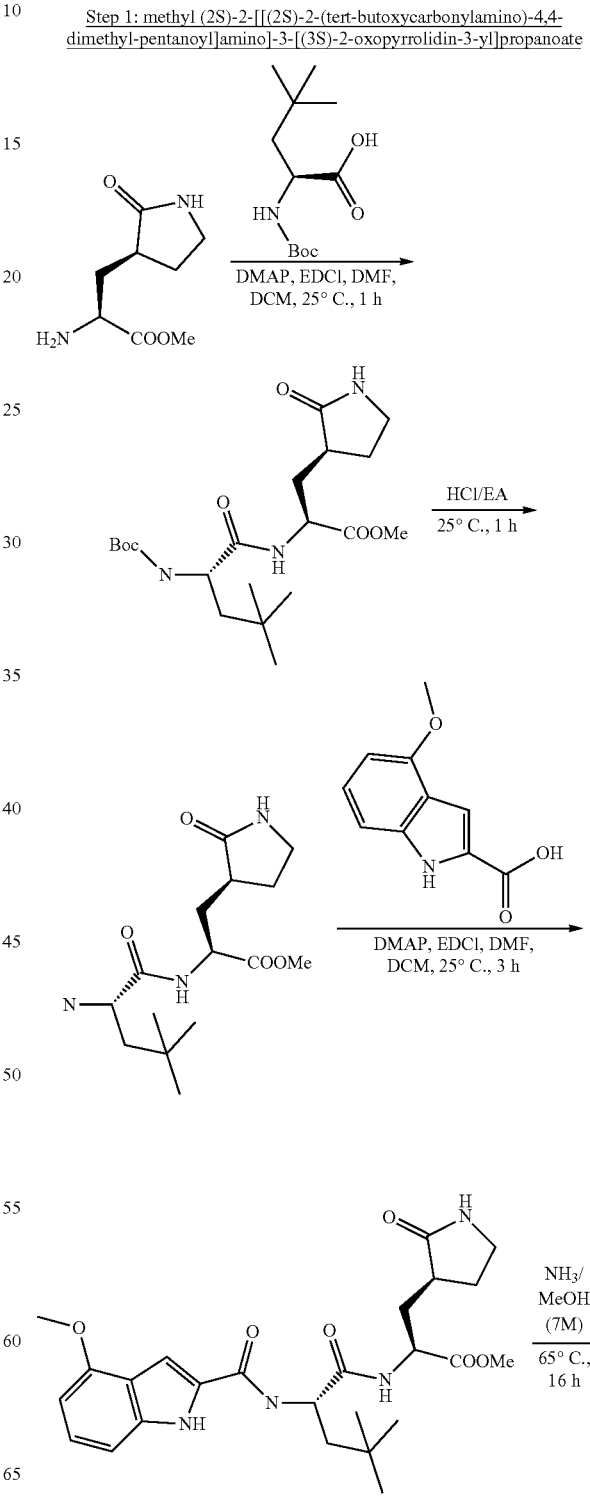

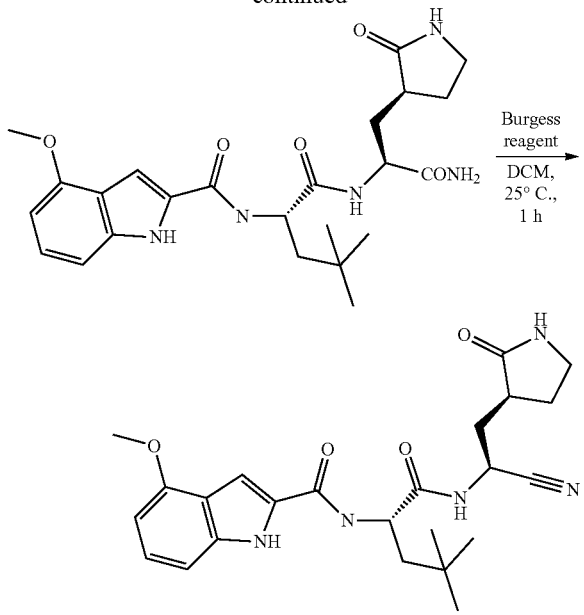

To a solution of methyl (2S)-2-amino-3-[(3S)-2-oxopyrrolidin-3-yl]propanoate (225 mg, 1.21 mmol, 1 eq) in DMF (2 mL) and DCM (4 mL) was added TEA (733.62 mg, 7.25 mmol, 1.01 mL, 6 eq) and T$_3$P (1.15 g, 3.62 mmol, 1.08 mL, 3 eq) and (2S)-2-(tert-butoxycarbonylamino)-4,4-dimethyl-pentanoic acid (296.42 mg, 1.21 mmol, 1 eq). The solution was stirred for 1 h at 25° C. The reaction was diluted with H$_2$O (40 mL) and extracted with ethyl acetate (50 mL*3) and the organic layer was cautiously concentrated to give crude Compound methyl (2S)-2-[[(2S)-2-(tert-butoxycarbonylamino)-4,4-dimethyl-pentanoyl]amino]-3-[(3S)-2-oxopyrrolidin-3-yl]propanoate (440 mg, crude) as a yellow solid used directly for the next step. MS (ESI) m/z 414.1 [M+H]$^+$ Step 2: methyl (2S)-2-[[(2S)-2-amino-4,4-dimethyl-pentanoyl]amino]-3-[(3S)-2-oxopyrrolidin-3-yl]propanoate A solution of methyl (2S)-2-[[(2S)-2-(tert-butoxycarbonylamino)-4,4-dimethyl-pentanoyl]amino]-3-[(3S)-2-oxopyrrolidin-3-yl]propanoate (440 mg, 1.06 mmol, 1 eq) in HCl/MeOH (10 mL) was stirred for 1 h at 25° C. TLC (DCM:MeOH=10:1) showed desired, and the reaction was cautiously concentrated to give crude. Compound methyl (2S)-2-[[(2S)-2-amino-4,4-dimethyl-pentanoyl]amino]-3-[(3S)-2-oxopyrrolidin-3-yl]propanoate (310 mg, crude) as a yellow solid used directly for the next step. MS (ESI) m/z 314.3 [M+H]$^+$ Step 3: methyl (2S)-2-[[(2S)-2-[(4-methoxy-1H-indole-2-carbonyl)amino]-4,4-dimethyl-pentanoyl]amino]-3-[(3S)-2-oxopyrrolidin-3-yl]propanoate To a solution of methyl (2S)-2-[[(2S)-2-amino-4,4-dimethyl-pentanoyl]amino]-3-[(3S)-2-oxopyrrolidin-3-yl]propanoate (310 mg, 989.18 umol, 1 eq) in DMF (4 mL) and DCM (4 mL) was added EDCI (379.25 mg, 1.98 mmol, 2 eq) was added DMAP (241.70 mg, 1.98 mmol, 2 eq) and 4-methoxy-1H-indole-2-carboxylic acid (189.11 mg, 989.18 umol, 1 eq). The solution was stirred for 3 h at 25° C., and then the reaction was diluted with H$_2$O (40 mL) and extracted with ethyl acetate (80 mL*3) and the organic layer was cautiously concentrated to give crude. The crude was purified by pre-TLC (SiO$_2$, EA:MeOH=10:1) to give product. Compound methyl (2S)-2-[[(2S)-2-[(4-methoxy-1H-indole-2-carbonyl)amino]-4,4-dimethyl-pentanoyl]amino]-3-[(3S)-2-oxopyrrolidin-3-yl]propanoate (200 mg, 411.05 umol, 41.55% yield) was obtained. MS (ESI) m/z 487.2 [M–H]$^+$ Step 4: N-[(1S)-1-[[(1S)-2-amino-2-oxo-1-[[(3S)-2-oxopyrrolidin-3-yl]methyl]ethyl]carbamoyl]-3,3-dimethyl-butyl]-4-methoxy-1H-indole-2-carboxamide A solution of methyl (2S)-2-[[(2S)-2-[(4-methoxy-1H-indole-2-carbonyl)amino]-4,4-dimethyl-pentanoyl]amino]-3-[(3S)-2-oxopyrrolidin-3-yl]propanoate (135 mg, 277.46 umol, 1 eq) in NH$_3$/MeOH (7 M, 8 mL, 201.83 eq) was stirred for 16 h at 65° C. HPLC showed desired. The reaction was cautiously concentrated to give crude. Compound N-[(1S)-1-[[(1S)-2-amino-2-oxo-1-[[(3S)-2-oxopyrrolidin-3-yl]methyl]ethyl]carbamoyl]-3,3-dimethyl-butyl]-4-methoxy-1H-indole-2-carboxamide (130 mg, crude) was obtained as a yellow solid used directly for the next step. MS (ESI) m/z 472.3 [M+H]$^+$ Prep-HPLC condition: column: Phenomenex Gemini-NX C18 75*30 mm*3 um; mobile phase: [water(0.05% NH$_3$H$_2$O+10 mM NH$_4$HCO$_3$)-ACN]; B %: 35%-55%, 8 min Step 5: N-[(1S)-1-[[(1S)-1-cyano-2-[(3S)-2-oxopyrrolidin-3-yl]ethyl]carbamoyl]-3,3-dimethyl-butyl]-4-methoxy-1H-indole-2-carboxamide To a solution of N-[(1S)-1-[[(1S)-2-amino-2-oxo-1-[[(3S)-2-oxopyrrolidin-3-yl]methyl]ethyl]carbamoyl]-3,3-dimethyl-butyl]-4-methoxy-1H-indole-2-carboxamide (130 mg, 275.69 umol, 1 eq) in DCM (7 mL) was added Burgess reagent (197.09 mg, 827.06 umol, 3 eq). The solution was stirred for 1 h at 25° C. The reaction was cautiously concentrated to give crude, and the crude was purified by pre-HPLC (TFA) to give N-[(1S)-1-[[(1S)-1-cyano-2-[(3S)-2-oxopyrrolidin-3-yl]ethyl]carbamoyl]-3,3-dimethyl-butyl]-4-methoxy-1H-indole-2-carboxamide (36 mg, 75.41 umol, 27.35% yield, 95% purity) as a white solid. MS (ESI) m/z 454.1 [M+H]$^+$.

Prep-HPLC condition: column: Phenomenex luna C18 80*40 mm*3 um; mobile phase: [water(0.04% HCl)-ACN]; B %: 30%-55%, 7 min $^1$H NMR (400 MHz, METHANOL-d$_4$) δ ppm 1.02 (s, 9H) 1.74-1.94 (m, 4H) 2.21-2.37 (m, 2H) 2.52-2.63 (m, 1H) 3.16-3.26 (m, 2H) 3.92 (s, 3H) 4.63 (dd, J=8.49, 4.30 Hz, 1H) 4.98-5.06 (m, 1H) 6.50 (d, J=7.72 Hz, 1H) 7.02 (d, J=8.38 Hz, 1H) 7.10-7.16 (m, 1H) 7.23 (d, J=0.88 Hz, 1H).

Example 132. Synthesis of Viral Protease Inhibitor Compound 409

Step 1: (S)-2-amino-3-((S)-2-oxopyrrolidin-3-yl)propanamide

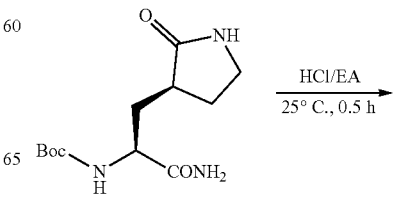

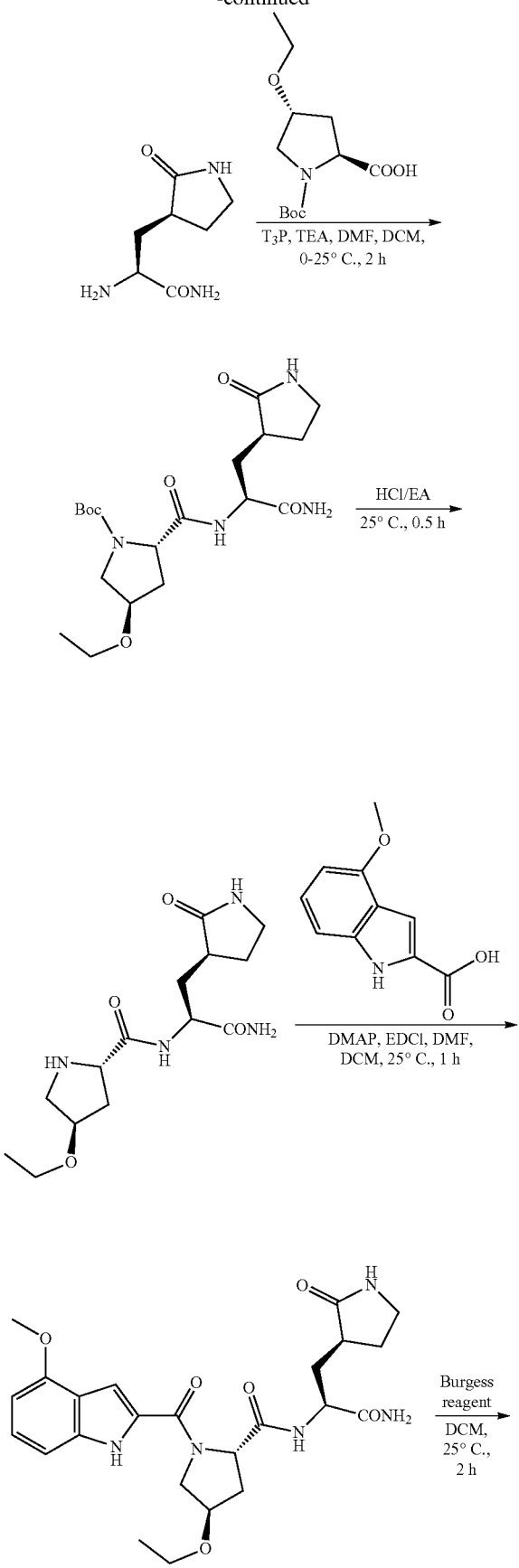

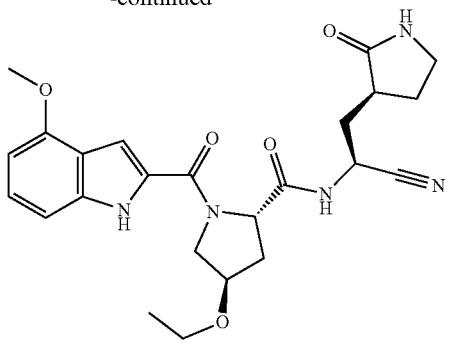

A mixture of tert-butyl N-[(1S)-2-amino-2-oxo-1-[[(3S)-2-oxopyrrolidin-3-yl]methyl]ethyl] carbamate (300 mg, 1.11 mmol, 1 eq) in HCl/EtOAc (4 M, 10 mL, 36.17 eq) was stirred at 25° C. for 0.5 h. Upon completion, the mixture was concentrated under the reduced pressure affording the product (2S)-2-amino-3-[(3S)-2-oxopyrrolidin-3-yl]propanamide (200 mg, crude, HCl) as a white solid.

Step 2: (2S,4R)-tert-butyl2-(((S)-1-amino-1-oxo-3-((S)-2-oxopyrrolidin-3-yl)propan-2-yl)carbamoyl)-4-ethoxypyrrolidine-1-carboxylate (2S)-2-amino-3-[(3S)-2-oxopyrrolidin-3-yl]propanamide (200 mg, 963.12 umol, 1 eq, HCl) and (2S,4R)-1-tert-butoxycarbonyl-4-ethoxy-pyrrolidine-2-carboxylic acid (249.74 mg, 963.12 umol, 1 eq) in DMF (4 mL) and DCM (8 mL) was added TEA (487.29 mg, 4.82 mmol, 670.27 uL, 5 eq) and T3P (1.84 g, 2.89 mmol, 1.72 mL, 50% purity, 3 eq) at 0° C. The mixture was stirred at 25° C. for 2 h. Upon completion, the mixture was quenched by addition H$_2$O (30 mL) and then extracted with DCM (30 mL*3). The combined organic layers were washed with brine (30 mL), dried over Na$_2$SO$_4$, filtered and concentrated under reduced pressure to give a residue. The residue was purified by prep-TLC (SiO$_2$, DCM:MeOH=10:1) affording the product tert-butyl (2S,4R)-2-[[(1S)-2-amino-2-oxo-1-[[(3S)-2-oxopyrrolidin-3-yl]methyl]ethyl]carbamoyl]-4-ethoxypyrrolidine-1-carboxylate (140 mg, 339.41 umol, 35.24% yield) as a yellow solid. MS (ESI) m/z 413.1 [M+H]$^+$ Step 3: (2S,4R)-N-((S)-1-amino-1-oxo-3-((S)-2-oxopyrrolidin-3-yl)propan-2-yl)-4-ethoxypyrrolidine-2-carboxamide A mixture of tert-butyl(2S,4R)-2-[[(1S)-2-amino-2-oxo-1-[[(3S)-2-oxopyrrolidin-3-yl]methyl]ethyl] carbamoyl]-4-ethoxypyrrolidine-1-carboxylate (100 mg, 242.44 umol, 1 eq) in HCl/EtOAc (4 M, 10 mL, 164.99 eq) was stirred at 25° C. for 0.5 h. Upon completion, the mixture was concentrated under the reduced pressure affording the product (2S,4R)-N-[(1S)-2-amino-2-oxo-1-[[(3S)-2-oxopyrrolidin-3-yl]methyl]ethyl]-4-ethoxy-pyrrolidine-2-carboxamide (80 mg, crude, HCl) as a white solid.

Step 4: (2S,4R)-N-((S)-1-amino-1-oxo-3-((S)-2-oxopyrrolidin-3-yl)propan-2-yl)-4-ethoxy-1-(4-methoxy-1H-indole-2-carbonyl)pyrrolidine-2-carboxamide A mixture of (2S,4R)-N-[(1S)-2-amino-2-oxo-1-[[(3S)-2-oxopyrrolidin-3-yl]methyl]ethyl]-4-ethoxy-pyrrolidine-2-carboxamide (80 mg, 229.34 umol, 1 eq, HCl) and 4-methoxy-1H-indole-2-carboxylic acid (65.77 mg, 344.01 umol, 1.5 eq) in DCM (3 mL) and DMF (1 mL) was added DMAP (56.04 mg, 458.68 umol, 2 eq) and EDCI (87.93 mg, 458.68 umol, 2 eq). The mixture was stirred at 25° C. for 1 h. Upon completion, the mixture was quenched by addition H$_2$O (30 mL) and then extracted with DCM (30 mL*3). The combined organic layers were washed with brine (30 mL), dried over Na$_2$SO$_4$, filtered and concentrated under reduced pressure to give a residue. The residue was purified by prep-TLC (SiO$_2$, DCM:MeOH=10:1) affording the product (2S,4R)-N-[(1S)-2-amino-2-oxo-1-[[(3S)-2-oxopyrrolidin-3-yl]methyl]ethyl]-4-ethoxy-1-(4-methoxy-1Hindole-2-carbonyl)pyrrolidine-2-carboxamide (100 mg, crude) as a yellow oil. MS (ESI) m/z 486.2 [M+H]$^+$ Step 5: (2S,4R)-N-((S)-1-cyano-2-((S)-2-oxopyrrolidin-3-yl)ethyl)-4-ethoxy-1-(4-methoxy-1H-indole-2-carbonyl)pyrrolidine-2-carboxamide To a mixture of (2S,4R)-N-[(1S)-2-amino-2-oxo-1-[[(3S)-2-oxopyrrolidin-3-yl]methyl]ethyl]-4-ethoxy-1-(4-methoxy-1H-indole-2-carbonyl)pyrrolidine-2-carboxamide (80 mg, 164.77 umol, 1 eq) in DCM (3 mL) was added Burgess reagent (196.33 mg, 823.84 umol, 5 eq). The mixture was stirred at 25° C. for 2 h. Upon completion, the mixture was concentrated under the reduced pressure to give a residue. The residue was purified by prep-HPLC (column: Waters Xbridge BEH C18 100*25 mm*5 um; mobile phase: [water (10 mM NH$_4$HCO$_3$)-ACN]; B %: 20%-45%, 10 min) affording the product (2S,4R)-N-[(1S)-1-cyano-2-[(3S)-2-oxopyrrolidin-3-yl]ethyl]-4-ethoxy-1-(4-methoxy-1H-indole-2-carbonyl)pyrrolidine-2-carboxamide (28 mg, 58.81 umol, 35.69% yield, 98.2% purity) as a white solid. MS (ESI) m/z 468.2 [M+H]$^+$ $^1$H NMR (400 MHz, MeOD-d$_4$) δ=7.19-7.13 (m, 1H), 7.09-6.86 (m, 2H), 6.57-6.42 (m, 1H), 5.17-5.01 (m, 1H), 4.69-4.58 (m, 1H), 4.36-4.18 (m, 1H), 4.16-3.97 (m, 2H), 3.96-3.85 (m, 3H), 3.68-3.44 (m, 2H), 3.00-2.54 (m, 2H), 2.50-2.31 (m, 2H), 2.25-2.02 (m, 2H), 2.01-1.72 (m, 2H), 1.69-1.26 (m, 1H), 1.25-1.13 (m, 3H).

Example 133. Synthesis of Viral Protease Inhibitor Compound 433

Step 1: methyl 2-amino-2-(3-pyridyl)acetate

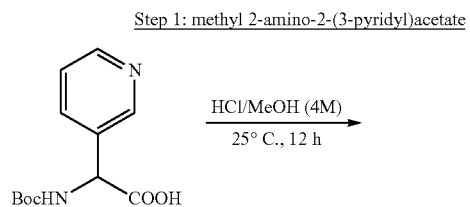

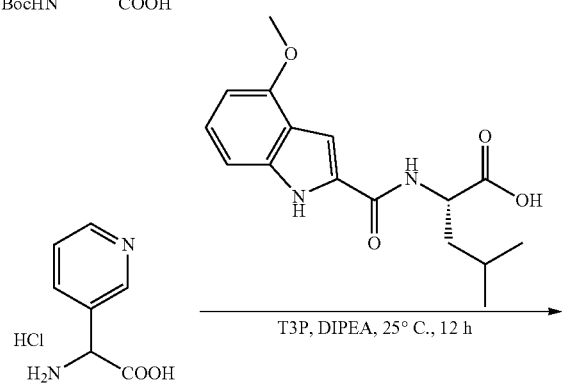

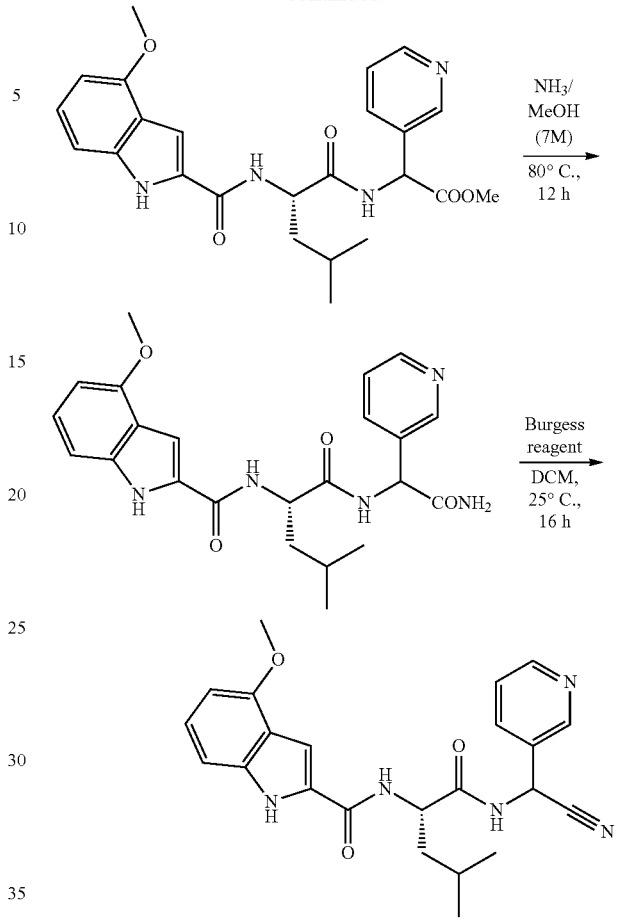

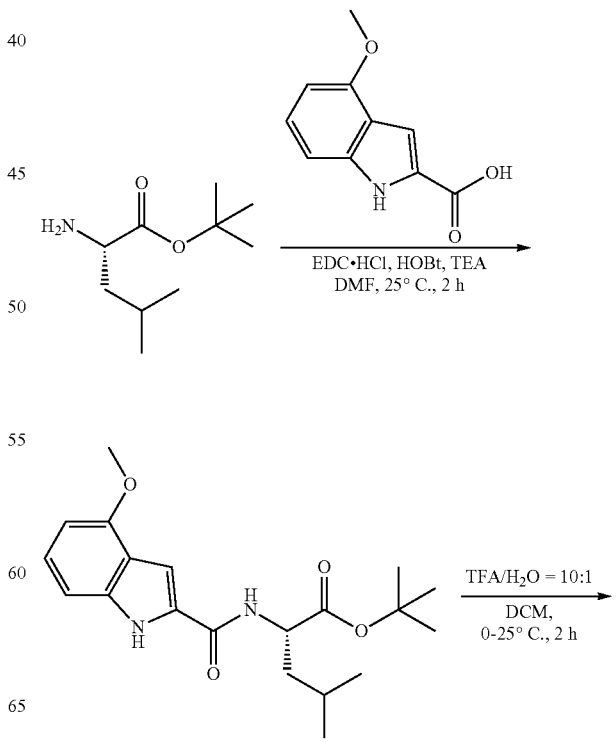

-continued

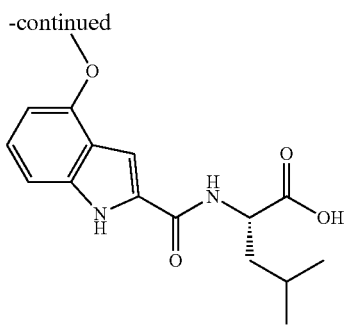

To 2-(tert-butoxycarbonylamino)-2-(3-pyridyl)acetic acid (0.5 g, 1.98 mmol, 1 eq) was added HC/MeOH (4 M, 20 mL, 40.36 eq) in one portion at 25° C. under $N_2$. The mixture was stirred at 25° C. for 12 h. The reaction mixture was concentrated to get the crude product. The crude product was used the next step without purification. Methyl 2-amino-2-(3-pyridyl)acetate (400 mg, crude, HCl) was obtained as a yellow oil and used directly next step. MS (ESI) m/z 167.1 $[M+H]^+$ Step 2: methyl 2-[[(2S)-2-[(4-methoxy-1H-indole-2-carbonyl)amino]-4-methyl-pentanoyl]amino]-2-(3-pyridyl)acetate To a mixture of (2S)-2-[(4-methoxy-1H-indole-2-carbonyl)amino]-4-methyl-pentanoic acid (600.76 mg, 1.97 mmol, 1 eq) and methyl 2-amino-2-(3-pyridyl)acetate (400 mg, 1.97 mmol, 1 eq, HCl), DIPEA (1.28 g, 9.87 mmol, 1.72 mL, 5 eq) in THF (1.2 mL) and DCM (1.2 mL) was added T3P (1.88 g, 2.96 mmol, 1.76 mL, 50% purity, 1.5 eq) at 0° C. under $N_2$. The mixture was stirred at 25° C. for 12 h. The reaction mixture was added saturated sodium bicarbonate solution (10 mL) and extracted with DCM (10 mL*2) to get the organic phase. The organic phase was concentrated to get the crude product. The residue was purified by pre-HPLC. Methyl 2-[[(2S)-2-[(4-methoxy-1H-indole-2-carbonyl)amino]-4-methyl-pentanoyl]amino]-2-(3-pyridyl)acetate (0.3 g, crude) was obtained as a white solid. MS (ESI) m/z 453.2 $[M+H]^+$ Prep-HPLC condition: column: Kromasil C18 (250*50 mm*10 um); mobile phase: [water (10 mM $NH_4HCO_3$)-ACN]; B %: 30%-50%, 10 min.

Step 3: N-[(1S)-1-[[2-amino-2-oxo-1-(3-pyridyl)ethyl]carbamoyl]-3-methyl-butyl]-4-methoxy-1H-indole-2-carboxamide To a mixture of methyl 2-[[(2S)-2-[(4-methoxy-1H-indole-2-carbonyl)amino]-4-methyl-pentanoyl] amino]-2-(3-pyridyl)acetate (0.2 g, 441.99 umol, 1 eq) was added $NH_3$/MeOH (7 M, 6 mL, 95.03 eq) in one portion at 25° C. under $N_2$. The mixture was stirred at 80° C. for 12 h. The reaction mixture was cooled to the 25° C. and concentrated to get the product. The residue was purified by prep-TLC (SiO$_2$, DCM:MeOH=10:1, $R_f$=0.22). N-[(1S)-1-[[2-amino-2-oxo-1-(3-pyridyl)ethyl]carbamoyl]-3-methyl-butyl]-4-methoxy-1H-indole-2-carboxamide (70 mg, crude) was obtained as a light yellow solid. MS (ESI) m/z 438.2 $[M+H]^+$ Step 4: N-[(1S)-1-[[cyano(3-pyridyl)methyl]carbamoyl]-3-methyl-butyl]-4-methoxy-1H-indole-2-carboxamide To a mixture of N-[(1S)-1-[[2-amino-2-oxo-1-(3-pyridyl)ethyl]carbamoyl]-3-methyl-butyl]-4-methoxy-1H-indole-2-carboxamide (60 mg, 137.15 umol, 1 eq) in DCM (0.2 mL) was added Burgess reagent (65.37 mg, 274.29 umol, 2 eq) in one portion at 25° C. under $N_2$. The mixture was stirred at 25° C. for 16 h. The reaction mixture was concentrated to get the crude product. The crude product was purified by pre-HPLC twice. N-[(1S)-1-[[cyano(3-pyridyl)methyl]carbamoyl]-3-methyl-butyl]-4-methoxy-1H-indole-2-carboxamide (12.78 mg, 29.52 umol, 21.52% yield, 96.878% purity) was obtained as a white solid. MS (ESI) m/z 423.2 $[M+H]^+$ Prep-HPLC condition: column: Waters Xbridge BEH C18 100*25 mm*5 um; mobile phase: [water (10 mM $NH_4HCO_3$)-ACN]; B %: 25%-55%, 10 min.

Column: Phenomenex Gemini-NX C18 75*30 mm*3 um; mobile phase: [water (10 mM $NH_4HCO_3$)-ACN]; B %: 30%-55%, 8 min.

$^1$H NMR (400 MHz, DMSO-d$_6$) δ ppm 11.61 (dd, J=7.03, 1.77 Hz, 1H), 9.49 (dd, J=17.24, 7.83 Hz, 1H), 8.59-8.71 (m, 2H), 8.53 (d, J=7.82 Hz, 1H), 7.85-7.93 (m, 1H), 7.47-7.55 (m, 1H), 7.38 (t, J=2.51 Hz, 1H), 7.06-7.14 (m, 1H), 7.01-7.01 (m, 1H), 7.01 (dd, J=8.25, 3.24 Hz, 1H), 6.51 (dd, J=7.70, 1.34 Hz, 1H), 6.32 (dd, J=12.41, 7.76 Hz, 1H), 4.44-4.61 (m, 1H), 3.89 (d, J=1.10 Hz, 3H), 1.62-1.81 (m, 2H), 1.46-1.60 (m, 1H), 0.81-1.03 (m, 7H).

Step 6: (S)-tert-butyl 2-(4-methoxy-1H-indole-2-carboxamido)-4-methylpentanoate

To a mixture of 4-methoxy-1H-indole-2-carboxylic acid (15 g, 78.46 mmol, 1 eq) and tert-butyl (2S)-2-amino-4-methyl-pentanoate (21.07 g, 94.15 mmol, 1.2 eq, HCl) in DMF (150 mL) was added EDCI (19.55 g, 102.00 mmol, 1.3 eq), HOBt (13.78 g, 102.00 mmol, 1.3 eq), TEA (23.82 g, 235.38 mmol, 32.76 mL, 3 eq) at 25° C. under $N_2$. The mixture was stirred at 25° C. and stirred for 2 h. The reaction mixture was added water (450 mL) and extracted with ethyl acetate (250 mL*3) to get the organic phase. The organic phase was washed with 5% citric acid (300 mL) and 5% aqueous solution of sodium bicarbonate (300 mL) and dried over anhydrous sodium sulfate, filtered and concentrated to get the product. The residue was purified by column chromatography (SiO$_2$, petroleum ether:ethyl acetate=30:1 to 10:1) to afford tert-butyl (2S)-2-[(4-methoxy-1H-indole-2-carbonyl)amino]-4-methyl-pentanoate (24 g, 66.58 mmol, 84.87% yield) as light yellow solid. MS (ESI) m/z 361.2 $[M+H]^+$ Step 7: (S)-2-(4-methoxy-1H-indole-2-carboxamido)-4-methylpentanoic acid To a mixture of tert-butyl (2S)-2-[(4-methoxy-1H-indole-2-carbonyl)amino]-4-methyl-pentanoate (10 g, 27.74 mmol, 1 eq) in DCM (30 mL) was added TFA (61.60 g, 540.26 mmol, 40 mL, 19.47 eq) and $H_2O$ (4.00 g, 221.98 mmol, 4.00 mL, 8.00 eq) in one portion at 0° C. under $N_2$. The mixture was stirred at 25° C. and stirred for 2 h. The reaction mixture was concentrated to get the crude product. The crude product was purified by pulping with petroleum ether:ethyl acetate=10:1 (20 mL) and filtered to get the product. (2S)-2-[(4-methoxy-1H-indole-2-carbonyl)amino]-4-methyl-pentanoic acid (6 g, 19.22 mmol, 69.27% yield, 97.48% purity) was obtained as a light yellow solid. MS (ESI) m/z 305.1 $[M+H]^+$

Example 134. Synthesis of Viral Protease Inhibitor Compound 439

Step 1: methyl (2S)-2-amino-3-(2-pyridyl)propanoate

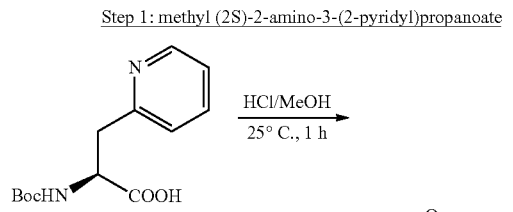

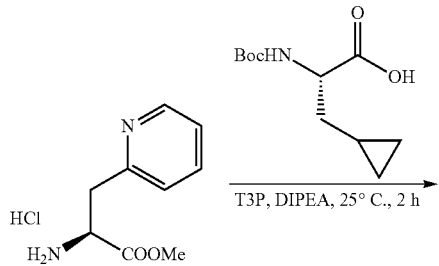

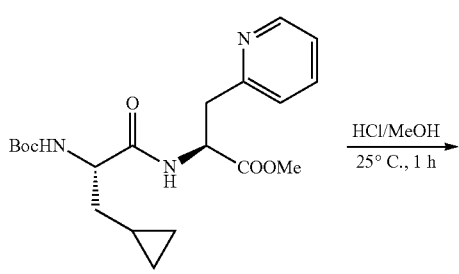

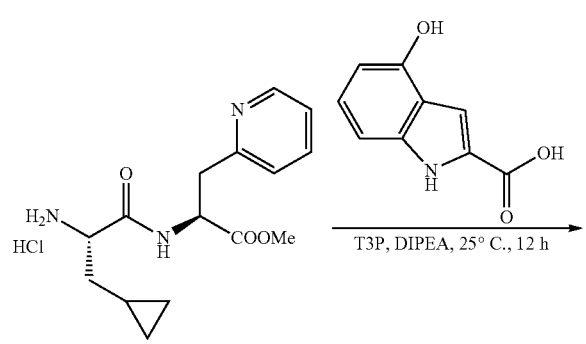

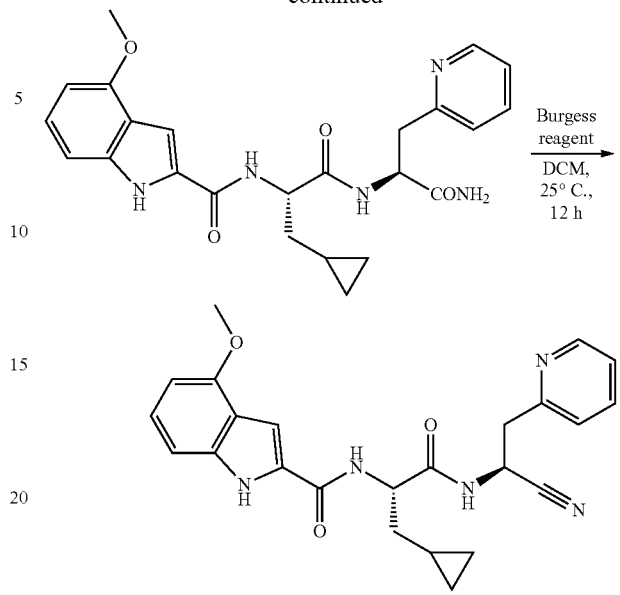

To a mixture of (2S)-2-(tert-butoxycarbonylamino)-3-(2-pyridyl)propanoic acid (1 g, 3.76 mmol, 1 eq) was added HCl/MeOH (4 M, 10 mL, 10.65 eq) in one portion at 25° C. under $N_2$. The mixture was stirred at 25° C. for 1 h. The reaction mixture was concentrated to get the product. Methyl (2S)-2-amino-3-(2-pyridyl)propanoate (900 mg, 3.48 mmol, 92.79% yield, 98% purity, 2HCl) was obtained as a white solid and used directly next step. MS (ESI) m/z 181.1 [M+H]$^+$ Step 2: methyl (2S)-2-[[(2S)-2-(tert-butoxycarbonylamino)-3-cyclopropyl-propanoyl]amino]-3-(2-pyridyl)propanoate To a mixture of methyl (2S)-2-amino-3-(2-pyridyl)propanoate (0.9 g, 3.56 mmol, 1 eq, 2HCl) and (2S)-2-(tert-butoxycarbonylamino)-3-cyclopropyl-propanoic acid (978.23 mg, 4.27 mmol, 1.2 eq) and DIPEA (2.30 g, 17.78 mmol, 3.10 mL, 5 eq) in DCM (6 mL) and THF (6 mL) was added $T_3P$ (3.39 g, 5.33 mmol, 3.17 mL, 50% purity, 1.5 eq) at 0° C. under $N_2$. The mixture was stirred at 25° C. for 2 h. The reaction mixture was added saturated sodium bicarbonate solution (10 mL) and extracted with DCM (10 mL×2) to get the organic phase. The organic phase was concentrated to get the crude product. Methyl (2S)-2-[[(2S)-2-(tert-butoxycarbonylamino)-3-cyclopropyl-propanoyl]amino]-3-(2-pyridyl)propanoate (1.1 g, 2.81 mmol, 79.03% yield) was obtained as a light yellow solid and used directly next step. MS (ESI) m/z 392.2 [M+H]$^+$ Step 3: methyl (2S)-2-[[(2S)-2-amino-3-cyclopropyl-propanoyl]amino]-3-(2-pyridyl)propanoate To a mixture of methyl (2S)-2-[[(2S)-2-(tert-butoxycarbonylamino)-3-cyclopropyl-propanoyl]amino]-3-(2-pyridyl)propanoate (1.1 g, 2.81 mmol, 1 eq) was added HCl/MeOH (4 M, 11 mL, 15.66 eq) in one portion at 25° C. under $N_2$. The mixture was stirred at 25° C. for 1 h. The reaction mixture was concentrated to get the product. Methyl (2S)-2-[[(2S)-2-amino-3-cyclopropyl-propanoyl]amino]-3-(2-pyridyl)propanoate (1 g, crude, HCl) was obtained as a brown solid and used directly next step. MS (ESI) m/z 292.2 [M+H]$^+$ Step 4: methyl (2S)-2-[[(2S)-3-cyclopropyl-2-[(4-methoxy-1H-indole-2-carbonyl)amino]propanoyl]amino]-3-(2-pyridyl)propanoate To a mixture of methyl (2S)-2-[[(2S)-2-amino-3-cyclopropyl-propanoyl]amino]-3-(2-pyridyl)propanoate (0.8 g, 2.20 mmol, 1 eq, 2HCl) and 4-methoxy-1H-indole-2-carboxylic acid (461.86 mg, 2.42 mmol, 1.1 eq) and DIPEA (1.42 g, 10.98 mmol, 1.91 mL, 5 eq) in DCM (0.5 mL) and THF (0.5 mL) was added T₃P (2.10 g, 3.29 mmol, 1.96 mL, 50% purity, 1.5 eq) at 0° C. under N₂. The mixture was stirred at 25° C. for 12 h. The reaction mixture was added saturated sodium bicarbonate solution (10 mL) and extracted with DCM (10 mL×2) to get the organic phase. The organic phase was concentrated to get the crude product. The residue was purified by flash silica gel chromatography. Methyl (2S)-2-[[(2S)-3-cyclopropyl-2-[(4-methoxy-1H-indole-2-carbonyl)amino] propanoyl]amino]-3-(2-pyridyl)propanoate (0.8 g, 1.50 mmol, 68.38% yield, 87.2% purity) was obtained as a light yellow solid. MS (ESI) m/z 465.2 [M+H]⁺

Step 5: N-[(1S)-1-(cyclopropylmethyl)-2-[[(1S)-1-(nitrosomethyl)-2-(2-pyridyl)ethyl]amino]-2-oxo-ethyl]-4-methoxy-1H-indole-2-carboxamide To a mixture of methyl (2S)-2-[[(2S)-3-cyclopropyl-2-[(4-methoxy-1H-indole-2-carbonyl)amino] propanoyl]amino]-3-(2-pyridyl)propanoate (0.2 g, 430.56 umol, 1 eq) was added NH₃/MeOH (7 M, 4 mL, 65.03 eq) in one portion at 25° C. under N₂. The mixture was stirred at 80° C. for 12 h. The reaction mixture was cooled to 25° C. and concentrated to get the crude product. N-[(1S)-1-(cyclopropylmethyl)-2-[[(1S)-1-(nitrosomethyl)-2-(2-pyridyl)ethyl]amino]-2-oxo-ethyl]-4-methoxy-1H-indole-2-carboxamide (200 mg, crude) was obtained as a light yellow solid and used directly next step. MS (ESI) m/z 450.2 [M+H]⁺

Step 6: N-[(1S)-2-[[(1S)-1-cyano-2-(2-pyridyl)ethyl]amino]-1-(cyclopropylmethyl)-2-oxo-ethyl]-4-methoxy-1H-indole-2-carboxamide To a mixture of N-[(1S)-1-(cyclopropylmethyl)-2-[[(1S)-1-(nitrosomethyl)-2-(2-pyridyl)ethyl]amino]-2-oxo-ethyl]-4-methoxy-1H-indole-2-carboxamide (0.1 g, 222.47 umol, 1 eq) in DCM (1 mL) was added Burgess reagent (212.06 mg, 889.88 umol, 4 eq) in one portion at 25° C. under N₂. The mixture was stirred at 25° C. for 12 h. The reaction mixture was concentrated to get the crude product. The crude product was purified by pre-HPLC. N-[(1S)-2-[[(1S)-1-cyano-2-(2-pyridyl)ethyl]amino]-1-(cyclopropylmethyl)-2-oxo-ethyl]-4-methoxy-1H-indole-2-carboxamide (25.44 mg, 58.27 umol, 26.19% yield, 98.833% purity) was obtained as a white solid. MS (ESI) m/z 432.2 [M+H]⁺

Prep-HPLC condition: column: Phenomenex Gemini-NX C18 75*30 mm*3 um; mobile phase: [water (10 mM NH₄HCO₃)-ACN]; B %: 30%-50%, 8 min ¹H NMR (400 MHz, MeOD-d₄) δ ppm 8.27-8.39 (m, 1H), 7.64-7.73 (m, 1H), 7.31-7.39 (m, 1H), 7.23-7.30 (m, 1H), 7.12-7.23 (m, 2H), 7.00-7.07 (m, 1H), 6.52 (d, J=7.50 Hz, 1H), 5.28 (t, J=7.17 Hz, 1H), 4.51-4.63 (m, 1H), 3.87-3.98 (m, 3H), 3.30-3.31 (m, 2H), 1.57-1.83 (m, 2H), 0.62-0.85 (m, 1H), 0.34-0.54 (m, 2H), 0.05-0.22 (m, 2H).

¹H NMR (400 MHz, CHLOROFORM-d) δ ppm 9.35 (br s, 1H), 8.50-8.68 (m, 1H), 8.04-8.26 (m, 1H), 7.51 (td, J=7.69, 1.75 Hz, 1H), 6.93-7.11 (m, 4H), 6.77-6.90 (m, 2H), 6.34-6.42 (m, 1H), 5.11-5.23 (m, 1H), 4.61-4.71 (m, 1H), 3.76-3.87 (m, 3H), 3.07-3.25 (m, 2H), 1.55-1.69 (m, 2H), 0.48-0.67 (m, 1H), 0.28-0.40 (m, 2H), −0.09-0.08 (m, 2H).

Example 135. Synthesis of Viral Protease Inhibitor Compound 448

Step 1: Methyl (2S)-3-cyclopropyl-2-(4-methyl-3-nitro-2-oxo-1-pyridyl)propanoate

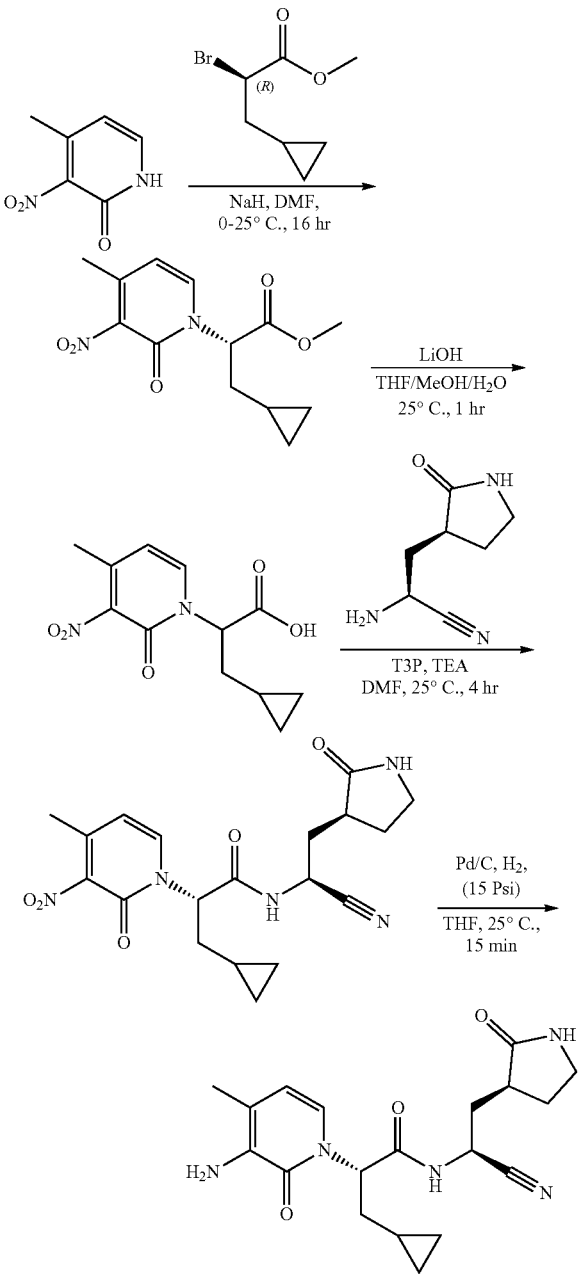

A solution of 4-methyl-3-nitro-1H-pyridin-2-one (500 mg, 3.24 mmol, 1 eq) in DMF (10 mL) was added NaH (181.6 mg, 4.54 mmol, 60% purity, 1.4 eq) at 0° C., and the reaction mixture was stirred at 25° C. for 0.5 hr. Then methyl (2R)-2-bromo-3-cyclopropyl-propanoate (671.7 mg, 3.24 mmol, 1 eq) was added at 0° C. The mixture was stirred at 25° C. for 16 h under N₂. LCMS showed one peak with desired MS was detected. The mixture was quenched with H₂O (50 mL), and extracted with ethyl acetate (150 mL*3). The combined organic layers was washed with brine (10 mL) dried over Na₂SO₄, filtered and concentrated under reduce pressure. The residue was purified by flash silica gel chromatography (ISCO®; 24 g SepaFlash® Silica Flash Column, Eluent of 0~50% ethyl acetate/petroleum ethergradient @ 35 mL/min) to give methyl (2S)-3-cyclopropyl-2-(4-methyl-3-nitro-2-oxo-1-pyridyl)propanoate (453 mg, 45.1% yield) as a yellow solid.

LCMS: Rt=0.780 min; for $C_{13}H_{16}N_2O_5$ MS Calcd.: 280.11; MS Found: 281.0 [M+H⁺].

¹H NMR (400 MHz, DMSO-d₆) δ 7.93 (d, J=7.03 Hz, 1H), 6.43 (d, J=7.03 Hz, 1H), 5.30 (t, J=7.65 Hz, 1H), 3.65 (s, 3H), 2.23 (s, 3H), 1.99 (t, J=7.40 Hz, 2H), 0.56-0.45 (m, 1H), 0.38-0.25 (m, 2H), 0.15-0.13 (m, 2H).

Step 2: (2S)-3-cyclopropyl-2-(4-methyl-3-nitro-2-oxo-1-pyridyl)propanoic acid

A mixture of methyl (2S)-3-cyclopropyl-2-(4-methyl-3-nitro-2-oxo-1-pyridyl)propanoate (253 mg, 0.90 mmol, 1 eq), LiOH·H₂O (151.5 mg, 3.61 mmol, 4 eq) in THF (2.1 mL), MeOH (0.7 mL), H₂O (0.7 mL) was degassed and purged with N₂ for 3 times, and then the mixture was stirred at 25° C. for 1 hr under N₂ atmosphere. LCMS showed one peak with desired MS was detected. The mixture was added H₂O (5 mL), then the mixture was added 2 M HCl (2 mL) to adjust the pH to about 6-7. The mixture was added H₂O (10 mL), and extracted with ethyl acetate (30 mL*3). The combined organic layers was washed with brine (10 mL) dried over Na₂SO₄, filtered and concentrated under reduce pressure to give (2S)-3-cyclopropyl-2-(4-methyl-3-nitro-2-oxo-1-pyridyl)propanoic acid (207 mg, 77.9% yield) as a yellow solid.

LCMS: Rt=0.732 min; for $C_{12}H_{14}N_2O_5$ MS Calcd.: 266.09; MS Found: 267.0 [M+H⁺].

Step 3: (2S)-N-[(11S)-1-cyano-2-[(3S)-2-oxopyrrolidin-3-yl]ethyl]-3-cyclopropyl-2-(4-methyl-3-nitro-2-oxo-1-pyridyl)propanamide To a solution of (2S)-3-cyclopropyl-2-(4-methyl-3-nitro-2-oxo-1-pyridyl)propanoic acid (207 mg, 0.77 mmol, 1 eq) in DMF (2 mL) was added T₃P (989.5 mg, 1.55 mmol, 0.92 mL, 50% purity, 2 eq), TEA (314.6 mg, 3.11 mmol, 0.43 mL, 4 eq) and (2S)-2-amino-3-[(3S)-2-oxopyrrolidin-3-yl]propanenitrile (147.4 mg, 0.77 mmol, 1 eq, HCl). The mixture was stirred at 25° C. for 4 h. LCMS showed the peak with desired MS was detected. The mixture was quenched with H₂O (20 mL), and extracted with ethyl acetate (30 mL*3). The combined organic layers was washed with brine (10 mL) dried over Na₂SO₄, filtered and concentrated under reduce pressure. The residue was purified by flash silica gel chromatography (ISCO®; 12 g SepaFlash® Silica Flash Column, Eluent of 0~10% DCM/MeOH @ 30 mL/min) to give Compound (2S)-N-[(1S)-1-cyano-2-[(3S)-2-oxopyrrolidin-3-yl]ethyl]-3-cyclopropyl-2-(4-methyl-3-nitro-2-oxo-1-pyridyl)propanamide (60 mg, 17.8% yield) as a yellow solid.

LCMS: Rt=1.336 min; for $C_{19}H_{23}N_5O_5$ MS Calcd.: 401.17; MS Found: 402.1 [M+H⁺].

(2S)-2-(3-amino-4-methyl-2-oxo-1-pyridyl)-N-[(1S)-1-cyano-2-[(3S)-2-oxopyrrolidin-3-yl]ethyl]-3-cyclopropyl-propanamide To a solution of (2S)-N-[(1S)-1-cyano-2-[(3S)-2-oxopyrrolidin-3-yl]ethyl]-3-cyclopropyl-2-(4-methyl-3-nitro-2-oxo-1-pyridyl)propanamide (60 mg, 0.14 mmol, 1 eq) in THF (2 mL) was added Pd/C (70 mg, 65.7 umol, 10% purity, 0.44 eq). The mixture was stirred at 25° C. for 15 min under H₂. LCMS showed one peak with desired MS was detected. The reaction mixture was filtered and the filtrate was concentrated. The residue was purified by prep-HPLC (column: Phenomenex Gemini-NX 80*30 mm*3 um; mobile phase: [water(0.05% NH₃H₂O+10 mM NH₄HCO₃)-ACN]; B %: 13%-43%, 9.5 min) to give (2S)-2-(3-amino-4-methyl-2-oxo-1-pyridyl)-N-[(1S)-1-cyano-2-[(3S)-2-oxopyrrolidin-3-yl]ethyl]-3-cyclopropyl-propanamide (7.45 mg, 19.7 umol, 13.2% yield, 98.4% purity) as a brown solid.

LCMS: Rt=0.698 min; for $C_{19}H_{25}N_5O_3$ MS Calcd.: 371.20; MS Found: 372.1 [M+H⁺].

¹H NMR (400 MHz, CD₃OD) δ 6.94-6.82 (m, 1H), 6.11-6.01 (m, 1H), 5.40-5.23 (m, 1H), 4.86 (br dd, J=6.0, 9.8 Hz, 1H), 3.14-3.08 (m, 2H), 2.47-2.27 (m, 1H), 2.23-2.03 (m, 2H), 1.99-1.91 (m, 3H), 1.83-1.57 (m, 4H), 0.48 (br d, J=7.3 Hz, 1H), 0.34-0.19 (m, 2H), 0.02-0.16 (m, 2H).

Example 136. Synthesis of Viral Protease Inhibitor Compound 449

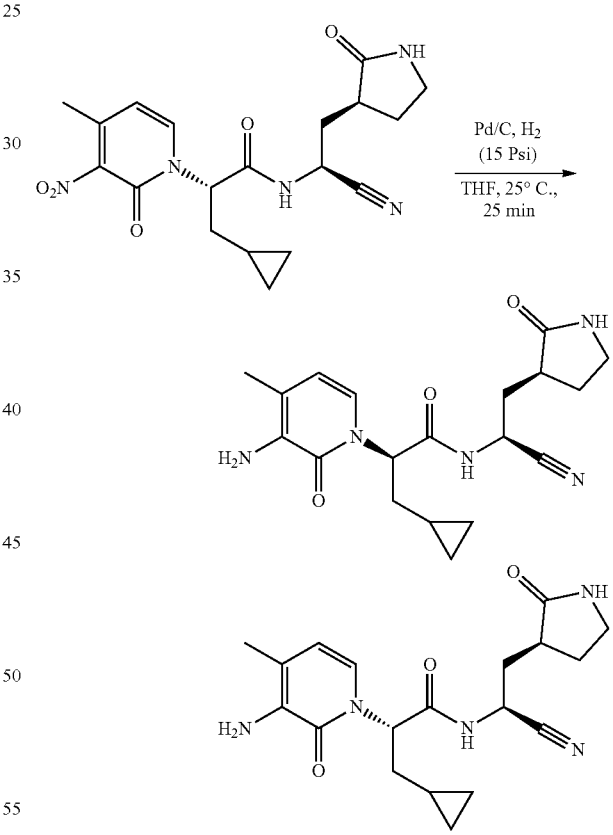

To a solution of (2S)-N-[(1S)-1-cyano-2-[(3S)-2-oxopyrrolidin-3-yl]ethyl]-3-cyclopropyl-2-(4-methyl-3-nitro-2-oxo-1-pyridyl)propanamide (345.0 mg, 0.85 mmol, 1 eq) in THF (5 mL) was added Pd/C (233.1 mg, 0.21 mmol, 10% purity). The mixture was stirred at 25° C. for 25 min under H₂. LCMS showed one peak with desired MS was detected. The reaction mixture was filtered and the filtrate was quenched with H₂O (20 mL), and extracted with ethyl acetate (30 mL*3). The combined organic layers was washed with brine (10 mL) dried over Na₂SO₄, filtered and concentrated under reduce pressure. The residue was purified by flash silica gel chromatography (ISCO®; 12 g SepaFlash® Silica Flash Column, Eluent of 0~10% DCM/MeOH @ 30 mL/min) to give the product (203 mg). 70 mg of product was separated by SFC (column: DAICEL CHIRALPAK AD (250 mm*30 mm, 10 um); mobile phase: [0.1% NH₃H₂O IPA]; B %: 45%-45%, min) to give 2-[(1S)-3-amino-4-methyl-2-oxo-1-pyridyl]-N-[(1S)-1-cyano-2-[(3S)-2-oxopyrrolidin-3-yl]ethyl]-3-cyclopropyl-propanamide (20.08 mg, 6.2% yield) and 2-[(1R)-3-amino-4-methyl-2-oxo-1-pyridyl]-N-[(1S)-1-cyano-2-[(3S)-2-oxopyrrolidin-3-yl]ethyl]-3-cyclopropyl-propanamide (23.04 mg, 7.0% yield) as a white solid.

Isomer 1: LCMS: Rt=0.659 min; for $C_{19}H_{25}N_5O_3$ MS Calcd.: 371.20; MS Found: 394.1 [M+Na$^+$]. $^1$H NMR (400 MHz, CD₃OD) δ 7.02 (d, J=7.0 Hz, 1H), 6.22 (d, J=7.1 Hz, 1H), 5.50 (t, J=7.8 Hz, 1H), 5.04-4.98 (m, 1H), 3.37-3.32 (m, 2H), 2.52-2.46 (m, 1H), 2.38-2.24 (m, 2H), 2.11 (s, 3H), 1.94-1.81 (m, 4H), 0.61-0.56 (m, 1H), 0.42-0.38 (m, 2H), 0.13-0.02 (m, 2H).

Isomer 2: LCMS: Rt=0.704 min; for $C_{19}H_{25}N_5O_3$ MS Calcd.: 371.20; MS Found: 372.1 [M+H$^+$]. $^1$H NMR (400 MHz, CD₃OD) δ 7.03 (d, J=7.1 Hz, 1H), 6.20 (d, J=7.0 Hz, 1H), 5.41 (dd, J=7.1, 8.4 Hz, 1H), 5.00 (br dd, J=6.1, 10.0 Hz, 1H), 3.29-3.24 (m, 2H), 2.49 (dq, J=5.4, 9.3 Hz, 1H), 2.31-2.21 (m, 2H), 2.09 (s, 3H), 1.98-1.76 (m, 4H), 0.69-0.57 (m, 1H), 0.50-0.41 (m, 2H), 0.17-0.04 (m, 2H).

Example 137. Synthesis of Viral Protease Inhibitor Compound 450

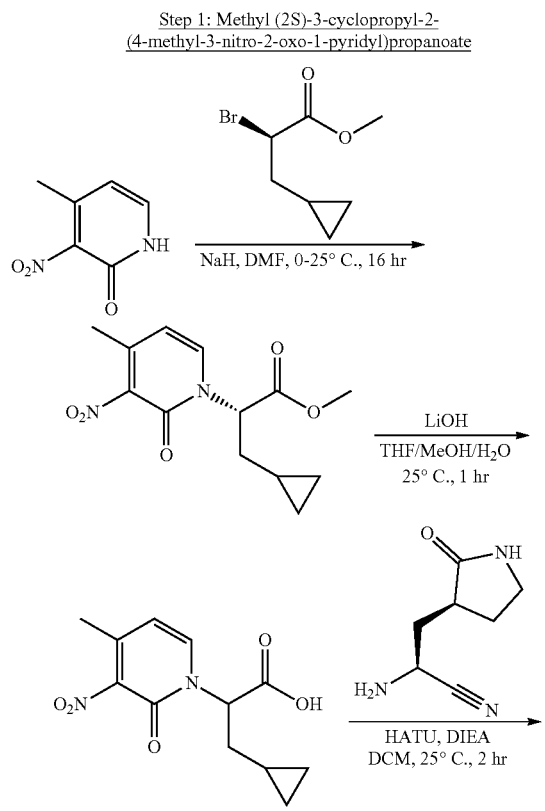

Step 1: Methyl (2S)-3-cyclopropyl-2-(4-methyl-3-nitro-2-oxo-1-pyridyl)propanoate

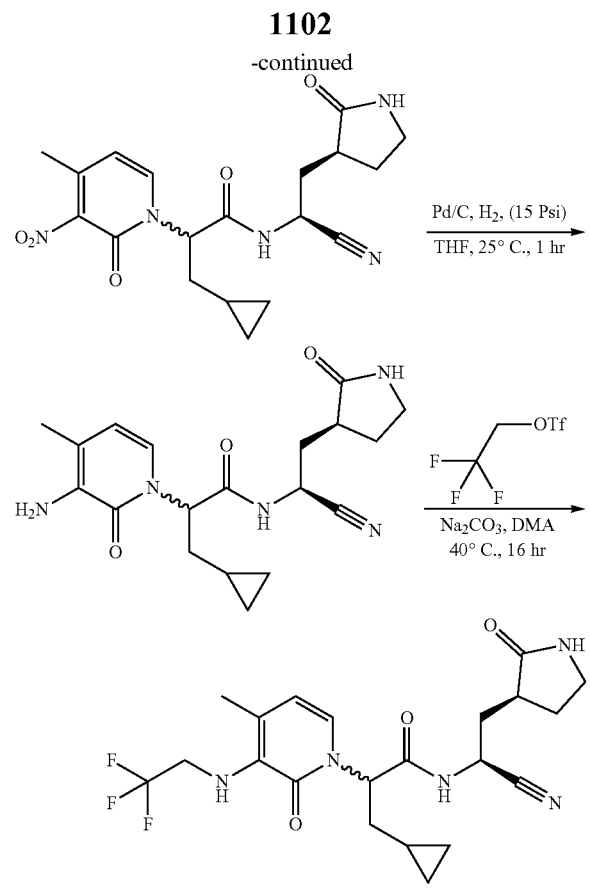

To a solution of 4-methyl-3-nitro-1H-pyridin-2-one (1 g, 6.49 mmol, 1 eq) in DMF (15 mL) was added NaH (363.3 mg, 9.08 mmol, 60% purity, 1.4 eq) at 0° C., and the reaction mixture was stirred at 25° C. for 0.5 hr. Then methyl (2R)-2-bromo-3-cyclopropyl-propanoate (1.34 g, 6.49 mmol, 1 eq) was added at 0° C. The mixture was stirred at 25° C. for 16 h under N₂. LCMS showed one peak with desired MS was detected. The mixture was quenched with H₂O (20 mL), and extracted with ethyl acetate (50 mL*3). The combined organic layers was washed with brine (40 mL) dried over Na₂SO₄, filtered and concentrated under reduce pressure. The residue was purified by flash silica gel chromatography (ISCO®; 24 g SepaFlash® Silica Flash Column, Eluent of 0~50% Ethyl acetate/Petroleum ether-gradient @ 35 mL/min) to give methyl (2S)-3-cyclopropyl-2-(4-methyl-3-nitro-2-oxo-1-pyridyl)propanoate (867 mg, 47.4% yield) as a yellow solid.

LCMS: Rt=0.785 min; for $C_{13}H_{16}N_2O_5$ MS Calcd.: 280.11; MS Found: 281.1 [M+H$^+$].

Step 2: (2S)-3-cyclopropyl-2-(4-methyl-3-nitro-2-oxo-1-pyridyl)propanoic acid

A mixture of methyl (2S)-3-cyclopropyl-2-(4-methyl-3-nitro-2-oxo-1-pyridyl)propanoate (867 mg, 3.09 mmol, 1 eq), LiOH·H₂O (519.2 mg, 12.37 mmol, 4 eq) in THF (6 mL), MeOH (2 mL), H₂O (2 mL) was degassed and purged with N₂ for 3 times, and then the mixture was stirred at 25° C. for 1 h under N₂ atmosphere. LCMS showed one peak with desired MS was detected. The mixture was added H₂O (5 mL), then the mixture was added 2 M HCl (4 mL) to adjust the pH to about 6-7. The mixture was extracted with ethyl acetate (30 mL*3). The combined organic layers was washed with brine (20 mL) dried over Na₂SO₄, filtered and concentrated under reduce pressure to give product. Compound (2S)-3-cyclopropyl-2-(4-methyl-3-nitro-2-oxo-1-pyridyl)propanoic acid (791 mg, 94.8% yield) was obtained as a yellow solid.

LCMS: Rt=0.735 min; for $C_{12}H_{14}N_2O_5$ MS Calcd.: 266.09; MS Found: 267.0 [M+H⁺].

Step 3: N-[(1S)-1-cyano-2-[(3S)-2-oxopyrrolidin-3-yl]ethyl]-3-cyclopropyl-2-(4-methyl-3-nitro-2-oxo-1-pyridyl)propanamide To a solution of (2S)-3-cyclopropyl-2-(4-methyl-3-nitro-2-oxo-1-pyridyl)propanoic acid (791 mg, 2.97 mmol, 1 eq) in DCM (10 mL) was added HATU (1.36 g, 3.57 mmol, 1.2 eq), DIPEA (1.15 g, 8.91 mmol, 1.55 mL, 3 eq) and (2S)-2-amino-3-[(3S)-2-oxopyrrolidin-3-yl]propanenitrile (676.0 mg, 3.57 mmol, 1.2 eq, HCl). The mixture was stirred at 25° C. for 2 h. LCMS showed one peak with desired MS was detected. The mixture was quenched with H₂O (20 mL), and extracted with DCM (40 mL*3). The combined organic layers was washed with brine (20 mL) dried over Na₂SO₄, filtered and concentrated under reduce pressure. The residue was purified by flash silica gel chromatography (ISCO®; 24 g SepaFlash® Silica Flash Column, Eluent of 0~10% DCM/MeOH ethergradient @ 35 mL/min) to give N-[(1S)-1-cyano-2-[(3S)-2-oxopyrrolidin-3-yl]ethyl]-3-cyclopropyl-2-(4-methyl-3-nitro-2-oxo-1-pyridyl)propanamide (838 mg, 64.5% yield) as yellow oil. LCMS: R'=0.741 min; for $C_{19}H_{23}N_5O_5$ MS Calcd.: 401.17; MS Found: 402.1 [M+H⁺].

Step 4: 2-(3-Amino-4-methyl-2-oxo-1-pyridyl)-N-[(1S)-1-cyano-2-[(3S)-2-oxopyrrolidin-3-yl]ethyl]-3-cyclopropyl-propanamide To a solution of N-[(1S)-1-cyano-2-[(3S)-2-oxopyrrolidin-3-yl]ethyl]-3-cyclopropyl-2-(4-methyl-3-nitro-2-oxo-1-pyridyl)propanamide (838 mg, 2.09 mmol, 1 eq) in THF (10 mL) was added Pd/C (566.5 mg, 0.53 mmol, 10% purity). The mixture was stirred at 25° C. for 1 h under H₂. LCMS showed one peak with desired MS was detected. The mixture was filtered and concentrated under reduce pressure to give 2-(3-amino-4-methyl-2-oxo-1-pyridyl)-N-[(1S)-1-cyano-2-[(3S)-2-oxopyrrolidin-3-yl]ethyl]-3-cyclopropyl-propanamide (616 mg, 68.7% yield) as a white solid.

LCMS: Rt=0.703 min; for $C_{19}H_{25}N_5O_3$ MS Calcd.: 371.20; MS Found: 372.1 [M+H⁺].

N-[(1S)-1-Cyano-2-[(3S)-2-oxopyrrolidin-3-yl]ethyl]-3-cyclopropyl-2-[4-methyl-2-oxo-3-(2,2,2-trifluoroethylamino)-1-pyridyl]propanamide To a solution of 2-(3-amino-4-methyl-2-oxo-1-pyridyl)-N-[(1S)-1-cyano-2-[(3S)-2-oxopyrrolidin-3-yl]ethyl]-3-cyclopropyl-propanamide (100 mg, 0.26 mmol, 1 eq) in DMA (5 mL) was added Na₂CO₃ (730.5 mg, 6.89 mmol, 25.60 eq) and 2,2,2-trifluoroethyl trifluoromethanesulfonate (1.6 g, 6.89 mmol, 25.6 eq). The mixture was stirred at 40° C. for 16 h. The mixture was filtered, and then the filtrate was quenched with H₂O (20 mL) and extracted with ethyl acetate (30 mL*3). The combined organic layers was washed with brine (10 mL) dried over Na₂SO₄, filtered and concentrated under reduce pressure. The residue was purified by prep-HPLC (column: Phenomenex Gemini-NX 80*40 mm*3 um; mobile phase: [water(0.05% NH₃H₂O+10 mM NH₄HCO₃)-ACN]; B %: 23%-53%, 7.8 min). Compound N-[(1S)-1-cyano-2-[(3S)-2-oxopyrrolidin-3-yl]ethyl]-3-cyclopropyl-2-[4-methyl-2-oxo-3-(2,2,2-trifluoroethylamino)-1-pyridyl]propanamide (71.7 mg, 57.9% yield) was obtained as a white solid. LCMS: Rt=0.794 min; for $C_{21}H_{26}F_3N_5O_3$ MS Calcd.: 453.20; MS Found: 454.1 [M+H⁺].

¹H NMR (400 MHz, CD₃OD) δ 7.24 (dd, J=3.9, 7.2 Hz, 1H), 6.22 (dd, J=5.5, 7.0 Hz, 1H), 5.52-5.32 (m, 1H), 5.01 (dd, J=6.1, 9.9 Hz, 1H), 4.03-3.73 (m, 2H), 3.36-3.32 (m, 1H), 3.29-3.21 (m, 1H), 2.56-2.45 (m, 1H), 2.41-2.22 (m, 2H), 2.21 (d, J=5.3 Hz, 3H), 2.04-1.91 (m, 2H), 1.91-1.71 (m, 2H), 0.67-0.55 (m, 1H), 0.48-0.35 (m, 2H), 0.18-0.02 (m, 2H).

Example 138. Synthesis of Viral Protease Inhibitor Compound 451

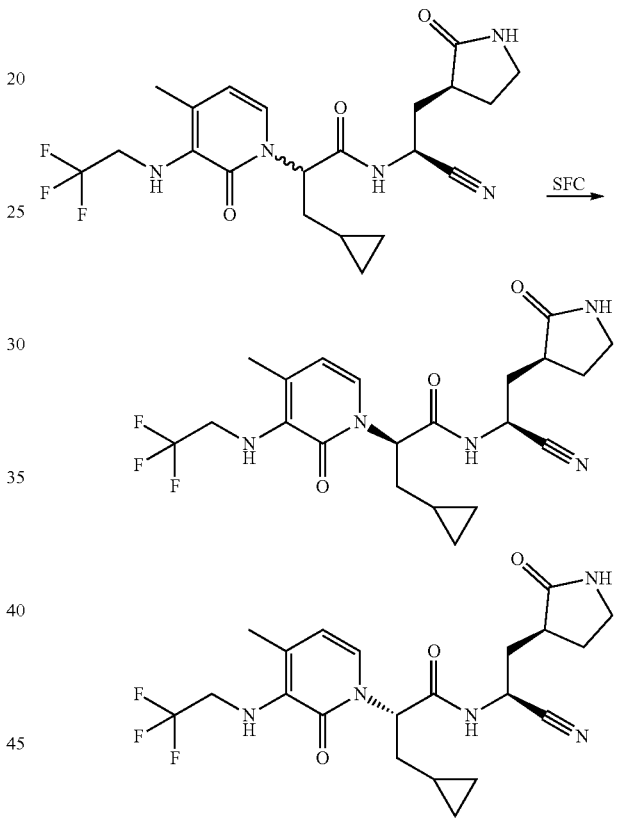

N-[(1S)-1-cyano-2-[(3S)-2-oxopyrrolidin-3-yl]ethyl]-3-cyclopropyl-2-[4-methyl-2-oxo-3-(2,2,2-trifluoroethylamino)-1-pyridyl]propanamide (69 mg, 0.15 mmol, 1 eq) was separated by SFC (condition: column: DAICEL CHIRALPAK AD (250 mm*30 mm, 10 um); mobile phase: [0.1% NH3H2O ETOH]; B %: 45%-45%, min) to afford (2R)-N-[(1S)-1-cyano-2-[(3S)-2-oxopyrrolidin-3-yl]ethyl]-3-cyclopropyl-2-[4-methyl-2-oxo-3-(2,2,2-trifluoroethylamino)-1-pyridyl]propanamide (17.12 mg, 24.8% yield) as a white solid.

Isomer 1: LCMS: Rt=0.799 min; for $C_{21}H_{26}F_3N_5O_3$ MS Calcd.: 453.20; MS Found: 454.1 [M+H⁺]. ¹H NMR (400 MHz, CD₃OD) δ 7.24 (d, J=7.0 Hz, 1H), 6.23 (d, J=7.3 Hz, 1H), 5.45 (t, J=7.8 Hz, 1H), 5.01 (dd, J=6.7, 9.4 Hz, 1H), 4.03-3.70 (m, 2H), 3.36-3.32 (m, 2H), 2.56-2.46 (m, 1H), 2.41-2.24 (m, 2H), 2.21 (s, 3H), 1.98-1.93 (m, 2H), 1.93-1.76 (m, 2H), 0.64-0.50 (m, 1H), 0.44-0.33 (m, 2H), 0.17-0.04 (m, 2H).

Isomer 2: LCMS: Rt=0.800 min; for $C_{21}H_{26}F_3N_5O_3$ MS Calcd.: 453.20; MS Found: 454.1 [M+H$^+$]. $^1$H NMR (400 MHz, CD$_3$OD) δ 7.25 (d, J=7.3 Hz, 1H), 6.22 (d, J=7.0 Hz, 1H), 5.38 (dd, J=7.0, 8.5 Hz, 1H), 5.01 (dd, J=6.0, 10.0 Hz, 1H), 3.89 (q, J=9.5 Hz, 2H), 3.30-3.21 (m, 2H), 2.50 (dq, J=5.3, 9.3 Hz, 1H), 2.32-2.22 (m, 2H), 2.20 (s, 3H), 2.06-1.90 (m, 2H), 1.89-1.68 (m, 2H), 0.69-0.57 (m, 1H), 0.50-0.36 (m, 2H), 0.22-0.04 (m, 2H).

Example 139. Synthesis of Viral Protease Inhibitor Compound 455

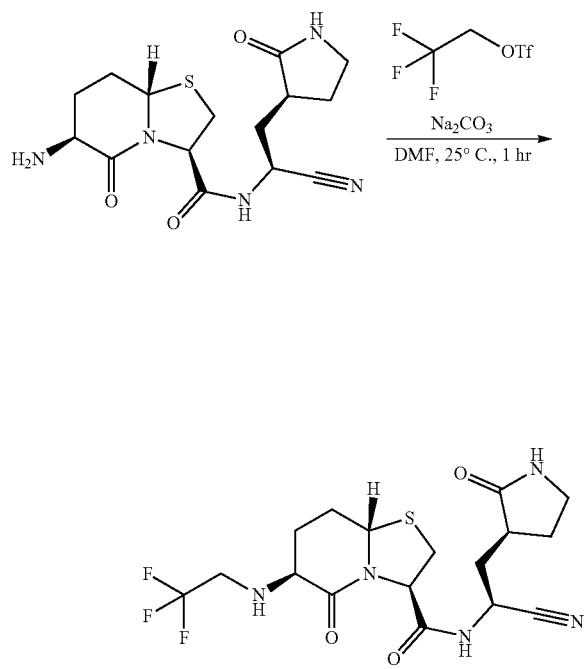

To a solution of (3R,6S)-6-amino-N-[(1S)-1-cyano-2-[(3S)-2-oxopyrrolidin-3-yl]ethyl]-5-oxo-2,3,6,7,8,8a-hexahydrothiazolo[3,2-a]pyridine-3-carboxamide (40.0 mg, 0.11 mmol, 1 eq) in DMF (0.5 mL) was added Na$_2$CO$_3$ (24.1 mg, 0.22 mmol, 2 eq) and 2,2,2-trifluoroethyl trifluoromethanesulfonate (26.4 mg, 0.11 mmol, 1 eq). The mixture was stirred at 25° C. for 1 h. The reaction mixture was added H$_2$O (10 mL) and extracted with ethyl acetate (10 mL*3). The combined organic layers were washed with brine (20 mL), dried with anhydrous Na$_2$SO$_4$, filtered and concentrated under reduced pressure to give a residue. The residue was purified by prep-HPLC (column: Phenomenex Gemini-NX 80*30 mm*3 um; mobile phase: [water(0.05% NH$_3$H$_2$O+10 mM NH4HCO3)-ACN]; B %: 8%-38%, 9.5 min). (3R,6S,8aS)-N-[(1S)-1-cyano-2-[(3S)-2-oxopyrrolidin-3-yl]ethyl]-5-oxo-6-(2,2,2-trifluoroethylamino)-2,3,6,7,8,8a-hexahydrothiazolo[3,2-a]pyridine-3-carboxamide (8.02 mg, 18.5 umol, 16.2% yield, 100% purity) was obtained as a white solid.

LCMS: Rt=0.686 min; for $C_{17}H_{22}F_3N_5O_3S$ MS Calcd.: 433.45; MS Found: 434.0 [M+H$^+$].

$^1$H NMR (400 MHz, CD$_3$OD) δ 5.02 (dd, J=10.79, 5.27 Hz, 1H), 4.90-4.98 (m, 2H), 4.77-4.83 (m, 1H), 3.33-3.49 (m, 4H), 3.20-3.29 (m, 1H), 3.11-3.20 (m, 1H), 2.67 (qd, J=9.29, 5.27 Hz, 1H), 2.17-2.45 (m, 4H), 1.72-1.99 (m, 4H).

Example 140. Synthesis of Viral Protease Inhibitor Compound 457

(3R,6S,8aS)-6-amino-N-((S)-cyano-2-((S)-2-oxopyrrolidin-3-yl)ethyl)-5-oxohexahydro-2H-thiazolo[3,2-a]pyridine-3-carboxamide

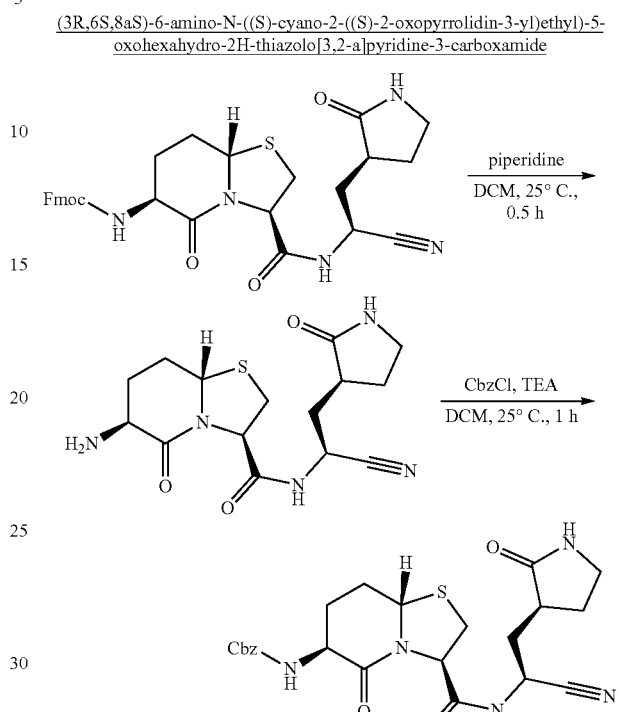

To a solution of 9H-fluoren-9-ylmethyl N-[(3R,6S)-3-[[(1S)-1-cyano-2-[(3S)-2-oxopyrrolidin-3-yl]ethyl]carbamoyl]-5-oxo-2,3,6,7,8,8a-hexahydrothiazolo[3,2-a]pyridin-6-yl]carbamate (50 mg, 87.1 umol, 1 eq) in DCM (0.2 mL) was added piperidine (14.8 mg, 0.17 mmol, 17 uL, 2 eq). The mixture was stirred at 25° C. for 0.5 hr. Compound (3R,6S)-6-amino-N-[(1S)-1-cyano-2-[(3S)-2-oxopyrrolidin-3-yl]ethyl]-5-oxo-2,3,6,7,8,8a-hexahydrothiazolo[3,2-a]pyridine-3-carboxamide (30 mg, crude) was obtained as a yellow oil.

Benzyl((3R,6S,8aS)-3-(((S)-1-cyano-2-((S)-2-oxopyrrolidin-3-yl)ethyl)carbamoyl)-5-oxohexahydro-2H-thiazolo[3,2-a]pyridin-6-yl)carbamate To a solution of (3R,6S)-6-amino-N-[(1S)-1-cyano-2-[(3S)-2-oxopyrrolidin-3-yl]ethyl]-5-oxo-2,3,6,7,8,8a-hexahydrothiazolo[3,2-a]pyridine-3-carboxamide (30 mg, 85.3 umol, 1 eq) in DCM (1 mL) was added benzyl carbonochloridate (29.1 mg, 0.17 mmol, 24 uL, 2 eq) and TEA (25.9 mg, 0.25 mmol, 35 uL, 3 eq). The mixture was stirred at 25° C. for 2 h. LCMS detected desired compound. The reaction mixture was added H$_2$O (10 mL) and extracted with ethyl acetate (10 mL*3). The combined organic layers were washed with brine (20 mL), dried with anhydrous Na$_2$SO$_4$, filtered and concentrated under reduced pressure to give a residue. The residue was purified by prep-HPLC (column: Phenomenex Gemini 150*25 mm*10 um; mobile phase: [water (0.05% NH$_3$H$_2$O+10 mM NH4HCO3)-ACN]; B %: 15%-45%, 9.5 min). Then the residue was purified by prep-HPLC (column: Waters Xbridge 150*25 mm*5 um; mobile phase: [water (0.04% NH$_3$H$_2$O+10 mM NH4HCO3)-MeOH]; B %: 40%-80%, 9.5 min). Compound benzyl N-[(3R,6S)-3-[[(1S)-1-cyano-2-[(3S)-2-oxopyrrolidin-3-yl]ethyl]carbamoyl]-5-oxo-2,3,6,7,8,8a-hexahydrothiazolo[3,2-a]pyridin-6-yl]carbamate (1.41 mg, 2.8 umol, 3.3% yield, 99% purity) was obtained as a white solid. LCMS: Rt=0.751 min; for $C_{23}H_{27}N_5O_5S$ MS Calcd.: 485.56; MS Found: 486.1 [M+H$^+$].

$^1$H NMR (400 MHz, CDCl$_3$) δ8.32 (br s, 1H), 7.37 (br s, 5H), 6.07 (br s, 1H), 5.67 (br s, 1H), 5.38 (br s, 1H), 5.17 (br d, J=10.26 Hz, 2H), 4.90 (br s, 1H), 4.80 (br s, 1H), 3.97 (br s, 1H), 3.52 (br s, 1H), 3.25 (br s, 1H), 3.33 (br s, 3H), 2.44 (br s, 1H), 2.33 (br d, J=15.38 Hz, 1H), 1.97-2.13 (m, 2H), 1.85 (br s, 3H).

Example 141. Synthesis of Viral Protease Inhibitor Compound 459

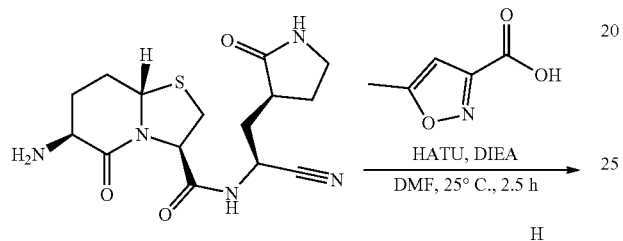

N-((3R,6S,8aS)-3-(((S)-1-cyano-2-((S)-2-oxopyrrolidin-3-yl)ethyl)carbamoyl)-5-oxohexahydro-2H-thiazolo[3,2-a]pyridin-6-yl)-5-methylisoxazole-3-carboxamide A mixture of 5-methylisoxazole-3-carboxylic acid (36.1 mg, 0.28 mmol, 2 eq), HATU (108.2 mg, 0.28 mmol, 2 eq) and DIEA (73.5 mg, 0.56 mmol, 99 uL, 4 eq) in DMF (1 mL) was stirred at 25° C. for 0.5 h, and then (3R,6S)-6-amino-N-[(1S)-1-cyano-2-[(3S)-2-oxopyrrolidin-3-yl]ethyl]-5-oxo-2,3,6,7,8,8a-hexahydrothiazolo[3,2-a]pyridine-3-carboxamide (50.0 mg, 0.14 mmol, 1 eq) was added into the reaction. The resulting mixture was stirred at 25° C. for 2 h. The reaction mixture was added H$_2$O (10 mL) and extracted with ethyl acetate (10 mL*3). The combined organic layers were washed with brine (20 mL), dried with anhydrous Na$_2$SO$_4$, filtered and concentrated under reduced pressure to give a residue. The residue was purified by prep-HPLC (column: Phenomenex Gemini-NX 80*30 mm*3 um; mobile phase: [water(0.05% NH$_3$H$_2$O+10 mM NH$_4$HCO$_3$)-ACN]; B %: 7%-37%, 9.5 min). Compound N-[(3R,6S,8aS)-3-[[(1S)-1-cyano-2-[(3S)-2-oxopyrrolidin-3-yl]ethyl]carbamoyl]-5-oxo-2,3,6,7,8,8a-hexahydrothiazolo[3,2-a]pyridin-6-yl]-5-methyl-isoxazole-3-carboxamide (15.28 mg, 33.0 umol, 23.2% yield, 99.7% purity) was obtained as a white solid. LCMS: Rt=0.698 min; for $C_{20}H_{24}N_6O_5S$ MS Calcd.: 460.51; MS Found: 461.1 [M+H$^+$].

$^1$H NMR (400 MHz, CD$_3$OD) δ ppm 6.52 (d, J=0.75 Hz, 1H), 4.98-5.07 (m, 3H), 4.44 (dd, J=11.17, 6.90 Hz, 1H), 3.41 (dd, J=11.67, 7.65 Hz, 1H), 3.23-3.29 (m, 3H), 2.58-2.69 (m, 1H), 2.48 (s, 3H), 2.27-2.44 (m, 4H), 2.08-2.21 (m, 1H), 1.79-2.01 (m, 3H).

Example 142. Synthesis of Viral Protease Inhibitor Compound 465

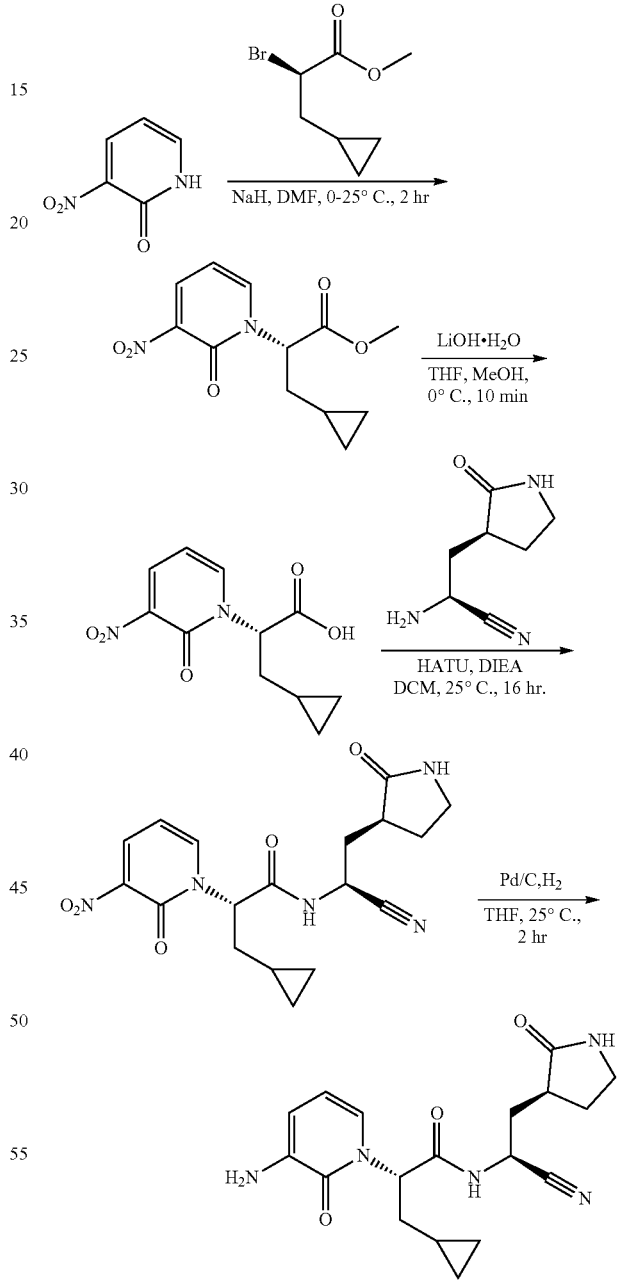

To a solution of 3-nitro-1H-pyridin-2-one (1 g, 7.14 mmol, 1 eq) in DMF (10 mL) was added NaH (428.2 mg, 10.71 mmol, 60% purity, 1.5 eq) at 0° C. for 15 min. Then, methyl (2R)-2-bromo-3-cyclopropyl-propanoate (1.6 g, 7.85 mmol, 1.1 eq) was added into the mixture, and the mixture was stirred at 25° C. for 2 hr. TLC (petroleum ether:ethyl acetate=1:1) showed new spot was detected. The reaction mixture was quenched by addition H₂O (10 mL) at 0° C., and extracted with ethyl acetate (10 mL*3). The combined organic phase was washed with brine (10 mL*3), dried with anhydrous Na₂SO₄, filtered and concentrated in vacuum. The residue was purified by flash silica gel chromatography (ISCO®; 25 g SepaFlash® Silica Flash Column, Eluent of 0~50% petroleum ether/ethyl acetate ethergradient @ 30 mL/min) to give methyl (2S)-3-cyclopropyl-2-(3-nitro-2-oxo-1-pyridyl)propanoate (552 mg, 28.7% yield, 98.9% purity) as a yellow solid.

(2S)-3-cyclopropyl-2-(3-nitro-2-oxo-1-pyridyl)pro-
panoic acid

To a solution of methyl (2S)-3-cyclopropyl-2-(3-nitro-2-oxo-1-pyridyl)propanoate (230 mg, 0.86 mmol, 1 eq) in THF (1 mL) and MeOH (0.2 mL) was added LiOH·H₂O (108.7 mg, 2.59 mmol, 3 eq) in H₂O (0.2 mL). The mixture was stirred at 0° C. for 10 min. LC-MS showed the desired compound was detected. The reaction was adjusted with 4 M HCl to pH=4. The reaction mixture was diluted with H₂O (5 mL) and extracted with ethyl acetate (5 mL*3). The combined organic phase was washed with brine (5 mL*3), dried with anhydrous Na₂SO₄, filtered and concentrated in vacuum. The crude product was used into the next step without further purification. Compound (2S)-3-cyclopropyl-2-(3-nitro-2-oxo-1-pyridyl)propanoic acid (210 mg, 96.3% yield) was obtained as a yellow solid.

(2S)-N-[(1S)-1-cyano-2-[(3S)-2-oxopyrrolidin-3-yl]
ethyl]-3-cyclopropyl-2-(3-nitro-2-oxo-1-pyridyl)
propanamide To a solution of (2S)-3-cyclopropyl-2-(3-nitro-2-oxo-1-pyridyl)propanoic acid (260 mg, 1.03 mmol, 1 eq) in DCM (3 mL) was added HATU (470.3 mg, 1.24 mmol, 1.2 eq), DIPEA (266.4 mg, 2.06 mmol, 0.35 mL, 2 eq) and (2S)-2-amino-3-[(3S)-2-oxopyrrolidin-3-yl]propanenitrile (234.5 mg, 1.24 mmol, 1.2 eq, HCl). The mixture was stirred at 25° C. for 16 h. TLC (DCM/MeOH=10:1) showed new spot was detected. The reaction mixture was diluted with H₂O (10 mL) and extracted with ethyl acetate (10 mL*3). The combined organic phase was washed with brine (10 mL*3), dried with anhydrous Na₂SO₄, filtered and concentrated in vacuum. The residue was purified by flash silica gel chromatography (ISCO®; 4 g SepaFlash® Silica Flash Column, Eluent of 0~10% DCM/MeOH ethergradient @ 20 mL/min) to give (2S)-N-[(1S)-1-cyano-2-[(3S)-2-oxopyrrolidin-3-yl]ethyl]-3-cyclopropyl-2-(3-nitro-2-oxo-1-pyridyl)propanamide (225 mg, 54.0% yield, 96% purity) as a yellow solid.

(2S)-2-(3-amino-2-oxo-1-pyridyl)-N-[(1S)-1-cyano-
2-[(3S)-2-oxopyrrolidin-3-yl]ethyl]-3-cyclopropyl-
propanamide To a solution of (2S)-N-[(1S)-1-cyano-2-[(3S)-2-oxopyrrolidin-3-yl]ethyl]-3-cyclopropyl-2-(3-nitro-2-oxo-1-pyridyl)propanamide (200 mg, 0.51 mmol, 1 eq) in THF (0.5 mL) was added Pd/C (200 mg, 0.18 mmol, 10% purity, 3.64 e−1 eq) under N₂. The suspension was degassed under vacuum and purged with H₂ several times. The mixture was stirred under H₂ (15 psi) at 25° C. for 10 min. LC-MS showed the desired compound was detected. TLC (DCM/MeOH=10:1) showed new spot was detected. The resulting product was dissolved in MeOH (5 mL) and filtered to remove the insoluble. The filter liquor was concentrated in vacuo. The residue was purified by flash silica gel chromatography (ISCO®; 4 g SepaFlash® Silica Flash Column, Eluent of 0~5% petroleum ether/ethyl acetate ethergradient @ 20 mL/min) to give (2S)-2-(3-amino-2-oxo-1-pyridyl)-N-[(1S)-1-cyano-2-[(3S)-2-oxopyrrolidin-3-yl]ethyl]-3-cyclopropyl-propanamide (119 mg, 64.3% yield, 99.7% purity) as a brown solid.

LCMS: Rt=0.669 min; for C₁₈H₂₃N₅O₃ MS Calcd.: 357.18; MS Found: 358.1 [M+H⁺].

¹H NMR (400 MHz, CD₃OD) δ 7.06-7.01 (m, 1H), 6.70-6.64 (m, 1H), 6.24 (s, 1H), 5.56-5.41 (m, 1H), 5.06-4.97 (m, 1H), 3.30-3.24 (m, 2H), 2.57-2.43 (m, 1H), 2.38-2.18 (m, 2H), 2.04-1.85 (m, 3H), 1.85-1.69 (m, 1H), 0.70-0.54 (m, 1H), 0.50-0.36 (m, 2H), 0.21-0.12 (m, 1H), 0.10-0.02 (m, 1H).

Example 143. Synthesis of Viral Protease Inhibitor
Compound 465

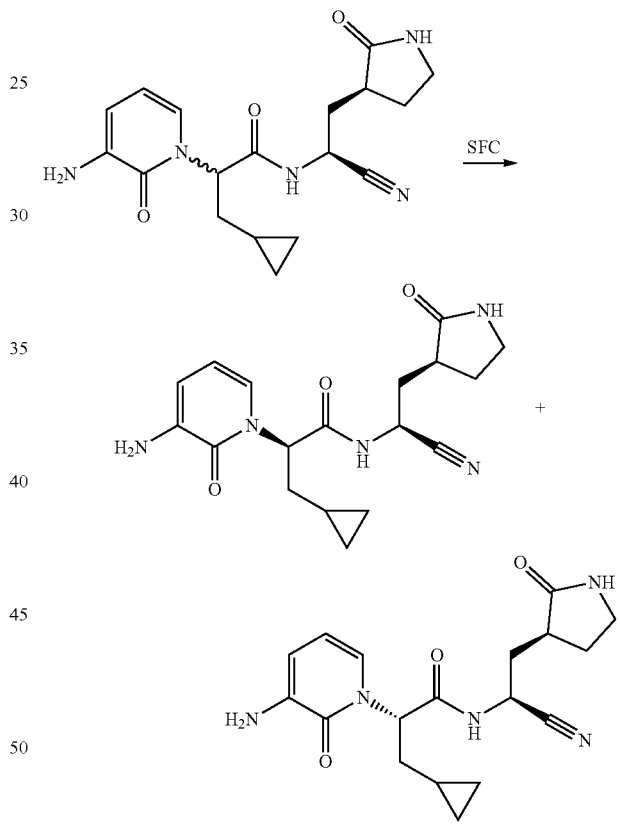

The residue was purification by SFC. LC-MS showed the desired compound was detected. The residue was purified by SFC (column: DAICEL CHIRALPAK AS (250 mm*30 mm, 10 um); mobile phase: [0.1% NH₃H₂O EtOH]; B %: 30%-30%, min).

Isomer 1: 2-[(1S)-3-amino-2-oxo-1-pyridyl]-N-[(1S)-1-cyano-2-[(3S)-2-oxopyrrolidin-3-yl]ethyl]-3-cyclopropyl-propanamide (2.84 mg, 6.3% yield, 98.9% purity) as a brown solid. LCMS: Rt=0.660 min; for C₁₈H₂₃N₅O₃ MS Calcd.: 357.41; MS Found: 358.1 [M+H⁺]. ¹H NMR (400 MHz, CD₃OD) δ 7.03 (dd, J=1.4, 7.0 Hz, 1H), 6.68 (dd, J=1.4, 7.2 Hz, 1H), 6.26 (t, J=7.1 Hz, 1H), 5.53 (t, J=7.7 Hz, 1H), 5.02 (dd, J=6.8, 9.3 Hz, 1H), 3.38-3.32 (m, 2H), 2.56-2.46 (m, 1H), 2.36 (m, 1H), 2.32-2.23 (m, 1H), 1.97-1.87 (m, 3H), 1.87-1.79 (m, 1H), 0.67-0.54 (m, 1H), 0.45-0.34 (m, 2H), 0.19-0.10 (m, 1H), 0.07-0.02 (m, 1H).

Isomer 2: Compound 2-[(1R)-3-amino-2-oxo-1-pyridyl]-N-[(1S)-1-cyano-2-[(3S)-2-oxopyrrolidin-3-yl]ethyl]-3-cyclopropyl-propanamide (21.3 mg, 46.5% yield) was obtained as a brown solid. LCMS: Rt=0.671 min; for $C_{18}H_{23}N_5O_3$ MS Calcd.: 357.41; MS Found: 358.1 [M+H$^+$].
$^1$H NMR (400 MHz, CD$_3$OD) δ 7.04 (dd, J=1.5, 7.0 Hz, 1H), 6.67 (dd, J=1.5, 7.3 Hz, 1H), 6.24 (t, J=7.1 Hz, 1H), 5.44 (t, J=7.7 Hz, 1H), 5.01 (dd, J=6.1, 10.1 Hz, 1H), 3.30-3.24 (m, 2H), 2.49 (dq, J=5.4, 9.3 Hz, 1H), 2.32-2.20 (m, 2H), 2.01-1.83 (m, 3H), 1.83-1.70 (m, 1H), 0.70-0.59 (m, 1H), 0.51-0.38 (m, 2H), 0.20-0.12 (m, 1H), 0.10-0.00 (m, 1H).

Example 144. Synthesis of Viral Protease Inhibitor Compound 466

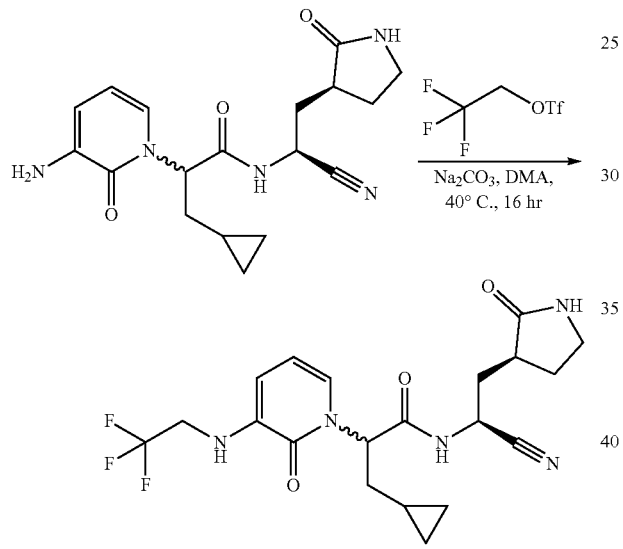

To a solution of 2-(3-amino-2-oxo-1-pyridyl)-N-[(1S)-1-cyano-2-[(3S)-2-oxopyrrolidin-3-yl]ethyl]-3-cyclopropyl-propanamide (110 mg, 0.30 mmol, 1 eq) in DMA (1 mL) was added Na$_2$CO$_3$ (326.2 mg, 3.08 mmol, 10 eq) and 2,2,2-trifluoroethyl trifluoromethanesulfonate (2.1 g, 9.23 mmol, 30 eq). The mixture was stirred at 40° C. for 16 h. TLC (DCM:MeOH=10:1) showed new spot was detected. The reaction mixture was diluted with H$_2$O (10 mL) and extracted with ethyl acetate (10 mL*3). The combined organic phase was washed with brine (10 mL*3), dried with anhydrous Na$_2$SO$_4$, filtered and concentrated in vacuum. The residue was purified by prep-TLC (SiO$_2$, DCM:MeOH=10:1) to give N-[(1S)-1-cyano-2-[(3S)-2-oxopyrrolidin-3-yl]ethyl]-3-cyclopropyl-2-[2-oxo-3-(2,2,2-trifluoroethylamino)-1-pyridyl]propanamide (23 mg, 16.8% yield, 98.8% purity) as a white solid.

LCMS: Rt=0.797 min; for $C_{20}H_{24}F_3N_5O_3$ MS Calcd.: 439.18; MS Found: 440.1 [M+H$^+$].

$^1$H NMR (400 MHz, CD$_3$OD) δ 7.06 (dt, J=1.5, 6.8 Hz, 1H), 6.65-6.55 (m, 1H), 6.37-6.27 (m, 1H), 5.56-5.40 (m, 1H), 5.05-4.98 (m, 1H), 3.88 (dq, J=6.0, 9.2 Hz, 2H), 3.34 (br d, J=3.0 Hz, 1H), 3.30-3.24 (m, 1H), 2.57-2.42 (m, 1H), 2.39-2.20 (m, 2H), 2.08-1.88 (m, 3H), 1.86-1.74 (m, 1H), 0.71-0.52 (m, 1H), 0.50-0.36 (m, 2H), 0.22-0.11 (m, 1H), 0.10-0.03 (m, 1H).

Example 145. Synthesis of Viral Protease Inhibitor Compound 467

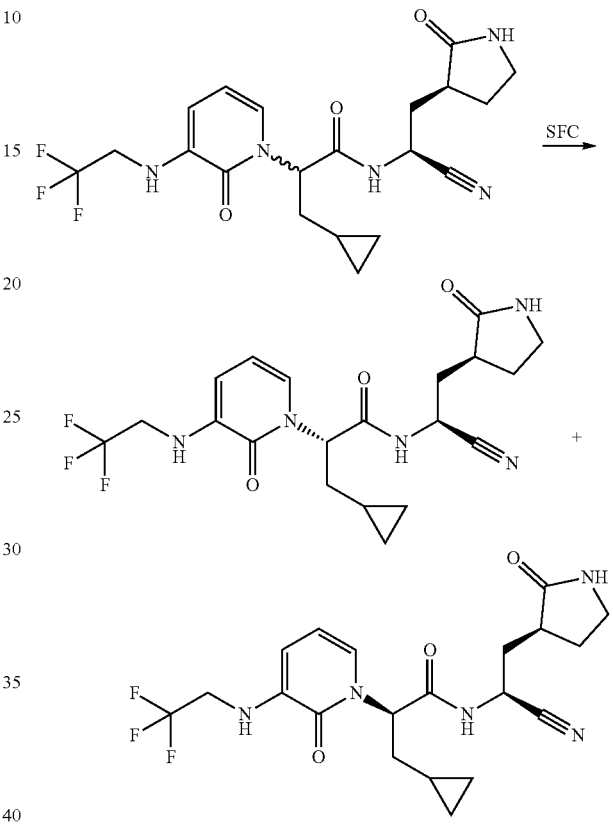

The residue was further separated by SFC. The residue was further separated by SFC (column: DAICEL CHIRALCEL OD-H (250 mm*30 mm, 5 um); mobile phase: [0.1% NH$_3$H$_2$O ETOH]; B %: 20%-20%, min).

Isomer 1: (2R)-N-[(1S)-1-cyano-2-[(3S)-2-oxopyrrolidin-3-yl]ethyl]-3-cyclopropyl-2-[2-oxo-3-(2,2,2-trifluoroethylamino)-1-pyridyl]propanamide (2.56 mg, 12.3% yield) as a white solid. LCMS: Rt=0.837 min; for $C_{23}H_{31}N_5O_5$ MS Calcd.: 457.23; MS Found: 458.1 [M+H$^+$]. $^1$H NMR (400 MHz, CD$_3$OD) δ 7.06 (dt, J=1.5, 6.8 Hz, 1H), 6.65-6.55 (m, 1H), 6.37-6.27 (m, 1H), 5.56-5.40 (m, 1H), 5.05-4.98 (m, 1H), 3.88 (dq, J=6.0, 9.2 Hz, 2H), 3.34 (br d, J=3.0 Hz, 1H), 3.30-3.24 (m, 1H), 2.57-2.42 (m, 1H), 2.39-2.20 (m, 2H), 2.08-1.88 (m, 3H), 1.86-1.74 (m, 1H), 0.71-0.52 (m, 1H), 0.50-0.36 (m, 2H), 0.22-0.11 (m, 1H), 0.10-0.03 (m, 1H).

Isomer 2: Compound (2R)-N-[(1S)-1-cyano-2-[(3S)-2-oxopyrrolidin-3-yl]ethyl]-3-cyclopropyl-2-[2-oxo-3-(2,2,2-trifluoroethylamino)-1-pyridyl]propanamide (2.56 mg, 12.3% yield, 96.3% purity) as a white solid. LCMS: Rt=0.794 min; for $C_{20}H_{24}F_3N_5O_3$ MS Calcd.: 439.18; MS Found: 440.1 [M+H$^+$]. $^1$H NMR (400 MHz, CD$_3$OD) δ 7.04 (dd, J=1.5, 7.0 Hz, 1H), 6.61 (d, J=7.0 Hz, 1H), 6.32 (t, J=7.2 Hz, 1H), 5.52 (t, J=7.8 Hz, 1H), 5.01 (dd, J=6.5, 9.3 Hz, 1H), 3.89 (q, J=9.3 Hz, 2H), 3.37-3.32 (m, 2H), 2.55-2.46 (m, 1H), 2.36 (m, 1H), 2.32-2.24 (m, 1H), 1.99-1.93 (m, 2H), 1.93-1.87 (m, 1H), 1.87-1.78 (m, 1H), 0.64-0.54 (m, 1H), 0.46-0.34 (m, 2H), 0.18-0.09 (m, 1H), 0.07-0.02 (m, 1H).

Example 146. Synthesis of Viral Protease Inhibitor Compound 468

Step 1: tert-Butyl 7-[(1S)-1-cyclopropylmethyl)-2-methoxy-2-oxo-ethyl]-6-oxo-1,7-diazaspiro[4.4]nonane-1-carboxylate

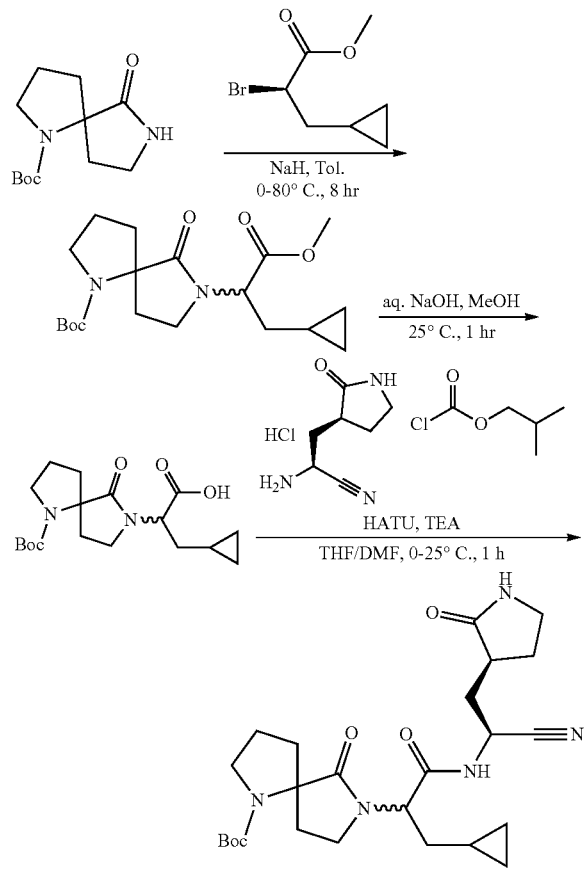

To a solution of tert-butyl 6-oxo-1,7-diazaspiro[4.4]nonane-1-carboxylate (0.5 g, 2.08 mmol, 1 eq) in toluene (7 mL) was added NaH (124.8 mg, 3.12 mmol, 60% purity, 1.5 eq) at 0° C. After stirring at 25° C. for 1 h, methyl (R)-2-bromo-3-cyclopropylpropanoate (517.0 mg, 2.50 mmol, 1.2 eq) was added at 0° C. and the mixture was stirred at 80° C. for 8 h. The reaction mixture was quenched by addition H$_2$O (15 mL) and extracted with EtOAc (15 mL*3). The combined organic layers were washed with brine (20 mL*2), dried over Na$_2$SO$_4$, filtered and concentrated under reduced pressure to give tert-butyl 7-(3-cyclopropyl-1-methoxy-1-oxopropan-2-yl)-6-oxo-1,7-diazaspiro[4.4]nonane-1-carboxylate (600 mg, crude) as a colorless oil.

Step 2: 2-(1-tert-butoxycarbonyl-6-oxo-1,7-diazaspiro[4.4]nonan-7-yl)-3-cyclopropyl-propanoic acid To a solution of 2 (450.0 mg, 1.23 mmol, 1 eq) in H$_2$O (1 mL) and MeOH (3 mL) was added NaOH (196.4 mg, 4.91 mmol, 4 eq). The mixture was stirred at 25° C. for 1 h. LC-MS showed 2 was consumed completely and 66% of desired compound was detected. The reaction mixture was quenched by addition H$_2$O (15 mL). The pH of the mixture was adjusted whit HCl (2 M) to 5-6. And then the mixture extracted with EtOAc (20 mL*3). The combined organic layers were washed with brine (20 mL*2), dried over Na$_2$SO$_4$, filtered and concentrated under reduced pressure to give a residue, and 2-(1-tert-butoxycarbonyl-6-oxo-1,7-diazaspiro[4.4]nonan-7-yl)-3-cyclopropyl-propanoic acid (0.4 g, crude) was obtained as a colorless oil.

468: tert-butyl 7-[2-[[(1S)-1-cyano-2-[(3S)-2-oxopyrrolidin-3-yl]ethyl]amino]-1-(cyclo propylmethyl)-2-oxo-ethyl]-6-oxo-1,7-diazaspiro[4.4]nonane-1-carboxylate To a solution of 2-(1-tert-butoxycarbonyl-6-oxo-1,7-diazaspiro[4.4]nonan-7-yl)-3-cyclopropyl-propanoic acid (50.0 mg, 0.14 mmol, 1 eq) and in THF (1 mL) was added Et$_3$N (14.3 mg, 0.14 mmol, 19.7 uL, 1.0 eq) and isobutyl carbonochloridate (21.3 mg, 0.15 mmol, 20.4 uL, 1.1 eq) at 0° C. The mixture was stirred at 25° C. for 1 h. A solution of (2S)-2-amino-3-[(3S)-2-oxopyrrolidin-3-yl]propanenitrile (32.2 mg, 0.17 mmol, 1.2 eq, HCl) and Et$_3$N (15.7 mg, 0.15 mmol, 21.7 uL, 1.1 eq) in DMF (1 mL) was added and the mixture was stirred at 25° C. for 1 h. The reaction mixture was concentrated under reduced pressure to give a residue. The residue was purified by prep-HPLC (column: Phenomenex Gemini 150*25 mm*10 um; mobile phase: [water (0.05% NH$_3$H$_2$O+10 mM NH4HCO3)-ACN]; B %: 23%-53%, 9.5 min) to give 468 (9.02 mg, 13% yield) as a white solid.

LCMS: Rt=0.821 min; for C$_{25}$H$_{37}$N$_5$O$_5$ MS Calcd.: 487.28; MS Found: 388.1 [M−Boc+H$^+$].

$^1$H NMR (400 MHz, CD$_3$OD) δ 8.34-8.15 (m, 1H), 5.72 (d, J=10.0 Hz, 1H), 5.29-4.98 (m, 1H), 4.95-4.81 (m, 1H), 3.59-3.47 (m, 2H), 3.46-3.19 (m, 4H), 2.64-2.29 (m, 4H), 2.28-2.16 (m, 1H), 2.10-2.00 (m, 2H), 1.97-1.84 (m, 4H), 1.73-1.60 (m, 2H), 1.53-1.38 (m, 9H), 0.71-0.52 (m, 1H), 0.51-0.38 (m, 2H), 0.17-0.07 (m, 2H).

Example 147. Synthesis of Viral Protease Inhibitor Compound 469

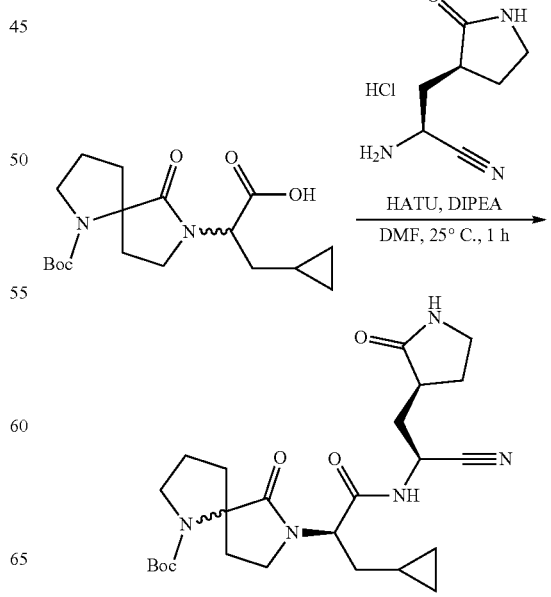

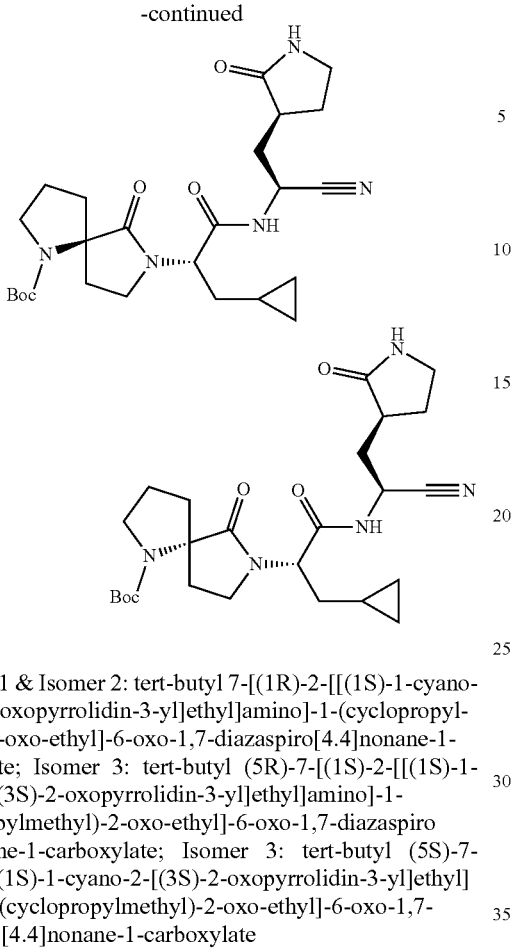

Isomer 1 & Isomer 2: tert-butyl 7-[(1R)-2-[[(1S)-1-cyano-2-[(3S)-2-oxopyrrolidin-3-yl]ethyl]amino]-1-(cyclopropylmethyl)-2-oxo-ethyl]-6-oxo-1,7-diazaspiro[4.4]nonane-1-carboxylate; Isomer 3: tert-butyl (5R)-7-[(1S)-2-[[(1S)-1-cyano-2-[(3S)-2-oxopyrrolidin-3-yl]ethyl]amino]-1-(cyclopropylmethyl)-2-oxo-ethyl]-6-oxo-1,7-diazaspiro[4.4]nonane-1-carboxylate; Isomer 3: tert-butyl (5S)-7-[(1S)-2-[[(1S)-1-cyano-2-[(3S)-2-oxopyrrolidin-3-yl]ethyl]amino]-1-(cyclopropylmethyl)-2-oxo-ethyl]-6-oxo-1,7-diazaspiro[4.4]nonane-1-carboxylate To a solution of 2-(1-(tert-butoxycarbonyl)-6-oxo-1,7-diazaspiro[4.4]nonan-7-yl)-3-cyclopropylpropanoic acid (200 mg, 0.56 mmol, 1 eq) and in DMF (2 mL) was added HATU (431.5 mg, 1.13 mmol, 2.0 eq), (S)-2-amino-3-((S)-2-oxopyrrolidin-3-yl)propanenitrile (129.1 mg, 0.68 mmol, 1.2 eq, HCl) and DIPEA (146.6 mg, 1.13 mmol, 197.7 uL, 2.0 eq). The mixture was stirred at 25° C. for 0.5 h. TLC (Dichloromethane: Methanol=10/1, PMA) indicated reactant 1 was consumed completely and one new spot formed. The reaction mixture was concentrated under reduced pressure to give a residue. The residue was purified by column chromatography (SiO$_2$, Dichloromethane:Methanol=100/1 to 10/1) to give S4N_20 (150 mg) as a white solid. S4N_20 (150 mg) was purified by prep-HPLC column: Phenomenex Gemini-NX 80*30 mm*3 um; mobile phase: [water (0.05% NH$_3$H$_2$O+10 mM NH$_4$HCO$_3$)-ACN]; B %: 25%-55%, 9.5 min) to give S4N_20 (60 mg) as a white solid. S4N_20 (60 mg) was purified by prep-SFC (column: DAICEL CHIRALPAK IC (250 mm*30 mm, 10 um); mobile phase: [0.1% NH$_3$H$_2$O ETOH]; B %: 55%-55%, min) to Isomer 1 & Isomer 2 (15 mg, 30.7 umol, 5.42% yield), Isomer 3 (8.46 mg, 16.3 umol, 2% yield, 94% purity) Isomer 4 (9.97 mg, 18.2 umol, 3% yield, 89% purity) as three white solids.

Isomer 1 & 2: LCMS: Rt=1.610 for C$_{25}$H$_{37}$N$_5$O$_5$ MS Calcd.: 487.28; MS Found: 488.2 [M+H$^+$]. $^1$H NMR (400 MHz, CD$_3$OD) δ 5.20-4.98 (m, 1H), 4.81-4.71 (m, 1H), 3.61-3.41 (m, 3H), 3.38-3.32 (m, 3H), 2.61-2.41 (m, 2H), 2.40-2.19 (m, 2H), 2.18-1.66 (m, 9H), 1.52-1.33 (m, 9H), 0.78-0.57 (m, 1H), 0.56-0.38 (m, 2H), 0.25-0.04 (m, 2H).

Isomer 3: LCMS: Rt=1.631 for C$_{25}$H$_{37}$N$_5$O$_5$ MS Calcd.: 487.28; MS Found: 488.2 [M+H$^+$]. $^1$H NMR (400 MHz, CD$_3$OD) δ 5.20-4.97 (m, 1H), 4.53-4.32 (m, 1H), 3.64-3.41 (m, 3H), 3.31 (s, 3H), 2.63-2.35 (m, 2H), 2.35-2.12 (m, 2H), 2.12-1.74 (m, 8H), 1.73-1.52 (m, 1H), 1.73-1.52 (m, 1H), 1.50-1.35 (m, 9H), 0.75 (s, 1H), 0.62-0.36 (m, 2H), 0.24-0.07 (m, 2H).

Isomer 4: LCMS: Rt=1.630 for C$_{25}$H$_{37}$N$_5$O$_5$ MS Calcd.: 487.28; MS Found: 488.2 [M+H$^+$]. $^1$H NMR (400 MHz, CD$_3$OD) δ 5.23-5.01 (m, 1H), 4.81-4.74 (m, 1H), 3.64-3.37 (m, 3H), 3.35 (s, 3H), 2.67-2.42 (m, 2H), 2.42-2.10 (m, 3H), 2.10-1.68 (m, 8H), 1.54-1.39 (m, 9H), 0.68-0.57 (m, 1H), 0.55-0.39 (m, 2H), 0.24-0.05 (m, 2H).

Example 148. Synthesis of Viral Protease Inhibitor Compound 471

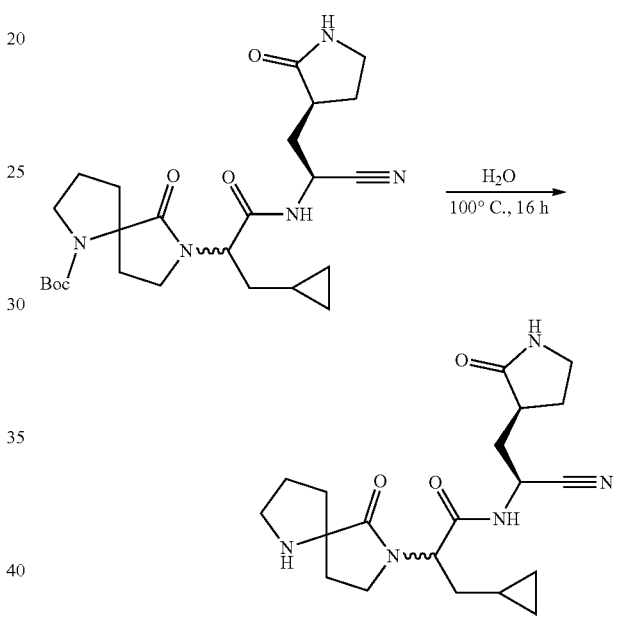

A solution of tert-butyl 7-(1-(((S)-1-cyano-2-((S)-2-oxopyrrolidin-3-yl)ethyl)amino)-3-cyclopropyl-1-oxopropan-2-yl)-6-oxo-1,7-diazaspiro[4.4]nonane-1-carboxylate (90 mg, 0.18 mmol, 1 eq) in H$_2$O (4 mL) was stirred at 100° C. for 16 hr. The reaction mixture was concentrated under reduced pressure to give a residue. The residue was purified by prep-HPLC (column: Phenomenex Gemini-NX 80*30 mm*3 um; mobile phase: [water (0.05% NH$_3$H$_2$O+10 mM NH$_4$HCO$_3$)-ACN]; B %: 11%-41%, 9.5 min) to give N-[(1S)-1-cyano-2-[(3S)-2-oxopyrrolidin-3-yl]ethyl]-3-cyclopropyl-2-(6-oxo-1,7-diazaspiro[4.4]nonan-7-yl)propanamide (2.41 mg, 6.10 umol, 3% yield, 98% purity) as a white solid.

LCMS: Rt=0.603 min; for C$_{20}$H$_{29}$N$_5$O$_3$ MS Calcd.: 387.23; MS Found: 388.1 [M+H$^+$].

$^1$H NMR (400 MHz, CD$_3$OD) δ 5.01 (dd, J=6.3, 9.8 Hz, 1H), 4.55 (s, 1H), 3.57-3.47 (m, 2H), 3.37-3.32 (m, 2H), 3.18-3.08 (m, 1H), 2.99-2.87 (m, 1H), 2.61-2.48 (m, 1H), 2.34-2.24 (m, 2H), 2.13-2.00 (m, 2H), 1.93-1.80 (m, 7H), 1.65-1.56 (m, 1H), 0.75-0.63 (m, 1H), 0.56-0.45 (m, 2H), 0.17 (d, J=3.5 Hz, 2H).

Example 149. Synthesis of Viral Protease Inhibitor Compound 473

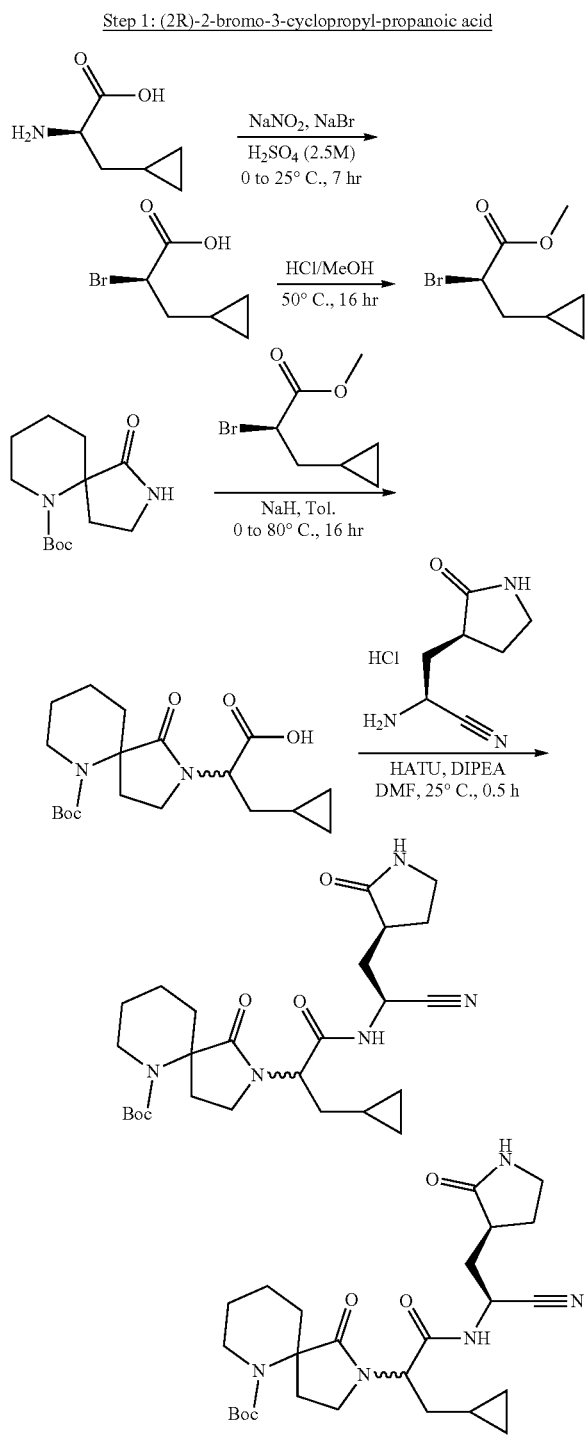

Step 1: (2R)-2-bromo-3-cyclopropyl-propanoic acid

To a solution of (2R)-2-amino-3-cyclopropyl-propanoic acid (3.5 g, 27.10 mmol, 1 eq) and NaBr (9.76 g, 94.85 mmol, 3.05 mL, 3.5 eq) in a 2.5 M solution of $H_2SO_4$ (35 mL) was added $NaNO_2$ (2.43 g, 35.23 mmol, 1.3 eq) in $H_2O$ (7 mL) dropwise at 0° C. The reaction mixture was stirred at 0° C. for 1 h and 25° C. for 6 h. The mixture was diluted with water (60 mL) and the resultant mixture was extracted with DCM (80 mL*3). The combined organic layers were dried over $Na_2SO_4$, filtered and concentrated to dryness under reduced pressure to give (2R)-2-bromo-3-cyclopropyl-propanoic acid (7.4 g, crude) as colorless oil.

$^1$H NMR (400 MHz, $CDCl_3$) δ 4.33 (t, J=7.4 Hz, 1H), 1.99 (dt, J=2.1, 7.1 Hz, 2H), 0.91-0.79 (m, 1H), 0.58-0.51 (m, 2H), 0.22-0.15 (m, 2H).

Step 2: Methyl (2R)-2-bromo-3-cyclopropyl-propanoate

To a solution of (2R)-2-bromo-3-cyclopropyl-propanoic acid (7.4 g, 38.33 mmol, 1 eq) in MeOH (70 mL) was added HCl (12 M, 7.40 mL, 2.32 eq), and then the reaction mixture was stirred at 50° C. for 16 h. TLC (Petroleum ether:Ethyl acetate=10:1, PMA) showed the starting material was consumed. The reaction mixture was concentrated under reduced pressure. The mixture was diluted with water (10 mL) and the resultant mixture was extracted with ethyl acetate (30 mL*3). The combined organic layers were dried over $Na_2SO_4$, filtered and concentrated to dryness under reduced pressure. The residue was purified by column chromatography over silica gel (petroleum ether:ethyl acetate=1:0 to 10:1) to afford methyl (2R)-2-bromo-3-cyclopropyl-propanoate (4.9 g, 59.2% yield) as colorless oil.

$^1$H NMR (400 MHz, $CDCl_3$) δ 4.31 (t, J=7.4 Hz, 1H), 3.80 (s, 3H), 2.00-1.94 (m, 2H), 0.86-0.75 (m, 1H), 0.57-0.44 (m, 2H), 0.22-0.09 (m, 2H).

Step 3: 2-(6-tert-butoxycarbonyl-1-oxo-2,6-diazaspiro[4.5]decan-2-yl)-3-cyclopropyl-propanoic acid To a solution of tert-butyl 1-oxo-2,6-diazaspiro[4.5]decane-6-carboxylate (500 mg, 1.97 mmol, 1 eq) in Toluene (10 mL) was added NaH (94.37 mg, 2.36 mmol, 60% purity, 1.2 eq) at 0° C., and then the mixture was stirred for 0.5 h at 25° C. The reaction mixture was cooled to 0° C. Methyl (2R)-2-bromo-3-cyclopropyl-propanoate (488.5 mg, 2.36 mmol, 1.2 eq) was added, and the reaction mixture was allowed to warm up to 80° C. and stirred for 16 h at 80° C. LC-MS showed starting material was consumed completely and one main peak with desired MS was detected. TLC (petroleum ether:ethyl acetate=1:1, PMA) showed the starting material was consumed. The reaction mixture was concentrated under reduced pressure. The mixture was diluted with water (10 mL) and the resultant mixture was extracted with ethyl acetate (30 mL*3). The combined organic layers were dried over $Na_2SO_4$, filtered and concentrated to dryness under reduced pressure to give tert-butyl 2-[1-(cyclopropylmethyl)-2-methoxy-2-oxo-ethyl]-1-oxo-2,6-diazaspiro[4.5]decane-6-carboxylate (480 mg, crude) as light yellow oil. The aqueous was acidified with HCl (0.5 N) to pH=5, and the resultant mixture was extracted with ethyl acetate (20 mL*3). The combined organic layers were dried over $Na_2SO_4$, filtered and concentrated to dryness under reduced pressure to give 2-(6-tert-butoxycarbonyl-1-oxo-2,6-diazaspiro[4.5]decan-2-yl)-3-cyclopropyl-propanoic acid (120 mg, crude) as light yellow oil.

Isomer 1: tert-butyl 2-[2-[[(1S)-1-cyano-2-[(3S)-2-oxopyrrolidin-3-yl]ethyl]amino]-1-(cyclopropylmethyl)-2-oxo-ethyl]-1-oxo-2,6-diazaspiro[4.5]decane-6-carboxylate; Isomer 2: tert-butyl 2-[2-[[(1S)-1-cyano-2-[(3S)-2-oxopyrrolidin-3-yl]ethyl]amino]-1-(cyclopropylmethyl)-2-oxo-ethyl]-1-oxo-2,6-diazaspiro[4.5]decane-6-carboxylate To a solution of 2-(6-(tert-butoxycarbonyl)-1-oxo-2,6-diazaspiro[4.5]decan-2-yl)-3-cyclopropylpropanoic acid (0.1 g, 0.27 mmol, 1 eq) in DMF (1 mL) was added HATU (207.5 mg, 0.54 mmol, 2.0 eq), (S)-2-amino-3-((S)-2-oxopyrrolidin-3-yl)propanenitrile hydrochloride (62.1 mg, 0.32 mmol, 1.2 eq, HCl) and DIPEA (52.9 mg, 0.40 mmol, 71.3 uL, 1.5 eq). The mixture was stirred at 25° C. for 0.5 h. The reaction mixture was concentrated under reduced pressure to give a residue. The residue was purified by prep-HPLC (column: Phenomenex Gemini-NX 80*30 mm*3 um; mobile phase: [water (0.05% NH$_3$H$_2$O+10 mM NH$_4$HCO$_3$)-ACN]; B %: 27%-57%, 9.5 min) to give Isomer 1 (18.9 mg, 13% yield) and Isomer 2 (2.54 mg, 1.8% yield) as two white solids.

Isomer 1: LCMS: Rt=0.831 min; for C$_{26}$H$_{39}$N$_5$O$_5$ MS Calcd.: 501.30; MS Found: 502.2 [M+H$^+$]. $^1$H NMR (400 MHz, CD$_3$OD) δ 5.20-5.01 (m, 1H), 4.81-4.68 (m, 1H), 3.90 (td, J=4.6, 8.6 Hz, 1H), 3.59-3.40 (m, 1H), 3.34 (d, J=3.3 Hz, 3H), 3.07-2.85 (m, 1H), 2.64-2.45 (m, 1H), 2.45-2.22 (m, 3H), 2.21-2.07 (m, 1H), 2.05-1.92 (m, 1H), 1.90-1.62 (m, 7H), 1.57 (d, J=10.5 Hz, 2H), 1.51-1.39 (m, 9H), 0.81-0.57 (m, 1H), 0.55-0.33 (m, 2H), 0.22-0.04 (m, 2H).

Isomer 2: LCMS: Rt=0.845 min; for C$_{26}$H$_{39}$N$_5$O$_5$ MS Calcd.: 501.30; MS Found: 502.2 [M+H$^+$]. $^1$H NMR (400 MHz, CD$_3$OD) δ 5.28-5.14 (m, 1H), 5.28-5.14 (m, 1H), 4.77 (t, J=7.7 Hz, 1H), 3.93 (br d, J=13.1 Hz, 1H), 3.51-3.38 (m, 1H), 3.35-3.31 (m, 1H), 3.35-3.31 (m, 2H), 3.06-2.92 (m, 1H), 2.61-2.48 (m, 1H), 2.45-2.22 (m, 3H), 2.19-2.08 (m, 1H), 1.97 (td, J=8.2, 13.7 Hz, 1H), 1.89-1.65 (m, 7H), 1.64-1.52 (m, 2H), 1.49 (s, 9H), 0.64-0.54 (m, 1H), 0.53-0.30 (m, 2H), 0.22-0.00 (m, 2H).

Example 150. Synthesis of Viral Protease Inhibitor Compound 475

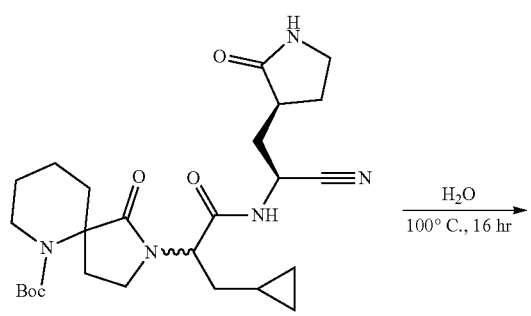

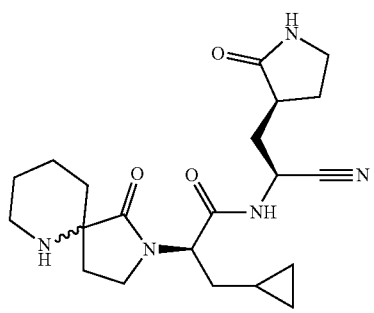

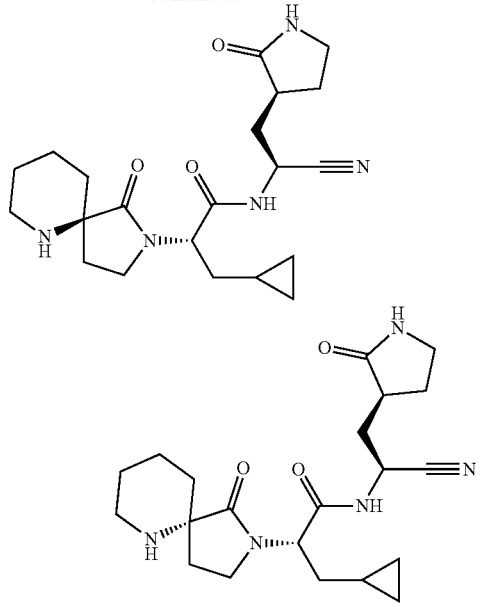

Isomer 1 & Isomer 2: (2R)-N-[(1S)-1-cyano-2-[(3S)-2-oxopyrrolidin-3-yl]ethyl]-3-cyclopropyl-2-(1-oxo-2,6-diazaspiro[4.5]decan-2-yl)propenamide; Isomer 3: (2S)-N-[(1S)-1-cyano-2-[(3S)-2-oxopyrrolidin-3-yl]ethyl]-3-cyclopropyl-2-[(5R)-1-oxo-2,6-diazaspiro[4.5]decan-2-yl]propenamide; Isomer 4: (2S)-N-[(1S)-1-cyano-2-[(3S)-2-oxopyrrolidin-3-yl]ethyl]-3-cyclopropyl-2-[(5S)-1-oxo-2,6-diazaspiro[4.5]decan-2-yl]propanamide A solution of tert-butyl 2-(1-(((S)-1-cyano-2-((S)-2-oxopyrrolidin-3-yl)ethyl)amino)-3-cyclopropyl-1-oxopropan-2-yl)-1-oxo-2,6-diazaspiro[4.5]decane-6-carboxylate (0.15 g, 0.29 mmol, 1 eq) in H$_2$O (5 mL) was stirred at 100° C. for 16 h. The reaction mixture was concentrated under reduced pressure to give a residue. The residue was purified by prep-HPLC (column: Phenomenex Gemini-NX 80*30 mm*3 um; mobile phase: [water (0.05% NH$_3$H$_2$O+10 mM NH$_4$HCO$_3$)-ACN]; B %: 1%-31%, 9.5 min) to give 475 Isomer 1 & Isomer 2 (6.00 mg, 5% yield) and 475 Isomer 3 & Isomer 4 (24.65 mg) as two white solids. 475 Isomer 3 & Isomer 4 was purified by prep-SFC (column: DAICEL CHIRALPAK AD (250 mm*30 mm, 10 um); mobile phase: [0.1% NH$_3$H$_2$O ETOH]; B %: 40%-40%, min) to give 475 Isomer 3 (5.53 mg, 4% yield) and 475 Isomer 4 (4.84 mg, 3% yield) as two white solids.

475 Isomer 1 & Isomer 2: LCMS: Rt=1.232 min; for C$_{21}$H$_{31}$N$_5$O$_3$ MS Calcd.: 401.24; MS Found: 402.1 [M+H$^+$]. $^1$H NMR (400 MHz, CD$_3$OD) δ 5.04-4.92 (m, 1H), 4.67-4.60 (m, 1H), 3.73-3.39 (m, 2H), 3.37-3.32 (m, 2H), 3.15-3.00 (m, 1H), 2.88 (d, J=6.5 Hz, 1H), 2.62-2.42 (m, 1H), 2.40-2.15 (m, 6H), 2.11-1.76 (m, 8H), 1.68-1.51 (m, 1H), 0.75-0.57 (m, 1H), 0.57-0.39 (m, 2H), 0.23-0.11 (m, 2H).

Isomer 3: LCMS: Rt=1.332 min; for C$_{21}$H$_{31}$N$_5$O$_3$ MS Calcd.: 401.24; MS Found: 402.2 [M+H$^+$]. $^1$H NMR (400 MHz, CD$_3$OD) δ 4.90-4.82 (m, 1H), 4.47 (dd, J=6.5, 9.0 Hz, 1H), 3.46-3.34 (m, 1H), 3.31-3.23 (m, 1H), 3.20-3.15 (m, 3H), 3.02-2.89 (m, 1H), 2.64-2.48 (m, 1H), 2.43-2.32 (m, 1H), 2.27-2.01 (m, 3H), 1.92-1.65 (m, 5H), 1.55-1.39 (m, 5H), 0.53-0.41 (m, 1H), 0.39-0.23 (m, 2H), 0.07-0.08 (m, 2H).

Isomer 4: LCMS: Rt=1.329 min; for C$_{21}$H$_{31}$N$_5$O$_3$ MS Calcd.: 401.24; MS Found: 402.2 [M+H$^+$]. $^1$H NMR (400

MHz, CD$_3$OD) δ 4.96 (d, J=3.0 Hz, 1H), 4.66 (dd, J=6.0, 9.5 Hz, 1H), 3.65-3.56 (m, 1H), 3.49-3.40 (m, 1H), 3.37-3.32 (m, 3H), 3.20-3.09 (m, 1H), 2.82-2.69 (m, 1H), 2.50 (td, J=8.1, 16.3 Hz, 1H), 2.41-2.31 (m, 2H), 2.25 (ddd, J=6.3, 9.5, 13.9 Hz, 1H), 2.10 (td, J=9.0, 12.6 Hz, 1H), 2.01-1.79 (m, 4H), 1.71-1.57 (m, 5H), 0.65-0.55 (m, 1H), 0.54-0.37 (m, 2H), 0.21-0.08 (m, 2H).

Example 151. Synthesis of Viral Protease Inhibitor Compound 477

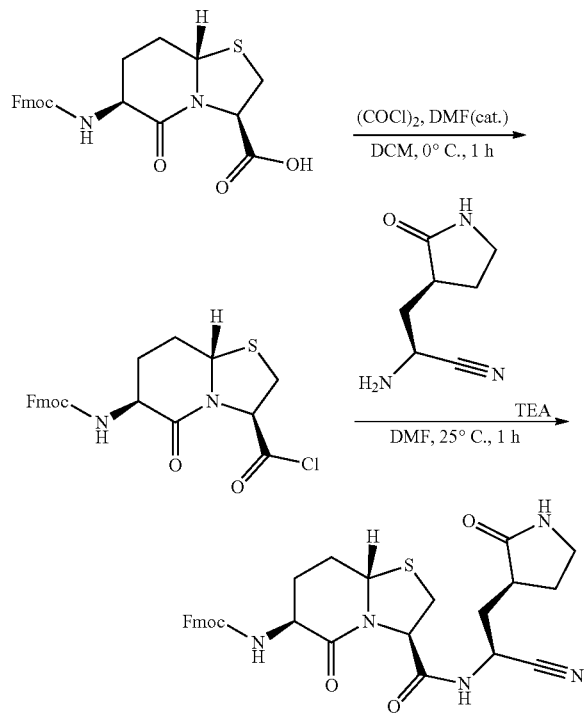

Step 1: (9H-fluoren-9-yl)methyl((3S,6S,8aS)-3-(chlorocarbonyl)-5-oxohexahydro-2H-thiazolo[3,2-a]pyridin-6-yl)carbamate To a solution of (3R,6S)-6-(9H-fluoren-9-ylmethoxycarbonylamino)-5-oxo-2,3,6,7,8,8a-hexahydrothiazolo[3,2-a]pyridine-3-carboxylic acid (200 mg, 0.45 mmol, 1 eq) in DCM (4 mL) was added (COCl)$_2$ (86.8 mg, 0.68 mmol, 59 uL, 1.5 eq) and DMF (3.3 mg, 45.6 umol, 3 uL, 0.1 eq) at 0° C. under N$_2$. The mixture was stirred at 0° C. for 1 hr. The reaction mixture was concentrated under reduced pressure to give a residue. It was used into next step without purification. Compound 9H-fluoren-9-ylmethylN-[(3S,6S)-3-chlorocarbonyl-5-oxo-2,3,6,7,8,8a-hexahydrothiazolo[3,2-a]pyridin-6-yl]carbamate (200 mg, crude) was obtained as a yellow solid.

(9H-fluoren-9-yl)methyl((3R,6S,8aS)-3-(((S)-1-cyano-2-((S)-2-oxopyrrolidin-3-yl)ethyl)carbamoyl)-5-oxohexahydro-2H-thiazolo[3,2-a]pyridin-6-yl)carbamate To a solution of 9H-fluoren-9-ylmethyl N-[(3S,6S)-3-chlorocarbonyl-5-oxo-2,3,6,7,8,8a-hexahydrothiazolo[3,2-a]pyridin-6-yl]carbamate (200 mg, 0.43 mmol, 1 eq) in DMF (5 mL) was added TEA (132.8 mg, 1.31 mmol, 0.18 mL, 3 eq) and (2S)-2-amino-3-[(3S)-2-oxopyrrolidin-3-yl]propanenitrile (99.6 mg, 0.52 mmol, 1.2 eq, HCl). The mixture was stirred at 25° C. for 1 hr. TLC (petroleum ether/ethyl acetate=0:1, UV 254). The reaction mixture was added with H$_2$O (10 mL) and extracted with ethyl acetate (30 mL*3). The combined organic layers were washed with brine (20 mL), dried with anhydrous Na$_2$SO$_4$, filtered and concentrated under reduced pressure to give a residue. The residue was purified by flash silica gel chromatography (ISCO®; 4 g SepaFlash® Silica Flash Column, Eluent of 0~100% ethyl acetate/petroleum ethergradient @ 30 mL/min) to give a yellow solid. The residue purified by prep-HPLC (column: 3_Phenomenex Luna C18 75*30 mm*3 um; mobile phase: [water(0.05% HCl)-ACN]; B %: 30%-60%, 8.5 min). Compound 9H-fluoren-9-ylmethyl N-[(3R,6S)-3-[[(1S)-1-cyano-2-[(3S)-2-oxopyrrolidin-3-yl]ethyl]carbamoyl]-5-oxo-2,3,6,7,8,8a-hexahydrothiazolo[3,2-a]pyridin-6-yl]carbamate (10.63 mg, 18.4 umol, 4.2% yield, 99.7% purity) was obtained as a white solid. LCMS: R$^t$=0.834 min; for C$_{30}$H$_{31}$N$_5$O$_5$S MS Calcd.: 573.66; MS Found: 574.2 [M+H$^+$].

$^1$H NMR (400 MHz, CD$_3$OD) δ 7.82 (d, J=7.53 Hz, 2H), 7.65-7.72 (m, 2H), 7.37-7.45 (m, 2H), 7.29-7.36 (m, 2H), 5.02-5.11 (m, 3H), 4.43 (d, J=6.78 Hz, 2H), 4.23-4.30 (m, 1H), 4.01 (br dd, J=11.29, 6.78 Hz, 1H), 3.42 (dd, J=11.54, 7.78 Hz, 1H), 3.19-3.30 (m, 3H), 2.52-2.65 (m, 1H), 2.17-2.43 (m, 4H), 2.03-2.13 (m, 1H), 1.84-1.97 (m, 2H), 1.73-1.83 (m, 1H).

Example 152. Synthesis of Viral Protease Inhibitor Compound 479

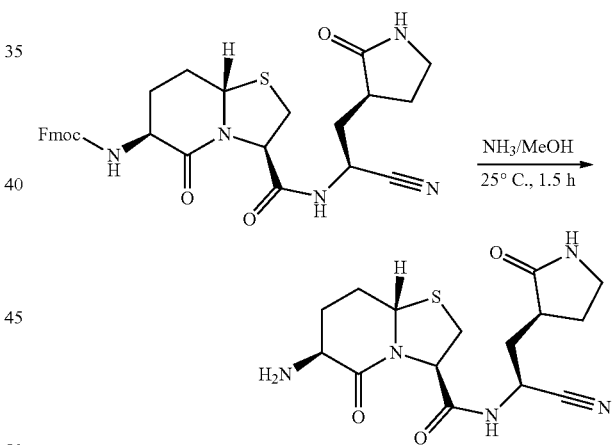

To a solution of 9H-fluoren-9-ylmethyl N-[(3R,6S)-3-[[(1S)-1-cyano-2-[(3S)-2-oxopyrrolidin-3-yl]ethyl]carbamoyl]-5-oxo-2,3,6,7,8,8a-hexahydrothiazolo[3,2-a]pyridin-6-yl]carbamate (100 mg, 0.17 mmol, 1 eq) in MeOH (0.1 mL) was added NH$_3$ (7 M, 2.00 mL, 80.31 eq). The mixture was stirred at 25° C. for 1.5 h. The reaction mixture was added H$_2$O (10 mL) and extracted with ethyl acetate (10 mL*3). The aqueous phase were concentrated under reduced pressure to give a residue. The residue was purified by prep-HPLC (column: Phenomenex Gemini-NX 80*30 mm*3 um; mobile phase: [water(0.05% NH$_3$H$_2$O+10 mM NH$_4$HCO$_3$)-ACN]; B %: 0%-23%, 7.8 min). Compound (3R,6S)-6-amino-N-[(1S)-1-cyano-2-[(3S)-2-oxopyrrolidin-3-yl]ethyl]-5-oxo-2,3,6,7,8,8a-hexahydrothiazolo[3,2-a]pyridine-3-carboxamide (16.59 mg, 47.2 umol, 27.0% yield, 100% purity) was obtained as a white solid.

LCMS: Rt=1.495 min; for $C_{15}H_{21}N_5O_3S$ MS Calcd.: 351.42; MS Found: 352.1 [M+H$^+$].

$^1$H NMR (400 MHz, CD$_3$OD) δ ppm 4.99 (br dd, J=10.63, 5.63 Hz, 3H), 3.33-3.45 (m, 4H), 3.14-3.25 (m, 1H), 2.58-2.71 (m, 1H), 2.19-2.44 (m, 4H), 1.75-2.00 (m, 4H).

Example 153. Synthesis of Viral Protease Inhibitor Compound 483

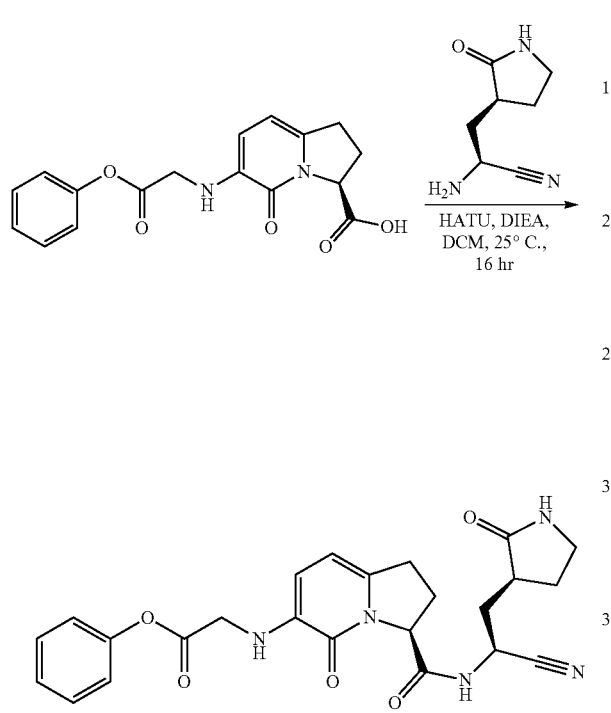

To a solution of (3S)-5-oxo-6-[(2-oxo-2-phenoxy-ethyl) amino]-2,3-dihydro-1H-indolizine-3-carboxylic acid (100 mg, 0.30 mmol, 1 eq) in DCM (3 mL) was added HATU (138.9 mg, 0.36 mmol, 1.2 eq) and DIPEA (118.0 mg, 0.91 mmol, 0.15 mL, 3 eq) for 1 h. Then, (2S)-2-amino-3-[(3S)-2-oxopyrrolidin-3-yl]propanenitrile (55.9 mg, 0.29 mmol, 9.69 e–1 eq, HCl) was added into the mixture, and the resulting mixture was stirred at 25° C. for 15 h. TLC (DCM/MeOH=10:1). The reaction mixture was diluted with H$_2$O (5 mL) and extracted with ethyl acetate (5 mL*3). The combined organic phase was washed with brine (5 mL*3), dried with anhydrous Na$_2$SO$_4$, filtered and concentrated in vacuum. The residue was purified by flash silica gel chromatography (ISCO®; 4 g SepaFlash® Silica Flash Column, Eluent of 0~10% DCM/MeOH ethergradient @ 20 mL/min) to give phenyl 2-[[(3S)-3-[[(1S)-1-cyano-2-[(3S)-2-oxopyrrolidin-3-yl]ethyl]carbamoyl]-5-oxo-2,3-dihydro-1H-indolizin-6-yl]amino]acetate (35 mg, 75.3 umol, 24.7% yield, 99.8% purity) as a white solid.

LCMS: Rt=0.770 min; for $C_{24}H_{25}N_5O_5$ MS Calcd.: 463.19; MS Found: 464.1 [M+H$^+$].

$^1$H NMR (400 MHz, CD$_3$OD) δ 8.03 (br s, 1H), 7.46-7.24 (m, 5H), 6.32 (br d, J=7.6 Hz, 1H), 5.19 (s, 2H), 5.10-4.99 (m, 3H), 3.34 (br d, J=3.3 Hz, 1H), 3.24-3.06 (m, 2H), 2.74-2.63 (m, 1H), 2.62-2.45 (m, 2H), 2.40-2.23 (m, 3H), 1.97-1.80 (m, 2H).

Example 154. Synthesis of Viral Protease Inhibitor Compound 489

Step 1: (1R,2S,6R,7R)-8-trimethylsilyloxy-4-azatricyclo[5.2.2.0$^{2,6}$]undec-8-ene-3,5-dione

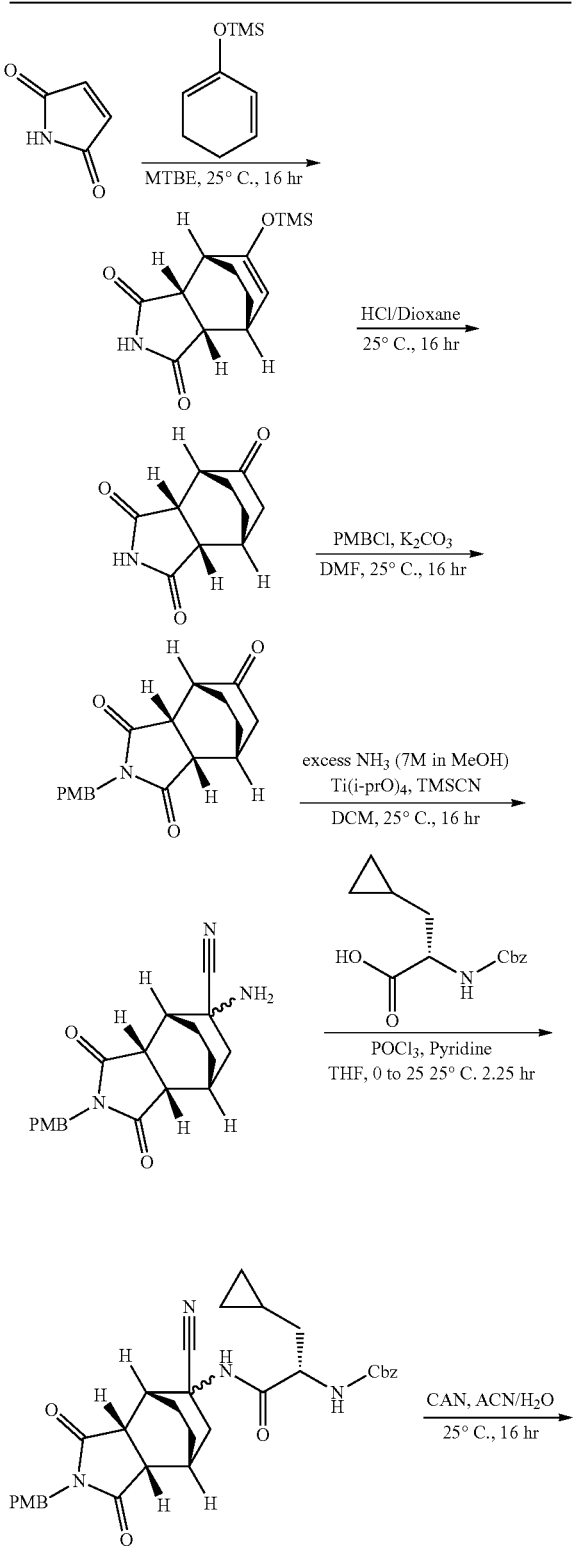

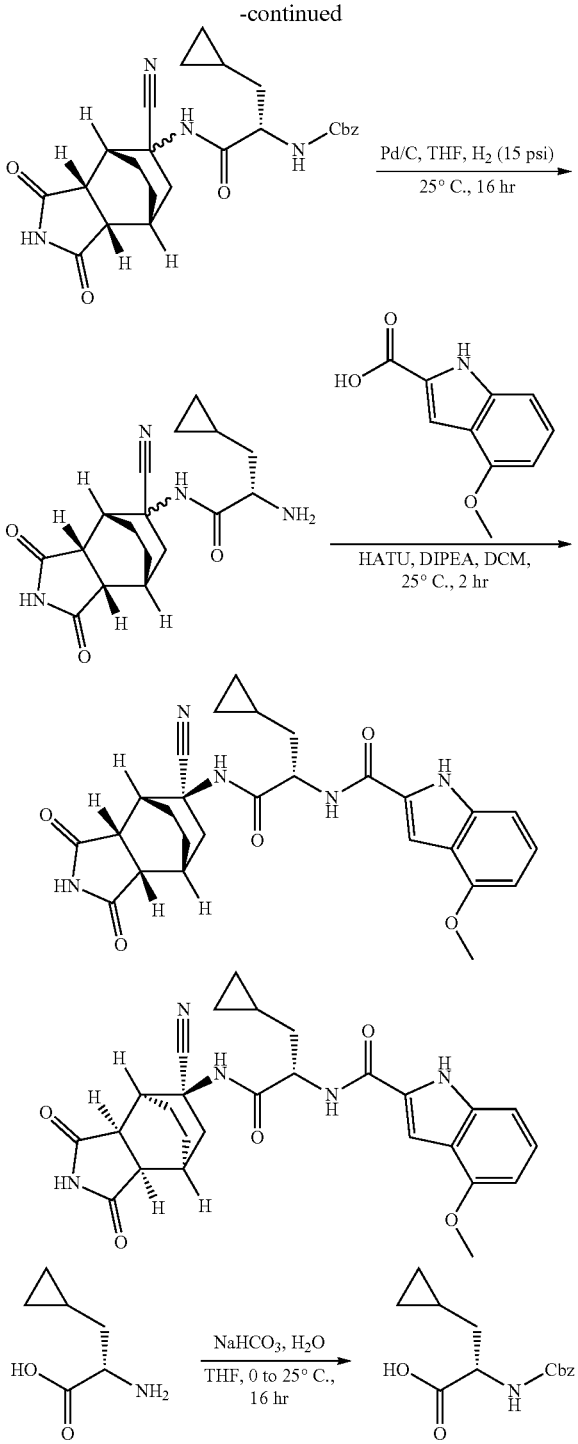

A solution of cyclohexa-1,5-dien-1-yloxy(trimethyl)silane (5.0 g, 29.71 mmol, 5.50 mL, 1 eq) and pyrrole-2,5-dione (2.88 g, 29.71 mmol, 1 eq) in MTBE (50 mL) was stirred at 25° C. for 16 h. TLC (petroleum ether:ethyl acetate=2:1, I₂) was conducted. The reaction mixture was concentrated under reduced pressure. MTBA (15 mL) and PE (15 mL) was added, and then the suspension was filtered to give the title compound as a white solid. Compound (1R,2S,6R,7R)-8-trimethylsilyloxy-4-azatricyclo[5.2.2.0$^{2,6}$]undec-8-ene-3,5-dione (5.2 g, 65.9% yield) was obtained as a white solid Step 2: (1R,2S,6R,7R)-4-azatricyclo[5.2.2.0$^{2,6}$]undecane-3,5,8-trione A solution of (1R,2S,6R,7R)-8-trimethylsilyloxy-4-azatricyclo[5.2.2.0$^{2,6}$]undec-8-ene-3,5-dione (2.9 g, 10.93 mmol, 1 eq) in HCl/dioxane (25 mL) was stirred at 25° C. for 16 hr. TLC (petroleum ether:ethyl acetate=5:1). The reaction mixture was concentrated in vacuum. No purification. The crude product was used into the next step without further purification. Compound (1R,2S,6R,7R)-4-azatricyclo[5.2.2.0$^{2,6}$]undecane-3,5,8-trione (2.16 g, crude) was obtained as a white solid.

Step 3: (1R,2S,6R,7R)-4-[(4-methoxyphenyl)methyl]-4-azatricyclo[5.2.2.0$^{2,6}$]undecane-3,5,8-trione To a solution of (1R,2S,6R,7R)-4-azatricyclo[5.2.2.0$^{2,6}$]undecane-3,5,8-trione (2.1 g, 11.18 mmol, 1 eq) in DMF (20 mL) was added PMBCl (2.1 g, 13.42 mmol, 1.83 mL, 1.2 eq) and K₂CO₃ (2.3 g, 16.77 mmol, 1.5 eq). The mixture was stirred at 25° C. for 16 h. LCMS showed the desired compound was detected. TLC (petroleum ether:ethyl acetate=1:1). The reaction mixture was diluted with H₂O (10 mL) and extracted with ethyl acetate (10 mL*3). The combined organic phase was washed with brine (10 mL*3), dried with anhydrous Na₂SO₄, filtered and concentrated in vacuum. The residue was purified by flash silica gel chromatography (ISCO®; 12 g SepaFlash® Silica Flash Column, Eluent of 0-40% petroleum ether/ethyl acetate ether-gradient @ 25 mL/min). Compound (1R,2S,6R,7R)-4-[(4-methoxyphenyl)methyl]-4-azatricyclo[5.2.2.0$^{2,6}$]undecane-3,5,8-trione (3.03 g, 86.4% yield) was obtained as a white solid.

Step 4: (1R,2S,6R,7R)-8-Amino-4-[(4-methoxyphenyl)methyl]-3,5-dioxo-4-azatricyclo[5.2.2.0$^{2,6}$]undecane-8-carbonitrile To a solution of (1R,2S,6R,7R)-4-[(4-methoxyphenyl)methyl]-4-azatricyclo[5.2.2.0$^{2,6}$]undecane-3,5,8-trione (1.7 g, 5.43 mmol, 1 eq) in DCM (25 mL) were added NH₃ (7 M, 7.75 mL, 10 eq) and Ti(i-PrO)₄ (1.85 g, 6.51 mmol, 1.92 mL, 1.2 eq). The reaction mixture was stirred at 25° C. for 2 hr. TMSCN (807.3 mg, 8.14 mmol, 1.02 mL, 1.5 eq) was added and the solution was stirred at 25° C. for 16 h. Ethyl acetate (100 mL) and H₂O (10 mL) were added, the reaction mixture was filtered, the filtrate was concentrated to reduce pressure. Compound (1R,2S,6R,7R)-8-amino-4-[(4-methoxyphenyl)methyl]-3,5-dioxo-4-azatricyclo[5.2.2.0$^{2,6}$]undecane-8-carbonitrile (1.75 g, crude) was obtained as a white solid.

Step 5: (2S)-2-(benzyloxycarbonylamino)-3-cyclopropyl-propanoic acid

To a solution of (2S)-2-amino-3-cyclopropyl-propanoic acid (3.0 g, 23.23 mmol, 1 eq) in THF (45 mL) was added Na₂CO₃ (2 M, 13.94 mL, 1.2 eq) at 0° C. CbzCl (5.15 g, 30.20 mmol, 4.29 mL, 1.3 eq) was added, and the reaction mixture was stirred at 25° C. for 16 h. The reaction mixture was concentrated under reduced pressure. The mixture was diluted with water (30 mL) and the resultant mixture was extracted with ethyl acetate (50 mL*3). The combined organic layers were dried over Na₂SO₄, filtered and concentrated to dryness under reduced pressure. The residue was purified by column chromatography over silica gel (petroleum ether:ethyl acetate=1:0 to 3:1) to afford (2S)-2-(benzyloxycarbonylamino)-3-cyclopropyl-propanoic acid as a colorless oil. Compound (2S)-2-(benzyloxycarbonylamino)-3-cyclopropyl-propanoic acid (3.2 g, 10.21 mmol, 43.9% yield, 84% purity) was obtained as colorless oil. $^1$H NMR (400 MHz, CD$_3$OD) δ 7.43-7.20 (m, 5H), 5.09 (s, 2H), 4.23 (dd, J=5.5, 8.0 Hz, 1H), 1.73-1.58 (m, 2H), 0.86-0.72 (m, 1H), 0.53-0.39 (m, 2H), 0.20-0.02 (m, 2H).

Step 6: Benzyl N-[(1S)-2-[[(1R,2S,6R,7R)-8-cyano-4-[(4-methoxyphenyl)methyl]-3,5-dioxo-4-azatricyclo[5.2.2.0$^{2,6}$]undecan-8-yl]amino]-1-(cyclopropylmethyl)-2-oxo-ethyl]carbamate A solution of (1R,2S,6R,7R)-8-amino-4-[(4-methoxyphenyl)methyl]-3,5-dioxo-4-azatricyclo[5.2.2.0$^{2,6}$]undecane-8-carbonitrile (1.7 g, 5.01 mmol, 1 eq), (2S)-2-(benzyloxycarbonylamino)-3-cyclopropyl-propanoic acid (1.45 g, 5.51 mmol, 1.1 eq) and pyridine (3.96 g, 50.09 mmol, 4.04 mL, 10 eq) in THF (35 mL) was stirred at 25° C. for 15 min. After POCl$_3$ (1.92 g, 12.52 mmol, 1.16 mL, 2.5 eq) was added dropwise at 0° C., the reaction mixture was stirred at 25° C. for 2 hours. The reaction mixture was concentrated under reduced pressure. The mixture was diluted with water (30 mL) and the resultant mixture was extracted with ethyl acetate (80 mL*3). The combined organic layers were dried over Na$_2$SO$_4$, filtered and concentrated to dryness under reduced pressure. The residue was purified by column chromatography over silica gel (DCM:McOH=1:0 to 20:1) to afford N-[(1S)-2-[[(1R,2S,6R,7R)-8-cyano-4-[(4-methoxyphenyl)methyl]-3,5-dioxo-4-azatricyclo[5.2.2.0$^{2,6}$]undecan-8-yl]amino]-1-(cyclopropylmethyl)-2-oxo-ethyl]carbamate (2.4 g, 72.9% yield, 89% purity) as a colorless oil.

Step 7: Benzyl N-[(1S)-2-[[(1R,2S,6R,7R)-8-cyano-3,5-dioxo-4-azatricyclo[5.2.2.0$^{2,6}$]

To a solution of benzyl N-[(1S)-2-[[(1R,2S,6R,7R)-8-cyano-4-[(4-methoxyphenyl)methyl]-3,5-dioxo-4-azatricyclo[5.2.2.0$^{2,6}$]undecan-8-yl]amino]-1-(cyclopropylmethyl)-2-oxo-ethyl]carbamate (500 mg, 0.85 mmol, 1 eq) in ACN (15 mL) and H$_2$O (5 mL) was added CAN (1.41 g, 2.57 mmol, 1.28 mL, 3 eq), and then the reaction mixture was stirred at 25° C. for 4 h. The reaction mixture was concentrated under reduced pressure. The mixture was diluted with water (30 mL) and the resultant mixture was extracted with ethyl acetate (50 mL*3). The combined organic layers were dried over Na$_2$SO$_4$, filtered and concentrated to dryness under reduced pressure. The residue was purified by column chromatography over silica gel (petroleum ether:ethyl acetate=1:0 to 1:1) to afford benzyl N-[(1S)-2-[[(1R,2S,6R,7R)-8-cyano-3,5-dioxo-4-azatricyclo[5.2.2.0$^{2,6}$]undecan-8-yl]amino]-1-(cyclopropylmethyl)-2-oxo-ethyl]carbamate (260 mg, 62.8% yield, 96% purity) as a white solid.

Step 8: (2S)-2-amino-N-[(1R,2S,6R,7R)-8-cyano-3,5-dioxo-4-azatricyclo[5.2.2.0$^{2,6}$]undecan-8-yl]-3-cyclopropyl-propanamide To a solution of benzyl N-[(1S)-2-[[(1R,2S,6R,7R)-8-cyano-3,5-dioxo-4-azatricyclo[5.2.2.0$^{2,6}$]undecan-8-yl]amino]-1-(cyclopropylmethyl)-2-oxo-ethyl]carbamate (200 mg, 0.43 mmol, 1 eq) in THF (2 mL) was added Pd/C (100 mg, 10% purity) under N$_2$. The suspension was degassed under vacuum and purged with H$_2$ several times. The mixture was stirred under H$_2$ (15 psi) 25° C. for 16 h. The reaction mixture was filtered and the filtrate was concentrated under pressure reduce. Compound (2S)-2-amino-N-[(1R,2S,6R,7R)-8-cyano-3,5-dioxo-4-azatricyclo[5.2.2.0$^{2,6}$]undecan-8-yl]-3-cyclopropyl-propanamide (140 mg, crude) was obtained as colorless oil.

Isomer 1: N-[(1S)-2-[[(1R,2S,6R,7R,8S)-8-Cyano-3,5-dioxo-4-azatricyclo[5.2.2.02,6]undecan-8-yl]amino]-1-(cyclopropylmethyl)-2-oxo-ethyl]-4-methoxy-1H-indole-2-carboxamide; Isomer 2: N-[(1S)-2-[[(1S,2R,6S,7S,8S)-8-Cyano-3,5-dioxo-4-azatricyclo[5.2.2.02,6]undecan-8-yl]amino]-1-(cyclopropylmethyl)-2-oxo-ethyl]-4-methoxy-1H-indole-2-carboxamide To a solution of (2S)-2-amino-N-[(1R,2S,6R,7R)-8-cyano-3,5-dioxo-4-azatricyclo[5.2.2.0$^{2,6}$]undecan-8-yl]-3-cyclopropyl-propanamide (140 mg, 0.42 mmol, 1 eq), 4-methoxy-1H-indole-2-carboxylic acid (81.01 mg, 0.42 mmol, 1 eq) and DIPEA (109.5 mg, 0.84 mmol, 147.62 uL, 2 eq) in DCM (4 mL) was added HATU (193.3 mg, 0.50 mmol, 1.2 eq). The reaction mixture was stirred at 25° C. for 2 h. The reaction mixture was concentrated under reduced pressure. The mixture was diluted with water (10 mL) and the resultant mixture was extracted with DCM (20 mL*3). The combined organic layers were dried over Na$_2$SO$_4$, filtered and concentrated to dryness under reduced pressure. The residue was purified by Pre-TLC (DCM:MeOH=10:1) to give the crude product. The residue was purified by prep-HPLC (column: Phenomenex Gemini-NX 80*40 mm*3 um; mobile phase: [water (0.05% NH$_3$H$_2$O+10 mM NH$_4$HCO$_3$)-ACN]; B %: 23%-53%, 9.5 min) to give Isomer 1 (13.30 mg, 6.0% yield, 97.4% purity) and Isomer 2 (31.40 mg, 14.6% yield, 99.5% purity) as two white solids.

Isomer 1: LCMS: Rt=0.808 min; for C$_{27}$H$_{29}$N$_5$O$_5$ MS Calcd.: 503.22; MS Found: 504.2 [M+H$^+$].

$^1$H NMR (400 MHz, CD$_3$OD) δ 7.28 (s, 1H), 7.18-7.12 (m, 1H), 7.03 (d, J=8.3 Hz, 1H), 6.52 (d, J=7.5 Hz, 1H), 4.56 (dd, J=4.4, 9.9 Hz, 1H), 3.93 (s, 3H), 3.17 (d, J=2.5 Hz, 1H), 3.02-2.97 (m, 1H), 2.96-2.90 (m, 1H), 2.41 (d, J=15.3 Hz, 1H), 2.33 (d, J=2.3 Hz, 1H), 2.22-2.10 (m, 1H), 1.94 (d, J=15.3 Hz, 1H), 1.88-1.63 (m, 5H), 0.90-0.75 (m, 1H), 0.56-0.40 (m, 2H), 0.31-0.13 (m, 2H).

Isomer 2: LCMS: Rt=0.806 min; for C$_{27}$H$_{29}$N$_5$O$_5$ MS Calcd.: 503.22; MS Found: 504.2 [M+H$^+$].

$^1$H NMR (400 MHz, CD$_3$OD) δ 7.25 (s, 1H), 7.18-7.11 (m, 1H), 7.03 (d, J=8.3 Hz, 1H), 6.51 (d, J=7.8 Hz, 1H), 4.64-4.60 (m, 1H), 3.93 (s, 3H), 3.17 (d, J=2.0 Hz, 1H), 3.00-2.93 (m, 1H), 2.92-2.86 (m, 1H), 2.43 (d, J=15.6 Hz, 1H), 2.31 (s, 1H), 2.23-2.11 (m, 1H), 1.94 (d, J=15.6 Hz, 1H), 1.84-1.61 (m, 5H), 0.85-0.70 (m, 1H), 0.55-0.40 (m, 2H), 0.23-0.09 (m, 2H).

Example 155. Synthesis of Viral Protease Inhibitor Compound 491

Step 1: methyl (2S)-2-[[3-cyclopropyl-2-[(4-methoxy-1H-indole-2-carbonyl)amino]propanoyl]amino]-3-[(3S)-2-oxo-3-piperidyl]propanoate

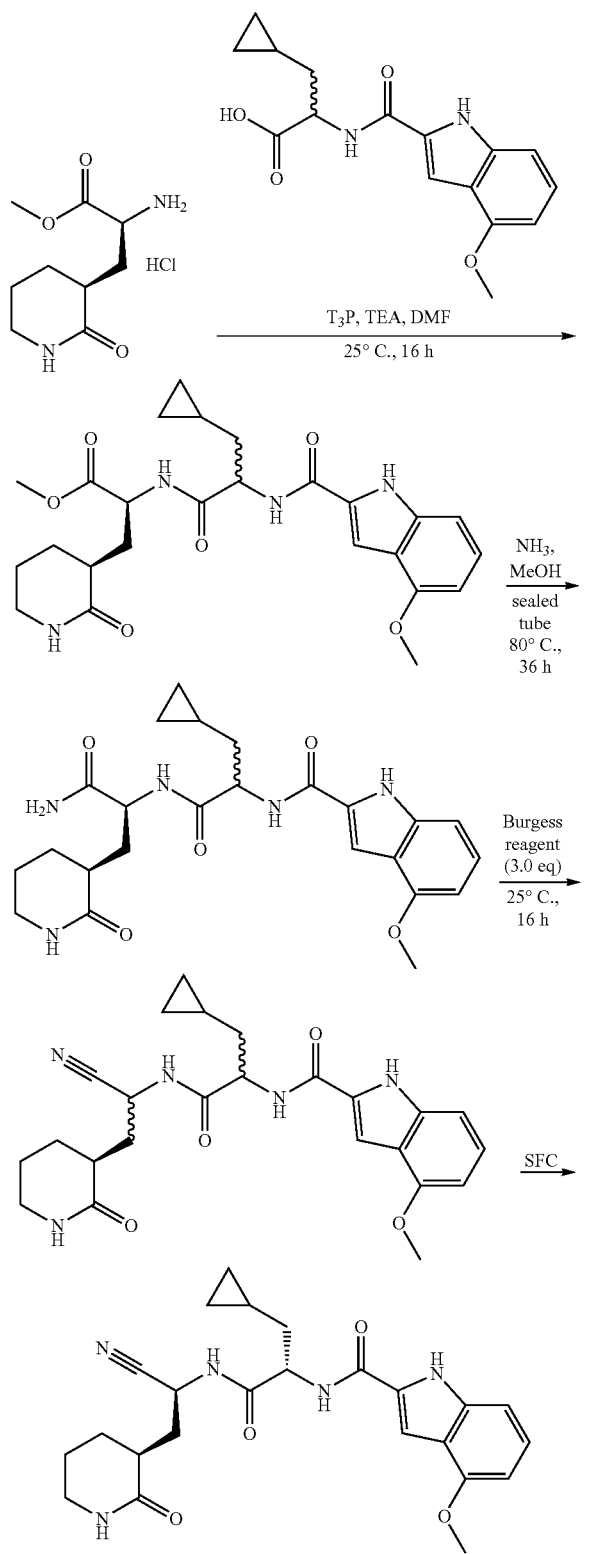

To the mixture of methyl (2S)-2-amino-3-[(3S)-2-oxo-3-piperidyl]propanoate (240 mg, 1.01 mmol, 1 eq, HCl), (2S)-3-cyclopropyl-2-[(4-methoxy-1H-indole-2-carbonyl)amino]propanoic acid (412.2 mg, 1.22 mmol, 1.2 eq, HCl) and TEA (410.4 mg, 4.06 mmol, 0.56 mL, 4 eq) in DMF (3 mL) was added T₃P (1.2 g, 2.03 mmol, 1.21 mL, 50% purity, 2 eq) at 25° C. The mixture was stirred at 25° C. for 16 h. TLC (DCM:MeOH=10:1/UV254 nm). The reaction mixture was diluted with H₂O (10 mL) and the mixture was extracted with ethyl acetate (10 mL*3). The combined organic phase was washed with brine (10 mL*2), dried with anhydrous Na₂SO₄, filtered and concentrated in vacuum. The residue was purified by flash silica gel chromatography (ISCO®; 12 g SepaFlash® Silica Flash Column, Eluent of 100~25% Ethyl acetate/MeOH@ 30 mL/min). Compound methyl (2S)-2-[[(2S)-3-cyclopropyl-2-[(4-methoxy-1H-indole-2-carbonyl)amino]propanoyl]amino]-3-[(3S)-2-oxo-3-piperidyl]propanoate (256 mg, 0.48 mmol, 48.2% yield, 92.5% purity) was obtained as yellow solid.

Step 2: N-[2-[[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-indole-2-carboxamide A mixture of methyl (2S)-2-[[(2S)-3-cyclopropyl-2-[(4-methoxy-1H-indole-2-carbonyl)amino]propanoyl]amino]-3-[(3S)-2-oxo-3-piperidyl]propanoate (246.3 mg, 0.47 mmol, 92.5% purity, 1 eq) in NH₃ (7 M, 6.72 mL, 100 eq) (7M in MeOH) was stirred at 80° C. for 36 h in a sealed tube. The reaction mixture was concentrated in vacuum. Compound N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-indole-2-carboxamide (220 mg, crude) was obtained as yellow solid, which was used into the next step without further purification.

Step 3: N-[2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide A mixture of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-indole-2-carboxamide (250 mg, 0.53 mmol, 1 eq) and methoxycarbonyl-(triethylammonio)sulfonyl-azanide (444.0 mg, 1.86 mmol, 3.5 eq) in DCM (3 mL) was stirred at 25° C. for 16 h. LC-MS showed the desired compound was detected. The reaction mixture was diluted with $H_2O$ (10 mL) and the mixture was extracted with ethyl acetate (10 mL*3). The combined organic phase was washed with brine (10 mL*2), dried with anhydrous $Na_2SO_4$, filtered and concentrated in vacuum. The residue was purified by prep-HPLC (column: Phenomenex Gemini-NX 80*30 mm*3 um; mobile phase: [water (0.05% $NH_3H_2O$+10 mM $NH_4HCO_3$)-ACN]; B %: 23%-53%, 9.5 min). Compound N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide (83 mg, 0.18 mmol, 34.2% yield, 99.0% purity) was obtained as a white solid.

Isomer 1: N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide; Isomer 2: N-[(1S)-2-[[(1R)-1-cyano-2-[(3S)-2-oxo-3-piperidyl]ethyl]amino]-1-(cyclopropylmethyl)-2-oxo-ethyl]-4-methoxy-1H-indole-2-carboxamide; Isomer 3: N-[(1R)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide; Isomer 3: N-[(1R)-2-[[(1R)-1-cyano-2-[(3S)-2-oxo-3-piperidyl]ethyl]amino]-1-(cyclopropylmethyl)-2-oxo-ethyl]-4-methoxy-1H-indole-2-carboxamide N-[2-[[1-cyano-2-[(3S)-2-oxo-3-piperidyl]ethyl]amino]-1-(cyclopropylmethyl)-2-oxo-ethyl]-4-methoxy-1H-indole-2-carboxamide (50 mg, 0.11 mmol, 1 eq) was purified by SFC (column: DAICEL CHIRALPAK AD (250 mm*30 mm, 10 um); mobile phase: [0.1% $NH_3H_2O$ ETOH]; B %: 55%-55%, min) to get three fragments: Isomer 1, mixture of Isomer 2 &3 and Isomer 4.

Isomer 1: N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide (28.1 mg, 62.2 umol, 56.2% yield, 100% purity) was obtained as white solid.

LCMS: Rt=0.755 min; for $C_{24}H_{29}N_5O_4$ MS Calcd.: 451.22, MS Found: 452 [M+H$^+$].

$^1$H NMR (400 MHz, DMSO-d$_6$) δ 11.57 (s, 1H), 8.91 (br d, J=8.0 Hz, 1H), 8.50 (br d, J=7.5 Hz, 1H), 7.53 (br s, 1H), 7.37 (d, J=1.4 Hz, 1H), 7.15-7.06 (m, 1H), 7.04-6.97 (m, 1H), 6.51 (d, J=7.6 Hz, 1H), 5.07 (q, J=8.2 Hz, 1H), 4.49-4.40 (m, 1H), 3.89 (s, 3H), 3.15-3.01 (m, 2H), 2.34-2.20 (m, 2H), 1.91-1.76 (m, 3H), 1.70 (br dd, J=4.4, 8.7 Hz, 1H), 1.64-1.53 (m, 1H), 1.35 (br s, 1H), 0.86-0.76 (m, 1H), 0.48-0.35 (m, 2H), 0.25-0.04 (m, 2H).

Isomer 4: N-[(1R)-2-[[(1R)-1-cyano-2-[(3S)-2-oxo-3-piperidyl]ethyl]amino]-1-(cyclopropylmethyl)-2-oxo-ethyl]-4-methoxy-1H-indole-2-carboxamide (6.1 mg, 13.5 umol, 12.2% yield, 100% purity) was obtained as white solid.

LCMS: Rt=0.752 min; for $C_{24}H_{29}N_5O_4$ MS Calcd.: 451.22, MS Found: 452.2 [M+H$^+$].

$^1$H NMR (400 MHz, CD$_3$OD) δ 7.27 (s, 1H), 7.18-7.12 (m, 1H), 7.03 (d, J=8.4 Hz, 1H), 6.51 (d, J=7.6 Hz, 1H), 5.12 (dd, J=6.4, 7.7 Hz, 1H), 4.85 (br s, 1H), 3.93 (s, 3H), 3.24-3.16 (m, 2H), 2.50-2.32 (m, 2H), 2.06-1.92 (m, 2H), 1.92-1.82 (m, 2H), 1.70 (dt, J 7.0, 14.2 Hz, 2H), 1.63-1.54 (m, 1H), 1.31-1.31 (m, 1H), 1.41-1.27 (m, 1H), 0.91-0.80 (m, 1H), 0.53 (br d, J=8.0 Hz, 2H), 0.25-0.14 (m, 2H).

The mixture of Isomer 2 & Isomer 3 (20.0 mg, 44.3 umol, 1 eq) was purified by SFC (column: DAICEL CHIRALCEL OD-H (250 mm*30 mm, 5 um); mobile phase: [0.1% $NH_3H_2O$ ETOH]; B %: 45%-45%, min) to get two fragments.

Isomer 3: N-[(1R)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide (5.1 mg, 11.3 umol, 25.6% yield, 100% purity) was obtained as white solid.

LCMS: Rt=0.754 min; for $C_{24}H_{29}N_5O_4$ MS Calcd: 451.22, MS Found: 452.1 [M+H$^+$].

$^1$H NMR (400 MHz, CD$_3$OD) δ 7.28 (s, 1H), 7.18-7.12 (m, 1H), 7.03 (d, J=8.3 Hz, 1H), 6.52 (d, J=7.5 Hz, 1H), 5.06 (dd, J=6.5, 9.8 Hz, 1H), 4.81 (br s, 1H), 3.93 (s, 3H), 3.18 (br s, 2H), 2.43-2.35 (m, 1H), 2.45-2.27 (m, 1H), 2.31 (br s, 1H), 2.06-1.95 (m, 1H), 1.94-1.78 (m, 3H), 1.76-1.59 (m, 2H), 1.58-1.45 (m, 1H), 1.40 (s, 1H), 1.29 (s, 1H), 0.92-0.79 (m, 1H), 0.58-0.44 (m, 2H), 0.26-0.12 (m, 2H).

Isomer 2: N-[(1S)-2-[[(1R)-1-cyano-2-[(3S)-2-oxo-3-piperidyl]ethyl]amino]-1-(cyclopropylmethyl)-2-oxo-ethyl]-4-methoxy-1H-indole-2-carboxamide (6.3 mg, 14.0 umol, 31.6% yield, 100% purity) was obtained white solid.

LCMS: Rt=0.754 min; for $C_{24}H_{29}N_5O_4$ MS Calcd: 451.22, MS Found: 452.1 [M+H$^+$].

$^1$H NMR (400 MHz, CD$_3$OD) δ 7.12 (s, 1H), 7.01-6.96 (m, 1H), 6.87 (d, J=8.3 Hz, 1H), 6.35 (d, J=7.8 Hz, 1H), 4.89 (t, J=7.2 Hz, 1H), 4.43 (dd, J=6.3, 8.3 Hz, 2H), 3.77 (s, 3H), 3.08-3.00 (m, 2H), 2.32-2.22 (m, 1H), 2.20-2.10 (m, 1H), 2.27-2.07 (m, 1H), 1.84-1.73 (m, 2H), 1.72-1.62 (m, 2H), 1.60-1.50 (m, 2H), 1.43-1.34 (m, 1H), 0.75-0.62 (m, 1H), 0.40-0.27 (m, 2H), 0.08-0.04 (m, 2H).

Example 156. Synthesis of Viral Protease Inhibitor Compound 493

Step 1: Methyl (2R)-2-(benzyloxycarbonylamino)-3-bromo-propanoate

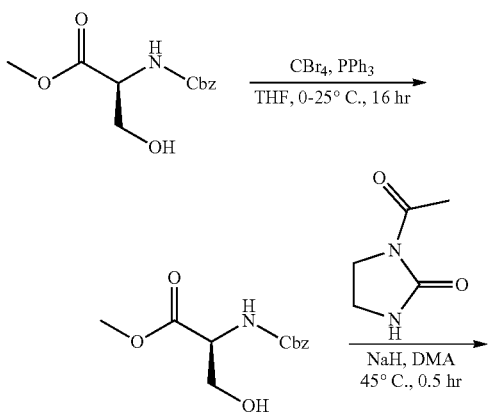

1133
-continued

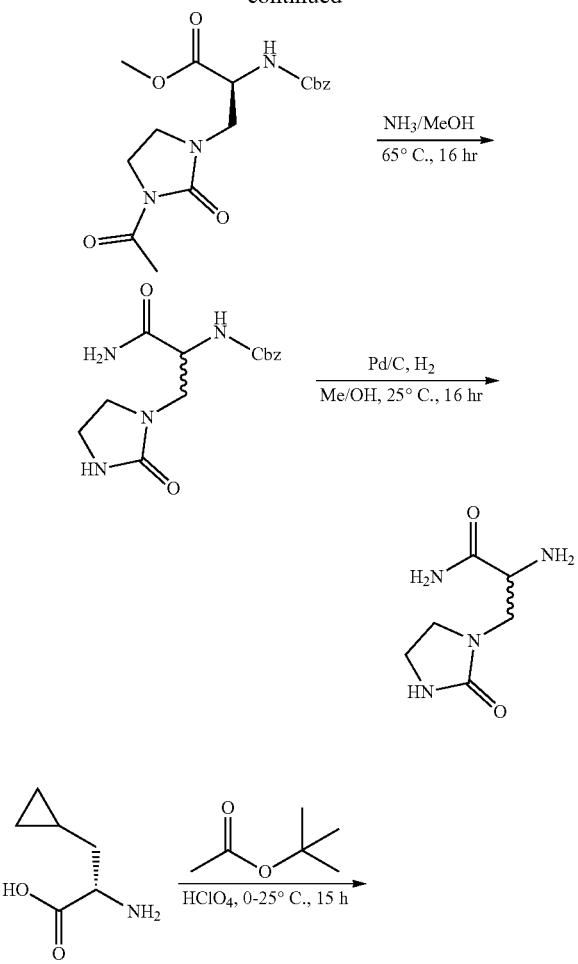

NH₃/MeOH
65° C., 16 hr

Pd/C, H₂
Me/OH, 25° C., 16 hr

HClO₄, 0-25° C., 15 h

EDCl, HOBt,
DCM, 25° C., 16 h

TFA/DCM = 5/1
25° C., 1 h

1134
-continued

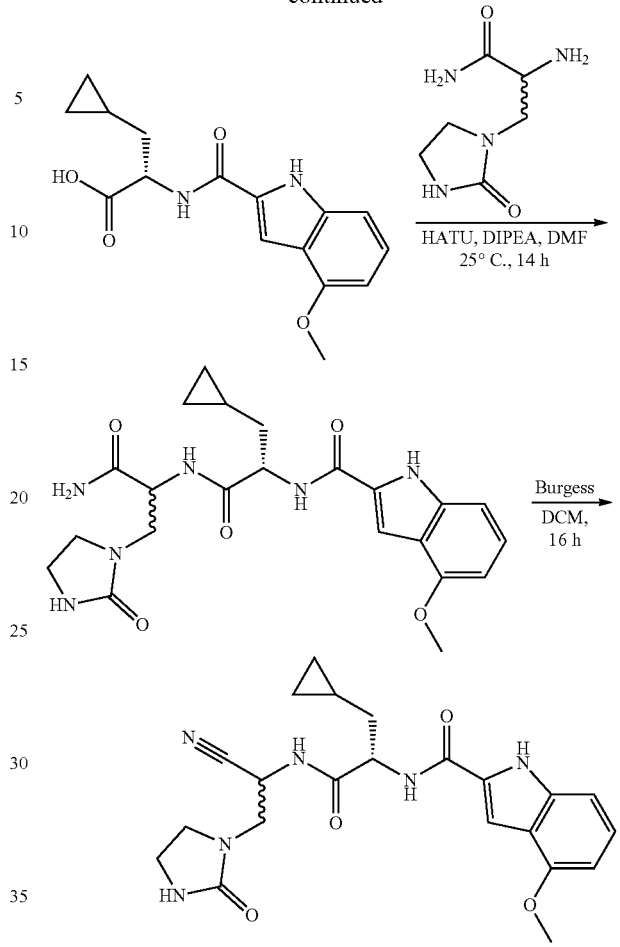

HATU, DIPEA, DMF
25° C., 14 h

Burgess
DCM,
16 h

To a solution of methyl (2S)-2-(benzyloxycarbonylamino)-3-hydroxy-propanoate (10 g, 39.49 mmol, 1 eq) and CBr₄ (15.7 g, 47.38 mmol, 1.2 eq) in THF (120 mL) was added PPh₃ (12.4 g, 47.38 mmol, 1.2 eq) in THF (20 mL) at 0° C. Then the mixture was stirred at 25° C. for 16 hr. TLC (petroleum ether/ethyl acetate=5/1, I₂). The reaction mixture was filtered and the filtrate was concentrated in vacuum. The residue was purified by flash silica gel chromatography (ISCO®; 25 g SepaFlash® Silica Flash Column, Eluent of 0~20% Ethylacetate/Petroleum ethergradient @ 30 mL/min) to give methyl (2R)-2-(benzyloxycarbonylamino)-3-bromo-propanoate (8.2 g, 65.6% yield) as a white solid.

Step 2: methyl (2S)-3-(3-acetyl-2-oxo-imidazolidin-1-yl)-2-(benzyloxycarbonylamino) propanoate To a solution of 1-acetylimidazolidin-2-one (1.3 g, 10.31 mmol, 1 eq) in DMA (10 mL) was added NaH (618.6 mg, 15.47 mmol, 60% purity, 1.5 eq) at 25° C. and the mixture was stirred at 45° C. for 15 min. Then methyl (2R)-2-(benzyloxycarbonylamino)-3-bromo-propanoate (3.2 g, 10.31 mmol, 1 eq) in DMA (30 mL) was added to the mixture at 45° C. and the resulting mixture was stirred at 45° C. for 15 min. LC-MS showed the desired compound was detected. TLC (petroleum ether:ethyl acetate=0:1) showed new spot was detected. The reaction mixture was diluted with H₂O (20 mL) and extracted with ethyl acetate (20 mL*3). The combined organic phase was washed with brine (10 mL*3), dried with anhydrous Na₂SO₄, filtered and concentrated in vacuum. The residue was purified by flash silica gel chromatography (ISCO®; 20 g SepaFlash® Silica Flash Column, Eluent of 0-80% petroleum ether/ethyl acetate ethergradient @ 30 mL/min). Compound methyl (2S)-3-(3-acetyl-2-oxo-imidazolidin-1-yl)-2-(benzyloxycarbonylamino)propanoate (1.5 g, 40.0% yield) was obtained as yellow oil.

Step 3: benzyl N-[2-amino-2-oxo-1-[(2-oxoimidazolidin-1-yl)methyl]ethyl]carbamate A solution of methyl 3-(3-acetyl-2-oxo-imidazolidin-1-yl)-2-(benzyloxycarbonylamino)propanoate (2.0 g, 5.50 mmol, 1 eq) in ammonia (7 M, 14.94 mL, 19 eq) was stirred at 65° C. for 16 hr. TLC (DCM:MeOH=10:1). The reaction mixture was filtered and concentrated in vacuum. The residue was purified by flash silica gel chromatography (ISCO®; 25 g SepaFlash® Silica Flash Column, Eluent of 0-30% DCM/MeOH ethergradient @30 mL/min). Compound benzyl N-[2-amino-2-oxo-1-[(2-oxoimidazolidin-1-yl)methyl]ethyl]carbamate (462 mg, 27.4% yield) was obtained as a white solid.

Step 4: 2-amino-3-(2-oxoimidazolidin-1-yl)propanamide

To a solution of 4 (450 mg, 1.47 mmol, 1 eq) in MeOH (3 mL) was added Pd/C (0.2 g, 10% purity) under $N_2$. The suspension was degassed under vacuum and purged with $H_2$ several times. The mixture was stirred under $H_2$ (15 psi) at 25° C. for 1 h. TLC (dichloromethane:methanol=10/1, Ninhydrin). The reaction mixture was filtered and concentrated under reduced pressure to give a residue. The crude product was used into the next step without further purification, and 2-amino-3-(2-oxoimidazolidin-1-yl)propanamide (250 mg, crude) was obtained as a white solid.

Step 5: tert-butyl (2S)-2-amino-3-cyclopropyl-propanoate

To a solution of 2-amino-3-(2-oxoimidazolidin-1-yl)propanamide (0.3 g, 2.3 mmol, 1 eq) in tert-butyl acetate (4.33 g, 37.2 mmol, 5 mL, 16.0 eq) was added $HClO_4$ (533.3 mg, 3.7 mmol, 0.32 mL, 70% purity, 1.6 eq) slowly at 0° C. The mixture was stirred at 25° C. for 15 h. TLC (petroleum ether:ethyl acetate=2/1, ninhydrin). The reaction mixture was diluted with $H_2O$ (10 mL) followed by an addition of 1 N HCl (8 mL). The pH of the mixture was adjusted to about 9 with 10% aq $Na_2CO_3$, and then extracted with DCM (3*15 mL). The combined organic layers were dried over $Na_2SO_4$ to give tert-butyl (2S)-2-amino-3-cyclopropyl-propanoate (0.4 g, crude) as a colorless oil.

Step 6: tert-butyl (2S)-3-cyclopropyl-2-[(4-methoxy-1H-indole-2-carbonyl)amino]propanoate To a solution of 4-methoxy-1H-indole-2-carboxylic acid (206.3 mg, 1.08 mmol, 1 eq) and HOBt (153.1 mg, 1.1 mmol, 1.0 eq) in DCM (6 mL) was added EDCI (223.5 mg, 1.17 mmol, 1.0 eq) and tert-butyl (2S)-2-amino-3-cyclopropyl-propanoate (200 mg, 1.08 mmol, 1 eq). The mixture was stirred at 25° C. for 16 h. TLC (petroleum ether:ethyl acetate=2/1, UV). The reaction mixture was concentrated under reduced pressure to give a residue. The residue was purified by column chromatography ($SiO_2$, petroleum ether/ethyl acetate=100/1 to 2/1) to give tert-butyl (2S)-3-cyclopropyl-2-[(4-methoxy-1H-indole-2-carbonyl)amino]propanoate (150 mg, 38% yield) as a yellow solid.

Step 7: (2S)-3-cyclopropyl-2-[(4-methoxy-1H-indole-2-carbonyl)amino]propanoic acid To a solution of tert-butyl (2S)-3-cyclopropyl-2-[(4-methoxy-1H-indole-2-carbonyl)amino]propanoate (100 mg, 0.27 mmol, 1 eq) in DCM (1 mL) was added TFA (7.7 g, 67.5 mmol, 5.0 mL, 242.05 eq) and the resulting mixture was stirred at 25° C. for 1 h. TLC (petroleum ether:ethyl acetate=2/1, UV). The reaction mixture was concentrated under reduced pressure to give a residue. The residue was purified by column chromatography ($SiO_2$, petroleum ether/ethyl acetate=100/1 to 2/1) to give (2S)-3-cyclopropyl-2-[(4-methoxy-1H-indole-2-carbonyl)amino]propanoic acid (50 mg, 59.2% yield) as a white solid.

Step 8: N-[(1S)-2-[[2-amino-2-oxo-1-[(2-oxoimidazolidin-1-yl)methyl]ethyl]amino]-1-(cyclopropylmethyl)-2-oxo-ethyl]-4-methoxy-1H-indole-2-carboxamide To a solution of (2S)-3-cyclopropyl-2-[(4-methoxy-1H-indole-2-carbonyl)amino]propanoic acid (50 mg, 0.16 mmol, 1 eq) in DMF (2 mL) was added HATU (94.3 mg, 0.24 mmol, 1.5 eq), 2-amino-3-(2-oxoimidazolidin-1-yl)propanamide (42.7 mg, 0.24 mmol, 1.5 eq) and DIPEA (53.4 mg, 0.41 mmol, 72.0 uL, 2.5 eq). The mixture was stirred at 25° C. for 1 h. TLC (dichloromethane:methanol=10/1, UV). The reaction mixture was concentrated under reduced pressure to give a residue. The residue was purified by column chromatography ($SiO_2$, petroleum ether/ethyl acetate=100/1 to 10/1) to give 10 (60 mg, 79% yield) as a white solid.

Step 9: N-[(1S)-2-[[1-cyano-2-(2-oxoimidazolidin-1-yl)ethyl]amino]-1-(cyclopropylmethyl)-2-oxo-ethyl]-4-methoxy-1H-indole-2-carboxamide To a solution of 10 (60 mg, 0.13 mmol, 1 eq) in DCM (3.0 mL) was added Burgess reagent (93.9 mg, 0.39 mmol, 3.0 eq). The mixture was stirred at 25° C. for 16 hr. The reaction mixture was concentrated under reduced pressure to give a residue. The residue was purified by prep-HPLC (column: Phenomenex Gemini-NX 80*40 mm*3 um; mobile phase: [water (0.05% $NH_3H_2O$+10 mM $NH_4HCO_3$)-ACN]; B %: 21%-51%, 9.5 min) to give N-[(1S)-2-[[1-cyano-2-(2-oxo-imidazolidin-1-yl)ethyl]amino]-1-(cyclopropylmethyl)-2-oxo-ethyl]-4-methoxy-1H-indole-2-carboxamide (9.72 mg, 16% yield) as a white solid.

LCMS: Rt=0.772 min; for $C_{22}H_{26}N_6O_4$ MS Calcd.: 438.20; MS Found: 439.1 [M+H$^+$].

$^1$H NMR (400 MHz, $CD_3OD$) δ 7.28 (s, 1H), 7.19-7.12 (m, 1H), 7.03 (d, J=8.3 Hz, 1H), 6.52 (d, J=7.6 Hz, 1H), 5.22-5.01 (m, 1H), 4.59 (s, 1H), 3.93 (s, 3H), 3.62-3.52 (m, 4H), 3.44-3.34 (m, 2H), 1.92-1.78 (m, 1H), 1.70 (tt, J=6.8, 13.2 Hz, 1H), 0.83 (d, J=6.0 Hz, 1H), 0.61-0.40 (m, 2H), 0.27-0.08 (m, 2H).

Example 157. Synthesis of Viral Protease Inhibitor Compound 495

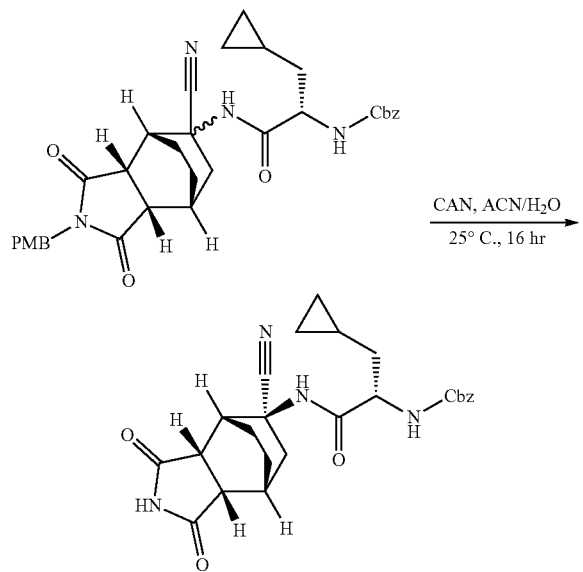

Isomer 1: benzyl N-[(1S)-2-[[(1R,2S,6R,7R,8S)-8-cyano-3,5-dioxo-4-azatricyclo[5.2.2.0²,⁶]undecan-8-yl]amino]-1-(cyclopropylmethyl)-2-oxo-ethyl]carbamate; Isomer 2: Benzyl N-[(1S)-2-[[(1S,2R,6S,7S,8R)-8-cyano-3,5-dioxo-4-azatricyclo[5.2.2.0²,⁶]undecan-8-yl]amino]-1-(cyclopropylmethyl)-2-oxo-ethyl]carbamate A mixture of benzyl N-((1S)-2-[[(1R,2S,6R,7R)-8-cyano-4-[(4-methoxyphenyl)methyl]-3,5-dioxo-4-azatricyclo[5.2.2.0²,⁶]undecan-8-yl]amino]-1-(cyclopropylmethyl)-2-oxo-ethyl]carbamate (200 mg, 0.34 mmol, 1 eq), ammonia; cerium (4+); nitric acid; tetranitrate (1.13 g, 2.05 mmol, 1.02 mL, 6 eq) in H₂O (1 mL) and MeCN (3 mL) was degassed and purged with N₂ for 3 times, and then the mixture was stirred at 25° C. for 16 h under N₂ atmosphere. The mixture was quenched with H₂O (20 mL), and extracted with ethyl acetate (40 mL*3). The combined organic layers was washed with brine (10 mL) dried over Na₂SO₄, filtered and concentrated under reduce pressure. The residue was purified by prep-HPLC (column: 3_Phenomenex Luna C18 75*30 mm*3 um; mobile phase: [water(0.05% HCl)-ACN]; B %: 25%-55%, 8.5 min) to give benzyl N-[(1S)-2-[[(1R,2S,6R,7R,8S)-8-cyano-3,5-dioxo-4-azatricyclo[5.2.2.0²,⁶] undecan-8-yl]amino]-1-(cyclopropylmethyl)-2-oxo-ethyl]carbamate (17.25 mg, 35.6 umol, 10.4% yield, 96.1% purity) was obtained as a white solid and benzyl N-[(1S)-2-[[(1S,2R,6S,7S,8R)-8-cyano-3,5-dioxo-4-azatricyclo[5.2.2.0²,⁶]undecan-8-yl]amino]-1-(cyclopropylmethyl)-2-oxo-ethyl]carbamate (17.56 mg, 36.37 umol, 10.63% yield, 96.2% purity) was obtained as a white solid.

Isomer 1: LCMS: Rt=0.798 min; for $C_{25}H_{28}N_4O_5$ MS Calcd.: 464.21; MS Found: 465.1 [M+H⁺]. ¹H NMR (400 MHz, CD₃OD) δ 7.47-7.21 (m, 5H), 5.17-5.08 (m, 2H), 4.10 (dd, J=4.3, 9.8 Hz, 1H), 3.12 (br d, J=2.5 Hz, 1H), 3.01-2.88 (m, 2H), 2.42-2.28 (m, 2H), 2.20-2.09 (m, 1H), 1.89 (br d, J=15.3 Hz, 1H), 1.80-1.73 (m, 2H), 1.72-1.61 (m, 2H), 1.56 (br d, J=7.5 Hz, 1H), 0.82-0.67 (m, 1H), 0.42-0.42 (m, 1H), 0.48-0.38 (m, 1H), 0.23-0.09 (m, 2H).

Isomer 2: LCMS: Rt=0.818 min; for $C_{25}H_{28}N_4O_5$ MS Calcd.: 464.21; MS Found: 465.1 [M+H⁺]. ¹H NMR (400 MHz, CD₃OD) δ 7.45-7.25 (m, 5H), 5.18-5.09 (m, 2H), 4.17 (br dd, J=6.0, 7.6 Hz, 1H), 3.35 (s, 1H), 3.11-2.93 (m, 2H), 2.42 (br d, J=15.6 Hz, 1H), 2.31 (br s, 1H), 2.23-2.12 (m, 1H), 1.91 (br d, J=15.3 Hz, 1H), 1.76 (br d, J=6.8 Hz, 2H), 1.68 (br d, J=11.4 Hz, 1H), 1.65-1.58 (m, 1H), 1.56-1.45 (m, 1H), 0.78-0.67 (m, 1H), 0.44 (d, J=5.1 Hz, 2H), 0.12 (br s, 2H).

Example 158. Synthesis of Viral Protease Inhibitor Compound 496

Step 1: Methyl 4,4-difluoro-2-[(4-methoxy-1H-indole-2-carbonyl)amino]pentanoate

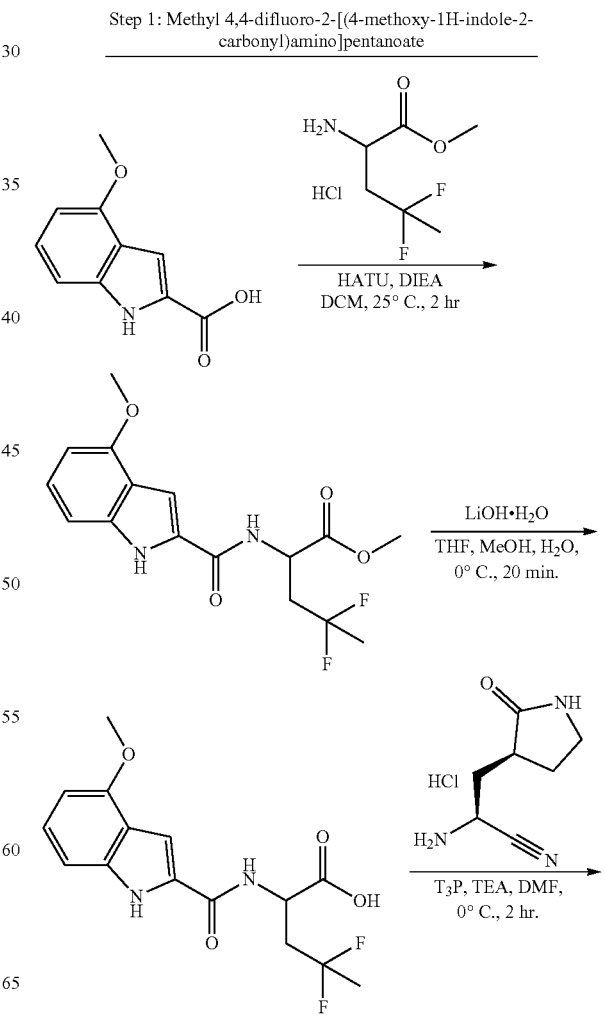

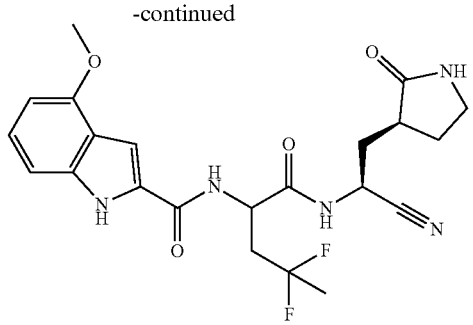

To a solution of 4-methoxy-1H-indole-2-carboxylic acid (281.6 mg, 1.47 mmol, 1 eq) in DCM (1 mL) was added HATU (672.2 mg, 1.77 mmol, 1.2 eq), DIPEA (571.2 mg, 4.42 mmol, 0.76 mL, 3 eq) and methyl 2-amino-4,4-difluoro-pentanoate (300 mg, 1.47 mmol, 1 eq, HCl). The mixture was stirred at 25° C. for 2 h. TLC (petroleum ether:ethyl acetate=0:1). The reaction mixture was diluted with H$_2$O (10 mL) and extracted with DCM (10 mL*3). The combined organic phase was washed with brine (10 mL*3), dried with anhydrous Na$_2$SO$_4$, filtered and concentrated in vacuum. The residue was purified by flash silica gel chromatography (ISCO®; 4 g SepaFlash® Silica Flash Column, Eluent of 0~30% petroleum ether/ethyl acetate ethergradient @ 20 mL/min) to give methyl 4,4-difluoro-2-[(4-methoxy-1H-indole-2-carbonyl)amino]pentanoate (357 mg, 1.04 mmol, 70.7% yield, 99.4% purity) as a yellow solid.

Step 2: 4,4-Difluoro-2-[(4-methoxy-1H-indole-2-carbonyl)amino]pentanoic acid

To a solution of methyl 4,4-difluoro-2-[(4-methoxy-1H-indole-2-carbonyl)amino]pentanoate (357 mg, 1.05 mmol, 1 eq) in THF (3 mL) and MeOH (1 mL) was added LiOH·H$_2$O (132.0 mg, 3.15 mmol, 3 eq) in H$_2$O (2 mL) at 0° C., The mixture was stirred at 0° C. for 20 min. The pH of the reaction was adjusted to about 4 with 4 M HCl. The reaction mixture was diluted with H$_2$O (5 mL) and extracted with ethyl acetate (5 mL*3). The combined organic phase was washed with brine (5 mL*3), dried with anhydrous Na$_2$SO$_4$, filtered and concentrated in vacuum. The crude product was used into the next step without further purification. Compound 4,4-difluoro-2-[(4-methoxy-1H-indole-2-carbonyl)amino]pentanoic acid (321 mg, 93.7% yield) was obtained as a light yellow solid.

Step 3: N-[1-[[(1S)-1-cyano-2-[(3S)-2-oxopyrrolidin-3-yl]ethyl]carbamoyl]-3,3-difluoro-butyl]-4-methoxy-1H-indole-2-carboxamide To a solution of 4,4-difluoro-2-[(4-methoxy-1H-indole-2-carbonyl)amino]pentanoic acid (20 mg, 61.2 umol, 1 eq) in DCM (0.5 mL) was added (2S)-2-amino-3-[(3S)-2-oxopyrrolidin-3-yl]propanenitrile (13.9 mg, 73.5 umol, 1.2 eq, HCl), TEA (18.6 mg, 0.18 mmol, 25.5 uL, 3 eq) and T$_3$P (50.7 mg, 79.6 umol, 50% purity, 1.3 eq) in DMF (0.2 mL). The mixture was stirred at 0° C. for 2 h. The reaction mixture was diluted with H$_2$O (10 mL) and extracted with DCM (10 mL*3). The combined organic phase was washed with brine (10 mL*3), dried with anhydrous Na$_2$SO$_4$, filtered and concentrated in vacuum. The residue was purified by prep-HPLC (column: Phenomenex Gemini-NX 80*40 mm*3 um; mobile phase: [water(0.05% NH$_3$H$_2$O+10 mM NH$_4$HCO$_3$)-ACN]; B %: 17%-47%, 9.5 min) to give N-[1-[[(1S)-1-cyano-2-[(3S)-2-oxopyrrolidin-3-yl]ethyl]carbamoyl]-3,3-difluoro-butyl]-4-methoxy-1H-indole-2-carboxamide (2.54 mg, 8.7% yield, 97.7% purity) as a white solid.

LCMS: Rt=0.772 min; for C$_{22}$H$_{25}$F$_2$N$_5$O$_4$ MS Calcd.: 461.19; MS Found: 462.1 [M+H$^+$].

$^1$H NMR (400 MHz, CD$_3$OD) δ 7.24 (d, J=3.8 Hz, 1H), 7.15 (dt, J=2.3, 8.0 Hz, 1H), 7.03 (dd, J=2.5, 8.3 Hz, 1H), 6.52 (dd, J=1.5, 7.5 Hz, 1H), 5.07-5.00 (m, 1H), 4.84 (br s, 1H), 3.93 (d, J=1.8 Hz, 3H), 3.30-3.18 (m, 2H), 2.67-2.57 (m, 1H), 2.56-2.40 (m, 2H), 2.37-2.25 (m, 2H), 1.95-1.85 (m, 1H), 1.85-1.76 (m, 1H), 1.69 (dt, J=2.6, 18.8 Hz, 3H).

Example 159. Synthesis of Viral Protease Inhibitor Compound 501

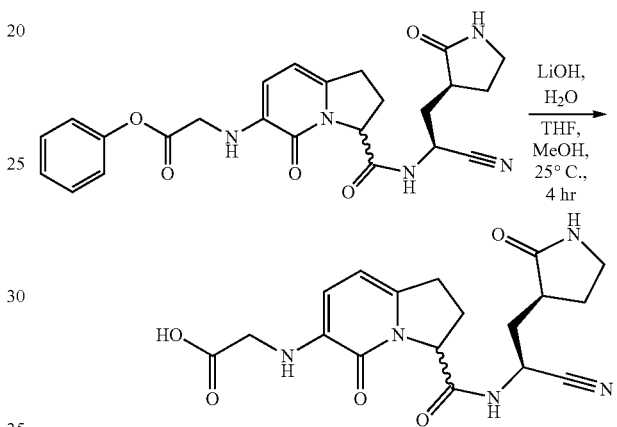

To a solution of phenyl 2-[[(3S)-3-[[(1S)-1-cyano-2-[(3S)-2-oxopyrrolidin-3-yl]ethyl]carbamoyl]-5-oxo-2,3-dihydro-1H-indolizin-6-yl]amino]acetate (100 mg, 0.21 mmol, 1 eq) in THF (1 mL) and MeOH (0.3 mL) was added LiOH·H$_2$O (27.1 mg, 0.64 mmol, 3 eq) in H$_2$O (0.5 mL). The mixture was stirred at 25° C. for 4 h. LC-MS and HPLC showed the desired compound was detected. The pH of the reaction was adjusted to about 1 with 4 M HCl. The reaction mixture was diluted with H$_2$O (5 mL) and extracted with ethyl acetate (5 mL*3). The combined organic phase was washed with brine (5 mL*3), dried with anhydrous Na$_2$SO$_4$, filtered and concentrated in vacuum. The residue was purified by prep-HPLC (column: 3_Phenomenex Luna C18 75*30 mm*3 um; mobile phase: [water (0.05% HCl)-ACN]; B %: 0%-30%, 8.5 min). The residue was checked by LCMS and HPLC. The residue was purified by prep-HPLC (column: 3_Phenomenex Luna C18 75*30 mm*3 um; mobile phase: [water (0.05% HCl)-ACN]; B %: 0%-30%, 8.5 min). Compound 2-[[(3S)-3-[[(1S)-1-cyano-2-[(3S)-2-oxopyrrolidin-3-yl]ethyl]carbamoyl]-5-oxo-2,3-dihydro-1H-indolizin-6-yl]amino]acetic acid (1.2 mg, 1.27% yield, 98.9% purity, CHOOH) was obtained as a white solid.

LCMS: Rt=0.643 min; for C$_{18}$H$_{21}$N$_5$O$_5$ MS Calcd.: 387.15; MS Found: 388.1 [M+H$^+$].

$^1$H NMR (400 MHz, CD$_3$OD) δ 8.49 (br s, 1H), 8.03 (s, 1H), 6.32 (d, J=7.5 Hz, 1H), 5.09-5.03 (m, 2H), 3.74 (s, 2H), 3.34 (br s, 1H), 3.26-3.18 (m, 2H), 3.17-3.07 (m, 1H), 2.74-2.64 (m, 1H), 2.62-2.51 (m, 1H), 2.40-2.26 (m, 3H), 2.24-2.15 (m, 1H), 1.97-1.88 (m, 1H), 1.87-1.77 (m, 1H).

Example 160. Synthesis of Viral Protease Inhibitor Compound 505

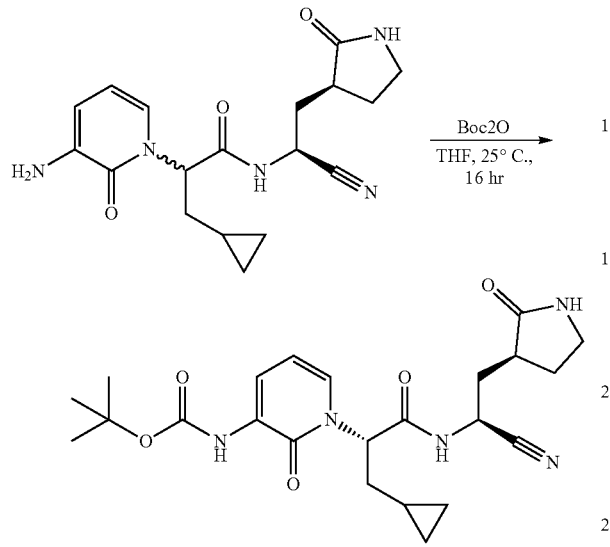

To a solution of 2-(3-amino-2-oxo-1-pyridyl)-N-[(1S)-1-cyano-2-[(3S)-2-oxopyrrolidin-3-yl]ethyl]-3-cyclopropyl-propanamide (100 mg, 0.27 mmol, 1 eq) in THF (1 mL) was added Boc2O (610.6 mg, 2.80 mmol, 0.64 mL, 10 eq). The mixture was stirred at 25° C. for 16 h. TLC (DCM:MeOH=10:1). The reaction mixture was diluted with H₂O (10 mL) and extracted with ethyl acetate (10 mL*3). The combined organic phase was washed with brine (10 mL*3), dried with anhydrous Na₂SO₄, filtered and concentrated in vacuum. The residue was purified by prep-TLC (SiO₂, DCM:MeOH=20:1) to give tert-butyl N-[1-[2-[[(1S)-1-cyano-2-[(3S)-2-oxopyrrolidin-3-yl]ethyl]amino]-1-(cyclopropylmethyl)-2-oxo-ethyl]-2-oxo-3-pyridyl]carbamate (12.62 mg, 9.0% yield, 91.4% purity) as a white solid.

LCMS: Rt=0.832 min; for $C_{23}H_{31}N_5O_5$ MS Calcd.: 457.23; MS Found: 458.2 [M+H⁺].

¹H NMR (400 MHz, CD₃OD) δ 7.98 (d, J=6.3 Hz, 1H), 7.39-7.31 (m, 1H), 6.45-6.34 (m, 1H), 5.56-5.39 (m, 1H), 5.03 (d, J=6.8 Hz, 1H), 3.34 (s, 1H), 3.29-3.22 (m, 1H), 2.57-2.43 (m, 1H), 2.41-2.30 (m, 1H), 2.29-2.20 (m, 1H), 2.01-1.94 (m, 2H), 1.92-1.72 (m, 2H), 1.52 (d, J=2.5 Hz, 9H), 0.62 (dd, J=7.4, 12.3 Hz, 1H), 0.50-0.36 (m, 2H), 0.21-0.12 (m, 1H), 0.09-0.02 (m, 1H).

Example 161. Synthesis of Viral Protease Inhibitor Compound 504

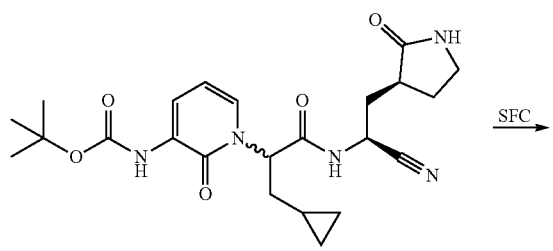

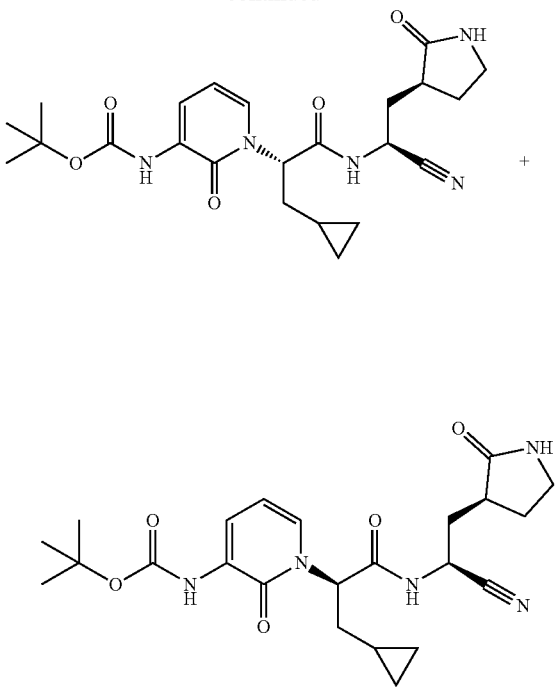

The residue was further separated by SFC. The residue was further separated by SFC (column: DAICEL CHIRAL-PAK AS (250 mm*30 mm, 10 um); mobile phase: [0.1% NH₃H₂O ETOH]; B %: 30%-30%, min).

Isomer 1: Compound tert-butyl N-[1-[(1R)-2-[[(1S)-1-cyano-2-[(3S)-2-oxopyrrolidin-3-yl]ethyl]amino]-1-(cyclopropylmethyl)-2-oxo-ethyl]-2-oxo-3-pyridyl]carbamate (2.47 mg, 23.1% yield) was obtained as a white solid. LCMS: Rt=0.837 min; for $C_{23}H_{31}N_5O_5$ MS Calcd.: 457.23; MS Found: 458.1 [M+H⁺]. ¹H NMR (400 MHz, CD₃OD) δ 7.98 (d, J=7.1 Hz, 1H), 7.34 (dd, J=1.7, 7.1 Hz, 1H), 6.39 (t, J=7.2 Hz, 1H), 5.56-5.31 (m, 1H), 5.01 (dd, J=6.8, 9.3 Hz, 1H), 3.34 (d, J=2.8 Hz, 2H), 2.56-2.44 (m, 1H), 2.41-2.32 (m, 1H), 2.32-2.24 (m, 1H), 2.00-1.91 (m, 3H), 1.89-1.82 (m, 1H), 1.52 (s, 9H), 0.59 (s, 1H), 0.46-0.37 (m, 2H), 0.15 (d, J=8.4 Hz, 1H), 0.03 (d, J=11.3 Hz, 1H).

Isomer 2: Compound tert-butyl N-[1-[(1S)-2-[[(1S)-1-cyano-2-[(3S)-2-oxopyrrolidin-3-yl]ethyl]amino]-1-(cyclopropylmethyl)-2-oxo-ethyl]-2-oxo-3-pyridyl]carbamate (2.71 mg, 25.5% yield) was obtained as a white solid. LCMS: Rt=0.837 min; for $C_{23}H_{31}N_5O_5$ MS Calcd.: 457.23; MS Found: 458.1 [M+H⁺]. ¹H NMR (400 MHz, CD₃OD) δ 7.97 (d, J=7.3 Hz, 1H), 7.35 (dd, J=1.8, 7.0 Hz, 1H), 6.38 (t, J=7.3 Hz, 1H), 5.42 (dd, J=7.0, 8.5 Hz, 1H), 5.44-5.40 (m, 1H), 5.03-4.99 (m, 1H), 3.30-3.25 (m, 2H), 2.48 (dq, J=5.3, 9.2 Hz, 1H), 2.29-2.22 (m, 1H), 2.32-2.22 (m, 1H), 2.02-1.94 (m, 2H), 1.91-1.85 (m, 1H), 1.84-1.73 (m, 1H), 1.51 (s, 9H), 0.63 (br d, J=6.8 Hz, 1H), 0.49-0.42 (m, 2H), 0.18-0.13 (m, 1H), 0.06 (dd, J=4.3, 8.8 Hz, 1H).

Example 162. Synthesis of Viral Protease Inhibitor Compound 509

Step 1: methyl (2S)-2-[[(2S)-2-[[4-(difluoromethoxy)-1H-indole-2-carbonyl]amino]-4-methyl-pentanoyl]amino]-3-[(3S)-2-oxopyrrolidin-3-yl]propanoate

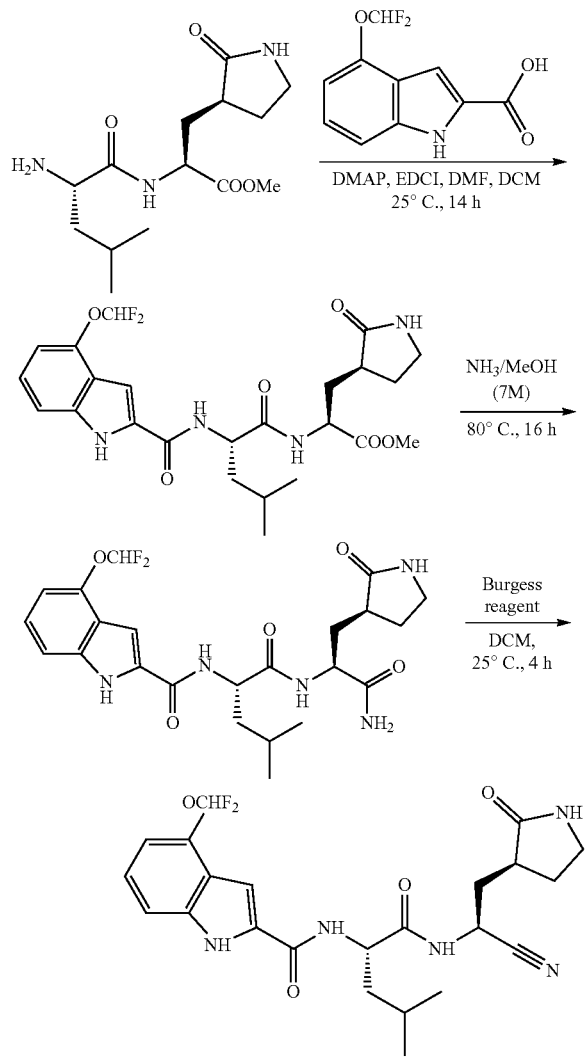

To a mixture of methyl (2S)-2-[[(2S)-2-amino-4-methyl-pentanoyl]amino]-3-[(3S)-2-oxopyrrolidin-3-yl]propanoate (160 mg, 476.44 umol, 1 eq, HCl) and 4-(difluoromethoxy)-1H-indole-2-carboxylic acid (108.23 mg, 476.44 umol, 1 eq) in DCM (4 mL) was added DMAP (174.62 mg, 1.43 mmol, 3 eq) and EDCI (274.00 mg, 1.43 mmol, 3 eq), The mixture was added DMF (1 mL) and stirred at 25° C. for 14 h. The reaction mixture was concentrated under reduced pressure to give a residue. The residue was purified by prep-HPLC (neutral condition, column: Waters Xbridge BEH C18 100*30 mm*10 um; mobile phase: [water (10 mM NH$_4$HCO$_3$)-ACN]; B %: 30%-60%, 10 min). Compound methyl (2S)-2-[[(2S)-2-[[4-(difluoromethoxy)-1H-indole-2-carbonyl]amino]-4-methyl-pentanoyl]amino]-3-[(3S)-2-oxopyrrolidin-3-yl]propanoate (150 mg, 294.98 umol, 61.91% yield) was obtained as a white solid. MS (ESI) m/z 494.3 [M+H]$^+$ Step 2: N-[(1S)-1-[[(1S)-2-amino-2-oxo-1-[[(3S)-2-oxopyrrolidin-3-yl]methyl]ethyl]carbamoyl]-3-methyl-butyl]-4-(difluoromethoxy)-1H-indole-2-carboxamide A mixture of methyl (2S)-2-[[(2S)-2-[[4-(difluoromethoxy)-1H-indole-2-carbonyl]amino]-4-methyl-pentanoyl]amino]-3-[(3S)-2-oxopyrrolidin-3-yl]propanoate (150 mg, 294.98 umol, 1 eq) in ammonia (7.65 g, 449.19 mmol, 7.50 mL, 1522.81 eq) was stirred at 80° C. for 16 h. The reaction mixture was concentrated under reduced pressure to give a residue. Compound N-[(1S)-1-[[(1S)-2-amino-2-oxo-1-[[(3S)-2-oxopyrrolidin-3-yl]methyl]ethyl]carbamoyl]-3-methyl-butyl]-4-(difluoromethoxy)-1H-indole-2-carboxamide (100 mg, 202.63 umol, 68.69% yield) was obtained as a white solid and used for the next step. MS (ESI) m/z 494.3 [M+H]$^+$ Step 3: N-[(1S)-1-[[(1S)-1-cyano-2-[(3S)-2-oxopyrrolidin-3-yl]ethyl]carbamoyl]-3-methyl-butyl]-4-(difluoromethoxy)-1H-indole-2-carboxamide To a mixture of N-[(1S)-1-[[(1S)-2-amino-2-oxo-1-[[(3S)-2-oxopyrrolidin-3-yl]methyl]ethyl]carbamoyl]-3-methyl-butyl]-4-(difluoromethoxy)-1H-indole-2-carboxamide (100 mg, 202.63 umol, 1 eq) in DCM (3 mL) was added Burgess reagent (193.16 mg, 810.53 umol, 4 eq) in one portion at 25° C. The mixture was stirred at 25° C. for 4 h. The reaction mixture was concentrated under reduced pressure to give a residue. The residue was purified by prep-HPLC (neutral condition, column: Waters Xbridge BEH C18 100*30 mm*10 um; mobile phase: [water (10 mM NH$_4$HCO$_3$)-ACN]; B %: 30%-60%, 10 min). Compound N-[(1S)-1-[[(1S)-1-cyano-2-[(3S)-2-oxopyrrolidin-3-yl]ethyl]carbamoyl]-3-methyl-butyl]-4-(difluoromethoxy)-1H-indole-2-carboxamide (30 mg, 63.09 umol, 31.14% yield) was obtained as a white solid. MS (ESI) m/z 476.3 [M+H]$^+$ $^1$H NMR (400 MHz, DMSO-d$_6$) δ=11.88 (d, J=1.8 Hz, 1H), 8.93 (d, J=8.1 Hz, 1H), 8.65 (d, J=7.7 Hz, 1H), 7.78-7.67 (m, 1H), 7.43 (d, J=1.5 Hz, 1H), 7.35-7.27 (m, 1H), 7.21-7.12 (m, 1H), 6.82 (d, J=7.6 Hz, 1H), 5.04-4.85 (m, 1H), 4.56-4.40 (m, 1H), 3.20-3.03 (m, 2H), 2.42-2.04 (m, 3H), 1.85-1.47 (m, 5H), 1.00-0.84 (m, 6H)

Example 163. Synthesis of Viral Protease Inhibitor Compound 515

Step 1: 4-hydroxy-1H-indole-2-carboxylic acid

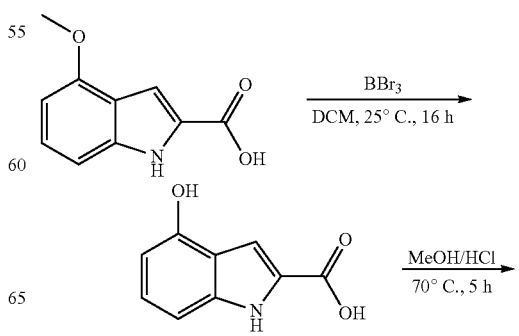

-continued

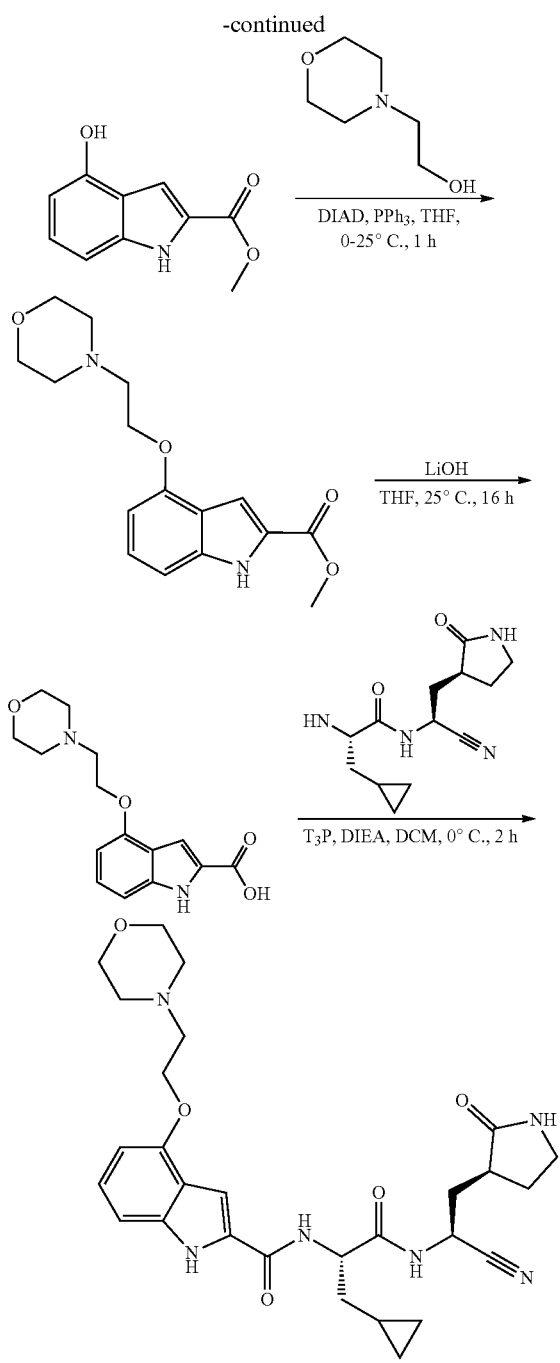

To a mixture of 4-methoxy-1H-indole-2-carboxylic acid (500 mg, 2.62 mmol, 1 eq) in DCM (10 mL) was added BBr₃ (1.31 g, 5.23 mmol, 2 eq) at 0° C. The mixture was stirred at 25° C. for 16 h. The mixture was diluted with H₂O (30 mL) and extracted with DCM (60 mL, which was extracted as 30 mL*2). The combined organic layers were washed with brine (20 mL), dried over Na₂SO₄, filtered and concentrated under reduced pressure to give 4-hydroxy-1H-indole-2-carboxylic acid (200 mg, crude) as a red solid. MS (ESI) m/z 176.1 [M−H]⁺

Step 2: methyl 4-hydroxy-1H-indole-2-carboxylate 4-hydroxy-1H-indole-2-carboxylic acid (200 mg, 1.13 mmol, 1 eq) was added HCl/MeOH (4 M, 10 mL, 35.43 eq). The mixture was stirred at 70° C. for 5 h. The reaction mixture was concentrated under reduced pressure to give the crude product. The crude was purified by column chromatography (SiO₂, petroleum ether/ethyl acetate=9/1 to 8/1) to give methyl 4-hydroxy-1H-indole-2-carboxylate (170 mg, 800.28 umol, 70.89% yield, 90% purity) as a yellow solid. MS (ESI) m/z 190.1 [M−H]⁺

Step 3: methyl 4-(2-morpholinoethoxy)-1H-indole-2-carboxylate

To a mixture of methyl 4-hydroxy-1H-indole-2-carboxylate (300 mg, 1.57 mmol, 1 eq) and 2-morpholinoethanol (205.83 mg, 1.57 mmol, 192.37 uL, 1 eq) in THF (4 mL) was added PPh₃ (452.73 mg, 1.73 mmol, 1.1 eq), DIAD (317.30 mg, 1.57 mmol, 305.10 uL, 1 eq) was added at 0° C. under N₂. The mixture was stirred at 25° C. for 60 min. The reaction mixture was diluted with H₂O (10 mL) and extracted with ethyl acetate (10 mL*2). The combined organic layers were washed with brine 20 mL, filtered and concentrated under reduced pressure to give a residue. The residue was purified by prep-TLC (petroleum ether:ethyl acetate=0:1) to give methyl 4-(2-morpholinoethoxy)-1H-indole-2-carboxylate (200 mg, 591.44 umol, 37.69% yield, 90% purity) as a yellow solid. MS (ESI) m/z 304.9 [M+H]⁺

Step 4: 4-(2-morpholinoethoxy)-1H-indole-2-carboxylic acid

To a mixture of methyl 4-(2-morpholinoethoxy)-1H-indole-2-carboxylate (200 mg, 657.16 umol, 1 eq) in THF (2 mL) and H₂O (1 mL) was added LiOH·H₂O (41.37 mg, 985.74 umol, 1.5 eq) at 25° C. The mixture was stirred at 25° C. for 16 h. The reaction mixture was concentrated under reduced pressure to give a residue. The crude was purified by HCl prep-HPLC to give 4-(2-morpholinoethoxy)-1H-indole-2-carboxylic acid (80 mg, 261.79 umol, 39.84% yield, 95% purity) as a white solid. MS (ESI) m/z 289.2 [M−H]⁺
column: Phenomenex luna C18 80*40 mm*3 um; mobile phase: [water(0.04% HCl)-ACN]; B %: 1%-32%, 6.5 min Step 5: N-[(1S)-2-[[(1S)-1-cyano-2-[(3S)-2-oxopyrrolidin-3-yl]ethyl]amino]-1-(cyclopropylmethyl)-2-oxo-ethyl]-4-(2-morpholinoethoxy)-1H-indole-2-carboxamide To a mixture of 4-(2-morpholinoethoxy)-1H-indole-2-carboxylic acid (70 mg, 241.12 umol, 1 eq) and (2S)-2-amino-N-[(1S)-1-cyano-2-[(3S)-2-oxopyrrolidin-3-yl]ethyl]-3-cyclopropyl-propanamide (159.33 mg, 241.12 umol, 40% purity, 1 eq) in DCM (2 mL) was added DIEA (93.49 mg, 723.36 umol, 125.99 uL, 3 eq) and T₃P (230.16 mg, 361.68 umol, 215.10 uL, 50% purity, 1.5 eq) in one portion at 0° C. The mixture was stirred at 0° C. for 2 h. The reaction mixture was added EDTA solution (2 mL) and stirred at 25° C. for 10 min, and then extracted with DCM (6 mL, which was extracted as 2 mL*3). The combined organic layers were washed with brine (5 mL, which was washed as 5 mL*3), and concentrated under reduced pressure to give a residue. The residue was purified by prep-HPLC (neutral condition) to give N-[(1S)-2-[[(1S)-1-cyano-2-[(3S)-2-oxopyrrolidin-3-yl]ethyl]amino]-1-(cyclopropylmethyl)-2-oxo-ethyl]-4-(2-morpholinoethoxy)-1H-indole-2-carboxamide (13 mg, 24.23 umol, 10.05% yield) as a white solid. MS (ESI) m/z 537.3 [M+H]⁺ column: Waters Xbridge Prep OBD C18 150*40 mm*10 um; mobile phase: [water (10 mM NH₄HCO₃)-ACN]; B %: 20%-50%, 8 min ¹H NMR (400 MHz, DMSO-d₆) δ=11.57 (s, 1H), 8.92 (d, J=7.9 Hz, 1H), 8.60 (br d, J=7.5 Hz, 1H), 7.79-7.68 (m, 1H), 7.35 (d, J=1.5 Hz, 1H), 7.14-6.93 (m, 2H), 6.51 (d, J=7.5 Hz, 1H), 4.98 (q, J=7.9 Hz, 1H), 4.54-4.38 (m, 1H), 4.21 (br d, J=3.5 Hz, 2H), 3.59 (t, J=4.5 Hz, 4H), 3.20-3.05 (m, 2H), 2.78 (t, J=5.6 Hz, 2H), 2.60-2.52 (m, 4H), 2.43-2.28 (m, 1H), 2.23-2.04 (m, 2H), 1.92-1.60 (m, 3H), 1.56-1.38 (m, 1H), 0.80 (br d, J=5.3 Hz, 1H), 0.51-0.30 (m, 2H), 0.25-0.05 (m, 2H)

¹H NMR (400 MHz, METHANOL-d₄) δ=7.34-7.28 (m, 1H), 7.18-7.11 (m, 1H), 7.04 (d, J=8.4 Hz, 1H), 6.53 (d, J=7.5 Hz, 1H), 5.08 (dd, J=5.8, 10.3 Hz, 1H), 4.54 (t, J=7.4 Hz, 1H), 4.30 (t, J=5.3 Hz, 2H), 3.77-3.72 (m, 4H), 3.30-3.27 (m, 2H), 2.92 (t, J=5.3 Hz, 2H), 2.75-2.59 (m, 5H), 2.40-2.26 (m, 2H), 1.99-1.79 (m, 3H), 1.78-1.60 (m, 1H), 0.93-0.76 (m, 1H), 0.58-0.52 (m, 2H), 0.20 (br dd, J=5.0, 11.6 Hz, 2H)

Example 164. Synthesis of Viral Protease Inhibitor Compound 519

Step 1: methyl(2S)-2-[[(2S)-2-amino-3-cyclopropyl-propanoyl]amino]-3-[(3S)-2-oxopyrrolidin-3-yl] propanoate

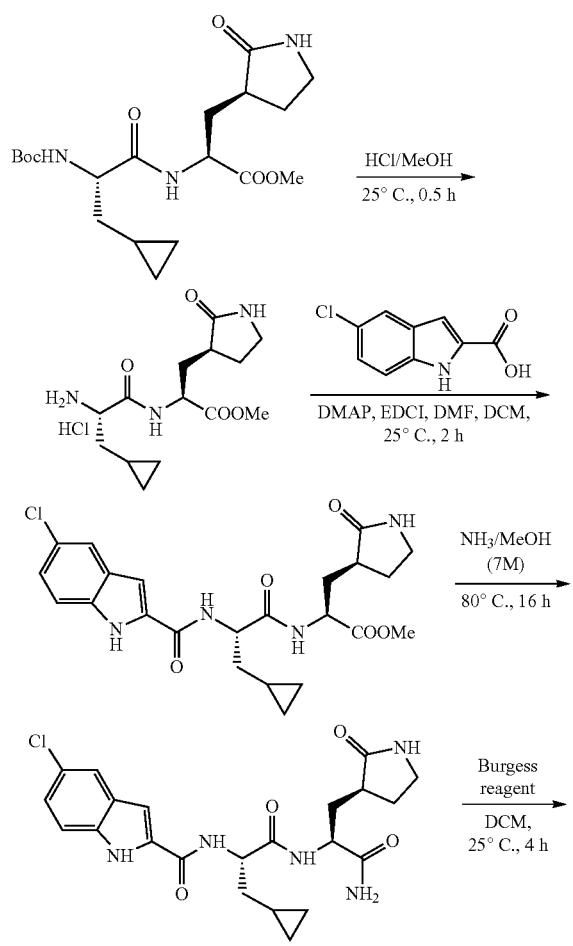

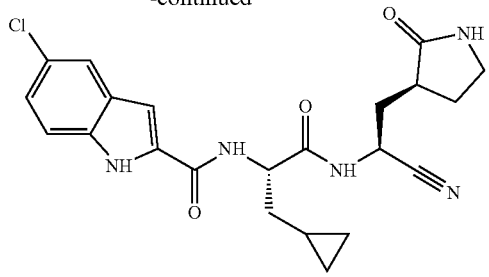

A mixture of methyl (2S)-2-[[(2S)-2-(tert-butoxycarbonylamino)-3-cyclopropyl-propanoyl]amino]-3-[(3S)-2-oxopyrrolidin-3-yl]propanoate (230 mg, 578.67 umol, 1 eq) in HCl/MeOH (3 mL) was stirred at 25° C. for 30 min. The reaction mixture was concentrated under reduced pressure to give the crude methyl (2S)-2-[[(2S)-2-amino-3-cyclopropyl-propanoyl]amino]-3-[(3S)-2-oxopyrrolidin-3-yl]propanoate (170 mg, 571.72 umol, 98.80% yield) as a white solid.

Step 2: methyl(2S)-2-[[(2S)-2-[(5-chloro-1H-indole-2-carbonyl)amino]-3-cyclopropyl-propanoyl]amino]-3-[(3S)-2-oxopyrrolidin-3-yl]propanoate To a mixture of methyl (2S)-2-[[(2S)-2-amino-3-cyclopropyl-propanoyl]amino]-3-[(3S)-2-oxopyrrolidin-3-yl]propanoate (170 mg, 571.72 umol, 1 eq) in DCM (2 mL) and DMF (0.5 mL) was added DMAP (209.54 mg, 1.72 mmol, 3 eq) in one portion at 25° C. The mixture was added with 5-chloro-1H-indole-2-carboxylic acid (134.20 mg, 686.06 umol, 1.2 eq) and EDCI (328.80 mg, 1.72 mmol, 3 eq) and stirred at 25° C. for 2 h. The reaction mixture was concentrated under reduced pressure to give a residue. The crude product was purified by prep-TLC (SiO₂, EA:MeOH=10:1) to give methyl(2S)-2-[[(2S)-2-[(5-chloro-1H-indole-2-carbonyl)amino]-3-cyclopropyl-propanoyl] amino]-3-[(3S)-2-oxopyrrolidin-3-yl]propanoate (140 mg, 294.78 umol, 51.56% yield) as a white solid. MS (ESI) m/z 475.2 [M+H]⁺

Step 3: N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-5-chloro-1H-indole-2-carboxamide To a mixture of methyl (2S)-2-[[(2S)-2-[(5-chloro-1H-indole-2-carbonyl)amino]-3-cyclopropyl-propanoyl] amino]-3-[(3S)-2-oxopyrrolidin-3-yl]propanoate (130 mg, 273.72 umol, 1 eq) in NH₃/MeOH (7M) (5 mL), the mixture was stirred at 80° C. for 16 h. The reaction mixture was concentrated under reduced pressure to give N-[(1S)-2-[[(1S)-2-amino-2-oxo-1-[[(3S)-2-oxopyrrolidin-3-yl] methyl]ethyl]amino]-1-(cyclopropylmethyl)-2-oxo-ethyl]-5-chloro-1H-indole-2-carboxamide (100 mg, 217.43 umol, 79.43% yield) as a white solid. MS (ESI) m/z 460.2 [M+H]⁺

Step 4: 5-chloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-indole-2-carboxamide To a mixture of N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-5-chloro-1H-indole-2-carboxamide (100 mg, 217.43 umol, 1 eq) in DCM (2 mL) was added Burgess reagent (103.63 mg, 434.85 umol, 2 eq) in one portion at 25° C. The mixture was stirred at 25° C. for 4 h. The reaction mixture was concentrated under reduced pressure to give a residue. The residue was purified by prep-HPLC (neutral condition) to give 5-chloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-indole-2-carboxamide (33 mg, 74.68 umol, 34.35% yield) as a white solid. MS (ESI) m/z 442.1 [M+H]+

Column: Waters Xbridge Prep OBD C18 150*40 mm*10 um; mobile phase: [water (10 mM NH4HCO3)-ACN]; B %: 30%-60%, 8 min 1H NMR (400 MHz, DMSO-d6) δ=11.71 (s, 1H), 8.85 (d, J=8.2 Hz, 1H), 8.59 (d, J=7.5 Hz, 1H), 7.71-7.56 (m, 2H), 7.34 (d, J=8.6 Hz, 1H), 7.19 (s, 1H), 7.10 (dd, J=1.5, 8.8 Hz, 1H), 4.97-4.80 (m, 1H), 4.48-4.30 (m, 1H), 3.12-2.94 (m, 2H), 2.36-2.21 (m, 1H), 2.13-1.96 (m, 2H), 1.83-1.54 (m, 3H), 1.47-1.34 (m, 1H), 0.82-0.65 (m, 1H), 0.39-0.26 (m, 2H), 0.19-0.04 (m, 2H)

Example 165. Synthesis of Viral Protease Inhibitor Compound 531

Step 1: methyl(2S)-2-[[(2S)-2-[(7-chloro-1H-indole-2-carbonyl)amino]-3-cyclopropyl-propanoyl]amino]-3-[(3S)-2-oxopyrrolidin-3-yl]propanoate

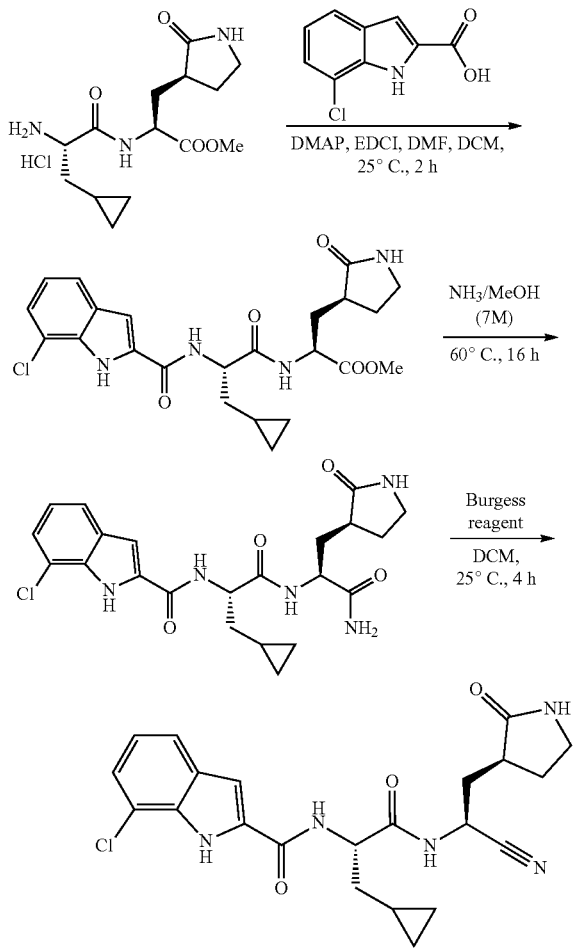

A mixture of methyl (2S)-2-[[(2S)-2-amino-3-cyclopropyl-propanoyl]amino]-3-[(3S)-2-oxopyrrolidin-3-yl]propanoate (500 mg, 1.68 mmol, 1 eq) in DCM (10 mL) and DMF (2.5 mL), the mixture was added DMAP (616.30 mg, 5.04 mmol, 3 eq) in one portion at 25° C. The mixture was added with 7-chloro-1H-indole-2-carboxylic acid (394.69 mg, 2.02 mmol, 1.2 eq) and EDCI (967.04 mg, 5.04 mmol, 3 eq) and the reaction was stirred at 25° C. for 2 h. The reaction mixture was concentrated under reduced pressure to give the crude product. The crude was purified by column chromatography (SiO2, petroleum ether/ethyl acetate=5/1 to 0/1) to give methyl (2S)-2-[[(2S)-2-[(7-chloro-1H-indole-2-carbonyl)amino]-3-cyclopropyl-propanoyl]amino]-3-[(3S)-2-oxopyrrolidin-3-yl]propanoate (550 mg, 1.16 mmol, 68.87% yield) as a white solid. MS (ESI) m/z 475.1 [M+H]+

Step 2: N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-7-chloro-1H-indole-2-carboxamide A mixture of methyl (2S)-2-[[(2S)-2-[(7-chloro-1H-indole-2-carbonyl)amino]-3-cyclopropyl-propanoyl]amino]-3-[(3S)-2-oxopyrrolidin-3-yl]propanoate (500 mg, 1.05 mmol, 1 eq) in NH3/MeOH (7 M, 10 mL, 66.49 eq) was stirred at 60° C. for 16 h. The reaction mixture was concentrated under reduced pressure to give N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-7-chloro-1H-indole-2-carboxamide (440 mg, 956.68 umol, 90.87% yield) as a white solid. MS (ESI) m/z 460.3 [M+H]+

Step 3: 7-chloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-indole-2-carboxamide To a mixture of N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-7-chloro-1H-indole-2-carboxamide (430 mg, 934.94 umol, 1 eq) in DCM (6 mL) was added Burgess reagent (445.61 mg, 1.87 mmol, 2 eq) in one portion at 25° C. The mixture was stirred at 25° C. for 4 h. The reaction mixture was concentrated under reduced pressure to give the crude product. The crude was purified by prep-HPLC (column: Phenomenex Gemini-NX C18 75*30 mm*3 um; mobile phase: [water(0.05% NH3H2O+10 mM NH4HCO3)-ACN]; B %: 30%-60%, 8 min) to give 7-chloro-N-[(1S)-2-[[(1S)-1-cyano-2-[(3S)-2-oxopyrrolidin-3-yl]ethyl]amino]-1-(cyclopropylmethyl)-2-oxo-ethyl]-1H-indole-2-carboxamide (180 mg, 407.32 umol, 43.57% yield) as a white solid. MS (ESI) m/z 442.2 [M+H]+

1H NMR (400 MHz, DMSO-d6) δ=11.71 (br s, 1H), 9.01 (d, J=7.9 Hz, 1H), 8.72 (d, J=7.5 Hz, 1H), 7.71 (s, 1H), 7.63 (dd, J=0.7, 7.9 Hz, 1H), 7.34-7.25 (m, 2H), 7.07 (t, J=7.8 Hz, 1H), 5.00 (q, J=7.9 Hz, 1H), 4.58-4.49 (m, 1H), 3.13 (quin, J=9.2 Hz, 2H), 2.42-2.31 (m, 1H), 2.22-2.05 (m, 2H), 1.89-1.64 (m, 3H), 1.57-1.46 (m, 1H), 0.89-0.75 (m, 1H), 0.50-0.37 (m, 2H), 0.25-0.07 (m, 2H)

Example 166. Synthesis of Viral Protease Inhibitor Compound 539

Step 1: (S)-methyl 2-amino-3-((S)-2-oxopyrrolidin-3-yl)propanoate hydrochloride

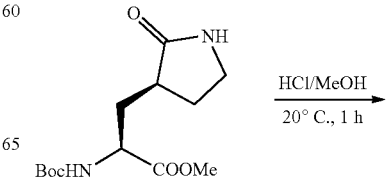

-continued

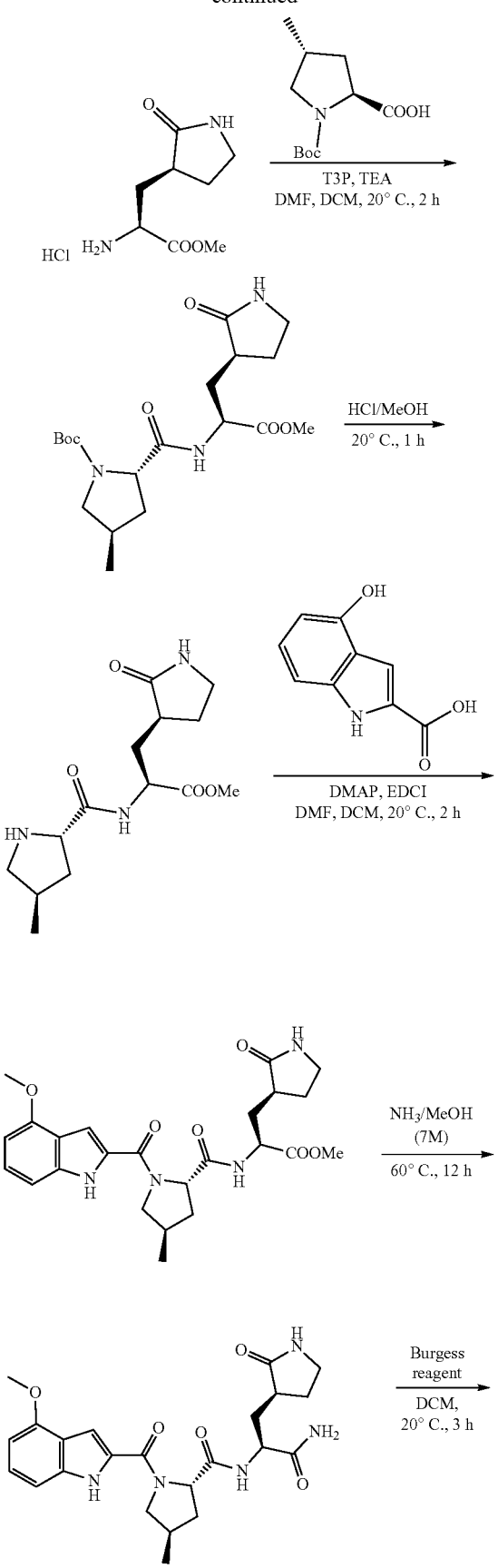

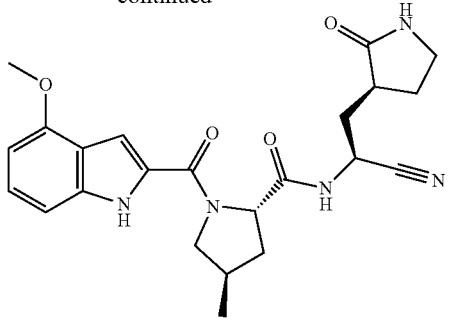

A solution of methyl (2S)-2-(tert-butoxycarbonylamino)-3-[(3S)-2-oxopyrrolidin-3-yl]propanoate (500 mg, 1.75 mmol, 1 eq) in HCl/MeOH (4 M, 20 mL, 45.81 eq) was stirred at 20° C. for 1 h. The reaction mixture was concentrated under reduced pressure to get the product methyl (2S)-2-amino-3-[(3S)-2-oxopyrrolidin-3-yl]propanoate (350 mg, crude, HCl) as a yellow solid.

Step 2: (2S,4R)-tert-butyl 2-(((S)-1-methoxy-1-oxo-3-((S)-2-oxopyrrolidin-3-yl)propan-2-yl)carbamoyl)-4-methylpyrrolidine-1-carboxylate To a solution of (2S,4R)-1-tert-butoxycarbonyl-4-methyl-pyrrolidine-2-carboxylic acid (250 mg, 1.09 mmol, 1 eq) and methyl (2S)-2-amino-3-[(3S)-2-oxopyrrolidin-3-yl]propanoate (304.45 mg, 1.64 mmol, 1.5 eq) in DCM (10 mL) was added drop-wise T3P (1.04 g, 1.64 mmol, 972.75 uL, 50% purity, 1.5 eq) and Et₃N (662.02 mg, 6.54 mmol, 910.62 uL, 6 eq), and the reaction was stirred at 20° C. for 2 h. The reaction mixture was quenched by addition H₂O (40 mL) at 0° C., and then extracted with DCM (30 mL*3). The combined organic layers were washed with brine 40 mL, dried over Na₂SO₄, filtered and concentrated under reduced pressure to give a residue. The residue was purified by column chromatography (SiO₂, petroleum ether:ethyl acetate=10:1 to 0:1) to get the product tert-butyl (2S,4R)-2-[[(1S)-2-methoxy-2-oxo-1-[[(3S)-2-oxopyrrolidin-3-yl]methyl]ethyl]carbamoyl]-4-methyl-pyrrolidine-1-carboxylate (320 mg, 805.10 umol, 73.86% yield) as a colorless oil. MS (ESI) m/z 398.2 [M+H]⁺.

Step 3: (S)-methyl 2-((2S,4R)-4-methylpyrrolidine-2-carboxamido)-3-((S)-2-oxopyrrolidin-3-yl)propanoate A solution of tert-butyl (2S,4R)-2-[[(1S)-2-methoxy-2-oxo-1-[[(3S)-2-oxopyrrolidin-3-yl]methyl]ethyl]carbamoyl]-4-methyl-pyrrolidine-1-carboxylate (260 mg, 654.15 umol, 1 eq) in HCl/MeOH (4 M, 8 mL, 48.92 eq) was stirred at 20° C. for 1 h. The reaction mixture was concentrated under reduced pressure to get the product methyl (2S)-2-[[(2S,4R)-4-methylpyrrolidine-2-carbonyl]amino]-3-[(3S)-2-oxopyrrolidin-3-yl]propanoate (200 mg, crude, HCl) as a colorless oil. MS (ESI) m/z 298.2 [M+H]⁺.

Step 4: (S)-methyl 2-((2S,4R)-1-(4-methoxy-1H-indole-2-carbonyl)-4-methylpyrrolidine-2-carboxamido)-3-((S)-2-oxopyrrolidin-3-yl)propanoate To a solution of methyl (2S)-2-[[(2S,4R)-4-methylpyrrolidine-2-carbonyl]amino]-3-[(3S)-2-oxopyrrolidin-3-yl]propanoate (200 mg, 599.14 umol, 1 eq, HCl) and 4-methoxy- 1H-indole-2-carboxylic acid (229.09 mg, 1.20 mmol, 2.0 eq) in DMF (2.0 mL) was added DMAP (219.59 mg, 1.80 mmol, 3.0 eq) and EDCI (229.71 mg, 1.20 mmol, 2 eq) and DCM (8.0 mL), the mixture was stirred at 20° C. for 2 h. The reaction mixture was quenched by addition H$_2$O (50 mL) at 0° C., and then extracted with DCM (40 mL*3). The combined organic layers were washed with brine 60 mL, dried over Na$_2$SO$_4$, filtered and concentrated under reduced pressure to give a residue. The residue was purified by column chromatography (SiO$_2$, petroleum ether:ethyl acetate=1:1 to 0:1) to get the product methyl (2S)-2-[[(2S,4R)-1-(4-methoxy-1H-indole-2-carbonyl)-4-methyl-pyrrolidine-2-carbonyl]amino]-3-[(3S)-2-oxopyrrolidin-3-yl]propanoate (250 mg, 494.14 umol, 82.47% yield, 93% purity) as a yellow solid. MS (ESI) m/z 471.3 [M+H]$^+$.

Step 5: (2S,4R)-N-[(1S)-2-amino-2-oxo-1-[[(3S)-2-oxopyrrolidin-3-yl]methyl]ethyl]-1-(4-methoxy-1H-indole-2-carbonyl)-4-methyl-pyrrolidine-2-carboxamide A solution of methyl (2S)-2-[[(2S,4R)-1-(4-methoxy-1H-indole-2-carbonyl)-4-methyl-pyrrolidine-2-carbonyl]amino]-3-[(3S)-2-oxopyrrolidin-3-yl]propanoate (220 mg, 434.84 umol, 93% purity, 1 eq) in NH$_3$/MeOH (7 M, 20 mL, 321.96 eq) was stirred at 60° C. for 12 h. The reaction mixture was concentrated under reduced pressure to get the product (2S,4R)-N-[(1S)-2-amino-2-oxo-1-[[(3S)-2-oxopyrrolidin-3-yl]methyl]ethyl]-1-(4-methoxy-1H-indole-2-carbonyl)-4-methyl-pyrrolidine-2-carboxamide (200 mg, crude) as a yellow solid. MS (ESI) m/z 456.2 [M+H]$^+$.

Step 6: (2S,4R)-N-[(1S)-1-cyano-2-[(3S)-2-oxopyrrolidin-3-yl]ethyl]-1-(4-methoxy-1H-indole-2-carbonyl)-4-methyl-pyrrolidine-2-carboxamide To a solution of (2S,4R)-N-[(1S)-2-amino-2-oxo-1-[[(3S)-2-oxopyrrolidin-3-yl]methyl]ethyl]-1-(4-methoxy-1H-indole-2-carbonyl)-4-methyl-pyrrolidine-2-carboxamide (100 mg, 219.54 umol, 1 eq) in DCM (5 mL) was added methoxycarbonyl-(triethylammonio)sulfonyl-azanide (313.90 mg, 1.32 mmol, 6 eq), and the mixture was stirred at 20° C. for 3 h. The reaction mixture was concentrated under reduced pressure to give a residue. The residue was purified by prep-HPLC (column: Phenomenex Luna C18 75*30 mm*3 um; mobile phase: [water (0.2% FA)-ACN]; B %: 25%-60%, 8 min) to get the product (2S,4R)-N-[(1S)-1-cyano-2-[(3S)-2-oxopyrrolidin-3-yl]ethyl]-1-(4-methoxy-1H-indole-2-carbonyl)-4-methyl-pyrrolidine-2-carboxamide (33 mg, 75.43 umol, 34.36% yield, 100% purity) as a white solid. MS (ESI) m/z 438.2 [M+H]$^+$.

$^1$H NMR (400 MHz, DMSO-d$_6$) δ=11.73-11.47 (m, 1H), 8.85 (br d, J=8.3 Hz, 1H), 7.84-7.54 (m, 1H), 7.24-6.84 (m, 3H), 6.74-6.48 (m, 1H), 5.10-4.47 (m, 2H), 4.20-3.75 (m, 4H), 3.47 (t, J=9.0 Hz, 1H), 3.16 (d, J=7.9 Hz, 1H), 2.61 (s, 1H), 2.43-2.36 (m, 1H), 2.27-1.43 (m, 7H), 1.07 (d, J=6.4 Hz, 3H).

$^1$H NMR (400 MHz, METHANOL-d$_4$) δ=7.25-6.75 (m, 3H), 6.59-6.40 (m, 1H), 5.15-5.00 (m, 1H), 4.84-4.61 (m, 1H), 4.30-4.06 (m, 1H), 3.98-3.84 (m, 3H), 3.55 (t, J=8.9 Hz, 1H), 3.30-3.24 (m, 1H), 3.01-2.54 (m, 2H), 2.46-2.09 (m, 4H), 2.01-1.38 (m, 3H), 1.15 (br d, J=6.6 Hz, 3H).

Example 167. Synthesis of Viral Protease Inhibitor Compound 547

Step 1: 9H-fluoren-9-ylmethyl (1S,2S,5R)-2-[[(1S)-1-cyano-2-[(3S)-2-oxopyrrolidin-3-yl]ethyl]carbamoyl]-3-azabicyclo[3.2.0]heptane-3-carboxylate

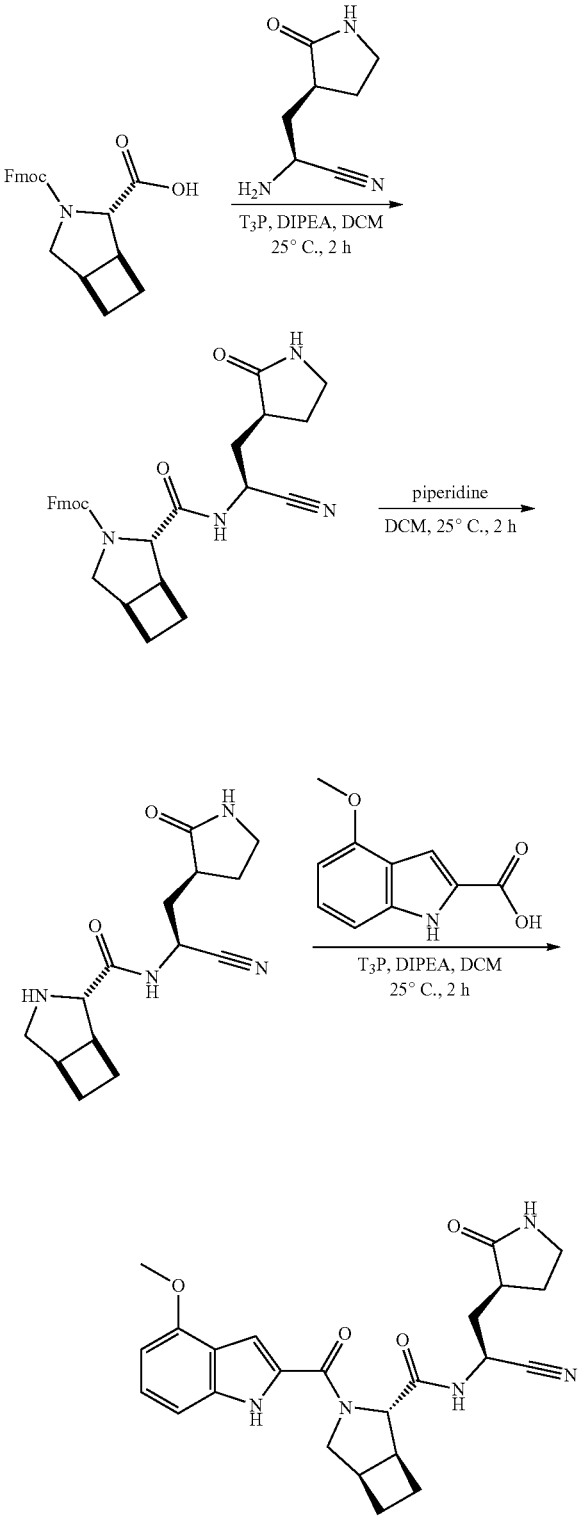

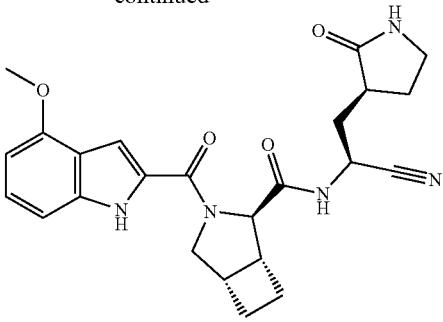

(1S,2S,5R)-3-(9H-fluoren-9-ylmethoxycarbonyl)-3-azabicyclo[3.2.0]heptane-2-carboxylic acid (250 mg, 687.94 umol, 1 eq), (2S)-2-amino-3-[(3S)-2-oxopyrrolidin-3-yl]propanenitrile (486.36 mg, 825.52 umol, 26% purity, 1.2 eq) in DCM (3 mL) was added T$_3$P (656.67 mg, 1.03 mmol, 613.71 uL, 50% purity, 1.5 eq) and DIEA (266.73 mg, 2.06 mmol, 359.48 uL, 3 eq), the solution was stirred at 25° C. for 2 h. After completion, the solution was diluted with H$_2$O (20 mL), extracted with ethyl acetate (30 mL*3), the combined organic phase was dried over Na$_2$SO$_4$, filtrated and concentrated to give the crude. The residue was purified by prep-TLC (SiO$_2$, DCM:MeOH=10:1). 9H-fluoren-9-ylmethyl (1S,2S,5R)-2-[[(1S)-1-cyano-2-[(3S)-2-oxopyrrolidin-3-yl]ethyl]carbamoyl]-3-azabicyclo[3.2.0]heptane-3-carboxylate (185 mg, 371.06 umol, 53.94% yield, 100% purity) was obtained as yellow solid. MS (ESI) m/z 499.2 [M+H]$^+$.

Step 2: (1S,2S,5R)-N-[(1S)-1-cyano-2-[(3S)-2-oxopyrrolidin-3-yl]ethyl]-3-azabicyclo[3.2.0]heptane-2-carboxamide To a solution of 9H-fluoren-9-ylmethyl (1S,2S,5R)-2-[[(1S)-1-cyano-2-[(3S)-2-oxopyrrolidin-3-yl]ethyl]carbamoyl]-3-azabicyclo[3.2.0]heptane-3-carboxylate (440 mg, 706.02 umol, 80% purity, 1 eq) in DCM (4.5 mL) was added the piperidine (60.11 mg, 706.02 umol, 69.72 uL, 1 eq) and the solution was stirred at 25° C. for 1 h. The solution was blow dry to remove the DCM and give the residue. The residue was purified by prep-TLC (SiO$_2$, DCM:MeOH=10:1). (1S,2S,5R)-N-[(1S)-1-cyano-2-[(3S)-2-oxopyrrolidin-3-yl]ethyl]-3-azabicyclo[3.2.0]heptane-2-carboxamide (165 mg, 597.10 umol, 84.57% yield, 100% purity) was obtained as yellow solid.

Step 3: (1S,2S,5R)-N-[(1S)-1-cyano-2-[(3S)-2-oxopyrrolidin-3-yl]ethyl]-3-(4-methoxy-1H-indole-2-carbonyl)-3-azabicyclo[3.2.0]heptane-2-carboxamide To a solution of N-[(1S)-1-cyano-2-[(3S)-2-oxopyrrolidin-3-yl]ethyl]-3-azabicyclo[3.2.0]heptane-2-carboxamide (165.00 mg, 597.10 umol, 1 eq), 4-methoxy-1H-indole-2-carboxylic acid (171.23 mg, 895.66 umol, 1.5 eq) in DCM (2 mL) was added the T$_3$P (284.98 mg, 895.66 umol, 266.34 uL, 1.5 eq), DIEA (154.34 mg, 1.19 mmol, 208.01 uL, 2 eq), the solution was stirred at 25° C. for 1 h. Upon completion, the solution was diluted with H$_2$O (20 mL), extracted with ethyl acetate (30 mL*3), the combined organic phase was dried over Na$_2$SO$_4$, filtrated and concentrated to give the crude. The residue was purified by prep-HPLC (neutral condition).

Column: Waters Xbridge Prep OBD C18 150*40 mm*10 um; mobile phase: [water (10 mM NH$_4$HCO$_3$)-ACN]; B %: 25%-45%, 8 min.

(1S,2S,5R)-N-[(1S)-1-cyano-2-[(3S)-2-oxopyrrolidin-3-yl]ethyl]-3-(4-methoxy-1H-indole-2-carbonyl)-3-azabicyclo[3.2.0]heptane-2-carboxamide (98 mg, 218.02 umol, 36.51% yield, 100% purity) was obtained as white solid. $^1$H NMR (400 MHz, DMSO-d6) δ=11.57 (br s, 1H), 8.79 (br d, J=7.4 Hz, 1H), 7.69 (br s, 1H), 7.17-6.95 (m, 3H), 6.52 (br d, J=7.3 Hz, 1H), 4.97 (br d, J=6.8 Hz, 1H), 4.63 (br d, J=8.2 Hz, 1H), 4.33-3.97 (m, 2H), 3.89 (br s, 3H), 3.28-2.79 (m, 4H), 2.30-1.55 (m, 9H). MS (ESI) m/z 450.3 [M+H]+.

(1R,2R,5S)-N-[(1S)-1-cyano-2-[(3S)-2-oxopyrrolidin-3-yl]ethyl]-3-(4-methoxy-1H-indole-2-carbonyl)-3-azabicyclo[3.2.0]heptane-2-carboxamide (23 mg, 51.17 umol, 8.57% yield, 100% purity) was obtained as white solid. $^1$H NMR (400 MHz, DMSO-d6) δ=11.56 (br s, 1H), 9.13-8.71 (m, 1H), 7.83-7.44 (m, 1H), 7.23-6.89 (m, 3H), 6.77-6.36 (m, 1H), 5.18-4.57 (m, 2H), 4.32-3.94 (m, 2H), 3.92-3.74 (m, 3H), 3.71-3.40 (m, 1H), 3.23-2.76 (m, 3H), 2.32-1.47 (m, 9H). MS (ESI) m/z 450.3 [M+H]$^+$.

Example 168. Synthesis of Viral Protease Inhibitor Compound 549

Step 1: tert-butyl (2S,4R)-2-[[[(1S)-2-methoxy-2-oxo-1-[[(3S)-2-oxopyrrolidin-3-yl]methyl] ethyl] carbamoyl]-4-(trifluoromethyl)pyrrolidine-1-carboxylate

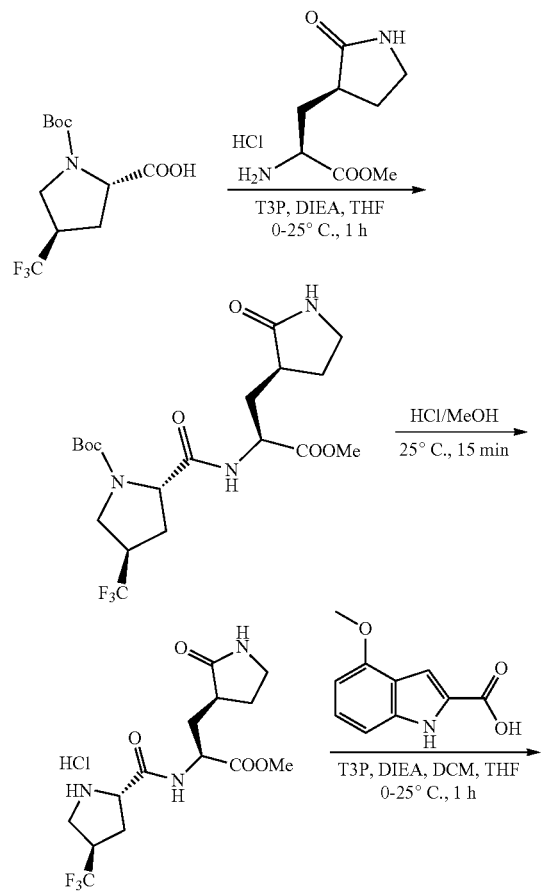

-continued

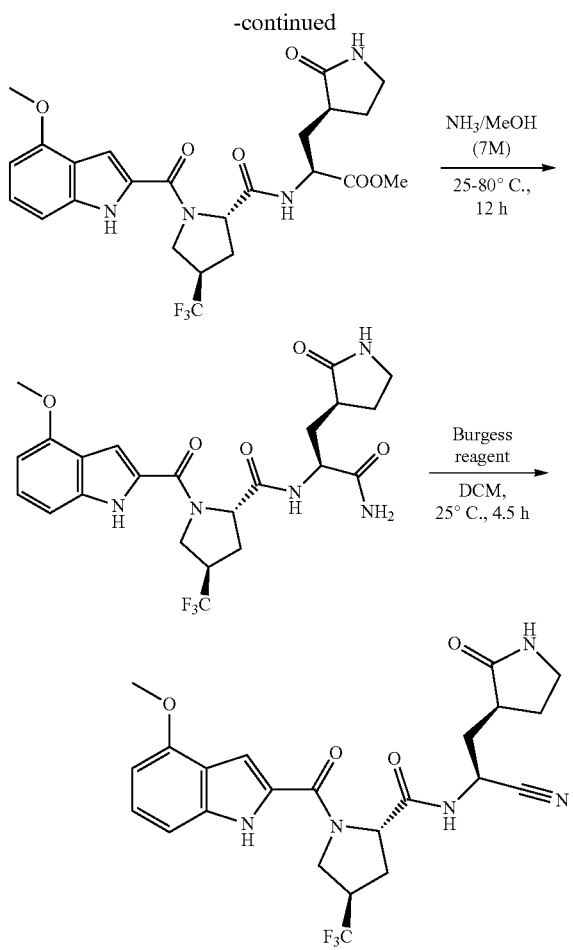

To a mixture of methyl (2S)-2-amino-3-[(3S)-2-oxopyrrolidin-3-yl]propanoate (283.01 mg, 1.27 mmol, 1.2 eq, HCl) and (2S,4R)-1-tert-butoxycarbonyl-4-(trifluoromethyl)pyrrolidine-2-carboxylic acid (300 mg, 1.06 mmol, 1 eq), DIEA (684.44 mg, 5.30 mmol, 922.43 uL, 5 eq) in THF (3 mL) was added T$_3$P (1.01 g, 1.59 mmol, 944.87 uL, 50% purity, 1.5 eq) at 0° C. under N$_2$. The mixture was stirred at 25° C. for 1 h. Upon completion, the residue was poured into saturated sodium bicarbonate solution (10 mL) and stirred for 1 min. The aqueous phase was extracted with ethyl acetate (10 mL*2). The combined organic phase was washed with brine (10 mL), dried with anhydrous Na$_2$SO$_4$, filtered and concentrated in vacuum to give Tert-butyl(2S,4R)-2-[[(1S)-2-methoxy-2-oxo-1-[[(3S)-2-oxopyrrolidin-3-yl]methyl]ethyl]carbamoyl]-4-(trifluoromethyl)pyrrolidine-1-carboxylate (0.5 g, crude) as light yellow oil and used directly next step. MS (ESI) m/z 452.1 [M+H]$^+$.

Step 2: methyl (2S)-3-[(3S)-2-oxopyrrolidin-3-yl]-2-[[(2S,4R)-4-(trifluoromethyl)pyrrolidine-2-carbonyl]amino]propanoate To a mixture of tert-butyl (2S,4R)-2-[[(1S)-2-methoxy-2-oxo-1-[[(3S)-2-oxopyrrolidin-3-yl]methyl] ethyl]carbamoyl]-4-(trifluoromethyl)pyrrolidine-1-carboxylate (0.5 g, 1.11 mmol, 1 eq) was added HCl/MeOH (4 M, 3 mL, 10.83 eq) at 25° C. under N$_2$. The mixture was stirred at 25° C. for 15 min. Upon completion, the reaction mixture was concentrated to get the crude product Methyl (2S)-3-[(3S)-2-oxopyrrolidin-3-yl]-2-[[(2S,4R)-4-(trifluoromethyl)pyrrolidine-2-carbonyl]amino]propanoate (450 mg, crude, HCl) as the light yellow oil. MS (ESI) m/z 352.1 [M+H]$^+$.

Step 3: methyl (2S)-2-[[(2S,4R)-1-(4-methoxy-1H-indole-2-carbonyl)-4-(trifluoromethyl)pyrrolidine-2-carbonyl]amino]-3-[(3S)-2-oxopyrrolidin-3-yl]propanoate To a mixture of methyl (2S)-3-[(3S)-2-oxopyrrolidin-3-yl]-2-[[(2S,4R)-4-(trifluoromethyl) pyrrolidine-2-carbonyl]amino]propanoate (395.52 mg, 1.02 mmol, 1.3 eq, HCl) and 4-methoxy-1H-indole-2-carboxylic acid (150 mg, 784.59 umol, 1 eq) and DIPEA (507.01 mg, 3.92 mmol, 683.31 uL, 5 eq) in THF (3 mL) and DCM (3 mL) was added T$_3$P (748.92 mg, 1.18 mmol, 699.93 uL, 50% purity, 1.5 eq) at 0° C. under N$_2$. The mixture was stirred at 25° C. for 1 h. Upon completion, the reaction mixture was poured into saturated sodium bicarbonate solution (5 mL) and stirred for 2 min. The aqueous phase was extracted with ethyl acetate (5 mL*2). The combined organic phase was washed with brine (5 mL), dried with anhydrous Na$_2$SO$_4$, filtered and concentrated in vacuum. The crude product was purified by prep-TLC (dichloromethane:methanol=10:1, R$_f$=0.43) to give methyl (2S)-2-[[(2S,4R)-1-(4-methoxy-1H-indole-2-carbonyl)-4-(trifluoromethyl)pyrrolidine-2-carbonyl]amino]-3-[(3S)-2-oxopyrrolidin-3-yl]propanoate (250 mg, crude) as a light yellow solid. MS (ESI) m/z 525.2 [M+H]$^+$.

Step 4: (2S,4R)-1-(4-methoxy-1H-indole-2-carbonyl)-N-[(1S)-1-(nitrosomethyl)-2-[(3S)-2-oxopyrrolidin-3-yl]ethyl]-4-(trifluoromethyl)pyrrolidine-2-carboxamide To a mixture of methyl (2S)-2-[[(2S,4R)-1-(4-methoxy-1H-indole-2-carbonyl)-4-(trifluoromethyl)pyrrolidine-2-carbonyl]amino]-3-[(3S)-2-oxopyrrolidin-3-yl]propanoate (250 mg, 476.65 umol, 1 eq) was added NH$_3$/MeOH (7 M, 3 mL, 44.06 eq) in one portion at 25° C. under N$_2$. The mixture was stirred at 80° C. for 12 h. Upon completion, the reaction mixture was cooled to 25° C. and concentrated to get the crude product. The crude product was purified by prep-TLC (dichloromethane:methanol=10:1, Rf=0.3) to give (2S,4R)-1-(4-methoxy-1H-indole-2-carbonyl)-N-[(1S)-1-(nitrosomethyl)-2-[(3S)-2-oxopyrrolidin-3-yl] ethyl]-4-(trifluoromethyl)pyrrolidine-2-carboxamide (130 mg, 247.51 umol, 51.93% yield, 97% purity) as a light yellow solid. MS (ESI) m/z 510.2 [M+H]$^+$.

Step 5: (2S,4R)-N-[(1S)-1-cyano-2-[(3S)-2-oxopyrrolidin-3-yl]ethyl]-1-(4-methoxy-1H-indole-2-carbonyl)-4-(trifluoromethyl)pyrrolidine-2-carboxamide To a mixture of (2S,4R)-1-(4-methoxy-1H-indole-2-carbonyl)-N-[(1S)-1-(nitrosomethyl)-2-[(3S)-2-oxopyrrolidin-3-yl]ethyl]-4-(trifluoromethyl)pyrrolidine-2-carboxamide (120 mg, 235.54 umol, 1 eq) in DCM (6 mL) was added Burgess reagent (112.26 mg, 471.07 umol, 2 eq) in one portion at 25° C. under N$_2$. The mixture was stirred at 25° C. for 4.5 h. Upon completion, the residue was poured into water (0.5 mL) and stirred for 10 min. Then the reaction mixture was concentrated to get the crude product. The crude product was purified by prep-HPLC (column: Phenomenex Gemini-NX 80*40 mm*3 um; mobile phase: [water (10 mM NH$_4$HCO$_3$)-ACN]; B %: 25%-45%, 8 min) to give (2S,4R)-N-[(1S)-1-cyano-2-[(3S)-2-oxopyrrolidin-3-yl]ethyl]-1-(4-methoxy-1H-indole-2-carbonyl)-4-(trifluoromethyl)pyrrolidine-2-carboxamide (22.56 mg, 45.90 umol, 19.49% yield, 100% purity) as a white solid. MS (ESI) m/z 492.2 [M+H]+.

1H NMR (400 MHz, METHANOL-d4) δ ppm 7.12-7.21 (m, 1H), 6.84-7.10 (m, 2H), 6.50 (br s, 1H), 4.94-5.26 (m, 1H), 4.75 (br s, 1H), 4.07-4.47 (m, 2H), 3.79-4.01 (m, 3H), 3.45 (br s, 1H), 2.16-2.98 (m, 6H), 1.62-2.02 (m, 2H), 1.39 (br s, 1H)

Example 169. Synthesis of Viral Protease Inhibitor Corn

Step 1: 9H-fluoren-9-ylmethyl (2S,4R)-2-[[(1S)-2-amino-2-oxo-1-[[(3S)-2-oxopyrrolidin-3-yl]methyl]ethyl]carbamoyl]-4-methylsulfanyl-pyrrolidine-1-carboxylate

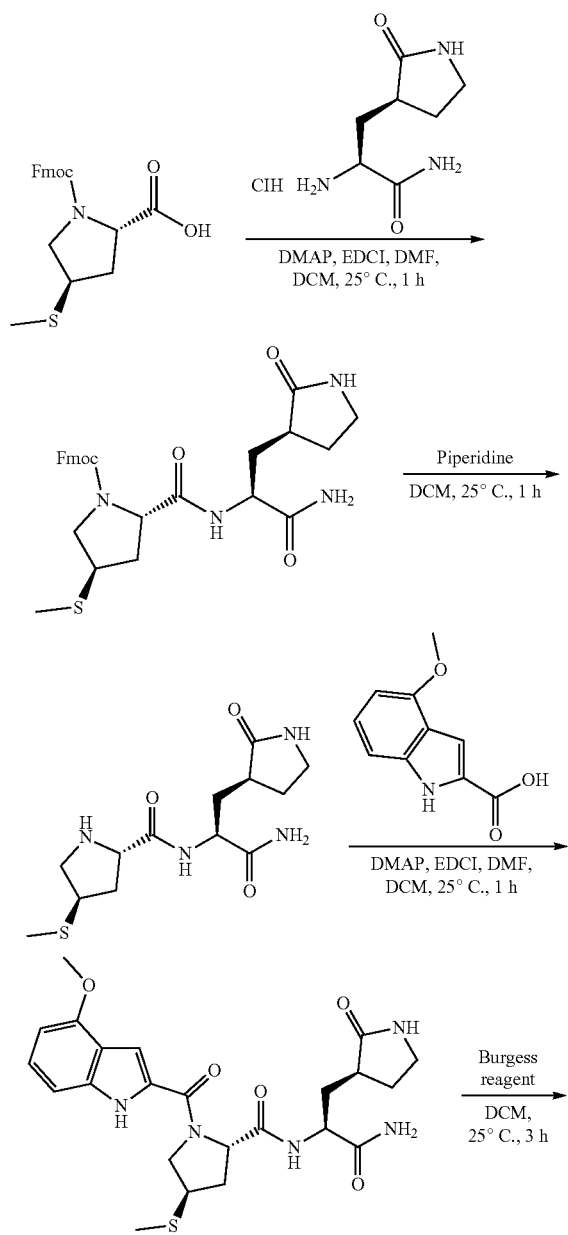

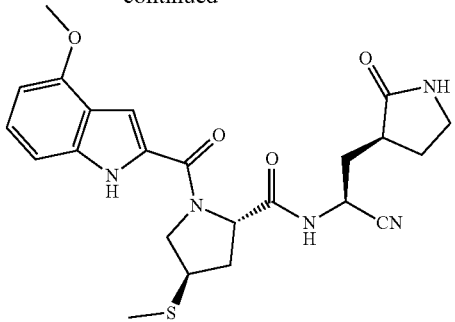

To a mixture (2S)-2-amino-3-[(3S)-2-oxopyrrolidin-3-yl] propanamide (200.57 mg, 782.35 umol, 81% purity, 1 eq, HCl) and (2S,4R)-1-(9H-fluoren-9-ylmethoxycarbonyl)-4-methylsulfanyl-pyrrolidine-2-carboxylic acid (300 mg, 782.35 umol, 1 eq) in DCM (4 mL) and DMF (2 mL) was added EDCI (299.96 mg, 1.56 mmol, 2 eq) and DMAP (191.16 mg, 1.56 mmol, 2 eq) in one portion at 25° C. under N2. The mixture was stirred at 25° C. and stirred for 1 hours. Upon completion. The aqueous phase was extracted with ethyl acetate (30 mL*3) and H2O (40 mL). The combined organic phase was washed with brine (30 mL*3), dried with anhydrous Na2SO4, filtered and concentrated in vacuum. To afford 9H-fluoren-9-ylmethyl (2S,4R)-2-[[(1S)-2-amino-2-oxo-1-[[(3S)-2-oxopyrrolidin-3-yl]methyl]ethyl]carbamoyl]-4-methylsulfanyl-pyrrolidine-1-carboxylate (180 mg, 322.00 umol, 41.16% yield, 96% purity) as white solid. MS (ESI) m/z 537.3 [M+H]+

Step 2: (2S,4R)-N-[(1S)-2-amino-2-oxo-1-[[(3S)-2-oxopyrrolidin-3-yl]methyl]ethyl]-4-methylsulfanyl-pyrrolidine-2-carboxamide To a mixture of 9H-fluoren-9-ylmethyl (2S,4R)-2-[[(1S)-2-amino-2-oxo-1-[[(3S)-2-oxopyrrolidin-3-yl]methyl]ethyl]carbamoyl]-4-methylsulfanyl-pyrrolidine-1-carboxylate (180 mg, 335.42 umol, 1 eq) in DCM (2 mL) was added piperidine (344.88 mg, 4.05 mmol, 0.4 mL, 12.08 eq) in one portion at 20° C. The mixture was stirred at 20° C. for 1 h. Upon completion. The crude was purified by pre-TLC (SiO2, DCM/MEOH=5/1). To afford (2S,4R)-N-[(1S)-2-amino-2-oxo-1-[[(3S)-2-oxopyrrolidin-3-yl]methyl]ethyl]-4-methylsulfanyl-pyrrolidine-2-carboxamide (80 mg, 127.23 umol, 37.93% yield, 50% purity) as a white solid.

1H NMR (400 MHz, DMSO-d6) δ=8.15 (br d, J=9.6 Hz, 1H), 7.63 (s, 1H), 7.53 (s, 1H), 7.12 (br s, 1H), 4.28 (br s, 1H), 3.73 (br t, J=7.2 Hz, 1H), 3.22-3.03 (m, 4H), 2.99 (br s, 2H), 2.78 (br d, J=7.2 Hz, 1H), 2.28-1.86 (m, 8H), 1.74-1.43 (m, 6H).

Step 3: (2S,4R)-N-[(1S)-2-amino-2-oxo-1-[[(3S)-2-oxopyrrolidin-3-yl]methyl]ethyl]-1-(4-methoxy-1H-indole-2-carbonyl)-4-methylsulfanyl-pyrrolidine-2-carboxamide To a mixture of (2S,4R)-N-[(1S)-2-amino-2-oxo-1-[[(3S)-2-oxopyrrolidin-3-yl]methyl]ethyl]-4-methylsulfanyl-pyrrolidine-2-carboxamide (80 mg, 254.45 umol, 1 eq) and 4-methoxy-1H-indole-2-carboxylic acid (48.65 mg, 254.45 umol, 1 eq) in DCM (2 mL) and DMF (1 mL) was added EDCI (97.56 mg, 508.90 umol, 2 eq) and DMAP (62.17 mg, 508.90 umol, 2 eq) in one portion at 20° C. and stirred for 1 h. Upon completion, the mixture was dried by N₂. The crude was purified by pre-HPLC, column: Phenomenex Gemini-NX C18 75*30 mm*3 um; mobile phase: [water (10 mM NH₄HCO₃)-ACN]; B %: 25%-45%, 8 min. To afford (2S,4R)-N-[(1S)-2-amino-2-oxo-1-[[(3S)-2-oxopyrrolidin-3-yl]methyl]ethyl]-1-(4-methoxy-1H-indole-2-carbonyl)-4-methylsulfanyl-pyrrolidine-2-carboxamide (80 mg, 164.08 umol, 64.48% yield, 100% purity) as white solid. MS (ESI) m/z 488.3 [M+H]⁺

Step 4: (2S,4R)-N-[(1S)-1-cyano-2-[(3S)-2-oxopyrrolidin-3-yl]ethyl]-1-(4-methoxy-1H-indole-2-carbonyl)-4-methylsulfanyl-pyrrolidine-2-carboxamide To a mixture of (2S,4R)-N-[(1S)-2-amino-2-oxo-1-[[(3S)-2-oxopyrrolidin-3-yl]methyl]ethyl]-1-(4-methoxy-1H-indole-2-carbonyl)-4-methylsulfanyl-pyrrolidine-2-carboxamide (80 mg, 164.08 umol, 1 eq) in DCM (4 mL) was added methoxycarbonyl-(triethylammonio)sulfonyl-azanide (312.81 mg, 1.31 mmol, 8 eq) in one portion at 20° C. and stirred for 3 h. Upon completion. The crude was dried by N₂. The crude was purified by pre-HPLC, column: Waters Xbridge BEH C18 100*30 mm*10 um; mobile phase: [water (10 mM NH₄HCO₃)-ACN]; B %: 15%-45%, 10 min. To afford (2S,4R)-N-[(1S)-1-cyano-2-[(3S)-2-oxopyrrolidin-3-yl]ethyl]-1-(4-methoxy-1H-indole-2-carbonyl)-4-methylsulfanyl-pyrrolidine-2-carboxamide (31.9 mg, 67.94 umol, 41.40% yield, 100% purity) as white solid. MS (ESI) m/z 470.2 [M+H]⁺

¹H NMR (400 MHz, DMSO-d₆) δ=11.38 (br s, 1H), 8.85 (br s, 1H), 7.46 (br s, 1H), 7.17-7.09 (m, 1H), 7.09-7.02 (m, 1H), 6.91 (br s, 1H), 6.52 (d, J=7.5 Hz, 1H), 4.95 (br d, J=7.1 Hz, 1H), 4.86-4.60 (m, 1H), 4.27 (br s, 1H), 3.90 (s, 4H), 3.54 (br s, 1H), 3.18-3.12 (m, 2H), 2.50-2.39 (br s, 8H), 1.89-1.61 (m, 2H).

Example 170. Synthesis of Viral Protease Inhibitor Compound 555

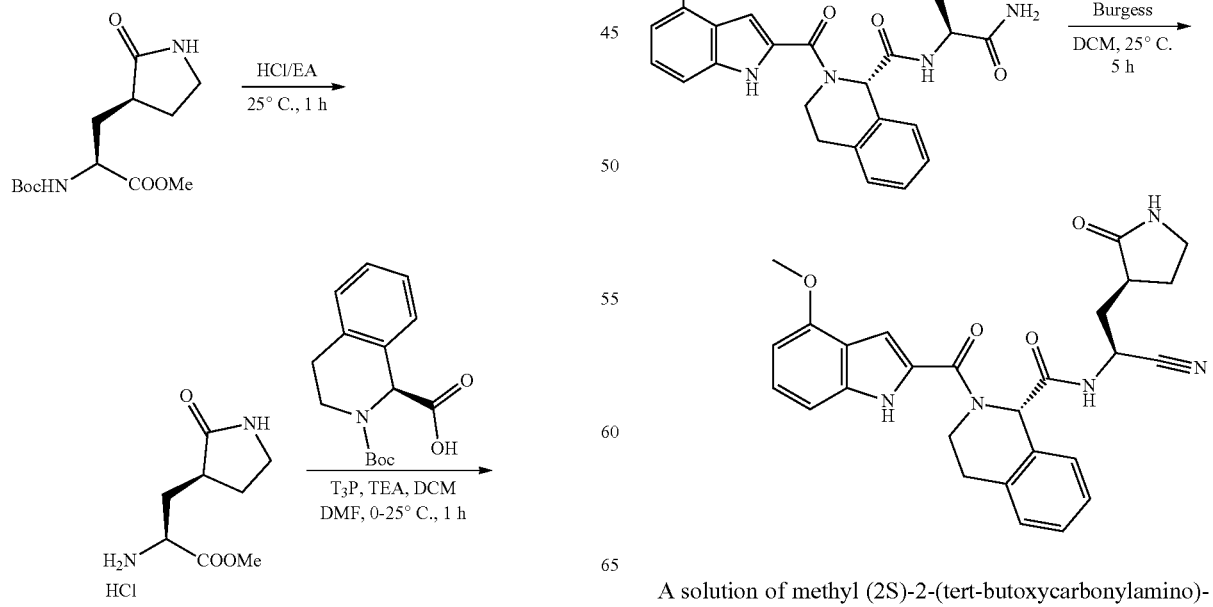

A solution of methyl (2S)-2-(tert-butoxycarbonylamino)-3-[(3S)-2-oxopyrrolidin-3-yl]propanoate (300 mg, 1.05 mmol, 1 eq) and HCl/EA (3 mL) was stirred at 25° C. for 0.5 h. Upon completion, the residue was concentrated under reduced pressure to get the product methyl (2S)-2-amino-3-[(3S)-2-oxopyrrolidin-3-yl]propanoate (200 mg, crude, HCl) as white solid MS (ESI) m/z 187.1 [M+H]⁺.

Step 2: tert-butyl (1S)-1-[[(1S)-2-methoxy-2-oxo-1-[[(3S)-2-oxopyrrolidin-3-yl]methyl]ethyl]carbamoyl]-3,4-dihydro-1H-isoquinoline-2-carboxylate A solution of methyl (2S)-2-amino-3-[(3S)-2-oxopyrrolidin-3-yl]propanoate (200 mg, 898.19 umol, 1 eq, HCl), (1S)-2-tert-butoxycarbonyl-3,4-dihydro-1H-isoquinoline-1-carboxylic acid (249.08 mg, 898.19 umol, 1 eq) and TEA (454.44 mg, 4.49 mmol, 625.09 uL, 5 eq) in DCM (2 mL) and DMF (1 mL) was cooled to 0° C. After adding T3P (1.71 g, 2.69 mmol, 1.60 mL, 50% purity, 3 eq) at 0° C., the mixture was stirred for 1 h and warmed to 25° C. gradually. Upon completion, the mixture was added H₂O (30 mL) and then extracted with ethyl acetate (30 mL*3). The combined organic layers were washed with brine (30 mL), dried over Na₂SO₄, filtered and concentrated under reduced pressure to get the product tert-butyl (1S)-1-[[(1S)-2-methoxy-2-oxo-1-[[(3S)-2-oxopyrrolidin-3-yl]methyl]ethyl]carbamoyl]-3,4-dihydro-1H-isoquinoline-2-carboxylate (300 mg, crude) as a yellow solid. MS (ESI) m/z 446.2 [M+H]⁺.

Step 3: methyl (2S)-3-[(3S)-2-oxopyrrolidin-3-yl]-2-[[(1S)-1,2,3,4-tetrahydroisoquinoline-1-carbonyl]amino]propanoate A solution of tert-butyl (1S)-1-[[(1S)-2-methoxy-2-oxo-1-[[(3S)-2-oxopyrrolidin-3-yl]methyl]ethyl]carbamoyl]-3,4-dihydro-1H-isoquinoline-2-carboxylate (300 mg, 673.39 umol, 1 eq) in HCl/EA (4 M) was stirred at 25° C. for 1 h. Upon completion, the reaction mixture was concentrated under reduced pressure to get the product methyl(2S)-3-[(3S)-2-oxopyrrolidin-3-yl]-2-[[(1S)-1,2,3,4-tetrahydroisoquinoline-1-carbonyl]amino]propanoate (210 mg, crude) as white solid. MS (ESI) m/z 346.2 [M+H]⁺.

Step 4: methyl (2S)-2-[[(1S)-2-(4-methoxy-1H-indole-2-carbonyl)-3,4-dihydro-1H-isoquinoline-1-carbonyl]amino]-3-[(3S)-2-oxopyrrolidin-3-yl]propanoate A solution of methyl (2S)-3-[(3S)-2-oxopyrrolidin-3-yl]-2-[[(1S)-1,2,3,4-tetrahydroisoquinoline-1-carbonyl]amino]propanoate (190 mg, 497.57 umol, 1 eq, HCl), 4-methoxy-1H-indole-2-carboxylic acid (95.13 mg, 497.57 umol, 1 eq), EDCI (286.16 mg, 1.49 mmol, 3 eq) and DMAP (182.36 mg, 1.49 mmol, 3 eq) in DCM (4 mL) was stirred at 25° C. for 1 h. Upon completion, the mixture was added H₂O (30 mL) and then extracted with ethyl acetate (30 mL*3). The combined organic layers were washed with brine (30 mL), dried over Na₂SO₄, filtered and concentrated under reduced pressure to give a residue. The residue was purified by prep-HPLC (column: Phenomenex Gemini-NX C18 75*30 mm*3 um; mobile phase: [water (0.05% NH₃H₂O+10 mM NH₄HCO₃)-ACN]; B %: 30%-60%, 8 min) to get the product methyl (2S)-2-[[(1S)-2-(4-methoxy-1H-indole-2-carbonyl)-3,4-dihydro-1H-isoquinoline-1-carbonyl]amino]-3-[(3S)-2-oxopyrrolidin-3-yl]propanoate (40.1 mg, 73.46 umol, 14.76% yield, 95% purity) as a white solid. MS (ESI) m/z 519.2 [M+H]⁺.

Step 5: (1S)-N-[(1S)-2-amino-2-oxo-1-[[(3S)-2-oxopyrrolidin-3-yl]methyl]ethyl]-2-(4-methoxy-1H-indole-2-carbonyl)-3,4-dihydro-1H-isoquinoline-1-carboxamide A solution of methyl (2S)-2-[[(1S)-2-(4-methoxy-1H-indole-2-carbonyl)-3,4-dihydro-1H-isoquinoline-1-carbonyl]amino]-3-[(3S)-2-oxopyrrolidin-3-yl]propanoate (40 mg, 77.14 umol, 1 eq) and NH₃/MeOH (7 M, 10 mL, 907.48 eq) was stirred at 25° C. for 16 h. Upon completion, the reaction mixture was concentrated under reduced pressure to afford (1S)-N-[(1S)-2-amino-2-oxo-1-[[(3S)-2-oxopyrrolidin-3-yl]methyl]ethyl]-2-(4-methoxy-1H-indole-2-carbonyl)-3,4-dihydro-1H-isoquinoline-1-carboxamide (35 mg, crude) as a yellow solid. MS (ESI) m/z 504.2 [M+H]⁺.

Step 6: (1S)-N-[(1S)-1-cyano-2-[(3S)-2-oxopyrrolidin-3-yl]ethyl]-2-(4-methoxy-1H-indole-2-carbonyl)-3,4-dihydro-1H-isoquinoline-1-carboxamide A solution of (1S)-N-[(1S)-2-amino-2-oxo-1-[[(3S)-2-oxopyrrolidin-3-yl]methyl]ethyl]-2-(4-methoxy-1H-indole-2-carbonyl)-3,4-dihydro-1H-isoquinoline-1-carboxamide (35 mg, 69.51 umol, 1 eq) and methoxycarbonyl-(triethylammonio)sulfonyl-azanide (82.82 mg, 347.53 umol, 5 eq) in DCM (5 mL) was stirred at 25° C. for 5 h. Upon completion, the reaction mixture was concentrated under reduced pressure to give a residue. The residue was purified by prep-HPLC (column: Phenomenex Gemini-NX C18 75*30 mm*3 um; mobile phase: [water (0.05% NH₃H₂O+10 mM NH₄HCO₃)-ACN]; B %: 20%-50%, 8 min) to get the product (1S)-N-[(1S)-1-cyano-2-[(3S)-2-oxopyrrolidin-3-yl]ethyl]-2-(4-methoxy-1H-indole-2-carbonyl)-3,4-dihydro-1H-isoquinoline-1-carboxamide (6 mg, 12.08 umol, 17.38% yield, 97.74% purity) as white solid. MS (ESI) m/z 486.2 [M+H]⁺.

¹H NMR (400 MHz, METHANOL-d₄) δ=7.57-7.47 (m, 1H), 7.40-7.25 (m, 1H), 7.12-7.11 (m, 1H), 7.10-6.99 (m, 2H), 6.59-6.50 (m, 1H), 6.82-6.61 (m, 1H), 5.67 (s, 1H), 5.03-4.96 (m, 1H), 4.46 (s, 1H), 4.05-3.95 (m, 1H), 3.94-3.86 (m, 3H), 3.37-3.32 (m, 1H), 3.28-3.16 (m, 2H), 3.05-2.90 (m, 2H), 2.62 (s, 1H), 2.44-2.20 (m, 2H), 1.98-1.67 (m, 2H)

Example 171. Synthesis of Viral Protease Inhibitor Compound 557

Step 1: (S)-methyl 2-amino-3-((S)-2-oxopyrrolidin-3-yl)propanoate hydrochloride

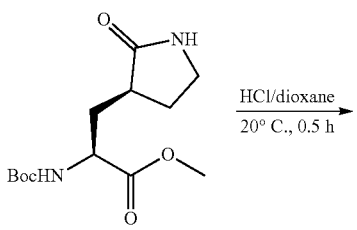

1165  
-continued

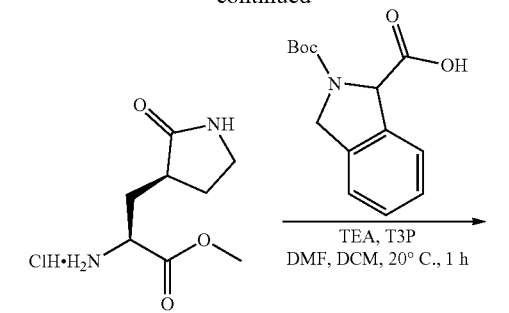

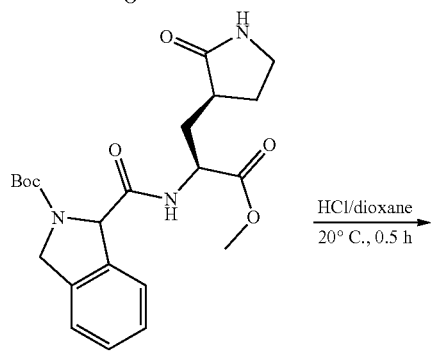

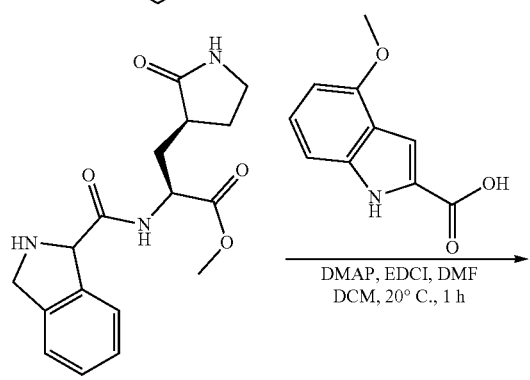

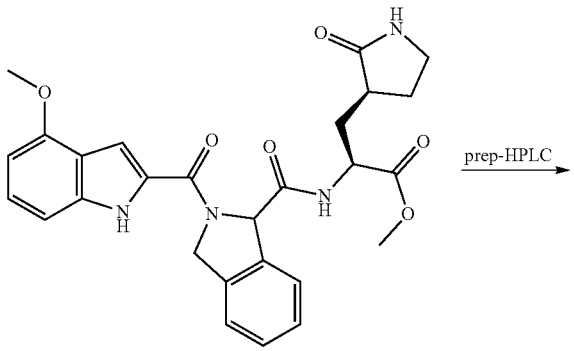

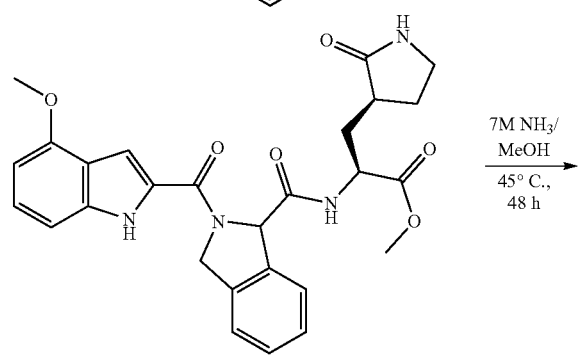

1166  
-continued

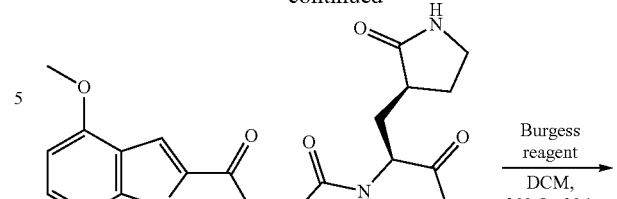

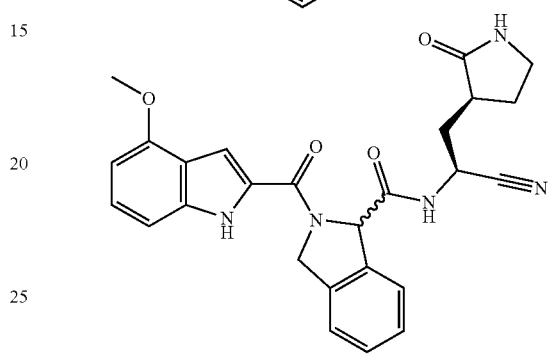

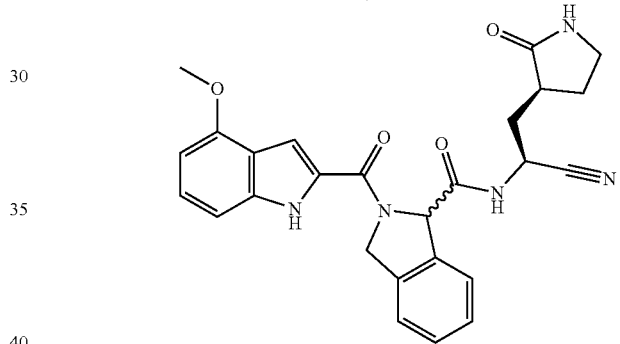

A mixture of methyl (2S)-2-(tert-butoxycarbonylamino)-3-[(3S)-2-oxopyrrolidin-3-yl]propanoate (500 mg, 1.75 mmol, 1 eq) in HCl/dioxane (4 M, 8.73 mL, 20 eq) was degassed and purged with $N_2$ for 3 times, and then the mixture was stirred at 20° C. for 0.5 h under $N_2$ atmosphere. Upon completion, the reaction mixture was concentrated under reduced pressure to afford methyl (2S)-2-amino-3-[(3S)-2-oxopyrrolidin-3-yl]propanoate (630 mg, crude, HCl) as yellow oil. MS (ESI) m/z 223.2 [M+H]$^+$.

Step 2: tert-butyl 1-(((S)-1-methoxy-1-oxo-3-((S)-2-oxopyrrolidin-3-yl)propan-2-yl)carbamoyl)isoindoline-2-carboxylate To a solution of 2-tert-butoxycarbonylisoindoline-1-carboxylic acid (436.93 mg, 1.66 mmol, 1 eq) methyl (2S)-2-amino-3-[(3S)-2-oxopyrrolidin-3-yl]propanoate (630 mg, 1.74 mmol, 61.58% purity, 1.05 eq, HCl) in DCM (5 mL) and DMF (5 mL) was added $T_3P$ (1.58 g, 2.49 mmol, 1.48 mL, 50% purity, 1.5 eq) and TEA (1.01 g, 9.96 mmol, 1.39 mL, 6 eq). The mixture was stirred at 20° C. for 1 h. Upon completion, the reaction mixture was quenched by addition $H_2O$ (20 mL), and extracted with ethyl acetate (10 mL*3). The combined organic layers were washed with brine (15 mL), dried over $Na_2SO_4$, filtered and concentrated under reduced pressure to get the product tert-butyl 1-[[(1S)-2-methoxy-2-oxo-1-[[(3S)-2-oxopyrrolidin-3-yl]methyl]ethyl]carbamoyl]isoindoline-2-carboxylate (720 mg, crude) as a white solid. MS (ESI) m/z 432.2 [M+H]$^+$.

Step 3: (2S)-methyl 2-(isoindoline-1-carboxamido)-3-((S)-2-oxopyrrolidin-3-yl)propanoate A mixture of tert-butyl 1-[[(1S)-2-methoxy-2-oxo-1-[[(3S)-2-oxopyrrolidin-3-yl]methyl]ethyl]carbamoyl]isoindoline-2-carboxylate (720 mg, 1.67 mmol, 1 eq) in HCl/dioxane (4 M, 8.34 mL, 20 eq) was degassed and purged with N$_2$ for 3 times, and then the mixture was stirred at 20° C. for 0.5 h under N$_2$ atmosphere. Upon completion, the reaction mixture was concentrated under reduced pressure to get the product methyl (2S)-2-(isoindoline-1-carbonylamino)-3-[(3S)-2-oxopyrrolidin-3-yl]propanoate (770 mg, crude, HCl) as a brown oil. MS (ESI) m/z 332.3[M+H]$^+$.

Step 4: (2S)-methyl 2-(2-(4-methoxy-1H-indole-2-carbonyl)isoindoline-1-carboxamido)-3-((S)-2-oxopyrrolidin-3-yl)propanoate A mixture of 4-methoxy-1H-indole-2-carboxylic acid (287.43 mg, 1.50 mmol, 1 eq), methyl (2S)-2-(isoindoline-1-carbonylamino)-3-[(3S)-2-oxopyrrolidin-3-yl]propanoate (770 mg, 1.65 mmol, 79% purity, 1.1 eq, HCl), DMAP (367.34 mg, 3.01 mmol, 2 eq), EDCI (576.42 mg, 3.01 mmol, 2 eq) in DCM (8 mL) and DMF (2.7 mL) was degassed and purged with N$_2$ for 3 times, and then the mixture was stirred at 20° C. for 1 h under N$_2$ atmosphere. Upon completion, the reaction mixture was quenched by addition H$_2$O (25 mL), and then extracted with DCM (10 mL*3). The combined organic layers were washed with brine (15 mL), dried over Na$_2$SO$_4$, filtered and concentrated under reduced pressure to give a residue. The residue was purified by neutral prep-HPLC (column: Kromasil C18 (250*50 mm*10 um); mobile phase: [water (10 mM NH$_4$HCO$_3$)-ACN]; B %: 25%-45%, 10 min) to get the product methyl (2S)-2-[[2-(4-methoxy-1H-indole-2-carbonyl)isoindoline-1-carbonyl]amino]-3-[(3S)-2-oxopyrrolidin-3-yl]propanoate (Isomer 1: 150 mg, 297.30 umol, 19.78% yield) as a white solid. MS (ESI) m/z 505.3[M+H]$^+$.

To get methyl (2S)-2-[[2-(4-methoxy-1H-indole-2-carbonyl)isoindoline-1-carbonyl]amino]-3-[(3S)-2-oxopyrrolidin-3-yl]propanoate (Isomer 2: 140 mg, 277.48 umol, 18.46% yield) as white solid. MS (ESI) m/z 505.3[M+H]+.

Step 5.1: N-((S)-1-amino-1-oxo-3-((S)-2-oxopyrrolidin-3-yl)propan-2-yl)-2-(4-methoxy-1H-indole-2-carbonyl)isoindoline-1-carboxamide A solution of methyl (2S)-2-[[2-(4-methoxy-1H-indole-2-carbonyl)isoindoline-1-carbonyl]amino]-3-[(3S)-2-oxopyrrolidin-3-yl]propanoate (150 mg, 297.30 umol, 1 eq) in MeOH/NH$_3$ (7 M, 849.44 uL, 20 eq) was stirred at 45° C. for 48 h. Upon completion, the reaction mixture was concentrated under reduced pressure to get the product N-[(1S)-2-amino-2-oxo-1-[[(3S)-2-oxopyrrolidin-3-yl]methyl]ethyl]-2-(4-methoxy-1H-indole-2-carbonyl)isoindoline-1-carboxamide (130 mg, crude) as a colorless oil. MS (ESI) m/z 490.3[M+H]$^+$.

Step 5.2: N-((S)-1-amino-1-oxo-3-((S)-2-oxopyrrolidin-3-yl)propan-2-yl)-2-(4-methoxy-1H-indole-2-carbonyl)isoindoline-1-carboxamide A solution of methyl (2S)-2-[[2-(4-methoxy-1H-indole-2-carbonyl)isoindoline-1-carbonyl] amino]-3-[(3S)-2-oxopyrrolidin-3-yl]propanoate (140 mg, 277.48 umol, 1 eq) in MeOH/NH$_3$ (7 M, 792.81 uL, 20 eq) was stirred at 45° C. for 24 h. Upon completion, the reaction mixture was concentrated under reduced pressure to get the product N-[(1S)-2-amino-2-oxo-1-[[(3S)-2-oxopyrrolidin-3-yl]methyl]ethyl]-2-(4-methoxy-1H-indole-2-carbonyl)isoindoline-1-carboxamide (110 mg, crude) as a colorless oil. MS (ESI) m/z 490.3[M+H]$^+$.

Step 6.1: N-((S)-1-cyano-2-((S)-2-oxopyrrolidin-3-yl)ethyl)-2-(4-methoxy-1H-indole-2-carbonyl)isoindoline-1-carboxamide To a solution of N-[(1S)-2-amino-2-oxo-1-[[(3S)-2-oxopyrrolidin-3-yl]methyl]ethyl]-2-(4-methoxy-1H-indole-2-carbonyl)isoindoline-1-carboxamide (125 mg, 255.35 umol, 1 eq) in DCM (8 mL) was added Burgess reagent (273.84 mg, 1.15 mmol, 4.5 eq). The mixture was stirred at 30° C. for 20 h. Upon completion, the reaction mixture was quenched by addition H$_2$O (0.5 mL), and then concentrated under reduced pressure to give a residue. The residue was purified by neutral prep-HPLC (column: Waters Xbridge BEH C18 100*25 mm*5 um; mobile phase: [water (10 mM NH$_4$HCO$_3$)-ACN]; B %: 20%-50%, 10 min) to get the product N-[(1S)-1-cyano-2-[(3S)-2-oxopyrrolidin-3-yl]ethyl]-2-(4-methoxy-1H-indole-2-carbonyl)isoindoline-1-carboxamide (31.50 mg, 66.81 umol, 26.16% yield, 100% purity) as a white solid. MS (ESI) m/z 472.3[M+H]$^+$.

$^1$H NMR (400 MHz, DMSO-d$_6$) δ ppm 11.53-11.83 (m, 1H) 9.11-9.78 (m, 1H) 7.31-7.78 (m, 5H) 6.95-7.29 (m, 3H) 6.42-6.63 (m, 1H) 5.73 (s, 1H) 5.27-5.41 (m, 1H) 4.91-5.05 (m, 1H) 3.76-3.99 (m, 3H) 2.71-3.19 (m, 2H) 2.00-2.30 (m, 3H) 1.20-1.87 (m, 2H).

Step 6.2: N-((S)-1-cyano-2-((S)-2-oxopyrrolidin-3-yl)ethyl)-2-(4-methoxy-1H-indole-2-carbonyl)isoindoline-1-carboxamide To a solution of N-[(1S)-2-amino-2-oxo-1-[[(3S)-2-oxopyrrolidin-3-yl]methyl]ethyl]-2-(4-methoxy-1H-indole-2-carbonyl)isoindoline-1-carboxamide (105 mg, 214.49 umol, 1 eq) in DCM (6 mL) was added Burgess reagent (204.47 mg, 857.98 umol, 4 eq). The mixture was stirred at 30° C. for 7 h. Upon completion, the reaction mixture was quenched by addition H$_2$O (0.5 mL), and then concentrated under reduced pressure to give a residue. The residue was purified by neutral prep-HPLC (column: Waters Xbridge Prep OBD C18 150*40 mm*10 um; mobile phase: [water (10 mM NH4HCO3)-ACN]; B %: 25%-55%, 8 min) to get the product N-[(1S)-1-cyano-2-[(3S)-2-oxopyrrolidin-3-yl]ethyl]-2-(4-methoxy-1H-indole-2-carbonyl)isoindoline-1-carboxamide (34.83 mg, 73.72 umol, 34.37% yield, 99.791% purity) as a white solid. MS (ESI) m/z 472.3[M+H]$^+$.

$^1$H NMR (400 MHz, DMSO-d$_6$) δ ppm 11.72 (s, 1H) 9.19 (d, J=8.11 Hz, 1H) 7.31-7.76 (m, 5H) 6.92-7.29 (m, 3H) 6.56 (d, J=7.75 Hz, 1H) 5.74 (s, 1H) 5.34 (br d, J=10.13 Hz, 1H) 4.96 (q, J=8.23 Hz, 1H) 3.86-3.89 (m, 1H) 3.86-4.55 (m, 1H) 3.84-4.01 (m, 3H) 2.96-3.22 (m, 2H) 2.25-2.41 (m, 1H) 2.02-2.20 (m, 2H) 1.47-1.87 (m, 2H).

Example 172. Synthesis of Viral Protease Inhibitor Compound 577

Step 1: (S)-methyl 2-amino-3-((S)-2-oxopyrrolidin-3-yl)propanoate

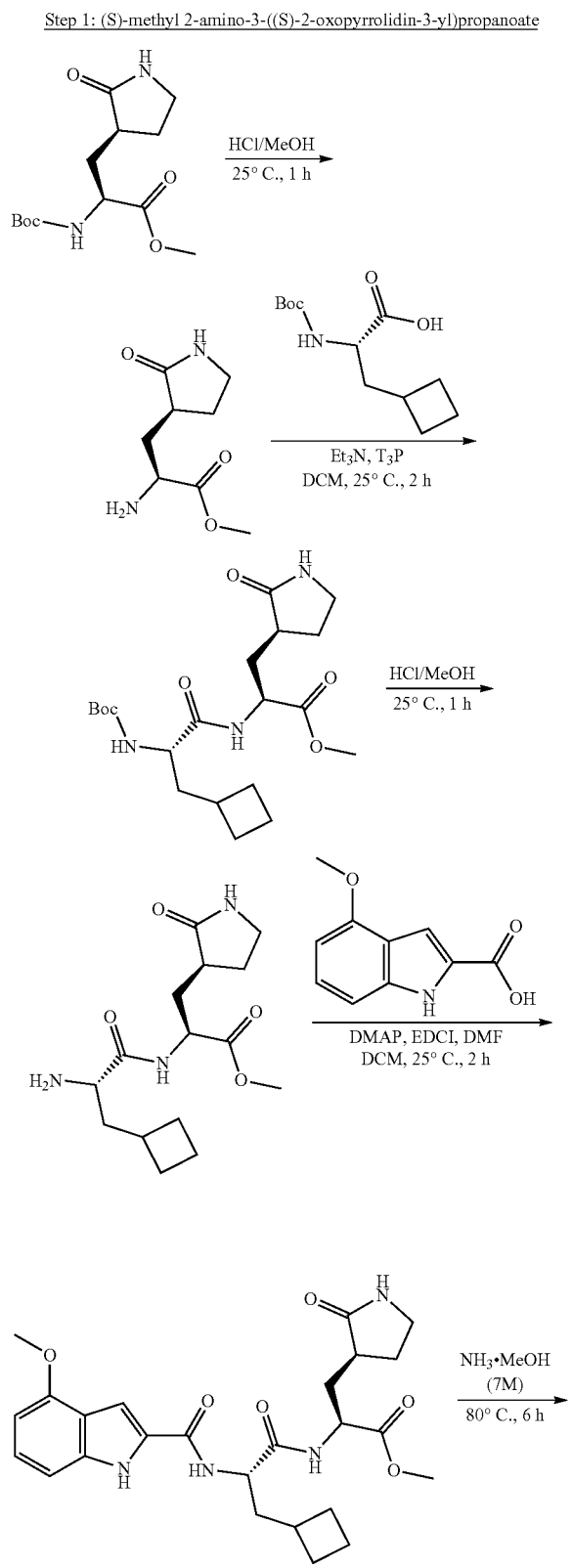

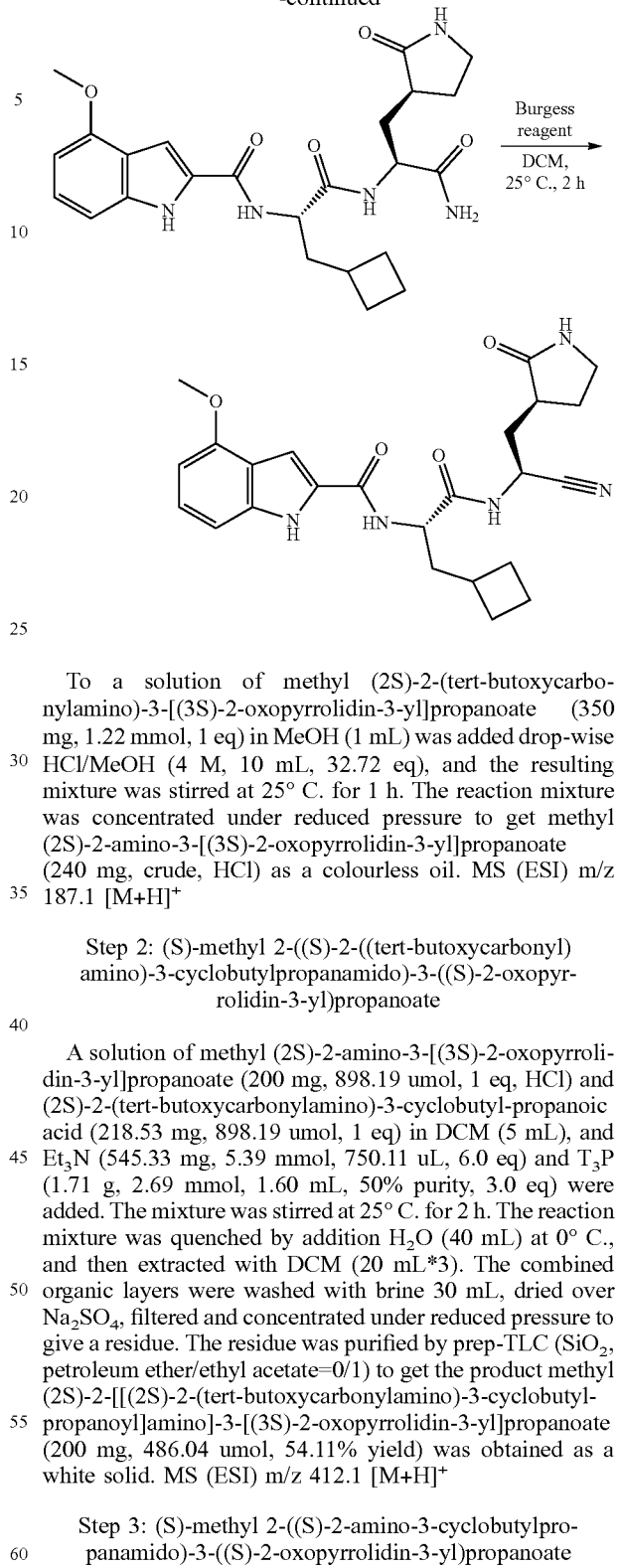

To a solution of methyl (2S)-2-(tert-butoxycarbonylamino)-3-[(3S)-2-oxopyrrolidin-3-yl]propanoate (350 mg, 1.22 mmol, 1 eq) in MeOH (1 mL) was added drop-wise HCl/MeOH (4 M, 10 mL, 32.72 eq), and the resulting mixture was stirred at 25° C. for 1 h. The reaction mixture was concentrated under reduced pressure to get methyl (2S)-2-amino-3-[(3S)-2-oxopyrrolidin-3-yl]propanoate (240 mg, crude, HCl) as a colourless oil. MS (ESI) m/z 187.1 [M+H]+

Step 2: (S)-methyl 2-((S)-2-((tert-butoxycarbonyl)amino)-3-cyclobutylpropanamido)-3-((S)-2-oxopyrrolidin-3-yl)propanoate A solution of methyl (2S)-2-amino-3-[(3S)-2-oxopyrrolidin-3-yl]propanoate (200 mg, 898.19 umol, 1 eq, HCl) and (2S)-2-(tert-butoxycarbonylamino)-3-cyclobutyl-propanoic acid (218.53 mg, 898.19 umol, 1 eq) in DCM (5 mL), and Et₃N (545.33 mg, 5.39 mmol, 750.11 uL, 6.0 eq) and T₃P (1.71 g, 2.69 mmol, 1.60 mL, 50% purity, 3.0 eq) were added. The mixture was stirred at 25° C. for 2 h. The reaction mixture was quenched by addition H₂O (40 mL) at 0° C., and then extracted with DCM (20 mL*3). The combined organic layers were washed with brine 30 mL, dried over Na₂SO₄, filtered and concentrated under reduced pressure to give a residue. The residue was purified by prep-TLC (SiO₂, petroleum ether/ethyl acetate=0/1) to get the product methyl (2S)-2-[[(2S)-2-(tert-butoxycarbonylamino)-3-cyclobutyl-propanoyl]amino]-3-[(3S)-2-oxopyrrolidin-3-yl]propanoate (200 mg, 486.04 umol, 54.11% yield) was obtained as a white solid. MS (ESI) m/z 412.1 [M+H]+

Step 3: (S)-methyl 2-((S)-2-amino-3-cyclobutylpropanamido)-3-((S)-2-oxopyrrolidin-3-yl)propanoate To a solution of methyl (2S)-2-[[(2S)-2-(tert-butoxycarbonylamino)-3-cyclobutyl-propanoyl]amino]-3-[(3S)-2-oxopyrrolidin-3-yl]propanoate (180 mg, 437.43 umol, 1 eq) in MeOH (1 mL) was added drop-wise HCl/MeOH (4 M, 12.00 mL, 109.73 eq), and the resulting mixture was stirred at 25° C. for 1 h. The reaction mixture was concentrated under reduced pressure to afford methyl (2S)-2-[[(2S)-2-amino-3-cyclobutyl-propanoyl]amino]-3-[(3S)-2-oxopyrrolidin-3-yl]propanoate (150 mg, HCl) as a white solid. MS (ESI) m/z 312.2 [M+H]$^+$ Step 4: (S)-methyl 2-((S)-3-cyclobutyl-2-(4-methoxy-1H-indole-2-carboxamido)propanamido)-3-((S)-2-oxopyrrolidin-3-yl)propanoate To a solution of methyl (2S)-2-[[(2S)-2-amino-3-cyclobutyl-propanoyl]amino]-3-[(3S)-2-oxopyrrolidin-3-yl]propanoate (150 mg, 431.24 umol, 1 eq, HCl) and 4-methoxy-1H-indole-2-carboxylic acid (82.45 mg, 431.24 umol, 1 eq) in DMF (1.5 mL) was added DMAP (105.37 mg, 862.47 umol, 2.0 eq), EDCI (165.34 mg, 862.47 umol, 2.0 eq) and DCM (6 mL). The mixture was stirred at 25° C. for 2 h. The reaction mixture was quenched by addition H$_2$O (40 mL) at 0° C., and extracted with DCM (20 mL*3). The combined organic layers were washed with brine 30 mL, dried over Na$_2$SO$_4$, filtered and concentrated under reduced pressure to give a residue. The residue was purified by prep-TLC (SiO$_2$, petroleum ether/ethyl acetate=0/1) to afford methyl (2S)-2-[[(2S)-3-cyclobutyl-2-[(4-methoxy-1H-indole-2-carbonyl)amino]propanoyl]amino]-3-[(3S)-2-oxopyrrolidin-3-yl]propanoate (120 mg, 247.66 umol, 57.43% yield) as a yellow oil. MS (ESI) m/z 485.2 [M+H]$^+$ Step 5: N-((S)-1-(((S)-1-amino-1-oxo-3-((S)-2-oxopyrrolidin-3-yl)propan-2-yl)amino)-3-cyclobutyl-1-oxopropan-2-yl)-4-methoxy-1H-indole-2-carboxamide A solution of methyl (2S)-2-[[(2S)-3-cyclobutyl-2-[(4-methoxy-1H-indole-2-carbonyl)amino]propanoyl]amino]-3-[(3S)-2-oxopyrrolidin-3-yl]propanoate (100 mg, 206.38 umol, 1 eq) in NH$_3$/MeOH (7 M, 10 mL, 339.18 eq) was stirred at 80° C. for 6 h. The reaction mixture was concentrated under reduced pressure to afford N-[(1S)-2-[[(1S)-2-amino-2-oxo-1-[[(3S)-2-oxopyrrolidin-3-yl]methyl]ethyl]amino]-1-(cyclobutylmethyl)-2-oxo-ethyl]-4-methoxy-1H-indole-2-carboxamide (90 mg, crude) as a yellow solid. MS (ESI) m/z 470.1 [M+H]$^+$ Step 7: N-((S)-1-(((S)-1-cyano-2-((S)-2-oxopyrrolidin-3-yl)ethyl)amino)-3-cyclobutyl-1-oxopropan-2-yl)-4-methoxy-1H-indole-2-carboxamide To a solution of N-[(1S)-2-[[(1S)-2-amino-2-oxo-1-[[(3S)-2-oxopyrrolidin-3-yl]methyl]ethyl]amino]-1-(cyclobutylmethyl)-2-oxo-ethyl]-4-methoxy-1H-indole-2-carboxamide (90 mg, 191.68 umol, 1 eq) in DCM (2 mL) was added methoxycarbonyl-(triethylammonio)sulfonyl-azanide (228.40 mg, 958.40 umol, 5.0 eq), and the mixture was stirred at 25° C. for 2 h. The reaction mixture was concentrated under reduced pressure to give a residue. The residue was purified by prep-HPLC (column: Waters Xbridge Prep OBD C18 150*40 mm*10 um; mobile phase: [water (10 mM NH$_4$HCO$_3$)-ACN]; B %: 30%-60%, 8 min) to afford N-[(1S)-2-[[(1S)-1-cyano-2-[(3S)-2-oxopyrrolidin-3-yl]ethyl]amino]-1-(cyclobutylmethyl)-2-oxo-ethyl]-4-methoxy-1H-indole-2-carboxamide (18.04 mg, 39.95 umol, 20.84% yield, 100% purity) as a white solid. MS (ESI) m/z 452.3 [M+H]$^+$.

$^1$H NMR (400 MHz, METHANOL-d$_4$) δ ppm 7.26 (d, J=0.7 Hz, 1H), 7.11-7.18 (m, 1H), 7.02 (d, J=8.3 Hz, 1H), 6.51 (d, J=7.6 Hz, 1H), 5.05 (dd, J=10.1, 5.9 Hz, 1H), 4.41 (dd, J=8.6, 6.2 Hz, 1H), 3.93 (s, 3H), 3.25-3.30 (m, 2H), 2.61 (dd, J=8.7, 5.3 Hz, 1H), 2.42-2.53 (m, 1H), 2.25-2.39 (m, 2H), 2.06-2.18 (m, 2H), 1.73-2.01 (m, 8H).

Example 173. Synthesis of Viral Protease Inhibitor Compound 589

Step 1: tert-butyl(1-(bicyclo[3.1.0]hexan-3-yl)-2-(((S)-1-cyano-2-((S)-2-oxopyrrolidin-3-yl)ethyl)amino)-2-oxoethyl)carbamate

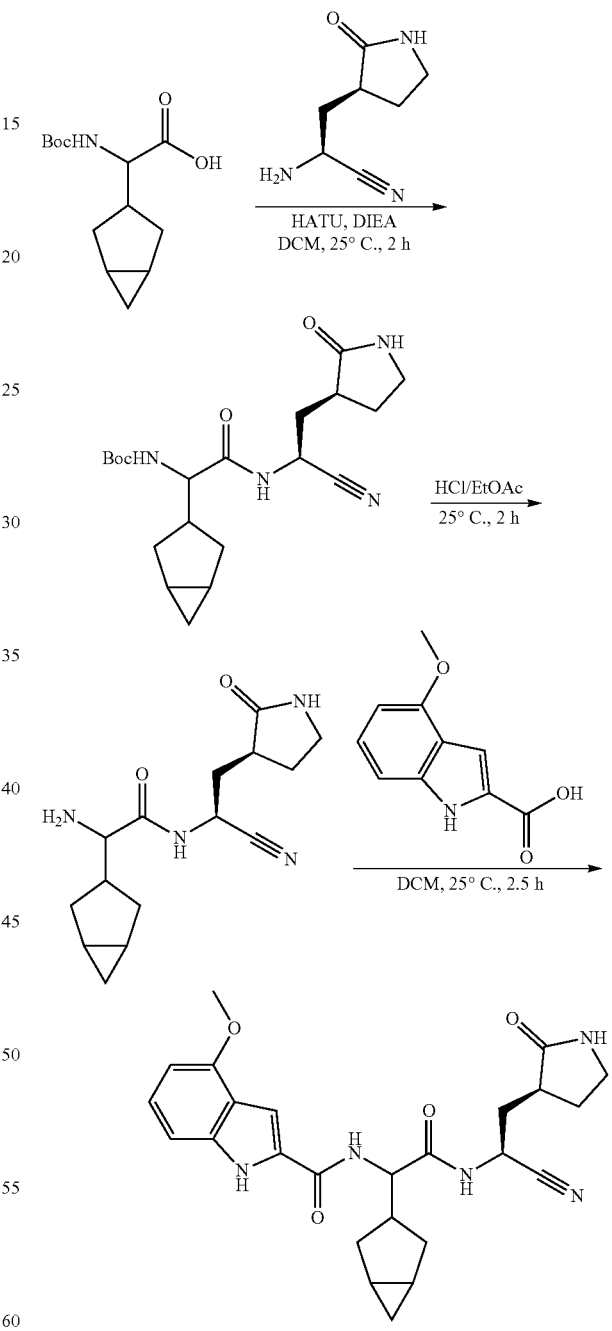

A mixture of (2S)-2-amino-3-[(3S)-2-oxopyrrolidin-3-yl]propanenitrile (89.1 mg, 0.47 mmol, 1.2 eq, HCl), HATU (223.3 mg, 0.58 mmol, 1.5 eq) and DIEA (151.8 mg, 1.18 mmol, 0.20 mL, 3 eq) in DCM (2 mL) was stirred at 25° C. for 0.5 h, and then 2-(3-bicyclo[3.1.0]hexanyl)-2-(tert-butoxycarbonylamino)acetic acid (100 mg, 0.39 mmol, 1 eq)

was added into the reaction. The resulting mixture was stirred 25° C. for 2 h. LCMS detected desired compound. The reaction mixture was added H₂O (10 mL) and extracted with ethyl acetate (10 mL*3). The combined organic layers were washed with brine (20 mL), dried with anhydrous Na₂SO₄, filtered and concentrated under reduced pressure to give a residue. The residue was purified by flash silica gel chromatography (ISCO®; 4 g SepaFlash® Silica Flash Column, Eluent of 0~100% ethyl acetate/petroleum ether-gradient @ 20 mL/min). Compound tert-butyl N-[1-(3-bicyclo[3.1.0]hexanyl)-2-[[(1S)-1-cyano-2-[(3S)-2-oxopyrrolidin-3-yl]ethyl]amino]-2-oxo-ethyl]carbamate (150 mg, 0.23 mmol, 58.8% yield, 60% purity) was obtained as colorless oil.

Step 2: 2-amino-2-(bicyclo[3.1.0]hexan-3-yl)-N-((S)-1-cyano-2-((S)-2-oxopyrrolidin-3-yl)ethyl)acetamide To a solution of tert-butyl N-[1-(3-bicyclo[3.1.0]hexanyl)-2-[[(1S)-1-cyano-2-[(3S)-2-oxopyrrolidin-3-yl]ethyl]amino]-2-oxo-ethyl]carbamate (140 mg, 0.21 mmol, 60% purity, 1 eq) in EtOAc (0.1 mL) was added HCl/EtOAc (4 M, 0.84 mL, 15.62 eq). The mixture was stirred at 25° C. for 2 h. The reaction mixture was concentrated under reduced pressure to give a residue. It was used into next step without purification. Compound 2-amino-2-(3-bicyclo[3.1.0]hexanyl)-N-[(1S)-1-cyano-2-[(3S)-2-oxopyrrolidin-3-yl]ethyl]acetamide (110 mg, crude, HCl) was obtained as a white solid.

Step 3: N-(1-(bicyclo[3.1.0]hexan-3-yl)-2-(((S)-1-cyano-2-((S)-2-oxopyrrolidin-3-yl)ethyl)amino)-2-oxoethyl)-4-methoxy-1H-indole-2-carboxamide A mixture of 4-methoxy-1H-indole-2-carboxylic acid (52.1 mg, 0.27 mmol, 1.2 eq), HATU (129.6 mg, 0.34 mmol, 1.5 eq) and DIEA (88.1 mg, 0.68 mol, 0.11 mL, 3 eq) in DCM (2 mL) was stirred at 25° C. for 0.5 h, and then 2-amino-2-(3-bicyclo[3.1.0]hexanyl)-N-[(1S)-1-cyano-2-[(3S)-2-oxopyrrolidin-3-yl]ethyl]acetamide (110 mg, 0.22 mmol, 60% purity, 1 eq) was added into the reaction. The resulting mixture was stirred 25° C. for 2 h. TLC (petroleum ether/ethyl acetate=0:1, UV 254) indicated starting material was consumed completely and new spots formed. LCMS detected desired compound. The reaction mixture was added H₂O (10 mL) and extracted with DCM (10 mL*3). The combined organic layers were washed with brine (20 mL), dried with anhydrous Na₂SO₄, filtered and concentrated under reduced pressure to give a residue. The residue was purified by flash silica gel chromatography (ISCO®; 4 g SepaFlash® Silica Flash Column, Eluent of 0~100% ethyl acetate/petroleum ethergradient @ 30 mL/min) to give 50 mg 46% of desire compound. Then it was purified by prep-HPLC (column: Phenomenex Gemini-NX 80*40 mm*3 um; mobile phase: [water(0.05% NH₃H₂O+10 mM NH₄HCO₃)-ACN]; B %: 25%-55%, 9.5 min). Compound N-[1-(3-bicyclo[3.1.0]hexanyl)-2-[[(1S)-1-cyano-2-[(3S)-2-oxopyrrolidin-3-yl]ethyl]amino]-2-oxo-ethyl]-4-methoxy-1H-indole-2-carboxamide (7 mg, 15.1 umol, 6.6% yield, 100% purity) was obtained as a white solid.

LCMS: Rt=0.813 min; for C₂₅H₂₉N₅O₄ MS Calcd.: 463.53; MS Found: 464.1 [M+H⁺].

¹H NMR (400 MHz, CD₃OD) δ 7.22-7.31 (m, 1H), 7.11-7.18 (m, 1H), 7.00-7.06 (m, 1H), 6.51 (d, J=7.63 Hz, 1H), 4.93-5.01 (m, 2H), 4.16-4.34 (m, 1H), 3.93 (s, 3H), 3.24-3.29 (m, 1H), 2.45-2.67 (m, 1H), 2.25-2.38 (m, 2H), 2.00-2.17 (m, 2H), 1.76-1.95 (m, 3H), 1.60-1.71 (m, 1H), 1.27-1.45 (m, 3H), 0.74 (br d, J=5.00 Hz, 1H), 0.13-0.38 (m, 2H).

Example 174. Synthesis of Viral Protease Inhibitor Compound 590

Step 2: Methyl (2S)-3-cyclopropyl-2-(4-methyl-3-nitro-2-oxo-1-pyridyl)propanoate

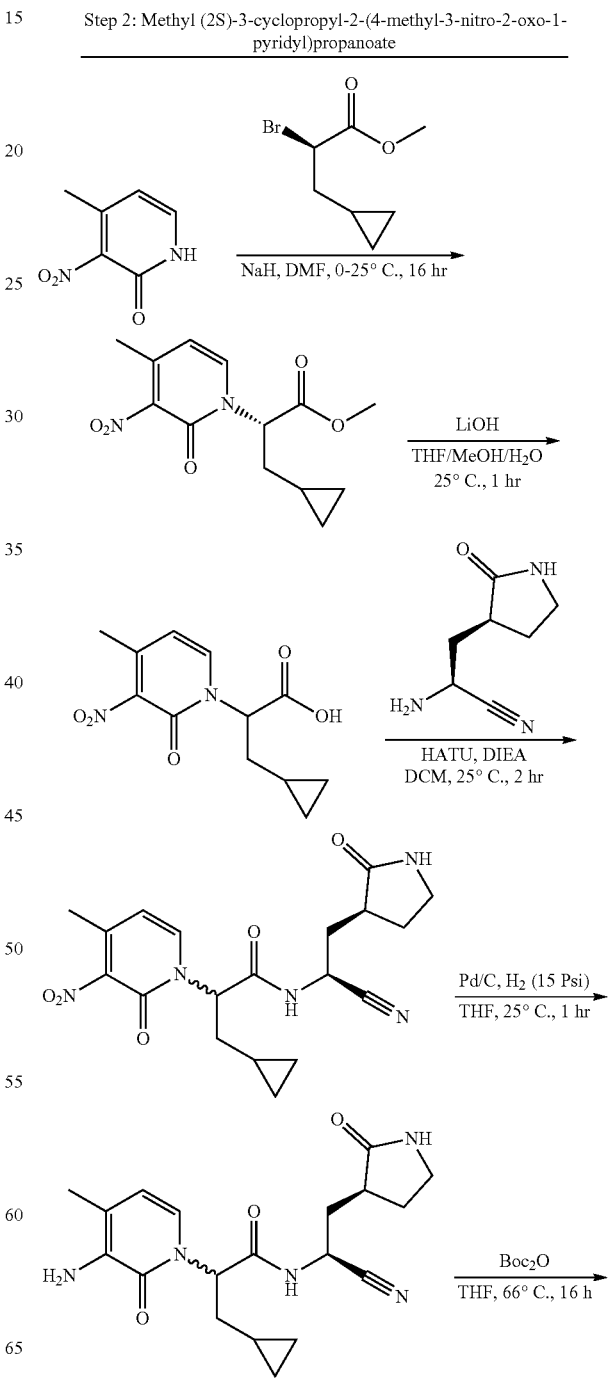

-continued

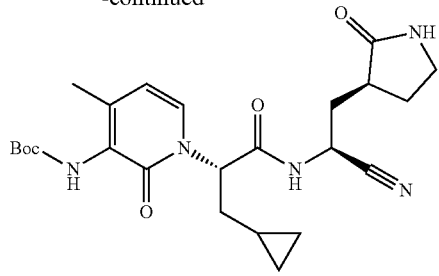

To a solution of 4-methyl-3-nitro-1H-pyridin-2-one (1 g, 6.49 mmol, 1 eq) in DMF (15 mL) was added NaH (363.3 mg, 9.08 mmol, 60% purity, 1.4 eq) at 0° C., and the reaction mixture was stirred at 25° C. for 0.5 h. Then, to the reaction was added methyl (2R)-2-bromo-3-cyclopropyl-propanoate (1.34 g, 6.49 mmol, 1 eq) at 0° C. The mixture was stirred at 25° C. for 16 h under $N_2$. The mixture was quenched with $H_2O$ (20 mL), and extracted with ethyl acetate (50 mL*3). The combined organic layers was washed with brine (40 mL) dried over $Na_2SO_4$, filtered and concentrated under reduce pressure. The residue was purified by flash silica gel chromatography (ISCO®; 24 g SepaFlash® Silica Flash Column, Eluent of 0~50% ethyl acetate/petroleum ether gradient @ 35 mL/min) to give methyl (2S)-3-cyclopropyl-2-(4-methyl-3-nitro-2-oxo-1-pyridyl)propanoate (867 mg, 47.4% yield) as a yellow solid.

LCMS: Rt=0.785 min; for $C_{13}H_{16}N_2O_5$ MS Calcd.: 280.11; MS Found: 281.1 [M+H$^+$].

Step 3: (2S)-3-cyclopropyl-2-(4-methyl-3-nitro-2-oxo-1-pyridyl)propanoic acid

A mixture of methyl (2S)-3-cyclopropyl-2-(4-methyl-3-nitro-2-oxo-1-pyridyl)propanoate (867 mg, 3.09 mmol, 1 eq), LiOH·$H_2O$ (519.2 mg, 12.37 mmol, 4 eq) in THF (6 mL), MeOH (2 mL), $H_2O$ (2 mL) was degassed and purged with $N_2$ for 3 times, and then the mixture was stirred at 25° C. for 1 h under $N_2$ atmosphere. LCMS showed one peak with desired MS was detected. The mixture was added $H_2O$ (5 mL), and then the mixture was added 2 M HCl (4 mL) to adjust the pH of the mixture to about 6~7. The mixture was extracted with ethyl acetate (30 mL*3). The combined organic layers was washed with brine (20 mL) dried over $Na_2SO_4$, filtered and concentrated under reduce pressure to give (2S)-3-cyclopropyl-2-(4-methyl-3-nitro-2-oxo-1-pyridyl)propanoic acid (791 mg, 94.8% yield) as a yellow solid.

LCMS: Rt=0.735 min; for $C_{12}H_{14}N_2O_5$ MS Calcd.: 266.09; MS Found: 267.0 [M+H$^+$].

Step 4: N-[(1S)-1-cyano-2-[(3S)-2-oxopyrrolidin-3-yl]ethyl]-3-cyclopropyl-2-(4-methyl-3-nitro-2-oxo-1-pyridyl)propanamide To a solution of (2S)-3-cyclopropyl-2-(4-methyl-3-nitro-2-oxo-1-pyridyl)propanoic acid (791 mg, 2.97 mmol, 1 eq) in DCM (10 mL) was added HATU (1.36 g, 3.57 mmol, 1.2 eq), DIPEA (1.15 g, 8.91 mmol, 1.55 mL, 3 eq) and (2S)-2-amino-3-[(3S)-2-oxopyrrolidin-3-yl]propanenitrile (676.0 mg, 3.57 mmol, 1.2 eq, HCl). The mixture was stirred at 25° C. for 2 h. The mixture was quenched with $H_2O$ (20 mL) and extracted with DCM (40 mL*3). The combined organic layers was washed with brine (20 mL) dried over $Na_2SO_4$, filtered and concentrated under reduce pressure. The residue was purified by flash silica gel chromatography (ISCO®; 24 g SepaFlash® Silica Flash Column, Eluent of 0~10% DCM/MeOH ethergradient @ 35 mL/min) to give N-[(1S)-1-cyano-2-[(3S)-2-oxopyrrolidin-3-yl]ethyl]-3-cyclopropyl-2-(4-methyl-3-nitro-2-oxo-1-pyridyl)propanamide (838 mg, 64.5% yield) as a yellow oil.

LCMS: Rt=0.741 min; for $C_{19}H_{23}N_5O_5$ MS Calcd.: 401.17; MS Found: 402.1 [M+H$^+$].

Step 5: 2-(3-Amino-4-methyl-2-oxo-1-pyridyl)-N-[(1S)-1-cyano-2-[(3S)-2-oxopyrrolidin-3-yl]ethyl]-3-cyclopropyl-propanamide To a solution of N-[(1S)-1-cyano-2-[(3S)-2-oxopyrrolidin-3-yl]ethyl]-3-cyclopropyl-2-(4-methyl-3-nitro-2-oxo-1-pyridyl)propanamide (838 mg, 2.09 mmol, 1 eq) in THF (10 mL) was added Pd/C (566.5 mg, 0.53 mmol, 10% purity). The mixture was stirred at 25° C. for 1 h under $H_2$. The mixture was filtered and concentrated under reduce pressure to give 2-(3-amino-4-methyl-2-oxo-1-pyridyl)-N-[(1S)-1-cyano-2-[(3S)-2-oxopyrrolidin-3-yl]ethyl]-3-cyclopropyl-propanamide (616 mg, 1.43 mmol, 68.7% yield, 86.5% purity) as a white solid.

LCMS: Rt=0.703 min; for $C_{19}H_{25}N_5O_3$ MS Calcd.: 371.20; MS Found: 372.1 [M+H$^+$].

Step 6: tert-Butyl N-[1-[2-[[(1S)-1-cyano-2-[(3S)-2-oxopyrrolidin-3-yl]ethyl]amino]-1-(cyclopropylmethyl)-2-oxo-ethyl]-4-methyl-2-oxo-3-pyridyl]carbamate A mixture of 2-(3-amino-4-methyl-2-oxo-1-pyridyl)-N-[(1S)-1-cyano-2-[(3S)-2-oxopyrrolidin-3-yl]ethyl]-3-cyclopropyl-propanamide (100 mg, 0.26 mmol, 1 eq) in $Boc_2O$ (1 mL) and THF (1 mL), and then the mixture was stirred at 66° C. for 16 h under $N_2$ atmosphere. The mixture was concentrated under reduce pressure. The mixture was quenched with $H_2O$ (20 mL), and extracted with ethyl acetate (30 mL*3). The combined organic layers was washed with brine (10 mL) dried over $Na_2SO_4$, filtered and concentrated under reduce pressure. The residue was purified by prep-HPLC (column: Phenomenex Gemini-NX 80*40 mm*3 um; mobile phase: [water(0.05% $NH_3H_2O$+10 mM $NH_4HCO_3$)-ACN]; B %: 26%-56%, 7.8 min) to give tert-butyl N-[1-[2-[[(1S)-1-cyano-2-[(3S)-2-oxopyrrolidin-3-yl]ethyl]amino]-1-(cyclopropylmethyl)-2-oxo-ethyl]-4-methyl-2-oxo-3-pyridyl]carbamate (44.33 mg, 33.5% yield) as a white solid.

LCMS: Rt=0.798 min; for $C_{34}H_{51}N_5O_{10}$ MS Calcd.: 471.55; MS Found: 472.2 [M+H$^+$].

$^1$H NMR (400 MHz, $CD_3OD$) δ 7.53 (dd, J=1.5, 7.3 Hz, 1H), 6.36-6.27 (m, 1H), 5.56-5.35 (m, 1H), 5.18-4.97 (m, 1H), 3.35-3.32 (m, 1H), 3.29-3.25 (m, 1H), 2.52 (tq, J=4.8, 9.3 Hz, 1H), 2.45-2.22 (m, 2H), 2.18 (d, J=5.0 Hz, 3H), 2.06-1.92 (m, 2H), 1.91-1.71 (m, 2H), 1.48 (d, J=2.5 Hz, 9H), 0.69-0.56 (m, 1H), 0.50-0.37 (m, 2H), 0.19-0.01 (m, 2H).

1177
Example 175. Synthesis of Viral Protease Inhibitor Compound 591

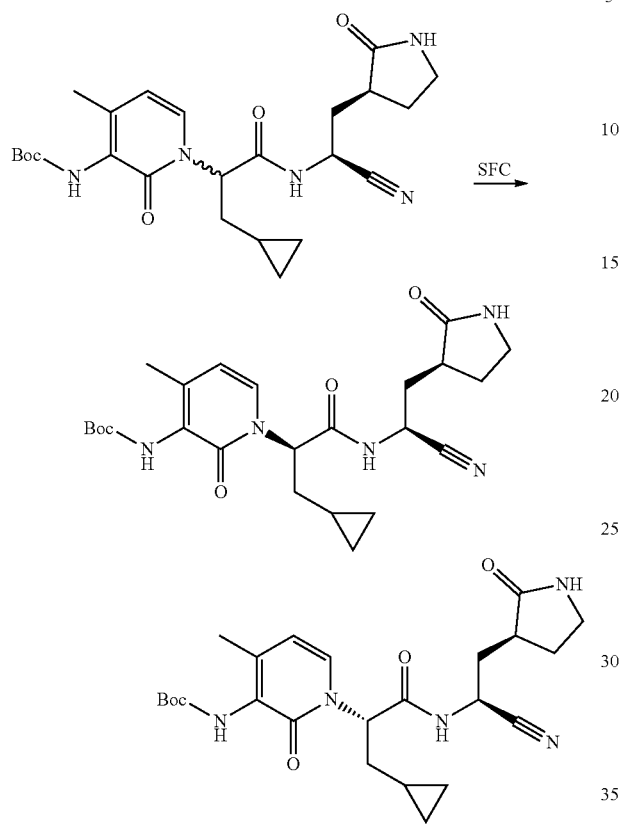

tert-Butyl N-[1-[2-[[(1S)-1-cyano-2-[(3S)-2-oxopyrrolidin-3-yl]ethyl]amino]-1-(cyclopropylmethyl)-2-oxo-ethyl]-4-methyl-2-oxo-3-pyridyl]carbamate (42 mg, 89.0 umol, 1 eq) was further separated by SFC (condition: column: DAICEL CHIRALPAK AD (250 mm*30 mm, 10 um); mobile phase: [0.1% NH₃H₂O ETOH]; B %: 45%-45%, min) to afford tert-butyl N-[1-[(1R)-2-[[(1S)-1-cyano-2-[(3S)-2-oxopyrrolidin-3-yl]ethyl]amino]-1-(cyclopropylmethyl)-2-oxo-ethyl]-4-methyl-2-oxo-3-pyridyl]carbamate (8.32 mg, 19.8% yield) as a white solid.

Isomer 1: LCMS: Rt=0.803 min; for $C_{34}H_{51}N_5O_{10}$ MS Calcd.: 471.55; MS Found: 472.2 [M+H⁺]. ¹H NMR (400 MHz, CD₃OD) δ 7.53 (d, J=7.3 Hz, 1H), 6.32 (d, J=7.3 Hz, 1H), 5.50 (t, J=7.8 Hz, 1H), 5.01 (dd, J=7.0, 9.0 Hz, 1H), 3.35-3.32 (m, 1H), 2.56-2.45 (m, 1H), 2.42-2.23 (m, 2H), 2.19 (s, 3H), 2.00-1.92 (m, 2H), 1.92-1.78 (m, 2H), 1.49 (s, 9H), 0.65-0.55 (m, 1H), 0.46-0.36 (m, 2H), 0.20-0.01 (m, 2H).

Isomer 2: LCMS: Rt=0.794 min; for $C_{34}H_{51}N_5O_{10}$ MS Calcd.: 471.55; MS Found: 472.2 [M+H⁺]. ¹H NMR (400 MHz, CD₃OD) δ 7.53 (d, J=7.0 Hz, 1H), 6.31 (d, J=7.3 Hz, 1H), 5.41 (t, J=7.8 Hz, 1H), 5.10-4.97 (m, 1H), 3.30-3.25 (m, 2H), 2.52 (dq, J=5.5, 9.2 Hz, 1H), 2.33-2.19 (m, 2H), 2.18 (s, 3H), 2.05-1.90 (m, 2H), 1.89-1.71 (m, 2H), 1.48 (s, 9H), 0.70-0.58 (m, 1H), 0.52-0.35 (m, 2H), 0.20-0.04 (m, 2H).

1178
Example 176. Synthesis of Viral Protease Inhibitor Compound 611

Step 1: tert-Butyl (2S,4S)-2-[[(1S)-2-methoxy-2-oxo-1-[[(3S)-2-oxo-3-piperidyl]methyl]ethyl]carbamoyl]-4-phenyl-pyrrolidine-1-carboxylate

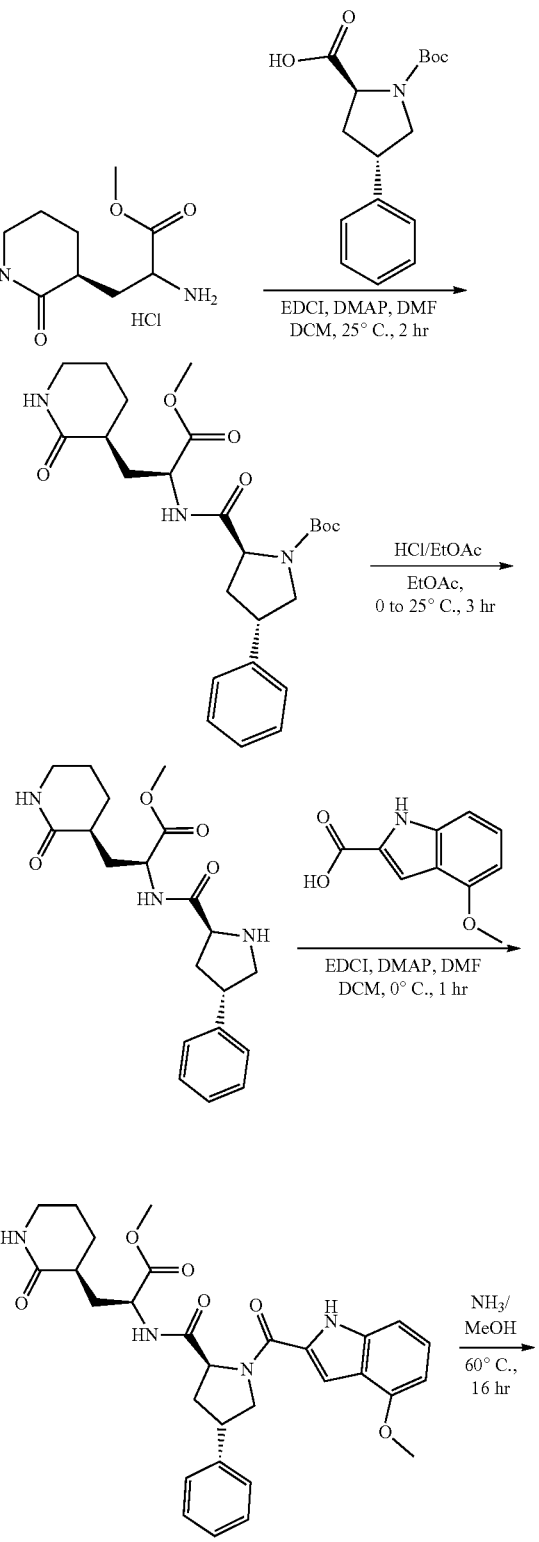

-continued

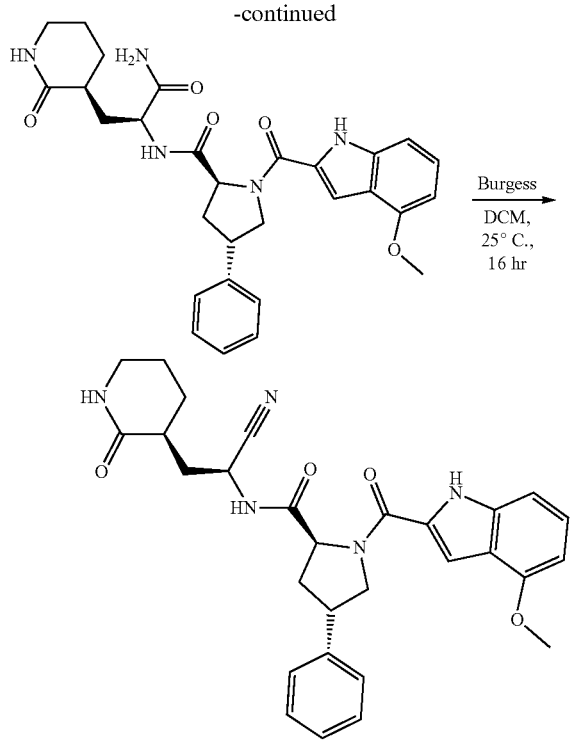

Burgess
DCM,
25° C.,
16 hr

To a solution of (2S,4S)-1-tert-butoxycarbonyl-4-phenyl-pyrrolidine-2-carboxylic acid (100 mg, 0.34 mmol, 1 eq) and DMAP (125.8 mg, 1.03 mmol, 3 eq) in DCM (0.7 mL) was added EDCI (78.9 mg, 0.41 mmol, 1.2 eq), and then a solution of methyl (2S)-2-amino-3-[(3S)-2-oxo-3-piperidyl]propanoate (81.2 mg, 0.34 mmol, 1 eq, HCl) in DMF (0.7 mL) was added. The reaction mixture was stirred at 25° C. for 2 h. LCMS showed one peak with desired MS was detected. The mixture was quenched with H$_2$O (10 mL), and extracted with ethyl acetate (20 mL*3). The combined organic layers was washed with brine (10 mL) dried over Na$_2$SO$_4$, filtered and concentrated under reduce pressure. The residue was purified by flash silica gel chromatography (ISCO®; 12 g SepaFlash® Silica Flash Column, Eluent of 0~10% DCM/MeOH @ 30 mL/min) to give tert-butyl (2S,4S)-2-[[(1S)-2-methoxy-2-oxo-1-[[(3S)-2-oxo-3-piperidyl]methyl]ethyl]carbamoyl]-4-phenyl-pyrrolidine-1-carboxylate (100 mg, 60.4% yield) as a white solid.

LCMS: Rt=0.826 min; for C$_{25}$H$_{35}$N$_3$O$_6$ MS Calcd.: 473.25; MS Found: 474.1 [M+H$^+$].

Step 2: Methyl (2S)-3-[(3S)-2-oxo-3-piperidyl]-2-[[(2S,4S)-4-phenylpyrrolidine-2-carbonyl]amino]propanoate A mixture of tert-butyl (2S,4S)-2-[[(1S)-2-methoxy-2-oxo-1-[[(3S)-2-oxo-3-piperidyl]methyl]ethyl]carbamoyl]-4-phenyl-pyrrolidine-1-carboxylate (90 mg, 0.17 mmol, 1 eq, HCl) in 2 M HCl/EtOAc (6 mL), and then the mixture was stirred at 25° C. for 3 h under N$_2$ atmosphere. LCMS showed one peak with desired MS was detected. The mixture was concentrated under reduce pressure to give methyl (2S)-3-[(3S)-2-oxo-3-piperidyl]-2-[[(2S,4S)-4-phenylpyrrolidine-2-carbonyl]amino]propanoate (70 mg, 83.3% yield, HCl) was obtained as a yellow solid.

Step 3: Methyl (2S)-2-[[(2S,4S)-1-(4-methoxy-1H-indole-2-carbonyl)-4-phenyl-pyrrolidine-2-carbonyl]amino]-3-[(3S)-2-oxo-3-piperidyl]propanoate To a solution of 4-methoxy-1H-indole-2-carboxylic acid (40.5 mg, 0.21 mmol, 1.5 eq) and DMAP (51.8 mg, 0.42 mmol, 3 eq) in DCM (0.5 mL) was added EDCI (32.5 mg, 0.16 mmol, 1.2 eq), and then a solution of methyl (2S)-3-[(3S)-2-oxo-3-piperidyl]-2-[[(2S,4S)-4-phenylpyrrolidine-2-carbonyl]amino]propanoate (58 mg, 0.14 mmol, 1 eq, HCl) in DMF (0.5 mL) was added. The reaction mixture was stirred at 0° C. for 1 h. LCMS showed one peak with desired MS was detected. The mixture was quenched with H$_2$O (20 mL) and then extracted with ethyl acetate (30 mL*3). The combined organic layers was washed with brine (10 mL) dried over Na$_2$SO$_4$, filtered and concentrated under reduce pressure. The residue was purified by flash silica gel chromatography (ISCO®; 12 g SepaFlash® Silica Flash Column, Eluent of 0~10% DCM/MeOH @ 30 mL/min) to give methyl (2S)-2-[[(2S,4S)-1-(4-methoxy-1H-indole-2-carbonyl)-4-phenyl-pyrrolidine-2-carbonyl]amino]-3-[(3S)-2-oxo-3-piperidyl]propanoate (30 mg, 36.6% yield) as a white solid.

LCMS: Rt=1.730 min; for C$_{30}$H$_{34}$N$_4$O$_6$ MS Calcd.: 546.25; MS Found: 547.1 [M+H$^+$].

Step 4: (2S,4S)-N-[(1S)-2-amino-2-oxo-1-[[(3S)-2-oxo-3-piperidyl]methyl]ethyl]-1-(4-methoxy-1H-indole-2-carbonyl)-4-phenyl-pyrrolidine-2-carboxamide To a solution of methyl (2S)-2-[[(2S,4S)-1-(4-methoxy-1H-indole-2-carbonyl)-4-phenyl-pyrrolidine-2-carbonyl]amino]-3-[(3S)-2-oxo-3-piperidyl]propanoate (30 mg, 54.8 umol, 1 eq) and NH$_3$ (7 M, 6 mL, 765.2 eq) and MeOH (6 mL) in sealed tube. The mixture was stirred at 60° C. for 16 h. LCMS showed one peak with desired MS was detected. The mixture was concentrated under reduce pressure to give compound (2S,4S)-N-[(1S)-2-amino-2-oxo-1-[[(3S)-2-oxo-3-piperidyl]methyl]ethyl]-1-(4-methoxy-1H-indole-2-carbonyl)-4-phenyl-pyrrolidine-2-carboxamide (29 mg, 99.40% yield) as a yellow solid.

Step 5: (2S,4S)-N-[(1S)-1-cyano-2-[(3S)-2-oxo-3-piperidyl]ethyl]-1-(4-methoxy-1H-indole-2-carbonyl)-4-phenyl-pyrrolidine-2-carboxamide To a solution of (2S,4S)-N-[(1S)-2-amino-2-oxo-1-[[(3S)-2-oxo-3-piperidyl]methyl]ethyl]-1-(4-methoxy-1H-indole-2-carbonyl)-4-phenyl-pyrrolidine-2-carboxamide (29 mg, 54.5 umol, 1 eq) in DCM (1 mL) was added Burgess reagent (39.0 mg, 0.16 mmol, 3 eq) at 0° C. The mixture was stirred at 25° C. for 16 hr. LCMS showed one peak with desired MS was detected. The mixture was quenched with H$_2$O (5 mL), and extracted with ethyl acetate (10 mL*3). The combined organic layers was washed with brine (10 mL) dried over Na$_2$SO$_4$, filtered and concentrated under reduce pressure. The residue was purified by prep-HPLC (column: Welch Xtimate C18 150*25 mm*5 um; mobile phase: [water(0.225% FA)-ACN]; B %: 37%-67%, 9.5 min) to give compound (2S,4S)-N-[(1S)-1-cyano-2-[(3S)-2-oxo-3-piperidyl]ethyl]-1-(4-methoxy-1H-indole-2-carbonyl)-4-phenyl-pyrrolidine-2-carboxamide (1.9 mg, 6.6% yield) as a white solid.

LCMS: Rt=1.730 min; for C$_{30}$H$_{34}$N$_4$O$_6$ MS Calcd.: 546.25; MS Found: 547.1 [M+H$^+$].

¹H NMR (400 MHz, CD₃OD) δ 7.38-7.31 (m, 1H), 7.30-7.23 (m, 4H), 7.19-7.13 (m, 1H), 7.10-7.04 (m, 1H), 6.95 (d, J=8.5 Hz, 1H), 6.41 (br d, J=7.5 Hz, 1H), 5.17-5.02 (m, 1H), 4.43-4.20 (m, 1H), 3.96-3.76 (m, 4H), 3.74-3.41 (m, 1H), 3.18-3.11 (m, 1H), 3.01-2.55 (m, 2H), 2.51-2.20 (m, 3H), 2.15-1.62 (m, 4H), 1.55-1.27 (m, 2H).

Example 177. Synthesis of Viral Protease Inhibitor Compound 619

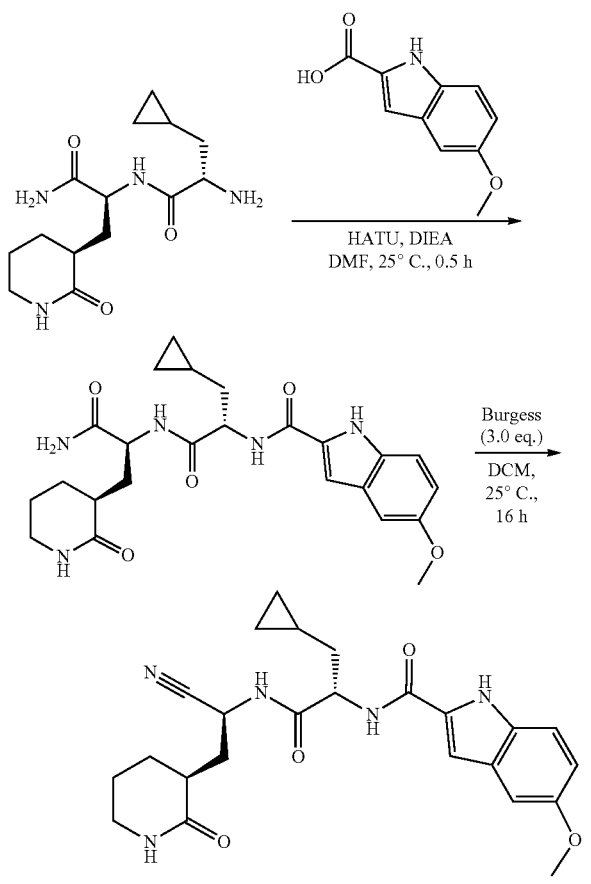

Step 1: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-5-methoxy-1H-indole-2-carboxamide To a solution of (2S)-2-amino-N-[(1S)-2-amino-2-oxo-1-[[(3S)-2-oxo-3-piperidyl]methyl]ethyl]-3-cyclopropyl-propanamide (120.0 mg, 0.40 mmol, 1 eq) and 5-methoxy-1H-indole-2-carboxylic acid (77.4 mg, 0.40 mmol, 1 eq) DMF (2 mL) was added HATU (184.7 mg, 0.48 mmol, 1.2 eq) and DIEA (104.6 mg, 0.8 mmol, 0.14 mL, 2 eq). The mixture was stirred at 25° C. for 0.5 h, and then the reaction mixture was concentrated under reduced pressure to remove DMF. The residue was diluted with H₂O (10 mL) and extracted with ethyl acetate (25 mL*3). The combined organic layers were washed with Brine (10 mL*3), dried over Na2SO4, filtered and concentrated under reduced pressure to give a residue. The residue was purified by flash silica gel chromatography (ISCO®; 4 g SepaFlash® Silica Flash Column, Eluent of 0~10% Methanol/Dichloromethane@ 20 mL/min). Compound N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-5-methoxy-1H-indole-2-carboxamide (180.0 mg, 94.6% yield) was obtained as a white solid.

Step 2: N-[(1S)-2-[[(1S)-1-cyano-2-[(3S)-2-oxo-3-piperidyl]ethyl]amino]-1-(cyclopropylmethyl)-2-oxo-ethyl]-5-methoxy-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-5-methoxy-1H-indole-2-carboxamide (180.0 mg, 0.38 mmol, 1 eq) in DCM (0.5 mL) was added Burgess reagent (274.0 mg, 1.15 mmol, 3 eq) at 0° C. After the mixture was stirred at 25° C. for 16 h, the reaction mixture was concentrated under reduced pressure to remove DCM. The residue was diluted with H₂O (5 mL) and extracted with DCM (10 mL*3). The combined organic layers were washed with Brine (5 mL*3), dried over Na₂SO₄, filtered and concentrated under reduced pressure to give a residue. The residue was purified by prep-HPLC (column: Phenomenex Gemini-NX 80*40 mm*3 um; mobile phase: [water (0.05% NH₃H₂O+10 mM NH₄HCO₃)-ACN]; B %: 24%-54%, 7.8 min). Compound N-[(1S)-2-[[(1S)-1-cyano-2-[(3S)-2-oxo-3-piperidyl]ethyl]amino]-1-(cyclopropylmethyl)-2-oxo-ethyl]-5-methoxy-1H-indole-2-carboxamide (37.3 mg, 82.6 umol, 5.4 yield) was obtained as a white solid.

LCMS: Rt=0.785 min; for C₂₄H₂₉N₅O₄ MS Calcd.: 451.52; MS Found: 452.1 [M+H⁺].

¹H NMR (400 MHz, CD₃OD) δ 7.32 (d, J=8.8 Hz, 1H), 7.13-7.06 (m, 2H), 6.89 (dd, J=2.4, 8.9 Hz, 1H), 5.16-5.10 (m, 1H), 4.55 (t, J=7.4 Hz, 1H), 3.81 (s, 3H), 3.26-3.20 (m, 2H), 2.54-2.41 (m, 2H), 2.04-1.85 (m, 3H), 1.84-1.77 (m, 1H), 1.74-1.62 (m, 2H), 1.56-1.47 (m, 1H), 0.95-0.79 (m, 1H), 0.60-0.47 (m, 2H), 0.19 (br dd, J=4.8, 10.0 Hz, 2H).

Example 178. Synthesis of Viral Protease Inhibitor Compound 621

Step 1: (2S)-2-amino-N-[(1S)-2-amino-2-oxo-1-[[(3S)-2-oxo-3-piperidyl]methyl]ethyl]-3-cyclopropyl-propanamide

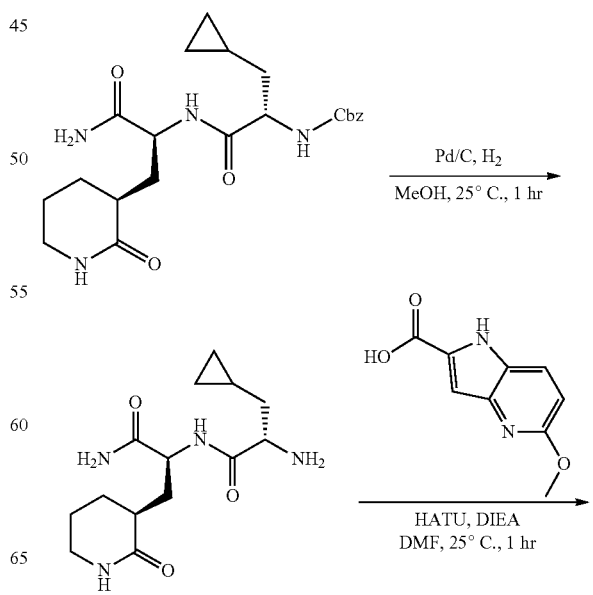

1183
-continued

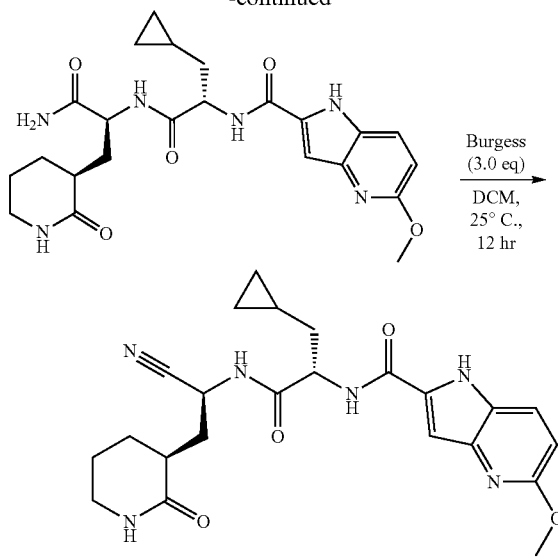

To a solution of benzyl N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]carbamate (400 mg, 0.92 mmol, 1 eq) in MeOH (5 mL) was added Pd (200 mg, 10% purity) and H₂ (0.92 mmol). The mixture was stirred at 25° C. under 15 psi for 1 h. LCMS showed one peak with desired MS was detected. The mixture was filtered to give the filter liquor. The mixture was concentrated under reduce pressure to give (2S)-2-amino-N-[(1S)-2-amino-2-oxo-1-[[(3S)-2-oxo-3-piperidyl]methyl]ethyl]-3-cyclopropyl-propanamide (274 mg, 99.5% yield) as a white solid.

Step 2: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-5-methoxy-1H-pyrrolo[3,2-b]pyridine-2-carboxamide To a solution of (2S)-2-amino-N-[(1S)-2-amino-2-oxo-1-[[(3S)-2-oxo-3-piperidyl]methyl]ethyl]-3-cyclopropyl-propanamide (137 mg, 0.46 mmol, 1 eq) and 5-methoxy-1H-pyrrolo[3,2-b]pyridine-2-carboxylic acid (88.8 mg, 0.46 mmol, 1 eq) in DMF (2 mL) was added DIPEA (119.4 mg, 0.92 mmol, 0.16 mL, 2 eq) and HATU (210.9 mg, 0.55 mmol, 1.2 eq). The mixture was stirred at 25° C. for 1 h. LCMS showed one peak with desired MS was detected. The mixture was concentrated under reduce pressure. The residue was purified by flash silica gel chromatography (ISCO®; 12 g SepaFlash® Silica Flash Column, Eluent of 0~10% DCM/MeOH @ 30 mL/min) to give Compound N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-5-methoxy-1H-pyrrolo[3,2-b]pyridine-2-carboxamide (144 mg, 63.1% yield) as a white solid.

LCMS: Rt=0.675 min; for $C_{23}H_{30}N_6O_5$ MS Calcd.: 470.23; MS Found: 471.1 [M+H⁺].

Step 3: N-[(1S)-2-[[(1S)-1-cyano-2-[(3S)-2-oxo-3-piperidyl]ethyl]amino]-1-(cyclopropylmethyl)-2-oxo-ethyl]-5-methoxy-1H-pyrrolo[3,2-b]pyridine-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-5-methoxy-1H-pyrrolo[3,2-b]pyridine-2-carboxamide (44 mg, 93.5 umol, 1 eq) in DCM (1 mL) was added Burgess reagent (66.86 mg, 0.28 mmol, 3 eq) at 0° C. The mixture was stirred at 25° C. for 12 hr. LCMS showed one peak with desired MS was detected. The mixture was quenched with H₂O (10 mL), and extracted with DCM (20 mL*3). The combined organic layers was washed with brine (10 mL) dried over Na₂SO₄, filtered and concentrated under reduce pressure. The residue was purified by prep-HPLC (column: Phenomenex Gemini-NX 80*40 mm*3 um; mobile phase: [water(0.05% NH₃H₂O+10 mM NH₄HCO₃)-ACN]; B %: 23%-53%, 7.8 min) to give compound N-[(1S)-2-[[(1S)-1-cyano-2-[(3S)-2-oxo-3-piperidyl]ethyl]amino]-1-(cyclopropylmethyl)-2-oxo-ethyl]-5-methoxy-1H-pyrrolo[3,2-b]pyridine-2-carboxamide (12.08 mg, 9.3% yield) as a white solid.

LCMS: Rt=0.727 min; for $C_{23}H_{28}N_6O_4$ MS Calcd.: 452.22; MS Found: 453.1 [M+H⁺].

¹H NMR (400 MHz, CD₃OD) δ 7.79-7.74 (m, 1H), 7.17 (s, 1H), 6.72 (d, J=9.0 Hz, 1H), 5.17-5.04 (m, 1H), 4.56 (t, J=7.4 Hz, 1H), 3.97-3.96 (m, 1H), 3.95 (s, 2H), 3.26-3.19 (m, 2H), 2.56-2.40 (m, 2H), 2.02-1.87 (m, 3H), 1.85-1.78 (m, 1H), 1.76-1.63 (m, 2H), 1.59-1.46 (m, 1H), 0.90-0.77 (m, 1H), 0.59-0.46 (m, 2H), 0.27-0.07 (m, 2H).

Example 179. Synthesis of Viral Protease Inhibitor Compound 623

Step 1: Methoxy-1H-pyrrolo[3,2-c]pyridine-2-carboxylic acid

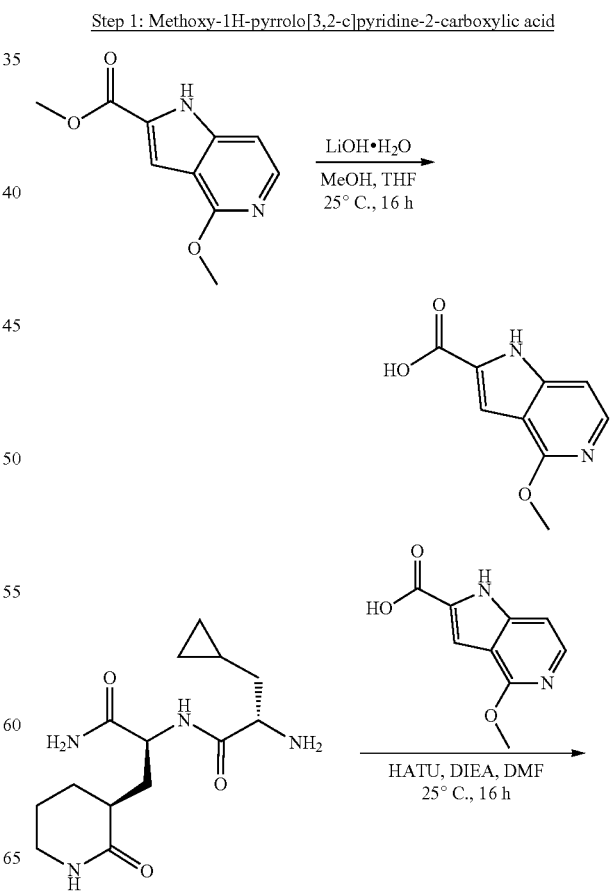

-continued

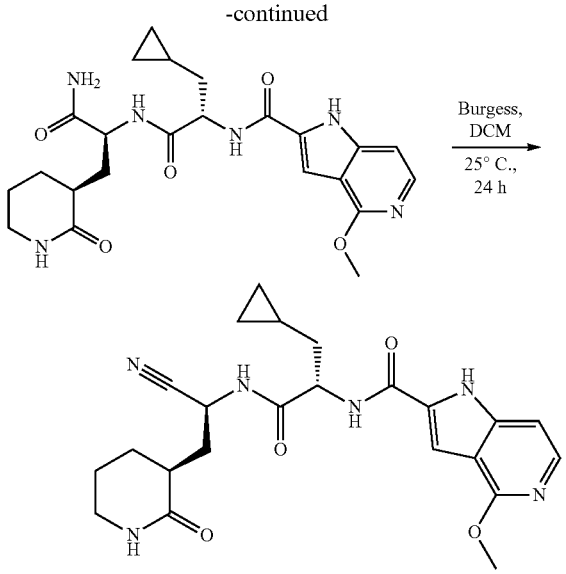

To a solution of methyl 4-methoxy-1H-pyrrolo[3,2-c]pyridine-2-carboxylate (150 mg, 0.72 mmol, 1 eq) in THF (1 mL) was added LiOH·H$_2$O (30.5 mg, 0.72 mmol, 1 eq) and MeOH (0.5 mL). The mixture was stirred at 25° C. for 16 h. The reaction mixture was diluted with H$_2$O (30 mL) and extracted with DCM (30 mL*3). The aqueous layer acidified with concentrated HCl and extracted with DCM. The combined organic layers were washed with brine (30 mL*2), dried with anhydrous Na$_2$SO$_4$, filtered and concentrated under reduced pressure to give a residue. The crude product was triturated with petroleum ether at 25° C. for 60 min. Compound 4-methoxy-1H-pyrrolo[3,2-c]pyridine-2-carboxylic acid (120 mg, 84.9% yield, 99% purity) was obtained as white solid.

Step 2: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-pyrrolo[3,2-c]pyridine-2-carboxamide A solution of (2S)-2-amino-N-[(1S)-2-amino-2-oxo-1-[[(3S)-2-oxo-3-piperidyl]methyl]ethyl]-3-cyclopropyl-propanamide (150 mg, 0.50 mmol, 1 eq) in DMF (1 mL) was added HATU (192.4 mg, 0.50 mmol, 1 eq), 4-methoxy-1H-pyrrolo[3,2-c]pyridine-2-carboxylic acid (106.9 mg, 0.55 mmol, 1.1 eq) and DIEA (130.8 mg, 1.01 mmol, 0.17 mL, 2 eq) was stirred at 25° C. for 16 hr. The reaction mixture was diluted with H$_2$O (30 mL) and extracted with ethyl acetate (30 mL*3). The combined organic layers were washed with brine (30 mL*2), dried with anhydrous Na$_2$SO$_4$, filtered and concentrated under reduced pressure to give a residue. Compound N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-pyrrolo[3,2-c]pyridine-2-carboxamide (110 mg, crude) was obtained as white solid.

Step 3: N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-pyrrolo[3,2-c]pyridine-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-methoxy-1H-pyrrolo[3,2-c]pyridine-2-carboxamide (110 mg, 0.23 mmol, 1 eq) in DCM (1 mL) was added methoxycarbonyl-(triethylammonio)sulfonyl-azanide (167.1 mg, 0.70 mmol, 3 eq). The mixture was stirred at 25° C. for 24 h. The reaction mixture was diluted with H$_2$O (30 mL) and extracted with DCM (30 mL*3). The combined organic layers were washed with brine (30 mL*2), dried with anhydrous Na$_2$SO$_4$, filtered and concentrated under reduced pressure to give a residue. The residue was purified by prep-HPLC (column: Phenomenex Gemini-NX 80*40 mm*3 um; mobile phase: [water (0.05% NH$_3$H$_2$O+10 mM NH$_4$HCO$_3$)-ACN]; B %: 15%-45%, 9.5 min). Compound N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-pyrrolo[3,2-c]pyridine-2-carboxamide (40.69 mg, 38.4% yield, 100% purity) was obtained as white solid.

LCMS: Rt=1.387 min; for C$_{23}$H$_{28}$N$_6$O$_4$ MS Calcd.: 452.51; MS Found: 453.1 [M+H$^+$].

$^1$H NMR (400 MHz, CD$_3$OD) δ 7.77 (d, J=6.0 Hz, 1H), 7.34 (s, 1H), 7.05 (d, J=6.3 Hz, 1H), 4.47 (dd, J=4.0, 11.8 Hz, 1H), 4.57 (dd, J=6.0, 8.3 Hz, 1H), 4.05 (s, 3H), 3.28-3.17 (m, 2H), 2.47-2.35 (m, 1H), 2.28 (ddd, J=4.4, 12.0, 14.0 Hz, 1H), 2.08-1.95 (m, 1H), 1.90-1.77 (m, 3H), 1.77-1.63 (m, 2H), 1.62-1.48 (m, 1H), 0.96-0.78 (m, 1H), 0.59-0.42 (m, 2H), 0.26-0.11 (m, 2H).

Example 180. Synthesis of Viral Protease Inhibitor Compound 625

Step 1: (2S)-2-(benzyloxycarbonylamino)-3-cyclopropyl-propanoic acid

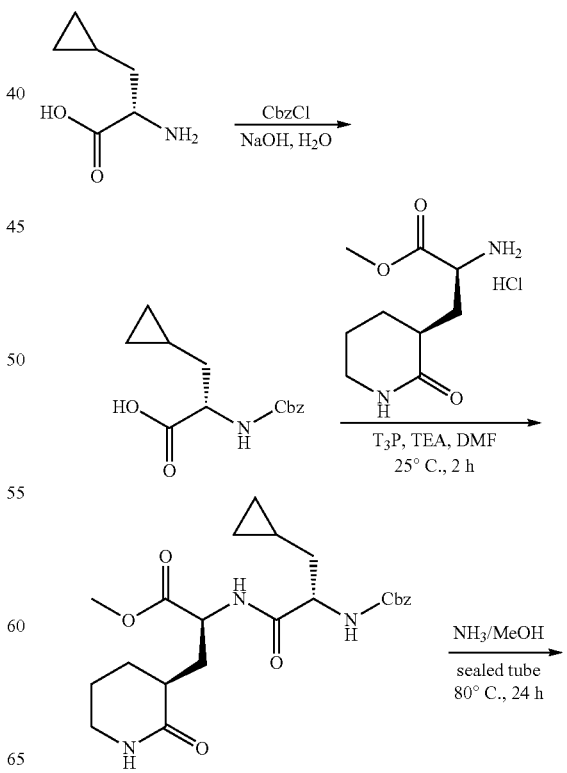

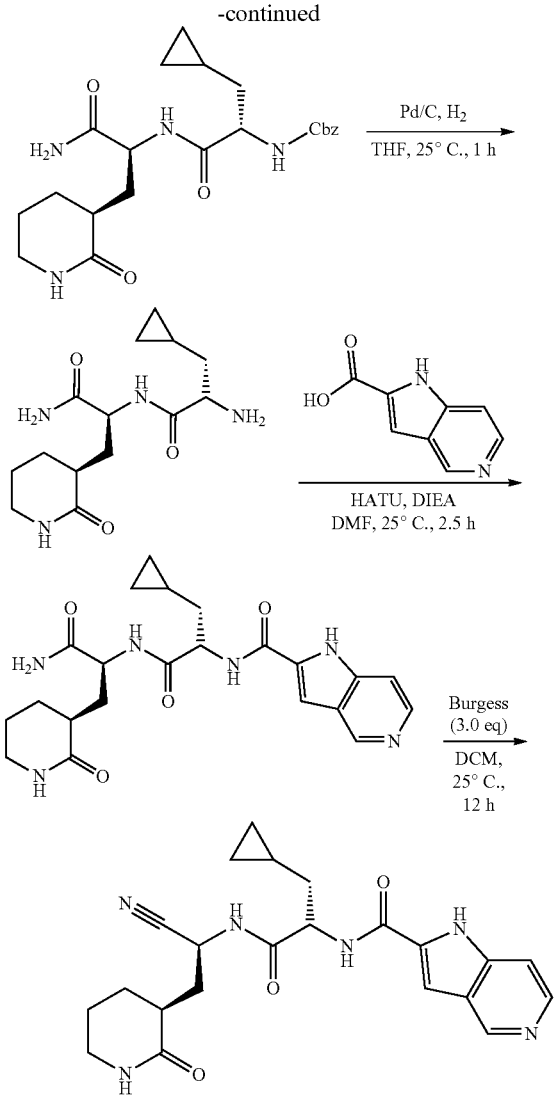

A solution of (2S)-2-amino-3-cyclopropyl-propanoic acid (5 g, 38.71 mmol, 1 eq) was added NaOH (1 M, 135.4 mL, 3.5 eq) and benzyl carbonochloridate (8.5 g, 50.33 mmol, 7.1 mL, 1.3 eq) was stirred at 25° C. for 2 hr. TLC (petroleum ether/ethyl acetate=1:1, PMA). The reaction mixture was diluted with H$_2$O (30 mL) and extracted with DCM (30 mL*3). The aqueous layer acidified with concentrated HCl and extracted with DCM. The combined organic layers were washed with brine (30 mL*2), dried with anhydrous Na$_2$SO$_4$, filtered and concentrated under reduced pressure to give a residue. Compound (2S)-2-(benzyloxycarbonylamino)-3-cyclopropyl-propanoic acid (7.7 g, 68.1% yield, 90% purity) was obtained as white solid.

Step 2: (S)-methyl2-((S)-2-(((benzyloxy)carbonyl)amino)-3-cyclopropylpropanamido)-3-((S)-2-oxopiperidin-3-yl)propanoate To a solution of (2S)-2-(benzyloxycarbonylamino)-3-cyclopropyl-propanoic acid (3.5 g, 13.29 mmol, 1 eq) and methyl (2S)-2-amino-3-[(3S)-2-oxo-3-piperidyl]propanoate (3.15 g, 13.29 mmol, 1 eq, HCl) in DMF (60 mL) was added TEA (4.04 g, 39.88 mmol, 5.55 mL, 3 eq) and T$_3$P (8.46 g, 13.29 mmol, 7.91 mL, 50% purity, 1 eq). The mixture was stirred at 25° C. for 2 hr. TLC (petroleum ether/ethyl acetate=0:1, I$_2$). LCMS detected desired compound. The reaction mixture was added H$_2$O (10 mL) and extracted with ethyl acetate (30 mL*3). The combined organic layers were washed with brine (20 mL), dried with anhydrous Na$_2$SO$_4$, filtered and concentrated under reduced pressure to give a residue. The residue was purified by flash silica gel chromatography (ISCO®; 12 g SepaFlash® Silica Flash Column, Eluent of 0~100% ethyl acetate/petroleum ether gradient @ 40 mL/min). Compound methyl(2S)-2-[[(2S)-2-(benzyloxycarbonylamino)-3-cyclopropyl-propanoyl]amino]-3-[(3S)-2-oxo-3-piperidyl]propanoate (4.5 g, 9.49 mmol, 71.4% yield, 94% purity) was obtained as a colorless oil.

Step 3: benzyl((S)-1-(((S)-1-amino-1-oxo-3-((S)-2-oxopiperidin-3-yl)propan-2-yl)amino)-3-cyclopropyl-1-oxopropan-2-yl)carbamate To a stirred solution of methyl (2S)-2-[[(2S)-2-(benzyloxycarbonylamino)-3-cyclopropyl-propanoyl]amino]-3-[(3S)-2-oxo-3-piperidyl]propanoate (4.5 g, 10.10 mmol, 1 eq) in MeOH (10 mL) was added with a solution of NH$_3$ (7 M, 50 mL, 34.65 eq). The mixture was allowed to stir at 80° C. for 24 h in a sealed tube. TLC (DCM/MeOH=10:1, I$_2$). LCMS detected the desired compound. The reaction mixture concentrated under reduced pressure to give a residue. The residue was purified by flash silica gel chromatography (ISCO®; 24 g SepaFlash® Silica Flash Column, Eluent of 0~5% DCM/MeOH @ 40 mL/min). Compound benzyl N-[(1S)-2-[[(1S)-2-amino-2-oxo-1-[[(3S)-2-oxo-3-piperidyl]methyl]ethyl]amino]-1-(cyclopropylmethyl)-2-oxoethyl]carbamate (3.6 g, 7.69 mmol, 76.17% yield, 92% purity) was obtained as a white solid.

Step 4: (S)-2-amino-N-((S)-1-amino-1-oxo-3-((S)-2-oxopiperidin-3-yl)propan-2-yl)-3-cyclopropylpropanamide To a solution of benzyl N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]carbamate (800 mg, 1.86 mmol, 1 eq) in MeOH (3 mL) was added Pd/C (100 mg, 1.86 mmol, 10% purity, 1 eq). The mixture was stirred at 25° C. for 2 h under H$_2$ (15 psi). LCMS indicated starting was consumed completely and detected desired compound. The reaction mixture was filtered and concentrated under reduced pressure to give a residue. Compound (2S)-2-amino-N-[(1S)-2-amino-2-oxo-1-[[(3S)-2-oxo-3-piperidyl]methyl]ethyl]-3-cyclopropyl-propanamide (550 mg, 1.86 mmol, 99.87% yield) was obtained as colorless oil.

Step 5: N-((S)-1-(((S)-1-amino-1-oxo-3-((S)-2-oxopiperidin-3-yl)propan-2-yl)amino)-3-cyclopropyl-1-oxopropan-2-yl)-1H-pyrrolo[3,2-c]pyridine-2-carboxamide A mixture of 1H-pyrrolo[3,2-c]pyridine-2-carboxylic acid (90.2 mg, 0.55 mmol, 1.1 eq), HATU (288.6 mg, 0.75 mmol, 1.5 eq) and DIPEA (196.2 mg, 1.52 mmol, 0.26 mL, 3 eq) in DMF (2 mL) was stirred at 25° C. for 0.5 h, and then (2S)-2-amino-N-[(1S)-2-amino-2-oxo-1-[[(3S)-2-oxo-3-piperidyl]methyl]ethyl]-3-cyclopropyl-propanamide (150 mg, 0.50 mmol, 1 eq) was added into the reaction. The resulting mixture was stirred 25° C. for 2 hr. TLC (DCM/MeOH=5:1, UV 254) indicated starting material was consumed completely and new spots formed. LCMS detected desired compound. The reaction mixture was added H₂O (10 mL) and extracted with DCM (10 mL*3). The combined organic layers were washed with brine (20 mL), dried with anhydrous Na₂SO₄, filtered and concentrated under reduced pressure to give a residue. The residue was purified by flash silica gel chromatography (ISCO®; 12 g SepaFlash® Silica Flash Column, Eluent of 0~20% MeOH/DCM @ 30 mL/min). Compound N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-1H-pyrrolo[3,2-c]pyridine-2-carboxamide (200 mg, 0.43 mmol, 86.1% yield, 96% purity) was obtained as a white solid.

Step 6: N-((S)-1-(((S)-1-cyano-2-((S)-2-oxopiperidin-3-yl)ethyl)amino)-3-cyclopropyl-1-oxopropan-2-yl)-1H-pyrrolo[3,2-c]pyridine-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-1H-pyrrolo[3,2-c]pyridine-2-carboxamide (120 mg, 0.27 mmol, 1 eq) in DCM (10 mL) was added Burgess reagent (194.7 mg, 0.81 mmol, 3 eq). The mixture was stirred at 25° C. for 16 h under N₂. LCMS detected desired compound. The reaction mixture was added H₂O (10 mL) and extracted with DCM (10 mL*3). The combined organic layers were washed with brine (20 mL), dried with anhydrous Na₂SO₄, filtered and concentrated under reduced pressure to give a residue. The residue was purified by prep-HPLC (column: Phenomenex Gemini-NX 80*40 mm*3 um; mobile phase: [water(0.05% NH₃H₂O+10 mM NH₄HCO₃)-ACN]; B %: 7%-37%, 9.5 min) to give ~20 mg crude product. The residue was purified by prep-HPLC (column: Welch Xtimate C18 150*25 mm*5 um; mobile phase: [water (0.05% ammonia hydroxide v/v)-MeOH]; B %: 0%-60%, 7.8 min). Compound N-[(1S)-2-[[(1S)-1-cyano-2-[(3S)-2-oxo-3-piperidyl]ethyl]amino]-1-(cyclopropylmethyl)-2-oxo-ethyl]-1H-pyrrolo[3,2-c]pyridine-2-carboxamide (2.37 mg, 5.4 umol, 1.9% yield, 96.8% purity) was obtained as a white solid.

LCMS: Rt=1.321 min; for C₂₂H₂₆N₆O₃ MS Calcd.: 422.48; MS Found: 423.1 [M+H⁺].

¹H NMR (400 MHz, CD₃OD) δ 9.03 (s, 1H), 8.43 (br d, J=6.27 Hz, 1H), 8.25 (d, J=6.27 Hz, 1H), 7.14-7.26 (m, 1H), 5.16 (t, J=8.16 Hz, 1H), 4.64 (br d, J=2.01 Hz, 1H), 3.25-3.29 (m, 2H), 2.41-2.60 (m, 2H), 1.93-2.09 (m, 2H), 1.71-1.91 (m, 4H), 1.49-1.63 (m, 1H), 0.88 (br s, 1H), 0.46-0.53 (m, 2H), 0.12-0.26 (m, 2H).

Example 181. Synthesis of Viral Protease Inhibitor Compound 669

Step 1: 4-chloro-1H-pyrrolo[2,3-c]pyridine-2-carboxylic acid

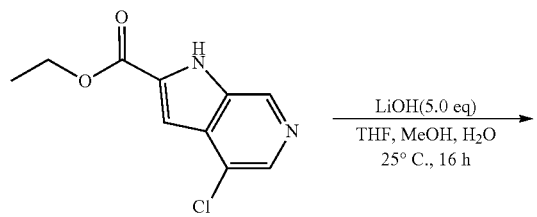

LiOH(5.0 eq)
THF, MeOH, H₂O
25° C., 16 h

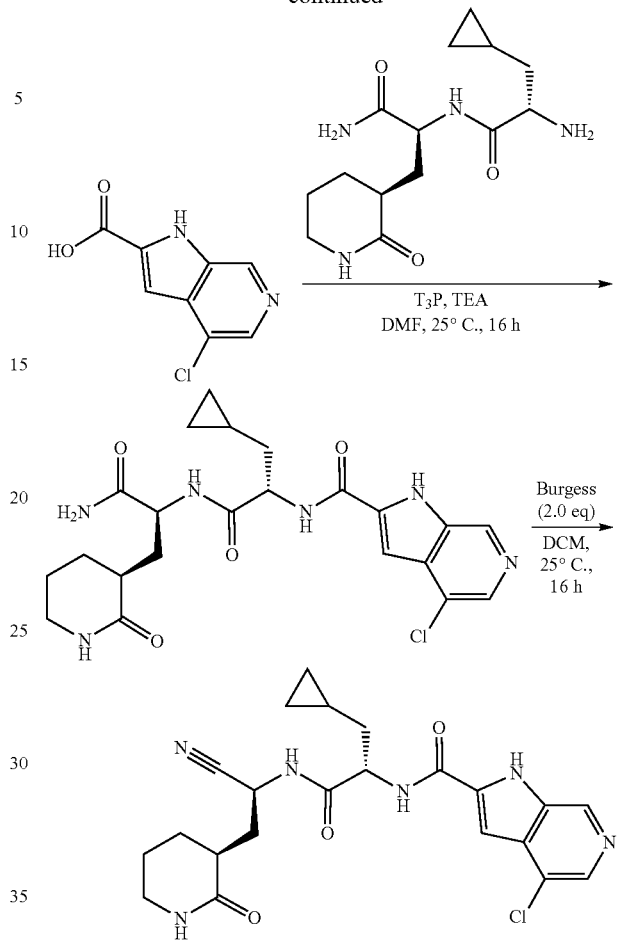

To a solution of ethyl 4-chloro-1H-pyrrolo[2,3-c]pyridine-2-carboxylate (300 mg, 1.34 mmol, 1 eq) in THF (5 mL) and MeOH (2 mL) was added LiOH·H₂O (280.2 mg, 6.68 mmol, 5 eq) and H₂O (2 mL). The mixture was stirred at 25° C. for 16 h. The reaction mixture was concentrated under reduced pressure to remove MeOH and THF. Then the pH of the residue was adjusted (neutralized) to about 6-7 with 2 M HCl, filtered, and then the cake concentrated under reduced pressure to give a residue. 4-chloro-1H-pyrrolo[2,3-c]pyridine-2-carboxylic acid (190 mg, 0.96 mmol, 72.3% yield) was obtained as a white solid.

Step 3: N-((S)-1-(((S)-1-amino-1-oxo-3-((S)-2-oxopiperidin-3-yl)propan-2-yl)amino)-3-cyclopropyl-1-oxopropan-2-yl)-4-chloro-1H-pyrrolo[2,3-c]pyridine-2-carboxamide To a solution of 4-chloro-1H-pyrrolo[2,3-c]pyridine-2-carboxylic acid (70 mg, 0.35 mmol, 1 eq) and (2S)-2-amino-N-[(1S)-2-amino-2-oxo-1-[[(3S)-2-oxo-3-piperidyl]methyl]ethyl]-3-cyclopropyl-propanamide (105.5 mg, 0.35 mmol, 1 eq) in DMF (2 mL) was added T₃P (226.5 mg, 0.35 mmol, 0.21 mL, 50% purity, 1 eq) and TEA (108.0 mg, 1.07 mmol, 0.14 mL, 3 eq). The mixture was stirred at 25° C. for 2 h. TLC (DCM/MeOH=5:1, UV 254). The reaction mixture was added with H₂O (10 mL) and extracted with ethyl acetate (10 mL*3). The combined organic layers were washed with brine (20 mL), dried with anhydrous Na₂SO₄, filtered and concentrated under reduced pressure to give a residue. The residue was purified by flash silica gel chromatography (ISCO®; 12 g SepaFlash® Silica Flash Column, Eluent of 0~15% MeOH/DCM @ 30 mL/min). Compound N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-chloro-1H-pyrrolo[2,3-c]pyridine-2-carboxamide (80 mg, 0.16 mmol, 46.8% yield, 99% purity) was obtained as a white solid.

Step 3: 4-chloro-N-((S)-1-(((S)-1-cyano-2-((S)-2-oxopiperidin-3-yl)ethyl)amino)-3-cyclopropyl-1-oxopropan-2-yl)-1H-pyrrolo[2,3-c]pyridine-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-chloro-1H-pyrrolo[2,3-c]pyridine-2-carboxamide (60 mg, 0.12 mmol, 1 eq) in DCM (2 mL) was added Burgess (60.2 mg, 0.25 mmol, 2 eq). The mixture was stirred at 25° C. for 16 h under $N_2$. The reaction mixture was added with $H_2O$ (10 mL) and extracted with DCM (10 mL*3). The combined organic layers were washed with brine (20 mL), dried with anhydrous $Na_2SO_4$, filtered and concentrated under reduced pressure to give a residue. The residue was purified by prep-HPLC (column: Welch Xtimate C18 150*25 mm*5 um; mobile phase: [water (0.05% ammonia hydroxide v/v)-MeOH]; B %: 53%-83%, 7.8 min). Compound 4-chloro-N-[(1S)-2-[[(1S)-1-cyano-2-[(3S)-2-oxo-3-piperidyl]ethyl]amino]-1-(cyclopropylmethyl)-2-oxo-ethyl]-1H-pyrrolo[2,3-c]pyridine-2-carboxamide (9.41 mg, 19.8 umol, 15.7% yield, 96.6% purity) was obtained as a white solid.

LCMS: Rt=1.895 min; for $C_{22}H_{25}ClN_6O_3$ MS Calcd.: 456.93; MS Found: 457.1 [M+H$^+$].

$^1$H NMR (400 MHz, CD$_3$OD) δ 8.72 (s, 1H), 8.13 (s, 1H), 7.35-7.39 (m, 1H), 5.14 (dd, J=10.04, 6.02 Hz, 1H), 4.56 (t, J=7.53 Hz, 1H), 3.22-3.28 (m, 2H), 2.40-2.57 (m, 2H), 1.88-2.05 (m, 3H), 1.82 (td, J=9.16, 4.27 Hz, 1H), 1.68 (dd, J=14.43, 7.15 Hz, 1H), 1.47-1.58 (m, 1H), 1.31 (t, J=7.28 Hz, 1H), 0.80-0.91 (m, 1H), 0.48-0.57 (m, 2H), 0.15-0.26 (m, 2H).

Example 182. Synthesis of Viral Protease Inhibitor Compound 633

Step 1: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-5-chloro-1H-indole-2-carboxamide

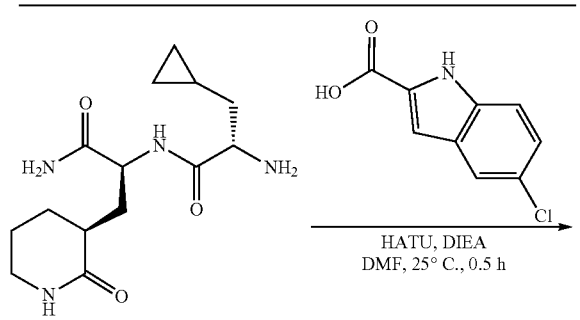

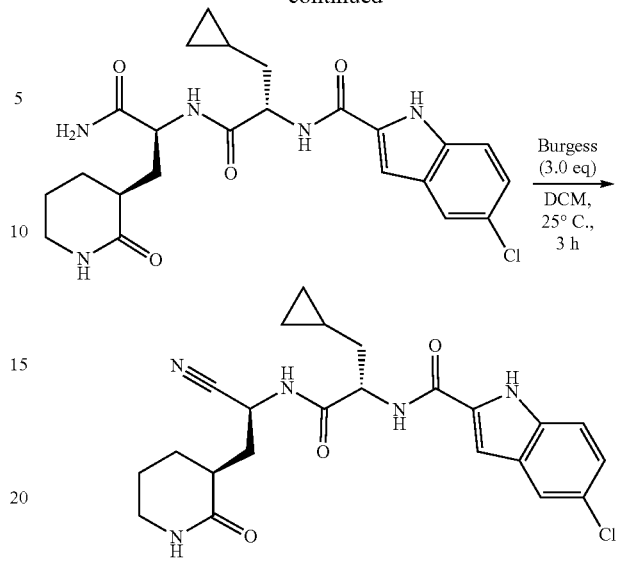

To a solution of (2S)-2-amino-N-[(1S)-2-amino-2-oxo-1-[[(3S)-2-oxo-3-piperidyl]methyl]ethyl]-3-cyclopropyl-propanamide (100.0 mg, 0.33 mmol, 1 eq) and 5-chloro-1H-indole-2-carboxylic acid (66.0 mg, 0.33 mmol, 1 eq) in DMF (2 mL) was added HATU (153.9 mg, 0.40 mmol, 1.2 eq) and DIEA (87.2 mg, 0.67 mmol, 0.11 mL, 2 eq). The mixture was stirred at 25° C. for 0.5 h. The reaction mixture was concentrated under reduced pressure to remove DMF. The residue was diluted with $H_2O$ (10 mL) and extracted with ethyl acetate (25 mL*3). The combined organic layers were washed with Brine (10 mL), dried over $Na_2SO_4$, filtered and concentrated under reduced pressure to give a residue. The residue was purified by flash silica gel chromatography (ISCO®; 4 g SepaFlash® Silica Flash Column, Eluent of 0~10% Methanol/Dichloromethane@ 20 mL/min). Compound N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-5-chloro-1H-indole-2-carboxamide (150.0 mg, 90.9% yield) was obtained as a yellow solid.

Step 2: 5-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-5-chloro-1H-indole-2-carboxamide (129.0 mg, 0.27 mmol, 1 eq) in DCM (2.5 mL) was added Burgess reagent (259.4 mg, 1.09 mmol, 4 eq) at 0° C. The mixture was stirred at 25° C. for 3 h. The reaction mixture was concentrated under reduced pressure to remove DCM. The residue was diluted with $H_2O$ (15 mL) and extracted with ethyl acetate (30 mL*3). The combined organic layers were washed with brine (20 mL), dried over $Na_2SO_4$, filtered and concentrated under reduced pressure to give a residue. The residue was purified by prep-HPLC (column: Phenomenex Gemini-NX 80*40 mm*3 um; mobile phase: [water (0.05% NH$_3$H$_2$O+10 mM NH$_4$HCO$_3$)-ACN]; B %: 31%-61%, 7.8 min). Compound 5-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide (40.2 mg, 30.2% yield) was obtained as a white solid.

LCMS: Rt=0.832 min; for C₂₃H₂₆ClN₅O₃ MS Calcd.: 455.94; MS Found: 456.1 [M+H⁺].

¹H NMR (400 MHz, CD₃OD) δ 7.61 (d, J=1.8 Hz, 1H), 7.41 (d, J=8.8 Hz, 1H), 7.19 (dd, J=2.0, 8.8 Hz, 1H), 7.14 (s, 1H), 5.13 (br dd, J=6.1, 10.2 Hz, 1H), 4.57-4.52 (m, 1H), 3.24-3.20 (m, 1H), 2.56-2.40 (m, 2H), 2.05-1.84 (m, 4H), 1.80-1.59 (m, 3H), 1.57-1.42 (m, 1H), 0.85 (br s, 1H), 0.54 (br d, J=8.3 Hz, 2H), 0.19 (br dd, J=5.1, 9.9 Hz, 2H).

Example 183. Synthesis of Viral Protease Inhibitor Compound 635

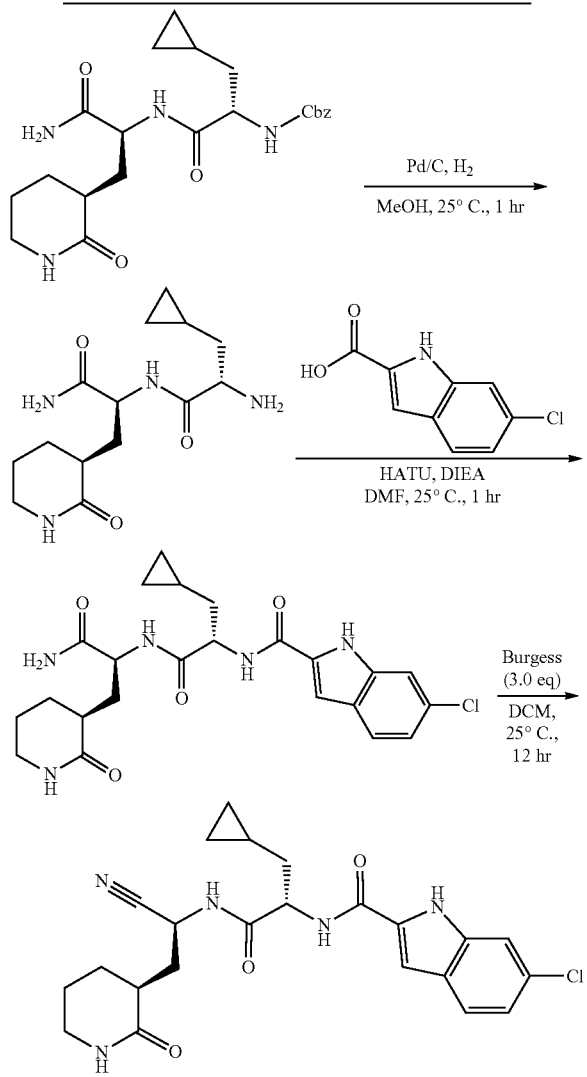

To a solution of benzyl N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]carbamate (400 mg, 0.92 mmol, 1 eq) in MeOH (5 mL) was added Pd (200 mg, 10% purity) and H₂ (0.92 mmol). The mixture was stirred at 25° C. under 15 psi for 1 h. The mixture was filtered to give the filter liquor and the reaction was concentrated under reduce pressure to give (2S)-2-amino-N-[(1S)-2-amino-2-oxo-1-[[(3S)-2-oxo-3-piperidyl]methyl]ethyl]-3-cyclopropyl-propanamide (274 mg, 0.92 mmol, 99.5% yield) as a white solid.

Step 2: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-chloro-1H-indole-2-carboxamide To a solution of (2S)-2-amino-N-[(1S)-2-amino-2-oxo-1-[[(3S)-2-oxo-3-piperidyl]methyl]ethyl]-3-cyclopropyl-propanamide (137 mg, 0.46 mmol, 1 eq) and 6-chloro-1H-indole-2-carboxylic acid (90.4 mg, 0.46 mmol, 1 eq) in DMF (2 mL) was added DIPEA (119.4 mg, 0.92 mmol, 0.16 mL, 2 eq) and HATU (210.9 mg, 0.55 mmol, 1.2 eq). The mixture was stirred at 25° C. for 1 h. The mixture was concentrated under reduce pressure, and the residue was purified by flash silica gel chromatography (ISCO®; 12 g SepaFlash® Silica Flash Column, Eluent of 0~10% DCM/MeOH @ 30 mL/min) to give N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-chloro-1H-indole-2-carboxamide (200 mg, 89.0% yield) as a white solid.

LCMS: Rt=0.780 min; for C₂₃H₂₈ClN₅O₄ MS Calcd.: 473.18; MS Found: 474.1 [M+H⁺].

Step 3: 6-Chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-chloro-1H-indole-2-carboxamide (47.5 mg, 0.1 mmol, 1 eq) in DCM (1 mL) was added Burgess reagent (71.6 mg, 0.3 mmol, 3 eq) at 0° C. The mixture was stirred at 25° C. for 12 h. The mixture was concentrated under reduce pressure, and the residue was purified by prep-HPLC (column: Phenomenex Gemini-NX 80*40 mm*3 um; mobile phase: [water(0.05% NH₃H₂O+10 mM NH₄HCO₃)-ACN]; B %: 31%-61%, 7.8 min) to give 6-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide (64.33 mg, 34.7% yield) as a white solid.

LCMS: Rt=0.832 min; for C₂₃H₂₆ClN₅O₃; MS Calcd.: 455.17; MS Found: 456.1 [M+H⁺].

¹H NMR (400 MHz, DMSO-d₆) δ 11.73 (br s, 1H), 8.95 (br d, J=8.0 Hz, 1H), 8.66 (br d, J=7.5 Hz, 1H), 7.66 (d, J=8.5 Hz, 1H), 7.53 (br s, 1H), 7.44 (s, 1H), 7.31 (s, 1H), 7.05 (dd, J=1.8, 8.5 Hz, 1H), 5.11-4.96 (m, 1H), 4.52-4.42 (m, 1H), 3.09 (br s, 2H), 2.34-2.21 (m, 2H), 1.89-1.75 (m, 3H), 1.74-1.65 (m, 1H), 1.56 (br s, 1H), 1.51-1.29 (m, 2H), 0.79 (br s, 1H), 0.42 (br d, J=7.0 Hz, 2H), 0.23-0.01 (m, 2H).

Example 184. Synthesis of Viral Protease Inhibitor Compound 637

Step 1: 4,7-Dichloro-2-(trichloromethyl)-1H-benzimidazole

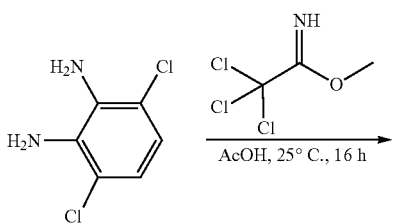

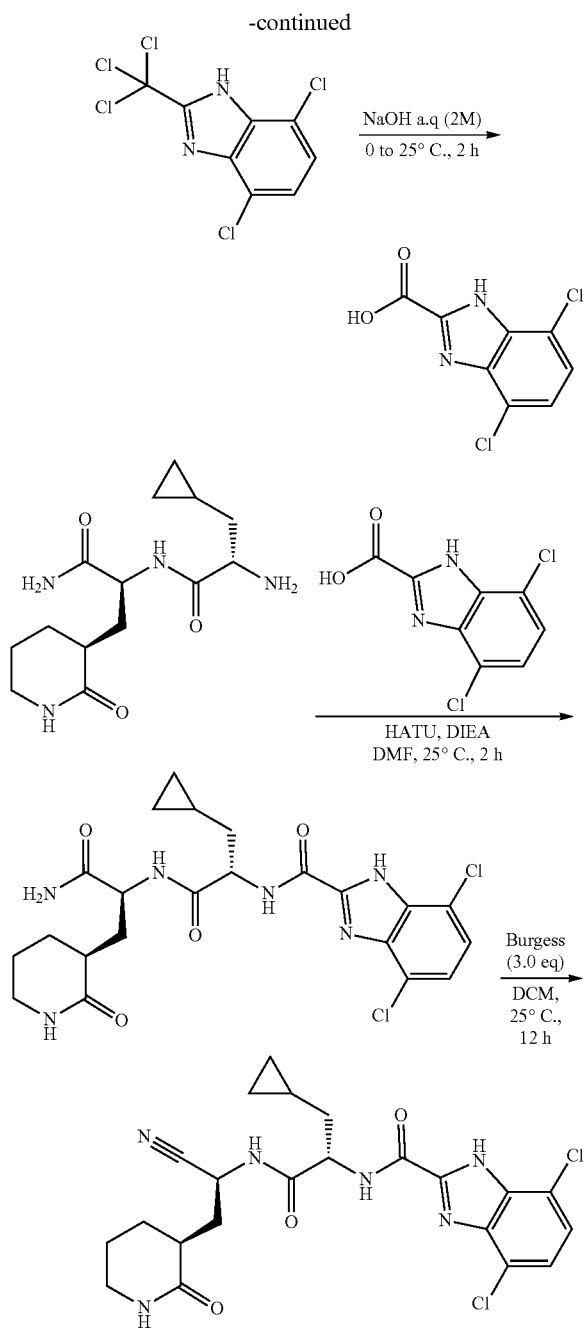

mixture was stirred at 25° C. for 1 h. The pH of the mixture was adjusted with HCl (2 M) to 2-3 and then the mixture was filtered to give 4,7-dichloro-1H-benzo[d]imidazole-2-carboxylic acid (0.2 g, crude) as a white solid.

Step 3: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4,6-dichloro-1H-benzimidazole-2-carboxamide To a solution of (S)-2-amino-N-((S)-1-amino-1-oxo-3-((S)-2-oxopiperidin-3-yl)propan-2-yl)-3-cyclopropylpropanamide (130 mg, 0.43 mmol, 1 eq) and 4,7-dichloro-1H-benzo[d]imidazole-2-carboxylic acid (101.3 mg, 0.43 mmol, 1.0 eq) in DMF (3 mL) was added HATU (250.1 mg, 0.65 mmol, 1.5 eq) and DIPEA (113.3 mg, 0.87 mmol, 0.15 mL, 2.0 eq). The mixture was stirred at 25° C. for 1 h. TLC (Dichloromethane:Methanol=10/1, UV). The reaction mixture was concentrated under reduced pressure to give a residue. The residue was purified by column chromatography (SiO$_2$, petroleum ether/ethyl acetate=100/1 to 10/1) to give N-((S)-1-(((S)-1-amino-1-oxo-3-((S)-2-oxopiperidin-3-yl)propan-2-yl)amino)-3-cyclopropyl-1-oxopropan-2-yl)-4,7-dichloro-1H-benzo[d]imidazole-2-carboxamide (0.2 g, 0.39 mmol, 89% yield) as a white solid.

Step 4: 4,7-dichloro-N-[(1S)-2-[[(1S)-1-cyano-2-[(3S)-2-oxo-3-piperidyl]ethyl]amino]-1-(cyclopropylmethyl)-2-oxo-ethyl]-1H-benzimidazole-2-carboxamide To a solution of N-((S)-1-(((S)-1-amino-1-oxo-3-((S)-2-oxopiperidin-3-yl)propan-2-yl)amino)-3-cyclopropyl-1-oxopropan-2-yl)-4,7-dichloro-1H-benzo[d]imidazole-2-carboxamide (100.00 mg, 0.19 mmol, 1 eq) in DCM (3.0 mL) was added Burgess reagent (140.3 mg, 0.58 mmol, 3.0 eq). The mixture was stirred at 25° C. for 1 h. The reaction mixture was concentrated under reduced pressure to give a residue. The residue was purified by prep-HPLC (column: Phenomenex Gemini-NX 80*40 mm*3 um; mobile phase: [water (0.05% NH$_3$H$_2$O+10 mM NH4HCO3)-ACN]; B %: 20%-50%, 7.8 min) to give S4C_50 (22.11 mg, 22% yield) as a white solid.

LCMS: Rt=0.824 min; for C$_{22}$H$_{24}$Cl$_2$N$_6$O$_3$ MS Calcd.: 490.13; MS Found: 491.1 [M+H$^+$].

$^1$H NMR (400 MHz, CD$_3$OD) δ 7.30 (s, 2H), 5.22-5.09 (m, 1H), 4.60 (t, J=7.1 Hz, 1H), 3.27-3.19 (m, 2H), 2.56-2.37 (m, 2H), 2.06-1.88 (m, 3H), 1.87-1.79 (m, 1H), 1.73 (td, J=7.2, 14.0 Hz, 2H), 1.60-1.44 (m, 1H), 0.96-0.75 (m, 1H), 0.54 (d, J=6.9 Hz, 2H), 0.21 (dd, J=4.8, 10.4 Hz, 2H).

Example 185. Synthesis of Viral Protease Inhibitor Compound 639

To a solution of 3,6-dichlorobenzene-1,2-diamine (0.3 g, 1.69 mmol, 1 eq) in AcOH (12.57 g, 209.2 mmol, 11.97 mL, 123.8 eq) was added methyl 2,2,2-trichloroacetimidate (313.0 mg, 1.77 mmol, 0.21 mL, 1.05 eq) at 0° C. The mixture was stirred at 25° C. for 16 h. LC-MS showed 48% of 1 was remained and 43% of desired compound was detected. The reaction mixture was diluted with H$_2$O (40 mL) and filtered to give 2 (300 mg, crude) as a white solid.

Step 2: 4,7-Dichloro-1H-benzimidazole-2-carboxylic acid

To a solution of NaOH (0.8 g, 20.0 mmol, 20.2 eq) in H$_2$O (10 mL) was added 4,7-dichloro-2-(trichloromethyl)-1H-benzo[d]imidazole (0.3 g, 985.58 umol, 1 eq) at 0° C. The Step 1: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-1H-indole-2-carboxamide

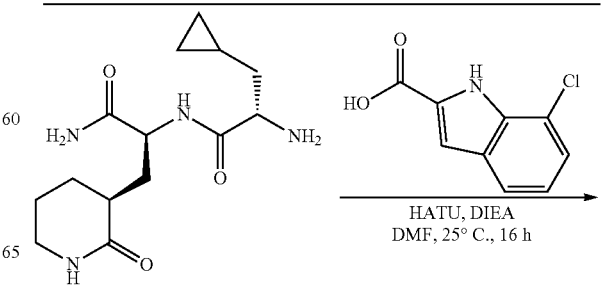

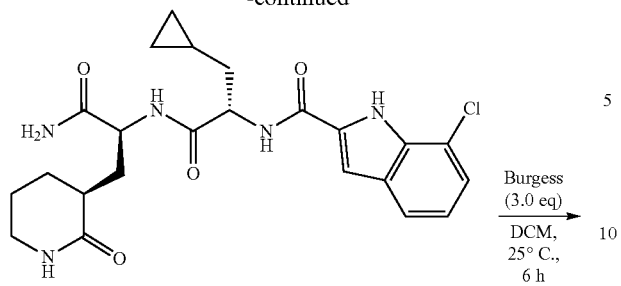

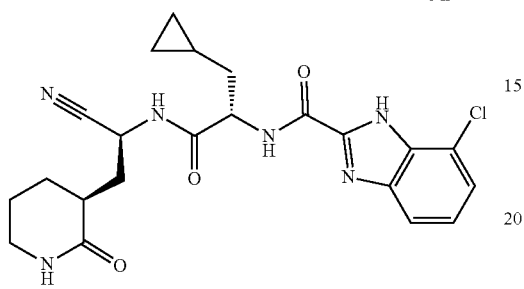

To a solution of (2S)-2-amino-N-[(1S)-2-amino-2-oxo-1-[[(3S)-2-oxo-3-piperidyl]methyl]ethyl]-3-cyclopropyl-propanamide (70 mg, 0.23 mmol, 1 eq) in DMF (1 mL) was added HATU (89.8 mg, 0.23 mmol, 1 eq), 7-chloro-1H-indole-2-carboxylic acid (50.8 mg, 0.25 mmol, 1.1 eq) and DIEA (61.0 mg, 0.47 mmol, 82.2 uL, 2 eq). The mixture was stirred at 25° C. for 16 h. The reaction mixture was diluted with H$_2$O (30 mL) and extracted with ethyl acetate (30 mL*3). The combined organic layers were washed with brine (30 mL*2), dried with anhydrous Na$_2$SO$_4$, filtered and concentrated under reduced pressure to give a residue. The residue was purified by prep-HPLC (column: Phenomenex Gemini-NX 80*40 mm*3 um; mobile phase: [water(0.05% NH$_3$H$_2$O+10 mM NH$_4$HCO$_3$)-ACN]; B %: 16%-46%, 9.5 min). Compound N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-1H-indole-2-carboxamide (67 mg, 0.12 mmol, 53.8% yield, 90% purity) was obtained as a white solid.

Step 2: 7-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-1H-indole-2-carboxamide (60 mg, 0.12 mmol, 1 eq) in DCM (1 mL) was added methoxycarbonyl-(triethylammonio)sulfonyl-azanide (90.5 mg, 0.37 mmol, 3 eq). The mixture was stirred at 25° C. for 6 h. The reaction mixture was diluted with H$_2$O (30 mL) and extracted with DCM (30 mL*3). The combined organic layers were washed with brine (30 mL*2), dried with anhydrous Na$_2$SO$_4$, filtered and concentrated under reduced pressure to give a residue. The residue was purified by prep-HPLC (column: Phenomenex Gemini-NX 80*40 mm*3 um; mobile phase: [water(0.05% NH$_3$H$_2$O+10 mM NH$_4$HCO$_3$)-ACN]; B %: 26%-56%, 7.8 min). 7-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide (12.34 mg, 21.3% yield, 100% purity) was obtained as white solid.

LCMS: Rt=2.130 min; for C$_{23}$H$_{26}$ClN$_5$O$_3$ MS Calcd.: 455.94; MS Found: 456.1 [M+H$^+$].

$^1$H NMR (400 MHz, CD$_3$OD) δ 7.58 (d, J=8.0 Hz, 1H), 7.32-7.21 (m, 2H), 7.07 (t, J=7.8 Hz, 1H), 5.14 (dd, J=6.0, 10.0 Hz, 1H), 4.57 (t, J=7.4 Hz, 1H), 3.28-3.16 (m, 2H), 2.56-2.28 (m, 2H), 2.05-1.88 (m, 3H), 1.87-1.78 (m, 1H), 1.77-1.61 (m, 2H), 1.59-1.44 (m, 1H), 0.92-0.80 (m, 1H), 0.60-0.49 (m, 2H), 0.26-0.14 (m, 2H).

Example 185a. Synthesis of Viral Protease Inhibitor Compound 639 & 639A

Step 1: Methyl (2S)-2-[[(2S)-2-(tert-butoxycarbonylamino)-3-cyclopropyl-propanoyl]amino]-3-[(3S)-2-oxo-3-piperidyl]propanoate

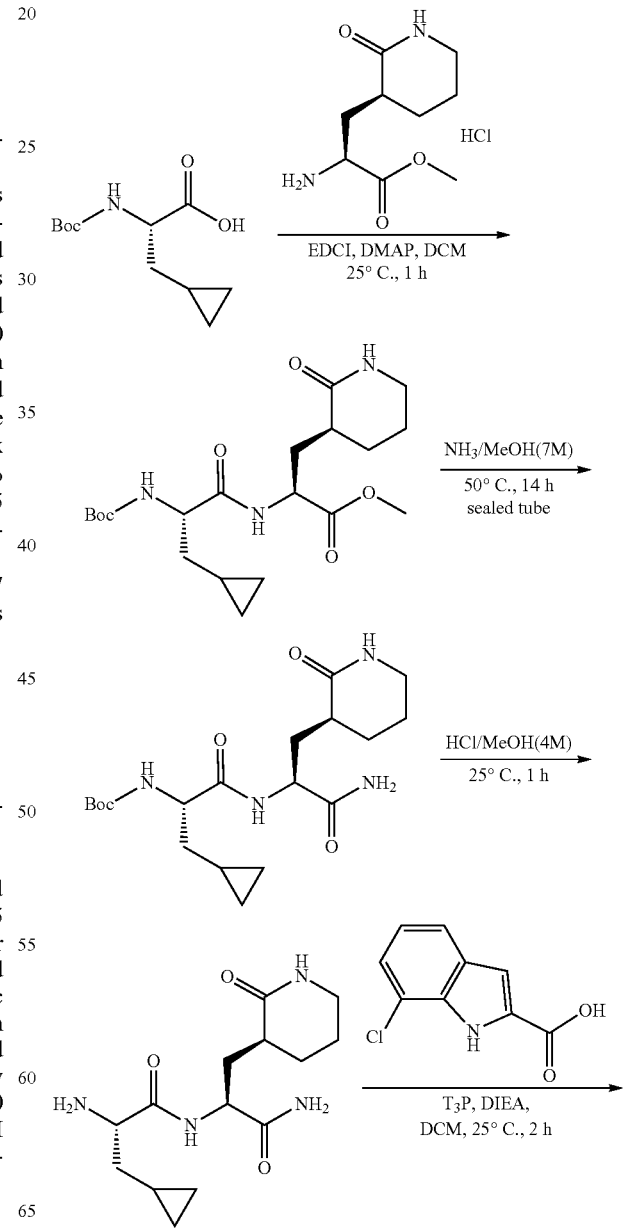

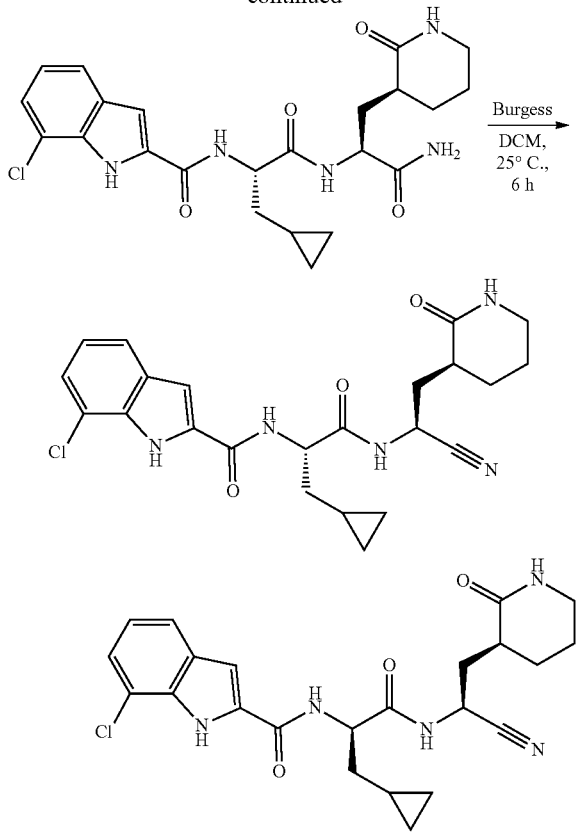

To a solution of (2S)-2-(tert-butoxycarbonylamino)-3-cyclopropyl-propanoic acid (1.07 g, 4.65 mmol, 1.1 eq), methyl (2S)-2-amino-3-[(3S)-2-oxo-3-piperidyl]propanoate (1 g, 4.22 mmol, 1 eq, HCl) in DCM (10 mL) was added the DMAP (1.55 g, 12.67 mmol, 3 eq), EDCI (1.62 g, 8.45 mmol, 2 eq), and the resulting solution was stirred at 25° C. for 1 h. Upon completion, the solution was diluted with H₂O (30 mL), extracted with ethyl acetate (30 mL*3), the combined organic phase was dried over Na₂SO₄, filtrated and concentrated to give the crude. The residue was purified by column chromatography (SiO₂, DCM/MeOH=30/1 to 10/1) to give methyl (2S)-2-[[(2S)-2-(tert-butoxycarbonylamino)-3-cyclopropyl-propanoyl]amino]-3-[(3S)-2-oxo-3-piperidyl] propanoate (1.2 g, 2.92 mmol, 68.97% yield, 100% purity) as a yellow oil. MS (ESI) m/z 412.3 [M+H]⁺.

Step 2: (2R)-N-(4-(tert-butyl)phenyl)-N-(2-oxo-1-(pyridin-3-yl)-2-((pyridin-4-ylmethyl)amino)ethyl) pyrrolidine-2-carboxamide Methyl (2S)-2-[[(2S)-2-(tert-butoxycarbonylamino)-3-cyclopropyl-propanoyl]amino]-3-[(3S)-2-oxo-3-piperidyl] propanoate (600 mg, 1.46 mmol, 1 eq) in ammonia (7 M, 7.2 mL, 8.30 eq) was stirred at 50° C. for 14 h. Upon completion, the solution was concentrated to give Tert-butyl N-[(1S)-2-[[(1S)-2-amino-2-oxo-1-[[(3S)-2-oxo-3-piperidyl] methyl] ethyl] amino]-1-(cyclopropylmethyl)-2-oxo-ethyl] carbamate (580 mg, crude) as a yellow oil. MS (ESI) m/z 397.3 [M+H]⁺.

Step 3: (2S)-2-amino-N-[(1S)-2-amino-2-oxo-1-[[(3S)-2-oxo-3-piperidyl]methyl]ethyl]-3-cyclopropyl-propanamide A solution of tert-butyl N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]carbamate (580 mg, 1.46 mmol, 1 eq) in HCl/MeOH (4 M, 10.00 mL, 7.93 eq) was stirred at 25° C. for 1 h. Upon completion, the solution was concentrated to give (2S)-2-amino-N-[(1S)-2-amino-2-oxo-1-[[(3S)-2-oxo-3-piperidyl]methyl]ethyl]-3-cyclopropyl-propanamide (380 mg, crude) was obtained as a yellow oil. MS (ESI) m/z 297.2 [M+H]⁺.

Step 4: (2S)-2-amino-N-[(1S)-2-amino-2-oxo-1-[[(3S)-2-oxo-3-piperidyl]methyl]ethyl]-3-cyclopropyl-propanamide To a solution of (2S)-2-amino-N-[(1S)-2-amino-2-oxo-1-[[(3S)-2-oxo-3-piperidyl]methyl]ethyl]-3-cyclopropyl-propanamide (380 mg, 1.28 mmol, 1 eq) in DCM (3 mL) was added 7-chloro-1H-indole-2-carboxylic acid (275.88 mg, 1.41 mmol, 1.1 eq), T3P (1.22 g, 1.93 mmol, 1.14 mL, 50% purity, 1.5 eq) and DIEA (331.44 mg, 2.56 mmol, 446.68 uL, 2 eq) The mixture was stirred at 25° C. for 2 h. Upon completion, the solution was diluted with H₂O (20 mL), extracted with DCM (30 mL*3), the combined organic phase was dried over Na₂SO₄, filtrated and concentrated to give the crude. The residue was purified by prep-TLC (SiO₂, DCM:MeOH=10:1) to give N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-1H-indole-2-carboxamide (350 mg, 738.47 umol, 57.59% yield, 100% purity) as yellow oil. MS (ESI) m/z 474.3 [M+H]⁺.

Step 5: 7-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-1H-indole-2-carboxamide (350 mg, 738.47 umol, 1 eq) in DCM (4 mL) was added Burgess reagent (527.94 mg, 2.22 mmol, 3 eq), and the solution was stirred at 25° C. for 6 h. Upon completion, DCM was removed using blow dry to give a residue. The residue was purified by prep-HPLC (column: Waters Xbridge Prep OBD C18 150*40 mm*10 um; mobile phase: [water(0.05% NH₃H₂O+10 mM NH4HCO₃)-ACN]; B %: 25%-55%, 8 min) to give desired compound as a white solid, which was further separated by SFC (column: DAICEL CHIRALPAK AS (250 mm*30 mm, 10 um); mobile phase: [0.1% NH₃H₂O ETOH]; B %: 33%-33%, 8 min) to give 7-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide (250 mg, 530.89 umol, 74.25% yield, 96.82% purity) as a white solid. MS (ESI) m/z 456.2 [M+H]⁺.

¹H NMR (400 MHz, METHANOL-d₄) δ=7.58 (d, J=7.9 Hz, 1H), 7.35-7.20 (m, 2H), 7.06 (t, J=7.8 Hz, 1H), 5.22-5.05 (m, 1H), 4.57 (t, J=7.5 Hz, 1H), 3.27-3.14 (m, 2H), 2.61-2.34 (m, 2H), 2.09-1.61 (m, 6H), 1.59-1.43 (m, 1H), 0.98-0.76 (m, 1H), 0.55 (dd, J=1.3, 8.2 Hz, 2H), 0.31-0.09 (m, 2H).

7-Chloro-N-[(1R)-2-[[(1S)-1-cyano-2-[(3S)-2-oxo-3-piperidyl]ethyl]amino]-1-(cyclopropylmethyl)-2-oxo-ethyl]-1H-indole-2-carboxamide (45 mg, 98.70 umol, 13.37% yield, 100% purity) was obtained as white solid. MS (ESI) m/z 456.2 [M+H]⁺.

¹H NMR (400 MHz, METHANOL-d₄) δ=7.59 (dd, J=0.9, 7.9 Hz, 1H), 7.32-7.21 (m, 2H), 7.07 (t, J=7.8 Hz, 1H), 5.12-5.02 (m, 1H), 4.59 (dd, J=6.4, 7.9 Hz, 1H), 3.21 (dd,

J=4.6, 7.7 Hz, 2H), 2.44-2.23 (m, 2H), 2.09-1.62 (m, 6H), 1.60-1.47 (m, 1H), 0.94-0.78 (m, 1H), 0.62-0.43 (m, 2H), 0.27-0.11 (m, 2H).

Example 186. Synthesis of Viral Protease Inhibitor Compound 643

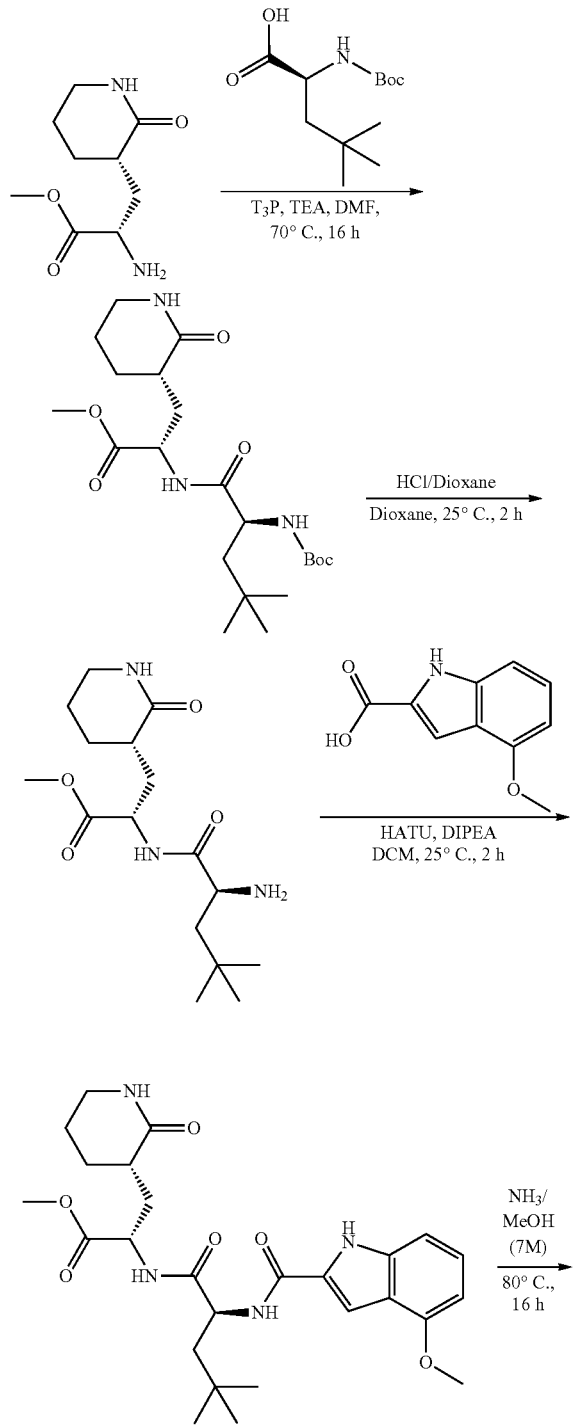

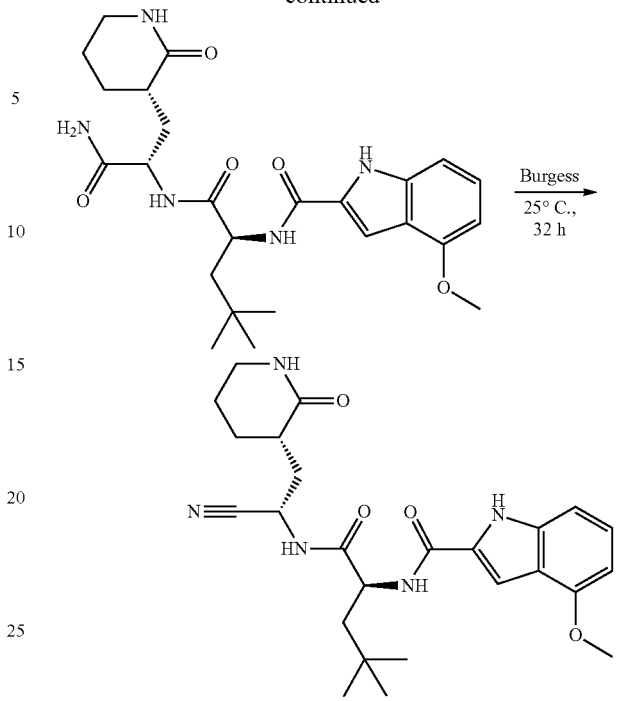

T₃P (2.69 g, 4.22 mmol, 2.51 mL, 50% purity, 2 eq) was added to a mixture of methyl (2S)-2-amino-3-[(3S)-2-oxo-3-piperidyl]propanoate (500 mg, 2.11 mmol, 1 eq, HCl), (2S)-2-(tert-butoxycarbonylamino)-4,4-dimethyl-pentanoic acid (570.0 mg, 2.32 mmol, 1.1 eq) and TEA (855.0 mg, 8.45 mmol, 1.18 mL, 4 eq) in DMF (5 mL). Then the mixture was stirred at 70° C. for 16 h. TLC (petroleum ether:ethyl acetate=0:1/PMA). The reaction mixture was diluted with H₂O (10 mL) and the mixture was extracted with ethyl acetate (10 mL*3). The combined organic phase was washed with brine (10 mL*2), dried with anhydrous Na₂SO₄, filtered and concentrated in vacuum. The residue was purified by flash silica gel chromatography (ISCO®; 20 g SepaFlash® Silica Flash Column, Eluent of 0~100% ethyl acetate/petroleum ether gradient @30 mL/min). Methyl (2S)-2-[[(2S)-2-(tert-butoxycarbonylamino)-4,4-dimethyl-pentanoyl]amino]-3-[(3S)-2-oxo-3-piperidyl]propanoate (436 mg, 0.99 mmol, 47.2% yield, 97.9% purity) was obtained as white solid and confirmed by LC-MS, SFC and HNMR.

Step 2: methyl (2S)-2-[[(2S)-2-amino-4,4-dimethyl-pentanoyl]amino]-3-[(3S)-2-oxo-3-piperidyl]propanoate A solution of methyl (2S)-2-[[(2S)-2-(tert-butoxycarbonylamino)-4,4-dimethyl-pentanoyl]amino]-3-[(3S)-2-oxo-3-piperidyl]propanoate (300 mg, 0.70 mmol, 1 eq) in HCl/dioxane (4 M, 175.42 uL, 1 eq) was stirred at 25° C. for 2 h. The reaction mixture was filtered to afford ethyl (2S)-2-[[(2S)-2-amino-4,4-dimethyl-pentanoyl]amino]-3-[(3S)-2-oxo-3-piperidyl]propanoate (250 mg, crude, HCl) as a white solid.

Step 3: methyl (2S)-2-[[(2S)-2-[(4-methoxy-1H-indole-2-carbonyl)amino]-4,4-dimethyl-pentanoyl]amino]-3-[(3S)-2-oxo-3-piperidyl]propanoate A mixture of methyl (2S)-2-[[(2S)-2-amino-4,4-dimethyl-pentanoyl]amino]-3-[(3S)-2-oxo-3-piperidyl]propanoate (310 mg, 0.85 mmol, 1 eq, HCl), 4-methoxy-1H-indole-2-carboxylic acid (179.1 mg, 0.93 mmol, 1.1 eq), HATU (647.8 mg, 1.70 mmol, 2 eq) and DIPEA (440.4 mg, 3.41 mmol, 0.60 mL, 4 eq) in DCM (4 mL) was stirred at 25° C. for 2 h. TLC (PE:EA=0:1/UV254 nm). The reaction mixture was diluted with H$_2$O (10 mL) and the mixture was extracted with ethyl acetate (10 mL*3). The combined organic phase was washed with brine (10 mL*2), dried with anhydrous Na$_2$SO$_4$, filtered and concentrated in vacuum. The residue was purified by flash silica gel chromatography (ISCO®; 12 g SepaFlash® Silica Flash Column, Eluent of 0~100% ethyl acetate/petroleum ether gradient @ 30 mL/min). Methyl (2S)-2-[[(2S)-2-[(4-methoxy-1H-indole-2-carbonyl)amino]-4,4-dimethyl-pentanoyl]amino]-3-[(3S)-2-oxo-3-piperidyl] propanoate (451 mg, 0.68 mmol, 80.1% yield, 75.8% purity) was obtained as a yellow oil.

Step 4: N-[(1S)-1-[[(1S)-2-amino-2-oxo-1-[[(3S)-2-oxo-3-piperidyl]methyl]ethyl]carbamoyl]-3,3-dimethyl-butyl]-4-methoxy-1H-indole-2-carboxamide To a mixture of methyl (2S)-2-[[(2S)-2-[(4-methoxy-1H-indole-2-carbonyl)amino]-4,4-dimethyl-pentanoyl]amino]-3-[(3S)-2-oxo-3-piperidyl]propanoate (400 mg, 0.79 mmol, 1 eq) was added NH$_3$ (7 M, 11.42 mL, 100 eq), and then the resulting mixture was stirred at 80° C. for 16 h. TLC (DCM:MeOH=10:1/UV254 nm). The reaction mixture was concentrated in vacuum, and the residue was purified by flash silica gel chromatography (ISCO®; 12 g SepaFlash® Silica Flash Column, Eluent of 0~50% Ethyl acetate/MeOH@30 mL/min). N-[(1S)-1-[[(1S)-2-amino-2-oxo-1-[[(3S)-2-oxo-3-piperidyl]methyl]ethyl]carbamoyl]-3,3-dimethyl-butyl]-4-methoxy-1H-indole-2-carboxamide (295 mg, 0.60 mmol, 75.1% yield, 98.9% purity) was obtained as white a solid.

Step 5: N-[(1S)-1-[[(1 S)-1-cyano-2-[(3S)-2-oxo-3-piperidyl]ethyl]carbamoyl]-3,3-dimethyl-butyl]-4-methoxy-1H-indole-2-carboxamide Methoxycarbonyl-(triethylammonio)sulfonyl-azanide (284.6 mg, 1.19 mmol, 2 eq) was added to a mixture of N-[(1S)-1-[[(1S)-2-amino-2-oxo-1-[[(3S)-2-oxo-3-piperidyl]methyl]ethyl]carbamoyl]-3,3-dimethyl-butyl]-4-methoxy-1H-indole-2-carboxamide (290 mg, 0.59 mmol, 1 eq) in DCM (3 mL) at 25° C. Then the mixture was stirred at 25° C. for 16 h. Then, methoxycarbonyl-(triethylammonio)sulfonyl-azanide (142.3 mg, 0.59 mmol, 1 eq) was added to the mixture and the mixture was stirred at 25° C. for another 16 h. The reaction mixture was diluted with H$_2$O (10 mL) and the mixture was extracted with ethyl acetate (10 mL*3). The combined organic phase was washed with brine (10 mL*2), dried with anhydrous Na$_2$SO$_4$, filtered and concentrated in vacuum. The residue was purified by prep-HPLC (column: Welch Xtimate C18 150*25 mm*5 um; mobile phase: [water (0.05% ammonia hydroxide v/v)-MeOH]; B %: 55%-85%, 9.5 min). N-[(1S)-1-[[(1S)-1-cyano-2-[(3S)-2-oxo-3-piperidyl]ethyl]carbamoyl]-3,3-dimethyl-butyl]-4-methoxy-1H-indole-2-carboxamide (28.1 mg, 59.3 umol, 9.9% yield, 98.7% purity) was obtained as a white solid.

LCMS: Rt=0.832 min; for C$_{25}$H$_{33}$N$_5$O$_4$ MS Calcd.: 467.25, MS Found: 468.2 [M+H$^+$].

$^1$H NMR (400 MHz, CD$_3$OD) δ 7.26-7.22 (m, 1H), 7.18-7.12 (m, 1H), 7.05-7.00 (m, 1H), 6.51 (d, J=7.5 Hz, 1H), 5.08 (dd, J=6.3, 9.8 Hz, 1H), 4.67-4.63 (m, 1H), 3.93 (s, 3H), 3.21-3.15 (m, 2H), 2.47-2.38 (m, 2H), 1.98-1.72 (m, 6H), 1.70-1.58 (m, 1H), 1.54-1.43 (m, 1H), 1.02 (s, 8H), 1.04-1.01 (m, 2H).

Example 187. Synthesis of Viral Protease Inhibitor Compound 653

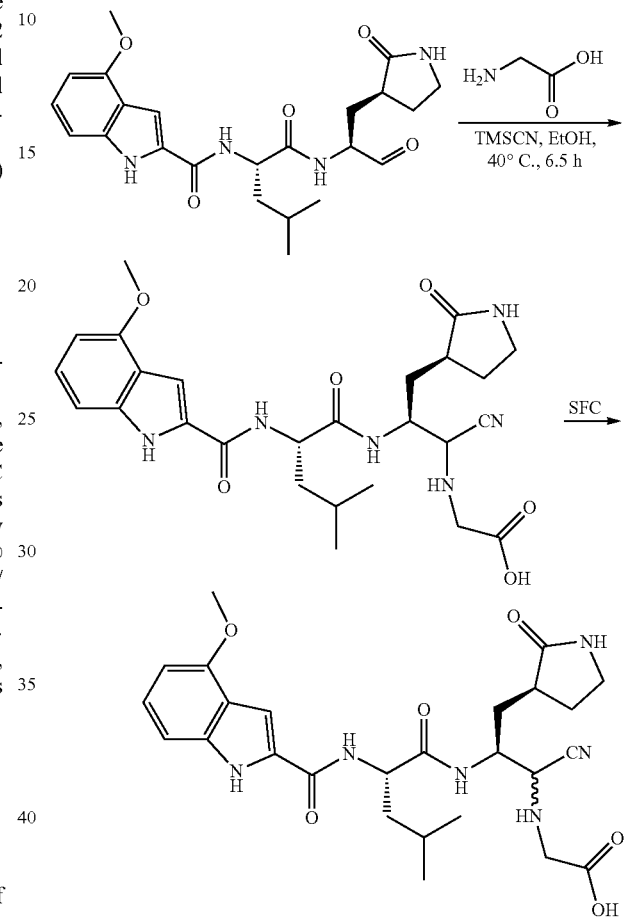

To a mixture of N-[(1S)-1-[[(1S)-1-formyl-2-[(3S)-2-oxopyrrolidin-3-yl]ethyl]carbamoyl]-3-methyl-butyl]-4-methoxy-1H-indole-2-carboxamide (1 g, 1.81 mmol, 80% purity, 1 eq) in EtOH (20 mL) was added 2-aminoacetic acid (271.74 mg, 3.62 mmol, 20.52 uL, 2 eq), ZnCl$_2$ (1 M, 18.10 uL, 0.01 eq). The mixture was stirred at 25° C. for 30 min, and then added TMSCN (359.14 mg, 3.62 mmol, 452.89 uL, 2 eq). The mixture was stirred at 40° C. for 6 h. Upon the reaction was completed, the reaction mixture was filtered and concentrated under reduced pressure to give a residue. The residue was purified by HCl prep-HPLC (column: Phenomenex luna C18 80*40 mm*3 um; mobile phase: [water (0.04% HCl)-ACN]; B %: 25%-45%, 7 min) to get a mixture. The mixture was separated by SFC (column: DAICEL CHIRALPAK AD (250 mm*30 mm, 10 um); mobile phase: [Neu-ETOH]; B %: 50%-50%, 10 min) to get the compound 2-[[(2S)-1-cyano-2-[[(2S)-2-[(4-methoxy-1H-indole-2-carbonyl)amino]-4-methyl-pentanoyl]amino]-3-[(3S)-2-oxopyrrolidin-3-yl]propyl]amino]acetic acid (125 mg, 235.87 umol, 13.03% yield, 99.363% purity) and 2-[[(2S)-1-cyano-2-[[(2S)-2-[(4-methoxy-1H-indole-2-carbonyl)amino]-4-methyl-pentanoyl]amino]-3-[(3S)-2- oxopyrrolidin-3-yl]propyl]amino]acetic acid (205 mg, 373.82 umol, 20.65% yield, 96.023% purity) as white solid. MS (ESI) m/z 527.3 [M+H]⁺.

Isomer 1: ¹H NMR (400 MHz, DMSO-d6) δ=11.56 (d, J=2.0 Hz, 1H), 8.52-8.21 (m, 2H), 7.58 (s, 1H), 7.35 (d, J=1.7 Hz, 1H), 7.14-7.05 (m, 1H), 7.03-6.97 (m, 1H), 6.50 (d, J=7.7 Hz, 1H), 4.57-4.41 (m, 1H), 4.14 (tdd, J=4.2, 8.2, 12.2 Hz, 1H), 3.97-3.82 (m, 4H), 3.52-3.36 (m, 2H), 3.18-2.98 (m, 2H), 2.41-2.27 (m, 1H), 2.12-2.04 (m, 2H), 1.82-1.36 (m, 5H), 0.91 (dd, J=6.4, 15.8 Hz, 6H)

Isomer 2: ¹H NMR (400 MHz, DMSO-d6) δ=11.57 (d, J=2.0 Hz, 1H), 8.39 (d, J=7.8 Hz, 1H), 8.20 (d, J=9.5 Hz, 1H), 7.54 (s, 1H), 7.37 (d, J=1.6 Hz, 1H), 7.16-6.94 (m, 2H), 6.50 (d, J=7.6 Hz, 1H), 4.53-4.36 (m, 1H), 4.18-4.01 (m, 1H), 3.88 (s, 3H), 3.77 (d, J=8.8 Hz, 1H), 3.43-3.33 (m, 2H), 3.15-2.96 (m, 2H), 2.38-2.25 (m, 1H), 2.08-2.01 (m, 1H), 1.91-1.47 (m, 6H), 0.91 (dd, J=6.4, 14.8 Hz, 6H).

Example 188. Synthesis of Viral Protease Inhibitor Compound 655

Step 1: (2S,4R)-di-tert-butyl 4-hydroxypyrrolidine-1,2-dicarboxylate

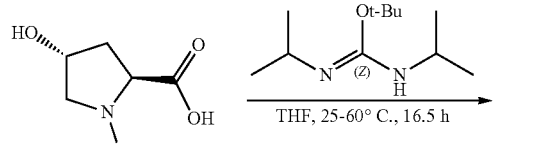

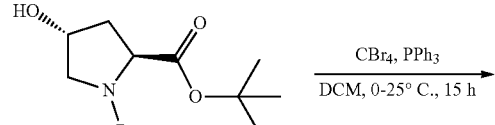

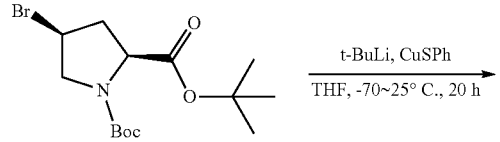

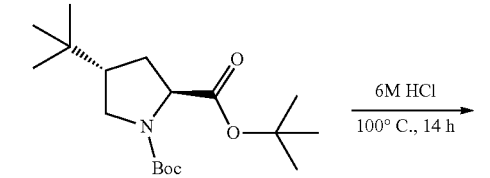

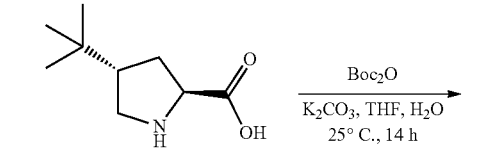

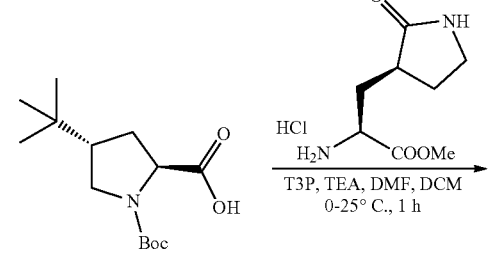

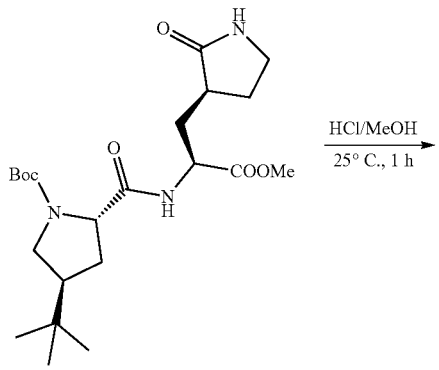

-continued

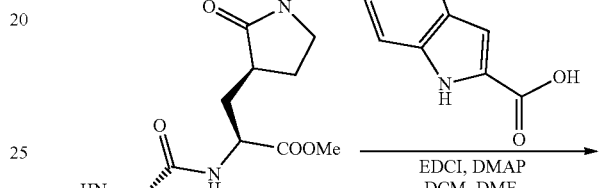

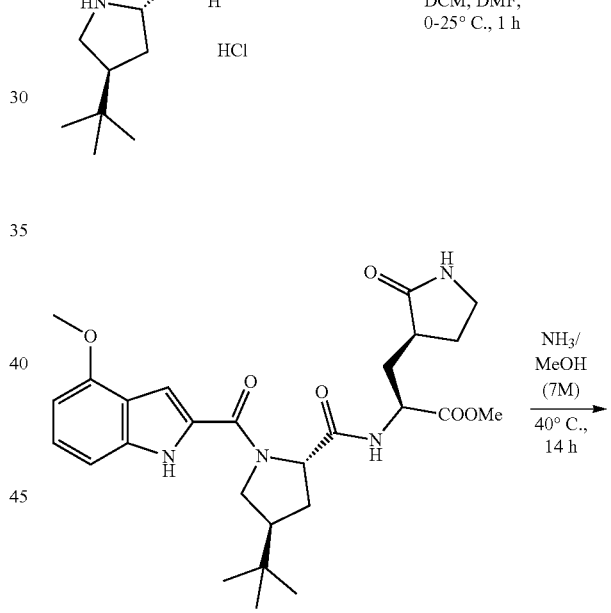

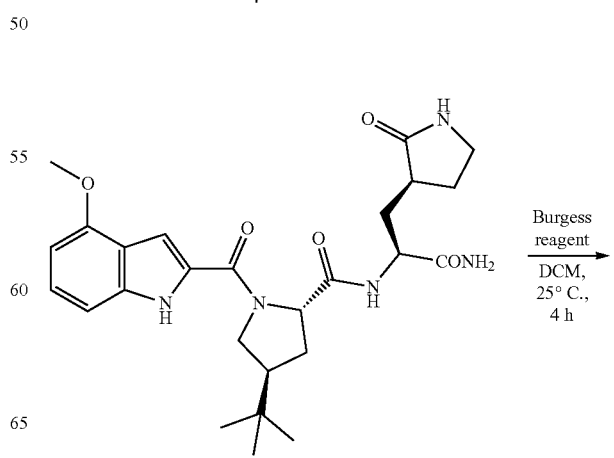

-continued

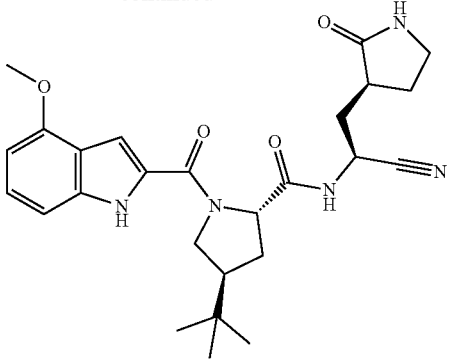

A solution of (2S,4R)-1-tert-butoxycarbonyl-4-hydroxypyrrolidine-2-carboxylic acid (5 g, 21.62 mmol, 1 eq) in THF (75 mL) was added 2-tert-butyl-1,3-diisopropyl-isourea (6.50 g, 32.43 mmol, 1.5 eq) at 25° C., and then the solution was stirred at 60° C. for 2.5 h. Additional 2-tert-butyl-1,3-diisopropyl-isourea (6.50 g, 32.43 mmol, 1.5 eq) was added to the mixture and then was stirred at 60° C. for 14 h. Upon completion, the reaction mixture was filtered through Celite and the filtrate was concentrated under reduced pressure to give (2S,4R)-di-tert-butyl 4-hydroxypyrrolidine-1,2-dicarboxylate (4.3 g, 14.22 mmol, 65.75% yield, 95% purity) as colorless oil. MS (ESI) m/z 288.2 $[M+H]^+$ Step 2: (2S,4S)-di-tert-butyl 4-bromopyrrolidine-1,2-dicarboxylate A solution of (2S,4R)-di-tert-butyl 4-hydroxypyrrolidine-1,2-dicarboxylate (4 g, 13.92 mmol, 1 eq) in DCM (40 mL) was added $CBr_4$ (14.08 g, 42.46 mmol, 3.05 eq) at 25° C. The mixture was cooled to 0° C., and $PPh_3$ (11.32 g, 43.15 mmol, 3.1 eq) was added carefully. The reaction was stirred at 25° C. for 15 h. Upon completion, ethanol (4 mL) was added, and the solution was stirred for 2 h. MTBE (40 mL) was added dropwise to precipitate the phosphine oxide, which was filtered off, and the filter cake was washed with DCM (30 mL*2). The filtrate was concentrated under reduced pressure to give a brown oil. The residue was purified by column chromatography ($SiO_2$, petroleum ether:ethyl acetate=100:0 to 10:1) to give (2S,4S)-di-tert-butyl 4-bromopyrrolidine-1,2-dicarboxylate (1.5 g, 4.07 mmol, 29.23% yield, 95% purity) as a light yellow oil.

Step 3: (2S,4S)-di-tert-butyl 4-(tert-butyl)pyrrolidine-1,2-dicarboxylate

A mixture of phenylsulfanylcopper (1.58 g, 9.14 mmol, 6.4 eq) in dry THF (30 mL) was cooled to −70° C. and treated with careful addition of t-BuLi (1.3 M, 7.03 mL, 6.4 eq). This yellow mixture was stirred for 30 min, and a precooled (−20° C.) solution of (2S,4S)-di-tert-butyl 4-bromopyrrolidine-1,2-dicarboxylate (500 mg, 1.43 mmol, 1 eq) in dry THF (5 mL) was added. The reaction was stirred at −70° C. for 5 h, and then warmed to 25° C. for 15 h under $N_2$. Upon completion, the reaction was quenched by pouring into a solution of saturated aqueous $NH_4Cl$ (30 mL). The aqueous mixture was stirred vigorously for 30 min. Solids were filtered off, and the phases were separated. The aqueous phase was extracted with MTBE (10 mL*3), and the combined organic phases were washed with saturated aqueous $NaHCO_3$ (10 mL) and brine (10 mL), dried over $Na_2SO_4$, concentrated under reduced pressure to give a crude. The residue was purified by column chromatography ($SiO_2$, petroleum ether:ethyl acetate=100:0 to 10:1) to give (2S,4S)-di-tert-butyl 4-(tert-butyl)pyrrolidine-1,2-dicarboxylate (290 mg, 797.05 umol, 55.83% yield, 90% purity) as an off-white solid.

Step 4: (2S,4S)-4-(tert-butyl)pyrrolidine-2-carboxylic acid

A mixture of (2S,4S)-di-tert-butyl 4-(tert-butyl)pyrrolidine-1,2-dicarboxylate (250 mg, 763.46 umol, 1 eq) in HCl (6 M, 2.5 mL, 19.65 eq) was stirred at 100° C. for 14 h. Upon completion, the reaction mixture was concentrated under reduced pressure to give (2S,4S)-4-tert-butylpyrrolidine-2-carboxylic acid (158 mg, crude, HCl) as a yellow solid.

Step 5: (2S,4S)-1-(tert-butoxycarbonyl)-4-(tert-butyl)pyrrolidine-2-carboxylic acid A mixture of (2S,4S)-4-tert-butylpyrrolidine-2-carboxylic acid (158 mg, 760.72 umol, 1 eq, HCl) in THF (1 mL) and $H_2O$ (1 mL) was added $K_2CO_3$ (315.41 mg, 2.28 mmol, 3 eq) and $Boc_2O$ (199.23 mg, 912.87 umol, 209.72 uL, 1.2 eq). The reaction was stirred at 25° C. for 14 h under $N_2$. Upon completion, the reaction mixture was concentrated under reduced pressure to give (2S,4S)-1-(tert-butoxycarbonyl)-4-(tert-butyl)pyrrolidine-2-carboxylic acid (650 mg, crude) as a yellow solid.

Step 6: (2S,4S)-tert-butyl 4-(tert-butyl)-2-(((S)-1-methoxy-1-oxo-3-((S)-2-oxopyrrolidin-3-yl)propan-2-yl)carbamoyl)pyrrolidine-1-carboxylate To a solution of (2S,4S)-1-(tert-butoxycarbonyl)-4-(tert-butyl)pyrrolidine-2-carboxylic acid (630 mg, 696.51 umol, 30% purity, 1 eq) in DCM (6 mL) and DMF (3 mL) was added TEA (422.88 mg, 4.18 mmol, 581.68 uL, 6 eq), methyl (2S)-2-amino-3-[(3S)-2-oxopyrrolidin-3-yl]propanoate (186.11 mg, 835.82 umol, 1.2 eq, HCl). After adding T3P (1.33 g, 2.09 mmol, 1.24 mL, 50% purity, 3 eq) at 0° C., the mixture was stirred at 25° C. for 1 h. Upon completion, the mixture was quenched with water (10.0 mL) and extracted with DCM (10 mL*3). The organic layers were washed with brine (10.0 mL), dried over $Na_2SO_4$, filtered and concentrated under reduced pressure to give a residue. The residue was purified by column chromatography ($SiO_2$, petroleum ether:ethyl acetate=10:1 to 0:1) to give tert-butyl (2S,4S)-tert-butyl 4-(tert-butyl)-2-(((S)-1-methoxy-1-oxo-3-((S)-2-oxopyrrolidin-3-yl)propan-2-yl)carbamoyl)pyrrolidine-1-carboxylate (240 mg, 546.02 umol, 78.39% yield) as a yellow solid. MS (ESI) m/z 440.3 $[M+H]^+$.

Step 7: (S)-methyl 2-((2S,4S)-4-(tert-butyl)pyrrolidine-2-carboxamido)-3-((S)-2-oxopyrrolidin-3-yl)propanoate A solution of tert-butyl (2S,4S)-tert-butyl 4-(tert-butyl)-2-(((S)-1-methoxy-1-oxo-3-((S)-2-oxopyrrolidin-3-yl)propan-2-yl)carbamoyl)pyrrolidine-1-carboxylate (230 mg, 523.27 umol, 1 eq) in HCl/MeOH (4 M, 2.3 mL, 17.58 eq) was stirred at 25° C. for 1 h. Upon completion, the reaction mixture was concentrated under reduced pressure to give (S)-methyl 2-((2S,4S)-4-(tert-butyl)pyrrolidine-2-carboxamido)-3-((S)-2-oxopyrrolidin-3-yl)propanoate (196 mg, crude, HCl) as a light yellow solid. MS (ESI) m/z 340.2 [M+H]+.

Step 8: (S)-methyl 2-((2S,4S)-4-(tert-butyl)-1-(4-methoxy-1H-indole-2-carbonyl)pyrrolidine-2-carboxamido)-3-((S)-2-oxopyrrolidin-3-yl)propanoate To a solution of (S)-methyl 2-((2S,4S)-4-(tert-butyl)pyrrolidine-2-carboxamido)-3-((S)-2-oxopyrrolidin-3-yl)propanoate (196 mg, 521.43 umol, 1 eq, HCl) in DCM (2 mL) and DMF (1 mL) was added 4-methoxy-1H-indole-2-carboxylic acid (99.69 mg, 521.43 umol, 1 eq), DMAP (127.41 mg, 1.04 mmol, 2 eq), and then EDCI (199.92 mg, 1.04 mmol, 2 eq) at 0° C. The mixture was then stirred at 25° C. for 1 h. Upon completion, the mixture was quenched with water (10.0 mL) and extracted with DCM (10 mL*3). The organic layers were washed with brine (10.0 mL), dried over Na$_2$SO$_4$, filtered and concentrated under reduced pressure to give a residue. The residue was purified by column chromatography (SiO$_2$, dichloromethane:methanol=10:1 to 4:1) to give (S)-methyl 2-((2S,4S)-4-(tert-butyl)-1-(4-methoxy-1H-indole-2-carbonyl)pyrrolidine-2-carboxamido)-3-((S)-2-oxopyrrolidin-3-yl)propanoate (250 mg, 414.56 umol, 79.50% yield, 85% purity) as a yellow solid. MS (ESI) m/z 513.3 [M+H]+.

Step 9: (2S,4S)-N-((S)-1-amino-1-oxo-3-((S)-2-oxopyrrolidin-3-yl)propan-2-yl)-4-(tert-butyl)-1-(4-methoxy-1H-indole-2-carbonyl)pyrrolidine-2-carboxamide A solution of (S)-methyl 2-((2S,4S)-4-(tert-butyl)-1-(4-methoxy-1H-indole-2-carbonyl)pyrrolidine-2-carboxamido)-3-((S)-2-oxopyrrolidin-3-yl)propanoate (235 mg, 389.68 umol, 85% purity, 1 eq) in NH$_3$/MeOH (7 M, 5 mL) was stirred at 40° C. for 14 h. Upon completion, the reaction mixture was concentrated under reduced pressure to give (2S,4S)-N-((S)-1-amino-1-oxo-3-((S)-2-oxopyrrolidin-3-yl)propan-2-yl)-4-(tert-butyl)-1-(4-methoxy-1H-indole-2-carbonyl)pyrrolidine-2-carboxamide (193 mg, crude) as a yellow solid. MS (ESI) m/z 498.3 [M+H]+.

Step 10: (2S,4S)-4-(tert-butyl)-N-((S)-1-cyano-2-((S)-2-oxopyrrolidin-3-yl)ethyl)-1-(4-methoxy-1H-indole-2-carbonyl)pyrrolidine-2-carboxamide To a solution of (2S,4S)-N-((S)-1-amino-1-oxo-3-((S)-2-oxopyrrolidin-3-yl)propan-2-yl)-4-(tert-butyl)-1-(4-methoxy-1H-indole-2-carbonyl)pyrrolidine-2-carboxamide (193 mg, 329.69 umol, 85% purity, 1 eq) in DCM (3 mL) was added Burgess reagent (235.71 mg, 989.08 umol, 3 eq), and then the reaction was stirred at 25° C. for 4 h. Upon completion, the reaction mixture was concentrated under reduced pressure to give a residue. The residue was purified by prep-HPLC (column: Waters Xbridge BEH C18 100*25 mm*5 um; mobile phase: [water (10 mM NH$_4$HCO$_3$)-ACN]; B %: 30%-55%, 10 min) to give (2S,4S)-4-(tert-butyl)-N-((S)-1-cyano-2-((S)-2-oxopyrrolidin-3-yl)ethyl)-1-(4-methoxy-1H-indole-2-carbonyl)pyrrolidine-2-carboxamide (59.58 mg, 124.24 umol, 37.68% yield, 100% purity) as a white solid. MS (ESI) m/z 480.2 [M+H]+.

$^1$H NMR (400 MHz, DMSO-d$_6$) δ=11.69-11.55 (m, 1H), 9.17-8.75 (m, 1H), 7.81-7.44 (m, 1H), 7.16-7.07 (m, 1H), 7.06-6.98 (m, 2H), 6.55-6.46 (m, 1H), 5.03-4.53 (m, 2H), 4.04-3.74 (m, 4H), 3.69-3.36 (m, 1H), 3.22-2.55 (m, 2H), 2.35-1.95 (m, 5H), 1.83-1.51 (m, 3H), 1.00-0.82 (m, 9H).

$^1$H NMR (400 MHz, DMSO-d$_6$, 273+80K) δ=11.31 (s, 1H), 8.68 (s, 1H), 7.38 (s, 1H), 7.18-7.02 (m, 2H), 6.90 (s, 1H), 6.60-6.47 (m, 1H), 4.96 (q, J=7.6 Hz, 1H), 4.72 (s, 1H), 4.07-3.80 (m, 4H), 3.66-3.50 (m, 1H), 3.28-3.05 (m, 2H), 2.32-1.97 (m, 5H), 1.95-1.64 (m, 3H), 0.95 (s, 9H).

Example 189. Synthesis of Viral Protease Inhibitor Compound 659

Step 1: (S)-tert-butyl (1-hydroxy-4,4-dimethylpentan-2-yl)carbamate

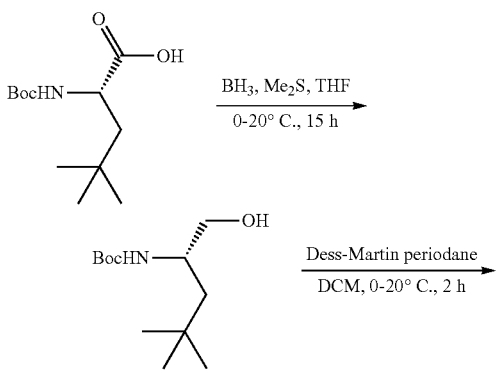

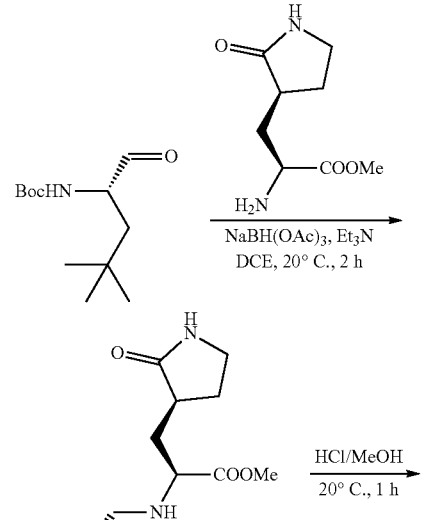

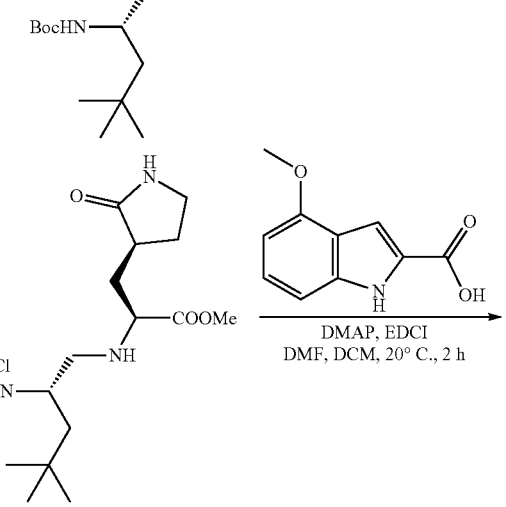

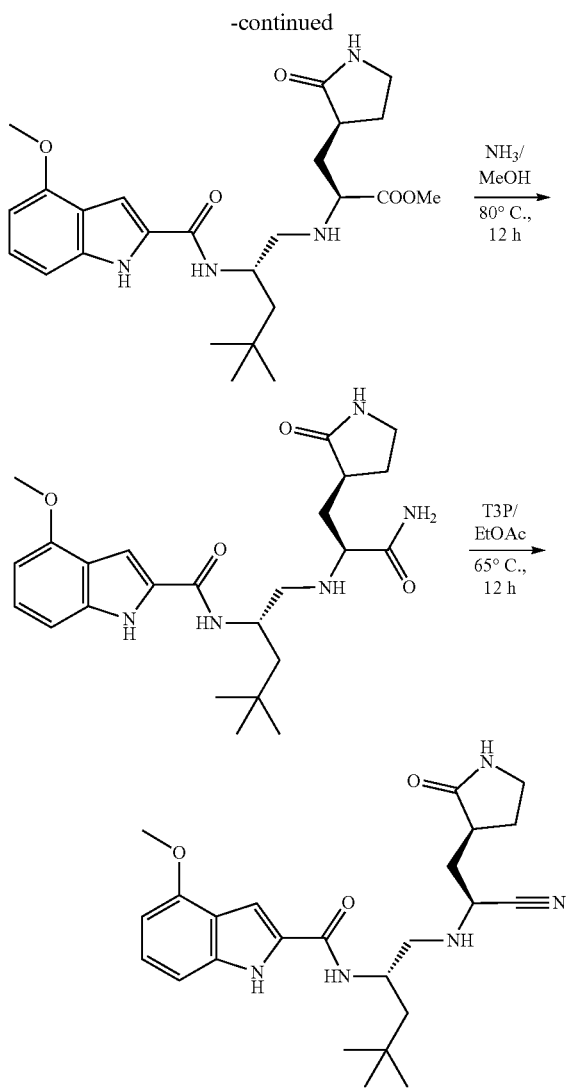

To a solution of (2S)-2-(tert-butoxycarbonylamino)-4,4-dimethyl-pentanoic acid (5 g, 20.38 mmol, 1 eq) in THF (100 mL) at 0° C. was added BH₃-Me₂S (10 M, 4.08 mL, 2.0 eq) drop-wise slowly, and then the mixture was stirred at 20° C. for 15 h. The reaction mixture was added into MeOH (40 mL) and stirred for 20 min. After concentrating the mixture, the residue was diluted with aq. NaHCO₃ (150 mL) and extracted with DCM (100 mL*3). The combined organic layers were washed with brine (100 mL), dried over Na₂SO₄, filtered and concentrated under reduced pressure to give a residue. The residue was purified by column chromatography (SiO₂, petroleum ether:ethyl acetate=1:0 to 1:1) to afford tert-butyl N-[(1S)-1-(hydroxymethyl)-3,3-dimethyl-butyl]carbamate (2.5 g, 10.81 mmol, 53.02% yield) as a colorless oil.

Step 2: (S)-tert-butyl (4,4-dimethyl-1-oxopentan-2-yl)carbamate

To a solution of tert-butyl N-[(1S)-1-(hydroxymethyl)-3,3-dimethyl-butyl]carbamate (2.4 g, 10.37 mmol, 1 eq) in DCM (40 mL) was added Dess-Martin periodinane (5.72 g, 13.49 mmol, 4.18 mL, 1.3 eq) at 0° C. stirred for 1 h, and then the mixture was warm to 20° C. and stirred for 1 h. The reaction mixture was quenched by addition H₂O 60 mL at 0° C., and then aq. NaHCO₃ was added drop-wise to adjust the pH of the mixture to about 8 at 0° C. and extracted with EtOAc (40 mL*3). The combined organic layers were washed with brine (50 mL), dried over Na₂SO₄, filtered and concentrated under reduced pressure to give a residue. The residue was purified by column chromatography (SiO₂, petroleum ether:ethyl acetate=0:1 to 1:1) to afford tert-butyl N-[(1S)-1-formyl-3,3-dimethyl-butyl]carbamate (1.6 g, 6.98 mmol, 67.25% yield) as a colorless oil.

¹H NMR (400 MHz, DMSO-d₆) δ ppm 9.40 (s, 1H) 7.30 (br d, J=8.00 Hz, 1H) 3.91-3.82 (m, 1H) 1.66 (dd, J=14.38, 2.75 Hz, 1H) 1.39 (s, 9H) 1.32 (br d, J=9.26 Hz, 1H) 0.90 (s, 9H).

Step 3: (S)-methyl 2-(((S)-2-((tert-butoxycarbonyl)amino)-4,4-dimethylpentyl)amino)-3-((S)-2-oxopyrrolidin-3-yl)propanoate To a solution of tert-butyl N-[(1S)-1-formyl-3,3-dimethyl-butyl]carbamate (0.8 g, 3.49 mmol, 1 eq) and methyl (2S)-2-amino-3-[(3S)-2-oxopyrrolidin-3-yl]propanoate (1.17 g, 5.23 mmol, 1.5 eq, HCl) in DCE (20 mL) was added Et₃N (529.52 mg, 5.23 mmol, 728.36 uL, 1.5 eq) and NaBH(OAc)₃ (2.22 g, 10.47 mmol, 3 eq). The reaction was stirred at 20° C. for 2 h. The reaction mixture was quenched by addition aq. NaHCO₃ (100 mL) at 0° C. and stirred for 0.5 h, and then extracted with DCM (60 mL*3). The combined organic layers were washed with brine (50 mL), dried over Na₂SO₄, filtered and concentrated under reduced pressure to give a residue. The residue was purified by column chromatography (SiO₂, petroleum ether:ethyl acetate=0:1 to 1:3) to afford methyl (2S)-2-[[(2S)-2-(tert-butoxycarbonylamino)-4,4-dimethyl-pentyl]amino]-3-[(3S)-2-oxopyrrolidin-3-yl]propanoate (450 mg, 1.13 mmol, 32.29% yield) as a white solid. MS (ESI) m/z 400.3 [M+H]⁺

Step 4: (S)-methyl 2-(((S)-2-amino-4,4-dimethylpentyl)amino)-3-((S)-2-oxopyrrolidin-3-yl)propanoate A solution of methyl (2S)-2-[[(2S)-2-(tert-butoxycarbonylamino)-4,4-dimethyl-pentyl]amino]-3-[(3S)-2-oxopyrrolidin-3-yl]propanoate (200 mg, 500.60 umol, 1 eq) in HCl/MeOH (4 M, 4.00 mL, 31.96 eq) was stirred at 20° C. for 1 h. The reaction mixture was concentrated under reduced pressure to afford methyl (2S)-2-[[(2S)-2-amino-4,4-dimethyl-pentyl]amino]-3-[(3S)-2-oxopyrrolidin-3-yl]propanoate (168 mg, crude, HCl) as a white solid.

Step 5: (S)-methyl 2-(((S)-2-(4-methoxy-1H-indole-2-carboxamido)-4,4-dimethylpentyl)amino)-3-((S)-2-oxopyrrolidin-3-yl)propanoate To a solution of methyl (2S)-2-[[(2S)-2-amino-4,4-dimethyl-pentyl]amino]-3-[(3S)-2-oxopyrrolidin-3-yl]propanoate (168 mg, 500.20 umol, 1 eq, HCl) and 4-methoxy-1H-indole-2-carboxylic acid (95.63 mg, 500.20 umol, 1 eq) in DMF (1 mL) was added DMAP (183.32 mg, 1.50 mmol, 3.0 eq), EDCI (191.78 mg, 1.00 mmol, 2 eq) and DCM (3 mL).

The mixture was stirred at 20° C. for 2 h. The reaction mixture was quenched by addition H₂O 40 mL at 0° C., and then extracted with DCM (20 mL*3). The combined organic layers were washed with brine (40 mL), dried over Na₂SO₄, filtered and concentrated under reduced pressure to give a residue. The residue was purified by column chromatography (SiO₂, petroleum ether:ethyl acetate=1:0 to 0:1) to afford methyl (2S)-2-[[(2S)-2-[(4-methoxy-1H-indole-2-carbonyl)amino]-4,4-dimethyl-pentyl]amino]-3-[(3S)-2-oxopyrrolidin-3-yl]propanoate (150 mg, 301.54 umol, 60.28% yield, 95% purity) as a yellow oil. MS (ESI) m/z 473.2 [M+H]⁺

Step 6: N-((S)-1-(((S)-1-amino-1-oxo-3-((S)-2-oxopyrrolidin-3-yl)propan-2-yl)amino)-4,4-dimethylpentan-2-yl)-4-methoxy-1H-indole-2-carboxamide A solution of methyl (2S)-2-[[(2S)-2-[(4-methoxy-1H-indole-2-carbonyl)amino]-4,4-dimethyl-pentyl]amino]-3-[(3S)-2-oxopyrrolidin-3-yl]propanoate (130 mg, 275.09 umol, 1 eq) in NH₃/MeOH (7 M, 15 mL, 381.70 eq) was stirred at 80° C. for 12 h. Upon completion, the reaction mixture was concentrated under reduced pressure to give a residue. The residue was purified by prep-TLC (SiO₂, ethyl acetate:MeOH=50:3) to afford product N-[(1S)-1-[[[(1S)-2-amino-2-oxo-1-[[(3S)-2-oxopyrrolidin-3-yl]methyl]ethyl]amino]methyl]-3,3-dimethyl-butyl]-4-methoxy-1H-indole-2-carboxamide (60 mg, 131.13 umol, 47.67% yield) as a yellow solid. MS (ESI) m/z 458.3 [M+H]⁺

Step 7: N-((S)-1-(((S)-1-cyano-2-((S)-2-oxopyrrolidin-3-yl)ethyl)amino)-4,4-dimethylpentan-2-yl)-4-methoxy-1H-indole-2-carboxamide To a solution of N-[(1S)-1-[[[(1S)-2-amino-2-oxo-1-[[(3S)-2-oxopyrrolidin-3-yl]methyl]ethyl]amino]methyl]-3,3-dimethyl-butyl]-4-methoxy-1H-indole-2-carboxamide (50 mg, 109.27 umol, 1 eq) in EtOAc (2 mL) was added T₃P (2.14 g, 3.36 mmol, 2 mL, 50% purity, 30.77 eq) drop-wise, and then the resulting mixture was stirred at 65° C. for 12 h. The reaction mixture was concentrated under reduced pressure to give a residue. The residue was purified by prep-HPLC (column: Phenomenex Luna C18 75*30 mm*3 um; mobile phase: [water (0.2% FA)-ACN]; B %: 15%-45%, 8 min) and was separated by SFC (column: DAICEL CHIRALPAK AD (250 mm*30 mm, 10 um); mobile phase: [0.1% NH₃H₂O ETOH]; B %: 25%-25%, 20 min) to afford N-[(1S)-1-[[[(1S)-1-cyano-2-[(3S)-2-oxopyrrolidin-3-yl]ethyl]amino]methyl]-3,3-dimethyl-butyl]-4-methoxy-1H-indole-2-carboxamide (4.4 mg, 9.92 umol, 29.07% yield, 99.1% purity) as a white solid. MS (ESI) m/z 440.2 [M+H]⁺.

¹H NMR (400 MHz, METHANOL-d₄) δ=7.22-6.99 (m, 3H) 6.52 (br d, J=7.72 Hz, 1H) 4.74-4.65 (m, 1H) 4.61-4.48 (m, 1H) 4.03-3.91 (m, 4H) 3.62-3.51 (m, 1H) 3.47-3.36 (m, 1H) 3.27-3.19 (m, 1H) 2.50-2.41 (m, 1H) 2.29-2.18 (m, 1H) 1.81 (br s, 1H) 1.74-1.64 (m, 2H) 1.60 (br d, J=10.14 Hz, 1H) 1.34-1.28 (m, 1H) 0.98 (s, 9H).

Example 190. Synthesis of Viral Protease Inhibitor Compound 667

Step 1: methyl (2S)-2-[[(2S)-2-(tert-butoxycarbonylamino)-4-fluoro-4-methyl-pentanoyl]amino]-3-[(3S)-2-oxo-3-piperidyl]propanoate

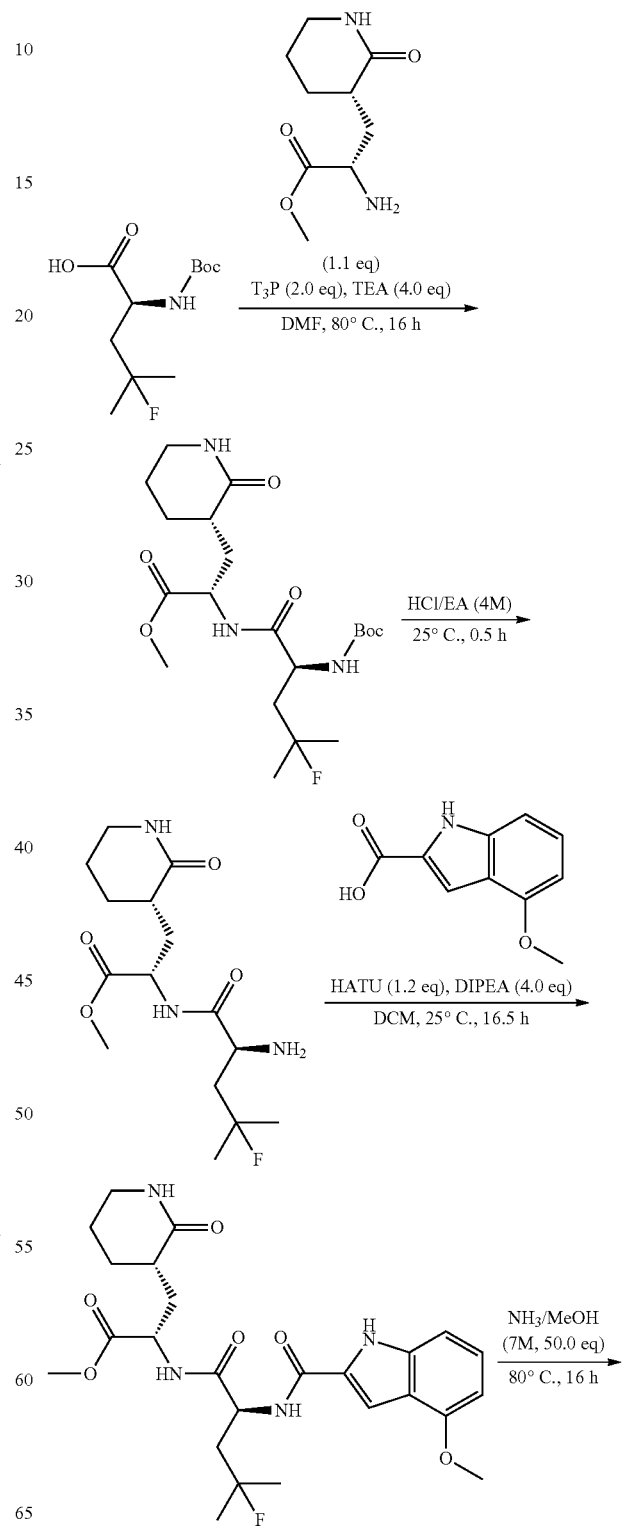

-continued

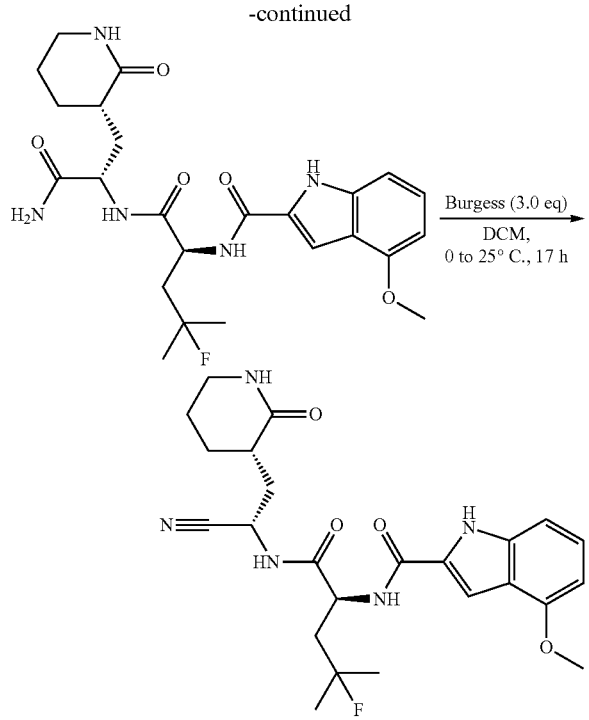

To a solution of compound (S)-2-((tert-butoxycarbonyl) amino)-4-fluoro-4-methylpentanoic acid (300.0 mg, 1.20 mmol, 1.0 eq) and compound methyl (S)-2-amino-3-((S)-2-oxopiperidin-3-yl)propanoate (313.3 mg, 1.32 mmol, 1.1 eq, HCl) in DMF (3 mL) was added $T_3P$ (1.53 g, 2.41 mmol, 1.43 mL, 50% purity, 2.0 eq) and TEA (487.1 mg, 4.81 mmol, 0.67 mL, 4.0 eq). The mixture was stirred at 80° C. for 16 h. TLC (petroleum ether/ethyl acetate=0/1, PMA). The mixture was concentrated under reduced pressure to give a residue. The residue was purified by flash silica gel chromatography (ISCO®; 12 g SepaFlash® Silica Flash Column, Eluent of 0~1% MeOH/DCM @ 25 mL/min) to give methyl (S)-2-((S)-2-((tert-butoxycarbonyl)amino)-4-fluoro-4-methylpentanamido)-3-((S)-2-oxopiperidin-3-yl) propanoate (620 mg, 1.15 mmol, 95.5% yield, 80% purity) as a yellow solid.

LCMS: Rt=0.773 min; for $C_{20}H_{34}FN_3O_6$ MS Calcd.: 431.24; MS Found: 432.2 [M+H$^+$].

Step 2: Methyl (2S)-2-[[(2S)-2-amino-4-fluoro-4-methyl-pentanoyl]amino]-3-[(3S)-2-oxo-3-piperidyl] propanoate A mixture of compound methyl (S)-2-((S)-2-((tert-butoxycarbonyl)amino)-4-fluoro-4-methylpentanamido)-3-((S)-2-oxopiperidin-3-yl)propanoate (520 mg, 1.21 mmol, 1 eq) in HCl/EtOAc (4 mL) was stirred at 25° C. for 0.5 h. The mixture was concentrated under reduced pressure to give compound methyl (S)-2-((S)-2-amino-4-fluoro-4-methylpentanamido)-3-((S)-2-oxopiperidin-3-yl)propanoate (550 mg, crude, HCl, yellow oil) was used into the next step.

Step 3: Methyl (2S)-2-[[(2S)-4-fluoro-2-[(4-methoxy-1H-indole-2-carbonyl)amino]-4-methyl-pentanoyl]amino]-3-[(3S)-2-oxo-3-piperidyl]propanoate To a solution of compound 4-methoxy-1H-indole-2-carboxylic acid (200 mg, 1.05 mmol, 1 eq) in DCM (5 mL) were added HATU (477.3 mg, 1.26 mmol, 1.2 eq) and DIEA (540.8 mg, 4.18 mmol, 0.73 mL, 4 eq). The mixture was stirred at 25° C. for 0.5 h. Compound methyl (S)-2-((S)-2-amino-4-fluoro-4-methylpentanamido)-3-((S)-2-oxopiperidin-3-yl)propanoate (461.8 mg, 1.26 mmol, 1.2 eq, HCl) was added into the mixture. The mixture was stirred at 25° C. for 16 h. TLC (DCM/MeOH=10/1, UV). The reaction mixture was diluted with H$_2$O (15 mL) and extracted with DCM (30 mL*3). The combined organic layers were washed with brine (20 mL), dried with anhydrous Na$_2$SO$_4$, filtered and concentrated under reduced pressure to give a residue. The residue was purified by flash silica gel chromatography (ISCO®; 12 g SepaFlash® Silica Flash Column, Eluent of 0-100% ethyl acetate/petroleum ether gradient @ 30 mL/min) to give methyl (S)-2-((S)-4-fluoro-2-(4-methoxy-1H-indole-2-carboxamido)-4-methylpentanamido)-3-((S)-2-oxopiperidin-3-yl)propanoate (480 mg, 83.9% yield) as a yellow solid.

LCMS: Rt=0.794 min; for $C_{25}H_{33}FN_4O_6$ MS Calcd.: 504.24; MS Found: 505.2 [M+H$^+$].

$^1$H NMR (400 MHz, CDCl$_3$) δ 9.56-9.81 (m, 1H), 8.24 (br s, 1H), 7.23-7.06 (m, 3H), 7.01 (d, J=8.28 Hz, 1H), 6.49 (d, J=7.78 Hz, 1H), 6.17 (br s, 1H), 4.95-4.82 (m, 1H), 4.60-4.51 (m, 1H), 3.94 (s, 3H), 3.80-3.60 (m, 5H), 3.16 (br d, J=7.28 Hz, 2H), 3.00-2.77 (m, 1H), 1.98 (br d, J=6.02 Hz, 2H), 1.92-1.83 (m, 2H), 1.77 (br s, 2H), 1.51-1.44 (m, 6H).

Step 4: N-[(1S)-1-[[(1S)-2-amino-2-oxo-1-[[(3S)-2-oxo-3-piperidyl]methyl]ethyl]carbamoyl]-3-fluoro-3-methyl-butyl]-4-methoxy-1H-indole-2-carboxamide A solution of compound methyl (S)-2-((S)-4-fluoro-2-(4-methoxy-1H-indole-2-carboxamido)-4-methylpentanamido)-3-((S)-2-oxopiperidin-3-yl)propanoate (1 g, 1.98 mmol, 1 eq) in NH$_3$ (7 M in MeOH, 14.16 mL, 50 eq) was stirred at 80° C. for 16 h in a 30 mL of sealed tube. TLC (DCM/MeOH=10/1, UV). The reaction mixture was concentrated under reduced pressure to give a residue. The residue was purified by flash silica gel chromatography (ISCO®; 20 g SepaFlash® Silica Flash Column, Eluent of 0~15% MeOH/Ethyl acetate @ 30 mL/min) to give compound N-((S)-1-(((S)-1-amino-1-oxo-3-((S)-2-oxopiperidin-3-yl)propan-2-yl)amino)-4-fluoro-4-methyl-1-oxopentan-2-yl)-4-methoxy-1H-indole-2-carboxamide (370 mg, 0.74 mmol, 37.2% yield, 97.6% purity) as a yellow solid.

LCMS: Rt=0.743 min; for $C_{24}H_{32}FN_5O_5$ MS Calcd.: 489.24; MS Found: 490.2 [M+H$^+$].

Step 5: N-[(1S)-1-[[(1S)-1-cyano-2-[(3S)-2-oxo-3-piperidyl]ethyl]carbamoyl]-3-fluoro-3-methyl-butyl]-4-methoxy-1H-indole-2-carboxamide To a solution of compound N-((S)-1-(((S)-1-amino-1-oxo-3-((S)-2-oxopiperidin-3-yl)propan-2-yl)amino)-4-fluoro-4-methyl-1-oxopentan-2-yl)-4-methoxy-1H-indole-2-carboxamide (350 mg, 0.71 mmol, 1 eq) in DCM (6 mL) was added methoxycarbonyl-(triethylammonio)sulfonyl-azanide (170.4 mg, 0.71 mmol, 1 eq) at 0° C. The mixture was stirred at 25° C. for 0.5 h. Methoxycarbonyl-(triethylammonio)sulfonyl-azanide (170.4 mg, 0.71 mmol, 1 eq) was added into the mixture at 0° C. The mixture was stirred at 25° C. for 0.5 h. methoxycarbonyl-(triethylammonio)sulfonyl-azanide (170.4 mg, 0.71 mmol, 1 eq) was added into the mixture at 0° C. The mixture was stirred at 25° C. for 16 h. The mixture was diluted with H$_2$O (20 mL) and extracted with ethyl acetate (40 mL*3). The combined organic layers were washed with brine (30 mL), dried with anhydrous Na₂SO₄, filtered and concentrated under reduced pressure to give a residue. The residue was checked by LCMS. The residue was purified by prep-HPLC (column: Phenomenex Gemini-NX 80*40 mm*3 um; mobile phase: [water (0.05% NH₃H₂O+10 mM NH₄HCO₃)-ACN]; B %: 28%-58%, 7.8 min) to give N-((S)-1-(((S)-1-cyano-2-((S)-2-oxopiperidin-3-yl)ethyl)amino)-4-fluoro-4-methyl-1-oxopentan-2-yl)-4-methoxy-1H-indole-2-carboxamide (95 mg, 28.1% yield) as a white solid.

LCMS: Rt=0.780 min; for $C_{24}H_{30}FN_5O_4$ MS Calcd.: 471.23; MS Found: 472.2 [M+H⁺].

¹H NMR (400 MHz, CD₃OD) δ 7.24-7.20 (m, 1H), 7.18-7.11 (m, 1H), 7.07-7.01 (m, 1H), 6.51 (d, J=7.78 Hz, 1H), 5.13-5.01 (m, 1H), 4.81-4.71 (m, 1H), 3.93 (s, 3H), 3.18 (dd, J=7.40, 5.14 Hz, 2H), 2.49-2.34 (m, 2H), 2.32-2.11 (m, 2H), 2.00-1.87 (m, 2H), 1.83-1.73 (m, 1H), 1.72-1.60 (m, 1H), 1.54-1.37 (m, 7H).

Example 191. Synthesis of Viral Protease Inhibitor Compound 681

Step 1: (2S)-methyl 2-(2-(4-methoxy-1H-indole-2-carbonyl)-2-azaspiro[4.5]decane-3-carboxamido)-3-((S)-2-oxopiperidin-3-yl)propanoate

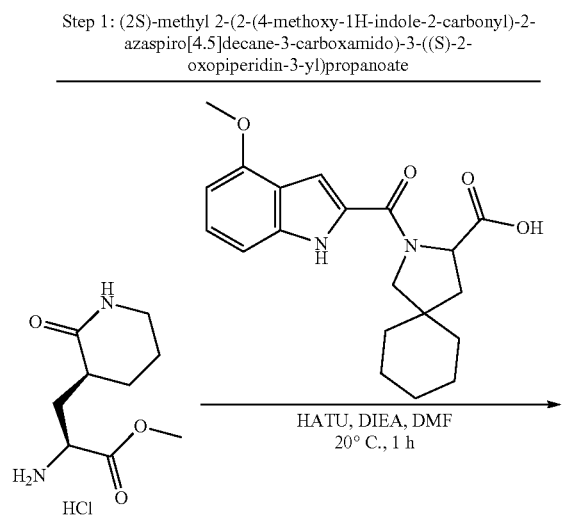

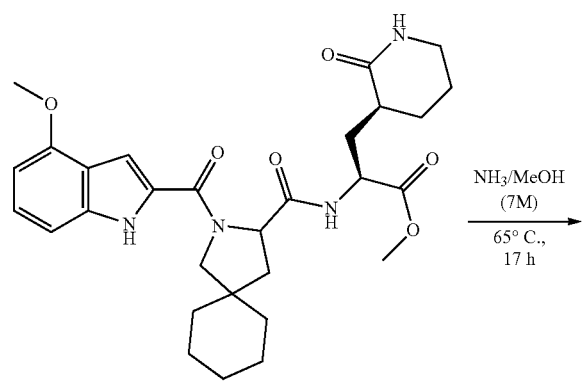

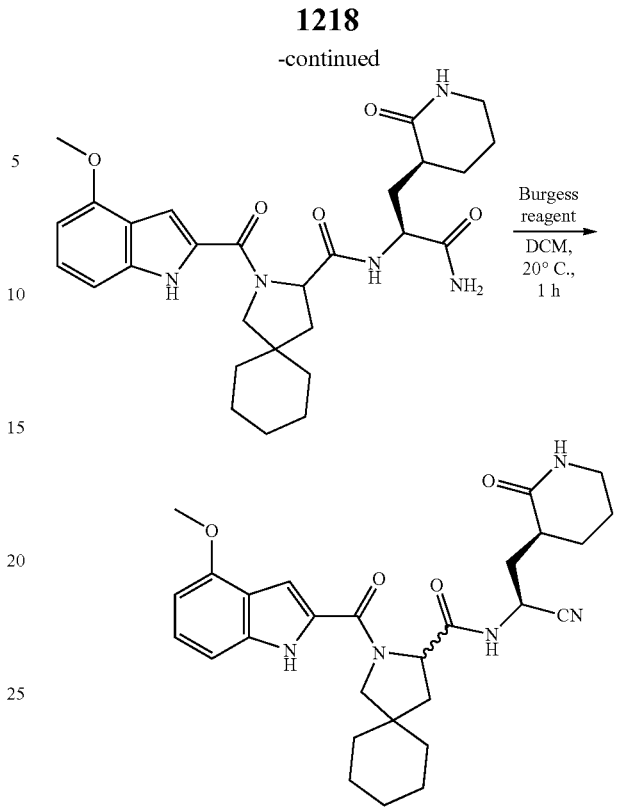

To a solution of methyl (2S)-2-amino-3-[(3S)-2-oxo-3-piperidyl]propanoate (500 mg, 2.11 mmol, 1.1 eq, HCl) 2-(4-methoxy-1H-indole-2-carbonyl)-2-azaspiro[4.5]decane-3-carboxylic acid (684.45 mg, 1.92 mmol, 1 eq) in DMF (15 mL) was added DIPEA (744.57 mg, 5.76 mmol, 1.00 mL, 3 eq) and HATU (730.19 mg, 1.92 mmol, 1 eq). The mixture was stirred at 20° C. for 1 h. Upon completion, the two batch reaction mixture was quenched by addition H₂O (80 mL), and extracted with ethyl acetate (40 mL*3). The combined organic layers were washed with brine (40 mL), dried over Na₂SO₄, filtered and concentrated under reduced pressure to get the product methyl (2S)-2-[[2-(4-methoxy-1H-indole-2-carbonyl)-2-azaspiro[4.5]decane-3-carbonyl]amino]-3-[(3S)-2-oxo-3-piperidyl]propanoate (1.35 g, crude) was obtained as white solid. MS (ESI) m/z 539.3 [M+H]⁺.

Step 2: N-((S)-1-amino-1-oxo-3-((S)-2-oxopiperidin-3-yl)propan-2-yl)-2-(4-methoxy-1H-indole-2-carbonyl)-2-azaspiro[4.5]decane-3-carboxamide A solution of methyl (2S)-2-[[2-(4-methoxy-1H-indole-2-carbonyl)-2-azaspiro[4.5]decane-3-carbonyl]amino]-3-[(3S)-2-oxo-3-piperidyl]propanoate (650 mg, 1.21 mmol, 1 eq) in NH₃/MeOH (7 M, 3.45 mL, 20 eq) was stirred at 65° C. for 17 h. Upon completion, the two batch reaction mixture was concentrated under reduced pressure to get the product N-[(1S)-2-amino-2-oxo-1-[[(3S)-2-oxo-3-piperidyl]methyl]ethyl]-2-(4-methoxy-1H-indole-2-carbonyl)-2-azaspiro[4.5]decane-3-carboxamide (1.22 g, crude) as a colorless oil. MS (ESI) m/z 524.3 [M+H]⁺.

Step 3: N-((S)-1-cyano-2-((S)-2-oxopiperidin-3-yl)ethyl)-2-(4-methoxy-1H-indole-2-carbonyl)-2-azaspiro[4.5]decane-3-carboxamide To a solution of N-[(1S)-2-amino-2-oxo-1-[[(3S)-2-oxo-3-piperidyl]methyl]ethyl]-2-(4-methoxy-1H-indole-2-carbonyl)-2-azaspiro[4.5]decane-3-carboxamide (1.22 g, 2.33 mmol, 1 eq) in DCM (20 mL) was added Burgess reagent (1.39 g, 5.82 mmol, 2.5 eq). The mixture was stirred at 20° C. for 1 h. Upon completion, the reaction mixture was quenched by addition H₂O (3 mL) and then concentrated under reduced pressure to give a residue. The residue was purified by prep-HPLC (column: Agela DuraShell C18 250*70 mm*10 um; mobile phase: [water (10 mM NH₄HCO₃)-ACN]; B %: 43%-63%, 20 min) to give desired compound (490 mg) as a white solid, which was further separated by SFC (column: DAICEL CHIRALPAK AD (250 mm*30 mm, 10 um); mobile phase: [0.1% NH₃H₂O IPA]; B %: 58%-58%, 10 min) to afford N-[(1S)-1-cyano-2-[(3S)-2-oxo-3-piperidyl]ethyl]-2-(4-methoxy-1H-indole-2-carbonyl)-2-azaspiro[4.5]decane-3-carboxamide Isomer 1 (201.77 mg, 394.36 umol, 16.93% yield, 98.820% purity) as a white solid. MS (ESI) m/z 506.3[M+H]⁺. ¹H NMR (400 MHz, DMSO-d₆) δ ppm 11.26 (br s, 1H) 8.50-8.85 (m, 1H) 7.23 (br s, 1H) 7.00-7.16 (m, 2H) 6.89 (br s, 1H) 6.52 (br d, J=7.46 Hz, 1H) 4.86-5.06 (m, 1H) 4.48-4.79 (m, 1H) 3.80-3.98 (m, 4H) 3.59 (br d, J=4.65 Hz, 1H) 3.09 (br s, 2H) 2.15-2.31 (m, 3H) 1.73-2.01 (m, 2H) 1.67 (br dd, J=12.17, 8.62 Hz, 2H) 1.33-1.61 (m, 12H).

N-[(1S)-1-cyano-2-[(3S)-2-oxo-3-piperidyl]ethyl]-2-(4-methoxy-1H-indole-2-carbonyl)-2-azaspiro[4.5]decane-3-carboxamide Isomer 2 (200.95 mg, 394.35 umol, 16.93% yield, 99.222% purity) was obtained as a white solid. MS (ESI) m/z 506.3[M+H]⁺. ¹H NMR (400 MHz, DMSO-d₆) δ ppm 11.27 (br s, 1H) 8.61 (br d, J=1.22 Hz, 1H) 7.02-7.26 (m, 3H) 6.91 (br s, 1H) 6.53 (d, J=7.46 Hz, 1H) 4.91-5.06 (m, 1H) 4.62 (br s, 1H) 3.82-3.98 (m, 4H) 3.52-3.75 (m, 1H) 3.09 (br s, 2H) 2.09-2.28 (m, 3H) 1.63-1.92 (m, 4H) 1.33-1.62 (m, 12H).

Example 192. Synthesis of Viral Protease Inhibitor Compound 711

Step 1: methyl (2S)-2-[[(2S)-2-amino-3-cyclopropyl-propanoyl]amino]-3-[(3S)-2-oxopyrrolidin-3-yl]propanoate

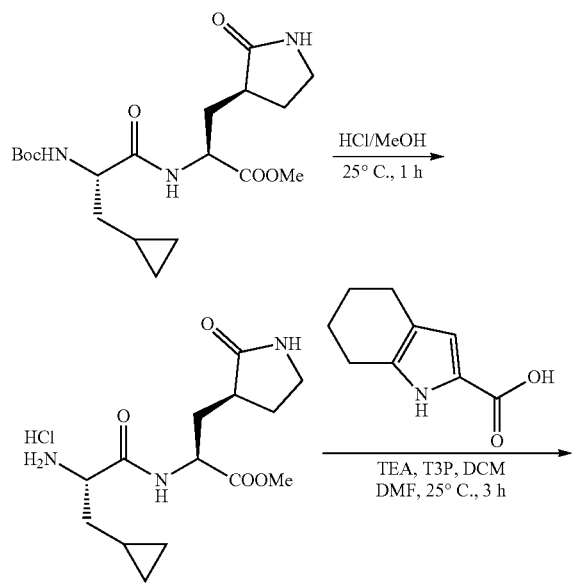

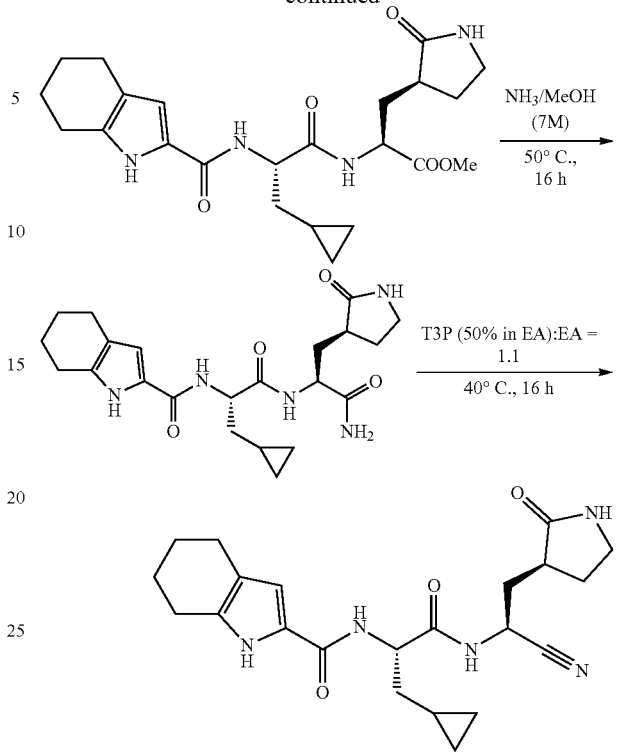

A mixture of methyl (2S)-2-[[(2S)-2-(tert-butoxycarbonylamino)-3-cyclopropyl-propanoyl]amino]-3-[(3S)-2-oxopyrrolidin-3-yl]propanoate (900 mg, 1.81 mmol, 80% purity, 1 eq) in HCl/MeOH (4 M, 12.00 mL, 26.50 eq) was stirred at 25° C. for 1 h. Upon completion, the mixture was concentrated under reduced pressure to give a residue, then was dissolved with DCM (10 mL*3) and concentrated under reduced pressure to get product methyl (2S)-2-[[(2S)-2-amino-3-cyclopropyl-propanoyl]amino]-3-[(3S)-2-oxopyrrolidin-3-yl]propanoate (600 mg, crude, HCl) as a white oil. MS (ESI) m/z 298.1 [M+H]⁺.

Step 2: methyl (2S)-2-[[(2S)-3-cyclopropyl-2-(4,5,6,7-tetrahydro-1H-indole-2-carbonylamino)propanoyl]amino]-3-[(3S)-2-oxopyrrolidin-3-yl]propanoate To a mixture of methyl (2S)-2-[[(2S)-2-amino-3-cyclopropyl-propanoyl]amino]-3-[(3S)-2-oxopyrrolidin-3-yl]propanoate (600 mg, 1.80 mmol, 1 eq, HCl) in DCM (7 mL) and DMF (0.5 mL) was added 4,5,6,7-tetrahydro-1H-indole-2-carboxylic acid (415.68 mg, 2.52 mmol, 1.4 eq), TEA (1.09 g, 10.78 mmol, 1.50 mL, 6 eq) and T3P (1.72 g, 2.70 mmol, 1.60 mL, 50% purity, 1.5 eq). The mixture was stirred at 25° C. for 3 h. Upon completion, the reaction mixture was diluted with water (10 mL) and extracted with DCM (3 mL*3). The combined organic layers were dried over Na₂SO₄, filtered and concentrated under reduced pressure to give a residue. The residue was purified by prep-TLC (SiO2, DCM:MeOH=10:1) and TLC (SiO2, DCM:MeOH=10:1) to afford methyl (2S)-2-[[(2S)-3-cyclopropyl-2-(4,5,6,7-tetrahydro-1H-indole-2-carbonylamino)propanoyl]amino]-3-[(3S)-2-oxopyrrolidin-3-yl]propanoate (350 mg, 787.36 umol, 43.80% yield) as a yellow oil. MS (ESI) m/z 445.3 [M+H]⁺.

Step 3: N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4,5,6,7-tetrahydro-1H-indole-2-carboxamide A mixture of methyl (2S)-2-[[(2S)-3-cyclopropyl-2-(4,5,6,7-tetrahydro-1H-indole-2-carbonylamino)propanoyl]amino]-3-[(3S)-2-oxopyrrolidin-3-yl]propanoate (350 mg, 787.36 umol, 1 eq) in NH₃/MeOH (7 M, 10 mL, 88.90 eq) was stirred at 50° C. for 16 h. Upon completion, the reaction mixture was concentrated under reduced pressure to afford N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4,5,6,7-tetrahydro-1H-indole-2-carboxamide (300 mg, crude) as a yellow solid. MS (ESI) m/z 430.2 [M+H]⁺.

Step 4: N-[(1S)-2-[[(1S)-1-cyano-2-[(3S)-2-oxopyrrolidin-3-yl]ethyl]amino]-1-(cyclopropylmethyl)-2-oxo-ethyl]-4,5,6,7-tetrahydro-1H-indole-2-carboxamide A mixture of N-[(1S)-2-[[(1S)-2-amino-2-oxo-1-[[(3S)-2-oxopyrrolidin-3-yl]methyl]ethyl]amino]-1-(cyclopropylmethyl)-2-oxo-ethyl]-4,5,6,7-tetrahydro-1H-indole-2-carboxamide (290 mg, 675.19 umol, 1 eq) in T3P (3 mL, 50% purity) and ethyl acetate (3 mL) was stirred at 40° C. for 16 h. Upon completion, the reaction mixture was diluted with water (10 mL) and extracted with ethyl acetate (3 mL*3). The combined organic layers were dried over Na₂SO₄, filtered and concentrated under reduced pressure to give a residue. The residue was purified by prep-HPLC (column: Waters X bridge BEH C18 100*25 mm*5 um; mobile phase: [water (10 mM NH₄HCO₃)-ACN]; B %: 25%-55%, 10 min) to afford N-[(1S)-2-[[(1S)-1-cyano-2-[(3S)-2-oxopyrrolidin-3-yl]ethyl]amino]-1-(cyclopropylmethyl)-2-oxo-ethyl]-4,5,6,7-tetrahydro-1H-indole-2-carboxamide (61.92 mg, 150.48 umol, 22.29% yield, 100% purity) as a white solid. MS (ESI) m/z 412.3 [M+H]⁺.

¹H NMR (400 MHz, DMSO-d₆) δ=10.96 (br s, 1H), 9.00-8.77 (m, 1H), 7.89-7.66 (m, 2H), 6.60 (br s, 1H), 5.04-4.81 (m, 1H), 4.48-4.28 (m, 1H), 3.24-3.04 (m, 2H), 2.47-1.96 (m, 7H), 1.81-1.61 (m, 7H), 1.40 (br dd, J=6.6, 13.1 Hz, 1H), 0.74 (br s, 1H), 0.38 (br s, 2H), 0.22-0.03 (m, 2H).

¹H NMR (400 MHz, DMSO-d₆) δ=10.67 (br s, 1H), 8.74-8.49 (m, 1H), 7.53-7.28 (m, 2H), 6.54 (d, J=2.2 Hz, 1H), 5.05-4.84 (m, 1H), 4.54-4.38 (m, 1H), 3.17 (br d, J=7.2 Hz, 2H), 2.54 (br t, J=6.1 Hz, 2H), 2.43 (br t, J=5.6 Hz, 3H), 2.28-2.08 (m, 2H), 1.90-1.79 (m, 1H), 1.77-1.65 (m, 6H), 1.56 (qd, J=6.7, 13.7 Hz, 1H), 0.83-0.70 (m, 1H), 0.42 (br d, J=7.8 Hz, 2H), 0.20-0.04 (m, 2H).

Example 193. Synthesis of Viral Protease Inhibitor Compound 715

Step 1: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-chloro-1H-pyrrolo[3,2-c]pyridine-2-carboxamide

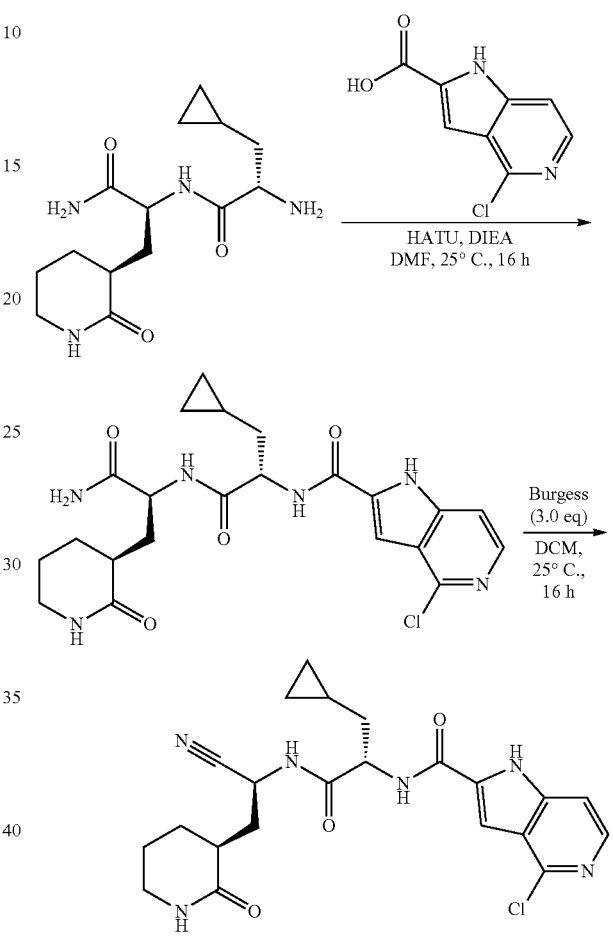

To a solution of 4-chloro-1H-pyrrolo[3,2-c]pyridine-2-carboxylic acid (110.5 mg, 0.56 mmol, 1 eq) in DMF (2 mL) was added HATU (256.6 mg, 0.67 mmol, 1.2 eq), DIEA (218.0 mg, 1.69 mmol, 0.29 mL, 3 eq) and (2S)-2-amino-N-[(1S)-2-amino-2-oxo-1-([(3S)-2-oxo-3-piperidyl]methyl]ethyl]-3-cyclopropyl-propanamide (200 mg, 0.67 mmol, 1.2 eq). The mixture was stirred at 25° C. for 16 hr. LC-MS showed the desired compound was detected. TLC (DCM/MeOH=10:1). The reaction mixture was diluted with H₂O (10 mL) and extracted with ethyl acetate (10 mL*3). The combined organic phase was washed with brine (10 mL*3), dried with anhydrous Na₂SO₄, filtered and concentrated in vacuum. The residue was purified by flash silica gel chromatography (ISCO®; 4 g SepaFlash® Silica Flash Column, Eluent of 0~20% DCM/MeOH ethergradient @ 20 mL/min) to afford N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-chloro-1H-pyrrolo[3,2-c]pyridine-2-carboxamide (214 mg, 76.2% yield) as a yellow solid.

Step 2: 4-chloro-N-[(1S)-2-[[(1S)-1-cyano-2-[(3S)-2-oxo-3-piperidyl]ethyl]amino]-1-(cyclopropylmethyl)-2-oxo-ethyl]-1H-pyrrolo[3,2-c]pyridine-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-chloro-1H-pyrrolo[3,2-c]pyridine-2-carboxamide (214 mg, 0.45 mmol, 1 eq) in DCM (3 mL) was added methoxycarbonyl-(triethylammonio)sulfonyl-azanide (322.1 mg, 1.35 mmol, 3 eq) at 0° C. The mixture was stirred at 25° C. for 16 h. TLC (DCM:MeOH=10:1). The reaction mixture was filtered and concentrated in vacuum. The residue was purified by flash silica gel chromatography (ISCO®; 12 g SepaFlash® Silica Flash Column, Eluent of 0~10% petroleum ether/ethyl acetate ethergradient @ 25 mL/min) to give 4-chloro-N-[(1S)-2-[[(1S)-1-cyano-2-[(3S)-2-oxo-3-piperidyl]ethyl]amino]-1-(cyclopropylmethyl)-2-oxo-ethyl]-1H-pyrrolo[3,2-c]pyridine-2-carboxamide (80 mg, 36.5% yield) as a white solid.

LCMS: Rt=1.356 min; for $C_{22}H_{25}ClN_6O_3$ MS Calcd.: 456.17; MS Found: 457.1 [M+H$^+$].

$^1$H NMR (400 MHz, CD$_3$OD) δ 8.75-8.65 (m, 1H), 7.53-7.43 (m, 1H), 7.41-7.31 (m, 1H), 5.14 (br d, J=9.5 Hz, 1H), 4.54 (br t, J=7.2 Hz, 1H), 3.24 (br s, 2H), 2.56-2.41 (m, 2H), 2.02-1.87 (m, 2H), 1.86-1.61 (m, 4H), 1.59-1.45 (m, 1H), 0.85 (br s, 1I), 0.54 (br d, J=8.0 Hz, 2H), 0.23-0.15 (m, 2H).

Example 194. Synthesis of Viral Protease Inhibitor Compound 639

7-chloro-N-((S)-1-(((S)-1-cyano-2-((S)-2-oxopiperidin-3-yl)ethyl)amino)-3-cyclopropyl-1-oxopropan-2-yl)-1H-indole-2-carboxamide Step 1: (S)-methyl 2-((S)-2-((tert-butoxycarbonyl)amino)-3-cyclopropylpropanamido)-3-((S)-2-oxopiperidin-3-yl)propanoate

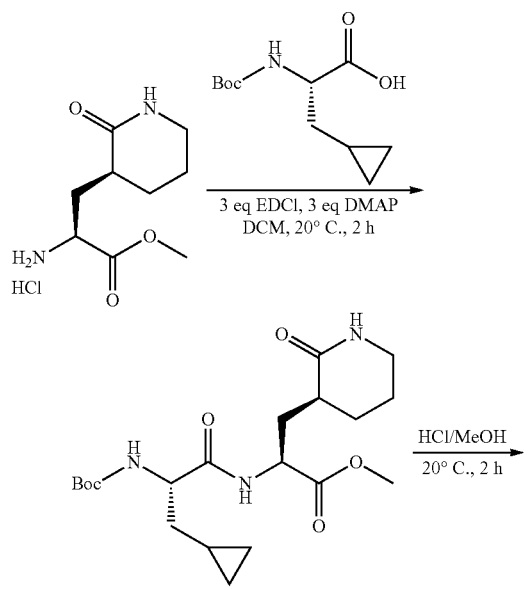

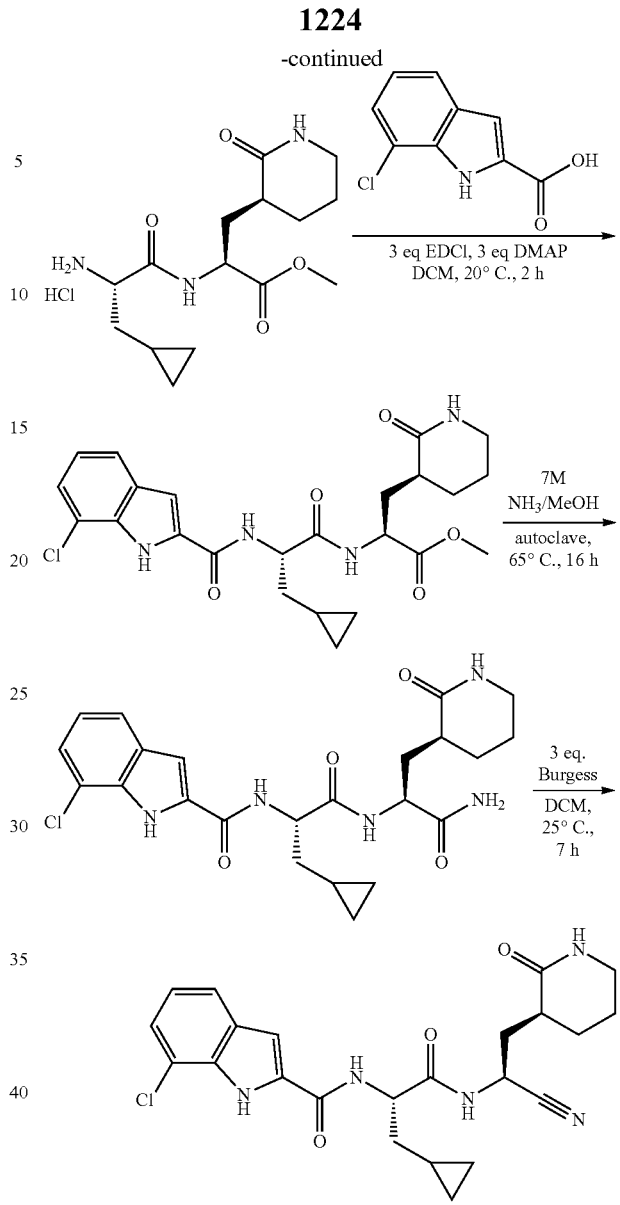

To a solution of (2S)-2-(tert-butoxycarbonylamino)-3-cyclopropyl-propanoic acid (1.45 g, 6.34 mmol, 1.5 eq), methyl (2S)-2-amino-3-[(3S)-2-oxo-3-piperidyl]propanoate (1 g, 4.22 mmol, 1 eq, HCl), DMAP (1.55 g, 12.67 mmol, 3 eq) in DCM (10 mL) was added EDCI (2.43 g, 12.67 mmol, 3 eq). The mixture was stirred at 20° C. for 2 h. Upon completion, the reaction mixture was poured into H$_2$O 50 mL at 20° C., and then extracted with DCM (50 mL*3). The combined organic layers were washed with brine (50 mL*2), dried over Na$_2$SO$_4$, filtered and concentrated under reduced pressure to give a residue. The residue was purified by column chromatography (SiO$_2$, petroleum ether/ethyl acetate=80/1 to 1/2) to give methyl (2S)-2-[[(2S)-2-(tert-butoxycarbonylamino)-3-cyclopropyl-propanoyl]amino]-3-[(3S)-2-oxo-3-piperidyl]propanoate (1.5 g, 3.10 mmol, 73.34% yield, 85% purity) as a yellow oil. MS (ESI) m/z 412.2 [M+H]$^+$.

To a solution of (2S)-2-(tert-butoxycarbonylamino)-3-cyclopropyl-propanoic acid (29.06 g, 126.75 mmol, 1.5 eq), methyl (2S)-2-amino-3-[(3S)-2-oxo-3-piperidyl]propanoate (20 g, 84.50 mmol, 1 eq, HCl) and DMAP (25.81 g, 211.24 mmol, 2.5 eq) in DCM (200 mL), then EDCI (32.40 g, 168.99 mmol, 2.0 eq) was added. The mixture was stirred at 20° C. for 2 hrs. The reaction mixture was quenched by addition H₂O 300 mL at 0° C., and extracted with DCM 300 mL (100 mL*3). The combined organic layers were washed with 0.5N HCl 100 mL and brine (100 mL*2), dried over Na2SO4, filtered and concentrated under reduced pressure to give a residue. The residue was purified by column chromatography (SiO2, Petroleum ether/Ethyl acetate=10/1 to 1/2). To give methyl (2S)-2-[[(2S)-2-(tert-butoxycarbonylamino)-3-cyclopropyl-propanoyl]amino]-3-[(3S)-2-oxo-3-piperidyl]propanoate (23 g, 54.83 mmol, 64.89% yield, 98.1% purity) was obtained as a white solid.

Step 2: (S)-methyl 2-((S)-2-amino-3-cyclopropyl-propanamido)-3-((S)-2-oxopiperidin-3-yl)propanoate To a solution of methyl (2S)-2-[[(2S)-2-(tert-butoxycarbonylamino)-3-cyclopropyl-propanoyl]amino]-3-[(3S)-2-oxo-3-piperidyl]propanoate (1.5 g, 3.65 mmol, 1 eq) in HCl/MeOH (4 M, 15.00 mL, 16.46 eq). The mixture was stirred at 20° C. for 2 h. Upon completion, the reaction mixture was concentrated under reduced pressure to remove solvent to give methyl (2S)-2-[[(2S)-2-amino-3-cyclopropyl-propanoyl]amino]-3-[(3S)-2-oxo-3-piperidyl]propanoate (1.27 g, crude, HCl) as a yellow oil. MS (ESI) m/z 312.2 [M+H]⁺.

Step 3: (S)-methyl 2-((S)-2-(7-chloro-1H-indole-2-carboxamido)-3-cyclopropylpropanamido)-3-((S)-2-oxopiperidin-3-yl)propanoate To a solution of methyl (2S)-2-[[(2S)-2-amino-3-cyclopropyl-propanoyl]amino]-3-[(3S)-2-oxo-3-piperidyl]propanoate (1.27 g, 3.65 mmol, 1 eq, HCl), 7-chloro-1H-indole-2-carboxylic acid (714.17 mg, 3.65 mmol, 1 eq), DMAP (1.34 g, 10.95 mmol, 3 eq) in DCM (13 mL) was added EDCI (1.75 g, 9.13 mmol, 2.5 eq) at 0° C., the mixture was stirred at 20° C. for 2 h. Upon completion, the reaction mixture was poured into H₂O (20 mL) at 20° C., and then extracted with DCM (25 mL*3). The combined organic layers were washed with brine (20 mL*2), dried over Na₂SO₄, filtered and concentrated under reduced pressure to give a residue. The residue was purified by column chromatography (SiO₂, petroleum ether/ethyl acetate=80/1 to 1/0) to give methyl (2S)-2-[[(2S)-2-[(7-chloro-1H-indole-2-carbonyl)amino]-3-cyclopropyl-propanoyl]amino]-3-[(3S)-2-oxo-3-piperidyl]propanoate (1.3 g, 2.53 mmol, 69.18% yield, 95% purity) as a yellow solid. MS (ESI) m/z 489.2 [M+H]⁺.

Step 4: N-((S)-1-(((S)-1-amino-1-oxo-3-((S)-2-oxopiperidin-3-yl)propan-2-yl)amino)-3-cyclopropyl-1-oxopropan-2-yl)-7-chloro-1H-indole-2-carboxamide A solution of methyl (2S)-2-[[(2S)-2-[(7-chloro-1H-indole-2-carbonyl)amino]-3-cyclopropyl-propanoyl]amino]-3-[(3S)-2-oxo-3-piperidyl]propanoate (1.3 g, 2.66 mmol, 1 eq) in NH₃/MeOH (7 M, 26 mL, 68.45 eq) was stirred at 65° C. for 16 h. The reaction mixture was concentrated under reduced pressure to remove solvent to give N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-1H-indole-2-carboxamide (1.26 g, crude) as a yellow solid. MS (ESI) m/z 474.2 [M+H]⁺.

Step 5: 7-chloro-N-((S)-1-(((S)-1-cyano-2-((S)-2-oxopiperidin-3-yl)ethyl)amino)-3-cyclopropyl-1-oxopropan-2-yl)-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-1H-indole-2-carboxamide (1.26 g, 2.66 mmol, 1 eq) in DCM (13 mL) was added Burgess reagent (1.58 g, 6.65 mmol, 2.5 eq). The mixture was stirred at 25° C. for 7 h. Upon completion, the reaction mixture was concentrated by N2 remove solvent. The residue was purified by column chromatography (SiO₂, petroleum ether/ethyl acetate=1/0 to 0/1) to give 7-chloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide (950 mg, crude) as a white solid. MS (ESI) m/z 456.2 [M+H]⁺.

Example 195. Synthesis of Viral Protease Inhibitor Compound 717

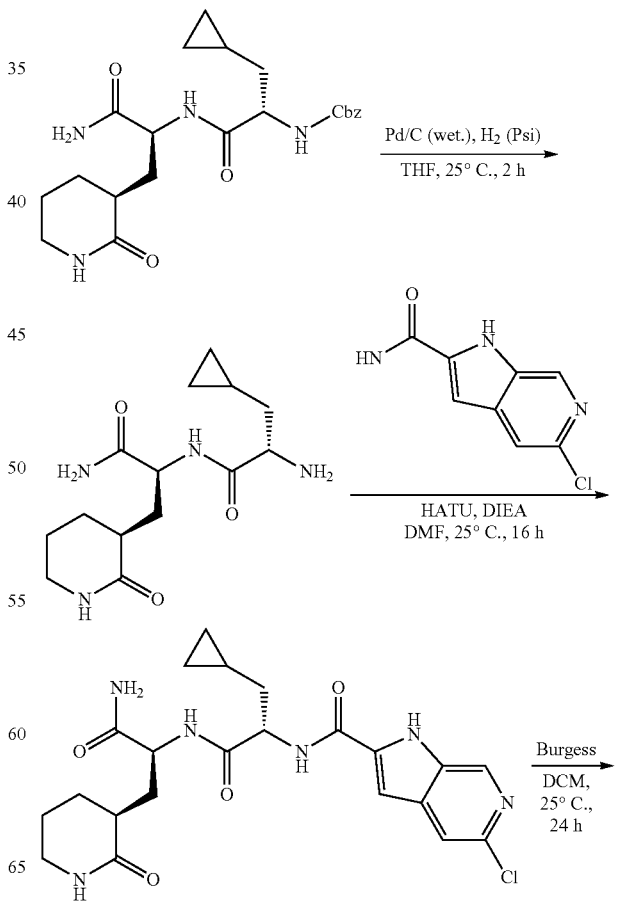

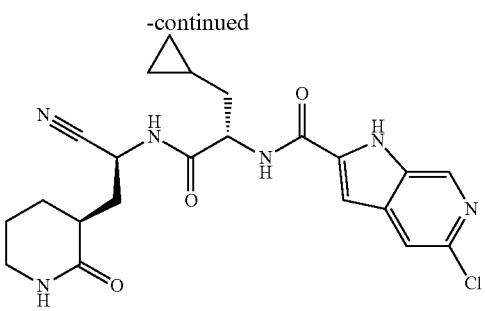

To a solution of benzyl N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]carbamate (600 mg, 1.39 mmol, 1 eq) in THF (1 mL) was added Pd/C under $N_2$ atmosphere. The suspension was degassed and purged with $H_2$ for 3 times. The mixture was stirred under $H_2$ (15 Psi or atm.) at 25° C. for 2 h. Pd/C was filtered and the reaction was concentrated under reduced pressure to give a residue. Compound (2S)-2-amino-N-[(1S)-2-amino-2-oxo-1-[[(3S)-2-oxo-3-piperidyl]methyl]ethyl]-3-cyclopropyl-propanamide (400 mg, crude) was obtained as a colorless oil.

Step 2: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-5-chloro-1H-pyrrolo[2,3-c]pyridine-2-carboxamide A solution of (2S)-2-amino-N-[(1S)-2-amino-2-oxo-1-[[(3S)-2-oxo-3-piperidyl]methyl]ethyl]-3-cyclopropyl-propanamide (250 mg, 0.84 mmol, 1 eq) in DMF (1 mL) was added HATU (320.7 mg, 0.84 mmol, 1 eq), 5-chloro-1H-pyrrolo[2,3-c]pyridine-2-carboxylic acid (182.4 mg, 0.92 mmol, 1.1 eq) and DIEA (218.0 mg, 1.69 mmol, 0.29 mL, 2 eq) was stirred at 25° C. for 16 hr. TLC (DCM/MeOH=10:1, $I_2$). The reaction mixture was diluted with $H_2O$ (30 mL) and extracted with ethyl acetate (30 mL*3). The combined organic layers were washed with brine (30 mL*2), dried with anhydrous $Na_2SO_4$, filtered and concentrated under reduced pressure to give a residue. The residue was purified by flash silica gel chromatography (ISCO®; 12 g SepaFlash® Silica Flash Column, Eluent of 0~7% DCM/MeOH @ 35 mL/min). N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-5-chloro-1H-pyrrolo[2,3-c]pyridine-2-carboxamide (260 mg, 64.3% yield, 99.2% purity) was obtained as a white solid.

Step 3: 5-chloro-N-[(1S)-2-[[(1S)-1-cyano-2-[(3S)-2-oxo-3-piperidyl]ethyl]amino]-1-(cyclopropylmethyl)-2-oxo-ethyl]-1H-pyrrolo[2,3-c]pyridine-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-5-chloro-1H-pyrrolo[2,3-c]pyridine-2-carboxamide (100 mg, 0.21 mmol, 1 eq) in DCM (1 mL) was added methoxycarbonyl-(triethylammonio)sulfonyl-azanide (150.5 mg, 0.63 mmol, 3 eq). The mixture was stirred at 25° C. for 24 h. The reaction mixture was diluted with $H_2O$ (30 mL) and extracted with DCM (30 mL*3). The combined organic layers were washed with brine (30 mL*2), dried with anhydrous $Na_2SO_4$, filtered and concentrated under reduced pressure to give a residue. The residue was purified by prep-HPLC (column: Phenomenex Gemini-NX 80*40 mm*3 um; mobile phase: [water(0.05% $NH_3H_2O$+10 mM $NH_4HCO_3$)-ACN]; B %: 15%-45%, 9.5 min). 5-Chloro-N-[(1S)-2-[[(1S)-1-cyano-2-[(3S)-2-oxo-3-piperidyl]ethyl]amino]-1-(cyclopropylmethyl)-2-oxo-ethyl]-1H-pyrrolo[2,3-c]pyridine-2-carboxamide (94 mg, 96.7% yield, 99% purity) was obtained as a yellow solid.

LCMS: Rt=0.754 min; for $C_{22}H_{25}ClN_6O_3$ MS Calcd.: 456.93; MS Found: 457.1 [M+H$^+$].

$^1$H NMR (400 MHz, $CD_3OD$) δ 8.58 (s, 1H), 7.72-7.65 (m, 1H), 7.20 (s, 1H), 5.13 (dd, J=6.1, 10.2 Hz, 1H), 4.58-4.52 (m, 1H), 3.28-3.16 (m, 2H), 2.59-2.39 (m, 2H), 2.07-1.87 (m, 3H), 1.87-1.79 (m, 1H), 1.78-1.62 (m, 2H), 1.60-1.44 (m, 1H), 0.91-0.78 (m, 1H), 0.58-0.47 (m, 2H), 0.26-0.13 (m, 2H).

Example 196. Synthesis of Viral Protease Inhibitor Compound Potassium (2S)-1-hydroxy-2-((2S,4S)-1-(4-methoxy-1H-indole-2-carbonyl)-4-phenylpyrrolidine-2-carboxamido)-3-((S)-2-oxopyrrolidin-3-yl)propane-1-sulfonate Step 1: [(2S)-1-hydroxy-2-[[(2S,4S)-1-(4-methoxy-1H-indole-2-carbonyl)-4-phenyl-pyrrolidine-2-carbonyl]amino]-3-[(3S)-2-oxopyrrolidin-3-yl]propyl]sulfonyloxypotassium

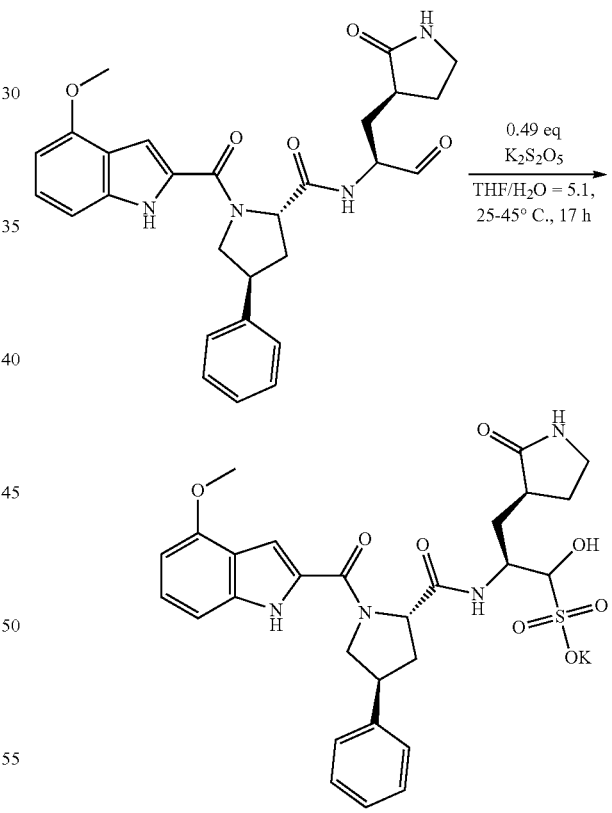

To a mixture of (2S,4S)-N-[(1S)-1-formyl-2-[(3S)-2-oxopyrrolidin-3-yl]ethyl]-1-(4-methoxy-1H-indole-2-carbonyl)-4-phenyl-pyrrolidine-2-carboxamide (40 mg, 79.59 umol, 1 eq) in THF (0.5 mL) was added $K_2S_2O_5$ (8.67 mg, 39.00 umol, 0.49 eq) in $H_2O$ (0.1 mL) at 45° C. under $N_2$. The mixture was stirred at 45° C. for 3 h, and then stirred at 25° C. for 14 h under $N_2$. Upon completion, the reaction mixture was concentrated under reduced pressure, and then triturated with THF (1 mL) at 25° C. for 1 h to give

[(2S)-1-hydroxy-2-[[(2S,4S)-1-(4-methoxy-1H-indole-2-carbonyl)-4-phenyl-pyrrolidine-2-carbonyl]amino]-3-[(3S)-2-oxopyrrolidin-3-yl]propyl]sulfonyloxypotassium (14.09 mg, 20.36 umol, 25.58% yield, 90% purity) as an off-white solid. MS (ESI) m/z 585.3 [M−36.8]+.

¹H NMR (400 MHz, DMSO-d₆) δ ppm 11.68-11.40 (m, 1H), 8.08-7.64 (m, 0.5H), 7.52-7.43 (m, 0.5H), 7.41-7.29 (m, 4H), 7.28-7.19 (m, 1H), 7.15-6.97 (m, 2H), 6.96-6.76 (m, 1H), 6.55-6.37 (m, 1H), 5.48-5.27 (m, 1H), 5.25-4.92 (m, 0.511), 4.80-4.60 (m, 0.5H), 4.46-4.07 (m, 2H), 4.02-3.93 (m, 0.511), 3.93-3.63 (m, 5H), 3.62-3.36 (m, 1H), 3.18-3.02 (m, 1H), 2.94-2.69 (m, 0.5H), 2.35-2.17 (m, 3H), 2.10-1.87 (m, 1H), 1.82-1.27 (m, 3H).

Example 197. Synthesis of (S)-2-amino-3-((S)-2-oxopyrrolidin-3-yl)propanenitrile hydrochloride

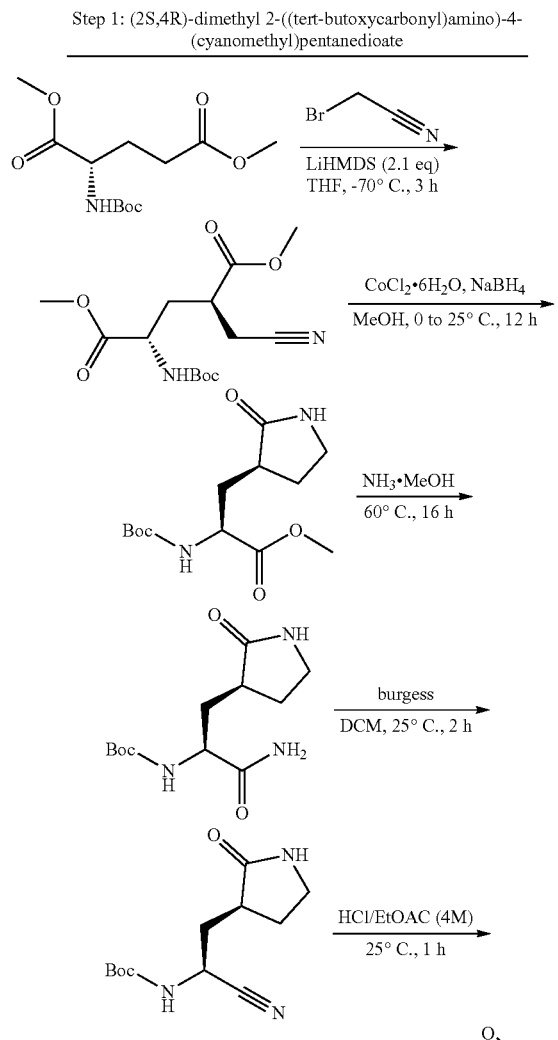

Step 1: (2S,4R)-dimethyl 2-((tert-butoxycarbonyl)amino)-4-(cyanomethyl)pentanedioate To a solution of dimethyl 2-(tert-butoxycarbonylamino)pentanedioate (10 g, 36.32 mmol, 1 eq) in THF (150 mL) was added LiHMDS (1 M, 83.55 mL, 2.3 eq) at −78° C. under N₂. The mixture was stirred at −78° C. for 1.5 h. Then, 2-bromoacetonitrile (6.54 g, 54.49 mmol, 3.63 mL, 1.5 eq) was added dropwise to the reaction at −78° C. The mixture was stirred at −78° C. for 2.5 h. TLC (PE:EA=3:1, I₂). The reaction was completed, pre-cooled methanol (15 mL) and glacial acetic acid (12 mL) were sequentially added to quench the reaction. The reaction was warmed to 25° C., and the solvent was distilled off under reduced pressure. The residue was purified by flash silica gel chromatography (ISCO®; 120 g SepaFlash® Silica Flash Column, Eluent of 0~20% ethyl acetate/petroleum ether gradient @ 80 mL/min). Dimethyl (4R)-2-(tert-butoxycarbonylamino)-4-(cyanomethyl)pentanedioate (15 g, 47.72 mmol, 43.79% yield) was obtained as a yellow oil.

Step 2: (S)-methyl2-((tert-butoxycarbonyl)amino)-3-((S)-2-oxopyrrolidin-3-yl)propanoate Dimethyl (4R)-2-(tert-butoxycarbonylamino)-4-(cyanomethyl)pentanedioate (15 g, 47.72 mmol, 1 eq) was dissolved in MeOH (250 mL), and CoCl₂·6H₂O (6.81 g, 28.63 mmol, 0.6 eq) was added under 0° C. After adding NaBH4 (10.83 g, 286.32 mmol, 6 eq) slowly in batches, the reaction was carried out at 25° C. for 12 h. TLC (petroleum ether/ethyl acetate=1:2, I₂). After the reaction was completed, 100 mL of saturated ammonium chloride solution was added to quench the reaction. The organic phase was collected by filtration, the solvent was distilled off under reduced pressure, and extracted with EtOAc (150 mL*3), and the organic phase was collected. The organic phase was washed with saturated brine (100 mL). The organic phase was dried over anhydrous Na₂SO₄, the filtrate was collected by filtration, and the solvent was evaporated under reduced pressure. The residue was purified by flash silica gel chromatography (ISCO®; 40 g SepaFlash® Silica Flash Column, Eluent of 0~80% ethyl acetate/petroleum ether gradient @ 40 mL/min). (S)-Methyl 2-((tert-butoxycarbonyl)amino)-3-((S)-2-oxopyrrolidin-3-yl)propanoate (7 g, 24.45 mmol, 51.2% yield, 100% purity) was obtained as a white solid.

Step 3: tert-butyl ((S)-1-amino-1-oxo-3-((S)-2-oxopyrrolidin-3-yl)propan-2-yl)carbamate To a solution of methyl (2S)-2-(tert-butoxycarbonylamino)-3-[(3S)-2-oxopyrrolidin-3-yl]propanoate (2 g, 6.99 mmol, 1 eq) in MeOH (10 mL) was added a solution of NH₃ (7 M, 24.00 mL, 24.05 eq). The mixture was allowed to stir at 60° C. for 16 h in sealed tube. The reaction mixture was concentrated under reduced pressure to give a residue. Compound tert-butyl ((S)-1-amino-1-oxo-3-((S)-2-oxopyrrolidin-3-yl)propan-2-yl)carbamate (1.8 g, 6.63 mmol, 94.9% yield) was obtained as a yellow solid.

Step 4: Tert-butyl ((S)-1-cyano-2-((S)-2-oxopyrrolidin-3-yl)ethyl)carbamate

To a solution of tert-butyl N-[(1S)-2-amino-2-oxo-1-[[(3S)-2-oxopyrrolidin-3-yl]methyl]ethyl]carbamate (1 g, 3.69 mmol, 1 eq) in DCM (10 mL) was added Burgess reagent (3.51 g, 14.74 mmol, 4 eq). The mixture was stirred at 25° C. for 1 h under N₂. The reaction mixture was added H₂O (10 mL) and extracted with DCM (10 mL*3). The combined organic layers were washed with brine (20 mL), dried with anhydrous Na$_2$SO$_4$, filtered and concentrated under reduced pressure to give a residue. The residue was purified by flash silica gel chromatography (ISCO®; 12 g SepaFlash® Silica Flash Column, Eluent of 0-70% ethyl acetate/petroleum ether gradient @ 30 mL/min). Compound tert-butyl N-[(1S)-1-cyano-2-[(3S)-2-oxopyrrolidin-3-yl]ethyl]carbamate (900 mg, 3.23 mmol, 87.7% yield, 91% purity) was obtained as a white solid.

Step 5: (S)-2-amino-3-((S)-2-oxopyrrolidin-3-yl)propanenitrile hydrochloride

To a solution of tert-butyl N-[(1S)-1-cyano-2-[(3S)-2-oxopyrrolidin-3-yl]ethyl]carbamate (600 mg, 2.37 mmol, 1 eq) in EtOAc (20 mL) was added HCl/EtOAc (4 M, 4.00 mL, 6.75 eq). The mixture was stirred at 25° C. for 2 h. LCMS showed starting material was consumed and detected desired compound. The reaction mixture was concentrated under reduced pressure to give a residue. Compound (2S)-2-amino-3-[(3S)-2-oxopyrrolidin-3-yl]propanenitrile (440 mg, 2.32 mmol, 97.9% yield, HCl) was obtained as a white solid.

Example 198. Synthesis of Viral Protease Inhibitor Compound 842

Step 1: methyl (2S)-2-[[(2S)-3-cyclopropyl-2-[(5,7-dichloro-1H-indole-2-carbonyl)amino]propanoyl]amino]-3-[(3S)-2-oxo-3-piperidyl]propanoate

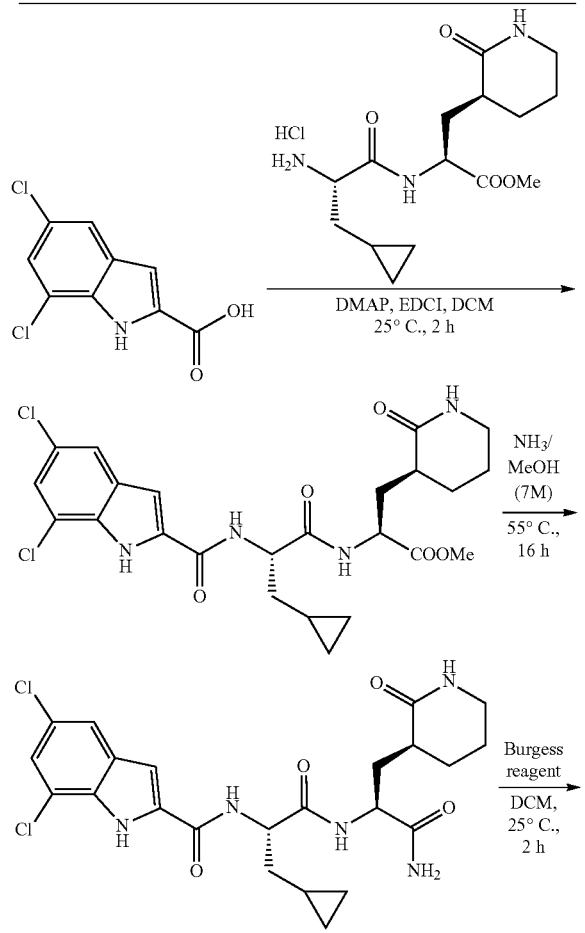

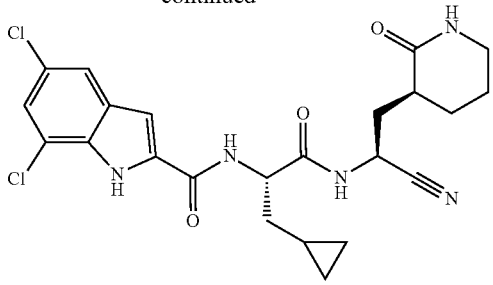

To a mixture of 5,7-dichloro-1H-indole-2-carboxylic acid (1 g, 4.35 mmol, 1 eq) and methyl (2S)-2-[[(2S)-2-amino-3-cyclopropyl-propanoyl]amino]-3-[(3S)-2-oxo-3-piperidyl]propanoate (1.35 g, 3.89 mmol, 8.95 e−1 eq, HCl) in DCM (24 mL) was added DMAP (1.59 g, 13.04 mmol, 3 eq) and EDCI (1.67 g, 8.69 mmol, 2 eq) in one portion at 25° C. The mixture was stirred at 25° C. for 2 h. Upon completion, the reaction mixture was diluted with H$_2$O (20 mL) and extracted with ethyl acetate (20 mL*4). The combined organic layers were washed with brine (40 mL*1), dried over Na$_2$SO$_4$, filtered and concentrated under reduced pressure to give the crude product. The crude was purified by column chromatography (SiO$_2$, petroleum ether/ethyl acetate=3/1 to 0/1) to give methyl (2S)-2-[[(2S)-3-cyclopropyl-2-[(5,7-dichloro-1H-indole-2-carbonyl)amino]propanoyl]amino]-3-[(3S)-2-oxo-3-piperidyl]propanoate (1.2 g, 2.29 mmol, 52.74% yield) as a white solid. MS (ESI) m/z 521.0 [M−H]$^+$ Step 2: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-5,7-dichloro-1H-indole-2-carboxamide A mixture of methyl (2S)-2-[[(2S)-3-cyclopropyl-2-[(5,7-dichloro-1H-indole-2-carbonyl)amino]propanoyl]amino]-3-[(3S)-2-oxo-3-piperidyl]propanoate (1.2 g, 2.29 mmol, 1 eq) in NH$_3$/MeOH (7M, 30 mL) was stirred at 55° C. for 16 hours. Upon completion, the reaction mixture was concentrated under reduced pressure to give N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-5,7-dichloro-1H-indole-2-carboxamide (1 g, 1.97 mmol, 85.79% yield) as a white solid. MS (ESI) m/z 508.2 [M+H]$^+$ Step 3: 5,7-dichloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide To a mixture of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-5,7-dichloro-1H-indole-2-carboxamide (260 mg, 475.61 umol, 93% purity, 1 eq) in DCM (5 mL) was added Burgess reagent (226.68 mg, 951.23 umol, 2 eq) in one portion at 25° C. The mixture was stirred at 25° C. for 2 hours. Upon completion, the reaction mixture was concentrated under reduced pressure to give the crude product. The crude was purified by prep-HPLC (neutral condition; column: Phenomenex Gemini-NX C18 75*30 mm*3 um; mobile phase: [water (10 mM NH$_4$HCO$_3$)-ACN]; B %: 40%-60%, 8 min) to give 5,7-dichloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2- carboxamide (100 mg, 203.92 umol, 42.88% yield) as a white solid. MS (ESI) m/z 490.1 [M+H]$^+$ $^1$H NMR (400 MHz, DMSO-d$_6$) δ=11.98 (br s, 1H), 9.00 (d, J=7.9 Hz, 1H), 8.77 (d, J=7.7 Hz, 1H), 7.75 (d, J=1.8 Hz, 1H), 7.54 (br s, 1H), 7.41 (d, J=1.8 Hz, 1H), 7.26 (s, 1H), 5.07 (q, J=8.0 Hz, 1H), 4.55-4.47 (m, 1H), 3.16-3.02 (m, 2H), 2.30-2.20 (m, 2H), 1.90-1.65 (m, 4H), 1.63-1.33 (m, 3H), 0.87-0.75 (m, 1H), 0.50-0.36 (m, 2H), 0.24-0.07 (m, 2H).

Example 199. Synthesis of Viral Protease Inhibitor Compound 852

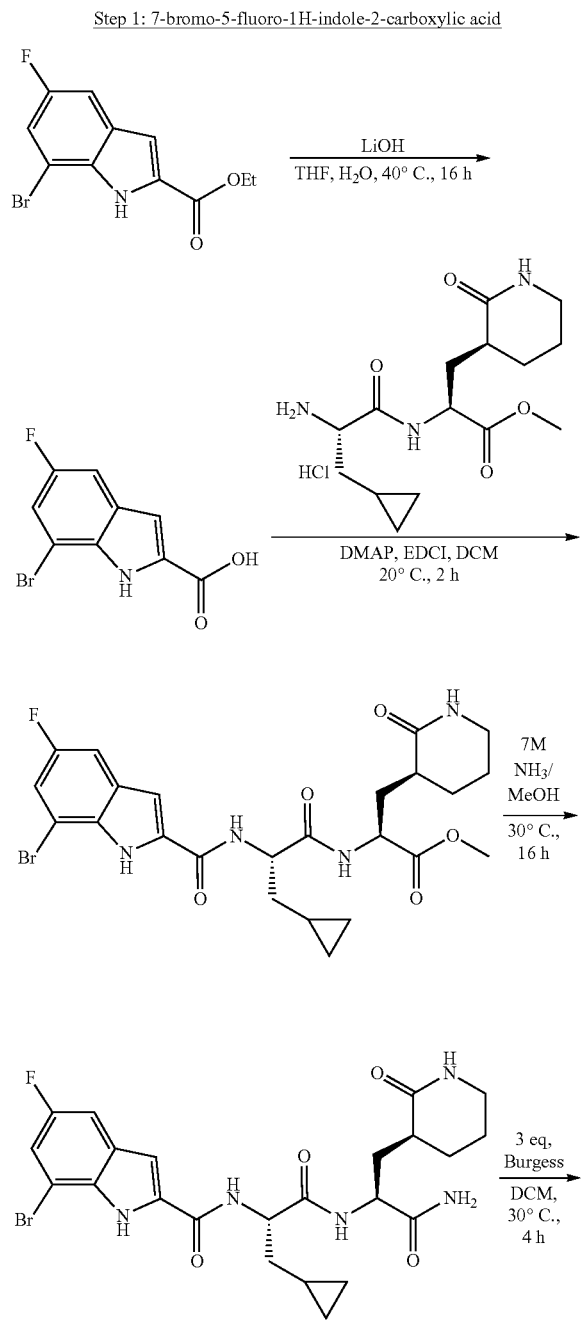

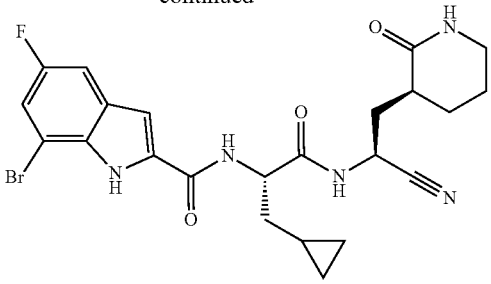

To a solution of ethyl 7-bromo-5-fluoro-1H-indole-2-carboxylate (800 mg, 2.80 mmol, 1 eq) in THF (8 mL) and H$_2$O (4 mL) was added LiOH·H$_2$O (117.34 mg, 2.80 mmol, 1 eq) at 40° C. The mixture was stirred at 40° C. for 16 h. Upon completion of reaction, the mixture was concentrated in vacuum and then the pH was adjusted to about 1 with 1 M HCl (10 mL), and was extracted with ethyl acetate (10 mL*3) to obtain 7-bromo-5-fluoro-1H-indole-2-carboxylic acid (700 mg, crude) as a yellow solid. MS (ESI) m/z 256.0 [M−H]$^+$ Step 2: (S)-methyl 2-((S)-2-(7-bromo-5-fluoro-1H-indole-2-carboxamido)-3-cyclopropylpropanamido)-3-((S)-2-oxopiperidin-3-yl)propanoate To a solution of methyl (2S)-2-[[(2S)-2-amino-3-cyclopropyl-propanoyl]amino]-3-[(3S)-2-oxo-3-piperidyl] propanoate (800 mg, 2.30 mmol, 1 eq, HCl) and 7-bromo-5-fluoro-1H-indole-2-carboxylic acid (700 mg, 2.76 mmol, 1.2 eq) in DCM (10 mL) was added DMAP (561.96 mg, 4.60 mmol, 2 eq), and then the mixture was added with EDCI (881.79 mg, 4.60 mmol, 2 eq). After stirring at 20° C. for 2 h, the mixture was poured into water (30 mL) and was extracted with DCM (10 mL*3) and dried with anhydrous Na$_2$SO$_4$, filtered and concentrated in vacuum and was purified by column (SiO$_2$, PE/EA=1:0 to 0:1) to obtain (S)-methyl 2-((S)-2-(7-bromo-5-fluoro-1H-indole-2-carboxamido)-3-cyclopropylpropanamido)-3-((S)-2-oxopiperidin-3-yl)propanoate (1 g, 1.75 mmol, 76.09% yield, 96.5% purity) as a light yellow solid. MS (ESI) m/z 551.1 [M+H]$^+$ Step 3: N-((S)-1-(((S)-1-amino-1-oxo-3-((S)-2-oxopiperidin-3-yl)propan-2-yl)amino)-3-cyclopropyl-1-oxopropan-2-yl)-7-bromo-5-fluoro-1H-indole-2-carboxamide A solution of (S)-methyl 2-((S)-2-(7-bromo-5-fluoro-1H-indole-2-carboxamido)-3-cyclopropylpropanamido)-3-((S)-2-oxopiperidin-3-yl) propanoate (1 g, 1.81 mmol, 1 eq) in NH$_3$/MeOH (30 mL, 7M) was stirred at 30° C. for 16 h. The mixture was concentrated in vacuum. Upon completion of reaction, the mixture was concentrated in vacuum to obtain N-((S)-1-(((S)-1-amino-1-oxo-3-((S)-2-oxopiperidin-3-yl)propan-2-yl)amino)-3-cyclopropyl-1-oxopropan-2-yl)-7-bromo-5-fluoro-1H-indole-2-carboxamide (800 mg, crude) as a light yellow solid. MS (ESI) m/z 536.2 [M+H]$^+$ Step 4: 7-bromo-N-((S)-1-(((S)-1-cyano-2-((S)-2-oxopiperidin-3-yl)ethyl)amino)-3-cyclopropyl-1-oxopropan-2-yl)-5-fluoro-1H-indole-2-carboxamide To a solution of N-((S)-1-(((S)-1-amino-1-oxo-3-((S)-2-oxopiperidin-3-yl)propan-2-yl)amino)-3-cyclopropyl-1-oxopropan-2-yl)-7-bromo-5-fluoro-1H-indole-2-carboxamide (800 mg, 1.81 mmol, 1 eq) in DCM (10 mL) was added Burgess reagent (1.30 g, 5.44 mmol, 3 eq), and the mixture was stirred at 30° C. for 4 h. Upon completion of reaction, the reaction mixture was quenched by water (1 mL) and was dried with using N₂ and was purified by prep-HPLC (column: Welch Xtimate C18 250*70 mm #10 um; mobile phase: [water (10 mM NH₄HCO₃)-ACN]; B %: 30%-60%, 20 min) to obtain 7-bromo-N-((S)-1-(((S)-1-cyano-2-((S)-2-oxopiperidin-3-yl)ethyl)amino)-3-cyclopropyl-1-oxopropan-2-yl)-5-fluoro-1H-indole-2-carboxamide (740 mg, 1.33 mmol, 53.51% yield, 98% purity) as a white solid. MS (ESI) m/z 518.1 [M+H]⁺

¹H NMR (400 MHz, DMSO-d₆) δ ppm 9.01 (d, J=7.7 Hz, 1H), 8.81 (d, J=7.5 Hz, 1H), 7.59-7.48 (m, 2H), 7.45 (dd, J=2.4, 9.0 Hz, 1H), 7.26 (s, 1H), 5.07 (q, J=7.8 Hz, 1H), 4.57-4.46 (m, 1H), 3.14-3.01 (m, 2H), 2.31-2.19 (m, 2H), 1.90-1.64 (m, 4H), 1.63-1.34 (m, 3H), 0.85-0.75 (m, 1H), 0.49-0.37 (m, 2H), 0.24-0.06 (m, 2H).

Example 200. Synthesis of Viral Protease Inhibitor Compound 876

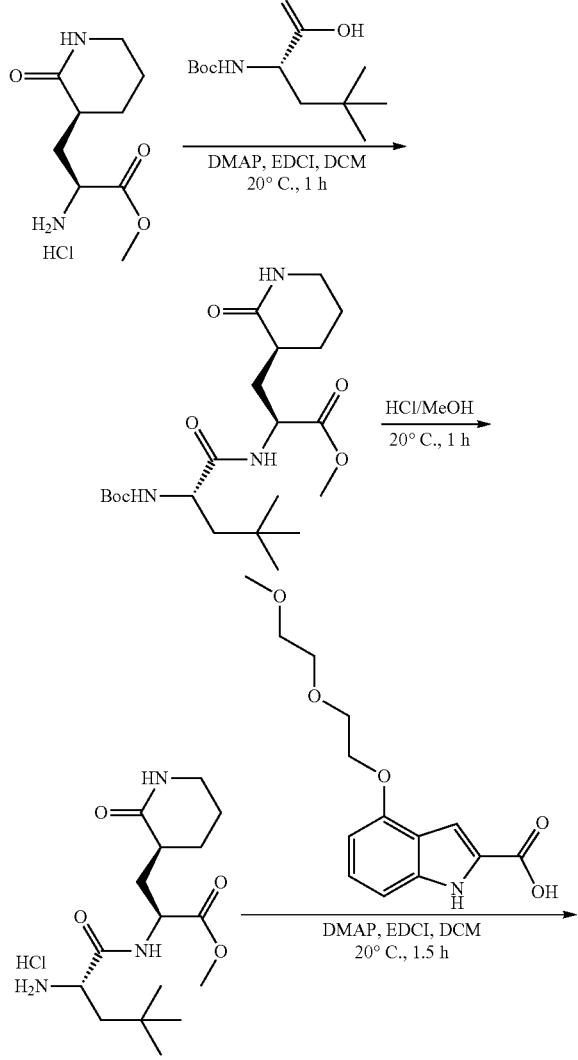

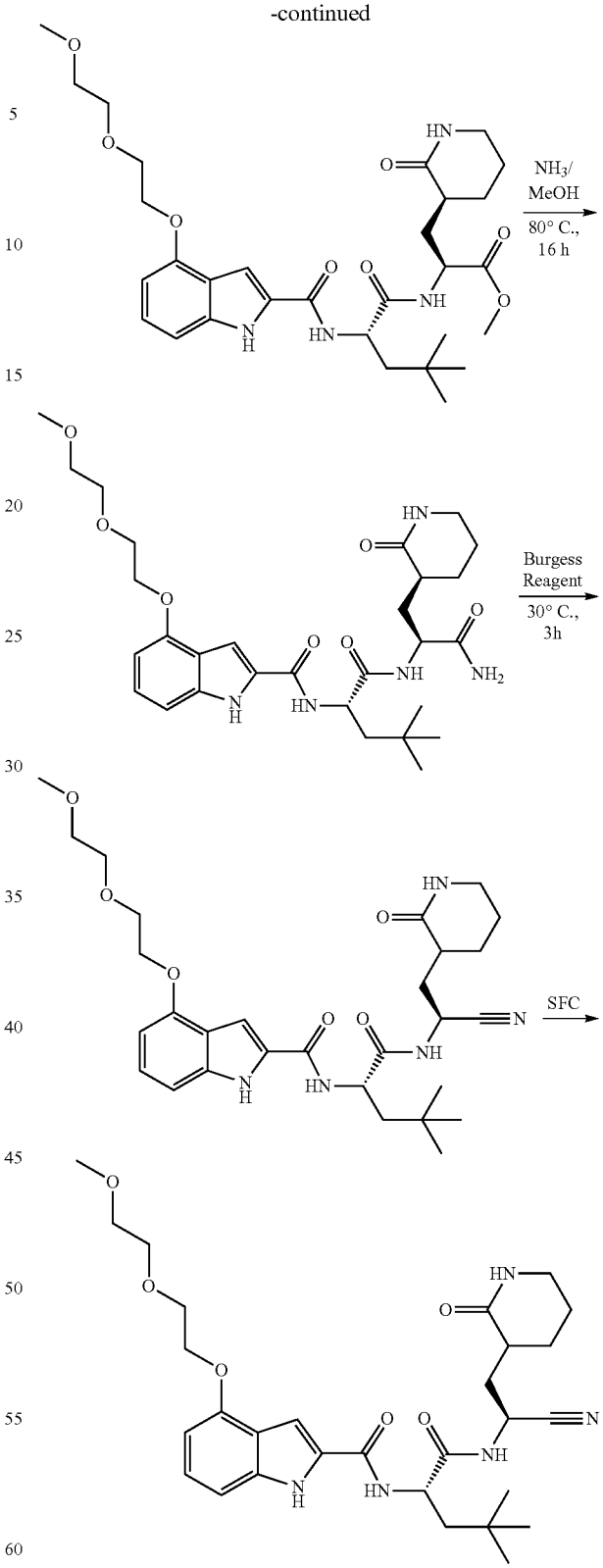

A mixture of methyl (2S)-2-amino-3-[(3S)-2-oxo-3-piperidyl]propanoate (1.3 g, 5.49 mmol, 1 eq, HCl) in DCM (20 mL) was added (2S)-2-(tert-butoxycarbonylamino)-4,4-dimethyl-pentanoic acid (1.62 g, 6.59 mmol, 1.2 eq), DMAP (1.68 g, 13.73 mmol, 2.5 eq) and EDCI (2.11 g, 10.98 mmol, 2 eq). After stirring at 20° C. for 1 h, the reaction mixture was diluted with water (50 mL) and extracted with DCM (30 mL*3). The combined organic layers were dried over $Na_2SO_4$, filtered and concentrated under reduced pressure to give a residue. The residue was purified by column ($SiO_2$, PE:EA=6/1~4/1) to get product methyl (2S)-2-[[(2S)-2-(tert-butoxycarbonylamino)-4,4-dimethyl-pentanoyl]amino]-3-[(3S)-2-oxo-3-piperidyl]propanoate (1.9 g, 4.00 mmol, 72.82% yield, 90% purity) as yellow oil. MS (ESI) m/z 428.3 $[M+H]^+$.

Step 2: methyl (2S)-2-amino-3-[(3S)-2-oxo-3-piperidyl]propanoate

A mixture of methyl (2S)-2-(tert-butoxycarbonylamino)-3-[(3S)-2-oxo-3-piperidyl]propanoate (1.71 g, 5.69 mmol, 1 eq) in HCl/MeOH (4 M, 20.00 mL, 14.05 eq) was stirred at 20° C. for 1 h. Upon completion, the mixture was concentrated under reduced pressure to give a residue, then was dissolved with DCM (30 mL*3) and concentrated under reduced pressure to get the product methyl (2S)-2-amino-3-[(3S)-2-oxo-3-piperidyl]propanoate (1.35 g, crude, HCl) as white oil. MS (ESI) m/z 328.3 $[M+H]^+$.

Step 3: methyl (2S)-2-[[(2S)-2-[[4-[2-(2-methoxyethoxy)ethoxy]-1H-indole-2-carbonyl]amino]-4,4-dimethyl-pentanoyl]amino]-3-[(3S)-2-oxo-3-piperidyl]propanoate A mixture of methyl (2S)-2-[[(2S)-2-amino-4,4-dimethyl-pentanoyl]amino]-3-[(3S)-2-oxo-3-piperidyl]propanoate (1.35 g, 3.71 mmol, 1 eq, HCl) in DCM (20 mL) then added 4-[2-(2-methoxyethoxy)ethoxy]-1H-indole-2-carboxylic acid (1.24 g, 4.45 mmol, 1.2 eq), DMAP (1.13 g, 9.28 mmol, 2.5 eq) and EDCI (1.42 g, 7.42 mmol, 2 eq) was stirred at 20° C. for 1.5 h. Upon completion, the reaction mixture was diluted with water (50 mL) and extracted with DCM (30 mL*3). The combined organic layers were dried over $Na_2SO_4$, filtered and concentrated under reduced pressure to give a residue. The residue was purified by column ($SiO_2$, PE:EA=8/1~4/1) to get methyl (2S)-2-[[(2S)-2-[[4-[2-(2-methoxyethoxy)ethoxy]-1H-indole-2-carbonyl]amino]-4,4-dimethyl-pentanoyl]amino]-3-[(3S)-2-oxo-3-piperidyl]propanoate (2.1 g, 2.85 mmol, 76.92% yield, 80% purity) as a yellow solid. MS (ESI) m/z 589.4 $[M+H]^+$.

Step 4: 2-(7-chloro-4-methoxy-1H-indole-2-carbonyl)-N-[(1S)-1-cyano-2-[(3S)-2-oxopyrrolidin-3-yl]ethyl]-2-azaspiro[4.5]decane-3-carboxamide A mixture of methyl (2S)-2-[[(2S)-2-[[4-[2-(2-methoxyethoxy)ethoxy]-1H-indole-2-carbonyl]amino]-4,4-dimethyl-pentanoyl]amino]-3-[(3S)-2-oxo-3-piperidyl]propanoate (0.52 g, 4 batches in parallel, 706.65 umol, 80% purity, 1 eq) in $NH_3$/MeOH (7 M, 8 mL, 79.25 eq) was stirred at 80° C. for 16 h. Upon completion, the mixture was concentrated under reduced pressure to give a residue, and then was dissolved with DCM (30 mL*3). The reaction was concentrated under reduced pressure to afford N-[(1S)-1-[[(1S)-2-amino-2-oxo-1-[[(3S)-2-oxo-3-piperidyl]methyl]ethyl]carbamoyl]-3,3-dimethyl-butyl]-4-[2-(2-methoxyethoxy)ethoxy]-1H-indole-2-carboxamide (1.3 g, crude) as a white solid. MS (ESI) m/z 574.4 $[M+H]^+$.

Step 5: N-[1-[[1-cyano-2-[(3S)-2-oxo-3-piperidyl]ethyl]carbamoyl]-3,3-dimethyl-butyl]-4-[2-(2-methoxyethoxy)ethoxy]-1H-indole-2-carboxamide A mixture of N-[(1S)-1-[[(1S)-2-amino-2-oxo-1-[[(3S)-2-oxo-3-piperidyl]methyl]ethyl]carbamoyl]-3,3-dimethyl-butyl]-4-[2-(2-methoxyethoxy)ethoxy]-1H-indole-2-carboxamide (1.1 g, 1.92 mmol, 1 eq) in DCM (15 mL) was added with BURGESS REAGENT (1.37 g, 5.76 mmol, 3 eq). The resulting mixture was stirred at 30° C. for 3 h. Upon completion, the mixture were quenched with water (1 mL) and dried with using N2. The residue was purified by prep-HPLC (column: Waters X bridge C18 150*50 mm*10 um; mobile phase: [water (10 mM $NH_4HCO_3$)-ACN]; B %: 30%-60%, 10 min), which was further separated by SFC (column: DAICEL CHIRALPAK AD (250 mm*30 mm, 10 um); mobile phase: [Neu-ETOH]; B %: 53%-53%, 10 min): to afford N-[1-[[1-cyano-2-[(3S)-2-oxo-3-piperidyl]ethyl]carbamoyl]-3,3-dimethyl-butyl]-4-[2-(2-methoxyethoxy)ethoxy]-1H-indole-2-carboxamide Isomer 1 (250.32 mg, 450.49 umol, 23.46% yield) as a white solid. MS (ESI) m/z 556.3 $[M+H]^+$.

$^1$H NMR (400 MHz, MeOD-$d_4$) δ 7.29 (s, 1H), 7.17-7.10 (m, 1H), 7.07-7.01 (m, 1H), 6.52 (d, J=7.5 Hz, 1H), 5.08 (dd, J=6.2, 9.9 Hz, 1H), 4.64 (dd, J=4.2, 8.6 Hz, 1H), 4.29-4.23 (m, 2H), 3.93 (dd, J=4.0, 5.3 Hz, 2H), 3.79-3.74 (m, 2H), 3.62-3.54 (m, 2H), 3.37 (s, 3H), 3.23-3.14 (m, 2H), 2.49-2.37 (m, 2H), 2.00-1.41 (m, 7H), 1.03 (s, 9H).

N-[1-[[1-cyano-2-[(3S)-2-oxo-3-piperidyl]ethyl]carbamoyl]-3,3-dimethyl-butyl]-4-[2-(2-methoxyethoxy)ethoxy]-1H-indole-2-carboxamide Isomer 2 (27.92 mg, 50.25 umol, 2.62% yield) was obtained as a white solid. MS (ESI) m/z 556.3 $[M+H]^+$.

$^1$H NMR (400 MHz, MeOD-$d_4$) δ=7.29 (d, J=0.9 Hz, 1H), 7.17-7.11 (m, 1H), 7.04 (d, J=8.4 Hz, 1H), 6.52 (d, J=7.5 Hz, 1H), 5.08 (dd, J=5.8, 8.0 Hz, 1H), 4.68 (dd, J=4.0, 8.8 Hz, 1H), 4.30-4.23 (m, 2H), 3.93 (dd, J=3.9, 5.2 Hz, 2H), 3.80-3.73 (m, 2H), 3.62-3.56 (m, 2H), 3.37 (s, 3H), 3.22-3.13 (m, 2H), 2.45-2.28 (m, 2H), 2.01-1.76 (m, 5H), 1.71-1.49 (m, 2H), 1.02 (s, 9H).

N-[1-[[1-cyano-2-[(3S)-2-oxo-3-piperidyl]ethyl]carbamoyl]-3,3-dimethyl-butyl]-4-[2-(2-methoxyethoxy)ethoxy]-1H-indole-2-carboxamide Isomer 3 (31.42 mg, 56.54 umol, 2.95% yield) was obtained as a white solid. MS (ESI) m/z 556.3 $[M+H]^+$.

$^1$H NMR (400 MHz, MeOD-$d_4$) δ=7.30 (d, J=0.9 Hz, 1H), 7.13 (d, J=7.7 Hz, 1H), 7.08-7.01 (m, 1H), 6.53 (d, J=7.3 Hz, 1H), 5.01 (s, 1H), 4.65 (s, 1H), 4.30-4.23 (m, 2H), 3.93 (dd, J=4.0, 5.3 Hz, 2H), 3.81-3.73 (m, 2H), 3.63-3.55 (m, 2H), 3.37 (s, 3H), 3.21 (br d, J=4.6 Hz, 2H), 2.49-2.37 (m, 1H), 2.34-2.23 (m, 1H), 1.97-1.88 (m, 2H), 1.87-1.63 (m, 4H), 1.58-1.45 (m, 1H), 1.02 (s, 9H).

Example 201. Synthesis of Viral Protease Inhibitor Compound 880

Step 1: methyl (Z)-2-azido-3-(2-chloro-3-methoxy-phenyl)prop-2-enoate

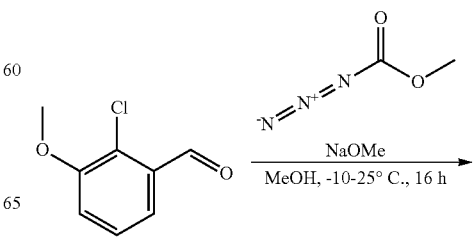

1239

-continued

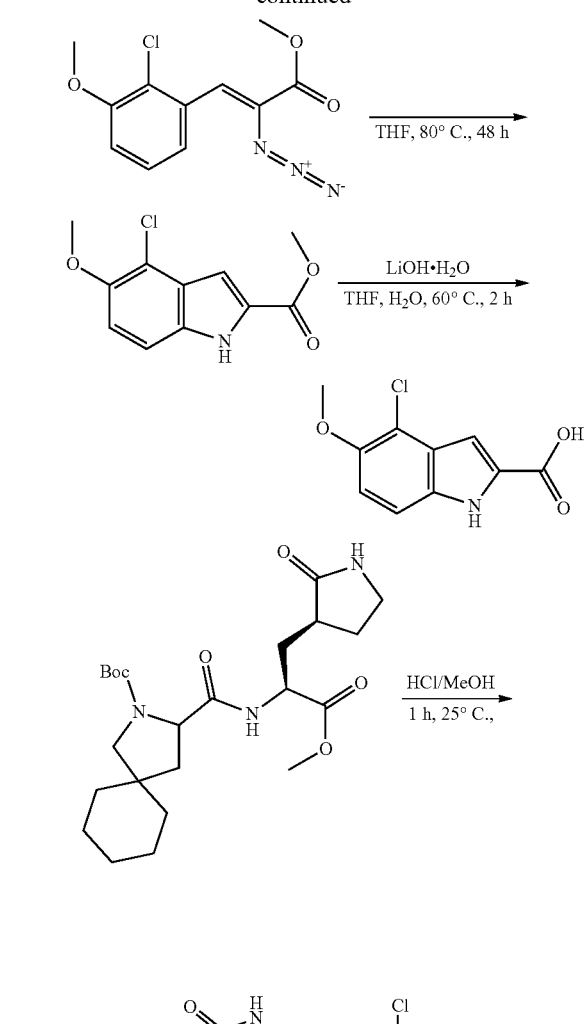

1240

-continued

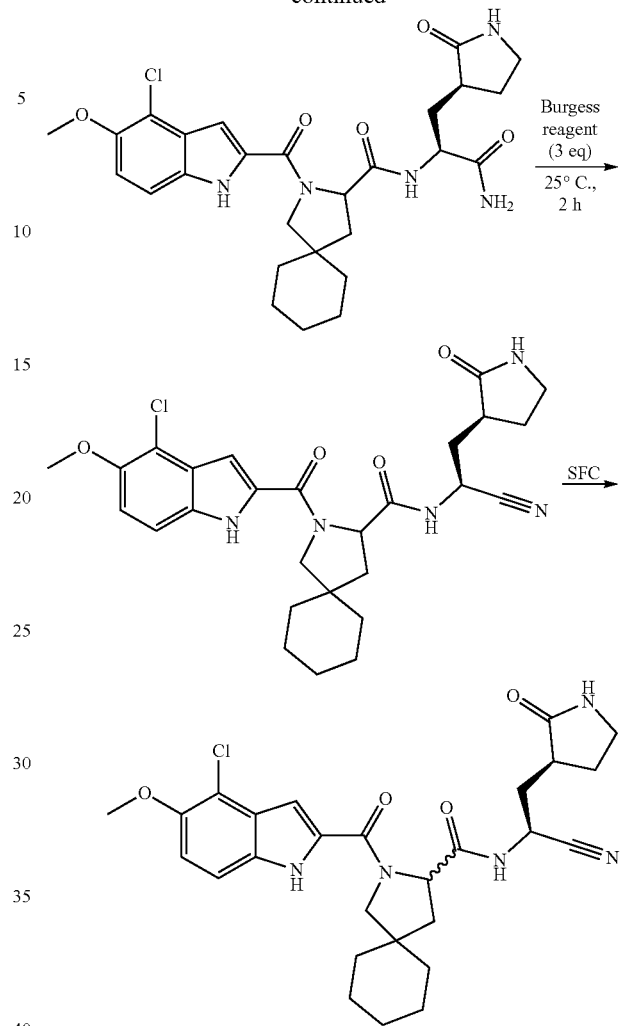

A mixture 2-chloro-3-methoxy-benzaldehyde (4 g, 23.45 mmol, 1 eq) and NaOMe (2.53 g, 46.90 mmol, 2 eq) with MeOH (20 mL) was cooled to −10° C., and then a mixture of methyl azide acetate (5.49 g, 46.90 mmol, 2 eq) in MeOH (50 mL) was added dropwise. The mixture was stirred at 25° C. for 16 h and white solid was observed. Upon completion, the reaction mixture was filtered to give the compound methyl (Z)-2-azido-3-(2-chloro-3-methoxy-phenyl)prop-2-enoate (3 g, 10.09 mmol, 43.02% yield, 90% purity) as a white solid. MS (ESI) m/z 267.0 [M+H]+

Step 2: methyl 4-chloro-5-methoxy-1H-indole-2-carboxylate

To a solution of methyl (Z)-2-azido-3-(2-chloro-3-methoxy-phenyl)prop-2-enoate (1 g, 3.74 mmol, 1 eq) in THF (30 mL) was added bis(trifluoromethylsulfonyloxy) iron (2.64 g, 7.47 mmol, 2 eq) and the mixture was stirred at 80° C. for 48 h. Upon completion, the reaction was concentrated in the vacuum and quenched by addition H₂O (100 mL) and then extracted with DCM (100 mL*3). The combined organic layers were washed with brine (100 mL), dried over Na₂SO₄, filtered and concentrated under reduced pressure and was purified by column chromatography (SiO₂, petroleum ether/ethyl acetate=10/1 to 5/1) to afford methyl

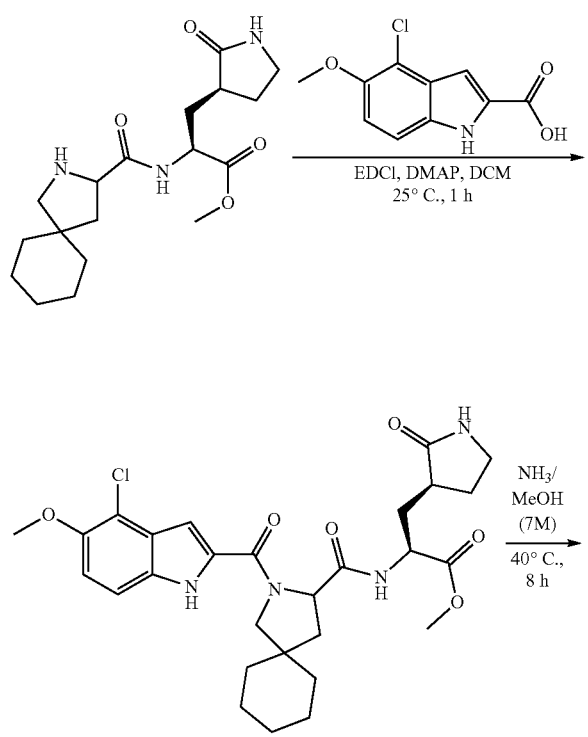

4-chloro-5-methoxy-1H-indole-2-carboxylate (140 mg, 584.17 umol, 15.64% yield) was a brown solid. MS (ESI) m/z 240.0 [M+H]+

Step 3: 4-chloro-5-methoxy-1H-indole-2-carboxylic acid

To a solution of methyl 4-chloro-5-methoxy-1H-indole-2-carboxylate (0.55 g, 2.29 mmol, 1 eq) in THF (5 mL), H$_2$O (2.5 mL) was added LiOH·H$_2$O (96.31 mg, 2.29 mmol, 1 eq), and the mixture was stirred at 60° C. for 2 h. Upon completion, the pH of the reaction mixture was adjusted to ~3 with HCl. The mixture was extracted with ethyl acetate (100 mL*3). The combined organic layer was dried over Na$_2$SO$_4$, filtered, concentrated to give 4-chloro-5-methoxy-1H-indole-2-carboxylic acid (340 mg, crude) as a brown solid. MS (ESI) m/z 226.0 [M+H]+

Step 4: (2S)-methyl 3-((S)-2-oxopyrrolidin-3-yl)-2-(2-azaspiro[4.5]decane-3-carboxamido)propanoate A solution of tert-butyl 3-(((S)-1-methoxy-1-oxo-3-((S)-2-oxopyrrolidin-3-yl)propan-2-yl)carbamoyl)-2-azaspiro[4.5]decane-2-carboxylate (1.3 g, 2.88 mmol, 1 eq) in HCl/MeOH (15 mL) was stirred for 1 h at 25° C. Upon completion, the mixture was quenched by the addition NaHCO$_3$ (200 mL) and then extracted with DCM (100 mL*3). The combined organic layers were washed with brine (100 mL), dried over Na$_2$SO$_4$, filtered and concentrated under reduced pressure to give a crude product (2S)-methyl 3-((S)-2-oxopyrrolidin-3-yl)-2-(2-azaspiro[4.5]decane-3-carboxamido)propanoate (1.1 g, crude) was yellow solid. MS (ESI) m/z 352.2 [M+H]+

Step 5: (2S)-methyl 2-(2-(4-chloro-5-methoxy-1H-indole-2-carbonyl)-2-azaspiro[4.5]decane-3-carboxamido)-3-((S)-2-oxopyrrolidin-3-yl)propanoate To a solution of (2S)-methyl 3-((S)-2-oxopyrrolidin-3-yl)-2-(2-azaspiro[4.5]decane-3-carboxamido)propanoate (934.56 mg, 2.66 mmol, 1 eq) in DCM (20 mL) was added 4-chloro-5-methoxy-1H-indole-2-carboxylic acid (600 mg, 2.66 mmol, 1 eq), EDCI (1.02 g, 5.32 mmol, 2 eq), and DMAP (974.62 mg, 7.98 mmol, 3 eq). After stirring the mixture at 25° C. for 1 h, the reaction was quenched by addition H$_2$O (200 mL) and then extracted with ethyl acetate (100 mL*3). The combined organic layers were washed with brine (100 mL), dried over Na$_2$SO$_4$, filtered and concentrated under reduced pressure and was purified by prep-TLC (SiO$_2$, DCM:MeOH=10:1) to afford (2S)-methyl 2-(2-(4-chloro-5-methoxy-1H-indole-2-carbonyl)-2-azaspiro[4.5]decane-3-carboxamido)-3-((S)-2-oxopyrrolidin-3-yl)propanoate (1.2 g, 1.93 mmol, 72.57% yield, 89.9% purity) as a yellow solid. MS (ESI) m/z 559.2 [M+H]+

Step 6: N-((S)-1-amino-1-oxo-3-((S)-2-oxopyrrolidin-3-yl)propan-2-yl)-2-(4-chloro-5-methoxy-1H-indole-2-carbonyl)-2-azaspiro[4.5]decane-3-carboxamide A solution of (2S)-methyl 2-(2-(4-chloro-5-methoxy-1H-indole-2-carbonyl)-2-azaspiro[4.5]decane-3-carboxamido)-3-((S)-2-oxopyrrolidin-3-yl)propanoate (1.2 g, 2.15 mmol, 1 eq) in NH$_3$ (in MeOH, 7 M, 30 mL, 97.83 eq) was stirred at 40° C. for 8 h. Upon completion, the reaction was concentrated in the vacuum to give crude product N-((S)-1-amino-1-oxo-3-((S)-2-oxopyrrolidin-3-yl)propan-2-yl)-2-(4-chloro-5-methoxy-1H-indole-2-carbonyl)-2-azaspiro[4.5]decane-3-carboxamide (1.15 g, crude) as a yellow solid. MS (ESI) m/z 544.2 [M+H]+

Step 7: (2S)-methyl 2-(2-(4-chloro-5-methoxy-1H-indole-2-carbonyl)-2-azaspiro[4.5]decane-3-carboxamido)-3-((S)-2-oxopyrrolidin-3-yl)propanoate To a solution of N-((S)-1-amino-1-oxo-3-((S)-2-oxopyrrolidin-3-yl)propan-2-yl)-2-(4-chloro-5-methoxy-1H-indole-2-carbonyl)-2-azaspiro[4.5]decane-3-carboxamide (1.15 g, 2.11 mmol, 1 eq) in DCM (20 mL) was added BURGESS REAGENT (1.51 g, 6.34 mmol, 3 eq), and the mixture was stirred at 25° C. for 2 h. Upon completion, the reaction was purified by prep-HPLC (column: Waters Xbridge C18 150*50 mm*10 um; mobile phase: [water (10 mM NH$_4$HCO$_3$)-ACN]; B %: 35%-65%, 10 min) to give 2-(4-chloro-5-methoxy-1H-indole-2-carbonyl)-N-((S)-1-cyano-2-((S)-2-oxopyrrolidin-3-yl)ethyl)-2-azaspiro[4.5]decane-3-carboxamide (400 mg, 760.42 umol, 35.97% yield) as a white solid. MS (ESI) m/z 526.2 [M+H]+

Step 8: (2S)-methyl 2-(2-(4-chloro-5-methoxy-1H-indole-2-carbonyl)-2-azaspiro[4.5]decane-3-carboxamido)-3-((S)-2-oxopyrrolidin-3-yl)propanoate 2-(4-chloro-5-methoxy-1H-indole-2-carbonyl)-N-((S)-1-cyano-2-((S)-2-oxopyrrolidin-3-yl)ethyl)-2-azaspiro[4.5]decane-3-carboxamide was separated by SFC (column: DAICEL CHIRALPAK AS (250 mm*30 mm, 10 um); mobile phase: [0.1% NH$_3$H$_2$O MEOH]; B %: 43%-43%, 8 min) to afford 2-(4-chloro-5-methoxy-1H-indole-2-carbonyl)-N-((S)-1-cyano-2-((S)-2-oxopyrrolidin-3-yl)ethyl)-2-azaspiro[4.5]decane-3-carboxamide (170 mg, 323.18 umol, 42.50% yield, 100% purity) as a white solid. MS (ESI) m/z 526.2 [M+H]+

$^1$H NMR (400 MHz, DMSO-d$_6$) δ=11.80-11.70 (m, 1H), 9.07-8.78 (m, 1H), 7.72-7.50 (m, 1H), 7.41-7.33 (m, 1H), 7.21-7.12 (m, 1H), 6.92-6.57 (m, 1H), 5.00-4.89 (m, 1H), 4.82-4.46 (m, 1H), 3.88-3.81 (m, 4H), 3.73-3.38 (m, 1H), 3.17-2.90 (m, 2H), 2.40-2.20 (m, 2H) 2.17-2.05 (m, 2H), 1.82-1.64 (m, 2H), 1.61-1.51 (m, 2H), 1.49-1.27 (m, 9H)

$^1$H NMR (400 MHz, DMSO-d$_6$) δ=11.52 (br s, 1H), 8.65 (br s, 1H), 7.40-7.39 (m, 2H), 7.16-7.13 (m, 1H), 6.86 (br s, 1H), 4.94 (br s, 1H), 4.59 (br s, 1H), 3.90-3.68 (m, 5H), 3.15-3.06 (m, 2H), 2.26-2.05 (m, 4H), 1.80 (br s, 1H), 1.68 (br s, 1H), 1.56-1.52 (m, 3H), 1.45-1.40 (m, 8H)

2-(4-chloro-5-methoxy-1H-indole-2-carbonyl)-N-((S)-1-cyano-2-((S)-2-oxopyrrolidin-3-yl)ethyl)-2-azaspiro[4.5]decane-3-carboxamide (170 mg, 323.18 umol, 42.50% yield, 100% purity) was obtained as white solid. MS (ESI) m/z 526.2 [M+H]+

$^1$H NMR (400 MHz, DMSO-d$_6$) δ=11.79-11.65 (m, 1H), 9.10-8.87 (m, 1H), 7.75-7.55 (m, 1H), 7.43-7.27 (m, 1H), 7.21-7.08 (m, 1H), 6.93-6.58 (m, 1H), 4.99-4.94 (m, 1H), 4.69-4.44 (m, 1H), 3.92-3.79 (m, 4H), 3.77-3.67 (m, 1H), 3.31-3.06 (m, 2H), 2.48-2.34 (m, 1H), 2.46-2.34 (m, 1H), 2.20-2.05 (m, 2H), 1.97-1.64 (m, 2H), 1.63-1.52 (m, 2H), 1.50-1.29 (m, 9H)

$^1$H NMR (400 MHz, DMSO-d$_6$) δ=11.52 (br s, 1H), 8.75 (br s, 1H), 7.57-7.34 (m, 2H), 7.15-7.13 (m, 1H), 6.84 (br s, 1H), 4.91 (br s, 1H), 4.61 (br s, 1H), 3.86-3.68 (m, 5H), 3.17-3.09 (m, 2H), 2.43-2.02 (m, 4H), 1.81 (br s, 1H), 1.67 (br s, 1H), 1.53 (br s, 3H), 1.45-1.41 (m, 8H)

Example 202. Synthesis of Viral Protease Inhibitor Compound 882

Step 1: methyl (2S)-2-(2-azaspiro[4.5]decane-3-carbonylamino)-3-[(3S-2-oxopyrrolidin-3-yl]propanoate

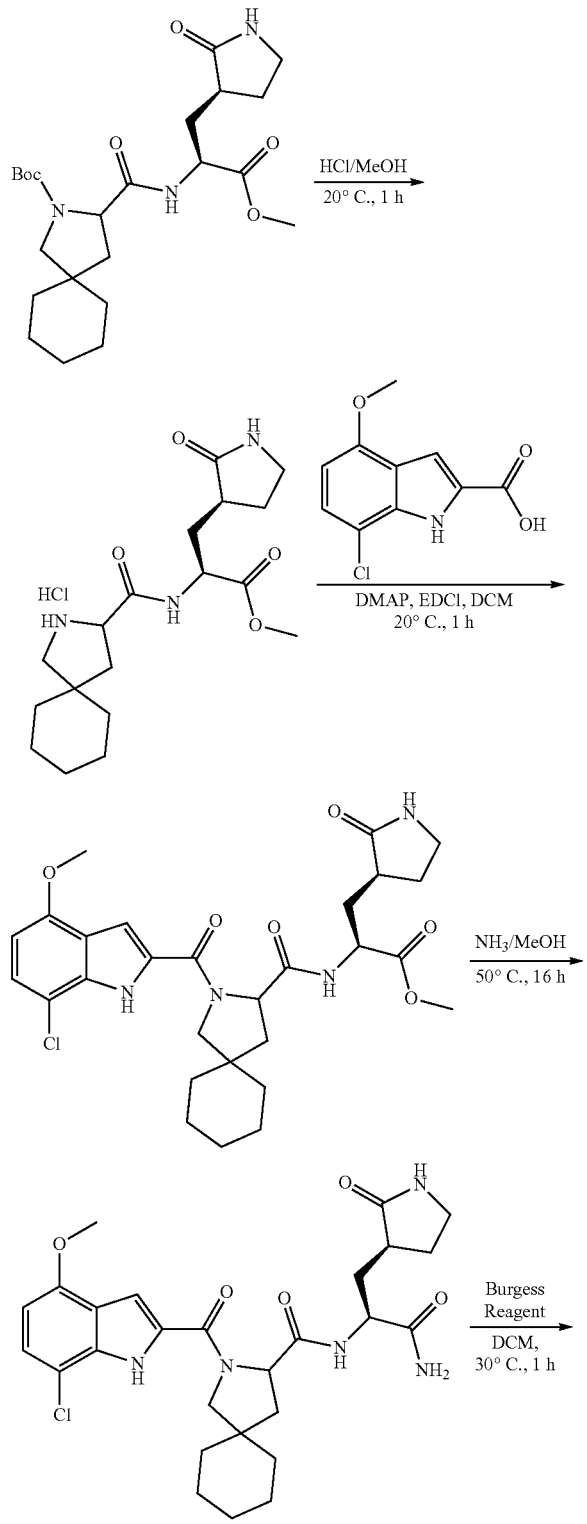

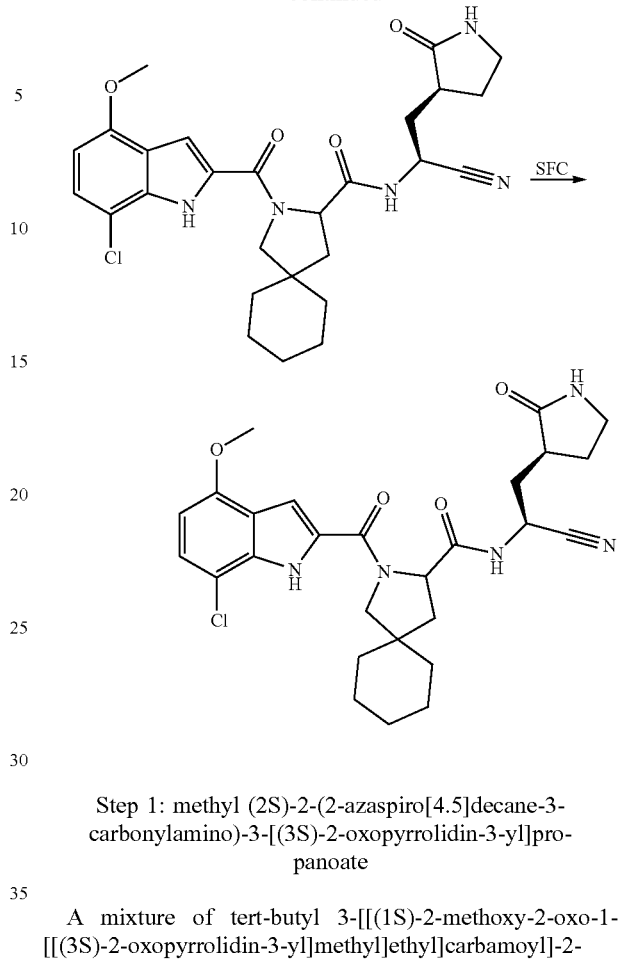

Step 1: methyl (2S)-2-(2-azaspiro[4.5]decane-3-carbonylamino)-3-[(3S)-2-oxopyrrolidin-3-yl]propanoate A mixture of tert-butyl 3-[[(1S)-2-methoxy-2-oxo-1-[[[(3S)-2-oxopyrrolidin-3-yl]methyl]ethyl]carbamoyl]-2-azaspiro[4.5]decane-2-carboxylate (1.5 g, 3.32 mmol, 1 eq) in HCl/MeOH (4 M, 20 mL, 24.08 eq) was stirred at 20° C. for 1 h. Upon completion, the mixture was concentrated under reduced pressure to give a residue, then was dissolved with DCM (30 mL*3) and concentrated under reduced pressure to get product methyl (2S)-2-(2-azaspiro[4.5]decane-3-carbonylamino)-3-[(3S)-2-oxopyrrolidin-3-yl]propanoate (1.29 g, crude, HCl) as a white oil MS (ESI) m/z 352.2 [M+H]$^+$.

Step 2: methyl (2S)-2-[[2-(7-chloro-4-methoxy-1H-indole-2-carbonyl)-2-azaspiro[4.5]decane-3-carbonyl]amino]-3-[(3S)-2-oxopyrrolidin-3-yl]propanoate To a mixture of methyl (2S)-2-(2-azaspiro[4.5]decane-3-carbonylamino)-3-[(3S)-2-oxopyrrolidin-3-yl]propanoate (1.24 g, 3.20 mmol, 1 eq, HCl) in DCM (15 mL) was added 7-chloro-4-methoxy-1H-indole-2-carboxylic acid (865.52 mg, 3.84 mmol, 1.2 eq), DMAP (976.35 mg, 7.99 mmol, 2.5 eq) and EDCI (1.23 g, 6.39 mmol, 2 eq). The resulting mixture was stirred at 20° C. for 1 h, and then the reaction mixture was diluted with water (50 mL) and extracted with DCM (30 mL*3). The combined organic layers were dried over Na$_2$SO$_4$, filtered and concentrated under reduced pressure to give a residue. The residue was purified by column (SiO$_2$, PE:EA=8/1~5/1) to afford methyl (2S)-2-[[2-(7-chloro-4-methoxy-1H-indole-2-carbonyl)-2-azaspiro[4.5]decane-carbonyl]amino]-3-[(3S)-2-oxopyrrolidin-3-yl]propanoate (1.6 g, 2.46 mmol, 77.00% yield, 86% purity) as a yellow oil. MS (ESI) m/z 559.3 [M+H]$^+$.

Step 3: N-[(1S)-2-amino-2-oxo-1-[[(3S)-2-oxopyr-rolidin-3-yl]methyl]ethyl]-2-(7-chloro-4-methoxy-1H-indole-2-carbonyl)-2-azaspiro[4.5]decane-3-carboxamide A mixture of methyl (2S)-2-[[2-(7-chloro-4-methoxy-1H-indole-2-carbonyl)-2-azaspiro[4.5]decane-3-carbonyl]amino]-3-[(3S)-2-oxopyrrolidin-3-yl]propanoate (400 mg, 4 batches in parallel, 615.33 umol, 86% purity, 1 eq) in $NH_3$/MeOH (7 M, 20 mL, 227.52 eq) was stirred at 50° C. for 16 h. Upon completion, the mixture was concentrated under reduced pressure to give a residue, then was dissolved with DCM (10 mL*3) and concentrated under reduced pressure to get the product N-[(1S)-2-amino-2-oxo-1-[[(3S)-2-oxopyrrolidin-3-yl]methyl]ethyl]-2-(7-chloro-4-methoxy-1H-indole-2-carbonyl)-2-azaspiro[4.5]decane-3-carboxamide (1.3 g, crude) as yellow solid. MS (ESI) m/z 544.3 [M+H]$^+$.

Step 4: 2-(7-chloro-4-methoxy-1H-indole-2-carbo-nyl)-N-[(1S)-1-cyano-2-[(3S)-2-oxopyrrolidin-3-yl]ethyl]-2-azaspiro[4.5]decane-3-carboxamide To a mixture of N-[(1S)-2-amino-2-oxo-1-[[(3S)-2-oxopyrrolidin-3-yl]methyl]ethyl]-2-(7-chloro-4-methoxy-1H-indole-2-carbonyl)-2-azaspiro[4.5]decane-3-carboxamide (1.2 g, 2.21 mmol, 1 eq) in DCM (15 mL) was added BURGESS REAGENT (1.58 g, 6.62 mmol, 3 eq). After stirring at 30° C. for 1 h, the mixture was quenched with water (1 mL) and dried with using $N_2$. The residue was purified by prep-HPLC (column: Waters X bridge C18 150*50 mm*10 um; mobile phase: [water (10 mM $NH_4HCO_3$)-ACN]; B %: 35%-65%, 10 min), which was further separated by SFC (column: DAICEL CHIRALPAK IC (250 mm*30 mm, 10 um); mobile phase: [Neu-IPA]; B %: 60%-60%, 9 min) to afford 2-(7-chloro-4-methoxy-1H-indole-2-carbonyl)-N-[(1S)-1-cyano-2-[(3S)-2-oxopyrroli-din-3-yl]ethyl]-2-azaspiro[4.5]decane-3-carboxamide Isomer 1 (378.42 mg, 719.39 umol, 32.62% yield, 100% purity) as a white solid. MS (ESI) m/z 526.2 [M+H]$^+$.

$^1$H NMR (400 MHz, MeOD-d$_4$) δ=7.20-7.13 (m, 1H), 7.11 (s, 1H), 6.59-6.42 (m, 1H), 5.11-5.02 (m, 1H), 4.80-4.58 (m, 1H), 3.99-3.89 (m, 3H), 3.89-3.82 (m, 1H), 3.77-3.38 (m, 1H), 3.28 (br s, 1H), 2.99-2.66 (m, 1H), 2.52-2.25 (m, 3H), 2.17-1.69 (m, 3H), 1.65-1.26 (m, 1H).

2-(7-Chloro-4-methoxy-1H-indole-2-carbonyl)-N-[(1S)-1-cyano-2-[(3S)-2-oxopyrrolidin-3-yl]ethyl]-2-azaspiro [4.5]decane-3-carboxamide Isomer 2 (367.22 mg, 698.10 umol, 31.65% yield, 100% purity) was obtained as a white solid. MS (ESI) m/z 526.2 [M+H]$^+$.

$^1$H NMR (400 MHz, MeOD-d$_4$) δ=7.18 (d, J=8.2 Hz, 1H), 7.14 (s, 1H), 6.54 (d, J=8.3 Hz, 1H), 5.03 (dd, J=6.0, 10.1 Hz, 1H), 4.63 (dd, J=7.8, 9.7 Hz, 1H), 3.99-3.88 (m, 4H), 3.76 (d, J=10.3 Hz, 1H), 3.30-3.23 (m, 1H), 2.53-2.40 (m, 1H), 2.39-1.96 (m, 3H), 1.95-1.70 (m, 3H), 1.68-1.38 (m, 1H).

Example 203. Synthesis of Viral Protease Inhibitor Compound 886

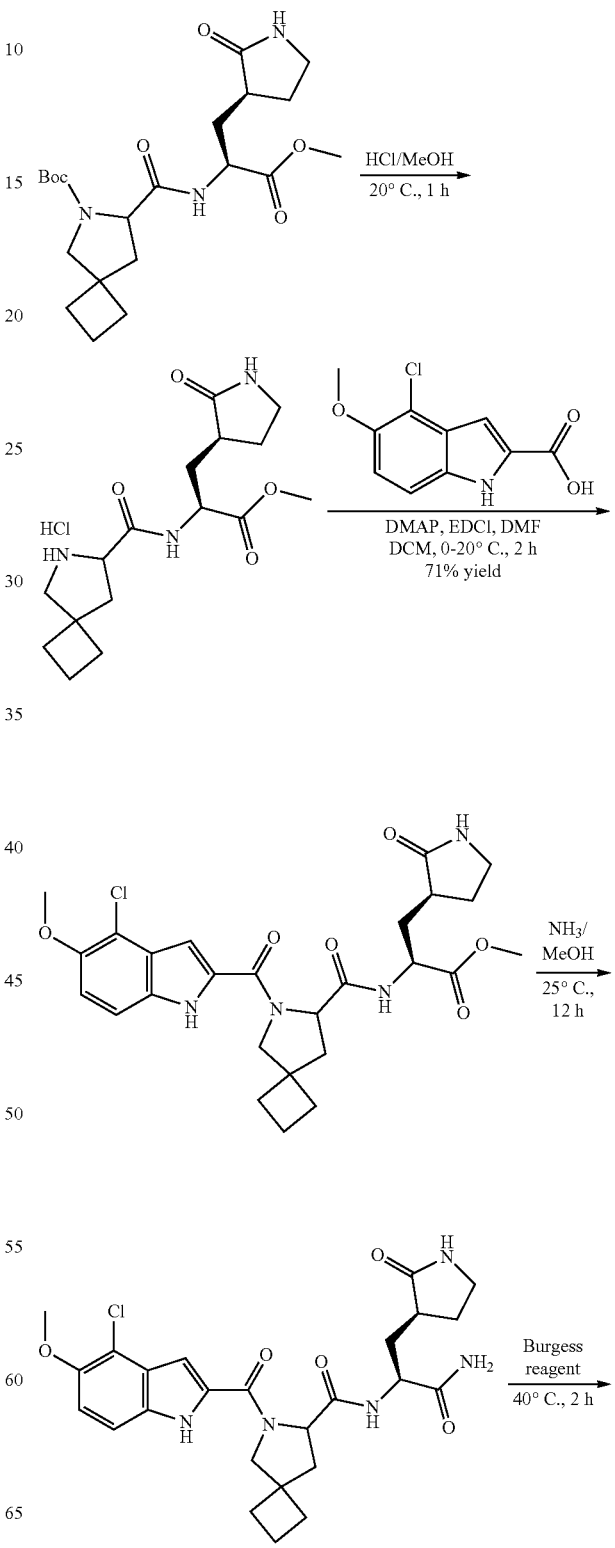

-continued

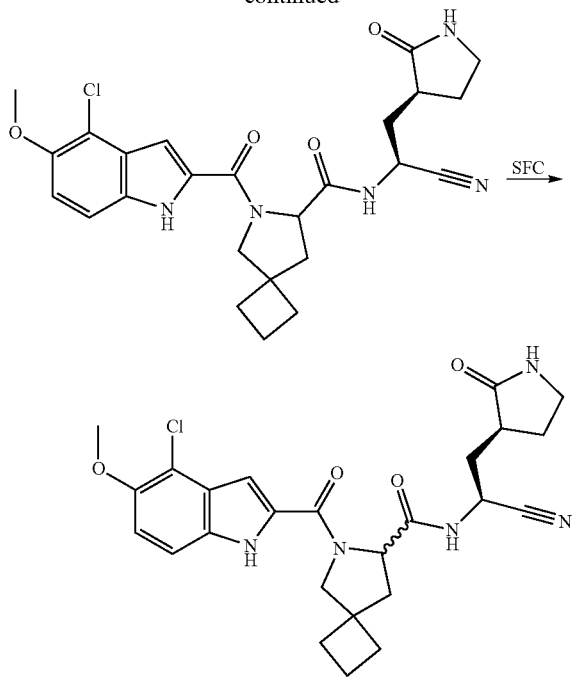

A solution of tert-butyl 7-[[(1S)-2-methoxy-2-oxo-1-[[(3S)-2-oxopyrrolidin-3-yl]methyl]ethyl]carbamoyl]-6-azaspiro[3.4]octane-6-carboxylate (1.5 g, 3.54 mmol, 1 eq) in HCl/MeOH (4 M, 37.50 mL, 42.35 eq) was stirred at 20° C. for 1 h. Upon completion, the reaction mixture was concentrated under reduced pressure to give the product methyl (2S)-2-(6-azaspiro[3.4]octane-7-carbonylamino)-3-[(3S)-2-oxopyrrolidin-3-yl]propanoate (1.2 g, crude, HCl) as a white solid.

Step 2. (2S)-methyl 2-(6-(4-chloro-5-methoxy-1H-indole-2-carbonyl)-6-azaspiro[3.4]octane-7-carboxamido)-3-((S)-2-oxopyrrolidin-3 yl)propanoate To a solution of methyl (2S)-2-(6-azaspiro[3.4]octane-7-carbonylamino)-3-[(3S)-2-oxopyrrolidin-3-yl]propanoate (1.1 g, 3.06 mmol, 1 eq, HCl) and 4-chloro-5-methoxy-1H-indole-2-carboxylic acid (700 mg, 3.10 mmol, 1.01 eq) in DMF (7 mL) and DCM (30 mL) at 0° C. was added DMAP (1.12 g, 9.17 mmol, 3 eq) and EDCI (1.17 g, 6.11 mmol, 2 eq), and then the mixture was stirred at 20° C. for 2 h. Upon completion, the reaction mixture was quenched by addition H₂O 100 mL at 0° C., and then extracted with DCM (50 mL*3). The combined organic layers were washed with brine 50 mL, dried over Na₂SO₄, filtered and concentrated under reduced pressure to give a residue. The residue was purified by column chromatography (SiO₂, petroleum ether: ethyl acetate=5:1 to 0:1) to give methyl (2S)-2-[[6-(4-chloro-5-methoxy-1H-indole-2-carbonyl)-6-azaspiro[3.4]octane-7-carbonyl]amino]-3-[(3S)-2-oxopyrrolidin-3-yl]propanoate (1.2 g, 2.19 mmol, 71.71% yield, 97% purity) as a yellow solid. MS (ESI) m/z 531.2 [M+H]⁺.

Step 3: N-((S)-1-amino-1-oxo-3-((S)-2-oxopyrrolidin-3-yl)propan-2-yl)-6-(4-chloro-5-methoxy-1H-indole-2-carbonyl)-6-azaspiro[3.4]octane-7-carboxamide A solution of methyl (2S)-2-[[6-(4-chloro-5-methoxy-1H-indole-2-carbonyl)-6-azaspiro[3.4]octane-7-carbonyl]amino]-3-[(3S)-2-oxopyrrolidin-3-yl]propanoate (1.2 g, 2.26 mmol, 1 eq) in NH₃/MeOH (7 M, 50 mL, 154.87 eq) was stirred at 25° C. for 12 h. Upon completion, the reaction mixture was concentrated under reduced pressure to give N-[(1S)-2-amino-2-oxo-1-[[(3S)-2-oxopyrrolidin-3-yl]methyl]ethyl]-6-(4-chloro-5-methoxy-1H-indole-2-carbonyl)-6-azaspiro[3.4]octane-7-carboxamide (1.1 g, crude) as a yellow solid. MS (ESI) m/z 516.2 [M+H]⁺.

Step 4: 6-(4-chloro-5-methoxy-1H-indole-2-carbonyl)-N-((S)-1-cyano-2-((S)-2-oxopyrrolidin-3-yl)ethyl)-6-azaspiro[3.4]octane-7-carboxamide To a solution of N-[(1S)-2-amino-2-oxo-1-[[(3S)-2-oxopyrrolidin-3-yl]methyl]ethyl]-6-(4-chloro-5-methoxy-1H-indole-2-carbonyl)-6-azaspiro[3.4]octane-7-carboxamide (1.1 g, 2.13 mmol, 1 eq) in DCM (40 mL) was added BURGESS REAGENT (1.27 g, 5.33 mmol, 2.5 eq), and then the mixture was stirred at 40° C. for 2 h. Upon completion, the reaction mixture was concentrated under reduced pressure to give a residue. The residue was purified by prep-HPLC (column: Phenomenex Titank C18 Bulk 250*70 mm 10 u; mobile phase: [water (10 mM NH₄HCO₃)-ACN]; B %: 6%-36%, 20 min) to give desired compound (500 mg, 47% yield, 99% purity) as a white solid, which was further separated by SFC (column: DAICEL CHIRALPAK AS (250 mm*30 mm, 10 um); mobile phase: [Neu-MeOH]; B %: 55%-55%, 7 min) to afford 6-(4-chloro-5-methoxy-1H-indole-2-carbonyl)-N-[(1S)-1-cyano-2-[(3S)-2-oxopyrrolidin-3-yl]ethyl]-6-azaspiro[3.4]octane-7-carboxamide Isomer 1 (232.45 mg, 466.79 umol, 21.90% yield, 100% purity) as a white solid. MS (ESI) m/z 498.2 [M+H]⁺.

¹H NMR (400 MHz, DMSO-d₆) δ=11.85-11.68 (m, 1H), 9.09-8.67 (m, 1H), 7.74-7.42 (m, 1H), 7.42-7.32 (m, 1H), 7.21-7.10 (m, 1H), 7.01-6.46 (m, 1H), 5.02-4.40 (m, 2H), 4.11-3.65 (m, 5H), 3.20-2.90 (m, 2H), 2.36-1.63 (m, 13H)

6-(4-Chloro-5-methoxy-1H-indole-2-carbonyl)-N-[(1S)-1-cyano-2-[(3S)-2-oxopyrrolidin-3-yl]ethyl]-6-azaspiro[3.4]octane-7-carboxamide Isomer 2 (232.89 mg, 467.68 umol, 21.94% yield, 100% purity) was obtained as a white solid. MS (ESI) m/z 498.2 [M+H]⁺.

¹H NMR (400 MHz, DMSO-d₆) δ=11.79-11.70 (m, 1H), 9.19-8.76 (m, 1H), 7.76-7.60 (m, 1H), 7.42-7.29 (m, 1H), 7.20-7.08 (m, 1H), 6.96-6.48 (m, 1H), 5.04-4.37 (m, 2H), 4.05-3.78 (m, 5H), 3.18-2.92 (m, 2H), 2.43-1.79 (m, 13H)

Example 204. Synthesis of Viral Protease Inhibitor Compound 888

Step 1: methyl (2S)-2-amino-3-[(3S)-2-oxopyrrolidin-3-yl]propanoate

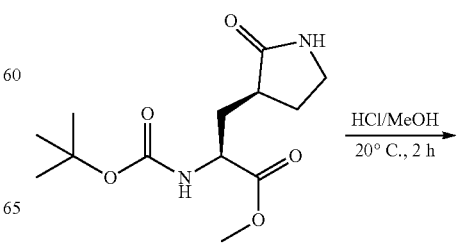

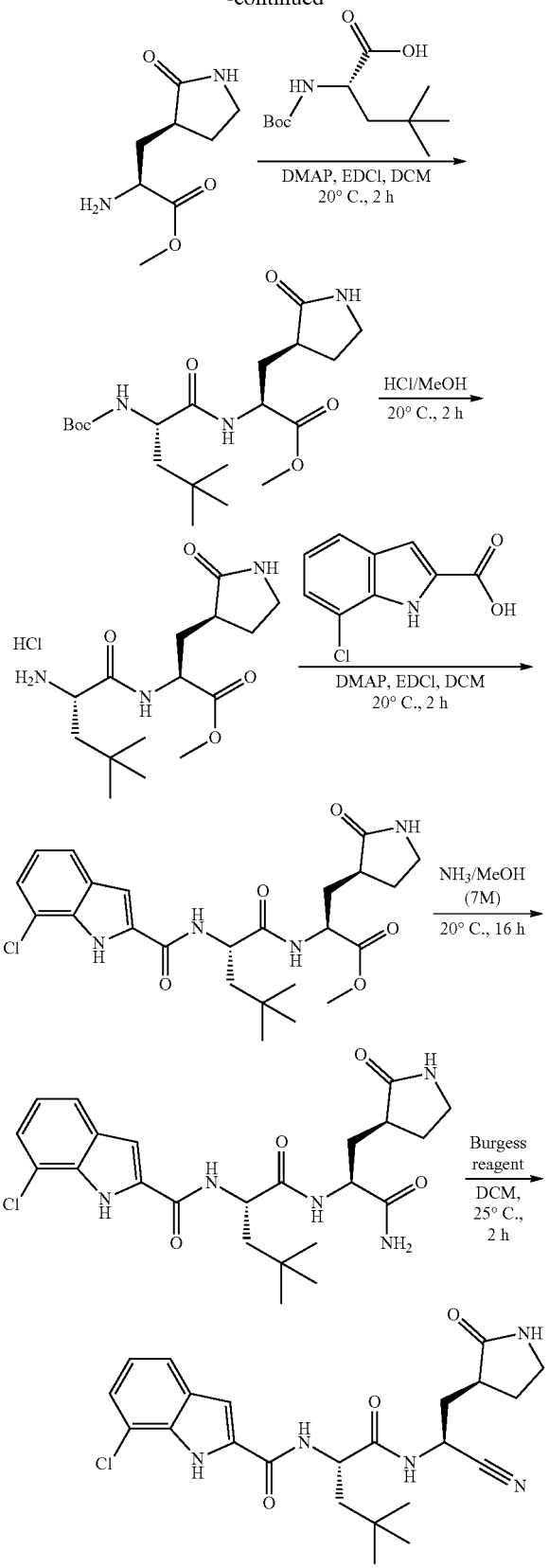

A solution of methyl (2S)-2-(tert-butoxycarbonylamino)-3-[(3S)-2-oxopyrrolidin-3-yl]propanoate (20 g, 69.85 mmol, 1 eq) in HCl/MeOH (200 mL) was stirred at 20° C. for 2 h. Upon completion, the reaction mixture was concentrated under reduced pressure to remove solvent to give methyl (2S)-2-amino-3-[(3S)-2-oxopyrrolidin-3-yl]propanoate (13 g, crude, HCl) as a white solid. MS (ESI) m/z 187.1 [M+H]+

Step 2: methyl (2S)-2-[[(2S)-2-(tert-butoxycarbonylamino)-4,4-dimethyl-pentanoyl]amino]-3-[(3S)-2-oxopyrrolidin-3-yl]propanoate To a solution of methyl (2S)-2-amino-3-[(3S)-2-oxopyrrolidin-3-yl]propanoate (13 g, 58.38 mmol, 1 eq, HCl) and (2S)-2-(tert-butoxycarbonylamino)-4,4-dimethyl-pentanoic acid (14.32 g, 58.38 mmol, 1 eq) in DCM (200 mL) was added DMAP (21.40 g, 175.15 mmol, 3 eq), and then EDCI (33.58 g, 175.15 mmol, 3 eq) was added. The mixture was stirred at 20° C. for 2 h. Upon completion, the reaction mixture was quenched by addition H$_2$O 100 mL, and then extracted with DCM 100 mL (50 mL*2). The combined organic layers were washed with HCl (1 M) 100 mL (50 mL*2), then were washed with brine 100 mL, dried over Na$_2$SO$_4$, filtered and concentrated under reduced pressure to give a residue. The residue was purified by column chromatography (SiO$_2$, petroleum ether/ethyl acetate=3/1 to 0/1) to give methyl (2S)-2-[[(2S)-2-(tert-butoxycarbonylamino)-4,4-dimethyl-pentanoyl]amino]-3-[(3S)-2-oxopyrrolidin-3-yl]propanoate (23 g, 50.62 mmol, 86.70% yield, 91% purity) as a white solid. MS (ESI) m/z 414.3 [M+H]+

Step 3: methyl (2S)-2-[[(2S)-2-amino-4,4-dimethyl-pentanoyl]amino]-3-[(3S)-2-oxopyrrolidin-3-yl]propanoate A solution of methyl (2S)-2-[[(2S)-2-(tert-butoxycarbonylamino)-4,4-dimethyl-pentanoyl]amino]-3-[(3S)-2-oxopyrrolidin-3-yl]propanoate (23 g, 55.62 mmol, 1 eq) in HCl/MeOH (200 mL) was stirred at 20° C. for 2 h. Upon completion, the reaction mixture was concentrated under reduced pressure to remove solvent to give methyl (2S)-2-[[(2S)-2-amino-4,4-dimethyl-pentanoyl]amino]-3-[(3S)-2-oxopyrrolidin-3-yl]propanoate (19 g, crude, HCl) as a yellow solid. MS (ESI) m/z 314.2 [M+H]+

Step 4: methyl (2S)-2-[[(2S)-2-[(7-chloro-1H-indole-2-carbonyl)amino]-4,4-dimethyl-pentanoyl]amino]-3-[(3S)-2-oxopyrrolidin-3-yl]propanoate A solution of methyl (2S)-2-[[(2S)-2-amino-4,4-dimethyl-pentanoyl]amino]-3-[(3S)-2-oxopyrrolidin-3-yl]propanoate (1 g, 2.86 mmol, 1 eq, HCl) and 7-chloro-1H-indole-2-carboxylic acid (559.10 mg, 2.86 mmol, 1 eq) in DCM (40 mL) was added with DMAP (1.05 g, 8.58 mmol, 3 eq). After the addition of EDCI (1.64 g, 8.58 mmol, 3 eq), the resulting mixture was stirred at 20° C. for 2 h. Upon completion, the reaction mixture was quenched by addition H$_2$O (30 mL), and then extracted with DCM 40 mL (20 mL*2). The combined organic layers were washed with HCl (1M) 30 mL (15 mL*2), the combined organic layers were washed with brine (40 mL), dried over Na$_2$SO$_4$, filtered and concentrated under reduced pressure to give a residue. The residue was purified by column chromatography (SiO$_2$, petroleum ether/ethyl acetate=3/1 to 0/1) to afford methyl (2S)-2-[[(2S)-2-[(7-chloro-1H-indole-2-carbonyl)amino]-4,4-dimethyl-pentanoyl]amino]-3-[(3S)-2-oxopyrrolidin-3-yl]propanoate (930 mg, 1.84 mmol, 64.28% yield, 97% purity) as a white solid. MS (ESI) m/z 491.2 [M+H]+.

Step 5: N-[(1S)-1-[[(1S)-2-amino-2-oxo-1-[[(3S)-2-oxopyrrolidin-3-yl]methyl]ethyl]carbamoyl]-3,3-dimethyl-butyl]-7-chloro-1H-indole-2-carboxamide A solution of methyl (2S)-2-[[(2S)-2-[(7-chloro-1H-indole-2-carbonyl)amino]-4,4-dimethyl-pentanoyl]amino]-3-[(3S)-2-oxopyrrolidin-3-yl]propanoate (900 mg, 1.83 mmol, 1 eq) in NH$_3$/MeOH (7 M, 30 mL, 114.56 eq) was stirred at 20° C. for 16 h. Upon completion, the reaction mixture was concentrated under reduced pressure to remove solvent to give N-[(1S)-1-[[(1S)-2-amino-2-oxo-1-[[(3S)-2-oxopyrrolidin-3-yl]methyl]ethyl]carbamoyl]-3,3-dimethyl-butyl]-7-chloro-1H-indole-2-carboxamide (770 mg, crude) as a white solid. MS (ESI) m/z 476.2 [M+H]$^+$.

Step 6: 7-chloro-N-[(1S)-1-[[(1S)-1-cyano-2-[(3S)-2-oxopyrrolidin-3-yl]ethyl]carbamoyl]-3,3-dimethyl-butyl]-1H-indole-2-carboxamide To a solution of N-[(1S)-1-[[(1S)-2-amino-2-oxo-1-[[(3S)-2-oxopyrrolidin-3-yl]methyl]ethyl]carbamoyl]-3,3-dimethyl-butyl]-7-chloro-1H-indole-2-carboxamide (760 mg, 1.60 mmol, 1 eq) in DCM (15 mL) was added Burgess reagent (761.03 mg, 3.19 mmol, 2 eq). The mixture was stirred at 25° C. for 2 h, and then the reaction mixture was concentrated under reduced pressure to remove solvent. The residue was purified by prep-HPLC (column: Waters Xbridge C18 150*50 mm*10 um; mobile phase: [water (10 mM NH$_4$HCO$_3$)-ACN]; B %: 35%-55%, 10 min) to give 7-chloro-N-[(1S)-1-[[(1S)-1-cyano-2-[(3S)-2-oxopyrrolidin-3-yl]ethyl]carbamoyl]-3,3-dimethyl-butyl]-1H-indole-2-carboxamide (421 mg, 919.31 umol, 57.57% yield, 100% purity) as a white solid. MS (ESI) m/z 458.2 [M+H]$^+$.

1H NMR (400 MHz, DMSO-d$_6$) δ=11.70 (s, 1H), 9.01 (d, J=7.8 Hz, 1H), 8.72 (d, J=8.1 Hz, 1H), 7.74-7.58 (m, 2H), 7.37-7.22 (m, 2H), 7.07 (t, J=7.8 Hz, 1H), 4.98 (q, J=7.8 Hz, 1H), 4.65-4.52 (m, 1H), 3.19-3.03 (m, 2H), 2.42-2.27 (m, 1H), 2.20-2.06 (m, 2H), 1.82 (d, J=7.4 Hz, 1H), 1.75-1.64 (m, 3H), 0.95 (s, 9H).

Example 205. Synthesis of Viral Protease Inhibitor Compound 898

Step 1: (S)-methyl 2-((S)-2-amino-3-cyclopropylpropanamido)-3-((S)-2-oxopiperidin-3-yl)propanoate hydrochloride

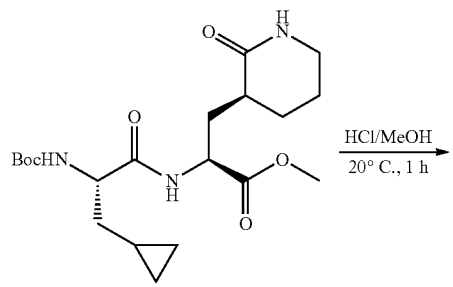

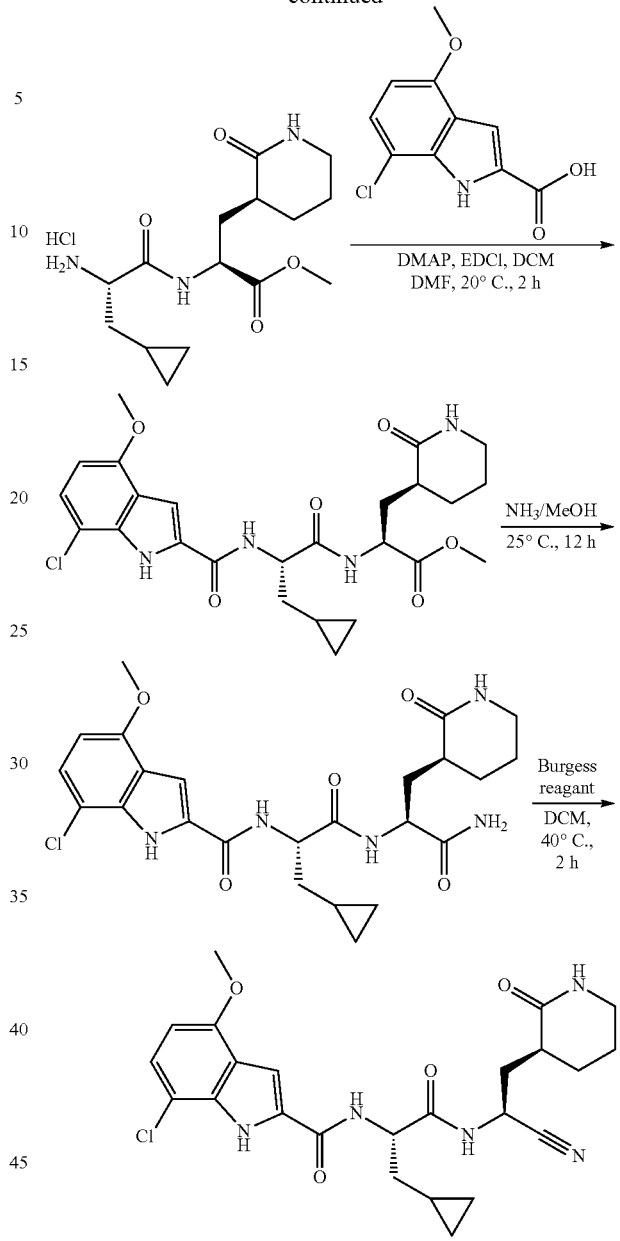

A solution of methyl (2S)-2-[[(2S)-2-(tert-butoxycarbonylamino)-3-cyclopropyl-propanoyl]amino]-3-(3S)-2-oxo-3-piperidyl]propanoate (23 g, 55.89 mmol, 1 eq) in HCl/MeOH (4 M, 230 mL, 16.46 eq) was stirred at 20° C. for 1 h. Upon completion, the reaction mixture was concentrated under reduced pressure to give the produce methyl (2S)-2-[[(2S)-2-amino-3-cyclopropyl-propanoyl]amino]-3 [(3 S)-2-oxo-3-piperidyl]propanoate (20 g, crude, HCl) as a white solid. MS (ESI) m/z 312.1 [M+H]$^+$.

Step 2: (S)-methyl 2-((S)-2-(7-chloro-4-methoxy-1H-indole-2-carboxamido)-3-cyclopropylpropanamido)-3-((S)-2-oxopiperidin-3-yl)propanoate To a solution of methyl (2S)-2-[[(2S)-2-amino-3-cyclopropyl-propanoyl]amino]-3-[(3S)-2-oxo-3-piperidyl]propanoate (0.8 g, 2.30 mmol, 1 eq, HCl) and 7-chloro-4-methoxy-1H-indole-2-carboxylic acid (622.71 mg, 2.76 mmol, 1.2 eq) in DMF (5 mL) and DCM (20 mL) was added DMAP (842.95 mg, 6.90 mmol, 3 eq) and EDCI (881.79 mg, 4.60 mmol, 2 eq), and then the mixture was stirred at 20° C. for 2 h. Upon completion, the reaction mixture was quenched by the addition of H₂O (100 mL) at 0° C., and then extracted with DCM (50 mL*3). The combined organic layers were washed with brine (50 mL), dried over Na₂SO₄, filtered and concentrated under reduced pressure to give a residue. The residue was purified by column chromatography (SiO₂, petroleum ether:ethyl acetate=5:1 to 0:1) to give the product methyl (2S)-2-[[(2S)-2-[(7-chloro-4-methoxy-1H-indole-2-carbonyl)amino]-3-cyclopropyl-propanoyl]amino]-3-[(3S)-2-oxo-3-piperidyl]propanoate (1 g, 1.83 mmol, 79.59% yield, 95% purity) as a yellow solid. MS (ESI) m/z 519.2 [M+H]⁺.

Step 3: N-((S)-1-(((S)-1-amino-1-oxo-3-((S)-2-oxopiperidin-3-yl)propan-2-yl)amino)-3-cyclopropyl-1-oxopropan-2-yl)-7-chloro-4-methoxy-1H-indole-2-carboxamide A solution of methyl (2S)-2-[[(2S)-2-[(7-chloro-4-methoxy-1H-indole-2-carbonyl)amino]-3-cyclopropyl-propanoyl]amino]-3-[(3S)-2-oxo-3-piperidyl]propanoate (0.9 g, 1.73 mmol, 1 eq) in NH₃/MeOH (7 M, 36.00 mL, 145.32 eq) was stirred at 25° C. for 12 h. Upon completion, the reaction mixture was concentrated under reduced pressure to afford N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-4-methoxy-1H-indole-2-carboxamide (0.8 g, crude) as a yellow solid. MS (ESI) m/z 504.2 [M+H]⁺.

Step 4: 7-chloro-N-((S)-1-(((S)-1-cyano-2-((S)-2-oxopiperidin-3-yl)ethyl)amino)-3-cyclopropyl-1-oxopropan-2-yl)-4-methoxy-1H-indole-2-carboxamide A solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-4-methoxy-1H-indole-2-carboxamide (0.8 g, 1.59 mmol, 1 eq) in DCM (30 mL) was added with Burgess reagent (945.70 mg, 3.97 mmol, 2.5 eq), and then the mixture was stirred at 40° C. for 2 h. Upon completion, the reaction mixture was concentrated under reduced pressure to give a residue. The residue was purified by prep-HPLC (column: Phenomenex Gemini C18 250*50 mm*10 um; mobile phase: [water (10 mM NH₄HCO₃)-ACN]; B %: 28%-48%, 20 min) to give the product 7-chloro-N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide (0.21 g, 432.13 umol, 27.22% yield, 100% purity) as a white solid. MS (ESI) m/z 486.2 [M+H]⁺.

¹H NMR (400 MHz, DMSO-d₆) δ=11.70 (br d, J=1.6 Hz, 1H), 8.97 (d, J=7.9 Hz, 1H), 8.65 (d, J=7.5 Hz, 1H), 7.53 (br s, 1H), 7.28 (s, 1H), 7.21 (d, J=8.3 Hz, 1H), 6.56 (d, J=8.3 Hz, 1H), 5.07 (q, J=7.8 Hz, 1H), 4.56-4.43 (m, 1H), 3.89 (s, 3H), 3.15-3.02 (m, 2H), 2.30-2.22 (m, 2H), 1.87-1.68 (m, 4H), 1.59-1.39 (br s, 3H), 0.86-0.77 (m, 1H), 0.48-0.38 (m, 2H), 0.23-0.08 (m, 2H)

Example 206. Synthesis of Viral Protease Inhibitor Compound 902

Step 1: (Z)-ethyl 3-bromo-2-(hydroxyimino)propanoate

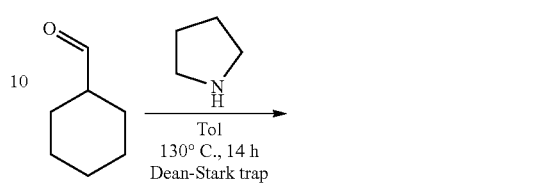

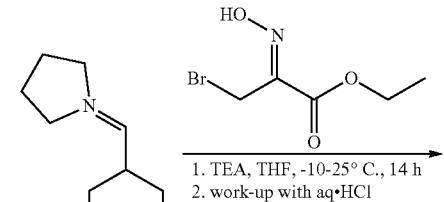

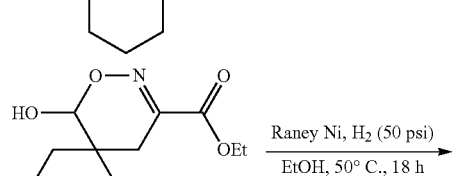

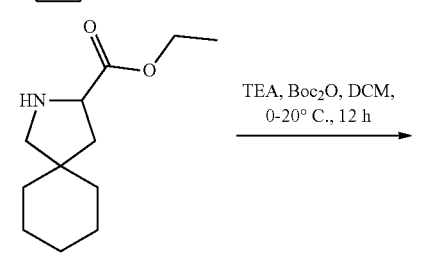

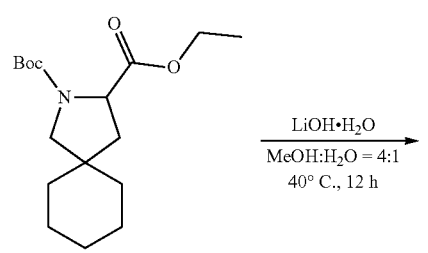

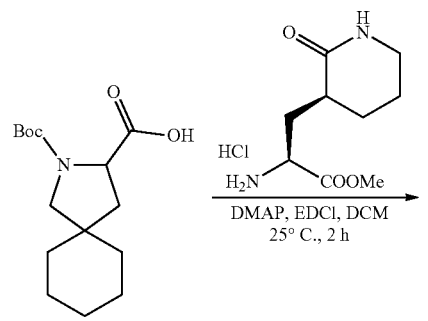

1255

-continued

1256

-continued

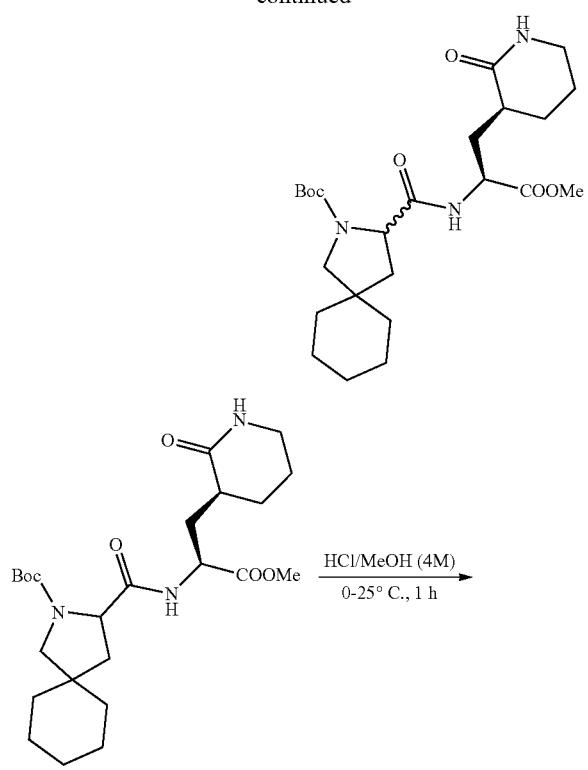

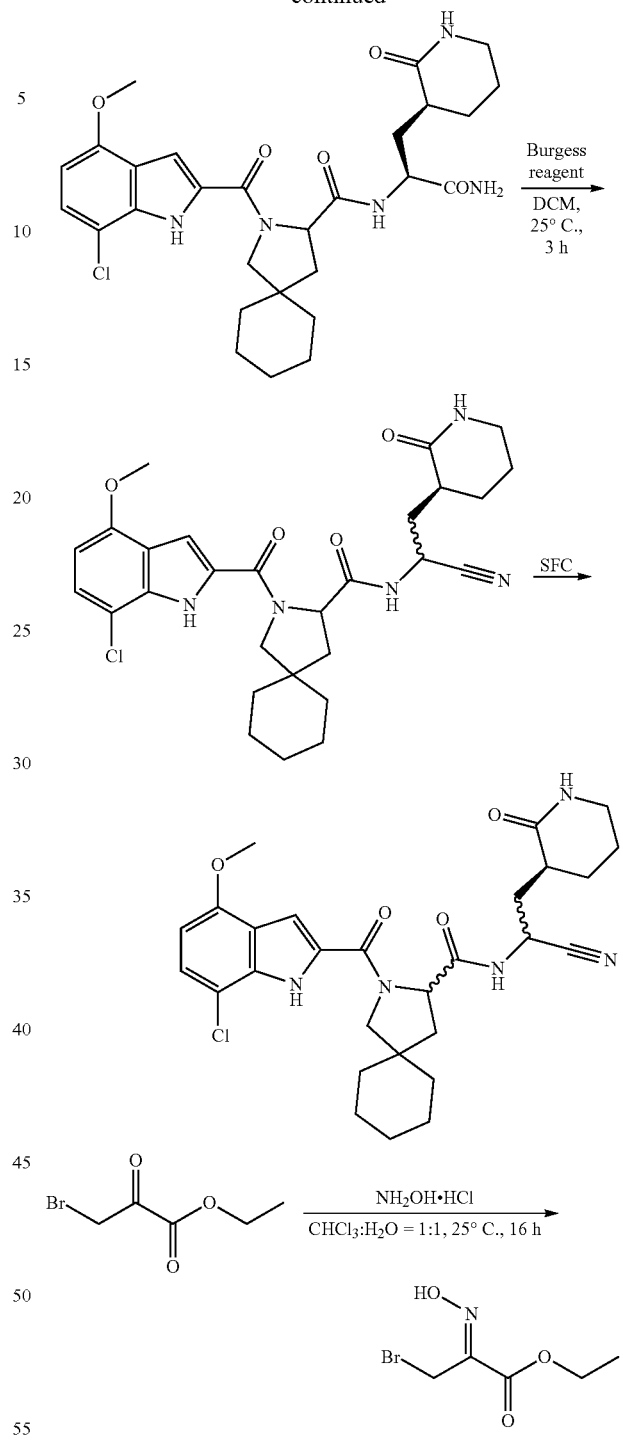

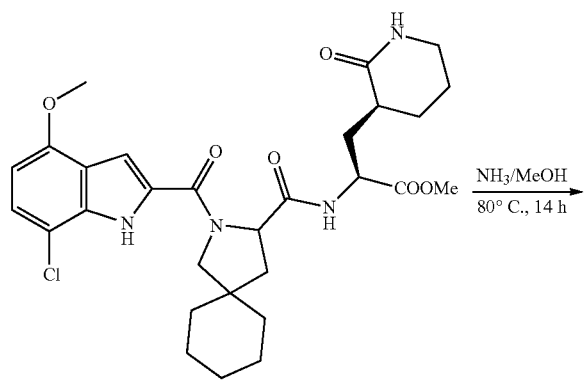

To a solution of ethyl 3-bromo-2-oxo-propanoate (60 g, 307.67 mmol, 38.46 mL, 1 eq) in CHCl₃ (250 mL) was added NH₂OH·HCl (23.52 g, 338.44 mmol, 1.1 eq) in H₂O (250 mL) under N₂. The mixture was stirred at 25° C. for 16 h. The reaction was quenched by H₂O (500 mL) and then extracted with DCM (300 mL*4). The combined organic phase was washed with brine (400 mL), dried over anhydrous Na₂SO₄, filtered and concentrated in vacuo to give a (Z)-ethyl 3-bromo-2-(hydroxyimino)propanoate (51 g, crude) as a yellow solid. MS (ESI) m/z 210.3 [M+H]⁺.

Step 2: 1-(cyclohexylidenemethyl)pyrrolidine

A mixture of cyclohexanecarbaldehyde (15 g, 133.73 mmol, 16.09 mL, 1 eq), pyrrolidine (11.41 g, 160.47 mmol, 13.40 mL, 1.2 eq) in toluene (300 mL) was heated at 130° C. for 14 h and water was removed by Dean-Stark trap. The reaction mixture was concentrated under reduced pressure to give a residue at 50° C. to give 1-(cyclohexylidenemethyl) pyrrolidine (20 g, crude) as a yellow oil. MS (ESI) m/z 166.2 $[M+H]^+$.

Step 3: ethyl 1-hydroxy-2-oxa-3-azaspiro[5.5]undec-3-ene-4-carboxylate

To a solution of 1-(cyclohexylidenemethyl)pyrrolidine (20 g, 121.01 mmol, 1 eq) in THF (200 mL) was added a solution of ethyl (2Z)-3-bromo-2-hydroxyimino-propanoate (25.42 g, 121.01 mmol, 1 eq) in THF (200 mL) drop-wise at −10° C. under $N_2$. After 1 h, TEA (12.24 g, 121.01 mmol, 16.84 mL, 1 eq) was added drop-wise at −10° C. under $N_2$. The reaction mixture was stirred at 25° C. for 12 h under $N_2$. The reaction was added with HCl (36%, 2.2 eq, 26 mL in 3.5 vol $H_2O$) drop-wise at 25° C., and stirred at 25° C. for 1 h. The reaction mixture was quenched by the addition of $H_2O$ (350 mL) at 25° C., and extracted with ethyl acetate (200 mL*3). The combined organic layers were washed with brine (300 mL), dried over $Na_2SO_4$, filtered and concentrated under reduced pressure to give a residue. The residue was purified by column chromatography ($SiO_2$, petroleum ether/ethyl acetate=1/0 to 1/1) to give a ethyl 1-hydroxy-2-oxa-3-azaspiro[5.5]undec-3-ene-4-carboxylate (15 g, 58.44 mmol, 48.29% yield, 94% purity) as a yellow oil. MS (ESI) m/z 242.2 $[M+H]^+$.

Step 4: ethyl 2-azaspiro[4.5]decane-3-carboxylate

To a solution of ethyl 1-hydroxy-2-oxa-3-azaspiro[5.5]undec-3-ene-4-carboxylate (15 g, 62.17 mmol, 1 eq) in EtOH (150 mL) was added Raney Nickel (10.65 g, 124.34 mmol, 2 eq) under $Ar_2$. The suspension was degassed under vacuum and purged with $H_2$ (125.58 mg, 62.17 mmol, 1 eq) several times. The mixture was stirred under $H_2$ (125.58 mg, 62.17 mmol, 1 eq) (50 psi) at 50° C. for 18 h. The reaction mixture was filtered and concentrated under reduced pressure to give a residue. The residue was purified by column chromatography ($SiO_2$, petroleum ether/ethyl acetate=4/1 to ethyl acetate/methanol=10/1) to give a ethyl 2-azaspiro[4.5]decane-3-carboxylate (6 g, 22.72 mmol, 36.54% yield, 80% purity) as a yellow and ethyl 2-azaspiro[4.5]decane-3-carboxylate (3 g, 5.11 mmol, 8.22% yield, 36% purity) was obtained as a yellow oil. MS (ESI) m/z 212.2 $[M+H]^+$.

Step 5: 2-tert-butyl 3-ethyl 2-azaspiro[4.5]decane-2,3-dicarboxylate

To a solution of ethyl 2-azaspiro[4.5]decane-3-carboxylate (6 g, 28.40 mmol, 1 eq) in DCM (60 mL) was added TEA (5.75 g, 56.79 mmol, 7.90 mL, 2 eq) and $Boc_2O$ (7.44 g, 34.07 mmol, 7.83 mL, 1.2 eq) at 0° C. The mixture was stirred at 20° C. for 12 h. The reaction mixture was quenched by the addition of $H_2O$ (300 mL), and extracted with ethyl acetate (150 mL*3). The combined organic layers were washed with brine (200 mL), dried over $Na_2SO_4$, filtered and concentrated under reduced pressure to give a residue. The residue was purified by column chromatography ($SiO_2$, petroleum ether/ethyl acetate=1/0 to 9/1) to give a 2-tert-butyl 3-ethyl 2-azaspiro[4.5]decane-2,3-dicarboxylate (6 g, 19.27 mmol, 67.85% yield, N/A purity) was obtained as a yellow oil. MS (ESI) m/z 312.2 $[M+H]^+$.

Step 6: 2-(tert-butoxycarbonyl)-2-azaspiro[4.5]decane-3-carboxylic acid

To a solution of 2-tert-butyl 3-ethyl 2-azaspiro[4.5]decane-2,3-dicarboxylate (7 g, 22.48 mmol, 1 eq) in $H_2O$ (14 mL) and MeOH (56 mL) was added LiOH·$H_2O$ (1.89 g, 44.96 mmol, 2 eq). The mixture was stirred at 40° C. for 12 h. The reaction mixture was concentrated under reduced pressure to remove MeOH. The residue was diluted with $H_2O$ (80 mL) and extracted with ethyl acetate.

Step 7: tert-butyl 3-(((S)-1-methoxy-1-oxo-3-((S)-2-oxopiperidin-3-yl)propan-2-yl)carbamoyl)-2-azaspiro[4.5]decane-2-carboxylate To a solution of methyl (2S)-2-amino-3-[(3S)-2-oxo-3-piperidyl]propanoate (6.25 g, 26.40 mmol, 1.1 eq, HCl) and 2-tert-butoxycarbonyl-2-azaspiro[4.5]decane-3-carboxylic acid (6.8 g, 24.00 mmol, 1 eq) in DCM (90 mL) was added DMAP (5.86 g, 48.00 mmol, 2 eq) and EDCI (6.90 g, 36.00 mmol, 1.5 eq). The mixture was stirred at 25° C. for 2 h. The reaction was quenched by 0.5 M HCl (200 mL) and then extracted with DCM (100 mL*3). The combined organic phase was washed with brine (150 mL), dried over anhydrous $Na_2SO_4$, filtered and concentrated in vacuo. The residue was purified by column chromatography ($SiO_2$, petroleum ether/ethyl acetate=3/1 to 0/1) to give a tert-butyl 3-[[(1S)-2-methoxy-2-oxo-1-[[(3S)-2-oxo-3-piperidyl]methyl]ethyl]carbamoyl]-2-azaspiro[4.5]decane-2-carboxylate (9 g, 18.36 mmol, 76.53% yield, 95% purity) as a white solid. MS (ESI) m/z 466.2 $[M+H]^+$

Step 8: (2S)-methyl 3-((S)-2-oxopiperidin-3-yl)-2-(2-azaspiro[4.5]decane-3-carboxamido)propanoate A mixture of tert-butyl 3-(((S)-1-methoxy-1-oxo-3-((S)-2-oxopiperidin-3-yl)propan-2-yl)carbamoyl)-2-azaspiro[4.5]decane-2-carboxylate (1.5 g, 2.90 mmol, 90% purity, 1 eq) in HCl/MeOH (4 M, 20 mL, 27.59 eq) was cooled to 0° C., and then stirred at 25° C. for 1 h. Upon completion, the mixture was concentrated under reduced pressure to give (2S)-methyl 3-((S)-2-oxopiperidin-3-yl)-2-(2-azaspiro[4.5]decane-3-carboxamido)propanoate (1.5 g, crude, HCl) as a white solid. MS (ESI) m/z 366.1 $[M+H]^+$.

Step 9: (2S)-methyl 2-(2-(7-chloro-4-methoxy-1H-indole-2-carbonyl)-2-azaspiro[4.5]decane-3-carboxamido)-3-((S)-2-oxopiperidin-3-yl)propanoate To a mixture of (2S)-methyl 3-((S)-2-oxopiperidin-3-yl)-2-(2-azaspiro[4.5]decane-3-carboxamido)propanoate (1.5 g, 3.55 mmol, 1 eq, HCl) in DCM (30 mL) and DMF (10 mL) was added 7-chloro-4-methoxy-1H-indole-2-carboxylic acid (959.94 mg, 4.25 mmol, 1.2 eq), followed by DMAP (1.30 g, 10.64 mmol, 3 eq) and EDCI (1.36 g, 7.09 mmol, 2 eq) at 0° C. The resulting mixture was stirred at 25° C. for 2 h. and then the reaction mixture was quenched with water (10 mL) at 0° C. After extraction with DCM (10 mL*3). the combined organic layers were washed with brine (10 mL), dried over $Na_2SO_4$, filtered and concentrated under reduced pressure. The residue was purified by column chromatography ($SiO_2$, DCM:MeOH=100:1 to 10:1) to give methyl (2S)-2-[[2-(7-chloro-4-methoxy-1H-indole-2-carbonyl)-2-azaspiro[4.5]decane-3-carbonyl]amino]-3-[(3S)-2-oxo-3- piperidyl]propanoate (1.91 g, 3.00 mmol, 84.60% yield, 90% purity) as a yellow oil. MS (ESI) m/z 573.3 [M+H]+.

Step 10: N-((S)-1-amino-1-oxo-3-((S)-2-oxopiperidin-3-yl)propan-2-yl)-2-(7-chloro-4-methoxy-1H-indole-2-carbonyl)-2-azaspiro[4.5]decane-3-carboxamide A mixture of methyl (2S)-2-[[2-(7-chloro-4-methoxy-1H-indole-2-carbonyl)-2-azaspiro[4.5]decane-3-carbonyl]amino]-3-[(3S)-2-oxo-3-piperidyl]propanoate (1.91 g, 3.00 mmol, 90% purity, 1 eq) in NH$_3$/MeOH (7 M, 17.79 mL, 41.52 eq) was stirred at 80° C. for 14 h. Upon completion, the reaction mixture was concentrated under reduced pressure to give N-((S)-1-amino-1-oxo-3-((S)-2-oxopiperidin-3-yl)propan-2-yl)-2-(7-chloro-4-methoxy-1H-indole-2-carbonyl)-2-azaspiro[4.5]decane-3-carboxamide (1.3 g, crude) as a yellow solid. MS (ESI) m/z 558.3 [M+H]+.

Step 11: 2-(7-chloro-4-methoxy-H-indole-2-carbonyl)-N-(1-cyano-2-((S)-2-oxopiperidin-3-yl)ethyl)-2-azaspiro[4.5]decane-3-carboxamide To a mixture of N-((S)-1-amino-1-oxo-3-((S)-2-oxopiperidin-3-yl)propan-2-yl)-2-(7-chloro-4-methoxy-1H-indole-2-carbonyl)-2-azaspiro[4.5]decane-3-carboxamide (1.3 g, 1.98 mmol, 1 eq) in DCM (25 mL) was added Burgess reagent (1.42 g, 5.94 mmol, 3 eq). After stirring at 25° C. for 3 h, the mixture was quenched with water (1 mL) and concentrated under reduced pressure to give a residue (<30° C.). The residue was purified by prep-HPLC (column: Phenomenex Titank C18 Bulk (250*100 mm*10 um); mobile phase: [water (10 mM NH$_4$HCO$_3$)-ACN]; B %: 40%-75%, 20 min) to give 2-(7-chloro-4-methoxy-1H-indole-2-carbonyl)-N-(1-cyano-2-((S)-2-oxopiperidin-3-yl)ethyl)-2-azaspiro[4.5]decane-3-carboxamide (350 mg, 648.09 umol, 32.73% yield) as a white solid. MS (ESI) m/z 540.1 [M+H]+.

Step 12: 2-(7-chloro-4-methoxy-1H-indole-2-carbonyl)-N-(1-cyano-2-((S)-2-oxopiperidin-3-yl)ethyl)-2-azaspiro[4.5]decane-3-carboxamide 2-(7-Chloro-4-methoxy-1H-indole-2-carbonyl)-N-(1-cyano-2-((S)-2-oxopiperidin-3-yl)ethyl)-2-azaspiro[4.5]decane-3-carboxamide (350.00 mg, 550.87 umol, 95% purity, 1 eq) was purified by SFC (column: Waters Xbridge BEH C18 (100*30 mm*10 um; mobile phase: [water (10 mM NH$_4$HCO$_3$)-ACN]; B %: 35%-60%, 8 min) to give 2-(7-chloro-4-methoxy-1H-indole-2-carbonyl)-N-(1-cyano-2-((S)-2-oxopiperidin-3-yl)ethyl)-2-azaspiro[4.5]decane-3-carboxamide Isomer 1 (62.40 mg, 112.77 umol, 20.47% yield, 97.6% purity) as a white solid. MS (ESI) m/z 540.2 [M+H]+.

$^1$H NMR (400 MHz, METHANOL-d$_4$) δ=7.23-6.79 (m, 2H), 6.58-6.39 (m, 1H), 5.11 (dd, J=5.7, 10.6 Hz, 1H), 4.77-4.52 (m, 1H), 4.03-3.76 (m, 4H), 3.74-3.37 (m, 1H), 3.47-2.89 (m, 2H), 2.65-2.10 (m, 3H), 2.09-1.27 (m, 16H).

2-(7-Chloro-4-methoxy-1H-indole-2-carbonyl)-N-(1-cyano-2-((S)-2-oxopiperidin-3-yl)ethyl)-2-azaspiro[4.5]decane-3-carboxamide Isomer 2 (131.81 mg, 244.07 umol, 44.31% yield, 100% purity) was obtained as a white solid. MS (ESI) m/z 540.2 [M+H]+.

$^1$H NMR (400 MHz, METHANOL-d$_4$) δ=7.22-6.84 (m, 2H), 6.59-6.44 (m, 1H), 5.07-4.95 (m, 1H), 4.69-4.50 (m, 1H), 4.02-3.81 (m, 4H), 3.80-3.43 (m, 1H), 3.23-3.02 (m, 2H), 2.54-2.13 (m, 3H), 2.11-1.36 (m, 16H).

2-(7-Chloro-4-methoxy-1H-indole-2-carbonyl)-N-(1-cyano-2-((S)-2-oxopiperidin-3-yl)ethyl)-2-azaspiro[4.5]decane-3-carboxamide Isomer 3 (34.64 mg, 64.14 umol, 11.64% yield, 100% purity) was obtained as a white solid. MS (ESI) m/z 540.2 [M+H]+.

1H NMR (400 MHz, METHANOL-d$_4$) δ=7.31-6.74 (m, 2H), 6.63-6.43 (m, 1H), 5.29-4.96 (m, 1H), 4.87-4.58 (m, 1H), 3.91 (br d, J=9.0 Hz, 4H), 3.80-3.38 (m, 1H), 3.29-3.02 (m, 2H), 2.64-2.13 (m, 3H), 2.10-1.35 (m, 16H).

2-(7-Chloro-4-methoxy-1H-indole-2-carbonyl)-N-(1-cyano-2-((S)-2-oxopiperidin-3-yl)ethyl)-2-azaspiro[4.5]decane-3-carboxamide Isomer 4 (5.66 mg, 10.45 umol, 1.90% yield, 99.7% purity) was obtained as a white solid. MS (ESI) m/z 540.2 [M+H]+.

1H NMR (400 MHz, METHANOL-d$_4$) δ=7.31-6.77 (m, 2H), 6.62-6.46 (m, 1H), 5.17-4.91 (m, 1H), 4.75-4.56 (m, 1H), 4.04-3.80 (m, 4H), 3.73 (d, J=10.4 Hz, 1H), 3.28-3.01 (m, 2H), 2.55-2.44 (m, 1H), 2.44-2.25 (m, 2H), 2.08-1.40 (m, 16H).

(50 mL*2). The aqueous phase were added HCl aq adjust to pH=2 and extracted with EA (90 mL*3), The combined organic layers were washed with brine (90 mL), dried over Na$_2$SO$_4$, filtered and concentrated under reduced pressure to give a 2-tert-butoxycarbonyl-2-azaspiro[4.5]decane-3-carboxylic acid (6.1 g, crude) was obtained as a white solid. MS (ESI) m/z 284.2 [M+H]+

Example 207. Synthesis of Viral Protease Inhibitor Compound 906

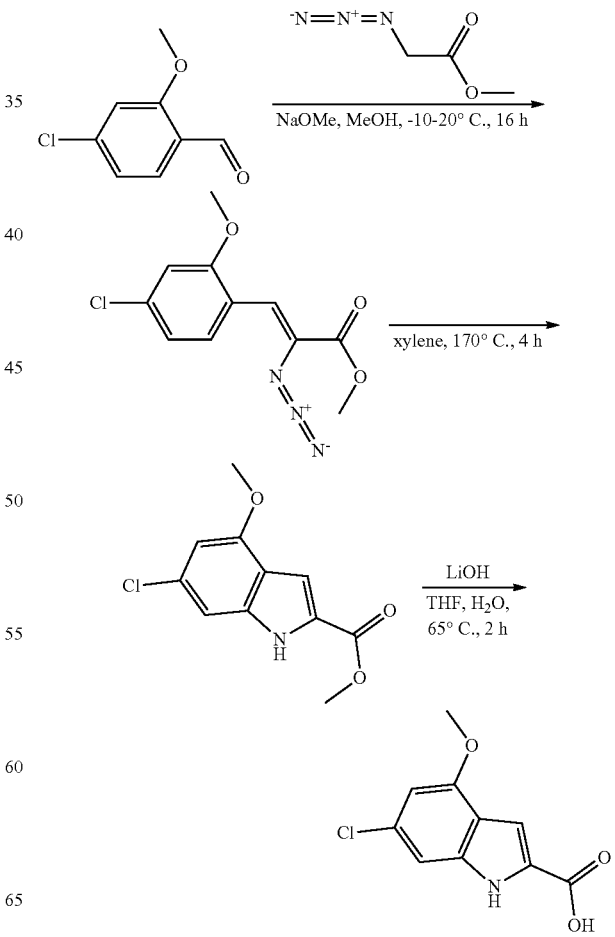

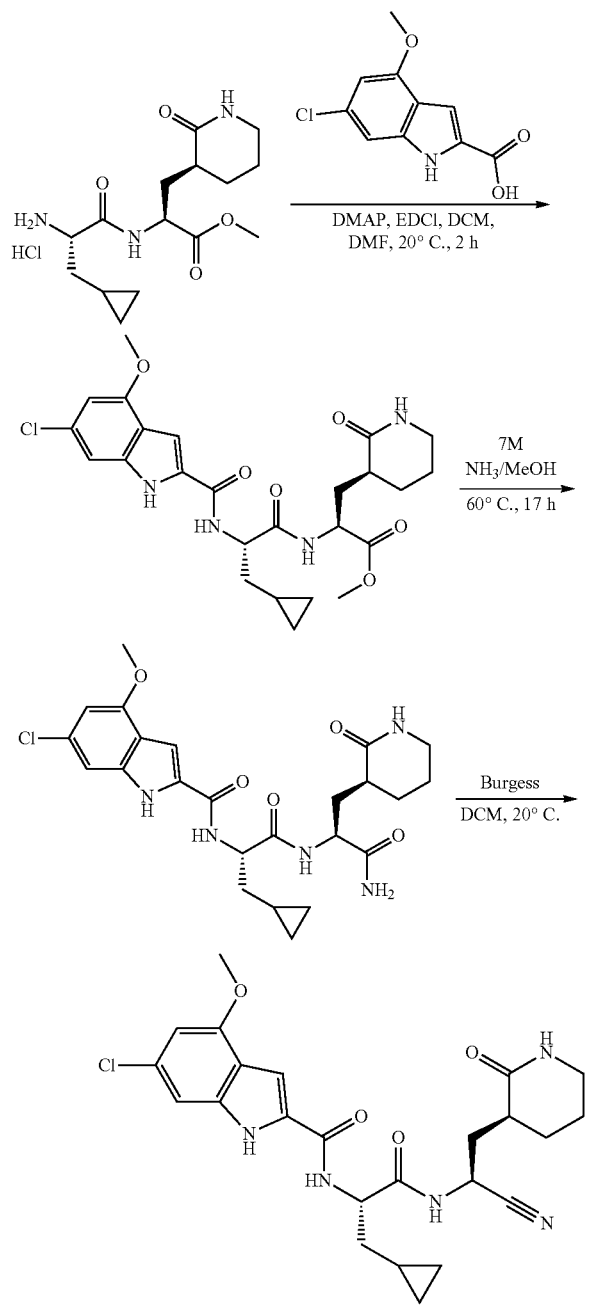

To a solution of CH₃ONa (2.53 g, 46.90 mmol, 2 eq) in MeOH (40 mL) was added a mixture of 4-chloro-2-methoxy-benzaldehyde (4 g, 23.45 mmol, 1 eq) and methyl 2-azidoacetate (5.40 g, 46.90 mmol, 2 eq) in MeOH (15 mL) at −10° C. After stirring for 16 h at 20° C., the solution was diluted with H₂O (60 mL) and concentrated and extracted with ethyl acetate (50 mL*3) and concentrated to give crude. The crude was purified by column (SiO₂, petroleum ether: ethyl acetate=20:1 to 3:1) to give product methyl (Z)-2-azido-3-(4-chloro-2-methoxy-phenyl)prop-2-enoate (3.3 g, 12.33 mmol, 52.58% yield) as a white solid. MS (ESI) m/z 268.1 [M+H]⁺

Step 2: methyl 6-chloro-4-methoxy-1H-indole-2-carboxylate

A solution of methyl (Z)-2-azido-3-(4-chloro-2-methoxy-phenyl)prop-2-enoate (3000 mg, 11.21 mmol, 1 eq) in xylene (30 mL) was stirred for 4 h at 170° C. Upon completion, the solution was concentrated to give crude. The crude was purified by column (SiO₂, petroleum ether:ethyl acetate=10:1 to 1:10) to give product methyl 6-chloro-4-methoxy-1H-indole-2-carboxylate (1500 mg, 6.26 mmol, 55.84% yield) as a white solid. MS (ESI) m/z 240.1 [M+H]⁺

Step 3: 6-chloro-4-methoxy-1H-indole-2-carboxylic acid

A solution of methyl 6-chloro-4-methoxy-1H-indole-2-carboxylate (1500 mg, 6.26 mmol, 1 eq) in THF (15 mL) and H₂O (15 mL) was added with LiOH·H₂O (787.95 mg, 18.78 mmol, 3 eq). After stirring for 2 h at 65° C., the solution was concentrated and extracted with ethyl acetate (50 mL*2) and the water layer was adjusted pH=4-5 with HCl (con) and extracted with ethyl acetate (80 mL*3) and dried over Na₂SO₄ and concentrated to give crude. The crude was used directly for the next step. 6-chloro-4-methoxy-1H-indole-2-carboxylic acid (1070 mg, 4.74 mmol, 75.77% yield) as a brown solid. MS (ESI) m/z 226.2 [M+H]⁺

Step 4: methyl (2S)-2-[[(2S)-2-[(6-chloro-4-methoxy-1H-indole-2-carbonyl)amino]-3-cyclopropyl-propanoyl]amino]-3-[(3S)-2-oxo-3-piperidyl]propanoate To a solution of methyl (2S)-2-[[(2S)-2-amino-3-cyclopropyl-propanoyl]amino]-3-[(3S)-2-oxo-3-piperidyl]propanoate (500 mg, 1.44 mmol, 1 eq, HCl) in DCM (10 mL) and DMF (10 mL) was added DMAP (351.22 mg, 2.87 mmol, 2 eq), 6-chloro-4-methoxy-1H-indole-2-carboxylic acid (372.98 mg, 1.65 mmol, 1.15 eq) and EDCI (551.13 mg, 2.87 mmol, 2 eq). After stirring for 2 h at 20° C., the mixture was diluted with H₂O (30 mL) and extracted with ethyl acetate (50 mL*3) and concentrated to give crude. The crude was purified by column (SiO₂, petroleum ether:ethyl acetate=10:1 to EA:MeOH=10:1) to give methyl (2S)-2-[[(2S)-2-[(6-chloro-4-methoxy-1H-indole-2-carbonyl)amino]-3-cyclopropyl-propanoyl]amino]-3-[(3S)-2-oxo-3-piperidyl]propanoate (500 mg, 963.41 umol, 67.02% yield) as a white solid. MS (ESI) m/z 519.3 [M+H]⁺

Step 5: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-chloro-4-methoxy-1H-indole-2-carboxamide A solution of methyl (2S)-2-[[(2S)-2-[(6-chloro-4-methoxy-1H-indole-2-carbonyl)amino]-3-cyclopropyl-propanoyl]amino]-3-[(3S)-2-oxo-3-piperidyl]propanoate (500 mg, 963.41 umol, 1 eq) in NH₃/MeOH (7 M, 20 mL, 145.32 eq) was stirred for 17 h at 60° C. The solution was concentrated to afford N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-chloro-4-methoxy-1H-indole-2-carboxamide (485 mg, crude) as a white solid. The crude was used directly for the next step. MS (ESI) m/z 504.3 [M+H]⁺

Step 6: 6-chloro-N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-chloro-4-methoxy-1H-indole-2-carboxamide (470 mg, 932.58 umol, 1 eq) in DCM (25 mL) was added Burgess reagent (666.72 mg, 2.80 mmol, 3 eq). After stirring for 3 h at 20° C., the solution was washed with brine (50 mL) and dried with using $N_2$ to give a crude. The crude was purified by pre-HPLC (neutral) to afford 6-chloro-N-[(1S)-2-[[(1S)-1-cyano-2-[(3S)-2-oxo-3-piperidyl]ethyl]amino]-1-(cyclopropylmethyl)-2-oxo-ethyl]-4-methoxy-1H-indole-2-carboxamide (210 mg, 432.13 umol, 46.34% yield) as a white solid. MS (ESI) m/z 486.3 [M+H]$^+$ Pre-HPLC condition: column: Waters Xbridge C18 150*50 mm*10 um; mobile phase: [water (10 mM NH4HCO3)-ACN]; B %: 30%-60%, 10 min $^1$H NMR (400 MHz, DMSO-d$_6$) δ=11.72 (s, 1H), 8.91 (br d, J=8.2 Hz, 1H), 8.58 (br d, J=7.3 Hz, 1H), 7.53 (br s, 1H), 7.38 (s, 1H), 7.03 (s, 1H), 6.56 (s, 1H), 5.17-4.93 (m, 1H), 4.53-4.31 (m, 1H), 3.91 (s, 3H), 3.09 (br s, 2H), 2.37-2.15 (m, 2H), 1.89-1.27 (m, 7H), 0.80 (br s, 1H), 0.40 (br s, 1H), 0.23-0.10 (m, 2H).

Example 208. Synthesis of Viral Protease Inhibitor Compound 1511 (S4H_25)

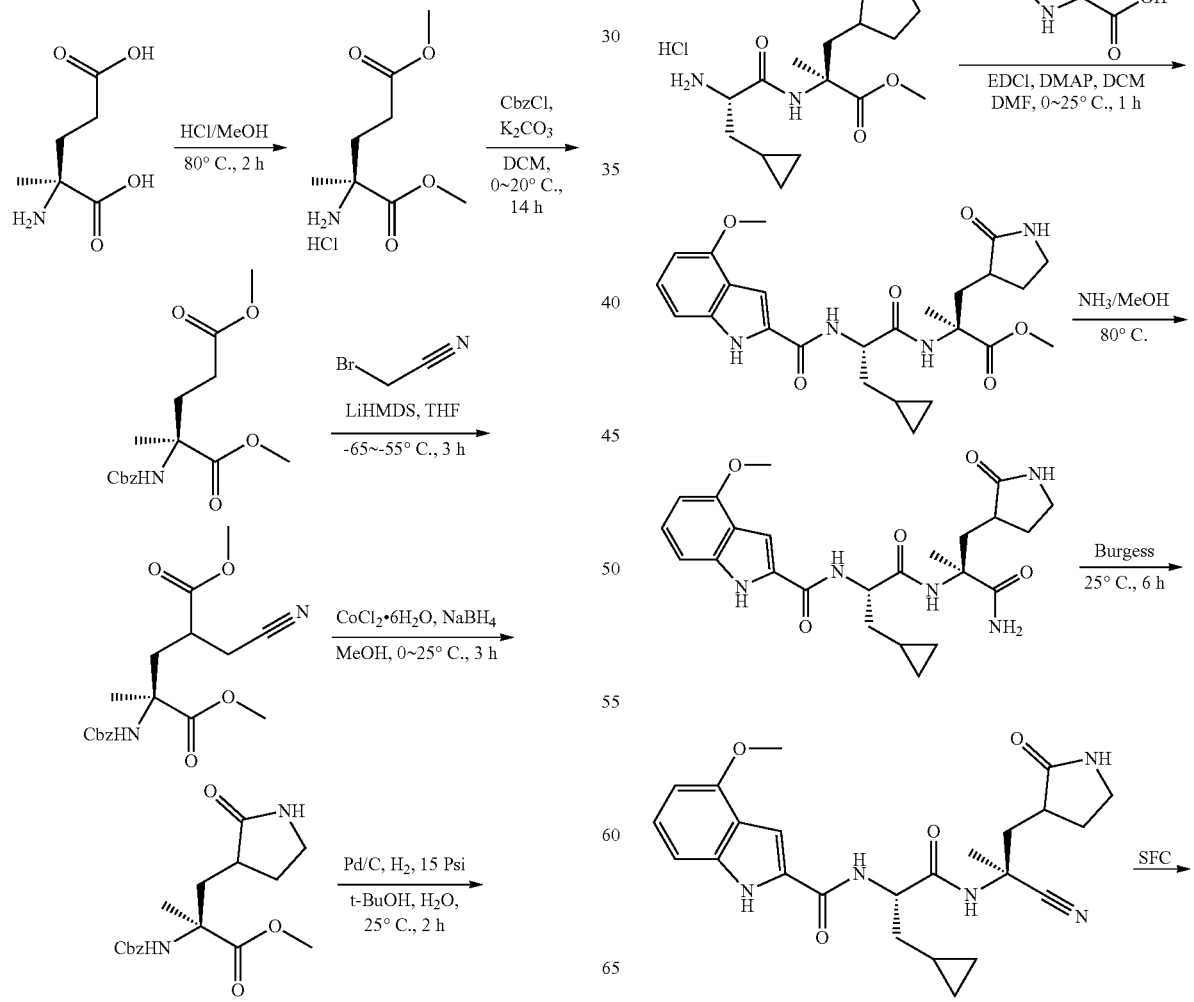

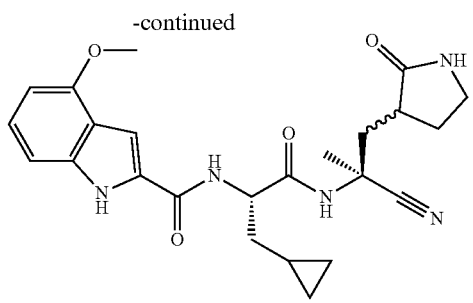

A mixture of (2S)-2-amino-2-methyl-pentanedioic acid (1 g, 6.21 mmol, 1 eq) in HCl/MeOH (4 M, 10 mL, 6.45 eq) was stirred at 80° C. for 2 h. Upon completion, the reaction mixture was concentrated under reduced pressure to give (S)-dimethyl 2-amino-2-methylpentanedioate (1.4 g, crude) as a yellow oil. MS (ESI) m/z 190.2 [M+H]$^+$.

Step 2: (S)-dimethyl 2-(((benzyloxy)carbonyl)amino)-2-methylpentanedioate

To a mixture of (S)-dimethyl 2-amino-2-methylpentanedioate (1.1 g, 4.87 mmol, 1 eq, HCl) in DCM (11 mL) was added K$_2$CO$_3$ (2.02 g, 14.62 mmol, 3 eq) and CbzCl (914.69 mg, 5.36 mmol, 762.24 uL, 1.1 eq) at 0° C. After stirring at 20° C. for 14 h, the reaction mixture was diluted with water (10 mL) and extracted with DCM (10 mL*3). The combined organic layers were washed with brine (10 mL), dried over Na$_2$SO$_4$, filtered and concentrated under reduced pressure to give a residue. The residue was purified by column chromatography (SiO$_2$, petroleum ether:ethyl acetate=10:1 to 2:1) to give (S)-dimethyl 2-(((benzyloxy)carbonyl)amino)-2-methylpentanedioate (920 mg, 2.85 mmol, 58.37% yield) as a yellow oil. MS (ESI) m/z 324.1 [M+H]$^+$.

Step 3: (2S)-dimethyl 2-(((benzyloxy)carbonyl)amino)-4-(cyanomethyl)-2-methylpentanedioate To a mixture of (S)-dimethyl 2-(((benzyloxy)carbonyl)amino)-2-methylpentanedioate (920 mg, 2.42 mmol, 85% purity, 1 eq) in anhydrous THF (18.4 mL) was added LiHMDS (1 M, 5.32 mL, 2.2 eq) drop-wise under N$_2$ atmosphere at −65~−55° C. for 0.5 h. After a further 1 h of stirring at −65~−55° C., 2-bromoacetonitrile (435.14 mg, 3.63 mmol, 241.75 uL, 1.5 eq) was added drop-wise to the mixture solution over a period of 0.5 h while maintaining the temperature under −65~−55° C. The reaction mixture was stirred at −65~−55° C. for 1 h under N$_2$. Upon completion, the reaction mixture was quenched with pre-cooled (dry-ice in EtOH) MeOH (2.8 mL) and a pre-cooled (dry-ice in EtOH) acetic acid in THF solution (0.46 mL HOAc/3.7 mL THF) in order at −60° C. After further 30 min of stirring at −60° C., the cooling bath was removed and replaced with water bath. The reaction mixture was allowed to warm up to 0 f 5° C. and then concentrated under reduced pressure at 30° C. to give a black brown solid. The obtained residue was dissolved in ethyl acetate (37 mL), washed with brine (18 mL*2). The organic phase was dried over Na$_2$SO$_4$, filtered, and concentrated under reduced pressure to give a residue. The residue was purified by column chromatography (SiO$_2$, petroleum ether:ethyl acetate=10:1 to 2:1) to give (2S)-dimethyl 2-(((benzyloxy)carbonyl)amino)-4-(cyanomethyl)-2-methylpentanedioate (740 mg, 1.84 mmol, 75.99% yield, 90% purity) as a yellow oil. MS (ESI) m/z 363.1 [M+H]$^+$.

Step 4: (2S)-methyl 2-(((benzyloxy)carbonyl)amino)-2-methyl-3-(2-oxopyrrolidin-3-yl)propanoate To a stirred solution of (2S)-dimethyl 2-(((benzyloxy)carbonyl)amino)-4-(cyanomethyl)-2-methylpentanedioate (740 mg, 1.84 mmol, 90% purity, 1 eq) in MeOH (34 mL) was added CoCl$_2$·6H$_2$O (262.37 mg, 1.10 mmol, 0.6 eq) at 0° C., and then NaBH$_4$ (419 mg, 11.08 mmol, 6.03 eq) was added into the mixture in 4 batches at 0° C. for 1 h, and then the black mixture was stirred at 25° C. for 2 h. Upon completion, the mixture was quenched with NH$_4$Cl aq. (41 mL) at 0° C., the mixture was filtered through celite, then extracted with DCM (41 mL*3), the organic layer was dried over Na$_2$SO$_4$, filtered, and concentrated under reduced pressure to get the crude product. The residue was purified by column chromatography (SiO$_2$, petroleum ether:ethyl acetate=10:1 to 1:1) to give (2S)-methyl 2-(((benzyloxy)carbonyl)amino)-2-methyl-3-(2-oxopyrrolidin-3-yl)propanoate (320 mg, 957.03 umol, 52.07% yield) as a white solid. MS (ESI) m/z 335.2 [M+H]$^+$.

Step 5: (2S)-methyl 2-amino-2-methyl-3-(2-oxopyrrolidin-3-yl)propanoate

To a mixture of (2S)-methyl 2-(((benzyloxy)carbonyl)amino)-2-methyl-3-(2-oxopyrrolidin-3-yl)propanoate (320 mg, 957.03 umol, 1 eq) in H$_2$O (1.5 mL) and t-BuOH (6 mL) under N$_2$ was added Pd/C (160 mg, 10% purity). The resulting mixture was degassed and purged with H$_2$ for 3 times, and then the mixture was stirred under H$_2$ (15 Psi) at 25° C. for 2 h. Upon completion, the mixture was filtered through celite and the filtrate was concentrated under reduced pressure to give (2S)-methyl 2-amino-2-methyl-3-(2-oxopyrrolidin-3-yl)propanoate (140 mg, crude) as a white solid. MS (ESI) m/z 201.1 [M+H]$^+$.

Step 6: (2S)-methyl 2-((S)-2-((tert-butoxycarbonyl)amino)-3-cyclopropylpropanamido)-2-methyl-3-(2-oxopyrrolidin-3-yl)propanoate To a solution of (2S)-methyl 2-amino-2-methyl-3-(2-oxopyrrolidin-3-yl)propanoate (140 mg, 699.18 umol, 1 eq) in DCM (2 mL) and DMF (1 mL) was added (2S)-2-(tert-butoxycarbonylamino)-3-cyclopropyl-propanoic acid (192.36 mg, 839.02 umol, 1.2 eq), TEA (212.25 mg, 2.10 mmol, 291.95 uL, 3 eq). After the addition of T$_3$P (667.40 mg, 1.05 mmol, 623.74 uL, 50% purity, 1.5 eq) at 0° C., the mixture was stirred at 25° C. for 1 h. Upon completion, the reaction mixture was diluted with water (10 mL) and extracted with DCM (10 mL*3). The combined organic layers were washed with brine (10 mL), dried over Na$_2$SO$_4$, filtered and concentrated under reduced pressure to give a residue. The residue was purified by prep-TLC (SiO$_2$, DCM:MeOH=10:1) to give (2S)-methyl 2-((S)-2-((tert-butoxycarbonyl)amino)-3-cyclopropylpropanamido)-2-methyl-3-(2-oxopyrrolidin-3-yl)propanoate (280 mg, 612.41 umol, 87.59% yield, 90% purity) as yellow oil. MS (ESI) m/z 412.3 [M+H]$^+$.

Step 7: (2S)-methyl 2-((S)-2-amino-3-cyclopropylpropanamido)-2-methyl-3-(2-oxopyrrolidin-3-yl)propanoate A solution of (2S)-methyl 2-((S)-2-((tert-butoxycarbonyl)amino)-3-cyclopropylpropanamido)-2-methyl-3-(2-oxopyrrolidin-3-yl)propanoate (260 mg, 568.66 umol, 90% purity, 1 eq) in HCl/MeOH (4 M, 2.6 mL, 18.29 eq) was stirred at 25° C. for 1 h. Upon completion, the reaction mixture was concentrated under reduced pressure to give (2S)-methyl 2-((S)-2-amino-3-cyclopropylpropanamido)-2-methyl-3-(2-oxopyrrolidin-3-yl)propanoate (200 mg, crude, HCl) as yellow solid. MS (ESI) m/z 312.2 [M+H]$^+$.

Step 8: (2S)-methyl 2-((S)-3-cyclopropyl-2-(4-methoxy-1H-indole-2-carboxamido)propanamido)-2-methyl-3-(2-oxopyrrolidin-3-yl)propanoate To a solution of (2S)-methyl 2-((S)-2-amino-3-cyclopropylpropanamido)-2-methyl-3-(2-oxopyrrolidin-3-yl)propanoate (200 mg, 546.23 umol, 95% purity, 1 eq, HCl) in DCM (4 mL) and DMF (2 mL) was added 4-methoxy-1H-indole-2-carboxylic acid (125.32 mg, 655.48 umol, 1.2 eq), DMAP (200.20 mg, 1.64 mmol, 3 eq), and EDCI (209.43 mg, 1.09 mmol, 2 eq) at 0° C. The mixture was stirred at 25° C. for 1 h, and then the reaction mixture was diluted with water (20 mL) and extracted with DCM (10 mL*3). The combined organic layers were washed with brine (10 mL), dried over Na$_2$SO$_4$, filtered and concentrated under reduced pressure to give a residue. The residue was purified by prep-TLC (SiO$_2$, DCM:MeOH=10:1) to give (2S)-methyl 2-((S)-3-cyclopropyl-2-(4-methoxy-1H-indole-2-carboxamido)propanamido)-2-methyl-3-(2-oxopyrrolidin-3-yl)propanoate (300 mg, 451.97 umol, 82.74% yield, 73% purity) as a yellow oil. MS (ESI) m/z 485.3 [M+H]$^+$.

Step 9: N-((2S)-1-(((2S)-1-amino-2-methyl-1-oxo-3-(2-oxopyrrolidin-3-yl)propan-2-yl)amino)-3-cyclopropyl-1-oxopropan-2-yl)-4-methoxy-1H-indole-2-carboxamide A solution of (2S)-methyl 2-((S)-3-cyclopropyl-2-(4-methoxy-1H-indole-2-carboxamido)propanamido)-2-methyl-3-(2-oxopyrrolidin-3-yl)propanoate (280.00 mg, 421.84 umol, 73% purity, 1 eq) in NH$_3$/MeOH (7 M, 6 mL, 99.56 eq) was stirred at 80° C. for 86 h. Upon completion, the reaction mixture was concentrated under reduced pressure to give a residue. The residue was purified by prep-TLC (SiO$_2$, DCM:MeOH=10:1) to give N-((2S)-1-(((2S)-1-amino-2-methyl-1-oxo-3-(2-oxopyrrolidin-3-yl)propan-2-yl)amino)-3-cyclopropyl-1-oxopropan-2-yl)-4-methoxy-1H-indole-2-carboxamide (35 mg, 70.82 umol, 16.79% yield, 95% purity) as a yellow solid. MS (ESI) m/z 470.3 [M+H]$^+$.

Step 10: N-((2S)-1-(((2S)-2-cyano-1-(2-oxopyrrolidin-3-yl)propan-2-yl)amino)-3-cyclopropyl-1-oxopropan-2-yl)-4-methoxy-1H-indole-2-carboxamide To a solution of N-((2S)-1-(((2S)-1-amino-2-methyl-1-oxo-3-(2-oxopyrrolidin-3-yl)propan-2-yl)amino)-3-cyclopropyl-1-oxopropan-2-yl)-4-methoxy-1H-indole-2-carboxamide (30 mg, 60.70 umol, 95% purity, 1 eq) in DCM (1 mL) was added Burgess reagent (43.40 mg, 182.10 umol, 3 eq), and then was stirred at 25° C. for 6 h. Upon completion, the reaction mixture was quenched by addition H$_2$O (0.1 mL) at 20° C. and then concentrated under reduced pressure (<20° C.) to give a residue. The residue was purified by prep-HPLC (column: Waters Xbridge BEH C18 100*25 mm*5 um; mobile phase: [water (10 mM NH$_4$HCO$_3$)-ACN]; B %: 20%-50%, 10 min) to give N-((2S)-1-(((2S)-2-cyano-1-(2-oxopyrrolidin-3-yl)propan-2-yl)amino)-3-cyclopropyl-1-oxopropan-2-yl)-4-methoxy-1H-indole-2-carboxamide (25 mg, 52.60 umol, 86.66% yield, 95% purity) as a white solid. MS (ESI) m/z 452.2 [M+H]$^+$.

Step 11: N-((2S)-1-(((2S)-2-cyano-1-(2-oxopyrrolidin-3-yl)propan-2-yl)amino)-3-cyclopropyl-1-oxopropan-2-yl)-4-methoxy-1H-indole-2-carboxamide N-((2S)-1-(((2S)-2-cyano-1-(2-oxopyrrolidin-3-yl)propan-2-yl)amino)-3-cyclopropyl-1-oxopropan-2-yl)-4-methoxy-1H-indole-2-carboxamide (25 mg, 52.60 umol, 95% purity, 1 eq) was purified by SFC (column: DAICEL CHIRALPAK AD (250 mm*30 mm, 10 um); mobile phase: [0.1% NH$_3$H$_2$O IPA]; B %: 50%-50%, 7 min) to give N-((2S)-1-(((2S)-2-cyano-1-(2-oxopyrrolidin-3-yl)propan-2-yl)amino)-3-cyclopropyl-1-oxopropan-2-yl)-4-methoxy-1H-indole-2-carboxamide Isomer 1 (2.35 mg, 5.10 umol, 9.69% yield, 97.9% purity) as a white solid. MS (ESI) m/z 452.1 [M+H]$^+$.

$^1$H NMR (400 MHz, MeOD-d$_4$) δ=7.26 (d, J=0.7 Hz, 1H), 7.19-7.11 (m, 1H), 7.03 (d, J=8.2 Hz, 1H), 6.51 (d, J=7.7 Hz, 1H), 4.59 (t, J=7.3 Hz, 1H), 3.93 (s, 3H), 3.38-3.32 (m, 2H), 2.77-2.66 (m, 1H), 2.54-2.45 (m, 1H), 2.40 (dd, J=5.1, 14.3 Hz, 1H), 2.07 (dd, J=7.3, 14.3 Hz, 1H), 2.02-1.91 (m, 1H), 1.86 (td, J=7.1, 14.0 Hz, 1H), 1.74 (s, 3H), 1.68 (td, J=7.1, 14.1 Hz, 1H), 0.93-0.79 (m, 1H), 0.59-0.44 (m, 2H), 0.26-0.14 (m, 2H).

N-((2S)-1-(((2S)-2-cyano-1-(2-oxopyrrolidin-3-yl)propan-2-yl)amino)-3-cyclopropyl-1-oxopropan-2-yl)-4-methoxy-1H-indole-2-carboxamide Isomer 2 (2.08 mg, 4.53 umol, 8.62% yield, 98.4% purity) was obtained as a white solid. MS (ESI) m/z 452.1 [M+H]$^+$.

$^1$H NMR (400 MHz, MeOD-d$_4$) δ=7.26 (s, 1H), 7.20-7.13 (m, 1H), 7.03 (d, J=8.2 Hz, 1H), 6.52 (d, J=7.7 Hz, 1H), 4.62 (dd, J=6.4, 7.9 Hz, 1H), 3.93 (s, 3H), 3.28-3.16 (m, 2H), 2.73-2.61 (m, 1H), 2.39 (td, J=6.6, 12.8 Hz, 1H), 2.27 (dd, J=7.4, 14.9 Hz, 1H), 2.01-1.92 (m, 1H), 1.92-1.78 (m, 2H), 1.76-1.66 (m, 4H), 0.89-0.78 (m, 1H), 0.55-0.44 (m, 2H), 0.24-0.14 (m, 2H)

Example 209. Synthesis of Viral Protease Inhibitor Compound 749

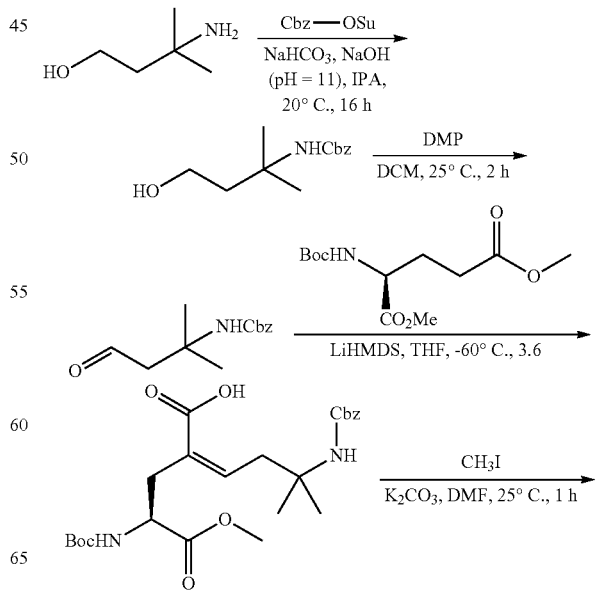

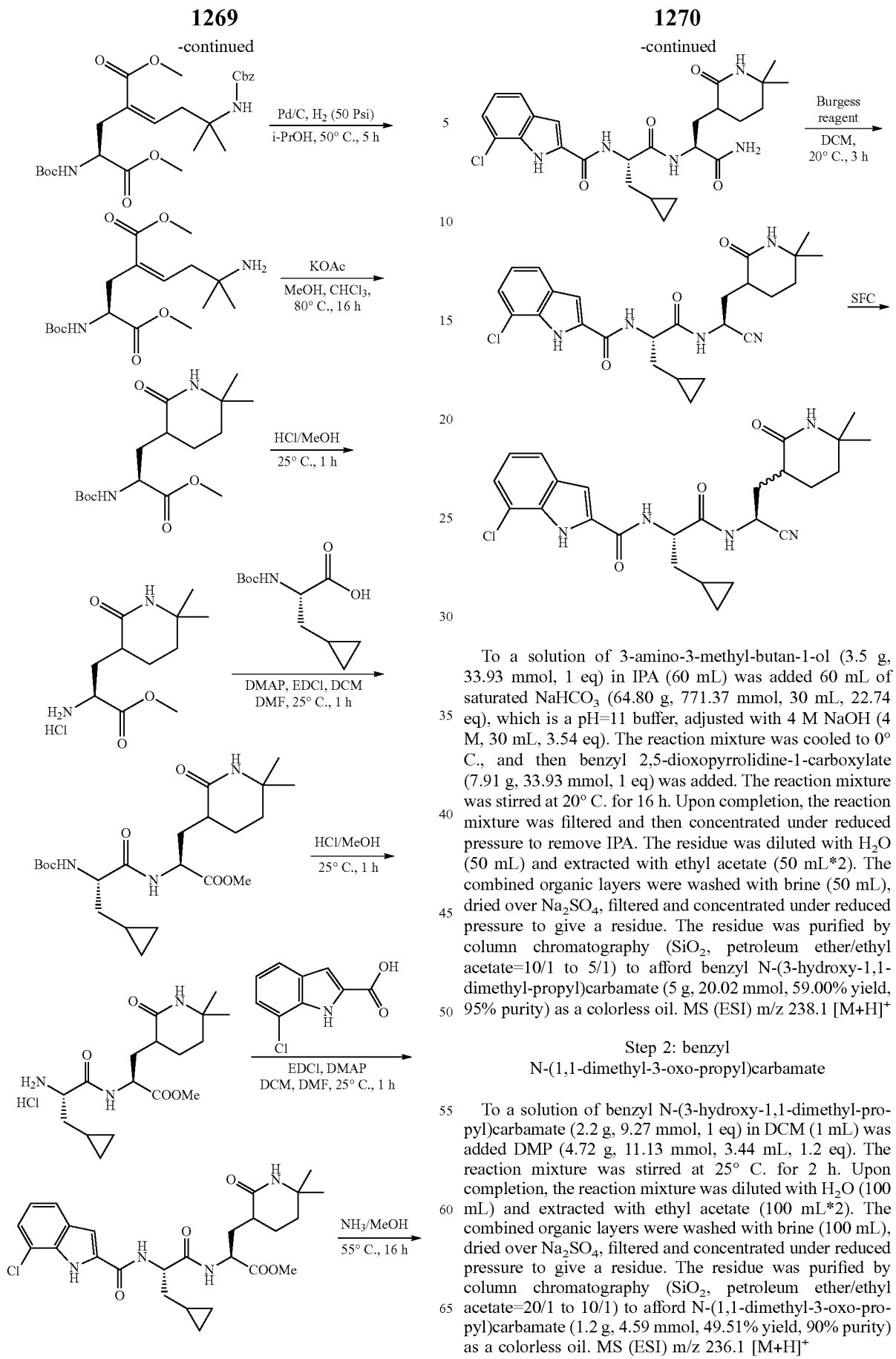

To a solution of 3-amino-3-methyl-butan-1-ol (3.5 g, 33.93 mmol, 1 eq) in IPA (60 mL) was added 60 mL of saturated NaHCO$_3$ (64.80 g, 771.37 mmol, 30 mL, 22.74 eq), which is a pH=11 buffer, adjusted with 4 M NaOH (4 M, 30 mL, 3.54 eq). The reaction mixture was cooled to 0° C., and then benzyl 2,5-dioxopyrrolidine-1-carboxylate (7.91 g, 33.93 mmol, 1 eq) was added. The reaction mixture was stirred at 20° C. for 16 h. Upon completion, the reaction mixture was filtered and then concentrated under reduced pressure to remove IPA. The residue was diluted with H$_2$O (50 mL) and extracted with ethyl acetate (50 mL*2). The combined organic layers were washed with brine (50 mL), dried over Na$_2$SO$_4$, filtered and concentrated under reduced pressure to give a residue. The residue was purified by column chromatography (SiO$_2$, petroleum ether/ethyl acetate=10/1 to 5/1) to afford benzyl N-(3-hydroxy-1,1-dimethyl-propyl)carbamate (5 g, 20.02 mmol, 59.00% yield, 95% purity) as a colorless oil. MS (ESI) m/z 238.1 [M+H]$^+$ Step 2: benzyl N-(1,1-dimethyl-3-oxo-propyl)carbamate To a solution of benzyl N-(3-hydroxy-1,1-dimethyl-propyl)carbamate (2.2 g, 9.27 mmol, 1 eq) in DCM (1 mL) was added DMP (4.72 g, 11.13 mmol, 3.44 mL, 1.2 eq). The reaction mixture was stirred at 25° C. for 2 h. Upon completion, the reaction mixture was diluted with H$_2$O (100 mL) and extracted with ethyl acetate (100 mL*2). The combined organic layers were washed with brine (100 mL), dried over Na$_2$SO$_4$, filtered and concentrated under reduced pressure to give a residue. The residue was purified by column chromatography (SiO$_2$, petroleum ether/ethyl acetate=20/1 to 10/1) to afford N-(1,1-dimethyl-3-oxo-propyl)carbamate (1.2 g, 4.59 mmol, 49.51% yield, 90% purity) as a colorless oil. MS (ESI) m/z 236.1 [M+H]$^+$

Step 3: (Z)-5-(benzyloxycarbonylamino)-2-[(2S)-2-(tert-butoxycarbonylamino)-3-methoxy-3-oxo-propyl]-5-methyl-hex-2-enoic acid To a solution of dimethyl (2S)-2-(tert-butoxycarbonylamino)pentanedioate (1.4 g, 5.09 mmol, 1 eq) in THF (15 mL) was added a solution of LiHMDS (1 M, 10.68 mL, 2.1 eq) drop-wise at −60° C. under $N_2$. After stirring at −60° C. for 0.5 h, benzyl N-(1,1-dimethyl-3-oxo-propyl)carbamate (1.20 g, 5.09 mmol, 1 eq) in THF (10 mL) was added at below −60° C. and the reaction mixture was stirred at −60° C. for 3 h. Upon completion, the reaction mixture was quenched by addition AcOH 5 mL in THF (20 mL) at 0° C. and concentrated under reduced pressure to give a residue. The residue was purified by neutral prep-HPLC (column: Welch Xtimate C18 250*70 mm #10 um; mobile phase: [water (10 mM $NH_4HCO_3$)-ACN]; B %: 20%-50%, 20 min) to get (Z)-5-(benzyloxycarbonylamino)-2-[(2S)-2-(tert-butoxycarbonylamino)-3-methoxy-3-oxo-propyl]-5-methyl-hex-2-enoic acid (230 mg, 456.60 umol, 8.98% yield, 95% purity) as a white solid. MS (ESI) m/z 379.1 $[M+H-100]^+$

Step 4: dimethyl (2Z,4S)-2-[3-(benzyloxycarbonylamino)-3-methyl-butylidene]-4-(tert-butoxycarbonylamino)pentanedioate To a mixture of (Z)-5-(benzyloxycarbonylamino)-2-[(2S)-2-(tert-butoxycarbonylamino)-3-methoxy-3-oxo-propyl]-5-methyl-hex-2-enoic acid (250 mg, 522.43 umol, 1 eq) in DMF (2.5 mL) was added $K_2CO_3$ (144.41 mg, 1.04 mmol, 2 eq) and $CH_3I$ (222.46 mg, 1.57 mmol, 97.57 uL, 3 eq). The mixture was stirred at 25° C. for 1 h. Upon completion, the reaction mixture was quenched by the addition of $H_2O$ (10 mL) at 0° C., and then diluted with $H_2O$ (10 mL) and extracted with ethyl acetate (10 mL*2). The combined organic layers were washed with brine (10 mL), dried over $Na_2SO_4$, filtered and concentrated under reduced pressure to give a residue compound dimethyl (2Z,4S)-2-[3-(benzyloxycarbonylamino)-3-methyl-butylidene]-4-(tert-butoxycarbonylamino)pentanedioate (230 mg, 420.25 umol, 80.44% yield, 90% purity) as a colorless oil. The residue was used next step directly. MS (ESI) m/z 393.2 $[M+H-100]^+$

Step 5: dimethyl (4S)-2-(3-amino-3-methyl-butyl)-4-(tert-butoxy carbonylamino)pentanedioate To a mixture of dimethyl (2Z,4S)-2-[3-(benzyloxycarbonylamino)-3-methyl-butylidene]-4-(tert-butoxycarbonylamino)pentanedioate (230 mg, 466.95 umol, 1 eq) in i-PrOH (10 mL) was added Pd/C (300 mg, 466.95 umol, 10% purity, 1 eq). The mixture was stirred at 50° C. for 5 h under $H_2$ (50 Psi). Upon completion, the reaction mixture was filtered and concentrated under reduced pressure to give a residue compound dimethyl (4S)-2-(3-amino-3-methyl-butyl)-4-(tert-butoxycarbonylamino) pentanedioate (120 mg, 299.63 umol, 64.17% yield, 90% purity) as a colorless oil and used directly next step. MS (ESI) m/z 361.2 $[M+H]^+$

Step 6: methyl (2S)-2-(tert-butoxycarbonylamino)-3-(6,6-dimethyl-2-oxo-3-piperidyl)propanoate To a mixture of dimethyl (4S)-2-(3-amino-3-methyl-butyl)-4-(tert-butoxycarbonylamino) pentanedioate (120 mg, 332.92 umol, 1 eq) in MeOH (0.5 mL) and $CHCl_3$ (0.05 mL) was added KOAc (65.35 mg, 665.84 umol, 2 eq). The mixture was stirred at 80° C. for 16 h. Upon completion, the residue was diluted with $H_2O$ 5 mL and extracted with ethyl acetate (5 mL*2). The combined organic layers were washed with brine (10 mL), dried over $Na_2SO_4$, filtered and concentrated under reduced pressure to give a residue compound methyl (2S)-2-(tert-butoxycarbonylamino)-3-(6,6-dimethyl-2-oxo-3-piperidyl)propanoate (100 mg, 274.05 umol, 82.32% yield, 90% purity) as a colorless oil and used directly. MS (ESI) m/z 329.2 $[M+H]^+$

Step 7: methyl (2S)-2-amino-3-(6,6-dimethyl-2-oxo-3-piperidyl)propanoate

Methyl (2S)-2-(tert-butoxycarbonylamino)-3-(6,6-dimethyl-2-oxo-3-piperidyl)propanoate (100 mg, 304.50 umol, 1 eq) was added with HCl/MeOH (4 M, 76.13 uL, 1 eq). The resulting mixture was stirred at 25° C. for 1 h. Upon completion, the reaction mixture was concentrated under reduced pressure to give a residue compound methyl (2S)-2-amino-3-(6,6-dimethyl-2-oxo-3-piperidyl)propanoate (80 mg, 287.07 umol, 94.27% yield, 95% purity, HCl) as a colorless oil.

Step 8: methyl (2S)-2-[[(2S)-2-(tert-butoxycarbonylamino)-3-cyclopropyl-propanoyl]amino]-3-(6,6-dimethyl-2-oxo-3-piperidyl)propanoate To a mixture of methyl (2S)-2-amino-3-(6,6-dimethyl-2-oxo-3-piperidyl)propanoate (80 mg, 302.17 umol, 1 eq, HCl) and (2S)-2-(tert-butoxycarbonylamino)-3-cyclopropyl-propanoic acid (69.28 mg, 302.17 umol, 1 eq) in DCM (2 mL) and DMF (1 mL) was added DMAP (73.83 mg, 604.35 umol, 2 eq) and EDCI (115.85 mg, 604.35 umol, 2 eq). The mixture was stirred at 25° C. for 1 h. Upon completion, the reaction mixture was diluted with $H_2O$ (20 mL) and extracted with ethyl acetate (20 mL*2). The combined organic layers were washed with brine (20 mL), dried over $Na_2SO_4$, filtered and concentrated under reduced pressure to give a residue. The residue was purified by column chromatography ($SiO_2$, petroleum ether/ethyl acetate=10/1 to 3/1) to afford methyl (2S)-2-[[(2S)-2-(tert-butoxycarbonylamino)-3-cyclopropyl-propanoyl]amino]-3-(6,6-dimethyl-2-oxo-3-piperidyl)propanoate (110 mg, 225.23 umol, 74.54% yield, 90% purity) as a colorless oil. MS (ESI) m/z 440.3 $[M+H]^+$

Step 9: methyl (2S)-2-[[(2S)-2-amino-3-cyclopropyl-propanoyl]amino]-3-(6,6-dimethyl-2-oxo-3-piperidyl)propanoate Methyl (2S)-2-[[(2S)-2-(tert-butoxycarbonylamino)-3-cyclopropyl-propanoyl]amino]-3-(6,6-dimethyl-2-oxo-3-piperidyl)propanoate (110 mg, 250.26 umol, 1 eq) was added with HCl/MeOH (4 M, 7.33 mL, 117.21 eq). The mixture was stirred at 25° C. for 1 h. Upon completion, the reaction mixture was concentrated under reduced pressure to give a residue compound methyl (2S)-2-[[(2S)-2-amino-3-cyclopropyl-propanoyl]amino]-3-(6,6-dimethyl-2-oxo-3-piperidyl)propanoate (90 mg, 239.43 umol, 95.67% yield, HCl) as a colorless oil.

Step 10: methyl (2S)-2-[[(2S)-2-[(7-chloro-1H-indole-2-carbonyl)amino]-3-cyclopropyl-propanoyl]amino]-3-(6,6-dimethyl-2-oxo-3-piperidyl)propanoate To a mixture of 7-chloro-1H-indole-2-carboxylic acid (46.83 mg, 239.43 umol, 1 eq) and methyl (2S)-2-[[(2S)-2-amino-3-cyclopropyl-propanoyl]amino]-3-(6,6-dimethyl-2- oxo-3-piperidyl)propanoate (90 mg, 239.43 umol, 1 eq, HCl) in DCM (4 mL) and DMF (2 mL) was added EDCI (91.80 mg, 478.86 umol, 2 eq) and DMAP (58.50 mg, 478.86 umol, 2 eq). The mixture was stirred at 25° C. for 1 h. Upon completion, the reaction mixture was diluted with H₂O 20 mL and extracted with EA 40 mL (20 mL*2). The combined organic layers were washed with brine (20 mL), dried over Na₂SO₄, filtered and concentrated under reduced pressure to give a residue. The residue was purified by prep-TLC (SiO₂, petroleum ether:ethyl acetate=0:1) to get the compound methyl (2S)-2-[[(2S)-2-[(7-chloro-1H-indole-2-carbonyl) amino]-3-cyclopropyl-propanoyl]amino]-3-(6,6-dimethyl-2-oxo-3-piperidyl)propanoate (100 mg, 183.75 umol, 76.74% yield, 95% purity) as a white solid. MS (ESI) m/z 517.3 [M+H]⁺

Step 11: N-[(1S)-2-[[(1S)-2-amino-1-[(6,6-dimethyl-2-oxo-3-piperidyl)methyl]-2-oxo-ethyl]amino]-1-(cyclopropylmethyl)-2-oxo-ethyl]-7-chloro-1H-indole-2-carboxamide A solution of methyl (2S)-2-[[(2S)-2-[(7-chloro-1H-indole-2-carbonyl)amino]-3-cyclopropyl-propanoyl]amino]-3-(6,6-dimethyl-2-oxo-3-piperidyl)propanoate (100 mg, 193.42 umol, 1 eq) in NH₃/MeOH (7 M, 10.00 mL, 361.91 eq) was stirred at 55° C. for another 16 h. Upon completion, the reaction mixture concentrated under reduced pressure to give a residue and used next step directly. Compound N-[(1S)-2-[[(1S)-2-amino-1-[(6,6-dimethyl-2-oxo-3-piperidyl)methyl]-2-oxo-ethyl]amino]-1-(cyclopropylmethyl)-2-oxo-ethyl]-7-chloro-1H-indole-2-carboxamide (100 mg, 185.26 umol, 95.78% yield, 93% purity) was obtained as a white solid. MS (ESI) m/z 502.2 [M+H]⁺

Step 12: 7-chloro-N-[(1S)-2-[[(1S)-1-cyano-2-(6,6-dimethyl-2-oxo-3-piperidyl)ethyl]amino]-1-(cyclopropylmethyl)-2-oxo-ethyl]-1H-indole-2-carboxamide To a mixture of N-[(1S)-2-[[(1S)-2-amino-1-[(6,6-dimethyl-2-oxo-3-piperidyl)methyl]-2-oxo-ethyl]amino]-1-(cyclopropylmethyl)-2-oxo-ethyl]-7-chloro-1H-indole-2-carboxamide (80 mg, 159.36 umol, 1 eq) in DCM (5 mL) was added Burgess reagent (75.95 mg, 318.72 umol, 2 eq). The mixture was stirred at 20° C. for 3 h. Upon completion, the reaction mixture was diluted with H₂O (5 mL) and extracted with DCM (5 mL*2). The combined organic layers were concentrated with using blow-dry to give a residue. The residue was purified by prep-HPLC (column: Waters Xbridge BEH C18 100*30 mm*10 um; mobile phase: [water (10 mM NH₄HCO₃)-ACN]; B %: 30%-60%, 8 min) to give the mixture product (65 mg) as a white solid. The white solid (65 mg) was separated by SFC (column: REGIS (s,s) WHELK-O1 (250 mm*30 mm, 5 um); mobile phase: [0.1% NH₃H₂O IPA]; B %: 55%-55%, 8 min) to get the compound 7-chloro-N-[(1S)-2-[[(1S)-1-cyano-2-(6,6-dimethyl-2-oxo-3-piperidyl)ethyl]amino]-1-(cyclopropylmethyl)-2-oxo-ethyl]-1H-indole-2-carboxamide (35 mg, 72.32 umol, 45.38% yield, 100% purity) and 7-chloro-N-[(1S)-2-[[(1S)-1-cyano-2-(6,6-dimethyl-2-oxo-3-piperidyl)ethyl]amino]-1-(cyclopropylmethyl)-2-oxo-ethyl]-1H-indole-2-carboxamide (25 mg, 51.65 umol, 32.41% yield, 100% purity) as a white solid. MS (ESI) m/z 484.2 [M+H]⁺

Isomer 1:

¹H NMR (400 MHz, DMSO-d₆) δ=11.86-11.59 (m, 1H), 9.00 (d, J=8.0 Hz, 1H), 8.72 (d, J=7.6 Hz, 1H), 7.63 (d, J=8.0 Hz, 1H), 7.49 (s, 1H), 7.31 (d, J=7.5 Hz, 1H), 7.28-7.23 (m, 1H), 7.07 (t, J=7.8 Hz, 1H), 5.09 (q, J=8.0 Hz, 1H), 4.61-4.46 (m, 1H), 2.30-2.08 (m, 2H), 1.88-1.67 (m, 3H), 1.64-1.38 (m, 4H), 1.17-1.03 (m, 6H), 0.89-0.70 (m, 1H), 0.51-0.36 (m, 2H), 0.28-0.01 (m, 2H).

Isomer 2:

¹H NMR (400 MHz, DMSO-d₆) δ=11.73 (s, 1H), 9.04 (d, J=7.4 Hz, 1H), 8.74 (d, J=7.7 Hz, 1H), 7.63 (d, J=7.9 Hz, 1H), 7.51 (s, 1H), 7.31 (d, J=7.5 Hz, 1H), 7.26 (s, 1H), 7.07 (t, J=7.7 Hz, 1H), 5.02 (q, J=7.4 Hz, 1H), 4.61-4.52 (m, 1H), 2.32 (td, J=6.8, 13.7 Hz, 1H), 2.20-2.06 (m, 1H), 1.88-1.49 (m, 7H), 1.12 (d, J=8.0 Hz, 6H), 0.88-0.70 (m, 1H), 0.52-0.34 (m, 2H), 0.26-0.05 (m, 2H).

Example 210. Synthesis of Viral Protease Inhibitor Compound 928

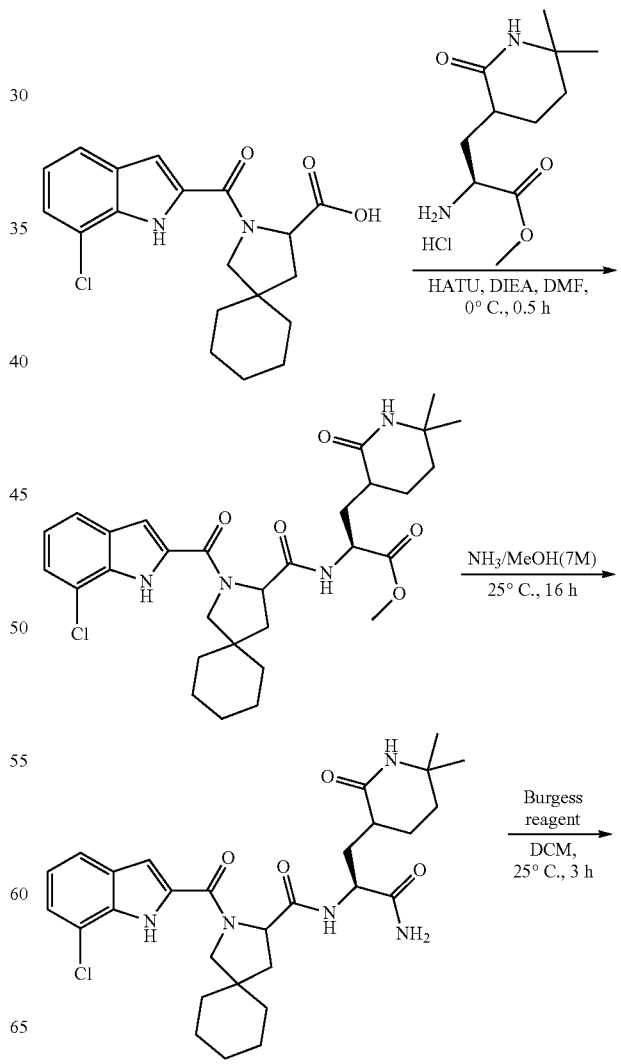

1275

-continued

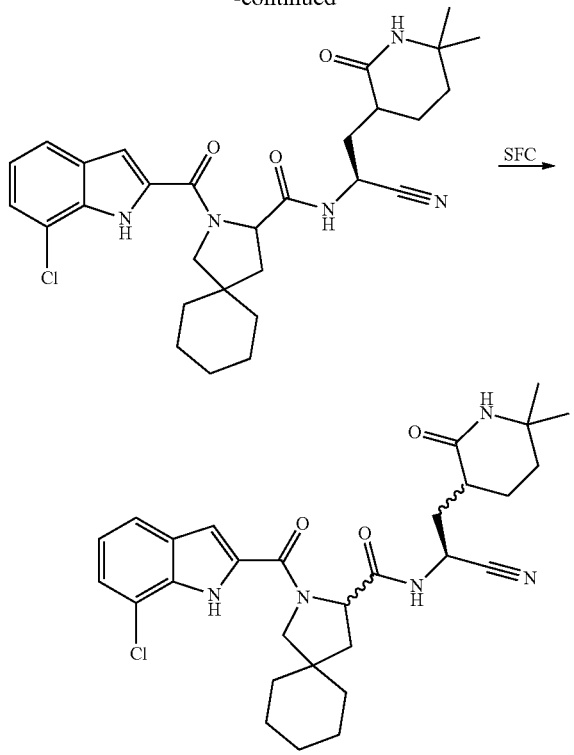

Step 1: methyl (2S)-2-[[2-(7-chloro-1H-indole-2-carbonyl)-2-azaspiro[4.5]decane-3-carbonyl]amino]-3-(6,6-dimethyl-2-oxo-3-piperidyl)propanoate To a mixture of 2-(7-chloro-1H-indole-2-carbonyl)-2-azaspiro[4.5]decane-3-carboxylic acid (354.36 mg, 982.06 umol, 1 eq) and methyl (2S)-2-amino-3-(6,6-dimethyl-2-oxo-3-piperidyl)propanoate (260 mg, 982.06 umol, 1 eq, HCl) in DMF (10 mL) was added HATU (448.09 mg, 1.18 mmol, 1.2 eq), DIEA (380.78 mg, 2.95 mmol, 513.17 uL, 3 eq) in DMF (5 mL) was added at 0° C. The mixture was stirred at 0° C. for 30 min. Upon completion, the reaction mixture was diluted with H$_2$O 50 mL and extracted with EA 100 mL (50 mL*2). The combined organic layers were washed with brine 50 mL (50 mL*1), dried over Na$_2$SO$_4$, filtered and concentrated under reduced pressure to give a residue. The residue was purified by column chromatography (SiO2, Petroleum ether/Ethyl acetate=10/1 to 0/1) to get the compound methyl (2S)-2-[[2-(7-chloro-1H-indole-2-carbonyl)-2-azaspiro[4.5]decane-3-carbonyl] amino]-3-(6,6-dimethyl-2-oxo-3-piperidyl)propanoate (550 mg, 866.74 umol, 88.26% yield, 90% purity) as a white solid. MS (ESI) m/z 571.3 [M+H]$^+$ Step 2: N-[(1S)-2-amino-1-[(6,6-dimethyl-2-oxo-3-piperidyl)methyl]-2-oxo-ethyl]-2-(7-chloro-1H-indole-2-carbonyl)-2-azaspiro[4.5]decane-3-carboxamide To a mixture of methyl (2S)-2-[[2-(7-chloro-1H-indole-2-carbonyl)-2-azaspiro[4.5]decane-3-carbonyl]amino]-3-(6,6-dimethyl-2-oxo-3-piperidyl)propanoate (550 mg, 963.04 umol, 1 eq) was added NH$_3$/MeOH (7 M, 137.58 uL, 1 eq) at 25° C. The mixture was stirred at 25° C. for 16 h. Upon completion, the reaction mixture was concentrated under reduced pressure to give a residue compound N-[(1S)-2-amino-1-[(6,6-dimethyl-2-oxo-3-piperidyl)methyl]-2-oxo-ethyl]-2-(7-chloro-1H-indole-2-carbonyl)-2-azaspiro[4.5] decane-3-carboxamide (520 mg, 841.58 umol, 87.39% yield, 90% purity) as a white solid and the residue was used next step directly. MS (ESI) m/z 556.3 [M+H]$^+$ Step 3: 2-(7-chloro-1H-indole-2-carbonyl)-N-[(1S)-1-cyano-2-(6,6-dimethyl-2-oxo-3-piperidyl)ethyl]-2-azaspiro[4.5]decane-3-carboxamide To a mixture of N-[(1S)-2-amino-1-[(6,6-dimethyl-2-oxo-3-piperidyl)methyl]-2-oxo-ethyl]-2-(7-chloro-1H-indole-2-carbonyl)-2-azaspiro[4.5]decane-3-carboxamide (500 mg, 899.13 umol, 1 eq) in DCM (10 mL) was added BURGESS REAGENT (428.53 mg, 1.80 mmol, 2 eq) at 25° C. The mixture was stirred at 25° C. for 3 h. Upon completion, the reaction mixture was diluted with H$_2$O 10 mL and extracted with DCM 20 mL (10 mL*2). The combined organic layers were washed with brine 10 mL (10 mL*1) and blow-drying by N2 to give a residue. The residue was purified by neutral prep-HPLC (column: Waters Xbridge C18 150*50 mm*10 um; mobile phase: [water (10 mM NH4HCO3)-ACN]; B %: 40%-60%, 10 min). MS (ESI) m/z 538.2 [M+H]$^+$ Isomer 1&2:
2-(7-chloro-1H-indole-2-carbonyl)-N-[(1S)-1-cyano-2-(6,6-dimethyl-2-oxo-3-piperidyl)ethyl]-2-azaspiro[4.5]decane-3-carboxamide (100 mg, 185.10 umol, 20.59% yield, 99.6% purity) was obtained as a white solid.
$^1$H NMR (400 MHz, DMSO-d6) δ=11.10 (br s, 1H), 8.70 (br d, J=16.5 Hz, 1H), 7.62 (br s, 1H), 7.38-6.82 (m, 4H), 4.98 (br s, 1H), 4.60 (br s, 1H), 3.83 (br d, J=10.1 Hz, 1H), 3.62 (br s, 1H), 2.31-1.96 (m, 3H), 1.94-1.26 (m, 16H), 1.22-1.01 (m, 6H)

Isomer 3:
2-(7-chloro-1H-indole-2-carbonyl)-N-[(1S)-1-cyano-2-(6,6-dimethyl-2-oxo-3-piperidyl)ethyl]-2-azaspiro[4.5]decane-3-carboxamide (50 mg, 92.92 umol, 10.33% yield, 100% purity) was obtained as a white solid.
$^1$H NMR (400 MHz, DMSO-d6) δ=11.12 (br s, 1H), 9.01-8.62 (m, 1H), 7.83-7.52 (m, 1H), 7.49-6.65 (m, 4H), 4.94 (br d, J=5.7 Hz, 1H), 4.61 (br s, 1H), 4.00-3.33 (m, 2H), 2.35-1.99 (m, 3H), 1.91-1.28 (m, 16H), 1.20-1.07 (m, 6H)

Isomer 4:
2-(7-chloro-1H-indole-2-carbonyl)-N-[(1S)-1-cyano-2-(6,6-dimethyl-2-oxo-3-piperidyl)ethyl]-2-azaspiro[4.5]decane-3-carboxamide (50 mg, 90.69 umol, 10.09% yield, 97.6% purity) was obtained as a white solid.
$^1$H NMR (400 MHz, DMSO-d6) δ=11.54-10.62 (m, 1H), 8.96-8.58 (m, 1H), 7.63 (br d, J=7.3 Hz, 1H), 7.39-6.91 (m, 4H), 4.94 (q, J=6.8 Hz, 1H), 4.60 (br s, 1H), 3.92-3.46 (m, 2H), 2.31-2.01 (m, 3H), 1.76-1.29 (m, 16H), 1.14 (d, J=18.3 Hz, 6H)

Example 211. Synthesis of Viral Protease Inhibitor Compound 930

Step 1: methyl 2-azaspiro[4.5]decane-3-carboxylate

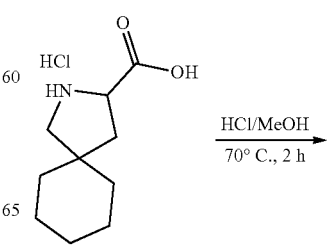

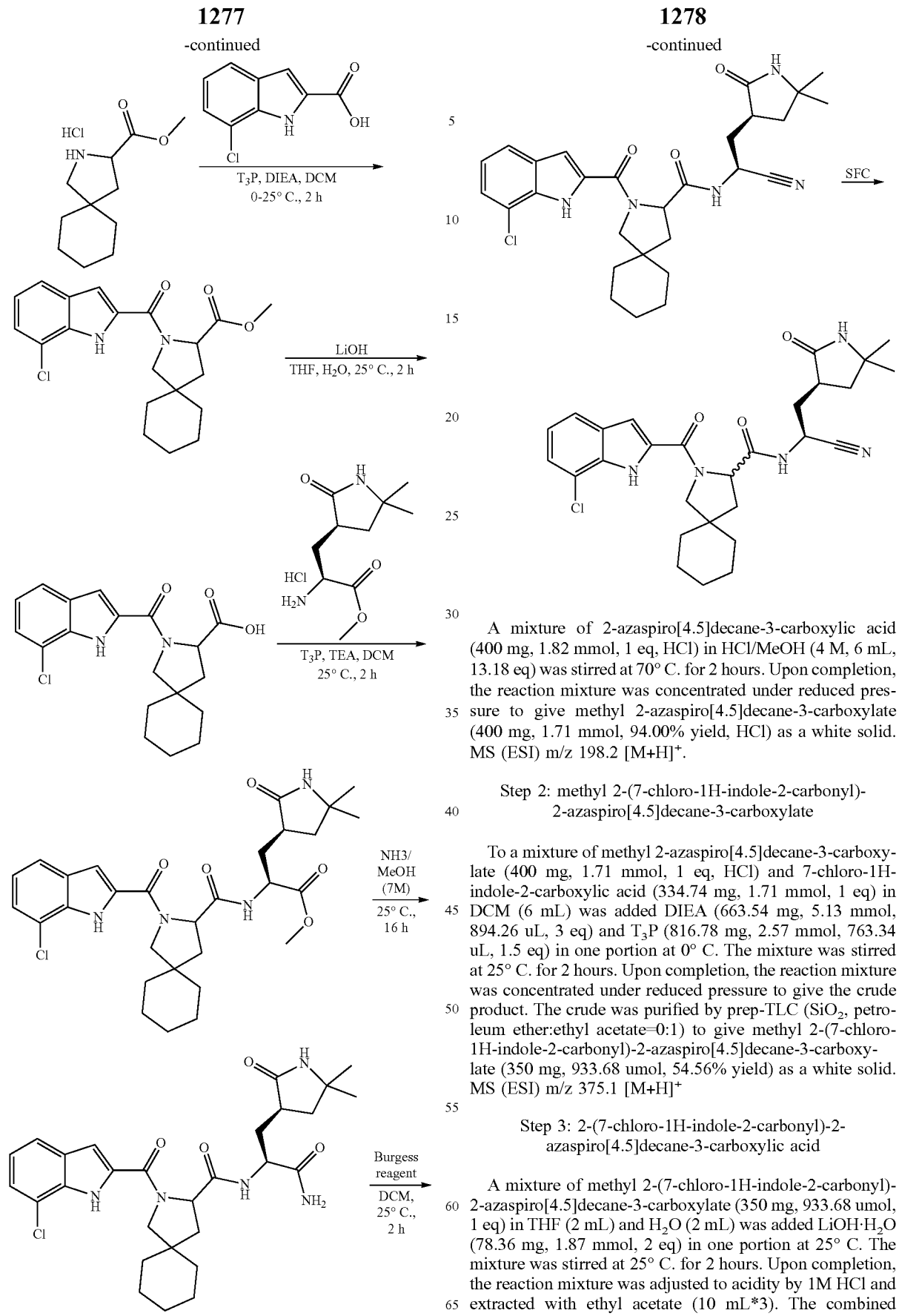

A mixture of 2-azaspiro[4.5]decane-3-carboxylic acid (400 mg, 1.82 mmol, 1 eq, HCl) in HCl/MeOH (4 M, 6 mL, 13.18 eq) was stirred at 70° C. for 2 hours. Upon completion, the reaction mixture was concentrated under reduced pressure to give methyl 2-azaspiro[4.5]decane-3-carboxylate (400 mg, 1.71 mmol, 94.00% yield, HCl) as a white solid. MS (ESI) m/z 198.2 [M+H]$^+$.

Step 2: methyl 2-(7-chloro-1H-indole-2-carbonyl)-2-azaspiro[4.5]decane-3-carboxylate To a mixture of methyl 2-azaspiro[4.5]decane-3-carboxylate (400 mg, 1.71 mmol, 1 eq, HCl) and 7-chloro-1H-indole-2-carboxylic acid (334.74 mg, 1.71 mmol, 1 eq) in DCM (6 mL) was added DIEA (663.54 mg, 5.13 mmol, 894.26 uL, 3 eq) and T$_3$P (816.78 mg, 2.57 mmol, 763.34 uL, 1.5 eq) in one portion at 0° C. The mixture was stirred at 25° C. for 2 hours. Upon completion, the reaction mixture was concentrated under reduced pressure to give the crude product. The crude was purified by prep-TLC (SiO$_2$, petroleum ether:ethyl acetate=0:1) to give methyl 2-(7-chloro-1H-indole-2-carbonyl)-2-azaspiro[4.5]decane-3-carboxylate (350 mg, 933.68 umol, 54.56% yield) as a white solid. MS (ESI) m/z 375.1 [M+H]$^+$ Step 3: 2-(7-chloro-1H-indole-2-carbonyl)-2-azaspiro[4.5]decane-3-carboxylic acid A mixture of methyl 2-(7-chloro-1H-indole-2-carbonyl)-2-azaspiro[4.5]decane-3-carboxylate (350 mg, 933.68 umol, 1 eq) in THF (2 mL) and H$_2$O (2 mL) was added LiOH·H$_2$O (78.36 mg, 1.87 mmol, 2 eq) in one portion at 25° C. The mixture was stirred at 25° C. for 2 hours. Upon completion, the reaction mixture was adjusted to acidity by 1M HCl and extracted with ethyl acetate (10 mL*3). The combined organic layers were washed with brine (15 mL*1), dried over Na$_2$SO$_4$, and filtered and concentrated under reduced pressure to give 2-(7-chloro-1H-indole-2-carbonyl)-2-azaspiro[4.5]decane-3-carboxylic acid (280 mg, 775.98 umol, 83.11% yield) as a white solid. MS (ESI) m/z 361.0 [M+H]$^+$ Step 4: methyl (2S)-2-[[2-(7-chloro-1H-indole-2-carbonyl)-2-azaspiro[4.5]decane-3-carbonyl]amino]-3-[(3R)-5,5-dimethyl-2-oxo-pyrrolidin-3-yl]propanoate To a mixture of 2-(7-chloro-1H-indole-2-carbonyl)-2-azaspiro[4.5]decane-3-carboxylic acid (250 mg, 692.84 umol, 1 eq) and methyl (2S)-2-amino-3-[(3R)-5,5-dimethyl-2-oxo-pyrrolidin-3-yl]propanoate (225.82 mg, 900.69 umol, 1.3 eq, HCl) in DCM (4 mL) was added T$_3$P (661.35 mg, 1.04 mmol, 618.08 uL, 50% purity, 1.5 eq) and TEA (210.32 mg, 2.08 mmol, 289.30 uL, 3 eq) in one portion at 0° C. The mixture was stirred at 25° C. for 2 hours. Upon completion, the reaction mixture was concentrated under reduced pressure to give the crude product. The crude was purified by prep-TLC (SiO2, PE:ethyl acetate=0: 1) to give methyl (2S)-2-[[2-(7-chloro-1H-indole-2-carbonyl)-2-azaspiro[4.5]decane-3-carbonyl]amino]-3-[(3R)-5,5-dimethyl-2-oxo-pyrrolidin-3-yl]propanoate (270 mg, 484.67 umol, 69.95% yield) as a white solid. MS (ESI) m/z 557.1 [M+H]$^+$ Step 5: N-[(1S)-2-amino-1-[(5,5-dimethyl-2-oxo-pyrrolidin-3-yl)methyl]-2-oxo-ethyl]-2-(7-chloro-1H-indole-2-carbonyl)-2-azaspiro[4.5]decane-3-carboxamide A mixture of methyl (2S)-2-[[2-(7-chloro-1H-indole-2-carbonyl)-2-azaspiro[4.5]decane-3-carbonyl]amino]-3-(5,5-dimethyl-2-oxo-pyrrolidin-3-yl)propanoate (250 mg, 448.77 umol, 1 eq) in NH$_3$/MeOH (7 M, 5 mL, 77.99 eq) was stirred at 25° C. for 16 h. Upon completion, the reaction mixture was concentrated under reduced pressure to give N-[(1S)-2-amino-1-[(5,5-dimethyl-2-oxo-pyrrolidin-3-yl)methyl]-2-oxo-ethyl]-2-(7-chloro-1H-indole-2-carbonyl)-2-azaspiro[4.5]decane-3-carboxamide (240 mg, 442.75 umol, 98.66% yield) as a white solid. MS (ESI) m/z 542.2 [M+H]$^+$ Step 6: 2-(7-chloro-1H-indole-2-carbonyl)-N-[(1S)-1-cyano-2-(5,5-dimethyl-2-oxo-pyrrolidin-3-yl)ethyl]-2-azaspiro[4.5]decane-3-carboxamide A mixture of N-[(1S)-2-amino-1-[(5,5-dimethyl-2-oxo-pyrrolidin-3-yl)methyl]-2-oxo-ethyl]-2-(7-chloro-1H-indole-2-carbonyl)-2-azaspiro[4.5]decane-3-carboxamide (250 mg, 392.02 umol, 85% purity, 1 eq) in DCM (5 mL) was added Burgess reagent (186.84 mg, 784.03 umol, 2 eq) in one portion at 25° C. The mixture was stirred at 25° C. for 2 hours. Upon completion, the reaction mixture was concentrated under reduced pressure to give the crude product. The crude was purified by prep-HPLC (neutral condition; column: Waters Xbridge Prep OBD C18 150*40 mm*10 um; mobile phase: [water (10 mM NH$_4$HCO$_3$)-ACN]; B %: 35%-65%, 8 min) to give 2-(7-chloro-1H-indole-2-carbonyl)-N-[(1S)-1-cyano-2-(5,5-dimethyl-2-oxo-pyrrolidin-3-yl)ethyl]-2-azaspiro[4.5]decane-3-carboxamide (100 mg, 190.82 umol, 48.68% yield) as a white solid. MS (ESI) m/z 524.2 [M+H]$^+$ Step 7: 2-(7-chloro-1H-indole-2-carbonyl)-N-[(1S)-1-cyano-2-(5,5-dimethyl-2-oxo-pyrrolidin-3-yl)ethyl]-2-azaspiro[4.5]decane-3-carboxamide The white solid was separated by SFC (column: REGIS (S,S)WHELK-O1 (250 mm*25 mm, 10 um); mobile phase: [0.1% NH$_3$H$_2$O ETOH]; B %: 55%-55%, 10 min) to give 2-(7-chloro-1H-indole-2-carbonyl)-N-[(1S)-1-cyano-2-(5,5-dimethyl-2-oxo-pyrrolidin-3-yl)ethyl]-2-azaspiro[4.5]decane-3-carboxamide (2 mg, 3.82 umol, 2.00% yield), 2-(7-chloro-1H-indole-2-carbonyl)-N-[(1S)-1-cyano-2-(5,5-dimethyl-2-oxo-pyrrolidin-3-yl)ethyl]-2-azaspiro[4.5]decane-3-carboxamide (2 mg, 3.82 umol, 2.00% yield), 2-(7-chloro-1H-indole-2-carbonyl)-N-[(1S)-1-cyano-2-(5,5-dimethyl-2-oxo-pyrrolidin-3-yl)ethyl]-2-azaspiro[4.5]decane-3-carboxamide (30 mg, 57.25 umol, 30.00% yield), 2-(7-chloro-1H-indole-2-carbonyl)-N-[(1S)-1-cyano-2-(5,5-dimethyl-2-oxo-pyrrolidin-3-yl)ethyl]-2-azaspiro[4.5]decane-3-carboxamide (5 mg, 9.54 umol, 5.00% yield), 2-(7-chloro-1H-indole-2-carbonyl)-N-[(1S)-1-cyano-2-(5,5-dimethyl-2-oxo-pyrrolidin-3-yl)ethyl]-2-azaspiro[4.5]decane-3-carboxamide (20 mg, 38.16 umol, 20.00% yield) and 2-(7-chloro-1H-indole-2-carbonyl)-N-[(1S)-1-cyano-2-(5,5-dimethyl-2-oxo-pyrrolidin-3-yl)ethyl]-2-azaspiro[4.5]decane-3-carboxamide (15 mg) as a white solid. MS (ESI) m/z 524.2 [M+H]$^+$ Isomer 1:
$^1$H NMR (400 MHz, DMSO-d$_6$) δ=11.69-11.44 (m, 1H), 8.95 (br d, J=7.9 Hz, 1H), 7.87-7.75 (m, 1H), 7.68-7.43 (m, 1H), 7.33-7.20 (m, 1H), 7.14 (s, 1H), 7.11-6.97 (m, 1H), 4.99-4.75 (m, 1H), 4.50 (t, J=8.6 Hz, 1H), 3.83 (br d, J=10.4 Hz, 1H), 3.66 (d, J=10.6 Hz, 1H), 2.75-2.63 (m, 1H), 2.36-2.12 (m, 2H), 1.99 (dd, J=8.5, 12.2 Hz, 1H), 1.83-1.69 (m, 1H), 1.60 (br dd, J=9.9, 11.9 Hz, 1H), 1.55-1.28 (m, 1H), 1.17-1.06 (m, 3H), 1.05-0.91 (m, 3H)

$^1$H NMR (400 MHz, DMSO-d$_6$) δ=11.07 (br s, 1H), 8.73 (br d, J=7.5 Hz, 1H), 7.75-7.47 (m, 2H), 7.28 (d, J=7.5 Hz, 1H), 7.07 (br t, J=7.7 Hz, 2H), 4.91 (br d, J=7.3 Hz, 1H), 4.59 (br s, 1H), 3.84 (d, J=10.1 Hz, 1H), 3.63 (br s, 1H), 2.30-1.92 (m, 3H), 1.78 (br s, 1H), 1.72-1.63 (m, 1H), 1.60-1.33 (m, 12H), 1.18 (s, 3H), 1.09 (s, 3H) Isomer 2:

$^1$H NMR (400 MHz, DMSO-d$_6$) δ=11.56 (br s, 1H), 9.00-8.79 (m, 1H), 7.82 (s, 1H), 7.68-7.48 (m, 1H), 7.32-7.22 (m, 1H), 7.15 (s, 1H), 7.12-6.99 (m, 1H), 4.98-4.71 (m, 1H), 4.50 (t, J=8.7 Hz, 1H), 3.90-3.77 (m, 1H), 3.73-3.60 (m, 1H), 2.47-2.39 (m, 1H), 2.24 (br dd, J=7.9, 12.3 Hz, 1H), 2.17-2.08 (m, 1H), 1.98 (br dd, J=8.4, 11.9 Hz, 1H), 1.83-1.68 (m, 1H), 1.61-1.51 (m, 2H), 1.50-1.36 (m, 7H), 1.35-1.21 (m, 3H), 1.15 (s, 3H), 1.08-0.97 (m, 3H)

$^1$H NMR (400 MHz, DMSO-d$_6$) δ=11.09 (br s, 1H), 8.66 (br s, 1H), 7.65-7.53 (m, 2H), 7.26 (d, J=7.7 Hz, 1H), 7.12-6.97 (m, 2H), 4.89 (br d, J=5.7 Hz, 1H), 4.57 (br s, 1H), 3.88-3.56 (m, 2H), 2.28-1.96 (m, 3H), 1.85-1.60 (m, 2H), 1.58-1.22 (m, 12H), 1.16 (s, 3H), 1.07 (s, 2H), 1.09-0.99 (m, 1H) Isomer 3:

$^1$H NMR (400 MHz, DMSO-d$_6$) δ=11.66-11.45 (m, 1H), 8.94 (d, J=8.2 Hz, 1H), 7.92-7.75 (m, 1H), 7.64 (d, J=7.9 Hz, 1H), 7.29 (d, J=7.3 Hz, 1H), 7.17-7.12 (m, 1H), 7.11-6.98 (m, 1H), 5.00-4.73 (m, 1H), 4.50 (br t, J=8.6 Hz, 1H), 3.83 (br d, J=10.4 Hz, 1H), 3.72-3.62 (m, 1H), 2.75-2.63 (m, 1H), 2.31-2.12 (m, 2H), 2.08-1.94 (m, 1H), 1.80-1.57 (m, 2H), 1.54-1.36 (m, 8H), 1.35-1.18 (m, 3H), 1.17-1.07 (m, 3H), 1.07-0.92 (m, 3H)

$^1$H NMR (400 MHz, DMSO-d$_6$) δ=11.07 (br s, 1H), 8.86-8.69 (m, 1H), 7.70-7.55 (m, 2H), 7.28 (d, J=7.5 Hz, 1H), 7.07 (br t, J=7.6 Hz, 2H), 4.98-4.85 (m, 1H), 4.60 (br s, 1H), 3.84 (d, J=10.6 Hz, 1H), 3.64 (s, 1H), 2.29-1.96 (m, 3H), 1.77 (br s, 1H), 1.73-1.63 (m, 1H), 1.61-1.32 (m, 12H), 1.20-1.14 (m, 3H), 1.13-1.06 (m, 3H) Isomer 4:

1H NMR (400 MHz, DMSO-d$_6$) δ=11.69-11.53 (m, 1H), 9.11-8.97 (m, 1H), 7.98-7.85 (m, 1H), 7.68-7.45 (m, 1H), 7.33-7.20 (m, 1H), 7.15 (s, 1H), 7.12-6.96 (m, 1H), 4.97-4.72 (m, 1H), 4.70-4.48 (m, 1H), 3.83 (br d, J=10.4 Hz, 1H), 3.72-3.59 (m, 1H), 2.70-2.54 (m, 1H), 2.35-2.12 (m, 3H), 2.01-1.53 (m, 3H), 1.53-1.39 (m, 6H), 1.39-1.27 (m, 4H), 1.20-1.01 (m, 6H)

$^1$H NMR (400 MHz, DMSO-$d_6$) δ=11.13 (br s, 1H), 8.85 (br s, 1H), 7.74-7.57 (m, 2H), 7.28 (br d, J=7.7 Hz, 1H), 7.18-6.96 (m, 2H), 4.90 (br s, 1H), 4.62 (br s, 1H), 3.85 (br d, J=10.4 Hz, 1H), 3.64 (s, 1H), 2.31-2.22 (m, 1H), 2.14 (br s, 2H), 1.89-1.75 (m, 1H), 1.73-1.64 (m, 1H), 1.60-1.28 (m, 12H), 1.20 (s, 3H), 1.14 (s, 3H) Isomer 5:

1H NMR (400 MHz, DMSO-$d_6$) δ=11.55 (br s, 1H), 9.02-8.77 (m, 1H), 7.82 (s, 1H), 7.69-7.47 (m, 1H), 7.32-7.22 (m, 1H), 7.15 (s, 1H), 7.11-6.98 (m, 1H), 4.98-4.71 (m, 1H), 4.50 (t, J=8.5 Hz, 1H), 3.87-3.77 (m, 1H), 3.74-3.59 (m, 1H), 2.47-2.40 (m, 1H), 2.35-2.20 (m, 1H), 2.19-2.08 (m, 1H), 1.98 (dd, J=8.5, 12.5 Hz, 1H), 1.89-1.70 (m, 1H), 1.69-1.52 (m, 2H), 1.51-1.39 (m, 6H), 1.38-1.28 (m, 4H), 1.15 (s, 3H), 1.07-0.97 (m, 3H)

$^1$H NMR (400 MHz, DMSO-d6) δ=11.12 (br s, 1H), 8.65 (br s, 1H), 7.67-7.52 (m, 2H), 7.28 (d, J=7.7 Hz, 1H), 7.14-6.92 (m, 2H), 4.91 (br d, J=7.1 Hz, 1H), 4.59 (br s, 1H), 3.83 (br d, J=11.0 Hz, 1H), 3.63 (s, 1H), 2.31-2.20 (m, 1H), 2.19-1.96 (m, 2H), 1.81 (br s, 1H), 1.68 (br d, J=10.6 Hz, 1H), 1.61-1.34 (m, 12H), 1.18 (s, 3H), 1.09 (s, 3H) Isomer 6:

$^1$H NMR (400 MHz, DMSO-$d_6$) δ=11.69-11.50 (m, 1H), 9.10-8.98 (m, 1H), 7.97-7.88 (m, 1H), 7.68-7.45 (m, 1H), 7.33-7.19 (m, 1H), 7.15 (s, 1H), 7.11-6.97 (m, 1H), 4.96-4.71 (m, 1H), 4.69-4.47 (m, 1H), 3.83 (br d, J=10.1 Hz, 1H), 3.66 (d, J=10.4 Hz, 1H), 2.69-2.54 (m, 1H), 2.39-2.12 (m, 3H), 1.97-1.56 (m, 2H), 1.55-1.47 (m, 3H), 1.42 (br s, 4H), 1.38-1.28 (m, 4H), 1.21-1.01 (m, 6H)

1H NMR (400 MHz, DMSO-$d_6$) δ=11.12 (br s, 1H), 8.84 (br d, J=7.3 Hz, 1H), 7.74-7.56 (m, 2H), 7.28 (br d, J=7.5 Hz, 1H), 7.07 (br t, J=7.6 Hz, 2H), 4.89 (br s, 1H), 4.61 (br s, 1H), 3.84 (br d, J=10.4 Hz, 1H), 3.62 (br s, 1H), 2.29-2.06 (m, 3H), 1.85-1.61 (m, 2H), 1.59-1.33 (m, 12H), 1.20 (s, 3H), 1.14 (s, 3H)

Step 8: 2-(7-chloro-1H-indole-2-carbonyl)-N-[(1S)-1-cyano-2-(5,5-dimethyl-2-oxo-pyrrolidin-3-yl)ethyl]-2-azaspiro[4.5]decane-3-carboxamide The white solid was separated by SFC (column: REGIS (S,S)WHELK-O1 (250 mm*25 mm, 10 um); mobile phase: [0.1% NH$_3$H$_2$O ETOH]; B %: 55%-55%, 10 min) to give 2-(7-chloro-1H-indole-2-carbonyl)-N-[(1S)-1-cyano-2-(5,5-dimethyl-2-oxo-pyrrolidin-3-yl)ethyl]-2-azaspiro[4.5]decane-3-carboxamide (18 mg, 34.35 umol, 60.00% yield) and 2-(7-chloro-1H-indole-2-carbonyl)-N-[(1S)-1-cyano-2-(5,5-dimethyl-2-oxo-pyrrolidin-3-yl)ethyl]-2-azaspiro[4.5]decane-3-carboxamide (4 mg, 7.63 umol, 13.33% yield) as a white solid. MS (ESI) m/z 524.2 [M+H]$^+$
Isomer 1:

$^1$H NMR (400 MHz, DMSO-$d_6$) δ=11.68-11.45 (m, 1H), 8.95 (br d, J=7.9 Hz, 1H), 7.86-7.76 (m, 1H), 7.68-7.44 (m, 1H), 7.33-7.20 (m, 1H), 7.14 (s, 1H), 7.11-6.97 (m, 1H), 4.98-4.77 (m, 1H), 4.50 (br t, J=8.5 Hz, 1H), 3.83 (br d, J=10.1 Hz, 1H), 3.66 (br d, J=10.1 Hz, 1H), 2.76-2.63 (m, 1H), 2.36-2.10 (m, 2H), 2.05-1.94 (m, 1H), 1.82-1.56 (m, 2H), 1.54-1.18 (m, 1H), 1.17-1.06 (m, 3H), 1.05-0.92 (m, 3H).
Isomer 2:

$^1$H NMR (400 MHz, DMSO-$d_6$) δ=11.58 (br s, 1H), 9.10-8.90 (m, 1H), 7.89 (s, 1H), 7.70-7.44 (m, 1H), 7.30 (d, J=7.5 Hz, 1H), 7.16 (s, 1H), 7.12-6.99 (m, 1H), 4.94-4.82 (m, 1H), 4.51 (t, J=8.6 Hz, 1H), 3.81 (br d, J=10.4 Hz, 1H), 3.70 (br d, J=10.4 Hz, 1H), 2.30-2.10 (m, 2H), 2.03 (dd, J=8.5, 12.0 Hz, 1H), 1.81-1.65 (m, 1H), 1.62-1.18 (m, 13H), 1.16-1.01 (m, 6H).

Example 212. Synthesis of Viral Protease Inhibitor Compound 820

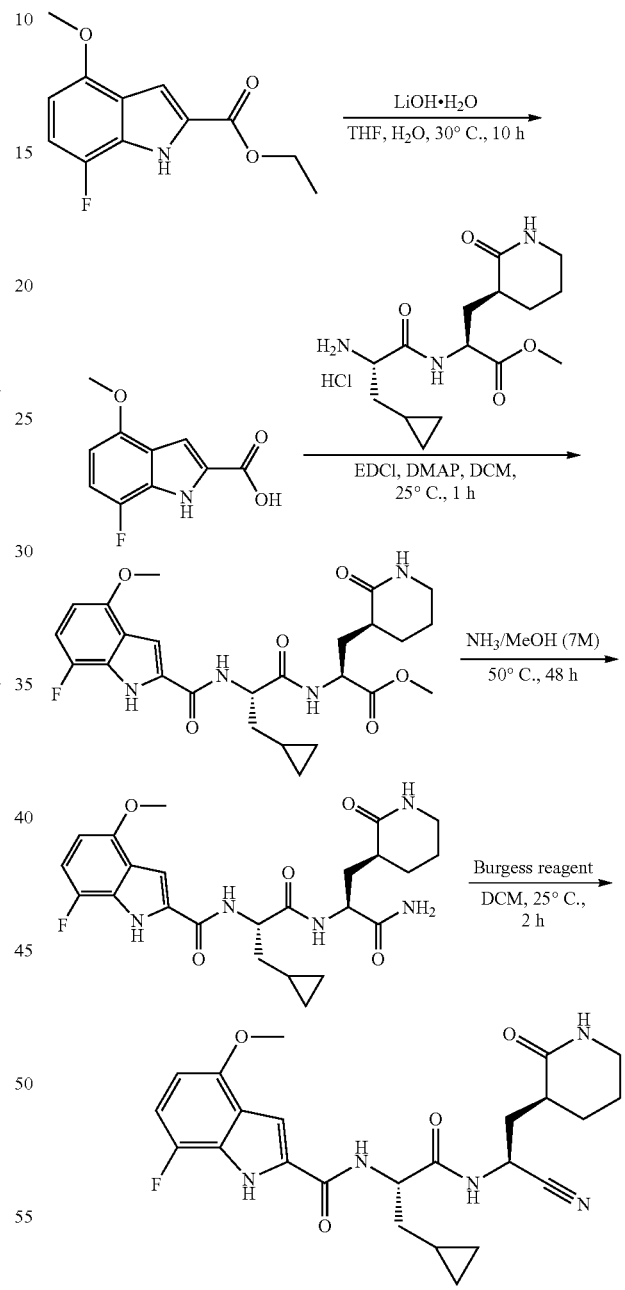

To a solution of ethyl 7-fluoro-4-methoxy-1H-indole-2-carboxylate (800 mg, 3.37 mmol, 1 eq) in THF (10 mL) and H$_2$O (5 mL) was added LiOH·H$_2$O (283.03 mg, 6.74 mmol, 2 eq), and then the mixture was stirred at 30° C. for 10 h. Upon completion, the pH of the reaction mixture was adjust to about 3 with HCl aq (1M). The mixture was extracted with EtOAc (100 mL*3). The combined organic layer was dried over Na$_2$SO$_4$, filtered, concentrated to give product 7-fluoro-4-methoxy-1H-indole-2-carboxylic acid (680 mg, crude) as white solid. MS (ESI) m/z 210.0 [M+H]+

Step 2: (S)-methyl 2-((S)-3-cyclopropyl-2-(7-fluoro-4-methoxy-1H-indole-2-carboxamido)propanamido)-3-((S)-2-oxopiperidin-3-yl)propanoate To a solution of 7-fluoro-4-methoxy-1H-indole-2-carboxylic acid (0.68 g, 3.25 mmol, 1 eq) in DCM (20 mL) was added (S)-methyl 2-((S)-2-amino-3-cyclopropylpropanamido)-3-((S)-2-oxopiperidin-3-yl)propanoate (1.24 g, 3.58 mmol, 1.1 eq, HCl), EDCI (1.25 g, 6.50 mmol, 2 eq), DMAP (1.19 g, 9.75 mmol, 3 eq) and the mixture was stirred at 25° C. for 1 h. Upon completion, the reaction was quenched by the addition of H₂O (200 mL) and then extracted with EtOAc (100 mL*3). The combined organic layers were washed with brine (100 mL), dried over Na₂SO₄, filtered and concentrated under reduced pressure and was purified by column chromatography (SiO₂, EtOAc:MEOH=10:1) to give product (S)-methyl 2-((S)-3-cyclopropyl-2-(7-fluoro-4-methoxy-1H-indole-2-carboxamido)propanamido)-3-((S)-2-oxopiperidin-3-yl)propanoate (1.15 g, 2.11 mmol, 65.01% yield, 92.35% purity) as white solid. MS (ESI) m/z 503.2 [M+H]+

Step 3: N-((S)-1-(((S)-1-amino-1-oxo-3-((S)-2-oxopiperidin-3-yl)propan-2-yl)amino)-3-cyclopropyl-1-oxopropan-2-yl)-7-fluoro-4-methoxy-1H-indole-2-carboxamide To a solution of (S)-methyl 2-((S)-3-cyclopropyl-2-(7-fluoro-4-methoxy-1H-indole-2-carboxamido)propanamido)-3-((S)-2-oxopiperidin-3-yl)propanoate (1.08 g, 2.15 mmol, 1 eq) in NH₃ (7 M in MeOH, 60 mL, 195.43 eq) was stirred at 50° C. for 48 h. Upon completion, the reaction was concentrated in the vacuum to give crude product N-((S)-1-(((S)-1-amino-1-oxo-3-((S)-2-oxopiperidin-3-yl)propan-2-yl)amino)-3-cyclopropyl-1-oxopropan-2-yl)-7-fluoro-4-methoxy-1H-indole-2-carboxamide (1.06 g, crude) as white solid. MS (ESI) m/z 488.2 [M+H]+

Step 4: N-((S)-1-(((S)-1-cyano-2-((S)-2-oxopiperidin-3-yl)ethyl)amino)-3-cyclopropyl-1-oxopropan-2-yl)-7-fluoro-4-methoxy-1H-indole-2-carboxamide To a solution of N-((S)-1-(((S)-1-amino-1-oxo-3-((S)-2-oxopiperidin-3-yl)propan-2-yl)amino)-3-cyclopropyl-1-oxopropan-2-yl)-7-fluoro-4-methoxy-1H-indole-2-carboxamide (1.03 g, 2.11 mmol, 1 eq) in DCM (60 mL) was added Burgess reagent (1.51 g, 6.34 mmol, 3 eq), and the mixture was stirred at 25° C. for 2 h. Upon completion, the reaction was concentrated in the vacuum and was purified by prep-HPLC (column: Waters Xbridge Prep OBD C18 150*40 mm*10 um; mobile phase: [water(0.05% NH₃H₂O+10 mM NH₄HCO₃)-ACN]; B %: 20%-50%, 8 min) to give N-((S)-1-(((S)-1-cyano-2-((S)-2-oxopiperidin-3-yl)ethyl)amino)-3-cyclopropyl-1-oxopropan-2-yl)-7-fluoro-4-methoxy-1H-indole-2-carboxamide (400 mg, 845.40 umol, 40.01% yield, 99.23% purity) as white solid. MS (ESI) m/z 470.1 [M+H]+
¹H NMR (400 MHz, DMSO-d₆) δ=8.95-8.94 (m, 1H), 8.57-8.55 (m, 1H), 7.54 (br s, 1H), 7.36-7.33 (m, 1H), 6.95-6.90 (m, 1H), 6.43-6.40 (m, 1H), 5.09-5.04 (m, 1H), 4.52-4.41 (m, 1H), 3.87 (s, 3H), 3.15-3.03 (m, 2H), 2.33-2.19 (m, 2H), 1.89-1.75 (m, 3H), 1.72-1.69 (m, 1H), 1.64-1.52 (m, 1H), 1.51-1.34 (m, 2H), 0.86-0.76 (m, 1H), 0.47-0.37 (m, 2H), 0.24-0.15 (m, 1H), 0.14-0.06 (m, 1H).

Example 213. Synthesis of Viral Protease Inhibitor Compound 838

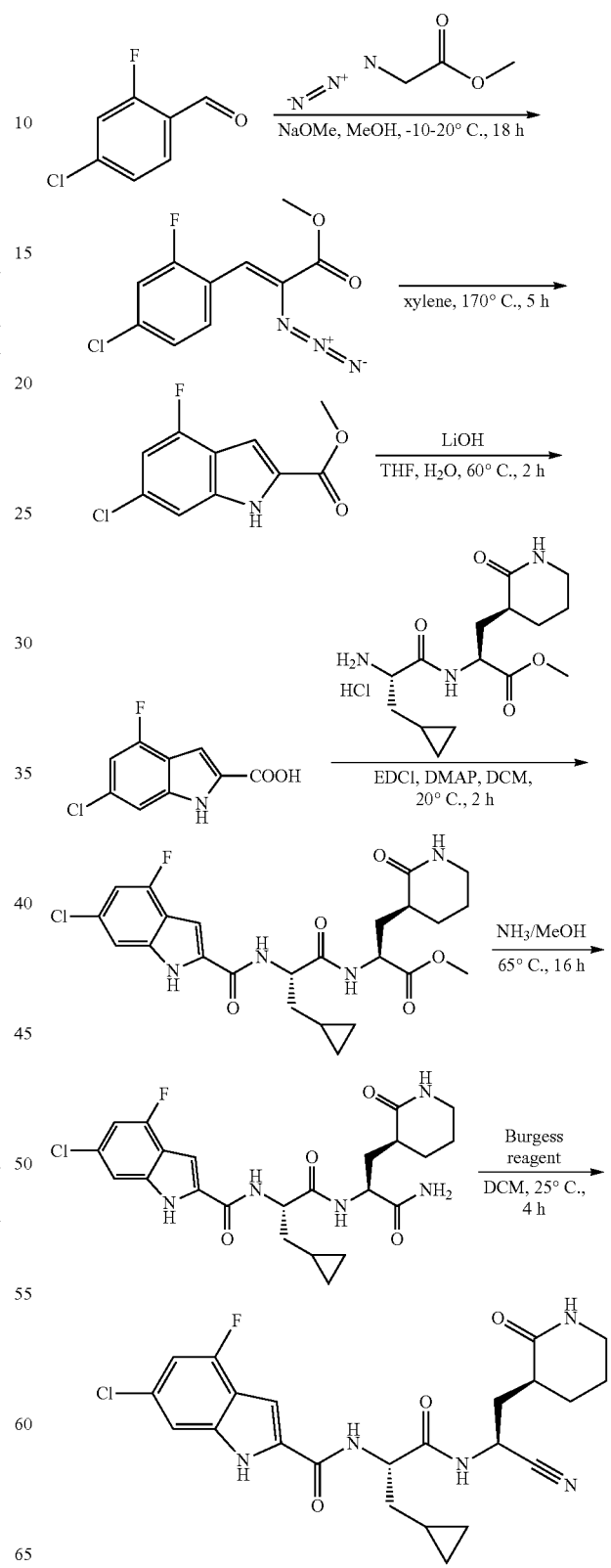

A mixture of NaOMe (3.41 g, 63.07 mmol, 2 eq) in MeOH (40 mL) was cooled to −10° C., and then a mixture 4-chloro-2-fluoro-benzaldehyde (5 g, 31.53 mmol, 1 eq) and methyl 2-azidoacetate (7.26 g, 63.07 mmol, 2 eq) with MeOH (10 mL) was added dropwise. The mixture was stirred at 20° C. for 18 h. Upon completion, the reaction mixture was quenched by the addition to H$_2$O (20 mL) at 25° C., diluted with H$_2$O 100 mL and extracted with ethyl acetate (100 mL*2). The combined organic layers were washed with brine (100 mL), dried over Na$_2$SO$_4$, filtered and concentrated under reduced pressure to give a residue. The residue was purified by column chromatography (SiO$_2$, petroleum ether/ethyl acetate=1/0) to afford methyl (Z)-2-azido-3-(4-chloro-2-fluoro-phenyl)prop-2-enoate (4 g, 14.87 mmol, 47.14% yield, 95% purity) as a white solid.

Step 2: methyl 6-chloro-4-fluoro-1H-indole-2-carboxylate

A mixture of methyl (Z)-2-azido-3-(4-chloro-2-fluoro-phenyl)prop-2-enoate (4 g, 15.65 mmol, 1 eq) in xylene (20 mL) was stirred at 170° C. for 5 h. Upon completion, the reaction mixture was concentrated under reduced pressure to give a residue. The crude product was triturated with petroleum ether:ethyl acetate=10:1 to afford methyl 6-chloro-4-fluoro-1H-indole-2-carboxylate (2 g, 8.35 mmol, 53.35% yield, 95% purity) as a white solid.

Step 3: 6-chloro-4-fluoro-1H-indole-2-carboxylic acid

To a mixture of methyl 6-chloro-4-fluoro-1H-indole-2-carboxylate (1.4 g, 6.15 mmol, 1 eq) in THF (10 mL) and H$_2$O (5 mL) was added LiOH·H$_2$O (516.20 mg, 12.30 mmol, 2 eq). After stirring at 60° C. for 2 h, the pH of the reaction mixture was adjusted to 3 with HCl (1 M), and then diluted with H$_2$O (30 mL) and extracted with ethyl acetate (30 mL*3). The combined organic layers were washed with brine 30 mL (30 mL*1), dried over Na$_2$SO$_4$, filtered and concentrated under reduced pressure to give a residue. The residue was used next step directly. Compound 6-chloro-4-fluoro-1H-indole-2-carboxylic acid (1.3 g, 5.78 mmol, 94.01% yield, 95% purity) was obtained as a white solid.

Step 4: methyl (2S)-2-[[(2S)-2-[(6-chloro-4-fluoro-1H-indole-2-carbonyl)amino]-3-cyclopropyl-propanoyl]amino]-3-[(3S)-2-oxo-3-piperidyl]propanoate To a mixture of 6-chloro-4-fluoro-1H-indole-2-carboxylic acid (600 mg, 2.81 mmol, 1 eq) and methyl (2S)-2-[[(2S)-2-amino-3-cyclopropyl-propanoyl]amino]-3-[(3S)-2-oxo-3-piperidyl]propanoate (977.10 mg, 2.81 mmol, 1 eq, HCl) in DCM (2 mL) and DMF (1 mL) was added EDCI (1.08 g, 5.62 mmol, 2 eq) and DMAP (686.36 mg, 5.62 mmol, 2 eq). The mixture was stirred at 20° C. for 2 h. Upon completion, the reaction mixture was diluted with H$_2$O (100 mL) and extracted with ethyl acetate (100 mL*2). The combined organic layers were washed with brine (100 mL*1), dried over Na$_2$SO$_4$, filtered and concentrated under reduced pressure to give a residue. The residue was purified by column chromatography (SiO$_2$, petroleum ether/ethyl acetate=8/1 to 0/1) to get the compound methyl (2S)-2-[[(2S)-2-[(6-chloro-4-fluoro-1H-indole-2-carbonyl)amino]-3-cyclopropyl-propanoyl] amino]-3-[(3S)-2-oxo-3-piperidyl]propanoate (1.1 g, 1.95 mmol, 69.52% yield, 90% purity) as a white solid. MS (ESI) m/z 507.2 [M+H]$^+$ Step 5: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-chloro-4-fluoro-1H-indole-2-carboxamide A solution of methyl (2S)-2-[[(2S)-2-[(6-chloro-4-fluoro-1H-indole-2-carbonyl)amino]-3-cyclopropyl-propanoyl] amino]-3-[(3S)-2-oxo-3-piperidyl]propanoate (1 g, 1.97 mmol, 1 eq) in NH$_3$/MeOH (7 M, 20 mL, 70.97 eq) was stirred at 65° C. for 16 h. Upon completion, the reaction mixture concentrated under reduced pressure to give a residue and used next step directly. Compound N-[(1S)-2-[[(1S)-2-amino-2-oxo-1-[[(3S)-2-oxo-3-piperidyl]methyl] ethyl] amino]-1-(cyclopropylmethyl)-2-oxo-ethyl]-6-chloro-4-fluoro-1H-indole-2-carboxamide (950 mg, 1.74 mmol, 88.11% yield, 90% purity) was obtained as a white solid. MS (ESI) m/z 492.2 [M+H]$^+$ Step 6: 6-chloro-N-[(1S)-2-[[(1S)-1-cyano-2-[(3S)-2-oxo-3-piperidyl]ethyl]amino]-1-(cyclopropylmethyl)-2-oxo-ethyl]-4-fluoro-1H-indole-2-carboxamide To a mixture of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-chloro-4-fluoro-1H-indole-2-carboxamide (500 mg, 1.02 mmol, 1 eq) in DCM (20 mL) was added Burgess reagent (484.42 mg, 2.03 mmol, 2 eq). The mixture was stirred at 25° C. for 4 h. Upon completion, the reaction mixture was diluted with H$_2$O (5 mL) and extracted with DCM (20 mL*2). The combined organic layers were concentrated with using blow-dry to give a residue. The residue was purified by prep-HPLC (column: Waters Xbridge BEH C18 100*30 mm*10 um; mobile phase: [water (10 mM NH$_4$HCO$_3$)-ACN]; B %: 40%-70%, 10 min) to get 6-chloro-N-[(1S)-2-[[(1S)-1-cyano-2-[(3S)-2-oxo-3-piperidyl]ethyl]amino]-1-(cyclopropylmethyl)-2-oxo-ethyl]-4-fluoro-1H-indole-2-carboxamide (120 mg, 253.20 umol, 24.91% yield, 100% purity) as a white solid. MS (ESI) m/z 474.1 [M+H]$^+$ $^1$H NMR (400 MHz, DMSO-d$_6$) δ=12.08 (br s, 1H), 8.94 (d, J=8.0 Hz, 1H), 8.73 (d, J=7.5 Hz, 1H), 7.61-7.23 (m, 3H), 6.99 (d, J=10.1 Hz, 1H), 5.06 (q, J=8.1 Hz, 1H), 4.57-4.37 (m, 1H), 3.18-2.98 (m, 2H), 2.37-2.17 (m, 2H), 1.89-1.26 (m, 7H), 0.89-0.65 (m, 1H), 0.51-0.32 (m, 2H), 0.27-0.01 (m, 2H).

Example 214. Synthesis of Viral Protease Inhibitor Compound 848

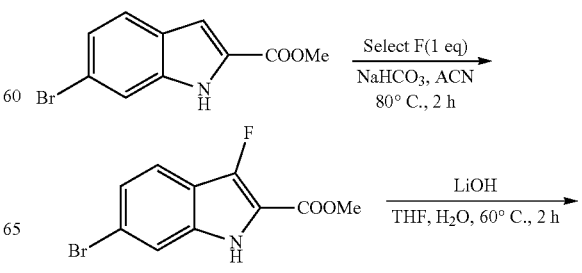

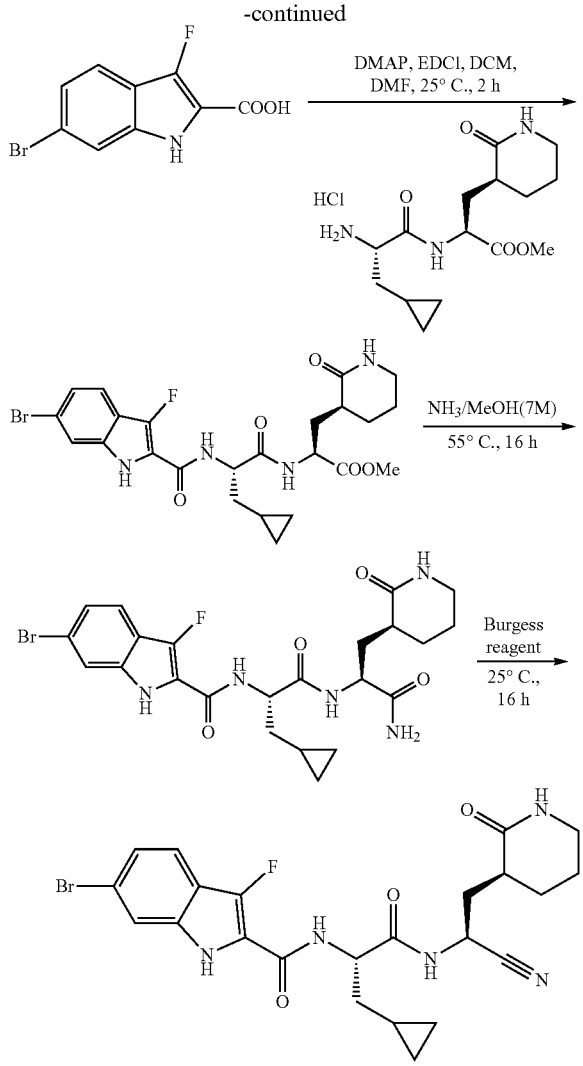

To a mixture of methyl 6-bromo-1H-indole-2-carboxylate (2 g, 7.87 mmol, 1 eq) in ACN (84 mL) was added NaHCO$_3$ (36.42 g, 433.52 mmol, 16.86 mL, 55.07 eq) in one portion at 25° C. Select F (3.07 g, 8.66 mmol, 1 eq) was added and stirred at 80° C. for 2 hours. Upon completion, the reaction mixture was concentrated under reduced pressure to give a crude product. The crude was purified by prep-HPLC (neutral condition, column: Agela DuraShell C18 250*50 mm*10 um; mobile phase: [water (10 mM NH4HCO3)-ACN]; B %: 50%-55%, 20 min) to give methyl 6-bromo-3-fluoro-1H-indole-2-carboxylate (500 mg, 1.84 mmol, 23.35% yield) as a yellow solid.

Step 2: 6-bromo-3-fluoro-1H-indole-2-carboxylic acid

To a mixture of methyl 6-bromo-3-fluoro-1H-indole-2-carboxylate (500 mg, 1.84 mmol, 1 eq) in THF (5 mL) and H$_2$O (5 mL) was added LiOH·H$_2$O (154.22 mg, 3.68 mmol, 2 eq) in one portion at 25° C. The mixture was stirred at 60° C. for 2 h. Upon completion, the reaction mixture was adjusted to acidity by 1M HCl and extracted with ethyl acetate (6 mL*3). The combined organic layers were washed with brine (9 mL*1), dried over Na$_2$SO$_4$, filtered and concentrated under reduced pressure to give 6-bromo-3-fluoro-1H-indole-2-carboxylic acid (440 mg, 1.71 mmol, 92.78% yield) as a yellow solid. (ESI) m/z 256.0 [M−H]$^+$ Step 3: methyl (2S)-2-[[(2S)-2-[(6-bromo-3-fluoro-1H-indole-2-carbonyl)amino]-3-cyclopropyl-propanoyl]amino]-3-[(3S)-2-oxo-3-piperidyl]propanoate To a mixture of 6-bromo-3-fluoro-1H-indole-2-carboxylic acid (440 mg, 1.71 mmol, 1 eq) and methyl (2S)-2-[[(2S)-2-amino-3-cyclopropyl-propanoyl]amino]-3-[(3S)-2-oxo-3-piperidyl]propanoate (654.28 mg, 1.88 mmol, 1.1 eq, HCl) in DCM (8 mL) and DMF (2 mL) was added DMAP (626.73 mg, 5.13 mmol, 3 eq) and EDCI (655.61 mg, 3.42 mmol, 2 eq) in one portion at 25° C. The mixture was stirred at 25° C. for 2 h. Upon completion, the reaction mixture was diluted with H$_2$O (20 mL) and extracted with ethyl acetate (15 mL*4). The combined organic layers were washed with brine 30 mL (30 mL*1), dried over Na$_2$SO$_4$, filtered and concentrated under reduced pressure to give the crude product. The crude was purified by column chromatography (SiO$_2$, petroleum ether/ethyl acetate=5/1 to 0/1) to give methyl (2S)-2-[[(2S)-2-[(6-bromo-3-fluoro-1H-indole-2-carbonyl)amino]-3-cyclopropyl-propanoyl]amino]-3-[(3S)-2-oxo-3-piperidyl]propanoate (510 mg, 924.91 umol, 54.09% yield) as a white solid. (ESI) m/z 551.1 [M+H]$^+$ Step 4: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-bromo-3-fluoro-1H-indole-2-carboxamide A mixture of methyl (2S)-2-[[(2S)-2-[(6-bromo-3-fluoro-1H-indole-2-carbonyl)amino]-3-cyclopropyl-propanoyl]amino]-3-[(3S)-2-oxo-3-piperidyl]propanoate (510 mg, 924.91 umol, 1 eq) in NH$_3$/MeOH (7 M, 10 mL, 75.68 eq) was stirred at 55° C. for 16 hours. Upon completion, the reaction mixture was concentrated under reduced pressure to give N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-bromo-3-fluoro-1H-indole-2-carboxamide (500 mg, crude) as a yellow solid. MS (ESI) m/z 536.2 [M+H]$^+$ Step 5: 6-bromo-N-[(1S)-2-[[(1S)-1-cyano-2-[(3S)-2-oxo-3-piperidyl]ethyl]amino]-1-(cyclopropylmethyl)-2-oxo-ethyl]-3-fluoro-1H-indole-2-carboxamide To a mixture of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-bromo-3-fluoro-1H-indole-2-carboxamide (500 mg, 745.72 umol, 80% purity, 1 eq) in DCM (8 mL) was added Burgess reagent (533.14 mg, 2.24 mmol, 3 eq) in one portion at 25° C. The mixture was stirred at 25° C. for 16 hours. Upon completion, the reaction mixture was concentrated under reduced pressure to give the crude product. The crude was purified by prep-HPLC (neutral condition; column: Phenomenex Gemini-NX C18 75*30 mm*3 um; mobile phase: [water (10 mM NH4HCO3)-ACN]; B %: 40%-65%, 8 min) to give 6-bromo-N-[(1S)-2-[[(1S)-1-cyano-2-[(3S)-2-oxo-3-piperidyl]ethyl]amino]-1-(cyclopropylmethyl)-2-oxo-ethyl]-3-fluoro-1H-indole-2-carboxamide (170 mg, 327.95 umol, 43.98% yield) as a white solid. MS (ESI) m/z 518.1 [M+H]$^+$ $^1$H NMR (400 MHz, DMSO-d$_6$) δ=11.70 (s, 1H), 8.98 (d, J=7.9 Hz, 1H), 7.84 (dd, J=3.1, 7.3 Hz, 1H), 7.65-7.58 (m, 2H), 7.55 (br s, 1H), 7.26 (dd, J=1.5, 8.6 Hz, 1H), 5.09 (q, J=8.1 Hz, 1H), 4.57-4.49 (m, 1H), 3.13-3.05 (m, 2H), 2.30-2.20 (m, 2H), 1.82 (dt, J=6.6, 14.0 Hz, 3H), 1.77-1.67 (m, 1H), 1.64-1.51 (m, 2H), 1.47-1.35 (m, 1H), 0.81-0.70 (m, 1H), 0.48-0.37 (m, 2H), 0.21-0.07 (m, 2H)

Example 215. Synthesis of Viral Protease Inhibitor Compound 862

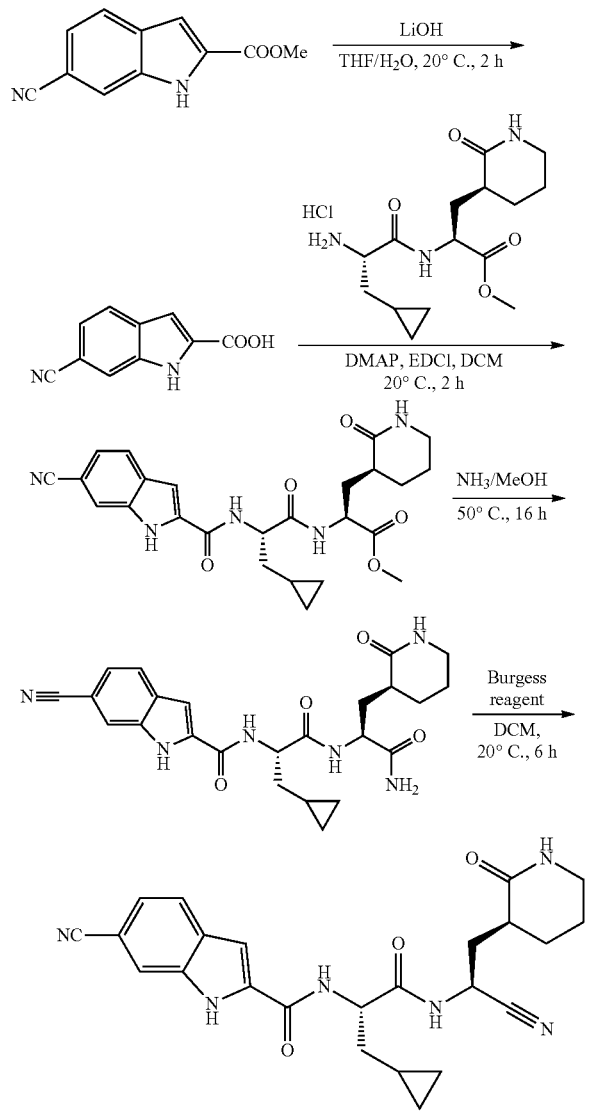

To a solution of methyl 6-cyano-1H-indole-2-carboxylate (1 g, 5.00 mmol, 1 eq) in H₂O (4 mL) and THF (8 mL) was added LiOH·H₂O (358.88 mg, 14.99 mmol, 3 eq). The mixture was stirred at 20° C. for 2 h. Upon completion, the reaction mixture was concentrated under reduced pressure to remove solvent to give 6-cyano-1H-indole-2-carboxylic acid (805 mg, crude) as a white solid. MS (ESI) m/z 187.0 [M+H]$^+$ Step 2: methyl (2S)-2-[[(2S)-2-[(6-cyano-1H-indole-2-carbonyl)amino]-3-cyclopropyl-propanoyl] amino]-3-[(3S)-2-oxo-3-piperidyl]propanoate To a solution of 6-cyano-1H-indole-2-carboxylic acid (776.06 mg, 4.17 mmol, 1 eq) and methyl (2S)-2-[[(2S)-2-amino-3-cyclopropyl-propanoyl]amino]-3-[(3S)-2-oxo-3-piperidyl]propanoate (1.45 g, 4.17 mmol, 1 eq, HCl) in DCM (50 mL) was added DMAP (1.53 g, 12.51 mmol, 3 eq) and EDCI (2.40 g, 12.51 mmol, 3 eq). The mixture was stirred at 20° C. for 2 h. Upon completion, the reaction mixture was quenched by addition H₂O (30 mL), and then extracted with DCM (10 mL*2). The combined organic layers were washed with HCl (1M) 20 mL (10 mL*2), then were washed with brine (20 mL), dried over Na₂SO₄, filtered and concentrated under reduced pressure to give a residue. The residue was purified by column chromatography (SiO₂, petroleum ether/ethyl acetate=3/1 to 0/1, dichloromethane:methanol=10:1, (UV 254 nm)) to give methyl (2S)-2-[[(2S)-2-[(6-cyano-1H-indole-2-carbonyl)amino]-3-cyclopropyl-propanoyl]amino]-3-[(3S)-2-oxo-3-piperidyl]propanoate (1.3 g, 2.56 mmol, 61.46% yield, 94.5% purity) as a white solid. MS (ESI) m/z 480.2 [M+H]$^+$ Step 3: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-cyano-1H-indole-2-carboxamide A solution of methyl (2S)-2-[[(2S)-2-[(6-cyano-1H-indole-2-carbonyl)amino]-3-cyclopropyl-propanoyl]amino]-3-[(3S)-2-oxo-3-piperidyl]propanoate (1.2 g, 2.50 mmol, 1 eq) in NH₃/MeOH (7 M, 20 mL, 55.94 eq) was stirred at 50° C. for 16 h. The reaction mixture was concentrated under reduced pressure to remove solvent to give N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-cyano-1H-indole-2-carboxamide (1.1 g, crude) as a white solid. MS (ESI) m/z 465.2 [M+H]$^+$ Step 4: 6-cyano-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-6-cyano-1H-indole-2-carboxamide (1 g, 2.15 mmol, 1 eq) in DCM (20 mL) was added Burgess reagent (1.03 g, 4.31 mmol, 2 eq). The mixture was stirred at 20° C. for 6 h. Upon completion, the reaction mixture was concentrated under reduced pressure to remove solvent. The residue was purified by prep-HPLC (column: Waters Xbridge C18 150*50 mm*10 um; mobile phase: [water (10 mM NH₄HCO₃)-ACN]; B %: 25%-55%, 10 min) to give 6-cyano-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide (414.8 mg, 929.00 umol, 43.15% yield, 100% purity) as a white solid. MS (ESI) m/z 447.2 [M+H]$^+$.

1H NMR (400 MHz, DMSO-d₆) δ=12.08 (s, 1H), 8.96 (d, J=8.4 Hz, 1H), 8.82 (d, J=7.8 Hz, 1H), 7.89-7.81 (m, 2H), 7.53 (s, 1H), 7.45-7.33 (m, 2H), 5.07 (q, J=8.2 Hz, 1H), 4.54-4.46 (m, 1H), 3.17-3.01 (m, 2H), 2.35-2.20 (m, 2H), 1.91-1.65 (m, 4H), 1.63-1.32 (m, 3H), 0.88-0.73 (m, 1H), 0.50-0.35 (m, 2H), 0.25-0.07 (m, 2H)

Example 216. Synthesis of Viral Protease Inhibitor Compound 866

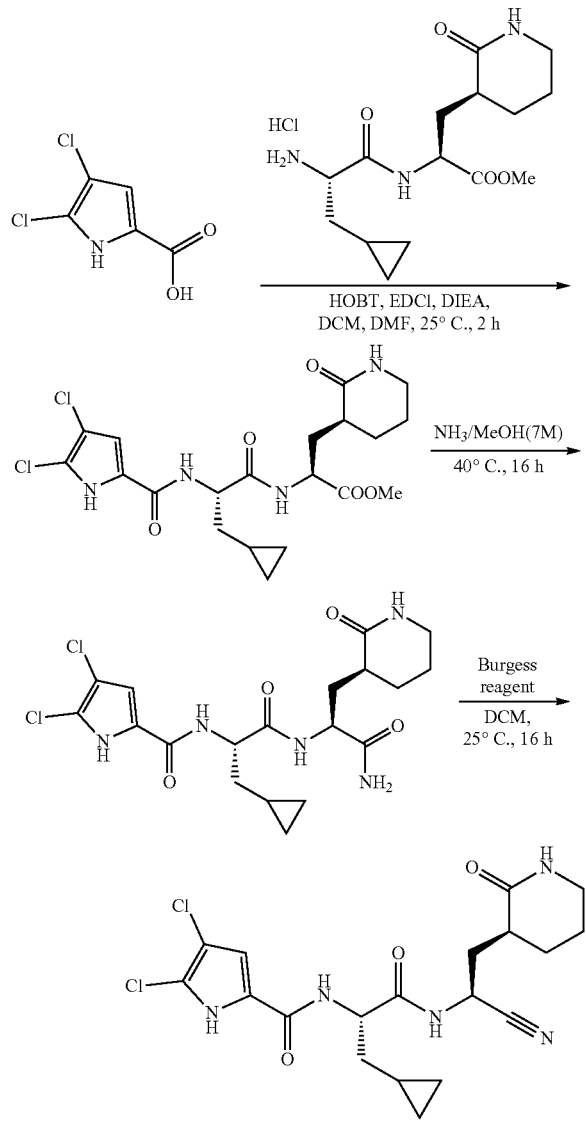

To a mixture of 4,5-dichloro-1H-pyrrole-2-carboxylic acid (300 mg, 1.67 mmol, 1 eq) and methyl (2S)-2-[[(2S)-2-amino-3-cyclopropyl-propanoyl]amino]-3-[(3S)-2-oxo-3-piperidyl]propanoate (637.74 mg, 1.83 mmol, 1.1 eq, HCl) in DCM (8 mL) and DMF (2 mL) was added DIEA (430.84 mg, 3.33 mmol, 580.64 uL, 2 eq), HOBt (450.44 mg, 3.33 mmol, 2 eq) and EDCI (639.05 mg, 3.33 mmol, 2 eq) in one portion at 25° C. The mixture was stirred at 25° C. for 2 hours. Upon completion, the reaction mixture was diluted with H₂O (20 mL) and extracted with ethyl acetate (15 mL*4). The combined organic layers were washed with brine (30 mL*1), dried over Na₂SO₄, filtered and concentrated under reduced pressure to give the crude product. The crude was purified by column chromatography (SiO₂, petroleum ether/ethyl acetate=5/1 to 0/1) to give methyl (2S)-2-[[(2S)-3-cyclopropyl-2-[(4,5-dichloro-1H-pyrrole-2-carbonyl)amino]propanoyl]amino]-3-[(3S)-2-oxo-3-piperidyl]propanoate (550 mg, 1.16 mmol, 69.71% yield) as a white solid. MS (ESI) m/z 473.1 [M+H]⁺

Step 2: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4,5-dichloro-1H-pyrrole-2-carboxamide A mixture of methyl (2S)-2-[[(2S)-3-cyclopropyl-2-[(4,5-dichloro-1H-pyrrole-2-carbonyl)amino]propanoyl]amino]-3-[(3S)-2-oxo-3-piperidyl]propanoate (500 mg, 1.06 mmol, 1 eq) in NH₃/MeOH (7 M, 20 mL, 132.54 eq) was stirred at 40° C. for 16 hours. Upon completion, the reaction mixture was concentrated under reduced pressure to give N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4,5-dichloro-1H-pyrrole-2-carboxamide (480 mg, 1.05 mmol, 99.14% yield) as a yellow solid. MS (ESI) m/z 458.1 [M+H]⁺

Step 3: 4,5-dichloro-N-[(1S)-2-[[(1S)-1-cyano-2-[(3S)-2-oxo-3-piperidyl]ethyl]amino]-1-(cyclopropylmethyl)-2-oxo-ethyl]-1H-pyrrole-2-carboxamide To a mixture of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4,5-dichloro-1H-pyrrole-2-carboxamide (480 mg, 555.05 umol, 53% purity, 1 eq) in DCM (8 mL) was added Burgess reagent (396.82 mg, 1.67 mmol, 3 eq) in one portion at 25° C. The mixture was stirred at 25° C. for 16 hours. Upon completion, the reaction mixture was concentrated under reduced pressure to give the crude product. The crude was purified by prep-HPLC (neutral condition; column: column: Phenomenex Gemini-NX C18 75*30 mm*3 um; mobile phase: [water (10 mM NH4HCO3)-ACN]; B %: 25%-50%, 8 min) to give 4,5-dichloro-N-[(1S)-2-[[(1S)-1-cyano-2-[(3S)-2-oxo-3-piperidyl]ethyl]amino]-1-(cyclopropylmethyl)-2-oxo-ethyl]-1H-pyrrole-2-carboxamide (108 mg, 245.27 umol, 44.19% yield) as a white solid. MS (ESI) m/z 440.1 [M+H]⁺

¹H NMR (400 MHz, DMSO-d₆) δ=12.74 (br s, 1H), 8.88 (d, J=8.2 Hz, 1H), 8.22 (br d, J=7.1 Hz, 1H), 7.53 (br s, 1H), 7.05 (s, 1H), 5.10-5.00 (m, 1H), 4.44-4.33 (m, 1H), 3.15-3.02 (m, 2H), 2.30-2.17 (m, 2H), 1.91-1.65 (m, 4H), 1.55 (br dd, J=3.5, 9.9 Hz, 1H), 1.47-1.32 (m, 2H), 0.82-0.70 (m, 1H), 0.45-0.34 (m, 2H), 0.21-0.02 (m, 2H)

Example 217. Synthesis of Viral Protease Inhibitor Compound 872

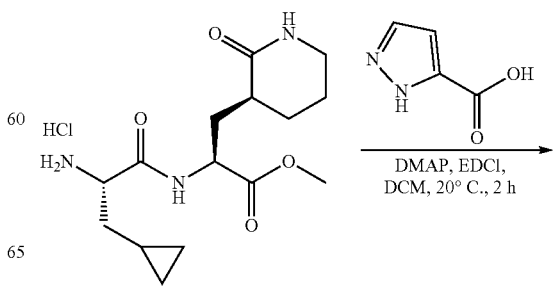

1293

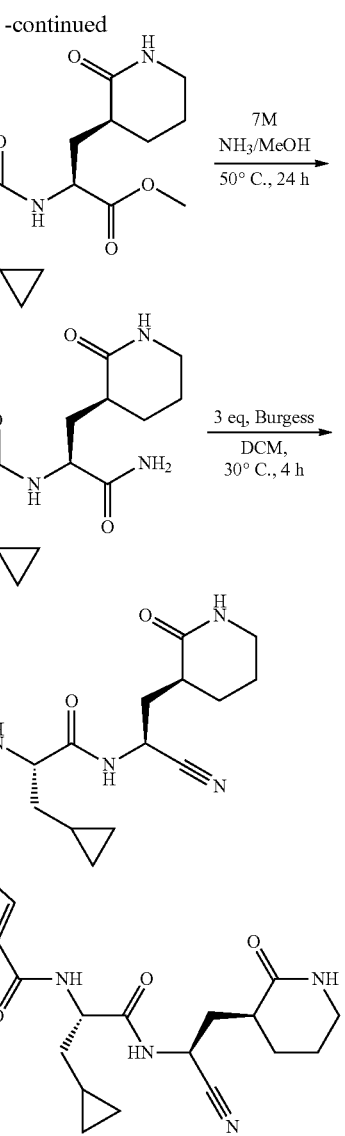

To a solution of 1H-pyrazole-5-carboxylic acid (500 mg, 4.46 mmol, 1 eq) and methyl (2S)-2-[[(2S)-2-amino-3-cyclopropyl-propanoyl]amino]-3-[(3S)-2-oxo-3-piperidyl] propanoate (1.24 g, 3.57 mmol, 0.8 eq, HCl) in DCM (40 mL) was added DMAP (1.09 g, 8.92 mmol, 2 eq) and EDCI (1.71 g, 8.92 mmol, 2 eq), and then the mixture was stirred at 20° C. for 2 h. Upon the reaction completement, the mixture was poured into water (40 mL) and was extracted with DCM (15 mL*3) and dried with anhydrous Na$_2$SO$_4$, filtered and concentrated in vacuum and was purified by prep-HPLC (column: Waters Xbridge C18 150*50 mm*10 um; mobile phase: [water (10 mM NH$_4$HCO$_3$)-ACN]; B %: 1%-40%, 10 min) to obtained (S)-methyl 2-((S)-3-cyclopropyl-2-(1H-pyrazole-5-carboxamido)propanamido)-3-((S)-2-oxopiperidin-3-yl)propanoate (550 mg, 1.26 mmol, 28.25% yield, 92.9% purity) as a white solid. MS (ESI) m/z 406.2 [M+H]$^+$ Step 2: N-((S)-1-(((S)-1-amino-1-oxo-3-((S)-2-oxopiperidin-3-yl)propan-2-yl)amino)-3-cyclopropyl-1-oxopropan-2-yl)-1H-pyrazole-5-carboxamide A solution of (S)-methyl 2-((S)-3-cyclopropyl-2-(1H-pyrazole-5-carboxamido) propanamido)-3-((S)-2-oxopip-

1294 eridin-3-yl) propanoate (500 mg, 1.23 mmol, 1 eq) in NH$_3$/MeOH (20 mL, 7M) was stirred at 50° C. for 24 h. Upon the reaction completement, the mixture was concentrated in vacuum to obtain N-((S)-1-(((S)-1-amino-1-oxo-3-((S)-2-oxopiperidin-3-yl) propan-2-yl)amino)-3-cyclopropyl-1-oxopropan-2-yl)-1H-pyrazole-5-carboxamide (500 mg, crude) as a light yellow solid. MS (ESI) m/z 391.2 [M+H]$^+$ Step 3: N-((S)-1-(((S)-1-cyano-2-((S)-2-oxopiperidin-3-yl)ethyl)amino)-3-cyclopropyl-1-oxopropan-2-yl)-1H-pyrazole-5-carboxamide & methyl(5-(((S)-1-(((S)-1-cyano-2-((S)-2-oxopiperidin-3-yl)ethyl) amino)-3-cyclopropyl-1-oxopropan-2-yl) carbamoyl)-1H-pyrazol-1-yl)sulfonylcarbamate To a solution of N-((S)-1-(((S)-1-amino-1-oxo-3-((S)-2-oxopiperidin-3-yl) propan-2-yl)amino)-3-cyclopropyl-1-oxopropan-2-yl)-1H-pyrazole-5-carboxamide (500 mg, 1.28 mmol, 1 eq) in DCM (8 mL) was added Burgess reagent (915.53 mg, 3.84 mmol, 3 eq), and then the mixture was stirred at 30° C. for 4 h. Upon completion of the reaction, the reaction mixture was quenched with water (1 mL) and was dried with using N$_2$, and then was purified by prep-HPLC (column: Waters Xbridge Prep OBD C18 150*40 mm*10 um; mobile phase: [water (10 mM NH$_4$HCO$_3$)-ACN]; B %: 15%-45%, 8 min) to obtain N-((S)-1-(((S)-1-cyano-2-((S)-2-oxopiperidin-3-yl)ethyl)amino)-3-cyclopropyl-1-xopropan2-yl)-1H-pyrazole-5-carboxamide (S4C_104, 160 mg, 425.76 umol, 33.25% yield, 99.1% purity) as a white solid. MS (ESI) m/z 373.1[M+H]$^+$ $^1$H NMR (400 MHz, DMSO-d$_6$) δ ppm 13.57-13.18 (m, 1H), 8.91 (d, J=8.0 Hz, 1H), 7.92 (d, J=8.0 Hz, 1H), 7.83 (s, 1H), 7.52 (s, 1H), 7.02-6.59 (m, 1H), 5.05 (q, J=7.9 Hz, 1H), 4.48 (q, J=7.4 Hz, 1H), 3.16-3.02 (m, 2H), 2.31-2.17 (m, 2H), 1.89-1.65 (m, 4H), 1.63-1.32 (m, 3H), 0.71 (d, J=6.4 Hz, 1H), 0.40 (d, J=8.0 Hz, 2H), 0.09 (dd, J=4.6, 14.9 Hz, 2H).

Methyl(5-(((S)-1-(((S)-1-cyano-2-((S)-2-oxopiperidin-3-yl)ethyl)amino)-3-cyclopropyl-1-oxopropan-2-yl)carbamoyl)-1H-pyrazol-1-yl)sulfonylcarbamate (S4C_104A, 20 mg, 425.76 umol, 33.25% yield, 99.1% purity) was obtained as a white solid. MS (ESI) m/z 510.1[M+H]$^+$ $^1$H NMR (400 MHz, DMSO-d$_6$) δ ppm 9.06 (s, 1H), 8.91 (d, J=8.0 Hz, 1H), 8.03 (s, 1H), 7.77 (s, 1H), 7.52 (s, 1H), 7.21 (s, 1H), 7.08 (s, 1H), 7.01-6.92 (m, 1H), 6.77-6.32 (m, 2H), 5.05 (q, J=7.9 Hz, 1H), 4.56-4.40 (m, 1H), 3.47 (s, 3H), 3.16-3.01 (m, 2H), 2.30-2.15 (m, 2H), 1.89-1.65 (m, 4H), 1.63-1.31 (m, 3H), 0.77-0.65 (m, 1H), 0.45-0.32 (m, 2H), 0.21-0.00 (m, 2H).

Example 218. Synthesis of Viral Protease Inhibitor Compound 731

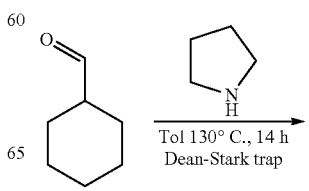

1295
-continued
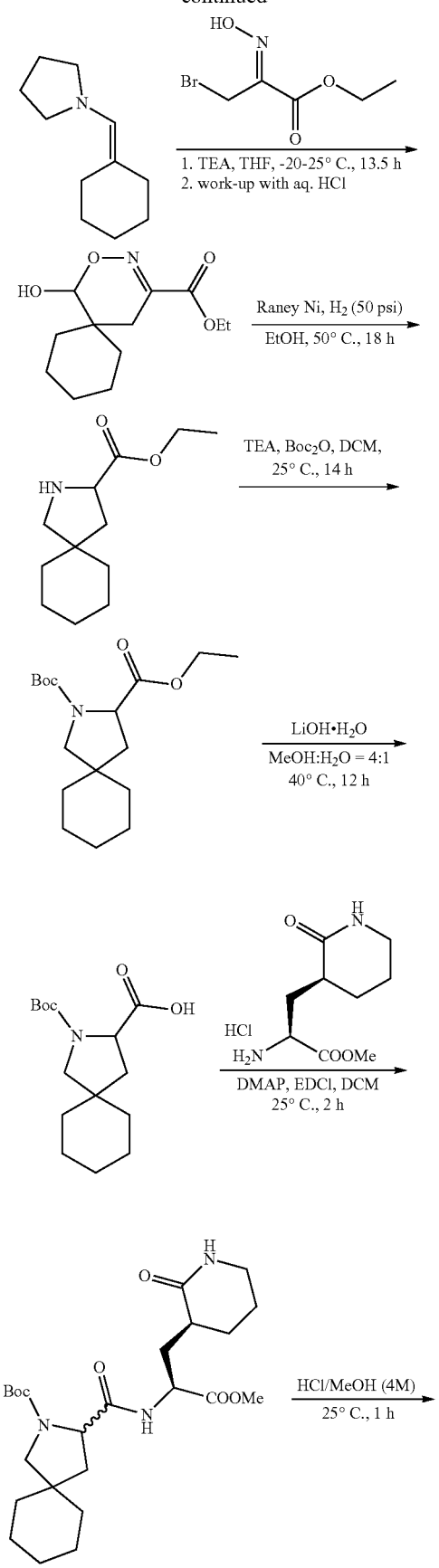
1296
-continued
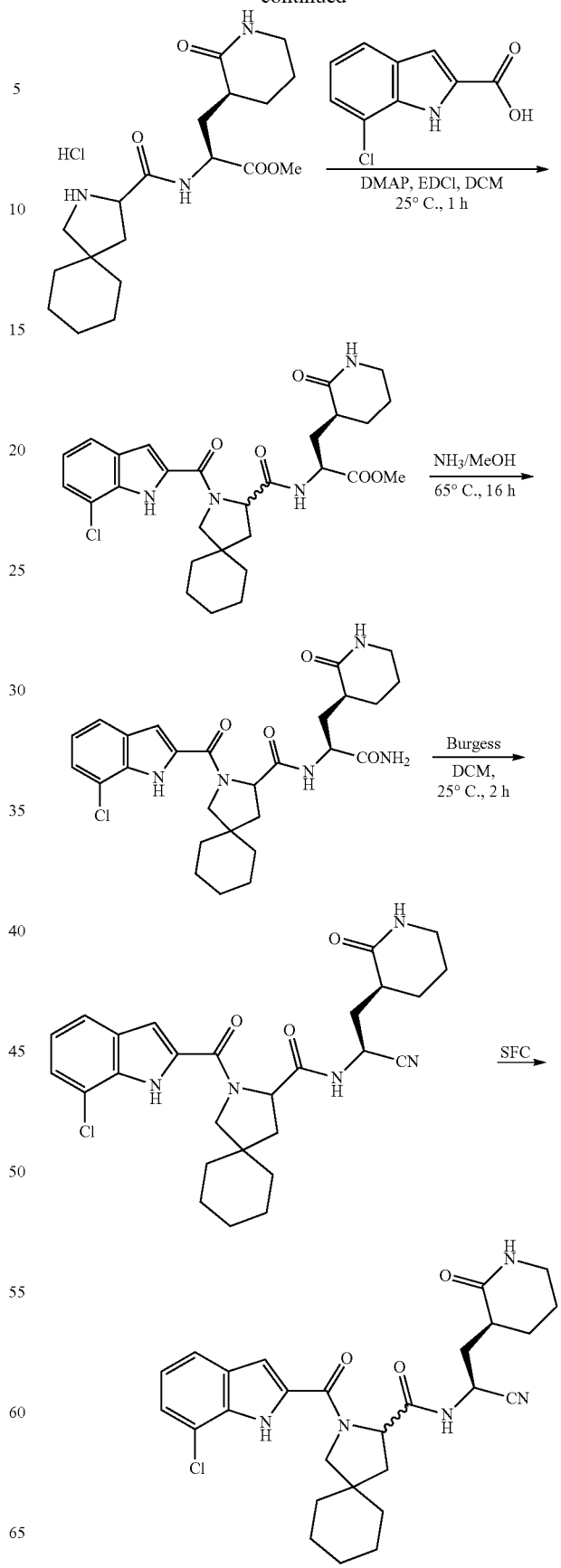

-continued

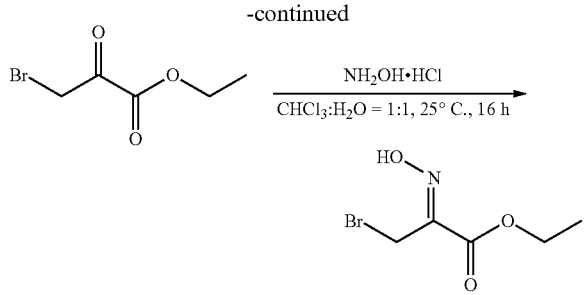

To a solution of ethyl 3-bromo-2-oxo-propanoate (167 g, 428.18 mmol, 107.05 mL, 50% purity, 1 eq) in CHCl$_3$ (800 mL) was added NH$_2$OH·HCl (32.73 g, 471.00 mmol, 1.1 eq) in H$_2$O (800 mL) under N$_2$. The mixture was stirred at 25° C. for 16 h. Upon completion, the reaction was extracted with DCM (1000 mL*4). The combined organic phase was washed with brine (2000 mL), dried over anhydrous Na$_2$SO$_4$, filtered and concentrated in vacuo to give (Z)-ethyl 3-bromo-2-(hydroxyimino)propanoate (440 g, crude) as a white solid. MS (ESI) m/z 210.3 [M+H]$^+$.

Step 2: 1-(cyclohexylidenemethyl)pyrrolidine

A mixture of cyclohexanecarbaldehyde (100 g, 891.51 mmol, 107.30 mL, 1 eq), pyrrolidine (82.43 g, 1.16 mol, 96.74 mL, 1.3 eq) in toluene (1.6 L) was heated to 130° C. for 14 h, and then water was removed by Dean-Stark trap. Upon completion, the reaction mixture was concentrated under reduced pressure at 55° C. to afford 1-(cyclohexylidenemethyl)pyrrolidine (420 g, crude) as a yellow oil. MS (ESI) m/z 166.2 [M+H]$^+$.

Step 3: ethyl 1-hydroxy-2-oxa-3-azaspiro[5.5]undec-3-ene-4-carboxylate

To a solution of 1-(cyclohexylidenemethyl)pyrrolidine (140 g, 847.08 mmol, 1 eq) in THF (1000 mL) was added a solution of ethyl (2Z)-3-bromo-2-hydroxyimino-propanoate (177.91 g, 847.08 mmol, 1 eq) in THF (1000 mL) drop-wise at −20° C. under N$_2$. After 1 h, TEA (85.72 g, 847.08 mmol, 117.90 mL, 1 eq) was added drop-wise at −20° C. under N$_2$. The reaction mixture was stirred at 25° C. for 12 h under N$_2$. Upon completion, the residue was poured into HCl (2M, 2500 mL) and stirred for 30 min, and extracted with ethyl acetate (1500 mL*4). The combined organic layers were washed with brine (2000 mL), dried over Na$_2$SO$_4$, filtered and concentrated under reduced pressure to give a residue. The residue was purified by column chromatography (SiO$_2$, petroleum ether/ethyl acetate=1/0 to 1/1) to give a ethyl 1-hydroxy-2-oxa-3-azaspiro[5.5]undec-3-ene-4-carboxylate (200 g, 497.34 mmol, 19.57% yield, 60% purity) as a yellow oil. MS (ESI) m/z 242.2 [M+H]$^+$.

Step 4: ethyl 2-azaspiro[4.5]decane-3-carboxylate

To a solution of ethyl 1-hydroxy-2-oxa-3-azaspiro[5.5]undec-3-ene-4-carboxylate (20 g, 49.73 mmol, 60% purity, 1 eq) in EtOH (150 mL) was added Raney nickel (12.00 g, 140.07 mmol, 2.82 eq) under Ar$_2$. The suspension was degassed under vacuum and purged with H$_2$ (100.46 mg, 49.73 mmol, 1 eq) several times. The mixture was stirred under H$_2$ (100.46 mg, 49.73 mmol, 1 eq) (50 psi) at 50° C. for 18 h. Upon completion, the reaction mixture was filtered and concentrated under reduced pressure to give a residue. The residue was purified by column chromatography (SiO$_2$, petroleum ether/ethyl acetate=20/1 to ethyl acetate: MeOH=10/1) to give a ethyl 2-azaspiro[4.5]decane-3-carboxylate (35 g, 165.64 mmol, 33.31% yield) as a yellow oil. MS (ESI) m/z 212.2 [M+H]$^+$.

Step 5: 2-tert-butyl 3-ethyl 2-azaspiro[4.5]decane-2,3-dicarboxylate

To a solution of ethyl 2-azaspiro[4.5]decane-3-carboxylate (35 g, 132.51 mmol, 80% purity, 1 eq) in DCM (350 mL) was added Boc$_2$O (34.70 g, 159.02 mmol, 36.53 mL, 1.2 eq) and TEA (26.82 g, 265.03 mmol, 36.89 mL, 2 eq) at 0° C. The mixture was stirred at 25° C. for 14 h. Upon completion, the reaction mixture was quenched by addition H$_2$O (400 mL), and extracted with ethyl acetate (200 mL*3). The combined organic layers were washed with brine (300 mL), dried over Na$_2$SO$_4$, filtered and concentrated under reduced pressure to give a residue. The residue was purified by column chromatography (SiO$_2$, petroleum ether/ethyl acetate=1/0 to 10/1) to give 2-tert-butyl 3-ethyl 2-azaspiro[4.5]decane-2,3-dicarboxylate (40 g, 95.05 mmol, 71.73% yield, 74% purity) as a yellow oil. MS (ESI) m/z 312.2 [M+H]$^+$.

Step 6: 2-(tert-butoxycarbonyl)-2-azaspiro[4.5]decane-3-carboxylic acid

To a solution of 2-tert-butyl 3-ethyl 2-azaspiro[4.5]decane-2,3-dicarboxylate (40 g, 128.45 mmol, 1 eq) in H$_2$O (120 mL) and MeOH (480 mL) was added LiOH·H$_2$O (16.17 g, 385.34 mmol, 3 eq). The mixture was stirred at 40° C. for 12 h. Upon completion, the reaction mixture was concentrated under reduced pressure to remove MeOH. The residue was diluted with H$_2$O (800 mL) and extracted with ethyl acetate (500 mL*2). The aqueous phase were added with HCl (aq) to adjust the pH to 2 and extracted with ethyl acetate (900 mL*3). The combined organic layers were washed with brine (900 mL), dried over Na$_2$SO$_4$, filtered and concentrated under reduced pressure to yield 2-tert-butoxycarbonyl-2-azaspiro[4.5]decane-3-carboxylic acid (35 g, crude) as a yellow oil. MS (ESI) m/z 284.2 [M+H]$^+$ Step 7: tert-butyl 3-(((S)-1-methoxy-1-oxo-3-((S)-2-oxopiperidin-3-yl)propan-2-yl)carbamoyl)-2-azaspiro[4.5]decane-2-carboxylate To a solution of methyl (2S)-2-amino-3-[(3S)-2-oxo-3-piperidyl]propanoate (22.97 g, 97.05 mmol, 1.1 eq, HCl) and 2-tert-butoxycarbonyl-2-azaspiro[4.5]decane-3-carboxylic acid (25 g, 88.23 mmol, 1 eq) in DCM (400 mL) was added DMAP (21.56 g, 176.45 mmol, 2 eq) and EDCI (25.37 g, 132.34 mmol, 1.5 eq). The mixture was stirred at 25° C. for 2 h. Upon completion, the reaction was quenched by 0.5 M HCl (400 mL) and then extracted with DCM (150 mL*3). The combined organic phase was washed with brine (150 mL), dried over anhydrous Na$_2$SO$_4$, filtered and concentrated in vacuo. The residue was purified by column chromatography (SiO$_2$, petroleum ether/ethyl acetate=1/1 to 0/1) to give tert-butyl 3-[[(1S)-2-methoxy-2-oxo-1-[[(3S)-2-oxo-3-piperidyl]methyl]ethyl]carbamoyl]-2-azaspiro[4.5]decane-2-carboxylate (27 g, 47.84 mmol, 54.23% yield, 82.5% purity) as a yellow solid. MS (ESI) m/z 466.2 [M+H]$^+$ Step 8: (2S)-methyl 3-((S)-2-oxopiperidin-3-yl)-2-(2-azaspiro[4.5]decane-3-carboxamido)propanoate To a solution of tert-butyl 3-[[(1S)-2-methoxy-2-oxo-1-[[(3S)-2-oxo-3-piperidyl]methyl]ethyl]carbamoyl]-2-azaspiro[4.5]decane-2-carboxylate (27 g, 47.84 mmol, 82.5% purity, 1 eq) in HCl/MeOH (300 mL). The mixture was stirred at 25° C. for 1 h. Upon completion, the reaction mixture was concentrated under reduced pressure to remove HCl/MeOH, and added DCM (150 mL) (three times) was concentrated under reduced pressure to give methyl (2S)-2-(2-azaspiro[4.5]decane-3-carbonylamino)-3-[(3S)-2-oxo-3-piperidyl]propanoate (25 g, crude, HCl) as a yellow solid. MS (ESI) m/z 366.3 [M+H]$^+$ Step 9: (2S)-methyl 2-(2-(7-chloro-1H-indole-2-carbonyl)-2-azaspiro[4.5]decane-3-carboxamido)-3-((S)-2-oxopiperidin-3-yl)propanoate To a solution of methyl (2S)-2-(2-azaspiro[4.5]decane-3-carbonylamino)-3-[(3S)-2-oxo-3-piperidyl]propanoate (25 g, 62.20 mmol, 1 eq, HCl) and 7-chloro-1H-indole-2-carboxylic acid (13.38 g, 68.42 mmol, 1.1 eq) in DCM (400 mL) was added EDCI (17.89 g, 93.30 mmol, 1.5 eq) and DMAP (15.20 g, 124.40 mmol, 2 eq). The mixture was stirred at 25° C. for 1 h. Upon completion, the reaction was quenched by 0.5 M HCl (400 mL) and then extracted with DCM (300 mL*2). The combined organic phase was washed with brine (400 mL), dried over anhydrous Na$_2$SO$_4$, filtered and concentrated in vacuo. The residue was purified by column chromatography (SiO$_2$, petroleum ether/ethyl acetate=1/1 to 0/1) to give methyl (2S)-2-[[2-(7-chloro-1H-indole-2-carbonyl)-2-azaspiro[4.5]decane-3-carbonyl]amino]-3-[(3S)-2-oxo-3-piperidyl]propanoate (25 g, 44.19 mmol, 71.05% yield, 96% purity) as a yellow solid. MS (ESI) m/z 543.3 [M+H]$^+$ Step 10: N-((S)-1-amino-1-oxo-3-((S)-2-oxopiperidin-3-yl)propan-2-yl)-2-(7-chloro-1H-indole-2-carbonyl)-2-azaspiro[4.5]decane-3-carboxamide A solution of methyl (2S)-2-[[2-(7-chloro-1H-indole-2-carbonyl)-2-azaspiro[4.5]decane-3-carbonyl]amino]-3-[(3S)-2-oxo-3-piperidyl]propanoate (5 g, 8.84 mmol, 96% purity, 1 eq) in NH$_3$ (7 M in MeOH, 57.60 mL, 45.62 eq) (15 Psi) was stirred at 65° C. for 16 h in a 100 mL of autoclave. Upon completion, the reaction mixture was concentrated under reduced pressure to remove NH$_3$/MeOH, and added DCM (300 mL) (three times) was concentrated under reduced pressure to give N-[(1S)-2-amino-2-oxo-1-[[(3S)-2-oxo-3-piperidyl]methyl]ethyl]-2-(7-chloro-1H-indole-2-carbonyl)-2-azaspiro[4.5]decane-3-carboxamide (24 g, crude) as a yellow solid. MS (ESI) m/z 528.3 [M+H]$^+$ Step 11: 2-(7-chloro-1H-indole-2-carbonyl)-N-((S)-1-cyano-2-((S)-2-oxopiperidin-3-yl)ethyl)-2-azaspiro[4.5]decane-3-carboxamide To a solution of N-[(1S)-2-amino-2-oxo-1-[[(3S)-2-oxo-3-piperidyl]methyl]ethyl]-2-(7-chloro-1H-indole-2-carbonyl)-2-azaspiro[4.5]decane-3-carboxamide (12 g, 22.73 mmol, 1 eq) in DCM (200 mL) was added Burgess reagent (11.91 g, 50.00 mmol, 2.2 eq). The mixture was stirred at 25° C. for 2 h. The reaction mixture was quenched by addition H$_2$O (10 mL) at 20° C., and then to remove solvent by N$_2$. The residue was purified by prep-HPLC (column: Phenomenex Titank C18 Bulk 250*100 mm 10 u; mobile phase: [water (10 mM NH$_4$HCO$_3$)-ACN]; B %: 30%-65%, 20 min) to give 2-(7-chloro-1H-indole-2-carbonyl)-N-((S)-1-cyano-2-((S)-2-oxopiperidin-3-yl)ethyl)-2-azaspiro[4.5]decane-3-carboxamide (17 g, 99.29% purity) as a yellow solid. MS (ESI) m/z 510.3 [M+H]$^+$ Step 12: 2-(7-chloro-1H-indole-2-carbonyl)-N-((S)-1-cyano-2-((S)-2-oxopiperidin-3-yl)ethyl)-2-azaspiro[4.5]decane-3-carboxamide Isomer 1:

The desired compound was further separated by SFC (condition: column: REGIS (s,s) WHELK-O1 (250 mm*50 mm, 10 um); mobile phase: [0.1% NH$_3$H$_2$O ETOH]; B %: 60%-60%, 9.5 min) to give 2-(7-chloro-1H-indole-2-carbonyl)-N-[(1S)-1-cyano-2-[(3S)-2-oxo-3-piperidyl]ethyl]-2-azaspiro[4.5]decane-3-carboxamide (6.1 g, 11.96 mmol, 26.31% yield) as a yellow solid. MS (ESI) m/z 510.3 [M+H]$^+$ $^1$H NMR (400 MHz, DMSO-d$_6$) δ=11.64-11.51 (m, 1H), 8.98-8.86 (m, 1H), 7.70-7.38 (m, 2H), 7.32-7.21 (m, 1H), 7.16-6.69 (m, 2H), 5.08-4.47 (m, 2H), 3.88-3.76 (m, 1H), 3.70-3.60 (m, 1H), 3.27-2.93 (m, 2H), 2.35 (br s, 3H), 1.88-1.31 (m, 16H).

$^1$H NMR (400 MHz, DMSO-d$_6$, 273+80K) δ=11.28-11.09 (m, 1H), 8.82-8.62 (m, 1H), 7.73-7.52 (m, 1H), 7.37-7.22 (m, 2H), 7.20-6.96 (m, 2H), 5.08-4.86 (m, 1H), 4.70-4.46 (m, 1H), 3.88-3.78 (m, 1H), 3.70-3.51 (m, 1H), 3.14-3.09 (m, 2H), 2.40-2.13 (m, 3H), 1.87-1.37 (m, 16H).

$^1$H NMR (400 MHz, MeOD-d$_4$) δ 7.67-7.46 (m, 1H), 7.32-7.22 (m, 1H), 7.14-6.81 (m, 2H), 5.16-4.97 (m, 1H), 4.83-4.58 (m, 1H), 3.98-3.81 (m, 1H), 3.76-3.38 (m, 1H), 3.27-2.98 (m, 2H), 2.67-2.20 (m, 3H), 2.05-1.43 (m, 16H).

Isomer 2:

2-(7-Chloro-1H-indole-2-carbonyl)-N-[(1S)-1-cyano-2-[(3S)-2-oxo-3-piperidyl]ethyl]-2-azaspiro[4.5]decane-3-carboxamide (7 g, 13.72 mmol, 30.20% yield) was obtained as a yellow solid. MS (ESI) m/z 510.3 [M+H]$^+$ $^1$H NMR (400 MHz, DMSO-d$_6$) δ=11.59-11.47 (m, 1H), 8.98-8.77 (m, 1H), 7.69-7.63 (m, 1H), 7.54-7.46 (m, 1H), 7.32-7.23 (m, 1H), 7.18-6.68 (m, 2H), 5.06-4.84 (m, 1H), 4.80-4.47 (m, 1H), 3.90-3.78 (m, 1H), 3.74-3.61 (m, 1H), 3.28-3.00 (m, 2H), 2.33-2.09 (m, 1H), 2.08-2.06 (m, 1H), 1.88-1.32 (m, 16H).

$^1$H NMR (400 MHz, DMSO-d$_6$, 273+80K) δ=11.26-11.02 (m, 1H), 8.74-8.57 (m, 1H), 7.76-7.51 (m, 1H), 7.32-7.21 (m, 2H), 7.17-6.93 (m, 2H), 5.07-4.87 (m, 1H), 4.73-4.51 (m, 1H), 3.87-3.79 (m, 1H), 3.73-3.52 (m, 1H), 3.08 (s, 2H), 2.29-2.12 (m, 3H), 1.86-1.38 (m, 16H).

$^1$H NMR (400 MHz, MeOD-d$_4$) δ=7.72-7.52 (m, 1H), 7.33-7.19 (m, 1H), 7.14-6.79 (m, 2H), 5.09-4.92 (m, 1H), 4.70-4.54 (m, 1H), 3.99-3.89 (m, 1H), 3.83-3.40 (m, 1H), 3.22-3.00 (m, 2H), 2.57-2.12 (m, 3H), 2.01-1.40 (m, 16H).

Example 219. Synthesis of Viral Protease Inhibitor Compound 900

Step 1: (S)-methyl2-((S)-2-(7-chloro-5-methoxy-1H-indole-2-carboxamido)-3-cyclopropylpropanamido)-3-((S)-2-oxopiperidin-3-yl)propanoate

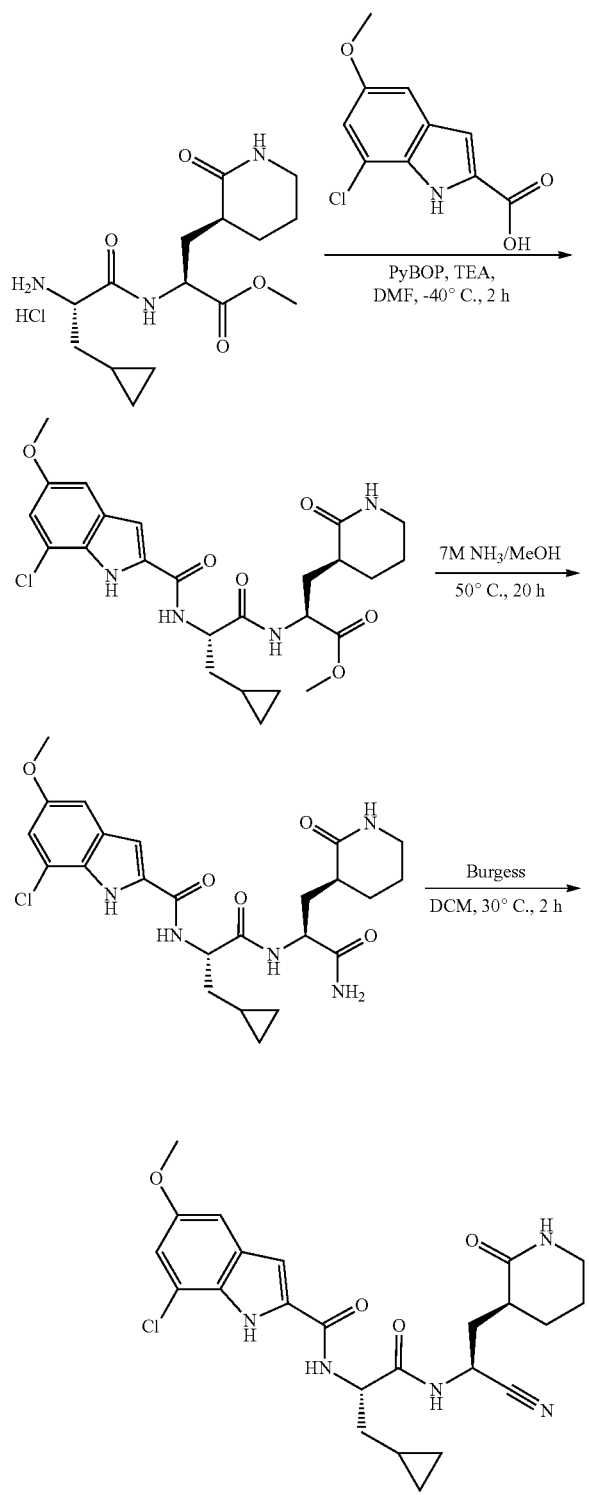

To a solution of 7-chloro-5-methoxy-1H-indole-2-carboxylic acid (1 g, 3.24 mmol, 85% purity, 1.1 eq, HCl) and methyl (2S)-2-[[(2S)-2-amino-3-cyclopropyl-propanoyl]amino]-3-[(3S)-2-oxo-3-piperidyl] propanoate (918.04 mg, 2.95 mmol, 1 eq) in DMF (15 mL) was added PyBOP (1.53 g, 2.95 mmol, 1 eq). TEA (895.02 mg, 8.85 mmol, 1.23 mL, 3 eq) in DMF (5 mL) was added, and then the mixture was stirred at −40° C. for 2 h. Upon completion, the mixture was quenched by water (60 mL) and was extracted with DCM (20 mL*3), then was concentration in vacuum and was purified by column (SiO$_2$, petroleum ether:ethyl acetate=5:1 to 0:1) to obtain (S)-methyl2-((S)-2-(7-chloro-5-methoxy-1H-indole-2-carboxamido)-3-cyclopropylpropanamido)-3-((S)-2-oxopiperidin-3-yl)propanoate (1.5 g, 2.02 mmol, 68.62% yield, 70% purity) as a brown gum. MS (ESI) m/z 519.2 [M+H]$^+$ Step 2: N-((S)-1-(((S)-1-amino-1-oxo-3-((S)-2-oxopiperidin-3 yl)propan-2-yl)amino)-3-cyclopropyl-1-oxopropan-2 yl)-7-chloro-5-methoxy-1H-indole-2-carboxamide A solution of (S)-methyl2-((S)-2-(7-chloro-5-methoxy-1H-indole-2-carboxamido)-3-cyclopropylpropanamido)-3-((S)-2-oxopiperidin-3-yl) propanoate (350 mg, 674.39 umol, 1 eq) in NH$_3$/MeOH (7M, 4 mL) was stirred at 50° C. for 20 h. Upon completion, the mixture was concentrated in vacuum to obtain N-((S)-1-(((S)-1-amino-1-oxo-3-((S)-2-oxopiperidin-3-yl)propan-2-yl)amino)-3-cyclopropyl-1-oxopropan-2-yl)-7-chloro-5-methoxy-1H-indole-2-carboxamide (1.3 g, crude) as a brown gum. MS (ESI) m/z 502.1 [M−H]$^+$ Step 3: 7-chloro-N-((S)-1-(((S)-1-cyano-2-((S)-2-oxopiperidin-3-yl)ethyl)amino)-3-cyclopropyl-1-oxopropan-2-yl)-5-methoxy-1H-indole-2-carboxamide To a solution of N-((S)-1-(((S)-1-amino-1-oxo-3-((S)-2-oxopiperidin-3-yl)propan-2-yl) amino)-3-cyclopropyl-1-oxopropan-2-yl)-7-chloro-5-methoxy-1H-indole-2-carboxamide (1.3 g, 2.58 mmol, 1 eq) in DCM (20 mL) was added Burgess reagent (1.84 g, 7.74 mmol, 3 eq) at 30° C. The resulting mixture was stirred at 30° C. for 2 h. Upon completion, the mixture was quenched by water (2 mL) and was dried by blowing N$_2$. The mixture was purified by prep-HPLC (column: Waters Xbridge C18 150*50 mm*10 um; mobile phase: [water (10 mM NH$_4$HCO$_3$)-ACN]; B %: 25%-55%, 10 min) to obtain 7-chloro-N-((S)-1-(((S)-1-cyano-2-((S)-2-oxopiperidin-3-yl)ethyl)amino)-3-cyclopropyl-1-oxopropan-2-yl)-5-methoxy-1H-indole-2-carboxamide (260 mg, 535.02 umol, 20.74% yield, 100% purity) as a white solid. MS (ESI) m/z 486.1[M+H]$^+$ $^1$H NMR (400 MHz, DMSO-d$_6$) δ ppm 11.57 (s, 1H), 8.99 (d, J=8.0 Hz, 1H), 8.65 (d, J=7.6 Hz, 1H), 7.53 (s, 1H), 7.15 (dd, J=2.2, 11.3 Hz, 2H), 7.00 (d, J=2.2 Hz, 1H), 5.07 (q, J=8.0 Hz, 1H), 4.58-4.44 (m, 1H), 3.84-3.72 (m, 3H), 3.17-3.00 (m, 2H), 2.30-2.20 (m, 2H), 1.91-1.65 (m, 4H), 1.64-1.33 (m, 3H), 0.87-0.73 (m, 1H), 0.50-0.35 (m, 2H), 0.26-0.05 (m, 2H).

Example 220. Synthesis of Viral Protease Inhibitor Compound 908

Step 1: methyl (2S)-2-(2-azaspiro[4.5]decane-3-carbonylamino)-3-[(3S)-2-oxo-3-piperidyl]propanoatemethyl

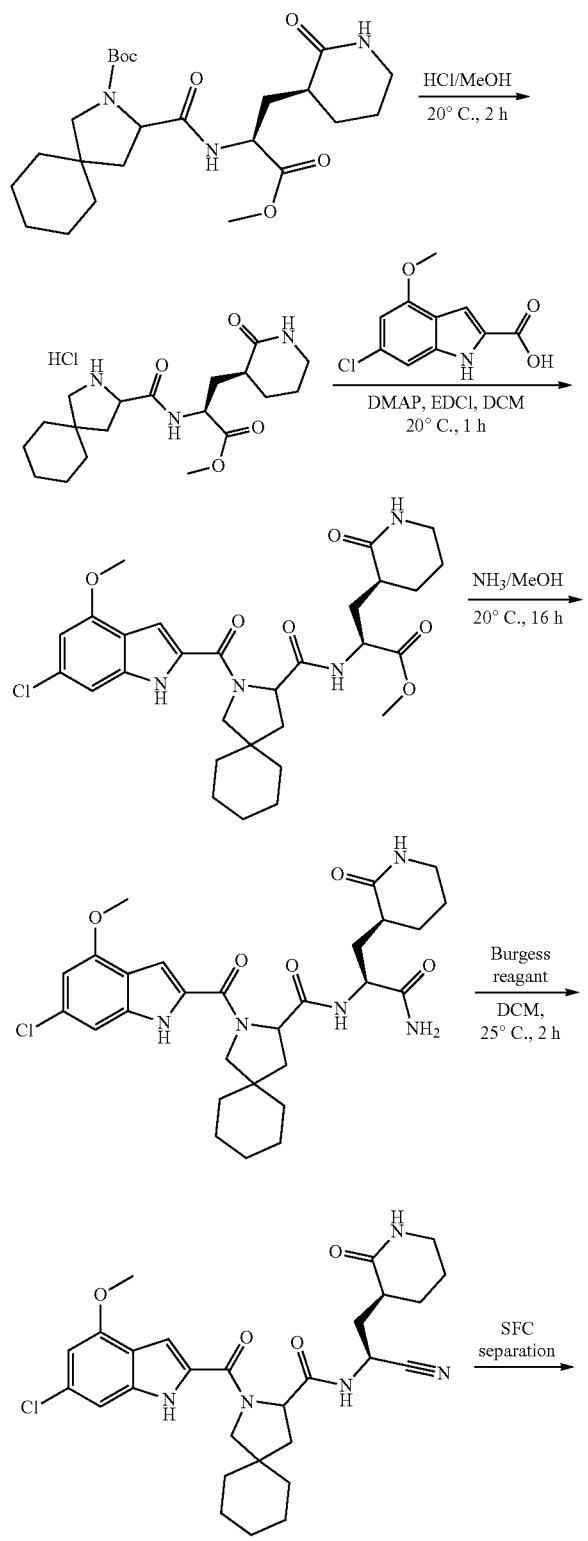

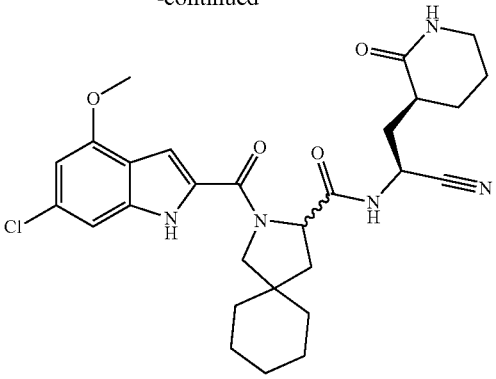

A solution of tert-butyl 3-[[(1S)-2-methoxy-2-oxo-1-[[(3S)-2-oxo-3-piperidyl]methyl]ethyl]carbamoyl]-2-azaspiro[4.5]decane-2-carboxylate (1.5 g, 3.22 mmol, 1 eq) in HCl/MeOH (15 mL) was stirred at 20° C. for 2 h. Upon completion, the reaction mixture was concentrated under reduced pressure to remove solvent to afford methyl (2S)-2-(2-azaspiro[4.5]decane-3-carbonylamino)-3-[(3S)-2-oxo-3-piperidyl]propanoate (1.25 g, crude, HCl) as a white solid. MS (ESI) m/z 366.2 [M+H]$^+$ Step 2: methyl (2S)-2-[[2-(6-chloro-4-methoxy-1H-indole-2-carbonyl)-2-azaspiro[4.5]decane-3-carbonyl]amino]-3-[(3S)-2-oxo-3-piperidyl]propanoate To a solution of methyl (2S)-2-(2-azaspiro[4.5]decane-3-carbonylamino)-3-[(3S)-2-oxo-3-piperidyl]propanoate (1.25 g, 3.10 mmol, 1 eq, HCl) and 6-chloro-4-methoxy-1H-indole-2-carboxylic acid (700 mg, 3.10 mmol, 1 eq) in DCM (40 mL) was added DMAP (1.14 g, 9.31 mmol, 3 eq). After adding EDCI (1.78 g, 9.31 mmol, 3 eq), the mixture was stirred at 20° C. for 1 h. Upon completion, the reaction mixture was quenched by addition H$_2$O (30 mL), and then extracted with DCM (15 mL*2). The combined organic layers were washed with HCl (1 M) (10 mL*2), and then the combined organic layers were washed with brine (20 mL), dried over Na$_2$SO$_4$, filtered and concentrated under reduced pressure to give a residue. The residue was purified by column chromatography (SiO$_2$, petroleum ether/ethyl acetate=3/1 to 0/1, dichloromethane:methanol=10:1, (UV 254 nm)) to give methyl (2S)-2-[[2-(6-chloro-4-methoxy-1H-indole-2-carbonyl)-2-azaspiro[4.5]decane-3-carbonyl]amino]-3-[(3S)-2-oxo-3-piperidyl]propanoate (1.2 g, 1.96 mmol, 63.24% yield, 93.7% purity) as a yellow solid. MS (ESI) m/z 573.2 [M+H]$^+$ Step 3: N-[(1S)-2-amino-2-oxo-1-[[(3S)-2-oxo-3-piperidyl]methyl]ethyl]-2-(6-chloro-4-methoxy-1H-indole-2-carbonyl)-2-azaspiro[4.5]decane-3-carboxamide A solution of methyl (2S)-2-[[2-(6-chloro-4-methoxy-1H-indole-2-carbonyl)-2-azaspiro[4.5]decane-3-carbonyl]amino]-3-[(3S)-2-oxo-3-piperidyl]propanoate (1.1 g, 1.92 mmol, 1 eq) in NH$_3$/MeOH (7 M, 60 mL, 218.81 eq) was stirred at 20° C. for 16 h. The reaction mixture was concentrated under reduced pressure to remove solvent to give N-[(1S)-2-amino-2-oxo-1-[[(3S)-2-oxo-3-piperidyl]methyl]ethyl]-2-(6-chloro-4-methoxy-1H-indole-2-carbonyl)-2-azaspiro[4.5]decane-3-carboxamide (1.05 g, crude) as a yellow solid. MS (ESI) m/z 558.2 [M+H]$^+$

Step 4: 2-(6-chloro-4-methoxy-1H-indole-2-carbonyl)-N-[(1S)-1-cyano-2-[(3S)-2-oxo-3-piperidyl]ethyl]-2-azaspiro[4.5]decane-3-carboxamide To a solution of N-[(1S)-2-amino-2-oxo-1-[[(3S)-2-oxo-3-piperidyl]methyl]ethyl]-2-(6-chloro-4-methoxy-1H-indole-2-carbonyl)-2-azaspiro[4.5]decane-3-carboxamide (1.04 g, 1.86 mmol, 1 eq) in DCM (20 mL) was added Burgess reagent (888.20 mg, 3.73 mmol, 2 eq). The mixture was stirred at 25° C. for 2 h. Upon completion, the reaction mixture was concentrated under reduced pressure to remove solvent. The residue was purified by prep-HPLC (column: Waters Xbridge C18 150*50 mm*10 um; mobile phase: [water (10 mM NH$_4$HCO$_3$)-ACN]; B %: 50%-70%, 10 min) to give 2-(6-chloro-4-methoxy-1H-indole-2-carbonyl)-N-[(1S)-1-cyano-2-[(3S)-2-oxo-3-piperidyl]ethyl]-2-azaspiro[4.5]decane-3-carboxamide (500 mg, 886.03 umol, 47.54% yield, 95.7% purity) as a white solid. MS (ESI) m/z 540.2 [M+H]$^+$.

Step 5: 2-(6-chloro-4-methoxy-1H-indole-2-carbonyl)-N-[(1S)-1-cyano-2-[(3S)-2-oxo-3-piperidyl]ethyl]-2-azaspiro[4.5]decane-3-carboxamide Isomer 1:

2-(6-Chloro-4-methoxy-1H-indole-2-carbonyl)-N-[(1S)-1-cyano-2-[(3S)-2-oxo-3-piperidyl]ethyl]-2-azaspiro[4.5]decane-3-carboxamide (500 mg) was separated by SFC (column: REGIS (s,s) WHELK-O1 (250 mm*30 mm, 5 um); mobile phase: [0.1% NH$_3$H$_2$O ETOH]; B %: 50%-50%, 6 min) to give 2-(6-chloro-4-methoxy-1H-indole-2-carbonyl)-N-[(1S)-1-cyano-2-[(3S)-2-oxo-3-piperidyl]ethyl]-2-azaspiro[4.5]decane-3-carboxamide (66.7 mg, 123.01 umol, 13.29% yield, 99.6% purity) as a white solid. MS (ESI) m/z 540.2 [M+H]$^+$.

1H NMR (400 MHz, DMSO-d$_6$) δ=11.76-11.61 (m, 1H), 8.88 (d, J=8.4 Hz, 1H), 7.67-7.33 (m, 1H), 7.14-6.86 (m, 2H), 6.67-6.48 (m, 1H), 5.06-4.87 (m, 1H), 4.49 (t, J=8.8 Hz, 1H), 3.92 (s, 2H), 3.88-3.80 (m, 1H), 3.66 (d, J=10.3 Hz, 1H), 3.33 (s, 6H), 2.38-2.17 (m, 2H), 2.03-0.83 (m, 14H)

$^1$H NMR (400 MHz, DMSO-d$_6$, 273+80K) δ=11.46 (s, 1H), 8.71 (s, 1H), 7.27 (s, 1H), 7.09 (s, 2H), 6.55 (s, 1H), 4.97 (s, 1H), 4.61 (s, 1H), 3.92 (s, 2H), 3.85 (d, J=10.4 Hz, 1H), 3.61 (s, 1H), 3.08 (s, 6H), 2.38-2.12 (m, 2H), 2.01-1.02 (m, 14H)

Isomer 2:

2-(6-Chloro-4-methoxy-1H-indole-2-carbonyl)-N-[(1S)-1-cyano-2-[(3S)-2-oxo-3-piperidyl]ethyl]-2-azaspiro[4.5]decane-3-carboxamide (111.6 mg, 206.65 umol, 22.32% yield, 100% purity) was obtained as a white solid. MS (ESI) m/z 540.2 [M+H]$^+$.

$^1$H NMR (400 MHz, DMSO-d$_6$) δ=11.76-11.64 (m, 1H), 8.81 (d, J=8.4 Hz, 1H), 7.53-7.41 (m, 1H), 7.06 (s, 1H), 6.97 (s, 1H), 6.65-6.51 (m, 1H), 5.04-4.86 (m, 1H), 4.58-4.38 (m, 1H), 3.92 (s, 2H), 3.84 (d, J=9.8 Hz, 1H), 3.76-3.57 (m, 1H), 3.33 (s, 6H), 2.24-2.11 (m, 2H), 1.88-1.10 (m, 14H)

1H NMR (400 MHz, DMSO-d$_6$, 273+80K) δ=11.48 (s, 1H), 8.64 (s, 1H), 7.23 (s, 1H), 7.09 (s, 1H), 6.93 (s, 1H), 6.56 (s, 1H), 4.97 (s, 1H), 4.59 (s, 1H), 3.93 (s, 2H), 3.85 (d, J=10.8 Hz, 1H), 3.65 (s, 1H), 3.08 (s, 6H), 2.20 (s, 2H), 2.01-1.23 (m, 14H)

Example 221. Synthesis of Viral Protease Inhibitor Compound 1057

Step 1: methyl (2S)-2-[[(2S)-3-cyclopropyl-2-[[4-[2-(2-methoxyethoxy)ethoxy]-1H-indole-2-carbonyl]amino]propanoyl]amino]-3-[(3S)-2-oxo-3-piperidyl]propanoate

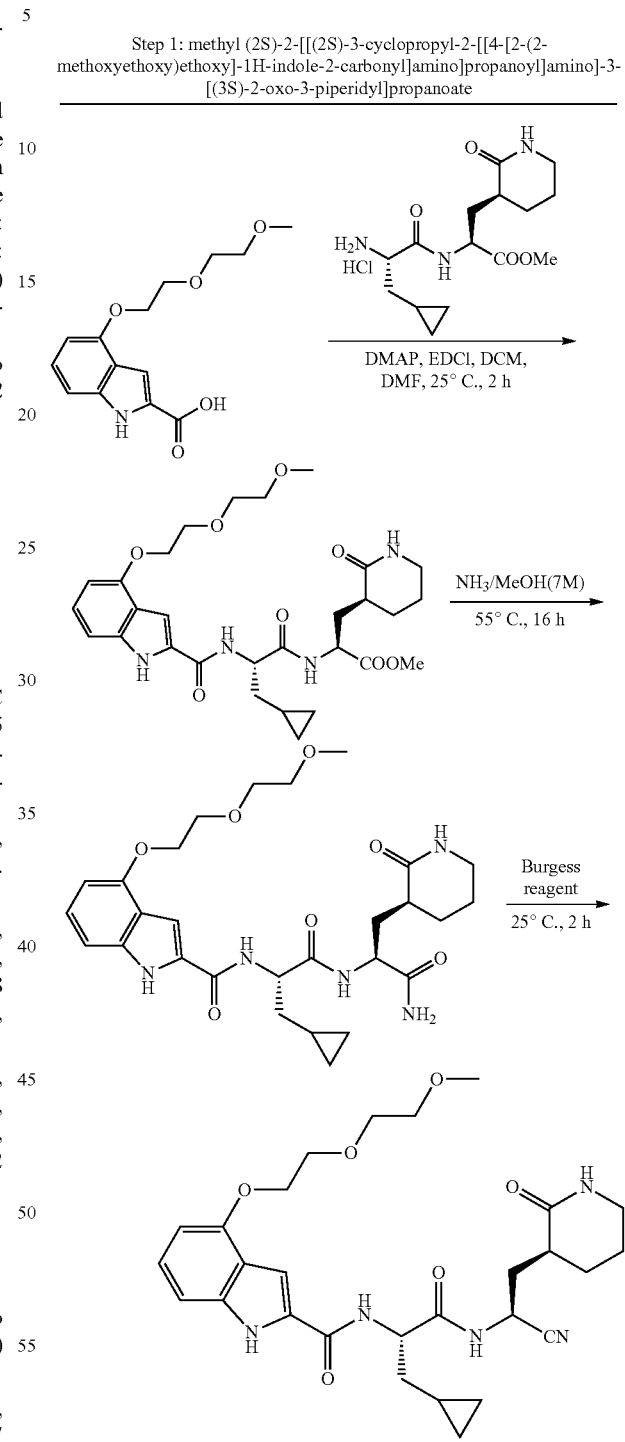

To a mixture of 4-[2-(2-methoxyethoxy)ethoxy]-1H-indole-2-carboxylic acid (500 mg, 1.79 mmol, 1 eq) and methyl (2S)-2-[[(2S)-2-amino-3-cyclopropyl-propanoyl]amino]-3-[(3S)-2-oxo-3-piperidyl]propanoate (684.99 mg, 1.97 mmol, 1.1 eq, HCl) in DCM (9 mL) and DMF (3 mL) was added DMAP (656.15 mg, 5.37 mmol, 3 eq) and EDCI (686.39 mg, 3.58 mmol, 2 eq) in one portion at 25° C. The mixture was stirred at 25° C. for 2 hours. Upon completion, the reaction mixture was diluted with H₂O (10 mL) and extracted with ethyl acetate (10 mL*3). The combined organic layers were washed with brine (15 mL*1), dried over Na₂SO₄, filtered and concentrated under reduced pressure to give the crude product. The crude was purified by column chromatography (SiO₂, petroleum ether/ethyl acetate=3/1 to 0/1) to give methyl (2S)-2-[[(2S)-3-cyclopropyl-2-[[4-[2-(2-methoxyethoxy)ethoxy]-1H-indole-2-carbonyl]amino]propanoyl]amino]-3-[(3S)-2-oxo-3-piperidyl] propanoate (850 mg, 1.48 mmol, 82.91% yield) as a yellow solid. MS (ESI) m/z 573.3 [M+H]⁺

Step 2: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-[2-(2-methoxyethoxy)ethoxy]-1H-indole-2-carboxamide A mixture of methyl (2S)-2-[[(2S)-3-cyclopropyl-2-[[4-[2-(2-methoxyethoxy)ethoxy]-1H-indole-2-carbonyl]amino]propanoyl]amino]-3-[(3S)-2-oxo-3-piperidyl]propanoate (850 mg, 1.41 mmol, 95% purity, 1 eq) in NH₃/MeOH (7 M, 25 mL, 124.10 eq) was stirred at 55° C. for 16 hours. Upon completion, the reaction mixture was concentrated under reduced pressure to give N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-[2-(2-methoxyethoxy)ethoxy]-1H-indole-2-carboxamide (781 mg, 1.22 mmol, 86.41% yield, 87% purity) as a yellow solid. MS (ESI) m/z 558.3 [M+H]⁺

Step 3: N-[(1S)-2-[[(1S)-1-cyano-2-[(3S)-2-oxo-3-piperidyl]ethyl]amino]-1-(cyclopropylmethyl)-2-oxo-ethyl]-4-[2-(2-methoxyethoxy)ethoxy]-1H-indole-2-carboxamide A mixture of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-[2-(2-methoxyethoxy)ethoxy]-1H-indole-2-carboxamide (730 mg, 1.14 mmol, 87% purity, 1 eq) in DCM (10 mL) was added Burgess reagent (542.82 mg, 2.28 mmol, 2 eq) in one portion at 25° C. The mixture was stirred at 25° C. for 2 h. Upon completion, the reaction mixture was concentrated under reduced pressure to give the crude product. The crude was purified by prep-HPLC (neutral condition; column: Waters Xbridge Prep OBD C18 150*40 mm*10 um; mobile phase: [water (10 mM NH4HCO3)-ACN]; B %: 20%-50%, 8 min) to give N-[(1S)-2-[[(1S)-1-cyano-2-[(3S)-2-oxo-3-piperidyl]ethyl]amino]-1-(cyclopropylmethyl)-2-oxo-ethyl]-4-[2-(2-methoxyethoxy)ethoxy]-1H-indole-2-carboxamide (230 mg, 426.22 umol, 37.42% yield) as a white solid. MS (ESI) m/z 540.2 [M+H]⁺

¹H NMR (400 MHz, DMSO-d₆) δ=11.56 (s, 1H), 8.89 (d, J=8.2 Hz, 1H), 8.58 (d, J=7.5 Hz, 1H), 7.52 (br s, 1H), 7.39 (d, J=1.5 Hz, 1H), 7.11-6.99 (m, 2H), 6.50 (d, J=7.5 Hz, 1H), 5.10-5.01 (m, 1H), 4.49-4.41 (m, 1H), 4.21 (t, J=4.4 Hz, 2H), 3.86-3.79 (m, 2H), 3.63 (dd, J=3.7, 5.7 Hz, 2H), 3.49 (dd, J=3.7, 5.5 Hz, 2H), 3.26 (s, 3H), 3.13-3.03 (m, 2H), 2.36-2.20 (m, 2H), 1.90-1.76 (m, 3H), 1.75-1.65 (m, 1H), 1.62-1.50 (m, 1H), 1.49-1.34 (m, 2H), 0.88-0.75 (m, 1H), 0.48-0.33 (m, 2H), 0.24-0.07 (m, 2H)

Example 221. Synthesis of Viral Protease Inhibitor Compound 822

Step 1: methyl (Z)-2-azido-3-(2-chloro-3-fluoro-phenyl)prop-2-enoate

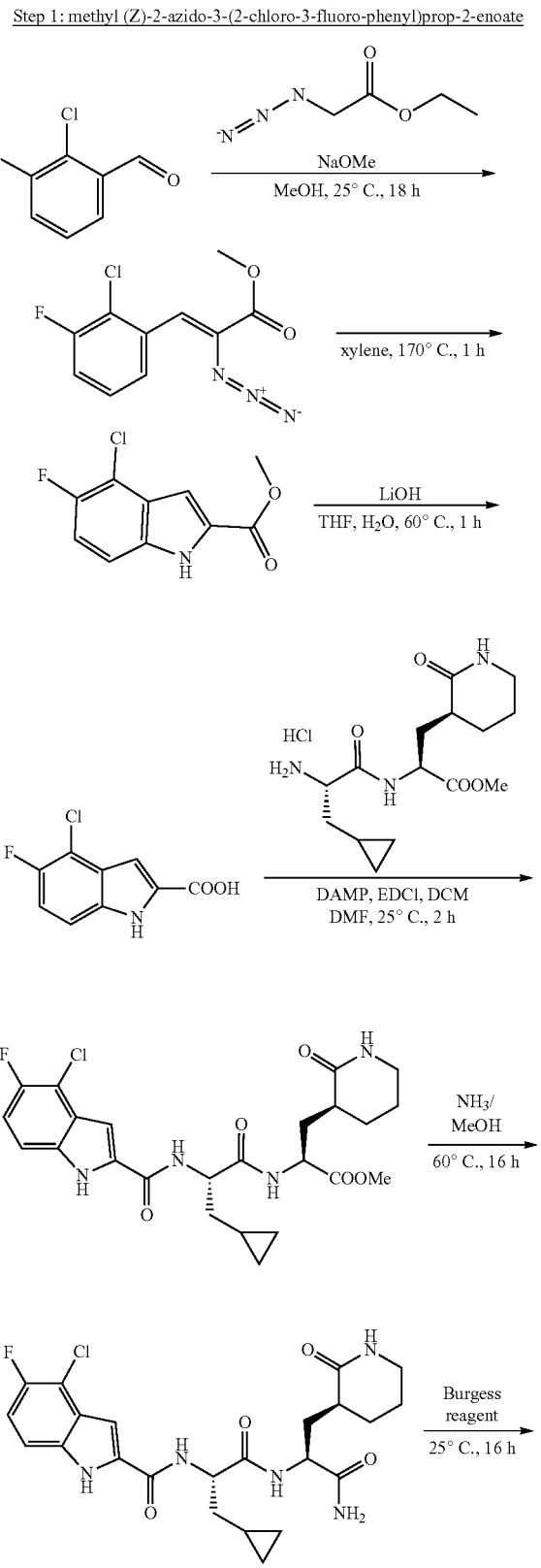

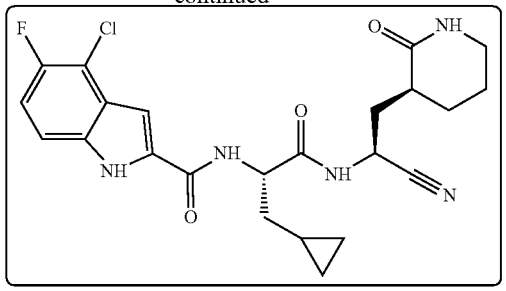

A mixture of NaOMe (3.41 g, 63.07 mmol, 2 eq) in MeOH (30 mL) was cooled to −10° C., a mixture of 2-chloro-3-fluoro-benzaldehyde (5 g, 31.53 mmol, 1 eq) and ethyl 2-azidoacetate (8.14 g, 63.07 mmol, 7.21 mL, 2 eq) in MeOH (100 mL) was added drop-wise to the former solution, the mixture was stirred at 25° C. for 18 h. Upon completion, the reaction mixture was concentrated under reduced pressure to give a residue, the residue was diluted with H2O 60 mL and extracted with EA 90 mL (30 mL*3). The combined organic layers were washed with brine 45 mL (45 mL*1), dried over $Na_2SO_4$, filtered and concentrated under reduced pressure to give the crude product. The crude was purified by column chromatography (SiO2, Petroleum ether/Ethyl acetate=1/0) to give methyl (Z)-2-azido-3-(2-chloro-3-fluoro-phenyl)prop-2-enoate (2.5 g, 9.78 mmol, 31.01% yield) as a yellow solid.

Step 2: methyl 4-chloro-5-fluoro-1H-indole-2-carboxylate

A mixture of methyl (Z)-2-azido-3-(2-chloro-3-fluoro-phenyl)prop-2-enoate (2.3 g, 9.00 mmol, 1 eq) in xylene (25 mL) was stirred at 170° C. for 1 h. Upon completion, the reaction mixture was filtered to give methyl 4-chloro-5-fluoro-1H-indole-2-carboxylate (1.4 g, 6.15 mmol, 68.36% yield) as a white solid.

Step 3: 4-chloro-5-fluoro-1H-indole-2-carboxylic acid

A mixture of methyl 4-chloro-5-fluoro-1H-indole-2-carboxylate (1.4 g, 6.15 mmol, 1 eq) in THF (7 mL) and $H_2O$ (7 mL) was added LiOH·$H_2O$ (516.20 mg, 12.30 mmol, 2 eq) in one portion at 25° C. The mixture was stirred at 60° C. for 1 hour. Upon completion, the reaction mixture was adjusted to acidity by 1M HCl solution, and extracted with EA 45 mL (15 mL*3). The combined organic layers were washed with brine 20 mL (20 mL*1), dried over Na2SO4, filtered and concentrated under reduced pressure to give 4-chloro-5-fluoro-1H-indole-2-carboxylic acid (1 g, 4.68 mmol, 76.12% yield) as a white solid. (ESI) m/z 211.9 $[M-H]^+$ Step 4: methyl (2S)-2-[[(2S)-2-[(4-chloro-5-fluoro-1H-indole-2-carbonyl)amino]-3-cyclopropyl-propanoyl]amino]-3-[(3S)-2-oxo-3-piperidyl]propanoate To a mixture of 4-chloro-5-fluoro-1H-indole-2-carboxylic acid (500 mg, 2.34 mmol, 1 eq) and methyl (2S)-2-[[(2S)-2-amino-3-cyclopropyl-propanoyl]amino]-3-[(3S)-2-oxo-3-piperidyl]propanoate (895.68 mg, 2.57 mmol, 1.1 eq, HCl) in DCM (10 mL) and DMF (3 mL) was added DMAP (857.96 mg, 7.02 mmol, 3 eq) and EDCI (897.50 mg, 4.68 mmol, 2 eq) in one portion at 25° C. The mixture was stirred at 25° C. for 2 hours. Upon completion, the reaction mixture was diluted with $H_2O$ 30 mL and extracted with EA 60 mL (20 mL*3). The combined organic layers were washed with brine 30 mL (30 mL*1), dried over Na2SO4, filtered and concentrated under reduced pressure to give the crude product. The crude was purified by column chromatography (SiO2, Petroleum ether/Ethyl acetate=5/1 to 0/1) to give methyl (2S)-2-[[(2S)-2-[(4-chloro-5-fluoro-1H-indole-2-carbonyl)amino]-3-cyclopropyl-propanoyl]amino]-3-[(3S)-2-oxo-3-piperidyl]propanoate (800 mg, 1.58 mmol, 67.41% yield) as a white solid. MS (ESI) m/z 505.0 $[M-H]^+$ Step 5: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-chloro-5-fluoro-1H-indole-2-carboxamide A mixture of methyl (2S)-2-[[(2S)-2-[(4-chloro-5-fluoro-1H-indole-2-carbonyl)amino]-3-cyclopropyl-propanoyl]amino]-3-[(3S)-2-oxo-3-piperidyl]propanoate (800 mg, 1.58 mmol, 1 eq) in $NH_3$/MeOH (7 M, 20 mL, 88.72 eq) was stirred at 60° C. for 16 h. Upon completion, the reaction mixture was concentrated under reduced pressure to give N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-chloro-5-fluoro-1H-indole-2-carboxamide (730 mg, 1.35 mmol, 85.57% yield, 91% purity) as a white solid. MS (ESI) m/z 492.2 $[M+H]^+$ Step 6: 4-chloro-N-[(1S)-2-[[(1S)-1-cyano-2-[(3S)-2-oxo-3-piperidyl]ethyl]amino]-1-(cyclopropylmethyl)-2-oxo-ethyl]-5-fluoro-1H-indole-2-carboxamide A mixture of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-chloro-5-fluoro-1H-indole-2-carboxamide (730 mg, 1.26 mmol, 85% purity, 1 eq) in DCM (20 mL) was added Burgess reagent (1.05 g, 4.41 mmol, 3.5 eq) in one portion at 25° C. The mixture was stirred at 25° C. for 16 hours. Upon completion, the reaction mixture was concentrated under reduced pressure to give the crude. The crude was purified by prep-HPLC (neutral condition; column: Phenomenex Gemini-NX C18 75*30 mm*3 um; mobile phase: [water (10 mM NH4HCO3)-ACN]; B %: 25%-55%, 8 min) to give 4-chloro-N-[(1S)-2-[[(1S)-1-cyano-2-[(3S)-2-oxo-3-piperidyl]ethyl]amino]-1-(cyclopropylmethyl)-2-oxo-ethyl]-5-fluoro-1H-indole-2-carboxamide (300 mg, 633.01 umol, 50.19% yield) as a white solid. MS (ESI) m/z 474.1 [M+H]

$^1$H NMR (400 MHz, DMSO-$d_6$) δ=12.06 (br s, 1H), 8.94 (d, J=8.2 Hz, 1H), 8.81 (d, J=7.5 Hz, 1H), 7.54 (br s, 1H), 7.47 (s, 1H), 7.40 (dd, J=4.0, 9.0 Hz, 1H), 7.23 (t, J=9.4 Hz, 1H), 5.11-5.03 (m, 1H), 4.51-4.42 (m, 1H), 3.09 (br s, 2H), 2.31-2.20 (m, 2H), 1.92-1.76 (m, 3H), 1.76-1.64 (m, 1H), 1.56 (br d, J=3.3 Hz, 1H), 1.51-1.33 (m, 2H), 0.88-0.76 (m, 1H), 0.49-0.35 (m, 2H), 0.26-0.05 (m, 2H)

Example 222. Synthesis of Viral Protease Inhibitor Compound 824

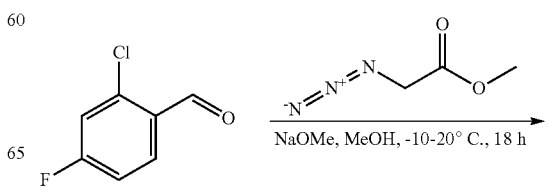

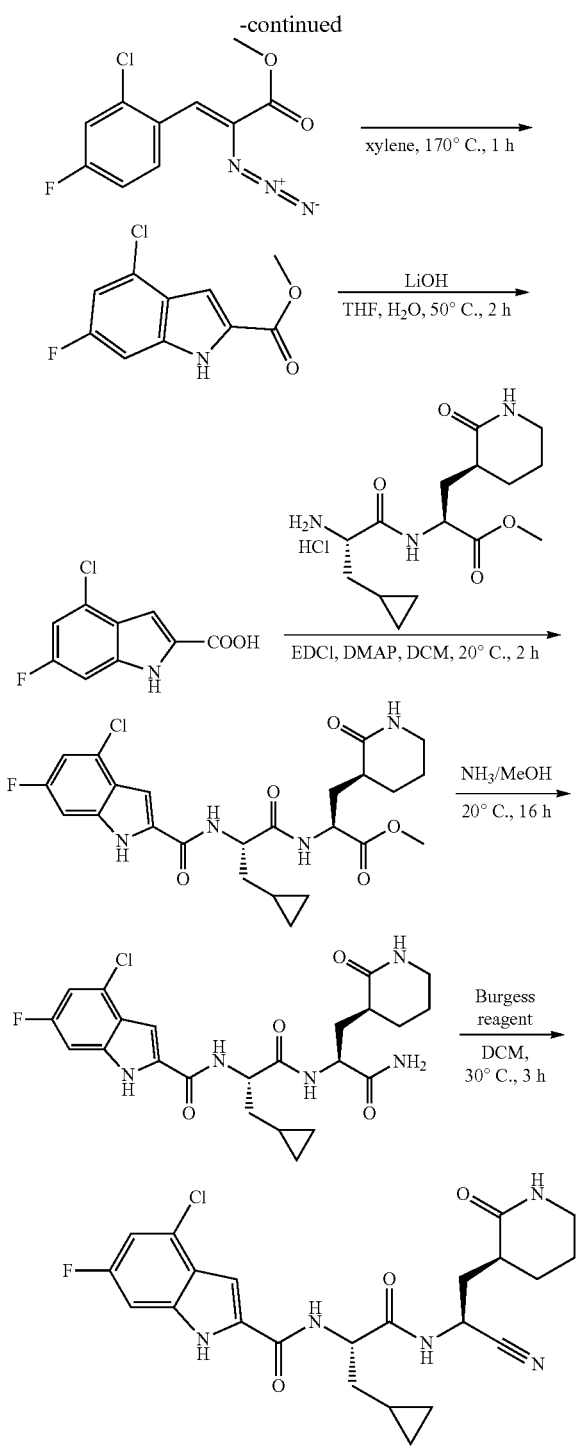

Step 1: (Z)-methyl 2-azido-3-(2-chloro-4-fluorophenyl)acrylate

To a solution of NaOMe (13.63 g, 252.27 mmol, 4 eq) in MeOH (50 mL), then 2-chloro-4-fluoro-benzaldehyde (10 g, 63.07 mmol, 1 eq) and methyl 2-azidoacetate (30.49 g, 264.89 mmol, 4.2 eq) in MeOH (50 mL) was added at −10° C. The mixture was stirred at 20° C. for 18 h. Upon completion, the reaction mixture was filtered and concentrated under reduced pressure to give methyl (Z)-2-azido-3-(2-chloro-4-fluoro-phenyl)prop-2-enoate (7 g, crude) as a yellow solid.

Step 2: methyl 4-chloro-6-fluoro-1H-indole-2-carboxylate

To a solution of methyl (Z)-2-azido-3-(2-chloro-4-fluorophenyl)prop-2-enoate (6 g, 23.47 mmol, 1 eq) in XYLENE (70 mL). The mixture was stirred at 170° C. for 1 h. Upon completion, the reaction mixture was concentrated under reduced pressure to remove solvent. The residue was purified by column chromatography (SiO$_2$, Petroleum ether/Ethyl acetate=1/0 to 8/1) to give methyl 4-chloro-6-fluoro-1H-indole-2-carboxylate (2 g, 8.79 mmol, 37.44% yield) as a yellow solid. MS (ESI) m/z 228.1 [M+H]$^+$.

Step 3: 4-chloro-6-fluoro-1H-indole-2-carboxylic acid

To a solution of methyl 4-chloro-6-fluoro-1H-indole-2-carboxylate (2 g, 8.79 mmol, 1 eq) in THF (20 mL) and H$_2$O (10 mL) was added LiOH·H$_2$O (1.11 g, 26.36 mmol, 3 eq). The mixture was stirred at 50° C. for 2 h. Upon completion, the reaction mixture was concentrated under reduced pressure to remove solvent. Then 1M HCl was added, adjust pH=3, then was filtered and concentrated under reduced pressure to give 4-chloro-6-fluoro-1H-indole-2-carboxylic acid (1.6 g, crude) as a yellow solid. MS (ESI) m/z 214.0 [M+H]$^+$.

Step 4: (S)-methyl 2-((S)-2-(4-chloro-6-fluoro-1H-indole-2-carboxamido)-3-cyclopropylpropanamido)-3-((S)-2-oxopiperidin-3-yl)propanoate To a solution of 4-chloro-6-fluoro-1H-indole-2-carboxylic acid (1 g, 4.68 mmol, 1 eq), methyl (2S)-2-[[(2S)-2-amino-3-cyclopropyl-propanoyl]amino]-3-[(3S)-2-oxo-3-piperidyl]propanoate (1.63 g, 4.68 mmol, 1 eq, HCl), DMAP (1.72 g, 14.05 mmol, 3 eq) in DCM (10 mL), then EDCI (1.80 g, 9.36 mmol, 2 eq) was added. The mixture was stirred at 20° C. for 2 h. Upon completion, the reaction mixture was poured into H$_2$O 35 mL at 20° C., and then extracted with DCM (35 mL*3). The combined organic layers were washed with 1M HCl (40 mL*2), then the combined organic layers were washed with brine (40 mL*2), dried over Na$_2$SO$_4$, filtered and concentrated under reduced pressure to give a residue. The residue was purified by column chromatography (SiO$_2$, Petroleum ether/Ethyl acetate=1/0 to 0/1) to give methyl (2S)-2-[[(2S)-2-[(4-chloro-6-fluoro-1H-indole-2-carbonyl)amino]-3-cyclopropyl-propanoyl]amino]-3-[(3S)-2-oxo-3-piperidyl]propanoate (1.1 g, 2.17 mmol, 46.35% yield, 100% purity) as a yellow solid. MS (ESI) m/z 507.2 [M+H]$^+$.

Step 5: N-((S)-1-(((S)-1-amino-1-oxo-3-((S)-2-oxopiperidin-3-yl)propan-2-yl)amino)-3-cyclopropyl-1-oxopropan-2-yl)-4-chloro-6-fluoro-1H-indole-2-carboxamide To a solution of methyl (2S)-2-[[(2S)-2-[(4-chloro-6-fluoro-1H-indole-2-carbonyl)amino]-3-cyclopropyl-propanoyl]amino]-3-[(3S)-2-oxo-3-piperidyl]propanoate (1.06 g, 2.09 mmol, 1 eq) in NH$_3$/MeOH (7 M, 20 mL, 66.96 eq). The mixture was stirred at 20° C. for 16 h. Upon completion, the reaction mixture was concentrated under reduced pressure to remove solvent to give N-[(1S)-2-[[(1S)-2-amino-2- oxo-1-[[(3S)-2-oxo-3-piperidyl]methyl]ethyl]amino]-1-(cyclopropylmethyl)-2-oxo-ethyl]-4-chloro-6-fluoro-1H-indole-2-carboxamide (1 g, crude) as a yellow solid. MS (ESI) m/z 492.2 [M+H]⁺.

Step 6: 4-chloro-N-((S)-1-(((S)-1-cyano-2-((S)-2-oxopiperidin-3-yl)ethyl)amino)-3-cyclopropyl-1-oxopropan-2-yl)-6-fluoro-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4-chloro-6-fluoro-1H-indole-2-carboxamide (980 mg, 1.99 mmol, 1 eq) in DCM (10 mL) was added BURGESS REAGENT (949.46 mg, 3.98 mmol, 2 eq). The mixture was stirred at 30° C. for 3 h. Upon completion, the reaction mixture was concentrated under reduced pressure to remove solvent. The residue was purified by prep-HPLC (column: Waters Xbridge C18 150*50 mm*10 um; mobile phase: [water (10 mM NH4HCO3)-ACN]; B %: 35%-60%, 10 min) to give 4-chloro-N-[(1S)-2-[[(1S)-1-cyano-2-[(3S)-2-oxo-3-piperidyl]ethyl]amino]-1-(cyclopropylmethyl)-2-oxo-ethyl]-6-fluoro-1H-indole-2-carboxamide (375 mg, 791.26 umol, 39.72% yield, 100% purity) as a white solid. MS (ESI) m/z 474.1 [M+H]⁺.

¹H NMR (400 MHz, DMSO-d₆) δ=12.04 (s, 1H), 8.94 (d, J=8.1 Hz, 1H), 8.77 (d, J=7.5 Hz, 1H), 7.53 (s, 1H), 7.45 (s, 1H), 7.15 (d, J=9.4 Hz, 2H), 5.07 (d, J=7.9 Hz, 1H), 4.46 (d, J=5.7 Hz, 1H), 3.16-2.98 (m, 2H), 2.26 (d, J=9.0 Hz, 2H), 1.97-1.63 (m, 4H), 1.46 (s, 3H), 0.81 (dd, J=5.7, 7.7 Hz, 1H), 0.41 (dd, J=3.5, 7.5 Hz, 2H), 0.26-0.03 (m, 2H).

Example 223. Synthesis of Viral Protease Inhibitor Compound 828

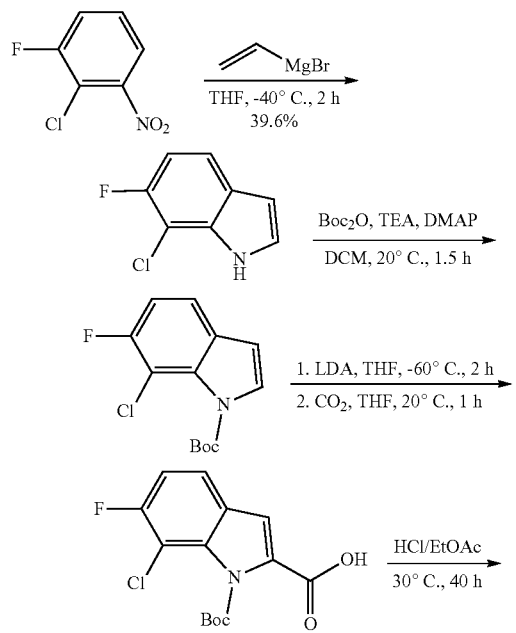

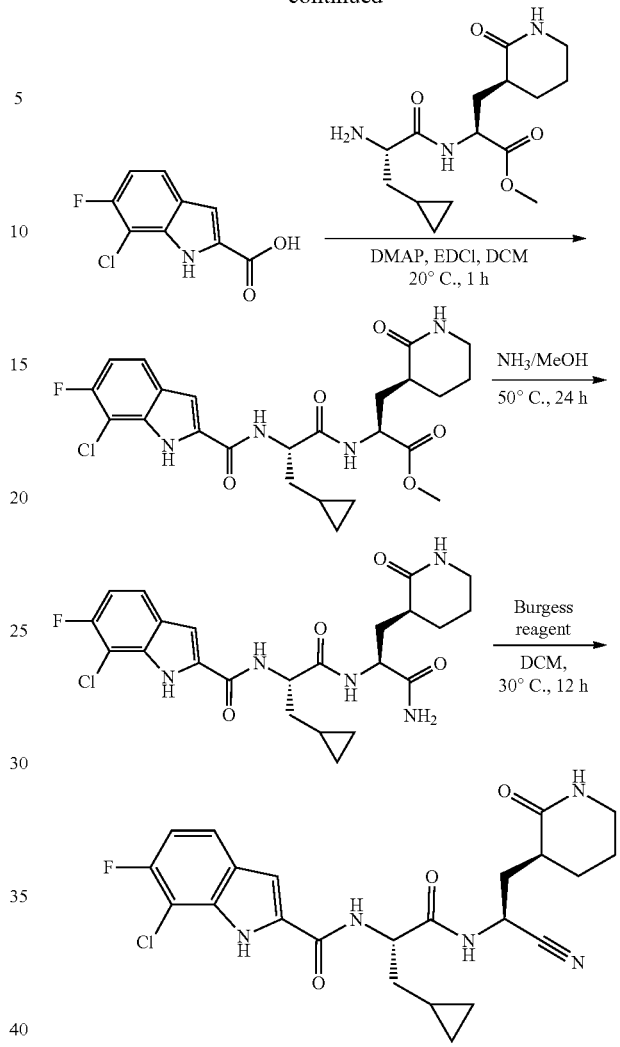

Step 1: 7-chloro-6-fluoro-1H-indole

To a mixture of 2-chloro-1-fluoro-3-nitro-benzene (10 g, 56.97 mmol, 1 eq) in THF (100 mL) was added bromo(vinyl)magnesium (1 M, 199.38 mL, 3.5 eq) drop-wise at −40° C. under N₂. The mixture was stirred at −40° C. for 2 h under N₂. Upon completion, the reaction was quenched by addition NH₄Cl (500 mL) and then extracted with EtOAc (300 mL*2). The combined organic layers were dried over Na₂SO₄, filtered and concentrated under reduced pressure and was purified by column chromatography (SiO₂, EtOAc:MEOH=10:1) to give product 7-chloro-6-fluoro-1H-indole (4.8 g, 25.47 mmol, 44.72% yield, 90% purity) as yellow oil. MS (ESI) m/z 170.0 [M+H]⁺

Step 2: tert-butyl 7-chloro-6-fluoro-indole-1-carboxylate

To a mixture of 7-chloro-6-fluoro-1H-indole (4.8 g, 28.30 mmol, 1 eq) in DCM (50 mL) was added Boc₂O (6.80 g, 31.14 mmol, 1.1 eq), TEA (3.44 g, 33.97 mmol, 4.73 mL, 1.2 eq) and DMAP (691.60 mg, 5.66 mmol, 0.2 eq) at 20° C. under N₂. The mixture was stirred at 20° C. for 1.5 h. Upon completion, the reaction mixture was poured into water (50 mL) and extracted with DCM (40 mL*2). The combined organic layers were concentrated under reduced pressure and was purified by column chromatography (SiO$_2$, Petroleum ether/Ethyl acetate=50/1 to 20/1) to give product tert-butyl 7-chloro-6-fluoro-indole-1-carboxylate (6 g, 22.25 mmol, 78.60% yield) as white solid. MS (ESI) m/z 270.0 [M+H]$^+$ Step 3: 1-tert-butoxycarbonyl-7-chloro-6-fluoro-indole-2-carboxylic acid To a mixture of tert-butyl 7-chloro-6-fluoro-indole-1-carboxylate (2.3 g, 8.53 mmol, 1 eq) in THF (25 mL) was added LDA (2M, 7.25 mL, 1.7 eq) at −60° C. under N$_2$. The mixture was stirred at −60° C. for 2 h, then the above solution was added into drikold (18.77 g, 426.50 mmol, 50 eq) and let stand for 1 h at 20° C. Upon completion, the reaction mixture was poured into water (100 mL) under N$_2$ and stirred for 10 min. The aqueous phase was added 1 M HCl to pH~3-4 at 0° C. and extracted with ethyl acetate (50 mL*3). The combined organic phase was washed with brine (80 mL), dried with anhydrous Na$_2$SO$_4$, filtered and concentrated in vacuum. It was triturated with Petroleum ether: Ethyl acetate=50:1 (100 mL) to give product 1-tert-butoxycarbonyl-7-chloro-6-fluoro-indole-2-carboxylic acid (1.5 g, 4.78 mmol, 56.06% yield) as white powder. MS (ESI) m/z 314.0 [M+H]$^+$ Step 4: 7-chloro-6-fluoro-1H-indole-2-carboxylic acid A solution of 1-tert-butoxycarbonyl-7-chloro-6-fluoro-indole-2-carboxylic acid (4.3 g, 13.71 mmol, 1 eq) in HCl/EtOAc (4 M, 50 mL, 14.59 eq) was stirred at 30° C. for 40 h. Upon completion, the reaction mixture was concentrated under pressure reduced to get the crude product 7-chloro-6-fluoro-1H-indole-2-carboxylic acid (2.9 g, crude) as white solid. MS (ESI) m/z 212.0 [M+H]$^+$ Step 5: methyl (2S)-2-[[(2S)-2-[(7-chloro-6-fluoro-1H-indole-2-carbonyl)amino]-3-cyclopropyl-propanoyl]amino]-3-[(3S)-2-oxo-3-piperidyl]propanoate To a solution of 7-chloro-6-fluoro-1H-indole-2-carboxylic acid (0.7 g, 3.28 mmol, 1.5 eq) and methyl (2S)-2-[[(2S)-2-amino-3-cyclopropyl-propanoyl]amino]-3-[(3S)-2-oxo-3-piperidyl]propanoate (759.97 mg, 2.18 mmol, 1 eq, HCl) in DCM (7 mL) was added EDCI (837.67 mg, 4.37 mmol, 2 eq), DMAP (800.77 mg, 6.55 mmol, 3 eq). The solution was stirred at 20° C., for 1 h. Upon completion, the mixture was quenched by addition H$_2$O (40 mL) and extracted with DCM (10 mL*4). The combined organic layers were dried over Na$_2$SO$_4$, filtered and concentrated under reduced pressure and purified by column chromatography (SiO$_2$, Petroleum ether/Ethyl acetate=1/1 to 0/1 and then DCM:MeOH=5:1) to give product methyl (2S)-2-[[(2S)-2-[(7-chloro-6-fluoro-1H-indole-2-carbonyl)amino]-3-cyclopropyl-propanoyl]amino]-3-[(3S)-2-oxo-3-piperidyl]propanoate (0.8 g, 1.50 mmol, 68.62% yield, 95% purity) as yellow solid. MS (ESI) m/z 505.1 [M+H]$^+$ Step 6: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-6-fluoro-1H-indole-2-carboxamide The methyl (2S)-2-[[(2S)-2-[(7-chloro-6-fluoro-1H-indole-2-carbonyl)amino]-3-cyclopropyl-propanoyl]amino]-3-[(3S)-2-oxo-3-piperidyl]propanoate (0.78 g, 1.54 mmol, 1 eq) in NH$_3$/MEOH (15 mL) was stirred at 50° C. for 24 h. Upon completion, the reaction mixture was concentrated under pressure reduced to give the product N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-6-fluoro-1H-indole-2-carboxamide (0.75 g, crude) as white solid. MS (ESI) m/z 492.2 [M+H]$^+$ Step 7: 7-chloro-N-[(1S)-2-[[(1S)-1-cyano-2-[(3S)-2-oxo-3-piperidyl]ethyl]amino]-1-(cyclopropylmethyl)-2-oxo-ethyl]-6-fluoro-1H-indole-2-carboxamide The N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-6-fluoro-1H-indole-2-carboxamide (0.7 g, 1.31 mmol, 92% purity, 1 eq) in DCM (10 mL) was add BURGESS REAGENT (935.91 mg, 3.93 mmol, 3 eq). The mixture was stirred at 30° C. for 12 h. Upon completion, the reaction was quenched with water (2 mL) and blow-dried with N$_2$ and was purified by prep-HPLC (column: Waters Xbridge C18 150*50 mm*10 um; mobile phase: [water (10 mM NH$_4$HCO$_3$)-ACN]; B %: 25%-55%, 10 min) to give product 7-chloro-N-[(1S)-2-[[(1S)-1-cyano-2-[(3S)-2-oxo-3-piperidyl]ethyl]amino]-1-(cyclopropylmethyl)-2-oxo-ethyl]-6-fluoro-1H-indole-2-carboxamide (0.23 g, 480.45 umol, 36.70% yield, 99% purity) as white solid. MS (ESI) m/z 474.1 [M+H]$^+$ $^1$H NMR (400 MHz, DMSO-d$_6$) δ=8.99 (d, J=7.9 Hz, 1H), 8.68 (d, J=7.5 Hz, 1H), 7.66 (dd, J=4.9, 8.7 Hz, 1H), 7.53 (br s, 1H), 7.29 (s, 1H), 7.18-7.07 (m, 1H), 5.07 (q, J=7.9 Hz, 1H), 4.59-4.42 (m, 1H), 3.18-3.04 (m, 2H), 2.32-2.18 (m, 2H), 2.07 (s, 1H), 1.93-1.76 (m, 3H), 1.71 (dt, J=4.0, 8.9 Hz, 1H), 1.63-1.34 (m, 3H), 0.89-0.74 (m, 1H), 0.53-0.36 (m, 2H), 0.24-0.16 (m, 1H), 0.15-0.06 (m, 1H).

Example 224. Synthesis of Viral Protease Inhibitor Compound 830

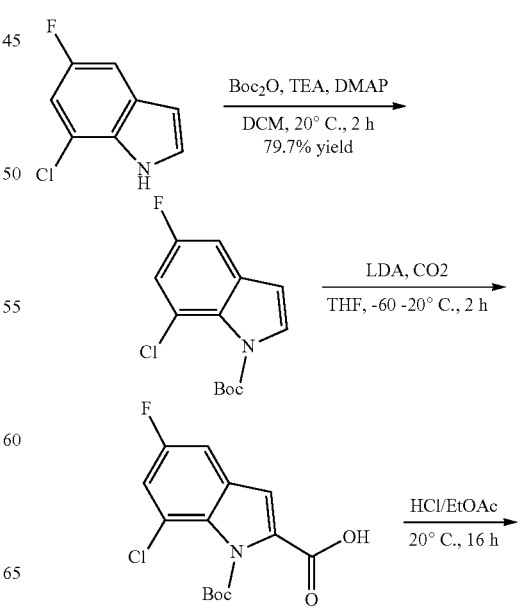

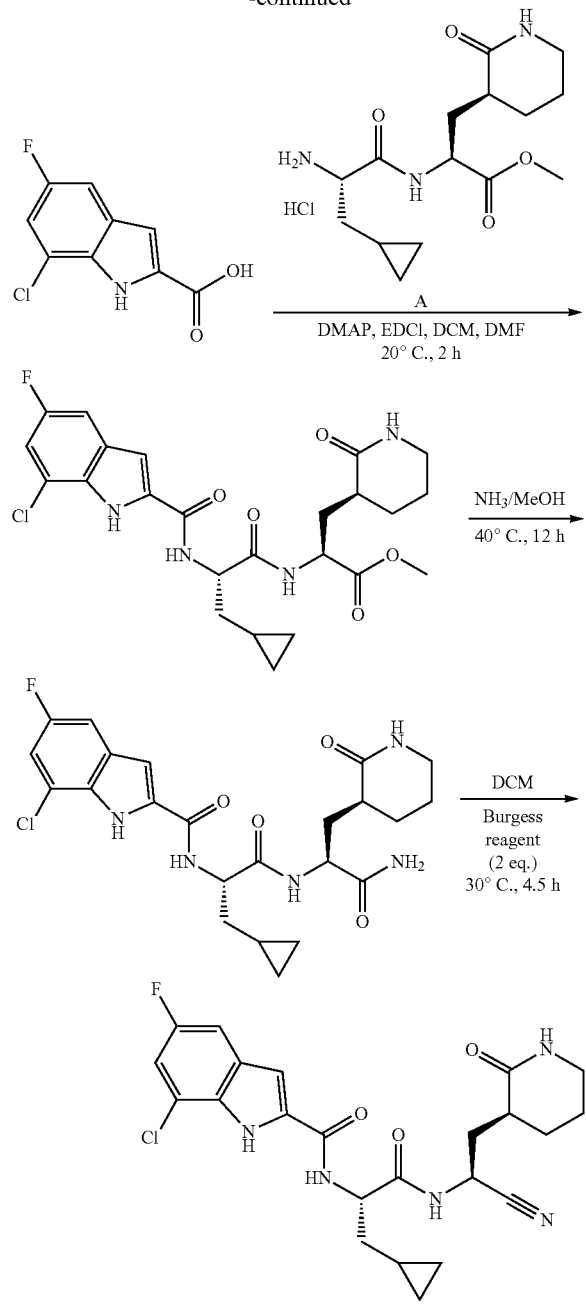

Step 1: tert-butyl
7-chloro-5-fluoro-1H-indole-1-carboxylate

To a solution of 7-chloro-5-fluoro-1H-indole (4.5 g, 26.54 mmol, 1 eq) and TEA (3.22 g, 31.84 mmol, 4.43 mL, 1.2 eq) in DCM (20 mL) was added DMAP (648.36 mg, 5.31 mmol, 0.2 eq) and Boc₂O (6.37 g, 29.19 mmol, 6.71 mL, 1.1 eq) under N₂, then the mixture was stirred at 20° C. for 2 h. Upon completion, the reaction mixture was quenched by addition H₂O 100 mL, and then extracted with DCM 150 ml (50 mL*3). The combined organic layers were washed with brine (50 mL*1), dried over Na₂SO₄, filtered and concentrated under reduced pressure to give a residue. The residue was purified by column chromatography (SiO₂, Petroleum ether:Ethyl acetate=1:0 to 15:1) to give the product tert-butyl 7-chloro-5-fluoro-indole-1-carboxylate (6 g, 21.13 mmol, 79.65% yield, 95% purity) as a yellow oil.

Step 2: 1-(tert-butoxycarbonyl)-7-chloro-5-fluoro-1H-indole-2-carboxylic acid

To a mixture of tert-butyl 7-chloro-5-fluoro-indole-1-carboxylate (3 g, 11.12 mmol, 1 eq) in THF (40 mL) was added LDA (2 M, 7.23 mL, 1.3 eq) at −60° C. under N₂. The mixture was stirred at −60° C. for 1.5 h, then the above solution was added into drikold (24.48 g, 556.18 mmol, 50 eq) and let stand for 0.5 h at 20° C. Upon completion, the reaction mixture was poured into ice-water (100 mL) under N₂ and stirred for 10 min. The aqueous phase was added 1 M HCl to pH ~3-4 at 0° C. and extracted with ethyl acetate (60 mL*3). The combined organic phase was washed with brine (100 mL), dried with anhydrous Na₂SO₄, filtered and concentrated in vacuum. The residue was purified by prep-HPLC to give the product 1-tert-butoxycarbonyl-7-chloro-5-fluoro-indole-2-carboxylic acid (1.8 g, 5.74 mmol, 51.58% yield, N/A purity) as a white solid.

Step 3: 7-chloro-5-fluoro-1H-indole-2-carboxylic acid

To a solution of 1-tert-butoxycarbonyl-7-chloro-5-fluoro-indole-2-carboxylic acid (1 g, 3.19 mmol, 1 eq) in HCl/EtOAc (4 M, 40.00 mL, 50.19 eq), and then the mixture was stirred at 20° C. for 16 h. Upon completion, the reaction mixture was concentrated under reduced pressure to give the product 7-chloro-5-fluoro-1H-indole-2-carboxylic acid (660 mg, crude, HCl) as a yellow solid.

Step 4: (S)-methyl 2-((S)-2-(7-chloro-5-fluoro-1H-indole-2-carboxamido)-3-cyclopropylpropanamido)-3-((S)-2-oxopiperidin-3-yl)propanoate To a solution of 7-chloro-5-fluoro-1H-indole-2-carboxylic acid (660 mg, 2.64 mmol, 1 eq, HCl) and methyl (2S)-2-[[(2S)-2-amino-3-cyclopropyl-propanoyl]amino]-3-[(3S)-2-oxo-3-piperidyl]propanoate (1.07 g, 3.43 mmol, 1.3 eq) in DMF (5 mL) and DCM (20 mL), and then DMAP (967.38 mg, 7.92 mmol, 3 eq) and EDCI (1.01 g, 5.28 mmol, 2 eq) was added, then the mixture was stirred at 20° C. for 2 h. Upon completion, the reaction mixture was quenched by addition H₂O 50 mL at 0° C., and then extracted with DCM 150 mL (50 mL*3). The combined organic layers were washed with brine (50 mL*1), dried over Na₂SO₄, filtered and concentrated under reduced pressure to give a residue. The residue was purified by column chromatography (SiO₂, Petroleum ether:Ethyl acetate=5:1 to 0:1) to give the product methyl (2S)-2-[[(2S)-2-[(7-chloro-5-fluoro-1H-indole-2-carbonyl)amino]-3-cyclopropyl-propanoyl]amino]-3-[(3S)-2-oxo-3-piperidyl]propanoate (770 mg, 1.41 mmol, 53.52% yield, 93% purity) as a yellow solid. MS (ESI) m/z 507.2 [M+H]⁺.

Step 5: (S)-methyl 2-((S)-2-(7-chloro-5-fluoro-1H-indole-2-carboxamido)-3-cyclopropylpropanamido)-3-((S)-2-oxopiperidin-3-yl)propanoate To a solution of methyl (2S)-2-[[(2S)-2-[(7-chloro-5-fluoro-1H-indole-2-carbonyl)amino]-3-cyclopropyl-propanoyl]amino]-3-[(3S)-2-oxo-3-piperidyl]propanoate (770 mg, 1.52 mmol, 1 eq) in NH3/MeOH (7 M, 40.00 mL, 184.35 eq), and then the mixture was stirred at 40° C. for 12 h. Upon completion, the reaction mixture was concentrated under reduced pressure to give the product N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-5-fluoro-1H-indole-2-carboxamide (720 mg, crude) as a yellow solid. MS (ESI) m/z 492.2 [M+H]⁺.

Step 6: 7-chloro-N-((S)-1-(((S)-1-cyano-2-((S)-2-oxopiperidin-3-yl)ethyl)amino)-3-cyclopropyl-1-oxopropan-2-yl)-5-fluoro-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-7-chloro-5-fluoro-1H-indole-2-carboxamide (660 mg, 1.34 mmol, 1 eq) in DCM (15 mL) and BURGESS REAGENT (639.44 mg, 2.68 mmol, 2 eq) was added, and then the mixture was stirred at 30° C. for 4.5 h. Upon completion, the reaction mixture was concentrated under reduced pressure to give a residue. The residue was purified by prep-HPLC (column: Waters Xbridge C18 150*50 mm*10 um; mobile phase: [water (10 mM NH₄HCO₃)-ACN]; B %: 30%-60%, 10 min) to give the product 7-chloro-N-[(1S)-2-[[(1S)-1-cyano-2-[(3S)-2-oxo-3-piperidyl]ethyl]amino]-1-(cyclopropylmethyl)-2-oxo-ethyl]-5-fluoro-1H-indole-2-carboxamide (232.57 mg, 490.73 umol, 36.58% yield, 100% purity) as a white solid. MS (ESI) m/z 474.2 [M+H]⁺.

¹H NMR (400 MHz, DMSO-d₆) δ=11.87 (s, 1H), 9.00 (d, J=7.9 Hz, 1H), 8.74 (br d, J=7.6 Hz, 1H), 7.53 (br s, 1H), 7.47 (dd, J=2.2, 9.3 Hz, 1H), 7.33 (dd, J=2.2, 9.3 Hz, 1H), 7.26 (s, 1H), 5.07 (br d, J=7.8 Hz, 1H), 4.51 (s, 1H), 3.15-3.04 (m, 2H), 2.25 (br t, J=8.7 Hz, 1H), 1.88-1.75 (m, 3H), 1.74-1.67 (m, 1H), 1.39-1.57 (s, 3H), 0.86-0.76 (m, 1H), 0.48-0.37 (m, 2H), 0.23-0.07 (m, 2H)

Example 225. Synthesis of Viral Protease Inhibitor Compound 832

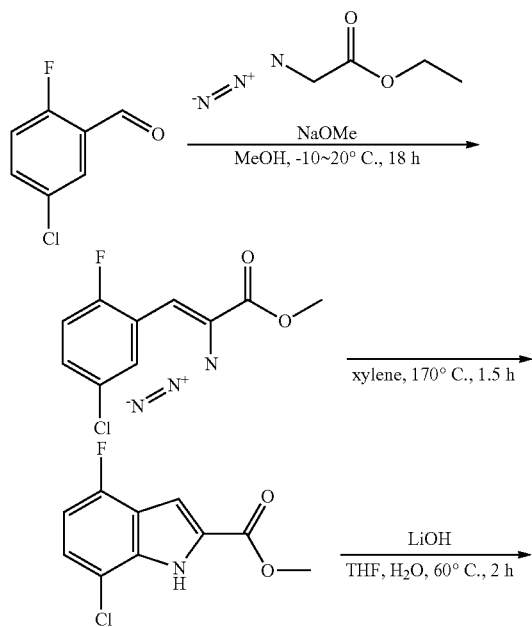

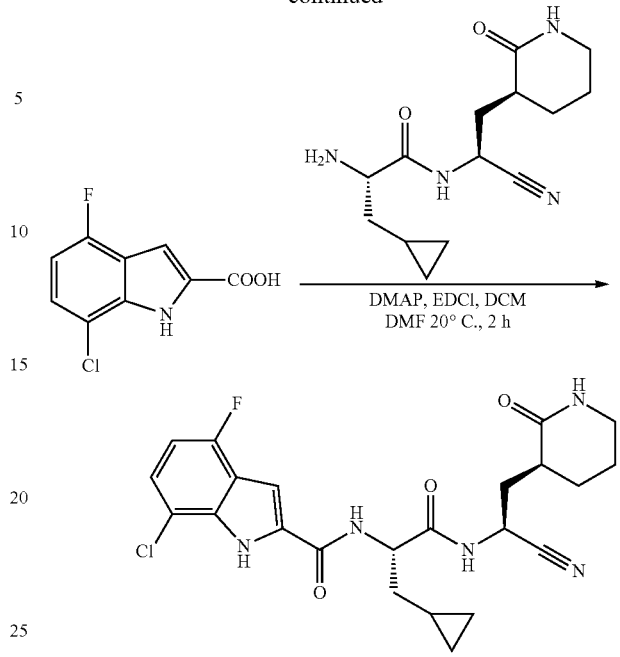

Step 1: (Z)-methyl 2-azido-3-(5-chloro-2-fluorophenyl)acrylate

To a solution of NaOMe (3.41 g, 63.06 mmol, 2 eq) in MeOH (50 mL), then 5-chloro-2-fluoro-benzaldehyde (5 g, 31.53 mmol, 1 eq) and ethyl 2-azidoacetate (8.14 g, 63.06 mmol, 7.21 mL, 2 eq) in MeOH (50 mL) was added at −10° C. The mixture was stirred at 20° C. for 18 h. Upon completion, the reaction mixture was quenched by addition H₂O 50 mL at 0° C., and then extracted with DCM 150 mL (50 mL*3). The combined organic layers were washed with brine (50 mL*1), dried over Na₂SO₄, filtered and concentrated under reduced pressure to give a residue. The residue was purified by column chromatography (SiO₂, Petroleum ether:Ethyl acetate=1:0 to 5:1) to give the product methyl (Z)-2-azido-3-(5-chloro-2-fluoro-phenyl)prop-2-enoate (3.7 g, 13.75 mmol, 43.61% yield, 95% purity) as a white solid.

Step 2: methyl 7-chloro-4-fluoro-1H-indole-2-carboxylate

To a solution of methyl (Z)-2-azido-3-(5-chloro-2-fluoro-phenyl)prop-2-enoate (3.7 g, 14.47 mmol, 1 eq) in XYLENE (40 mL) and the mixture was stirred at 170° C. for 1.5 h. Upon completion, the reaction mixture was concentrated under reduced pressure to give a residue. The residue was triturated with PE:EA=20:1 (100 mL) at 20° C. for 10 min to give the product methyl 7-chloro-4-fluoro-1H-indole-2-carboxylate (1.6 g, 6.68 mmol, 46.14% yield, 95% purity) as a white solid. MS (ESI) m/z 228.1 [M+H]⁺.

Step 3: 7-chloro-4-fluoro-1H-indole-2-carboxylic acid

To a solution of methyl 7-chloro-4-fluoro-1H-indole-2-carboxylate (1.5 g, 6.59 mmol, 1 eq) THF (10 mL) and H₂O (5 mL), then LiOH (315.64 mg, 13.18 mmol, 2 eq) was added, and the mixture was stirred at 60° C. for 2 h. Upon completion, the reaction mixture was quenched by addition H₂O 100 mL at 0° C., and then HCl (1 M) was added dropwise to pH to 3~4, and extracted with EA (50 mL*3). The combined organic layers were washed with brine 50 mL, dried over Na₂SO₄, filtered and concentrated under reduced pressure to give the product 7-chloro-4-fluoro-1H-indole-2-carboxylic acid (1.4 g, crude) as a white solid.

Step 4: 7-chloro-N-((S)-1-(((S)-1-cyano-2-((S)-2-oxopiperidin-3-yl)ethyl)amino)-3-cyclopropyl-1-oxopropan-2-yl)-4-fluoro-1H-indole-2-carboxamide To a solution of 7-chloro-4-fluoro-1H-indole-2-carboxylic acid (100 mg, 468.18 umol, 1.30 eq) and (2S)-2-amino-N-[(1S)-1-cyano-2-[(3S)-2-oxo-3-piperidyl]ethyl]-3-cyclopropyl-propanamide (200 mg, 359.26 umol, 50% purity, 1 eq) in DMF (2 mL) and DCM (5 mL), and then DMAP (131.67 mg, 1.08 mmol, 3 eq) and EDCI (137.74 mg, 718.52 umol, 2 eq) was added, then the mixture was stirred at 20° C. for 2 h. Upon completion, the reaction mixture was quenched by addition H₂O 50 mL at 0° C., and then extracted with DCM 150 mL (50 mL*3). The combined organic layers were washed with brine (50 mL*1), dried over Na₂SO₄, filtered and concentrated under reduced pressure to give a residue. The residue was purified by prep-HPLC (column: Waters Xbridge BEH C18 100*30 mm*10 um; mobile phase: [water (10 mM NH₄HCO₃)-ACN]; B %: 30%-50%, 8 min) to give the product 7-chloro-N-[(1S)-2-[[(1S)-1-cyano-2-[(3S)-2-oxo-3-piperidyl]ethyl]amino]-1-(cyclopropylmethyl)-2-oxo-ethyl]-4-fluoro-1H-indole-2-carboxamide (112.98 mg, 238.39 umol, 66.36% yield, 100% purity) as a white solid. MS (ESI) m/z 474.2 [M+H]⁺.

¹H NMR (400 MHz, DMSO-d₆) δ=12.12 (br s, 1H), 9.10-8.97 (m, 1H), 8.79 (d, J=7.2 Hz, 1H), 7.55 (br s, 1H), 7.36-7.33 (m, 1H), 7.33-7.26 (m, 1H), 6.90 (dd, J=8.6, 9.6 Hz, 1H), 5.13-4.98 (m, 1H), 4.58-4.47 (m, 1H), 3.14-3.03 (m, 2H), 2.30-2.17 (m, 2H), 1.88-1.67 (m, 4H), 1.61-1.38 (m, 3H), 0.86-0.77 (m, 1H), 0.48-0.38 (m, 2H), 0.24-0.18 (m, 1H), 0.14-0.08 (m, 1H)

Example 226. Synthesis of Viral Protease Inhibitor Compound 840

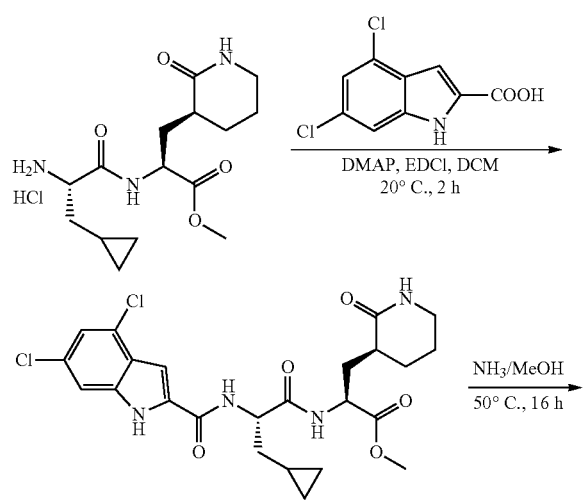

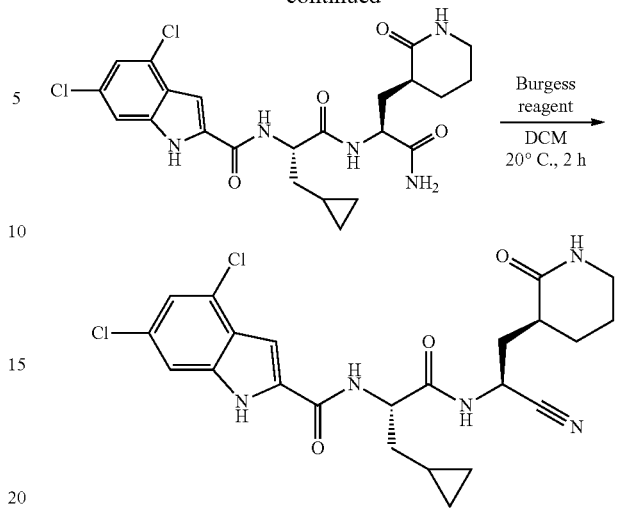

Step 1: methyl (2S)-2-[[(2S)-3-cyclopropyl-2-[(4,6-dichloro-1H-indole-2-carbonyl)amino]propanoyl]amino]-3-[(3S)-2-oxo-3-piperidyl]propanoate To a solution of methyl (2S)-2-[[(2S)-2-amino-3-cyclopropyl-propanoyl]amino]-3-[(3S)-2-oxo-3-piperidyl]propanoate (1 g, 2.87 mmol, 1 eq, HCl) and 4,6-dichloro-1H-indole-2-carboxylic acid (661.37 mg, 2.87 mmol, 1 eq) in DCM (40 mL), then DMAP (1.05 g, 8.62 mmol, 3 eq) was added, and then EDCI (1.65 g, 8.62 mmol, 3 eq) was added. The mixture was stirred at 20° C. for 2 h. Upon completion, the reaction mixture was quenched by addition H₂O 30 mL, and then extracted with DCM 40 mL (20 mL*2). The combined organic layers were washed with HCl (1 M) 30 mL (15 mL*2), the combined organic layers were washed with brine 30 mL, dried over Na₂SO₄, filtered and concentrated under reduced pressure to give a residue. The residue was purified by column chromatography (SiO₂, Petroleum ether/Ethyl acetate=3/1 to 0/1) to give methyl (2S)-2-[[(2S)-3-cyclopropyl-2-[(4,6-dichloro-1H-indole-2-carbonyl)amino]propanoyl]amino]-3-[(3S)-2-oxo-3-piperidyl]propanoate (1 g, 1.85 mmol, 64.46% yield, 97% purity) as a white solid. MS (ESI) m/z 523.1 [M+H]⁺

Step 2: N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4,6-dichloro-1H-indole-2-carboxamide To a solution of methyl (2S)-2-[[(2S)-3-cyclopropyl-2-[(4,6-dichloro-1H-indole-2-carbonyl)amino]propanoyl]amino]-3-[(3S)-2-oxo-3-piperidyl]propanoate (960 mg, 1.83 mmol, 1 eq) in NH₃/MeOH (7 M, 20 mL, 76.33 eq). The mixture was stirred at 50° C. for 16 h. Upon completion, the reaction mixture was concentrated under reduced pressure to remove solvent to give N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4,6-dichloro-1H-indole-2-carboxamide (820 mg, crude) as a white solid. MS (ESI) m/z 508.1 [M+H]⁺

Step 3: 4,6-dichloro-N-[(1S)-2-[[(1S)-1-cyano-2-[(3S)-2-oxo-3-piperidyl]ethyl]amino]-1-(cyclopropylmethyl)-2-oxo-ethyl]-1H-indole-2-carboxamide To a solution of N-[(1S)-2-[[(1S)-2-amino-2-oxo-1-[[(3S)-2-oxo-3-piperidyl]methyl]ethyl]amino]-1-(cyclopropylmethyl)-2-oxo-ethyl]-4,6-dichloro-1H-indole-2-carboxamide (800 mg, 1.57 mmol, 1 eq) in DCM (15 mL), then BURGESSREAGENT (749.98 mg, 3.15 mmol, 2 eq) was added. The mixture was stirred at 20° C. for 2 h. Upon completion, the reaction mixture was concentrated under reduced pressure to remove solvent. The residue was purified by prep-HPLC (column: Waters Xbridge C18 150*50 mm*10 um; mobile phase: [water (10 mM $NH_4HCO_3$)-ACN]; B %: 40%-60%, 10 min), to give 4,6-dichloro-N-[(1 S)-2-[[(1 S)-1-cyano-2-[(3S)-2-oxo-3-piperidyl]ethyl]amino]-1-(cyclopropylmethyl)-2-oxo-ethyl]-1H-indole-2-carboxamide (213.1 mg, 434.56 umol, 27.62% yield, 100% purity) as a white solid. MS (ESI) m/z 490.1 $[M+H]^+$ $^1$H NMR (400 MHz, DMSO-$d_6$) δ=12.11 (s, 1H), 8.95 (d, J=8.4 Hz, 1H), 8.84 (d, J=7.4 Hz, 1H), 7.53 (s, 1H), 7.44 (d, J=17.4 Hz, 2H), 7.24 (d, J=1.8 Hz, 1H), 5.13-5.01 (m, 1H), 4.52-4.41 (m, 1H), 3.19-3.00 (m, 2H), 2.35-2.18 (m, 2H), 1.97-1.63 (m, 4H), 1.61-1.33 (m, 3H), 0.88-0.75 (m, 1H), 0.51-0.32 (m, 2H), 0.25-0.05 (m, 2H)

Example 227. Synthesis of Viral Protease Inhibitor Compound 856

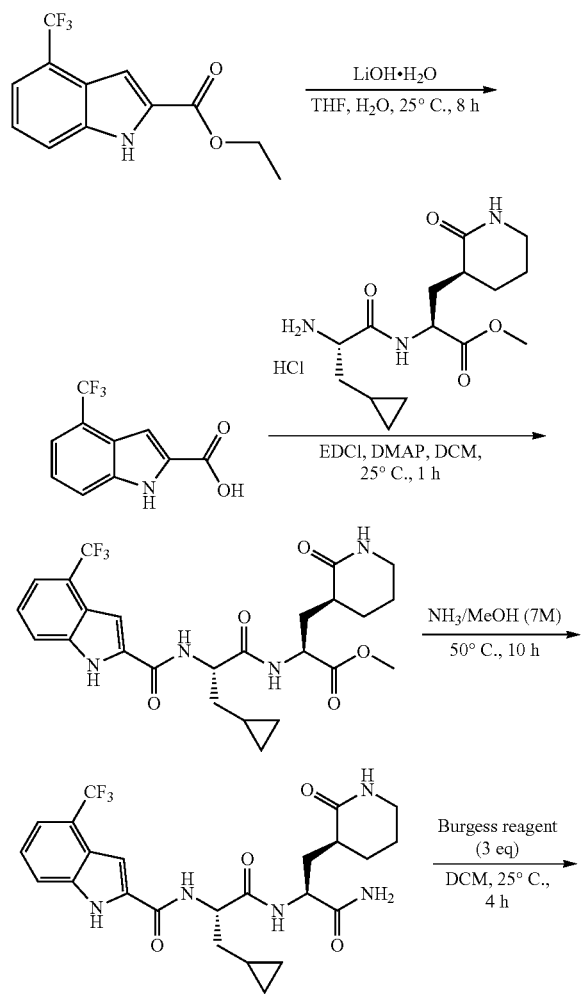

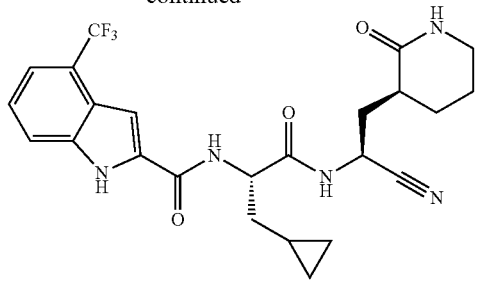

Step 1: 4-(trifluoromethyl)-1H-indole-2-carboxylic acid

To a solution of ethyl 4-(trifluoromethyl)-1H-indole-2-carboxylate (800 mg, 3.11 mmol, 1 eq) in THF (10 mL), $H_2O$ (5 mL) was added LiOH·$H_2O$ (261.02 mg, 6.22 mmol, 2 eq) and the mixture was stirred at 25° C. for 8 h. The reaction mixture was adjust to pH-3 with HCl (1M, aq). The mixture was extracted with EtOAc (100*3 mL). The combined organic layer was dried over $Na_2SO_4$, filtered, concentrated to give product 4-(trifluoromethyl)-1H-indole-2-carboxylic acid (700 mg, crude) was white solid. MS (ESI) m/z 230.0 $[M+H]^+$ Step 2: (S)-methyl 2-((S)-3-cyclopropyl-2-(4-(trifluoromethyl)-1H-indole-2-carboxamido)propanamido)-3-((S)-2-oxopiperidin-3-yl)propanoate To a solution of 4-(trifluoromethyl)-1H-indole-2-carboxylic acid (650 mg, 2.84 mmol, 1 eq) in DCM (20 mL) was added (S)-methyl 2-((S)-2-amino-3-cyclopropylpropanamido)-3-((S)-2-oxopiperidin-3-yl)propanoate (986.64 mg, 2.84 mmol, 1 eq, HCl), DMAP (1.04 g, 8.51 mmol, 3 eq), EDCI (1.09 g, 5.67 mmol, 2 eq) and the mixture was stirred at 25° C. for 1 h. Upon completion, the reaction was quenched by addition $H_2O$ (200 mL) and then extracted with EtOAc (100 mL*3). The combined organic layers were washed with (brine 100 mL), dried over $Na_2SO_4$, filtered and concentrated under reduced pressure and was purified by column chromatography ($SiO_2$, EtOAc/MeOH=1/0 to 10/1) to give product (S)-methyl 2-((S)-3-cyclopropyl-2-(4-(trifluoromethyl)-1H-indole-2-carboxamido)propanamido)-3-((S)-2-oxopiperidin-3-yl)propanoate (800 mg, 1.50 mmol, 52.83% yield, 97.87% purity) as yellow solid. MS (ESI) m/z 523.2 $[M+H]^+$ Step 3: N-((S)-1-(((S)-1-amino-1-oxo-3-((S)-2-oxopiperidin-3-yl)propan-2-yl)amino)-3-cyclopropyl-1-oxopropan-2-yl)-4-(trifluoromethyl)-1H-indole-2-carboxamide To a solution of (S)-methyl 2-((S)-3-cyclopropyl-2-(4-(trifluoromethyl)-1H-indole-2-carboxamido)propanamido)-3-((S)-2-oxopiperidin-3-yl)propanoate (700 mg, 1.34 mmol, 1 eq) in ammonia (7 M, 40 mL, 209.01 eq) was stirred at 50° C. for 10 h. Upon completion, the reaction was concentrated in the vacuum to give crude product N-((S)-1-(((S)-1-amino-1-oxo-3-((S)-2-oxopiperidin-3-yl)propan-2-yl)amino)-3-cyclopropyl-1-oxopropan-2-yl)-4-(trifluoromethyl)-1H-indole-2-carboxamide (690 mg, crude) as white solid. MS (ESI) m/z 508.2 $[M+H]^+$ Step 4: N-((S)-1-(((S)-1-cyano-2-((S)-2-oxopiperidin-3-yl)ethyl)amino)-3-cyclopropyl-1-oxopropan-2-yl)-4-(trifluoromethyl)-1H-indole-2-carboxamide To a solution of N-((S)-1-(((S)-1-amino-1-oxo-3-((S)-2-oxopiperidin-3-yl)propan-2-yl)amino)-3-cyclopropyl-1-oxopropan-2-yl)-4-(trifluoromethyl)-1H-indole-2-carboxamide (670 mg, 1.32 mmol, 1 eq) in DCM (30 mL) was added BURGESS REAGENT (943.82 mg, 3.96 mmol, 3 eq) and the mixture was stirred at 25° C. for 4 h. Upon completion, the reaction was concentrated in the vacuum and was purified by prep-HPLC (column: Waters Xbridge C18 150*50 mm*10 um; mobile phase: [water (10 mM NH$_4$HCO$_3$)-ACN]; B %: 30%-60%, 10 min) to give product N-((S)-1-(((S)-1-cyano-2-((S)-2-oxopiperidin-3-yl)ethyl)amino)-3-cyclopropyl-1-oxopropan-2-yl)-4-(trifluoromethyl)-1H-indole-2-carboxamide (200 mg, 408.59 umol, 30.95% yield, 100% purity) as white solid. MS (ESI) m/z 490.1 [M+H]$^+$ $^1$H NMR (400 MHz, DMSO-d$_6$) δ=12.14 (br s, 1H), 8.97-8.95 (m, 1H), 8.88-8.86 (m, 1H), 7.75-7.71 (m, 1H), 7.54 (s, 2H), 7.45-7.43 (m, 1H), 7.37-7.31 (m, 1H), 5.11-5.03 (m, 1H), 4.52-4.45 (m, 1H), 3.15-3.04 (m, 2H), 2.35-2.21 (m, 2H), 1.93-1.76 (m, 3H), 1.76-1.64 (m, 1H), 1.62-1.51 (m, 1H), 1.49-1.34 (m, 2H), 0.84-0.81 (m, 1H), 0.48-0.36 (m, 2H), 0.26-0.07 (m, 2H).

Example 228. Synthesis of Viral Protease Inhibitor Compound 896

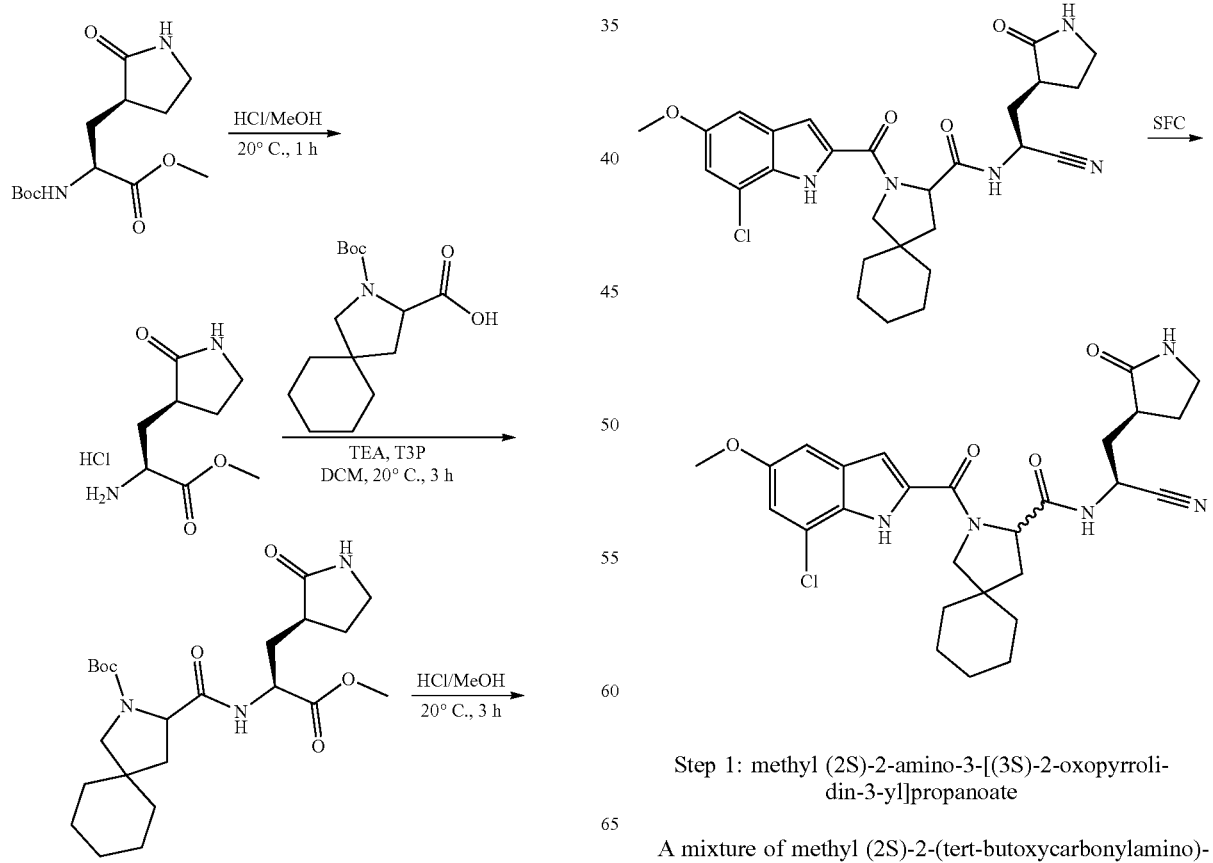

Step 1: methyl (2S)-2-amino-3-[(3S)-2-oxopyrrolidin-3-yl]propanoate

A mixture of methyl (2S)-2-(tert-butoxycarbonylamino)-3-[(3S)-2-oxopyrrolidin-3-yl]propanoate (2.6 g, 9.08 mmol, 1 eq) in HCl/MeOH (4 M, 30 mL, 13.21 eq) was stirred at 20° C. for 1.5 h. Upon completion, the mixture was concentrated under reduced pressure to give a residue, then was dissolved with DCM (30 mL*3) and concentrated under reduced pressure to get product methyl (2S)-2-amino-3-[(3S)-2-oxopyrrolidin-3-yl]propanoate (2 g, crude, HCl) as yellow oil. MS (ESI) m/z 187.1 [M+H]$^+$.

Step 2: tert-butyl 3-[[(1S)-2-methoxy-2-oxo-1-[[(3S)-2-oxopyrrolidin-3-yl]methyl]ethyl]carbamoyl]-2-azaspiro[4.5]decane-2-carboxylate A mixture of methyl (2S)-2-amino-3-[(3S)-2-oxopyrrolidin-3-yl]propanoate (2 g, 8.98 mmol, 1 eq, HCl) in DCM (20 mL) and DMF (2 mL) then added 2-tert-butoxycarbonyl-2-azaspiro[4.5]decane-3-carboxylic acid (2.80 g, 9.88 mmol, 1.1 eq), T3P (11.43 g, 17.96 mmol, 10.68 mL, 50% purity, 2 eq) and TEA (5.45 g, 53.89 mmol, 7.50 mL, 6 eq) was stirred at 20° C. for 3 h. Upon completion, the reaction mixture was diluted with water (50 mL) and extracted with DCM (30 mL*3). The combined organic layers were dried over Na$_2$SO$_4$, filtered and concentrated under reduced pressure to give a residue. The residue was purified by column (SiO$_2$, PE:EA=4/1~0/1) to get the product tert-butyl 3-[[(1S)-2-methoxy-2-oxo-1-[[(3S)-2-oxopyrrolidin-3-yl]methyl]ethyl]carbamoyl]-2-azaspiro[4.5]decane-2-carboxylate (2.5 g, 4.43 mmol, 49.31% yield, 80% purity) as white solid. MS (ESI) m/z 452.3 [M+H]$^+$.

Step 3: methyl (2S)-2-(2-azaspiro[4.5]decane-3-carbonylamino)-3-[(3S)-2-oxopyrrolidin-3-yl]propanoate A mixture of tert-butyl 3-[[(1S)-2-methoxy-2-oxo-1-[[(3S)-2-oxopyrrolidin-3-yl]methyl]ethyl]carbamoyl]-2-azaspiro[4.5]decane-2-carboxylate (2.1 g, 3.72 mmol, 80% purity, 1 eq) in HCl/MeOH (4 M, 25 mL, 26.88 eq) was stirred at 20° C. for 3 h. Upon completion, The mixture was concentrated under reduced pressure to give a residue, then was dissolved with DCM (10 mL*3) and concentrated under reduced pressure to get the product methyl (2S)-2-(2-azaspiro[4.5]decane-3-carbonylamino)-3-[(3S)-2-oxopyrrolidin-3-yl]propanoate (1.4 g, crude, HCl) as white oil. MS (ESI) m/z 352.2 [M+H]$^+$.

Step 4: methyl (2S)-2-(2-azaspiro[4.5]decane-3-carbonylamino)-3-[(3S)-2-oxopyrrolidin-3-yl]propanoate A mixture of methyl (2S)-2-(2-azaspiro[4.5]decane-3-carbonylamino)-3-[(3S)-2-oxopyrrolidin-3-yl]propanoate (1.4 g, 3.61 mmol, 1 eq, HCl) in DCM (20 mL) then added 7-chloro-5-methoxy-1H-indole-2-carboxylic acid (1.06 g, 4.69 mmol, 1.3 eq), DMAP (1.10 g, 9.02 mmol, 2.5 eq) and EDCI (1.38 g, 7.22 mmol, 2 eq) was stirred at 20° C. for 1 h. Upon completion, the reaction mixture was diluted with water (50 mL) and extracted with DCM (30 mL*3). The combined organic layers were dried over Na$_2$SO$_4$, filtered and concentrated under reduced pressure to give a residue. The residue was purified by column (SiO$_2$, PE:EA=2/1~0/1) to get the product methyl (2S)-2-[[2-(7-chloro-5-methoxy-1H-indole-2-carbonyl)-2-azaspiro[4.5]decane-3-carbonyl]amino]-3-[(3S)-2-oxopyrrolidin-3-yl]propanoate (1.5 g, 2.68 mmol, 74.34% yield) as white solid. MS (ESI) m/z 559.2 [M+H]$^+$.

Step 5: N-[(1S)-2-amino-2-oxo-1-[[(3S)-2-oxopyrrolidin-3-yl]methyl]ethyl]-2-(7-chloro-5-methoxy-1H-indole-2-carbonyl)-2-azaspiro[4.5]decane-3-carboxamide A mixture of methyl (2S)-2-[[2-(7-chloro-5-methoxy-1H-indole-2-carbonyl)-2-azaspiro[4.5]decane-3-carbonyl]amino]-3-[(3S)-2-oxopyrrolidin-3-yl]propanoate (1.46 g, 2.61 mmol, 1 eq) in NH$_3$/MeOH (7 M, 20 mL, 53.61 eq) was stirred at 30° C. for 20 h. Upon completion, the mixture was concentrated under reduced pressure to give a residue, then was dissolved with DCM (30 mL*3) and concentrated under reduced pressure to get the product N-[(1S)-2-amino-2-oxo-1-[[(3S)-2-oxopyrrolidin-3-yl]methyl]ethyl]-2-(7-chloro-5-methoxy-1H-indole-2-carbonyl)-2-azaspiro[4.5]decane-3-carboxamide (1.35 g, crude) as yellow oil. MS (ESI) m/z 544.2 [M+H]$^+$.

Step 6: 2-(7-chloro-5-methoxy-1H-indole-2-carbonyl)-N-[(1S)-1-cyano-2-[(3S)-2-oxopyrrolidin-3-yl]ethyl]-2-azaspiro[4.5]decane-3-carboxamide A mixture of N-[(1S)-2-amino-2-oxo-1-[[(3S)-2-oxopyrrolidin-3-yl]methyl]ethyl]-2-(7-chloro-5-methoxy-1H-indole-2-carbonyl)-2-azaspiro[4.5]decane-3-carboxamide (1.35 g, 2.11 mmol, 85% purity, 1 eq) in DCM (15 mL) added BURGESS REAGENT (1.51 g, 6.33 mmol, 3 eq) was stirred at 30° C. for 1 h. Upon completion, the mixture were quenched with water (1 mL) and blow-dried with N$_2$. The residue was purified by prep-HPLC (column: Waters X bridge Prep OBD C18 150*40 mm*10 um; mobile phase: [water (10 mM NH$_4$HCO$_3$)-ACN]; B %: 35%-65%, 8 min), which was further separated by SFC (column: REGIS(S,S) WHELK-O1 (250 mm*25 mm, 10 um); mobile phase: [Neu-ETOH]; B %: 60%-60%, 12 min) to get the product 2-(7-chloro-5-methoxy-1H-indole-2-carbonyl)-N-[(1S)-1-cyano-2-[(3S)-2-oxopyrrolidin-3-yl]ethyl]-2-azaspiro[4.5]decane-3-carboxamide (322.82 mg, 613.70 umol, 29.10% yield) as white solid. MS (ESI) m/z 526.2 [M+H]$^+$.

$^1$H NMR (400 MHz, MeOD-d$_4$) δ=7.12 (d, J=1.7 Hz, 1H), 7.02 (s, 1H), 6.97 (br d, J=1.8 Hz, 1H), 5.12-5.00 (m, 1H), 4.62 (dd, J=7.9, 9.7 Hz, 1H), 3.92 (br d, J=10.3 Hz, 1H), 3.86-3.33 (m, 5H), 3.30-3.26 (m, 1H), 2.77-2.55 (m, 1H), 2.52-2.23 (m, 3H), 1.98-1.67 (m, 3H), 1.62-1.41 (m, 10H).

$^1$H NMR (400 MHz, DMSO-d$_6$) δ=11.07 (br d, J=1.1 Hz, 1H), 8.72 (br d, J=7.5 Hz, 1H), 7.44 (br d, J=0.7 Hz, 1H), 7.12 (br s, 1H), 6.97 (s, 2H), 4.92 (br s, 1H), 4.60 (br s, 1H), 3.85-3.77 (m, 4H), 3.61 (br s, 1H), 3.14 (br s, 2H), 2.43-2.21 (m, 2H), 2.20-1.89 (m, 2H), 1.80 (br s, 1H), 1.72-1.58 (m, 2H), 1.57-1.35 (m, 10H).

To get the product 2-(7-chloro-5-methoxy-1H-indole-2-carbonyl)-N-[(1S)-1-cyano-2-[(3S)-2-oxopyrrolidin-3-yl]ethyl]-2-azaspiro[4.5]decane-3-carboxamide (289.32 mg, 550.01 umol, 26.08% yield) as white solid. MS (ESI) m/z 526.2 [M+H]$^+$.

$^1$H NMR (400 MHz, MeOD-d$_4$) δ=7.12 (d, J=2.0 Hz, 1H), 7.04 (s, 1H), 6.99-6.93 (m, 1H), 5.06-4.97 (m, 1H), 4.63 (dd, J=7.9, 9.5 Hz, 1H), 3.94 (br d, J=10.4 Hz, 1H), 3.88-3.68 (m, 4H), 3.30-2.73 (m, 2H), 2.68-2.10 (m, 4H), 1.94-1.69 (m, 3H), 1.62-1.40 (m, 10H).

$^1$H NMR (400 MHz, DMSO-d$_6$) δ=11.46-10.49 (m, 1H), 8.67 (br d, J=6.6 Hz, 1H), 7.44 (br s, 1H), 7.21-7.07 (m, 1H), 6.98 (s, 2H), 5.06-4.83 (m, 1H), 4.59 (br dd, J=2.1, 4.1 Hz, 1H), 3.80 (s, 4H), 3.70-3.44 (m, 1H), 3.22-3.10 (m, 2H), 2.25 (s, 4H), 1.82 (br s, 1H), 1.68 (br d, J=10.4 Hz, 2H), 1.59-1.33 (m, 10H).

1329

Example 229. Synthesis of Viral Protease Inhibitor Compound 1059

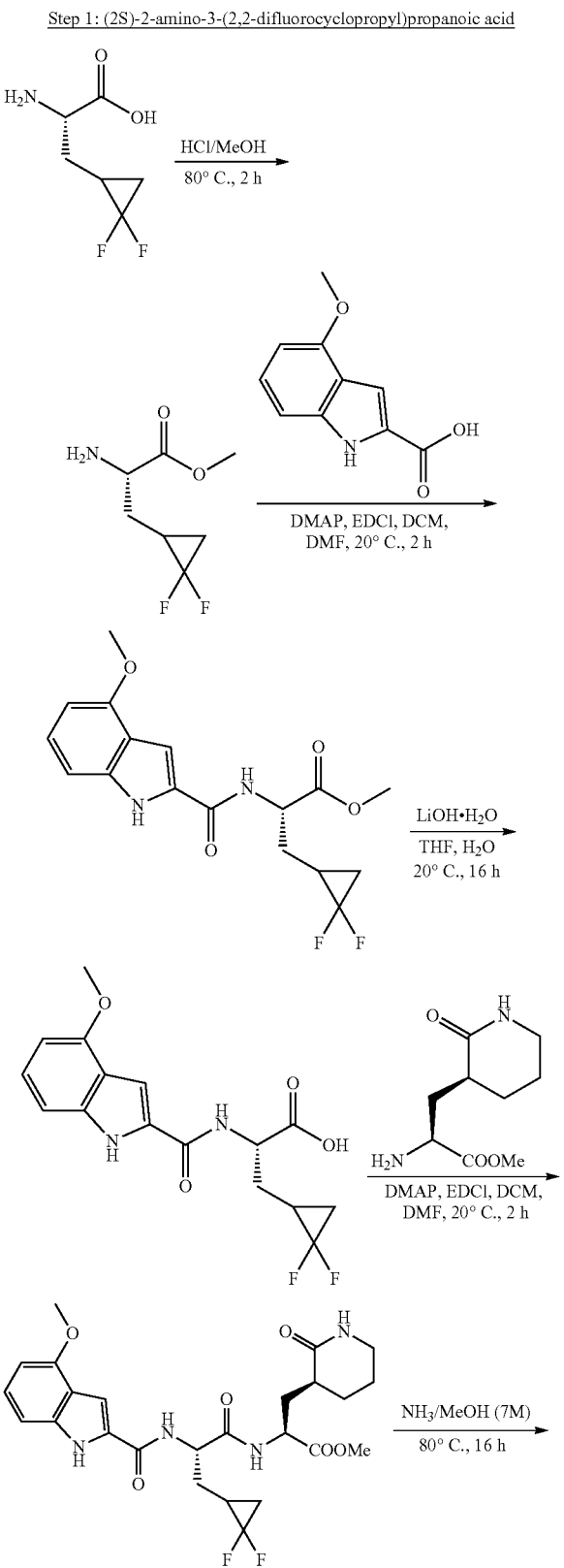

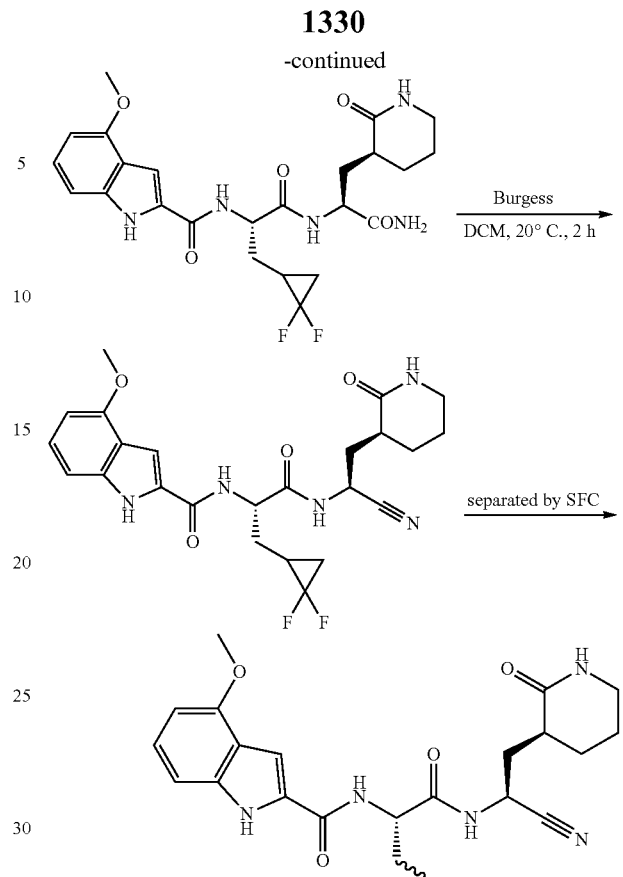

Step 1: (2S)-2-amino-3-(2,2-difluorocyclopropyl)propanoic acid

A mixture of (2S)-2-amino-3-(2,2-difluorocyclopropyl) propanoic acid (630 mg, 3.13 mmol, 1 eq, HC) in HCl/MeOH (4 M, 6 mL, 7.68 eq) was stirred at 80° C. for 2 h. Upon completion, the mixture was concentrated under the reduced pressure to give methyl(2S)-2-amino-3-(2,2-difluorocyclopropyl)propanoate (700 mg, crude, HCl) as a yellow oil.

Step 2: (2S)-methyl 3-(2,2-difluorocyclopropyl)-2-(4-methoxy-1H-indole-2-carboxamido)propanoate To a solution of methyl (2S)-2-amino-3-(2,2-difluorocyclopropyl)propanoate (700 mg, 3.25 mmol, 1 eq, HCl) and 4-methoxy-1H-indole-2-carboxylic acid (930.98 mg, 4.87 mmol, 1.5 eq) in DCM (15 mL) and DMF (3 mL) was added DMAP (793.21 mg, 6.49 mmol, 2 eq) and EDCI (1.24 g, 6.49 mmol, 2 eq). The mixture was stirred at 20° C. for 2 h. Upon completion, the reaction mixture was quenched by addition H$_2$O (30 mL), and then extracted with EA (30 mL*3). The combined organic layers were washed with brine (30 mL), dried over Na$_2$SO$_4$, filtered and concentrated under reduced pressure to give a residue. The residue was purified by column chromatography (SiO$_2$, Petroleum ether: Ethyl acetate=10:1 to 0:1) to give methyl (2S)-3-(2,2-difluorocyclopropyl)-2-[(4-methoxy-1H-indole-2-carbonyl)

amino]propanoate (I g, 2.84 mmol, 87.43% yield) as a yellow oil. MS (ESI) m/z 353.1 [M+H]+

Step 3: (2S)-3-(2,2-difluorocyclopropyl)-2-(4-methoxy-1H-indole-2-carboxamido)propanoic acid To a solution of methyl (2S)-3-(2,2-difluorocyclopropyl)-2-[(4-methoxy-1H-indole-2-carbonyl)amino]propanoate (1 g, 2.84 mmol, 1 eq) in THF (10 mL) and H₂O (3 mL) was added LiOH·H₂O (357.31 mg, 8.51 mmol, 3 eq). The mixture was stirred at 20° C. for 16 h. Upon completion, the mixture was quenched by addition H₂O (30 mL), and then added aq. HCl (1 M) to adjust the pH to 3-4, and extracted with EA (20 mL*3). The combined organic layers were washed with brine (30 mL), dried over Na₂SO₄, filtered and concentrated under reduced pressure to give (2S)-3-(2,2-difluorocyclopropyl)-2-[(4-methoxy-1H-indole-2-carbonyl)amino]propanoic acid (1 g, crude) as a yellow solid. MS (ESI) m/z 339.1 [M+H]+

Step 4: (2S)-methyl2-((2S)-3-(2,2-difluorocyclopropyl)-2-(4-methoxy-1H-indole-2-carboxamido)propanamido)-3-((S)-2-oxopiperidin-3-yl)propanoate To a solution of (2S)-3-(2,2-difluorocyclopropyl)-2-[(4-methoxy-1H-indole-2-carbonyl)amino]propanoic acid (1 g, 2.96 mmol, 1 eq) and methyl (2S)-2-amino-3-[(3S)-2-oxo-3-piperidyl]propanoate (887.81 mg, 3.75 mmol, 1.27 eq, HCl) in DCM (15 mL) and DMF (3 mL) was added DMAP (722.23 mg, 5.91 mmol, 2 eq) and EDCI (1.13 g, 5.91 mmol, 2 eq). The mixture was stirred at 20° C. for 2 h. Upon completion, the reaction mixture was quenched by addition H₂O (30 mL), and then extracted with DCM (30 mL*3). The combined organic layers were washed with brine (30 mL), dried over Na₂SO₄, filtered and concentrated under reduced pressure to give a residue. The residue was purified by column chromatography (SiO₂, Petroleum ether:Ethyl acetate=10:1 to 0:1) to give methyl (2S)-2-[[(2S)-3-(2,2-difluorocyclopropyl)-2-[(4-methoxy-1H-indole-2-carbonyl)amino]propanoyl]amino]-3-[(3S)-2-oxo-3-piperidyl]propanoate (1 g, 1.92 mmol, 64.99% yield) as a yellow solid. MS (ESI) m/z 521.2 [M+H]+

Step 5: N-((2S)-1-(((S)-1-amino-1-oxo-3-((S)-2-oxopiperidin-3-yl)propan-2-yl)amino)-3-(2,2-difluorocyclopropyl)-1-oxopropan-2-yl)-4-methoxy-1H-indole-2-carboxamide methyl(2S)-2-[[(2S)-3-(2,2-difluorocyclopropyl)-2-[(4-methoxy-1H-indole-2-carbonyl)amino]propanoyl]amino]-3-[(3S)-2-oxo-3-piperidyl]propanoate (1 g, 1.92 mmol, 1 eq) in NH₃/MeOH (7 M, 15 mL, 54.66 eq) was stirred at 80° C. for 16 h. Upon completion, the mixture was concentrated under the reduced pressure to give N-[(1S)-2-[[(1S)-2-amino-2-oxo-1-[[(3S)-2-oxo-3-piperidyl]methyl]ethyl]amino]-1-[(2,2-difluorocyclopropyl)methyl]-2-oxo-ethyl]-4-methoxy-1H-indole-2-carboxamide (1 g, crude) as a brown solid. MS (ESI) m/z 506.2 [M+H]+

Step 6: N-((2S)-1-(((S)-1-cyano-2-((S)-2-oxopiperidin-3-yl)ethyl)amino)-3-(2,2-difluorocyclopropyl)-1-oxopropan-2-yl)-4-methoxy-1H-indole-2-carboxamide To a solution of N-[(1S)-2-[[(1S)-2-amino-2-oxo-1-[[(3S)-2-oxo-3-piperidyl]methyl]ethyl]amino]-1-[(2,2-difluorocyclopropyl)methyl]-2-oxo-ethyl]-4-methoxy-1H-indole-2-carboxamide (1 g, 1.98 mmol, 1 eq) in DCM (15 mL) was added BURGESS REAGENT (1.41 g, 5.93 mmol, 3 eq). The mixture was stirred at 20° C. for 2 h. Upon completion, the mixture was concentrated under the reduced pressure to give a residue. The residue was purified by prep-HPLC (column: Waters Xbridge C18 150*50 mm*10 um; mobile phase: [water (10 mM NH₄HCO₃)-ACN]; B %: 25%-50%, 10 min) to give N-[(1S)-2-[[(1S)-1-cyano-2-[(3S)-2-oxo-3-piperidyl]ethyl]amino]-1-[(2,2-difluorocyclopropyl)methyl]-2-oxoethyl]-4-methoxy-1H-indole-2-carboxamide (0.6 g, 1.23 mmol, 62.22% yield) as a yellow solid. MS (ESI) m/z 488.2 [M+H]+

Step 7: N-((2S)-1-(((S)-1-cyano-2-((S)-2-oxopiperidin-3-yl)ethyl)amino)-3-(2,2-difluorocyclopropyl)-1-oxopropan-2-yl)-4-methoxy-1H-indole-2-carboxamide N-[(1S)-2-[[(1S)-1-cyano-2-[(3S)-2-oxo-3-piperidyl]ethyl]amino]-1-[(2,2-difluorocyclopropyl)methyl]-2-oxoethyl]-4-methoxy-1H-indole-2-carboxamide (0.6 g, 1.23 mmol) was separated by SFC (column: DAICEL CHIRALPAK AD (250 mm*30 mm, 10 um); mobile phase: [0.1% NH₃H₂O IPA]; B %: 46%-46%, 7 min) to give N-[(1S)-2-[[(1S)-1-cyano-2-[(3S)-2-oxo-3-piperidyl]ethyl]amino]-1-[(2,2-difluorocyclopropyl)methyl]-2-oxoethyl]-4-methoxy-1H-indole-2-carboxamide Isomer 1 (210 mg, 429.91 umol, 34.93% yield, 99.8% purity) as a white solid. MS (ESI) m/z 488.2 [M+H]+

¹H NMR (400 MHz, MeOD-d₄) δ=7.27-7.26 (m, 1H), 7.17-7.15 (m, 1H), 7.13-7.04 (m, 1H), 6.52-6.50 (m, 1H), 5.14-5.09 (m, 1H), 4.61-4.56 (m, 1H), 3.93 (s, 3H), 3.23-3.21 (m, 2H), 2.46-2.42 (m, 2H), 1.96-1.95 (m, 1H), 1.93-1.92 (m, 3H), 1.85-1.70 (m, 3H), 1.56-1.44 (m, 2H), 1.22-1.12 (m, 1H)

To give N-[(1S)-2-[[(1S)-1-cyano-2-[(3S)-2-oxo-3-piperidyl]ethyl]amino]-1-[(2,2-difluorocyclopropyl)methyl]-2-oxoethyl]-4-methoxy-1H-indole-2-carboxamide Isomer 2 (210 mg, 429.05 umol, 34.86% yield, 99.6% purity) as a white solid. MS (ESI) m/z 488.2 [M+H]+

1H NMR (400 MHz, MeOD-d₄) δ=7.32-7.24 (m, 1H), 7.20-7.11 (m, 1H), 7.13-7.05 (m, 1H), 6.53-6.51 (m, 1H), 5.14-5.00 (m, 1H), 4.66-4.61 (m, 1H), 3.94 (s, 3H), 3.20-3.19 (m, 2H), 2.43-2.25 (m, 2H), 1.95-1.90 (m, 4H), 1.85-1.63 (m, 3H), 1.56-1.44 (m, 2H), 1.22-1.03 (m, 1H)

Example 230. Synthesis of Viral Protease Inhibitor Compound 1155

Step 1: tert-butyl (2S,4S)-4-methoxy-2-[[(1S)-2-methoxy-2-oxo-1-[[(3S)-2-oxo-3-piperidyl]methyl]ethyl]carbamoyl]-4-(trifluoromethyl)pyrrolidine-1-carboxylate

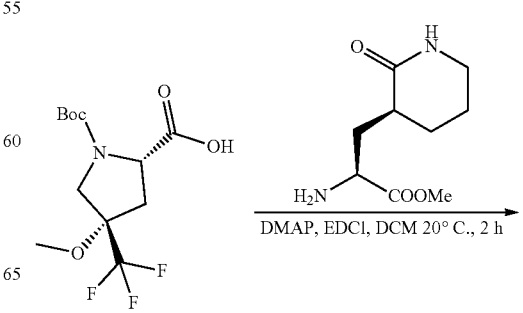

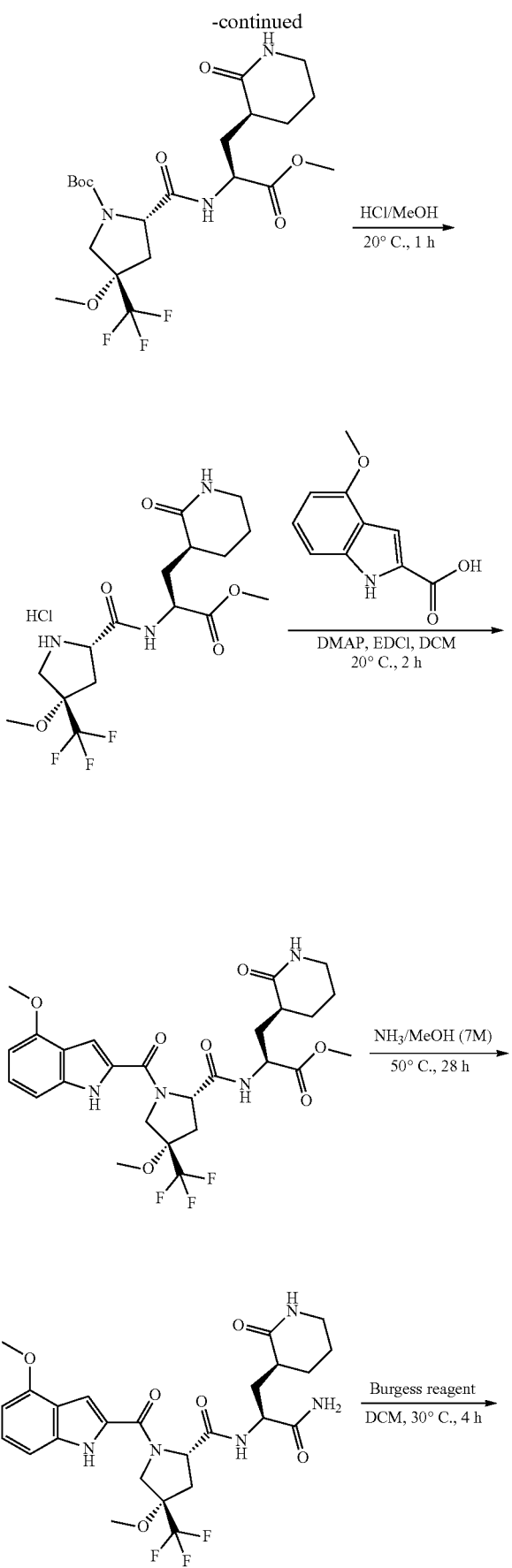

Step 1: tert-butyl (2S,4S)-4-methoxy-2-[[(1S)-2-methoxy-2-oxo-1-[[(3S)-2-oxo-3-piperidyl]methyl]ethyl]carbamoyl]-4-(trifluoromethyl)pyrrolidine-1-carboxylate To a solution of (2S,4S)-1-tert-butoxycarbonyl-4-methoxy-4-(trifluoromethyl)pyrrolidine-2-carboxylic acid (0.5 g, 1.60 mmol, 1.2 eq), methyl (2S)-2-amino-3-[(3S)-2-oxo-3-piperidyl]propanoate (314.82 mg, 1.33 mmol, 1 eq, HCl), EDCI (509.94 mg, 2.66 mmol, 2 eq) in DCM (5 mL) was added DMAP (487.48 mg, 3.99 mmol, 3 eq) and the mixture was stirred at 20° C. for 2 h. Upon completion, the reaction mixture was quenched by addition H₂O (100 mL) and extracted with DCM (15 mL*4). The combined organic layers were dried over Na₂SO₄, filtered and concentrated under reduced pressure and was purified by column chromatography (SiO₂, Petroleum ether/Ethyl acetate=1/1 to 0/1 and then DCM:MeOH=5:1) to give product tert-butyl (2S,4S)-4-methoxy-2-[[(1S)-2-methoxy-2-oxo-1-[[(3S)-2-oxo-3-piperidyl]methyl]ethyl]carbamoyl]-4-(trifluoromethyl) pyrrolidine-1-carboxylate (0.9 g, 1.27 mmol, 95.60% yield, 70% purity) as yellow oil. MS (ESI) m/z 496.2 [M+H]⁺

Step 2: methyl (2S)-2-[[(2S,4S)-4-methoxy-4-(trifluoromethyl)pyrrolidine-2-carbonyl]amino]-3-[(3S)-2-oxo-3-piperidyl]propanoate To a solution of tert-butyl (2S,4S)-4-methoxy-2-[[(1S)-2-methoxy-2-oxo-1-[[(3S)-2-oxo-3-piperidyl]methyl]ethyl]carbamoyl]-4-(trifluoromethyl)pyrrolidine-1-carboxylate (0.8 g, 1.61 mmol, 1 eq) in HCl/MeOH (4 M, 9 mL, 22.30 eq) was stirred at 20° C. for 1 h. Upon completion, the reaction was concentrated under pressure reduced to give crude product methyl (2S)-2-[[(2S,4S)-4-methoxy-4-(trifluoromethyl)pyrrolidine-2-carbonyl]amino]-3-[(3S)-2-oxo-3-piperidyl]propanoate (0.65 g, crude, HCl) as yellow oil. MS (ESI) m/z 396.1 [M+H]⁺

Step 3: methyl (2S)-2-[[(2S,4S)-4-methoxy-1-(4-methoxy-1H-indole-2-carbonyl)-4-(trifluoromethyl)pyrrolidine-2-carbonyl]amino]-3-[(3S)-2-oxo-3-piperidyl]propanoate To a solution of methyl (2S)-2-[[(2S,4S)-4-methoxy-4-(trifluoromethyl)pyrrolidine-2-carbonyl]amino]-3-[(3S)-2-oxo-3-piperidyl]propanoate (0.65 g, 1.51 mmol, 1 eq, HCl), 4-methoxy-1H-indole-2-carboxylic acid (345.32 mg, 1.81 mmol, 1.2 eq) in DCM (5 mL) was added DMAP (551.67 mg, 4.52 mmol, 3 eq) and EDCI (577.10 mg, 3.01 mmol, 2 eq). The mixture was stirred at 20° C. for 2 h. Upon completion, the reaction was quenched by addition H₂O (80 mL) and extracted with DCM (10 mL*4). The combined organic layers were dried over Na₂SO₄, filtered and concentrated under reduced pressure and was purified by column chromatography (SiO₂, Petroleum ether/Ethyl acetate=1/1 to 0/1) to give the product methyl (2S)-2-[[(2S,4S)-4-methoxy-1-(4-methoxy-1H-indole-2-carbonyl)-4-(trifluoromethyl)pyrrolidine-2-carbonyl]amino]-3-[(3S)-2-oxo-3-piperidyl]propanoate (0.65 g, crude) as yellow oil. MS (ESI) m/z 569.2 [M+H]⁺

Step 4: (2S,4S)-N-[(1S)-2-amino-2-oxo-1-[[(3S)-2-oxo-3-piperidyl]methyl]ethyl]-4-methoxy-1-(4-methoxy-1H-indole-2-carbonyl)-4-(trifluoromethyl)pyrrolidine-2-carboxamide To a solution of methyl (2S)-2-[[(2S,4S)-4-methoxy-1-(4-methoxy-1H-indole-2-carbonyl)-4-(trifluoromethyl)pyrrolidine-2-carbonyl]amino]-3-[(3S)-2-oxo-3-piperidyl]propanoate (0.53 g, 932.21 umol, 1 eq) in NH₃/MeOH (3 mL) was stirred at 50° C. for 28 h. Upon completion, the reaction was concentrated under pressure reduced to get the crude product (2S,4S)-N-[(1S)-2-amino-2-oxo-1-[[(3S)-2-oxo-3-piperidyl]methyl]ethyl]-4-methoxy-1-(4-methoxy-1H-indole-2-carbonyl)-4-(trifluoromethyl)pyrrolidine-2-carboxamide (0.5 g, crude) as yellow solid. MS (ESI) m/z 554.2 [M+H]⁺

Step 5: (2S,4S)-N-[(1S)-1-cyano-2-[(3S)-2-oxo-3-piperidyl]ethyl]-4-methoxy-1-(4-methoxy-1H-indole-2-carbonyl)-4-(trifluoromethyl)pyrrolidine-2-carboxamide To a solution of (2S,4S)-N-[(1S)-2-amino-2-oxo-1-[[(3S)-2-oxo-3-piperidyl]methyl]ethyl]-4-methoxy-1-(4-methoxy-11H-indole-2-carbonyl)-4-(trifluoromethyl)pyrrolidine-2-carboxamide (0.5 g, 812.96 umol, 90% purity, 1 eq) in DCM (8 mL) was added BURGESS REAGENT (581.21 mg, 2.44 mmol, 3 eq) and the mixture was stirred at 30° C. for 4 h. Upon completion, the mixture were quenched with water (1.5 mL) and blow-dried with N₂ and was purified by prep-HPLC (column: Waters Xbridge Prep OBD C18 150*40 mm*10 um; mobile phase: [water (10 mM NH₄HCO₃)-ACN]; B %: 25%-50%, 8 min) to give product (2S,4S)-N-[(1S)-1-cyano-2-[(3S)-2-oxo-3-piperidyl]ethyl]-4-methoxy-1-(4-methoxy-1H-indole-2-carbonyl)-4-(trifluoromethyl)pyrrolidine-2-carboxamide (0.21 g, 392.15 umol, 48.24% yield, 100% purity) as white solid. MS (ESI) m/z 536.2 [M+H]⁺

¹H NMR (400 MHz, DMSO-d₆) δ=7.25-7.13 (m, 1H), 7.05 (br d, J=8.2 Hz, 2H), 6.63-6.40 (m, 1H), 5.36-4.89 (m, 2H), 4.47-4.04 (m, 2H), 4.02-3.79 (m, 3H), 3.45 (br s, 3H), 3.26-2.90 (m, 2H), 2.86-2.50 (m, 2H), 2.49-2.14 (m, 2H), 2.04-1.04 (m, 5H).

Example 231. Synthesis of Viral Protease Inhibitor Compound 1053

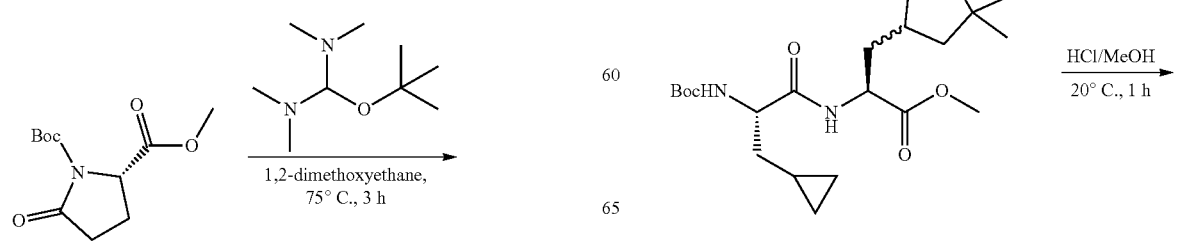

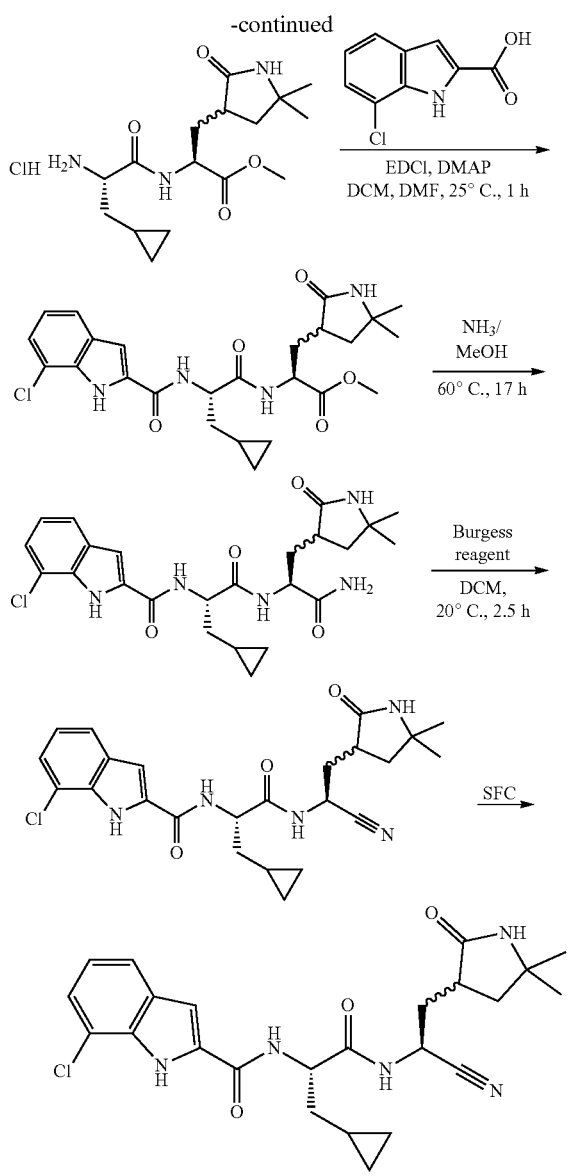

Step 1: O1-tert-butylO2-methyl(2S,4E)-4-(dimethyl-aminomethylene)-5-oxo-pyrrolidine-1,2-dicarboxylate A mixture of O1-tert-butyl O2-methyl (2S)-5-oxopyrro-lidine-1,2-dicarboxylate (282 g, 1.16 mol, 1 eq), 1-tert-butoxy-N,N,N',N'-tetramethyl-methanediamine (303.06 g, 1.74 mol, 359.08 mL, 1.5 eq) in DME (282 mL) was stirred at 75° C. for 3 h. Upon completion, the mixture was cooled to 0° C. and then filtered, the filter cake was concentrated under the reduced pressure to give the product O1-tert-butylO2-methyl(2S,4E)-4-(dimethylaminomethylene)-5-oxo-pyrrolidine-1,2-dicarboxylate (272 g, crude) as a white solid.

Step 2: O1-tert-butyl O2-methyl (2S)-4-methylene-5-oxo-pyrrolidine-1,2-dicarboxylate To a solution of O1-tert-butyl O2-methyl (2S,4E)-4-(dimethylaminomethylene)-5-oxo-pyrrolidine-1,2-dicarboxy-late (70 g, 234.64 mmol, 1 eq) in THF (700 mL) was added DIBAL-H (1 M, 703.91 mL, 3 eq) at −78° C. The mixture was stirred at −78° C. for 2 h. Upon completion, the reaction mixture was quenched by added to sat. NH$_4$Cl (2500 mL) and then extracted with EA (1000 mL*3). The combined organic layers were washed with brine (2000 mL), dried over Na$_2$SO$_4$, filtered and concentrated under reduced pressure to give a residue. The residue was purified by column chromatography (SiO$_2$, Petroleum ether/Ethyl acetate=10/1 to 1/1) to give the product. The product O1-tert-butyl O2-methyl (2S)-4-methylene-5-oxo-pyrrolidine-1,2-dicarboxylate (35 g, 137.11 mmol, 58.44% yield) was obtained as a white solid.

Step 3: dimethyl (2S)-2-(tert-butoxycarbo-nylamino)-4-methylene-pentanedioate

To a solution of O1-tert-butyl O2-methyl (2S)-4-methyl-ene-5-oxo-pyrrolidine-1,2-dicarboxylate (25 g, 97.94 mmol, 1 eq) in THF (250 mL) was added lithium; methanolate (1 M, 117.52 mL, 1.2 eq) at −40° C. The solution was stirred for 2 h at −40° C. Upon completion, the solution was quenched with NH$_4$Cl (70 mL) and concentrated and extracted with EA (80 mL*2) and concentrated to give crude dimethyl (2S)-2-(tert-butoxycarbonylamino)-4-methylene-pentanedioate (24 g, crude) as a yellow oil and used directly for the next step. MS (ESI) m/z 188.1 [M+H−100]$^+$ Step 4: dimethyl (2S)-2-(tert-butoxycarbo-nylamino)-4-(2-methyl-2-nitro-propyl)pentanedioate To a solution of dimethyl (2S)-2-(tert-butoxycarbo-nylamino)-4-methylene-pentanedioate (34 g, 118.34 mmol, 1 eq) and 2-nitropropane (11.60 g, 130.17 mmol, 11.69 mL, 1.1 eq) in ACN (350 mL) was added DBU (21.62 g, 142.01 mmol, 21.40 mL, 1.2 eq). The solution was stirred for 2 h at 20° C. Upon completion, the solution was concentrated to give crude. The crude was purified by column (SiO$_2$, PE:EA=20:1 to 1:1) to give product compound dimethyl (2S)-2-(tert-butoxycarbonylamino)-4-(2-methyl-2-nitro-propyl)pentanedioate (30 g, 79.70 mmol, 67.35% yield) as a white solid. MS (ESI) m/z 277.1 [M+H−100]$^+$ Step 5: methyl (2S)-2-(tert-butoxycarbonylamino)-3-(5,5-dimethyl-2-oxo-pyrrolidin-3-yl)propanoate To a solution of dimethyl (2S)-2-(tert-butoxycarbo-nylamino)-4-(2-methyl-2-nitro-propyl)pentanedioate (26 g, 69.08 mmol, 1 eq) in IPA (250 mL) was added Pd/C (24.54 g, 20.72 mmol, 10% purity, 0.3 eq) under N$_2$. The suspension was degassed under vacuum and purged with H$_2$ several times. The mixture was stirred under H$_2$ (15 psi) at 40° C. for 15 h. Upon completion, the mixture was filtered and concentrated to give crude compound. The crude was purified by column (SiO$_2$, PE:EA=20:1 to 0:1) to give product methyl (2S)-2-(tert-butoxycarbonylamino)-3-(5,5-dimethyl-2-oxo-pyrrolidin-3-yl)propanoate (14.6 g, 46.44 mmol, 67.23%) as a white solid and continue purified by SFC (column: DAICEL CHIRALPAK IC (250 mm*50 mm, 10 um); mobile phase: [0.1% NH$_3$H$_2$O IPA]; B %: 30%-30%, 11.5 min) to give BB7 methyl (2S)-2-(tert-butoxycarbo-nylamino)-3-(5,5-dimethyl-2-oxo-pyrrolidin-3-yl)propano-ate (4.8 g, 15.27 mmol, 32.65% yield) as a white solid. MS (ESI) m/z 315.2 [M+H]$^+$ Step 6: methyl (2S)-2-amino-3-(5,5-dimethyl-2-oxo-pyrrolidin-3-yl)propanoate A solution of methyl (2S)-2-(tert-butoxycarbonylamino)-3-(5,5-dimethyl-2-oxo-pyrrolidin-3-yl) propanoate (500 mg, 1.59 mmol, 1 eq) in HCl/MeOH (10 mL) was stirred at 20° C. for 2 h. Upon completion, the solution was concentrated to dryness to give crude compound methyl (2S)-2-amino-3-(5,5-dimethyl-2-oxo-pyrrolidin-3-yl)propanoate (398 mg, crude, HCl) as a white solid and used directly for the next step.

Step 7: methyl (2S)-2-[[(2S)-2-(tert-butoxycarbonylamino)-3-cyclopropyl-propanoyl]amino]-3-(5,5-dimethyl-2-oxo-pyrrolidin-3-yl)propanoate To a solution of methyl (2S)-2-amino-3-(5,5-dimethyl-2-oxo-pyrrolidin-3-yl)propanoate (370 mg, 1.48 mmol, 1 eq, HCl) in DCM (10 mL) and DMF (5 mL) was added DMAP (360.58 mg, 2.95 mmol, 2 eq) and (2S)-2-(tert-butoxycarbonylamino)-3-cyclopropyl-propanoic acid (372.18 mg, 1.62 mmol, 1.1 eq) and EDCI (565.80 mg, 2.95 mmol, 2 eq). The mixture was stirred at 25° C. for 1 h. Upon completion, the mixture was diluted with H$_2$O (60 mL) and extracted with EA (60 mL*3) and concentrated to give crude. The crude was purified by column (SiO$_2$, PE:EA=10:1 to 0:1) to give compound methyl (2S)-2-[[(2S)-2-(tert-butoxycarbonylamino)-3-cyclopropyl-propanoyl] amino]-3-(5,5-dimethyl-2-oxo-pyrrolidin-3-yl)propanoate (550 mg, 1.29 mmol, 87.59% yield) as a yellow oil. MS (ESI) m/z 426.2 [M+H]$^+$ Step 8: methyl (2S)-2-[[(2S)-2-amino-3-cyclopropyl-propanoyl]amino]-3-(5,5-dimethyl-2-oxo-pyrrolidin-3-yl)propanoate A solution of methyl (2S)-2-[[(2S)-2-(tert-butoxycarbonylamino)-3-cyclopropyl-propanoyl]amino]-3-(5,5-dimethyl-2-oxo-pyrrolidin-3-yl)propanoate (540 mg, 1.27 mmol, 1 eq) in HCl/MeOH (15 mL) was stirred at 20° C. for 1 h. Upon completion, the solution was concentrated to dryness to give crude compound methyl (2S)-2-[[(2S)-2-amino-3-cyclopropyl-propanoyl]amino]-3-(5,5-dimethyl-2-oxo-pyrrolidin-3-yl)propanoate (456 mg, crude, HCl) as a white solid.

Step 9: methyl (2S)-2-[[(2S)-2-[(7-chloro-1H-indole-2-carbonyl)amino]-3-cyclopropyl-propanoyl] amino]-3-(5,5-dimethyl-2-oxo-pyrrolidin-3-yl)propanoate To a solution of methyl (2S)-2-[[(2S)-2-amino-3-cyclopropyl-propanoyl]amino]-3-(5,5-dimethyl-2-oxo-pyrrolidin-3-yl)propanoate (450 mg, 1.24 mmol, 1 eq, HCl) in DCM (10 mL) and DMF (5 mL) was added DMAP (303.85 mg, 2.49 mmol, 2 eq) and 7-chloro-1H-indole-2-carboxylic acid (243.24 mg, 1.24 mmol, 1 eq) and EDCI (476.79 mg, 2.49 mmol, 2 eq). The mixture was stirred at 25° C. for 1 h. Upon completion, the solution was diluted with H$_2$O (60 mL) and extracted with EA (70 mL*3) and washed with brine (100 mL*2) and concentrated to give crude. The crude was purified by column (SiO$_2$, PE:EA=3:1 to 0:1) to give product methyl (2S)-2-[[(2S)-2-[(7-chloro-1H-indole-2-carbonyl) amino]-3-cyclopropyl-propanoyl]amino]-3-(5,5-dimethyl-2-oxo-pyrrolidin-3-yl)propanoate (550 mg, 1.09 mmol, 87.93% yield) as a white solid. MS (ESI) m/z 503.2 [M+H]$^+$ Step 10: N-[(1S)-2-[[(1S)-2-amino-1-[(5,5-dimethyl-2-oxo-pyrrolidin-3-yl)methyl]-2-oxo-ethyl] amino]-1-(cyclopropylmethyl)-2-oxo-ethyl]-7-chloro-1H-indole-2-carboxamide A solution of methyl (2S)-2-[[(2S)-2-[(7-chloro-1H-indole-2-carbonyl)amino]-3-cyclopropyl-propanoyl]amino]-3-(5,5-dimethyl-2-oxo-pyrrolidin-3-yl)propanoate (550 mg, 1.09 mmol, 1 eq) in NH$_3$/MeOH (7 M, 7.81 mL, 50 eq) was stirred at 60° C. for 17 h. Upon completion, the solution was concentrated to dryness to give crude. The crude was used directly for the next step. Compound N-[(1S)-2-[[(1S)-2-amino-1-[(5,5-dimethyl-2-oxo-pyrrolidin-3-yl)methyl]-2-oxo-ethyl]amino]-1-(cyclopropylmethyl)-2-oxo-ethyl]-7-chloro-1H-indole-2-carboxamide (530 mg, crude) was obtained as a white solid. MS (ESI) m/z 488.2 [M+H]$^+$ Step 11: 7-chloro-N-[(1S)-2-[[(1S)-1-cyano-2-(5,5-dimethyl-2-oxo-pyrrolidin-3-yl)ethyl]amino]-1-(cyclopropylmethyl)-2-oxo-ethyl]-1H-indole-2-carboxamide To a solution of N-[(1S)-2-[[(1S)-2-amino-1-[(5,5-dimethyl-2-oxo-pyrrolidin-3-yl)methyl]-2-oxo-ethyl]amino]-1-(cyclopropylmethyl)-2-oxo-ethyl]-7-chloro-1H-indole-2-carboxamide (530 mg, 1.09 mmol, 1 eq) in DCM (20 mL) was added BURGESS REAGENT (517.65 mg, 2.17 mmol, 2 eq). The mixture was stirred at 20° C. for 2.5 h. Upon the reaction was completion, the solution was washed with H$_2$O (30 mL) and the organic phase was blowed dry with N$_2$ to give crude. The crude was purified by neutral pre-HPLC (Waters Xbridge C18 150*50 mm*10 um; mobile phase: [water (10 mM NH$_4$HCO$_3$)-ACN]; B %: 30%-70%, 10 min) to give product. MS (ESI) m/z 470.2 [M+H]$^+$ 7-chloro-N-[(1 S)-2-[[(1 S)-1-cyano-2-(5,5-dimethyl-2-oxo-pyrrolidin-3-yl)ethyl]amino]-1-(cyclopropylmethyl)-2-oxo-ethyl]-1H-indole-2-carboxamide (330 mg, 702.18 umol, 64.65% yield) was obtained as a white solid.

$^1$H NMR (400 MHz, DMSO-d$_6$) Shift=11.56 (br s, 1H), 8.89 (d, J=7.9 Hz, 1H), 8.60 (d, J=7.5 Hz, 1H), 7.70 (s, 1H), 7.50 (d, J=7.9 Hz, 1H), 7.19 (d, J=7.6 Hz, 1H), 7.12 (s, 1H), 6.95 (t, J=7.8 Hz, 1H), 4.95-4.76 (m, 1H), 4.46-4.20 (m, 1H), 2.52-2.44 (m, 1H), 2.12-1.99 (m, 1H), 1.88 (dd, J=8.6, 12.2 Hz, 1H), 1.76-1.60 (m, 2H), 1.45-1.33 (m, 2H), 1.03 (s, 3H), 0.95 (s, 3H), 0.76-0.62 (m, 1H), 0.38-0.25 (m, 2H), 0.14-0.06 (m, 2H).

Example 232. Synthesis of Viral Protease Inhibitor Compound 1111

Step 1: methyl (2S)-2-amino-3-(6,6-dimethyl-2-oxo-3-piperidyl)propanoate

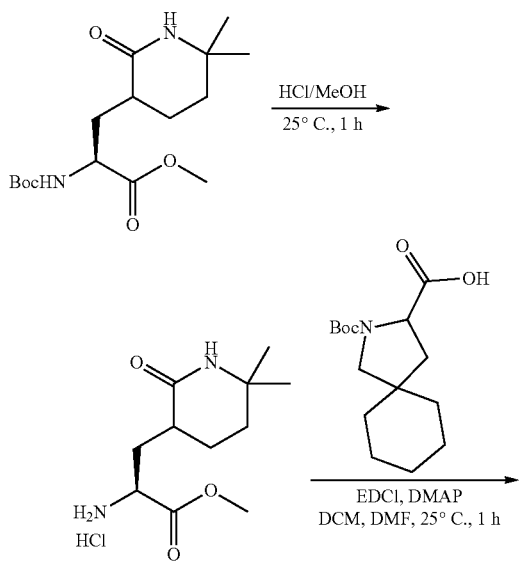

1341
-continued

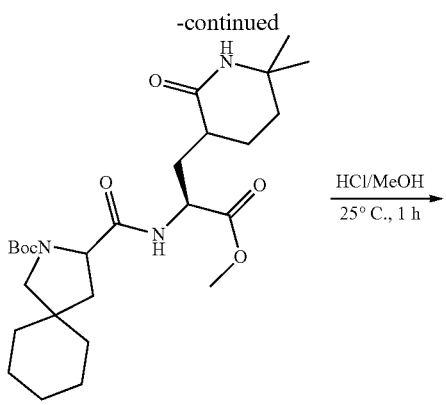

HCl/MeOH
25° C., 1 h

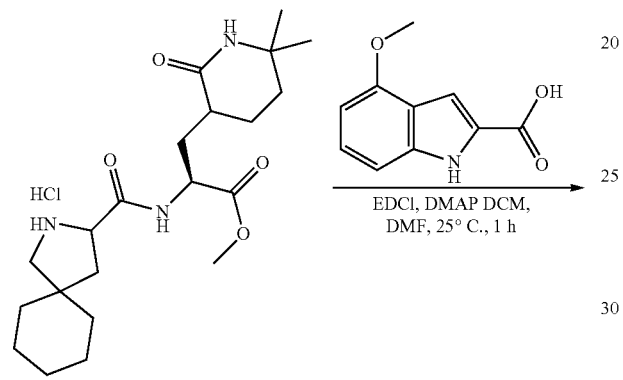

EDCl, DMAP DCM,
DMF, 25° C., 1 h

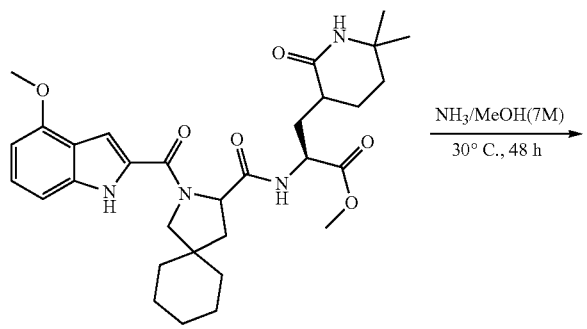

NH₃/MeOH(7M)
30° C., 48 h

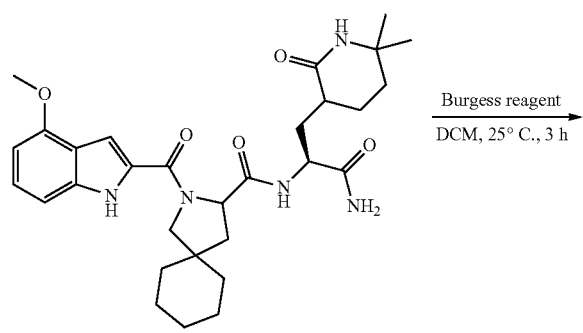

Burgess reagent
DCM, 25° C., 3 h

1342
-continued

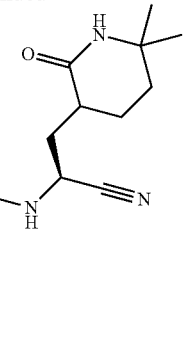

SFC

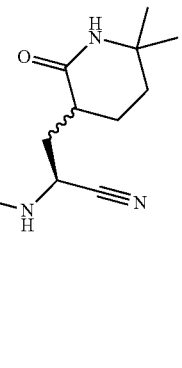

Step 1: methyl (2S)-2-amino-3-(6,6-dimethyl-2-oxo-3-piperidyl)propanoate methyl (2S)-2-(tert-butoxycarbonylamino)-3-(6,6-dimethyl-2-oxo-3-piperidyl)propanoate (20 mg, 60.90 umol, 1 eq) was added HCl/MeOH (4 M, 5 mL, 328.40 eq). The mixture was stirred at 25° C. for 1 h. Upon completion, the reaction mixture was concentrated under reduced pressure to give a residue. The residue was used next step directly. Compound methyl (2S)-2-amino-3-(6,6-dimethyl-2-oxo-3-piperidyl)propanoate (16 mg, 57.41 umol, 94.27% yield, 95% purity, HCl) was obtained as a colourless oil.

Step 2: tert-butyl 3-[[(1S)-1-[(6,6-dimethyl-2-oxo-3-piperidyl)methyl]-2-methoxy-2-oxo-ethyl] carbamoyl]-2-azaspiro[4.5]decane-2-carboxylate To a mixture of 2-tert-butoxycarbonyl-2-azaspiro[4.5]decane-3-carboxylic acid (171.25 mg, 604.35 umol, 1 eq) and methyl (2S)-2-amino-3-(6,6-dimethyl-2-oxo-3-piperidyl)propanoate (160 mg, 604.35 umol, 1 eq, HCl) in DMF (3 mL) and DCM (6 mL) was added EDCI (231.71 mg, 1.21 mmol, 2 eq) and DMAP (147.67 mg, 1.21 mmol, 2 eq). The mixture was stirred at 25° C. for 1 h. Upon completion, the reaction mixture was diluted with H₂O 20 mL and extracted with DCM 50 mL (25 mL*2). The combined organic layers were washed with BRINE 20 mL (20 mL*1), dried over Na₂SO₄, filtered and concentrated under reduced pressure to give a residue. The residue was purified by column chromatography (SiO₂, Petroleum ether/Ethyl acetate=7/1 to 1/1) to get the compound tert-butyl 3-[[(1S)-1-[(6,6-dimethyl-2-oxo-3-piperidyl)methyl]-2-methoxy-2-oxo-ethyl] carbamoyl]-2-azaspiro[4.5]decane-2-carboxylate (195 mg, 395.03 umol, 65.36% yield, N/A purity) as a colourless oil.

Step 3: methyl (2S)-2-(2-azaspiro[4.5]decane-3-carbonylamino)-3-(6,6-dimethyl-2-oxo-3-piperidyl)propanoate tert-butyl 3-[[(1S)-1-[(6,6-dimethyl-2-oxo-3-piperidyl)methyl]-2-methoxy-2-oxo-ethyl]carbamoyl]-2-azaspiro[4.5]decane-2-carboxylate (170 mg, 344.38 umol, 1 eq) was added HCl/MeOH (4 M, 17.00 mL, 197.45 eq). The mixture was stirred at 25° C. for 1 h. Upon completion, the reaction mixture was concentrated under reduced pressure to give a residue. The residue was used next step directly. Compound methyl (2S)-2-(2-azaspiro[4.5]decane-3-carbonylamino)-3-(6,6-dimethyl-2-oxo-3-piperidyl)propanoate (145 mg, 320.36 umol, 93.03% yield, 95% purity, HCl) was obtained as a colourless oil.

Step 4: methyl (2S)-3-(6,6-dimethyl-2-oxo-3-piperidyl)-2-[[2-(4-methoxy-1H-indole-2-carbonyl)-2-azaspiro[4.5]decane-3-carbonyl]amino]propanoate To a mixture of 4-methoxy-1H-indole-2-carboxylic acid (64.47 mg, 337.23 umol, 1 eq) and methyl (2S)-2-(2-azaspiro[4.5]decane-3-carbonylamino)-3-(6,6-dimethyl-2-oxo-3-piperidyl)propanoate (145 mg, 337.23 umol, 1 eq, HCl) in DCM (6 mL) and DMF (3 mL) was added DMAP (82.40 mg, 674.45 umol, 2 eq) and EDCI (129.29 mg, 674.45 umol, 2 eq). The mixture was stirred at 25° C. for 1 h. Upon completion, the reaction mixture was diluted with $H_2O$ 30 mL and extracted with EA 100 mL (50 mL*2). The combined organic layers were washed with BRINE 50 mL (50 mL*1), dried over $Na_2SO_4$, filtered and concentrated under reduced pressure to give a residue. The residue was purified by prep-TLC (DCM:MeOH=10: 1) to get the compound methyl (2S)-3-(6,6-dimethyl-2-oxo-3-piperidyl)-2-[[2-(4-methoxy-1H-indole-2-carbonyl)-2-azaspiro[4.5]decane-3-carbonyl]amino]propanoate (200 mg, 335.28 umol, 99.42% yield, 95% purity) as a yellow oil. MS (ESI) m/z 567.3 $[M+H]^+$

Step 5: N-[(1S)-2-amino-1-[(6,6-dimethyl-2-oxo-3-piperidyl)methyl]-2-oxo-ethyl]-2-(4-methoxy-1H-indole-2-carbonyl)-2-azaspiro[4.5]decane-3-carboxamide To a mixture of methyl (2S)-3-(6,6-dimethyl-2-oxo-3-piperidyl)-2-[[2-(4-methoxy-1H-indole-2-carbonyl)-2-azaspiro[4.5]decane-3-carbonyl]amino]propanoate (200 mg, 352.93 umol, 1 eq) was added $NH_3$/MeOH (7 M, 50.42 uL, 1 eq). The mixture was stirred at 30° C. for 48 h. Upon completion, the reaction mixture was concentrated under reduced pressure to give a residue and the residue was used next step directly. Compound N-[(1S)-2-amino-1-[(6,6-dimethyl-2-oxo-3-piperidyl) methyl]-2-oxo-ethyl]-2-(4-methoxy-1H-indole-2-carbonyl)-2-azaspiro[4.5]decane-3-carboxamide (190 mg, 309.96 umol, 87.83% yield, 90% purity) was obtained as a white solid. MS (ESI) m/z 552.3 $[M+H]^+$

Step 6: N-[(1S)-1-cyano-2-(6,6-dimethyl-2-oxo-3-piperidyl)ethyl]-2-(4-methoxy-1H-indole-2-carbonyl)-2-azaspiro[4.5]decane-3-carboxamide To a mixture of N-[(1S)-2-amino-1-[(6,6-dimethyl-2-oxo-3-piperidyl)methyl]-2-oxo-ethyl]-2-(4-methoxy-1H-indole-2-carbonyl)-2-azaspiro[4.5]decane-3-carboxamide (190 mg, 344.41 umol, 1 eq) in DCM (2 mL) was added BURGESS REAGENT (164.15 mg, 688.81 umol, 2 eq). The mixture was stirred at 25° C. for 3 h. Upon completion, the reaction mixture was diluted with $H_2O$ 5 mL and extracted with DCM 10 mL (5 mL*2). The combined organic layers were concentrated by blow-drying to give a residue. The residue was purified by prep-HPLC (neutral condition) (column: Waters Xbridge BEH C18 100*30 mm*10 um; mobile phase: [water (10 mM NH4HCO3)-ACN]; B %: 30%-60%, 10 min) to give desired compound (80 mg) as a white solid. The white solid was separated by SFC (column: REGIS(S,S)WHELK-O1 (250 mm*25 mm, 10 um); mobile phase: [Neu-ETOH]; B %: 60%-60%, 7 min) to get the P1, P2 & P3, P4. The mixture (P2 & P3) was separated by SFC (column: REGIS(S,S)WHELK-O1 (250 mm*25 mm, 10 um); mobile phase: [Neu-MeOH]; B %: 50%-50%, 15 min). MS (ESI) m/z 534.2 $[M+H]^+$ Isomer 1: Compound N-[(1S)-1-cyano-2-(6,6-dimethyl-2-oxo-3-piperidyl)ethyl]-2-(4-methoxy-1H-indole-2-carbonyl)-2-azaspiro[4.5]decane-3-carboxamide (13 mg, 24.36 umol, 7.07% yield, 100% purity) was obtained as a white solid.

$^1$H NMR (400 MHz, DMSO-d6) δ=11.29 (br s, 1H), 8.69 (br s, 1H), 7.28-6.72 (m, 4H), 6.52 (d, J=7.7 Hz, 1H), 4.99 (br s, 1H), 4.78-4.46 (m, 1H), 3.95-3.82 (m, 4H), 3.73-3.40 (m, 1H), 2.34-2.04 (m, 3H), 1.89-1.31 (m, 16H), 1.13 (br d, J=10.6 Hz, 6H)

Isomer 2: Compound N-[(1S)-1-cyano-2-(6,6-dimethyl-2-oxo-3-piperidyl)ethyl]-2-(4-methoxy-1H-indole-2-carbonyl)-2-azaspiro[4.5]decane-3-carboxamide (17 mg, 31.86 umol, 9.25% yield, 100% purity) was obtained as a white solid.

$^1$H NMR (400 MHz, DMSO-d6) δ=11.31 (br s, 1H), 8.64 (br s, 1H), 7.25-6.75 (m, 4H), 6.52 (d, J=7.7 Hz, 1H), 4.99 (q, J=8.0 Hz, 1H), 4.61 (br s, 1H), 4.01-3.80 (m, 4H), 3.66 (br s, 1H), 2.30-1.94 (m, 3H), 1.92-1.31 (m, 16H), 1.12 (d, J=6.4 Hz, 6H)

Isomer 3: Compound N-[(1S)-1-cyano-2-(6,6-dimethyl-2-oxo-3-piperidyl)ethyl]-2-(4-methoxy-1H-indole-2-carbonyl)-2-azaspiro[4.5]decane-3-carboxamide (14 mg, 26.23 umol, 7.62% yield, 100% purity) was obtained as a white solid.

$^1$H NMR (400 MHz, DMSO-d6) δ=11.30 (br s, 1H), 8.92-8.52 (m, 1H), 7.41-6.74 (m, 4H), 6.52 (br d, J=7.3 Hz, 1H), 4.94 (br s, 1H), 4.63 (br s, 1H), 4.03-3.78 (m, 4H), 3.73-3.44 (m, 1H), 2.35-2.04 (m, 3H), 1.93-1.32 (m, 16H), 1.14 (s, 6H)

Isomer 4: Compound N-[(1S)-1-cyano-2-(6,6-dimethyl-2-oxo-3-piperidyl)ethyl]-2-(4-methoxy-1H-indole-2-carbonyl)-2-azaspiro[4.5]decane-3-carboxamide (28 mg, 52.23 umol, 15.16% yield, 99.538% purity) was obtained as a white solid.

$^1$H NMR (400 MHz, DMSO-d6) δ=11.31 (br s, 1H), 8.69 (br s, 1H), 7.27-6.77 (m, 4H), 6.53 (d, J=7.5 Hz, 1H), 4.94 (br s, 1H), 4.61 (br s, 1H), 4.06-3.83 (m, 4H), 3.66 (br s, 1H), 2.32-1.98 (m, 3H), 1.83-1.32 (m, 16H), 1.13 (d, J=18.1 Hz, 6H)

Example 233. Evaluation of Antiviral Activity of Compounds Against COVID-19 (nCoV-2019, SARS-CoV2) Mpro in the Enzymatic Assay Compounds are assayed using standard methods to assess compound activity and IC50. As an exemplary for assessment of the SARS-COV2 Mpro, the C-His6-tagged Mpro (NC_045512) is cloned, expressed in *E. coli* and purified. The assay buffer contains 20 mM of Tris-HCl (pH 7.3), 100 mM of NaCl, 1 mM of EDTA, 5 mM of TCEP and 0.1% BSA. The final concentrations of the Mpro protein and substrate are 25 nM and 25 µM, respectively, in the Mpro enzymatic assay. The Km of the Mpro substrate for the protease was 13.5 µM.

The compounds are added to an assay plate. For 100% inhibition control (HPE, hundred percent effect), 1 µM GC376 is added. For no inhibition control (ZPE, zero percent effect), no compound is added. Each activity testing point has a relevant background control to normalize the fluorescence interference of compound.

IC50 values of compounds are calculated with the GraphPad Prism software using the nonlinear regression model of log(inhibitor) vs. response—Variable slope (four parameters). The inhibition activity is calculated using the formula below, IC50 values is calculated using the Inhibition % data.

Inhibition %=[(Sample−Average ZPE)/(Average HPE−Average ZPE)]*100%#

HEP: Hundred percent effect controls. Containing substrate+enzyme+1 µM GC376.
ZPE: Zero percent effective controls. Containing enzyme+substrate, no compound.
Sample: Compound activity testing wells. Containing compound+enzyme+substrate.
BG: Compound background control wells. Containing compound+substrate, no enzyme.

Example 234. Evaluation of Antiviral Activity of Compounds Against Human Coronavirus (HCov) 229E and OC43 in the Cytopathic Effect (CPE) Assays Compounds are assayed using standard methods against multiple coronaviral strains, including HCoV 229E and OC43 strains. The antiviral activity of compounds is calculated based on the protection of the virus-induced CPE at each concentration normalized by the virus control.

Reagents and instruments used in this assay include luminescent cell viability assay kit CellTiter Glo (Promega) and Microplate Reader Synergy2 (BioTek).
Virus—HCoV 229E
Cytopathic effect (CPE) is measured by CellTiter Glo following the manufacturer's manual. The antiviral activity of compounds is calculated based on the protection of the virus-induced CPE at each concentration normalized by the virus control.
Virus—HCov OC43
Reference compound used is remdesivir; detection reagent: CellTiter Glo.) The CPE are measured by CellTiter Glo following the manufacturer's manual. The antiviral activity of compounds is calculated based on the protection of the virus-induced CPE at each concentration normalized by the virus control.

The cytotoxicity of compounds is assessed under the same conditions, but without virus infection, in parallel. Cell viability is measured with CellTiter Glo. The antiviral activity and cytotoxicity of compounds are expressed as % Inhibition and % Viability, respectively, and calculated with formulas.

Table 3, Table 4 and Table 5 below show activity data.

TABLE 3

Activity data for compounds.

| Compound No. | 229E Mpro $EC_{50}$ | SARS-CoV2 Mpro $IC_{50}$ |
|---|---|---|
| 101 | D | D |
| 103 | D | D |
| 127 | B | C |
| 129 | C | D |
| 131 | D | D |
| 133 | D | D |
| 134 | D | D |
| 134 (Isomer 1) | D | D |
| 134 (Isomer 2) | D | D |
| 135 | D | D |
| 135 (Isomer 1) | C | C |
| 135 (Isomer 2) | D | D |
| 136 | D | D |
| 143 | C | C |
| 145 | D | D |
| 147 | A | D |
| 149 | C | D |
| 153 | B | D |
| 163 | B | C |
| 165 | A | B |
| 167 | C | D |
| 171 | D | D |
| 183 | C | D |
| 185 | D | D |
| 191 | A | C |
| 197 | D | D |
| 199 | A | B |
| 201 | C | C |
| 205 | D | D |
| 209 | C | C |
| 213 | A | B |
| 223 (Isomer 1) | B | B |
| 223 (Isomer 2) | A | A |
| 225 | A | A |
| 227 | A | C |
| 231 | A | A |
| 237 | A | A |
| 241 | A | A |
| 245 | A | C |
| 249 | A | A |
| 253 | C | C |
| 265 | C | C |
| 267 | D | D |
| 267A | A | A |
| 269 | A | A |
| 269 | A | A |
| 271 | A | A |
| 271A (Isomer 1) | A | A |
| 271A (Isomer 2) | A | A |
| 271A (Isomer 3) | A | A |
| 271A (Isomer 4) | A | A |
| 273A | A | A |
| 273B | A | A |
| 273C | C | A |
| 279 | A | A |
| 305 | D | D |
| 323 (Isomer 1) | D | D |
| 323 (Isomer 2) | D | D |
| 325 | B | B |
| 327 | D | D |
| 329 | D | D |
| 331 (Isomer 1) | D | D |
| 331 (Isomer 2) | D | D |
| 344D | D | D |
| 344C | D | D |
| 344A | D | D |
| 345 | D | D |
| 345 (Isomer 1) | D | D |
| 345 (Isomer 2) | D | D |
| 355 | C | D |

TABLE 3-continued

Activity data for compounds.

| Compound No. | 229E Mpro EC$_{50}$ | SARS-CoV2 Mpro IC$_{50}$ |
|---|---|---|
| 357 | A | B |
| 359 | B | C |
| 361 | D | D |
| 363 | D | D |
| 365 (Isomer 1) | C | D |
| 365 (Isomer 2) | C | B |
| 369 (Isomer 1) | B | C |
| 369 (Isomer 2) | C | C |
| 375A | D | D |
| 377 | D | D |
| 379 | D | D |
| 383 | C | C |
| 385 (Isomer 1) | D | D |
| 385 (Isomer 2) | D | C |
| 387 | A | B |
| 389A (Isomer 1) | D | D |
| 391 | A | A |
| 393 | D | D |
| 395 (Isomer 1) | D | D |
| 395 (Isomer 2) | D | D |
| 397 | D | D |
| 399 (Isomer 1) | D | C |
| 399A (Isomer 1) | D | D |
| 399A (Isomer 2) | B | A |
| 401 | D | D |
| 401 (Isomer 1) | D | D |
| 401 (Isomer 2) | C | C |
| 405 | D | D |
| 407 | D | C |
| 409 | A | C |
| 413 | D | C |
| 429A (Isomer 1) | A | B |
| 429A (Isomer 2) | A | A |
| 431 | B | B |
| 433 | D | D |
| 439 | A | B |
| 449 | B | B |
| 449 (Isomer 1) | A | A |
| 449 (Isomer 2) | B | C |
| 451 (Isomer 1) | A | A |
| 451 (Isomer 2) | B | C |
| 455 | A | A |
| 457 | A | A |
| 459 | A | A |
| 465 | B | B |
| 465 (Isomer 1) | A | A |
| 465 (Isomer 2) | B | C |
| 467 (Isomer 1) | C | C |
| 467 (Isomer 2) | A | A |
| 469 | A | B |
| 469 (Isomer 1 & Isomer 2) | A | A |
| 469 (Isomer 3) | A | A |
| 469 (Isomer 4) | A | A |
| 471 | B | A |
| 473 (Isomer 1) | A | A |
| 473 (Isomer 2) | A | A |
| 475 (Isomer 1 & Isomer 2) | C | B |
| 475 (Isomer 3) | B | A |
| 475 (Isomer 4) | A | A |
| 477 | A | B |
| 479 | B | A |
| 481 (Isomer 1) | A | A |
| 481 (Isomer 2) | A | A |
| 483 | A | A |
| 483 (Isomer 1) | A | A |
| 483 (Isomer 2) | A | A |
| 489 (Isomer 1) | A | A |
| 489 (Isomer 2) | A | A |
| 491 | D | D |
| 491 (Isomer 1) | D | D |
| 491 (Isomer 2) | A | B |
| 491 (Isomer 4) | D | D |
| 491A (Isomer 1) | A | A |
| 491A (Isomer 2) | D | D |
| 491B | B | B |
| 493 | A | A |
| 495 (Isomer 1) | A | A |
| 495 (Isomer 2) | A | A |
| 497 (Isomer 2) | D | D |
| 499 | D | D |
| 501 | A | A |
| 505 (Isomer 1) | A | A |
| 505 (Isomer 2) | A | C |
| 507 (Isomer 1.1) | D | D |
| 507 (Isomer 1.2) | D | D |
| 507 (Isomer 2.1) | D | D |
| 507 (Isomer 2.2) | D | D |
| 509 | D | D |
| 511 | D | D |
| 511 (Isomer 1) | D | D |
| 511 (Isomer 2) | D | D |
| 513 (Isomer 1) | C | C |
| 513 (Isomer 2) | C | D |
| 515 | D | D |
| 519 | D | D |
| 525 | D | D |
| 529 | D | D |
| 531 | D | D |
| 535 | A | C |
| 547 (Isomer 2) | D | C |
| 549 | D | D |
| 551 | D | D |
| 555 | B | B |
| 577 | D | D |
| 581 | A | B |
| 583 | A | B |
| 591 (Isomer 1) | A | A |
| 591 (Isomer 2) | A | C |
| 595 | D | D |
| 598 | C | D |
| 603a (Isomer 1) | D | D |
| 603a (Isomer 2) | A | B |
| 611 | D | D |
| 619 | D | D |
| 621 | D | D |
| 623 | A | A |
| 625 | D | D |
| 633 | D | D |
| 635 | D | D |
| 637 | D | D |
| 639 | D | D |
| 639A | D | D |
| 643 | D | D |
| 647 | D | D |
| 649 | C | C |
| 653 (Isomer 1) | D | D |
| 653 (Isomer 2) | D | D |
| 655 | B | A |
| 659 | A | A |
| 667 | D | D |
| 669 | D | D |
| 671 | B | C |
| 681 (Isomer 1) | D | D |
| 691 | D | D |
| 695 | D | D |
| 711 | D | D |
| 715 | D | D |
| 717 | D | D |
| 719 (Isomer 2) | D | D |
| 719A (Isomer 1) | B | B |
| 721 | D | D |
| 723 (Isomer 1) | B | B |
| 723 (Isomer 2) | D | D |

TABLE 3-continued

Activity data for compounds.

| Compound No. | 229E Mpro EC$_{50}$ | SARS-CoV2 Mpro IC$_{50}$ |
|---|---|---|
| 725 | D | D |
| 727 | D | D |
| 729 (Isomer 1) | D | D |
| 729 (Isomer 2) | D | C |
| 731 (Isomer 1) | D | D |
| 731 (Isomer 2) | B | C |
| 733 (Isomer 1) | D | D |
| 733 (Isomer 2) | C | C |
| 735 | D | D |
| 737 | D | D |
| 739 | D | D |
| 740 | B | C |
| 741 | D | D |
| 743 (Isomer 1) | A | A |
| 743 (Isomer 2) | D | D |
| 745 | D | D |
| 747 | D | D |
| 749A (Isomer 1) | C | D |
| 749A (Isomer 2) | C | D |
| 787A (Isomer 1) | C | D |
| 787A (Isomer 2) | C | D |
| 791 (Isomer 1) | A | A |
| 791 (Isomer 2) | D | D |
| 793 | D | D |
| 795 | D | D |
| 799 | D | D |
| 801 (Isomer 1) | D | D |
| 801 (Isomer 2) | B | B |
| 803 (Isomer 1) | A | A |
| 803 (Isomer 2) | A | A |
| 803 (Isomer 3) | D | D |
| 803 (Isomer 4) | D | C |
| 805 (Isomer 1) | A | B |
| 805 (Isomer 2) | D | D |
| 808 | D | D |
| 810 | D | D |
| 812 | D | D |
| 814 (Isomer 1) | A | A |
| 814 (Isomer 2) | D | D |
| 816 | A | A |
| 820 | D | D |
| 822 | D | D |
| 824 | D | D |
| 826 | D | D |
| 828 | D | D |
| 830 | D | D |
| 832 | D | D |
| 838 | D | D |
| 840 | D | D |
| 842 | D | D |
| 846 | D | D |
| 848 | D | D |
| 850 | B | D |
| 852 | D | D |
| 854 | D | D |
| 856 | D | D |
| 858 | D | D |
| 860 | D | D |
| 862 | D | D |
| 864 | D | D |
| 866 | D | D |
| 868 | D | D |
| 872 | C | C |
| 875 (Isomer 1) | D | D |
| 875 (Isomer 2) | D | D |
| 875 (Isomer 3) | B | B |
| 876 | D | D |
| 878 (Isomer 1) | D | D |
| 878 (Isomer 2) | B | A |
| 880 (Isomer 1) | B | A |
| 880 (Isomer 2) | D | D |
| 882 (Isomer 1) | D | D |
| 882 (Isomer 2) | B | B |
| 886 (Isomer 1) | A | A |
| 886 (Isomer 2) | D | D |
| 888 | D | D |
| 892 | D | D |
| 894 | D | D |
| 896 (Isomer 1) | D | D |
| 896 (Isomer 2) | A | A |
| 898 | D | D |
| 900 | D | D |
| 902 (Isomer 1) | D | D |
| 902 (Isomer 2) | B | C |
| 902 (Isomer 3) | D | D |
| 902 (Isomer 4) | A | A |
| 906 | D | D |
| 908 (Isomer 1) | D | D |
| 908 (Isomer 2) | C | C |
| 928 (Isomer 3) | C | D |
| 928 (Isomer 4) | A | C |
| 930 (Isomer 1) | A | B |
| 930 (Isomer 2) | A | B |
| 930 (Isomer 3) | D | D |
| 930 (Isomer 3.1) | D | D |
| 930 (Isomer 3.2) | B | C |
| 930 (Isomer 4) | B | C |
| 930 (Isomer 5) | A | B |
| 930 (Isomer 6) | D | D |
| 932 | D | D |
| 982 (Isomer 1) | D | D |
| 982 (Isomer 2) | A | A |
| 984 (Isomer 1) | D | D |
| 984 (Isomer 2) | A | B |
| 986 (Isomer 1) | D | D |
| 986 (Isomer 2) | A | A |
| 988 (Isomer 1) | A | A |
| 988 (Isomer 2) | D | D |
| 990 (Isomer 1) | A | A |
| 990 (Isomer 2) | D | D |
| 992 (Isomer 1) | D | D |
| 992 (Isomer 2) | A | A |
| 1057 | D | D |
| 1137 | C | D |
| 1149 | D | D |
| 1258 | C | C |
| 1053 (Isomer 1) | A | C |
| 1053 (Isomer 2) | B | C |
| 1053 (Isomer 3) | C | D |
| 1053 (Isomer 4) | D | D |
| 1055 (Isomer 1) | A | A |
| 1055 (Isomer 2) | A | A |
| 1059 (Isomer 1) | D | D |
| 1059 (Isomer 2) | B | B |
| 1111 (Isomer 1) | C | D |
| 1111 (Isomer 2) | A | A |
| 1111 (Isomer 3) | C | D |
| 1111 (Isomer 4) | A | A |
| 1147A (Isomer 1) | D | D |
| 1147A (Isomer 2) | B | C |

A ≥ 30 μM, B > 10 μM and < 30 μM, C ≥ 2 μM and ≤ 10 μM, D < 2 μM.

TABLE 4

Activity data for compounds.

| Compound No. | 229E CPE EC$_{50}$ (μM) |
|---|---|
| 101 | D |
| 103 | D |
| 127 | C |
| 131 | C |
| 133 | D |
| 134 | D |
| 134 (Isomer 1) | D |
| 134 (Isomer 2) | D |
| 135 | D |
| 135 (Isomer 2) | D |
| 136 | A |
| 149 | C |
| 171 | D |
| 185 | D |
| 197 | D |
| 205 | D |
| 323 (Isomer 1) | D |
| 323 (Isomer 2) | D |
| 327 | C |
| 329 | D |
| 331 (Isomer 1) | D |
| 331 (Isomer 2) | D |
| 344D | D |
| 344C | D |
| 344A | D |
| 345 | D |
| 345 (Isomer 1) | D |
| 345 (Isomer 2) | D |
| 355 | A |
| 361 | D |
| 363 | D |
| 375A | D |
| 377 | D |
| 379 | D |
| 385 (Isomer 1) | D |
| 385 (Isomer 2) | D |
| 389A (Isomer 1) | D |
| 393 | D |
| 397 | D |
| 399 (Isomer 1) | D |
| 401 | D |
| 401 (Isomer 1) | D |
| 405 | D |
| 407 | D |
| 433 | C |
| 491 | D |
| 497 (Isomer 2) | D |
| 507 (Isomer 1.1) | D |
| 507 (Isomer 1.2) | D |
| 507 (Isomer 2.1) | D |
| 507 (Isomer 2.2) | D |
| 509 | D |
| 511 | D |
| 511 (Isomer 1) | D |
| 511 (Isomer 2) | D |
| 513 (Isomer 2) | C |
| 519 | D |
| 531 | D |
| 551 | C |
| 577 | D |
| 598 | D |
| 635 | D |
| 637 | D |
| 639 (Isomer 1) | D |
| 643 | D |
| 653 | D |
| 681 (Isomer 1) | D |
| 711 | D |
| 715 | D |
| 717 | D |
| 719 (Isomer 2) | D |
| 721 | D |
| 723 (Isomer 2) | D |
| 725 | D |

TABLE 4-continued

Activity data for compounds.

| Compound No. | 229E CPE EC$_{50}$ (μM) |
|---|---|
| 729 (Isomer 1) | D |
| 731 (Isomer 1) | D |
| 733 (Isomer 1) | D |
| 735 | D |
| 737 | D |
| 739 | D |
| 743 (Isomer 2) | D |
| 745 | D |
| 747 | D |

A>30 μM, B>10 μM and ≤30 μM, C≥2 μM and ≤10 μM, D<2 μM.

TABLE 5

Activity data for compounds.

| Compound No. | 229E CC$_{50}$ |
|---|---|
| 130 (Isomer 1) | A |
| 135 | A |
| 170 | A |

A>30 μM, B>10 μM and ≤30 μM, C≥2 μM and ≤10 μM, D<2 μM.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:
1. A compound represented by:
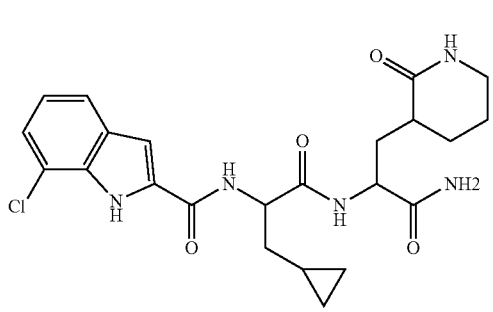
2. The compound of claim 1, wherein the compound is represented by:
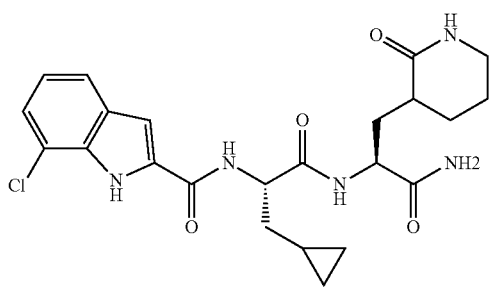
3. A compound represented by:
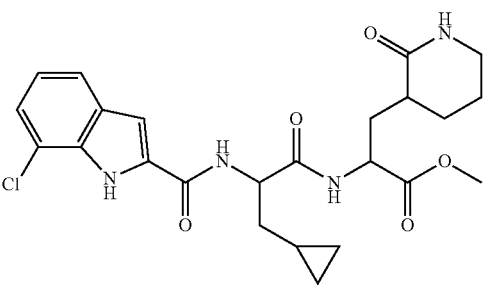
4. The compound of claim 3, wherein the compound is represented by:
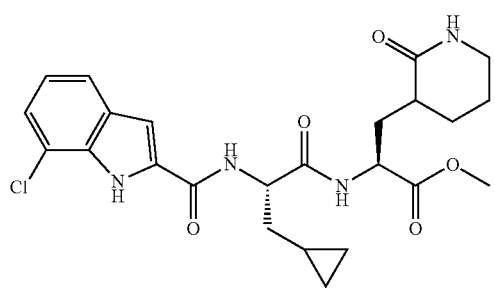
* * * * *